(12) United States Patent
Kc et al.

(10) Patent No.: US 10,703,748 B2
(45) Date of Patent: Jul. 7, 2020

(54) DIAZANAPHTHALEN-3-YL CARBOXAMIDES AND PREPARATION AND USE THEREOF

(71) Applicant: Samumed, LLC, San Diego, CA (US)

(72) Inventors: Sunil Kumar Kc, San Diego, CA (US); Chi Ching Mak, San Diego, CA (US); Jianguo Cao, San Diego, CA (US); Venkataiah Bollu, San Diego, CA (US); Chandramouli Chiruta, San Diego, CA (US); Gopi Kumar Mittapalli, San Diego, CA (US); Brian Walter Eastman, San Diego, CA (US); Brian Joseph Hofilena, San Diego, CA (US)

(73) Assignee: Samumed, LLC, San Diego, CA (US)

( * ) Notice: Subject to any disclaimer, the term of this patent is extended or adjusted under 35 U.S.C. 154(b) by 0 days.

(21) Appl. No.: 16/177,149

(22) Filed: Oct. 31, 2018

(65) Prior Publication Data

US 2019/0127370 A1 May 2, 2019

Related U.S. Application Data

(60) Provisional application No. 62/579,883, filed on Oct. 31, 2017.

(51) Int. Cl.
| | | |
|---|---|---|
| *C07D 471/04* | (2006.01) | |
| *C07D 401/14* | (2006.01) | |
| *A61P 35/00* | (2006.01) | |
| *A61P 25/28* | (2006.01) | |
| *A61P 29/00* | (2006.01) | |
| *C07D 417/14* | (2006.01) | |
| *A61P 25/00* | (2006.01) | |
| *C07D 487/04* | (2006.01) | |

(52) U.S. Cl.
CPC ............ *C07D 471/04* (2013.01); *A61P 25/00* (2018.01); *A61P 25/28* (2018.01); *A61P 29/00* (2018.01); *A61P 35/00* (2018.01); *C07D 401/14* (2013.01); *C07D 417/14* (2013.01); *C07D 487/04* (2013.01)

(58) Field of Classification Search
CPC .. C07D 401/04; C07D 471/08; C07D 417/14; C07D 487/04
See application file for complete search history.

(56) References Cited

U.S. PATENT DOCUMENTS

| | | | |
|---|---|---|---|
| 4,164,559 A | 8/1979 | Miyata et al. | |
| 4,474,752 A | 10/1984 | Haslam et al. | |
| 6,120,484 A | 9/2000 | Silverstein | |
| 6,377,849 B1 | 4/2002 | Lenarz | |
| 6,440,102 B1 | 8/2002 | Arenber | |
| 6,648,873 B2 | 11/2003 | Arenberg et al. | |
| 6,911,211 B2 | 6/2005 | Eini | |
| 7,998,978 B2 | 8/2011 | Huang et al. | |
| 9,951,048 B1 * | 4/2018 | Kc | C07D 471/08 |
| 10,100,038 B2 * | 10/2018 | Kc | C07D 471/08 |
| 10,106,527 B2 * | 10/2018 | Kc | C07D 471/08 |
| 10,287,267 B2 * | 5/2019 | Kc | C07D 401/04 |
| 2013/0079329 A1 | 3/2013 | Hood | |
| 2017/0247365 A1 | 8/2017 | Jones et al. | |
| 2017/0313681 A1 | 11/2017 | Kumar et al. | |
| 2017/0313682 A1 | 11/2017 | Kumar et al. | |
| 2018/0222887 A1 * | 8/2018 | Kc | C07D 401/04 |
| 2019/0119263 A1 * | 4/2019 | Kc | C07D 401/04 |
| 2019/0125740 A1 * | 5/2019 | Kc | A61P 7/00 |
| 2019/0125741 A1 * | 5/2019 | Kc | A61P 7/00 |
| 2019/0233396 A1 * | 8/2019 | Kc | C07D 471/08 |

FOREIGN PATENT DOCUMENTS

| | | |
|---|---|---|
| WO | WO 1987/005297 | 2/1987 |
| WO | WO 2001/053268 | 7/2001 |
| WO | WO 2005/009997 | 2/2005 |
| WO | WO 2007/125405 | 11/2007 |
| WO | WO 2017/151786 | 11/2007 |
| WO | WO 2012/080284 | 6/2012 |
| WO | WO 2013/040215 | 3/2013 |
| WO | 2013/169793 | * 5/2013 |
| WO | WO 2013/16793 | 11/2013 |
| WO | WO 2013/169793 | 11/2013 |
| WO | WO 2013/169793 | 2/2014 |
| WO | WO 2016/046530 | 3/2016 |
| WO | WO 2017/005137 | 1/2017 |
| WO | WO 2017/189823 | 11/2017 |

(Continued)

OTHER PUBLICATIONS

U.S. Appl. No. 16/528,023, filed Jul. 2019.*
PCT Internationa Search Report and Written Opinion in International Appln. No. PCT/US2018/057853, dated Dec. 19, 2018, 19 pages.
He et al, "Synthesis and SAR of novel quinazolines as potent and brain-penetrant c-jun N-terminal kinase (JNK) inhibiotrs," Bioorganic & Medicinal Chemistry Letters, Jan. 19, 2011, 21:6:1719-1723.
Liang et al, "Identification of an imidazopyridine scaffold to generate patent and selective TYK2 inhibitors that demonstrate activity in as in vivo psoriasis model," Bioorganic & Medicinal Chemistry Letters, Aug. 12, 2017, 27:18:4370-4376.
PCT Internationa Search Report and Written Opinion in International Appln. No. PCT/US2018/057854, dated Jan. 4, 2019, 15 pages.

(Continued)

*Primary Examiner* — D Margaret M Seaman

(74) *Attorney, Agent, or Firm* — Fish & Richardson P.C.

(57) ABSTRACT

Diazanaphthalene compounds for treating various diseases and pathologies are disclosed. More particularly, the present disclosure concerns the use of a diazanaphthalene compound or analogs thereof, in the treatment of disorders characterized by the activation of Wnt pathway signaling (e.g., cancer, abnormal cellular proliferation, angiogenesis, Alzheimer's disease, lung disease, inflammation, auto-immune diseases and osteoarthritis), the modulation of cellular events mediated by Wnt pathway signaling, as well as neurological conditions/disorders/diseases linked to overexpression of DYRK1A.

17 Claims, No Drawings

(56) References Cited

FOREIGN PATENT DOCUMENTS

| WO | WO 2017/189829 | 11/2017 |
|---|---|---|
| WO | WO 2018/183964 | 10/2018 |

OTHER PUBLICATIONS

PCT Internationa Search Report and Written Opinion in International Appln. No. PCT/US2018/058564, dated Feb. 4, 2019, 16 pages.

Chou and Talalay, "Quantitative analysis of dose-effect relationships: the combined effects of multiple drugs or enzyme inhibitors," Advances in Enzyme Regulation, 1984, 22:27-55.

U.S. Appl. No. 11/337,815, filed Jan. 24, 2006, Lobi et al.
U.S. Appl. No. 13/614,296, filed Sep. 13, 2012, Hood & Kumar.
U.S. Appl. No. 14/019,229, filed Sep. 5, 2013, Hood & Kumar.
U.S. Appl. No. 14/664,517, filed Mar. 20, 2015, Hood et al.

King et al, "Build-3: a randomized, controlled trial of bosentan in idiopathic pulmonary fibrosis," American Journal of Respiratory and Critical Care Medicine, Jul. 1, 2011, 184:92-99.

Datta et al, "Novel therapeutic approaches for pulmonary fibrosis," British Journal of Pharmacology, Jan. 26, 2011, 163:141-172.

Leyns et al, "Frzb-1 is a secreted antagonist of Wnt signaling expressed in the spemann organizer," Cell, Mar. 21, 1997, 88:747-756.

Liu et al., "Fibrotic lung fibroblasts show blunted inhibition by cAMP due to deficient cAMP response element-binding protein phosphorylation," Journal of Pharmacology and Experimental Therapeutics, 2005, 315(2):678-687.

PCT International Search Report and Written Opinion in International Appln. No. PCT/US2018/056560, dated Dec. 6, 2018, 15 pages.

Watts et al, "RhoA signaling modulates cyclin DI expression in human lung fibroblasts; implications for idiopathic pulmonary fibrosis," Respiratory Research, Jun. 15, 2006, pp. 1-14.

U.S. Appl. No. 16/172,553, filed Oct. 26, 2018, Kumar et al.
U.S. Appl. No. 16/172,589, filed Oct. 26, 2018, Kumar et al.
U.S. Appl. No. 16/164,447, filed Oct. 18, 2018, Kumar et al.

* cited by examiner

DIAZANAPHTHALEN-3-YL CARBOXAMIDES AND PREPARATION AND USE THEREOF

RELATED APPLICATIONS

This application claims the benefit of U.S. Provisional Application No. 62/579,883, filed Oct. 31, 2017, which is incorporated herein by reference in its entirety.

BACKGROUND

Technical Field

This disclosure relates to inhibitors of one or more proteins in the Wnt pathway, including inhibitors of one or more Wnt proteins, and compositions comprising the same. More particularly, it concerns the use of a diazanaphthalene compound or salts or analogs thereof, in the treatment of disorders characterized by the activation of Wnt pathway signaling (e.g., cancer, abnormal cellular proliferation, angiogenesis, Alzheimer's disease, lung disease, inflammation, auto-immune diseases fibrotic disorders, cartilage (chondral) defects, and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states, as well as neurological conditions/disorders/diseases linked to overexpression of DYRK1A.

Background

The Wnt growth factor family includes more than 10 genes identified in the mouse and at least 19 genes identified in the human. Members of the Wnt family of signaling molecules mediate many short- and long-range patterning processes during invertebrate and vertebrate development. The Wnt signaling pathway is known for its role in the inductive interactions that regulate growth and differentiation, and it also plays roles in the homeostatic maintenance of post-embryonic tissue integrity. Wnt stabilizes cytoplasmic β-catenin, which stimulates the expression of genes including c-myc, c jun, fra-1, and cyclin D1. In addition, misregulation of Wnt signaling can cause developmental defects and is implicated in the genesis of several human cancers. The Wnt pathway has also been implicated in the maintenance of stem or progenitor cells in a growing list of adult tissues including skin, blood, gut, prostate, muscle, and the nervous system.

Dual specificity tyrosine-phosphorylation-regulated kinase 1A is an enzyme that in humans is encoded by the DYRK1A gene. DYRK1A is a member of the dual-specificity tyrosine phosphorylation-regulated kinase (DYRK) family. DYRK1A contains a nuclear targeting signal sequence, a protein kinase domain, a leucine zipper motif, and a highly conservative 13-consecutive-histidine repeat. It catalyzes its autophosphorylation on serine/threonine and tyrosine residues. It may play a significant role in a signaling pathway regulating cell proliferation and may be involved in brain development. DYRK1A is localized in the Down syndrome critical region of chromosome 21, and is considered to be a candidate gene for learning defects associated with Down syndrome. DYRK1A is also expressed in adult brain neurons, indicating that DYRK1A may play a role in the mature central nervous system. Thus, several lines of evidence point to some synaptic functions of DYRK1A. For instance, it has been found that DYRK1A phosphorylates and modulates the interaction of several components of the endocytic protein complex machinery (Dynamin 1, Amphiphysin, and Synaptojanin), suggesting a role in synaptic vesicle recycling. In addition, a polymorphism (SNP) in DYRK1A was found to be associated with HIV-1 replication in monocyte-derived macrophages, as well as with progression to AIDS in two independent cohorts of HIV-1-infected individuals.

SUMMARY

The present disclosure provides methods and reagents, involving contacting a cell with an agent, such as a diazanaphthalene compound, in a sufficient amount to antagonize a Wnt activity, e.g., to reverse or control an aberrant growth state or correct a genetic disorder due to mutations in Wnt signaling components.

The present disclosure also provides methods and reagents, involving contacting a cell with an agent, such as a diazanaphthalene compound, in a sufficient amount to antagonize DYRK1A activity, e.g., i) to normalize prenatal and early postnatal brain development; ii) to improve cognitive function in youth and adulthood; and/or iii) to attenuate Alzheimer's-type neurodegeneration.

Some embodiments disclosed herein include Wnt and/or DYRK1A inhibitors containing a diazanaphthalene core. Other embodiments disclosed herein include pharmaceutical compositions and methods of treatment using these compounds.

One embodiment disclosed herein includes a compound having the structure of Formula I:

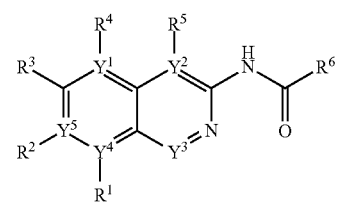

as well as prodrugs and pharmaceutically acceptable salts thereof.

In some embodiments of Formula (I):

$R^1$, $R^2$, $R^4$, and $R^5$ are independently absent or selected from the group consisting of H, halide, unsubstituted —($C_{1-3}$ haloalkyl), and unsubstituted —($C_{1-3}$ alkyl);

$R^3$ is selected from the group consisting of -aryl optionally substituted with 1-5 $R^7$ and -heteroaryl optionally substituted with 1-4 $R^8$;

$R^6$ is selected from the group consisting of —($C_{1-4}$ alkylene)$_p$aryl substituted with 1-5 $R^9$, —($C_{2-4}$ alkenylene)$_p$aryl substituted with 1-5 $R^9$, —($C_{1-4}$ alkylene)$_p$heteroaryl optionally substituted with 1-6 $R^{10}$; —($C_{1-4}$ alkylene)$_p$heterocyclyl optionally substituted with 1-10 $R^{11}$, —($C_{1-4}$ alkylene)$_p$carbocyclyl optionally substituted with 1-12 $R^{12}$, —($C_{1-4}$ alkylene)N($R^{13}$)($R^{14}$), —N($R^{15}$)($R^{16}$), —CF($C_{1-9}$ alkyl)$_2$, —($C_{1-4}$ alkylene)$_p$O($C_{3-9}$ alkyl), and —($C_{2-9}$ alkynyl) optionally substituted with one or more halides; wherein each alkyl of —CF($C_{1-9}$ alkyl)$_2$ is, independently, optionally substituted with one or more halides; wherein each —($C_{1-4}$ alkylene) is, independently, optionally substituted with one or more substituents as defined anywhere herein; wherein —($C_{1-4}$ alkenylene) is, optionally substituted with one or more substituents as defined anywhere herein;

$R^7$ is selected from the group consisting of halide and —N($R^{17}$)$_2$;

each $R^8$ is independently selected from the group consisting of H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —N($R^{15}$)($R^{18}$), —($C_{1-4}$ alkylene)$_p$X$R^{19}$, —C(=O)N($R^{15}$)$_2$, —($C_{1-4}$ alkylene)$_p$heterocyclyl optionally substituted with 1-10 $R^{20}$, and -carbocyclyl optionally substituted with 1-12 $R^{21}$; wherein each —($C_{1-4}$ alkylene) is, independently, optionally substituted with one or more substituents as defined anywhere herein;

alternatively, two adjacent $R^8$ are taken together to form a ring which is selected from the group consisting of -heterocyclyl optionally substituted with 1-10 $R^{22}$ and -carbocyclyl optionally substituted with 1-12 $R^{21}$;

each $R^9$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —X$R^{23}$, —C(=O)N($R^{15}$)$_2$, —($C_{1-4}$ alkylene)$_p$N($R^{24}$)$_2$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents as defined anywhere herein;

with the proviso that when $Y^2$ is N then $R^9$ is not —OMe or

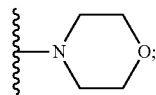

each $R^{10}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —X$R^{23}$, —C(=O)N($R^{15}$)$_2$, —($C_{1-4}$ alkylene)$_p$N($R^{24}$)$_2$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents as defined anywhere herein;

each $R^{11}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$O$R^{19}$, —($C_{1-4}$ alkylene)$_p$heterocyclyl optionally substituted with 1-10 $R^{22}$, —($C_{1-4}$ alkylene)$_p$carbocyclyl optionally substituted with 1-12 $R^{21}$, —N($R^{15}$)($R^{25}$), —C(=O)($R^{26}$), —($C_{1-4}$ alkylene)C(=O)O$R^{27}$, —($C_{1-4}$ alkylene)aryl optionally substituted with one or more halides, —($C_{1-4}$ alkylene)$_p$heteroaryl optionally substituted with one or more halides, and —SO$_2$($R^{28}$); wherein each —($C_{1-4}$ alkylene) is, independently, optionally substituted with one or more substituents as defined anywhere herein;

alternatively, two $R^{11}$ attached to the same carbon atom can together represent =O to form a carbonyl group;

each $R^{12}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$O$R^{19}$, —N($R^{15}$)($R^{29}$), —C(=O)($R^{26}$), —C(=O)O$R^{27}$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents as defined anywhere herein;

$R^{13}$ is selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{20}$, and -carbocyclyl optionally substituted with 1-12 $R^{21}$; wherein —($C_{1-4}$ alkylene) is, optionally substituted with one or more substituents as defined anywhere herein;

$R^{14}$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{20}$, and -carbocyclyl optionally substituted with 1-12 $R^{21}$; wherein —($C_{1-4}$ alkylene) is, optionally substituted with one or more substituents as defined anywhere herein;

each $R^{15}$ is selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

$R^{16}$ is selected from the group consisting of —($C_{1-4}$ alkylene)$_p$heterocyclyl optionally substituted with 1-10 $R^{20}$, and —($C_{1-4}$ alkylene)$_p$carbocyclyl optionally substituted with 1-12 $R^{21}$; wherein each —($C_{1-4}$ alkylene) is, independently, optionally substituted with one or more substituents as defined anywhere herein;

$R^{17}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

alternatively, two adjacent $R^{17}$ are taken together to form a -heterocyclyl ring optionally substituted with 1-10 $R^{22}$;

$R^{18}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —(C=O)$R^{15}$, and —($C_{1-4}$ alkylene)$_p$heterocyclyl optionally substituted with one or more halides or one or more unsubstituted —($C_{1-5}$ alkyl); wherein —($C_{1-4}$ alkylene) is, independently, optionally substituted with one or more substituents as defined anywhere herein;

each $R^{19}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with one or more halides or one or more unsubstituted —($C_{1-5}$ alkyl), and —($C_{1-4}$ alkylene)$_p$carbocyclyl optionally substituted with 1-12 $R^{21}$; wherein each —($C_{1-4}$ alkylene) is, independently, optionally substituted with one or more substituents as defined anywhere herein;

each $R^{20}$ independently is selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —N($R^{15}$)$_2$, and —($C_{1-4}$ alkylene)$_p$carbocyclyl optionally substituted with 1-12 $R^{21}$; wherein each —($C_{1-4}$ alkylene) is, independently, optionally substituted with one or more substituents as defined anywhere herein;

each $R^{21}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{22}$ is independently selected from the group consisting of halide, unsubstituted —($C_{1-5}$ alkyl), unsubstituted —(C$_{2-5}$ alkenyl), unsubstituted —(C$_{2-5}$ alkynyl), unsubstituted —(C$_{1-5}$ haloalkyl), —CN, —OH, —N(R$^{15}$)$_2$, —C(=O)R$^{34}$, and —(C$_{1-4}$ alkylene)$_p$carbocyclyl optionally substituted with 1-12 R$^{21}$; wherein each —(C$_{1-4}$ alkylene) is, independently, optionally substituted with one or more substituents as defined anywhere herein;

each R$^{23}$ is independently selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)N(R$^{15}$)$_2$, —(C$_{1-4}$ alkylene)$_p$aryl optionally substituted with 1-10 R$^{30}$, —(C$_{1-4}$ alkylene)$_p$heterocyclyl optionally substituted with 1-12 R$^{31}$, and —(C$_{1-4}$ alkylene)$_p$carbocyclyl optionally substituted with 1-12 R$^{21}$; wherein each —(C$_{1-4}$ alkylene) is, independently, optionally substituted with one or more substituents as defined anywhere herein;

each R$^{24}$ is independently selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$heterocyclyl optionally substituted with one or more halides or one or more unsubstituted —(C$_{1-5}$ alkyl), and —(C$_{1-4}$ alkylene)N(R$^{15}$)$_2$; wherein each —(C$_{1-4}$ alkylene) is, independently, optionally substituted with one or more substituents as defined anywhere herein;

each R$^{25}$ is selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$heterocyclyl optionally substituted with 1-10 R$^{32}$, —(C$_{1-4}$ alkylene)$_p$carbocyclyl optionally substituted with 1-12 R$^{21}$, —(C$_{1-4}$ alkylene)OR$^{33}$; wherein each —(C$_{1-4}$ alkylene) is, independently, optionally substituted with one or more substituents as defined anywhere herein;

R$^{26}$ is selected from the group consisting of H, unsubstituted —(C$_{3-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$aryl optionally substituted with one or more halides or unsubstituted —(C$_{1-5}$ alkyl), —(C$_{1-4}$ alkylene)$_p$heteroaryl optionally substituted with one or more halides or one or more unsubstituted —(C$_{1-5}$ alkyl), and —(C$_{1-4}$ alkylene)$_p$heterocyclyl optionally substituted with one or more halides or one or more unsubstituted —(C$_{1-5}$ alkyl); wherein each —(C$_{1-4}$ alkylene) is, independently, optionally substituted with one or more substituents as defined anywhere herein;

R$^{27}$ is selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$aryl optionally substituted with one or more halides or one or more unsubstituted —(C$_{1-5}$ alkyl), —(C$_{1-4}$ alkylene)$_p$heteroaryl optionally substituted with one or more halides or unsubstituted —(C$_{1-5}$ alkyl), and —(C$_{1-4}$ alkylene)$_p$heterocyclyl optionally substituted with one or more halides or one or more unsubstituted —(C$_{1-5}$ alkyl); wherein each —(C$_{1-4}$ alkylene) is, independently, optionally substituted with one or more substituents as defined anywhere herein;

R$^{28}$ is selected from the group consisting of unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$aryl optionally substituted with one or more halides or one or more unsubstituted —(C$_{1-5}$ alkyl), —(C$_{1-4}$ alkylene)$_p$heteroaryl optionally substituted with one or more halides or one or more unsubstituted —(C$_{1-5}$ alkyl), and —(C$_{1-4}$ alkylene)$_p$heterocyclyl optionally substituted with one or more halides or one or more unsubstituted —(C$_{1-5}$ alkyl); wherein —(C$_{1-4}$ alkylene) is, optionally substituted with one or more substituents as defined anywhere herein;

each R$^{29}$ is selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$heterocyclyl optionally substituted with 1-10 R$^{32}$, —(C$_{1-4}$ alkylene)$_p$carbocyclyl optionally substituted with 1-12 R$^{21}$, —(C$_{1-4}$ alkylene)OR$^{33}$; wherein each —(C$_{1-4}$ alkylene) is, independently, optionally substituted with one or more substituents as defined anywhere herein;

each R$^{30}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), and —CN;

each R$^{31}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —CN, —OH, —C(=O)R$^{34}$, —N(R$^{24}$)$_2$, and —(C$_{1-4}$ alkylene)$_p$carbocyclyl optionally substituted with 1-12 R$^{21}$; wherein each —(C$_{1-4}$ alkylene) is, independently, optionally substituted with one or more substituents as defined anywhere herein;

each R$^{32}$ is independently selected from the group consisting of halide and unsubstituted —(C$_{1-5}$ alkyl);

each R$^{33}$ is independently selected from the group consisting of H and unsubstituted —(C$_{1-5}$ alkyl);

each R$^{34}$ is a heteroaryl optionally substituted with 1-6 R$^{35}$;

each R$^{35}$ is a -heterocyclyl optionally substituted with one or more halides or one or more unsubstituted —(C$_{1-5}$ alkyl);

each X is selected from the group consisting of O and S;
Y$^3$ is CH or nitrogen;
Y$^1$, Y$^2$, Y$^4$, and Y$^5$ are independently selected from the group consisting of carbon and nitrogen; wherein
if Y$^1$ is nitrogen then Y$^2$, Y$^4$, and Y$^5$ are carbon, Y$^3$ is CH, and R$^4$ is absent;
if Y$^2$ is nitrogen then Y$^1$, Y$^4$, and Y$^5$ are carbon, Y$^3$ is CH, and R$^5$ is absent;
if Y$^3$ is nitrogen then Y$^1$, Y$^2$, Y$^4$, and Y$^5$ are carbon;
if Y$^4$ is nitrogen then Y$^1$, Y$^2$, and Y$^5$ are carbon, Y$^3$ is CH, and R$^1$ is absent;
if Y$^5$ is nitrogen then Y$^1$, Y$^2$, and Y$^4$ are carbon, Y$^3$ is CH, and R$^2$ is absent; and
each p is independently 0 or 1.

One embodiment disclosed herein includes a compound having the structure of Formula I:

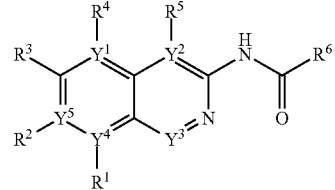

as well as prodrugs and pharmaceutically acceptable salts thereof.

In another embodiment of Formula (I):
R$^1$, R$^2$, R$^4$, and R$^5$ are independently absent or selected from the group consisting of H, halide, unsubstituted —(C$_{1-3}$ haloalkyl), and unsubstituted —(C$_{1-3}$ alkyl);
R$^3$ is selected from the group consisting of -aryl optionally substituted with 1-5 R$^7$ and -heteroaryl optionally substituted with 1-4 R$^8$;

$R^6$ is selected from the group consisting of —($C_{1-4}$ alkylene)$_p$aryl substituted with 1-5 $R^9$, —($C_{2-4}$ alkenylene)$_p$aryl substituted with 1-5 $R^9$, —($C_{1-4}$ alkylene)$_p$heteroaryl optionally substituted with 1-6 $R^{10}$; —($C_{1-4}$ alkylene)$_p$heterocyclyl optionally substituted with 1-10 $R^{11}$, —($C_{1-4}$ alkylene)$_p$carbocyclyl optionally substituted with 1-12 $R^{12}$, —($C_{1-4}$ alkylene)N($R^{13}$)($R^{14}$), —N($R^{15}$)($R^{16}$), —CF($C_{1-9}$ alkyl)$_2$, —($C_{1-4}$ alkylene)$_p$O ($C_{3-9}$ alkyl), and —($C_{2-9}$ alkynyl) optionally substituted with one or more halides; wherein each alkyl of —CF($C_{1-9}$ alkyl)$_2$ is, independently, optionally substituted with one or more halides; wherein each —($C_{1-4}$ alkylene) is, independently, optionally substituted with one or more substituents; wherein —($C_{1-4}$ alkenylene) is, optionally substituted with one or more substituents;

$R^7$ is selected from the group consisting of halide and —N($R^{17}$)$_2$;

each $R^8$ is independently selected from the group consisting of H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —N($R^{15}$)($R^{18}$), —($C_{1-4}$ alkylene)$_p$X$R^{19}$, —C(=O)N($R^{15}$)$_2$, —($C_{1-4}$ alkylene)$_p$heterocyclyl optionally substituted with 1-10 $R^{20}$, and -carbocyclyl optionally substituted with 1-12 $R^{21}$; wherein each —($C_{1-4}$ alkylene) is, independently, optionally substituted with one or more substituents;

alternatively, two adjacent $R^8$ are taken together to form a ring which is selected from the group consisting of -heterocyclyl optionally substituted with 1-10 $R^{22}$ and -carbocyclyl optionally substituted with 1-12 $R^{21}$;

each $R^9$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —X$R^{23}$, —C(=O)N($R^{15}$)$_2$, —($C_{1-4}$ alkylene)$_p$N($R^{24}$)$_2$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

with the proviso that when $Y^2$ is N then $R^9$ is not —OMe or

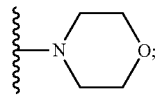

each $R^{10}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —X$R^{23}$, —C(=O)N($R^{15}$)$_2$, —($C_{1-4}$ alkylene)$_p$N($R^{24}$)$_2$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{11}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$O$R^9$, —($C_{1-4}$ alkylene)$_p$heterocyclyl optionally substituted with 1-10 $R^{22}$, —($C_{1-4}$ alkylene)$_p$carbocyclyl optionally substituted with 1-12 $R^{21}$, —N($R^{15}$)($R^{25}$), —C(=O)($R^{26}$), —($C_{1-4}$ alkylene) C(=O)O$R^{27}$, —($C_{1-4}$ alkylene)aryl optionally substituted with one or more halides, —($C_{1-4}$ alkylene)$_p$heteroaryl optionally substituted with one or more halides, and —SO$_2$ ($R^{28}$); wherein each —($C_{1-4}$ alkylene) is, independently, optionally substituted with one or more substituents;

alternatively, two $R^{11}$ attached to the same carbon atom can together represent =O to form a carbonyl group;

each $R^{12}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$O$R^{19}$, —N($R^{15}$) ($R^{29}$), —C(=O)($R^{26}$), —C(=O)O$R^{27}$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

$R^{13}$ is selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{20}$, and -carbocyclyl optionally substituted with 1-12 $R^{21}$; wherein —($C_{1-4}$ alkylene) is, optionally substituted with one or more substituents;

$R^{14}$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{20}$, and -carbocyclyl optionally substituted with 1-12 $R^{21}$; wherein —($C_{1-4}$ alkylene) is, optionally substituted with one or more substituents;

each $R^{15}$ is selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

$R^{16}$ is selected from the group consisting of —($C_{1-4}$ alkylene)$_p$heterocyclyl optionally substituted with 1-10 $R^{20}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

$R^{17}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

alternatively, two adjacent $R^{17}$ are taken together to form a -heterocyclyl ring optionally substituted with 1-10 $R^{22}$;

$R^{18}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —(C=O)$R^{15}$, and —($C_{1-4}$ alkylene)$_p$heterocyclyl optionally substituted with one or more halides or one or more unsubstituted —($C_{1-5}$ alkyl); wherein —($C_{1-4}$ alkylene) is, independently, optionally substituted with one or more substituents;

each $R^{19}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with one or more halides or one or more unsubstituted —($C_{1-5}$ alkyl), and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{20}$ independently is selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —N($R^{15}$)$_2$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{21}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{22}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —N($R^{15}$)$_2$, —C(=O)$R^{34}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{23}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)N($R^{15}$)$_2$, —($C_{1-4}$ alkylene)$_p$aryl optionally substituted with 1-10 $R^{30}$, —($C_{1-4}$ alkylene)$_p$heterocyclyl optionally substituted with 1-12 $R^{31}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{24}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with one or more halides or one or more unsubstituted —($C_{1-5}$ alkyl), and —($C_{1-4}$ alkylene)N($R^{15}$)$_2$; wherein each —($C_{1-4}$ alkylene) is, independently, optionally substituted with one or more substituents;

each $R^{25}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with 1-10 $R^{32}$, —($C_{1-4}$ alkylene)$_p$carbocyclyl optionally substituted with 1-12 $R^{21}$, —($C_{1-4}$ alkylene)O$R^{33}$; wherein each —($C_{1-4}$ alkylene) is, independently, optionally substituted with one or more substituents;

$R^{26}$ is selected from the group consisting of H, unsubstituted —($C_{3-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with one or more halides or unsubstituted —($C_{1-5}$ alkyl), —($C_{1-4}$ alkylene)$_p$heteroaryl optionally substituted with one or more halides or one or more unsubstituted —($C_{1-5}$ alkyl), and —($C_{1-4}$ alkylene)$_p$heterocyclyl optionally substituted with one or more halides or one or more unsubstituted —($C_{1-5}$ alkyl); wherein each —($C_{1-4}$ alkylene) is, independently, optionally substituted with one or more substituents;

$R^{27}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with one or more halides or one or more unsubstituted —($C_{1-5}$ alkyl), —($C_{1-4}$ alkylene)$_p$heteroaryl optionally substituted with one or more halides or unsubstituted —($C_{1-5}$ alkyl), and —($C_{1-4}$ alkylene)$_p$heterocyclyl optionally substituted with one or more halides or one or more unsubstituted —($C_{1-5}$ alkyl); wherein each —($C_{1-4}$ alkylene) is, independently, optionally substituted with one or more substituents;

$R^{28}$ is selected from the group consisting of unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with one or more halides or one or more unsubstituted —($C_{1-5}$ alkyl), —($C_{1-4}$ alkylene)$_p$heteroaryl optionally substituted with one or more halides or one or more unsubstituted —($C_{1-5}$ alkyl), and —($C_{1-4}$ alkylene)$_p$heterocyclyl optionally substituted with one or more halides or one or more unsubstituted —($C_{1-5}$ alkyl); wherein —($C_{1-4}$ alkylene) is, optionally substituted with one or more substituents;

each $R^{29}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with 1-10 $R^{32}$, —($C_{1-4}$ alkylene)$_p$carbocyclyl optionally substituted with 1-12 $R^{21}$, —($C_{1-4}$ alkylene)O$R^{33}$, and —C(=O)O($C_{1-5}$ alkyl); wherein each —($C_{1-4}$ alkylene) is, independently, optionally substituted with one or more substituents;

each $R^{30}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{31}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —C(=O)$R^{34}$, —N($R^{24}$)$_2$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{32}$ is independently selected from the group consisting of halide and unsubstituted —($C_{1-5}$ alkyl);

each $R^{33}$ is independently selected from the group consisting of H and unsubstituted —($C_{1-5}$ alkyl);

each $R^{34}$ is independently selected from the group consisting of —O($C_{1-5}$ alkyl) and a heteroaryl optionally substituted with 1-6 $R^{35}$;

each $R^{35}$ is a -heterocyclyl optionally substituted with one or more halides or one or more unsubstituted —($C_{1-5}$ alkyl);

each X is selected from the group consisting of O and S;
$Y^3$ is CH or nitrogen;
$Y^1$, $Y^2$, $Y^4$, and $Y^5$ are independently selected from the group consisting of carbon and nitrogen; wherein
if $Y^1$ is nitrogen then $Y^2$, $Y^4$, and $Y^5$ are carbon, $Y^3$ is CH, and $R^4$ is absent;
if $Y^2$ is nitrogen then $Y^1$, $Y^4$, and $Y^5$ are carbon, $Y^3$ is CH, and $R^5$ is absent;
if $Y^3$ is nitrogen then $Y^1$, $Y^2$, $Y^4$, and $Y^5$ are carbon;
if $Y^4$ is nitrogen then $Y^1$, $Y^2$, and $Y^5$ are carbon, $Y^3$ is CH, and $R^1$ is absent;
if $Y^5$ is nitrogen then $Y^1$, $Y^2$, and $Y^4$ are carbon, $Y^3$ is CH, and $R^2$ is absent; and
each p is independently 0 or 1.

Another embodiment disclosed herein includes a compound having the structure of Formula Ia:

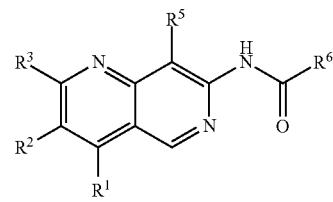

Ia as well as prodrugs and pharmaceutically acceptable salts thereof.

In another embodiment of Formula (Ia):
$R^1$, $R^2$, and $R^5$ are independently absent or selected from the group consisting of H, halide, unsubstituted —($C_{1-3}$ haloalkyl), and unsubstituted —($C_{1-3}$ alkyl);

$R^3$ is selected from the group consisting of -aryl optionally substituted with 1-5 $R^7$ and -heteroaryl optionally substituted with 1-4 $R^8$;

$R^6$ is selected from the group consisting of —($C_{1-4}$ alkylene)$_p$aryl substituted with 1-5 $R^9$, —($C_{2-4}$ alkenylene)$_p$aryl substituted with 1-5 $R^9$, —($C_{1-4}$ alkylene)$_p$heteroaryl optionally substituted with 1-6 $R^{10}$; —($C_{1-4}$ alkylene)$_p$heterocyclyl optionally substituted with 1-10 $R^{11}$, —($C_{1-4}$ alkylene)$_p$carbocyclyl optionally substituted with 1-12 $R^{12}$, —($C_{1-4}$ alkylene)N($R^{13}$)($R^{14}$), —N($R^{15}$)($R^{16}$), —CF($C_{1-9}$ alkyl)$_2$, —($C_{1-4}$ alkylene)$_p$O($C_{3-9}$ alkyl), and —($C_{2-9}$ alkynyl) optionally substituted with one or more halides; wherein each alkyl of —CF($C_{1-9}$ alkyl)$_2$ is, independently, optionally substituted with one or more halides; wherein each —($C_{1-4}$ alkylene) is, independently, optionally substituted with one or more substituents; wherein —($C_{1-4}$ alkenylene) is, optionally substituted with one or more substituents;

$R^7$ is selected from the group consisting of halide and —N($R^{17}$)$_2$;

each $R^8$ is independently selected from the group consisting of H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —N($R^{15}$)($R^{18}$), —($C_{1-4}$ alkylene)$_p$X$R^{19}$, —C(=O)N($R^{15}$)$_2$, —($C_{1-4}$ alkylene)$_p$heterocyclyl optionally substituted with 1-10 $R^{20}$, and -carbocyclyl optionally substituted with 1-12 $R^{21}$; wherein each —($C_{1-4}$ alkylene) is, independently, optionally substituted with one or more substituents;

alternatively, two adjacent $R^8$ are taken together to form a ring which is selected from the group consisting of -heterocyclyl optionally substituted with 1-10 $R^{22}$ and -carbocyclyl optionally substituted with 1-12 $R^{21}$;

each $R^9$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —X$R^{23}$, —C(=O)N($R^{15}$)$_2$, —($C_{1-4}$ alkylene)$_p$N($R^{24}$)$_2$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{10}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —X$R^{23}$, —C(=O)N($R^{15}$)$_2$, —($C_{1-4}$ alkylene)$_p$N($R^{24}$)$_2$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{11}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$O$R^{19}$, —($C_{1-4}$ alkylene)$_p$heterocyclyl optionally substituted with 1-10 $R^{22}$, —($C_{1-4}$ alkylene)$_p$carbocyclyl optionally substituted with 1-12 $R^{21}$, —N($R^{15}$)($R^{25}$), —C(=O)($R^{26}$), —($C_{1-4}$ alkylene)C(=O)O$R^{27}$, —($C_{1-4}$ alkylene)aryl optionally substituted with one or more halides, —($C_{1-4}$ alkylene)$_p$heteroaryl optionally substituted with one or more halides, and —SO$_2$($R^{28}$); wherein each —($C_{1-4}$ alkylene) is, independently, optionally substituted with one or more substituents;

alternatively, two $R^{11}$ attached to the same carbon atom can together represent =O to form a carbonyl group;

each $R^{12}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$O$R^{19}$, —N($R^{15}$)($R^{29}$), —C(=O)($R^{26}$), —C(=O)O$R^{27}$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

$R^{13}$ is selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{20}$, and -carbocyclyl optionally substituted with 1-12 $R^{21}$; wherein —($C_{1-4}$ alkylene) is, optionally substituted with one or more substituents;

$R^{14}$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{20}$, and -carbocyclyl optionally substituted with 1-12 $R^{21}$; wherein —($C_{1-4}$ alkylene) is, optionally substituted with one or more substituents;

each $R^{15}$ is selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

$R^{16}$ is selected from the group consisting of —($C_{1-4}$ alkylene)$_p$heterocyclyl optionally substituted with 1-10 $R^{20}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

$R^{17}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

alternatively, two adjacent $R^{17}$ are taken together to form a -heterocyclyl ring optionally substituted with 1-10 $R^{22}$;

$R^{18}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —(C=O)$R^5$, and —($C_{1-4}$ alkylene)$_p$heterocyclyl optionally substituted with one or more halides or one or more unsubstituted —($C_{1-5}$ alkyl); wherein —($C_{1-4}$ alkylene) is, independently, optionally substituted with one or more substituents;

each $R^{19}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with one or more halides or one or more unsubstituted —($C_{1-5}$ alkyl), and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{20}$ independently is selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —N($R^{15}$)$_2$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{21}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{22}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —N($R^{15}$)$_2$, —C(=O)$R^{34}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{23}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)N($R^{15}$)$_2$, —($C_{1-4}$ alkylene)$_p$aryl optionally substituted with 1-10 $R^{30}$, —($C_{1-4}$ alkylene)$_p$heterocyclyl optionally substituted with 1-12 $R^{31}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{24}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with one or more halides or one or more unsubstituted —($C_{1-5}$ alkyl), and —($C_{1-4}$ alkylene)N($R^{15}$)$_2$; wherein each —($C_{1-4}$ alkylene) is, independently, optionally substituted with one or more substituents;

each $R^{25}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with 1-10 $R^{32}$, —($C_{1-4}$ alkylene)$_p$carbocyclyl optionally substituted with 1-12 $R^{21}$, —($C_{1-4}$ alkylene)O$R^{33}$; wherein each —($C_{1-4}$ alkylene) is, independently, optionally substituted with one or more substituents;

$R^{26}$ is selected from the group consisting of H, unsubstituted —($C_{3-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with one or more halides or unsubstituted —($C_{1-5}$ alkyl), —($C_{1-4}$ alkylene)$_p$heteroaryl optionally substituted with one or more halides or one or more unsubstituted —($C_{1-5}$ alkyl), and —($C_{1-4}$ alkylene)$_p$heterocyclyl optionally substituted with one or more halides or one or more unsubstituted —($C_{1-5}$ alkyl); wherein each —($C_{1-4}$ alkylene) is, independently, optionally substituted with one or more substituents;

$R^{27}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with one or more halides or one or more unsubstituted —($C_{1-5}$ alkyl), —($C_{1-4}$ alkylene)$_p$heteroaryl optionally substituted with one or more halides or one or more unsubstituted —($C_{1-5}$ alkyl), and —($C_{1-4}$ alkylene)$_p$heterocyclyl optionally substituted with one or more halides or one or more unsubstituted —($C_{1-5}$ alkyl); wherein each —($C_{1-4}$ alkylene) is, independently, optionally substituted with one or more substituents;

$R^{28}$ is selected from the group consisting of unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with one or more halides or one or more unsubstituted —($C_{1-5}$ alkyl), —($C_{1-4}$ alkylene)$_p$heteroaryl optionally substituted with one or more halides or one or more unsubstituted —($C_{1-5}$ alkyl), and —($C_{1-4}$ alkylene)$_p$heterocyclyl optionally substituted with one or more halides or one or more unsubstituted —($C_{1-5}$ alkyl); wherein —($C_{1-4}$ alkylene) is, optionally substituted with one or more substituents;

each $R^{29}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with 1-10 $R^{32}$, —($C_{1-4}$ alkylene)$_p$carbocyclyl optionally substituted with 1-12 $R^{21}$, —($C_{1-4}$ alkylene)O$R^{33}$, and —C(=O)O($C_{1-5}$ alkyl); wherein each —($C_{1-4}$ alkylene) is, independently, optionally substituted with one or more substituents;

each $R^{30}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{31}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —C(=O)$R^{34}$, —N($R^{24}$)$_2$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{32}$ is independently selected from the group consisting of halide and unsubstituted —($C_{1-5}$ alkyl);

each $R^{33}$ is independently selected from the group consisting of H and unsubstituted —($C_{1-5}$ alkyl);

each $R^{34}$ is independently selected from the group consisting of —O($C_{1-5}$ alkyl) and a heteroaryl optionally substituted with 1-6 $R^{35}$;

each $R^{35}$ is a -heterocyclyl optionally substituted with one or more halides or one or more unsubstituted —($C_{1-5}$ alkyl);

each X is selected from the group consisting of O and S;

each p is independently 0 or 1.

Another embodiment disclosed herein includes a compound having the structure of Formula Ib:

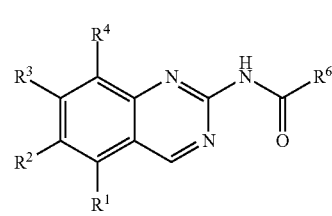

Ib as well as prodrugs and pharmaceutically acceptable salts thereof.

In another embodiment of Formula (Ib):

$R^1$, $R^2$, and $R^4$ are independently absent or selected from the group consisting of H, halide, unsubstituted —($C_{1-3}$ haloalkyl), and unsubstituted —($C_{1-3}$ alkyl);

$R^3$ is selected from the group consisting of -aryl optionally substituted with 1-5 $R^7$ and -heteroaryl optionally substituted with 1-4 $R^8$;

$R^6$ is selected from the group consisting of —($C_{1-4}$ alkylene)$_p$aryl substituted with 1-5 $R^9$, —($C_{2-4}$ alkenylene)$_p$aryl substituted with 1-5 $R^9$, —($C_{1-4}$ alkylene)$_p$heteroaryl optionally substituted with 1-6 $R^{10}$; —($C_{1-4}$ alkylene)$_p$heterocyclyl optionally substituted with 1-10 $R^{11}$, —($C_{1-4}$ alkylene)$_p$carbocyclyl optionally substituted with 1-12 $R^{12}$, —($C_{1-4}$ alkylene)N($R^{13}$)($R^{14}$), —N($R^{15}$)($R^{16}$), —CF($C_{1-9}$ alkyl)$_2$, —($C_{1-4}$ alkylene)$_p$O($C_{3-9}$ alkyl), and —($C_{2-9}$ alkynyl) optionally substituted with one or more halides; wherein each alkyl of —CF($C_{1-9}$ alkyl)$_2$ is, independently, optionally substituted with one or more halides; wherein each —($C_{1-4}$ alkylene) is, independently, optionally substituted with one or more substituents; wherein —($C_{1-4}$ alkenylene) is, optionally substituted with one or more substituents;

$R^7$ is selected from the group consisting of halide and —N($R^{17}$)$_2$;

each $R^8$ is independently selected from the group consisting of H, halide, unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —CN, —N($R^{15}$)($R^{18}$), —(C$_{1-4}$ alkylene)$_p$X$R^{19}$, —C(=O)N($R^{15}$)$_2$, —(C$_{1-4}$ alkylene)$_p$heterocyclyl optionally substituted with 1-10 $R^{20}$, and -carbocyclyl optionally substituted with 1-12 $R^{21}$; wherein each —(C$_{1-4}$ alkylene) is, independently, optionally substituted with one or more substituents;

alternatively, two adjacent $R^8$ are taken together to form a ring which is selected from the group consisting of -heterocyclyl optionally substituted with 1-10 $R^{22}$ and -carbocyclyl optionally substituted with 1-12 $R^{21}$;

each $R^9$ is independently selected from the group consisting of halide, unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —X$R^{23}$, —C(=O)N($R^{15}$)$_2$, —(C$_{1-4}$ alkylene)$_p$N($R^{24}$)$_2$, —(C$_{1-4}$ alkylene)$_p$heterocyclyl optionally substituted with 1-10 $R^{22}$, and —(C$_{1-4}$ alkylene)$_p$carbocyclyl optionally substituted with 1-12 $R^{21}$; wherein each —(C$_{1-4}$ alkylene) is, independently, optionally substituted with one or more substituents;

with the proviso that $R^9$ is not —OMe or

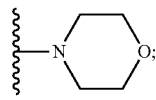

each $R^{10}$ is independently selected from the group consisting of halide, unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —CN, —X$R^{23}$, —C(=O)N($R^{15}$)$_2$, —(C$_{1-4}$ alkylene)$_p$N($R^{24}$)$_2$, —(C$_{1-4}$ alkylene)$_p$heterocyclyl optionally substituted with 1-10 $R^{22}$, and —(C$_{1-4}$ alkylene)$_p$carbocyclyl optionally substituted with 1-12 $R^{21}$; wherein each —(C$_{1-4}$ alkylene) is, independently, optionally substituted with one or more substituents;

each $R^{11}$ is independently selected from the group consisting of halide, unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —(C$_{1-4}$ alkylene)$_p$O$R^{19}$, —(C$_{1-4}$ alkylene)$_p$heterocyclyl optionally substituted with 1-10 $R^{22}$, —(C$_{1-4}$ alkylene)$_p$carbocyclyl optionally substituted with 1-12 $R^{21}$, —N($R^{15}$)($R^{25}$), —C(=O)($R^{26}$), —(C$_{1-4}$ alkylene)C(=O)O$R^{27}$, —(C$_{1-4}$ alkylene)aryl optionally substituted with one or more halides, —(C$_{1-4}$ alkylene)$_p$heteroaryl optionally substituted with one or more halides, and —SO$_2$($R^{28}$); wherein each —(C$_{1-4}$ alkylene) is, independently, optionally substituted with one or more substituents;

alternatively, two $R^{11}$ attached to the same carbon atom can together represent =O to form a carbonyl group;

each $R^{12}$ is independently selected from the group consisting of halide, unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —(C$_{1-4}$ alkylene)$_p$O$R^{19}$, —N($R^{15}$)($R^{29}$), —C(=O)($R^{26}$), —C(=O)O$R^{27}$, —(C$_{1-4}$ alkylene)$_p$heterocyclyl optionally substituted with 1-10 $R^{22}$, and —(C$_{1-4}$ alkylene)$_p$carbocyclyl optionally substituted with 1-12 $R^{21}$; wherein each —(C$_{1-4}$ alkylene) is, independently, optionally substituted with one or more substituents;

$R^{13}$ is selected from the group consisting of H, unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —(C$_{1-4}$ alkylene)$_p$heterocyclyl optionally substituted with 1-10 $R^{20}$, and -carbocyclyl optionally substituted with 1-12 $R^{21}$; wherein —(C$_{1-4}$ alkylene) is, optionally substituted with one or more substituents;

$R^{14}$ is selected from the group consisting of unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —(C$_{1-4}$ alkylene)$_p$heterocyclyl optionally substituted with 1-10 $R^{20}$, and -carbocyclyl optionally substituted with 1-12 $R^{21}$; wherein —(C$_{1-4}$ alkylene) is, optionally substituted with one or more substituents;

each $R^{15}$ is selected from the group consisting of H, unsubstituted —(C$_{1-5}$ alkyl), unsubstituted —(C$_{2-5}$ alkenyl), unsubstituted —(C$_{2-5}$ alkynyl), and unsubstituted —(C$_{1-5}$ haloalkyl);

$R^{16}$ is selected from the group consisting of —(C$_{1-4}$ alkylene)$_p$heterocyclyl optionally substituted with 1-10 $R^{20}$, and —(C$_{1-4}$ alkylene)$_p$carbocyclyl optionally substituted with 1-12 $R^{21}$; wherein each —(C$_{1-4}$ alkylene) is, independently, optionally substituted with one or more substituents;

$R^{17}$ is independently selected from the group consisting of H, unsubstituted —(C$_{1-5}$ alkyl), unsubstituted —(C$_{2-5}$ alkenyl), unsubstituted —(C$_{2-5}$ alkynyl), and unsubstituted —(C$_{1-5}$ haloalkyl);

alternatively, two adjacent $R^{17}$ are taken together to form a -heterocyclyl ring optionally substituted with 1-10 $R^{22}$;

$R^{18}$ is independently selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C=O)$R^{15}$, and —(C$_{1-4}$ alkylene)$_p$heterocyclyl optionally substituted with one or more halides or one or more unsubstituted —(C$_{1-5}$ alkyl); wherein —(C$_{1-4}$ alkylene) is, independently, optionally substituted with one or more substituents;

each $R^{19}$ is independently selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$heterocyclyl optionally substituted with one or more halides or one or more unsubstituted —(C$_{1-5}$ alkyl), and —(C$_{1-4}$ alkylene)$_p$carbocyclyl optionally substituted with 1-12 $R^{21}$; wherein each —(C$_{1-4}$ alkylene) is, independently, optionally substituted with one or more substituents;

each $R^{20}$ independently is selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —CN, —OH, —N($R^{15}$)$_2$, and —(C$_{1-4}$ alkylene)$_p$carbocyclyl optionally substituted with 1-12 $R^{21}$; wherein each —(C$_{1-4}$ alkylene) is, independently, optionally substituted with one or more substituents;

each $R^{21}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), and —CN;

each $R^{22}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —CN, —OH, —N($R^{15}$)$_2$, —C(=O)$R^{34}$, and —(C$_{1-4}$ alkylene)$_p$carbocyclyl optionally substituted with 1-12 $R^{21}$; wherein each —(C$_{1-4}$ alkylene) is, independently, optionally substituted with one or more substituents;

each $R^{23}$ is independently selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)N($R^{15}$)$_2$, —(C$_{1-4}$ alkylene)$_p$aryl optionally substituted with 1-10 $R^{30}$, —(C$_{1-4}$ alkylene)$_p$heterocyclyl optionally substituted with 1-12 R$^{31}$, and —(C$_{1-4}$ alkylene)$_p$carbocyclyl optionally substituted with 1-12 R$^{21}$; wherein each —(C$_{1-4}$ alkylene) is, independently, optionally substituted with one or more substituents;

each R$^{24}$ is independently selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$heterocyclyl optionally substituted with one or more halides or one or more unsubstituted —(C$_{1-5}$ alkyl), and —(C$_{1-4}$ alkylene)N(R$^{15}$)$_2$; wherein each —(C$_{1-4}$ alkylene) is, independently, optionally substituted with one or more substituents;

each R$^{25}$ is selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$heterocyclyl optionally substituted with 1-10 R$^{32}$, —(C$_{1-4}$ alkylene)$_p$carbocyclyl optionally substituted with 1-12 R$^{21}$, —(C$_{1-4}$ alkylene)OR$^{33}$; wherein each —(C$_{1-4}$ alkylene) is, independently, optionally substituted with one or more substituents;

R$^{26}$ is selected from the group consisting of H, unsubstituted —(C$_{3-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$aryl optionally substituted with one or more halides or unsubstituted —(C$_{1-5}$ alkyl), —(C$_{1-4}$ alkylene)$_p$heteroaryl optionally substituted with one or more halides or unsubstituted —(C$_{1-5}$ alkyl), and —(C$_{1-4}$ alkylene)$_p$heterocyclyl optionally substituted with one or more halides or one or more unsubstituted —(C$_{1-5}$ alkyl); wherein each —(C$_{1-4}$ alkylene) is, independently, optionally substituted with one or more substituents;

R$^{27}$ is selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$aryl optionally substituted with one or more halides or one or more unsubstituted —(C$_{1-5}$ alkyl), —(C$_{1-4}$ alkylene)$_p$heteroaryl optionally substituted with one or more halides or unsubstituted —(C$_{1-5}$ alkyl), and —(C$_{1-4}$ alkylene)$_p$heterocyclyl optionally substituted with one or more halides or one or more unsubstituted —(C$_{1-5}$ alkyl); wherein each —(C$_{1-4}$ alkylene) is, independently, optionally substituted with one or more substituents;

R$^{28}$ is selected from the group consisting of unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$aryl optionally substituted with one or more halides or unsubstituted —(C$_{1-5}$ alkyl), —(C$_{1-4}$ alkylene)$_p$heteroaryl optionally substituted with one or more halides or unsubstituted —(C$_{1-5}$ alkyl), and —(C$_{1-4}$ alkylene)$_p$heterocyclyl optionally substituted with one or more halides or one or more unsubstituted —(C$_{1-5}$ alkyl); wherein —(C$_{1-4}$ alkylene) is, optionally substituted with one or more substituents;

each R$^{29}$ is selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$heterocyclyl optionally substituted with 1-10 R$^{32}$, —(C$_{1-4}$ alkylene)$_p$carbocyclyl optionally substituted with 1-12 R$^{21}$, —(C$_{1-4}$ alkylene)OR$^{33}$, and —C(=O)O(C$_{1-5}$ alkyl); wherein each —(C$_{1-4}$ alkylene) is, independently, optionally substituted with one or more substituents;

each R$^{30}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), and —CN;

each R$^{31}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —CN, —OH, —C(=O)R$^{34}$, —N(R$^{24}$)$_2$, and —(C$_{1-4}$ alkylene)$_p$carbocyclyl optionally substituted with 1-12 R$^{21}$; wherein each —(C$_{1-4}$ alkylene) is, independently, optionally substituted with one or more substituents;

each R$^{32}$ is independently selected from the group consisting of halide and unsubstituted —(C$_{1-5}$ alkyl);

each R$^{33}$ is independently selected from the group consisting of H and unsubstituted —(C$_{1-5}$ alkyl);

each R$^{34}$ is independently selected from the group consisting of —O(C$_{1-5}$ alkyl) and a heteroaryl optionally substituted with 1-6 R$^{35}$;

each R$^{35}$ is a -heterocyclyl optionally substituted with one or more halides or one or more unsubstituted —(C$_{1-5}$ alkyl);

each X is selected from the group consisting of O and S;

each p is independently 0 or 1.

Another embodiment disclosed herein includes a compound having the structure of Formula Ic:

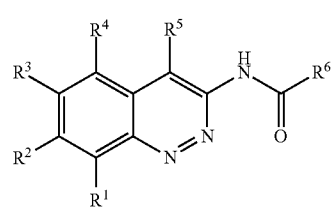

as well as prodrugs and pharmaceutically acceptable salts thereof.

In another embodiment of Formula (Ic):

R$^1$, R$^2$, R$^4$, and R$^5$ are independently absent or selected from the group consisting of H, halide, unsubstituted —(C$_{1-3}$ haloalkyl), and unsubstituted —(C$_{1-3}$ alkyl);

R$^3$ is selected from the group consisting of -aryl optionally substituted with 1-5 R$^7$ and -heteroaryl optionally substituted with 1-4 R$^8$;

R$^6$ is selected from the group consisting of —(C$_{1-4}$ alkylene)$_p$aryl substituted with 1-5 R$^9$, —(C$_{2-4}$ alkenylene)$_p$aryl substituted with 1-5 R$^9$, —(C$_{1-4}$ alkylene)$_p$heteroaryl optionally substituted with 1-6 R$^{10}$; —(C$_{1-4}$ alkylene)$_p$heterocyclyl optionally substituted with 1-10 R$^{11}$, —(C$_{1-4}$ alkylene)$_p$carbocyclyl optionally substituted with 1-12 R$^{12}$, —(C$_{1-4}$ alkylene)N(R$^{13}$)(R$^{14}$), —N(R$^{15}$)(R$^{16}$), —CF(C$_{1-9}$ alkyl)$_2$, —(C$_{1-4}$ alkylene)$_p$O(C$_{3-9}$ alkyl), and —(C$_{2-9}$ alkynyl) optionally substituted with one or more halides; wherein each alkyl of —CF(C$_{1-9}$ alkyl)$_2$ is, independently, optionally substituted with one or more halides; wherein each —(C$_{1-4}$ alkylene) is, independently, optionally substituted with one or more substituents; wherein —(C$_{1-4}$ alkenylene) is, optionally substituted with one or more substituents;

R$^7$ is selected from the group consisting of halide and —N(R$^{17}$)$_2$;

each R$^8$ is independently selected from the group consisting of H, halide, unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —CN, —N(R$^{15}$)(R$^{18}$), —(C$_{1-4}$ alkylene)$_p$XR$^{19}$, —C(=O)N(R$^{15}$)$_2$, —(C$_{1-4}$ alkylene)$_p$heterocyclyl optionally substituted with 1-10 R$^{20}$, and -carbocyclyl optionally substituted with 1-12 R$^{21}$; wherein each —($C_{1-4}$ alkylene) is, independently, optionally substituted with one or more substituents;

alternatively, two adjacent $R^8$ are taken together to form a ring which is selected from the group consisting of -heterocyclyl optionally substituted with 1-10 $R^{22}$ and -carbocyclyl optionally substituted with 1-12 $R^{21}$;

each $R^9$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —$XR^{23}$, —C(=O)N($R^{15}$)$_2$, —($C_{1-4}$ alkylene)$_p$N($R^{24}$)$_2$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{10}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —$XR^{23}$, —C(=O)N($R^{15}$)$_2$, —($C_{1-4}$ alkylene)$_p$N($R^{24}$)$_2$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{11}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$OR$^{19}$, —($C_{1-4}$ alkylene)$_p$heterocyclyl optionally substituted with 1-10 $R^{22}$, —($C_{1-4}$ alkylene)$_p$carbocyclyl optionally substituted with 1-12 $R^{21}$, —N($R^{15}$)($R^{25}$), —C(=O)($R^{26}$), —($C_{1-4}$ alkylene)C(=O)OR$^{27}$, —($C_{1-4}$ alkylene)aryl optionally substituted with one or more halides, —($C_{1-4}$ alkylene)$_p$heteroaryl optionally substituted with one or more halides, and —SO$_2$($R^{28}$); wherein each —($C_{1-4}$ alkylene) is, independently, optionally substituted with one or more substituents;

alternatively, two $R^{11}$ attached to the same carbon atom can together represent =O to form a carbonyl group;

each $R^{12}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$OR$^{19}$, —N($R^{15}$)($R^{29}$), —C(=O)($R^{26}$), —C(=O)OR$^{27}$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

$R^{13}$ is selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{20}$, and -carbocyclyl optionally substituted with 1-12 $R^{21}$; wherein —($C_{1-4}$ alkylene) is, optionally substituted with one or more substituents;

$R^{14}$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{20}$, and -carbocyclyl optionally substituted with 1-12 $R^{21}$; wherein —($C_{1-4}$ alkylene) is, optionally substituted with one or more substituents;

each $R^{15}$ is selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

$R^{16}$ is selected from the group consisting of —($C_{1-4}$ alkylene)$_p$heterocyclyl optionally substituted with 1-10 $R^{20}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

$R^{17}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

alternatively, two adjacent $R^{17}$ are taken together to form a -heterocyclyl ring optionally substituted with 1-10 $R^{22}$;

$R^{18}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —C(=O)R$^{15}$, and —($C_{1-4}$ alkylene)$_p$heterocyclyl optionally substituted with one or more halides or one or more unsubstituted —($C_{1-5}$ alkyl); wherein —($C_{1-4}$ alkylene) is, independently, optionally substituted with one or more substituents;

each $R^{19}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with one or more halides or one or more unsubstituted —($C_{1-5}$ alkyl), and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{20}$ independently is selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —N($R^{15}$)$_2$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{21}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{22}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —N($R^{15}$)$_2$, —C(=O)R$^{34}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{23}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)N($R^{15}$)$_2$, —($C_{1-4}$ alkylene)$_p$aryl optionally substituted with 1-10 $R^{30}$, —($C_{1-4}$ alkylene)$_p$heterocyclyl optionally substituted with 1-12 $R^{31}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{24}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with one or more halides or one or more unsubstituted —($C_{1-5}$ alkyl), and —($C_{1-4}$ alkylene)N($R^{15}$)$_2$; wherein each —($C_{1-4}$ alkylene) is, independently, optionally substituted with one or more substituents;

each $R^{25}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with 1-10 $R^{32}$, —($C_{1-4}$ alkylene)$_p$carbocyclyl optionally substituted with 1-12 $R^{21}$, —($C_{1-4}$ alkylene)$OR^{33}$; wherein each —($C_{1-4}$ alkylene) is, independently, optionally substituted with one or more substituents;

$R^{26}$ is selected from the group consisting of H, unsubstituted —($C_{3-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with one or more halides or unsubstituted —($C_{1-5}$ alkyl), —($C_{1-4}$ alkylene)$_p$heteroaryl optionally substituted with one or more halides or one or more unsubstituted —($C_{1-5}$ alkyl), and —($C_{1-4}$ alkylene)$_p$heterocyclyl optionally substituted with one or more halides or one or more unsubstituted —($C_{1-5}$ alkyl); wherein each —($C_{1-4}$ alkylene) is, independently, optionally substituted with one or more substituents;

$R^{27}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with one or more halides or one or more unsubstituted —($C_{1-5}$ alkyl), —($C_{1-4}$ alkylene)$_p$heteroaryl optionally substituted with one or more halides or unsubstituted —($C_{1-5}$ alkyl), and —($C_{1-4}$ alkylene)$_p$heterocyclyl optionally substituted with one or more halides or one or more unsubstituted —($C_{1-5}$ alkyl); wherein each —($C_{1-4}$ alkylene) is, independently, optionally substituted with one or more substituents;

$R^{28}$ is selected from the group consisting of unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with one or more halides or one or more unsubstituted —($C_{1-5}$ alkyl), —($C_{1-4}$ alkylene)$_p$heteroaryl optionally substituted with one or more halides or one or more unsubstituted —($C_{1-5}$ alkyl), and —($C_{1-4}$ alkylene)$_p$heterocyclyl optionally substituted with one or more halides or one or more unsubstituted —($C_{1-5}$ alkyl); wherein —($C_{1-4}$ alkylene) is, optionally substituted with one or more substituents;

each $R^{29}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with 1-10 $R^{32}$, —($C_{1-4}$ alkylene)$_p$carbocyclyl optionally substituted with 1-12 $R^{21}$, —($C_{1-4}$ alkylene)$OR^{33}$, and —C(=O)O($C_{1-5}$ alkyl); wherein each —($C_{1-4}$ alkylene) is, independently, optionally substituted with one or more substituents;

each $R^{30}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{31}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —C(=O)$R^{34}$, —N($R^{24}$)$_2$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{32}$ is independently selected from the group consisting of halide and unsubstituted —($C_{1-5}$ alkyl);

each $R^{33}$ is independently selected from the group consisting of H and unsubstituted —($C_{1-5}$ alkyl);

each $R^{34}$ is independently selected from the group consisting of —O($C_{1-5}$ alkyl) and a heteroaryl optionally substituted with 1-6 $R^{35}$;

each $R^{35}$ is a -heterocyclyl optionally substituted with one or more halides or one or more unsubstituted —($C_{1-5}$ alkyl);

each X is selected from the group consisting of O and S;
each p is independently 0 or 1.

Another embodiment disclosed herein includes a compound having the structure of Formula Id:

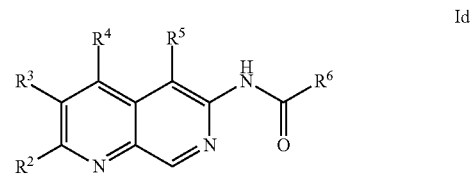

as well as prodrugs and pharmaceutically acceptable salts thereof.

In another embodiment of Formula (Id):

$R^2$, $R^4$, and $R^5$ are independently absent or selected from the group consisting of H, halide, unsubstituted —($C_{1-3}$ haloalkyl), and unsubstituted —($C_{1-3}$ alkyl);

$R^3$ is selected from the group consisting of -aryl optionally substituted with 1-5 $R^7$ and -heteroaryl optionally substituted with 1-4 $R^8$;

$R^6$ is selected from the group consisting of —($C_{1-4}$ alkylene)$_p$aryl substituted with 1-5 $R^9$, —($C_{2-4}$ alkenylene)$_p$aryl substituted with 1-5 $R^9$, —($C_{1-4}$ alkylene)$_p$heteroaryl optionally substituted with 1-6 $R^{10}$; —($C_{1-4}$ alkylene)$_p$heterocyclyl optionally substituted with 1-10 $R^{11}$, —($C_{1-4}$ alkylene)$_p$carbocyclyl optionally substituted with 1-12 $R^{12}$, —($C_{1-4}$ alkylene)N($R^{13}$)($R^4$), —N($R^{15}$)($R^{16}$), —CF($C_{1-9}$ alkyl)$_2$, —($C_{1-4}$ alkylene)$_p$O($C_{3-9}$ alkyl), and —($C_{2-9}$ alkynyl) optionally substituted with one or more halides; wherein each alkyl of —CF($C_{1-9}$ alkyl)$_2$ is, independently, optionally substituted with one or more halides; wherein each —($C_{1-4}$ alkylene) is, independently, optionally substituted with one or more substituents; wherein —($C_{1-4}$ alkenylene) is, optionally substituted with one or more substituents;

$R^7$ is selected from the group consisting of halide and —N($R^{17}$)$_2$;

each $R^8$ is independently selected from the group consisting of H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —N($R^{15}$)($R^{18}$), —($C_{1-4}$ alkylene)$_p$X$R^{19}$, —C(=O)N($R^{15}$)$_2$, —($C_{1-4}$ alkylene)$_p$heterocyclyl optionally substituted with 1-10 $R^{20}$, and -carbocyclyl optionally substituted with 1-12 $R^{21}$; wherein each —($C_{1-4}$ alkylene) is, independently, optionally substituted with one or more substituents;

alternatively, two adjacent $R^8$ are taken together to form a ring which is selected from the group consisting of -heterocyclyl optionally substituted with 1-10 $R^{22}$ and -carbocyclyl optionally substituted with 1-12 $R^{21}$;

each $R^9$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —X$R^{23}$, —C(=O)N($R^{15}$)$_2$, —($C_{1-4}$ alkylene)$_p$N($R^{24}$)$_2$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{10}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —X$R^{23}$, —C(=O)N($R^{15}$)$_2$, —($C_{1-4}$ alkylene)$_p$N($R^{24}$)$_2$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{11}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$O$R^{19}$, —($C_{1-4}$ alkylene)$_p$heterocyclyl optionally substituted with 1-10 $R^{22}$, —($C_{1-4}$ alkylene)$_p$carbocyclyl optionally substituted with 1-12 $R^{21}$, —N($R^{15}$)($R^{25}$), —C(=O)($R^{26}$), —($C_{1-4}$ alkylene)C(=O)O$R^{27}$, —($C_{1-4}$ alkylene)aryl optionally substituted with one or more halides, —($C_{1-4}$ alkylene)$_p$heteroaryl optionally substituted with one or more halides, and —SO$_2$($R^{28}$); wherein each —($C_{1-4}$ alkylene) is, independently, optionally substituted with one or more substituents;

alternatively, two $R^{11}$ attached to the same carbon atom can together represent =O to form a carbonyl group;

each $R^{12}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$O$R^{19}$, —N($R^{15}$)($R^{29}$), —C(=O)($R^{26}$), —C(=O)O$R^{27}$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

$R^{13}$ is selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{20}$, and -carbocyclyl optionally substituted with 1-12 $R^{21}$; wherein —($C_{1-4}$ alkylene) is, optionally substituted with one or more substituents;

$R^{14}$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{20}$, and -carbocyclyl optionally substituted with 1-12 $R^{21}$; wherein —($C_{1-4}$ alkylene) is, optionally substituted with one or more substituents;

each $R^{15}$ is selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

$R^{16}$ is selected from the group consisting of —($C_{1-4}$ alkylene)$_p$heterocyclyl optionally substituted with 1-10 $R^{20}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

$R^{17}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

alternatively, two adjacent $R^{17}$ are taken together to form a -heterocyclyl ring optionally substituted with 1-10 $R^{22}$;

$R^{18}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —(C=O)$R^{15}$, and —($C_{1-4}$ alkylene)$_p$heterocyclyl optionally substituted with one or more halides or one or more unsubstituted —($C_{1-5}$ alkyl); wherein —($C_{1-4}$ alkylene) is, independently, optionally substituted with one or more substituents;

each $R^{19}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with one or more halides or one or more unsubstituted —($C_{1-5}$ alkyl), and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{20}$ independently is selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —N($R^{15}$)$_2$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{21}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{22}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —N($R^{15}$)$_2$, —C(=O)$R^{34}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{23}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)N($R^{15}$)$_2$, —($C_{1-4}$ alkylene)$_p$aryl optionally substituted with 1-10 $R^{30}$, —($C_{1-4}$ alkylene)$_p$heterocyclyl optionally substituted with 1-12 $R^{31}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{24}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with one or more halides or one or more unsubstituted —($C_{1-5}$ alkyl), and —($C_{1-4}$ alkylene)N($R^{15}$)$_2$; wherein each —($C_{1-4}$ alkylene) is, independently, optionally substituted with one or more substituents;

each $R^{25}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with 1-10 $R^{32}$, —($C_{1-4}$ alkylene)$_p$carbocyclyl optionally substituted with 1-12 $R^{21}$, —($C_{1-4}$ alkylene)O$R^{33}$; wherein each —($C_{1-4}$ alkylene) is, independently, optionally substituted with one or more substituents;

$R^{26}$ is selected from the group consisting of H, unsubstituted —($C_{3-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with one or more halides or unsubstituted —($C_{1-5}$ alkyl), —($C_{1-4}$ alkylene)$_p$heteroaryl optionally substituted with one or more halides or one or more unsubstituted —($C_{1-5}$ alkyl), and —($C_{1-4}$ alkylene)$_p$heterocyclyl optionally substituted with one or more halides or one or more unsubstituted —($C_{1-5}$ alkyl); wherein each —($C_{1-4}$ alkylene) is, independently, optionally substituted with one or more substituents;

$R^{27}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with one or more halides or one or more unsubstituted —($C_{1-5}$ alkyl), —($C_{1-4}$ alkylene)$_p$heteroaryl optionally substituted with one or more halides or unsubstituted —($C_{1-5}$ alkyl), and —($C_{1-4}$ alkylene)$_p$heterocyclyl optionally substituted with one or more halides or one or more unsubstituted —(C$_{1-5}$ alkyl); wherein each —(C$_{1-4}$ alkylene) is, independently, optionally substituted with one or more substituents;

R$^{28}$ is selected from the group consisting of unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$aryl optionally substituted with one or more halides or one or more unsubstituted —(C$_{1-5}$ alkyl), —(C$_{1-4}$ alkylene)$_p$heteroaryl optionally substituted with one or more halides or one or more unsubstituted —(C$_{1-5}$ alkyl), and —(C$_{1-4}$ alkylene)$_p$heterocyclyl optionally substituted with one or more halides or one or more unsubstituted —(C$_{1-5}$ alkyl); wherein each —(C$_{1-4}$ alkylene) is, optionally substituted with one or more substituents;

each R$^{29}$ is selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$heterocyclyl optionally substituted with 1-10 R$^{32}$, —(C$_{1-4}$ alkylene)$_p$carbocyclyl optionally substituted with 1-12 R$^{21}$, —(C$_{1-4}$ alkylene)OR$^{33}$, and —C(=O)O(C$_{1-5}$ alkyl); wherein each —(C$_{1-4}$ alkylene) is, independently, optionally substituted with one or more substituents;

each R$^{30}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), and —CN;

each R$^{31}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —CN, —OH, —C(=O)R$^{34}$, —N(R$^{24}$)$_2$, and —(C$_{1-4}$ alkylene)$_p$carbocyclyl optionally substituted with 1-12 R$^{21}$; wherein each —(C$_{1-4}$ alkylene) is, independently, optionally substituted with one or more substituents;

each R$^{32}$ is independently selected from the group consisting of halide and unsubstituted —(C$_{1-5}$ alkyl);

each R$^{33}$ is independently selected from the group consisting of H and unsubstituted —(C$_{1-5}$ alkyl);

each R$^{34}$ is independently selected from the group consisting of —O(C$_{1-5}$ alkyl) and a heteroaryl optionally substituted with 1-6 R$^{35}$;

each R$^{35}$ is a -heterocyclyl optionally substituted with one or more halides or one or more unsubstituted —(C$_{1-5}$ alkyl);

each X is selected from the group consisting of O and S; each p is independently 0 or 1.

Another embodiment disclosed herein includes a compound having the structure of Formula Ie:

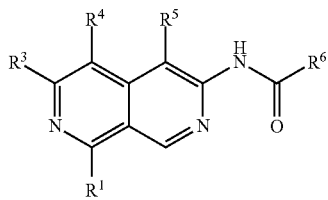

as well as prodrugs and pharmaceutically acceptable salts thereof.

In another embodiment of Formula (Ie):

R$^1$, R$^4$, and R$^5$ are independently absent or selected from the group consisting of H, halide, unsubstituted —(C$_{1-3}$ haloalkyl), and unsubstituted —(C$_{1-3}$ alkyl);

R$^3$ is selected from the group consisting of -aryl optionally substituted with 1-5 R$^7$ and -heteroaryl optionally substituted with 1-4 R$^8$;

R$^6$ is selected from the group consisting of —(C$_{1-4}$ alkylene)$_p$aryl substituted with 1-5 R$^9$, —(C$_{2-4}$ alkenylene)$_p$aryl substituted with 1-5 R$^9$, —(C$_{1-4}$ alkylene)$_p$heteroaryl optionally substituted with 1-6 R$^{10}$; —(C$_{1-4}$ alkylene)$_p$heterocyclyl optionally substituted with 1-10 R$^{11}$, —(C$_{1-4}$ alkylene)$_p$carbocyclyl optionally substituted with 1-12 R$^{12}$, —(C$_{1-4}$ alkylene)N(R$^{13}$)(R$^{14}$), —N(R$^{15}$)(R$^6$), —CF(C$_{1-9}$ alkyl)$_2$, —(C$_{1-4}$ alkylene)$_p$O(C$_{3-9}$ alkyl), and —(C$_{2-9}$ alkynyl) optionally substituted with one or more halides; wherein each alkyl of —CF(C$_{1-9}$ alkyl)$_2$ is, independently, optionally substituted with one or more halides; wherein each —(C$_{1-4}$ alkylene) is, independently, optionally substituted with one or more substituents; wherein —(C$_{1-4}$ alkenylene) is, optionally substituted with one or more substituents;

R$^7$ is selected from the group consisting of halide and —N(R$^{17}$)$_2$;

each R$^8$ is independently selected from the group consisting of H, halide, unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —CN, —N(R$^{15}$)(R$^{18}$), —(C$_{1-4}$ alkylene)$_p$XR$^{19}$, —C(=O)N(R$^{15}$)$_2$, —(C$_{1-4}$ alkylene)$_p$heterocyclyl optionally substituted with 1-10 R$^{20}$, and -carbocyclyl optionally substituted with 1-12 R$^{21}$; wherein each —(C$_{1-4}$ alkylene) is, independently, optionally substituted with one or more substituents;

alternatively, two adjacent R$^8$ are taken together to form a ring which is selected from the group consisting of -heterocyclyl optionally substituted with 1-10 R$^{22}$ and -carbocyclyl optionally substituted with 1-12 R$^{21}$;

each R$^9$ is independently selected from the group consisting of halide, unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —XR$^{23}$, —C(=O)N(R$^{15}$)$_2$, —(C$_{1-4}$ alkylene)$_p$N(R$^{24}$)$_2$, —(C$_{1-4}$ alkylene)$_p$heterocyclyl optionally substituted with 1-10 R$^{22}$, and —(C$_{1-4}$ alkylene)$_p$carbocyclyl optionally substituted with 1-12 R$^{21}$; wherein each —(C$_{1-4}$ alkylene) is, independently, optionally substituted with one or more substituents;

each R$^{10}$ is independently selected from the group consisting of halide, unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —CN, —XR$^{23}$, —C(=O)N(R$^{15}$)$_2$, —(C$_{1-4}$ alkylene)$_p$N(R$^{24}$)$_2$, —(C$_{1-4}$ alkylene)$_p$heterocyclyl optionally substituted with 1-10 R$^{22}$, and —(C$_{1-4}$ alkylene)$_p$carbocyclyl optionally substituted with 1-12 R$^{21}$; wherein each —(C$_{1-4}$ alkylene) is, independently, optionally substituted with one or more substituents;

each R$^{11}$ is independently selected from the group consisting of halide, unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —(C$_{1-4}$ alkylene)$_p$OR$^{19}$, —(C$_{1-4}$ alkylene)$_p$heterocyclyl optionally substituted with 1-10 R$^{22}$, —(C$_{1-4}$ alkylene)$_p$carbocyclyl optionally substituted with 1-12 R$^{21}$, —N(R$^{15}$)(R$^{25}$), —C(=O)(R$^{26}$), —(C$_{1-4}$ alkylene)C(=O)OR$^{27}$, —(C$_{1-4}$ alkylene)aryl optionally substituted with one or more halides, —(C$_{1-4}$ alkylene)$_p$heteroaryl optionally substituted with one or more halides, and —SO$_2$(R$^{28}$); wherein each —(C$_{1-4}$ alkylene) is, independently, optionally substituted with one or more substituents;

alternatively, two R$^{11}$ attached to the same carbon atom can together represent =O to form a carbonyl group;

each R$^{12}$ is independently selected from the group consisting of halide, unsubstituted —(C$_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$OR$^{19}$, —N(R$^{15}$)(R$^{29}$), —C(=O)(R$^{26}$), —C(=O)OR$^{27}$, —($C_{1-4}$ alkylene)$_p$heterocyclyl optionally substituted with 1-10 R$^{22}$, and —($C_{1-4}$ alkylene)$_p$carbocyclyl optionally substituted with 1-12 R$^{21}$; wherein each —($C_{1-4}$ alkylene) is, independently, optionally substituted with one or more substituents;

R$^{13}$ is selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 R$^{20}$, and -carbocyclyl optionally substituted with 1-12 R$^{21}$; wherein —($C_{1-4}$ alkylene) is, optionally substituted with one or more substituents;

R$^{14}$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 R$^{20}$, and -carbocyclyl optionally substituted with 1-12 R$^{21}$; wherein —($C_{1-4}$ alkylene) is, optionally substituted with one or more substituents;

each R$^{15}$ is selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

R$^{16}$ is selected from the group consisting of —($C_{1-4}$ alkylene)$_p$heterocyclyl optionally substituted with 1-10 R$^{20}$, and —($C_{1-4}$ alkylene)$_p$carbocyclyl optionally substituted with 1-12 R$^{21}$; wherein each —($C_{1-4}$ alkylene) is, independently, optionally substituted with one or more substituents;

R$^{17}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

alternatively, two adjacent R$^{17}$ are taken together to form a -heterocyclyl ring optionally substituted with 1-10 R$^{22}$;

R$^{18}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —C(=O)R$^{15}$, and —($C_{1-4}$ alkylene)$_p$heterocyclyl optionally substituted with one or more halides or one or more unsubstituted —($C_{1-5}$ alkyl); wherein —($C_{1-4}$ alkylene) is, independently, optionally substituted with one or more substituents;

each R$^{19}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with one or more halides or one or more unsubstituted —($C_{1-5}$ alkyl), and —($C_{1-4}$ alkylene)$_p$carbocyclyl optionally substituted with 1-12 R$^{21}$; wherein each —($C_{1-4}$ alkylene) is, independently, optionally substituted with one or more substituents;

each R$^{20}$ independently is selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —N(R$^{15}$)$_2$, and —($C_{1-4}$ alkylene)$_p$carbocyclyl optionally substituted with 1-12 R$^{21}$; wherein each —($C_{1-4}$ alkylene) is, independently, optionally substituted with one or more substituents;

each R$^{21}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each R$^{22}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —N(R$^{15}$)$_2$, —C(=O)R$^{34}$, and —($C_{1-4}$ alkylene)$_p$carbocyclyl optionally substituted with 1-12 R$^{21}$; wherein each —($C_{1-4}$ alkylene) is, independently, optionally substituted with one or more substituents;

each R$^{23}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)N(R$^{15}$)$_2$, —($C_{1-4}$ alkylene)$_p$aryl optionally substituted with 1-10 R$^{30}$, —($C_{1-4}$ alkylene)$_p$heterocyclyl optionally substituted with 1-12 R$^{31}$, and —($C_{1-4}$ alkylene)$_p$carbocyclyl optionally substituted with 1-12 R$^{21}$; wherein each —($C_{1-4}$ alkylene) is, independently, optionally substituted with one or more substituents;

each R$^{24}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with one or more halides or one or more unsubstituted —($C_{1-5}$ alkyl), and —($C_{1-4}$ alkylene)N(R$^{15}$)$_2$; wherein each —($C_{1-4}$ alkylene) is, independently, optionally substituted with one or more substituents;

each R$^{25}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with 1-10 R$^{32}$, —($C_{1-4}$ alkylene)$_p$carbocyclyl optionally substituted with 1-12 R$^{21}$, —($C_{1-4}$ alkylene)OR$^{33}$; wherein each —($C_{1-4}$ alkylene) is, independently, optionally substituted with one or more substituents;

R$^{26}$ is selected from the group consisting of H, unsubstituted —($C_{3-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with one or more halides or unsubstituted —($C_{1-5}$ alkyl), —($C_{1-4}$ alkylene)$_p$heteroaryl optionally substituted with one or more halides or one or more unsubstituted —($C_{1-5}$ alkyl), and —($C_{1-4}$ alkylene)$_p$heterocyclyl optionally substituted with one or more halides or one or more unsubstituted —($C_{1-5}$ alkyl); wherein each —($C_{1-4}$ alkylene) is, independently, optionally substituted with one or more substituents;

R$^{27}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with one or more halides or one or more unsubstituted —($C_{1-5}$ alkyl), —($C_{1-4}$ alkylene)$_p$heteroaryl optionally substituted with one or more halides or unsubstituted —($C_{1-5}$ alkyl), and —($C_{1-4}$ alkylene)$_p$heterocyclyl optionally substituted with one or more halides or one or more unsubstituted —($C_{1-5}$ alkyl); wherein each —($C_{1-4}$ alkylene) is, independently, optionally substituted with one or more substituents;

R$^{28}$ is selected from the group consisting of unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with one or more halides or one or more unsubstituted —($C_{1-5}$ alkyl), —($C_{1-4}$ alkylene)$_p$heteroaryl optionally substituted with one or more halides or one or more unsubstituted —($C_{1-5}$ alkyl), and —($C_{1-4}$ alkylene)$_p$heterocyclyl optionally substituted with one or more halides or one or more unsubstituted —($C_{1-5}$ alkyl); wherein —($C_{1-4}$ alkylene) is, optionally substituted with one or more substituents;

each R$^{29}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with 1-10 $R^{32}$, —($C_{1-4}$ alkylene)$_p$carbocyclyl optionally substituted with 1-12 $R^{21}$, —($C_{1-4}$ alkylene)$OR^{33}$, and —C(=O)O($C_{1-5}$ alkyl); wherein each —($C_{1-4}$ alkylene) is, independently, optionally substituted with one or more substituents;

each $R^{30}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN;

each $R^{31}$ is independently selected from the group consisting of halide, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —C(=O)$R^{34}$, —N($R^{24}$)$_2$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{32}$ is independently selected from the group consisting of halide and unsubstituted —($C_{1-5}$ alkyl);

each $R^{33}$ is independently selected from the group consisting of H and unsubstituted —($C_{1-5}$ alkyl);

each $R^{34}$ is independently selected from the group consisting of —O($C_{1-5}$ alkyl) and a heteroaryl optionally substituted with 1-6 $R^{35}$;

each $R^{35}$ is a -heterocyclyl optionally substituted with one or more halides or one or more unsubstituted —($C_{1-5}$ alkyl);

each X is selected from the group consisting of O and S;

each p is independently 0 or 1.

Some embodiments include stereoisomers and pharmaceutically acceptable salts of a compound of Formulas I, Ia, Ib, Ic, Id, and Ie. Some embodiments include pharmaceutically acceptable salts of a compound of Formulas I, Ia, Ib, Ic, Id, and Ie.

Some embodiments include pro-drugs of a compound of Formulas I, Ia, Ib, Ic, Id, and Ie.

Some embodiments of the present disclosure include pharmaceutical compositions comprising a compound of Formulas I, Ia, Ib, Ic, Id, and Ie and a pharmaceutically acceptable carrier, diluent, or excipient.

Other embodiments disclosed herein include methods of inhibiting one or more members of the Wnt pathway, including one or more Wnt proteins by administering to a patient affected by a disorder or disease in which aberrant Wnt signaling is implicated, such as cancer and other diseases associated with abnormal angiogenesis, cellular proliferation, cell cycling and mutations in Wnt signaling components, a compound according to Formula (I). Accordingly, the compounds and compositions provided herein can be used to treat cancer, to reduce or inhibit angiogenesis, to reduce or inhibit cellular proliferation and correct a genetic disorder due to mutations in Wnt signaling components.

Other embodiments disclosed herein include methods of inhibiting DYRK1A by administering to a patient affected by a disorder or disease in which DYRK1A overexpression is implicated, such as Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor and Stroke.

Non-limiting examples of diseases which can be treated with the compounds and compositions provided herein include a variety of cancers, diabetic retinopathy, pulmonary fibrosis, rheumatoid arthritis, sepsis, ankylosing spondylitis, psoriasis, scleroderma, mycotic and viral infections, osteochondrodysplasia, Alzheimer's disease, lung disease, bone/osteoporotic (wrist, spine, shoulder and hip) fractures, articular cartilage (chondral) defects, degenerative disc disease (or intervertebral disc degeneration), polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

Some embodiments of the present disclosure include methods to prepare compounds of Formulas I, Ia, Ib, Ic, Id, and Ie.

It is to be understood that both the foregoing general description and the following detailed description are exemplary and explanatory only and are not restrictive of the disclosure, as claimed.

DETAILED DESCRIPTION

Provided herein are compositions and methods for inhibiting one or more members of the Wnt pathway, including one or more Wnt proteins. Other Wnt inhibitors and methods for using the same are disclosed in U.S. application Ser. Nos. 13/614,296; 14/019,229; and Ser. No. 14/664,517, all of which are incorporated by reference in their entirety herein.

Provided herein are compositions and methods for inhibiting DYRK1A. Other DYRK1A inhibitors and methods for using the same are disclosed in U.S. application Ser. No. 14/664,517, which is incorporated by reference in its entirety herein.

Some embodiments provided herein relate to a method for treating a disease including, but not limited to, neurological diseases or disorders, cancers, chronic inflammation, diabetic retinopathy, pulmonary fibrosis, rheumatoid arthritis, sepsis, ankylosing spondylitis, psoriasis, scleroderma, mycotic and viral infections, bone and cartilage diseases, lung disease, osteoarthritis, articular cartilage (chondral) defects, degenerative disc disease (or intervertebral disc degeneration), polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman's syndrome, Prader-Willi syndrome, Beckwith-Wiedemann Syndrome, Norrie disease, and Rett syndrome.

In some embodiments, non-limiting examples of bone and cartilage diseases which can be treated with the compounds and compositions provided herein include bone spur (osteophytes), craniosynostosis, fibrodysplasia ossificans progressive, fibrous dysplasia, giant cell tumor of bone, hip labral tear, meniscal tears, osteoarthritis, articular cartilage (chondral) defects, degenerative disc disease (or intervertebral disc degeneration), osteochondritis dissecans, osteochondroma (bone tumor), osteopetrosis, relapsing polychondritis, and Salter-Harris fractures.

In some embodiments, non-limiting examples of a neurological disease or disorder associated with tau protein, amyloid or alpha-synuclein pathology which can be treated with the compounds and compositions provided herein include, but are not limited to, Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, and Stroke.

In some embodiments, non-limiting examples of diseases in which chronic inflammation is involved which can be treated with the compounds and compositions provided herein include eye disorders, joint pain, arthritis (rheumatoid, osteo, psoriatic gout), cancers (colon, breast, lung, pancreas, and others), gastrointestinal disorders (ulcerative colitis and inflammatory bowel diseases), pulmonary disorders (chronic obstructive pulmonary disorder and asthma), allergies, skin disorders (atopic dermatitis and psoriasis), diabetes, pancreatitis, tendonitis, hepatitis, heart disease, myocarditis, stroke, lupus, and neurological disorders such as multiple sclerosis, Parkinson's and dementia including Alzheimer's disease.

In some embodiments, non-limiting examples of cancers which can be treated with the compounds and compositions provided herein include colon, ovarian, pancreatic, breast, liver, prostate, and hematologic cancers.

In some embodiments, pharmaceutical compositions are provided that are effective for treatment of a disease of an animal, e.g., a mammal, caused by either the pathological activation or mutations of the Wnt pathway or DYRK1A overexpression. The composition includes a pharmaceutically acceptable carrier and a compound as described herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, "alkyl" means a branched, or straight chain chemical group containing only carbon and hydrogen, such as methyl, ethyl, n-propyl, iso-propyl, n-butyl, isobutyl, sec-butyl, tert-butyl, n-pentyl, iso-pentyl, sec-pentyl and neo-pentyl. Alkyl groups can either be unsubstituted or substituted with one or more substituents. In some embodiments, alkyl groups include 1 to 9 carbon atoms (for example, 1 to 6 carbon atoms, 1 to 4 carbon atoms, or 1 to 2 carbon atoms).

As used herein, "alkenyl" means a straight or branched chain chemical group containing only carbon and hydrogen and containing at least one carbon-carbon double bond, such as ethenyl, 1-propenyl, 2-propenyl, 2-methyl-1-propenyl, 1-butenyl, 2-butenyl, and the like. In various embodiments, alkenyl groups can either be unsubstituted or substituted with one or more substituents. Typically, alkenyl groups will comprise 2 to 9 carbon atoms (for example, 2 to 6 carbon atoms, 2 to 4 carbon atoms, or 2 carbon atoms).

As used herein, "alkynyl" means a straight or branched chain chemical group containing only carbon and hydrogen and containing at least one carbon-carbon triple bond, such as ethynyl, 1-propynyl, 1-butynyl, 2-butynyl, and the like. In various embodiments, alkynyl groups can either be unsubstituted or substituted with one or more substituents. Typically, alkynyl groups will comprise 2 to 9 carbon atoms (for example, 2 to 6 carbon atoms, 2 to 4 carbon atoms, or 2 carbon atoms).

As used herein, "alkylene" means a bivalent branched, or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. In some embodiments, alkylene groups include 1 to 9 carbon atoms (for example, 1 to 6 carbon atoms, 1 to 4 carbon atoms, or 1 to 2 carbon atoms).

As used herein, "alkenylene" means a bivalent branched, or straight chain chemical group containing only carbon and hydrogen and containing at least one carbon-carbon double bond, such as ethenylene, 1-propenylene, 2-propenylene, 2-methyl-1-propenylene, 1-butenylene, 2-butenylene, and the like. In various embodiments, alkenylene groups can either be unsubstituted or substituted with one or more substituents. Typically, alkenylene groups will comprise 2 to 9 carbon atoms (for example, 2 to 6 carbon atoms, 2 to 4 carbon atoms, or 2 carbon atoms).

As used herein, "alkynylene" means a bivalent branched, or straight chain chemical group containing only carbon and hydrogen and containing at least one carbon-carbon triple bond, such as ethynylene, 1-propynylene, 1-butynylene, 2-butynylene, and the like. In various embodiments, alkynylene groups can either be unsubstituted or substituted with one or more substituents. Typically, alkynylene groups will comprise 2 to 9 carbon atoms (for example, 2 to 6 carbon atoms, 2 to 4 carbon atoms, or 2 carbon atoms).

As used herein, "alkoxy" means an alkyl-O— group in which the alkyl group is as described herein. Exemplary alkoxy groups include methoxy, ethoxy, n-propoxy, i-propoxy, n-butoxy, s-butoxy, t-butoxy, pentoxy, hexoxy and heptoxy, and also the linear or branched positional isomers thereof.

As used herein, "haloalkoxy" means a haloalkyl-O— group in which the haloalkyl group is as described herein. Exemplary haloalkoxy groups include fluoromethoxy, difluoromethoxy, trifluoromethoxy, and also the linear or branched positional isomers thereof.

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that none of the rings in the ring system are aromatic. Carbocyclyl groups can either be unsubstituted or substituted with one or more substituents. In some embodiments, carbocyclyl groups include 3 to 10 carbon atoms, for example, 3 to 6 carbon atoms.

As used herein, "aryl" means a mono-, bi-, tri- or polycyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic. Aryl groups can either be unsubstituted or substituted with one or more substituents. Examples of aryl include phenyl, naphthyl, tetrahydronaphthyl, 2,3-dihydro-1H-indenyl, and others. In some embodiments, the aryl is phenyl.

As used herein, "arylalkylene" means an aryl-alkylene-group in which the aryl and alkylene moieties are as previously described. In some embodiments, arylalkylene groups contain a $C_{1-4}$alkylene moiety. Exemplary arylalkylene groups include benzyl and 2-phenethyl.

As used herein, the term "heteroaryl" means a mono-, bi-, tri- or polycyclic group having 5 to 14 ring atoms, alternatively 5, 6, 9, or 10 ring atoms; and having 6, 10, or 14 pi electrons shared in a cyclic array; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, and others. In some embodiments, the heteroaryl is selected from thienyl, pyridinyl, furyl, pyrazolyl, imidazolyl, isoindolinyl, pyranyl, pyrazinyl, and pyrimidinyl.

As used herein, "halo", "halide" or "halogen" is a chloro, bromo, fluoro, or iodo atom radical. In some embodiments, a halo is a chloro, bromo or fluoro. For example, a halide can be fluoro.

As used herein, "haloalkyl" means a hydrocarbon substituent, which is a linear or branched, alkyl, alkenyl or alkynyl substituted with one or more chloro, bromo, fluoro, and/or iodo atom(s). In some embodiments, a haloalkyl is a fluoroalkyls, wherein one or more of the hydrogen atoms have been substituted by fluoro. In some embodiments, haloalkyls are of 1 to about 3 carbons in length (e.g., 1 to about 2 carbons in length or 1 carbon in length). The term "haloalkylene" means a diradical variant of haloalkyl, and such diradicals may act as spacers between radicals, other atoms, or between a ring and another functional group.

As used herein, "heterocyclyl" means a nonaromatic cyclic ring system comprising at least one heteroatom in the ring system backbone. Heterocyclyls may include multiple fused rings. Heterocyclyls may be substituted or unsubstituted with one or more substituents. In some embodiments, heterocycles have 3-11 members. In six membered monocyclic heterocycles, the heteroatom(s) are selected from one to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others. In some embodiments, the heterocyclyl is selected from azetidinyl, morpholinyl, piperazinyl, pyrrolidinyl, and tetrahydropyridinyl.

As used herein, "monocyclic heterocyclyl" means a single nonaromatic cyclic ring comprising at least one heteroatom in the ring system backbone. Heterocyclyls may be substituted or unsubstituted with one or more substituents. In some embodiments, heterocycles have 3-7 members. In six membered monocyclic heterocycles, the heteroatom(s) are selected from one to three of O, N or S, and wherein when the heterocycle is five membered, it can have one or two heteroatoms selected from O, N, or S. Examples of heterocyclyls include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

As used herein, "bicyclic heterocyclyl" means a nonaromatic bicyclic ring system comprising at least one heteroatom in the ring system backbone. Bicyclic heterocyclyls may be substituted or unsubstituted with one or more substituents. In some embodiments, bicyclic heterocycles have 4-11 members with the heteroatom(s) being selected from one to five of O, N or S. Examples of bicyclic heterocyclyls include 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, and the like.

As used herein, "spirocyclic heterocyclyl" means a nonaromatic bicyclic ring system comprising at least one heteroatom in the ring system backbone and with the rings connected through just one atom. Spirocyclic heterocyclyls may be substituted or unsubstituted with one or more substituents. In some embodiments, spirocyclic heterocycles have 5-11 members with the heteroatom(s) being selected from one to five of O, N or S. Examples of spirocyclic heterocyclyls include 2-azaspiro[2.2]pentane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[4.5]decane, 2,5-diazaspiro[3.6]decane, and the like.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, —($C_{1-9}$ alkyl) optionally substituted with one or more of hydroxyl, —$NH_2$, —NH($C_{1-3}$ alkyl), and —N($C_{1-3}$ alkyl)$_2$; —($C_{1-9}$ haloalkyl); a halide; a hydroxyl; a carbonyl [such as —C(O)OR, and —C(O)R]; a thiocarbonyl [such as —C(S)OR, —C(O)SR, and —C(S)R]; —($C_{1-9}$ alkoxy) optionally substituted with one or more of halide, hydroxyl, —$NH_2$, —NH($C_{1-3}$ alkyl), and —N($C_{1-3}$ alkyl)$_2$; —OPO(OH)$_2$; a phosphonate [such as —PO(OH)$_2$ and —PO(OR')$_2$]; —OPO(OR')R''; —NRR'; —C(O)NRR'; —C(NR)NR'R''; —C(NR')R''; a cyano; a nitro; an azido; —SH; —S—R; —OSO$_2$(OR); a sulfonate [such as —SO$_2$(OH) and —SO$_2$(OR)]; —SO$_2$NR'R''; and —SO$_2$R; in which each occurrence of R, R' and R'' are independently selected from H; —($C_{1-9}$ alkyl); $C_{6-10}$ aryl optionally substituted with from 1-3R'''; 5-10 membered heteroaryl having from 1-4 heteroatoms independently selected from N, O, and S and optionally substituted with from 1-3 R'''; $C_{3-7}$ carbocyclyl optionally substituted with from 1-3 R'''; and 3-8 membered heterocyclyl having from 1-4 heteroatoms independently selected from N, O, and S and optionally substituted with from 1-3 R'''; wherein each R''' is independently selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl). In some embodiments, the substituent is selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl).

As used herein, when two groups are indicated to be "linked" or "bonded" to form a "ring", it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions. In some embodiments, such rings have from 3-7 members, for example, 5 or 6 members.

The skilled artisan will recognize that some chemical structures described herein may be represented on paper by one or more other resonance forms; or may exist in one or more other tautomeric forms, even when kinetically, the artisan recognizes that such tautomeric forms represent only a very small portion of a sample of such compound(s). Such compounds are clearly contemplated within the scope of this disclosure, though such resonance forms or tautomers are not explicitly represented herein.

The compounds provided herein may encompass various stereochemical forms. The compounds also encompass diastereomers as well as optical isomers, e.g., mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The present disclosure includes all pharmaceutically acceptable isotopically labeled compounds of Formulas I, Ia, Ib, Ic, Id, and Ie, wherein one or more atoms are replaced by atoms having the same atomic number, but an atomic mass or mass number different from the atomic mass or mass number which predominates in nature. Examples of isotopes suitable for inclusion in the compounds of the disclosure include, but are not limited to, isotopes of hydrogen, such as $^2$H (deuterium) and $^3$H (tritium), carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

The term "administration" or "administering" refers to a method of providing a dosage of a compound or pharmaceutical composition to a vertebrate or invertebrate, including a mammal, a bird, a fish, or an amphibian, where the method is, e.g., orally, subcutaneously, intravenously, intralymphatic, intranasally, topically, transdermally, intraperitoneally, intramuscularly, intrapulmonarilly, vaginally, rectally, ontologically, neuro-otologically, intraocularly, subconjuctively, via anterior eye chamber injection, intravitreally, intraperitoneally, intrathecally, intracystically, intrapleurally, via wound irrigation, intrabuccally, intraabdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. The method of administration can vary depending on various factors, e.g., the components of the pharmaceutical composition, the site of the disease, the disease involved, and the severity of the disease.

A "diagnostic" as used herein is a compound, method, system, or device that assists in the identification or characterization of a health or disease state. The diagnostic can be used in standard assays as is known in the art.

The term "mammal" is used in its usual biological sense. Thus, it specifically includes humans, cattle, horses, monkeys, dogs, cats, mice, rats, cows, sheep, pigs, goats, and non-human primates, but also includes many other species.

The term "pharmaceutically acceptable carrier", "pharmaceutically acceptable diluent" or "pharmaceutically acceptable excipient" includes any and all solvents, co-solvents, complexing agents, dispersion media, coatings, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Brunton et al. (Eds.) (2017); *Goodman and Gilman's: The Pharmacological Basis of Therapeutics,* 13th Ed., The McGraw-Hill Companies.

The term "pharmaceutically acceptable salt" refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Many such salts are known in the art, for example, as described in WO 87/05297. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases.

Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

"Patient" as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate. In some embodiments, the patient is a human.

A "therapeutically effective amount" of a compound as provided herein is one which is sufficient to achieve the desired physiological effect and may vary according to the nature and severity of the disease condition, and the potency of the compound. "Therapeutically effective amount" is also intended to include one or more of the compounds of Formulas I, Ia, Ib, Ic, Id, and Ie, in combination with one or more other agents that are effective to treat the diseases and/or conditions described herein. The combination of compounds can be a synergistic combination. Synergy, as described, for example, by Chou and Talalay, *Advances in Enzyme Regulation* (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease.

"Treat," "treatment," or "treating," as used herein refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

"Drug-eluting" and/or controlled release as used herein refers to any and all mechanisms, e.g., diffusion, migration, permeation, and/or desorption by which the drug(s) incorporated in the drug-eluting material pass therefrom over time into the surrounding body tissue.

"Drug-eluting material" and/or controlled release material as used herein refers to any natural, synthetic or semi-synthetic material capable of acquiring and retaining a desired shape or configuration and into which one or more drugs can be incorporated and from which incorporated drug(s) are capable of eluting over time.

"Elutable drug" as used herein refers to any drug or combination of drugs having the ability to pass over time from the drug-eluting material in which it is incorporated into the surrounding areas of the body.

Compounds

The compounds and compositions described herein can be used as anti-proliferative agents, e.g., anti-cancer and anti-angiogenesis agents, and/or as inhibitors of the Wnt signaling pathway, e.g., for treating diseases or disorders associated with aberrant Wnt signaling. In addition, the compounds can be used as inhibitors of one or more kinases, kinase receptors, or kinase complexes. Such compounds and compositions are also useful for controlling cellular proliferation, differentiation, and/or apoptosis.

The compounds and compositions described herein can be used to inhibit DYRK1A for treating a disorder or disease in which DYRK1A overexpression is implicated, such as Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, and Stroke.

Some embodiments of the present disclosure include compounds of Formula

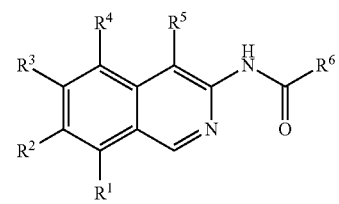

I or salts, pharmaceutically acceptable salts, or prodrugs thereof.

Some embodiments of the present disclosure include compounds of Formula Ia:

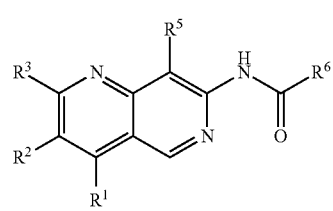

Ia or salts, pharmaceutically acceptable salts, or prodrugs thereof.

Some embodiments of the present disclosure include compounds of Formula Ib:

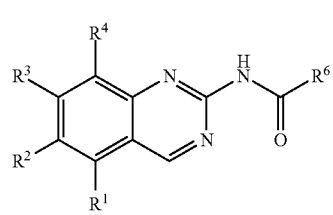

Ib or salts, pharmaceutically acceptable salts, or prodrugs thereof.

Some embodiments of the present disclosure include compounds of Formula Ic:

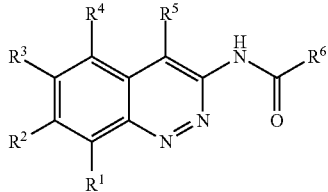

or salts, pharmaceutically acceptable salts, or prodrugs thereof.

Some embodiments of the present disclosure include compounds of Formula Id:

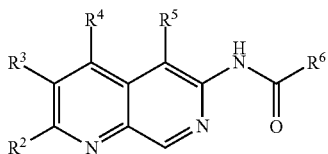

or salts, pharmaceutically acceptable salts, or prodrugs thereof.

Some embodiments of the present disclosure include compounds of Formula Ie:

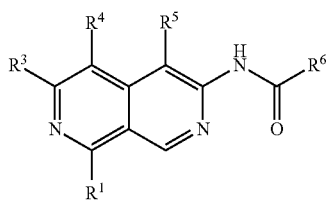

or salts, pharmaceutically acceptable salts, or prodrugs thereof.

In some embodiments of Formula I, $Y^3$ is CH or nitrogen.

In some embodiments of Formula I, $Y^1$, $Y^2$, $Y^4$, and $Y^5$ are independently selected from the group consisting of carbon and nitrogen.

In some embodiments of Formula I, $Y^1$ is nitrogen, $Y^2$, $Y^4$, and $Y^5$ are carbon, $Y^3$ is CH, and $R^4$ is absent.

In some embodiments of Formula I, $Y^2$ is nitrogen, $Y^1$, $Y^4$, and $Y^5$ are carbon, $Y^3$ is CH, and $R^5$ is absent.

In some embodiments of Formula I, $Y^3$ is nitrogen and $Y^1$, $Y^2$, $Y^4$, and $Y^5$ are carbon;

In some embodiments of Formula I, $Y^4$ is nitrogen, $Y^1$, $Y^2$, and $Y^5$ are carbon, $Y^3$ is CH, and $R^1$ is absent.

In some embodiments of Formula I, $Y^5$ is nitrogen, $Y^1$, $Y^2$, and $Y^4$ are carbon, $Y^3$ is CH, and $R^2$ is absent.

In some embodiments of Formulas I, Ia, Ib, Ic, Id, and Ie, $R^1$, $R^2$, $R^4$, and $R^5$ are independently absent or selected from the group consisting of H, halide (e.g., F, Cl, Br, I), unsubstituted —($C_{1-3}$ haloalkyl), and unsubstituted —($C_{1-3}$ alkyl) (e.g., $C_{1-3}$, $C_{1-2}$, $C_1$).

In some embodiments of Formulas I, Ia, Ib, Ic, Id, and Ie, $R^1$, $R^2$, $R^4$, and $R^5$ are independently selected from the group consisting of H and halide (e.g., F, Cl, Br, I).

In some embodiments of Formulas I, Ia, Ib, Ic, Id, and Ie, $R^1$, $R^2$, $R^4$, and $R^5$ are independently selected from the group consisting of H and F.

In some embodiments of Formulas I, Ia, Ib, Ic, Id, and Ie, $R^1$, $R^2$, $R^4$, and $R^5$ are all H.

In some embodiments of Formulas I, Ia, Ib, Ic, Id, and Ie, $R^1$ is F, and $R^2$, $R^4$, and $R^5$ are all H.

In some embodiments of Formulas I, Ia, Ib, Ic, Id, and Ie, $R^2$ is F, and $R^1$, $R^4$, and $R^5$ are all H.

In some embodiments of Formulas I, Ia, Ib, Ic, Id, and Ie, $R^4$ is F, and $R^1$, $R^2$, and $R^5$ are all H.

In some embodiments of Formulas I, Ia, Ib, Ic, Id, and Ie, $R^5$ is F, and $R^1$, $R^2$, and $R^4$ are all H.

In some embodiments of Formulas I, Ia, Ib, Ic, Id, and Ie, $R^3$ is selected from the group consisting of -aryl optionally substituted with 1-5 $R^7$ and -heteroaryl optionally substituted with 1-4 $R^8$.

In some embodiments of Formulas I, Ia, Ib, Ic, Id, and Ie, $R^3$ is phenyl ring optionally substituted with 1-5 (e.g., 1-4, 1-3, 1-2, 1) $R^7$.

In some embodiments of Formulas I, Ia, Ib, Ic, Id, and Ie, $R^7$ is selected from the group consisting of halide (e.g., F, Cl, Br, I) and —N($R^{17}$)$_2$.

In some embodiments of Formulas I, Ia, Ib, Ic, Id, and Ie, $R^7$ is one halide (e.g., F, Cl, Br, I) and one —N($R^{17}$)$_2$.

In some embodiments of Formulas I, Ia, Ib, Ic, Id, and Ie, $R^7$ is one F and one —$NH_2$.

In some embodiments of Formulas I, Ia, Ib, Ic, Id, and Ie, $R^7$ is one F and one —NH($C_{1-4}$ alkyl)(e.g., —NH($C_{1-3}$ alkyl), —NH($C_{1-2}$ alkyl), —NHMe).

In some embodiments of Formulas I, Ia, Ib, Ic, Id, and Ie, $R^3$ is a 5-membered heteroaryl ring optionally substituted as defined anywhere herein.

In some embodiments of Formulas I, Ia, Ib, Ic, Id, and Ie, $R^3$ is 5-membered heteroaryl ring optionally substituted with 1-4 (e.g., 1-3, 1-2, 1) $R^8$.

In some embodiments of Formulas I, Ia, Ib, Ic, Id, and Ie, $R^3$ is selected from the group consisting of:

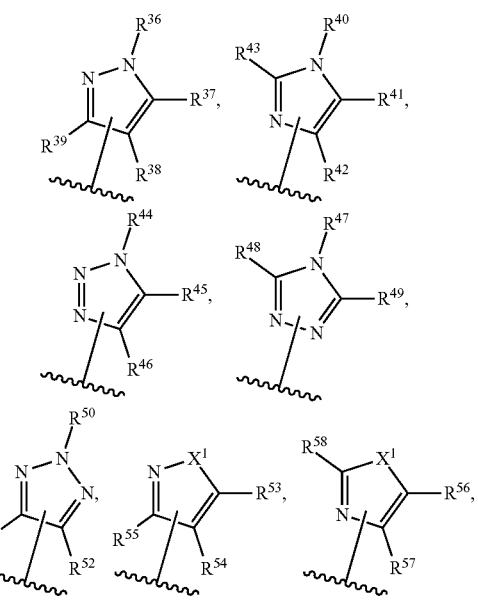

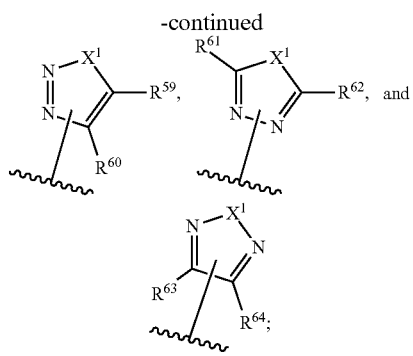

wherein each of $R^{36}$-$R^{64}$ is, independently, a substituent as defined anywhere herein or a single bond connecting $R^3$ to the diazanaphthalene ring; wherein only one of $R^{36}$-$R^{39}$ (when present) is a bond, only one of $R^{40}$-$R^{43}$ (when present) is a bond, only one of $R^{44}$-$R^{46}$ (when present) is a bond, only one of $R^{47}$-$R^{49}$ (when present) is a bond, only one of $R^{50}$-$R^{52}$ (when present) is a bond, only one of $R^{53}$-$R^{55}$ (when present) is a bond, only one of $R^{56}$-$R^{58}$ (when present) is a bond, only one of $R^{59}$-$R^{60}$ (when present) is a bond, only one of $R^{61}$-$R^{62}$ (when present) is a bond, and only one of $R^{63}$-$R^{64}$ (when present) is a bond; for purposes of clarification, any one of the nitrogen atoms attached to $R^{36}$, $R^{40}$, $R^{44}$, $R^{47}$, or $R^{50}$ can serve as the point of attachment of $R^3$ to the diazanaphthalene ring; likewise, any one of the carbon atoms attached to $R^{37}$, $R^{38}$, $R^{39}$, $R^{41}$, $R^{42}$, $R^{43}$, $R^{45}$, $R^{46}$, $R^{48}$, $R^{49}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, or $R^{64}$ can serve as the point of attachment of $R^3$ to the diazanaphthalene ring; so that:

when the nitrogen atom to which $R^{36}$ is attached serves as the point of attachment of $R^3$ to the diazanaphthalene ring, then $R^{36}$ is a single bond connecting $R^3$ to the diazanaphthalene ring;

when the carbon atom to which $R^{37}$ is attached serves as the point of attachment of $R^3$ to the diazanaphthalene ring, then $R^{37}$ is a single bond connecting $R^3$ to the diazanaphthalene ring;

when the carbon atom to which $R^{38}$ is attached serves as the point of attachment of $R^3$ to the diazanaphthalene ring, then $R^{38}$ is a single bond connecting $R^3$ to the diazanaphthalene ring;

when the carbon atom to which $R^{39}$ is attached serves as the point of attachment of $R^3$ to the diazanaphthalene ring, then $R^{39}$ is a single bond connecting $R^3$ to the diazanaphthalene ring;

when the nitrogen atom to which $R^{40}$ is attached serves as the point of attachment of $R^3$ to the diazanaphthalene ring, then $R^{40}$ is a single bond connecting $R^3$ to the diazanaphthalene ring;

when the carbon atom to which $R^{41}$ is attached serves as the point of attachment of $R^3$ to the diazanaphthalene ring, then $R^{41}$ is a single bond connecting $R^3$ to the diazanaphthalene ring;

when the carbon atom to which $R^{42}$ is attached serves as the point of attachment of $R^3$ to the diazanaphthalene ring, then $R^{42}$ is a single bond connecting $R^3$ to the diazanaphthalene ring;

when the carbon atom to which $R^{43}$ is attached serves as the point of attachment of $R^3$ to the diazanaphthalene ring, then $R^{43}$ is a single bond connecting $R^3$ to the diazanaphthalene ring;

when the nitrogen atom to which $R^{44}$ is attached serves as the point of attachment of $R^3$ to the diazanaphthalene ring, then $R^{44}$ is a single bond connecting $R^3$ to the diazanaphthalene ring;

when the carbon atom to which $R^{45}$ is attached serves as the point of attachment of $R^3$ to the diazanaphthalene ring, then $R^{45}$ is a single bond connecting $R^3$ to the diazanaphthalene ring;

when the carbon atom to which $R^{46}$ is attached serves as the point of attachment of $R^3$ to the diazanaphthalene ring, then $R^{46}$ is a single bond connecting $R^3$ to the diazanaphthalene ring;

when the nitrogen atom to which $R^{47}$ is attached serves as the point of attachment of $R^3$ to the diazanaphthalene ring, then $R^{47}$ is a single bond connecting $R^3$ to the diazanaphthalene ring;

when the carbon atom to which $R^{48}$ is attached serves as the point of attachment of $R^3$ to the diazanaphthalene ring, then $R^{48}$ is a single bond connecting $R^3$ to the diazanaphthalene ring;

when the carbon atom to which $R^{49}$ is attached serves as the point of attachment of $R^3$ to the diazanaphthalene ring, then $R^{49}$ is a single bond connecting $R^3$ to the diazanaphthalene ring;

when the nitrogen atom to which $R^{50}$ is attached serves as the point of attachment of $R^3$ to the diazanaphthalene ring, then $R^{50}$ is a single bond connecting $R^3$ to the diazanaphthalene ring;

when the carbon atom to which $R^{51}$ is attached serves as the point of attachment of $R^3$ to the diazanaphthalene ring, then $R^{51}$ is a single bond connecting $R^3$ to the diazanaphthalene ring;

when the carbon atom to which $R^{52}$ is attached serves as the point of attachment of $R^3$ to the diazanaphthalene ring, then $R^{52}$ is a single bond connecting $R^3$ to the diazanaphthalene ring;

when the carbon atom to which $R^{53}$ is attached serves as the point of attachment of $R^3$ to the diazanaphthalene ring, then $R^{53}$ is a single bond connecting $R^3$ to the diazanaphthalene ring;

when the carbon atom to which $R^{54}$ is attached serves as the point of attachment of $R^3$ to the diazanaphthalene ring, then $R^{54}$ is a single bond connecting $R^3$ to the diazanaphthalene ring;

when the carbon atom to which $R^{55}$ is attached serves as the point of attachment of $R^3$ to the diazanaphthalene ring, then $R^{55}$ is a single bond connecting $R^3$ to the diazanaphthalene ring;

when the carbon atom to which $R^{56}$ is attached serves as the point of attachment of $R^3$ to the diazanaphthalene ring, then $R^{56}$ is a single bond connecting $R^3$ to the diazanaphthalene ring;

when the carbon atom to which $R^{57}$ is attached serves as the point of attachment of $R^3$ to the diazanaphthalene ring, then $R^{57}$ is a single bond connecting $R^3$ to the diazanaphthalene ring;

when the carbon atom to which $R^{58}$ is attached serves as the point of attachment of $R^3$ to the diazanaphthalene ring, then $R^{58}$ is a single bond connecting $R^3$ to the diazanaphthalene ring;

when the carbon atom to which $R^{59}$ is attached serves as the point of attachment of $R^3$ to the diazanaphthalene ring, then $R^{59}$ is a single bond connecting $R^3$ to the diazanaphthalene ring;

when the carbon atom to which $R^{60}$ is attached serves as the point of attachment of $R^3$ to the diazanaphthalene ring, then $R^{60}$ is a single bond connecting $R^3$ to the diazanaphthalene ring;

when the carbon atom to which $R^{61}$ is attached serves as the point of attachment of $R^3$ to the diazanaphthalene ring, then $R^{61}$ is a single bond connecting $R^3$ to the diazanaphthalene ring;

when the carbon atom to which $R^{62}$ is attached serves as the point of attachment of $R^3$ to the diazanaphthalene ring, then $R^{62}$ is a single bond connecting $R^3$ to the diazanaphthalene ring;

when the carbon atom to which $R^{63}$ is attached serves as the point of attachment of $R^3$ to the diazanaphthalene ring, then $R^{63}$ is a single bond connecting $R^3$ to the diazanaphthalene ring; and when the carbon atom to which $R^{64}$ is attached serves as the point of attachment of $R^3$ to the diazanaphthalene ring, then $R^{64}$ is a single bond connecting $R^3$ to the diazanaphthalene ring.

In some embodiments of Formulas I, Ia, Ib, Ic, Id, and Ie, $R^{36}$ is selected from the group consisting of a single bond, H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$XR^{19}$, —C(=O)N($R^{15}$)$_2$, —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{20}$, and -carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formulas I, Ia, Ib, Ic, Id, and Ie, $R^{37}$, $R^{38}$, and $R^{39}$ are independently selected from the group consisting of a single bond, H, halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —N($R^{15}$)($R^{18}$), —($C_{1-4}$ alkylene)$_p$$XR^{19}$, —C(=O)N($R^{15}$)$_2$, —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{20}$, and -carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formulas I, Ia, Ib, Ic, Id, and Ie, one of $R^{36}$ and $R^{37}$, $R^{37}$ and $R^{38}$, or $R^{38}$ and $R^{39}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{22}$ and -carbocyclyl optionally substituted with 1-12 (e.g., 1-11, 1-10, 1-9, 1-8, 1-7, 1-6, 1-5, 1-4, 1-3, 1-2, 1) $R^{21}$.

In some embodiments of Formulas I, Ia, Ib, Ic, Id, and Ie, $R^{40}$ is selected from the group consisting of a single bond, H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$XR^{19}$, —C(=O)N($R^{15}$)$_2$, —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{20}$, and -carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formulas I, Ia, Ib, Ic, Id, and Ie, $R^{41}$, $R^{42}$, and $R^{43}$ are independently selected from the group consisting of a single bond, H, halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —N($R^{15}$)($R^{18}$), —($C_{1-4}$ alkylene)$_p$$XR^{19}$, —C(=O)N($R^{15}$)$_2$, —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{20}$, and -carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formulas I, Ia, Ib, Ic, Id, and Ie, one of $R^{40}$ and $R^{41}$, $R^{41}$ and $R^{42}$, or $R^{43}$ and $R^{40}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{22}$ and -carbocyclyl optionally substituted with 1-12 (e.g., 1-11, 1-10, 1-9, 1-8, 1-7, 1-6, 1-5, 1-4, 1-3, 1-2, 1) $R^{21}$;

In some embodiments of Formulas I, Ia, Ib, Ic, Id, and Ie, $R^{44}$ is selected from the group consisting of a single bond, H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$XR^{19}$, —C(=O)N($R^{15}$)$_2$, —($C_{1-4}$ alkylene)$_p$heterocyclyl optionally substituted with 1-10 (e.g., 1-9, 1-8, 1-7, 1-6, 1-5, 1-4, 1-3, 1-2, 1 $R^{20}$, and -carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formulas I, Ia, Ib, Ic, Id, and Ie, $R^{45}$ and $R^{46}$ are independently selected from the group consisting of a single bond, H, halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —N($R^{15}$)($R^{18}$), —($C_{1-4}$ alkylene)$_p$$XR^{19}$, —C(=O)N($R^{15}$)$_2$, —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{20}$, and -carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formulas I, Ia, Ib, Ic, Id, and Ie, one of $R^{44}$ and $R^{45}$ or $R^{45}$ and $R^{46}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{22}$ and -carbocyclyl optionally substituted with 1-12 (e.g., 1-11, 1-10, 1-9, 1-8, 1-7, 1-6, 1-5, 1-4, 1-3, 1-2, 1) $R^{21}$.

In some embodiments of Formulas I, Ia, Ib, Ic, Id, and Ie, $R^{47}$ is selected from the group consisting of a single bond, H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$XR^{19}$, —C(=O)N($R^{15}$)$_2$, —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{20}$, and -carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formulas I, Ia, Ib, Ic, Id, and Ie, $R^{48}$ and $R^{49}$ are independently selected from the group consisting of a single bond, H, halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —N($R^{15}$)($R^{18}$), —($C_{1-4}$ alkylene)$_p$$XR^{19}$, —C(=O)N(R$^{15}$)$_2$, —(C$_{1-4}$ alkylene)$_p$heterocyclyl optionally substituted with 1-10 (e.g., 1-9, 1-8, 1-7, 1-6, 1-5, 1-4, 1-3, 1-2, 1) R$^{20}$, and -carbocyclyl optionally substituted with 1-12 (e.g., 1-11, 1-10, 1-9, 1-8, 1-7, 1-6, 1-5, 1-4, 1-3, 1-2, 1) R$^{21}$; wherein each —(C$_{1-4}$ alkylene) is, independently, optionally substituted with one or more substituents as defined anywhere herein.

In some embodiments of Formulas I, Ia, Ib, Ic, Id, and Ie, one of R$^{47}$ and R$^{48}$ or R$^{47}$ and R$^{49}$ are taken together to form a heterocyclyl optionally substituted with 1-10 (e.g., 1-9, 1-8, 1-7, 1-6, 1-5, 1-4, 1-3, 1-2, 1) R$^{22}$.

In some embodiments of Formulas I, Ia, Ib, Ic, Id, and Ie, R$^{50}$ is selected from the group consisting of a single bond, H, unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —(C$_{1-4}$ alkylene)XR$^{19}$, —C(=O)N(R$^{15}$)$_2$, —(C$_{1-4}$ alkylene)$_p$heterocyclyl optionally substituted with 1-10 (e.g., 1-9, 1-8, 1-7, 1-6, 1-5, 1-4, 1-3, 1-2, 1) R$^{20}$, and -carbocyclyl optionally substituted with 1-12 (e.g., 1-11, 1-10, 1-9, 1-8, 1-7, 1-6, 1-5, 1-4, 1-3, 1-2, 1) R$^{21}$; wherein each —(C$_{1-4}$ alkylene) is, independently, optionally substituted with one or more substituents as defined anywhere herein.

In some embodiments of Formulas I, Ia, Ib, Ic, Id, and Ie, R$^{51}$ and R$^{52}$ are independently selected from the group consisting of a single bond, H, halide (e.g., F, Cl, Br, I), unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —CN, —N(R$^{15}$)(R$^{18}$), —(C$_{1-4}$ alkylene)$_p$XR$^{19}$, —C(=O)N(R$^{15}$)$_2$, —(C$_{1-4}$ alkylene)$_p$heterocyclyl optionally substituted with 1-10 (e.g., 1-9, 1-8, 1-7, 1-6, 1-5, 1-4, 1-3, 1-2, 1) R$^{20}$, and -carbocyclyl optionally substituted with 1-12 (e.g., 1-11, 1-10, 1-9, 1-8, 1-7, 1-6, 1-5, 1-4, 1-3, 1-2, 1) R$^{21}$; wherein each —(C$_{1-4}$ alkylene) is, independently, optionally substituted with one or more substituents as defined anywhere herein.

In some embodiments of Formulas I, Ia, Ib, Ic, Id, and Ie, R$^{51}$ and R$^{52}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) R$^{22}$ and -carbocyclyl optionally substituted with 1-12 (e.g., 1-11, 1-10, 1-9, 1-8, 1-7, 1-6, 1-5, 1-4, 1-3, 1-2, 1) R$^{21}$.

In some embodiments of Formulas I, Ia, Ib, Ic, Id, and Ie, R$^{53}$, R$^{54}$, and R$^{55}$ are independently selected from the group consisting of a single bond, H, halide (e.g., F, Cl, Br, I), unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —CN, —N(R$^{15}$)(R$^{18}$), —(C$_{1-4}$ alkylene)$_p$XR$^{19}$, —C(=O)N(R$^{15}$)$_2$, —(C$_{1-4}$ alkylene)$_p$heterocyclyl optionally substituted with 1-10 (e.g., 1-9, 1-8, 1-7, 1-6, 1-5, 1-4, 1-3, 1-2, 1) R$^{20}$, and -carbocyclyl optionally substituted with 1-12 (e.g., 1-11, 1-10, 1-9, 1-8, 1-7, 1-6, 1-5, 1-4, 1-3, 1-2, 1) R$^{21}$; wherein each —(C$_{1-4}$ alkylene) is, independently, optionally substituted with one or more substituents as defined anywhere herein.

In some embodiments of Formulas I, Ia, Ib, Ic, Id, and Ie, there is the proviso that when R$^{54}$ is a single bond connecting R$^3$ to the diazanaphthalene ring, R$^{53}$ and R$^{55}$ are not methyls.

In some embodiments of Formulas I, Ia, Ib, Ic, Id, and Ie, one of R$^{53}$ and R$^{54}$ or R$^{54}$ and R$^{55}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) R$^{22}$ and -carbocyclyl optionally substituted with 1-12 (e.g., 1-11, 1-10, 1-9, 1-8, 1-7, 1-6, 1-5, 1-4, 1-3, 1-2, 1) R$^{21}$.

In some embodiments of Formulas I, Ia, Ib, Ic, Id, and Ie, R$^{56}$, R$^{57}$, and R$^{58}$ are independently selected from the group consisting of a single bond, H, halide (e.g., F, Cl, Br, I), unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —CN, —N(R$^{15}$)(R$^{18}$), —(C$_{1-4}$ alkylene)$_p$XR$^{19}$, —C(=O)N(R$^{15}$)$_2$, —(C$_{1-4}$ alkylene)$_p$heterocyclyl optionally substituted with 1-10 (e.g., 1-9, 1-8, 1-7, 1-6, 1-5, 1-4, 1-3, 1-2, 1) R$^{20}$, and -carbocyclyl optionally substituted with 1-12 (e.g., 1-11, 1-10, 1-9, 1-8, 1-7, 1-6, 1-5, 1-4, 1-3, 1-2, 1) R$^{21}$; wherein each —(C$_{1-4}$ alkylene) is, independently, optionally substituted with one or more substituents as defined anywhere herein.

In some embodiments of Formulas I, Ia, Ib, Ic, Id, and Ie, R$^{56}$ and R$^{57}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) R$^{22}$ and -carbocyclyl optionally substituted with 1-12 (e.g., 1-11, 1-10, 1-9, 1-8, 1-7, 1-6, 1-5, 1-4, 1-3, 1-2, 1) R$^{21}$.

In some embodiments of Formulas I, Ia, Ib, Ic, Id, and Ie, R$^{59}$ and R$^{60}$ are independently selected from the group consisting of a single bond, H, halide (e.g., F, Cl, Br, I), unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —CN, —N(R$^{15}$)(R$^{18}$), —(C$_{1-4}$ alkylene)$_p$XR$^{19}$, —C(=O)N(R$^{15}$)$_2$, —(C$_{1-4}$ alkylene)$_p$heterocyclyl optionally substituted with 1-10 (e.g., 1-9, 1-8, 1-7, 1-6, 1-5, 1-4, 1-3, 1-2, 1) R$^{20}$, and -carbocyclyl optionally substituted with 1-12 (e.g., 1-11, 1-10, 1-9, 1-8, 1-7, 1-6, 1-5, 1-4, 1-3, 1-2, 1) R$^{21}$; wherein each —(C$_{1-4}$ alkylene) is, independently, optionally substituted with one or more substituents as defined anywhere herein.

In some embodiments of Formulas I, Ia, Ib, Ic, Id, and Ie, R$^{59}$ and R$^{60}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) R$^{22}$ and -carbocyclyl optionally substituted with 1-12 (e.g., 1-11, 1-10, 1-9, 1-8, 1-7, 1-6, 1-5, 1-4, 1-3, 1-2, 1) R$^{21}$.

In some embodiments of Formulas I, Ia, Ib, Ic, Id, and Ie, R$^{61}$ and R$^{62}$ are independently selected from the group consisting of a single bond, H, halide (e.g., F, Cl, Br, I), unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —CN, —N(R$^{15}$)(R$^{18}$), —(C$_{1-4}$ alkylene)$_p$XR$^{19}$, —C(=O)N(R$^{15}$)$_2$, —(C$_{1-4}$ alkylene)$_p$heterocyclyl optionally substituted with 1-10 (e.g., 1-9, 1-8, 1-7, 1-6, 1-5, 1-4, 1-3, 1-2, 1) R$^{20}$, and -carbocyclyl optionally substituted with 1-12 (e.g., 1-11, 1-10, 1-9, 1-8, 1-7, 1-6, 1-5, 1-4, 1-3, 1-2, 1) R$^{21}$; wherein each —(C$_{1-4}$ alkylene) is, independently, optionally substituted with one or more substituents as defined anywhere herein.

In some embodiments of Formulas I, Ia, Ib, Ic, Id, and Ie, R$^{63}$ and R$^{64}$ are independently selected from the group consisting of a single bond, H, halide (e.g., F, Cl, Br, I), unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —CN, —N(R$^{15}$)(R$^{18}$), —(C$_{1-4}$ alkylene)$_p$XR$^{19}$, —C(=O)N(R$^{15}$)$_2$, —(C$_{1-4}$ alkylene)$_p$heterocyclyl optionally substituted with 1-10 (e.g., 1-9, 1-8, 1-7, 1-6, 1-5, 1-4, 1-3, 1-2, 1) R$^{20}$, and -carbocyclyl optionally substituted with 1-12 (e.g., 1-11, 1-10, 1-9, 1-8, 1-7, 1-6, 1-5, 1-4, 1-3, 1-2, 1) R$^{21}$; wherein each —(C$_{1-4}$ alkylene) is, independently, optionally substituted with one or more substituents as defined anywhere herein.

In some embodiments of Formulas I, Ia, Ib, Ic, Id, and Ie, $R^{63}$ and $R^{64}$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{22}$ and -carbocyclyl optionally substituted with 1-12 (e.g., 1-11, 1-10, 1-9, 1-8, 1-7, 1-6, 1-5, 1-4, 1-3, 1-2, 1) $R^{21}$.

In some embodiments of Formulas I, Ia, Ib, Ic, Id, and Ie, each $X^1$ is O or S.

In some embodiments of Formulas I, Ia, Ib, Ic, Id, and Ie, $R^3$ is selected from the group consisting of: furanyl optionally substituted with 1-4 (e.g., 1-3, 1-2, 1) $R^8$, thiophenyl optionally substituted with 1-4 (e.g., 1-3, 1-2, 1) $R^8$, pyrrolyl optionally substituted with 1-4 (e.g., 1-3, 1-2, 1) $R^8$,

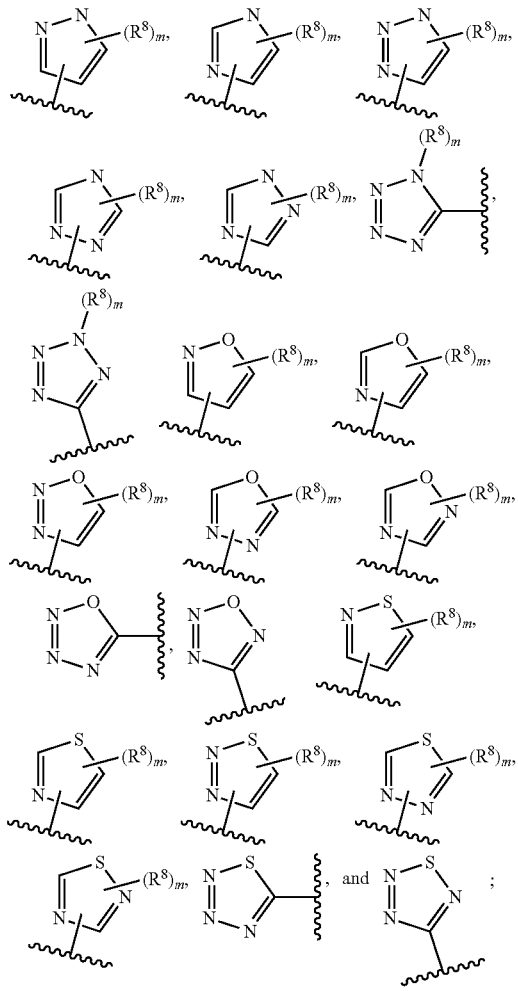

wherein each m is independently 1 to 4 (e.g., 1-3, 1-2, 1).

In some embodiments of Formulas I, Ia, Ib, Ic, Id, and Ie, $R^3$ is a 6-10-membered heteroaryl ring optionally substituted as defined anywhere herein.

In some embodiments of Formulas I, Ia, Ib, Ic, Id, and Ie, $R^3$ is 6-10-membered heteroaryl ring optionally substituted with 1-4 (e.g., 1-3, 1-2, 1) $R^8$.

In some embodiments of Formulas I, Ia, Ib, Ic, Id, and Ie, $R^6$ is selected from the group consisting of —($C_{1-4}$ alkylene)$_p$aryl substituted with 1-5 $R^9$, —($C_{2-4}$ alkenylene)$_p$aryl substituted with 1-5 $R^9$, —($C_{1-4}$ alkylene)$_p$heteroaryl optionally substituted with 1-6 $R^{10}$; —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{11}$, —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{12}$, —($C_{1-4}$ alkylene)N($R^{13}$)($R^{14}$), —N($R^{15}$)($R^6$), —CF($C_{1-9}$ alkyl)$_2$, —($C_{1-4}$ alkylene)$_p$O($C_{3-9}$ alkyl), and —($C_{2-9}$ alkynyl) optionally substituted with one or more halide (e.g., F, Cl, Br, I)s; wherein each alkyl of —CF($C_{1-9}$ alkyl)$_2$ is, independently, optionally substituted with one or more halides; wherein each —($C_{1-4}$ alkylene) is, independently, optionally substituted with one or more substituents as defined anywhere herein; wherein —($C_{1-4}$ alkenylene) is, optionally substituted with one or more substituents as defined anywhere herein.

In some embodiments of Formulas I, Ia, Ib, Ic, Id, and Ie, $R^6$ is -heterocyclyl optionally substituted with 1-2 $R^{11}$.

In some embodiments of Formulas I, Ia, Ib, Ic, Id, and Ie, $R^6$ is a —CH$_2$heterocyclyl optionally substituted with 1-2 $R^{11}$.

In some embodiments of Formulas I, Ia, Ib, Ic, Id, and Ie, $R^6$ is either a piperidinyl or a pyrrolidinyl both optionally substituted with 1-2 $R^{11}$.

In some embodiments of Formulas I, Ia, Ib, Ic, Id, and Ie, $R^6$ is a piperidinyl substituted with one —N($R^{15}$)($R^{25}$).

In some embodiments of Formulas I, Ia, Ib, Ic, Id, and Ie, $R^{15}$ and $R^{25}$ are independently selected from the group consisting of H, Me, and —$C_{1-4}$ haloalkyl.

In some embodiments of Formulas I, Ia, Ib, Ic, Id, and Ie, each $R^8$ is independently selected from the group consisting of H, halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —N($R^{15}$)($R^{18}$), —($C_{1-4}$ alkylene)$_p$X$R^{19}$, —C(=O)N($R^{15}$)$_2$, —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{20}$, and -carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formulas I, Ia, Ib, Ic, Id, and Ie, two adjacent $R^8$ are taken together to form a ring which is selected from the group consisting of -heterocyclyl optionally substituted with 1-10 (e.g., 1-9, 1-8, 1-7, 1-6, 1-5, 1-4, 1-3, 1-2, 1) $R^{22}$ and -carbocyclyl optionally substituted with 1-12 (e.g., 1-11, 1-10, 1-9, 1-8, 1-7, 1-6, 1-5, 1-4, 1-3, 1-2, 1) $R^{21}$.

In some embodiments of Formulas I, Ia, Ib, Ic, Id, and Ie, each $R^9$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —X$R^{23}$, —C(=O)N($R^{15}$)$_2$, —($C_{1-4}$ alkylene)$_p$N($R^{24}$)$_2$, —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{22}$, and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formula I, there is the proviso that when $Y^2$ is N then $R^9$ is not —OMe or

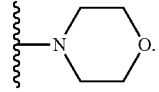

In some embodiments of Formula Ib, $R^9$ is not —OMe or

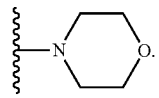 [SMILES: *N1CCOCC1]

In some embodiments of Formulas I, Ia, Ib, Ic, Id, and Ie, each $R^{10}$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —$XR^{23}$, —C(=O)N($R^{15}$)$_2$, —($C_{1-4}$ alkylene)$_p$N($R^{24}$)$_2$, —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{22}$, and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formulas I, Ia, Ib, Ic, Id, and Ie, each $R^{11}$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$O$R^{19}$, —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{22}$, —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{21}$, —N($R^{15}$)($R^{25}$), —C(=O)($R^{26}$), —($C_{1-4}$ alkylene)C(=O)O$R^{27}$, —($C_{1-4}$ alkylene)aryl optionally substituted with one or more halides, —($C_{1-4}$ alkylene)$_p$heteroaryl optionally substituted with one or more halides, and —SO$_2$($R^{28}$); wherein each —($C_{1-4}$ alkylene) is, independently, optionally substituted with one or more substituents as defined anywhere herein.

In some embodiments of Formulas I, Ia, Ib, Ic, Id, and Ie, two $R^{11}$ attached to the same carbon atom can together represent =O to form a carbonyl group.

In some embodiments of Formulas I, Ia, Ib, Ic, Id, and Ie, each $R^{12}$ is selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$O$R^{19}$, —N($R^{15}$)($R^{29}$), —C(=O)($R^{26}$), —C(=O)O$R^{27}$, —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{22}$, and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formulas I, Ia, Ib, Ic, Id, and Ie, $R^{13}$ is selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{20}$, and -carbocyclyl optionally substituted with 1-12 (e.g., 1-11, 1-10, 1-9, 1-8, 1-7, 1-6, 1-5, 1-4, 1-3, 1-2, 1) $R^{21}$; wherein —($C_{1-4}$ alkylene) is, optionally substituted with one or more substituents as defined anywhere herein.

In some embodiments of Formulas I, Ia, Ib, Ic, Id, and Ie, $R^{14}$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{20}$, and -carbocyclyl optionally substituted with 1-12 (e.g., 1-11, 1-10, 1-9, 1-8, 1-7, 1-6, 1-5, 1-4, 1-3, 1-2, 1) $R^{21}$; wherein —($C_{1-4}$ alkylene) is, optionally substituted with one or more substituents as defined anywhere herein.

In some embodiments of Formulas I, Ia, Ib, Ic, Id, and Ie, each $R^{15}$ is selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl).

In some embodiments of Formulas I, Ia, Ib, Ic, Id, and Ie, $R^{16}$ is selected from the group consisting of —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{20}$, and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formulas I, Ia, Ib, Ic, Id, and Ie, $R^{17}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl).

In some embodiments of Formulas I, Ia, Ib, Ic, Id, and Ie, two adjacent $R^{17}$ are taken together to form a -heterocyclyl ring optionally substituted with 1-10 (e.g., 1-9, 1-8, 1-7, 1-6, 1-5, 1-4, 1-3, 1-2, 1) $R^{22}$.

In some embodiments of Formulas I, Ia, Ib, Ic, Id, and Ie, $R^{18}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —(C=O)$R^{15}$, and —($C_{1-4}$ alkylene)$_p$heterocyclyl optionally substituted with one or more halides or one or more unsubstituted —($C_{1-5}$ alkyl); wherein —($C_{1-4}$ alkylene) is, independently, optionally substituted with one or more substituents as defined anywhere herein.

In some embodiments of Formulas I, Ia, Ib, Ic, Id, and Ie, each $R^{19}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with one or more halides or one or more unsubstituted —($C_{1-5}$ alkyl), and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formulas I, Ia, Ib, Ic, Id, and Ie, each $R^{20}$ independently is selected from the group consisting of halide (e.g., F, Cl, Br, I), unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —N($R^{15}$)$_2$, and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formulas I, Ia, Ib, Ic, Id, and Ie, each $R^{21}$ is independently selected from the group consisting of halide (e.g., F, Cl, Br, I), unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), and —CN.

In some embodiments of Formulas I, Ia, Ib, Ic, Id, and Ie, each $R^{22}$ is independently selected from the group consisting of halide (e.g., F, Cl, Br, I), unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —CN, —OH, —N($R^{15}$)$_2$, —C(=O)$R^{34}$, and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formulas I, Ia, Ib, Ic, Id, and Ie, each $R^{23}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)N($R^{15}$)$_2$, —($C_{1-4}$ alkylene)$_p$aryl optionally substituted with 1-10 (e.g., 1-9, 1-8, 1-7, 1-6, 1-5, 1-4, 1-3, 1-2, 1) $R^{30}$, —($C_{1-4}$ alkylene)$_p$heterocyclyl optionally substituted with 1-12 (e.g., 1-11, 1-10, 1-9, 1-8, 1-7, 1-6, 1-5, 1-4, 1-3, 1-2, 1) $R^{31}$, and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formulas I, Ia, Ib, Ic, Id, and Ie, each $R^{24}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with one or more halides or one or more unsubstituted —($C_{1-5}$ alkyl), and —($C_{1-4}$ alkylene)N($R^{15}$)$_2$; wherein each —($C_{1-4}$ alkylene) is, independently, optionally substituted with one or more substituents as defined anywhere herein.

In some embodiments of Formulas I, Ia, Ib, Ic, Id, and Ie, each $R^{25}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{32}$, —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{21}$, —($C_{1-4}$ alkylene)O$R^{33}$; wherein each —($C_{1-4}$ alkylene) is, independently, optionally substituted with one or more substituents as defined anywhere herein.

In some embodiments of Formulas I, Ia, Ib, Ic, Id, and Ie, $R^{26}$ is selected from the group consisting of H, unsubstituted —($C_{3-5}$ alkyl), unsubstituted —($C_{2-5}$ alkenyl), —($C_{2-5}$ alkynyl), unsubstituted —($C_{1-5}$ haloalkyl), —($C_{1-4}$ alkylene)$_p$aryl optionally substituted with one or more halides or unsubstituted —($C_{1-5}$ alkyl), —($C_{1-4}$ alkylene)$_p$heteroaryl optionally substituted with one or more halides or one or more unsubstituted —($C_{1-5}$ alkyl), and —($C_{1-4}$ alkylene)$_p$heterocyclyl optionally substituted with one or more halides or one or more unsubstituted —($C_{1-5}$ alkyl); wherein each —($C_{1-4}$ alkylene) is, independently, optionally substituted with one or more substituents as defined anywhere herein.

In some embodiments of Formulas I, Ia, Ib, Ic, Id, and Ie, $R^{27}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with one or more halides or one or more unsubstituted —($C_{1-5}$ alkyl), —($C_{1-4}$ alkylene)$_p$heteroaryl optionally substituted with one or more halides or unsubstituted —($C_{1-5}$ alkyl), and —($C_{1-4}$ alkylene)$_p$heterocyclyl optionally substituted with one or more halides or one or more unsubstituted —($C_{1-5}$ alkyl); wherein each —($C_{1-4}$ alkylene) is, independently, optionally substituted with one or more substituents as defined anywhere herein.

In some embodiments of Formulas I, Ia, Ib, Ic, Id, and Ie, $R^{28}$ is selected from the group consisting of unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$aryl optionally substituted with one or more halides or one or more unsubstituted —($C_{1-5}$ alkyl), —($C_{1-4}$ alkylene)$_p$heteroaryl optionally substituted with one or more halides or one or more unsubstituted —($C_{1-5}$ alkyl), and —($C_{1-4}$ alkylene)$_p$heterocyclyl optionally substituted with one or more halides or one or more unsubstituted —($C_{1-5}$ alkyl); wherein —($C_{1-4}$ alkylene) is, optionally substituted with one or more substituents as defined anywhere herein.

In some embodiments of Formulas I, Ia, Ib, Ic, Id, and Ie, each $R^{29}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{32}$, —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{21}$, —($C_{1-4}$ alkylene)O$R^{33}$; wherein each —($C_{1-4}$ alkylene) is, independently, optionally substituted with one or more substituents as defined anywhere herein.

In some embodiments of Formulas I, Ia, Ib, Ic, Id, and Ie, each $R^{29}$ is selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-4}$ alkylene)$_p$heterocyclyl optionally substituted with 1-10 (e.g., 1-9, 1-8, 1-7, 1-6, 1-5, 1-4, 1-3, 1-2, 1) $R^{32}$, —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{21}$, —($C_{1-4}$ alkylene)O$R^{33}$, and —C(=O)O($C_{1-5}$ alkyl); wherein each —($C_{1-4}$ alkylene) is, independently, optionally substituted with one or more substituents as defined anywhere herein.

In some embodiments of Formulas I, Ia, Ib, Ic, Id, and Ie, each $R^{30}$ is independently selected from the group consisting of halide (e.g., F, Cl, Br, I), unsubstituted —($C_{2-5}$ alkyl), unsubstituted —($C_{2-5}$ alkenyl), unsubstituted —($C_{2-5}$ alkynyl), unsubstituted —($C_{1-5}$ haloalkyl), and —CN.

In some embodiments of Formulas I, Ia, Ib, Ic, Id, and Ie, each $R^{31}$ is independently selected from the group consisting of halide (e.g., F, Cl, Br, I), unsubstituted —($C_{2-5}$ alkyl), unsubstituted —($C_{2-5}$ alkenyl), unsubstituted —($C_{2-5}$ alkynyl), unsubstituted —($C_{1-5}$ haloalkyl), —CN, —OH, —C(=O)$R^{34}$, —N($R^{24}$)$_2$, and —($C_{1-4}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{21}$; wherein each —($C_{1-4}$ alkylene) is, independently, optionally substituted with one or more substituents as defined anywhere herein.

In some embodiments of Formulas I, Ia, Ib, Ic, Id, and Ie, each $R^{32}$ is independently selected from the group consisting of halide (e.g., F, Cl, Br, I) and unsubstituted —($C_{1-5}$ alkyl).

In some embodiments of Formulas I, Ia, Ib, Ic, Id, and Ie, each $R^{33}$ is independently selected from the group consisting of H and unsubstituted —($C_{1-5}$ alkyl).

In some embodiments of Formulas I, Ia, Ib, Ic, Id, and Ie, each $R^{34}$ is a heteroaryl optionally substituted with 1-6 (e.g., 1-5, 1-4, 1-3, 1-2, 1) $R^{35}$.

In some embodiments of Formulas I, Ia, Ib, Ic, Id, and Ie, each $R^{34}$ is independently selected from the group consisting of —O($C_{1-5}$ alkyl) and a heteroaryl optionally substituted with 1-6 (e.g., 1-5, 1-4, 1-3, 1-2, 1) $R^{35}$.

In some embodiments of Formulas I, Ia, Ib, Ic, Id, and Ie, each $R^{35}$ is a -heterocyclyl optionally substituted with one or more halides or one or more unsubstituted —($C_{1-5}$ alkyl).

In some embodiments of Formulas I, Ia, Ib, Ic, Id, and Ie, each X is selected from the group consisting of O and S.

In some embodiments of Formulas I, Ia, Ib, Ic, Id, and Ie, each p is independently 0 or 1.

In some embodiments of Formulas I, Ia, Ib, Ic, Id, and Ie, each —($C_{1-4}$ alkylene) is —($C_{1-3}$ alkylene).

In some embodiments of Formulas I, Ia, Ib, Ic, Id, and Ie, each —($C_{1-4}$ alkylene) is —($C_{1-2}$ alkylene).

In some embodiments of Formulas I, Ia, Ib, Ic, Id, and Ie, each —($C_{1-4}$ alkylene) is —($C_1$ alkylene).

In some embodiments of Formulas I, Ia, Ib, Ic, Id, and Ie, each —($C_{1-4}$ alkylene) is —$CH_2$—.

In some embodiments of Formulas I, Ia, Ib, Ic, Id, and Ie, each —($C_{1-4}$ alkylene) is optionally substituted with halide (e.g., F, Cl, Br, I).

In some embodiments of Formulas I, each —($C_{1-4}$ alkylene) is optionally substituted with F.

In some embodiments of Formulas I, Ia, Ib, Ic, Id, and Ie, $R^3$ is selected from the group consisting of pyrazolyl, imidazolyl, triazolyl, thiadiazolyl, and oxazolyl, each optionally substituted with 1-4 $R^8$.

In some embodiments of Formulas I, Ia, Ib, Ic, Id, and Ie, $R^3$ is selected from the group consisting of pyrazol-4-yl, imidazol-5-yl, 1,2,3-triazol-4-yl, thiadiazol-2-yl, and oxazol-5-yl, each optionally substituted with 1-4 $R^8$.

In some embodiments of Formulas I, Ia, Ib, Ic, Id, and Ie, $R^3$ is an unsubstituted pyrazol-4-yl.

In some embodiments of Formulas I, Ia, Ib, Ic, Id, and Ie, $R^3$ is a pyrazol-4-yl, substituted with one —($C_{1-3}$ alkyl).

In some embodiments of Formulas I, Ia, Ib, Ic, Id, and Ie, $R^3$ is a imidazol-5-yl substituted with one —($C_{1-3}$ alkyl).

In some embodiments of Formulas I, Ia, Ib, Ic, Id, and Ie, $R^3$ is a imidazol-5-yl substituted with two —($C_{1-3}$ alkyl).

In some embodiments of Formulas I, Ia, Ib, Ic, Id, and Ie, $R^3$ is an unsubstituted 1,2,3-triazol-4-yl.

In some embodiments of Formulas I, Ia, Ib, Ic, Id, and Ie, $R^3$ is a 1,2,3-triazol-4-yl substituted with one —($C_{1-3}$ alkyl).

In some embodiments of Formulas I, Ia, Ib, Ic, Id, and Ie, $R^3$ is an unsubstituted thiadiazol-2-yl.

In some embodiments of Formulas I, Ia, Ib, Ic, Id, and Ie, $R^3$ is a thiadiazol-2-yl substituted with one —($C_{1-3}$ alkyl).

In some embodiments of Formulas I, Ia, Ib, Ic, Id, and Ie, $R^3$ is an unsubstituted oxazol-5-yl.

In some embodiments of Formulas I, Ia, Ib, Ic, Id, and Ie, $R^3$ is a oxazol-5-yl substituted with one —($C_{1-3}$ alkyl).

In some embodiments of Formulas I, Ia, Ib, Ic, Id, and Ie, $R^3$ is

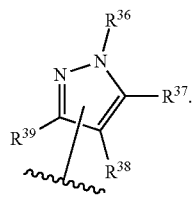

In some embodiments of Formulas I, Ia, Ib, Ic, Id, and Ie, $R^{38}$ is a single bond connecting $R^3$ to the diazanaphthalene ring, i.e., $R^3$ has the following formula:

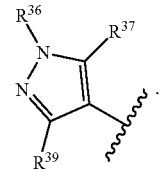

In some embodiments of Formulas I, Ia, Ib, Ic, Id, and Ie, $R^3$ is

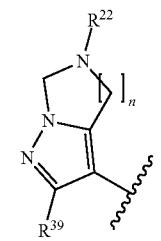

and n is 1 to 3.

In some embodiments of Formulas I, Ia, Ib, Ic, Id, and Ie, $R^{36}$ is selected from the group consisting of H, unsubstituted —($C_{1-3}$ alkyl), unsubstituted —($C_{1-2}$ haloalkyl), and —($C_{3-4}$ carbocyclyl) optionally substituted with 1-2 $R^{21}$.

In some embodiments of Formulas I, Ia, Ib, Ic, Id, and Ie, $R^{36}$ is selected from the group consisting of H, methyl, —$CF_3$, and cyclopropyl optionally substituted with 1-2 $R^{21}$.

In some embodiments of Formulas I, Ia, Ib, Ic, Id, and Ie, $R^{36}$ is selected from the group consisting of H and methyl.

In some embodiments of Formulas I, Ia, Ib, Ic, Id, and Ie, $R^{36}$ is methyl.

In some embodiments of Formulas I, Ia, Ib, Ic, Id, and Ie, $R^{36}$ is —$CD_3$.

In some embodiments of Formulas I, Ia, Ib, Ic, Id, and Ie, $R^{37}$ is selected from the group consisting of H, halide (e.g., F, Cl, Br, I), unsubstituted —($C_{1-2}$ alkyl), unsubstituted —($C_{1-2}$ haloalkyl), and —($C_{1-2}$ alkylene)$OR^{19}$.

In some embodiments of Formulas I, Ia, Ib, Ic, Id, and Ie, $R^{37}$ is selected from the group consisting of H, F, methyl, —$CF_3$, —($CH_2$)OH, and —($CH_2$)OMe.

In some embodiments of Formulas I, Ia, Ib, Ic, Id, and Ie, $R^{37}$ is selected from the group consisting of H, F, and methyl.

In some embodiments of Formulas I, Ia, Ib, Ic, Id, and Ie, $R^{37}$ is H.

In some embodiments of Formulas I, Ia, Ib, Ic, Id, and Ie, $R^{39}$ is selected from the group consisting of H and halide (e.g., F, Cl, Br, I).

In some embodiments of Formulas I, Ia, Ib, Ic, Id, and Ie, $R^{39}$ is selected from the group consisting of H and F.

In some embodiments of Formulas I, Ia, Ib, Ic, Id, and Ie, $R^{39}$ is H.

In some embodiments of Formulas I, Ia, Ib, Ic, Id, and Ie, $R^3$ is

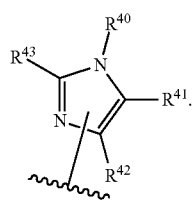

In some embodiments of Formulas I, Ia, Ib, Ic, Id, and Ie, $R^{12}$ is a single bond connecting $R^3$ to the diazanaphthalene ring, i.e., $R^3$ has the following formula:

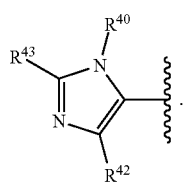

In some embodiments of Formulas I, Ia, Ib, Ic, Id, and Ie, $R^3$ is

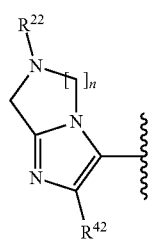

and n is 1 to 3.

In some embodiments of Formulas I, Ia, Ib, Ic, Id, and Ie, $R^{40}$ is selected from the group consisting of H, unsubstituted —($C_{1-3}$ alkyl), unsubstituted —($C_{1-2}$ haloalkyl), and —($C_{3-4}$ carbocyclyl) optionally substituted with 1-2 $R^{21}$.

In some embodiments of Formulas I, Ia, Ib, Ic, Id, and Ie, $R^{40}$ is selected from the group consisting of H, methyl, —$CF_3$, and cyclopropyl optionally substituted with 1-2 $R^{21}$.

In some embodiments of Formulas I, Ia, Ib, Ic, Id, and Ie, $R^{40}$ is selected from the group consisting of H and methyl.

In some embodiments of Formulas I, Ia, Ib, Ic, Id, and Ie, $R^{40}$ is methyl.

In some embodiments of Formulas I, Ia, Ib, Ic, Id, and Ie, $R^{40}$ is —$CD_3$.

In some embodiments of Formulas I, Ia, Ib, Ic, Id, and Ie, $R^{42}$ is selected from the group consisting of H and halide (e.g., F, Cl, Br, I).

In some embodiments of Formulas I, Ia, Ib, Ic, Id, and Ie, $R^{42}$ is selected from the group consisting of H and F.

In some embodiments of Formulas I, Ia, Ib, Ic, Id, and Ie, $R^{43}$ is selected from the group consisting of H, halide (e.g., F, Cl, Br, I), unsubstituted —($C_{1-2}$ alkyl), and unsubstituted —($C_{1-2}$ haloalkyl).

In some embodiments of Formulas I, Ia, Ib, Ic, Id, and Ie, $R^{43}$ is selected from the group consisting of H, F, methyl, and —$CF_3$.

In some embodiments of Formulas I, Ia, Ib, Ic, Id, and Ie, $R^{43}$ is selected from the group consisting of H and methyl.

In some embodiments of Formulas I, Ia, Ib, Ic, Id, and Ie, $R^{40}$ and $R^{43}$ are both methyl.

In some embodiments of Formulas I, Ia, Ib, Ic, Id, and Ie, $R^3$ is

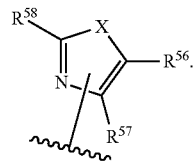

In some embodiments of Formulas I, Ia, Ib, Ic, Id, and Ie, $R^3$ is

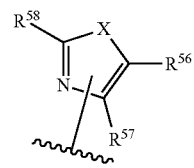

and X is S.

In some embodiments of Formulas I, Ia, Ib, Ic, Id, and Ie, $R^3$ is

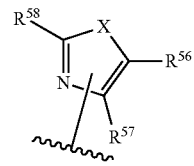

and X is O.

In some embodiments of Formulas I, Ia, Ib, Ic, Id, and Ie, $R^{56}$ is a single bond connecting $R^3$ to the diazanaphthalene ring, i.e., $R^3$ has the following formula:

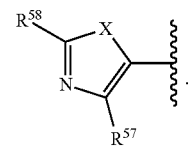

In some embodiments of Formulas I, Ia, Ib, Ic, Id, and Ie, $R^3$ is

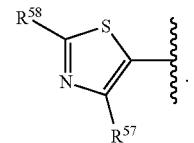

In some embodiments of Formulas I, Ia, Ib, Ic, Id, and Ie, $R^3$ is

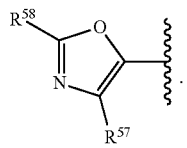

In some embodiments of Formulas I, Ia, Ib, Ic, Id, and Ie, R⁵⁷ is selected from the group consisting of H and halide (e.g., F, Cl, Br, I).

In some embodiments of Formulas I, Ia, Ib, Ic, Id, and Ie, R⁵⁷ is selected from the group consisting of H and F.

In some embodiments of Formulas I, Ia, Ib, Ic, Id, and Ie, R⁵⁸ is selected from the group consisting of H, halide (e.g., F, Cl, Br, I), unsubstituted —(C$_{1-2}$ alkyl), and unsubstituted —(C$_{1-2}$ haloalkyl).

In some embodiments of Formulas I, Ia, Ib, Ic, Id, and Ie, R⁵⁸ is selected from the group consisting of H, F, methyl, and —CF₃.

In some embodiments of Formulas I, Ia, Ib, Ic, Id, and Ie, R³ is

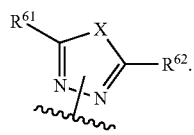

In some embodiments of Formulas I, Ia, Ib, Ic, Id, and Ie, R³ is

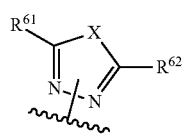

and X is S.

In some embodiments of Formulas I, Ia, Ib, Ic, Id, and Ie, R³ is

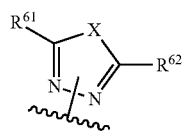

and X is O.

In some embodiments of Formulas I, Ia, Ib, Ic, Id, and Ie, R⁶² is a single bond connecting R³ to the diazanaphthalene ring, i.e., R³ has the following formula:

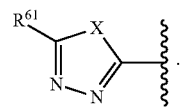

In some embodiments of Formulas I, Ia, Ib, Ic, Id, and Ie, R³ is

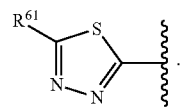

In some embodiments of Formulas I, Ia, Ib, Ic, Id, and Ie, R³ is

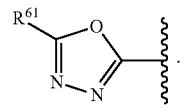

In some embodiments of Formulas I, Ia, Ib, Ic, Id, and Ie, R⁶¹ is selected from the group consisting of H, halide (e.g., F, Cl, Br, I), unsubstituted —(C$_{1-2}$ alkyl), unsubstituted —(C$_{1-2}$ haloalkyl), and —N(R¹⁵)(R¹⁸).

In some embodiments of Formulas I, Ia, Ib, Ic, Id, and Ie, R⁶¹ is selected from the group consisting of H, F, methyl, —CF₃, —NHMe, and —NMe₂.

In some embodiments of Formulas I, Ia, Ib, Ic, Id, and Ie, R⁶¹ is selected from the group consisting of H and methyl.

In some embodiments of Formulas I, Ia, Ib, Ic, Id, and Ie, R⁶¹ is methyl.

In some embodiments of Formulas I, Ia, Ib, Ic, Id, and Ie, R³ is

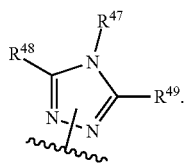

In some embodiments of Formulas I, Ia, Ib, Ic, Id, and Ie, R⁴⁹ is a single bond connecting R³ to the diazanaphthalene ring, i.e., R³ has the following formula:

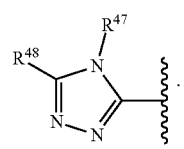

In some embodiments of Formulas I, Ia, Ib, Ic, Id, and Ie, is

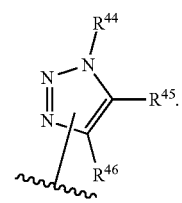

In some embodiments of Formulas I, Ia, Ib, Ic, Id, and Ie, R⁴⁵ is a single bond connecting R³ to the diazanaphthalene ring, i.e., R³ has the following formula:

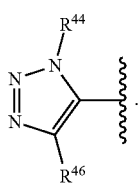

In some embodiments of Formulas I, Ia, Ib, Ic, Id, and Ie, $R^{46}$ is a single bond connecting $R^3$ to the diazanaphthalene ring, i.e., $R^3$ has the following formula:

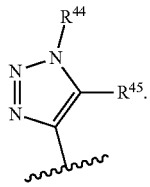

In some embodiments of Formulas I, Ia, Ib, Ic, Id, and Ie, $R^{44}$ is selected from the group consisting of H and unsubstituted —($C_{1-2}$ alkyl).

In some embodiments of Formulas I, Ia, Ib, Ic, Id, and Ie, $R^{44}$ is selected from the group consisting of H and methyl.

In some embodiments of Formulas I, Ia, Ib, Ic, Id, and Ie, $R^{44}$ is methyl.

In some embodiments of Formulas I, Ia, Ib, Ic, Id, and Ie, $R^{44}$ is —$CD_3$.

In some embodiments of Formulas I, Ia, Ib, Ic, Id, and Ie, $R^3$ is

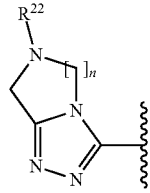

and n is 1 to 3.

In some embodiments of Formulas I, Ia, Ib, Ic, Id, and Ie, $R^{47}$ is selected from the group consisting of H, unsubstituted —($C_{1-3}$ alkyl), unsubstituted —($C_{1-2}$ haloalkyl), and —($C_{3-4}$ carbocyclyl) optionally substituted with 1-2 $R^{21}$.

In some embodiments of Formulas I, Ia, Ib, Ic, Id, and Ie, $R^{47}$ is selected from the group consisting of H, methyl, —$CF_3$, and cyclopropyl optionally substituted with 1-2 $R^{21}$.

In some embodiments of Formulas I, Ia, Ib, Ic, Id, and Ie, $R^{47}$ is selected from the group consisting of H and methyl.

In some embodiments of Formulas I, Ia, Ib, Ic, Id, and Ie, $R^{48}$ is selected from the group consisting of H, halide (e.g., F, Cl, Br, I), unsubstituted —($C_{1-2}$ alkyl), and unsubstituted —($C_{1-2}$ haloalkyl).

In some embodiments of Formulas I, Ia, Ib, Ic, Id, and Ie, $R^{48}$ is selected from the group consisting of H, F, methyl, and —$CF_3$.

In some embodiments of Formulas I, Ia, Ib, Ic, Id, and Ie, $R^{21}$ is selected from the group consisting of halide (e.g., F, Cl, Br, I), unsubstituted —($C_{1-3}$ alkyl), and unsubstituted —($C_{1-2}$ haloalkyl).

In some embodiments of Formulas I, Ia, Ib, Ic, Id, and Ie, $R^{21}$ is selected from the group consisting of F, methyl, and —$CF_3$.

In some embodiments of Formulas I, Ia, Ib, Ic, Id, and Ie, $R^{22}$ is selected from the group consisting of H and unsubstituted —($C_{1-2}$ alkyl).

In some embodiments of Formulas I, Ia, Ib, Ic, Id, and Ie, $R^{22}$ is selected from the group consisting of H and methyl.

Illustrative compounds of Formulas I, Ia, Ib, Ic, Id, and Ie are shown in Table 1 (below).

Illustrative compounds of Formula (I) are shown in Table 1.

TABLE 1

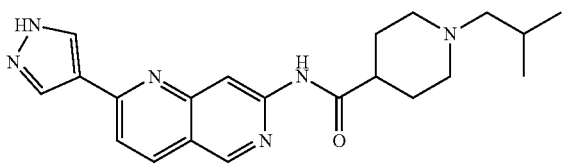 [SMILES: CC(C)CN1CCC(C(=O)Nc2cc3nc(-c4cn[nH]c4)ccc3cn2)CC1]

1

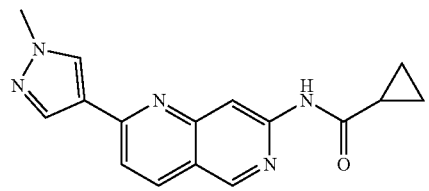 [SMILES: Cn1cc(-c2ccc3cnc(NC(=O)C4CC4)cc3n2)cn1]

2

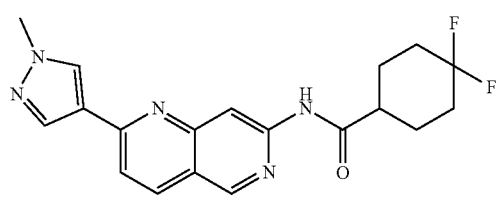 [SMILES: Cn1cc(-c2ccc3cnc(NC(=O)C4CCC(F)(F)CC4)cc3n2)cn1]

3

TABLE 1-continued
| | |
|---|---|
| 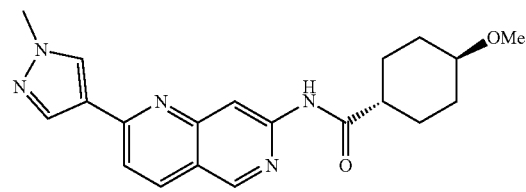 [SMILES: CO[C@H]1CC[C@H](C(=O)Nc2cc3nc(-c4cnn(C)c4)ccc3cn2)CC1] | 4 |
| 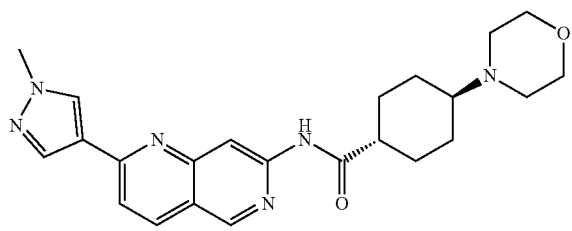 [SMILES: Cn1cc(-c2ccc3cnc(NC(=O)[C@H]4CC[C@H](N5CCOCC5)CC4)cc3n2)cn1] | 5 |
| 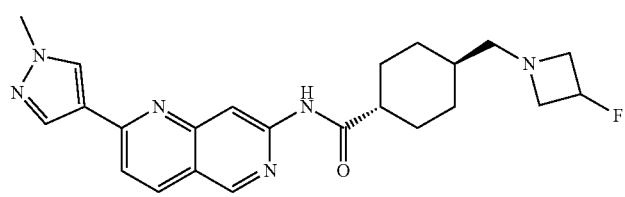 [SMILES: Cn1cc(-c2ccc3cnc(NC(=O)[C@H]4CC[C@H](CN5CC(F)C5)CC4)cc3n2)cn1] | 6 |
| 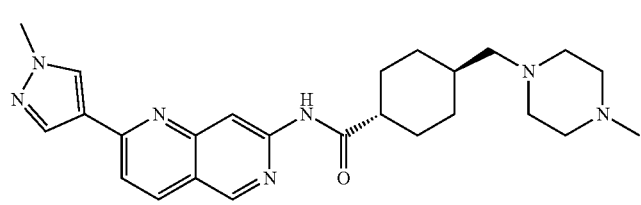 [SMILES: CN1CCN(C[C@H]2CC[C@H](C(=O)Nc3cc4nc(-c5cnn(C)c5)ccc4cn3)CC2)CC1] | 7 |
| 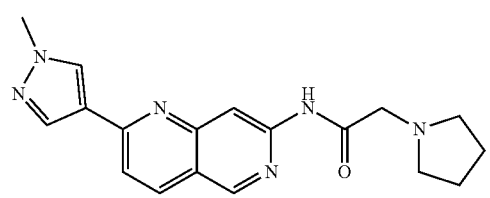 [SMILES: Cn1cc(-c2ccc3cnc(NC(=O)CN4CCCC4)cc3n2)cn1] | 8 |
| 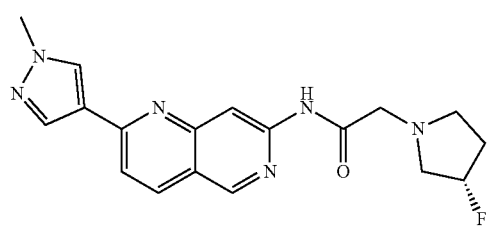 [SMILES: Cn1cc(-c2ccc3cnc(NC(=O)CN4CC[C@H](F)C4)cc3n2)cn1] | 9 |
| 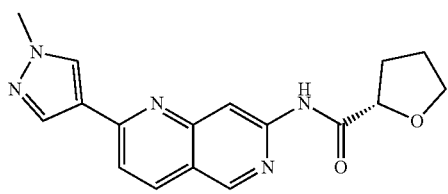 [SMILES: Cn1cc(-c2ccc3cnc(NC(=O)[C@@H]4CCCO4)cc3n2)cn1] | 10 |
| 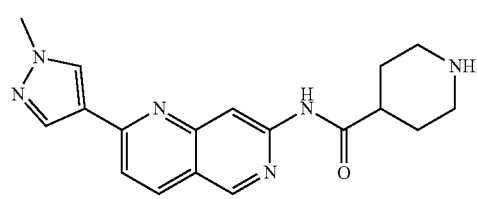 | 11 |

TABLE 1-continued
| | |
|---|---|
| 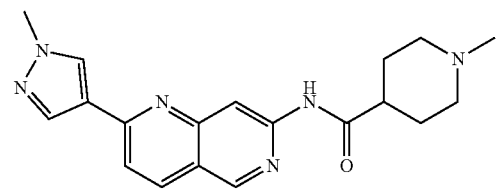 [SMILES: CN1CCC(C(=O)Nc2cc3nc(-c4cnn(C)c4)ccc3cn2)CC1] | 12 |
| 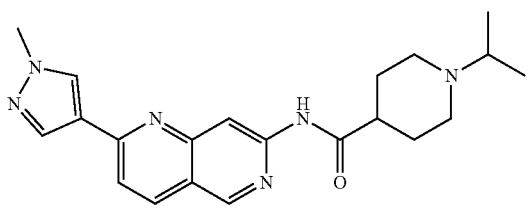 [SMILES: CC(C)N1CCC(C(=O)Nc2cc3nc(-c4cnn(C)c4)ccc3cn2)CC1] | 13 |
| 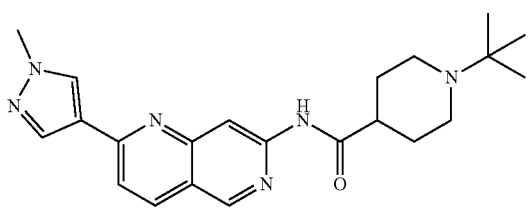 [SMILES: Cn1cc(-c2ccc3cnc(NC(=O)C4CCN(C(C)(C)C)CC4)cc3n2)cn1] | 14 |
| 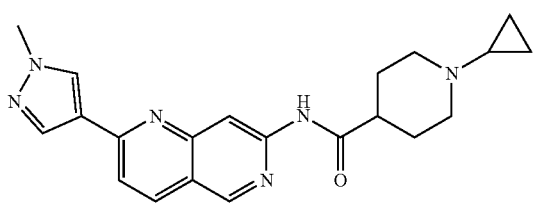 [SMILES: Cn1cc(-c2ccc3cnc(NC(=O)C4CCN(C5CC5)CC4)cc3n2)cn1] | 15 |
| 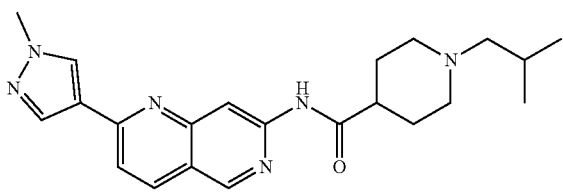 [SMILES: CC(C)CN1CCC(C(=O)Nc2cc3nc(-c4cnn(C)c4)ccc3cn2)CC1] | 16 |
| 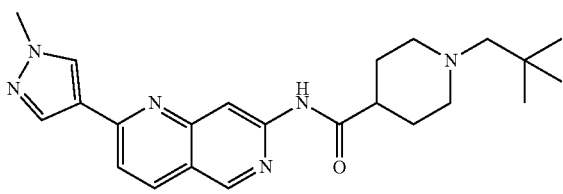 [SMILES: Cn1cc(-c2ccc3cnc(NC(=O)C4CCN(CC(C)(C)C)CC4)cc3n2)cn1] | 17 |
| 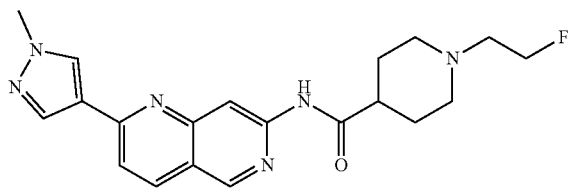 [SMILES: Cn1cc(-c2ccc3cnc(NC(=O)C4CCN(CCF)CC4)cc3n2)cn1] | 18 |
| 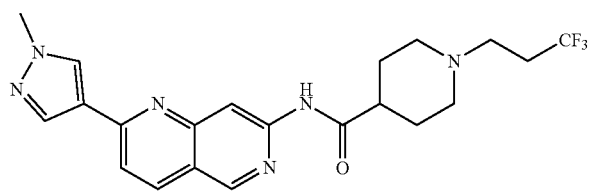 [SMILES: Cn1cc(-c2ccc3cnc(NC(=O)C4CCN(CCC(F)(F)F)CC4)cc3n2)cn1] | 19 |

TABLE 1-continued

TABLE 1-continued
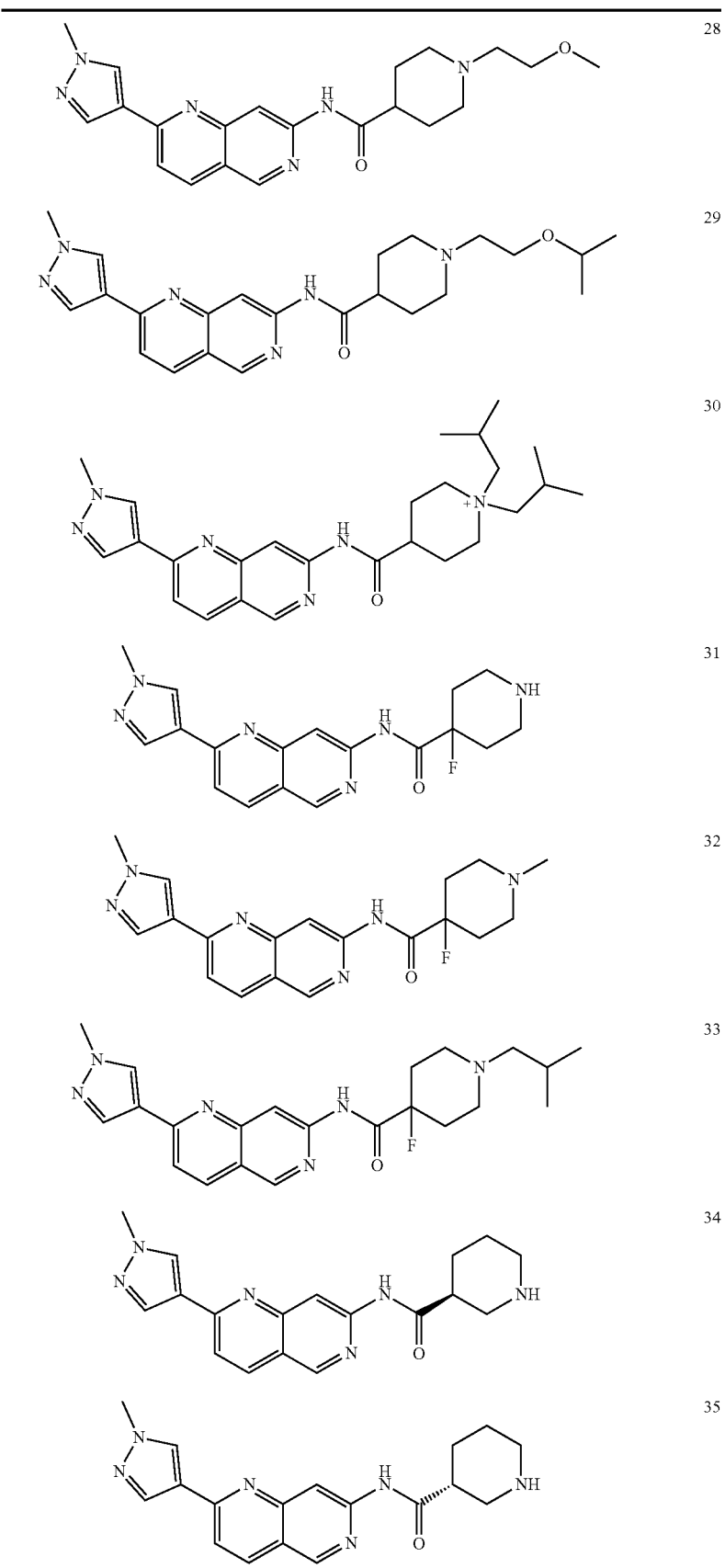

TABLE 1-continued
| | |
|---|---|
| 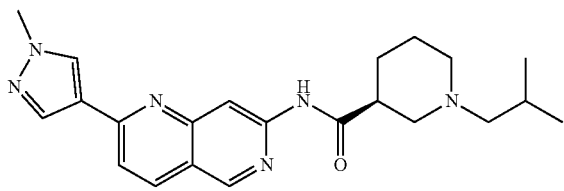 [SMILES: CC(C)CN1CCC[C@H](C(=O)Nc2cc3nc(-c4cnn(C)c4)ccc3cn2)C1] | 36 |
| 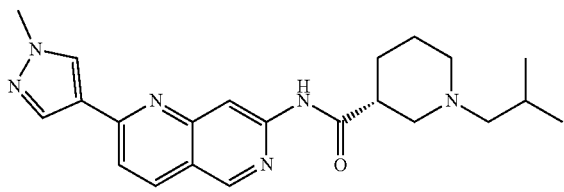 [SMILES: CC(C)CN1CCC[C@@H](C(=O)Nc2cc3nc(-c4cnn(C)c4)ccc3cn2)C1] | 37 |
| 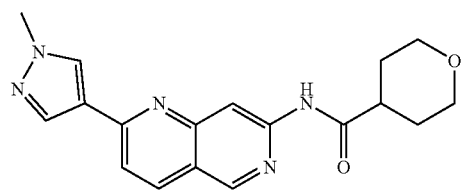 [SMILES: Cn1cc(-c2ccc3cnc(NC(=O)C4CCOCC4)cc3n2)cn1] | 38 |
| 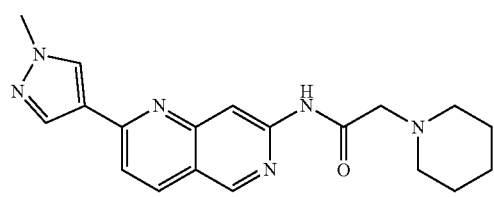 [SMILES: Cn1cc(-c2ccc3cnc(NC(=O)CN4CCCCC4)cc3n2)cn1] | 39 |
| 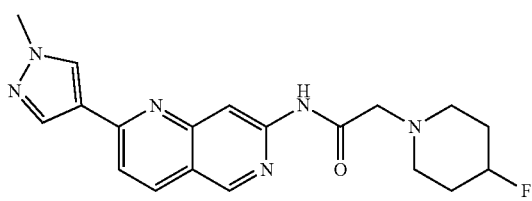 [SMILES: Cn1cc(-c2ccc3cnc(NC(=O)CN4CCC(F)CC4)cc3n2)cn1] | 40 |
| 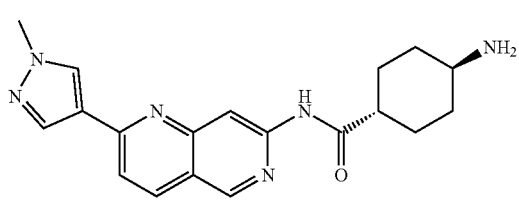 [SMILES: Cn1cc(-c2ccc3cnc(NC(=O)[C@H]4CC[C@H](N)CC4)cc3n2)cn1] | 41 |
| 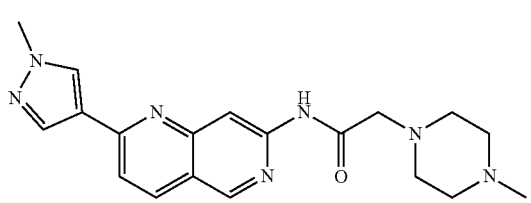 [SMILES: CN1CCN(CC(=O)Nc2cc3nc(-c4cnn(C)c4)ccc3cn2)CC1] | 42 |
| 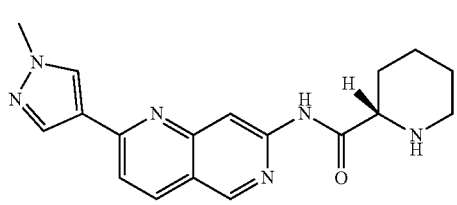 [SMILES: Cn1cc(-c2ccc3cnc(NC(=O)[C@@H]4CCCCN4)cc3n2)cn1] | 43 |

TABLE 1-continued
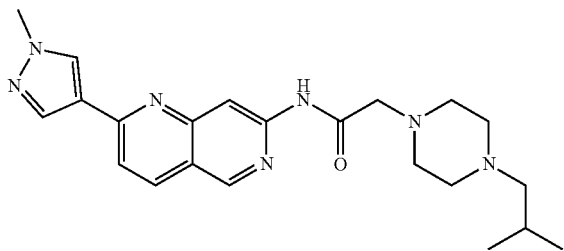 [SMILES: CC(C)CN1CCN(CC(=O)Nc2cc3nc(-c4cnn(C)c4)ccc3cn2)CC1]
44
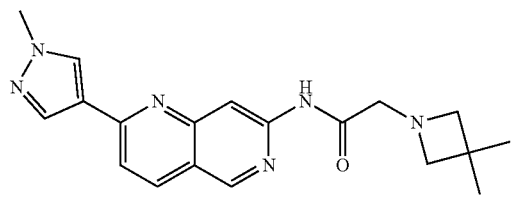 [SMILES: Cn1cc(-c2ccc3cnc(NC(=O)CN4CC(C)(C)C4)cc3n2)cn1]
45
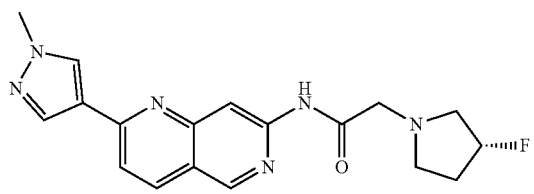 [SMILES: Cn1cc(-c2ccc3cnc(NC(=O)CN4CC[C@@H](F)C4)cc3n2)cn1]
46
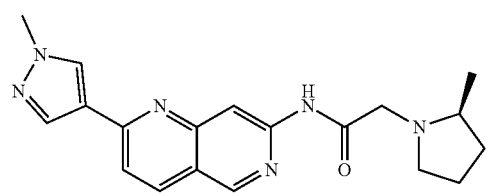 [SMILES: C[C@H]1CCCN1CC(=O)Nc1cc2nc(-c3cnn(C)c3)ccc2cn1]
47
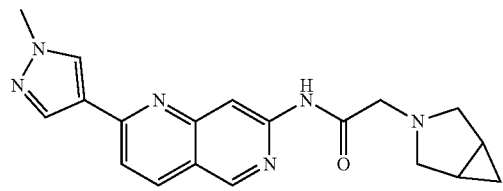 [SMILES: Cn1cc(-c2ccc3cnc(NC(=O)CN4CC5CC5C4)cc3n2)cn1]
48
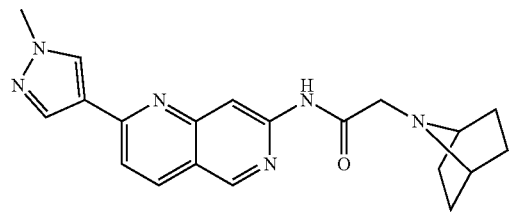 [SMILES: Cn1cc(-c2ccc3cnc(NC(=O)CN4C5CCC4CC5)cc3n2)cn1]
49
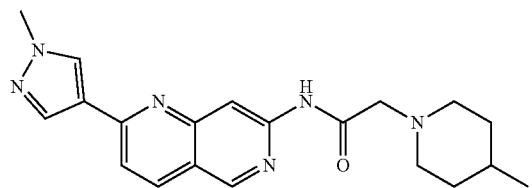 [SMILES: CC1CCN(CC(=O)Nc2cc3nc(-c4cnn(C)c4)ccc3cn2)CC1]
50

TABLE 1-continued
| | |
|---|---|
| 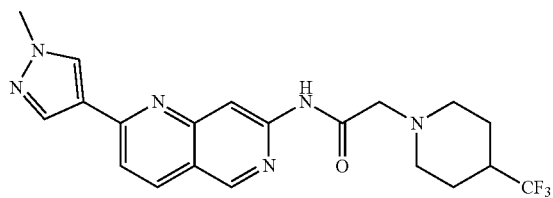 | 51 |
| 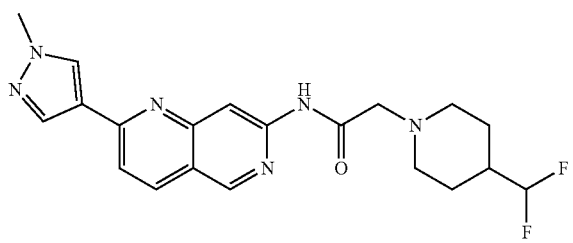 [SMILES: Cn1cc(-c2ccc3cnc(NC(=O)CN4CCC(C(F)F)CC4)cc3n2)cn1] | 52 |
| 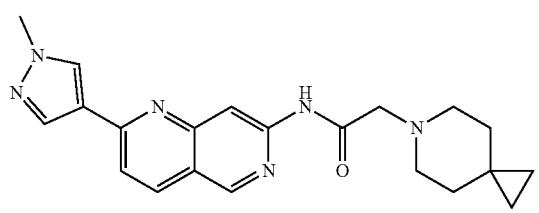 [SMILES: Cn1cc(-c2ccc3cnc(NC(=O)CN4CCC5(CC4)CC5)cc3n2)cn1] | 53 |
| 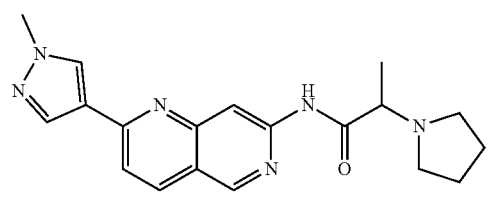 [SMILES: CC(C(=O)Nc1cc2nc(-c3cnn(C)c3)ccc2cn1)N1CCCC1] | 54 |
| 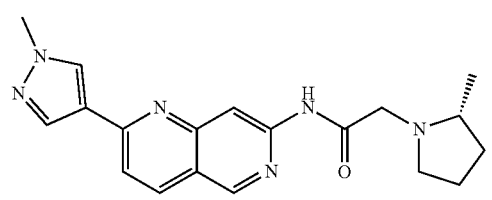 [SMILES: C[C@@H]1CCCN1CC(=O)Nc1cc2nc(-c3cnn(C)c3)ccc2cn1] | 55 |
| 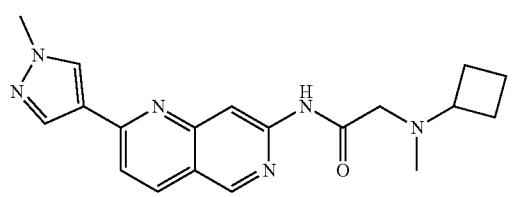 [SMILES: CN(CC(=O)Nc1cc2nc(-c3cnn(C)c3)ccc2cn1)C1CCC1] | 56 |
| 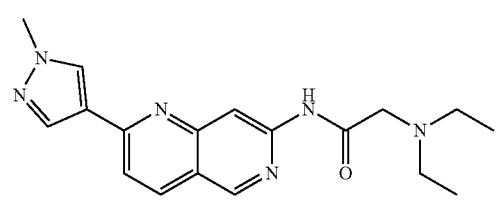 [SMILES: CCN(CC)CC(=O)Nc1cc2nc(-c3cnn(C)c3)ccc2cn1] | 57 |
| 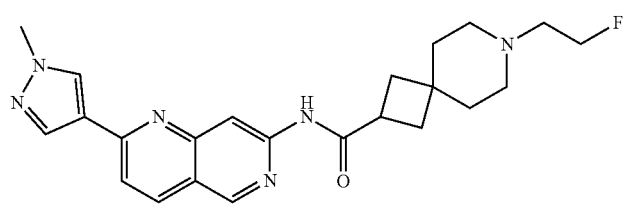 [SMILES: Cn1cc(-c2ccc3cnc(NC(=O)C4CC5(CCN(CCF)CC5)C4)cc3n2)cn1] | 58 |

TABLE 1-continued
| | |
|---|---|
| 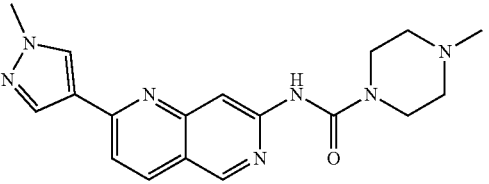 | 59 |
| 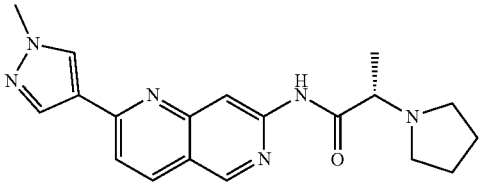 [SMILES: C[C@@H](C(=O)Nc1cc2nc(-c3cnn(C)c3)ccc2cn1)N1CCCC1] | 60 |
| 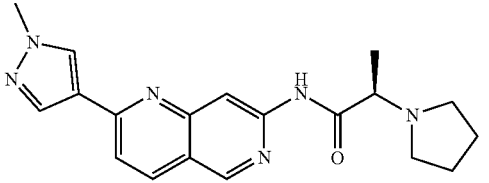 [SMILES: C[C@H](C(=O)Nc1cc2nc(-c3cnn(C)c3)ccc2cn1)N1CCCC1] | 61 |
| 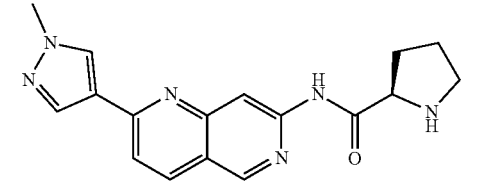 [SMILES: Cn1cc(-c2ccc3cnc(NC(=O)[C@H]4CCCN4)cc3n2)cn1] | 62 |
| 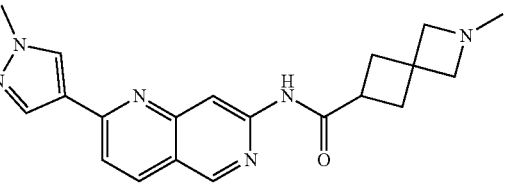 | 63 |
| 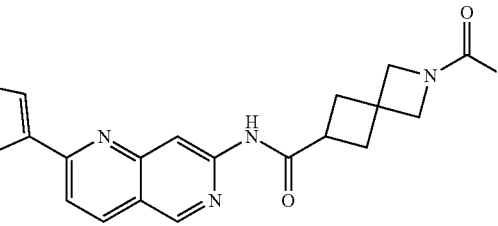 | 64 |
| 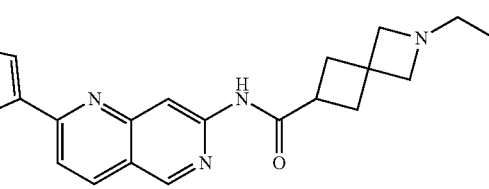 | 65 |
| 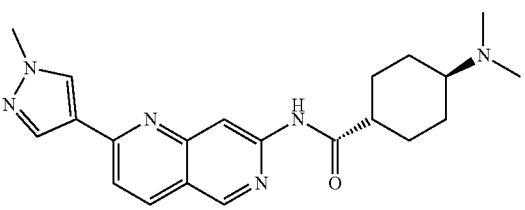 | 66 |

TABLE 1-continued
| | |
|---|---|
| 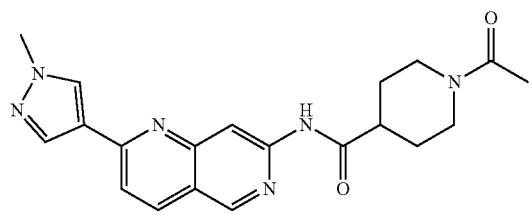 [SMILES: CC(=O)N1CCC(C(=O)Nc2cc3nc(-c4cnn(C)c4)ccc3cn2)CC1] | 67 |
| 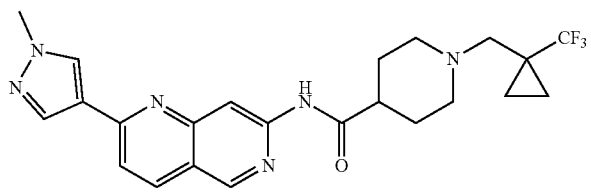 [SMILES: Cn1cc(-c2ccc3cnc(NC(=O)C4CCN(CC5(C(F)(F)F)CC5)CC4)cc3n2)cn1] | 68 |
| 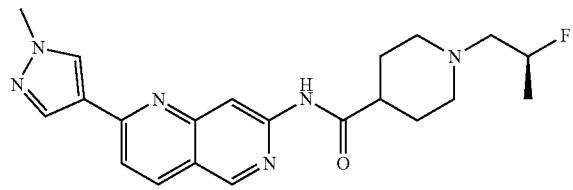 [SMILES: C[C@H](F)CN1CCC(C(=O)Nc2cc3nc(-c4cnn(C)c4)ccc3cn2)CC1] | 69 |
| 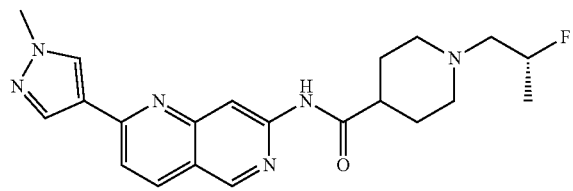 | 70 |
| 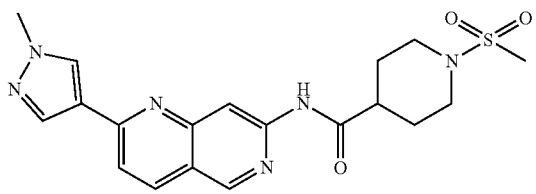 [SMILES: Cn1cc(-c2ccc3cnc(NC(=O)C4CCN(S(C)(=O)=O)CC4)cc3n2)cn1] | 71 |
| 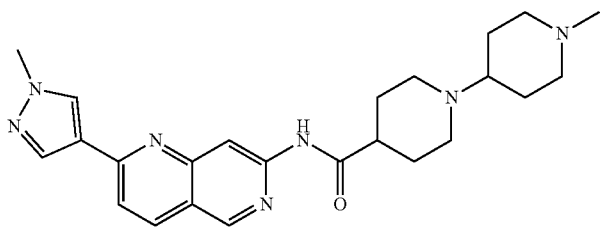 [SMILES: CN1CCC(N2CCC(C(=O)Nc3cc4nc(-c5cnn(C)c5)ccc4cn3)CC2)CC1] | 72 |
| 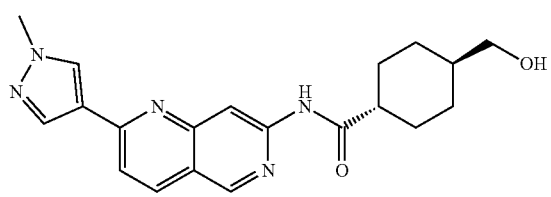 [SMILES: Cn1cc(-c2ccc3cnc(NC(=O)[C@H]4CC[C@H](CO)CC4)cc3n2)cn1] | 73 |
| 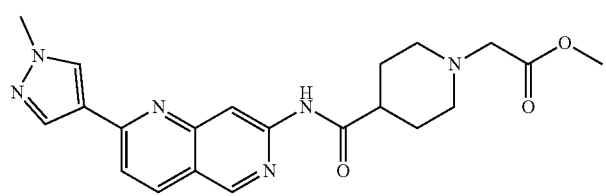 [SMILES: COC(=O)CN1CCC(C(=O)Nc2cc3nc(-c4cnn(C)c4)ccc3cn2)CC1] | 74 |

TABLE 1-continued
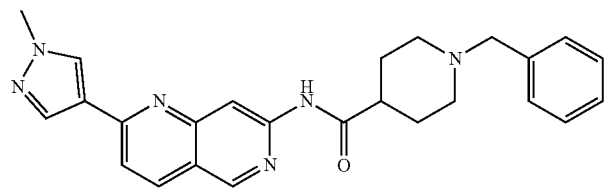 [SMILES: Cn1cc(-c2ccc3cnc(NC(=O)C4CCN(Cc5ccccc5)CC4)cc3n2)cn1] 75
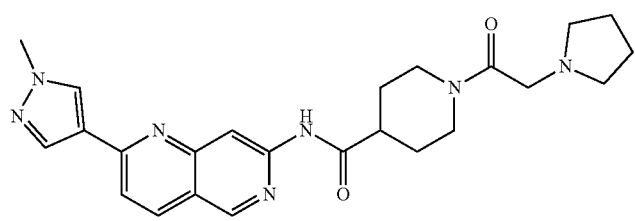 [SMILES: Cn1cc(-c2ccc3cnc(NC(=O)C4CCN(C(=O)CN5CCCC5)CC4)cc3n2)cn1] 76
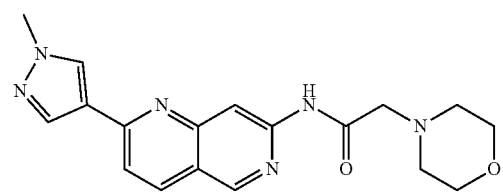 [SMILES: Cn1cc(-c2ccc3cnc(NC(=O)CN4CCOCC4)cc3n2)cn1] 77
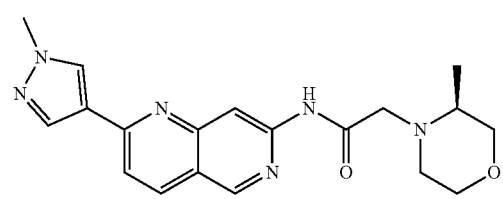 [SMILES: C[C@H]1COCCN1CC(=O)Nc1cc2nc(-c3cnn(C)c3)ccc2cn1] 78
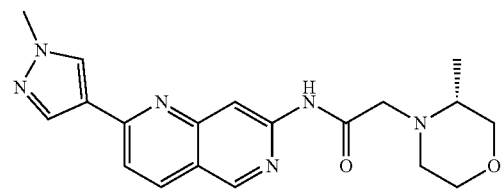 [SMILES: C[C@@H]1COCCN1CC(=O)Nc1cc2nc(-c3cnn(C)c3)ccc2cn1] 79
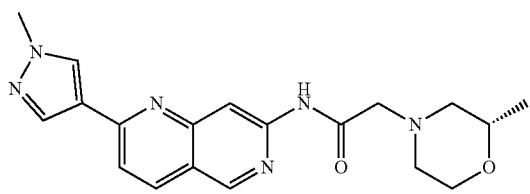 [SMILES: C[C@H]1CN(CC(=O)Nc2cc3nc(-c4cnn(C)c4)ccc3cn2)CCO1] 80
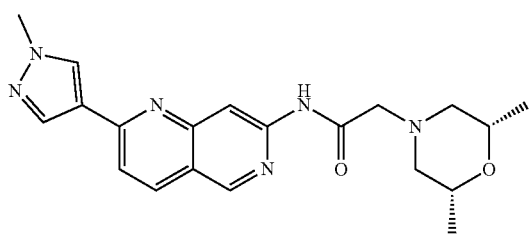 [SMILES: C[C@@H]1CN(CC(=O)Nc2cc3nc(-c4cnn(C)c4)ccc3cn2)C[C@H](C)O1] 81

TABLE 1-continued
| | |
|---|---|
| 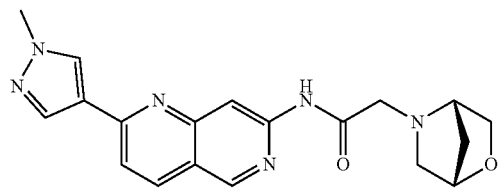 [SMILES: Cn1cc(-c2ccc3cnc(NC(=O)CN4C[C@@H]5C[C@H]4CO5)cc3n2)cn1] | 82 |
| 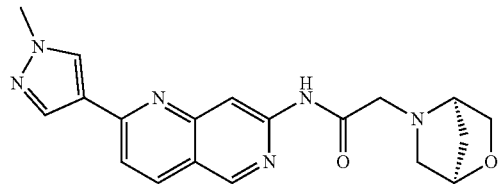 [SMILES: Cn1cc(-c2ccc3cnc(NC(=O)CN4C[C@H]5C[C@@H]4CO5)cc3n2)cn1] | 83 |
| 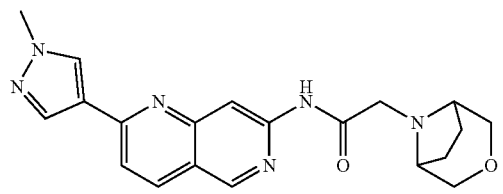 [SMILES: Cn1cc(-c2ccc3cnc(NC(=O)CN4C5CCC4COC5)cc3n2)cn1] | 84 |
| 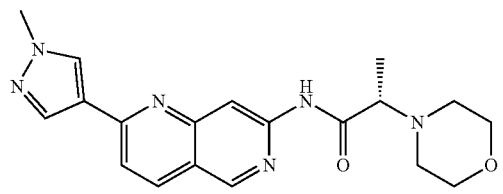 | 85 |
| 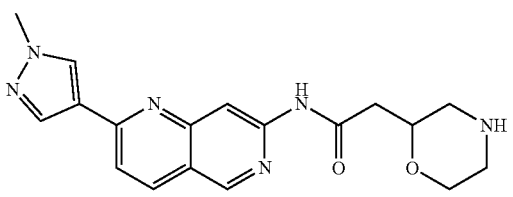 [SMILES: Cn1cc(-c2ccc3cnc(NC(=O)CC4CNCCO4)cc3n2)cn1] | 86 |
| 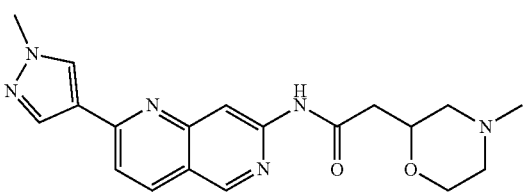 [SMILES: CN1CCOC(CC(=O)Nc2cc3nc(-c4cnn(C)c4)ccc3cn2)C1] | 87 |
| 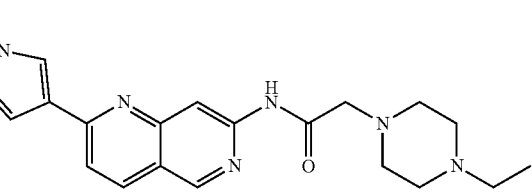 | 88 |
| 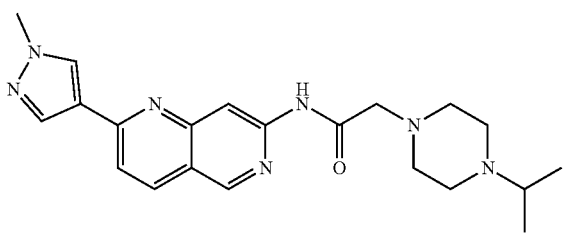 [SMILES: CC(C)N1CCN(CC(=O)Nc2cc3nc(-c4cnn(C)c4)ccc3cn2)CC1] | 89 |

TABLE 1-continued
| | |
|---|---|
| 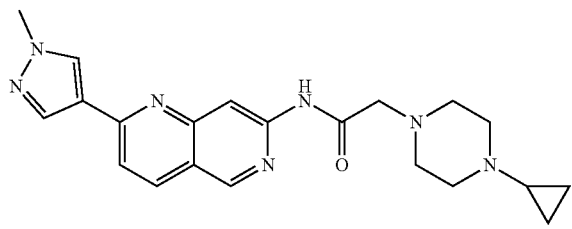 [SMILES: Cn1cc(-c2ccc3cnc(NC(=O)CN4CCN(C5CC5)CC4)cc3n2)cn1] | 90 |
| 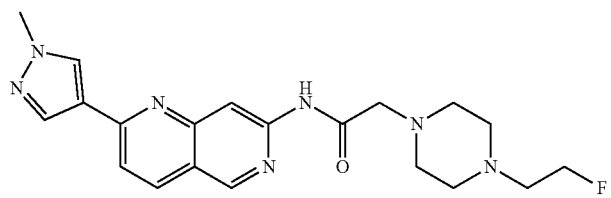 [SMILES: Cn1cc(-c2ccc3cnc(NC(=O)CN4CCN(CCF)CC4)cc3n2)cn1] | 91 |
| 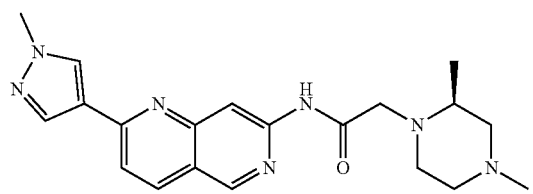 [SMILES: C[C@H]1CN(C)CCN1CC(=O)Nc1cc2nc(-c3cnn(C)c3)ccc2cn1] | 92 |
| 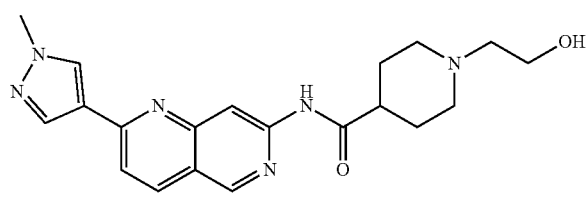 [SMILES: Cn1cc(-c2ccc3cnc(NC(=O)C4CCN(CCO)CC4)cc3n2)cn1] | 93 |
| 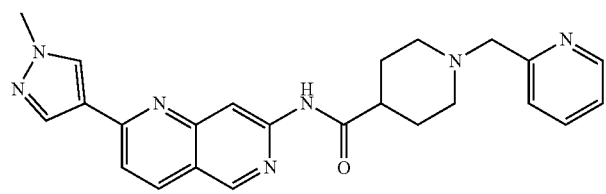 | 94 |
| 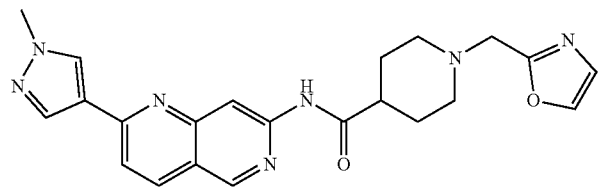 | 95 |
| 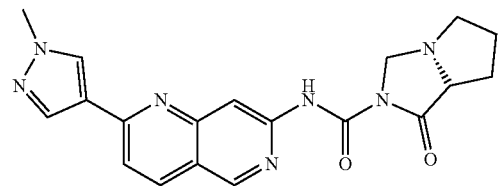 | 96 |
| 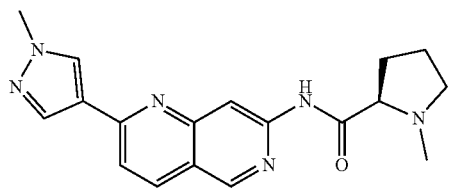 [SMILES: CN1CCC[C@@H]1C(=O)Nc1cc2nc(-c3cnn(C)c3)ccc2cn1] | 97 |

TABLE 1-continued
| | |
|---|---|
| 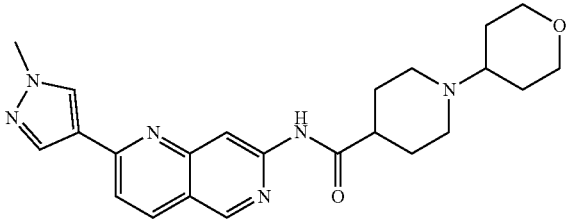 [SMILES: Cn1cc(-c2ccc3cnc(NC(=O)C4CCN(C5CCOCC5)CC4)cc3n2)cn1] | 98 |
|  | 99 |
| 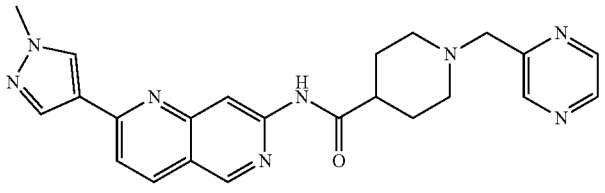 [SMILES: Cn1cc(-c2ccc3cnc(NC(=O)C4CCN(Cc5cnccn5)CC4)cc3n2)cn1] | 100 |
|  | 101 |
|  | 102 |
| 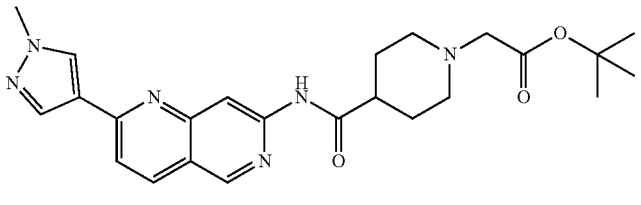 [SMILES: Cn1cc(-c2ccc3cnc(NC(=O)C4CCN(CC(=O)OC(C)(C)C)CC4)cc3n2)cn1] | 103 |
|  | 104 |
|  | 105 |

TABLE 1-continued
| | |
|---|---|
| 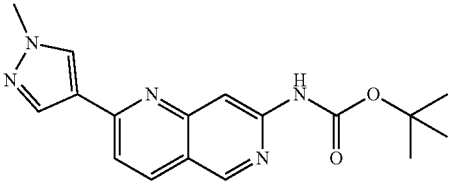 [SMILES: Cn1cc(-c2ccc3cnc(NC(=O)OC(C)(C)C)cc3n2)cn1] | 106 |
| 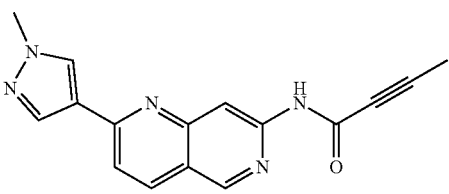 [SMILES: CC#CC(=O)Nc1cc2nc(-c3cnn(C)c3)ccc2cn1] | 107 |
| 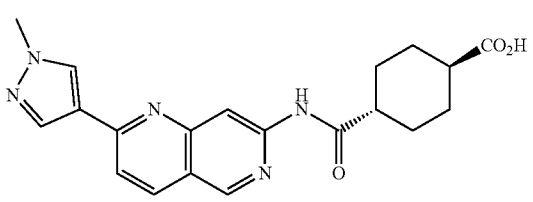 [SMILES: Cn1cc(-c2ccc3cnc(NC(=O)[C@H]4CC[C@H](C(=O)O)CC4)cc3n2)cn1] | 108 |
| 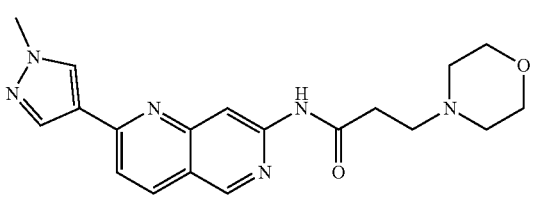 [SMILES: Cn1cc(-c2ccc3cnc(NC(=O)CCN4CCOCC4)cc3n2)cn1] | 109 |
| 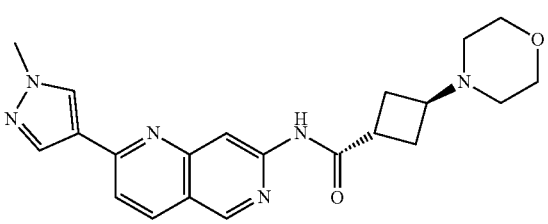 | 110 |
| 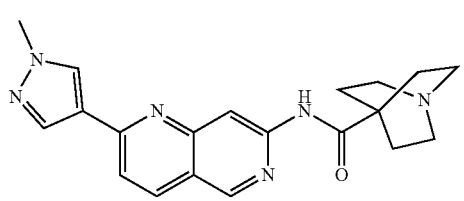 [SMILES: Cn1cc(-c2ccc3cnc(NC(=O)C45CCN(CC4)CC5)cc3n2)cn1] | 111 |
| 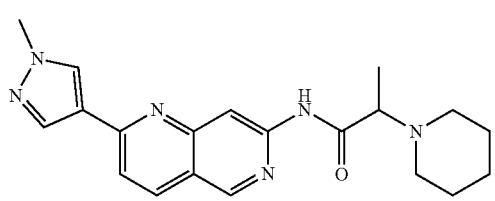 [SMILES: CC(C(=O)Nc1cc2nc(-c3cnn(C)c3)ccc2cn1)N1CCCCC1] | 112 |
| 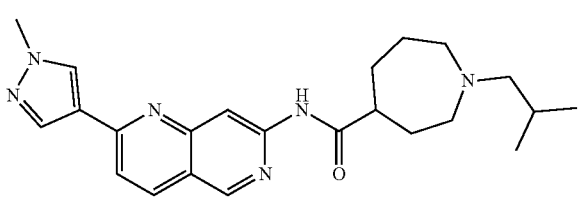 [SMILES: CC(C)CN1CCCC(C(=O)Nc2cc3nc(-c4cnn(C)c4)ccc3cn2)CC1] | 113 |

TABLE 1-continued
| | |
|---|---|
| 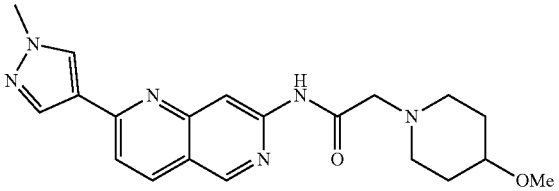 [SMILES: COC1CCN(CC(=O)Nc2cc3nc(-c4cnn(C)c4)ccc3cn2)CC1] | 114 |
| 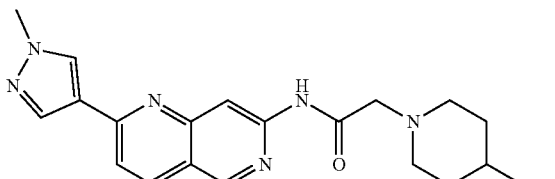 | 115 |
| 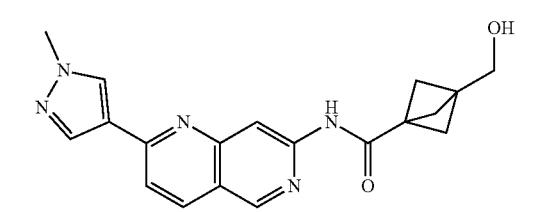 [SMILES: Cn1cc(-c2ccc3cnc(NC(=O)C45CC(CO)(C4)C5)cc3n2)cn1] | 116 |
| 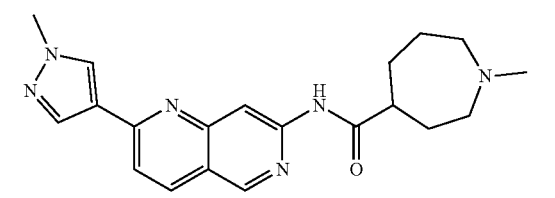 [SMILES: CN1CCCC(C(=O)Nc2cc3nc(-c4cnn(C)c4)ccc3cn2)CC1] | 117 |
| 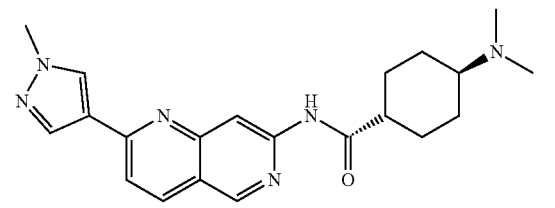 | 118 |
| 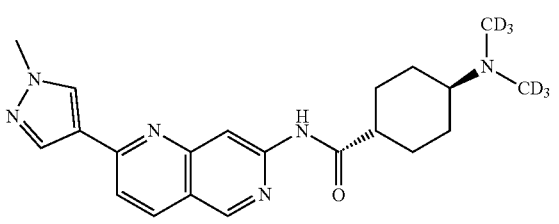 | 119 |
| 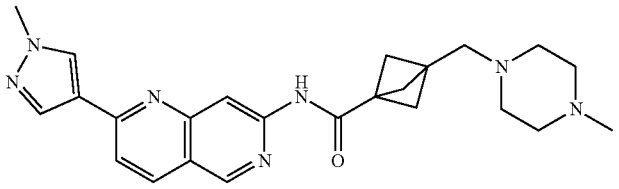 [SMILES: CN1CCN(CC23CC(C(=O)Nc4cc5nc(-c6cnn(C)c6)ccc5cn4)(C2)C3)CC1] | 120 |
| 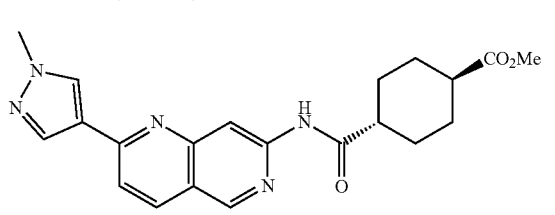 [SMILES: COC(=O)[C@H]1CC[C@H](C(=O)Nc2cc3nc(-c4cnn(C)c4)ccc3cn2)CC1] | 121 |

TABLE 1-continued
| | |
|---|---|
| 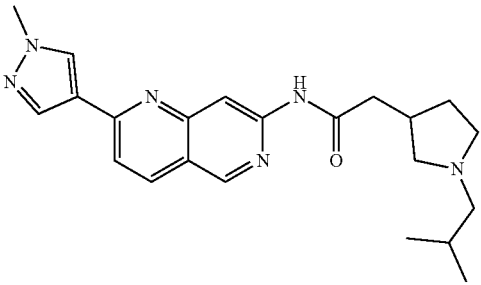 [SMILES: CC(C)CN1CCC(CC(=O)Nc2cc3nc(-c4cnn(C)c4)ccc3cn2)C1] | 122 |
| 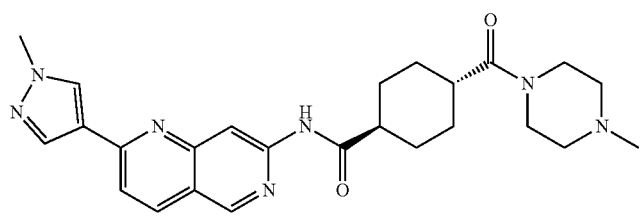 [SMILES: CN1CCN(C(=O)[C@H]2CC[C@H](C(=O)Nc3cc4nc(-c5cnn(C)c5)ccc4cn3)CC2)CC1] | 123 |
| 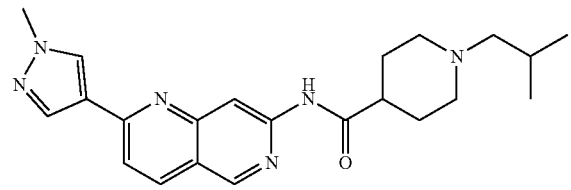 [SMILES: CC(C)CN1CCC(C(=O)Nc2cc3nc(-c4cnn(C)c4)ccc3cn2)CC1] | 124 |
| 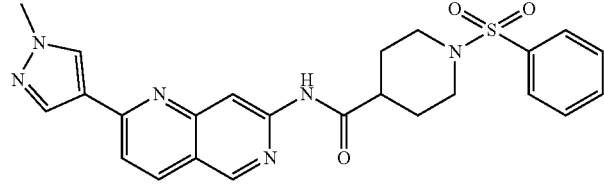 [SMILES: Cn1cc(-c2ccc3cnc(NC(=O)C4CCN(S(=O)(=O)c5ccccc5)CC4)cc3n2)cn1] | 125 |
| 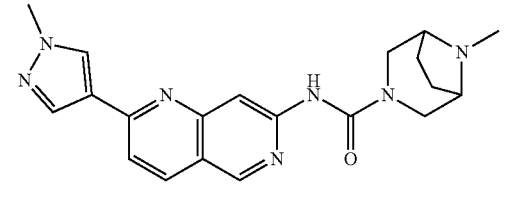 [SMILES: CN1C2CCC1CN(C(=O)Nc1cc3nc(-c4cnn(C)c4)ccc3cn1)C2] | 126 |
| 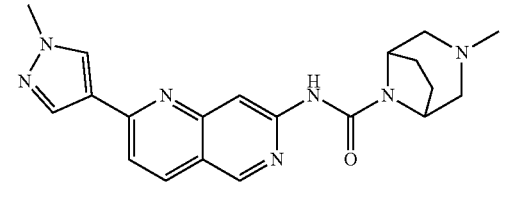 [SMILES: CN1CC2CCC(C1)N2C(=O)Nc1cc2nc(-c3cnn(C)c3)ccc2cn1] | 127 |
| 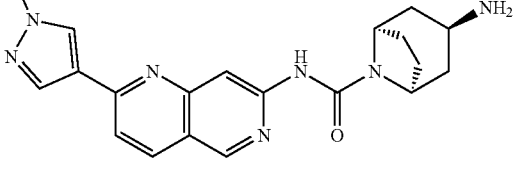 | 128 |

TABLE 1-continued
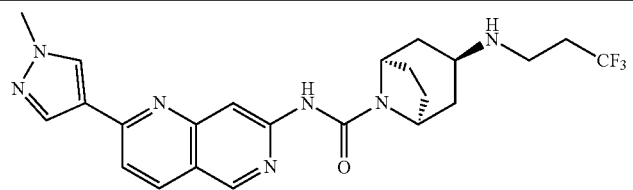 129
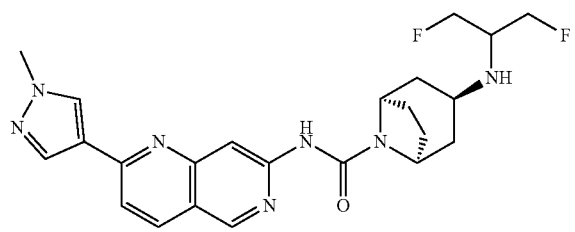 [SMILES: Cn1cc(-c2ccc3cnc(NC(=O)N4[C@@H]5CC[C@H]4C[C@H](NC(CF)CF)C5)cc3n2)cn1] 130
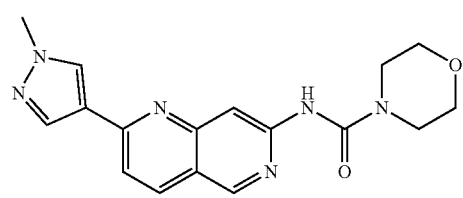 [SMILES: Cn1cc(-c2ccc3cnc(NC(=O)N4CCOCC4)cc3n2)cn1] 131
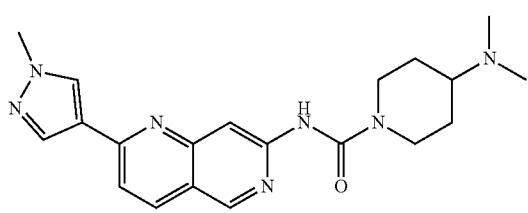 132
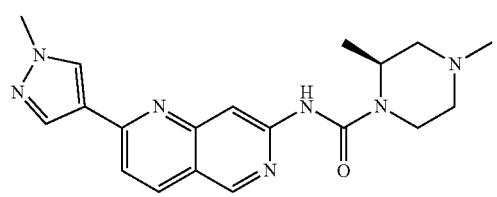 [SMILES: C[C@H]1CN(C)CCN1C(=O)Nc1cc2nc(-c3cnn(C)c3)ccc2cn1] 133
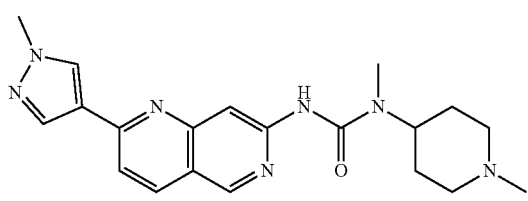 [SMILES: CN1CCC(N(C)C(=O)Nc2cc3nc(-c4cnn(C)c4)ccc3cn2)CC1] 134
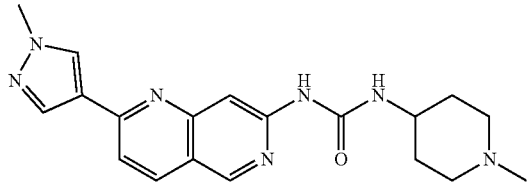 [SMILES: CN1CCC(NC(=O)Nc2cc3nc(-c4cnn(C)c4)ccc3cn2)CC1] 135
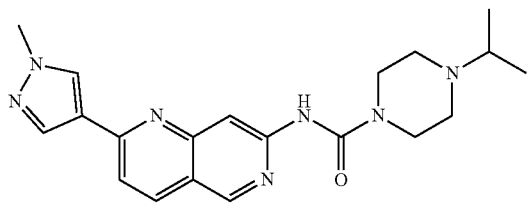 136

TABLE 1-continued
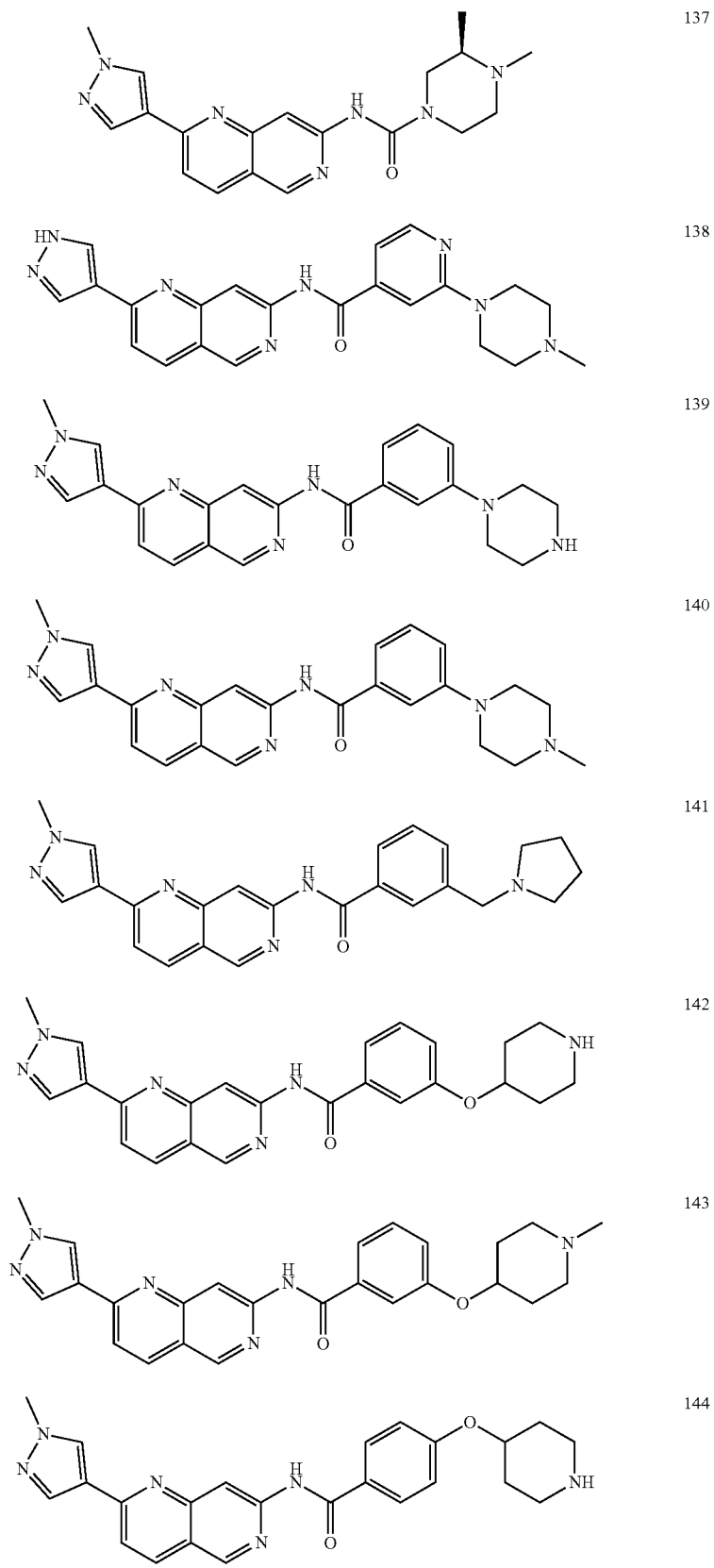
137
138
139
140
141
142
143
144

TABLE 1-continued
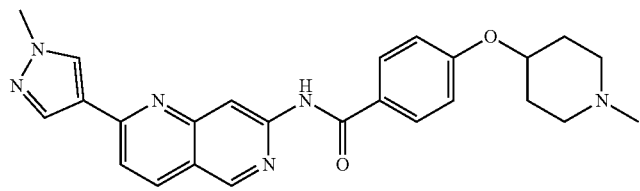 [SMILES: CN1CCC(Oc2ccc(C(=O)Nc3cc4nc(-c5cnn(C)c5)ccc4cn3)cc2)CC1] 145
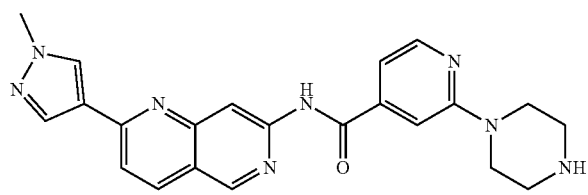 [SMILES: Cn1cc(-c2ccc3cnc(NC(=O)c4ccnc(N5CCNCC5)c4)cc3n2)cn1] 146
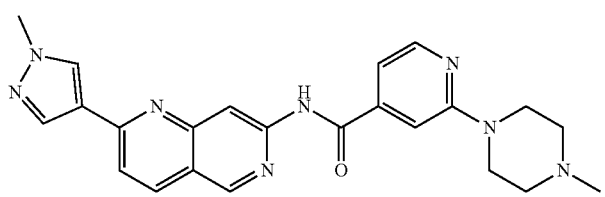 147
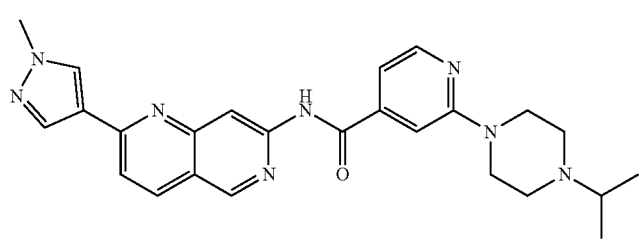 [SMILES: CC(C)N1CCN(c2cc(C(=O)Nc3cc4nc(-c5cnn(C)c5)ccc4cn3)ccn2)CC1] 148
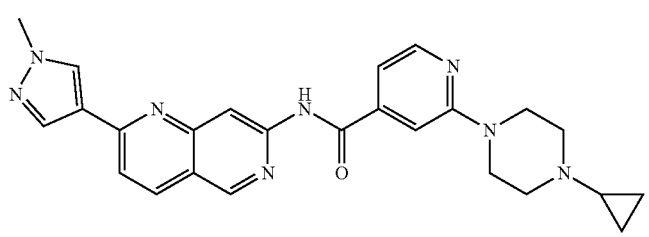 [SMILES: Cn1cc(-c2ccc3cnc(NC(=O)c4ccnc(N5CCN(C6CC6)CC5)c4)cc3n2)cn1] 149
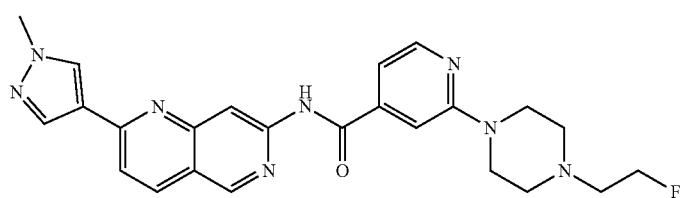 [SMILES: Cn1cc(-c2ccc3cnc(NC(=O)c4ccnc(N5CCN(CCF)CC5)c4)cc3n2)cn1] 150
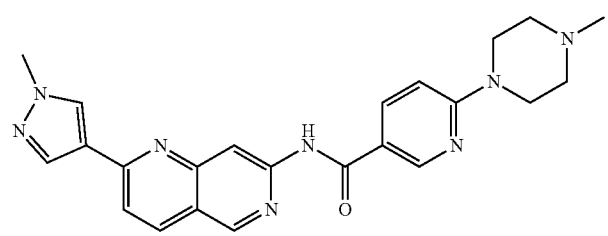 [SMILES: CN1CCN(c2ccc(C(=O)Nc3cc4nc(-c5cnn(C)c5)ccc4cn3)cn2)CC1] 151

TABLE 1-continued
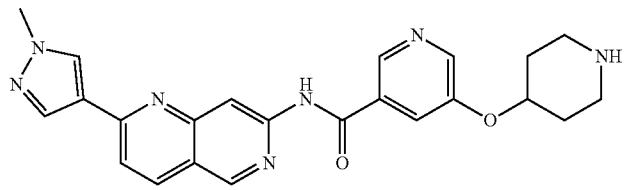 [SMILES: Cn1cc(-c2ccc3cnc(NC(=O)c4cncc(OC5CCNCC5)c4)cc3n2)cn1] 152
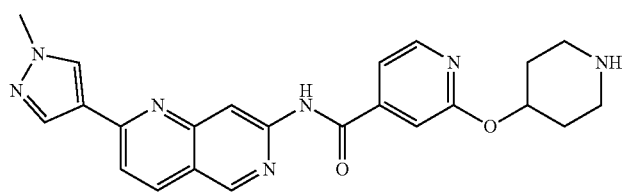 [SMILES: Cn1cc(-c2ccc3cnc(NC(=O)c4ccnc(OC5CCNCC5)c4)cc3n2)cn1] 153
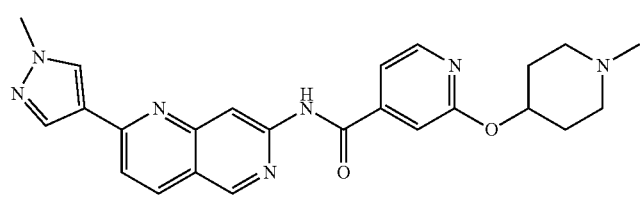 [SMILES: CN1CCC(Oc2cc(C(=O)Nc3cc4nc(-c5cnn(C)c5)ccc4cn3)ccn2)CC1] 154
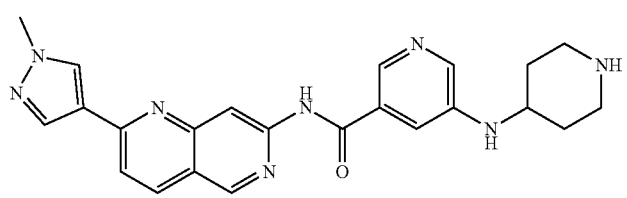 [SMILES: Cn1cc(-c2ccc3cnc(NC(=O)c4cncc(NC5CCNCC5)c4)cc3n2)cn1] 155
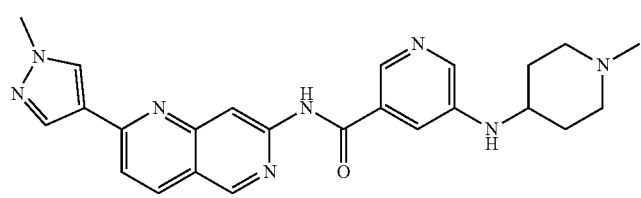 [SMILES: CN1CCC(Nc2cncc(C(=O)Nc3cc4nc(-c5cnn(C)c5)ccc4cn3)c2)CC1] 156
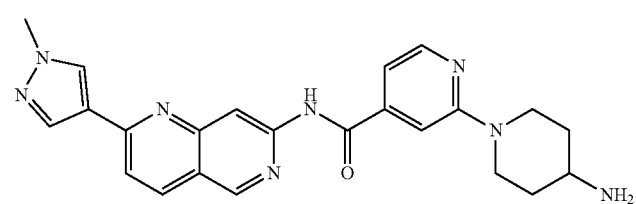 157
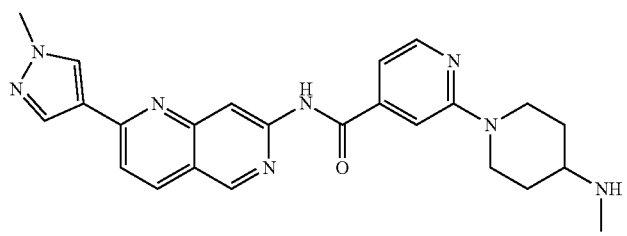 [SMILES: CNC1CCN(c2cc(C(=O)Nc3cc4nc(-c5cnn(C)c5)ccc4cn3)ccn2)CC1] 158

TABLE 1-continued
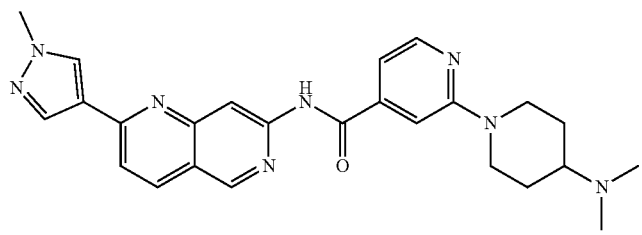 [SMILES: CN(C)C1CCN(c2cc(C(=O)Nc3cc4nc(-c5cnn(C)c5)ccc4cn3)ccn2)CC1]
159
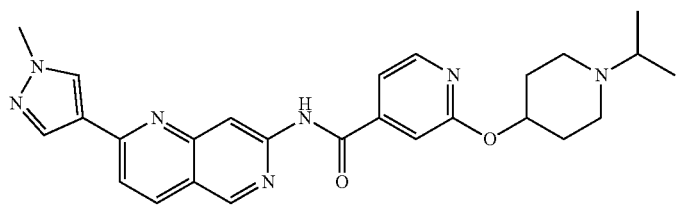 [SMILES: CC(C)N1CCC(Oc2cc(C(=O)Nc3cc4nc(-c5cnn(C)c5)ccc4cn3)ccn2)CC1]
160
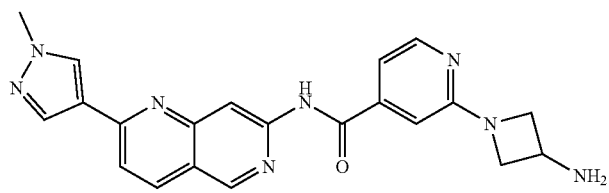 [SMILES: Cn1cc(-c2ccc3cnc(NC(=O)c4ccnc(N5CC(N)C5)c4)cc3n2)cn1]
161
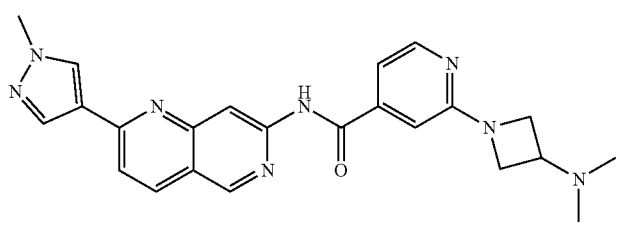 [SMILES: CN(C)C1CN(c2cc(C(=O)Nc3cc4nc(-c5cnn(C)c5)ccc4cn3)ccn2)C1]
162
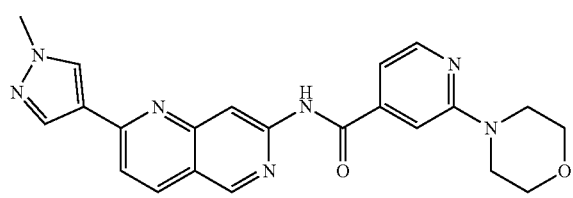 [SMILES: Cn1cc(-c2ccc3cnc(NC(=O)c4ccnc(N5CCOCC5)c4)cc3n2)cn1]
163
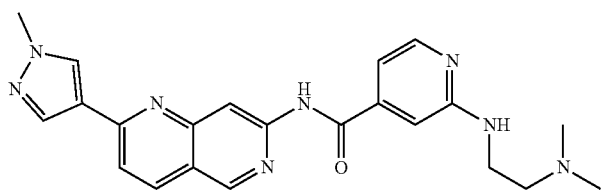 [SMILES: CN(C)CCNc1cc(C(=O)Nc2cc3nc(-c4cnn(C)c4)ccc3cn2)ccn1]
164
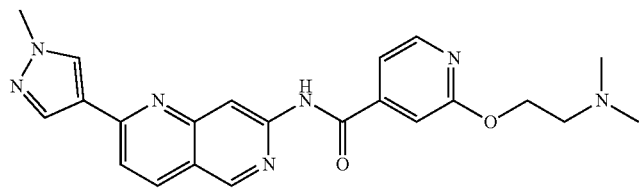 [SMILES: CN(C)CCOc1cc(C(=O)Nc2cc3nc(-c4cnn(C)c4)ccc3cn2)ccn1]
165

TABLE 1-continued
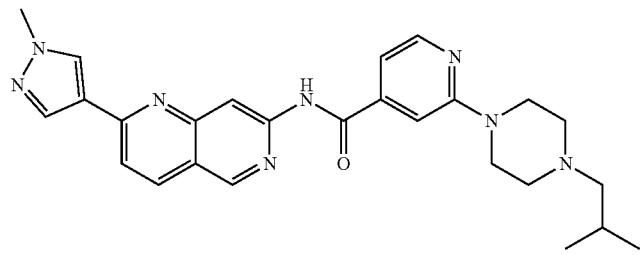 [SMILES: CC(C)CN1CCN(c2cc(C(=O)Nc3cc4nc(-c5cnn(C)c5)ccc4cn3)ccn2)CC1] 166
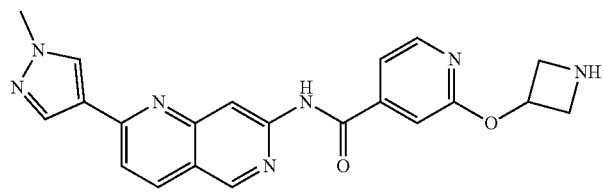 [SMILES: Cn1cc(-c2ccc3cnc(NC(=O)c4ccnc(OC5CNC5)c4)cc3n2)cn1] 167
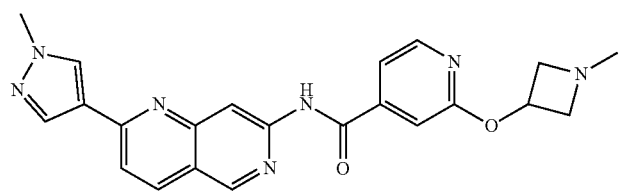 [SMILES: CN1CC(Oc2cc(C(=O)Nc3cc4nc(-c5cnn(C)c5)ccc4cn3)ccn2)C1] 168
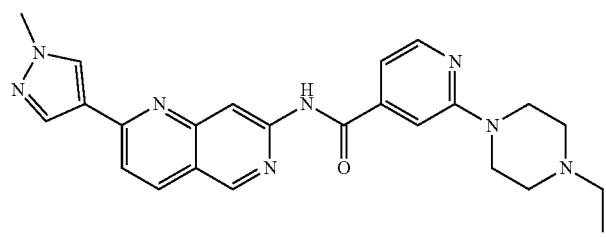 [SMILES: CCN1CCN(c2cc(C(=O)Nc3cc4nc(-c5cnn(C)c5)ccc4cn3)ccn2)CC1] 169
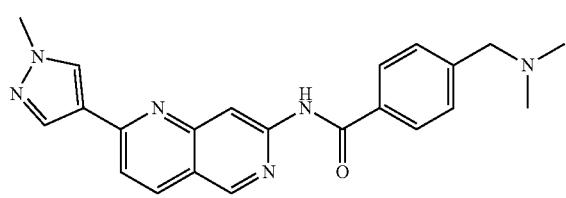 [SMILES: CN(C)Cc1ccc(C(=O)Nc2cc3nc(-c4cnn(C)c4)ccc3cn2)cc1] 170
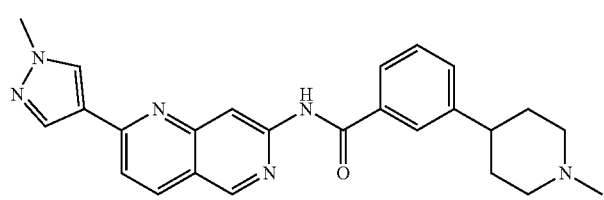 171
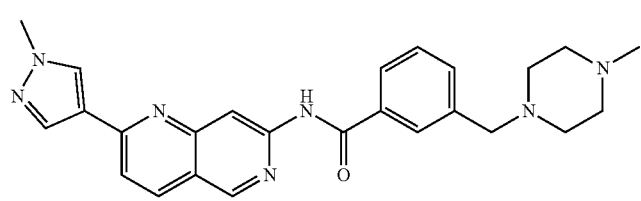 [SMILES: CN1CCN(Cc2cccc(C(=O)Nc3cc4nc(-c5cnn(C)c5)ccc4cn3)c2)CC1] 172

TABLE 1-continued
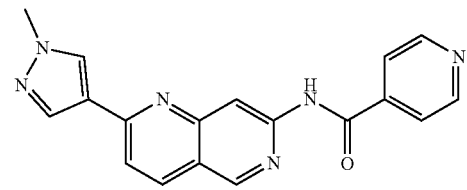 [SMILES: Cn1cc(-c2ccc3cnc(NC(=O)c4ccncc4)cc3n2)cn1]
173
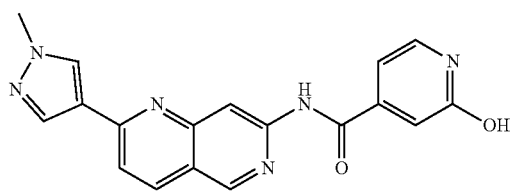 [SMILES: Cn1cc(-c2ccc3cnc(NC(=O)c4ccnc(O)c4)cc3n2)cn1]
174
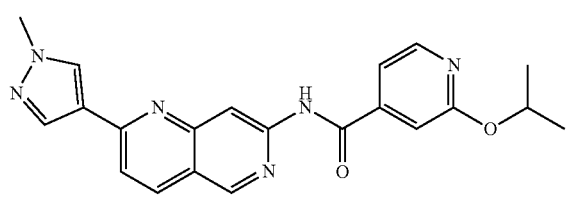 [SMILES: CC(C)Oc1cc(C(=O)Nc2cc3nc(-c4cnn(C)c4)ccc3cn2)ccn1]
175
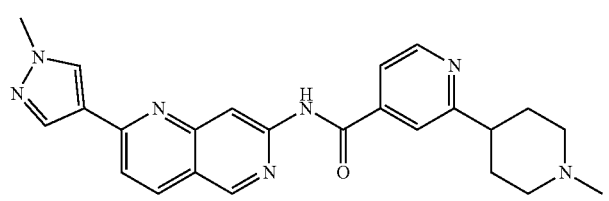
176
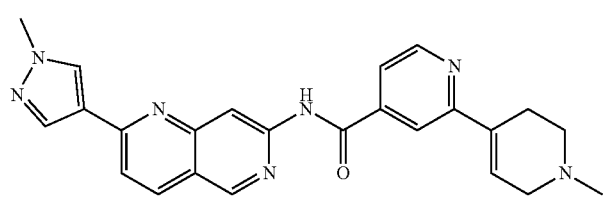 [SMILES: CN1CCC(c2cc(C(=O)Nc3cc4nc(-c5cnn(C)c5)ccc4cn3)ccn2)CC1]
177
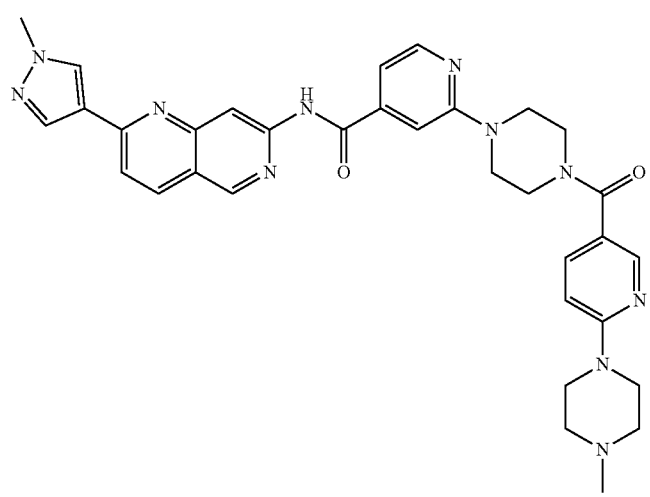 [SMILES: CN1CCN(c2ccc(C(=O)N3CCN(c4cc(C(=O)Nc5cc6nc(-c7cnn(C)c7)ccc6cn5)ccn4)CC3)cn2)CC1]
178

TABLE 1-continued
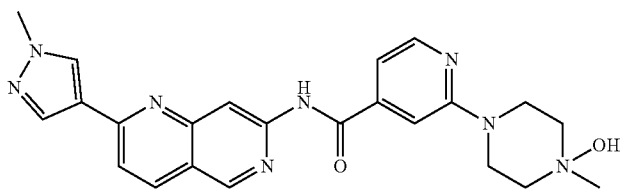 179
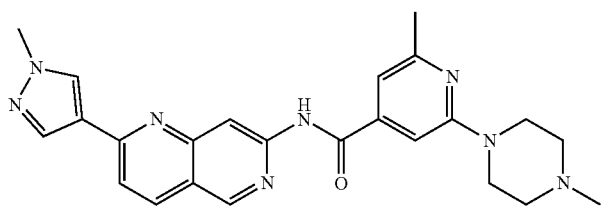 [SMILES: Cc1cc(C(=O)Nc2cc3nc(-c4cnn(C)c4)ccc3cn2)cc(N2CCN(C)CC2)n1] 180
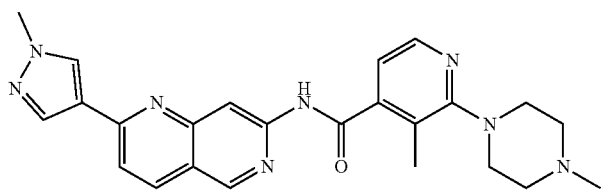 181
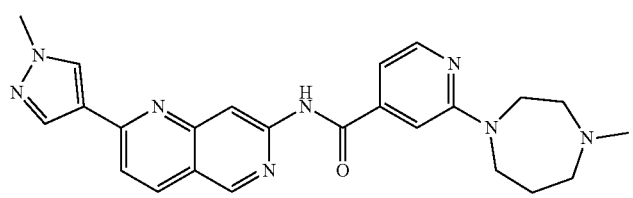 [SMILES: CN1CCCN(c2cc(C(=O)Nc3cc4nc(-c5cnn(C)c5)ccc4cn3)ccn2)CC1] 182
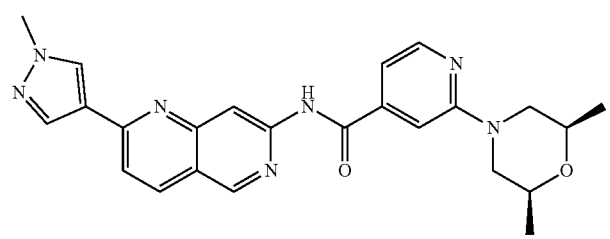 [SMILES: C[C@@H]1CN(c2cc(C(=O)Nc3cc4nc(-c5cnn(C)c5)ccc4cn3)ccn2)C[C@H](C)O1] 183
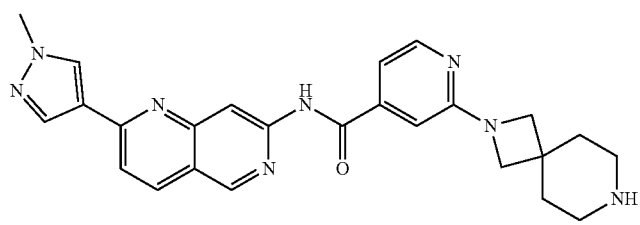 [SMILES: Cn1cc(-c2ccc3cnc(NC(=O)c4ccnc(N5CC6(CCNCC6)C5)c4)cc3n2)cn1] 184
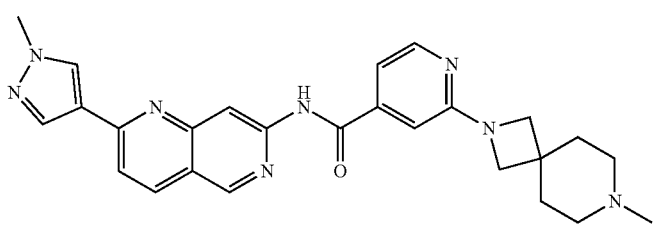 [SMILES: CN1CCC2(CC1)CN(c1cc(C(=O)Nc3cc4nc(-c5cnn(C)c5)ccc4cn3)ccn1)C2] 185

TABLE 1-continued
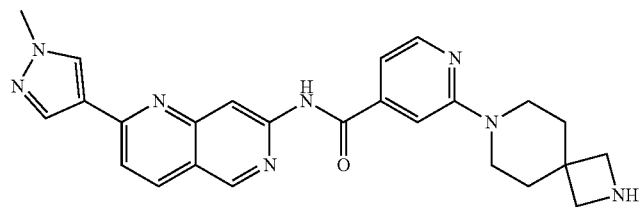 [SMILES: Cn1cc(-c2ccc3cnc(NC(=O)c4ccnc(N5CCC6(CC5)CNC6)c4)cc3n2)cn1] 186
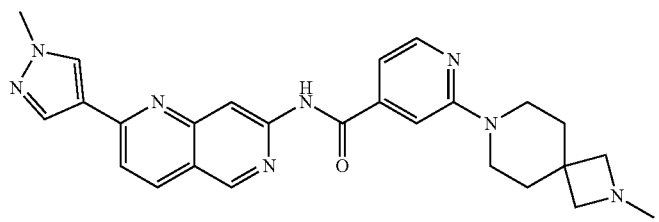 [SMILES: CN1CC2(CCN(c3cc(C(=O)Nc4cc5nc(-c6cnn(C)c6)ccc5cn4)ccn3)CC2)C1] 187
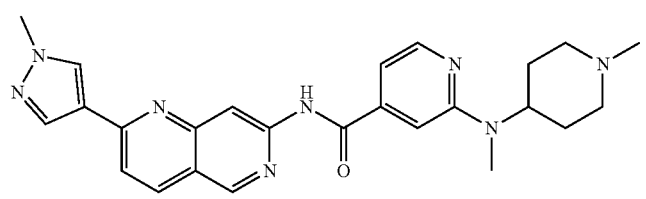 [SMILES: CN1CCC(N(C)c2cc(C(=O)Nc3cc4nc(-c5cnn(C)c5)ccc4cn3)ccn2)CC1] 188
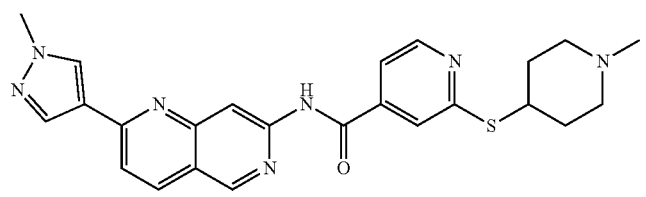 [SMILES: CN1CCC(Sc2cc(C(=O)Nc3cc4nc(-c5cnn(C)c5)ccc4cn3)ccn2)CC1] 189
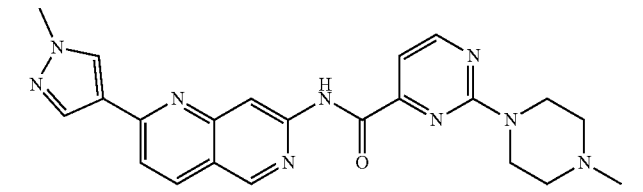 190
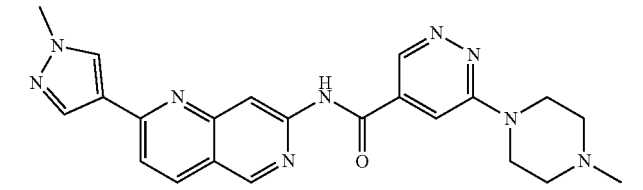 [SMILES: CN1CCN(c2cc(C(=O)Nc3cc4nc(-c5cnn(C)c5)ccc4cn3)cnn2)CC1] 191
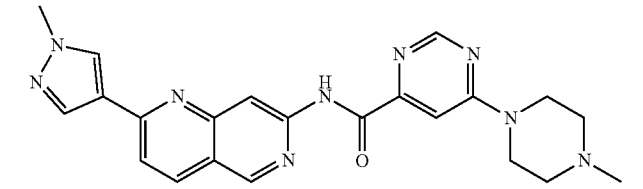 [SMILES: CN1CCN(c2cc(C(=O)Nc3cc4nc(-c5cnn(C)c5)ccc4cn3)ncn2)CC1] 192
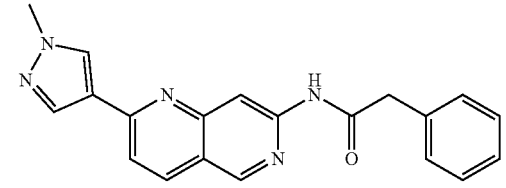 [SMILES: Cn1cc(-c2ccc3cnc(NC(=O)Cc4ccccc4)cc3n2)cn1] 193

TABLE 1-continued
| | |
|---|---|
| 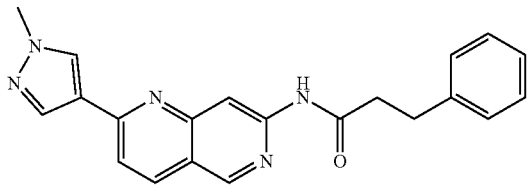 [SMILES: Cn1cc(-c2ccc3cnc(NC(=O)CCc4ccccc4)cc3n2)cn1] | 194 |
| 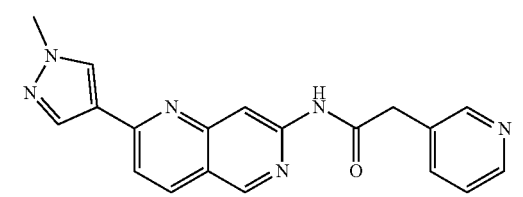 | 195 |
| 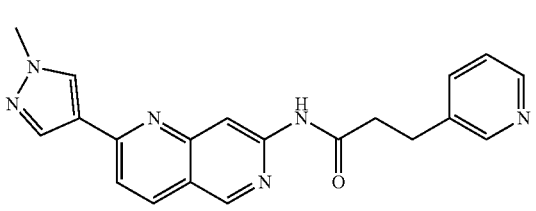 [SMILES: Cn1cc(-c2ccc3cnc(NC(=O)CCc4cccnc4)cc3n2)cn1] | 196 |
| 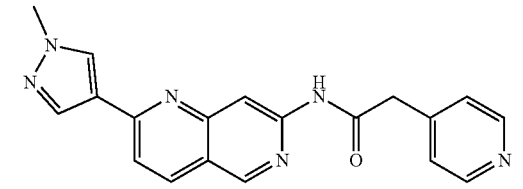 [SMILES: Cn1cc(-c2ccc3cnc(NC(=O)Cc4ccncc4)cc3n2)cn1] | 197 |
| 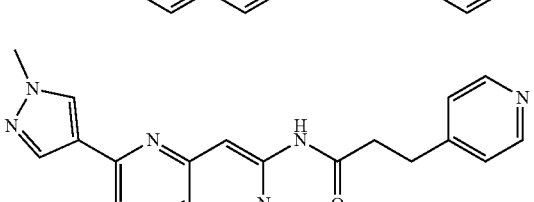 | 198 |
| 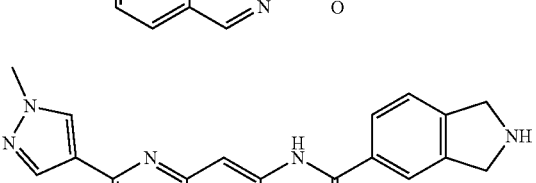 | 199 |
|  | 200 |
| 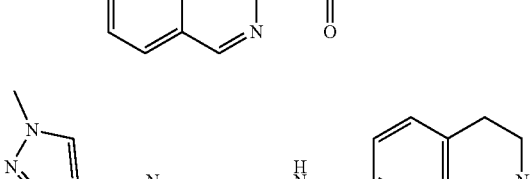 | 201 |

TABLE 1-continued
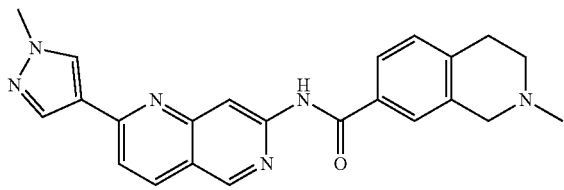 [SMILES: CN1CCc2ccc(C(=O)Nc3cc4nc(-c5cnn(C)c5)ccc4cn3)cc2C1]
202
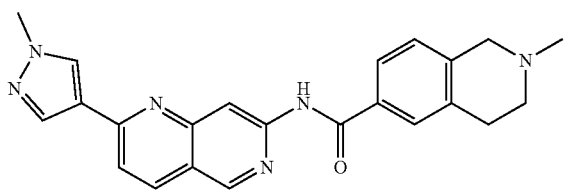 [SMILES: CN1CCc2cc(C(=O)Nc3cc4nc(-c5cnn(C)c5)ccc4cn3)ccc2C1]
203
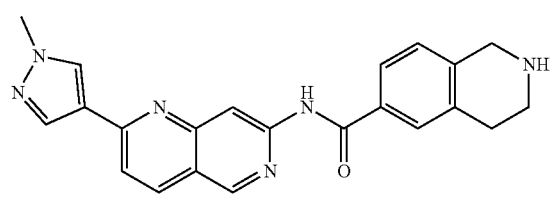 [SMILES: Cn1cc(-c2ccc3cnc(NC(=O)c4ccc5c(c4)CCNC5)cc3n2)cn1]
204
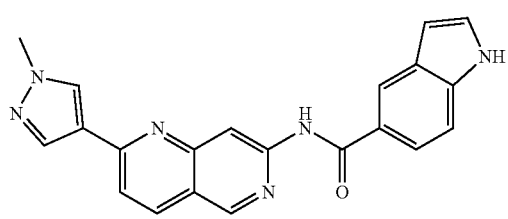
205
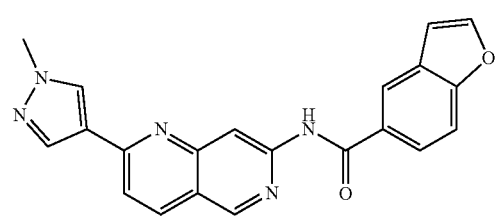 [SMILES: Cn1cc(-c2ccc3cnc(NC(=O)c4ccc5occc5c4)cc3n2)cn1]
206
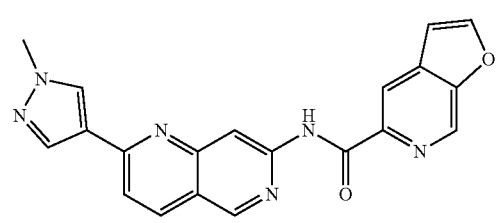 [SMILES: Cn1cc(-c2ccc3cnc(NC(=O)c4cc5ccoc5cn4)cc3n2)cn1]
207
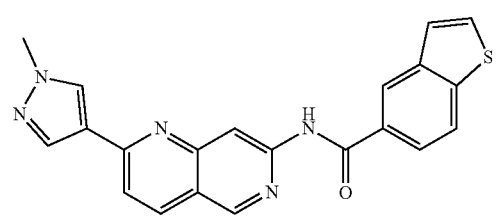 [SMILES: Cn1cc(-c2ccc3cnc(NC(=O)c4ccc5sccc5c4)cc3n2)cn1]
208

TABLE 1-continued
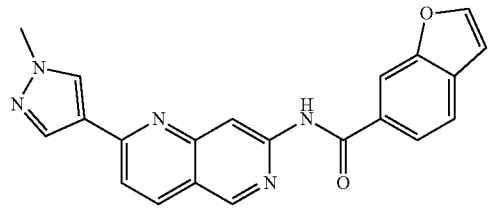 [SMILES: Cn1cc(-c2ccc3cnc(NC(=O)c4ccc5ccoc5c4)cc3n2)cn1]
209
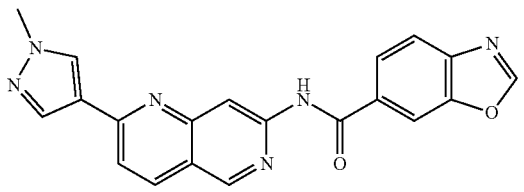 [SMILES: Cn1cc(-c2ccc3cnc(NC(=O)c4ccc5ncsc5c4)cc3n2)cn1]
210
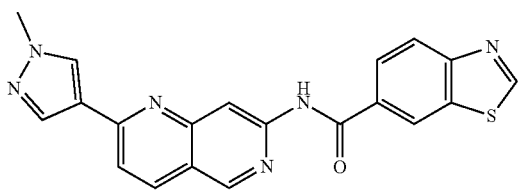
211
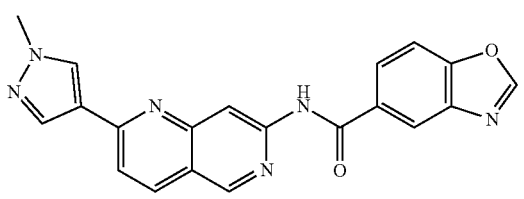 [SMILES: Cn1cc(-c2ccc3cnc(NC(=O)c4ccc5ocnc5c4)cc3n2)cn1]
212
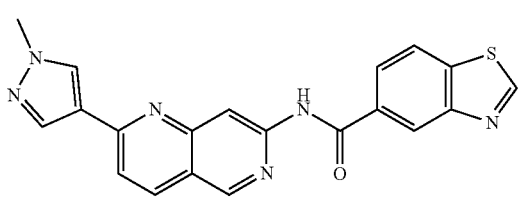 [SMILES: Cn1cc(-c2ccc3cnc(NC(=O)c4ccc5scnc5c4)cc3n2)cn1]
213
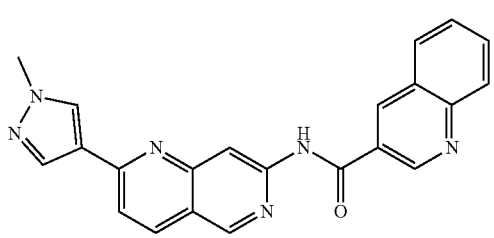
214
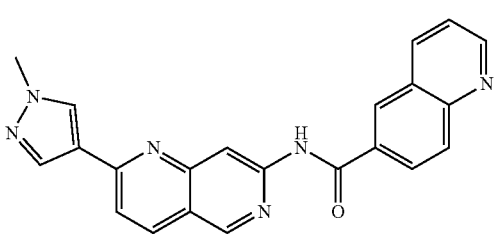 [SMILES: Cn1cc(-c2ccc3cnc(NC(=O)c4ccc5ncccc5c4)cc3n2)cn1]
215

TABLE 1-continued
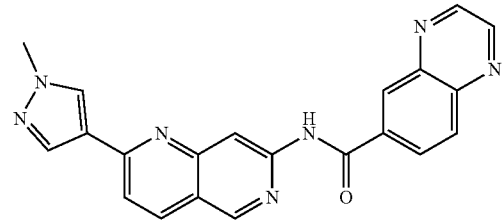 [SMILES: Cn1cc(-c2ccc3cnc(NC(=O)c4ccc5nccnc5c4)cc3n2)cn1]   216
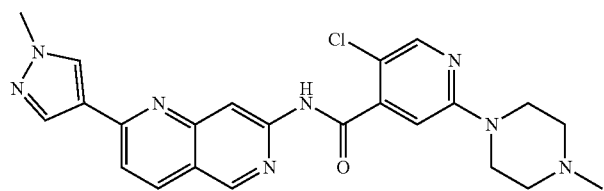   217
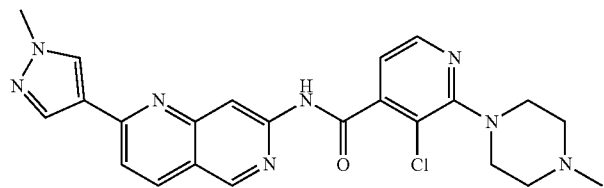   218
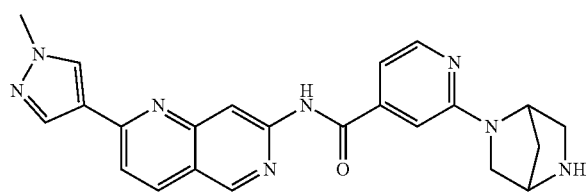 [SMILES: Cn1cc(-c2ccc3cnc(NC(=O)c4ccnc(N5CC6CC5CN6)c4)cc3n2)cn1]   219
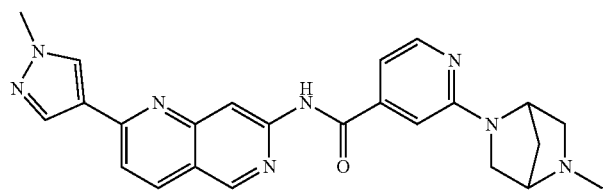 [SMILES: CN1CC2CC1CN2c1cc(C(=O)Nc2cc3nc(-c4cnn(C)c4)ccc3cn2)ccn1]   220
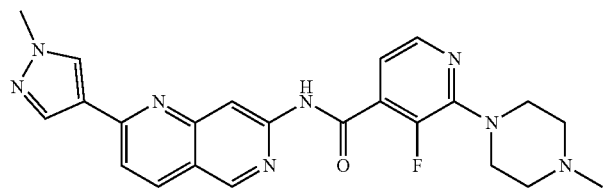 [SMILES: CN1CCN(c2nccc(C(=O)Nc3cc4nc(-c5cnn(C)c5)ccc4cn3)c2F)CC1]   221
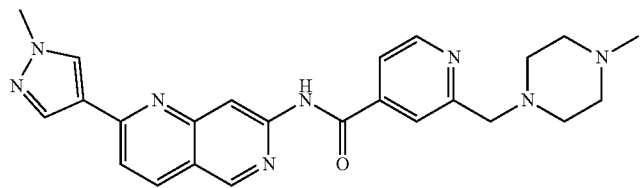   222
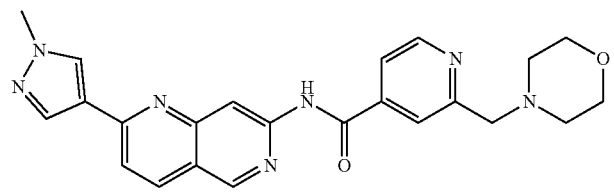 [SMILES: Cn1cc(-c2ccc3cnc(NC(=O)c4ccnc(CN5CCOCC5)c4)cc3n2)cn1]   223

TABLE 1-continued
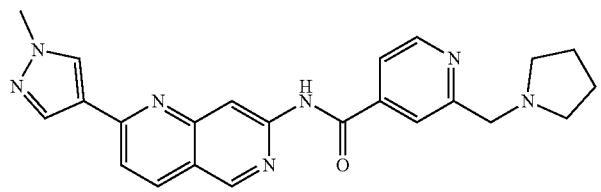 224
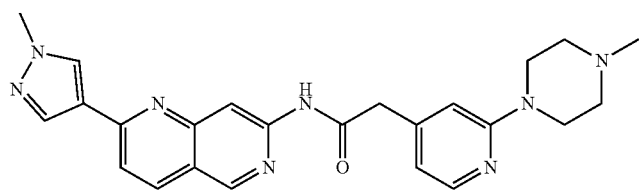 [SMILES: CN1CCN(c2cc(CC(=O)Nc3cc4nc(-c5cnn(C)c5)ccc4cn3)ccn2)CC1] 225
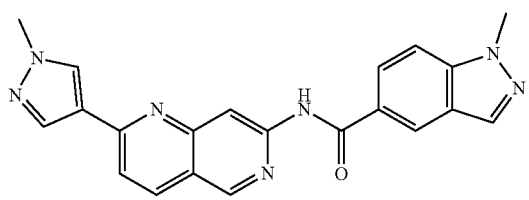 [SMILES: Cn1cc(-c2ccc3cnc(NC(=O)c4ccc5c(cnn5C)c4)cc3n2)cn1] 226
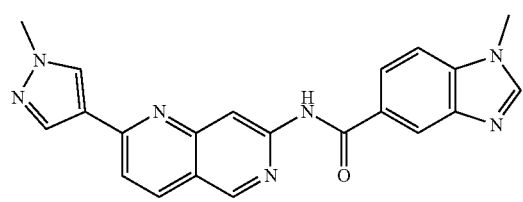 [SMILES: Cn1cc(-c2ccc3cnc(NC(=O)c4ccc5c(c4)ncn5C)cc3n2)cn1] 227
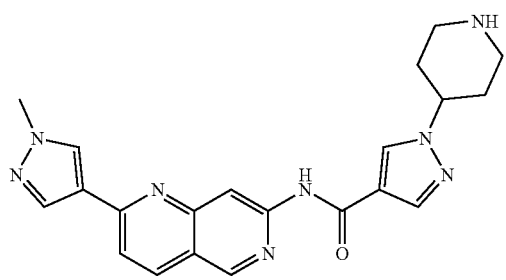 [SMILES: Cn1cc(-c2ccc3cnc(NC(=O)c4cnn(C5CCNCC5)c4)cc3n2)cn1] 228
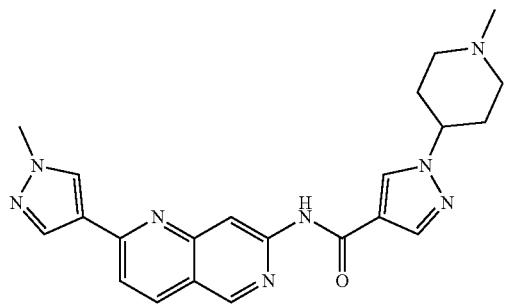 [SMILES: CN1CCC(n2cc(C(=O)Nc3cc4nc(-c5cnn(C)c5)ccc4cn3)cn2)CC1] 229

TABLE 1-continued
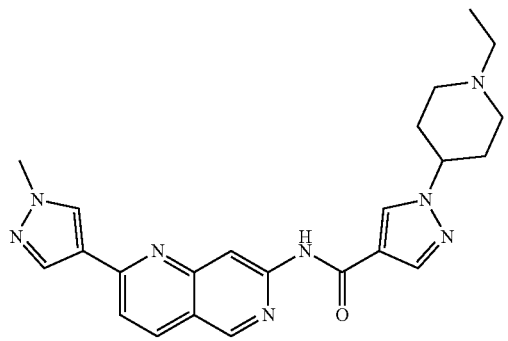 [SMILES: CCN1CCC(n2cc(C(=O)Nc3cc4nc(-c5cnn(C)c5)ccc4cn3)cn2)CC1]
230
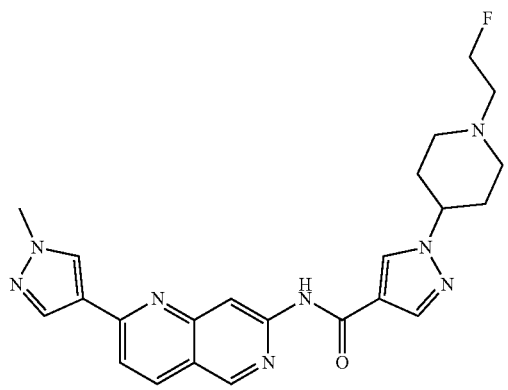 [SMILES: Cn1cc(-c2ccc3cnc(NC(=O)c4cnn(C5CCN(CCF)CC5)c4)cc3n2)cn1]
231
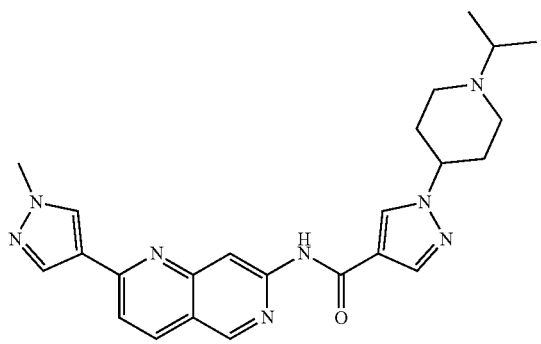 [SMILES: CC(C)N1CCC(n2cc(C(=O)Nc3cc4nc(-c5cnn(C)c5)ccc4cn3)cn2)CC1]
232
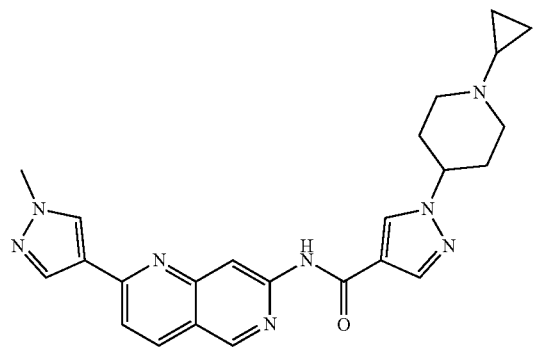 [SMILES: Cn1cc(-c2ccc3cnc(NC(=O)c4cnn(C5CCN(C6CC6)CC5)c4)cc3n2)cn1]
233

TABLE 1-continued
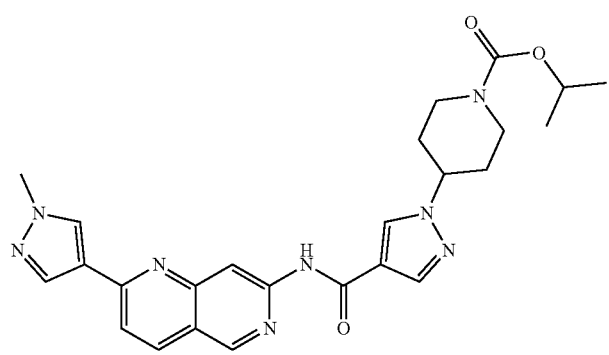 [SMILES: CC(C)OC(=O)N1CCC(n2cc(C(=O)Nc3cc4nc(-c5cnn(C)c5)ccc4cn3)cn2)CC1]
234
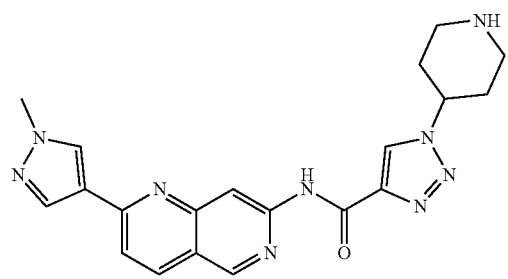 [SMILES: Cn1cc(-c2ccc3cnc(NC(=O)c4cn(C5CCNCC5)nn4)cc3n2)cn1]
235
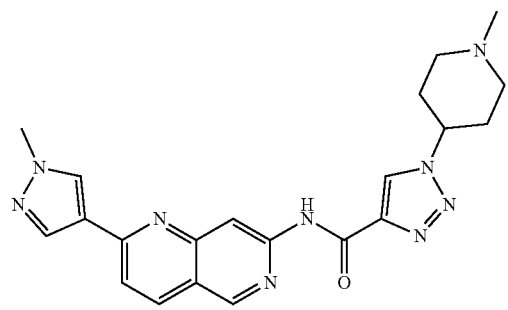 [SMILES: CN1CCC(n2cc(C(=O)Nc3cc4nc(-c5cnn(C)c5)ccc4cn3)nn2)CC1]
236
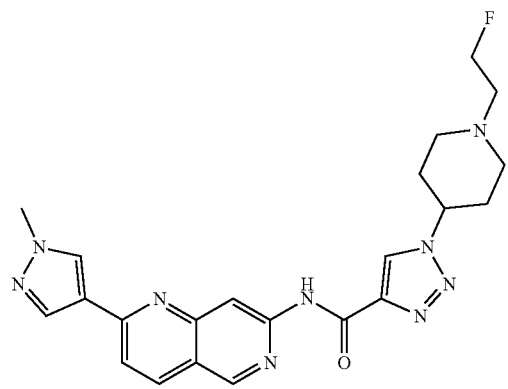 [SMILES: Cn1cc(-c2ccc3cnc(NC(=O)c4cn(C5CCN(CCF)CC5)nn4)cc3n2)cn1]
237

TABLE 1-continued
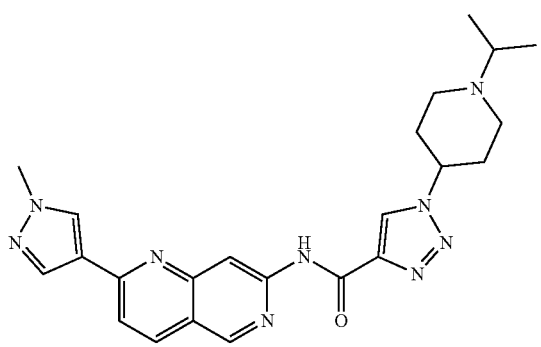 [SMILES: CC(C)N1CCC(n2cc(C(=O)Nc3cc4nc(-c5cnn(C)c5)ccc4cn3)nn2)CC1]
238
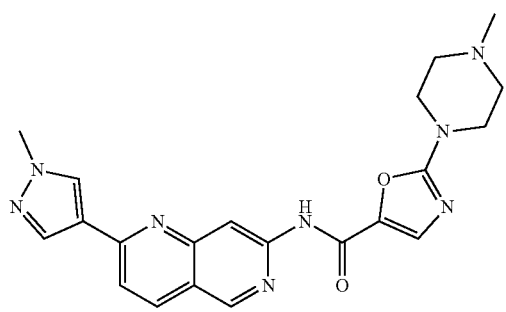 [SMILES: CN1CCN(c2ncc(C(=O)Nc3cc4nc(-c5cnn(C)c5)ccc4cn3)o2)CC1]
239
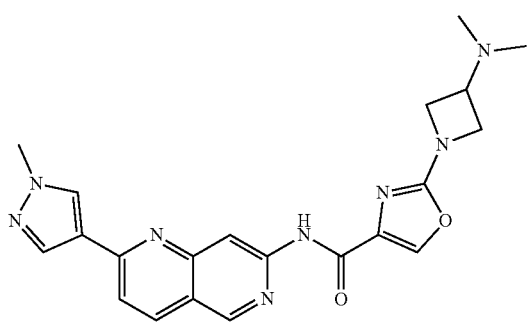 [SMILES: CN(C)C1CN(c2nc(C(=O)Nc3cc4nc(-c5cnn(C)c5)ccc4cn3)co2)C1]
240
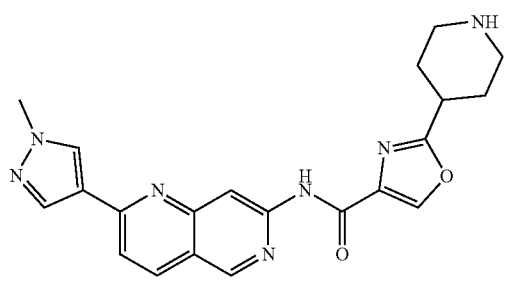 [SMILES: Cn1cc(-c2ccc3cnc(NC(=O)c4coc(C5CCNCC5)n4)cc3n2)cn1]
241
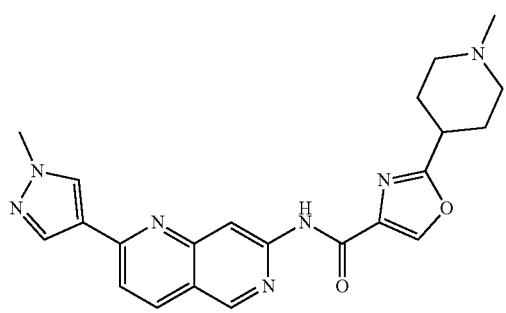 [SMILES: CN1CCC(c2nc(C(=O)Nc3cc4nc(-c5cnn(C)c5)ccc4cn3)co2)CC1]
242

TABLE 1-continued
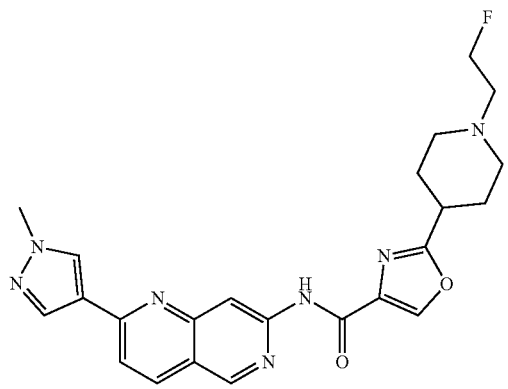
243
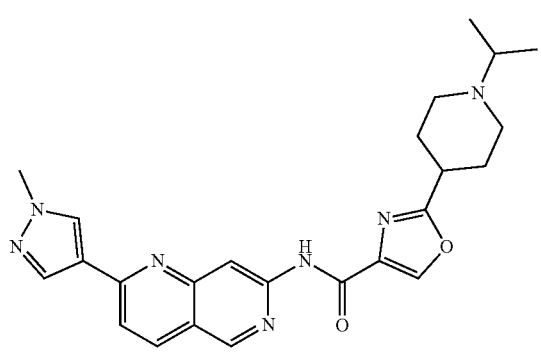
244
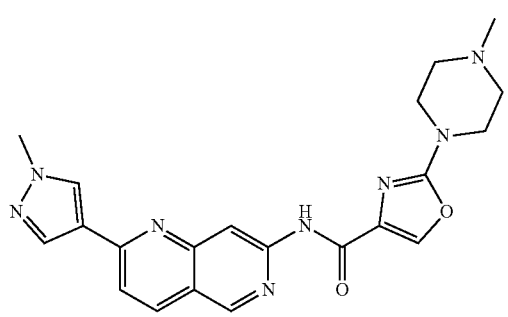
245
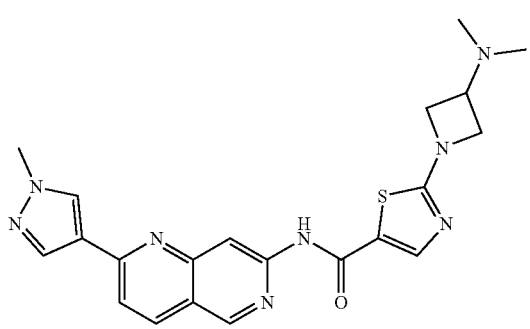 [SMILES: CN(C)C1CN(c2ncc(C(=O)Nc3cc4nc(-c5cnn(C)c5)ccc4cn3)s2)C1]
246
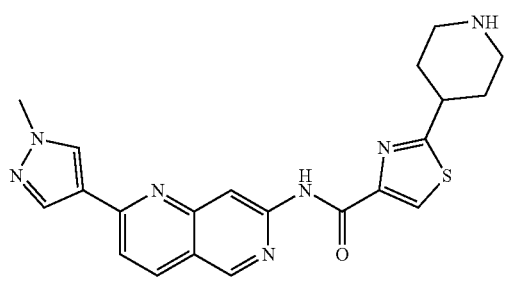
247

TABLE 1-continued
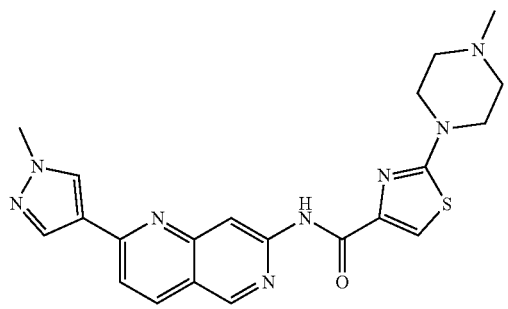 [SMILES: CN1CCN(c2nc(C(=O)Nc3cc4nc(-c5cnn(C)c5)ccc4cn3)cs2)CC1]
248
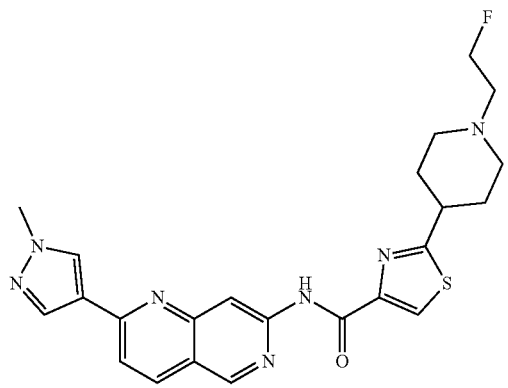 [SMILES: Cn1cc(-c2ccc3cnc(NC(=O)c4csc(C5CCN(CCF)CC5)n4)cc3n2)cn1]
249
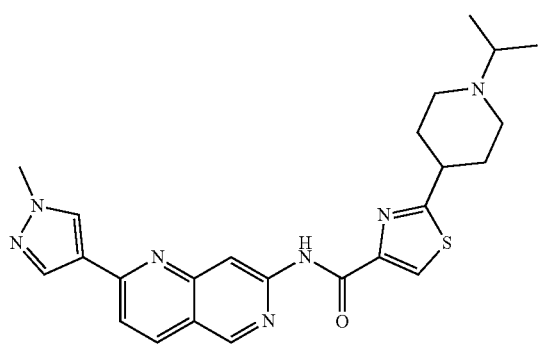 [SMILES: CC(C)N1CCC(c2nc(C(=O)Nc3cc4nc(-c5cnn(C)c5)ccc4cn3)cs2)CC1]
250
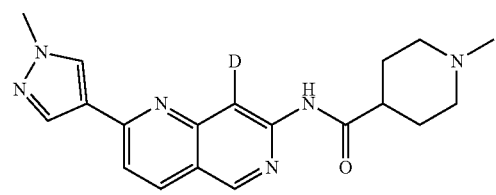 [SMILES: [2H]c1c(NC(=O)C2CCN(C)CC2)ncc2ccc(-c3cnn(C)c3)nc12]
251
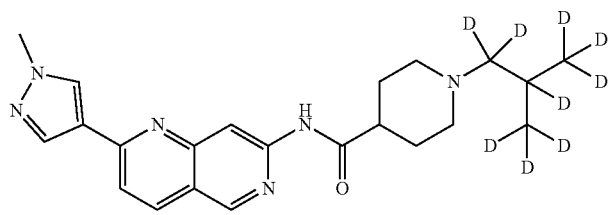 [SMILES: [2H]C([2H])([2H])C([2H])(C([2H])([2H])[2H])C([2H])([2H])N1CCC(C(=O)Nc2cc3nc(-c4cnn(C)c4)ccc3cn2)CC1]
252

TABLE 1-continued
| | |
|---|---|
| 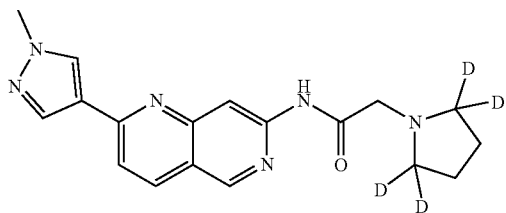 [SMILES: [2H]C1([2H])CCC([2H])([2H])N1CC(=O)Nc1cc2nc(-c3cnn(C)c3)ccc2cn1] | 253 |
| 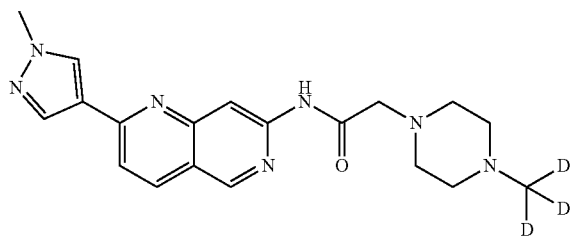 [SMILES: [2H]C([2H])([2H])N1CCN(CC(=O)Nc2cc3nc(-c4cnn(C)c4)ccc3cn2)CC1] | 254 |
| 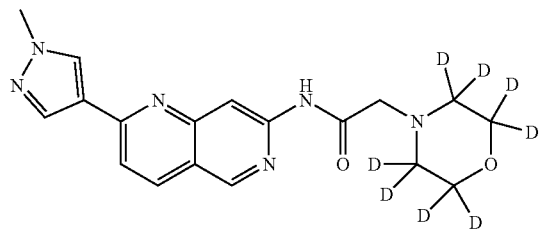 [SMILES: [2H]C1([2H])OC([2H])([2H])C([2H])([2H])N(CC(=O)Nc2cc3nc(-c4cnn(C)c4)ccc3cn2)C1([2H])[2H]] | 255 |
| 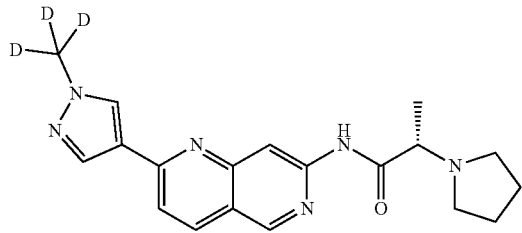 [SMILES: [2H]C([2H])([2H])n1cc(-c2ccc3cnc(NC(=O)[C@H](C)N4CCCC4)cc3n2)cn1] | 256 |
| 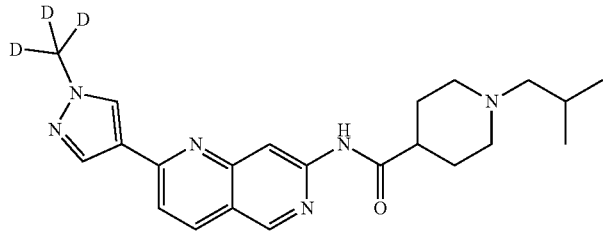 [SMILES: [2H]C([2H])([2H])n1cc(-c2ccc3cnc(NC(=O)C4CCN(CC(C)C)CC4)cc3n2)cn1] | 257 |
| 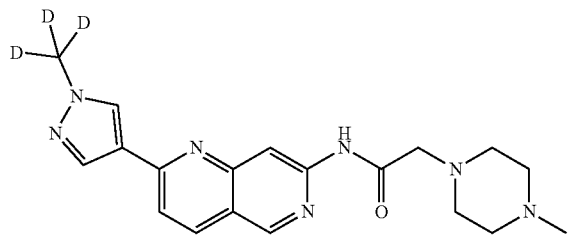 [SMILES: [2H]C([2H])([2H])n1cc(-c2ccc3cnc(NC(=O)CN4CCN(C)CC4)cc3n2)cn1] | 258 |

TABLE 1-continued
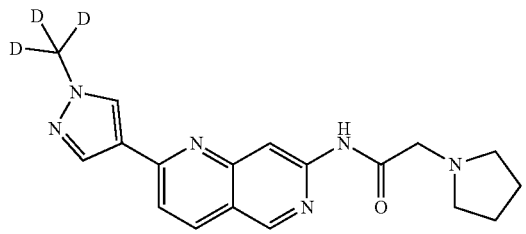 [SMILES: [2H]C([2H])([2H])n1cc(-c2ccc3cnc(NC(=O)CN4CCCC4)cc3n2)cn1]
259
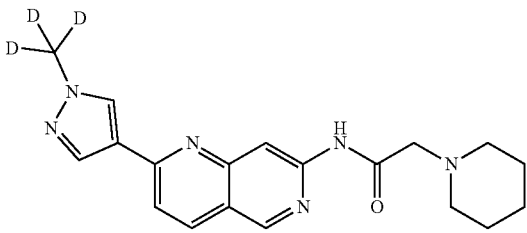 [SMILES: [2H]C([2H])([2H])n1cc(-c2ccc3cnc(NC(=O)CN4CCCCC4)cc3n2)cn1]
260
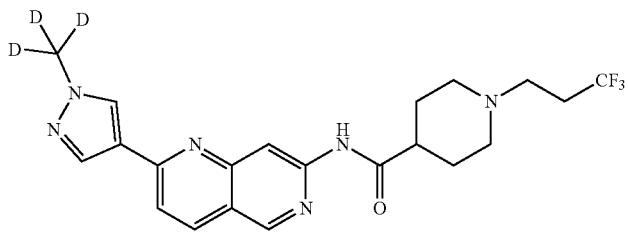 [SMILES: [2H]C([2H])([2H])n1cc(-c2ccc3cnc(NC(=O)C4CCN(CCC(F)(F)F)CC4)cc3n2)cn1]
261
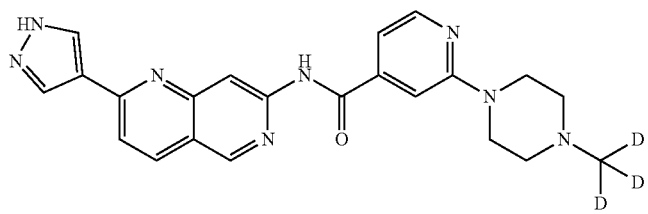 [SMILES: [2H]C([2H])([2H])N1CCN(c2cc(C(=O)Nc3cc4nc(-c5cn[nH]c5)ccc4cn3)ccn2)CC1]
262
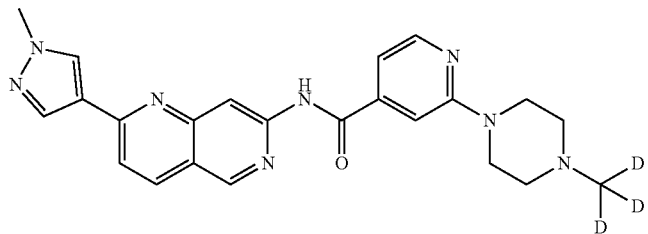 [SMILES: [2H]C([2H])([2H])N1CCN(c2cc(C(=O)Nc3cc4nc(-c5cnn(C)c5)ccc4cn3)ccn2)CC1]
263
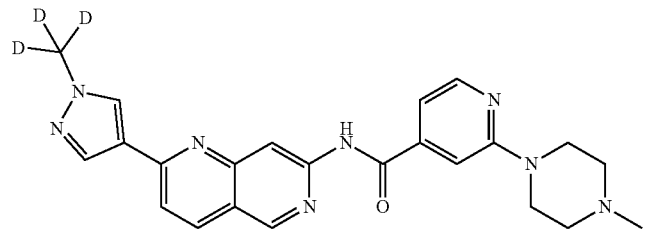 [SMILES: [2H]C([2H])([2H])n1cc(-c2ccc3cnc(NC(=O)c4ccnc(N5CCN(C)CC5)c4)cc3n2)cn1]
264

TABLE 1-continued
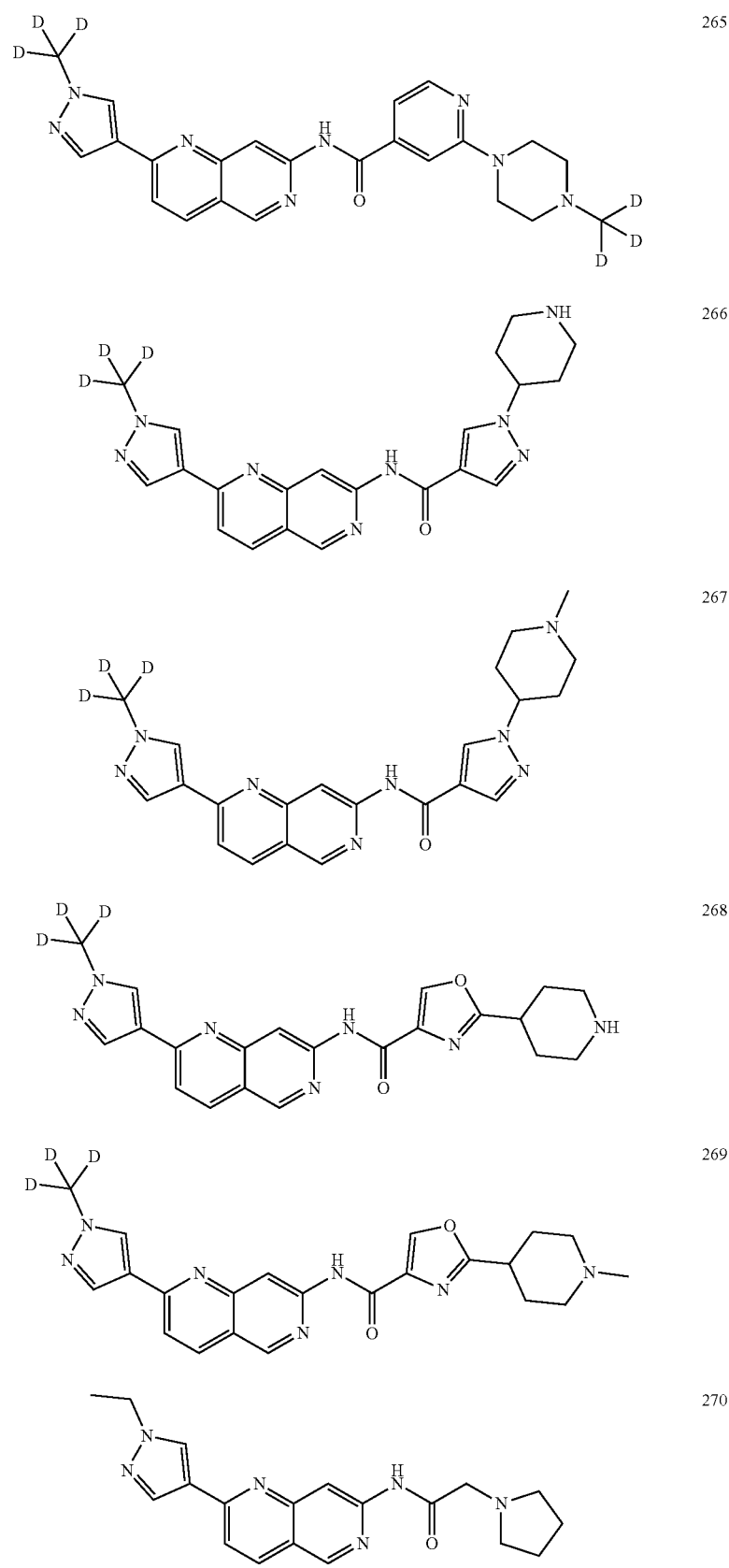

TABLE 1-continued
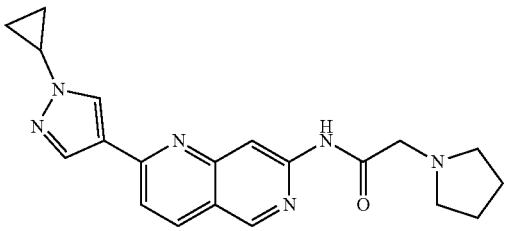 [SMILES: O=C(CN1CCCC1)Nc1cc2nc(-c3cnn(C4CC4)c3)ccc2cn1] 271
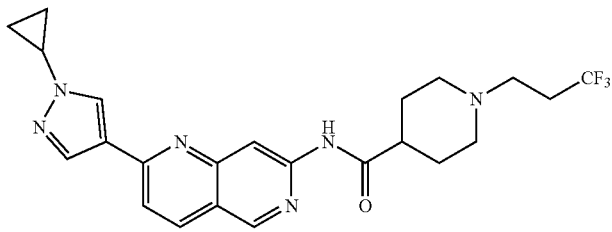 [SMILES: O=C(Nc1cc2nc(-c3cnn(C4CC4)c3)ccc2cn1)C1CCN(CCC(F)(F)F)CC1] 272
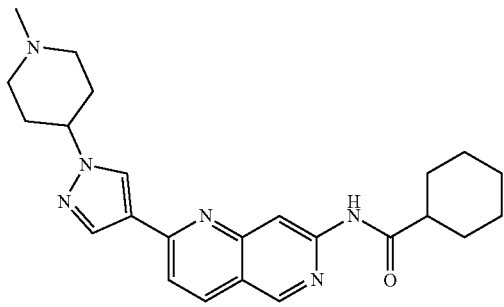 [SMILES: CN1CCC(n2cc(-c3ccc4cnc(NC(=O)C5CCCCC5)cc4n3)cn2)CC1] 273
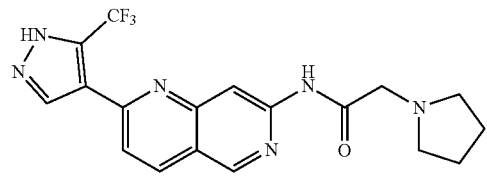 [SMILES: O=C(CN1CCCC1)Nc1cc2nc(-c3cn[nH]c3C(F)(F)F)ccc2cn1] 274
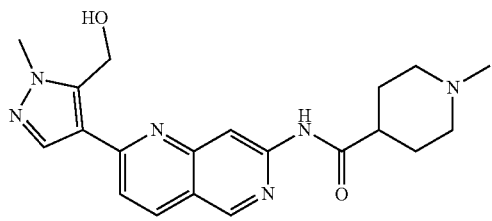 [SMILES: CN1CCC(C(=O)Nc2cc3nc(-c4cnn(C)c4CO)ccc3cn2)CC1] 275
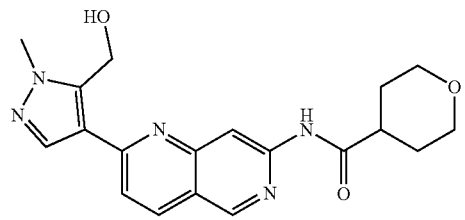 [SMILES: Cn1ncc(-c2ccc3cnc(NC(=O)C4CCOCC4)cc3n2)c1CO] 276

TABLE 1-continued
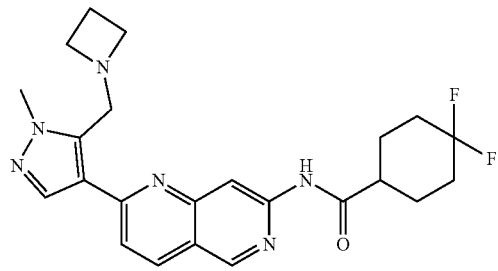 [SMILES: Cn1ncc(-c2ccc3cnc(NC(=O)C4CCC(F)(F)CC4)cc3n2)c1CN1CCC1]
277
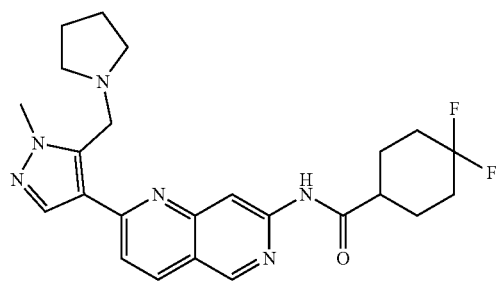
278
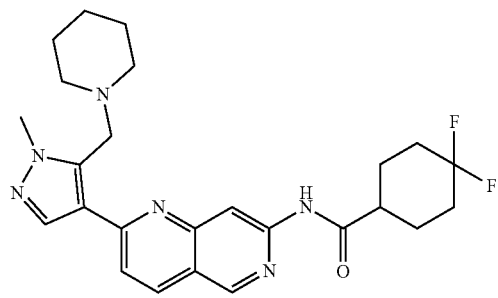 [SMILES: Cn1ncc(-c2ccc3cnc(NC(=O)C4CCC(F)(F)CC4)cc3n2)c1CN1CCCCC1]
279
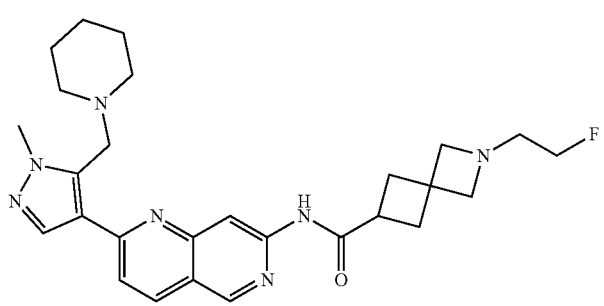 [SMILES: Cn1ncc(-c2ccc3cnc(NC(=O)C4CC5(C4)CN(CCF)C5)cc3n2)c1CN1CCCCC1]
280
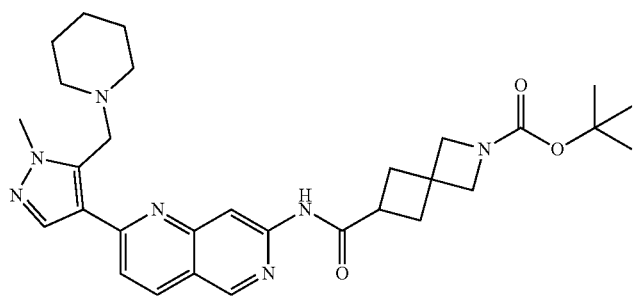 [SMILES: Cn1ncc(-c2ccc3cnc(NC(=O)C4CC5(C4)CN(C(=O)OC(C)(C)C)C5)cc3n2)c1CN1CCCCC1]
281

TABLE 1-continued
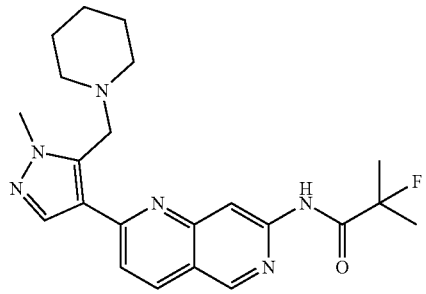 282
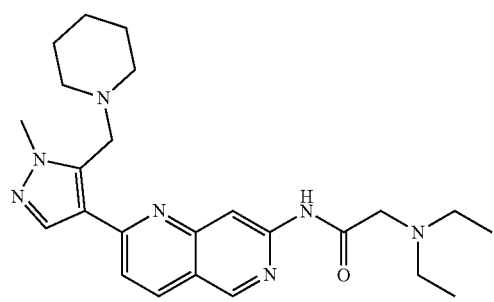 [SMILES: CCN(CC)CC(=O)Nc1cc2nc(-c3cnn(C)c3CN3CCCCC3)ccc2cn1] 283
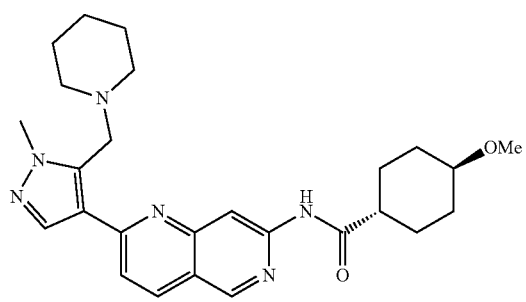 284
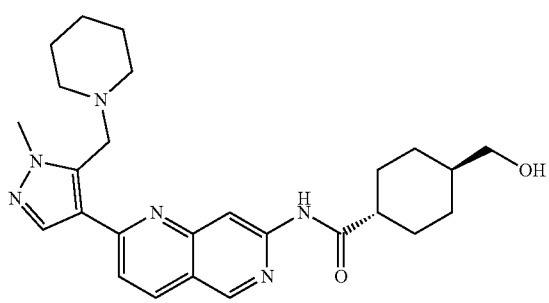 [SMILES: Cn1ncc(-c2ccc3cnc(NC(=O)[C@H]4CC[C@H](CO)CC4)cc3n2)c1CN1CCCCC1] 285
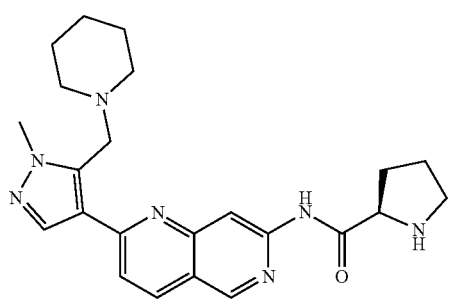 286

TABLE 1-continued
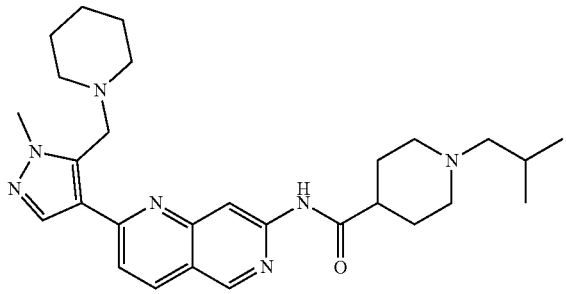 [SMILES: CC(C)CN1CCC(C(=O)Nc2cc3nc(-c4cnn(C)c4CN4CCCCC4)ccc3cn2)CC1]
287
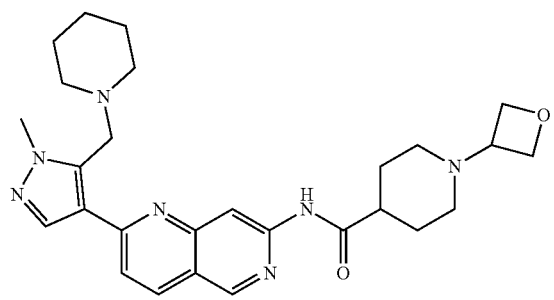 [SMILES: Cn1ncc(-c2ccc3cnc(NC(=O)C4CCN(C5COC5)CC4)cc3n2)c1CN1CCCCC1]
288
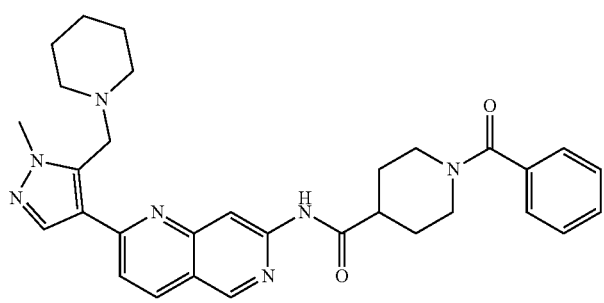
289
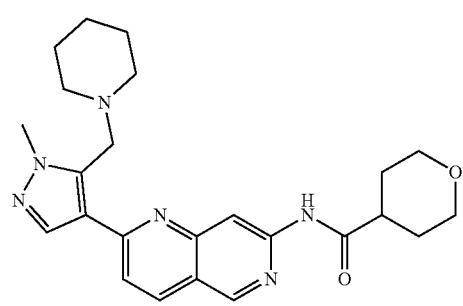 [SMILES: Cn1ncc(-c2ccc3cnc(NC(=O)C4CCOCC4)cc3n2)c1CN1CCCCC1]
290
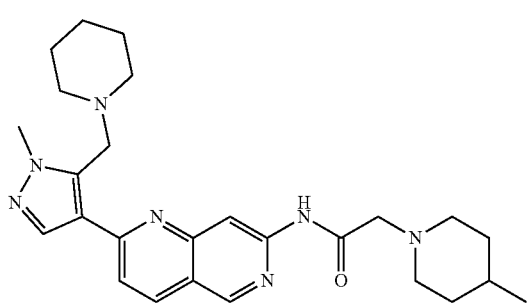 [SMILES: CC1CCN(CC(=O)Nc2cc3nc(-c4cnn(C)c4CN4CCCCC4)ccc3cn2)CC1]
291

TABLE 1-continued
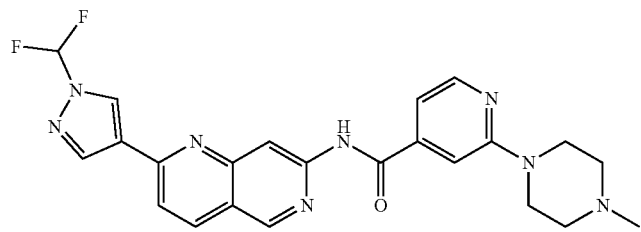 [SMILES: CN1CCN(c2cc(C(=O)Nc3cc4nc(-c5cnn(C(F)F)c5)ccc4cn3)ccn2)CC1] 292
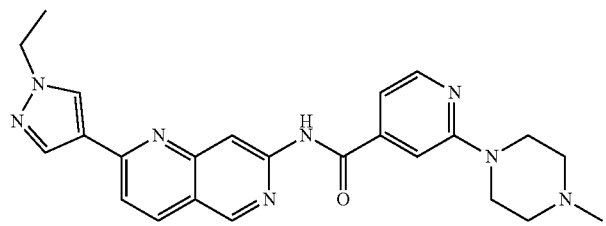 [SMILES: CCn1cc(-c2ccc3cnc(NC(=O)c4ccnc(N5CCN(C)CC5)c4)cc3n2)cn1] 293
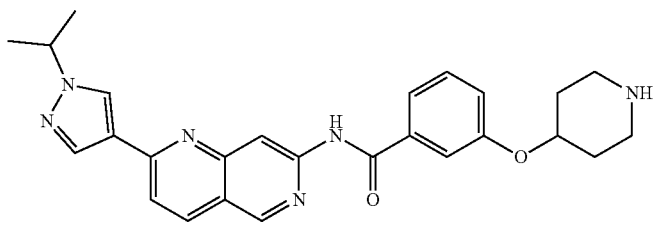 [SMILES: CC(C)n1cc(-c2ccc3cnc(NC(=O)c4cccc(OC5CCNCC5)c4)cc3n2)cn1] 294
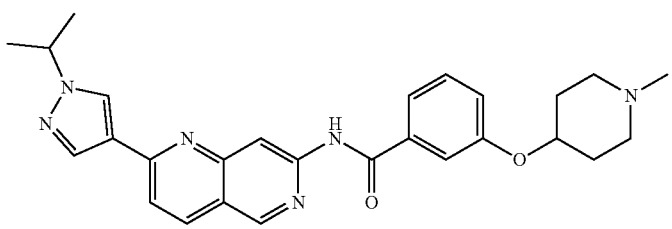 295
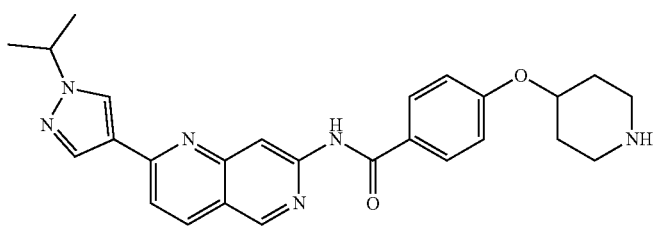 [SMILES: CC(C)n1cc(-c2ccc3cnc(NC(=O)c4ccc(OC5CCNCC5)cc4)cc3n2)cn1] 296
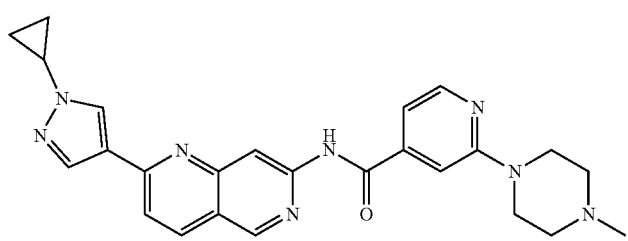 [SMILES: CN1CCN(c2cc(C(=O)Nc3cc4nc(-c5cnn(C6CC6)c5)ccc4cn3)ccn2)CC1] 297

TABLE 1-continued
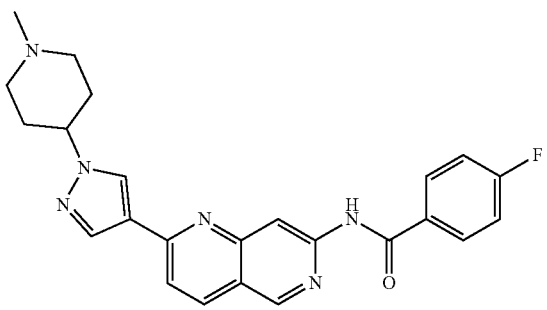
298
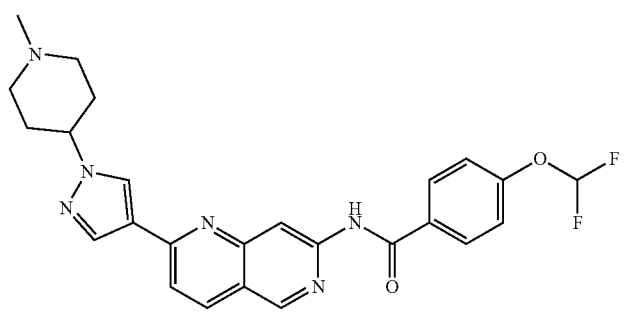 [SMILES: CN1CCC(n2cc(-c3ccc4cnc(NC(=O)c5ccc(OC(F)F)cc5)cc4n3)cn2)CC1]
299
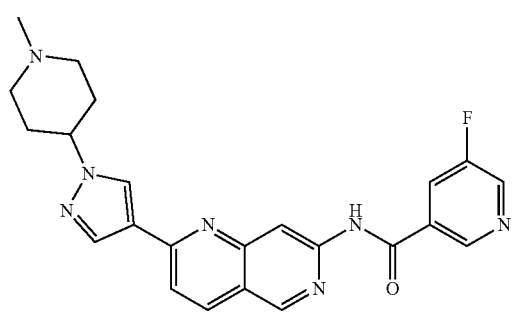 [SMILES: CN1CCC(n2cc(-c3ccc4cnc(NC(=O)c5cncc(F)c5)cc4n3)cn2)CC1]
300
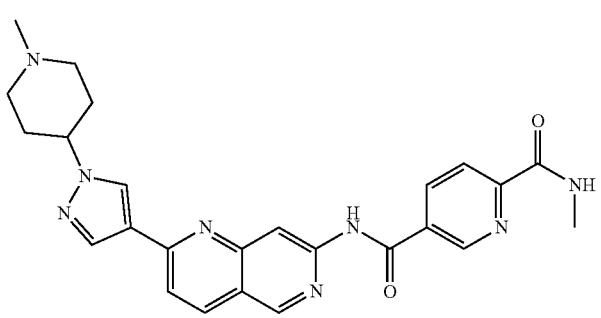 [SMILES: CNC(=O)c1ccc(C(=O)Nc2cc3nc(-c4cnn(C5CCN(C)CC5)c4)ccc3cn2)cn1]
301
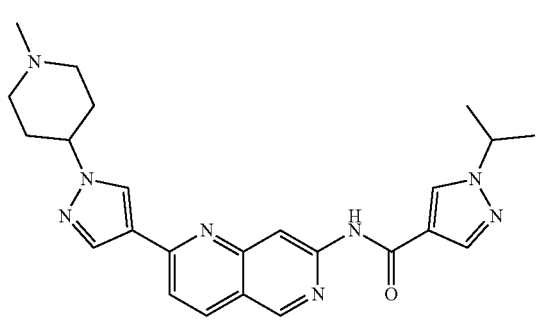 [SMILES: CC(C)n1cc(C(=O)Nc2cc3nc(-c4cnn(C5CCN(C)CC5)c4)ccc3cn2)cn1]
302

TABLE 1-continued
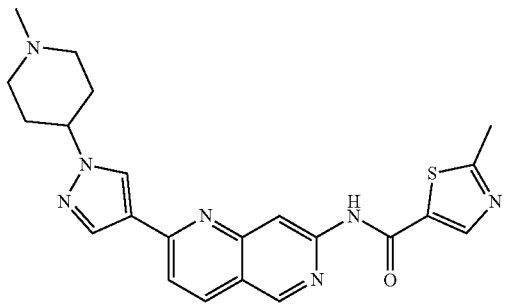 [SMILES: Cc1ncc(C(=O)Nc2cc3nc(-c4cnn(C5CCN(C)CC5)c4)ccc3cn2)s1]
303
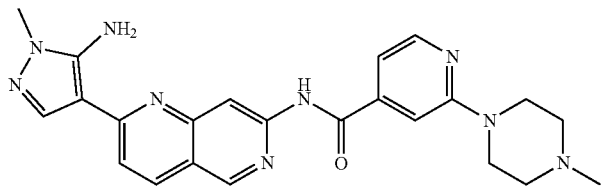 [SMILES: CN1CCN(c2cc(C(=O)Nc3cc4nc(-c5cnn(C)c5N)ccc4cn3)ccn2)CC1]
304
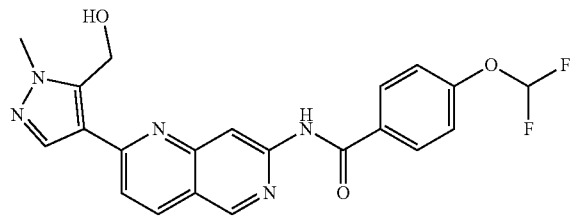 [SMILES: Cn1ncc(-c2ccc3cnc(NC(=O)c4ccc(OC(F)F)cc4)cc3n2)c1CO]
305
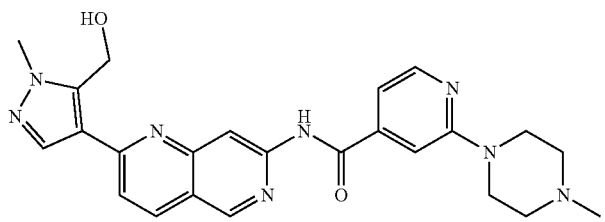 [SMILES: CN1CCN(c2cc(C(=O)Nc3cc4nc(-c5cnn(C)c5CO)ccc4cn3)ccn2)CC1]
306
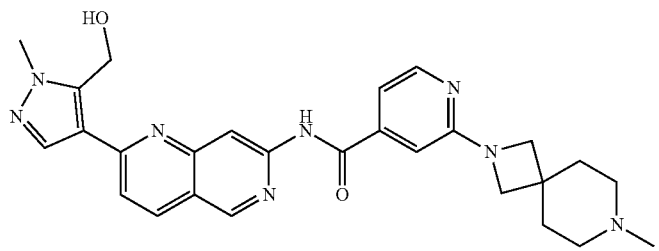 [SMILES: CN1CCC2(CC1)CN(c1cc(C(=O)Nc3cc4nc(-c5cnn(C)c5CO)ccc4cn3)ccn1)C2]
307
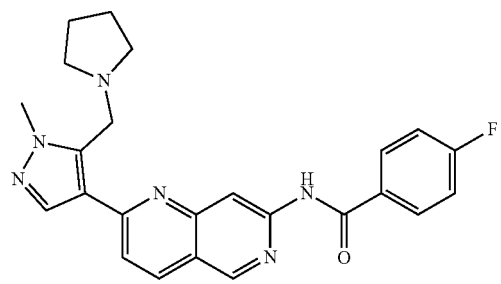 [SMILES: Cn1ncc(-c2ccc3cnc(NC(=O)c4ccc(F)cc4)cc3n2)c1CN1CCCC1]
308

TABLE 1-continued
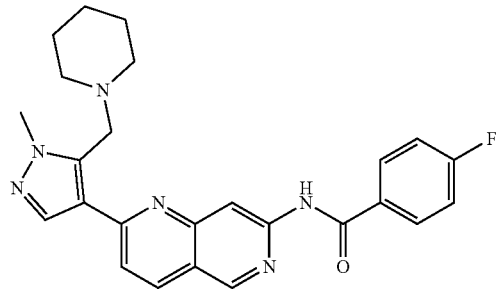 [SMILES: Cn1ncc(-c2ccc3cnc(NC(=O)c4ccc(F)cc4)cc3n2)c1CN1CCCCC1]
309
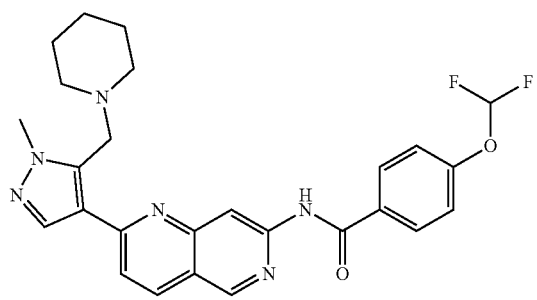 [SMILES: Cn1ncc(-c2ccc3cnc(NC(=O)c4ccc(OC(F)F)cc4)cc3n2)c1CN1CCCCC1]
310
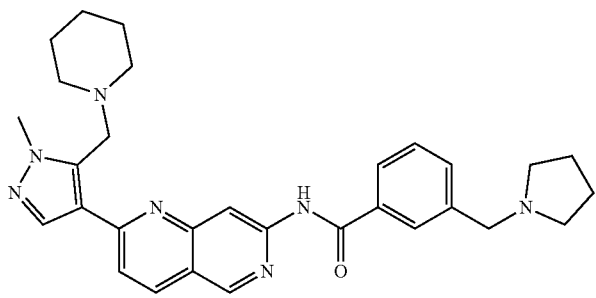 [SMILES: Cn1ncc(-c2ccc3cnc(NC(=O)c4cccc(CN5CCCC5)c4)cc3n2)c1CN1CCCCC1]
311
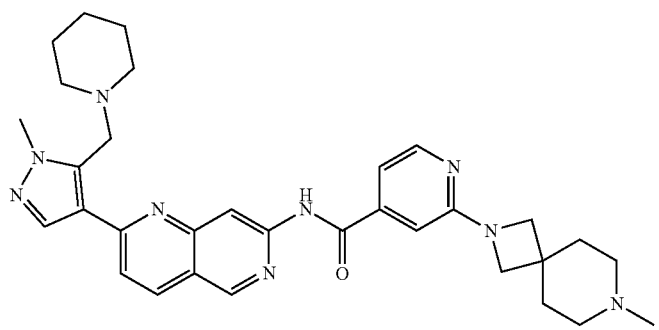 [SMILES: CN1CCC2(CC1)CN(c1cc(C(=O)Nc3cc4nc(-c5cnn(C)c5CN5CCCCC5)ccc4cn3)ccn1)C2]
312
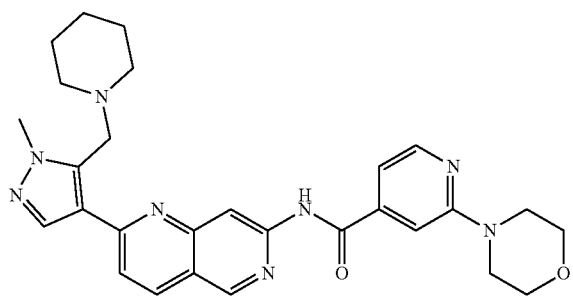
313

TABLE 1-continued
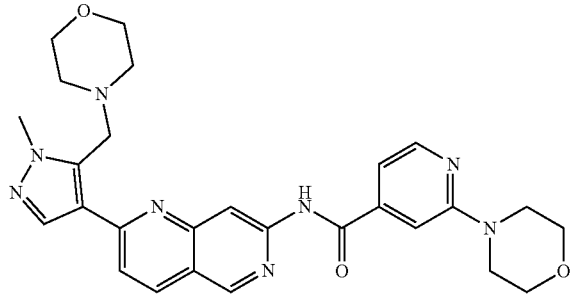 [SMILES: Cn1ncc(-c2ccc3cnc(NC(=O)c4ccnc(N5CCOCC5)c4)cc3n2)c1CN1CCOCC1] 314
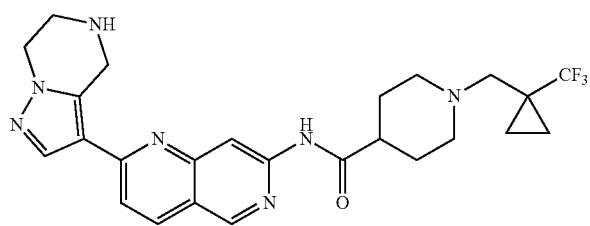 [SMILES: O=C(Nc1cc2nc(-c3cnn4c3CNCC4)ccc2cn1)C1CCN(CC2(C(F)(F)F)CC2)CC1] 315
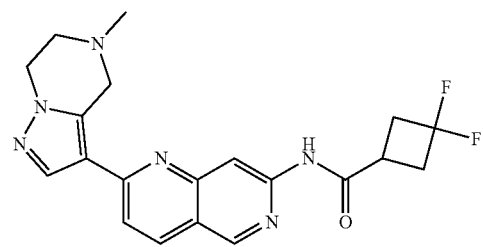 [SMILES: CN1CCn2ncc(-c3ccc4cnc(NC(=O)C5CC(F)(F)C5)cc4n3)c2C1] 316
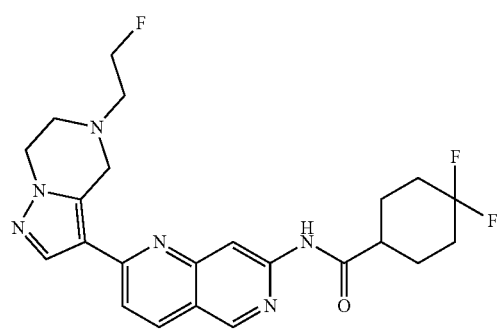 [SMILES: O=C(Nc1cc2nc(-c3cnn4c3CN(CCF)CC4)ccc2cn1)C1CCC(F)(F)CC1] 317
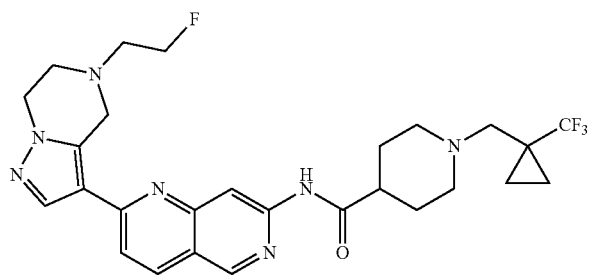 [SMILES: O=C(Nc1cc2nc(-c3cnn4c3CN(CCF)CC4)ccc2cn1)C1CCN(CC2(C(F)(F)F)CC2)CC1] 318

TABLE 1-continued
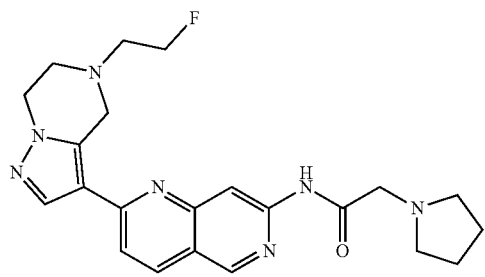 [SMILES: O=C(CN1CCCC1)Nc1cc2nc(-c3cnn4c3CN(CCF)CC4)ccc2cn1]
319
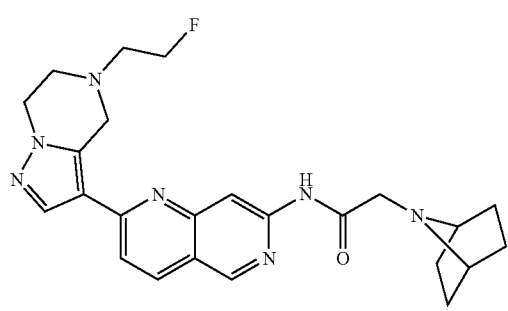 [SMILES: O=C(CN1C2CCC1CC2)Nc1cc2nc(-c3cnn4c3CN(CCF)CC4)ccc2cn1]
320
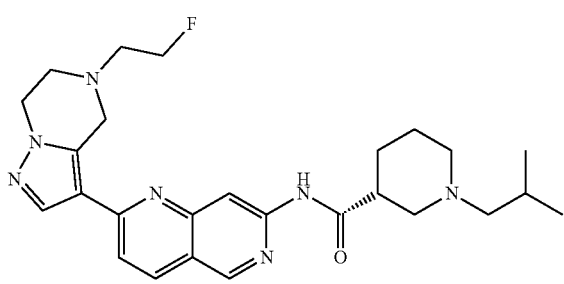
321
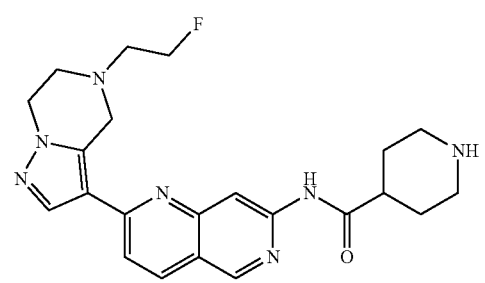 [SMILES: O=C(Nc1cc2nc(-c3cnn4c3CN(CCF)CC4)ccc2cn1)C1CCNCC1]
322
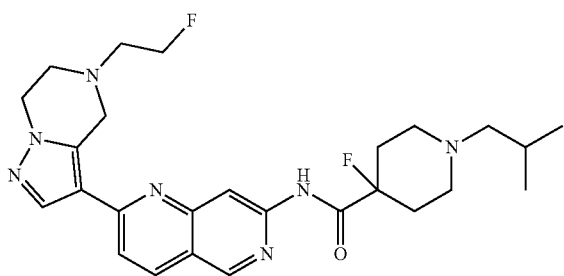 [SMILES: CC(C)CN1CCC(F)(C(=O)Nc2cc3nc(-c4cnn5c4CN(CCF)CC5)ccc3cn2)CC1]
323

TABLE 1-continued
| | |
|---|---|
| 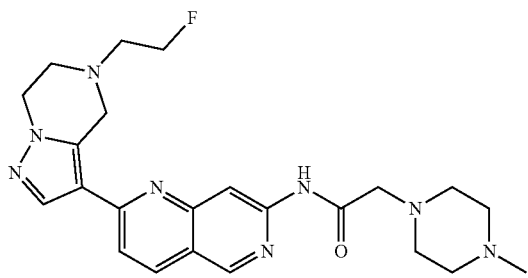 [SMILES: CN1CCN(CC(=O)Nc2cc3nc(-c4cnn5c4CN(CCF)CC5)ccc3cn2)CC1] | 324 |
| 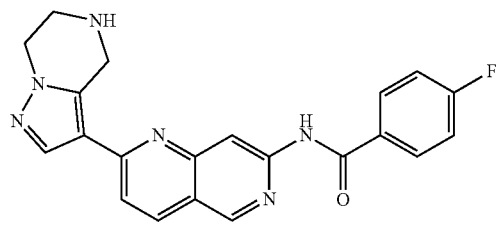 | 325 |
| 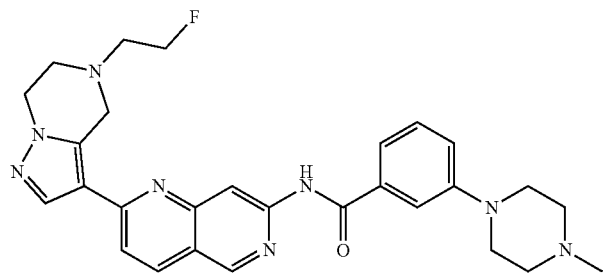 | 326 |
| 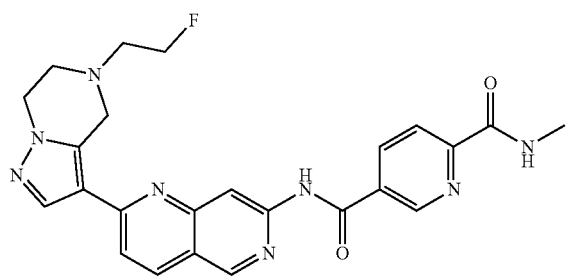 [SMILES: CNC(=O)c1ccc(C(=O)Nc2cc3nc(-c4cnn5c4CN(CCF)CC5)ccc3cn2)cn1] | 327 |
| 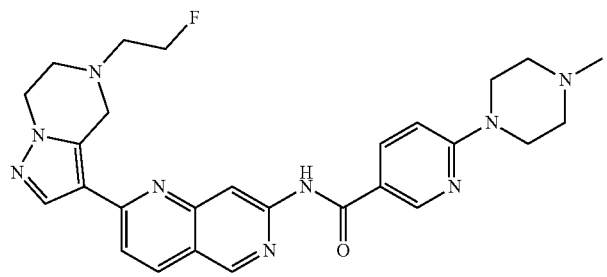 [SMILES: CN1CCN(c2ccc(C(=O)Nc3cc4nc(-c5cnn6c5CN(CCF)CC6)ccc4cn3)cn2)CC1] | 328 |
| 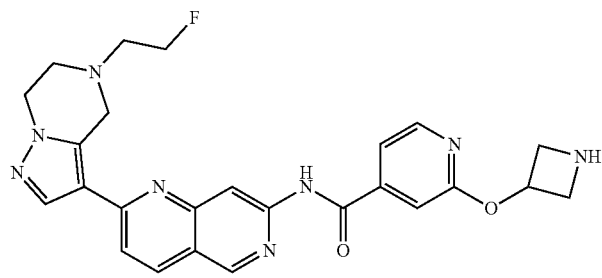 [SMILES: O=C(Nc1cc2nc(-c3cnn4c3CN(CCF)CC4)ccc2cn1)c1ccnc(OC2CNC2)c1] | 329 |

TABLE 1-continued
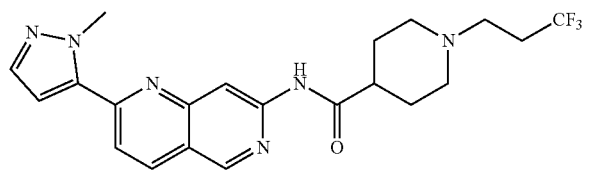 [SMILES: Cn1nccc1-c1ccc2cnc(NC(=O)C3CCN(CCC(F)(F)F)CC3)cc2n1] 330
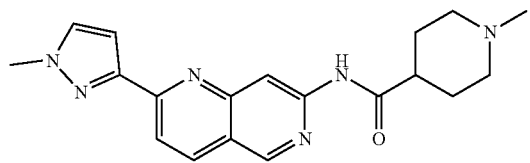 331
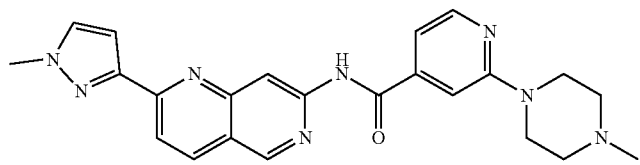 332
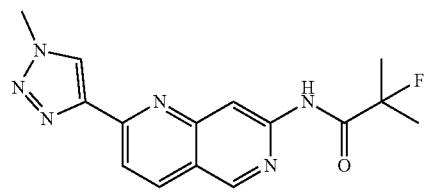 [SMILES: Cn1cc(-c2ccc3cnc(NC(=O)C(C)(C)F)cc3n2)nn1] 333
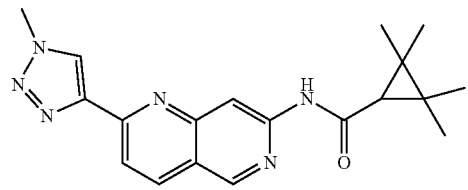 [SMILES: Cn1cc(-c2ccc3cnc(NC(=O)C4C(C)(C)C4(C)C)cc3n2)nn1] 334
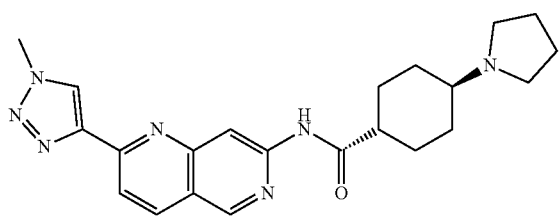 335
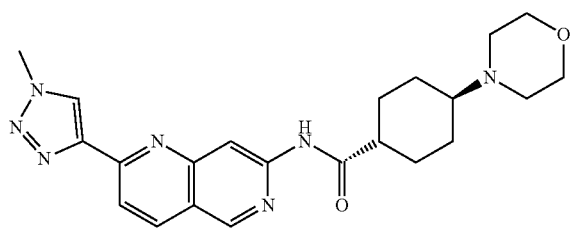 336
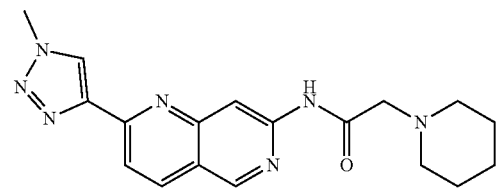 [SMILES: Cn1cc(-c2ccc3cnc(NC(=O)CN4CCCCC4)cc3n2)nn1] 337

TABLE 1-continued
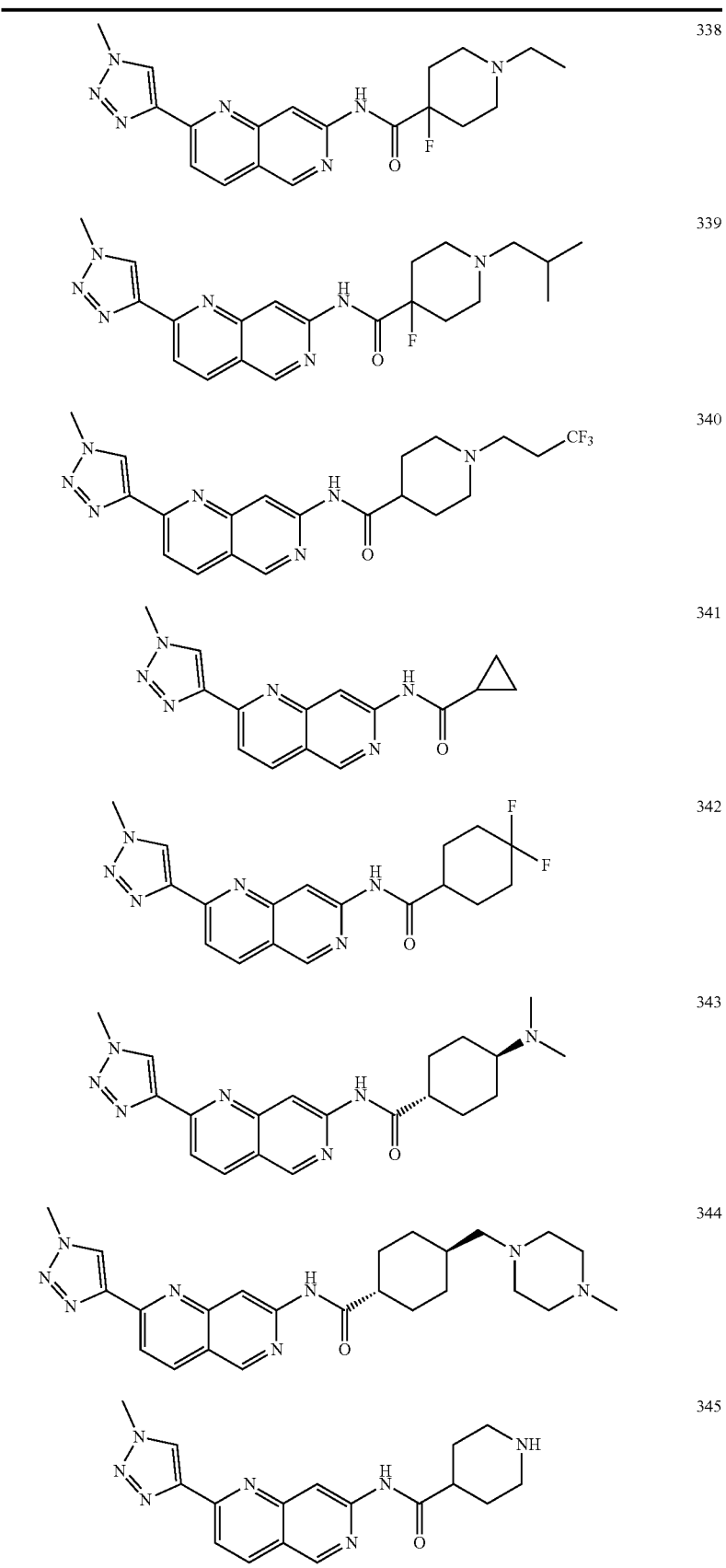

TABLE 1-continued
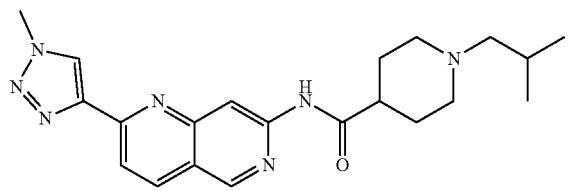 346
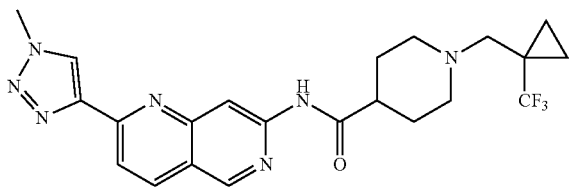 [SMILES: Cn1cc(-c2ccc3cnc(NC(=O)C4CCN(CC5(C(F)(F)F)CC5)CC4)cc3n2)nn1] 347
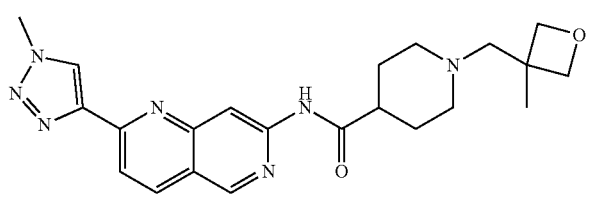 [SMILES: Cn1cc(-c2ccc3cnc(NC(=O)C4CCN(CC5(C)COC5)CC4)cc3n2)nn1] 348
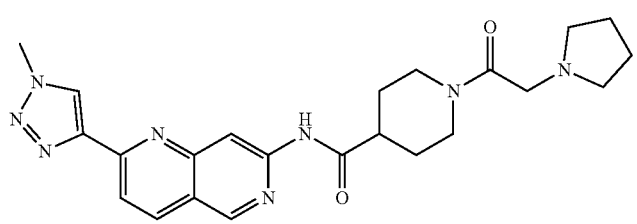 [SMILES: Cn1cc(-c2ccc3cnc(NC(=O)C4CCN(C(=O)CN5CCCC5)CC4)cc3n2)nn1] 349
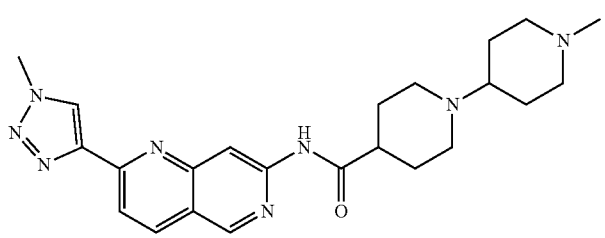 350
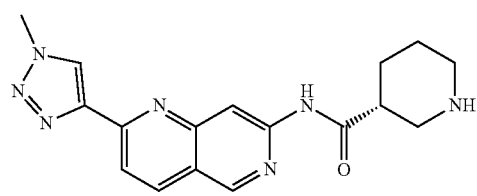 351
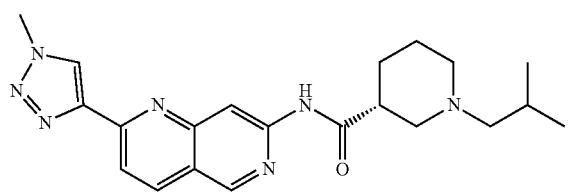 [SMILES: CC(C)CN1CCC[C@@H](C(=O)Nc2cc3nc(-c4cn(C)nn4)ccc3cn2)C1] 352
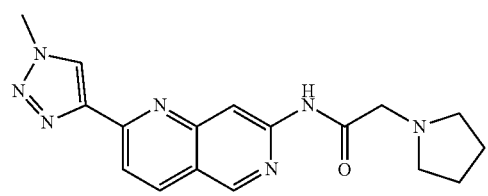 [SMILES: Cn1cc(-c2ccc3cnc(NC(=O)CN4CCCC4)cc3n2)nn1] 353

TABLE 1-continued
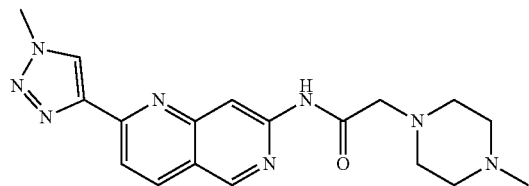 [SMILES: CN1CCN(CC(=O)Nc2cc3nc(-c4cn(C)nn4)ccc3cn2)CC1] 354
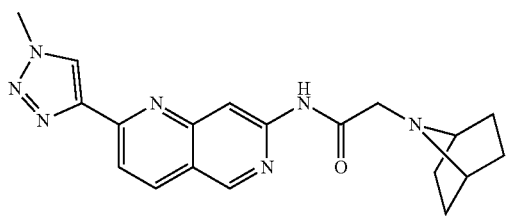 [SMILES: Cn1cc(-c2ccc3cnc(NC(=O)CN4C5CCC4CC5)cc3n2)nn1] 355
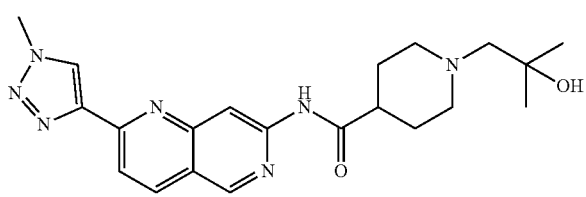 [SMILES: Cn1cc(-c2ccc3cnc(NC(=O)C4CCN(CC(C)(C)O)CC4)cc3n2)nn1] 356
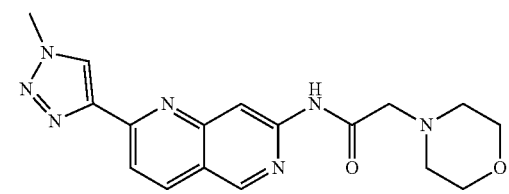 [SMILES: Cn1cc(-c2ccc3cnc(NC(=O)CN4CCOCC4)cc3n2)nn1] 357
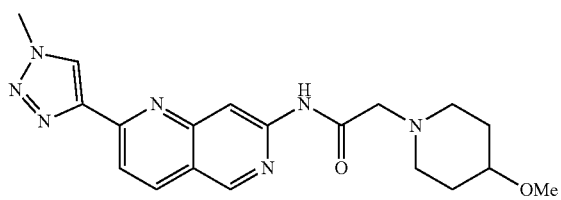 [SMILES: COC1CCN(CC(=O)Nc2cc3nc(-c4cn(C)nn4)ccc3cn2)CC1] 358
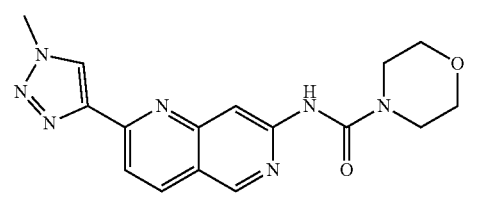 [SMILES: Cn1cc(-c2ccc3cnc(NC(=O)N4CCOCC4)cc3n2)nn1] 359
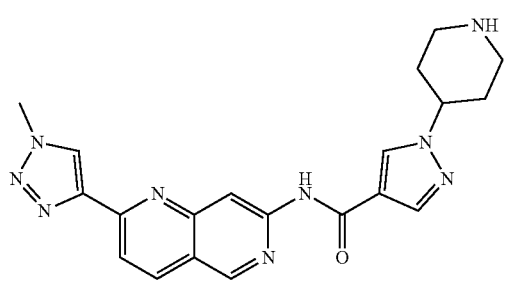 [SMILES: Cn1cc(-c2ccc3cnc(NC(=O)c4cnn(C5CCNCC5)c4)cc3n2)nn1] 360

TABLE 1-continued
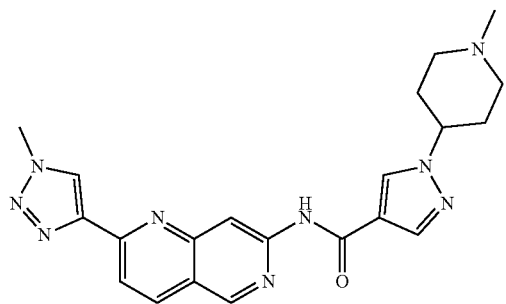 [SMILES: CN1CCC(n2cc(C(=O)Nc3cc4nc(-c5cn(C)nn5)ccc4cn3)cn2)CC1] 361
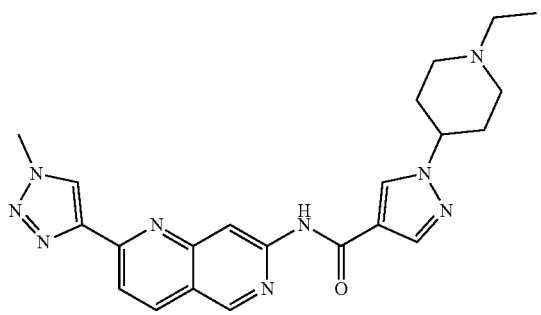 [SMILES: CCN1CCC(n2cc(C(=O)Nc3cc4nc(-c5cn(C)nn5)ccc4cn3)cn2)CC1] 362
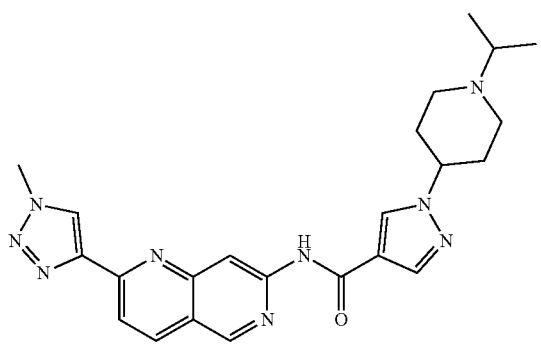 [SMILES: CC(C)N1CCC(n2cc(C(=O)Nc3cc4nc(-c5cn(C)nn5)ccc4cn3)cn2)CC1] 363
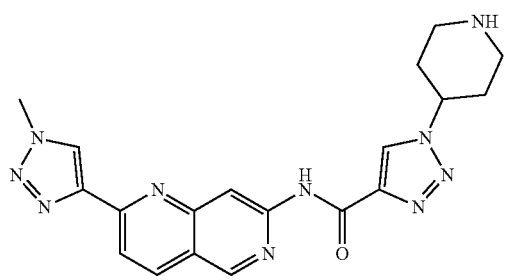 [SMILES: Cn1cc(-c2ccc3cnc(NC(=O)c4cn(C5CCNCC5)nn4)cc3n2)nn1] 364
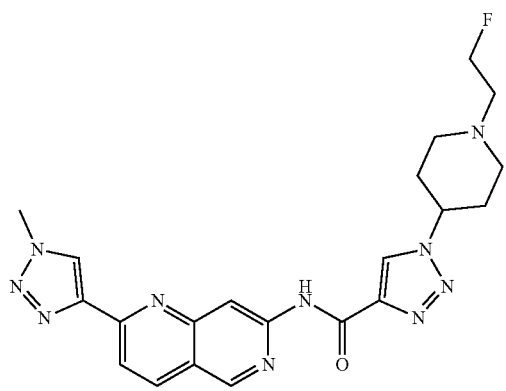 [SMILES: Cn1cc(-c2ccc3cnc(NC(=O)c4cn(C5CCN(CCF)CC5)nn4)cc3n2)nn1] 365

TABLE 1-continued
| | |
|---|---|
| 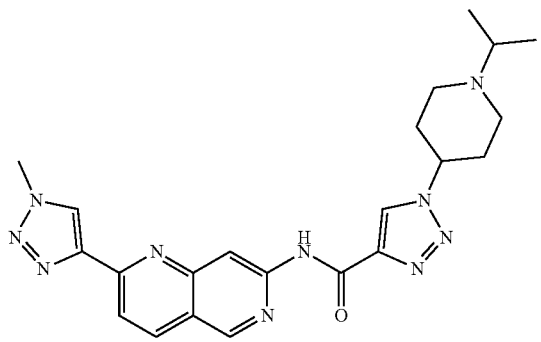 [SMILES: CC(C)N1CCC(n2cc(C(=O)Nc3cc4nc(-c5cn(C)nn5)ccc4cn3)nn2)CC1] | 366 |
| 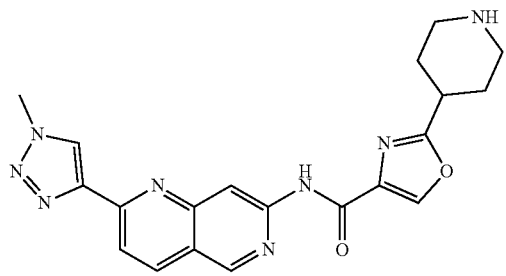 | 367 |
| 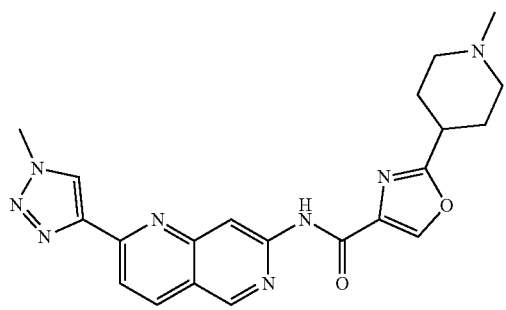 [SMILES: CN1CCC(c2nc(C(=O)Nc3cc4nc(-c5cn(C)nn5)ccc4cn3)co2)CC1] | 368 |
| 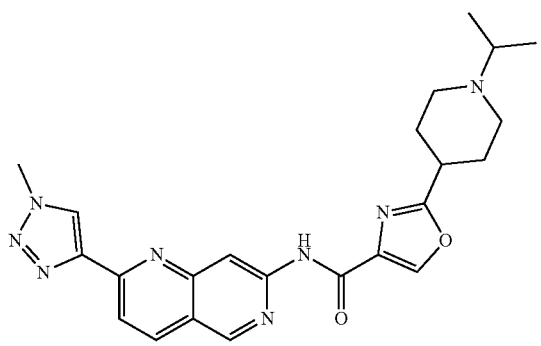 [SMILES: CC(C)N1CCC(c2nc(C(=O)Nc3cc4nc(-c5cn(C)nn5)ccc4cn3)co2)CC1] | 369 |
| 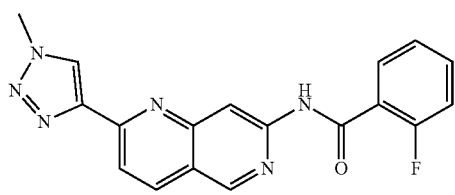 [SMILES: Cn1cc(-c2ccc3cnc(NC(=O)c4ccccc4F)cc3n2)nn1] | 370 |

TABLE 1-continued
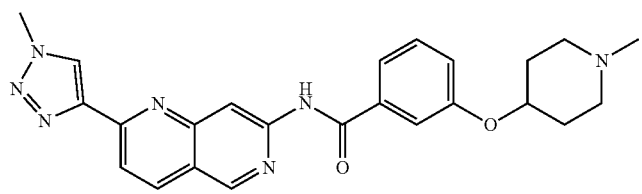 [SMILES: CN1CCC(Oc2cccc(C(=O)Nc3cc4nc(-c5cn(C)nn5)ccc4cn3)c2)CC1]
371
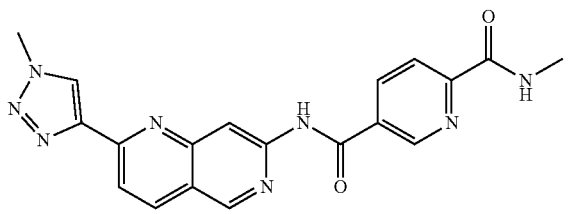 [SMILES: CNC(=O)c1ccc(C(=O)Nc2cc3nc(-c4cn(C)nn4)ccc3cn2)cn1]
372
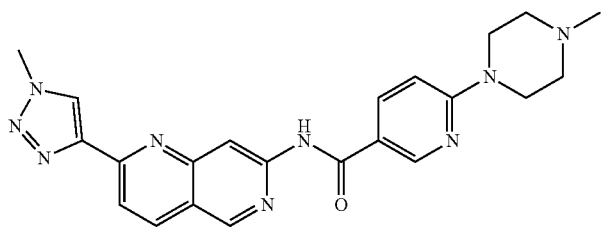
373
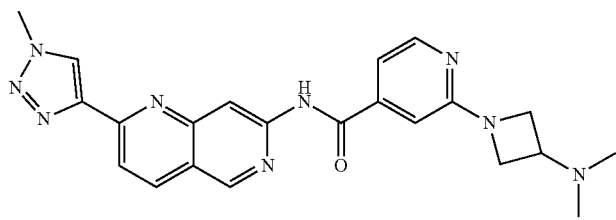 [SMILES: CN(C)C1CN(c2cc(C(=O)Nc3cc4nc(-c5cn(C)nn5)ccc4cn3)ccn2)C1]
374
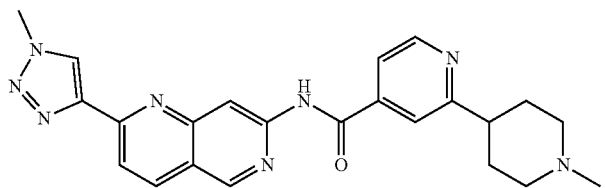
375
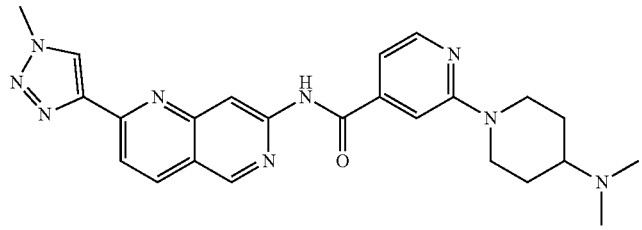 [SMILES: CN(C)C1CCN(c2cc(C(=O)Nc3cc4nc(-c5cn(C)nn5)ccc4cn3)ccn2)CC1]
376
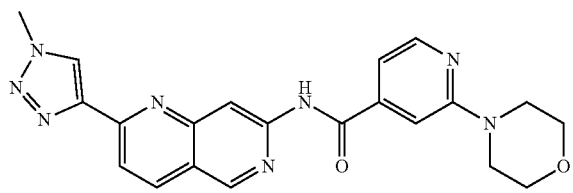 [SMILES: Cn1cc(-c2ccc3cnc(NC(=O)c4ccnc(N5CCOCC5)c4)cc3n2)nn1]
377

TABLE 1-continued

| | |
|---|---|
| (structure) | 378 |
| (structure) | 379 |
| (structure) | 380 |
| (structure) | 381 |
| (structure) | 382 |
| (structure) | 383 |
| (structure) | 384 |
| (structure) | 385 |

TABLE 1-continued
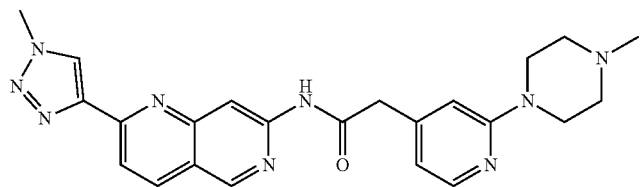 [SMILES: CN1CCN(c2cc(CC(=O)Nc3cc4nc(-c5cn(C)nn5)ccc4cn3)ccn2)CC1] 386
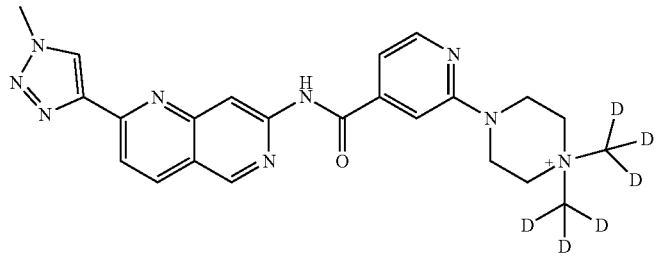 387
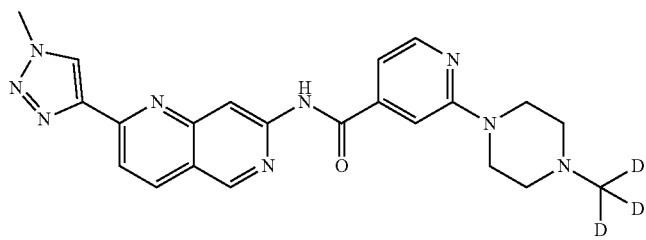 [SMILES: [2H]C([2H])([2H])N1CCN(c2cc(C(=O)Nc3cc4nc(-c5cn(C)nn5)ccc4cn3)ccn2)CC1] 388
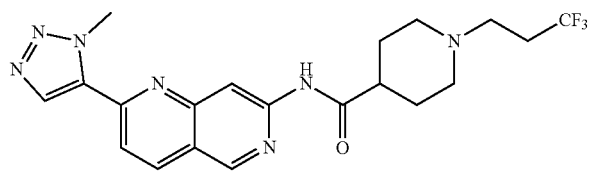 [SMILES: Cn1nncc1-c1ccc2cnc(NC(=O)C3CCN(CCC(F)(F)F)CC3)cc2n1] 389
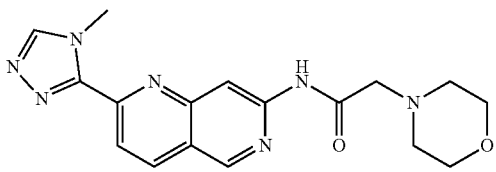 [SMILES: Cn1cnnc1-c1ccc2cnc(NC(=O)CN3CCOCC3)cc2n1] 390
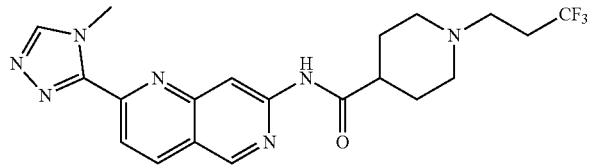 [SMILES: Cn1cnnc1-c1ccc2cnc(NC(=O)C3CCN(CCC(F)(F)F)CC3)cc2n1] 391
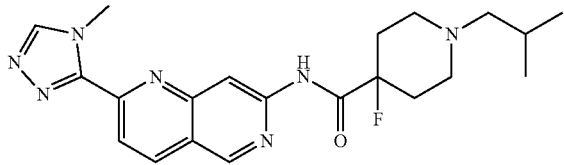 [SMILES: CC(C)CN1CCC(F)(C(=O)Nc2cc3nc(-c4nncn4C)ccc3cn2)CC1] 392
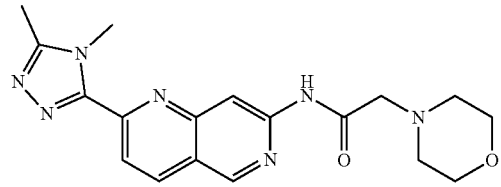 [SMILES: Cc1nnc(-c2ccc3cnc(NC(=O)CN4CCOCC4)cc3n2)n1C] 393

TABLE 1-continued
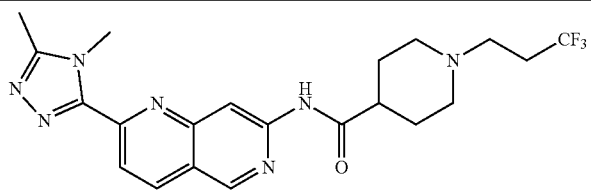 394
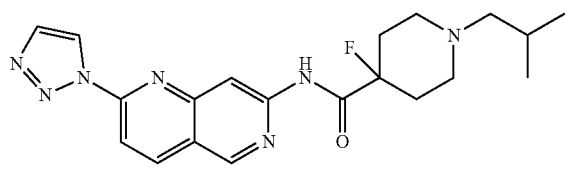 [SMILES: CC(C)CN1CCC(F)(C(=O)Nc2cc3nc(-n4ccnn4)ccc3cn2)CC1] 395
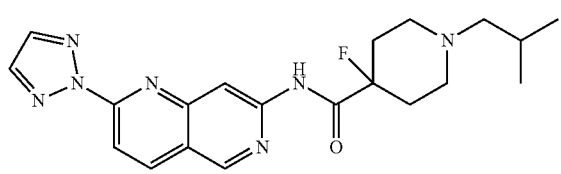 [SMILES: CC(C)CN1CCC(F)(C(=O)Nc2cc3nc(-n4nccn4)ccc3cn2)CC1] 396
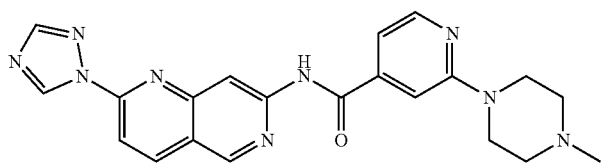 [SMILES: CN1CCN(c2cc(C(=O)Nc3cc4nc(-n5cncn5)ccc4cn3)ccn2)CC1] 397
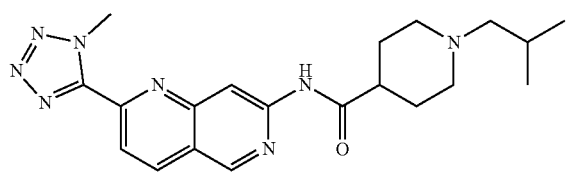 [SMILES: CC(C)CN1CCC(C(=O)Nc2cc3nc(-c4nnnn4C)ccc3cn2)CC1] 398
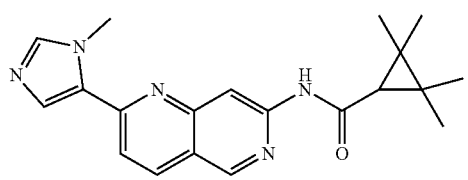 [SMILES: Cn1cncc1-c1ccc2cnc(NC(=O)C3C(C)(C)C3(C)C)cc2n1] 399
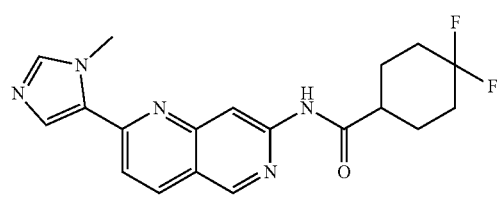 [SMILES: Cn1cncc1-c1ccc2cnc(NC(=O)C3CCC(F)(F)CC3)cc2n1] 400
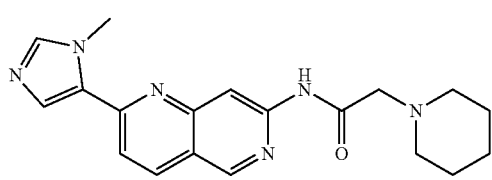 [SMILES: Cn1cncc1-c1ccc2cnc(NC(=O)CN3CCCCC3)cc2n1] 401
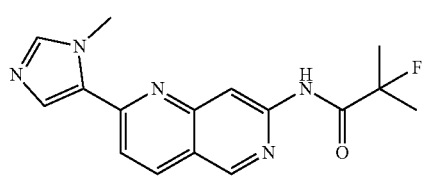 [SMILES: Cn1cncc1-c1ccc2cnc(NC(=O)C(C)(C)F)cc2n1] 402

TABLE 1-continued
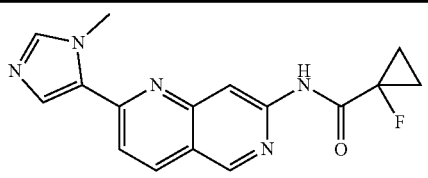 403
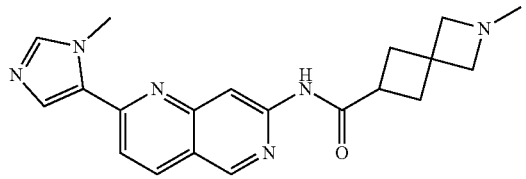 404
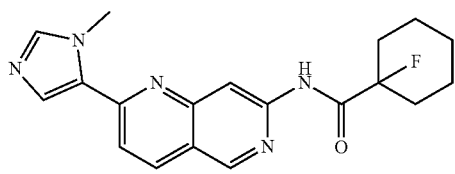 405
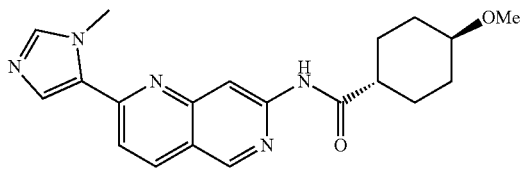 [SMILES: CO[C@H]1CC[C@H](C(=O)Nc2cc3nc(-c4cncn4C)ccc3cn2)CC1] 406
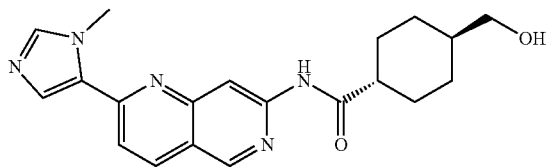 [SMILES: Cn1cncc1-c1ccc2cnc(NC(=O)[C@H]3CC[C@H](CO)CC3)cc2n1] 407
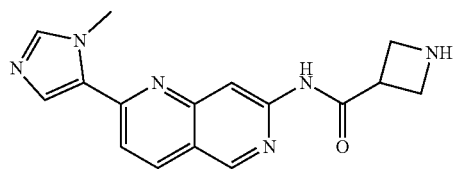 [SMILES: Cn1cncc1-c1ccc2cnc(NC(=O)C3CNC3)cc2n1] 408
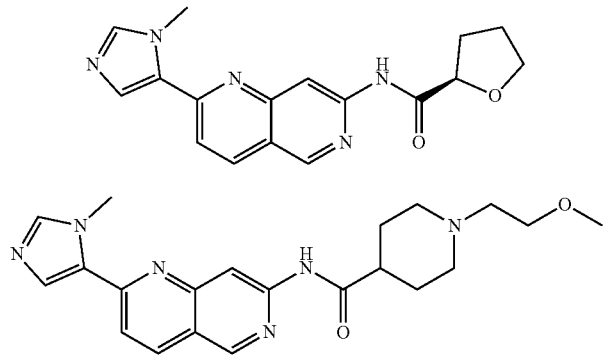 409
410
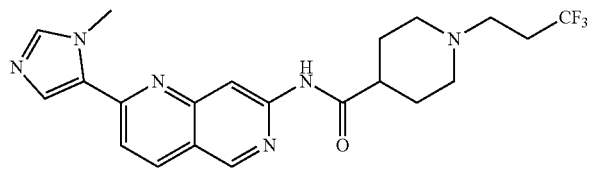 [SMILES: Cn1cncc1-c1ccc2cnc(NC(=O)C3CCN(CCC(F)(F)F)CC3)cc2n1] 411

TABLE 1-continued
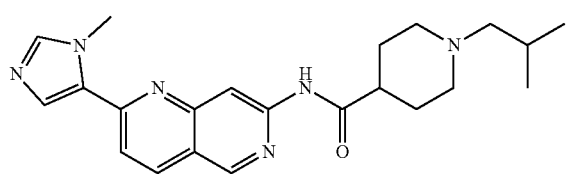 [SMILES: CC(C)CN1CCC(C(=O)Nc2cc3nc(-c4cncn4C)ccc3cn2)CC1] 412
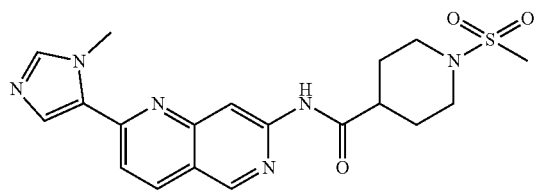 [SMILES: Cn1cncc1-c1ccc2cnc(NC(=O)C3CCN(S(C)(=O)=O)CC3)cc2n1] 413
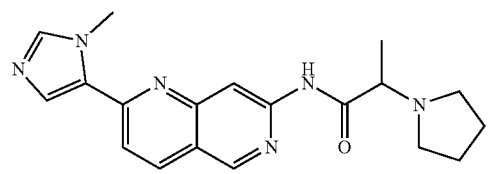 [SMILES: CC(C(=O)Nc1cc2nc(-c3cncn3C)ccc2cn1)N1CCCC1] 414
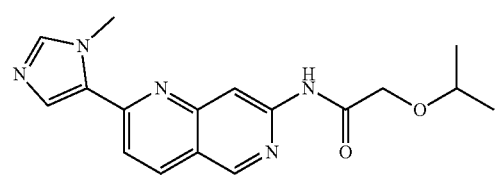 [SMILES: CC(C)OCC(=O)Nc1cc2nc(-c3cncn3C)ccc2cn1] 415
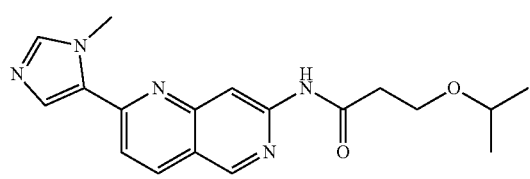 [SMILES: CC(C)OCCC(=O)Nc1cc2nc(-c3cncn3C)ccc2cn1] 416
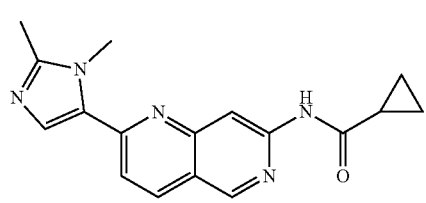 [SMILES: Cc1ncc(-c2ccc3cnc(NC(=O)C4CC4)cc3n2)n1C] 417
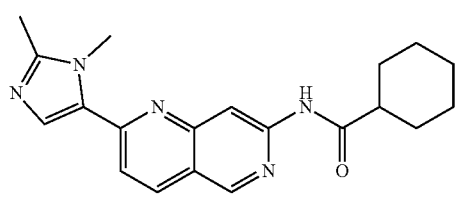 [SMILES: Cc1ncc(-c2ccc3cnc(NC(=O)C4CCCCC4)cc3n2)n1C] 418
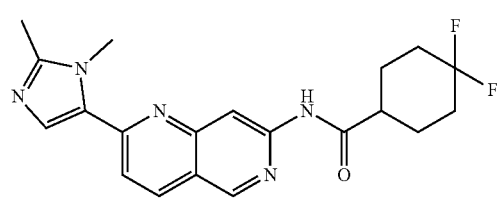 [SMILES: Cc1ncc(-c2ccc3cnc(NC(=O)C4CCC(F)(F)CC4)cc3n2)n1C] 419

TABLE 1-continued
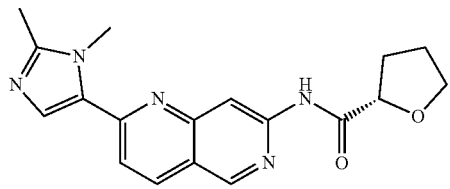 [SMILES: Cc1ncc(-c2ccc3cnc(NC(=O)[C@@H]4CCCO4)cc3n2)n1C] 420
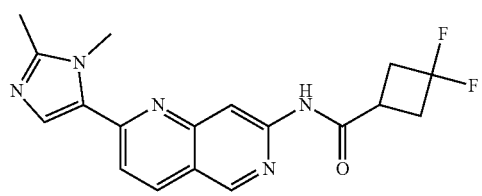 [SMILES: Cc1ncc(-c2ccc3cnc(NC(=O)C4CC(F)(F)C4)cc3n2)n1C] 421
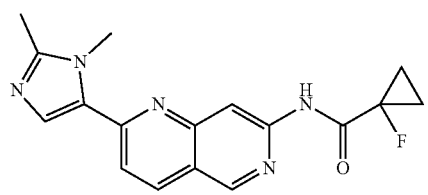 [SMILES: Cc1ncc(-c2ccc3cnc(NC(=O)C4(F)CC4)cc3n2)n1C] 422
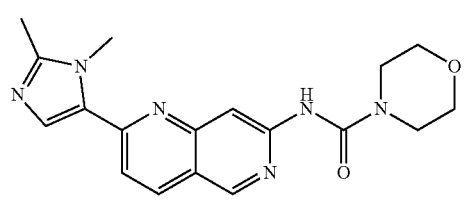 [SMILES: Cc1ncc(-c2ccc3cnc(NC(=O)N4CCOCC4)cc3n2)n1C] 423
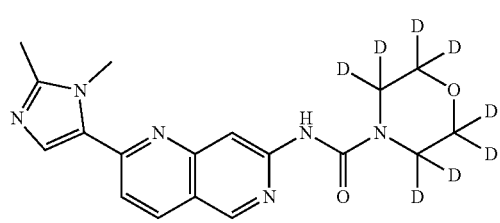 [SMILES: [2H]C1([2H])OC([2H])([2H])C([2H])([2H])N(C(=O)Nc2cc3nc(-c4cnc(C)n4C)ccc3cn2)C1([2H])[2H]] 424
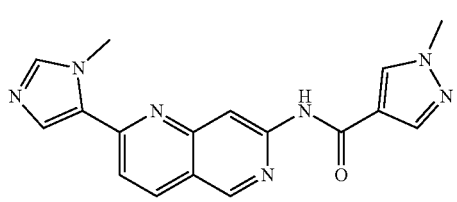 [SMILES: Cn1cc(C(=O)Nc2cc3nc(-c4cncn4C)ccc3cn2)cn1] 425
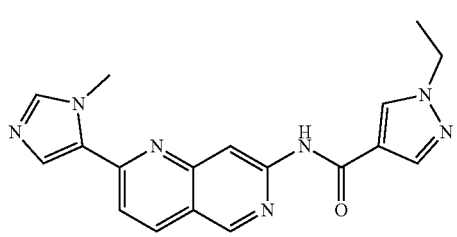 [SMILES: CCn1cc(C(=O)Nc2cc3nc(-c4cncn4C)ccc3cn2)cn1] 426

TABLE 1-continued
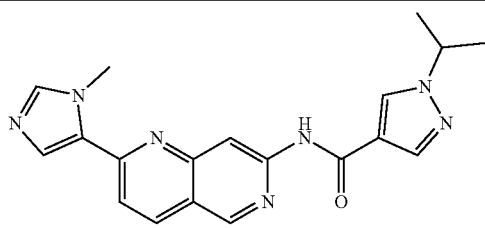 427
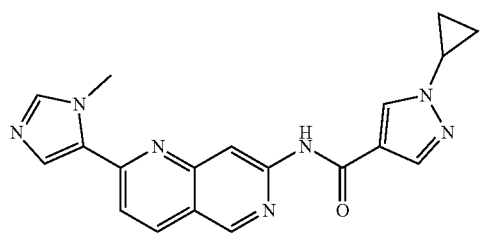 [SMILES: Cn1cncc1-c1ccc2cnc(NC(=O)c3cnn(C4CC4)c3)cc2n1] 428
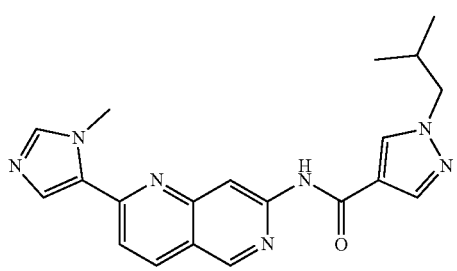 [SMILES: CC(C)Cn1cc(C(=O)Nc2cc3nc(-c4cncn4C)ccc3cn2)cn1] 429
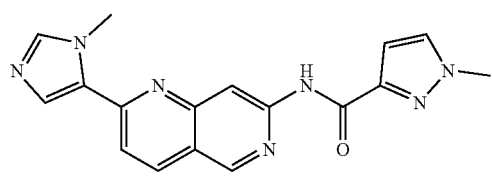 [SMILES: Cn1ccc(C(=O)Nc2cc3nc(-c4cncn4C)ccc3cn2)n1] 430
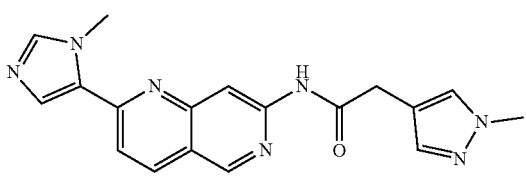 431
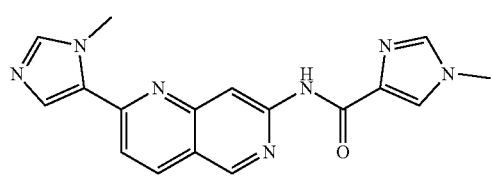 [SMILES: Cn1cnc(C(=O)Nc2cc3nc(-c4cncn4C)ccc3cn2)c1] 432
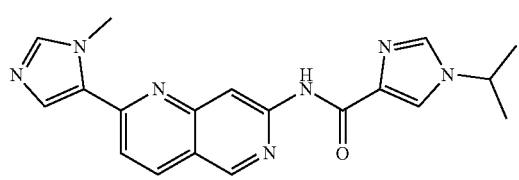 [SMILES: CC(C)n1cnc(C(=O)Nc2cc3nc(-c4cncn4C)ccc3cn2)c1] 433
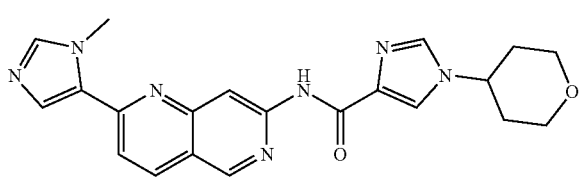 [SMILES: Cn1cncc1-c1ccc2cnc(NC(=O)c3cn(C4CCOCC4)cn3)cc2n1] 434

TABLE 1-continued
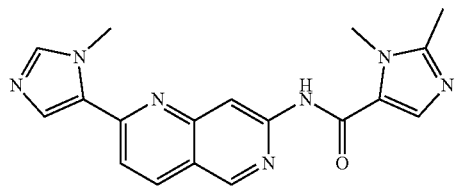 [SMILES: Cc1ncc(C(=O)Nc2cc3nc(-c4cncn4C)ccc3cn2)n1C] 435
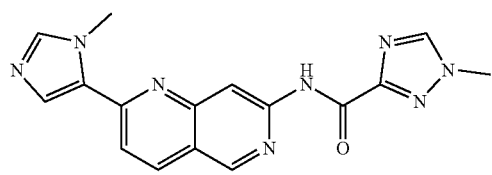 [SMILES: Cn1cnc(C(=O)Nc2cc3nc(-c4cncn4C)ccc3cn2)n1] 436
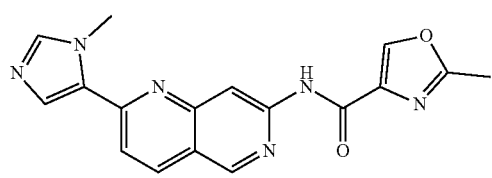 [SMILES: Cc1nc(C(=O)Nc2cc3nc(-c4cncn4C)ccc3cn2)co1] 437
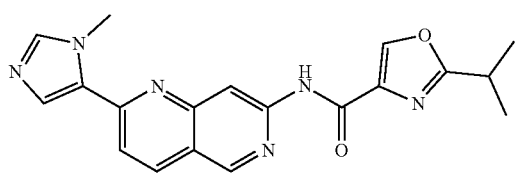 [SMILES: CC(C)c1nc(C(=O)Nc2cc3nc(-c4cncn4C)ccc3cn2)co1] 438
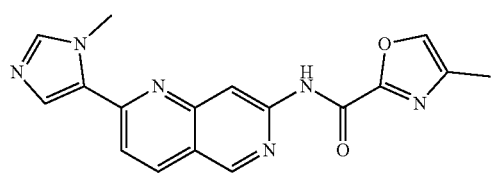 [SMILES: Cc1coc(C(=O)Nc2cc3nc(-c4cncn4C)ccc3cn2)n1] 439
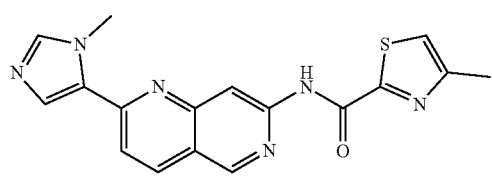 [SMILES: Cc1csc(C(=O)Nc2cc3nc(-c4cncn4C)ccc3cn2)n1] 440
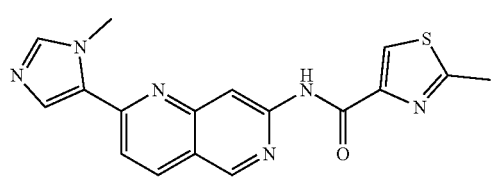 441
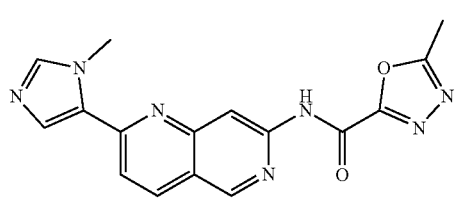 442

TABLE 1-continued
| | |
|---|---|
| 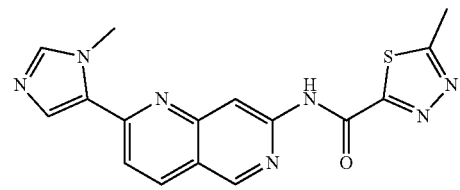 [SMILES: Cc1nnc(C(=O)Nc2cc3nc(-c4cncn4C)ccc3cn2)s1] | 443 |
| 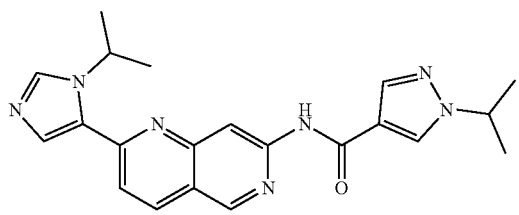 [SMILES: CC(C)n1cc(C(=O)Nc2cc3nc(-c4cncn4C(C)C)ccc3cn2)cn1] | 444 |
| 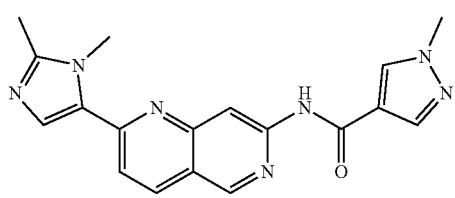 [SMILES: Cc1ncc(-c2ccc3cnc(NC(=O)c4cnn(C)c4)cc3n2)n1C] | 445 |
| 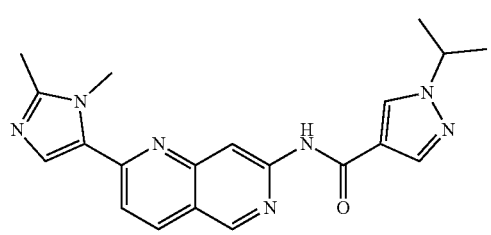 [SMILES: Cc1ncc(-c2ccc3cnc(NC(=O)c4cnn(C(C)C)c4)cc3n2)n1C] | 446 |
| 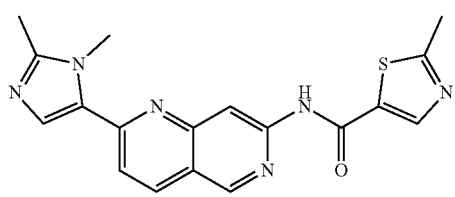 [SMILES: Cc1ncc(C(=O)Nc2cc3nc(-c4cnc(C)n4C)ccc3cn2)s1] | 447 |
| 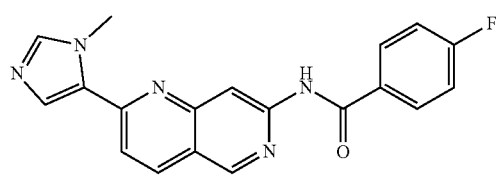 [SMILES: Cn1cncc1-c1ccc2cnc(NC(=O)c3ccc(F)cc3)cc2n1] | 448 |
| 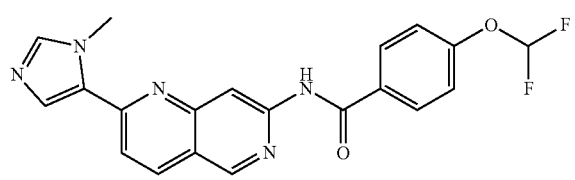 [SMILES: Cn1cncc1-c1ccc2cnc(NC(=O)c3ccc(OC(F)F)cc3)cc2n1] | 449 |
| 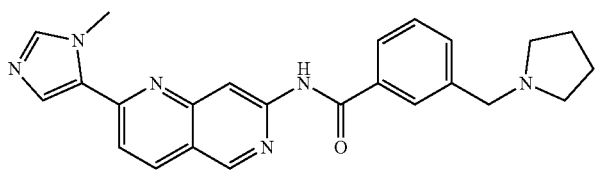 [SMILES: Cn1cncc1-c1ccc2cnc(NC(=O)c3cccc(CN4CCCC4)c3)cc2n1] | 450 |

TABLE 1-continued
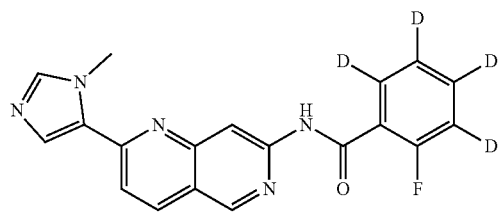 [SMILES: [2H]c1c([2H])c([2H])c(C(=O)Nc2cc3nc(-c4cncn4C)ccc3cn2)c(F)c1[2H]] 451
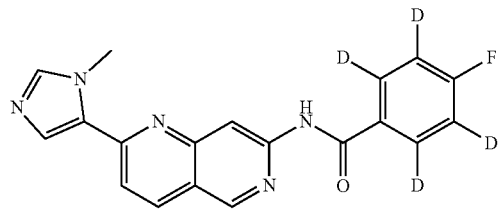 452
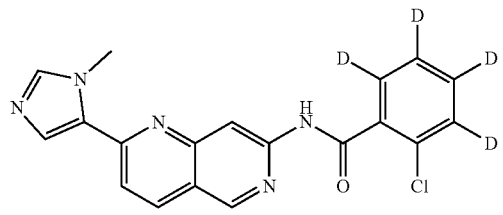 453
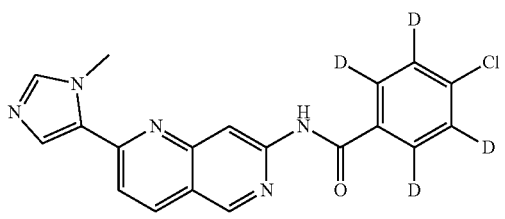 [SMILES: [2H]c1c([2H])c(C(=O)Nc2cc3nc(-c4cncn4C)ccc3cn2)c([2H])c([2H])c1Cl] 454
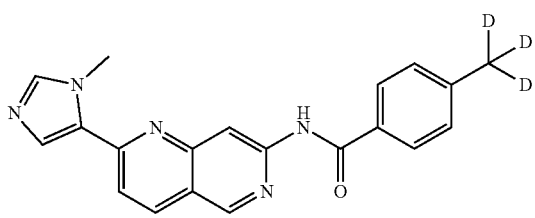 [SMILES: [2H]C([2H])([2H])c1ccc(C(=O)Nc2cc3nc(-c4cncn4C)ccc3cn2)cc1] 455
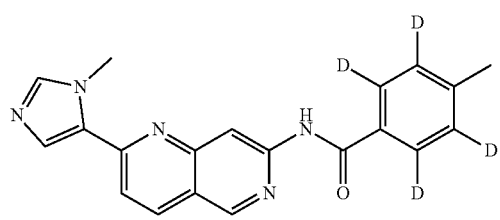 [SMILES: [2H]c1c([2H])c(C(=O)Nc2cc3nc(-c4cncn4C)ccc3cn2)c([2H])c([2H])c1C] 456
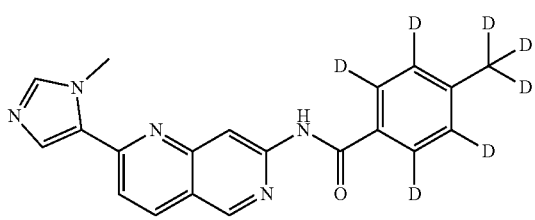 [SMILES: [2H]c1c([2H])c(C([2H])([2H])[2H])c([2H])c([2H])c1C(=O)Nc1cc2nc(-c3cncn3C)ccc2cn1] 457

TABLE 1-continued
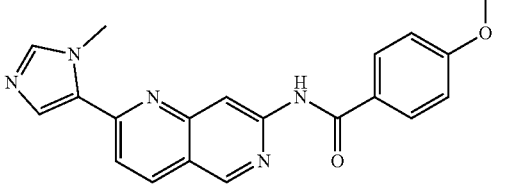
458
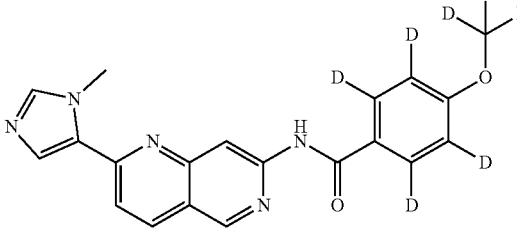
459
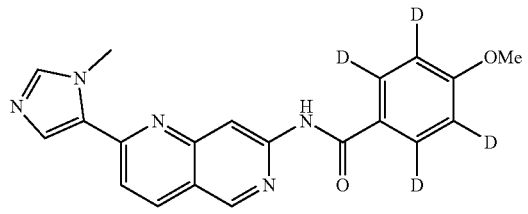 [SMILES: [2H]c1c([2H])c(C(=O)Nc2cc3nc(-c4cncn4C)ccc3cn2)c([2H])c([2H])c1OC]
460
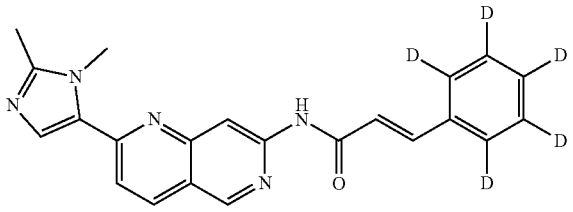 [SMILES: [2H]c1c([2H])c([2H])c(/C=C/C(=O)Nc2cc3nc(-c4cnc(C)n4C)ccc3cn2)c([2H])c1[2H]]
461
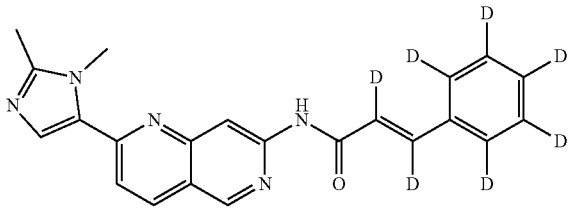 [SMILES: [2H]/C(C(=O)Nc1cc2nc(-c3cnc(C)n3C)ccc2cn1)=C(/[2H])c1c([2H])c([2H])c([2H])c([2H])c1[2H]]
462
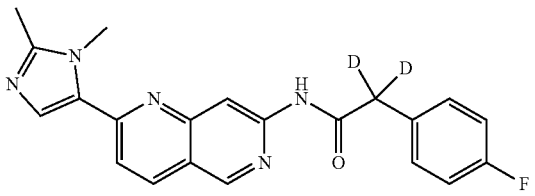 [SMILES: [2H]C([2H])(C(=O)Nc1cc2nc(-c3cnc(C)n3C)ccc2cn1)c1ccc(F)cc1]
463
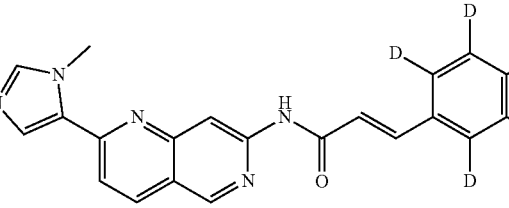
464

TABLE 1-continued
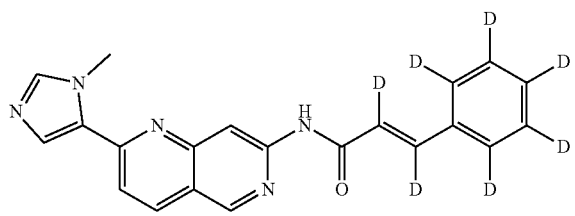 [SMILES: [2H]/C(C(=O)Nc1cc2nc(-c3cncn3C)ccc2cn1)=C(/[2H])c1c([2H])c([2H])c([2H])c([2H])c1[2H]]
465
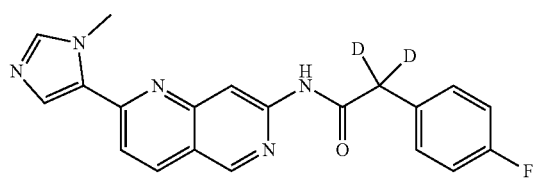 [SMILES: [2H]C([2H])(C(=O)Nc1cc2nc(-c3cncn3C)ccc2cn1)c1ccc(F)cc1]
466
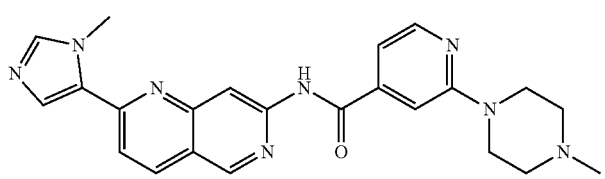 [SMILES: CN1CCN(c2cc(C(=O)Nc3cc4nc(-c5cncn5C)ccc4cn3)ccn2)CC1]
467
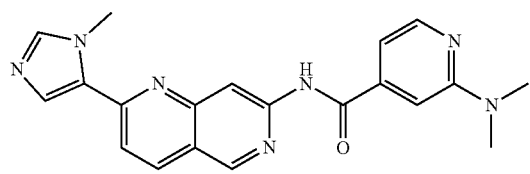 [SMILES: CN(C)c1cc(C(=O)Nc2cc3nc(-c4cncn4C)ccc3cn2)ccn1]
468
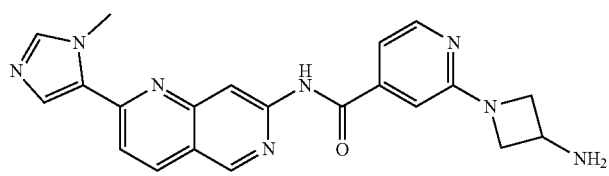
469
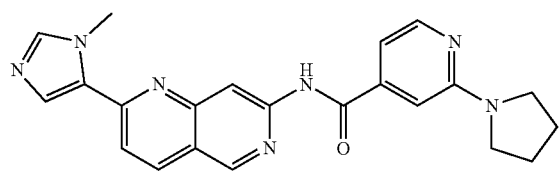 [SMILES: Cn1cncc1-c1ccc2cnc(NC(=O)c3ccnc(N4CCCC4)c3)cc2n1]
470
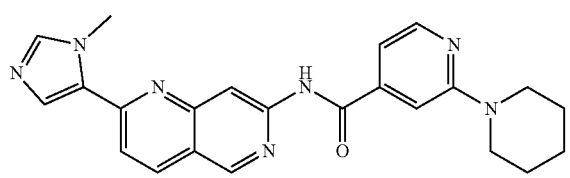 [SMILES: Cn1cncc1-c1ccc2cnc(NC(=O)c3ccnc(N4CCCCC4)c3)cc2n1]
471
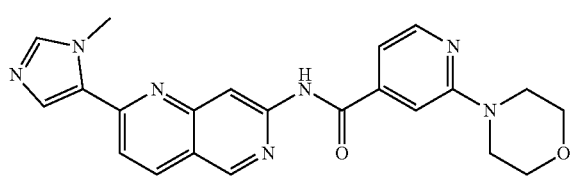 [SMILES: Cn1cncc1-c1ccc2cnc(NC(=O)c3ccnc(N4CCOCC4)c3)cc2n1]
472

TABLE 1-continued
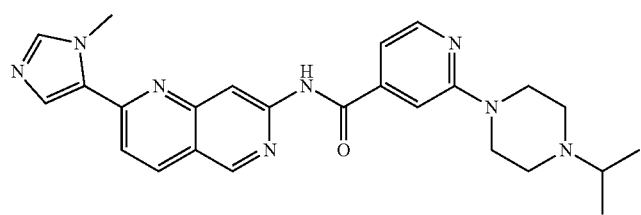 [SMILES: CC(C)N1CCN(c2cc(C(=O)Nc3cc4nc(-c5cncn5C)ccc4cn3)ccn2)CC1] 473
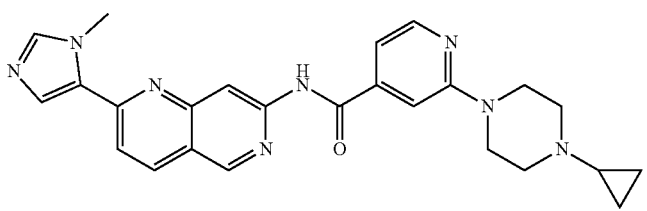 [SMILES: Cn1cncc1-c1ccc2cnc(NC(=O)c3ccnc(N4CCN(C5CC5)CC4)c3)cc2n1] 474
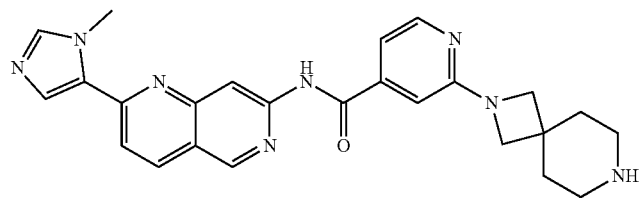 [SMILES: Cn1cncc1-c1ccc2cnc(NC(=O)c3ccnc(N4CC5(CCNCC5)C4)c3)cc2n1] 475
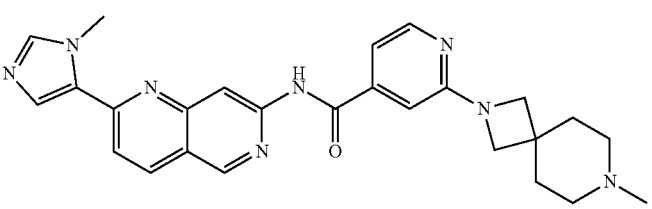 [SMILES: CN1CCC2(CC1)CN(c1cc(C(=O)Nc3cc4nc(-c5cncn5C)ccc4cn3)ccn1)C2] 476
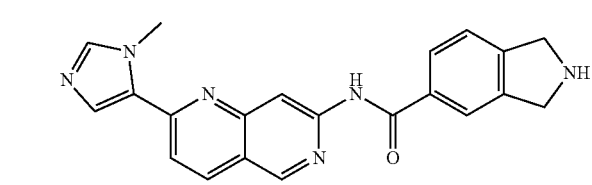 [SMILES: Cn1cncc1-c1ccc2cnc(NC(=O)c3ccc4c(c3)CNC4)cc2n1] 477
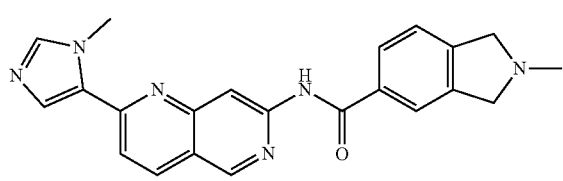 [SMILES: CN1Cc2ccc(C(=O)Nc3cc4nc(-c5cncn5C)ccc4cn3)cc2C1] 478
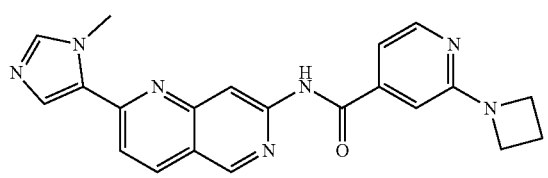 [SMILES: Cn1cncc1-c1ccc2cnc(NC(=O)c3ccnc(N4CCC4)c3)cc2n1] 479
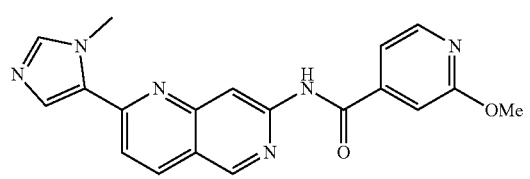 [SMILES: COc1cc(C(=O)Nc2cc3nc(-c4cncn4C)ccc3cn2)ccn1] 480

TABLE 1-continued
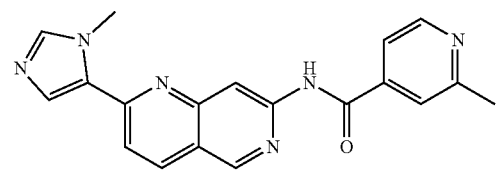 [SMILES: Cc1cc(C(=O)Nc2cc3nc(-c4cncn4C)ccc3cn2)ccn1] 481
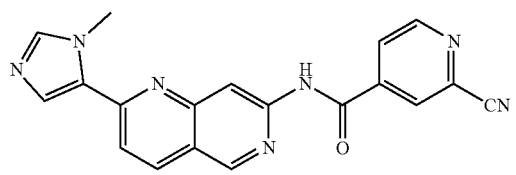 [SMILES: Cn1cncc1-c1ccc2cnc(NC(=O)c3ccnc(C#N)c3)cc2n1] 482
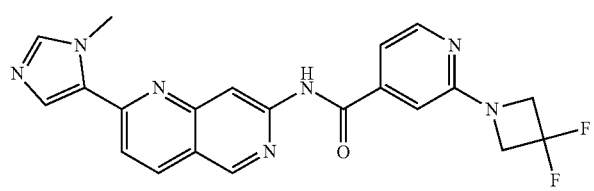 [SMILES: Cn1cncc1-c1ccc2cnc(NC(=O)c3ccnc(N4CC(F)(F)C4)c3)cc2n1] 483
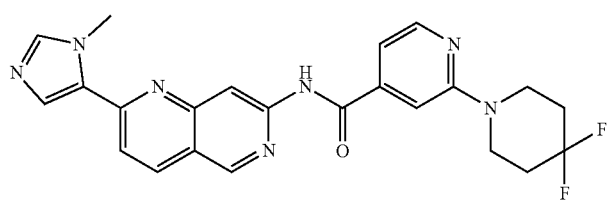 [SMILES: Cn1cncc1-c1ccc2cnc(NC(=O)c3ccnc(N4CCC(F)(F)CC4)c3)cc2n1] 484
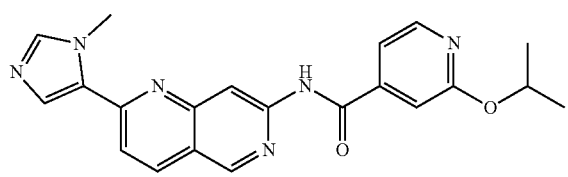 [SMILES: CC(C)Oc1cc(C(=O)Nc2cc3nc(-c4cncn4C)ccc3cn2)ccn1] 485
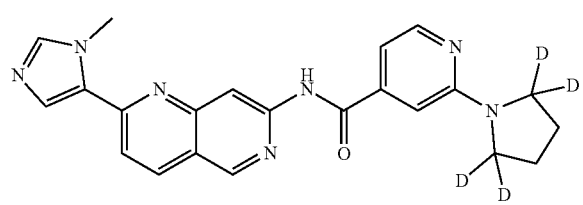 [SMILES: [2H]C1([2H])CCC([2H])([2H])N1c1cc(C(=O)Nc2cc3nc(-c4cncn4C)ccc3cn2)ccn1] 486
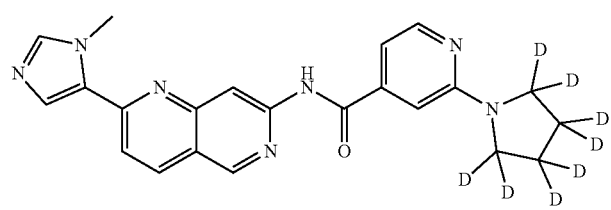 487
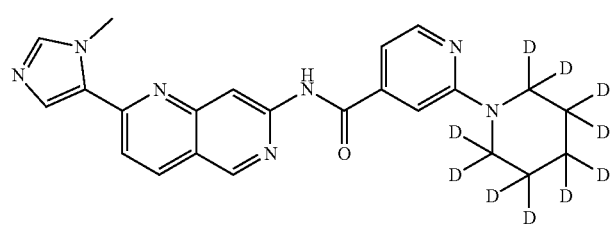 [SMILES: [2H]C1([2H])N(c2cc(C(=O)Nc3cc4nc(-c5cncn5C)ccc4cn3)ccn2)C([2H])([2H])C([2H])([2H])C([2H])([2H])C1([2H])[2H]] 488

TABLE 1-continued
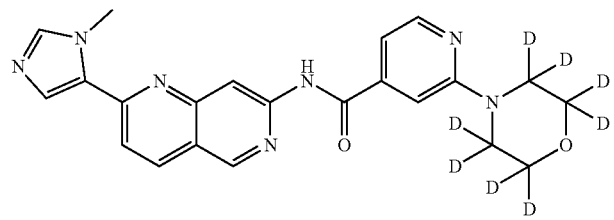 [SMILES: [2H]C1([2H])OC([2H])([2H])C([2H])([2H])N(c2cc(C(=O)Nc3cc4nc(-c5cncn5C)ccc4cn3)ccn2)C1([2H])[2H]] 489
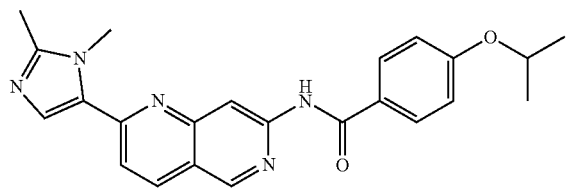 [SMILES: Cc1ncc(-c2ccc3cnc(NC(=O)c4ccc(OC(C)C)cc4)cc3n2)n1C] 490
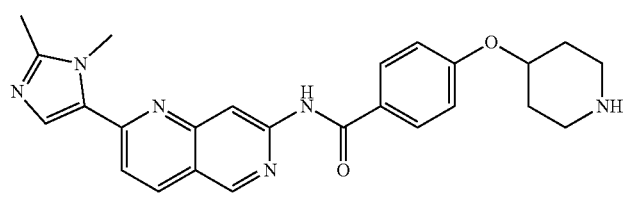 [SMILES: Cc1ncc(-c2ccc3cnc(NC(=O)c4ccc(OC5CCNCC5)cc4)cc3n2)n1C] 491
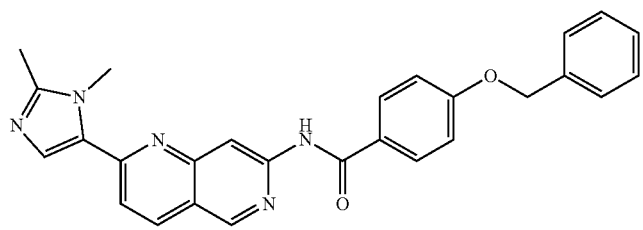 [SMILES: Cc1ncc(-c2ccc3cnc(NC(=O)c4ccc(OCc5ccccc5)cc4)cc3n2)n1C] 492
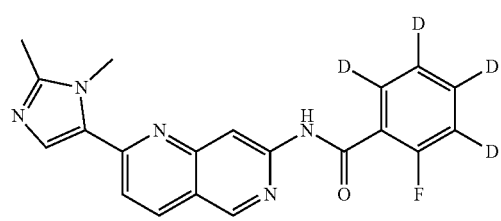 [SMILES: [2H]c1c([2H])c(C(=O)Nc2cc3nc(-c4cnc(C)n4C)ccc3cn2)c([2H])c([2H])c1F] 493
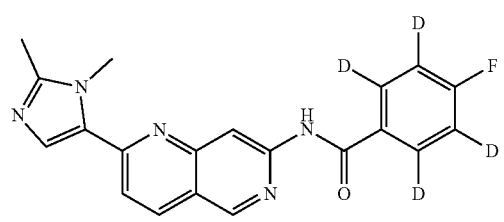 494
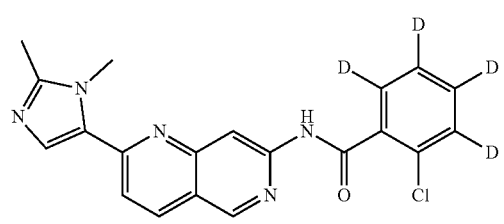 [SMILES: [2H]c1c([2H])c([2H])c(C(=O)Nc2cc3nc(-c4cnc(C)n4C)ccc3cn2)c(Cl)c1[2H]] 495

TABLE 1-continued

| | |
|---|---|
| [structure] | 496 |
| [structure] | 497 |
| [structure] | 498 |
| [structure] | 499 |
| [structure] | 500 |
| [structure] | 501 |
| [structure] | 502 |

TABLE 1-continued
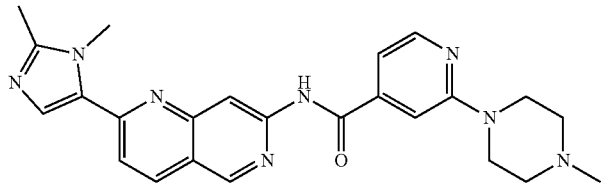 [SMILES: Cc1ncc(-c2ccc3cnc(NC(=O)c4ccnc(N5CCN(C)CC5)c4)cc3n2)n1C] 503
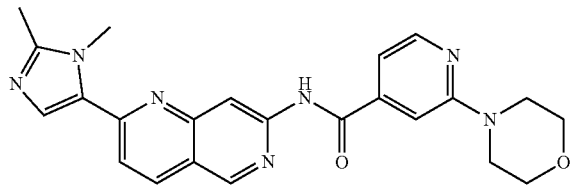 [SMILES: Cc1ncc(-c2ccc3cnc(NC(=O)c4ccnc(N5CCOCC5)c4)cc3n2)n1C] 504
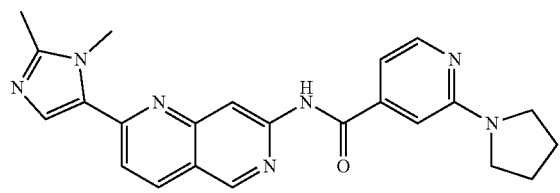 [SMILES: Cc1ncc(-c2ccc3cnc(NC(=O)c4ccnc(N5CCCC5)c4)cc3n2)n1C] 505
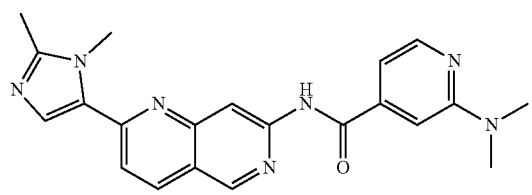 [SMILES: Cc1ncc(-c2ccc3cnc(NC(=O)c4ccnc(N(C)C)c4)cc3n2)n1C] 506
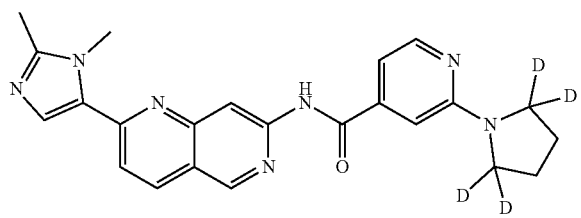 [SMILES: [2H]C1([2H])CCC([2H])([2H])N1c1cc(C(=O)Nc2cc3nc(-c4cnc(C)n4C)ccc3cn2)ccn1] 507
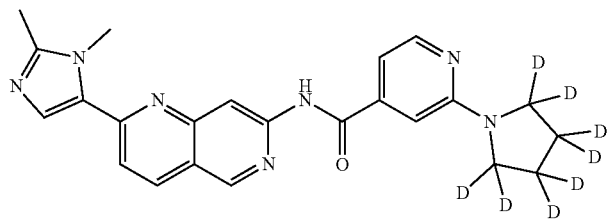 [SMILES: [2H]C1([2H])N(c2cc(C(=O)Nc3cc4nc(-c5cnc(C)n5C)ccc4cn3)ccn2)C([2H])([2H])C([2H])([2H])C1([2H])[2H]] 508
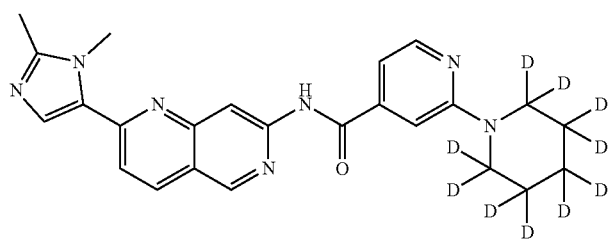 [SMILES: [2H]C1([2H])N(c2cc(C(=O)Nc3cc4nc(-c5cnc(C)n5C)ccc4cn3)ccn2)C([2H])([2H])C([2H])([2H])C([2H])([2H])C1([2H])[2H]] 509

TABLE 1-continued
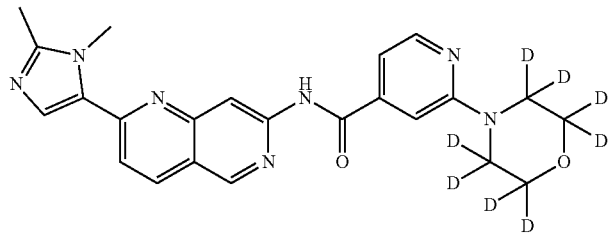 [SMILES: [2H]C1([2H])OC([2H])([2H])C([2H])([2H])N(c2cc(C(=O)Nc3cc4nc(-c5cnc(C)n5C)ccc4cn3)ccn2)C1([2H])[2H]] 510
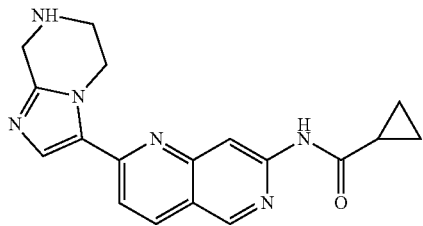 [SMILES: O=C(Nc1cc2nc(-c3cnc4n3CCNC4)ccc2cn1)C1CC1] 511
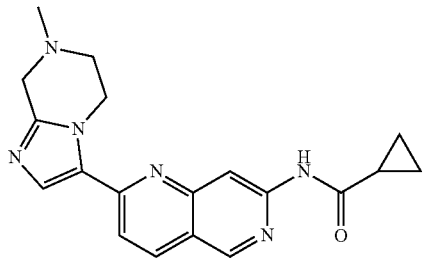 [SMILES: CN1CCn2c(-c3ccc4cnc(NC(=O)C5CC5)cc4n3)cnc2C1] 512
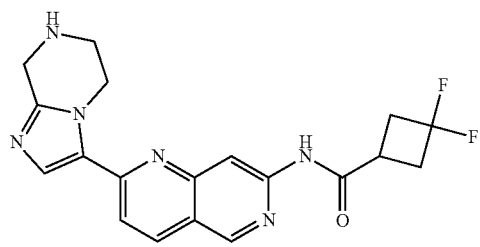 513
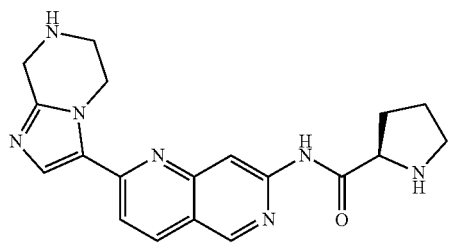 [SMILES: O=C(Nc1cc2nc(-c3cnc4n3CCNC4)ccc2cn1)[C@H]1CCCN1] 514
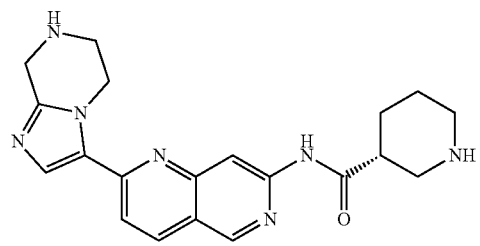 [SMILES: O=C(Nc1cc2nc(-c3cnc4n3CCNC4)ccc2cn1)[C@@H]1CCCNC1] 515

TABLE 1-continued
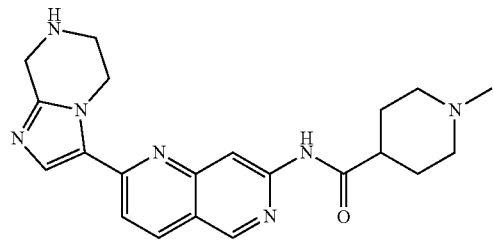 [SMILES: CN1CCC(C(=O)Nc2cc3nc(-c4cnc5n4CCNC5)ccc3cn2)CC1] 516
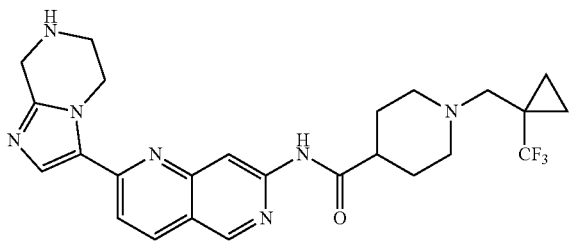 [SMILES: O=C(Nc1cc2nc(-c3cnc4n3CCNC4)ccc2cn1)C1CCN(CC2(C(F)(F)F)CC2)CC1] 517
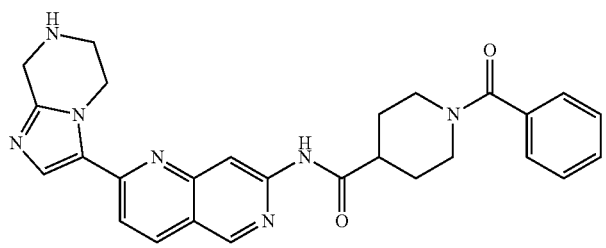 [SMILES: O=C(Nc1cc2nc(-c3cnc4n3CCNC4)ccc2cn1)C1CCN(C(=O)c2ccccc2)CC1] 518
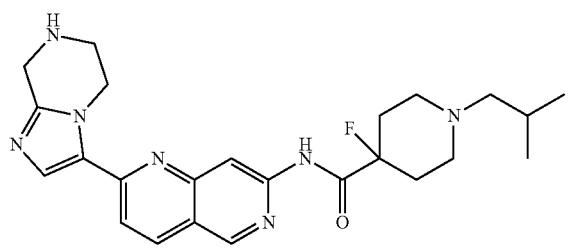 [SMILES: CC(C)CN1CCC(F)(C(=O)Nc2cc3nc(-c4cnc5n4CCNC5)ccc3cn2)CC1] 519
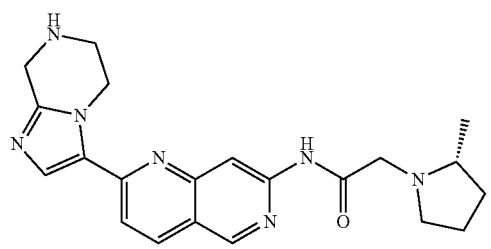 [SMILES: C[C@@H]1CCCN1CC(=O)Nc1cc2nc(-c3cnc4n3CCNC4)ccc2cn1] 520
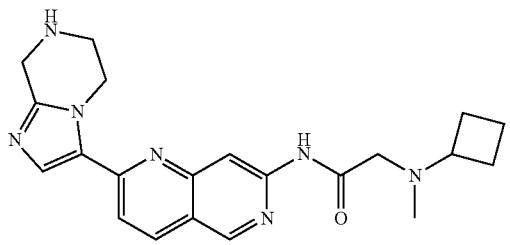 [SMILES: CN(CC(=O)Nc1cc2nc(-c3cnc4n3CCNC4)ccc2cn1)C1CCC1] 521

TABLE 1-continued
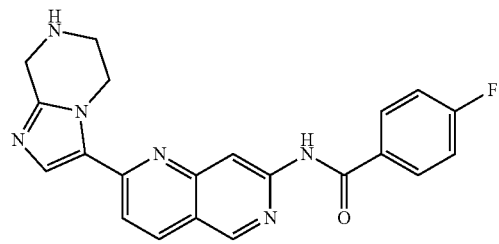 [SMILES: O=C(Nc1cc2nc(-c3cnc4n3CCNC4)ccc2cn1)c1ccc(F)cc1]
522
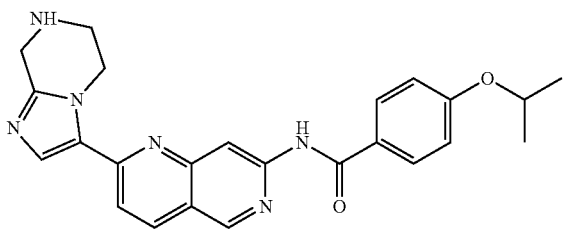 [SMILES: CC(C)Oc1ccc(C(=O)Nc2cc3nc(-c4cnc5n4CCNC5)ccc3cn2)cc1]
523
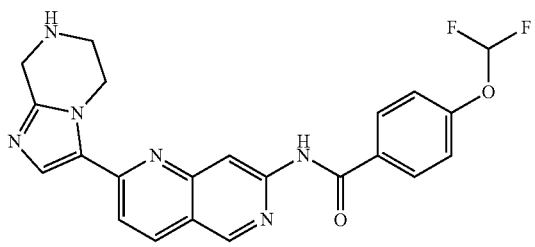 [SMILES: O=C(Nc1cc2nc(-c3cnc4n3CCNC4)ccc2cn1)c1ccc(OC(F)F)cc1]
524
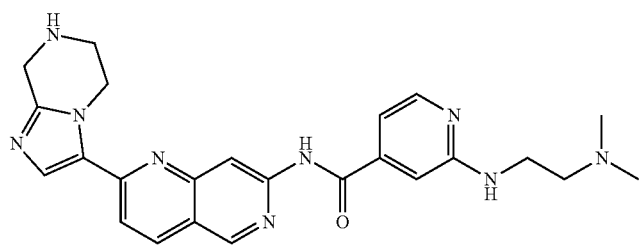 [SMILES: CN(C)CCNc1cc(C(=O)Nc2cc3nc(-c4cnc5n4CCNC5)ccc3cn2)ccn1]
525
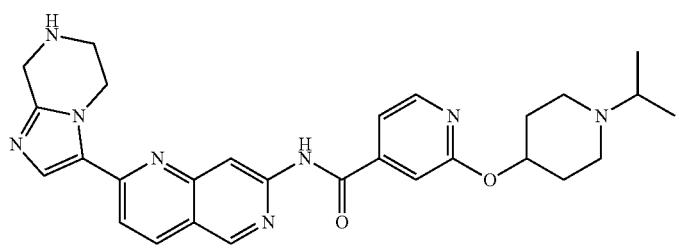 [SMILES: CC(C)N1CCC(Oc2cc(C(=O)Nc3cc4nc(-c5cnc6n5CCNC6)ccc4cn3)ccn2)CC1]
526
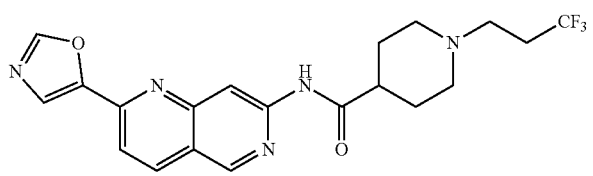 [SMILES: O=C(Nc1cc2nc(-c3cnco3)ccc2cn1)C1CCN(CCC(F)(F)F)CC1]
527
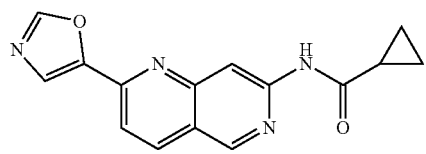 [SMILES: O=C(Nc1cc2nc(-c3cnco3)ccc2cn1)C1CC1]
528

TABLE 1-continued

| | |
|---|---|
| (structure) | 529 |
| (structure) | 530 |
| (structure) | 531 |
| (structure) | 532 |
| (structure) | 533 |
| (structure) | 534 |
| (structure) | 535 |
| (structure) | 536 |

TABLE 1-continued
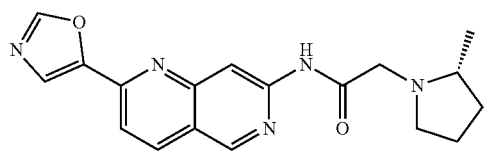 [SMILES: C[C@@H]1CCCN1CC(=O)Nc1cc2nc(-c3cnco3)ccc2cn1] 537
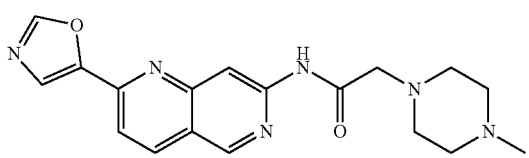 [SMILES: CN1CCN(CC(=O)Nc2cc3nc(-c4cnco4)ccc3cn2)CC1] 538
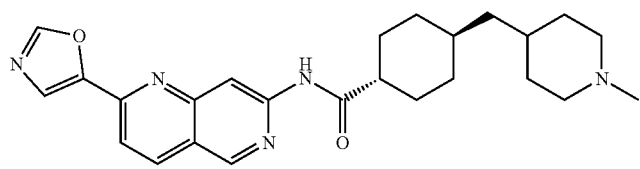 [SMILES: CN1CCC(C[C@H]2CC[C@H](C(=O)Nc3cc4nc(-c5cnco5)ccc4cn3)CC2)CC1] 539
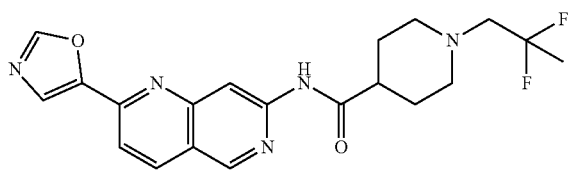 [SMILES: CC(F)(F)CN1CCC(C(=O)Nc2cc3nc(-c4cnco4)ccc3cn2)CC1] 540
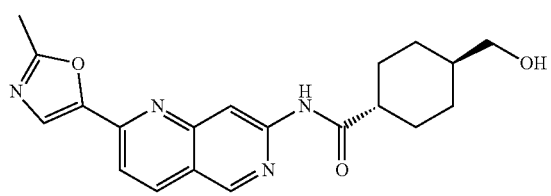 541
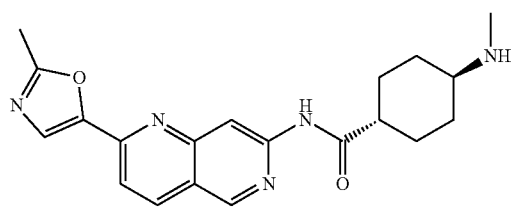 [SMILES: CN[C@H]1CC[C@H](C(=O)Nc2cc3nc(-c4cnc(C)o4)ccc3cn2)CC1] 542
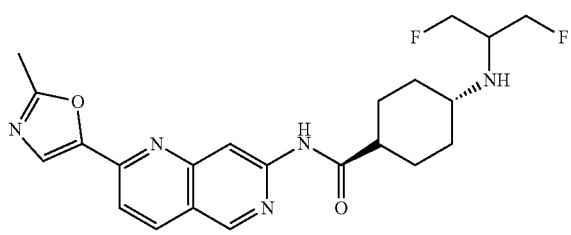 543
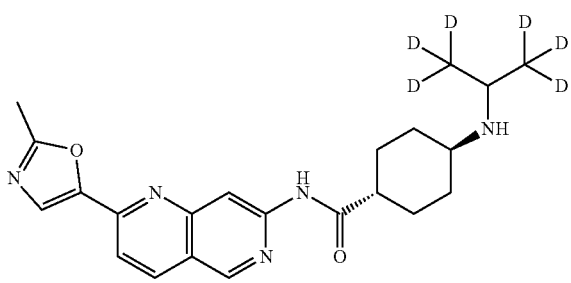 [SMILES: [2H]C([2H])([2H])C(N[C@H]1CC[C@H](C(=O)Nc2cc3nc(-c4cnc(C)o4)ccc3cn2)CC1)C([2H])([2H])[2H]] 544

TABLE 1-continued
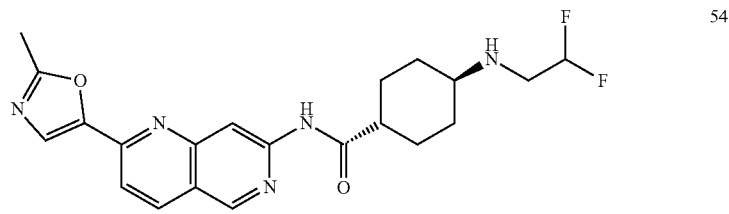 545
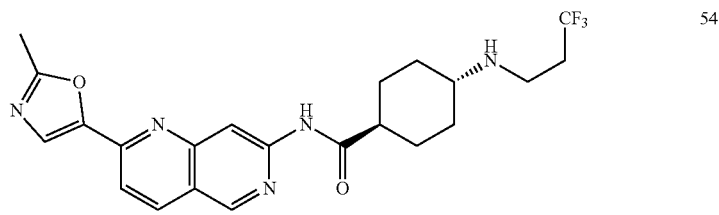 546
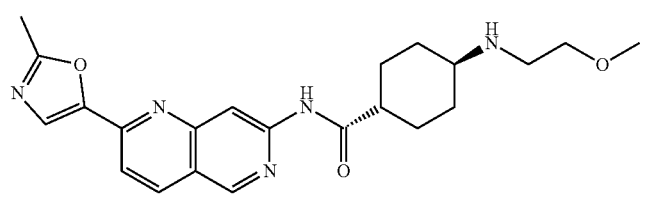 547
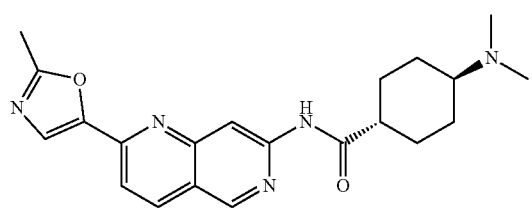 548
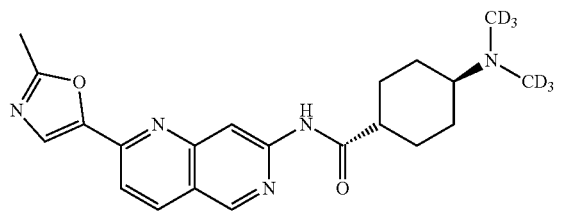 549
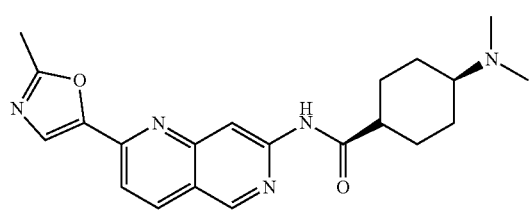 550
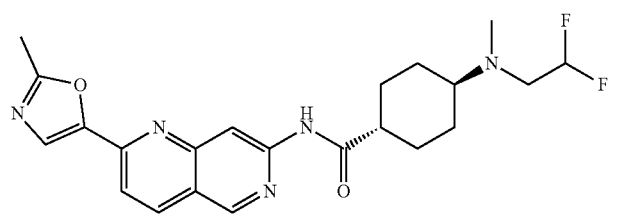 [SMILES: Cc1ncc(-c2ccc3cnc(NC(=O)[C@H]4CC[C@H](N(C)CC(F)F)CC4)cc3n2)o1] 551

TABLE 1-continued
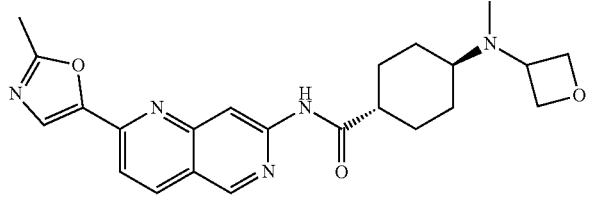 [SMILES: Cc1ncc(-c2ccc3cnc(NC(=O)[C@H]4CC[C@H](N(C)C5COC5)CC4)cc3n2)o1] 552
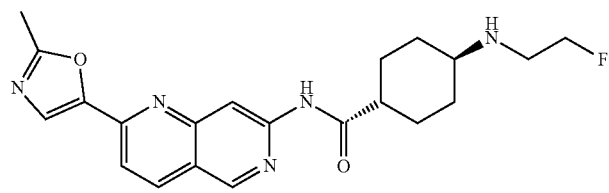 553
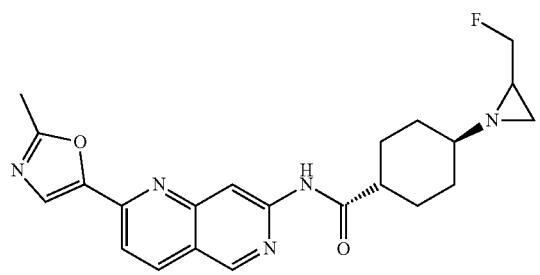 554
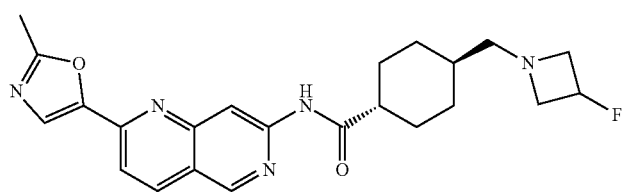 [SMILES: Cc1ncc(-c2ccc3cnc(NC(=O)[C@H]4CC[C@H](CN5CC(F)C5)CC4)cc3n2)o1] 555
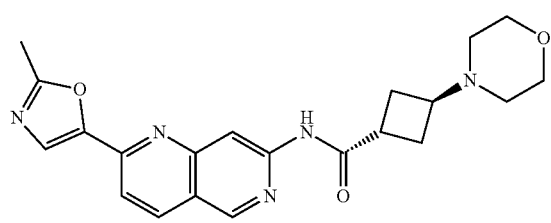 556
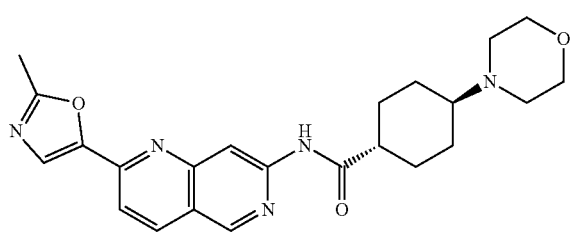 [SMILES: Cc1ncc(-c2ccc3cnc(NC(=O)[C@H]4CC[C@H](N5CCOCC5)CC4)cc3n2)o1] 557
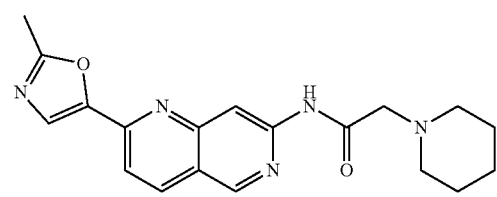 558

TABLE 1-continued

TABLE 1-continued
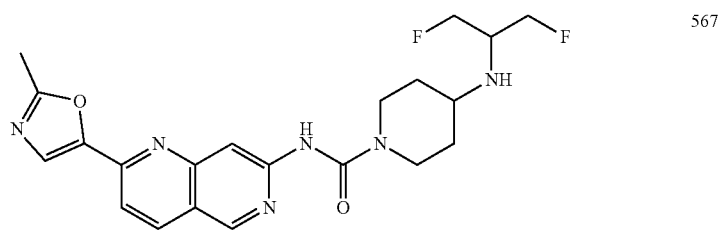 567
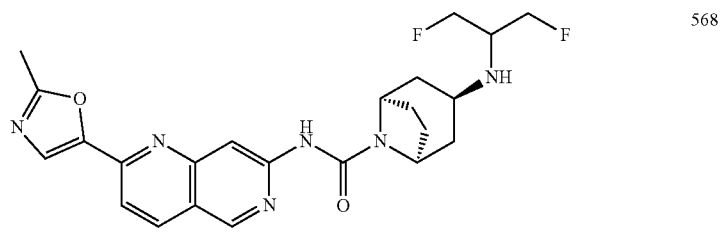 568
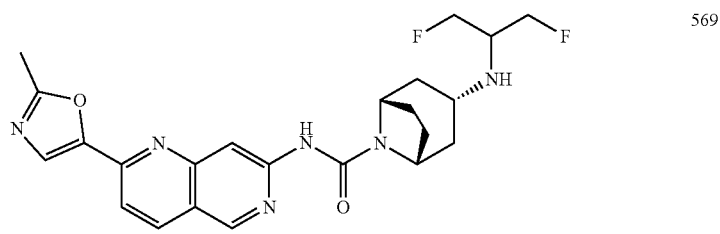 569
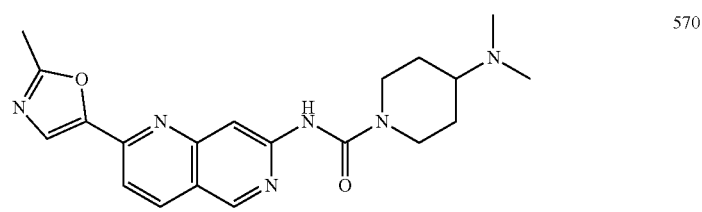 570
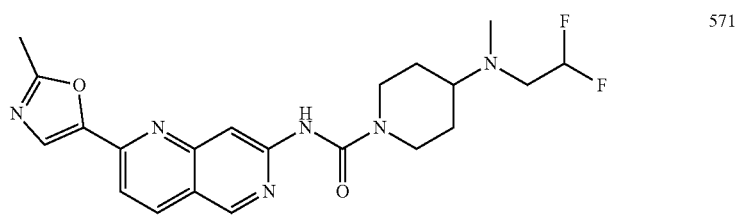 571
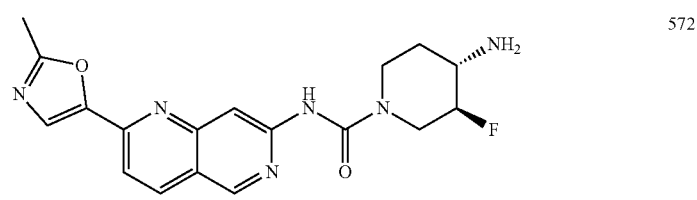 572
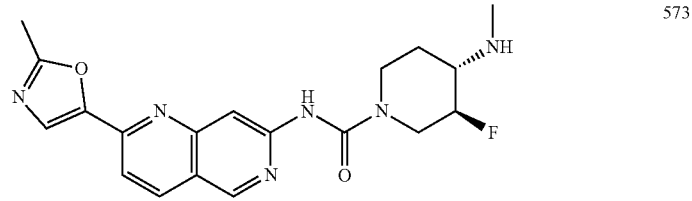 573

TABLE 1-continued
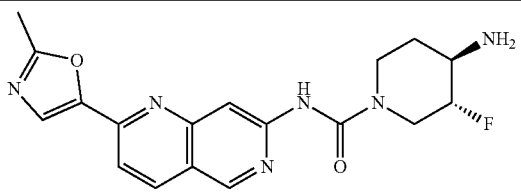 574
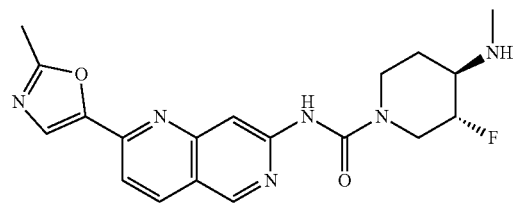 [SMILES: CN[C@@H]1CCN(C(=O)Nc2cc3nc(-c4cnc(C)o4)ccc3cn2)C[C@H]1F] 575
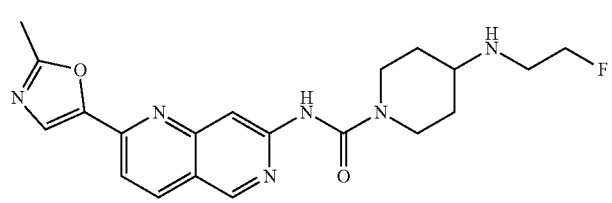 [SMILES: Cc1ncc(-c2ccc3cnc(NC(=O)N4CCC(NCCF)CC4)cc3n2)o1] 576
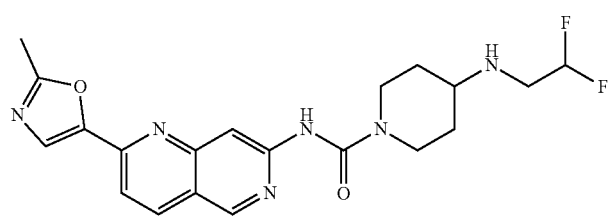 [SMILES: Cc1ncc(-c2ccc3cnc(NC(=O)N4CCC(NCC(F)F)CC4)cc3n2)o1] 577
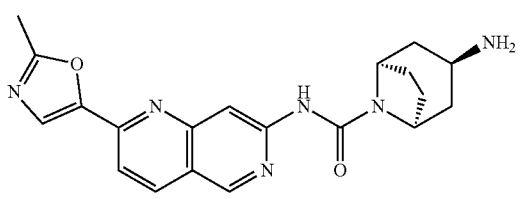 [SMILES: Cc1ncc(-c2ccc3cnc(NC(=O)N4[C@@H]5CC[C@H]4C[C@H](N)C5)cc3n2)o1] 578
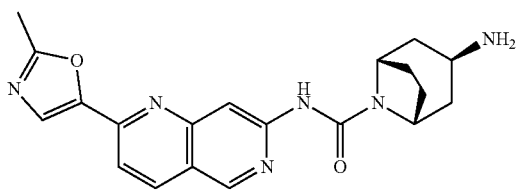 [SMILES: Cc1ncc(-c2ccc3cnc(NC(=O)N4[C@@H]5CC[C@H]4C[C@@H](N)C5)cc3n2)o1] 579
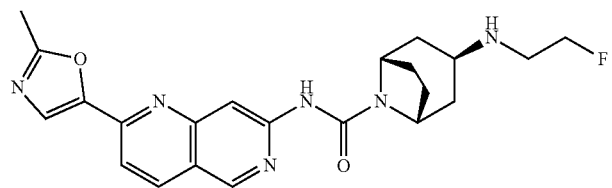 580
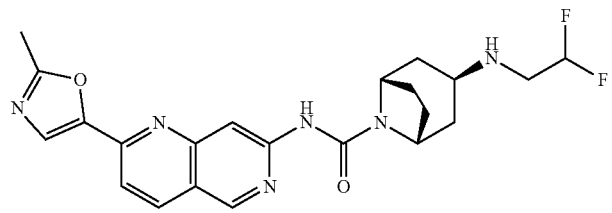 [SMILES: Cc1ncc(-c2ccc3cnc(NC(=O)N4[C@@H]5CC[C@H]4C[C@@H](NCC(F)F)C5)cc3n2)o1] 581

TABLE 1-continued
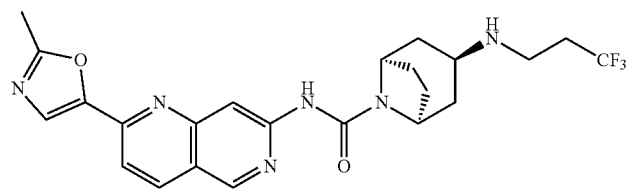 [SMILES: Cc1ncc(-c2ccc3cnc(NC(=O)N4[C@@H]5CC[C@H]4C[C@H](NCCC(F)(F)F)C5)cc3n2)o1] 582
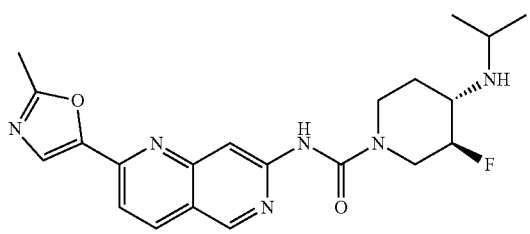 583
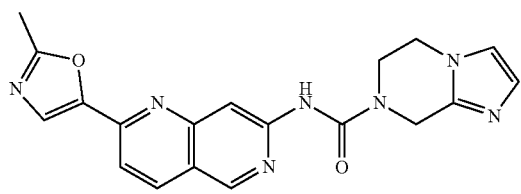 584
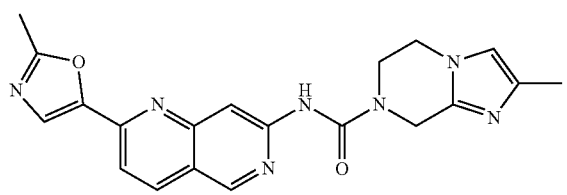 [SMILES: Cc1cn2c(n1)CN(C(=O)Nc1cc3nc(-c4cnc(C)o4)ccc3cn1)CC2] 585
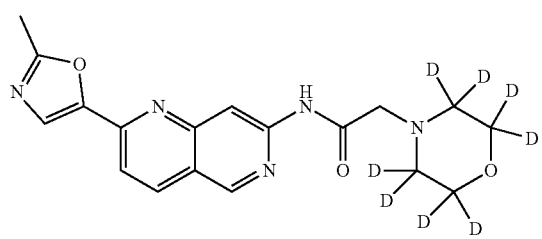 [SMILES: [2H]C1([2H])OC([2H])([2H])C([2H])([2H])N(CC(=O)Nc2cc3nc(-c4cnc(C)o4)ccc3cn2)C1([2H])[2H]] 586
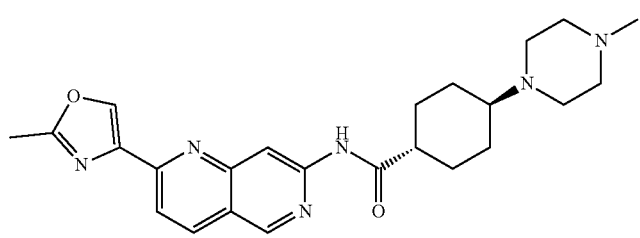 587
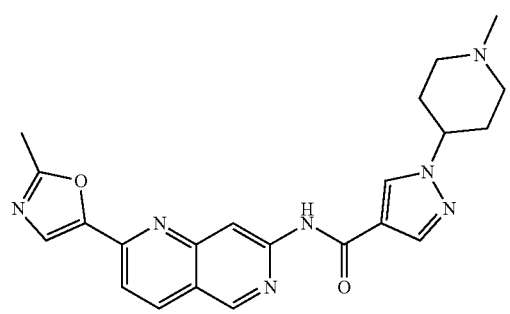 588

TABLE 1-continued

| | |
|---|---|
| (structure) | 589 |
| (structure) | 590 |
| (structure) | 591 |
| (structure) | 592 |
| (structure) | 593 |
| (structure) | 594 |
| (structure) | 595 |
| (structure) | 596 |
| (structure) | 597 |

TABLE 1-continued
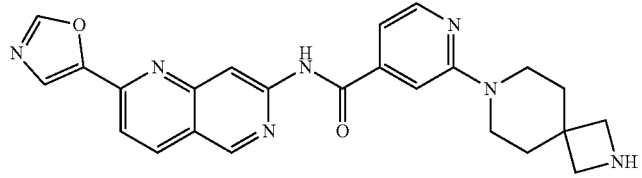 [SMILES: O=C(Nc1cc2nc(-c3cnco3)ccc2cn1)c1ccnc(N2CCC3(CC2)CNC3)c1] 598
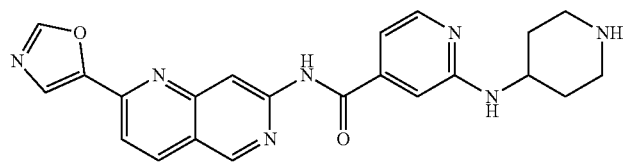 [SMILES: O=C(Nc1cc2nc(-c3cnco3)ccc2cn1)c1ccnc(NC2CCNCC2)c1] 599
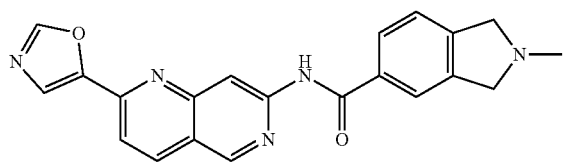 [SMILES: CN1Cc2ccc(C(=O)Nc3cc4nc(-c5cnco5)ccc4cn3)cc2C1] 600
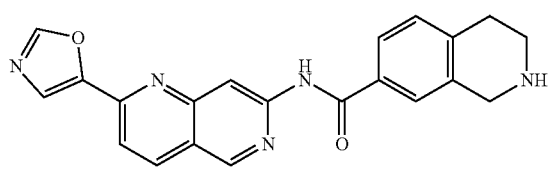 [SMILES: O=C(Nc1cc2nc(-c3cnco3)ccc2cn1)c1ccc2c(c1)CNCC2] 601
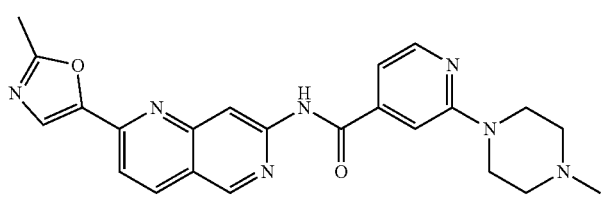 [SMILES: Cc1ncc(-c2ccc3cnc(NC(=O)c4ccnc(N5CCN(C)CC5)c4)cc3n2)o1] 602
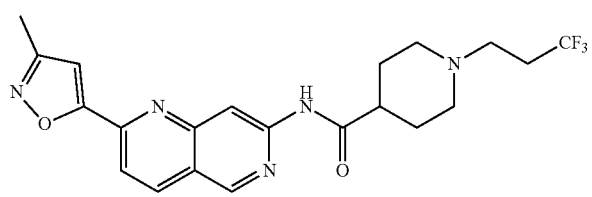 [SMILES: Cc1cc(-c2ccc3cnc(NC(=O)C4CCN(CCC(F)(F)F)CC4)cc3n2)on1] 603
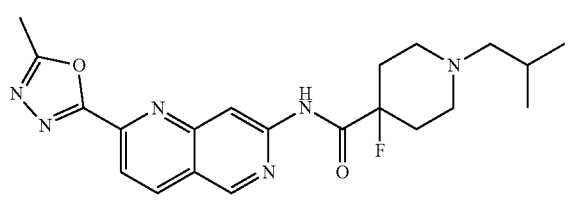 [SMILES: Cc1nnc(-c2ccc3cnc(NC(=O)C4(F)CCN(CC(C)C)CC4)cc3n2)o1] 604
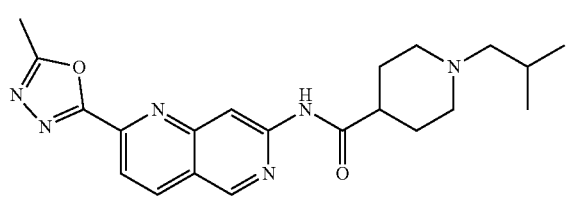 [SMILES: Cc1nnc(-c2ccc3cnc(NC(=O)C4CCN(CC(C)C)CC4)cc3n2)o1] 605

TABLE 1-continued
| | |
|---|---|
|  | 606 |
| 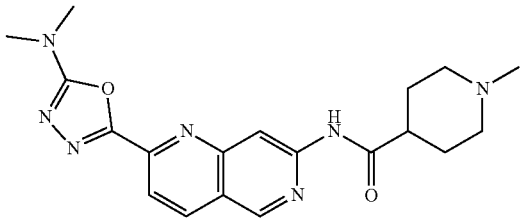 | 607 |
| 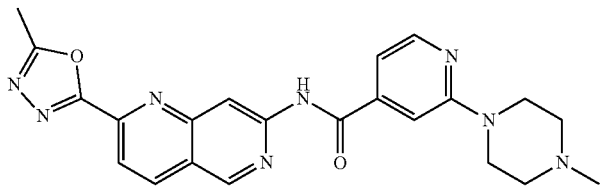 | 608 |
| 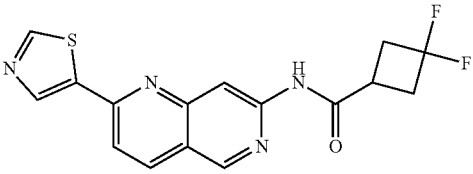 [SMILES: O=C(Nc1cc2nc(-c3cncs3)ccc2cn1)C1CC(F)(F)C1] | 609 |
| 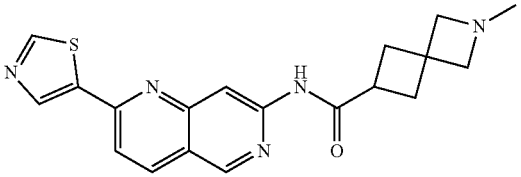 [SMILES: CN1CC2(CC(C(=O)Nc3cc4nc(-c5cncs5)ccc4cn3)C2)C1] | 610 |
| 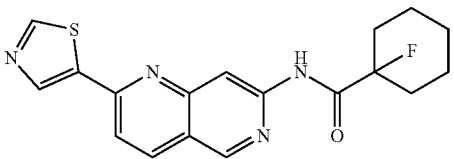 | 611 |
| 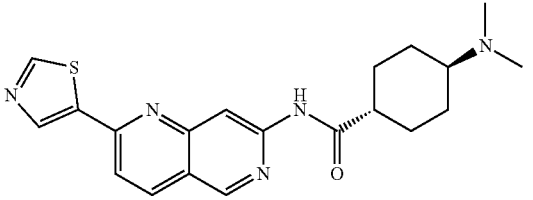 [SMILES: CN(C)[C@H]1CC[C@H](C(=O)Nc2cc3nc(-c4cncs4)ccc3cn2)CC1] | 612 |
| 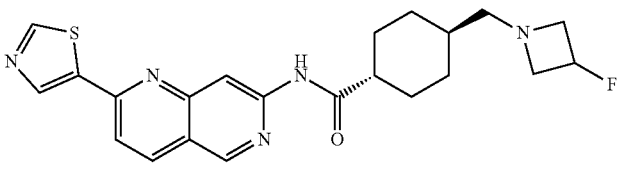 [SMILES: O=C(Nc1cc2nc(-c3cncs3)ccc2cn1)[C@H]1CC[C@H](CN2CC(F)C2)CC1] | 613 |

TABLE 1-continued
| | |
|---|---|
| 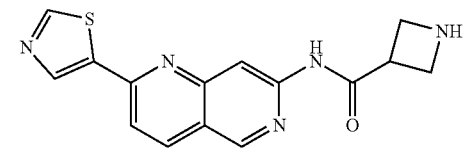 [SMILES: O=C(Nc1cc2nc(-c3cncs3)ccc2cn1)C1CNC1] | 614 |
| 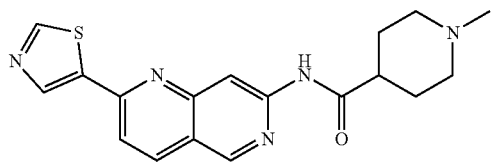 [SMILES: CN1CCC(C(=O)Nc2cc3nc(-c4cncs4)ccc3cn2)CC1] | 615 |
| 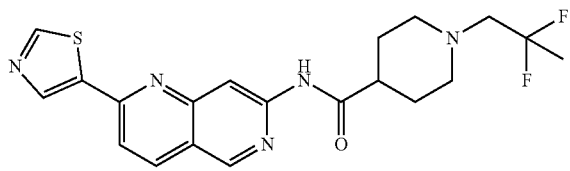 [SMILES: CC(F)(F)CN1CCC(C(=O)Nc2cc3nc(-c4cncs4)ccc3cn2)CC1] | 616 |
| 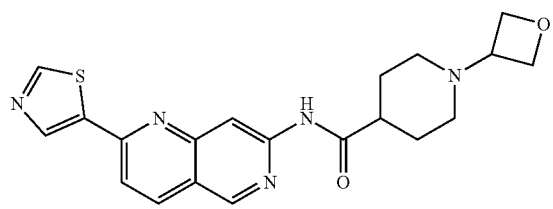 [SMILES: O=C(Nc1cc2nc(-c3cncs3)ccc2cn1)C1CCN(C2COC2)CC1] | 617 |
| 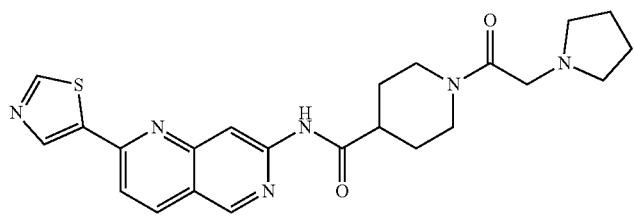 | 618 |
| 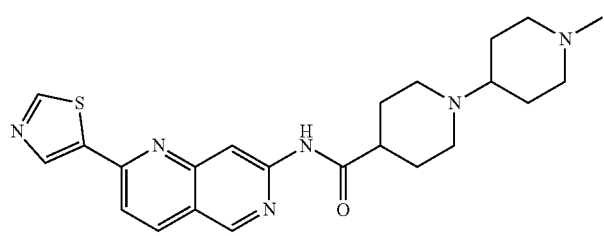 [SMILES: CN1CCC(N2CCC(C(=O)Nc3cc4nc(-c5cncs5)ccc4cn3)CC2)CC1] | 619 |
| 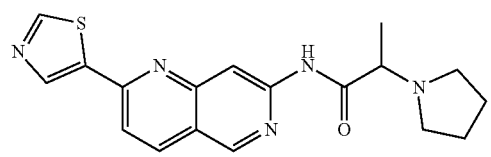 [SMILES: CC(C(=O)Nc1cc2nc(-c3cncs3)ccc2cn1)N1CCCC1] | 620 |
| 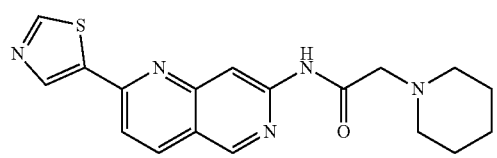 [SMILES: O=C(CN1CCCCC1)Nc1cc2nc(-c3cncs3)ccc2cn1] | 621 |

TABLE 1-continued
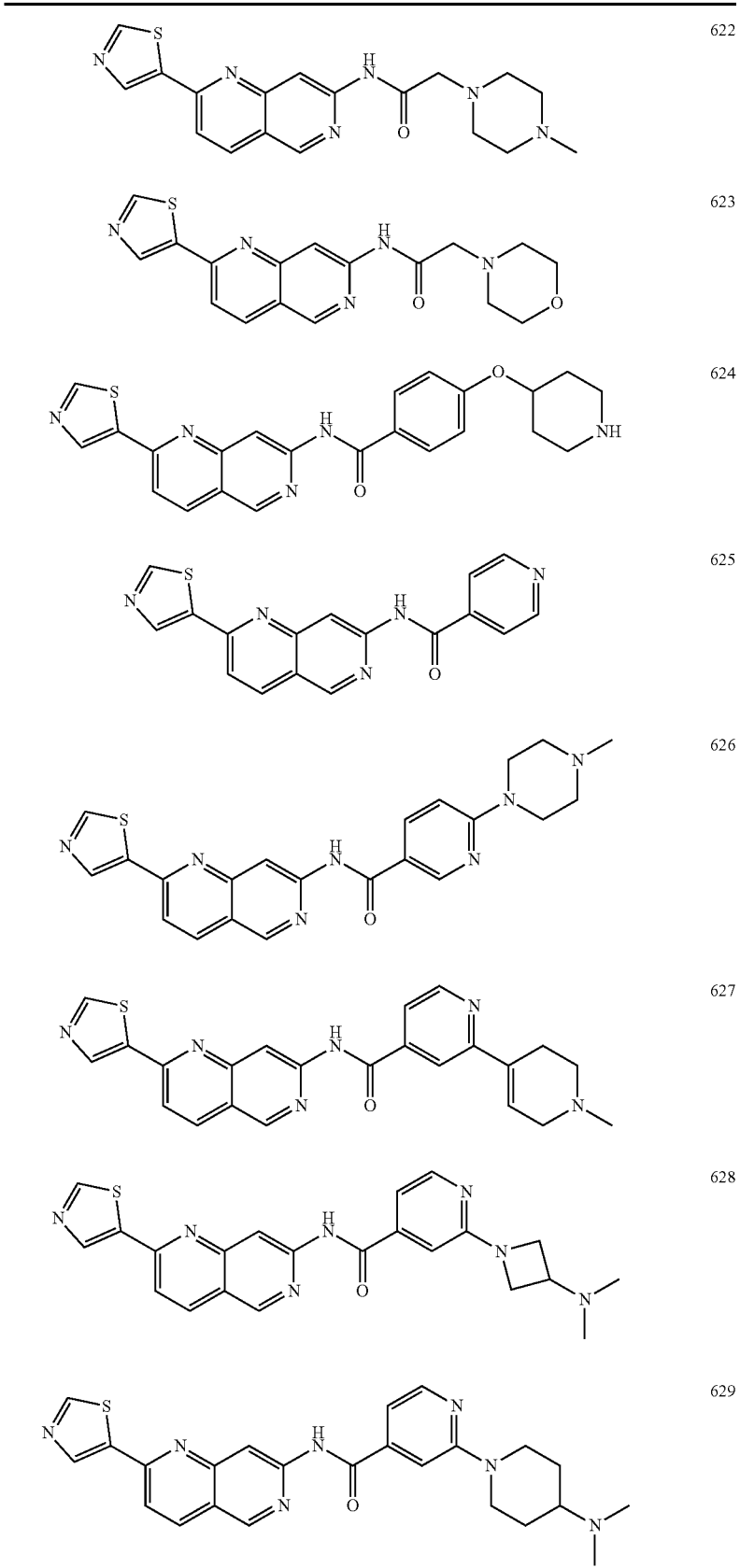

TABLE 1-continued
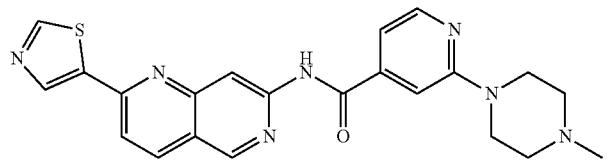 630
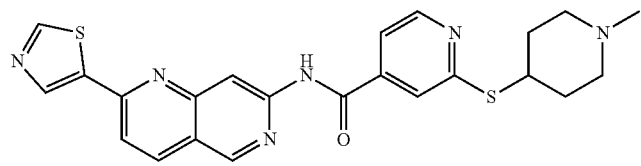 [SMILES: CN1CCC(Sc2cc(C(=O)Nc3cc4nc(-c5cncs5)ccc4cn3)ccn2)CC1] 631
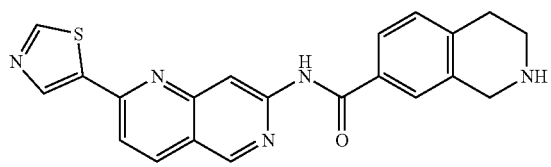 [SMILES: O=C(Nc1cc2nc(-c3cncs3)ccc2cn1)c1ccc2c(c1)CNCC2] 632
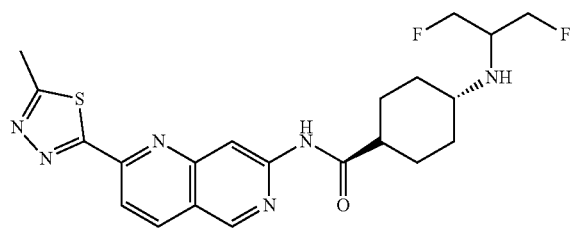 633
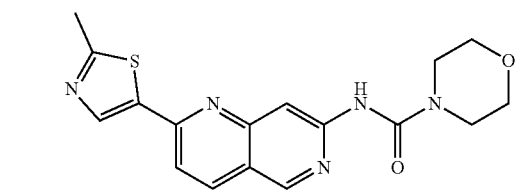 [SMILES: Cc1ncc(-c2ccc3cnc(NC(=O)N4CCOCC4)cc3n2)s1] 634
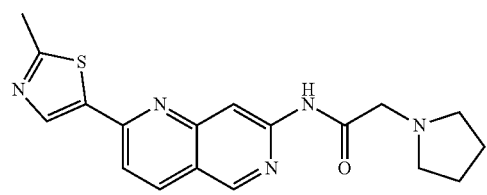 [SMILES: Cc1ncc(-c2ccc3cnc(NC(=O)CN4CCCC4)cc3n2)s1] 635
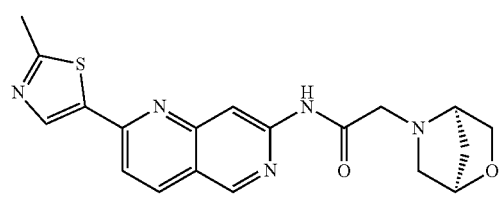 [SMILES: Cc1ncc(-c2ccc3cnc(NC(=O)CN4C[C@H]5C[C@@H]4CO5)cc3n2)s1] 636
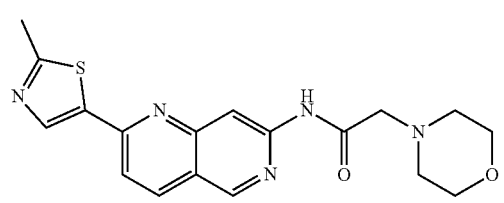 [SMILES: Cc1ncc(-c2ccc3cnc(NC(=O)CN4CCOCC4)cc3n2)s1] 637

TABLE 1-continued
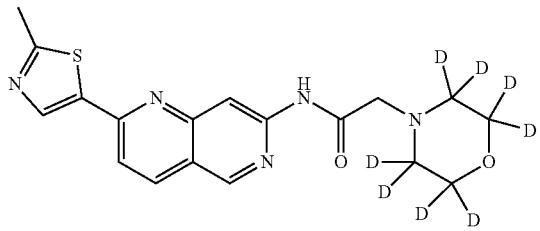 [SMILES: [2H]C1([2H])OC([2H])([2H])C([2H])([2H])N(CC(=O)Nc2cc3nc(-c4cnc(C)s4)ccc3cn2)C1([2H])[2H]]
638
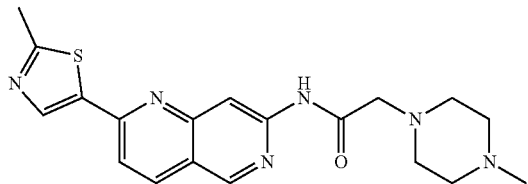
639
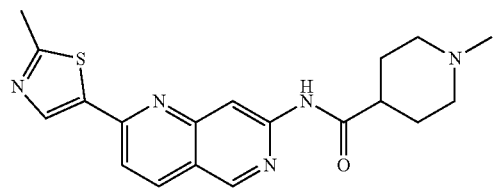
640
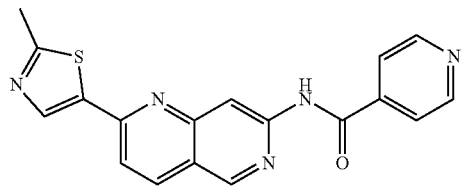 [SMILES: Cc1ncc(-c2ccc3cnc(NC(=O)c4ccncc4)cc3n2)s1]
641
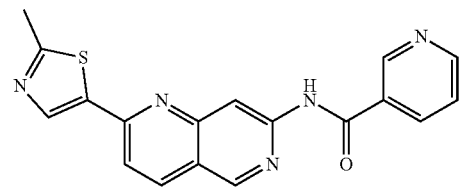 [SMILES: Cc1ncc(-c2ccc3cnc(NC(=O)c4cccnc4)cc3n2)s1]
642
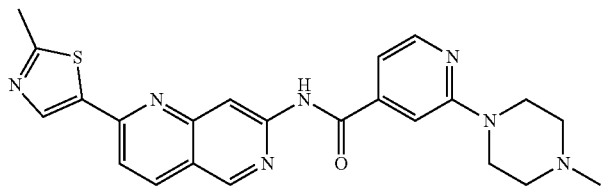
643
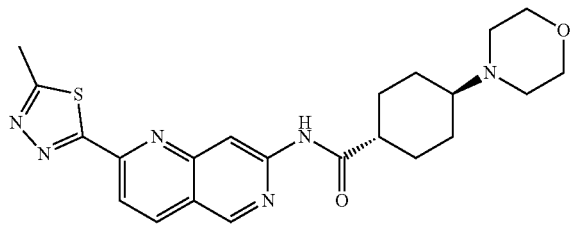 [SMILES: Cc1nnc(-c2ccc3cnc(NC(=O)[C@H]4CC[C@H](N5CCOCC5)CC4)cc3n2)s1]
644

TABLE 1-continued
| | |
|---|---|
| 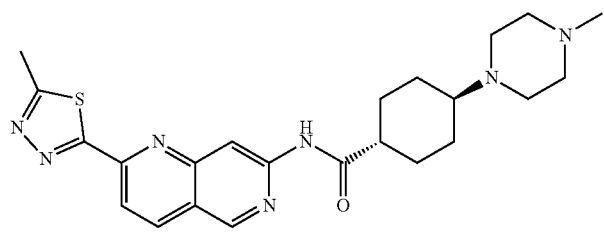 [SMILES: Cc1nnc(-c2ccc3cnc(NC(=O)[C@H]4CC[C@H](N5CCN(C)CC5)CC4)cc3n2)s1] | 645 |
| 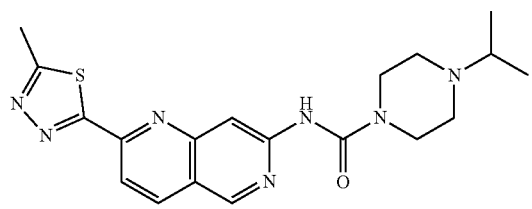 [SMILES: Cc1nnc(-c2ccc3cnc(NC(=O)N4CCN(C(C)C)CC4)cc3n2)s1] | 646 |
| 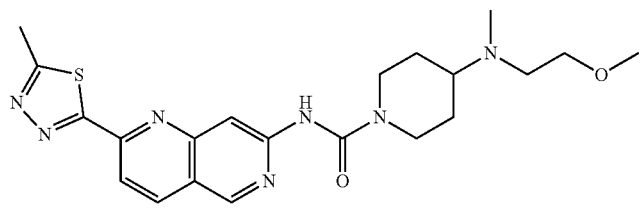 [SMILES: COCCN(C)C1CCN(C(=O)Nc2cc3nc(-c4nnc(C)s4)ccc3cn2)CC1] | 647 |
| 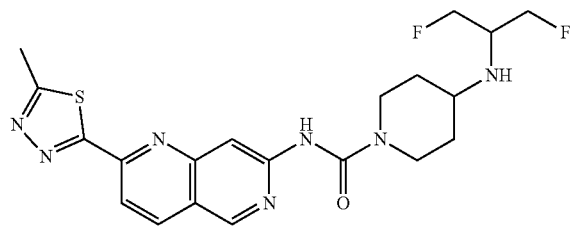 [SMILES: Cc1nnc(-c2ccc3cnc(NC(=O)N4CCC(NC(CF)CF)CC4)cc3n2)s1] | 648 |
| 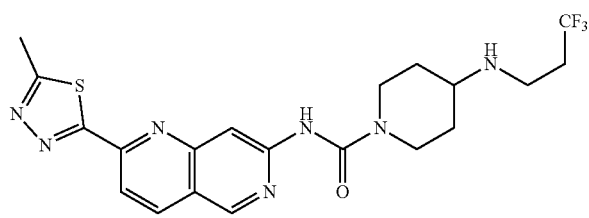 [SMILES: Cc1nnc(-c2ccc3cnc(NC(=O)N4CCC(NCCC(F)(F)F)CC4)cc3n2)s1] | 649 |
| 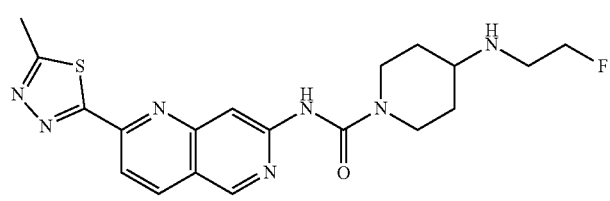 [SMILES: Cc1nnc(-c2ccc3cnc(NC(=O)N4CCC(NCCF)CC4)cc3n2)s1] | 650 |
| 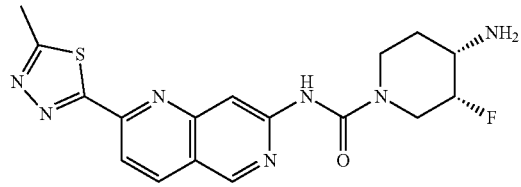 [SMILES: Cc1nnc(-c2ccc3cnc(NC(=O)N4CC[C@H](N)[C@H](F)C4)cc3n2)s1] | 651 |

TABLE 1-continued
| | |
|---|---|
| 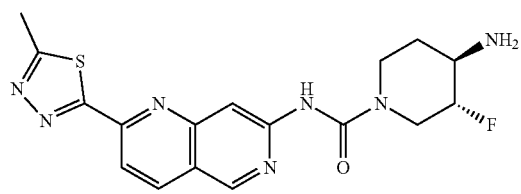 [SMILES: Cc1nnc(-c2ccc3cnc(NC(=O)N4CC[C@@H](N)[C@H](F)C4)cc3n2)s1] | 652 |
| 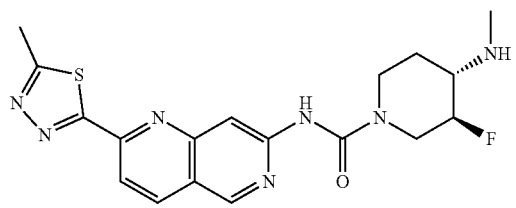 [SMILES: CN[C@H]1CCN(C(=O)Nc2cc3nc(-c4nnc(C)s4)ccc3cn2)C[C@@H]1F] | 653 |
| 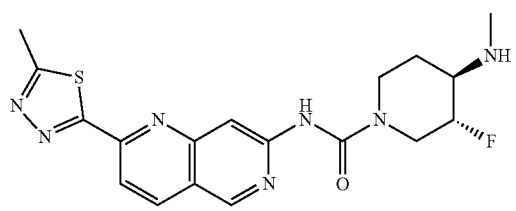 [SMILES: CN[C@@H]1CCN(C(=O)Nc2cc3nc(-c4nnc(C)s4)ccc3cn2)C[C@H]1F] | 654 |
| 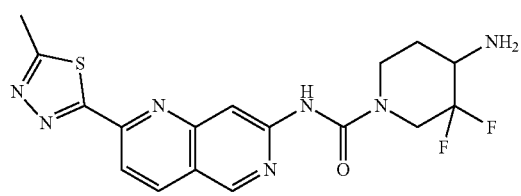 [SMILES: Cc1nnc(-c2ccc3cnc(NC(=O)N4CCC(N)C(F)(F)C4)cc3n2)s1] | 655 |
| 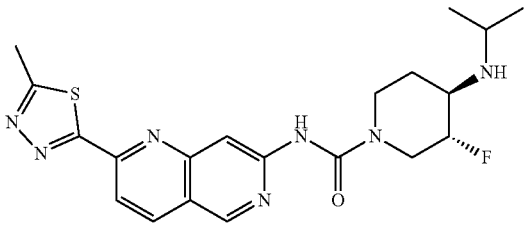 [SMILES: Cc1nnc(-c2ccc3cnc(NC(=O)N4CC[C@@H](NC(C)C)[C@H](F)C4)cc3n2)s1] | 656 |
| 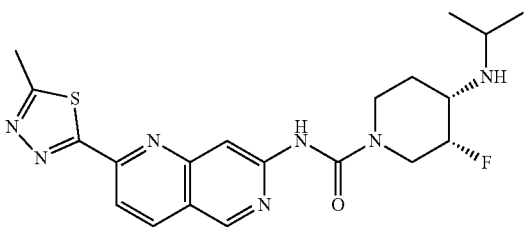 [SMILES: Cc1nnc(-c2ccc3cnc(NC(=O)N4CC[C@H](NC(C)C)[C@H](F)C4)cc3n2)s1] | 657 |
| 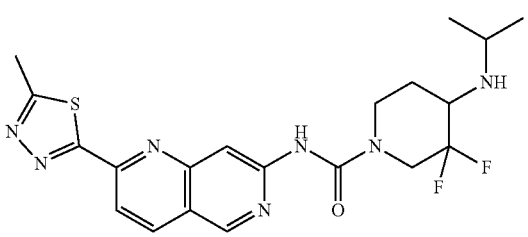 [SMILES: Cc1nnc(-c2ccc3cnc(NC(=O)N4CCC(NC(C)C)C(F)(F)C4)cc3n2)s1] | 658 |

TABLE 1-continued
| | |
|---|---|
| 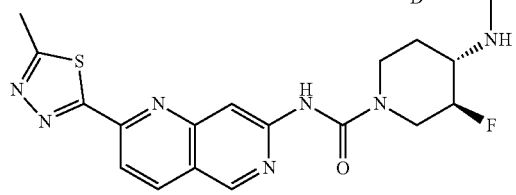 | 659 |
| 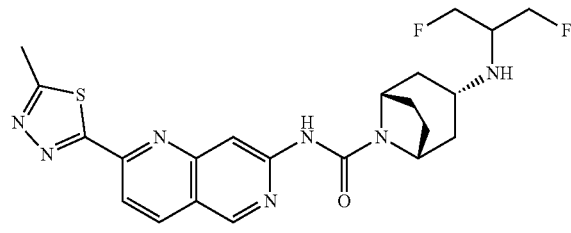 [SMILES: Cc1nnc(-c2ccc3cnc(NC(=O)N4[C@@H]5CC[C@H]4C[C@H](NC(CF)CF)C5)cc3n2)s1] | 660 |
| 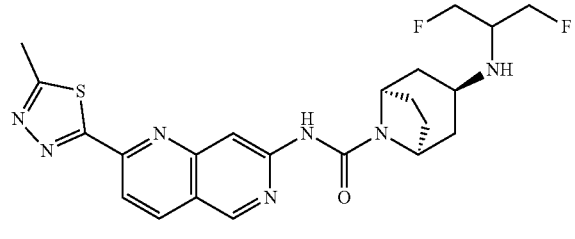 [SMILES: Cc1nnc(-c2ccc3cnc(NC(=O)N4[C@@H]5CC[C@H]4C[C@H](NC(CF)CF)C5)cc3n2)s1] | 661 |
| 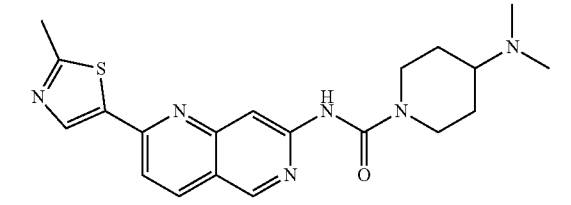 [SMILES: Cc1ncc(-c2ccc3cnc(NC(=O)N4CCC(N(C)C)CC4)cc3n2)s1] | 662 |
| 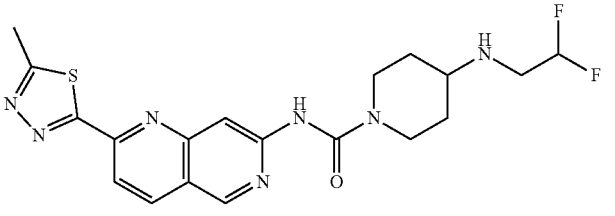 [SMILES: Cc1nnc(-c2ccc3cnc(NC(=O)N4CCC(NCC(F)F)CC4)cc3n2)s1] | 663 |
| 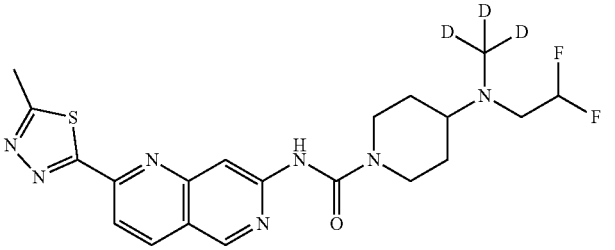 [SMILES: [2H]C([2H])([2H])N(CC(F)F)C1CCN(C(=O)Nc2cc3nc(-c4nnc(C)s4)ccc3cn2)CC1] | 664 |

TABLE 1-continued
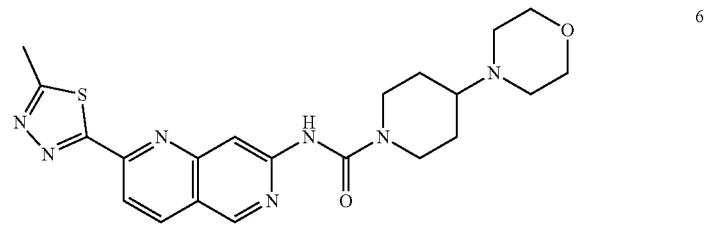
665
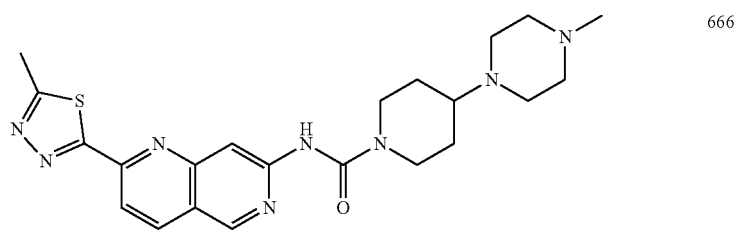
666
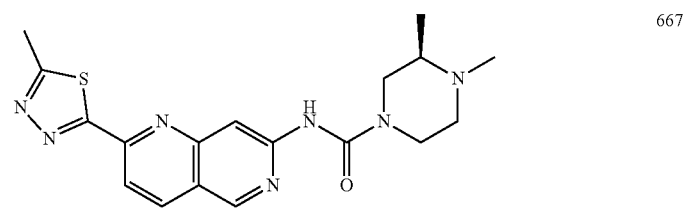
667
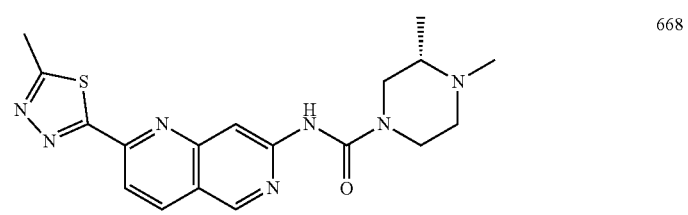
668
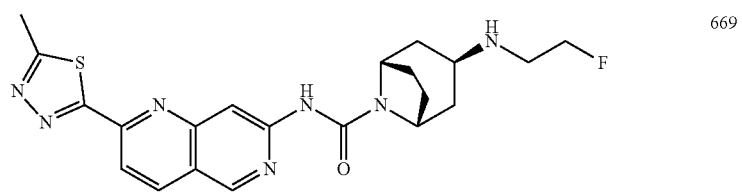
669
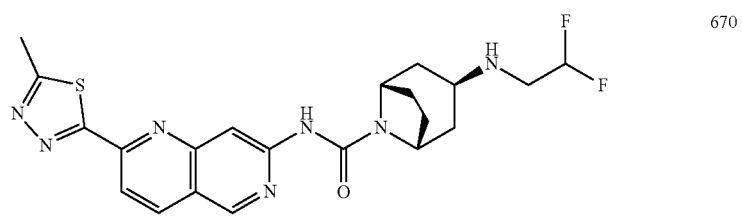
670
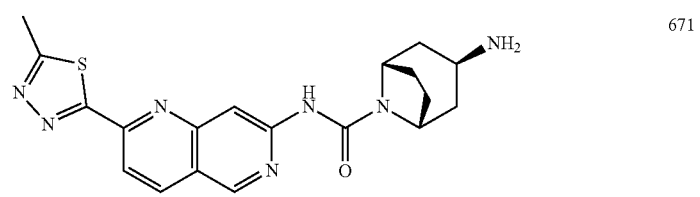
671

TABLE 1-continued
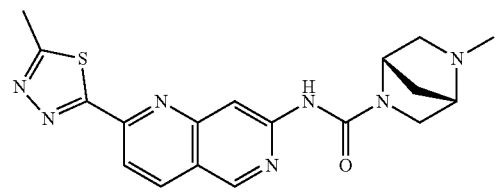 [SMILES: Cc1nnc(-c2ccc3cnc(NC(=O)N4C[C@@H]5C[C@H]4CN5C)cc3n2)s1] 672
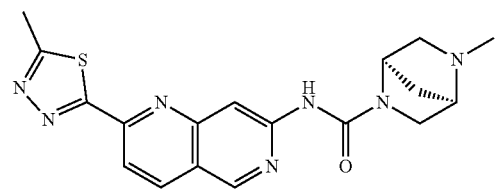 [SMILES: Cc1nnc(-c2ccc3cnc(NC(=O)N4C[C@H]5C[C@@H]4CN5C)cc3n2)s1] 673
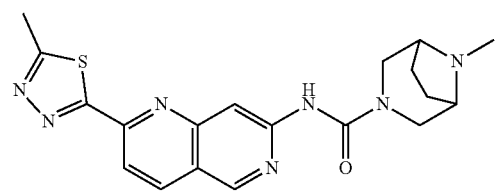 [SMILES: Cc1nnc(-c2ccc3cnc(NC(=O)N4CC5CCC(C4)N5C)cc3n2)s1] 674
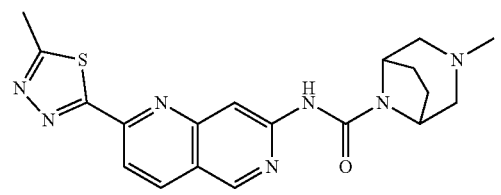 [SMILES: Cc1nnc(-c2ccc3cnc(NC(=O)N4C5CCC4CN(C)C5)cc3n2)s1] 675
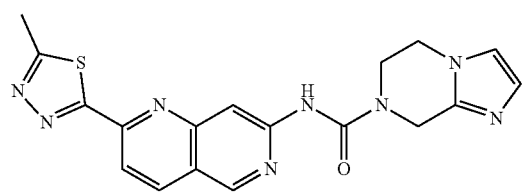 [SMILES: Cc1nnc(-c2ccc3cnc(NC(=O)N4CCn5ccnc5C4)cc3n2)s1] 676
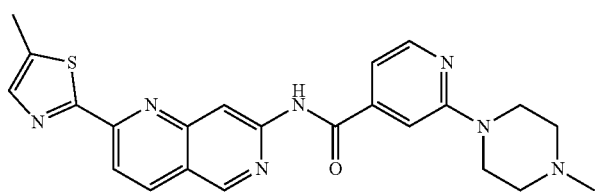 [SMILES: Cc1cnc(-c2ccc3cnc(NC(=O)c4ccnc(N5CCN(C)CC5)c4)cc3n2)s1] 677
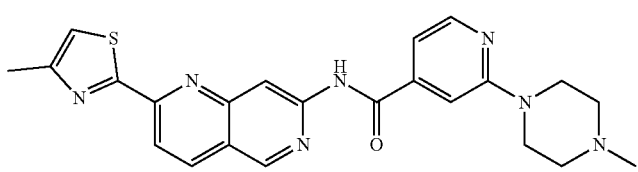 678
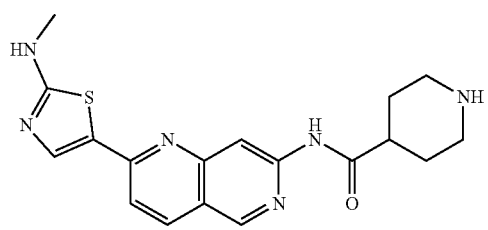 [SMILES: CNc1ncc(-c2ccc3cnc(NC(=O)C4CCNCC4)cc3n2)s1] 679

TABLE 1-continued
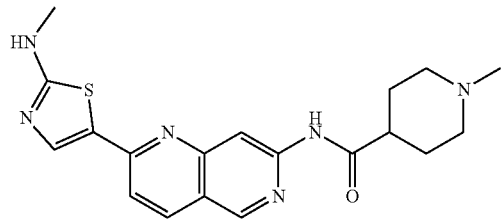 [SMILES: CNc1ncc(-c2ccc3cnc(NC(=O)C4CCN(C)CC4)cc3n2)s1]
680
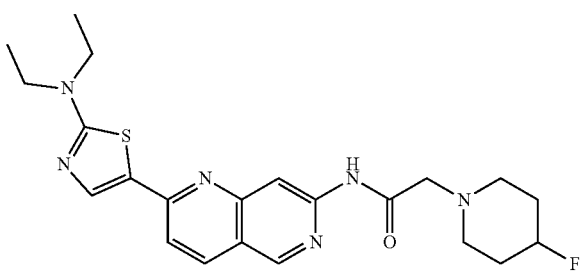 [SMILES: CCN(CC)c1ncc(-c2ccc3cnc(NC(=O)CN4CCC(F)CC4)cc3n2)s1]
681
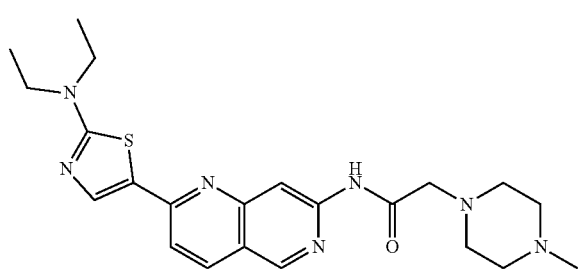 [SMILES: CCN(CC)c1ncc(-c2ccc3cnc(NC(=O)CN4CCN(C)CC4)cc3n2)s1]
682
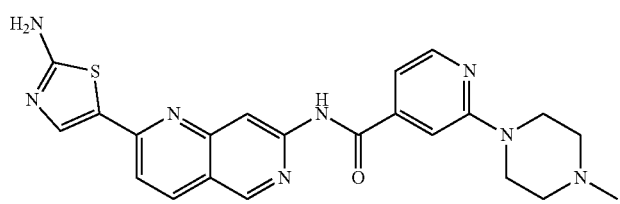 [SMILES: CN1CCN(c2cc(C(=O)Nc3cc4nc(-c5cnc(N)s5)ccc4cn3)ccn2)CC1]
683
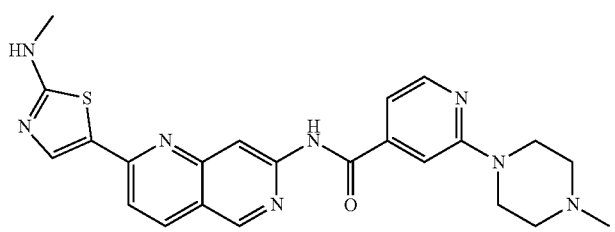 [SMILES: CNc1ncc(-c2ccc3cnc(NC(=O)c4ccnc(N5CCN(C)CC5)c4)cc3n2)s1]
684
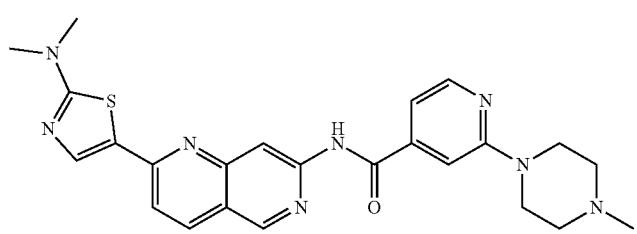
685

TABLE 1-continued
| | |
|---|---|
| 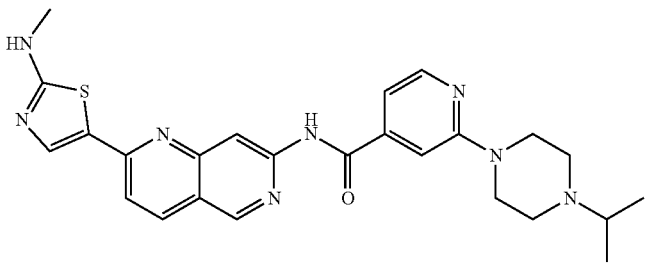 [SMILES: CNc1ncc(-c2ccc3cnc(NC(=O)c4ccnc(N5CCN(C(C)C)CC5)c4)cc3n2)s1] | 686 |
| 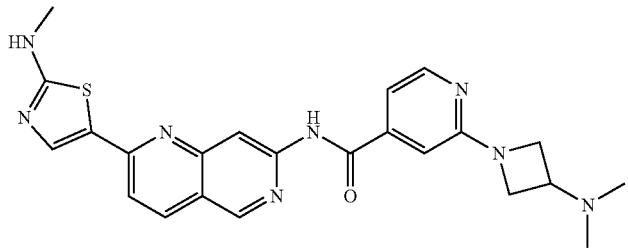 | 687 |
| 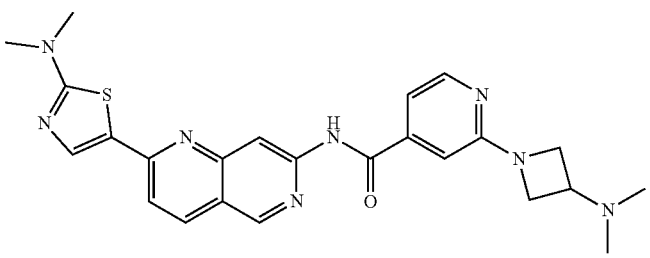 | 688 |
| 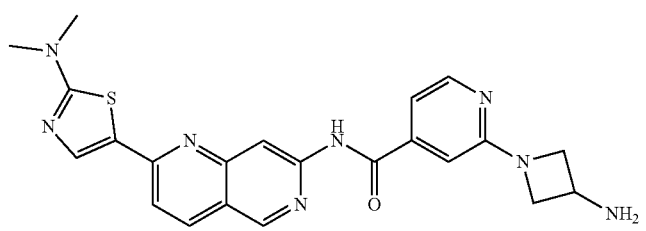 [SMILES: CN(C)c1ncc(-c2ccc3cnc(NC(=O)c4ccnc(N5CC(N)C5)c4)cc3n2)s1] | 689 |
| 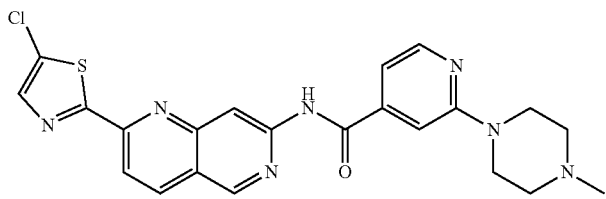 [SMILES: CN1CCN(c2cc(C(=O)Nc3cc4nc(-c5ncc(Cl)s5)ccc4cn3)ccn2)CC1] | 690 |
| 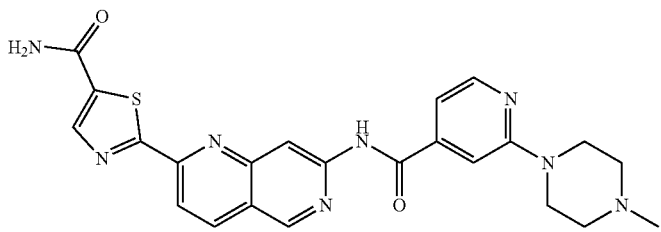 [SMILES: CN1CCN(c2cc(C(=O)Nc3cc4nc(-c5ncc(C(N)=O)s5)ccc4cn3)ccn2)CC1] | 691 |
| 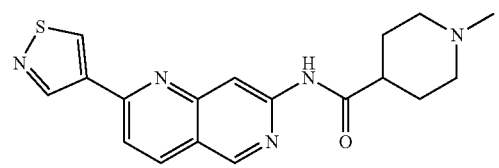 [SMILES: CN1CCC(C(=O)Nc2cc3nc(-c4cnsc4)ccc3cn2)CC1] | 692 |

TABLE 1-continued
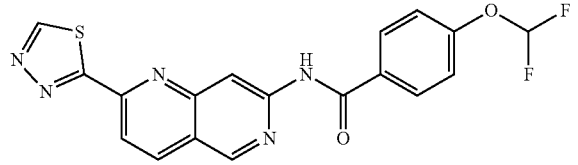 693
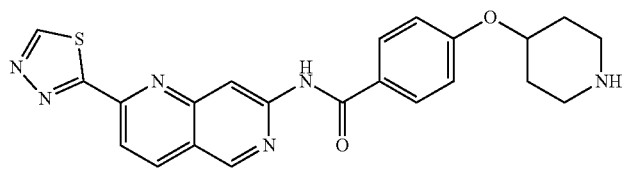 [SMILES: O=C(Nc1cc2nc(-c3nncs3)ccc2cn1)c1ccc(OC2CCNCC2)cc1] 694
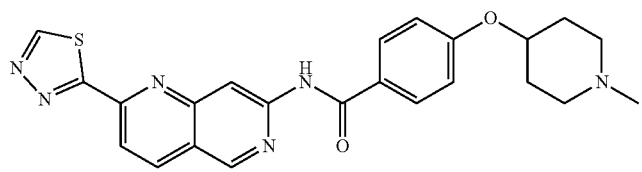 [SMILES: CN1CCC(Oc2ccc(C(=O)Nc3cc4nc(-c5nncs5)ccc4cn3)cc2)CC1] 695
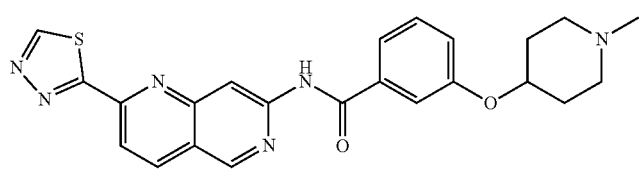 [SMILES: CN1CCC(Oc2cccc(C(=O)Nc3cc4nc(-c5nncs5)ccc4cn3)c2)CC1] 696
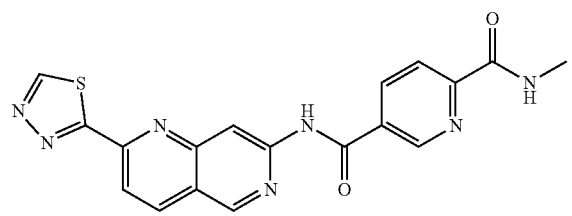 [SMILES: CNC(=O)c1ccc(C(=O)Nc2cc3nc(-c4nncs4)ccc3cn2)cn1] 697
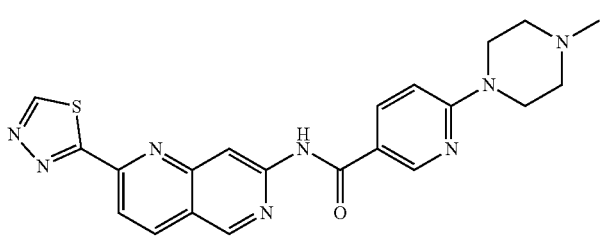 [SMILES: CN1CCN(c2ccc(C(=O)Nc3cc4nc(-c5nncs5)ccc4cn3)cn2)CC1] 698
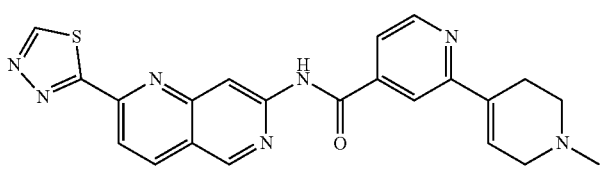 [SMILES: CN1CC=C(c2cc(C(=O)Nc3cc4nc(-c5nncs5)ccc4cn3)ccn2)CC1] 699
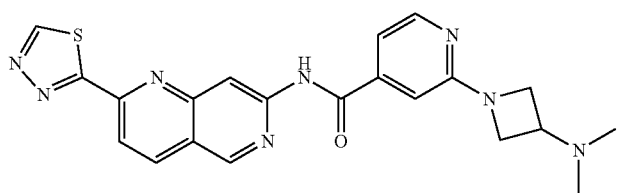 700

TABLE 1-continued
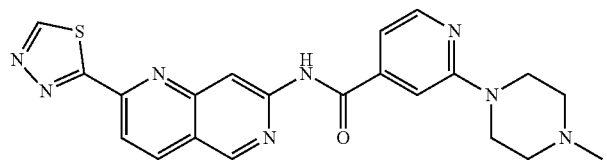 [SMILES: CN1CCN(c2cc(C(=O)Nc3cc4nc(-c5nncs5)ccc4cn3)ccn2)CC1] 701
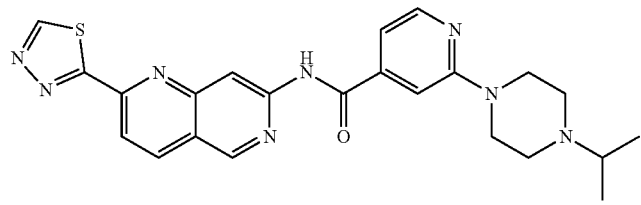 [SMILES: CC(C)N1CCN(c2cc(C(=O)Nc3cc4nc(-c5nncs5)ccc4cn3)ccn2)CC1] 702
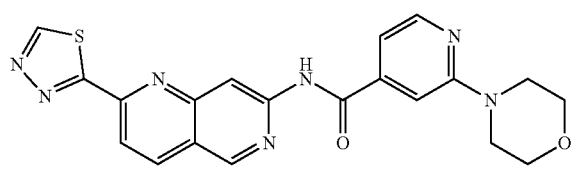 [SMILES: O=C(Nc1cc2nc(-c3nncs3)ccc2cn1)c1ccnc(N2CCOCC2)c1] 703
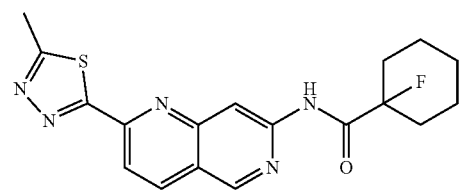 704
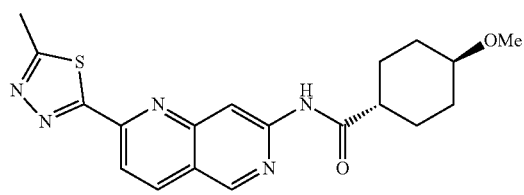 [SMILES: CO[C@H]1CC[C@H](C(=O)Nc2cc3nc(-c4nnc(C)s4)ccc3cn2)CC1] 705
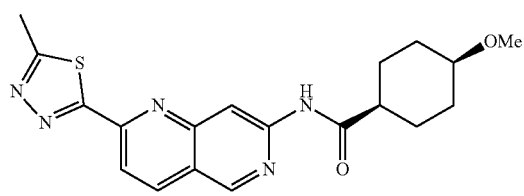 706
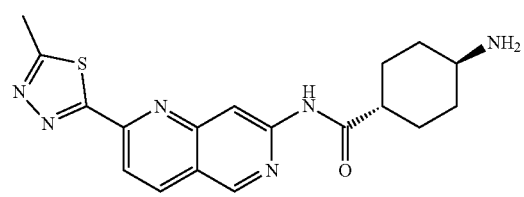 [SMILES: Cc1nnc(-c2ccc3cnc(NC(=O)[C@H]4CC[C@H](N)CC4)cc3n2)s1] 707
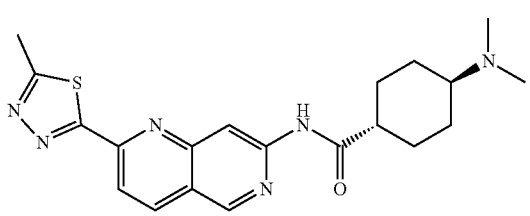 [SMILES: Cc1nnc(-c2ccc3cnc(NC(=O)[C@H]4CC[C@H](N(C)C)CC4)cc3n2)s1] 708

TABLE 1-continued
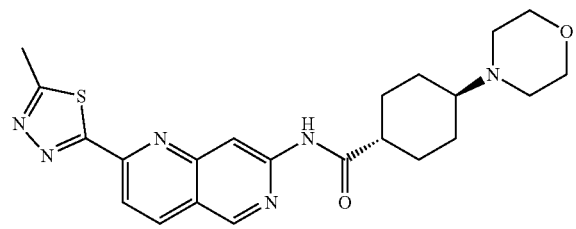 [SMILES: Cc1nnc(-c2ccc3cnc(NC(=O)[C@H]4CC[C@H](N5CCOCC5)CC4)cc3n2)s1] 709
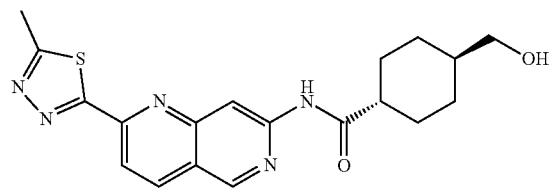 [SMILES: Cc1nnc(-c2ccc3cnc(NC(=O)[C@H]4CC[C@H](CO)CC4)cc3n2)s1] 710
 711
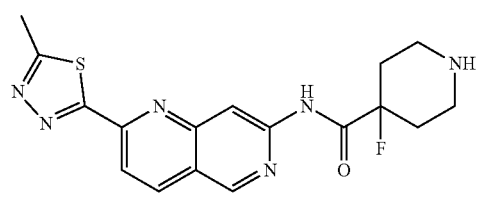 [SMILES: Cc1nnc(-c2ccc3cnc(NC(=O)C4(F)CCNCC4)cc3n2)s1] 712
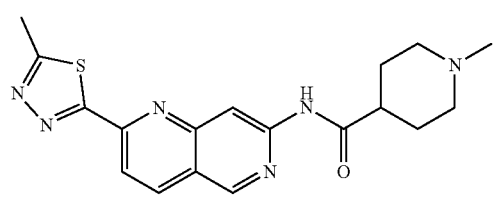 [SMILES: Cc1nnc(-c2ccc3cnc(NC(=O)C4CCN(C)CC4)cc3n2)s1] 713
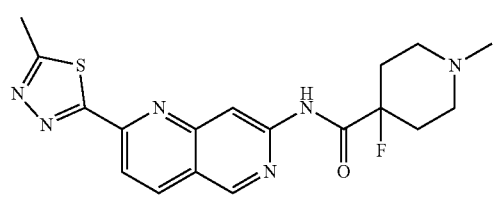 [SMILES: Cc1nnc(-c2ccc3cnc(NC(=O)C4(F)CCN(C)CC4)cc3n2)s1] 714
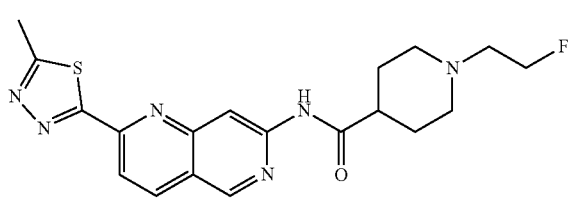 [SMILES: Cc1nnc(-c2ccc3cnc(NC(=O)C4CCN(CCF)CC4)cc3n2)s1] 715
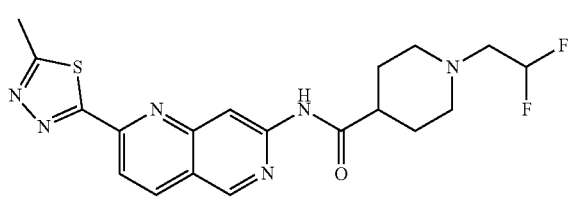 [SMILES: Cc1nnc(-c2ccc3cnc(NC(=O)C4CCN(CC(F)F)CC4)cc3n2)s1] 716

TABLE 1-continued
| | |
|---|---|
| 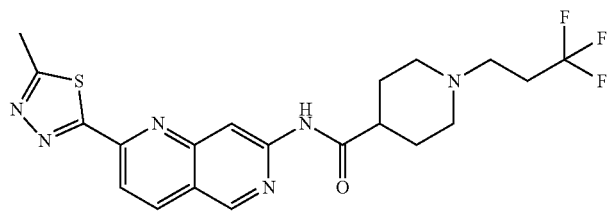 [SMILES: Cc1nnc(-c2ccc3cnc(NC(=O)C4CCN(CCC(F)(F)F)CC4)cc3n2)s1] | 717 |
| 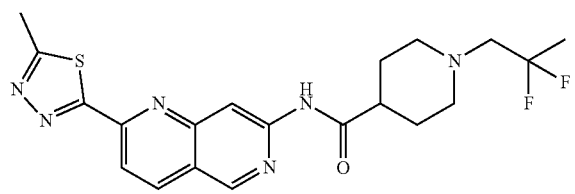 [SMILES: Cc1nnc(-c2ccc3cnc(NC(=O)C4CCN(CC(C)(F)F)CC4)cc3n2)s1] | 718 |
| 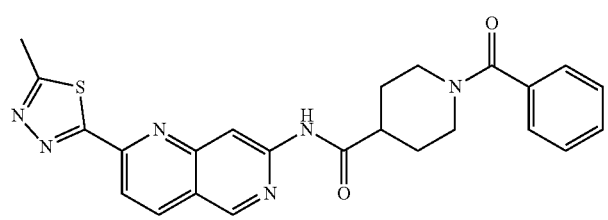 [SMILES: Cc1nnc(-c2ccc3cnc(NC(=O)C4CCN(C(=O)c5ccccc5)CC4)cc3n2)s1] | 719 |
| 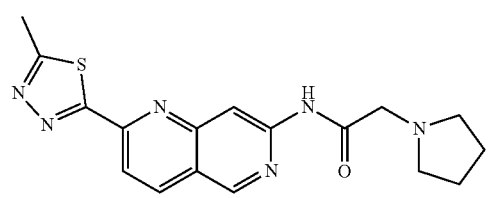 [SMILES: Cc1nnc(-c2ccc3cnc(NC(=O)CN4CCCC4)cc3n2)s1] | 720 |
| 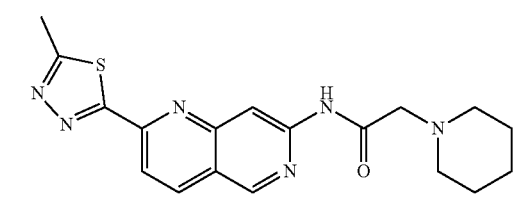 [SMILES: Cc1nnc(-c2ccc3cnc(NC(=O)CN4CCCCC4)cc3n2)s1] | 721 |
| 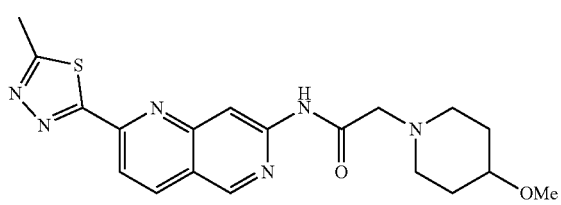 [SMILES: COC1CCN(CC(=O)Nc2cc3nc(-c4nnc(C)s4)ccc3cn2)CC1] | 722 |
| 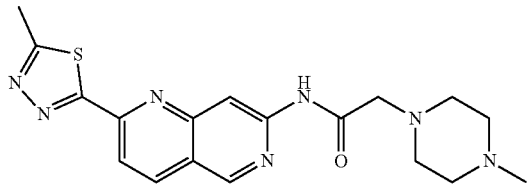 [SMILES: Cc1nnc(-c2ccc3cnc(NC(=O)CN4CCN(C)CC4)cc3n2)s1] | 723 |
| 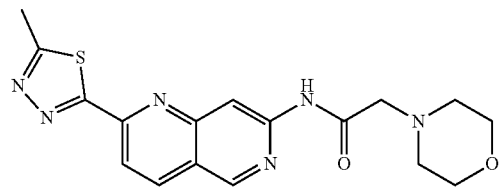 | 724 |

TABLE 1-continued
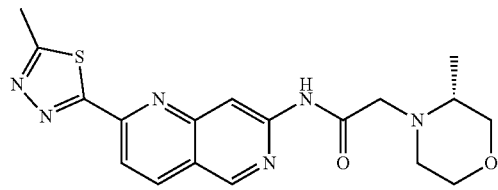 [SMILES: Cc1nnc(-c2ccc3cnc(NC(=O)CN4CCOC[C@H]4C)cc3n2)s1] 725
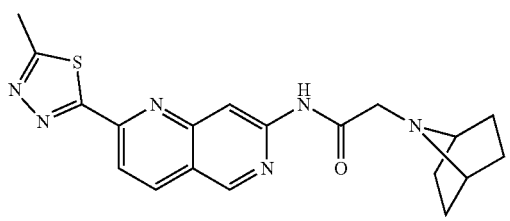 [SMILES: Cc1nnc(-c2ccc3cnc(NC(=O)CN4C5CCC4CC5)cc3n2)s1] 726
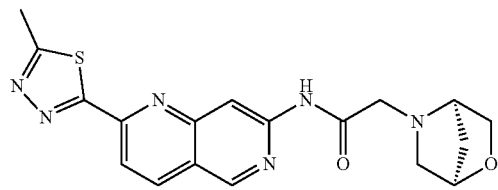 [SMILES: Cc1nnc(-c2ccc3cnc(NC(=O)CN4C[C@H]5C[C@@H]4CO5)cc3n2)s1] 727
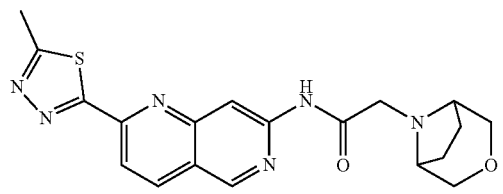 [SMILES: Cc1nnc(-c2ccc3cnc(NC(=O)CN4C5CCC4COC5)cc3n2)s1] 728
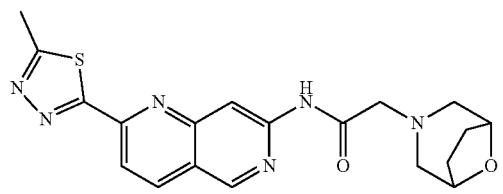 [SMILES: Cc1nnc(-c2ccc3cnc(NC(=O)CN4CC5CCC(C4)O5)cc3n2)s1] 729
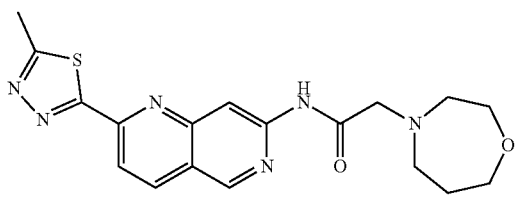 [SMILES: Cc1nnc(-c2ccc3cnc(NC(=O)CN4CCCOCC4)cc3n2)s1] 730
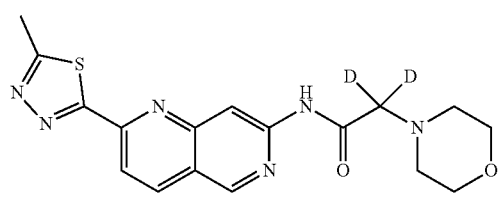 [SMILES: [2H]C([2H])(C(=O)Nc1cc2nc(-c3nnc(C)s3)ccc2cn1)N1CCOCC1] 731
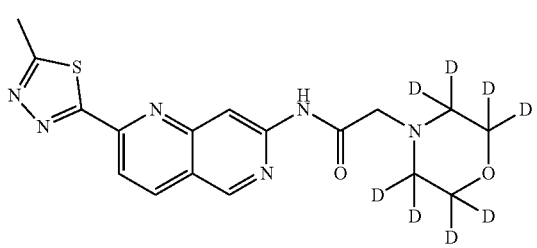 [SMILES: [2H]C1([2H])OC([2H])([2H])C([2H])([2H])N(CC(=O)Nc2cc3nc(-c4nnc(C)s4)ccc3cn2)C1([2H])[2H]] 732

TABLE 1-continued
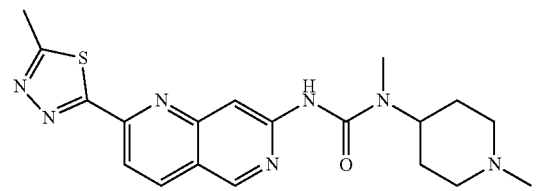 [SMILES: Cc1nnc(-c2ccc3cnc(NC(=O)N(C)C4CCN(C)CC4)cc3n2)s1] 733
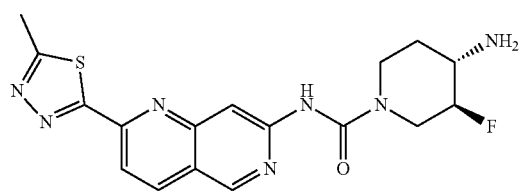 [SMILES: Cc1nnc(-c2ccc3cnc(NC(=O)N4CC[C@H](N)[C@@H](F)C4)cc3n2)s1] 734
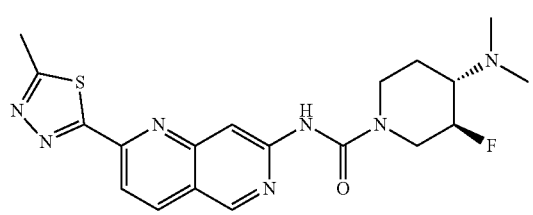 [SMILES: Cc1nnc(-c2ccc3cnc(NC(=O)N4CC[C@H](N(C)C)[C@@H](F)C4)cc3n2)s1] 735
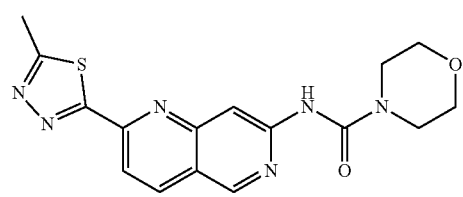 [SMILES: Cc1nnc(-c2ccc3cnc(NC(=O)N4CCOCC4)cc3n2)s1] 736
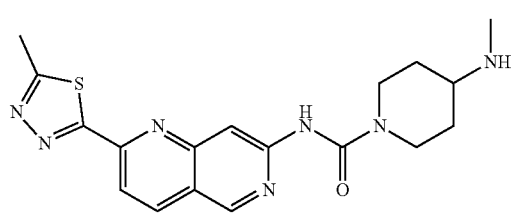 [SMILES: CNC1CCN(C(=O)Nc2cc3nc(-c4nnc(C)s4)ccc3cn2)CC1] 737
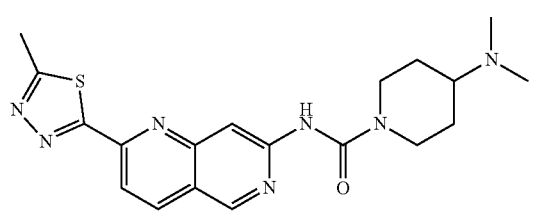 [SMILES: Cc1nnc(-c2ccc3cnc(NC(=O)N4CCC(N(C)C)CC4)cc3n2)s1] 738
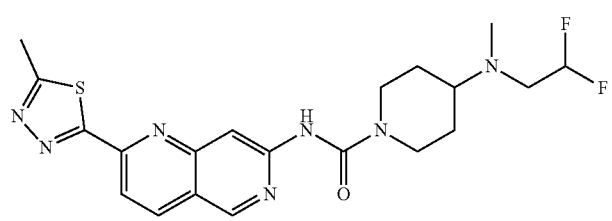 739

TABLE 1-continued
| | |
|---|---|
| 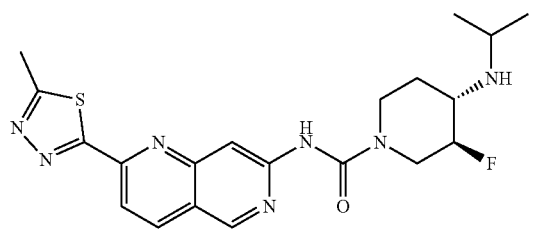 [SMILES: Cc1nnc(-c2ccc3cnc(NC(=O)N4CC[C@H](NC(C)C)[C@@H](F)C4)cc3n2)s1] | 740 |
| 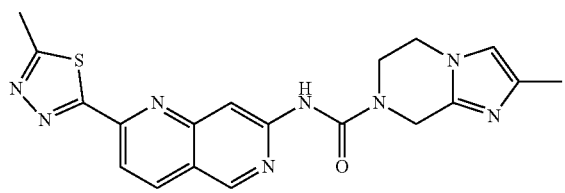 [SMILES: Cc1cn2c(n1)CN(C(=O)Nc1cc3nc(-c4nnc(C)s4)ccc3cn1)CC2] | 741 |
| 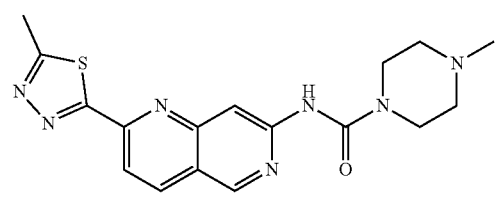 [SMILES: Cc1nnc(-c2ccc3cnc(NC(=O)N4CCN(C)CC4)cc3n2)s1] | 742 |
| 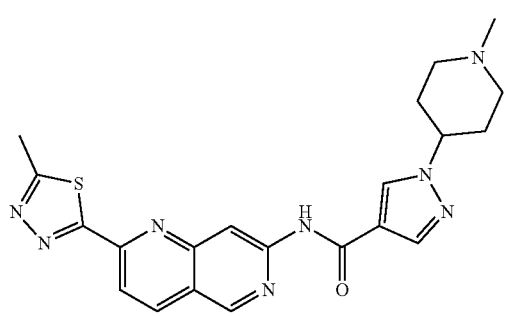 [SMILES: Cc1nnc(-c2ccc3cnc(NC(=O)c4cnn(C5CCN(C)CC5)c4)cc3n2)s1] | 743 |
| 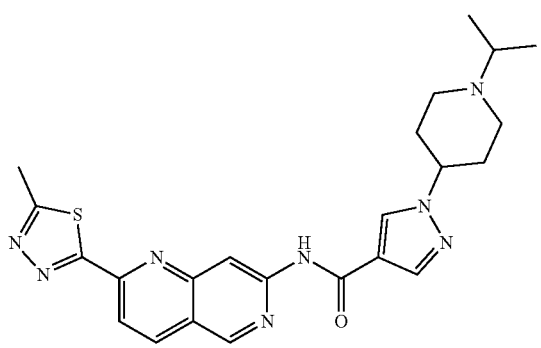 [SMILES: Cc1nnc(-c2ccc3cnc(NC(=O)c4cnn(C5CCN(C(C)C)CC5)c4)cc3n2)s1] | 744 |
| 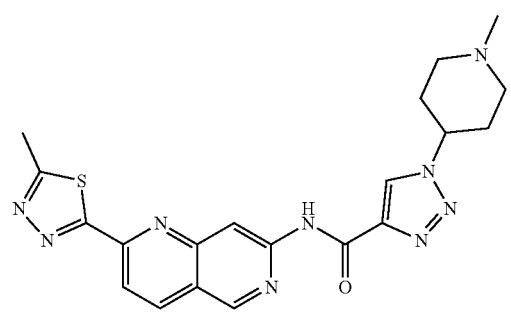 [SMILES: Cc1nnc(-c2ccc3cnc(NC(=O)c4cn(C5CCN(C)CC5)nn4)cc3n2)s1] | 745 |

TABLE 1-continued
| | |
|---|---|
| 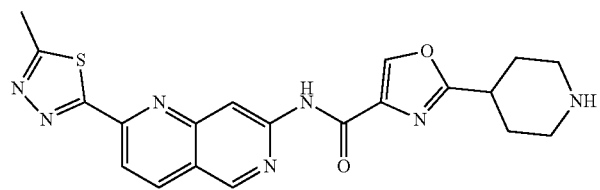 [SMILES: Cc1nnc(-c2ccc3cnc(NC(=O)c4coc(C5CCNCC5)n4)cc3n2)s1] | 746 |
| 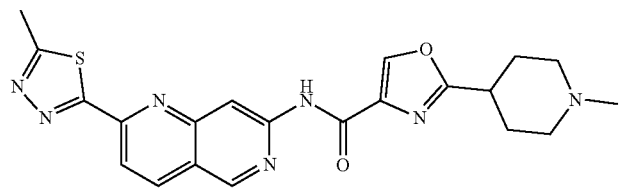 [SMILES: Cc1nnc(-c2ccc3cnc(NC(=O)c4coc(C5CCN(C)CC5)n4)cc3n2)s1] | 747 |
| 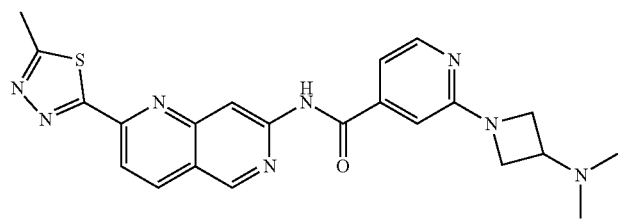 [SMILES: Cc1nnc(-c2ccc3cnc(NC(=O)c4ccnc(N5CC(N(C)C)C5)c4)cc3n2)s1] | 748 |
| 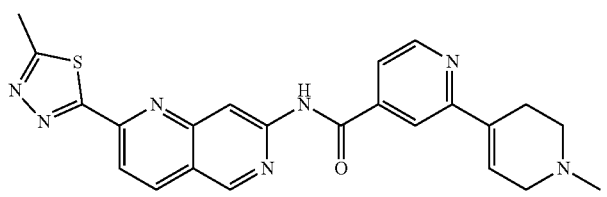 [SMILES: Cc1nnc(-c2ccc3cnc(NC(=O)c4ccnc(C5=CCN(C)CC5)c4)cc3n2)s1] | 749 |
| 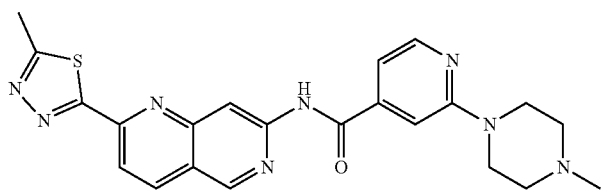 | 750 |
| 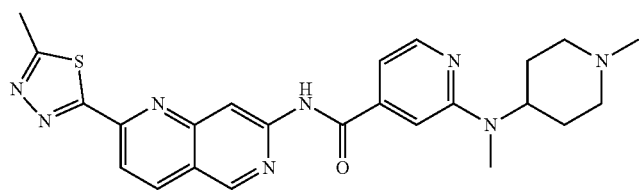 [SMILES: Cc1nnc(-c2ccc3cnc(NC(=O)c4ccnc(N(C)C5CCN(C)CC5)c4)cc3n2)s1] | 751 |
| 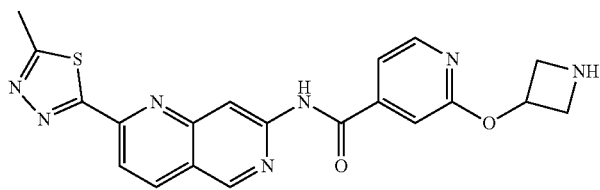 [SMILES: Cc1nnc(-c2ccc3cnc(NC(=O)c4ccnc(OC5CNC5)c4)cc3n2)s1] | 752 |
| 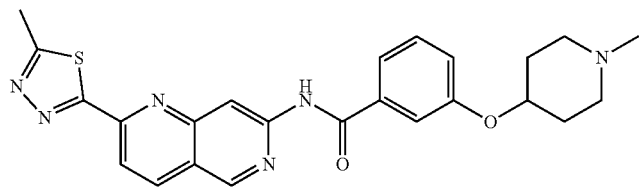 | 753 |

TABLE 1-continued
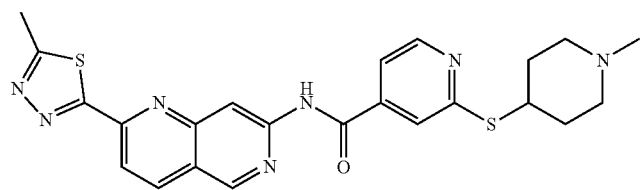 [SMILES: Cc1nnc(-c2ccc3cnc(NC(=O)c4cccc(OC5CCN(C)CC5)c4)cc3n2)s1]
754
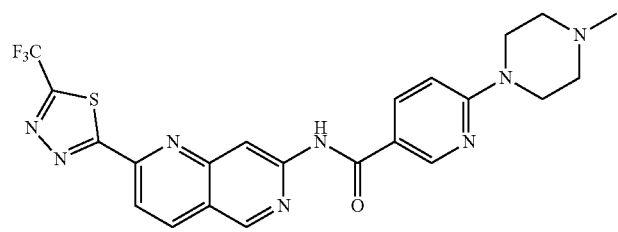 [SMILES: CN1CCN(c2ccc(C(=O)Nc3cc4nc(-c5nnc(C(F)(F)F)s5)ccc4cn3)cn2)CC1]
755
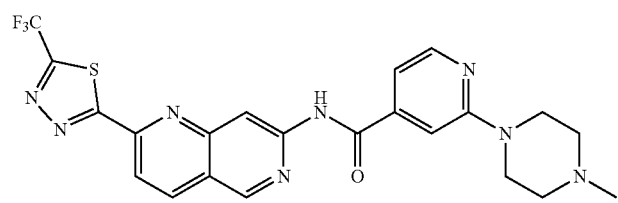 [SMILES: CN1CCN(c2cc(C(=O)Nc3cc4nc(-c5nnc(C(F)(F)F)s5)ccc4cn3)ccn2)CC1]
756
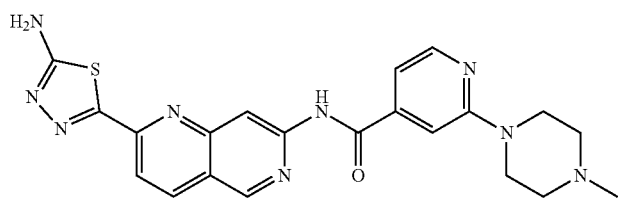 [SMILES: CN1CCN(c2cc(C(=O)Nc3cc4nc(-c5nnc(N)s5)ccc4cn3)ccn2)CC1]
757
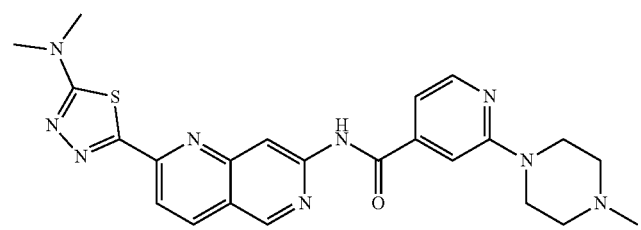
758
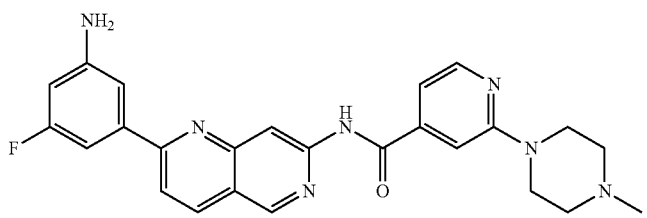 [SMILES: CN1CCN(c2cc(C(=O)Nc3cc4nc(-c5cc(N)cc(F)c5)ccc4cn3)ccn2)CC1]
759
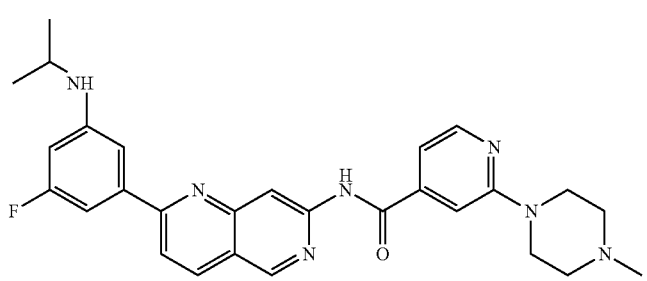 [SMILES: CC(C)Nc1cc(F)cc(-c2ccc3cnc(NC(=O)c4ccnc(N5CCN(C)CC5)c4)cc3n2)c1]
760

TABLE 1-continued
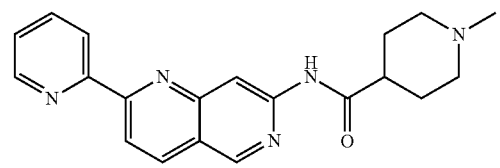 [SMILES: CN1CCC(C(=O)Nc2cc3nc(-c4ccccn4)ccc3cn2)CC1] 761
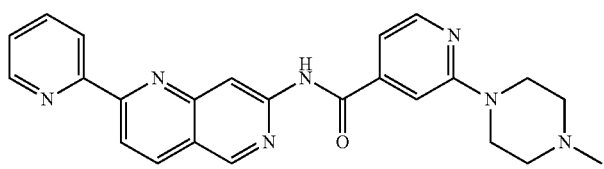 [SMILES: CN1CCN(c2cc(C(=O)Nc3cc4nc(-c5ccccn5)ccc4cn3)ccn2)CC1] 762
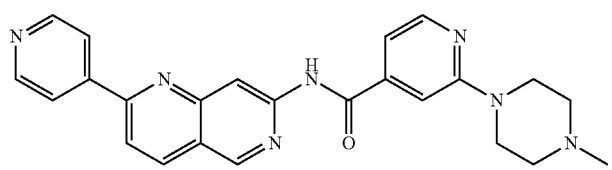 [SMILES: CN1CCN(c2cc(C(=O)Nc3cc4nc(-c5ccncc5)ccc4cn3)ccn2)CC1] 763
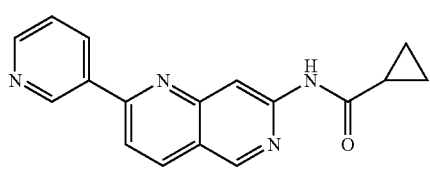 [SMILES: O=C(Nc1cc2nc(-c3cccnc3)ccc2cn1)C1CC1] 764
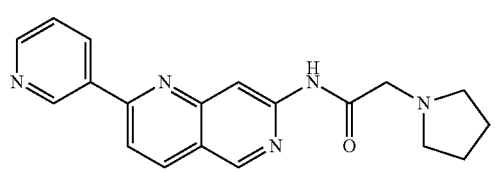 765
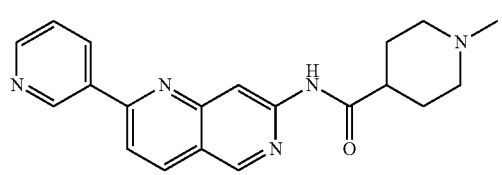 [SMILES: CN1CCC(C(=O)Nc2cc3nc(-c4cccnc4)ccc3cn2)CC1] 766
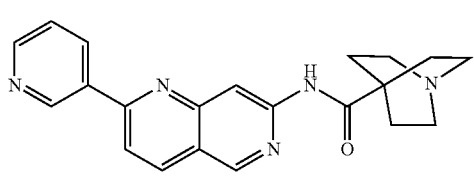 [SMILES: O=C(Nc1cc2nc(-c3cccnc3)ccc2cn1)C12CCN(CC1)CC2] 767
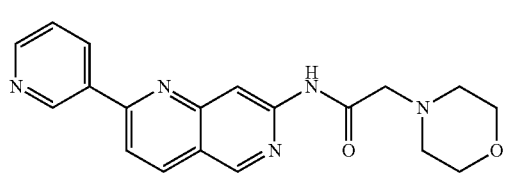 [SMILES: O=C(CN1CCOCC1)Nc1cc2nc(-c3cccnc3)ccc2cn1] 768
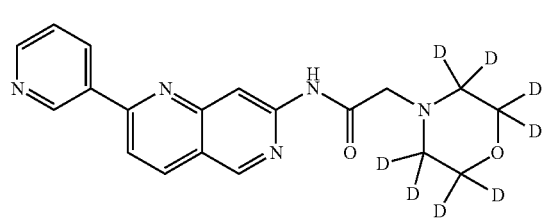 [SMILES: [2H]C1([2H])OC([2H])([2H])C([2H])([2H])N(CC(=O)Nc2cc3nc(-c4cccnc4)ccc3cn2)C1([2H])[2H]] 769

TABLE 1-continued
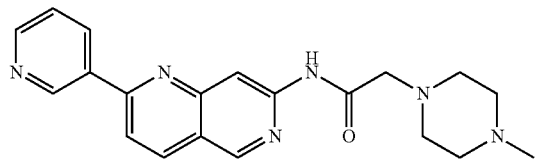 [SMILES: CN1CCN(CC(=O)Nc2cc3nc(-c4cccnc4)ccc3cn2)CC1] 770
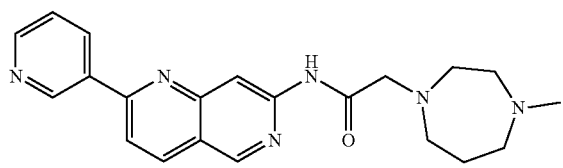 [SMILES: CN1CCCN(CC(=O)Nc2cc3nc(-c4cccnc4)ccc3cn2)CC1] 771
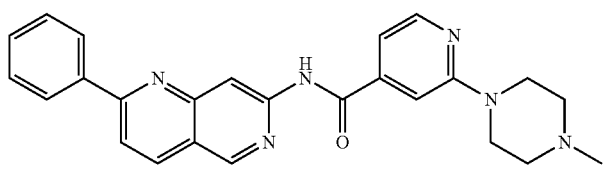 [SMILES: CN1CCN(c2cc(C(=O)Nc3cc4nc(-c5ccccc5)ccc4cn3)ccn2)CC1] 772
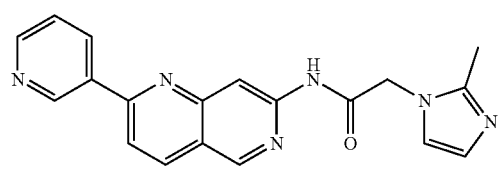 [SMILES: Cc1nccn1CC(=O)Nc1cc2nc(-c3cccnc3)ccc2cn1] 773
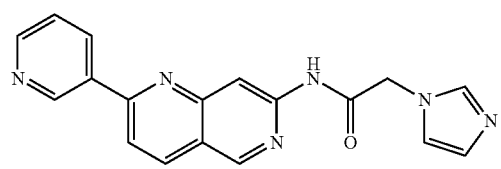 [SMILES: O=C(Cn1ccnc1)Nc1cc2nc(-c3cccnc3)ccc2cn1] 774
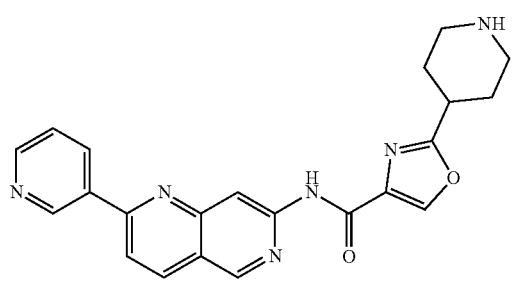 [SMILES: O=C(Nc1cc2nc(-c3cccnc3)ccc2cn1)c1coc(C2CCNCC2)n1] 775
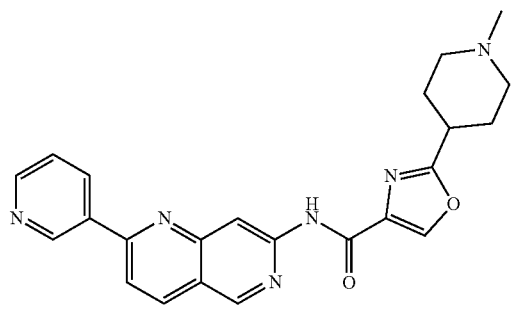 [SMILES: CN1CCC(c2nc(C(=O)Nc3cc4nc(-c5cccnc5)ccc4cn3)co2)CC1] 776

TABLE 1-continued
| | |
|---|---|
| 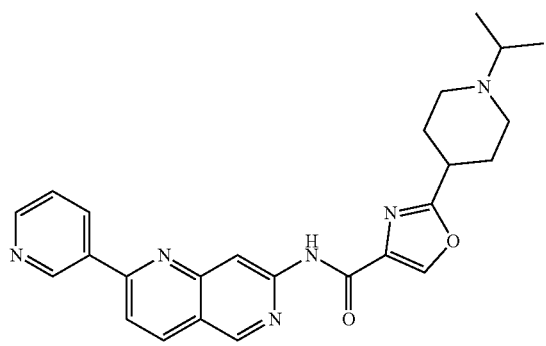 | 777 |
| 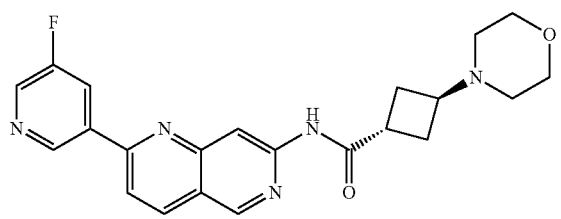 [SMILES: O=C(Nc1cc2nc(-c3cncc(F)c3)ccc2cn1)[C@H]1C[C@H](N2CCOCC2)C1] | 778 |
| 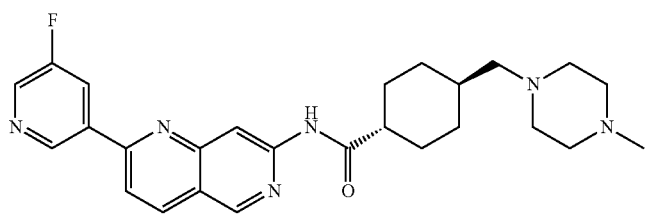 | 779 |
| 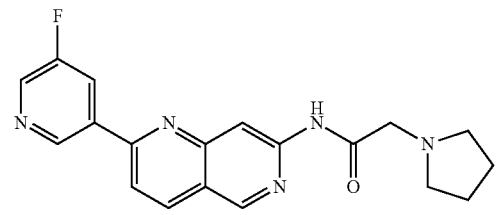 [SMILES: O=C(CN1CCCC1)Nc1cc2nc(-c3cncc(F)c3)ccc2cn1] | 780 |
| 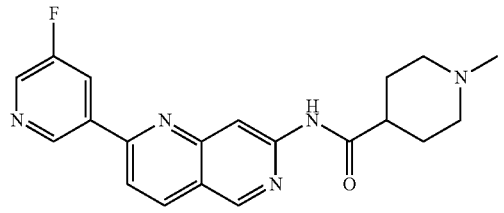 [SMILES: CN1CCC(C(=O)Nc2cc3nc(-c4cncc(F)c4)ccc3cn2)CC1] | 781 |
| 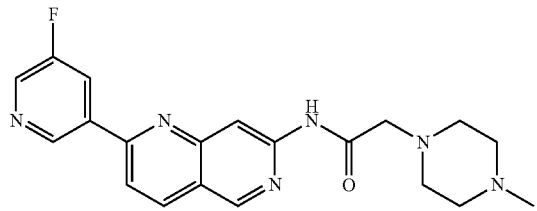 [SMILES: CN1CCN(CC(=O)Nc2cc3nc(-c4cncc(F)c4)ccc3cn2)CC1] | 782 |
| 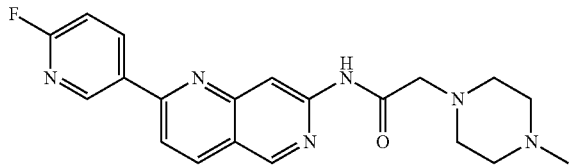 [SMILES: CN1CCN(CC(=O)Nc2cc3nc(-c4ccc(F)nc4)ccc3cn2)CC1] | 783 |

TABLE 1-continued
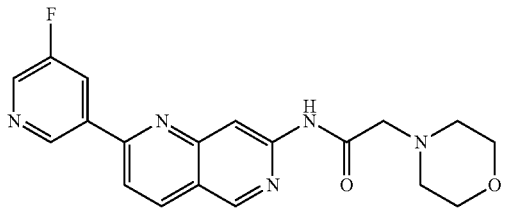 [SMILES: O=C(CN1CCOCC1)Nc1cc2nc(-c3cncc(F)c3)ccc2cn1] 784
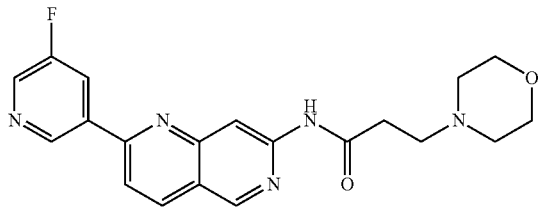 [SMILES: O=C(CCN1CCOCC1)Nc1cc2nc(-c3cncc(F)c3)ccc2cn1] 785
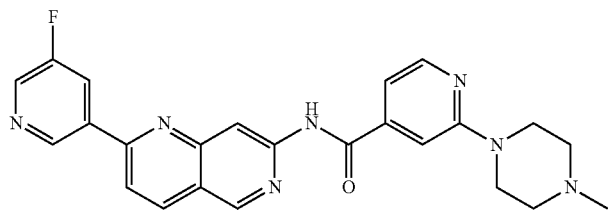 [SMILES: CN1CCN(c2cc(C(=O)Nc3cc4nc(-c5cncc(F)c5)ccc4cn3)ccn2)CC1] 786
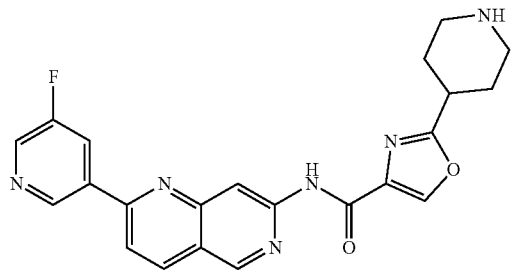 [SMILES: O=C(Nc1cc2nc(-c3cncc(F)c3)ccc2cn1)c1coc(C2CCNCC2)n1] 787
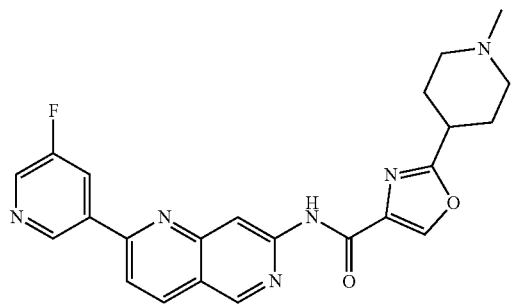 [SMILES: CN1CCC(c2nc(C(=O)Nc3cc4nc(-c5cncc(F)c5)ccc4cn3)co2)CC1] 788
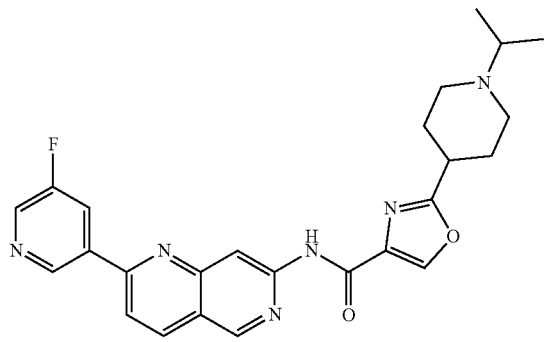 [SMILES: CC(C)N1CCC(c2nc(C(=O)Nc3cc4nc(-c5cncc(F)c5)ccc4cn3)co2)CC1] 789

TABLE 1-continued
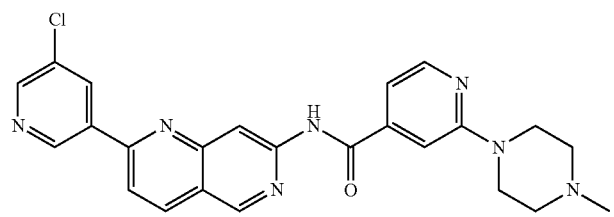 790
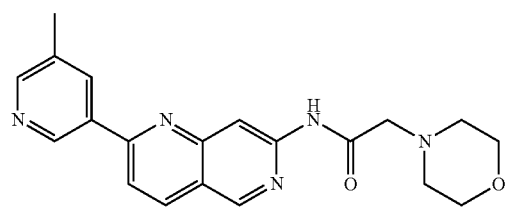 [SMILES: Cc1cncc(-c2ccc3cnc(NC(=O)CN4CCOCC4)cc3n2)c1] 791
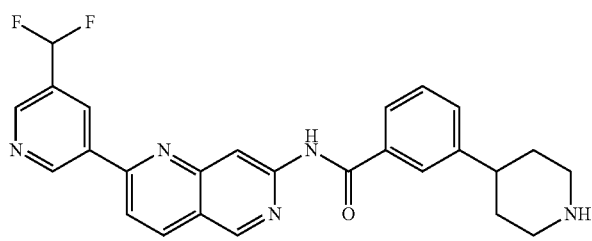 792
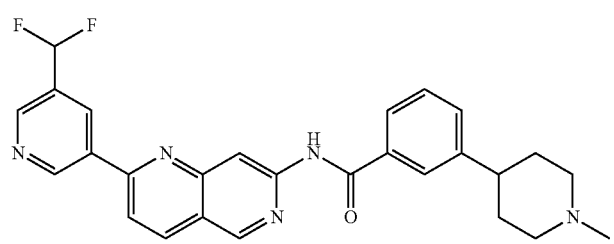 [SMILES: CN1CCC(c2cccc(C(=O)Nc3cc4nc(-c5cncc(C(F)F)c5)ccc4cn3)c2)CC1] 793
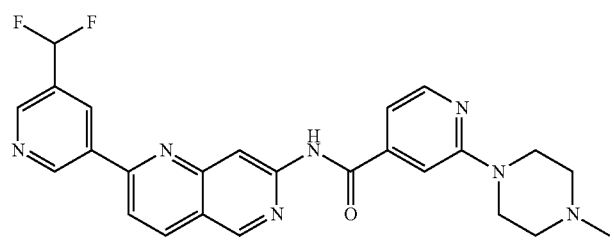 [SMILES: CN1CCN(c2cc(C(=O)Nc3cc4nc(-c5cncc(C(F)F)c5)ccc4cn3)ccn2)CC1] 794
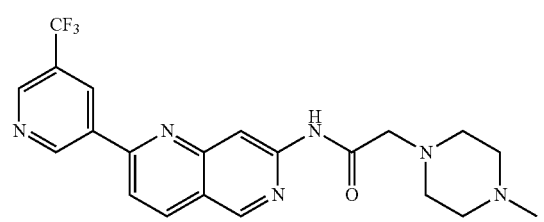 [SMILES: CN1CCN(CC(=O)Nc2cc3nc(-c4cncc(C(F)(F)F)c4)ccc3cn2)CC1] 795
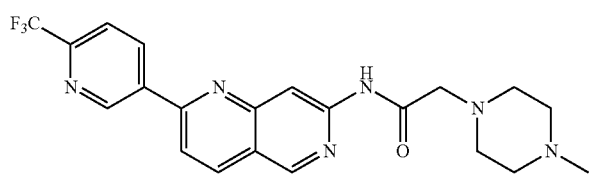 [SMILES: CN1CCN(CC(=O)Nc2cc3nc(-c4ccc(C(F)(F)F)nc4)ccc3cn2)CC1] 796

TABLE 1-continued
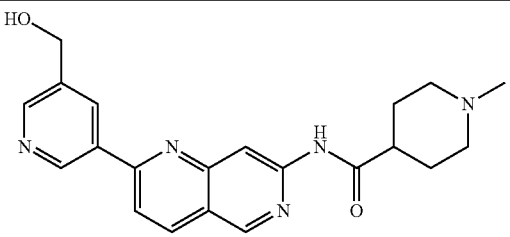
797
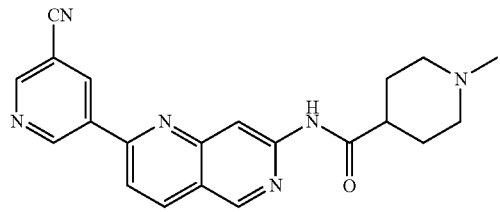
798
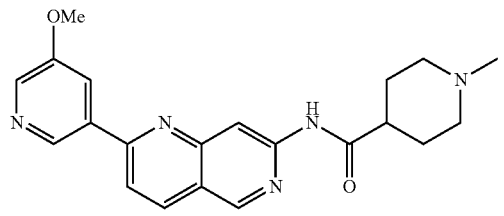 [SMILES: CN1CCC(C(=O)Nc2cc3nc(-c4cncc(C#N)c4)ccc3cn2)CC1]
799
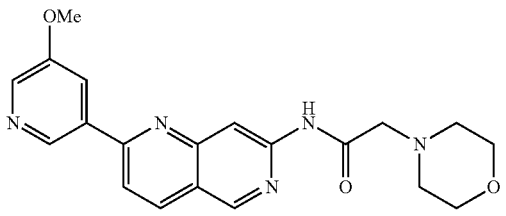 [SMILES: COc1cncc(-c2ccc3cnc(NC(=O)CN4CCOCC4)cc3n2)c1]
800
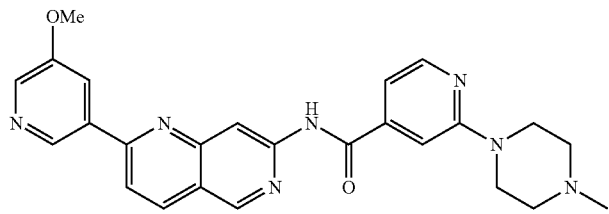 [SMILES: COc1cncc(-c2ccc3cnc(NC(=O)c4ccnc(N5CCN(C)CC5)c4)cc3n2)c1]
801
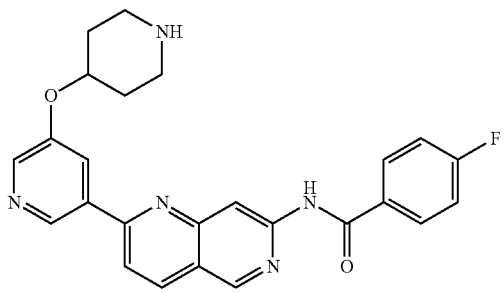 [SMILES: O=C(Nc1cc2nc(-c3cncc(OC4CCNCC4)c3)ccc2cn1)c1ccc(F)cc1]
802
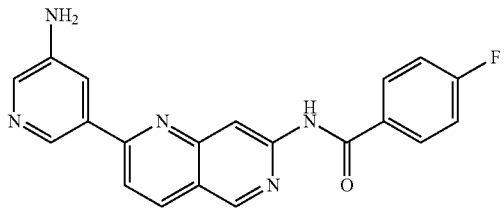 [SMILES: Nc1cncc(-c2ccc3cnc(NC(=O)c4ccc(F)cc4)cc3n2)c1]
803

TABLE 1-continued
| | |
|---|---|
| 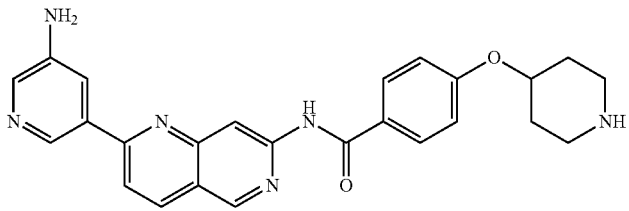 [SMILES: Nc1cncc(-c2ccc3cnc(NC(=O)c4ccc(OC5CCNCC5)cc4)cc3n2)c1] | 804 |
| 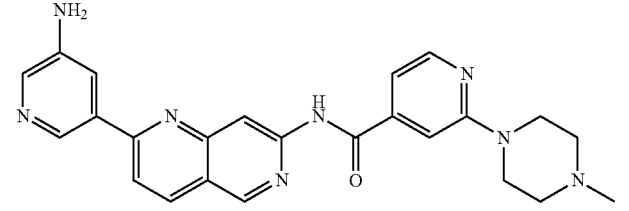 | 805 |
| 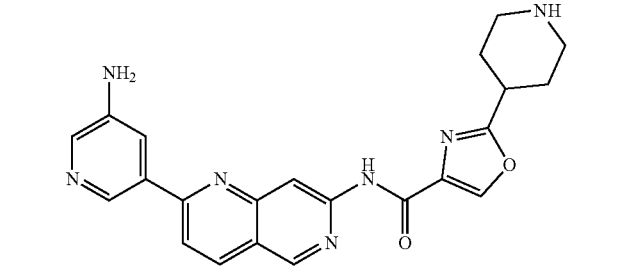 [SMILES: Nc1cncc(-c2ccc3cnc(NC(=O)c4coc(C5CCNCC5)n4)cc3n2)c1] | 806 |
| 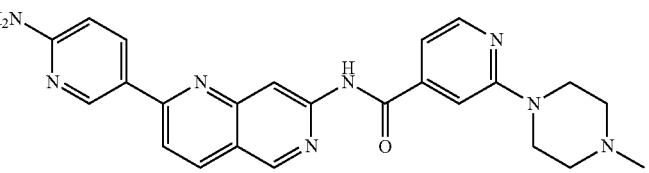 | 807 |
| 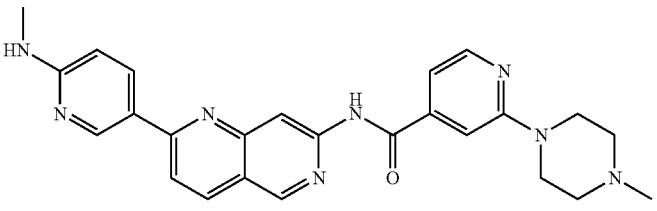 [SMILES: CNc1ccc(-c2ccc3cnc(NC(=O)c4ccnc(N5CCN(C)CC5)c4)cc3n2)cn1] | 808 |
| 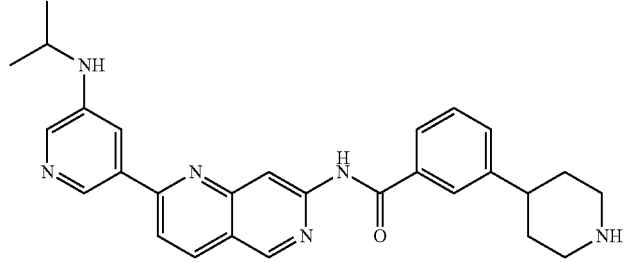 | 809 |
| 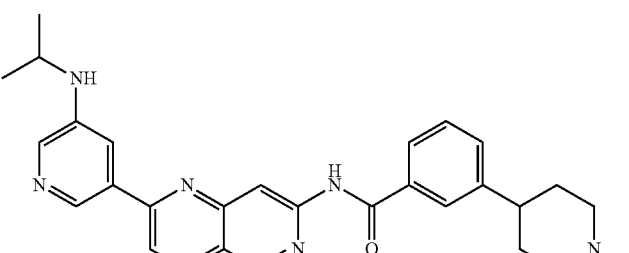 | 810 |

TABLE 1-continued
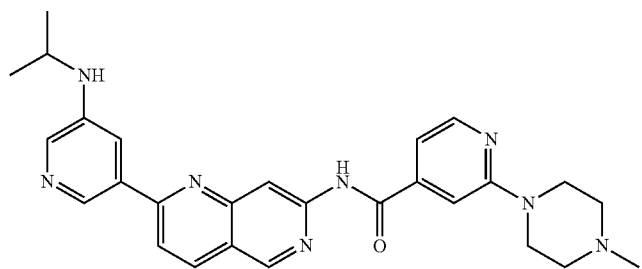 [SMILES: CC(C)Nc1cncc(-c2ccc3cnc(NC(=O)c4cccc(C5CCN(C)CC5)c4)cc3n2)c1] 811
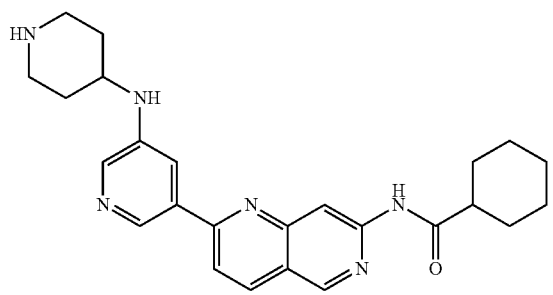 [SMILES: O=C(Nc1cc2nc(-c3cncc(NC4CCNCC4)c3)ccc2cn1)C1CCCCC1] 812
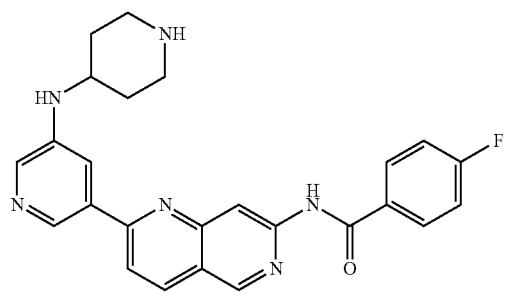 [SMILES: O=C(Nc1cc2nc(-c3cncc(NC4CCNCC4)c3)ccc2cn1)c1ccc(F)cc1] 813
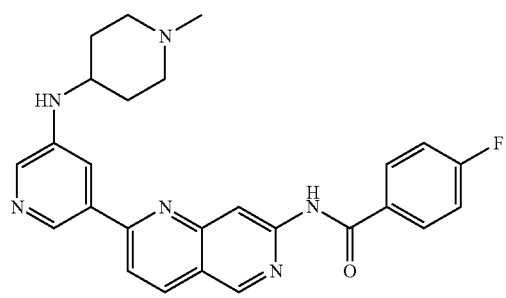 [SMILES: CN1CCC(Nc2cncc(-c3ccc4cnc(NC(=O)c5ccc(F)cc5)cc4n3)c2)CC1] 814
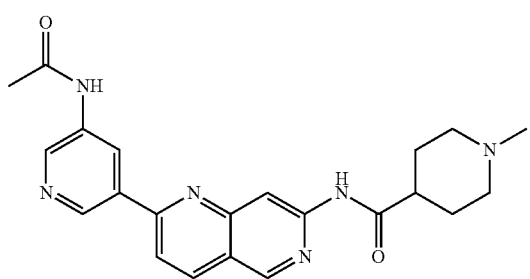 [SMILES: CC(=O)Nc1cncc(-c2ccc3cnc(NC(=O)C4CCN(C)CC4)cc3n2)c1] 815

TABLE 1-continued
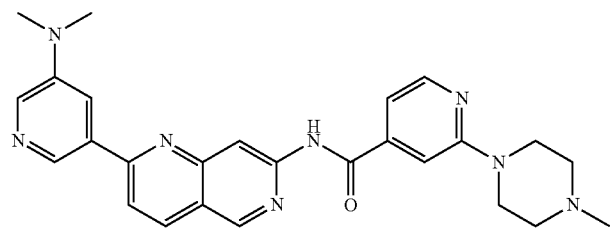 [SMILES: CN1CCN(c2cc(C(=O)Nc3cc4nc(-c5cncc(N(C)C)c5)ccc4cn3)ccn2)CC1]
816
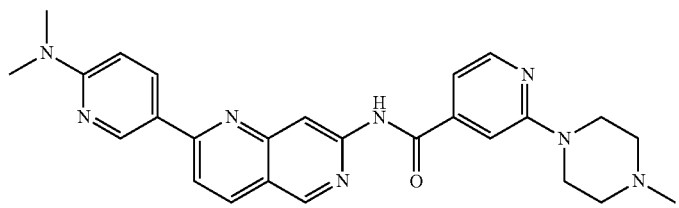
817
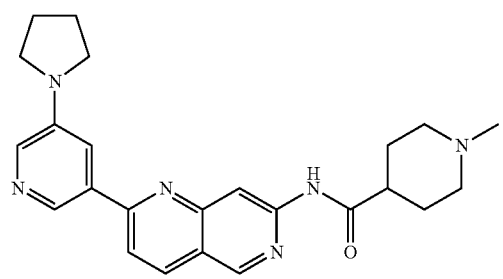 [SMILES: CN1CCC(C(=O)Nc2cc3nc(-c4cncc(N5CCCC5)c4)ccc3cn2)CC1]
818
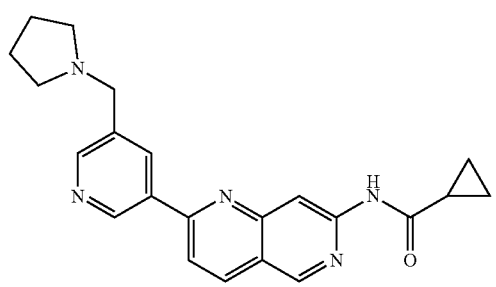
819
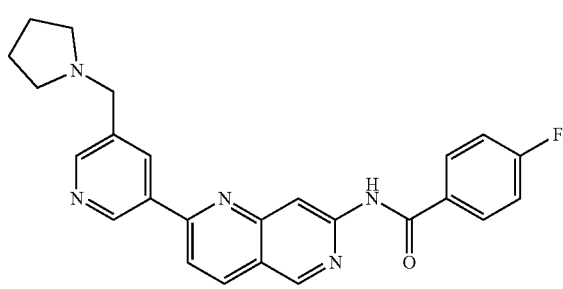 [SMILES: O=C(Nc1cc2nc(-c3cncc(CN4CCCC4)c3)ccc2cn1)c1ccc(F)cc1]
820
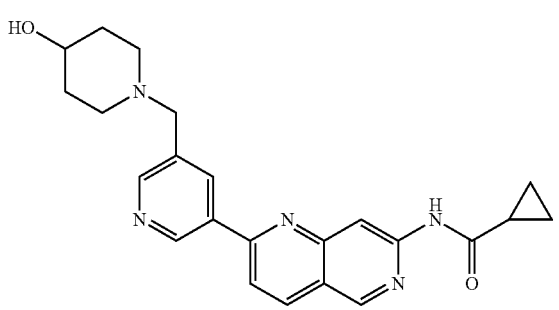 [SMILES: O=C(Nc1cc2nc(-c3cncc(CN4CCC(O)CC4)c3)ccc2cn1)C1CC1]
821

TABLE 1-continued
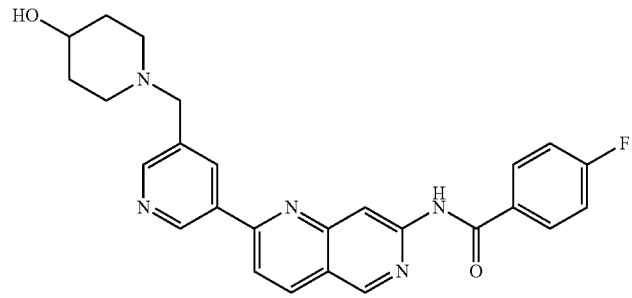 [SMILES: O=C(Nc1cc2nc(-c3cncc(CN4CCC(O)CC4)c3)ccc2cn1)c1ccc(F)cc1]
822
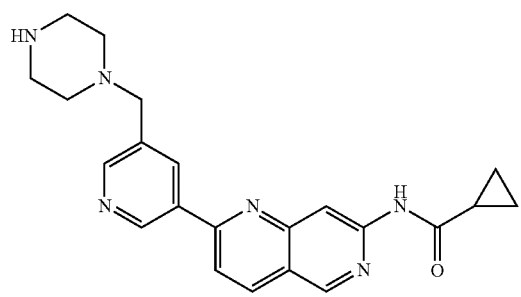 [SMILES: O=C(Nc1cc2nc(-c3cncc(CN4CCNCC4)c3)ccc2cn1)C1CC1]
823
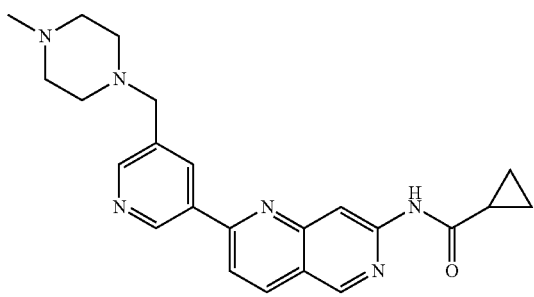 [SMILES: CN1CCN(Cc2cncc(-c3ccc4cnc(NC(=O)C5CC5)cc4n3)c2)CC1]
824
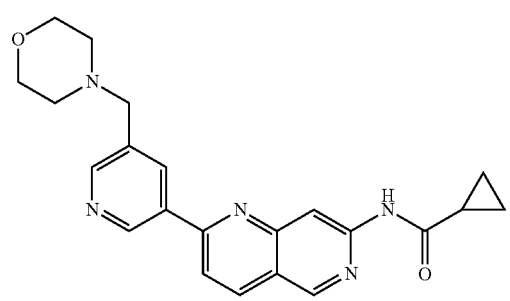 [SMILES: O=C(Nc1cc2nc(-c3cncc(CN4CCOCC4)c3)ccc2cn1)C1CC1]
825
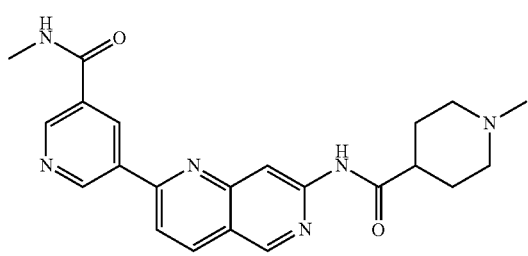
826

TABLE 1-continued
| | |
|---|---|
| 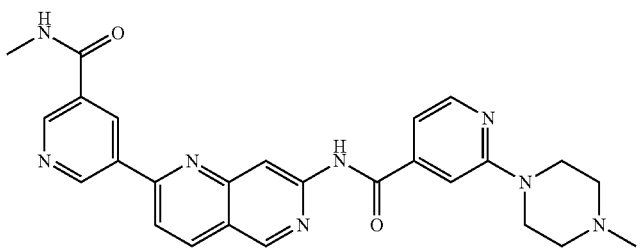 | 827 |
| 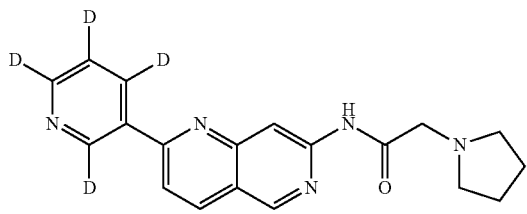 [SMILES: [2H]c1nc([2H])c(-c2ccc3cnc(NC(=O)CN4CCCC4)cc3n2)c([2H])c1[2H]] | 828 |
| 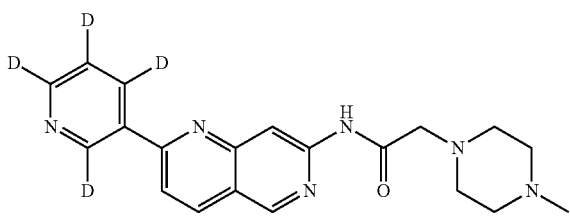 [SMILES: [2H]c1nc([2H])c(-c2ccc3cnc(NC(=O)CN4CCN(C)CC4)cc3n2)c([2H])c1[2H]] | 829 |
| 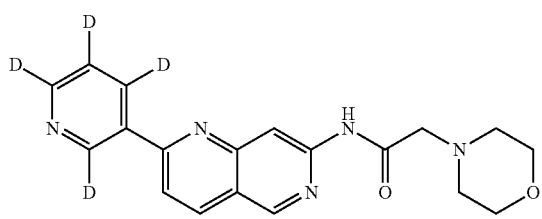 [SMILES: [2H]c1nc([2H])c(-c2ccc3cnc(NC(=O)CN4CCOCC4)cc3n2)c([2H])c1[2H]] | 830 |
| 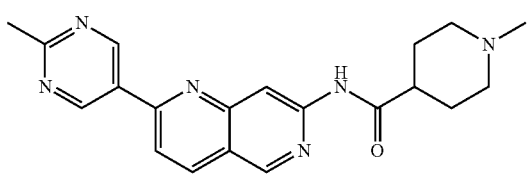 | 831 |
| 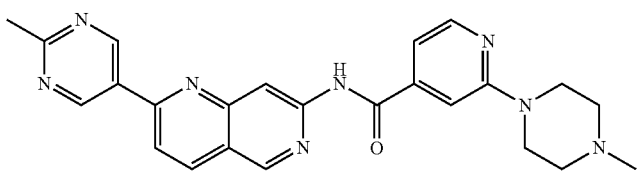 | 832 |
| 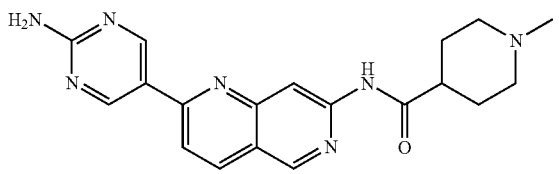 [SMILES: CN1CCC(C(=O)Nc2cc3nc(-c4cnc(N)nc4)ccc3cn2)CC1] | 833 |
| 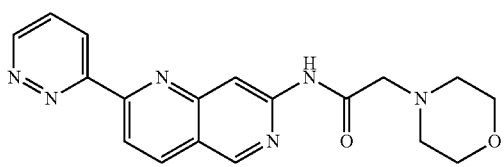 [SMILES: O=C(CN1CCOCC1)Nc1cc2nc(-c3cccnn3)ccc2cn1] | 834 |

TABLE 1-continued
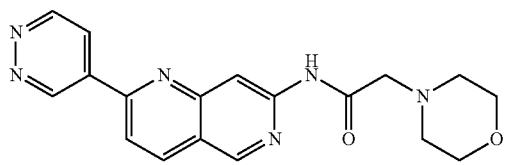 [SMILES: O=C(CN1CCOCC1)Nc1cc2nc(-c3ccnnc3)ccc2cn1]
835
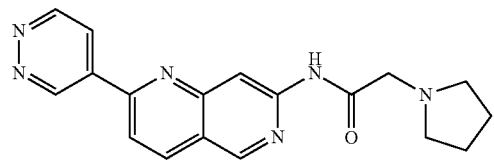 [SMILES: O=C(CN1CCCC1)Nc1cc2nc(-c3ccnnc3)ccc2cn1]
836
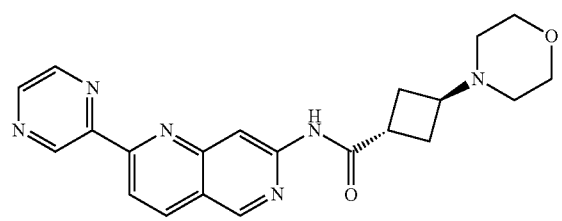 [SMILES: O=C(Nc1cc2nc(-c3cnccn3)ccc2cn1)[C@H]1C[C@H](N2CCOCC2)C1]
837
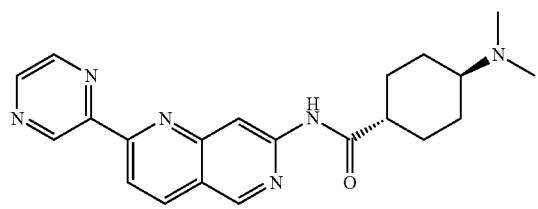 [SMILES: CN(C)[C@H]1CC[C@H](C(=O)Nc2cc3nc(-c4cnccn4)ccc3cn2)CC1]
838
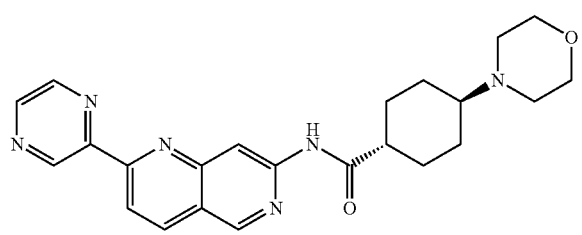 [SMILES: O=C(Nc1cc2nc(-c3cnccn3)ccc2cn1)[C@H]1CC[C@H](N2CCOCC2)CC1]
839
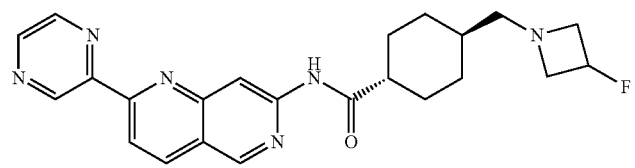 [SMILES: O=C(Nc1cc2nc(-c3cnccn3)ccc2cn1)[C@H]1CC[C@H](CN2CC(F)C2)CC1]
840
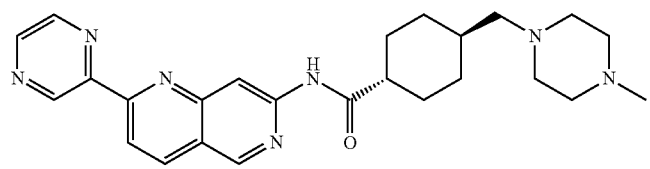 [SMILES: CN1CCN(C[C@H]2CC[C@H](C(=O)Nc3cc4nc(-c5cnccn5)ccc4cn3)CC2)CC1]
841
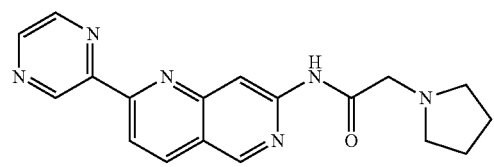 [SMILES: O=C(CN1CCCC1)Nc1cc2nc(-c3cnccn3)ccc2cn1]
842

TABLE 1-continued
| | |
|---|---|
| 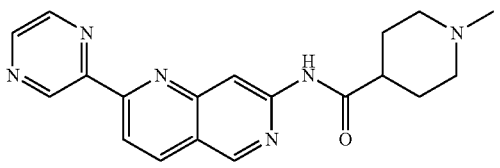 [SMILES: CN1CCC(C(=O)Nc2cc3nc(-c4cnccn4)ccc3cn2)CC1] | 843 |
| 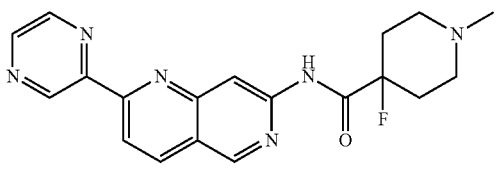 [SMILES: CN1CCC(F)(C(=O)Nc2cc3nc(-c4cnccn4)ccc3cn2)CC1] | 844 |
| 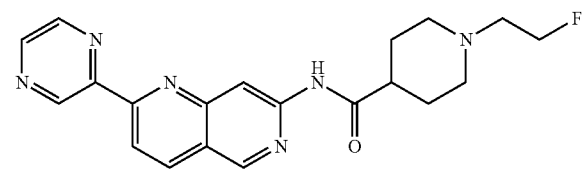 [SMILES: O=C(Nc1cc2nc(-c3cnccn3)ccc2cn1)C1CCN(CCF)CC1] | 845 |
| 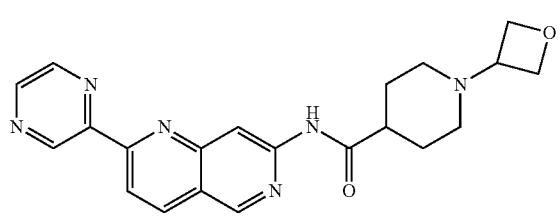 [SMILES: O=C(Nc1cc2nc(-c3cnccn3)ccc2cn1)C1CCN(C2COC2)CC1] | 846 |
| 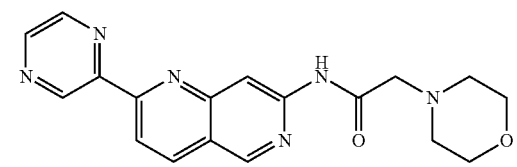 [SMILES: O=C(CN1CCOCC1)Nc1cc2nc(-c3cnccn3)ccc2cn1] | 847 |
| 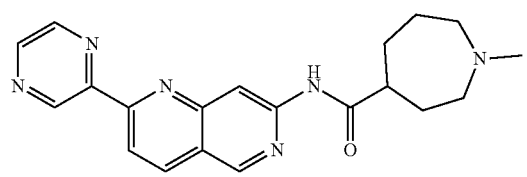 [SMILES: CN1CCCC(C(=O)Nc2cc3nc(-c4cnccn4)ccc3cn2)CC1] | 848 |
| 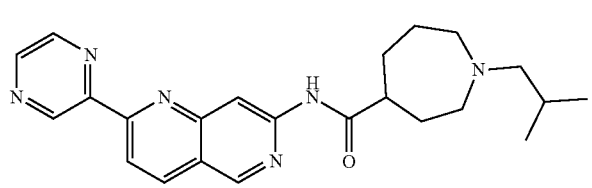 [SMILES: CC(C)CN1CCCC(C(=O)Nc2cc3nc(-c4cnccn4)ccc3cn2)CC1] | 849 |
| 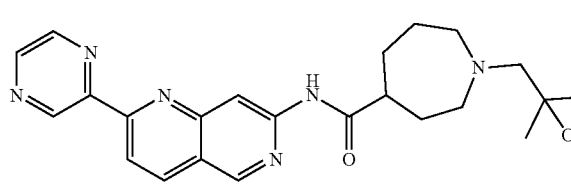 | 850 |
| 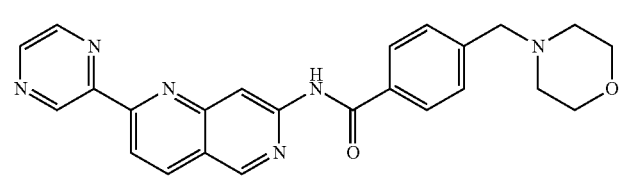 [SMILES: O=C(Nc1cc2nc(-c3cnccn3)ccc2cn1)c1ccc(CN2CCOCC2)cc1] | 851 |

TABLE 1-continued
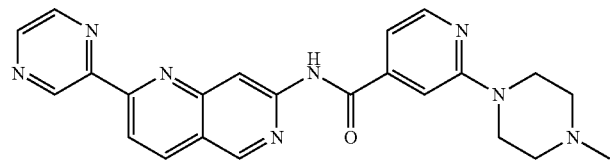 [SMILES: CN1CCN(c2cc(C(=O)Nc3cc4nc(-c5cnccn5)ccc4cn3)ccn2)CC1] 852
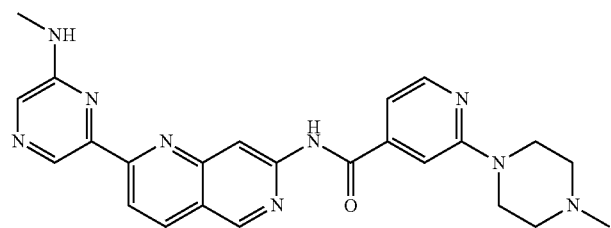 [SMILES: CNc1cncc(-c2ccc3cnc(NC(=O)c4ccnc(N5CCN(C)CC5)c4)cc3n2)n1] 853
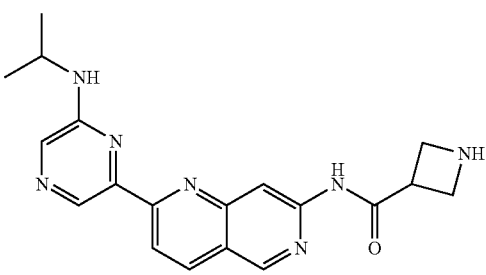 [SMILES: CC(C)Nc1cncc(-c2ccc3cnc(NC(=O)C4CNC4)cc3n2)n1] 854
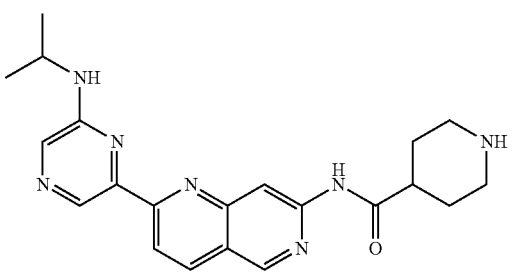 855
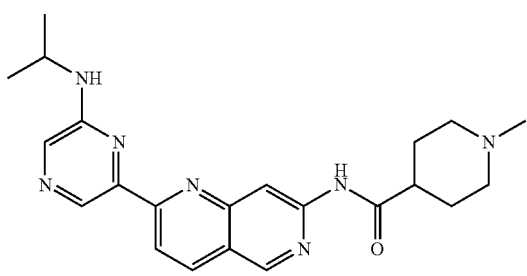 [SMILES: CC(C)Nc1cncc(-c2ccc3cnc(NC(=O)C4CCN(C)CC4)cc3n2)n1] 856
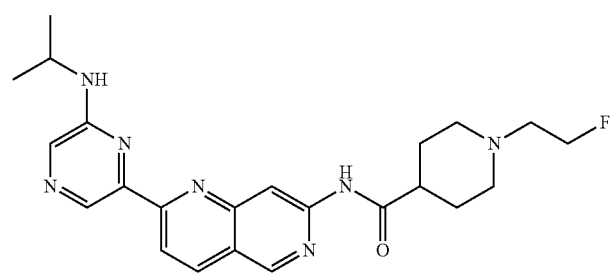 [SMILES: CC(C)Nc1cncc(-c2ccc3cnc(NC(=O)C4CCN(CCF)CC4)cc3n2)n1] 857

TABLE 1-continued
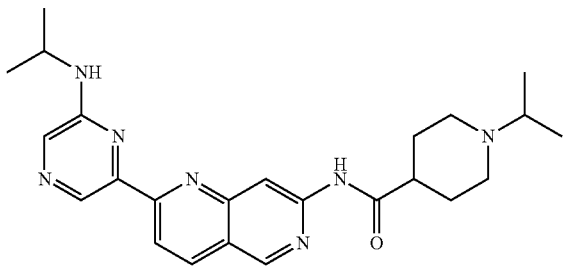 [SMILES: CC(C)Nc1cncc(-c2ccc3cnc(NC(=O)C4CCN(C(C)C)CC4)cc3n2)n1]
858
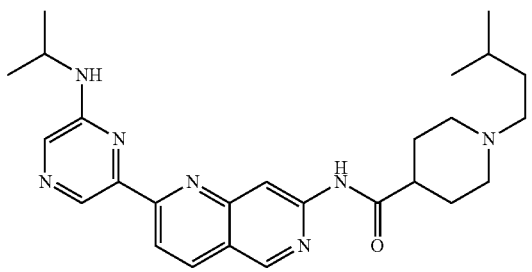 [SMILES: CC(C)CCN1CCC(C(=O)Nc2cc3nc(-c4cncc(NC(C)C)n4)ccc3cn2)CC1]
859
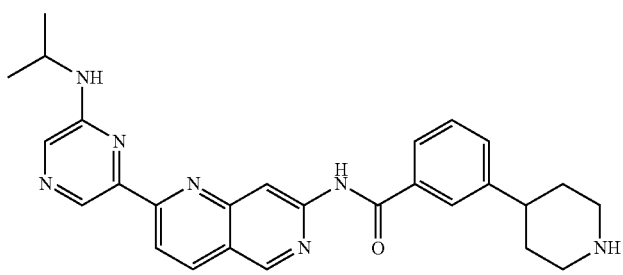 [SMILES: CC(C)Nc1cncc(-c2ccc3cnc(NC(=O)c4cccc(C5CCNCC5)c4)cc3n2)n1]
860
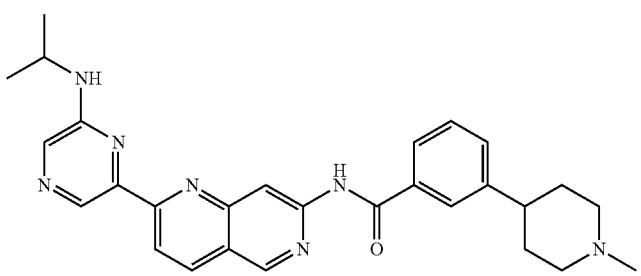
861
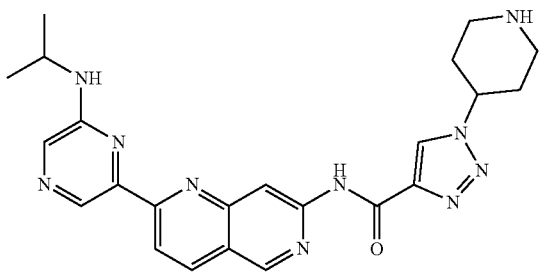 [SMILES: CC(C)Nc1cncc(-c2ccc3cnc(NC(=O)c4cn(C5CCNCC5)nn4)cc3n2)n1]
862

TABLE 1-continued
| | |
|---|---|
| 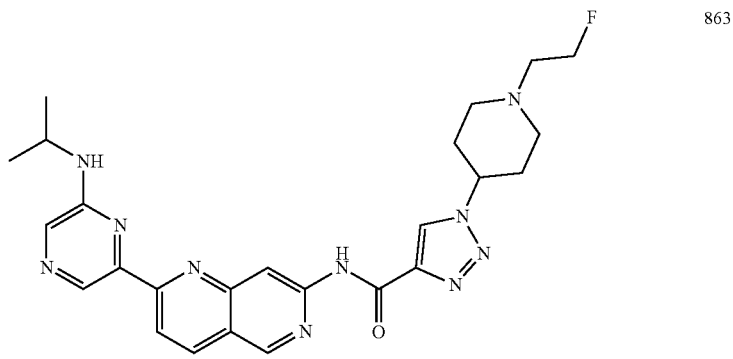 | 863 |
| 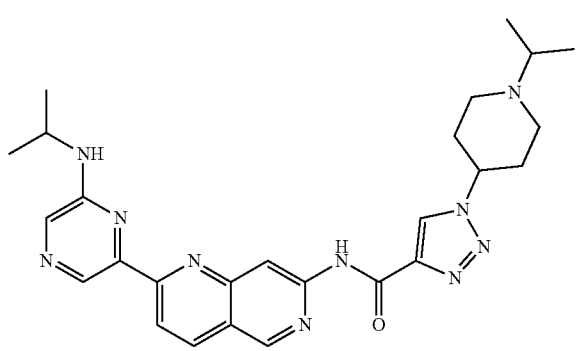 [SMILES: CC(C)Nc1cncc(-c2ccc3cnc(NC(=O)c4cn(C5CCN(C(C)C)CC5)nn4)cc3n2)n1] | 864 |
| 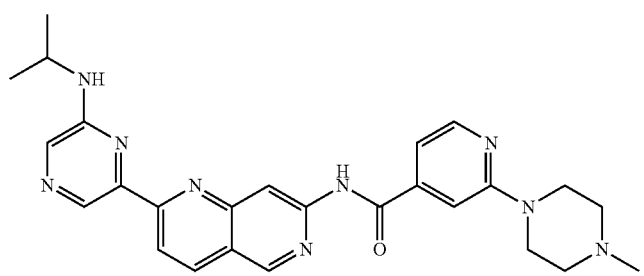 [SMILES: CC(C)Nc1cncc(-c2ccc3cnc(NC(=O)c4ccnc(N5CCN(C)CC5)c4)cc3n2)n1] | 865 |
| 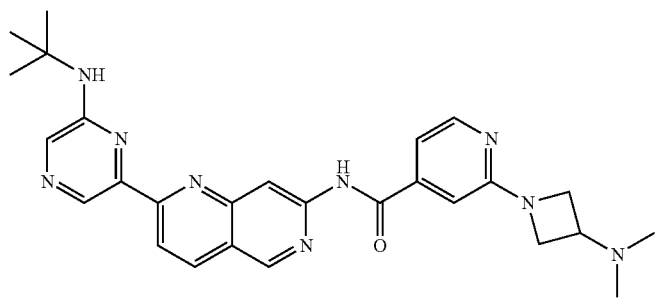 [SMILES: CN(C)C1CN(c2cc(C(=O)Nc3cc4nc(-c5cncc(NC(C)(C)C)n5)ccc4cn3)ccn2)C1] | 866 |
| 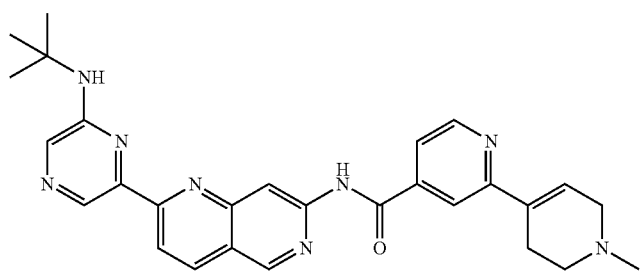 [SMILES: CN1CC=C(c2cc(C(=O)Nc3cc4nc(-c5cncc(NC(C)(C)C)n5)ccc4cn3)ccn2)CC1] | 867 |

TABLE 1-continued
868
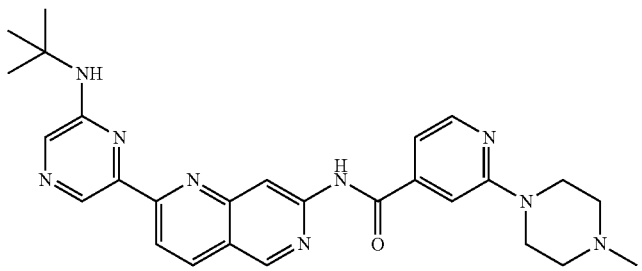
869
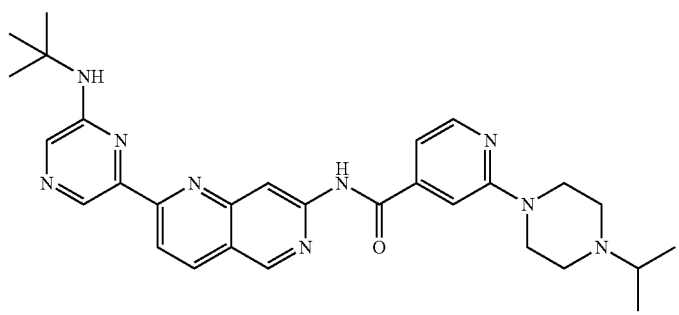 [SMILES: CC(C)N1CCN(c2cc(C(=O)Nc3cc4nc(-c5cncc(NC(C)(C)C)n5)ccc4cn3)ccn2)CC1]
870
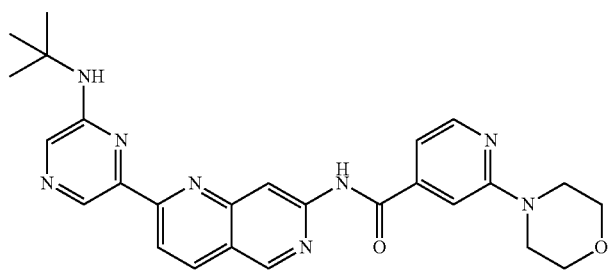 [SMILES: CC(C)(C)Nc1cncc(-c2ccc3cnc(NC(=O)c4ccnc(N5CCOCC5)c4)cc3n2)n1]
871
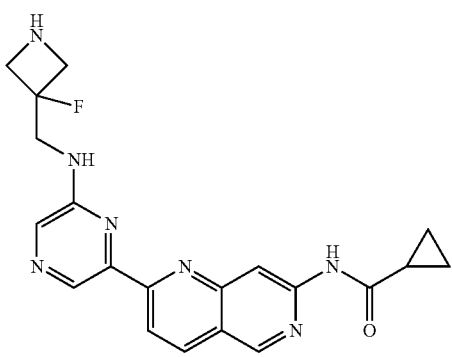
872
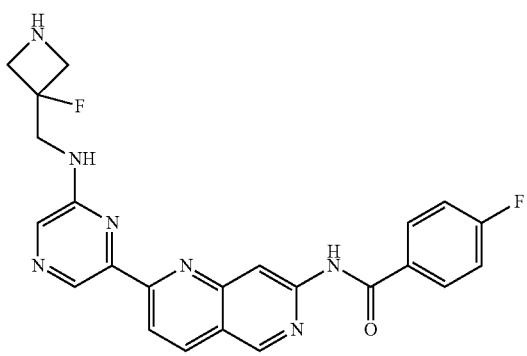 [SMILES: O=C(Nc1cc2nc(-c3cncc(NCC4(F)CNC4)n3)ccc2cn1)c1ccc(F)cc1]

TABLE 1-continued

| | |
|---|---|
| (structure) | 873 |
| (structure) | 874 |
| (structure) | 875 |
| (structure) | 876 |
| (structure) | 877 |

TABLE 1-continued
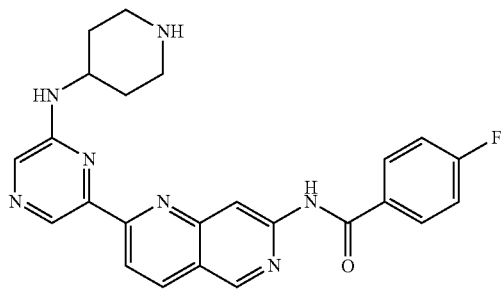 [SMILES: O=C(Nc1cc2nc(-c3cncc(NC4CCNCC4)n3)ccc2cn1)c1ccc(F)cc1] 878
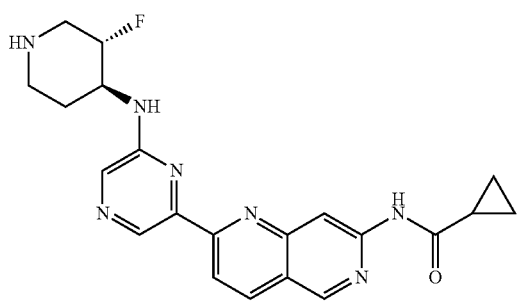 [SMILES: O=C(Nc1cc2nc(-c3cncc(N[C@H]4CCNC[C@@H]4F)n3)ccc2cn1)C1CC1] 879
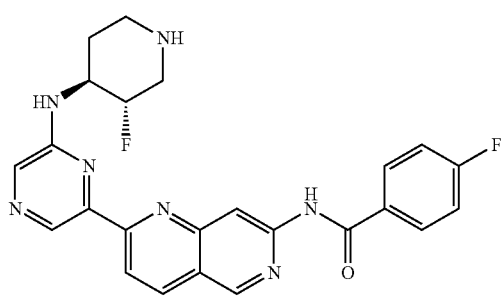 [SMILES: O=C(Nc1cc2nc(-c3cncc(N[C@H]4CCNC[C@@H]4F)n3)ccc2cn1)c1ccc(F)cc1] 880
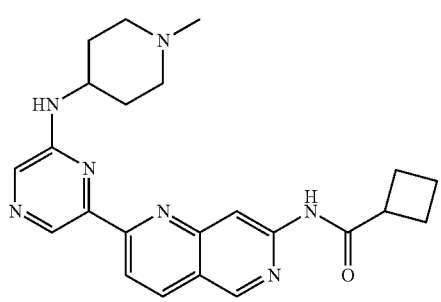 [SMILES: CN1CCC(Nc2cncc(-c3ccc4cnc(NC(=O)C5CCC5)cc4n3)n2)CC1] 881
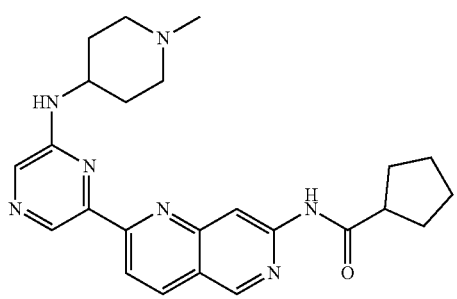 [SMILES: CN1CCC(Nc2cncc(-c3ccc4cnc(NC(=O)C5CCCC5)cc4n3)n2)CC1] 882

TABLE 1-continued
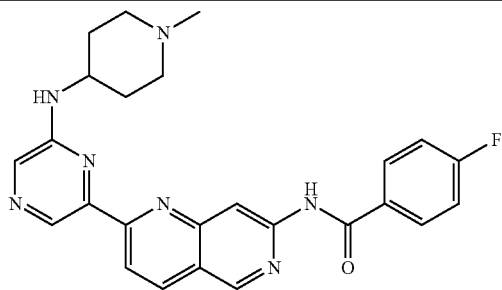
883
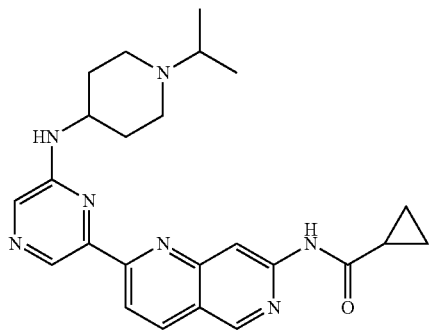 [SMILES: CC(C)N1CCC(Nc2cncc(-c3ccc4cnc(NC(=O)C5CC5)cc4n3)n2)CC1]
884
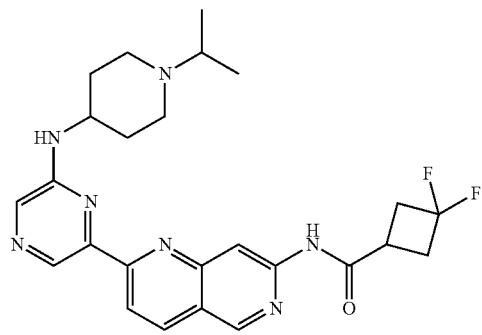 [SMILES: CC(C)N1CCC(Nc2cncc(-c3ccc4cnc(NC(=O)C5CC(F)(F)C5)cc4n3)n2)CC1]
885
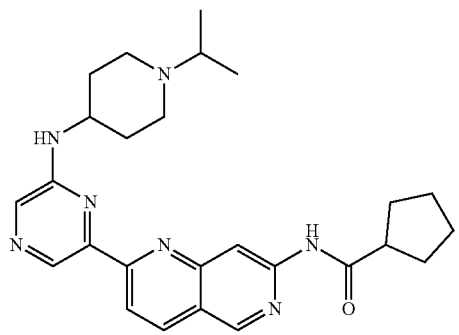 [SMILES: CC(C)N1CCC(Nc2cncc(-c3ccc4cnc(NC(=O)C5CCCC5)cc4n3)n2)CC1]
886
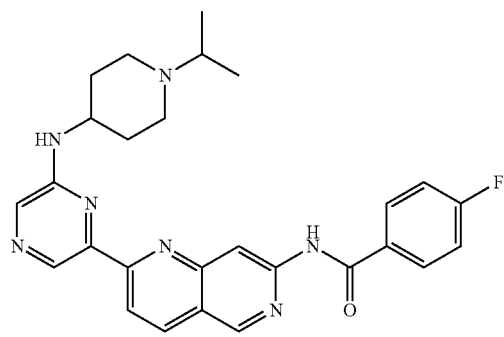 [SMILES: CC(C)N1CCC(Nc2cncc(-c3ccc4cnc(NC(=O)c5ccc(F)cc5)cc4n3)n2)CC1]
887

TABLE 1-continued
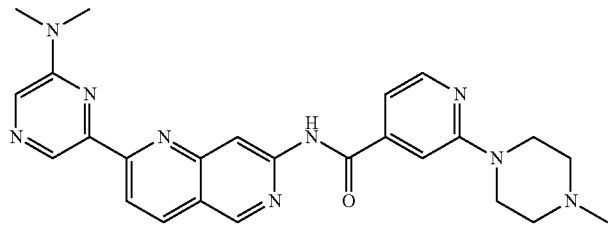
888
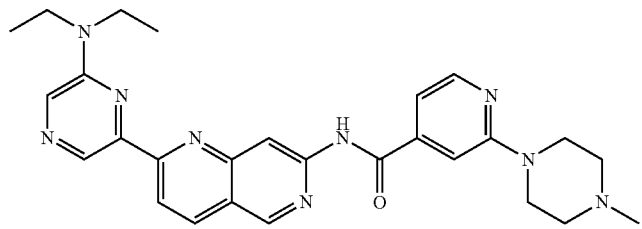 [SMILES: CCN(CC)c1cncc(-c2ccc3cnc(NC(=O)c4ccnc(N5CCN(C)CC5)c4)cc3n2)n1]
889
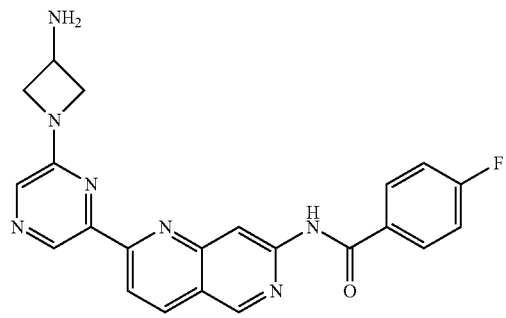 [SMILES: NC1CN(c2cncc(-c3ccc4cnc(NC(=O)c5ccc(F)cc5)cc4n3)n2)C1]
890
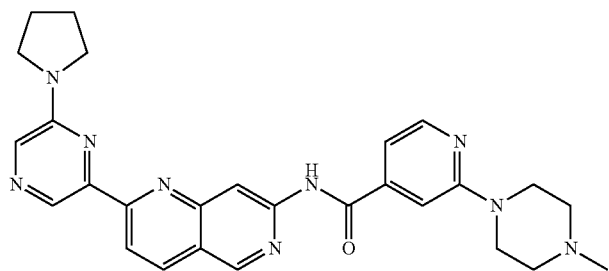
891
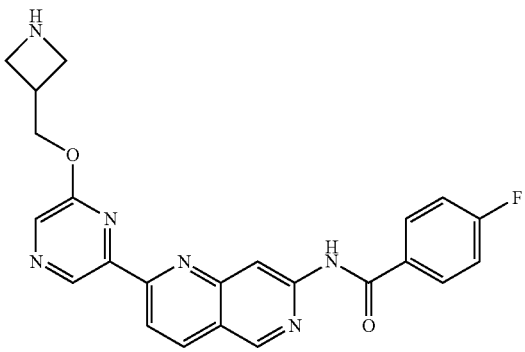 [SMILES: O=C(Nc1cc2nc(-c3cncc(OCC4CNC4)n3)ccc2cn1)c1ccc(F)cc1]
892

TABLE 1-continued
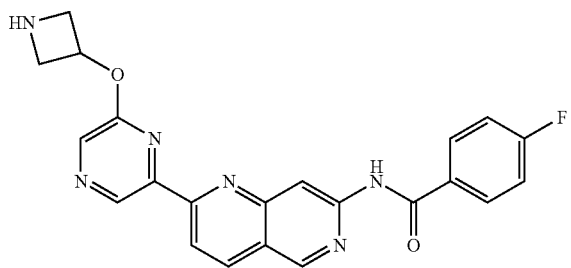 [SMILES: O=C(Nc1cc2nc(-c3cncc(OC4CNC4)n3)ccc2cn1)c1ccc(F)cc1]
893
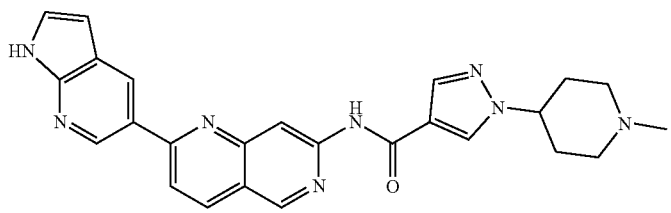 [SMILES: CN1CCC(n2cc(C(=O)Nc3cc4nc(-c5cnc6[nH]ccc6c5)ccc4cn3)cn2)CC1]
894
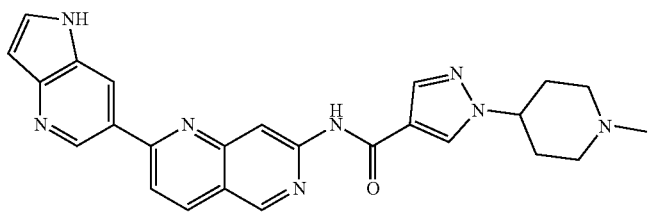 [SMILES: CN1CCC(n2cc(C(=O)Nc3cc4nc(-c5cnc6cc[nH]c6c5)ccc4cn3)cn2)CC1]
895
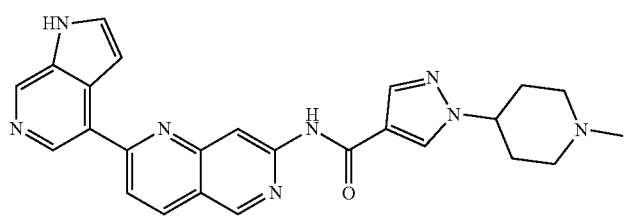
896
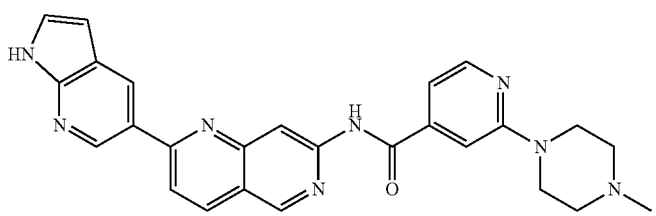 [SMILES: CN1CCN(c2cc(C(=O)Nc3cc4nc(-c5cnc6[nH]ccc6c5)ccc4cn3)ccn2)CC1]
897
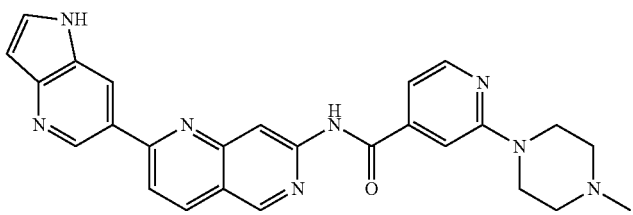 [SMILES: CN1CCN(c2cc(C(=O)Nc3cc4nc(-c5cnc6cc[nH]c6c5)ccc4cn3)ccn2)CC1]
898
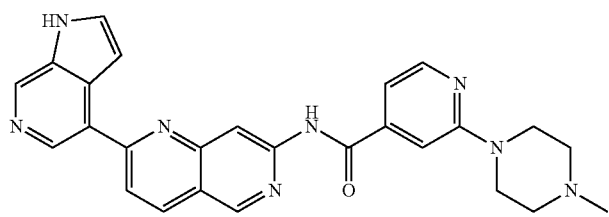
899

TABLE 1-continued
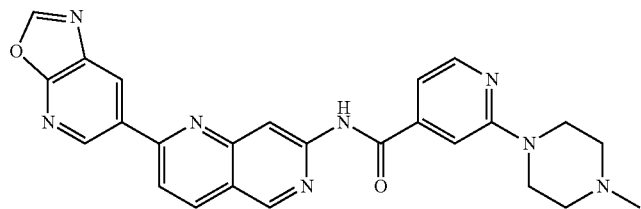 [SMILES: CN1CCN(c2cc(C(=O)Nc3cc4nc(-c5cnc6ocnc6c5)ccc4cn3)ccn2)CC1]
900
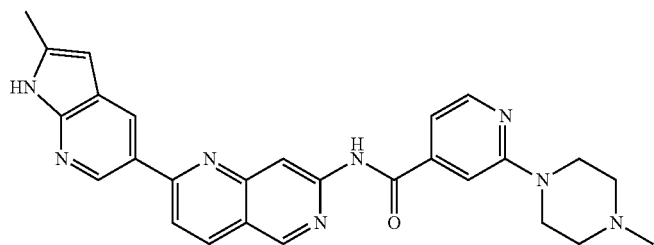
901
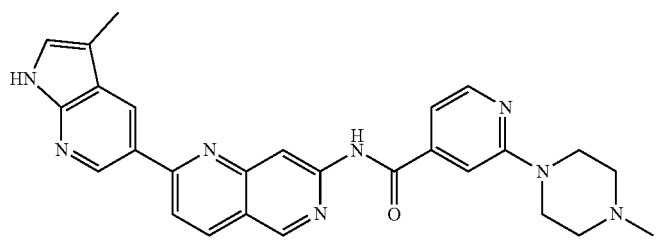 [SMILES: Cc1c[nH]c2ncc(-c3ccc4cnc(NC(=O)c5ccnc(N6CCN(C)CC6)c5)cc4n3)cc12]
902
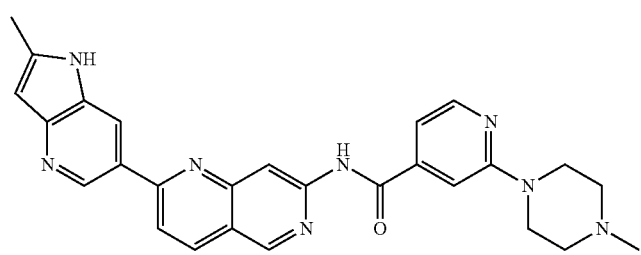
903
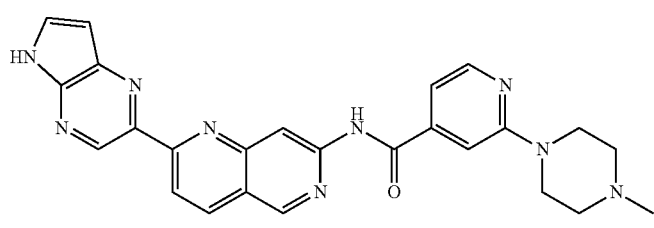 [SMILES: CN1CCN(c2cc(C(=O)Nc3cc4nc(-c5cnc6[nH]ccc6n5)ccc4cn3)ccn2)CC1]
904
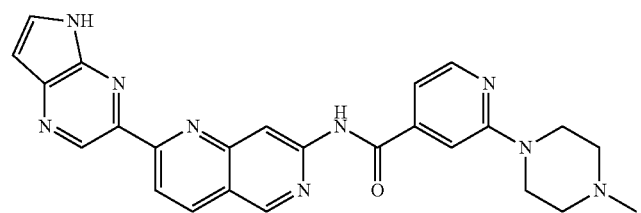
905

US 10,703,748 B2
TABLE 1-continued
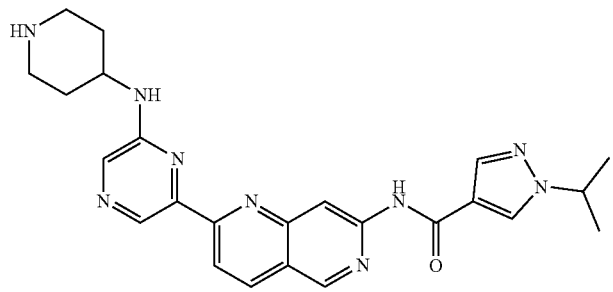 906
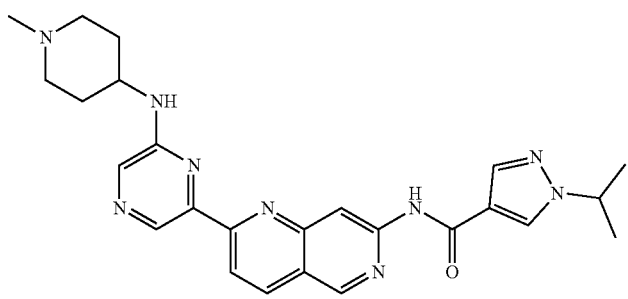 [SMILES: CC(C)n1cc(C(=O)Nc2cc3nc(-c4cncc(NC5CCN(C)CC5)n4)ccc3cn2)cn1] 907
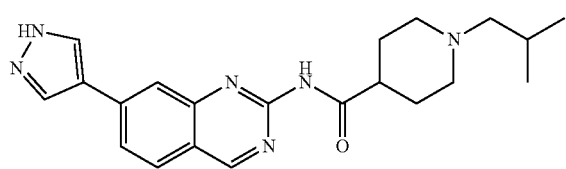 [SMILES: CC(C)CN1CCC(C(=O)Nc2ncc3ccc(-c4cn[nH]c4)cc3n2)CC1] 908
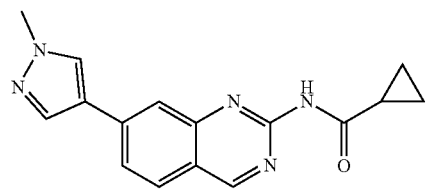 [SMILES: Cn1cc(-c2ccc3cnc(NC(=O)C4CC4)nc3c2)cn1] 909
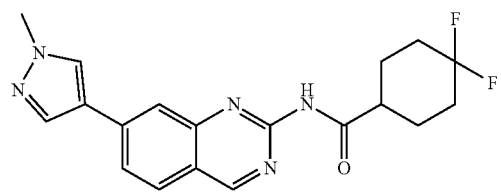 [SMILES: Cn1cc(-c2ccc3cnc(NC(=O)C4CCC(F)(F)CC4)nc3c2)cn1] 910
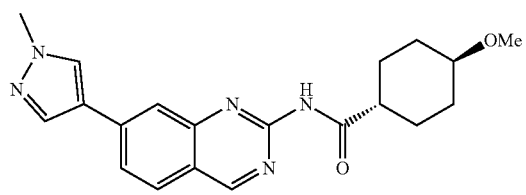 911
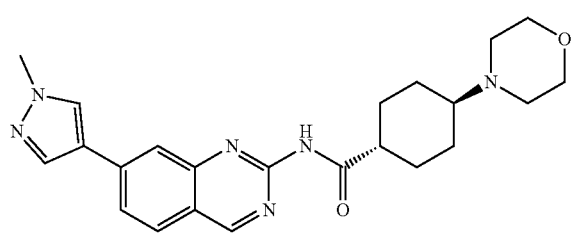 [SMILES: Cn1cc(-c2ccc3cnc(NC(=O)[C@H]4CC[C@H](N5CCOCC5)CC4)nc3c2)cn1] 912

TABLE 1-continued
| | |
|---|---|
| 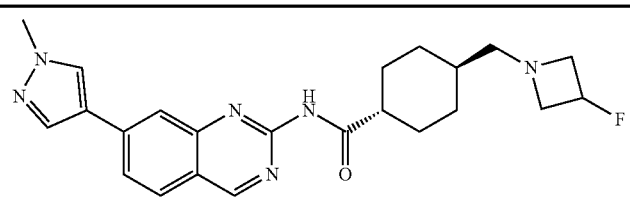 | 913 |
| 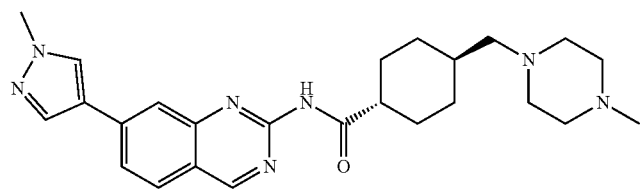 [SMILES: CN1CCN(C[C@H]2CC[C@H](C(=O)Nc3ncc4ccc(-c5cnn(C)c5)cc4n3)CC2)CC1] | 914 |
| 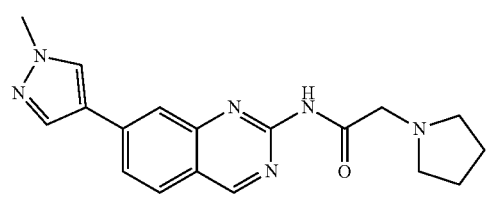 [SMILES: Cn1cc(-c2ccc3cnc(NC(=O)CN4CCCC4)nc3c2)cn1] | 915 |
| 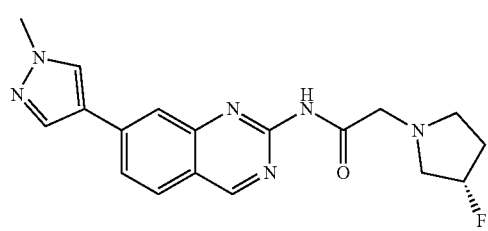 [SMILES: Cn1cc(-c2ccc3cnc(NC(=O)CN4CC[C@H](F)C4)nc3c2)cn1] | 916 |
| 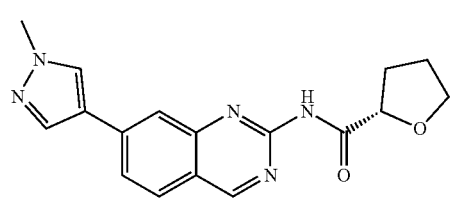 [SMILES: Cn1cc(-c2ccc3cnc(NC(=O)[C@@H]4CCCO4)nc3c2)cn1] | 917 |
| 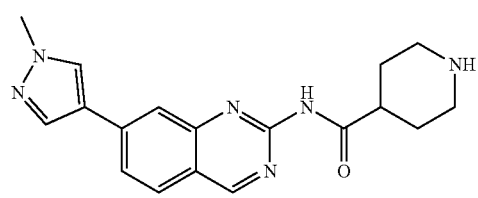 [SMILES: Cn1cc(-c2ccc3cnc(NC(=O)C4CCNCC4)nc3c2)cn1] | 918 |
| 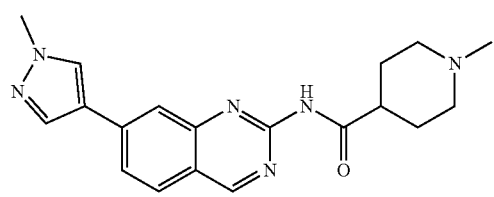 [SMILES: CN1CCC(C(=O)Nc2ncc3ccc(-c4cnn(C)c4)cc3n2)CC1] | 919 |
| 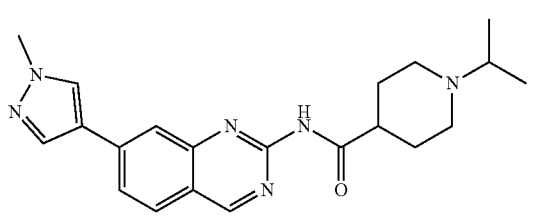 [SMILES: CC(C)N1CCC(C(=O)Nc2ncc3ccc(-c4cnn(C)c4)cc3n2)CC1] | 920 |

TABLE 1-continued
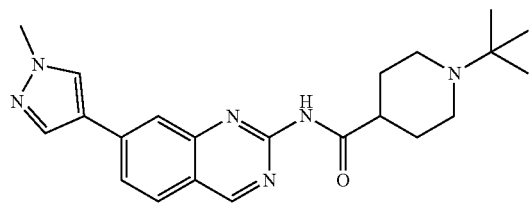 [SMILES: Cn1cc(-c2ccc3cnc(NC(=O)C4CCN(C(C)(C)C)CC4)nc3c2)cn1] 921
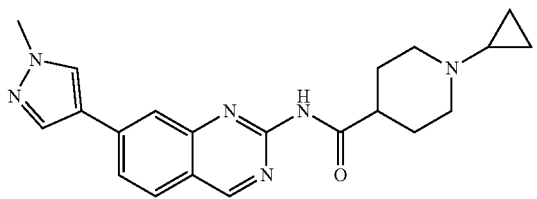 [SMILES: Cn1cc(-c2ccc3cnc(NC(=O)C4CCN(C5CC5)CC4)nc3c2)cn1] 922
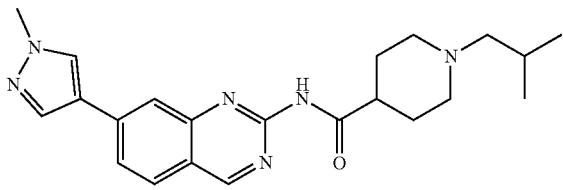 [SMILES: CC(C)CN1CCC(C(=O)Nc2ncc3ccc(-c4cnn(C)c4)cc3n2)CC1] 923
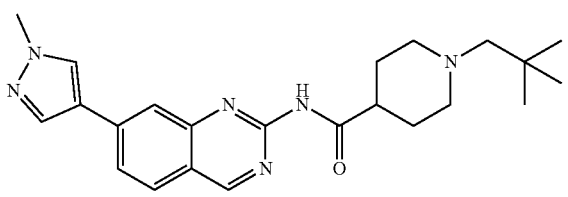 [SMILES: Cn1cc(-c2ccc3cnc(NC(=O)C4CCN(CC(C)(C)C)CC4)nc3c2)cn1] 924
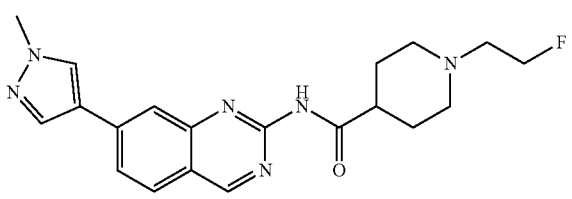 [SMILES: Cn1cc(-c2ccc3cnc(NC(=O)C4CCN(CCF)CC4)nc3c2)cn1] 925
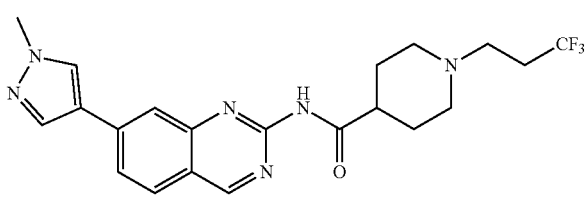 [SMILES: Cn1cc(-c2ccc3cnc(NC(=O)C4CCN(CCC(F)(F)F)CC4)nc3c2)cn1] 926
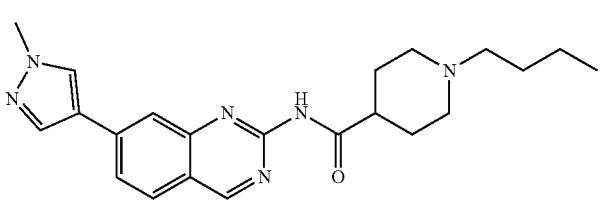 927
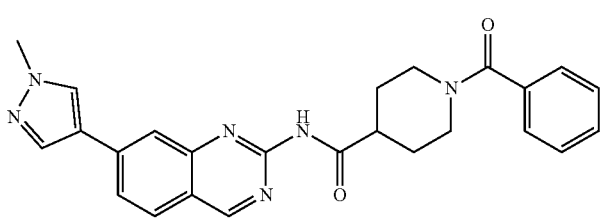 [SMILES: Cn1cc(-c2ccc3cnc(NC(=O)C4CCN(C(=O)c5ccccc5)CC4)nc3c2)cn1] 928

TABLE 1-continued
| | |
|---|---|
| 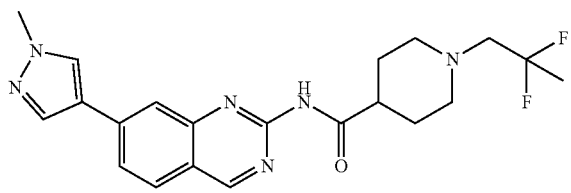 [SMILES: Cn1cc(-c2ccc3cnc(NC(=O)C4CCN(CC(C)(F)F)CC4)nc3c2)cn1] | 929 |
| 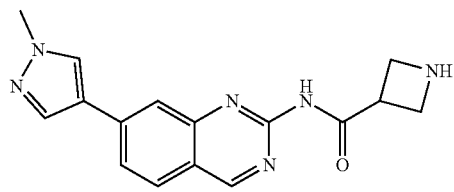 [SMILES: Cn1cc(-c2ccc3cnc(NC(=O)C4CNC4)nc3c2)cn1] | 930 |
| 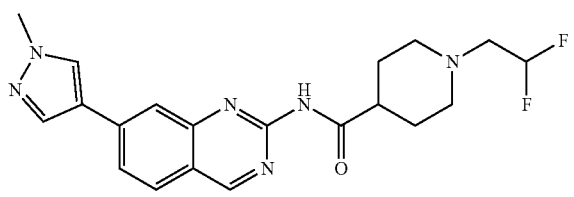 [SMILES: Cn1cc(-c2ccc3cnc(NC(=O)C4CCN(CC(F)F)CC4)nc3c2)cn1] | 931 |
| 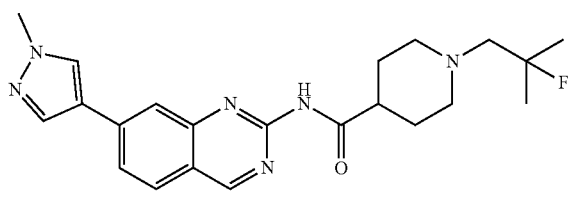 [SMILES: Cn1cc(-c2ccc3cnc(NC(=O)C4CCN(CC(C)(C)F)CC4)nc3c2)cn1] | 932 |
| 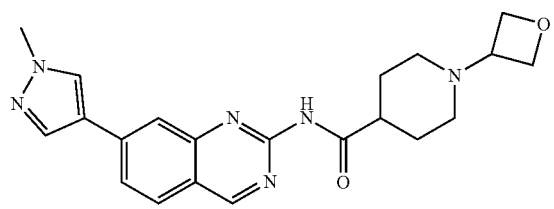 | 933 |
| 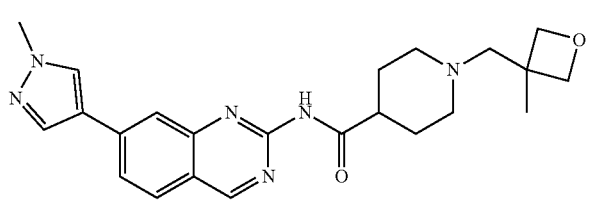 [SMILES: Cn1cc(-c2ccc3cnc(NC(=O)C4CCN(CC5(C)COC5)CC4)nc3c2)cn1] | 934 |
| 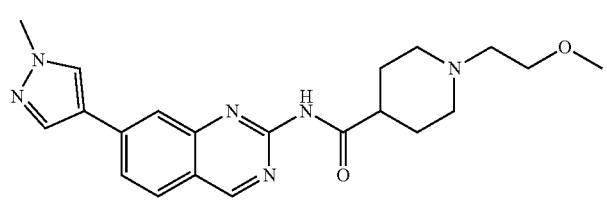 [SMILES: COCCN1CCC(C(=O)Nc2ncc3ccc(-c4cnn(C)c4)cc3n2)CC1] | 935 |
| 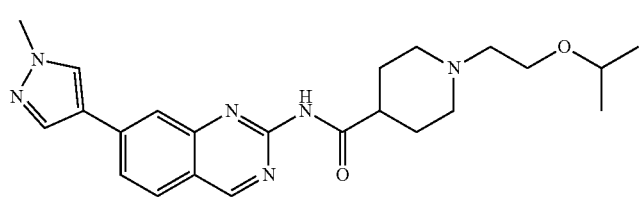 [SMILES: CC(C)OCCN1CCC(C(=O)Nc2ncc3ccc(-c4cnn(C)c4)cc3n2)CC1] | 936 |

TABLE 1-continued
| | |
|---|---|
| 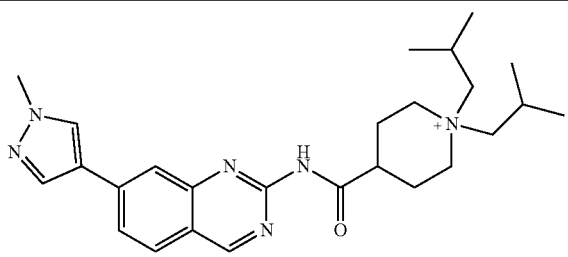 | 937 |
| 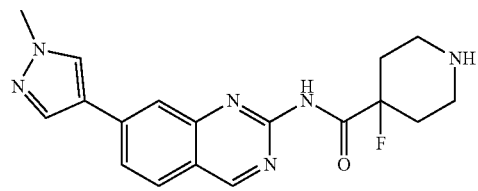 [SMILES: Cn1cc(-c2ccc3cnc(NC(=O)C4(F)CCNCC4)nc3c2)cn1] | 938 |
| 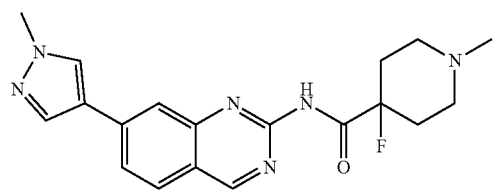 | 939 |
| 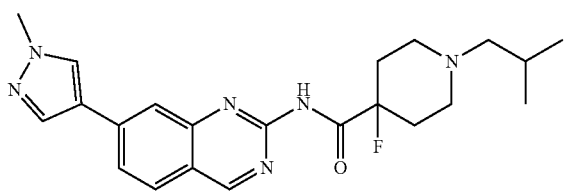 | 940 |
| 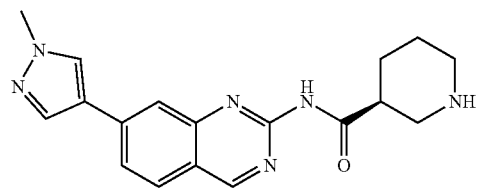 [SMILES: Cn1cc(-c2ccc3cnc(NC(=O)[C@H]4CCCNC4)nc3c2)cn1] | 941 |
| 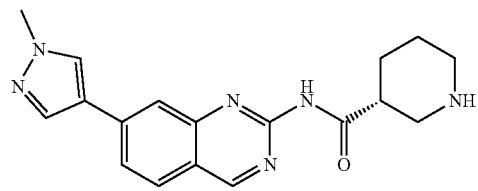 [SMILES: Cn1cc(-c2ccc3cnc(NC(=O)[C@@H]4CCCNC4)nc3c2)cn1] | 942 |
| 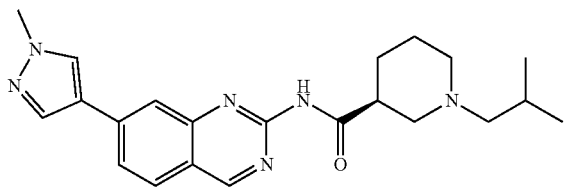 [SMILES: CC(C)CN1CCC[C@H](C(=O)Nc2ncc3ccc(-c4cnn(C)c4)cc3n2)C1] | 943 |
| 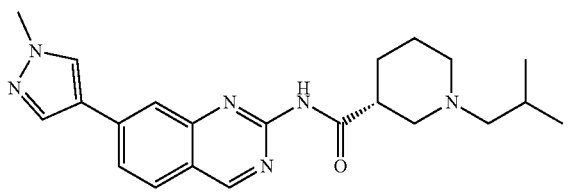 [SMILES: CC(C)CN1CCC[C@@H](C(=O)Nc2ncc3ccc(-c4cnn(C)c4)cc3n2)C1] | 944 |

TABLE 1-continued
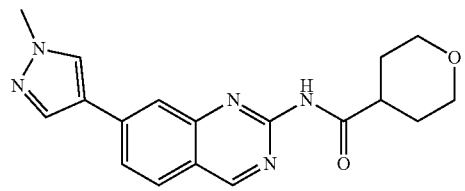 945
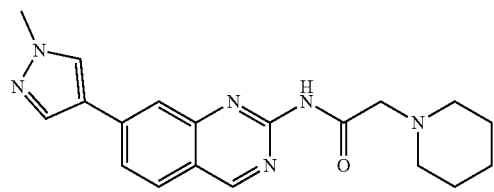 [SMILES: Cn1cc(-c2ccc3cnc(NC(=O)CN4CCCCC4)nc3c2)cn1] 946
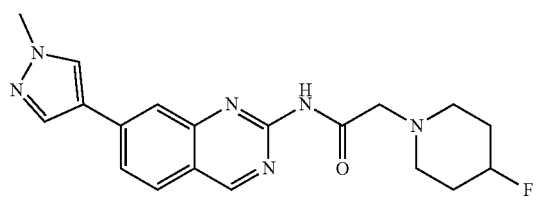 [SMILES: Cn1cc(-c2ccc3cnc(NC(=O)CN4CCC(F)CC4)nc3c2)cn1] 947
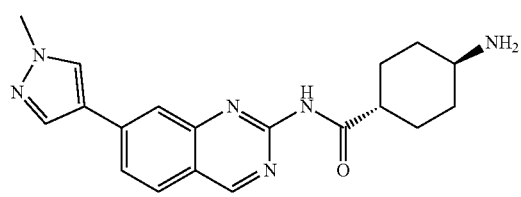 [SMILES: Cn1cc(-c2ccc3cnc(NC(=O)[C@H]4CC[C@H](N)CC4)nc3c2)cn1] 948
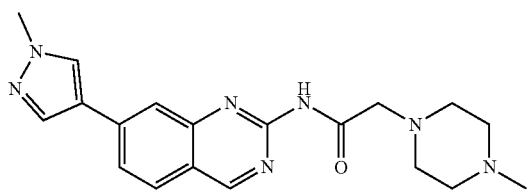 [SMILES: CN1CCN(CC(=O)Nc2ncc3ccc(-c4cnn(C)c4)cc3n2)CC1] 949
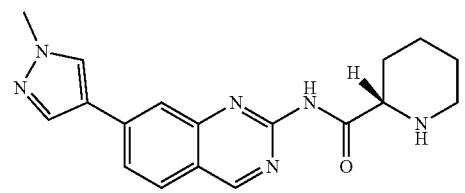 [SMILES: Cn1cc(-c2ccc3cnc(NC(=O)[C@@H]4CCCCN4)nc3c2)cn1] 950
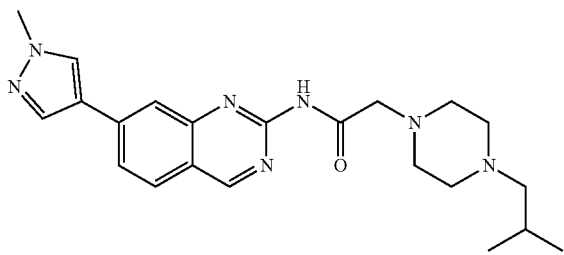 [SMILES: CC(C)CN1CCN(CC(=O)Nc2ncc3ccc(-c4cnn(C)c4)cc3n2)CC1] 951

TABLE 1-continued
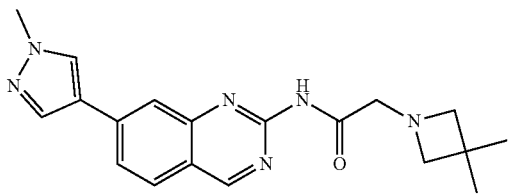 [SMILES: Cn1cc(-c2ccc3cnc(NC(=O)CN4CC(C)(C)C4)nc3c2)cn1] 952
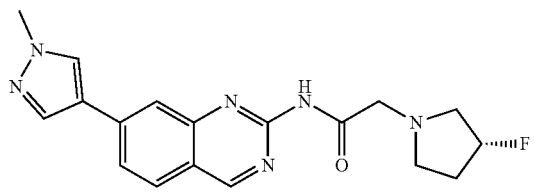 [SMILES: Cn1cc(-c2ccc3cnc(NC(=O)CN4CC[C@@H](F)C4)nc3c2)cn1] 953
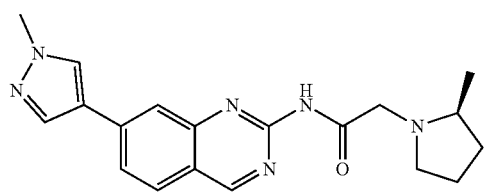 [SMILES: C[C@H]1CCCN1CC(=O)Nc1ncc2ccc(-c3cnn(C)c3)cc2n1] 954
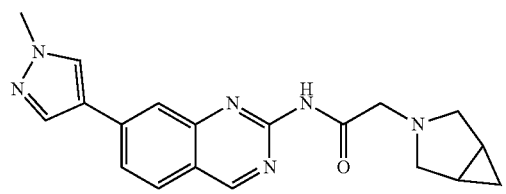 [SMILES: Cn1cc(-c2ccc3cnc(NC(=O)CN4CC5CC5C4)nc3c2)cn1] 955
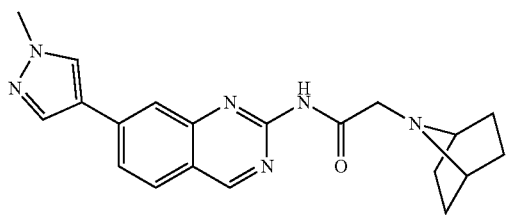 [SMILES: Cn1cc(-c2ccc3cnc(NC(=O)CN4C5CCC4CC5)nc3c2)cn1] 956
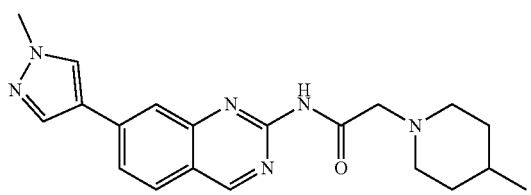 [SMILES: CC1CCN(CC(=O)Nc2ncc3ccc(-c4cnn(C)c4)cc3n2)CC1] 957
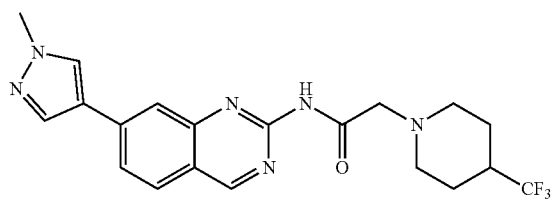 958

TABLE 1-continued
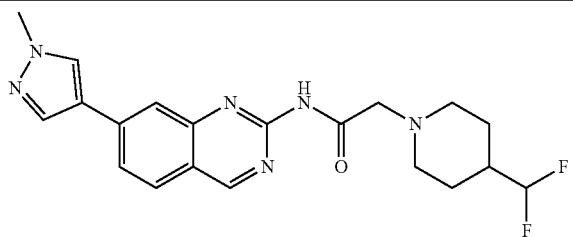 959
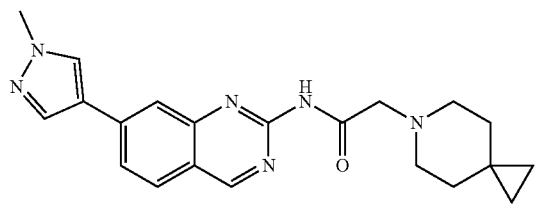 [SMILES: Cn1cc(-c2ccc3cnc(NC(=O)CN4CCC5(CC4)CC5)nc3c2)cn1] 960
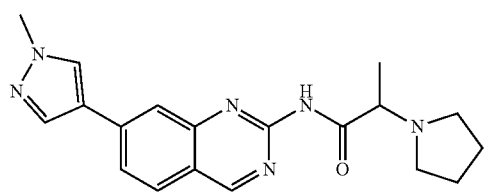 961
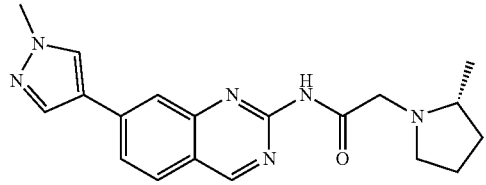 [SMILES: C[C@@H]1CCCN1CC(=O)Nc1ncc2ccc(-c3cnn(C)c3)cc2n1] 962
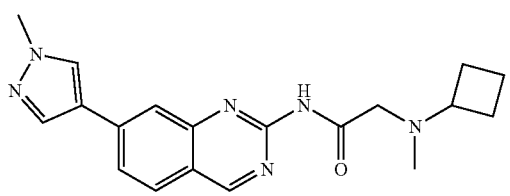 [SMILES: CN(CC(=O)Nc1ncc2ccc(-c3cnn(C)c3)cc2n1)C1CCC1] 963
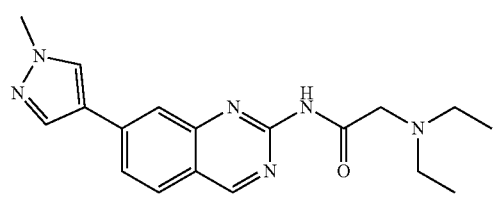 [SMILES: CCN(CC)CC(=O)Nc1ncc2ccc(-c3cnn(C)c3)cc2n1] 964
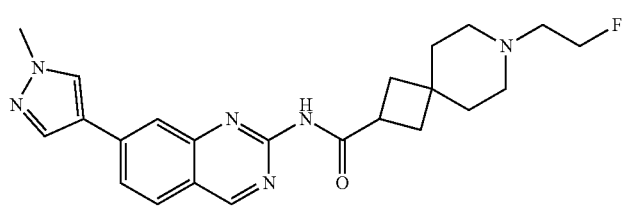 [SMILES: Cn1cc(-c2ccc3cnc(NC(=O)C4CC5(CCN(CCF)CC5)C4)nc3c2)cn1] 965
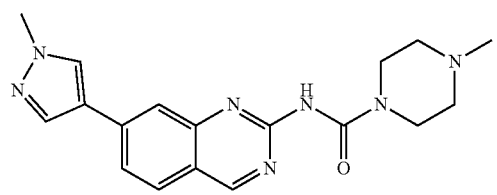 [SMILES: CN1CCN(C(=O)Nc2ncc3ccc(-c4cnn(C)c4)cc3n2)CC1] 966

TABLE 1-continued
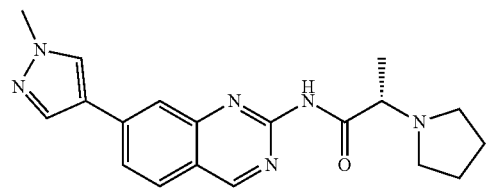 [SMILES: C[C@@H](C(=O)Nc1ncc2ccc(-c3cnn(C)c3)cc2n1)N1CCCC1] 967
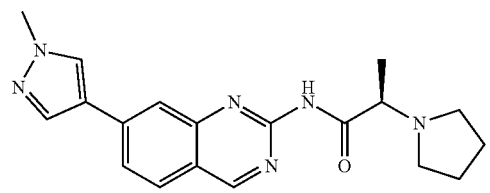 [SMILES: C[C@H](C(=O)Nc1ncc2ccc(-c3cnn(C)c3)cc2n1)N1CCCC1] 968
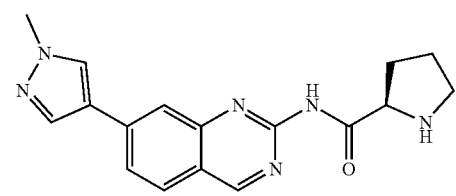 [SMILES: Cn1cc(-c2ccc3cnc(NC(=O)[C@H]4CCCN4)nc3c2)cn1] 969
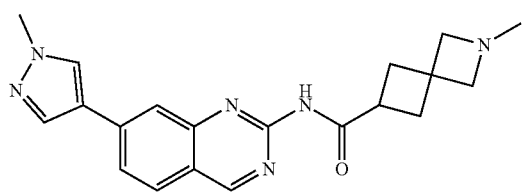 970
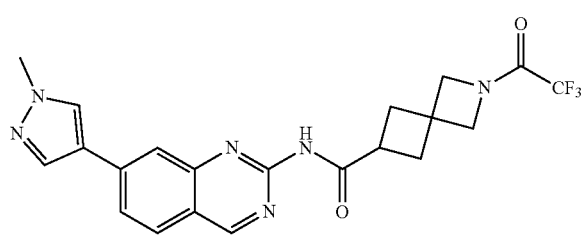 [SMILES: Cn1cc(-c2ccc3cnc(NC(=O)C4CC5(C4)CN(C(=O)C(F)(F)F)C5)nc3c2)cn1] 971
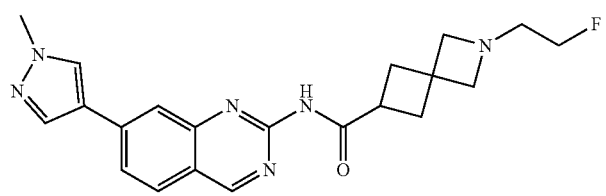 [SMILES: Cn1cc(-c2ccc3cnc(NC(=O)C4CC5(C4)CN(CCF)C5)nc3c2)cn1] 972
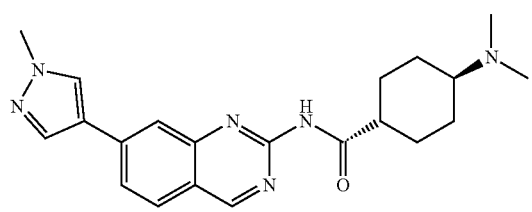 973

TABLE 1-continued
| | |
|---|---|
| 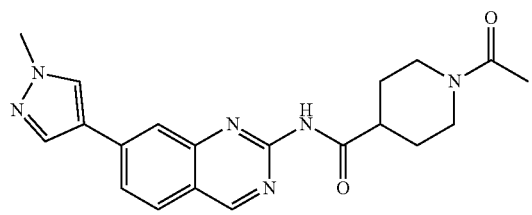 [SMILES: CC(=O)N1CCC(C(=O)Nc2ncc3ccc(-c4cnn(C)c4)cc3n2)CC1] | 974 |
| 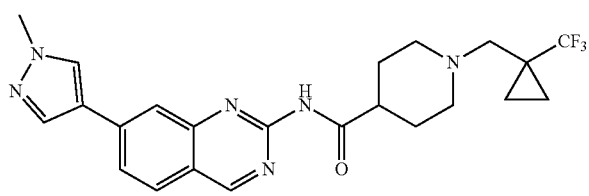 [SMILES: Cn1cc(-c2ccc3cnc(NC(=O)C4CCN(CC5(C(F)(F)F)CC5)CC4)nc3c2)cn1] | 975 |
| 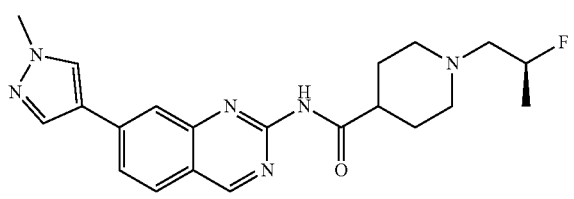 [SMILES: C[C@H](F)CN1CCC(C(=O)Nc2ncc3ccc(-c4cnn(C)c4)cc3n2)CC1] | 976 |
| 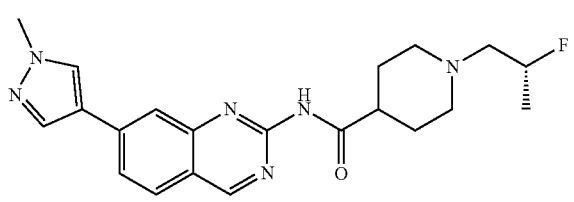 | 977 |
| 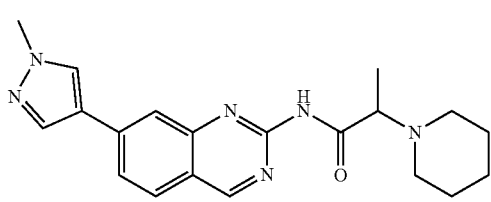 [SMILES: CC(C(=O)Nc1ncc2ccc(-c3cnn(C)c3)cc2n1)N1CCCCC1] | 978 |
| 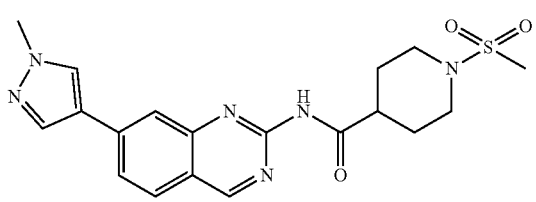 [SMILES: Cn1cc(-c2ccc3cnc(NC(=O)C4CCN(S(C)(=O)=O)CC4)nc3c2)cn1] | 979 |
| 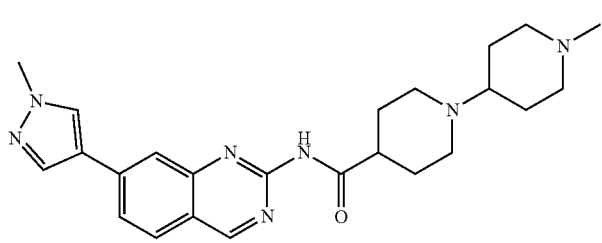 [SMILES: CN1CCC(N2CCC(C(=O)Nc3ncc4ccc(-c5cnn(C)c5)cc4n3)CC2)CC1] | 980 |
| 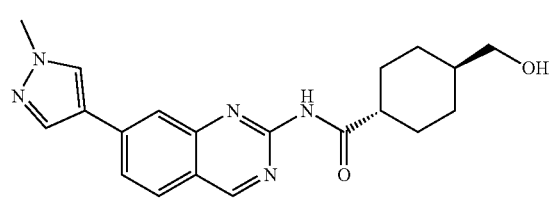 [SMILES: Cn1cc(-c2ccc3cnc(NC(=O)[C@H]4CC[C@H](CO)CC4)nc3c2)cn1] | 981 |

TABLE 1-continued
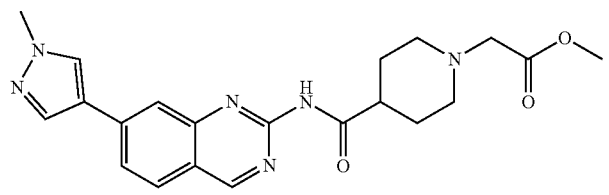 [SMILES: COC(=O)CN1CCC(C(=O)Nc2ncc3ccc(-c4cnn(C)c4)cc3n2)CC1] 982
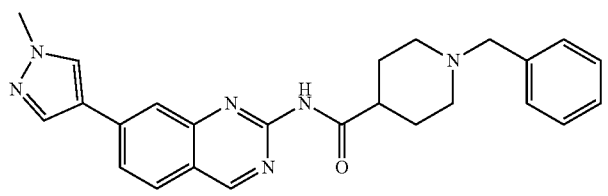 [SMILES: Cn1cc(-c2ccc3cnc(NC(=O)C4CCN(Cc5ccccc5)CC4)nc3c2)cn1] 983
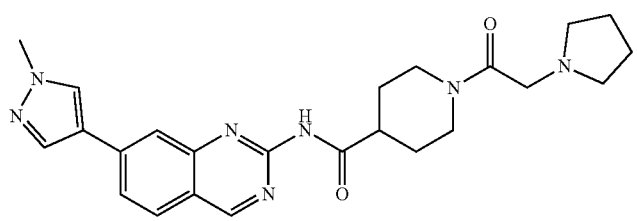 [SMILES: Cn1cc(-c2ccc3cnc(NC(=O)C4CCN(C(=O)CN5CCCC5)CC4)nc3c2)cn1] 984
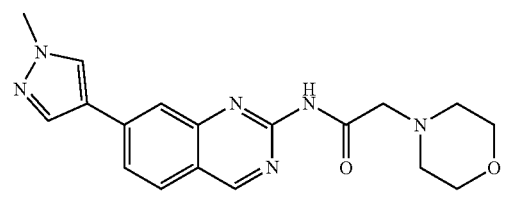 [SMILES: Cn1cc(-c2ccc3cnc(NC(=O)CN4CCOCC4)nc3c2)cn1] 985
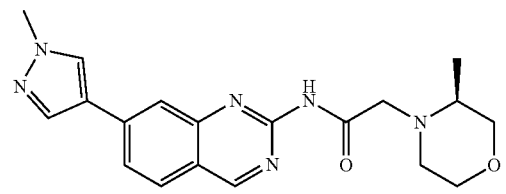 [SMILES: C[C@H]1COCCN1CC(=O)Nc1ncc2ccc(-c3cnn(C)c3)cc2n1] 986
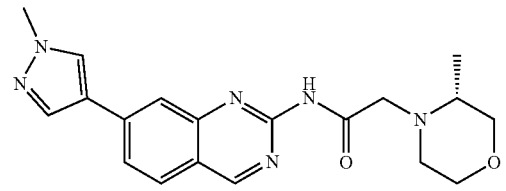 [SMILES: C[C@@H]1COCCN1CC(=O)Nc1ncc2ccc(-c3cnn(C)c3)cc2n1] 987
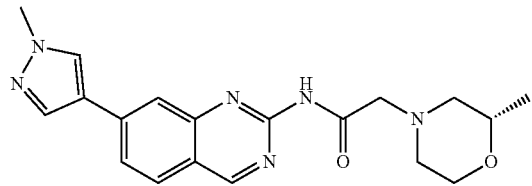 [SMILES: C[C@H]1CN(CC(=O)Nc2ncc3ccc(-c4cnn(C)c4)cc3n2)CCO1] 988

TABLE 1-continued
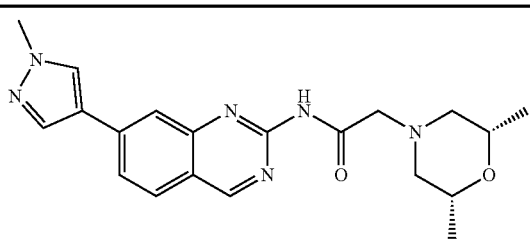 989
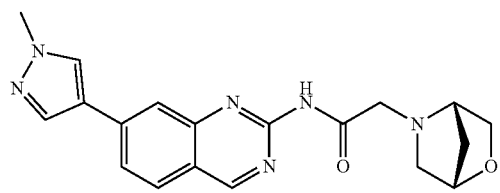 [SMILES: Cn1cc(-c2ccc3cnc(NC(=O)CN4C[C@@H]5C[C@H]4CO5)nc3c2)cn1] 990
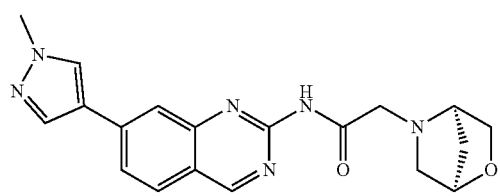 [SMILES: Cn1cc(-c2ccc3cnc(NC(=O)CN4C[C@H]5C[C@@H]4CO5)nc3c2)cn1] 991
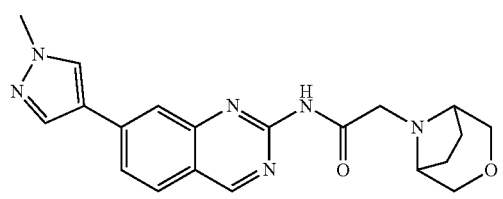 [SMILES: Cn1cc(-c2ccc3cnc(NC(=O)CN4C5CCC4COC5)nc3c2)cn1] 992
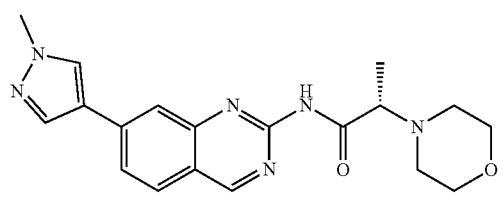 [SMILES: C[C@@H](C(=O)Nc1ncc2ccc(-c3cnn(C)c3)cc2n1)N1CCOCC1] 993
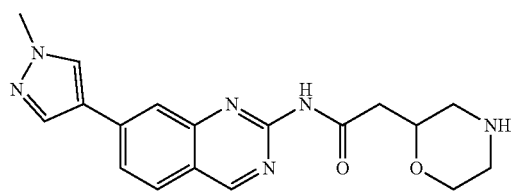 [SMILES: Cn1cc(-c2ccc3cnc(NC(=O)CC4CNCCO4)nc3c2)cn1] 994
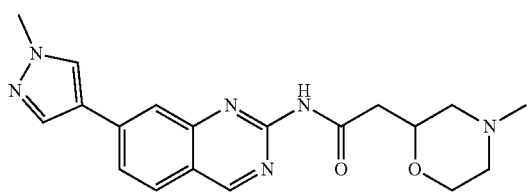 [SMILES: CN1CCOC(CC(=O)Nc2ncc3ccc(-c4cnn(C)c4)cc3n2)C1] 995
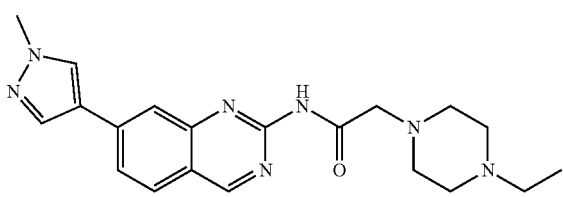 [SMILES: CCN1CCN(CC(=O)Nc2ncc3ccc(-c4cnn(C)c4)cc3n2)CC1] 996

TABLE 1-continued
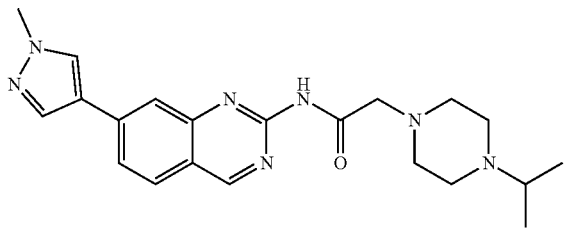 [SMILES: CC(C)N1CCN(CC(=O)Nc2ncc3ccc(-c4cnn(C)c4)cc3n2)CC1]
997
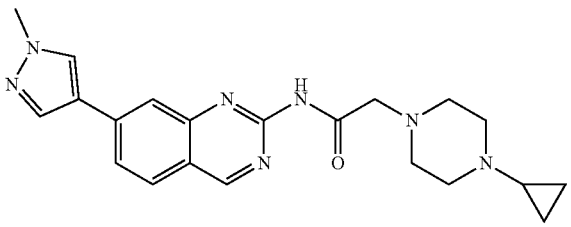 [SMILES: Cn1cc(-c2ccc3cnc(NC(=O)CN4CCN(C5CC5)CC4)nc3c2)cn1]
998
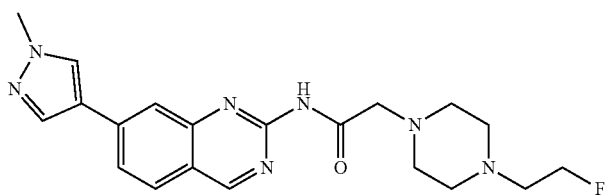 [SMILES: Cn1cc(-c2ccc3cnc(NC(=O)CN4CCN(CCF)CC4)nc3c2)cn1]
999
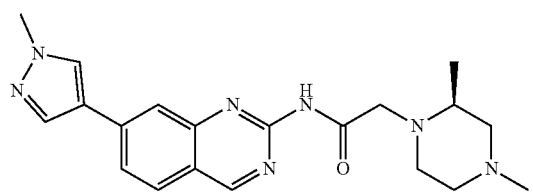 [SMILES: C[C@H]1CN(C)CCN1CC(=O)Nc1ncc2ccc(-c3cnn(C)c3)cc2n1]
1000
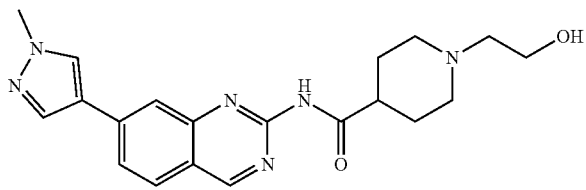 [SMILES: Cn1cc(-c2ccc3cnc(NC(=O)C4CCN(CCO)CC4)nc3c2)cn1]
1001
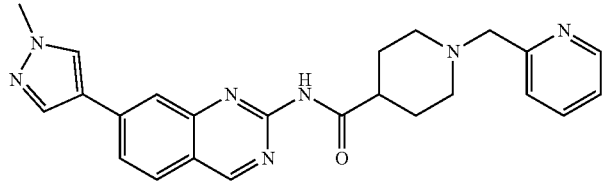 [SMILES: Cn1cc(-c2ccc3cnc(NC(=O)C4CCN(Cc5ccccn5)CC4)nc3c2)cn1]
1002
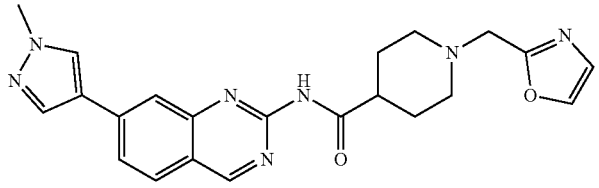 [SMILES: Cn1cc(-c2ccc3cnc(NC(=O)C4CCN(Cc5ncco5)CC4)nc3c2)cn1]
1003
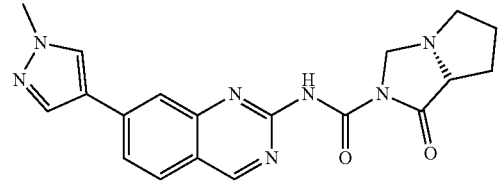
1004

TABLE 1-continued
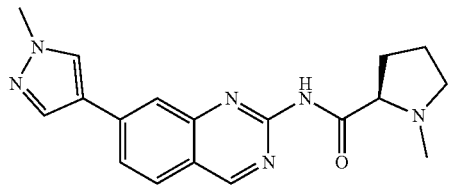 [SMILES: CN1CCC[C@@H]1C(=O)Nc1ncc2ccc(-c3cnn(C)c3)cc2n1] 1005
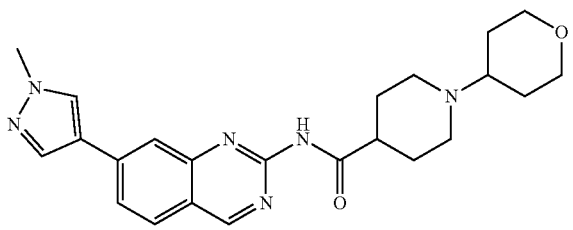 [SMILES: Cn1cc(-c2ccc3cnc(NC(=O)C4CCN(C5CCOCC5)CC4)nc3c2)cn1] 1006
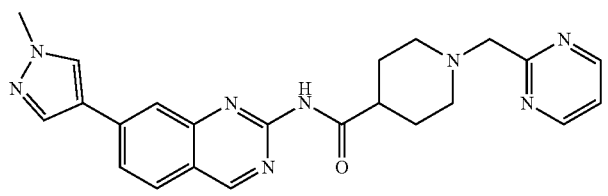 [SMILES: Cn1cc(-c2ccc3cnc(NC(=O)C4CCN(Cc5ncccn5)CC4)nc3c2)cn1] 1007
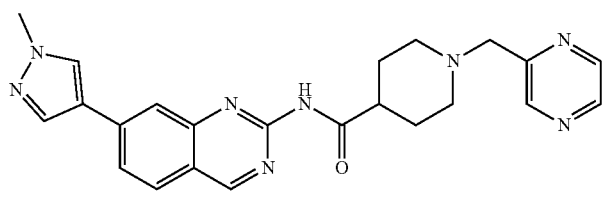 [SMILES: Cn1cc(-c2ccc3cnc(NC(=O)C4CCN(Cc5cnccn5)CC4)nc3c2)cn1] 1008
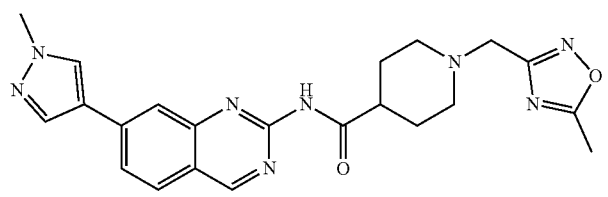 1009
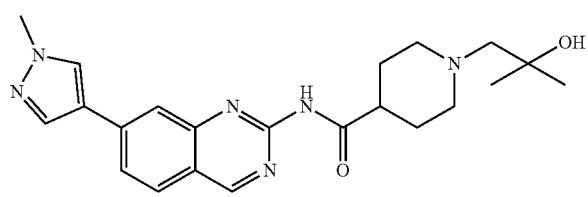 [SMILES: Cn1cc(-c2ccc3cnc(NC(=O)C4CCN(CC(C)(C)O)CC4)nc3c2)cn1] 1010
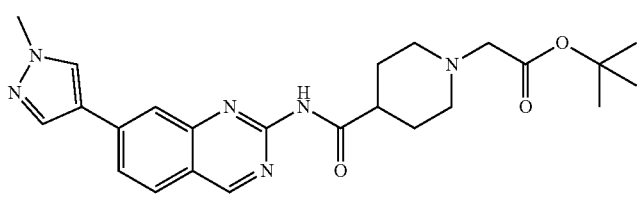 [SMILES: Cn1cc(-c2ccc3cnc(NC(=O)C4CCN(CC(=O)OC(C)(C)C)CC4)nc3c2)cn1] 1011
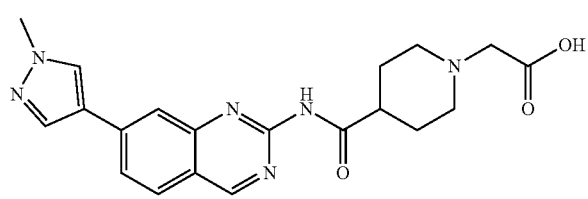 [SMILES: Cn1cc(-c2ccc3cnc(NC(=O)C4CCN(CC(=O)O)CC4)nc3c2)cn1] 1012

TABLE 1-continued
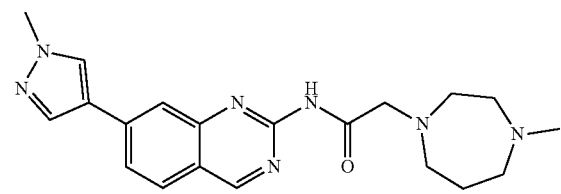 1013
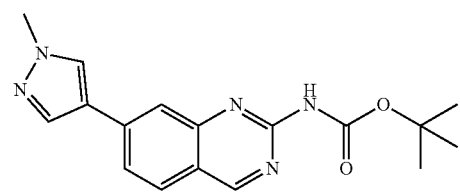 [SMILES: Cn1cc(-c2ccc3cnc(NC(=O)OC(C)(C)C)nc3c2)cn1] 1014
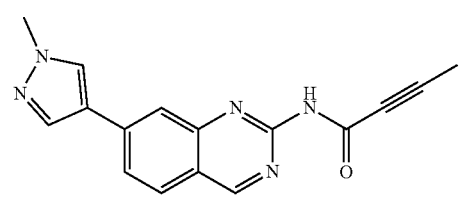 [SMILES: CC#CC(=O)Nc1ncc2ccc(-c3cnn(C)c3)cc2n1] 1015
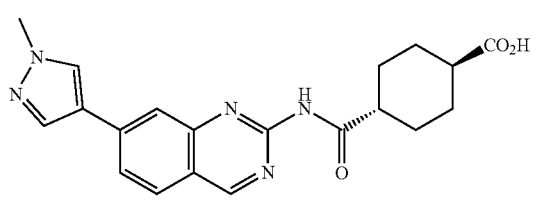 [SMILES: Cn1cc(-c2ccc3cnc(NC(=O)[C@H]4CC[C@H](C(=O)O)CC4)nc3c2)cn1] 1016
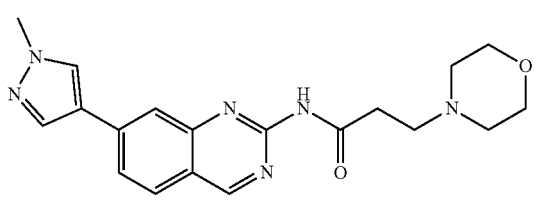 1017
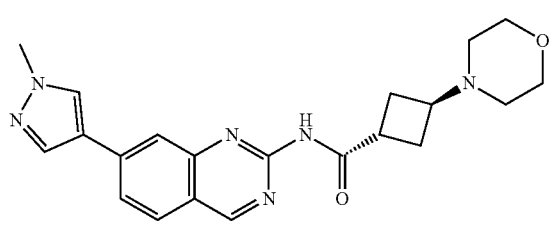 1018
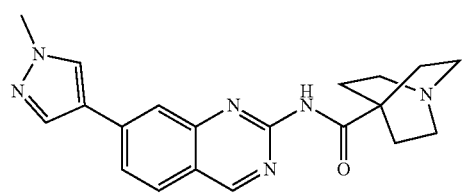 [SMILES: Cn1cc(-c2ccc3cnc(NC(=O)C45CCN(CC4)CC5)nc3c2)cn1] 1019
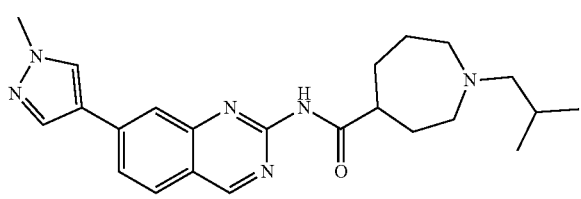 [SMILES: CC(C)CN1CCCC(C(=O)Nc2ncc3ccc(-c4cnn(C)c4)cc3n2)CC1] 1020

TABLE 1-continued

| | |
|---|---|
| (structure) | 1021 |
| (structure) | 1022 |
| (structure) | 1023 |
| (structure) | 1024 |
| (structure) | 1025 |
| (structure) | 1026 |
| (structure) | 1027 |
| (structure) | 1028 |

TABLE 1-continued
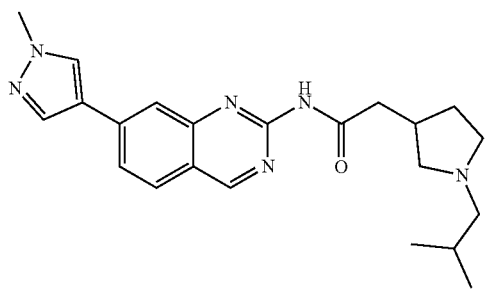 [SMILES: CC(C)CN1CCC(CC(=O)Nc2ncc3ccc(-c4cnn(C)c4)cc3n2)C1]
1029
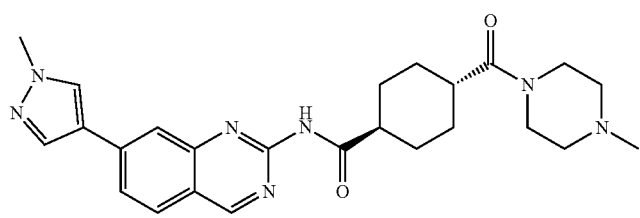 [SMILES: CN1CCN(C(=O)[C@H]2CC[C@H](C(=O)Nc3ncc4ccc(-c5cnn(C)c5)cc4n3)CC2)CC1]
1030
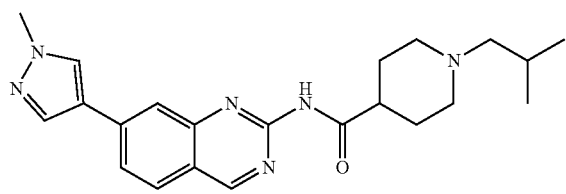 [SMILES: CC(C)CN1CCC(C(=O)Nc2ncc3ccc(-c4cnn(C)c4)cc3n2)CC1]
1031
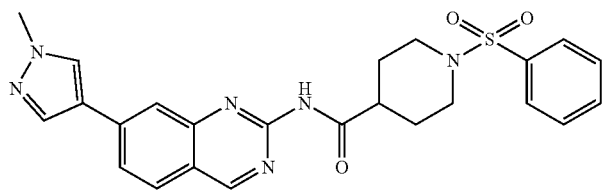 [SMILES: Cn1cc(-c2ccc3cnc(NC(=O)C4CCN(S(=O)(=O)c5ccccc5)CC4)nc3c2)cn1]
1032
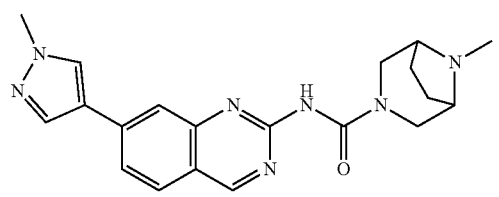 [SMILES: CN1C2CCC1CN(C(=O)Nc1ncc3ccc(-c4cnn(C)c4)cc3n1)C2]
1033
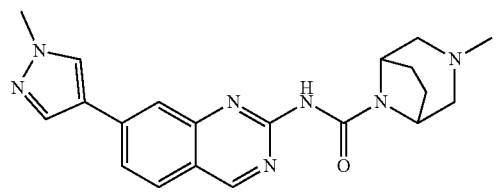 [SMILES: CN1CC2CCC(C1)N2C(=O)Nc1ncc2ccc(-c3cnn(C)c3)cc2n1]
1034
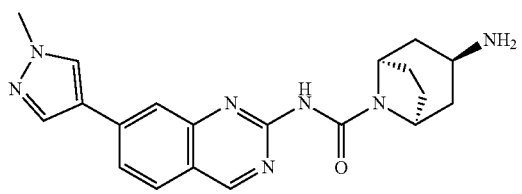 [SMILES: Cn1cc(-c2ccc3cnc(NC(=O)N4[C@@H]5CC[C@H]4C[C@H](N)C5)nc3c2)cn1]
1035

TABLE 1-continued
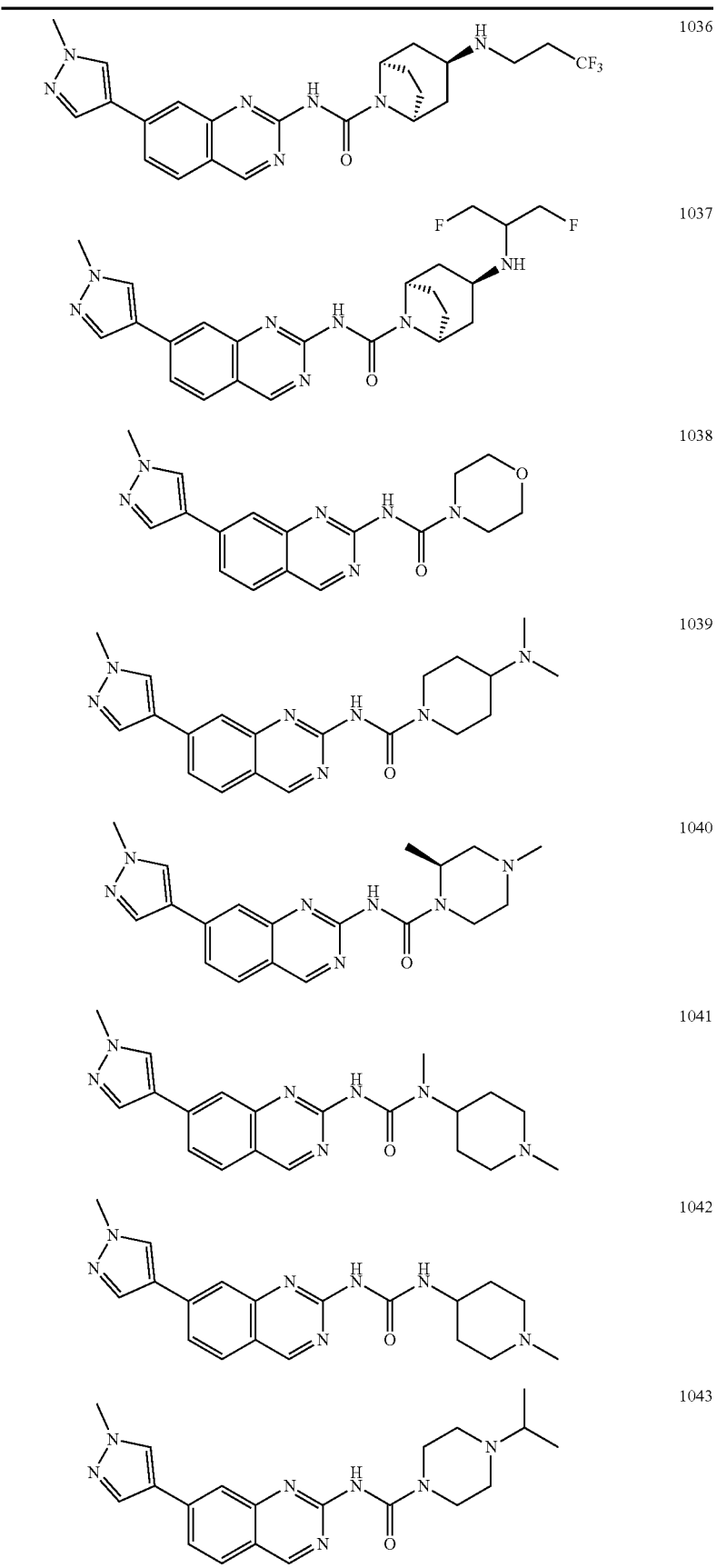

TABLE 1-continued
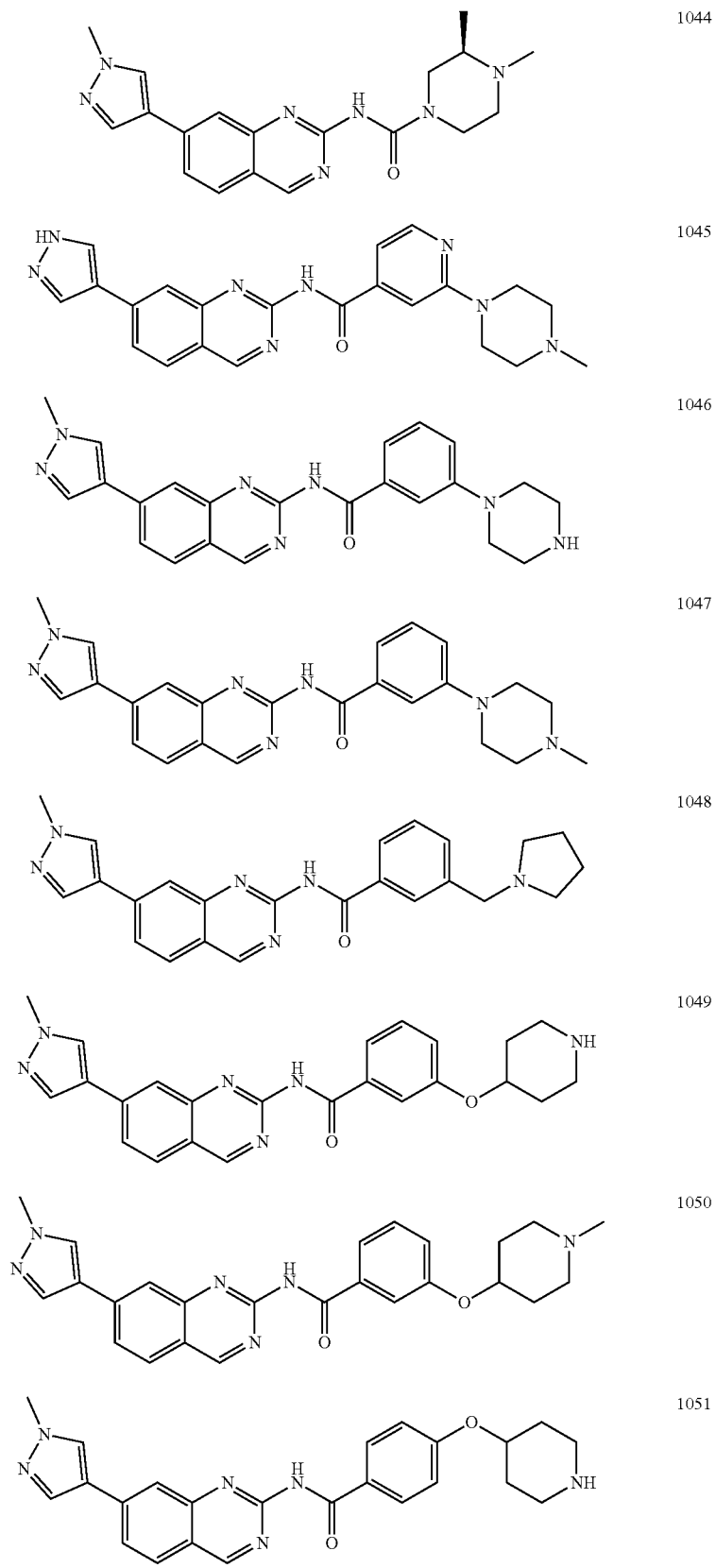
1044
1045
1046
1047
1048
1049
1050
1051

TABLE 1-continued
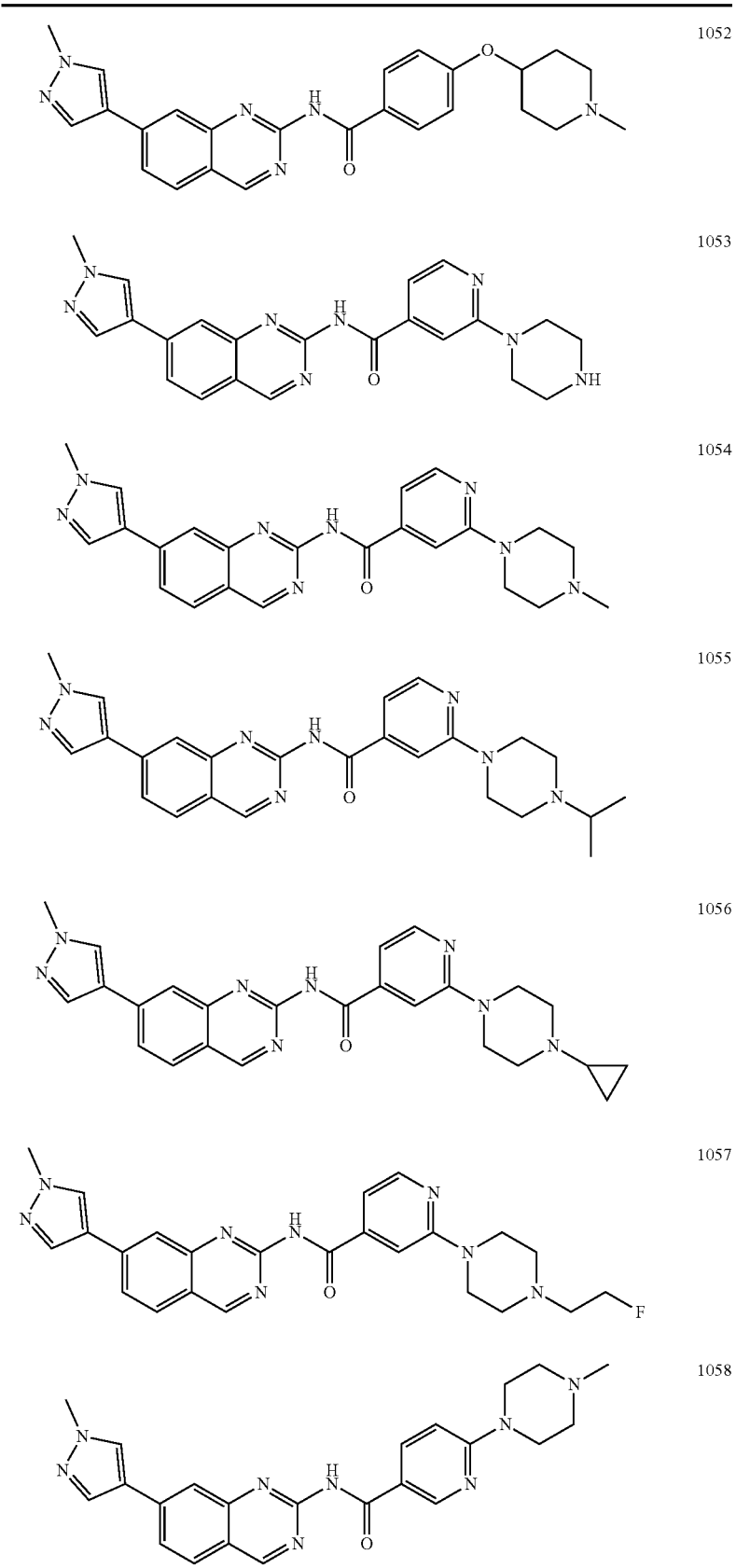

TABLE 1-continued
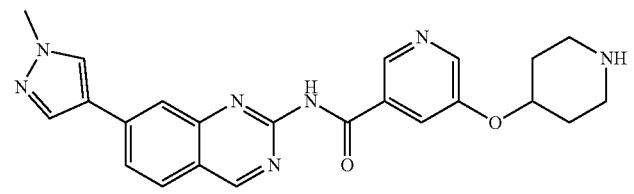 [SMILES: Cn1cc(-c2ccc3cnc(NC(=O)c4cncc(OC5CCNCC5)c4)nc3c2)cn1]
1059
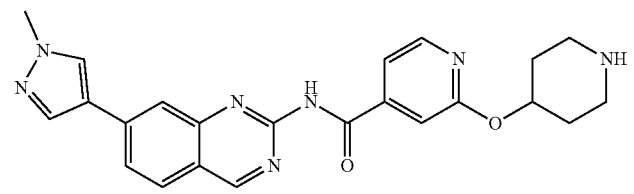 [SMILES: Cn1cc(-c2ccc3cnc(NC(=O)c4ccnc(OC5CCNCC5)c4)nc3c2)cn1]
1060
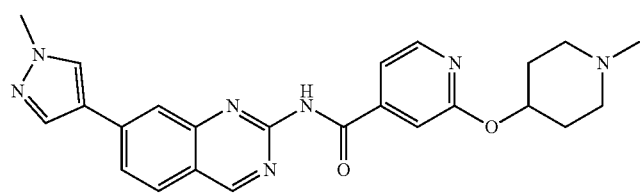 [SMILES: CN1CCC(Oc2cc(C(=O)Nc3ncc4ccc(-c5cnn(C)c5)cc4n3)ccn2)CC1]
1061
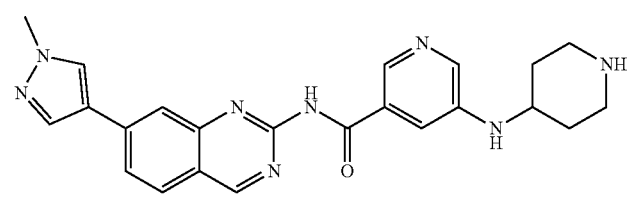
1062
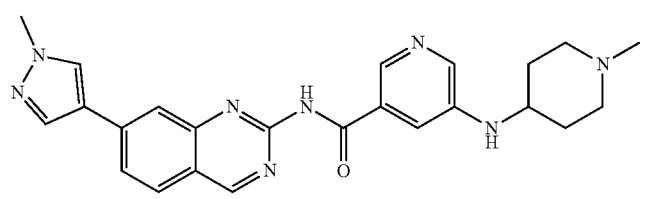 [SMILES: CN1CCC(Nc2cncc(C(=O)Nc3ncc4ccc(-c5cnn(C)c5)cc4n3)c2)CC1]
1063
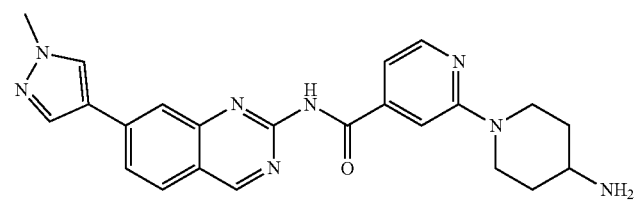 [SMILES: Cn1cc(-c2ccc3cnc(NC(=O)c4ccnc(N5CCC(N)CC5)c4)nc3c2)cn1]
1064
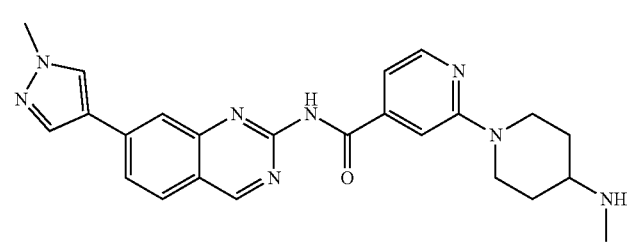 [SMILES: CNC1CCN(c2cc(C(=O)Nc3ncc4ccc(-c5cnn(C)c5)cc4n3)ccn2)CC1]
1065

TABLE 1-continued
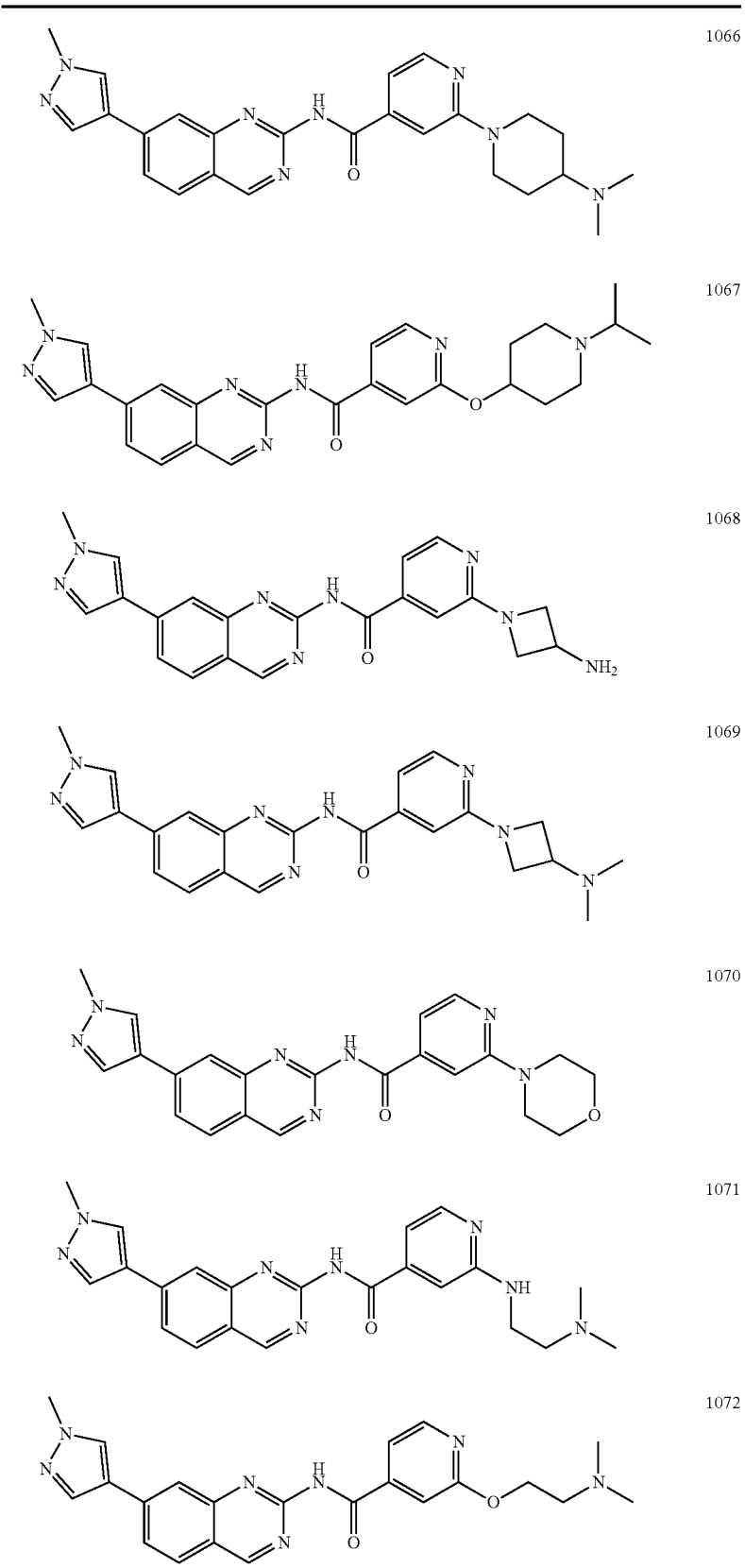

TABLE 1-continued
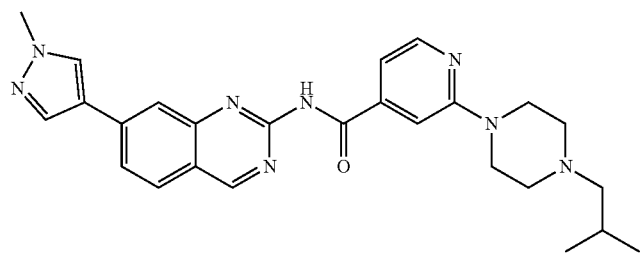 [SMILES: CC(C)CN1CCN(c2cc(C(=O)Nc3ncc4ccc(-c5cnn(C)c5)cc4n3)ccn2)CC1] 1073
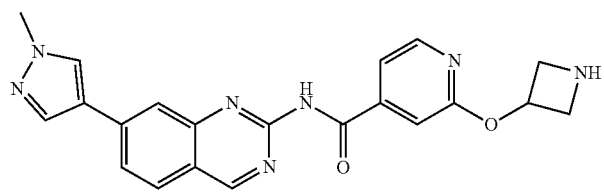 [SMILES: Cn1cc(-c2ccc3cnc(NC(=O)c4ccnc(OC5CNC5)c4)nc3c2)cn1] 1074
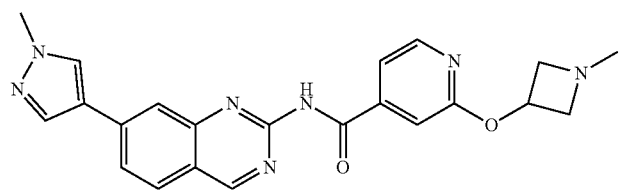 [SMILES: CN1CC(Oc2cc(C(=O)Nc3ncc4ccc(-c5cnn(C)c5)cc4n3)ccn2)C1] 1075
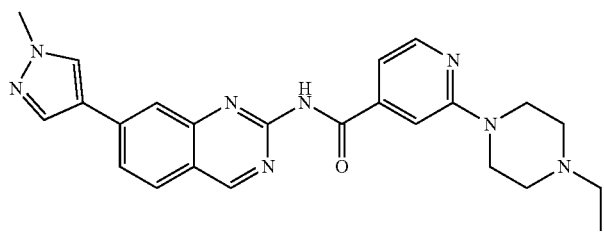 [SMILES: CCN1CCN(c2cc(C(=O)Nc3ncc4ccc(-c5cnn(C)c5)cc4n3)ccn2)CC1] 1076
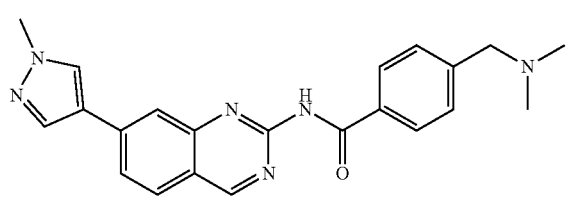 [SMILES: CN(C)Cc1ccc(C(=O)Nc2ncc3ccc(-c4cnn(C)c4)cc3n2)cc1] 1077
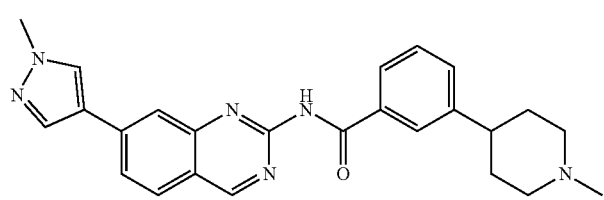 1078
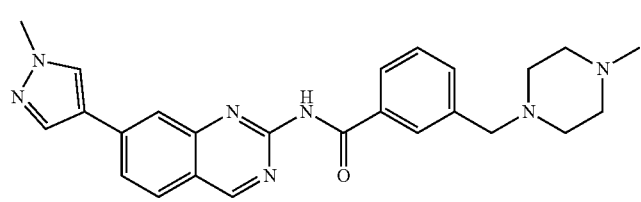 [SMILES: CN1CCN(Cc2cccc(C(=O)Nc3ncc4ccc(-c5cnn(C)c5)cc4n3)c2)CC1] 1079

TABLE 1-continued
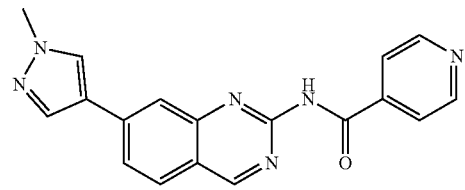 [SMILES: Cn1cc(-c2ccc3cnc(NC(=O)c4ccncc4)nc3c2)cn1]
1080
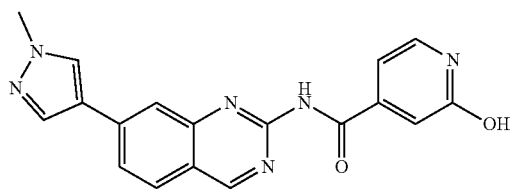 [SMILES: Cn1cc(-c2ccc3cnc(NC(=O)c4ccnc(O)c4)nc3c2)cn1]
1081
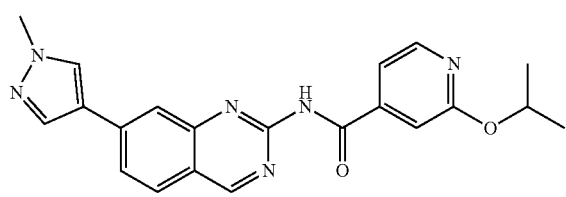 [SMILES: CC(C)Oc1cc(C(=O)Nc2ncc3ccc(-c4cnn(C)c4)cc3n2)ccn1]
1082
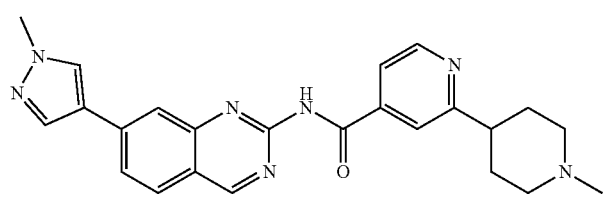
1083
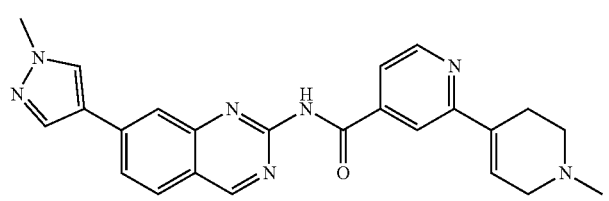 [SMILES: CN1CC=C(c2cc(C(=O)Nc3ncc4ccc(-c5cnn(C)c5)cc4n3)ccn2)CC1]
1084
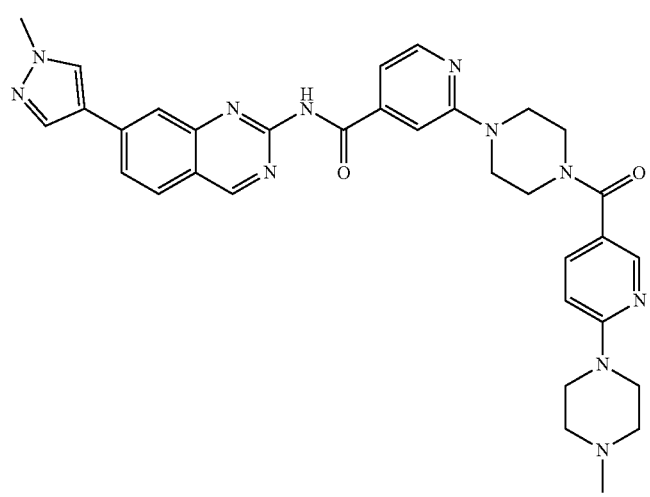 [SMILES: CN1CCN(c2ccc(C(=O)N3CCN(c4cc(C(=O)Nc5ncc6ccc(-c7cnn(C)c7)cc6n5)ccn4)CC3)cn2)CC1]
1085

TABLE 1-continued
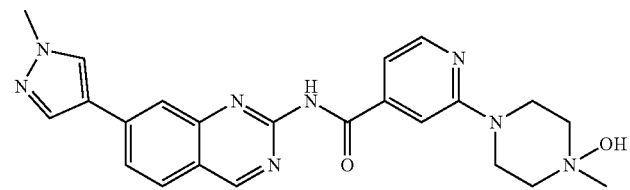
1086
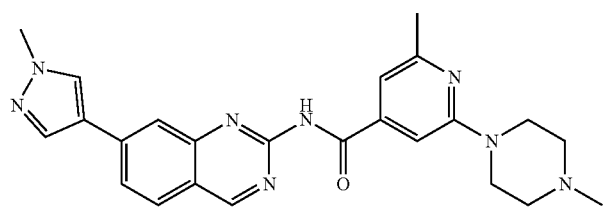
1087
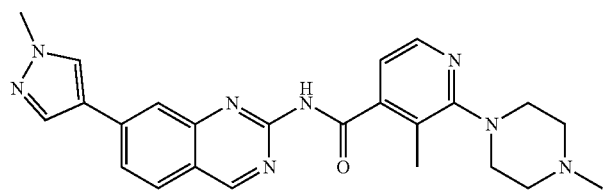 [SMILES: Cc1c(C(=O)Nc2ncc3ccc(-c4cnn(C)c4)cc3n2)ccnc1N1CCN(C)CC1]
1088
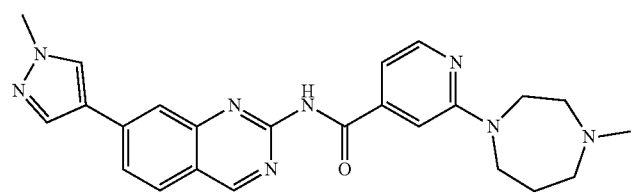
1089
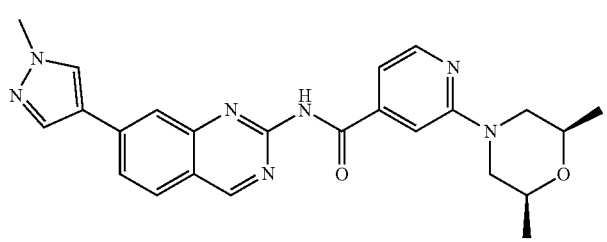 [SMILES: C[C@@H]1CN(c2cc(C(=O)Nc3ncc4ccc(-c5cnn(C)c5)cc4n3)ccn2)C[C@H](C)O1]
1090
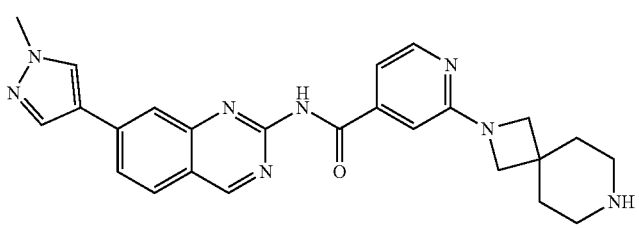 [SMILES: Cn1cc(-c2ccc3cnc(NC(=O)c4ccnc(N5CC6(CCNCC6)C5)c4)nc3c2)cn1]
1091
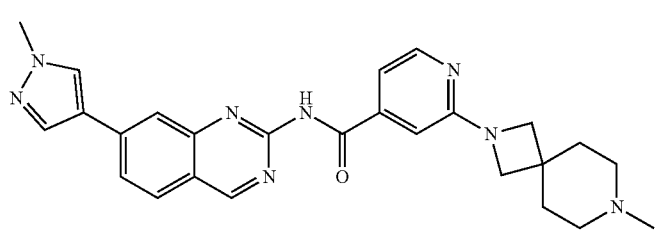 [SMILES: CN1CCC2(CC1)CN(c1cc(C(=O)Nc3ncc4ccc(-c5cnn(C)c5)cc4n3)ccn1)C2]
1092

TABLE 1-continued

| | |
|---|---|
| (structure) | 1093 |
| (structure) | 1094 |
| (structure) | 1095 |
| (structure) | 1096 |
| (structure) | 1097 |
| (structure) | 1098 |
| (structure) | 1099 |
| (structure) | 1100 |

TABLE 1-continued
| | |
|---|---|
| 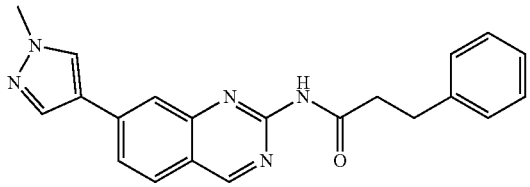 [SMILES: Cn1cc(-c2ccc3cnc(NC(=O)CCc4ccccc4)nc3c2)cn1] | 1101 |
| 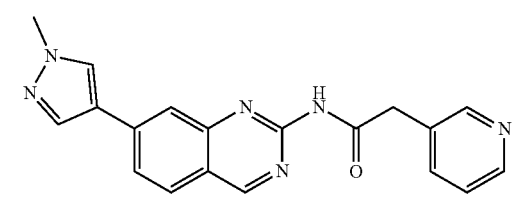 [SMILES: Cn1cc(-c2ccc3cnc(NC(=O)Cc4cccnc4)nc3c2)cn1] | 1102 |
| 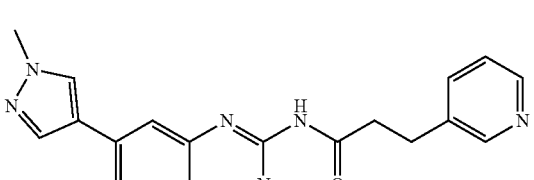 | 1103 |
| 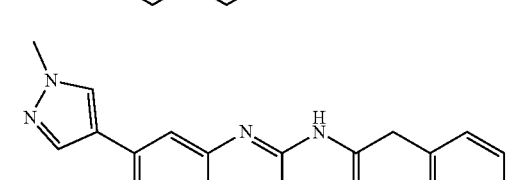 | 1104 |
| 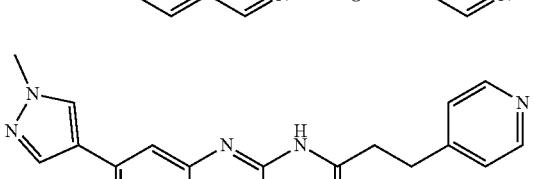 | 1105 |
| 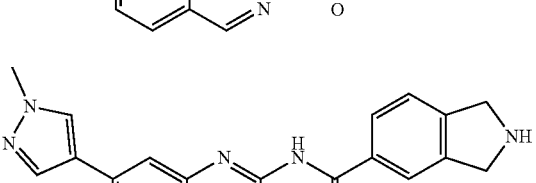 | 1106 |
| 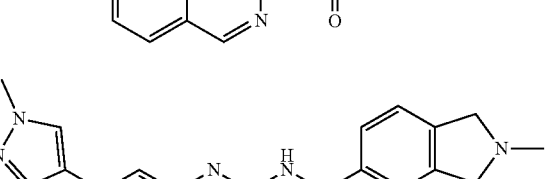 | 1107 |
| 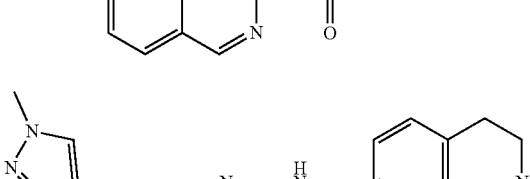 | 1108 |

TABLE 1-continued
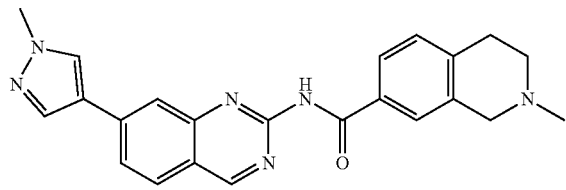 [SMILES: CN1CCc2ccc(C(=O)Nc3ncc4ccc(-c5cnn(C)c5)cc4n3)cc2C1] 1109
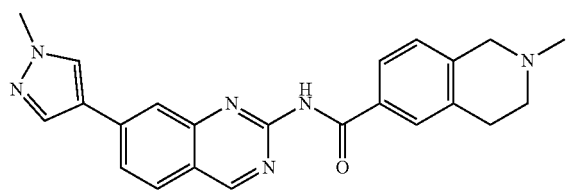 [SMILES: CN1CCc2cc(C(=O)Nc3ncc4ccc(-c5cnn(C)c5)cc4n3)ccc2C1] 1110
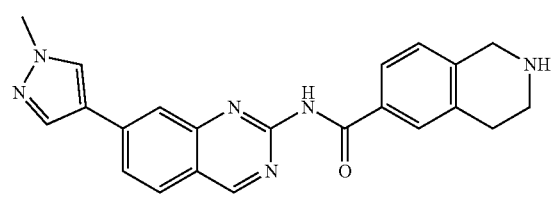 [SMILES: Cn1cc(-c2ccc3cnc(NC(=O)c4ccc5c(c4)CCNC5)nc3c2)cn1] 1111
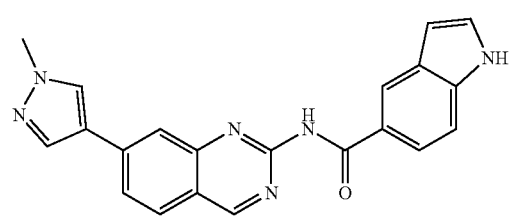 [SMILES: Cn1cc(-c2ccc3cnc(NC(=O)c4ccc5[nH]ccc5c4)nc3c2)cn1] 1112
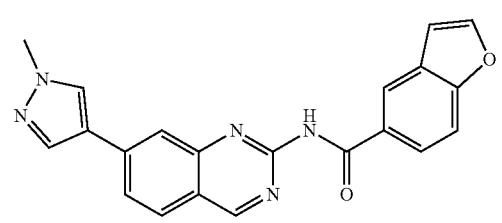 [SMILES: Cn1cc(-c2ccc3cnc(NC(=O)c4ccc5occc5c4)nc3c2)cn1] 1113
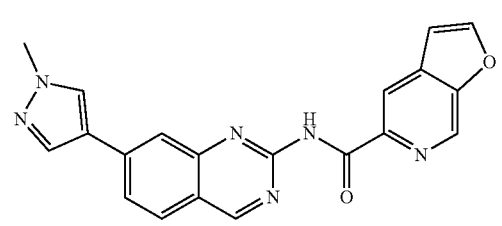 [SMILES: Cn1cc(-c2ccc3cnc(NC(=O)c4cc5ccoc5cn4)nc3c2)cn1] 1114
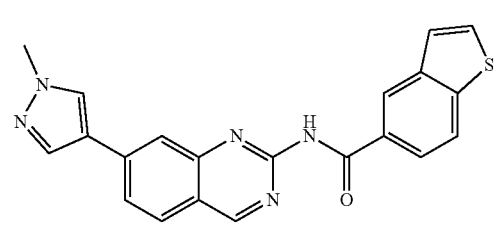 [SMILES: Cn1cc(-c2ccc3cnc(NC(=O)c4ccc5sccc5c4)nc3c2)cn1] 1115

TABLE 1-continued
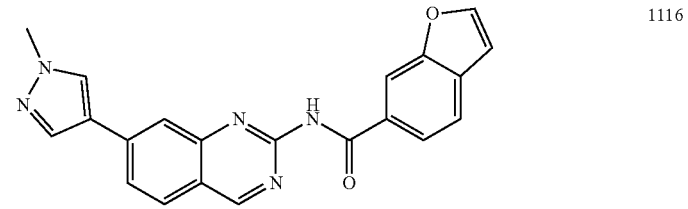
1116
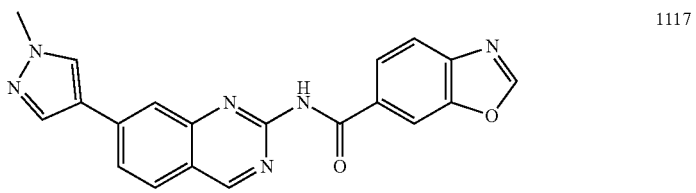
1117
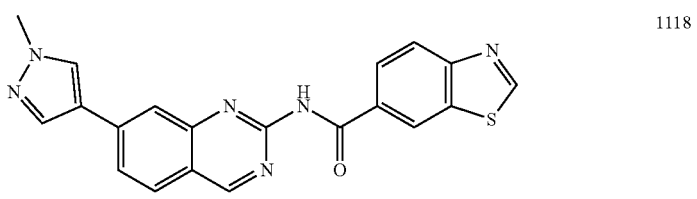
1118
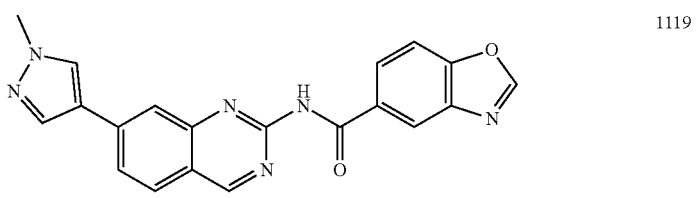
1119
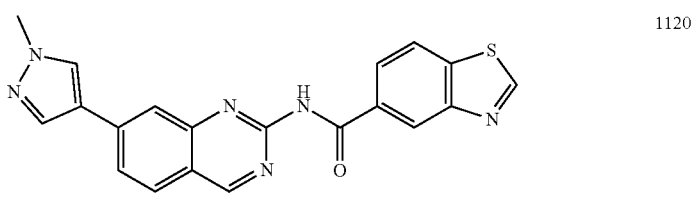
1120
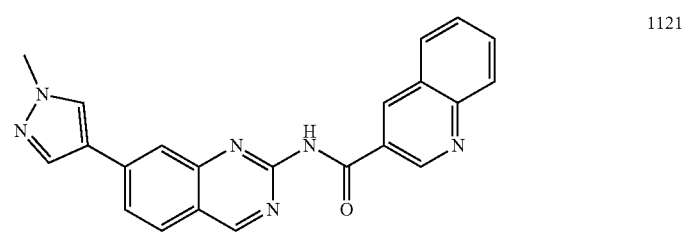
1121
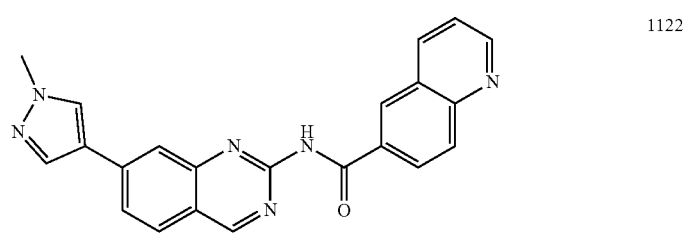
1122

TABLE 1-continued

| | |
|---|---|
| [structure] | 1123 |
| [structure] | 1124 |
| [structure] | 1125 |
| [structure] | 1126 |
| [structure] | 1127 |
| [structure] | 1128 |
| [structure] | 1129 |
| [structure] | 1130 |

TABLE 1-continued
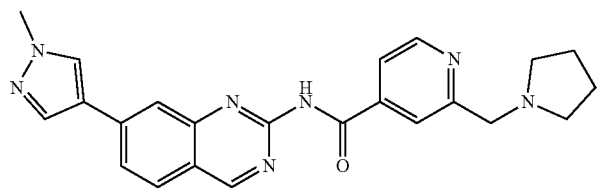 1131
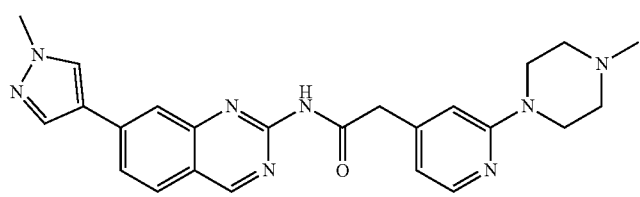 1132
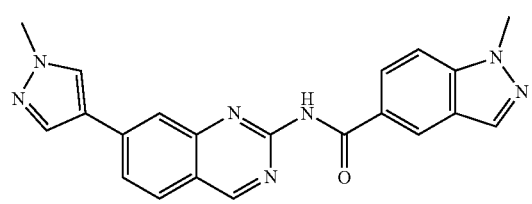 [SMILES: Cn1cc(-c2ccc3cnc(NC(=O)c4ccc5c(cnn5C)c4)nc3c2)cn1] 1133
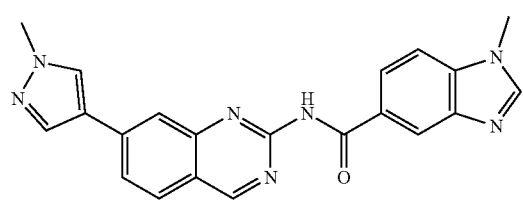 [SMILES: Cn1cc(-c2ccc3cnc(NC(=O)c4ccc5c(c4)ncn5C)nc3c2)cn1] 1134
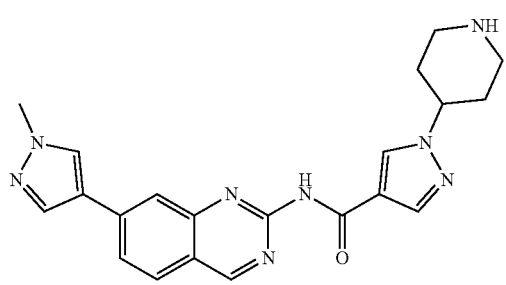 [SMILES: Cn1cc(-c2ccc3cnc(NC(=O)c4cnn(C5CCNCC5)c4)nc3c2)cn1] 1135
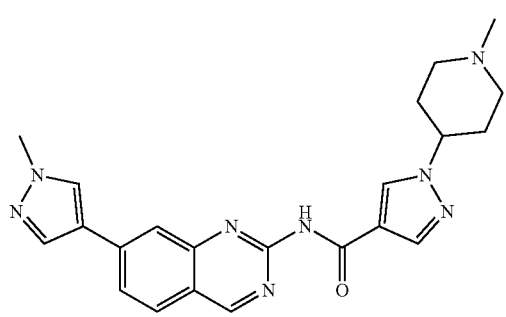 [SMILES: CN1CCC(n2cc(C(=O)Nc3ncc4ccc(-c5cnn(C)c5)cc4n3)cn2)CC1] 1136

TABLE 1-continued
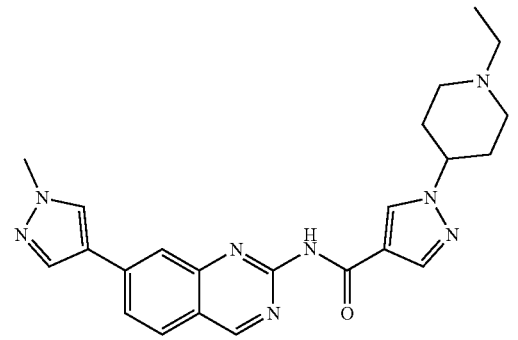 [SMILES: CCN1CCC(n2cc(C(=O)Nc3ncc4ccc(-c5cnn(C)c5)cc4n3)cn2)CC1]
1137
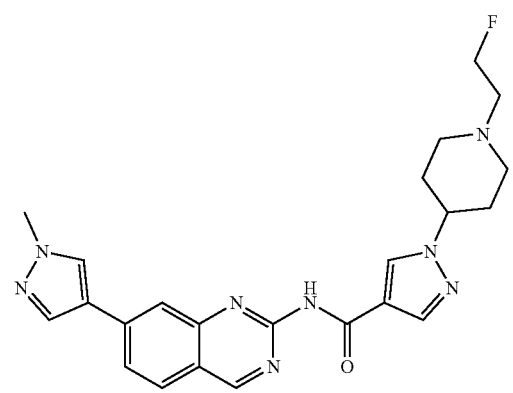 [SMILES: Cn1cc(-c2ccc3cnc(NC(=O)c4cnn(C5CCN(CCF)CC5)c4)nc3c2)cn1]
1138
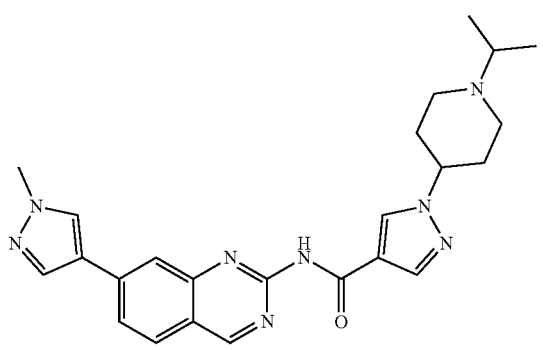 [SMILES: CC(C)N1CCC(n2cc(C(=O)Nc3ncc4ccc(-c5cnn(C)c5)cc4n3)cn2)CC1]
1139
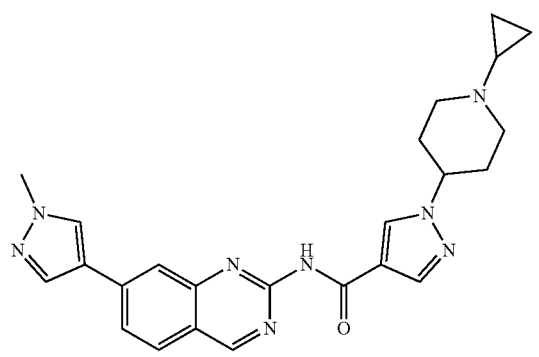 [SMILES: Cn1cc(-c2ccc3cnc(NC(=O)c4cnn(C5CCN(C6CC6)CC5)c4)nc3c2)cn1]
1140

TABLE 1-continued
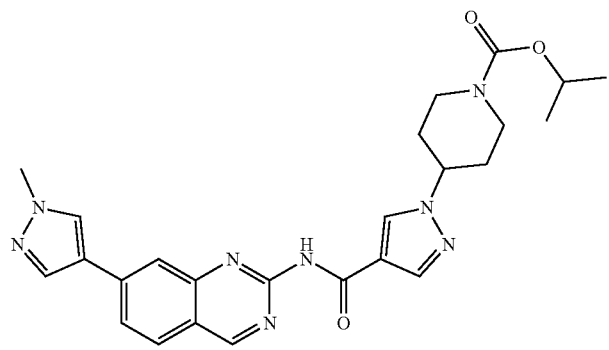 [SMILES: CC(C)OC(=O)N1CCC(n2cc(C(=O)Nc3ncc4ccc(-c5cnn(C)c5)cc4n3)cn2)CC1]
1141
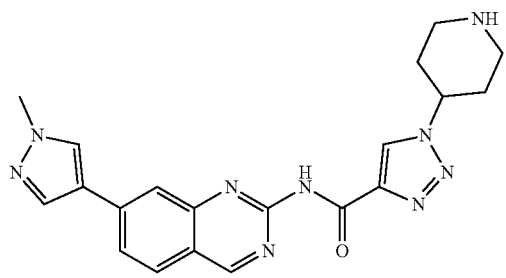 [SMILES: Cn1cc(-c2ccc3cnc(NC(=O)c4cn(C5CCNCC5)nn4)nc3c2)cn1]
1142
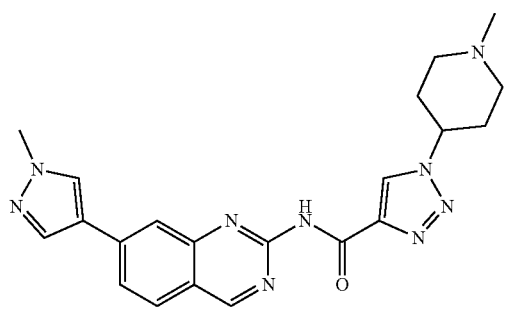 [SMILES: CN1CCC(n2cc(C(=O)Nc3ncc4ccc(-c5cnn(C)c5)cc4n3)nn2)CC1]
1143
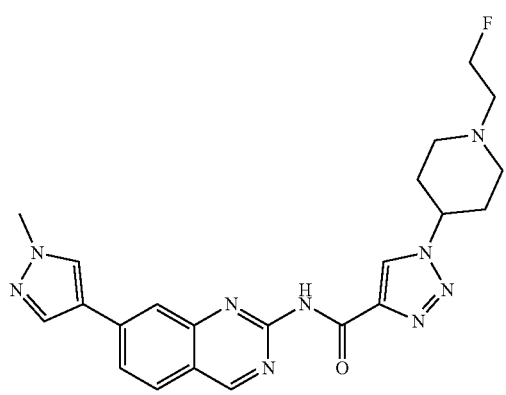 [SMILES: Cn1cc(-c2ccc3cnc(NC(=O)c4cn(C5CCN(CCF)CC5)nn4)nc3c2)cn1]
1144

TABLE 1-continued
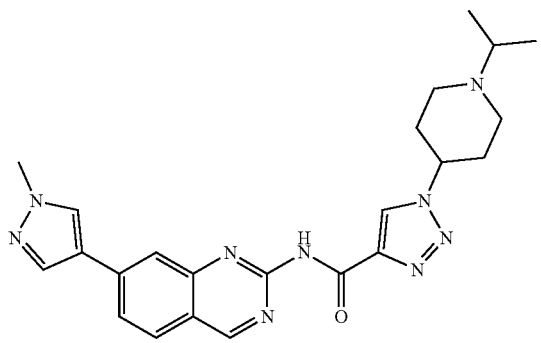 [SMILES: CC(C)N1CCC(n2cc(C(=O)Nc3ncc4ccc(-c5cnn(C)c5)cc4n3)nn2)CC1]
1145
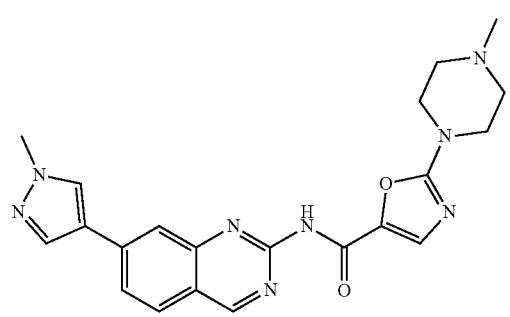 [SMILES: CN1CCN(c2ncc(C(=O)Nc3ncc4ccc(-c5cnn(C)c5)cc4n3)o2)CC1]
1146
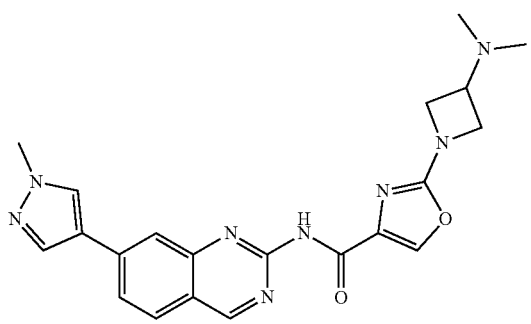 [SMILES: CN(C)C1CN(c2nc(C(=O)Nc3ncc4ccc(-c5cnn(C)c5)cc4n3)co2)C1]
1147
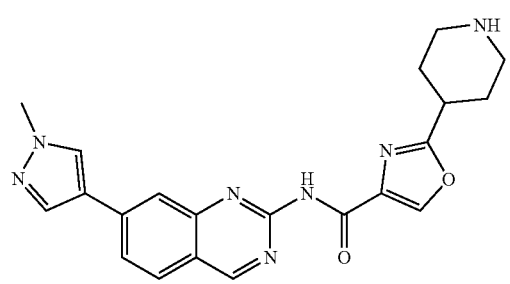 [SMILES: Cn1cc(-c2ccc3cnc(NC(=O)c4csc(C5CCNCC5)n4)nc3c2)cn1]
1148
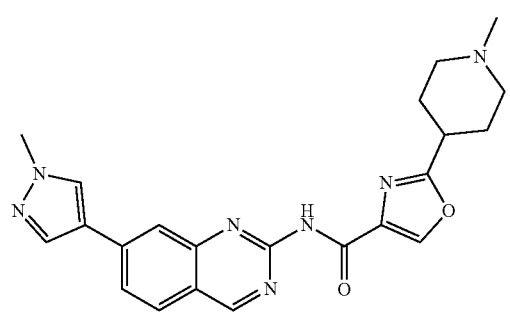
1149

TABLE 1-continued
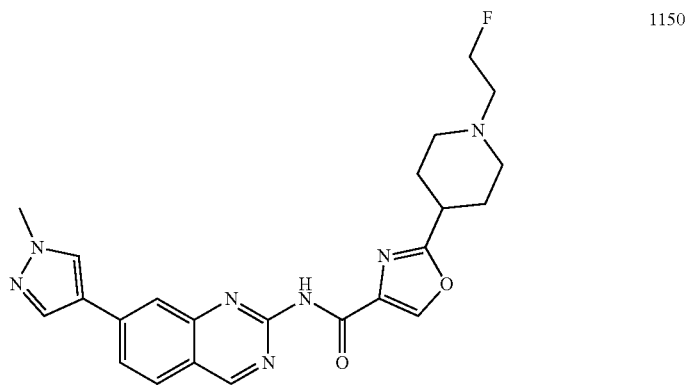
1150
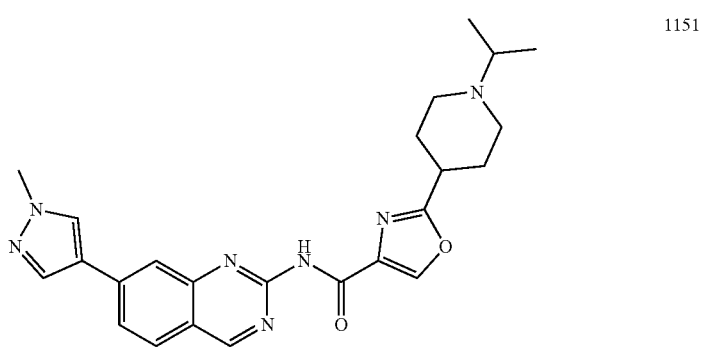
1151
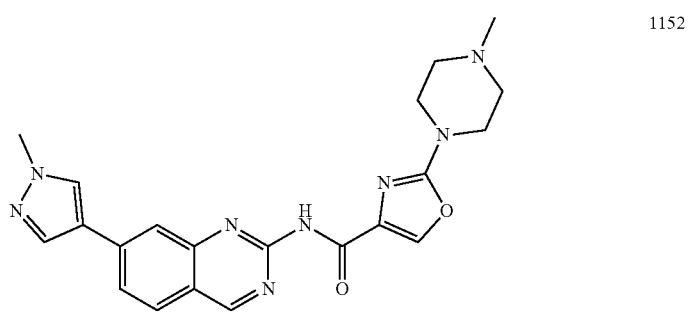
1152
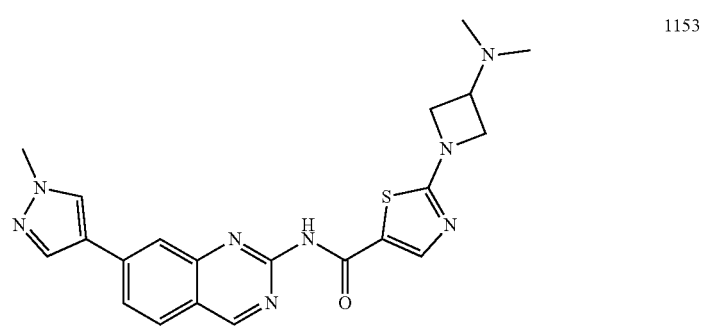
1153
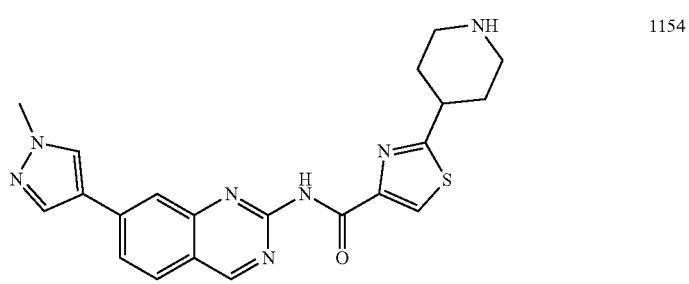
1154

TABLE 1-continued
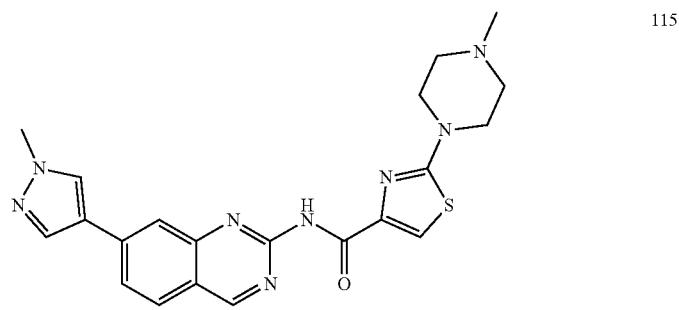
1155
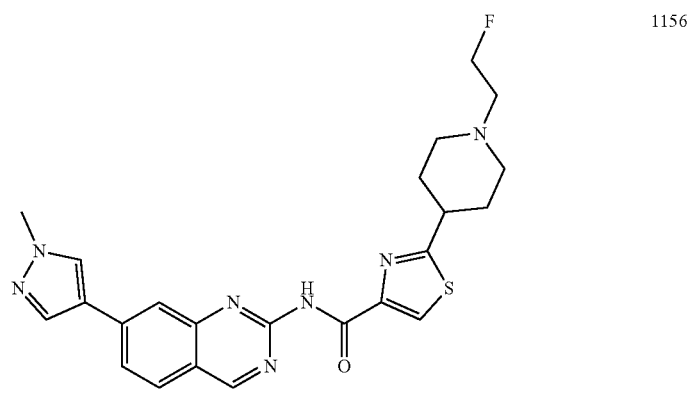
1156
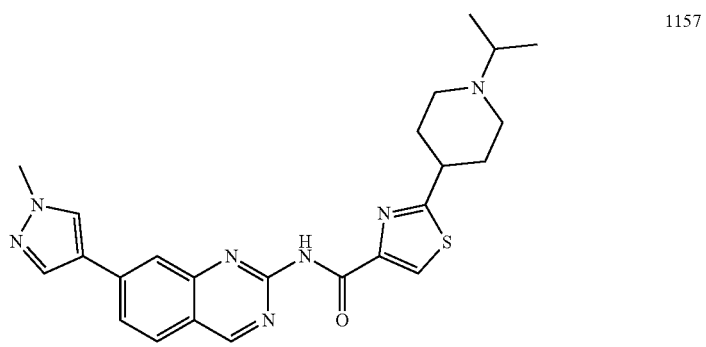
1157
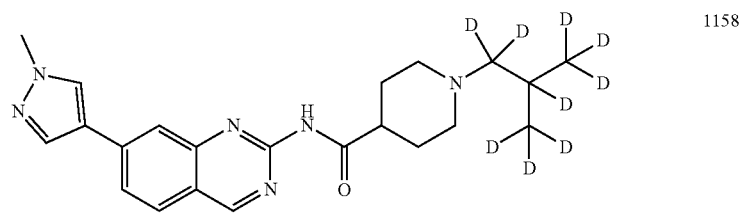
1158
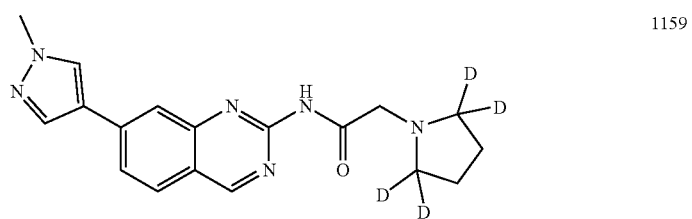
1159

TABLE 1-continued
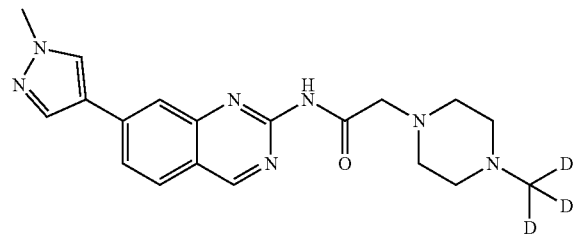 [SMILES: [2H]C([2H])([2H])N1CCN(CC(=O)Nc2ncc3ccc(-c4cnn(C)c4)cc3n2)CC1]
1160
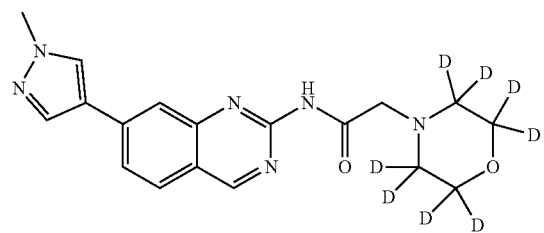 [SMILES: [2H]C1([2H])OC([2H])([2H])C([2H])([2H])N(CC(=O)Nc2ncc3ccc(-c4cnn(C)c4)cc3n2)C1([2H])[2H]]
1161
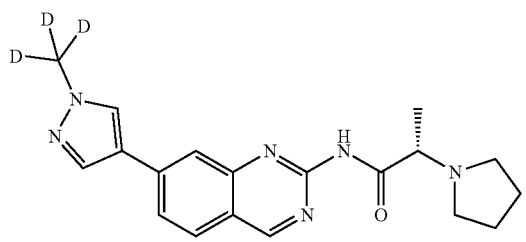 [SMILES: [2H]C([2H])([2H])n1cc(-c2ccc3cnc(NC(=O)[C@H](C)N4CCCC4)nc3c2)cn1]
1162
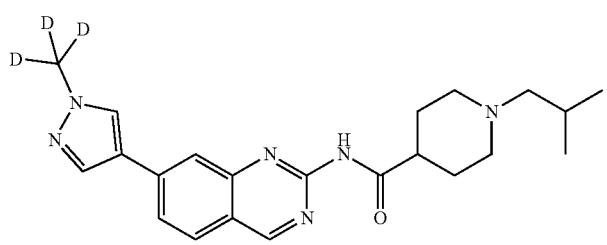
1163
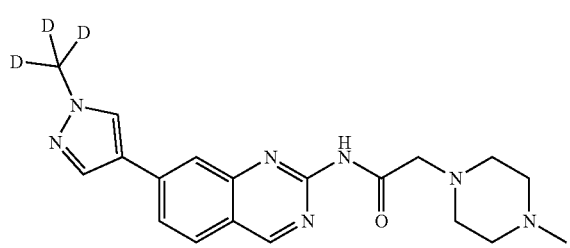 [SMILES: [2H]C([2H])([2H])n1cc(-c2ccc3cnc(NC(=O)CN4CCN(C)CC4)nc3c2)cn1]
1164
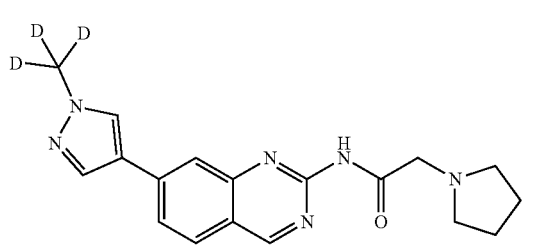 [SMILES: [2H]C([2H])([2H])n1cc(-c2ccc3cnc(NC(=O)CN4CCCC4)nc3c2)cn1]
1165

TABLE 1-continued
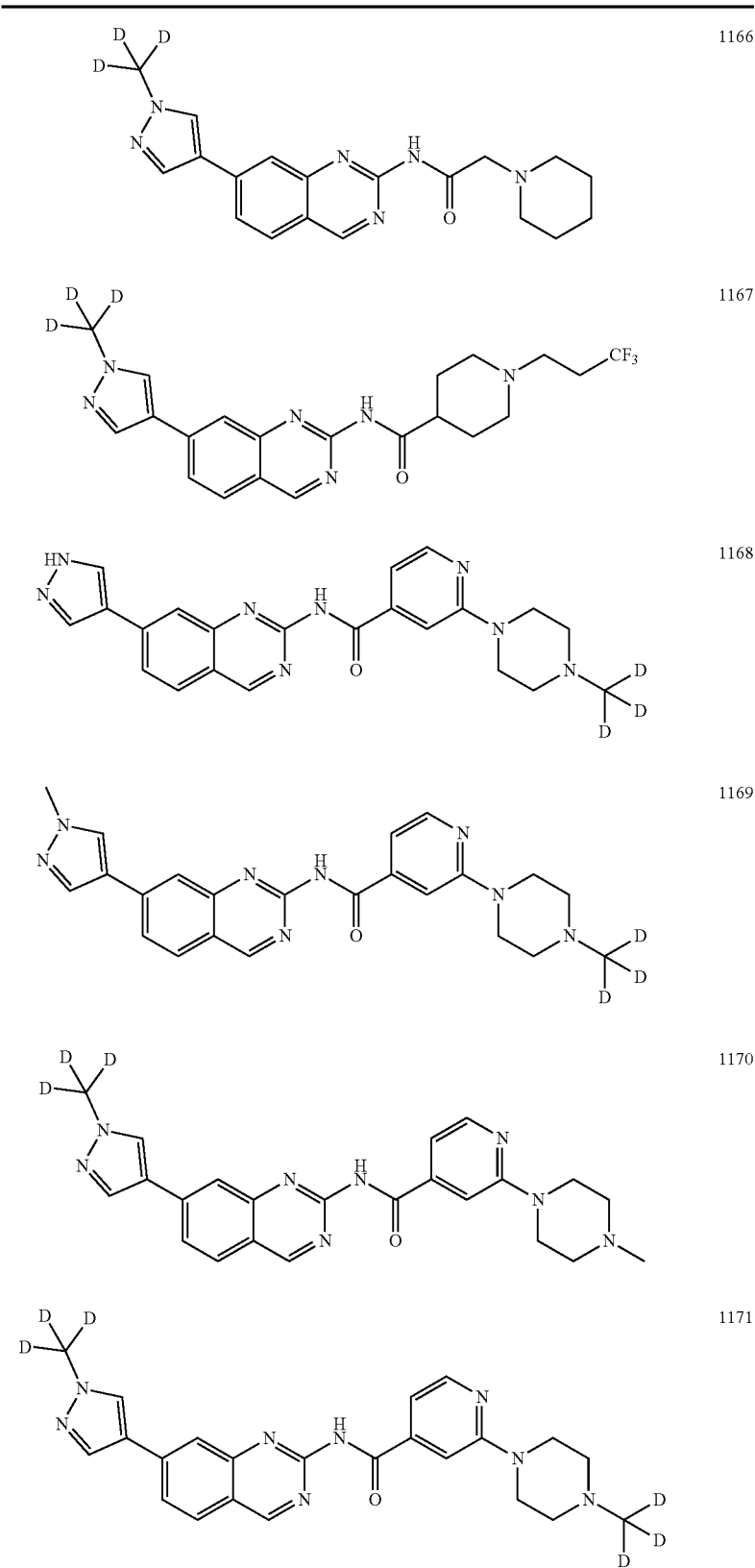

TABLE 1-continued
| | |
|---|---|
| 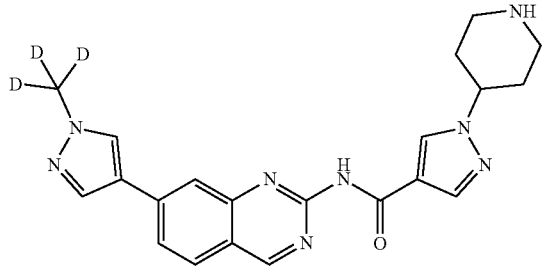 [SMILES: [2H]C([2H])([2H])n1cc(-c2ccc3cnc(NC(=O)c4cnn(C5CCNCC5)c4)nc3c2)cn1] | 1172 |
| 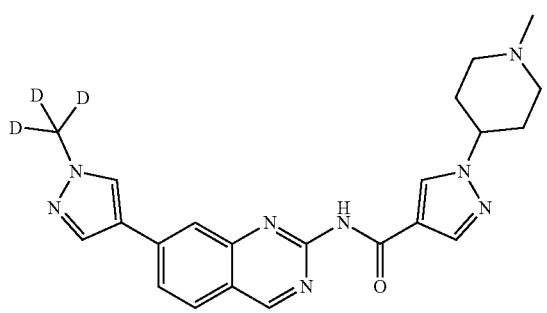 [SMILES: [2H]C([2H])([2H])n1cc(-c2ccc3cnc(NC(=O)c4cnn(C5CCN(C)CC5)c4)nc3c2)cn1] | 1173 |
| 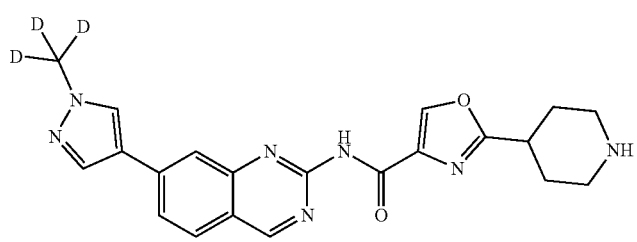 [SMILES: [2H]C([2H])([2H])n1cc(-c2ccc3cnc(NC(=O)c4coc(C5CCNCC5)n4)nc3c2)cn1] | 1174 |
| 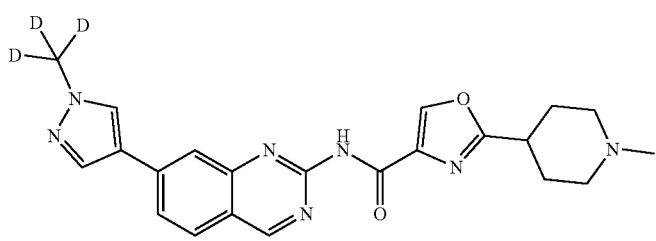 [SMILES: [2H]C([2H])([2H])n1cc(-c2ccc3cnc(NC(=O)c4coc(C5CCN(C)CC5)n4)nc3c2)cn1] | 1175 |
| 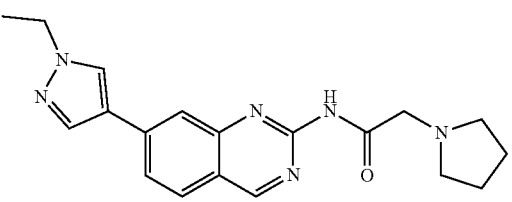 [SMILES: CCn1cc(-c2ccc3cnc(NC(=O)CN4CCCC4)nc3c2)cn1] | 1176 |
| 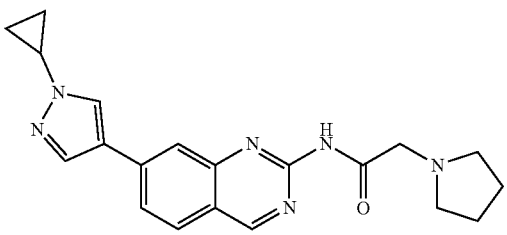 [SMILES: O=C(CN1CCCC1)Nc1ncc2ccc(-c3cnn(C4CC4)c3)cc2n1] | 1177 |

TABLE 1-continued
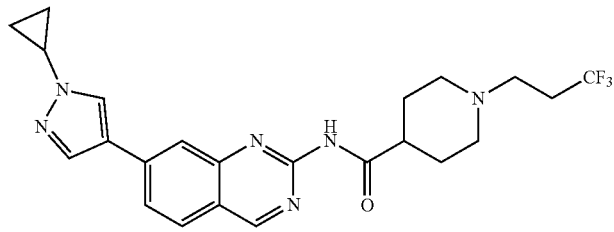 [SMILES: O=C(Nc1ncc2ccc(-c3cnn(C4CC4)c3)cc2n1)C1CCN(CCC(F)(F)F)CC1] 1178
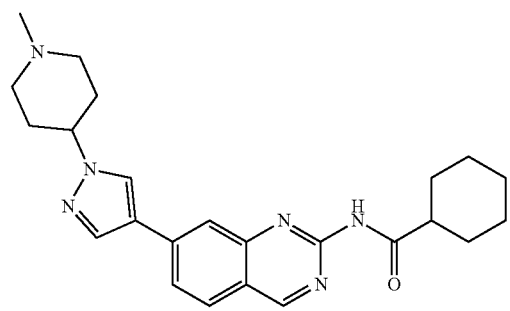 1179
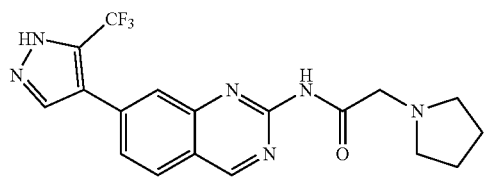 [SMILES: O=C(CN1CCCC1)Nc1ncc2ccc(-c3cn[nH]c3C(F)(F)F)cc2n1] 1180
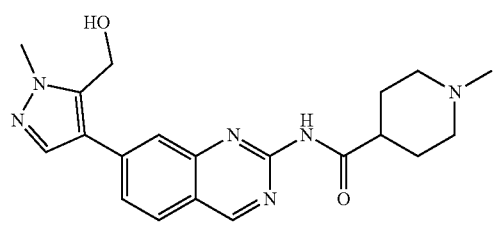 [SMILES: CN1CCC(C(=O)Nc2ncc3ccc(-c4cnn(C)c4CO)cc3n2)CC1] 1181
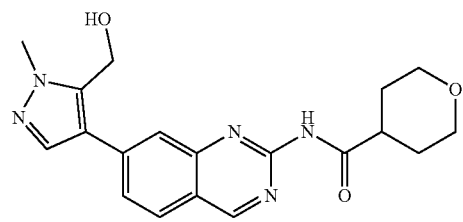 [SMILES: Cn1ncc(-c2ccc3cnc(NC(=O)C4CCOCC4)nc3c2)c1CO] 1182
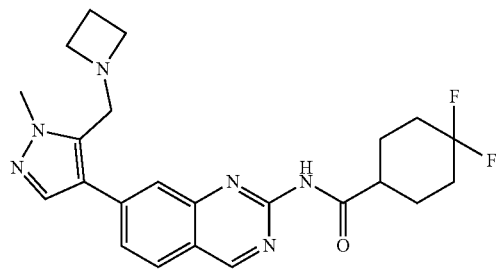 [SMILES: Cn1ncc(-c2ccc3cnc(NC(=O)C4CCC(F)(F)CC4)nc3c2)c1CN1CCC1] 1183

TABLE 1-continued
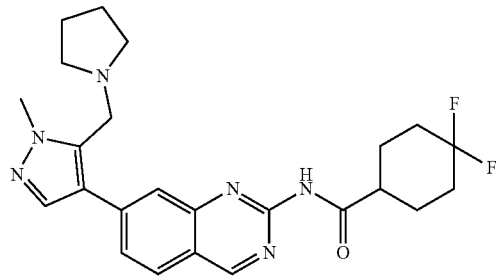 [SMILES: Cn1ncc(-c2ccc3cnc(NC(=O)C4CCC(F)(F)CC4)nc3c2)c1CN1CCCC1]
1184
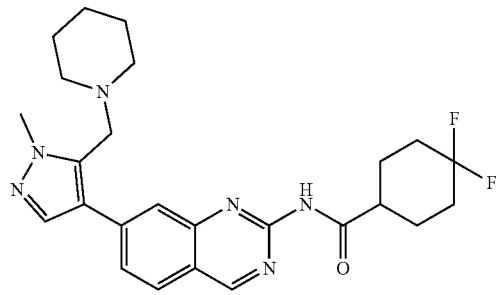 [SMILES: Cn1ncc(-c2ccc3cnc(NC(=O)C4CCC(F)(F)CC4)nc3c2)c1CN1CCCCC1]
1185
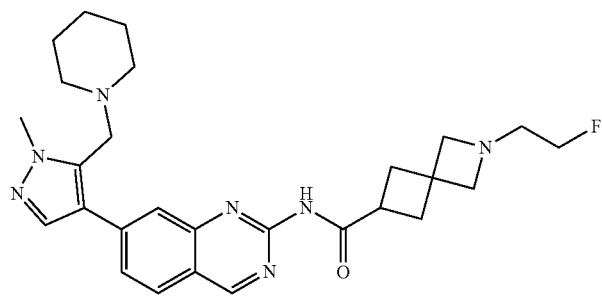
1186
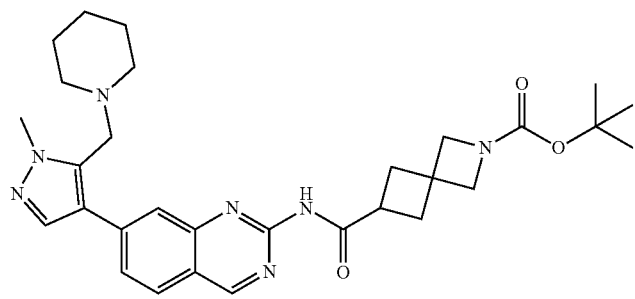 [SMILES: Cn1ncc(-c2ccc3cnc(NC(=O)C4CC5(C4)CN(C(=O)OC(C)(C)C)C5)nc3c2)c1CN1CCCCC1]
1187
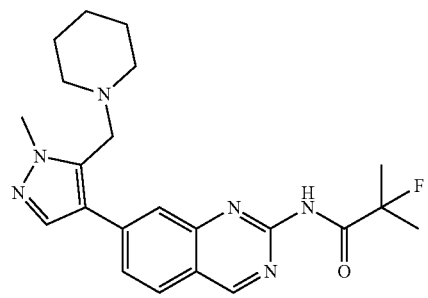 [SMILES: Cn1ncc(-c2ccc3cnc(NC(=O)C(C)(C)F)nc3c2)c1CN1CCCCC1]
1188

TABLE 1-continued
| | |
|---|---|
| 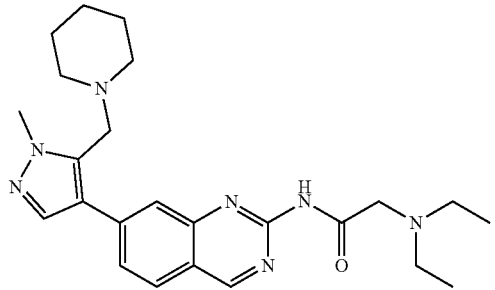 [SMILES: CCN(CC)CC(=O)Nc1ncc2ccc(-c3cnn(C)c3CN3CCCCC3)cc2n1] | 1189 |
| 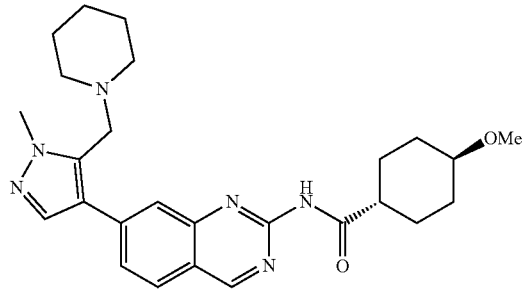 [SMILES: CO[C@H]1CC[C@H](C(=O)Nc2ncc3ccc(-c4cnn(C)c4CN4CCCCC4)cc3n2)CC1] | 1190 |
| 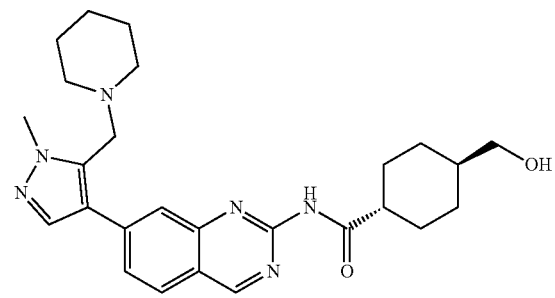 [SMILES: Cn1ncc(-c2ccc3cnc(NC(=O)[C@H]4CC[C@H](CO)CC4)nc3c2)c1CN1CCCCC1] | 1191 |
| 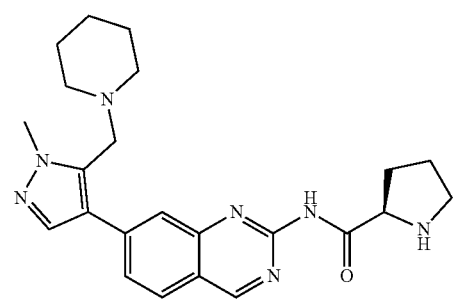 [SMILES: Cn1ncc(-c2ccc3cnc(NC(=O)[C@H]4CCCN4)nc3c2)c1CN1CCCCC1] | 1192 |
| 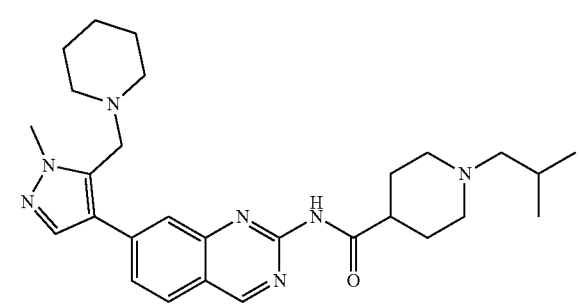 [SMILES: CC(C)CN1CCC(C(=O)Nc2ncc3ccc(-c4cnn(C)c4CN4CCCCC4)cc3n2)CC1] | 1193 |

TABLE 1-continued
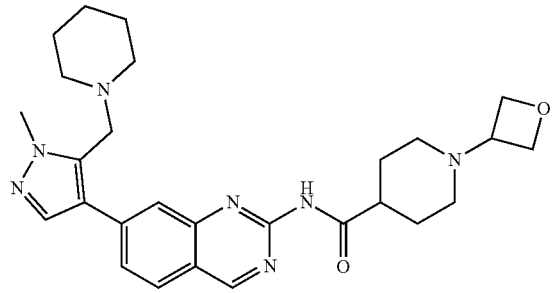 [SMILES: Cn1ncc(-c2ccc3cnc(NC(=O)C4CCN(C5COC5)CC4)nc3c2)c1CN1CCCCC1]
1194
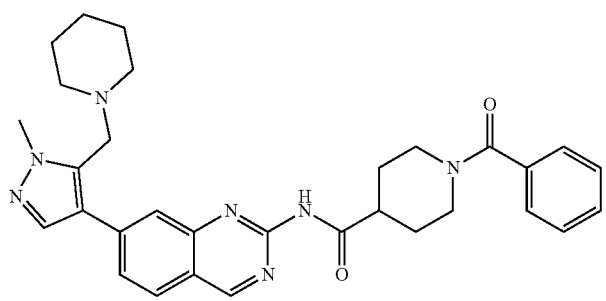 [SMILES: Cn1ncc(-c2ccc3cnc(NC(=O)C4CCN(C(=O)c5ccccc5)CC4)nc3c2)c1CN1CCCCC1]
1195
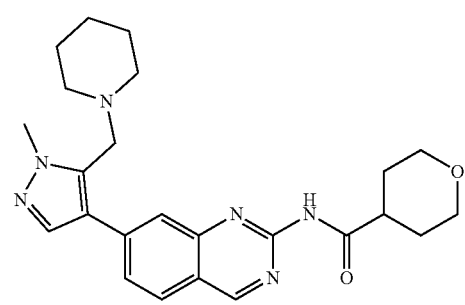 [SMILES: Cn1ncc(-c2ccc3cnc(NC(=O)C4CCOCC4)nc3c2)c1CN1CCCCC1]
1196
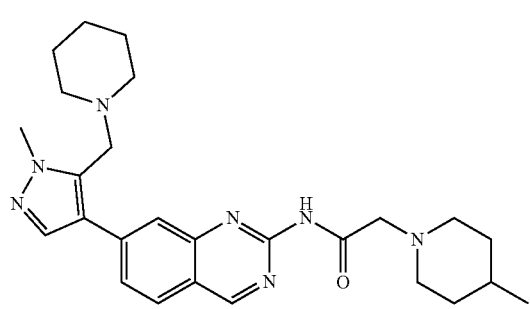
1197
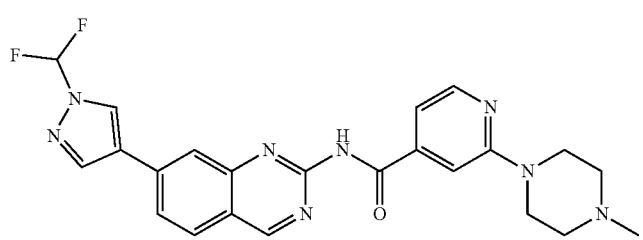 [SMILES: CN1CCN(c2cc(C(=O)Nc3ncc4ccc(-c5cnn(C(F)F)c5)cc4n3)ccn2)CC1]
1198

TABLE 1-continued
| | |
|---|---|
| 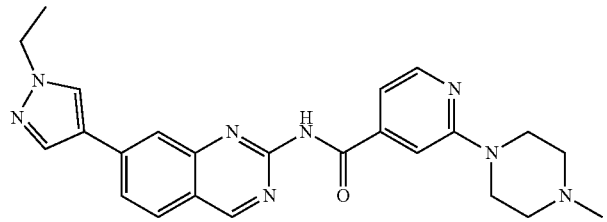 | 1199 |
| 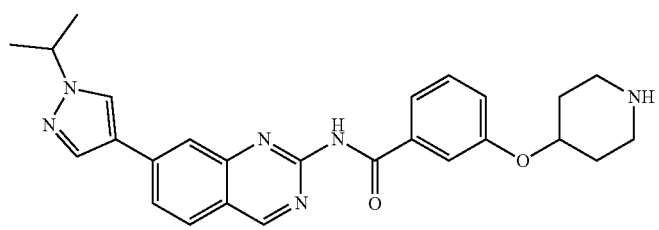 [SMILES: CC(C)n1cc(-c2ccc3cnc(NC(=O)c4cccc(OC5CCNCC5)c4)nc3c2)cn1] | 1200 |
| 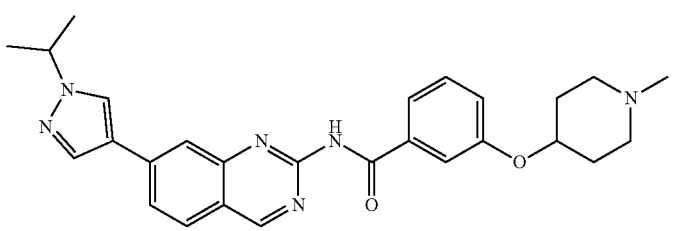 [SMILES: CC(C)n1cc(-c2ccc3cnc(NC(=O)c4cccc(OC5CCN(C)CC5)c4)nc3c2)cn1] | 1201 |
| 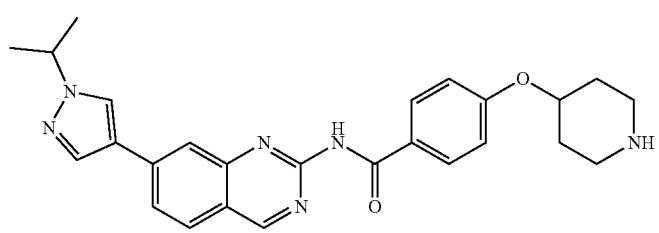 [SMILES: CC(C)n1cc(-c2ccc3cnc(NC(=O)c4ccc(OC5CCNCC5)cc4)nc3c2)cn1] | 1202 |
| 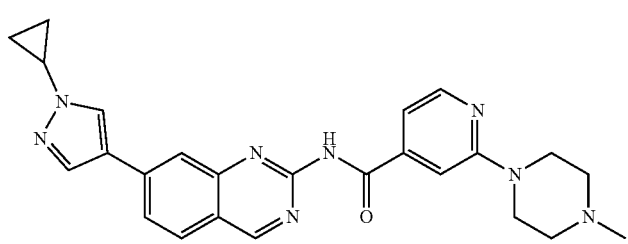 [SMILES: CN1CCN(c2cc(C(=O)Nc3ncc4ccc(-c5cnn(C6CC6)c5)cc4n3)ccn2)CC1] | 1203 |
| 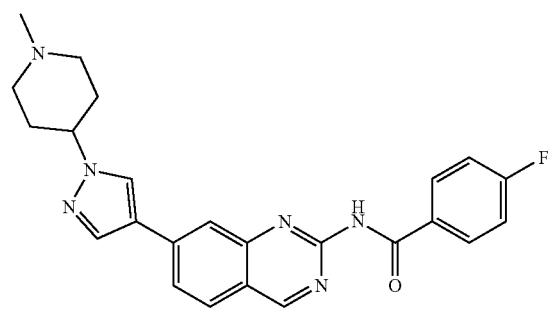 [SMILES: CN1CCC(n2cc(-c3ccc4cnc(NC(=O)c5ccc(F)cc5)nc4c3)cn2)CC1] | 1204 |

TABLE 1-continued
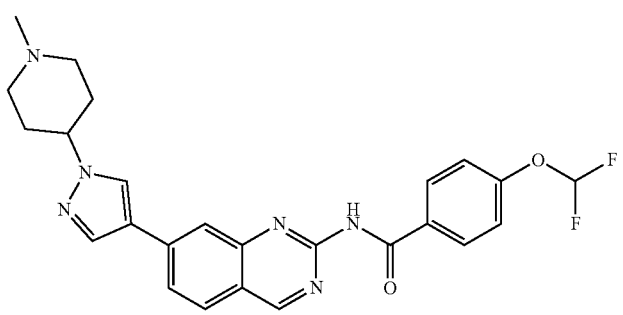 [SMILES: CN1CCC(n2cc(-c3ccc4cnc(NC(=O)c5ccc(OC(F)F)cc5)nc4c3)cn2)CC1]
1205
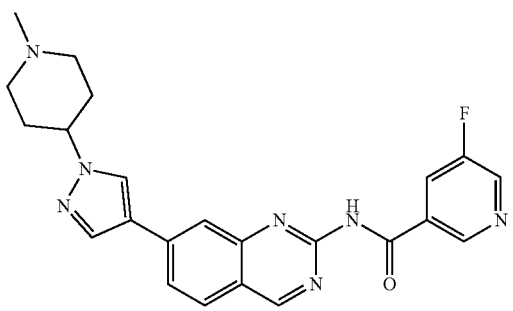 [SMILES: CN1CCC(n2cc(-c3ccc4cnc(NC(=O)c5cncc(F)c5)nc4c3)cn2)CC1]
1206
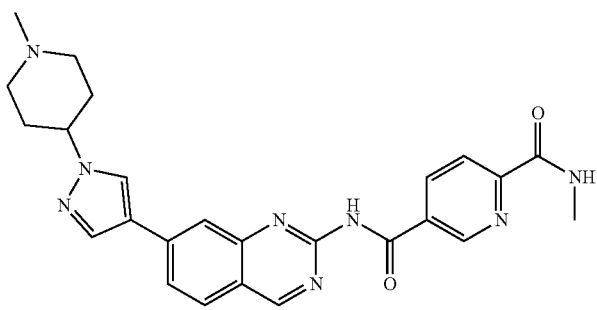 [SMILES: CNC(=O)c1ccc(C(=O)Nc2ncc3ccc(-c4cnn(C5CCN(C)CC5)c4)cc3n2)cn1]
1207
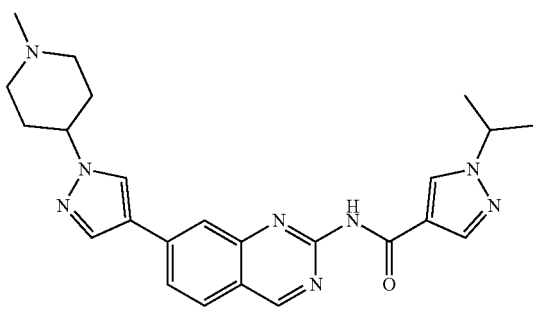 [SMILES: CC(C)n1cc(C(=O)Nc2ncc3ccc(-c4cnn(C5CCN(C)CC5)c4)cc3n2)cn1]
1208
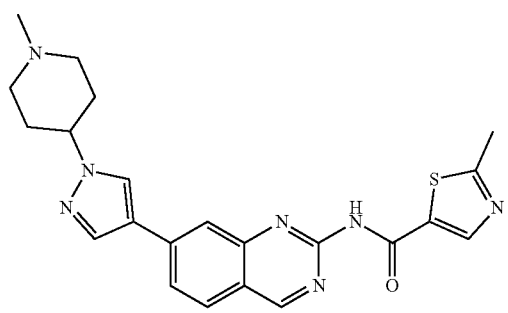 [SMILES: Cc1ncc(C(=O)Nc2ncc3ccc(-c4cnn(C5CCN(C)CC5)c4)cc3n2)s1]
1209

TABLE 1-continued
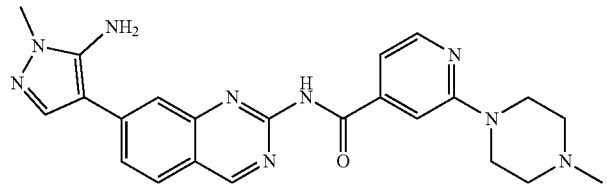
1210
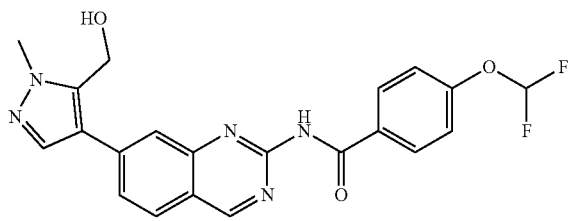 [SMILES: Cn1ncc(-c2ccc3cnc(NC(=O)c4ccc(OC(F)F)cc4)nc3c2)c1CO]
1211
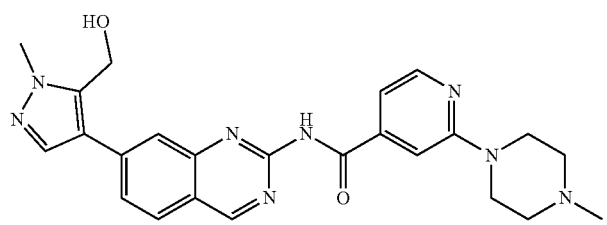
1212
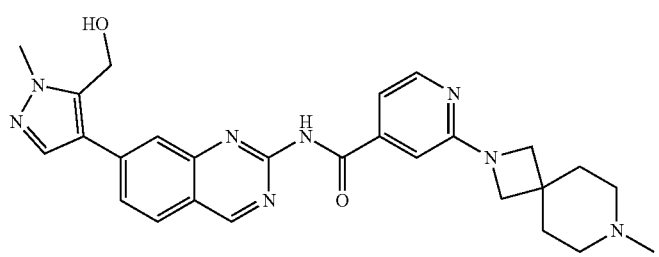 [SMILES: CN1CCC2(CC1)CN(c1cc(C(=O)Nc3ncc4ccc(-c5cnn(C)c5CO)cc4n3)ccn1)C2]
1213
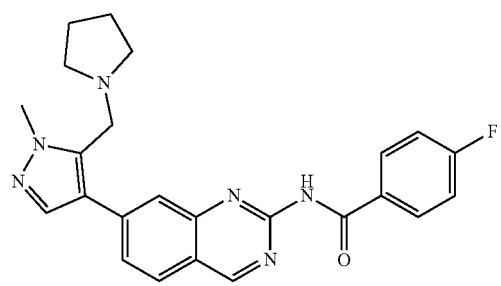 [SMILES: Cn1ncc(-c2ccc3cnc(NC(=O)c4ccc(F)cc4)nc3c2)c1CN1CCCC1]
1214
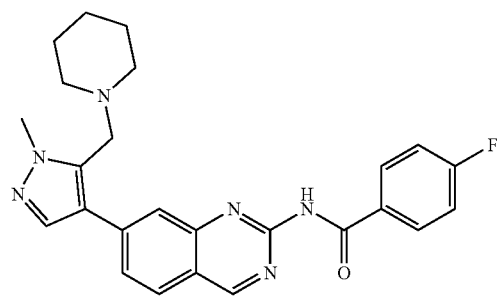 [SMILES: Cn1ncc(-c2ccc3cnc(NC(=O)c4ccc(F)cc4)nc3c2)c1CN1CCCCC1]
1215

TABLE 1-continued
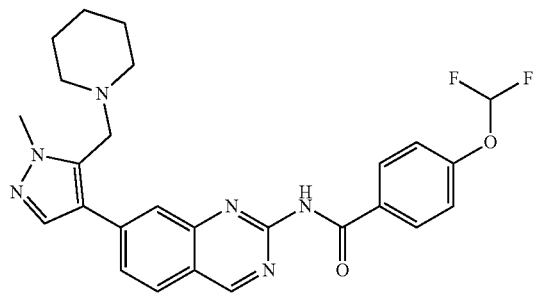 [SMILES: Cn1ncc(-c2ccc3cnc(NC(=O)c4ccc(OC(F)F)cc4)nc3c2)c1CN1CCCCC1]
1216
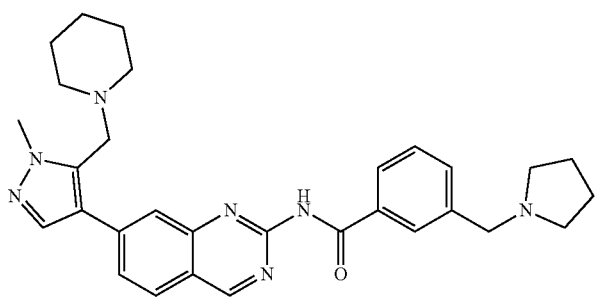 [SMILES: Cn1ncc(-c2ccc3cnc(NC(=O)c4cccc(CN5CCCC5)c4)nc3c2)c1CN1CCCCC1]
1217
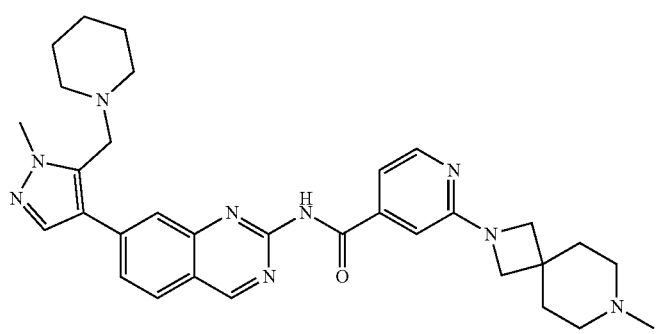
1218
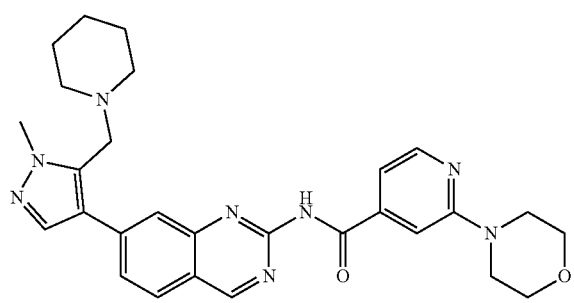 [SMILES: Cn1ncc(-c2ccc3cnc(NC(=O)c4ccnc(N5CCOCC5)c4)nc3c2)c1CN1CCCCC1]
1219
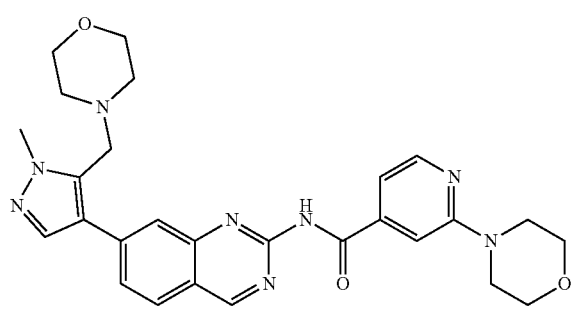 [SMILES: Cn1ncc(-c2ccc3cnc(NC(=O)c4ccnc(N5CCOCC5)c4)nc3c2)c1CN1CCOCC1]
1220

TABLE 1-continued
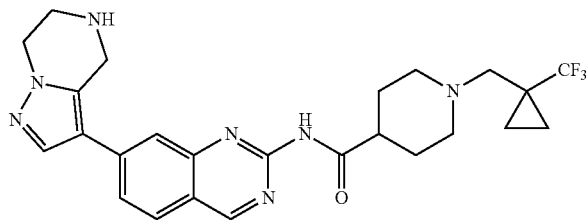 [SMILES: O=C(Nc1ncc2ccc(-c3cnn4c3CNCC4)cc2n1)C1CCN(CC2(C(F)(F)F)CC2)CC1] 1221
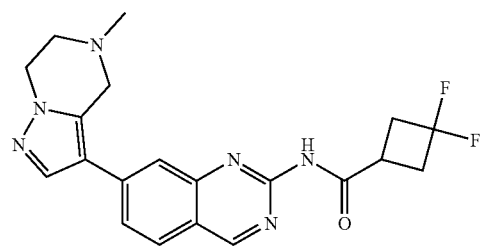 [SMILES: CN1CCn2ncc(-c3ccc4cnc(NC(=O)C5CC(F)(F)C5)nc4c3)c2C1] 1222
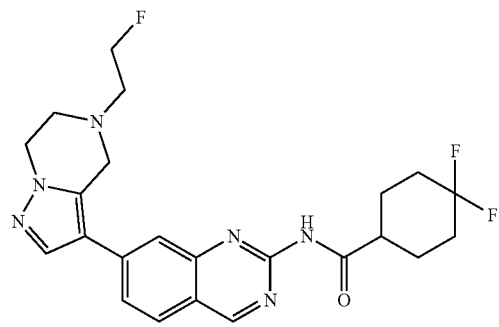 1223
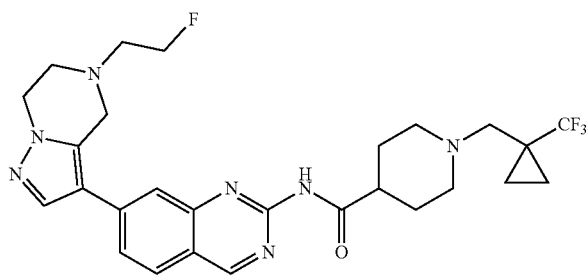 1224
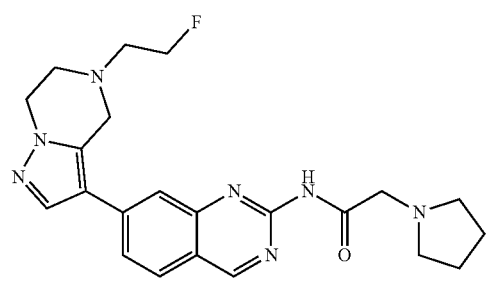 [SMILES: O=C(CN1CCCC1)Nc1ncc2ccc(-c3cnn4c3CN(CCF)CC4)cc2n1] 1225

TABLE 1-continued

| | |
|---|---|
| [structure] | 1226 |
| [structure] | 1227 |
| [structure] | 1228 |
| [structure] | 1229 |
| [structure] | 1230 |
| [structure] | 1231 |

TABLE 1-continued
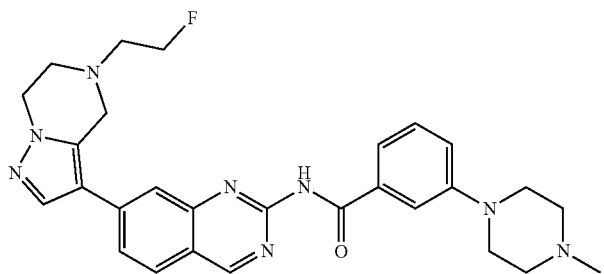 [SMILES: CN1CCN(c2cccc(C(=O)Nc3ncc4ccc(-c5cnn6c5CN(CCF)CC6)cc4n3)c2)CC1] 1232
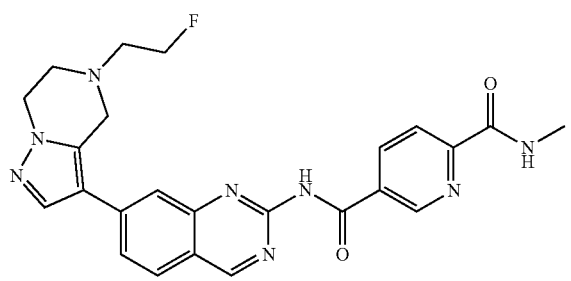 [SMILES: CNC(=O)c1ccc(C(=O)Nc2ncc3ccc(-c4cnn5c4CN(CCF)CC5)cc3n2)cn1] 1233
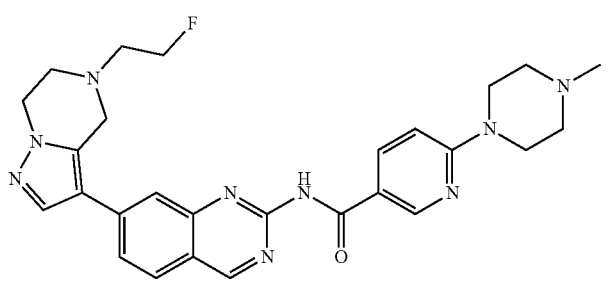 [SMILES: CN1CCN(c2ccc(C(=O)Nc3ncc4ccc(-c5cnn6c5CN(CCF)CC6)cc4n3)cn2)CC1] 1234
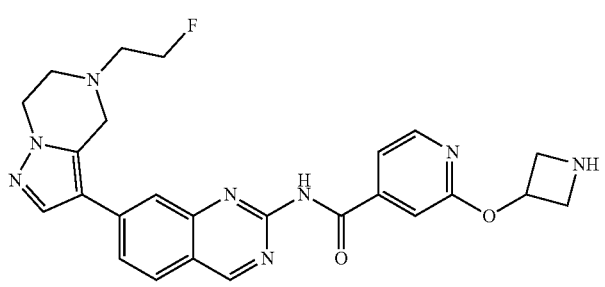 [SMILES: O=C(Nc1ncc2ccc(-c3cnn4c3CN(CCF)CC4)cc2n1)c1ccnc(OC2CNC2)c1] 1235
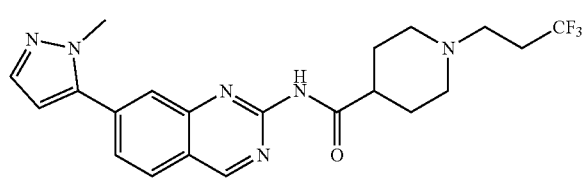 [SMILES: Cn1nccc1-c1ccc2cnc(NC(=O)C3CCN(CCC(F)(F)F)CC3)nc2c1] 1236
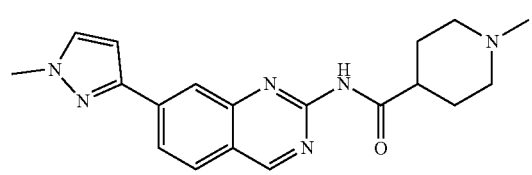 1237
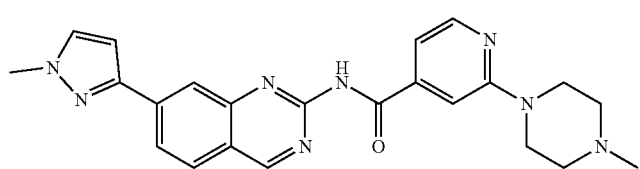 1238

TABLE 1-continued
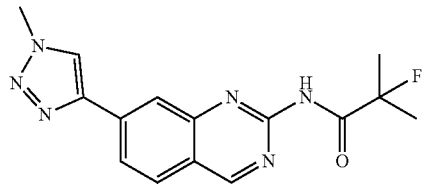 1239
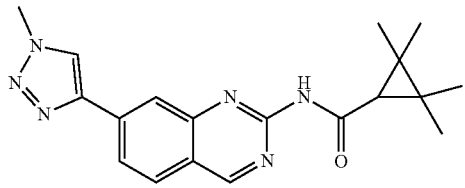 [SMILES: Cn1cc(-c2ccc3cnc(NC(=O)C4C(C)(C)C4(C)C)nc3c2)nn1] 1240
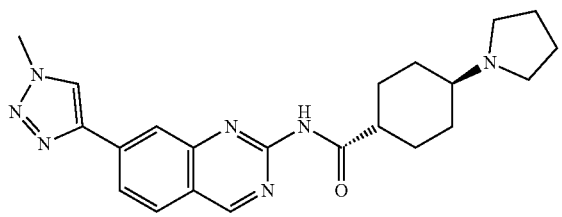 1241
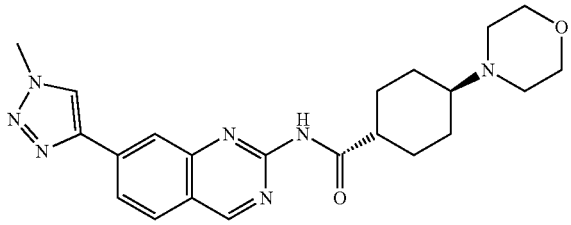 1242
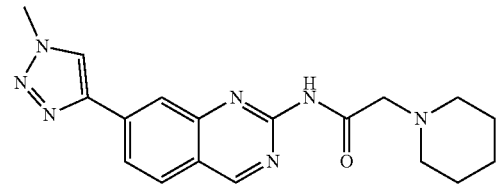 [SMILES: Cn1cc(-c2ccc3cnc(NC(=O)CN4CCCCC4)nc3c2)nn1] 1243
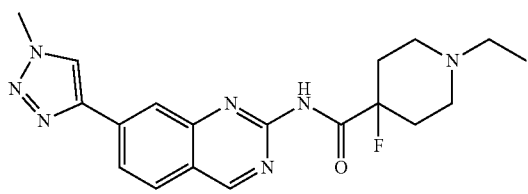 [SMILES: CCN1CCC(F)(C(=O)Nc2ncc3ccc(-c4cn(C)nn4)cc3n2)CC1] 1244
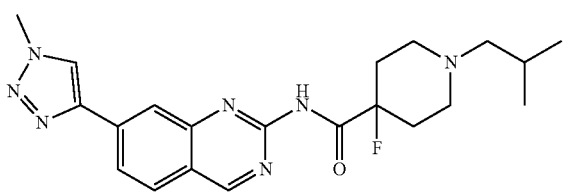 1245
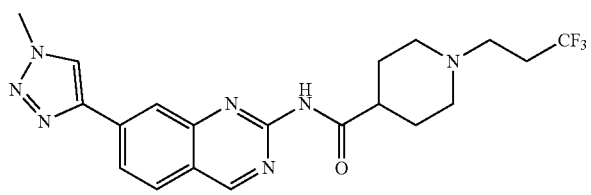 [SMILES: Cn1cc(-c2ccc3cnc(NC(=O)C4CCN(CCC(F)(F)F)CC4)nc3c2)nn1] 1246

TABLE 1-continued

| | |
|---|---|
| (structure) | 1247 |
| (structure) | 1248 |
| (structure) | 1249 |
| (structure) | 1250 |
| (structure) | 1251 |
| (structure) | 1252 |
| (structure) | 1253 |
| (structure) | 1254 |

TABLE 1-continued
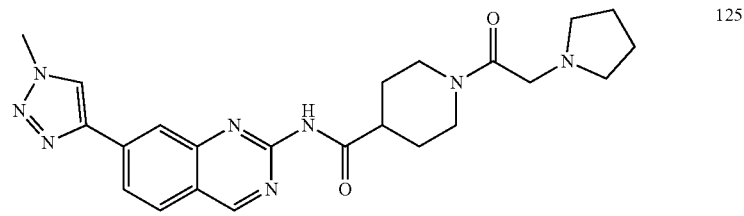
1255
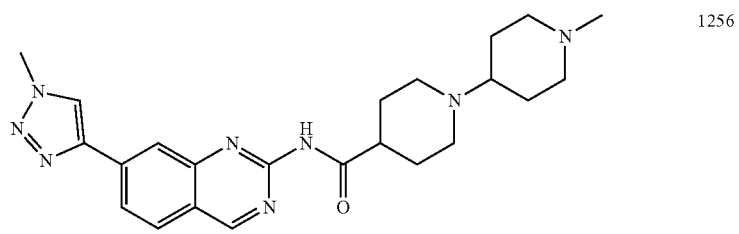
1256
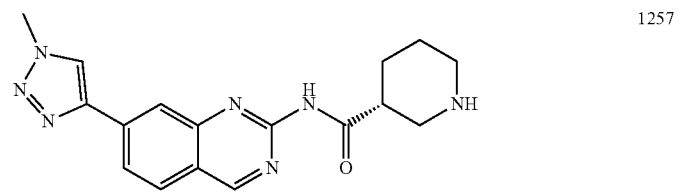
1257
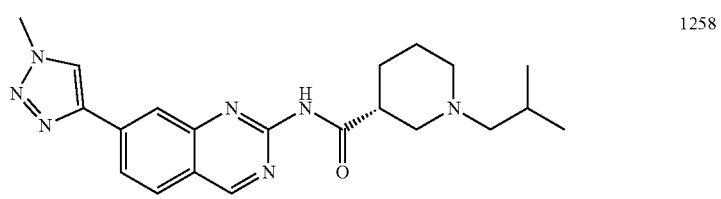
1258
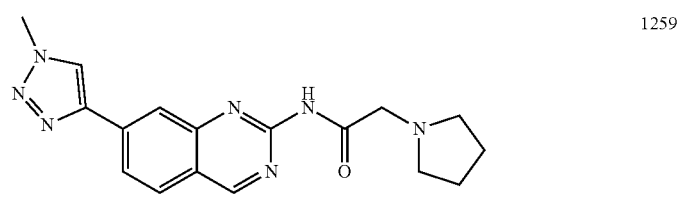
1259
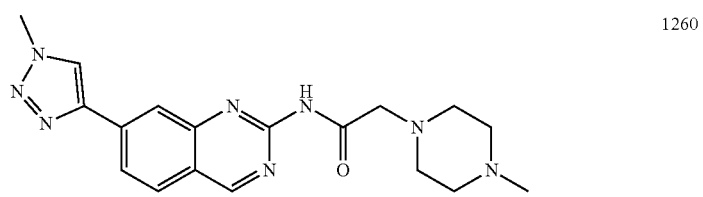
1260
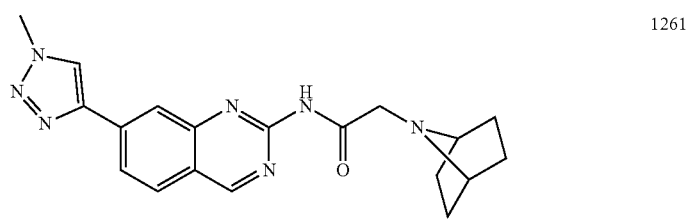
1261

TABLE 1-continued
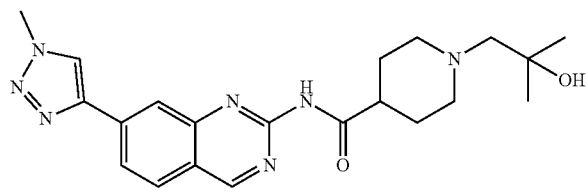 [SMILES: Cn1cc(-c2ccc3cnc(NC(=O)C4CCN(CC(C)(C)O)CC4)nc3c2)nn1]
1262
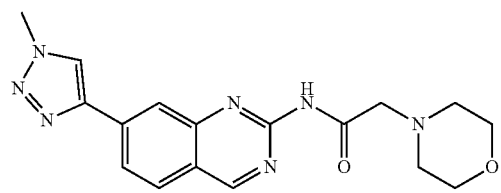 [SMILES: Cn1cc(-c2ccc3cnc(NC(=O)CN4CCOCC4)nc3c2)nn1]
1263
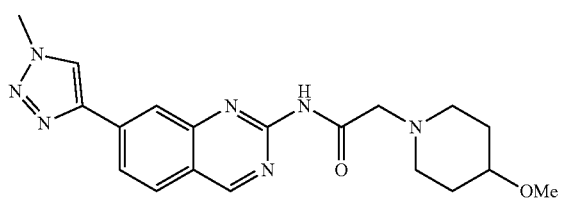 [SMILES: COC1CCN(CC(=O)Nc2ncc3ccc(-c4cn(C)nn4)cc3n2)CC1]
1264
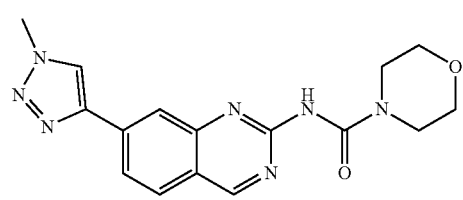 [SMILES: Cn1cc(-c2ccc3cnc(NC(=O)N4CCOCC4)nc3c2)nn1]
1265
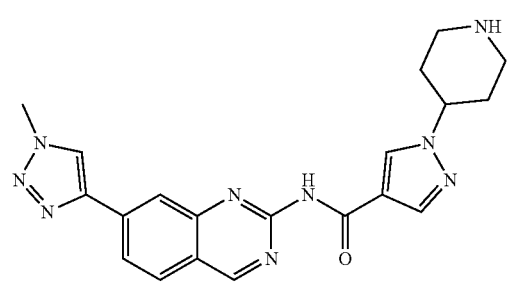 [SMILES: Cn1cc(-c2ccc3cnc(NC(=O)c4cnn(C5CCNCC5)c4)nc3c2)nn1]
1266
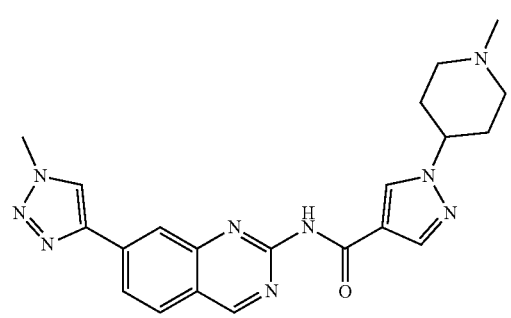 [SMILES: CN1CCC(n2cc(C(=O)Nc3ncc4ccc(-c5cn(C)nn5)cc4n3)cn2)CC1]
1267

TABLE 1-continued
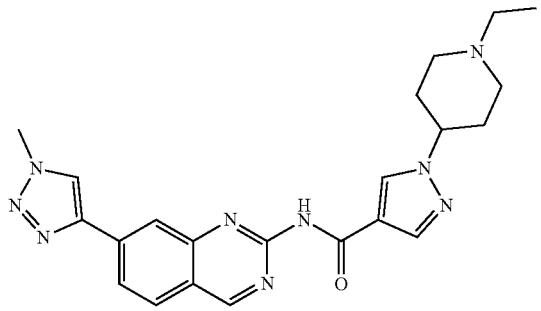 [SMILES: CCN1CCC(n2cc(C(=O)Nc3ncc4ccc(-c5cn(C)nn5)cc4n3)cn2)CC1]
1268
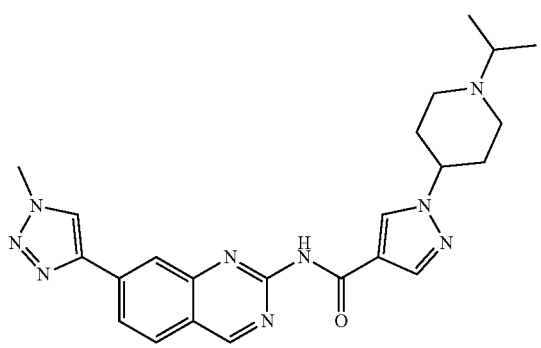
1269
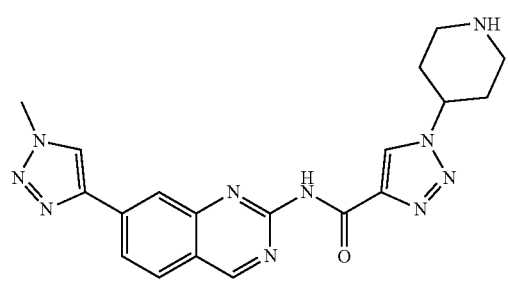 [SMILES: Cn1cc(-c2ccc3cnc(NC(=O)c4cn(C5CCNCC5)nn4)nc3c2)nn1]
1270
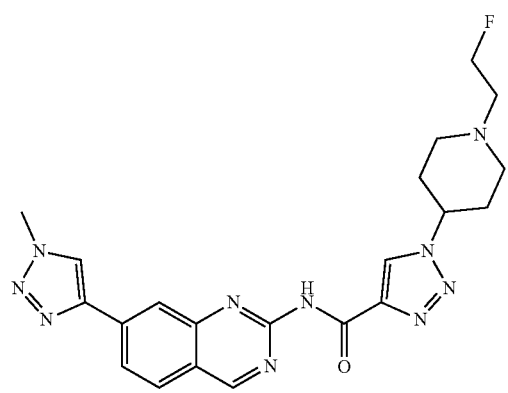 [SMILES: Cn1cc(-c2ccc3cnc(NC(=O)c4cn(C5CCN(CCF)CC5)nn4)nc3c2)nn1]
1271

TABLE 1-continued
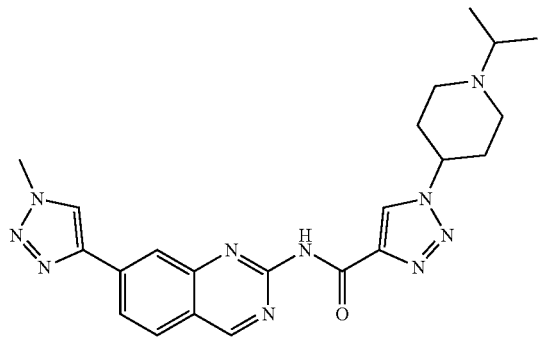 [SMILES: CC(C)N1CCC(n2cc(C(=O)Nc3ncc4ccc(-c5cn(C)nn5)cc4n3)nn2)CC1]
1272
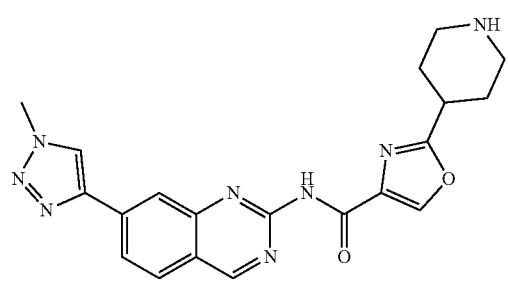 [SMILES: Cn1cc(-c2ccc3cnc(NC(=O)c4coc(C5CCNCC5)n4)nc3c2)nn1]
1273
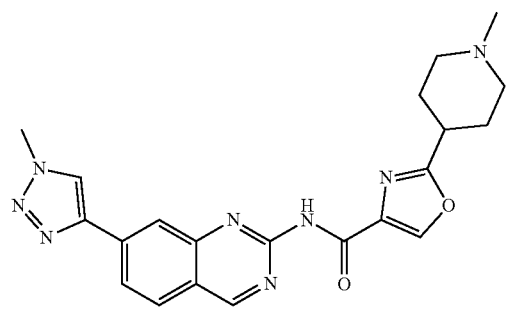 [SMILES: CN1CCC(c2nc(C(=O)Nc3ncc4ccc(-c5cn(C)nn5)cc4n3)co2)CC1]
1274
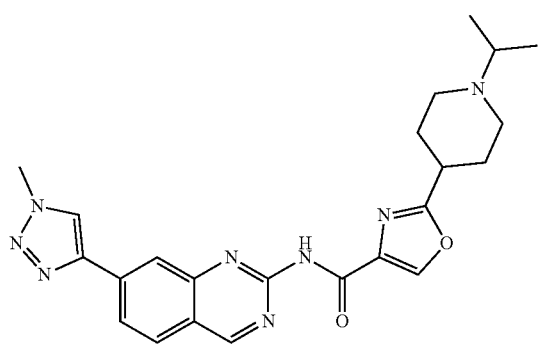
1275
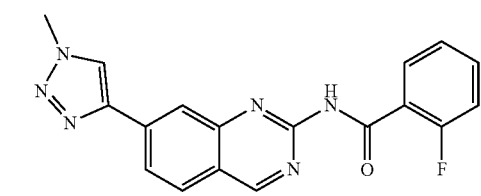 [SMILES: Cn1cc(-c2ccc3cnc(NC(=O)c4ccccc4F)nc3c2)nn1]
1276

TABLE 1-continued
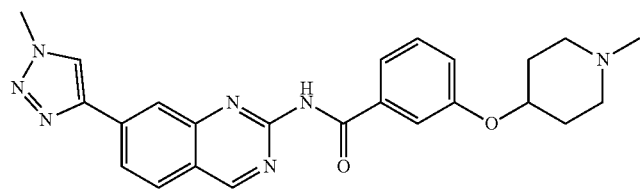 [SMILES: CN1CCC(Oc2cccc(C(=O)Nc3ncc4ccc(-c5cn(C)nn5)cc4n3)c2)CC1]
1277
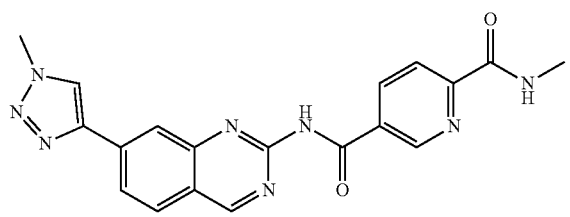 [SMILES: CNC(=O)c1ccc(C(=O)Nc2ncc3ccc(-c4cn(C)nn4)cc3n2)cn1]
1278
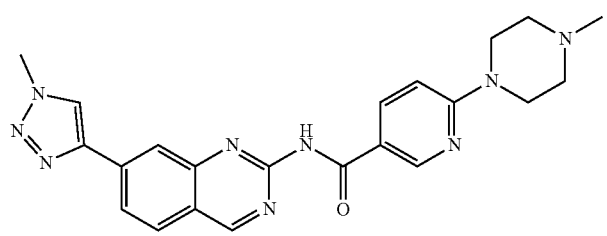 [SMILES: CN1CCN(c2ccc(C(=O)Nc3ncc4ccc(-c5cn(C)nn5)cc4n3)cn2)CC1]
1279
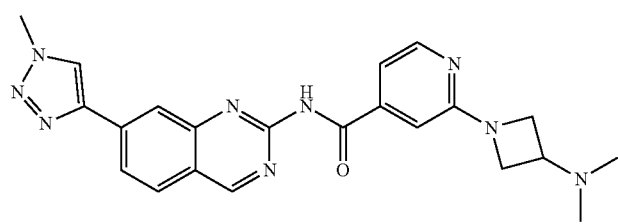 [SMILES: CN(C)C1CN(c2cc(C(=O)Nc3ncc4ccc(-c5cn(C)nn5)cc4n3)ccn2)C1]
1280
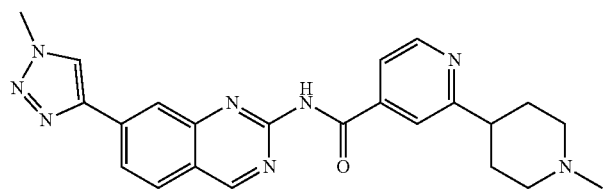 [SMILES: CN1CCC(c2cc(C(=O)Nc3ncc4ccc(-c5cn(C)nn5)cc4n3)ccn2)CC1]
1281
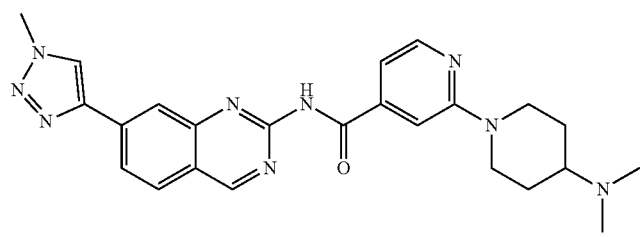 [SMILES: CN(C)C1CCN(c2cc(C(=O)Nc3ncc4ccc(-c5cn(C)nn5)cc4n3)ccn2)CC1]
1282
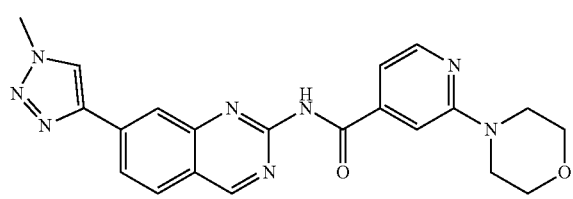 [SMILES: Cn1cc(-c2ccc3cnc(NC(=O)c4ccnc(N5CCOCC5)c4)nc3c2)nn1]
1283

TABLE 1-continued
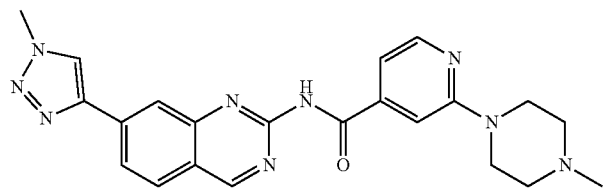 [SMILES: CN1CCN(c2cc(C(=O)Nc3ncc4ccc(-c5cn(C)nn5)cc4n3)ccn2)CC1] 1284
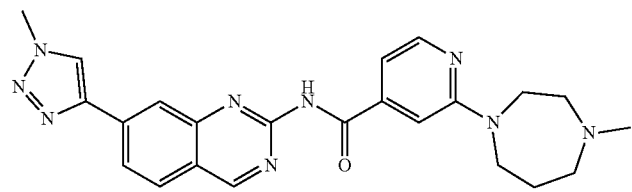 [SMILES: CN1CCCN(c2cc(C(=O)Nc3ncc4ccc(-c5cn(C)nn5)cc4n3)ccn2)CC1] 1285
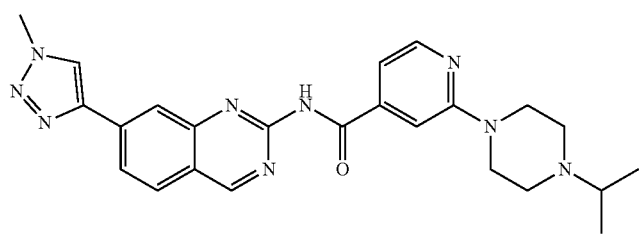 [SMILES: CC(C)N1CCN(c2cc(C(=O)Nc3ncc4ccc(-c5cn(C)nn5)cc4n3)ccn2)CC1] 1286
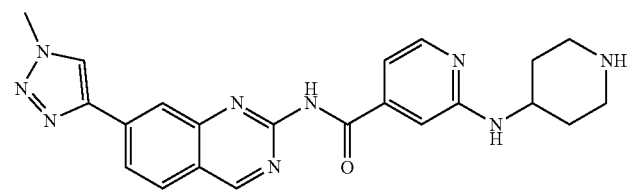 [SMILES: Cn1cc(-c2ccc3cnc(NC(=O)c4ccnc(NC5CCNCC5)c4)nc3c2)nn1] 1287
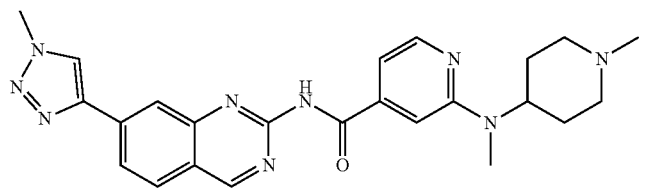 [SMILES: CN1CCC(N(C)c2cc(C(=O)Nc3ncc4ccc(-c5cn(C)nn5)cc4n3)ccn2)CC1] 1288
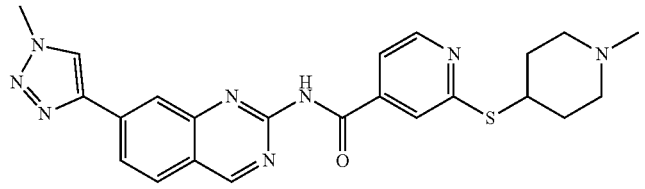 [SMILES: CN1CCC(Sc2cc(C(=O)Nc3ncc4ccc(-c5cn(C)nn5)cc4n3)ccn2)CC1] 1289
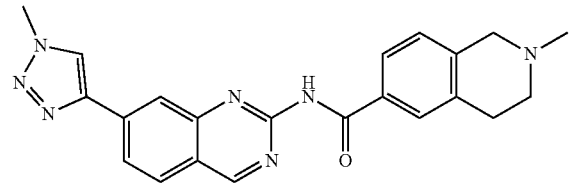 [SMILES: CN1CCc2cc(C(=O)Nc3ncc4ccc(-c5cn(C)nn5)cc4n3)ccc2C1] 1290
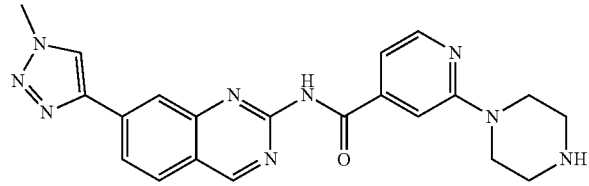 [SMILES: Cn1cc(-c2ccc3cnc(NC(=O)c4ccnc(N5CCNCC5)c4)nc3c2)nn1] 1291

TABLE 1-continued
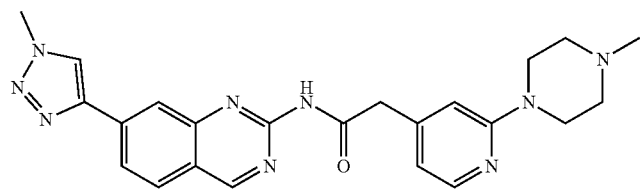 [SMILES: CN1CCN(c2cc(CC(=O)Nc3ncc4ccc(-c5cn(C)nn5)cc4n3)ccn2)CC1] 1292
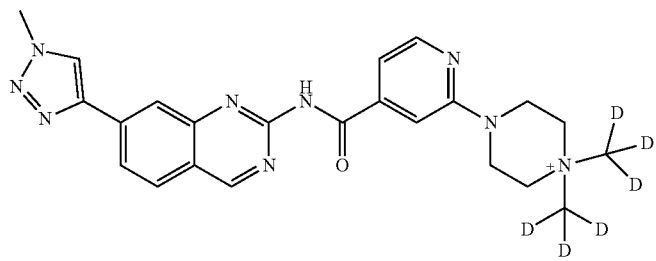 1293
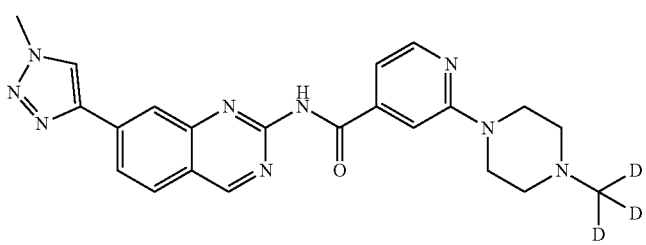 [SMILES: [2H]C([2H])([2H])N1CCN(c2cc(C(=O)Nc3ncc4ccc(-c5cn(C)nn5)cc4n3)ccn2)CC1] 1294
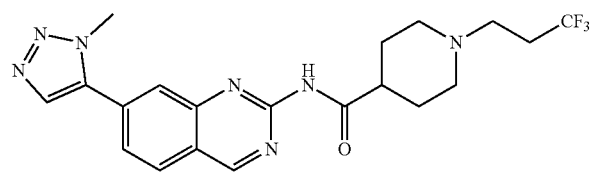 1295
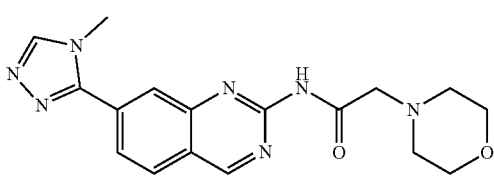 [SMILES: Cn1cnnc1-c1ccc2cnc(NC(=O)CN3CCOCC3)nc2c1] 1296
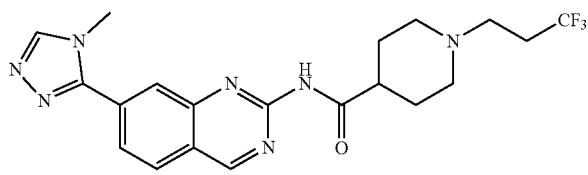 [SMILES: Cn1cnnc1-c1ccc2cnc(NC(=O)C3CCN(CCC(F)(F)F)CC3)nc2c1] 1297
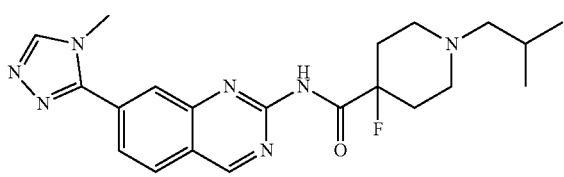 [SMILES: CC(C)CN1CCC(F)(C(=O)Nc2ncc3ccc(-c4nncn4C)cc3n2)CC1] 1298
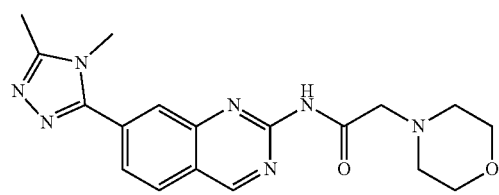 [SMILES: Cc1nnc(-c2ccc3cnc(NC(=O)CN4CCOCC4)nc3c2)n1C] 1299

TABLE 1-continued
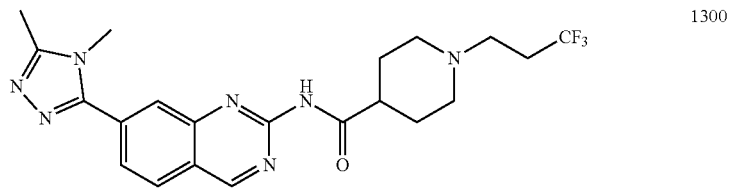 1300
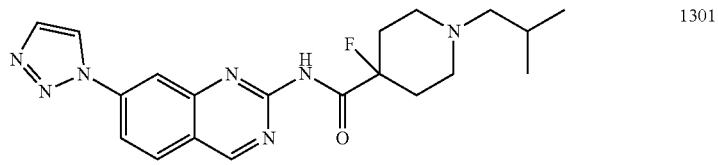 1301
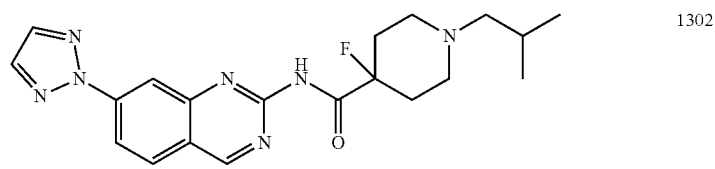 1302
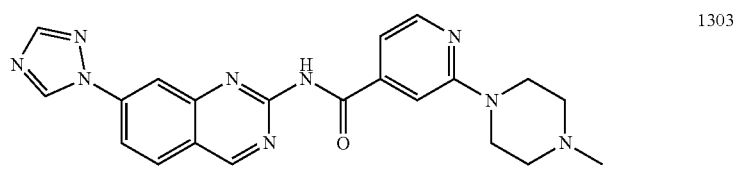 1303
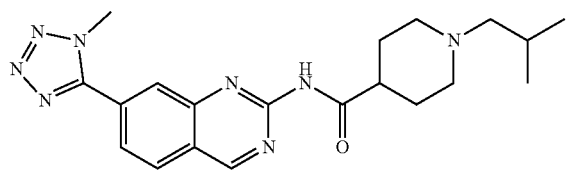 [SMILES: CC(C)CN1CCC(C(=O)Nc2ncc3ccc(-c4nnnn4C)cc3n2)CC1] 1304
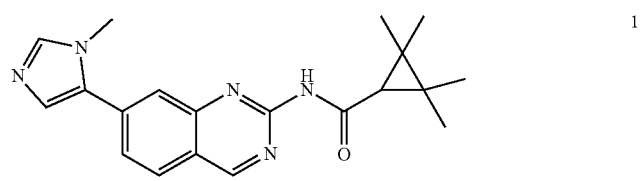 1305
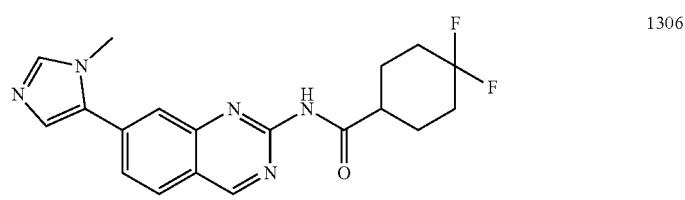 1306
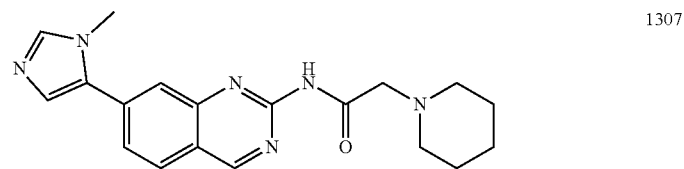 1307
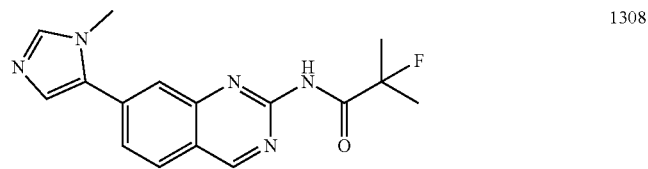 1308

TABLE 1-continued

| | |
|---|---|
| (structure) | 1309 |
| (structure) | 1310 |
| (structure) | 1311 |
| (structure) | 1312 |
| (structure) | 1313 |
| (structure) | 1314 |
| (structure) | 1315 |
| (structure) | 1316 |
| (structure) | 1317 |

TABLE 1-continued
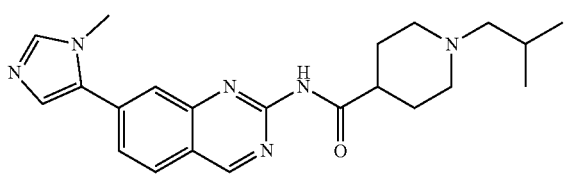 [SMILES: CC(C)CN1CCC(C(=O)Nc2ncc3ccc(-c4cncn4C)cc3n2)CC1] 1318
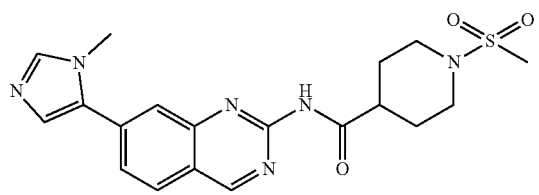 [SMILES: Cn1cncc1-c1ccc2cnc(NC(=O)C3CCN(S(C)(=O)=O)CC3)nc2c1] 1319
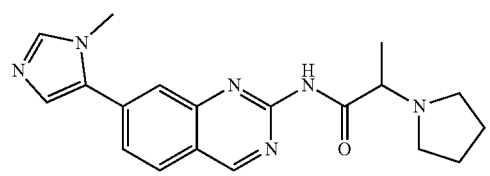 [SMILES: CC(C(=O)Nc1ncc2ccc(-c3cncn3C)cc2n1)N1CCCC1] 1320
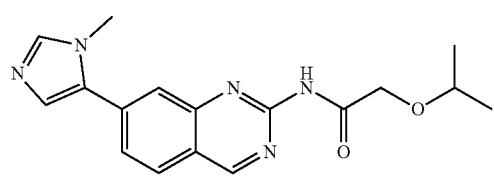 [SMILES: CC(C)OCC(=O)Nc1ncc2ccc(-c3cncn3C)cc2n1] 1321
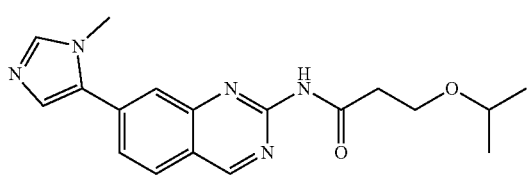 [SMILES: CC(C)OCCC(=O)Nc1ncc2ccc(-c3cncn3C)cc2n1] 1322
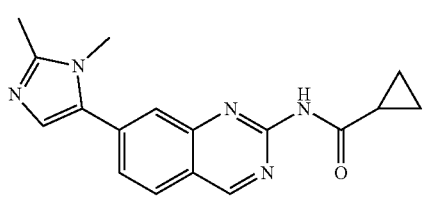 [SMILES: Cc1ncc(-c2ccc3cnc(NC(=O)C4CC4)nc3c2)n1C] 1323
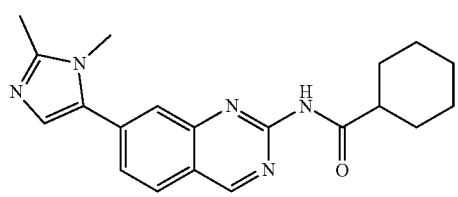 [SMILES: Cc1ncc(-c2ccc3cnc(NC(=O)C4CCCCC4)nc3c2)n1C] 1324
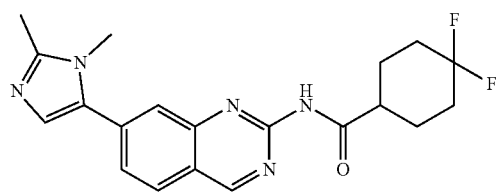 [SMILES: Cc1ncc(-c2ccc3cnc(NC(=O)C4CCC(F)(F)CC4)nc3c2)n1C] 1325

TABLE 1-continued
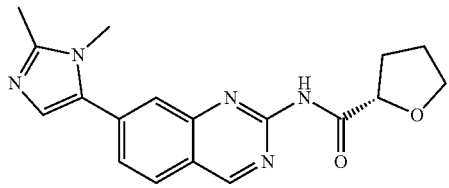 [SMILES: Cc1ncc(-c2ccc3cnc(NC(=O)[C@@H]4CCCO4)nc3c2)n1C] 1326
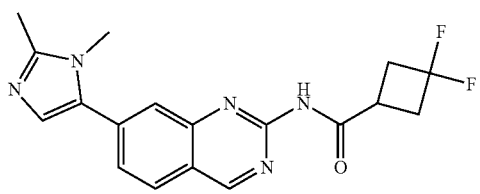 [SMILES: Cc1ncc(-c2ccc3cnc(NC(=O)C4CC(F)(F)C4)nc3c2)n1C] 1327
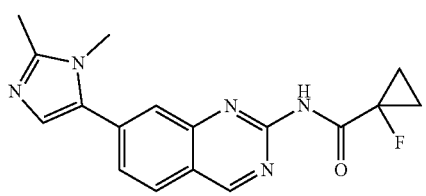 [SMILES: Cc1ncc(-c2ccc3cnc(NC(=O)C4(F)CC4)nc3c2)n1C] 1328
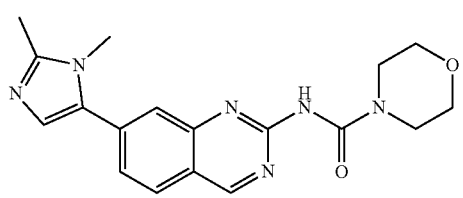 [SMILES: Cc1ncc(-c2ccc3cnc(NC(=O)N4CCOCC4)nc3c2)n1C] 1329
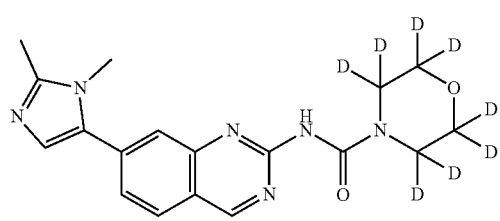 [SMILES: [2H]C1([2H])OC([2H])([2H])C([2H])([2H])N(C(=O)Nc2ncc3ccc(-c4cnc(C)n4C)cc3n2)C1([2H])[2H]] 1330
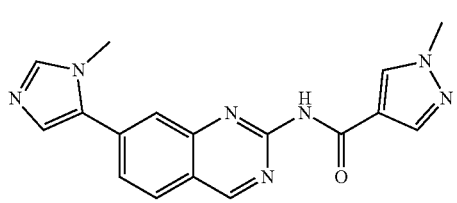 [SMILES: Cn1cc(C(=O)Nc2ncc3ccc(-c4cncn4C)cc3n2)cn1] 1331
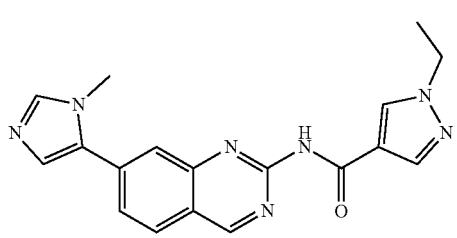 [SMILES: CCn1cc(C(=O)Nc2ncc3ccc(-c4cncn4C)cc3n2)cn1] 1332

TABLE 1-continued
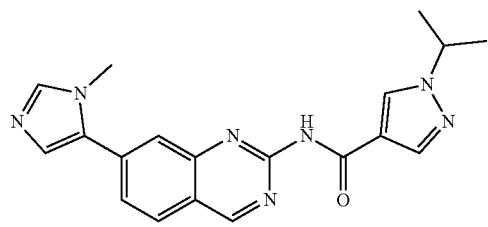 [SMILES: CC(C)n1cc(C(=O)Nc2ncc3ccc(-c4cncn4C)cc3n2)cn1] 1333
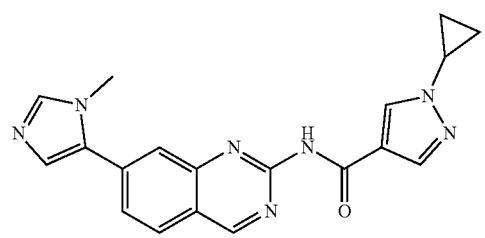 1334
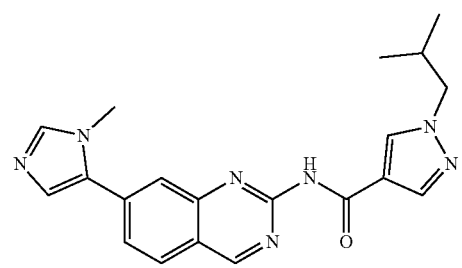 [SMILES: CC(C)Cn1cc(C(=O)Nc2ncc3ccc(-c4cncn4C)cc3n2)cn1] 1335
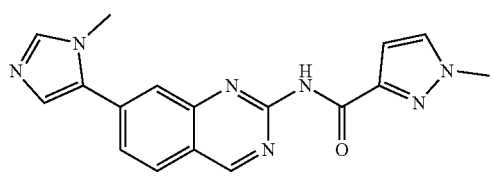 [SMILES: Cn1ccc(C(=O)Nc2ncc3ccc(-c4cncn4C)cc3n2)n1] 1336
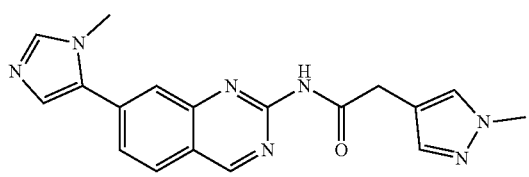 [SMILES: Cn1cc(CC(=O)Nc2ncc3ccc(-c4cncn4C)cc3n2)cn1] 1337
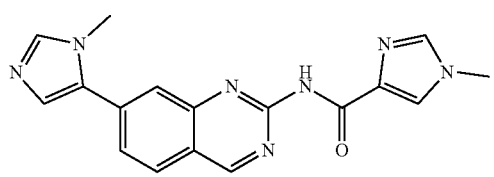 [SMILES: Cn1cnc(C(=O)Nc2ncc3ccc(-c4cncn4C)cc3n2)c1] 1338
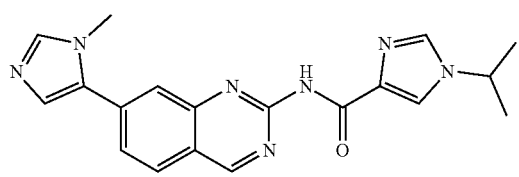 [SMILES: CC(C)n1cnc(C(=O)Nc2ncc3ccc(-c4cncn4C)cc3n2)c1] 1339
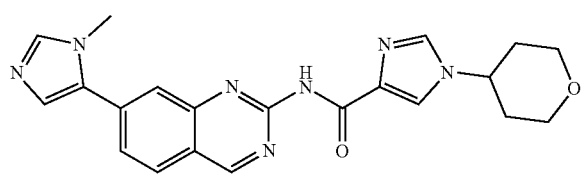 [SMILES: Cn1cncc1-c1ccc2cnc(NC(=O)c3cn(C4CCOCC4)cn3)nc2c1] 1340

TABLE 1-continued
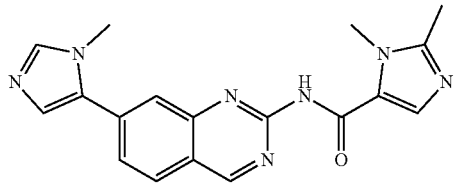 [SMILES: Cc1ncc(C(=O)Nc2ncc3ccc(-c4cncn4C)cc3n2)n1C] 1341
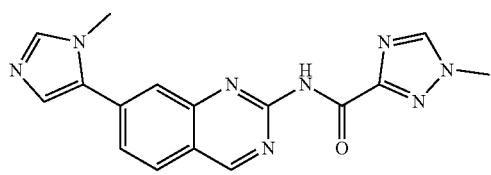 [SMILES: Cn1cnc(C(=O)Nc2ncc3ccc(-c4cncn4C)cc3n2)n1] 1342
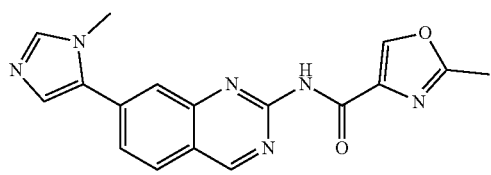 1343
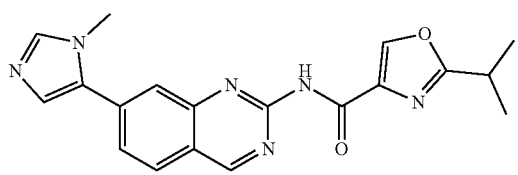 [SMILES: CC(C)c1nc(C(=O)Nc2ncc3ccc(-c4cncn4C)cc3n2)co1] 1344
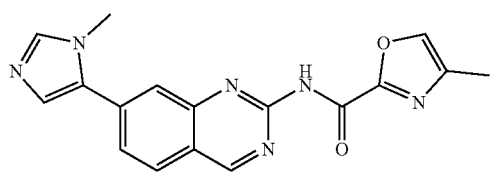 1345
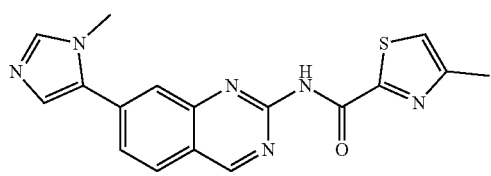 [SMILES: Cc1coc(C(=O)Nc2ncc3ccc(-c4cncn4C)cc3n2)n1] 1346
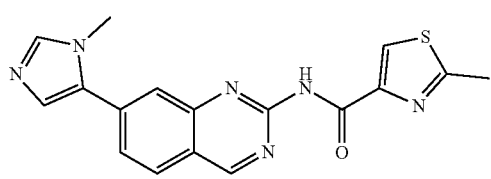 1347
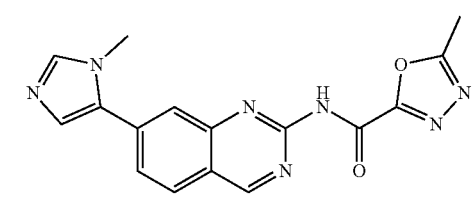 [SMILES: Cc1nnc(C(=O)Nc2ncc3ccc(-c4cncn4C)cc3n2)o1] 1348

TABLE 1-continued
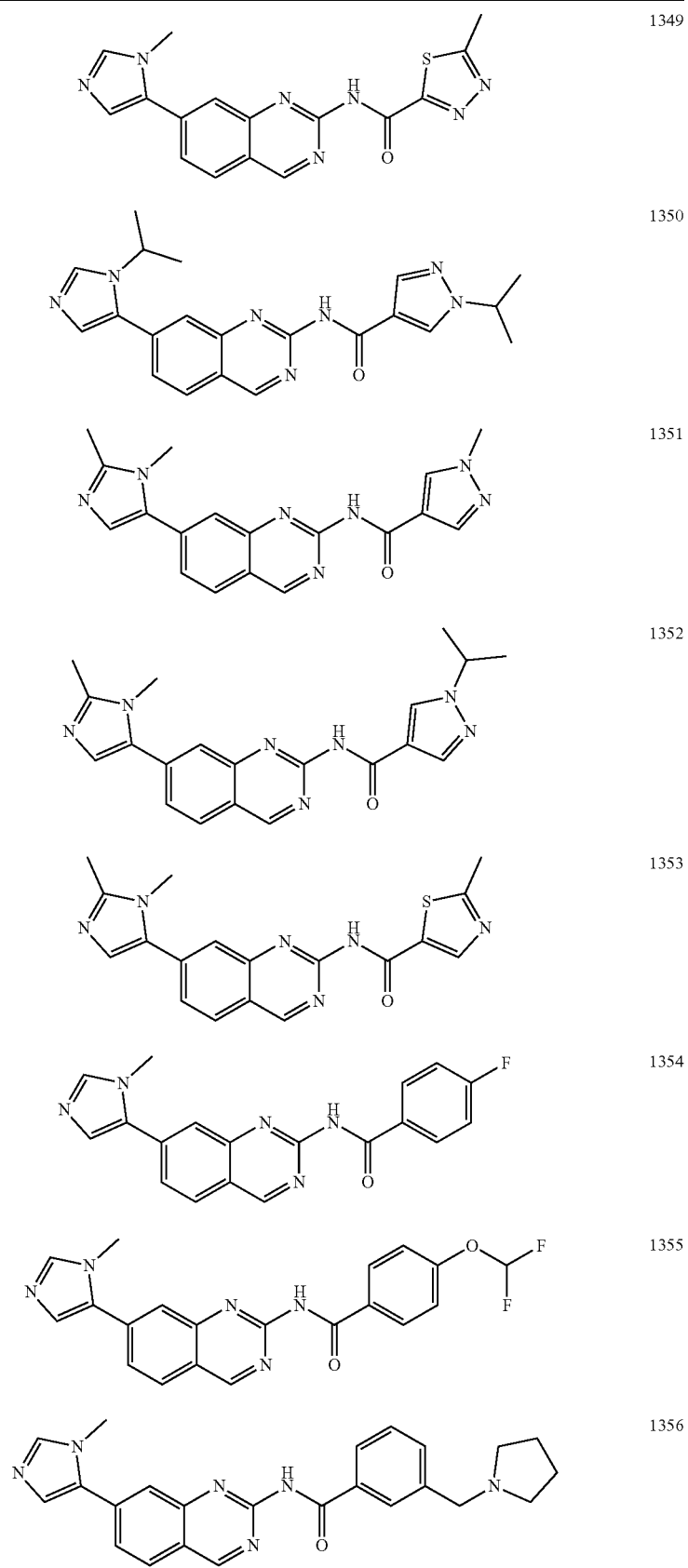

TABLE 1-continued
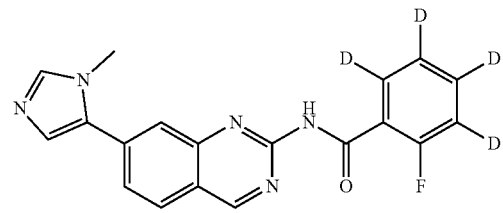
1357
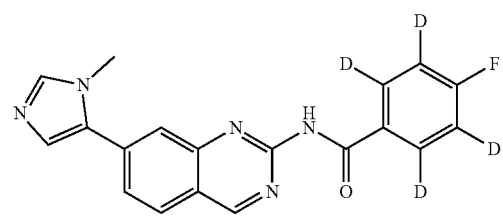
1358
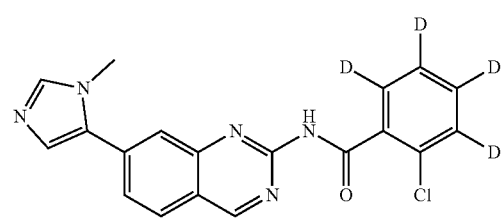 [SMILES: [2H]c1c([2H])c([2H])c(C(=O)Nc2ncc3ccc(-c4cncn4C)cc3n2)c(F)c1[2H]]
1359
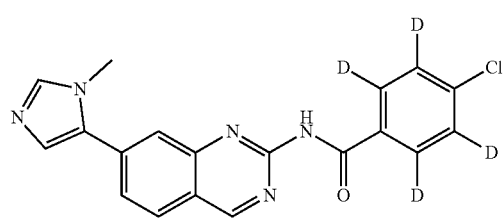 [SMILES: [2H]c1c([2H])c(C(=O)Nc2ncc3ccc(-c4cncn4C)cc3n2)c([2H])c([2H])c1Cl]
1360
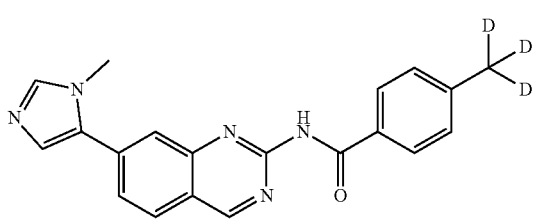 [SMILES: [2H]C([2H])([2H])c1ccc(C(=O)Nc2ncc3ccc(-c4cncn4C)cc3n2)cc1]
1361
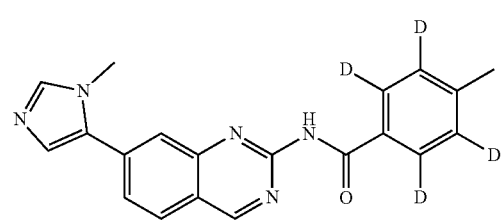
1362
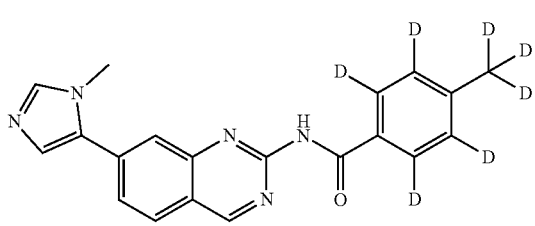 [SMILES: [2H]c1c([2H])c(C([2H])([2H])[2H])c([2H])c([2H])c1C(=O)Nc1ncc2ccc(-c3cncn3C)cc2n1]
1363

TABLE 1-continued
| | |
|---|---|
| 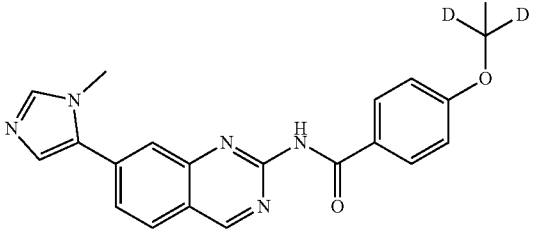 | 1364 |
| 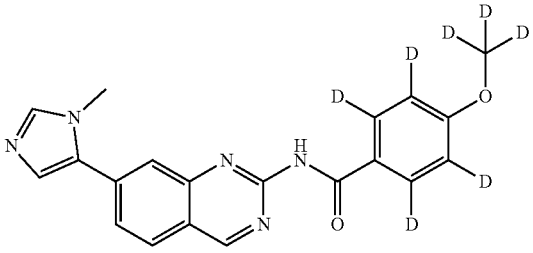 [SMILES: [2H]c1c([2H])c(C(=O)Nc2ncc3ccc(-c4cncn4C)cc3n2)c([2H])c([2H])c1OC([2H])([2H])[2H]] | 1365 |
| 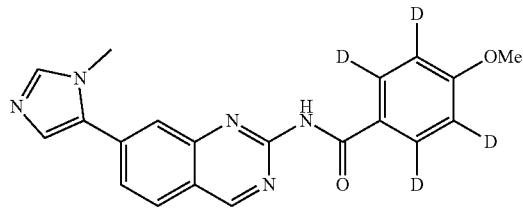 [SMILES: [2H]c1c([2H])c(C(=O)Nc2ncc3ccc(-c4cncn4C)cc3n2)c([2H])c([2H])c1OC] | 1366 |
| 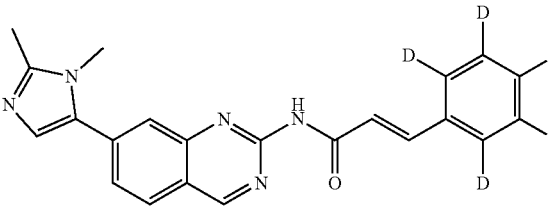 | 1367 |
| 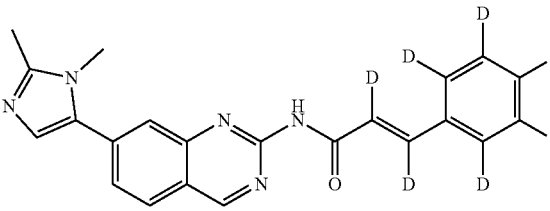 | 1368 |
| 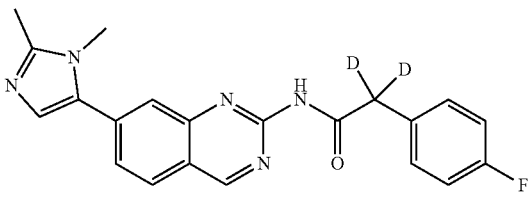 [SMILES: [2H]C([2H])(C(=O)Nc1ncc2ccc(-c3cnc(C)n3C)cc2n1)c1ccc(F)cc1] | 1369 |
| 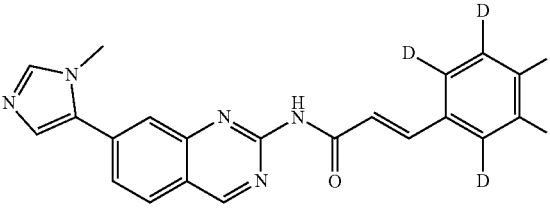 | 1370 |

TABLE 1-continued
| | |
|---|---|
| 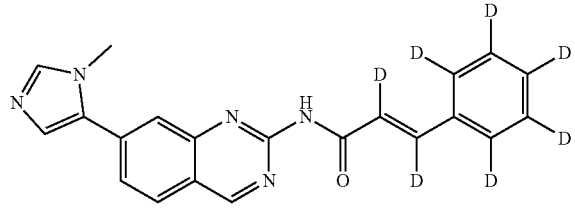 | 1371 |
| 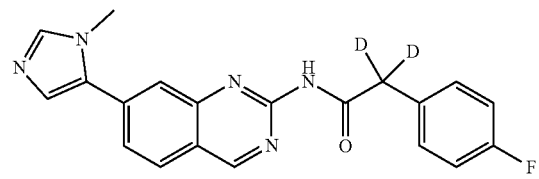 [SMILES: [2H]C([2H])(C(=O)Nc1ncc2ccc(-c3cncn3C)cc2n1)c1ccc(F)cc1] | 1372 |
| | 1373 |
| | 1374 |
| | 1375 |
| | 1376 |
| 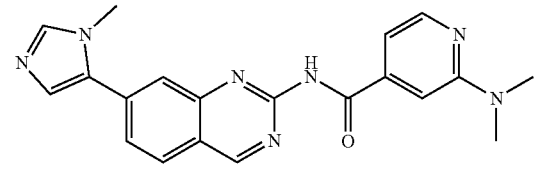 [SMILES: CN(C)c1cc(C(=O)Nc2ncc3ccc(-c4cncn4C)cc3n2)ccn1] | 1377 |
| 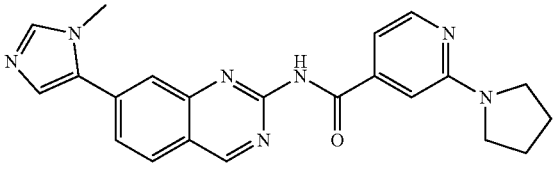 [SMILES: Cn1cncc1-c1ccc2cnc(NC(=O)c3ccnc(N4CCCC4)c3)nc2c1] | 1378 |

TABLE 1-continued
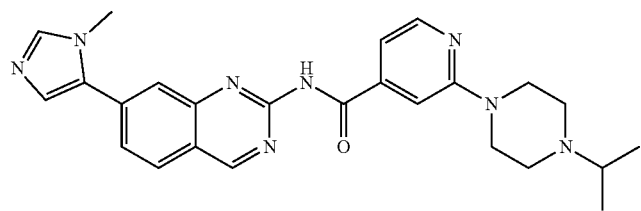 [SMILES: CC(C)N1CCN(c2cc(C(=O)Nc3ncc4ccc(-c5cncn5C)cc4n3)ccn2)CC1]
1379
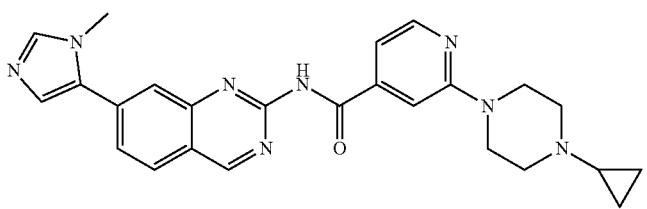 [SMILES: Cn1cncc1-c1ccc2cnc(NC(=O)c3ccnc(N4CCN(C5CC5)CC4)c3)nc2c1]
1380
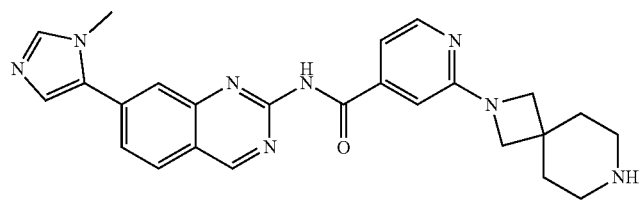 [SMILES: Cn1cncc1-c1ccc2cnc(NC(=O)c3ccnc(N4CC5(CCNCC5)C4)c3)nc2c1]
1381
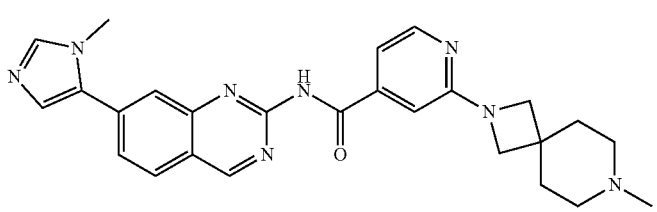
1382
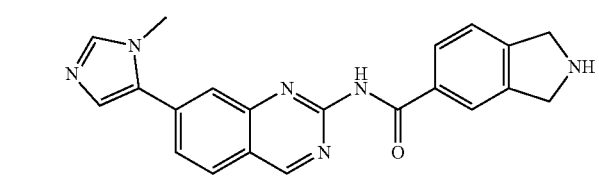
1383
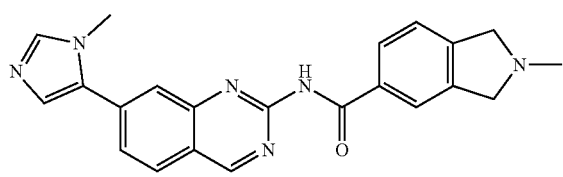
1384
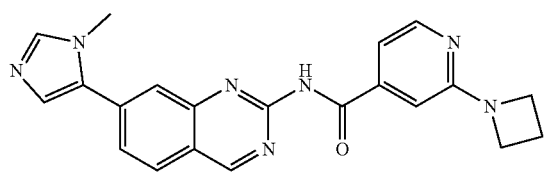 [SMILES: Cn1cncc1-c1ccc2cnc(NC(=O)c3ccnc(N4CCC4)c3)nc2c1]
1385
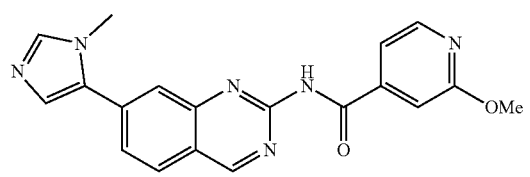 [SMILES: COc1cc(C(=O)Nc2ncc3ccc(-c4cncn4C)cc3n2)ccn1]
1386

TABLE 1-continued
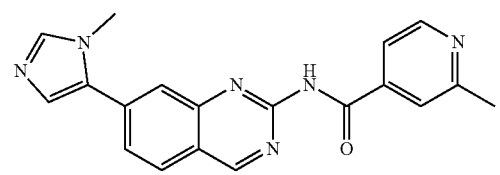 [SMILES: Cc1cc(C(=O)Nc2ncc3ccc(-c4cncn4C)cc3n2)ccn1]
1387
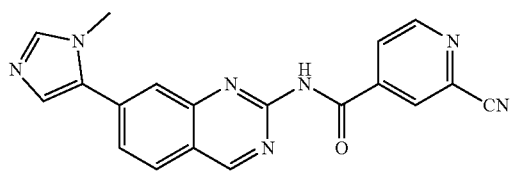 [SMILES: Cn1cncc1-c1ccc2cnc(NC(=O)c3ccnc(C#N)c3)nc2c1]
1388
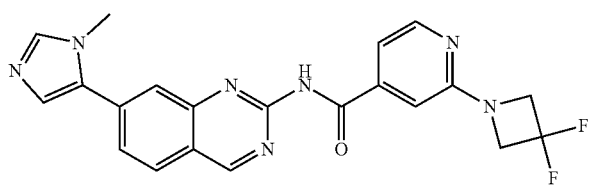 [SMILES: Cn1cncc1-c1ccc2cnc(NC(=O)c3ccnc(N4CC(F)(F)C4)c3)nc2c1]
1389
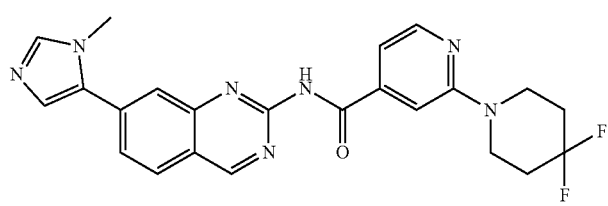 [SMILES: Cn1cncc1-c1ccc2cnc(NC(=O)c3ccnc(N4CCC(F)(F)CC4)c3)nc2c1]
1390
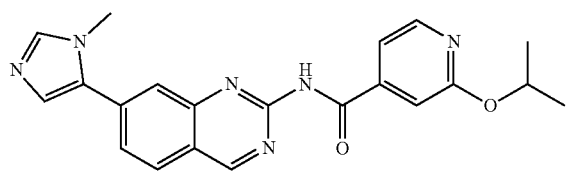 [SMILES: CC(C)Oc1cc(C(=O)Nc2ncc3ccc(-c4cncn4C)cc3n2)ccn1]
1391
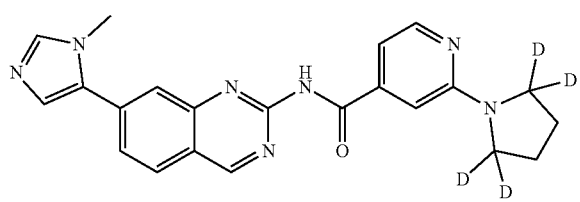 [SMILES: [2H]C1([2H])CCC([2H])([2H])N1c1cc(C(=O)Nc2ncc3ccc(-c4cncn4C)cc3n2)ccn1]
1392
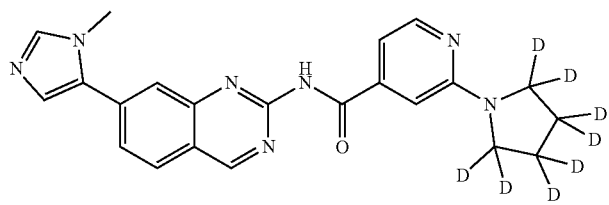 [SMILES: [2H]C1([2H])N(c2cc(C(=O)Nc3ncc4ccc(-c5cncn5C)cc4n3)ccn2)C([2H])([2H])C([2H])([2H])C1([2H])[2H]]
1393
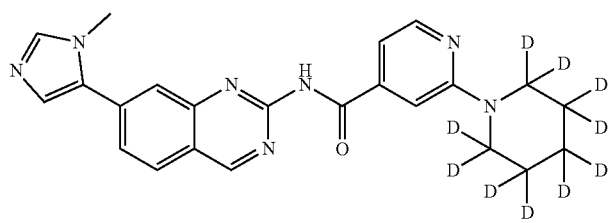 [SMILES: [2H]C1([2H])N(c2cc(C(=O)Nc3ncc4ccc(-c5cncn5C)cc4n3)ccn2)C([2H])([2H])C([2H])([2H])C([2H])([2H])C1([2H])[2H]]
1394

TABLE 1-continued
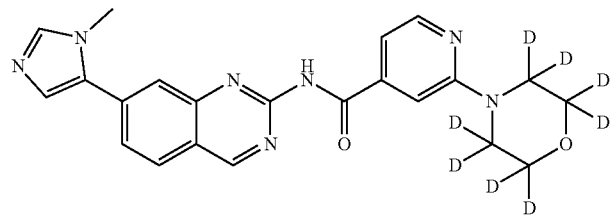 [SMILES: [2H]C1([2H])OC([2H])([2H])C([2H])([2H])N(c2cc(C(=O)Nc3ncc4ccc(-c5cncn5C)cc4n3)ccn2)C1([2H])[2H]] 1395
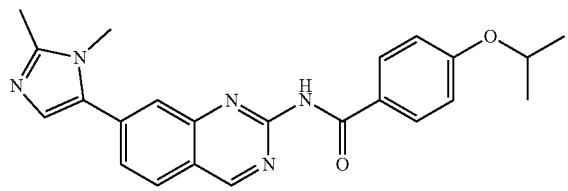 [SMILES: Cc1ncc(-c2ccc3cnc(NC(=O)c4ccc(OC(C)C)cc4)nc3c2)n1C] 1396
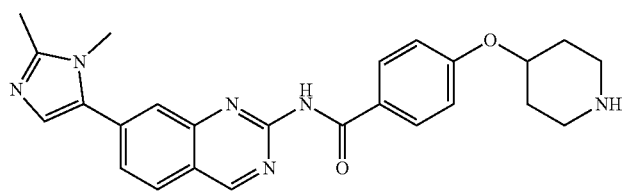 [SMILES: Cc1ncc(-c2ccc3cnc(NC(=O)c4ccc(OC5CCNCC5)cc4)nc3c2)n1C] 1397
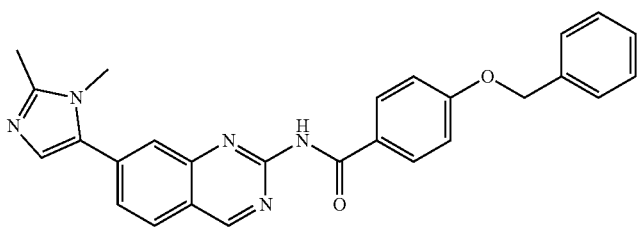 [SMILES: Cc1ncc(-c2ccc3cnc(NC(=O)c4ccc(OCc5ccccc5)cc4)nc3c2)n1C] 1398
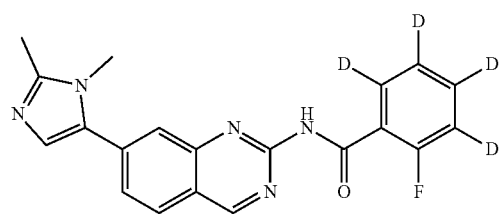 [SMILES: [2H]c1c([2H])c([2H])c(C(=O)Nc2ncc3ccc(-c4cnc(C)n4C)cc3n2)c(F)c1[2H]] 1399
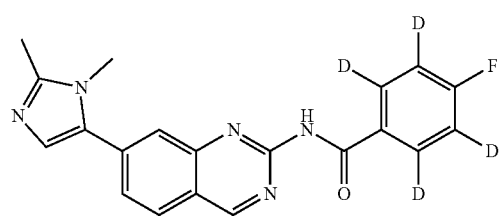 [SMILES: [2H]c1c([2H])c(C(=O)Nc2ncc3ccc(-c4cnc(C)n4C)cc3n2)c([2H])c([2H])c1F] 1400
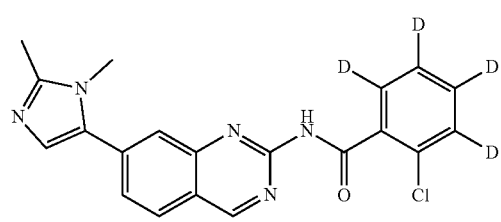 1401

TABLE 1-continued

| | |
|---|---|
| (structure) | 1402 |
| (structure) | 1403 |
| (structure) | 1404 |
| (structure) | 1405 |
| (structure) | 1406 |
| (structure) | 1407 |
| (structure) | 1408 |

TABLE 1-continued
| | |
|---|---|
| 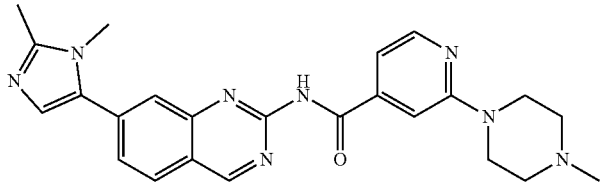 [SMILES: Cc1ncc(-c2ccc3cnc(NC(=O)c4ccnc(N5CCN(C)CC5)c4)nc3c2)n1C] | 1409 |
| | 1410 |
| | 1411 |
| | 1412 |
| | 1413 |
| | 1414 |
| | 1415 |

TABLE 1-continued
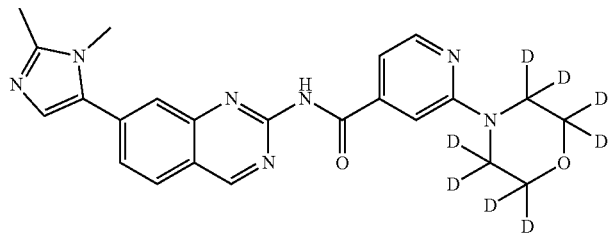 [SMILES: [2H]C1([2H])OC([2H])([2H])C([2H])([2H])N(c2cc(C(=O)Nc3ncc4ccc(-c5cnc(C)n5C)cc4n3)ccn2)C1([2H])[2H]]
1416
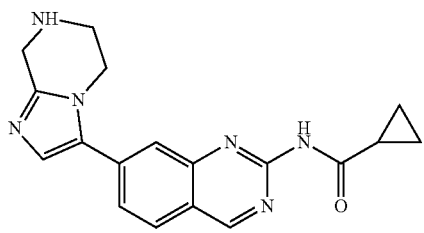 [SMILES: O=C(Nc1ncc2ccc(-c3cnc4n3CCNC4)cc2n1)C1CC1]
1417
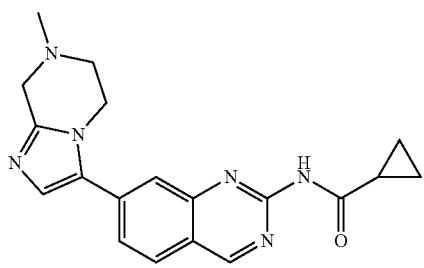 [SMILES: CN1CCn2c(-c3ccc4cnc(NC(=O)C5CC5)nc4c3)cnc2C1]
1418
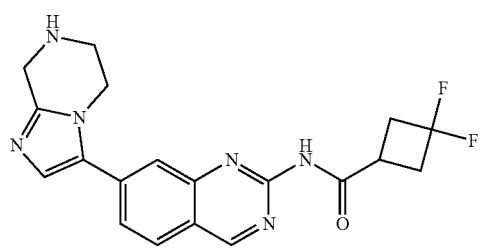 [SMILES: O=C(Nc1ncc2ccc(-c3cnc4n3CCNC4)cc2n1)C1CC(F)(F)C1]
1419
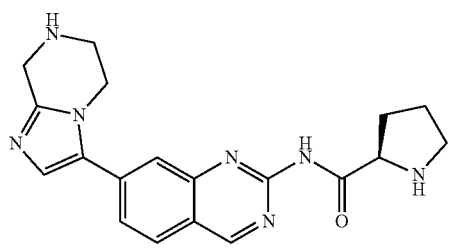 [SMILES: O=C(Nc1ncc2ccc(-c3cnc4n3CCNC4)cc2n1)[C@H]1CCCN1]
1420
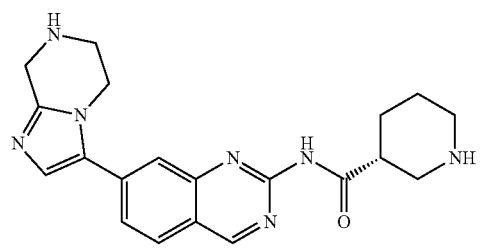 [SMILES: O=C(Nc1ncc2ccc(-c3cnc4n3CCNC4)cc2n1)[C@@H]1CCCNC1]
1421

TABLE 1-continued
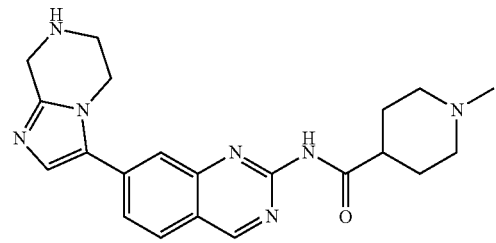 [SMILES: CN1CCC(C(=O)Nc2ncc3ccc(-c4cnc5n4CCNC5)cc3n2)CC1]
1422
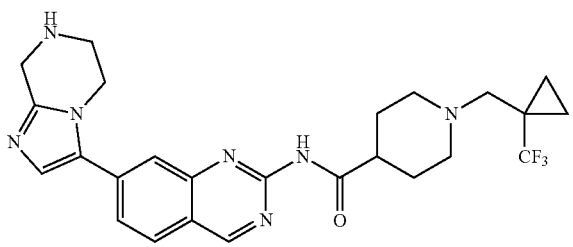 [SMILES: O=C(Nc1ncc2ccc(-c3cnc4n3CCNC4)cc2n1)C1CCN(CC2(C(F)(F)F)CC2)CC1]
1423
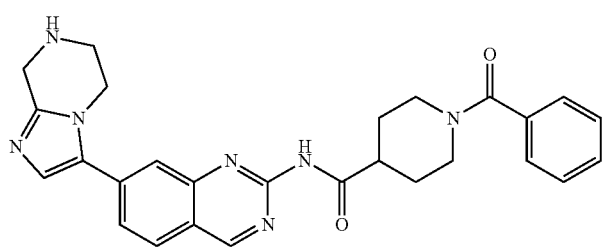 [SMILES: O=C(Nc1ncc2ccc(-c3cnc4n3CCNC4)cc2n1)C1CCN(C(=O)c2ccccc2)CC1]
1424
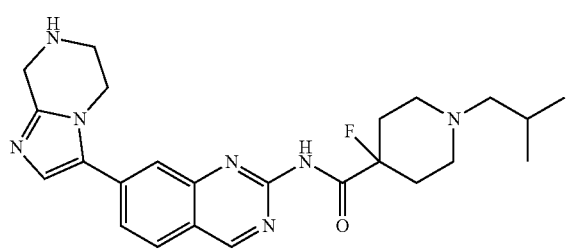 [SMILES: CC(C)CN1CCC(F)(C(=O)Nc2ncc3ccc(-c4cnc5n4CCNC5)cc3n2)CC1]
1425
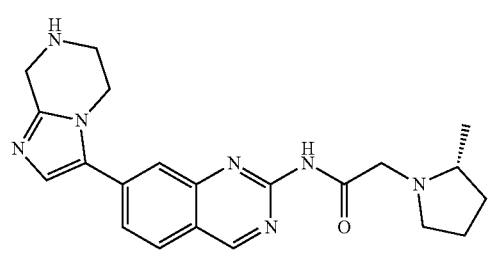 [SMILES: C[C@@H]1CCCN1CC(=O)Nc1ncc2ccc(-c3cnc4n3CCNC4)cc2n1]
1426
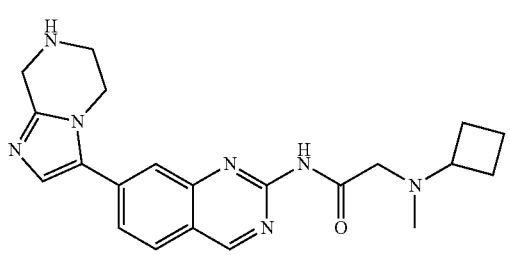 [SMILES: CN(CC(=O)Nc1ncc2ccc(-c3cnc4n3CCNC4)cc2n1)C1CCC1]
1427

TABLE 1-continued
| | |
|---|---|
| 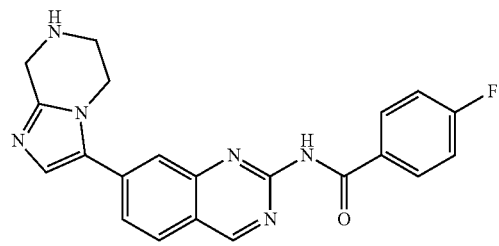 [SMILES: O=C(Nc1ncc2ccc(-c3cnc4n3CCNC4)cc2n1)c1ccc(F)cc1] | 1428 |
| 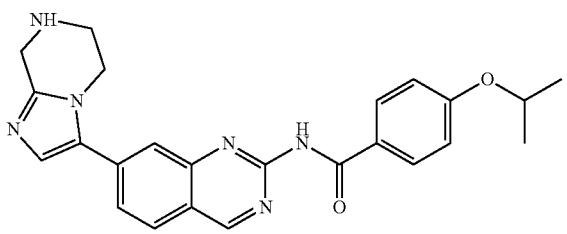 [SMILES: CC(C)Oc1ccc(C(=O)Nc2ncc3ccc(-c4cnc5n4CCNC5)cc3n2)cc1] | 1429 |
| 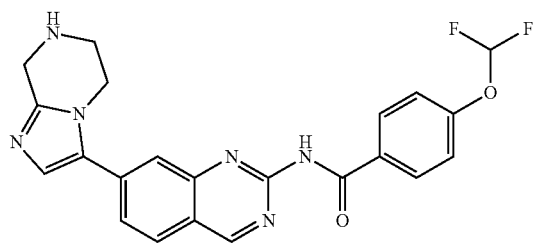 [SMILES: O=C(Nc1ncc2ccc(-c3cnc4n3CCNC4)cc2n1)c1ccc(OC(F)F)cc1] | 1430 |
| 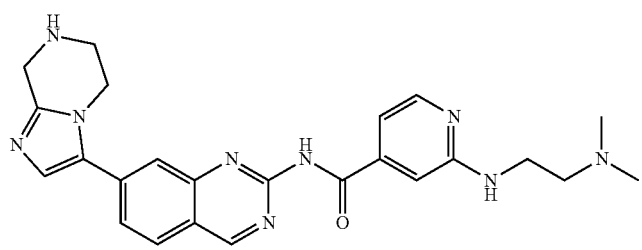 [SMILES: CN(C)CCNc1cc(C(=O)Nc2ncc3ccc(-c4cnc5n4CCNC5)cc3n2)ccn1] | 1431 |
| 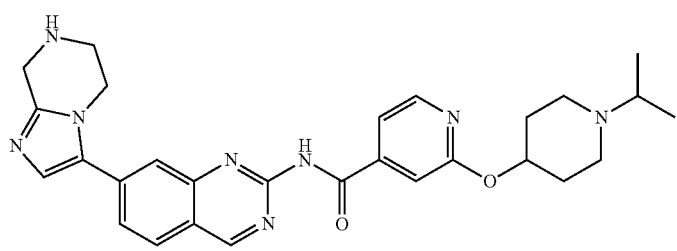 [SMILES: CC(C)N1CCC(Oc2cc(C(=O)Nc3ncc4ccc(-c5cnc6n5CCNC6)cc4n3)ccn2)CC1] | 1432 |
| 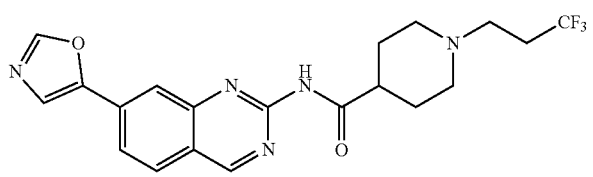 [SMILES: O=C(Nc1ncc2ccc(-c3cnco3)cc2n1)C1CCN(CCC(F)(F)F)CC1] | 1433 |
| 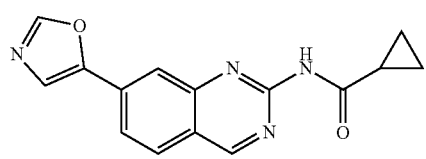 [SMILES: O=C(Nc1ncc2ccc(-c3cnco3)cc2n1)C1CC1] | 1434 |

TABLE 1-continued
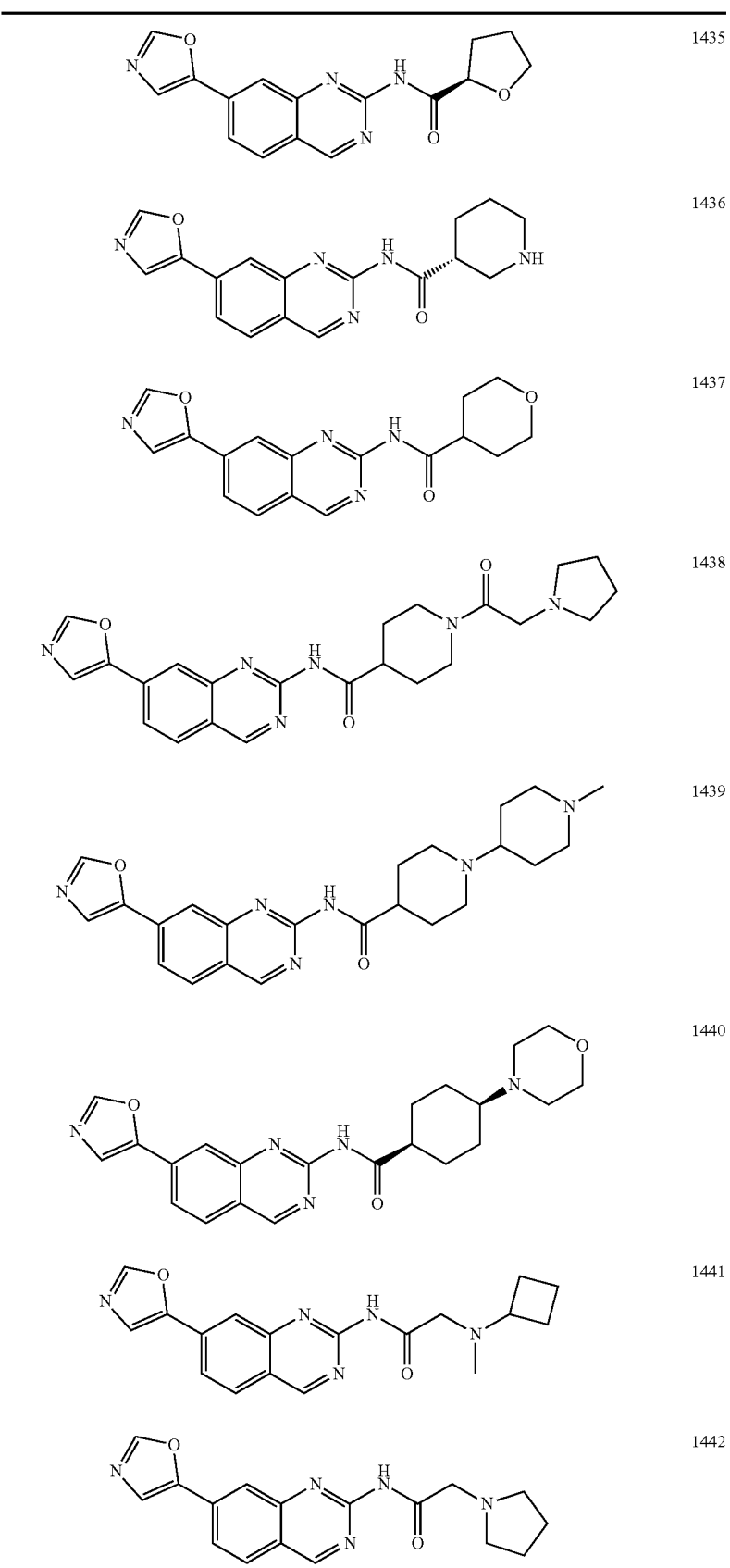

TABLE 1-continued
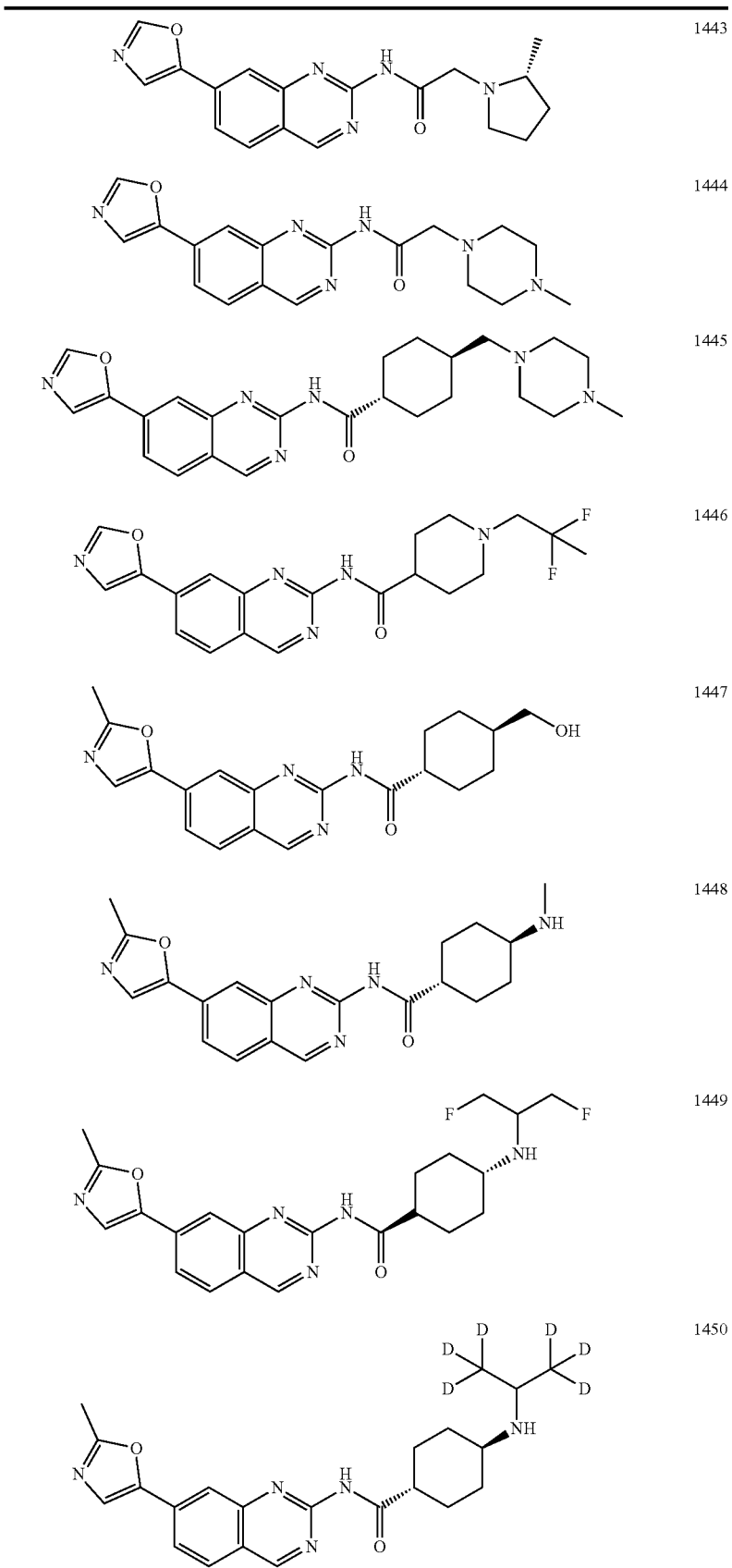

TABLE 1-continued
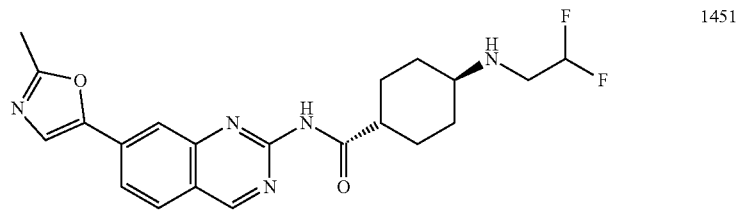 1451
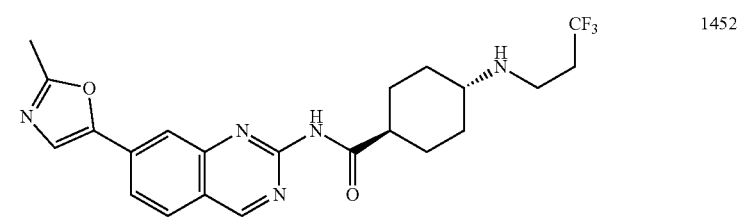 1452
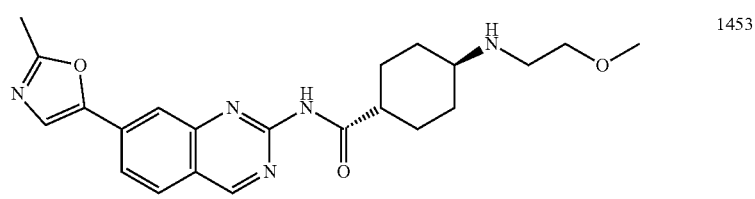 1453
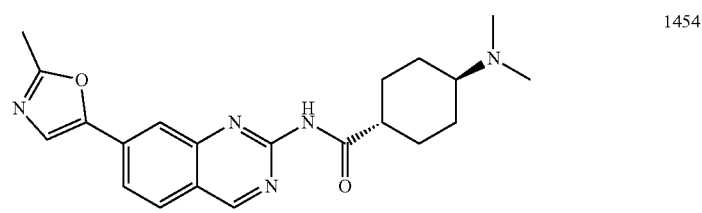 1454
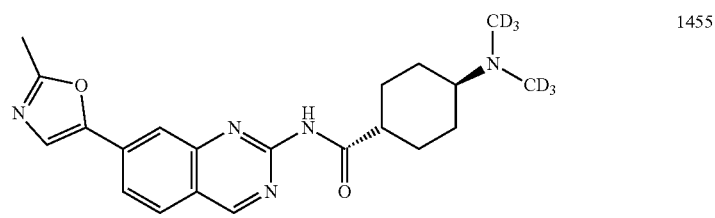 1455
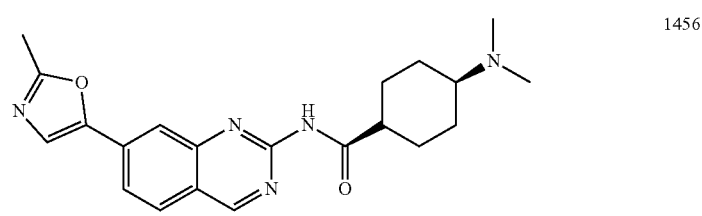 1456
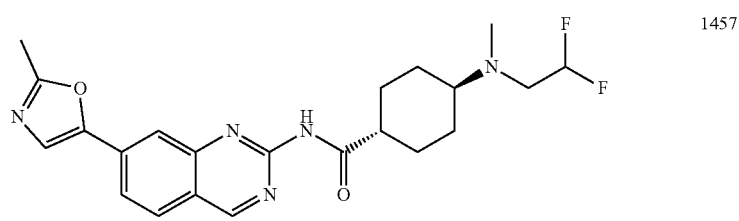 1457

TABLE 1-continued

| | |
|---|---|
| (structure) | 1458 |
| (structure) | 1459 |
| (structure) | 1460 |
| (structure) | 1461 |
| (structure) | 1462 |
| (structure) | 1463 |
| (structure) | 1464 |

TABLE 1-continued
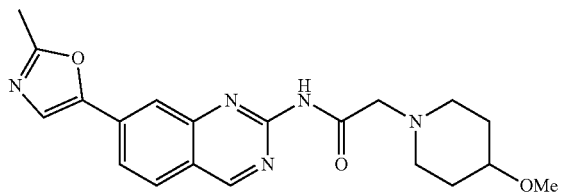 [SMILES: COC1CCN(CC(=O)Nc2ncc3ccc(-c4cnc(C)o4)cc3n2)CC1]
1465
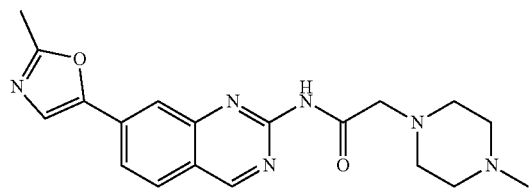 [SMILES: Cc1ncc(-c2ccc3cnc(NC(=O)CN4CCN(C)CC4)nc3c2)o1]
1466
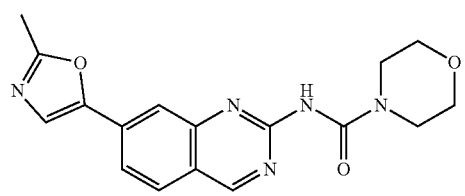 [SMILES: Cc1ncc(-c2ccc3cnc(NC(=O)N4CCOCC4)nc3c2)o1]
1467
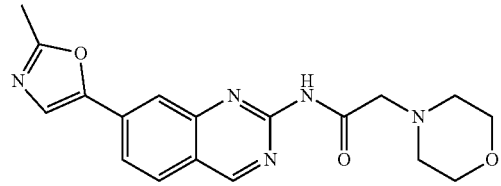 [SMILES: Cc1ncc(-c2ccc3cnc(NC(=O)CN4CCOCC4)nc3c2)o1]
1468
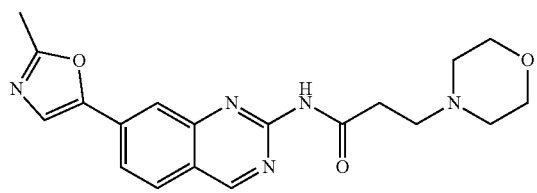 [SMILES: Cc1ncc(-c2ccc3cnc(NC(=O)CCN4CCOCC4)nc3c2)o1]
1469
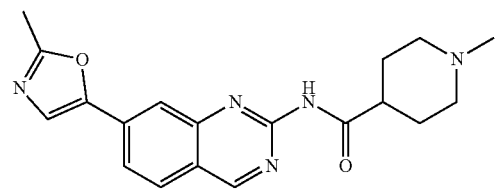
1470
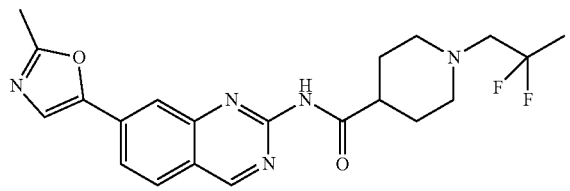 [SMILES: Cc1ncc(-c2ccc3cnc(NC(=O)C4CCN(CC(C)(F)F)CC4)nc3c2)o1]
1471
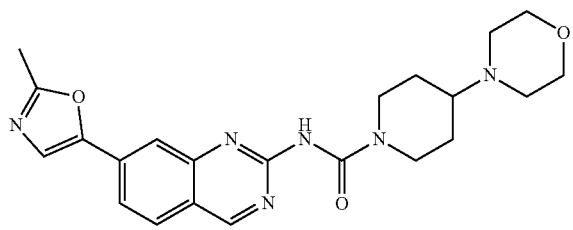 [SMILES: Cc1ncc(-c2ccc3cnc(NC(=O)N4CCC(N5CCOCC5)CC4)nc3c2)o1]
1472

TABLE 1-continued
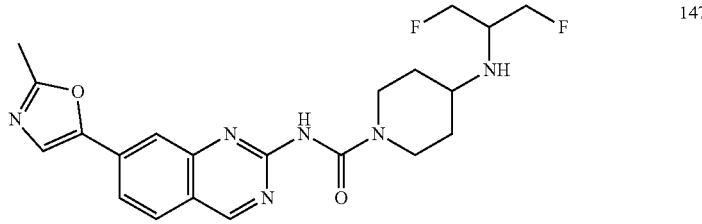
1473
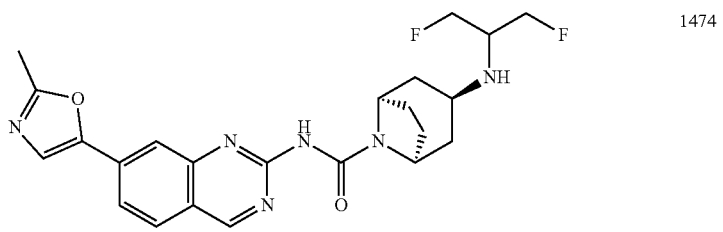
1474
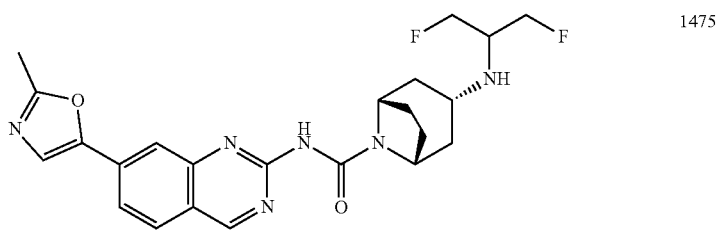
1475
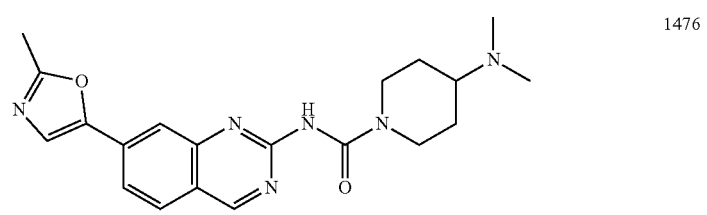
1476
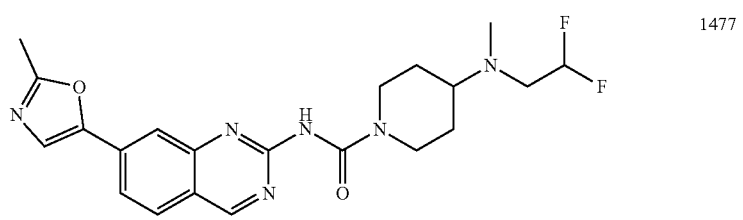
1477
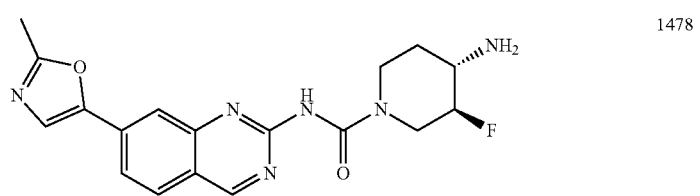
1478
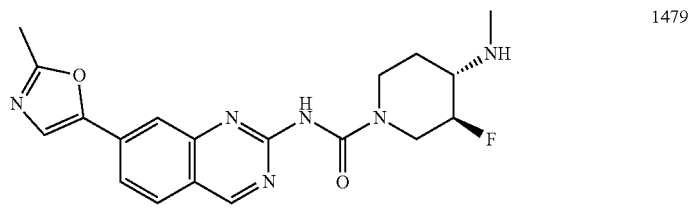
1479

TABLE 1-continued
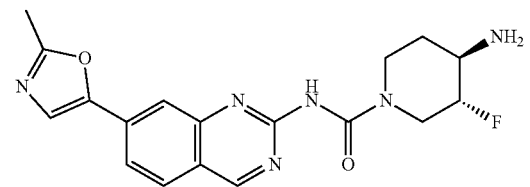 [SMILES: Cc1ncc(-c2ccc3cnc(NC(=O)N4CC[C@@H](N)[C@H](F)C4)nc3c2)o1]
1480
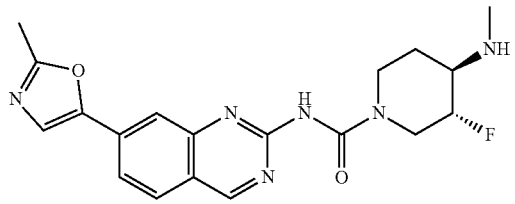 [SMILES: CN[C@@H]1CCN(C(=O)Nc2ncc3ccc(-c4cnc(C)o4)cc3n2)C[C@H]1F]
1481
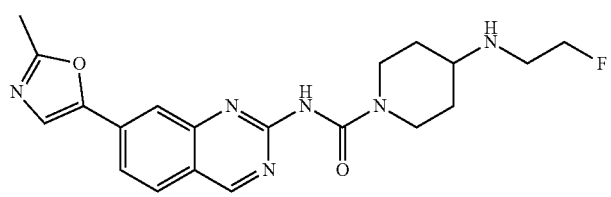 [SMILES: Cc1ncc(-c2ccc3cnc(NC(=O)N4CCC(NCCF)CC4)nc3c2)o1]
1482
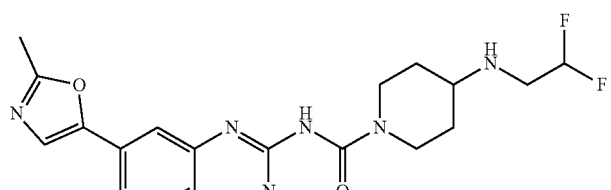
1483
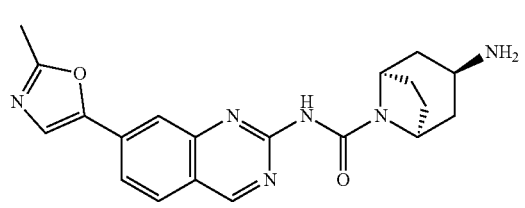 [SMILES: Cc1ncc(-c2ccc3cnc(NC(=O)N4[C@@H]5CC[C@H]4C[C@H](N)C5)nc3c2)o1]
1484
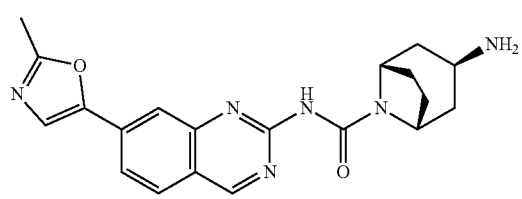 [SMILES: Cc1ncc(-c2ccc3cnc(NC(=O)N4[C@@H]5CC[C@H]4C[C@@H](N)C5)nc3c2)o1]
1485
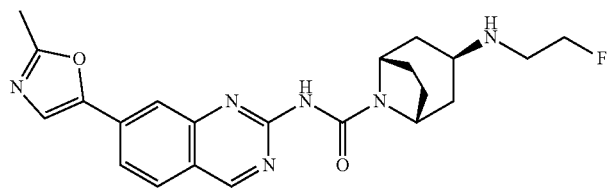 [SMILES: Cc1ncc(-c2ccc3cnc(NC(=O)N4[C@@H]5CC[C@H]4C[C@@H](NCCF)C5)nc3c2)o1]
1486
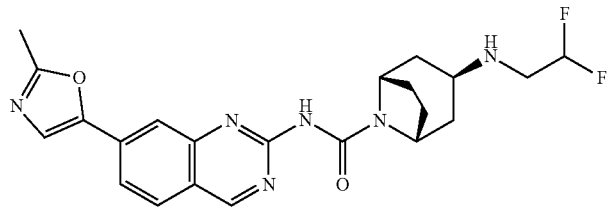 [SMILES: Cc1ncc(-c2ccc3cnc(NC(=O)N4[C@@H]5CC[C@H]4C[C@@H](NCC(F)F)C5)nc3c2)o1]
1487

TABLE 1-continued
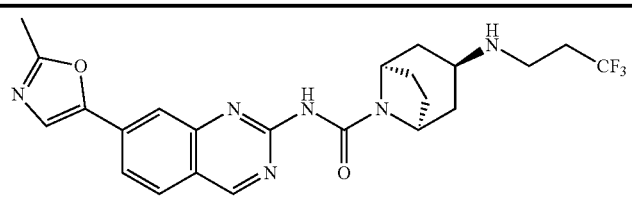 1488
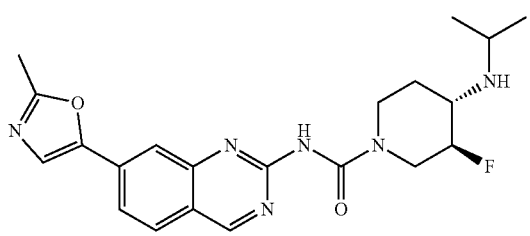 [SMILES: Cc1ncc(-c2ccc3cnc(NC(=O)N4CC[C@H](NC(C)C)[C@@H](F)C4)nc3c2)o1] 1489
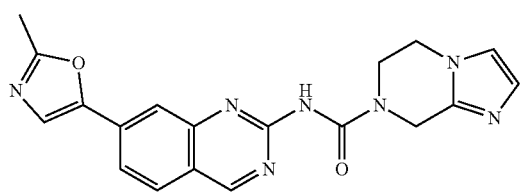 [SMILES: Cc1ncc(-c2ccc3cnc(NC(=O)N4CCn5ccnc5C4)nc3c2)o1] 1490
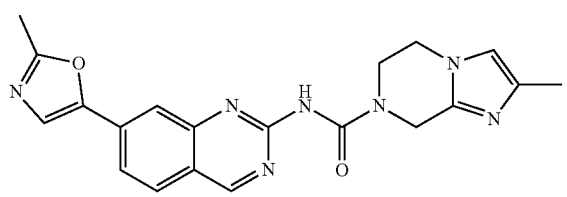 [SMILES: Cc1cn2c(n1)CN(C(=O)Nc1ncc3ccc(-c4cnc(C)o4)cc3n1)CC2] 1491
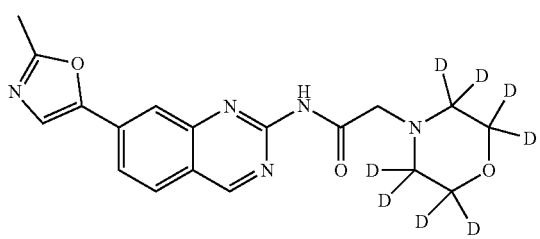 [SMILES: [2H]C1([2H])OC([2H])([2H])C([2H])([2H])N(CC(=O)Nc2ncc3ccc(-c4cnc(C)o4)cc3n2)C1([2H])[2H]] 1492
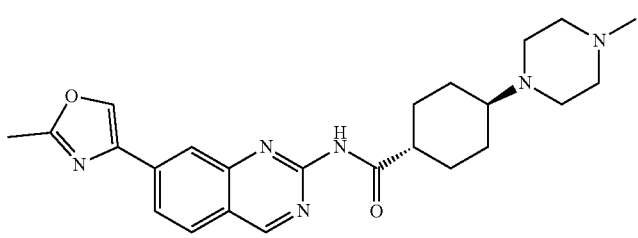 1493
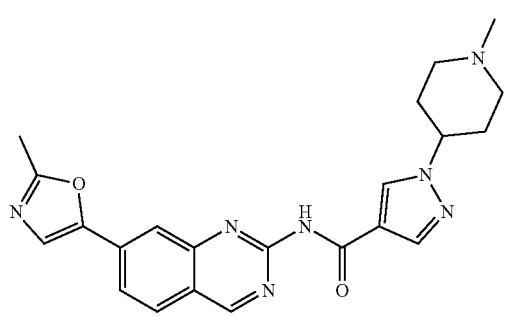 [SMILES: Cc1ncc(-c2ccc3cnc(NC(=O)c4cnn(C5CCN(C)CC5)c4)nc3c2)o1] 1494

TABLE 1-continued
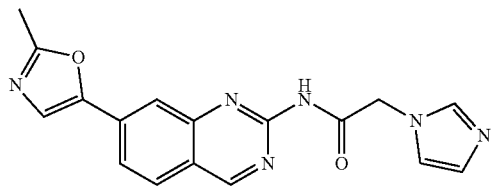 [SMILES: Cc1ncc(-c2ccc3cnc(NC(=O)Cn4ccnc4)nc3c2)o1] 1495
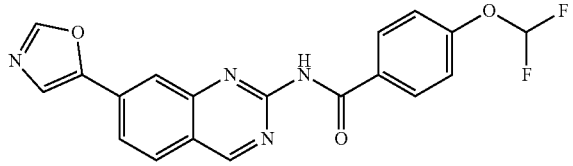 [SMILES: O=C(Nc1ncc2ccc(-c3cnco3)cc2n1)c1ccc(OC(F)F)cc1] 1496
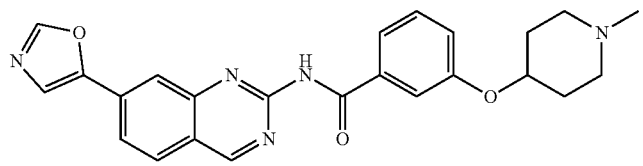 [SMILES: CN1CCC(Oc2cccc(C(=O)Nc3ncc4ccc(-c5cnco5)cc4n3)c2)CC1] 1497
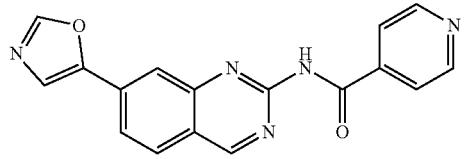 [SMILES: O=C(Nc1ncc2ccc(-c3cnco3)cc2n1)c1ccncc1] 1498
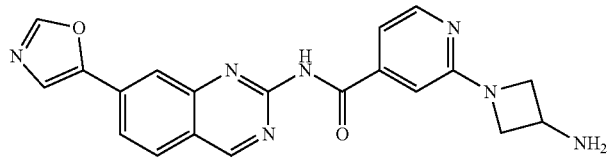 [SMILES: NC1CN(c2cc(C(=O)Nc3ncc4ccc(-c5cnco5)cc4n3)ccn2)C1] 1499
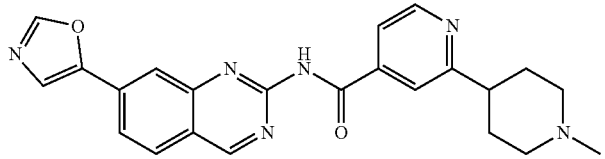 [SMILES: CN1CCC(c2cc(C(=O)Nc3ncc4ccc(-c5cnco5)cc4n3)ccn2)CC1] 1500
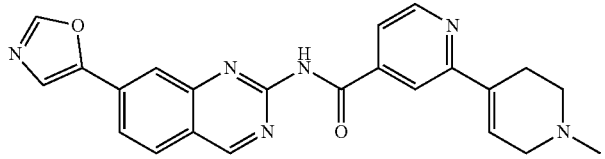 [SMILES: CN1CC=C(c2cc(C(=O)Nc3ncc4ccc(-c5cnco5)cc4n3)ccn2)CC1] 1501
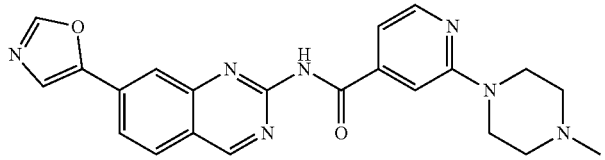 1502
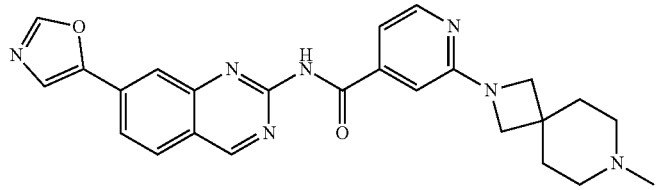 [SMILES: CN1CCC2(CC1)CN(c1cc(C(=O)Nc3ncc4ccc(-c5cnco5)cc4n3)ccn1)C2] 1503

TABLE 1-continued
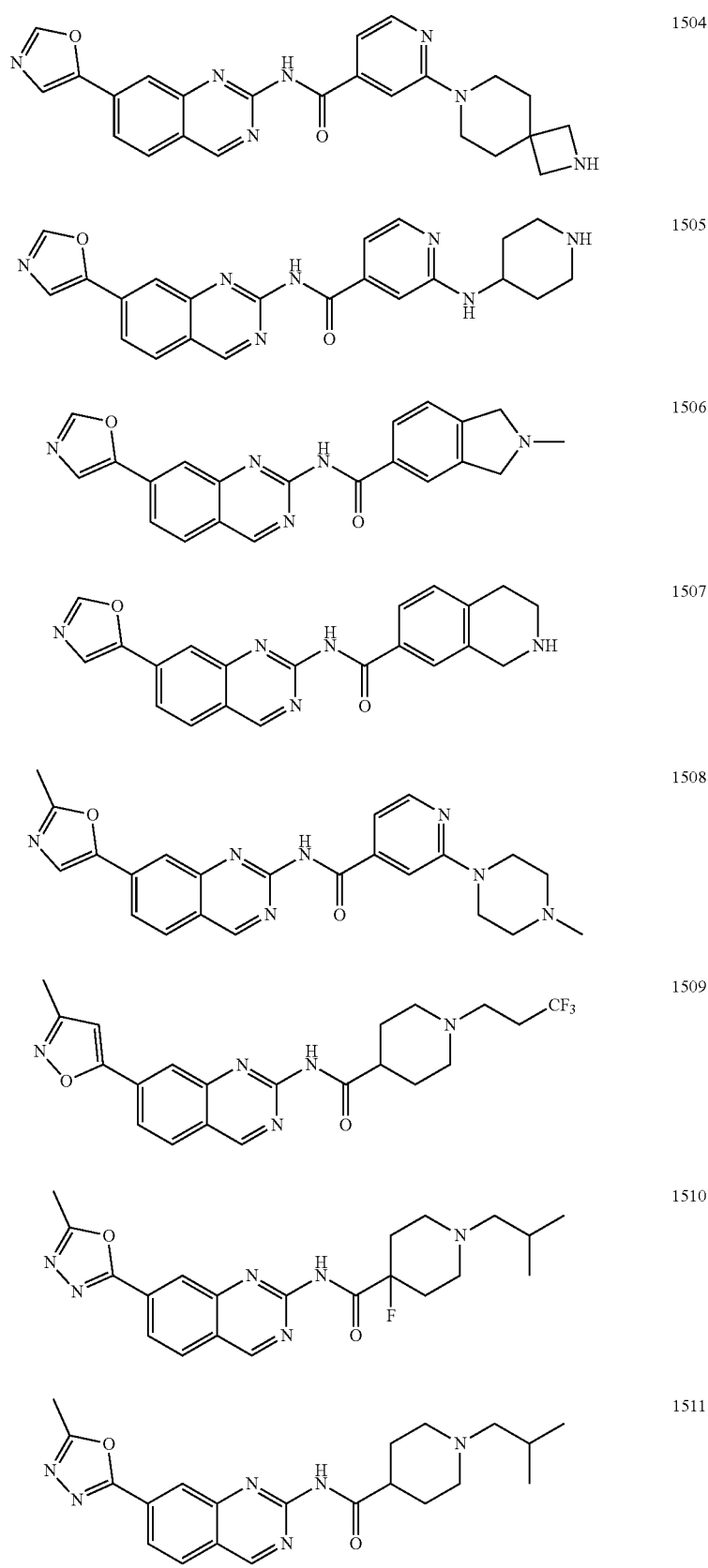
| | |
|---|---|
| | 1504 |
| | 1505 |
| | 1506 |
| | 1507 |
| | 1508 |
| | 1509 |
| | 1510 |
| | 1511 |

TABLE 1-continued
| | |
|---|---|
| 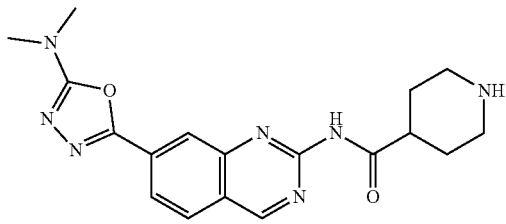 | 1512 |
| 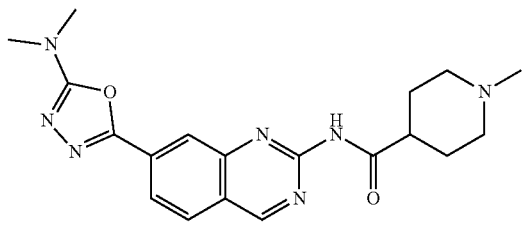 | 1513 |
| 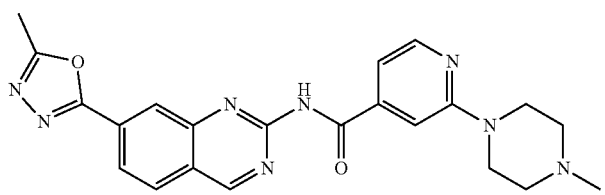 | 1514 |
| 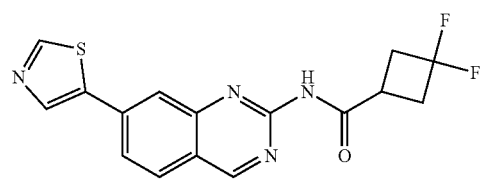 [SMILES: O=C(Nc1ncc2ccc(-c3cncs3)cc2n1)C1CC(F)(F)C1] | 1515 |
| 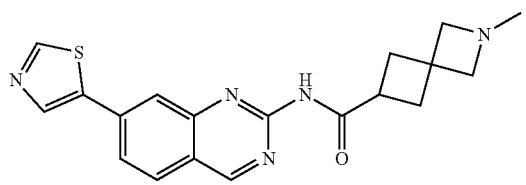 [SMILES: CN1CC2(CC(C(=O)Nc3ncc4ccc(-c5cncs5)cc4n3)C2)C1] | 1516 |
| 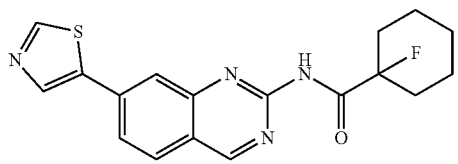 | 1517 |
| 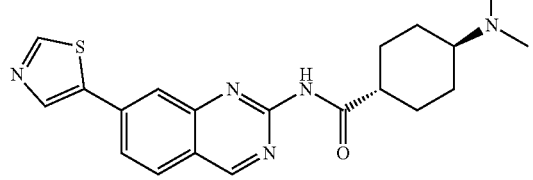 | 1518 |
| 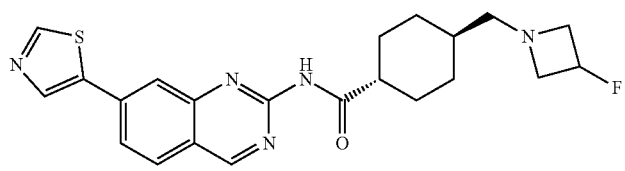 [SMILES: O=C(Nc1ncc2ccc(-c3cncs3)cc2n1)[C@H]1CC[C@H](CN2CC(F)C2)CC1] | 1519 |

TABLE 1-continued
| | |
|---|---|
| 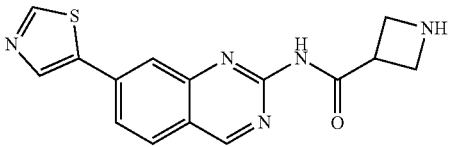 [SMILES: O=C(Nc1ncc2ccc(-c3cncs3)cc2n1)C1CNC1] | 1520 |
| 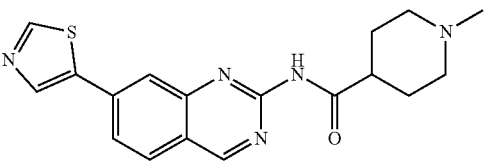 [SMILES: CN1CCC(C(=O)Nc2ncc3ccc(-c4cncs4)cc3n2)CC1] | 1521 |
| 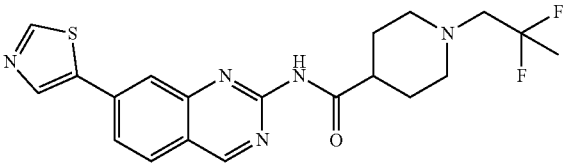 [SMILES: CC(F)(F)CN1CCC(C(=O)Nc2ncc3ccc(-c4cncs4)cc3n2)CC1] | 1522 |
| 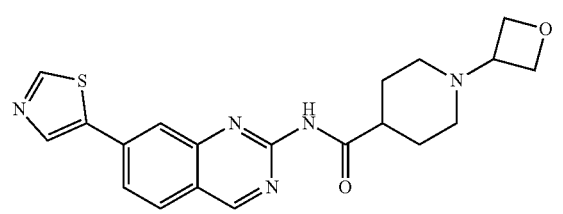 [SMILES: O=C(Nc1ncc2ccc(-c3cncs3)cc2n1)C1CCN(C2COC2)CC1] | 1523 |
| 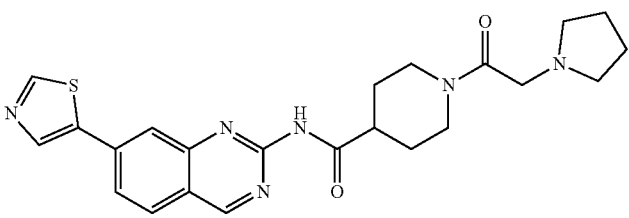 [SMILES: O=C(Nc1ncc2ccc(-c3cncs3)cc2n1)C1CCN(C(=O)CN2CCCC2)CC1] | 1524 |
| 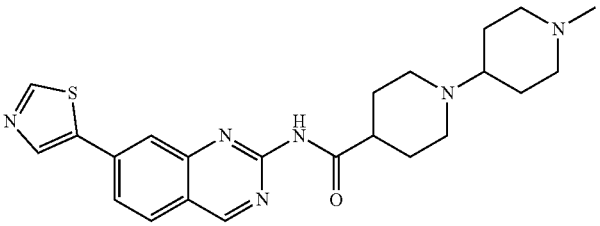 [SMILES: CN1CCC(N2CCC(C(=O)Nc3ncc4ccc(-c5cncs5)cc4n3)CC2)CC1] | 1525 |
| 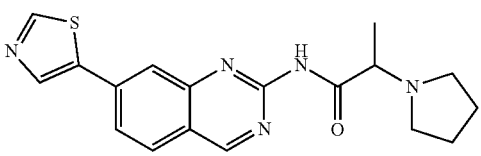 [SMILES: CC(C(=O)Nc1ncc2ccc(-c3cncs3)cc2n1)N1CCCC1] | 1526 |
| 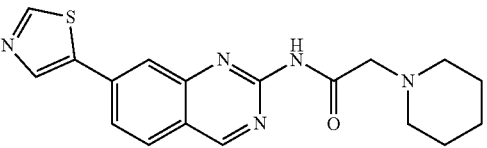 [SMILES: O=C(CN1CCCCC1)Nc1ncc2ccc(-c3cncs3)cc2n1] | 1527 |

TABLE 1-continued
| | |
|---|---|
| 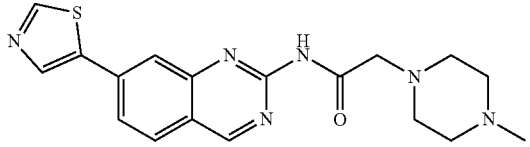 [SMILES: CN1CCN(CC(=O)Nc2ncc3ccc(-c4cncs4)cc3n2)CC1] | 1528 |
| 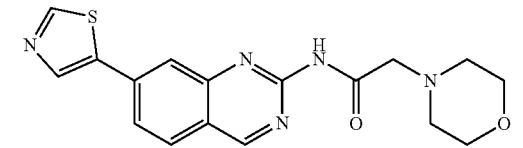 [SMILES: O=C(CN1CCOCC1)Nc1ncc2ccc(-c3cncs3)cc2n1] | 1529 |
| 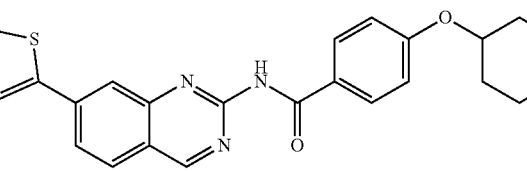 | 1530 |
| 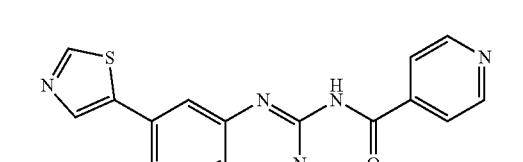 | 1531 |
| 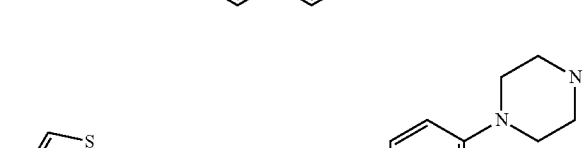 | 1532 |
| 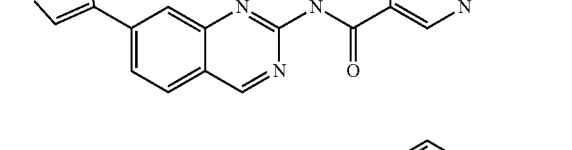 | 1533 |
| 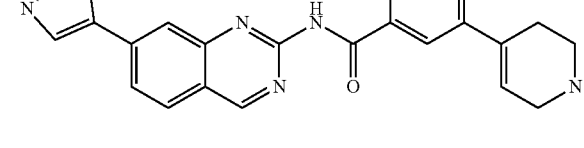 | 1534 |
| 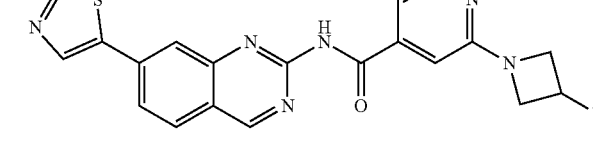 | 1535 |

TABLE 1-continued
| | |
|---|---|
| 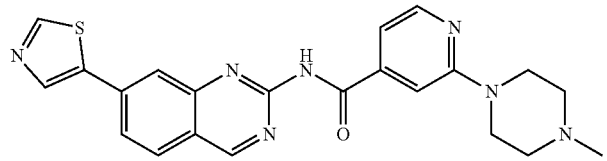 | 1536 |
| 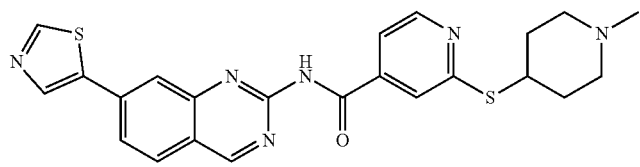 | 1537 |
| 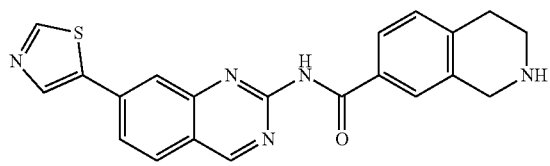 | 1538 |
| 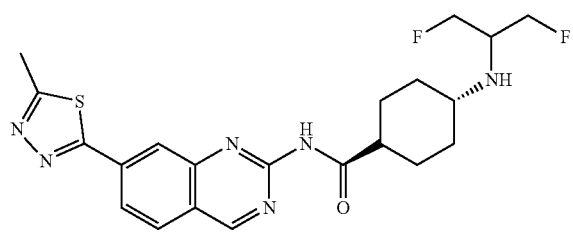 | 1539 |
| 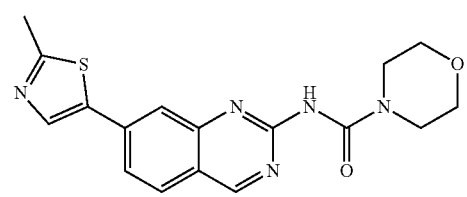 [SMILES: Cc1ncc(-c2ccc3cnc(NC(=O)N4CCOCC4)nc3c2)s1] | 1540 |
| 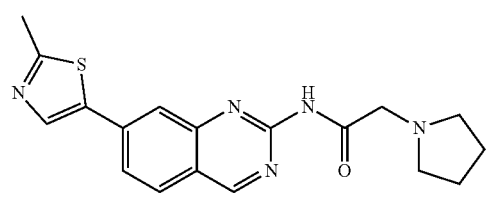 [SMILES: Cc1ncc(-c2ccc3cnc(NC(=O)CN4CCCC4)nc3c2)s1] | 1541 |
| 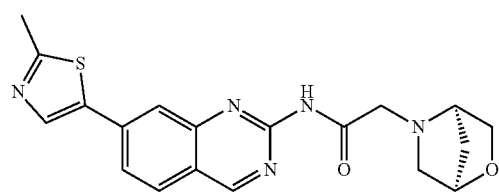 [SMILES: Cc1ncc(-c2ccc3cnc(NC(=O)CN4C[C@H]5C[C@@H]4CO5)nc3c2)s1] | 1542 |
| 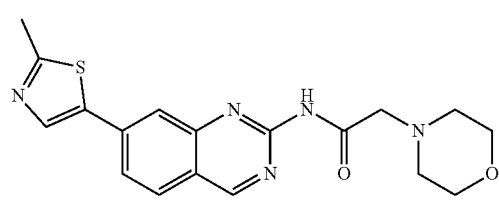 | 1543 |

TABLE 1-continued
| | |
|---|---|
| 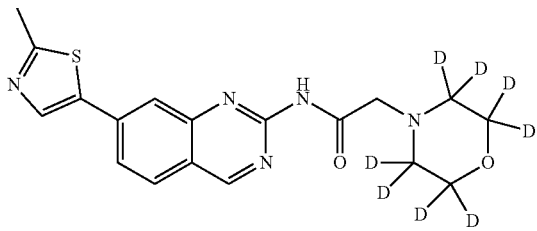 [SMILES: [2H]C1([2H])OC([2H])([2H])C([2H])([2H])N(CC(=O)Nc2ncc3ccc(-c4cnc(C)s4)cc3n2)C1([2H])[2H]] | 1544 |
| 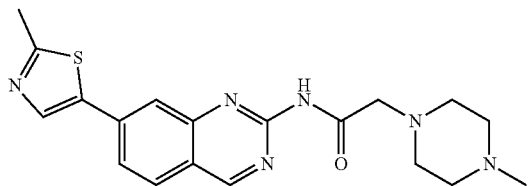 | 1545 |
| 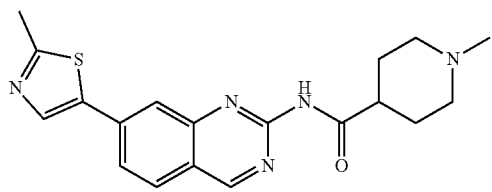 [SMILES: Cc1ncc(-c2ccc3cnc(NC(=O)C4CCN(C)CC4)nc3c2)s1] | 1546 |
| 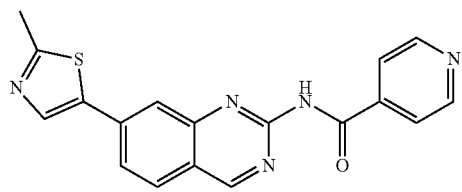 [SMILES: Cc1ncc(-c2ccc3cnc(NC(=O)c4ccncc4)nc3c2)s1] | 1547 |
| 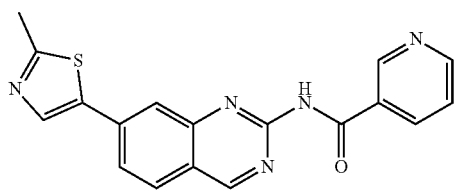 [SMILES: Cc1ncc(-c2ccc3cnc(NC(=O)c4cccnc4)nc3c2)s1] | 1548 |
| 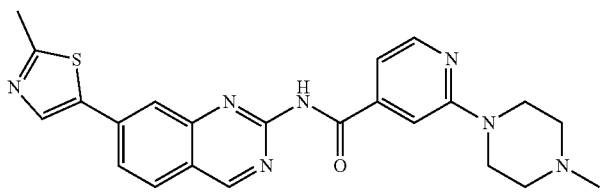 | 1549 |
| 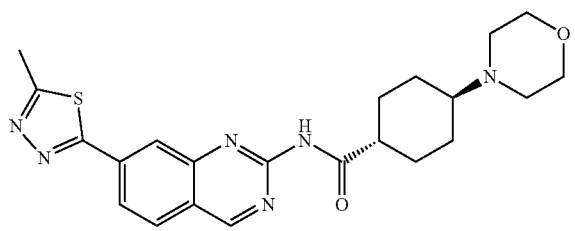 [SMILES: Cc1nnc(-c2ccc3cnc(NC(=O)[C@H]4CC[C@H](N5CCOCC5)CC4)nc3c2)s1] | 1550 |

TABLE 1-continued
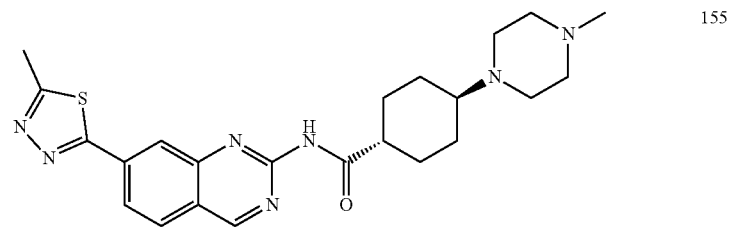 1551
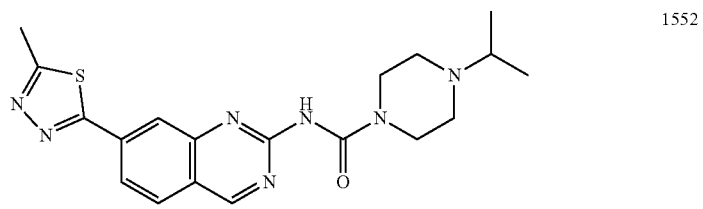 1552
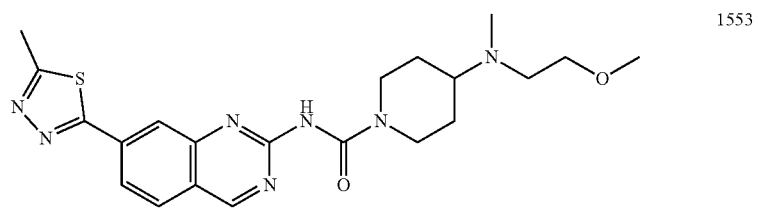 1553
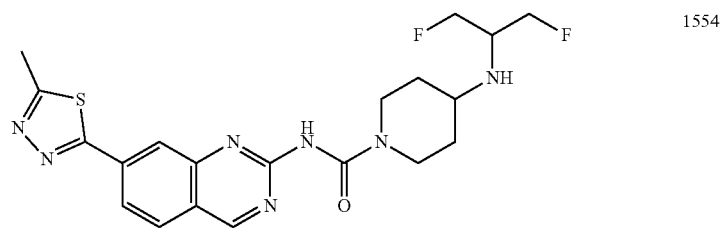 1554
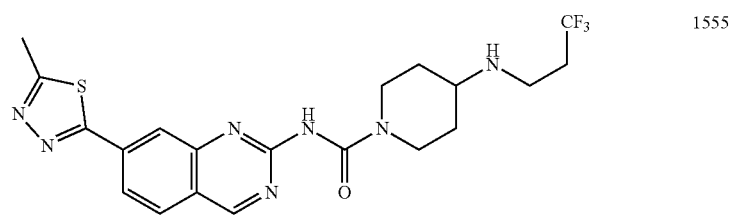 1555
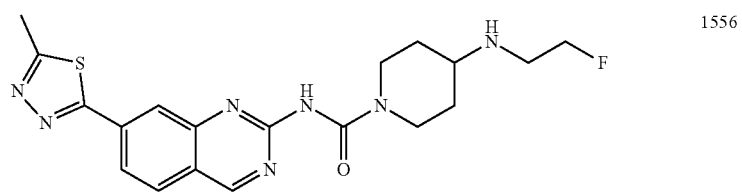 1556
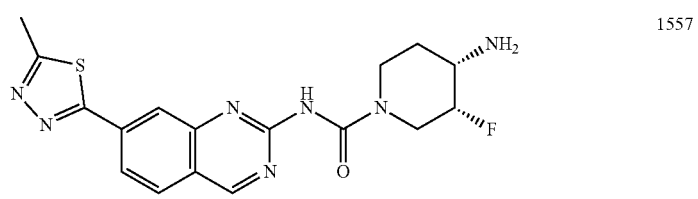 1557

TABLE 1-continued
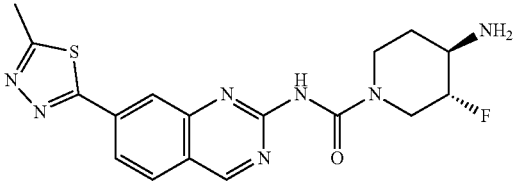 [SMILES: Cc1nnc(-c2ccc3cnc(NC(=O)N4CC[C@@H](N)[C@H](F)C4)nc3c2)s1]  1558
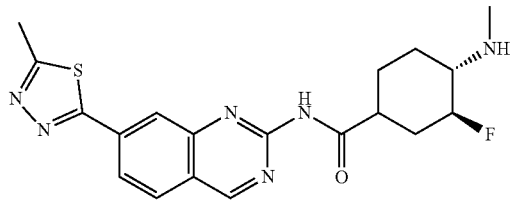 [SMILES: CN[C@H]1CCC(C(=O)Nc2ncc3ccc(-c4nnc(C)s4)cc3n2)C[C@@H]1F]  1559
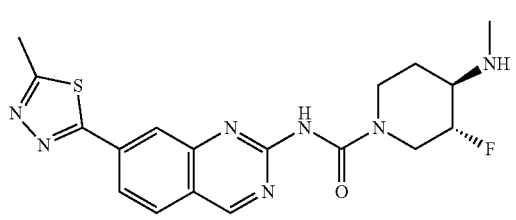  1560
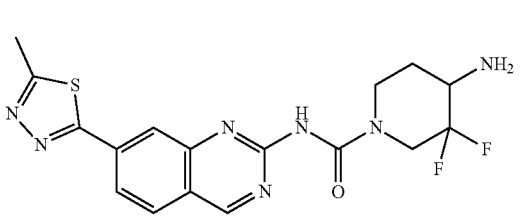 [SMILES: Cc1nnc(-c2ccc3cnc(NC(=O)N4CCC(N)C(F)(F)C4)nc3c2)s1]  1561
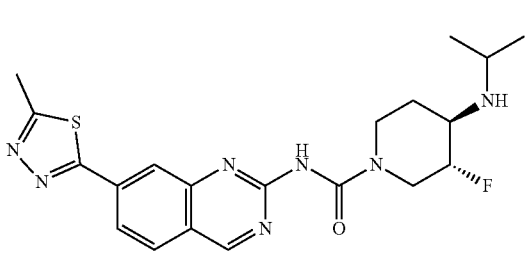 [SMILES: Cc1nnc(-c2ccc3cnc(NC(=O)N4CC[C@@H](NC(C)C)[C@H](F)C4)nc3c2)s1]  1562
  1563
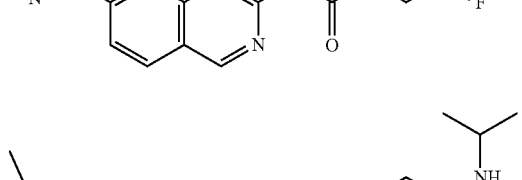  1564

TABLE 1-continued
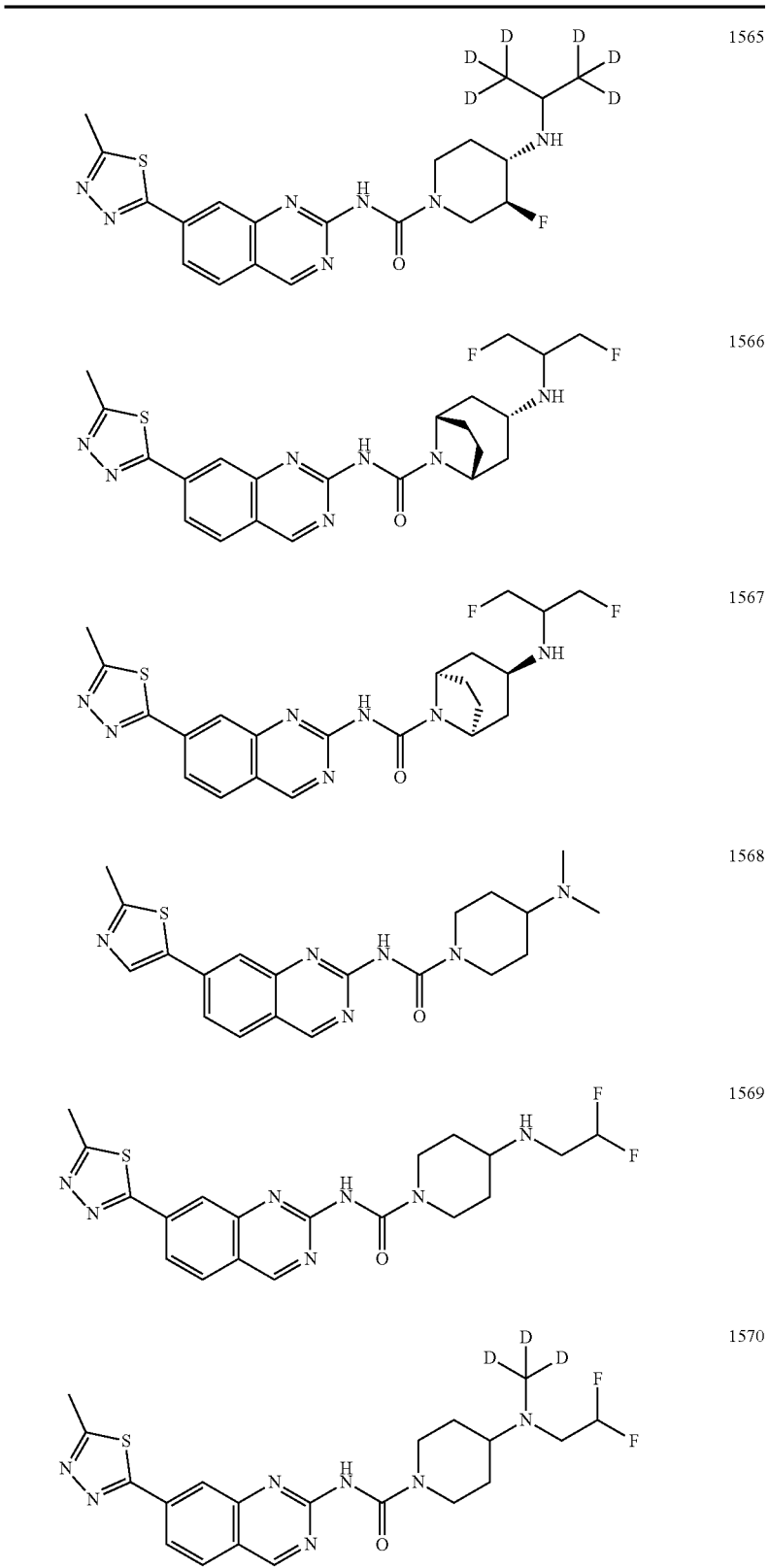

TABLE 1-continued
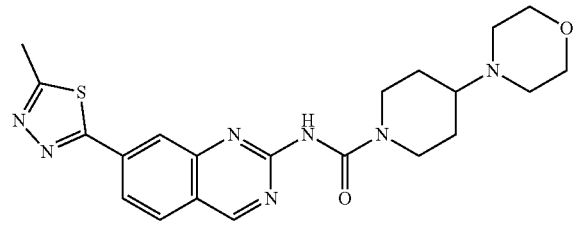 [SMILES: Cc1nnc(-c2ccc3cnc(NC(=O)N4CCC(N5CCOCC5)CC4)nc3c2)s1]
1571
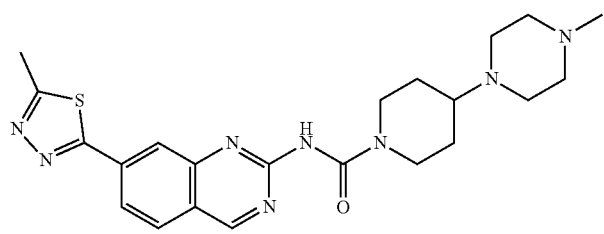 [SMILES: Cc1nnc(-c2ccc3cnc(NC(=O)N4CCC(N5CCN(C)CC5)CC4)nc3c2)s1]
1572
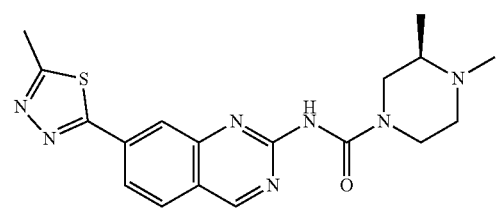 [SMILES: Cc1nnc(-c2ccc3cnc(NC(=O)N4CCN(C)[C@H](C)C4)nc3c2)s1]
1573
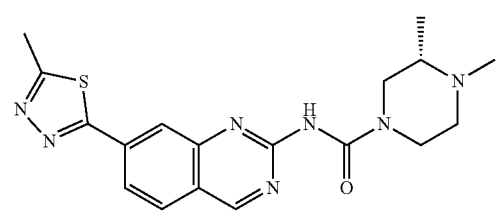 [SMILES: Cc1nnc(-c2ccc3cnc(NC(=O)N4CCN(C)[C@@H](C)C4)nc3c2)s1]
1574
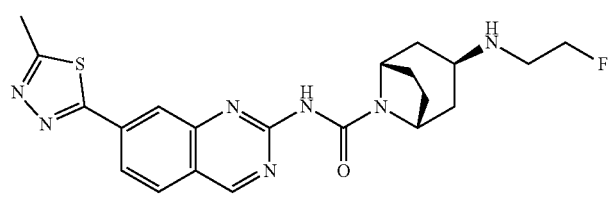 [SMILES: Cc1nnc(-c2ccc3cnc(NC(=O)N4[C@@H]5CC[C@H]4C[C@@H](NCCF)C5)nc3c2)s1]
1575
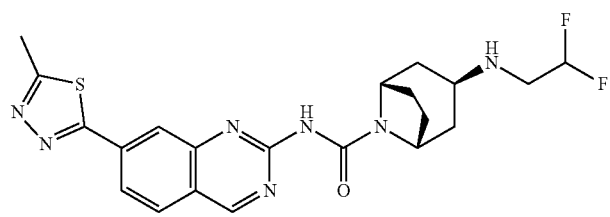 [SMILES: Cc1nnc(-c2ccc3cnc(NC(=O)N4[C@@H]5CC[C@H]4C[C@@H](NCC(F)F)C5)nc3c2)s1]
1576
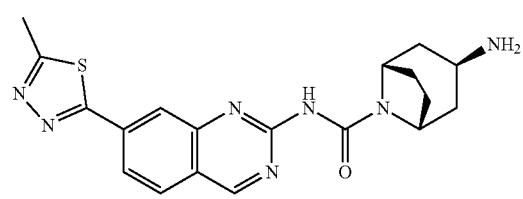 [SMILES: Cc1nnc(-c2ccc3cnc(NC(=O)N4[C@@H]5CC[C@H]4C[C@@H](N)C5)nc3c2)s1]
1577

TABLE 1-continued
| | |
|---|---|
| 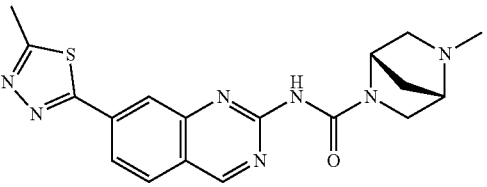 [SMILES: Cc1nnc(-c2ccc3cnc(NC(=O)N4C[C@@H]5C[C@H]4CN5C)nc3c2)s1] | 1578 |
| 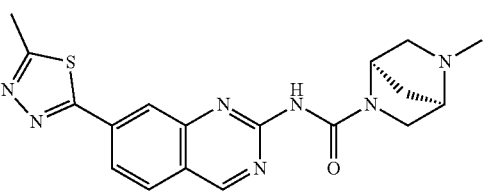 | 1579 |
| 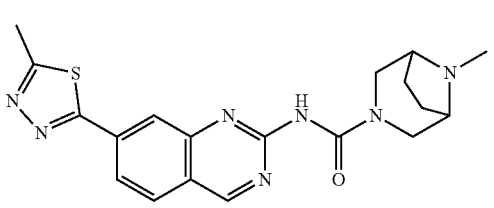 [SMILES: Cc1nnc(-c2ccc3cnc(NC(=O)N4CC5CCC(C4)N5C)nc3c2)s1] | 1580 |
| 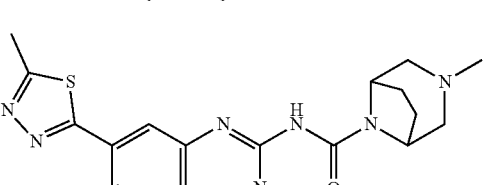 | 1581 |
| 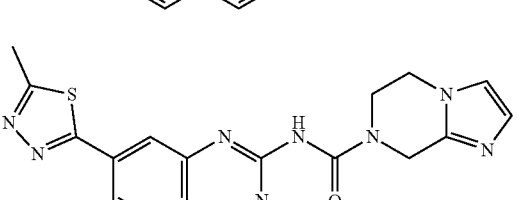 | 1582 |
| 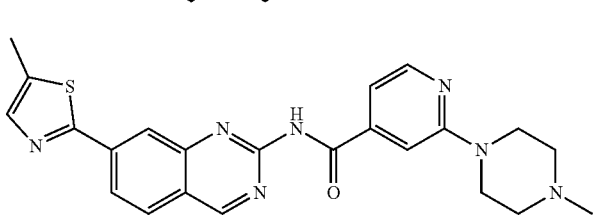 | 1583 |
| 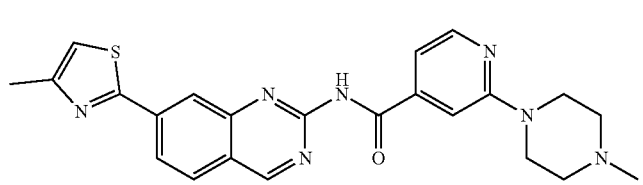 | 1584 |
| 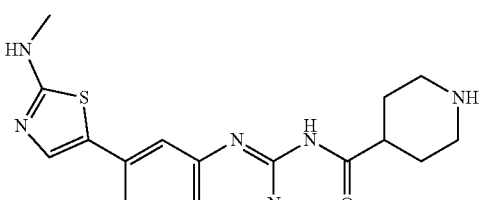 | 1585 |

TABLE 1-continued
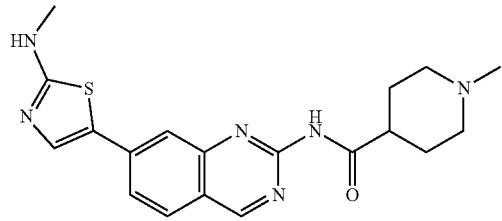 [SMILES: CNc1ncc(-c2ccc3cnc(NC(=O)C4CCN(C)CC4)nc3c2)s1]
1586
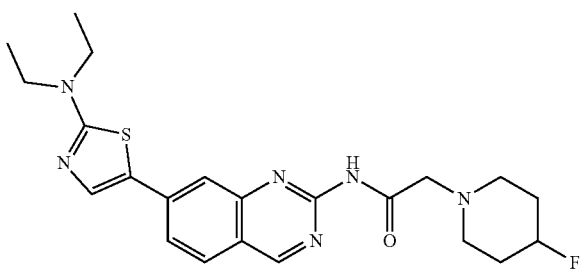 [SMILES: CCN(CC)c1ncc(-c2ccc3cnc(NC(=O)CN4CCC(F)CC4)nc3c2)s1]
1587
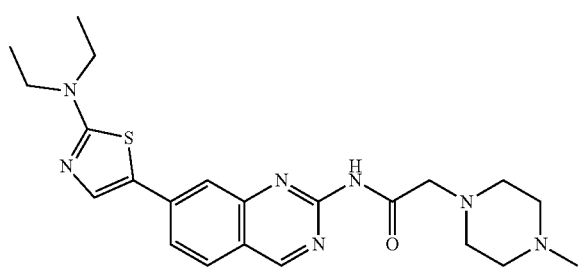 [SMILES: CCN(CC)c1ncc(-c2ccc3cnc(NC(=O)CN4CCN(C)CC4)nc3c2)s1]
1588
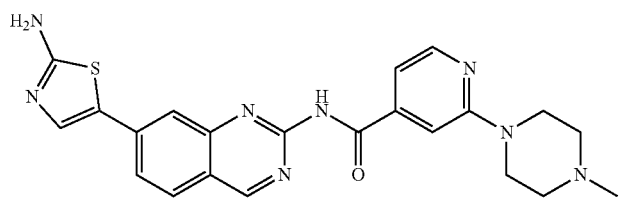 [SMILES: CN1CCN(c2cc(C(=O)Nc3ncc4ccc(-c5cnc(N)s5)cc4n3)ccn2)CC1]
1589
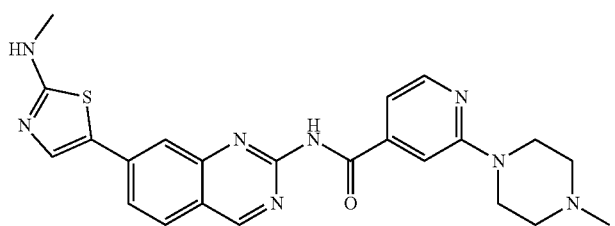 [SMILES: CNc1ncc(-c2ccc3cnc(NC(=O)c4ccnc(N5CCN(C)CC5)c4)nc3c2)s1]
1590
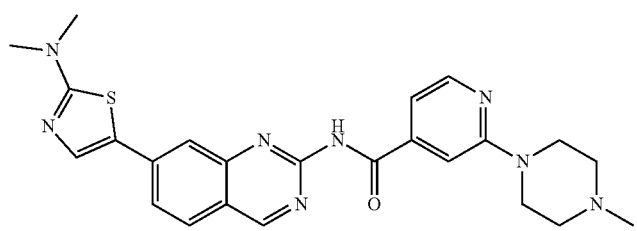
1591

TABLE 1-continued
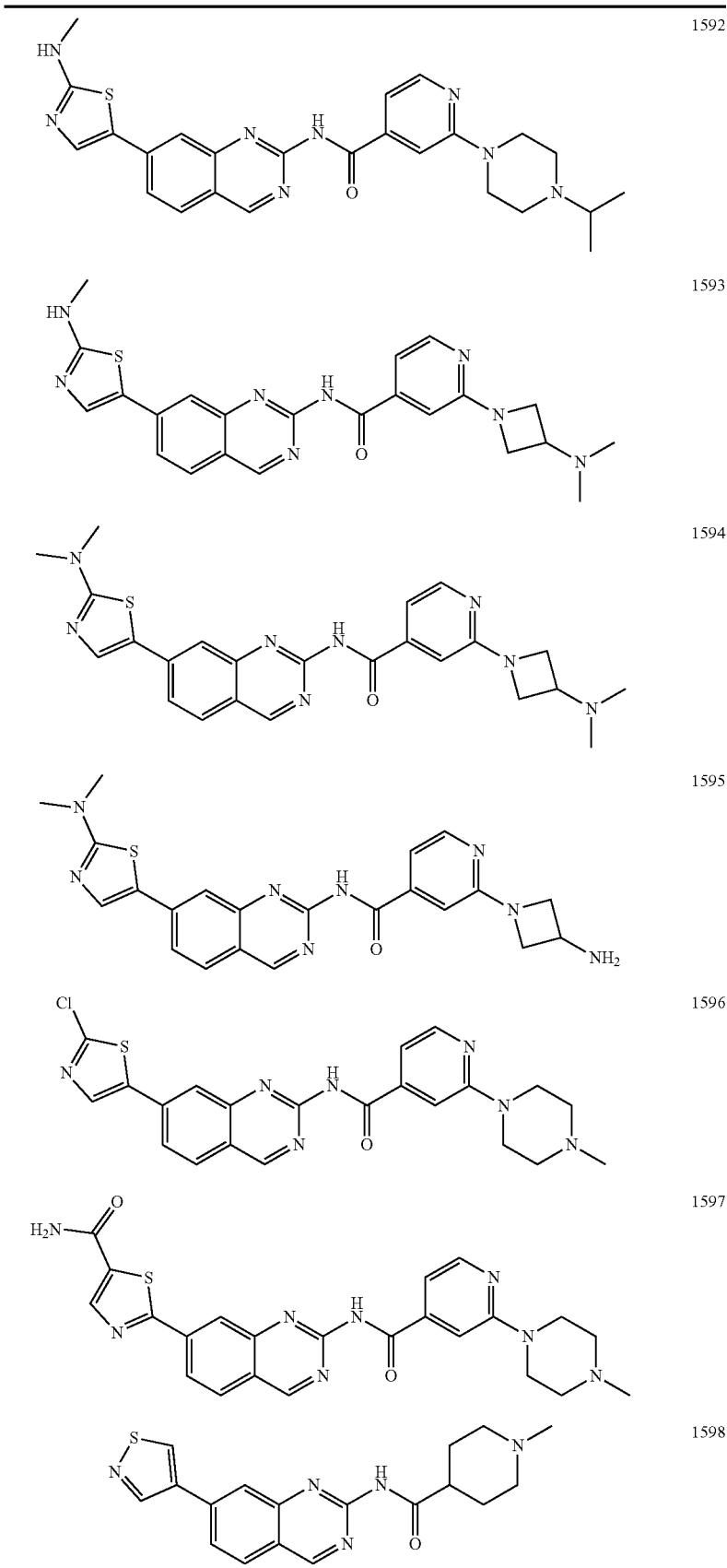

TABLE 1-continued
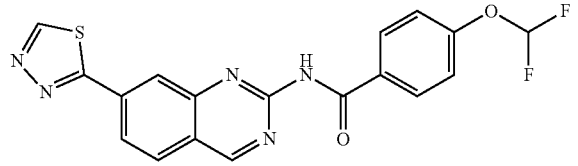 1599
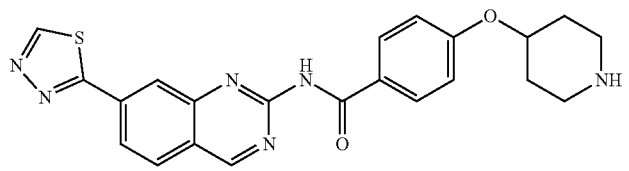 [SMILES: O=C(Nc1ncc2ccc(-c3nncs3)cc2n1)c1ccc(OC2CCNCC2)cc1] 1600
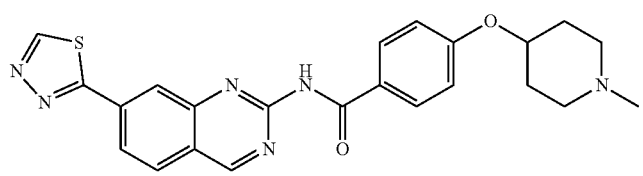 [SMILES: CN1CCC(Oc2ccc(C(=O)Nc3ncc4ccc(-c5nncs5)cc4n3)cc2)CC1] 1601
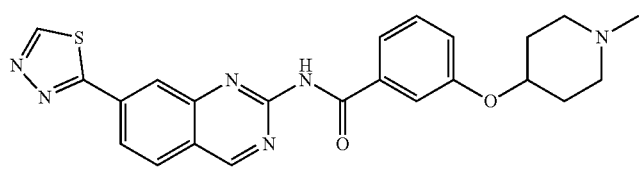 [SMILES: CN1CCC(Oc2cccc(C(=O)Nc3ncc4ccc(-c5nncs5)cc4n3)c2)CC1] 1602
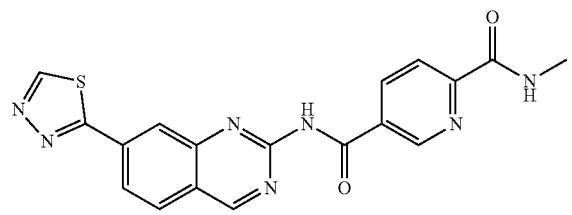 [SMILES: CNC(=O)c1ccc(C(=O)Nc2ncc3ccc(-c4nncs4)cc3n2)cn1] 1603
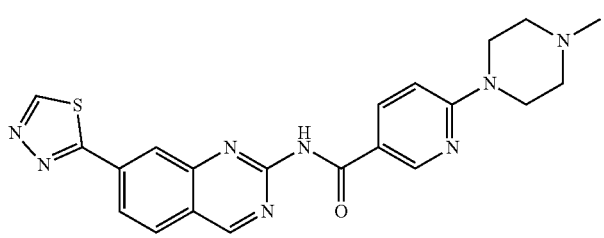 1604
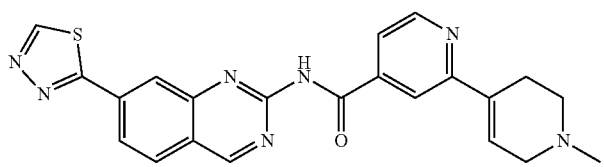 [SMILES: CN1CC=C(c2cc(C(=O)Nc3ncc4ccc(-c5nncs5)cc4n3)ccn2)CC1] 1605
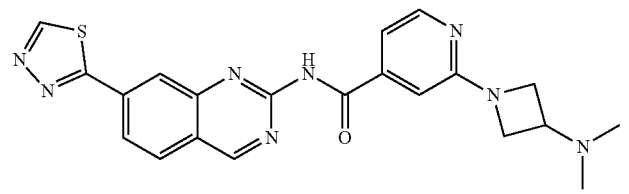 [SMILES: CN(C)C1CN(c2cc(C(=O)Nc3ncc4ccc(-c5nncs5)cc4n3)ccn2)C1] 1606

TABLE 1-continued
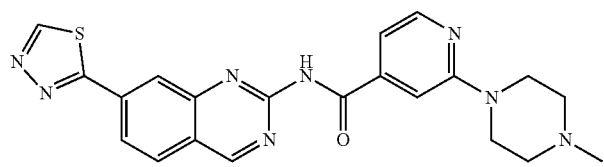 [SMILES: CN1CCN(c2cc(C(=O)Nc3ncc4ccc(-c5nncs5)cc4n3)ccn2)CC1] 1607
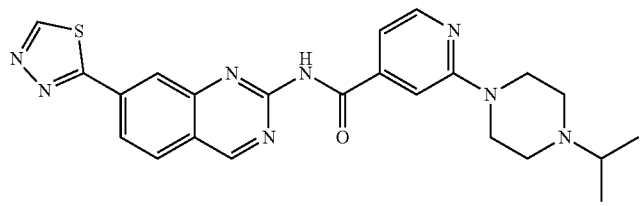 [SMILES: CC(C)N1CCN(c2cc(C(=O)Nc3ncc4ccc(-c5nncs5)cc4n3)ccn2)CC1] 1608
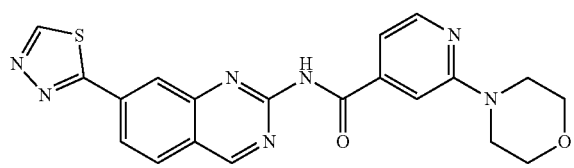 [SMILES: O=C(Nc1ncc2ccc(-c3nncs3)cc2n1)c1ccnc(N2CCOCC2)c1] 1609
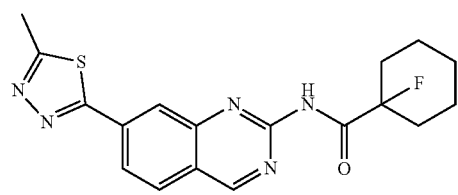 1610
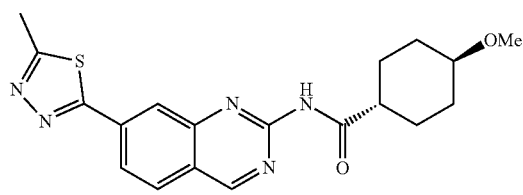 [SMILES: CO[C@H]1CC[C@H](C(=O)Nc2ncc3ccc(-c4nnc(C)s4)cc3n2)CC1] 1611
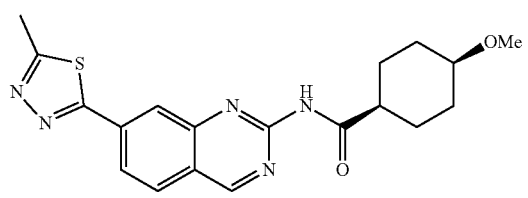 [SMILES: CO[C@H]1CC[C@@H](C(=O)Nc2ncc3ccc(-c4nnc(C)s4)cc3n2)CC1] 1612
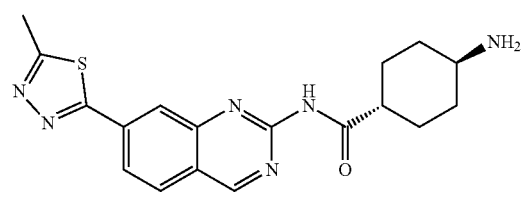 [SMILES: Cc1nnc(-c2ccc3cnc(NC(=O)[C@H]4CC[C@H](N)CC4)nc3c2)s1] 1613
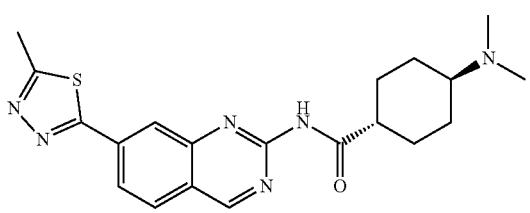 [SMILES: Cc1nnc(-c2ccc3cnc(NC(=O)[C@H]4CC[C@H](N(C)C)CC4)nc3c2)s1] 1614

TABLE 1-continued
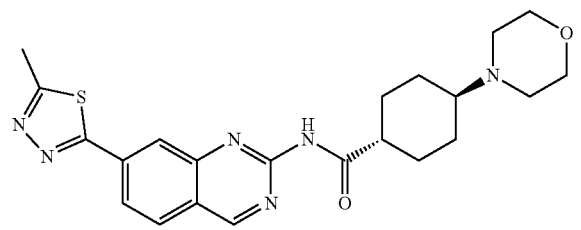
1615
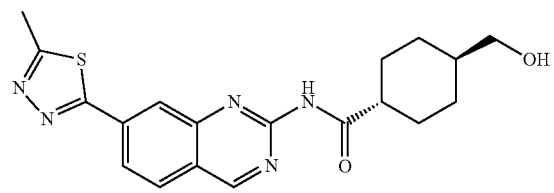 [SMILES: Cc1nnc(-c2ccc3cnc(NC(=O)[C@H]4CC[C@H](CO)CC4)nc3c2)s1]
1616
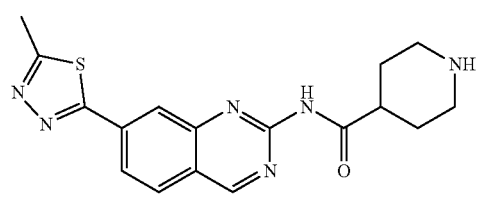 [SMILES: Cc1nnc(-c2ccc3cnc(NC(=O)C4CCNCC4)nc3c2)s1]
1617
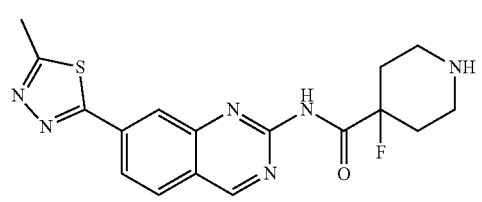 [SMILES: Cc1nnc(-c2ccc3cnc(NC(=O)C4(F)CCNCC4)nc3c2)s1]
1618
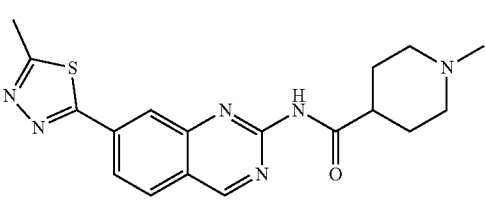
1619
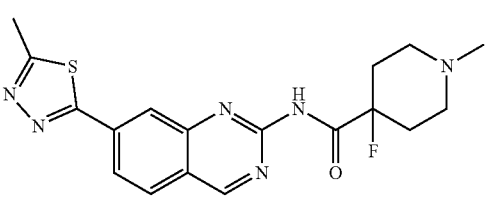 [SMILES: Cc1nnc(-c2ccc3cnc(NC(=O)C4(F)CCN(C)CC4)nc3c2)s1]
1620
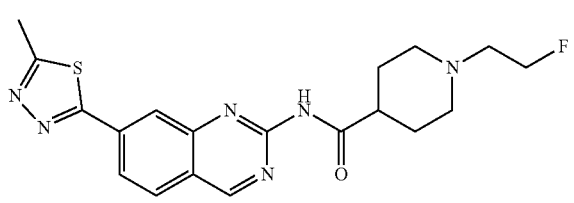 [SMILES: Cc1nnc(-c2ccc3cnc(NC(=O)C4CCN(CCF)CC4)nc3c2)s1]
1621
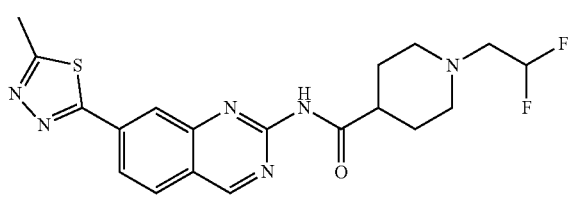 [SMILES: Cc1nnc(-c2ccc3cnc(NC(=O)C4CCN(CC(F)F)CC4)nc3c2)s1]
1622

TABLE 1-continued
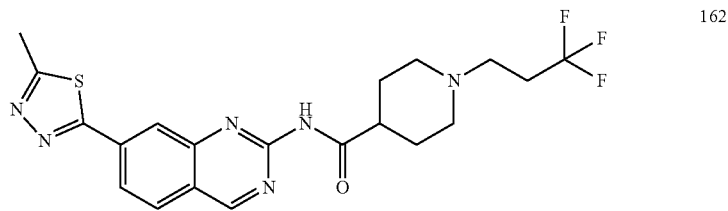
1623
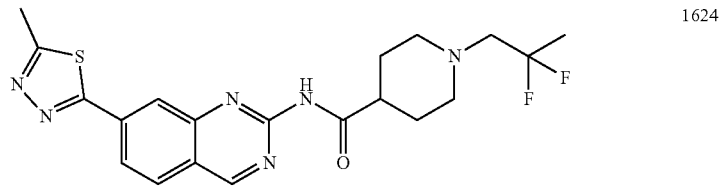
1624
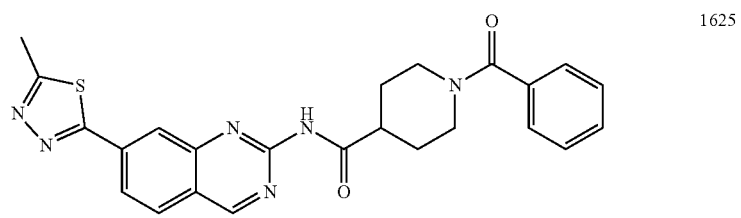
1625
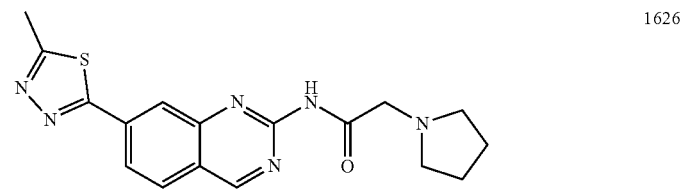
1626
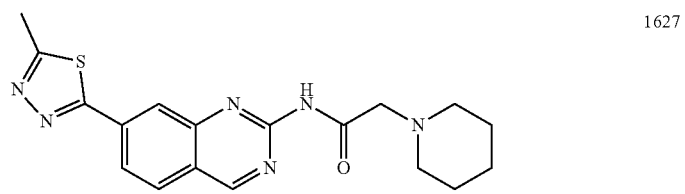
1627
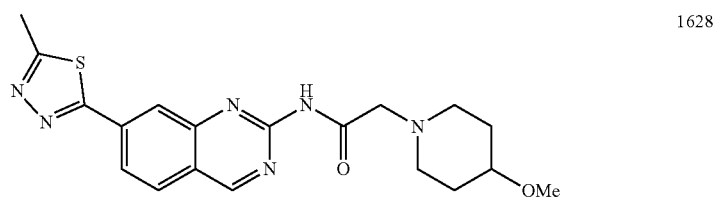
1628
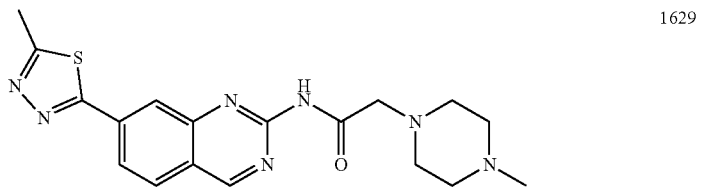
1629
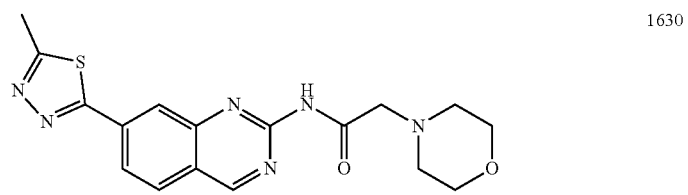
1630

TABLE 1-continued
| | |
|---|---|
| 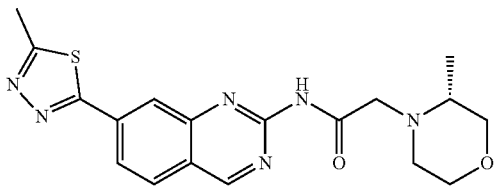 [SMILES: Cc1nnc(-c2ccc3cnc(NC(=O)CN4CCOC[C@H]4C)nc3c2)s1] | 1631 |
| 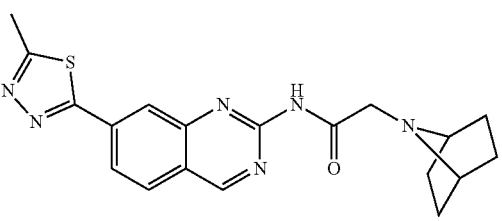 [SMILES: Cc1nnc(-c2ccc3cnc(NC(=O)CN4C5CCC4CC5)nc3c2)s1] | 1632 |
| 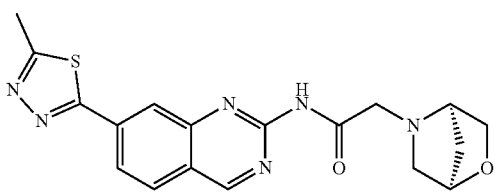 [SMILES: Cc1nnc(-c2ccc3cnc(NC(=O)CN4C[C@H]5C[C@@H]4CO5)nc3c2)s1] | 1633 |
| 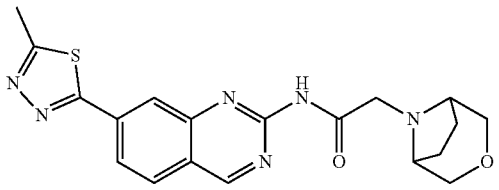 [SMILES: Cc1nnc(-c2ccc3cnc(NC(=O)CN4C5CCC4COC5)nc3c2)s1] | 1634 |
| 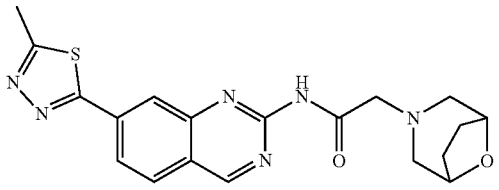 [SMILES: Cc1nnc(-c2ccc3cnc(NC(=O)CN4CC5CCC(C4)O5)nc3c2)s1] | 1635 |
| 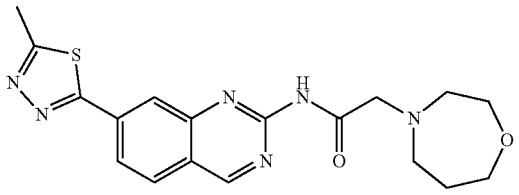 [SMILES: Cc1nnc(-c2ccc3cnc(NC(=O)CN4CCCOCC4)nc3c2)s1] | 1636 |
| 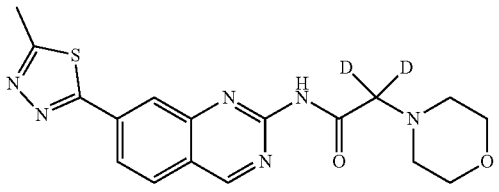 [SMILES: [2H]C([2H])(C(=O)Nc1ncc2ccc(-c3nnc(C)s3)cc2n1)N1CCOCC1] | 1637 |
| 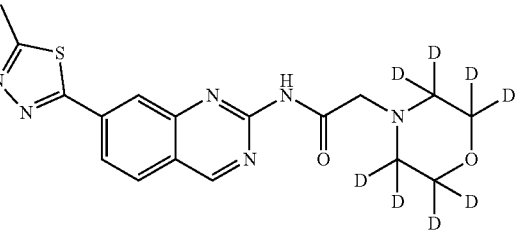 | 1638 |

TABLE 1-continued
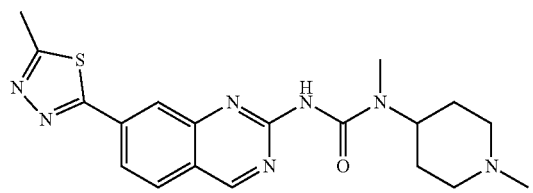 1639
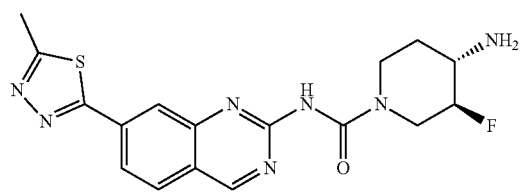 1640
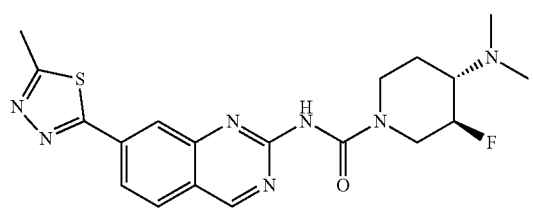 [SMILES: Cc1nnc(-c2ccc3cnc(NC(=O)N4CC[C@H](N(C)C)[C@@H](F)C4)nc3c2)s1] 1641
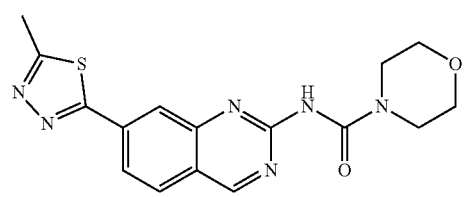 [SMILES: Cc1nnc(-c2ccc3cnc(NC(=O)N4CCOCC4)nc3c2)s1] 1642
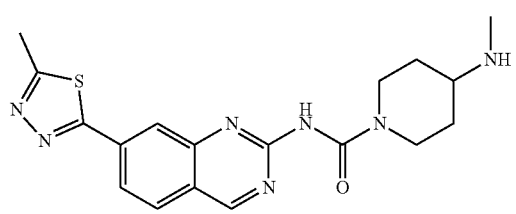 [SMILES: CNC1CCN(C(=O)Nc2ncc3ccc(-c4nnc(C)s4)cc3n2)CC1] 1643
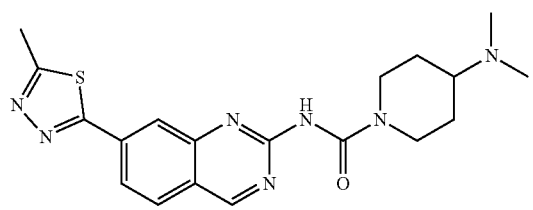 [SMILES: Cc1nnc(-c2ccc3cnc(NC(=O)N4CCC(N(C)C)CC4)nc3c2)s1] 1644
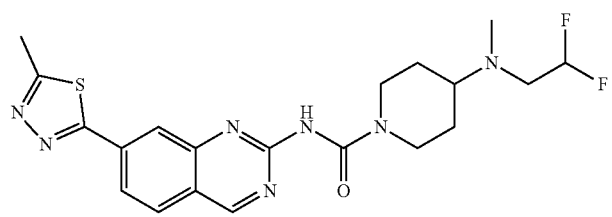 [SMILES: Cc1nnc(-c2ccc3cnc(NC(=O)N4CCC(N(C)CC(F)F)CC4)nc3c2)s1] 1645

TABLE 1-continued
| | |
|---|---|
| 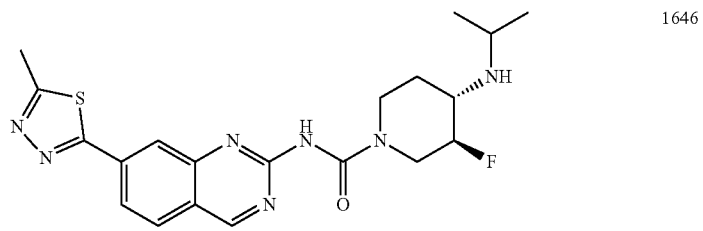 | 1646 |
| 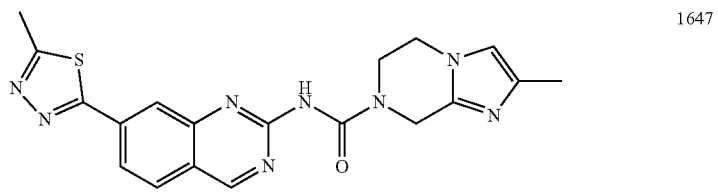 | 1647 |
| 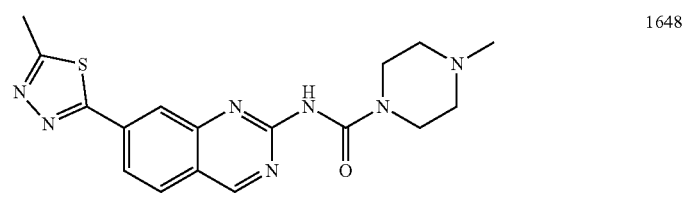 | 1648 |
| 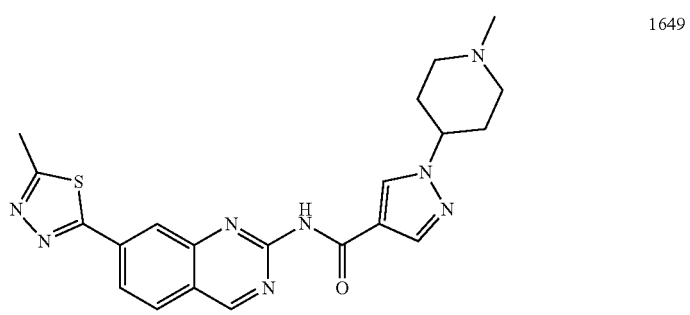 | 1649 |
| 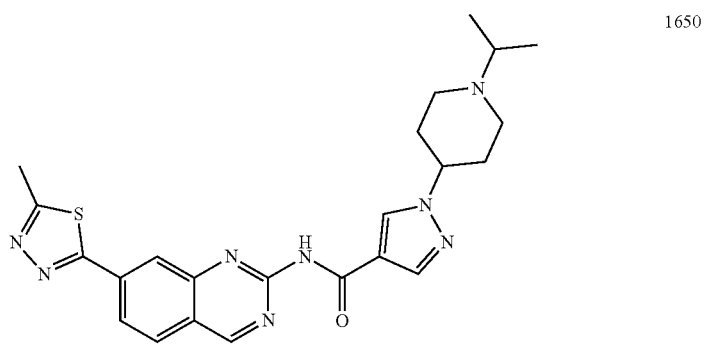 | 1650 |
| 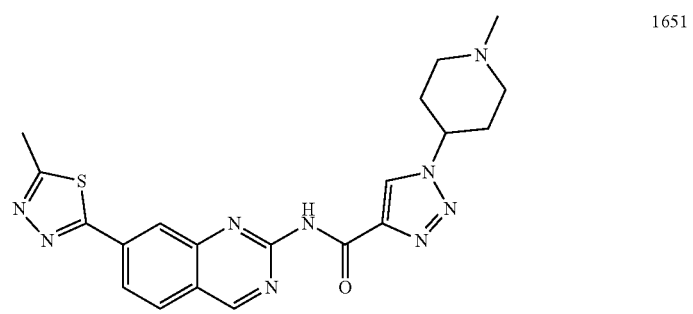 | 1651 |

TABLE 1-continued
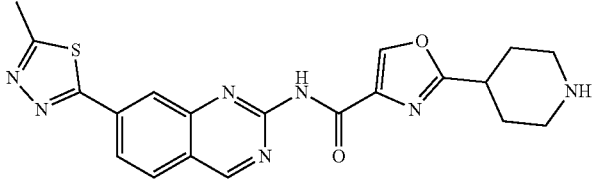 [SMILES: Cc1nnc(-c2ccc3cnc(NC(=O)c4coc(C5CCNCC5)n4)nc3c2)s1]
1652
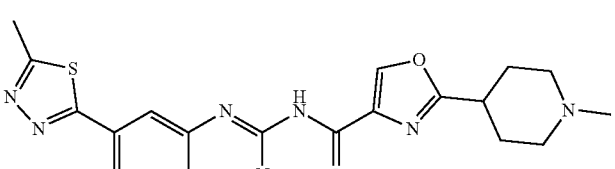
1653
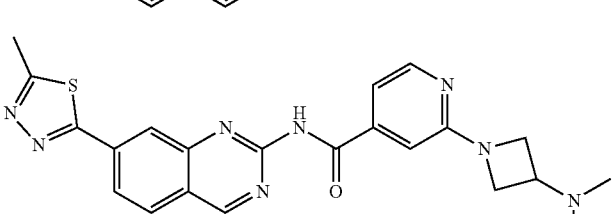
1654
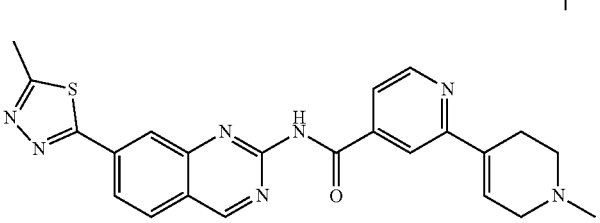
1655
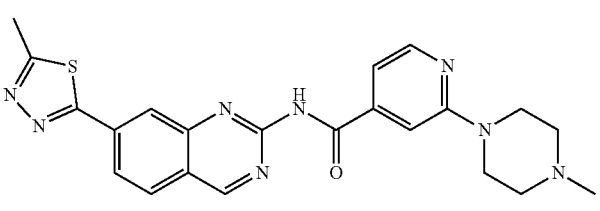
1656
1657
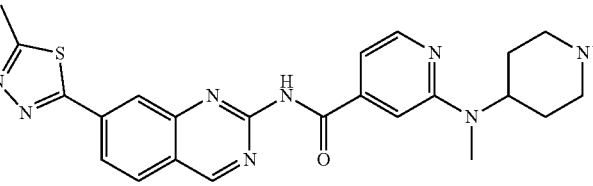
1658
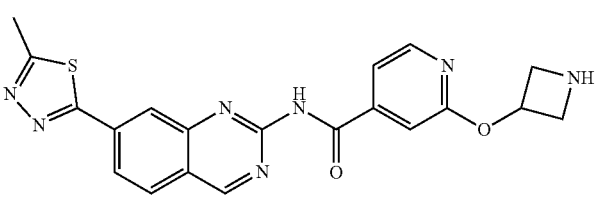 [SMILES: Cc1nnc(-c2ccc3cnc(NC(=O)c4ccnc(OC5CNC5)c4)nc3c2)s1]
1659

TABLE 1-continued
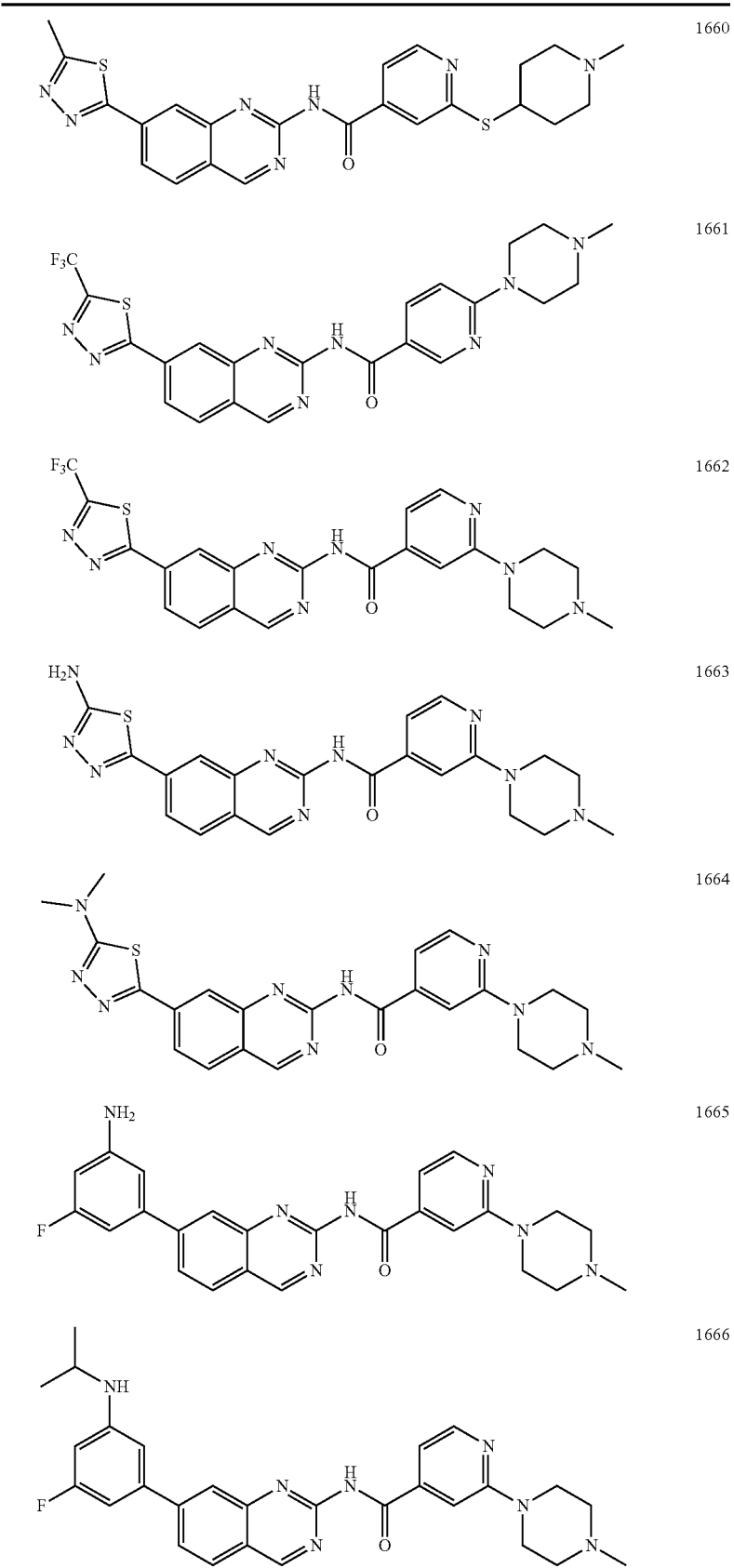
1660
1661
1662
1663
1664
1665
1666

TABLE 1-continued
| | |
|---|---|
| 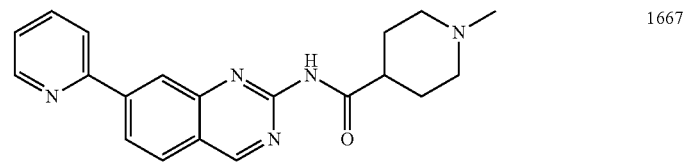 | 1667 |
| 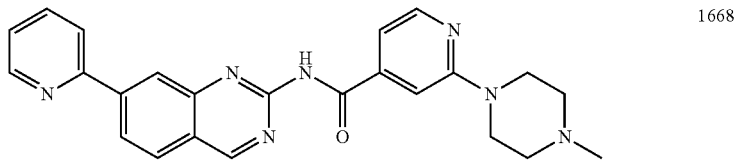 | 1668 |
| 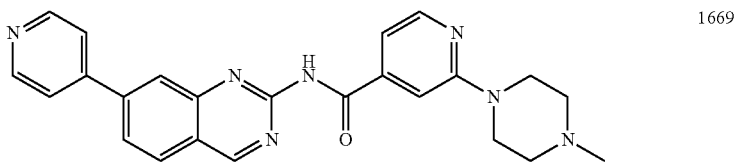 | 1669 |
| 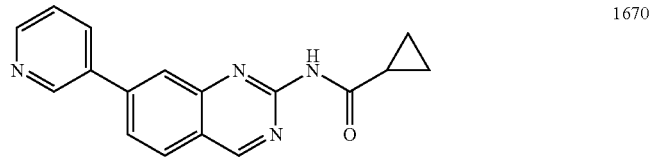 | 1670 |
| 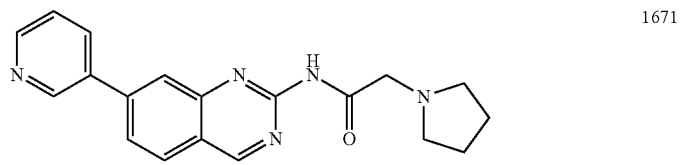 | 1671 |
| 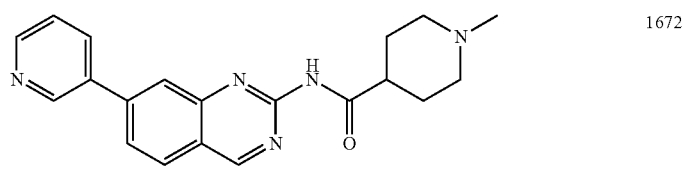 | 1672 |
| 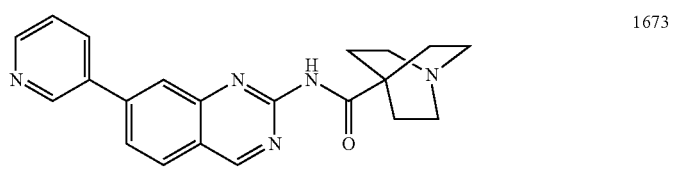 | 1673 |
| 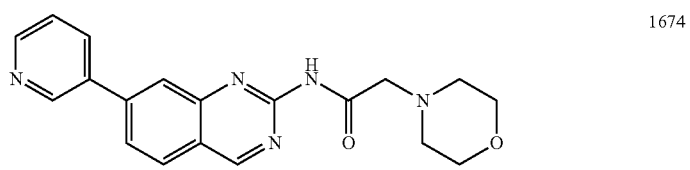 | 1674 |
| 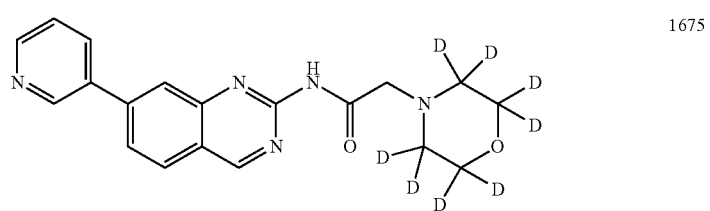 | 1675 |

TABLE 1-continued
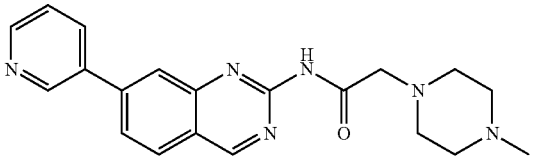 [SMILES: CN1CCN(CC(=O)Nc2ncc3ccc(-c4cccnc4)cc3n2)CC1] 1676
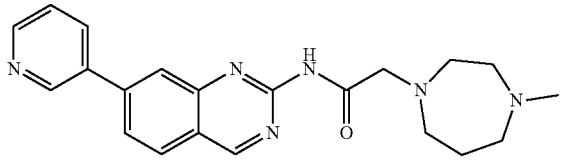 [SMILES: CN1CCCN(CC(=O)Nc2ncc3ccc(-c4cccnc4)cc3n2)CC1] 1677
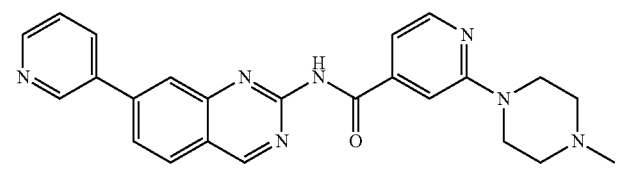 [SMILES: CN1CCN(c2cc(C(=O)Nc3ncc4ccc(-c5cccnc5)cc4n3)ccn2)CC1] 1678
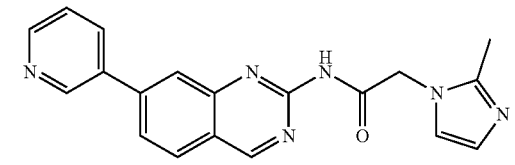 [SMILES: Cc1nccn1CC(=O)Nc1ncc2ccc(-c3cccnc3)cc2n1] 1679
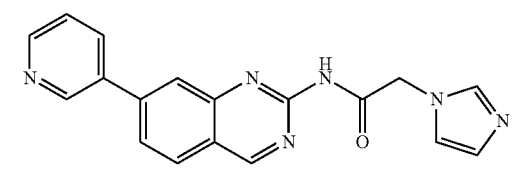 [SMILES: O=C(Cn1ccnc1)Nc1ncc2ccc(-c3cccnc3)cc2n1] 1680
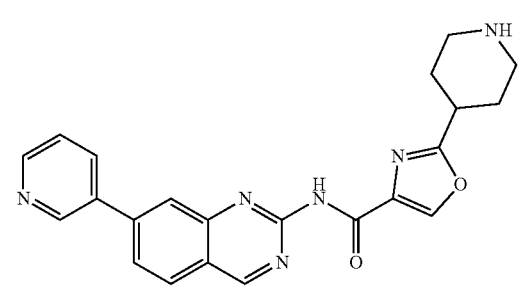 [SMILES: O=C(Nc1ncc2ccc(-c3cccnc3)cc2n1)c1coc(C2CCNCC2)n1] 1681
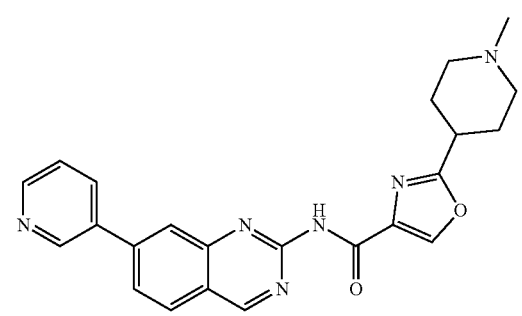 [SMILES: CN1CCC(c2nc(C(=O)Nc3ncc4ccc(-c5cccnc5)cc4n3)co2)CC1] 1682

TABLE 1-continued
| | |
|---|---|
| 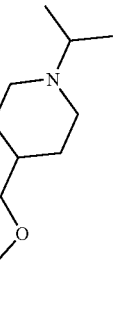 | 1683 |
| 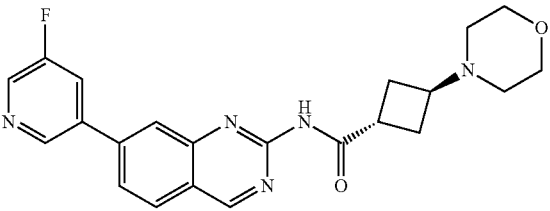 [SMILES: O=C(Nc1ncc2ccc(-c3cncc(F)c3)cc2n1)[C@H]1C[C@H](N2CCOCC2)C1] | 1684 |
| 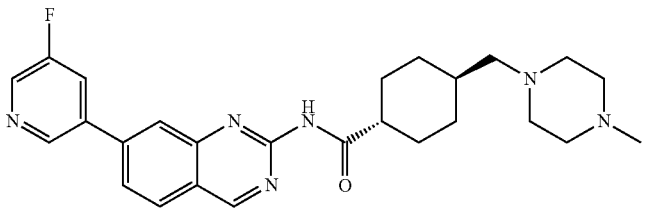 [SMILES: CN1CCN(C[C@H]2CC[C@H](C(=O)Nc3ncc4ccc(-c5cncc(F)c5)cc4n3)CC2)CC1] | 1685 |
| 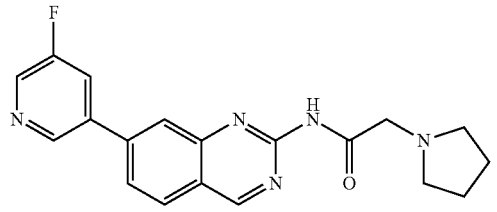 | 1686 |
| 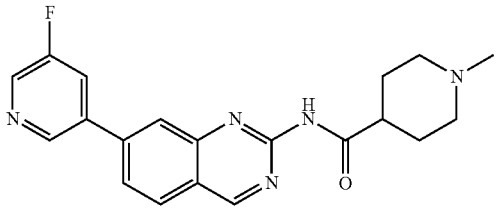 | 1687 |
| 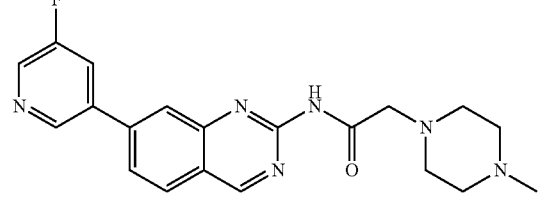 | 1688 |
| 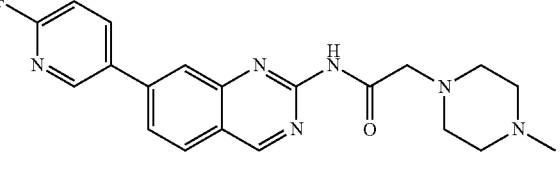 | 1689 |

TABLE 1-continued
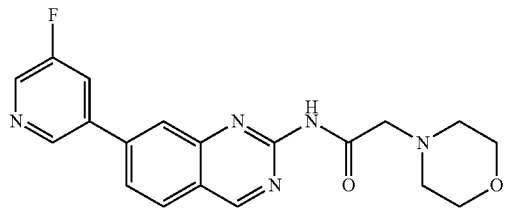 [SMILES: O=C(CN1CCOCC1)Nc1ncc2ccc(-c3cncc(F)c3)cc2n1] 1690
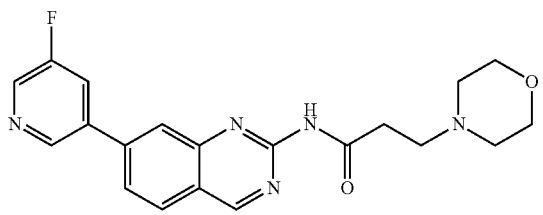 [SMILES: O=C(CCN1CCOCC1)Nc1ncc2ccc(-c3cncc(F)c3)cc2n1] 1691
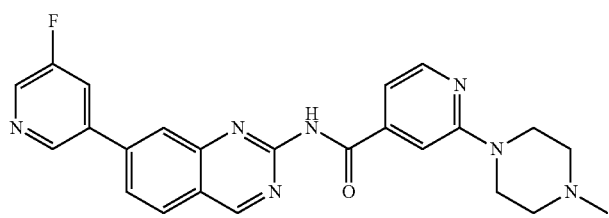 1692
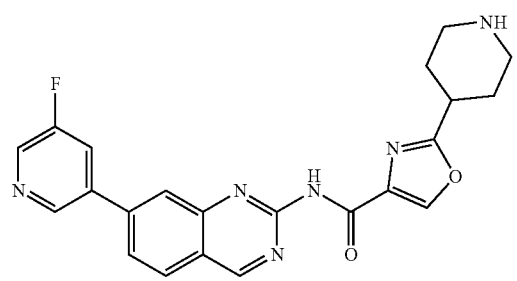 [SMILES: O=C(Nc1ncc2ccc(-c3cncc(F)c3)cc2n1)c1coc(C2CCNCC2)n1] 1693
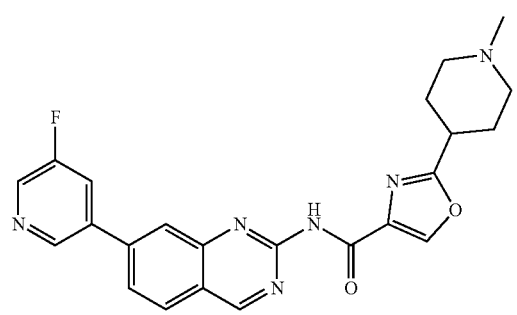 [SMILES: CN1CCC(c2nc(C(=O)Nc3ncc4ccc(-c5cncc(F)c5)cc4n3)co2)CC1] 1694
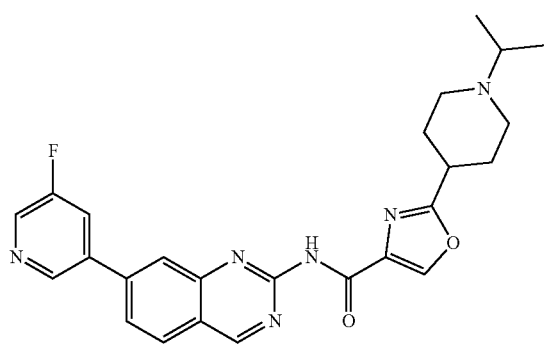 [SMILES: CC(C)N1CCC(c2nc(C(=O)Nc3ncc4ccc(-c5cncc(F)c5)cc4n3)co2)CC1] 1695

TABLE 1-continued
| | |
|---|---|
| 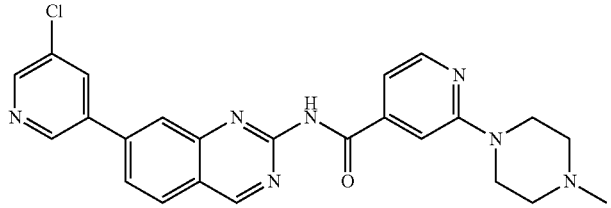 [SMILES: CN1CCN(c2cc(C(=O)Nc3ncc4ccc(-c5cncc(Cl)c5)cc4n3)ccn2)CC1] | 1696 |
| 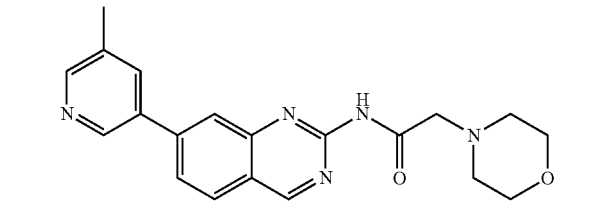 [SMILES: Cc1cncc(-c2ccc3cnc(NC(=O)CN4CCOCC4)nc3c2)c1] | 1697 |
| 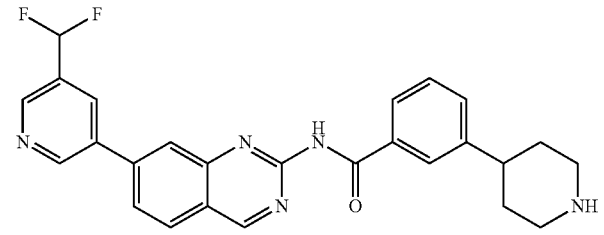 [SMILES: O=C(Nc1ncc2ccc(-c3cncc(C(F)F)c3)cc2n1)c1cccc(C2CCNCC2)c1] | 1698 |
| 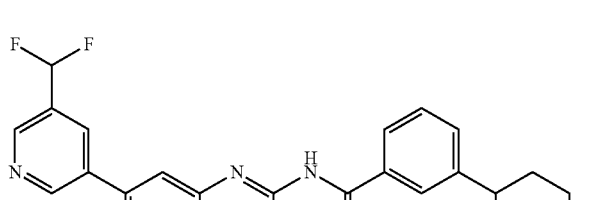 | 1699 |
|  | 1700 |
| | 1701 |
| | 1702 |

TABLE 1-continued
| | |
|---|---|
| 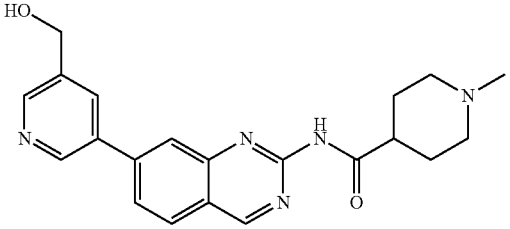 [SMILES: CN1CCC(C(=O)Nc2ncc3ccc(-c4cncc(CO)c4)cc3n2)CC1] | 1703 |
| 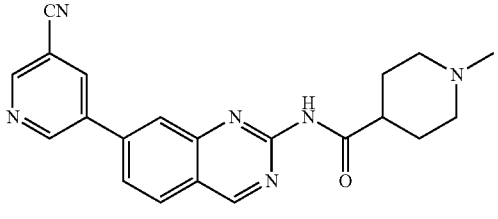 [SMILES: CN1CCC(C(=O)Nc2ncc3ccc(-c4cncc(C#N)c4)cc3n2)CC1] | 1704 |
| | 1705 |
| | 1706 |
| 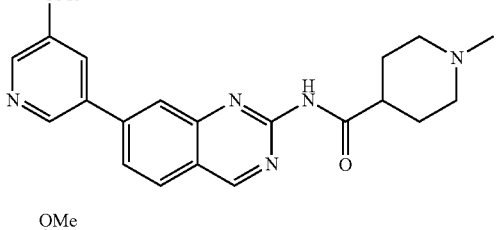 | 1707 |
| 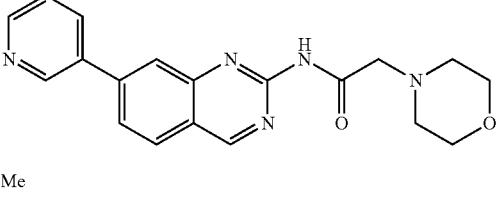 | 1708 |
| | 1709 |

TABLE 1-continued
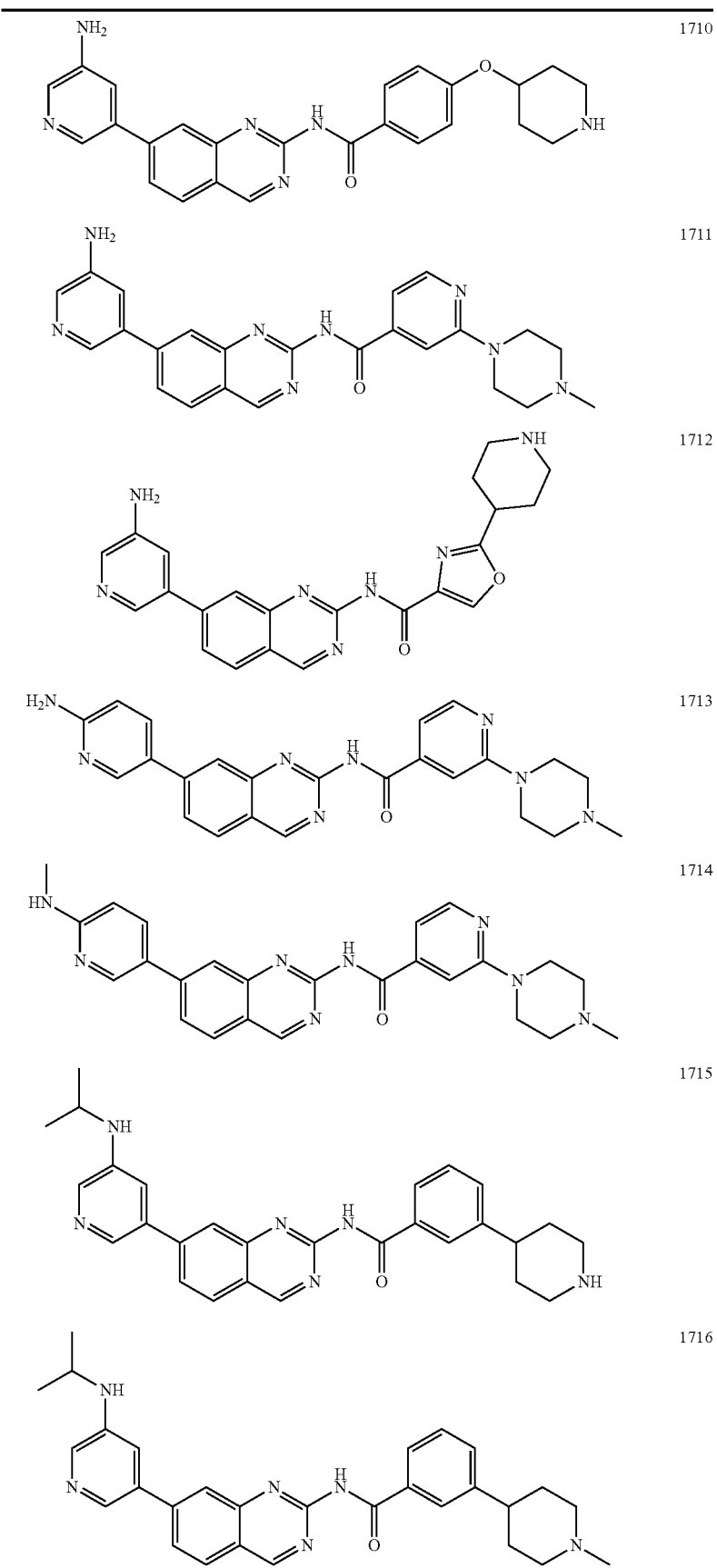

TABLE 1-continued
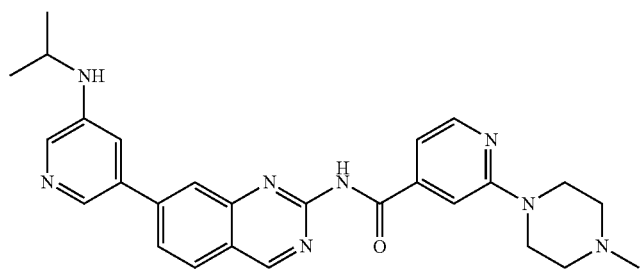
1717
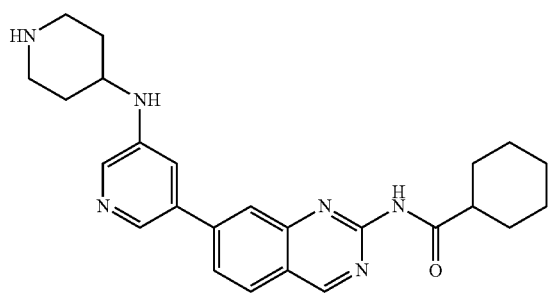 [SMILES: O=C(Nc1ncc2ccc(-c3cncc(NC4CCNCC4)c3)cc2n1)C1CCCCC1]
1718
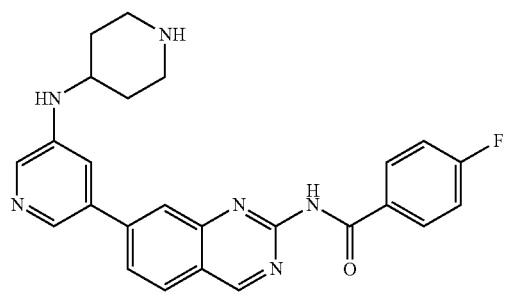 [SMILES: O=C(Nc1ncc2ccc(-c3cncc(NC4CCNCC4)c3)cc2n1)c1ccc(F)cc1]
1719
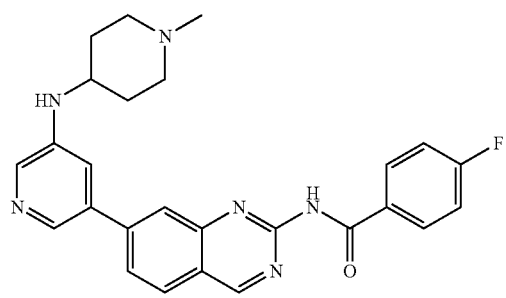 [SMILES: CN1CCC(Nc2cncc(-c3ccc4cnc(NC(=O)c5ccc(F)cc5)nc4c3)c2)CC1]
1720
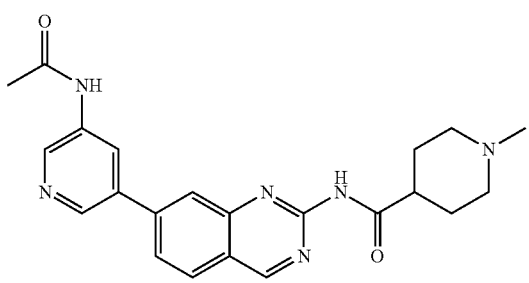
1721

TABLE 1-continued
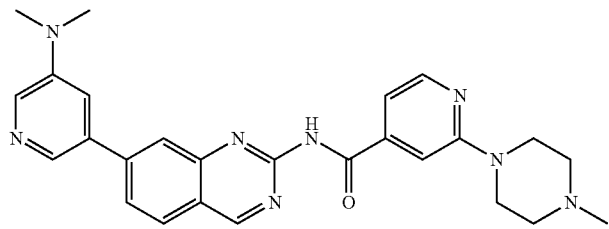 [SMILES: CN1CCN(c2cc(C(=O)Nc3ncc4ccc(-c5cncc(N(C)C)c5)cc4n3)ccn2)CC1]
1722
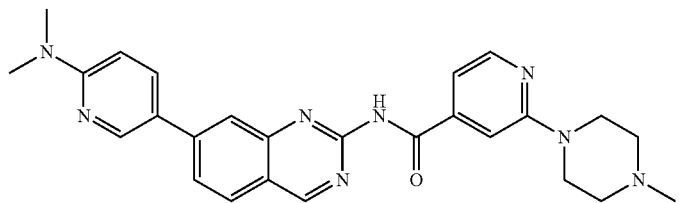
1723
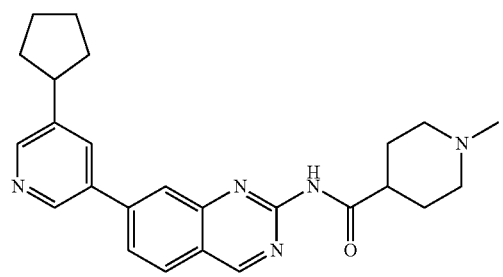 [SMILES: CN1CCC(C(=O)Nc2ncc3ccc(-c4cncc(C5CCCC5)c4)cc3n2)CC1]
1724
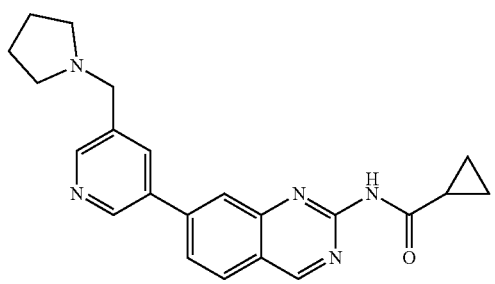 [SMILES: O=C(Nc1ncc2ccc(-c3cncc(CN4CCCC4)c3)cc2n1)C1CC1]
1725
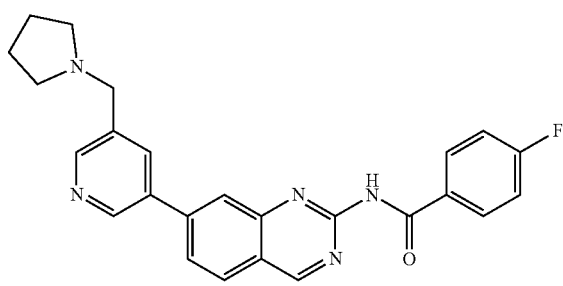 [SMILES: O=C(Nc1ncc2ccc(-c3cncc(CN4CCCC4)c3)cc2n1)c1ccc(F)cc1]
1726
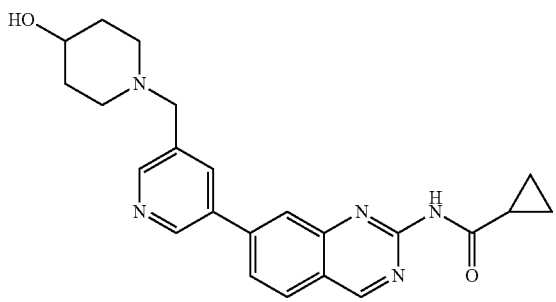 [SMILES: O=C(Nc1ncc2ccc(-c3cncc(CN4CCC(O)CC4)c3)cc2n1)C1CC1]
1727

TABLE 1-continued
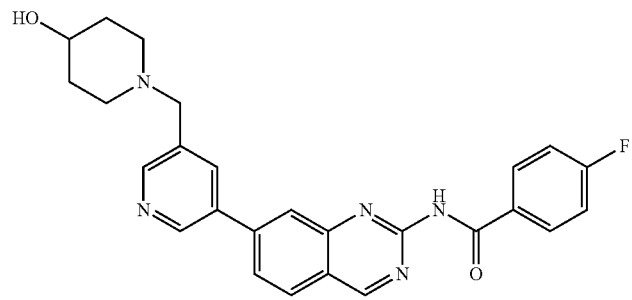 1728
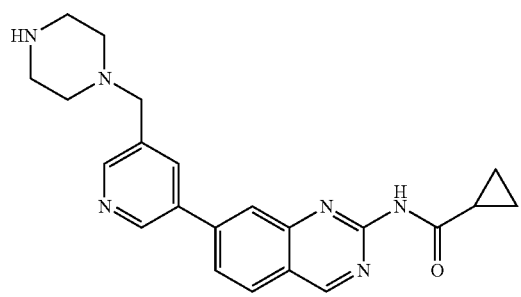 [SMILES: O=C(Nc1ncc2ccc(-c3cncc(CN4CCNCC4)c3)cc2n1)C1CC1] 1729
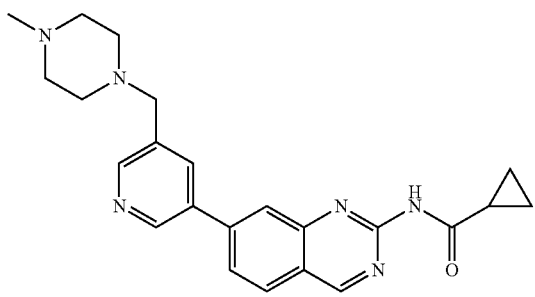 [SMILES: CN1CCN(Cc2cncc(-c3ccc4cnc(NC(=O)C5CC5)nc4c3)c2)CC1] 1730
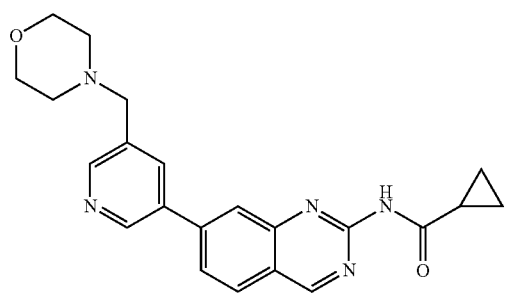 [SMILES: O=C(Nc1ncc2ccc(-c3cncc(CN4CCOCC4)c3)cc2n1)C1CC1] 1731
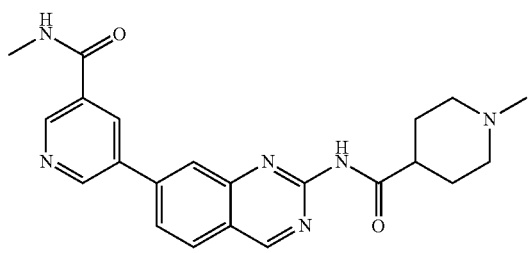 1732

TABLE 1-continued
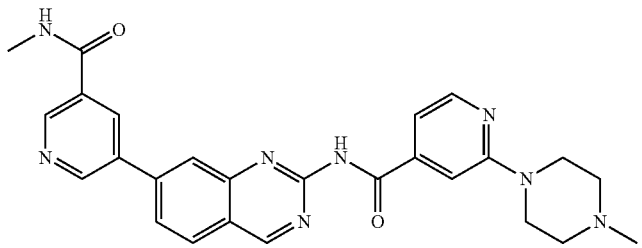
1733
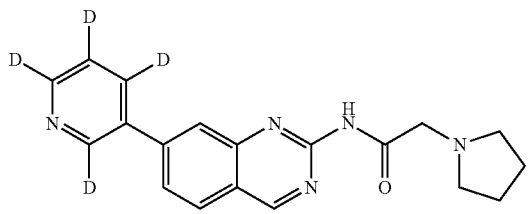 [SMILES: [2H]c1nc([2H])c(-c2ccc3cnc(NC(=O)CN4CCCC4)nc3c2)c([2H])c1[2H]]
1734
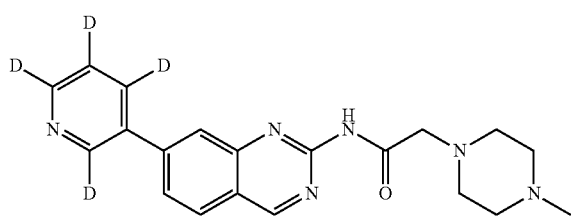 [SMILES: [2H]c1nc([2H])c(-c2ccc3cnc(NC(=O)CN4CCN(C)CC4)nc3c2)c([2H])c1[2H]]
1735
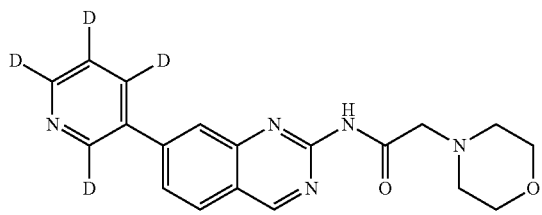
1736
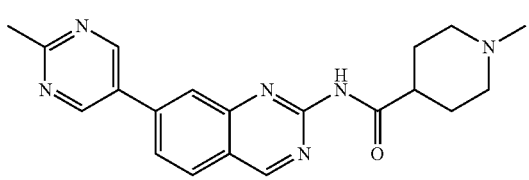
1737
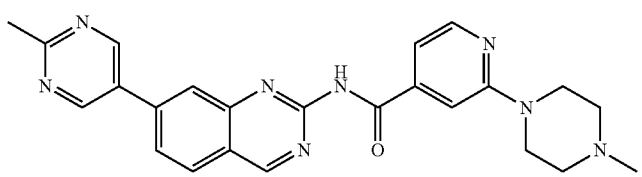
1738
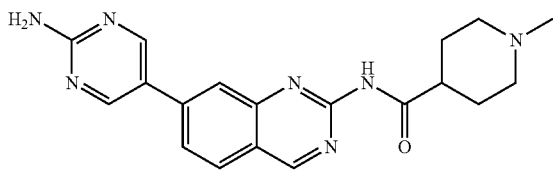 [SMILES: CN1CCC(C(=O)Nc2ncc3ccc(-c4cnc(N)nc4)cc3n2)CC1]
1739
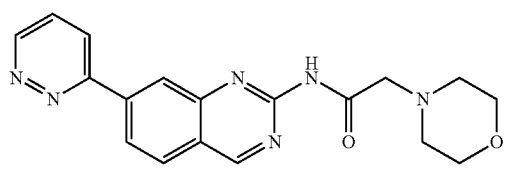 [SMILES: O=C(CN1CCOCC1)Nc1ncc2ccc(-c3cccnn3)cc2n1]
1740

TABLE 1-continued
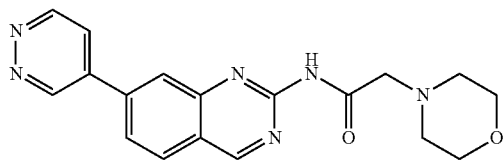 [SMILES: O=C(CN1CCOCC1)Nc1ncc2ccc(-c3ccnnc3)cc2n1] 1741
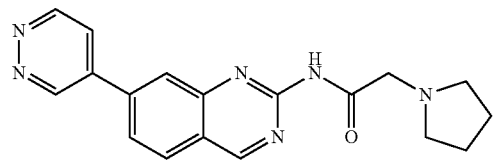 [SMILES: O=C(CN1CCCC1)Nc1ncc2ccc(-c3ccnnc3)cc2n1] 1742
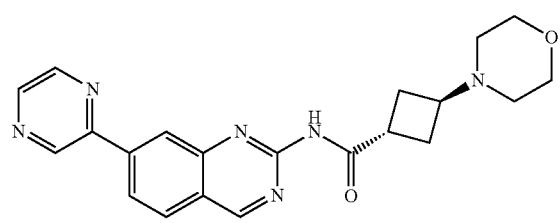 [SMILES: O=C(Nc1ncc2ccc(-c3cnccn3)cc2n1)[C@H]1C[C@H](N2CCOCC2)C1] 1743
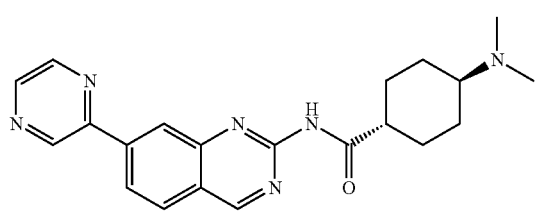 [SMILES: CN(C)[C@H]1CC[C@H](C(=O)Nc2ncc3ccc(-c4cnccn4)cc3n2)CC1] 1744
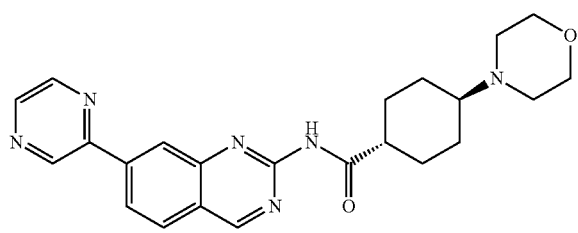 [SMILES: O=C(Nc1ncc2ccc(-c3cnccn3)cc2n1)[C@H]1CC[C@H](N2CCOCC2)CC1] 1745
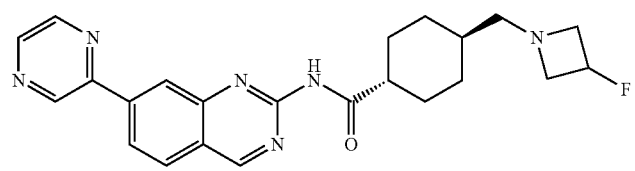 [SMILES: O=C(Nc1ncc2ccc(-c3cnccn3)cc2n1)[C@H]1CC[C@H](CN2CC(F)C2)CC1] 1746
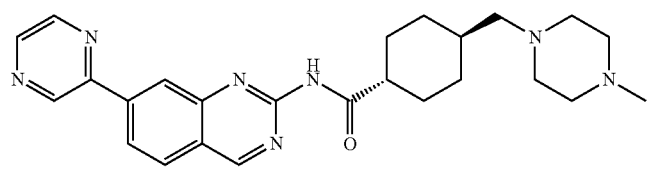 [SMILES: CN1CCN(C[C@H]2CC[C@H](C(=O)Nc3ncc4ccc(-c5cnccn5)cc4n3)CC2)CC1] 1747
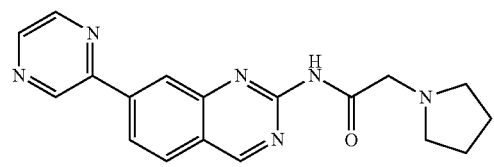 [SMILES: O=C(CN1CCCC1)Nc1ncc2ccc(-c3cnccn3)cc2n1] 1748

TABLE 1-continued
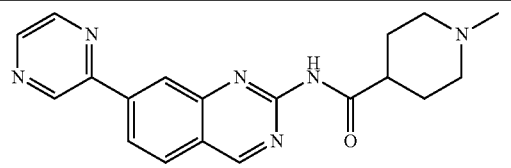 1749
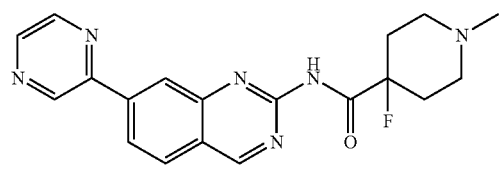 [SMILES: CN1CCC(F)(C(=O)Nc2ncc3ccc(-c4cnccn4)cc3n2)CC1] 1750
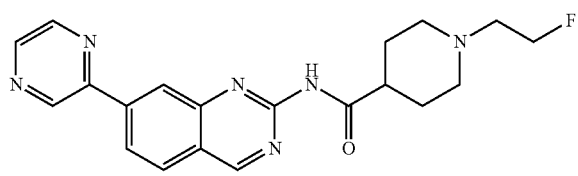 [SMILES: O=C(Nc1ncc2ccc(-c3cnccn3)cc2n1)C1CCN(CCF)CC1] 1751
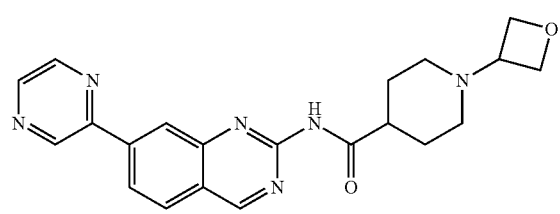 [SMILES: O=C(Nc1ncc2ccc(-c3cnccn3)cc2n1)C1CCN(C2COC2)CC1] 1752
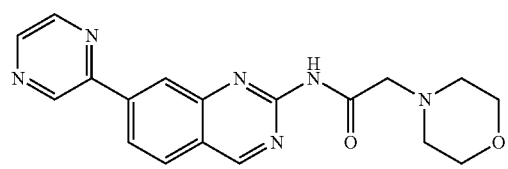 [SMILES: O=C(CN1CCOCC1)Nc1ncc2ccc(-c3cnccn3)cc2n1] 1753
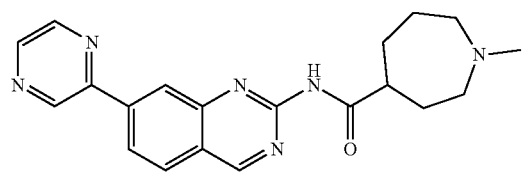 [SMILES: CN1CCCC(C(=O)Nc2ncc3ccc(-c4cnccn4)cc3n2)CC1] 1754
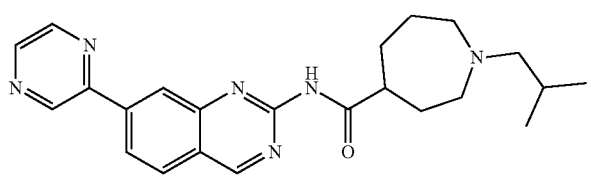 [SMILES: CC(C)CN1CCCC(C(=O)Nc2ncc3ccc(-c4cnccn4)cc3n2)CC1] 1755
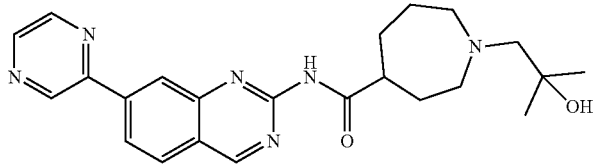 [SMILES: CC(C)(O)CN1CCCC(C(=O)Nc2ncc3ccc(-c4cnccn4)cc3n2)CC1] 1756
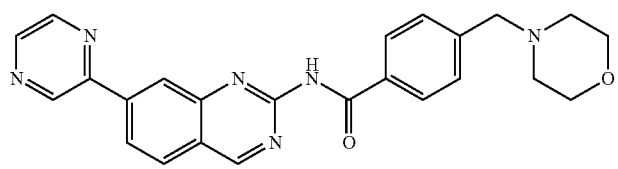 [SMILES: O=C(Nc1ncc2ccc(-c3cnccn3)cc2n1)c1ccc(CN2CCOCC2)cc1] 1757

TABLE 1-continued
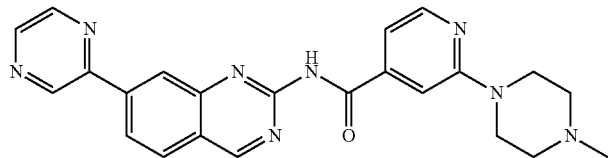 [SMILES: CN1CCN(c2cc(C(=O)Nc3ncc4ccc(-c5cnccn5)cc4n3)ccn2)CC1]
1758
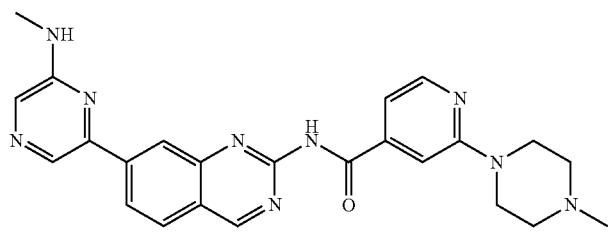 [SMILES: CNc1cncc(-c2ccc3cnc(NC(=O)c4ccnc(N5CCN(C)CC5)c4)nc3c2)n1]
1759
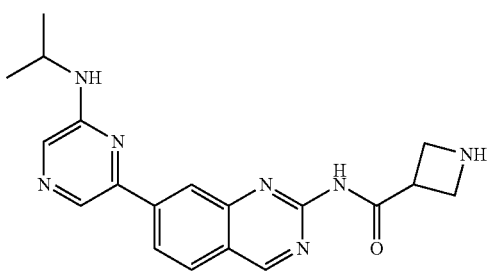 [SMILES: CC(C)Nc1cncc(-c2ccc3cnc(NC(=O)C4CNC4)nc3c2)n1]
1760
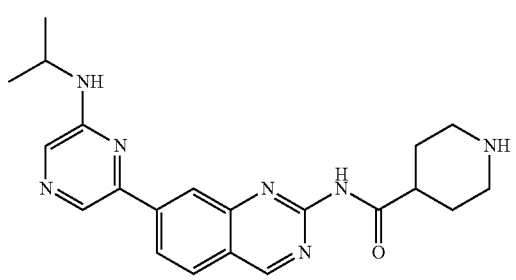 [SMILES: CC(C)Nc1cncc(-c2ccc3cnc(NC(=O)C4CCNCC4)nc3c2)n1]
1761
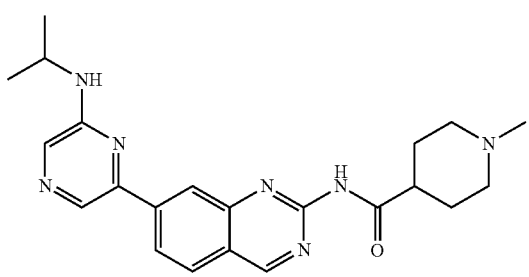 [SMILES: CC(C)Nc1cncc(-c2ccc3cnc(NC(=O)C4CCN(C)CC4)nc3c2)n1]
1762
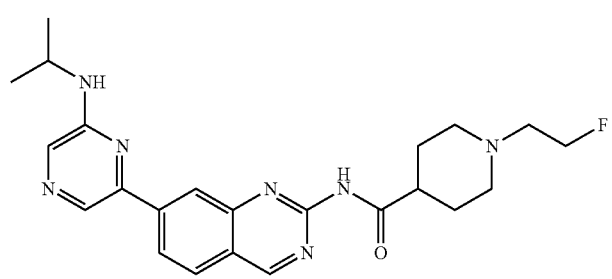 [SMILES: CC(C)Nc1cncc(-c2ccc3cnc(NC(=O)C4CCN(CCF)CC4)nc3c2)n1]
1763

TABLE 1-continued
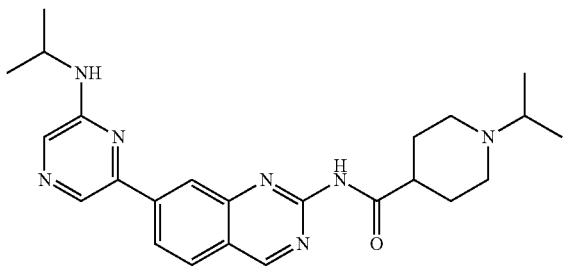 [SMILES: CC(C)Nc1cncc(-c2ccc3cnc(NC(=O)C4CCN(C(C)C)CC4)nc3c2)n1]
1764
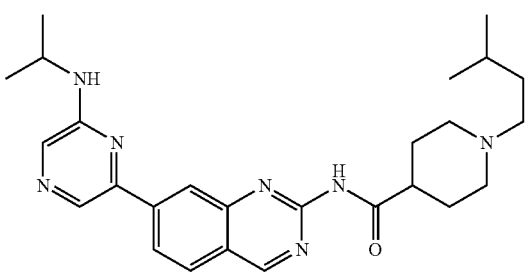 [SMILES: CC(C)CCN1CCC(C(=O)Nc2ncc3ccc(-c4cncc(NC(C)C)n4)cc3n2)CC1]
1765
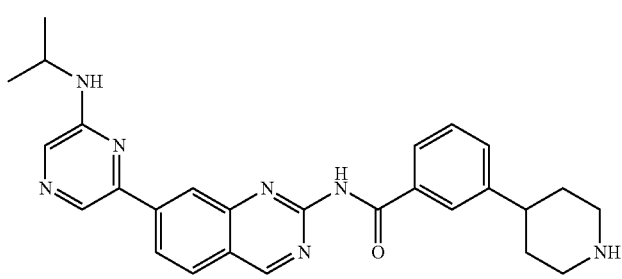 [SMILES: CC(C)Nc1cncc(-c2ccc3cnc(NC(=O)c4cccc(C5CCNCC5)c4)nc3c2)n1]
1766
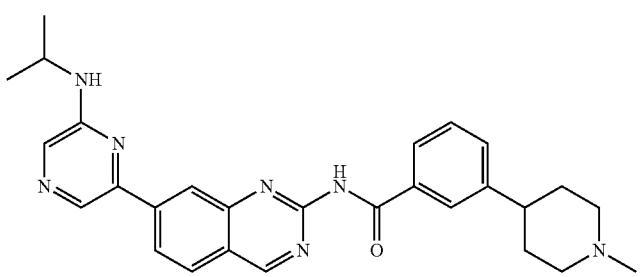 [SMILES: CC(C)Nc1cncc(-c2ccc3cnc(NC(=O)c4cccc(C5CCN(C)CC5)c4)nc3c2)n1]
1767
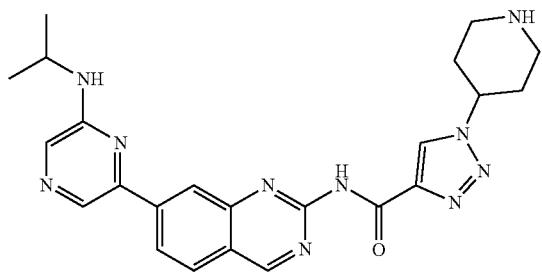 [SMILES: CC(C)Nc1cncc(-c2ccc3cnc(NC(=O)c4cn(C5CCNCC5)nn4)nc3c2)n1]
1768

TABLE 1-continued
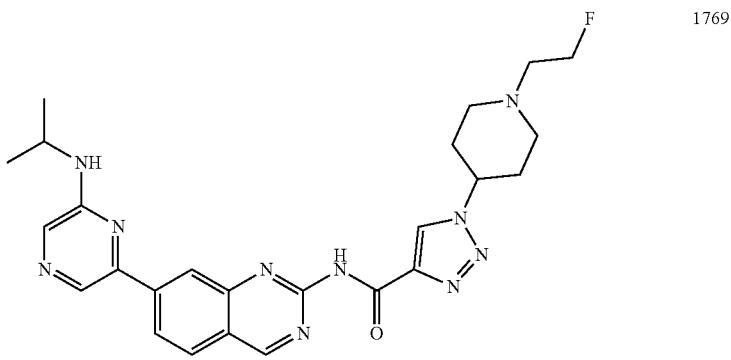
1769
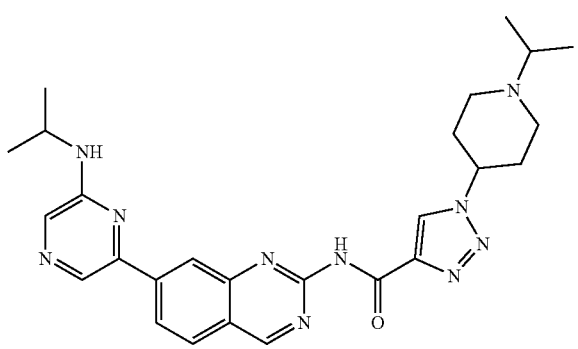 [SMILES: CC(C)Nc1cncc(-c2ccc3cnc(NC(=O)c4cn(C5CCN(C(C)C)CC5)nn4)nc3c2)n1]
1770
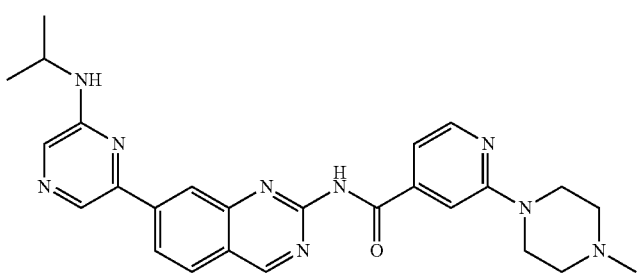 [SMILES: CC(C)Nc1cncc(-c2ccc3cnc(NC(=O)c4ccnc(N5CCN(C)CC5)c4)nc3c2)n1]
1771
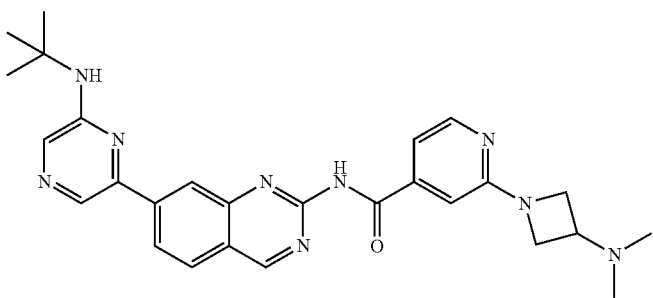 [SMILES: CN(C)C1CN(c2cc(C(=O)Nc3ncc4ccc(-c5cncc(NC(C)(C)C)n5)cc4n3)ccn2)C1]
1772
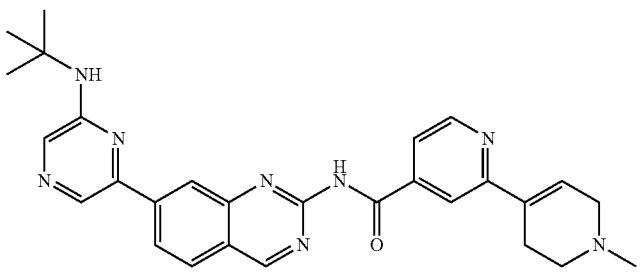
1773

TABLE 1-continued
1774
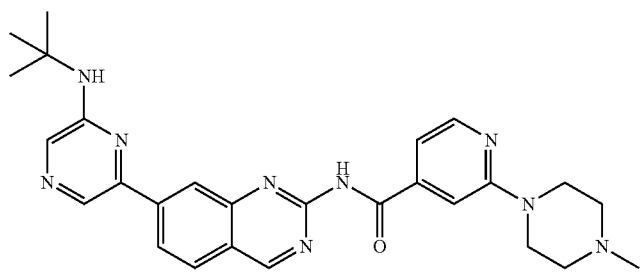 [SMILES: CN1CCN(c2cc(C(=O)Nc3ncc4ccc(-c5cncc(NC(C)(C)C)n5)cc4n3)ccn2)CC1]
1775
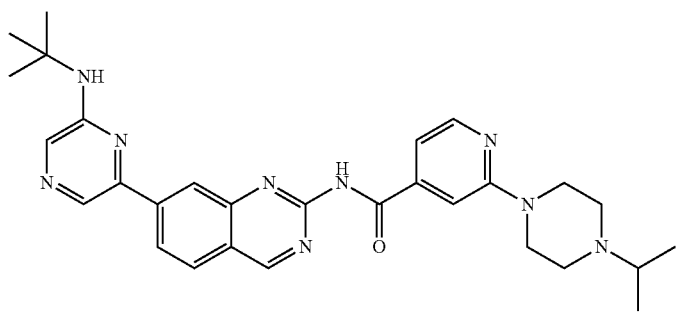 [SMILES: CC(C)N1CCN(c2cc(C(=O)Nc3ncc4ccc(-c5cncc(NC(C)(C)C)n5)cc4n3)ccn2)CC1]
1776
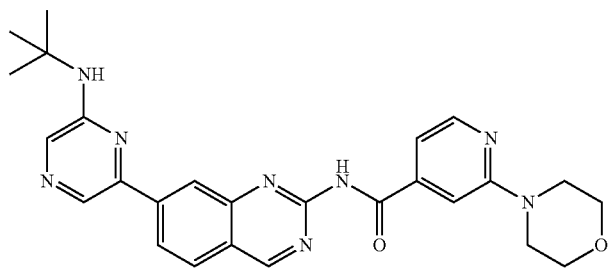 [SMILES: CC(C)(C)Nc1cncc(-c2ccc3cnc(NC(=O)c4ccnc(N5CCOCC5)c4)nc3c2)n1]
1777
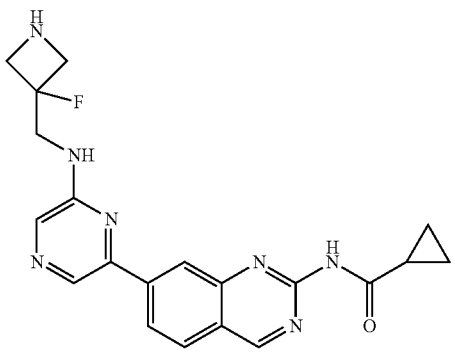 [SMILES: O=C(Nc1ncc2ccc(-c3cncc(NCC4(F)CNC4)n3)cc2n1)C1CC1]
1778
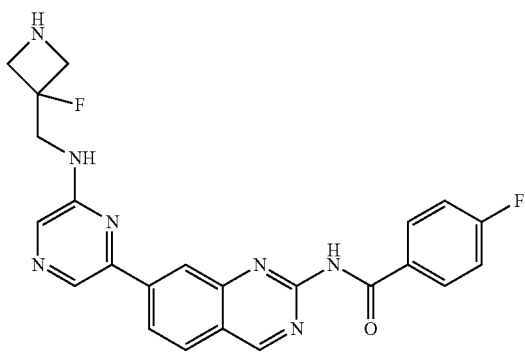 [SMILES: O=C(Nc1ncc2ccc(-c3cncc(NCC4(F)CNC4)n3)cc2n1)c1ccc(F)cc1]

TABLE 1-continued
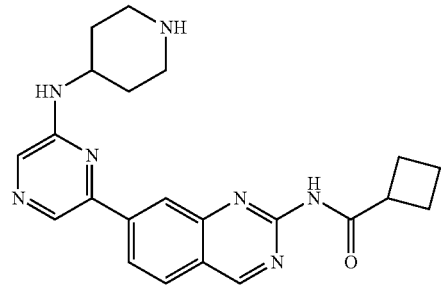 [SMILES: O=C(Nc1ncc2ccc(-c3cncc(NC4CCNCC4)n3)cc2n1)C1CCC1]
1779
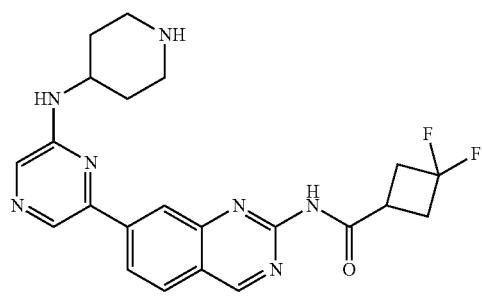 [SMILES: O=C(Nc1ncc2ccc(-c3cncc(NC4CCNCC4)n3)cc2n1)C1CC(F)(F)C1]
1780
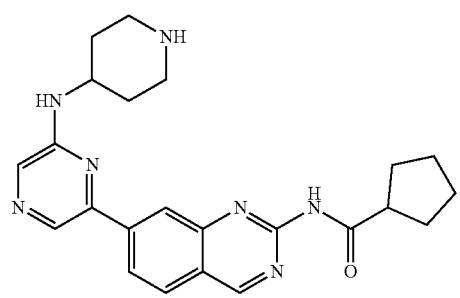 [SMILES: O=C(Nc1ncc2ccc(-c3cncc(NC4CCNCC4)n3)cc2n1)C1CCCC1]
1781
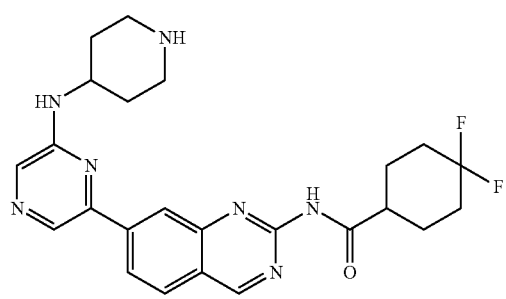 [SMILES: O=C(Nc1ncc2ccc(-c3cncc(NC4CCNCC4)n3)cc2n1)C1CCC(F)(F)CC1]
1782
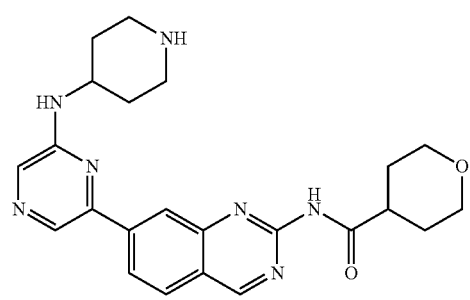 [SMILES: O=C(Nc1ncc2ccc(-c3cncc(NC4CCNCC4)n3)cc2n1)C1CCOCC1]
1783

TABLE 1-continued
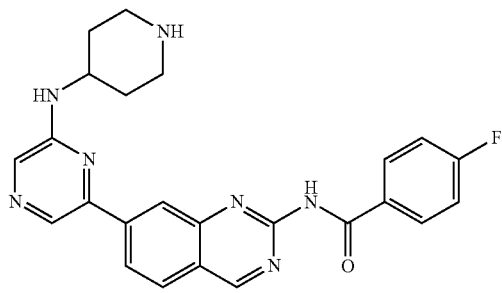 [SMILES: O=C(Nc1ncc2ccc(-c3cncc(NC4CCNCC4)n3)cc2n1)c1ccc(F)cc1]
1784
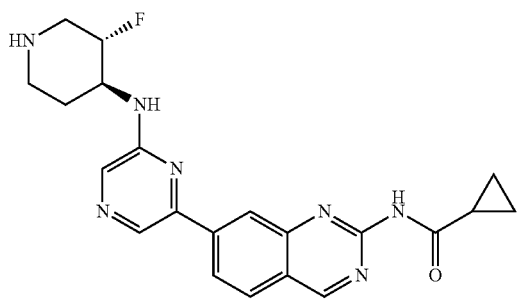 [SMILES: O=C(Nc1ncc2ccc(-c3cncc(N[C@H]4CCNC[C@@H]4F)n3)cc2n1)C1CC1]
1785
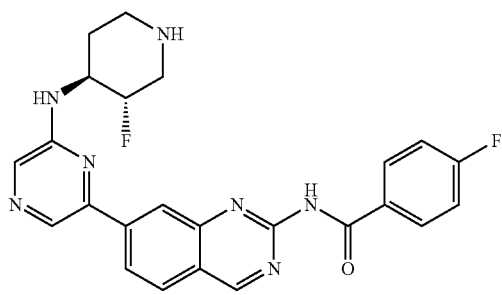 [SMILES: O=C(Nc1ncc2ccc(-c3cncc(N[C@H]4CCNC[C@@H]4F)n3)cc2n1)c1ccc(F)cc1]
1786
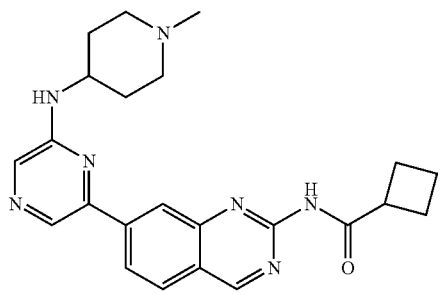 [SMILES: CN1CCC(Nc2cncc(-c3ccc4cnc(NC(=O)C5CCC5)nc4c3)n2)CC1]
1787
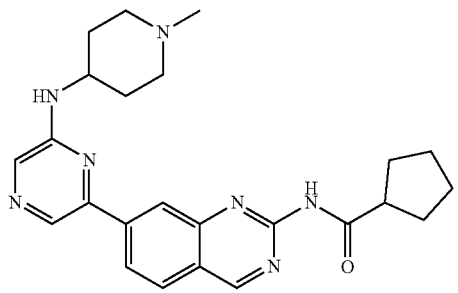 [SMILES: CN1CCC(Nc2cncc(-c3ccc4cnc(NC(=O)C5CCCC5)nc4c3)n2)CC1]
1788

TABLE 1-continued
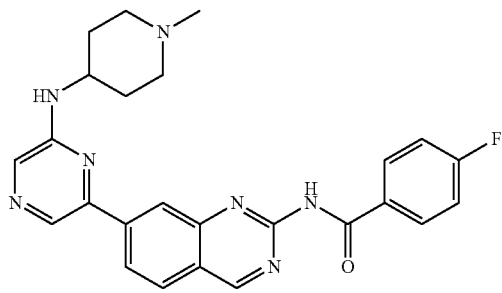 [SMILES: CN1CCC(Nc2cncc(-c3ccc4cnc(NC(=O)c5ccc(F)cc5)nc4c3)n2)CC1] 1789
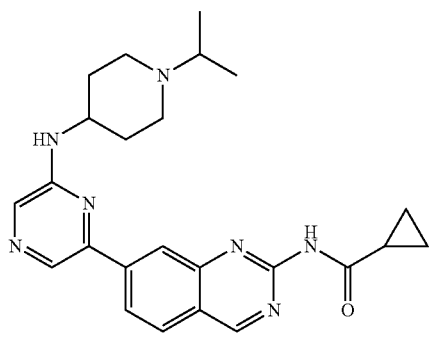 [SMILES: CC(C)N1CCC(Nc2cncc(-c3ccc4cnc(NC(=O)C5CC5)nc4c3)n2)CC1] 1790
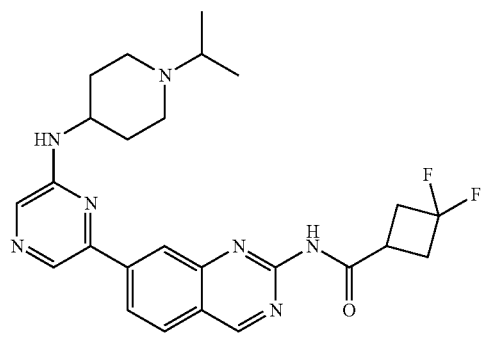 1791
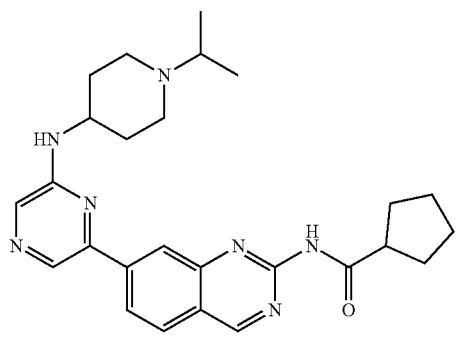 [SMILES: CC(C)N1CCC(Nc2cncc(-c3ccc4cnc(NC(=O)C5CCCC5)nc4c3)n2)CC1] 1792
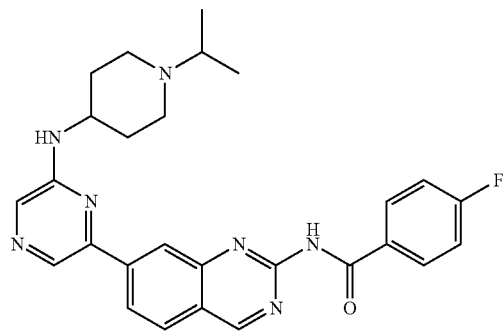 1793

TABLE 1-continued
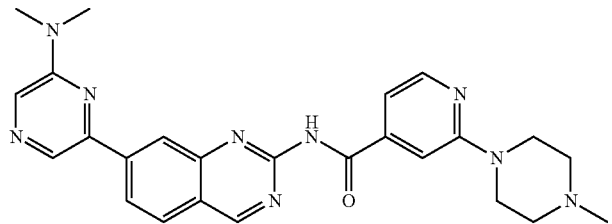 [SMILES: CN1CCN(c2cc(C(=O)Nc3ncc4ccc(-c5cncc(N(C)C)n5)cc4n3)ccn2)CC1]
1794
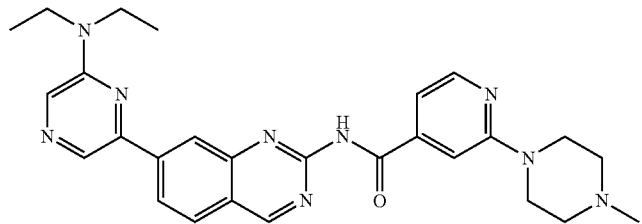 [SMILES: CCN(CC)c1cncc(-c2ccc3cnc(NC(=O)c4ccnc(N5CCN(C)CC5)c4)nc3c2)n1]
1795
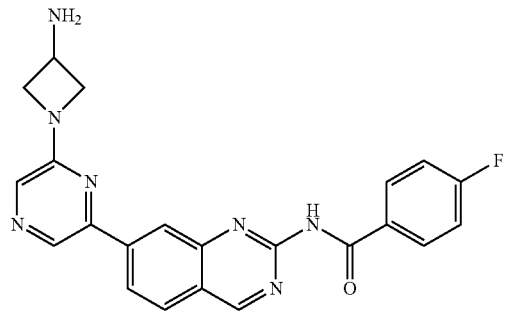
1796
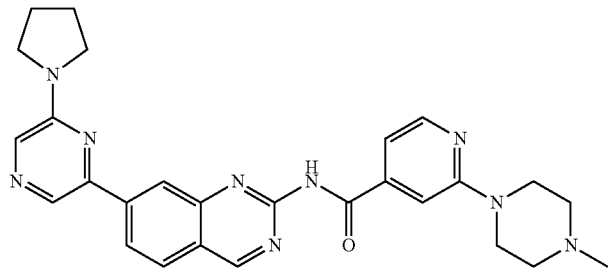 [SMILES: CN1CCN(c2cc(C(=O)Nc3ncc4ccc(-c5cncc(N6CCCC6)n5)cc4n3)ccn2)CC1]
1797
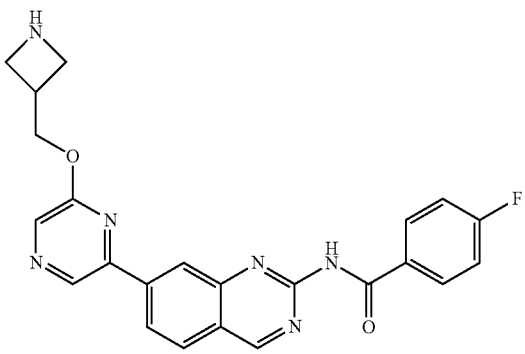 [SMILES: O=C(Nc1ncc2ccc(-c3cncc(OCC4CNC4)n3)cc2n1)c1ccc(F)cc1]
1798

TABLE 1-continued
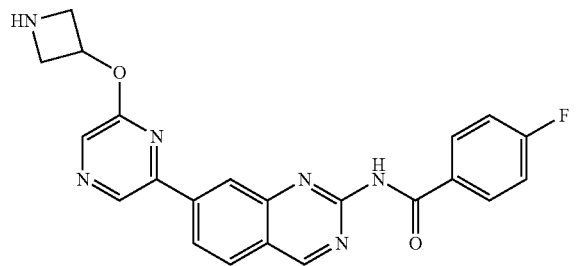 [SMILES: O=C(Nc1ncc2ccc(-c3cncc(OC4CNC4)n3)cc2n1)c1ccc(F)cc1] 1799
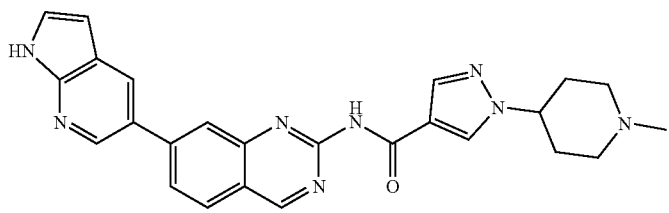 [SMILES: CN1CCC(n2cc(C(=O)Nc3ncc4ccc(-c5cnc6[nH]ccc6c5)cc4n3)cn2)CC1] 1800
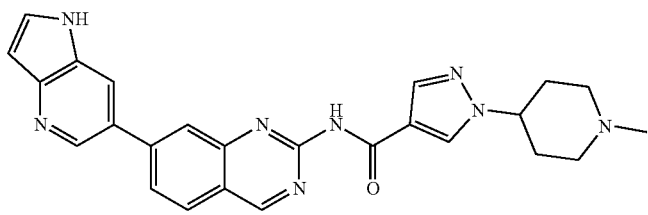 [SMILES: CN1CCC(n2cc(C(=O)Nc3ncc4ccc(-c5cnc6cc[nH]c6c5)cc4n3)cn2)CC1] 1801
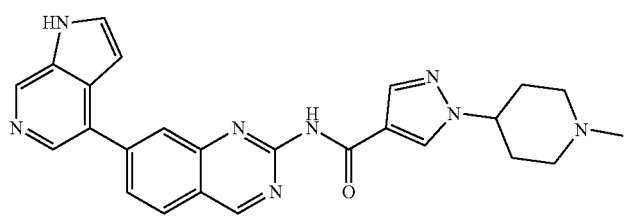 [SMILES: CN1CCC(n2cc(C(=O)Nc3ncc4ccc(-c5cncc6[nH]ccc56)cc4n3)cn2)CC1] 1802
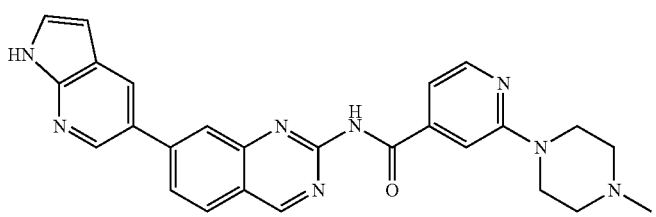 [SMILES: CN1CCN(c2cc(C(=O)Nc3ncc4ccc(-c5cnc6[nH]ccc6c5)cc4n3)ccn2)CC1] 1803
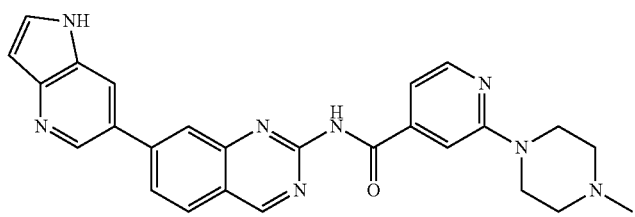 [SMILES: CN1CCN(c2cc(C(=O)Nc3ncc4ccc(-c5cnc6cc[nH]c6c5)cc4n3)ccn2)CC1] 1804
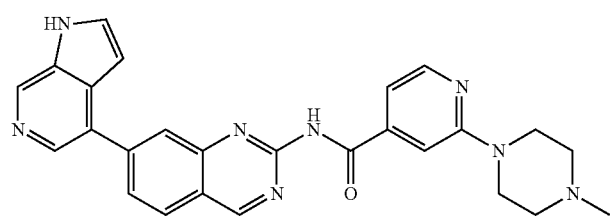 [SMILES: CN1CCN(c2cc(C(=O)Nc3ncc4ccc(-c5cncc6[nH]ccc56)cc4n3)ccn2)CC1] 1805

TABLE 1-continued
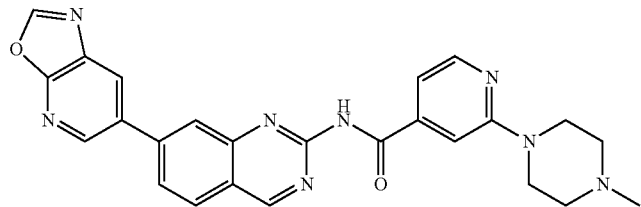 [SMILES: CN1CCN(c2cc(C(=O)Nc3ncc4ccc(-c5cnc6ocnc6c5)cc4n3)ccn2)CC1] 1806
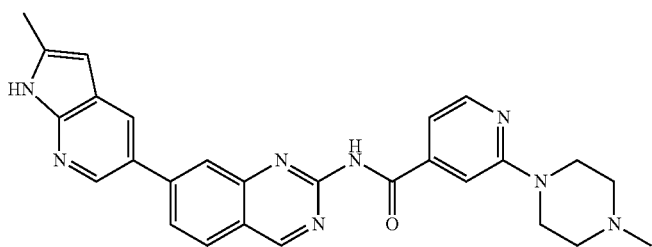 1807
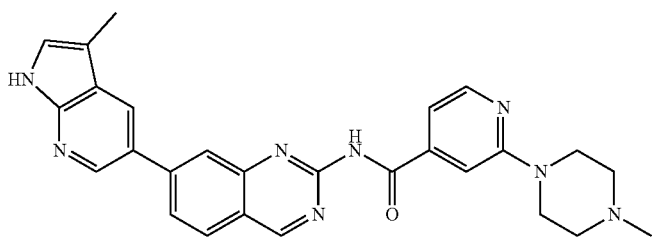 [SMILES: Cc1c[nH]c2ncc(-c3ccc4cnc(NC(=O)c5ccnc(N6CCN(C)CC6)c5)nc4c3)cc12] 1808
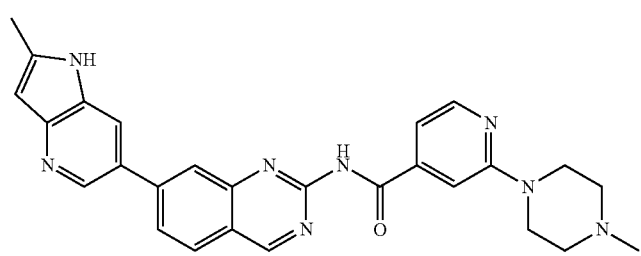 1809
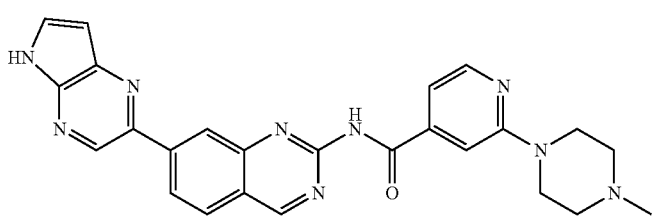 [SMILES: CN1CCN(c2cc(C(=O)Nc3ncc4ccc(-c5cnc6[nH]ccc6n5)cc4n3)ccn2)CC1] 1810
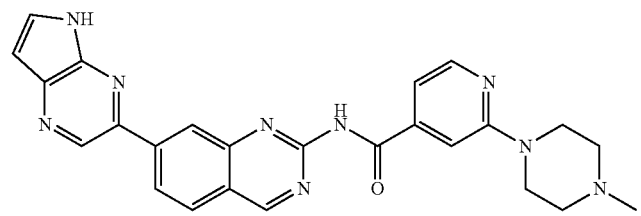 1811

TABLE 1-continued
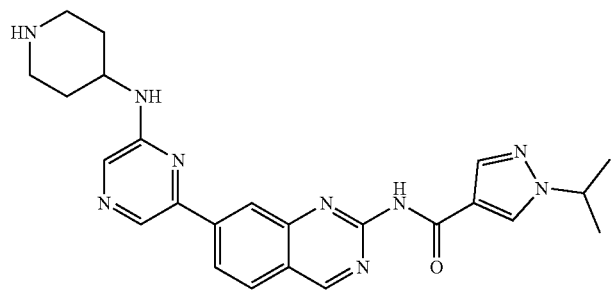
1812
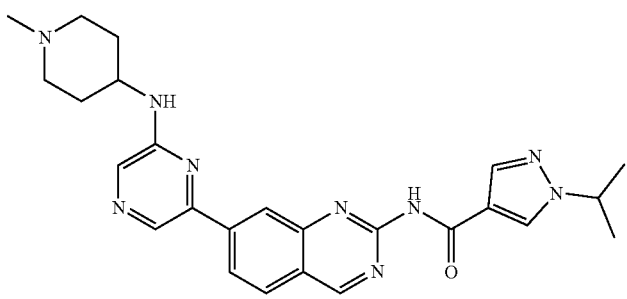 [SMILES: CC(C)n1cc(C(=O)Nc2ncc3ccc(-c4cncc(NC5CCN(C)CC5)n4)cc3n2)cn1]
1813
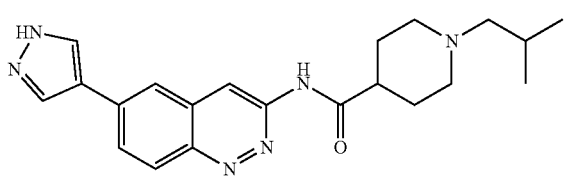 [SMILES: CC(C)CN1CCC(C(=O)Nc2cc3cc(-c4cn[nH]c4)ccc3nn2)CC1]
1814
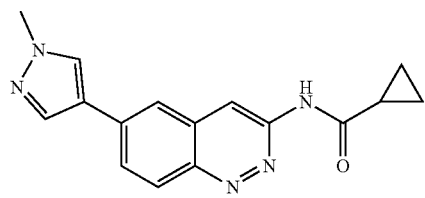 [SMILES: Cn1cc(-c2ccc3nnc(NC(=O)C4CC4)cc3c2)cn1]
1815
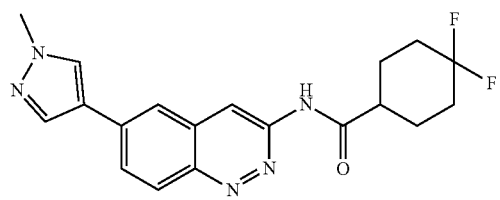 [SMILES: Cn1cc(-c2ccc3nnc(NC(=O)C4CCC(F)(F)CC4)cc3c2)cn1]
1816
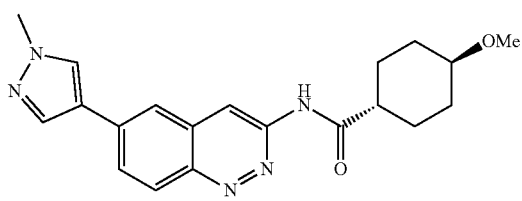 [SMILES: CO[C@H]1CC[C@H](C(=O)Nc2cc3cc(-c4cnn(C)c4)ccc3nn2)CC1]
1817
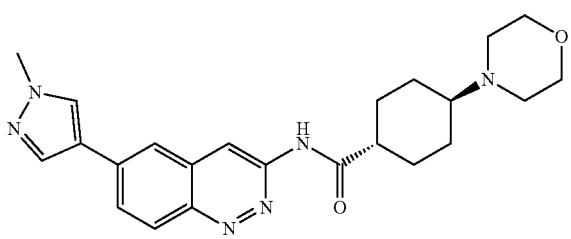 [SMILES: Cn1cc(-c2ccc3nnc(NC(=O)[C@H]4CC[C@H](N5CCOCC5)CC4)cc3c2)cn1]
1818

TABLE 1-continued
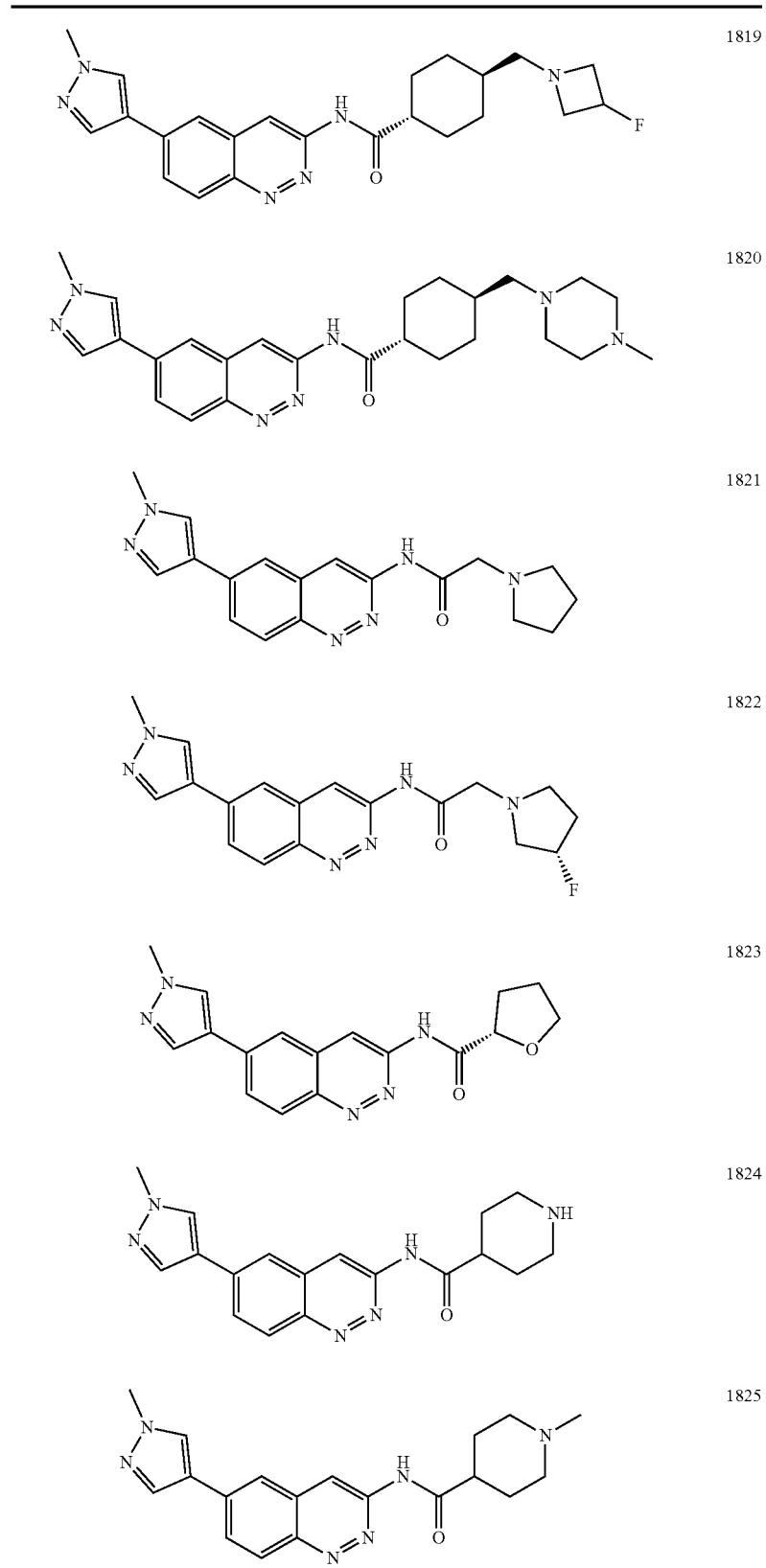

TABLE 1-continued
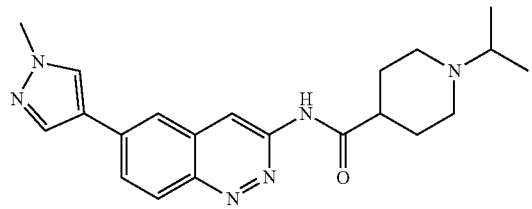 [SMILES: CC(C)N1CCC(C(=O)Nc2cc3cc(-c4cnn(C)c4)ccc3nn2)CC1] 1826
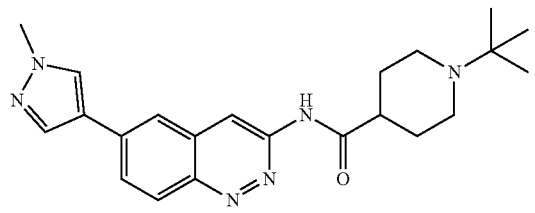 [SMILES: Cn1cc(-c2ccc3nnc(NC(=O)C4CCN(C(C)(C)C)CC4)cc3c2)cn1] 1827
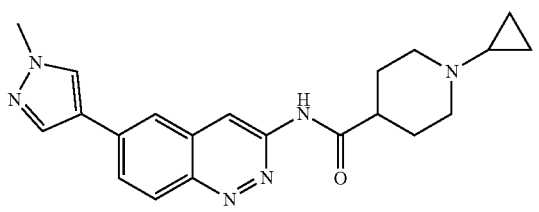 [SMILES: Cn1cc(-c2ccc3nnc(NC(=O)C4CCN(C5CC5)CC4)cc3c2)cn1] 1828
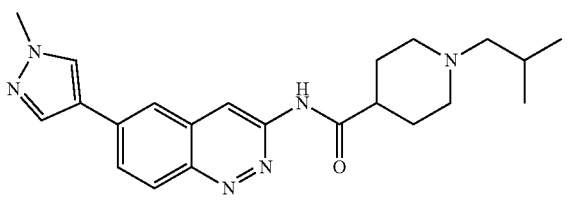 1829
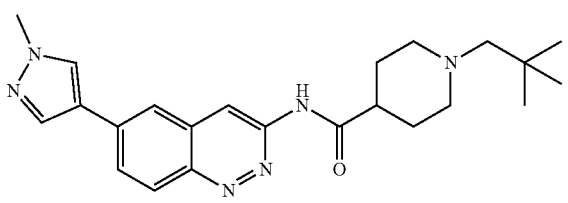 [SMILES: Cn1cc(-c2ccc3nnc(NC(=O)C4CCN(CC(C)(C)C)CC4)cc3c2)cn1] 1830
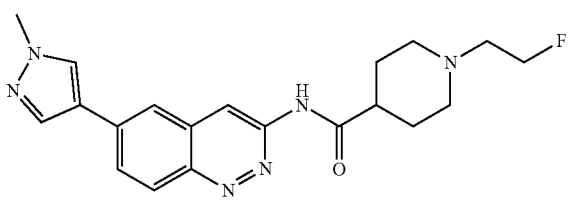 [SMILES: Cn1cc(-c2ccc3nnc(NC(=O)C4CCN(CCF)CC4)cc3c2)cn1] 1831
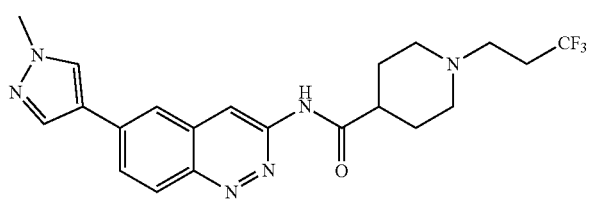 [SMILES: Cn1cc(-c2ccc3nnc(NC(=O)C4CCN(CCC(F)(F)F)CC4)cc3c2)cn1] 1832

TABLE 1-continued
| | |
|---|---|
| 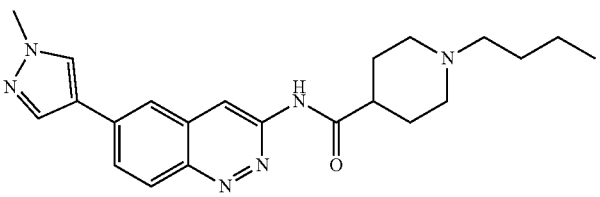 | 1833 |
| 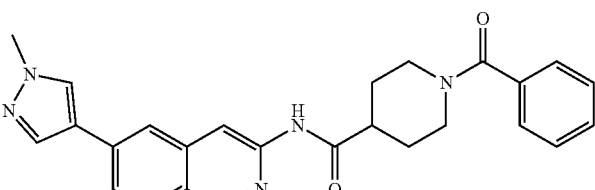 | 1834 |
| 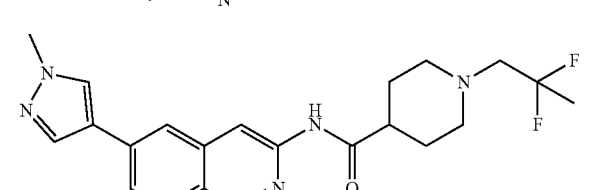 | 1835 |
| 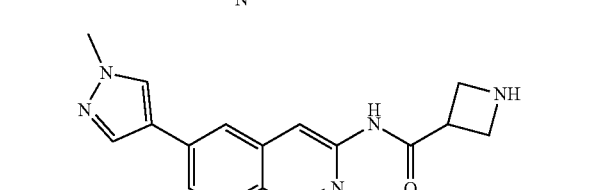 | 1836 |
| 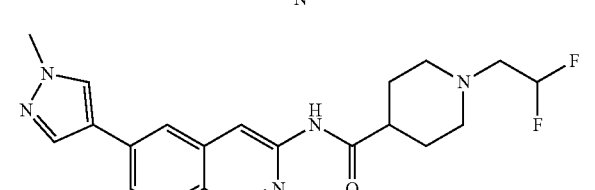 | 1837 |
| 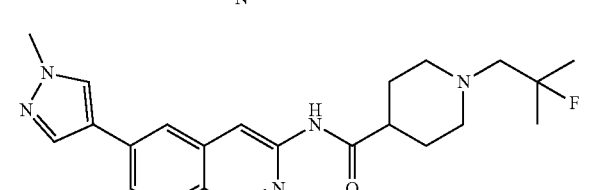 | 1838 |
| 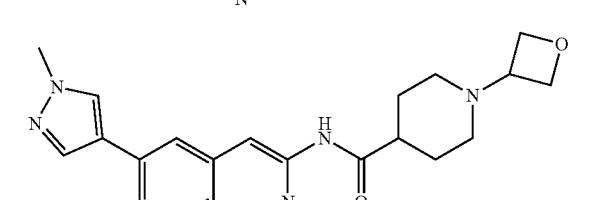 | 1839 |
| 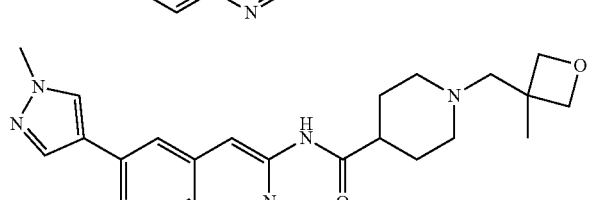 | 1840 |

TABLE 1-continued
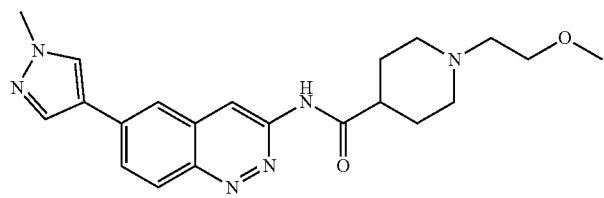 [SMILES: CCCCN1CCC(C(=O)Nc2cc3cc(-c4cnn(C)c4)ccc3nn2)CC1]
1841
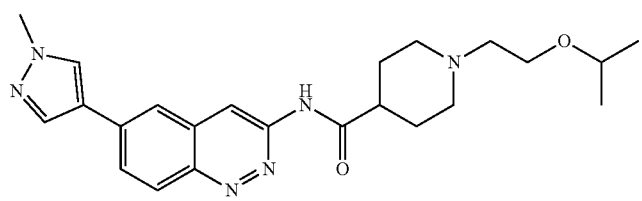 [SMILES: CC(C)OCCN1CCC(C(=O)Nc2cc3cc(-c4cnn(C)c4)ccc3nn2)CC1]
1842
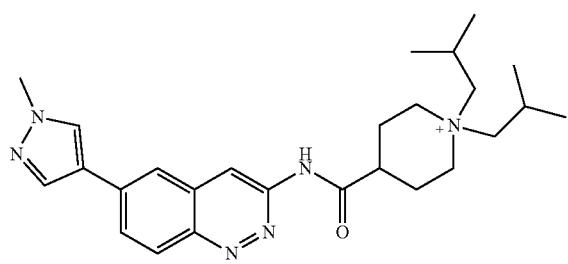
1843
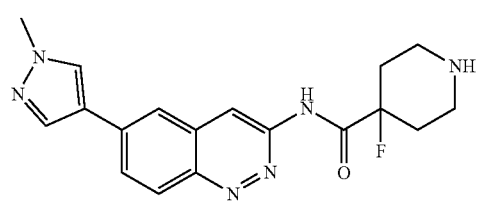 [SMILES: Cn1cc(-c2ccc3nnc(NC(=O)C4(F)CCNCC4)cc3c2)cn1]
1844
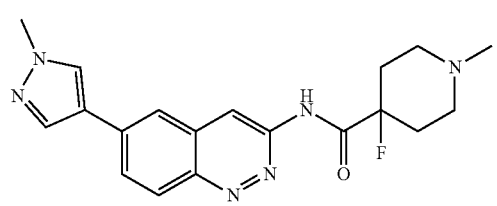 [SMILES: CN1CCC(F)(C(=O)Nc2cc3cc(-c4cnn(C)c4)ccc3nn2)CC1]
1845
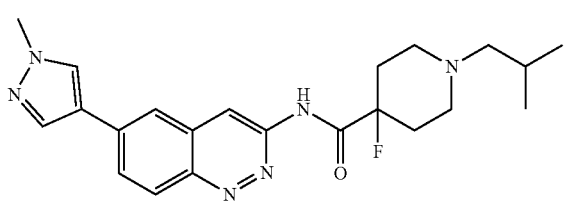 [SMILES: CC(C)CN1CCC(F)(C(=O)Nc2cc3cc(-c4cnn(C)c4)ccc3nn2)CC1]
1846
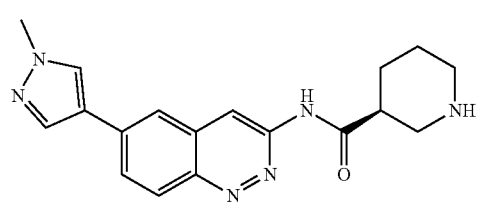 [SMILES: Cn1cc(-c2ccc3nnc(NC(=O)[C@H]4CCCNC4)cc3c2)cn1]
1847

TABLE 1-continued
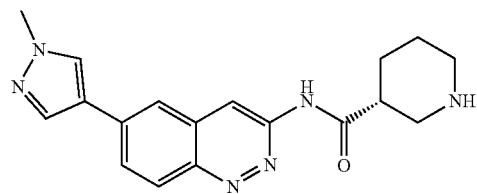 [SMILES: Cn1cc(-c2ccc3nnc(NC(=O)[C@@H]4CCCNC4)cc3c2)cn1]
1848
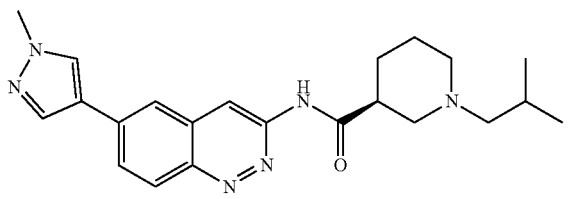 [SMILES: CC(C)CN1CCC[C@H](C(=O)Nc2cc3cc(-c4cnn(C)c4)ccc3nn2)C1]
1849
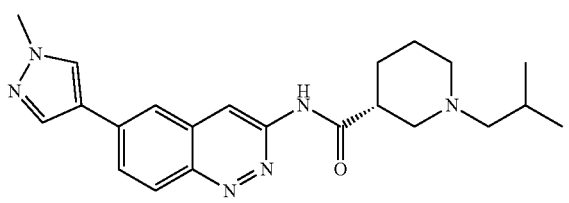 [SMILES: CC(C)CN1CCC[C@@H](C(=O)Nc2cc3cc(-c4cnn(C)c4)ccc3nn2)C1]
1850
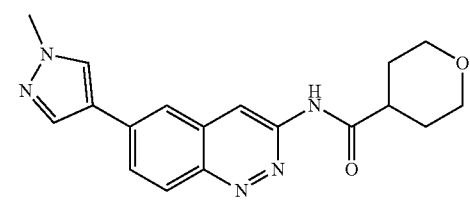 [SMILES: Cn1cc(-c2ccc3nnc(NC(=O)C4CCOCC4)cc3c2)cn1]
1851
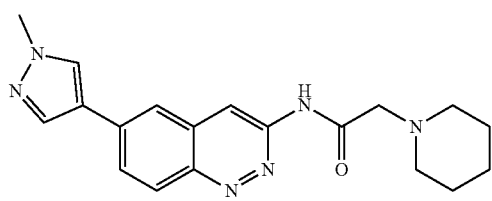 [SMILES: Cn1cc(-c2ccc3nnc(NC(=O)CN4CCCCC4)cc3c2)cn1]
1852
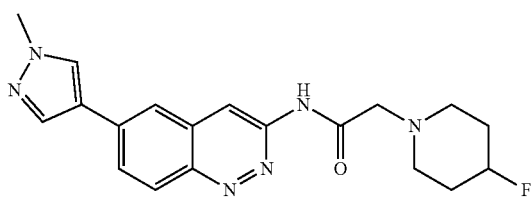 [SMILES: Cn1cc(-c2ccc3nnc(NC(=O)CN4CCC(F)CC4)cc3c2)cn1]
1853
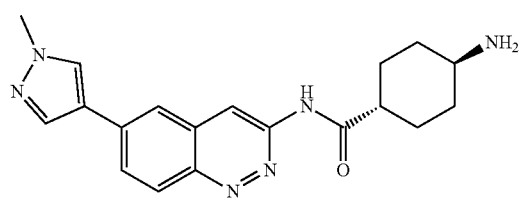 [SMILES: Cn1cc(-c2ccc3nnc(NC(=O)[C@H]4CC[C@H](N)CC4)cc3c2)cn1]
1854
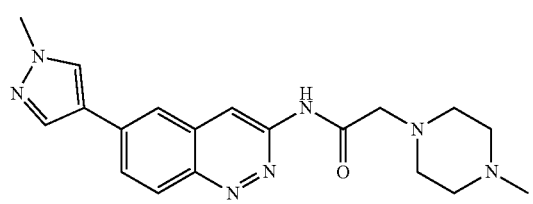 [SMILES: CN1CCN(CC(=O)Nc2cc3cc(-c4cnn(C)c4)ccc3nn2)CC1]
1855

TABLE 1-continued
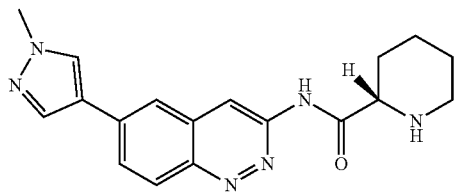 [SMILES: Cn1cc(-c2ccc3nnc(NC(=O)[C@@H]4CCCCN4)cc3c2)cn1]
1856
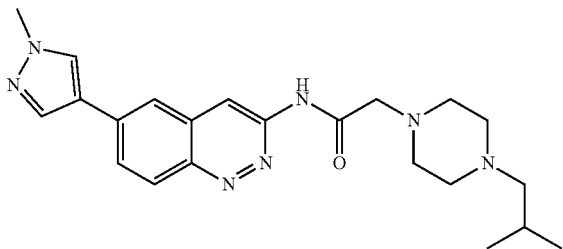 [SMILES: CC(C)CN1CCN(CC(=O)Nc2cc3cc(-c4cnn(C)c4)ccc3nn2)CC1]
1857
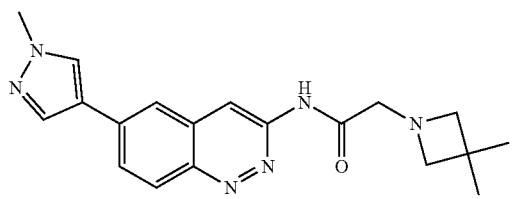 [SMILES: Cn1cc(-c2ccc3nnc(NC(=O)CN4CC(C)(C)C4)cc3c2)cn1]
1858
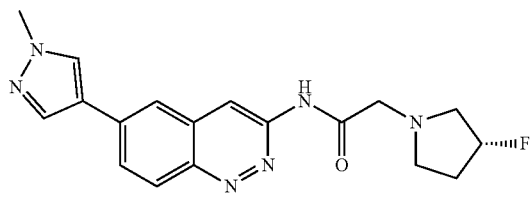 [SMILES: Cn1cc(-c2ccc3nnc(NC(=O)CN4CC[C@@H](F)C4)cc3c2)cn1]
1859
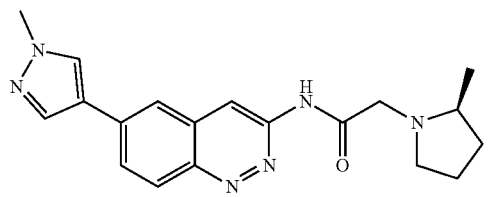 [SMILES: C[C@H]1CCCN1CC(=O)Nc1cc2cc(-c3cnn(C)c3)ccc2nn1]
1860
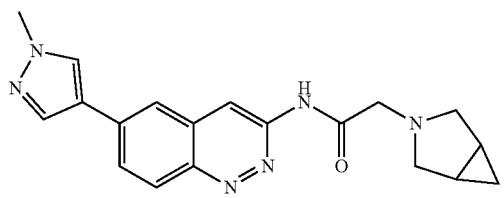 [SMILES: Cn1cc(-c2ccc3nnc(NC(=O)CN4CC5CC5C4)cc3c2)cn1]
1861
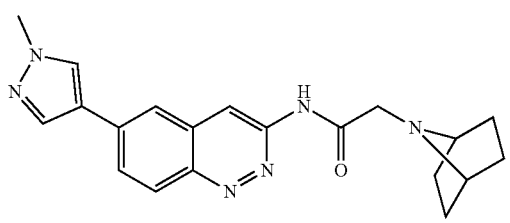 [SMILES: Cn1cc(-c2ccc3nnc(NC(=O)CN4C5CCC4CC5)cc3c2)cn1]
1862

TABLE 1-continued
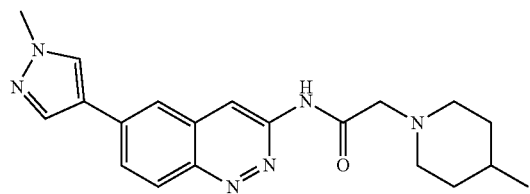 [SMILES: CC1CCN(CC(=O)Nc2cc3cc(-c4cnn(C)c4)ccc3nn2)CC1] 1863
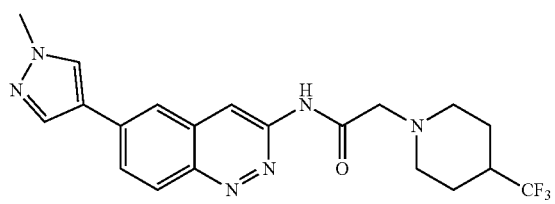 [SMILES: Cn1cc(-c2ccc3nnc(NC(=O)CN4CCC(C(F)(F)F)CC4)cc3c2)cn1] 1864
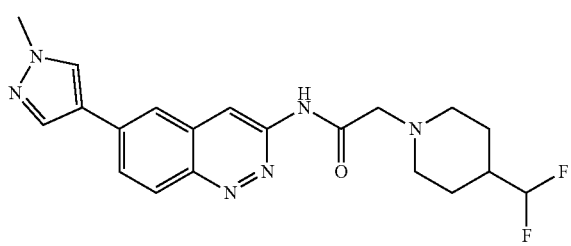 [SMILES: Cn1cc(-c2ccc3nnc(NC(=O)CN4CCC(C(F)F)CC4)cc3c2)cn1] 1865
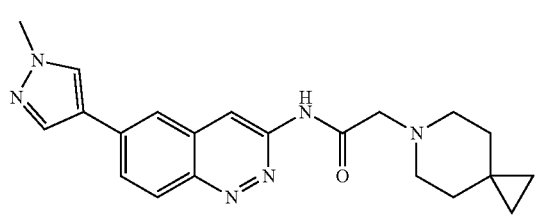 [SMILES: Cn1cc(-c2ccc3nnc(NC(=O)CN4CCC5(CC4)CC5)cc3c2)cn1] 1866
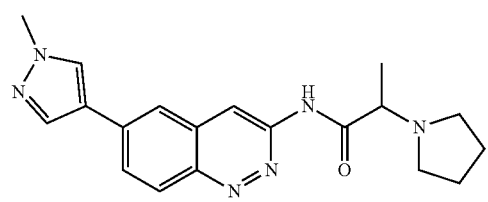 1867
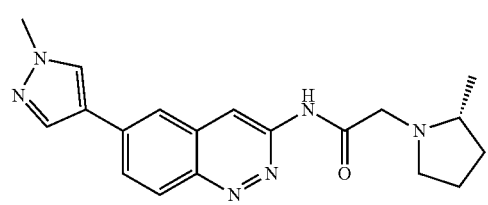 [SMILES: C[C@@H]1CCCN1CC(=O)Nc1cc2cc(-c3cnn(C)c3)ccc2nn1] 1868
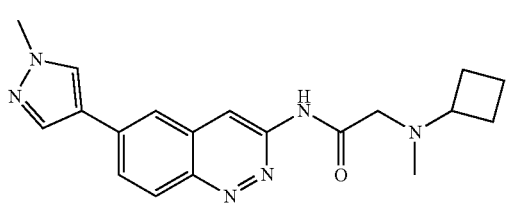 [SMILES: CN(CC(=O)Nc1cc2cc(-c3cnn(C)c3)ccc2nn1)C1CCC1] 1869

TABLE 1-continued
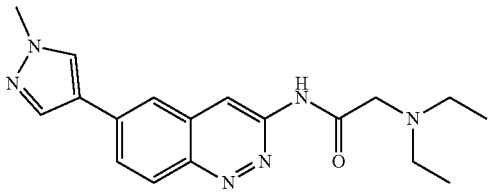 [SMILES: CCN(CC)CC(=O)Nc1cc2cc(-c3cnn(C)c3)ccc2nn1]
1870
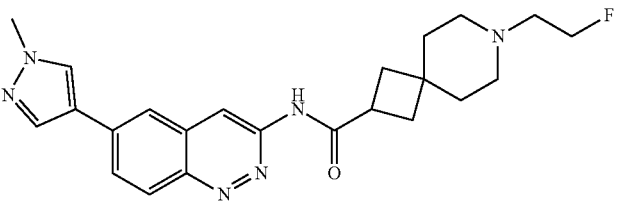 [SMILES: Cn1cc(-c2ccc3nnc(NC(=O)C4CC5(CCN(CCF)CC5)C4)cc3c2)cn1]
1871
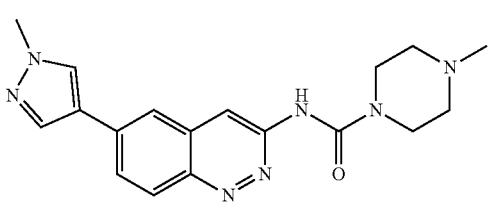 [SMILES: CN1CCN(C(=O)Nc2cc3cc(-c4cnn(C)c4)ccc3nn2)CC1]
1872
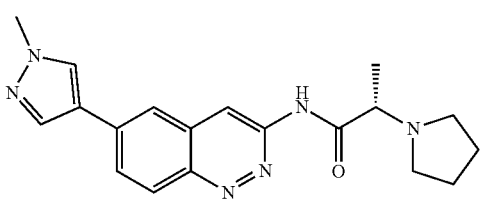 [SMILES: C[C@@H](C(=O)Nc1cc2cc(-c3cnn(C)c3)ccc2nn1)N1CCCC1]
1873
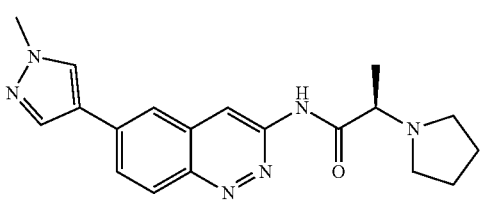 [SMILES: C[C@H](C(=O)Nc1cc2cc(-c3cnn(C)c3)ccc2nn1)N1CCCC1]
1874
1875
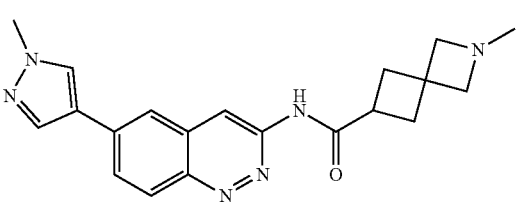 [SMILES: CN1CC2(CC(C(=O)Nc3cc4cc(-c5cnn(C)c5)ccc4nn3)C2)C1]
1876

TABLE 1-continued
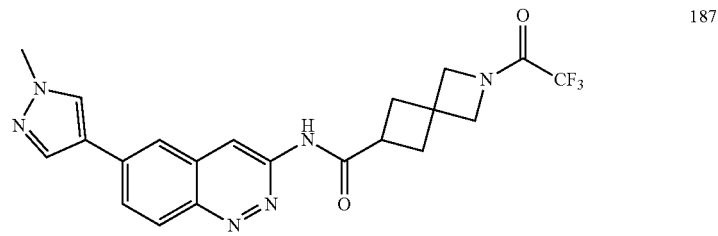   1877
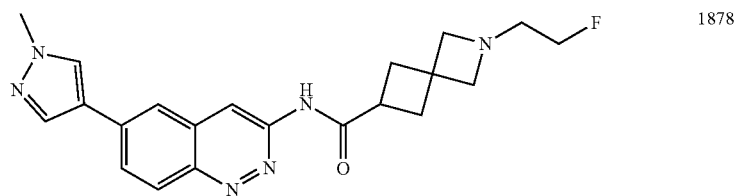   1878
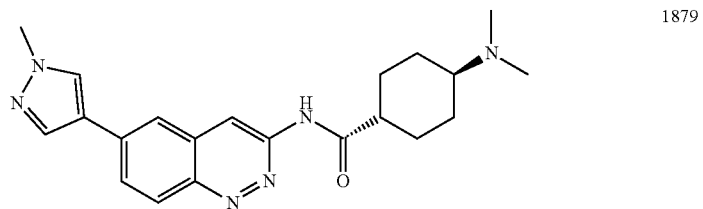   1879
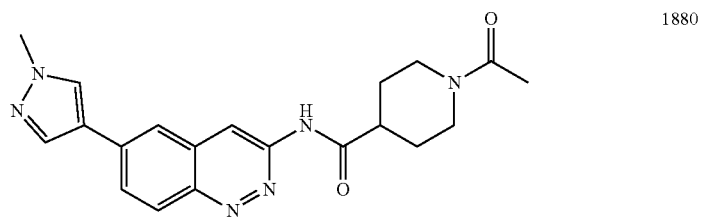   1880
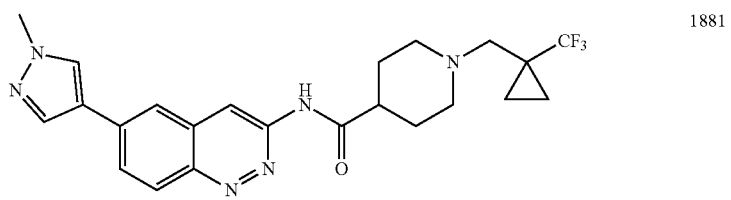   1881
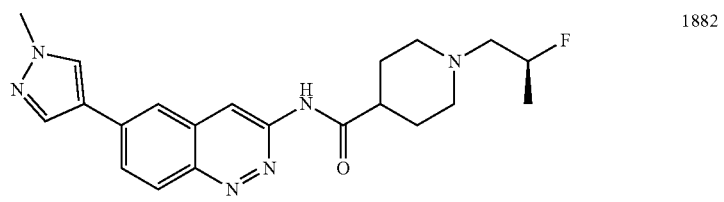   1882
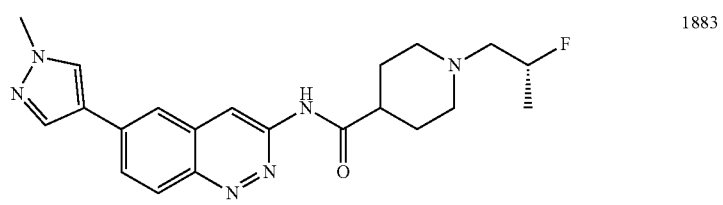   1883

TABLE 1-continued

| | |
|---|---|
| (structure) | 1884 |
| (structure) | 1885 |
| (structure) | 1886 |
| (structure) | 1887 |
| (structure) | 1888 |
| (structure) | 1889 |
| (structure) | 1890 |

TABLE 1-continued
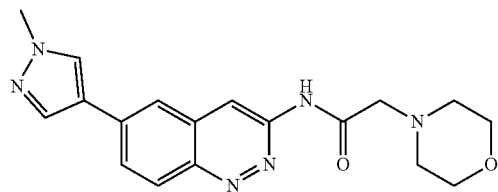 [SMILES: Cn1cc(-c2ccc3nnc(NC(=O)CN4CCOCC4)cc3c2)cn1]
1891
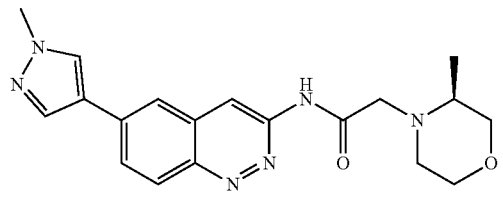 [SMILES: C[C@H]1COCCN1CC(=O)Nc1cc2cc(-c3cnn(C)c3)ccc2nn1]
1892
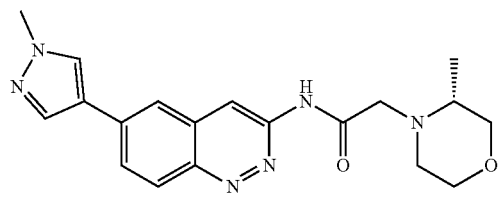 [SMILES: C[C@@H]1COCCN1CC(=O)Nc1cc2cc(-c3cnn(C)c3)ccc2nn1]
1893
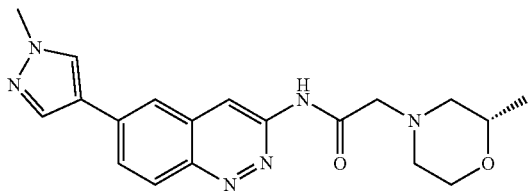 [SMILES: C[C@H]1CN(CC(=O)Nc2cc3cc(-c4cnn(C)c4)ccc3nn2)CCO1]
1894
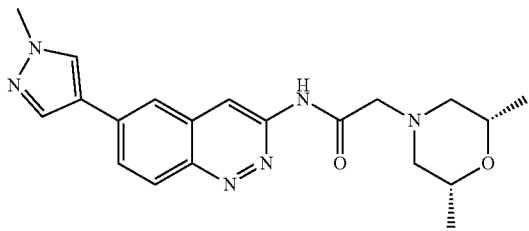 [SMILES: C[C@@H]1CN(CC(=O)Nc2cc3cc(-c4cnn(C)c4)ccc3nn2)C[C@H](C)O1]
1895
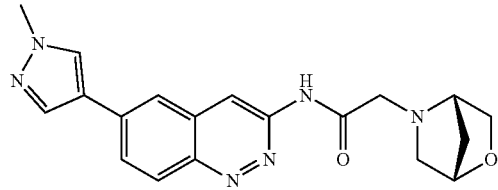 [SMILES: Cn1cc(-c2ccc3nnc(NC(=O)CN4C[C@@H]5C[C@H]4CO5)cc3c2)cn1]
1896
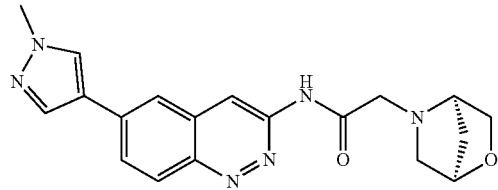 [SMILES: Cn1cc(-c2ccc3nnc(NC(=O)CN4C[C@H]5C[C@@H]4CO5)cc3c2)cn1]
1897
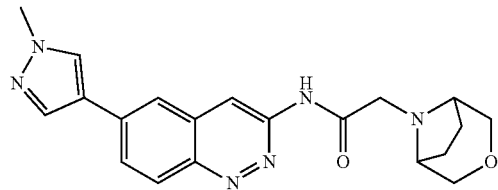 [SMILES: Cn1cc(-c2ccc3nnc(NC(=O)CN4C5CCC4COC5)cc3c2)cn1]
1898

TABLE 1-continued
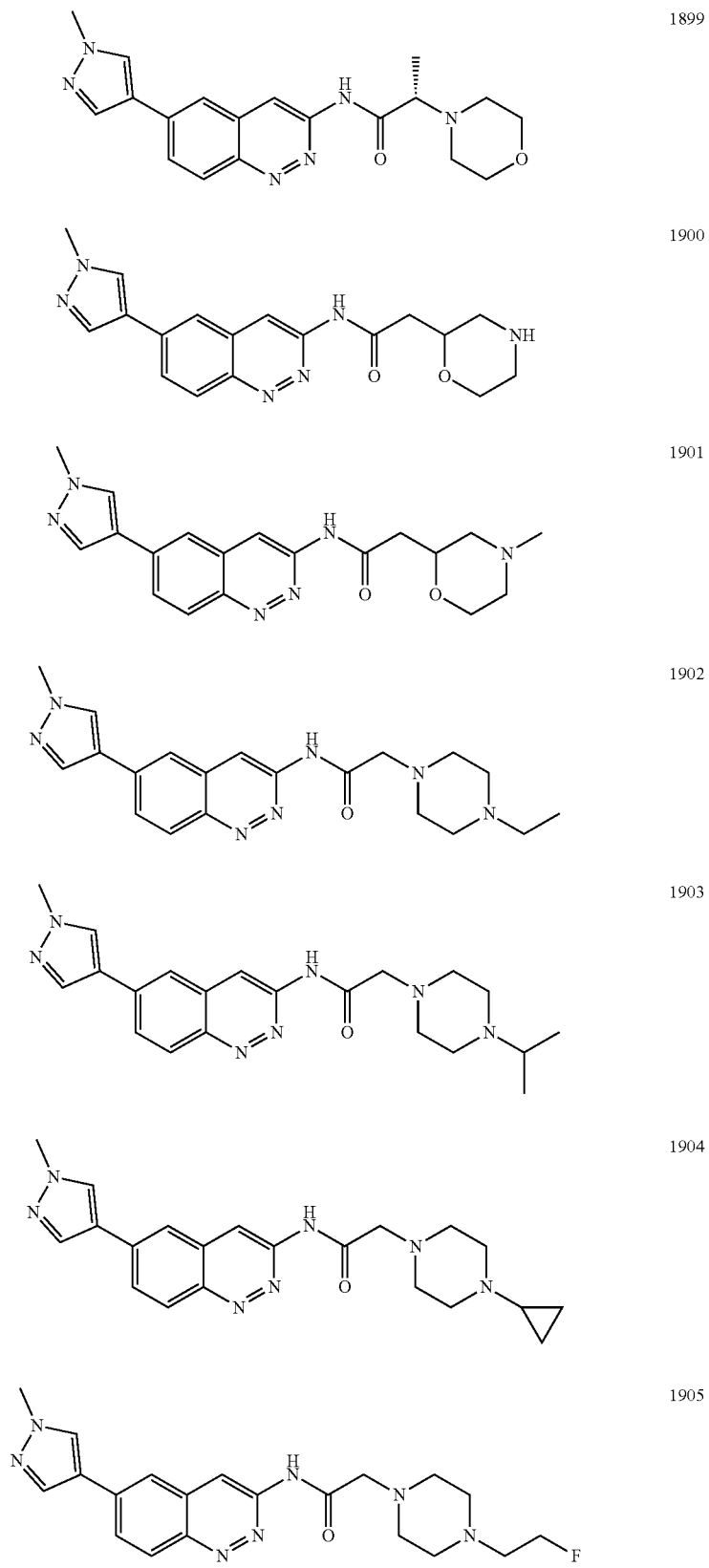
1899
1900
1901
1902
1903
1904
1905

TABLE 1-continued
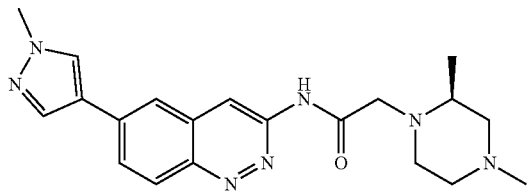 [SMILES: C[C@H]1CN(C)CCN1CC(=O)Nc1cc2cc(-c3cnn(C)c3)ccc2nn1]
1906
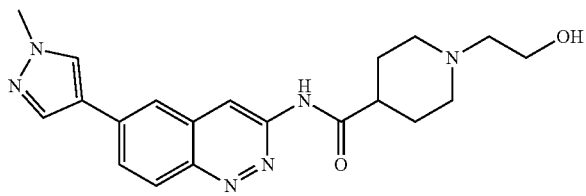 [SMILES: Cn1cc(-c2ccc3nnc(NC(=O)C4CCN(CCO)CC4)cc3c2)cn1]
1907
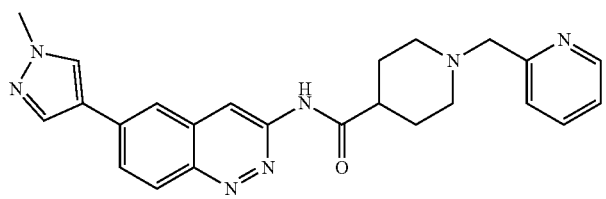
1908
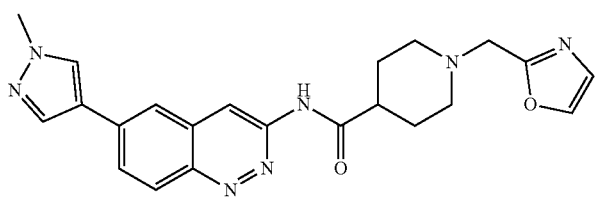 [SMILES: Cn1cc(-c2ccc3nnc(NC(=O)C4CCN(Cc5ncco5)CC4)cc3c2)cn1]
1909
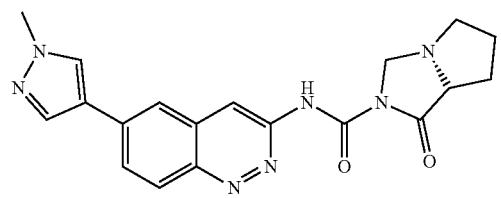
1910
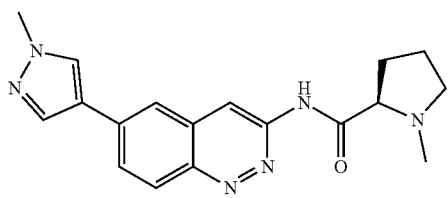 [SMILES: CN1CCC[C@@H]1C(=O)Nc1cc2cc(-c3cnn(C)c3)ccc2nn1]
1911
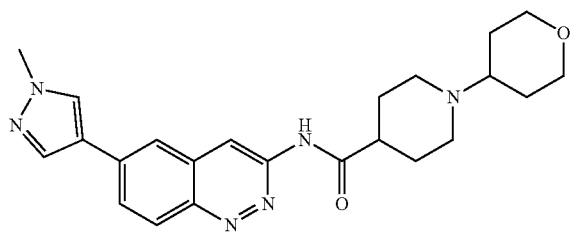 [SMILES: Cn1cc(-c2ccc3nnc(NC(=O)C4CCN(C5CCOCC5)CC4)cc3c2)cn1]
1912

TABLE 1-continued
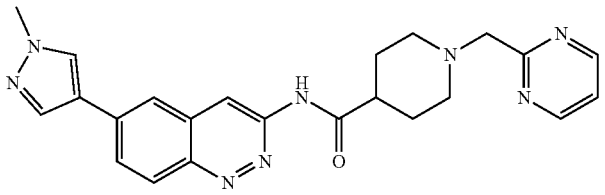
1913
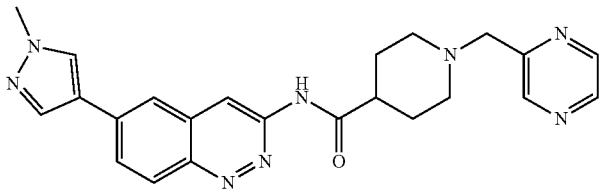 [SMILES: Cn1cc(-c2ccc3nnc(NC(=O)C4CCN(Cc5cnccn5)CC4)cc3c2)cn1]
1914
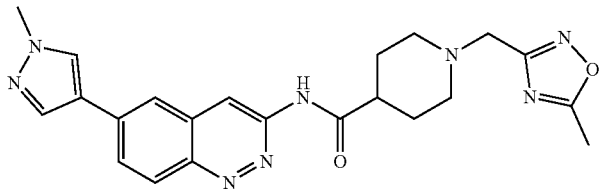 [SMILES: Cc1nc(CN2CCC(C(=O)Nc3cc4cc(-c5cnn(C)c5)ccc4nn3)CC2)no1]
1915
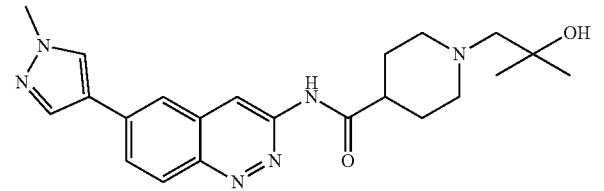 [SMILES: Cn1cc(-c2ccc3nnc(NC(=O)C4CCN(CC(C)(C)O)CC4)cc3c2)cn1]
1916
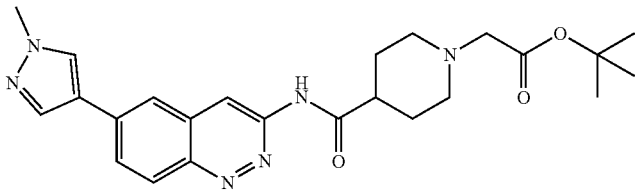 [SMILES: Cn1cc(-c2ccc3nnc(NC(=O)C4CCN(CC(=O)OC(C)(C)C)CC4)cc3c2)cn1]
1917
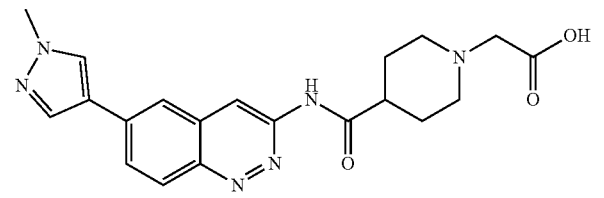 [SMILES: Cn1cc(-c2ccc3nnc(NC(=O)C4CCN(CC(=O)O)CC4)cc3c2)cn1]
1918
1919
1920

TABLE 1-continued
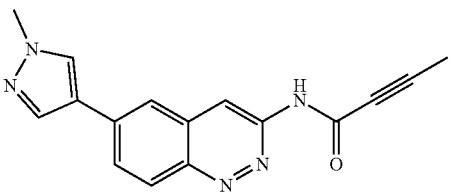 [SMILES: CC#CC(=O)Nc1cc2cc(-c3cnn(C)c3)ccc2nn1]
1921
1922
1923
1924
1925
1926
1927
1928

TABLE 1-continued
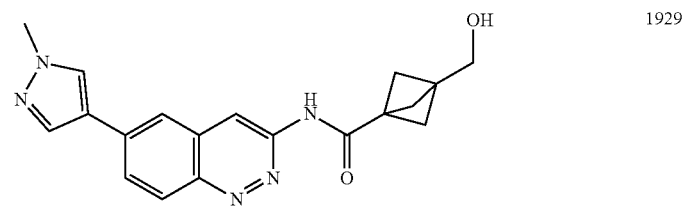 1929
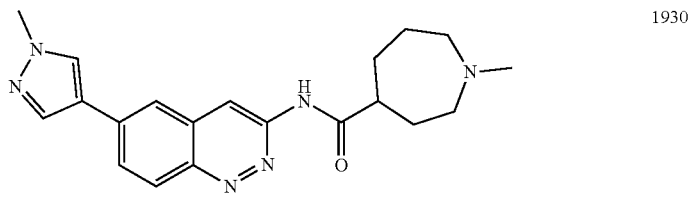 1930
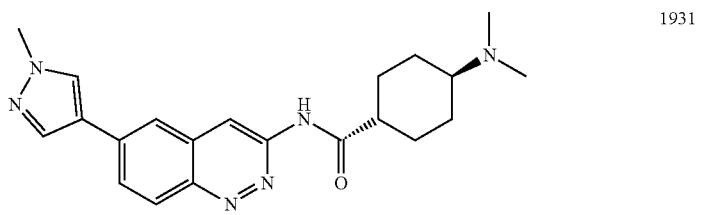 1931
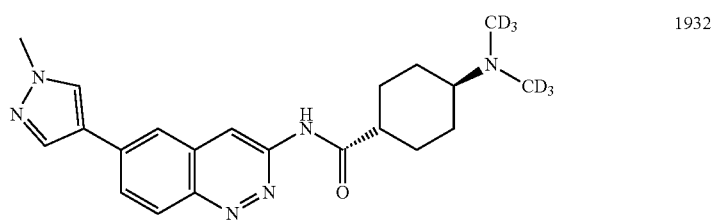 1932
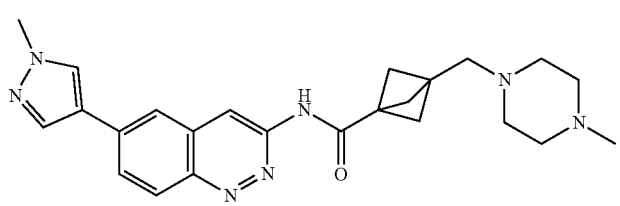 [SMILES: CN1CCN(CC23CC(C(=O)Nc4cc5cc(-c6cnn(C)c6)ccc5nn4)(C2)C3)CC1] 1933
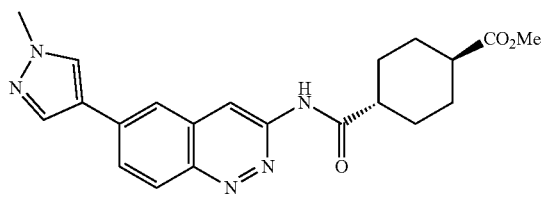 [SMILES: COC(=O)[C@H]1CC[C@H](C(=O)Nc2cc3cc(-c4cnn(C)c4)ccc3nn2)CC1] 1934
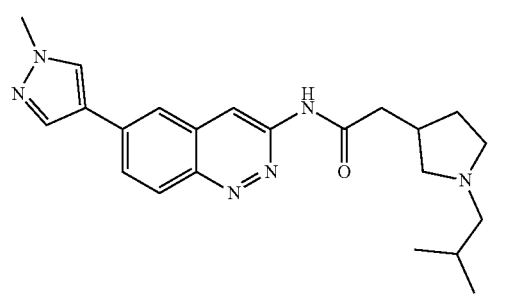 [SMILES: CC(C)CN1CCC(CC(=O)Nc2cc3cc(-c4cnn(C)c4)ccc3nn2)C1] 1935

TABLE 1-continued
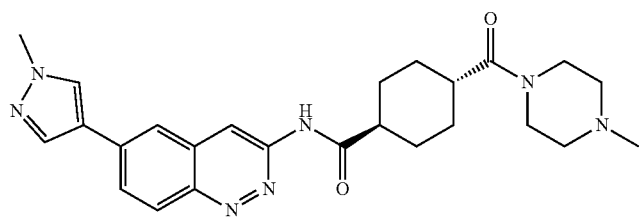 [SMILES: CN1CCN(C(=O)[C@H]2CC[C@H](C(=O)Nc3cc4cc(-c5cnn(C)c5)ccc4nn3)CC2)CC1]
1936
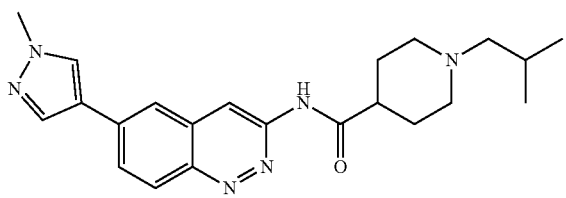 [SMILES: CC(C)CN1CCC(C(=O)Nc2cc3cc(-c4cnn(C)c4)ccc3nn2)CC1]
1937
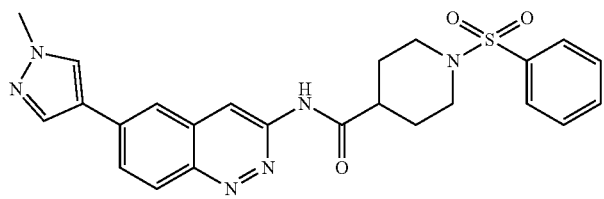 [SMILES: Cn1cc(-c2ccc3nnc(NC(=O)C4CCN(S(=O)(=O)c5ccccc5)CC4)cc3c2)cn1]
1938
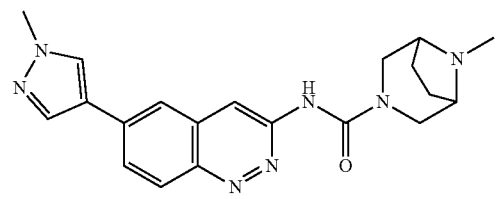 [SMILES: CN1C2CCC1CN(C(=O)Nc1cc3cc(-c4cnn(C)c4)ccc3nn1)C2]
1939
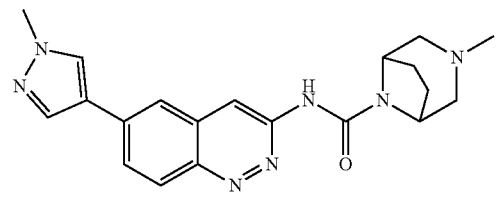 [SMILES: CN1CC2CCC(C1)N2C(=O)Nc1cc2cc(-c3cnn(C)c3)ccc2nn1]
1940
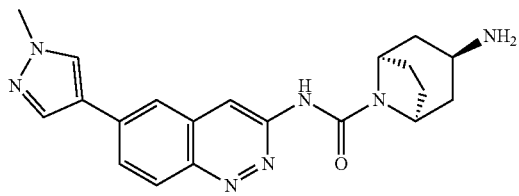 [SMILES: Cn1cc(-c2ccc3nnc(NC(=O)N4[C@@H]5CC[C@H]4C[C@H](N)C5)cc3c2)cn1]
1941
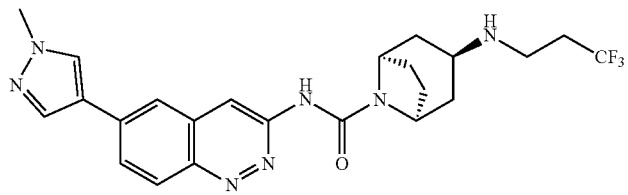 [SMILES: Cn1cc(-c2ccc3nnc(NC(=O)N4[C@@H]5CC[C@H]4C[C@H](NCCC(F)(F)F)C5)cc3c2)cn1]
1942

TABLE 1-continued
| | |
|---|---|
| 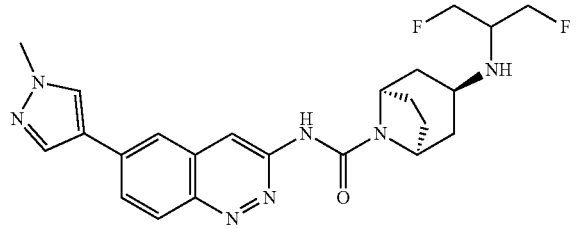 [SMILES: Cn1cc(-c2ccc3nnc(NC(=O)N4[C@@H]5CC[C@H]4C[C@H](NC(CF)CF)C5)cc3c2)cn1] | 1943 |
| 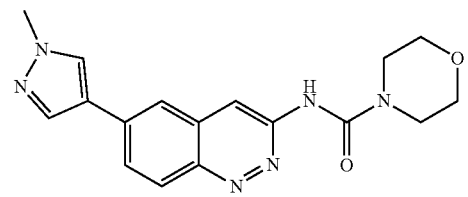 [SMILES: Cn1cc(-c2ccc3nnc(NC(=O)N4CCOCC4)cc3c2)cn1] | 1944 |
| 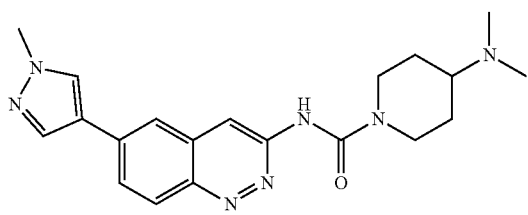 [SMILES: CN(C)C1CCN(C(=O)Nc2cc3cc(-c4cnn(C)c4)ccc3nn2)CC1] | 1945 |
| 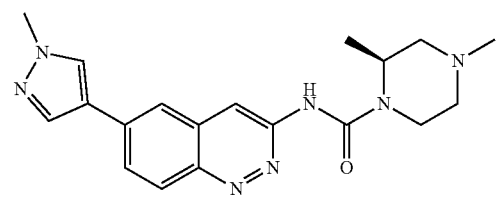 [SMILES: C[C@H]1CN(C)CCN1C(=O)Nc1cc2cc(-c3cnn(C)c3)ccc2nn1] | 1946 |
| 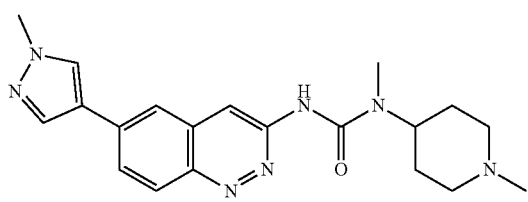 [SMILES: CN1CCC(N(C)C(=O)Nc2cc3cc(-c4cnn(C)c4)ccc3nn2)CC1] | 1947 |
| 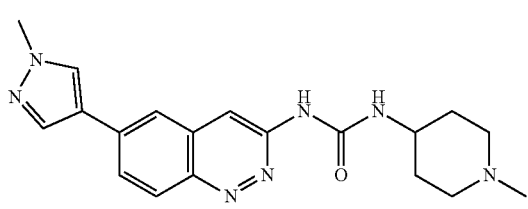 [SMILES: CN1CCC(NC(=O)Nc2cc3cc(-c4cnn(C)c4)ccc3nn2)CC1] | 1948 |
| 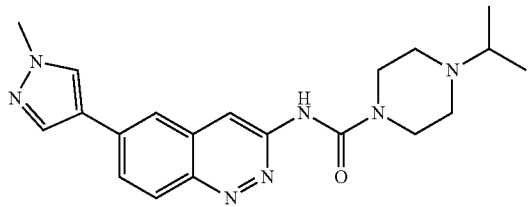 [SMILES: CC(C)N1CCN(C(=O)Nc2cc3cc(-c4cnn(C)c4)ccc3nn2)CC1] | 1949 |

TABLE 1-continued
| | |
|---|---|
| 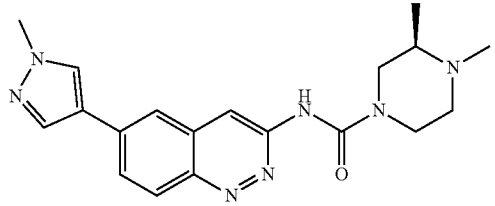 [SMILES: C[C@@H]1CN(C(=O)Nc2cc3cc(-c4cnn(C)c4)ccc3nn2)CCN1C] | 1950 |
| 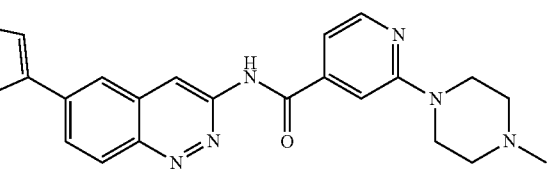 | 1951 |
| 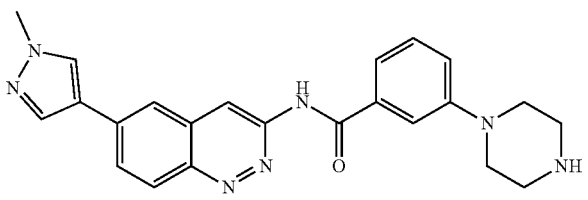 | 1952 |
| 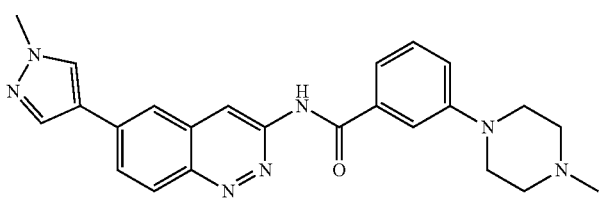 | 1953 |
| 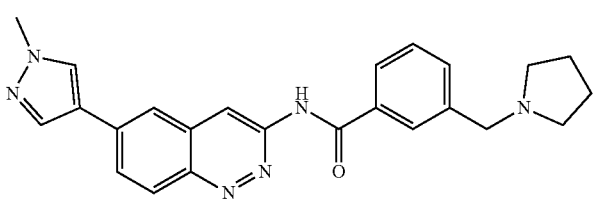 | 1954 |
| 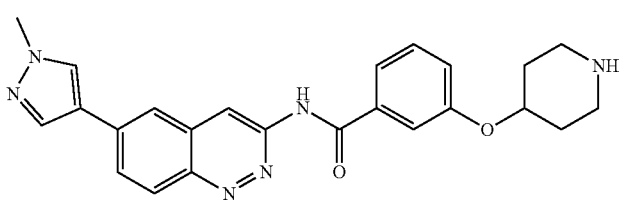 [SMILES: Cn1cc(-c2ccc3nnc(NC(=O)c4cccc(OC5CCNCC5)c4)cc3c2)cn1] | 1955 |
| 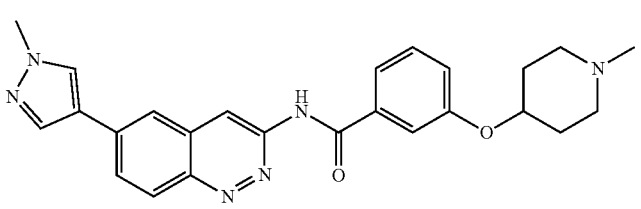 [SMILES: CN1CCC(Oc2cccc(C(=O)Nc3cc4cc(-c5cnn(C)c5)ccc4nn3)c2)CC1] | 1956 |
| 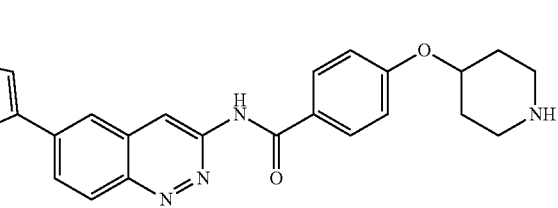 | 1957 |

TABLE 1-continued
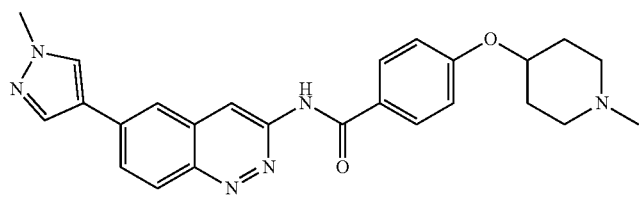 [SMILES: CN1CCC(Oc2ccc(C(=O)Nc3cc4cc(-c5cnn(C)c5)ccc4nn3)cc2)CC1]
1958
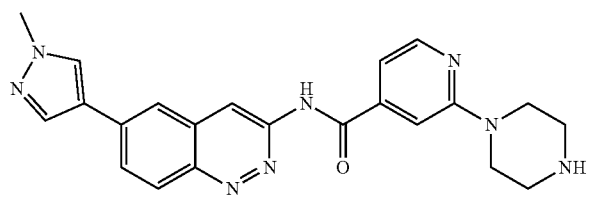 [SMILES: Cn1cc(-c2ccc3nnc(NC(=O)c4ccnc(N5CCNCC5)c4)cc3c2)cn1]
1959
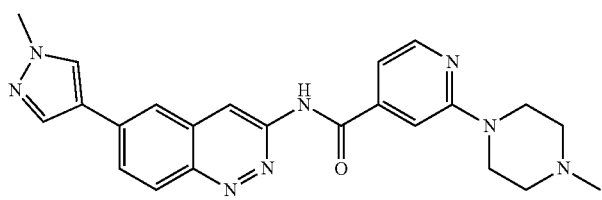 [SMILES: CN1CCN(c2cc(C(=O)Nc3cc4cc(-c5cnn(C)c5)ccc4nn3)ccn2)CC1]
1960
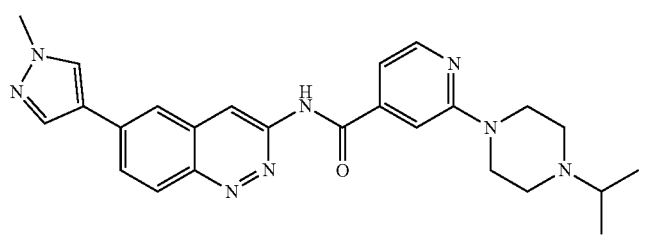 [SMILES: CC(C)N1CCN(c2cc(C(=O)Nc3cc4cc(-c5cnn(C)c5)ccc4nn3)ccn2)CC1]
1961
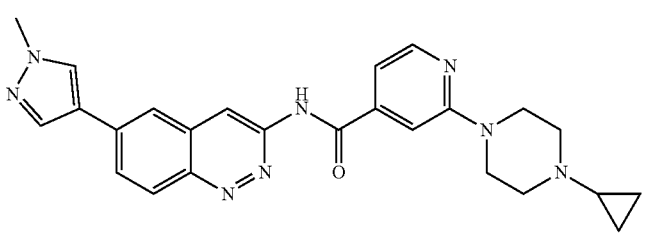
1962
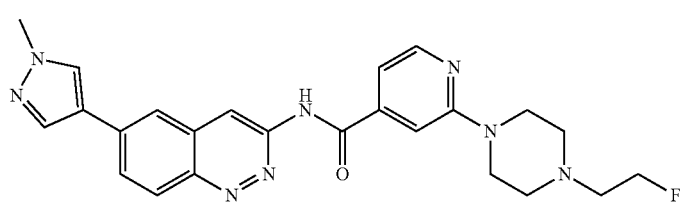 [SMILES: Cn1cc(-c2ccc3nnc(NC(=O)c4ccnc(N5CCN(CCF)CC5)c4)cc3c2)cn1]
1963
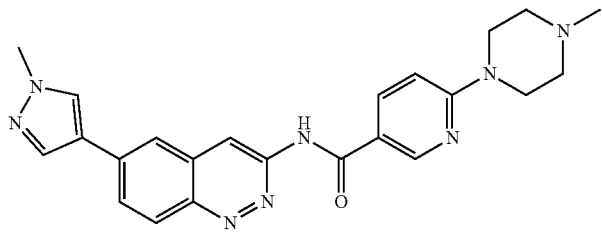 [SMILES: CN1CCN(c2ccc(C(=O)Nc3cc4cc(-c5cnn(C)c5)ccc4nn3)cn2)CC1]
1964

TABLE 1-continued
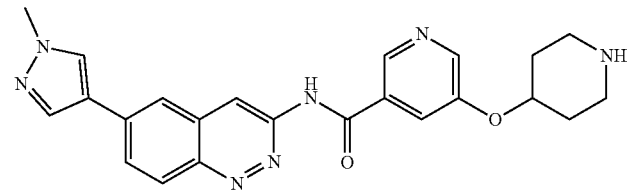 [SMILES: Cn1cc(-c2ccc3nnc(NC(=O)c4cncc(OC5CCNCC5)c4)cc3c2)cn1]
1965
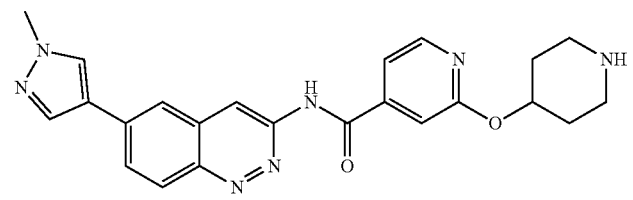
1966
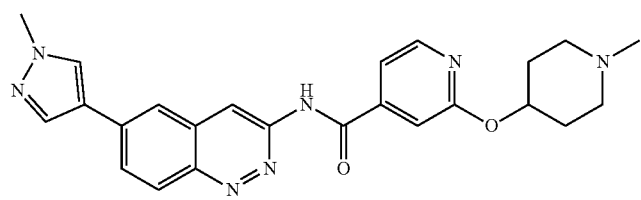 [SMILES: CN1CCC(Oc2cc(C(=O)Nc3cc4cc(-c5cnn(C)c5)ccc4nn3)ccn2)CC1]
1967
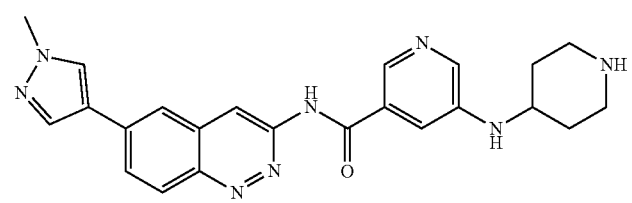 [SMILES: Cn1cc(-c2ccc3nnc(NC(=O)c4cncc(NC5CCNCC5)c4)cc3c2)cn1]
1968
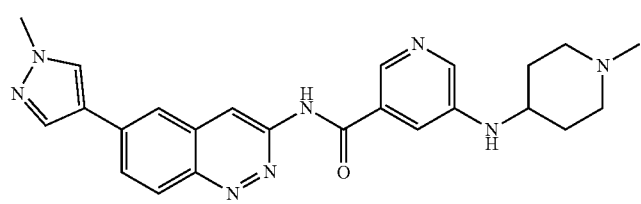 [SMILES: CN1CCC(Nc2cncc(C(=O)Nc3cc4cc(-c5cnn(C)c5)ccc4nn3)c2)CC1]
1969
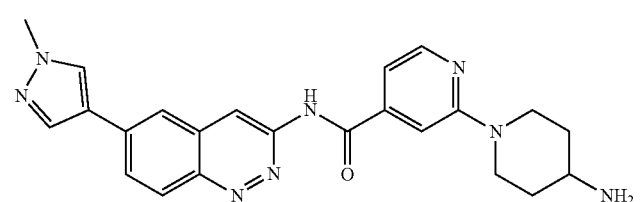
1970
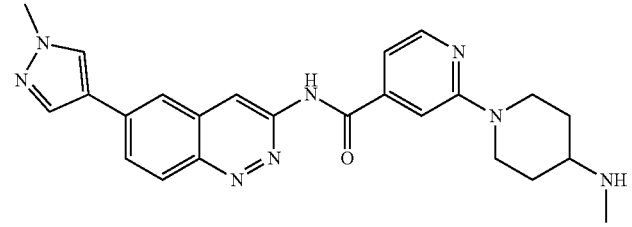 [SMILES: CNC1CCN(c2cc(C(=O)Nc3cc4cc(-c5cnn(C)c5)ccc4nn3)ccn2)CC1]
1971

TABLE 1-continued
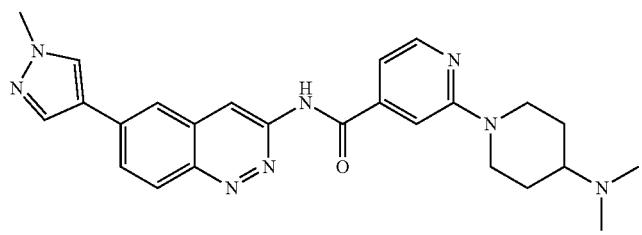 [SMILES: CN(C)C1CCN(c2cc(C(=O)Nc3cc4cc(-c5cnn(C)c5)ccc4nn3)ccn2)CC1] 1972
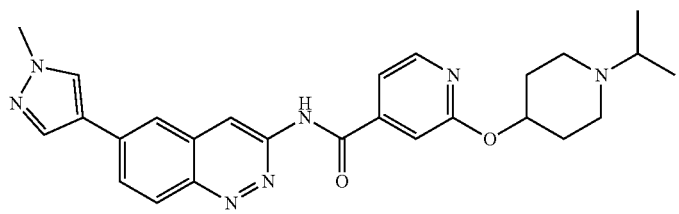 [SMILES: CC(C)N1CCC(Oc2cc(C(=O)Nc3cc4cc(-c5cnn(C)c5)ccc4nn3)ccn2)CC1] 1973
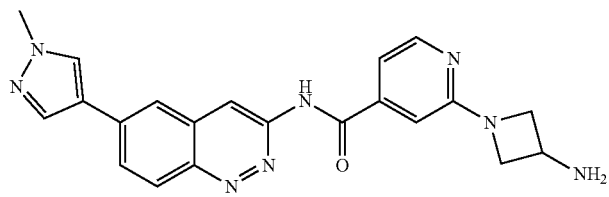 [SMILES: Cn1cc(-c2ccc3nnc(NC(=O)c4ccnc(N5CC(N)C5)c4)cc3c2)cn1] 1974
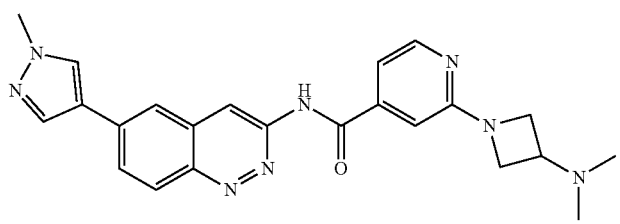 [SMILES: CN(C)C1CN(c2cc(C(=O)Nc3cc4cc(-c5cnn(C)c5)ccc4nn3)ccn2)C1] 1975
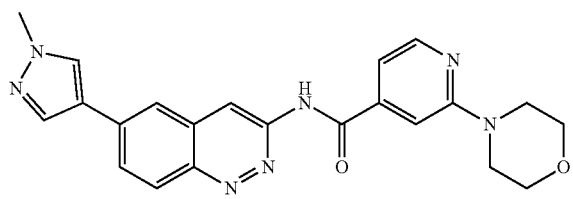 [SMILES: Cn1cc(-c2ccc3nnc(NC(=O)c4ccnc(N5CCOCC5)c4)cc3c2)cn1] 1976
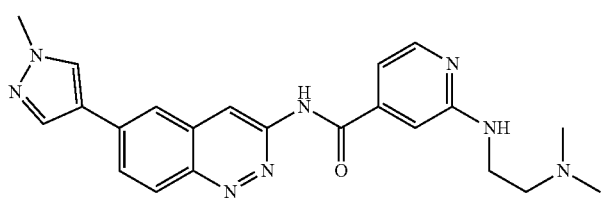 [SMILES: CN(C)CCNc1cc(C(=O)Nc2cc3cc(-c4cnn(C)c4)ccc3nn2)ccn1] 1977
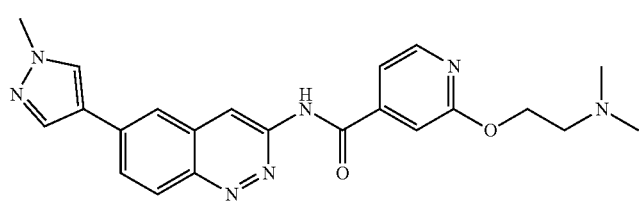 [SMILES: CN(C)CCOc1cc(C(=O)Nc2cc3cc(-c4cnn(C)c4)ccc3nn2)ccn1] 1978

TABLE 1-continued
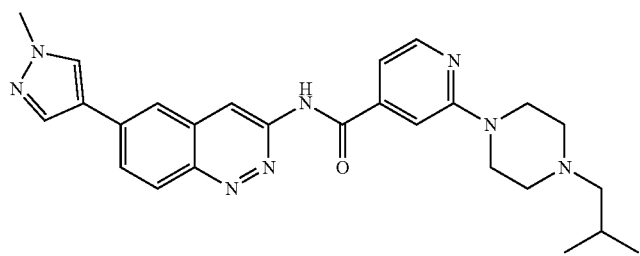 [SMILES: CC(C)CN1CCN(c2cc(C(=O)Nc3cc4cc(-c5cnn(C)c5)ccc4nn3)ccn2)CC1]
1979
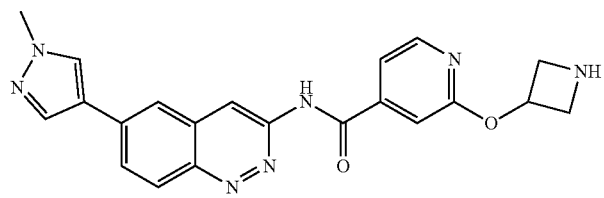 [SMILES: Cn1cc(-c2ccc3nnc(NC(=O)c4ccnc(OC5CNC5)c4)cc3c2)cn1]
1980
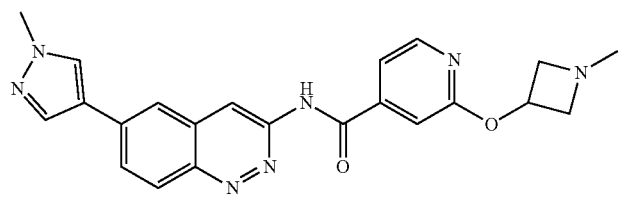 [SMILES: CN1CC(Oc2cc(C(=O)Nc3cc4cc(-c5cnn(C)c5)ccc4nn3)ccn2)C1]
1981
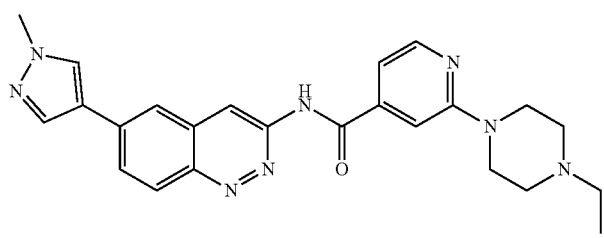 [SMILES: CCN1CCN(c2cc(C(=O)Nc3cc4cc(-c5cnn(C)c5)ccc4nn3)ccn2)CC1]
1982
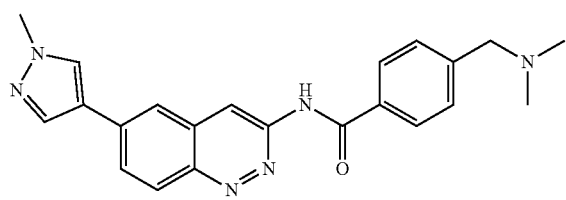 [SMILES: CN(C)Cc1ccc(C(=O)Nc2cc3cc(-c4cnn(C)c4)ccc3nn2)cc1]
1983
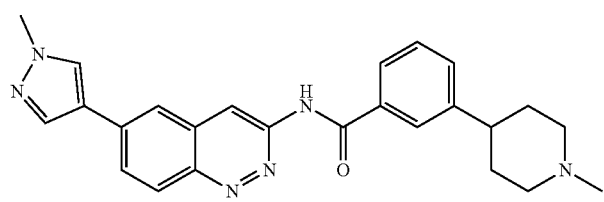 [SMILES: CN1CCC(c2cccc(C(=O)Nc3cc4cc(-c5cnn(C)c5)ccc4nn3)c2)CC1]
1984
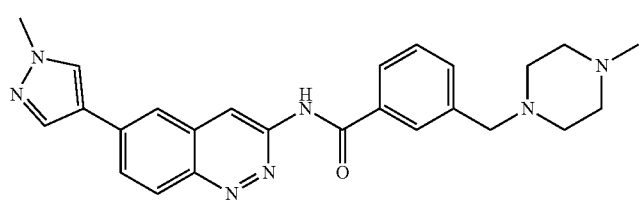 [SMILES: CN1CCN(Cc2cccc(C(=O)Nc3cc4cc(-c5cnn(C)c5)ccc4nn3)c2)CC1]
1985

TABLE 1-continued
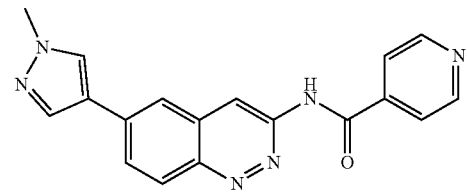 [SMILES: Cn1cc(-c2ccc3nnc(NC(=O)c4ccncc4)cc3c2)cn1] 1986
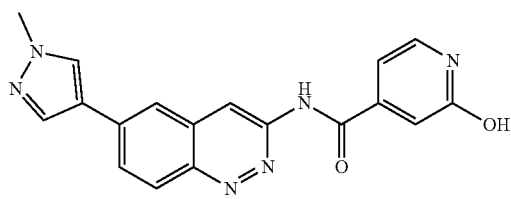 [SMILES: Cn1cc(-c2ccc3nnc(NC(=O)c4ccnc(O)c4)cc3c2)cn1] 1987
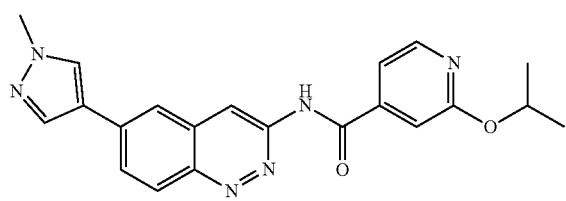 [SMILES: CC(C)Oc1cc(C(=O)Nc2cc3cc(-c4cnn(C)c4)ccc3nn2)ccn1] 1988
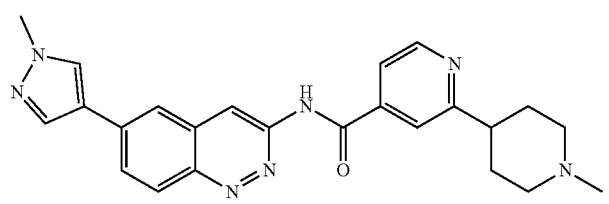 1989
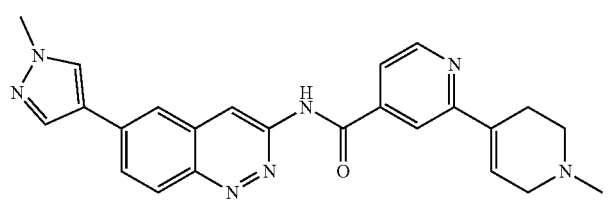 [SMILES: CN1CC=C(c2cc(C(=O)Nc3cc4cc(-c5cnn(C)c5)ccc4nn3)ccn2)CC1] 1990
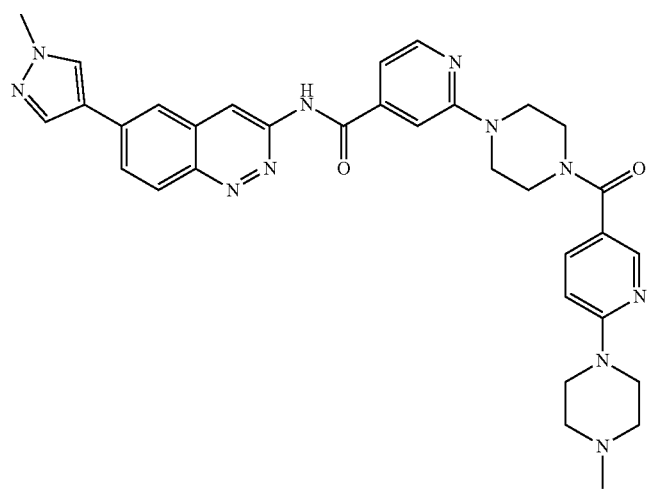 [SMILES: CN1CCN(c2ccc(C(=O)N3CCN(c4cc(C(=O)Nc5cc6cc(-c7cnn(C)c7)ccc6nn5)ccn4)CC3)cn2)CC1] 1991

TABLE 1-continued
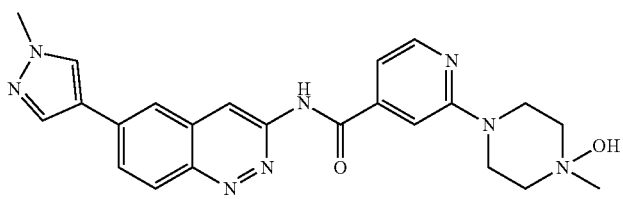
1992
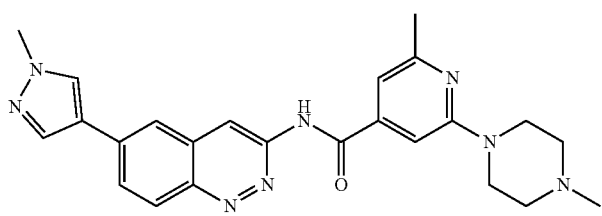 [SMILES: Cc1cc(C(=O)Nc2cc3cc(-c4cnn(C)c4)ccc3nn2)cc(N2CCN(C)CC2)n1]
1993
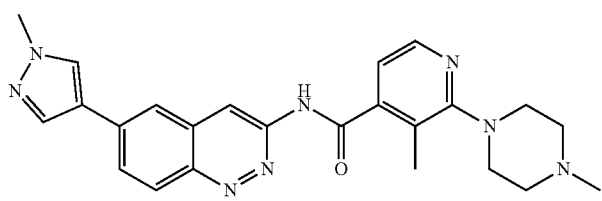
1994
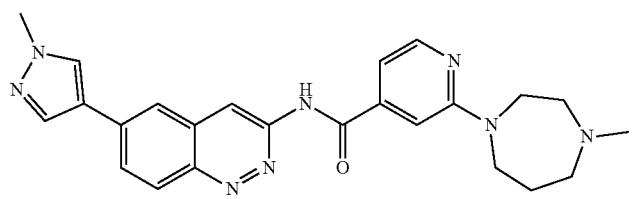 [SMILES: CN1CCCN(c2cc(C(=O)Nc3cc4cc(-c5cnn(C)c5)ccc4nn3)ccn2)CC1]
1995
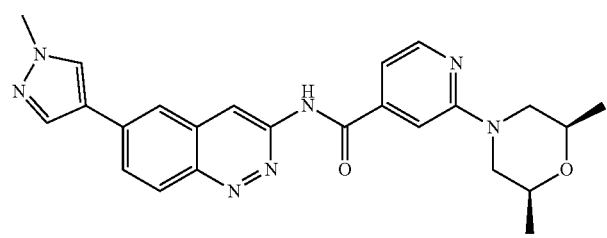 [SMILES: C[C@@H]1CN(c2cc(C(=O)Nc3cc4cc(-c5cnn(C)c5)ccc4nn3)ccn2)C[C@H](C)O1]
1996
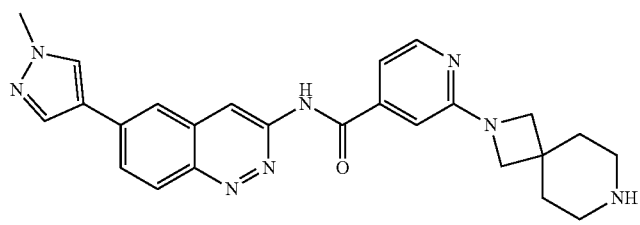 [SMILES: Cn1cc(-c2ccc3nnc(NC(=O)c4ccnc(N5CC6(CCNCC6)C5)c4)cc3c2)cn1]
1997
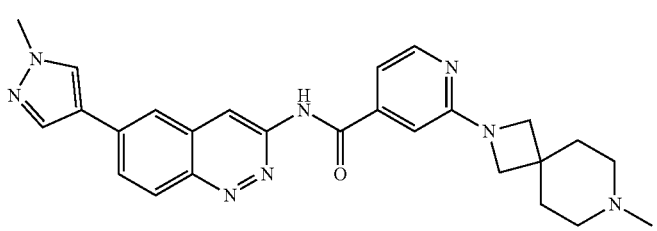 [SMILES: CN1CCC2(CC1)CN(c1cc(C(=O)Nc3cc4cc(-c5cnn(C)c5)ccc4nn3)ccn1)C2]
1998

TABLE 1-continued
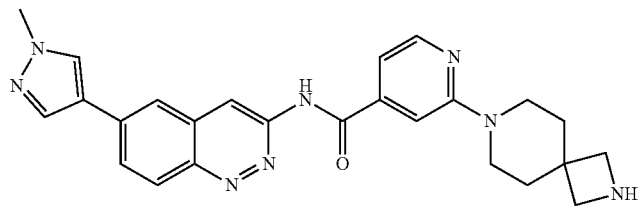 [SMILES: Cn1cc(-c2ccc3nnc(NC(=O)c4ccnc(N5CCC6(CC5)CNC6)c4)cc3c2)cn1] 1999
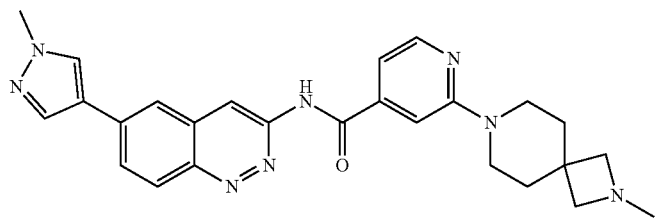 [SMILES: CN1CC2(CCN(c3cc(C(=O)Nc4cc5cc(-c6cnn(C)c6)ccc5nn4)ccn3)CC2)C1] 2000
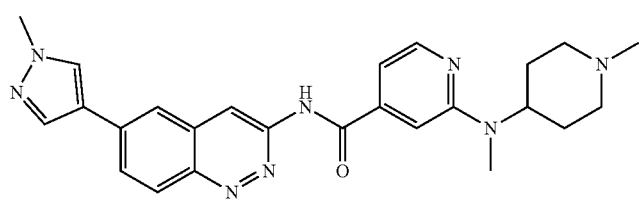 [SMILES: CN1CCC(N(C)c2cc(C(=O)Nc3cc4cc(-c5cnn(C)c5)ccc4nn3)ccn2)CC1] 2001
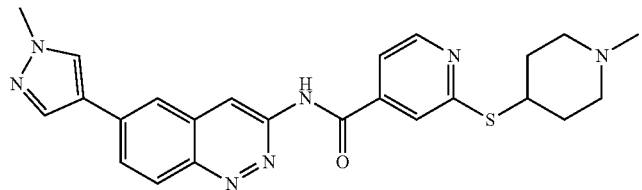 [SMILES: CN1CCC(Sc2cc(C(=O)Nc3cc4cc(-c5cnn(C)c5)ccc4nn3)ccn2)CC1] 2002
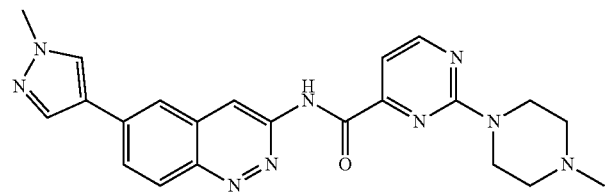 2003
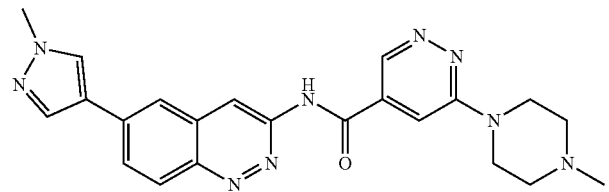 2004
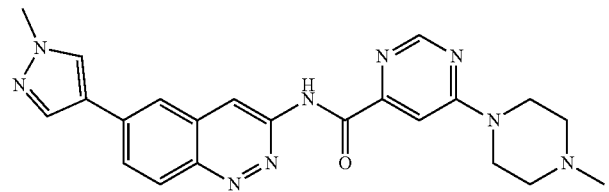 [SMILES: CN1CCN(c2cc(C(=O)Nc3cc4cc(-c5cnn(C)c5)ccc4nn3)ncn2)CC1] 2005
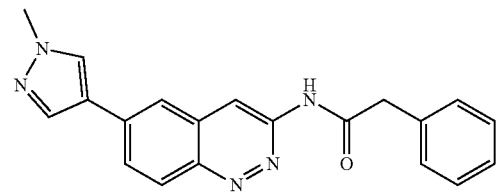 [SMILES: Cn1cc(-c2ccc3nnc(NC(=O)Cc4ccccc4)cc3c2)cn1] 2006

TABLE 1-continued
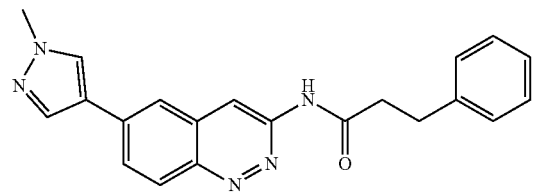 [SMILES: Cn1cc(-c2ccc3nnc(NC(=O)CCc4ccccc4)cc3c2)cn1] 2007
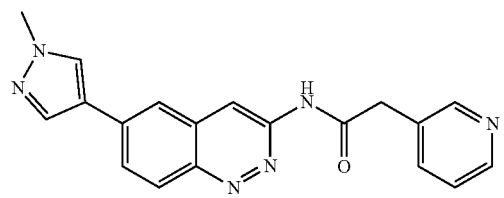 [SMILES: Cn1cc(-c2ccc3nnc(NC(=O)Cc4cccnc4)cc3c2)cn1] 2008
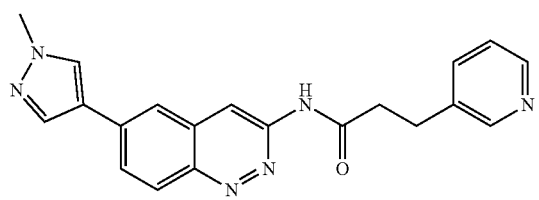 [SMILES: Cn1cc(-c2ccc3nnc(NC(=O)CCc4cccnc4)cc3c2)cn1] 2009
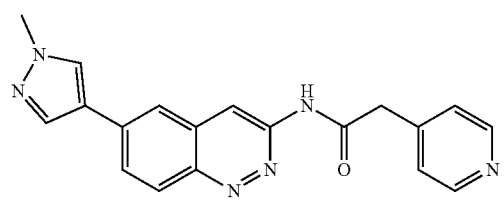 [SMILES: Cn1cc(-c2ccc3nnc(NC(=O)Cc4ccncc4)cc3c2)cn1] 2010
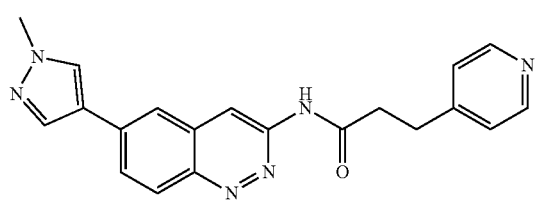 [SMILES: Cn1cc(-c2ccc3nnc(NC(=O)CCc4ccncc4)cc3c2)cn1] 2011
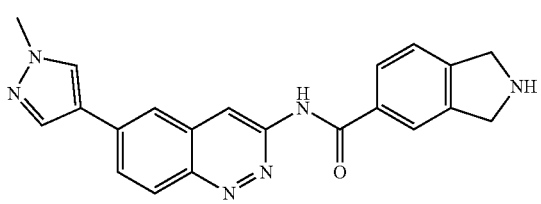 [SMILES: Cn1cc(-c2ccc3nnc(NC(=O)c4ccc5c(c4)CNC5)cc3c2)cn1] 2012
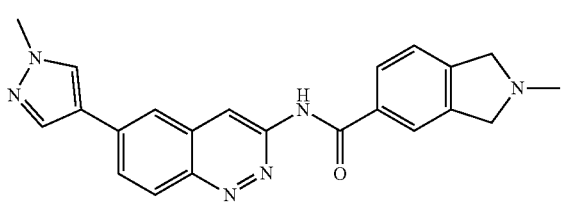 [SMILES: CN1Cc2ccc(C(=O)Nc3cc4cc(-c5cnn(C)c5)ccc4nn3)cc2C1] 2013
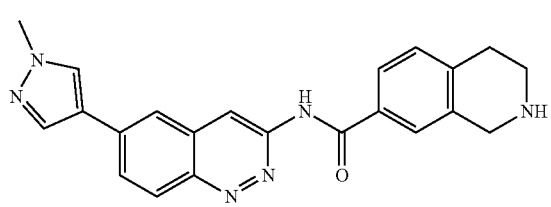 [SMILES: Cn1cc(-c2ccc3nnc(NC(=O)c4ccc5c(c4)CNCC5)cc3c2)cn1] 2014

TABLE 1-continued
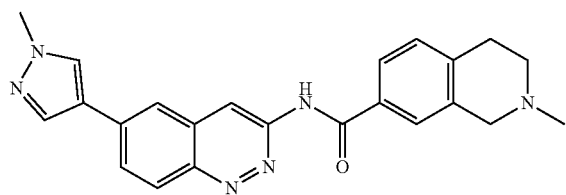 [SMILES: CN1CCc2ccc(C(=O)Nc3cc4cc(-c5cnn(C)c5)ccc4nn3)cc2C1] 2015
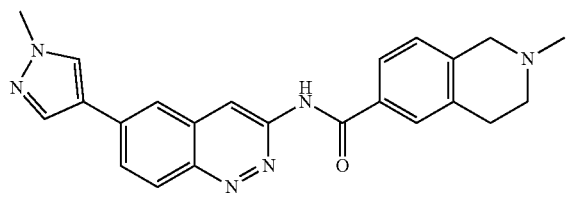 [SMILES: CN1CCc2cc(C(=O)Nc3cc4cc(-c5cnn(C)c5)ccc4nn3)ccc2C1] 2016
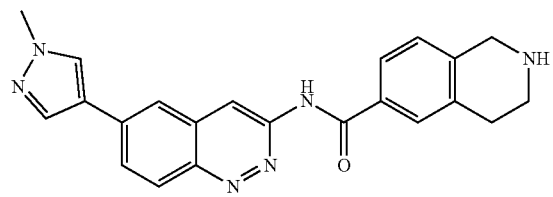 [SMILES: Cn1cc(-c2ccc3nnc(NC(=O)c4ccc5c(c4)CCNC5)cc3c2)cn1] 2017
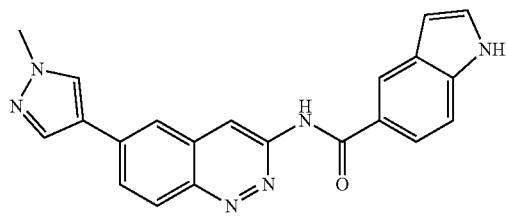 [SMILES: Cn1cc(-c2ccc3nnc(NC(=O)c4ccc5[nH]ccc5c4)cc3c2)cn1] 2018
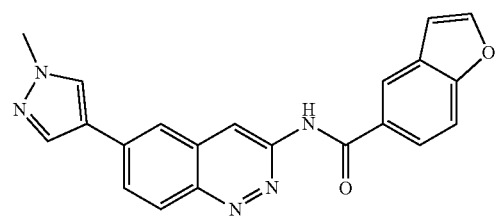 [SMILES: Cn1cc(-c2ccc3nnc(NC(=O)c4cc5ccoc5cn4)cc3c2)cn1] 2019
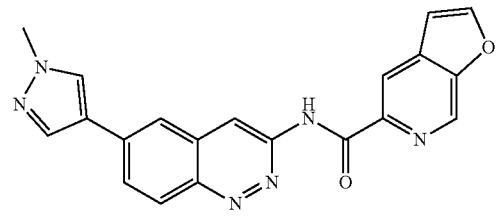 2020
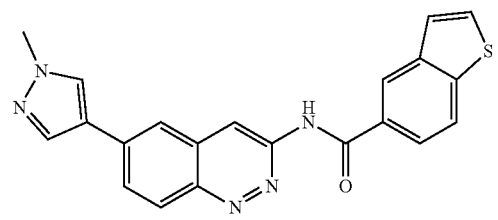 [SMILES: Cn1cc(-c2ccc3nnc(NC(=O)c4ccc5sccc5c4)cc3c2)cn1] 2021

TABLE 1-continued
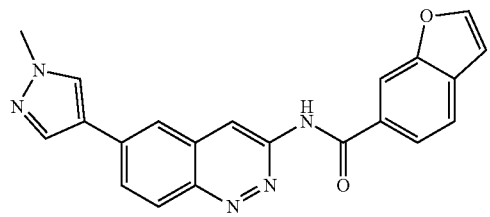 [SMILES: Cn1cc(-c2ccc3nnc(NC(=O)c4ccc5ccoc5c4)cc3c2)cn1] 2022
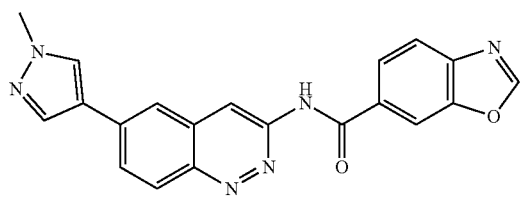 [SMILES: Cn1cc(-c2ccc3nnc(NC(=O)c4ccc5ncoc5c4)cc3c2)cn1] 2023
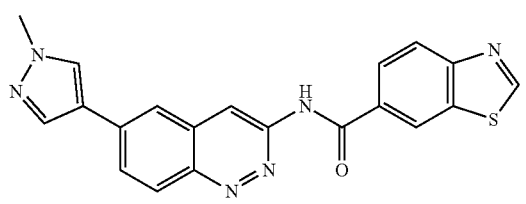 [SMILES: Cn1cc(-c2ccc3nnc(NC(=O)c4ccc5ncsc5c4)cc3c2)cn1] 2024
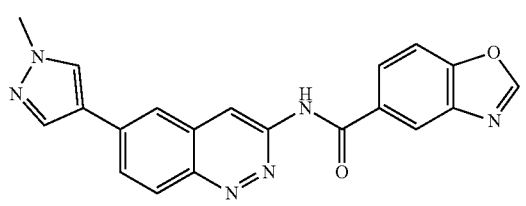 2025
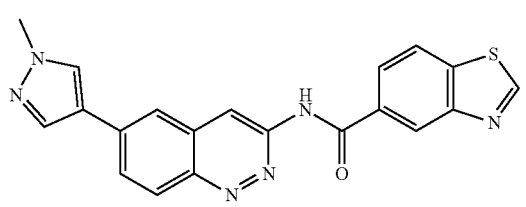 [SMILES: Cn1cc(-c2ccc3nnc(NC(=O)c4ccc5ocnc5c4)cc3c2)cn1] 2026
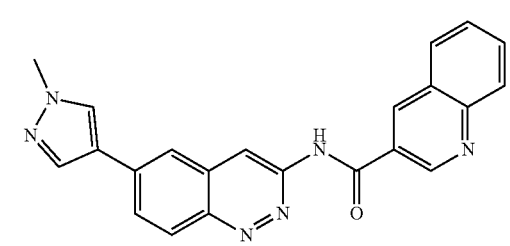 [SMILES: Cn1cc(-c2ccc3nnc(NC(=O)c4cnc5ccccc5c4)cc3c2)cn1] 2027
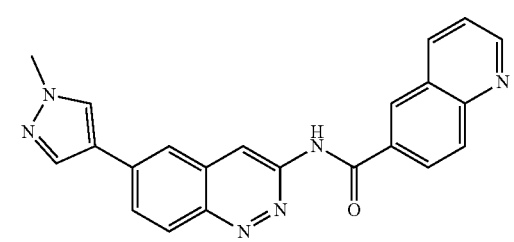 [SMILES: Cn1cc(-c2ccc3nnc(NC(=O)c4ccc5ncccc5c4)cc3c2)cn1] 2028

TABLE 1-continued
| | |
|---|---|
| 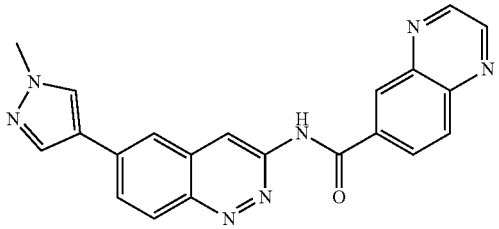 [SMILES: Cn1cc(-c2ccc3nnc(NC(=O)c4ccc5nccnc5c4)cc3c2)cn1] | 2029 |
| 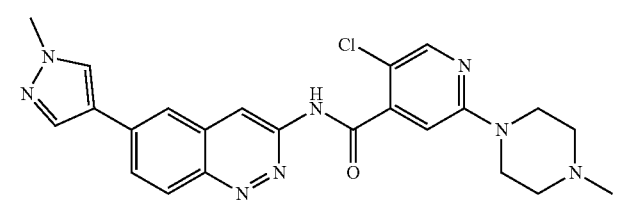 [SMILES: CN1CCN(c2cc(C(=O)Nc3cc4cc(-c5cnn(C)c5)ccc4nn3)c(Cl)cn2)CC1] | 2030 |
| 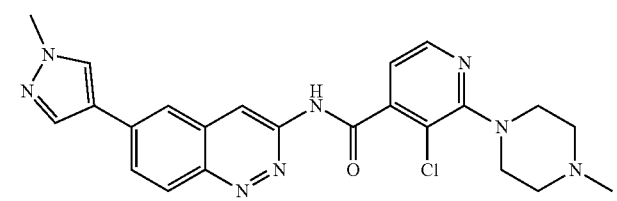 [SMILES: CN1CCN(c2nccc(C(=O)Nc3cc4cc(-c5cnn(C)c5)ccc4nn3)c2Cl)CC1] | 2031 |
| 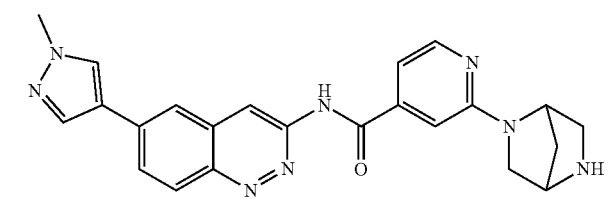 [SMILES: Cn1cc(-c2ccc3nnc(NC(=O)c4ccnc(N5CC6CC5CN6)c4)cc3c2)cn1] | 2032 |
| 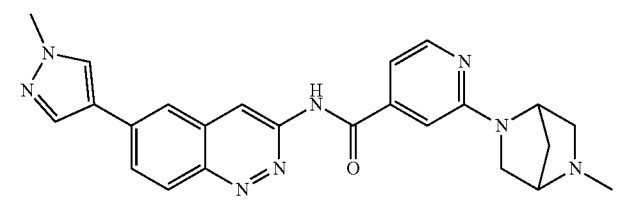 [SMILES: CN1CC2CC1CN2c1cc(C(=O)Nc2cc3cc(-c4cnn(C)c4)ccc3nn2)ccn1] | 2033 |
| 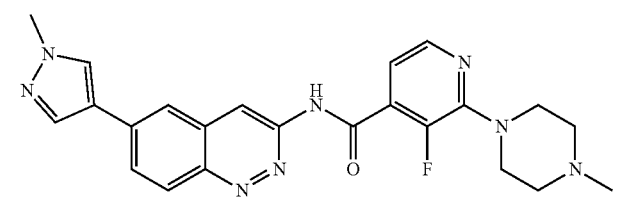 [SMILES: CN1CCN(c2nccc(C(=O)Nc3cc4cc(-c5cnn(C)c5)ccc4nn3)c2F)CC1] | 2034 |
| 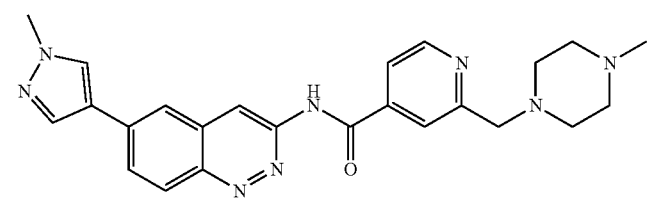 [SMILES: CN1CCN(Cc2cc(C(=O)Nc3cc4cc(-c5cnn(C)c5)ccc4nn3)ccn2)CC1] | 2035 |
| 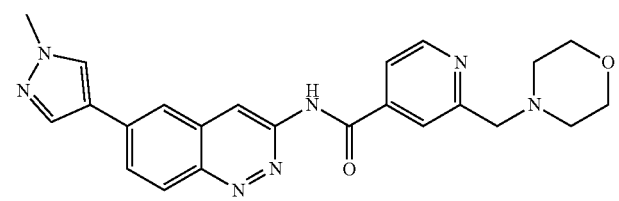 [SMILES: Cn1cc(-c2ccc3nnc(NC(=O)c4ccnc(CN5CCOCC5)c4)cc3c2)cn1] | 2036 |

TABLE 1-continued
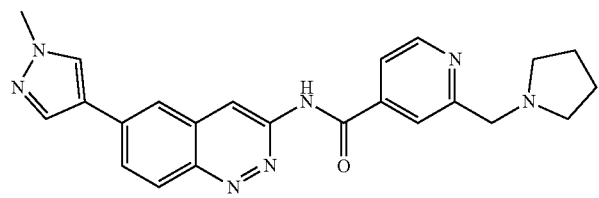 2037
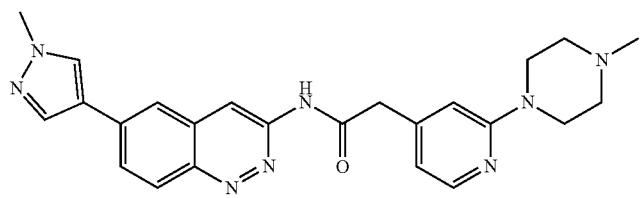 [SMILES: CN1CCN(c2cc(CC(=O)Nc3cc4cc(-c5cnn(C)c5)ccc4nn3)ccn2)CC1] 2038
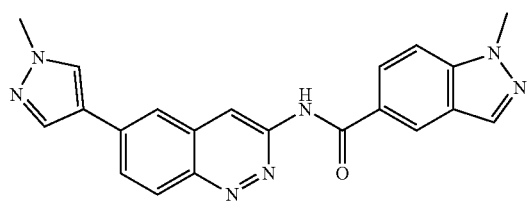 [SMILES: Cn1cc(-c2ccc3nnc(NC(=O)c4ccc5c(cnn5C)c4)cc3c2)cn1] 2039
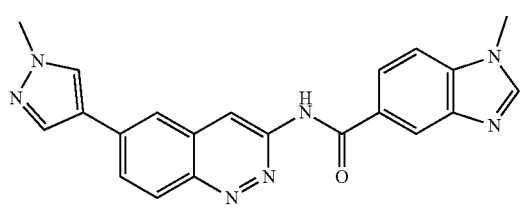 [SMILES: Cn1cc(-c2ccc3nnc(NC(=O)c4ccc5c(c4)ncn5C)cc3c2)cn1] 2040
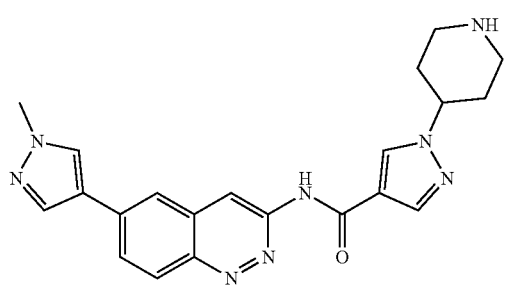 [SMILES: Cn1cc(-c2ccc3nnc(NC(=O)c4cnn(C5CCNCC5)c4)cc3c2)cn1] 2041
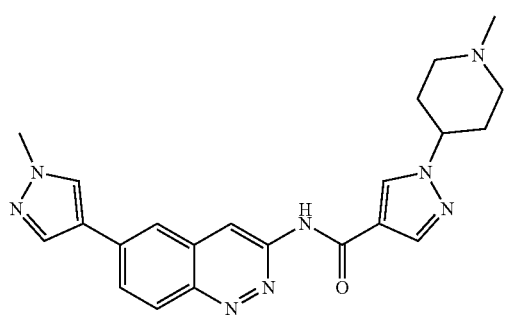 [SMILES: CN1CCC(n2cc(C(=O)Nc3cc4cc(-c5cnn(C)c5)ccc4nn3)cn2)CC1] 2042

TABLE 1-continued
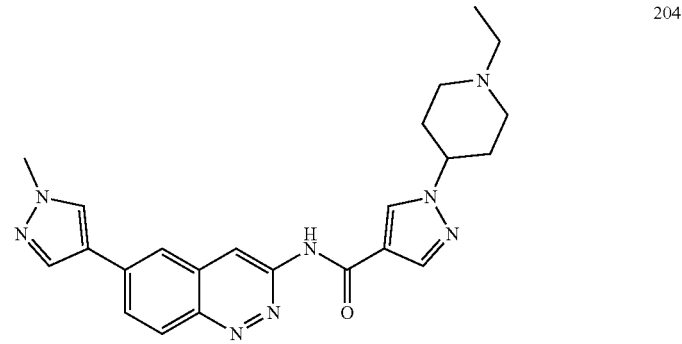 2043
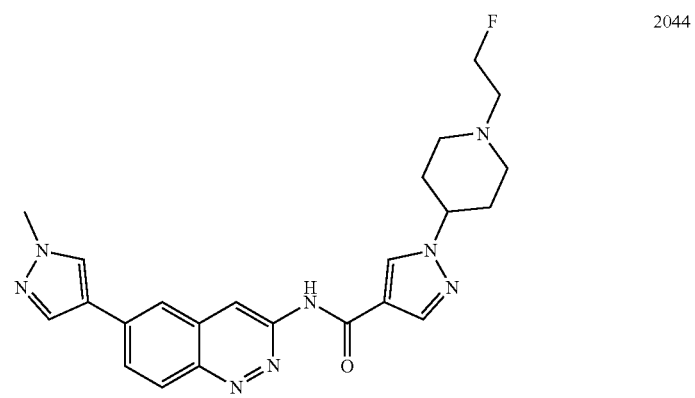 2044
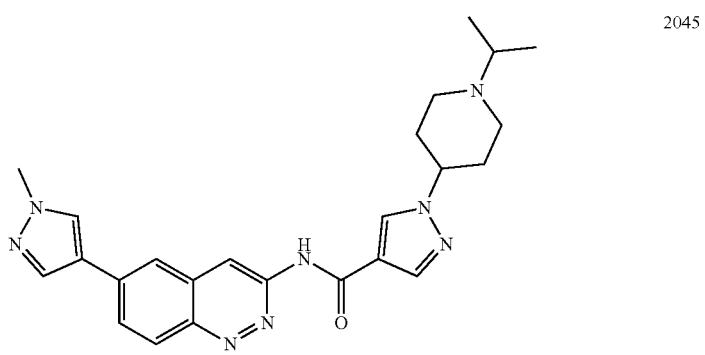 2045
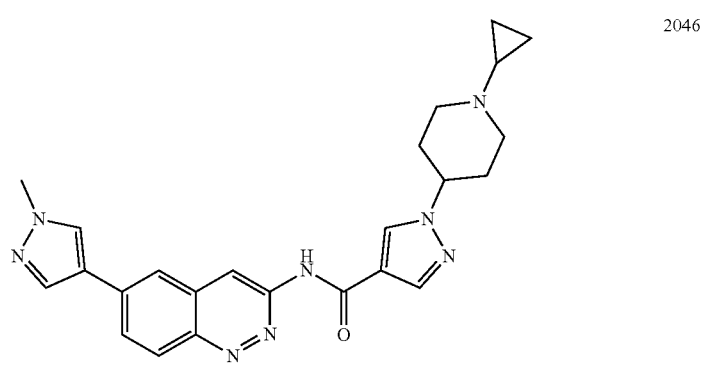 2046

TABLE 1-continued
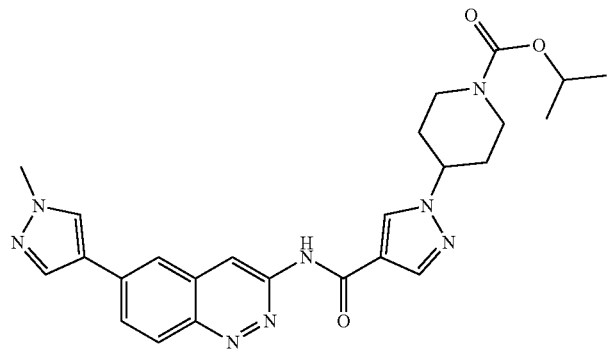 [SMILES: CC(C)OC(=O)N1CCC(n2cc(C(=O)Nc3cc4cc(-c5cnn(C)c5)ccc4nn3)cn2)CC1]
2047
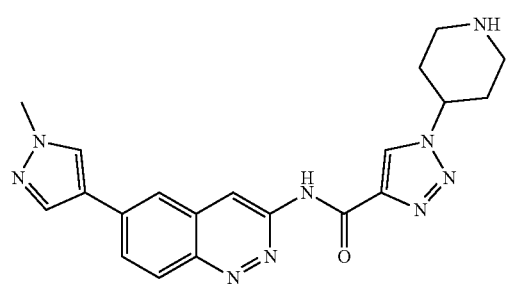 [SMILES: Cn1cc(-c2ccc3nnc(NC(=O)c4cn(C5CCNCC5)nn4)cc3c2)cn1]
2048
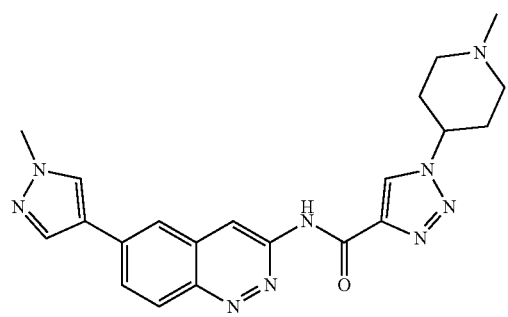
2049
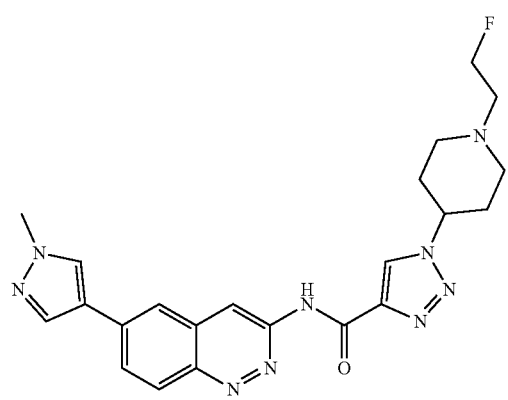 [SMILES: Cn1cc(-c2ccc3nnc(NC(=O)c4cn(C5CCN(CCF)CC5)nn4)cc3c2)cn1]
2050

TABLE 1-continued
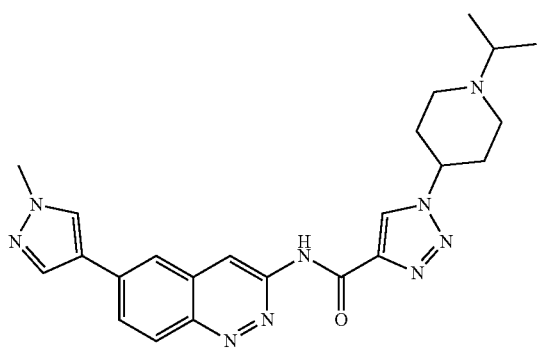 [SMILES: CC(C)N1CCC(n2cc(C(=O)Nc3cc4cc(-c5cnn(C)c5)ccc4nn3)nn2)CC1]
2051
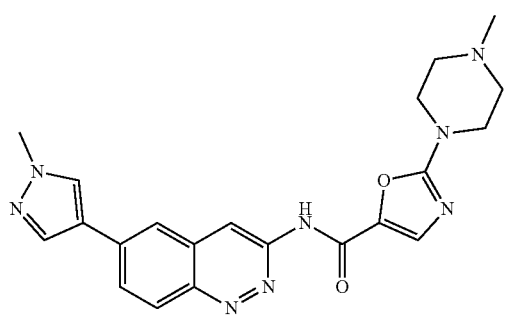 [SMILES: CN1CCN(c2ncc(C(=O)Nc3cc4cc(-c5cnn(C)c5)ccc4nn3)o2)CC1]
2052
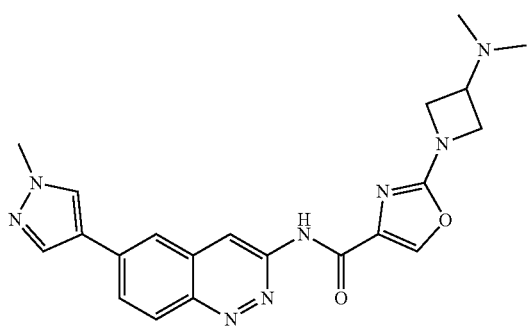 [SMILES: CN(C)C1CN(c2nc(C(=O)Nc3cc4cc(-c5cnn(C)c5)ccc4nn3)co2)C1]
2053
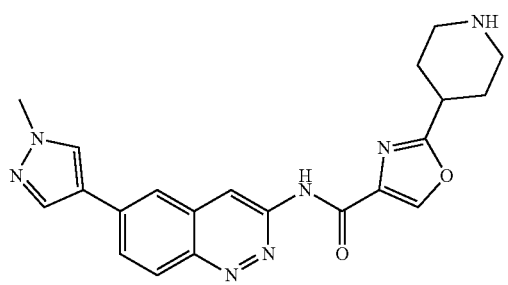 [SMILES: Cn1cc(-c2ccc3nnc(NC(=O)c4coc(C5CCNCC5)n4)cc3c2)cn1]
2054
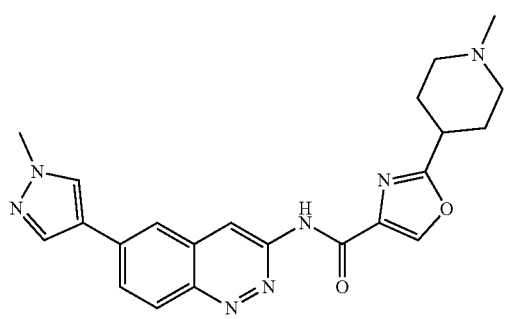 [SMILES: CN1CCC(c2nc(C(=O)Nc3cc4cc(-c5cnn(C)c5)ccc4nn3)co2)CC1]
2055

TABLE 1-continued
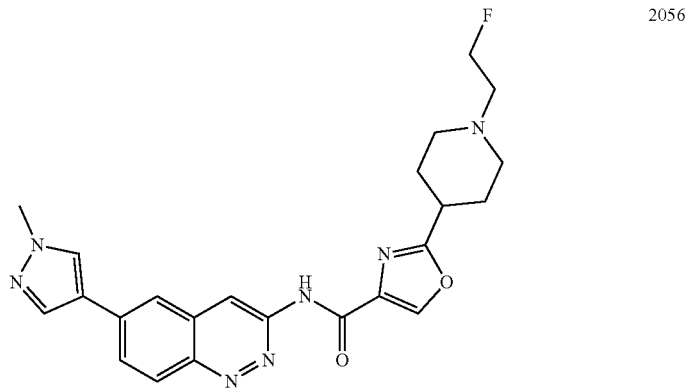 2056
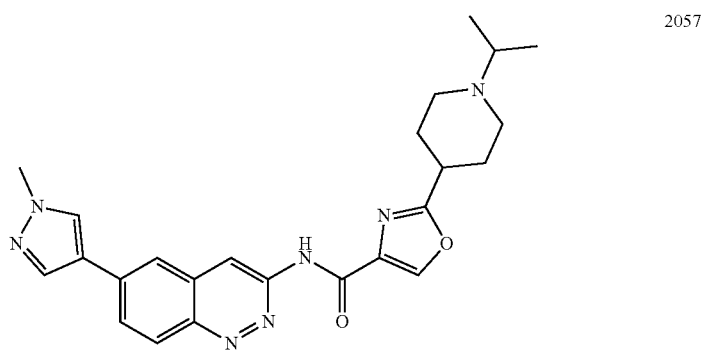 2057
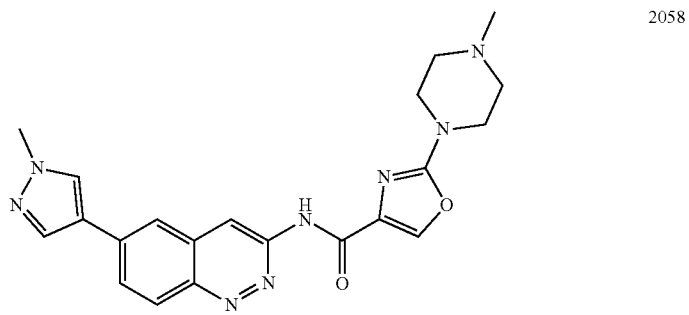 2058
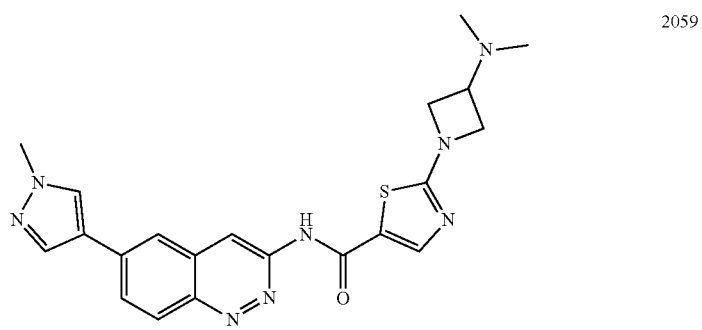 2059

TABLE 1-continued
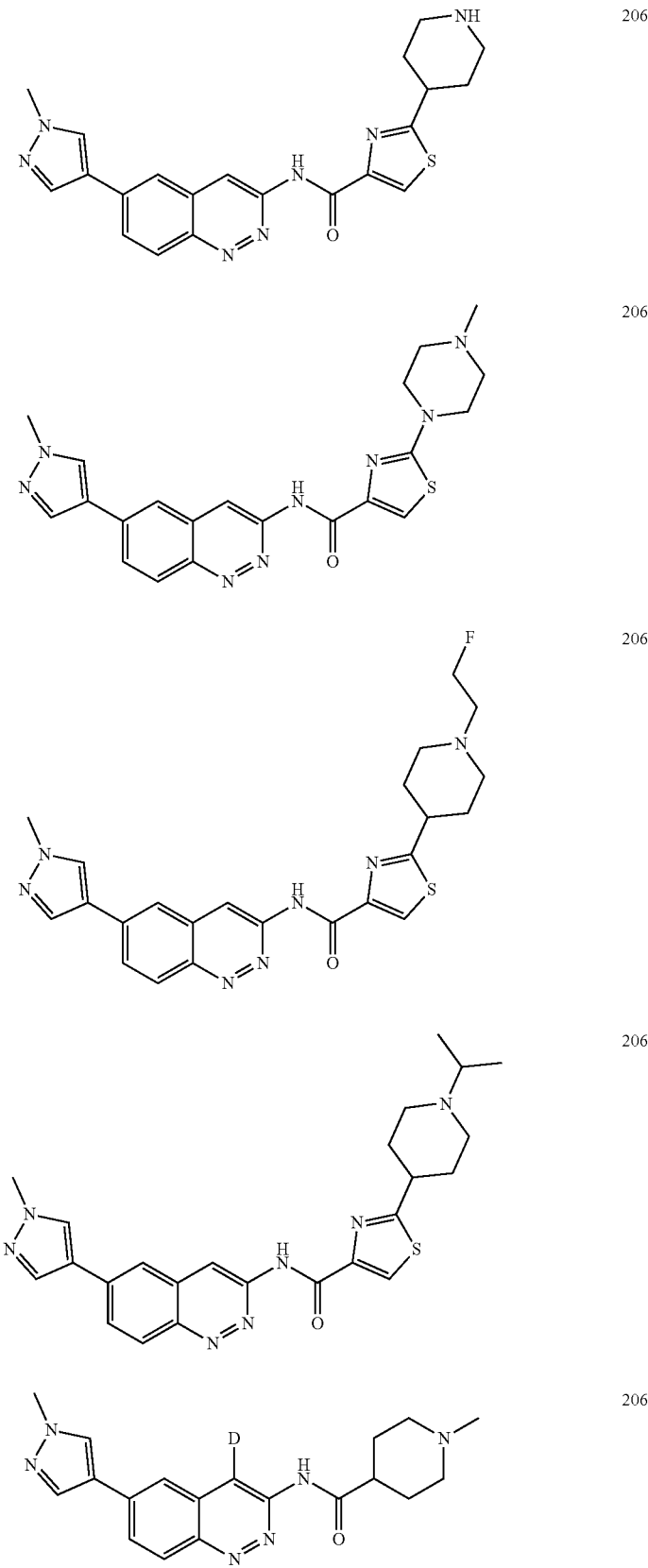

TABLE 1-continued
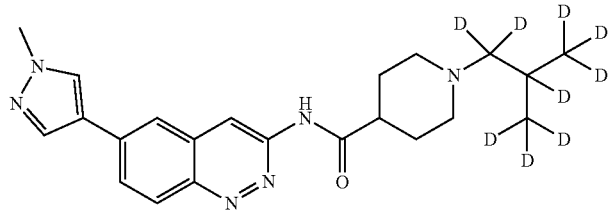 [SMILES: [2H]C([2H])([2H])C([2H])(C([2H])([2H])[2H])C([2H])([2H])N1CCC(C(=O)Nc2cc3cc(-c4cnn(C)c4)ccc3nn2)CC1] 2065
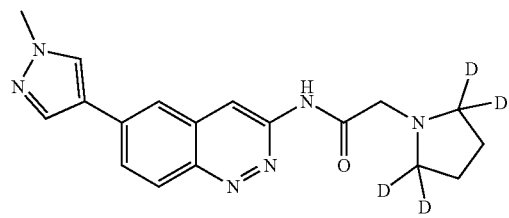 [SMILES: [2H]C1([2H])CCC([2H])([2H])N1CC(=O)Nc1cc2cc(-c3cnn(C)c3)ccc2nn1] 2066
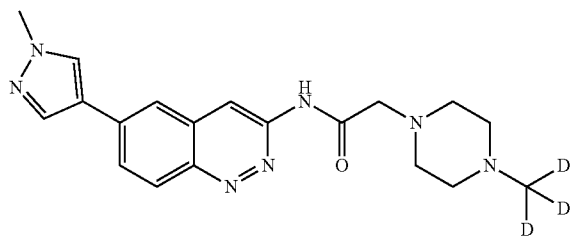 [SMILES: [2H]C([2H])([2H])N1CCN(CC(=O)Nc2cc3cc(-c4cnn(C)c4)ccc3nn2)CC1] 2067
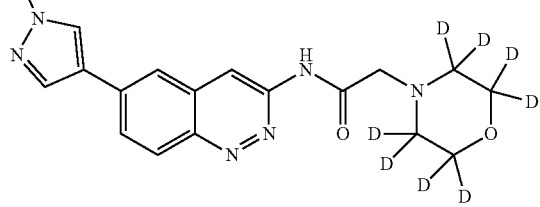 2068
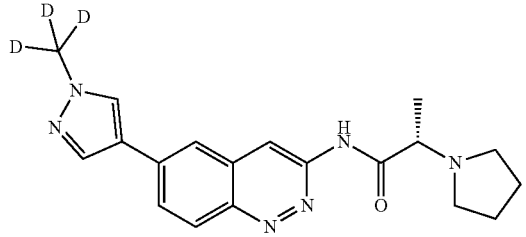 [SMILES: [2H]C([2H])([2H])n1cc(-c2ccc3nnc(NC(=O)[C@H](C)N4CCCC4)cc3c2)cn1] 2069
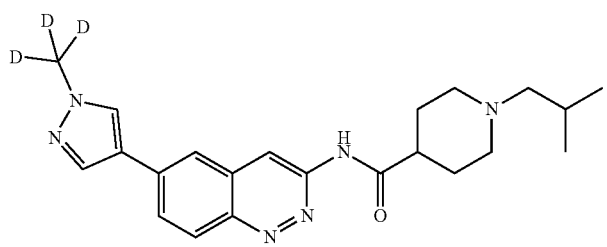 [SMILES: [2H]C([2H])([2H])n1cc(-c2ccc3nnc(NC(=O)C4CCN(CC(C)C)CC4)cc3c2)cn1] 2070

TABLE 1-continued
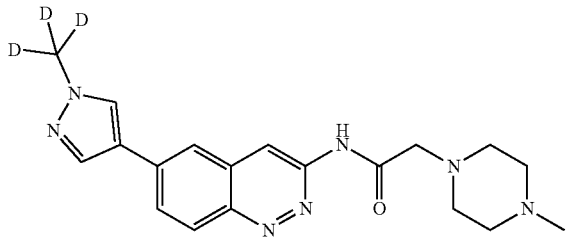 [SMILES: [2H]C([2H])([2H])n1cc(-c2ccc3nnc(NC(=O)CN4CCN(C)CC4)cc3c2)cn1]
2071
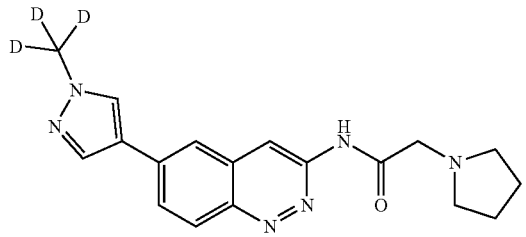 [SMILES: [2H]C([2H])([2H])n1cc(-c2ccc3nnc(NC(=O)CN4CCCC4)cc3c2)cn1]
2072
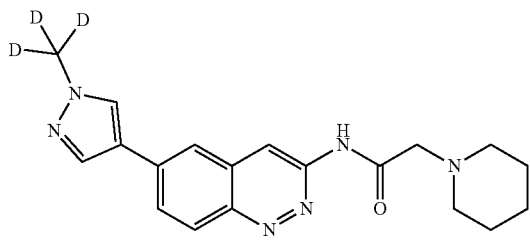 [SMILES: [2H]C([2H])([2H])n1cc(-c2ccc3nnc(NC(=O)CN4CCCCC4)cc3c2)cn1]
2073
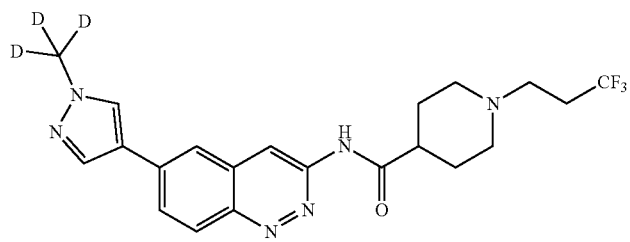 [SMILES: [2H]C([2H])([2H])n1cc(-c2ccc3nnc(NC(=O)C4CCN(CCC(F)(F)F)CC4)cc3c2)cn1]
2074
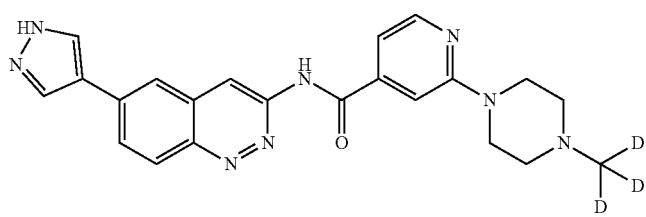 [SMILES: [2H]C([2H])([2H])N1CCN(c2cc(C(=O)Nc3cc4cc(-c5cn[nH]c5)ccc4nn3)ccn2)CC1]
2075
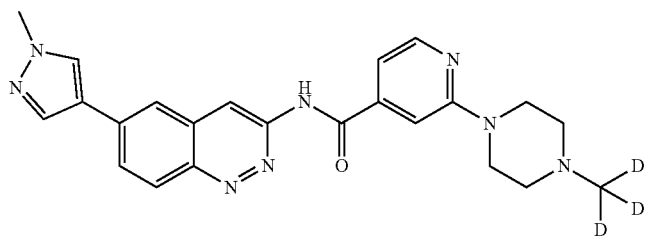 [SMILES: [2H]C([2H])([2H])N1CCN(c2cc(C(=O)Nc3cc4cc(-c5cnn(C)c5)ccc4nn3)ccn2)CC1]
2076

TABLE 1-continued
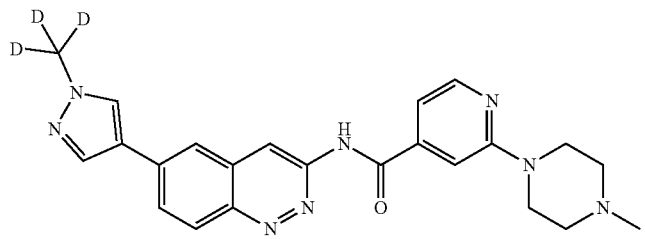 [SMILES: [2H]C([2H])([2H])n1cc(-c2ccc3nnc(NC(=O)c4ccnc(N5CCN(C)CC5)c4)cc3c2)cn1] 2077
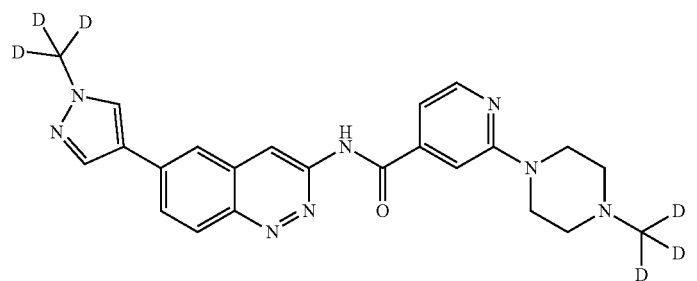 [SMILES: [2H]C([2H])([2H])N1CCN(c2cc(C(=O)Nc3cc4cc(-c5cnn(C([2H])([2H])[2H])c5)ccc4nn3)ccn2)CC1] 2078
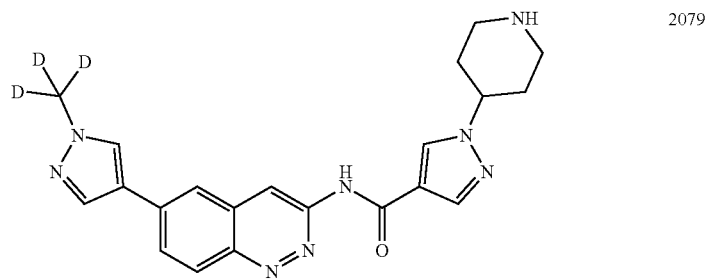 2079
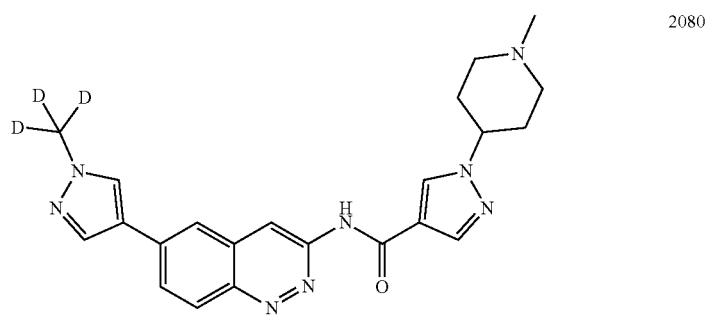 2080
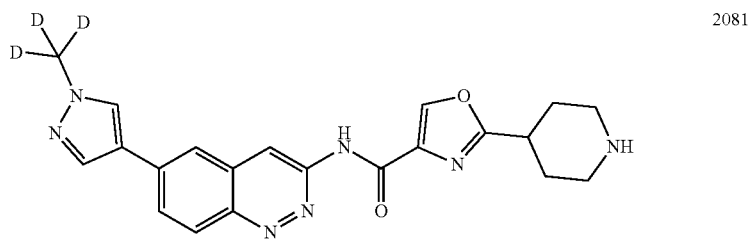 2081
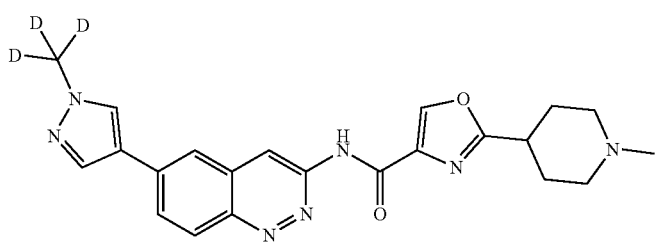 [SMILES: [2H]C([2H])([2H])n1cc(-c2ccc3nnc(NC(=O)c4coc(C5CCN(C)CC5)n4)cc3c2)cn1] 2082

TABLE 1-continued
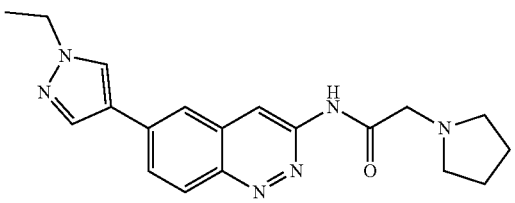 [SMILES: CCn1cc(-c2ccc3nnc(NC(=O)CN4CCCC4)cc3c2)cn1] 2083
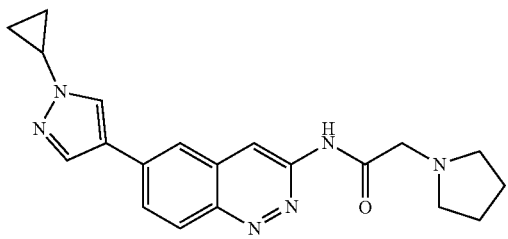 [SMILES: O=C(CN1CCCC1)Nc1cc2cc(-c3cnn(C4CC4)c3)ccc2nn1] 2084
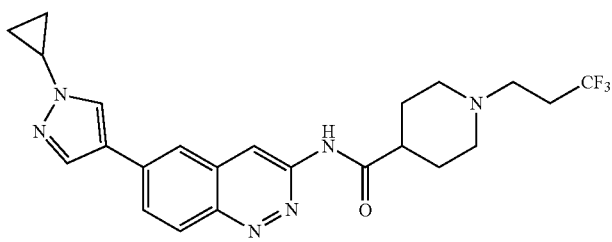 [SMILES: O=C(Nc1cc2cc(-c3cnn(C4CC4)c3)ccc2nn1)C1CCN(CCC(F)(F)F)CC1] 2085
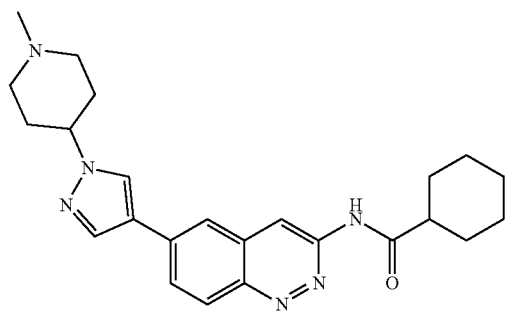 [SMILES: CN1CCC(n2cc(-c3ccc4nnc(NC(=O)C5CCCCC5)cc4c3)cn2)CC1] 2086
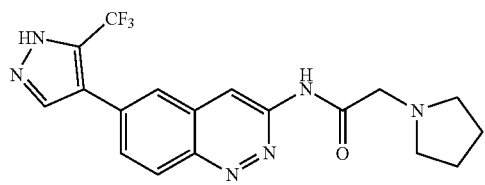 [SMILES: O=C(CN1CCCC1)Nc1cc2cc(-c3cn[nH]c3C(F)(F)F)ccc2nn1] 2087
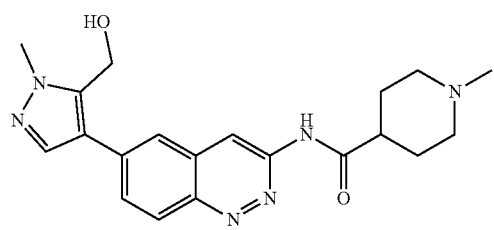 [SMILES: CN1CCC(C(=O)Nc2cc3cc(-c4cnn(C)c4CO)ccc3nn2)CC1] 2088

TABLE 1-continued
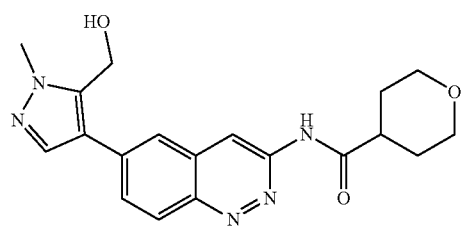 [SMILES: Cn1ncc(-c2ccc3nnc(NC(=O)C4CCOCC4)cc3c2)c1CO] 2089
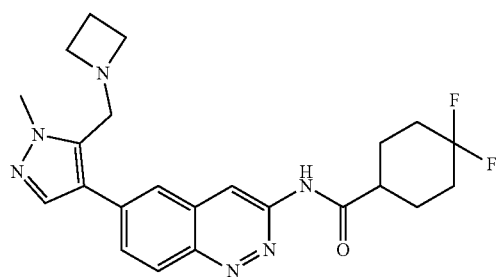 [SMILES: Cn1ncc(-c2ccc3nnc(NC(=O)C4CCC(F)(F)CC4)cc3c2)c1CN1CCC1] 2090
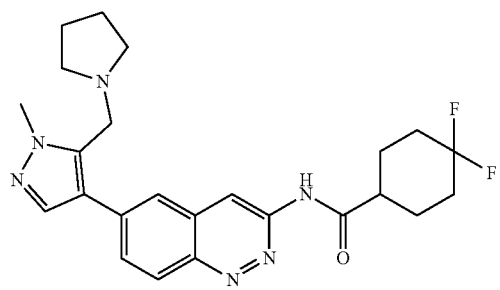 [SMILES: Cn1ncc(-c2ccc3nnc(NC(=O)C4CCC(F)(F)CC4)cc3c2)c1CN1CCCC1] 2091
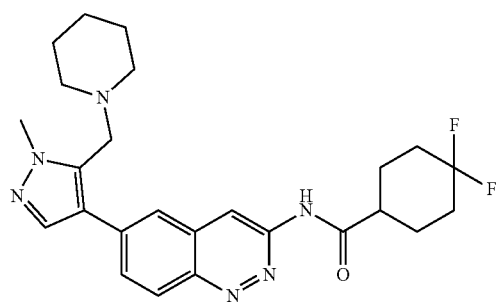 [SMILES: Cn1ncc(-c2ccc3nnc(NC(=O)C4CCC(F)(F)CC4)cc3c2)c1CN1CCCCC1] 2092
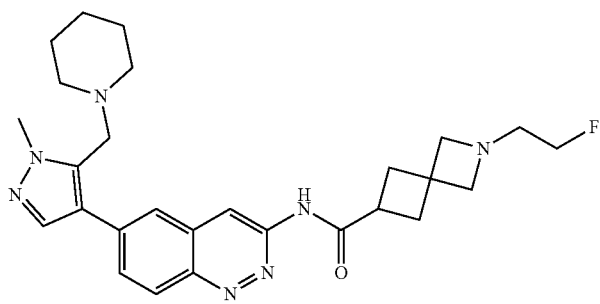 [SMILES: Cn1ncc(-c2ccc3nnc(NC(=O)C4CC5(C4)CN(CCF)C5)cc3c2)c1CN1CCCCC1] 2093

TABLE 1-continued
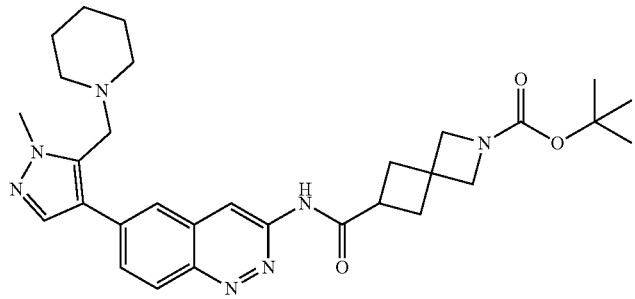 [SMILES: Cn1ncc(-c2ccc3nnc(NC(=O)C4CC5(C4)CN(C(=O)OC(C)(C)C)C5)cc3c2)c1CN1CCCCC1]
2094
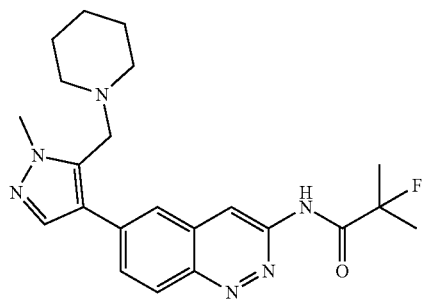 [SMILES: Cn1ncc(-c2ccc3nnc(NC(=O)C(C)(C)F)cc3c2)c1CN1CCCCC1]
2095
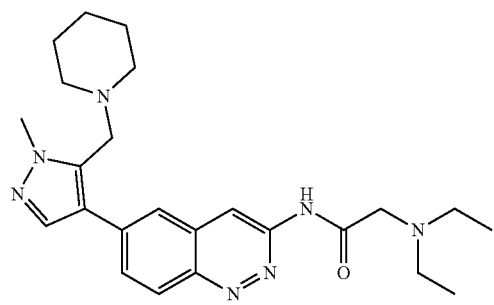 [SMILES: CCN(CC)CC(=O)Nc1cc2cc(-c3cnn(C)c3CN3CCCCC3)ccc2nn1]
2096
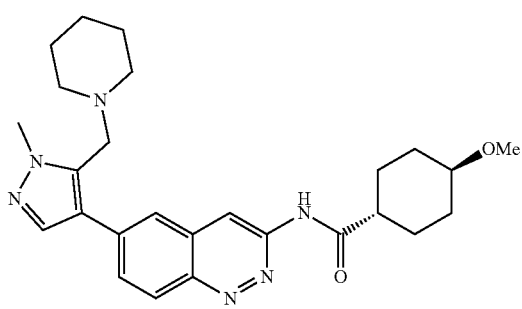 [SMILES: CO[C@H]1CC[C@H](C(=O)Nc2cc3cc(-c4cnn(C)c4CN4CCCCC4)ccc3nn2)CC1]
2097
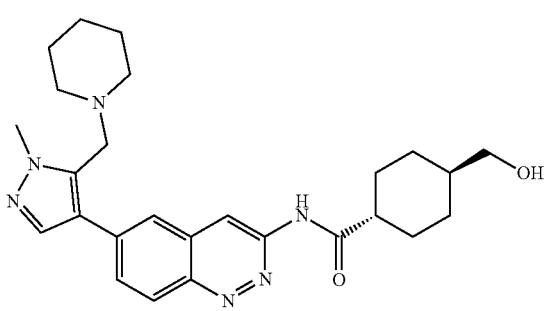 [SMILES: Cn1ncc(-c2ccc3nnc(NC(=O)[C@H]4CC[C@H](CO)CC4)cc3c2)c1CN1CCCCC1]
2098

TABLE 1-continued
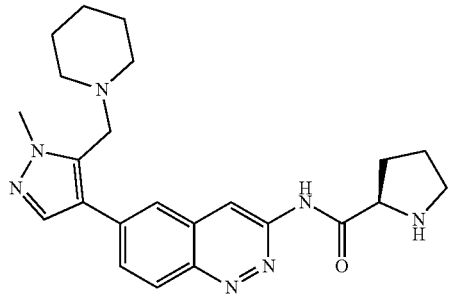 [SMILES: Cn1ncc(-c2ccc3nnc(NC(=O)[C@H]4CCCN4)cc3c2)c1CN1CCCCC1]
2099
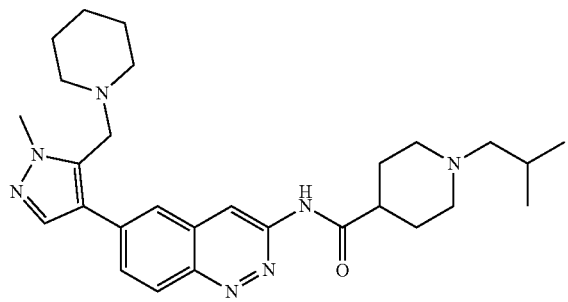 [SMILES: CC(C)CN1CCC(C(=O)Nc2cc3cc(-c4cnn(C)c4CN4CCCCC4)ccc3nn2)CC1]
2100
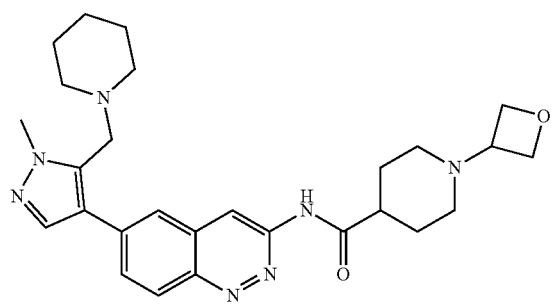 [SMILES: Cn1ncc(-c2ccc3nnc(NC(=O)C4CCN(C5COC5)CC4)cc3c2)c1CN1CCCCC1]
2101
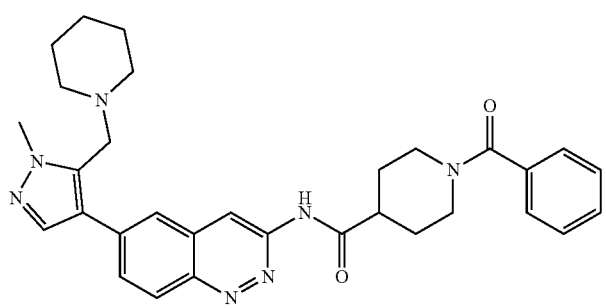 [SMILES: Cn1ncc(-c2ccc3nnc(NC(=O)C4CCN(C(=O)c5ccccc5)CC4)cc3c2)c1CN1CCCCC1]
2102
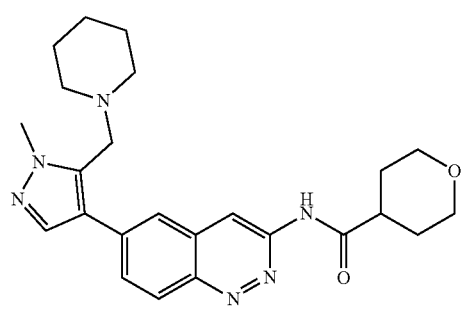 [SMILES: Cn1ncc(-c2ccc3nnc(NC(=O)C4CCOCC4)cc3c2)c1CN1CCCCC1]
2103

TABLE 1-continued
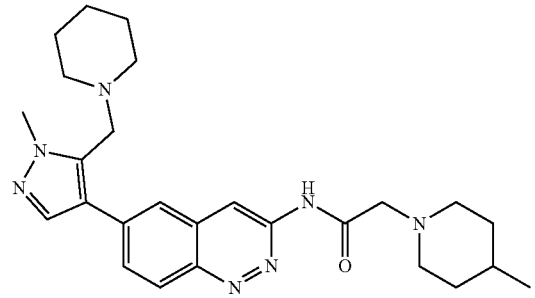 [SMILES: CC1CCN(CC(=O)Nc2cc3cc(-c4cnn(C)c4CN4CCCCC4)ccc3nn2)CC1]
2104
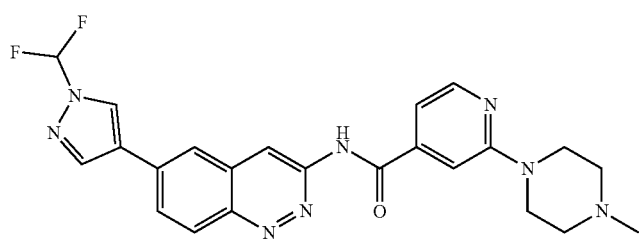 [SMILES: CN1CCN(c2cc(C(=O)Nc3cc4cc(-c5cnn(C(F)F)c5)ccc4nn3)ccn2)CC1]
2105
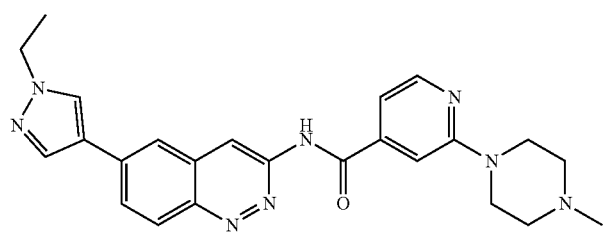 [SMILES: CCn1cc(-c2ccc3nnc(NC(=O)c4ccnc(N5CCN(C)CC5)c4)cc3c2)cn1]
2106
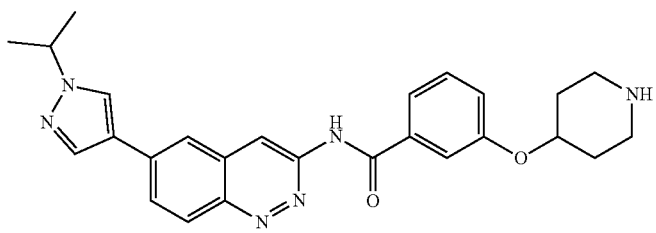 [SMILES: CC(C)n1cc(-c2ccc3nnc(NC(=O)c4cccc(OC5CCNCC5)c4)cc3c2)cn1]
2107
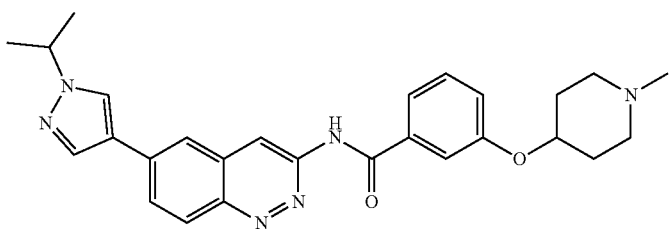 [SMILES: CC(C)n1cc(-c2ccc3nnc(NC(=O)c4cccc(OC5CCN(C)CC5)c4)cc3c2)cn1]
2108
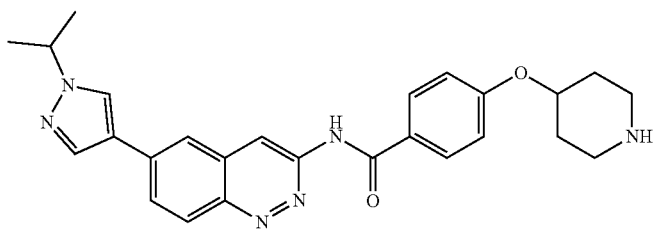 [SMILES: CC(C)n1cc(-c2ccc3nnc(NC(=O)c4ccc(OC5CCNCC5)cc4)cc3c2)cn1]
2109

TABLE 1-continued
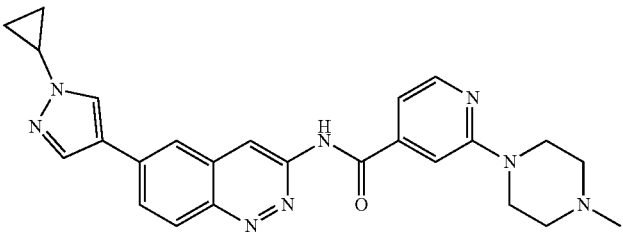 [SMILES: CN1CCN(c2cc(C(=O)Nc3cc4cc(-c5cnn(C6CC6)c5)ccc4nn3)ccn2)CC1]
2110
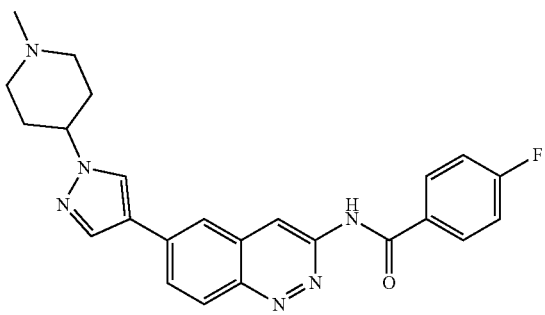 [SMILES: CN1CCC(n2cc(-c3ccc4nnc(NC(=O)c5ccc(F)cc5)cc4c3)cn2)CC1]
2111
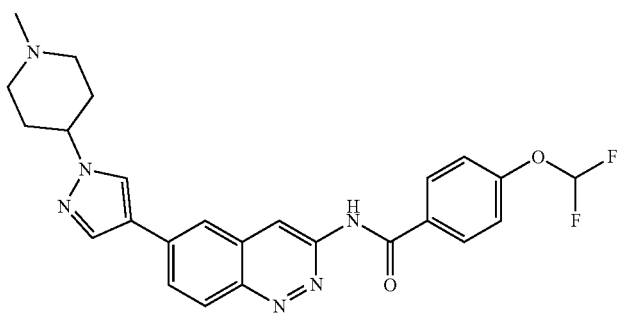 [SMILES: CN1CCC(n2cc(-c3ccc4nnc(NC(=O)c5ccc(OC(F)F)cc5)cc4c3)cn2)CC1]
2112
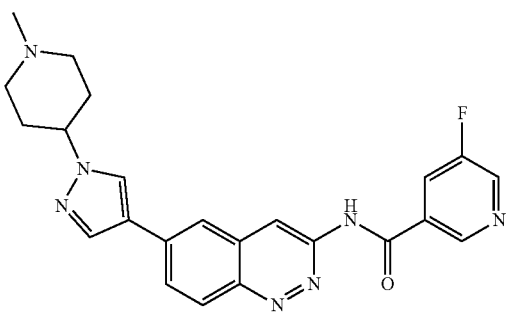 [SMILES: CN1CCC(n2cc(-c3ccc4nnc(NC(=O)c5cncc(F)c5)cc4c3)cn2)CC1]
2113
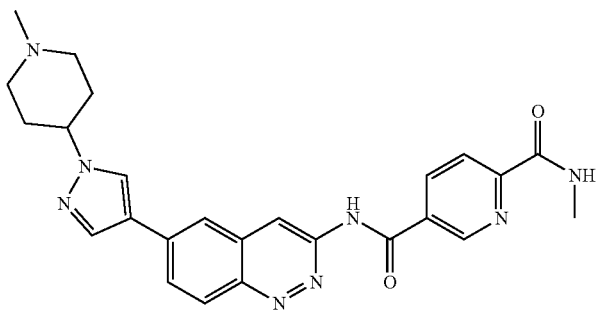 [SMILES: CNC(=O)c1ccc(C(=O)Nc2cc3cc(-c4cnn(C5CCN(C)CC5)c4)ccc3nn2)cn1]
2114

TABLE 1-continued
| | |
|---|---|
| 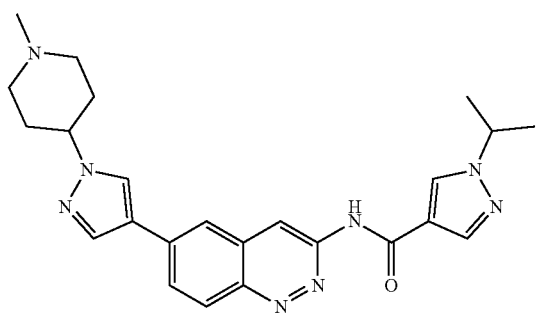 [SMILES: CC(C)n1cc(C(=O)Nc2cc3cc(-c4cnn(C5CCN(C)CC5)c4)ccc3nn2)cn1] | 2115 |
| 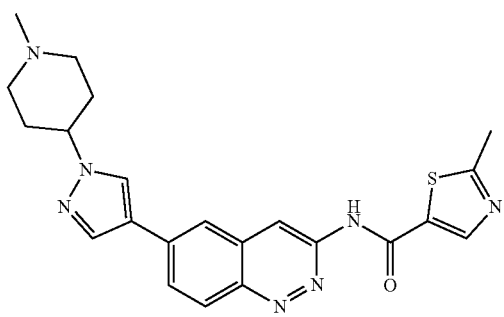 [SMILES: Cc1ncc(C(=O)Nc2cc3cc(-c4cnn(C5CCN(C)CC5)c4)ccc3nn2)s1] | 2116 |
| 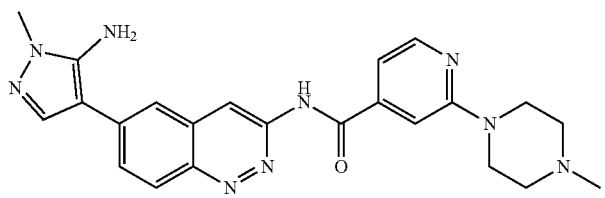 | 2117 |
| 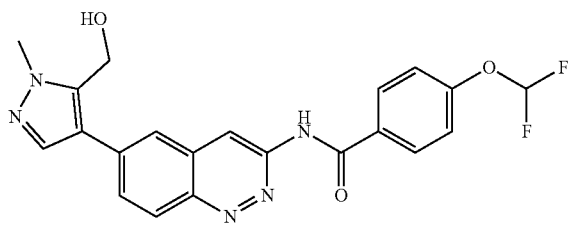 [SMILES: Cn1ncc(-c2ccc3nnc(NC(=O)c4ccc(OC(F)F)cc4)cc3c2)c1CO] | 2118 |
| 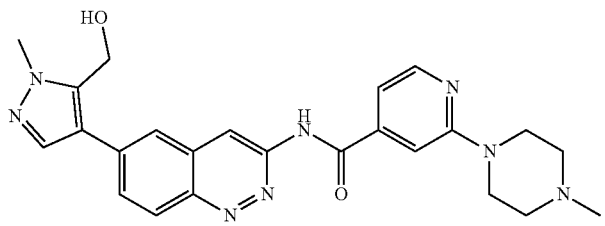 [SMILES: CN1CCN(c2cc(C(=O)Nc3cc4cc(-c5cnn(C)c5CO)ccc4nn3)ccn2)CC1] | 2119 |
| 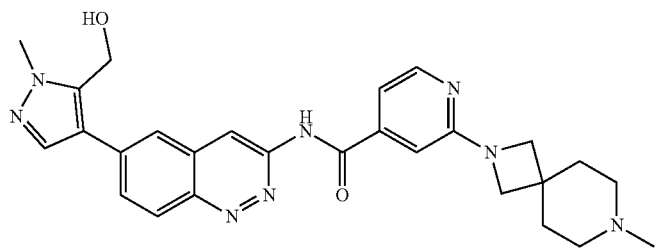 [SMILES: CN1CCC2(CC1)CN(c1cc(C(=O)Nc3cc4cc(-c5cnn(C)c5CO)ccc4nn3)ccn1)C2] | 2120 |

TABLE 1-continued
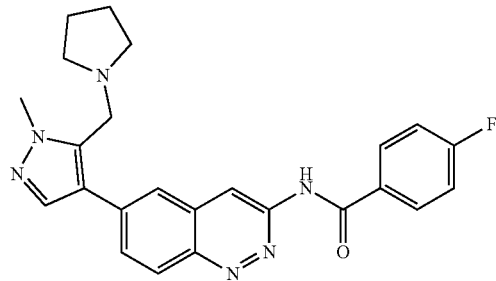 [SMILES: Cn1ncc(-c2ccc3nnc(NC(=O)c4ccc(F)cc4)cc3c2)c1CN1CCCC1] 2121
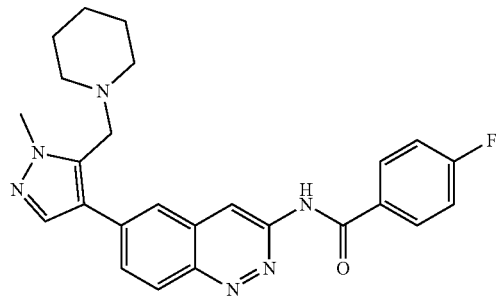 [SMILES: Cn1ncc(-c2ccc3nnc(NC(=O)c4ccc(F)cc4)cc3c2)c1CN1CCCCC1] 2122
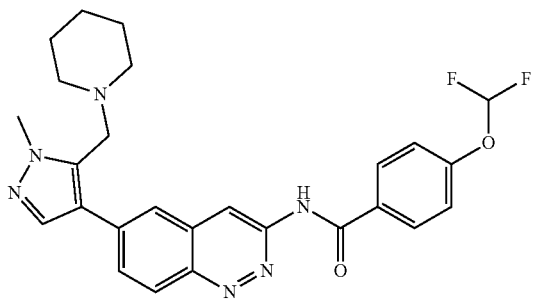 [SMILES: Cn1ncc(-c2ccc3nnc(NC(=O)c4ccc(OC(F)F)cc4)cc3c2)c1CN1CCCCC1] 2123
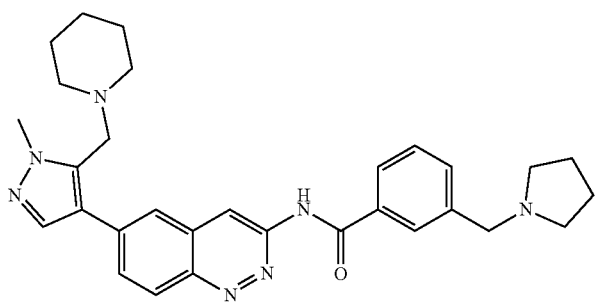 [SMILES: Cn1ncc(-c2ccc3nnc(NC(=O)c4cccc(CN5CCCC5)c4)cc3c2)c1CN1CCCCC1] 2124
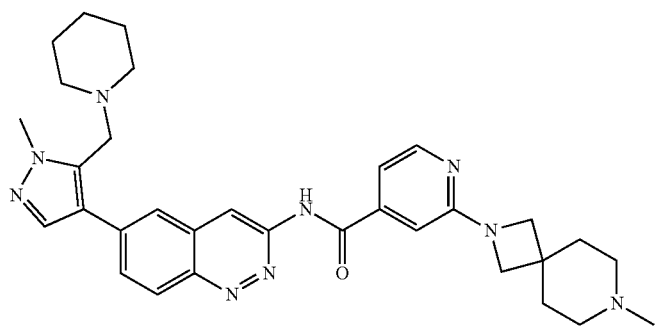 [SMILES: CN1CCC2(CC1)CN(c1cc(C(=O)Nc3cc4cc(-c5cnn(C)c5CN5CCCCC5)ccc4nn3)ccn1)C2] 2125

TABLE 1-continued
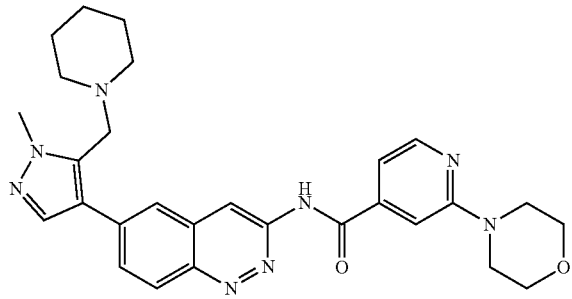 [SMILES: Cn1ncc(-c2ccc3nnc(NC(=O)c4ccnc(N5CCOCC5)c4)cc3c2)c1CN1CCCCC1] 2126
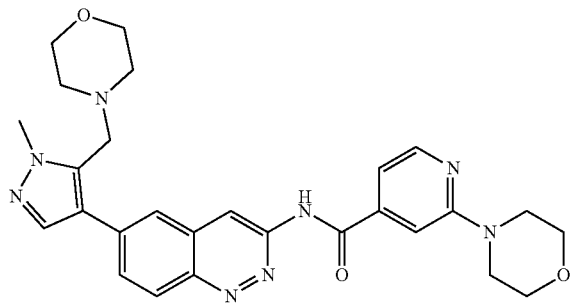 [SMILES: Cn1ncc(-c2ccc3nnc(NC(=O)c4ccnc(N5CCOCC5)c4)cc3c2)c1CN1CCOCC1] 2127
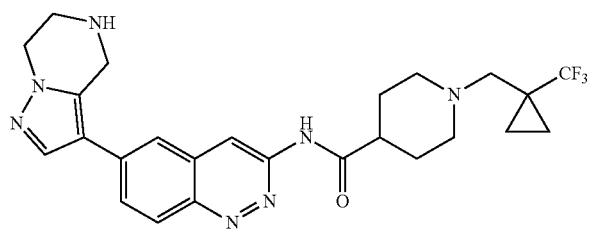 [SMILES: O=C(Nc1cc2cc(-c3cnn4c3CNCC4)ccc2nn1)C1CCN(CC2(C(F)(F)F)CC2)CC1] 2128
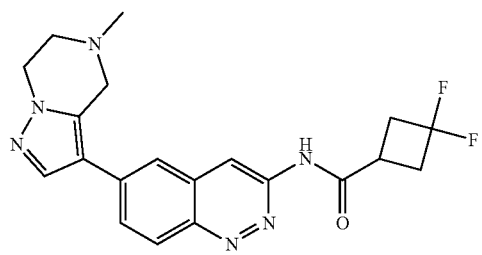 [SMILES: CN1CCn2ncc(-c3ccc4nnc(NC(=O)C5CC(F)(F)C5)cc4c3)c2C1] 2129
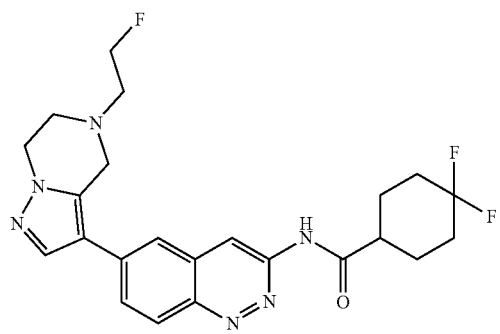 [SMILES: O=C(Nc1cc2cc(-c3cnn4c3CN(CCF)CC4)ccc2nn1)C1CCC(F)(F)CC1] 2130

TABLE 1-continued
| | |
|---|---|
| 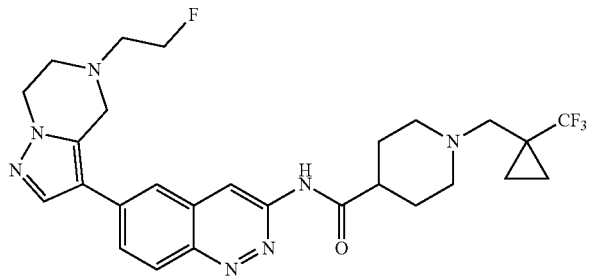 [SMILES: O=C(Nc1cc2cc(-c3cnn4c3CN(CCF)CC4)ccc2nn1)C1CCN(CC2(C(F)(F)F)CC2)CC1] | 2131 |
| 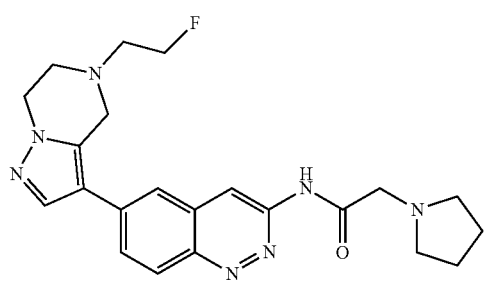 [SMILES: O=C(CN1CCCC1)Nc1cc2cc(-c3cnn4c3CN(CCF)CC4)ccc2nn1] | 2132 |
| 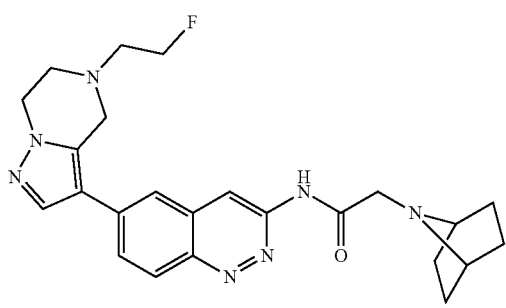 [SMILES: O=C(CN1C2CCC1CC2)Nc1cc2cc(-c3cnn4c3CN(CCF)CC4)ccc2nn1] | 2133 |
| 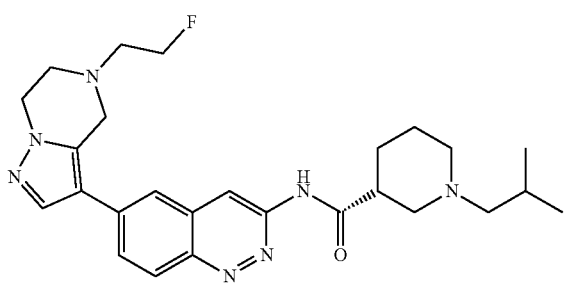 | 2134 |
| 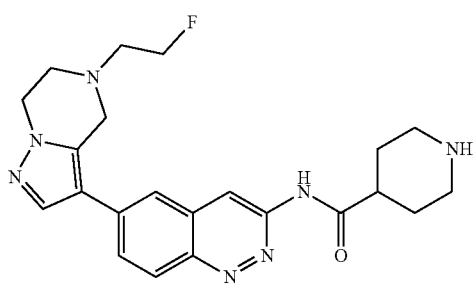 [SMILES: O=C(Nc1cc2cc(-c3cnn4c3CN(CCF)CC4)ccc2nn1)C1CCNCC1] | 2135 |

TABLE 1-continued
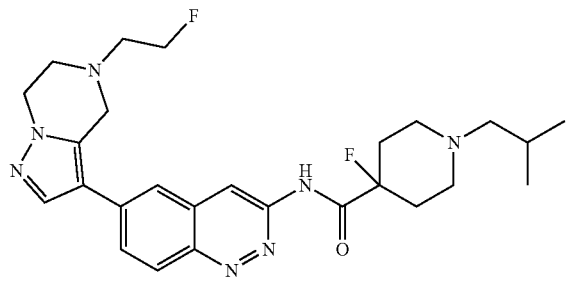 [SMILES: CC(C)CN1CCC(F)(C(=O)Nc2cc3cc(-c4cnn5c4CN(CCF)CC5)ccc3nn2)CC1]
2136
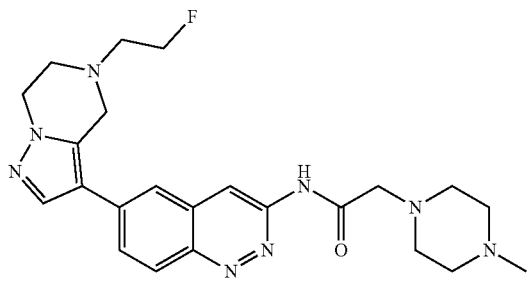 [SMILES: CN1CCN(CC(=O)Nc2cc3cc(-c4cnn5c4CN(CCF)CC5)ccc3nn2)CC1]
2137
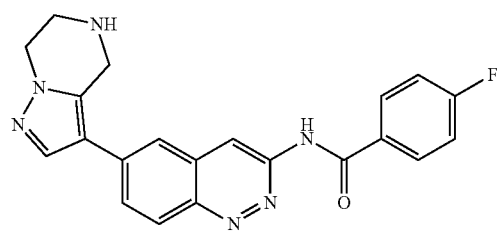 [SMILES: O=C(Nc1cc2cc(-c3cnn4c3CNCC4)ccc2nn1)c1ccc(F)cc1]
2138
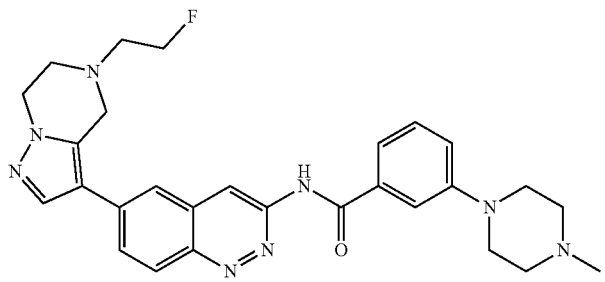
2139
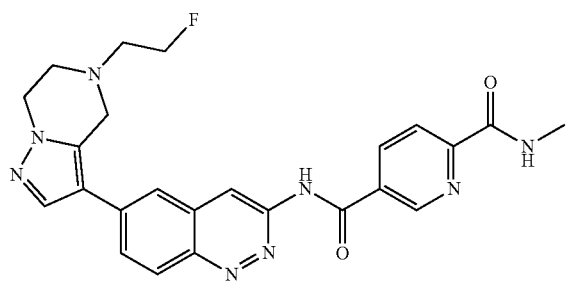 [SMILES: CNC(=O)c1ccc(C(=O)Nc2cc3cc(-c4cnn5c4CN(CCF)CC5)ccc3nn2)cn1]
2140
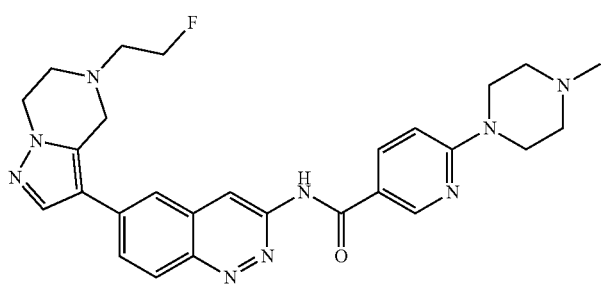
2141

TABLE 1-continued
| | |
|---|---|
| 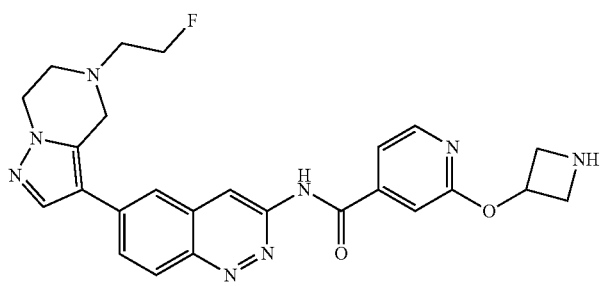 [SMILES: O=C(Nc1cc2cc(-c3cnn4c3CN(CCF)CC4)ccc2nn1)c1ccnc(OC2CNC2)c1] | 2142 |
| 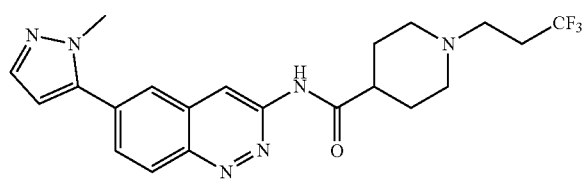 [SMILES: Cn1nccc1-c1ccc2nnc(NC(=O)C3CCN(CCC(F)(F)F)CC3)cc2c1] | 2143 |
| 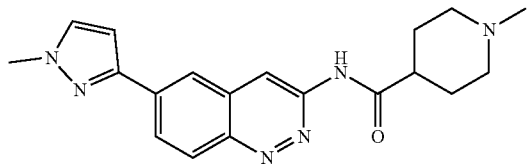 | 2144 |
| 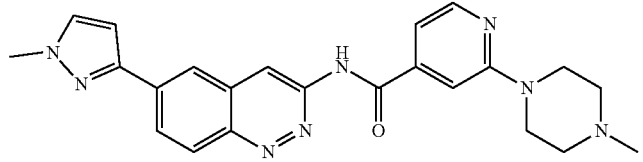 | 2145 |
| 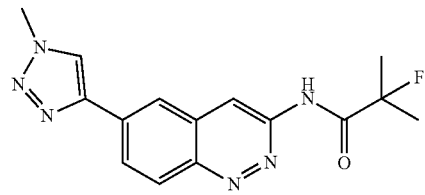 [SMILES: Cn1cc(-c2ccc3nnc(NC(=O)C(C)(C)F)cc3c2)nn1] | 2146 |
| 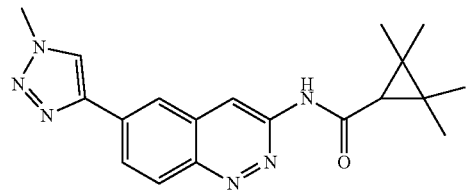 [SMILES: Cn1cc(-c2ccc3nnc(NC(=O)C4C(C)(C)C4(C)C)cc3c2)nn1] | 2147 |
| 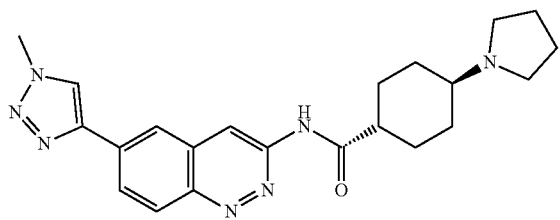 | 2148 |

TABLE 1-continued
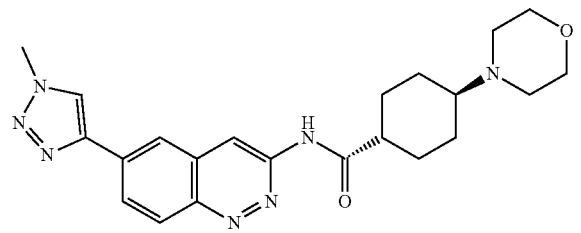 2149
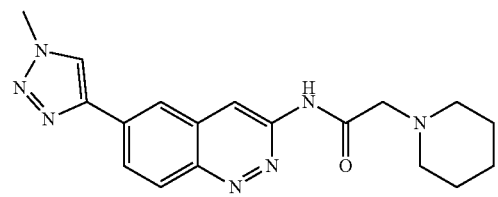 [SMILES: Cn1cc(-c2ccc3nnc(NC(=O)CN4CCCCC4)cc3c2)nn1] 2150
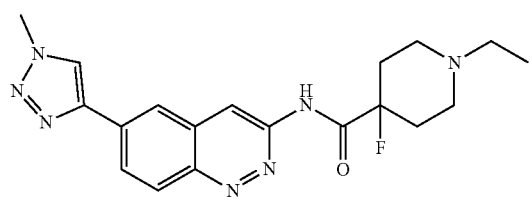 [SMILES: CCN1CCC(F)(C(=O)Nc2cc3cc(-c4cn(C)nn4)ccc3nn2)CC1] 2151
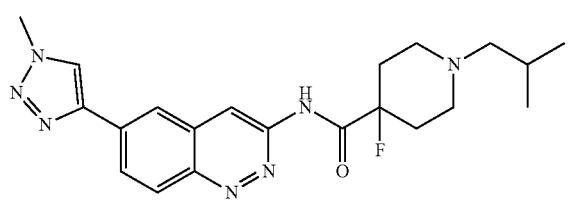 [SMILES: CC(C)CN1CCC(F)(C(=O)Nc2cc3cc(-c4cn(C)nn4)ccc3nn2)CC1] 2152
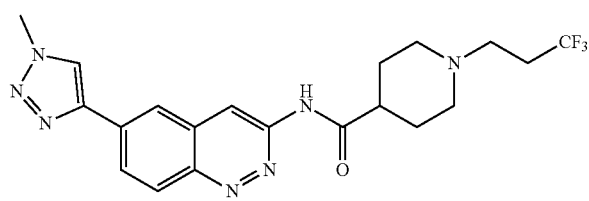 [SMILES: Cn1cc(-c2ccc3nnc(NC(=O)C4CCN(CCC(F)(F)F)CC4)cc3c2)nn1] 2153
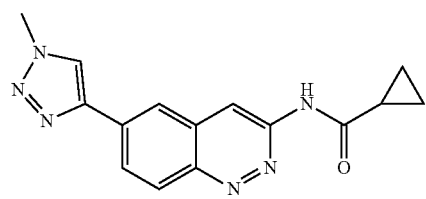 2154
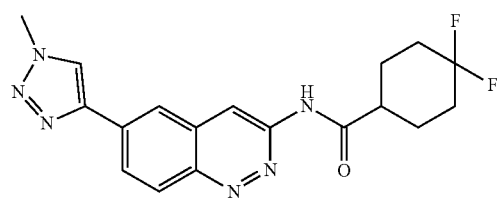 [SMILES: Cn1cc(-c2ccc3nnc(NC(=O)C4CCC(F)(F)CC4)cc3c2)nn1] 2155

TABLE 1-continued
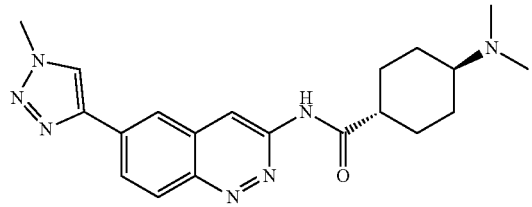 [SMILES: Cn1cc(-c2ccc3nnc(NC(=O)[C@H]4CC[C@H](N(C)C)CC4)cc3c2)nn1]
2156
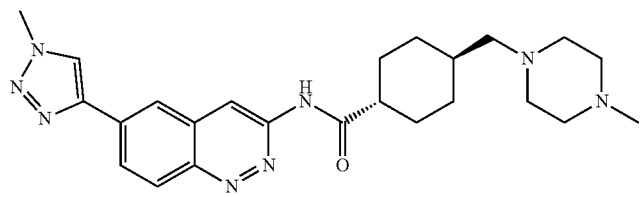 [SMILES: CN1CCN(C[C@H]2CC[C@H](C(=O)Nc3cc4cc(-c5cn(C)nn5)ccc4nn3)CC2)CC1]
2157
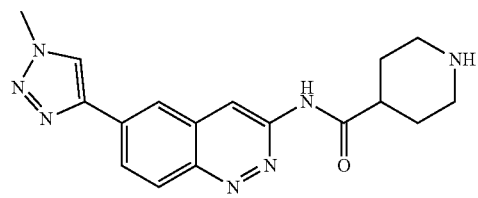 [SMILES: Cn1cc(-c2ccc3nnc(NC(=O)C4CCNCC4)cc3c2)nn1]
2158
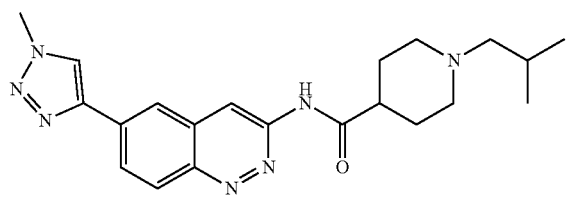 [SMILES: CC(C)CN1CCC(C(=O)Nc2cc3cc(-c4cn(C)nn4)ccc3nn2)CC1]
2159
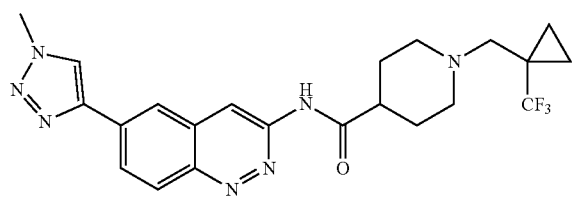 [SMILES: Cn1cc(-c2ccc3nnc(NC(=O)C4CCN(CC5(C(F)(F)F)CC5)CC4)cc3c2)nn1]
2160
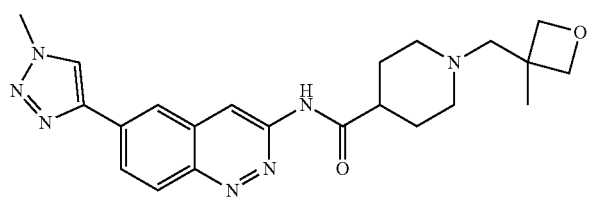 [SMILES: Cn1cc(-c2ccc3nnc(NC(=O)C4CCN(CC5(C)COC5)CC4)cc3c2)nn1]
2161
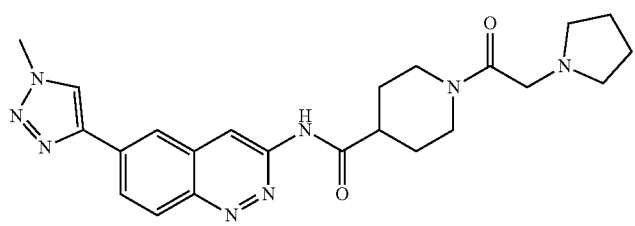
2162

TABLE 1-continued
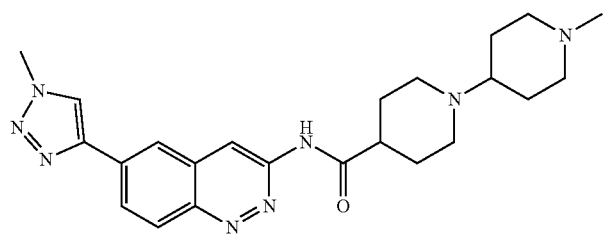 [SMILES: CN1CCC(N2CCC(C(=O)Nc3cc4cc(-c5cn(C)nn5)ccc4nn3)CC2)CC1] 2163
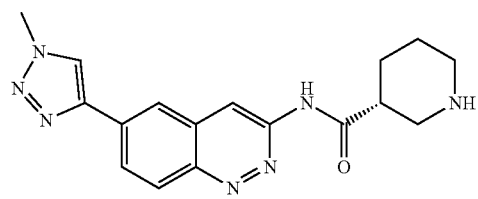 2164
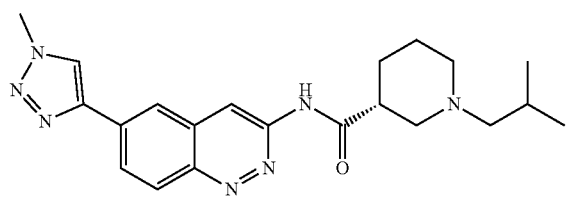 [SMILES: CC(C)CN1CCC[C@@H](C(=O)Nc2cc3cc(-c4cn(C)nn4)ccc3nn2)C1] 2165
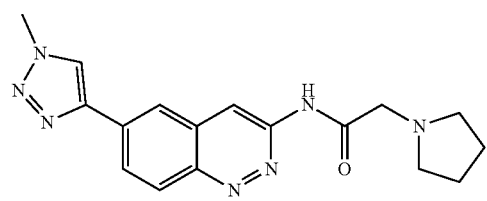 [SMILES: Cn1cc(-c2ccc3nnc(NC(=O)CN4CCCC4)cc3c2)nn1] 2166
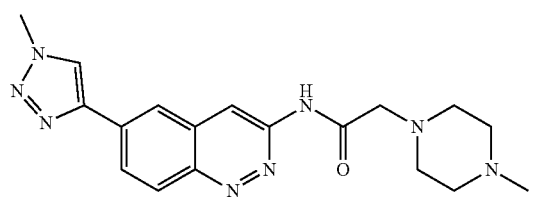 [SMILES: CN1CCN(CC(=O)Nc2cc3cc(-c4cn(C)nn4)ccc3nn2)CC1] 2167
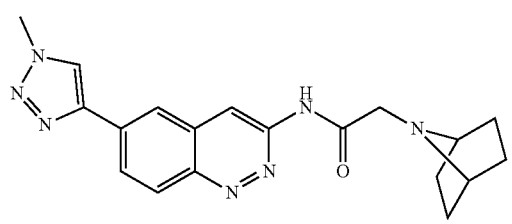 [SMILES: Cn1cc(-c2ccc3nnc(NC(=O)CN4C5CCC4CC5)cc3c2)nn1] 2168
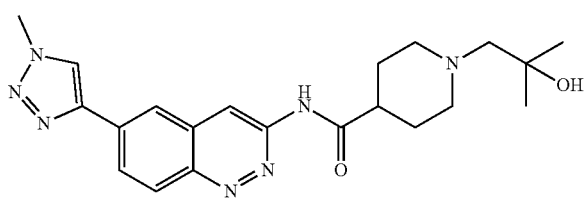 2169

TABLE 1-continued
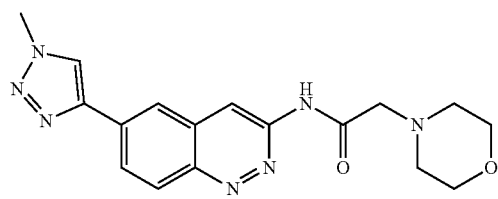 [SMILES: Cn1cc(-c2ccc3nnc(NC(=O)CN4CCOCC4)cc3c2)nn1] 2170
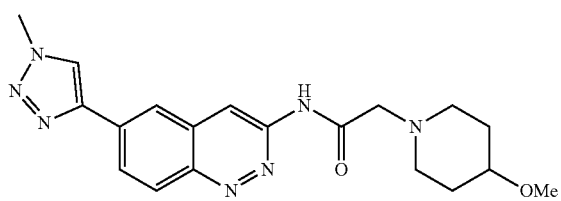 [SMILES: COC1CCN(CC(=O)Nc2cc3cc(-c4cn(C)nn4)ccc3nn2)CC1] 2171
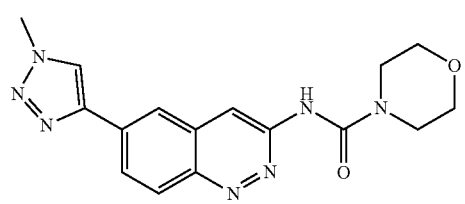 [SMILES: Cn1cc(-c2ccc3nnc(NC(=O)N4CCOCC4)cc3c2)nn1] 2172
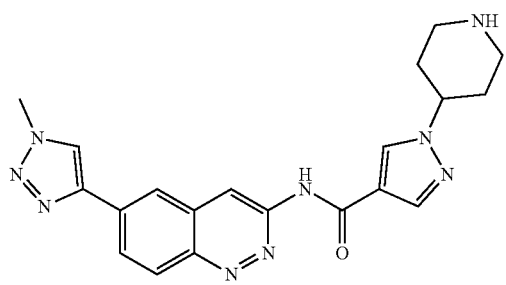 [SMILES: Cn1cc(-c2ccc3nnc(NC(=O)c4cnn(C5CCNCC5)c4)cc3c2)nn1] 2173
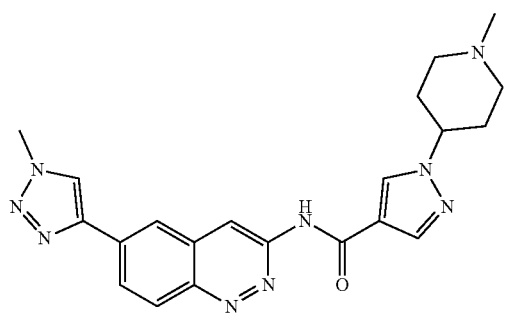 2174
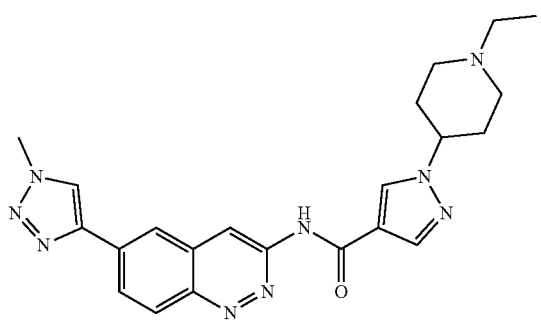 [SMILES: CCN1CCC(n2cc(C(=O)Nc3cc4cc(-c5cn(C)nn5)ccc4nn3)cn2)CC1] 2175

TABLE 1-continued
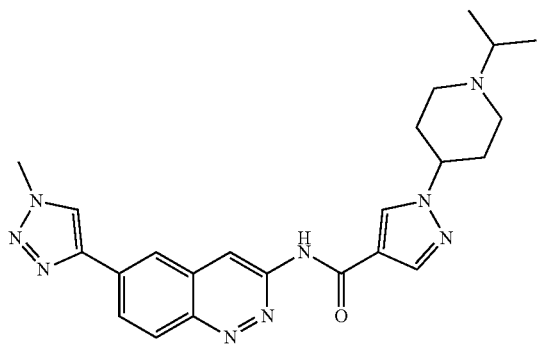 [SMILES: CC(C)N1CCC(n2cc(C(=O)Nc3cc4cc(-c5cn(C)nn5)ccc4nn3)cn2)CC1]
2176
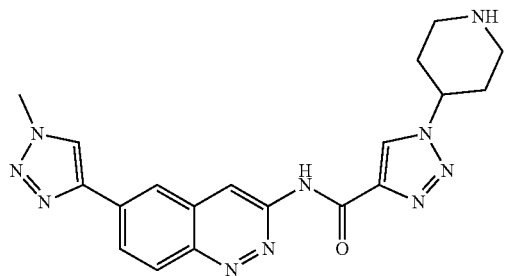
2177
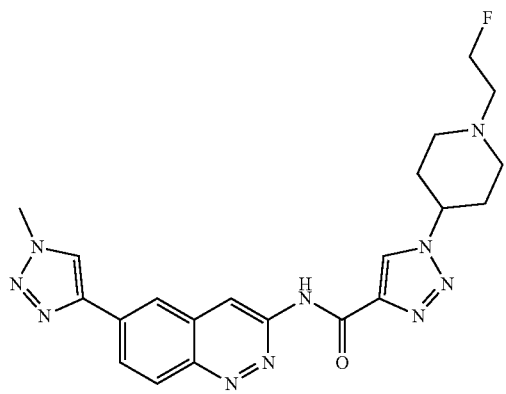 [SMILES: Cn1cc(-c2ccc3nnc(NC(=O)c4cn(C5CCN(CCF)CC5)nn4)cc3c2)nn1]
2178
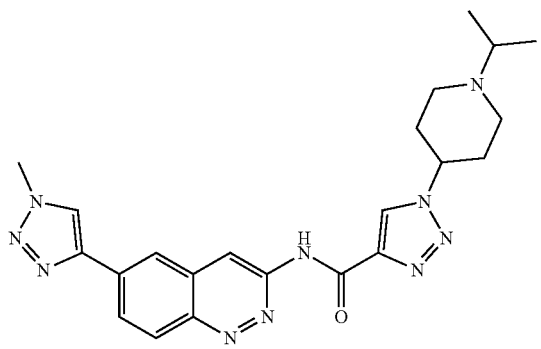 [SMILES: CC(C)N1CCC(n2cc(C(=O)Nc3cc4cc(-c5cn(C)nn5)ccc4nn3)nn2)CC1]
2179
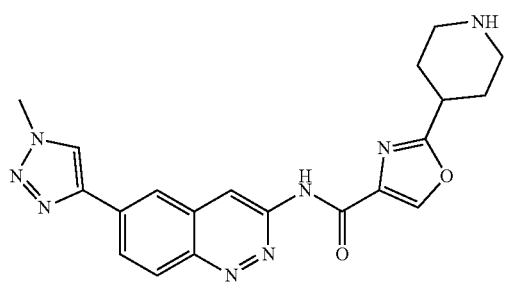 [SMILES: Cn1cc(-c2ccc3nnc(NC(=O)c4coc(C5CCNCC5)n4)cc3c2)nn1]
2180

TABLE 1-continued
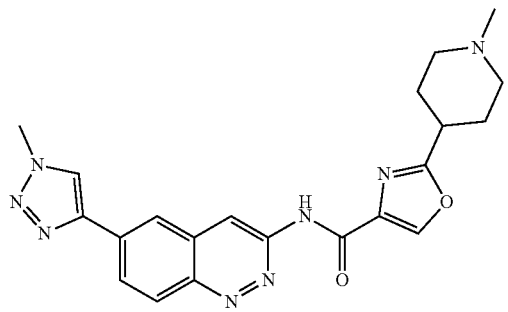 [SMILES: CN1CCC(c2nc(C(=O)Nc3cc4cc(-c5cn(C)nn5)ccc4nn3)co2)CC1]
2181
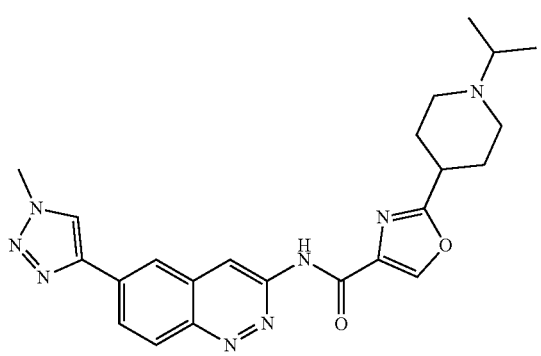 [SMILES: CC(C)N1CCC(c2nc(C(=O)Nc3cc4cc(-c5cn(C)nn5)ccc4nn3)co2)CC1]
2182
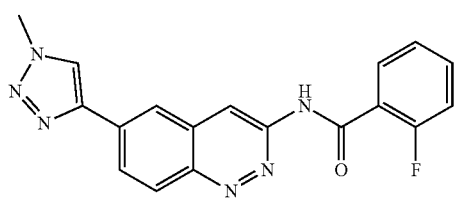 [SMILES: Cn1cc(-c2ccc3nnc(NC(=O)c4ccccc4F)cc3c2)nn1]
2183
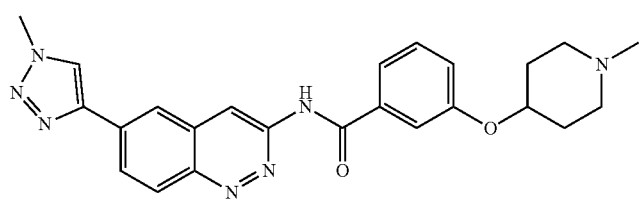 [SMILES: CN1CCC(Oc2cccc(C(=O)Nc3cc4cc(-c5cn(C)nn5)ccc4nn3)c2)CC1]
2184
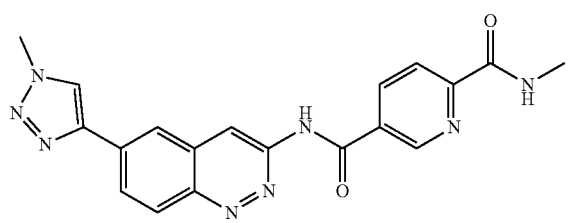 [SMILES: CNC(=O)c1ccc(C(=O)Nc2cc3cc(-c4cn(C)nn4)ccc3nn2)cn1]
2185
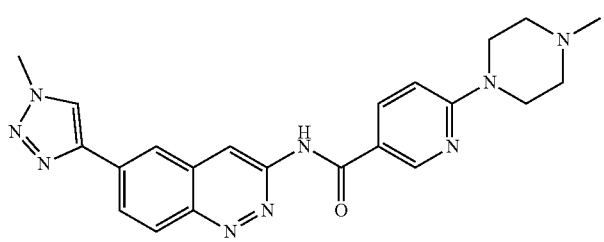 [SMILES: CN1CCN(c2ccc(C(=O)Nc3cc4cc(-c5cn(C)nn5)ccc4nn3)cn2)CC1]
2186

TABLE 1-continued
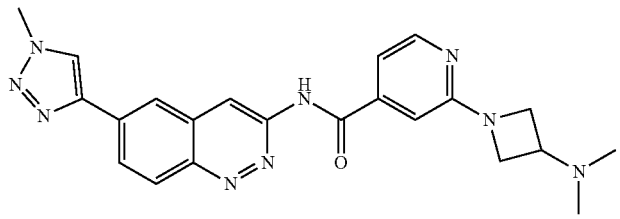 [SMILES: CN(C)C1CN(c2cc(C(=O)Nc3cc4cc(-c5cn(C)nn5)ccc4nn3)ccn2)C1] 2187
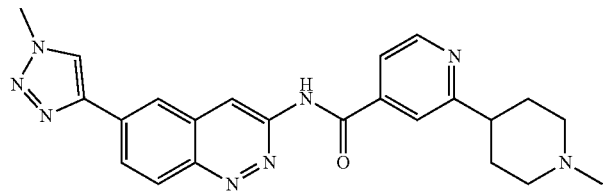 2188
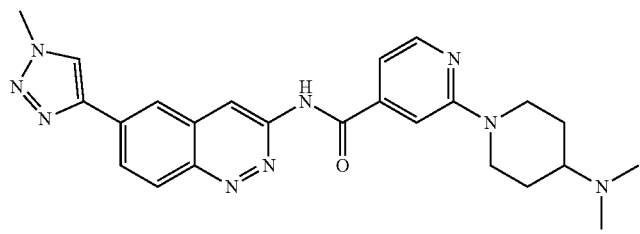 [SMILES: CN(C)C1CCN(c2cc(C(=O)Nc3cc4cc(-c5cn(C)nn5)ccc4nn3)ccn2)CC1] 2189
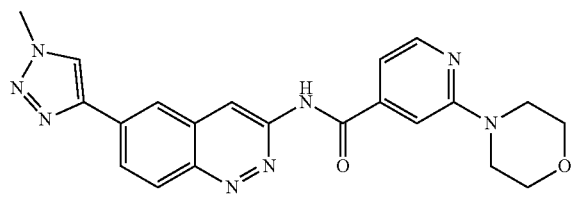 [SMILES: Cn1cc(-c2ccc3nnc(NC(=O)c4ccnc(N5CCOCC5)c4)cc3c2)nn1] 2190
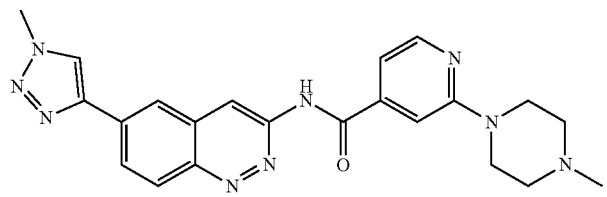 [SMILES: CN1CCN(c2cc(C(=O)Nc3cc4cc(-c5cn(C)nn5)ccc4nn3)ccn2)CC1] 2191
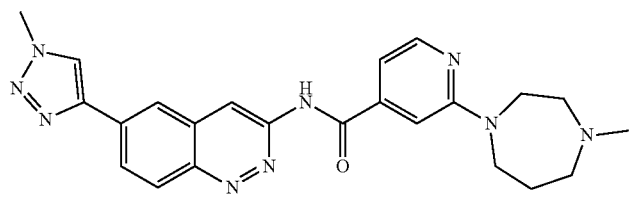 [SMILES: CN1CCCN(c2cc(C(=O)Nc3cc4cc(-c5cn(C)nn5)ccc4nn3)ccn2)CC1] 2192
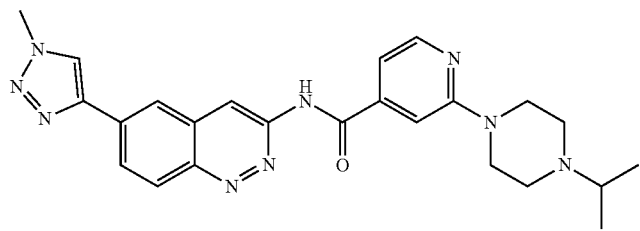 [SMILES: CC(C)N1CCN(c2cc(C(=O)Nc3cc4cc(-c5cn(C)nn5)ccc4nn3)ccn2)CC1] 2193

TABLE 1-continued
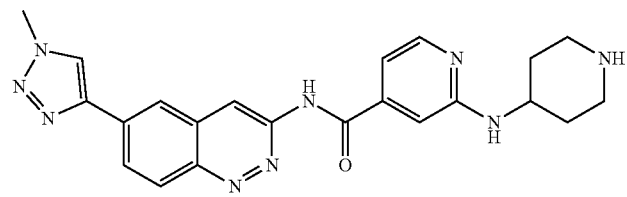 [SMILES: Cn1cc(-c2ccc3nnc(NC(=O)c4ccnc(NC5CCNCC5)c4)cc3c2)nn1] 2194
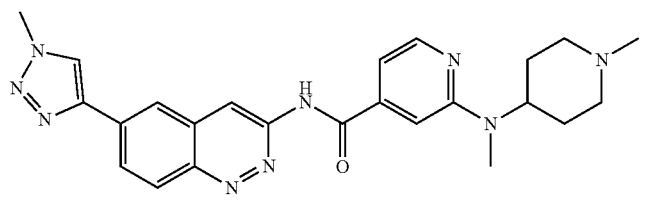 2195
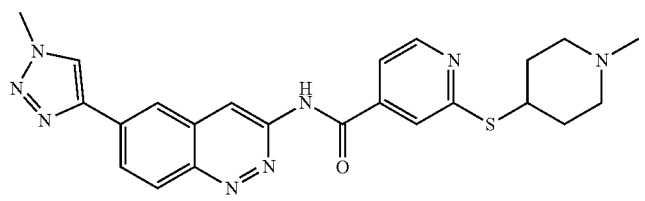 [SMILES: CN1CCC(Sc2cc(C(=O)Nc3cc4cc(-c5cn(C)nn5)ccc4nn3)ccn2)CC1] 2196
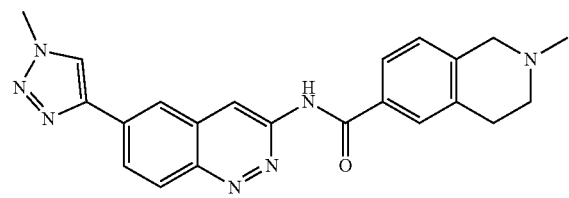 2197
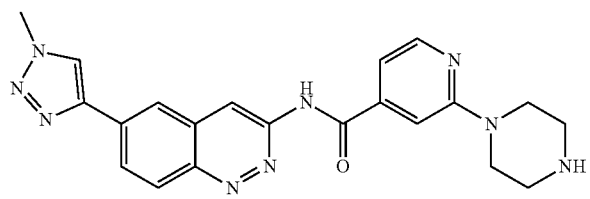 [SMILES: Cn1cc(-c2ccc3nnc(NC(=O)c4ccnc(N5CCNCC5)c4)cc3c2)nn1] 2198
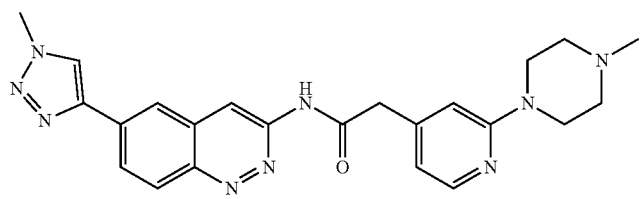 [SMILES: CN1CCN(c2cc(CC(=O)Nc3cc4cc(-c5cn(C)nn5)ccc4nn3)ccn2)CC1] 2199
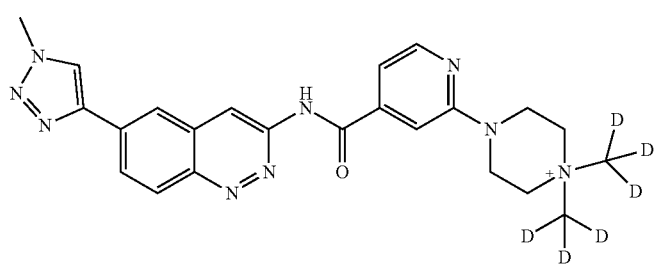 2200

TABLE 1-continued
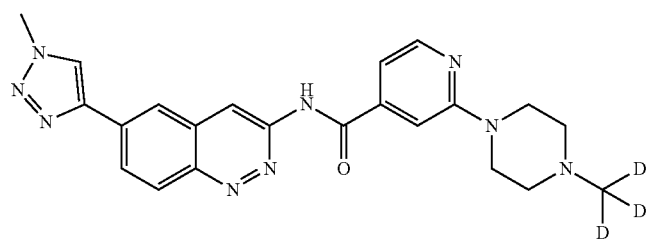 [SMILES: [2H]C([2H])([2H])N1CCN(c2cc(C(=O)Nc3cc4cc(-c5cn(C)nn5)ccc4nn3)ccn2)CC1]  2201
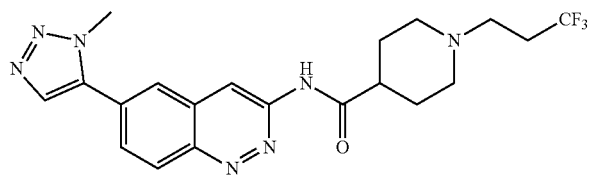 [SMILES: Cn1nncc1-c1ccc2nnc(NC(=O)C3CCN(CCC(F)(F)F)CC3)cc2c1]  2202
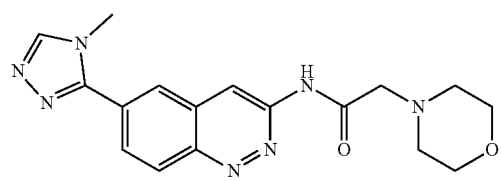 [SMILES: Cn1cnnc1-c1ccc2nnc(NC(=O)CN3CCOCC3)cc2c1]  2203
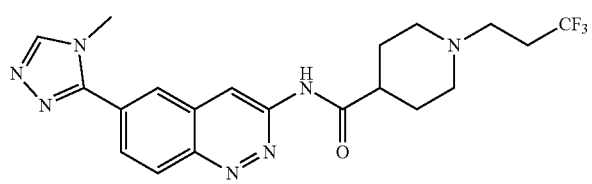 [SMILES: Cn1cnnc1-c1ccc2nnc(NC(=O)C3CCN(CCC(F)(F)F)CC3)cc2c1]  2204
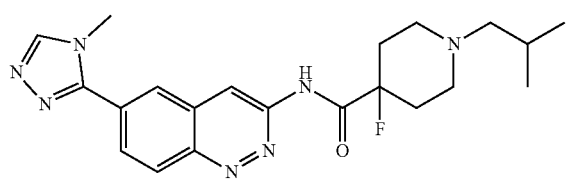 [SMILES: CC(C)CN1CCC(F)(C(=O)Nc2cc3cc(-c4nncn4C)ccc3nn2)CC1]  2205
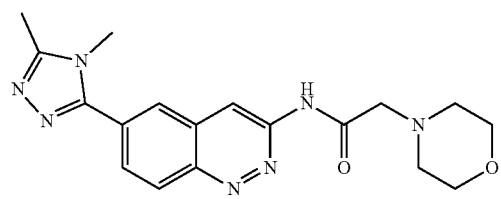 [SMILES: Cc1nnc(-c2ccc3nnc(NC(=O)CN4CCOCC4)cc3c2)n1C]  2206
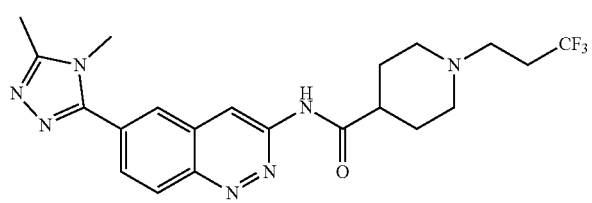 [SMILES: Cc1nnc(-c2ccc3nnc(NC(=O)C4CCN(CCC(F)(F)F)CC4)cc3c2)n1C]  2207
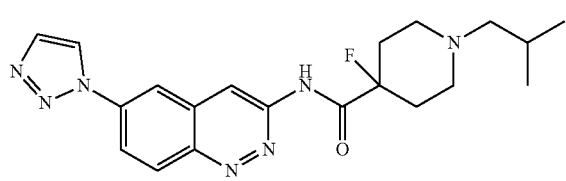 [SMILES: CC(C)CN1CCC(F)(C(=O)Nc2cc3cc(-n4ccnn4)ccc3nn2)CC1]  2208

TABLE 1-continued
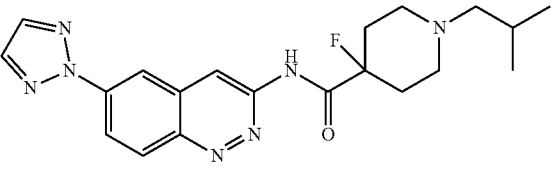 [SMILES: CC(C)CN1CCC(F)(C(=O)Nc2cc3cc(-n4nccn4)ccc3nn2)CC1] 2209
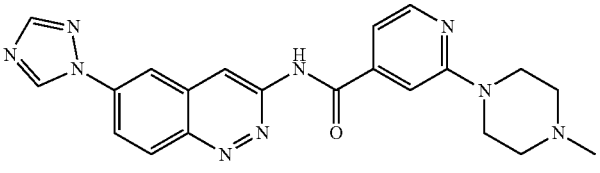 [SMILES: CN1CCN(c2cc(C(=O)Nc3cc4cc(-n5cncn5)ccc4nn3)ccn2)CC1] 2210
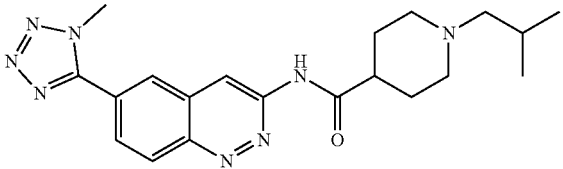 [SMILES: CC(C)CN1CCC(C(=O)Nc2cc3cc(-c4nnnn4C)ccc3nn2)CC1] 2211
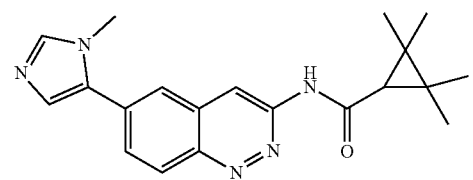 [SMILES: Cn1cncc1-c1ccc2nnc(NC(=O)C3C(C)(C)C3(C)C)cc2c1] 2212
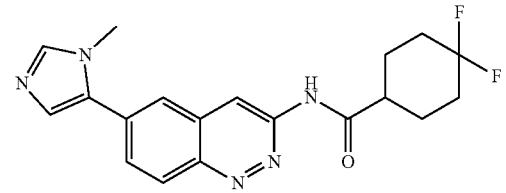 [SMILES: Cn1cncc1-c1ccc2nnc(NC(=O)C3CCC(F)(F)CC3)cc2c1] 2213
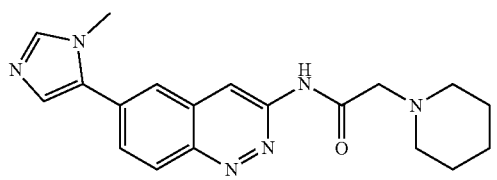 [SMILES: Cn1cncc1-c1ccc2nnc(NC(=O)CN3CCCCC3)cc2c1] 2214
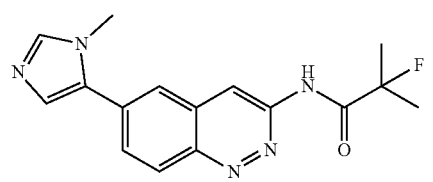 [SMILES: Cn1cncc1-c1ccc2nnc(NC(=O)C(C)(C)F)cc2c1] 2215
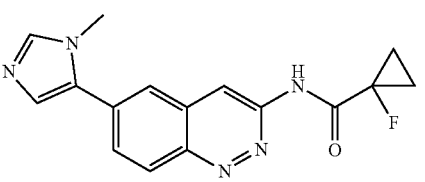 [SMILES: Cn1cncc1-c1ccc2nnc(NC(=O)C3(F)CC3)cc2c1] 2216

TABLE 1-continued

| | |
|---|---|
| (structure) | 2217 |
| (structure) | 2218 |
| (structure) | 2219 |
| (structure) | 2220 |
| (structure) | 2221 |
| (structure) | 2222 |
| (structure) | 2223 |
| (structure) | 2224 |

TABLE 1-continued
| | |
|---|---|
| 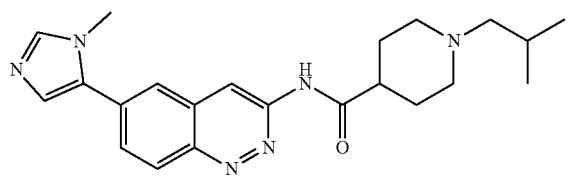 [SMILES: CC(C)CN1CCC(C(=O)Nc2cc3cc(-c4cncn4C)ccc3nn2)CC1] | 2225 |
| 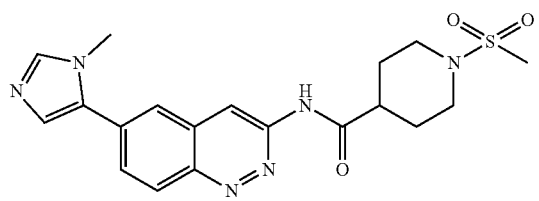 [SMILES: Cn1cncc1-c1ccc2nnc(NC(=O)C3CCN(S(C)(=O)=O)CC3)cc2c1] | 2226 |
| 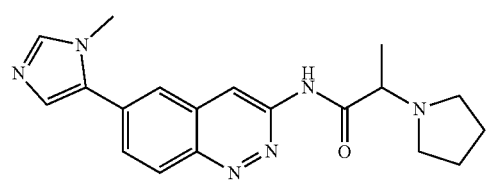 [SMILES: CC(C(=O)Nc1cc2cc(-c3cncn3C)ccc2nn1)N1CCCC1] | 2227 |
| 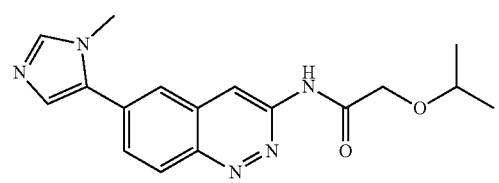 [SMILES: CC(C)OCC(=O)Nc1cc2cc(-c3cncn3C)ccc2nn1] | 2228 |
| 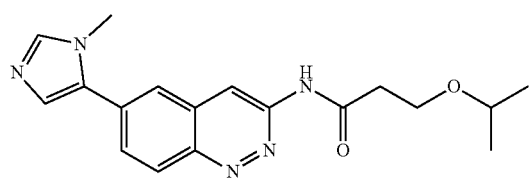 [SMILES: CC(C)OCCC(=O)Nc1cc2cc(-c3cncn3C)ccc2nn1] | 2229 |
| 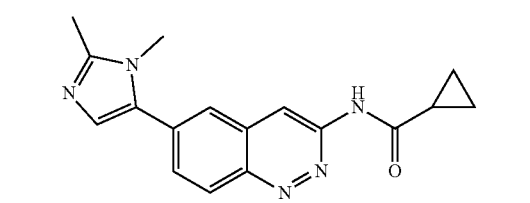 [SMILES: Cc1ncc(-c2ccc3nnc(NC(=O)C4CC4)cc3c2)n1C] | 2230 |
| 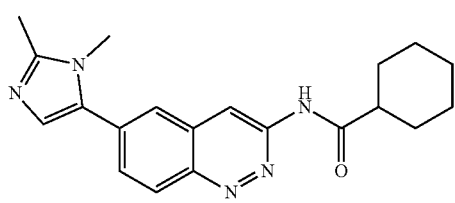 [SMILES: Cc1ncc(-c2ccc3nnc(NC(=O)C4CCCCC4)cc3c2)n1C] | 2231 |
| 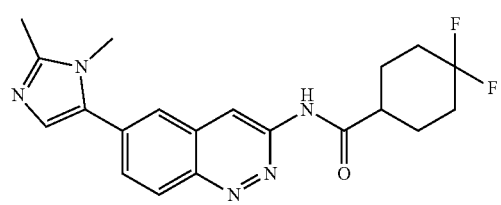 [SMILES: Cc1ncc(-c2ccc3nnc(NC(=O)C4CCC(F)(F)CC4)cc3c2)n1C] | 2232 |

TABLE 1-continued
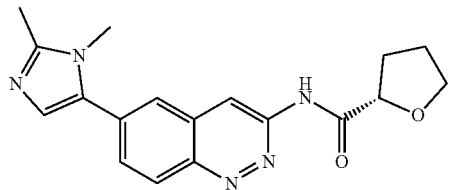 [SMILES: Cc1ncc(-c2ccc3nnc(NC(=O)[C@@H]4CCCO4)cc3c2)n1C]   2233
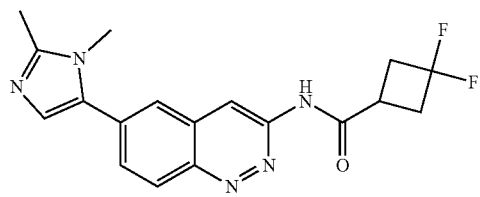 [SMILES: Cc1ncc(-c2ccc3nnc(NC(=O)C4CC(F)(F)C4)cc3c2)n1C]   2234
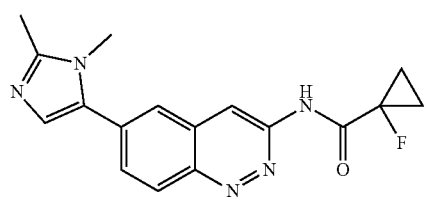 [SMILES: Cc1ncc(-c2ccc3nnc(NC(=O)C4(F)CC4)cc3c2)n1C]   2235
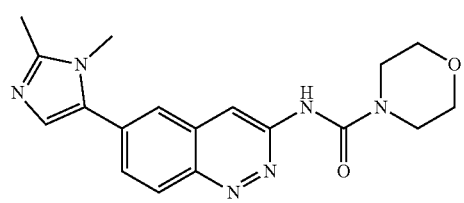 [SMILES: Cc1ncc(-c2ccc3nnc(NC(=O)N4CCOCC4)cc3c2)n1C]   2236
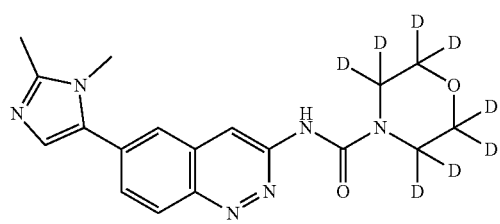 [SMILES: [2H]C1([2H])OC([2H])([2H])C([2H])([2H])N(C(=O)Nc2cc3cc(-c4cnc(C)n4C)ccc3nn2)C1([2H])[2H]]   2237
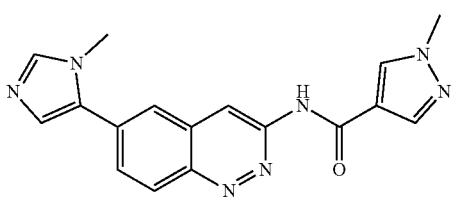 [SMILES: Cn1cc(C(=O)Nc2cc3cc(-c4cncn4C)ccc3nn2)cn1]   2238
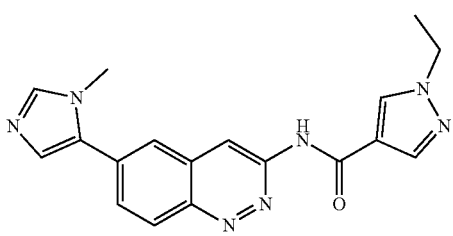 [SMILES: CCn1cc(C(=O)Nc2cc3cc(-c4cncn4C)ccc3nn2)cn1]   2239

TABLE 1-continued
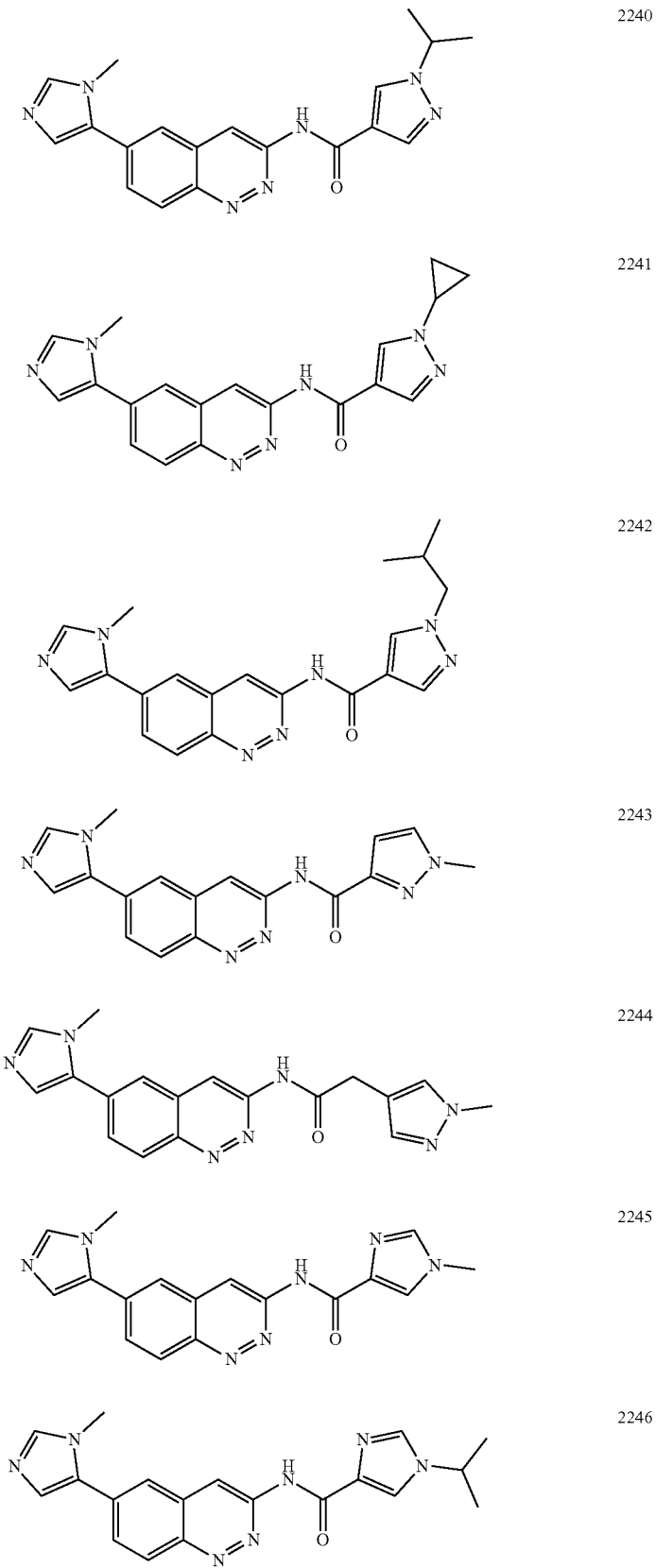
2240
2241
2242
2243
2244
2245
2246

TABLE 1-continued
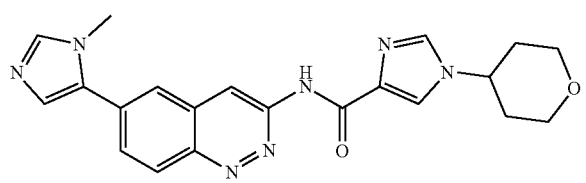 [SMILES: Cn1cncc1-c1ccc2nnc(NC(=O)c3cn(C4CCOCC4)cn3)cc2c1] 2247
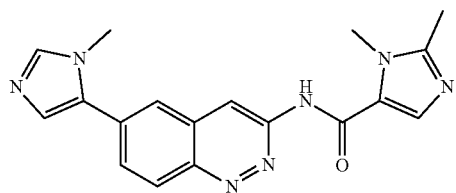 [SMILES: Cc1ncc(C(=O)Nc2cc3cc(-c4cncn4C)ccc3nn2)n1C] 2248
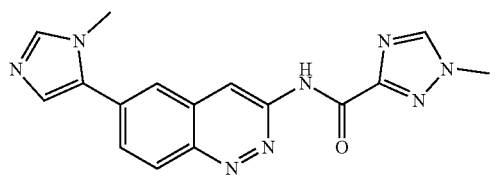 2249
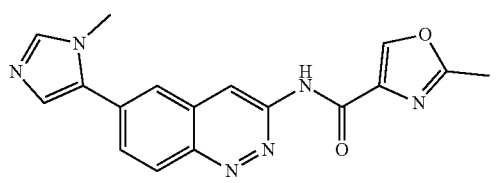 [SMILES: Cc1nc(C(=O)Nc2cc3cc(-c4cncn4C)ccc3nn2)co1] 2250
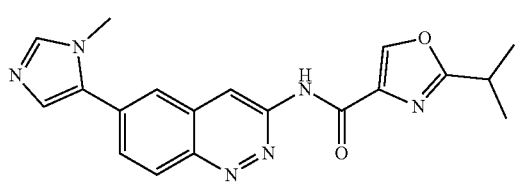 [SMILES: CC(C)c1nc(C(=O)Nc2cc3cc(-c4cncn4C)ccc3nn2)co1] 2251
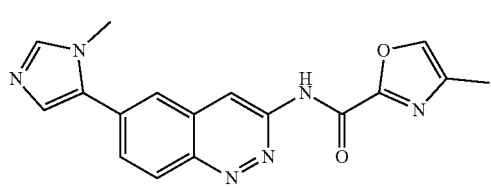 [SMILES: Cc1coc(C(=O)Nc2cc3cc(-c4cncn4C)ccc3nn2)n1] 2252
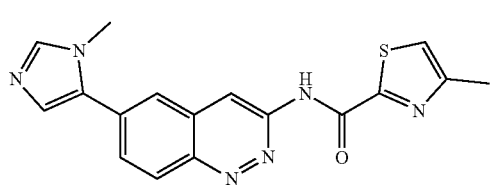 [SMILES: Cc1csc(C(=O)Nc2cc3cc(-c4cncn4C)ccc3nn2)n1] 2253
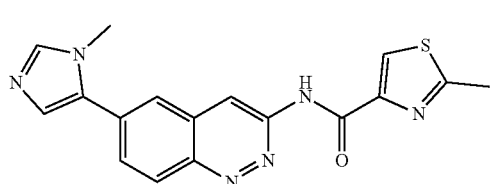 2254

TABLE 1-continued
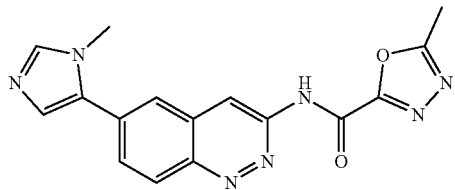 2255
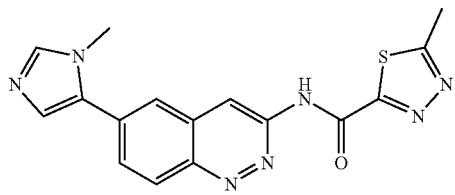 [SMILES: Cc1nnc(C(=O)Nc2cc3cc(-c4cncn4C)ccc3nn2)o1] 2256
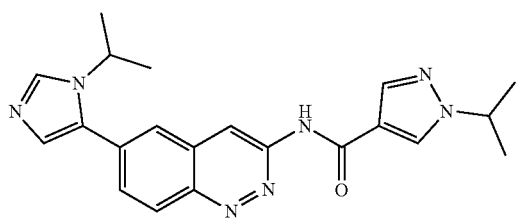 [SMILES: CC(C)n1cc(C(=O)Nc2cc3cc(-c4cncn4C(C)C)ccc3nn2)cn1] 2257
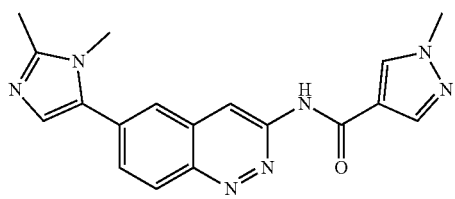 [SMILES: Cc1ncc(-c2ccc3nnc(NC(=O)c4cnn(C)c4)cc3c2)n1C] 2258
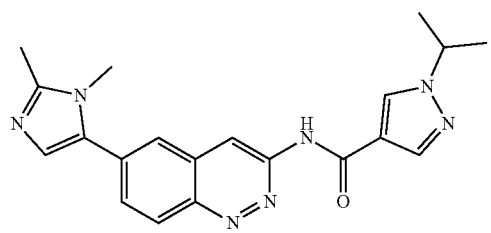 [SMILES: Cc1ncc(-c2ccc3nnc(NC(=O)c4cnn(C(C)C)c4)cc3c2)n1C] 2259
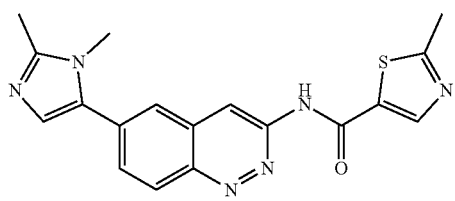 [SMILES: Cc1ncc(C(=O)Nc2cc3cc(-c4cnc(C)n4C)ccc3nn2)s1] 2260
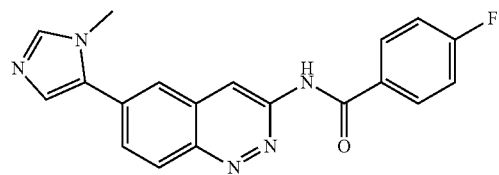 [SMILES: Cn1cncc1-c1ccc2nnc(NC(=O)c3ccc(F)cc3)cc2c1] 2261
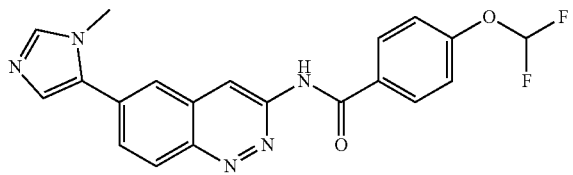 [SMILES: Cn1cncc1-c1ccc2nnc(NC(=O)c3ccc(OC(F)F)cc3)cc2c1] 2262

TABLE 1-continued
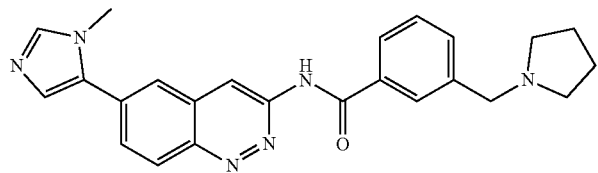 [SMILES: Cn1cncc1-c1ccc2nnc(NC(=O)c3cccc(CN4CCCC4)c3)cc2c1] 2263
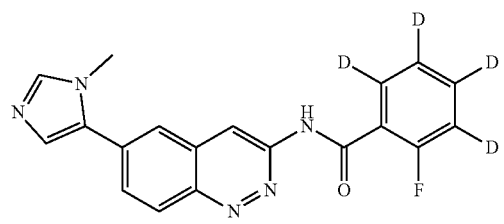 2264
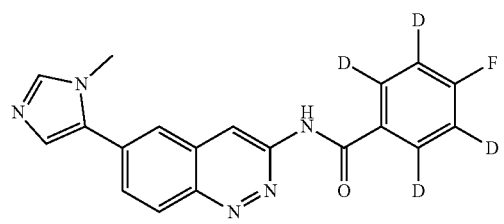 [SMILES: [2H]c1c([2H])c(C(=O)Nc2cc3cc(-c4cncn4C)ccc3nn2)c([2H])c([2H])c1F] 2265
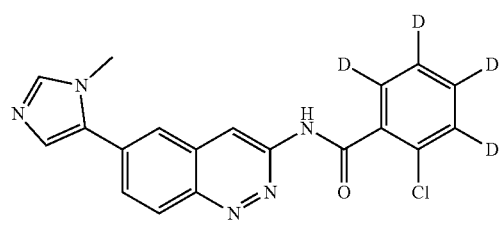 [SMILES: [2H]c1c([2H])c([2H])c(C(=O)Nc2cc3cc(-c4cncn4C)ccc3nn2)c(Cl)c1[2H]] 2266
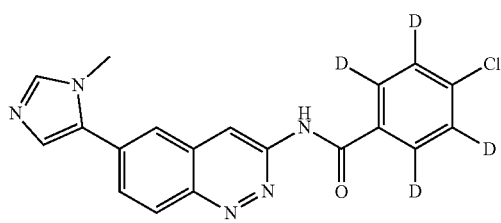 [SMILES: [2H]c1c([2H])c(C(=O)Nc2cc3cc(-c4cncn4C)ccc3nn2)c([2H])c([2H])c1Cl] 2267
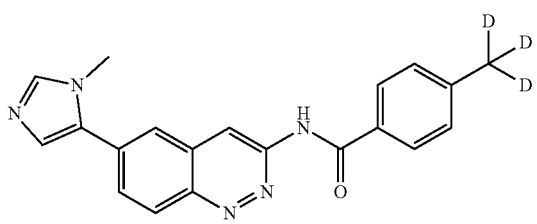 [SMILES: [2H]C([2H])([2H])c1ccc(C(=O)Nc2cc3cc(-c4cncn4C)ccc3nn2)cc1] 2268
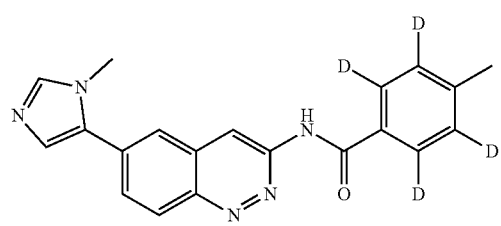 [SMILES: [2H]c1c([2H])c(C(=O)Nc2cc3cc(-c4cncn4C)ccc3nn2)c([2H])c([2H])c1C] 2269

TABLE 1-continued
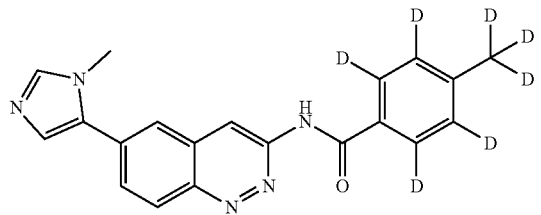 [SMILES: [2H]c1c([2H])c(C([2H])([2H])[2H])c([2H])c([2H])c1C(=O)Nc1cc2cc(-c3cncn3C)ccc2nn1] 2270
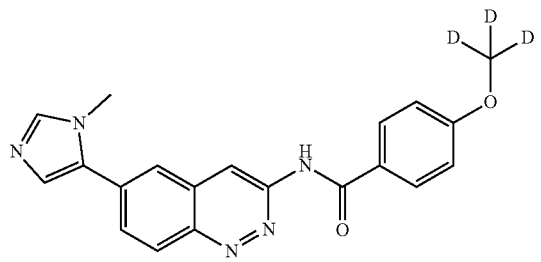 [SMILES: [2H]C([2H])([2H])Oc1ccc(C(=O)Nc2cc3cc(-c4cncn4C)ccc3nn2)cc1] 2271
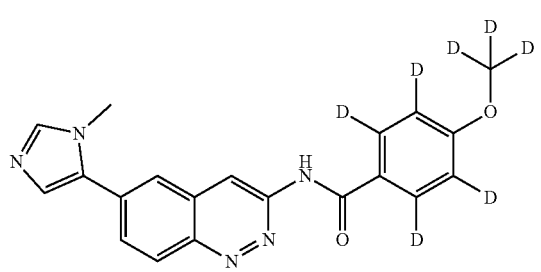 2272
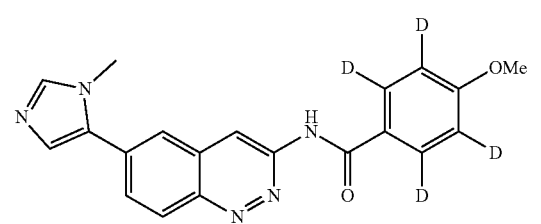 [SMILES: [2H]c1c([2H])c(C(=O)Nc2cc3cc(-c4cncn4C)ccc3nn2)c([2H])c([2H])c1OC] 2273
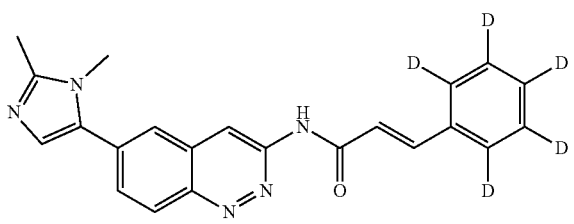 [SMILES: [2H]c1c([2H])c([2H])c(/C=C/C(=O)Nc2cc3cc(-c4cnc(C)n4C)ccc3nn2)c([2H])c1[2H]] 2274
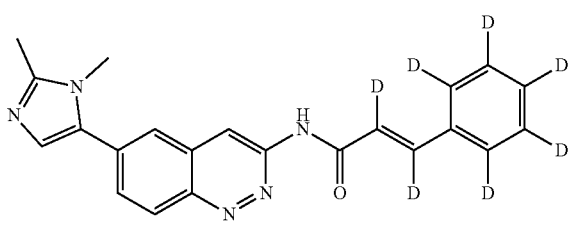 2275
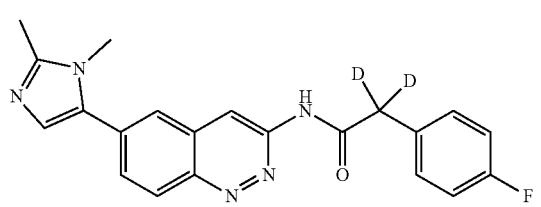 [SMILES: [2H]C([2H])(C(=O)Nc1cc2cc(-c3cnc(C)n3C)ccc2nn1)c1ccc(F)cc1] 2276

TABLE 1-continued
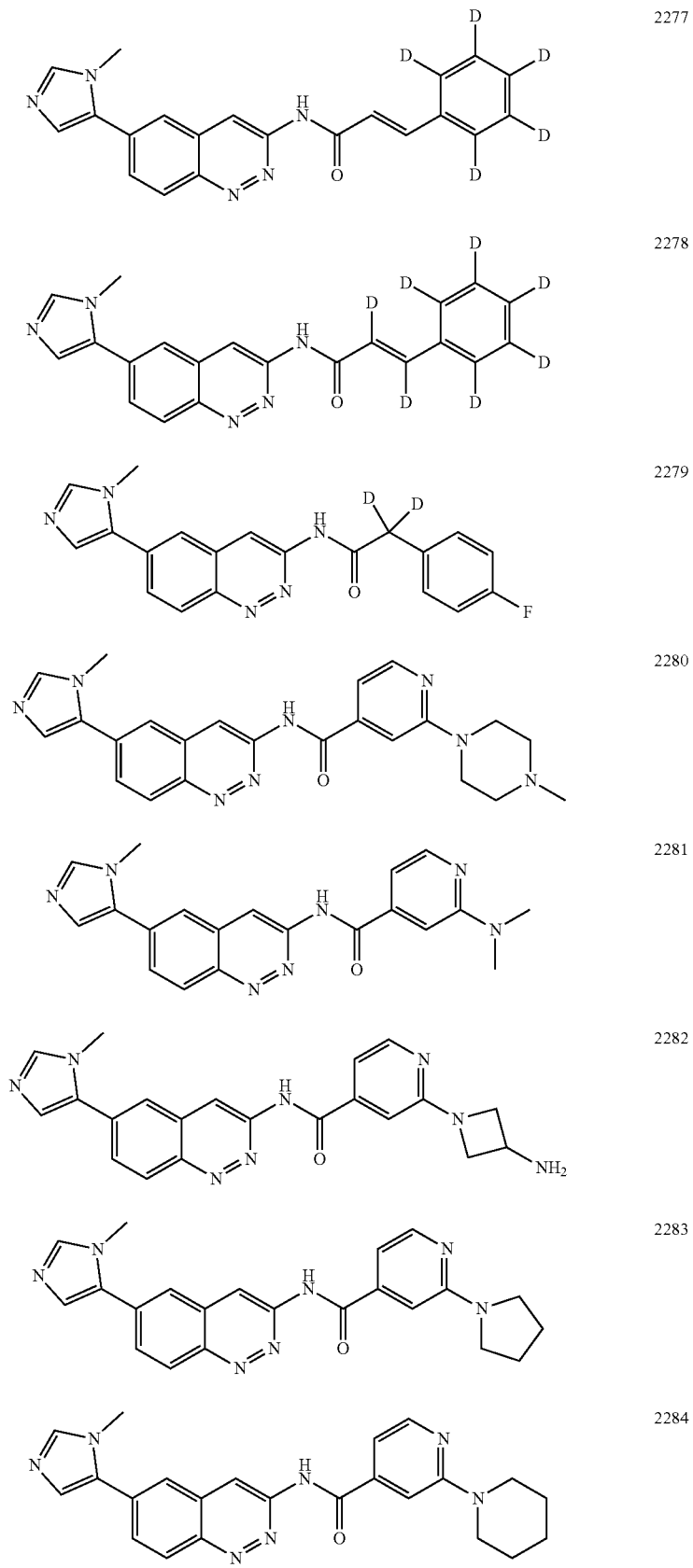

TABLE 1-continued
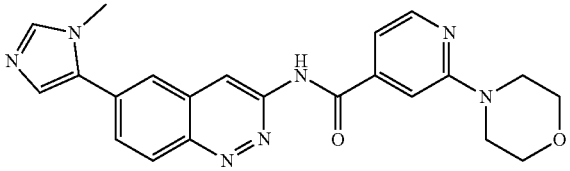 [SMILES: Cn1cncc1-c1ccc2nnc(NC(=O)c3ccnc(N4CCOCC4)c3)cc2c1] 2285
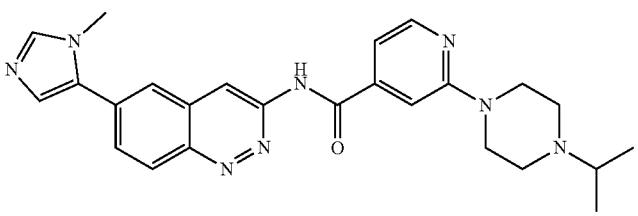 [SMILES: CC(C)N1CCN(c2cc(C(=O)Nc3cc4cc(-c5cncn5C)ccc4nn3)ccn2)CC1] 2286
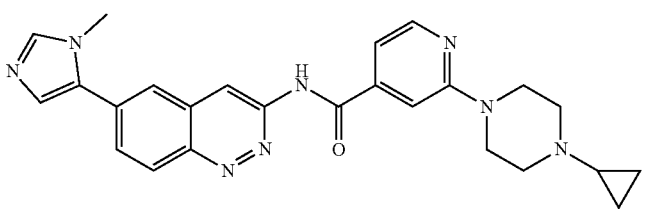 [SMILES: Cn1cncc1-c1ccc2nnc(NC(=O)c3ccnc(N4CCN(C5CC5)CC4)c3)cc2c1] 2287
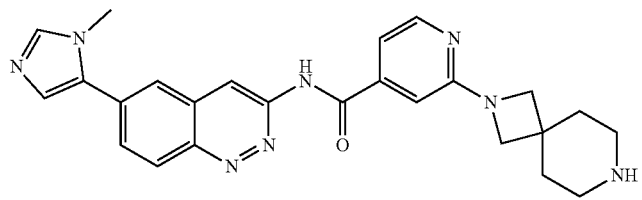 [SMILES: Cn1cncc1-c1ccc2nnc(NC(=O)c3ccnc(N4CC5(CCNCC5)C4)c3)cc2c1] 2288
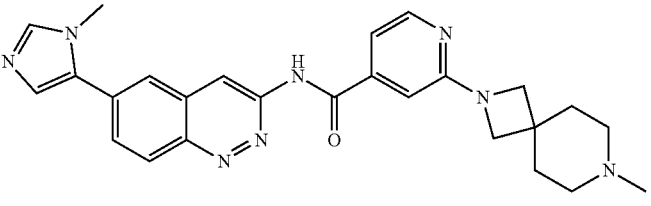 [SMILES: CN1CCC2(CC1)CN(c1cc(C(=O)Nc3cc4cc(-c5cncn5C)ccc4nn3)ccn1)C2] 2289
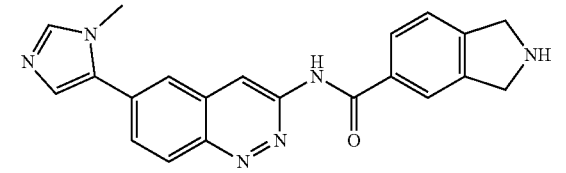 [SMILES: Cn1cncc1-c1ccc2nnc(NC(=O)c3ccc4c(c3)CNC4)cc2c1] 2290
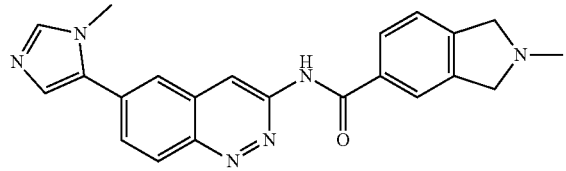 [SMILES: CN1Cc2ccc(C(=O)Nc3cc4cc(-c5cncn5C)ccc4nn3)cc2C1] 2291
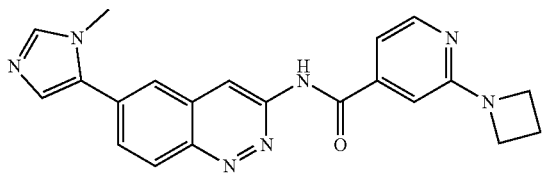 [SMILES: Cn1cncc1-c1ccc2nnc(NC(=O)c3ccnc(N4CCC4)c3)cc2c1] 2292

TABLE 1-continued
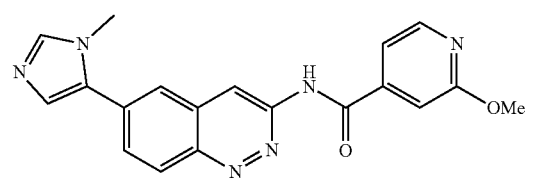 [SMILES: COc1cc(C(=O)Nc2cc3cc(-c4cncn4C)ccc3nn2)ccn1] 2293
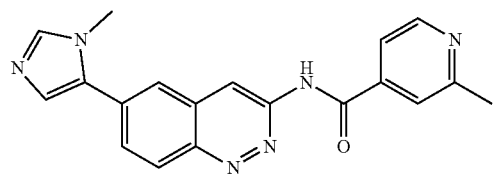 [SMILES: Cc1cc(C(=O)Nc2cc3cc(-c4cncn4C)ccc3nn2)ccn1] 2294
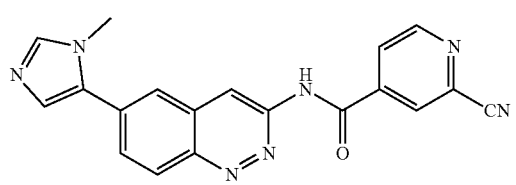 [SMILES: Cn1cncc1-c1ccc2nnc(NC(=O)c3ccnc(C#N)c3)cc2c1] 2295
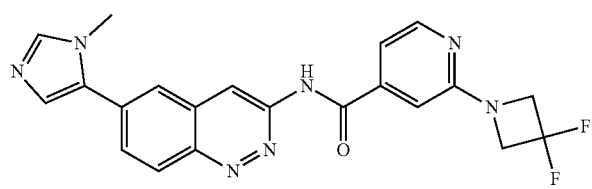 [SMILES: Cn1cncc1-c1ccc2nnc(NC(=O)c3ccnc(N4CC(F)(F)C4)c3)cc2c1] 2296
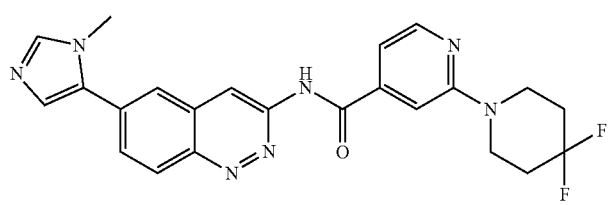 [SMILES: Cn1cncc1-c1ccc2nnc(NC(=O)c3ccnc(N4CCC(F)(F)CC4)c3)cc2c1] 2297
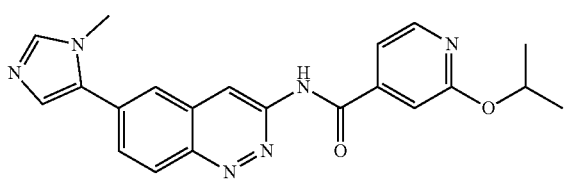 [SMILES: CC(C)Oc1cc(C(=O)Nc2cc3cc(-c4cncn4C)ccc3nn2)ccn1] 2298
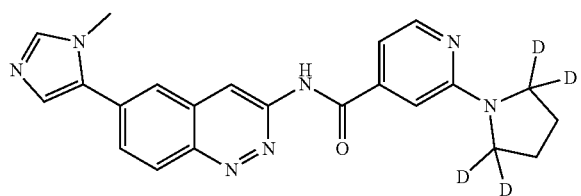 [SMILES: [2H]C1([2H])CCC([2H])([2H])N1c1cc(C(=O)Nc2cc3cc(-c4cncn4C)ccc3nn2)ccn1] 2299
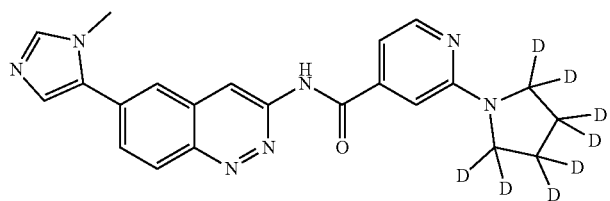 [SMILES: [2H]C1([2H])N(c2cc(C(=O)Nc3cc4cc(-c5cncn5C)ccc4nn3)ccn2)C([2H])([2H])C([2H])([2H])C1([2H])[2H]] 2300

TABLE 1-continued
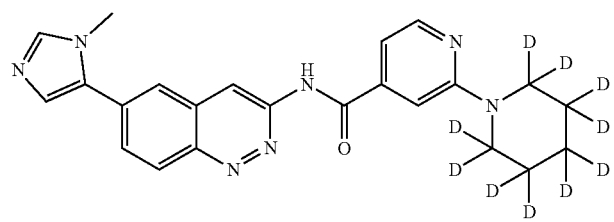 [SMILES: [2H]C1([2H])N(c2cc(C(=O)Nc3cc4cc(-c5cncn5C)ccc4nn3)ccn2)C([2H])([2H])C([2H])([2H])C([2H])([2H])C1([2H])[2H]] 2301
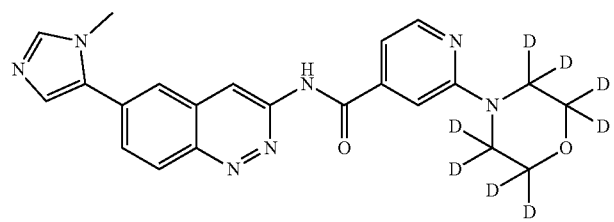 [SMILES: [2H]C1([2H])OC([2H])([2H])C([2H])([2H])N(c2cc(C(=O)Nc3cc4cc(-c5cncn5C)ccc4nn3)ccn2)C1([2H])[2H]] 2302
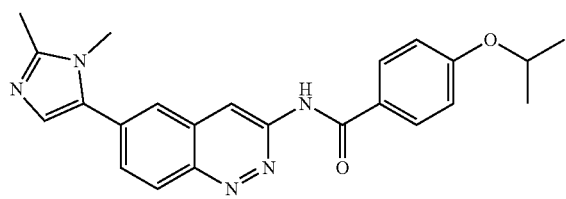 [SMILES: Cc1ncc(-c2ccc3nnc(NC(=O)c4ccc(OC(C)C)cc4)cc3c2)n1C] 2303
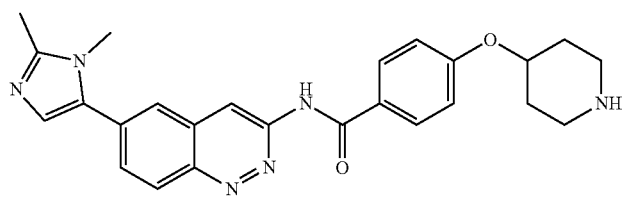 [SMILES: Cc1ncc(-c2ccc3nnc(NC(=O)c4ccc(OC5CCNCC5)cc4)cc3c2)n1C] 2304
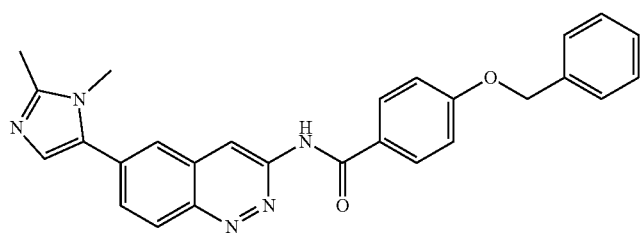 [SMILES: Cc1ncc(-c2ccc3nnc(NC(=O)c4ccc(OCc5ccccc5)cc4)cc3c2)n1C] 2305
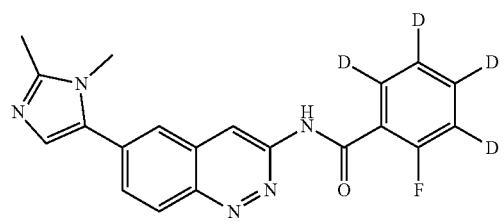 2306
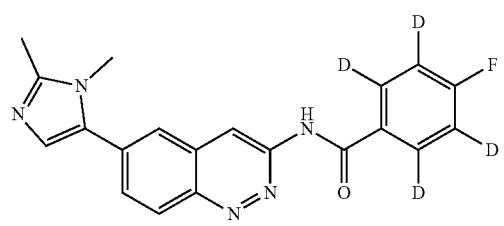 [SMILES: [2H]c1c([2H])c(C(=O)Nc2cc3cc(-c4cnc(C)n4C)ccc3nn2)c([2H])c([2H])c1F] 2307

TABLE 1-continued
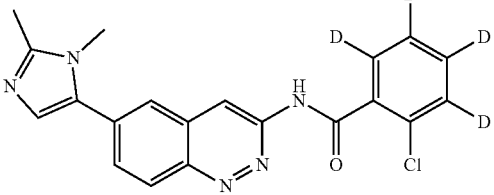 2308
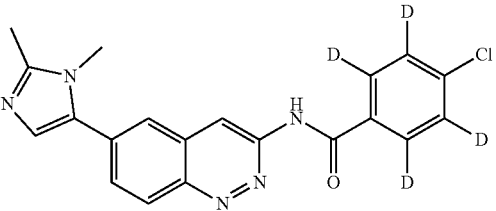 [SMILES: [2H]c1c([2H])c(C(=O)Nc2cc3cc(-c4cnc(C)n4C)ccc3nn2)c([2H])c([2H])c1Cl] 2309
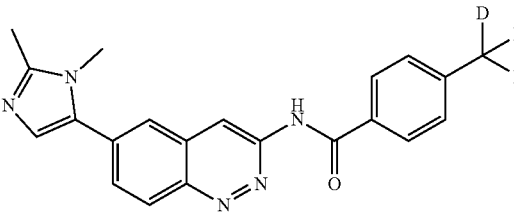 2310
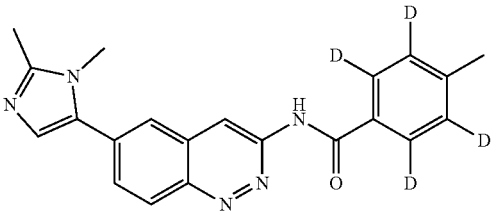 [SMILES: [2H]c1c([2H])c(C(=O)Nc2cc3cc(-c4cnc(C)n4C)ccc3nn2)c([2H])c([2H])c1C] 2311
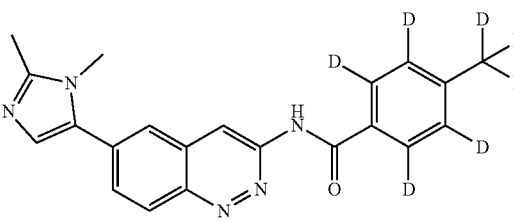 2312
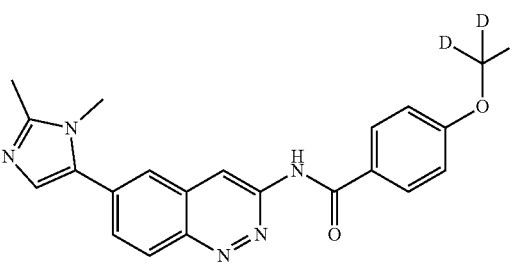 2313
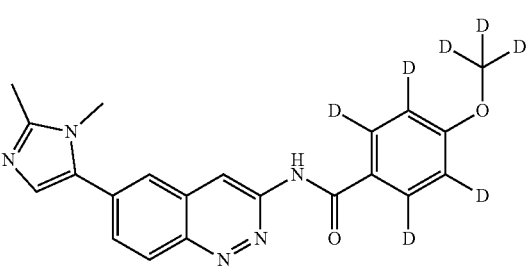 [SMILES: [2H]c1c([2H])c(C(=O)Nc2cc3cc(-c4cnc(C)n4C)ccc3nn2)c([2H])c([2H])c1OC([2H])([2H])[2H]] 2314

TABLE 1-continued
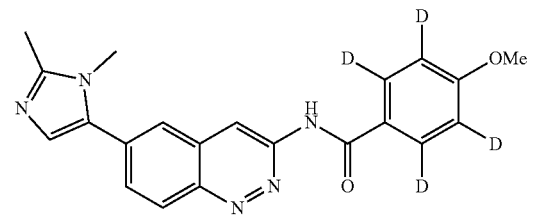 [SMILES: [2H]c1c([2H])c(C(=O)Nc2cc3cc(-c4cnc(C)n4C)ccc3nn2)c([2H])c([2H])c1OC] 2315
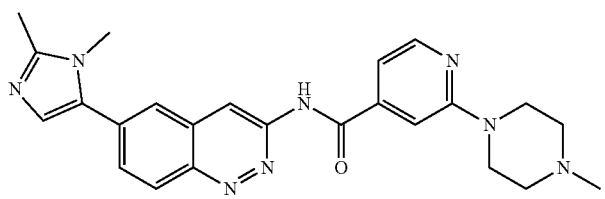 2316
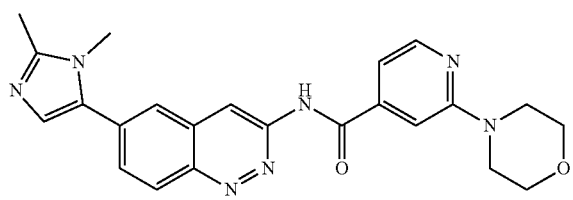 [SMILES: Cc1ncc(-c2ccc3nnc(NC(=O)c4ccnc(N5CCOCC5)c4)cc3c2)n1C] 2317
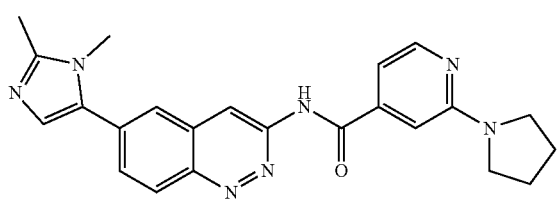 [SMILES: Cc1ncc(-c2ccc3nnc(NC(=O)c4ccnc(N5CCCC5)c4)cc3c2)n1C] 2318
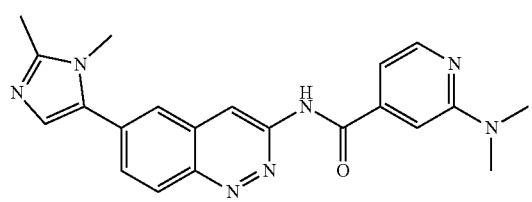 [SMILES: Cc1ncc(-c2ccc3nnc(NC(=O)c4ccnc(N(C)C)c4)cc3c2)n1C] 2319
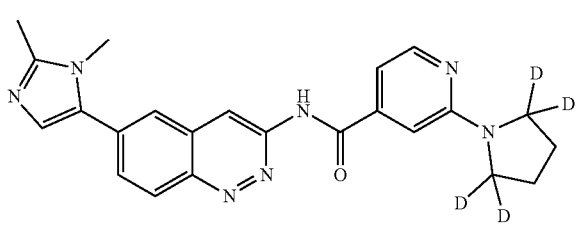 [SMILES: [2H]C1([2H])CCC([2H])([2H])N1c1cc(C(=O)Nc2cc3cc(-c4cnc(C)n4C)ccc3nn2)ccn1] 2320
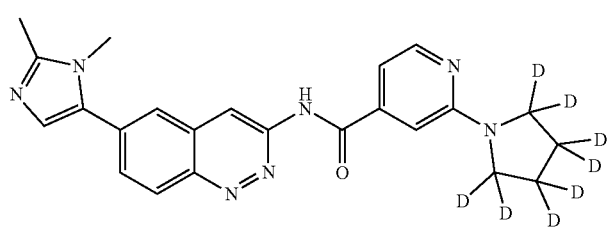 [SMILES: [2H]C1([2H])N(c2cc(C(=O)Nc3cc4cc(-c5cnc(C)n5C)ccc4nn3)ccn2)C([2H])([2H])C([2H])([2H])C1([2H])[2H]] 2321

TABLE 1-continued
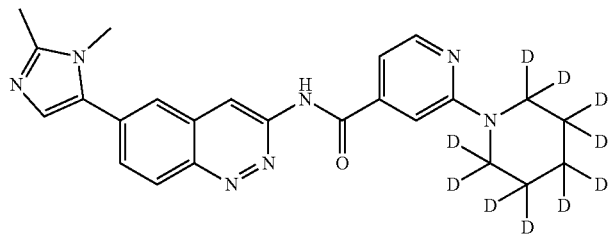 [SMILES: [2H]C1([2H])N(c2cc(C(=O)Nc3cc4cc(-c5cnc(C)n5C)ccc4nn3)ccn2)C([2H])([2H])C([2H])([2H])C([2H])([2H])C1([2H])[2H]]
2322
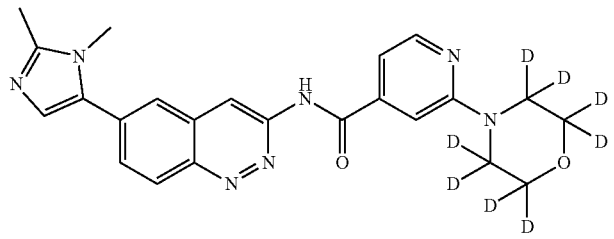
2323
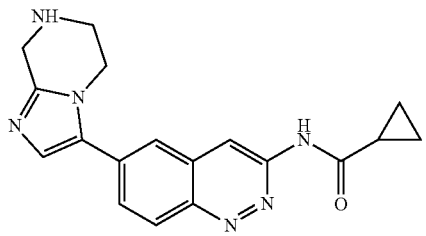 [SMILES: O=C(Nc1cc2cc(-c3cnc4n3CCNC4)ccc2nn1)C1CC1]
2324
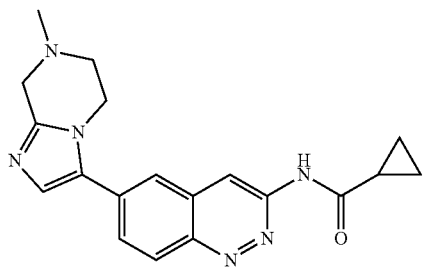 [SMILES: CN1CCn2c(-c3ccc4nnc(NC(=O)C5CC5)cc4c3)cnc2C1]
2325
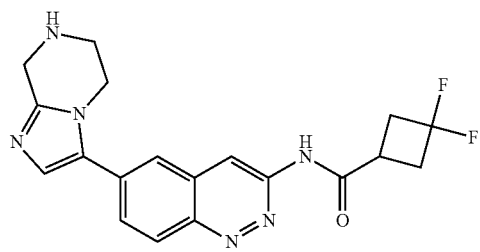 [SMILES: O=C(Nc1cc2cc(-c3cnc4n3CCNC4)ccc2nn1)C1CC(F)(F)C1]
2326
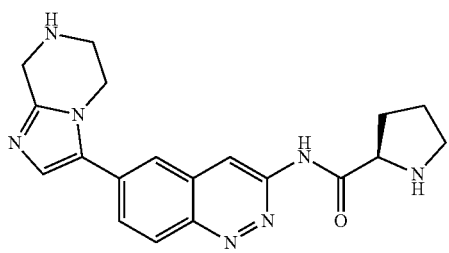 [SMILES: O=C(Nc1cc2cc(-c3cnc4n3CCNC4)ccc2nn1)[C@H]1CCCN1]
2327

TABLE 1-continued
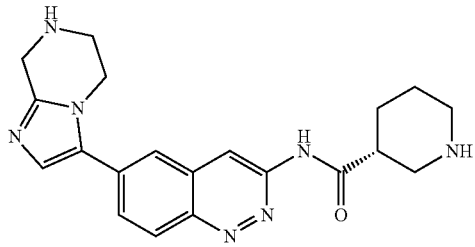 [SMILES: O=C(Nc1cc2cc(-c3cnc4n3CCNC4)ccc2nn1)[C@@H]1CCCNC1] 2328
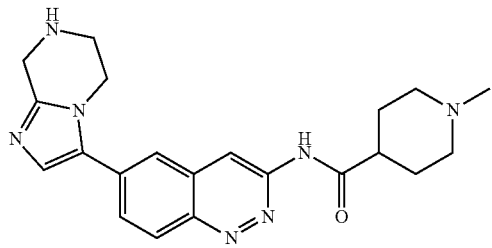 [SMILES: CN1CCC(C(=O)Nc2cc3cc(-c4cnc5n4CCNC5)ccc3nn2)CC1] 2329
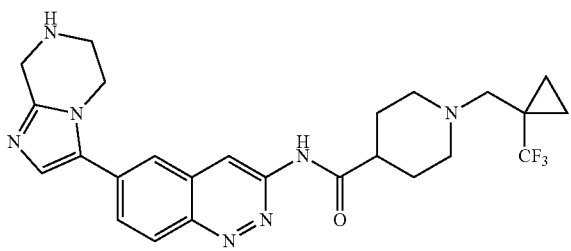 [SMILES: O=C(Nc1cc2cc(-c3cnc4n3CCNC4)ccc2nn1)C1CCN(CC2(C(F)(F)F)CC2)CC1] 2330
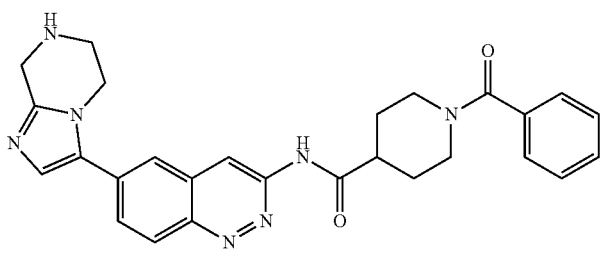 [SMILES: O=C(Nc1cc2cc(-c3cnc4n3CCNC4)ccc2nn1)C1CCN(C(=O)c2ccccc2)CC1] 2331
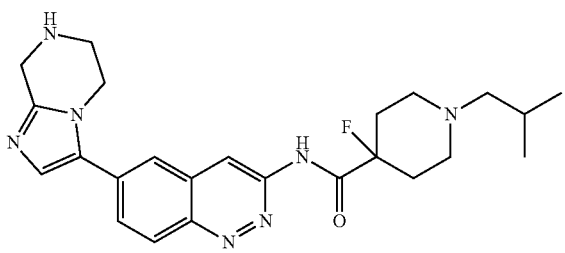 [SMILES: CC(C)CN1CCC(F)(C(=O)Nc2cc3cc(-c4cnc5n4CCNC5)ccc3nn2)CC1] 2332
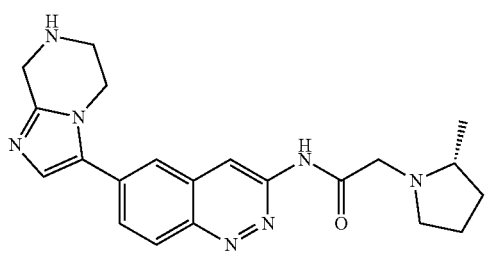 [SMILES: C[C@@H]1CCCN1CC(=O)Nc1cc2cc(-c3cnc4n3CCNC4)ccc2nn1] 2333

TABLE 1-continued
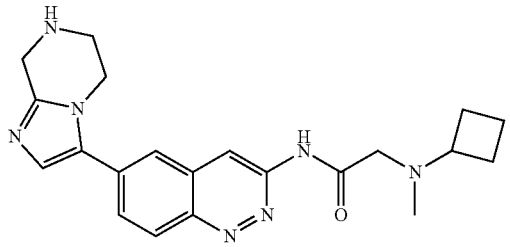 [SMILES: CN(CC(=O)Nc1cc2cc(-c3cnc4n3CCNC4)ccc2nn1)C1CCC1] 2334
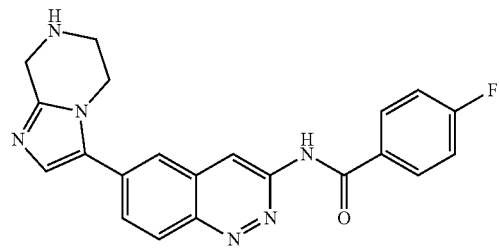 [SMILES: O=C(Nc1cc2cc(-c3cnc4n3CCNC4)ccc2nn1)c1ccc(F)cc1] 2335
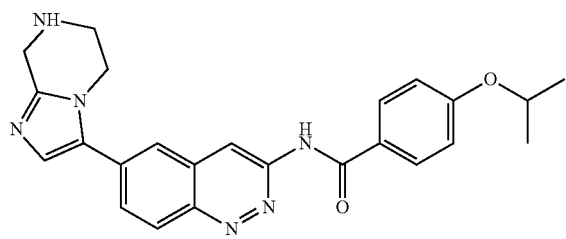 [SMILES: CC(C)Oc1ccc(C(=O)Nc2cc3cc(-c4cnc5n4CCNC5)ccc3nn2)cc1] 2336
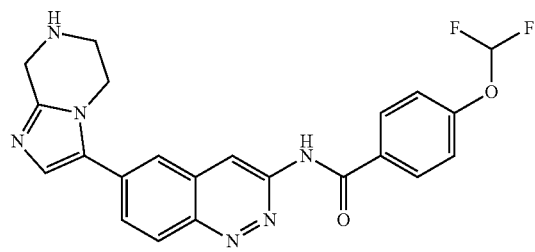 [SMILES: O=C(Nc1cc2cc(-c3cnc4n3CCNC4)ccc2nn1)c1ccc(OC(F)F)cc1] 2337
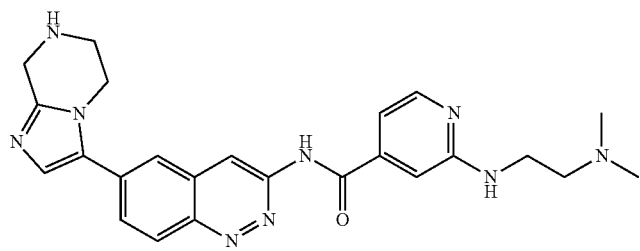 [SMILES: CN(C)CCNc1cc(C(=O)Nc2cc3cc(-c4cnc5n4CCNC5)ccc3nn2)ccn1] 2338
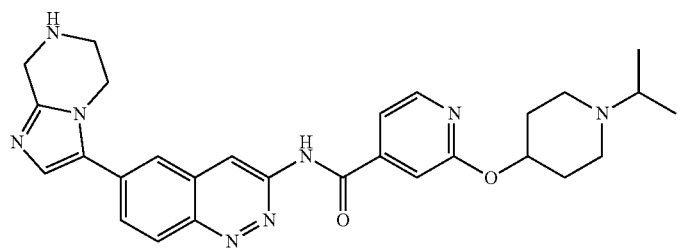 [SMILES: CC(C)N1CCC(Oc2cc(C(=O)Nc3cc4cc(-c5cnc6n5CCNC6)ccc4nn3)ccn2)CC1] 2339

TABLE 1-continued

| | |
|---|---|
| (structure) | 2340 |
| (structure) | 2341 |
| (structure) | 2342 |
| (structure) | 2343 |
| (structure) | 2344 |
| (structure) | 2345 |
| (structure) | 2346 |
| (structure) | 2347 |

TABLE 1-continued
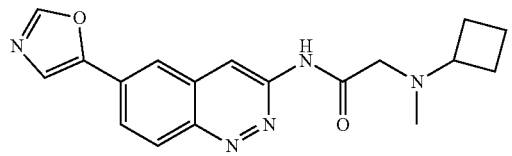 [SMILES: CN(CC(=O)Nc1cc2cc(-c3cnco3)ccc2nn1)C1CCC1] 2348
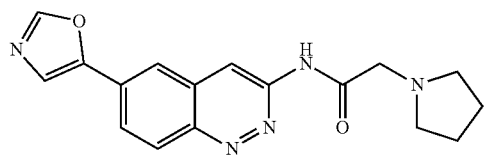 [SMILES: O=C(CN1CCCC1)Nc1cc2cc(-c3cnco3)ccc2nn1] 2349
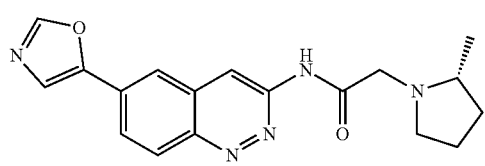 [SMILES: C[C@@H]1CCCN1CC(=O)Nc1cc2cc(-c3cnco3)ccc2nn1] 2350
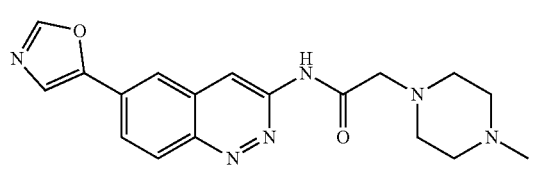 [SMILES: CN1CCN(CC(=O)Nc2cc3cc(-c4cnco4)ccc3nn2)CC1] 2351
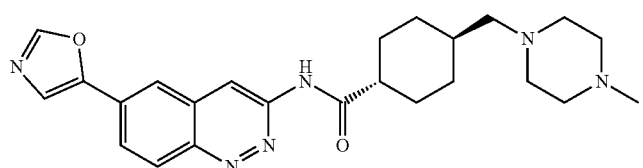 2352
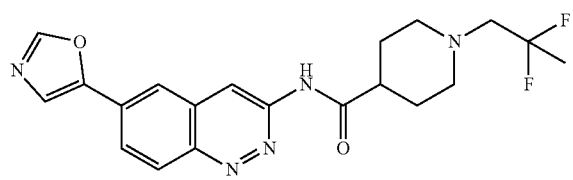 [SMILES: CC(F)(F)CN1CCC(C(=O)Nc2cc3cc(-c4cnco4)ccc3nn2)CC1] 2353
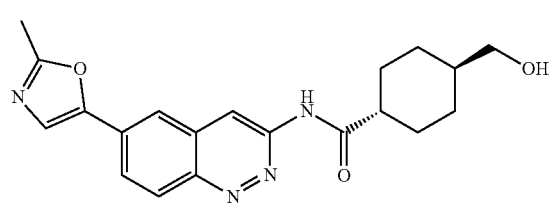 [SMILES: Cc1ncc(-c2ccc3nnc(NC(=O)[C@H]4CC[C@H](CO)CC4)cc3c2)o1] 2354
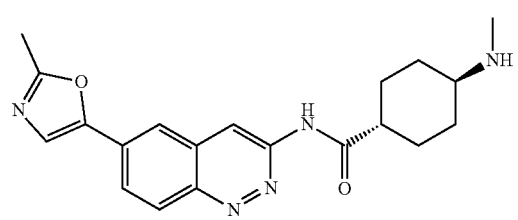 [SMILES: CN[C@H]1CC[C@H](C(=O)Nc2cc3cc(-c4cnc(C)o4)ccc3nn2)CC1] 2355

TABLE 1-continued
| | |
|---|---|
| 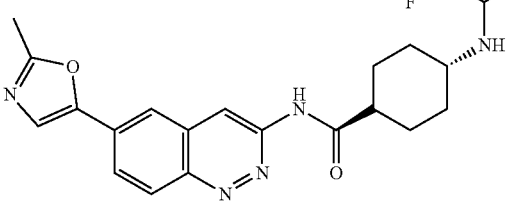 | 2356 |
| 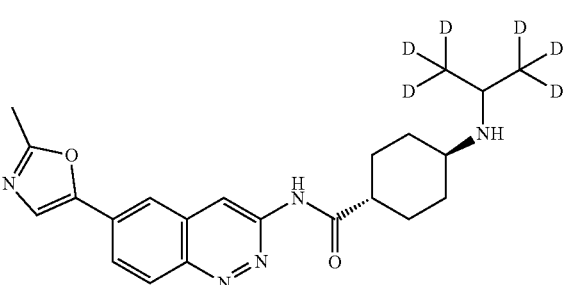 | 2357 |
| 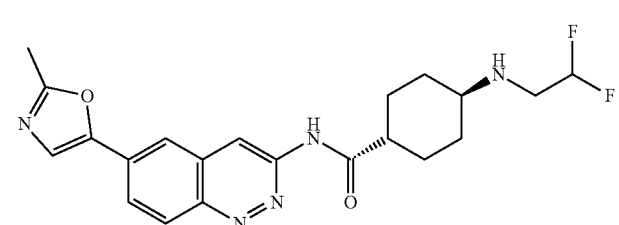 | 2358 |
| 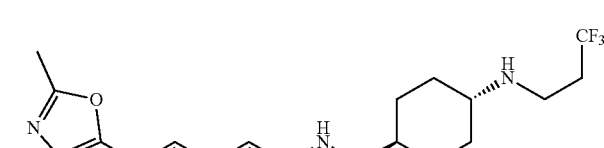 | 2359 |
| 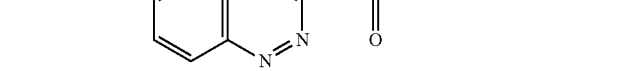 | 2360 |
|  | 2361 |
| 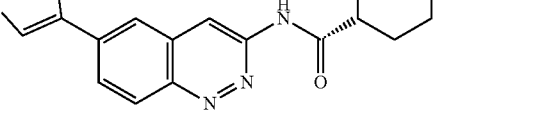 | 2362 |

TABLE 1-continued

| | |
|---|---|
| (structure) | 2363 |
| (structure) | 2364 |
| (structure) | 2365 |
| (structure) | 2366 |
| (structure) | 2367 |
| (structure) | 2368 |
| (structure) | 2369 |

TABLE 1-continued
| | |
|---|---|
| 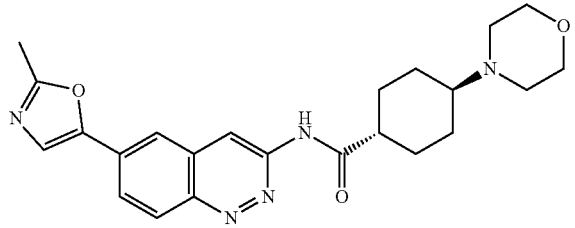 [SMILES: Cc1ncc(-c2ccc3nnc(NC(=O)[C@H]4CC[C@H](N5CCOCC5)CC4)cc3c2)o1] | 2370 |
| 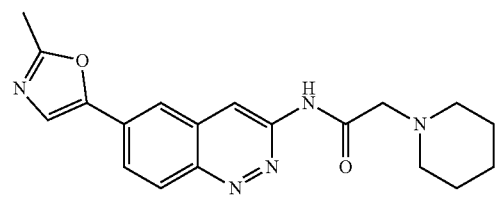 [SMILES: Cc1ncc(-c2ccc3nnc(NC(=O)CN4CCCCC4)cc3c2)o1] | 2371 |
| 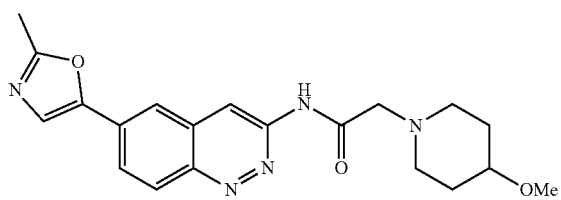 [SMILES: COC1CCN(CC(=O)Nc2cc3cc(-c4cnc(C)o4)ccc3nn2)CC1] | 2372 |
| 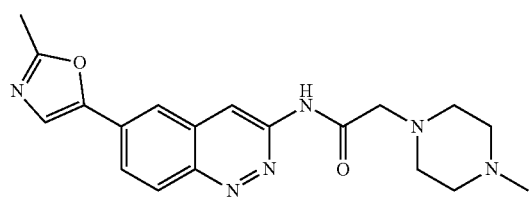 [SMILES: Cc1ncc(-c2ccc3nnc(NC(=O)CN4CCN(C)CC4)cc3c2)o1] | 2373 |
| 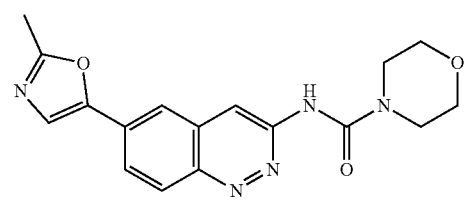 [SMILES: Cc1ncc(-c2ccc3nnc(NC(=O)N4CCOCC4)cc3c2)o1] | 2374 |
| 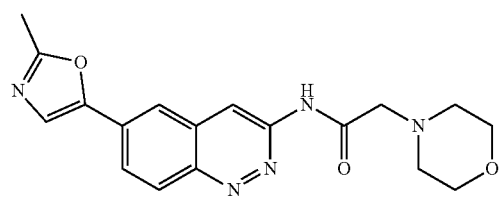 [SMILES: Cc1ncc(-c2ccc3nnc(NC(=O)CN4CCOCC4)cc3c2)o1] | 2375 |
| 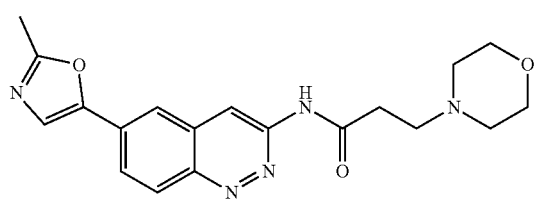 [SMILES: Cc1ncc(-c2ccc3nnc(NC(=O)CCN4CCOCC4)cc3c2)o1] | 2376 |
| 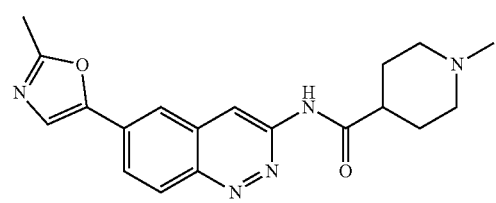 [SMILES: Cc1ncc(-c2ccc3nnc(NC(=O)C4CCN(C)CC4)cc3c2)o1] | 2377 |

TABLE 1-continued
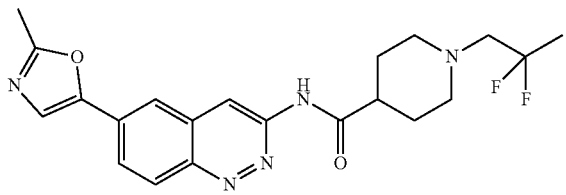 [SMILES: Cc1ncc(-c2ccc3nnc(NC(=O)C4CCN(CC(C)(F)F)CC4)cc3c2)o1] 2378
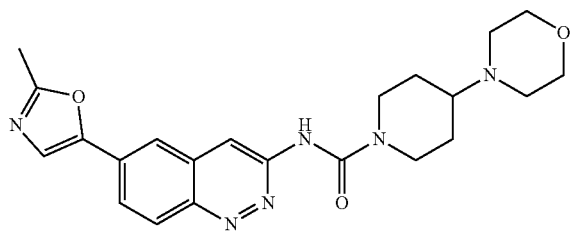 [SMILES: Cc1ncc(-c2ccc3nnc(NC(=O)N4CCC(N5CCOCC5)CC4)cc3c2)o1] 2379
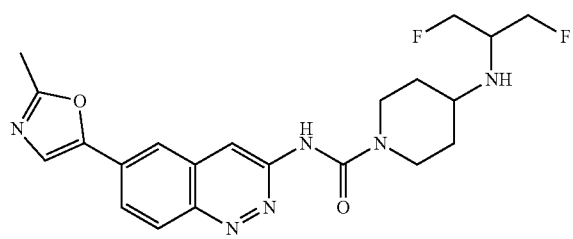 [SMILES: Cc1ncc(-c2ccc3nnc(NC(=O)N4CCC(NC(CF)CF)CC4)cc3c2)o1] 2380
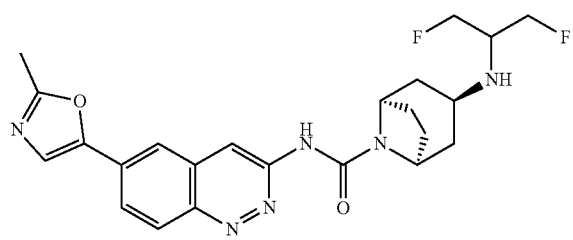 [SMILES: Cc1ncc(-c2ccc3nnc(NC(=O)N4[C@@H]5CC[C@H]4C[C@H](NC(CF)CF)C5)cc3c2)o1] 2381
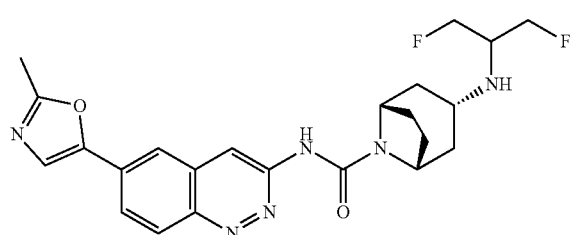 2382
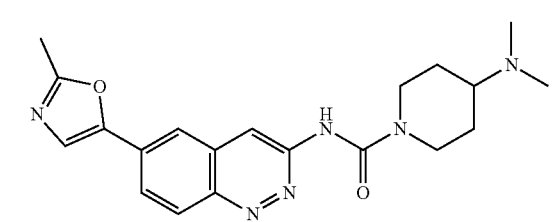 [SMILES: Cc1ncc(-c2ccc3nnc(NC(=O)N4CCC(N(C)C)CC4)cc3c2)o1] 2383
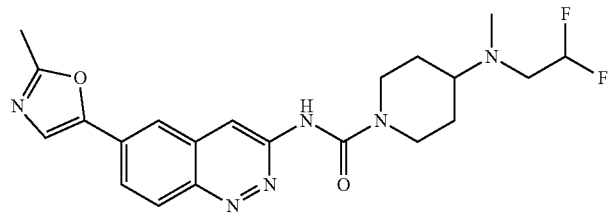 [SMILES: Cc1ncc(-c2ccc3nnc(NC(=O)N4CCC(N(C)CC(F)F)CC4)cc3c2)o1] 2384

TABLE 1-continued
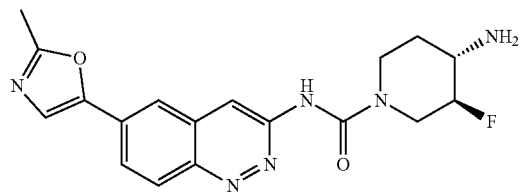 [SMILES: Cc1ncc(-c2ccc3nnc(NC(=O)N4CC[C@H](N)[C@@H](F)C4)cc3c2)o1] 2385
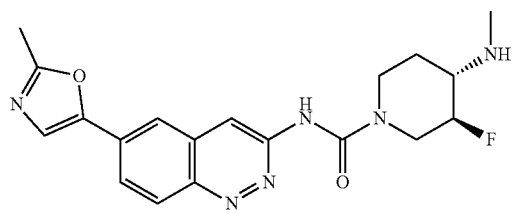 [SMILES: CN[C@H]1CCN(C(=O)Nc2cc3cc(-c4cnc(C)o4)ccc3nn2)C[C@@H]1F] 2386
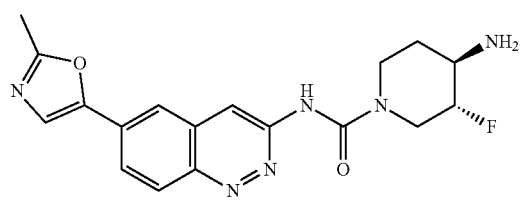 [SMILES: Cc1ncc(-c2ccc3nnc(NC(=O)N4CC[C@@H](N)[C@H](F)C4)cc3c2)o1] 2387
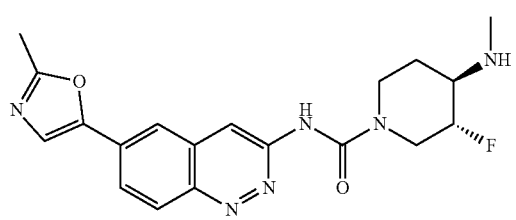 [SMILES: CN[C@@H]1CCN(C(=O)Nc2cc3cc(-c4cnc(C)o4)ccc3nn2)C[C@H]1F] 2388
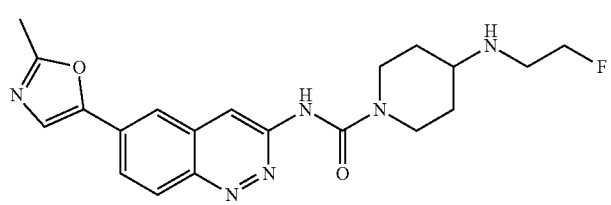 [SMILES: Cc1ncc(-c2ccc3nnc(NC(=O)N4CCC(NCCF)CC4)cc3c2)o1] 2389
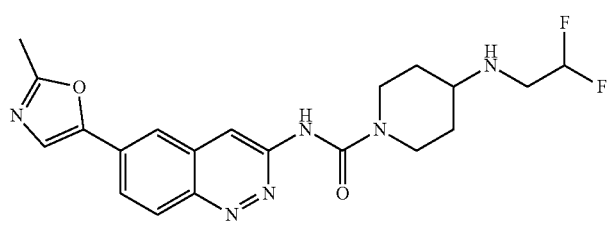 [SMILES: Cc1ncc(-c2ccc3nnc(NC(=O)N4CCC(NCC(F)F)CC4)cc3c2)o1] 2390
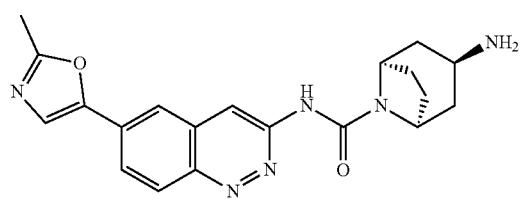 [SMILES: Cc1ncc(-c2ccc3nnc(NC(=O)N4[C@@H]5CC[C@H]4C[C@H](N)C5)cc3c2)o1] 2391

TABLE 1-continued
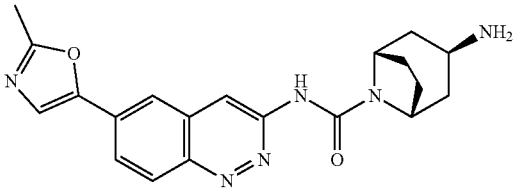 [SMILES: Cc1ncc(-c2ccc3nnc(NC(=O)N4[C@@H]5CC[C@H]4C[C@@H](N)C5)cc3c2)o1] 2392
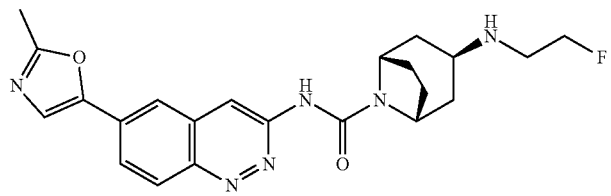 [SMILES: Cc1ncc(-c2ccc3nnc(NC(=O)N4[C@@H]5CC[C@H]4C[C@@H](NCCF)C5)cc3c2)o1] 2393
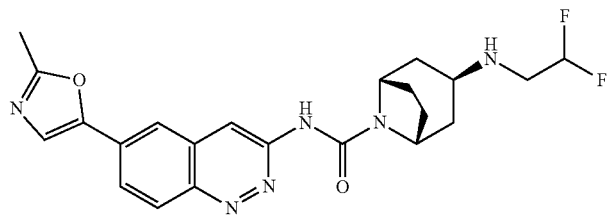 [SMILES: Cc1ncc(-c2ccc3nnc(NC(=O)N4[C@@H]5CC[C@H]4C[C@@H](NCC(F)F)C5)cc3c2)o1] 2394
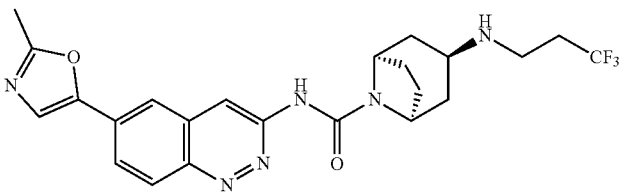 [SMILES: Cc1ncc(-c2ccc3nnc(NC(=O)N4[C@@H]5CC[C@H]4C[C@H](NCCC(F)(F)F)C5)cc3c2)o1] 2395
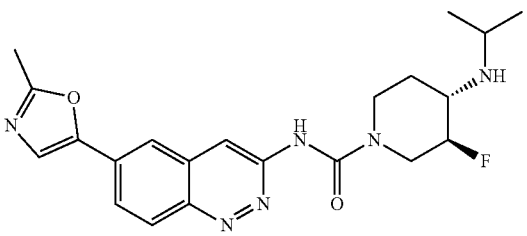 [SMILES: Cc1ncc(-c2ccc3nnc(NC(=O)N4CC[C@H](NC(C)C)[C@@H](F)C4)cc3c2)o1] 2396
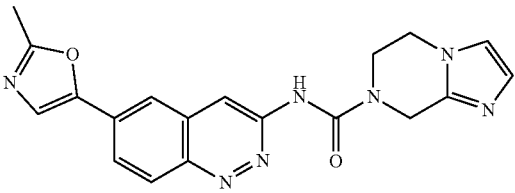 [SMILES: Cc1ncc(-c2ccc3nnc(NC(=O)N4CCn5ccnc5C4)cc3c2)o1] 2397
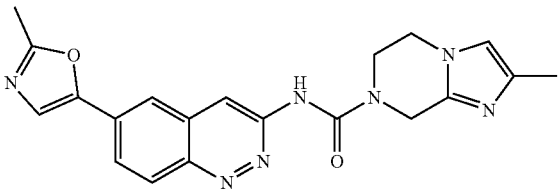 [SMILES: Cc1cn2c(n1)CN(C(=O)Nc1cc3cc(-c4cnc(C)o4)ccc3nn1)CC2] 2398

TABLE 1-continued
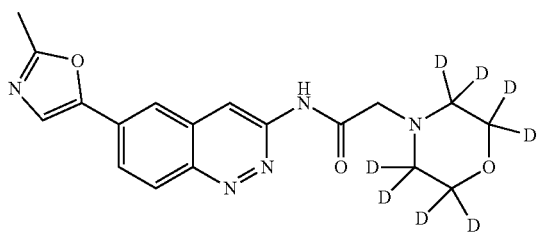 [SMILES: [2H]C1([2H])OC([2H])([2H])C([2H])([2H])N(CC(=O)Nc2cc3cc(-c4cnc(C)o4)ccc3nn2)C1([2H])[2H]] 2399
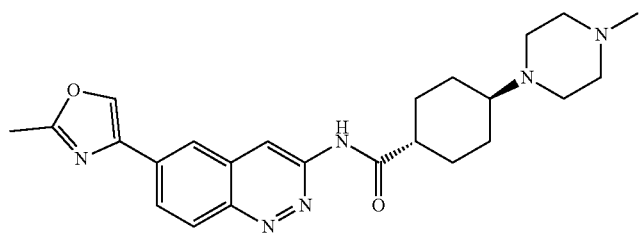 2400
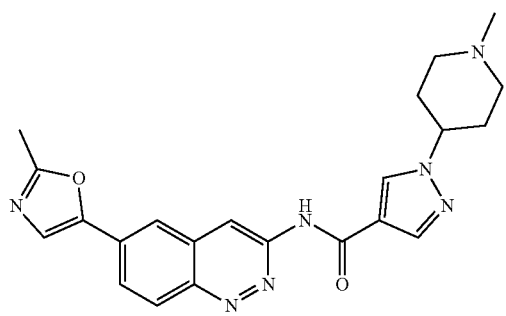 [SMILES: Cc1ncc(-c2ccc3nnc(NC(=O)c4cnn(C5CCN(C)CC5)c4)cc3c2)o1] 2401
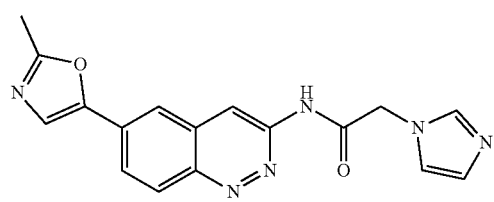 [SMILES: Cc1ncc(-c2ccc3nnc(NC(=O)Cn4ccnc4)cc3c2)o1] 2401
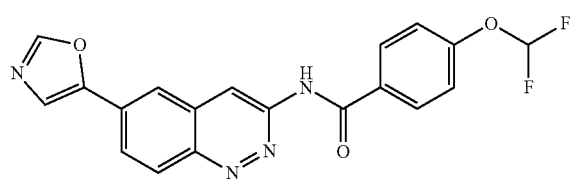 2403
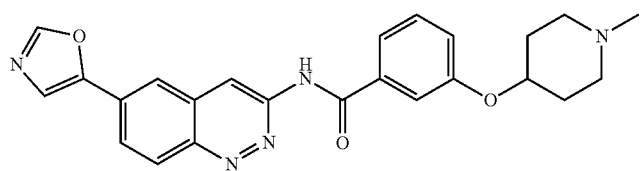 [SMILES: CN1CCC(Oc2cccc(C(=O)Nc3cc4cc(-c5cnco5)ccc4nn3)c2)CC1] 2404
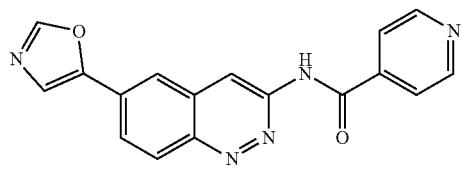 2405

TABLE 1-continued
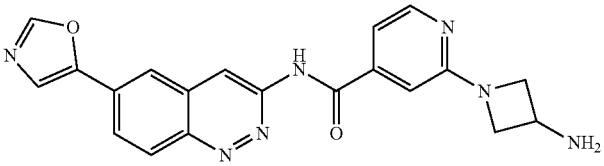 [SMILES: NC1CN(c2cc(C(=O)Nc3cc4cc(-c5cnco5)ccc4nn3)ccn2)C1] 2406
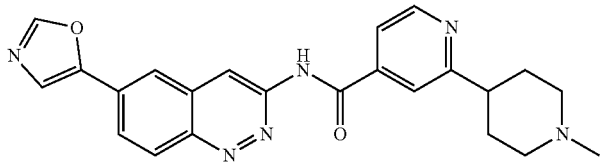 2407
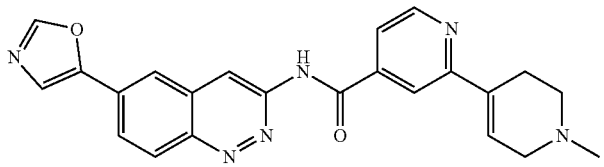 2408
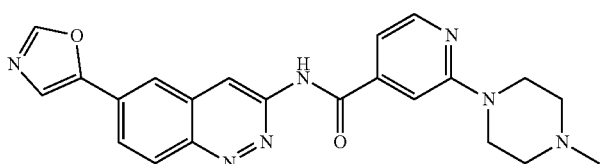 2409
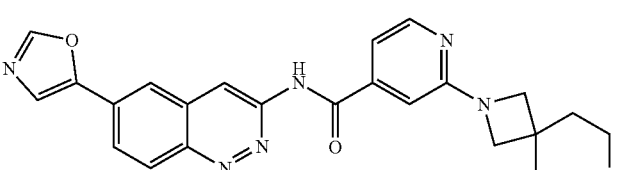 2410
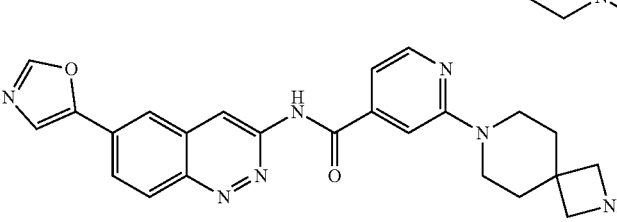 2411
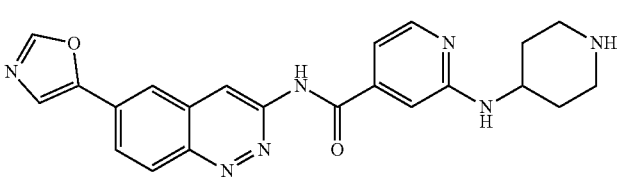 [SMILES: O=C(Nc1cc2cc(-c3cnco3)ccc2nn1)c1ccnc(NC2CCNCC2)c1] 2412
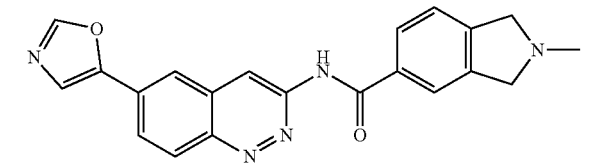 [SMILES: CN1Cc2ccc(C(=O)Nc3cc4cc(-c5cnco5)ccc4nn3)cc2C1] 2413
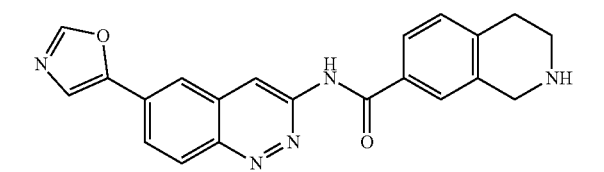 [SMILES: O=C(Nc1cc2cc(-c3cnco3)ccc2nn1)c1ccc2c(c1)CNCC2] 2414

TABLE 1-continued
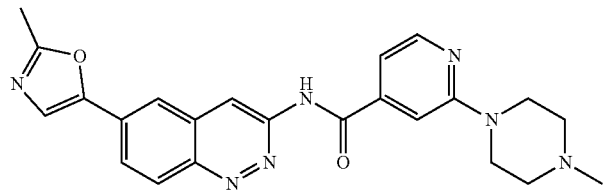 2415
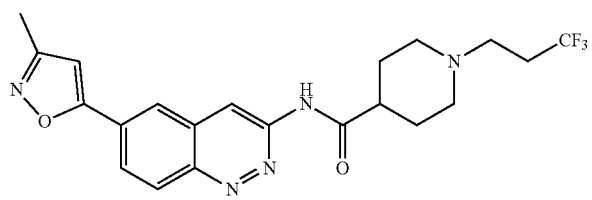 [SMILES: Cc1cc(-c2ccc3nnc(NC(=O)C4CCN(CCC(F)(F)F)CC4)cc3c2)on1] 2416
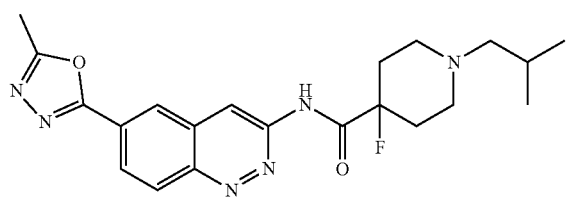 [SMILES: Cc1nnc(-c2ccc3nnc(NC(=O)C4(F)CCN(CC(C)C)CC4)cc3c2)o1] 2417
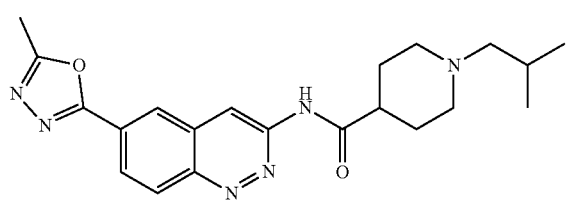 [SMILES: Cc1nnc(-c2ccc3nnc(NC(=O)C4CCN(CC(C)C)CC4)cc3c2)o1] 2418
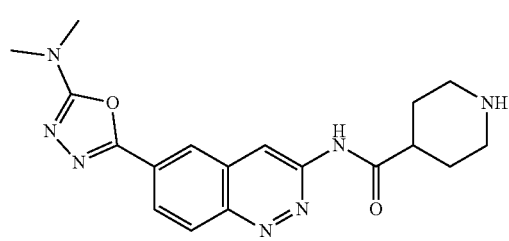 [SMILES: CN(C)c1nnc(-c2ccc3nnc(NC(=O)C4CCNCC4)cc3c2)o1] 2419
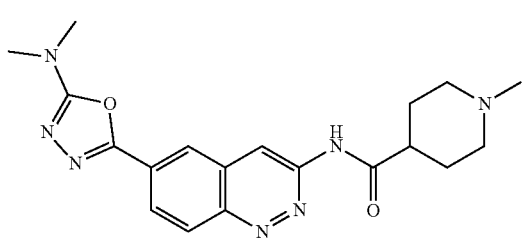 2420
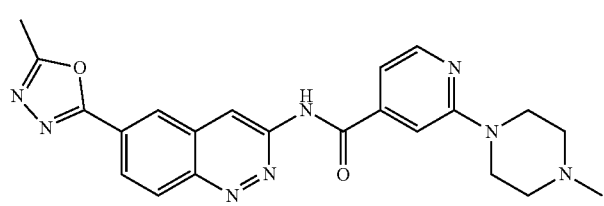 2421

TABLE 1-continued
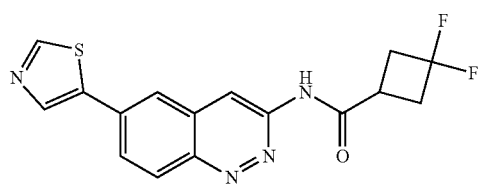 [SMILES: O=C(Nc1cc2cc(-c3cncs3)ccc2nn1)C1CC(F)(F)C1] 2422
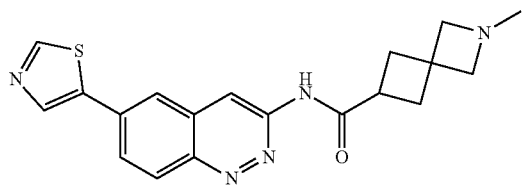 [SMILES: CN1CC2(CC(C(=O)Nc3cc4cc(-c5cncs5)ccc4nn3)C2)C1] 2423
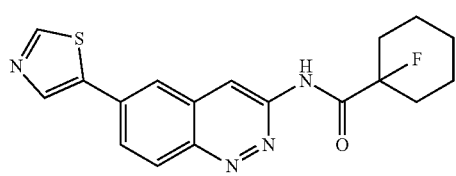 2424
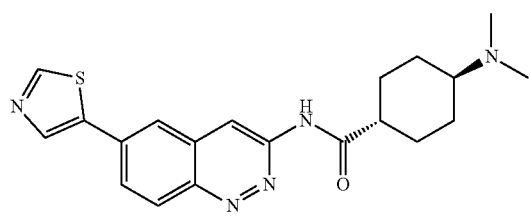 [SMILES: CN(C)[C@H]1CC[C@H](C(=O)Nc2cc3cc(-c4cncs4)ccc3nn2)CC1] 2425
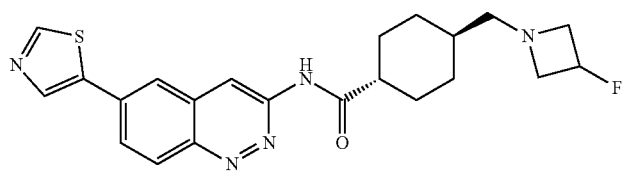 [SMILES: O=C(Nc1cc2cc(-c3cncs3)ccc2nn1)[C@H]1CC[C@H](CN2CC(F)C2)CC1] 2426
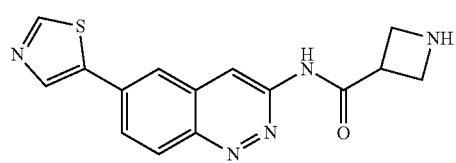 [SMILES: O=C(Nc1cc2cc(-c3cncs3)ccc2nn1)C1CNC1] 2427
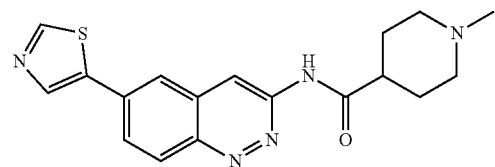 [SMILES: CN1CCC(C(=O)Nc2cc3cc(-c4cncs4)ccc3nn2)CC1] 2428
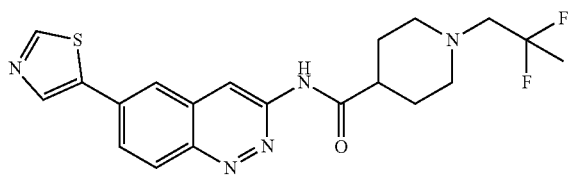 [SMILES: CC(F)(F)CN1CCC(C(=O)Nc2cc3cc(-c4cncs4)ccc3nn2)CC1] 2429

TABLE 1-continued
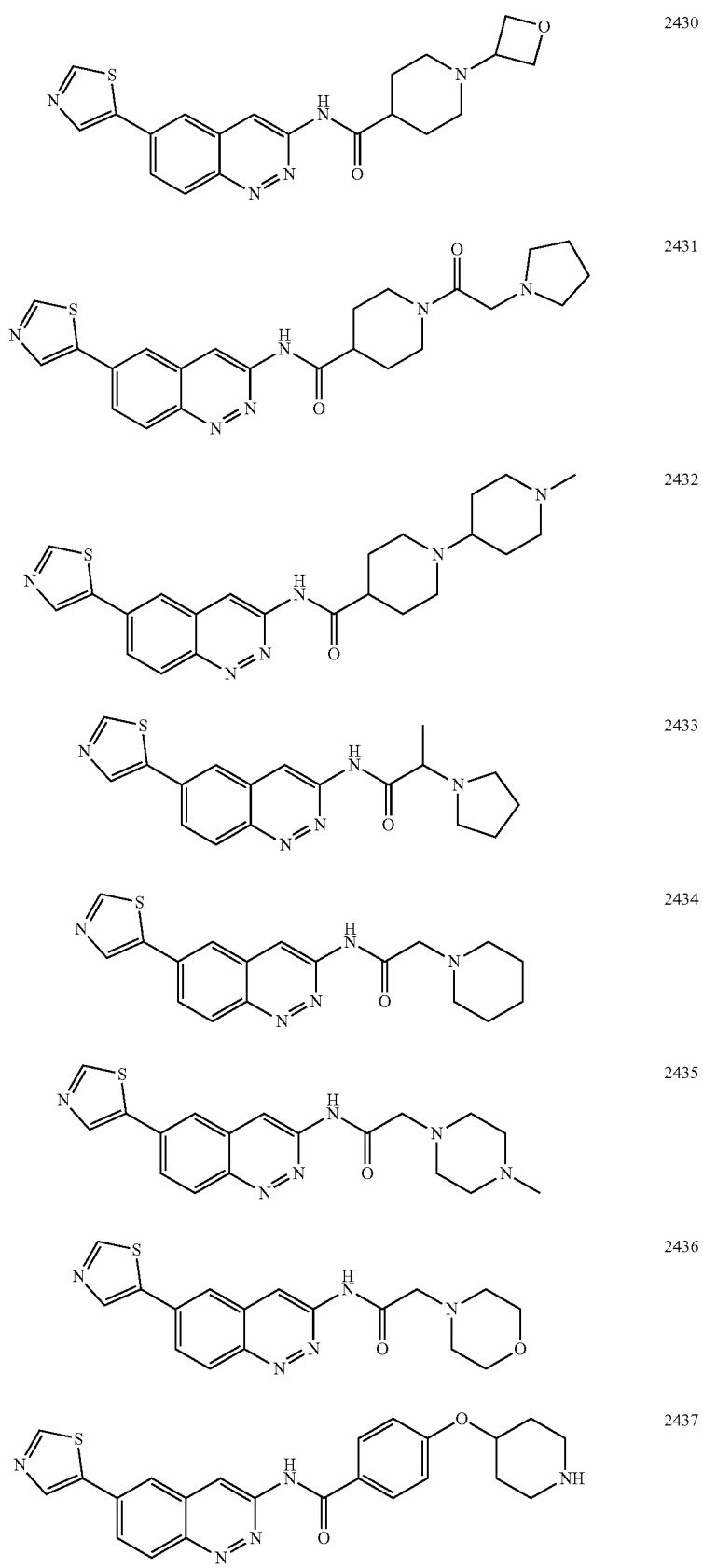

TABLE 1-continued
| | |
|---|---|
| 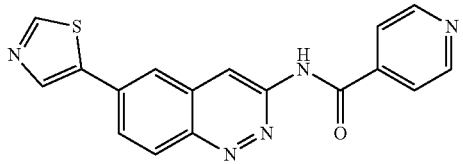 [SMILES: O=C(Nc1cc2cc(-c3cncs3)ccc2nn1)c1ccncc1] | 2438 |
| | 2439 |
| | 2440 |
| | 2441 |
| | 2442 |
| | 2443 |
| | 2444 |
| | 2445 |

TABLE 1-continued
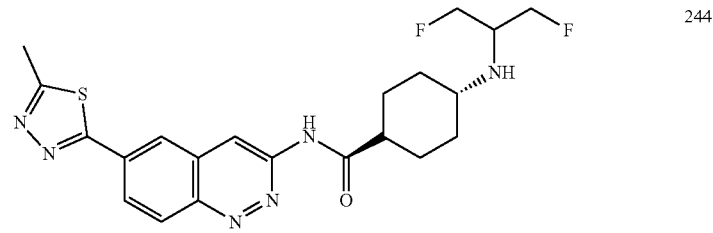 2446
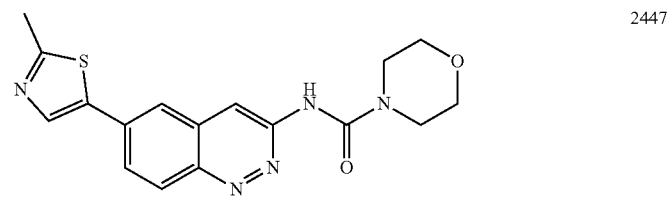 2447
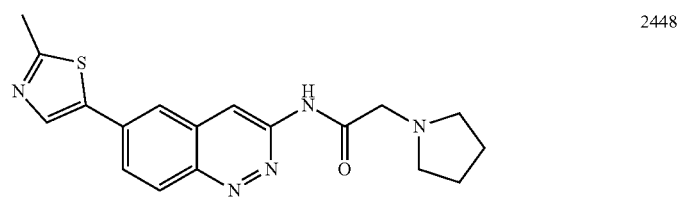 2448
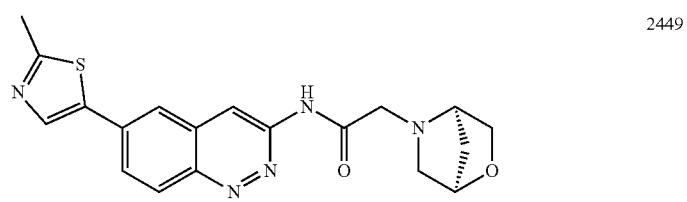 2449
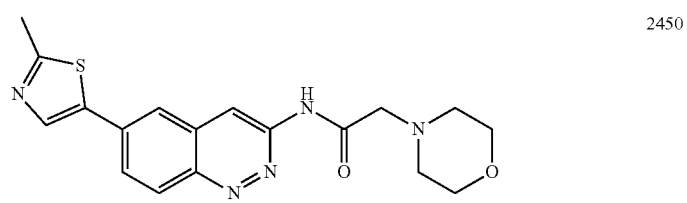 2450
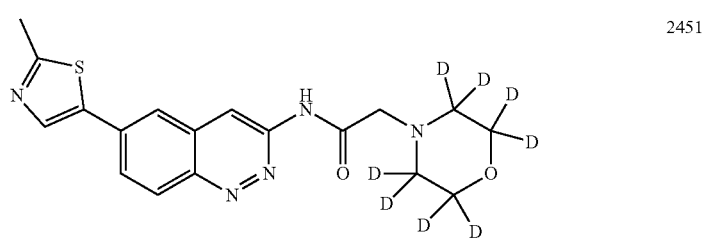 2451
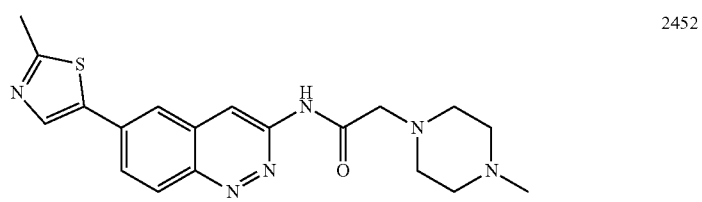 2452

TABLE 1-continued
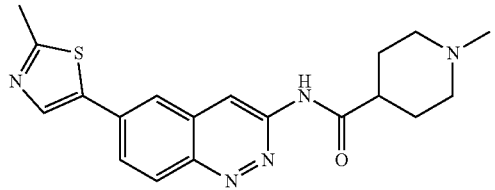 2453
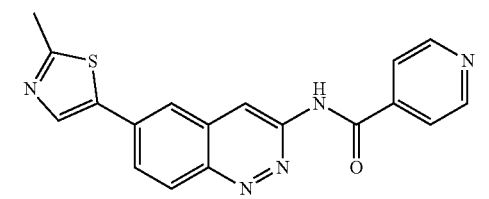 [SMILES: Cc1ncc(-c2ccc3nnc(NC(=O)c4ccncc4)cc3c2)s1] 2454
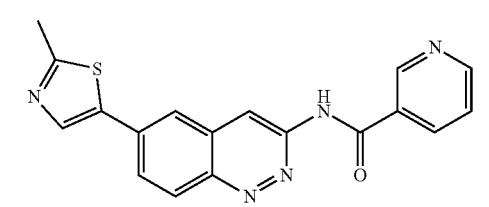 [SMILES: Cc1ncc(-c2ccc3nnc(NC(=O)c4cccnc4)cc3c2)s1] 2455
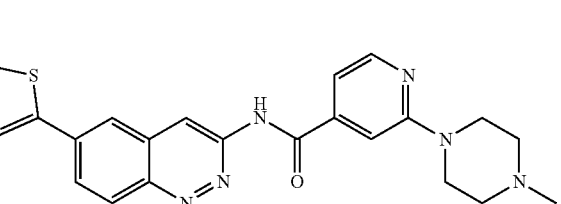 2456
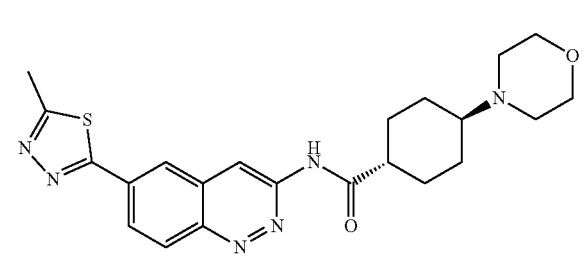 [SMILES: Cc1nnc(-c2ccc3nnc(NC(=O)[C@H]4CC[C@H](N5CCOCC5)CC4)cc3c2)s1] 2457
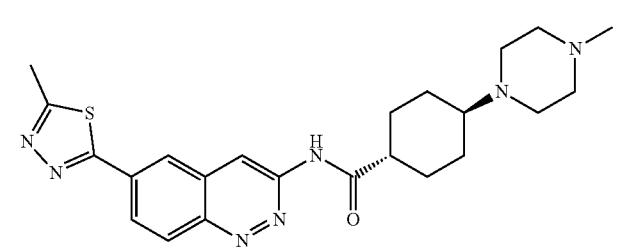 [SMILES: Cc1nnc(-c2ccc3nnc(NC(=O)[C@H]4CC[C@H](N5CCN(C)CC5)CC4)cc3c2)s1] 2458
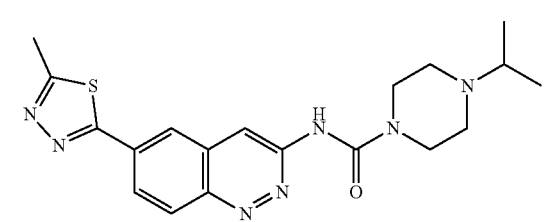 [SMILES: Cc1nnc(-c2ccc3nnc(NC(=O)N4CCN(C(C)C)CC4)cc3c2)s1] 2459

TABLE 1-continued
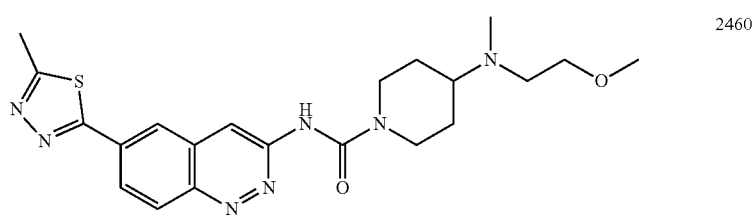 2460
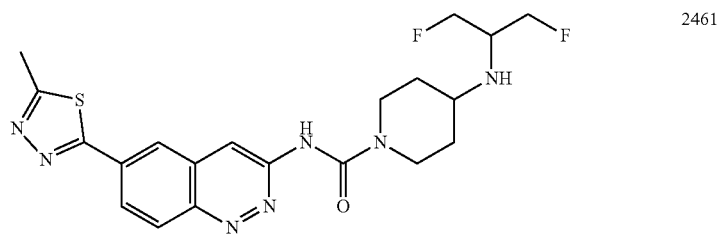 2461
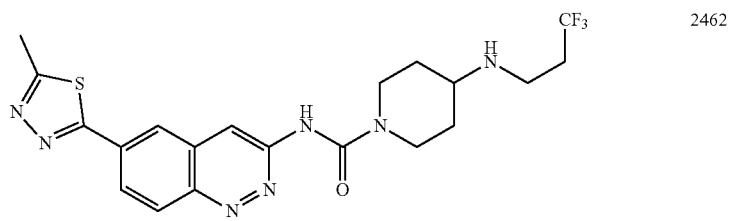 2462
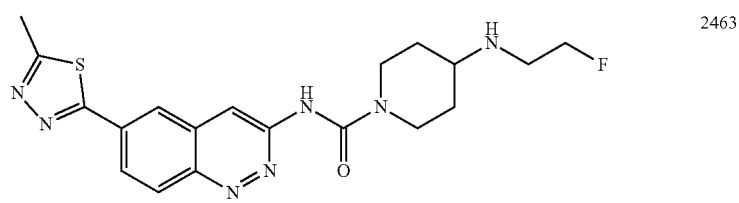 2463
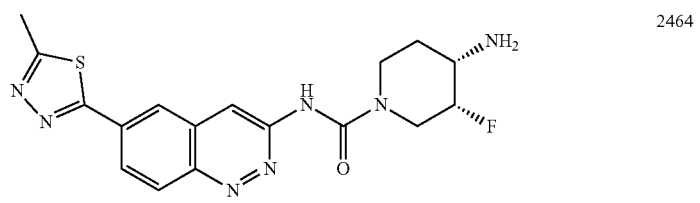 2464
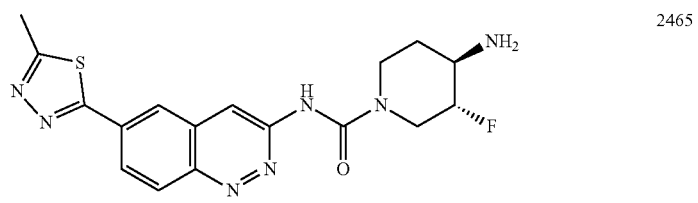 2465
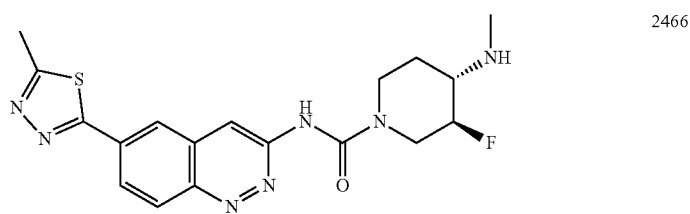 2466

TABLE 1-continued
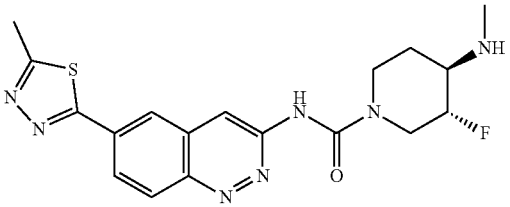 [SMILES: CN[C@@H]1CCN(C(=O)Nc2cc3cc(-c4nnc(C)s4)ccc3nn2)C[C@H]1F]
2467
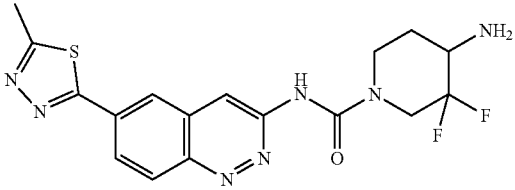 [SMILES: Cc1nnc(-c2ccc3nnc(NC(=O)N4CCC(N)C(F)(F)C4)cc3c2)s1]
2468
2469
2470
2471
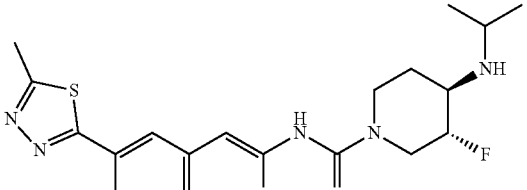
2472

TABLE 1-continued
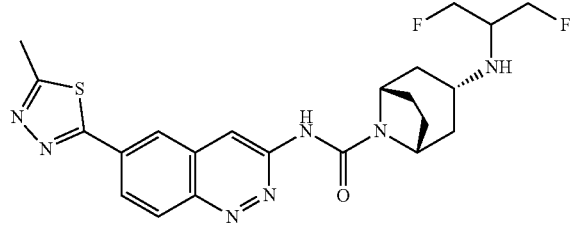 [SMILES: Cc1nnc(-c2ccc3nnc(NC(=O)N4[C@@H]5CC[C@H]4C[C@H](NC(CF)CF)C5)cc3c2)s1] 2473
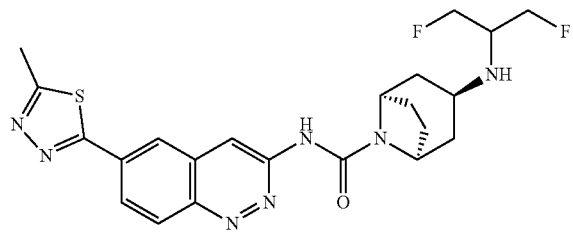 [SMILES: Cc1nnc(-c2ccc3nnc(NC(=O)N4[C@@H]5CC[C@H]4C[C@H](NC(CF)CF)C5)cc3c2)s1] 2474
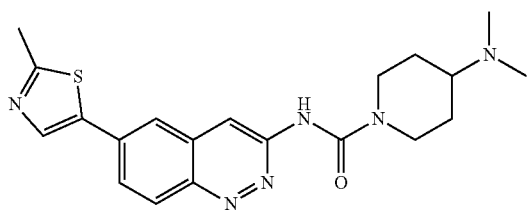 [SMILES: Cc1ncc(-c2ccc3nnc(NC(=O)N4CCC(N(C)C)CC4)cc3c2)s1] 2475
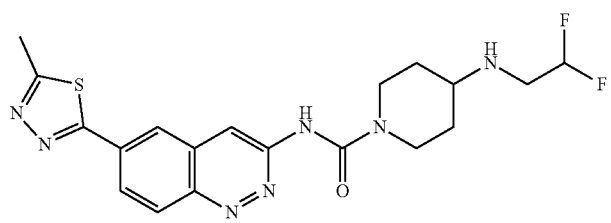 [SMILES: Cc1nnc(-c2ccc3nnc(NC(=O)N4CCC(NCC(F)F)CC4)cc3c2)s1] 2476
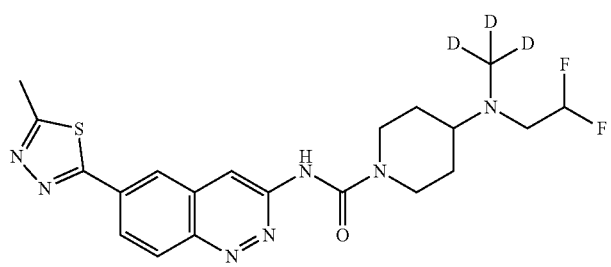 [SMILES: [2H]C([2H])([2H])N(CC(F)F)C1CCN(C(=O)Nc2cc3cc(-c4nnc(C)s4)ccc3nn2)CC1] 2477
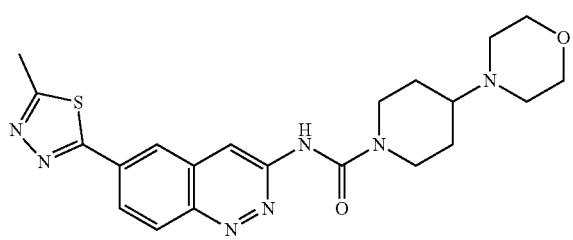 [SMILES: Cc1nnc(-c2ccc3nnc(NC(=O)N4CCC(N5CCOCC5)CC4)cc3c2)s1] 2478

TABLE 1-continued
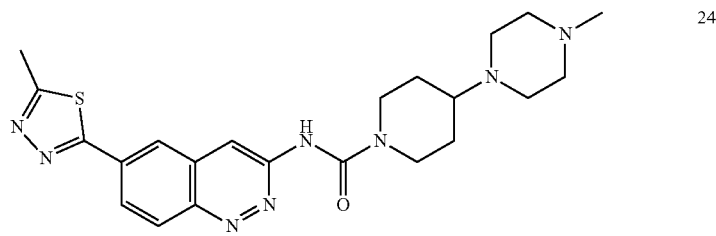
2479
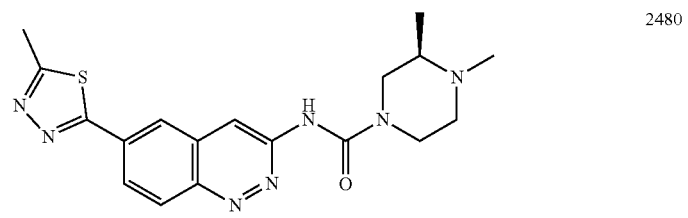
2480
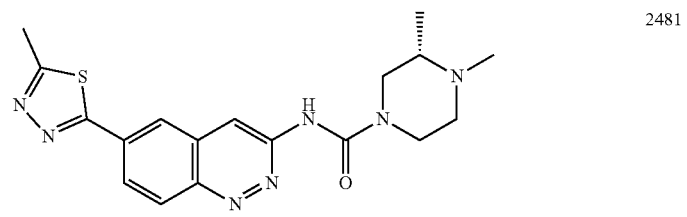
2481
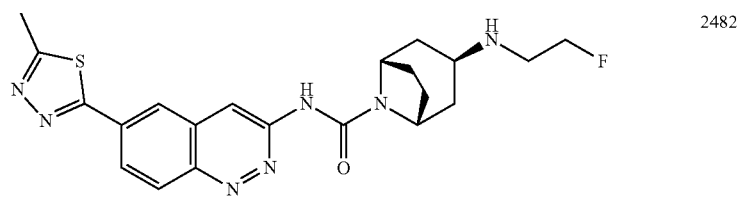
2482
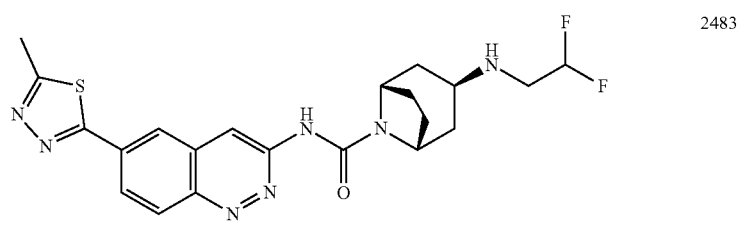
2483
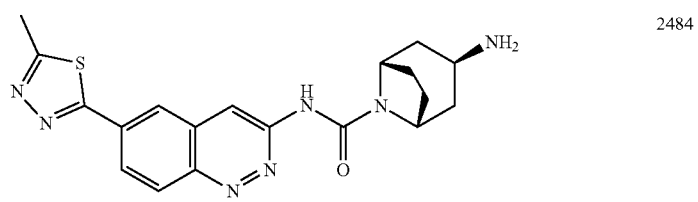
2484
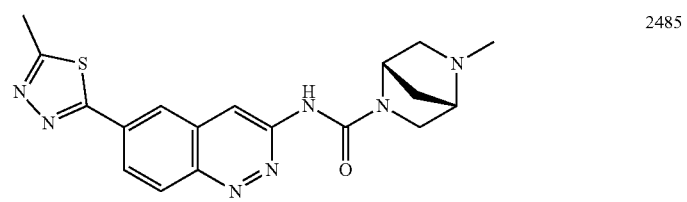
2485

TABLE 1-continued
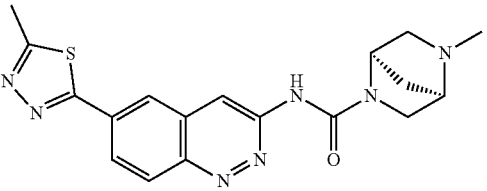 [SMILES: Cc1nnc(-c2ccc3nnc(NC(=O)N4C[C@H]5C[C@@H]4CN5C)cc3c2)s1] 2486
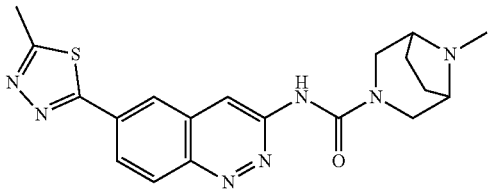 [SMILES: Cc1nnc(-c2ccc3nnc(NC(=O)N4CC5CCC(C4)N5C)cc3c2)s1] 2487
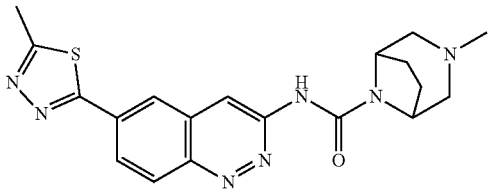 [SMILES: Cc1nnc(-c2ccc3nnc(NC(=O)N4C5CCC4CN(C)C5)cc3c2)s1] 2488
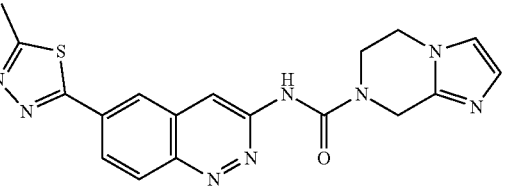 2489
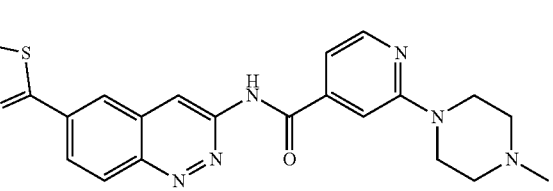 2490
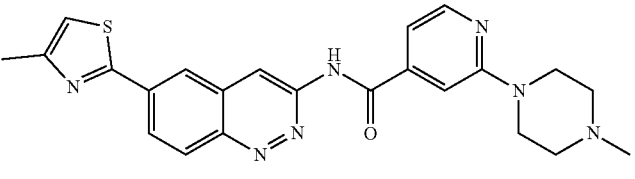 2491
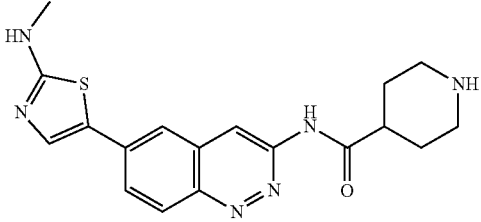 [SMILES: CNc1ncc(-c2ccc3nnc(NC(=O)C4CCNCC4)cc3c2)s1] 2492

TABLE 1-continued
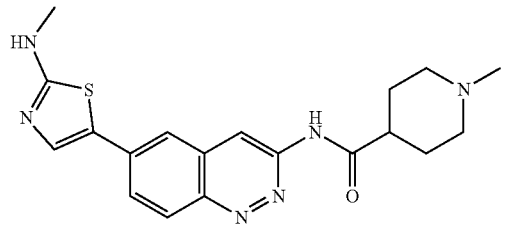 [SMILES: CNc1ncc(-c2ccc3nnc(NC(=O)C4CCN(C)CC4)cc3c2)s1]
2493
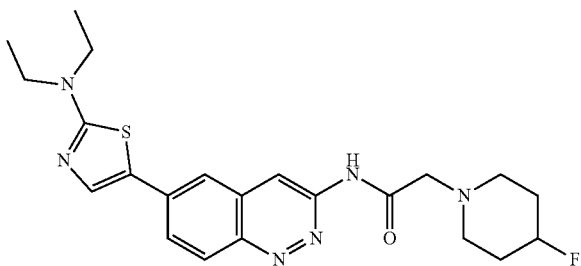 [SMILES: CCN(CC)c1ncc(-c2ccc3nnc(NC(=O)CN4CCC(F)CC4)cc3c2)s1]
2494
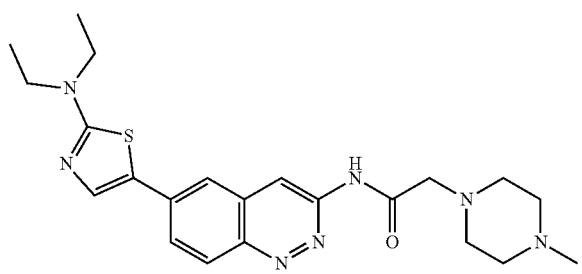 [SMILES: CCN(CC)c1ncc(-c2ccc3nnc(NC(=O)CN4CCN(C)CC4)cc3c2)s1]
2495
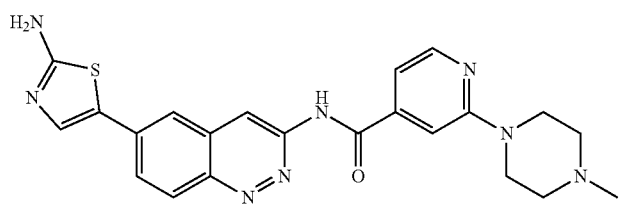 [SMILES: CN1CCN(c2cc(C(=O)Nc3cc4cc(-c5cnc(N)s5)ccc4nn3)ccn2)CC1]
2496
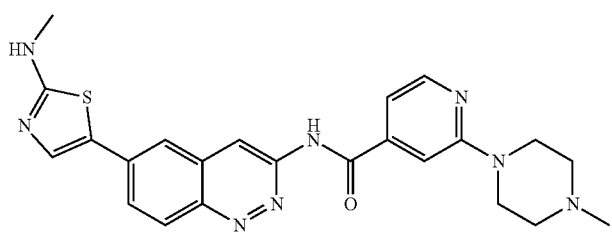 [SMILES: CNc1ncc(-c2ccc3nnc(NC(=O)c4ccnc(N5CCN(C)CC5)c4)cc3c2)s1]
2497
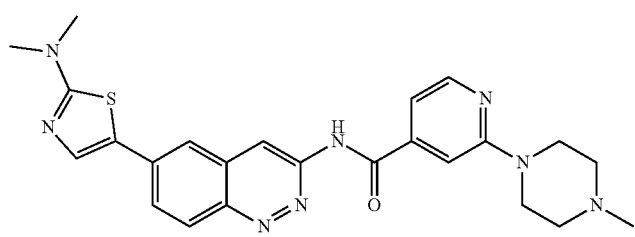
2498

TABLE 1-continued
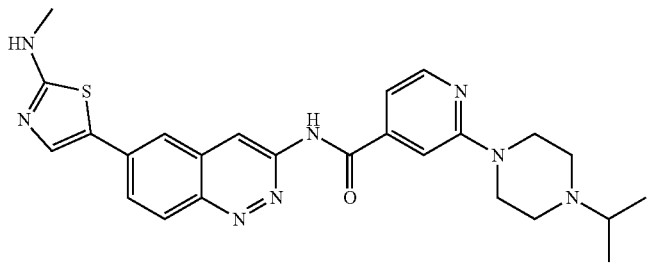 [SMILES: CNc1ncc(-c2ccc3nnc(NC(=O)c4ccnc(N5CCN(C(C)C)CC5)c4)cc3c2)s1] 2499
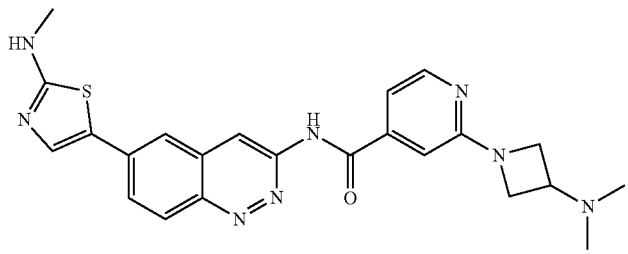 2500
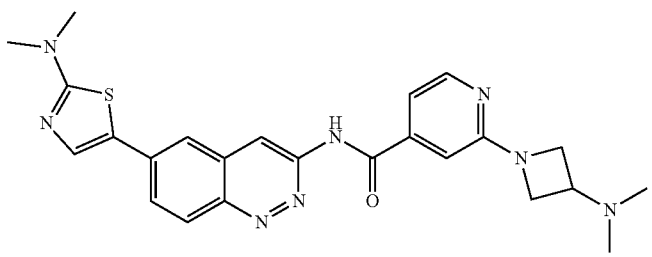 2501
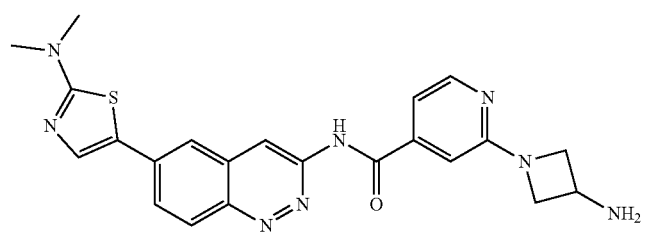 2502
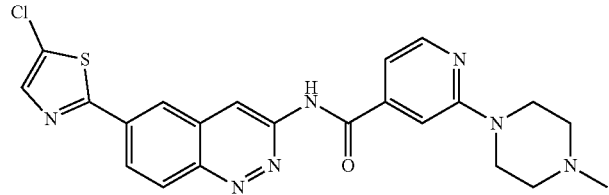 [SMILES: CN1CCN(c2cc(C(=O)Nc3cc4cc(-c5ncc(Cl)s5)ccc4nn3)ccn2)CC1] 2503
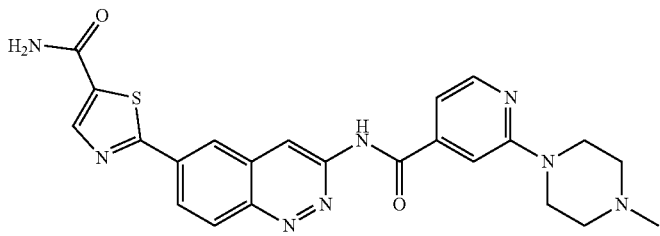 [SMILES: CN1CCN(c2cc(C(=O)Nc3cc4cc(-c5ncc(C(N)=O)s5)ccc4nn3)ccn2)CC1] 2504
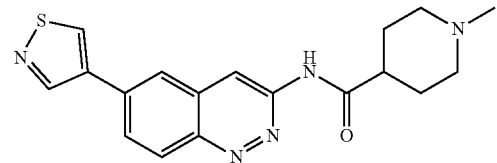 [SMILES: CN1CCC(C(=O)Nc2cc3cc(-c4cnsc4)ccc3nn2)CC1] 2505

TABLE 1-continued
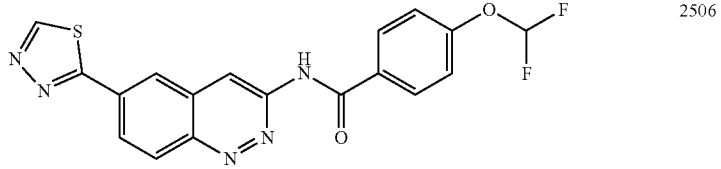
2506
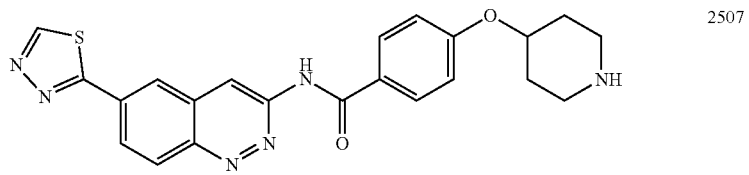
2507
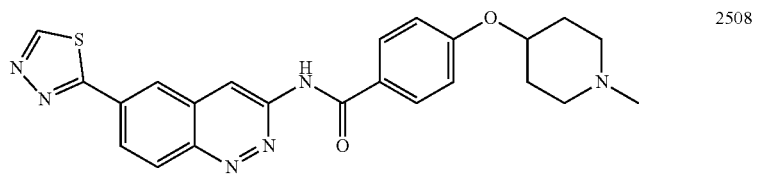
2508
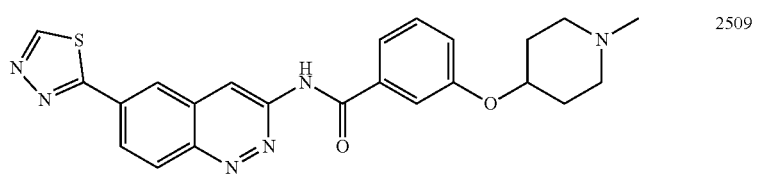
2509
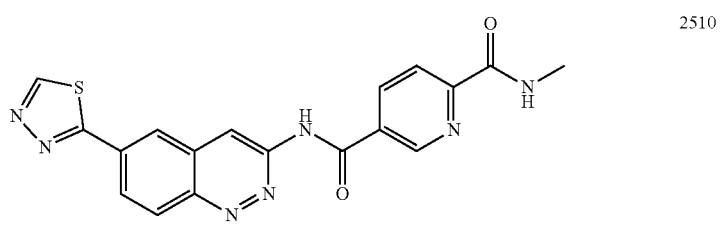
2510
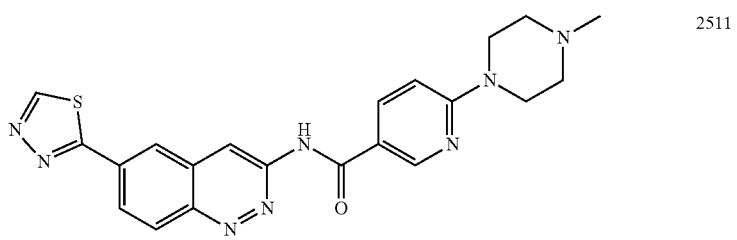
2511
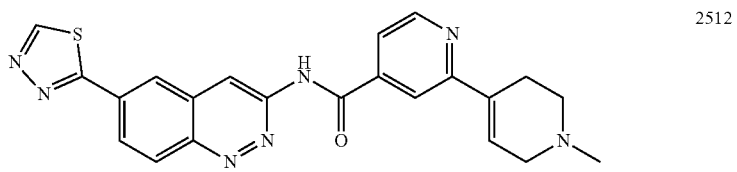
2512
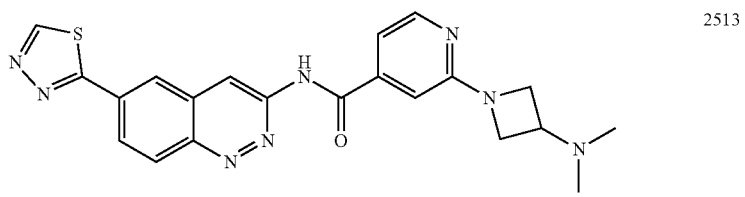
2513

TABLE 1-continued
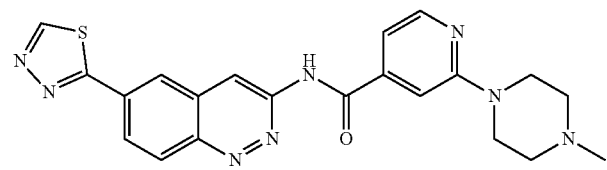 [SMILES: CN1CCN(c2cc(C(=O)Nc3cc4cc(-c5nncs5)ccc4nn3)ccn2)CC1] 2514
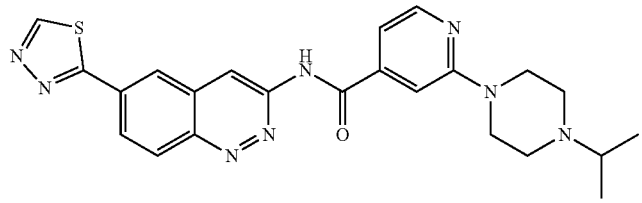 [SMILES: CC(C)N1CCN(c2cc(C(=O)Nc3cc4cc(-c5nncs5)ccc4nn3)ccn2)CC1] 2515
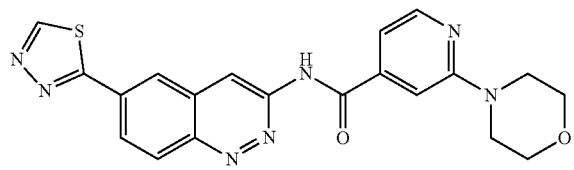 [SMILES: O=C(Nc1cc2cc(-c3nncs3)ccc2nn1)c1ccnc(N2CCOCC2)c1] 2516
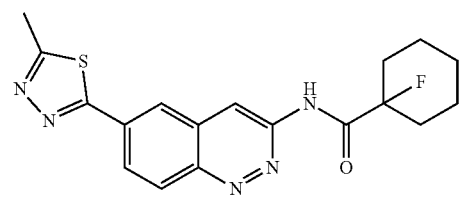 2517
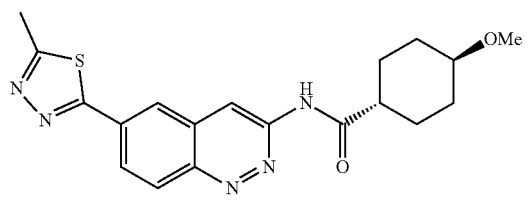 [SMILES: CO[C@H]1CC[C@H](C(=O)Nc2cc3cc(-c4nnc(C)s4)ccc3nn2)CC1] 2518
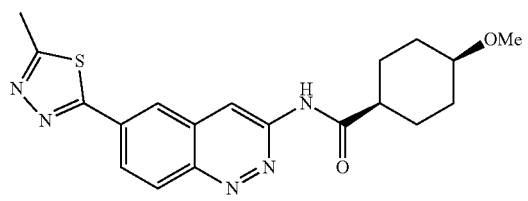 [SMILES: CO[C@H]1CC[C@@H](C(=O)Nc2cc3cc(-c4nnc(C)s4)ccc3nn2)CC1] 2519
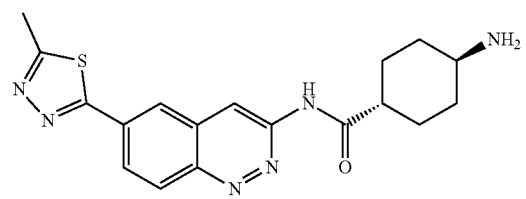 [SMILES: Cc1nnc(-c2ccc3nnc(NC(=O)[C@H]4CC[C@H](N)CC4)cc3c2)s1] 2520
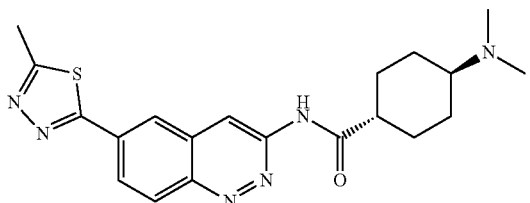 2521

TABLE 1-continued
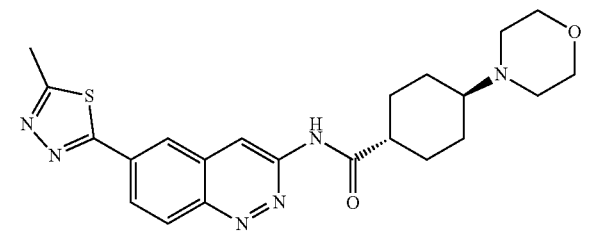 [SMILES: Cc1nnc(-c2ccc3nnc(NC(=O)[C@H]4CC[C@H](N5CCOCC5)CC4)cc3c2)s1] 2522
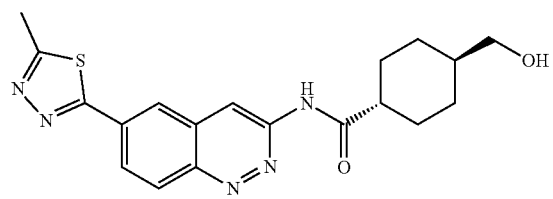 [SMILES: Cc1nnc(-c2ccc3nnc(NC(=O)[C@H]4CC[C@H](CO)CC4)cc3c2)s1] 2523
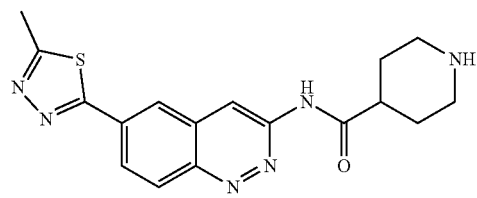 [SMILES: Cc1nnc(-c2ccc3nnc(NC(=O)C4CCNCC4)cc3c2)s1] 2524
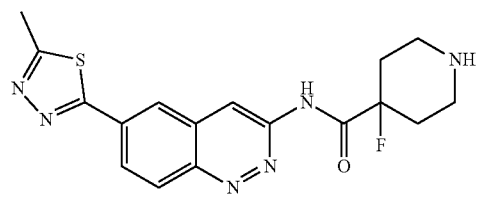 [SMILES: Cc1nnc(-c2ccc3nnc(NC(=O)C4(F)CCNCC4)cc3c2)s1] 2525
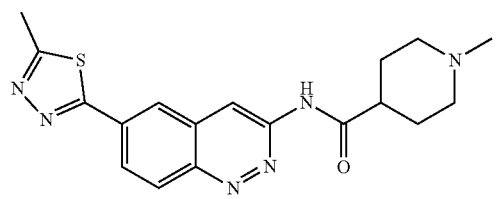 [SMILES: Cc1nnc(-c2ccc3nnc(NC(=O)C4CCN(C)CC4)cc3c2)s1] 2526
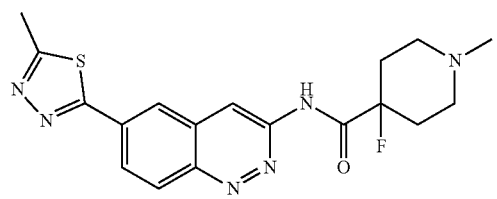 2527
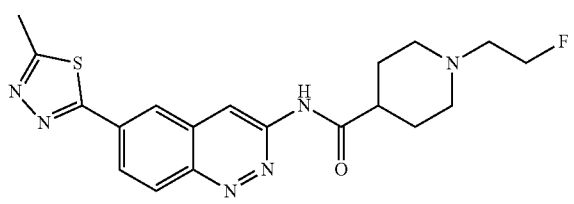 [SMILES: Cc1nnc(-c2ccc3nnc(NC(=O)C4CCN(CCF)CC4)cc3c2)s1] 2528
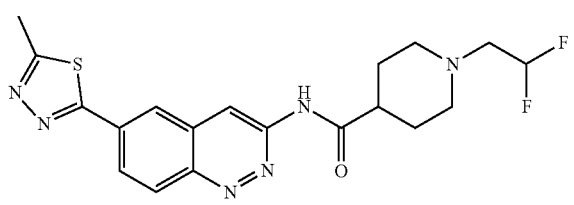 2529

TABLE 1-continued
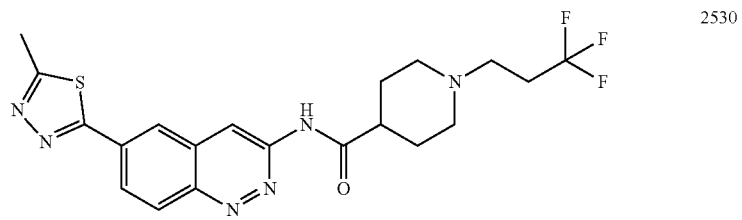 2530
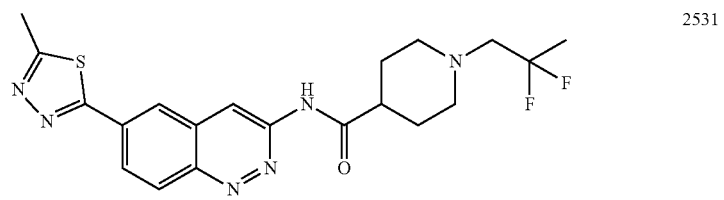 2531
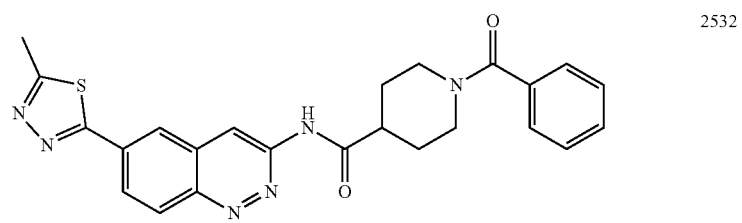 2532
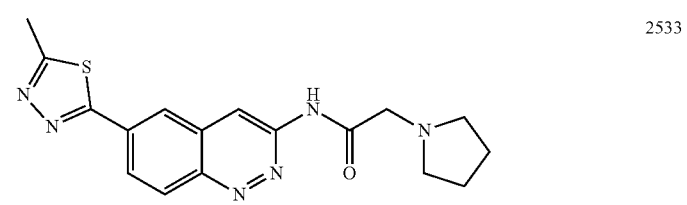 2533
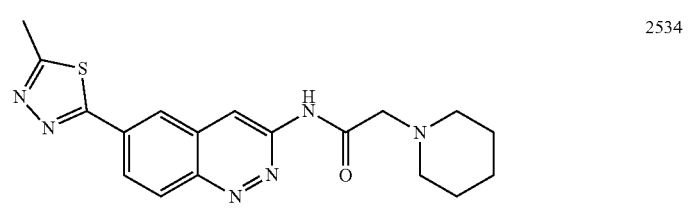 2534
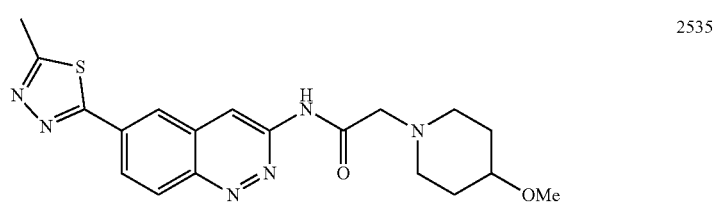 2535
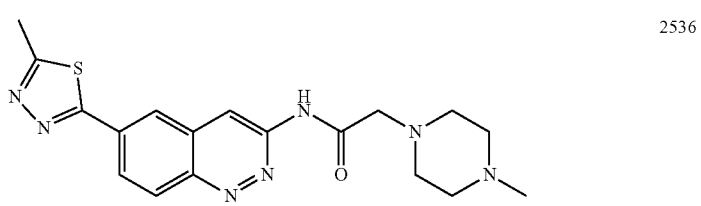 2536

TABLE 1-continued
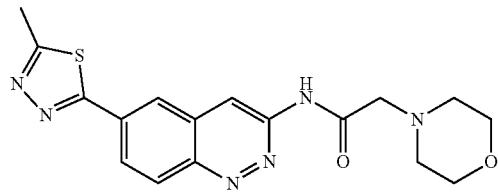
2537
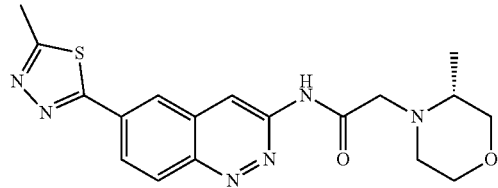 [SMILES: Cc1nnc(-c2ccc3nnc(NC(=O)CN4CCOC[C@H]4C)cc3c2)s1]
2538
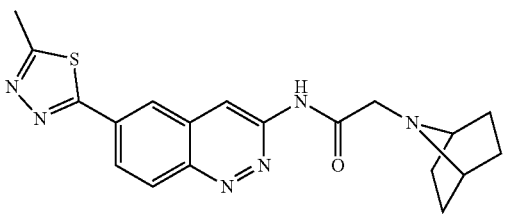 [SMILES: Cc1nnc(-c2ccc3nnc(NC(=O)CN4C5CCC4CC5)cc3c2)s1]
2539
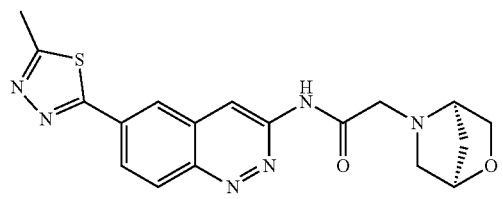 [SMILES: Cc1nnc(-c2ccc3nnc(NC(=O)CN4C[C@H]5C[C@@H]4CO5)cc3c2)s1]
2540
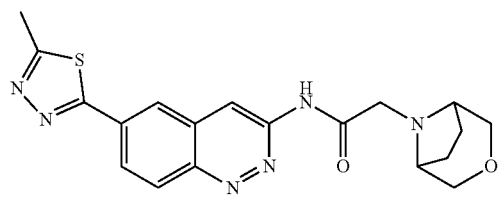 [SMILES: Cc1nnc(-c2ccc3nnc(NC(=O)CN4C5CCC4COC5)cc3c2)s1]
2541
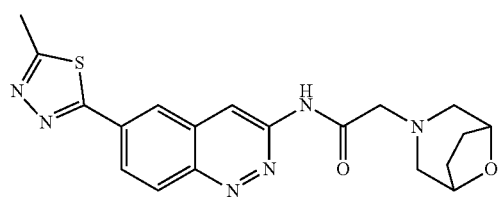 [SMILES: Cc1nnc(-c2ccc3nnc(NC(=O)CN4CC5CCC(C4)O5)cc3c2)s1]
2542
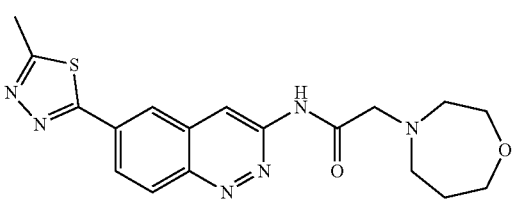 [SMILES: Cc1nnc(-c2ccc3nnc(NC(=O)CN4CCCOCC4)cc3c2)s1]
2543
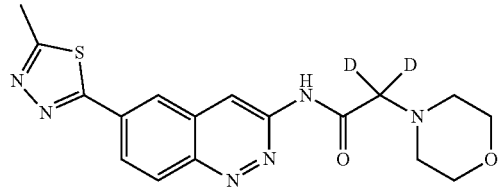 [SMILES: [2H]C([2H])(C(=O)Nc1cc2cc(-c3nnc(C)s3)ccc2nn1)N1CCOCC1]
2544

TABLE 1-continued
| | |
|---|---|
| 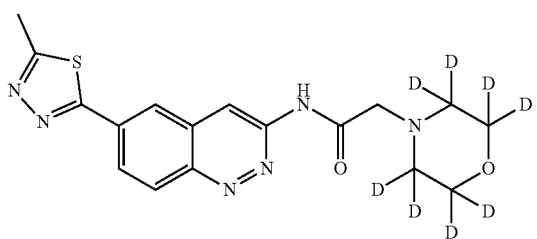 [SMILES: [2H]C1([2H])OC([2H])([2H])C([2H])([2H])N(CC(=O)Nc2cc3cc(-c4nnc(C)s4)ccc3nn2)C1([2H])[2H]] | 2545 |
| 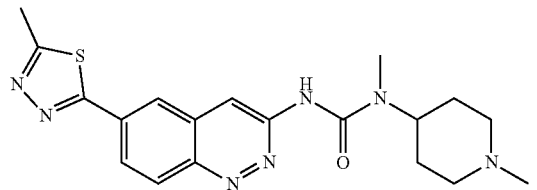 [SMILES: Cc1nnc(-c2ccc3nnc(NC(=O)N(C)C4CCN(C)CC4)cc3c2)s1] | 2546 |
| 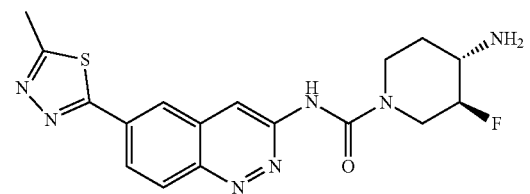 | 2547 |
| 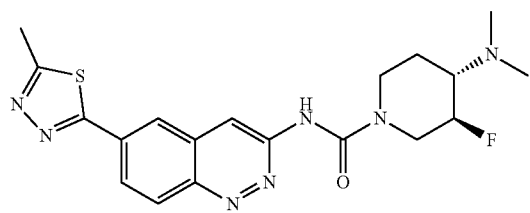 [SMILES: Cc1nnc(-c2ccc3nnc(NC(=O)N4CC[C@H](N(C)C)[C@@H](F)C4)cc3c2)s1] | 2548 |
| 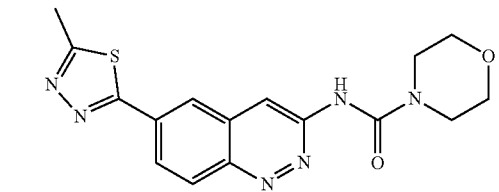 [SMILES: Cc1nnc(-c2ccc3nnc(NC(=O)N4CCOCC4)cc3c2)s1] | 2549 |
| 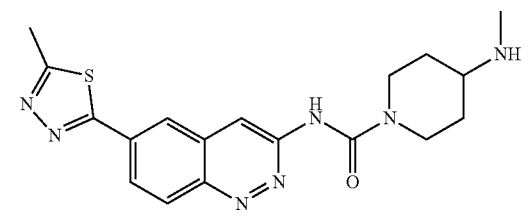 [SMILES: CNC1CCN(C(=O)Nc2cc3cc(-c4nnc(C)s4)ccc3nn2)CC1] | 2550 |
| 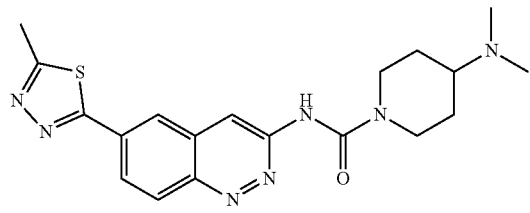 [SMILES: Cc1nnc(-c2ccc3nnc(NC(=O)N4CCC(N(C)C)CC4)cc3c2)s1] | 2551 |

TABLE 1-continued
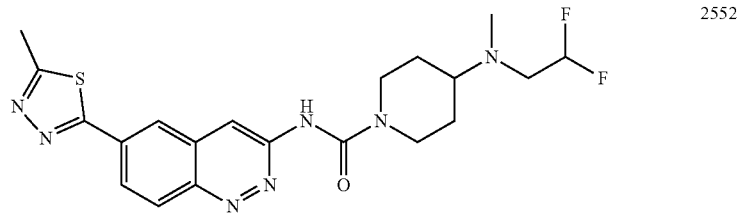 2552
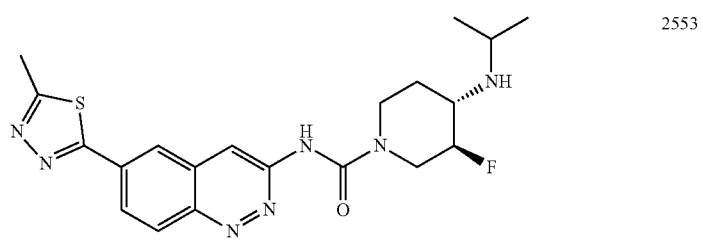 2553
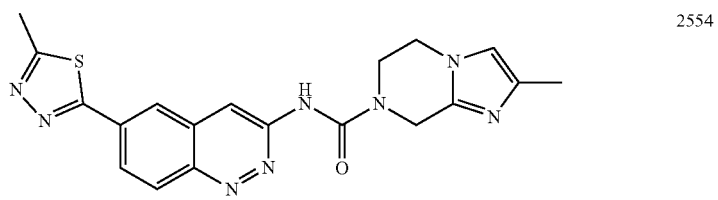 2554
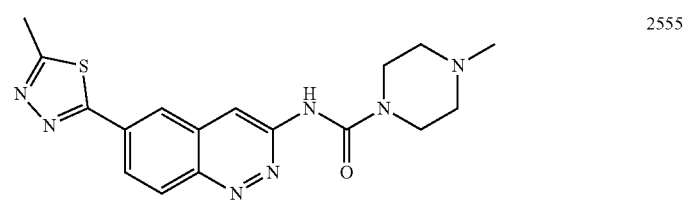 2555
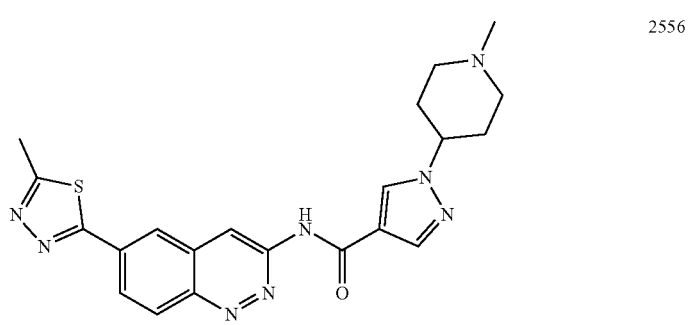 2556
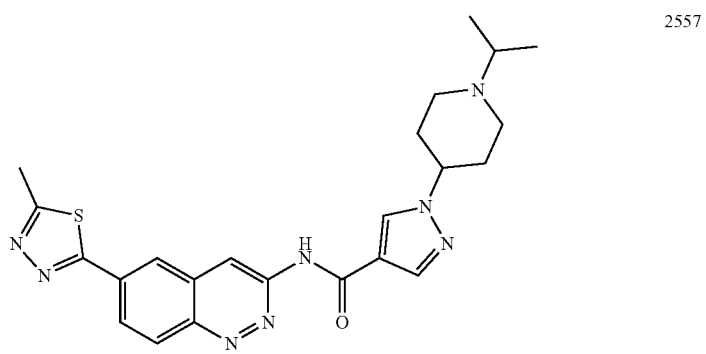 2557

TABLE 1-continued
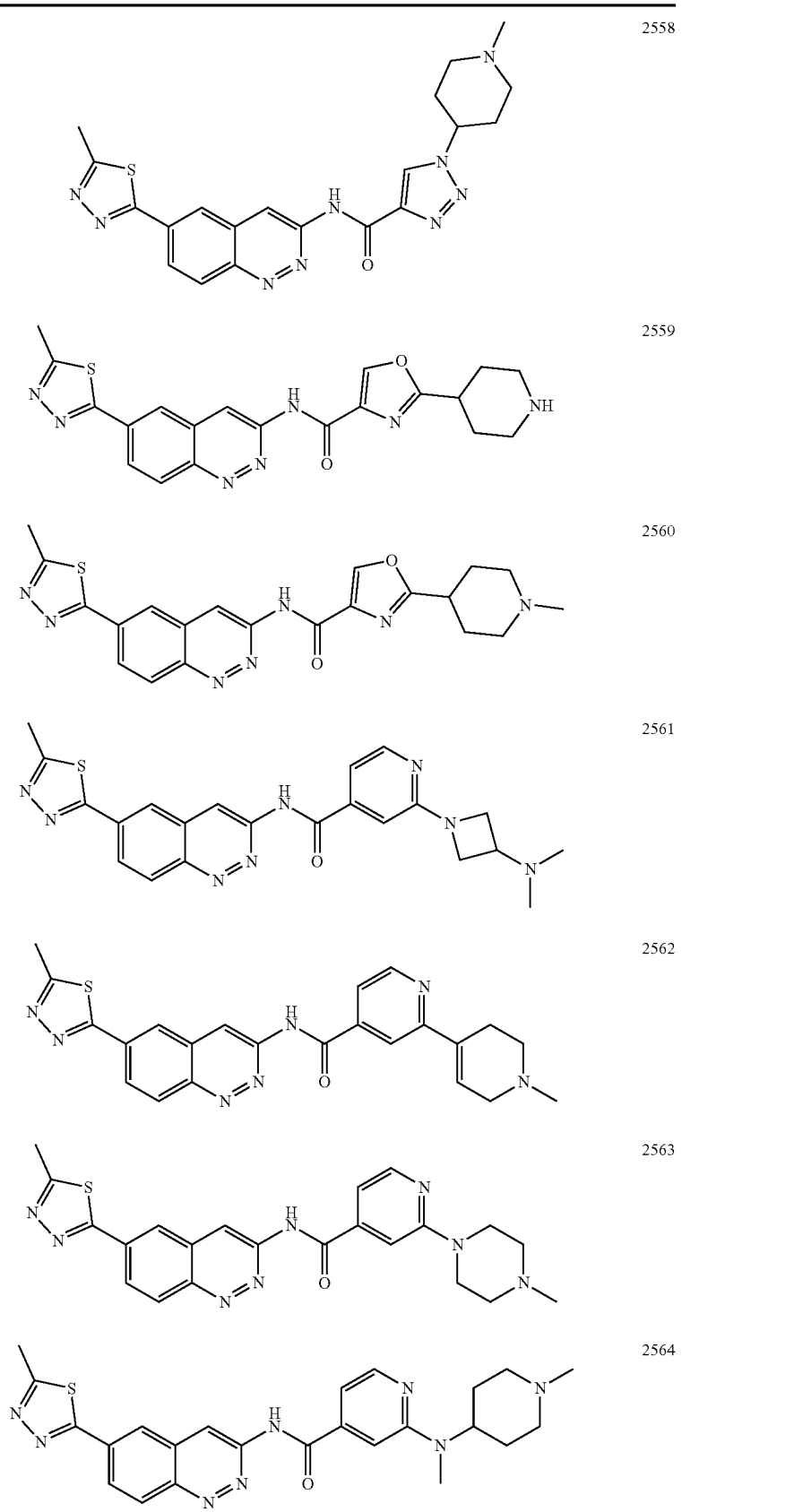

TABLE 1-continued
| | |
|---|---|
| 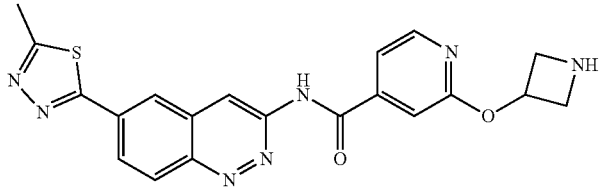 [SMILES: Cc1nnc(-c2ccc3nnc(NC(=O)c4ccnc(OC5CNC5)c4)cc3c2)s1] | 2565 |
| 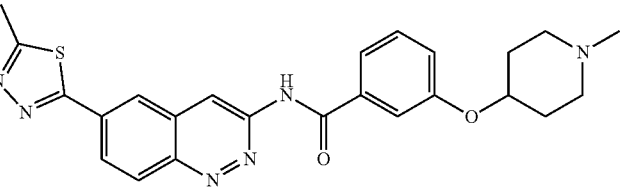 | 2566 |
| 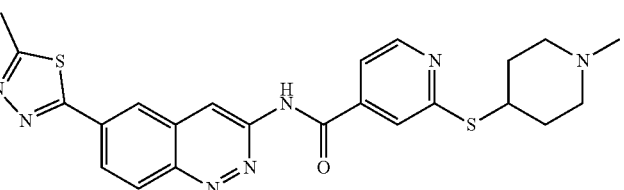 | 2567 |
| 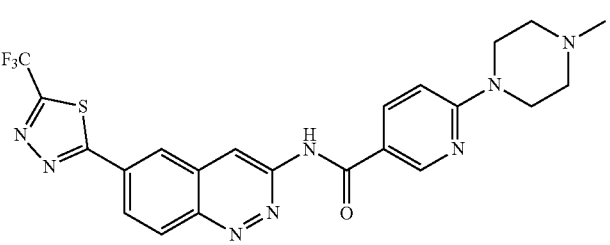 [SMILES: CN1CCN(c2ccc(C(=O)Nc3cc4cc(-c5nnc(C(F)(F)F)s5)ccc4nn3)cn2)CC1] | 2568 |
| 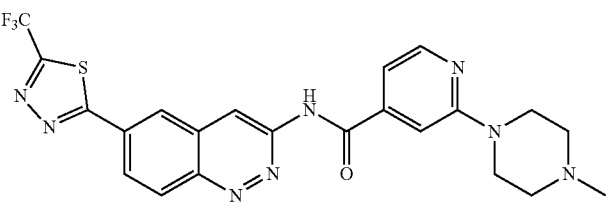 [SMILES: CN1CCN(c2cc(C(=O)Nc3cc4cc(-c5nnc(C(F)(F)F)s5)ccc4nn3)ccn2)CC1] | 2569 |
| 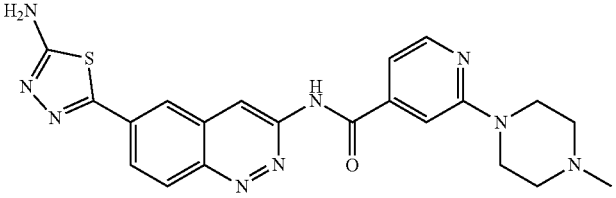 | 2570 |
| 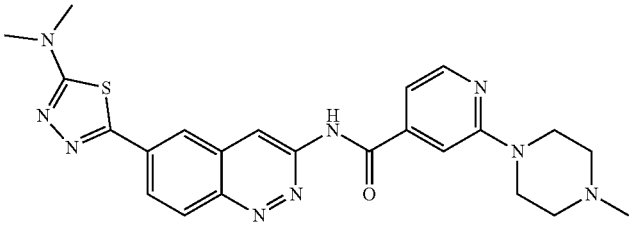 | 2571 |

TABLE 1-continued
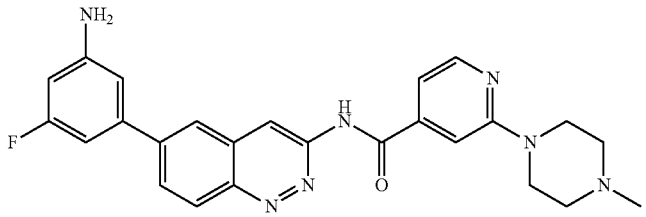 [SMILES: CN1CCN(c2cc(C(=O)Nc3cc4cc(-c5cc(N)cc(F)c5)ccc4nn3)ccn2)CC1] 2572
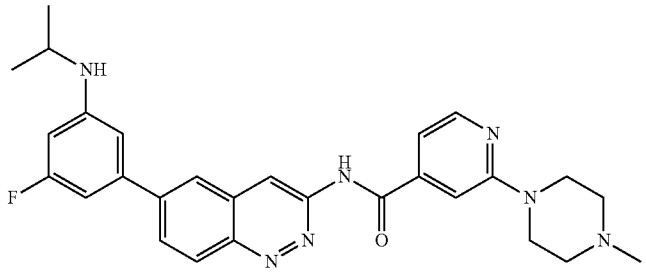 [SMILES: CC(C)Nc1cc(F)cc(-c2ccc3nnc(NC(=O)c4ccnc(N5CCN(C)CC5)c4)cc3c2)c1] 2573
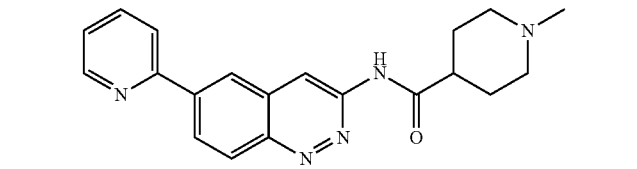 [SMILES: CN1CCC(C(=O)Nc2cc3cc(-c4ccccn4)ccc3nn2)CC1] 2574
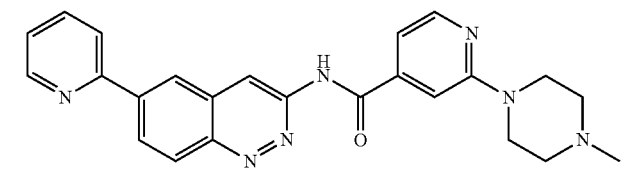 [SMILES: CN1CCN(c2cc(C(=O)Nc3cc4cc(-c5ccccn5)ccc4nn3)ccn2)CC1] 2575
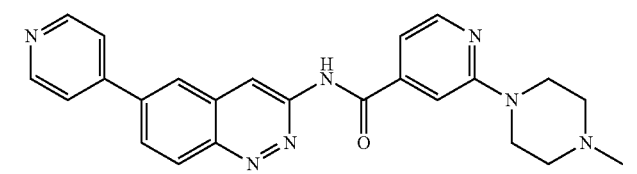 [SMILES: CN1CCN(c2cc(C(=O)Nc3cc4cc(-c5ccncc5)ccc4nn3)ccn2)CC1] 2576
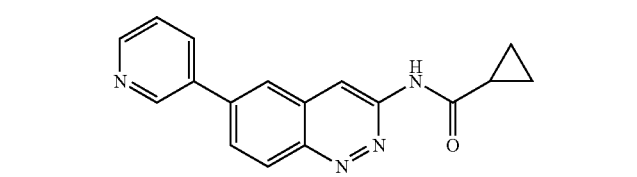 [SMILES: O=C(Nc1cc2cc(-c3cccnc3)ccc2nn1)C1CC1] 2577
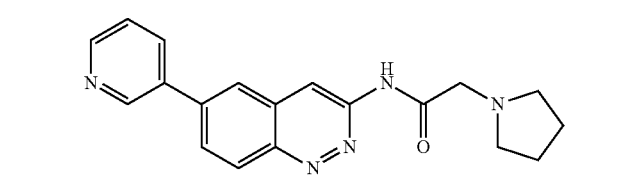 [SMILES: O=C(CN1CCCC1)Nc1cc2cc(-c3cccnc3)ccc2nn1] 2578
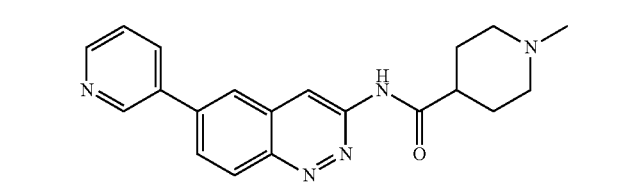 [SMILES: CN1CCC(C(=O)Nc2cc3cc(-c4cccnc4)ccc3nn2)CC1] 2579

TABLE 1-continued
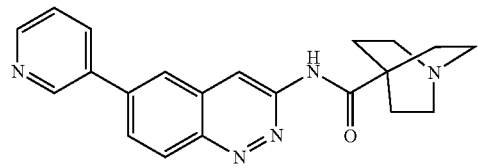 [SMILES: O=C(Nc1cc2cc(-c3cccnc3)ccc2nn1)C12CCN(CC1)CC2] 2580
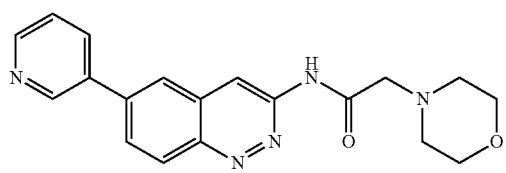 [SMILES: O=C(CN1CCOCC1)Nc1cc2cc(-c3cccnc3)ccc2nn1] 2581
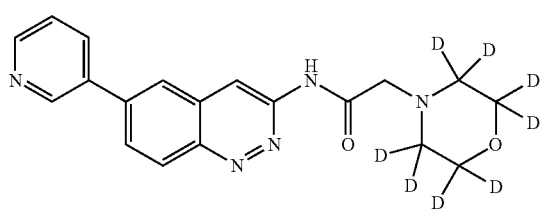 [SMILES: [2H]C1([2H])OC([2H])([2H])C([2H])([2H])N(CC(=O)Nc2cc3cc(-c4cccnc4)ccc3nn2)C1([2H])[2H]] 2582
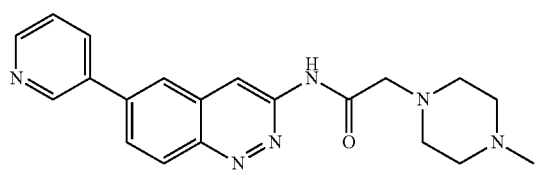 [SMILES: CN1CCN(CC(=O)Nc2cc3cc(-c4cccnc4)ccc3nn2)CC1] 2583
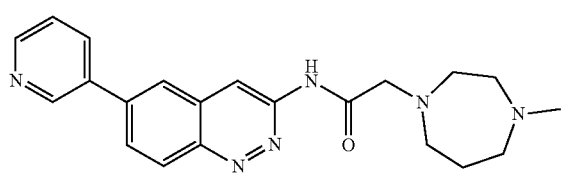 [SMILES: CN1CCCN(CC(=O)Nc2cc3cc(-c4cccnc4)ccc3nn2)CC1] 2584
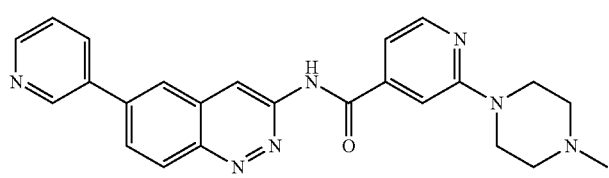 [SMILES: CN1CCN(c2cc(C(=O)Nc3cc4cc(-c5cccnc5)ccc4nn3)ccn2)CC1] 2585
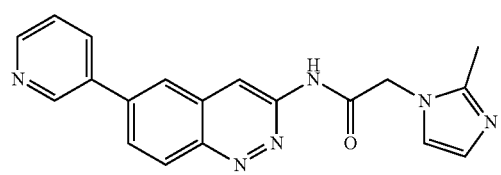 [SMILES: Cc1nccn1CC(=O)Nc1cc2cc(-c3cccnc3)ccc2nn1] 2586
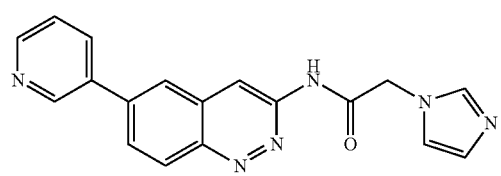 [SMILES: O=C(Cn1ccnc1)Nc1cc2cc(-c3cccnc3)ccc2nn1] 2587

TABLE 1-continued

| | |
|---|---|
| (structure) | 2588 |
| (structure) | 2589 |
| (structure) | 2590 |
| (structure) | 2591 |
| (structure) | 2592 |
| (structure) | 2593 |

TABLE 1-continued
| | |
|---|---|
| 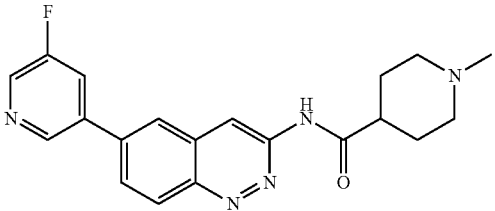 [SMILES: CN1CCC(C(=O)Nc2cc3cc(-c4cncc(F)c4)ccc3nn2)CC1] | 2594 |
| 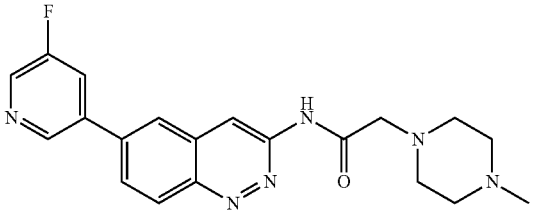 [SMILES: CN1CCN(CC(=O)Nc2cc3cc(-c4cncc(F)c4)ccc3nn2)CC1] | 2595 |
| 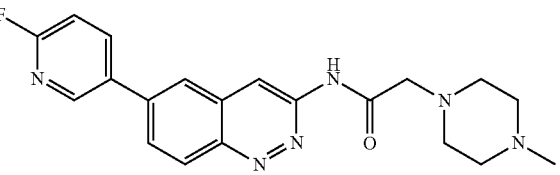 | 2596 |
| 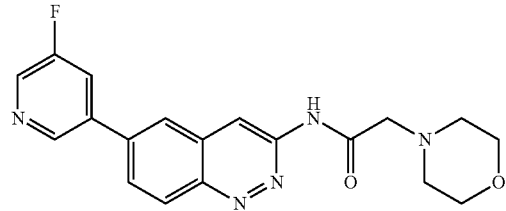 [SMILES: O=C(CN1CCOCC1)Nc1cc2cc(-c3cncc(F)c3)ccc2nn1] | 2597 |
| 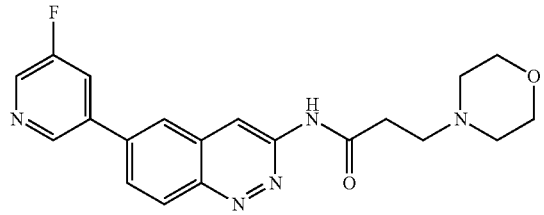 | 2598 |
| 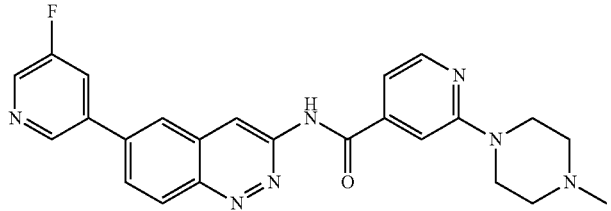 [SMILES: CN1CCN(c2cc(C(=O)Nc3cc4cc(-c5cncc(F)c5)ccc4nn3)ccn2)CC1] | 2599 |
| 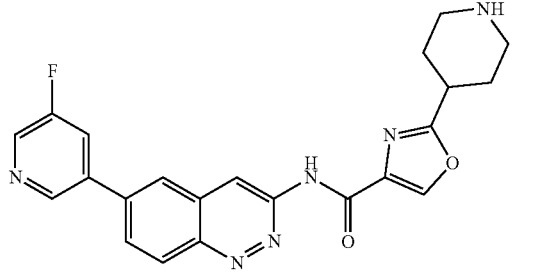 [SMILES: O=C(Nc1cc2cc(-c3cncc(F)c3)ccc2nn1)c1coc(C2CCNCC2)n1] | 2600 |

TABLE 1-continued
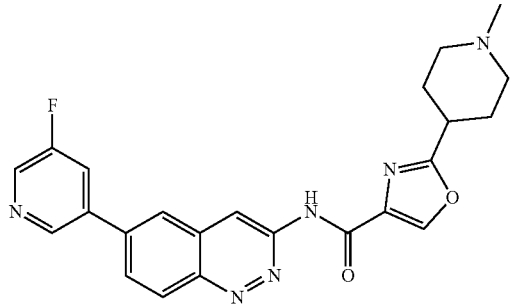 [SMILES: CN1CCC(c2nc(C(=O)Nc3cc4cc(-c5cncc(F)c5)ccc4nn3)co2)CC1] 2601
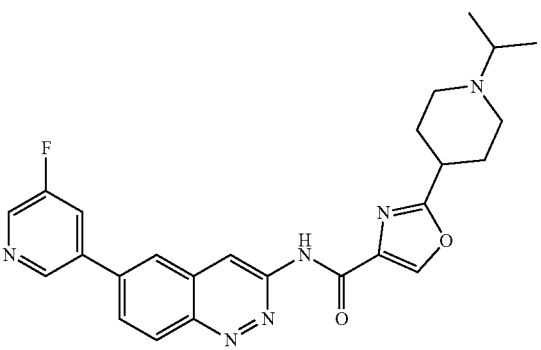 [SMILES: CC(C)N1CCC(c2nc(C(=O)Nc3cc4cc(-c5cncc(F)c5)ccc4nn3)co2)CC1] 2602
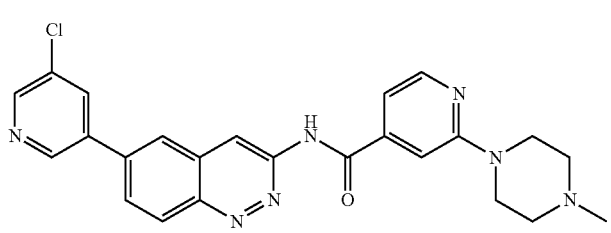 [SMILES: CN1CCN(c2cc(C(=O)Nc3cc4cc(-c5cncc(Cl)c5)ccc4nn3)ccn2)CC1] 2603
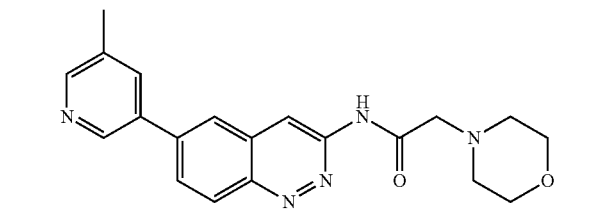 [SMILES: Cc1cncc(-c2ccc3nnc(NC(=O)CN4CCOCC4)cc3c2)c1] 2604
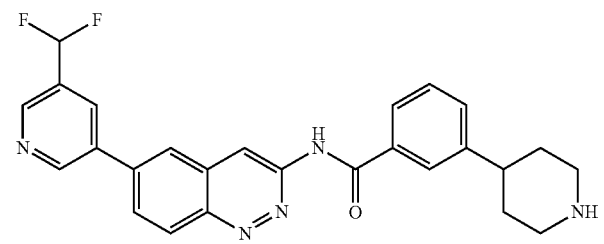 [SMILES: O=C(Nc1cc2cc(-c3cncc(C(F)F)c3)ccc2nn1)c1cccc(C2CCNCC2)c1] 2605
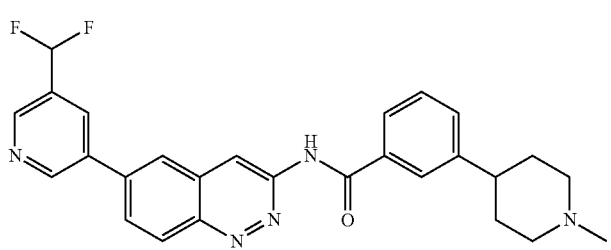 2606

TABLE 1-continued
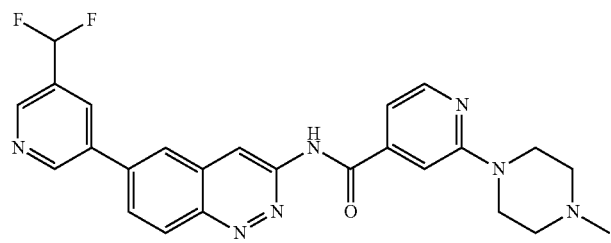 [SMILES: CN1CCN(c2cc(C(=O)Nc3cc4cc(-c5cncc(C(F)F)c5)ccc4nn3)ccn2)CC1]  2607
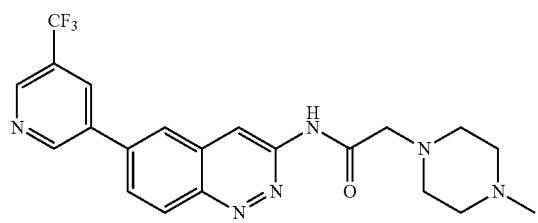 [SMILES: CN1CCN(CC(=O)Nc2cc3cc(-c4cncc(C(F)(F)F)c4)ccc3nn2)CC1]  2608
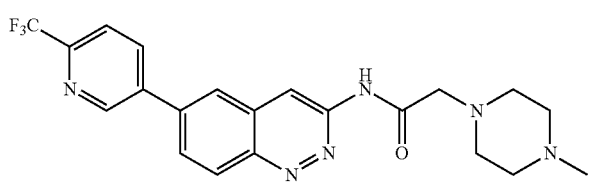 [SMILES: CN1CCN(CC(=O)Nc2cc3cc(-c4ccc(C(F)(F)F)nc4)ccc3nn2)CC1]  2609
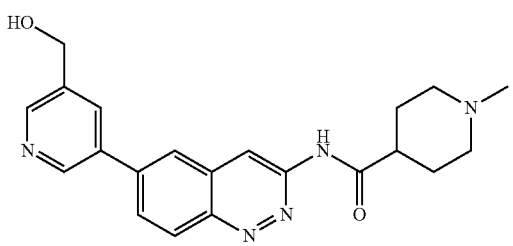 [SMILES: CN1CCC(C(=O)Nc2cc3cc(-c4cncc(CO)c4)ccc3nn2)CC1]  2610
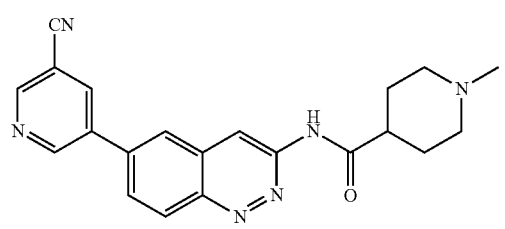 [SMILES: CN1CCC(C(=O)Nc2cc3cc(-c4cncc(C#N)c4)ccc3nn2)CC1]  2611
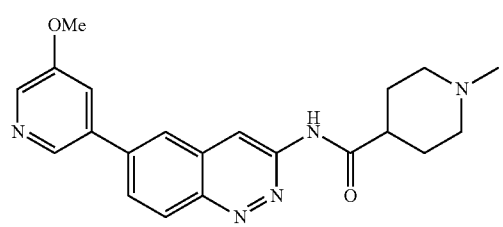 [SMILES: COc1cncc(-c2ccc3nnc(NC(=O)C4CCN(C)CC4)cc3c2)c1]  2612
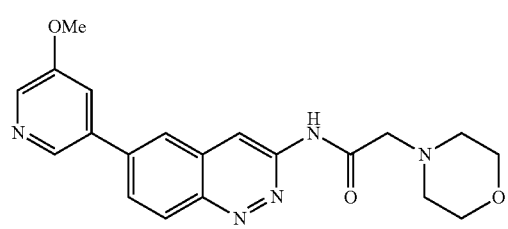 [SMILES: COc1cncc(-c2ccc3nnc(NC(=O)CN4CCOCC4)cc3c2)c1]  2613

TABLE 1-continued
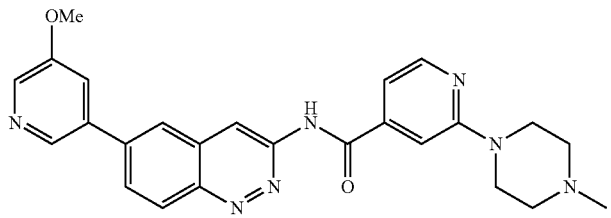 2614
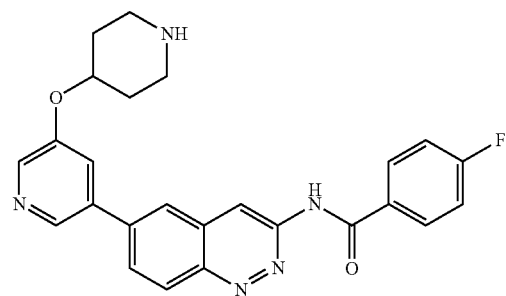 [SMILES: O=C(Nc1cc2cc(-c3cncc(OC4CCNCC4)c3)ccc2nn1)c1ccc(F)cc1] 2615
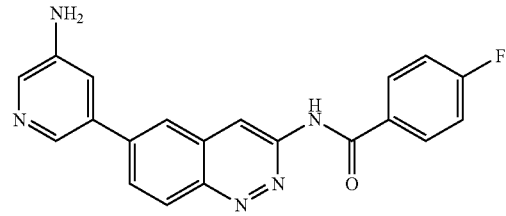 [SMILES: Nc1cncc(-c2ccc3nnc(NC(=O)c4ccc(F)cc4)cc3c2)c1] 2616
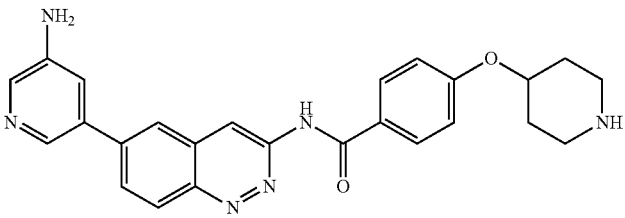 [SMILES: Nc1cncc(-c2ccc3nnc(NC(=O)c4ccc(OC5CCNCC5)cc4)cc3c2)c1] 2617
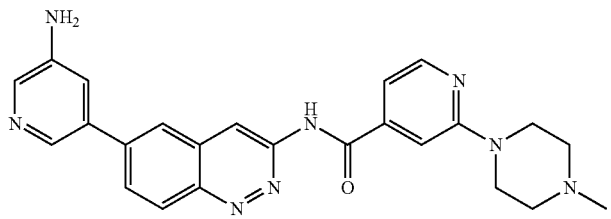 2618
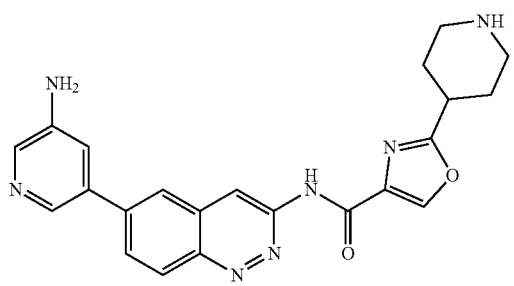 2619

TABLE 1-continued
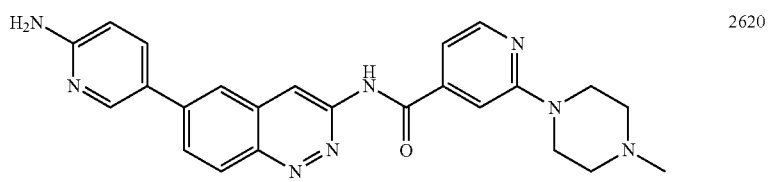
2620
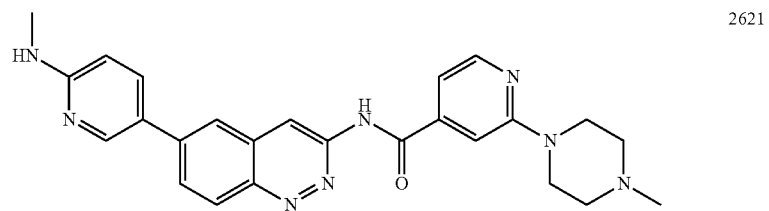
2621
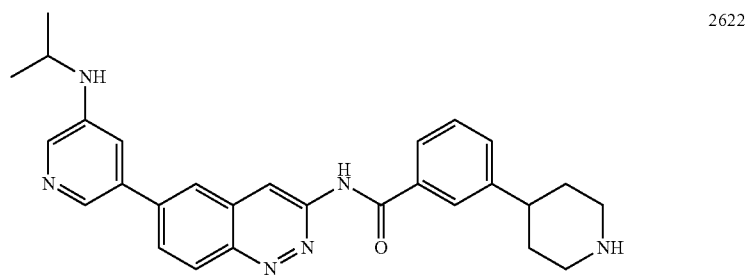
2622
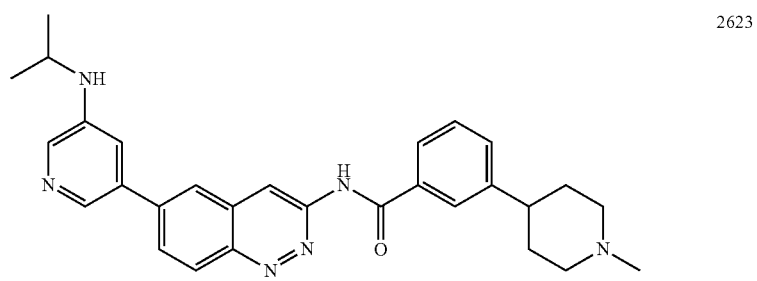
2623
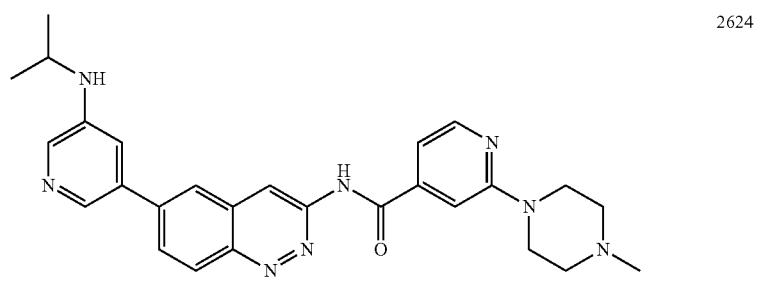
2624
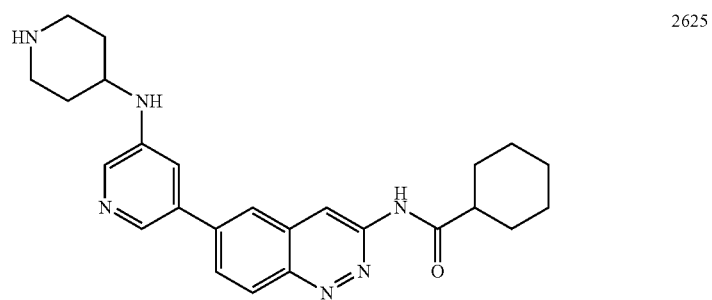
2625

TABLE 1-continued
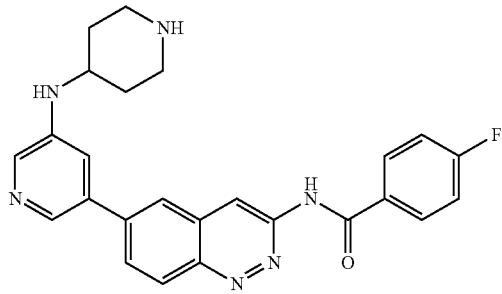 [SMILES: O=C(Nc1cc2cc(-c3cncc(NC4CCNCC4)c3)ccc2nn1)c1ccc(F)cc1] 2626
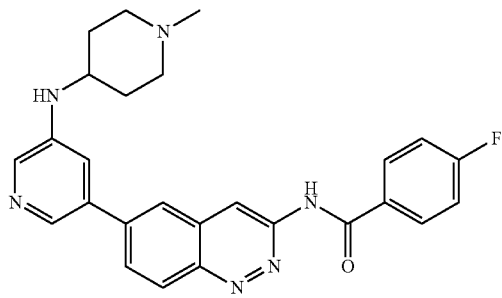 [SMILES: CN1CCC(Nc2cncc(-c3ccc4nnc(NC(=O)c5ccc(F)cc5)cc4c3)c2)CC1] 2627
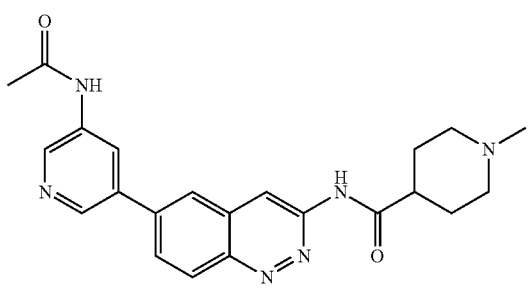 2628
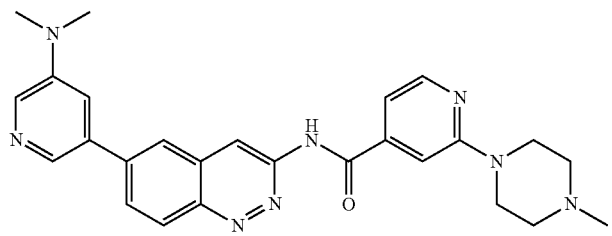 2629
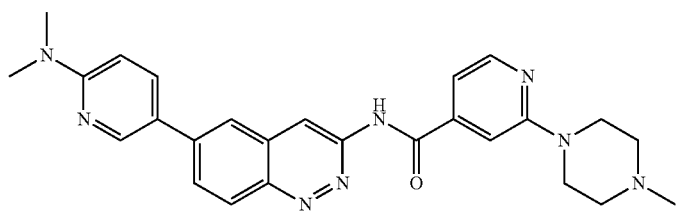 2630
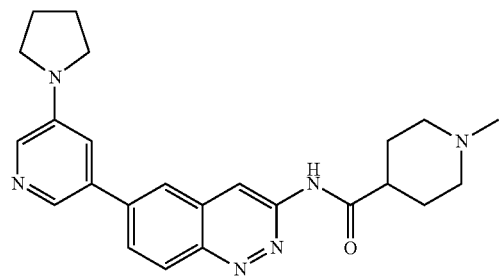 [SMILES: CN1CCC(C(=O)Nc2cc3cc(-c4cncc(N5CCCC5)c4)ccc3nn2)CC1] 2631

TABLE 1-continued
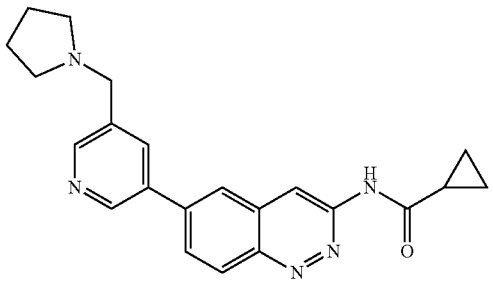 [SMILES: O=C(Nc1cc2cc(-c3cncc(CN4CCCC4)c3)ccc2nn1)C1CC1]
2632
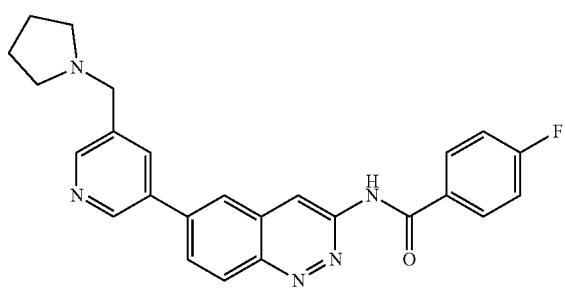 [SMILES: O=C(Nc1cc2cc(-c3cncc(CN4CCCC4)c3)ccc2nn1)c1ccc(F)cc1]
2633
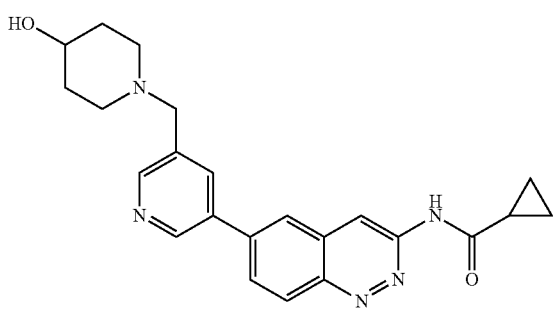 [SMILES: O=C(Nc1cc2cc(-c3cncc(CN4CCC(O)CC4)c3)ccc2nn1)C1CC1]
2634
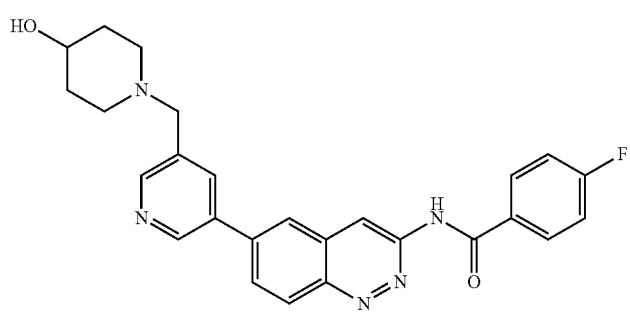 [SMILES: O=C(Nc1cc2cc(-c3cncc(CN4CCC(O)CC4)c3)ccc2nn1)c1ccc(F)cc1]
2635
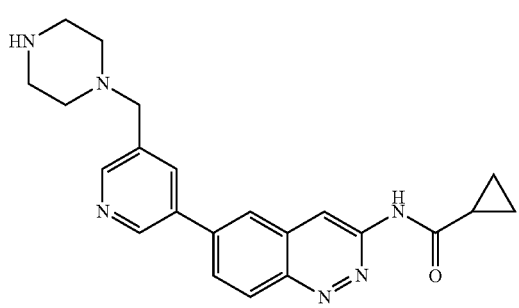 [SMILES: O=C(Nc1cc2cc(-c3cncc(CN4CCNCC4)c3)ccc2nn1)C1CC1]
2636

TABLE 1-continued
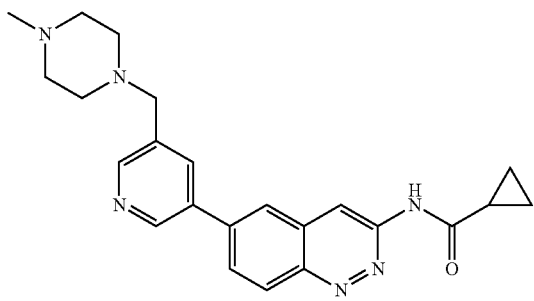 [SMILES: CN1CCN(Cc2cncc(-c3ccc4nnc(NC(=O)C5CC5)cc4c3)c2)CC1] 2637
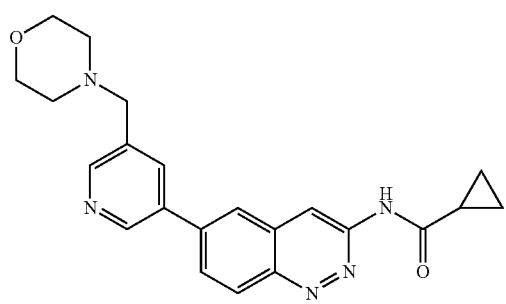 2638
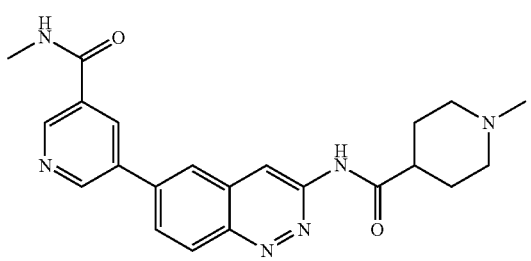 2639
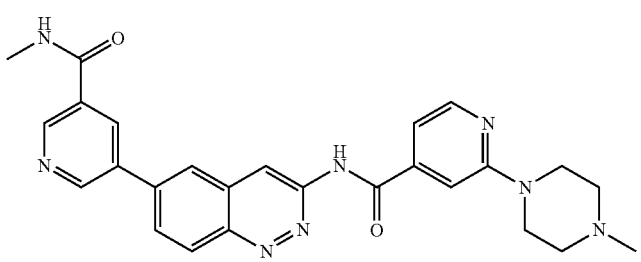 2640
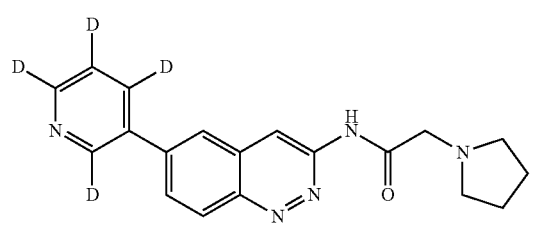 [SMILES: [2H]c1nc([2H])c(-c2ccc3nnc(NC(=O)CN4CCCC4)cc3c2)c([2H])c1[2H]] 2641
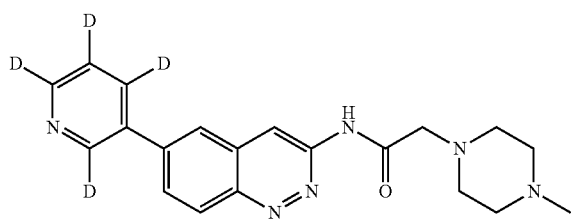 [SMILES: [2H]c1nc([2H])c(-c2ccc3nnc(NC(=O)CN4CCN(C)CC4)cc3c2)c([2H])c1[2H]] 2642

TABLE 1-continued
| | |
|---|---|
| 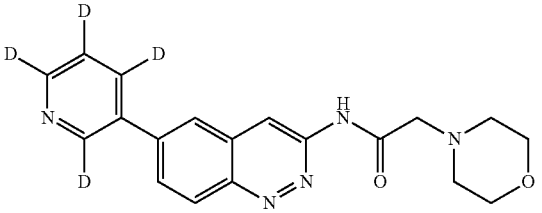 [SMILES: [2H]c1nc([2H])c(-c2ccc3nnc(NC(=O)CN4CCOCC4)cc3c2)c([2H])c1[2H]] | 2643 |
| 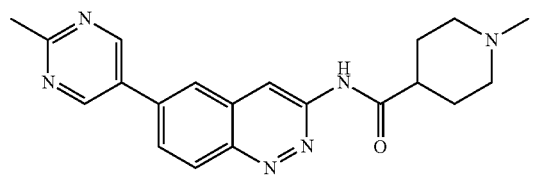 | 2644 |
| 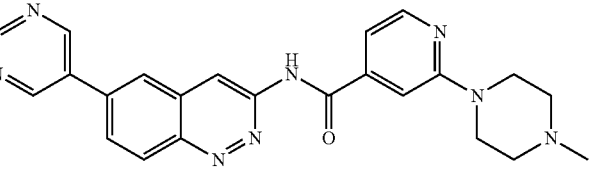 | 2645 |
| 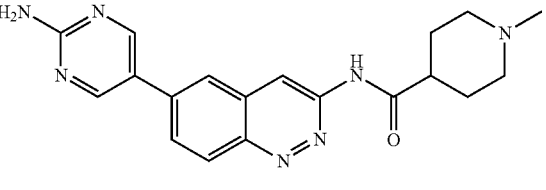 [SMILES: CN1CCC(C(=O)Nc2cc3cc(-c4cnc(N)nc4)ccc3nn2)CC1] | 2646 |
| 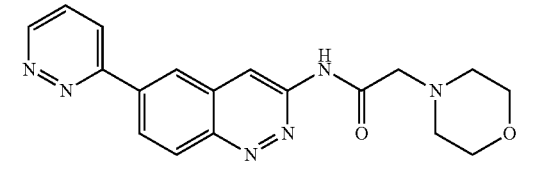 [SMILES: O=C(CN1CCOCC1)Nc1cc2cc(-c3cccnn3)ccc2nn1] | 2647 |
| 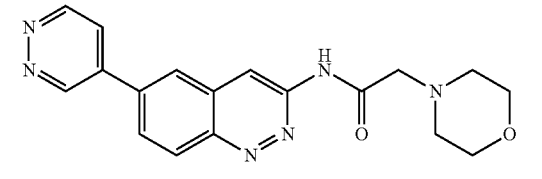 [SMILES: O=C(CN1CCOCC1)Nc1cc2cc(-c3ccnnc3)ccc2nn1] | 2648 |
| 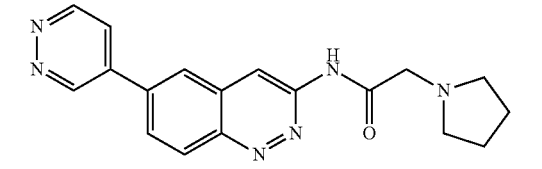 [SMILES: O=C(CN1CCCC1)Nc1cc2cc(-c3ccnnc3)ccc2nn1] | 2649 |
| 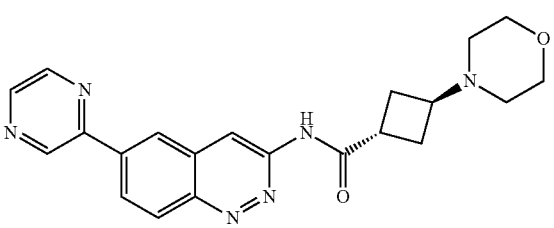 [SMILES: O=C(Nc1cc2cc(-c3cnccn3)ccc2nn1)[C@H]1C[C@H](N2CCOCC2)C1] | 2650 |

TABLE 1-continued
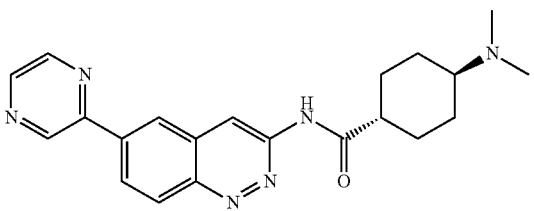 [SMILES: CN(C)[C@H]1CC[C@H](C(=O)Nc2cc3cc(-c4cnccn4)ccc3nn2)CC1] 2651
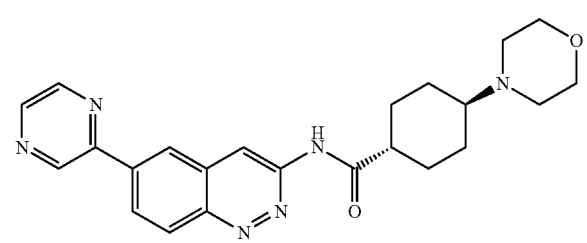 [SMILES: O=C(Nc1cc2cc(-c3cnccn3)ccc2nn1)[C@H]1CC[C@H](N2CCOCC2)CC1] 2652
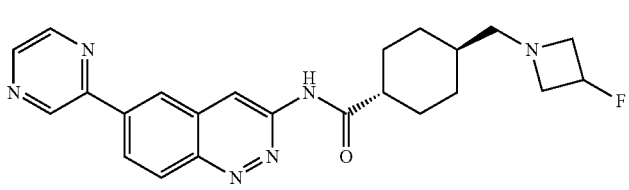 [SMILES: O=C(Nc1cc2cc(-c3cnccn3)ccc2nn1)[C@H]1CC[C@H](CN2CC(F)C2)CC1] 2653
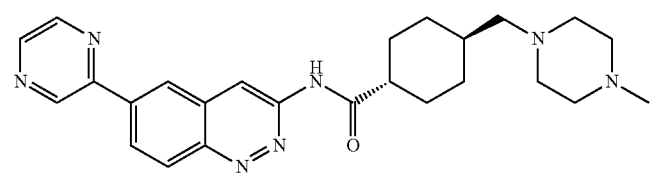 [SMILES: CN1CCN(C[C@H]2CC[C@H](C(=O)Nc3cc4cc(-c5cnccn5)ccc4nn3)CC2)CC1] 2654
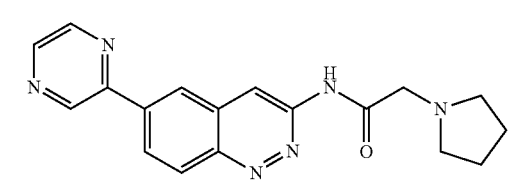 [SMILES: O=C(CN1CCCC1)Nc1cc2cc(-c3cnccn3)ccc2nn1] 2655
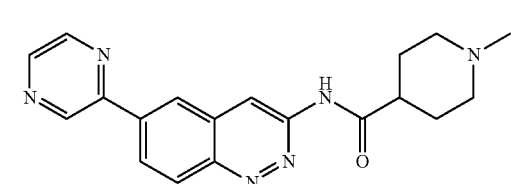 2656
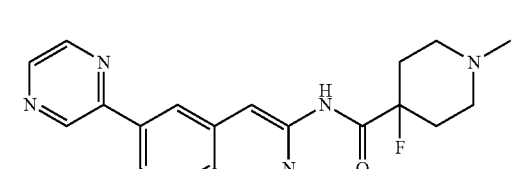 2657
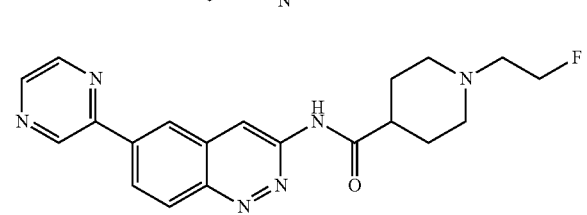 2658

TABLE 1-continued
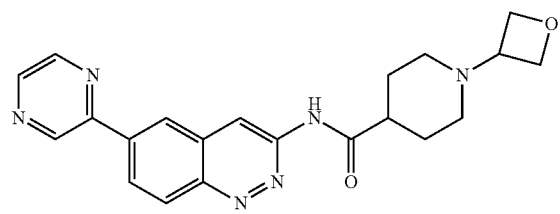 2659
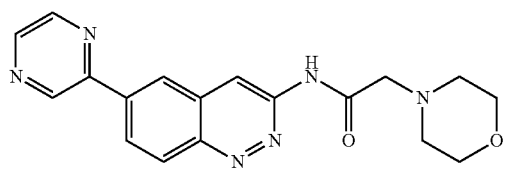 [SMILES: O=C(CN1CCOCC1)Nc1cc2cc(-c3cnccn3)ccc2nn1] 2660
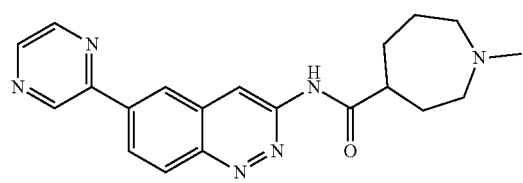 [SMILES: CN1CCCC(C(=O)Nc2cc3cc(-c4cnccn4)ccc3nn2)CC1] 2661
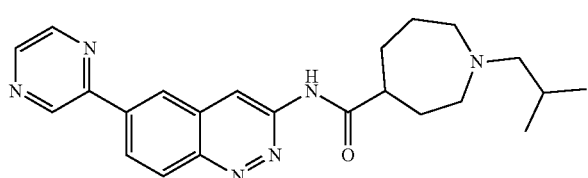 2662
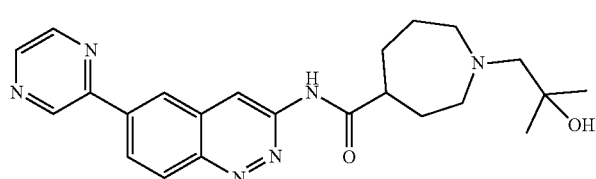 2663
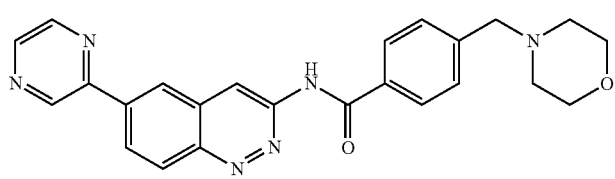 [SMILES: O=C(Nc1cc2cc(-c3cnccn3)ccc2nn1)c1ccc(CN2CCOCC2)cc1] 2664
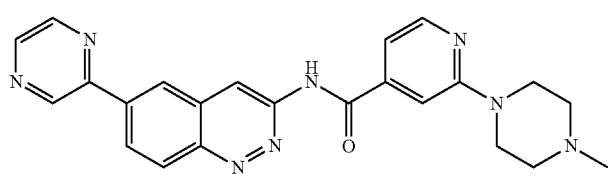 [SMILES: CN1CCN(c2cc(C(=O)Nc3cc4cc(-c5cnccn5)ccc4nn3)ccn2)CC1] 2665
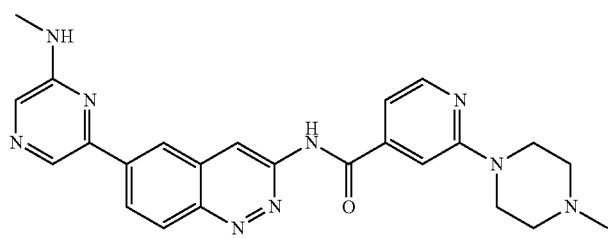 2666

TABLE 1-continued
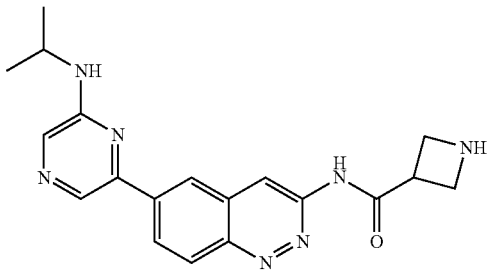 [SMILES: CC(C)Nc1cncc(-c2ccc3nnc(NC(=O)C4CNC4)cc3c2)n1]
2667
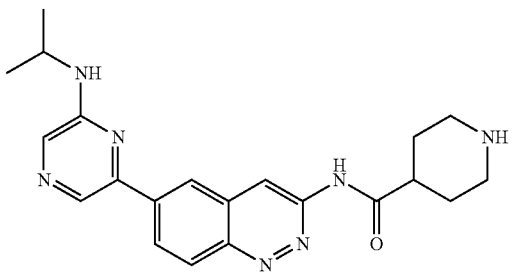 [SMILES: CC(C)Nc1cncc(-c2ccc3nnc(NC(=O)C4CCNCC4)cc3c2)n1]
2668
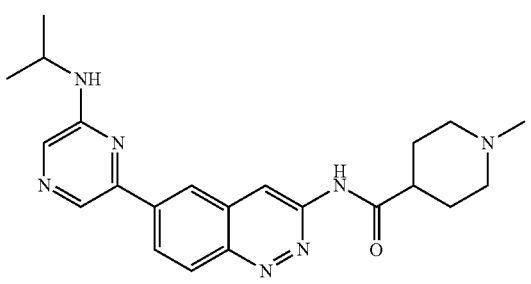 [SMILES: CC(C)Nc1cncc(-c2ccc3nnc(NC(=O)C4CCN(C)CC4)cc3c2)n1]
2669
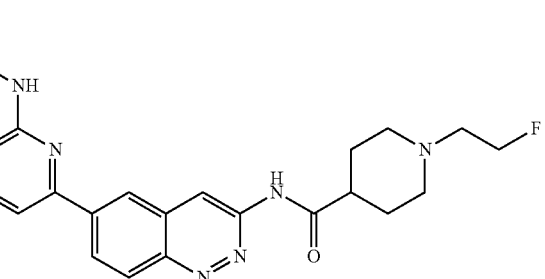
2670
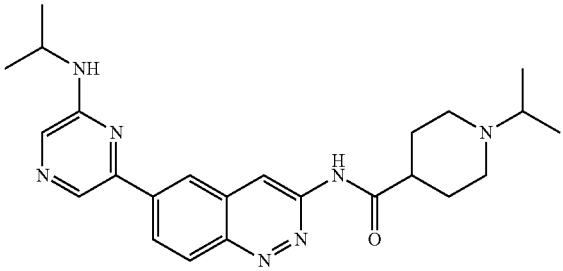 [SMILES: CC(C)Nc1cncc(-c2ccc3nnc(NC(=O)C4CCN(C(C)C)CC4)cc3c2)n1]
2671

TABLE 1-continued
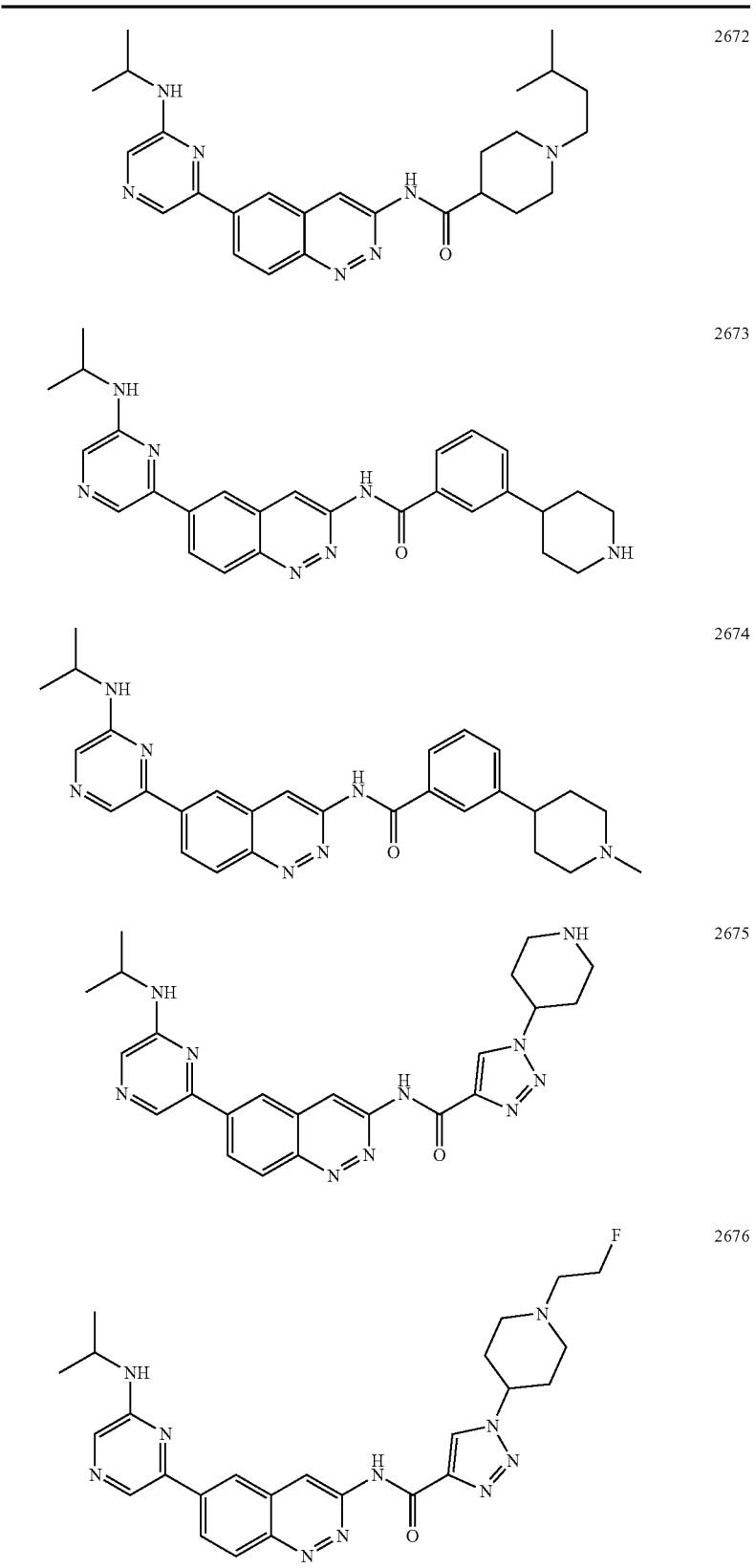

TABLE 1-continued
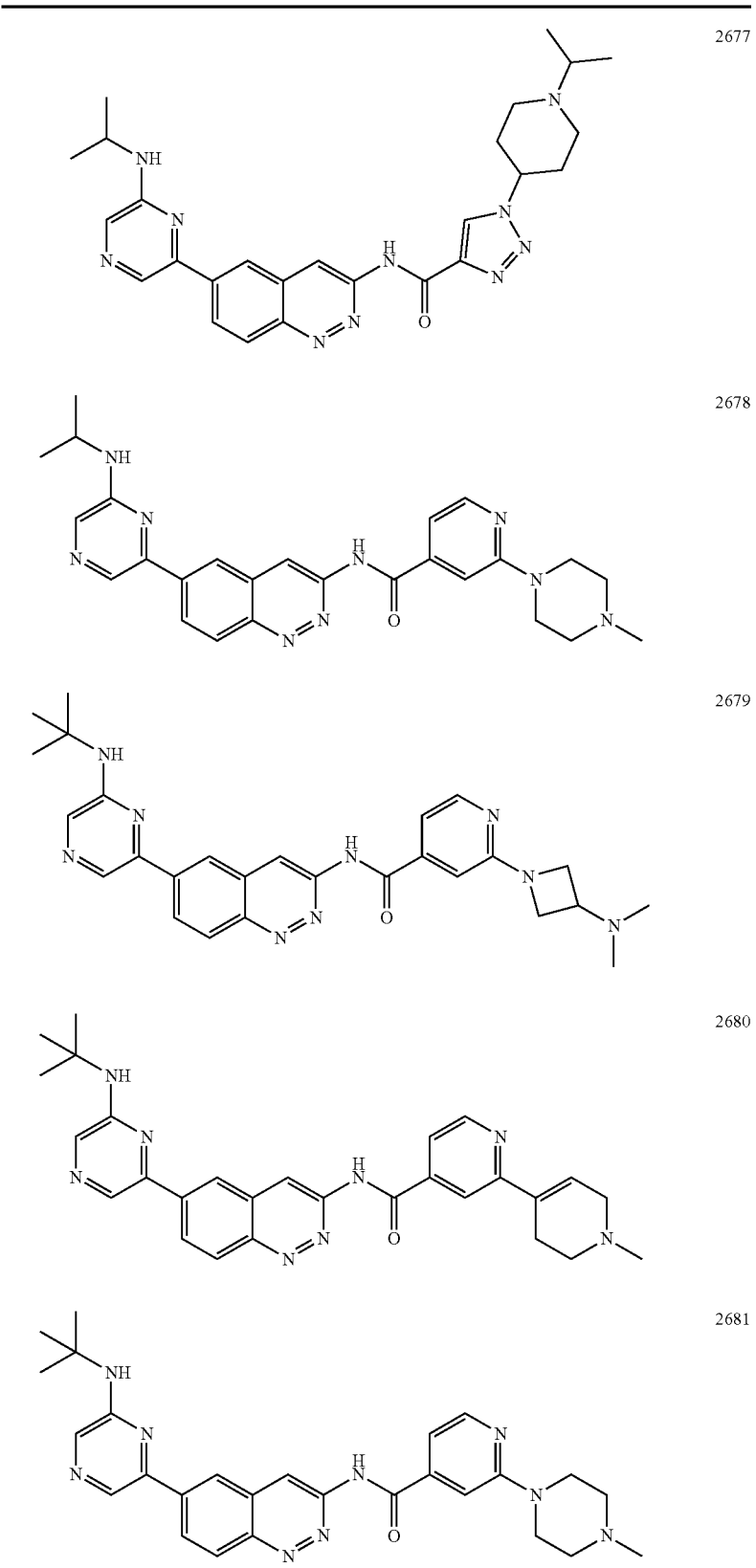

TABLE 1-continued
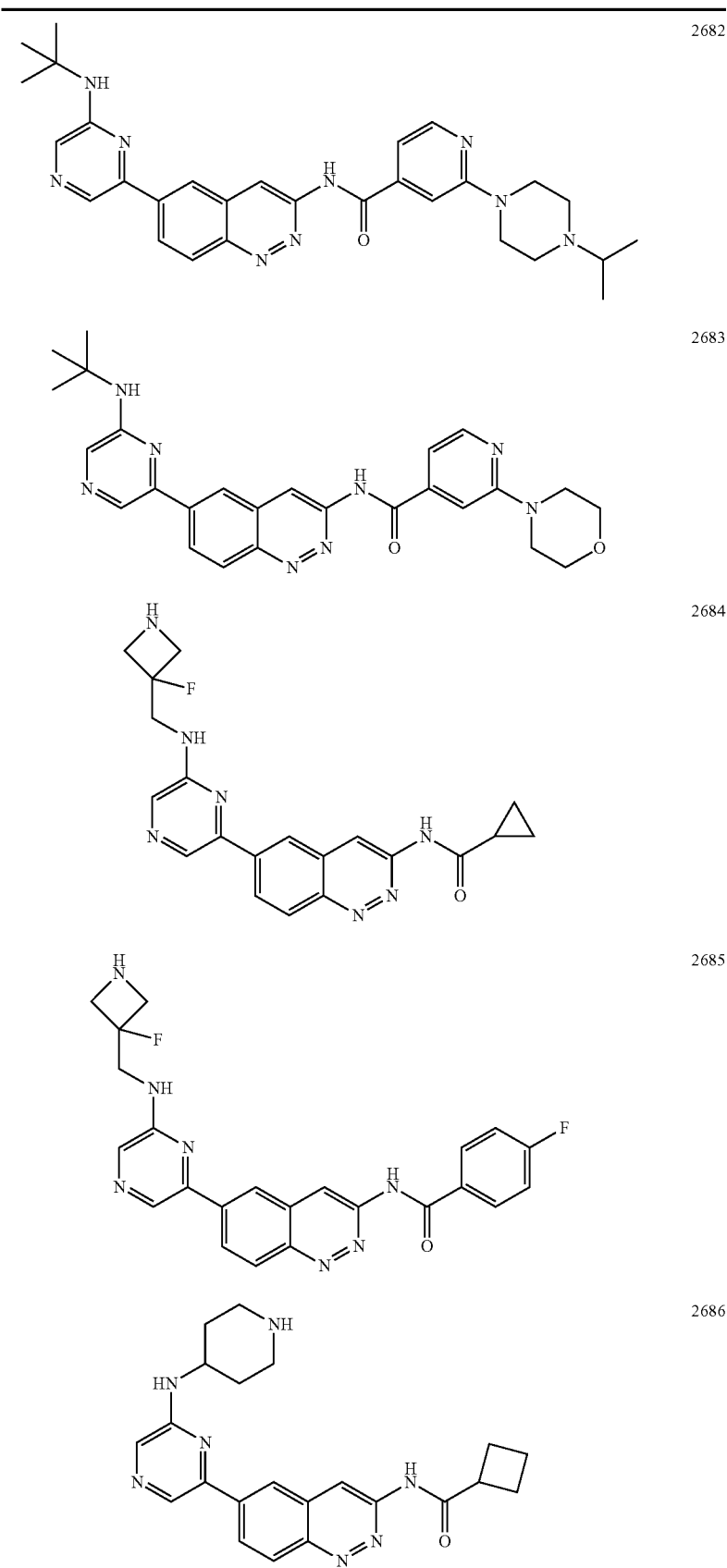

TABLE 1-continued
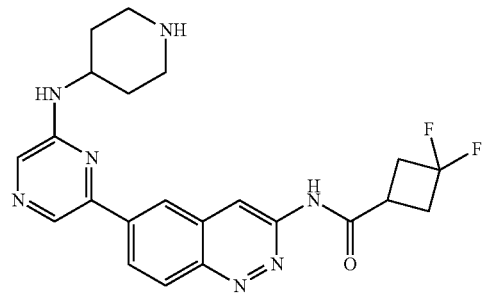 [SMILES: O=C(Nc1cc2cc(-c3cncc(NC4CCNCC4)n3)ccc2nn1)C1CC(F)(F)C1] 2687
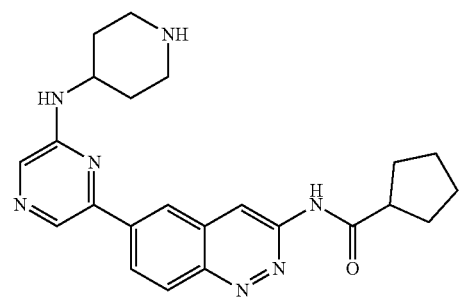 2688
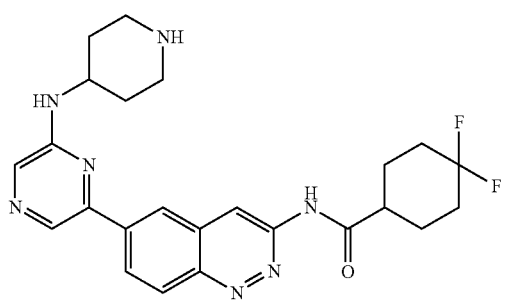 [SMILES: O=C(Nc1cc2cc(-c3cncc(NC4CCNCC4)n3)ccc2nn1)C1CCC(F)(F)CC1] 2689
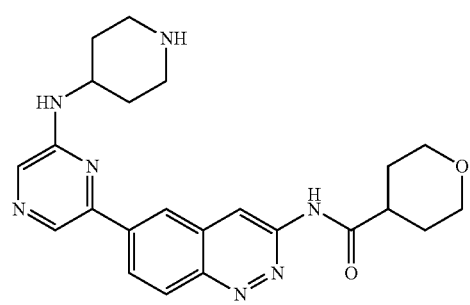 2690
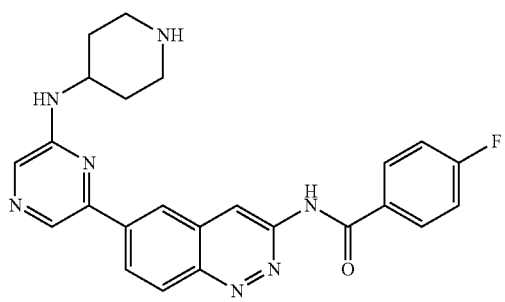 [SMILES: O=C(Nc1cc2cc(-c3cncc(NC4CCNCC4)n3)ccc2nn1)c1ccc(F)cc1] 2691

TABLE 1-continued
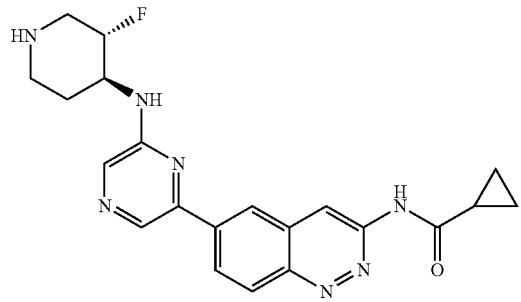 [SMILES: O=C(Nc1cc2cc(-c3cncc(N[C@H]4CCNC[C@@H]4F)n3)ccc2nn1)C1CC1] 2692
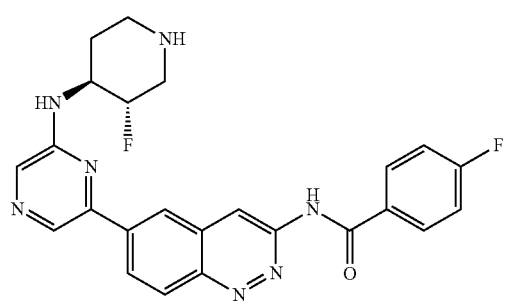 [SMILES: O=C(Nc1cc2cc(-c3cncc(N[C@H]4CCNC[C@@H]4F)n3)ccc2nn1)c1ccc(F)cc1] 2693
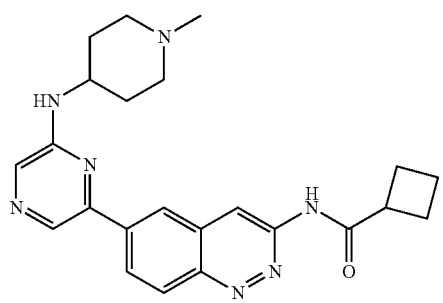 [SMILES: CN1CCC(Nc2cncc(-c3ccc4nnc(NC(=O)C5CCC5)cc4c3)n2)CC1] 2694
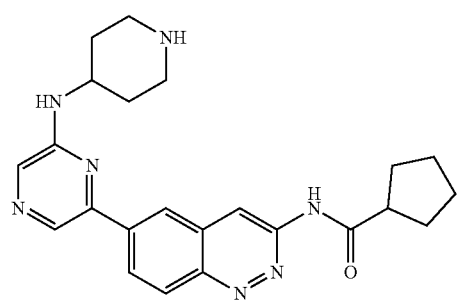 [SMILES: O=C(Nc1cc2cc(-c3cncc(NC4CCNCC4)n3)ccc2nn1)C1CCCC1] 2695
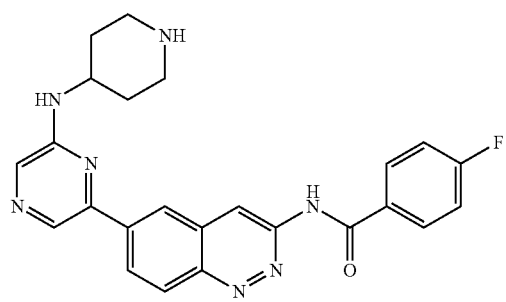 2696

TABLE 1-continued
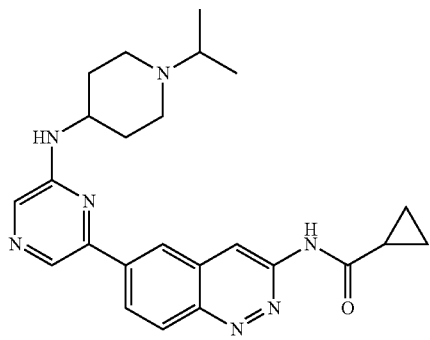
2697
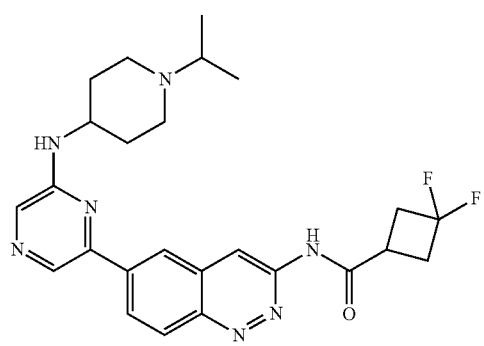 [SMILES: CC(C)N1CCC(Nc2cncc(-c3ccc4nnc(NC(=O)C5CC(F)(F)C5)cc4c3)n2)CC1]
2698
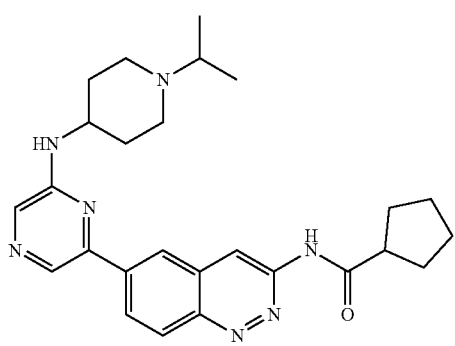 [SMILES: CC(C)N1CCC(Nc2cncc(-c3ccc4nnc(NC(=O)C5CCCC5)cc4c3)n2)CC1]
2699
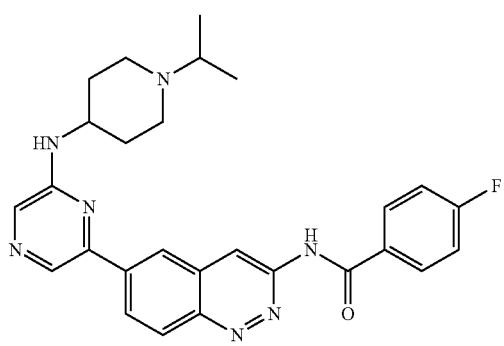 [SMILES: CC(C)N1CCC(Nc2cncc(-c3ccc4nnc(NC(=O)c5ccc(F)cc5)cc4c3)n2)CC1]
2700
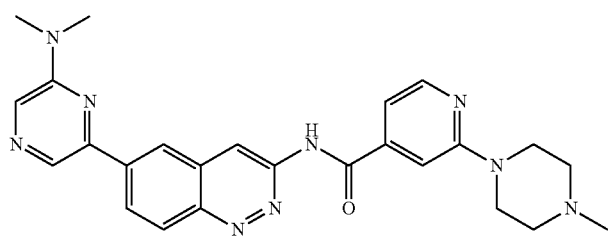 [SMILES: CN1CCN(c2cc(C(=O)Nc3cc4cc(-c5cncc(N(C)C)n5)ccc4nn3)ccn2)CC1]
2701

TABLE 1-continued
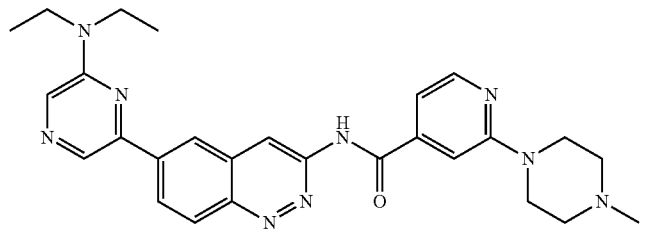 [SMILES: CCN(CC)c1cncc(-c2ccc3nnc(NC(=O)c4ccnc(N5CCN(C)CC5)c4)cc3c2)n1]
2702
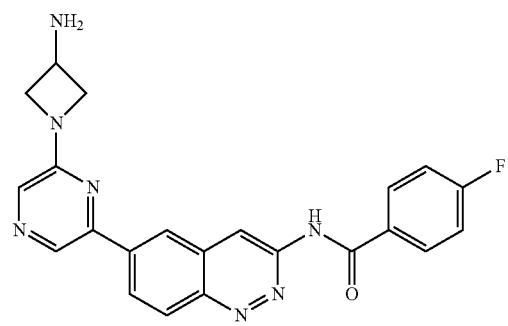 [SMILES: NC1CN(c2cncc(-c3ccc4nnc(NC(=O)c5ccc(F)cc5)cc4c3)n2)C1]
2703
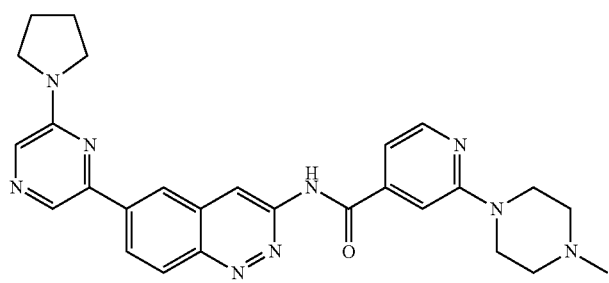
2704
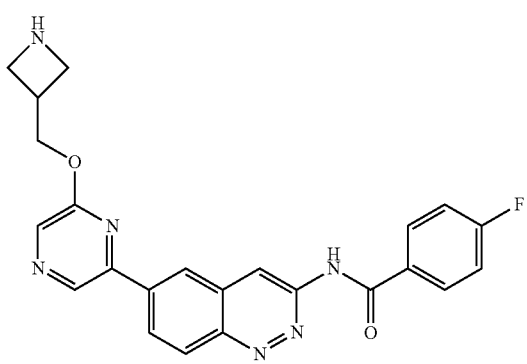 [SMILES: O=C(Nc1cc2cc(-c3cncc(OCC4CNC4)n3)ccc2nn1)c1ccc(F)cc1]
2705
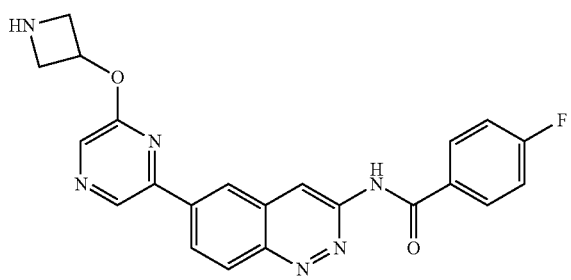 [SMILES: O=C(Nc1cc2cc(-c3cncc(OC4CNC4)n3)ccc2nn1)c1ccc(F)cc1]
2706

TABLE 1-continued
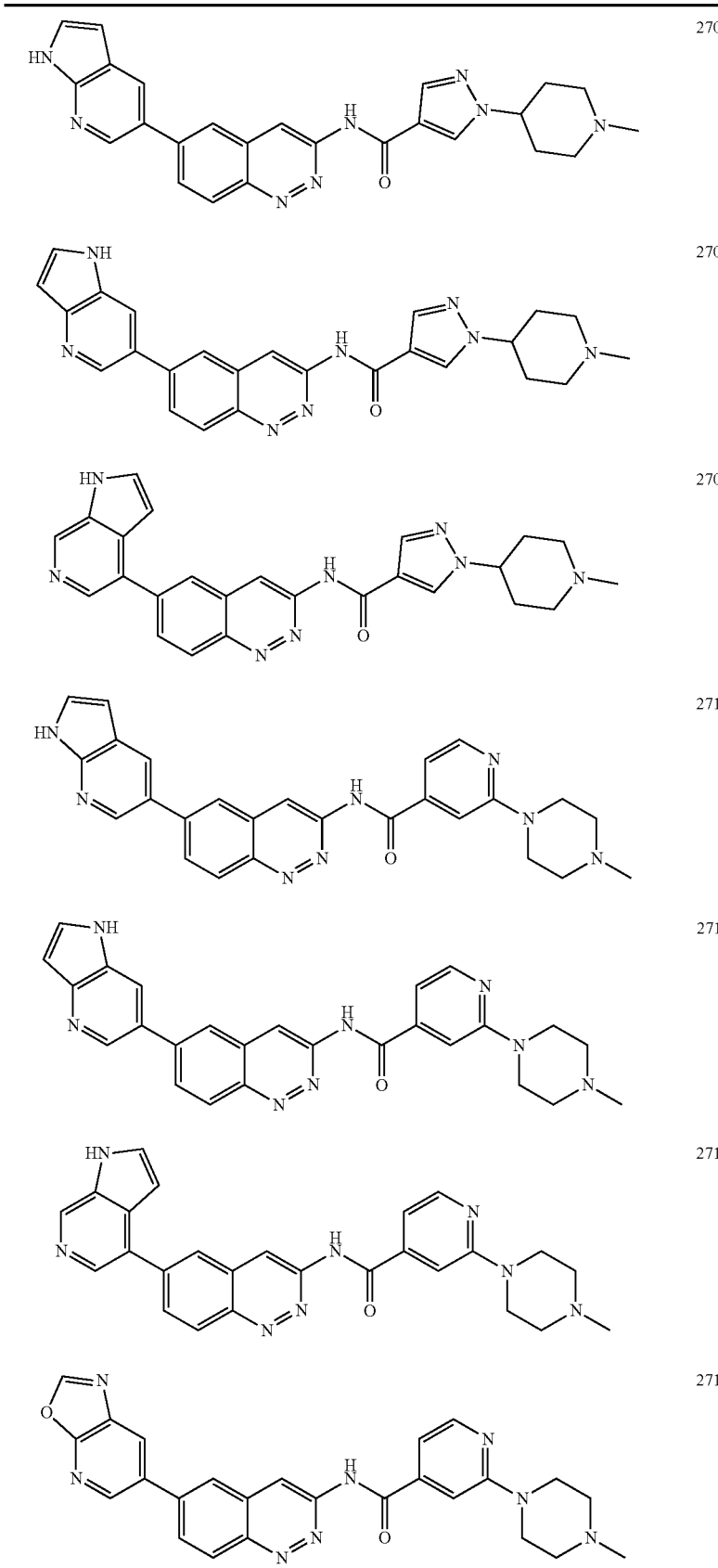

TABLE 1-continued
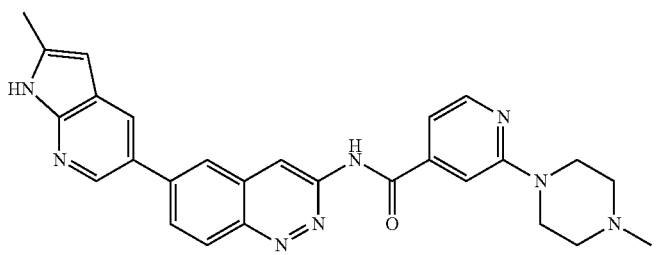 2714
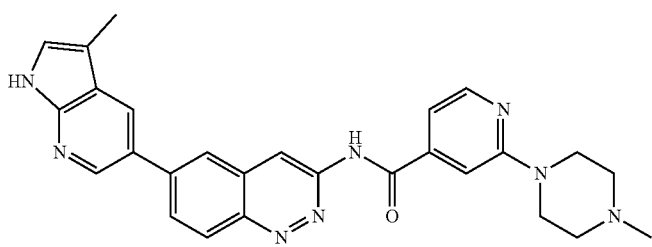 [SMILES: Cc1c[nH]c2ncc(-c3ccc4nnc(NC(=O)c5ccnc(N6CCN(C)CC6)c5)cc4c3)cc12] 2715
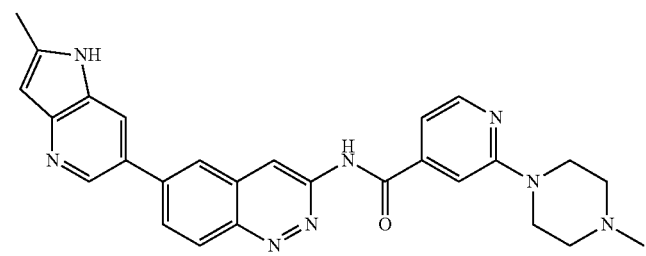 2716
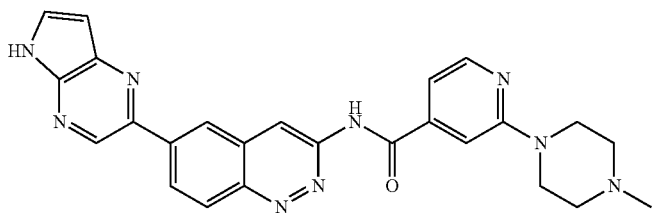 [SMILES: CN1CCN(c2cc(C(=O)Nc3cc4cc(-c5cnc6[nH]ccc6n5)ccc4nn3)ccn2)CC1] 2717
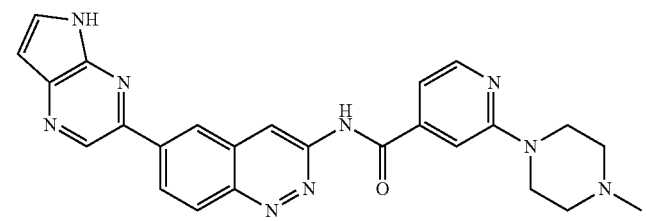 2718
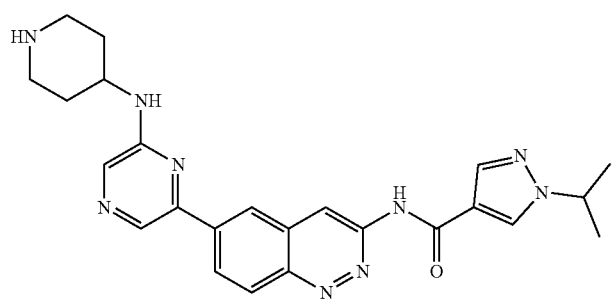 [SMILES: CC(C)n1cc(C(=O)Nc2cc3cc(-c4cncc(NC5CCNCC5)n4)ccc3nn2)cn1] 2719

TABLE 1-continued
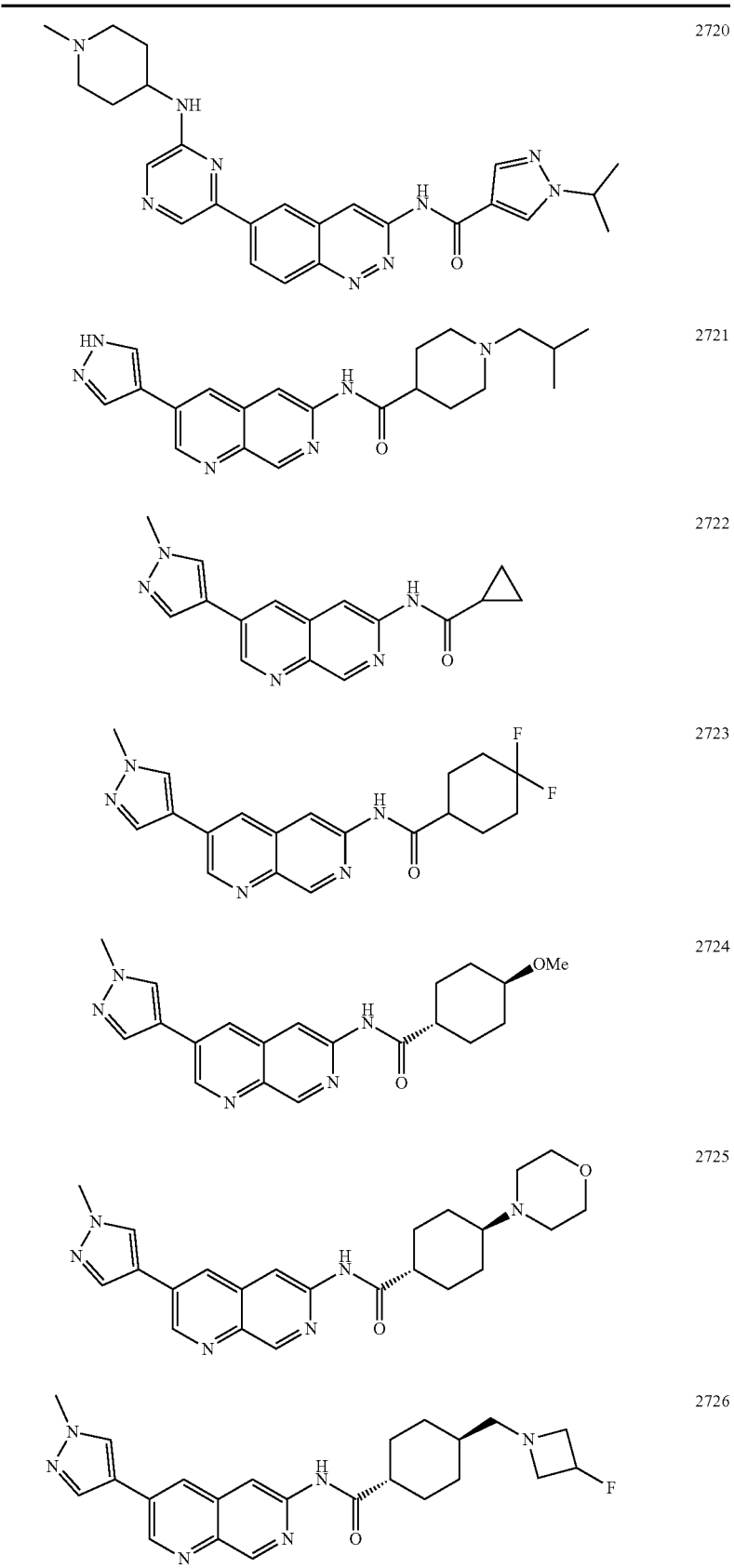
2720
2721
2722
2723
2724
2725
2726

TABLE 1-continued
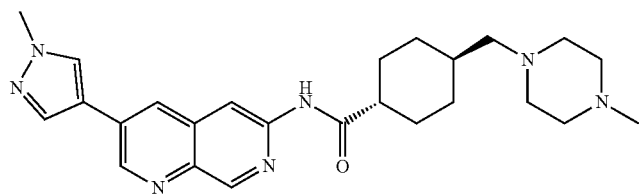 [SMILES: CN1CCN(C[C@H]2CC[C@H](C(=O)Nc3cc4cc(-c5cnn(C)c5)cnc4cn3)CC2)CC1] 2727
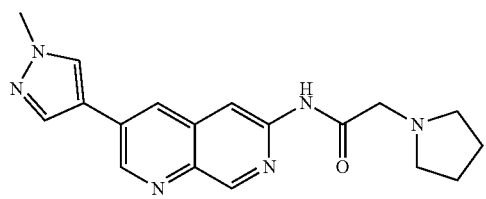 [SMILES: Cn1cc(-c2cnc3cnc(NC(=O)CN4CCCC4)cc3c2)cn1] 2728
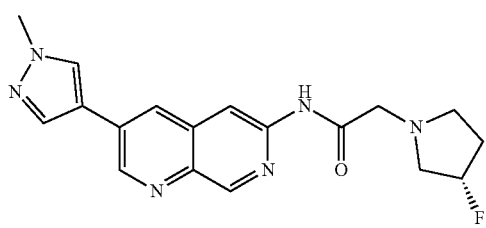 [SMILES: Cn1cc(-c2cnc3cnc(NC(=O)CN4CC[C@H](F)C4)cc3c2)cn1] 2729
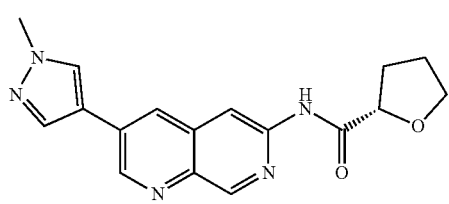 [SMILES: Cn1cc(-c2cnc3cnc(NC(=O)[C@@H]4CCCO4)cc3c2)cn1] 2730
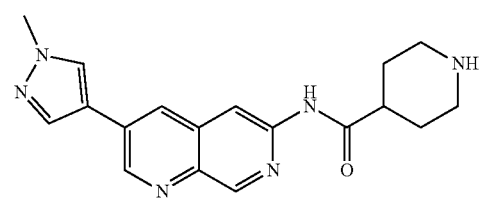 [SMILES: Cn1cc(-c2cnc3cnc(NC(=O)C4CCNCC4)cc3c2)cn1] 2731
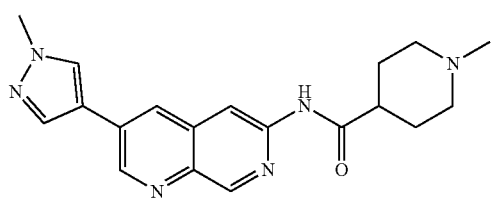 [SMILES: CN1CCC(C(=O)Nc2cc3cc(-c4cnn(C)c4)cnc3cn2)CC1] 2732
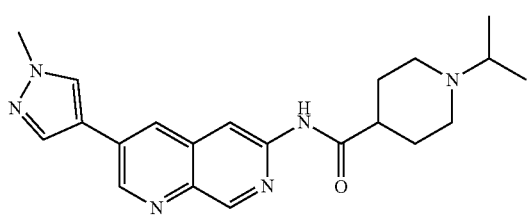 [SMILES: CC(C)N1CCC(C(=O)Nc2cc3cc(-c4cnn(C)c4)cnc3cn2)CC1] 2733

TABLE 1-continued
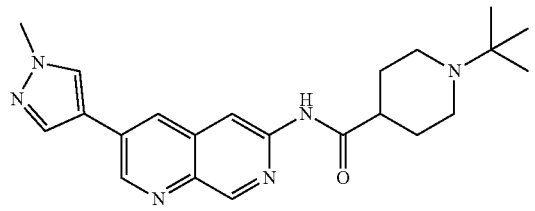 [SMILES: Cn1cc(-c2cnc3cnc(NC(=O)C4CCN(C(C)(C)C)CC4)cc3c2)cn1] 2734
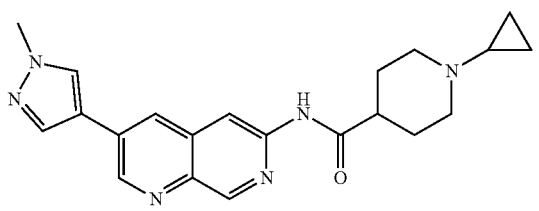 [SMILES: Cn1cc(-c2cnc3cnc(NC(=O)C4CCN(C5CC5)CC4)cc3c2)cn1] 2735
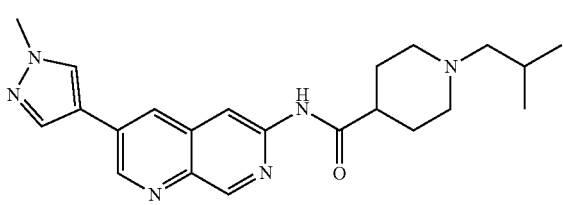 [SMILES: CC(C)CN1CCC(C(=O)Nc2cc3cc(-c4cnn(C)c4)cnc3cn2)CC1] 2736
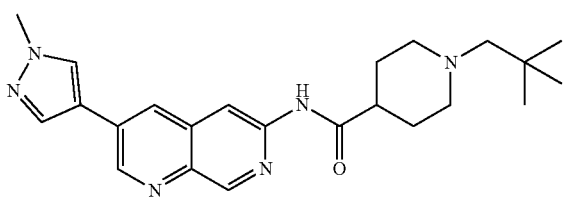 [SMILES: Cn1cc(-c2cnc3cnc(NC(=O)C4CCN(CC(C)(C)C)CC4)cc3c2)cn1] 2737
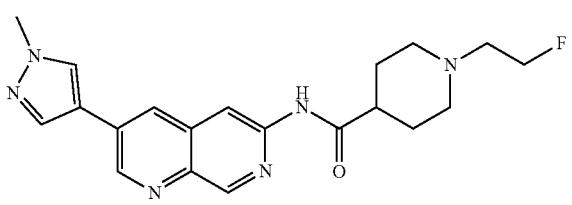 [SMILES: Cn1cc(-c2cnc3cnc(NC(=O)C4CCN(CCF)CC4)cc3c2)cn1] 2738
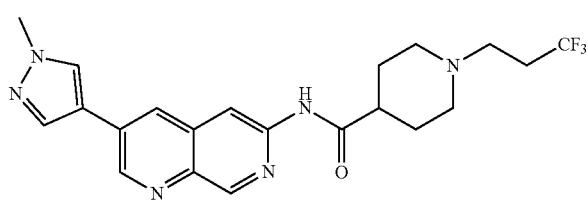 2739
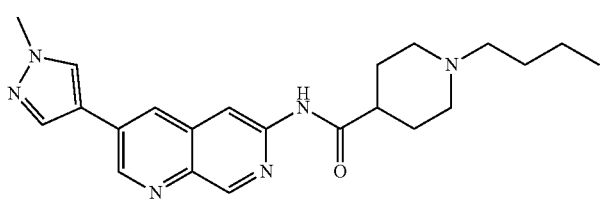 [SMILES: CCCCN1CCC(C(=O)Nc2cc3cc(-c4cnn(C)c4)cnc3cn2)CC1] 2740

TABLE 1-continued
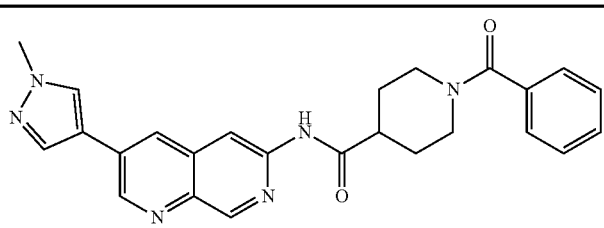 2741
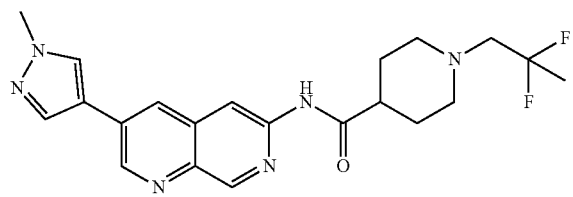 [SMILES: Cn1cc(-c2cnc3cnc(NC(=O)C4CCN(CC(C)(F)F)CC4)cc3c2)cn1] 2742
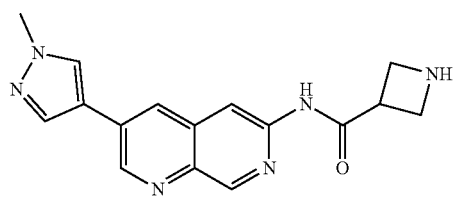 [SMILES: Cn1cc(-c2cnc3cnc(NC(=O)C4CNC4)cc3c2)cn1] 2743
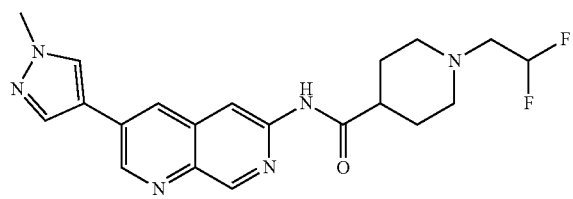 [SMILES: Cn1cc(-c2cnc3cnc(NC(=O)C4CCN(CC(F)F)CC4)cc3c2)cn1] 2744
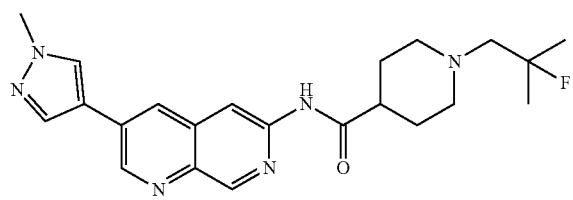 [SMILES: Cn1cc(-c2cnc3cnc(NC(=O)C4CCN(CC(C)(C)F)CC4)cc3c2)cn1] 2745
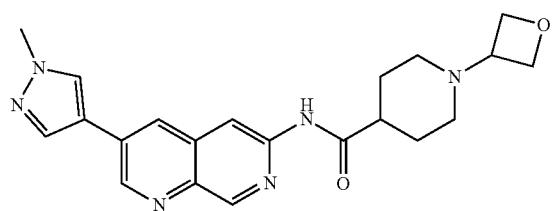 [SMILES: Cn1cc(-c2cnc3cnc(NC(=O)C4CCN(C5COC5)CC4)cc3c2)cn1] 2746
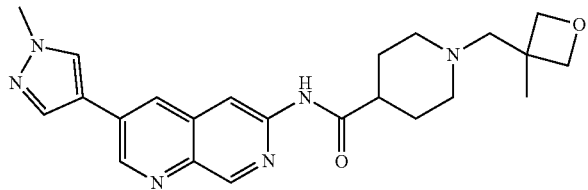 2747
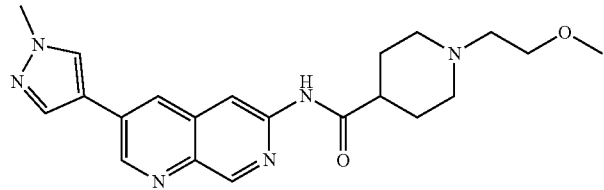 [SMILES: COCCN1CCC(C(=O)Nc2cc3cc(-c4cnn(C)c4)cnc3cn2)CC1] 2748

TABLE 1-continued
| | |
|---|---|
| 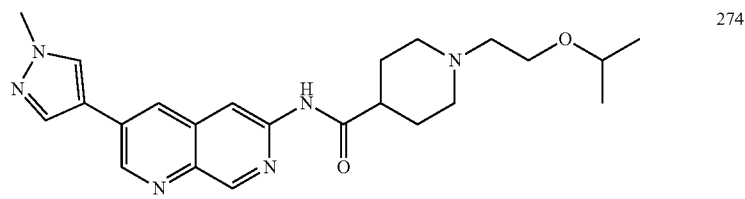 | 2749 |
| 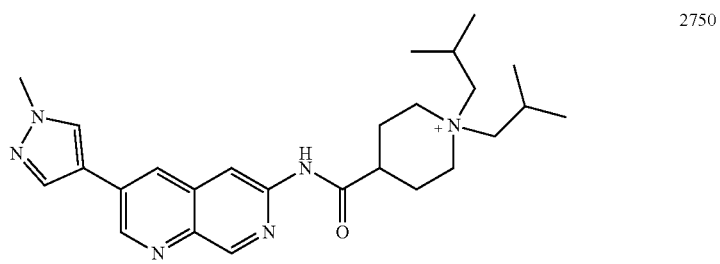 | 2750 |
| 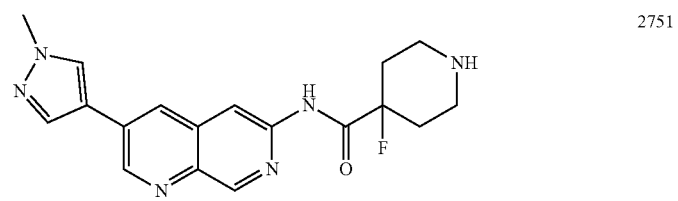 | 2751 |
| 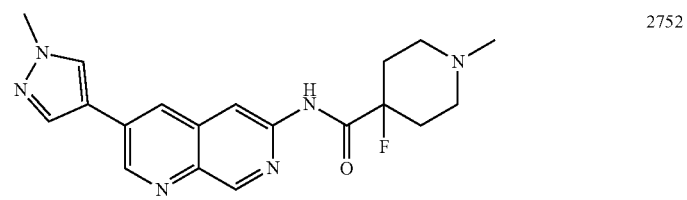 | 2752 |
| 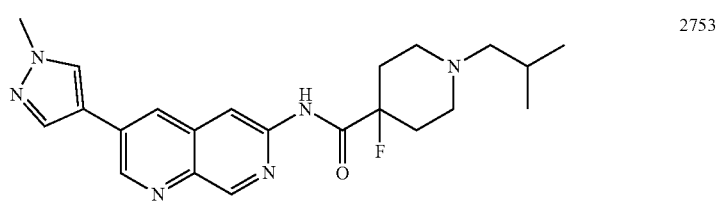 | 2753 |
| 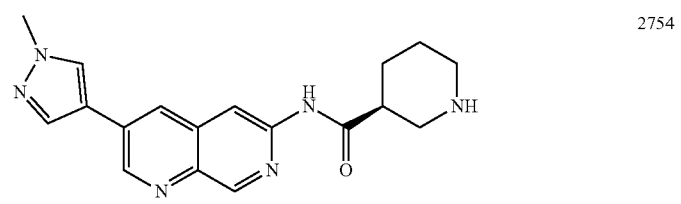 | 2754 |
| 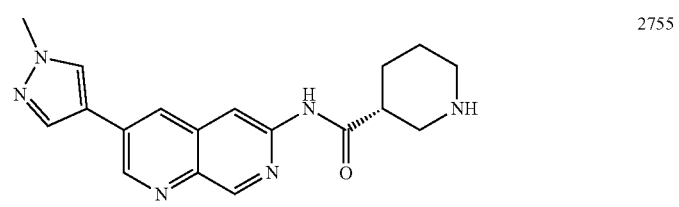 | 2755 |

TABLE 1-continued
| | |
|---|---|
| 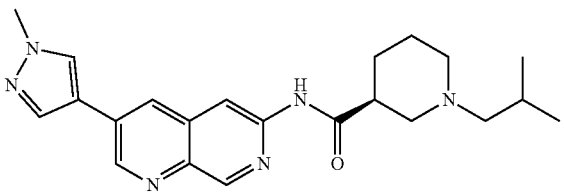 [SMILES: CC(C)CN1CCC[C@H](C(=O)Nc2cc3cc(-c4cnn(C)c4)cnc3cn2)C1] | 2756 |
| 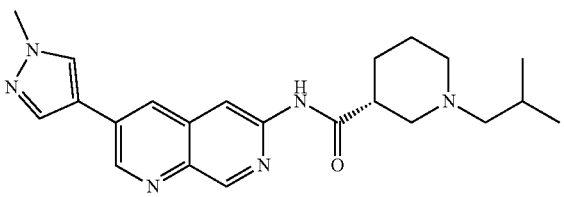 [SMILES: CC(C)CN1CCC[C@@H](C(=O)Nc2cc3cc(-c4cnn(C)c4)cnc3cn2)C1] | 2757 |
| 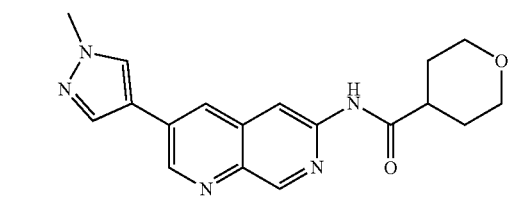 [SMILES: Cn1cc(-c2cnc3cnc(NC(=O)C4CCOCC4)cc3c2)cn1] | 2758 |
| 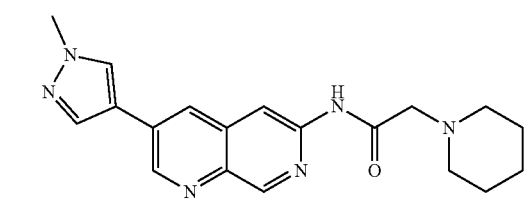 [SMILES: Cn1cc(-c2cnc3cnc(NC(=O)CN4CCCCC4)cc3c2)cn1] | 2759 |
| 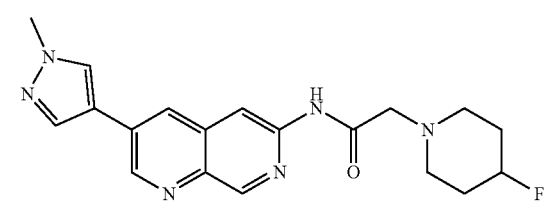 [SMILES: Cn1cc(-c2cnc3cnc(NC(=O)CN4CCC(F)CC4)cc3c2)cn1] | 2760 |
| 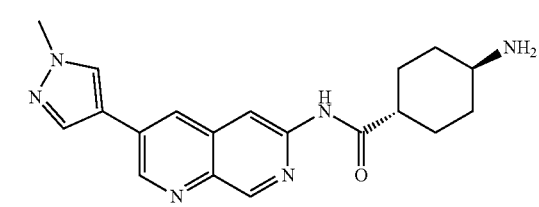 [SMILES: Cn1cc(-c2cnc3cnc(NC(=O)[C@H]4CC[C@H](N)CC4)cc3c2)cn1] | 2761 |
| 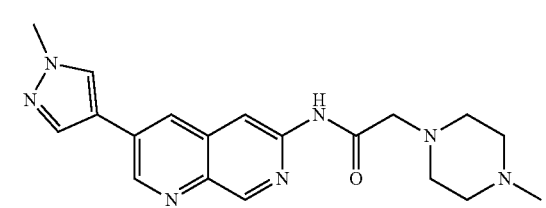 [SMILES: CN1CCN(CC(=O)Nc2cc3cc(-c4cnn(C)c4)cnc3cn2)CC1] | 2762 |
| | 2763 |

TABLE 1-continued
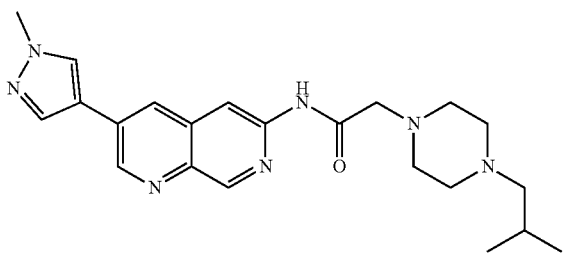 [SMILES: CC(C)CN1CCN(CC(=O)Nc2cc3cc(-c4cnn(C)c4)cnc3cn2)CC1] 2764
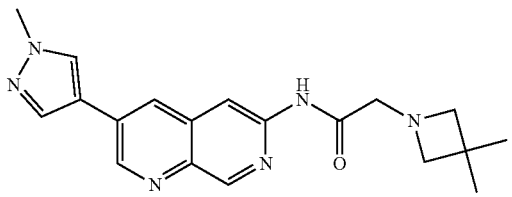 [SMILES: Cn1cc(-c2cnc3cnc(NC(=O)CN4CC(C)(C)C4)cc3c2)cn1] 2765
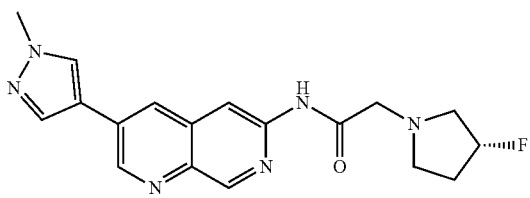 [SMILES: Cn1cc(-c2cnc3cnc(NC(=O)CN4CC[C@@H](F)C4)cc3c2)cn1] 2766
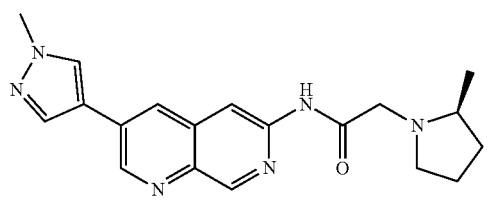 [SMILES: C[C@H]1CCCN1CC(=O)Nc1cc2cc(-c3cnn(C)c3)cnc2cn1] 2767
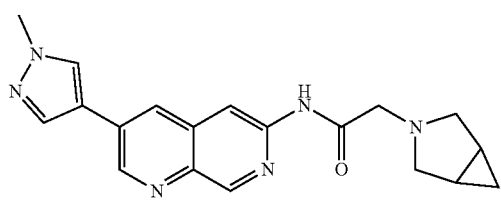 [SMILES: Cn1cc(-c2cnc3cnc(NC(=O)CN4CC5CC5C4)cc3c2)cn1] 2768
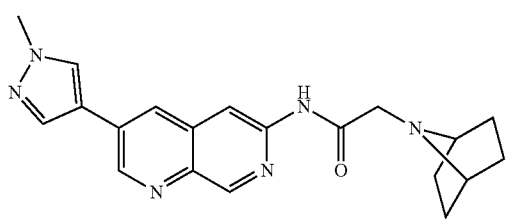 [SMILES: Cn1cc(-c2cnc3cnc(NC(=O)CN4C5CCC4CC5)cc3c2)cn1] 2769
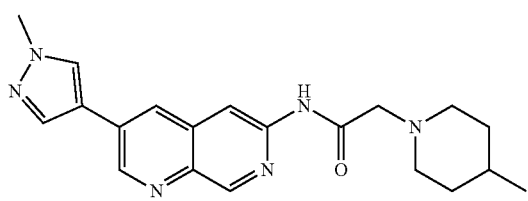 [SMILES: CC1CCN(CC(=O)Nc2cc3cc(-c4cnn(C)c4)cnc3cn2)CC1] 2770

TABLE 1-continued
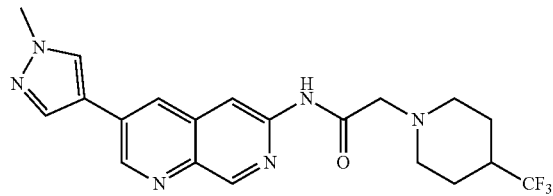 [SMILES: Cn1cc(-c2cnc3cnc(NC(=O)CN4CCC(C(F)(F)F)CC4)cc3c2)cn1] 2771
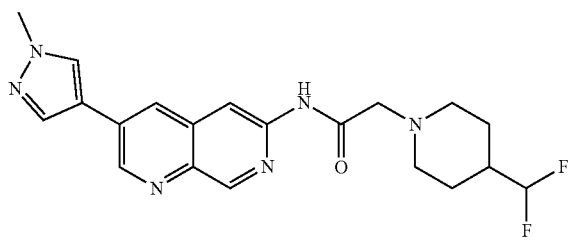 [SMILES: Cn1cc(-c2cnc3cnc(NC(=O)CN4CCC(C(F)F)CC4)cc3c2)cn1] 2772
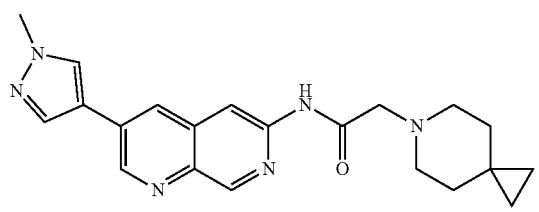 [SMILES: Cn1cc(-c2cnc3cnc(NC(=O)CN4CCC5(CC4)CC5)cc3c2)cn1] 2773
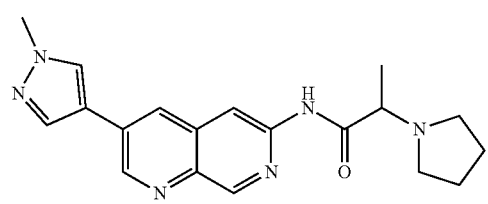 2774
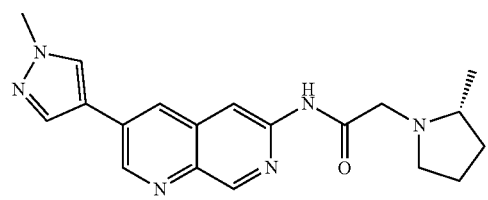 [SMILES: C[C@@H]1CCCN1CC(=O)Nc1cc2cc(-c3cnn(C)c3)cnc2cn1] 2775
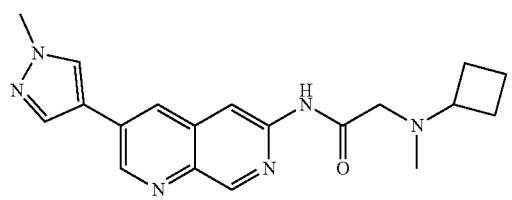 [SMILES: CN(CC(=O)Nc1cc2cc(-c3cnn(C)c3)cnc2cn1)C1CCC1] 2776
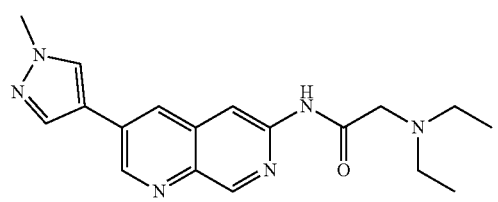 [SMILES: CCN(CC)CC(=O)Nc1cc2cc(-c3cnn(C)c3)cnc2cn1] 2777

TABLE 1-continued
| | |
|---|---|
| 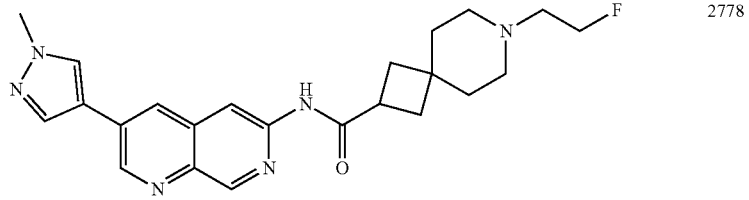 | 2778 |
| 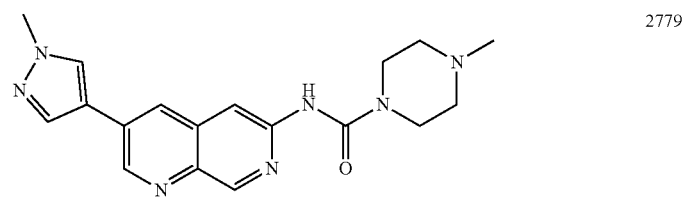 | 2779 |
| 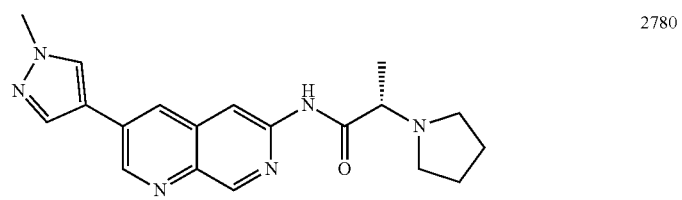 | 2780 |
| 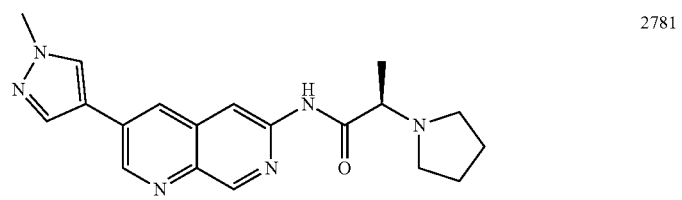 | 2781 |
| 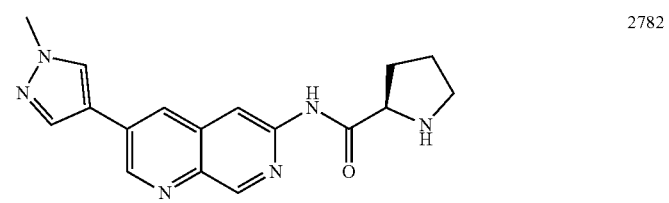 | 2782 |
| 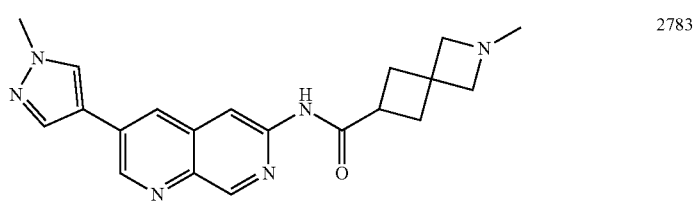 | 2783 |
| 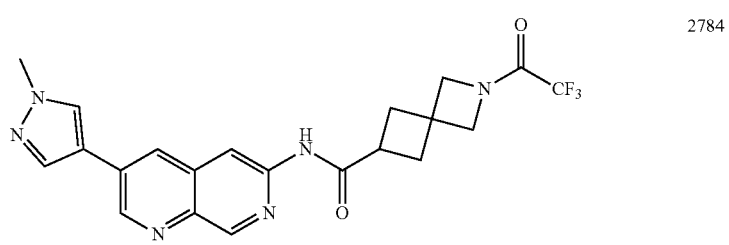 | 2784 |

TABLE 1-continued
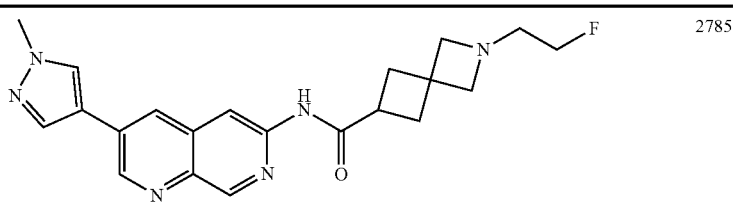 2785
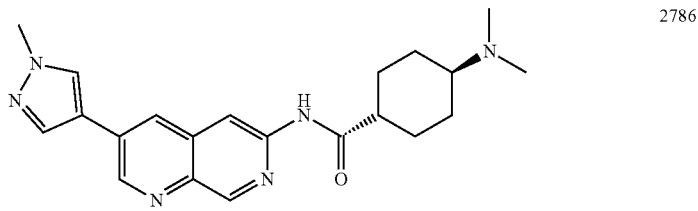 2786
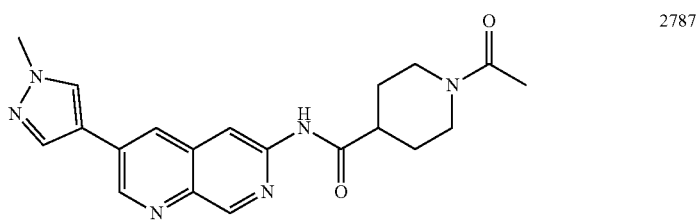 2787
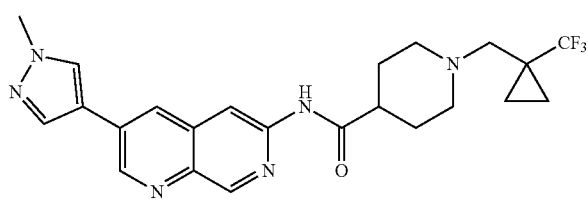 [SMILES: Cn1cc(-c2cnc3cnc(NC(=O)C4CCN(CC5(C(F)(F)F)CC5)CC4)cc3c2)cn1] 2788
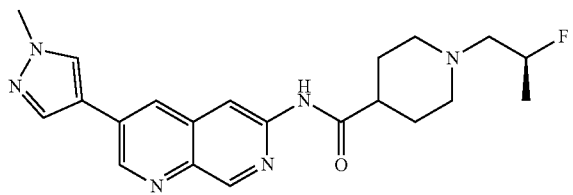 [SMILES: C[C@H](F)CN1CCC(C(=O)Nc2cc3cc(-c4cnn(C)c4)cnc3cn2)CC1] 2789
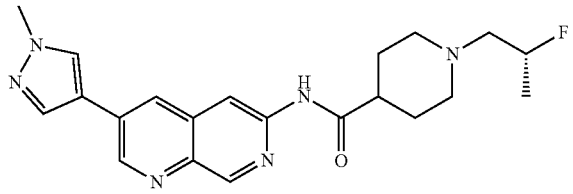 [SMILES: C[C@@H](F)CN1CCC(C(=O)Nc2cc3cc(-c4cnn(C)c4)cnc3cn2)CC1] 2790
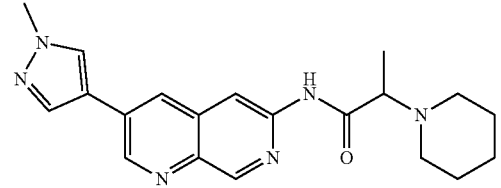 [SMILES: CC(C(=O)Nc1cc2cc(-c3cnn(C)c3)cnc2cn1)N1CCCCC1] 2791
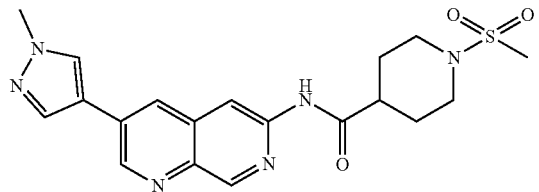 [SMILES: Cn1cc(-c2cnc3cnc(NC(=O)C4CCN(S(C)(=O)=O)CC4)cc3c2)cn1] 2792

TABLE 1-continued
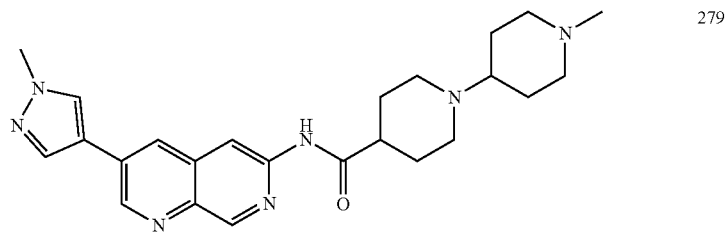 2793
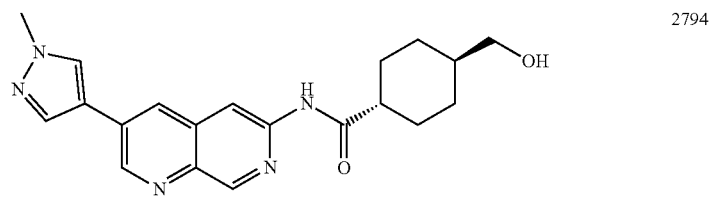 2794
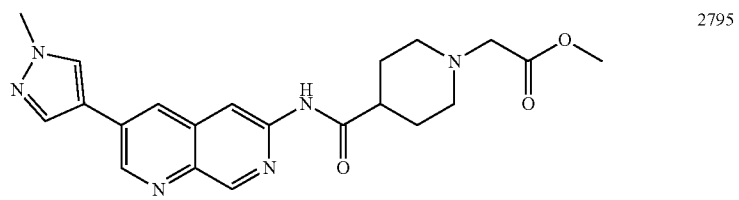 2795
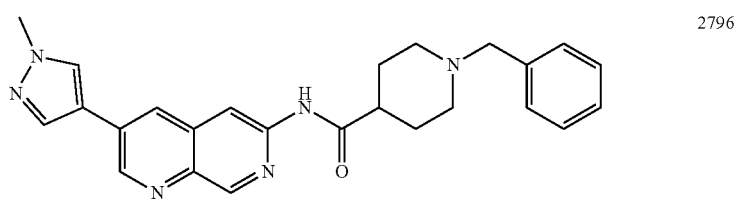 2796
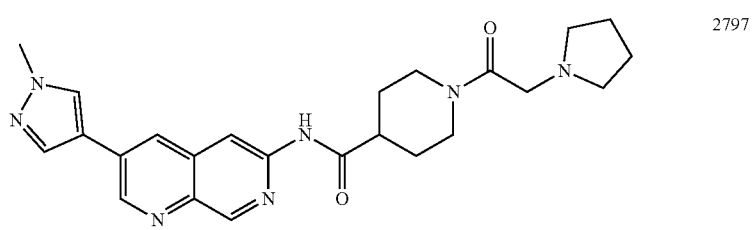 2797
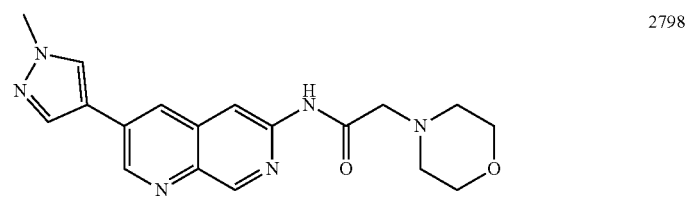 2798
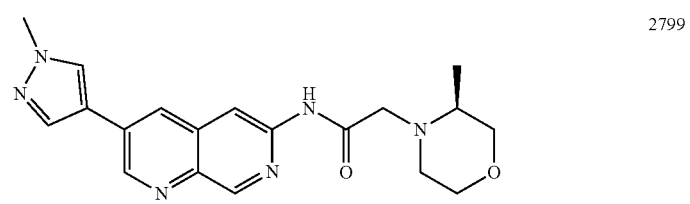 2799

TABLE 1-continued

| | |
|---|---|
| (structure) | 2800 |
| (structure) | 2801 |
| (structure) | 2802 |
| (structure) | 2803 |
| (structure) | 2804 |
| (structure) | 2805 |
| (structure) | 2806 |
| (structure) | 2807 |

TABLE 1-continued
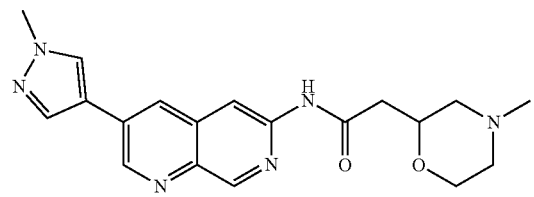 [SMILES: C[C@H]1CN(CC(=O)Nc2cc3cc(-c4cnn(C)c4)cnc3cn2)CCO1] 2808
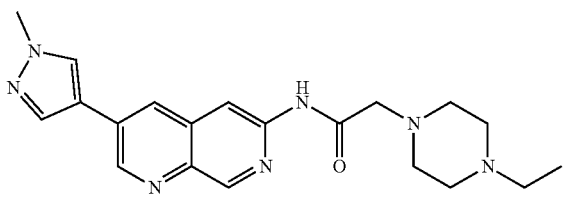 [SMILES: CCN1CCN(CC(=O)Nc2cc3cc(-c4cnn(C)c4)cnc3cn2)CC1] 2809
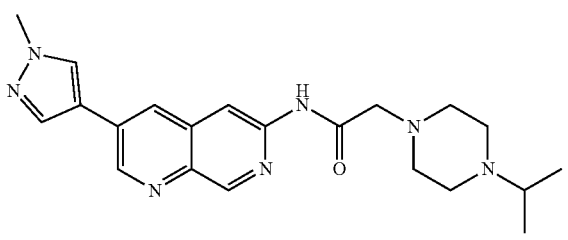 [SMILES: CC(C)N1CCN(CC(=O)Nc2cc3cc(-c4cnn(C)c4)cnc3cn2)CC1] 2810
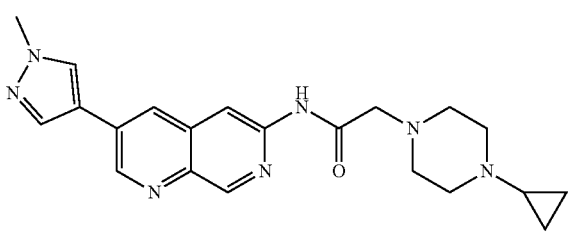 2811
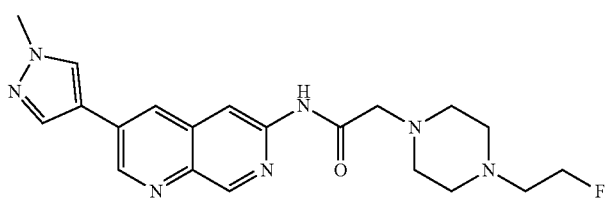 [SMILES: Cn1cc(-c2cnc3cnc(NC(=O)CN4CCN(CCF)CC4)cc3c2)cn1] 2812
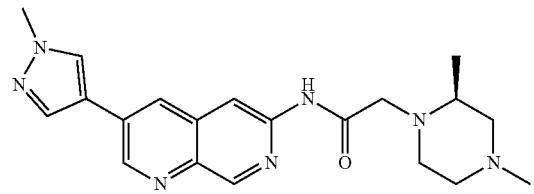 [SMILES: C[C@H]1CN(C)CCN1CC(=O)Nc1cc2cc(-c3cnn(C)c3)cnc2cn1] 2813
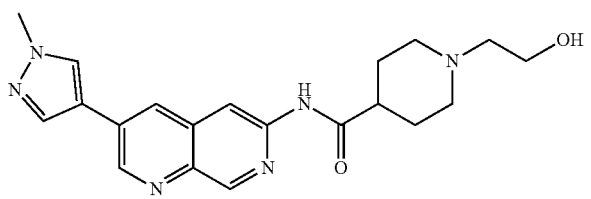 [SMILES: Cn1cc(-c2cnc3cnc(NC(=O)C4CCN(CCO)CC4)cc3c2)cn1] 2814

TABLE 1-continued
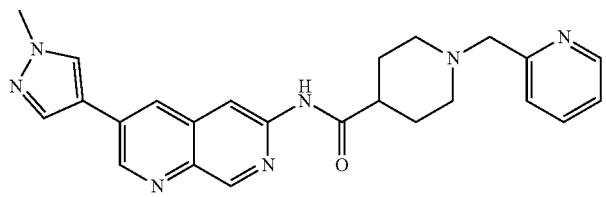 2815
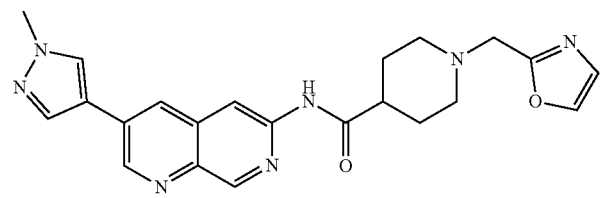 [SMILES: Cn1cc(-c2cnc3cnc(NC(=O)C4CCN(Cc5ncco5)CC4)cc3c2)cn1] 2816
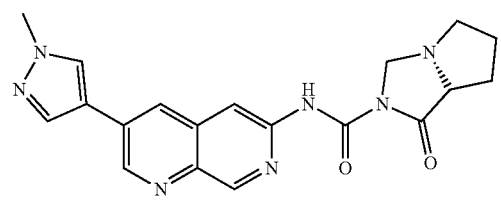 2817
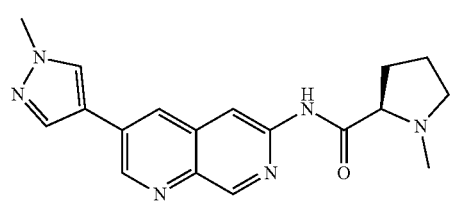 [SMILES: CN1CCC[C@@H]1C(=O)Nc1cc2cc(-c3cnn(C)c3)cnc2cn1] 2818
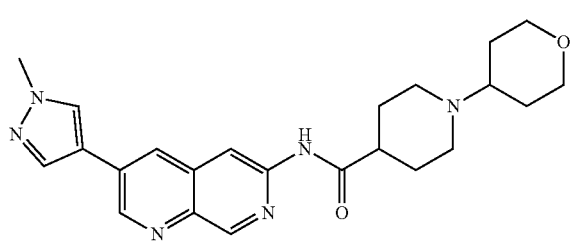 [SMILES: Cn1cc(-c2cnc3cnc(NC(=O)C4CCN(C5CCOCC5)CC4)cc3c2)cn1] 2819
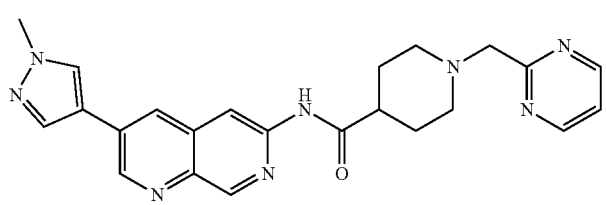 2820
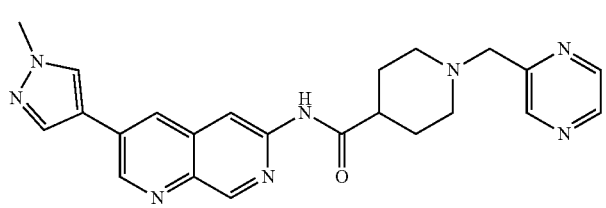 [SMILES: Cn1cc(-c2cnc3cnc(NC(=O)C4CCN(Cc5cnccn5)CC4)cc3c2)cn1] 2821
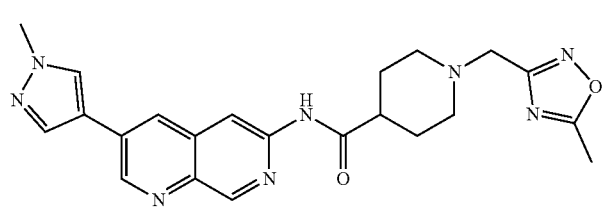 [SMILES: Cc1nc(CN2CCC(C(=O)Nc3cc4cc(-c5cnn(C)c5)cnc4cn3)CC2)no1] 2822

TABLE 1-continued
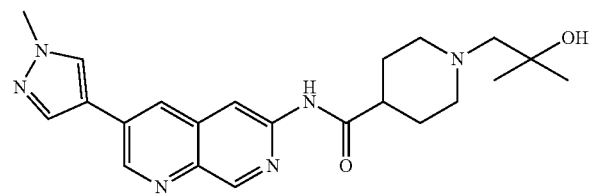 [SMILES: Cn1cc(-c2cnc3cnc(NC(=O)C4CCN(CC(C)(C)O)CC4)cc3c2)cn1] 2823
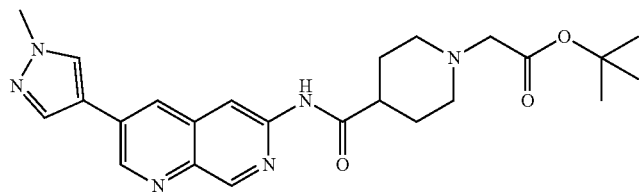 [SMILES: Cn1cc(-c2cnc3cnc(NC(=O)C4CCN(CC(=O)OC(C)(C)C)CC4)cc3c2)cn1] 2824
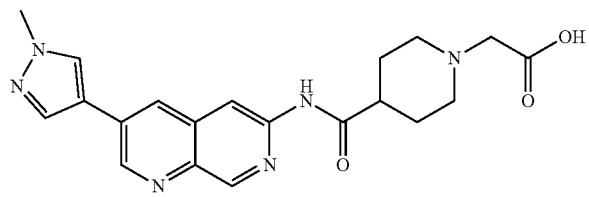 [SMILES: Cn1cc(-c2cnc3cnc(NC(=O)C4CCN(CC(=O)O)CC4)cc3c2)cn1] 2825
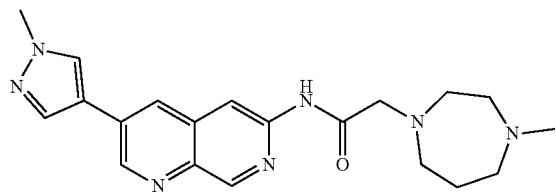 [SMILES: CN1CCCN(CC(=O)Nc2cc3cc(-c4cnn(C)c4)cnc3cn2)CC1] 2826
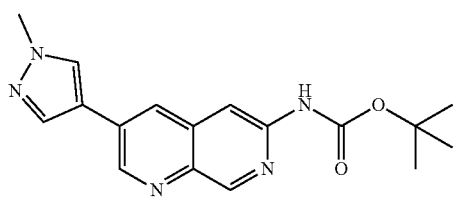 [SMILES: Cn1cc(-c2cnc3cnc(NC(=O)OC(C)(C)C)cc3c2)cn1] 2827
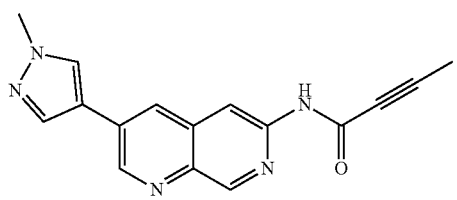 [SMILES: CC#CC(=O)Nc1cc2cc(-c3cnn(C)c3)cnc2cn1] 2828
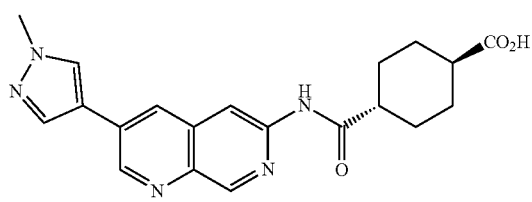 [SMILES: Cn1cc(-c2cnc3cnc(NC(=O)[C@H]4CC[C@H](C(=O)O)CC4)cc3c2)cn1] 2829
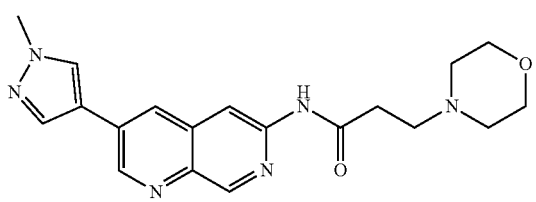 [SMILES: Cn1cc(-c2cnc3cnc(NC(=O)CCN4CCOCC4)cc3c2)cn1] 2830

TABLE 1-continued
| | |
|---|---|
| 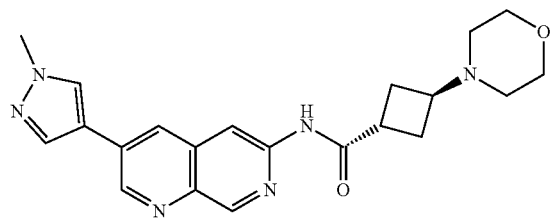 | 2831 |
| 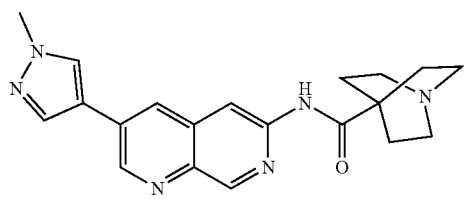 [SMILES: Cn1cc(-c2cnc3cnc(NC(=O)C45CCN(CC4)CC5)cc3c2)cn1] | 2832 |
| 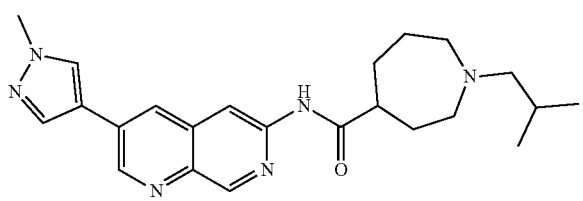 [SMILES: CC(C)CN1CCCC(C(=O)Nc2cc3cc(-c4cnn(C)c4)cnc3cn2)CC1] | 2833 |
| 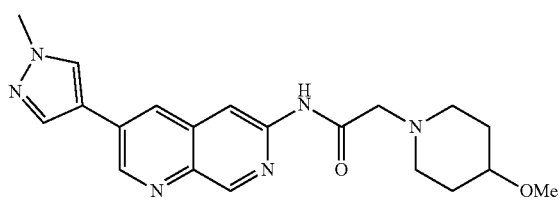 [SMILES: COC1CCN(CC(=O)Nc2cc3cc(-c4cnn(C)c4)cnc3cn2)CC1] | 2834 |
| 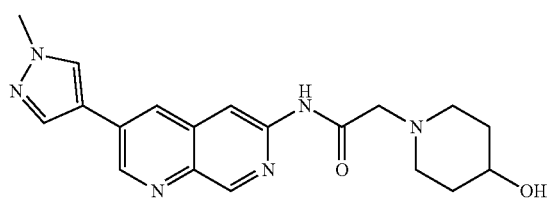 [SMILES: Cn1cc(-c2cnc3cnc(NC(=O)CN4CCC(O)CC4)cc3c2)cn1] | 2835 |
| 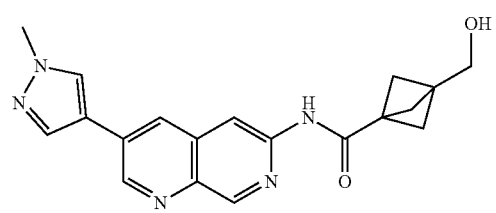 [SMILES: Cn1cc(-c2cnc3cnc(NC(=O)C45CC(CO)(C4)C5)cc3c2)cn1] | 2836 |
| 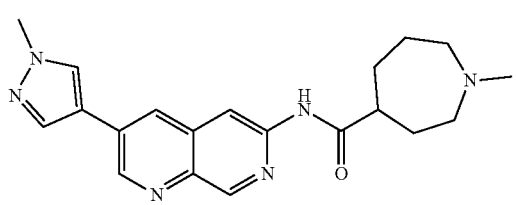 [SMILES: CN1CCCC(C(=O)Nc2cc3cc(-c4cnn(C)c4)cnc3cn2)CC1] | 2837 |

TABLE 1-continued
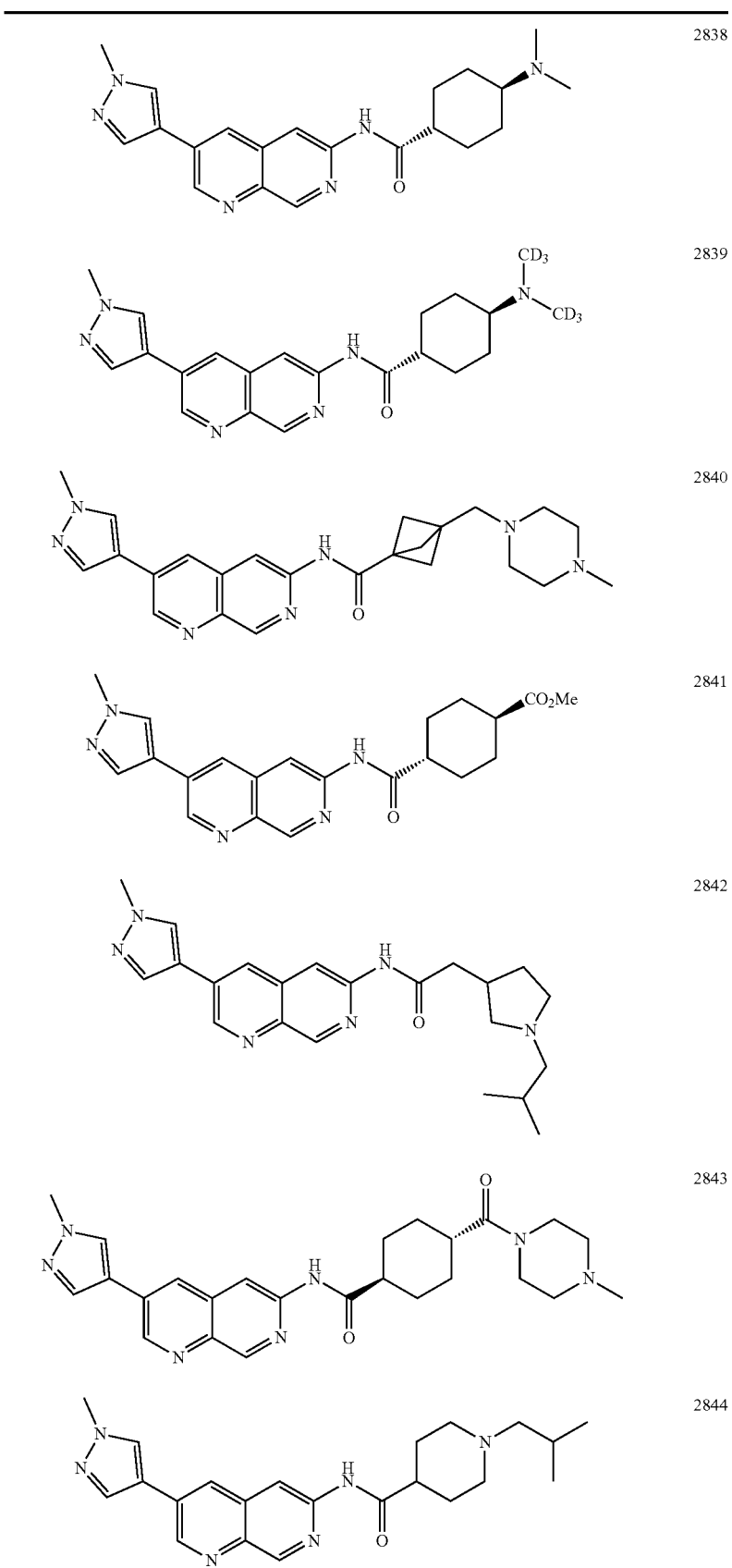

TABLE 1-continued
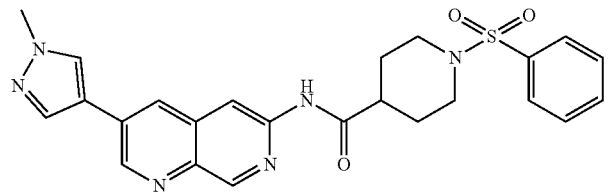 [SMILES: Cn1cc(-c2cnc3cnc(NC(=O)C4CCN(S(=O)(=O)c5ccccc5)CC4)cc3c2)cn1] 2845
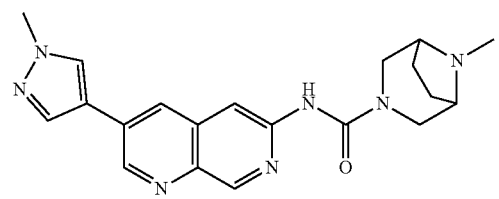 [SMILES: CN1C2CCC1CN(C(=O)Nc1cc3cc(-c4cnn(C)c4)cnc3cn1)C2] 2846
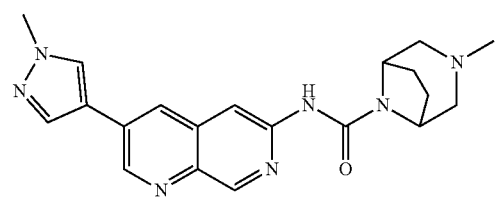 [SMILES: CN1CC2CCC(C1)N2C(=O)Nc1cc2cc(-c3cnn(C)c3)cnc2cn1] 2847
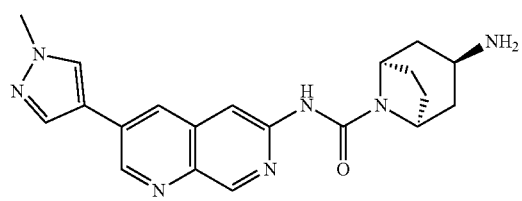 [SMILES: Cn1cc(-c2cnc3cnc(NC(=O)N4[C@@H]5CC[C@H]4C[C@H](N)C5)cc3c2)cn1] 2848
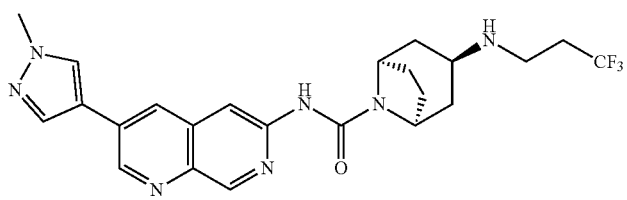 [SMILES: Cn1cc(-c2cnc3cnc(NC(=O)N4[C@@H]5CC[C@H]4C[C@H](NCCC(F)(F)F)C5)cc3c2)cn1] 2849
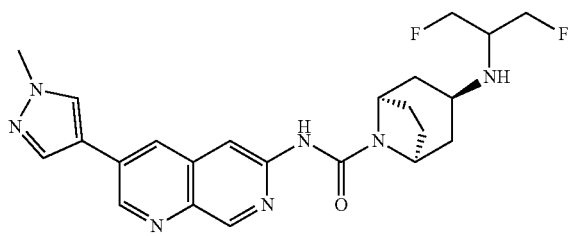 [SMILES: Cn1cc(-c2cnc3cnc(NC(=O)N4[C@@H]5CC[C@H]4C[C@H](NC(CF)CF)C5)cc3c2)cn1] 2850
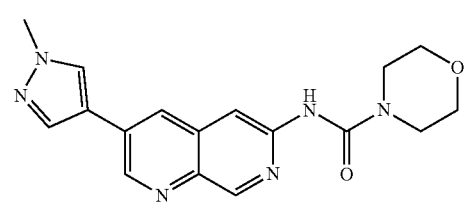 [SMILES: Cn1cc(-c2cnc3cnc(NC(=O)N4CCOCC4)cc3c2)cn1] 2851

TABLE 1-continued
| | |
|---|---|
| 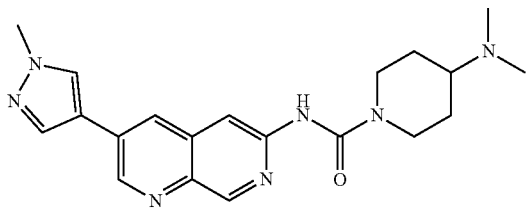 [SMILES: CN(C)C1CCN(C(=O)Nc2cc3cc(-c4cnn(C)c4)cnc3cn2)CC1] | 2852 |
| 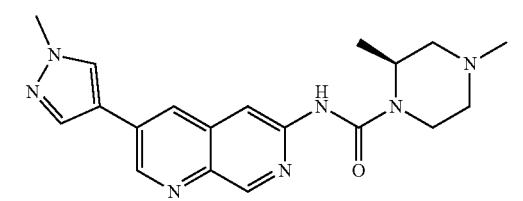 [SMILES: C[C@H]1CN(C)CCN1C(=O)Nc1cc2cc(-c3cnn(C)c3)cnc2cn1] | 2853 |
| 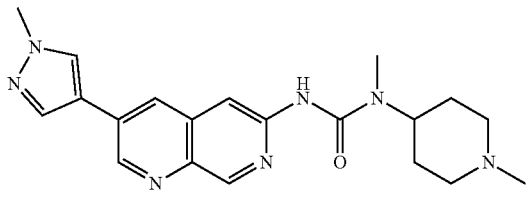 [SMILES: CN1CCC(N(C)C(=O)Nc2cc3cc(-c4cnn(C)c4)cnc3cn2)CC1] | 2854 |
| 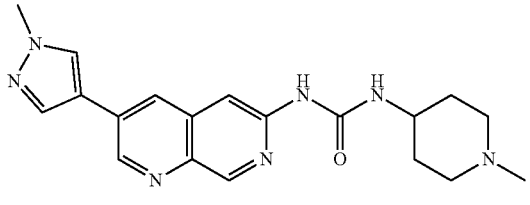 [SMILES: CN1CCC(NC(=O)Nc2cc3cc(-c4cnn(C)c4)cnc3cn2)CC1] | 2855 |
| 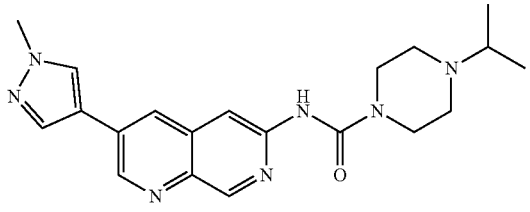 | 2856 |
| 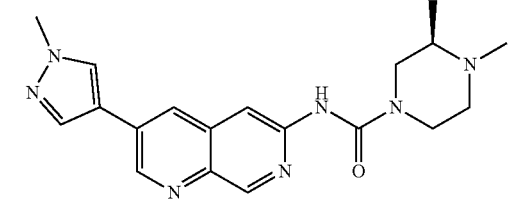 [SMILES: C[C@@H]1CN(C(=O)Nc2cc3cc(-c4cnn(C)c4)cnc3cn2)CCN1C] | 2857 |
| 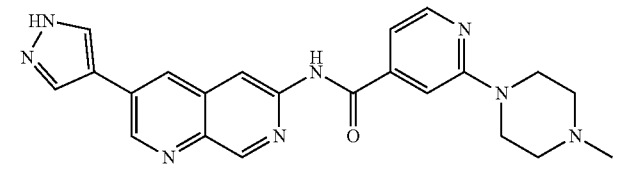 [SMILES: CN1CCN(c2cc(C(=O)Nc3cc4cc(-c5cn[nH]c5)cnc4cn3)ccn2)CC1] | 2858 |
| 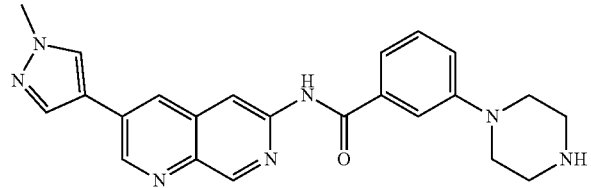 [SMILES: Cn1cc(-c2cnc3cnc(NC(=O)c4cccc(N5CCNCC5)c4)cc3c2)cn1] | 2859 |

TABLE 1-continued
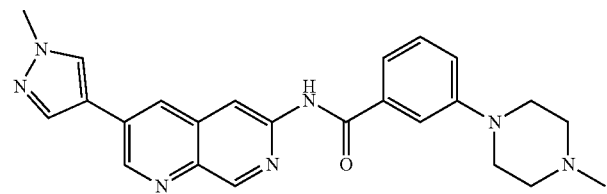 2860
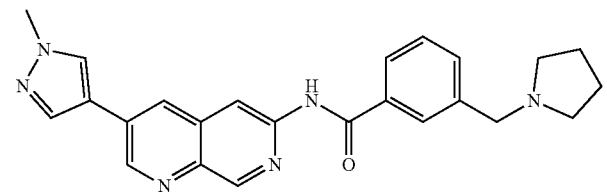 [SMILES: Cn1cc(-c2cnc3cnc(NC(=O)c4cccc(CN5CCCC5)c4)cc3c2)cn1] 2861
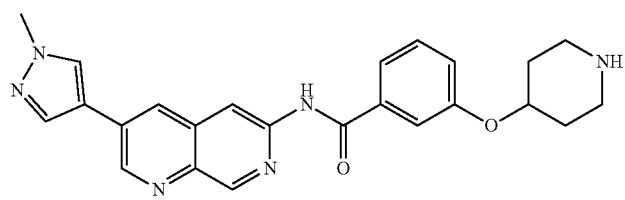 [SMILES: Cn1cc(-c2cnc3cnc(NC(=O)c4cccc(OC5CCNCC5)c4)cc3c2)cn1] 2862
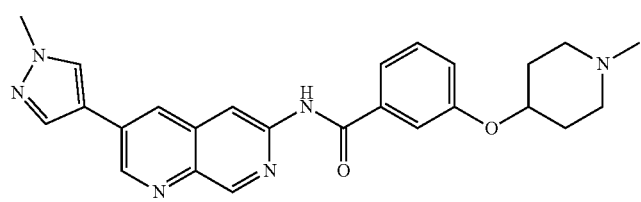 [SMILES: CN1CCC(Oc2cccc(C(=O)Nc3cc4cc(-c5cnn(C)c5)cnc4cn3)c2)CC1] 2863
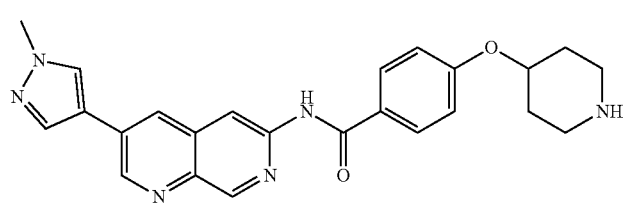 [SMILES: Cn1cc(-c2cnc3cnc(NC(=O)c4ccc(OC5CCNCC5)cc4)cc3c2)cn1] 2864
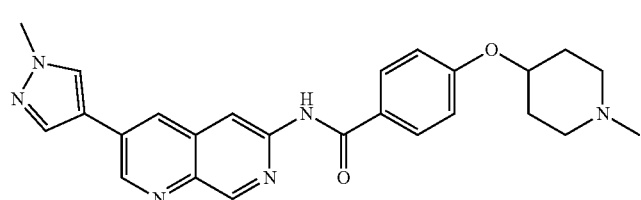 2865
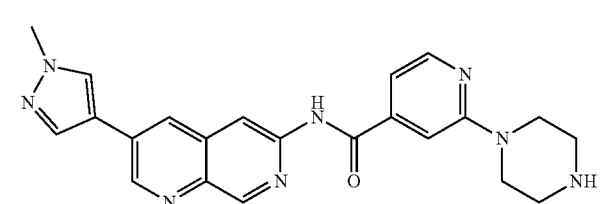 2866
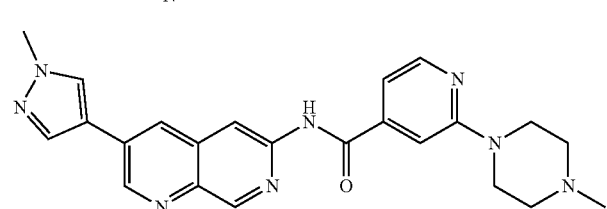 2867

TABLE 1-continued
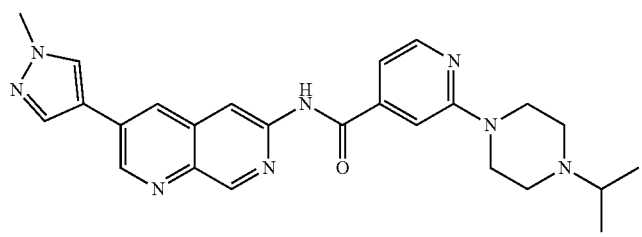 [SMILES: CC(C)N1CCN(c2cc(C(=O)Nc3cc4cc(-c5cnn(C)c5)cnc4cn3)ccn2)CC1]
2868
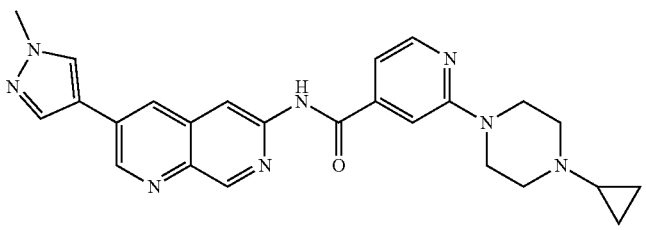 [SMILES: Cn1cc(-c2cnc3cnc(NC(=O)c4ccnc(N5CCN(C6CC6)CC5)c4)cc3c2)cn1]
2869
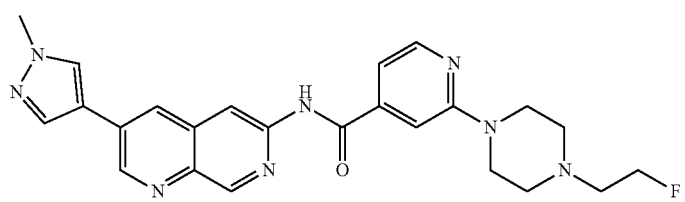
2870
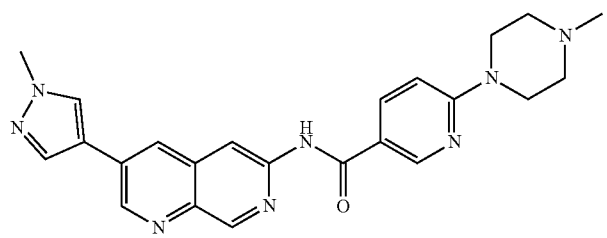 [SMILES: CN1CCN(c2ccc(C(=O)Nc3cc4cc(-c5cnn(C)c5)cnc4cn3)cn2)CC1]
2871
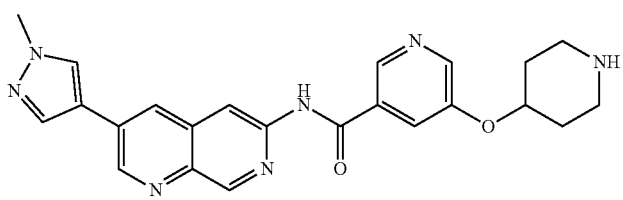 [SMILES: Cn1cc(-c2cnc3cnc(NC(=O)c4cncc(OC5CCNCC5)c4)cc3c2)cn1]
2872
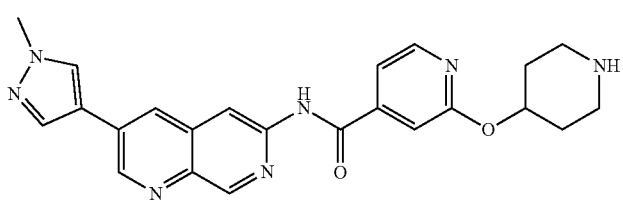 [SMILES: Cn1cc(-c2cnc3cnc(NC(=O)c4ccnc(OC5CCNCC5)c4)cc3c2)cn1]
2873
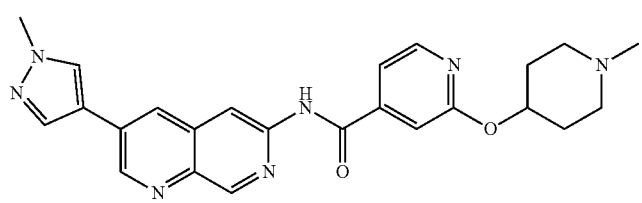 [SMILES: CN1CCC(Oc2cc(C(=O)Nc3cc4cc(-c5cnn(C)c5)cnc4cn3)ccn2)CC1]
2874

TABLE 1-continued
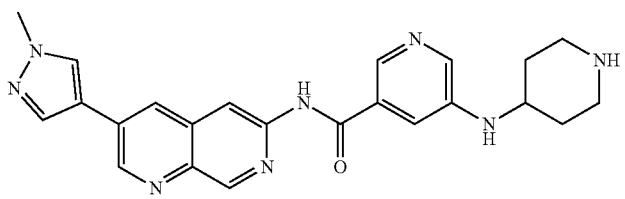 [SMILES: Cn1cc(-c2cnc3cnc(NC(=O)c4cncc(NC5CCNCC5)c4)cc3c2)cn1]
2875
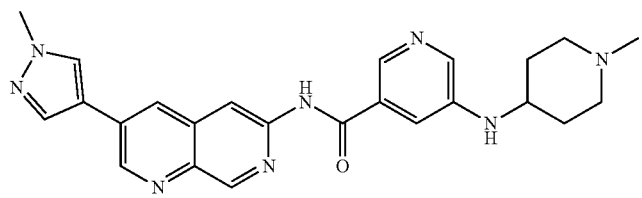 [SMILES: CN1CCC(Nc2cncc(C(=O)Nc3cc4cc(-c5cnn(C)c5)cnc4cn3)c2)CC1]
2876
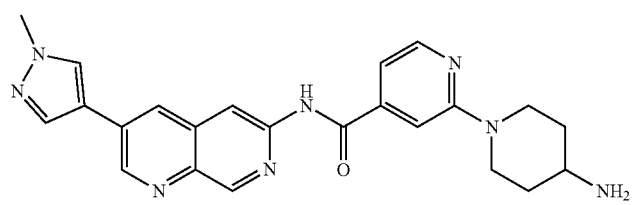
2877
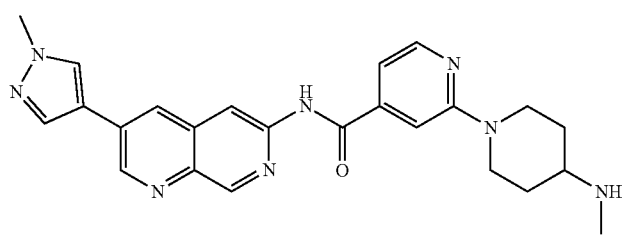 [SMILES: CNC1CCN(c2cc(C(=O)Nc3cc4cc(-c5cnn(C)c5)cnc4cn3)ccn2)CC1]
2878
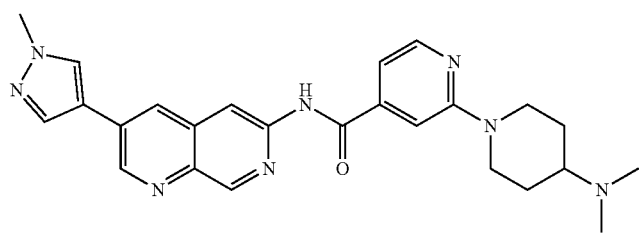 [SMILES: CN(C)C1CCN(c2cc(C(=O)Nc3cc4cc(-c5cnn(C)c5)cnc4cn3)ccn2)CC1]
2879
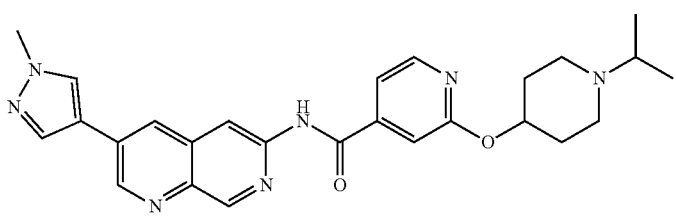 [SMILES: CC(C)N1CCC(Oc2cc(C(=O)Nc3cc4cc(-c5cnn(C)c5)cnc4cn3)ccn2)CC1]
2880
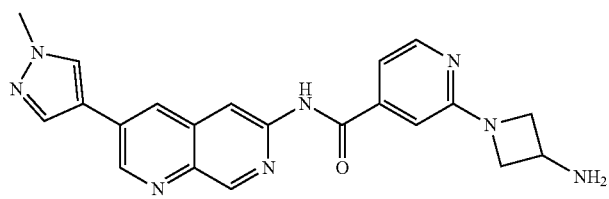 [SMILES: Cn1cc(-c2cnc3cnc(NC(=O)c4ccnc(N5CC(N)C5)c4)cc3c2)cn1]
2881

TABLE 1-continued
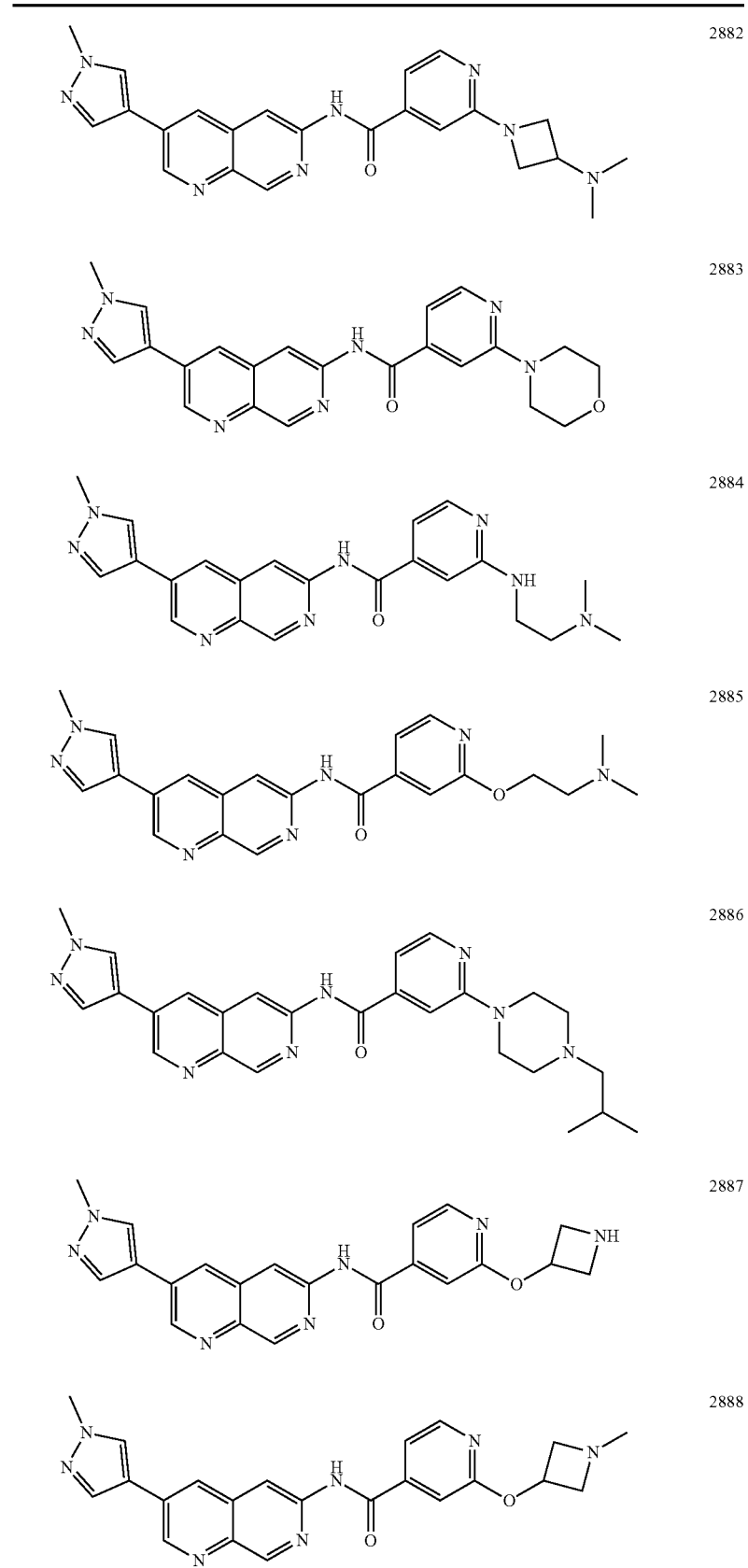

TABLE 1-continued
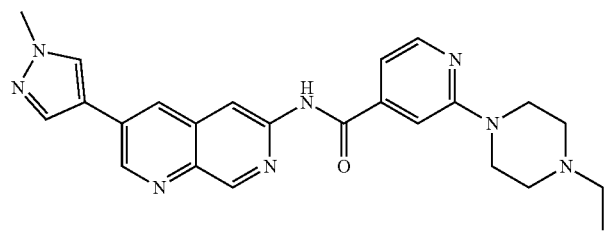 2889
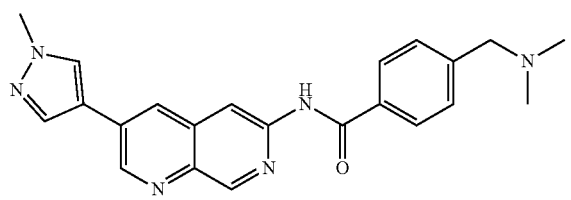 [SMILES: CN(C)Cc1ccc(C(=O)Nc2cc3cc(-c4cnn(C)c4)cnc3cn2)cc1] 2890
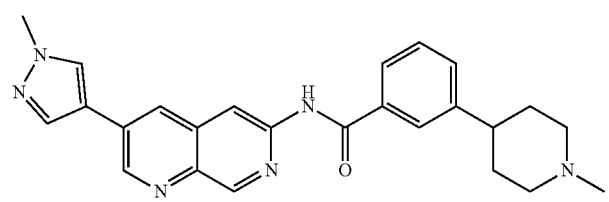 2891
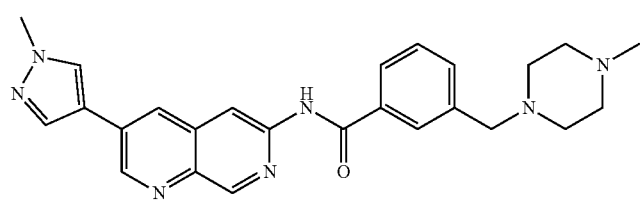 [SMILES: CN1CCN(Cc2cccc(C(=O)Nc3cc4cc(-c5cnn(C)c5)cnc4cn3)c2)CC1] 2892
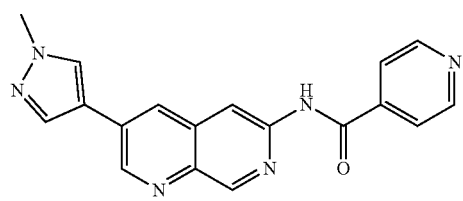 [SMILES: Cn1cc(-c2cnc3cnc(NC(=O)c4ccncc4)cc3c2)cn1] 2893
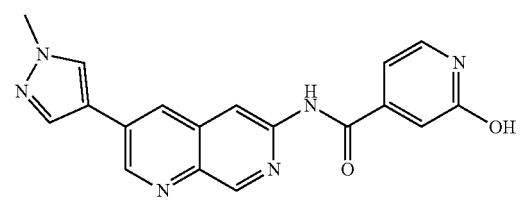 [SMILES: Cn1cc(-c2cnc3cnc(NC(=O)c4ccnc(O)c4)cc3c2)cn1] 2894
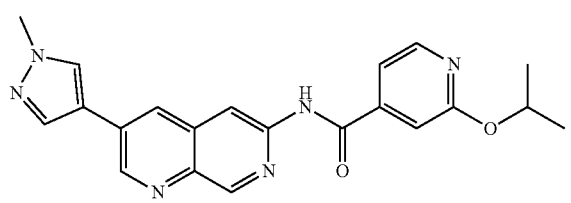 [SMILES: CC(C)Oc1cc(C(=O)Nc2cc3cc(-c4cnn(C)c4)cnc3cn2)ccn1] 2895

TABLE 1-continued
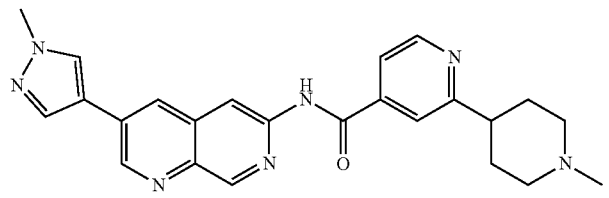 [SMILES: CN1CCC(c2cc(C(=O)Nc3cc4cc(-c5cnn(C)c5)cnc4cn3)ccn2)CC1]
2896
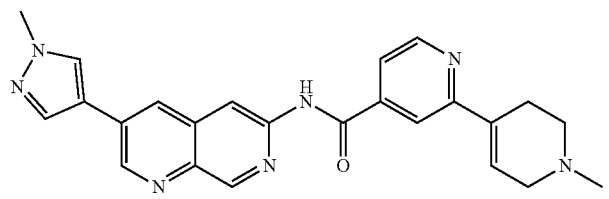
2897
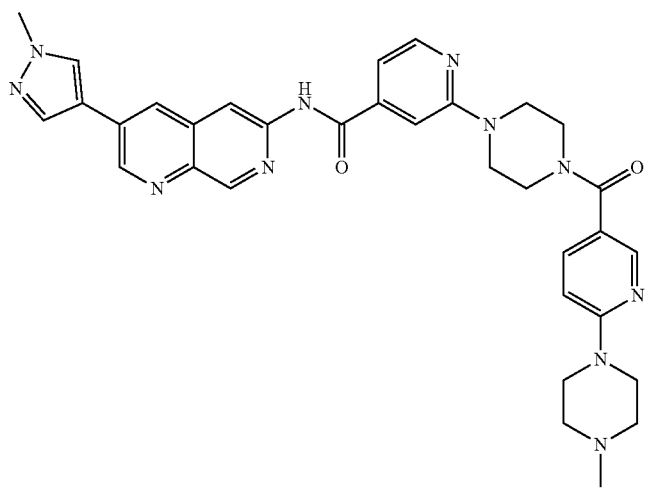 [SMILES: CN1CCN(c2ccc(C(=O)N3CCN(c4cc(C(=O)Nc5cc6cc(-c7cnn(C)c7)cnc6cn5)ccn4)CC3)cn2)CC1]
2898
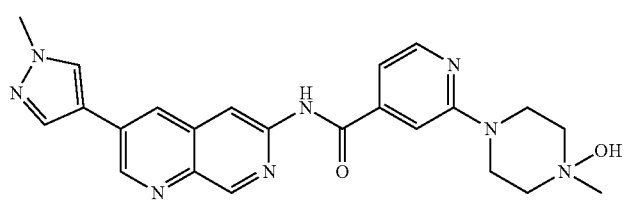
2899
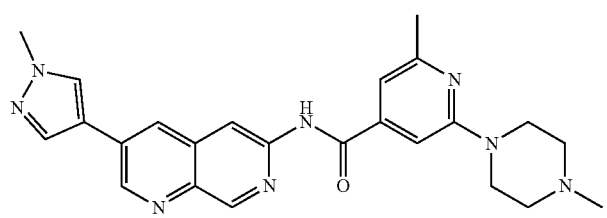 [SMILES: Cc1cc(C(=O)Nc2cc3cc(-c4cnn(C)c4)cnc3cn2)cc(N2CCN(C)CC2)n1]
2900
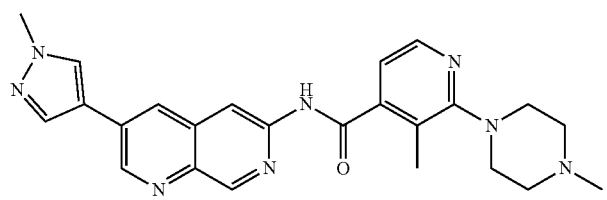
2901

TABLE 1-continued
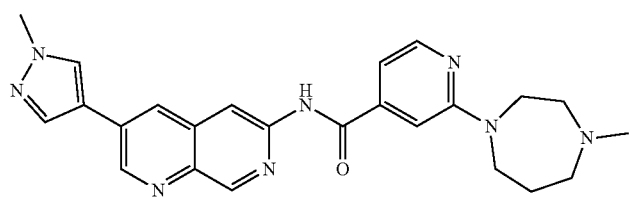 [SMILES: CN1CCCN(c2cc(C(=O)Nc3cc4cc(-c5cnn(C)c5)cnc4cn3)ccn2)CC1]
2902
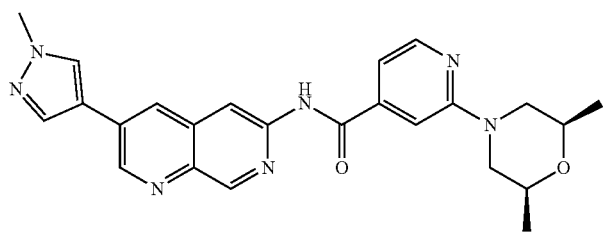
2903
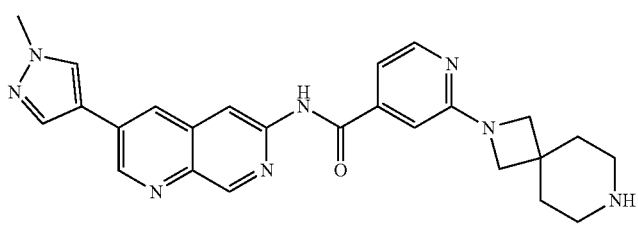 [SMILES: Cn1cc(-c2cnc3cnc(NC(=O)c4ccnc(N5CC6(CCNCC6)C5)c4)cc3c2)cn1]
2904
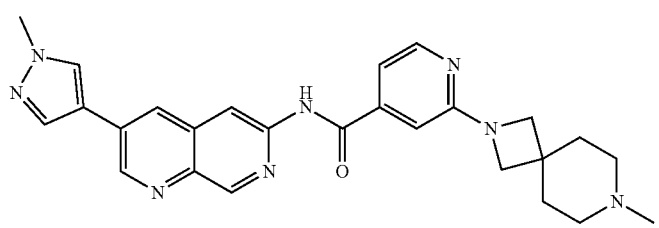 [SMILES: CN1CCC2(CC1)CN(c1cc(C(=O)Nc3cc4cc(-c5cnn(C)c5)cnc4cn3)ccn1)C2]
2905
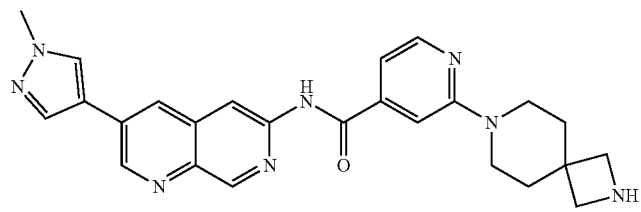 [SMILES: Cn1cc(-c2cnc3cnc(NC(=O)c4ccnc(N5CCC6(CC5)CNC6)c4)cc3c2)cn1]
2906
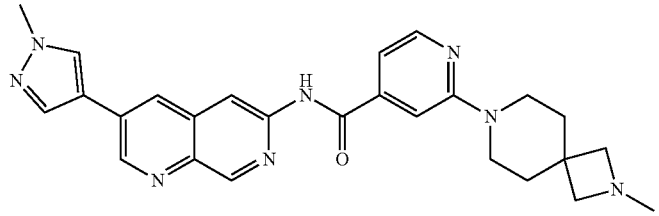 [SMILES: CN1CC2(CCN(c3cc(C(=O)Nc4cc5cc(-c6cnn(C)c6)cnc5cn4)ccn3)CC2)C1]
2907
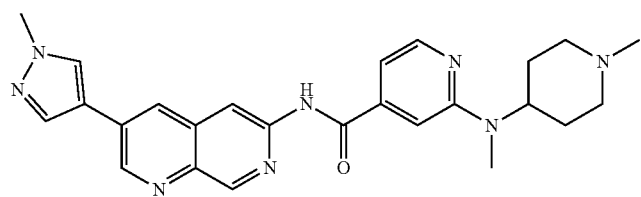 [SMILES: CN1CCC(N(C)c2cc(C(=O)Nc3cc4cc(-c5cnn(C)c5)cnc4cn3)ccn2)CC1]
2908

TABLE 1-continued
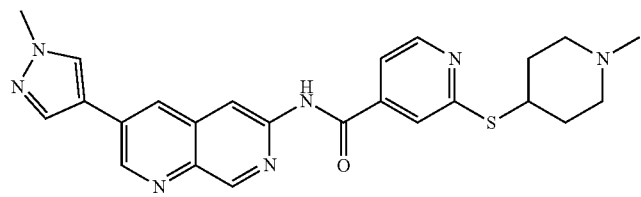
2909
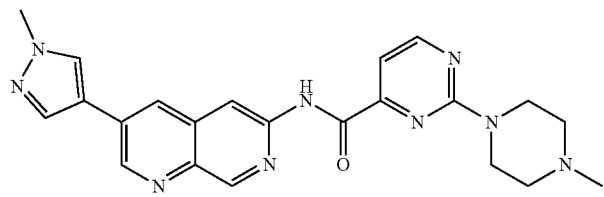
2910
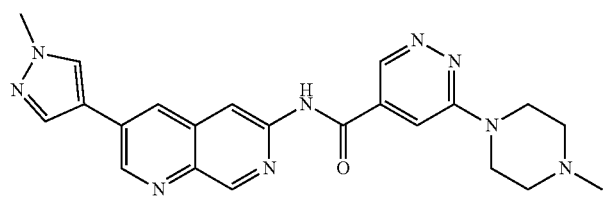 [SMILES: CN1CCN(c2cc(C(=O)Nc3cc4cc(-c5cnn(C)c5)cnc4cn3)cnn2)CC1]
2911
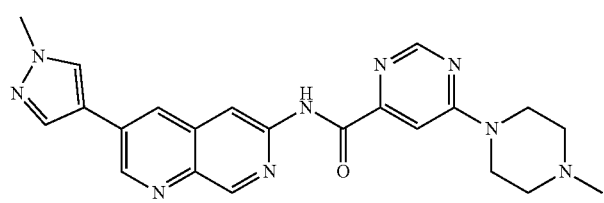 [SMILES: CN1CCN(c2cc(C(=O)Nc3cc4cc(-c5cnn(C)c5)cnc4cn3)ncn2)CC1]
2912
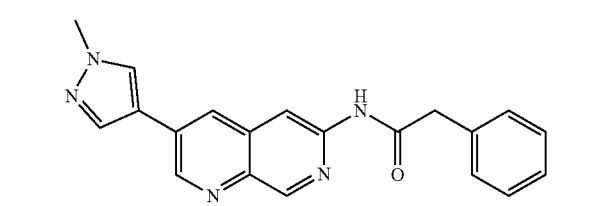 [SMILES: Cn1cc(-c2cnc3cnc(NC(=O)Cc4ccccc4)cc3c2)cn1]
2913
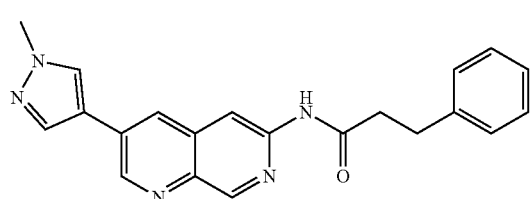
2914
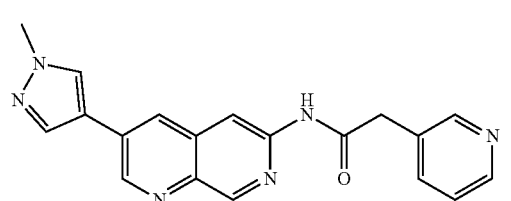
2915
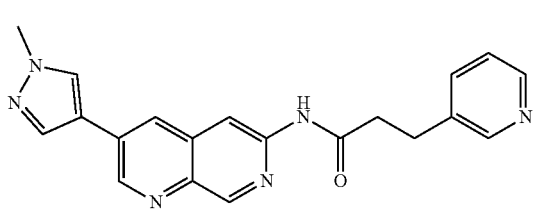 [SMILES: Cn1cc(-c2cnc3cnc(NC(=O)CCc4cccnc4)cc3c2)cn1]
2916

TABLE 1-continued
| | |
|---|---|
| 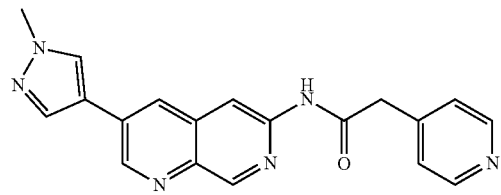 [SMILES: Cn1cc(-c2cnc3cnc(NC(=O)Cc4ccncc4)cc3c2)cn1] | 2917 |
| 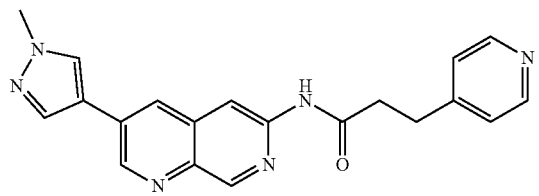 [SMILES: Cn1cc(-c2cnc3cnc(NC(=O)CCc4ccncc4)cc3c2)cn1] | 2918 |
| 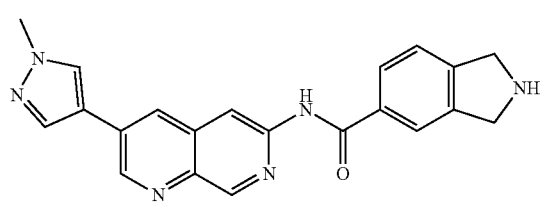 [SMILES: Cn1cc(-c2cnc3cnc(NC(=O)c4ccc5c(c4)CNC5)cc3c2)cn1] | 2919 |
| 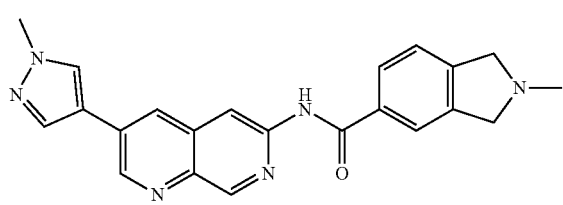 [SMILES: CN1Cc2ccc(C(=O)Nc3cc4cc(-c5cnn(C)c5)cnc4cn3)cc2C1] | 2920 |
| 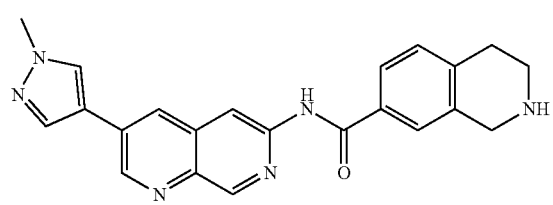 [SMILES: Cn1cc(-c2cnc3cnc(NC(=O)c4ccc5c(c4)CNCC5)cc3c2)cn1] | 2921 |
| 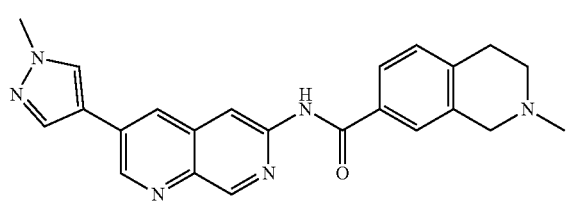 [SMILES: CN1CCc2ccc(C(=O)Nc3cc4cc(-c5cnn(C)c5)cnc4cn3)cc2C1] | 2922 |
| 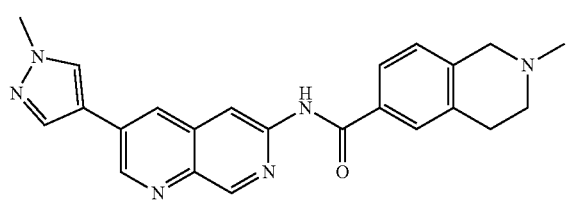 [SMILES: CN1CCc2cc(C(=O)Nc3cc4cc(-c5cnn(C)c5)cnc4cn3)ccc2C1] | 2923 |
| 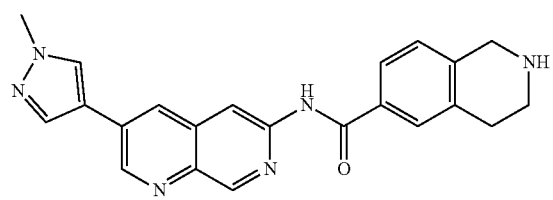 [SMILES: Cn1cc(-c2cnc3cnc(NC(=O)c4ccc5c(c4)CCNC5)cc3c2)cn1] | 2924 |

TABLE 1-continued
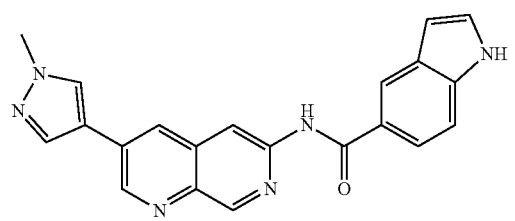 [SMILES: Cn1cc(-c2cnc3cnc(NC(=O)c4ccc5[nH]ccc5c4)cc3c2)cn1] 2925
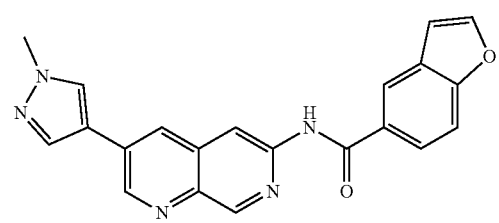 [SMILES: Cn1cc(-c2cnc3cnc(NC(=O)c4ccc5occc5c4)cc3c2)cn1] 2926
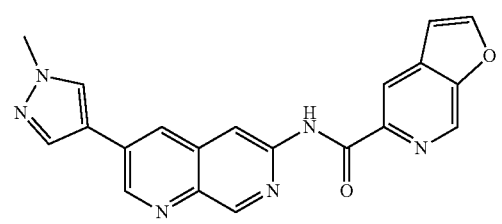 [SMILES: Cn1cc(-c2cnc3cnc(NC(=O)c4cc5ccoc5cn4)cc3c2)cn1] 2927
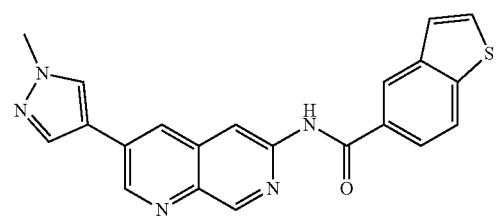 [SMILES: Cn1cc(-c2cnc3cnc(NC(=O)c4ccc5sccc5c4)cc3c2)cn1] 2928
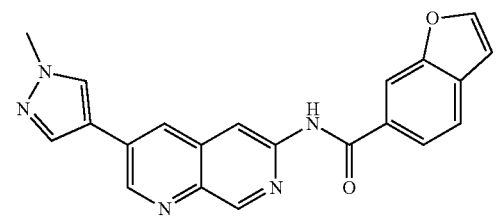 [SMILES: Cn1cc(-c2cnc3cnc(NC(=O)c4ccc5ccoc5c4)cc3c2)cn1] 2929
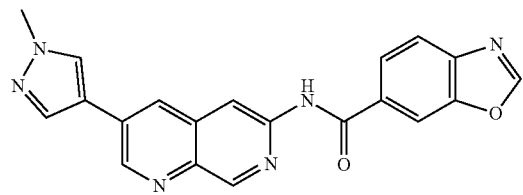 [SMILES: Cn1cc(-c2cnc3cnc(NC(=O)c4ccc5ncoc5c4)cc3c2)cn1] 2930
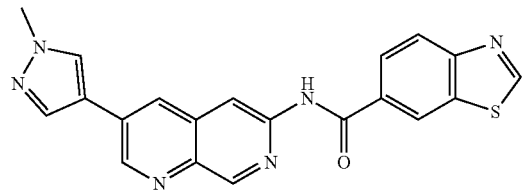 [SMILES: Cn1cc(-c2cnc3cnc(NC(=O)c4ccc5ncsc5c4)cc3c2)cn1] 2931

TABLE 1-continued
| | |
|---|---|
| 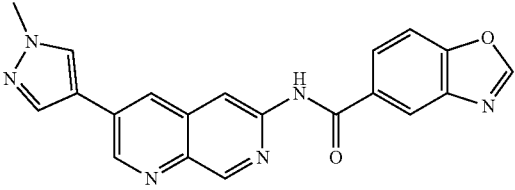 | 2932 |
| 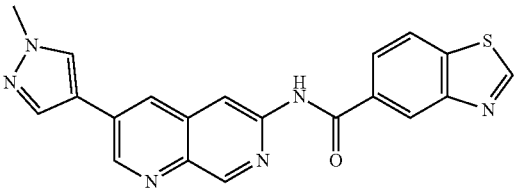 [SMILES: Cn1cc(-c2cnc3cnc(NC(=O)c4ccc5ocnc5c4)cc3c2)cn1] | 2933 |
| 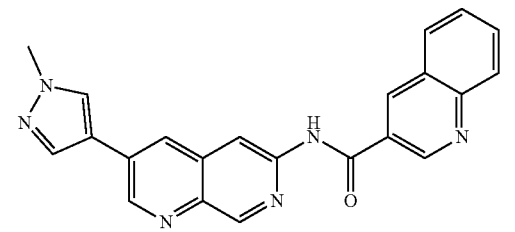 [SMILES: Cn1cc(-c2cnc3cnc(NC(=O)c4cnc5ccccc5c4)cc3c2)cn1] | 2934 |
| 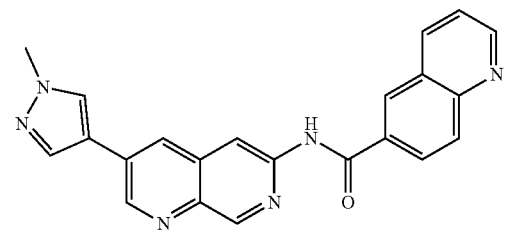 [SMILES: Cn1cc(-c2cnc3cnc(NC(=O)c4ccc5ncccc5c4)cc3c2)cn1] | 2935 |
| 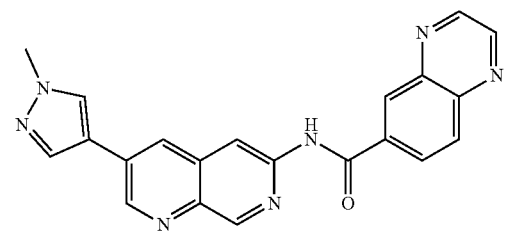 [SMILES: Cn1cc(-c2cnc3cnc(NC(=O)c4ccc5nccnc5c4)cc3c2)cn1] | 2936 |
| 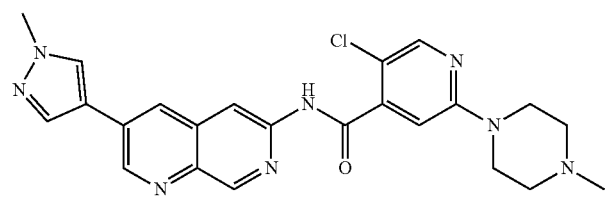 [SMILES: CN1CCN(c2cc(C(=O)Nc3cc4cc(-c5cnn(C)c5)cnc4cn3)c(Cl)cn2)CC1] | 2937 |
| 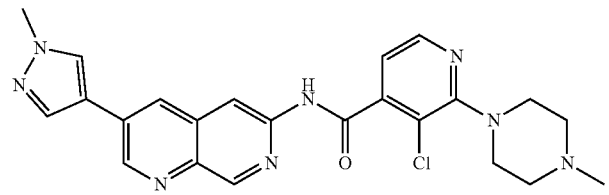 | 2938 |

TABLE 1-continued
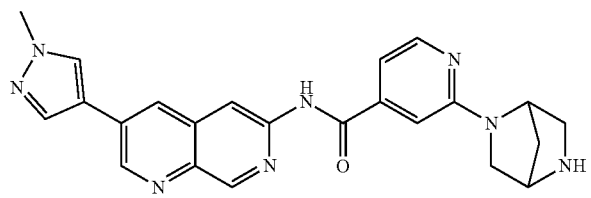 [SMILES: Cn1cc(-c2cnc3cnc(NC(=O)c4ccnc(N5CC6CC5CN6)c4)cc3c2)cn1] 2939
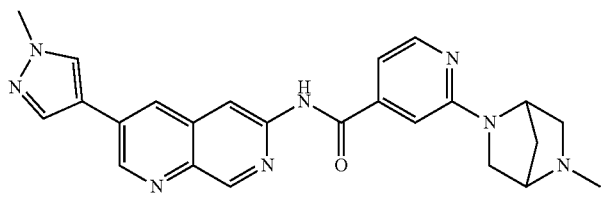 [SMILES: CN1CC2CC1CN2c1cc(C(=O)Nc2cc3cc(-c4cnn(C)c4)cnc3cn2)ccn1] 2940
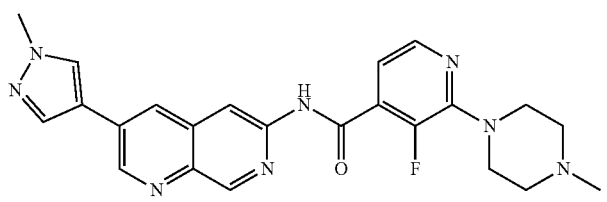 2941
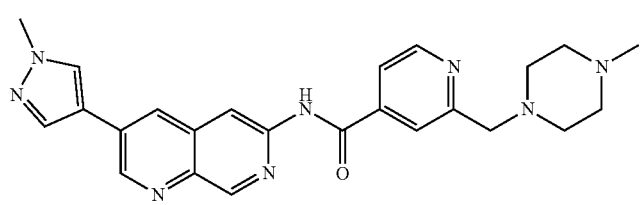 [SMILES: CN1CCN(Cc2cc(C(=O)Nc3cc4cc(-c5cnn(C)c5)cnc4cn3)ccn2)CC1] 2942
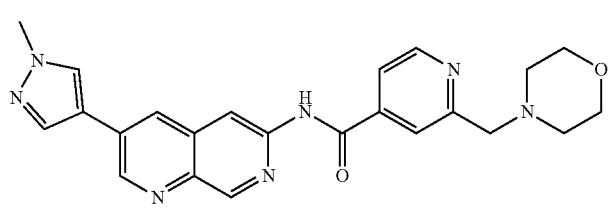 [SMILES: Cn1cc(-c2cnc3cnc(NC(=O)c4ccnc(CN5CCOCC5)c4)cc3c2)cn1] 2943
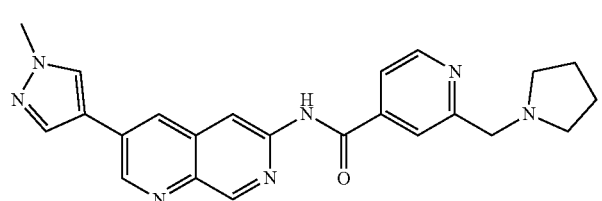 2944
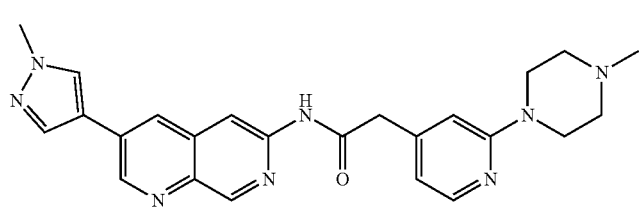 [SMILES: CN1CCN(c2cc(CC(=O)Nc3cc4cc(-c5cnn(C)c5)cnc4cn3)ccn2)CC1] 2945
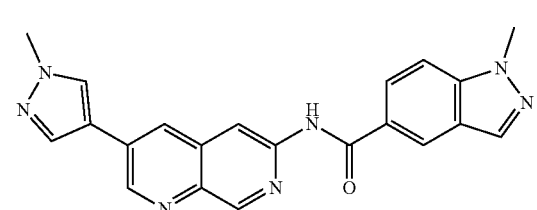 2946

TABLE 1-continued
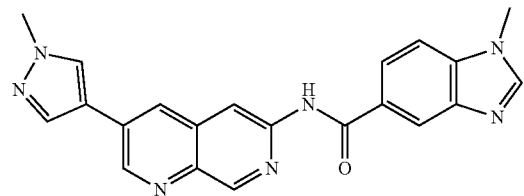 [SMILES: Cn1cc(-c2cnc3cnc(NC(=O)c4ccc5c(c4)ncn5C)cc3c2)cn1]
2947
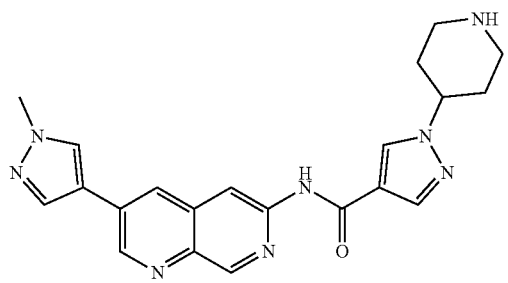 [SMILES: Cn1cc(-c2cnc3cnc(NC(=O)c4cnn(C5CCNCC5)c4)cc3c2)cn1]
2948
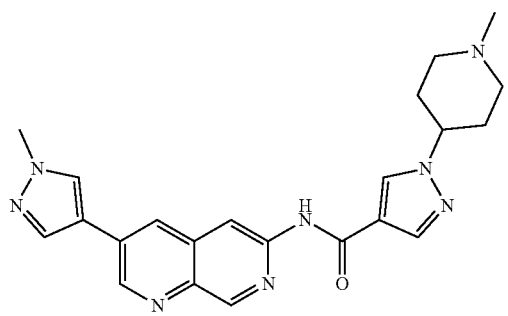
2949
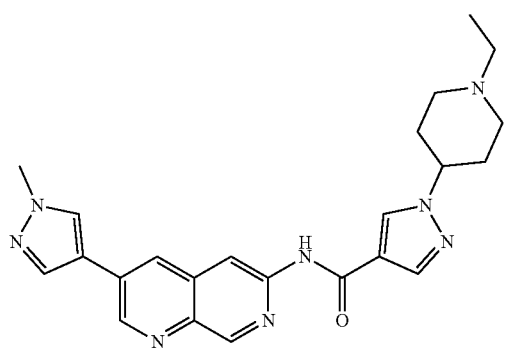 [SMILES: CCN1CCC(n2cc(C(=O)Nc3cc4cc(-c5cnn(C)c5)cnc4cn3)cn2)CC1]
2950
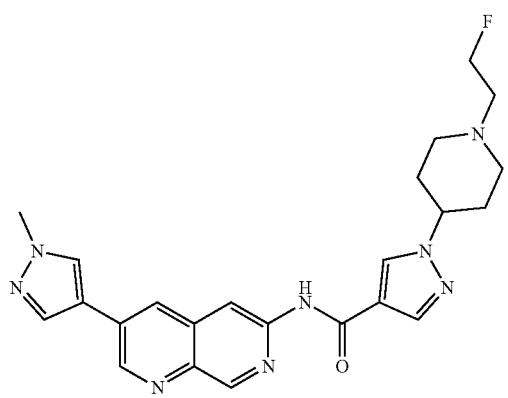 [SMILES: Cn1cc(-c2cnc3cnc(NC(=O)c4cnn(C5CCN(CCF)CC5)c4)cc3c2)cn1]
2951

TABLE 1-continued
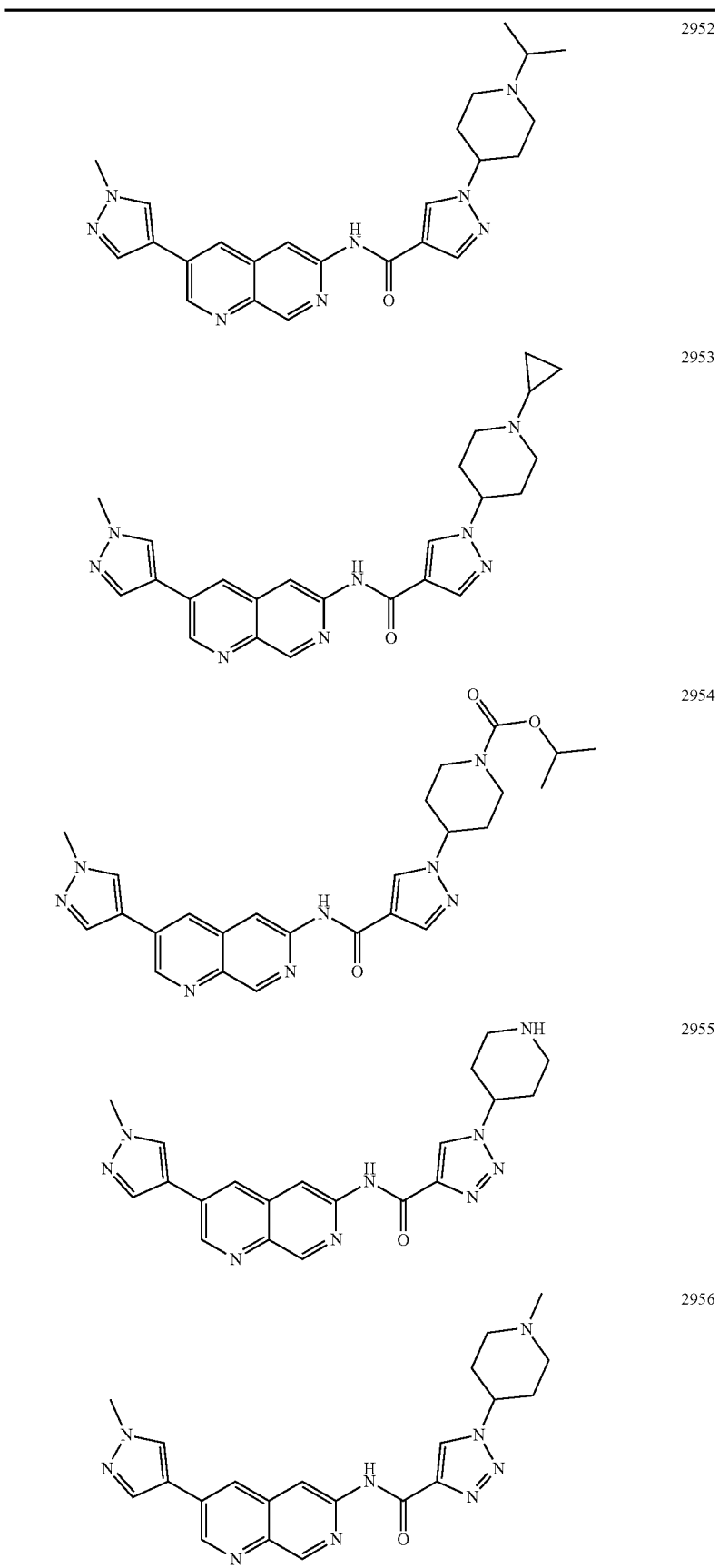

TABLE 1-continued
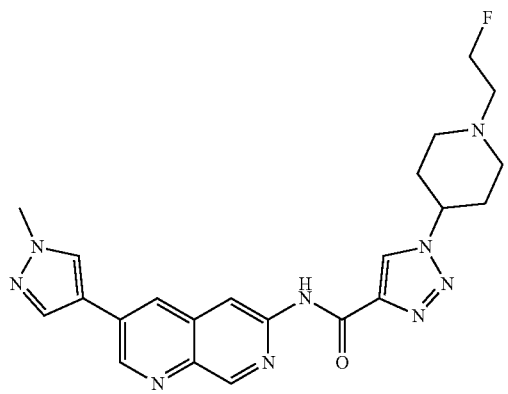 [SMILES: Cn1cc(-c2cnc3cnc(NC(=O)c4cn(C5CCN(CCF)CC5)nn4)cc3c2)cn1]
2957
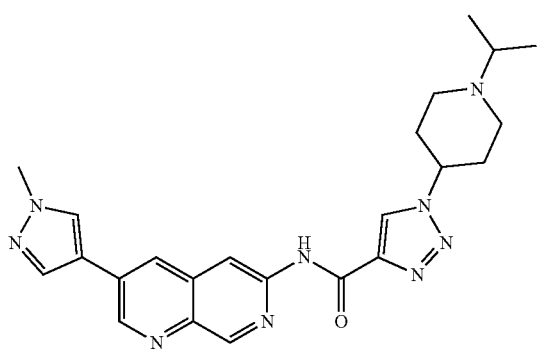 [SMILES: CC(C)N1CCC(n2cc(C(=O)Nc3cc4cc(-c5cnn(C)c5)cnc4cn3)nn2)CC1]
2958
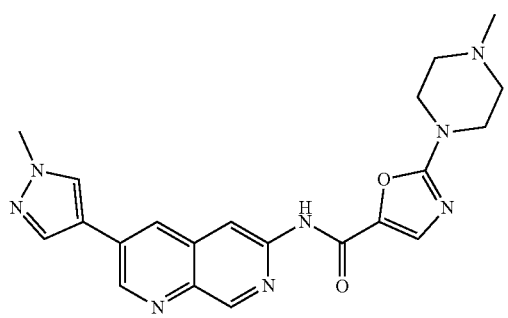 [SMILES: CN1CCN(c2ncc(C(=O)Nc3cc4cc(-c5cnn(C)c5)cnc4cn3)o2)CC1]
2959
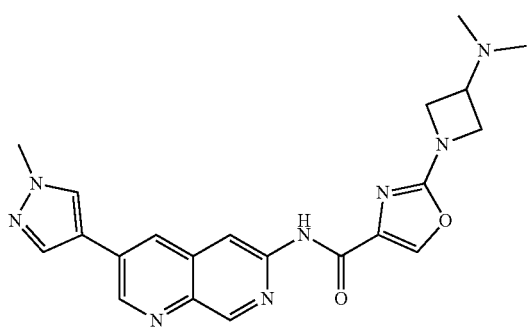 [SMILES: CN(C)C1CN(c2nc(C(=O)Nc3cc4cc(-c5cnn(C)c5)cnc4cn3)co2)C1]
2960

TABLE 1-continued
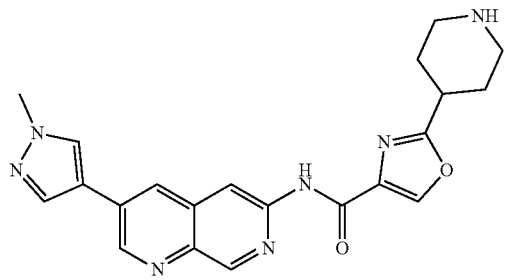
2961
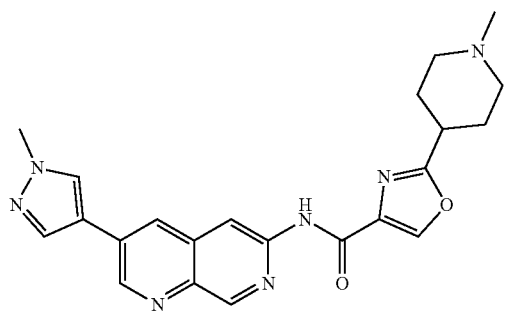 [SMILES: CN1CCC(c2nc(C(=O)Nc3cc4cc(-c5cnn(C)c5)cnc4cn3)co2)CC1]
2962
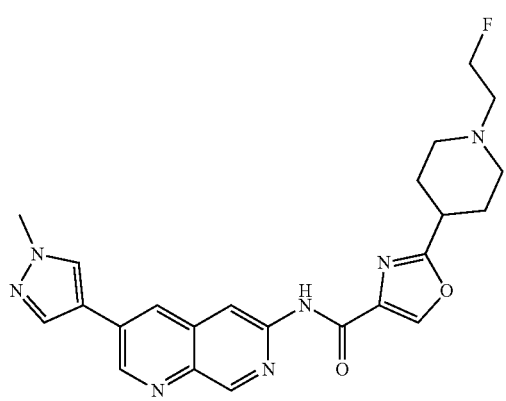
2963
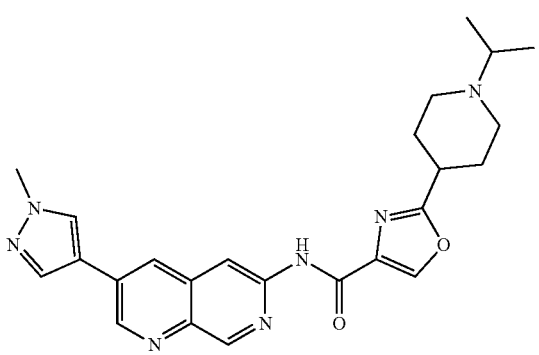
2964
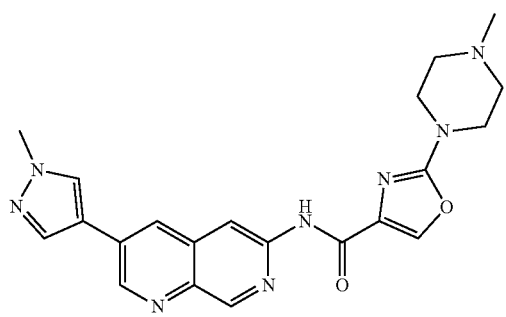 [SMILES: CN1CCN(c2nc(C(=O)Nc3cc4cc(-c5cnn(C)c5)cnc4cn3)co2)CC1]
2965

TABLE 1-continued
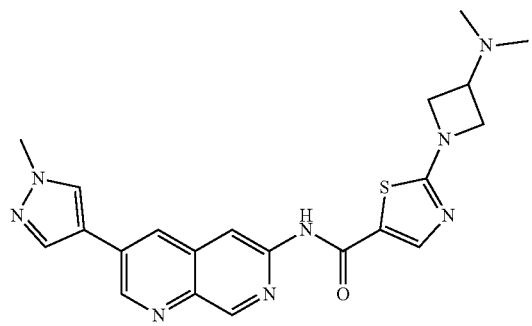 [SMILES: CN(C)C1CN(c2ncc(C(=O)Nc3cc4cc(-c5cnn(C)c5)cnc4cn3)s2)C1]
2966
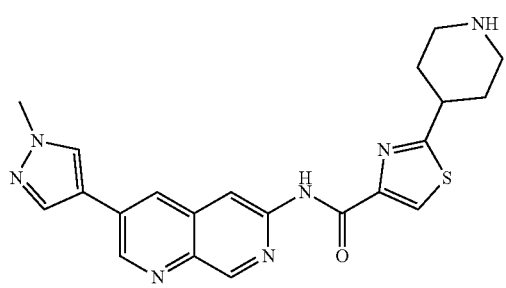 [SMILES: Cn1cc(-c2cnc3cnc(NC(=O)c4csc(C5CCNCC5)n4)cc3c2)cn1]
2967
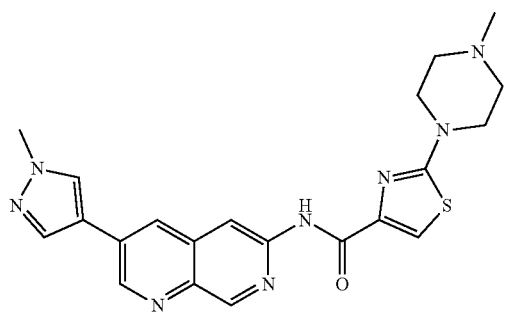
2968
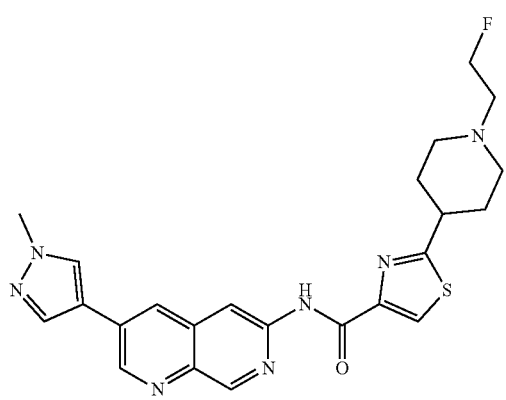
2969

TABLE 1-continued
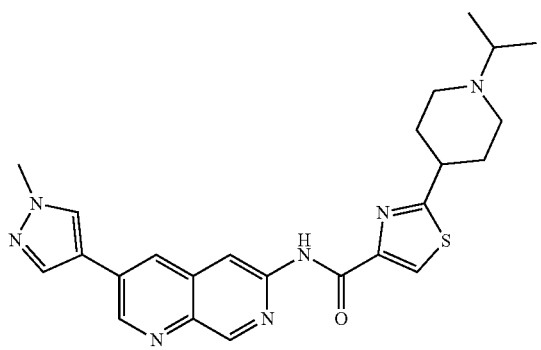
2970
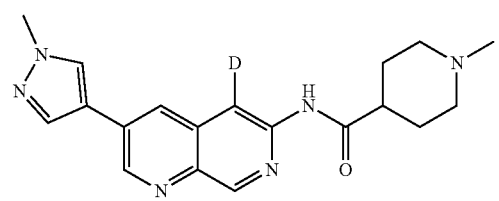 [SMILES: [2H]c1c(NC(=O)C2CCN(C)CC2)ncc2ncc(-c3cnn(C)c3)cc12]
2971
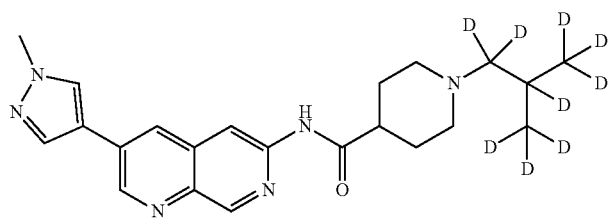 [SMILES: [2H]C([2H])([2H])C([2H])(C([2H])([2H])[2H])C([2H])([2H])N1CCC(C(=O)Nc2cc3cc(-c4cnn(C)c4)cnc3cn2)CC1]
2972
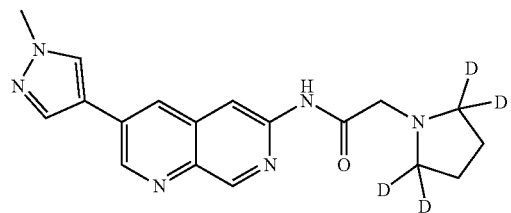 [SMILES: [2H]C1([2H])CCC([2H])([2H])N1CC(=O)Nc1cc2cc(-c3cnn(C)c3)cnc2cn1]
2973
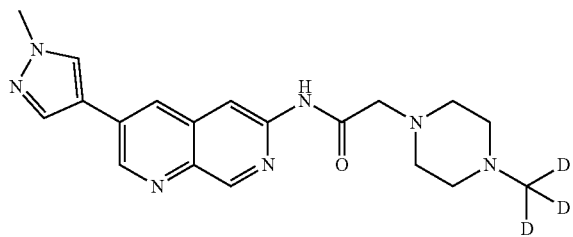 [SMILES: [2H]C([2H])([2H])N1CCN(CC(=O)Nc2cc3cc(-c4cnn(C)c4)cnc3cn2)CC1]
2974
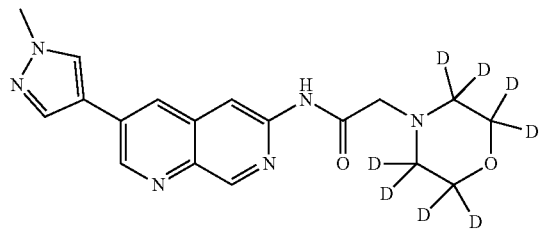 [SMILES: [2H]C1([2H])OC([2H])([2H])C([2H])([2H])N(CC(=O)Nc2cc3cc(-c4cnn(C)c4)cnc3cn2)C1([2H])[2H]]
2975

TABLE 1-continued
| | |
|---|---|
| 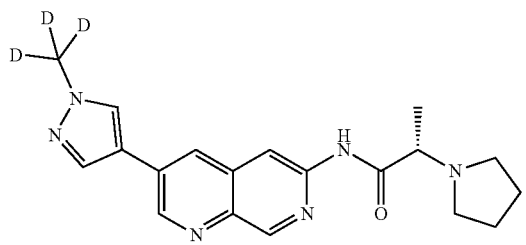 [SMILES: [2H]C([2H])([2H])n1cc(-c2cnc3cnc(NC(=O)[C@H](C)N4CCCC4)cc3c2)cn1] | 2976 |
| 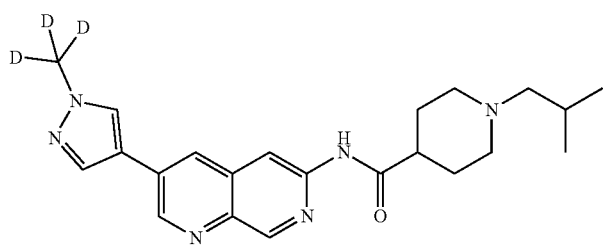 [SMILES: [2H]C([2H])([2H])n1cc(-c2cnc3cnc(NC(=O)C4CCN(CC(C)C)CC4)cc3c2)cn1] | 2977 |
| 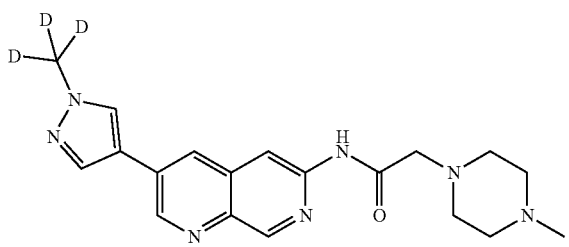 [SMILES: [2H]C([2H])([2H])n1cc(-c2cnc3cnc(NC(=O)CN4CCN(C)CC4)cc3c2)cn1] | 2978 |
| 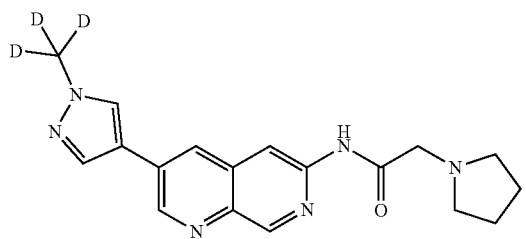 [SMILES: [2H]C([2H])([2H])n1cc(-c2cnc3cnc(NC(=O)CN4CCCC4)cc3c2)cn1] | 2979 |
| 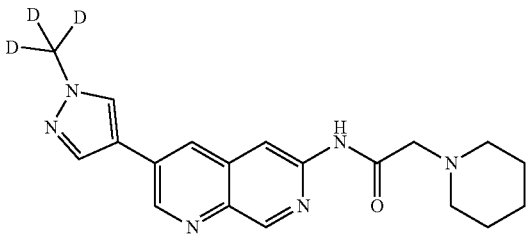 [SMILES: [2H]C([2H])([2H])n1cc(-c2cnc3cnc(NC(=O)CN4CCCCC4)cc3c2)cn1] | 2980 |
| 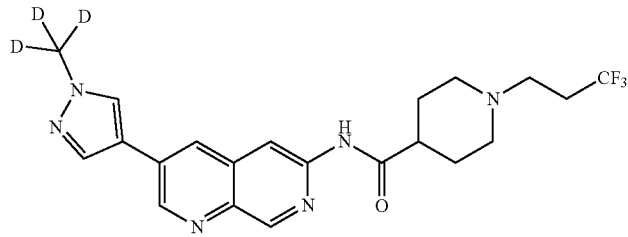 [SMILES: [2H]C([2H])([2H])n1cc(-c2cnc3cnc(NC(=O)C4CCN(CCC(F)(F)F)CC4)cc3c2)cn1] | 2981 |

TABLE 1-continued
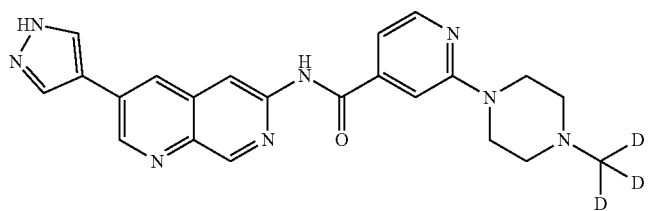 [SMILES: [2H]C([2H])([2H])N1CCN(c2cc(C(=O)Nc3cc4cc(-c5cn[nH]c5)cnc4cn3)ccn2)CC1]
2982
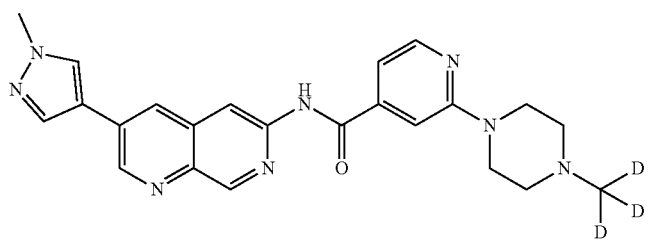
2983
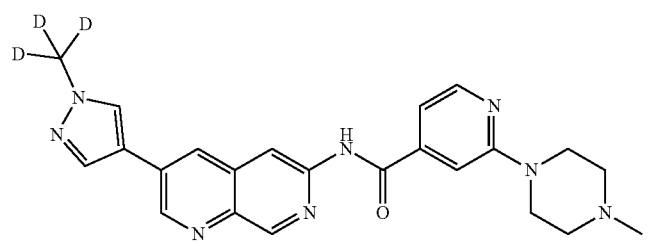 [SMILES: [2H]C([2H])([2H])n1cc(-c2cnc3cnc(NC(=O)c4ccnc(N5CCN(C)CC5)c4)cc3c2)cn1]
2984
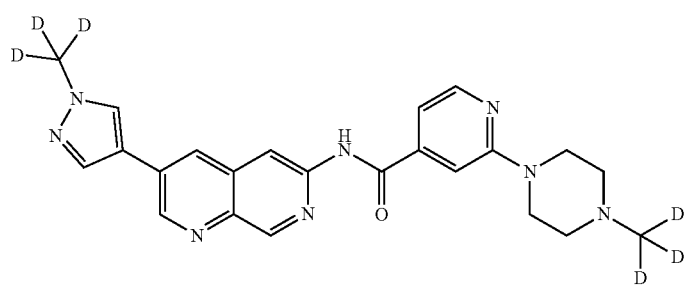 [SMILES: [2H]C([2H])([2H])N1CCN(c2cc(C(=O)Nc3cc4cc(-c5cnn(C([2H])([2H])[2H])c5)cnc4cn3)ccn2)CC1]
2985
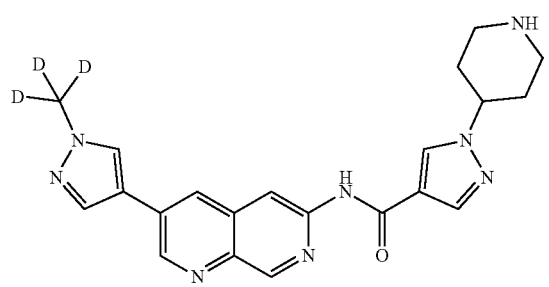 [SMILES: [2H]C([2H])([2H])n1cc(-c2cnc3cnc(NC(=O)c4cnn(C5CCNCC5)c4)cc3c2)cn1]
2986
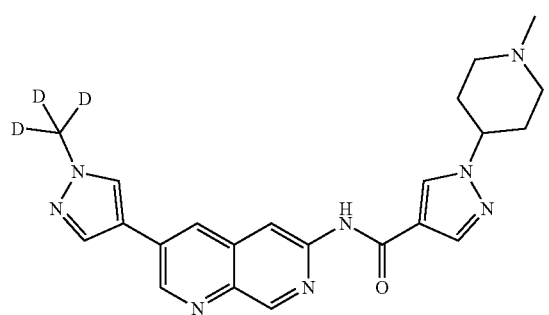 [SMILES: [2H]C([2H])([2H])n1cc(-c2cnc3cnc(NC(=O)c4cnn(C5CCN(C)CC5)c4)cc3c2)cn1]
2987

TABLE 1-continued
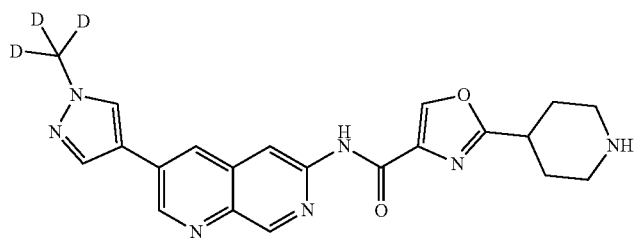 [SMILES: [2H]C([2H])([2H])n1cc(-c2cnc3cnc(NC(=O)c4coc(C5CCNCC5)n4)cc3c2)cn1]
2988
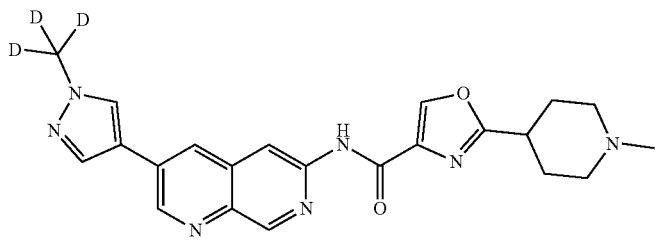 [SMILES: [2H]C([2H])([2H])n1cc(-c2cnc3cnc(NC(=O)c4coc(C5CCN(C)CC5)n4)cc3c2)cn1]
2989
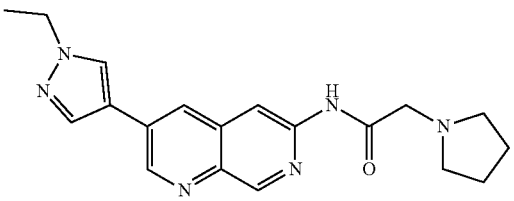 [SMILES: CCn1cc(-c2cnc3cnc(NC(=O)CN4CCCC4)cc3c2)cn1]
2990
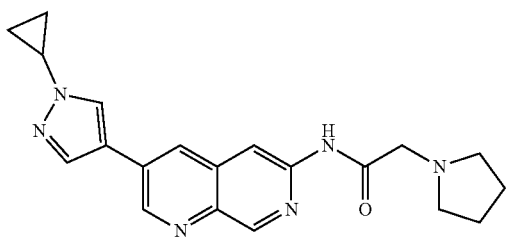 [SMILES: O=C(CN1CCCC1)Nc1cc2cc(-c3cnn(C4CC4)c3)cnc2cn1]
2991
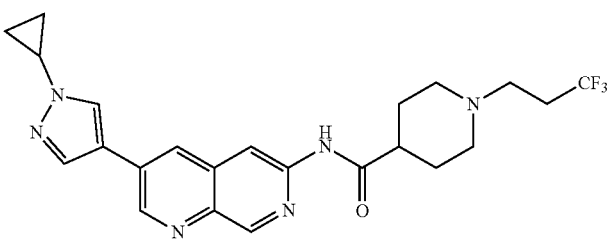 [SMILES: O=C(Nc1cc2cc(-c3cnn(C4CC4)c3)cnc2cn1)C1CCN(CCC(F)(F)F)CC1]
2992
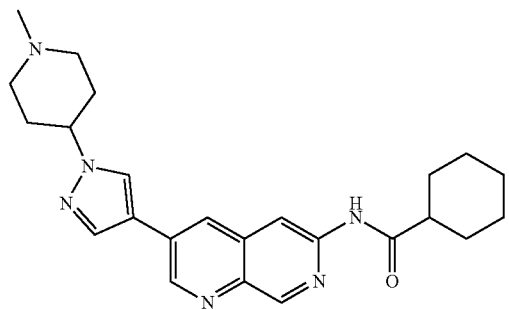 [SMILES: CN1CCC(n2cc(-c3cnc4cnc(NC(=O)C5CCCCC5)cc4c3)cn2)CC1]
2993

TABLE 1-continued
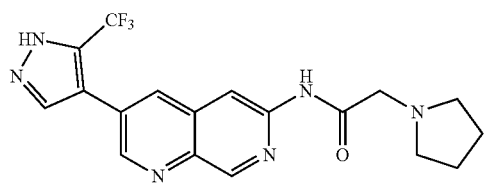 [SMILES: O=C(CN1CCCC1)Nc1cc2cc(-c3cn[nH]c3C(F)(F)F)cnc2cn1]
2994
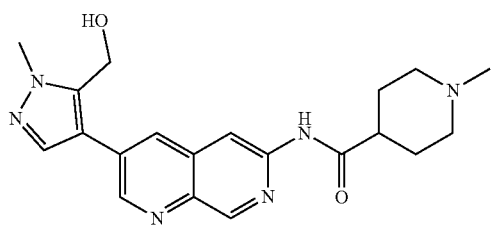 [SMILES: CN1CCC(C(=O)Nc2cc3cc(-c4cnn(C)c4CO)cnc3cn2)CC1]
2995
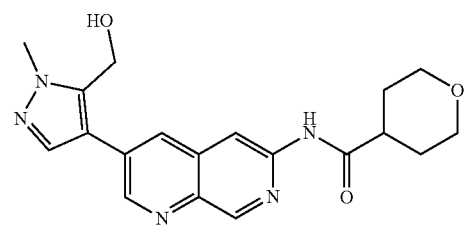 [SMILES: Cn1ncc(-c2cnc3cnc(NC(=O)C4CCOCC4)cc3c2)c1CO]
2996
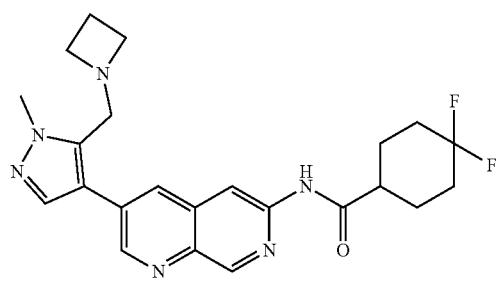 [SMILES: Cn1ncc(-c2cnc3cnc(NC(=O)C4CCC(F)(F)CC4)cc3c2)c1CN1CCC1]
2997
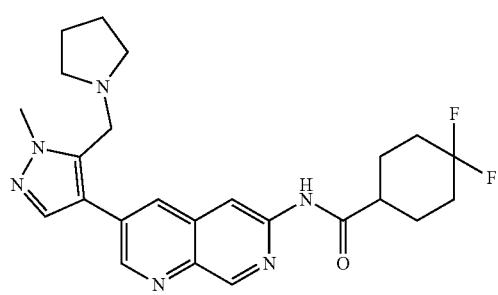 [SMILES: Cn1ncc(-c2cnc3cnc(NC(=O)C4CCC(F)(F)CC4)cc3c2)c1CN1CCCC1]
2998
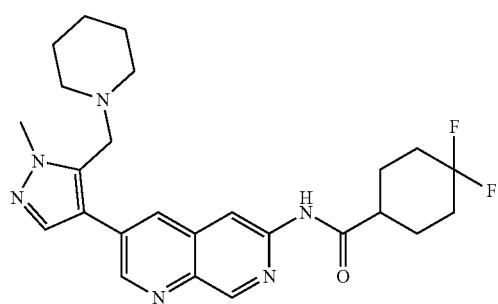 [SMILES: Cn1ncc(-c2cnc3cnc(NC(=O)C4CCC(F)(F)CC4)cc3c2)c1CN1CCCCC1]
2999

TABLE 1-continued
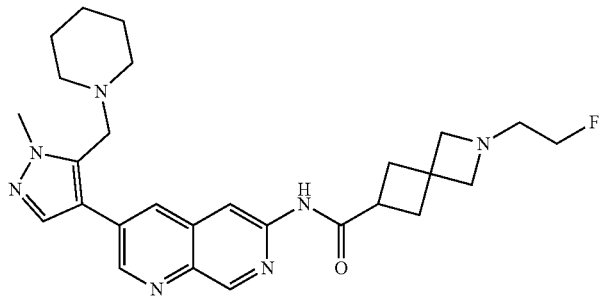 [SMILES: Cn1ncc(-c2cnc3cnc(NC(=O)C4CC5(C4)CN(CCF)C5)cc3c2)c1CN1CCCCC1]
3000
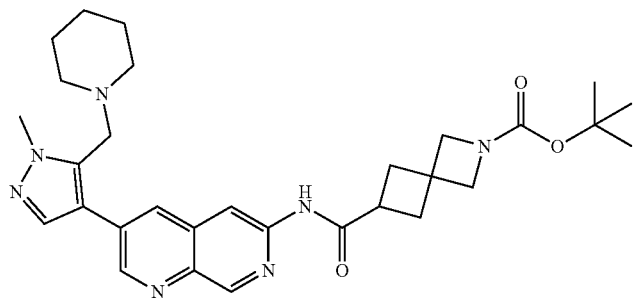 [SMILES: Cn1ncc(-c2cnc3cnc(NC(=O)C4CC5(C4)CN(C(=O)OC(C)(C)C)C5)cc3c2)c1CN1CCCCC1]
3001
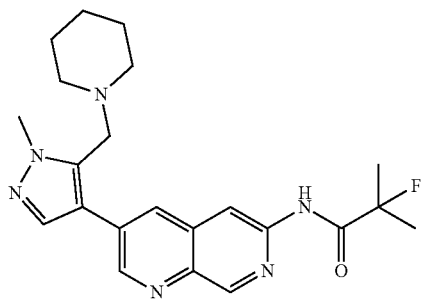 [SMILES: Cn1ncc(-c2cnc3cnc(NC(=O)C(C)(C)F)cc3c2)c1CN1CCCCC1]
3002
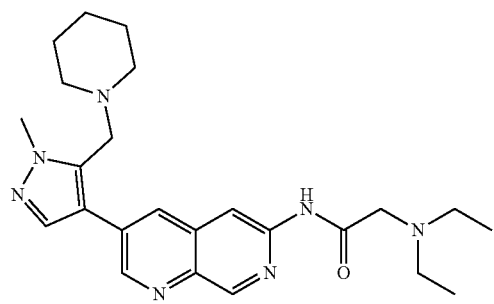 [SMILES: CCN(CC)CC(=O)Nc1cc2cc(-c3cnn(C)c3CN3CCCCC3)cnc2cn1]
3003
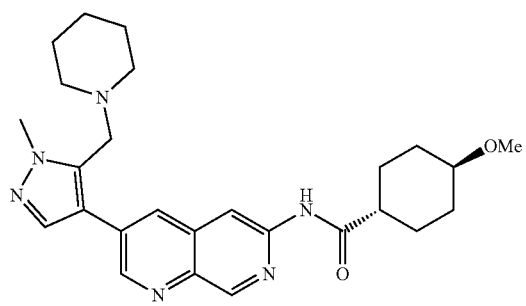 [SMILES: CO[C@H]1CC[C@H](C(=O)Nc2cc3cc(-c4cnn(C)c4CN4CCCCC4)cnc3cn2)CC1]
3004

TABLE 1-continued
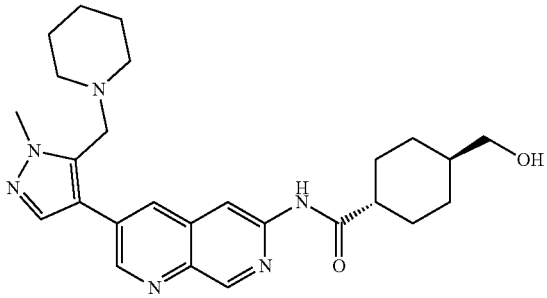 [SMILES: Cn1ncc(-c2cnc3cnc(NC(=O)[C@H]4CC[C@H](CO)CC4)cc3c2)c1CN1CCCCC1] 3005
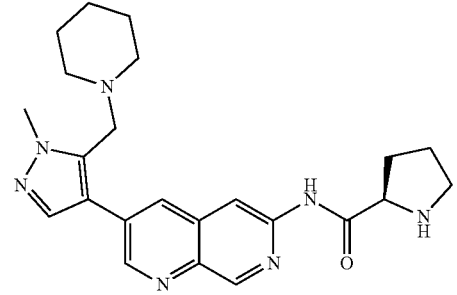 [SMILES: Cn1ncc(-c2cnc3cnc(NC(=O)[C@H]4CCCN4)cc3c2)c1CN1CCCCC1] 3006
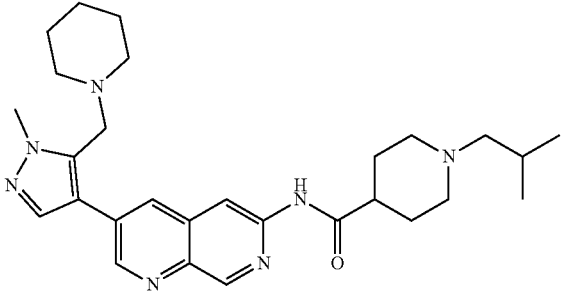 [SMILES: CC(C)CN1CCC(C(=O)Nc2cc3cc(-c4cnn(C)c4CN4CCCCC4)cnc3cn2)CC1] 3007
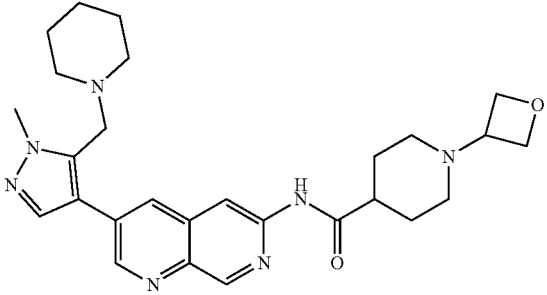 [SMILES: Cn1ncc(-c2cnc3cnc(NC(=O)C4CCN(C5COC5)CC4)cc3c2)c1CN1CCCCC1] 3008
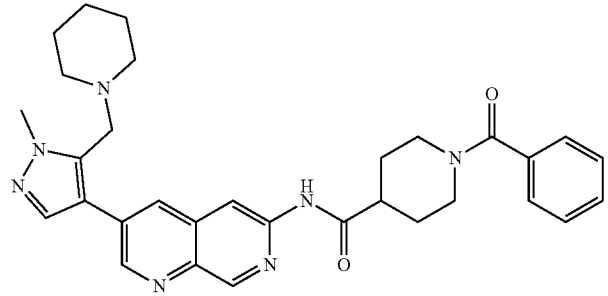 [SMILES: Cn1ncc(-c2cnc3cnc(NC(=O)C4CCN(C(=O)c5ccccc5)CC4)cc3c2)c1CN1CCCCC1] 3009

TABLE 1-continued
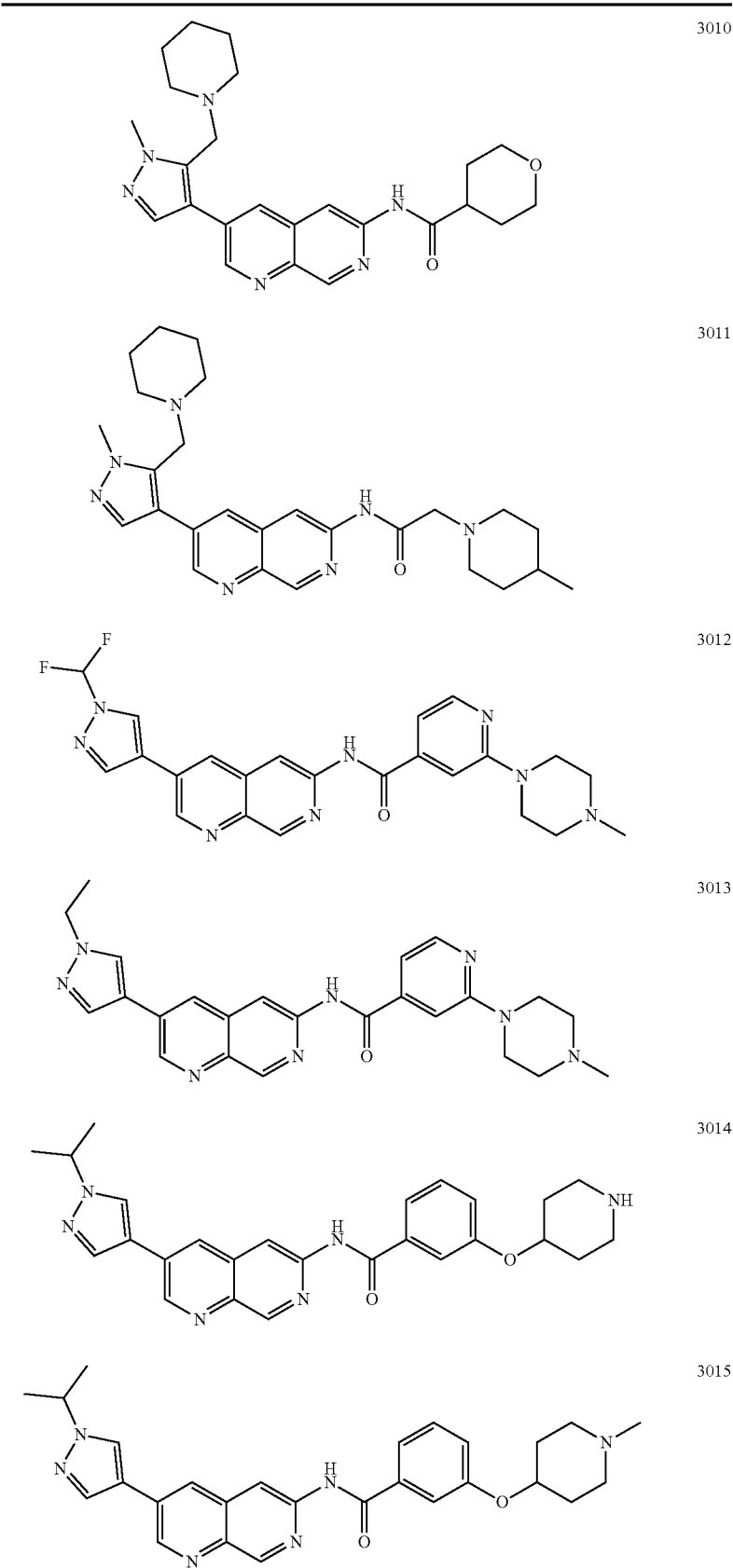

TABLE 1-continued
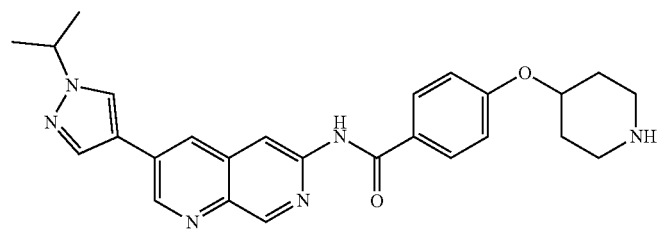 [SMILES: CC(C)n1cc(-c2cnc3cnc(NC(=O)c4ccc(OC5CCNCC5)cc4)cc3c2)cn1]
3016
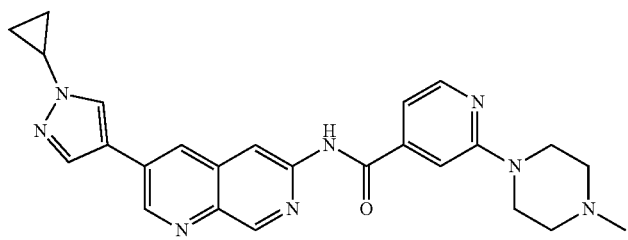 [SMILES: CN1CCN(c2cc(C(=O)Nc3cc4cc(-c5cnn(C6CC6)c5)cnc4cn3)ccn2)CC1]
3017
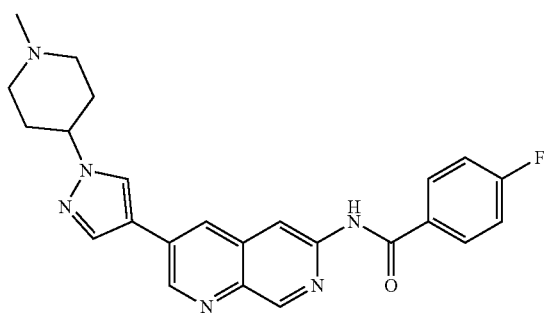 [SMILES: CN1CCC(n2cc(-c3cnc4cnc(NC(=O)c5ccc(F)cc5)cc4c3)cn2)CC1]
3018
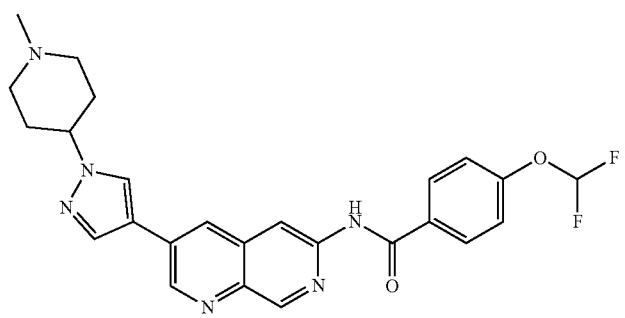 [SMILES: CN1CCC(n2cc(-c3cnc4cnc(NC(=O)c5ccc(OC(F)F)cc5)cc4c3)cn2)CC1]
3019
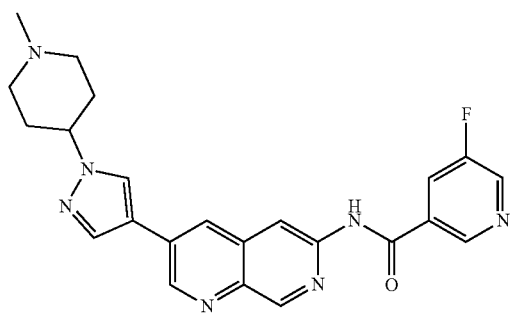 [SMILES: CN1CCC(n2cc(-c3cnc4cnc(NC(=O)c5cncc(F)c5)cc4c3)cn2)CC1]
3020

TABLE 1-continued
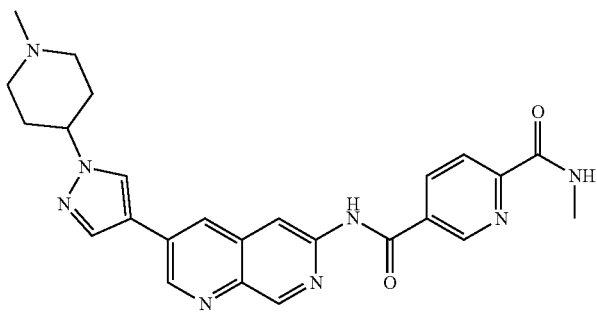 [SMILES: CNC(=O)c1ccc(C(=O)Nc2cc3cc(-c4cnn(C5CCN(C)CC5)c4)cnc3cn2)cn1]
3021
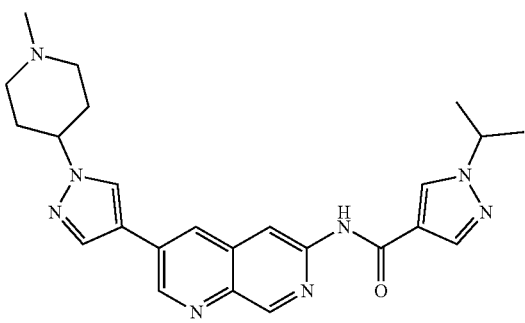 [SMILES: CC(C)n1cc(C(=O)Nc2cc3cc(-c4cnn(C5CCN(C)CC5)c4)cnc3cn2)cn1]
3022
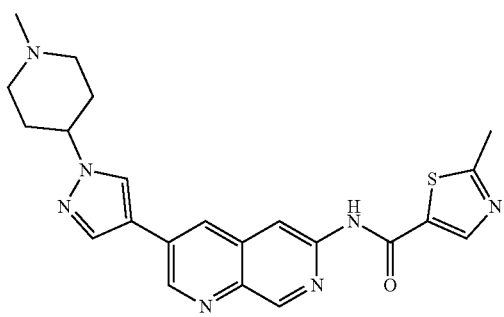 [SMILES: Cc1ncc(C(=O)Nc2cc3cc(-c4cnn(C5CCN(C)CC5)c4)cnc3cn2)s1]
3023
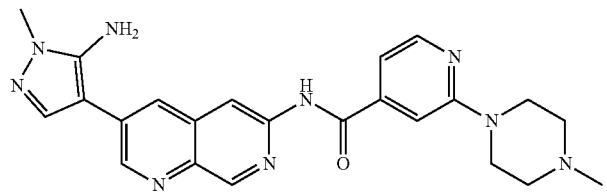 [SMILES: CN1CCN(c2cc(C(=O)Nc3cc4cc(-c5cnn(C)c5N)cnc4cn3)ccn2)CC1]
3024
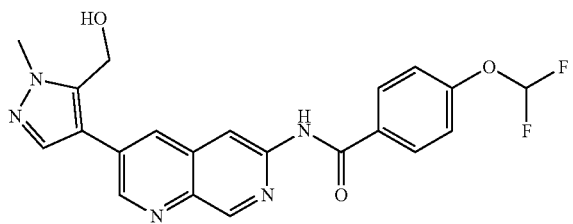 [SMILES: Cn1ncc(-c2cnc3cnc(NC(=O)c4ccc(OC(F)F)cc4)cc3c2)c1CO]
3025
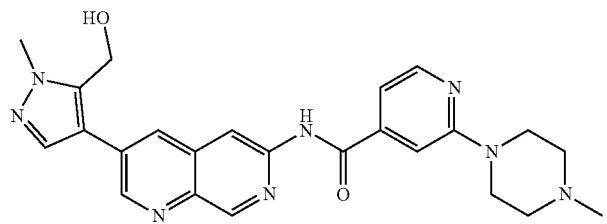 [SMILES: CN1CCN(c2cc(C(=O)Nc3cc4cc(-c5cnn(C)c5CO)cnc4cn3)ccn2)CC1]
3026

TABLE 1-continued
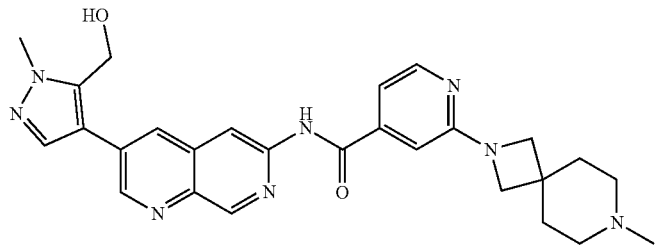 [SMILES: CN1CCC2(CC1)CN(c1cc(C(=O)Nc3cc4cc(-c5cnn(C)c5CO)cnc4cn3)ccn1)C2]
3027
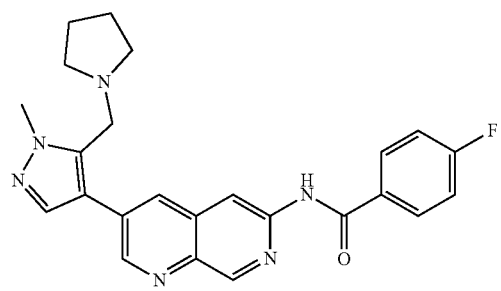 [SMILES: Cn1ncc(-c2cnc3cnc(NC(=O)c4ccc(F)cc4)cc3c2)c1CN1CCCC1]
3028
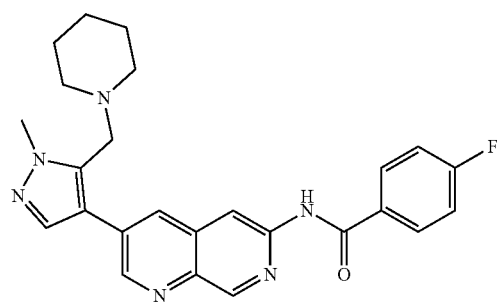 [SMILES: Cn1ncc(-c2cnc3cnc(NC(=O)c4ccc(F)cc4)cc3c2)c1CN1CCCCC1]
3029
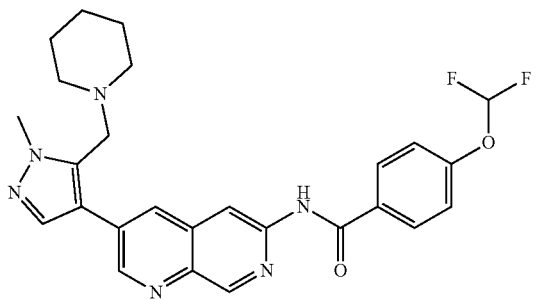 [SMILES: Cn1ncc(-c2cnc3cnc(NC(=O)c4ccc(OC(F)F)cc4)cc3c2)c1CN1CCCCC1]
3030
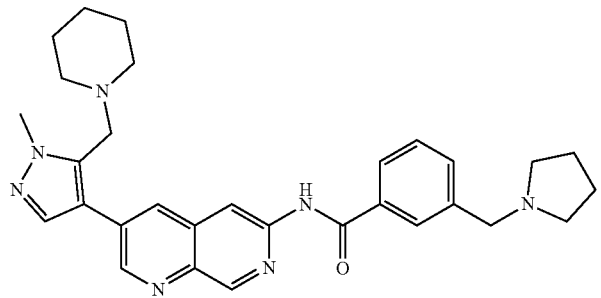 [SMILES: Cn1ncc(-c2cnc3cnc(NC(=O)c4cccc(CN5CCCC5)c4)cc3c2)c1CN1CCCCC1]
3031

TABLE 1-continued
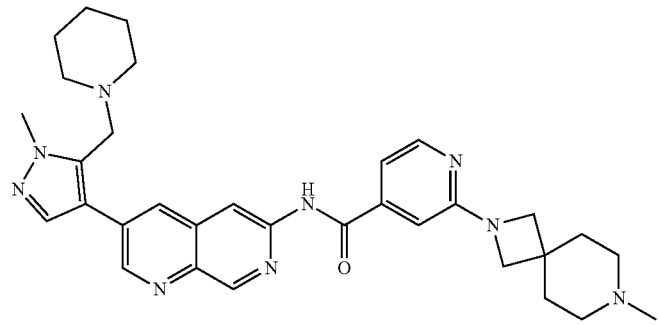 [SMILES: CN1CCC2(CC1)CN(c1cc(C(=O)Nc3cc4cc(-c5cnn(C)c5CN5CCCCC5)cnc4cn3)ccn1)C2]
3032
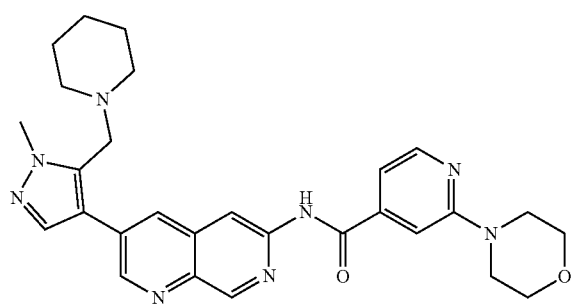
3033
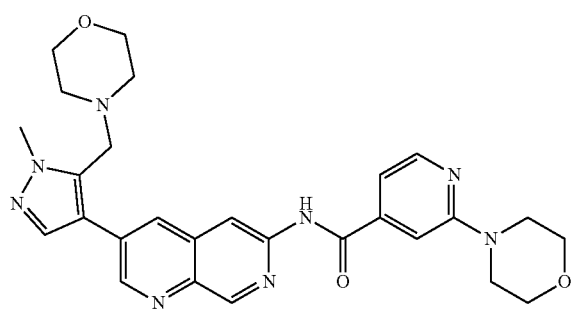 [SMILES: Cn1ncc(-c2cnc3cnc(NC(=O)c4ccnc(N5CCOCC5)c4)cc3c2)c1CN1CCOCC1]
3034
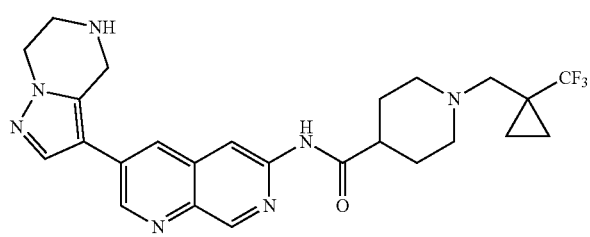 [SMILES: O=C(Nc1cc2cc(-c3cnn4c3CNCC4)cnc2cn1)C1CCN(CC2(C(F)(F)F)CC2)CC1]
3035
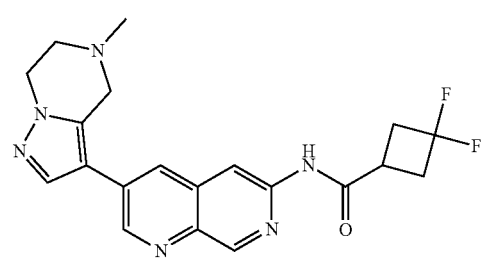 [SMILES: CN1CCn2ncc(-c3cnc4cnc(NC(=O)C5CC(F)(F)C5)cc4c3)c2C1]
3036

TABLE 1-continued
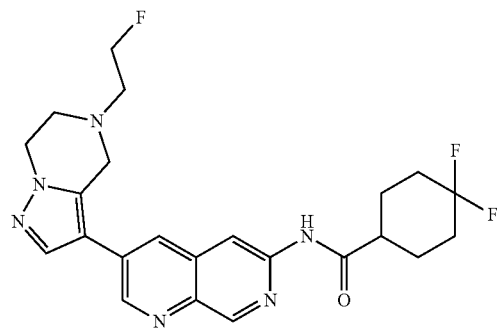 [SMILES: O=C(Nc1cc2cc(-c3cnn4c3CN(CCF)CC4)cnc2cn1)C1CCC(F)(F)CC1]
3037
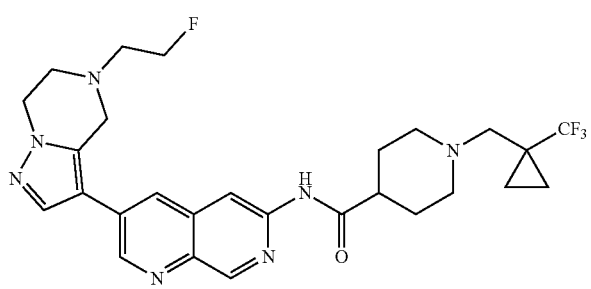
3038
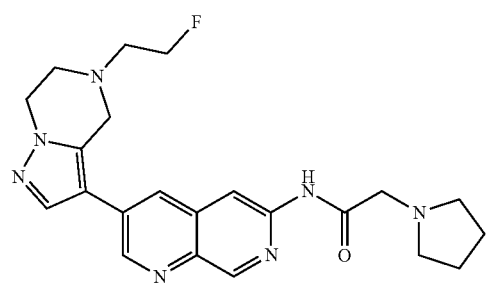 [SMILES: O=C(CN1CCCC1)Nc1cc2cc(-c3cnn4c3CN(CCF)CC4)cnc2cn1]
3039
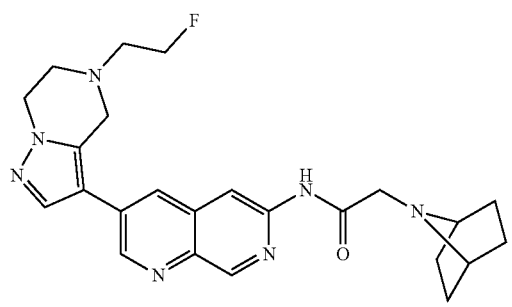 [SMILES: O=C(CN1C2CCC1CC2)Nc1cc2cc(-c3cnn4c3CN(CCF)CC4)cnc2cn1]
3040
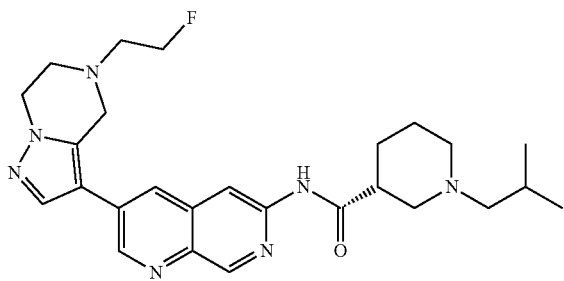
3041

TABLE 1-continued
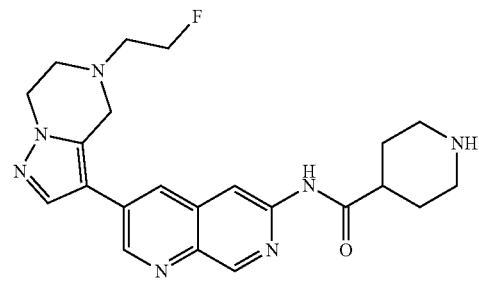 [SMILES: O=C(Nc1cc2cc(-c3cnn4c3CN(CCF)CC4)cnc2cn1)C1CCNCC1]
3042
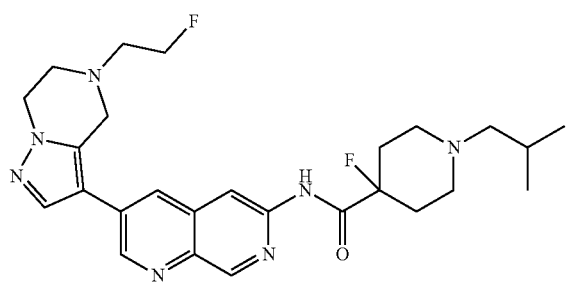
3043
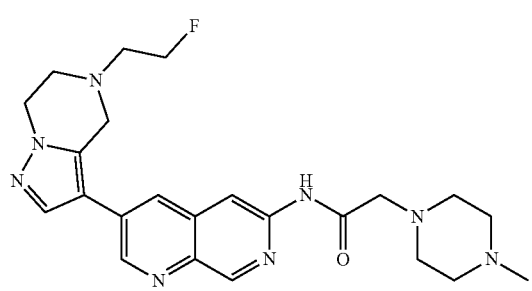 [SMILES: CN1CCN(CC(=O)Nc2cc3cc(-c4cnn5c4CN(CCF)CC5)cnc3cn2)CC1]
3044
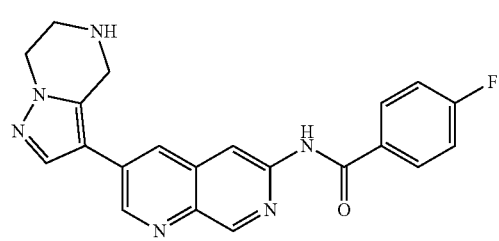 [SMILES: O=C(Nc1cc2cc(-c3cnn4c3CNCC4)cnc2cn1)c1ccc(F)cc1]
3045
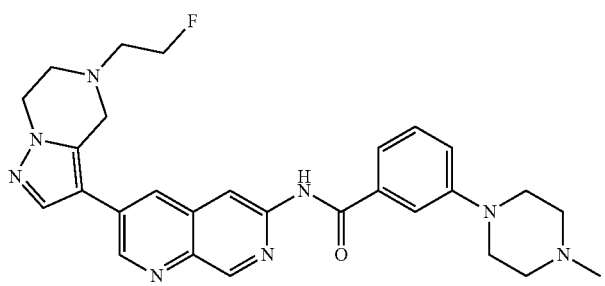 [SMILES: CN1CCN(c2cccc(C(=O)Nc3cc4cc(-c5cnn6c5CN(CCF)CC6)cnc4cn3)c2)CC1]
3046
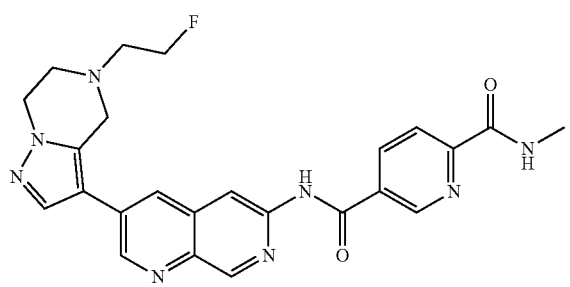 [SMILES: CNC(=O)c1ccc(C(=O)Nc2cc3cc(-c4cnn5c4CN(CCF)CC5)cnc3cn2)cn1]
3047

TABLE 1-continued
| | |
|---|---|
| 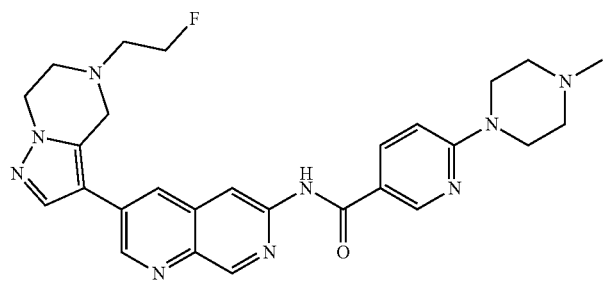 [SMILES: CN1CCN(c2ccc(C(=O)Nc3cc4cc(-c5cnn6c5CN(CCF)CC6)cnc4cn3)cn2)CC1] | 3048 |
| 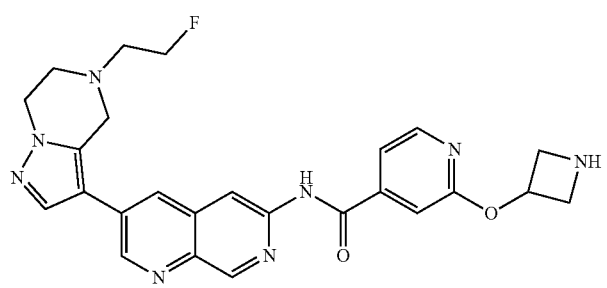 [SMILES: O=C(Nc1cc2cc(-c3cnn4c3CN(CCF)CC4)cnc2cn1)c1ccnc(OC2CNC2)c1] | 3049 |
| 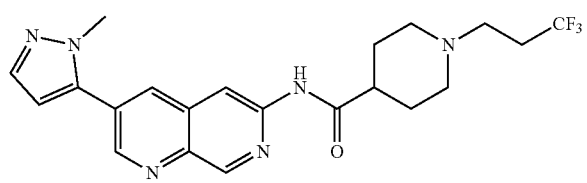 [SMILES: Cn1nccc1-c1cnc2cnc(NC(=O)C3CCN(CCC(F)(F)F)CC3)cc2c1] | 3050 |
| 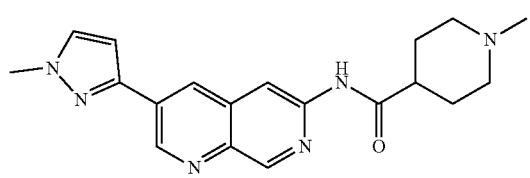 | 3051 |
| 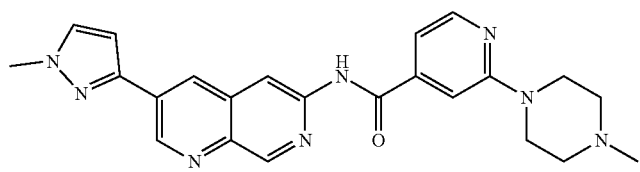 | 3052 |
| 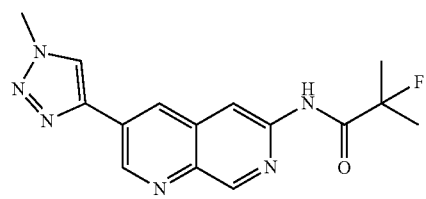 [SMILES: Cn1cc(-c2cnc3cnc(NC(=O)C(C)(C)F)cc3c2)nn1] | 3053 |
| 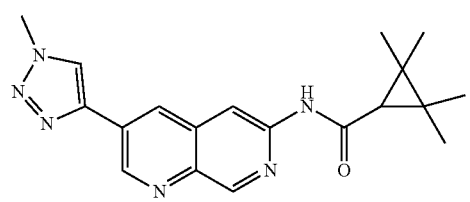 [SMILES: Cn1cc(-c2cnc3cnc(NC(=O)C4C(C)(C)C4(C)C)cc3c2)nn1] | 3054 |

TABLE 1-continued
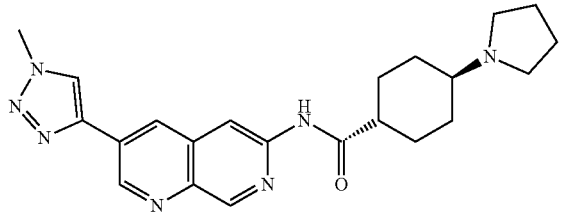
3055
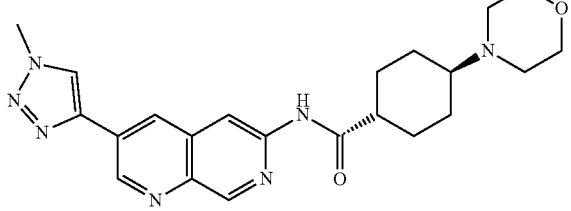
3056
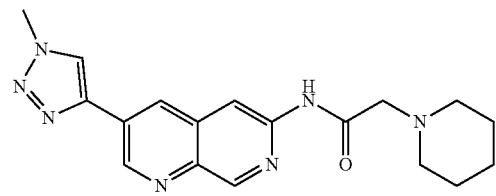 [SMILES: Cn1cc(-c2cnc3cnc(NC(=O)CN4CCCCC4)cc3c2)nn1]
3057
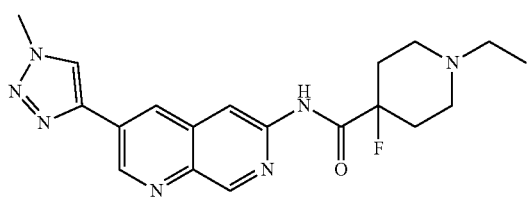 [SMILES: CCN1CCC(F)(C(=O)Nc2cc3cc(-c4cn(C)nn4)cnc3cn2)CC1]
3058
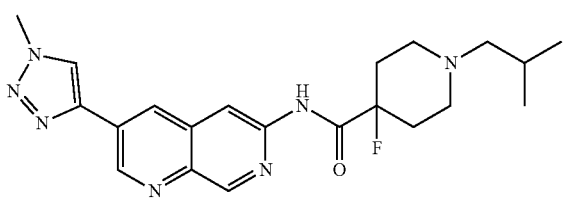 [SMILES: CC(C)CN1CCC(F)(C(=O)Nc2cc3cc(-c4cn(C)nn4)cnc3cn2)CC1]
3059
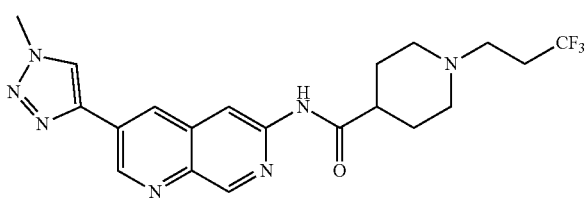 [SMILES: Cn1cc(-c2cnc3cnc(NC(=O)C4CCN(CCC(F)(F)F)CC4)cc3c2)nn1]
3060
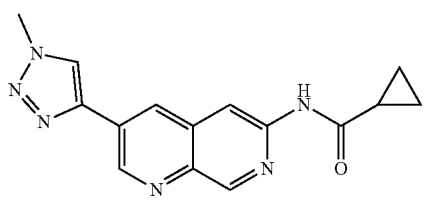 [SMILES: Cn1cc(-c2cnc3cnc(NC(=O)C4CC4)cc3c2)nn1]
3061

TABLE 1-continued
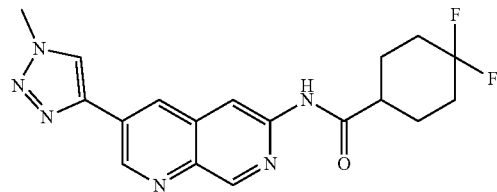 [SMILES: Cn1cc(-c2cnc3cnc(NC(=O)C4CCC(F)(F)CC4)cc3c2)nn1] 3062
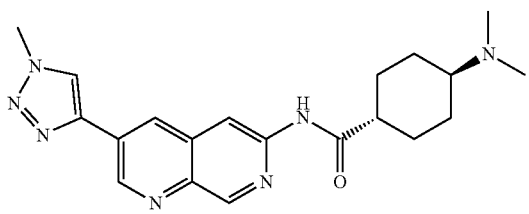 [SMILES: Cn1cc(-c2cnc3cnc(NC(=O)[C@H]4CC[C@H](N(C)C)CC4)cc3c2)nn1] 3063
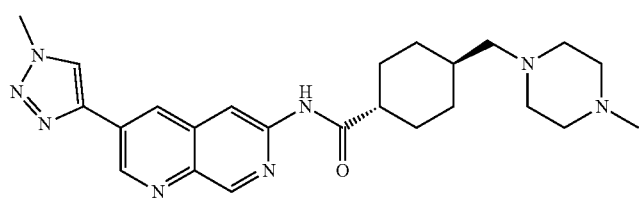 [SMILES: CN1CCN(C[C@H]2CC[C@H](C(=O)Nc3cc4cc(-c5cn(C)nn5)cnc4cn3)CC2)CC1] 3064
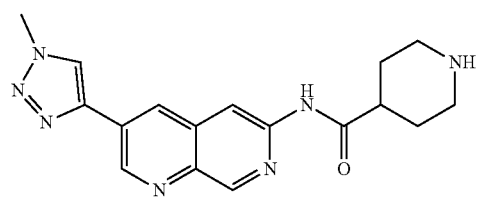 [SMILES: Cn1cc(-c2cnc3cnc(NC(=O)C4CCNCC4)cc3c2)nn1] 3065
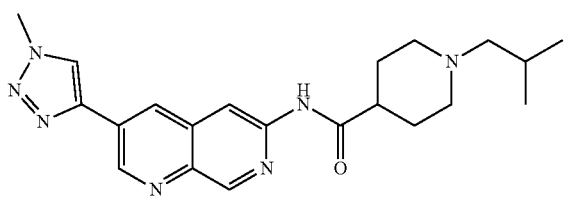 [SMILES: CC(C)CN1CCC(C(=O)Nc2cc3cc(-c4cn(C)nn4)cnc3cn2)CC1] 3066
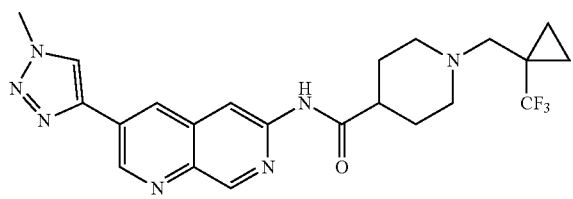 [SMILES: Cn1cc(-c2cnc3cnc(NC(=O)C4CCN(CC5(C(F)(F)F)CC5)CC4)cc3c2)nn1] 3067
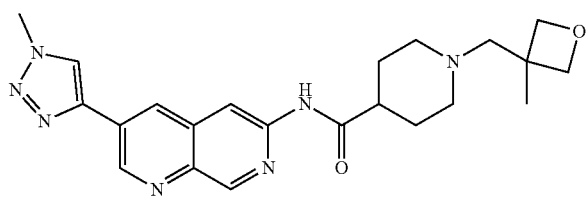 [SMILES: Cn1cc(-c2cnc3cnc(NC(=O)C4CCN(CC5(C)COC5)CC4)cc3c2)nn1] 3068

TABLE 1-continued
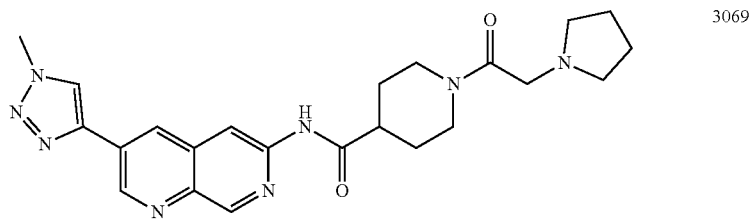 3069
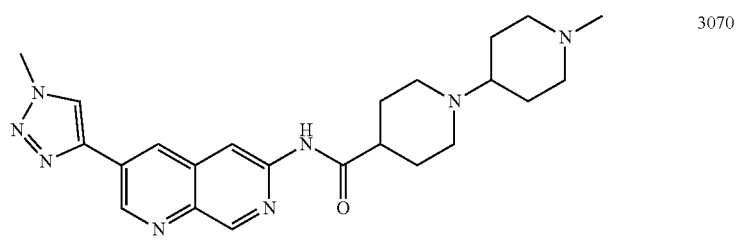 3070
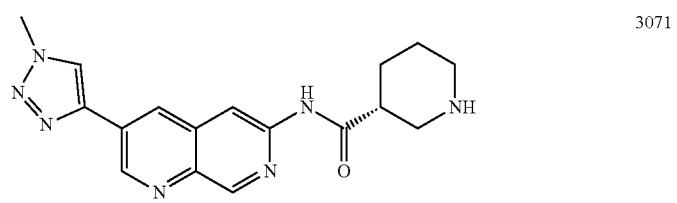 3071
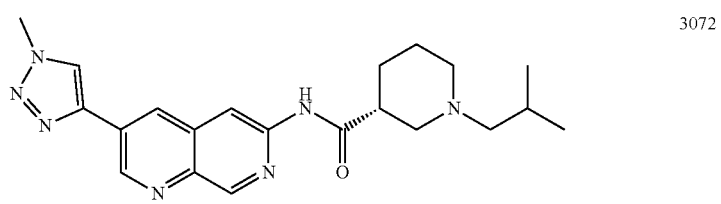 3072
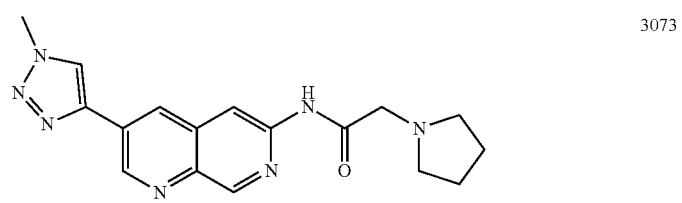 3073
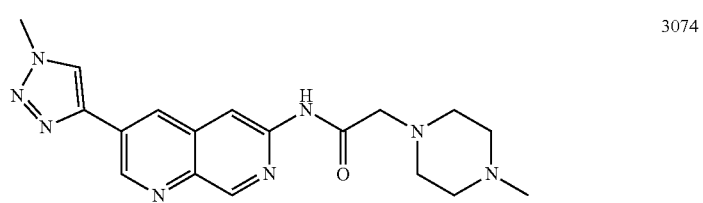 3074
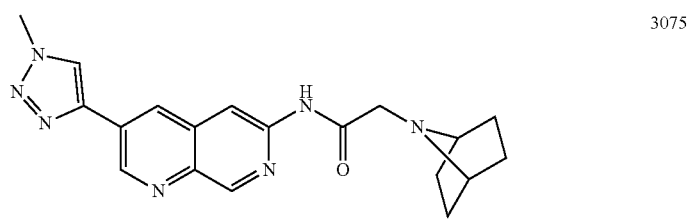 3075

TABLE 1-continued
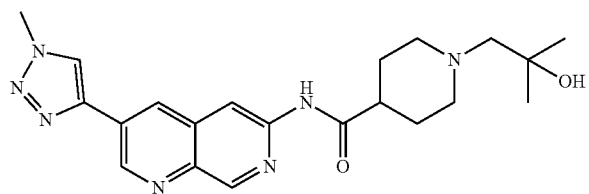 [SMILES: Cn1cc(-c2cnc3cnc(NC(=O)C4CCN(CC(C)(C)O)CC4)cc3c2)nn1] 3076
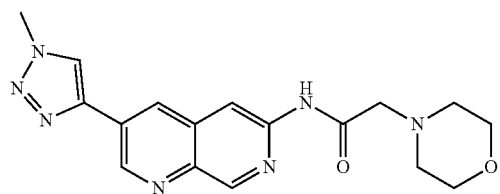 [SMILES: Cn1cc(-c2cnc3cnc(NC(=O)CN4CCOCC4)cc3c2)nn1] 3077
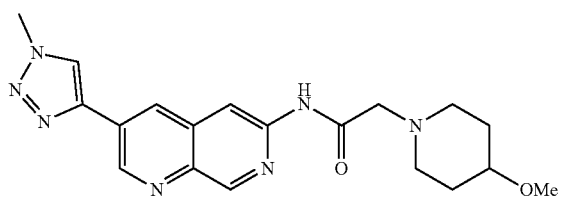 [SMILES: COC1CCN(CC(=O)Nc2cc3cc(-c4cn(C)nn4)cnc3cn2)CC1] 3078
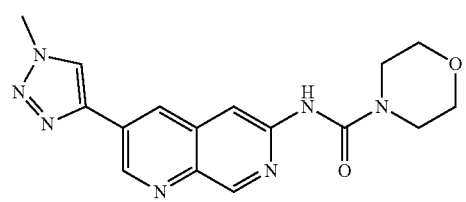 [SMILES: Cn1cc(-c2cnc3cnc(NC(=O)N4CCOCC4)cc3c2)nn1] 3079
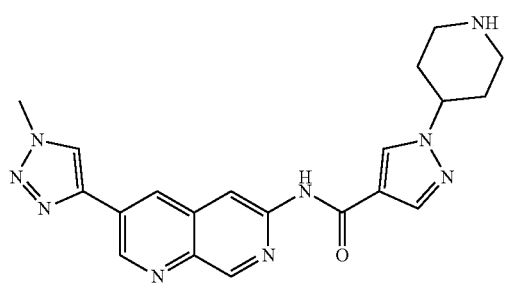 [SMILES: Cn1cc(-c2cnc3cnc(NC(=O)c4cnn(C5CCNCC5)c4)cc3c2)nn1] 3080
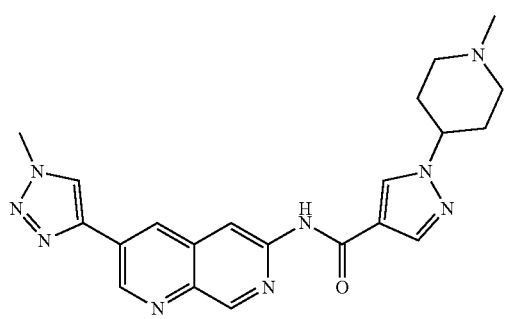 [SMILES: CN1CCC(n2cc(C(=O)Nc3cc4cc(-c5cn(C)nn5)cnc4cn3)cn2)CC1] 3081

TABLE 1-continued
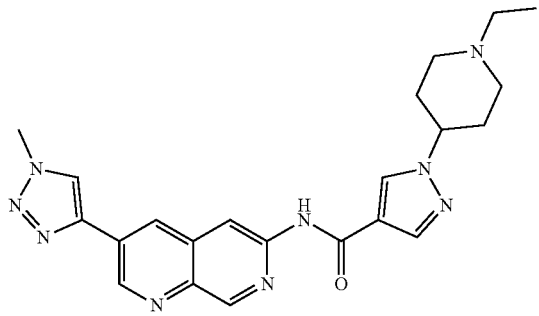 [SMILES: CCN1CCC(n2cc(C(=O)Nc3cc4cc(-c5cn(C)nn5)cnc4cn3)cn2)CC1]
3082
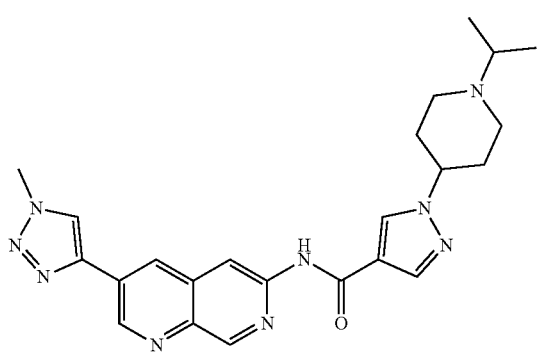 [SMILES: CC(C)N1CCC(n2cc(C(=O)Nc3cc4cc(-c5cn(C)nn5)cnc4cn3)cn2)CC1]
3083
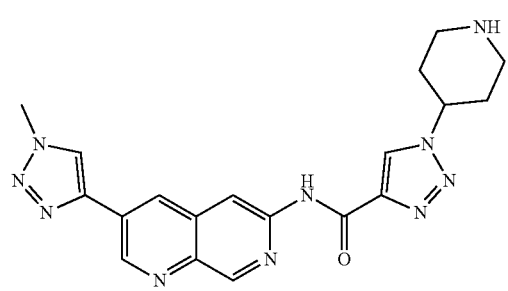 [SMILES: Cn1cc(-c2cnc3cnc(NC(=O)c4cn(C5CCNCC5)nn4)cc3c2)nn1]
3084
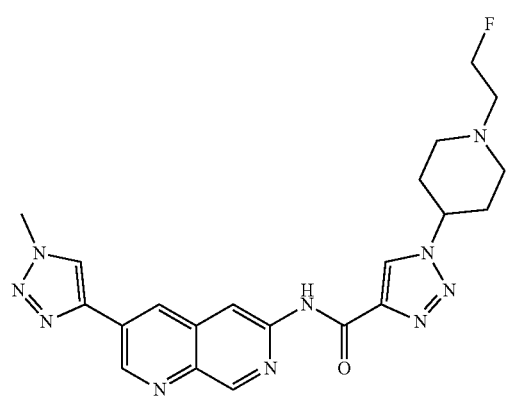 [SMILES: Cn1cc(-c2cnc3cnc(NC(=O)c4cn(C5CCN(CCF)CC5)nn4)cc3c2)nn1]
3085

| | |
|---|---|
| 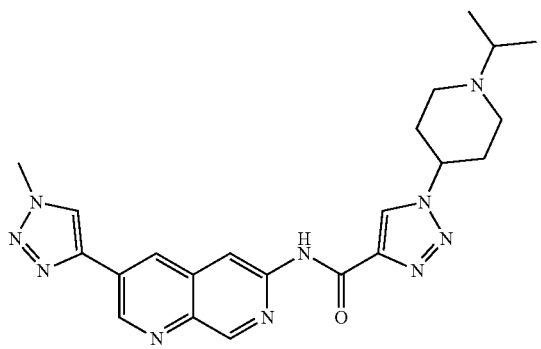 [SMILES: CC(C)N1CCC(n2cc(C(=O)Nc3cc4cc(-c5cn(C)nn5)cnc4cn3)nn2)CC1] | 3086 |
| 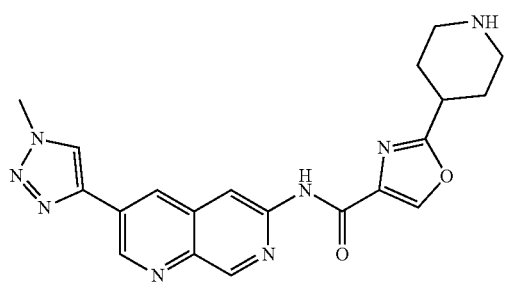 [SMILES: Cn1cc(-c2cnc3cnc(NC(=O)c4coc(C5CCNCC5)n4)cc3c2)nn1] | 3087 |
| 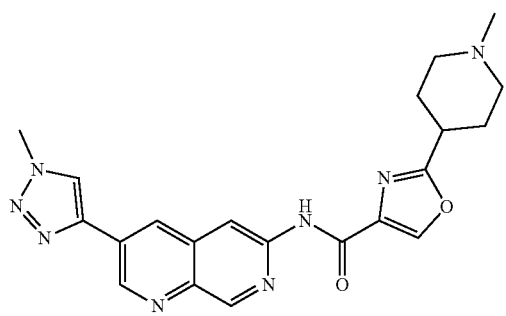 [SMILES: CN1CCC(c2nc(C(=O)Nc3cc4cc(-c5cn(C)nn5)cnc4cn3)co2)CC1] | 3088 |
| 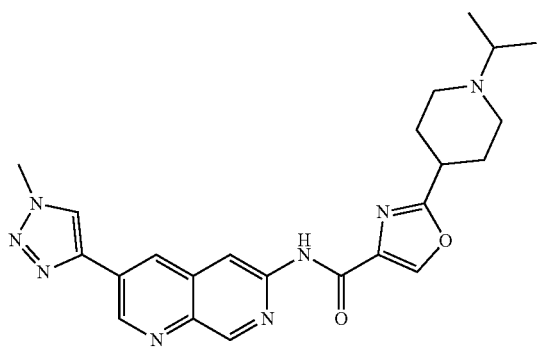 [SMILES: CC(C)N1CCC(c2nc(C(=O)Nc3cc4cc(-c5cn(C)nn5)cnc4cn3)co2)CC1] | 3089 |
| 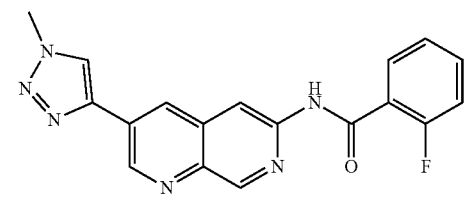 [SMILES: Cn1cc(-c2cnc3cnc(NC(=O)c4ccccc4F)cc3c2)nn1] | 3090 |

TABLE 1-continued
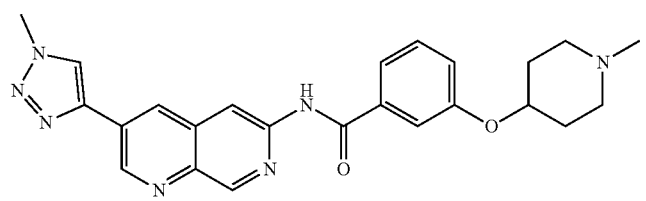
3091
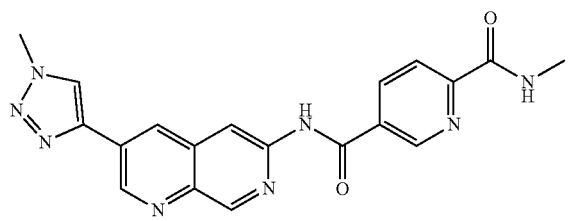 [SMILES: CNC(=O)c1ccc(C(=O)Nc2cc3cc(-c4cn(C)nn4)cnc3cn2)cn1]
3092
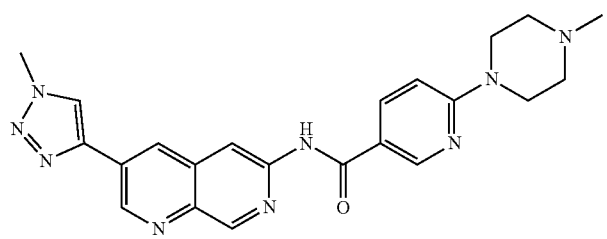 [SMILES: CN1CCN(c2ccc(C(=O)Nc3cc4cc(-c5cn(C)nn5)cnc4cn3)cn2)CC1]
3093
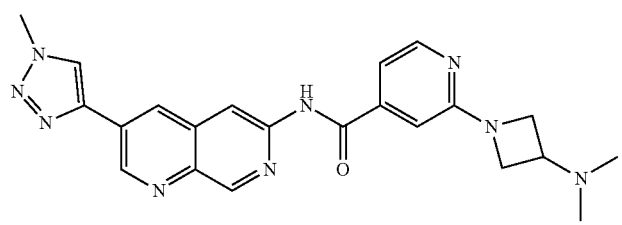 [SMILES: CN(C)C1CN(c2cc(C(=O)Nc3cc4cc(-c5cn(C)nn5)cnc4cn3)ccn2)C1]
3094
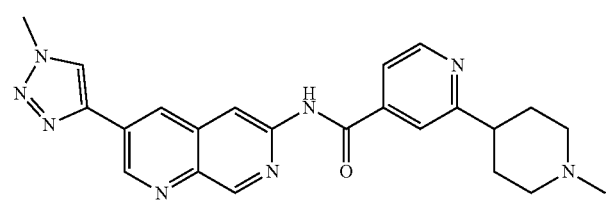
3095
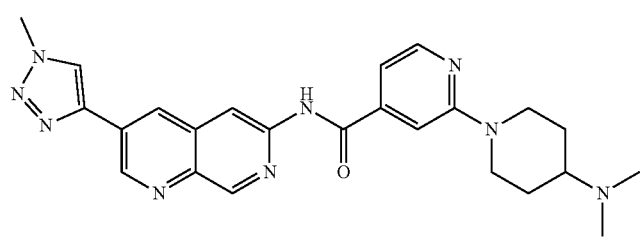 [SMILES: CN(C)C1CCN(c2cc(C(=O)Nc3cc4cc(-c5cn(C)nn5)cnc4cn3)ccn2)CC1]
3096
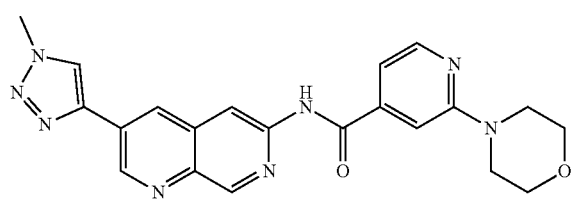 [SMILES: Cn1cc(-c2cnc3cnc(NC(=O)c4ccnc(N5CCOCC5)c4)cc3c2)nn1]
3097

TABLE 1-continued
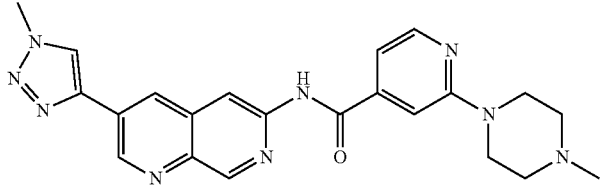 3098
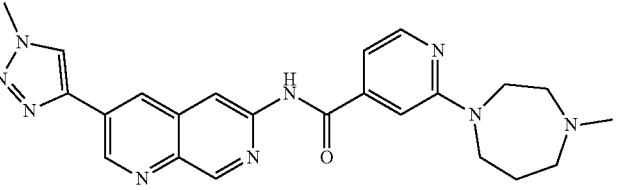 3099
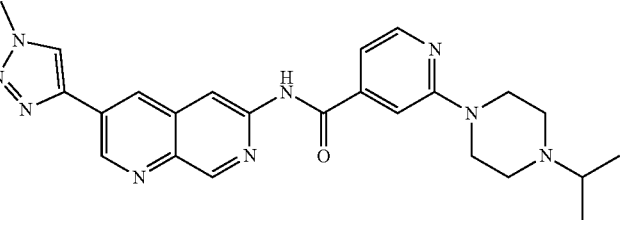 3100
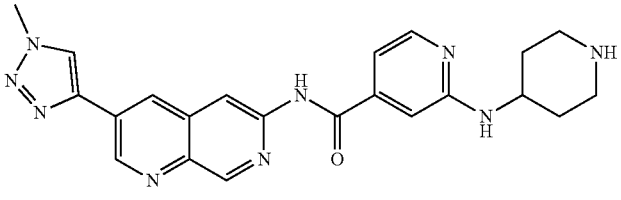 [SMILES: Cn1cc(-c2cnc3cnc(NC(=O)c4ccnc(NC5CCNCC5)c4)cc3c2)nn1] 3101
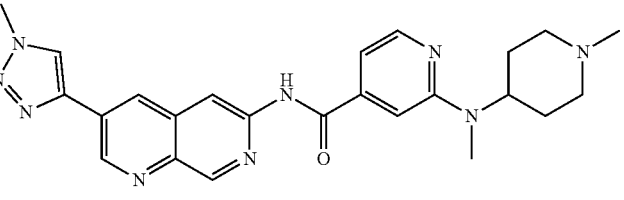 3102
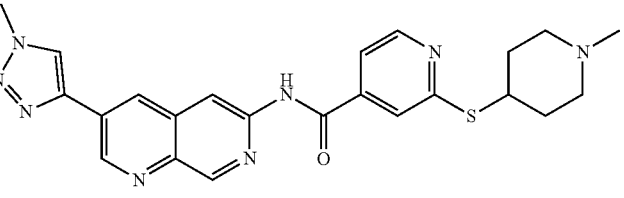 3103
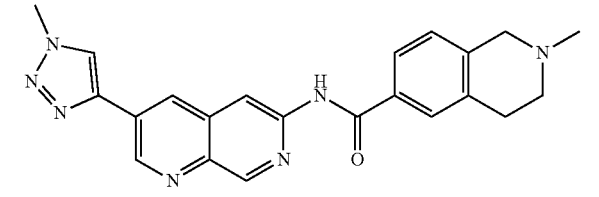 [SMILES: CN1CCc2cc(C(=O)Nc3cc4cc(-c5cn(C)nn5)cnc4cn3)ccc2C1] 3104
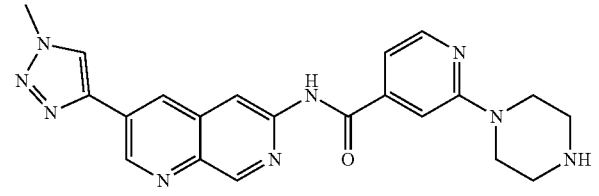 [SMILES: Cn1cc(-c2cnc3cnc(NC(=O)c4ccnc(N5CCNCC5)c4)cc3c2)nn1] 3105

TABLE 1-continued
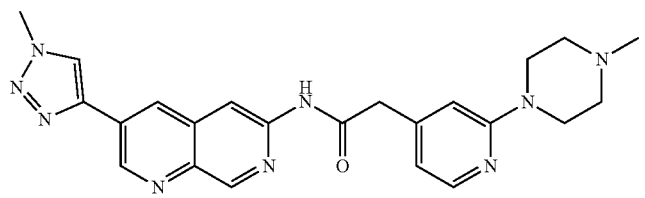 3106
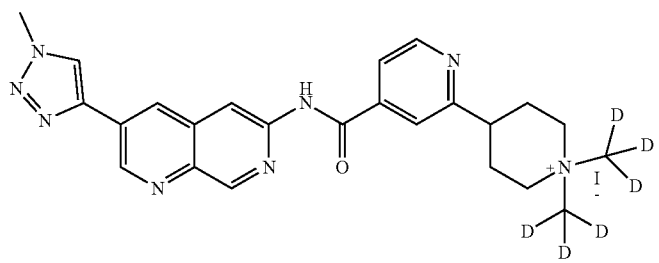 3107
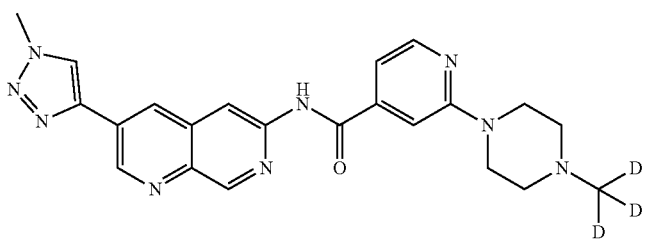 [SMILES: [2H]C([2H])([2H])N1CCN(c2cc(C(=O)Nc3cc4cc(-c5cn(C)nn5)cnc4cn3)ccn2)CC1] 3108
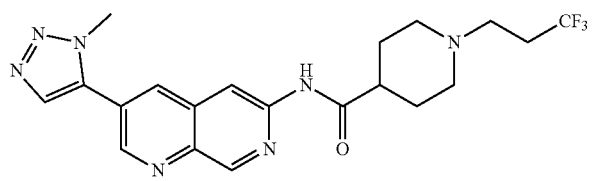 [SMILES: Cn1nncc1-c1cnc2cnc(NC(=O)C3CCN(CCC(F)(F)F)CC3)cc2c1] 3109
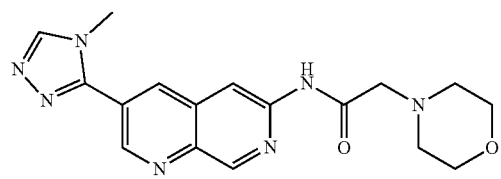 [SMILES: Cn1cnnc1-c1cnc2cnc(NC(=O)CN3CCOCC3)cc2c1] 3110
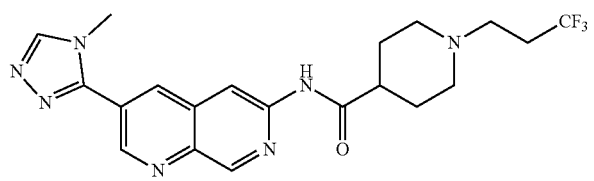 3111
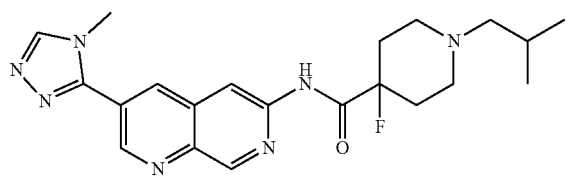 [SMILES: CC(C)CN1CCC(F)(C(=O)Nc2cc3cc(-c4nncn4C)cnc3cn2)CC1] 3112

TABLE 1-continued
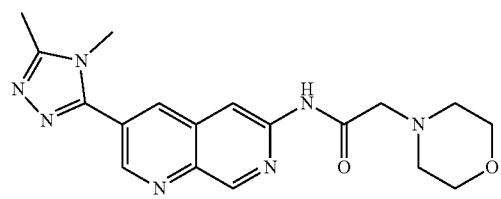 [SMILES: Cc1nnc(-c2cnc3cnc(NC(=O)CN4CCOCC4)cc3c2)n1C]
3113
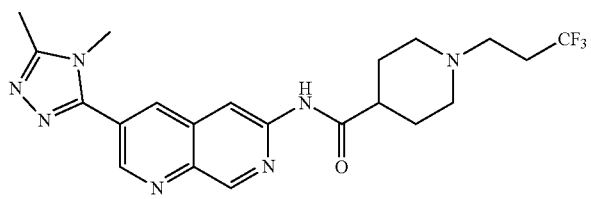 [SMILES: Cc1nnc(-c2cnc3cnc(NC(=O)C4CCN(CCC(F)(F)F)CC4)cc3c2)n1C]
3114
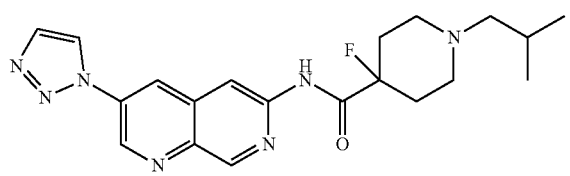 [SMILES: CC(C)CN1CCC(F)(C(=O)Nc2cc3cc(-n4ccnn4)cnc3cn2)CC1]
3115
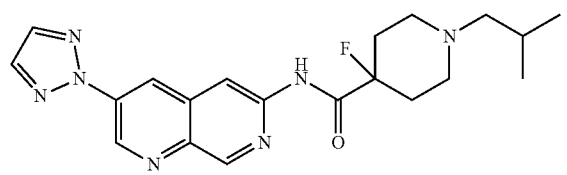 [SMILES: CC(C)CN1CCC(F)(C(=O)Nc2cc3cc(-n4nccn4)cnc3cn2)CC1]
3116
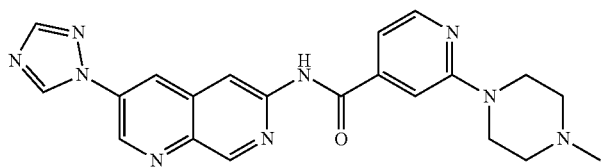 [SMILES: CN1CCN(c2cc(C(=O)Nc3cc4cc(-n5cncn5)cnc4cn3)ccn2)CC1]
3117
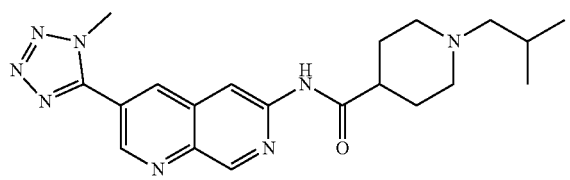 [SMILES: CC(C)CN1CCC(C(=O)Nc2cc3cc(-c4nnnn4C)cnc3cn2)CC1]
3118
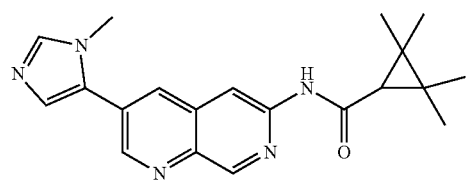 [SMILES: Cn1cncc1-c1cnc2cnc(NC(=O)C3C(C)(C)C3(C)C)cc2c1]
3119
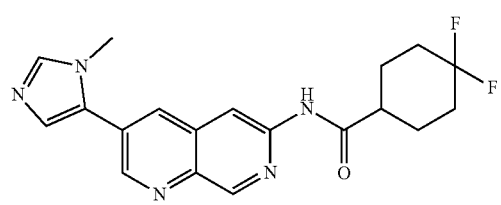 [SMILES: Cn1cncc1-c1cnc2cnc(NC(=O)C3CCC(F)(F)CC3)cc2c1]
3120

TABLE 1-continued
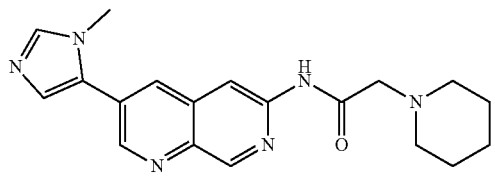 [SMILES: Cn1cncc1-c1cnc2cnc(NC(=O)CN3CCCCC3)cc2c1] 3121
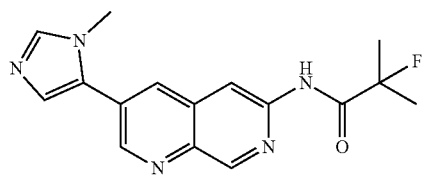 [SMILES: Cn1cncc1-c1cnc2cnc(NC(=O)C(C)(C)F)cc2c1] 3122
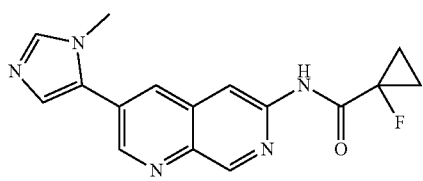 [SMILES: Cn1cncc1-c1cnc2cnc(NC(=O)C3(F)CC3)cc2c1] 3123
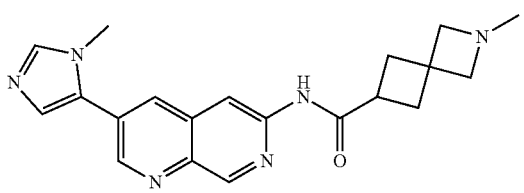 [SMILES: CN1CC2(CC(C(=O)Nc3cc4cc(-c5cncn5C)cnc4cn3)C2)C1] 3124
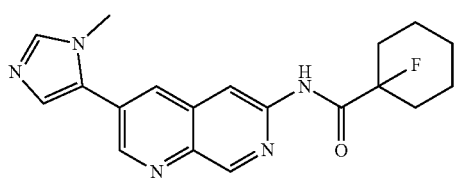 3125
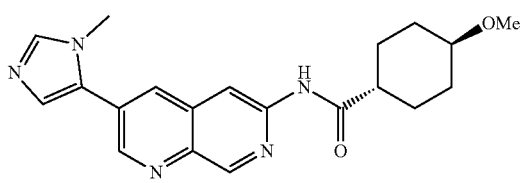 [SMILES: CO[C@H]1CC[C@H](C(=O)Nc2cc3cc(-c4cncn4C)cnc3cn2)CC1] 3126
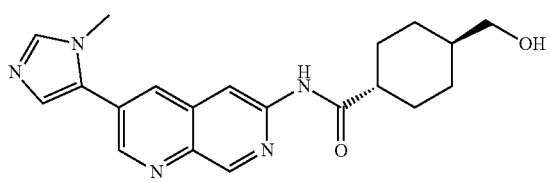 [SMILES: Cn1cncc1-c1cnc2cnc(NC(=O)[C@H]3CC[C@H](CO)CC3)cc2c1] 3127
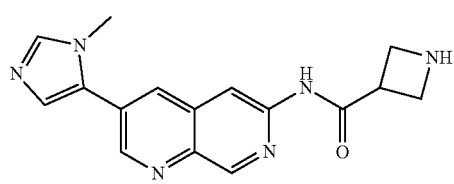 [SMILES: Cn1cncc1-c1cnc2cnc(NC(=O)C3CNC3)cc2c1] 3128

TABLE 1-continued
| | |
|---|---|
| 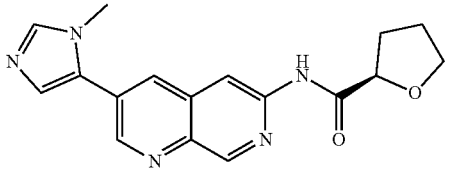 [SMILES: Cn1cncc1-c1cnc2cnc(NC(=O)[C@H]3CCCO3)cc2c1] | 3129 |
| | 3130 |
| | 3131 |
| | 3132 |
| 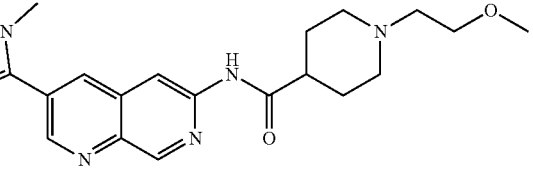 | 3133 |
| | 3134 |
| 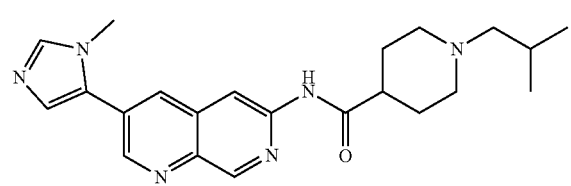 [SMILES: CC(C)CN1CCC(C(=O)Nc2cc3cc(-c4cncn4C)cnc3cn2)CC1] | 3135 |
| 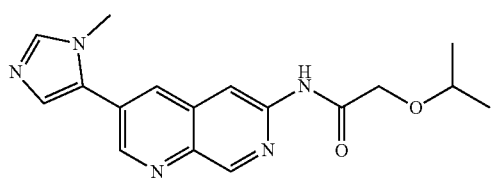 [SMILES: CC(C)OCC(=O)Nc1cc2cc(-c3cncn3C)cnc2cn1] | 3136 |

TABLE 1-continued
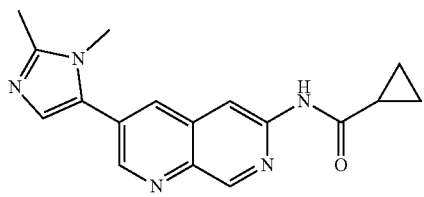 [SMILES: Cc1ncc(-c2cnc3cnc(NC(=O)C4CC4)cc3c2)n1C] 3137
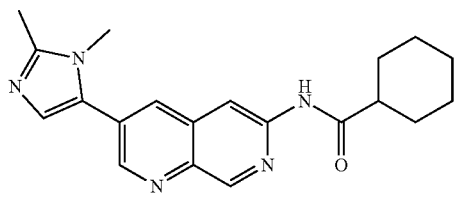 [SMILES: Cc1ncc(-c2cnc3cnc(NC(=O)C4CCCCC4)cc3c2)n1C] 3138
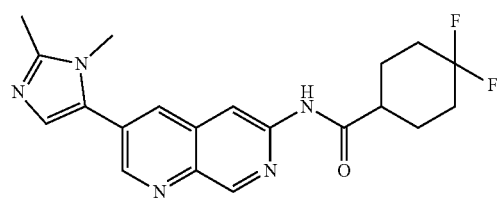 [SMILES: Cc1ncc(-c2cnc3cnc(NC(=O)C4CCC(F)(F)CC4)cc3c2)n1C] 3139
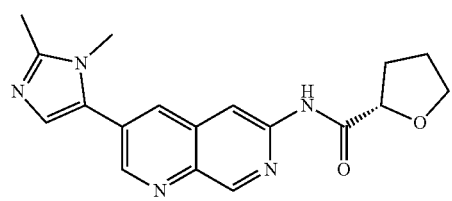 [SMILES: Cc1ncc(-c2cnc3cnc(NC(=O)[C@@H]4CCCO4)cc3c2)n1C] 3140
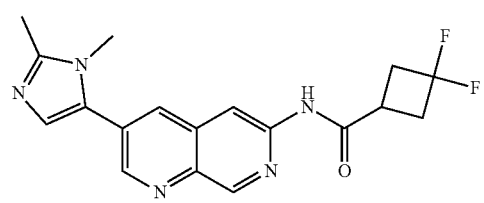 [SMILES: Cc1ncc(-c2cnc3cnc(NC(=O)C4CC(F)(F)C4)cc3c2)n1C] 3141
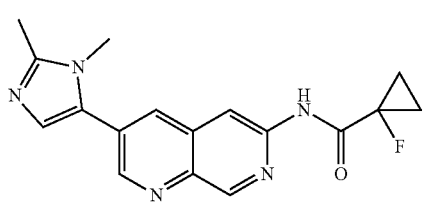 [SMILES: Cc1ncc(-c2cnc3cnc(NC(=O)C4(F)CC4)cc3c2)n1C] 3142
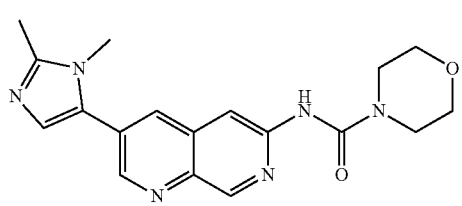 [SMILES: Cc1ncc(-c2cnc3cnc(NC(=O)N4CCOCC4)cc3c2)n1C] 3143
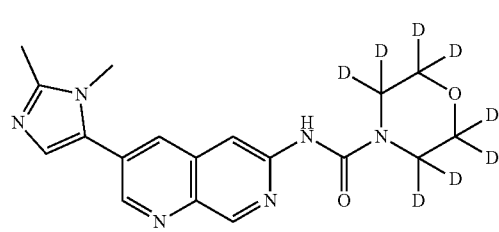 [SMILES: [2H]C1([2H])OC([2H])([2H])C([2H])([2H])N(C(=O)Nc2cc3cc(-c4cnc(C)n4C)cnc3cn2)C1([2H])[2H]] 3144

TABLE 1-continued
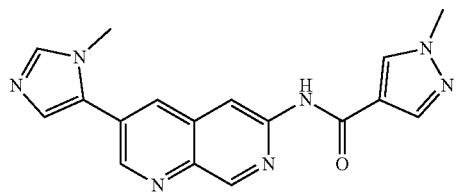 [SMILES: Cn1cc(C(=O)Nc2cc3cc(-c4cncn4C)cnc3cn2)cn1]
3145
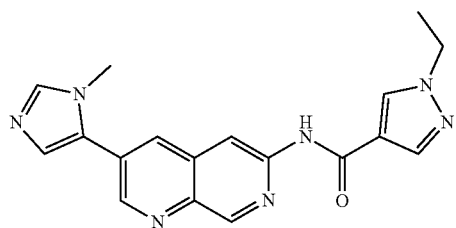 [SMILES: CCn1cc(C(=O)Nc2cc3cc(-c4cncn4C)cnc3cn2)cn1]
3146
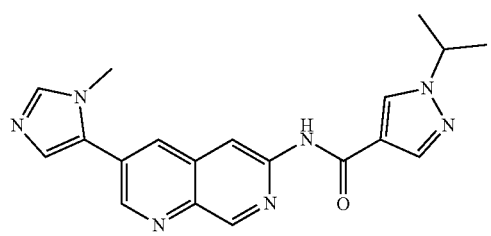 [SMILES: CC(C)n1cc(C(=O)Nc2cc3cc(-c4cncn4C)cnc3cn2)cn1]
3147
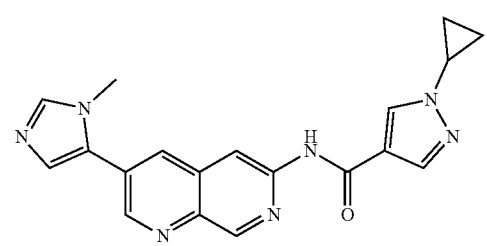 [SMILES: Cn1cncc1-c1cnc2cnc(NC(=O)c3cnn(C4CC4)c3)cc2c1]
3148
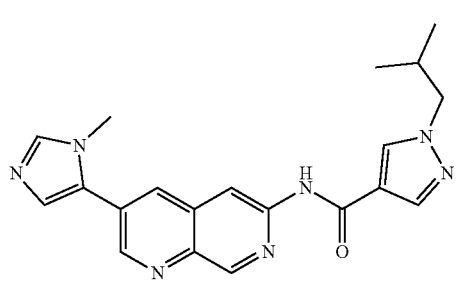 [SMILES: CC(C)Cn1cc(C(=O)Nc2cc3cc(-c4cncn4C)cnc3cn2)cn1]
3149
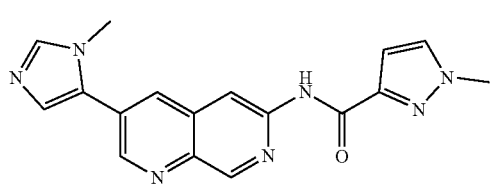
3150
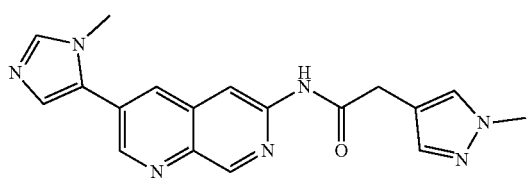 [SMILES: Cn1cc(CC(=O)Nc2cc3cc(-c4cncn4C)cnc3cn2)cn1]
3151

TABLE 1-continued

| | |
|---|---|
| (structure) | 3152 |
| (structure) | 3153 |
| (structure) | 3154 |
| (structure) | 3155 |
| (structure) | 3156 |
| (structure) | 3157 |
| (structure) | 3158 |
| (structure) | 3159 |

TABLE 1-continued

| | |
|---|---|
| (structure) | 3160 |
| (structure) | 3161 |
| (structure) | 3162 |
| (structure) | 3163 |
| (structure) | 3164 |
| (structure) | 3165 |
| (structure) | 3166 |
| (structure) | 3167 |

TABLE 1-continued
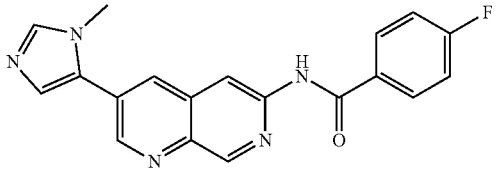 [SMILES: Cn1cncc1-c1cnc2cnc(NC(=O)c3ccc(F)cc3)cc2c1] 3168
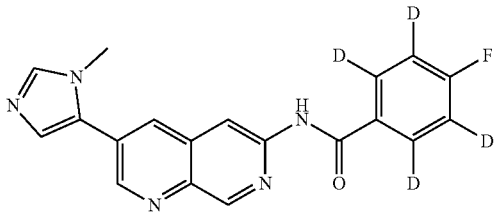 3169
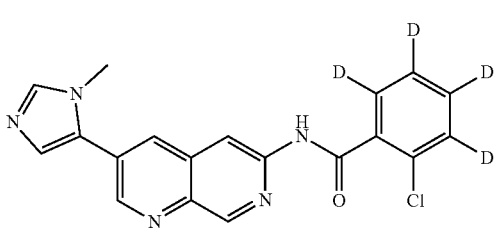 [SMILES: [2H]c1c([2H])c(C(=O)Nc2cc3cc(-c4cncn4C)cnc3cn2)c([2H])c([2H])c1F] 3170
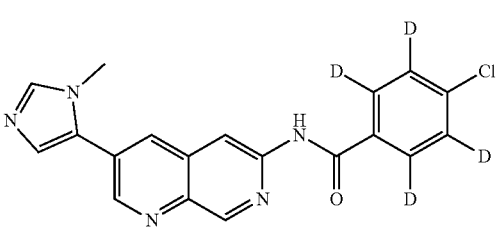 3171
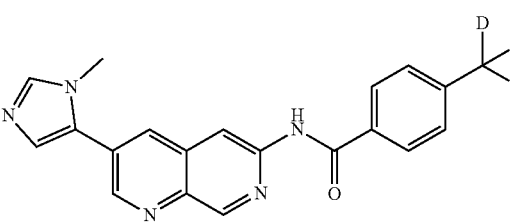 3172
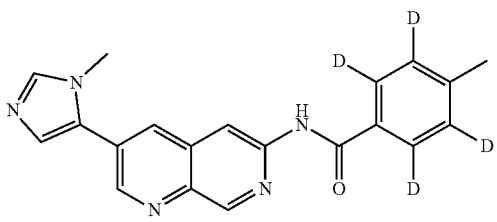 [SMILES: [2H]c1c([2H])c(C(=O)Nc2cc3cc(-c4cncn4C)cnc3cn2)c([2H])c([2H])c1C] 3173
3174

TABLE 1-continued
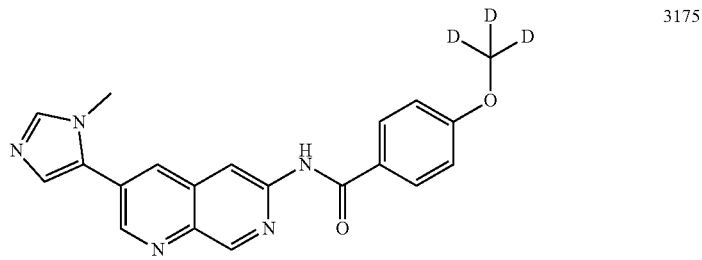 3175
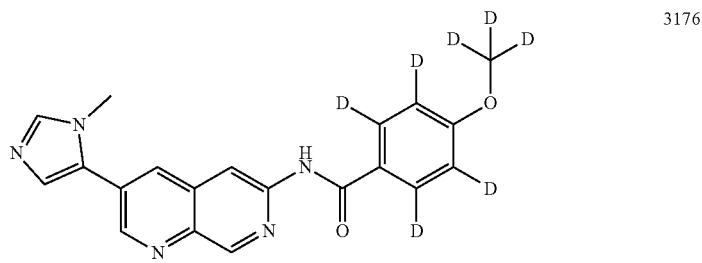 3176
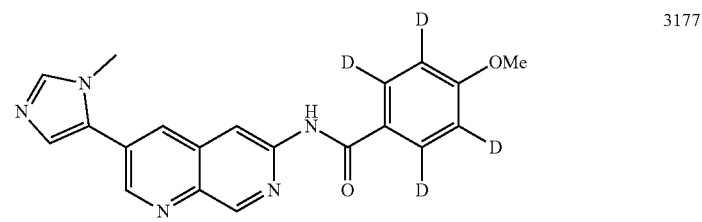 3177
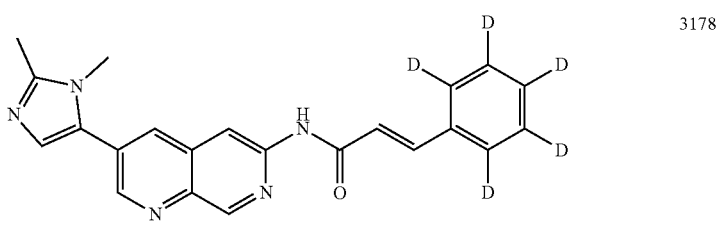 3178
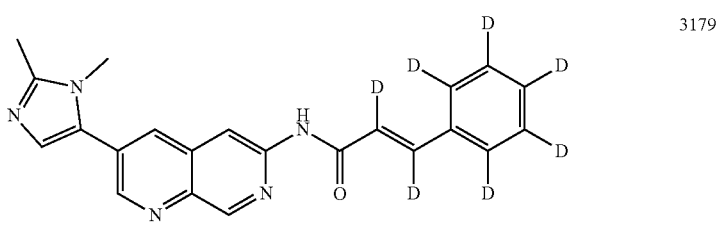 3179
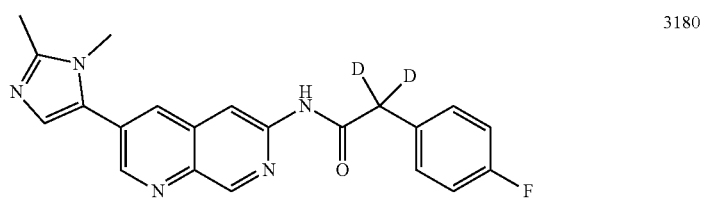 3180
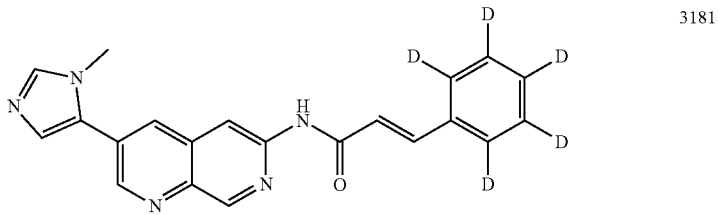 3181

TABLE 1-continued
| | |
|---|---|
| 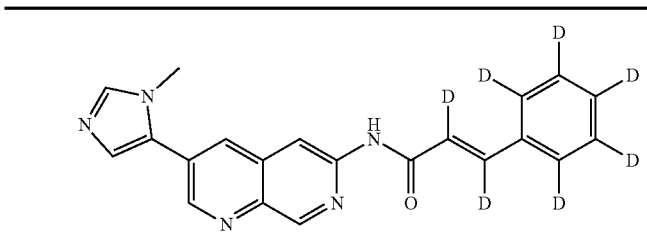 | 3182 |
| 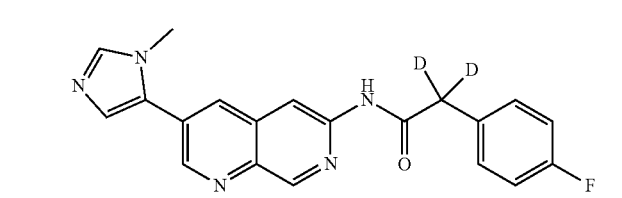 [SMILES: [2H]C([2H])(C(=O)Nc1cc2cc(-c3cncn3C)cnc2cn1)c1ccc(F)cc1] | 3183 |
| 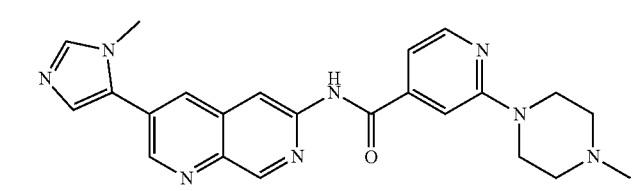 [SMILES: CN1CCN(c2cc(C(=O)Nc3cc4cc(-c5cncn5C)cnc4cn3)ccn2)CC1] | 3184 |
| 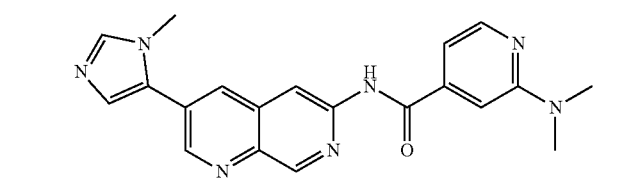 [SMILES: CN(C)c1cc(C(=O)Nc2cc3cc(-c4cncn4C)cnc3cn2)ccn1] | 3185 |
| 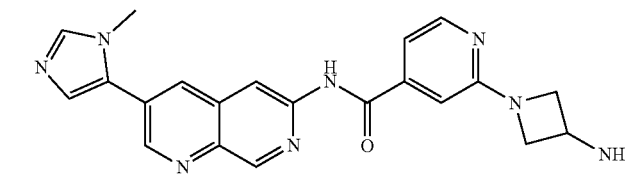 [SMILES: Cn1cncc1-c1cnc2cnc(NC(=O)c3ccnc(N4CC(N)C4)c3)cc2c1] | 3186 |
| 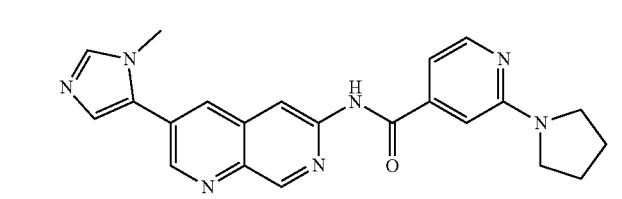 [SMILES: Cn1cncc1-c1cnc2cnc(NC(=O)c3ccnc(N4CCCC4)c3)cc2c1] | 3187 |
| 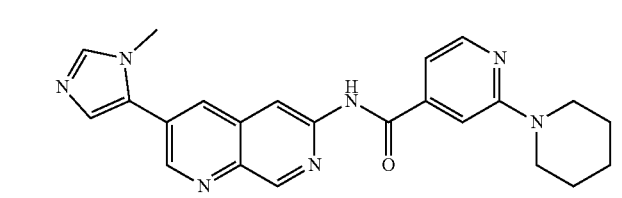 [SMILES: Cn1cncc1-c1cnc2cnc(NC(=O)c3ccnc(N4CCCCC4)c3)cc2c1] | 3188 |
| 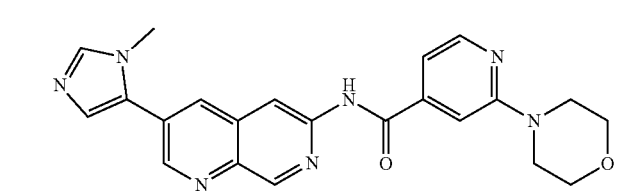 [SMILES: Cn1cncc1-c1cnc2cnc(NC(=O)c3ccnc(N4CCOCC4)c3)cc2c1] | 3189 |

TABLE 1-continued
| | |
|---|---|
| 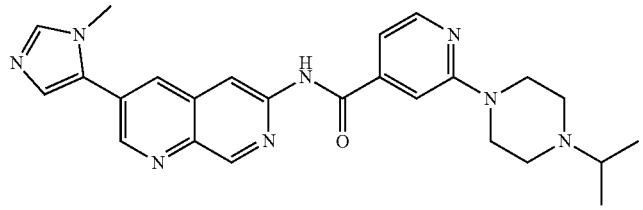 [SMILES: CC(C)N1CCN(c2cc(C(=O)Nc3cc4cc(-c5cncn5C)cnc4cn3)ccn2)CC1] | 3190 |
| 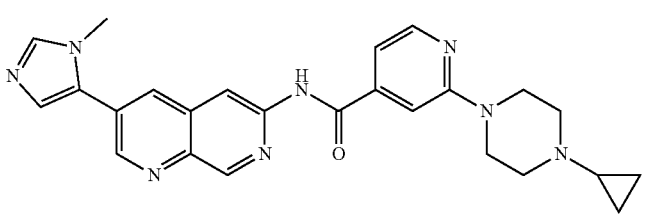 [SMILES: Cn1cncc1-c1cnc2cnc(NC(=O)c3ccnc(N4CCN(C5CC5)CC4)c3)cc2c1] | 3191 |
| 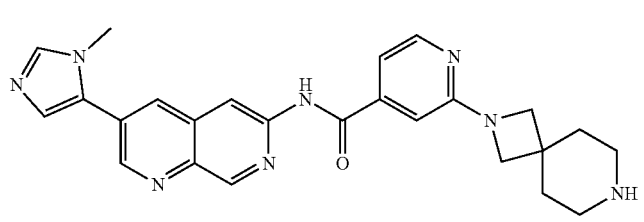 [SMILES: Cn1cncc1-c1cnc2cnc(NC(=O)c3ccnc(N4CC5(CCNCC5)C4)c3)cc2c1] | 3192 |
| 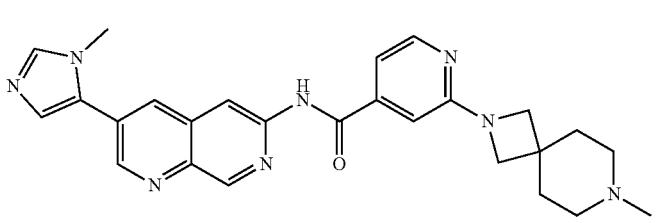 [SMILES: CN1CCC2(CC1)CN(c1cc(C(=O)Nc3cc4cc(-c5cncn5C)cnc4cn3)ccn1)C2] | 3193 |
| 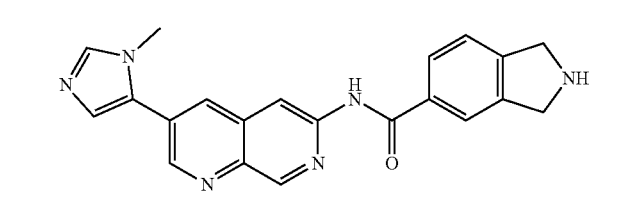 [SMILES: Cn1cncc1-c1cnc2cnc(NC(=O)c3ccc4c(c3)CNC4)cc2c1] | 3194 |
| 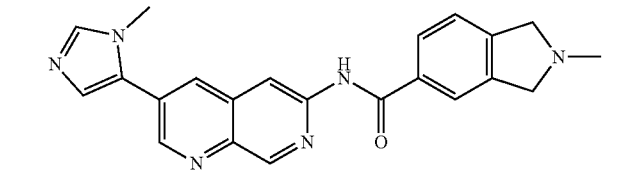 [SMILES: CN1Cc2ccc(C(=O)Nc3cc4cc(-c5cncn5C)cnc4cn3)cc2C1] | 3195 |
| 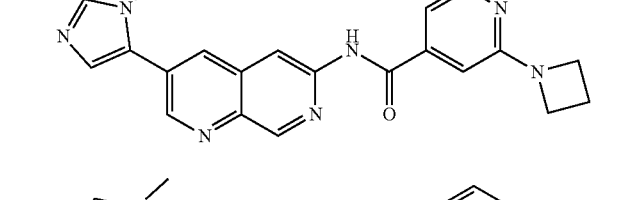 | 3196 |
| | 3197 |

TABLE 1-continued

| | |
|---|---|
| (structure) | 3198 |
| (structure) | 3199 |
| (structure) | 3200 |
| (structure) | 3201 |
| (structure) | 3202 |
| (structure) | 3203 |
| (structure) | 3204 |
| (structure) | 3205 |

TABLE 1-continued
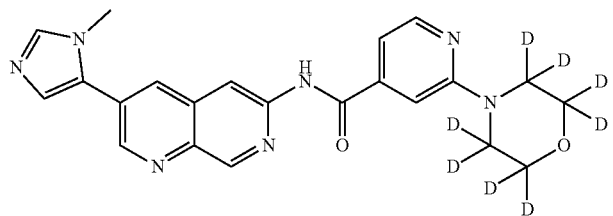 [SMILES: [2H]C1([2H])OC([2H])([2H])C([2H])([2H])N(c2cc(C(=O)Nc3cc4cc(-c5cncn5C)cnc4cn3)ccn2)C1([2H])[2H]] 3206
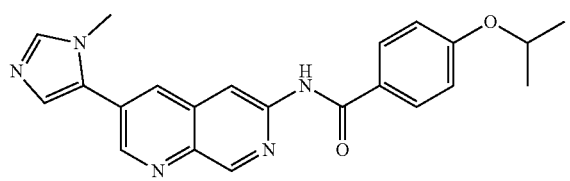 [SMILES: CC(C)Oc1ccc(C(=O)Nc2cc3cc(-c4cncn4C)cnc3cn2)cc1] 3207
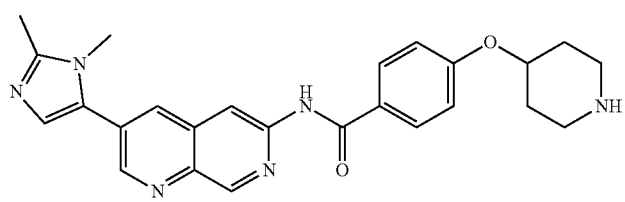 [SMILES: Cc1ncc(-c2cnc3cnc(NC(=O)c4ccc(OC5CCNCC5)cc4)cc3c2)n1C] 3208
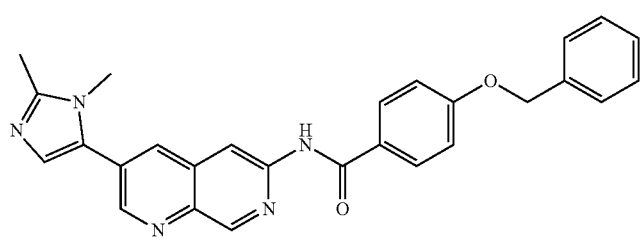 [SMILES: Cc1ncc(-c2cnc3cnc(NC(=O)c4ccc(OCc5ccccc5)cc4)cc3c2)n1C] 3209
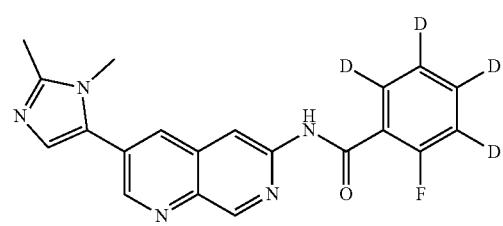 3210
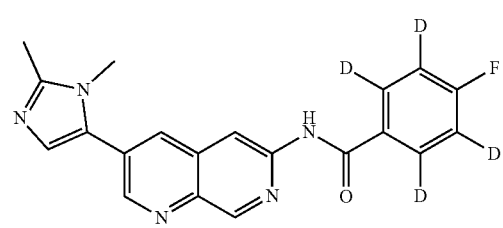 [SMILES: [2H]c1c([2H])c(C(=O)Nc2cc3cc(-c4cnc(C)n4C)cnc3cn2)c([2H])c([2H])c1F] 3211
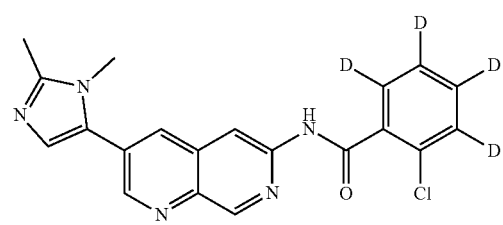 3212

TABLE 1-continued
| | |
|---|---|
| 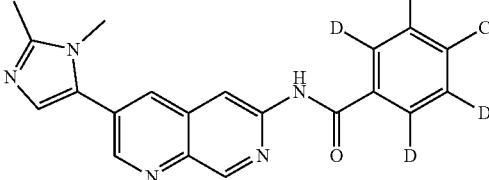 | 3213 |
| 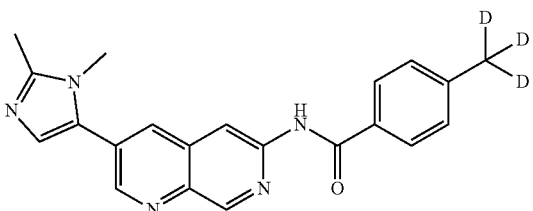 | 3214 |
| 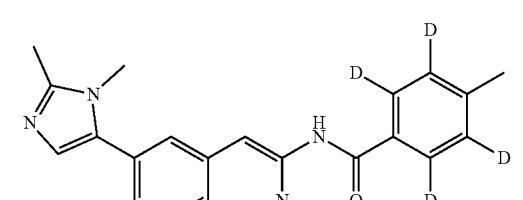 | 3215 |
| 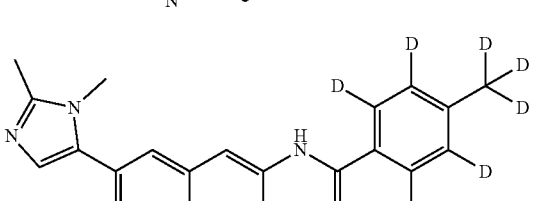 | 3216 |
| 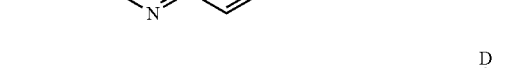 | 3217 |
|  | 3218 |
| 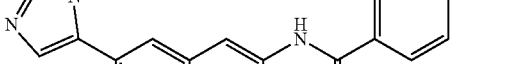 | 3219 |

TABLE 1-continued
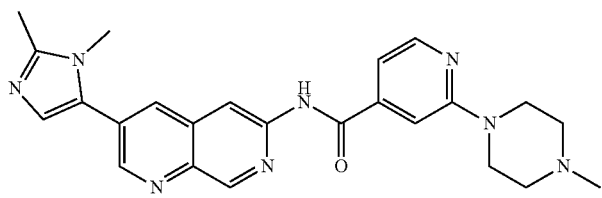 [SMILES: Cc1ncc(-c2cnc3cnc(NC(=O)c4ccnc(N5CCN(C)CC5)c4)cc3c2)n1C] 3220
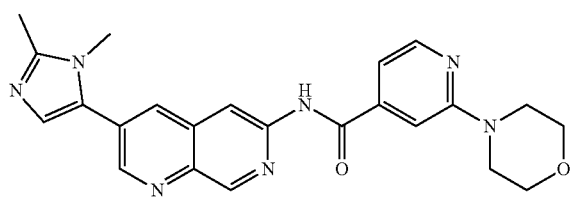 [SMILES: Cc1ncc(-c2cnc3cnc(NC(=O)c4ccnc(N5CCOCC5)c4)cc3c2)n1C] 3221
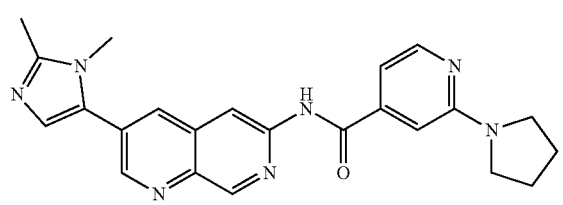 [SMILES: Cc1ncc(-c2cnc3cnc(NC(=O)c4ccnc(N5CCCC5)c4)cc3c2)n1C] 3222
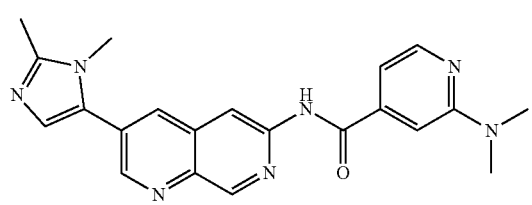 [SMILES: Cc1ncc(-c2cnc3cnc(NC(=O)c4ccnc(N(C)C)c4)cc3c2)n1C] 3223
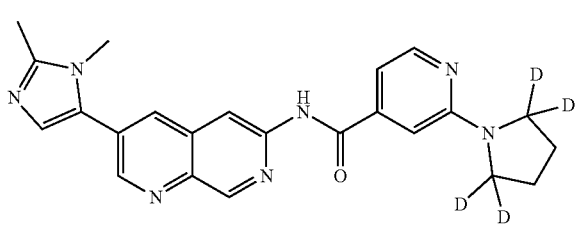 [SMILES: [2H]C1([2H])CCC([2H])([2H])N1c1cc(C(=O)Nc2cc3cc(-c4cnc(C)n4C)cnc3cn2)ccn1] 3224
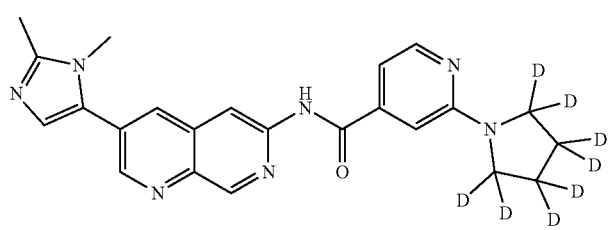 [SMILES: [2H]C1([2H])N(c2cc(C(=O)Nc3cc4cc(-c5cnc(C)n5C)cnc4cn3)ccn2)C([2H])([2H])C([2H])([2H])C1([2H])[2H]] 3225
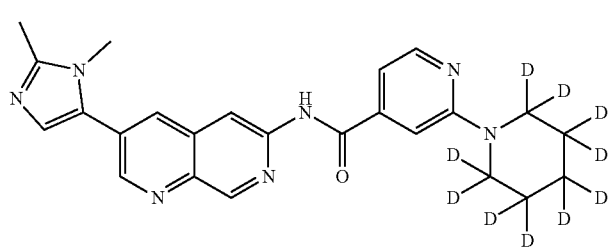 [SMILES: [2H]C1([2H])N(c2cc(C(=O)Nc3cc4cc(-c5cnc(C)n5C)cnc4cn3)ccn2)C([2H])([2H])C([2H])([2H])C([2H])([2H])C1([2H])[2H]] 3226

TABLE 1-continued
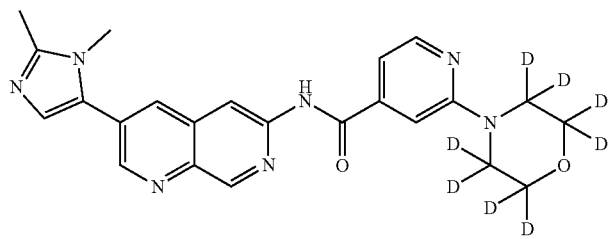 [SMILES: [2H]C1([2H])OC([2H])([2H])C([2H])([2H])N(c2cc(C(=O)Nc3cc4cc(-c5cnc(C)n5C)cnc4cn3)ccn2)C1([2H])[2H]]
3227
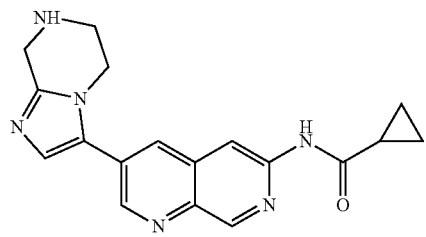 [SMILES: O=C(Nc1cc2cc(-c3cnc4n3CCNC4)cnc2cn1)C1CC1]
3228
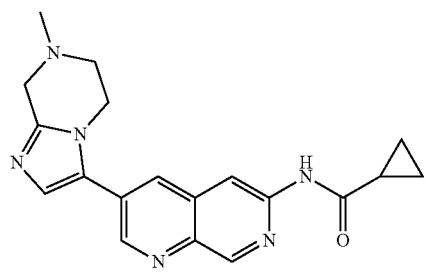 [SMILES: CN1CCn2c(-c3cnc4cnc(NC(=O)C5CC5)cc4c3)cnc2C1]
3229
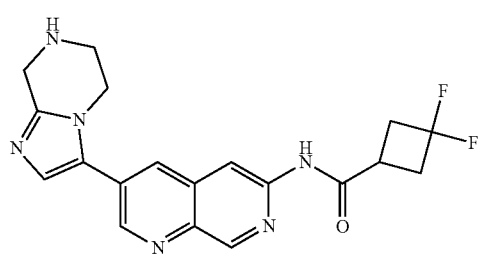 [SMILES: O=C(Nc1cc2cc(-c3cnc4n3CCNC4)cnc2cn1)C1CC(F)(F)C1]
3230
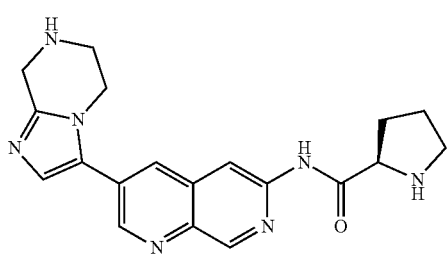 [SMILES: O=C(Nc1cc2cc(-c3cnc4n3CCNC4)cnc2cn1)[C@H]1CCCN1]
3231
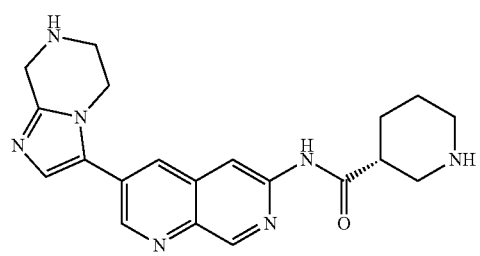 [SMILES: O=C(Nc1cc2cc(-c3cnc4n3CCNC4)cnc2cn1)[C@@H]1CCCNC1]
3232

TABLE 1-continued
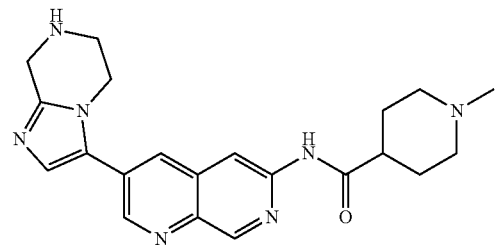 [SMILES: CN1CCC(C(=O)Nc2cc3cc(-c4cnc5n4CCNC5)cnc3cn2)CC1] 3233
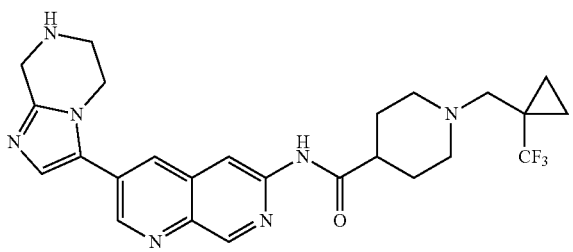 [SMILES: O=C(Nc1cc2cc(-c3cnc4n3CCNC4)cnc2cn1)C1CCN(CC2(C(F)(F)F)CC2)CC1] 3234
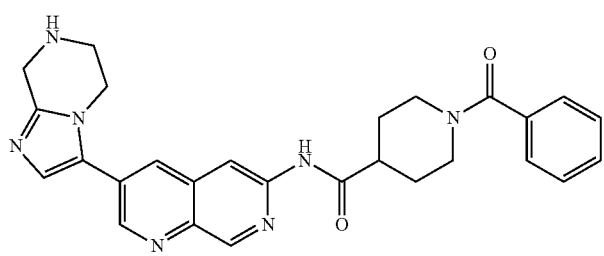 [SMILES: O=C(Nc1cc2cc(-c3cnc4n3CCNC4)cnc2cn1)C1CCN(C(=O)c2ccccc2)CC1] 3235
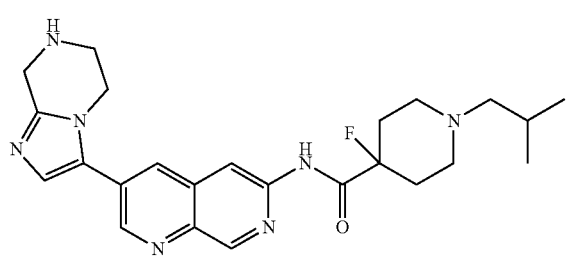 [SMILES: CC(C)CN1CCC(F)(C(=O)Nc2cc3cc(-c4cnc5n4CCNC5)cnc3cn2)CC1] 3236
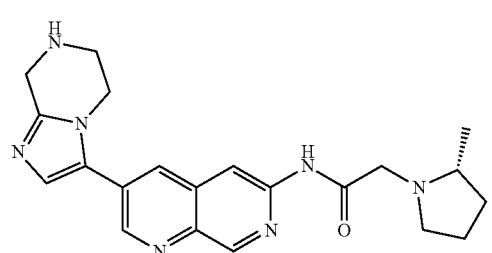 3237
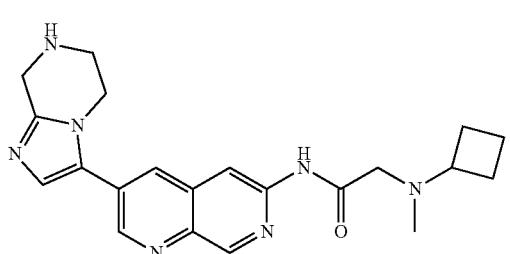 3238

TABLE 1-continued
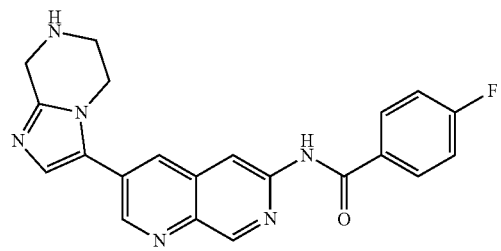 [SMILES: O=C(Nc1cc2cc(-c3cnc4n3CCNC4)cnc2cn1)c1ccc(F)cc1] 3239
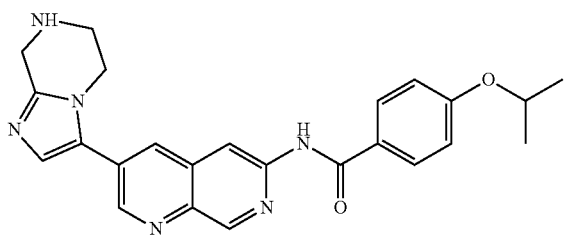 [SMILES: CC(C)Oc1ccc(C(=O)Nc2cc3cc(-c4cnc5n4CCNC5)cnc3cn2)cc1] 3240
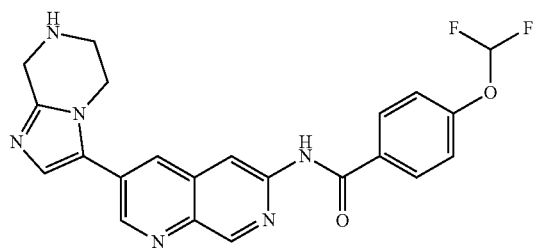 [SMILES: O=C(Nc1cc2cc(-c3cnc4n3CCNC4)cnc2cn1)c1ccc(OC(F)F)cc1] 3241
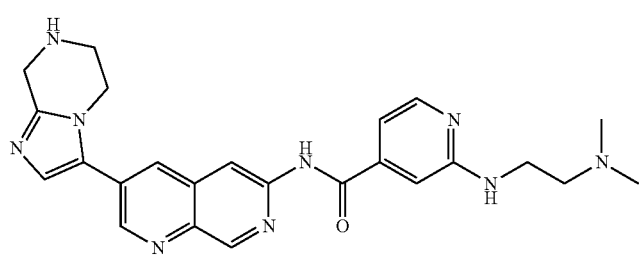 [SMILES: CN(C)CCNc1cc(C(=O)Nc2cc3cc(-c4cnc5n4CCNC5)cnc3cn2)ccn1] 3242
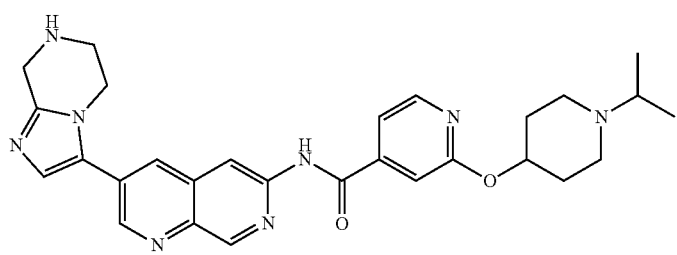 [SMILES: CC(C)N1CCC(Oc2cc(C(=O)Nc3cc4cc(-c5cnc6n5CCNC6)cnc4cn3)ccn2)CC1] 3243
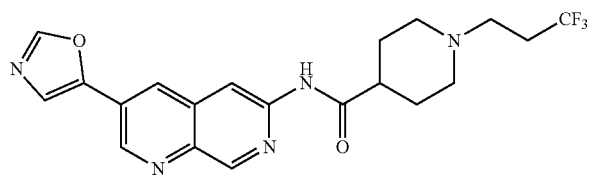 [SMILES: O=C(Nc1cc2cc(-c3cnco3)cnc2cn1)C1CCN(CCC(F)(F)F)CC1] 3244
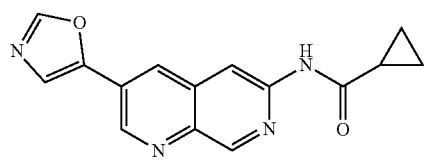 3245

TABLE 1-continued
| | |
|---|---|
| 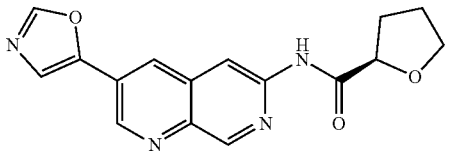 [SMILES: O=C(Nc1cc2cc(-c3cnco3)cnc2cn1)[C@H]1CCCO1] | 3246 |
| 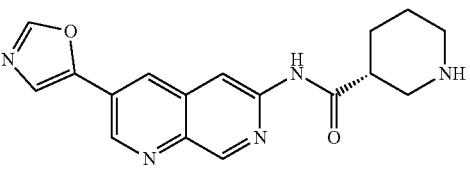 [SMILES: O=C(Nc1cc2cc(-c3cnco3)cnc2cn1)[C@@H]1CCCNC1] | 3247 |
| 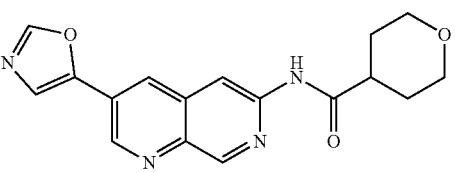 [SMILES: O=C(Nc1cc2cc(-c3cnco3)cnc2cn1)C1CCOCC1] | 3248 |
| 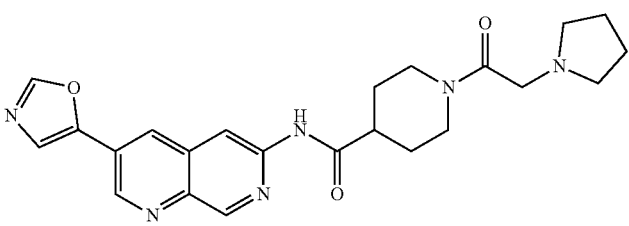 [SMILES: O=C(Nc1cc2cc(-c3cnco3)cnc2cn1)C1CCN(C(=O)CN2CCCC2)CC1] | 3249 |
| 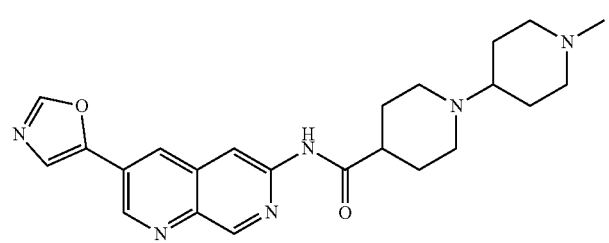 [SMILES: CN1CCC(N2CCC(C(=O)Nc3cc4cc(-c5cnco5)cnc4cn3)CC2)CC1] | 3250 |
| 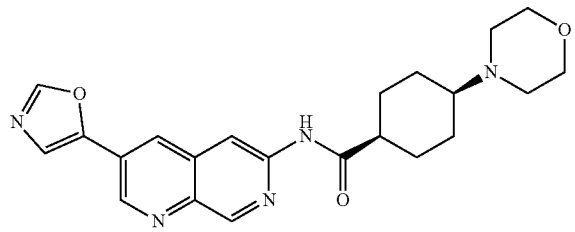 [SMILES: O=C(Nc1cc2cc(-c3cnco3)cnc2cn1)[C@H]1CC[C@@H](N2CCOCC2)CC1] | 3251 |
| 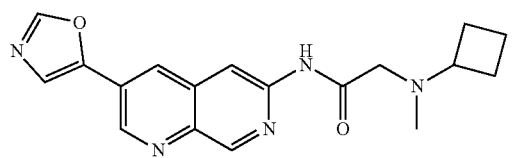 [SMILES: CN(CC(=O)Nc1cc2cc(-c3cnco3)cnc2cn1)C1CCC1] | 3252 |
| 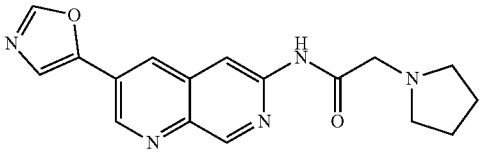 [SMILES: O=C(CN1CCCC1)Nc1cc2cc(-c3cnco3)cnc2cn1] | 3253 |

TABLE 1-continued
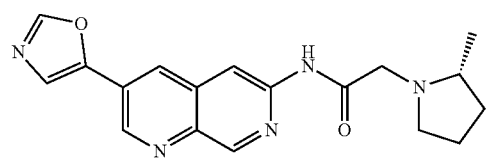 [SMILES: C[C@@H]1CCCN1CC(=O)Nc1cc2cc(-c3cnco3)cnc2cn1] 3254
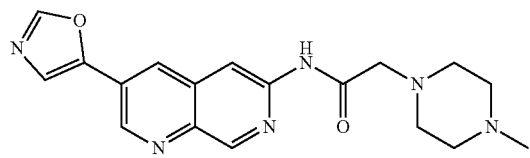 [SMILES: CN1CCN(CC(=O)Nc2cc3cc(-c4cnco4)cnc3cn2)CC1] 3255
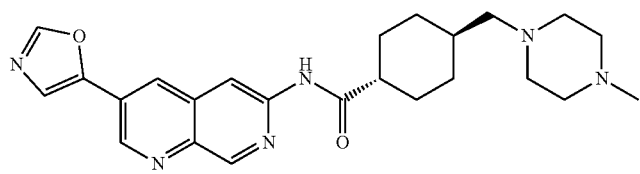 [SMILES: CN1CCN(C[C@H]2CC[C@H](C(=O)Nc3cc4cc(-c5cnco5)cnc4cn3)CC2)CC1] 3256
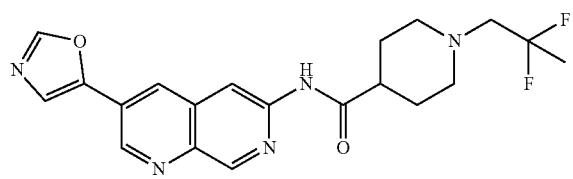 [SMILES: CC(F)(F)CN1CCC(C(=O)Nc2cc3cc(-c4cnco4)cnc3cn2)CC1] 3257
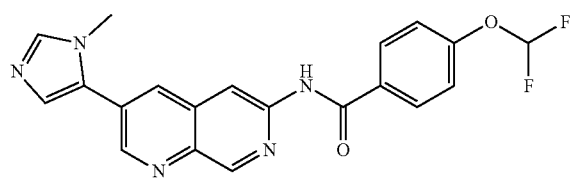 [SMILES: Cn1cncc1-c1cnc2cnc(NC(=O)c3ccc(OC(F)F)cc3)cc2c1] 3258
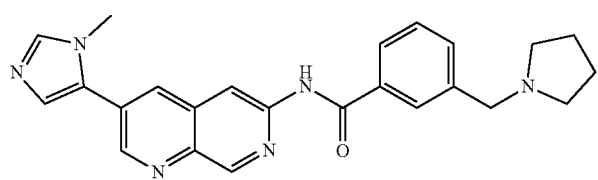 [SMILES: Cn1cncc1-c1cnc2cnc(NC(=O)c3cccc(CN4CCCC4)c3)cc2c1] 3259
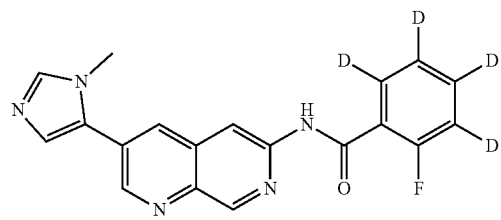 3260
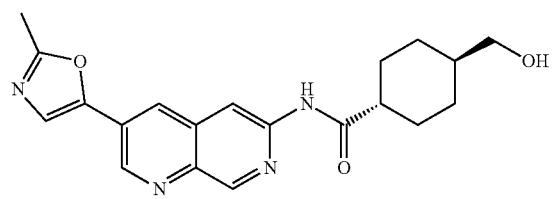 3261

TABLE 1-continued

| | |
|---|---|
| (structure) | 3262 |
| (structure) | 3263 |
| (structure) | 3264 |
| (structure) | 3265 |
| (structure) | 3266 |
| (structure) | 3267 |
| (structure) | 3268 |

TABLE 1-continued

| | |
|---|---|
| (structure) | 3269 |
| (structure) | 3270 |
| (structure) | 3271 |
| (structure) | 3272 |
| (structure) | 3273 |
| (structure) | 3274 |
| (structure) | 3275 |

TABLE 1-continued
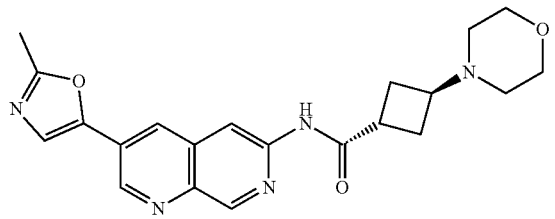 3276
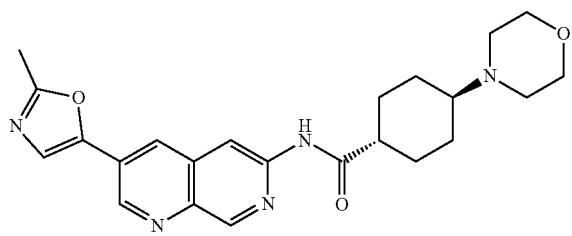 [SMILES: Cc1ncc(-c2cnc3cnc(NC(=O)[C@H]4CC[C@H](N5CCOCC5)CC4)cc3c2)o1] 3277
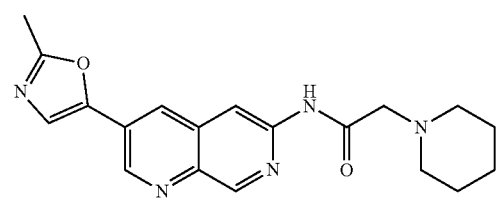 3278
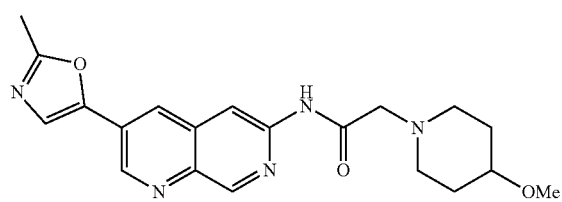 [SMILES: COC1CCN(CC(=O)Nc2cc3cc(-c4cnc(C)o4)cnc3cn2)CC1] 3279
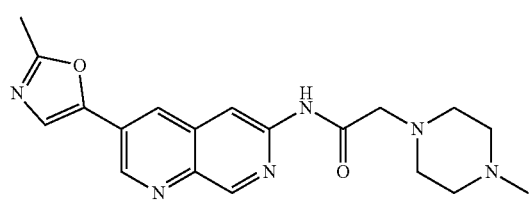 [SMILES: Cc1ncc(-c2cnc3cnc(NC(=O)CN4CCN(C)CC4)cc3c2)o1] 3280
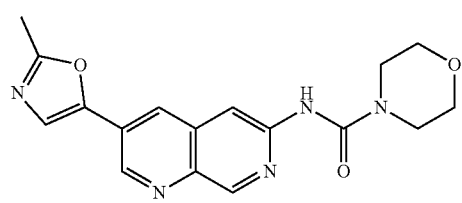 [SMILES: Cc1ncc(-c2cnc3cnc(NC(=O)N4CCOCC4)cc3c2)o1] 3281
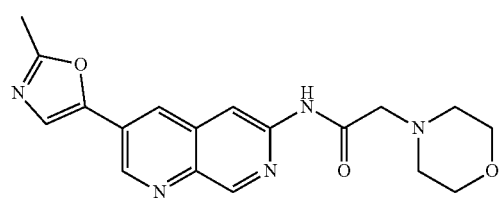 [SMILES: Cc1ncc(-c2cnc3cnc(NC(=O)CN4CCOCC4)cc3c2)o1] 3282

TABLE 1-continued
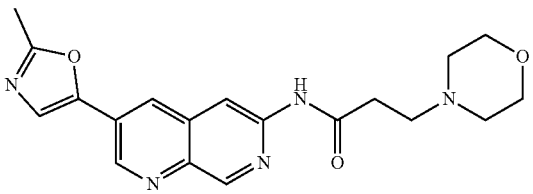 [SMILES: Cc1ncc(-c2cnc3cnc(NC(=O)CCN4CCOCC4)cc3c2)o1]
3283
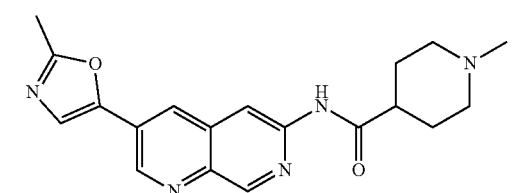
3284
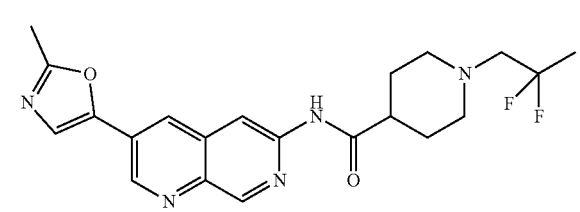 [SMILES: Cc1ncc(-c2cnc3cnc(NC(=O)C4CCN(CC(C)(F)F)CC4)cc3c2)o1]
3285
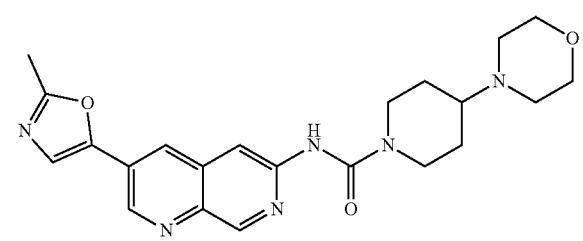 [SMILES: Cc1ncc(-c2cnc3cnc(NC(=O)N4CCC(N5CCOCC5)CC4)cc3c2)o1]
3286
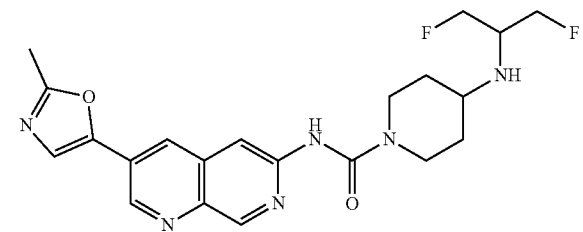 [SMILES: Cc1ncc(-c2cnc3cnc(NC(=O)N4CCC(NC(CF)CF)CC4)cc3c2)o1]
3287
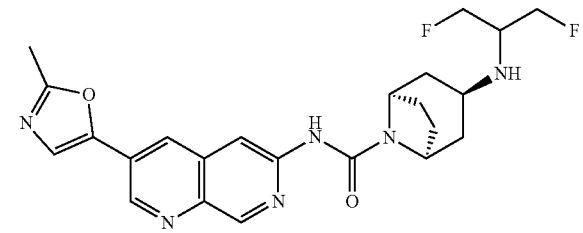 [SMILES: Cc1ncc(-c2cnc3cnc(NC(=O)N4[C@@H]5CC[C@H]4C[C@H](NC(CF)CF)C5)cc3c2)o1]
3288
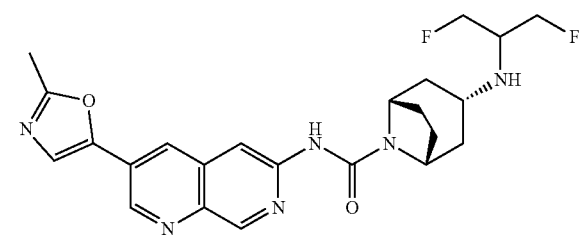 [SMILES: Cc1ncc(-c2cnc3cnc(NC(=O)N4[C@@H]5CC[C@H]4C[C@H](NC(CF)CF)C5)cc3c2)o1]
3289

TABLE 1-continued
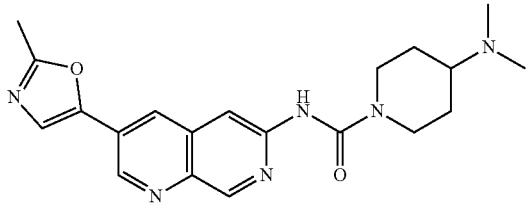 [SMILES: Cc1ncc(-c2cnc3cnc(NC(=O)N4CCC(N(C)C)CC4)cc3c2)o1]
3290
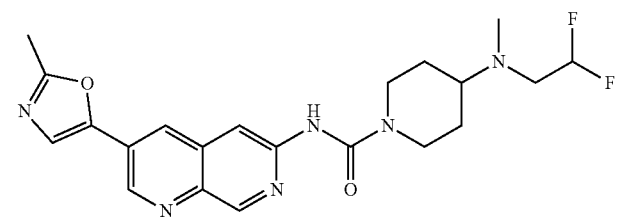 [SMILES: Cc1ncc(-c2cnc3cnc(NC(=O)N4CCC(N(C)CC(F)F)CC4)cc3c2)o1]
3291
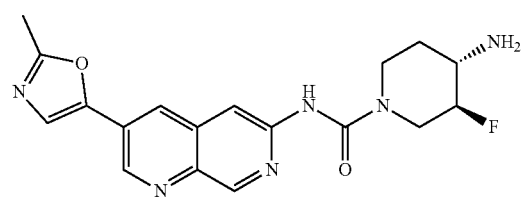 [SMILES: Cc1ncc(-c2cnc3cnc(NC(=O)N4CC[C@H](N)[C@@H](F)C4)cc3c2)o1]
3292
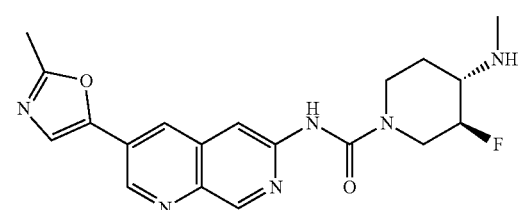
3293
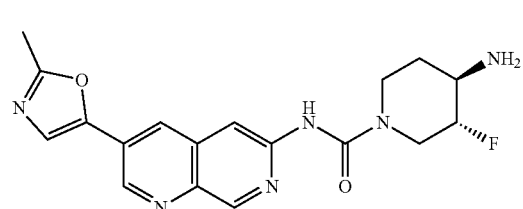
3294
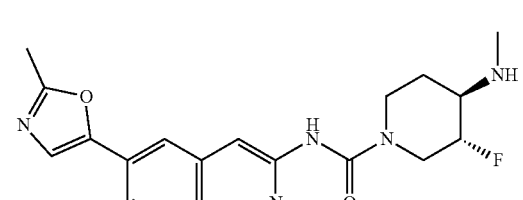
3295
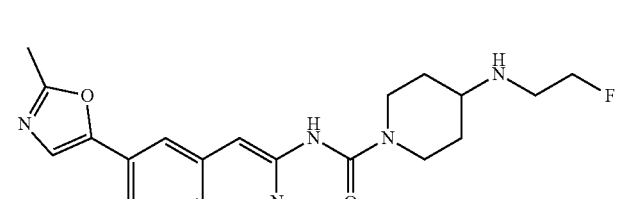
3296

TABLE 1-continued
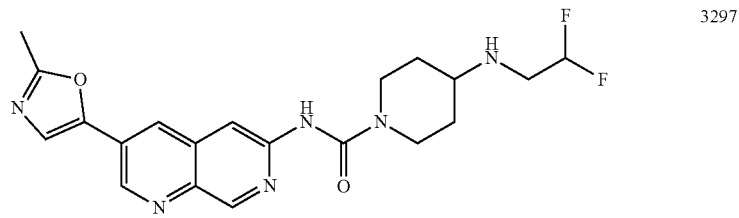 3297
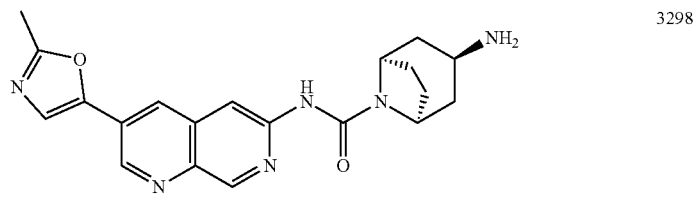 3298
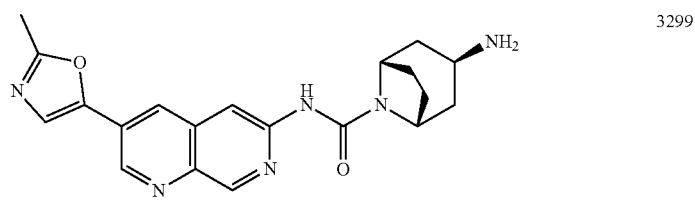 3299
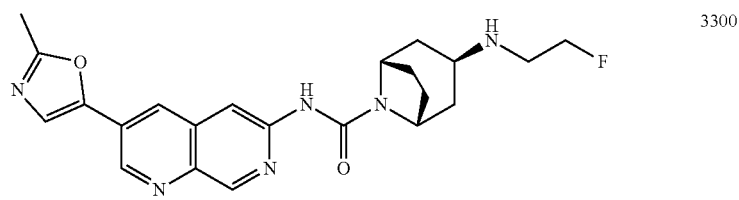 3300
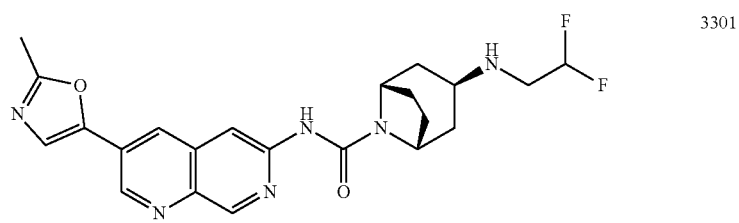 3301
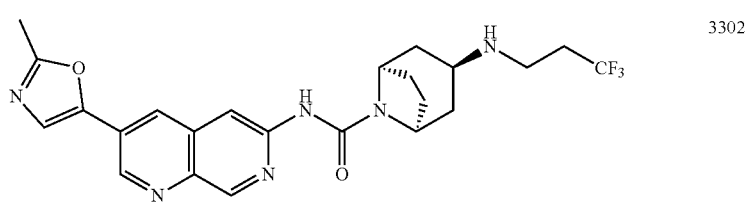 3302
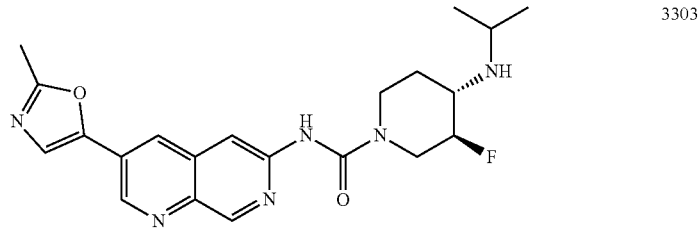 3303

TABLE 1-continued
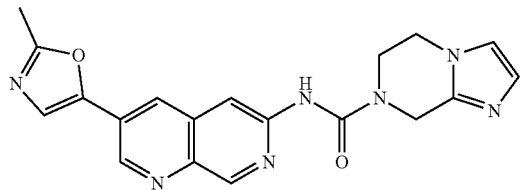 [SMILES: Cc1ncc(-c2cnc3cnc(NC(=O)N4CCn5ccnc5C4)cc3c2)o1] 3304
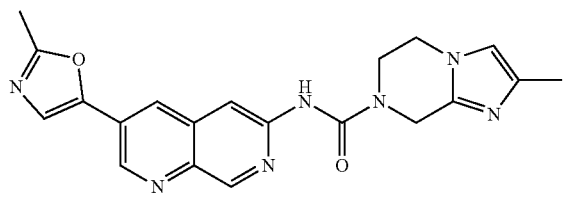 3305
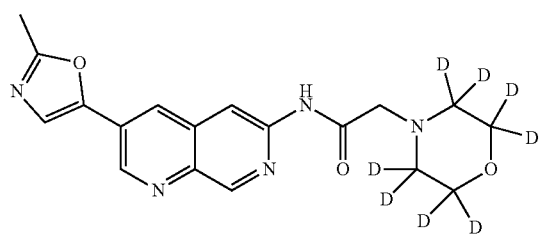 3306
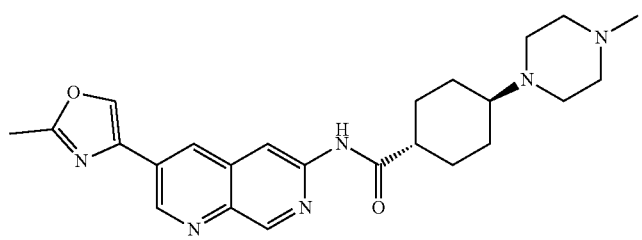 3307
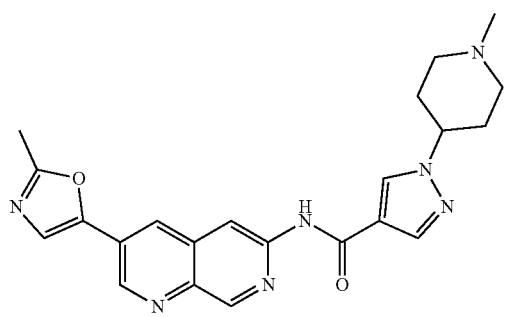 [SMILES: Cc1ncc(-c2cnc3cnc(NC(=O)c4cnn(C5CCN(C)CC5)c4)cc3c2)o1] 3308
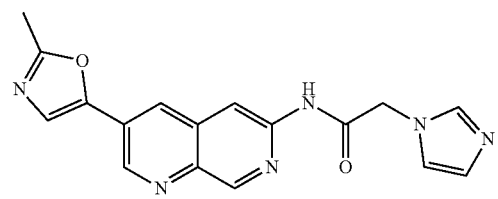 [SMILES: Cc1ncc(-c2cnc3cnc(NC(=O)Cn4ccnc4)cc3c2)o1] 3309
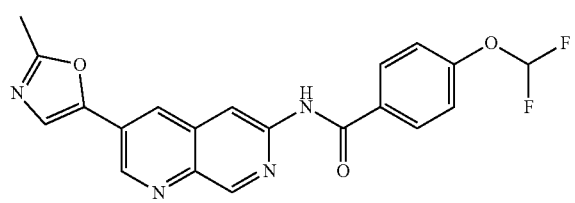 [SMILES: Cc1ncc(-c2cnc3cnc(NC(=O)c4ccc(OC(F)F)cc4)cc3c2)o1] 3310

TABLE 1-continued
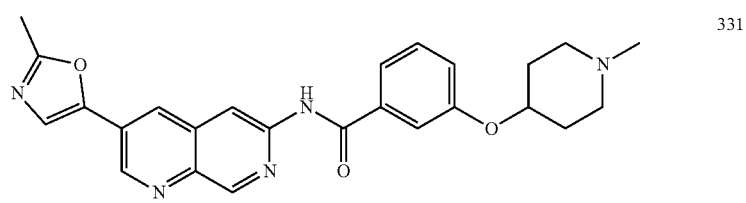  3311
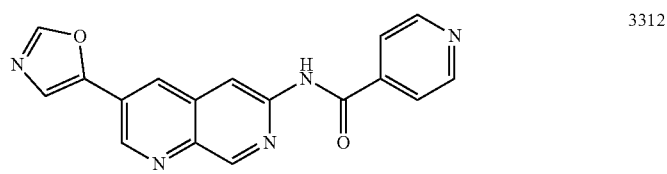  3312
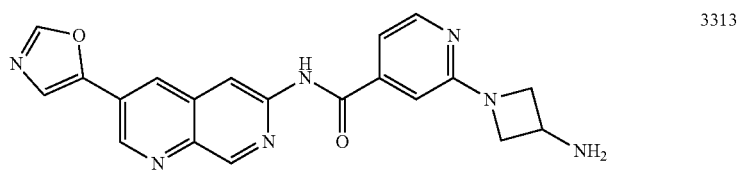  3313
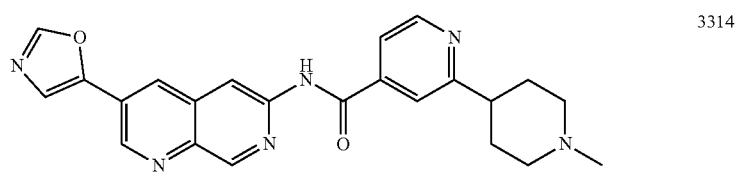  3314
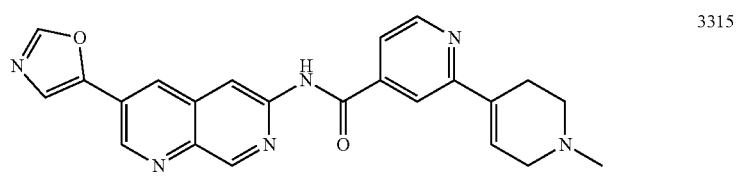  3315
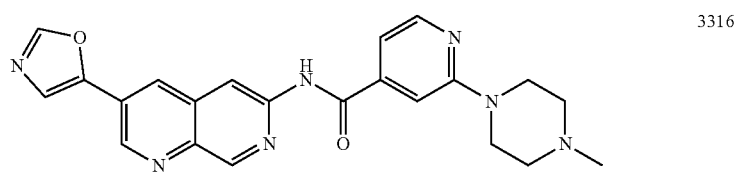  3316
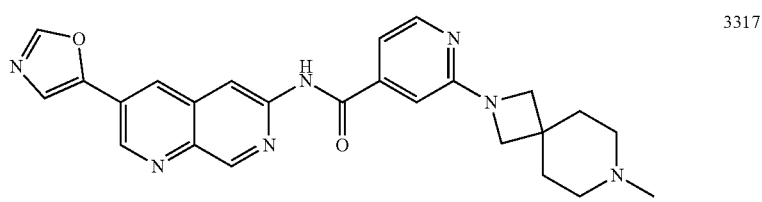  3317
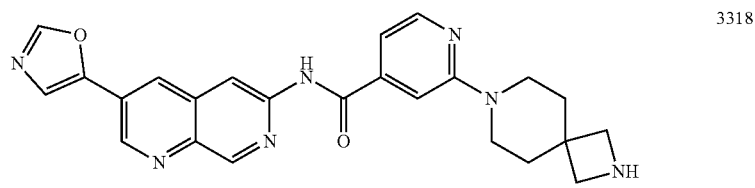  3318

TABLE 1-continued
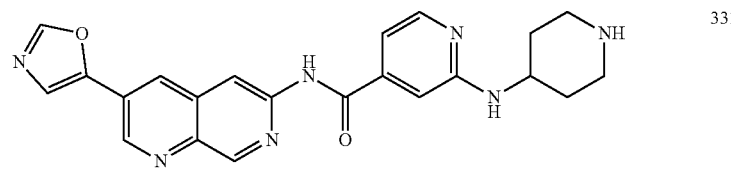 3319
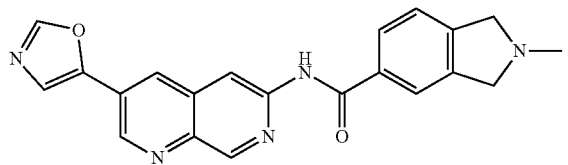 [SMILES: CN1Cc2ccc(C(=O)Nc3cc4cc(-c5cnco5)cnc4cn3)cc2C1] 3320
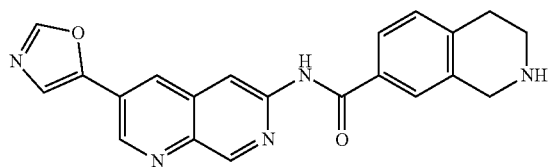 [SMILES: O=C(Nc1cc2cc(-c3cnco3)cnc2cn1)c1ccc2c(c1)CNCC2] 3321
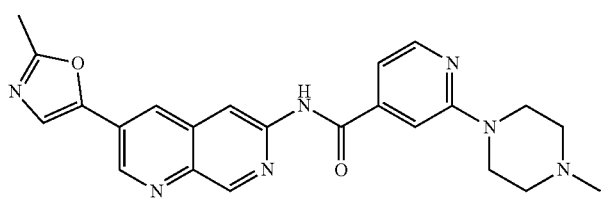 3322
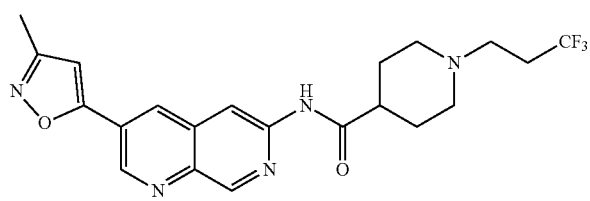 [SMILES: Cc1cc(-c2cnc3cnc(NC(=O)C4CCN(CCC(F)(F)F)CC4)cc3c2)on1] 3323
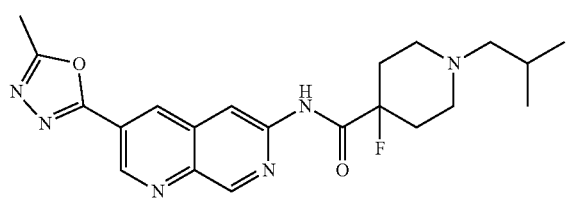 [SMILES: Cc1nnc(-c2cnc3cnc(NC(=O)C4(F)CCN(CC(C)C)CC4)cc3c2)o1] 3324
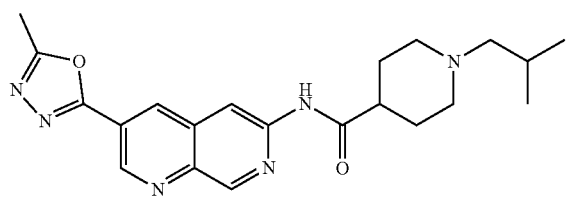 [SMILES: Cc1nnc(-c2cnc3cnc(NC(=O)C4CCN(CC(C)C)CC4)cc3c2)o1] 3325
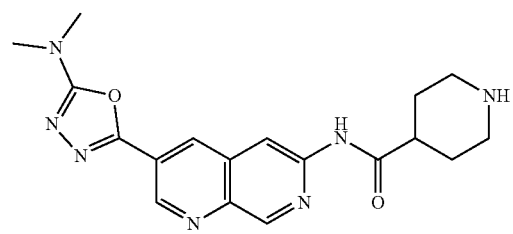 [SMILES: CN(C)c1nnc(-c2cnc3cnc(NC(=O)C4CCNCC4)cc3c2)o1] 3326

TABLE 1-continued
| | |
|---|---|
| 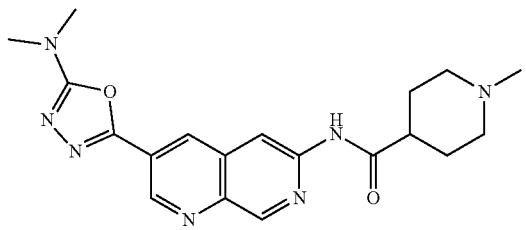 | 3327 |
| 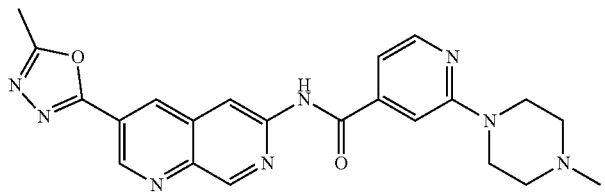 [SMILES: Cc1nnc(-c2cnc3cnc(NC(=O)c4ccnc(N5CCN(C)CC5)c4)cc3c2)o1] | 3328 |
| 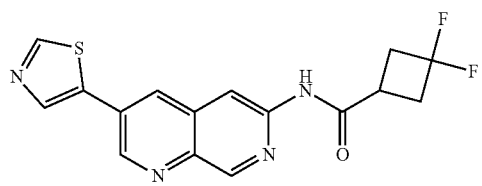 | 3329 |
| 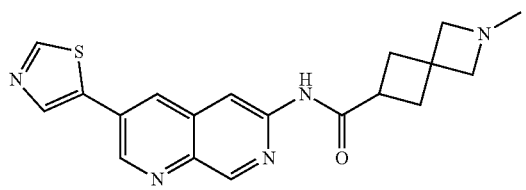 [SMILES: CN1CC2(CC(C(=O)Nc3cc4cc(-c5cncs5)cnc4cn3)C2)C1] | 3330 |
| 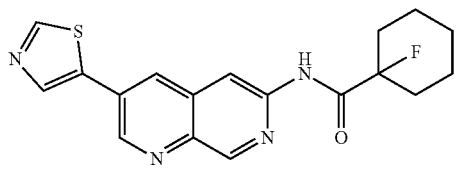 | 3331 |
| 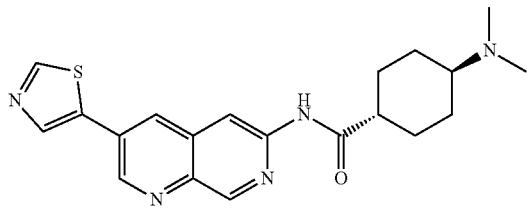 [SMILES: CN(C)[C@H]1CC[C@H](C(=O)Nc2cc3cc(-c4cncs4)cnc3cn2)CC1] | 3332 |
| 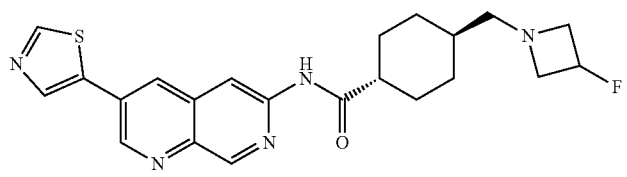 [SMILES: O=C(Nc1cc2cc(-c3cncs3)cnc2cn1)[C@H]1CC[C@H](CN2CC(F)C2)CC1] | 3333 |
| 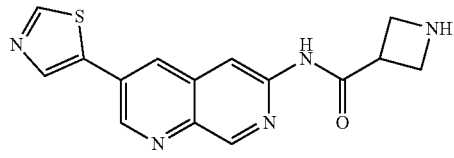 [SMILES: O=C(Nc1cc2cc(-c3cncs3)cnc2cn1)C1CNC1] | 3334 |

TABLE 1-continued
| | |
|---|---|
| 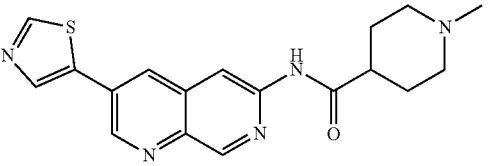 [SMILES: CN1CCC(C(=O)Nc2cc3cc(-c4cncs4)cnc3cn2)CC1] | 3335 |
| 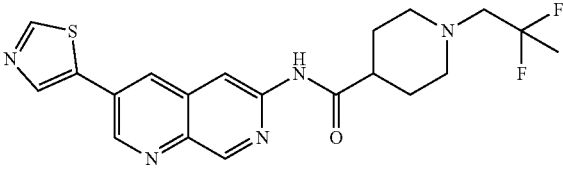 [SMILES: CC(F)(F)CN1CCC(C(=O)Nc2cc3cc(-c4cncs4)cnc3cn2)CC1] | 3336 |
| 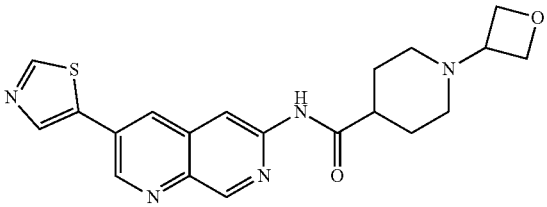 [SMILES: O=C(Nc1cc2cc(-c3cncs3)cnc2cn1)C1CCN(C2COC2)CC1] | 3337 |
| 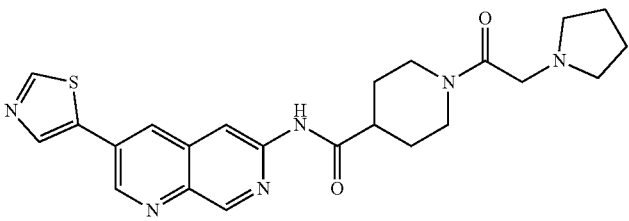 [SMILES: O=C(Nc1cc2cc(-c3cncs3)cnc2cn1)C1CCN(C(=O)CN2CCCC2)CC1] | 3338 |
| 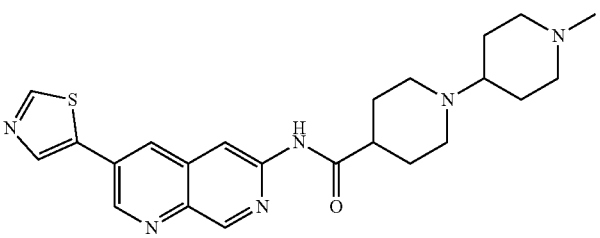 | 3339 |
| 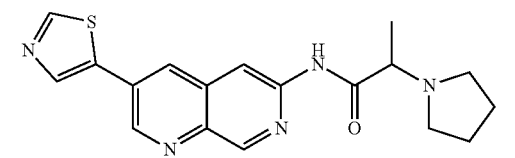 [SMILES: CC(C(=O)Nc1cc2cc(-c3cncs3)cnc2cn1)N1CCCC1] | 3340 |
| 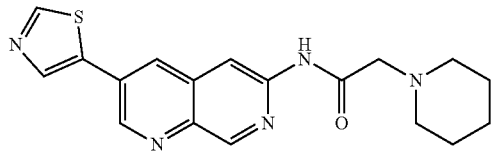 [SMILES: O=C(CN1CCCCC1)Nc1cc2cc(-c3cncs3)cnc2cn1] | 3341 |
| 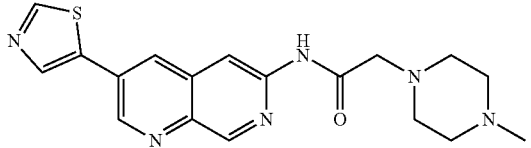 | 3342 |

TABLE 1-continued

| | |
|---|---|
| (structure) | 3343 |
| (structure) | 3344 |
| (structure) | 3345 |
| (structure) | 3346 |
| (structure) | 3347 |
| (structure) | 3348 |
| (structure) | 3349 |
| (structure) | 3350 |

TABLE 1-continued
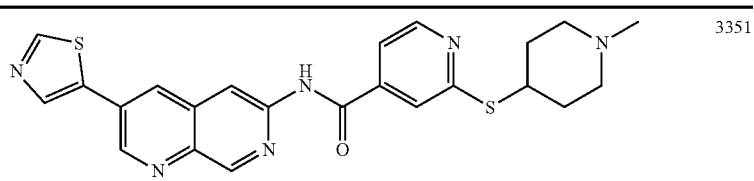
3351
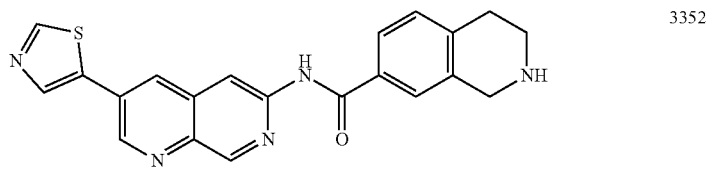
3352
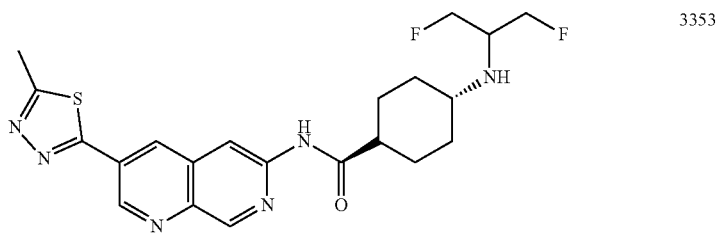
3353
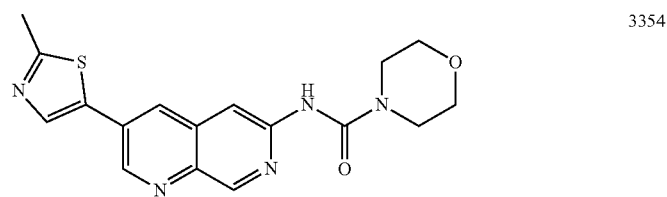
3354
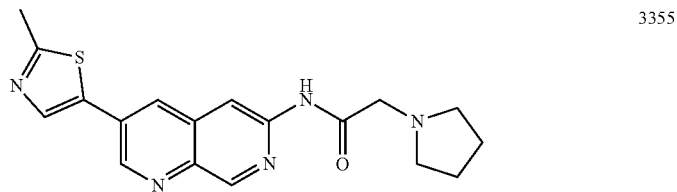
3355
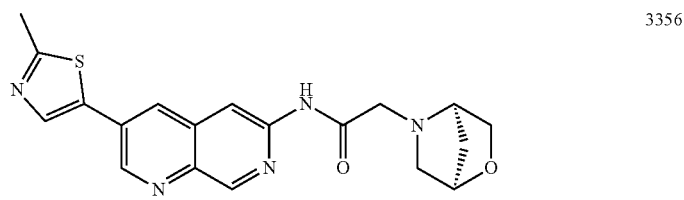
3356
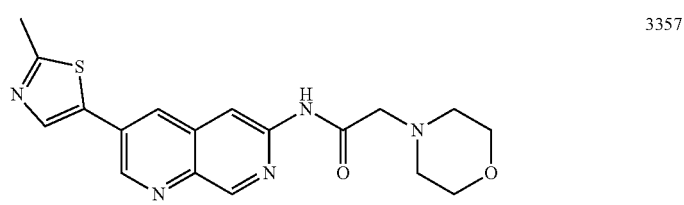
3357
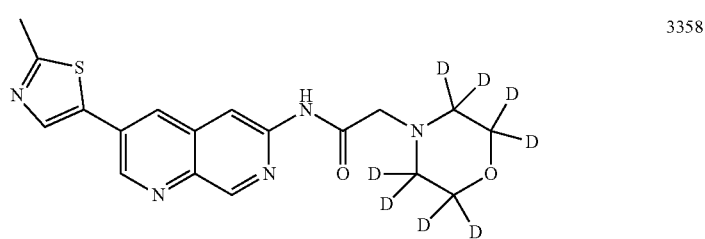
3358

TABLE 1-continued
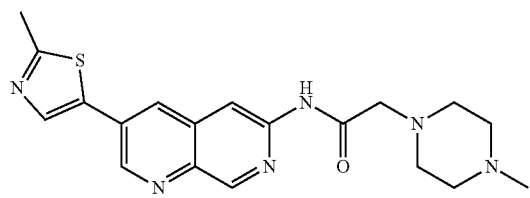 3359
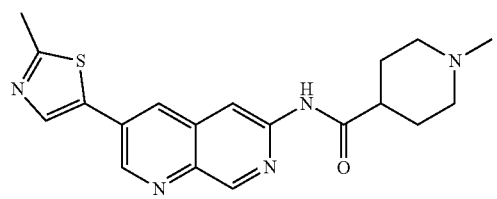 [SMILES: Cc1ncc(-c2cnc3cnc(NC(=O)C4CCN(C)CC4)cc3c2)s1] 3360
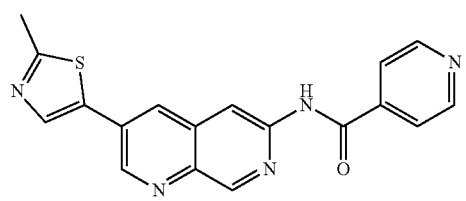 [SMILES: Cc1ncc(-c2cnc3cnc(NC(=O)c4ccncc4)cc3c2)s1] 3361
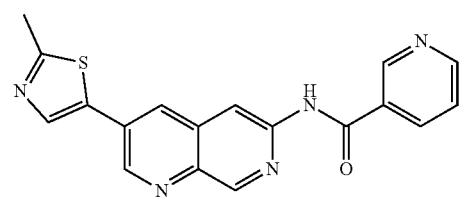 [SMILES: Cc1ncc(-c2cnc3cnc(NC(=O)c4cccnc4)cc3c2)s1] 3362
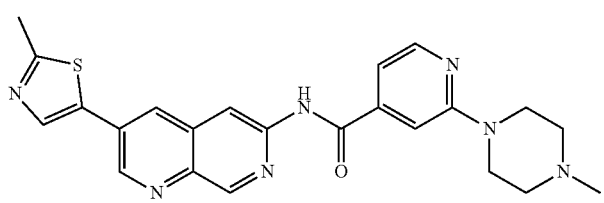 3363
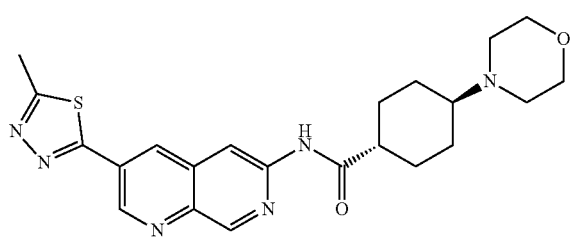 [SMILES: Cc1nnc(-c2cnc3cnc(NC(=O)[C@H]4CC[C@H](N5CCOCC5)CC4)cc3c2)s1] 3364
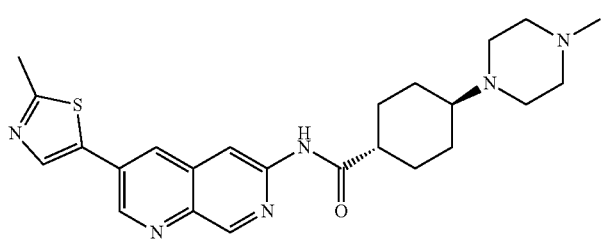 [SMILES: Cc1ncc(-c2cnc3cnc(NC(=O)[C@H]4CC[C@H](N5CCN(C)CC5)CC4)cc3c2)s1] 3365

TABLE 1-continued

| | |
|---|---|
| (structure) | 3366 |
| (structure) | 3367 |
| (structure) | 3368 |
| (structure) | 3369 |
| (structure) | 3370 |
| (structure) | 3371 |
| (structure) | 3372 |

TABLE 1-continued

| | |
|---|---|
| (structure) | 3373 |
| (structure) | 3374 |
| (structure) | 3375 |
| (structure) | 3376 |
| (structure) | 3377 |
| (structure) | 3378 |
| (structure) | 3379 |

TABLE 1-continued
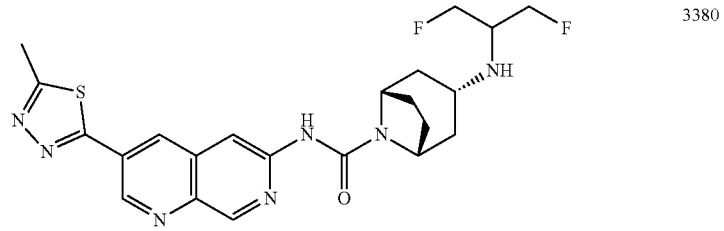
3380
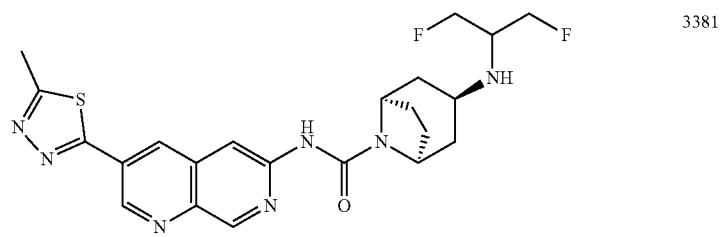
3381
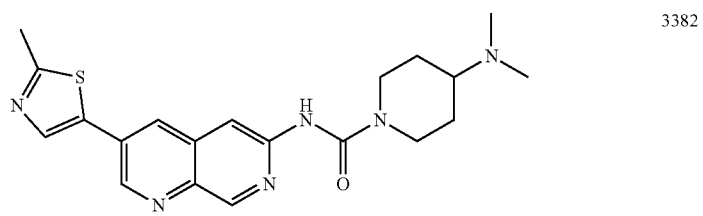
3382
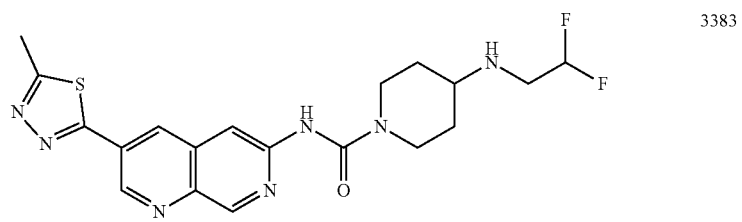
3383
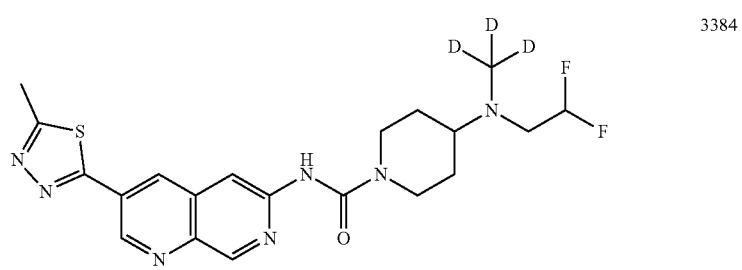
3384
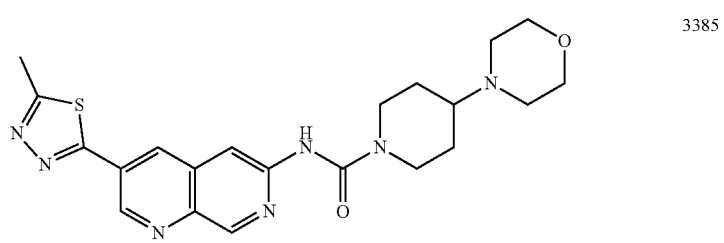
3385

TABLE 1-continued
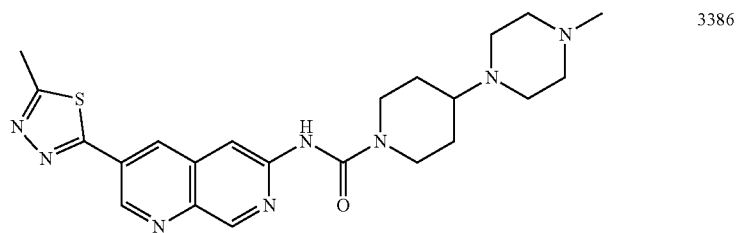
3386
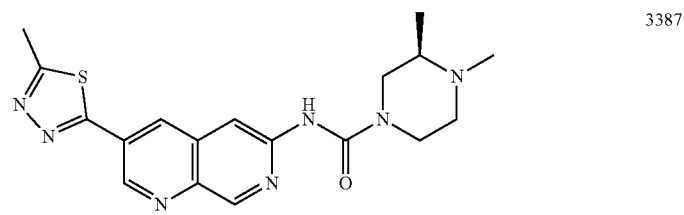
3387
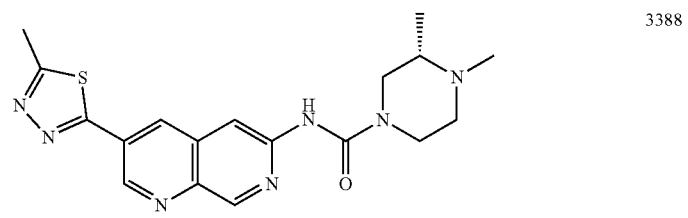
3388
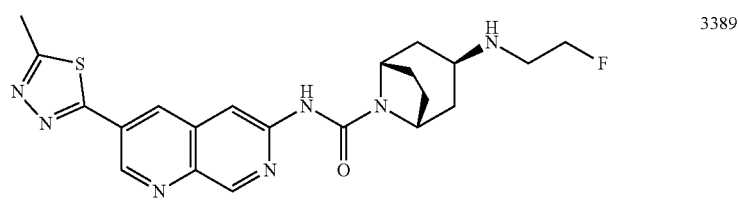
3389
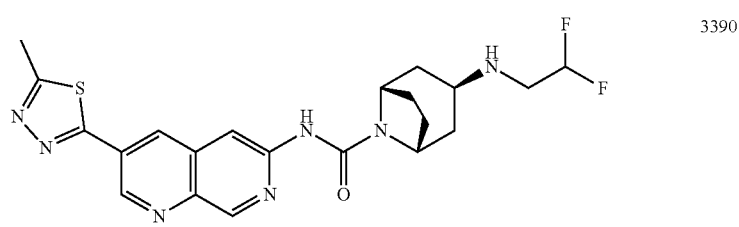
3390
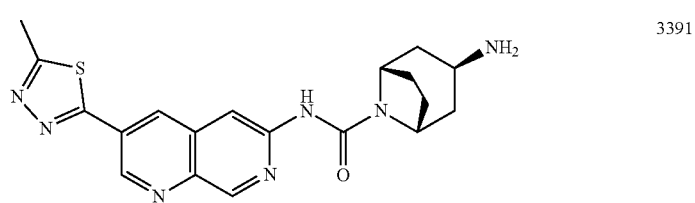
3391
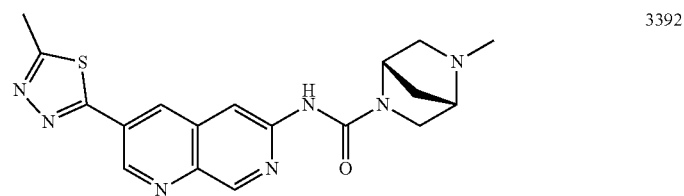
3392

TABLE 1-continued
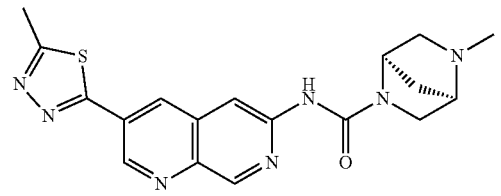 [SMILES: Cc1nnc(-c2cnc3cnc(NC(=O)N4C[C@H]5C[C@@H]4CN5C)cc3c2)s1] 3393
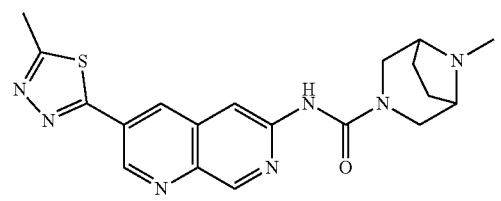 [SMILES: Cc1nnc(-c2cnc3cnc(NC(=O)N4CC5CCC(C4)N5C)cc3c2)s1] 3394
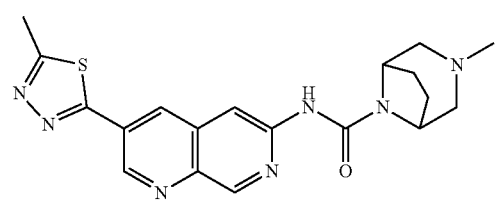 [SMILES: Cc1nnc(-c2cnc3cnc(NC(=O)N4C5CCC4CN(C)C5)cc3c2)s1] 3395
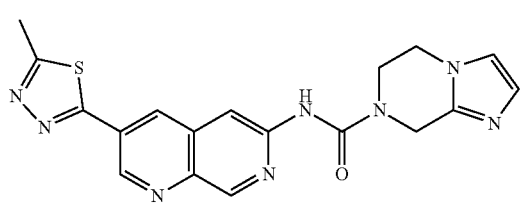 [SMILES: Cc1nnc(-c2cnc3cnc(NC(=O)N4CCn5ccnc5C4)cc3c2)s1] 3396
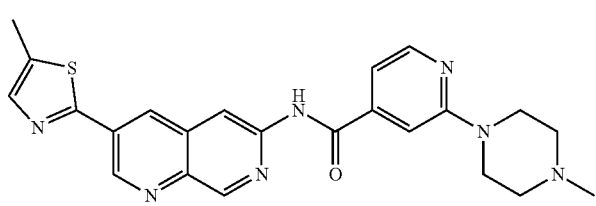 [SMILES: Cc1cnc(-c2cnc3cnc(NC(=O)c4ccnc(N5CCN(C)CC5)c4)cc3c2)s1] 3397
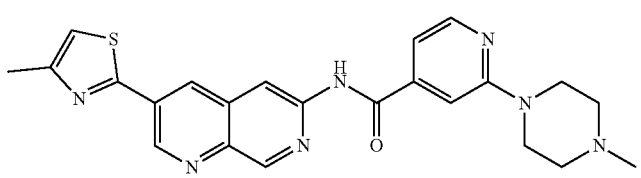 3398
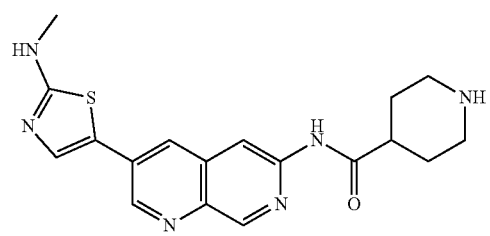 [SMILES: CNc1ncc(-c2cnc3cnc(NC(=O)C4CCNCC4)cc3c2)s1] 3399

TABLE 1-continued
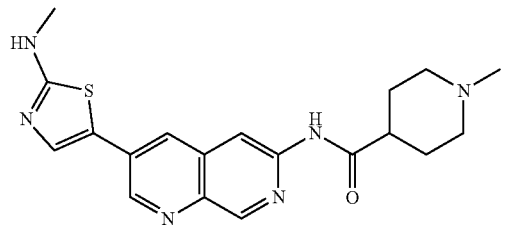 [SMILES: CNc1ncc(-c2cnc3cnc(NC(=O)C4CCN(C)CC4)cc3c2)s1]
3400
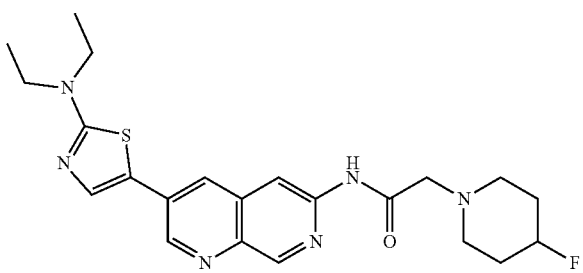 [SMILES: CCN(CC)c1ncc(-c2cnc3cnc(NC(=O)CN4CCC(F)CC4)cc3c2)s1]
3401
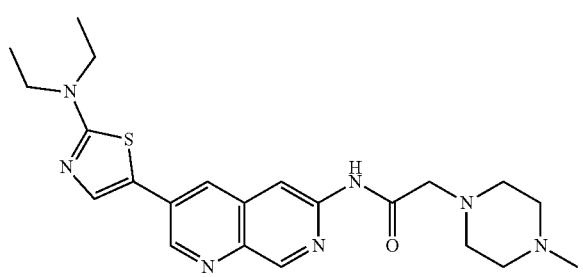 [SMILES: CCN(CC)c1ncc(-c2cnc3cnc(NC(=O)CN4CCN(C)CC4)cc3c2)s1]
3402
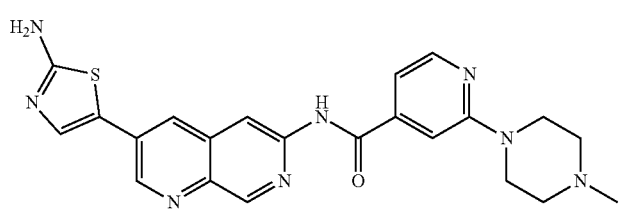 [SMILES: CN1CCN(c2cc(C(=O)Nc3cc4cc(-c5cnc(N)s5)cnc4cn3)ccn2)CC1]
3403
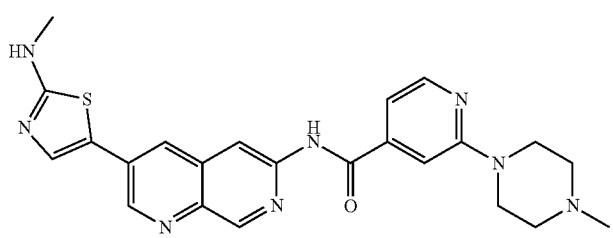 [SMILES: CNc1ncc(-c2cnc3cnc(NC(=O)c4ccnc(N5CCN(C)CC5)c4)cc3c2)s1]
3404
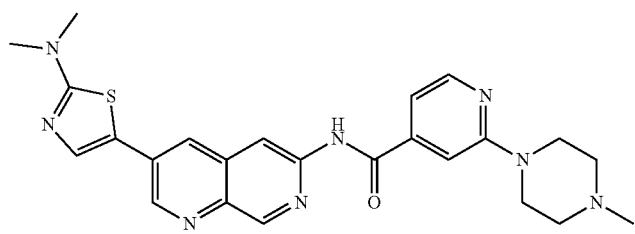
3405

TABLE 1-continued
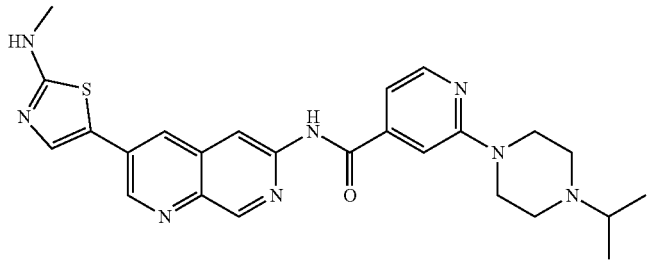 [SMILES: CNc1ncc(-c2cnc3cnc(NC(=O)c4ccnc(N5CCN(C(C)C)CC5)c4)cc3c2)s1]
3406
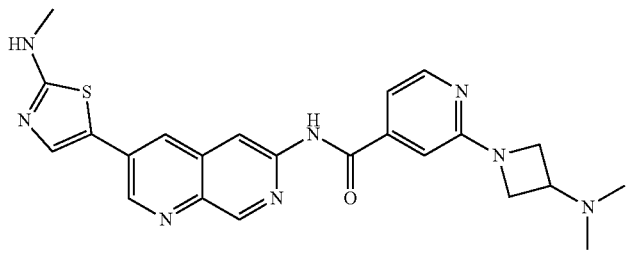 [SMILES: CNc1ncc(-c2cnc3cnc(NC(=O)c4ccnc(N5CC(N(C)C)C5)c4)cc3c2)s1]
3407
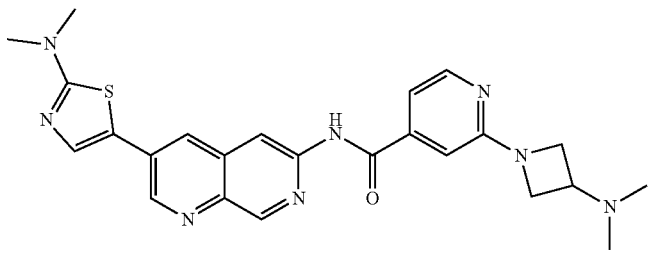
3408
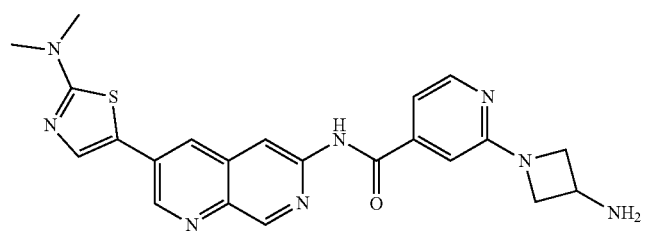 [SMILES: CN(C)c1ncc(-c2cnc3cnc(NC(=O)c4ccnc(N5CC(N)C5)c4)cc3c2)s1]
3409
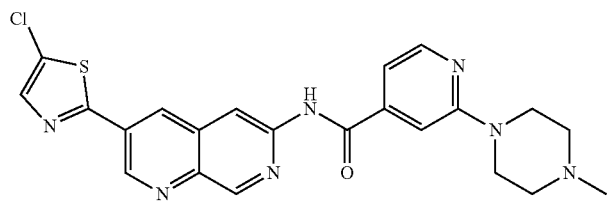 [SMILES: CN1CCN(c2cc(C(=O)Nc3cc4cc(-c5ncc(Cl)s5)cnc4cn3)ccn2)CC1]
3410
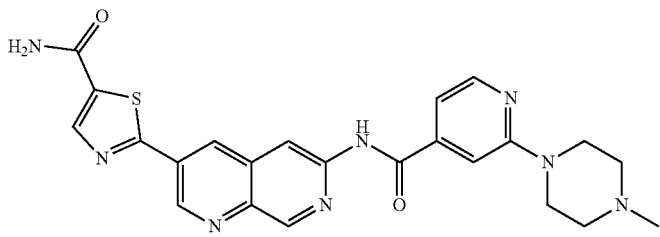 [SMILES: CN1CCN(c2cc(C(=O)Nc3cc4cc(-c5ncc(C(N)=O)s5)cnc4cn3)ccn2)CC1]
3411
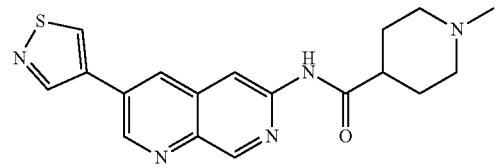 [SMILES: CN1CCC(C(=O)Nc2cc3cc(-c4cnsc4)cnc3cn2)CC1]
3412

TABLE 1-continued
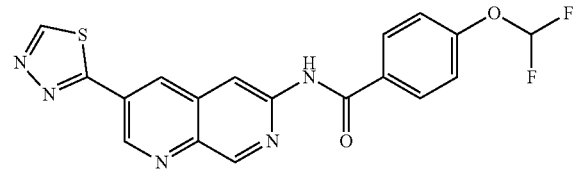 [SMILES: O=C(Nc1cc2cc(-c3nncs3)cnc2cn1)c1ccc(OC(F)F)cc1] 3413
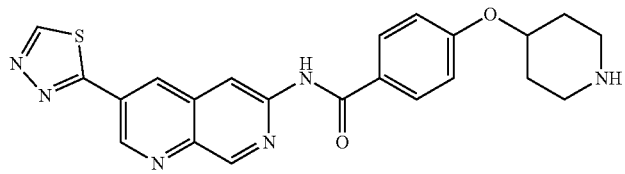 [SMILES: O=C(Nc1cc2cc(-c3nncs3)cnc2cn1)c1ccc(OC2CCNCC2)cc1] 3414
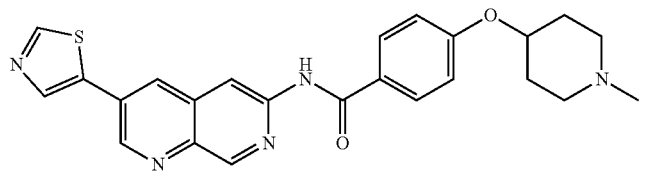 [SMILES: CN1CCC(Oc2ccc(C(=O)Nc3cc4cc(-c5cncs5)cnc4cn3)cc2)CC1] 3415
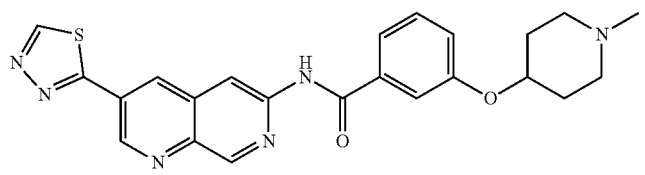 [SMILES: CN1CCC(Oc2cccc(C(=O)Nc3cc4cc(-c5nncs5)cnc4cn3)c2)CC1] 3416
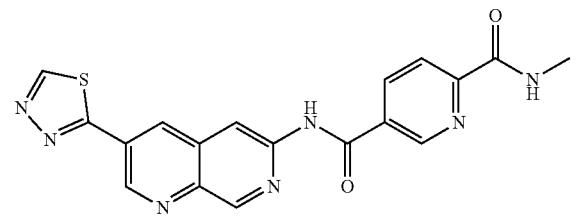 [SMILES: CNC(=O)c1ccc(C(=O)Nc2cc3cc(-c4nncs4)cnc3cn2)cn1] 3417
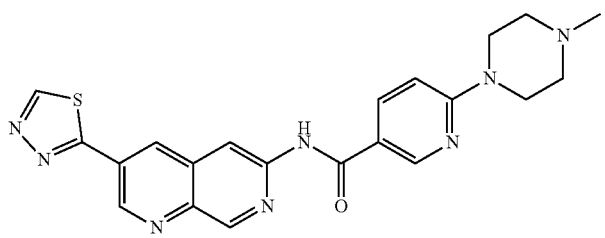 3418
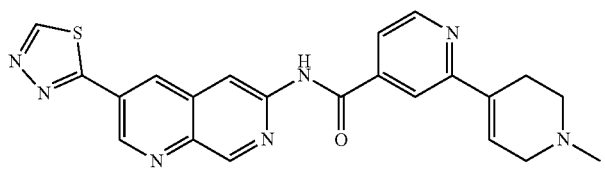 [SMILES: CN1CC=C(c2cc(C(=O)Nc3cc4cc(-c5nncs5)cnc4cn3)ccn2)CC1] 3419
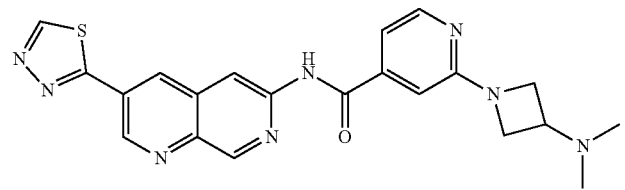 [SMILES: CN(C)C1CN(c2cc(C(=O)Nc3cc4cc(-c5nncs5)cnc4cn3)ccn2)C1] 3420

TABLE 1-continued
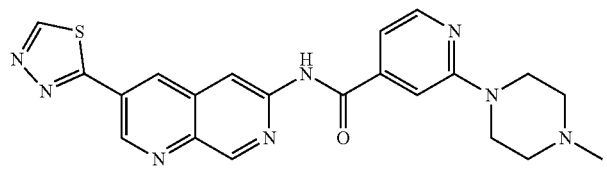 [SMILES: CN1CCN(c2cc(C(=O)Nc3cc4cc(-c5nncs5)cnc4cn3)ccn2)CC1] 3421
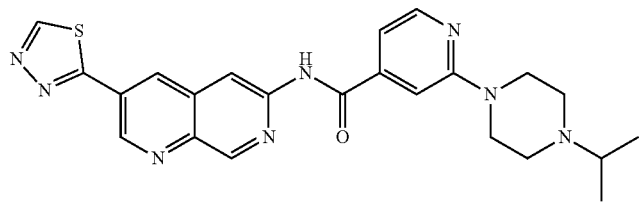 [SMILES: CC(C)N1CCN(c2cc(C(=O)Nc3cc4cc(-c5nncs5)cnc4cn3)ccn2)CC1] 3422
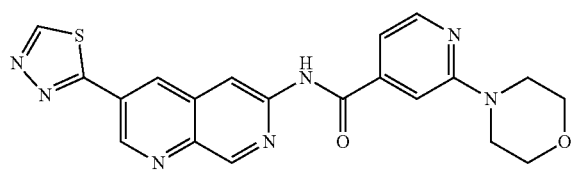 [SMILES: O=C(Nc1cc2cc(-c3nncs3)cnc2cn1)c1ccnc(N2CCOCC2)c1] 3423
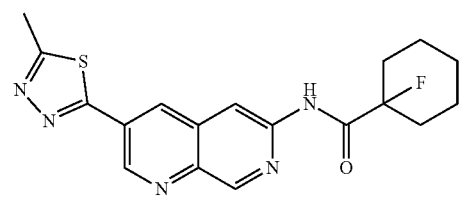 3424
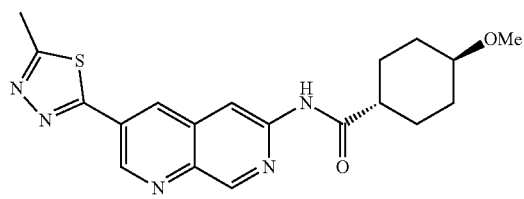 [SMILES: CO[C@H]1CC[C@H](C(=O)Nc2cc3cc(-c4nnc(C)s4)cnc3cn2)CC1] 3425
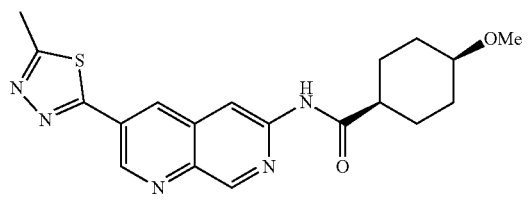 [SMILES: CO[C@H]1CC[C@@H](C(=O)Nc2cc3cc(-c4nnc(C)s4)cnc3cn2)CC1] 3426
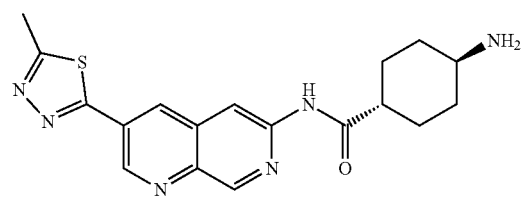 [SMILES: Cc1nnc(-c2cnc3cnc(NC(=O)[C@H]4CC[C@H](N)CC4)cc3c2)s1] 3427
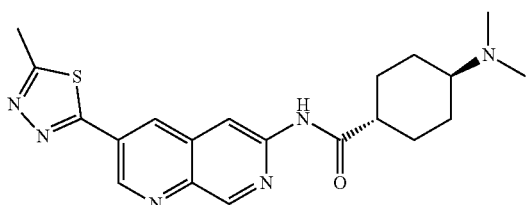 3428

TABLE 1-continued
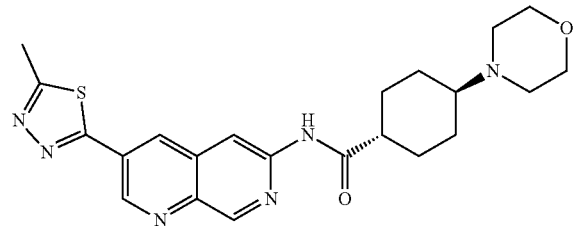 [SMILES: Cc1nnc(-c2cnc3cnc(NC(=O)[C@H]4CC[C@H](N5CCOCC5)CC4)cc3c2)s1]
3429
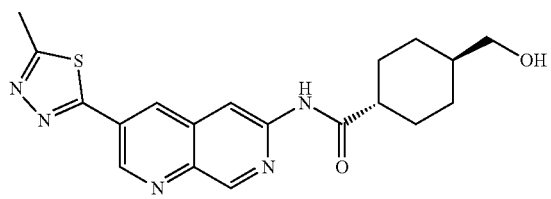
3430
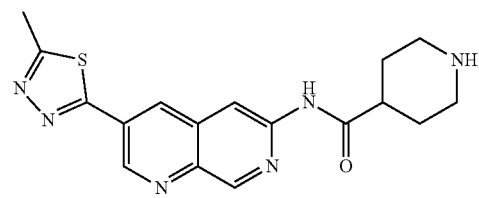 [SMILES: Cc1nnc(-c2cnc3cnc(NC(=O)C4CCNCC4)cc3c2)s1]
3431
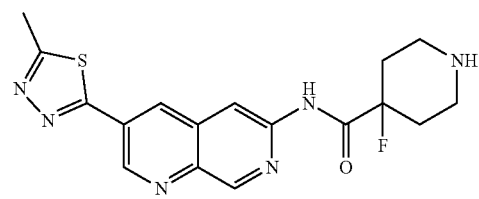 [SMILES: Cc1nnc(-c2cnc3cnc(NC(=O)C4(F)CCNCC4)cc3c2)s1]
3432
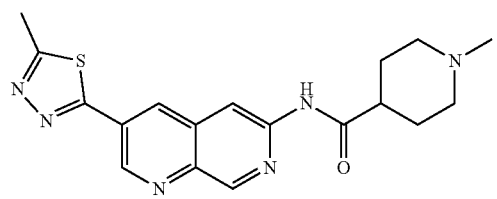 [SMILES: Cc1nnc(-c2cnc3cnc(NC(=O)C4CCN(C)CC4)cc3c2)s1]
3433
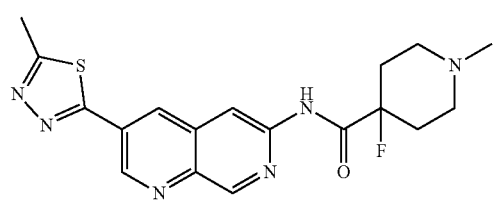 [SMILES: Cc1nnc(-c2cnc3cnc(NC(=O)C4(F)CCN(C)CC4)cc3c2)s1]
3434
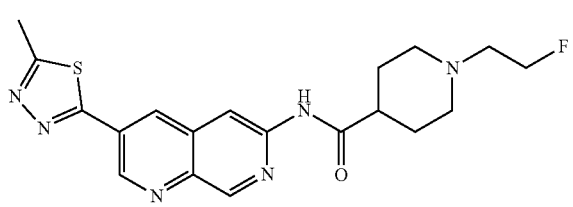 [SMILES: Cc1nnc(-c2cnc3cnc(NC(=O)C4CCN(CCF)CC4)cc3c2)s1]
3435

TABLE 1-continued
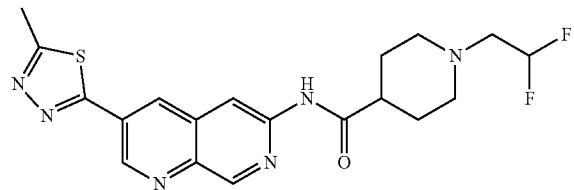 [SMILES: Cc1nnc(-c2cnc3cnc(NC(=O)C4CCN(CC(F)F)CC4)cc3c2)s1] 3436
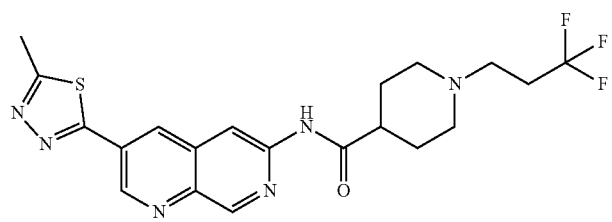 [SMILES: Cc1nnc(-c2cnc3cnc(NC(=O)C4CCN(CCC(F)(F)F)CC4)cc3c2)s1] 3437
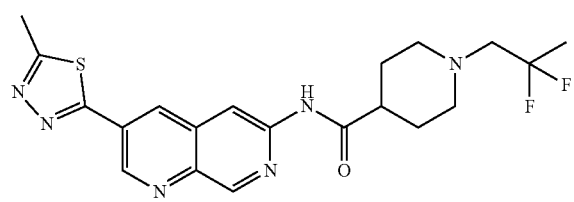 [SMILES: Cc1nnc(-c2cnc3cnc(NC(=O)C4CCN(CC(C)(F)F)CC4)cc3c2)s1] 3438
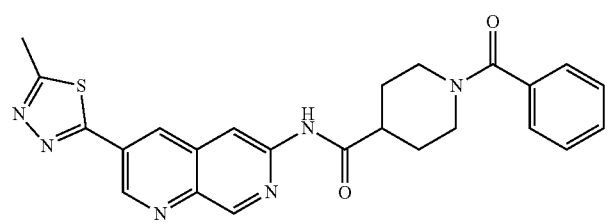 [SMILES: Cc1nnc(-c2cnc3cnc(NC(=O)C4CCN(C(=O)c5ccccc5)CC4)cc3c2)s1] 3439
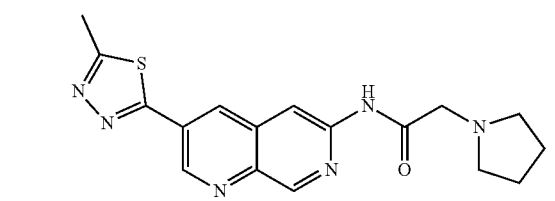 3440
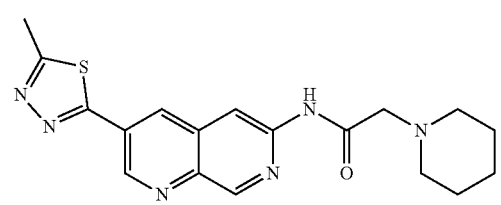 [SMILES: Cc1nnc(-c2cnc3cnc(NC(=O)CN4CCCCC4)cc3c2)s1] 3441
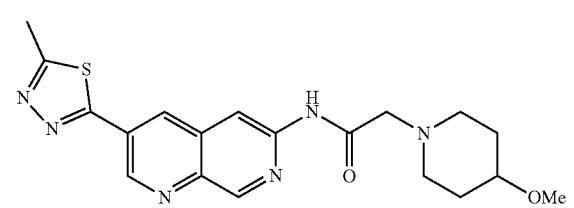 [SMILES: COC1CCN(CC(=O)Nc2cc3cc(-c4nnc(C)s4)cnc3cn2)CC1] 3442

TABLE 1-continued
| | |
|---|---|
| 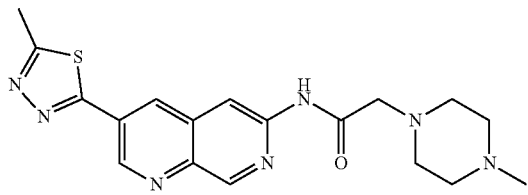 [SMILES: Cc1nnc(-c2cnc3cnc(NC(=O)CN4CCN(C)CC4)cc3c2)s1] | 3443 |
| 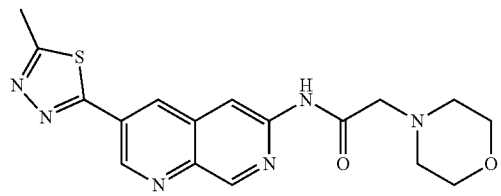 [SMILES: Cc1nnc(-c2cnc3cnc(NC(=O)CN4CCOCC4)cc3c2)s1] | 3444 |
| 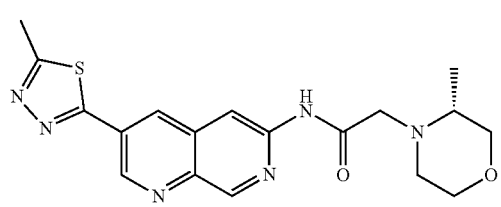 [SMILES: Cc1nnc(-c2cnc3cnc(NC(=O)CN4CCOC[C@H]4C)cc3c2)s1] | 3445 |
| 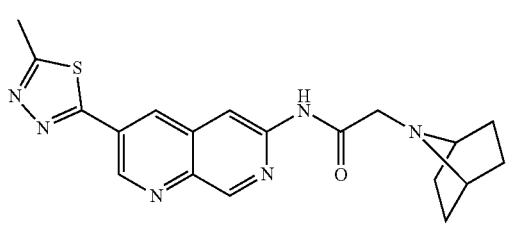 [SMILES: Cc1nnc(-c2cnc3cnc(NC(=O)CN4C5CCC4CC5)cc3c2)s1] | 3446 |
| 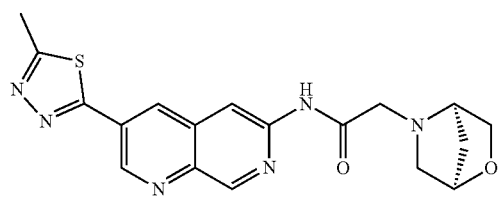 [SMILES: Cc1nnc(-c2cnc3cnc(NC(=O)CN4C[C@H]5C[C@@H]4CO5)cc3c2)s1] | 3447 |
| 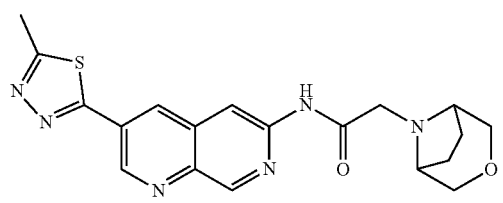 [SMILES: Cc1nnc(-c2cnc3cnc(NC(=O)CN4C5CCC4COC5)cc3c2)s1] | 3448 |
| 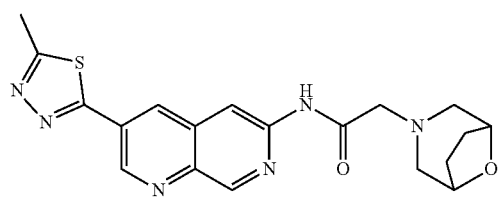 [SMILES: Cc1nnc(-c2cnc3cnc(NC(=O)CN4CC5CCC(C4)O5)cc3c2)s1] | 3449 |
| 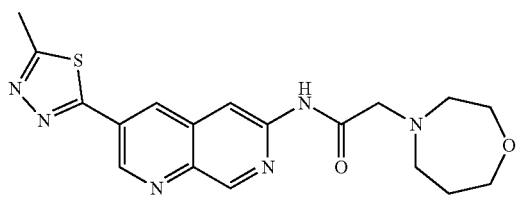 [SMILES: Cc1nnc(-c2cnc3cnc(NC(=O)CN4CCCOCC4)cc3c2)s1] | 3450 |

TABLE 1-continued
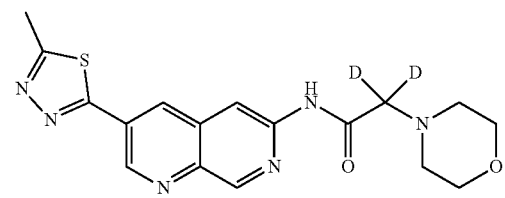 [SMILES: [2H]C([2H])(C(=O)Nc1cc2cc(-c3nnc(C)s3)cnc2cn1)N1CCOCC1] 3451
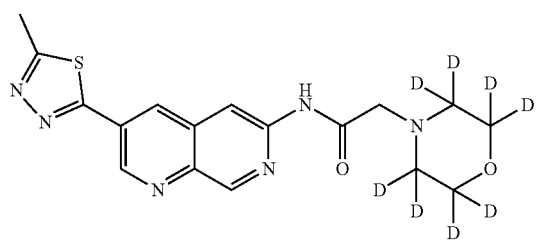 [SMILES: [2H]C1([2H])OC([2H])([2H])C([2H])([2H])N(CC(=O)Nc2cc3cc(-c4nnc(C)s4)cnc3cn2)C1([2H])[2H]] 3452
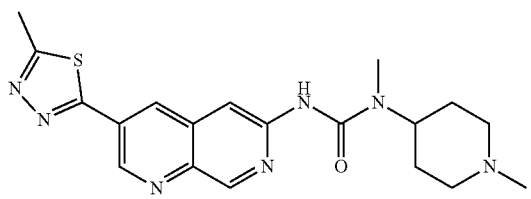 [SMILES: Cc1nnc(-c2cnc3cnc(NC(=O)N(C)C4CCN(C)CC4)cc3c2)s1] 3453
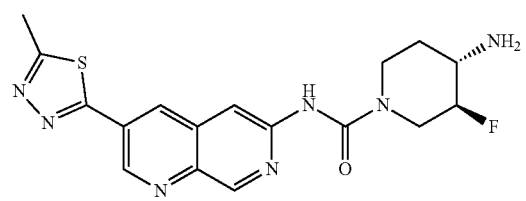 [SMILES: Cc1nnc(-c2cnc3cnc(NC(=O)N4CC[C@H](N)[C@@H](F)C4)cc3c2)s1] 3454
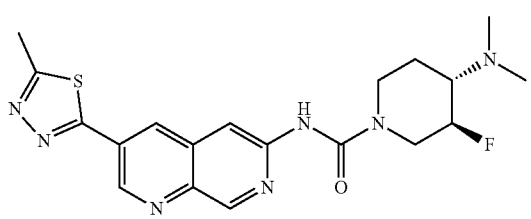 [SMILES: Cc1nnc(-c2cnc3cnc(NC(=O)N4CC[C@H](N(C)C)[C@@H](F)C4)cc3c2)s1] 3455
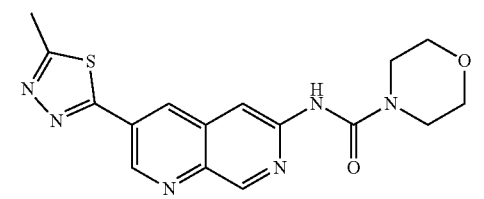 [SMILES: Cc1nnc(-c2cnc3cnc(NC(=O)N4CCOCC4)cc3c2)s1] 3456
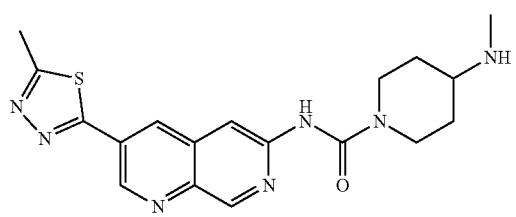 [SMILES: CNC1CCN(C(=O)Nc2cc3cc(-c4nnc(C)s4)cnc3cn2)CC1] 3457

TABLE 1-continued
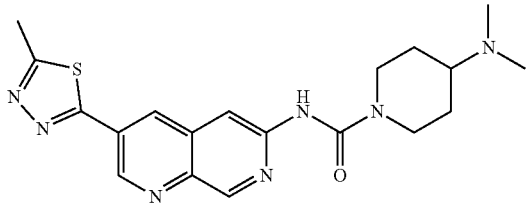 [SMILES: Cc1nnc(-c2cnc3cnc(NC(=O)N4CCC(N(C)C)CC4)cc3c2)s1] 3458
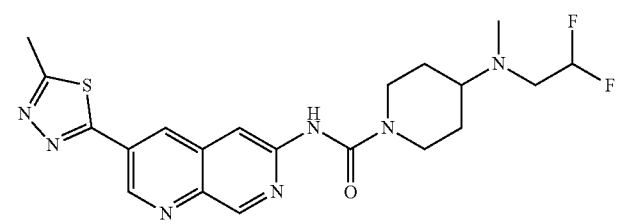 3459
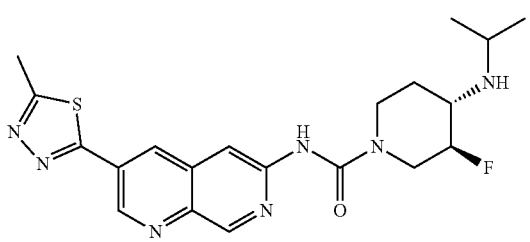 [SMILES: Cc1nnc(-c2cnc3cnc(NC(=O)N4CC[C@H](NC(C)C)[C@@H](F)C4)cc3c2)s1] 3460
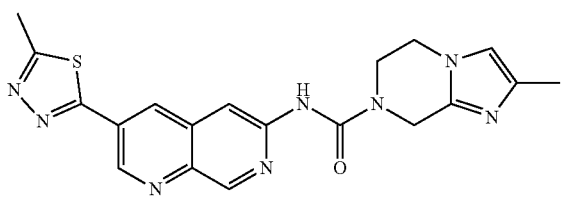 [SMILES: Cc1cn2c(n1)CN(C(=O)Nc1cc3cc(-c4nnc(C)s4)cnc3cn1)CC2] 3461
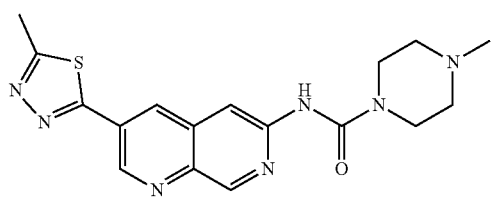 [SMILES: Cc1nnc(-c2cnc3cnc(NC(=O)N4CCN(C)CC4)cc3c2)s1] 3462
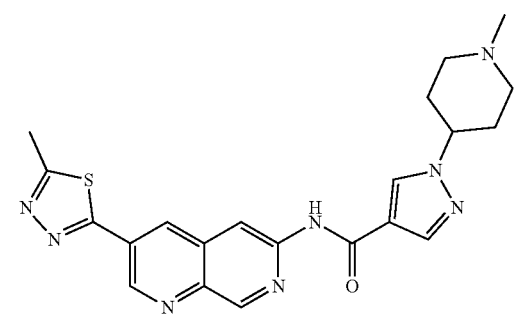 [SMILES: Cc1nnc(-c2cnc3cnc(NC(=O)c4cnn(C5CCN(C)CC5)c4)cc3c2)s1] 3463

TABLE 1-continued
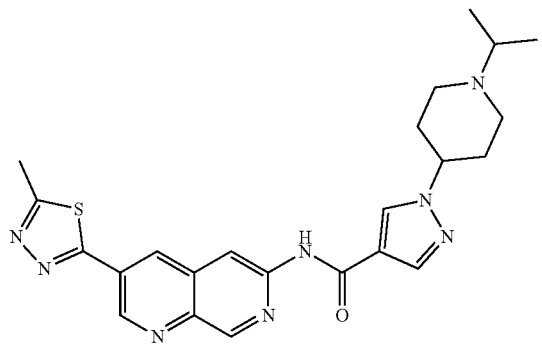 [SMILES: Cc1nnc(-c2cnc3cnc(NC(=O)c4cnn(C5CCN(C(C)C)CC5)c4)cc3c2)s1]
3464
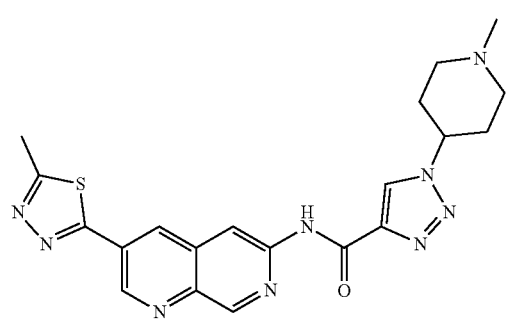 [SMILES: Cc1nnc(-c2cnc3cnc(NC(=O)c4cn(C5CCN(C)CC5)nn4)cc3c2)s1]
3465
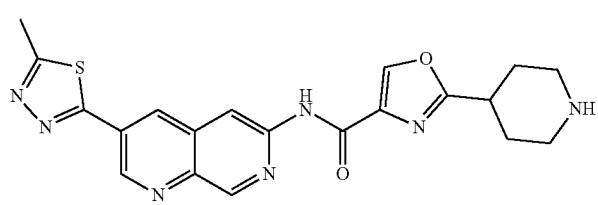 [SMILES: Cc1nnc(-c2cnc3cnc(NC(=O)c4coc(C5CCNCC5)n4)cc3c2)s1]
3466
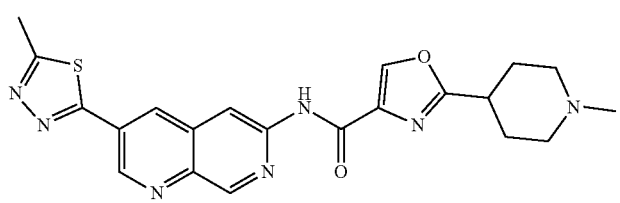 [SMILES: Cc1nnc(-c2cnc3cnc(NC(=O)c4coc(C5CCN(C)CC5)n4)cc3c2)s1]
3467
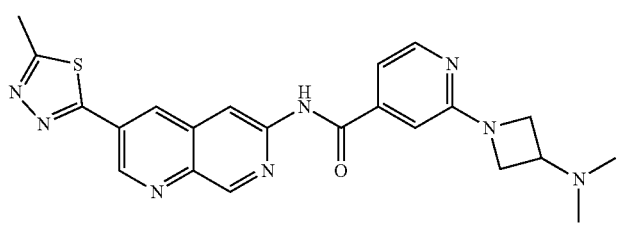 [SMILES: Cc1nnc(-c2cnc3cnc(NC(=O)c4ccnc(N5CC(N(C)C)C5)c4)cc3c2)s1]
3468
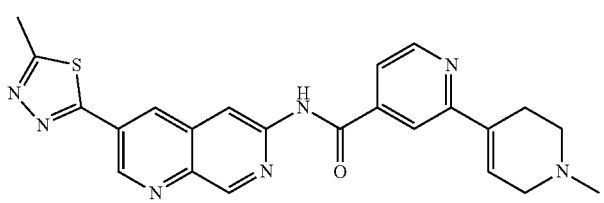 [SMILES: Cc1nnc(-c2cnc3cnc(NC(=O)c4ccnc(C5=CCN(C)CC5)c4)cc3c2)s1]
3469

TABLE 1-continued

| | |
|---|---|
| (structure) | 3470 |
| (structure) | 3471 |
| (structure) | 3472 |
| (structure) | 3473 |
| (structure) | 3474 |
| (structure) | 3475 |
| (structure) | 3476 |

TABLE 1-continued
| | |
|---|---|
| 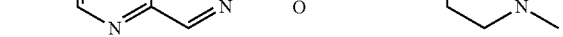 | 3477 |
| 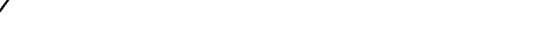 | 3478 |
| 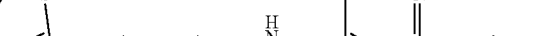 | 3479 |
|  | 3480 |
|  | 3481 |
|  | 3482 |
|  | 3483 |

TABLE 1-continued

| | |
|---|---|
| (structure) | 3484 |
| (structure) | 3485 |
| (structure) | 3486 |
| (structure) | 3487 |
| (structure) | 3488 |
| (structure) | 3489 |
| (structure) | 3490 |
| (structure) | 3491 |
| (structure) | 3492 |

TABLE 1-continued
| | |
|---|---|
| 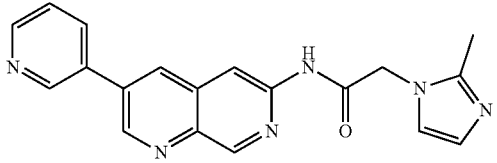 [SMILES: Cc1nccn1CC(=O)Nc1cc2cc(-c3cccnc3)cnc2cn1] | 3493 |
| 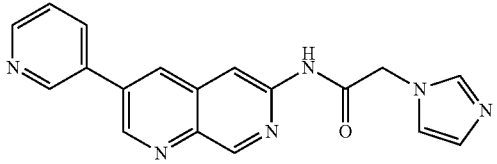 [SMILES: O=C(Cn1ccnc1)Nc1cc2cc(-c3cccnc3)cnc2cn1] | 3494 |
| 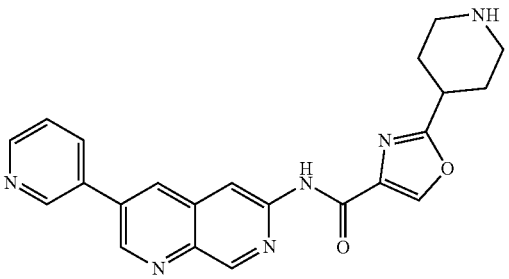 [SMILES: O=C(Nc1cc2cc(-c3cccnc3)cnc2cn1)c1coc(C2CCNCC2)n1] | 3495 |
| 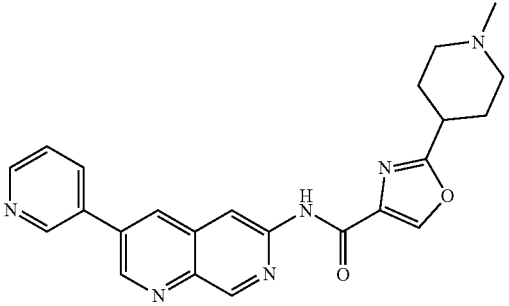 [SMILES: CN1CCC(c2nc(C(=O)Nc3cc4cc(-c5cccnc5)cnc4cn3)co2)CC1] | 3496 |
| 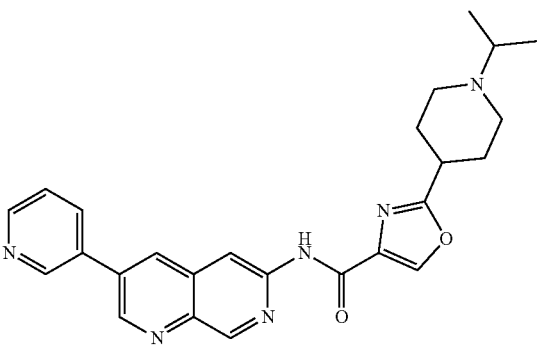 [SMILES: CC(C)N1CCC(c2nc(C(=O)Nc3cc4cc(-c5cccnc5)cnc4cn3)co2)CC1] | 3497 |
| 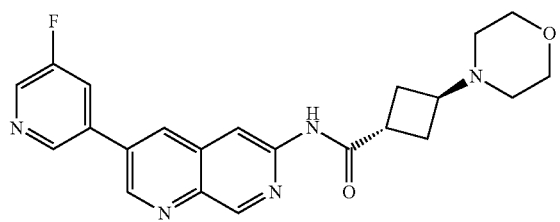 [SMILES: O=C(Nc1cc2cc(-c3cncc(F)c3)cnc2cn1)[C@H]1C[C@H](N2CCOCC2)C1] | 3498 |

TABLE 1-continued
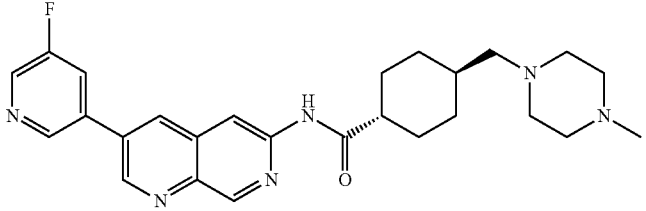 [SMILES: CN1CCN(C[C@H]2CC[C@H](C(=O)Nc3cc4cc(-c5cncc(F)c5)cnc4cn3)CC2)CC1]
3499
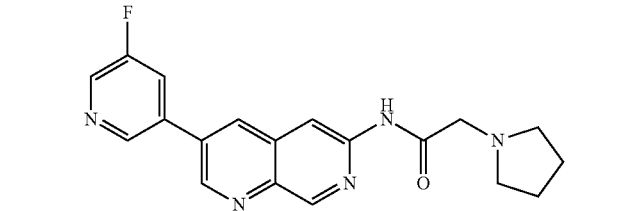 [SMILES: O=C(CN1CCCC1)Nc1cc2cc(-c3cncc(F)c3)cnc2cn1]
3500
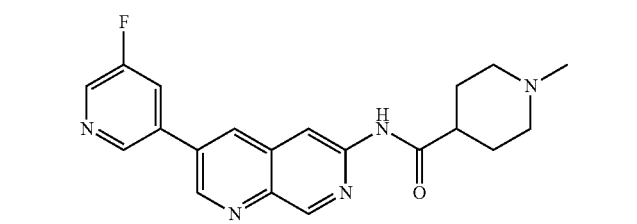 [SMILES: CN1CCC(C(=O)Nc2cc3cc(-c4cncc(F)c4)cnc3cn2)CC1]
3501
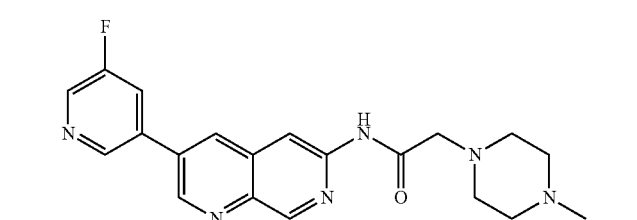
3502
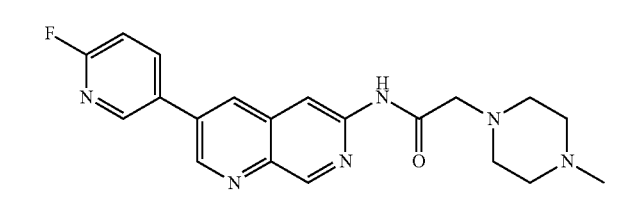
3503
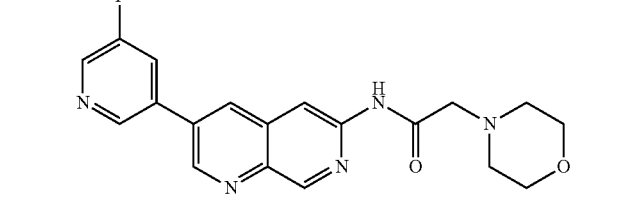
3504
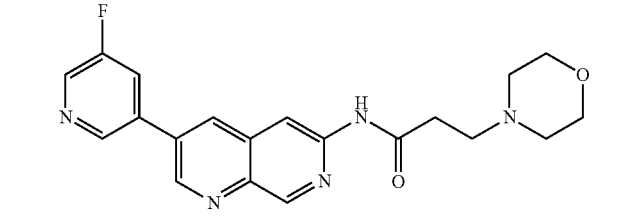 [SMILES: O=C(CCN1CCOCC1)Nc1cc2cc(-c3cncc(F)c3)cnc2cn1]
3505

TABLE 1-continued
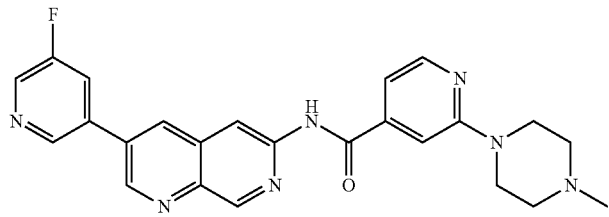
3506
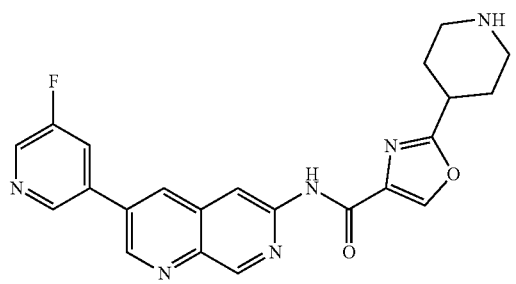 [SMILES: O=C(Nc1cc2cc(-c3cncc(F)c3)cnc2cn1)c1coc(C2CCNCC2)n1]
3507
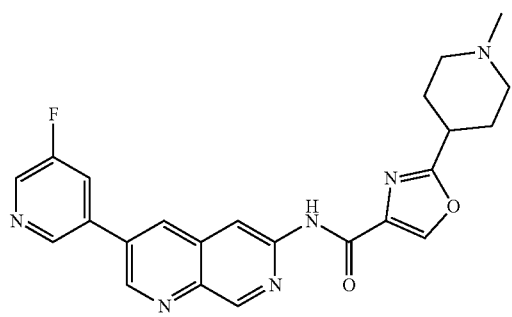 [SMILES: CN1CCC(c2nc(C(=O)Nc3cc4cc(-c5cncc(F)c5)cnc4cn3)co2)CC1]
3508
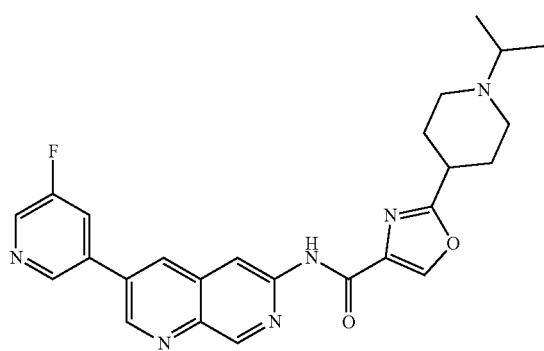 [SMILES: CC(C)N1CCC(c2nc(C(=O)Nc3cc4cc(-c5cncc(F)c5)cnc4cn3)co2)CC1]
3509
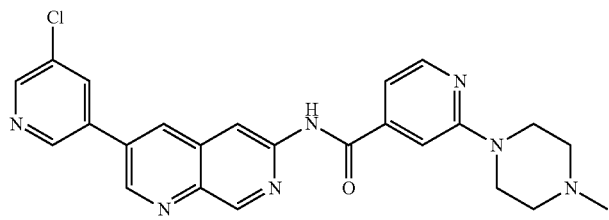 [SMILES: CN1CCN(c2cc(C(=O)Nc3cc4cc(-c5cncc(Cl)c5)cnc4cn3)ccn2)CC1]
3510
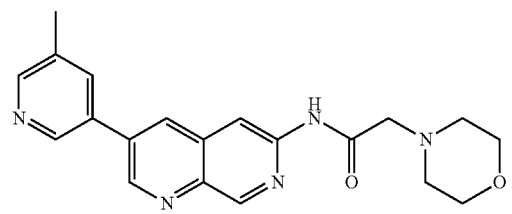 [SMILES: Cc1cncc(-c2cnc3cnc(NC(=O)CN4CCOCC4)cc3c2)c1]
3511

TABLE 1-continued
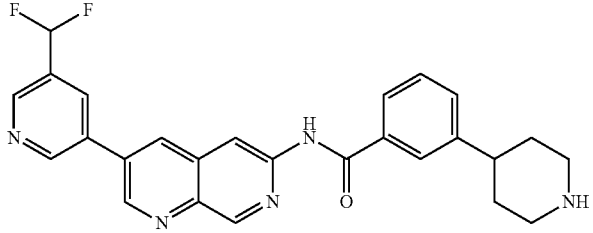 [SMILES: O=C(Nc1cc2cc(-c3cncc(C(F)F)c3)cnc2cn1)c1cccc(C2CCNCC2)c1] 3512
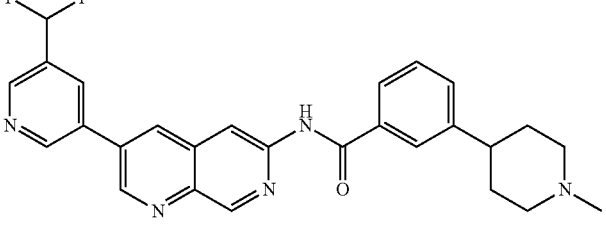 3513
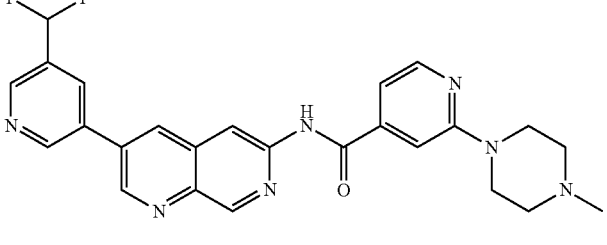 3514
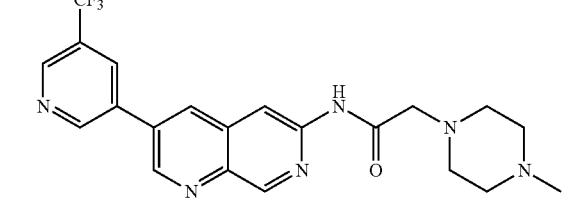 3515
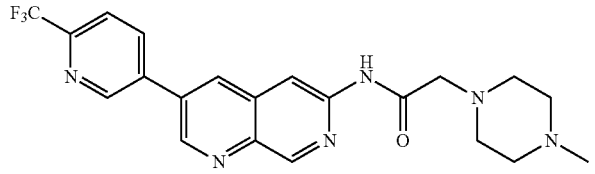 [SMILES: CN1CCN(CC(=O)Nc2cc3cc(-c4ccc(C(F)(F)F)nc4)cnc3cn2)CC1] 3516
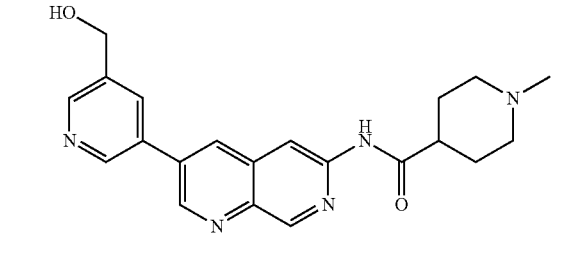 [SMILES: CN1CCC(C(=O)Nc2cc3cc(-c4cncc(CO)c4)cnc3cn2)CC1] 3517
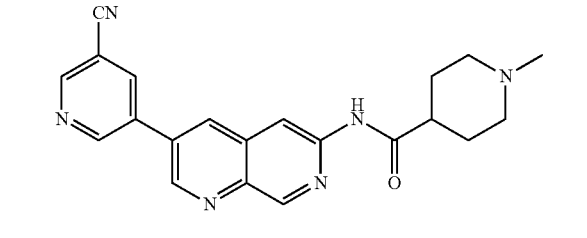 [SMILES: CN1CCC(C(=O)Nc2cc3cc(-c4cncc(C#N)c4)cnc3cn2)CC1] 3518

TABLE 1-continued
| | |
|---|---|
| 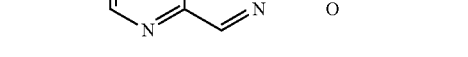 | 3519 |
|  | 3520 |
| 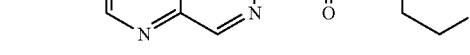 | 3521 |
|  | 3522 |
|  | 3523 |
| 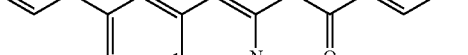 | 3524 |
|  | 3525 |

TABLE 1-continued
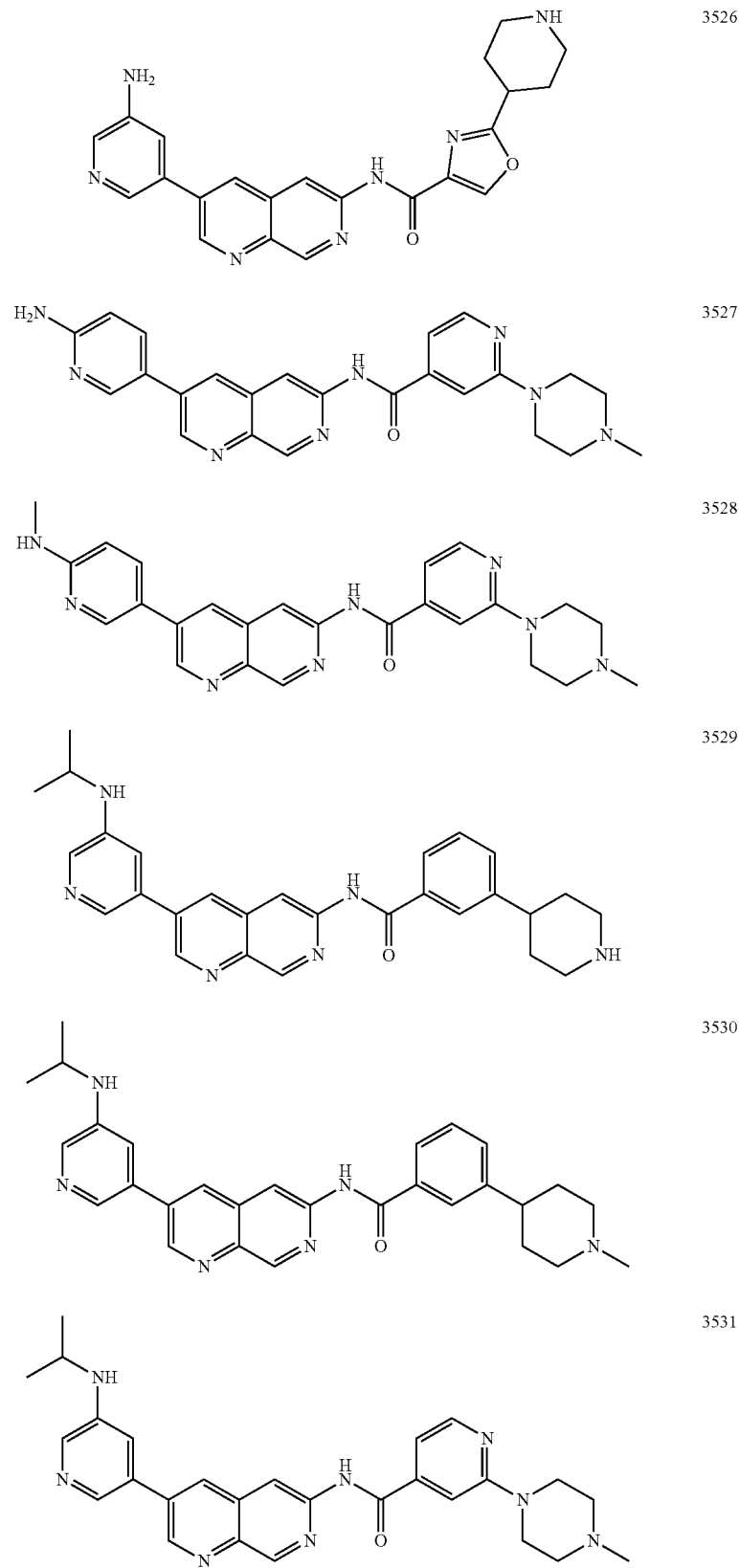

TABLE 1-continued
| | |
|---|---|
| 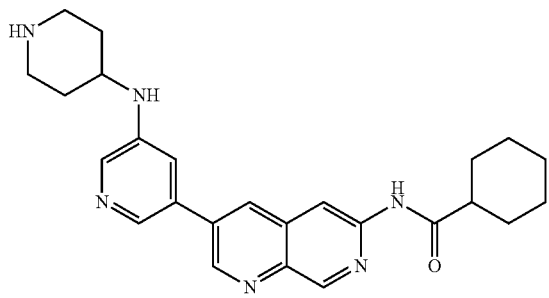 [SMILES: O=C(Nc1cc2cc(-c3cncc(NC4CCNCC4)c3)cnc2cn1)C1CCCCC1] | 3532 |
| 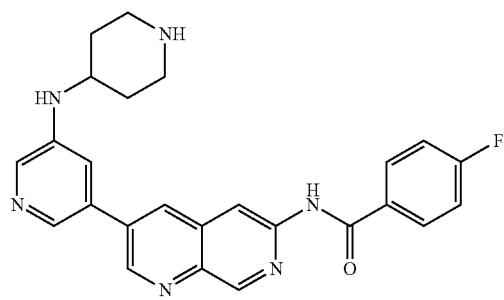 [SMILES: O=C(Nc1cc2cc(-c3cncc(NC4CCNCC4)c3)cnc2cn1)c1ccc(F)cc1] | 3533 |
| 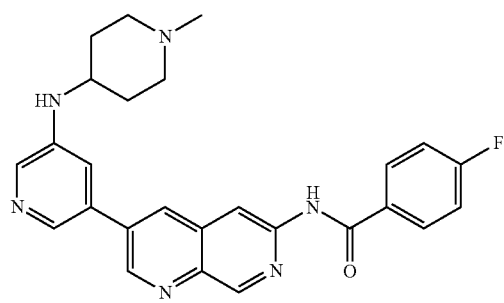 [SMILES: CN1CCC(Nc2cncc(-c3cnc4cnc(NC(=O)c5ccc(F)cc5)cc4c3)c2)CC1] | 3534 |
| 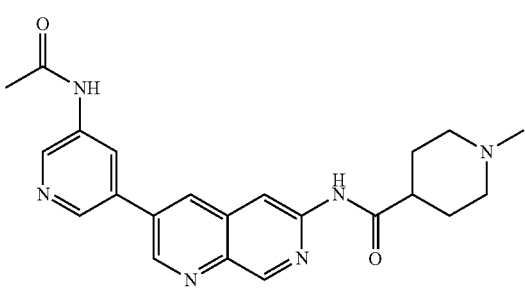 [SMILES: CC(=O)Nc1cncc(-c2cnc3cnc(NC(=O)C4CCN(C)CC4)cc3c2)c1] | 3535 |
| 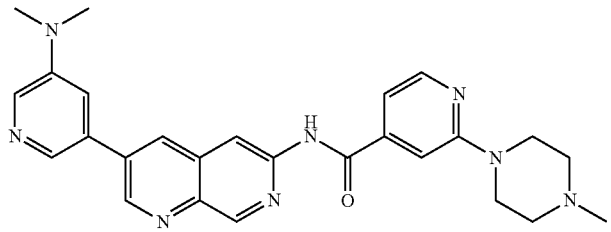 [SMILES: CN1CCN(c2cc(C(=O)Nc3cc4cc(-c5cncc(N(C)C)c5)cnc4cn3)ccn2)CC1] | 3536 |
| 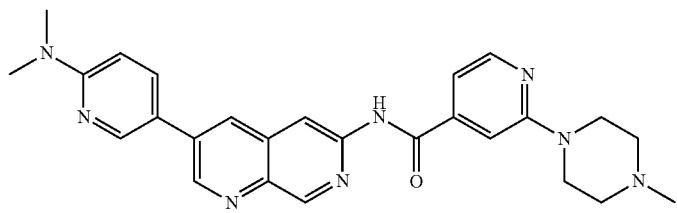 | 3537 |

TABLE 1-continued
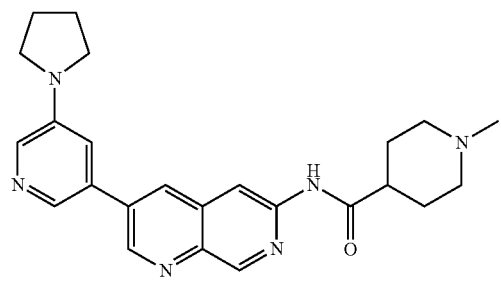 [SMILES: CN1CCC(C(=O)Nc2cc3cc(-c4cncc(N5CCCC5)c4)cnc3cn2)CC1] 3538
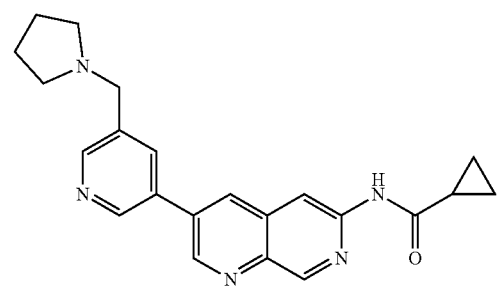 [SMILES: O=C(Nc1cc2cc(-c3cncc(CN4CCCC4)c3)cnc2cn1)C1CC1] 3539
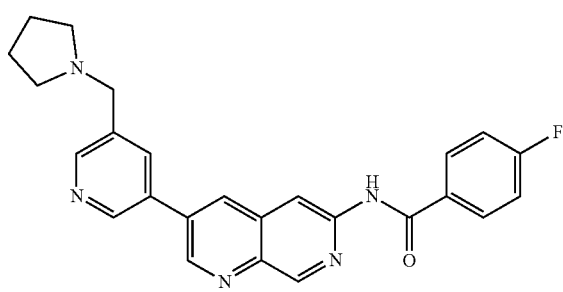 [SMILES: O=C(Nc1cc2cc(-c3cncc(CN4CCCC4)c3)cnc2cn1)c1ccc(F)cc1] 3540
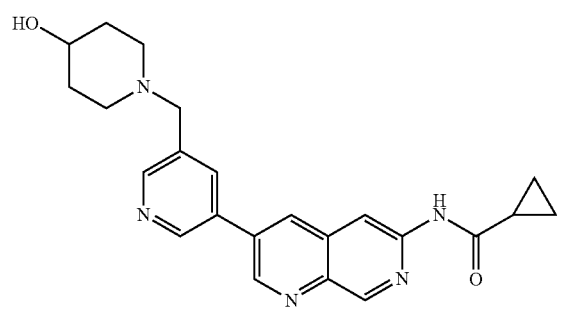 [SMILES: O=C(Nc1cc2cc(-c3cncc(CN4CCC(O)CC4)c3)cnc2cn1)C1CC1] 3541
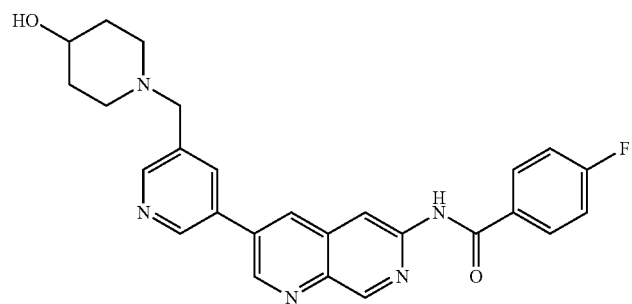 [SMILES: O=C(Nc1cc2cc(-c3cncc(CN4CCC(O)CC4)c3)cnc2cn1)c1ccc(F)cc1] 3542

TABLE 1-continued
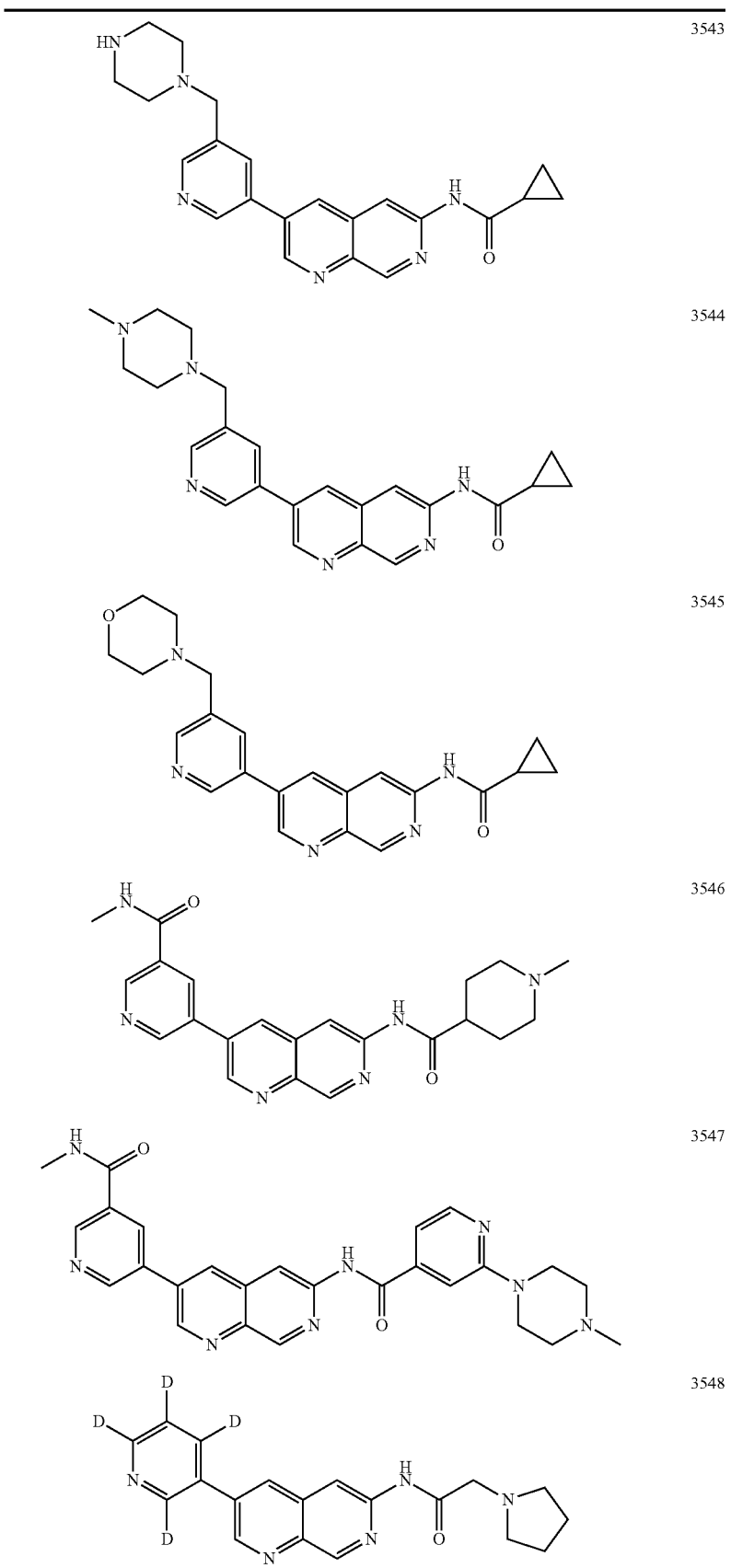
3543
3544
3545
3546
3547
3548

TABLE 1-continued
| | |
|---|---|
| 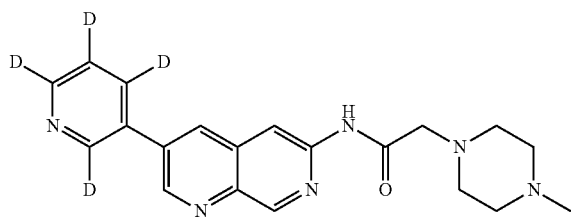 [SMILES: [2H]c1nc([2H])c(-c2cnc3cnc(NC(=O)CN4CCN(C)CC4)cc3c2)c([2H])c1[2H]] | 3549 |
| 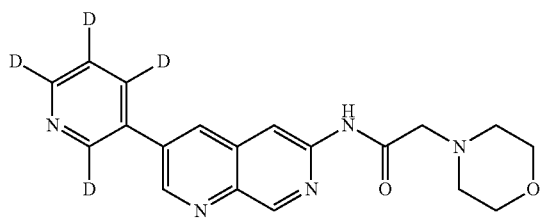 [SMILES: [2H]c1nc([2H])c(-c2cnc3cnc(NC(=O)CN4CCOCC4)cc3c2)c([2H])c1[2H]] | 3550 |
| 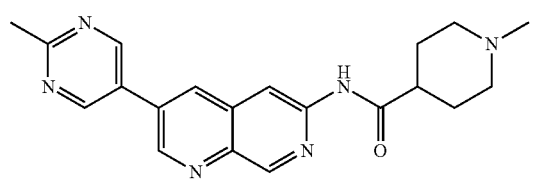 | 3551 |
| 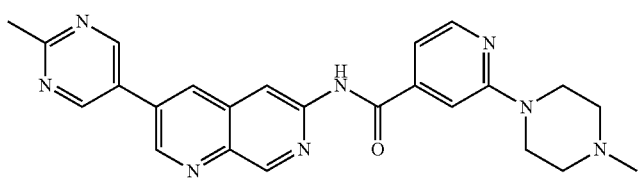 | 3552 |
| 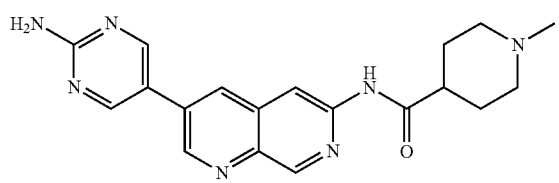 [SMILES: CN1CCC(C(=O)Nc2cc3cc(-c4cnc(N)nc4)cnc3cn2)CC1] | 3553 |
| 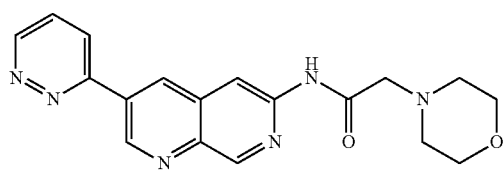 [SMILES: O=C(CN1CCOCC1)Nc1cc2cc(-c3cccnn3)cnc2cn1] | 3554 |
| 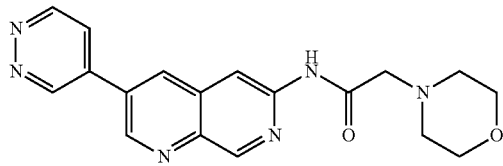 [SMILES: O=C(CN1CCOCC1)Nc1cc2cc(-c3ccnnc3)cnc2cn1] | 3555 |
| 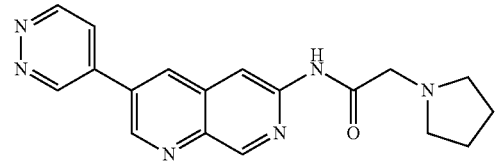 [SMILES: O=C(CN1CCCC1)Nc1cc2cc(-c3ccnnc3)cnc2cn1] | 3556 |

TABLE 1-continued
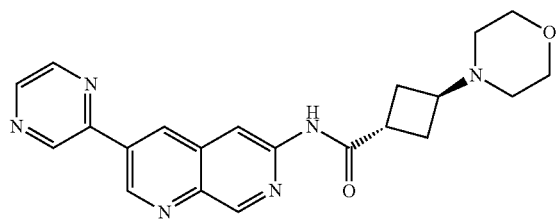 [SMILES: O=C(Nc1cc2cc(-c3cnccn3)cnc2cn1)[C@H]1C[C@H](N2CCOCC2)C1]
3557
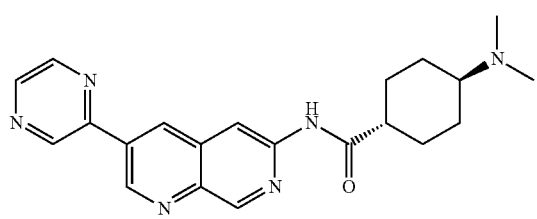 [SMILES: CN(C)[C@H]1CC[C@H](C(=O)Nc2cc3cc(-c4cnccn4)cnc3cn2)CC1]
3558
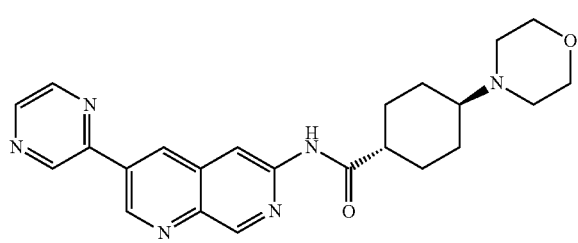 [SMILES: O=C(Nc1cc2cc(-c3cnccn3)cnc2cn1)[C@H]1CC[C@H](N2CCOCC2)CC1]
3559
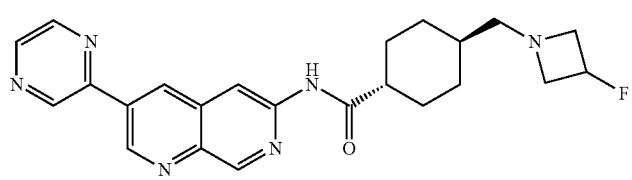 [SMILES: O=C(Nc1cc2cc(-c3cnccn3)cnc2cn1)[C@H]1CC[C@H](CN2CC(F)C2)CC1]
3560
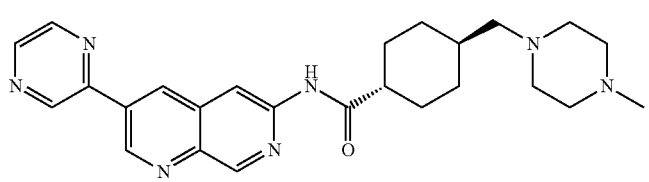 [SMILES: CN1CCN(C[C@H]2CC[C@H](C(=O)Nc3cc4cc(-c5cnccn5)cnc4cn3)CC2)CC1]
3561
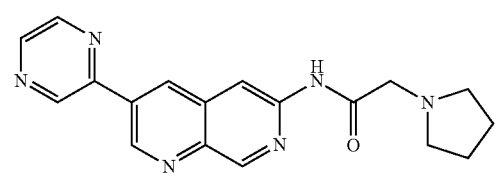
3562
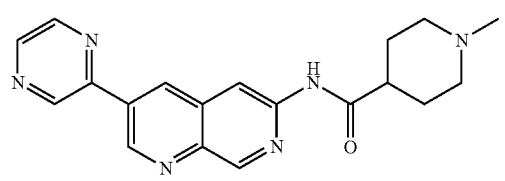 [SMILES: CN1CCC(C(=O)Nc2cc3cc(-c4cnccn4)cnc3cn2)CC1]
3563
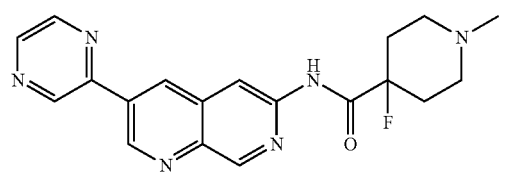 [SMILES: CN1CCC(F)(C(=O)Nc2cc3cc(-c4cnccn4)cnc3cn2)CC1]
3564

TABLE 1-continued
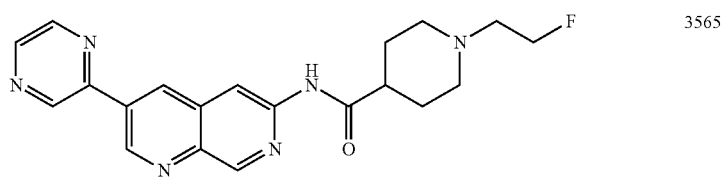 3565
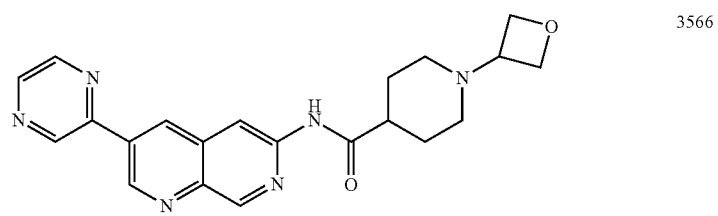 3566
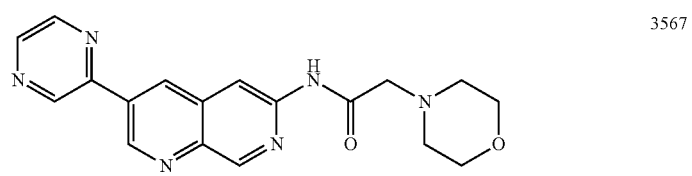 3567
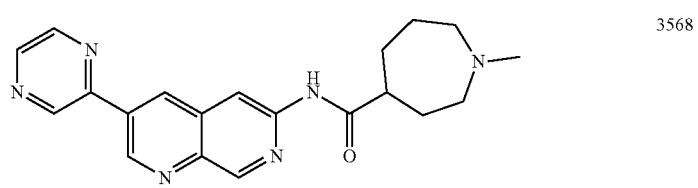 3568
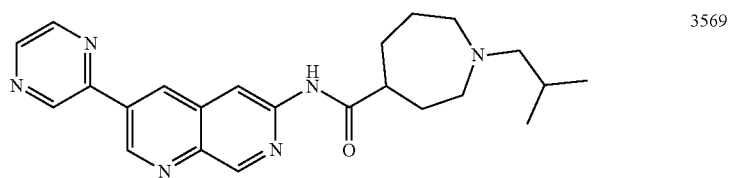 3569
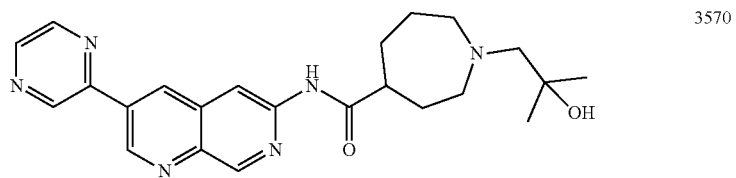 3570
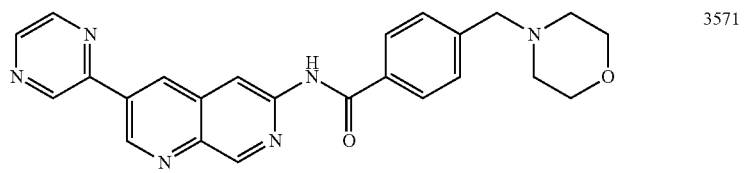 3571
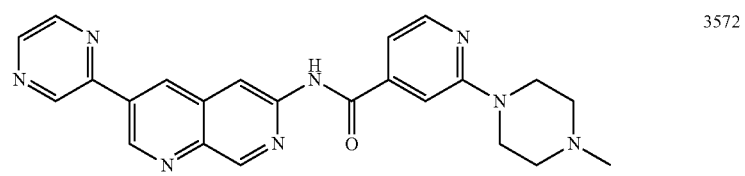 3572

TABLE 1-continued
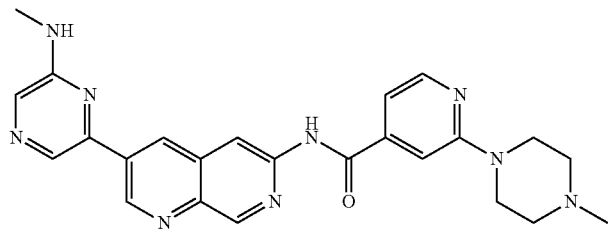 [SMILES: CNc1cncc(-c2cnc3cnc(NC(=O)c4ccnc(N5CCN(C)CC5)c4)cc3c2)n1]
3573
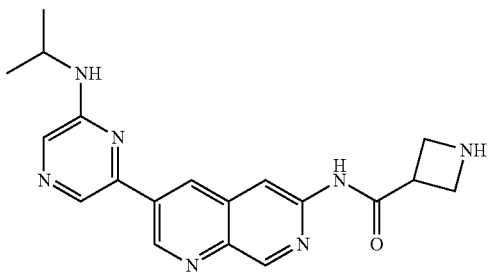
3574
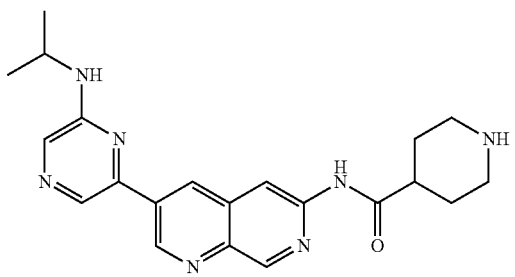 [SMILES: CC(C)Nc1cncc(-c2cnc3cnc(NC(=O)C4CCNCC4)cc3c2)n1]
3575
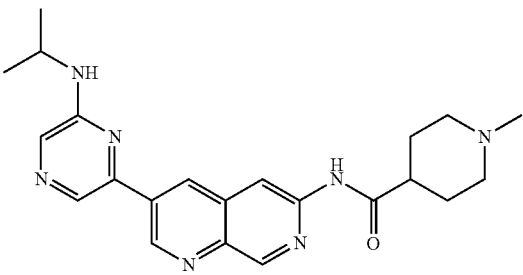 [SMILES: CC(C)Nc1cncc(-c2cnc3cnc(NC(=O)C4CCN(C)CC4)cc3c2)n1]
3576
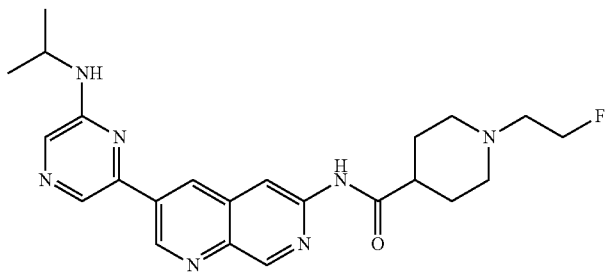 [SMILES: CC(C)Nc1cncc(-c2cnc3cnc(NC(=O)C4CCN(CCF)CC4)cc3c2)n1]
3577
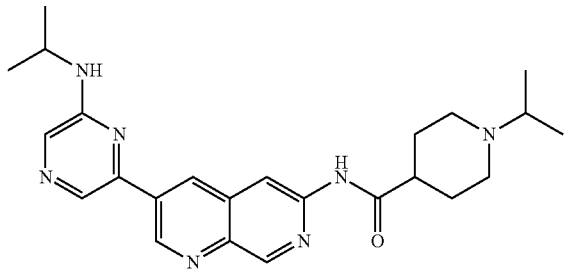 [SMILES: CC(C)Nc1cncc(-c2cnc3cnc(NC(=O)C4CCN(C(C)C)CC4)cc3c2)n1]
3578

TABLE 1-continued
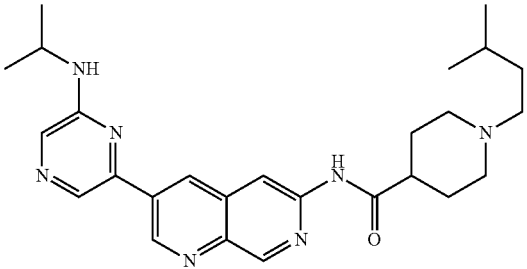 [SMILES: CC(C)CCN1CCC(C(=O)Nc2cc3cc(-c4cncc(NC(C)C)n4)cnc3cn2)CC1]
3579
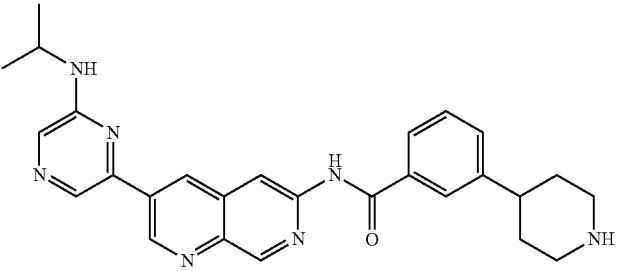 [SMILES: CC(C)Nc1cncc(-c2cnc3cnc(NC(=O)c4cccc(C5CCNCC5)c4)cc3c2)n1]
3580
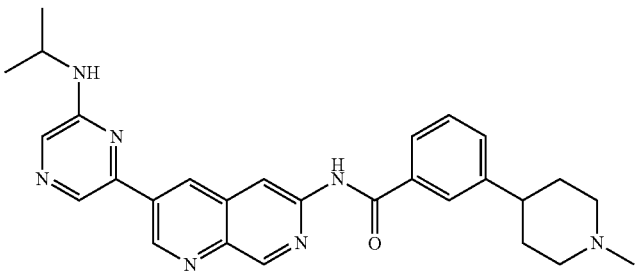 [SMILES: CC(C)Nc1cncc(-c2cnc3cnc(NC(=O)c4cccc(C5CCN(C)CC5)c4)cc3c2)n1]
3581
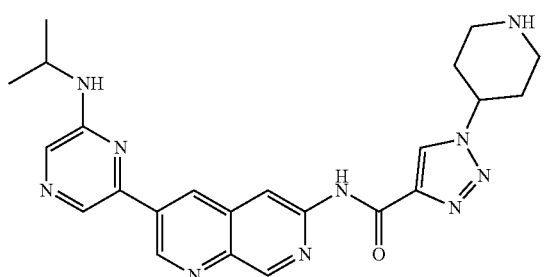
3582
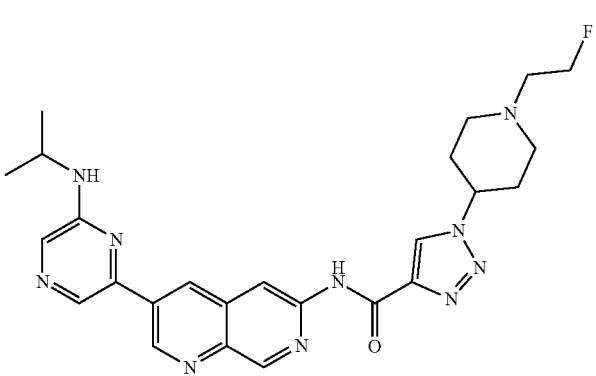 [SMILES: CC(C)Nc1cncc(-c2cnc3cnc(NC(=O)c4cn(C5CCN(CCF)CC5)nn4)cc3c2)n1]
3583

TABLE 1-continued
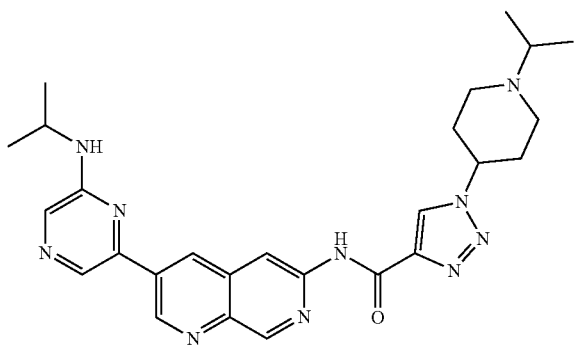 [SMILES: CC(C)Nc1cncc(-c2cnc3cnc(NC(=O)c4cn(C5CCN(C(C)C)CC5)nn4)cc3c2)n1]
3584
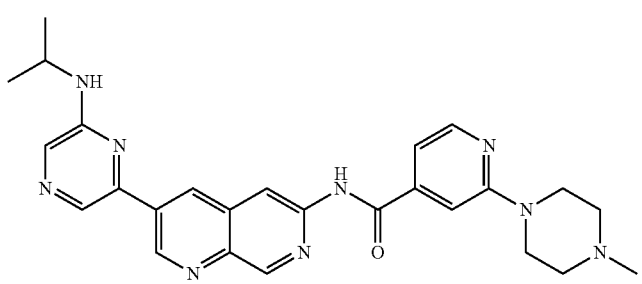 [SMILES: CC(C)Nc1cncc(-c2cnc3cnc(NC(=O)c4ccnc(N5CCN(C)CC5)c4)cc3c2)n1]
3585
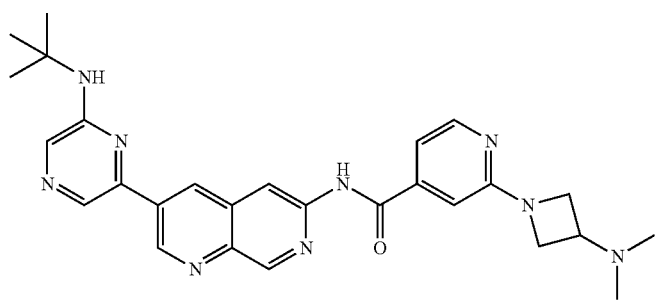 [SMILES: CN(C)C1CN(c2cc(C(=O)Nc3cc4cc(-c5cncc(NC(C)(C)C)n5)cnc4cn3)ccn2)C1]
3586
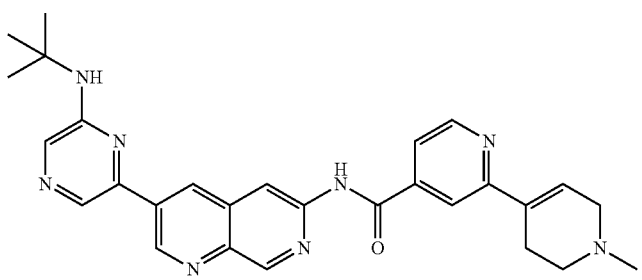 [SMILES: CN1CC=C(c2cc(C(=O)Nc3cc4cc(-c5cncc(NC(C)(C)C)n5)cnc4cn3)ccn2)CC1]
3587
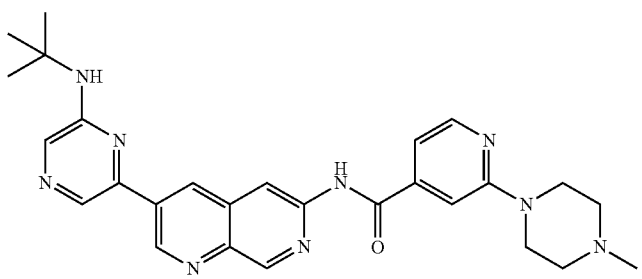 [SMILES: CN1CCN(c2cc(C(=O)Nc3cc4cc(-c5cncc(NC(C)(C)C)n5)cnc4cn3)ccn2)CC1]
3588

TABLE 1-continued
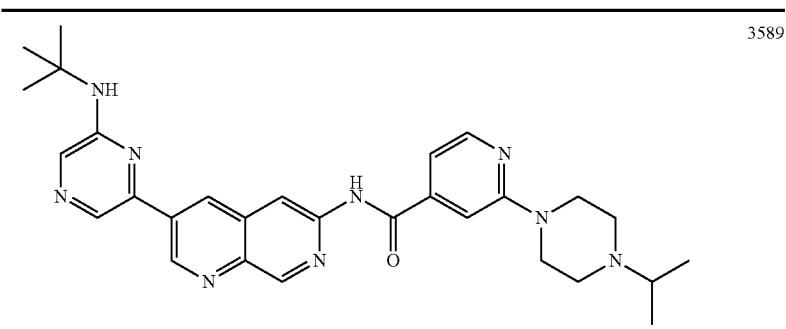
3589
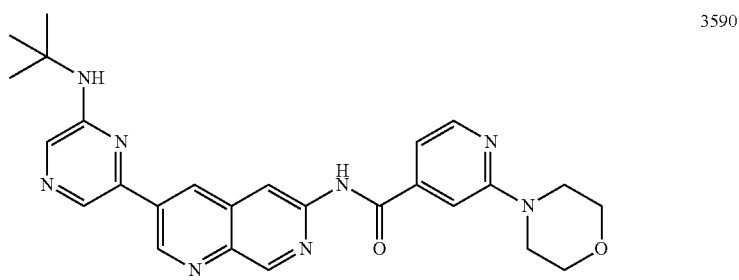
3590
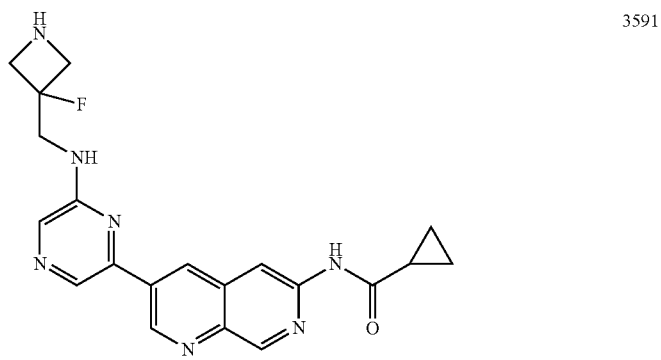
3591
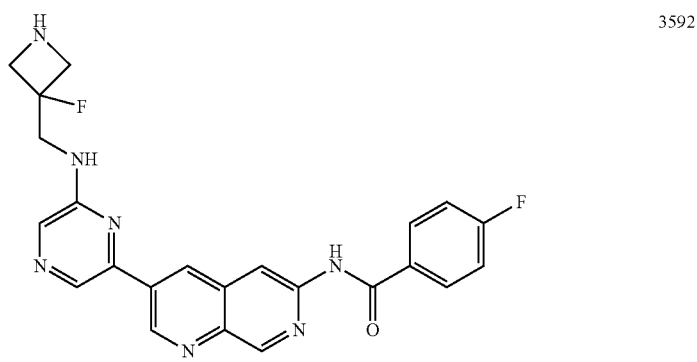
3592
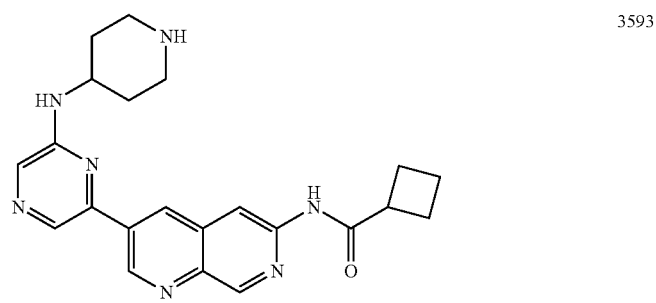
3593

TABLE 1-continued
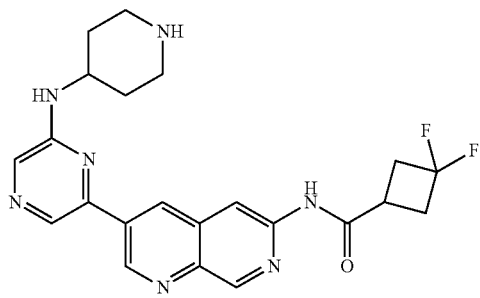 [SMILES: O=C(Nc1cc2cc(-c3cncc(NC4CCNCC4)n3)cnc2cn1)C1CC(F)(F)C1] 3594
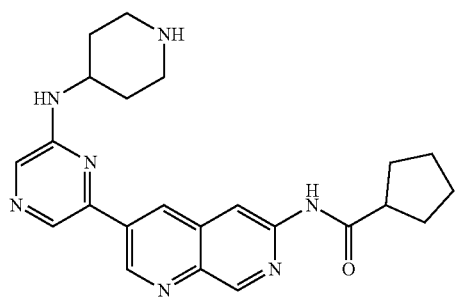 [SMILES: O=C(Nc1cc2cc(-c3cncc(NC4CCNCC4)n3)cnc2cn1)C1CCCC1] 3595
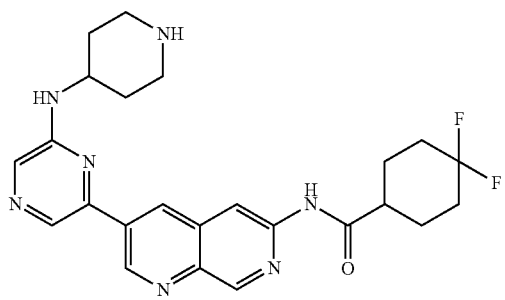 [SMILES: O=C(Nc1cc2cc(-c3cncc(NC4CCNCC4)n3)cnc2cn1)C1CCC(F)(F)CC1] 3596
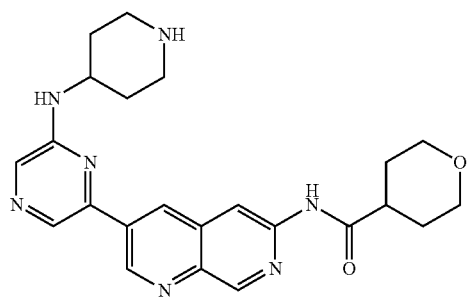 [SMILES: O=C(Nc1cc2cc(-c3cncc(NC4CCNCC4)n3)cnc2cn1)C1CCOCC1] 3597
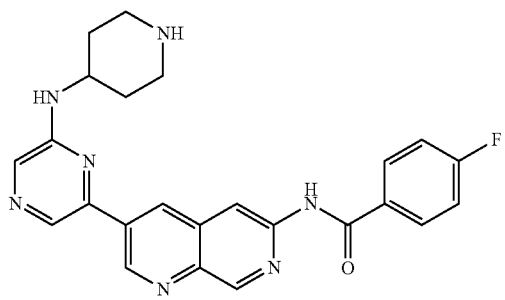 [SMILES: O=C(Nc1cc2cc(-c3cncc(NC4CCNCC4)n3)cnc2cn1)c1ccc(F)cc1] 3598

TABLE 1-continued
| | |
|---|---|
| 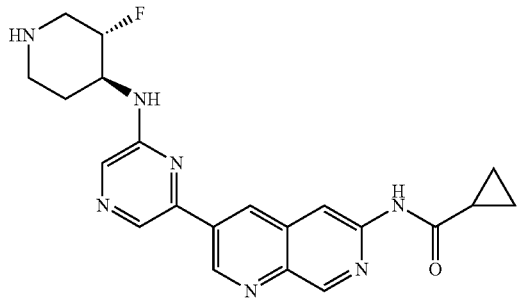 [SMILES: O=C(Nc1cc2cc(-c3cncc(N[C@H]4CCNC[C@@H]4F)n3)cnc2cn1)C1CC1] | 3599 |
| 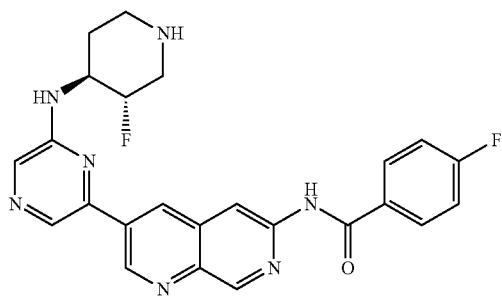 [SMILES: O=C(Nc1cc2cc(-c3cncc(N[C@H]4CCNC[C@@H]4F)n3)cnc2cn1)c1ccc(F)cc1] | 3600 |
| 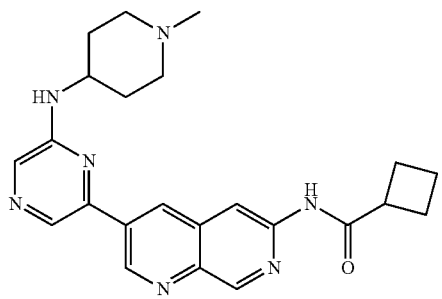 [SMILES: CN1CCC(Nc2cncc(-c3cnc4cnc(NC(=O)C5CCC5)cc4c3)n2)CC1] | 3601 |
| 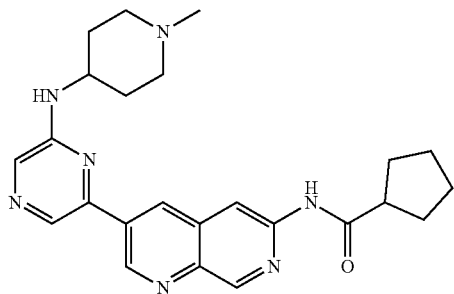 [SMILES: CN1CCC(Nc2cncc(-c3cnc4cnc(NC(=O)C5CCCC5)cc4c3)n2)CC1] | 3602 |
| 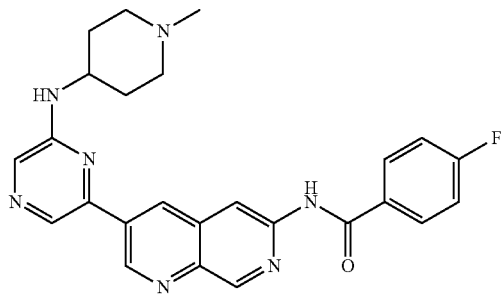 [SMILES: CN1CCC(Nc2cncc(-c3cnc4cnc(NC(=O)c5ccc(F)cc5)cc4c3)n2)CC1] | 3603 |

TABLE 1-continued
| | |
|---|---|
| 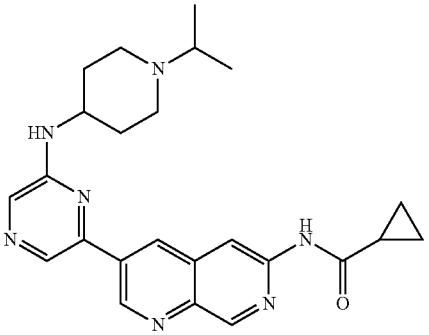 [SMILES: CC(C)N1CCC(Nc2cncc(-c3cnc4cnc(NC(=O)C5CC5)cc4c3)n2)CC1] | 3604 |
| | 3605 |
| | 3606 |
| | 3607 |
| | 3608 |

TABLE 1-continued
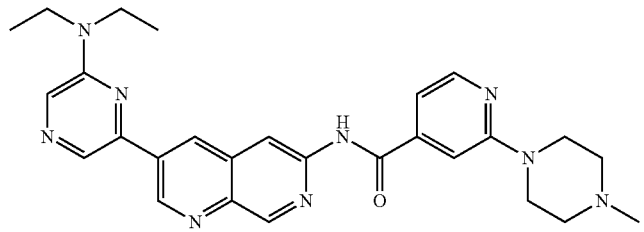 [SMILES: CCN(CC)c1cncc(-c2cnc3cnc(NC(=O)c4ccnc(N5CCN(C)CC5)c4)cc3c2)n1]
3609
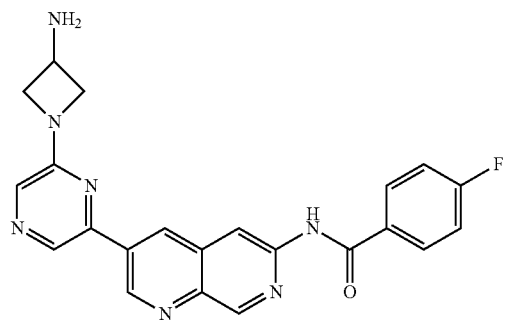 [SMILES: NC1CN(c2cncc(-c3cnc4cnc(NC(=O)c5ccc(F)cc5)cc4c3)n2)C1]
3610
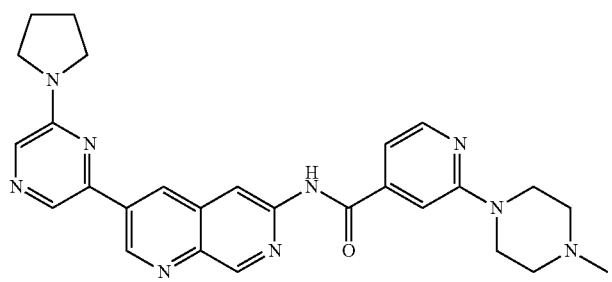 [SMILES: CN1CCN(c2cc(C(=O)Nc3cc4cc(-c5cncc(N6CCCC6)n5)cnc4cn3)ccn2)CC1]
3611
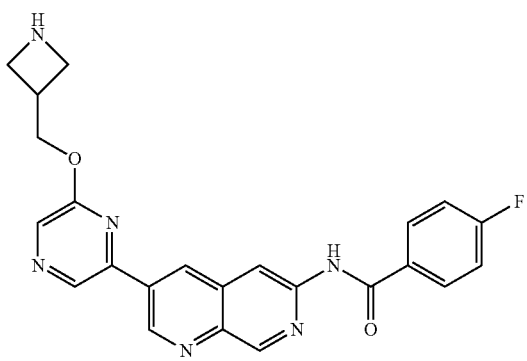 [SMILES: O=C(Nc1cc2cc(-c3cncc(OCC4CNC4)n3)cnc2cn1)c1ccc(F)cc1]
3612
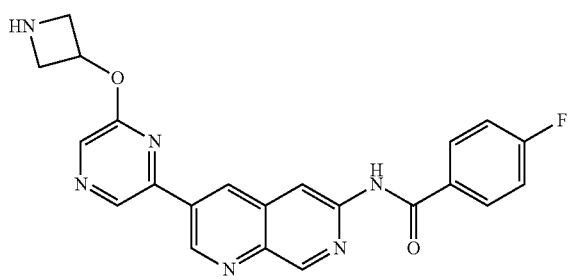 [SMILES: O=C(Nc1cc2cc(-c3cncc(OC4CNC4)n3)cnc2cn1)c1ccc(F)cc1]
3613

TABLE 1-continued
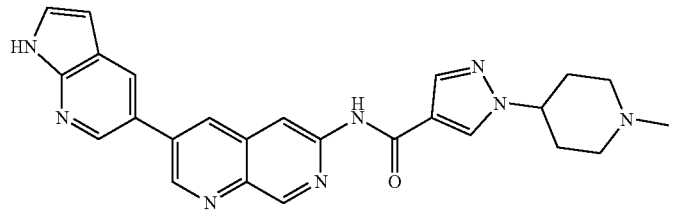 [SMILES: CN1CCC(n2cc(C(=O)Nc3cc4cc(-c5cnc6[nH]ccc6c5)cnc4cn3)cn2)CC1]
3614
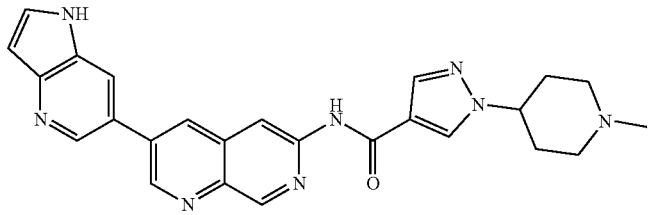 [SMILES: CN1CCC(n2cc(C(=O)Nc3cc4cc(-c5cnc6cc[nH]c6c5)cnc4cn3)cn2)CC1]
3615
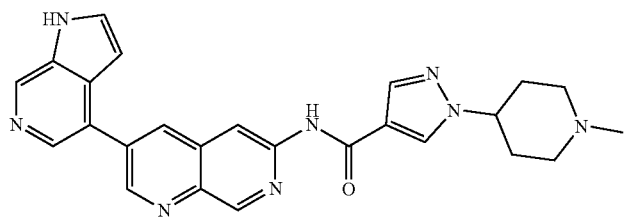 [SMILES: CN1CCC(n2cc(C(=O)Nc3cc4cc(-c5cncc6[nH]ccc56)cnc4cn3)cn2)CC1]
3616
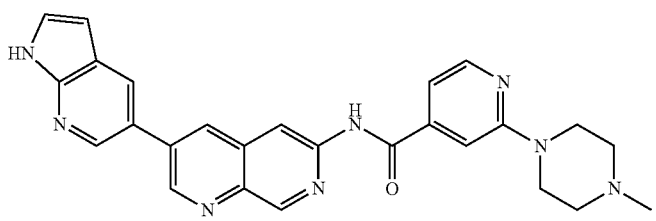 [SMILES: CN1CCN(c2cc(C(=O)Nc3cc4cc(-c5cnc6[nH]ccc6c5)cnc4cn3)ccn2)CC1]
3617
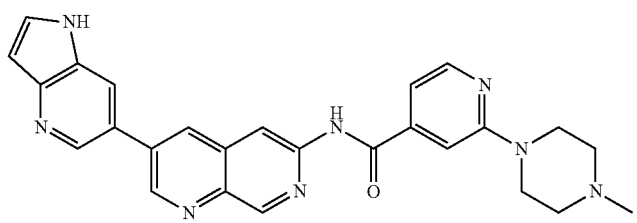
3618
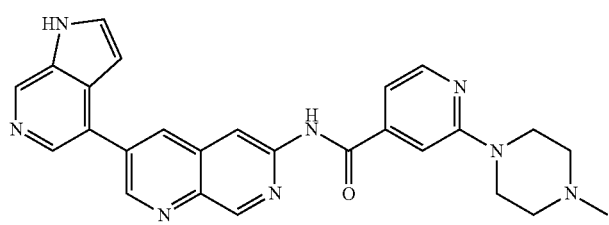 [SMILES: CN1CCN(c2cc(C(=O)Nc3cc4cc(-c5cncc6[nH]ccc56)cnc4cn3)ccn2)CC1]
3619
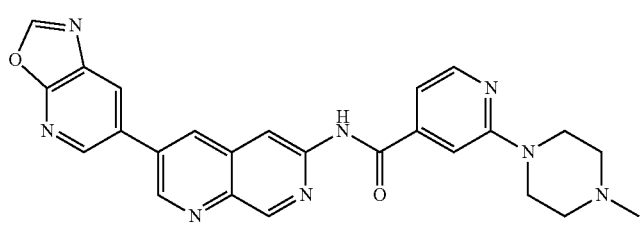 [SMILES: CN1CCN(c2cc(C(=O)Nc3cc4cc(-c5cnc6ocnc6c5)cnc4cn3)ccn2)CC1]
3620

TABLE 1-continued
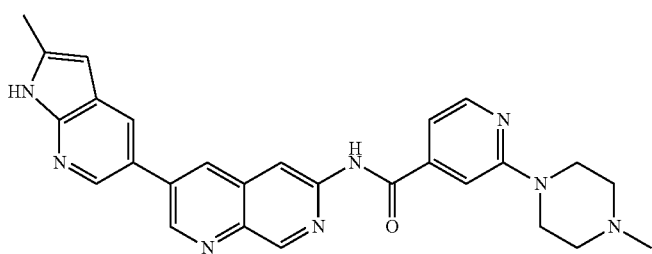
3621
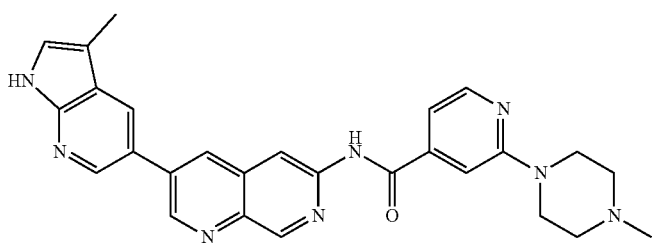 [SMILES: Cc1c[nH]c2ncc(-c3cnc4cnc(NC(=O)c5ccnc(N6CCN(C)CC6)c5)cc4c3)cc12]
3622
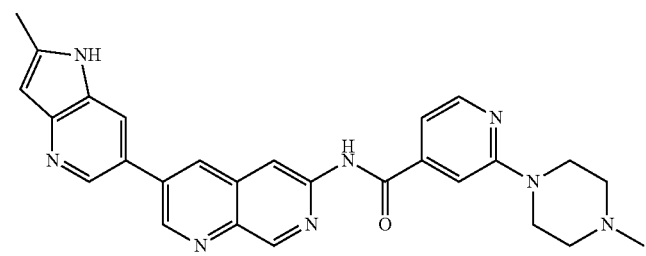
3623
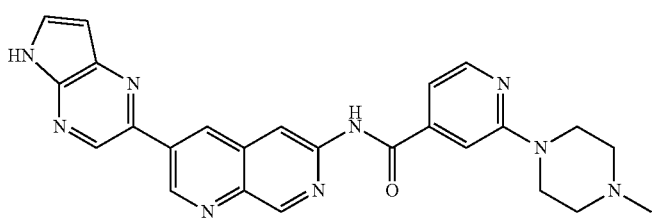 [SMILES: CN1CCN(c2cc(C(=O)Nc3cc4cc(-c5cnc6[nH]ccc6n5)cnc4cn3)ccn2)CC1]
3624
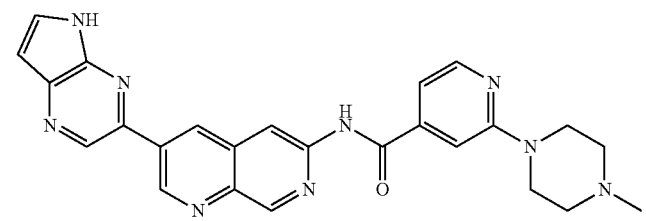 [SMILES: CN1CCN(c2cc(C(=O)Nc3cc4cc(-c5cnc6cc[nH]c6n5)cnc4cn3)ccn2)CC1]
3625
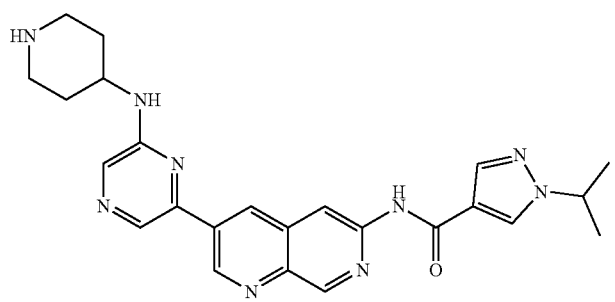
3626

TABLE 1-continued
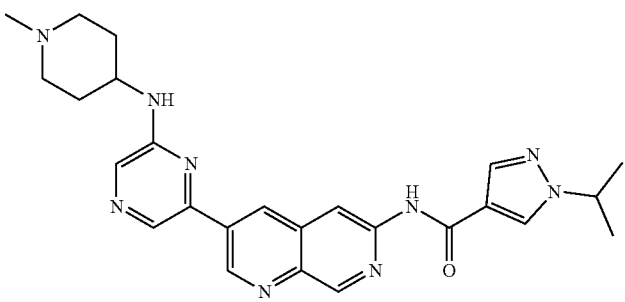 [SMILES: CC(C)n1cc(C(=O)Nc2cc3cc(-c4cncc(NC5CCN(C)CC5)n4)cnc3cn2)cn1] 3627
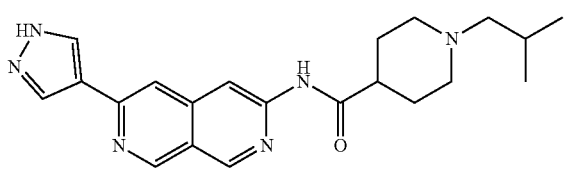 [SMILES: CC(C)CN1CCC(C(=O)Nc2cc3cc(-c4cn[nH]c4)ncc3cn2)CC1] 3628
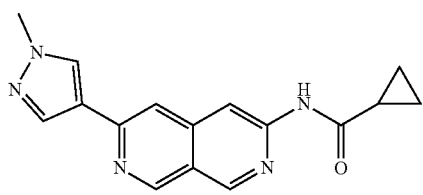 [SMILES: Cn1cc(-c2cc3cc(NC(=O)C4CC4)ncc3cn2)cn1] 3629
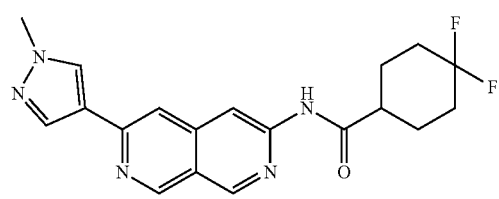 [SMILES: Cn1cc(-c2cc3cc(NC(=O)C4CCC(F)(F)CC4)ncc3cn2)cn1] 3630
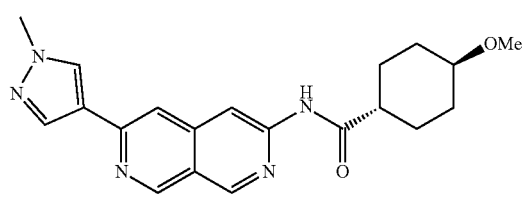 [SMILES: CO[C@H]1CC[C@H](C(=O)Nc2cc3cc(-c4cnn(C)c4)ncc3cn2)CC1] 3631
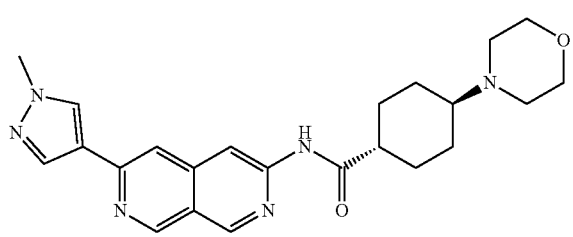 [SMILES: Cn1cc(-c2cc3cc(NC(=O)[C@H]4CC[C@H](N5CCOCC5)CC4)ncc3cn2)cn1] 3632
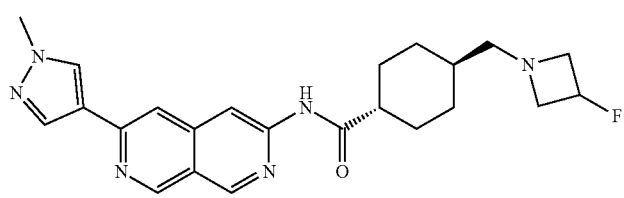 3633

TABLE 1-continued
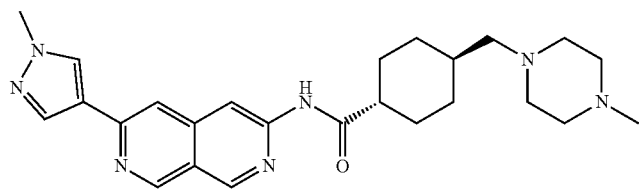 [SMILES: CN1CCN(C[C@H]2CC[C@H](C(=O)Nc3cc4cc(-c5cnn(C)c5)ncc4cn3)CC2)CC1]
3634
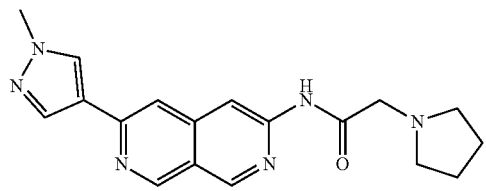 [SMILES: Cn1cc(-c2cc3cc(NC(=O)CN4CCCC4)ncc3cn2)cn1]
3635
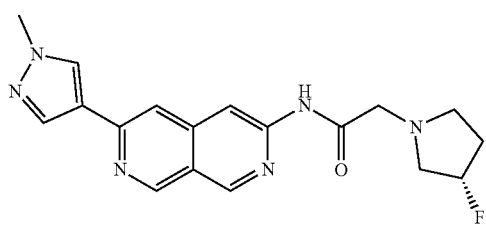
3636
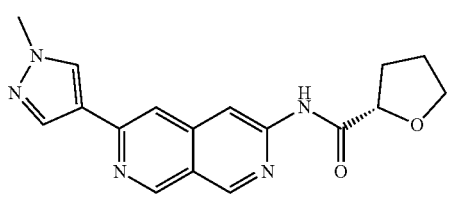 [SMILES: Cn1cc(-c2cc3cc(NC(=O)[C@@H]4CCCO4)ncc3cn2)cn1]
3637
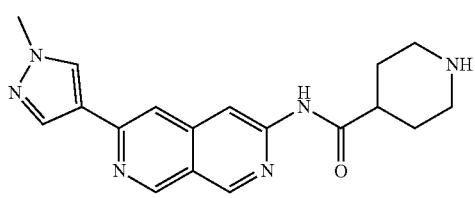 [SMILES: Cn1cc(-c2cc3cc(NC(=O)C4CCNCC4)ncc3cn2)cn1]
3638
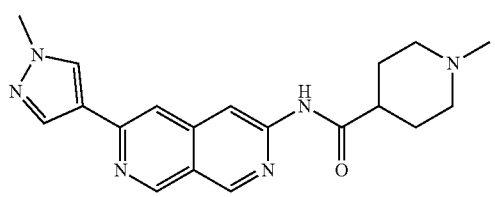 [SMILES: CN1CCC(C(=O)Nc2cc3cc(-c4cnn(C)c4)ncc3cn2)CC1]
3639
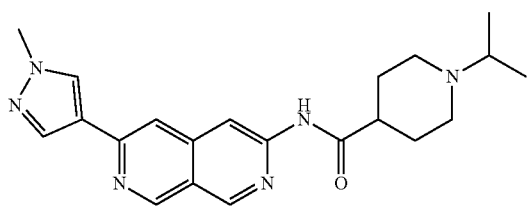
3640
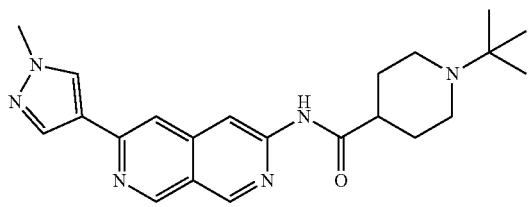 [SMILES: Cn1cc(-c2cc3cc(NC(=O)C4CCN(C(C)(C)C)CC4)ncc3cn2)cn1]
3641

TABLE 1-continued
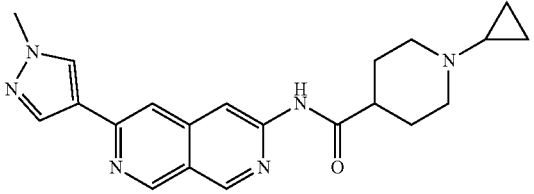 [SMILES: Cn1cc(-c2cc3cc(NC(=O)C4CCN(C5CC5)CC4)ncc3cn2)cn1] 3642
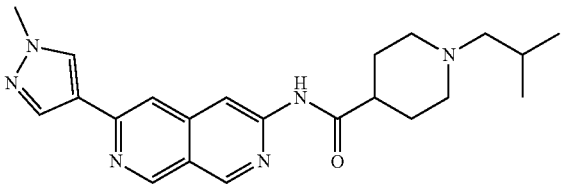 [SMILES: CC(C)CN1CCC(C(=O)Nc2cc3cc(-c4cnn(C)c4)ncc3cn2)CC1] 3643
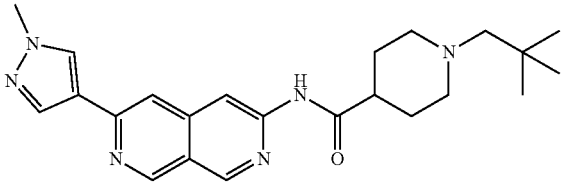 [SMILES: Cn1cc(-c2cc3cc(NC(=O)C4CCN(CC(C)(C)C)CC4)ncc3cn2)cn1] 3644
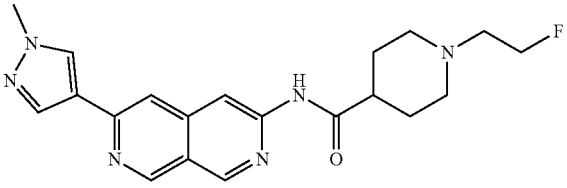 [SMILES: Cn1cc(-c2cc3cc(NC(=O)C4CCN(CCF)CC4)ncc3cn2)cn1] 3645
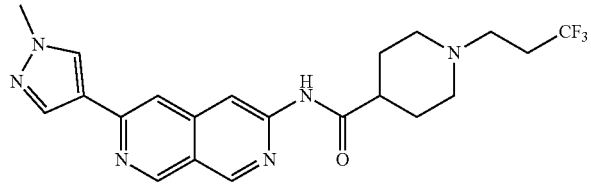 [SMILES: Cn1cc(-c2cc3cc(NC(=O)C4CCN(CCC(F)(F)F)CC4)ncc3cn2)cn1] 3646
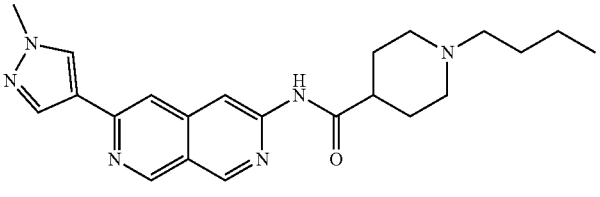 [SMILES: CCCCN1CCC(C(=O)Nc2cc3cc(-c4cnn(C)c4)ncc3cn2)CC1] 3647
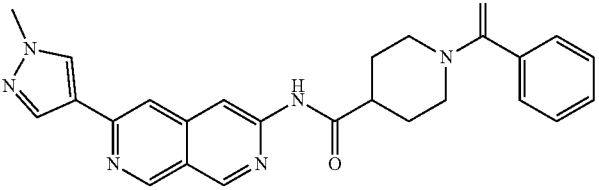 3648
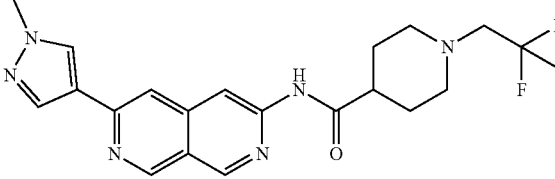 3649

TABLE 1-continued
| | |
|---|---|
| 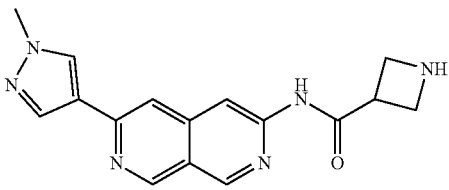 [SMILES: Cn1cc(-c2cc3cc(NC(=O)C4CNC4)ncc3cn2)cn1] | 3650 |
| 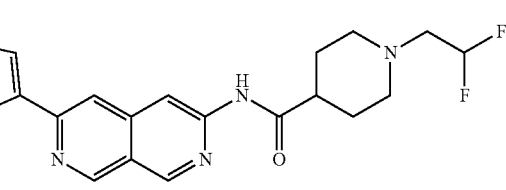 | 3651 |
| 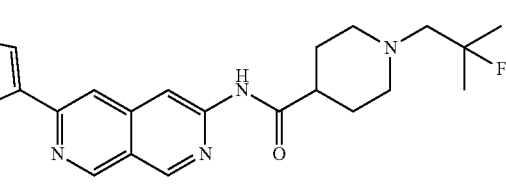 | 3652 |
| 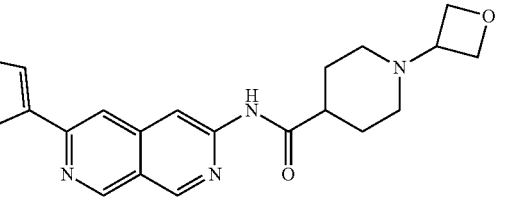 | 3653 |
| 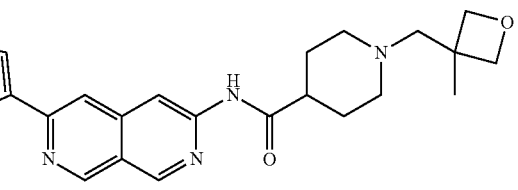 | 3654 |
| 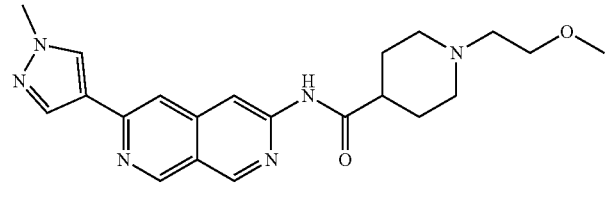 | 3655 |
| 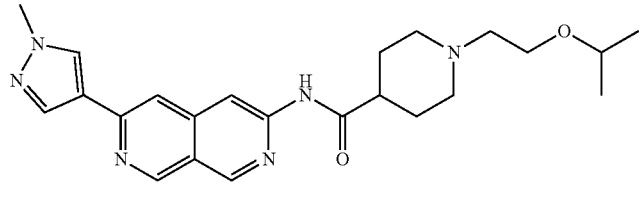 | 3656 |
| 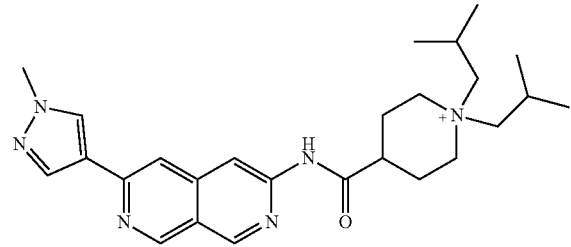 | 3657 |

TABLE 1-continued
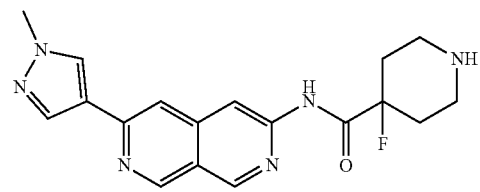 [SMILES: Cn1cc(-c2cc3cc(NC(=O)C4(F)CCNCC4)ncc3cn2)cn1] 3658
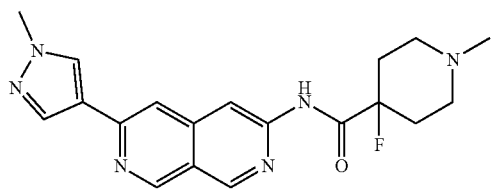 [SMILES: CN1CCC(F)(C(=O)Nc2cc3cc(-c4cnn(C)c4)ncc3cn2)CC1] 3659
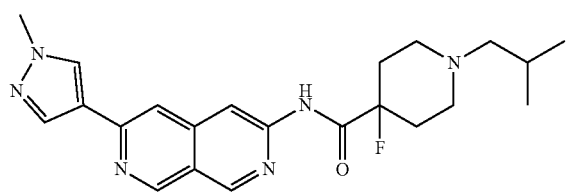 [SMILES: CC(C)CN1CCC(F)(C(=O)Nc2cc3cc(-c4cnn(C)c4)ncc3cn2)CC1] 3660
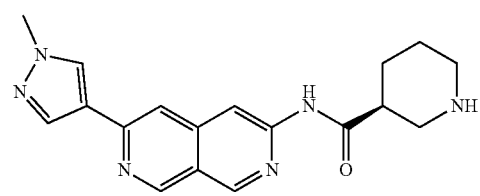 [SMILES: Cn1cc(-c2cc3cc(NC(=O)[C@H]4CCCNC4)ncc3cn2)cn1] 3661
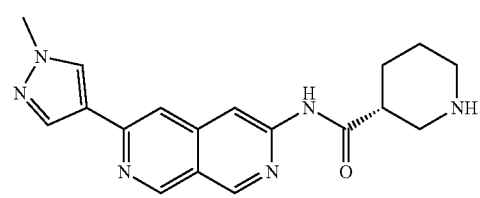 [SMILES: Cn1cc(-c2cc3cc(NC(=O)[C@@H]4CCCNC4)ncc3cn2)cn1] 3662
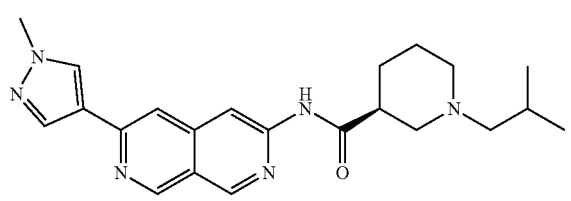 [SMILES: CC(C)CN1CCC[C@H](C(=O)Nc2cc3cc(-c4cnn(C)c4)ncc3cn2)C1] 3663
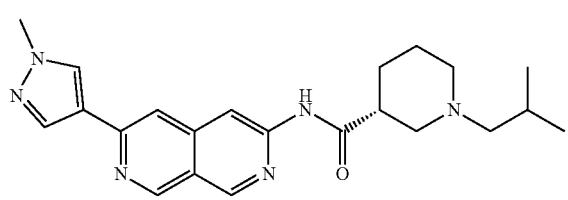 [SMILES: CC(C)CN1CCC[C@@H](C(=O)Nc2cc3cc(-c4cnn(C)c4)ncc3cn2)C1] 3664
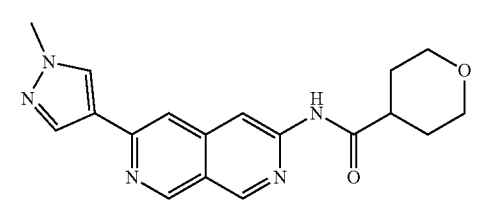 [SMILES: Cn1cc(-c2cc3cc(NC(=O)C4CCOCC4)ncc3cn2)cn1] 3665

TABLE 1-continued
| | |
|---|---|
| 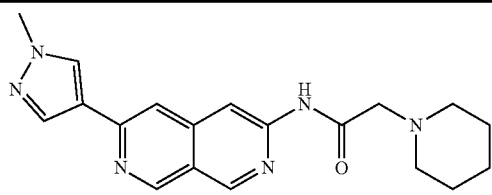 | 3666 |
| 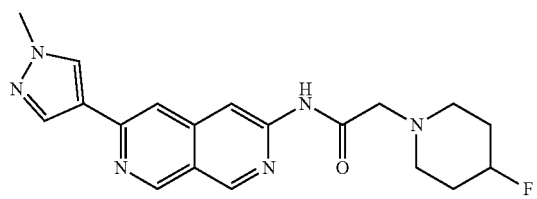 [SMILES: Cn1cc(-c2cc3cc(NC(=O)CN4CCC(F)CC4)ncc3cn2)cn1] | 3667 |
| 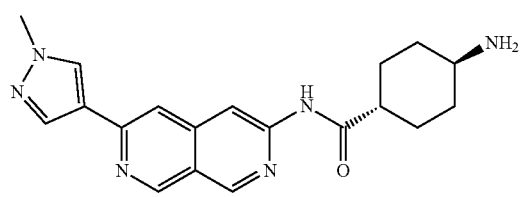 [SMILES: Cn1cc(-c2cc3cc(NC(=O)[C@H]4CC[C@H](N)CC4)ncc3cn2)cn1] | 3668 |
| 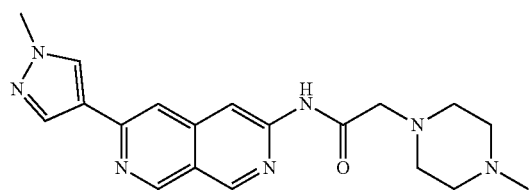 [SMILES: CN1CCN(CC(=O)Nc2cc3cc(-c4cnn(C)c4)ncc3cn2)CC1] | 3669 |
| 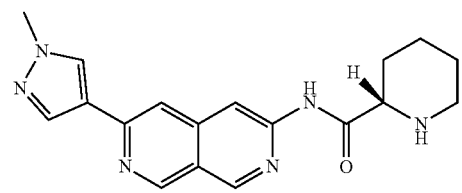 [SMILES: Cn1cc(-c2cc3cc(NC(=O)[C@@H]4CCCCN4)ncc3cn2)cn1] | 3670 |
| 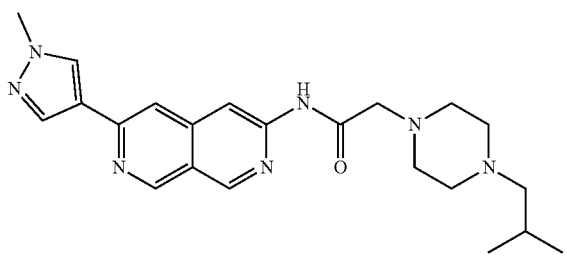 [SMILES: CC(C)CN1CCN(CC(=O)Nc2cc3cc(-c4cnn(C)c4)ncc3cn2)CC1] | 3671 |
| 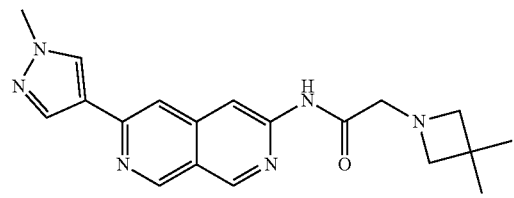 [SMILES: Cn1cc(-c2cc3cc(NC(=O)CN4CC(C)(C)C4)ncc3cn2)cn1] | 3672 |
| 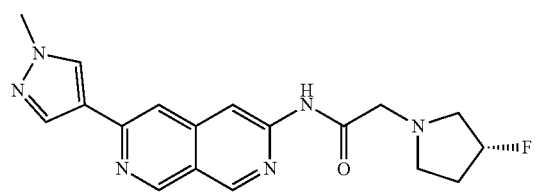 [SMILES: Cn1cc(-c2cc3cc(NC(=O)CN4CC[C@@H](F)C4)ncc3cn2)cn1] | 3673 |

TABLE 1-continued
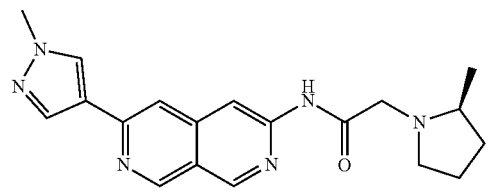 [SMILES: C[C@H]1CCCN1CC(=O)Nc1cc2cc(-c3cnn(C)c3)ncc2cn1] 3674
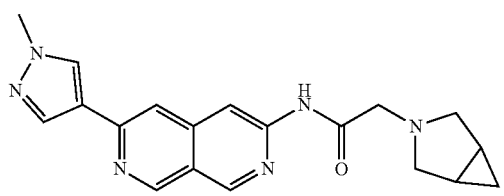 [SMILES: Cn1cc(-c2cc3cc(NC(=O)CN4CC5CC5C4)ncc3cn2)cn1] 3675
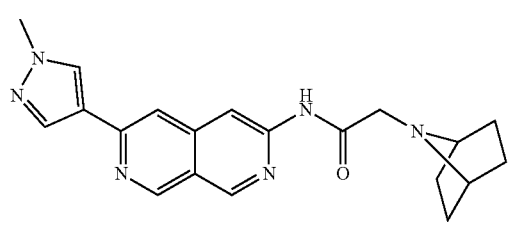 [SMILES: Cn1cc(-c2cc3cc(NC(=O)CN4C5CCC4CC5)ncc3cn2)cn1] 3676
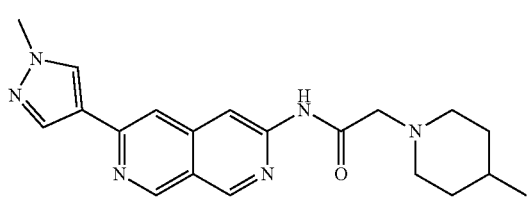 [SMILES: CC1CCN(CC(=O)Nc2cc3cc(-c4cnn(C)c4)ncc3cn2)CC1] 3677
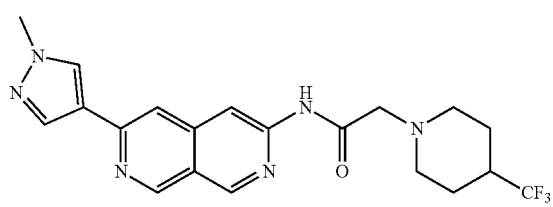 3678
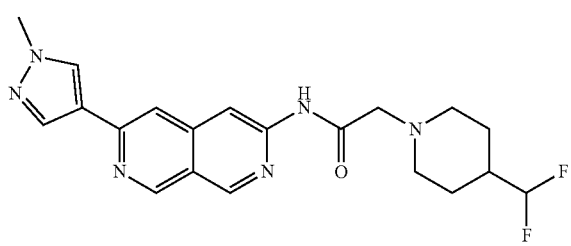 [SMILES: Cn1cc(-c2cc3cc(NC(=O)CN4CCC(C(F)F)CC4)ncc3cn2)cn1] 3679
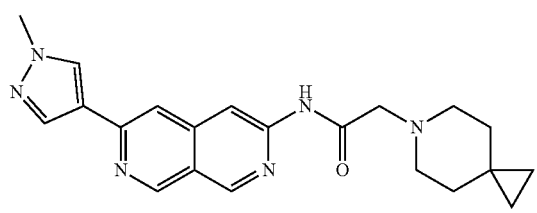 [SMILES: Cn1cc(-c2cc3cc(NC(=O)CN4CCC5(CC4)CC5)ncc3cn2)cn1] 3680

TABLE 1-continued
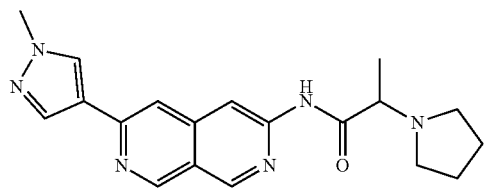 [SMILES: CC(C(=O)Nc1cc2cc(-c3cnn(C)c3)ncc2cn1)N1CCCC1] 3681
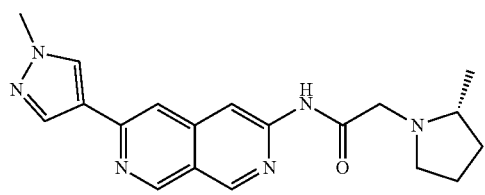 [SMILES: C[C@@H]1CCCN1CC(=O)Nc1cc2cc(-c3cnn(C)c3)ncc2cn1] 3682
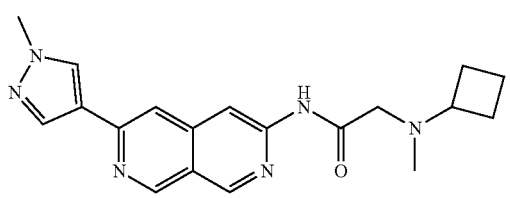 [SMILES: CN(CC(=O)Nc1cc2cc(-c3cnn(C)c3)ncc2cn1)C1CCC1] 3683
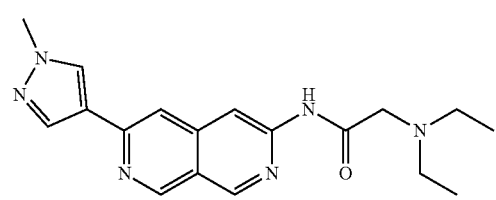 [SMILES: CCN(CC)CC(=O)Nc1cc2cc(-c3cnn(C)c3)ncc2cn1] 3684
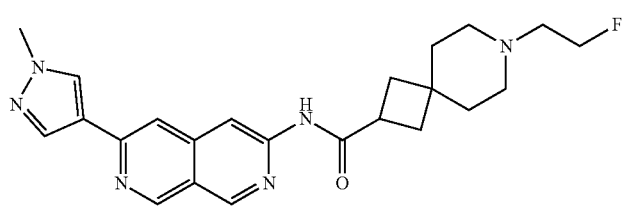 [SMILES: Cn1cc(-c2cc3cc(NC(=O)C4CC5(CCN(CCF)CC5)C4)ncc3cn2)cn1] 3685
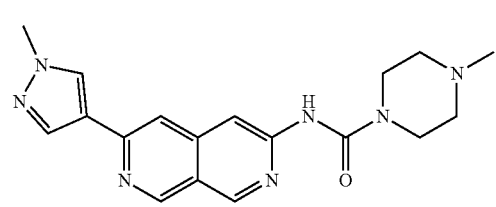 [SMILES: CN1CCN(C(=O)Nc2cc3cc(-c4cnn(C)c4)ncc3cn2)CC1] 3686
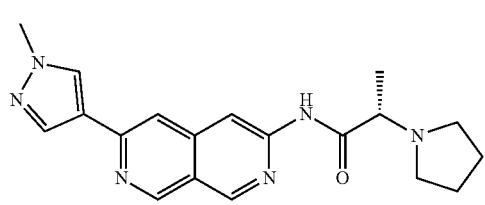 [SMILES: C[C@@H](C(=O)Nc1cc2cc(-c3cnn(C)c3)ncc2cn1)N1CCCC1] 3687
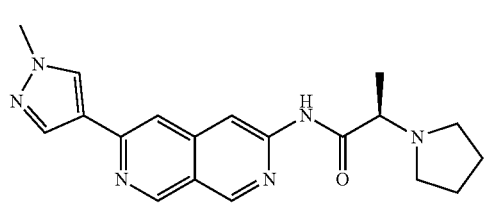 [SMILES: C[C@H](C(=O)Nc1cc2cc(-c3cnn(C)c3)ncc2cn1)N1CCCC1] 3688

TABLE 1-continued
| | |
|---|---|
| 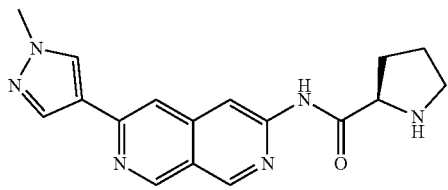 [SMILES: Cn1cc(-c2cc3cc(NC(=O)[C@H]4CCCN4)ncc3cn2)cn1] | 3689 |
| 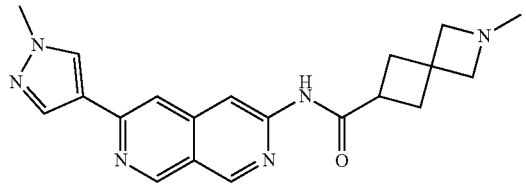 [SMILES: CN1CC2(CC(C(=O)Nc3cc4cc(-c5cnn(C)c5)ncc4cn3)C2)C1] | 3690 |
| 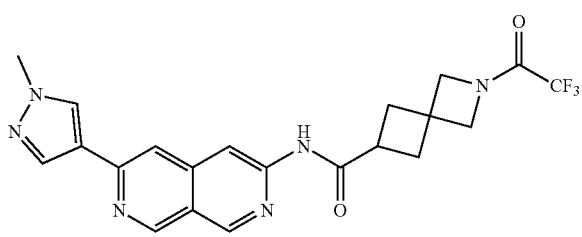 [SMILES: Cn1cc(-c2cc3cc(NC(=O)C4CC5(C4)CN(C(=O)C(F)(F)F)C5)ncc3cn2)cn1] | 3691 |
| 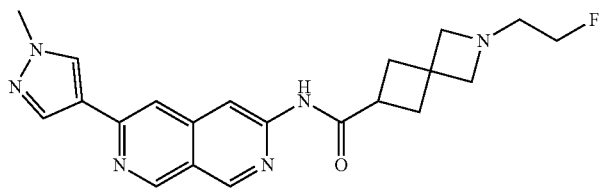 [SMILES: Cn1cc(-c2cc3cc(NC(=O)C4CC5(C4)CN(CCF)C5)ncc3cn2)cn1] | 3692 |
| 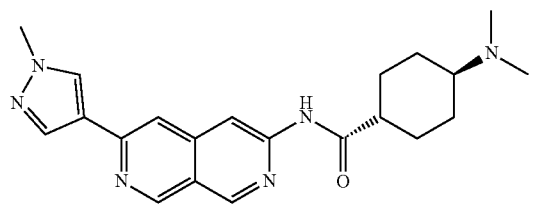 | 3693 |
| 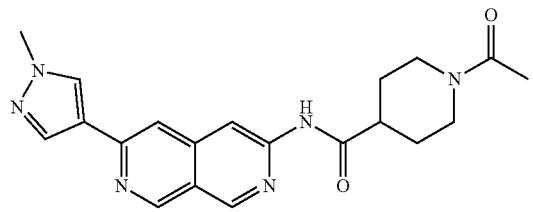 [SMILES: CC(=O)N1CCC(C(=O)Nc2cc3cc(-c4cnn(C)c4)ncc3cn2)CC1] | 3694 |
| 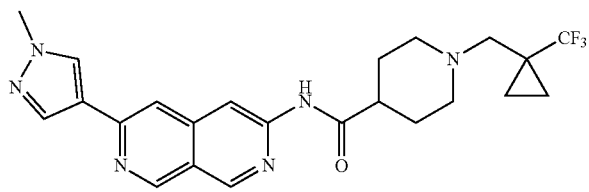 [SMILES: Cn1cc(-c2cc3cc(NC(=O)C4CCN(CC5(C(F)(F)F)CC5)CC4)ncc3cn2)cn1] | 3695 |
| 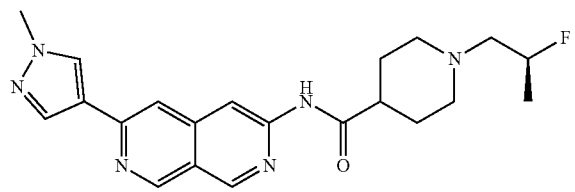 [SMILES: C[C@H](F)CN1CCC(C(=O)Nc2cc3cc(-c4cnn(C)c4)ncc3cn2)CC1] | 3696 |

TABLE 1-continued
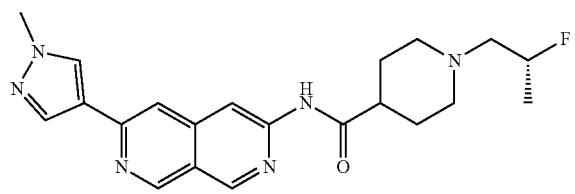 [SMILES: C[C@@H](F)CN1CCC(C(=O)Nc2cc3cc(-c4cnn(C)c4)ncc3cn2)CC1] 3697
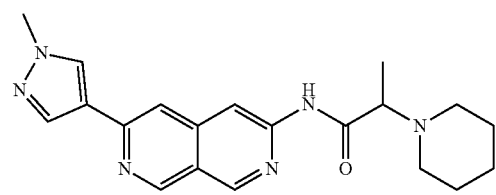 3698
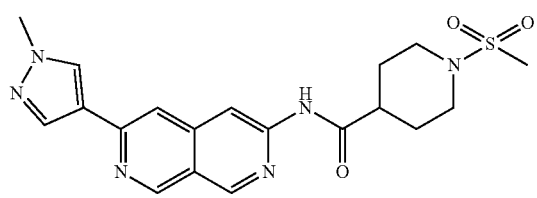 [SMILES: Cn1cc(-c2cc3cc(NC(=O)C4CCN(S(C)(=O)=O)CC4)ncc3cn2)cn1] 3699
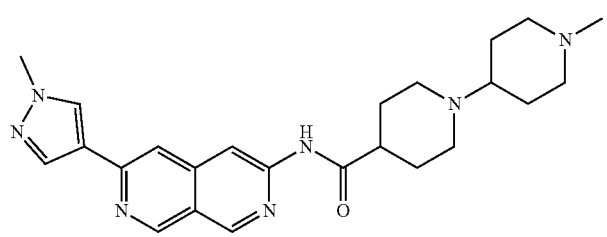 [SMILES: CN1CCC(N2CCC(C(=O)Nc3cc4cc(-c5cnn(C)c5)ncc4cn3)CC2)CC1] 3700
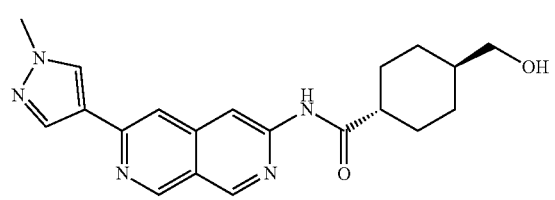 [SMILES: Cn1cc(-c2cc3cc(NC(=O)[C@H]4CC[C@H](CO)CC4)ncc3cn2)cn1] 3701
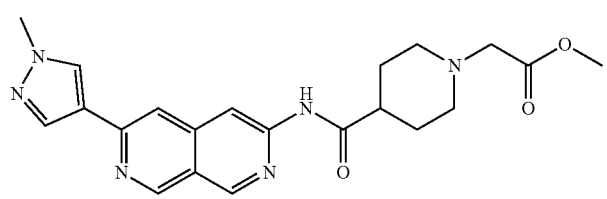 [SMILES: COC(=O)CN1CCC(C(=O)Nc2cc3cc(-c4cnn(C)c4)ncc3cn2)CC1] 3702
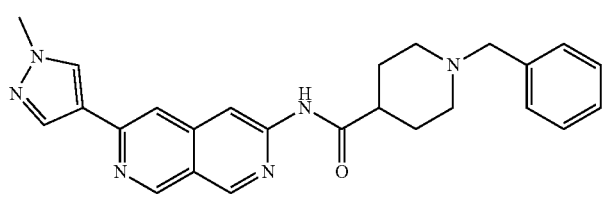 [SMILES: Cn1cc(-c2cc3cc(NC(=O)C4CCN(Cc5ccccc5)CC4)ncc3cn2)cn1] 3703

TABLE 1-continued
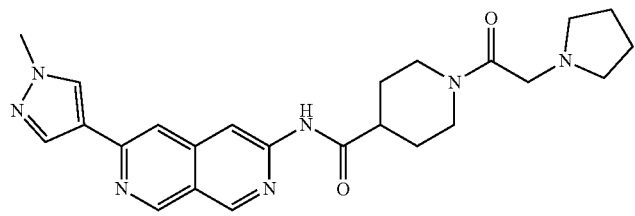 [SMILES: Cn1cc(-c2cc3cc(NC(=O)C4CCN(C(=O)CN5CCCC5)CC4)ncc3cn2)cn1]
3704
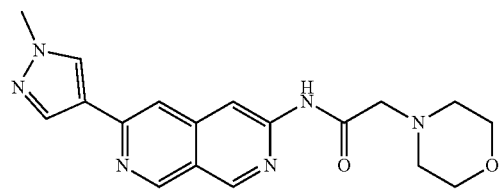 [SMILES: Cn1cc(-c2cc3cc(NC(=O)CN4CCOCC4)ncc3cn2)cn1]
3705
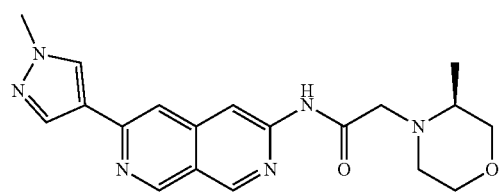 [SMILES: C[C@H]1COCCN1CC(=O)Nc1cc2cc(-c3cnn(C)c3)ncc2cn1]
3706
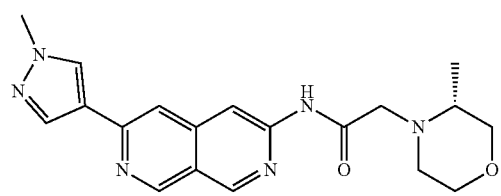 [SMILES: C[C@@H]1COCCN1CC(=O)Nc1cc2cc(-c3cnn(C)c3)ncc2cn1]
3707
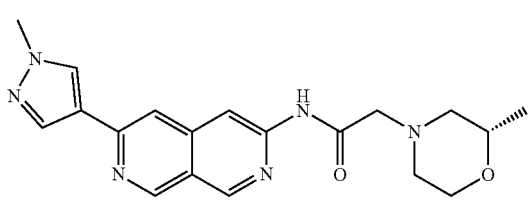 [SMILES: C[C@H]1CN(CC(=O)Nc2cc3cc(-c4cnn(C)c4)ncc3cn2)CCO1]
3708
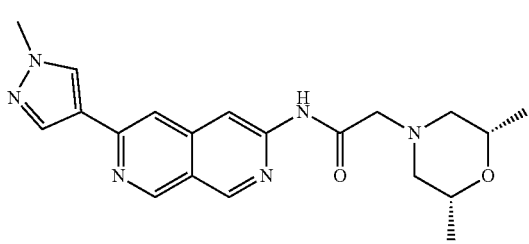 [SMILES: C[C@@H]1CN(CC(=O)Nc2cc3cc(-c4cnn(C)c4)ncc3cn2)C[C@H](C)O1]
3709
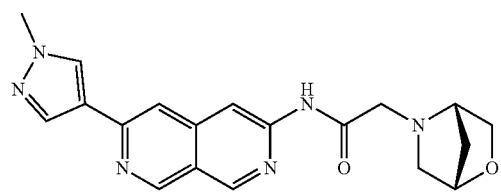 [SMILES: Cn1cc(-c2cc3cc(NC(=O)CN4C[C@@H]5C[C@H]4CO5)ncc3cn2)cn1]
3710
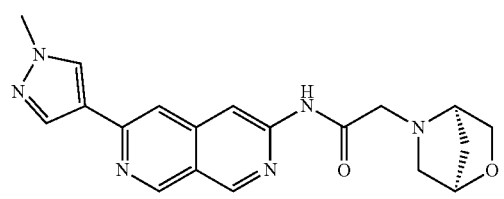
3711

TABLE 1-continued
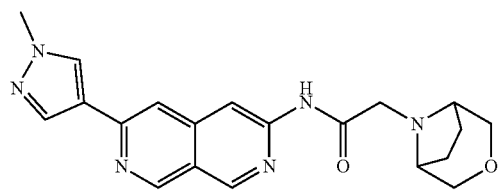 [SMILES: Cn1cc(-c2cc3cc(NC(=O)CN4C5CCC4COC5)ncc3cn2)cn1] 3712
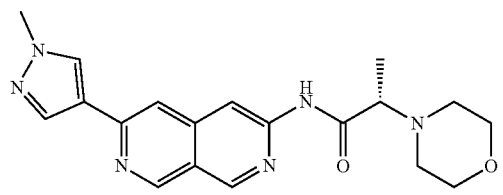 [SMILES: C[C@@H](C(=O)Nc1cc2cc(-c3cnn(C)c3)ncc2cn1)N1CCOCC1] 3713
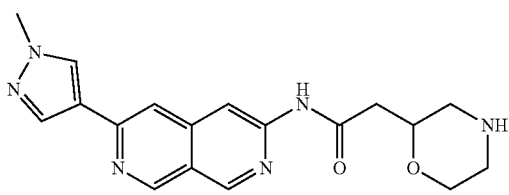 [SMILES: Cn1cc(-c2cc3cc(NC(=O)CC4CNCCO4)ncc3cn2)cn1] 3714
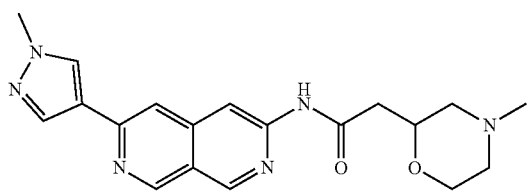 [SMILES: CN1CCOC(CC(=O)Nc2cc3cc(-c4cnn(C)c4)ncc3cn2)C1] 3715
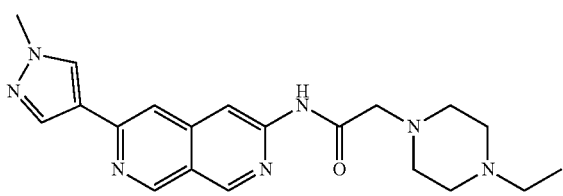 [SMILES: CCN1CCN(CC(=O)Nc2cc3cc(-c4cnn(C)c4)ncc3cn2)CC1] 3716
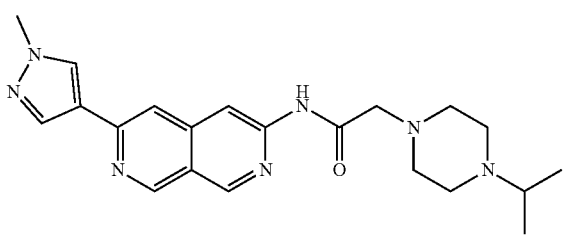 [SMILES: CC(C)N1CCN(CC(=O)Nc2cc3cc(-c4cnn(C)c4)ncc3cn2)CC1] 3717
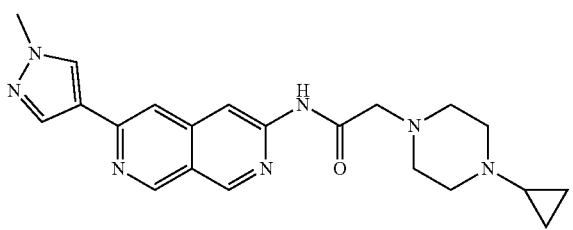 [SMILES: Cn1cc(-c2cc3cc(NC(=O)CN4CCN(C5CC5)CC4)ncc3cn2)cn1] 3718

TABLE 1-continued
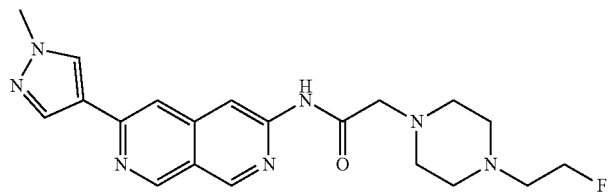 [SMILES: Cn1cc(-c2cc3cc(NC(=O)CN4CCN(CCF)CC4)ncc3cn2)cn1] 3719
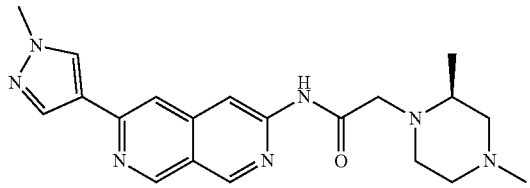 [SMILES: C[C@H]1CN(C)CCN1CC(=O)Nc1cc2cc(-c3cnn(C)c3)ncc2cn1] 3720
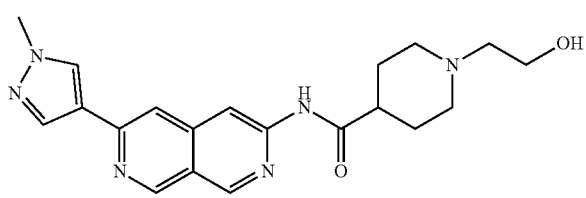 [SMILES: Cn1cc(-c2cc3cc(NC(=O)C4CCN(CCO)CC4)ncc3cn2)cn1] 3721
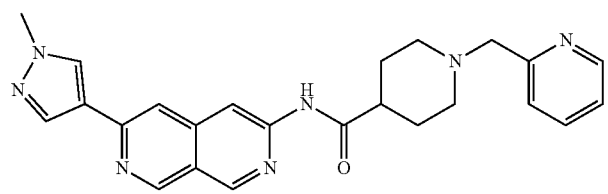 [SMILES: Cn1cc(-c2cc3cc(NC(=O)C4CCN(Cc5ccccn5)CC4)ncc3cn2)cn1] 3722
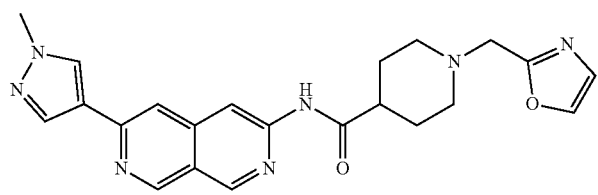 [SMILES: Cn1cc(-c2cc3cc(NC(=O)C4CCN(Cc5ncco5)CC4)ncc3cn2)cn1] 3723
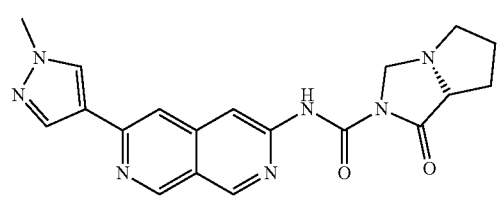 3724
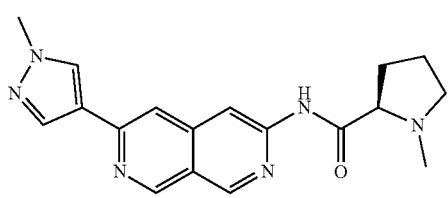 [SMILES: CN1CCC[C@@H]1C(=O)Nc1cc2cc(-c3cnn(C)c3)ncc2cn1] 3725
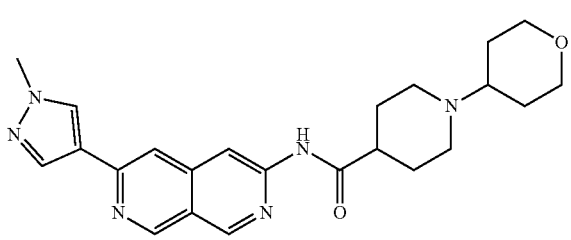 [SMILES: Cn1cc(-c2cc3cc(NC(=O)C4CCN(C5CCOCC5)CC4)ncc3cn2)cn1] 3726

TABLE 1-continued
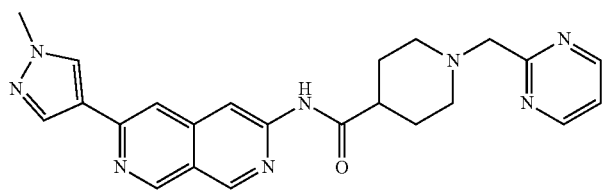 [SMILES: Cn1cc(-c2cc3cc(NC(=O)C4CCN(Cc5ncccn5)CC4)ncc3cn2)cn1]  3727
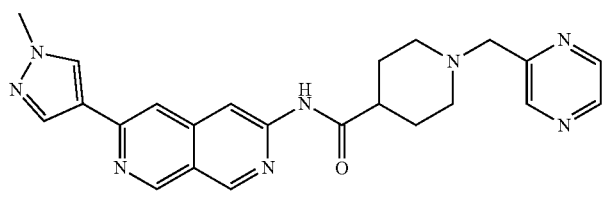 [SMILES: Cn1cc(-c2cc3cc(NC(=O)C4CCN(Cc5cnccn5)CC4)ncc3cn2)cn1]  3728
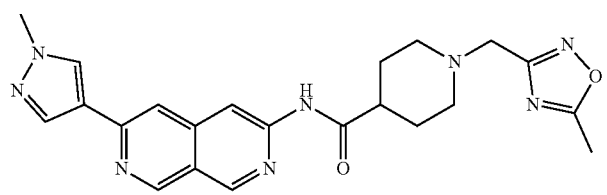 [SMILES: Cc1nc(CN2CCC(C(=O)Nc3cc4cc(-c5cnn(C)c5)ncc4cn3)CC2)no1]  3729
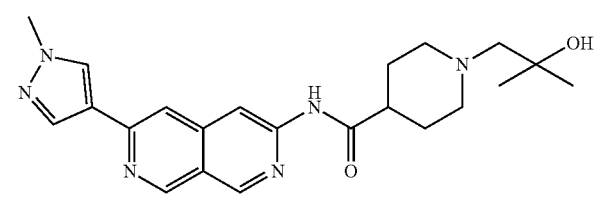 [SMILES: Cn1cc(-c2cc3cc(NC(=O)C4CCN(CC(C)(C)O)CC4)ncc3cn2)cn1]  3730
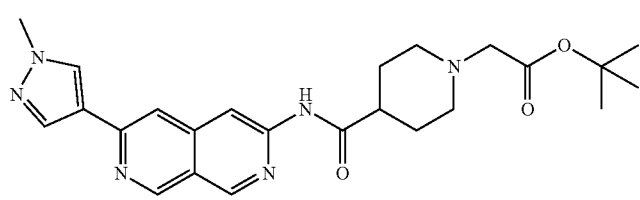 [SMILES: Cn1cc(-c2cc3cc(NC(=O)C4CCN(CC(=O)OC(C)(C)C)CC4)ncc3cn2)cn1]  3731
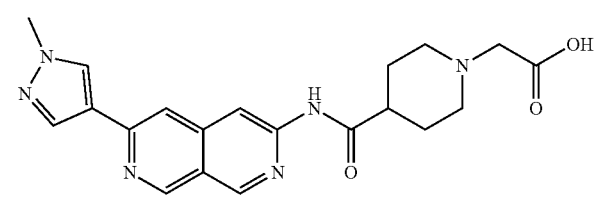 [SMILES: Cn1cc(-c2cc3cc(NC(=O)C4CCN(CC(=O)O)CC4)ncc3cn2)cn1]  3732
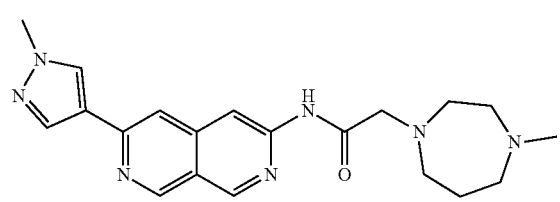 [SMILES: CN1CCCN(CC(=O)Nc2cc3cc(-c4cnn(C)c4)ncc3cn2)CC1]  3733
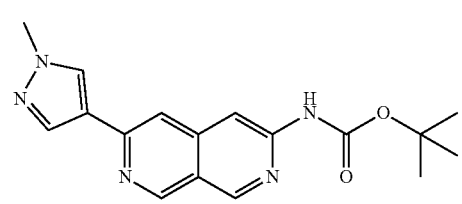 [SMILES: Cn1cc(-c2cc3cc(NC(=O)OC(C)(C)C)ncc3cn2)cn1]  3734

TABLE 1-continued
| | |
|---|---|
| 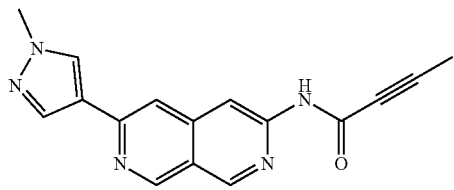 [SMILES: CC#CC(=O)Nc1cc2cc(-c3cnn(C)c3)ncc2cn1] | 3735 |
| 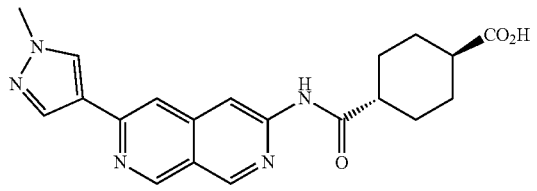 [SMILES: Cn1cc(-c2cc3cc(NC(=O)[C@H]4CC[C@H](C(=O)O)CC4)ncc3cn2)cn1] | 3736 |
| 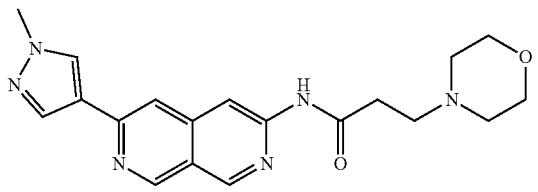 [SMILES: Cn1cc(-c2cc3cc(NC(=O)CCN4CCOCC4)ncc3cn2)cn1] | 3737 |
| 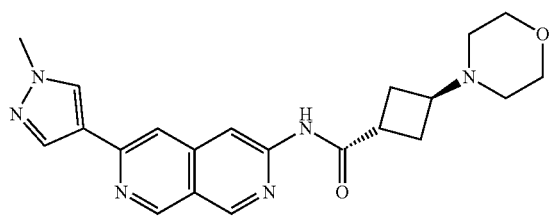 | 3738 |
| 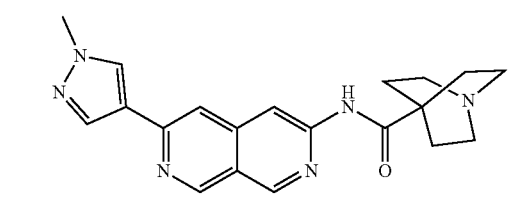 [SMILES: Cn1cc(-c2cc3cc(NC(=O)C45CCN(CC4)CC5)ncc3cn2)cn1] | 3739 |
| 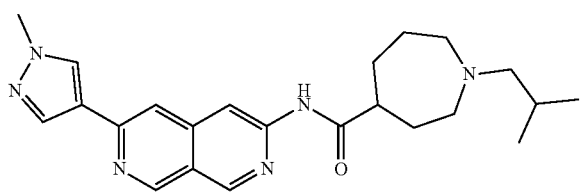 [SMILES: CC(C)CN1CCCC(C(=O)Nc2cc3cc(-c4cnn(C)c4)ncc3cn2)CC1] | 3740 |
| 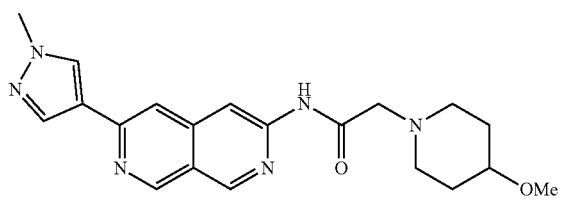 [SMILES: COC1CCN(CC(=O)Nc2cc3cc(-c4cnn(C)c4)ncc3cn2)CC1] | 3741 |
| 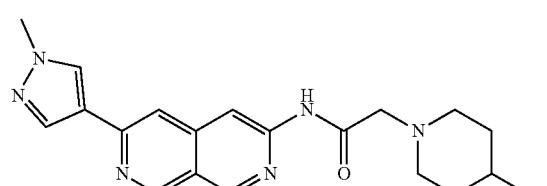 | 3742 |

TABLE 1-continued
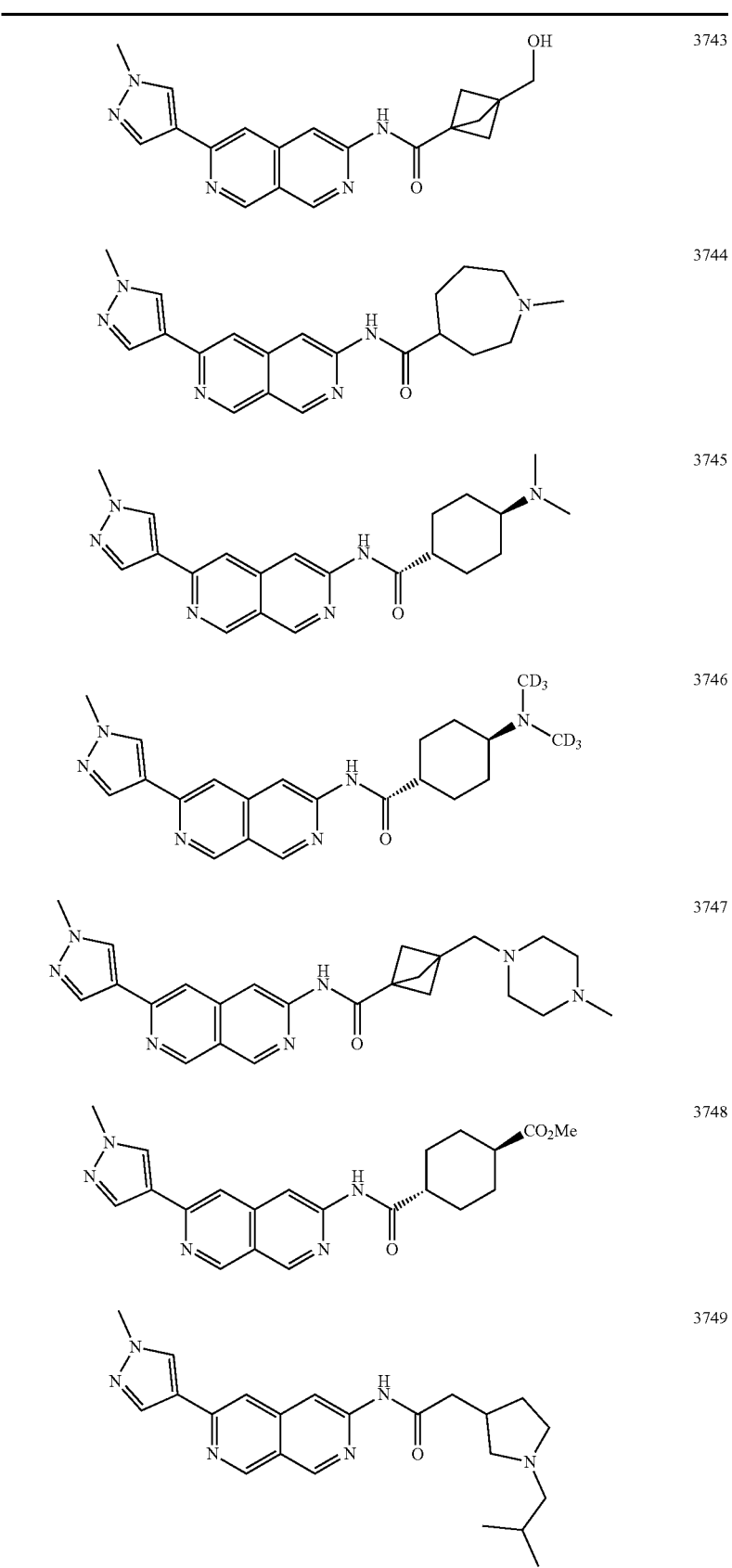
| | |
|---|---|
| | 3743 |
| | 3744 |
| | 3745 |
| | 3746 |
| | 3747 |
| | 3748 |
| | 3749 |

US 10,703,748 B2
1153                                                                                1154
TABLE 1-continued
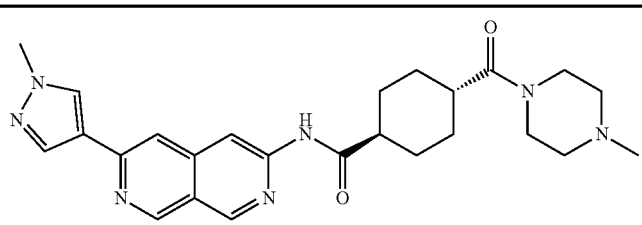 3750
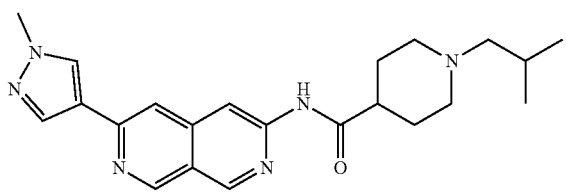 [SMILES: CC(C)CN1CCC(C(=O)Nc2cc3cc(-c4cnn(C)c4)ncc3cn2)CC1] 3751
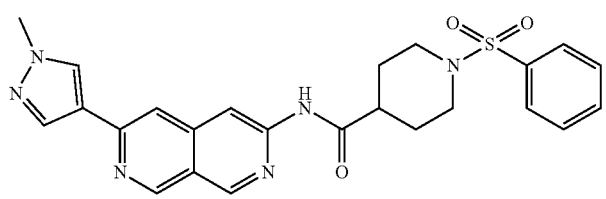 [SMILES: Cn1cc(-c2cc3cc(NC(=O)C4CCN(S(=O)(=O)c5ccccc5)CC4)ncc3cn2)cn1] 3752
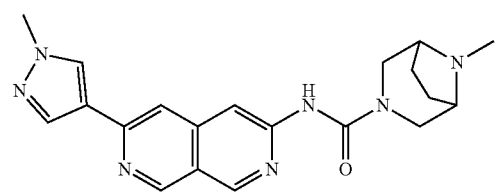 [SMILES: CN1C2CCC1CN(C(=O)Nc1cc3cc(-c4cnn(C)c4)ncc3cn1)C2] 3753
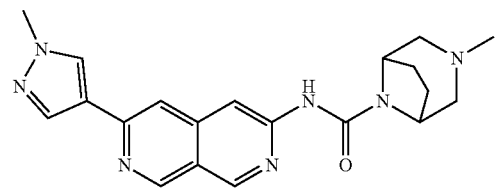 [SMILES: CN1CC2CCC(C1)N2C(=O)Nc1cc2cc(-c3cnn(C)c3)ncc2cn1] 3754
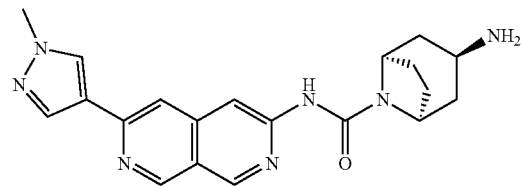 [SMILES: Cn1cc(-c2cc3cc(NC(=O)N4[C@@H]5CC[C@H]4C[C@H](N)C5)ncc3cn2)cn1] 3755
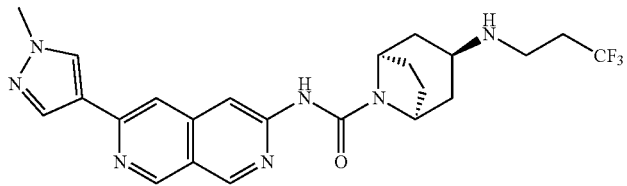 [SMILES: Cn1cc(-c2cc3cc(NC(=O)N4[C@@H]5CC[C@H]4C[C@H](NCCC(F)(F)F)C5)ncc3cn2)cn1] 3756
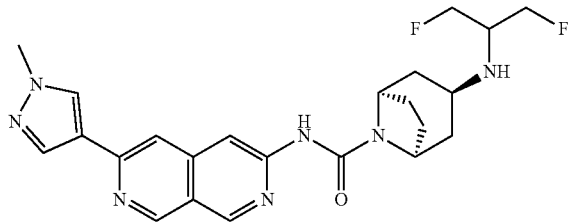 [SMILES: Cn1cc(-c2cc3cc(NC(=O)N4[C@@H]5CC[C@H]4C[C@H](NC(CF)CF)C5)ncc3cn2)cn1] 3757

TABLE 1-continued
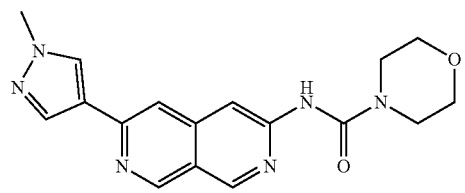 [SMILES: Cn1cc(-c2cc3cc(NC(=O)N4CCOCC4)ncc3cn2)cn1] 3758
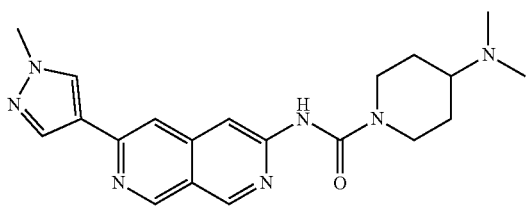 3759
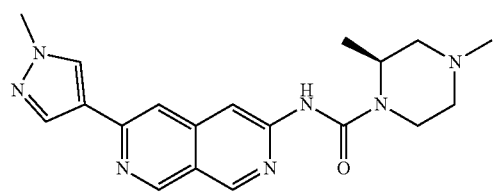 [SMILES: C[C@H]1CN(C)CCN1C(=O)Nc1cc2cc(-c3cnn(C)c3)ncc2cn1] 3760
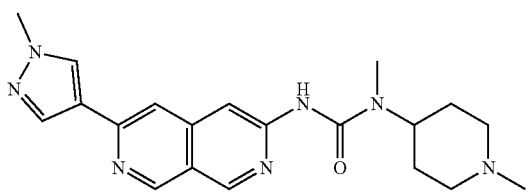 [SMILES: CN1CCC(N(C)C(=O)Nc2cc3cc(-c4cnn(C)c4)ncc3cn2)CC1] 3761
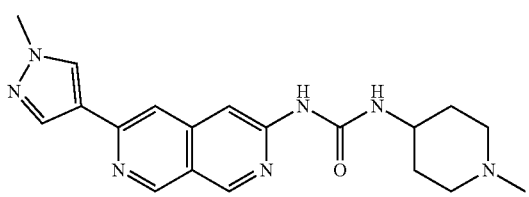 [SMILES: CN1CCC(NC(=O)Nc2cc3cc(-c4cnn(C)c4)ncc3cn2)CC1] 3762
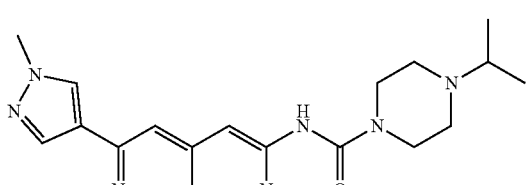 3763
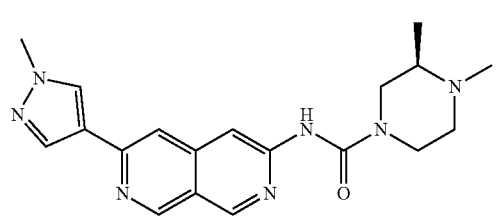 [SMILES: C[C@@H]1CN(C(=O)Nc2cc3cc(-c4cnn(C)c4)ncc3cn2)CCN1C] 3764
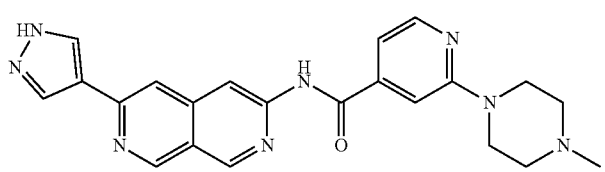 [SMILES: CN1CCN(c2cc(C(=O)Nc3cc4cc(-c5cn[nH]c5)ncc4cn3)ccn2)CC1] 3765

TABLE 1-continued
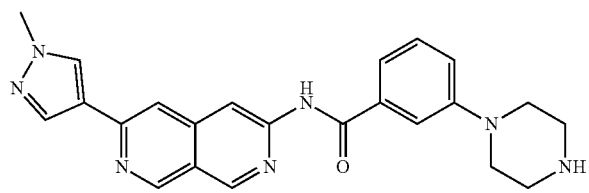 [SMILES: Cn1cc(-c2cc3cc(NC(=O)c4cccc(N5CCNCC5)c4)ncc3cn2)cn1]
3766
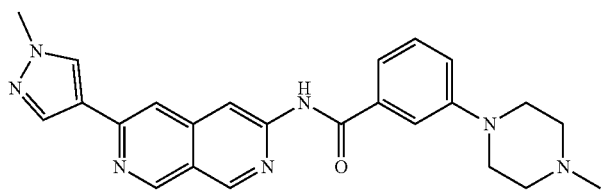 [SMILES: CN1CCN(c2cccc(C(=O)Nc3cc4cc(-c5cnn(C)c5)ncc4cn3)c2)CC1]
3767
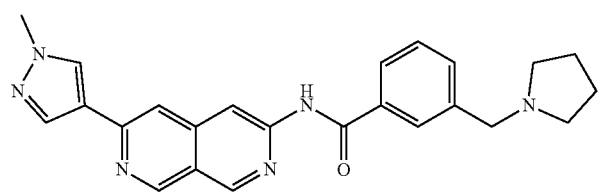
3768
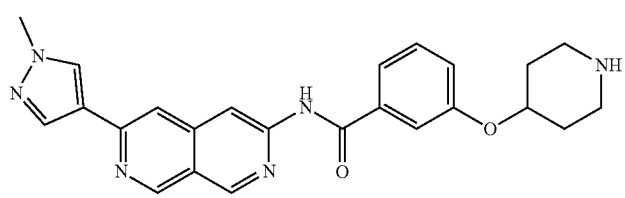 [SMILES: Cn1cc(-c2cc3cc(NC(=O)c4cccc(OC5CCNCC5)c4)ncc3cn2)cn1]
3769
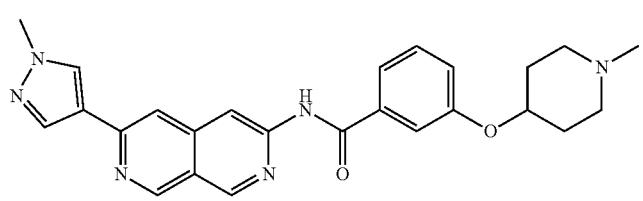 [SMILES: CN1CCC(Oc2cccc(C(=O)Nc3cc4cc(-c5cnn(C)c5)ncc4cn3)c2)CC1]
3770
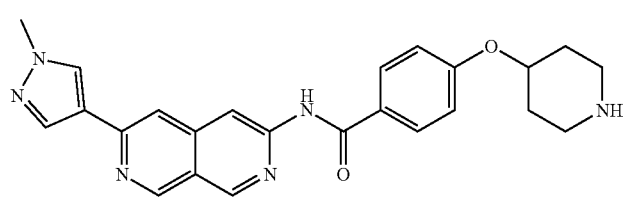 [SMILES: Cn1cc(-c2cc3cc(NC(=O)c4ccc(OC5CCNCC5)cc4)ncc3cn2)cn1]
3771
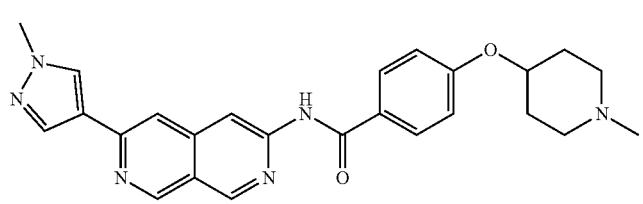 [SMILES: CN1CCC(Oc2ccc(C(=O)Nc3cc4cc(-c5cnn(C)c5)ncc4cn3)cc2)CC1]
3772
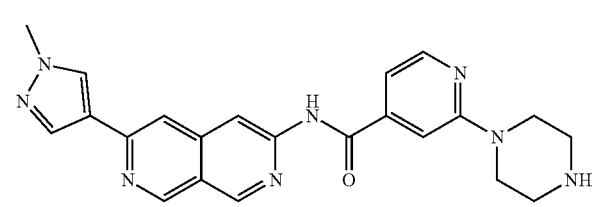 [SMILES: Cn1cc(-c2cc3cc(NC(=O)c4ccnc(N5CCNCC5)c4)ncc3cn2)cn1]
3773

TABLE 1-continued
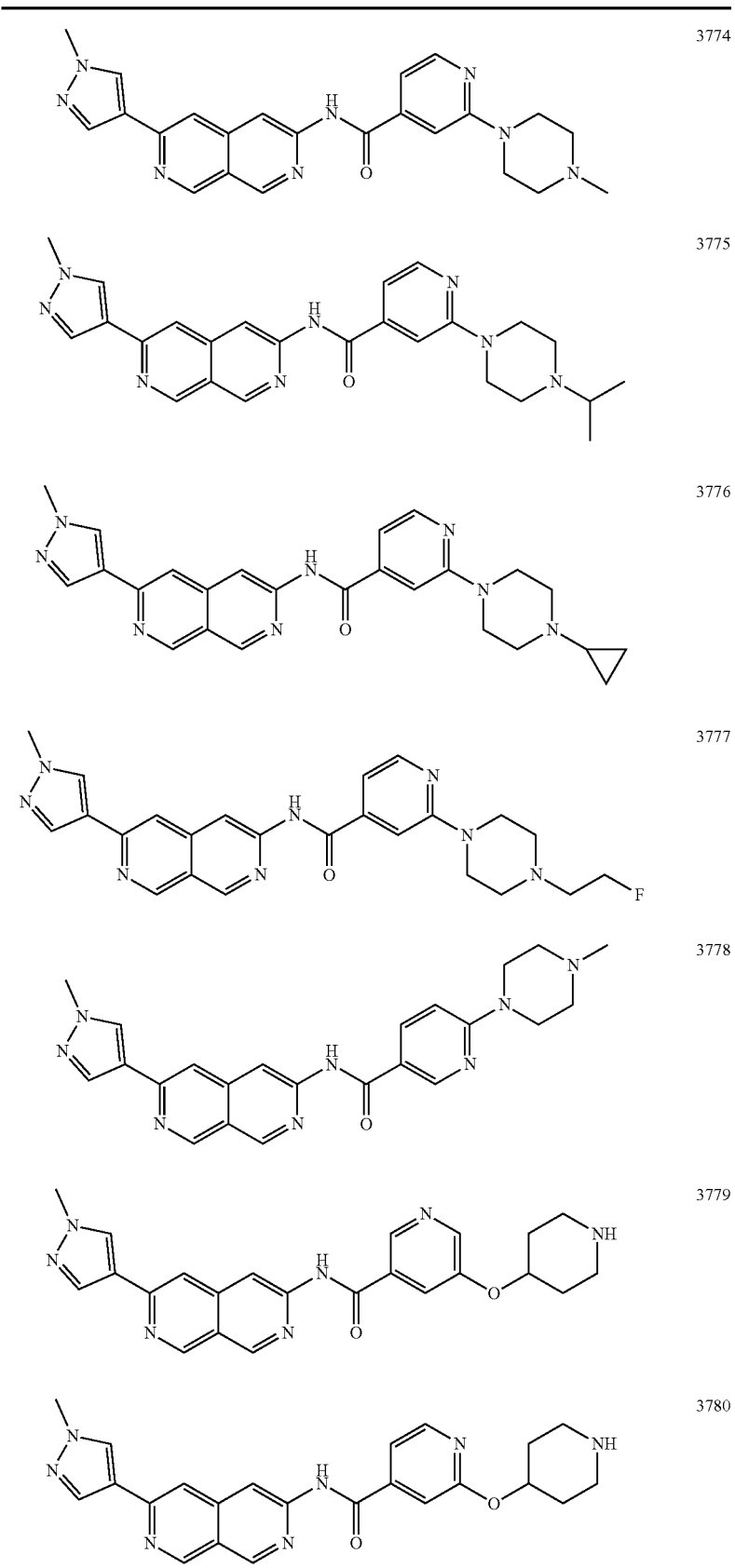
3774
3775
3776
3777
3778
3779
3780

TABLE 1-continued
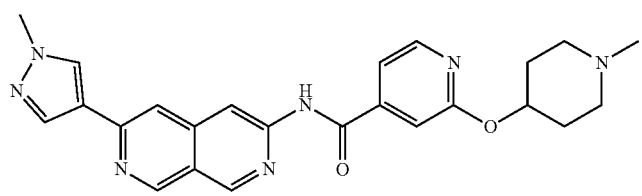 [SMILES: CN1CCC(Oc2cc(C(=O)Nc3cc4cc(-c5cnn(C)c5)ncc4cn3)ccn2)CC1] 3781
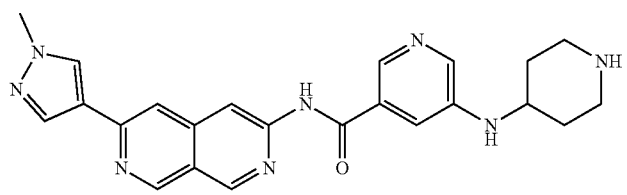 [SMILES: Cn1cc(-c2cc3cc(NC(=O)c4cncc(NC5CCNCC5)c4)ncc3cn2)cn1] 3782
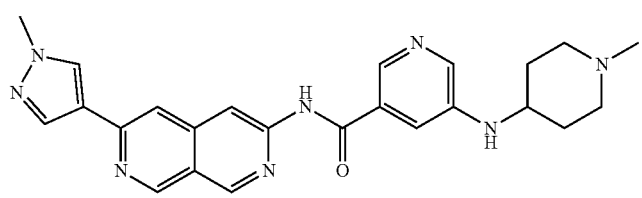 [SMILES: CN1CCC(Nc2cncc(C(=O)Nc3cc4cc(-c5cnn(C)c5)ncc4cn3)c2)CC1] 3783
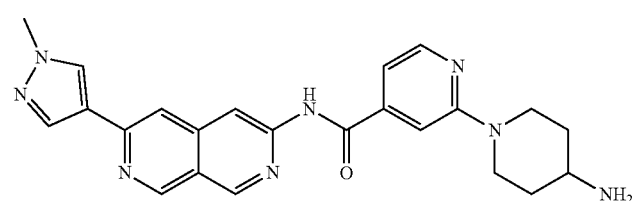 3784
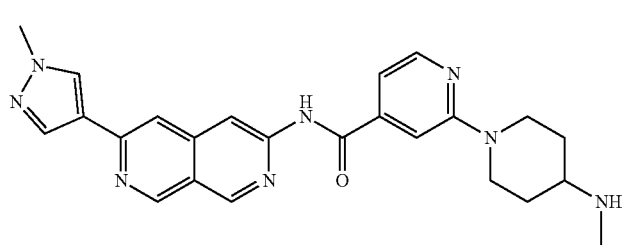 [SMILES: CNC1CCN(c2cc(C(=O)Nc3cc4cc(-c5cnn(C)c5)ncc4cn3)ccn2)CC1] 3785
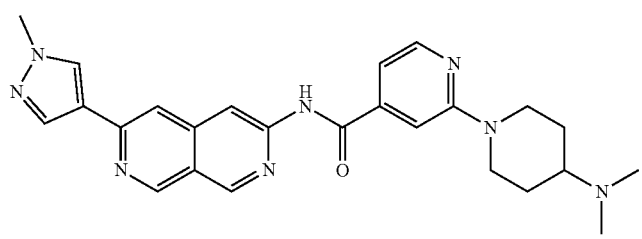 [SMILES: CN(C)C1CCN(c2cc(C(=O)Nc3cc4cc(-c5cnn(C)c5)ncc4cn3)ccn2)CC1] 3786
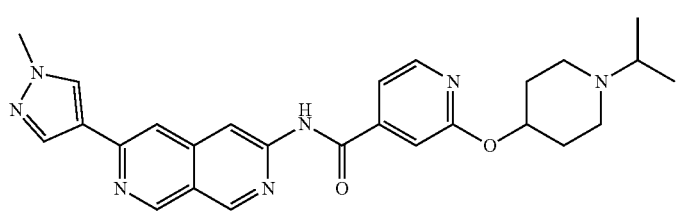 [SMILES: CC(C)N1CCC(Oc2cc(C(=O)Nc3cc4cc(-c5cnn(C)c5)ncc4cn3)ccn2)CC1] 3787

TABLE 1-continued
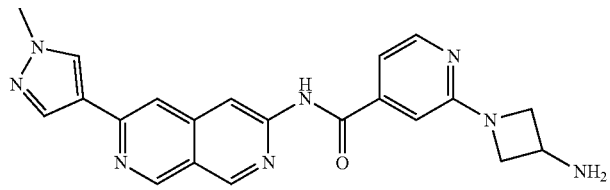 [SMILES: Cn1cc(-c2cc3cc(NC(=O)c4ccnc(N5CC(N)C5)c4)ncc3cn2)cn1] 3788
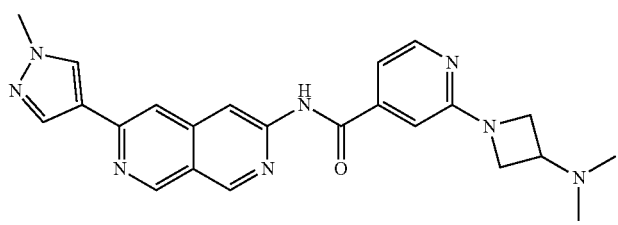 3789
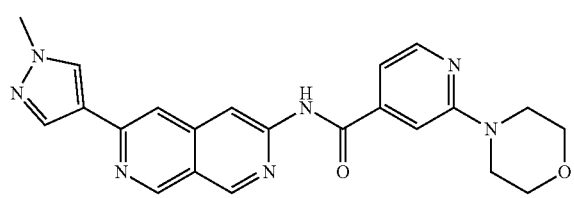 [SMILES: Cn1cc(-c2cc3cc(NC(=O)c4ccnc(N5CCOCC5)c4)ncc3cn2)cn1] 3790
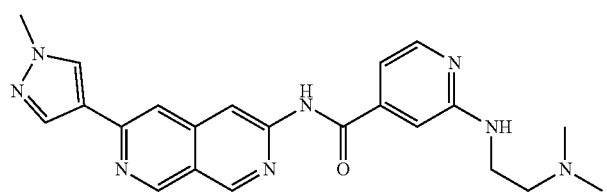 [SMILES: CN(C)CCNc1cc(C(=O)Nc2cc3cc(-c4cnn(C)c4)ncc3cn2)ccn1] 3791
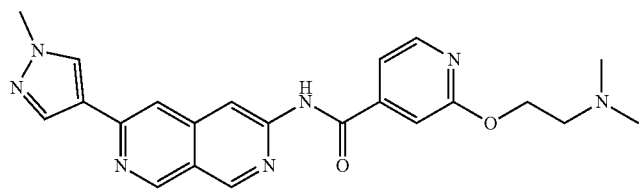 [SMILES: CN(C)CCOc1cc(C(=O)Nc2cc3cc(-c4cnn(C)c4)ncc3cn2)ccn1] 3792
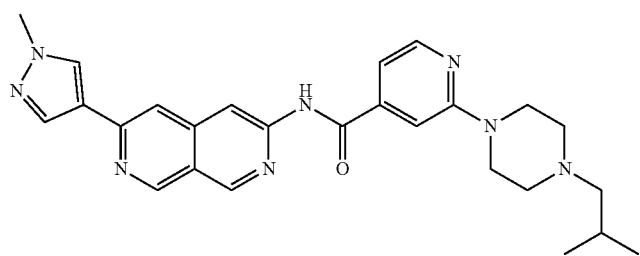 [SMILES: CC(C)CN1CCN(c2cc(C(=O)Nc3cc4cc(-c5cnn(C)c5)ncc4cn3)ccn2)CC1] 3793
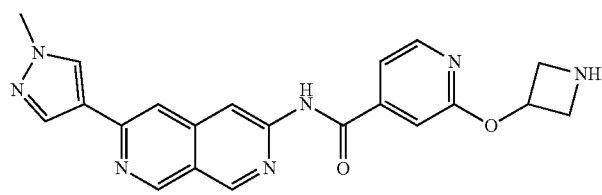 [SMILES: Cn1cc(-c2cc3cc(NC(=O)c4ccnc(OC5CNC5)c4)ncc3cn2)cn1] 3794

TABLE 1-continued
| | |
|---|---|
| 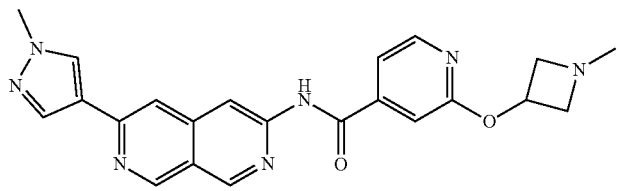 [SMILES: CN1CC(Oc2cc(C(=O)Nc3cc4cc(-c5cnn(C)c5)ncc4cn3)ccn2)C1] | 3795 |
| 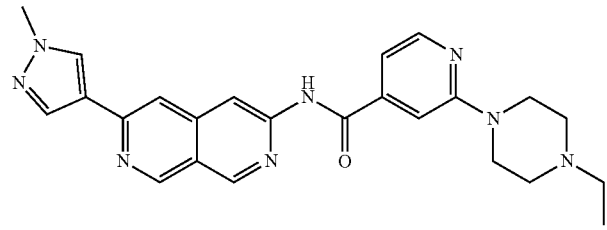 [SMILES: CCN1CCN(c2cc(C(=O)Nc3cc4cc(-c5cnn(C)c5)ncc4cn3)ccn2)CC1] | 3796 |
| 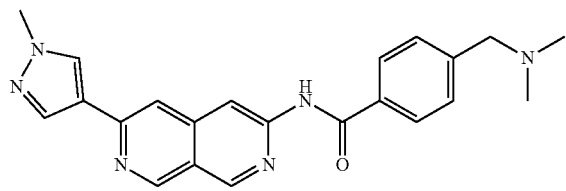 [SMILES: CN(C)Cc1ccc(C(=O)Nc2cc3cc(-c4cnn(C)c4)ncc3cn2)cc1] | 3797 |
| 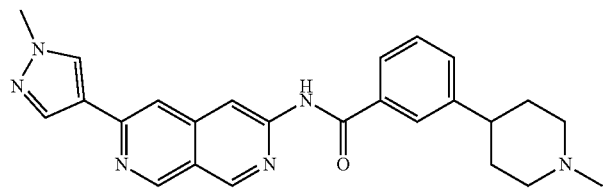 [SMILES: CN1CCC(c2cccc(C(=O)Nc3cc4cc(-c5cnn(C)c5)ncc4cn3)c2)CC1] | 3798 |
| 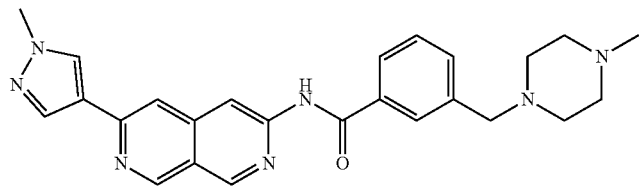 [SMILES: CN1CCN(Cc2cccc(C(=O)Nc3cc4cc(-c5cnn(C)c5)ncc4cn3)c2)CC1] | 3799 |
| 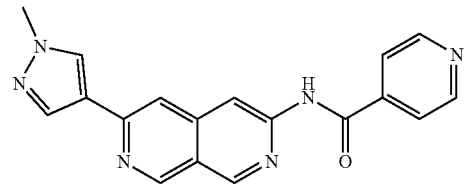 [SMILES: Cn1cc(-c2cc3cc(NC(=O)c4ccncc4)ncc3cn2)cn1] | 3800 |
| 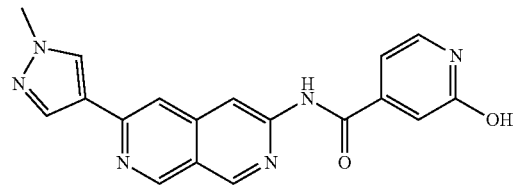 [SMILES: Cn1cc(-c2cc3cc(NC(=O)c4ccnc(O)c4)ncc3cn2)cn1] | 3801 |
| 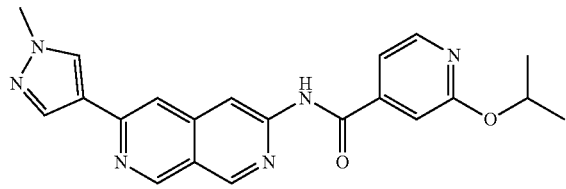 [SMILES: CC(C)Oc1cc(C(=O)Nc2cc3cc(-c4cnn(C)c4)ncc3cn2)ccn1] | 3802 |

TABLE 1-continued
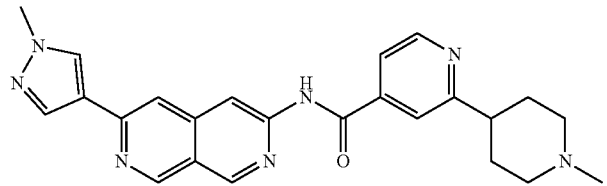 [SMILES: CN1CCC(c2cc(C(=O)Nc3cc4cc(-c5cnn(C)c5)ncc4cn3)ccn2)CC1]
3803
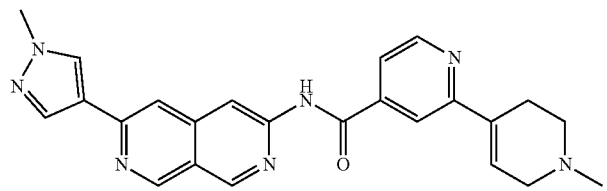
3804
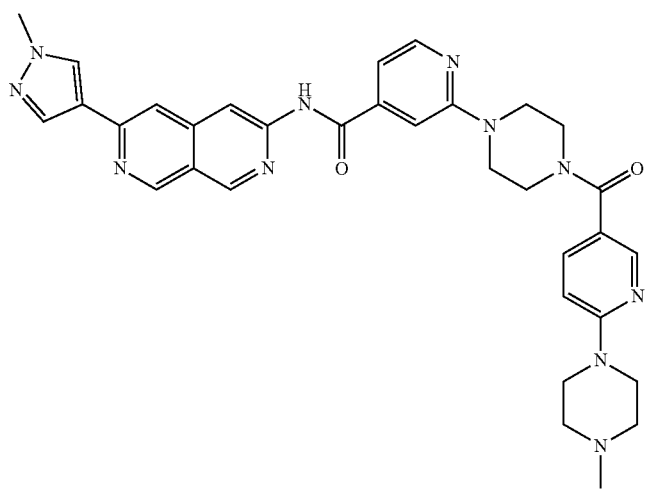 [SMILES: CN1CCN(c2ccc(C(=O)N3CCN(c4cc(C(=O)Nc5cc6cc(-c7cnn(C)c7)ncc6cn5)ccn4)CC3)cn2)CC1]
3805
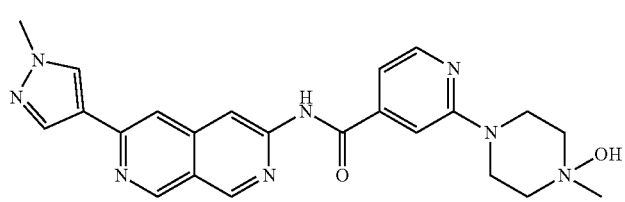
3806
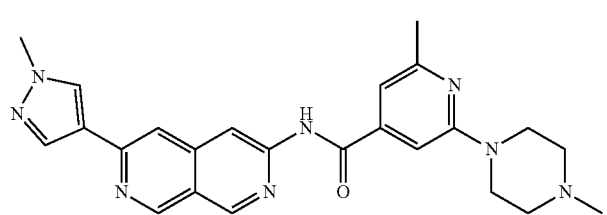
3807
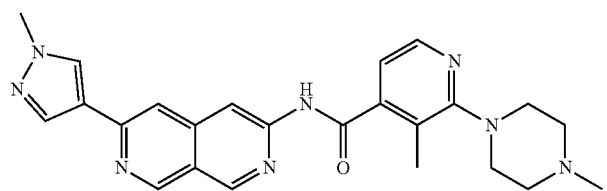 [SMILES: Cc1c(C(=O)Nc2cc3cc(-c4cnn(C)c4)ncc3cn2)ccnc1N1CCN(C)CC1]
3808

TABLE 1-continued
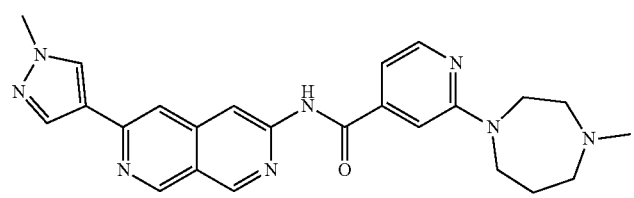 [SMILES: CN1CCCN(c2cc(C(=O)Nc3cc4cc(-c5cnn(C)c5)ncc4cn3)ccn2)CC1]
3809
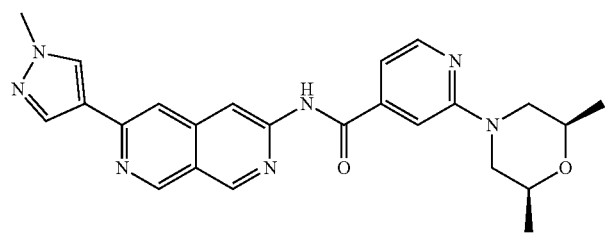 [SMILES: C[C@@H]1CN(c2cc(C(=O)Nc3cc4cc(-c5cnn(C)c5)ncc4cn3)ccn2)C[C@H](C)O1]
3810
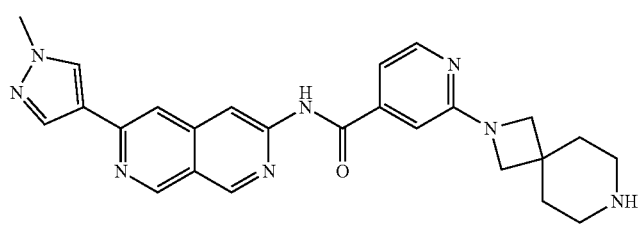 [SMILES: Cn1cc(-c2cc3cc(NC(=O)c4ccnc(N5CC6(CCNCC6)C5)c4)ncc3cn2)cn1]
3811
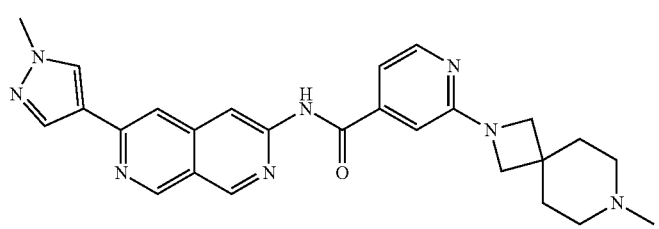 [SMILES: CN1CCC2(CC1)CN(c1cc(C(=O)Nc3cc4cc(-c5cnn(C)c5)ncc4cn3)ccn1)C2]
3812
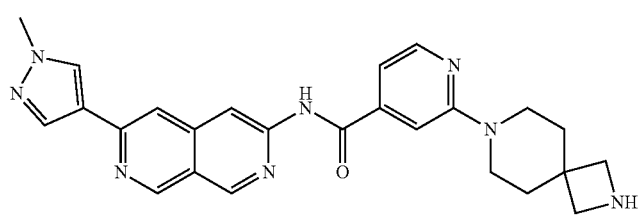 [SMILES: Cn1cc(-c2cc3cc(NC(=O)c4ccnc(N5CCC6(CC5)CNC6)c4)ncc3cn2)cn1]
3813
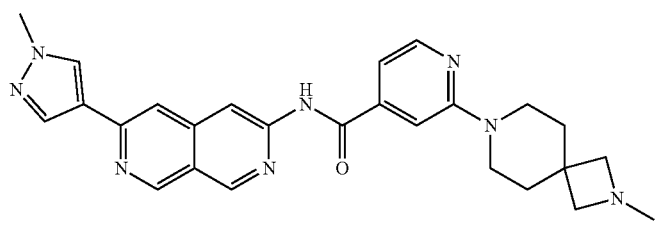 [SMILES: CN1CC2(CCN(c3cc(C(=O)Nc4cc5cc(-c6cnn(C)c6)ncc5cn4)ccn3)CC2)C1]
3814
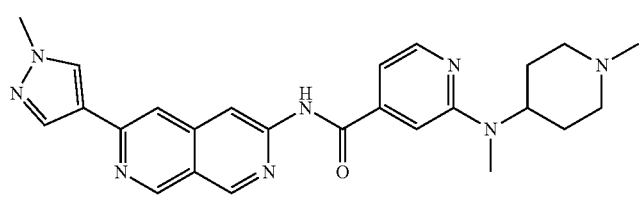 [SMILES: CN1CCC(N(C)c2cc(C(=O)Nc3cc4cc(-c5cnn(C)c5)ncc4cn3)ccn2)CC1]
3815

TABLE 1-continued
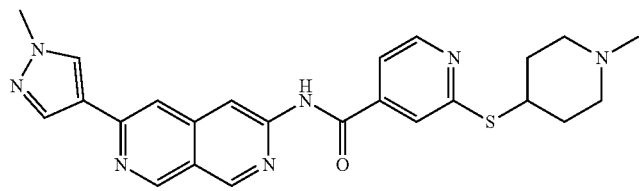 [SMILES: CN1CCC(Sc2cc(C(=O)Nc3cc4cc(-c5cnn(C)c5)ncc4cn3)ccn2)CC1]
3816
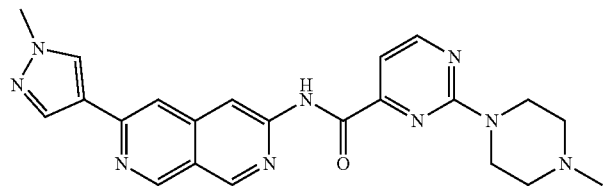
3817
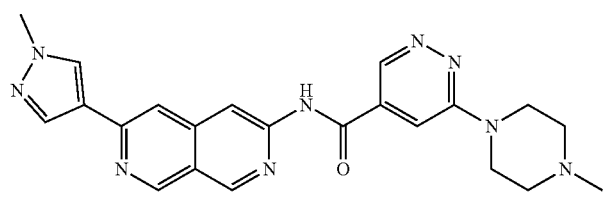
3818
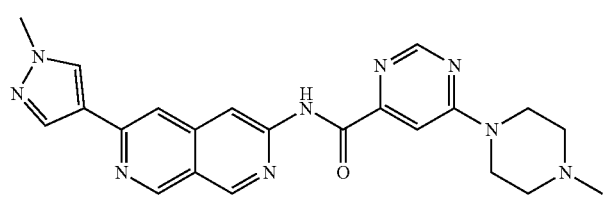 [SMILES: CN1CCN(c2cc(C(=O)Nc3cc4cc(-c5cnn(C)c5)ncc4cn3)ncn2)CC1]
3819
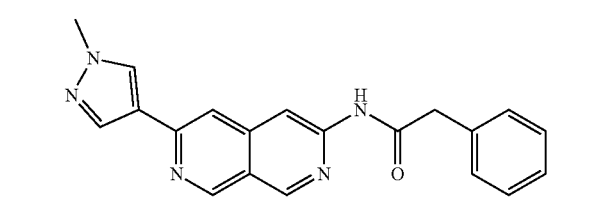 [SMILES: Cn1cc(-c2cc3cc(NC(=O)Cc4ccccc4)ncc3cn2)cn1]
3820
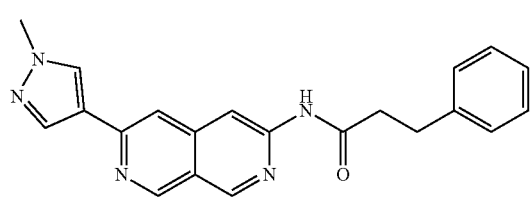 [SMILES: Cn1cc(-c2cc3cc(NC(=O)CCc4ccccc4)ncc3cn2)cn1]
3821
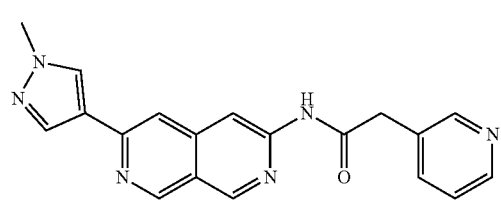 [SMILES: Cn1cc(-c2cc3cc(NC(=O)Cc4cccnc4)ncc3cn2)cn1]
3822
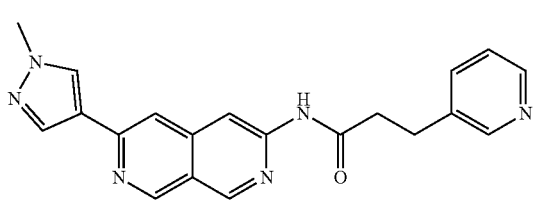 [SMILES: Cn1cc(-c2cc3cc(NC(=O)CCc4cccnc4)ncc3cn2)cn1]
3823

TABLE 1-continued
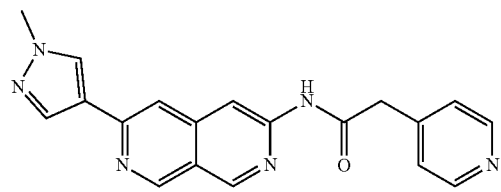 [SMILES: Cn1cc(-c2cc3cc(NC(=O)Cc4ccncc4)ncc3cn2)cn1]
3824
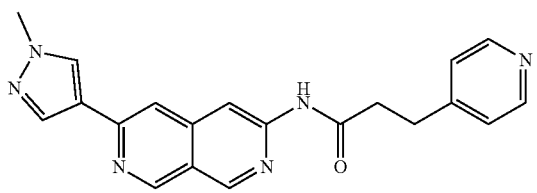 [SMILES: Cn1cc(-c2cc3cc(NC(=O)CCc4ccncc4)ncc3cn2)cn1]
3825
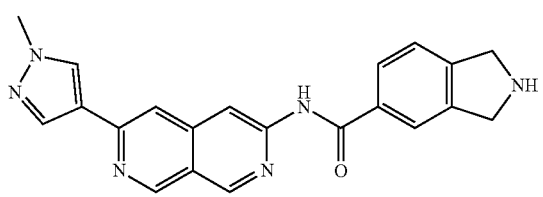 [SMILES: Cn1cc(-c2cc3cc(NC(=O)c4ccc5c(c4)CNC5)ncc3cn2)cn1]
3826
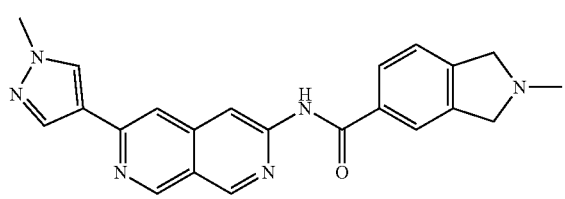 [SMILES: CN1Cc2ccc(C(=O)Nc3cc4cc(-c5cnn(C)c5)ncc4cn3)cc2C1]
3827
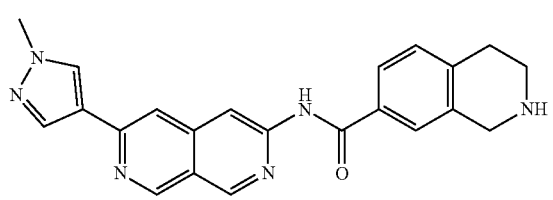 [SMILES: Cn1cc(-c2cc3cc(NC(=O)c4ccc5c(c4)CNCC5)ncc3cn2)cn1]
3828
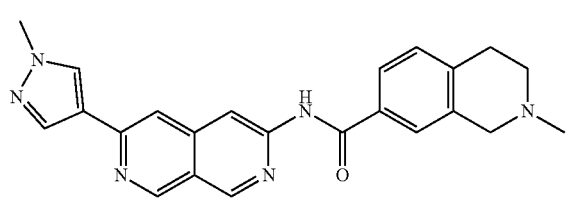 [SMILES: CN1CCc2ccc(C(=O)Nc3cc4cc(-c5cnn(C)c5)ncc4cn3)cc2C1]
3829
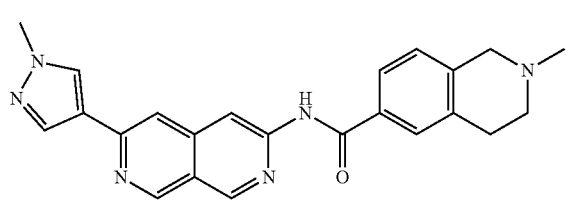 [SMILES: CN1CCc2cc(C(=O)Nc3cc4cc(-c5cnn(C)c5)ncc4cn3)ccc2C1]
3830
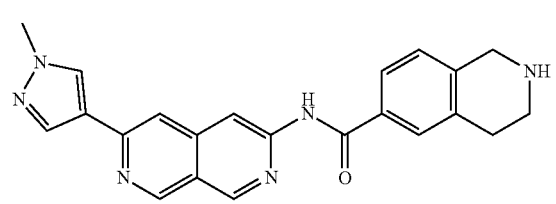 [SMILES: Cn1cc(-c2cc3cc(NC(=O)c4ccc5c(c4)CCNC5)ncc3cn2)cn1]
3831

TABLE 1-continued
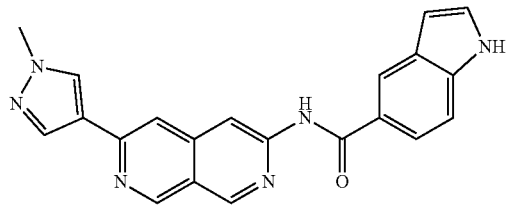 [SMILES: Cn1cc(-c2cc3cc(NC(=O)c4ccc5[nH]ccc5c4)ncc3cn2)cn1] 3832
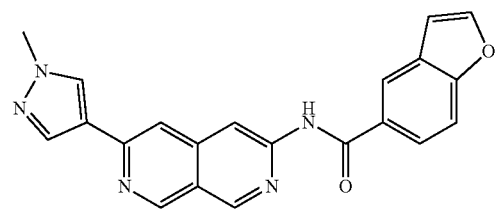 [SMILES: Cn1cc(-c2cc3cc(NC(=O)c4ccc5occc5c4)ncc3cn2)cn1] 3833
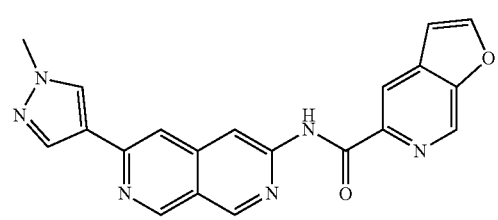 [SMILES: Cn1cc(-c2cc3cc(NC(=O)c4cc5ccoc5cn4)ncc3cn2)cn1] 3834
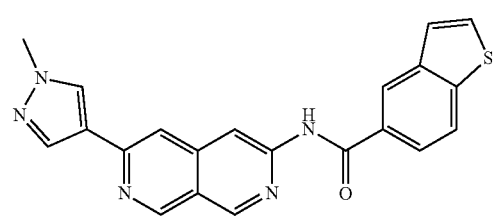 [SMILES: Cn1cc(-c2cc3cc(NC(=O)c4ccc5sccc5c4)ncc3cn2)cn1] 3835
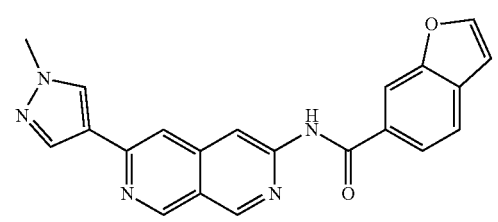 [SMILES: Cn1cc(-c2cc3cc(NC(=O)c4ccc5ccoc5c4)ncc3cn2)cn1] 3836
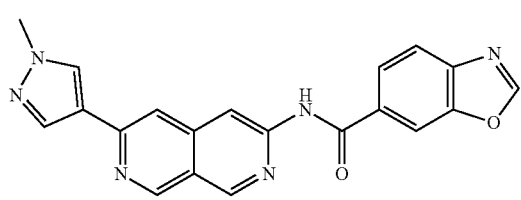 [SMILES: Cn1cc(-c2cc3cc(NC(=O)c4ccc5ncoc5c4)ncc3cn2)cn1] 3837
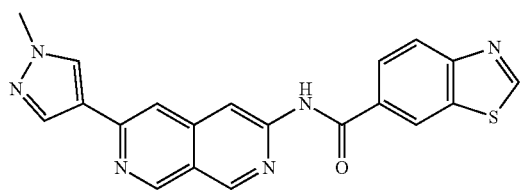 [SMILES: Cn1cc(-c2cc3cc(NC(=O)c4ccc5ncsc5c4)ncc3cn2)cn1] 3838

TABLE 1-continued
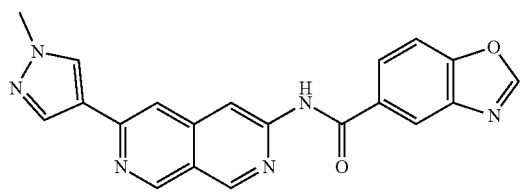 [SMILES: Cn1cc(-c2cc3cc(NC(=O)c4ccc5ocnc5c4)ncc3cn2)cn1] 3839
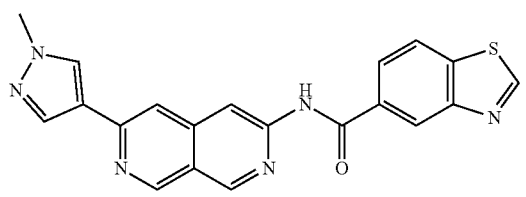 3840
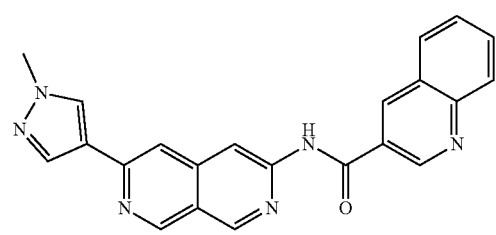 [SMILES: Cn1cc(-c2cc3cc(NC(=O)c4cnc5ccccc5c4)ncc3cn2)cn1] 3841
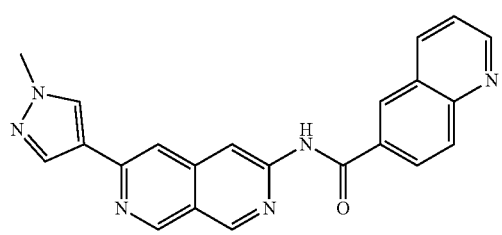 3842
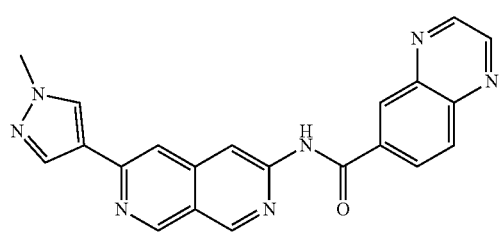 [SMILES: Cn1cc(-c2cc3cc(NC(=O)c4ccc5nccnc5c4)ncc3cn2)cn1] 3843
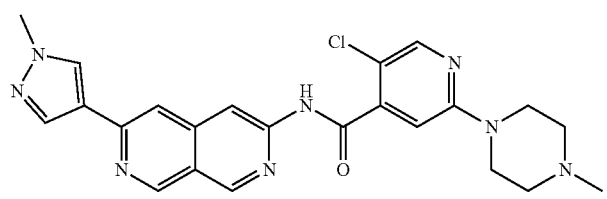 [SMILES: CN1CCN(c2cc(C(=O)Nc3cc4cc(-c5cnn(C)c5)ncc4cn3)c(Cl)cn2)CC1] 3844
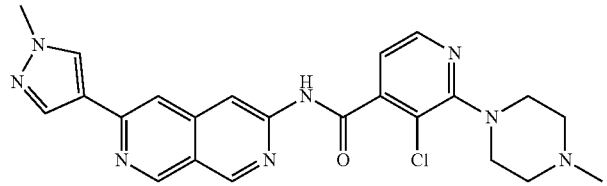 [SMILES: CN1CCN(c2nccc(C(=O)Nc3cc4cc(-c5cnn(C)c5)ncc4cn3)c2F)CC1] 3845

TABLE 1-continued

| | |
|---|---|
| 3846 | |
| 3847 | |
| 3848 | |
| 3849 | |
| 3850 | |
| 3851 | |
| 3852 | |
| 3853 | |

TABLE 1-continued
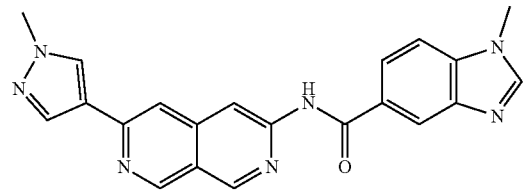 [SMILES: Cn1cc(-c2cc3cc(NC(=O)c4ccc5c(c4)ncn5C)ncc3cn2)cn1]
3854
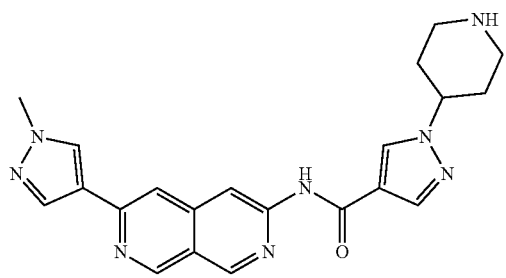 [SMILES: Cn1cc(-c2cc3cc(NC(=O)c4cnn(C5CCNCC5)c4)ncc3cn2)cn1]
3855
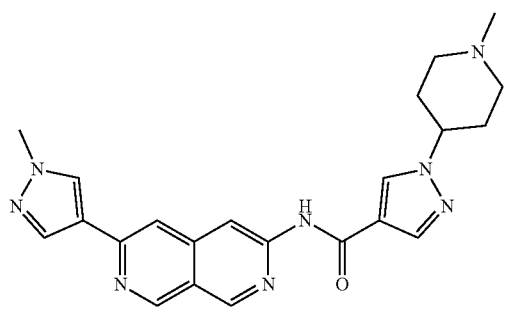
3856
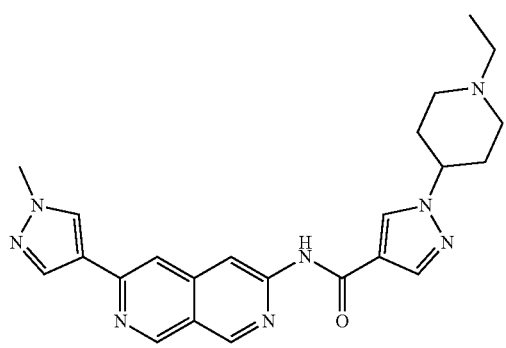 [SMILES: CCN1CCC(n2cc(C(=O)Nc3cc4cc(-c5cnn(C)c5)ncc4cn3)cn2)CC1]
3857
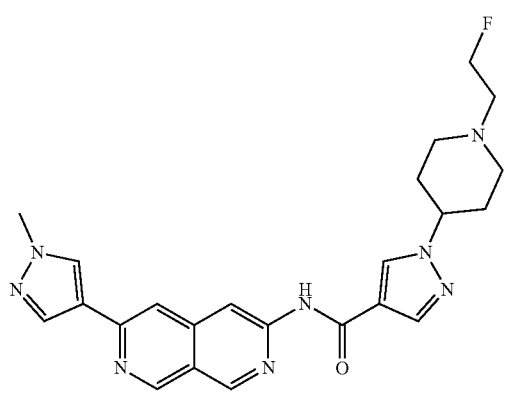 [SMILES: Cn1cc(-c2cc3cc(NC(=O)c4cnn(C5CCN(CCF)CC5)c4)ncc3cn2)cn1]
3858

TABLE 1-continued
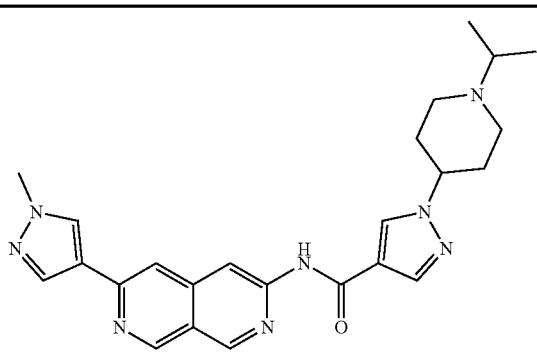
3859
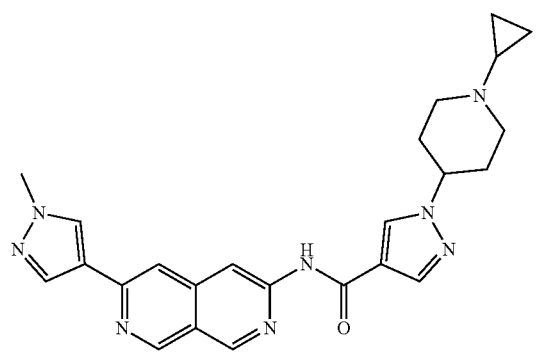 [SMILES: Cn1cc(-c2cc3cc(NC(=O)c4cnn(C5CCN(C6CC6)CC5)c4)ncc3cn2)cn1]
3860
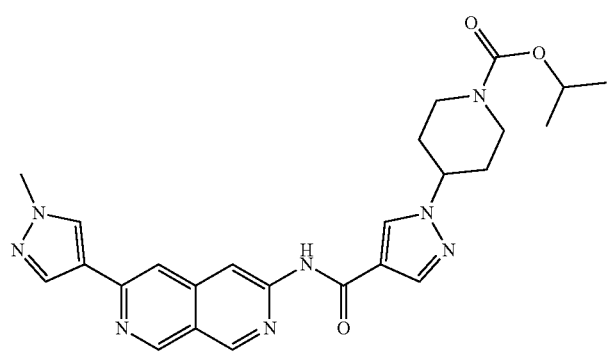 [SMILES: CC(C)OC(=O)N1CCC(n2cc(C(=O)Nc3cc4cc(-c5cnn(C)c5)ncc4cn3)cn2)CC1]
3861
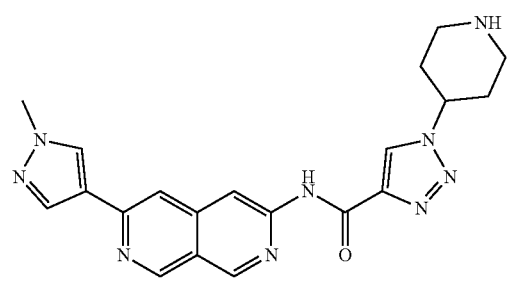
3862
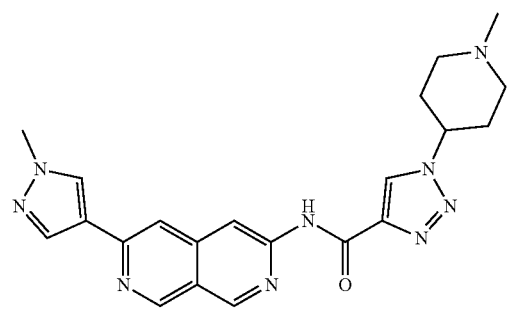 [SMILES: CN1CCC(n2cc(C(=O)Nc3cc4cc(-c5cnn(C)c5)ncc4cn3)nn2)CC1]
3863

TABLE 1-continued
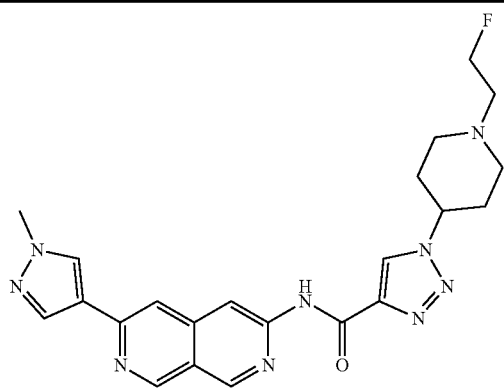
3864
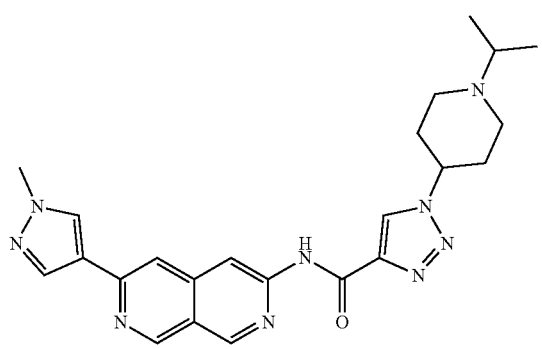 [SMILES: CC(C)N1CCC(n2cc(C(=O)Nc3cc4cc(-c5cnn(C)c5)ncc4cn3)nn2)CC1]
3865
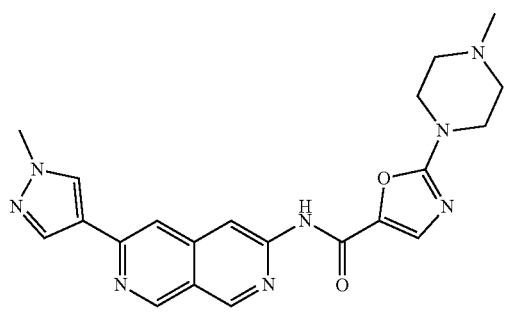
3866
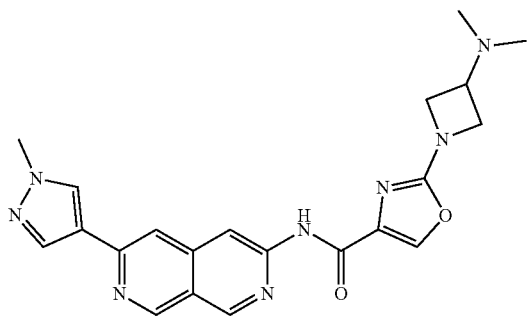 [SMILES: CN(C)C1CN(c2nc(C(=O)Nc3cc4cc(-c5cnn(C)c5)ncc4cn3)co2)C1]
3867
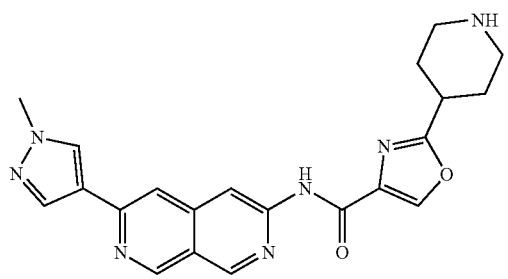 [SMILES: Cn1cc(-c2cc3cc(NC(=O)c4coc(C5CCNCC5)n4)ncc3cn2)cn1]
3868

TABLE 1-continued
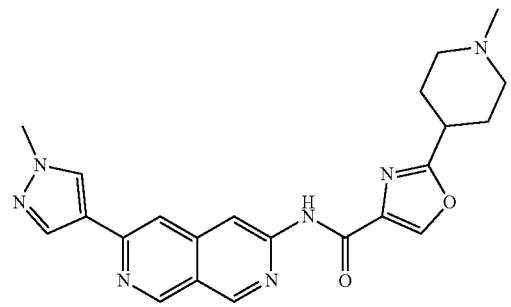
3869
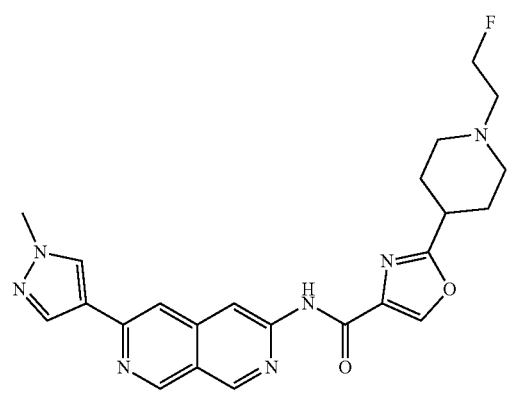 [SMILES: Cn1cc(-c2cc3cc(NC(=O)c4coc(C5CCN(CCF)CC5)n4)ncc3cn2)cn1]
3870
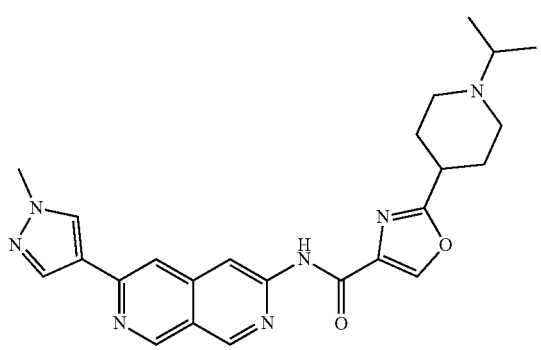 [SMILES: CC(C)N1CCC(c2nc(C(=O)Nc3cc4cc(-c5cnn(C)c5)ncc4cn3)co2)CC1]
3871
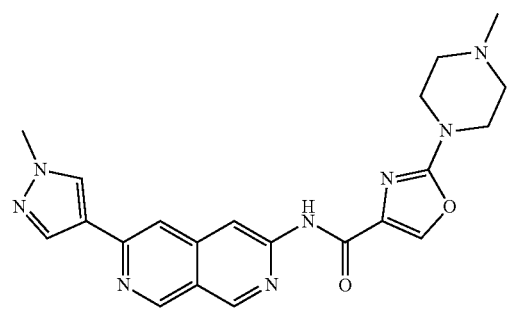
3872

TABLE 1-continued
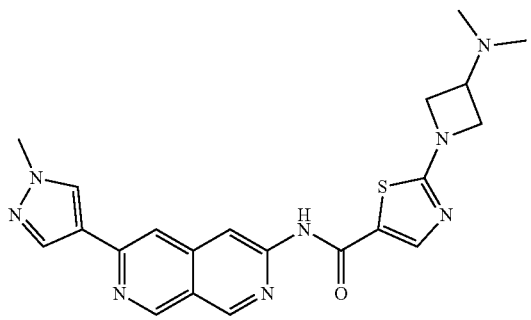 [SMILES: CN(C)C1CN(c2ncc(C(=O)Nc3cc4cc(-c5cnn(C)c5)ncc4cn3)s2)C1]
3873
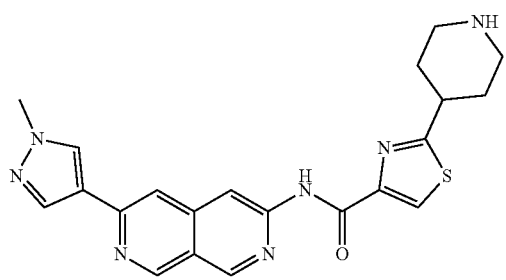 [SMILES: Cn1cc(-c2cc3cc(NC(=O)c4csc(C5CCNCC5)n4)ncc3cn2)cn1]
3874
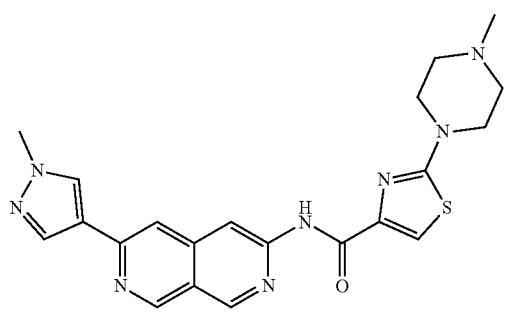 [SMILES: CN1CCN(c2nc(C(=O)Nc3cc4cc(-c5cnn(C)c5)ncc4cn3)cs2)CC1]
3875
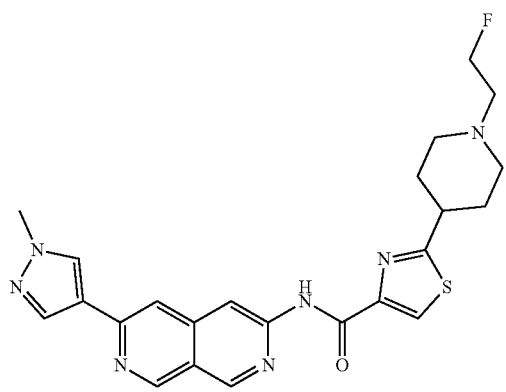 [SMILES: Cn1cc(-c2cc3cc(NC(=O)c4csc(C5CCN(CCF)CC5)n4)ncc3cn2)cn1]
3876
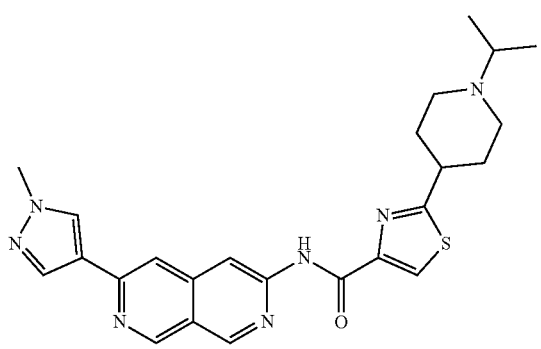 [SMILES: CC(C)N1CCC(c2nc(C(=O)Nc3cc4cc(-c5cnn(C)c5)ncc4cn3)cs2)CC1]
3877

TABLE 1-continued
| | |
|---|---|
| 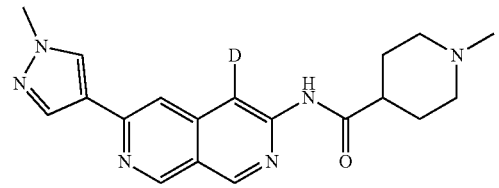 [SMILES: [2H]c1c(NC(=O)C2CCN(C)CC2)ncc2cnc(-c3cnn(C)c3)cc12] | 3878 |
| 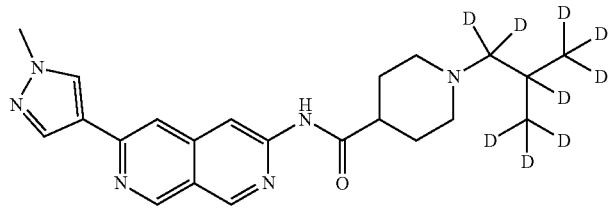 [SMILES: [2H]C([2H])([2H])C([2H])(C([2H])([2H])[2H])C([2H])([2H])N1CCC(C(=O)Nc2cc3cc(-c4cnn(C)c4)ncc3cn2)CC1] | 3879 |
| 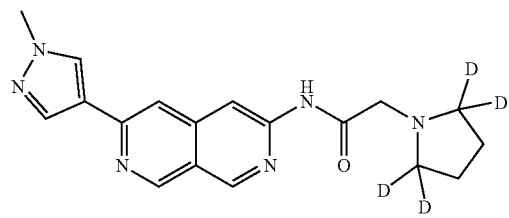 [SMILES: [2H]C1([2H])CCC([2H])([2H])N1CC(=O)Nc1cc2cc(-c3cnn(C)c3)ncc2cn1] | 3880 |
| 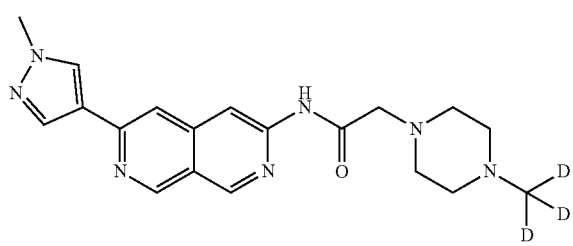 [SMILES: [2H]C([2H])([2H])N1CCN(CC(=O)Nc2cc3cc(-c4cnn(C)c4)ncc3cn2)CC1] | 3881 |
| 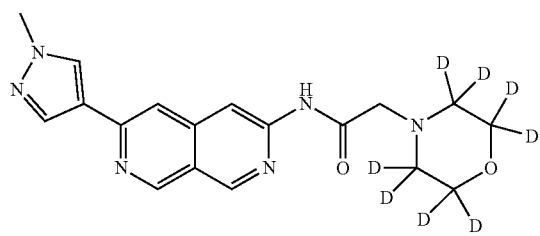 [SMILES: [2H]C1([2H])OC([2H])([2H])C([2H])([2H])N(CC(=O)Nc2cc3cc(-c4cnn(C)c4)ncc3cn2)C1([2H])[2H]] | 3882 |
| 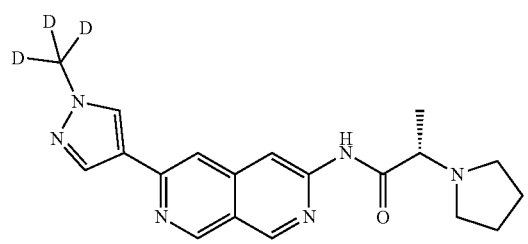 | 3883 |
| 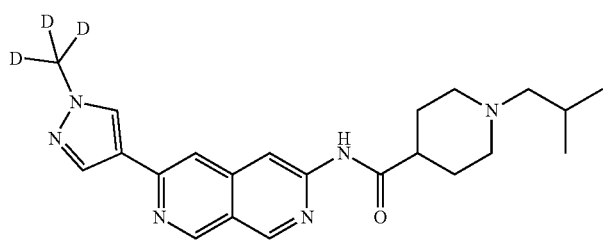 | 3884 |

TABLE 1-continued
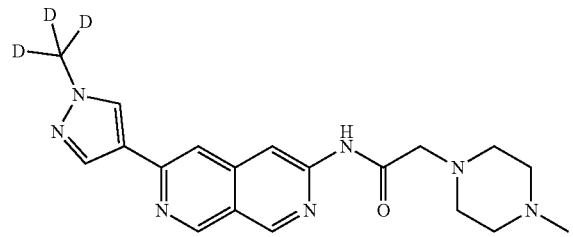 [SMILES: [2H]C([2H])([2H])n1cc(-c2cc3cc(NC(=O)CN4CCN(C)CC4)ncc3cn2)cn1]  3885
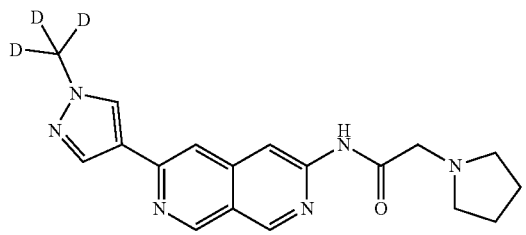 [SMILES: [2H]C([2H])([2H])n1cc(-c2cc3cc(NC(=O)CN4CCCC4)ncc3cn2)cn1]  3886
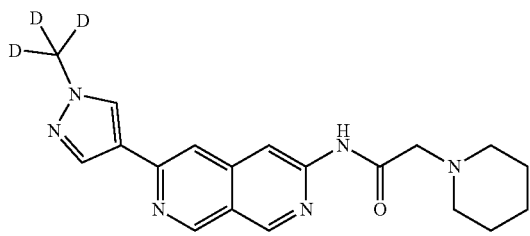 [SMILES: [2H]C([2H])([2H])n1cc(-c2cc3cc(NC(=O)CN4CCCCC4)ncc3cn2)cn1]  3887
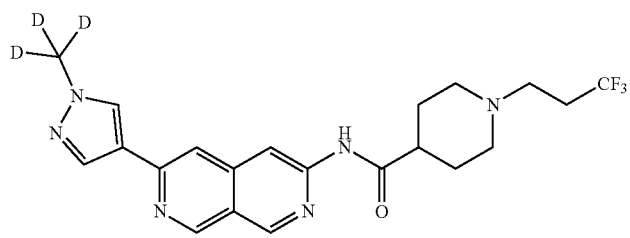 [SMILES: [2H]C([2H])([2H])n1cc(-c2cc3cc(NC(=O)C4CCN(CCC(F)(F)F)CC4)ncc3cn2)cn1]  3888
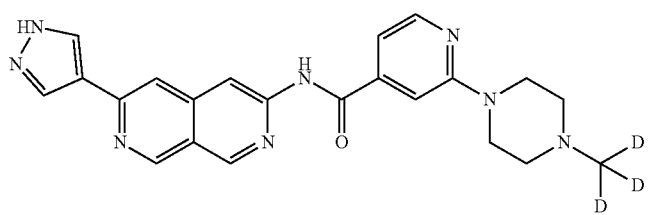  3889
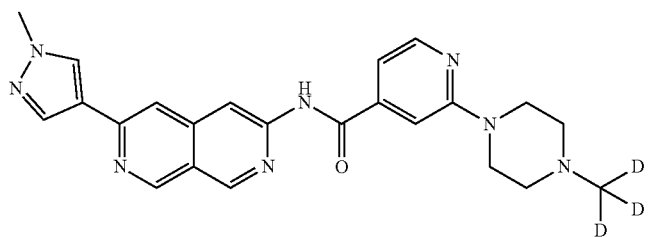 [SMILES: [2H]C([2H])([2H])N1CCN(c2cc(C(=O)Nc3cc4cc(-c5cnn(C)c5)ncc4cn3)ccn2)CC1]  3890

TABLE 1-continued
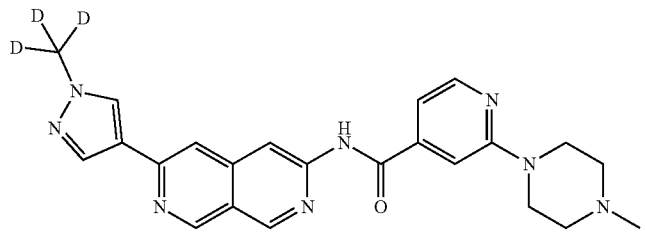 [SMILES: [2H]C([2H])([2H])n1cc(-c2cc3cc(NC(=O)c4ccnc(N5CCN(C)CC5)c4)ncc3cn2)cn1]
3891
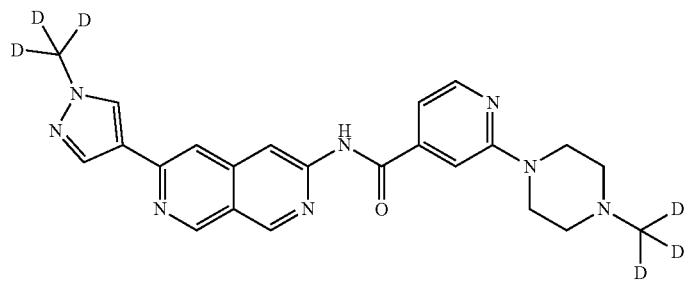 [SMILES: [2H]C([2H])([2H])N1CCN(c2cc(C(=O)Nc3cc4cc(-c5cnn(C([2H])([2H])[2H])c5)ncc4cn3)ccn2)CC1]
3892
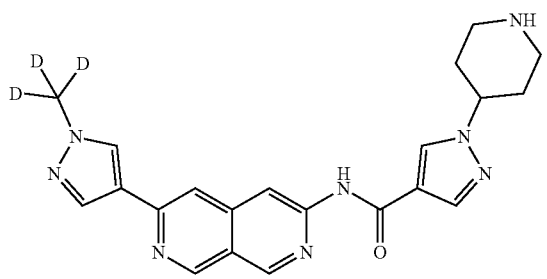 [SMILES: [2H]C([2H])([2H])n1cc(-c2cc3cc(NC(=O)c4cnn(C5CCNCC5)c4)ncc3cn2)cn1]
3893
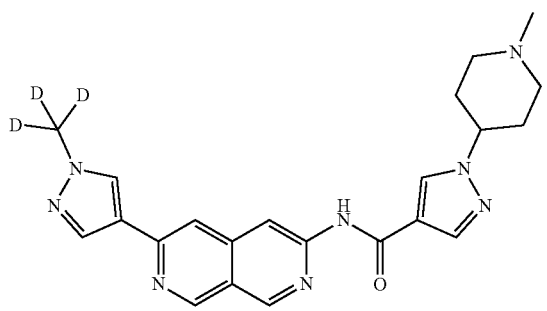 [SMILES: [2H]C([2H])([2H])n1cc(-c2cc3cc(NC(=O)c4cnn(C5CCN(C)CC5)c4)ncc3cn2)cn1]
3894
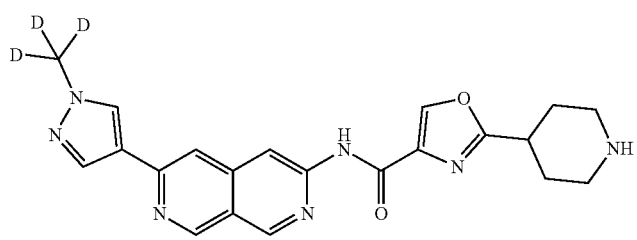 [SMILES: [2H]C([2H])([2H])n1cc(-c2cc3cc(NC(=O)c4coc(C5CCNCC5)n4)ncc3cn2)cn1]
3895
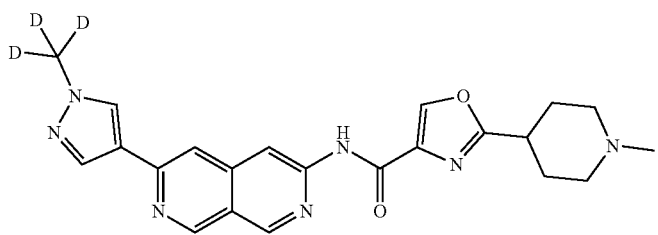 [SMILES: [2H]C([2H])([2H])n1cc(-c2cc3cc(NC(=O)c4coc(C5CCN(C)CC5)n4)ncc3cn2)cn1]
3896

TABLE 1-continued
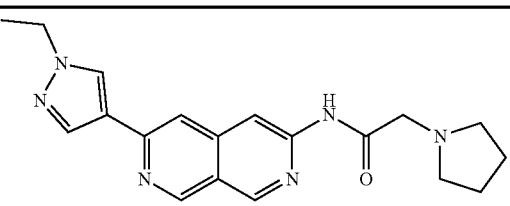 3897
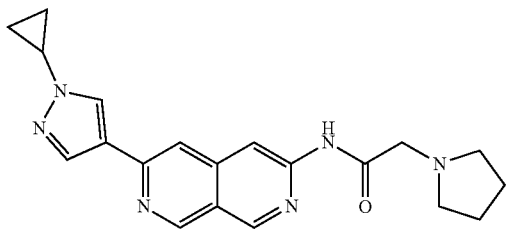 [SMILES: O=C(CN1CCCC1)Nc1cc2cc(-c3cnn(C4CC4)c3)ncc2cn1] 3898
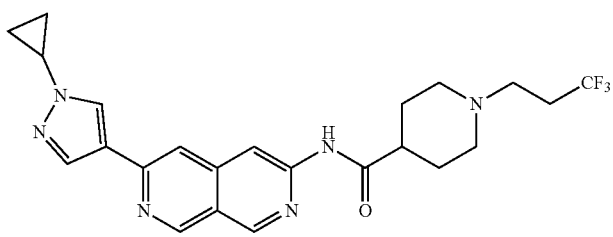 [SMILES: O=C(Nc1cc2cc(-c3cnn(C4CC4)c3)ncc2cn1)C1CCN(CCC(F)(F)F)CC1] 3899
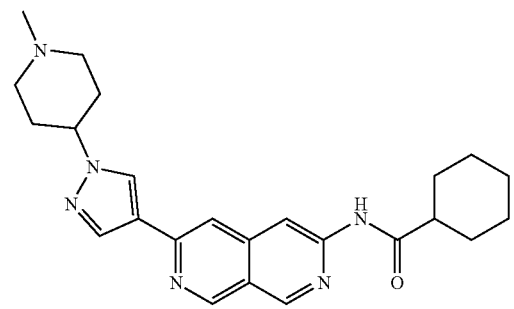 [SMILES: CN1CCC(n2cc(-c3cc4cc(NC(=O)C5CCCCC5)ncc4cn3)cn2)CC1] 3900
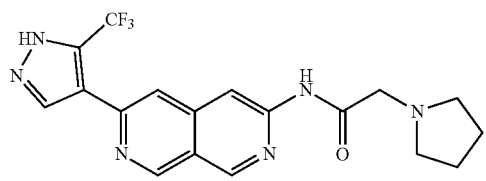 3901
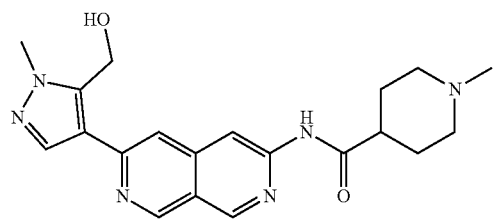 [SMILES: CN1CCC(C(=O)Nc2cc3cc(-c4cnn(C)c4CO)ncc3cn2)CC1] 3902
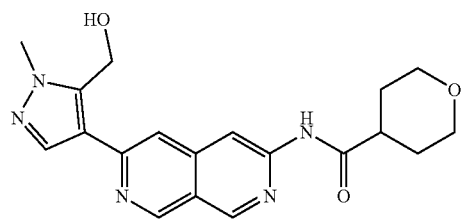 [SMILES: Cn1ncc(-c2cc3cc(NC(=O)C4CCOCC4)ncc3cn2)c1CO] 3903

TABLE 1-continued
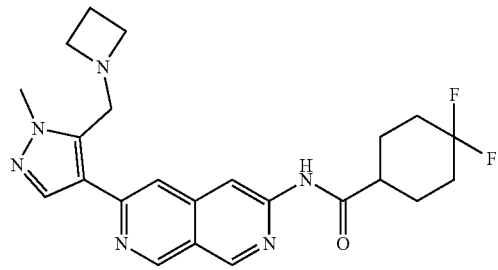 [SMILES: Cn1ncc(-c2cc3cc(NC(=O)C4CCC(F)(F)CC4)ncc3cn2)c1CN1CCC1]
3904
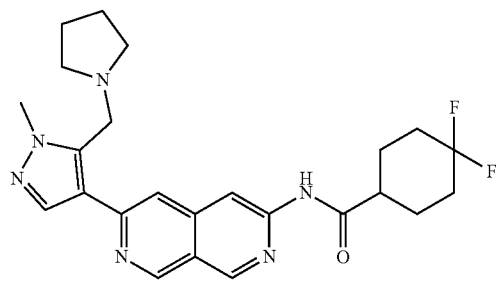 [SMILES: Cn1ncc(-c2cc3cc(NC(=O)C4CCC(F)(F)CC4)ncc3cn2)c1CN1CCCC1]
3905
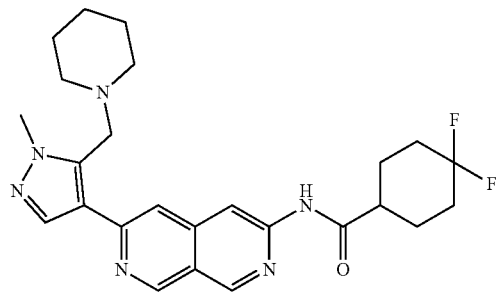 [SMILES: Cn1ncc(-c2cc3cc(NC(=O)C4CCC(F)(F)CC4)ncc3cn2)c1CN1CCCCC1]
3906
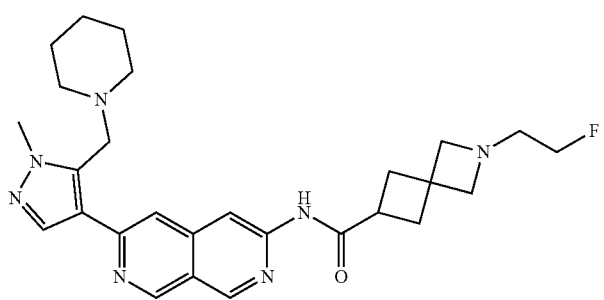 [SMILES: Cn1ncc(-c2cc3cc(NC(=O)C4CC5(C4)CN(CCF)C5)ncc3cn2)c1CN1CCCCC1]
3907
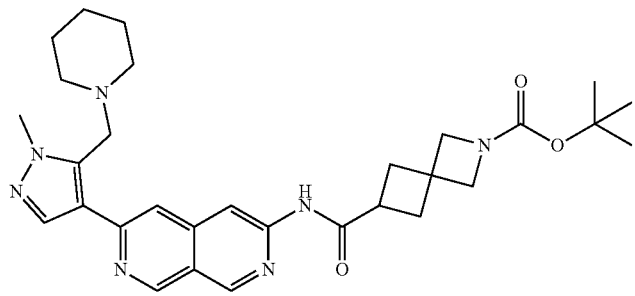 [SMILES: Cn1ncc(-c2cc3cc(NC(=O)C4CC5(C4)CN(C(=O)OC(C)(C)C)C5)ncc3cn2)c1CN1CCCCC1]
3908

TABLE 1-continued
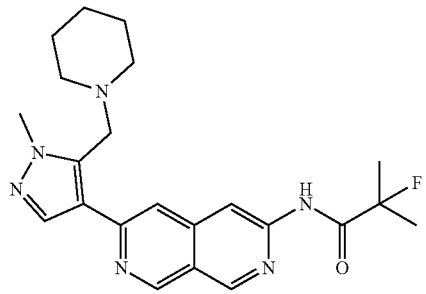 [SMILES: Cn1ncc(-c2cc3cc(NC(=O)C(C)(C)F)ncc3cn2)c1CN1CCCCC1] 3909
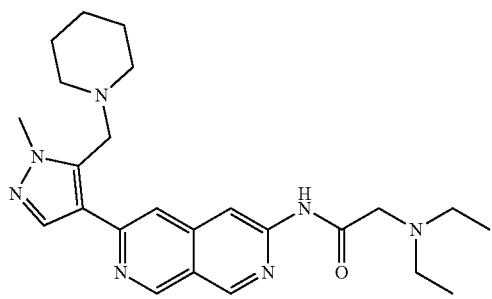 [SMILES: CCN(CC)CC(=O)Nc1cc2cc(-c3cnn(C)c3CN3CCCCC3)ncc2cn1] 3910
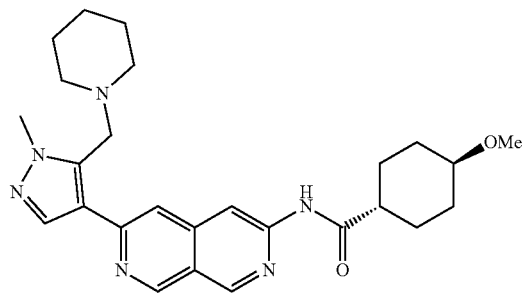 [SMILES: CO[C@H]1CC[C@H](C(=O)Nc2cc3cc(-c4cnn(C)c4CN4CCCCC4)ncc3cn2)CC1] 3911
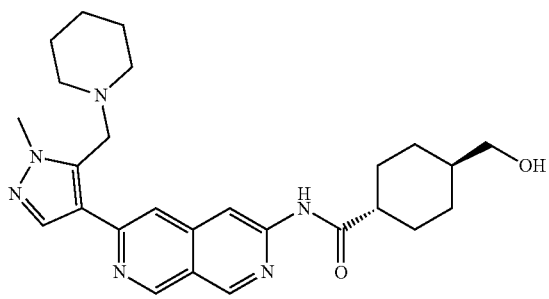 [SMILES: Cn1ncc(-c2cc3cc(NC(=O)[C@H]4CC[C@H](CO)CC4)ncc3cn2)c1CN1CCCCC1] 3912
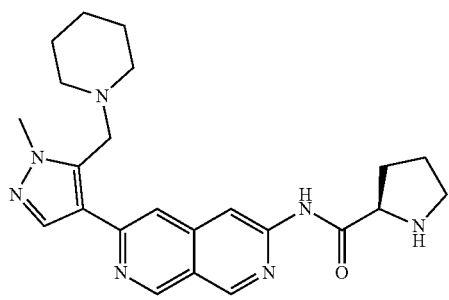 [SMILES: Cn1ncc(-c2cc3cc(NC(=O)[C@H]4CCCN4)ncc3cn2)c1CN1CCCCC1] 3913

TABLE 1-continued
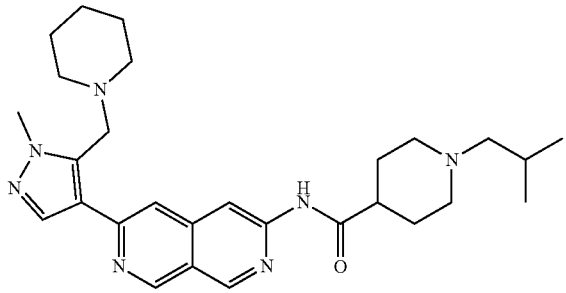 [SMILES: CC(C)CN1CCC(C(=O)Nc2cc3cc(-c4cnn(C)c4CN4CCCCC4)ncc3cn2)CC1]
3914
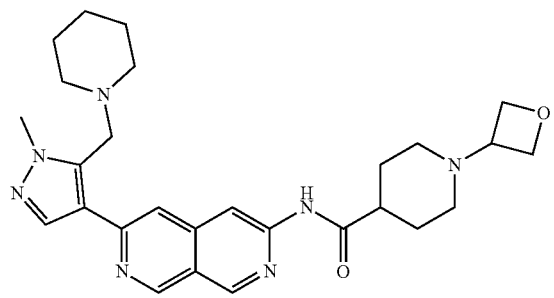 [SMILES: Cn1ncc(-c2cc3cc(NC(=O)C4CCN(C5COC5)CC4)ncc3cn2)c1CN1CCCCC1]
3915
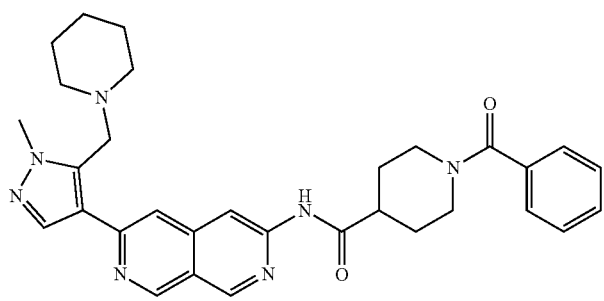 [SMILES: Cn1ncc(-c2cc3cc(NC(=O)C4CCN(C(=O)c5ccccc5)CC4)ncc3cn2)c1CN1CCCCC1]
3916
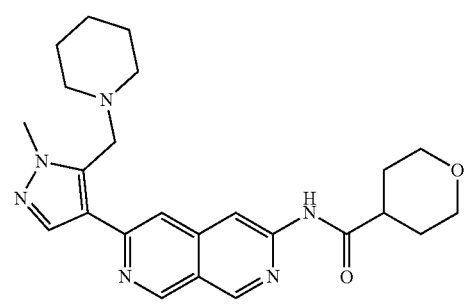 [SMILES: Cn1ncc(-c2cc3cc(NC(=O)C4CCOCC4)ncc3cn2)c1CN1CCCCC1]
3917
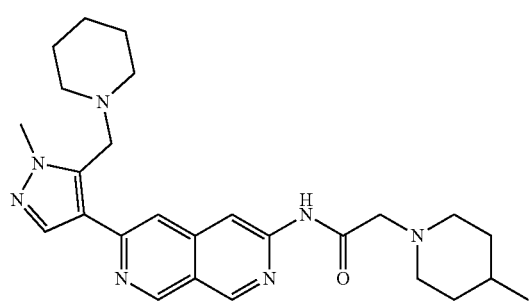 [SMILES: CC1CCN(CC(=O)Nc2cc3cc(-c4cnn(C)c4CN4CCCCC4)ncc3cn2)CC1]
3918

TABLE 1-continued
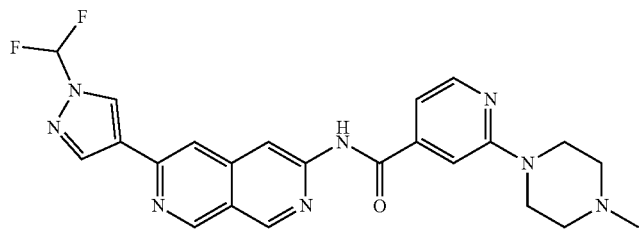 [SMILES: CN1CCN(c2cc(C(=O)Nc3cc4cc(-c5cnn(C(F)F)c5)ncc4cn3)ccn2)CC1]
3919
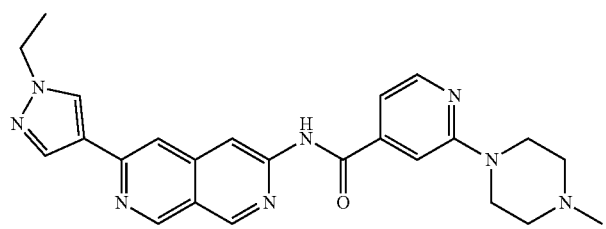 [SMILES: CCn1cc(-c2cc3cc(NC(=O)c4ccnc(N5CCN(C)CC5)c4)ncc3cn2)cn1]
3920
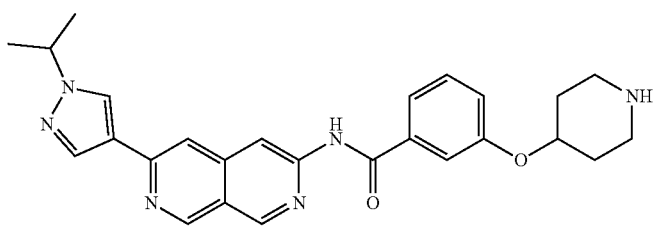 [SMILES: CC(C)n1cc(-c2cc3cc(NC(=O)c4cccc(OC5CCNCC5)c4)ncc3cn2)cn1]
3921
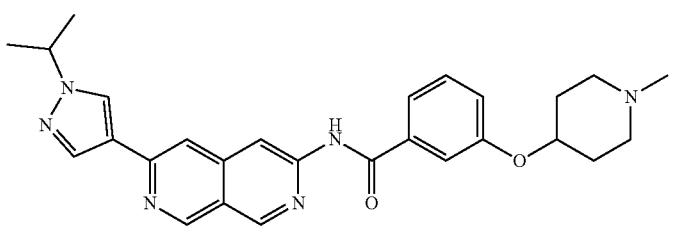 [SMILES: CC(C)n1cc(-c2cc3cc(NC(=O)c4cccc(OC5CCN(C)CC5)c4)ncc3cn2)cn1]
3922
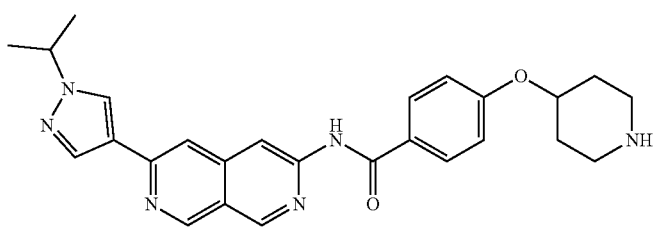 [SMILES: CC(C)n1cc(-c2cc3cc(NC(=O)c4ccc(OC5CCNCC5)cc4)ncc3cn2)cn1]
3923
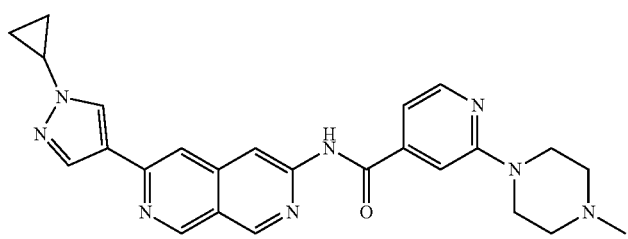 [SMILES: CN1CCN(c2cc(C(=O)Nc3cc4cc(-c5cnn(C6CC6)c5)ncc4cn3)ccn2)CC1]
3924

TABLE 1-continued
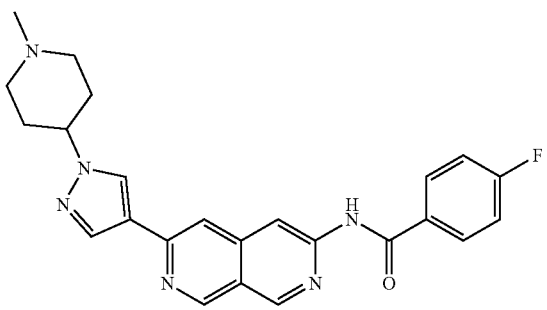 [SMILES: CN1CCC(n2cc(-c3cc4cc(NC(=O)c5ccc(F)cc5)ncc4cn3)cn2)CC1]
3925
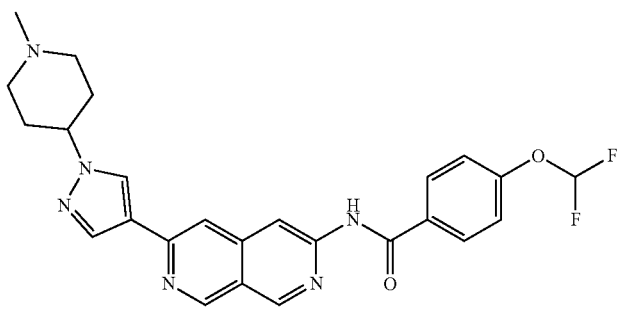 [SMILES: CN1CCC(n2cc(-c3cc4cc(NC(=O)c5ccc(OC(F)F)cc5)ncc4cn3)cn2)CC1]
3926
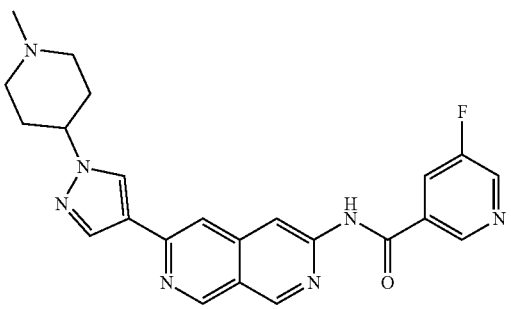 [SMILES: CN1CCC(n2cc(-c3cc4cc(NC(=O)c5cncc(F)c5)ncc4cn3)cn2)CC1]
3927
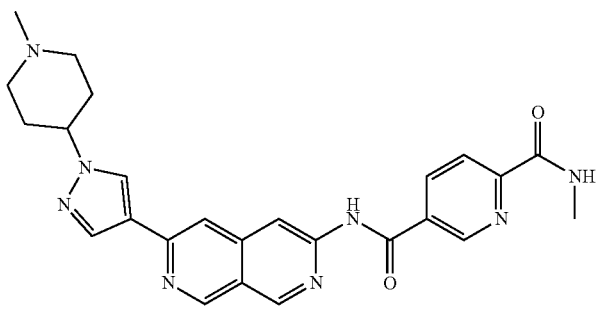 [SMILES: CNC(=O)c1ccc(C(=O)Nc2cc3cc(-c4cnn(C5CCN(C)CC5)c4)ncc3cn2)cn1]
3928
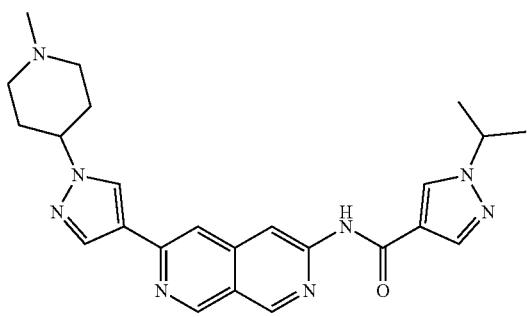 [SMILES: CC(C)n1cc(C(=O)Nc2cc3cc(-c4cnn(C5CCN(C)CC5)c4)ncc3cn2)cn1]
3929

TABLE 1-continued
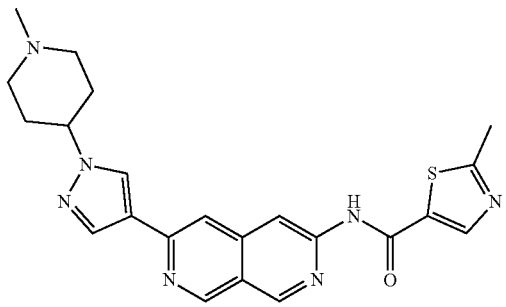 [SMILES: Cc1ncc(C(=O)Nc2cc3cc(-c4cnn(C5CCN(C)CC5)c4)ncc3cn2)s1]
3930
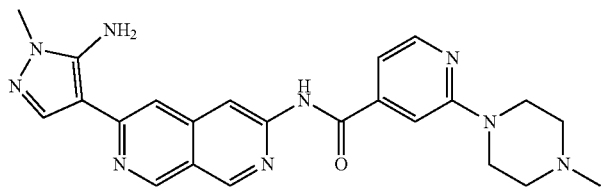 [SMILES: CN1CCN(c2cc(C(=O)Nc3cc4cc(-c5cnn(C)c5N)ncc4cn3)ccn2)CC1]
3931
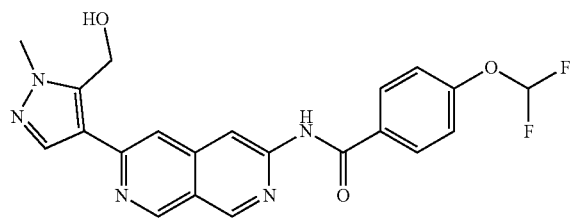 [SMILES: Cn1ncc(-c2cc3cc(NC(=O)c4ccc(OC(F)F)cc4)ncc3cn2)c1CO]
3932
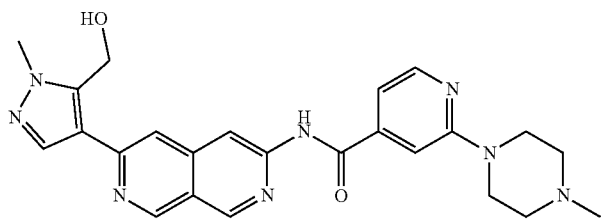
3933
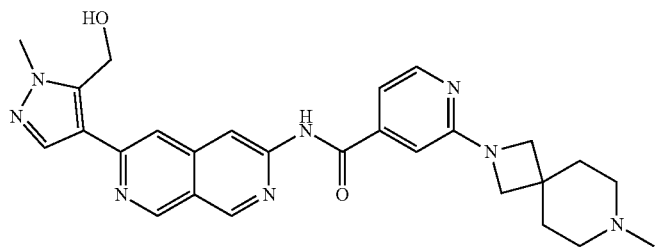 [SMILES: CN1CCC2(CC1)CN(c1cc(C(=O)Nc3cc4cc(-c5cnn(C)c5CO)ncc4cn3)ccn1)C2]
3934
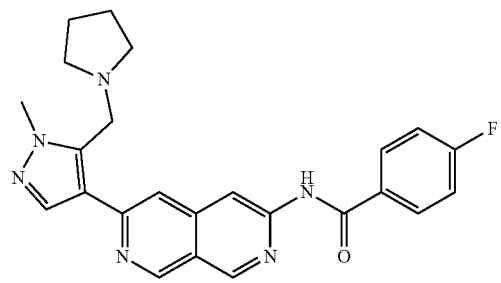 [SMILES: Cn1ncc(-c2cc3cc(NC(=O)c4ccc(F)cc4)ncc3cn2)c1CN1CCCC1]
3935

TABLE 1-continued
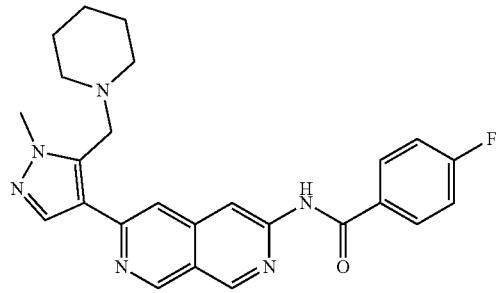 [SMILES: Cn1ncc(-c2cc3cc(NC(=O)c4ccc(F)cc4)ncc3cn2)c1CN1CCCCC1]
3936
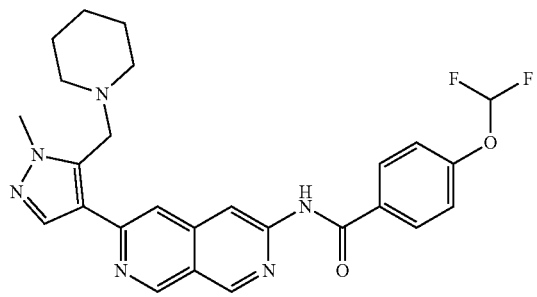 [SMILES: Cn1ncc(-c2cc3cc(NC(=O)c4ccc(OC(F)F)cc4)ncc3cn2)c1CN1CCCCC1]
3937
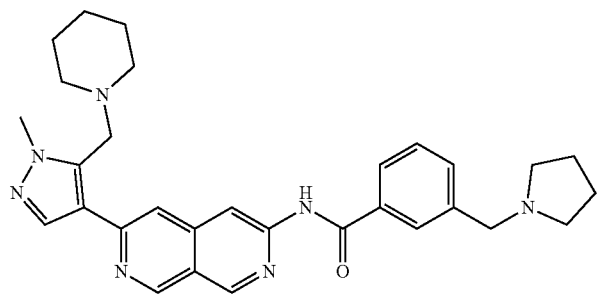 [SMILES: Cn1ncc(-c2cc3cc(NC(=O)c4cccc(CN5CCCC5)c4)ncc3cn2)c1CN1CCCCC1]
3938
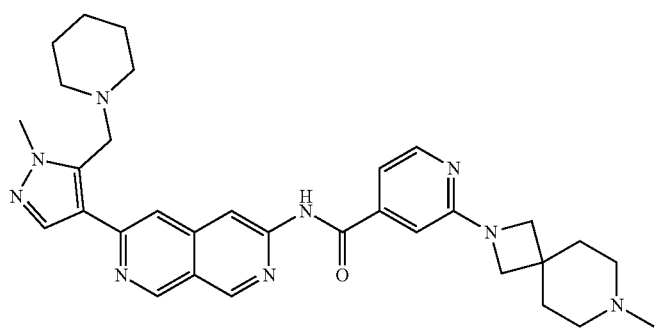 [SMILES: CN1CCC2(CC1)CN(c1cc(C(=O)Nc3cc4cc(-c5cnn(C)c5CN5CCCCC5)ncc4cn3)ccn1)C2]
3939
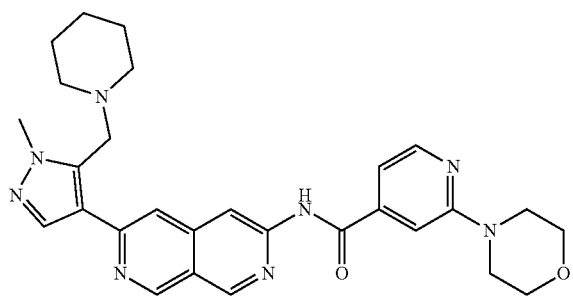 [SMILES: Cn1ncc(-c2cc3cc(NC(=O)c4ccnc(N5CCOCC5)c4)ncc3cn2)c1CN1CCCCC1]
3940

TABLE 1-continued
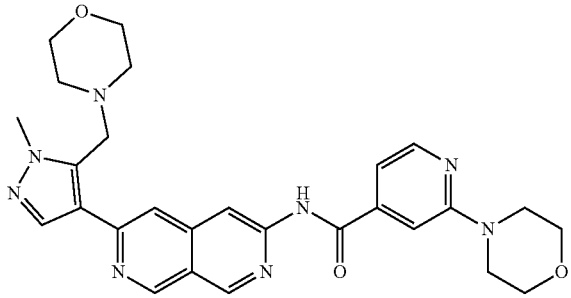 [SMILES: Cn1ncc(-c2cc3cc(NC(=O)c4ccnc(N5CCOCC5)c4)ncc3cn2)c1CN1CCOCC1]
3941
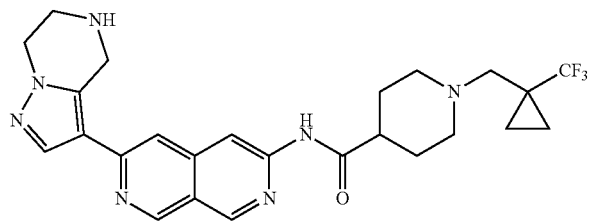 [SMILES: O=C(Nc1cc2cc(-c3cnn4c3CNCC4)ncc2cn1)C1CCN(CC2(C(F)(F)F)CC2)CC1]
3942
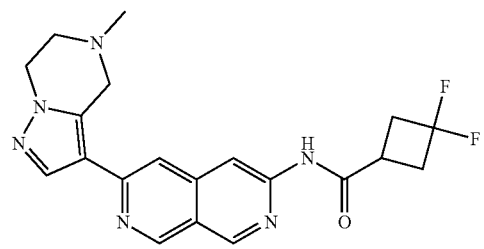 [SMILES: CN1CCn2ncc(-c3cc4cc(NC(=O)C5CC(F)(F)C5)ncc4cn3)c2C1]
3943
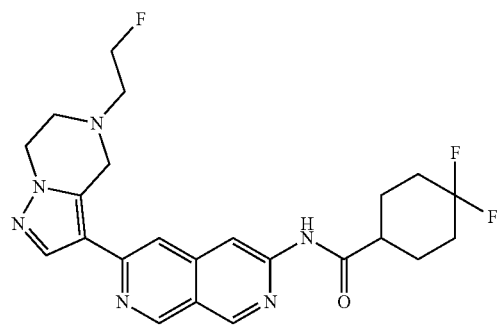 [SMILES: O=C(Nc1cc2cc(-c3cnn4c3CN(CCF)CC4)ncc2cn1)C1CCC(F)(F)CC1]
3944
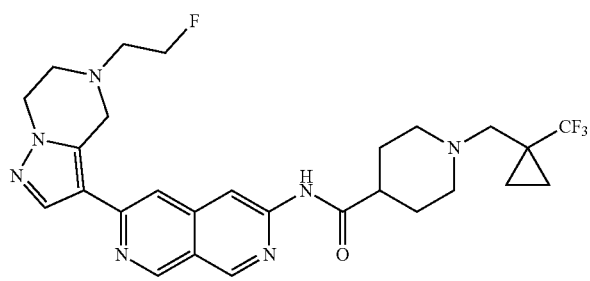 [SMILES: O=C(Nc1cc2cc(-c3cnn4c3CN(CCF)CC4)ncc2cn1)C1CCN(CC2(C(F)(F)F)CC2)CC1]
3945

TABLE 1-continued
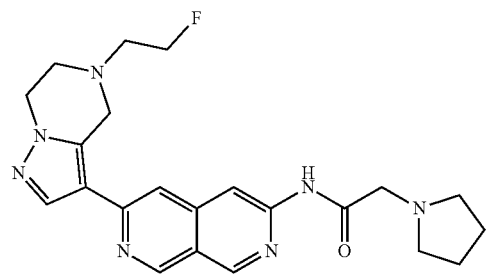 [SMILES: O=C(CN1CCCC1)Nc1cc2cc(-c3cnn4c3CN(CCF)CC4)ncc2cn1] 3946
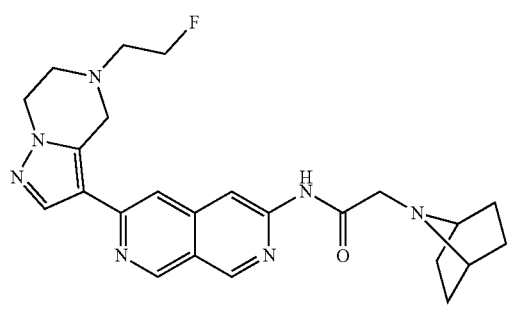 [SMILES: O=C(CN1C2CCC1CC2)Nc1cc2cc(-c3cnn4c3CN(CCF)CC4)ncc2cn1] 3947
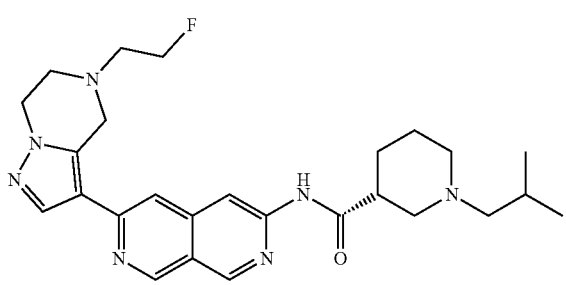 3948
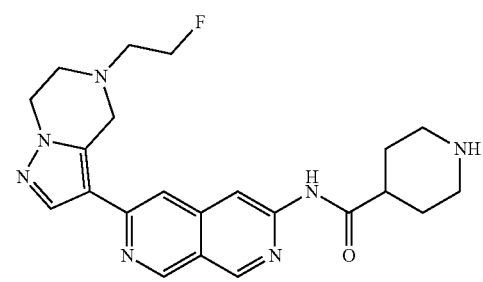 [SMILES: O=C(Nc1cc2cc(-c3cnn4c3CN(CCF)CC4)ncc2cn1)C1CCNCC1] 3949
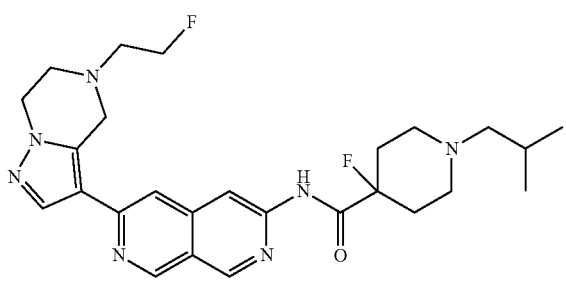 [SMILES: CC(C)CN1CCC(F)(C(=O)Nc2cc3cc(-c4cnn5c4CN(CCF)CC5)ncc3cn2)CC1] 3950

TABLE 1-continued
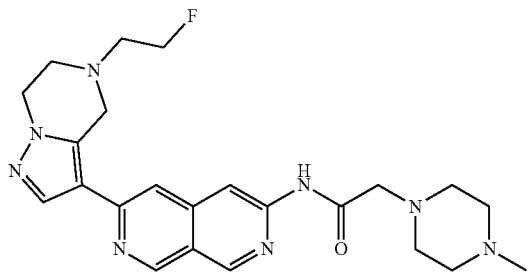 [SMILES: CN1CCN(CC(=O)Nc2cc3cc(-c4cnn5c4CN(CCF)CC5)ncc3cn2)CC1]
3951
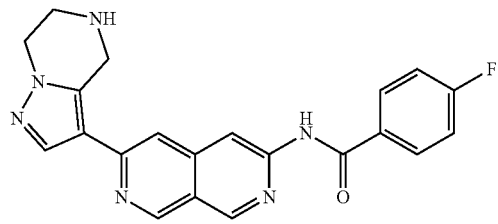 [SMILES: O=C(Nc1cc2cc(-c3cnn4c3CNCC4)ncc2cn1)c1ccc(F)cc1]
3952
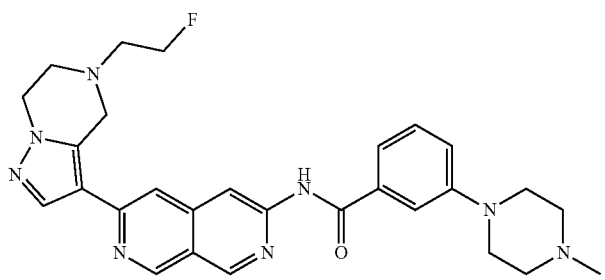 [SMILES: CN1CCN(c2cccc(C(=O)Nc3cc4cc(-c5cnn6c5CN(CCF)CC6)ncc4cn3)c2)CC1]
3953
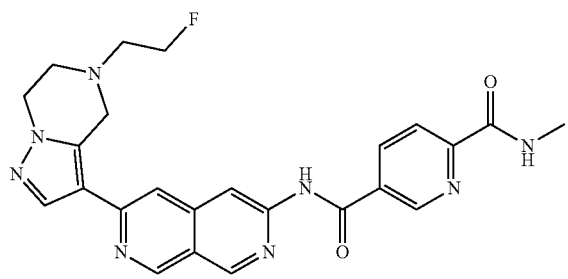 [SMILES: CNC(=O)c1ccc(C(=O)Nc2cc3cc(-c4cnn5c4CN(CCF)CC5)ncc3cn2)cn1]
3954
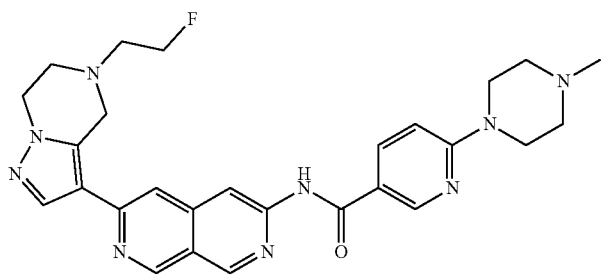 [SMILES: CN1CCN(c2ccc(C(=O)Nc3cc4cc(-c5cnn6c5CN(CCF)CC6)ncc4cn3)cn2)CC1]
3955
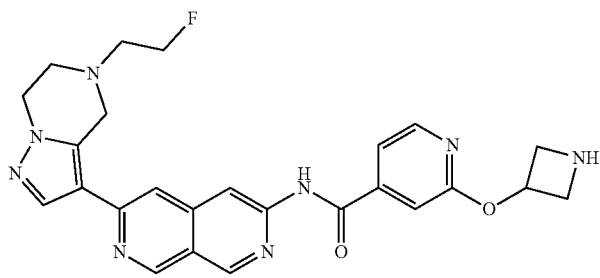 [SMILES: O=C(Nc1cc2cc(-c3cnn4c3CN(CCF)CC4)ncc2cn1)c1ccnc(OC2CNC2)c1]
3956

TABLE 1-continued
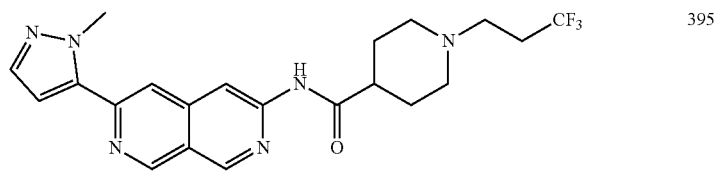 3957
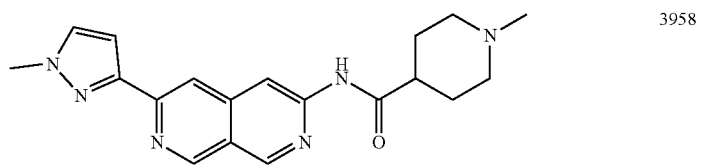 3958
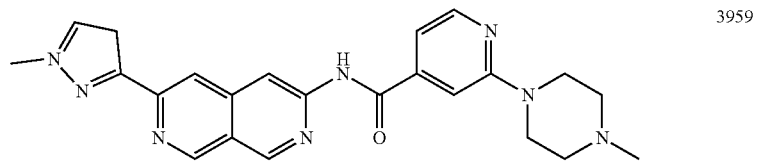 3959
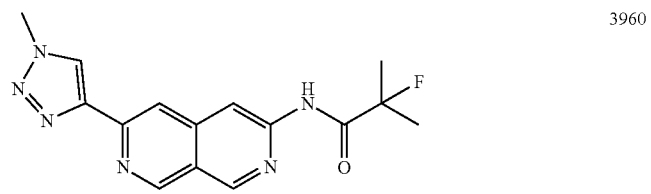 3960
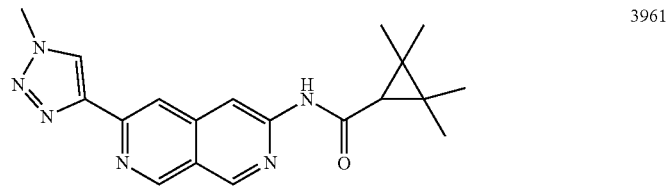 3961
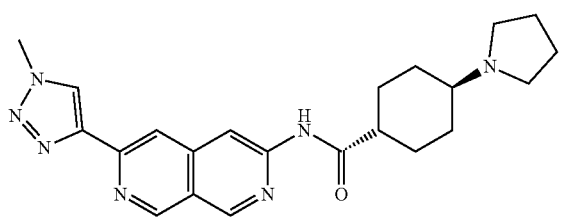 3962
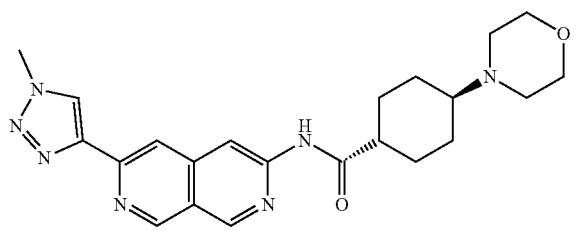 3963
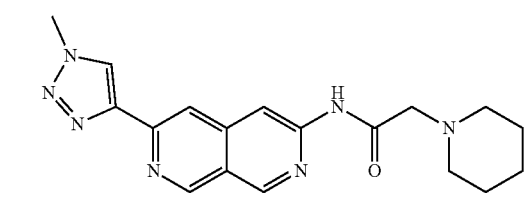 [SMILES: Cn1cc(-c2cc3cc(NC(=O)CN4CCCCC4)ncc3cn2)nn1] 3964

TABLE 1-continued
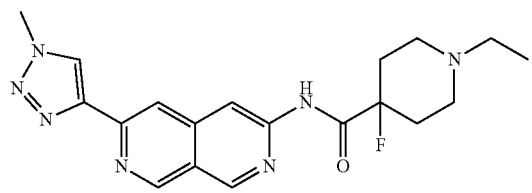 [SMILES: CCN1CCC(F)(C(=O)Nc2cc3cc(-c4cn(C)nn4)ncc3cn2)CC1] 3965
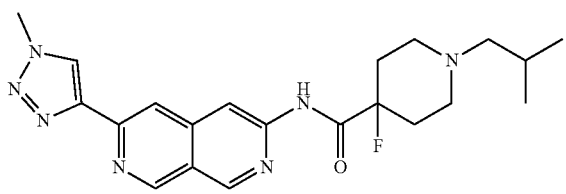 [SMILES: CC(C)CN1CCC(F)(C(=O)Nc2cc3cc(-c4cn(C)nn4)ncc3cn2)CC1] 3966
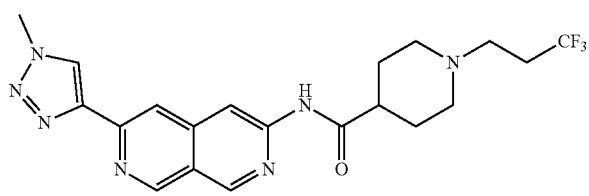 [SMILES: Cn1cc(-c2cc3cc(NC(=O)C4CCN(CCC(F)(F)F)CC4)ncc3cn2)nn1] 3967
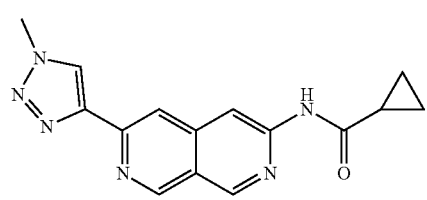 [SMILES: Cn1cc(-c2cc3cc(NC(=O)C4CC4)ncc3cn2)nn1] 3968
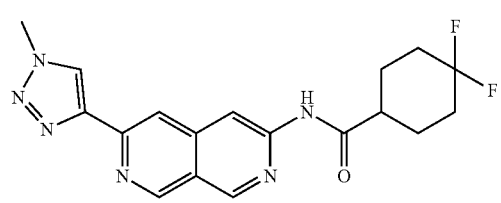 [SMILES: Cn1cc(-c2cc3cc(NC(=O)C4CCC(F)(F)CC4)ncc3cn2)nn1] 3969
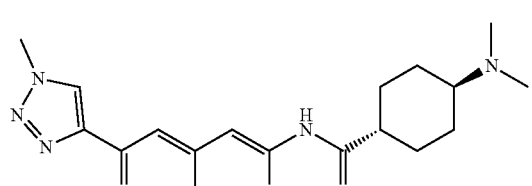 3970
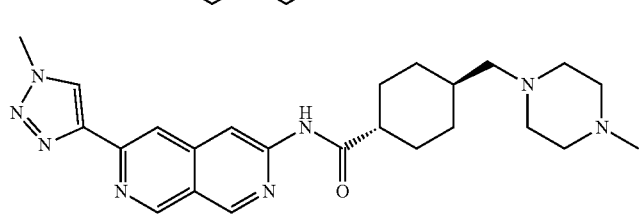 3971
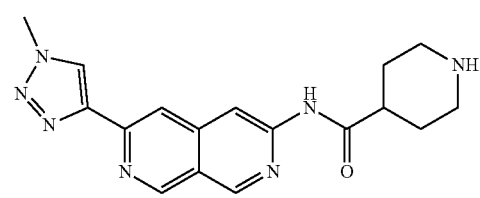 [SMILES: Cn1cc(-c2cc3cc(NC(=O)C4CCNCC4)ncc3cn2)nn1] 3972

TABLE 1-continued
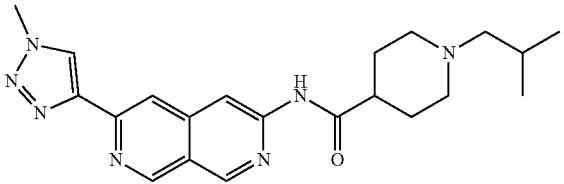 [SMILES: CC(C)CN1CCC(C(=O)Nc2cc3cc(-c4cn(C)nn4)ncc3cn2)CC1] 3973
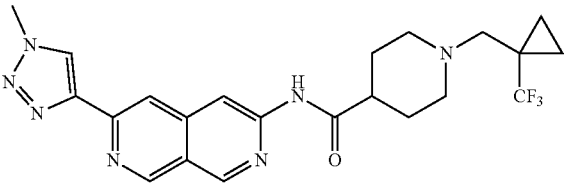 [SMILES: Cn1cc(-c2cc3cc(NC(=O)C4CCN(CC5(C(F)(F)F)CC5)CC4)ncc3cn2)nn1] 3974
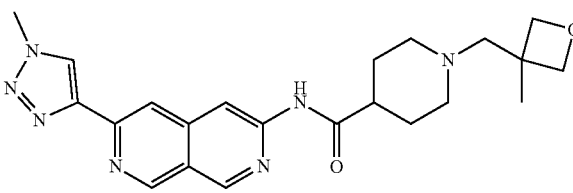 3975
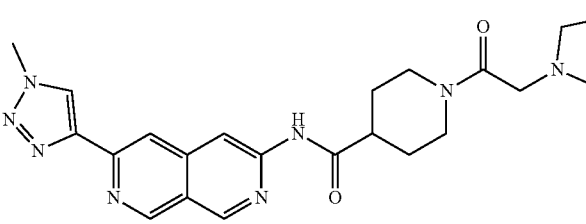 3976
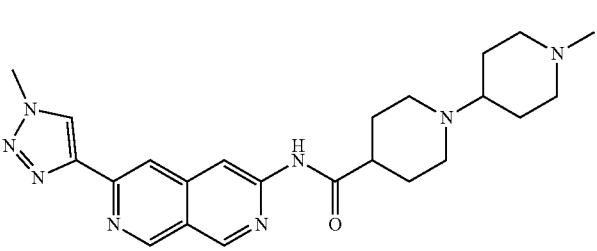 [SMILES: CN1CCC(N2CCC(C(=O)Nc3cc4cc(-c5cn(C)nn5)ncc4cn3)CC2)CC1] 3977
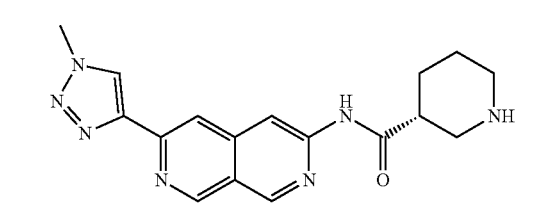 3978
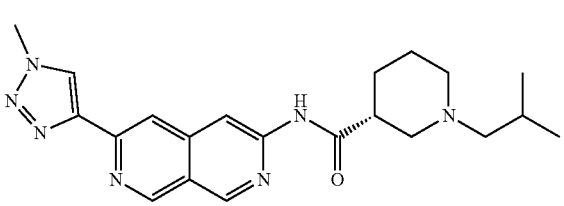 [SMILES: CC(C)CN1CCC[C@@H](C(=O)Nc2cc3cc(-c4cn(C)nn4)ncc3cn2)C1] 3979
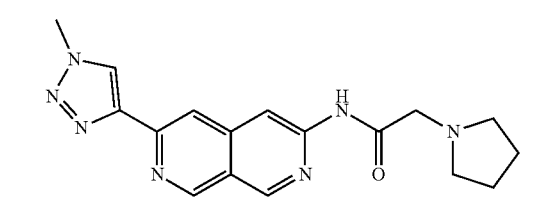 [SMILES: Cn1cc(-c2cc3cc(NC(=O)CN4CCCC4)ncc3cn2)nn1] 3980

TABLE 1-continued
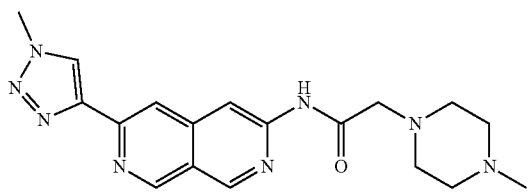 3981
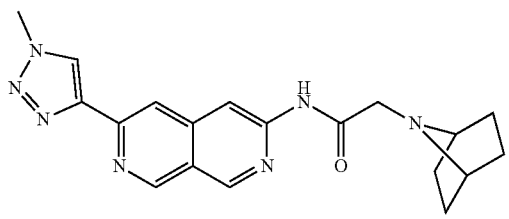 [SMILES: Cn1cc(-c2cc3cc(NC(=O)CN4C5CCC4CC5)ncc3cn2)nn1] 3982
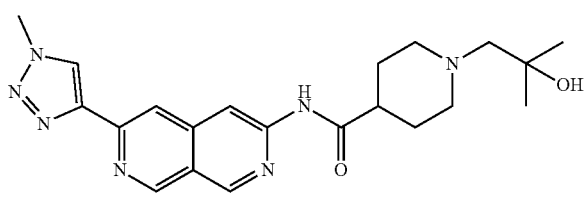 [SMILES: Cn1cc(-c2cc3cc(NC(=O)C4CCN(CC(C)(C)O)CC4)ncc3cn2)nn1] 3983
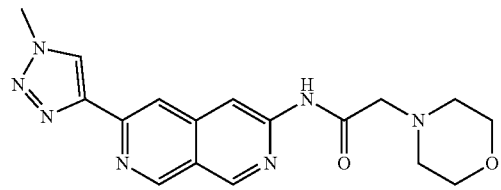 [SMILES: Cn1cc(-c2cc3cc(NC(=O)CN4CCOCC4)ncc3cn2)nn1] 3984
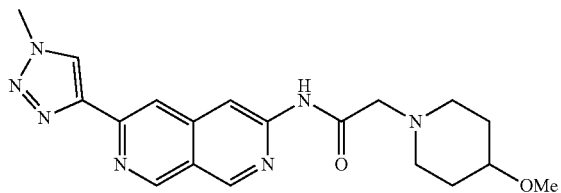 [SMILES: COC1CCN(CC(=O)Nc2cc3cc(-c4cn(C)nn4)ncc3cn2)CC1] 3985
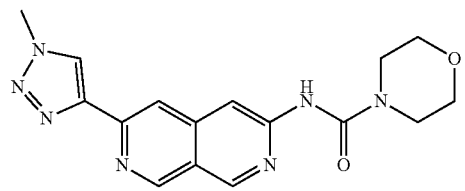 [SMILES: Cn1cc(-c2cc3cc(NC(=O)N4CCOCC4)ncc3cn2)nn1] 3986
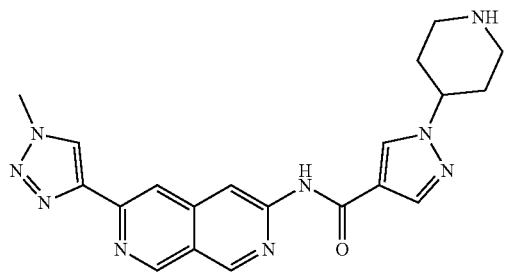 [SMILES: Cn1cc(-c2cc3cc(NC(=O)c4cnn(C5CCNCC5)c4)ncc3cn2)nn1] 3987

TABLE 1-continued
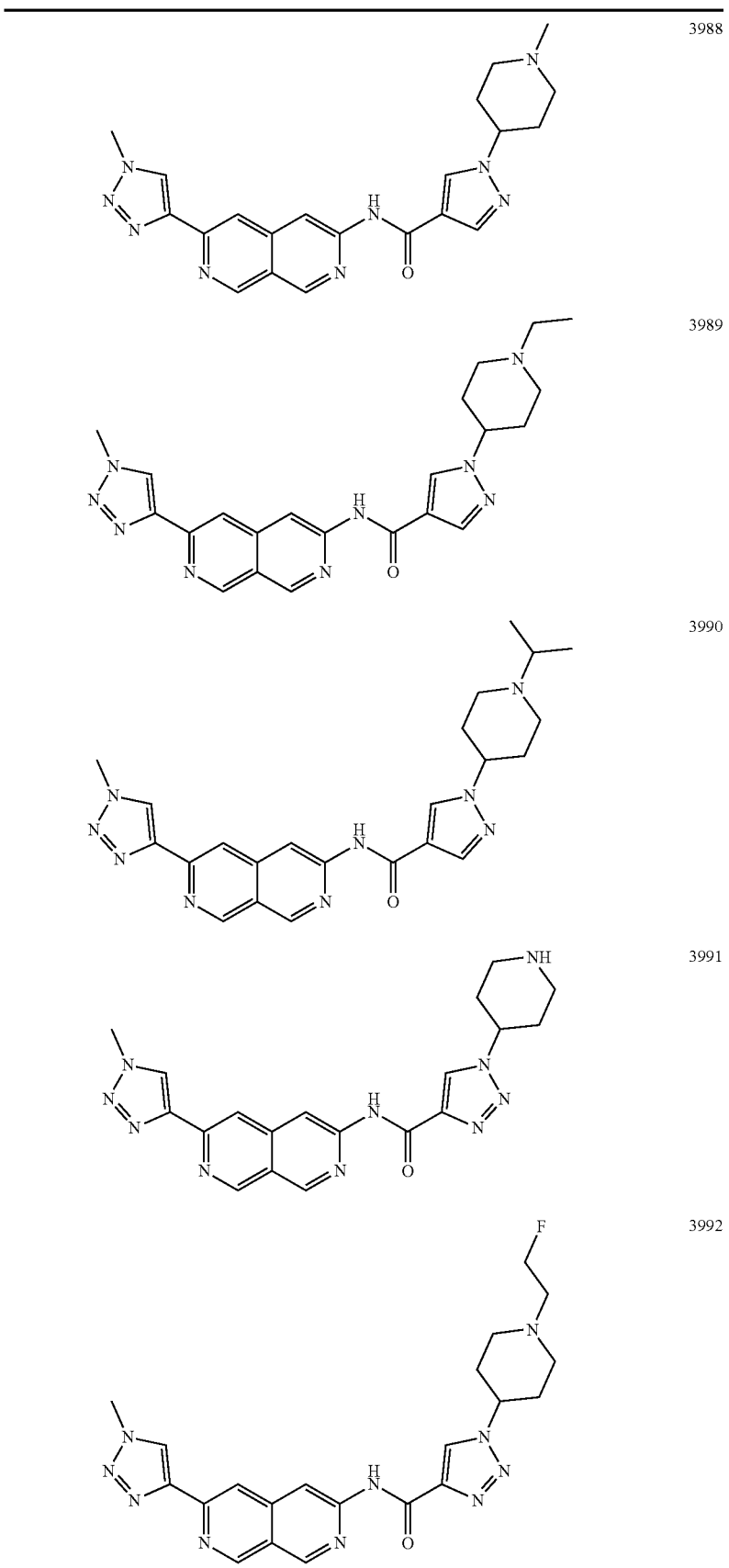

TABLE 1-continued
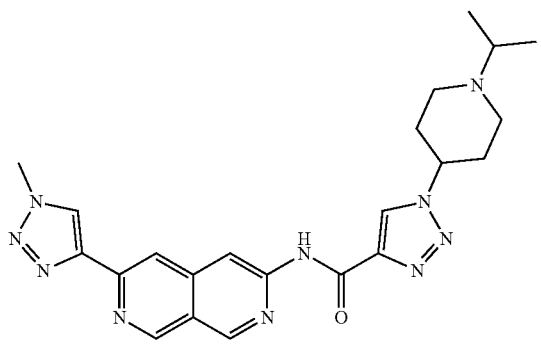 [SMILES: CC(C)N1CCC(n2cc(C(=O)Nc3cc4cc(-c5cn(C)nn5)ncc4cn3)cn2)CC1]
3993
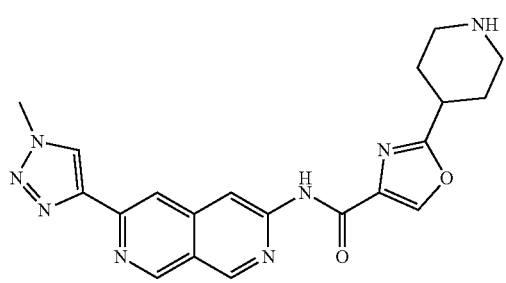 [SMILES: Cn1cc(-c2cc3cc(NC(=O)c4coc(C5CCNCC5)n4)ncc3cn2)nn1]
3994
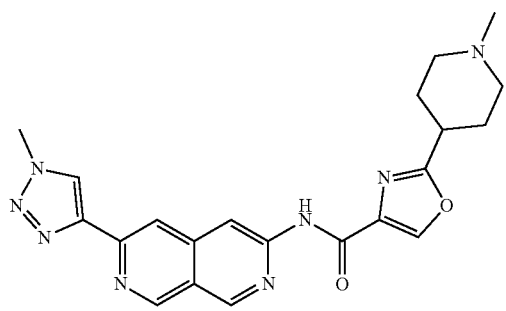 [SMILES: CN1CCC(c2nc(C(=O)Nc3cc4cc(-c5cn(C)nn5)ncc4cn3)co2)CC1]
3995
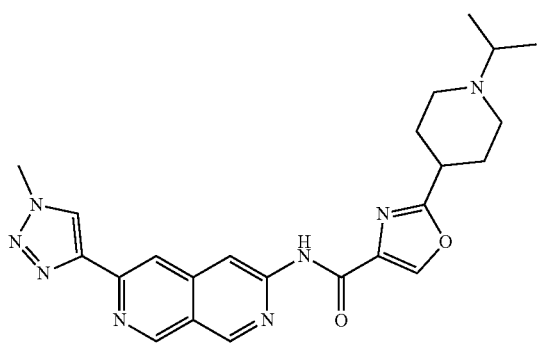 [SMILES: CC(C)N1CCC(c2nc(C(=O)Nc3cc4cc(-c5cn(C)nn5)ncc4cn3)co2)CC1]
3996
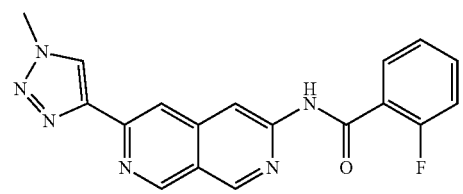 [SMILES: Cn1cc(-c2cc3cc(NC(=O)c4ccccc4F)ncc3cn2)nn1]
3997

TABLE 1-continued
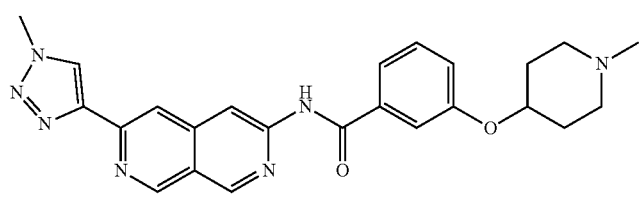 [SMILES: CN1CCC(Oc2cccc(C(=O)Nc3cc4cc(-c5cn(C)nn5)ncc4cn3)c2)CC1]
3998
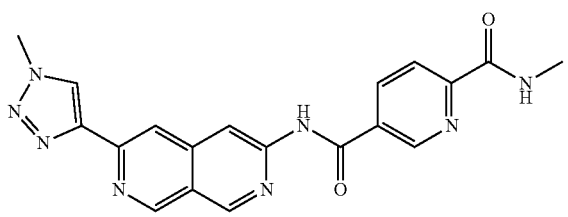 [SMILES: CNC(=O)c1ccc(C(=O)Nc2cc3cc(-c4cn(C)nn4)ncc3cn2)cn1]
3999
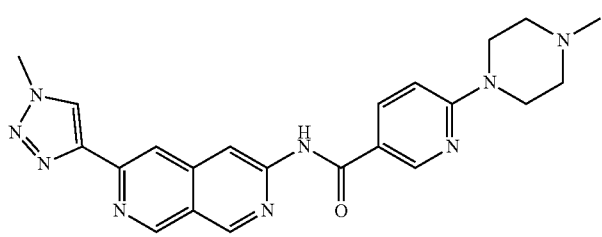 [SMILES: CN1CCN(c2ccc(C(=O)Nc3cc4cc(-c5cn(C)nn5)ncc4cn3)cn2)CC1]
4000
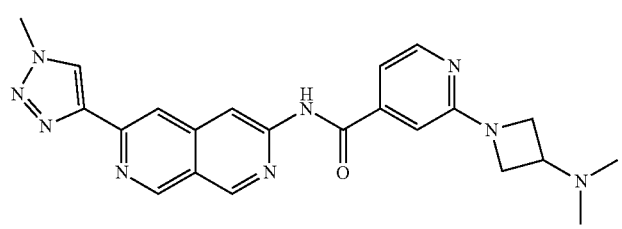
4001
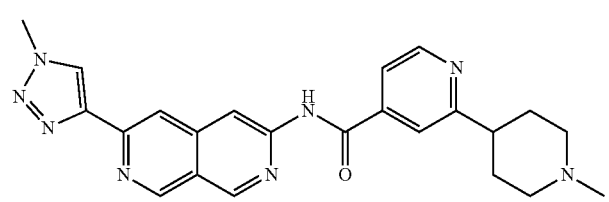 [SMILES: CN1CCC(c2cc(C(=O)Nc3cc4cc(-c5cn(C)nn5)ncc4cn3)ccn2)CC1]
4002
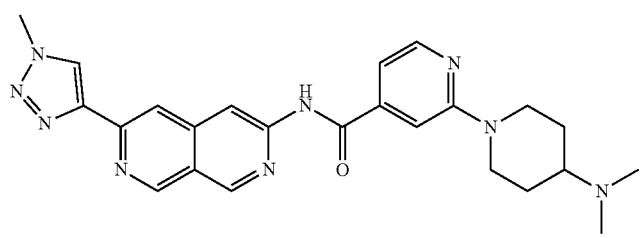 [SMILES: CN(C)C1CCN(c2cc(C(=O)Nc3cc4cc(-c5cn(C)nn5)ncc4cn3)ccn2)CC1]
4003
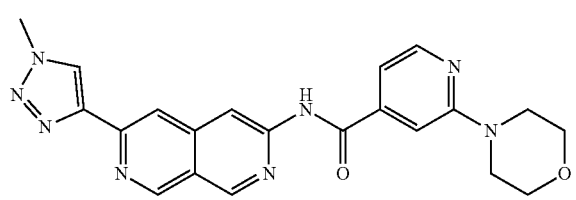 [SMILES: Cn1cc(-c2cc3cc(NC(=O)c4ccnc(N5CCOCC5)c4)ncc3cn2)nn1]
4004

TABLE 1-continued
| | |
|---|---|
| 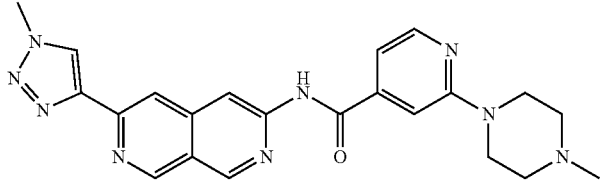 [SMILES: CN1CCN(c2cc(C(=O)Nc3cc4cc(-c5cn(C)nn5)ncc4cn3)ccn2)CC1] | 4005 |
| | 4006 |
| | 4007 |
| | 4008 |
| | 4009 |
| | 4010 |
| | 4011 |
| | 4012 |

TABLE 1-continued
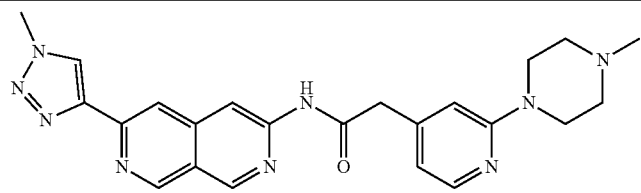
4013
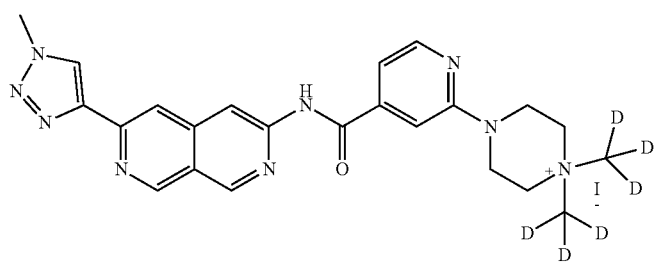
4014
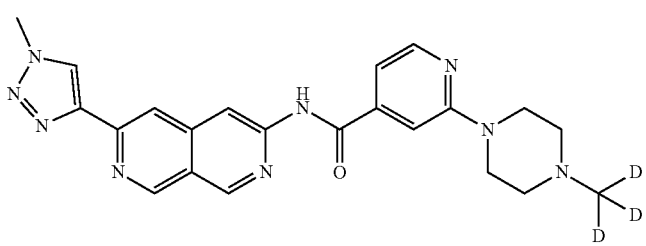
4015
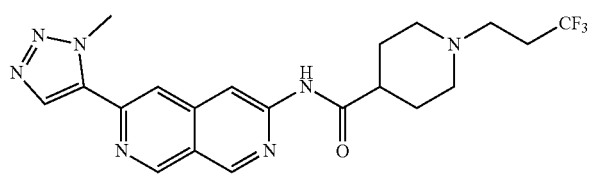 [SMILES: Cn1nncc1-c1cc2cc(NC(=O)C3CCN(CCC(F)(F)F)CC3)ncc2cn1]
4016
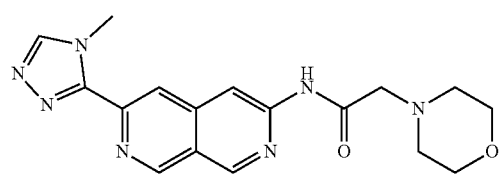 [SMILES: Cn1cnnc1-c1cc2cc(NC(=O)CN3CCOCC3)ncc2cn1]
4017
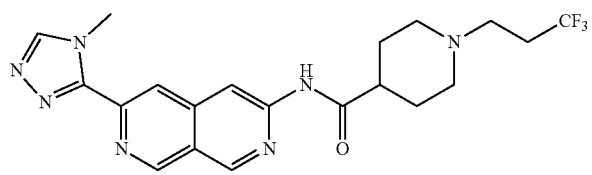 [SMILES: Cn1cnnc1-c1cc2cc(NC(=O)C3CCN(CCC(F)(F)F)CC3)ncc2cn1]
4018
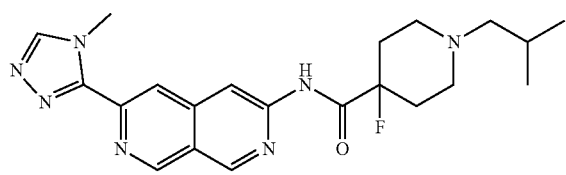 [SMILES: CC(C)CN1CCC(F)(C(=O)Nc2cc3cc(-c4nncn4C)ncc3cn2)CC1]
4019
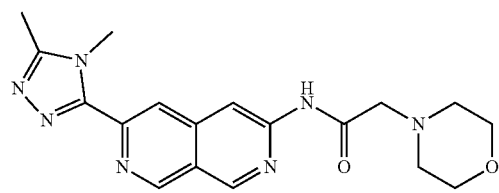 [SMILES: Cc1nnc(-c2cc3cc(NC(=O)CN4CCOCC4)ncc3cn2)n1C]
4020

TABLE 1-continued

| | |
|---|---|
| (structure) | 4021 |
| (structure) | 4022 |
| (structure) | 4023 |
| (structure) | 4024 |
| (structure) | 4025 |
| (structure) | 4026 |
| (structure) | 4027 |
| (structure) | 4028 |
| (structure) | 4029 |

TABLE 1-continued
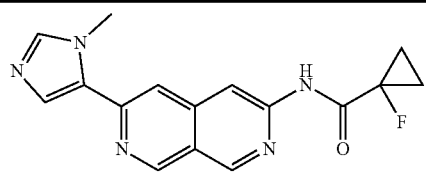 4030
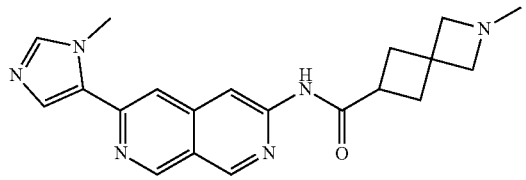 [SMILES: CN1CC2(CC(C(=O)Nc3cc4cc(-c5cncn5C)ncc4cn3)C2)C1] 4031
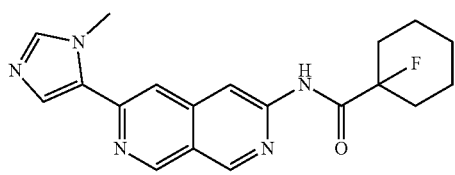 4032
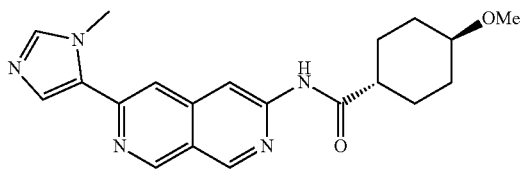 [SMILES: CO[C@H]1CC[C@H](C(=O)Nc2cc3cc(-c4cncn4C)ncc3cn2)CC1] 4033
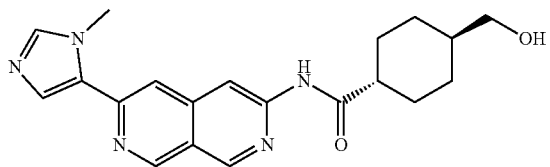 [SMILES: Cn1cncc1-c1cc2cc(NC(=O)[C@H]3CC[C@H](CO)CC3)ncc2cn1] 4034
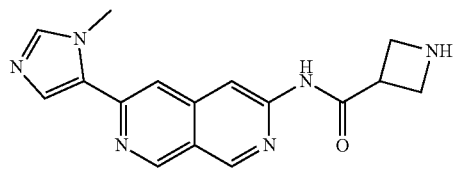 [SMILES: Cn1cncc1-c1cc2cc(NC(=O)C3CNC3)ncc2cn1] 4035
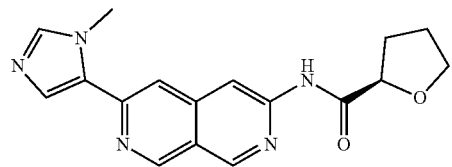 [SMILES: Cn1cncc1-c1cc2cc(NC(=O)[C@H]3CCCO3)ncc2cn1] 4036
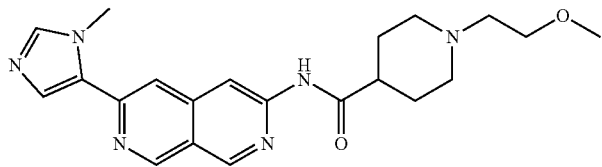 [SMILES: COCCN1CCC(C(=O)Nc2cc3cc(-c4cncn4C)ncc3cn2)CC1] 4037
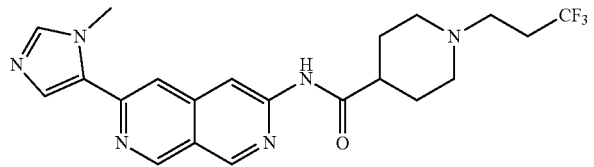 [SMILES: Cn1cncc1-c1cc2cc(NC(=O)C3CCN(CCC(F)(F)F)CC3)ncc2cn1] 4038

TABLE 1-continued
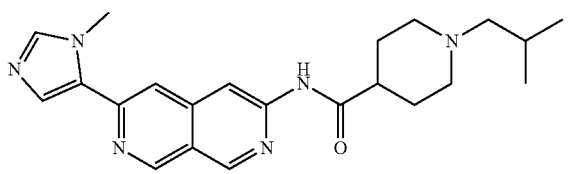 [SMILES: CC(C)CN1CCC(C(=O)Nc2cc3cc(-c4cncn4C)ncc3cn2)CC1] 4039
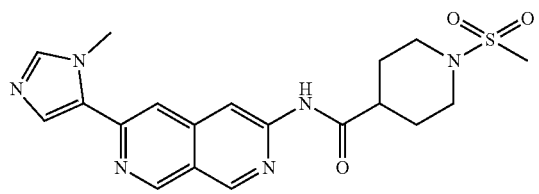 [SMILES: Cn1cncc1-c1cc2cc(NC(=O)C3CCN(S(C)(=O)=O)CC3)ncc2cn1] 4040
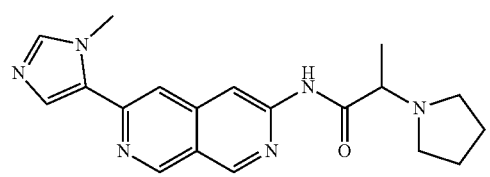 [SMILES: CC(C(=O)Nc1cc2cc(-c3cncn3C)ncc2cn1)N1CCCC1] 4041
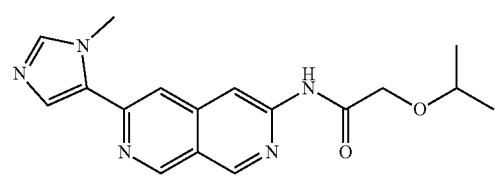 [SMILES: CC(C)OCC(=O)Nc1cc2cc(-c3cncn3C)ncc2cn1] 4042
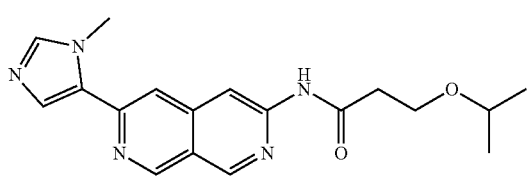 [SMILES: CC(C)OCCC(=O)Nc1cc2cc(-c3cncn3C)ncc2cn1] 4043
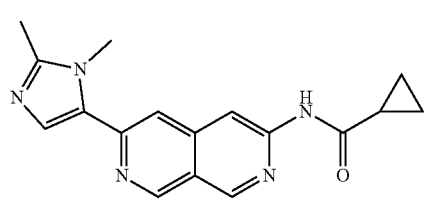 [SMILES: Cc1ncc(-c2cc3cc(NC(=O)C4CC4)ncc3cn2)n1C] 4044
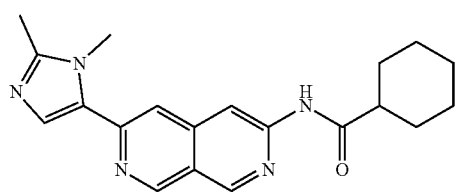 [SMILES: Cc1ncc(-c2cc3cc(NC(=O)C4CCCCC4)ncc3cn2)n1C] 4045
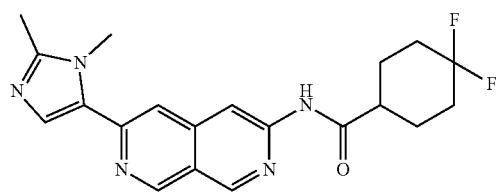 [SMILES: Cc1ncc(-c2cc3cc(NC(=O)C4CCC(F)(F)CC4)ncc3cn2)n1C] 4046

TABLE 1-continued
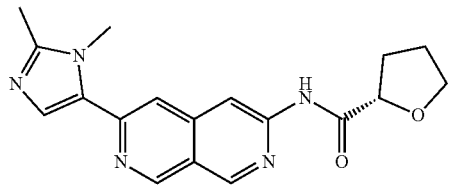 [SMILES: Cc1ncc(-c2cc3cc(NC(=O)[C@@H]4CCCO4)ncc3cn2)n1C] 4047
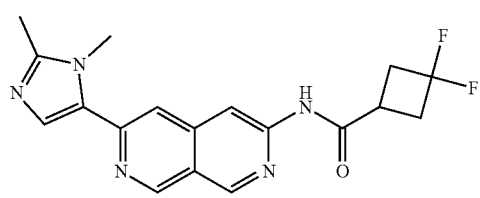 4048
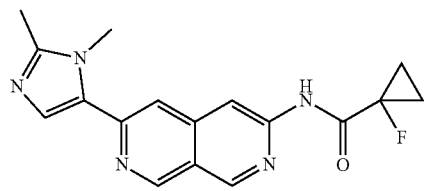 4049
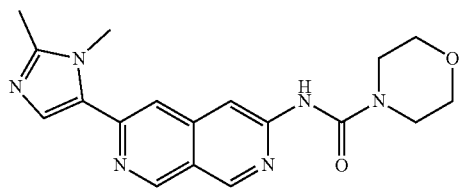 [SMILES: Cc1ncc(-c2cc3cc(NC(=O)N4CCOCC4)ncc3cn2)n1C] 4050
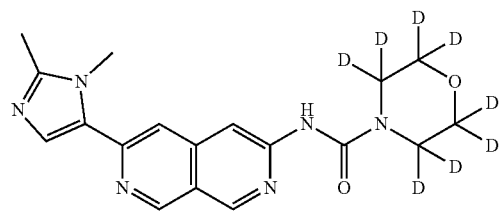 [SMILES: [2H]C1([2H])OC([2H])([2H])C([2H])([2H])N(C(=O)Nc2cc3cc(-c4cnc(C)n4C)ncc3cn2)C1([2H])[2H]] 4051
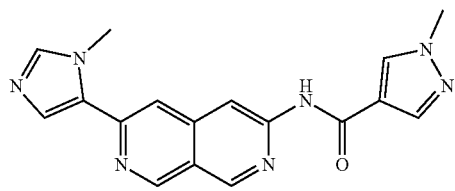 [SMILES: Cn1cc(C(=O)Nc2cc3cc(-c4cncn4C)ncc3cn2)cn1] 4052
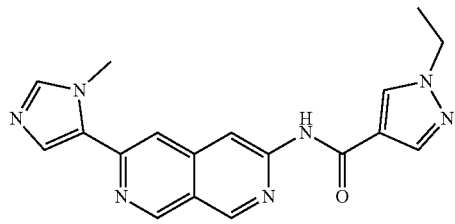 [SMILES: CCn1cc(C(=O)Nc2cc3cc(-c4cncn4C)ncc3cn2)cn1] 4053

TABLE 1-continued
| | |
|---|---|
| 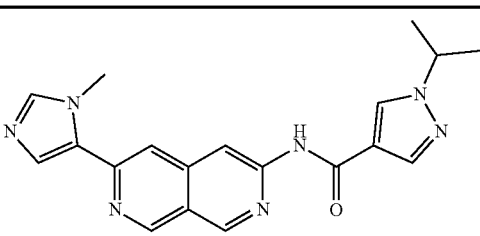 | 4054 |
| 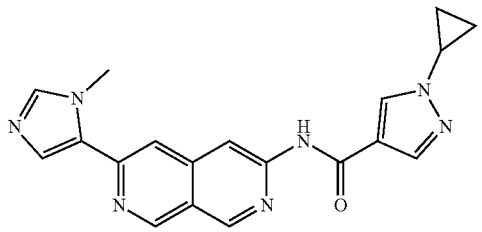 [SMILES: Cn1cncc1-c1cc2cc(NC(=O)c3cnn(C4CC4)c3)ncc2cn1] | 4055 |
| 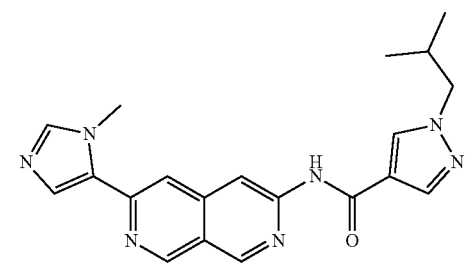 | 4056 |
| 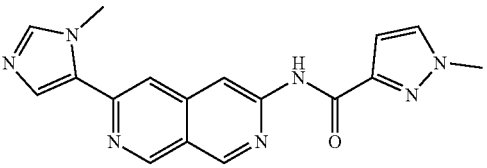 [SMILES: Cn1ccc(C(=O)Nc2cc3cc(-c4cncn4C)ncc3cn2)n1] | 4057 |
| 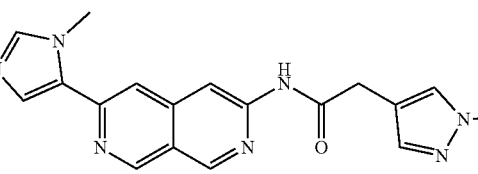 | 4058 |
| 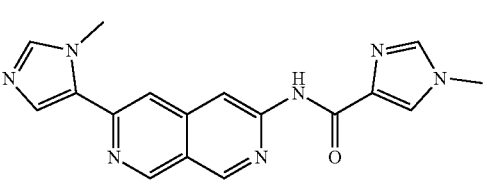 [SMILES: Cn1cnc(C(=O)Nc2cc3cc(-c4cncn4C)ncc3cn2)c1] | 4059 |
| 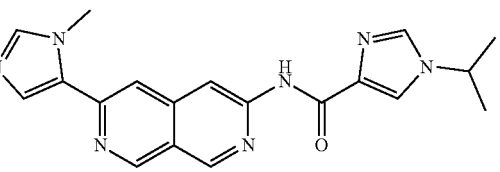 | 4060 |
|  | 4061 |

TABLE 1-continued
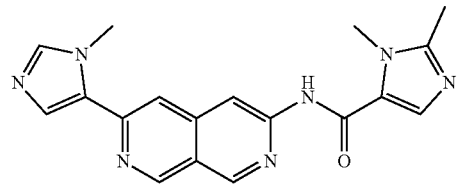 [SMILES: Cc1ncc(C(=O)Nc2cc3cc(-c4cncn4C)ncc3cn2)n1C]
4062
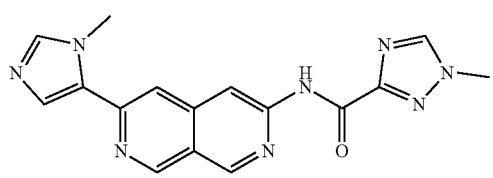
4063
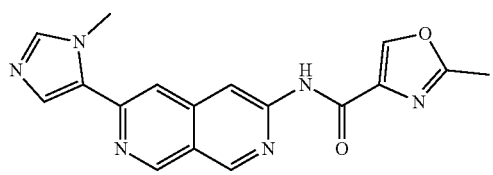 [SMILES: Cc1nc(C(=O)Nc2cc3cc(-c4cncn4C)ncc3cn2)co1]
4064
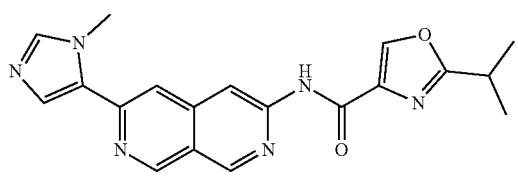 [SMILES: CC(C)c1nc(C(=O)Nc2cc3cc(-c4cncn4C)ncc3cn2)co1]
4065
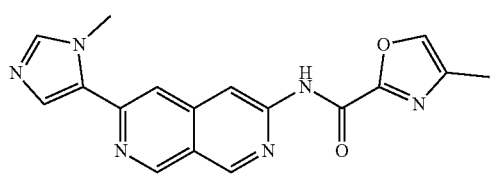 [SMILES: Cc1coc(C(=O)Nc2cc3cc(-c4cncn4C)ncc3cn2)n1]
4066
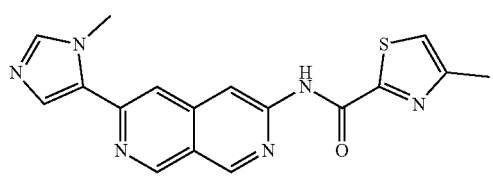 [SMILES: Cc1csc(C(=O)Nc2cc3cc(-c4cncn4C)ncc3cn2)n1]
4067
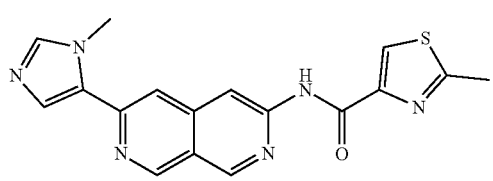
4068
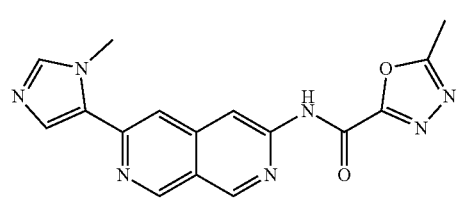 [SMILES: Cc1nnc(C(=O)Nc2cc3cc(-c4cncn4C)ncc3cn2)o1]
4069

TABLE 1-continued
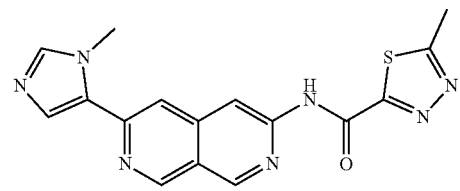 [SMILES: Cc1nnc(C(=O)Nc2cc3cc(-c4cncn4C)ncc3cn2)s1] 4070
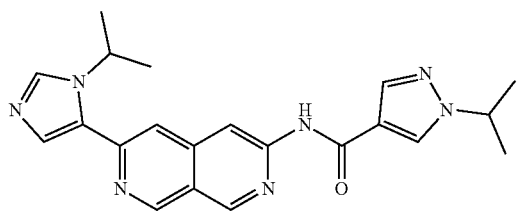 [SMILES: CC(C)n1cc(C(=O)Nc2cc3cc(-c4cncn4C(C)C)ncc3cn2)cn1] 4071
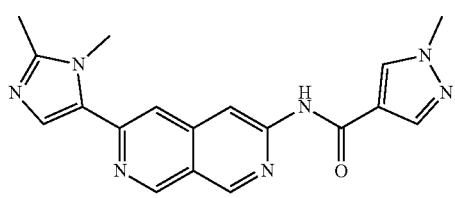 [SMILES: Cc1ncc(-c2cc3cc(NC(=O)c4cnn(C)c4)ncc3cn2)n1C] 4072
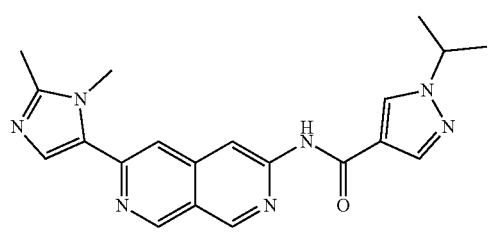 [SMILES: Cc1ncc(-c2cc3cc(NC(=O)c4cnn(C(C)C)c4)ncc3cn2)n1C] 4073
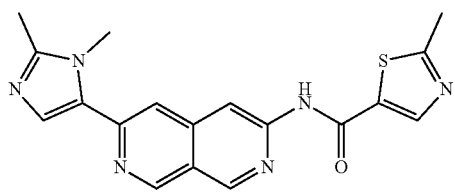 [SMILES: Cc1ncc(C(=O)Nc2cc3cc(-c4cnc(C)n4C)ncc3cn2)s1] 4074
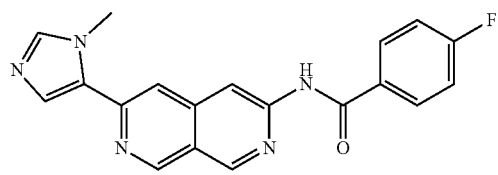 [SMILES: Cn1cncc1-c1cc2cc(NC(=O)c3ccc(F)cc3)ncc2cn1] 4075
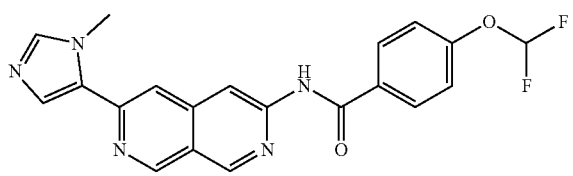 [SMILES: Cn1cncc1-c1cc2cc(NC(=O)c3ccc(OC(F)F)cc3)ncc2cn1] 4076
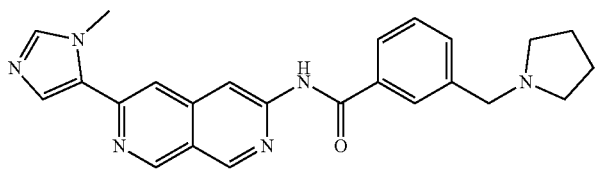 4077

TABLE 1-continued
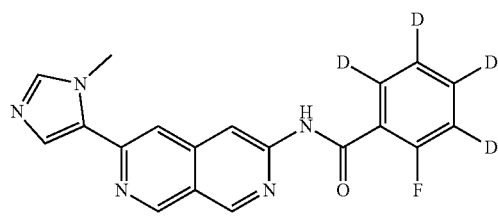 [SMILES: [2H]c1c([2H])c([2H])c(C(=O)Nc2cc3cc(-c4cncn4C)ncc3cn2)c(F)c1[2H]] 4078
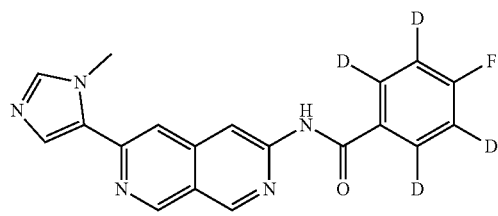 4079
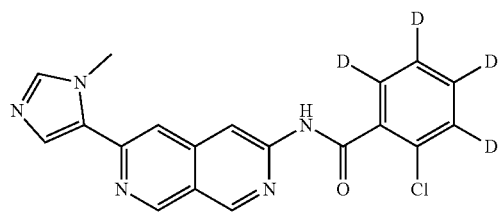 [SMILES: [2H]c1c([2H])c([2H])c(C(=O)Nc2cc3cc(-c4cncn4C)ncc3cn2)c(Cl)c1[2H]] 4080
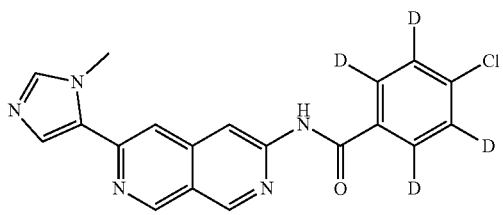 [SMILES: [2H]c1c([2H])c(C(=O)Nc2cc3cc(-c4cncn4C)ncc3cn2)c([2H])c([2H])c1Cl] 4081
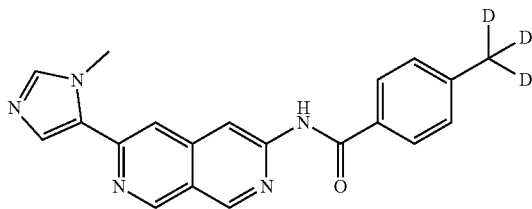 [SMILES: [2H]C([2H])([2H])c1ccc(C(=O)Nc2cc3cc(-c4cncn4C)ncc3cn2)cc1] 4082
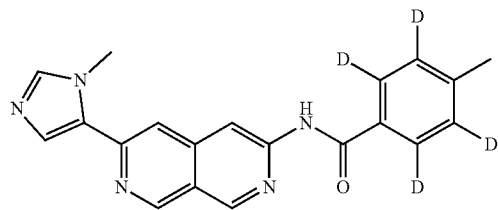 [SMILES: [2H]c1c([2H])c(C(=O)Nc2cc3cc(-c4cncn4C)ncc3cn2)c([2H])c([2H])c1C] 4083
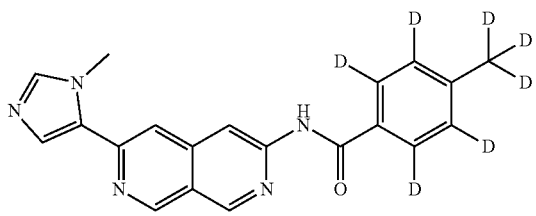 [SMILES: [2H]c1c([2H])c(C([2H])([2H])[2H])c([2H])c([2H])c1C(=O)Nc1cc2cc(-c3cncn3C)ncc2cn1] 4084

TABLE 1-continued
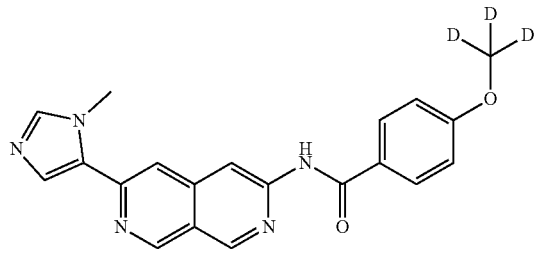 [SMILES: [2H]C([2H])([2H])Oc1ccc(C(=O)Nc2cc3cc(-c4cncn4C)ncc3cn2)cc1]
4085
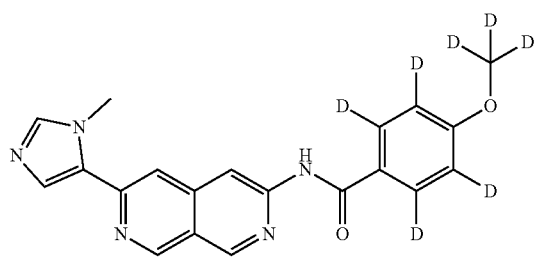 [SMILES: [2H]c1c([2H])c(C(=O)Nc2cc3cc(-c4cncn4C)ncc3cn2)c([2H])c([2H])c1OC([2H])([2H])[2H]]
4086
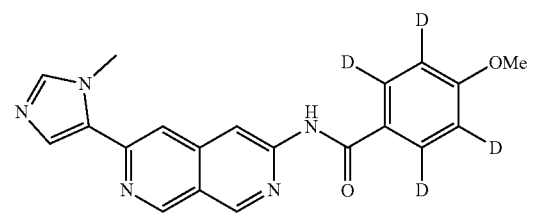 [SMILES: [2H]c1c([2H])c(C(=O)Nc2cc3cc(-c4cncn4C)ncc3cn2)c([2H])c([2H])c1OC]
4087
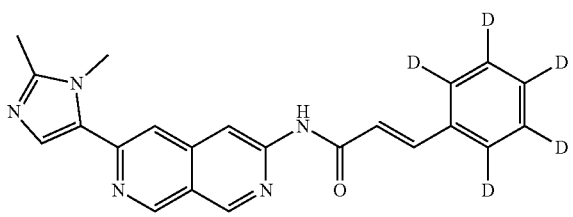 [SMILES: [2H]c1c([2H])c([2H])c(/C=C/C(=O)Nc2cc3cc(-c4cnc(C)n4C)ncc3cn2)c([2H])c1[2H]]
4088
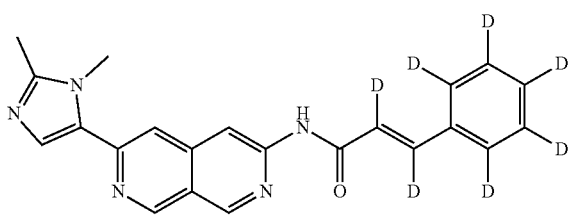 [SMILES: [2H]/C(C(=O)Nc1cc2cc(-c3cnc(C)n3C)ncc2cn1)=C(/[2H])c1c([2H])c([2H])c([2H])c([2H])c1[2H]]
4089
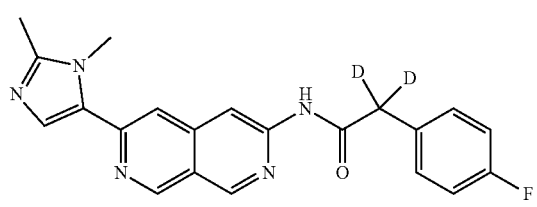 [SMILES: [2H]C([2H])(C(=O)Nc1cc2cc(-c3cnc(C)n3C)ncc2cn1)c1ccc(F)cc1]
4090
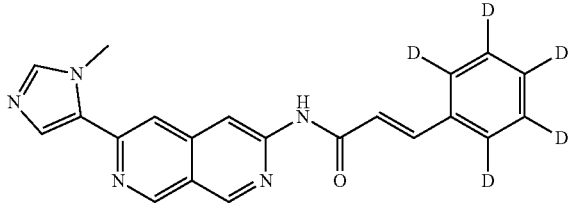 [SMILES: [2H]c1c([2H])c([2H])c(/C=C/C(=O)Nc2cc3cc(-c4cncn4C)ncc3cn2)c([2H])c1[2H]]
4091

TABLE 1-continued
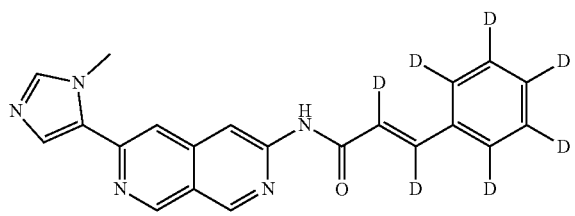 4092
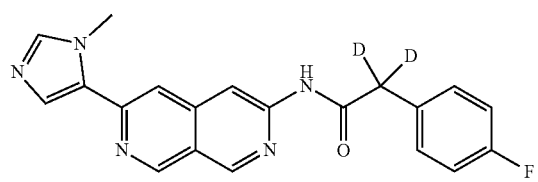 [SMILES: [2H]C([2H])(C(=O)Nc1cc2cc(-c3cncn3C)ncc2cn1)c1ccc(F)cc1] 4093
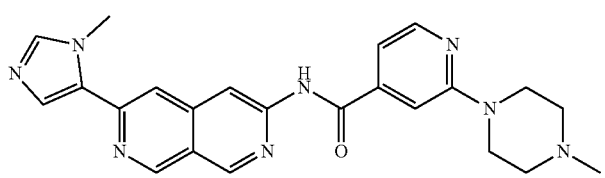 4094
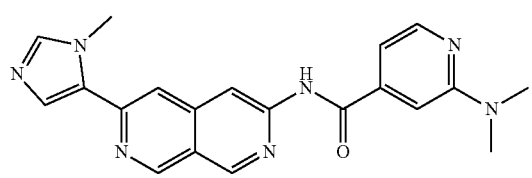 [SMILES: CN(C)c1cc(C(=O)Nc2cc3cc(-c4cncn4C)ncc3cn2)ccn1] 4095
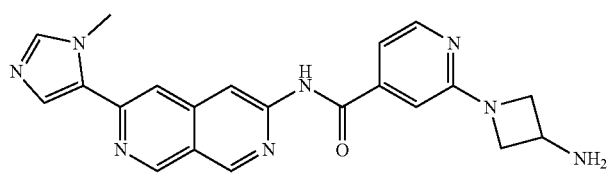 [SMILES: Cn1cncc1-c1cc2cc(NC(=O)c3ccnc(N4CC(N)C4)c3)ncc2cn1] 4096
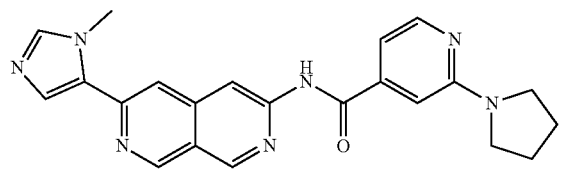 [SMILES: Cn1cncc1-c1cc2cc(NC(=O)c3ccnc(N4CCCC4)c3)ncc2cn1] 4097
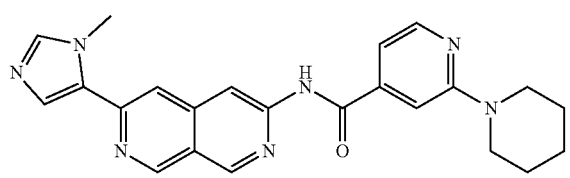 [SMILES: Cn1cncc1-c1cc2cc(NC(=O)c3ccnc(N4CCCCC4)c3)ncc2cn1] 4098
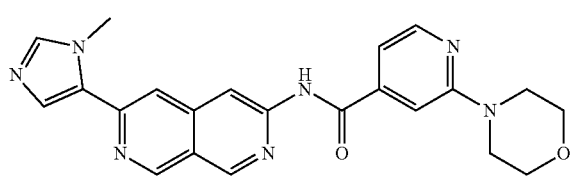 [SMILES: Cn1cncc1-c1cc2cc(NC(=O)c3ccnc(N4CCOCC4)c3)ncc2cn1] 4099

TABLE 1-continued
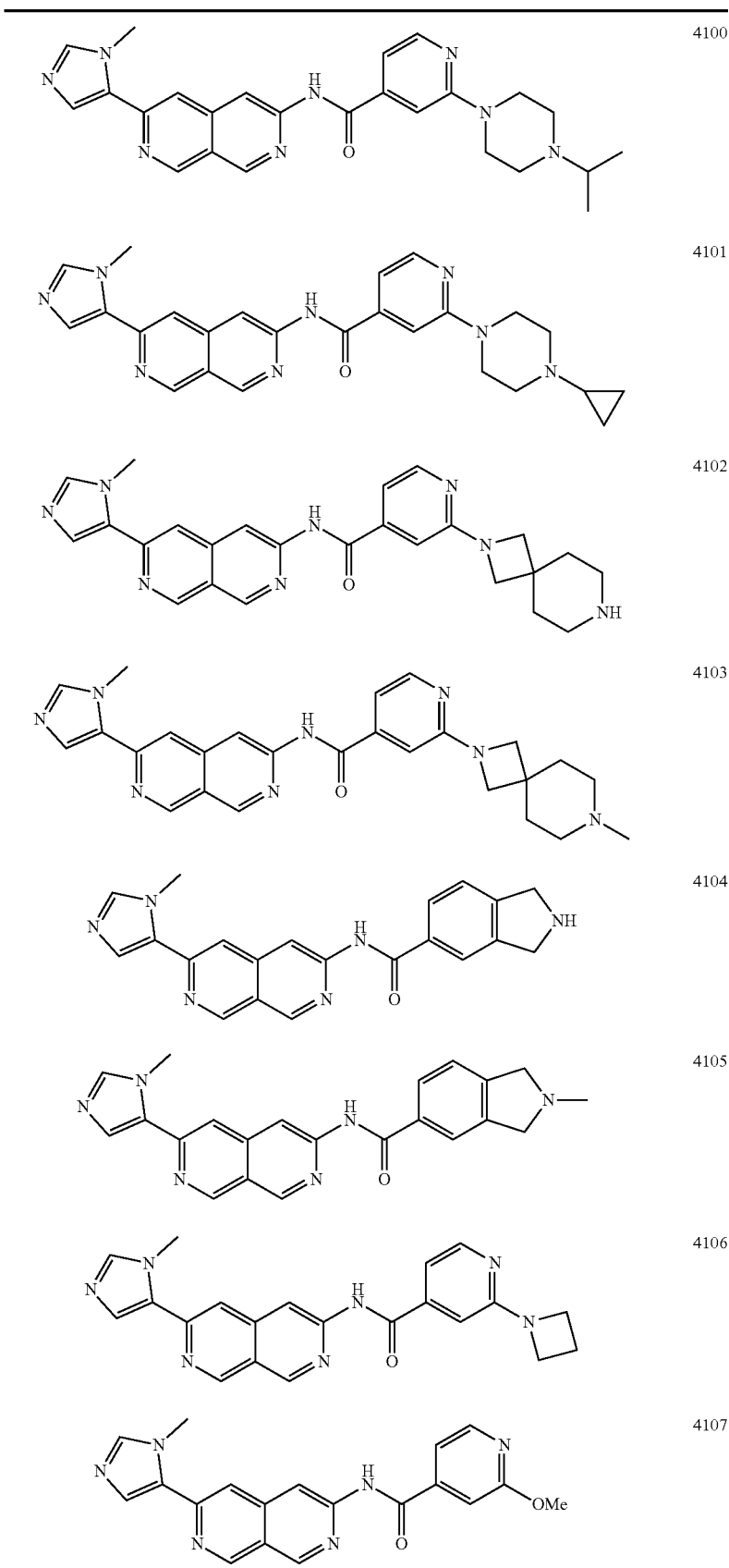
4100
4101
4102
4103
4104
4105
4106
4107

TABLE 1-continued
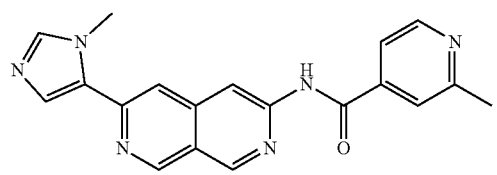 [SMILES: Cc1cc(C(=O)Nc2cc3cc(-c4cncn4C)ncc3cn2)ccn1] 4108
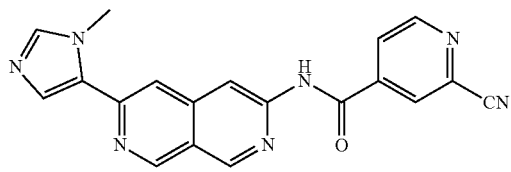 [SMILES: Cn1cncc1-c1cc2cc(NC(=O)c3ccnc(C#N)c3)ncc2cn1] 4109
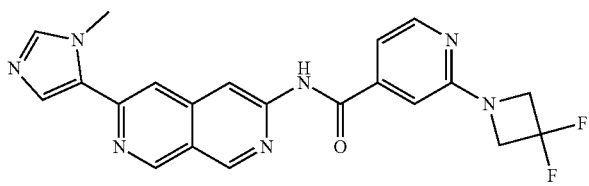 [SMILES: Cn1cncc1-c1cc2cc(NC(=O)c3ccnc(N4CC(F)(F)C4)c3)ncc2cn1] 4110
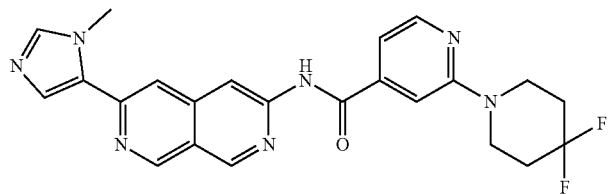 [SMILES: Cn1cncc1-c1cc2cc(NC(=O)c3ccnc(N4CCC(F)(F)CC4)c3)ncc2cn1] 4111
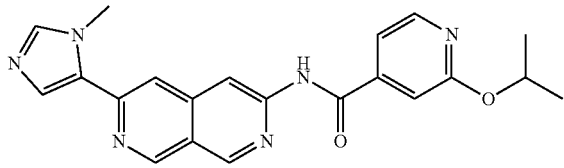 [SMILES: CC(C)Oc1cc(C(=O)Nc2cc3cc(-c4cncn4C)ncc3cn2)ccn1] 4112
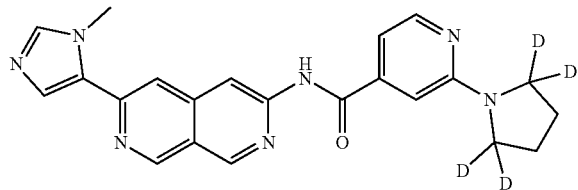 [SMILES: [2H]C1([2H])CCC([2H])([2H])N1c1cc(C(=O)Nc2cc3cc(-c4cncn4C)ncc3cn2)ccn1] 4113
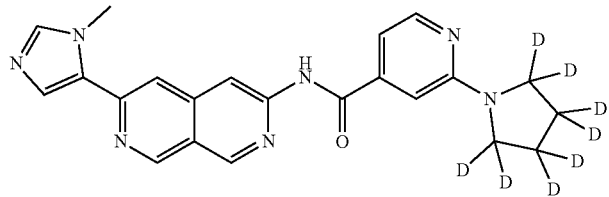 4114
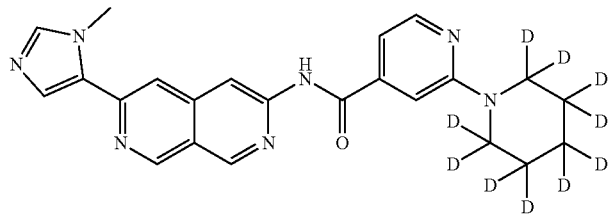 [SMILES: [2H]C1([2H])N(c2cc(C(=O)Nc3cc4cc(-c5cncn5C)ncc4cn3)ccn2)C([2H])([2H])C([2H])([2H])C([2H])([2H])C1([2H])[2H]] 4115

TABLE 1-continued
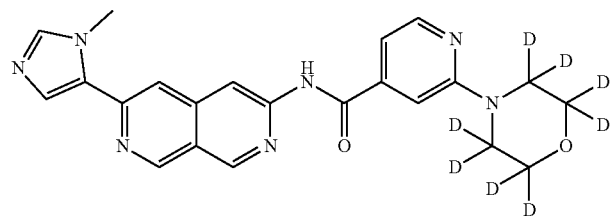 [SMILES: [2H]C1([2H])OC([2H])([2H])C([2H])([2H])N(c2cc(C(=O)Nc3cc4cc(-c5cncn5C)ncc4cn3)ccn2)C1([2H])[2H]] 4116
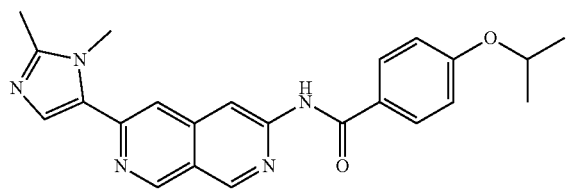 [SMILES: Cc1ncc(-c2cc3cc(NC(=O)c4ccc(OC(C)C)cc4)ncc3cn2)n1C] 4117
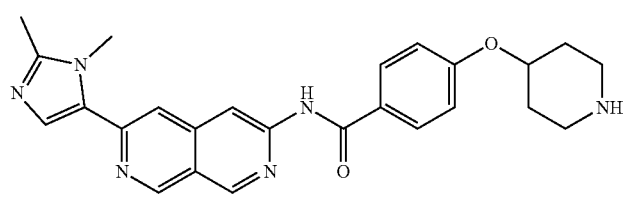 [SMILES: Cc1ncc(-c2cc3cc(NC(=O)c4ccc(OC5CCNCC5)cc4)ncc3cn2)n1C] 4118
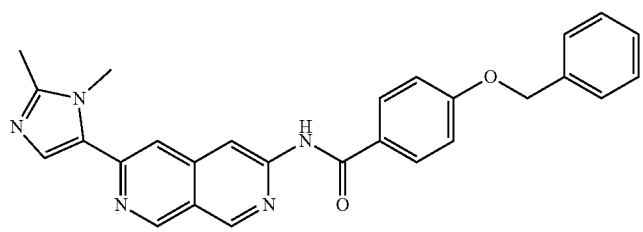 [SMILES: Cc1ncc(-c2cc3cc(NC(=O)c4ccc(OCc5ccccc5)cc4)ncc3cn2)n1C] 4119
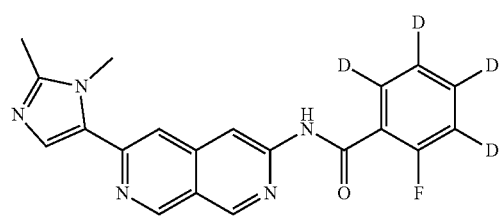 [SMILES: [2H]c1c([2H])c([2H])c(C(=O)Nc2cc3cc(-c4cnc(C)n4C)ncc3cn2)c(F)c1[2H]] 4120
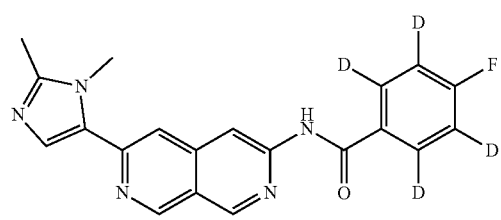 [SMILES: [2H]c1c([2H])c(C(=O)Nc2cc3cc(-c4cnc(C)n4C)ncc3cn2)c([2H])c([2H])c1F] 4121
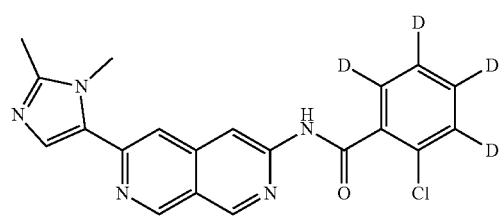 [SMILES: [2H]c1c([2H])c([2H])c(C(=O)Nc2cc3cc(-c4cnc(C)n4C)ncc3cn2)c(Cl)c1[2H]] 4122

TABLE 1-continued
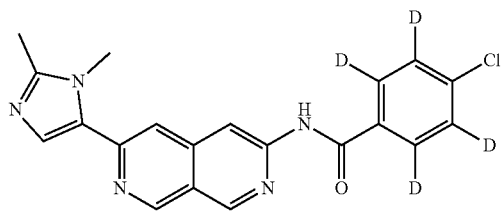 [SMILES: [2H]c1c([2H])c(C(=O)Nc2cc3cc(-c4cnc(C)n4C)ncc3cn2)c([2H])c([2H])c1Cl]
4123
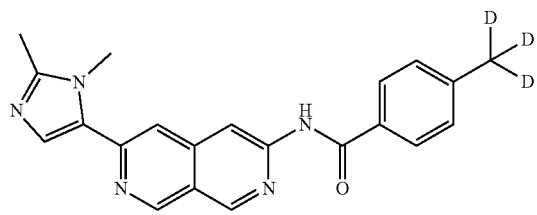 [SMILES: [2H]C([2H])([2H])c1ccc(C(=O)Nc2cc3cc(-c4cnc(C)n4C)ncc3cn2)cc1]
4124
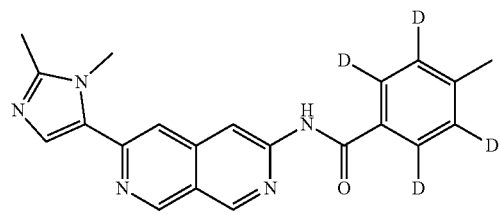 [SMILES: [2H]c1c([2H])c(C(=O)Nc2cc3cc(-c4cnc(C)n4C)ncc3cn2)c([2H])c([2H])c1C]
4125
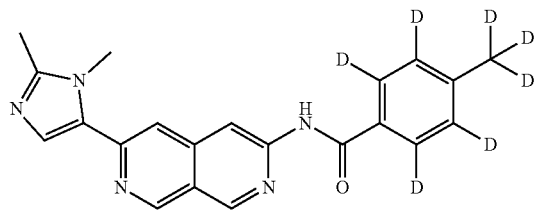 [SMILES: [2H]c1c([2H])c(C([2H])([2H])[2H])c([2H])c([2H])c1C(=O)Nc1cc2cc(-c3cnc(C)n3C)ncc2cn1]
4126
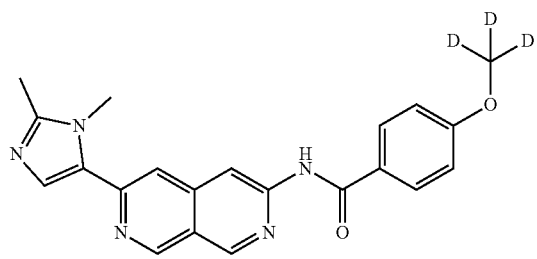 [SMILES: [2H]C([2H])([2H])Oc1ccc(C(=O)Nc2cc3cc(-c4cnc(C)n4C)ncc3cn2)cc1]
4127
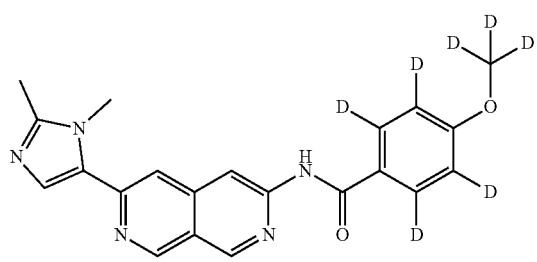 [SMILES: [2H]c1c([2H])c(C(=O)Nc2cc3cc(-c4cnc(C)n4C)ncc3cn2)c([2H])c([2H])c1OC([2H])([2H])[2H]]
4128
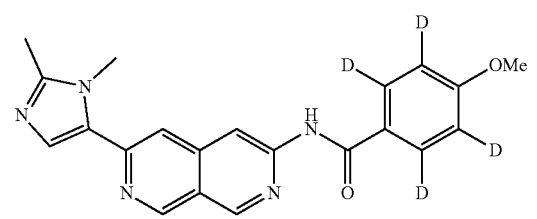 [SMILES: [2H]c1c([2H])c(C(=O)Nc2cc3cc(-c4cnc(C)n4C)ncc3cn2)c([2H])c([2H])c1OC]
4129

TABLE 1-continued
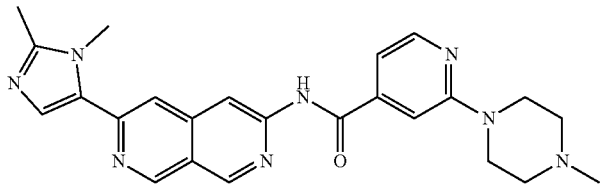 [SMILES: Cc1ncc(-c2cc3cc(NC(=O)c4ccnc(N5CCN(C)CC5)c4)ncc3cn2)n1C]
4130
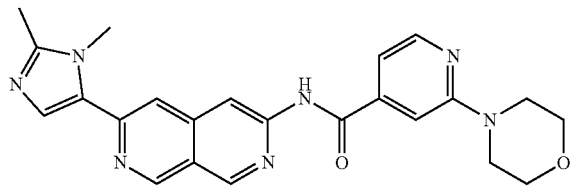 [SMILES: Cc1ncc(-c2cc3cc(NC(=O)c4ccnc(N5CCOCC5)c4)ncc3cn2)n1C]
4131
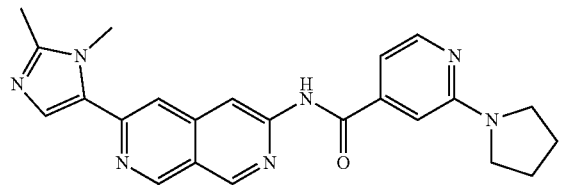 [SMILES: Cc1ncc(-c2cc3cc(NC(=O)c4ccnc(N5CCCC5)c4)ncc3cn2)n1C]
4132
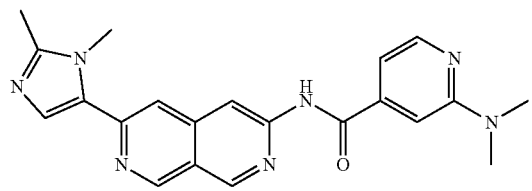 [SMILES: Cc1ncc(-c2cc3cc(NC(=O)c4ccnc(N(C)C)c4)ncc3cn2)n1C]
4133
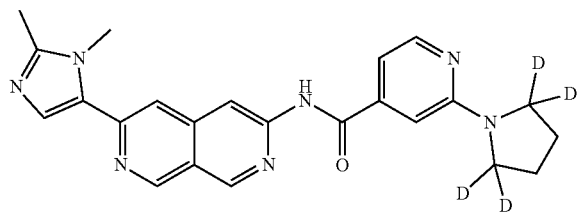 [SMILES: [2H]C1([2H])CCC([2H])([2H])N1c1cc(C(=O)Nc2cc3cc(-c4cnc(C)n4C)ncc3cn2)ccn1]
4134
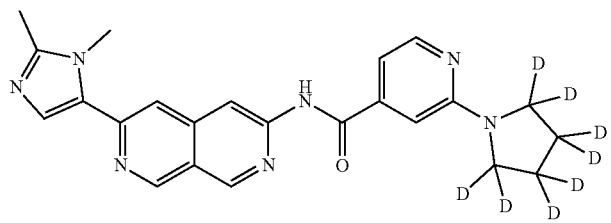 [SMILES: [2H]C1([2H])N(c2cc(C(=O)Nc3cc4cc(-c5cnc(C)n5C)ncc4cn3)ccn2)C([2H])([2H])C([2H])([2H])C1([2H])[2H]]
4135
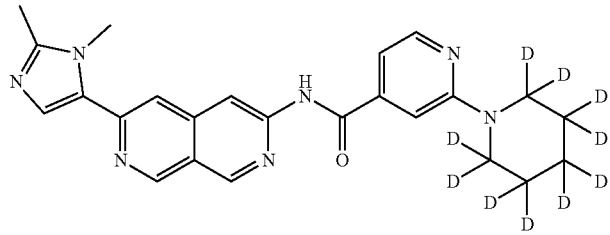 [SMILES: [2H]C1([2H])N(c2cc(C(=O)Nc3cc4cc(-c5cnc(C)n5C)ncc4cn3)ccn2)C([2H])([2H])C([2H])([2H])C([2H])([2H])C1([2H])[2H]]
4136

TABLE 1-continued
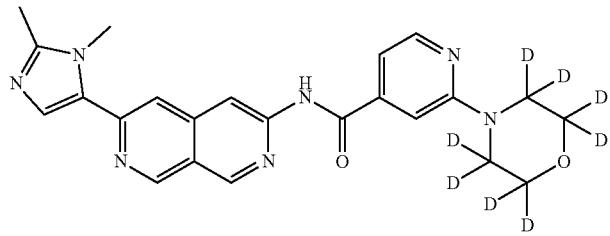 [SMILES: [2H]C1([2H])OC([2H])([2H])C([2H])([2H])N(c2cc(C(=O)Nc3cc4cc(-c5cnc(C)n5C)ncc4cn3)ccn2)C1([2H])[2H]] 4137
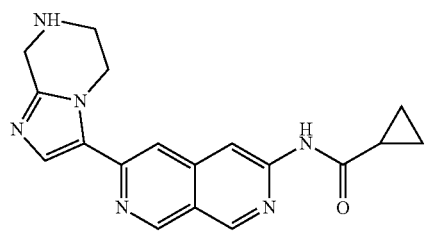 [SMILES: O=C(Nc1cc2cc(-c3cnc4n3CCNC4)ncc2cn1)C1CC1] 4138
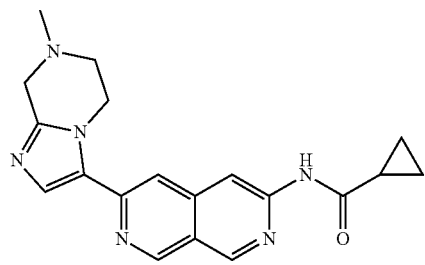 [SMILES: CN1CCn2c(-c3cc4cc(NC(=O)C5CC5)ncc4cn3)cnc2C1] 4139
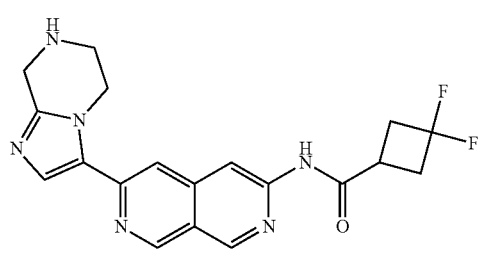 [SMILES: O=C(Nc1cc2cc(-c3cnc4n3CCNC4)ncc2cn1)C1CC(F)(F)C1] 4140
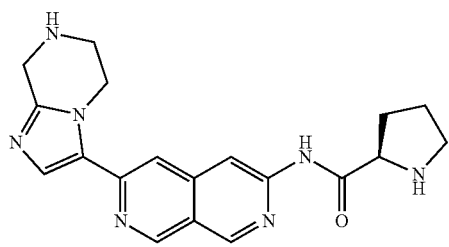 [SMILES: O=C(Nc1cc2cc(-c3cnc4n3CCNC4)ncc2cn1)[C@H]1CCCN1] 4141
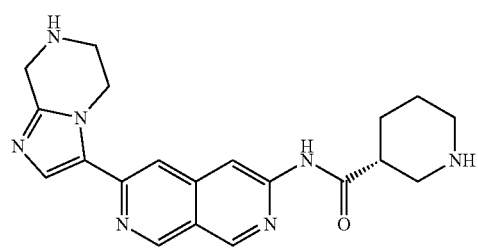 [SMILES: O=C(Nc1cc2cc(-c3cnc4n3CCNC4)ncc2cn1)[C@@H]1CCCNC1] 4142

TABLE 1-continued
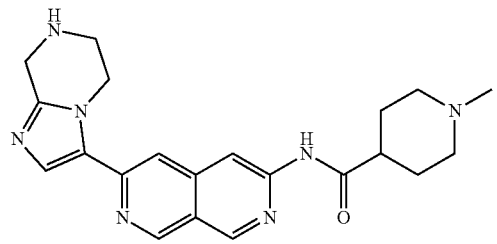 [SMILES: CN1CCC(C(=O)Nc2cc3cc(-c4cnc5n4CCNC5)ncc3cn2)CC1]
4143
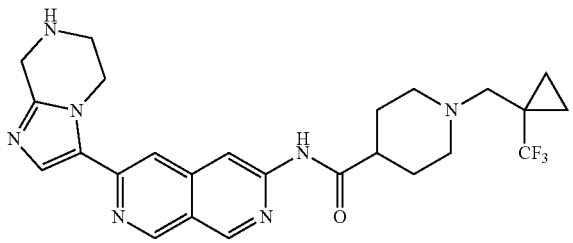 [SMILES: O=C(Nc1cc2cc(-c3cnc4n3CCNC4)ncc2cn1)C1CCN(CC2(C(F)(F)F)CC2)CC1]
4144
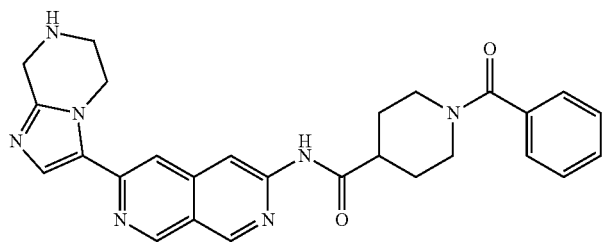 [SMILES: O=C(Nc1cc2cc(-c3cnc4n3CCNC4)ncc2cn1)C1CCN(C(=O)c2ccccc2)CC1]
4145
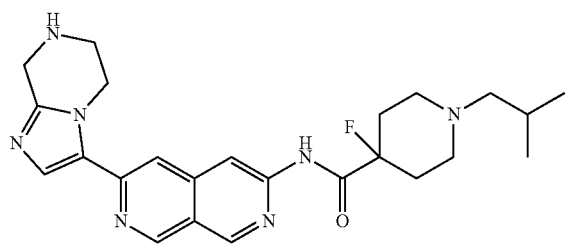 [SMILES: CC(C)CN1CCC(F)(C(=O)Nc2cc3cc(-c4cnc5n4CCNC5)ncc3cn2)CC1]
4146
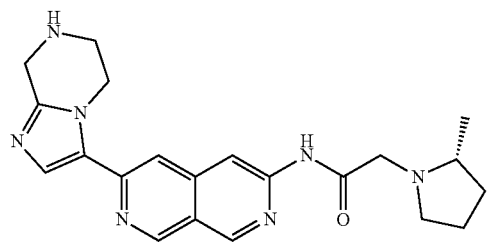 [SMILES: C[C@@H]1CCCN1CC(=O)Nc1cc2cc(-c3cnc4n3CCNC4)ncc2cn1]
4147
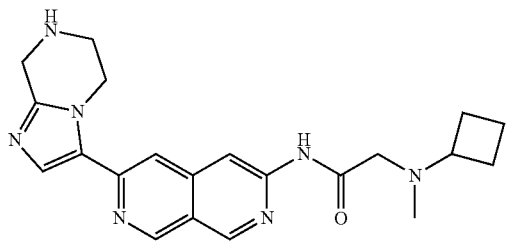 [SMILES: CN(CC(=O)Nc1cc2cc(-c3cnc4n3CCNC4)ncc2cn1)C1CCC1]
4148

TABLE 1-continued
| | |
|---|---|
| 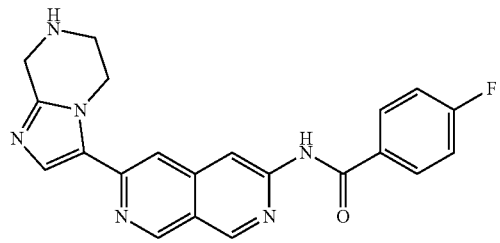 [SMILES: O=C(Nc1cc2cc(-c3cnc4n3CCNC4)ncc2cn1)c1ccc(F)cc1] | 4149 |
| 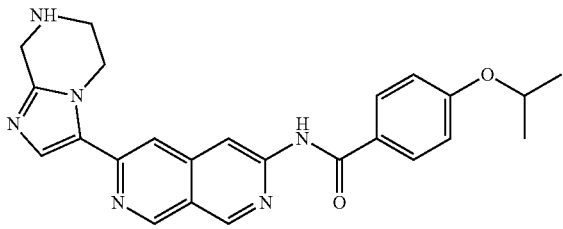 [SMILES: CC(C)Oc1ccc(C(=O)Nc2cc3cc(-c4cnc5n4CCNC5)ncc3cn2)cc1] | 4150 |
| 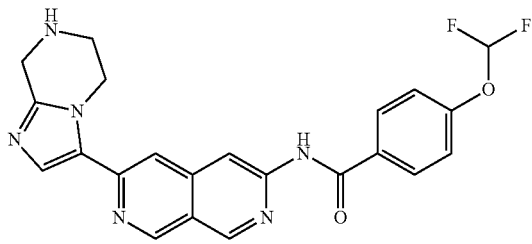 [SMILES: O=C(Nc1cc2cc(-c3cnc4n3CCNC4)ncc2cn1)c1ccc(OC(F)F)cc1] | 4151 |
| 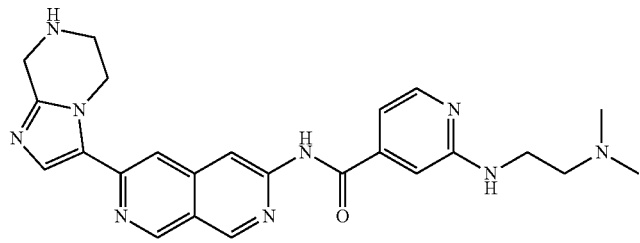 [SMILES: CN(C)CCNc1cc(C(=O)Nc2cc3cc(-c4cnc5n4CCNC5)ncc3cn2)ccn1] | 4152 |
| 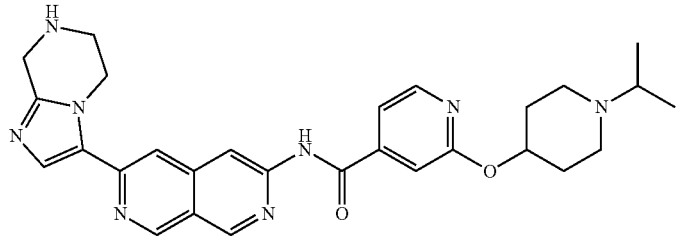 [SMILES: CC(C)N1CCC(Oc2cc(C(=O)Nc3cc4cc(-c5cnc6n5CCNC6)ncc4cn3)ccn2)CC1] | 4153 |
| 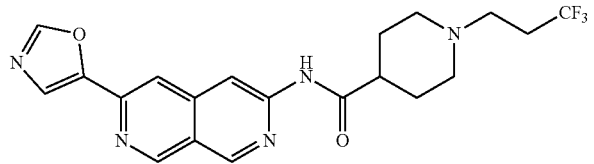 [SMILES: O=C(Nc1cc2cc(-c3cnco3)ncc2cn1)C1CCN(CCC(F)(F)F)CC1] | 4154 |
| 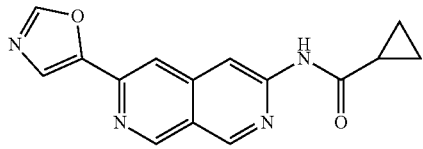 [SMILES: O=C(Nc1cc2cc(-c3cnco3)ncc2cn1)C1CC1] | 4155 |

TABLE 1-continued
| | |
|---|---|
| 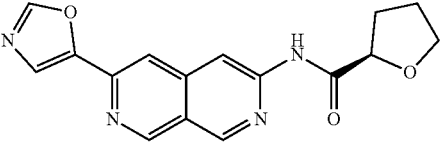 [SMILES: O=C(Nc1cc2cc(-c3cnco3)ncc2cn1)[C@H]1CCCO1] | 4156 |
| 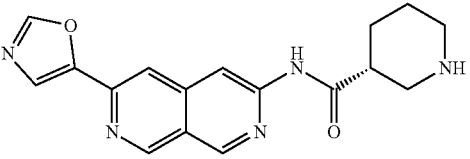 [SMILES: O=C(Nc1cc2cc(-c3cnco3)ncc2cn1)[C@@H]1CCCNC1] | 4157 |
| 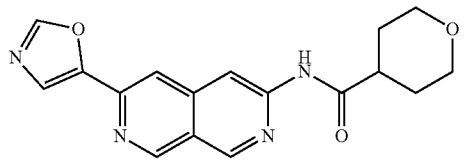 [SMILES: O=C(Nc1cc2cc(-c3cnco3)ncc2cn1)C1CCOCC1] | 4158 |
| 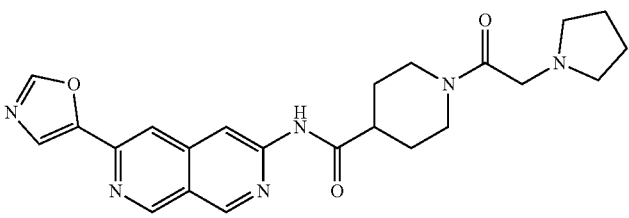 | 4159 |
| 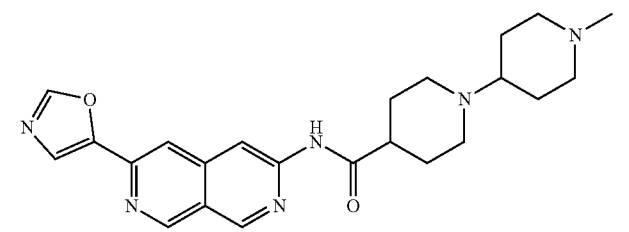 | 4160 |
| 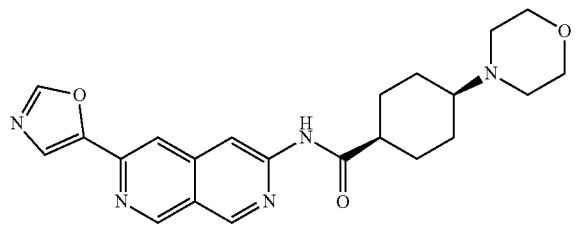 [SMILES: O=C(Nc1cc2cc(-c3cnco3)ncc2cn1)[C@H]1CC[C@@H](N2CCOCC2)CC1] | 4161 |
| 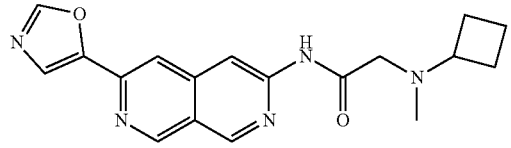 [SMILES: CN(CC(=O)Nc1cc2cc(-c3cnco3)ncc2cn1)C1CCC1] | 4162 |
| 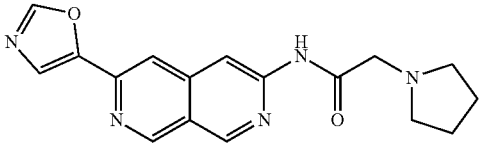 [SMILES: O=C(CN1CCCC1)Nc1cc2cc(-c3cnco3)ncc2cn1] | 4163 |

TABLE 1-continued
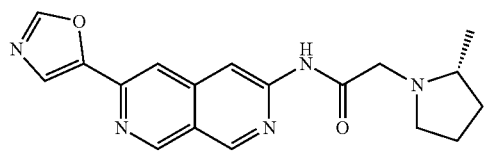 [SMILES: C[C@@H]1CCCN1CC(=O)Nc1cc2cc(-c3cnco3)ncc2cn1] 4164
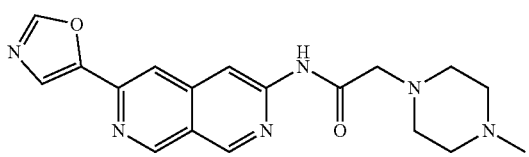 [SMILES: CN1CCN(CC(=O)Nc2cc3cc(-c4cnco4)ncc3cn2)CC1] 4165
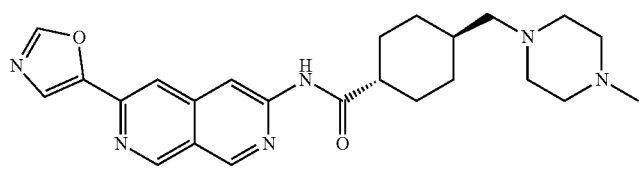 [SMILES: CN1CCN(C[C@H]2CC[C@H](C(=O)Nc3cc4cc(-c5cnco5)ncc4cn3)CC2)CC1] 4166
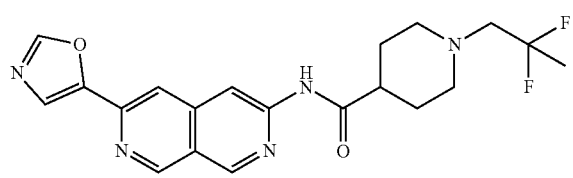 [SMILES: CC(F)(F)CN1CCC(C(=O)Nc2cc3cc(-c4cnco4)ncc3cn2)CC1] 4167
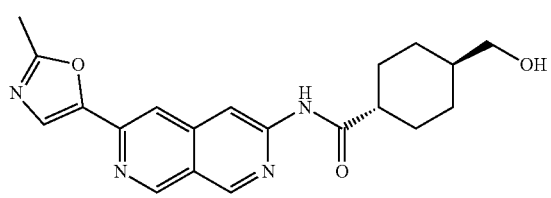 4168
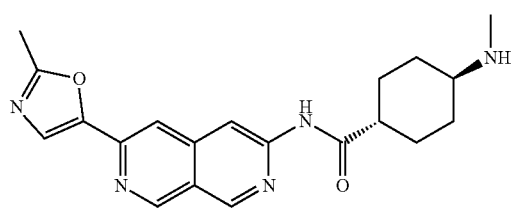 [SMILES: CN[C@H]1CC[C@H](C(=O)Nc2cc3cc(-c4cnc(C)o4)ncc3cn2)CC1] 4169
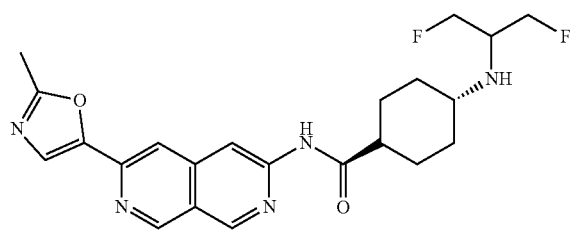 4170
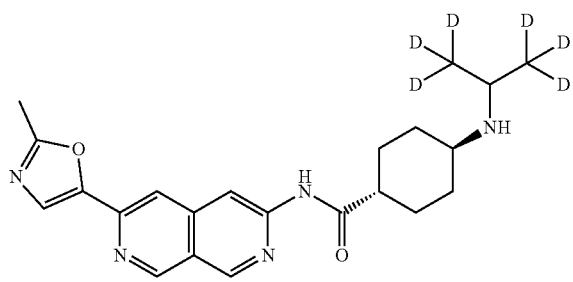 [SMILES: [2H]C([2H])([2H])C(N[C@H]1CC[C@H](C(=O)Nc2cc3cc(-c4cnc(C)o4)ncc3cn2)CC1)C([2H])([2H])[2H]] 4171

TABLE 1-continued
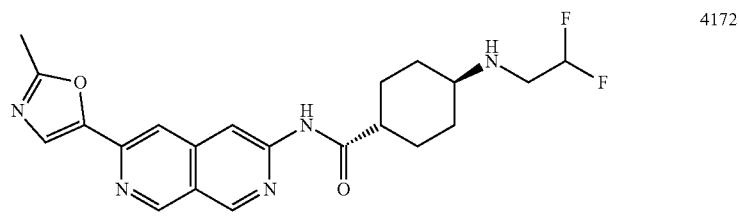 4172
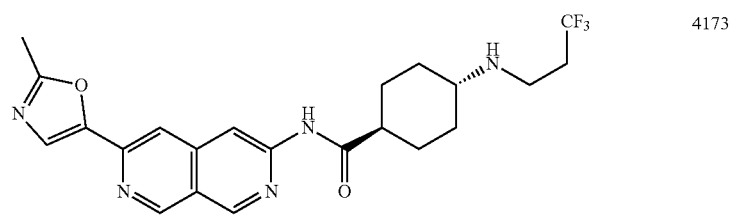 4173
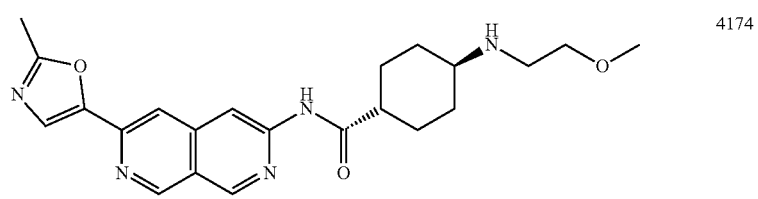 4174
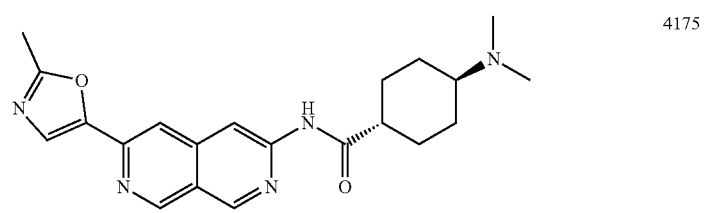 4175
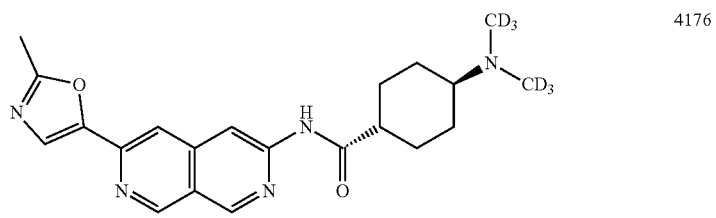 4176
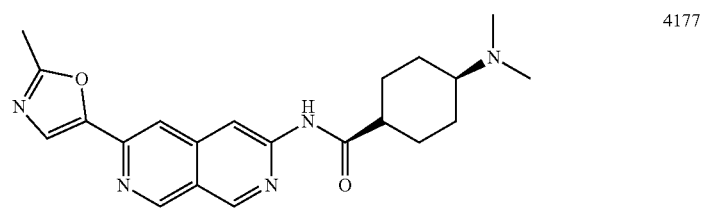 4177
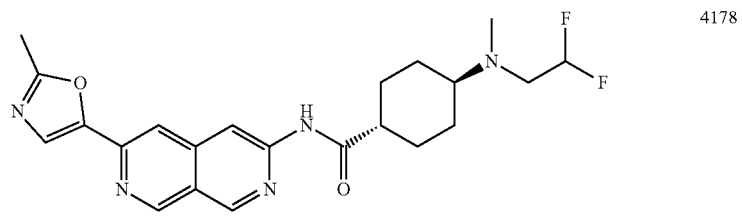 4178

TABLE 1-continued
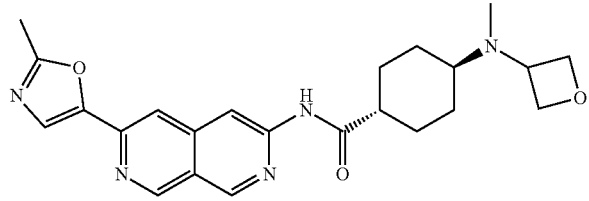 [SMILES: Cc1ncc(-c2cc3cc(NC(=O)[C@H]4CC[C@H](N(C)C5COC5)CC4)ncc3cn2)o1] 4179
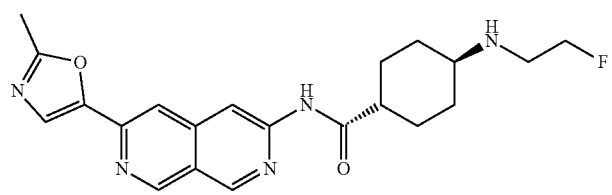 4180
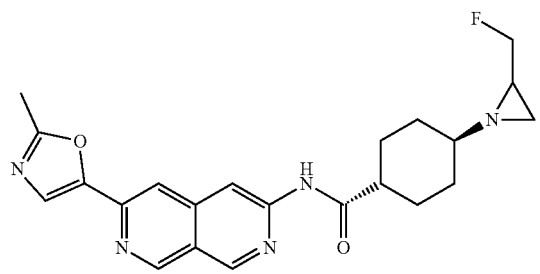 4181
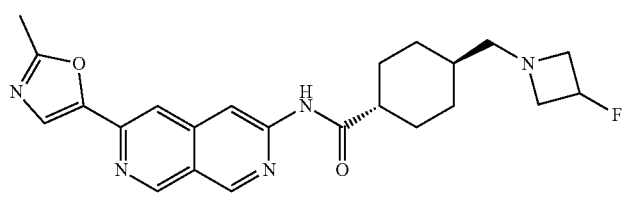 [SMILES: Cc1ncc(-c2cc3cc(NC(=O)[C@H]4CC[C@H](CN5CC(F)C5)CC4)ncc3cn2)o1] 4182
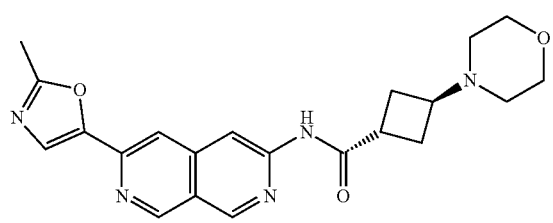 4183
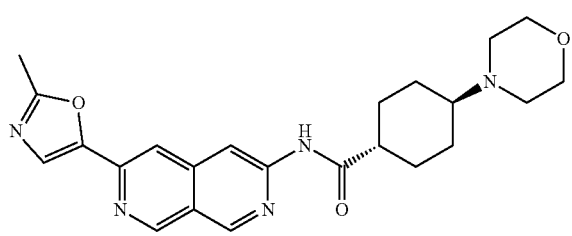 [SMILES: Cc1ncc(-c2cc3cc(NC(=O)[C@H]4CC[C@H](N5CCOCC5)CC4)ncc3cn2)o1] 4184
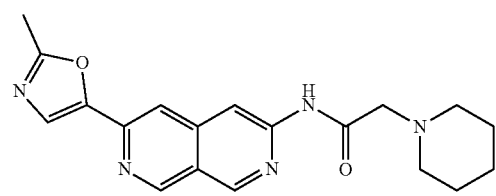 [SMILES: Cc1ncc(-c2cc3cc(NC(=O)CN4CCCCC4)ncc3cn2)o1] 4185

TABLE 1-continued
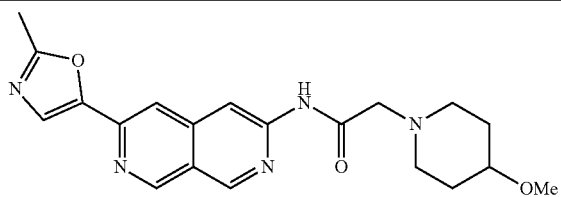
4186
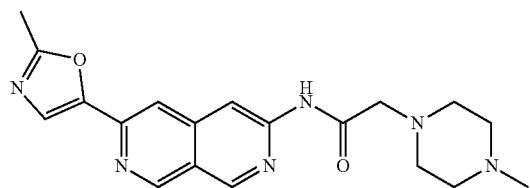
4187
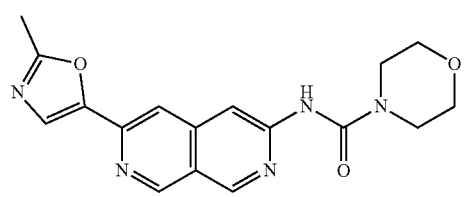 [SMILES: Cc1ncc(-c2cc3cc(NC(=O)N4CCOCC4)ncc3cn2)o1]
4188
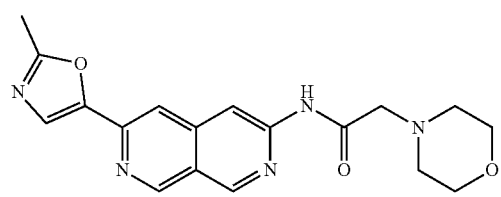 [SMILES: Cc1ncc(-c2cc3cc(NC(=O)CN4CCOCC4)ncc3cn2)o1]
4189
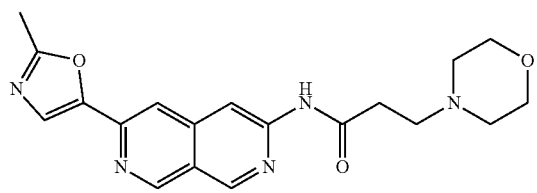 [SMILES: Cc1ncc(-c2cc3cc(NC(=O)CCN4CCOCC4)ncc3cn2)o1]
4190
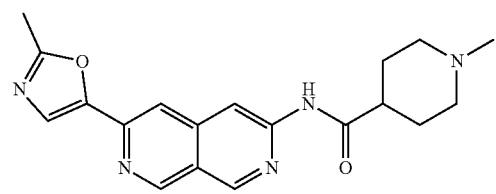 [SMILES: Cc1ncc(-c2cc3cc(NC(=O)C4CCN(C)CC4)ncc3cn2)o1]
4191
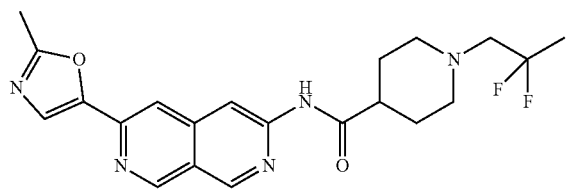 [SMILES: Cc1ncc(-c2cc3cc(NC(=O)C4CCN(CC(C)(F)F)CC4)ncc3cn2)o1]
4192
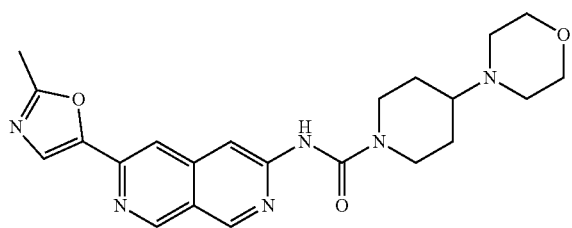 [SMILES: Cc1ncc(-c2cc3cc(NC(=O)N4CCC(N5CCOCC5)CC4)ncc3cn2)o1]
4193

TABLE 1-continued
| | |
|---|---|
| 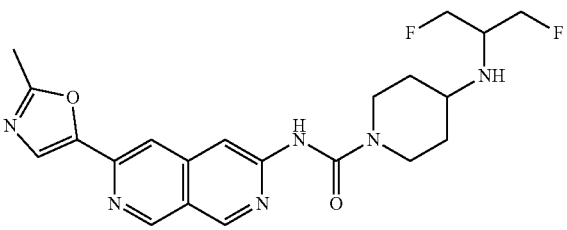 [SMILES: Cc1ncc(-c2cc3cc(NC(=O)N4CCC(NC(CF)CF)CC4)ncc3cn2)o1] | 4194 |
| 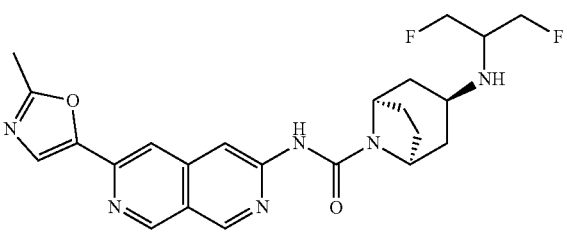 | 4195 |
| 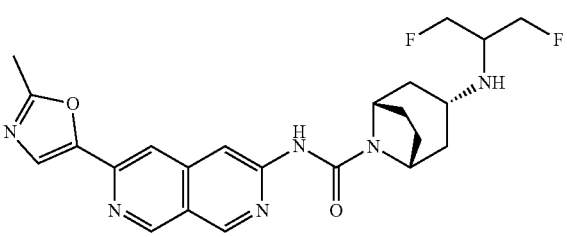 [SMILES: Cc1ncc(-c2cc3cc(NC(=O)N4[C@@H]5CC[C@H]4C[C@H](NC(CF)CF)C5)ncc3cn2)o1] | 4196 |
| 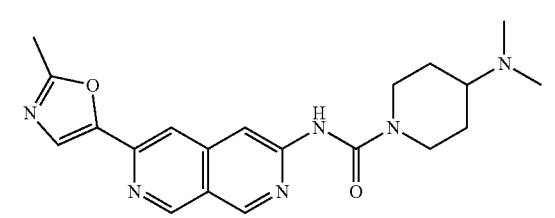 [SMILES: Cc1ncc(-c2cc3cc(NC(=O)N4CCC(N(C)C)CC4)ncc3cn2)o1] | 4197 |
| 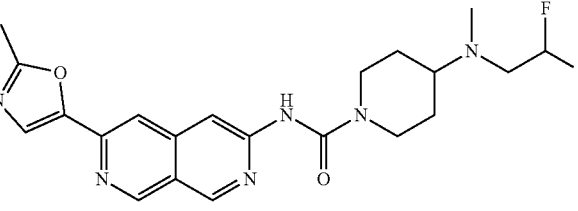 | 4198 |
| 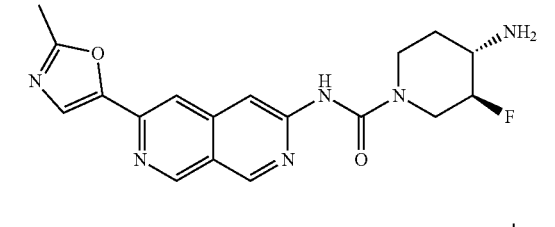 | 4199 |
| 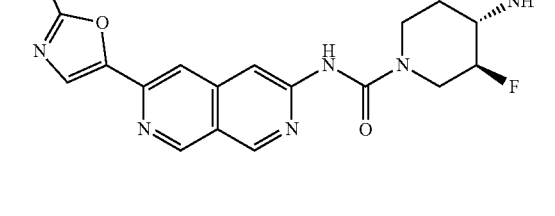 | 4200 |

TABLE 1-continued
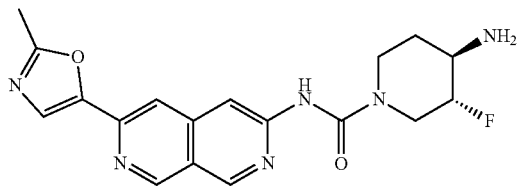 [SMILES: Cc1ncc(-c2cc3cc(NC(=O)N4CC[C@@H](N)[C@H](F)C4)ncc3cn2)o1]
4201
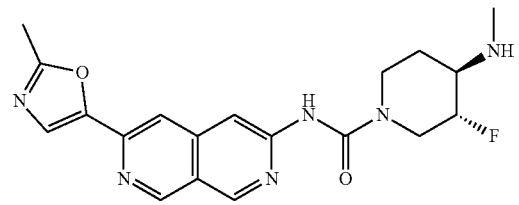 [SMILES: CN[C@@H]1CCN(C(=O)Nc2cc3cc(-c4cnc(C)o4)ncc3cn2)C[C@H]1F]
4202
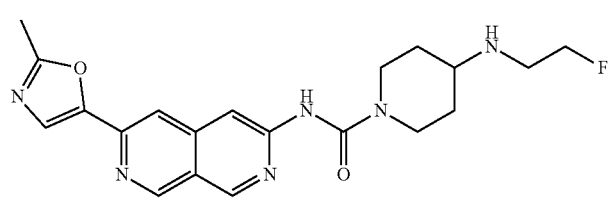 [SMILES: Cc1ncc(-c2cc3cc(NC(=O)N4CCC(NCCF)CC4)ncc3cn2)o1]
4203
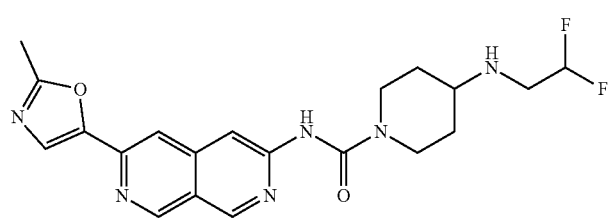 [SMILES: Cc1ncc(-c2cc3cc(NC(=O)N4CCC(NCC(F)F)CC4)ncc3cn2)o1]
4204
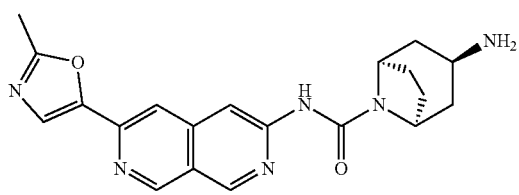 [SMILES: Cc1ncc(-c2cc3cc(NC(=O)N4[C@@H]5CC[C@H]4C[C@H](N)C5)ncc3cn2)o1]
4205
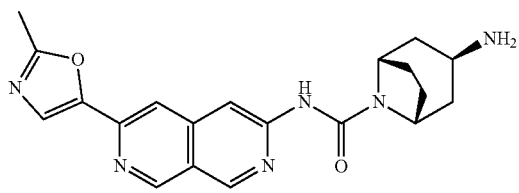 [SMILES: Cc1ncc(-c2cc3cc(NC(=O)N4[C@@H]5CC[C@H]4C[C@@H](N)C5)ncc3cn2)o1]
4206
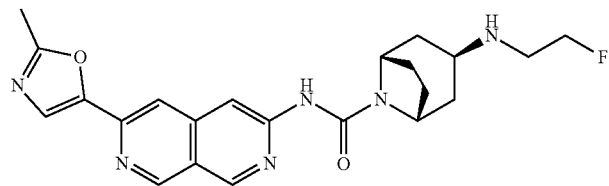 [SMILES: Cc1ncc(-c2cc3cc(NC(=O)N4[C@@H]5CC[C@H]4C[C@@H](NCCF)C5)ncc3cn2)o1]
4207
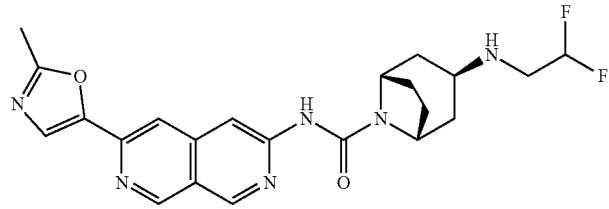 [SMILES: Cc1ncc(-c2cc3cc(NC(=O)N4[C@@H]5CC[C@H]4C[C@@H](NCC(F)F)C5)ncc3cn2)o1]
4208

TABLE 1-continued
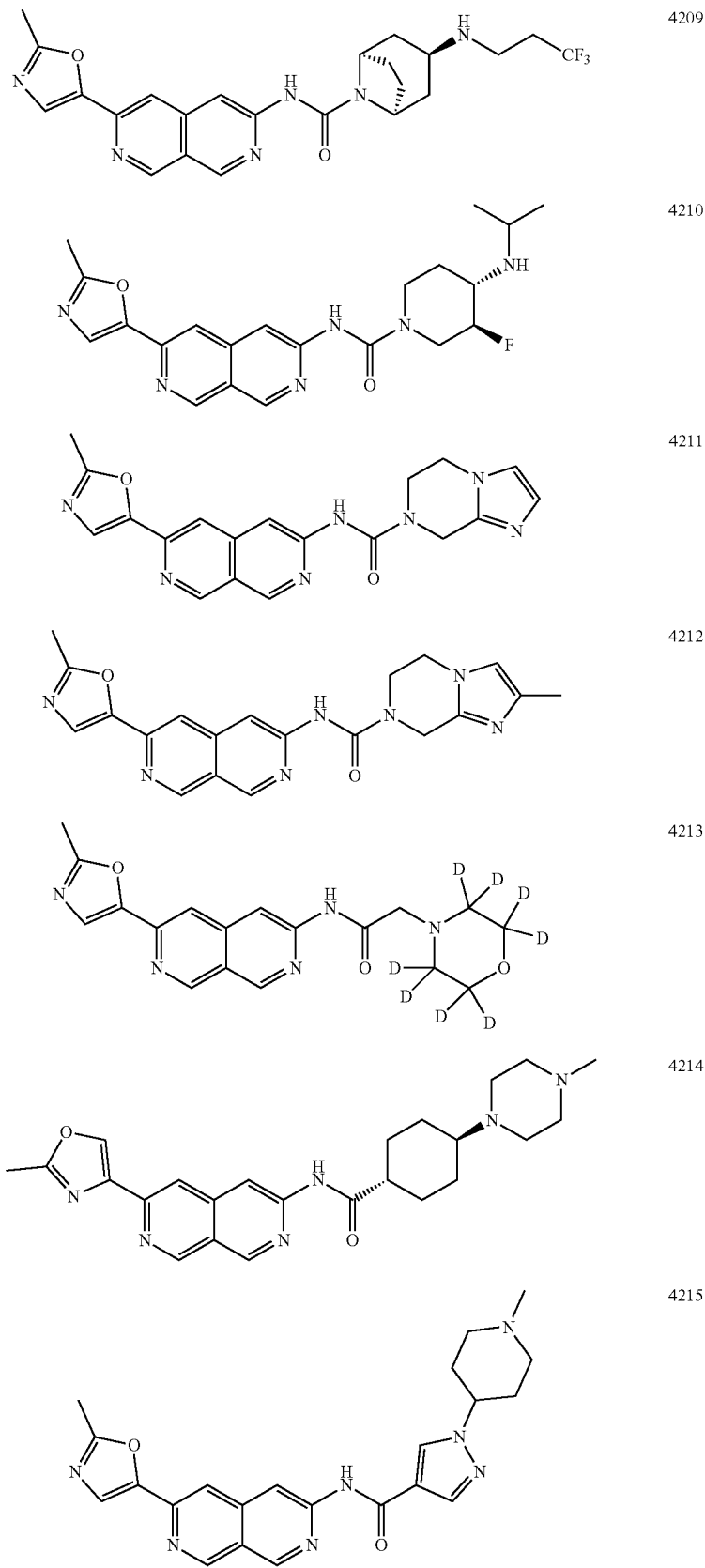
4209
4210
4211
4212
4213
4214
4215

TABLE 1-continued
| | |
|---|---|
| 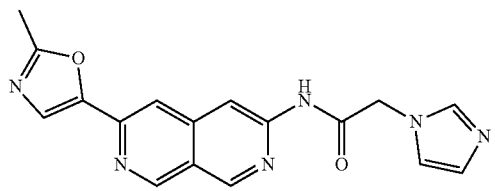 [SMILES: Cc1ncc(-c2cc3cc(NC(=O)Cn4ccnc4)ncc3cn2)o1] | 4216 |
| 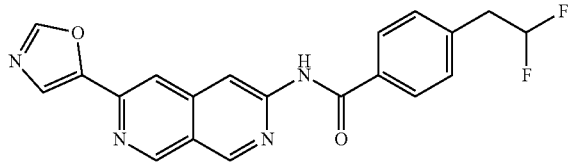 [SMILES: O=C(Nc1cc2cc(-c3cnco3)ncc2cn1)c1ccc(CC(F)F)cc1] | 4217 |
| 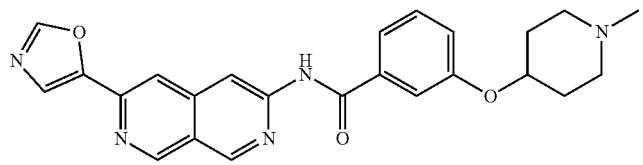 [SMILES: CN1CCC(Oc2cccc(C(=O)Nc3cc4cc(-c5cnco5)ncc4cn3)c2)CC1] | 4218 |
| 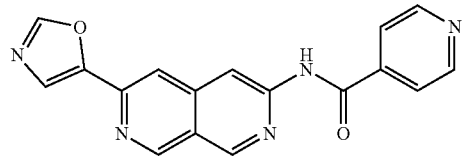 | 4219 |
| 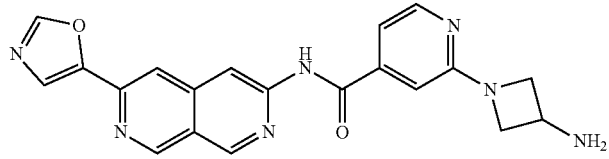 | 4220 |
| 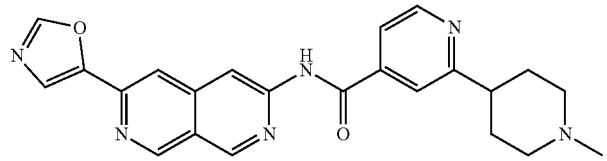 [SMILES: CN1CCC(c2cc(C(=O)Nc3cc4cc(-c5cnco5)ncc4cn3)ccn2)CC1] | 4221 |
| 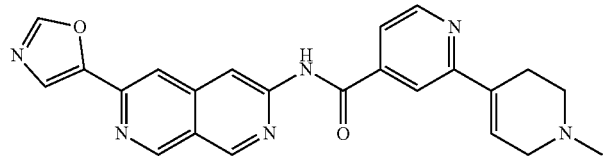 [SMILES: CN1CC=C(c2cc(C(=O)Nc3cc4cc(-c5cnco5)ncc4cn3)ccn2)CC1] | 4222 |
| 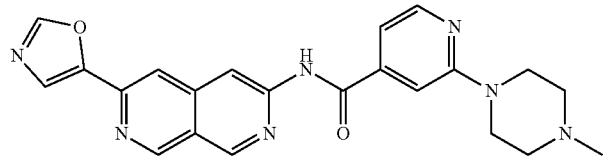 | 4223 |
| 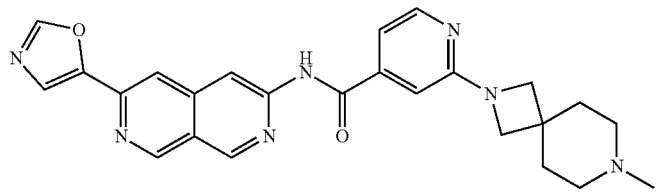 [SMILES: CN1CCC2(CC1)CN(c1cc(C(=O)Nc3cc4cc(-c5cnco5)ncc4cn3)ccn1)C2] | 4224 |

TABLE 1-continued
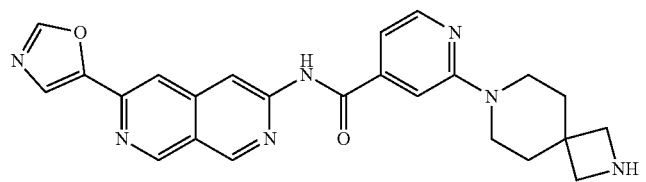 4225
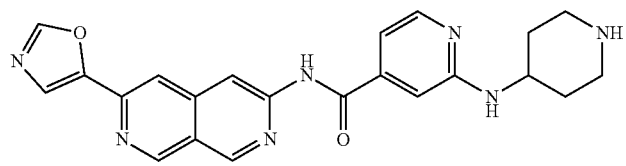 [SMILES: O=C(Nc1cc2cc(-c3cnco3)ncc2cn1)c1ccnc(NC2CCNCC2)c1] 4226
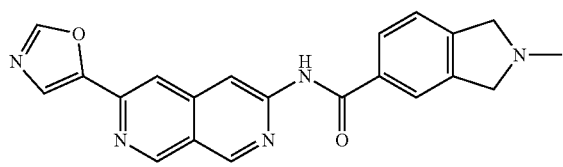 [SMILES: CN1Cc2ccc(C(=O)Nc3cc4cc(-c5cnco5)ncc4cn3)cc2C1] 4227
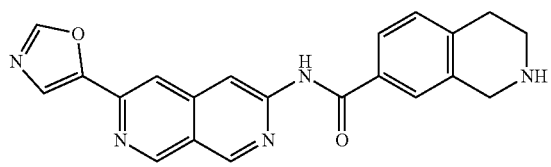 4228
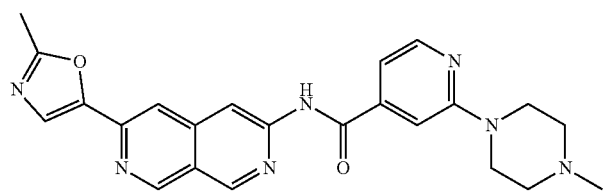 4229
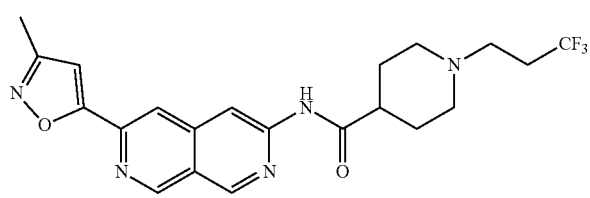 [SMILES: Cc1cc(-c2cc3cc(NC(=O)C4CCN(CCC(F)(F)F)CC4)ncc3cn2)on1] 4230
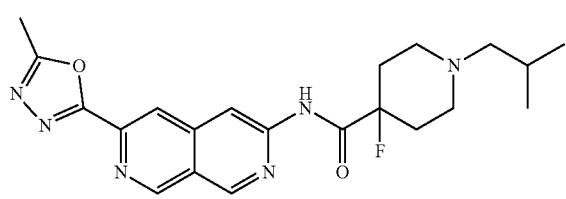 4231
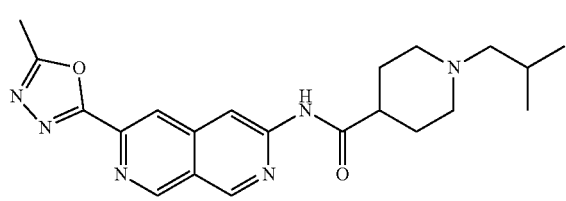 [SMILES: Cc1nnc(-c2cc3cc(NC(=O)C4CCN(CC(C)C)CC4)ncc3cn2)o1] 4232

TABLE 1-continued
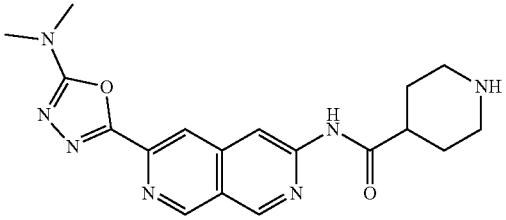 [SMILES: CN(C)c1nnc(-c2cc3cc(NC(=O)C4CCNCC4)ncc3cn2)o1]
4233
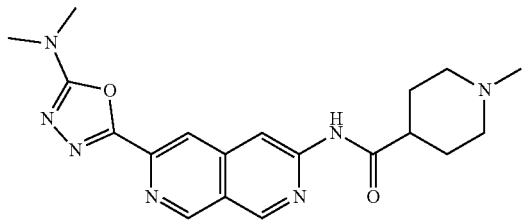
4234
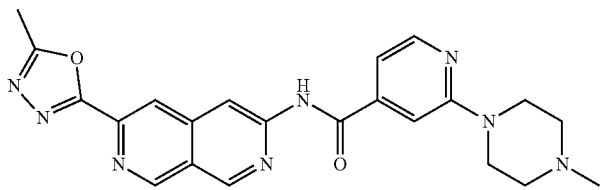
4235
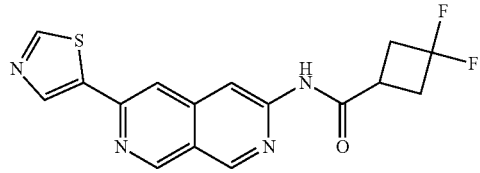 [SMILES: O=C(Nc1cc2cc(-c3cncs3)ncc2cn1)C1CC(F)(F)C1]
4236
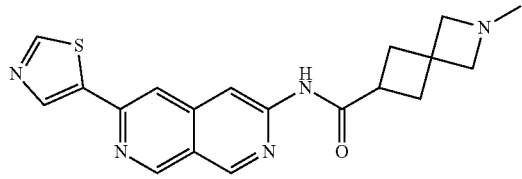
4237
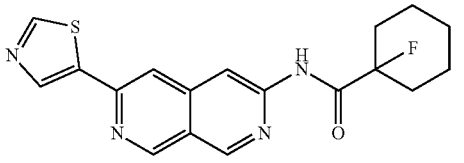
4238
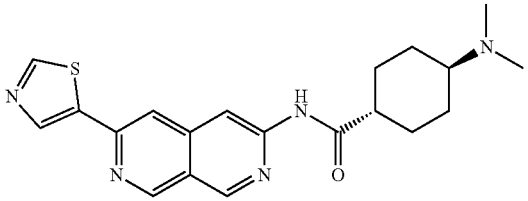 [SMILES: CN(C)[C@H]1CC[C@H](C(=O)Nc2cc3cc(-c4cncs4)ncc3cn2)CC1]
4239
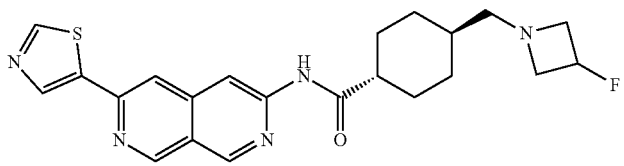 [SMILES: O=C(Nc1cc2cc(-c3cncs3)ncc2cn1)[C@H]1CC[C@H](CN2CC(F)C2)CC1]
4240

TABLE 1-continued

| | |
|---|---|
| (structure) | 4241 |
| (structure) | 4242 |
| (structure) | 4243 |
| (structure) | 4244 |
| (structure) | 4245 |
| (structure) | 4246 |
| (structure) | 4247 |
| (structure) | 4248 |
| (structure) | 4249 |

TABLE 1-continued
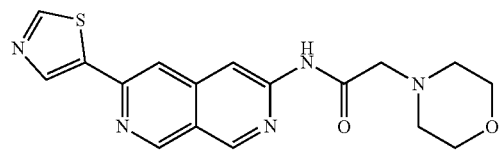 [SMILES: O=C(CN1CCOCC1)Nc1cc2cc(-c3cncs3)ncc2cn1] 4250
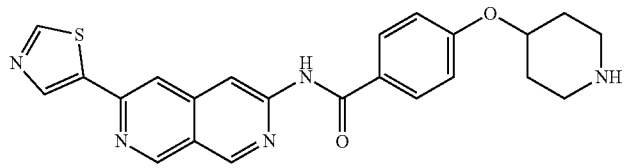 [SMILES: O=C(Nc1cc2cc(-c3cncs3)ncc2cn1)c1ccc(OC2CCNCC2)cc1] 4251
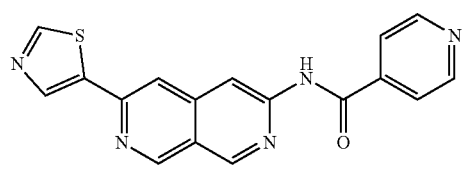 [SMILES: O=C(Nc1cc2cc(-c3cncs3)ncc2cn1)c1ccncc1] 4252
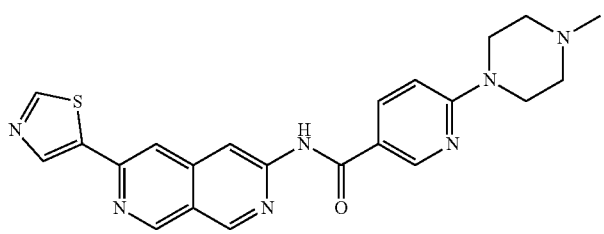 4253
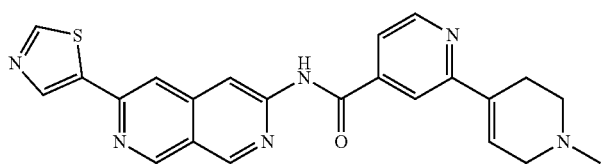 [SMILES: CN1CC=C(c2cc(C(=O)Nc3cc4cc(-c5cncs5)ncc4cn3)ccn2)CC1] 4254
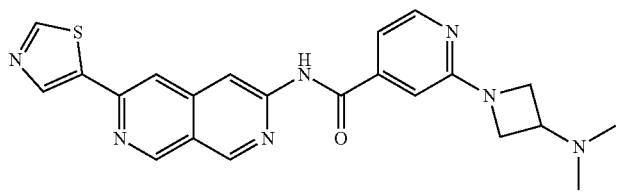 [SMILES: CN(C)C1CN(c2cc(C(=O)Nc3cc4cc(-c5cncs5)ncc4cn3)ccn2)C1] 4255
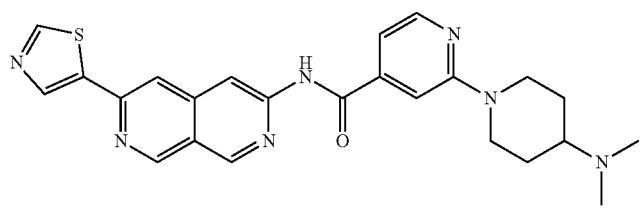 [SMILES: CN(C)C1CCN(c2cc(C(=O)Nc3cc4cc(-c5cncs5)ncc4cn3)ccn2)CC1] 4256
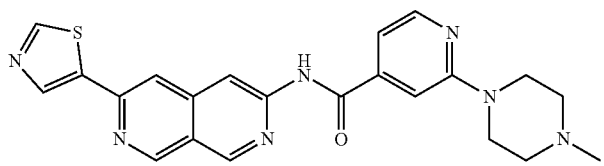 [SMILES: CN1CCN(c2cc(C(=O)Nc3cc4cc(-c5cncs5)ncc4cn3)ccn2)CC1] 4257

TABLE 1-continued
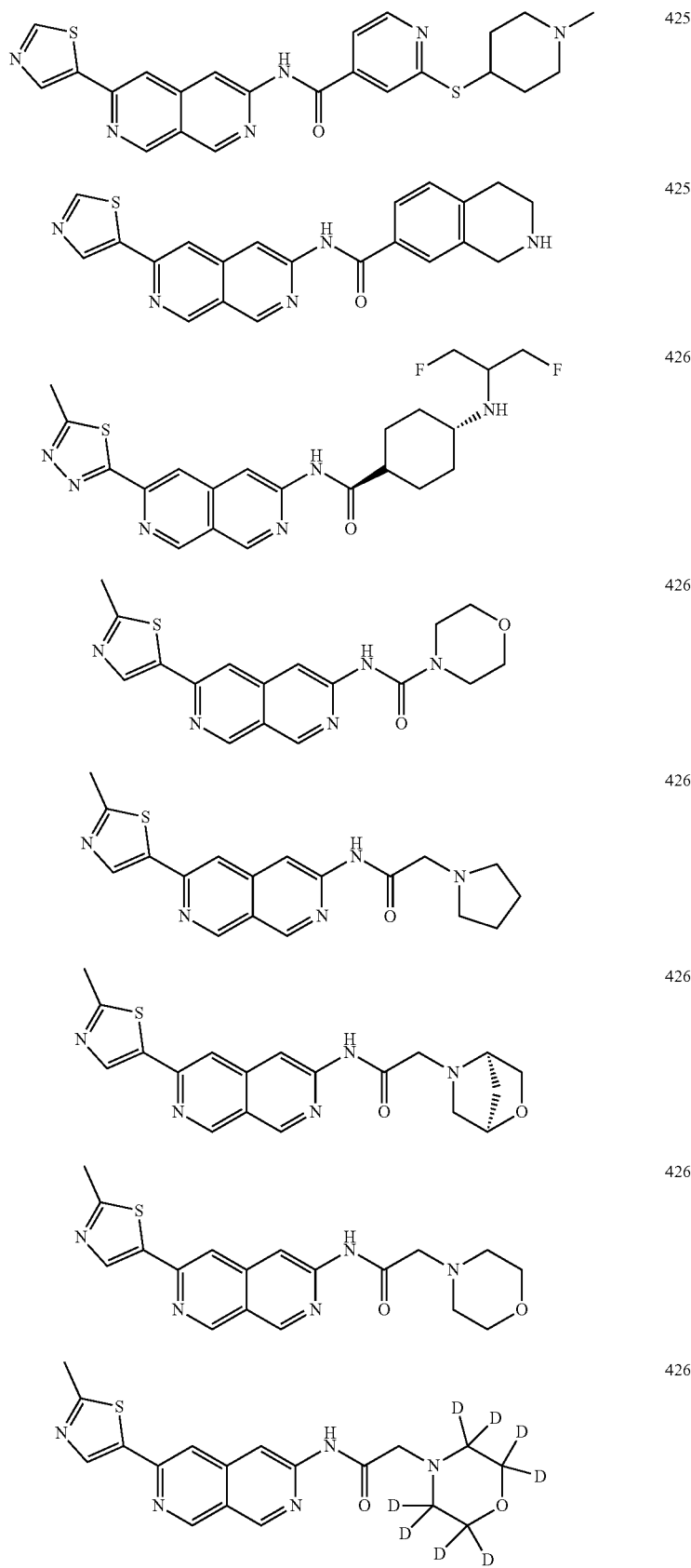

TABLE 1-continued
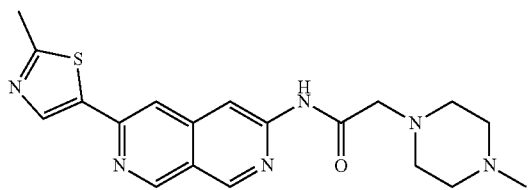 [SMILES: Cc1ncc(-c2cc3cc(NC(=O)CN4CCN(C)CC4)ncc3cn2)s1] 4266
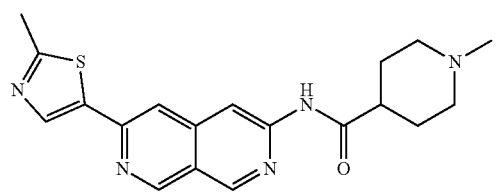 [SMILES: Cc1ncc(-c2cc3cc(NC(=O)C4CCN(C)CC4)ncc3cn2)s1] 4267
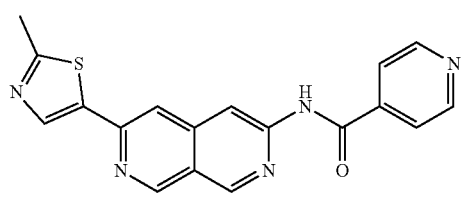 [SMILES: Cc1ncc(-c2cc3cc(NC(=O)c4ccncc4)ncc3cn2)s1] 4268
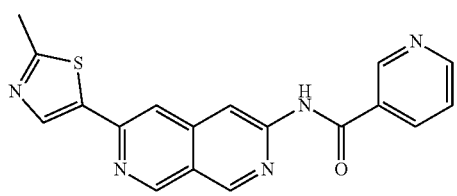 [SMILES: Cc1ncc(-c2cc3cc(NC(=O)c4cccnc4)ncc3cn2)s1] 4269
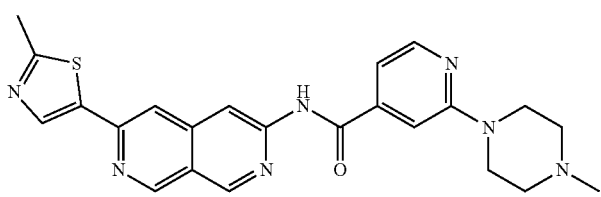 4270
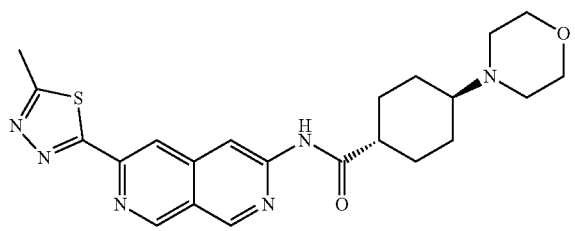 4271
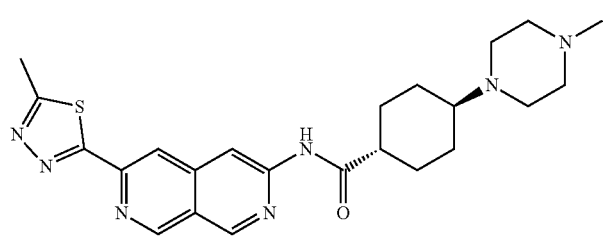 [SMILES: Cc1nnc(-c2cc3cc(NC(=O)[C@H]4CC[C@H](N5CCN(C)CC5)CC4)ncc3cn2)s1] 4272

TABLE 1-continued

| | |
|---|---|
| (structure) | 4273 |
| (structure) | 4274 |
| (structure) | 4275 |
| (structure) | 4276 |
| (structure) | 4277 |
| (structure) | 4278 |
| (structure) | 4279 |

TABLE 1-continued
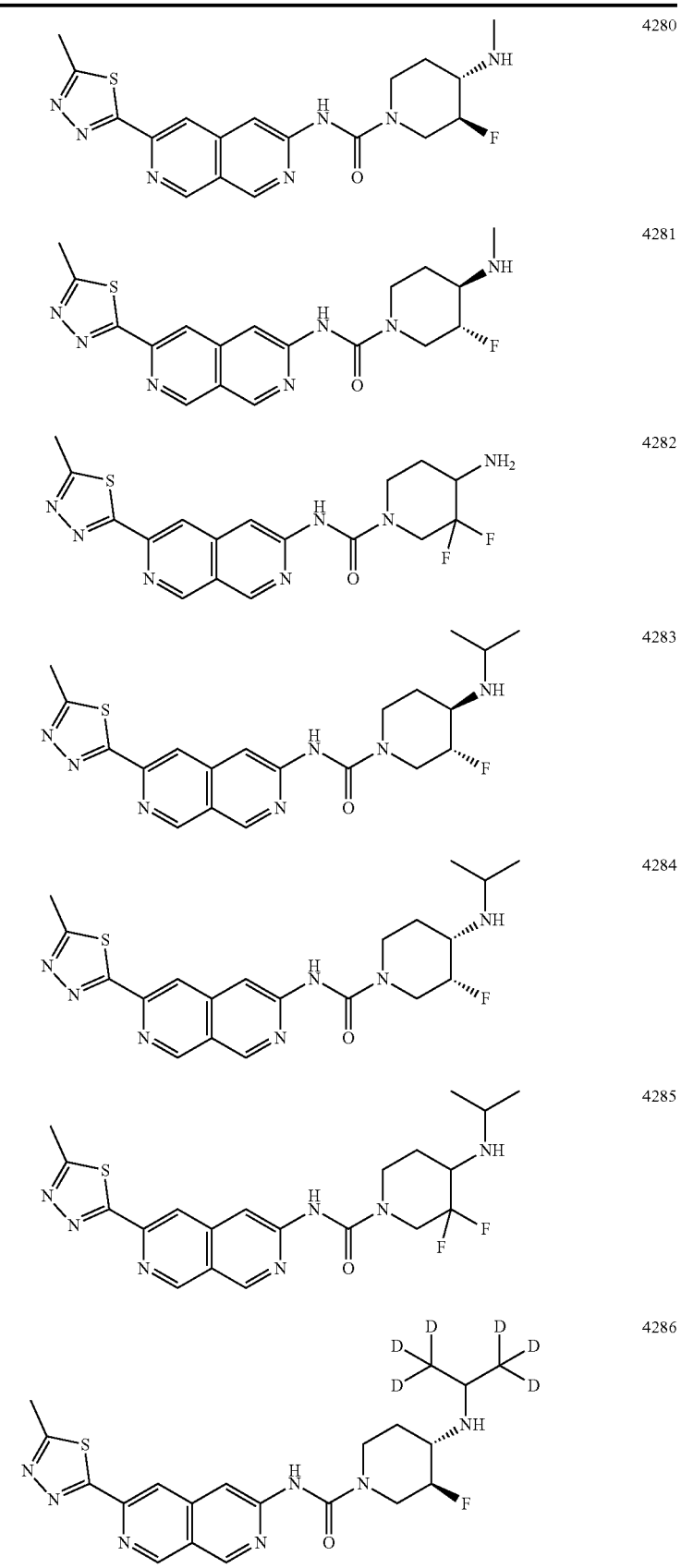
4280
4281
4282
4283
4284
4285
4286

TABLE 1-continued
| 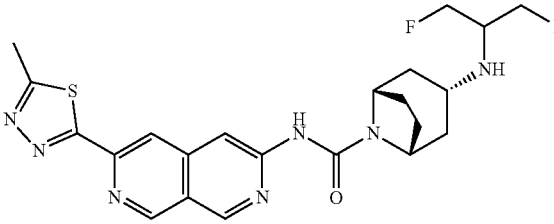 | 4287 |
| 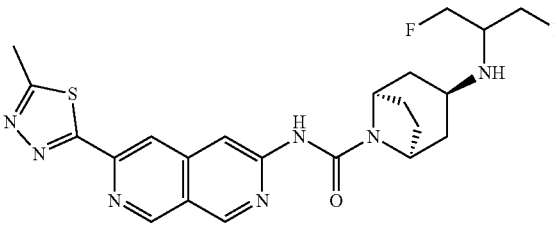 | 4288 |
| 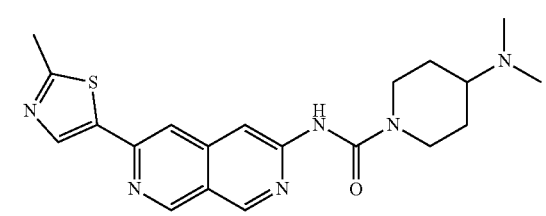 [SMILES: Cc1ncc(-c2cc3cc(NC(=O)N4CCC(N(C)C)CC4)ncc3cn2)s1] | 4289 |
| 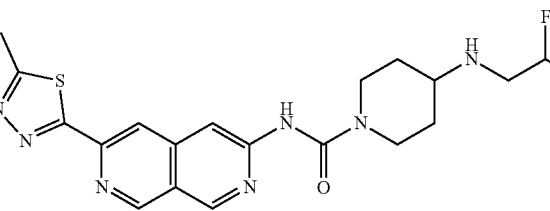 | 4290 |
| 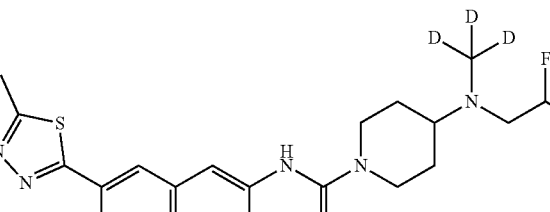 | 4291 |
| 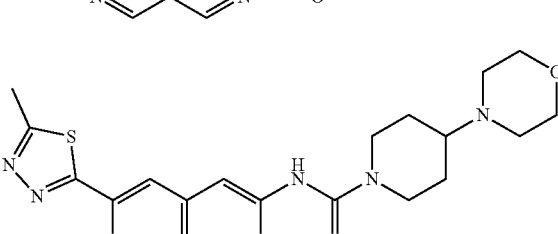 | 4292 |
|  | 4293 |

TABLE 1-continued
| | |
|---|---|
| 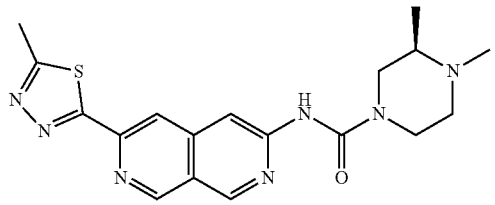 [SMILES: Cc1nnc(-c2cc3cc(NC(=O)N4CCN(C)[C@H](C)C4)ncc3cn2)s1] | 4294 |
| 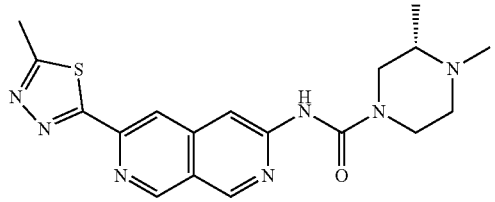 | 4295 |
| 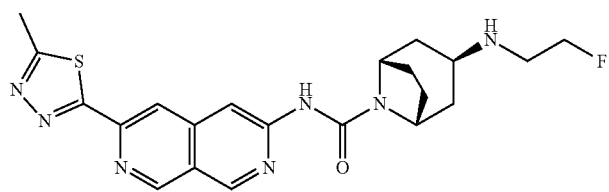 [SMILES: Cc1nnc(-c2cc3cc(NC(=O)N4[C@@H]5CC[C@H]4C[C@@H](NCCF)C5)ncc3cn2)s1] | 4296 |
| 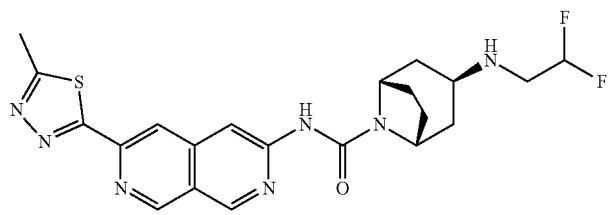 | 4297 |
| 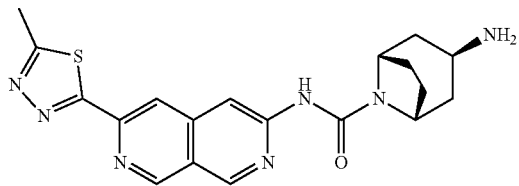 [SMILES: Cc1nnc(-c2cc3cc(NC(=O)N4[C@@H]5CC[C@H]4C[C@@H](N)C5)ncc3cn2)s1] | 4298 |
| 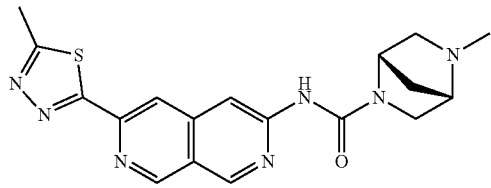 [SMILES: Cc1nnc(-c2cc3cc(NC(=O)N4C[C@@H]5C[C@H]4CN5C)ncc3cn2)s1] | 4299 |
| 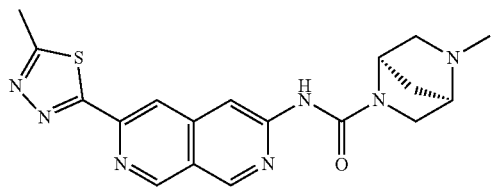 [SMILES: Cc1nnc(-c2cc3cc(NC(=O)N4C[C@H]5C[C@@H]4CN5C)ncc3cn2)s1] | 4300 |
| 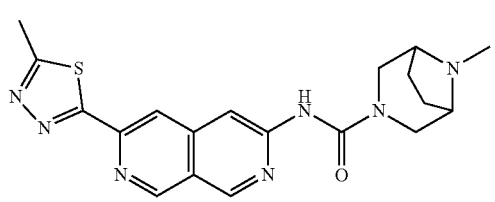 [SMILES: Cc1nnc(-c2cc3cc(NC(=O)N4CC5CCC(C4)N5C)ncc3cn2)s1] | 4301 |

TABLE 1-continued
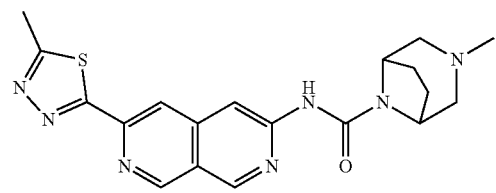 4302
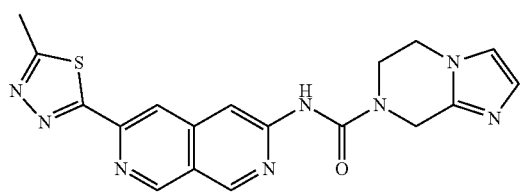 [SMILES: Cc1nnc(-c2cc3cc(NC(=O)N4CCn5ccnc5C4)ncc3cn2)s1] 4303
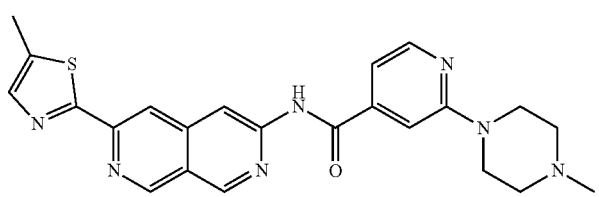 [SMILES: Cc1cnc(-c2cc3cc(NC(=O)c4ccnc(N5CCN(C)CC5)c4)ncc3cn2)s1] 4304
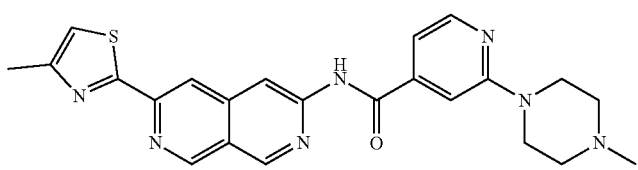 4305
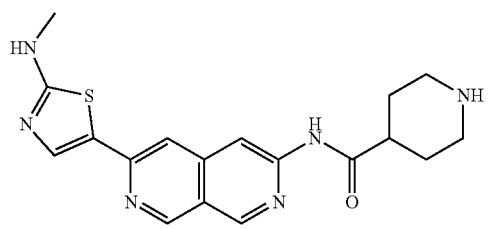 [SMILES: CNc1ncc(-c2cc3cc(NC(=O)C4CCNCC4)ncc3cn2)s1] 4306
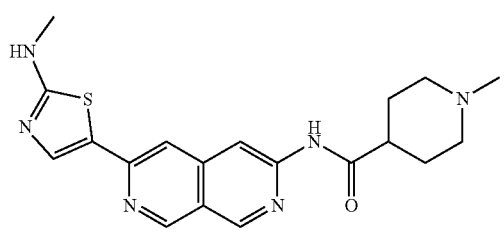 [SMILES: CNc1ncc(-c2cc3cc(NC(=O)C4CCN(C)CC4)ncc3cn2)s1] 4307
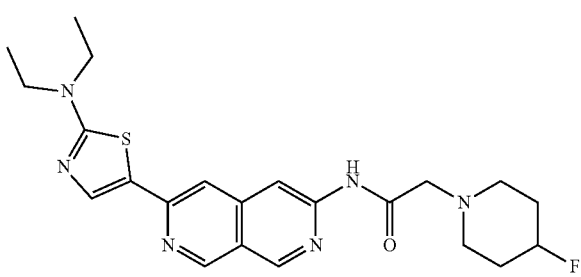 4308

US 10,703,748 B2
1313
TABLE 1-continued
1314
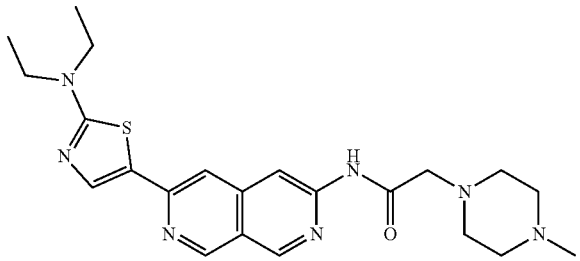 4309
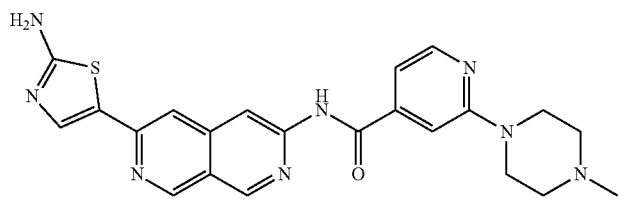 [SMILES: CN1CCN(c2cc(C(=O)Nc3cc4cc(-c5cnc(N)s5)ncc4cn3)ccn2)CC1] 4310
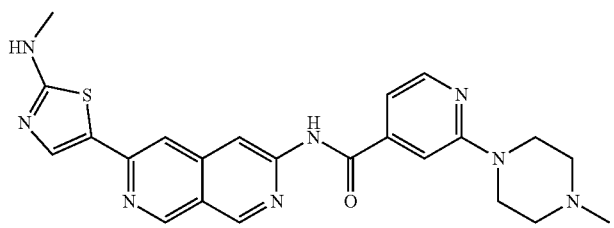 4311
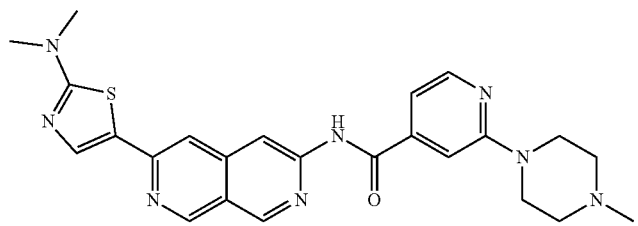 4312
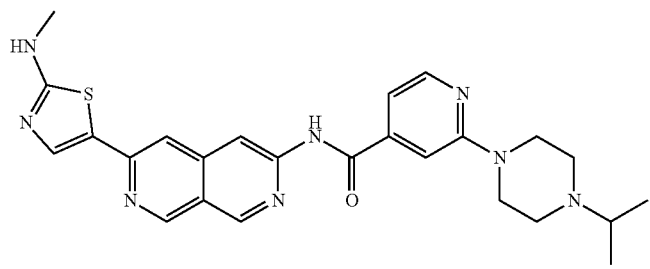 [SMILES: CNc1ncc(-c2cc3cc(NC(=O)c4ccnc(N5CCN(C(C)C)CC5)c4)ncc3cn2)s1] 4313
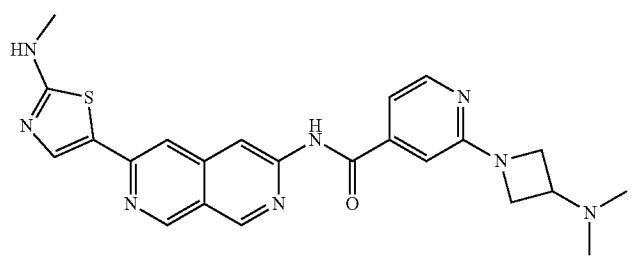 [SMILES: CNc1ncc(-c2cc3cc(NC(=O)c4ccnc(N5CC(N(C)C)C5)c4)ncc3cn2)s1] 4314

TABLE 1-continued
| | |
|---|---|
| 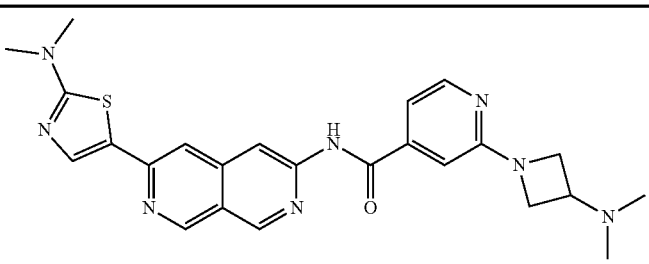 | 4315 |
| 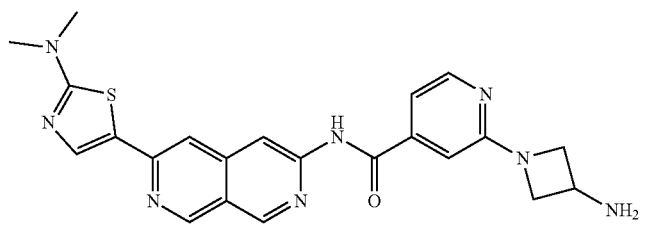 [SMILES: CN(C)c1ncc(-c2cc3cc(NC(=O)c4ccnc(N5CC(N)C5)c4)ncc3cn2)s1] | 4316 |
| 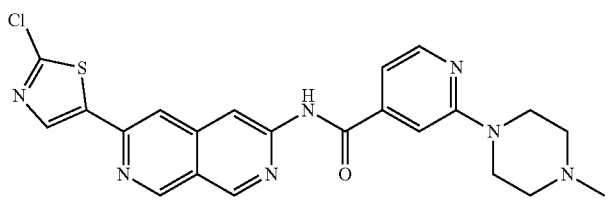 [SMILES: CN1CCN(c2cc(C(=O)Nc3cc4cc(-c5cnc(Cl)s5)ncc4cn3)ccn2)CC1] | 4317 |
| 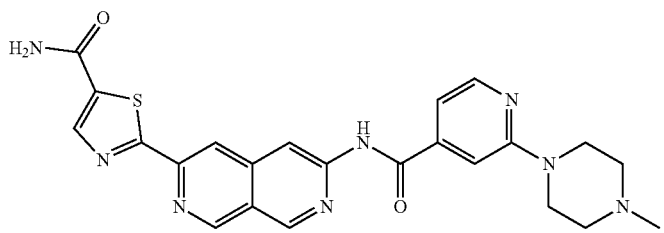 [SMILES: CN1CCN(c2cc(C(=O)Nc3cc4cc(-c5ncc(C(N)=O)s5)ncc4cn3)ccn2)CC1] | 4318 |
| 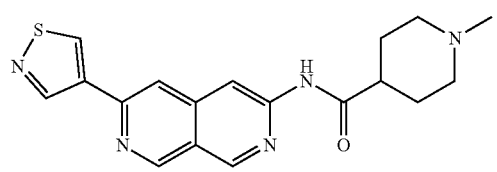 [SMILES: CN1CCC(C(=O)Nc2cc3cc(-c4cnsc4)ncc3cn2)CC1] | 4319 |
| 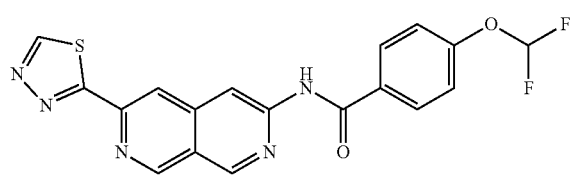 [SMILES: O=C(Nc1cc2cc(-c3nncs3)ncc2cn1)c1ccc(OC(F)F)cc1] | 4320 |
| 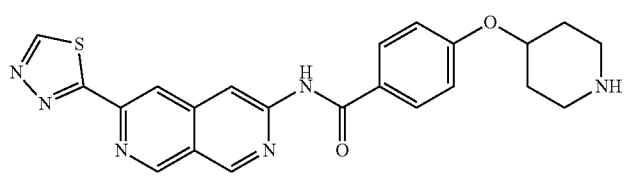 [SMILES: O=C(Nc1cc2cc(-c3nncs3)ncc2cn1)c1ccc(OC2CCNCC2)cc1] | 4321 |
| 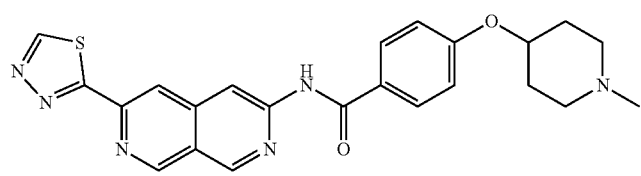 [SMILES: CN1CCC(Oc2ccc(C(=O)Nc3cc4cc(-c5nncs5)ncc4cn3)cc2)CC1] | 4322 |

TABLE 1-continued
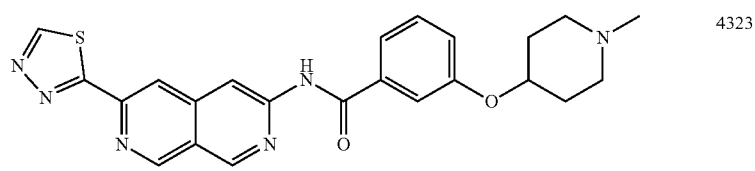 4323
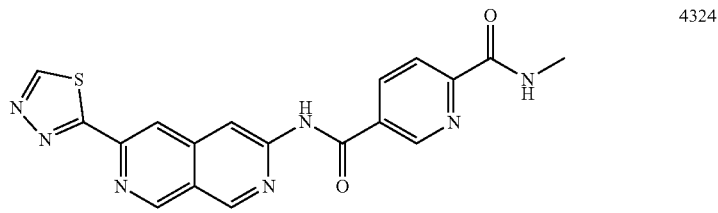 4324
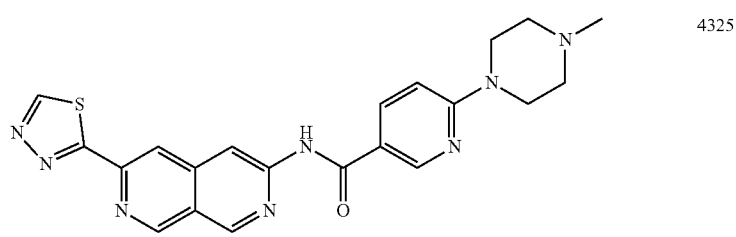 4325
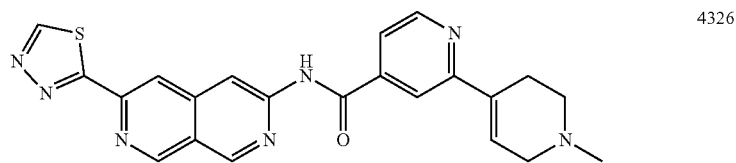 4326
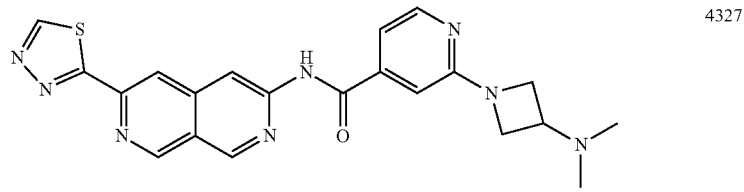 4327
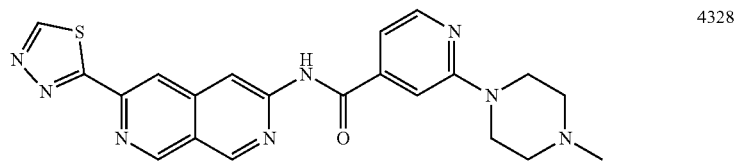 4328
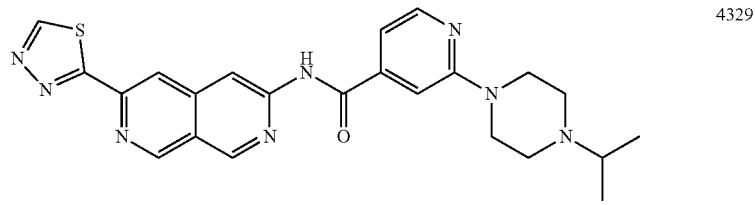 4329
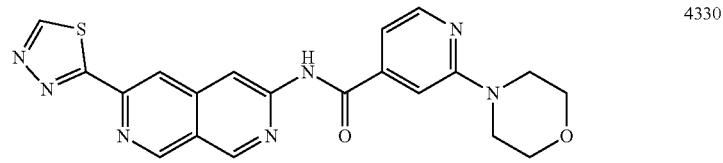 4330

TABLE 1-continued
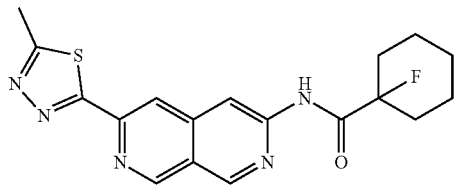 4331
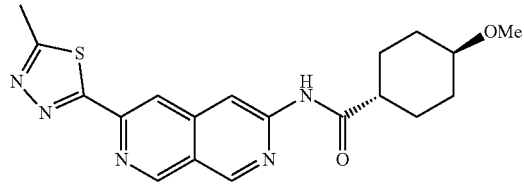 [SMILES: CO[C@H]1CC[C@H](C(=O)Nc2cc3cc(-c4nnc(C)s4)ncc3cn2)CC1] 4332
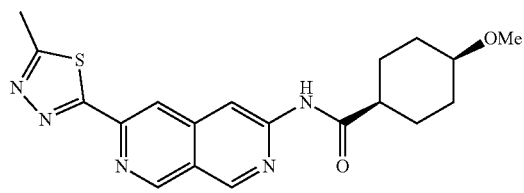 [SMILES: CO[C@H]1CC[C@@H](C(=O)Nc2cc3cc(-c4nnc(C)s4)ncc3cn2)CC1] 4333
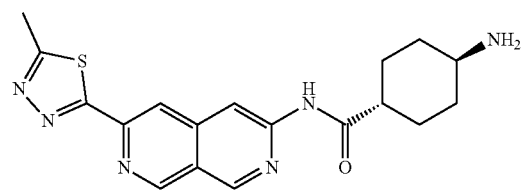 [SMILES: Cc1nnc(-c2cc3cc(NC(=O)[C@H]4CC[C@H](N)CC4)ncc3cn2)s1] 4334
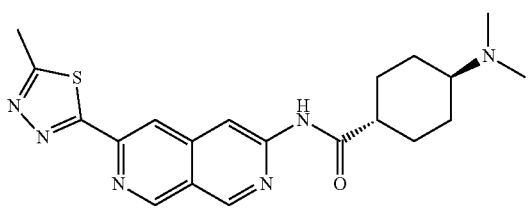 [SMILES: Cc1nnc(-c2cc3cc(NC(=O)[C@H]4CC[C@H](N(C)C)CC4)ncc3cn2)s1] 4335
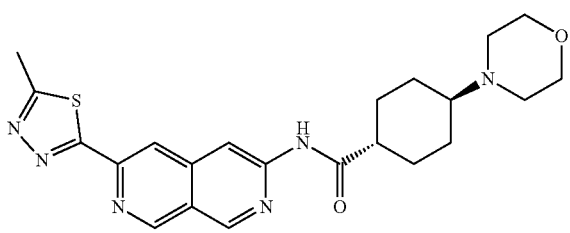 [SMILES: Cc1nnc(-c2cc3cc(NC(=O)[C@H]4CC[C@H](N5CCOCC5)CC4)ncc3cn2)s1] 4336
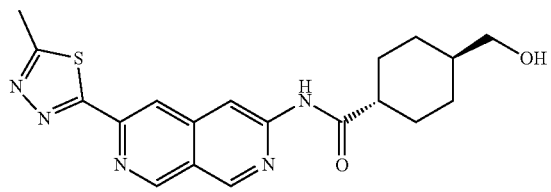 [SMILES: Cc1nnc(-c2cc3cc(NC(=O)[C@H]4CC[C@H](CO)CC4)ncc3cn2)s1] 4337
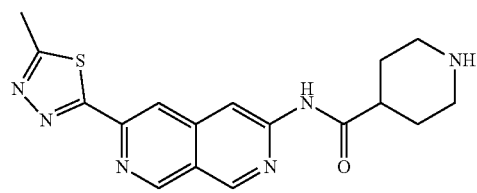 [SMILES: Cc1nnc(-c2cc3cc(NC(=O)C4CCNCC4)ncc3cn2)s1] 4338

TABLE 1-continued
| 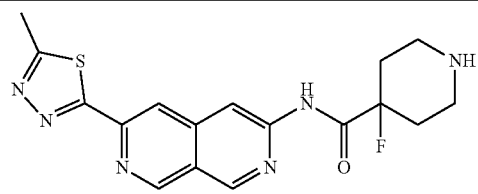 | 4339 |
| --- | --- |
| 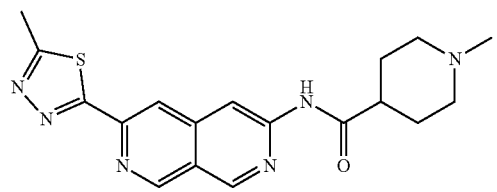 [SMILES: Cc1nnc(-c2cc3cc(NC(=O)C4CCN(C)CC4)ncc3cn2)s1] | 4340 |
| 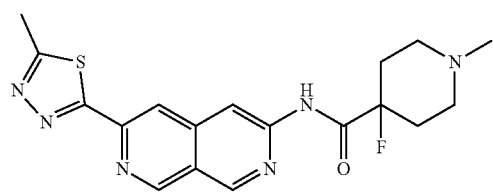 [SMILES: Cc1nnc(-c2cc3cc(NC(=O)C4(F)CCN(C)CC4)ncc3cn2)s1] | 4341 |
| 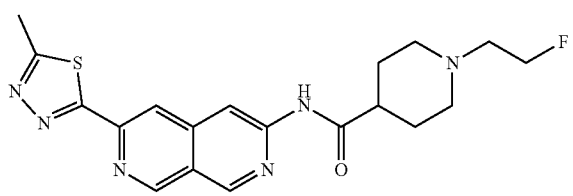 [SMILES: Cc1nnc(-c2cc3cc(NC(=O)C4CCN(CCF)CC4)ncc3cn2)s1] | 4342 |
| 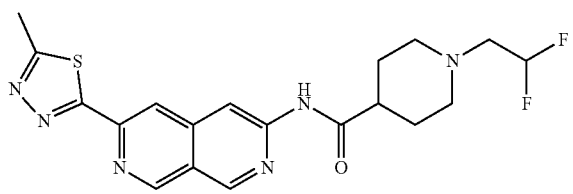 [SMILES: Cc1nnc(-c2cc3cc(NC(=O)C4CCN(CC(F)F)CC4)ncc3cn2)s1] | 4343 |
| 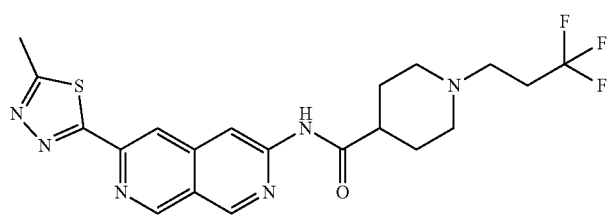 [SMILES: Cc1nnc(-c2cc3cc(NC(=O)C4CCN(CCC(F)(F)F)CC4)ncc3cn2)s1] | 4344 |
| 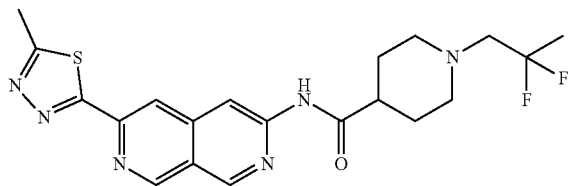 [SMILES: Cc1nnc(-c2cc3cc(NC(=O)C4CCN(CC(C)(F)F)CC4)ncc3cn2)s1] | 4345 |
| 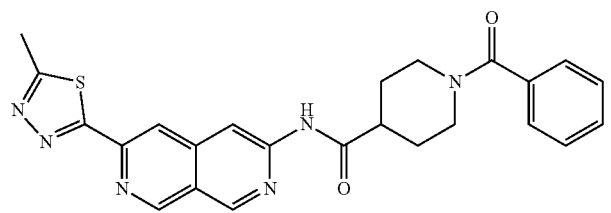 [SMILES: Cc1nnc(-c2cc3cc(NC(=O)C4CCN(C(=O)c5ccccc5)CC4)ncc3cn2)s1] | 4346 |

US 10,703,748 B2
1323
TABLE 1-continued
1324
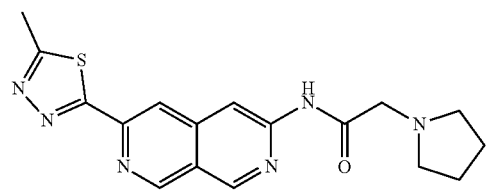 [SMILES: Cc1nnc(-c2cc3cc(NC(=O)CN4CCCC4)ncc3cn2)s1] 4347
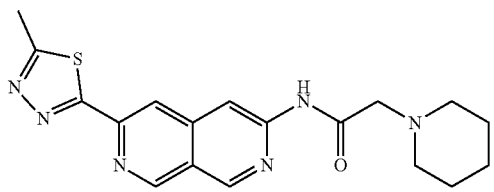 [SMILES: Cc1nnc(-c2cc3cc(NC(=O)CN4CCCCC4)ncc3cn2)s1] 4348
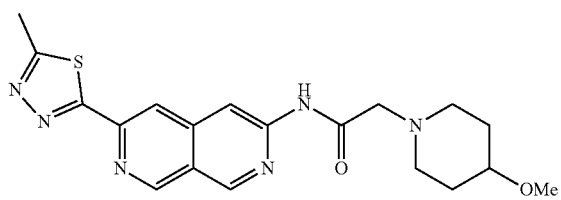 [SMILES: COC1CCN(CC(=O)Nc2cc3cc(-c4nnc(C)s4)ncc3cn2)CC1] 4349
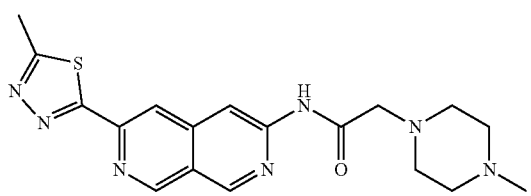 [SMILES: Cc1nnc(-c2cc3cc(NC(=O)CN4CCN(C)CC4)ncc3cn2)s1] 4350
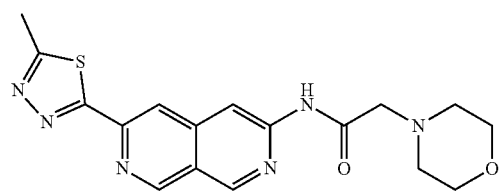 [SMILES: Cc1nnc(-c2cc3cc(NC(=O)CN4CCOCC4)ncc3cn2)s1] 4351
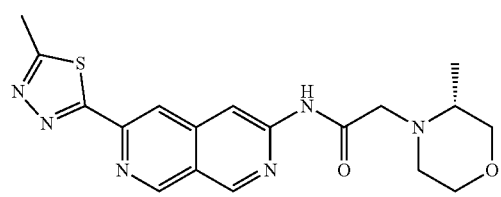 [SMILES: Cc1nnc(-c2cc3cc(NC(=O)CN4CCOC[C@H]4C)ncc3cn2)s1] 4352
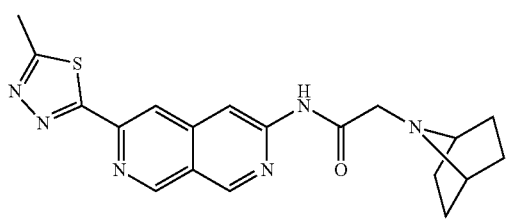 [SMILES: Cc1nnc(-c2cc3cc(NC(=O)CN4C5CCC4CC5)ncc3cn2)s1] 4353
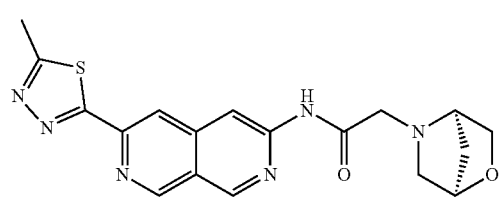 [SMILES: Cc1nnc(-c2cc3cc(NC(=O)CN4C[C@H]5C[C@@H]4CO5)ncc3cn2)s1] 4354

TABLE 1-continued
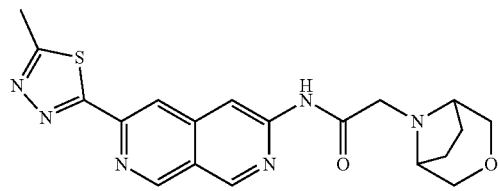 [SMILES: Cc1nnc(-c2cc3cc(NC(=O)CN4C5CCC4COC5)ncc3cn2)s1]
4355
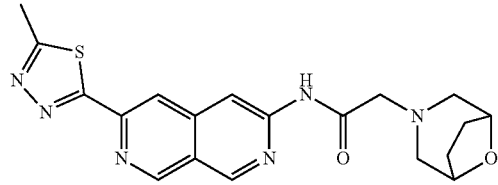 [SMILES: Cc1nnc(-c2cc3cc(NC(=O)CN4CC5CCC(C4)O5)ncc3cn2)s1]
4356
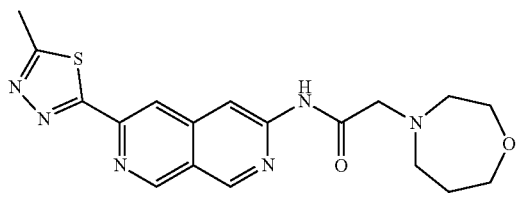 [SMILES: Cc1nnc(-c2cc3cc(NC(=O)CN4CCCOCC4)ncc3cn2)s1]
4357
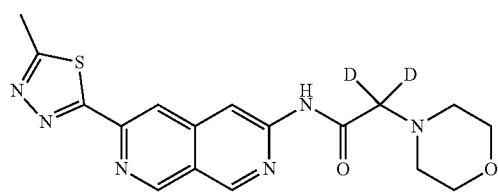 [SMILES: [2H]C([2H])(C(=O)Nc1cc2cc(-c3nnc(C)s3)ncc2cn1)N1CCOCC1]
4358
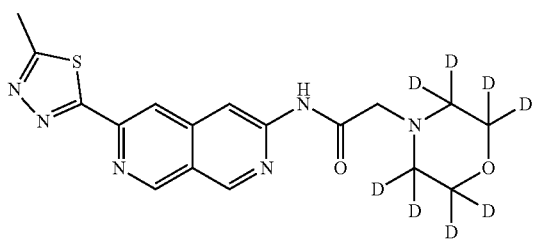 [SMILES: [2H]C1([2H])OC([2H])([2H])C([2H])([2H])N(CC(=O)Nc2cc3cc(-c4nnc(C)s4)ncc3cn2)C1([2H])[2H]]
4359
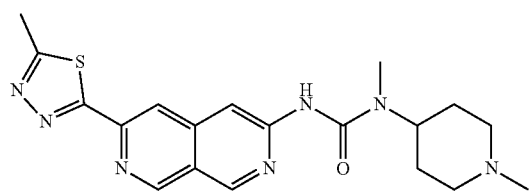 [SMILES: Cc1nnc(-c2cc3cc(NC(=O)N(C)C4CCN(C)CC4)ncc3cn2)s1]
4360
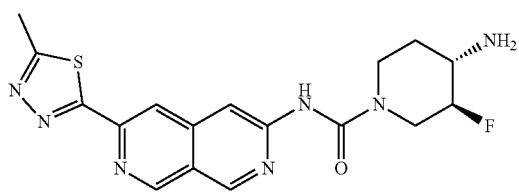 [SMILES: Cc1nnc(-c2cc3cc(NC(=O)N4CC[C@H](N)[C@@H](F)C4)ncc3cn2)s1]
4361
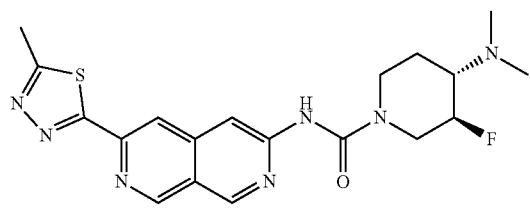 [SMILES: Cc1nnc(-c2cc3cc(NC(=O)N4CC[C@H](N(C)C)[C@@H](F)C4)ncc3cn2)s1]
4362

TABLE 1-continued
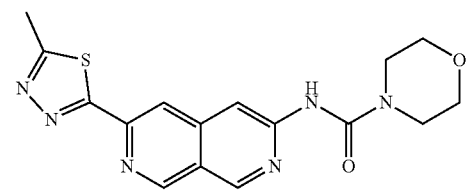 [SMILES: Cc1nnc(-c2cc3cc(NC(=O)N4CCOCC4)ncc3cn2)s1]
4363
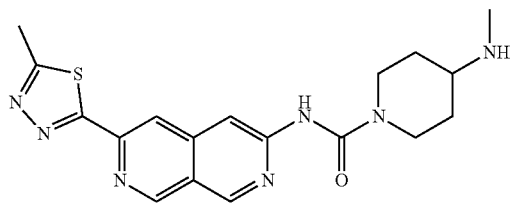 [SMILES: CNC1CCN(C(=O)Nc2cc3cc(-c4nnc(C)s4)ncc3cn2)CC1]
4364
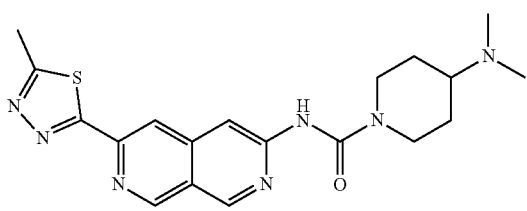 [SMILES: Cc1nnc(-c2cc3cc(NC(=O)N4CCC(N(C)C)CC4)ncc3cn2)s1]
4365
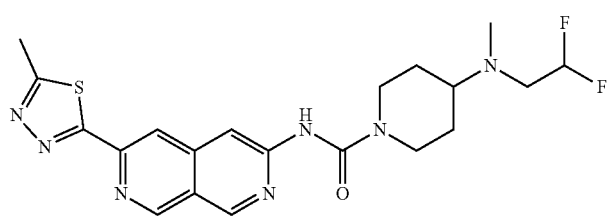 [SMILES: Cc1nnc(-c2cc3cc(NC(=O)N4CCC(N(C)CC(F)F)CC4)ncc3cn2)s1]
4366
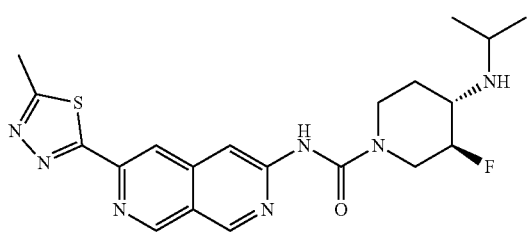
4367
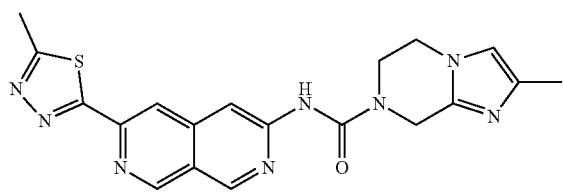 [SMILES: Cc1cn2c(n1)CN(C(=O)Nc1cc3cc(-c4nnc(C)s4)ncc3cn1)CC2]
4368
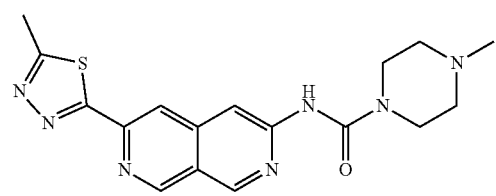
4369

TABLE 1-continued
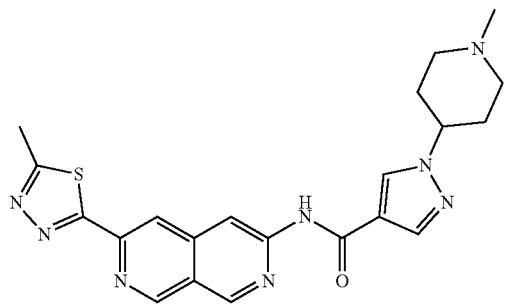 [SMILES: Cc1nnc(-c2cc3cc(NC(=O)c4cnn(C5CCN(C)CC5)c4)ncc3cn2)s1] 4370
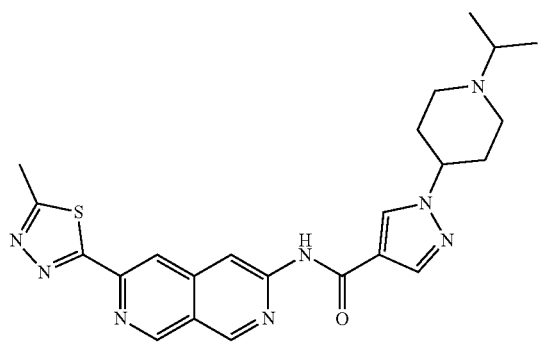 [SMILES: Cc1nnc(-c2cc3cc(NC(=O)c4cnn(C5CCN(C(C)C)CC5)c4)ncc3cn2)s1] 4371
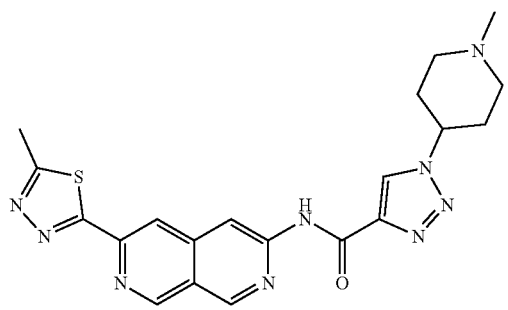 [SMILES: Cc1nnc(-c2cc3cc(NC(=O)c4cn(C5CCN(C)CC5)nn4)ncc3cn2)s1] 4372
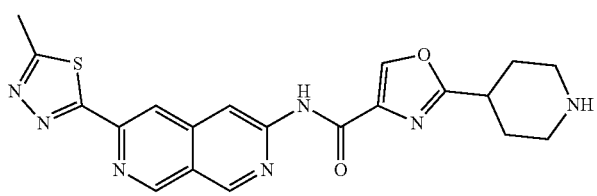 [SMILES: Cc1nnc(-c2cc3cc(NC(=O)c4coc(C5CCNCC5)n4)ncc3cn2)s1] 4373
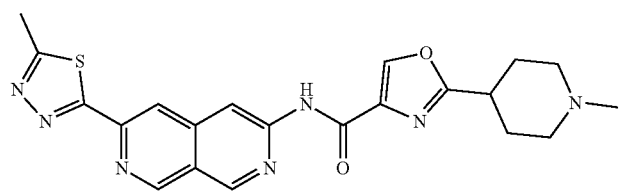 [SMILES: Cc1nnc(-c2cc3cc(NC(=O)c4coc(C5CCN(C)CC5)n4)ncc3cn2)s1] 4374
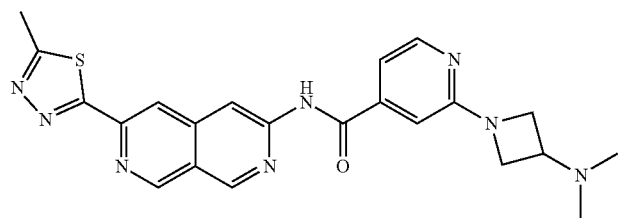 [SMILES: Cc1nnc(-c2cc3cc(NC(=O)c4ccnc(N5CC(N(C)C)C5)c4)ncc3cn2)s1] 4375

TABLE 1-continued
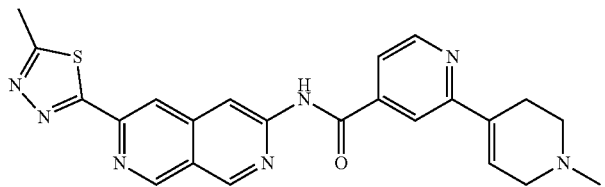 [SMILES: Cc1nnc(-c2cc3cc(NC(=O)c4ccnc(C5=CCN(C)CC5)c4)ncc3cn2)s1]
4376
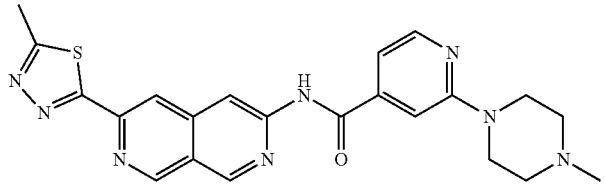 [SMILES: Cc1nnc(-c2cc3cc(NC(=O)c4ccnc(N5CCN(C)CC5)c4)ncc3cn2)s1]
4377
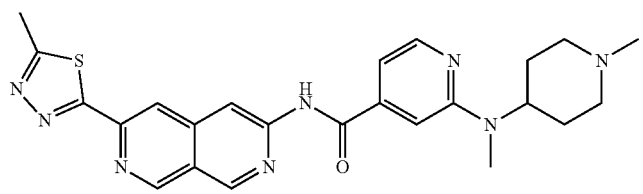 [SMILES: Cc1nnc(-c2cc3cc(NC(=O)c4ccnc(N(C)C5CCN(C)CC5)c4)ncc3cn2)s1]
4378
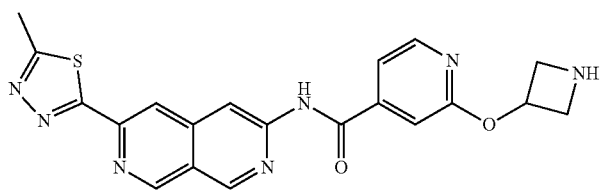 [SMILES: Cc1nnc(-c2cc3cc(NC(=O)c4ccnc(OC5CNC5)c4)ncc3cn2)s1]
4379
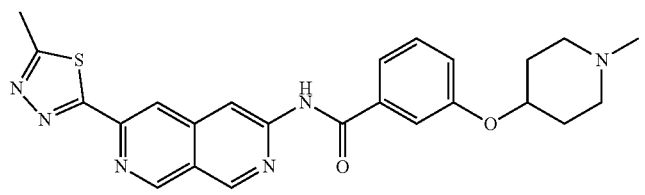 [SMILES: Cc1nnc(-c2cc3cc(NC(=O)c4cccc(OC5CCN(C)CC5)c4)ncc3cn2)s1]
4380
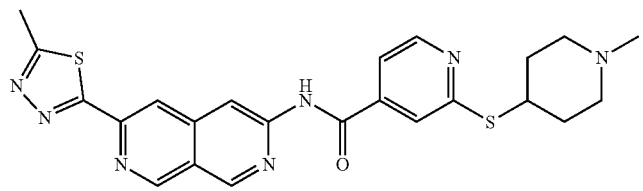 [SMILES: Cc1nnc(-c2cc3cc(NC(=O)c4ccnc(SC5CCN(C)CC5)c4)ncc3cn2)s1]
4381
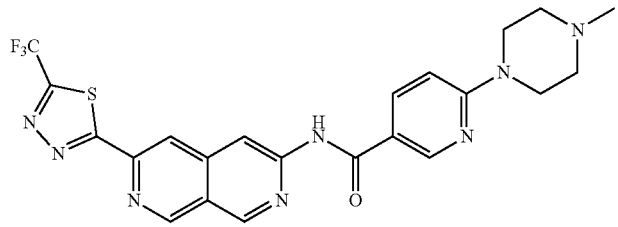 [SMILES: CN1CCN(c2ccc(C(=O)Nc3cc4cc(-c5nnc(C(F)(F)F)s5)ncc4cn3)cn2)CC1]
4382
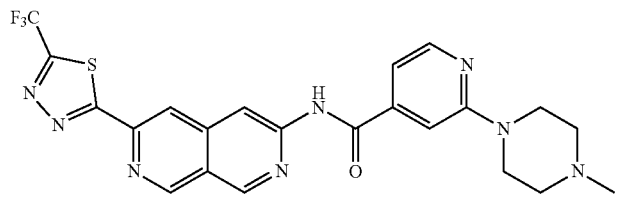
4383

TABLE 1-continued
| | |
|---|---|
| 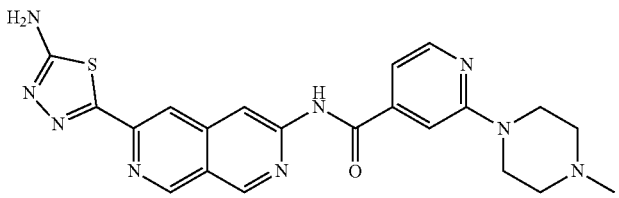 | 4384 |
| 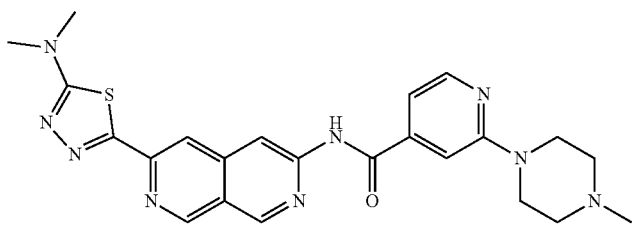 | 4385 |
| 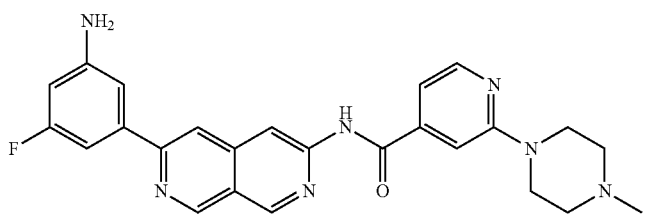 [SMILES: CN1CCN(c2cc(C(=O)Nc3cc4cc(-c5cc(N)cc(F)c5)ncc4cn3)ccn2)CC1] | 4386 |
| 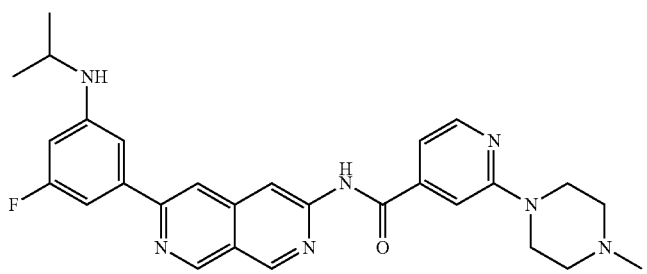 [SMILES: CC(C)Nc1cc(F)cc(-c2cc3cc(NC(=O)c4ccnc(N5CCN(C)CC5)c4)ncc3cn2)c1] | 4387 |
| 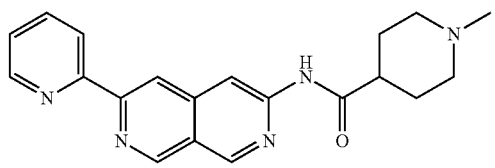 [SMILES: CN1CCC(C(=O)Nc2cc3cc(-c4ccccn4)ncc3cn2)CC1] | 4388 |
| 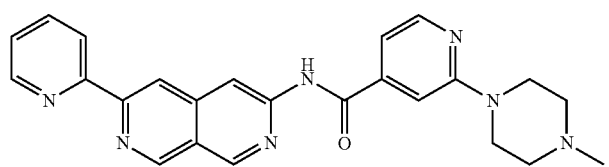 [SMILES: CN1CCN(c2cc(C(=O)Nc3cc4cc(-c5ccccn5)ncc4cn3)ccn2)CC1] | 4389 |
| 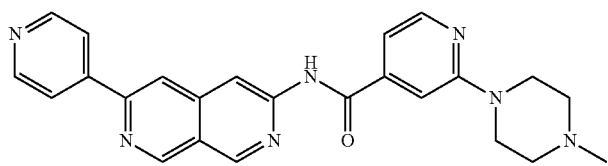 [SMILES: CN1CCN(c2cc(C(=O)Nc3cc4cc(-c5ccncc5)ncc4cn3)ccn2)CC1] | 4390 |
| 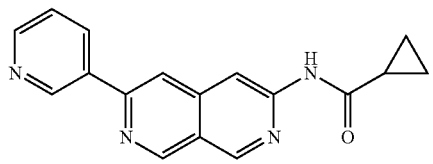 [SMILES: O=C(Nc1cc2cc(-c3cccnc3)ncc2cn1)C1CC1] | 4391 |

TABLE 1-continued
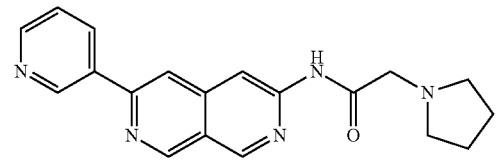 [SMILES: O=C(CN1CCCC1)Nc1cc2cc(-c3cccnc3)ncc2cn1] 4392
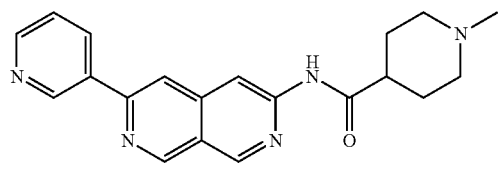 [SMILES: CN1CCC(C(=O)Nc2cc3cc(-c4cccnc4)ncc3cn2)CC1] 4393
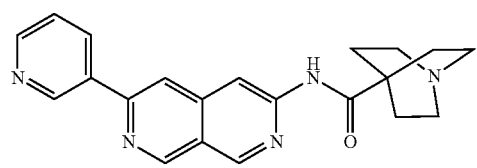 [SMILES: O=C(Nc1cc2cc(-c3cccnc3)ncc2cn1)C12CCN(CC1)CC2] 4394
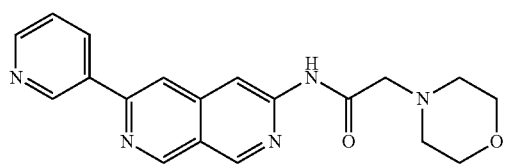 [SMILES: O=C(CN1CCOCC1)Nc1cc2cc(-c3cccnc3)ncc2cn1] 4395
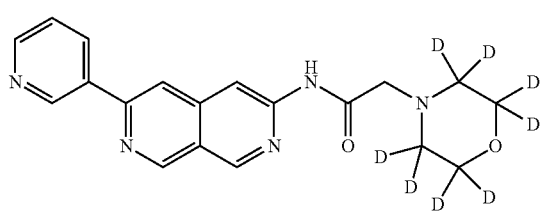 [SMILES: [2H]C1([2H])OC([2H])([2H])C([2H])([2H])N(CC(=O)Nc2cc3cc(-c4cccnc4)ncc3cn2)C1([2H])[2H]] 4396
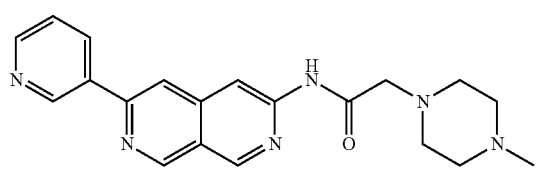 [SMILES: CN1CCN(CC(=O)Nc2cc3cc(-c4cccnc4)ncc3cn2)CC1] 4397
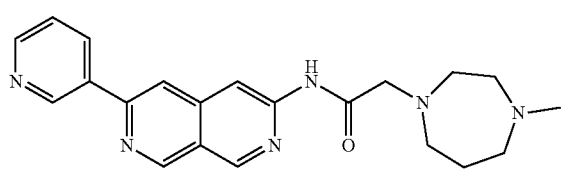 [SMILES: CN1CCCN(CC(=O)Nc2cc3cc(-c4cccnc4)ncc3cn2)CC1] 4398
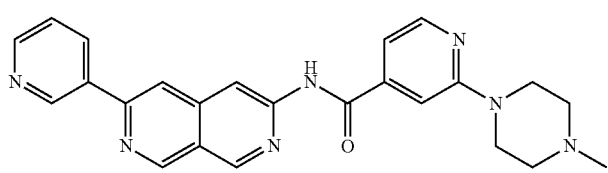 4399
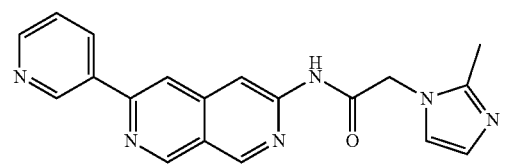 [SMILES: Cc1nccn1CC(=O)Nc1cc2cc(-c3cccnc3)ncc2cn1] 4400

TABLE 1-continued
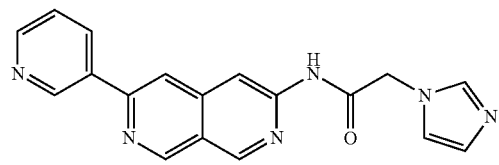 [SMILES: O=C(Cn1ccnc1)Nc1cc2cc(-c3cccnc3)ncc2cn1]
4401
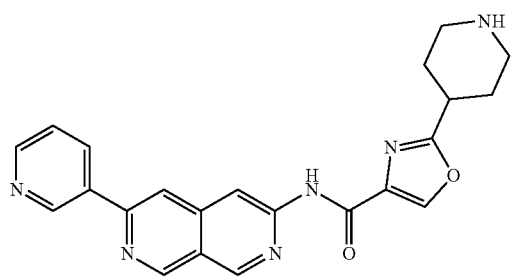 [SMILES: O=C(Nc1cc2cc(-c3cccnc3)ncc2cn1)c1coc(C2CCNCC2)n1]
4402
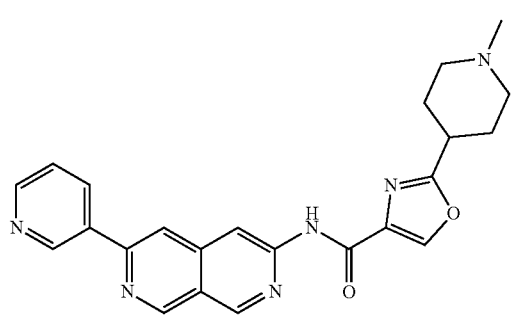 [SMILES: CN1CCC(c2nc(C(=O)Nc3cc4cc(-c5cccnc5)ncc4cn3)co2)CC1]
4403
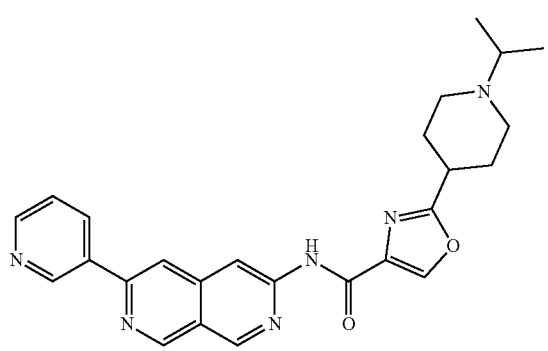
4404
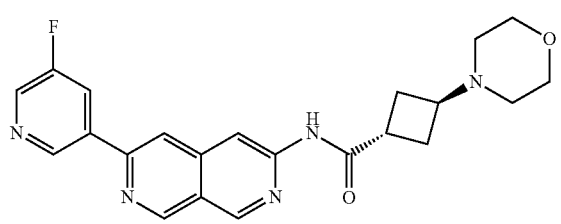 [SMILES: O=C(Nc1cc2cc(-c3cncc(F)c3)ncc2cn1)[C@H]1C[C@H](N2CCOCC2)C1]
4405
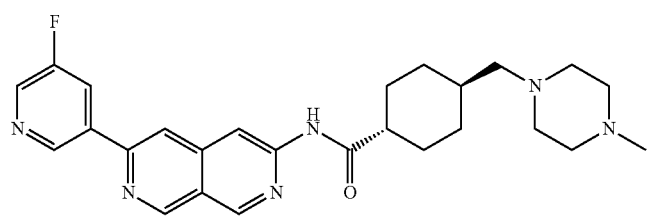 [SMILES: CN1CCN(C[C@H]2CC[C@H](C(=O)Nc3cc4cc(-c5cncc(F)c5)ncc4cn3)CC2)CC1]
4406

TABLE 1-continued
| | |
|---|---|
| 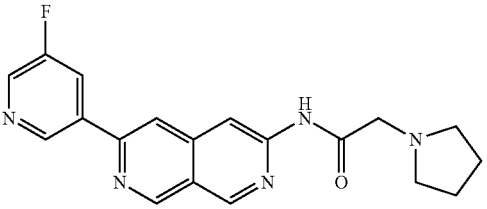 [SMILES: O=C(CN1CCCC1)Nc1cc2cc(-c3cncc(F)c3)ncc2cn1] | 4407 |
| 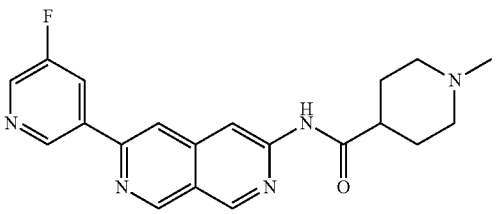 [SMILES: CN1CCC(C(=O)Nc2cc3cc(-c4cncc(F)c4)ncc3cn2)CC1] | 4408 |
| 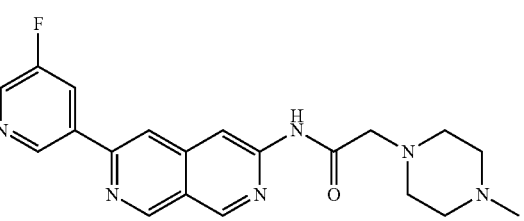 | 4409 |
| 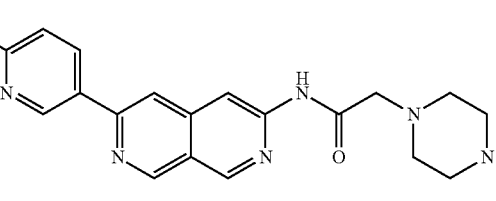 | 4410 |
| 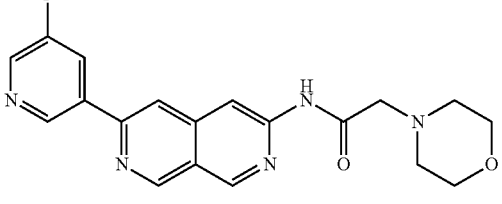 | 4411 |
| 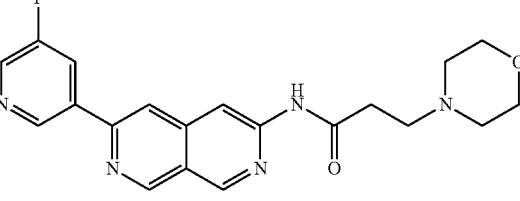 | 4412 |
| 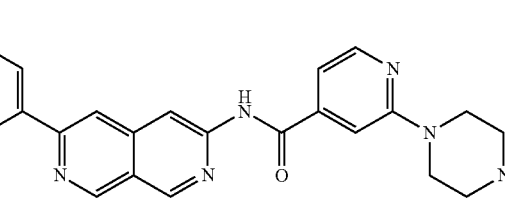 | 4413 |

TABLE 1-continued
| | |
|---|---|
| 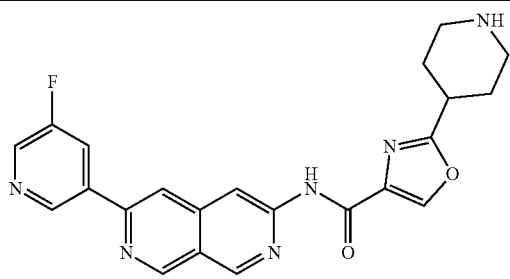 | 4414 |
| 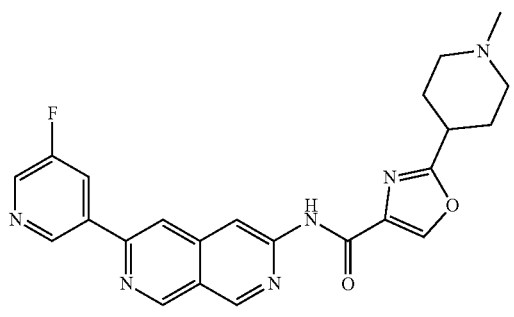 [SMILES: CN1CCC(c2nc(C(=O)Nc3cc4cc(-c5cncc(F)c5)ncc4cn3)co2)CC1] | 4415 |
| 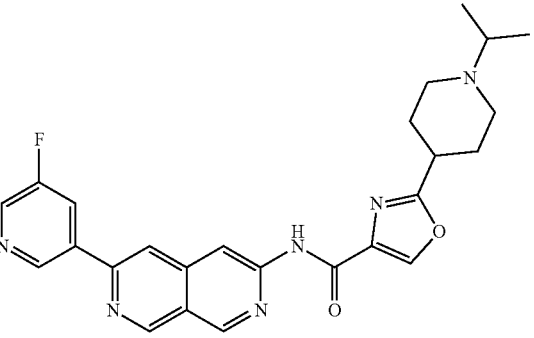 | 4416 |
| 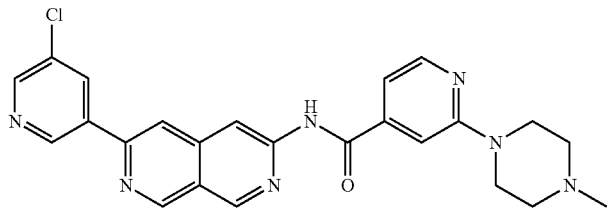 | 4417 |
| 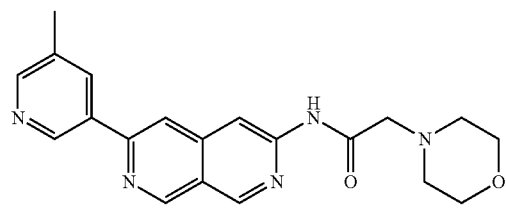 [SMILES: Cc1cncc(-c2cc3cc(NC(=O)CN4CCOCC4)ncc3cn2)c1] | 4418 |
| 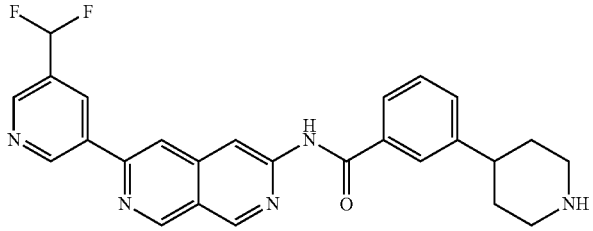 [SMILES: O=C(Nc1cc2cc(-c3cncc(C(F)F)c3)ncc2cn1)c1cccc(C2CCNCC2)c1] | 4419 |

TABLE 1-continued
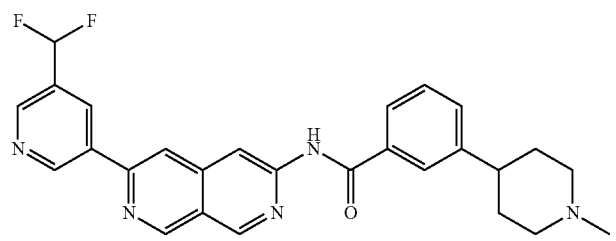 [SMILES: CN1CCC(c2cccc(C(=O)Nc3cc4cc(-c5cncc(C(F)F)c5)ncc4cn3)c2)CC1] 4420
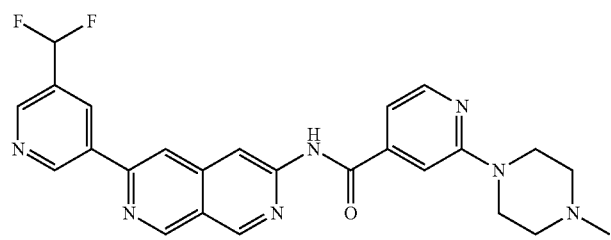 [SMILES: CN1CCN(c2cc(C(=O)Nc3cc4cc(-c5cncc(C(F)F)c5)ncc4cn3)ccn2)CC1] 4421
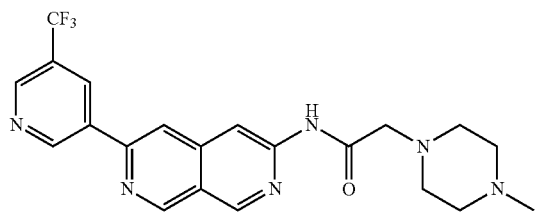 4422
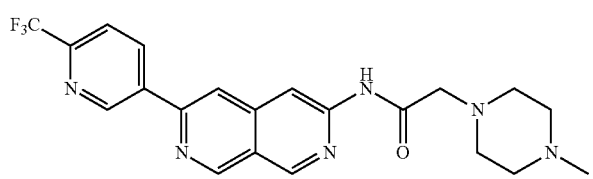 [SMILES: CN1CCN(CC(=O)Nc2cc3cc(-c4ccc(C(F)(F)F)nc4)ncc3cn2)CC1] 4423
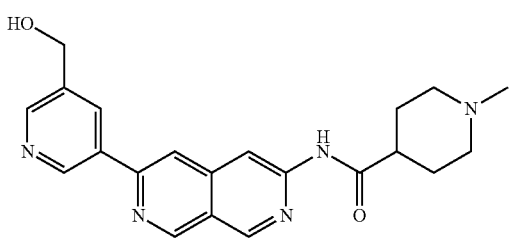 [SMILES: CN1CCC(C(=O)Nc2cc3cc(-c4cncc(CO)c4)ncc3cn2)CC1] 4424
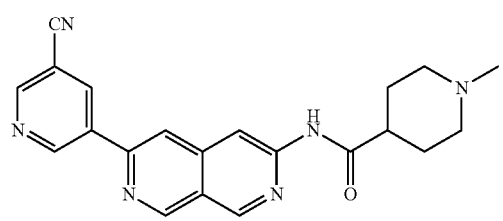 4425
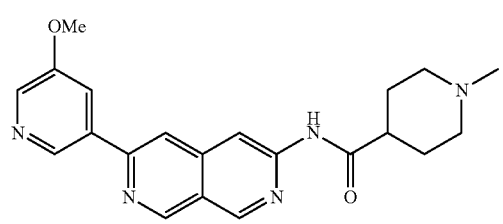 [SMILES: CN1CCC(C(=O)Nc2cc3cc(-c4cncc(C#N)c4)ncc3cn2)CC1] 4426

TABLE 1-continued
| | |
|---|---|
| 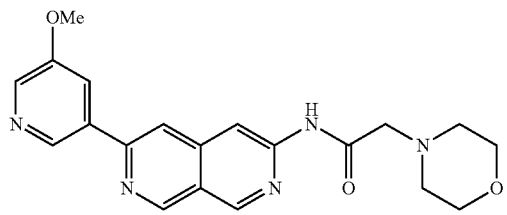 [SMILES: COc1cncc(-c2cc3cc(NC(=O)CN4CCOCC4)ncc3cn2)c1] | 4427 |
| 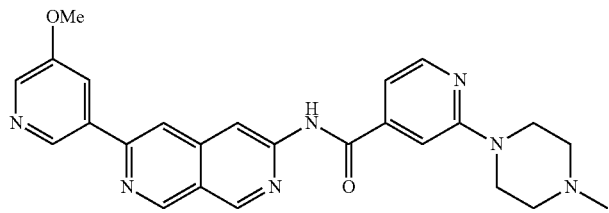 [SMILES: COc1cncc(-c2cc3cc(NC(=O)c4ccnc(N5CCN(C)CC5)c4)ncc3cn2)c1] | 4428 |
| 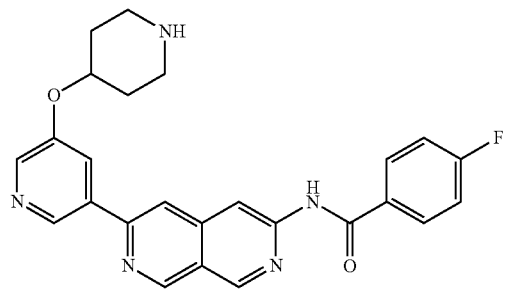 [SMILES: O=C(Nc1cc2cc(-c3cncc(OC4CCNCC4)c3)ncc2cn1)c1ccc(F)cc1] | 4429 |
| 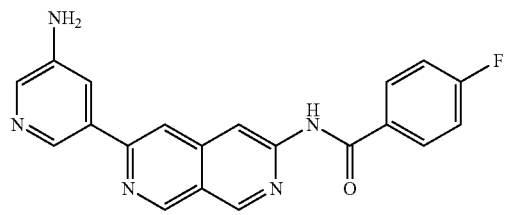 [SMILES: Nc1cncc(-c2cc3cc(NC(=O)c4ccc(F)cc4)ncc3cn2)c1] | 4430 |
| 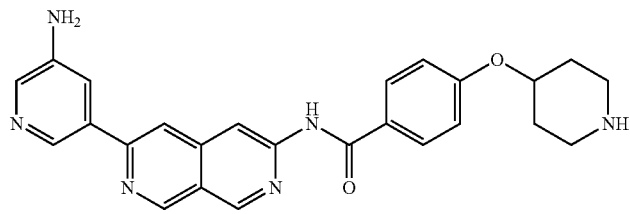 [SMILES: Nc1cncc(-c2cc3cc(NC(=O)c4ccc(OC5CCNCC5)cc4)ncc3cn2)c1] | 4431 |
| 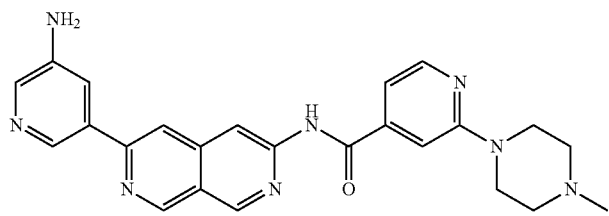 [SMILES: CN1CCN(c2cc(C(=O)Nc3cc4cc(-c5cncc(N)c5)ncc4cn3)ccn2)CC1] | 4432 |

TABLE 1-continued
| | |
|---|---|
| 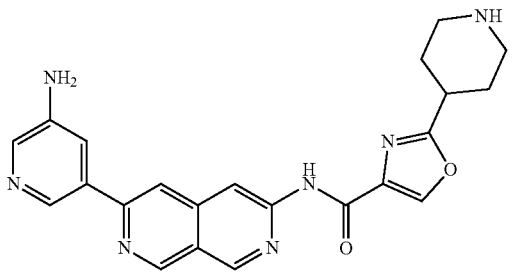 [SMILES: Nc1cncc(-c2cc3cc(NC(=O)c4coc(C5CCNCC5)n4)ncc3cn2)c1] | 4433 |
| 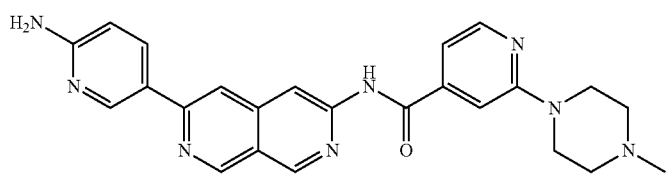 [SMILES: CN1CCN(c2cc(C(=O)Nc3cc4cc(-c5ccc(N)nc5)ncc4cn3)ccn2)CC1] | 4434 |
| 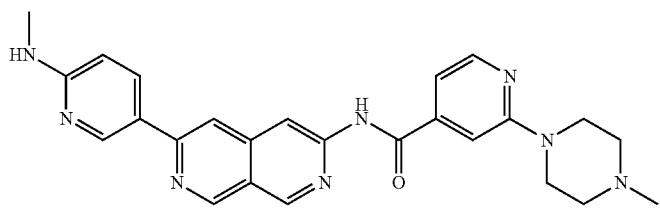 [SMILES: CNc1ccc(-c2cc3cc(NC(=O)c4ccnc(N5CCN(C)CC5)c4)ncc3cn2)cn1] | 4435 |
| 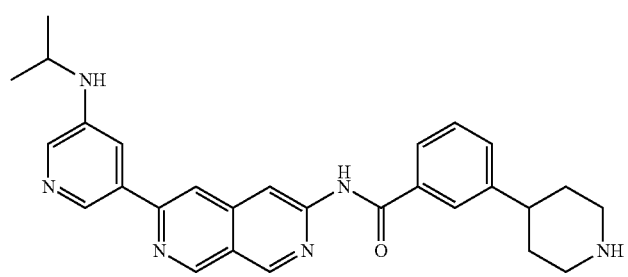 [SMILES: CC(C)Nc1cncc(-c2cc3cc(NC(=O)c4cccc(C5CCNCC5)c4)ncc3cn2)c1] | 4436 |
| 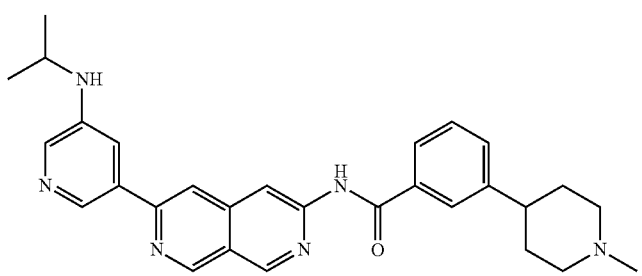 | 4437 |
| 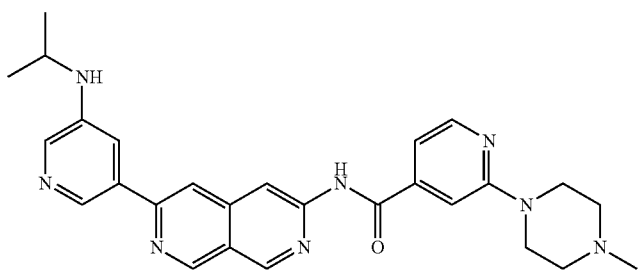 | 4438 |

TABLE 1-continued
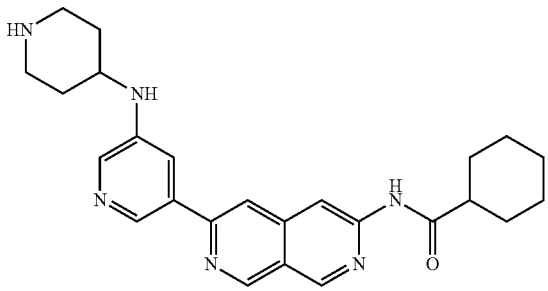 [SMILES: O=C(Nc1cc2cc(-c3cncc(NC4CCNCC4)c3)ncc2cn1)C1CCCCC1]
4439
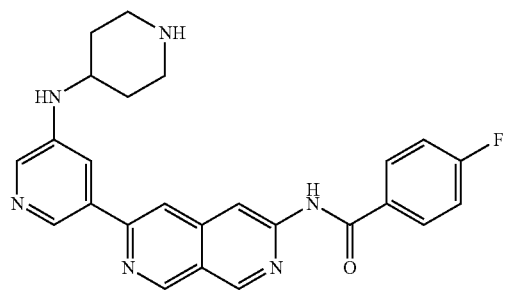 [SMILES: O=C(Nc1cc2cc(-c3cncc(NC4CCNCC4)c3)ncc2cn1)c1ccc(F)cc1]
4440
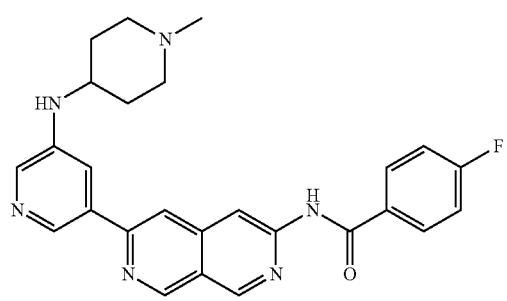 [SMILES: CN1CCC(Nc2cncc(-c3cc4cc(NC(=O)c5ccc(F)cc5)ncc4cn3)c2)CC1]
4441
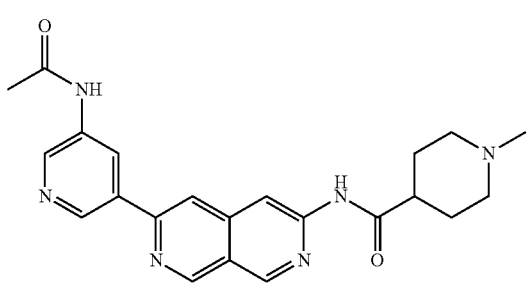 [SMILES: CC(=O)Nc1cncc(-c2cc3cc(NC(=O)C4CCN(C)CC4)ncc3cn2)c1]
4442
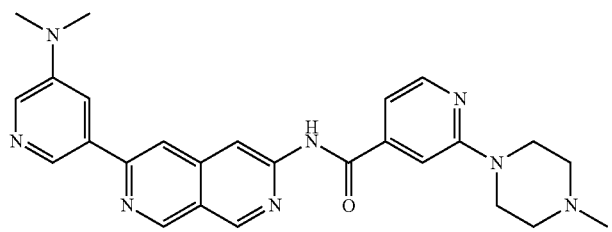
4443
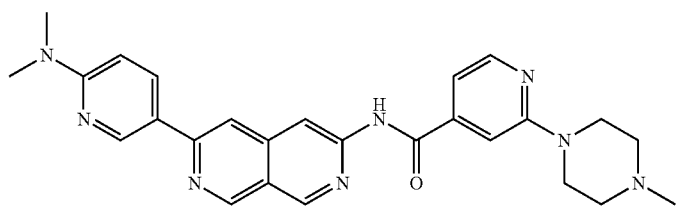
4444

TABLE 1-continued
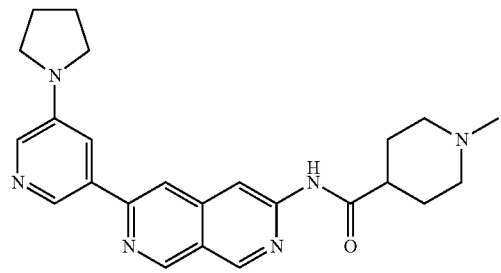 [SMILES: CN1CCC(C(=O)Nc2cc3cc(-c4cncc(N5CCCC5)c4)ncc3cn2)CC1]
4445
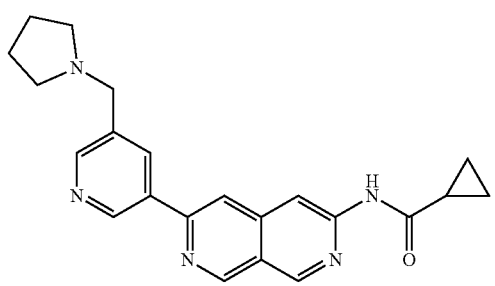 [SMILES: O=C(Nc1cc2cc(-c3cncc(CN4CCCC4)c3)ncc2cn1)C1CC1]
4446
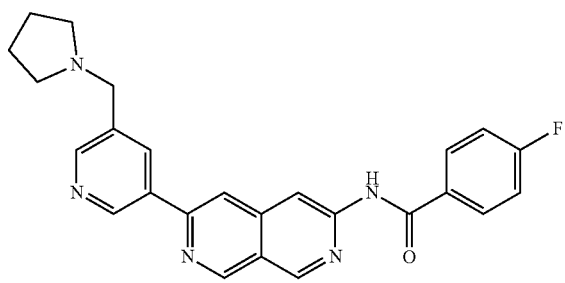 [SMILES: O=C(Nc1cc2cc(-c3cncc(CN4CCCC4)c3)ncc2cn1)c1ccc(F)cc1]
4447
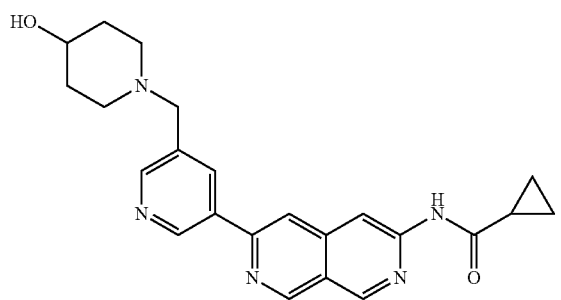 [SMILES: O=C(Nc1cc2cc(-c3cncc(CN4CCC(O)CC4)c3)ncc2cn1)C1CC1]
4448
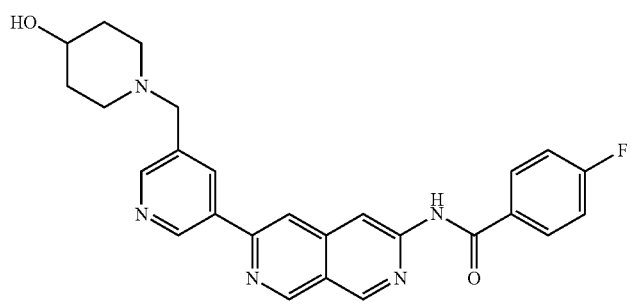
4449

TABLE 1-continued
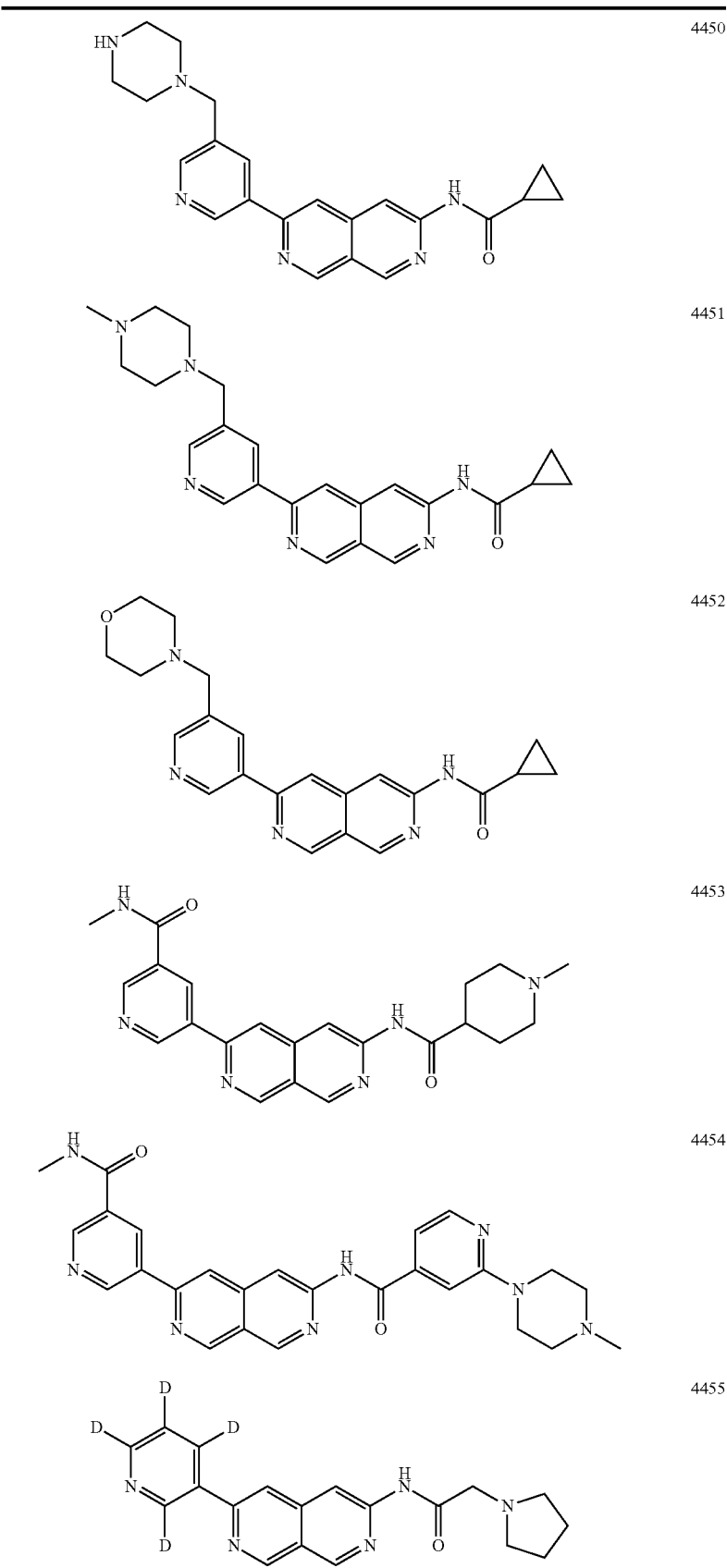
4450
4451
4452
4453
4454
4455

TABLE 1-continued
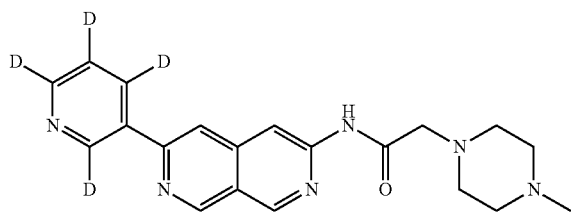 [SMILES: [2H]c1nc([2H])c(-c2cc3cc(NC(=O)CN4CCN(C)CC4)ncc3cn2)c([2H])c1[2H]] 4456
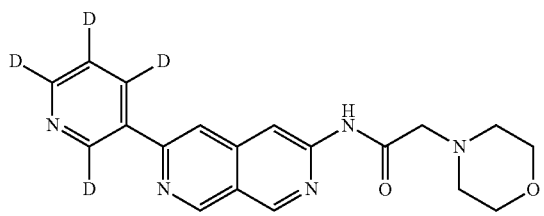 [SMILES: [2H]c1nc([2H])c(-c2cc3cc(NC(=O)CN4CCOCC4)ncc3cn2)c([2H])c1[2H]] 4457
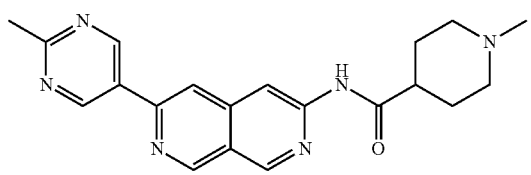 4458
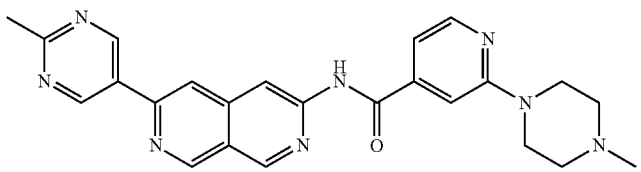 4459
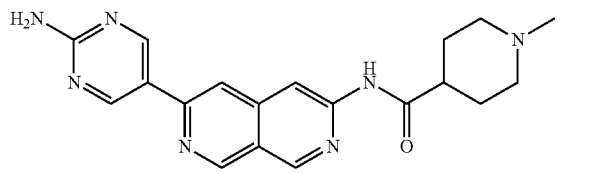 [SMILES: CN1CCC(C(=O)Nc2cc3cc(-c4cnc(N)nc4)ncc3cn2)CC1] 4460
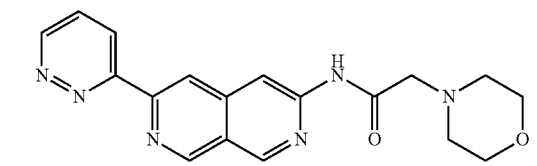 [SMILES: O=C(CN1CCOCC1)Nc1cc2cc(-c3cccnn3)ncc2cn1] 4461
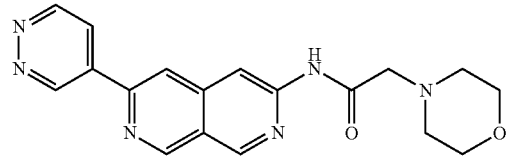 [SMILES: O=C(CN1CCOCC1)Nc1cc2cc(-c3ccnnc3)ncc2cn1] 4462
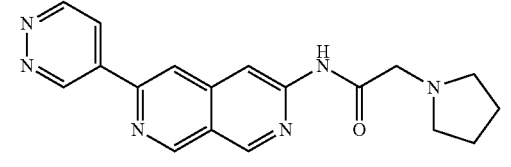 4463

TABLE 1-continued
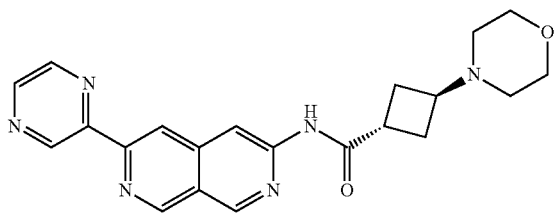 [SMILES: O=C(Nc1cc2cc(-c3cnccn3)ncc2cn1)[C@H]1C[C@H](N2CCOCC2)C1]
4464
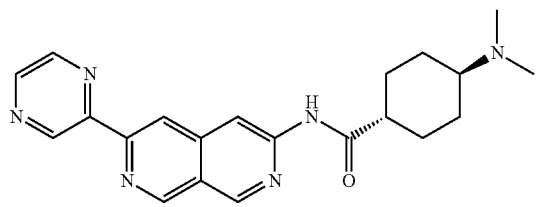 [SMILES: CN(C)[C@H]1CC[C@H](C(=O)Nc2cc3cc(-c4cnccn4)ncc3cn2)CC1]
4465
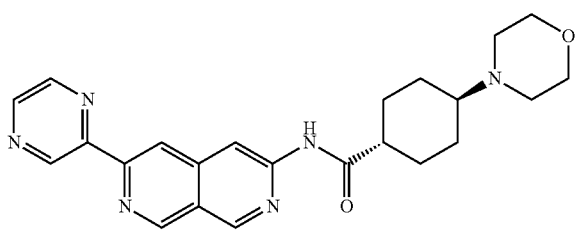 [SMILES: O=C(Nc1cc2cc(-c3cnccn3)ncc2cn1)[C@H]1CC[C@H](N2CCOCC2)CC1]
4466
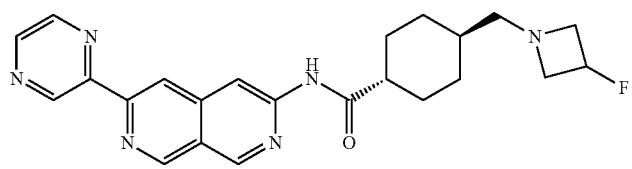 [SMILES: O=C(Nc1cc2cc(-c3cnccn3)ncc2cn1)[C@H]1CC[C@H](CN2CC(F)C2)CC1]
4467
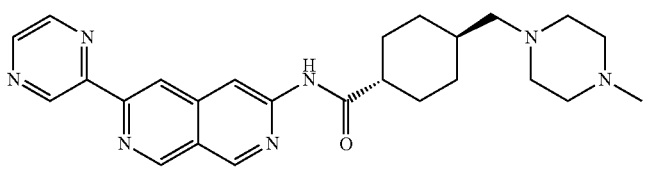 [SMILES: CN1CCN(C[C@H]2CC[C@H](C(=O)Nc3cc4cc(-c5cnccn5)ncc4cn3)CC2)CC1]
4468
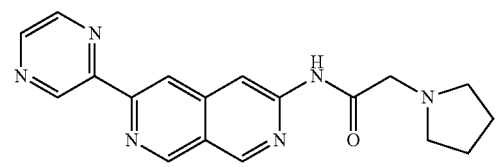 [SMILES: O=C(CN1CCCC1)Nc1cc2cc(-c3cnccn3)ncc2cn1]
4469
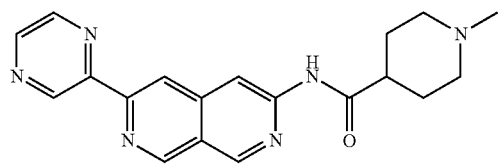 [SMILES: CN1CCC(C(=O)Nc2cc3cc(-c4cnccn4)ncc3cn2)CC1]
4470
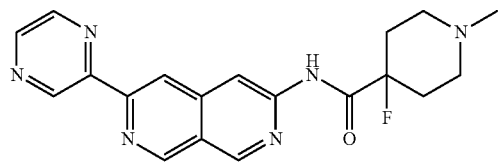 [SMILES: CN1CCC(F)(C(=O)Nc2cc3cc(-c4cnccn4)ncc3cn2)CC1]
4471

TABLE 1-continued
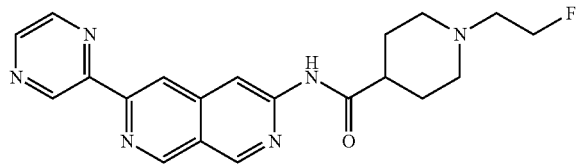 [SMILES: O=C(Nc1cc2cc(-c3cnccn3)ncc2cn1)C1CCN(CCF)CC1] 4472
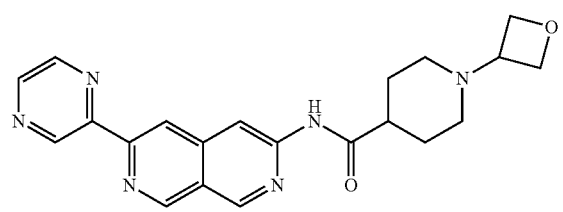 [SMILES: O=C(Nc1cc2cc(-c3cnccn3)ncc2cn1)C1CCN(C2COC2)CC1] 4473
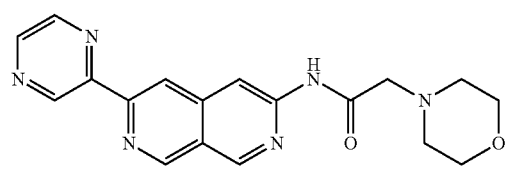 [SMILES: O=C(CN1CCOCC1)Nc1cc2cc(-c3cnccn3)ncc2cn1] 4474
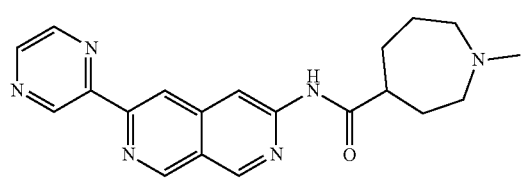 [SMILES: CN1CCCC(C(=O)Nc2cc3cc(-c4cnccn4)ncc3cn2)CC1] 4475
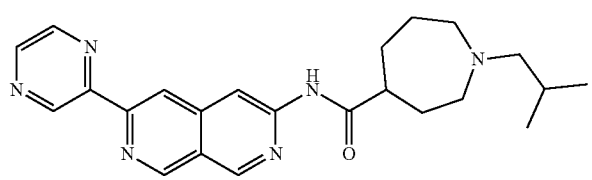 [SMILES: CC(C)CN1CCCC(C(=O)Nc2cc3cc(-c4cnccn4)ncc3cn2)CC1] 4476
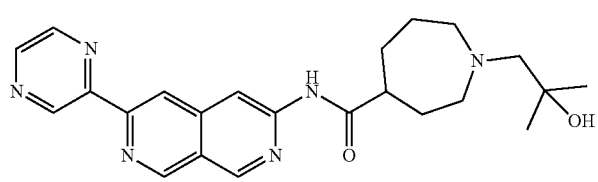 [SMILES: CC(C)(O)CN1CCCC(C(=O)Nc2cc3cc(-c4cnccn4)ncc3cn2)CC1] 4477
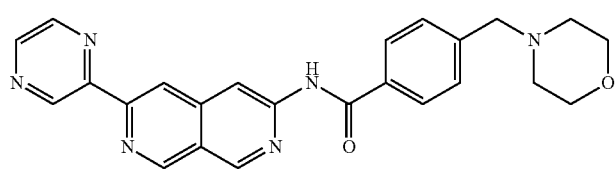 [SMILES: O=C(Nc1cc2cc(-c3cnccn3)ncc2cn1)c1ccc(CN2CCOCC2)cc1] 4478
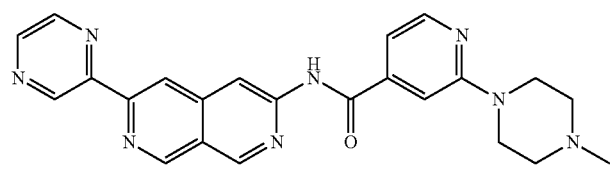 [SMILES: CN1CCN(c2cc(C(=O)Nc3cc4cc(-c5cnccn5)ncc4cn3)ccn2)CC1] 4479

US 10,703,748 B2
TABLE 1-continued
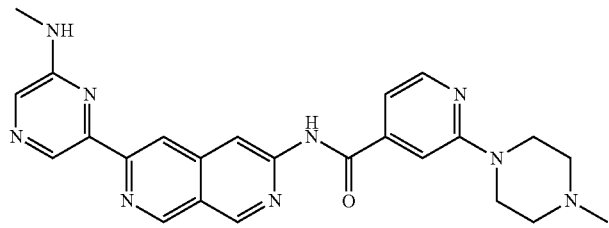 4480
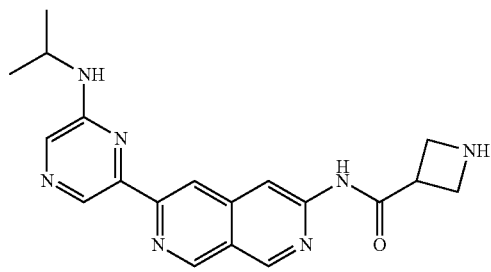 [SMILES: CC(C)Nc1cncc(-c2cc3cc(NC(=O)C4CNC4)ncc3cn2)n1] 4481
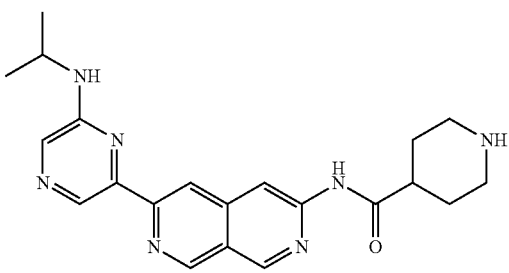 [SMILES: CC(C)Nc1cncc(-c2cc3cc(NC(=O)C4CCNCC4)ncc3cn2)n1] 4482
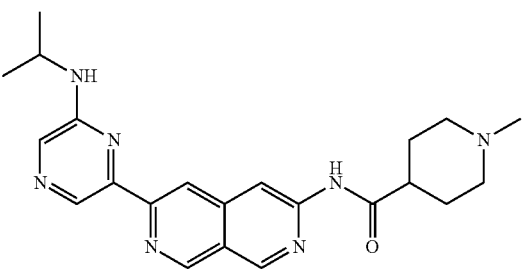 [SMILES: CC(C)Nc1cncc(-c2cc3cc(NC(=O)C4CCN(C)CC4)ncc3cn2)n1] 4483
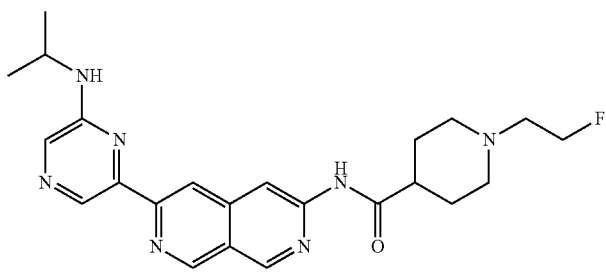 [SMILES: CC(C)Nc1cncc(-c2cc3cc(NC(=O)C4CCN(CCF)CC4)ncc3cn2)n1] 4484
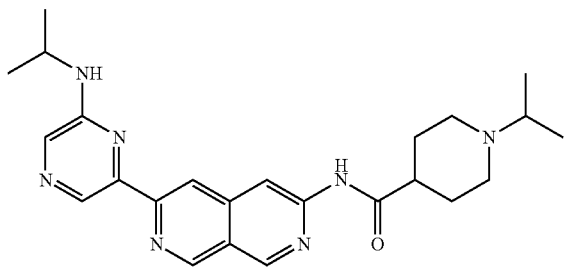 4485

TABLE 1-continued
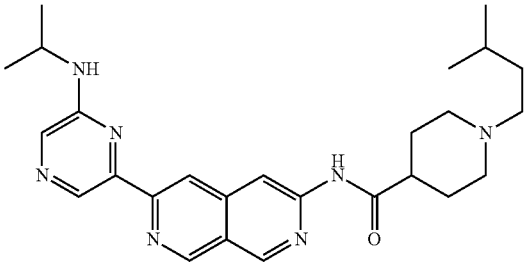 [SMILES: CC(C)CCN1CCC(C(=O)Nc2cc3cc(-c4cncc(NC(C)C)n4)ncc3cn2)CC1]
4486
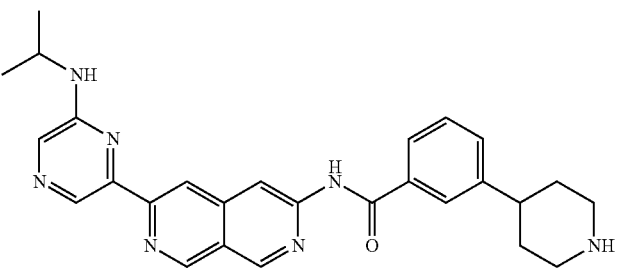
4487
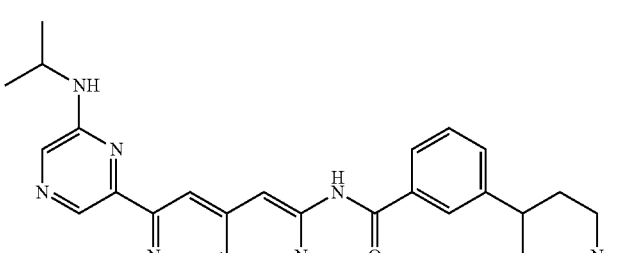
4488
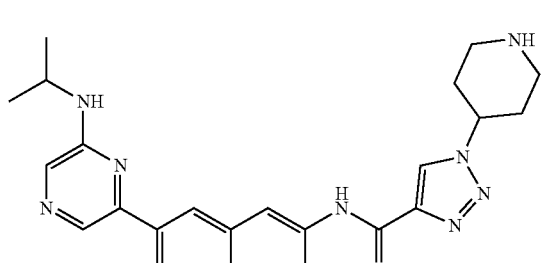
4489
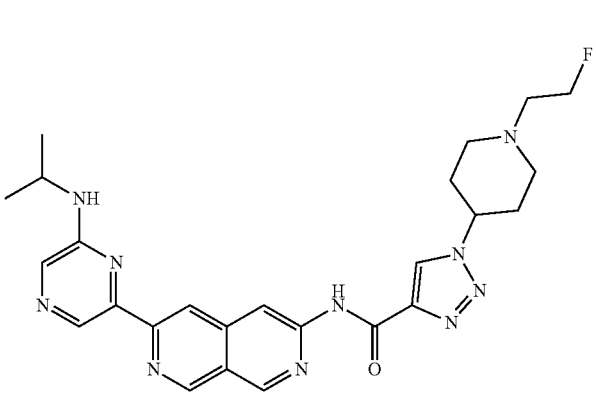 [SMILES: CC(C)Nc1cncc(-c2cc3cc(NC(=O)c4cn(C5CCN(CCF)CC5)nn4)ncc3cn2)n1]
4490

TABLE 1-continued
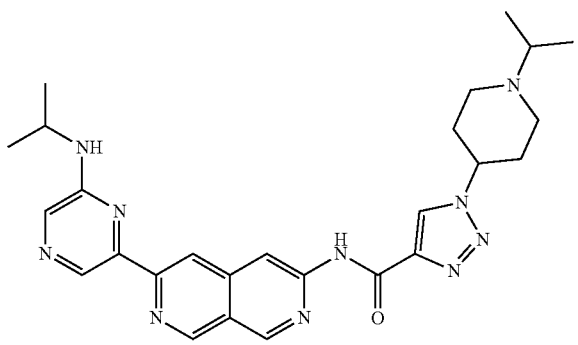 [SMILES: CC(C)Nc1cncc(-c2cc3cc(NC(=O)c4cn(C5CCN(C(C)C)CC5)nn4)ncc3cn2)n1]
4491
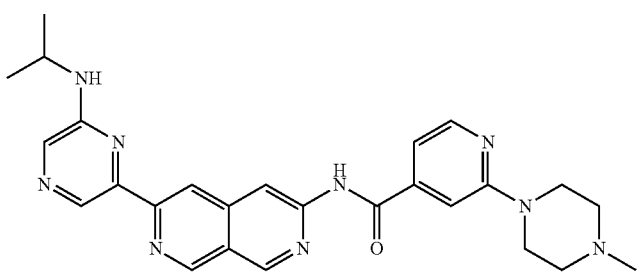 [SMILES: CC(C)Nc1cncc(-c2cc3cc(NC(=O)c4ccnc(N5CCN(C)CC5)c4)ncc3cn2)n1]
4492
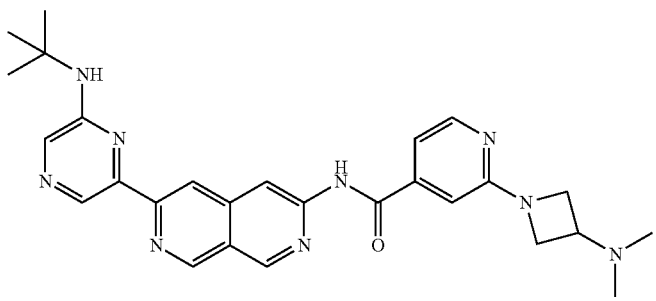 [SMILES: CN(C)C1CN(c2cc(C(=O)Nc3cc4cc(-c5cncc(NC(C)(C)C)n5)ncc4cn3)ccn2)C1]
4493
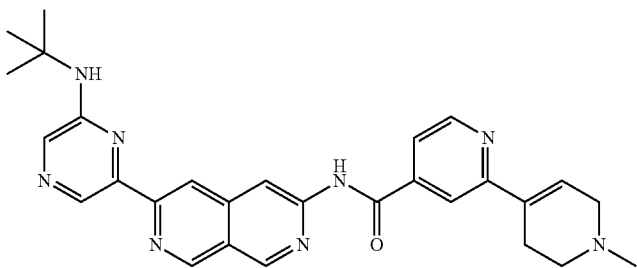 [SMILES: CN1CC=C(c2cc(C(=O)Nc3cc4cc(-c5cncc(NC(C)(C)C)n5)ncc4cn3)ccn2)CC1]
4494
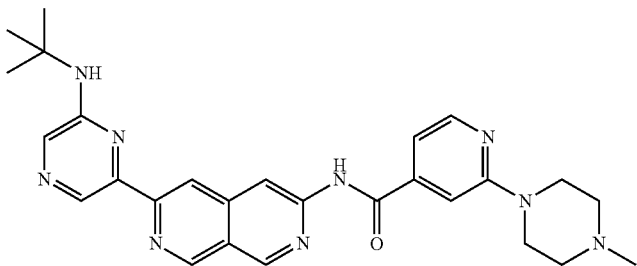 [SMILES: CN1CCN(c2cc(C(=O)Nc3cc4cc(-c5cncc(NC(C)(C)C)n5)ncc4cn3)ccn2)CC1]
4495

TABLE 1-continued
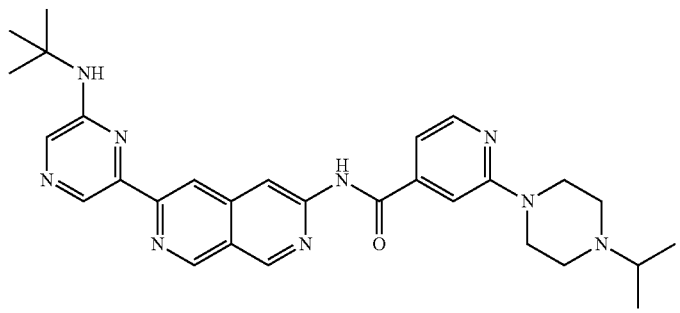 [SMILES: CC(C)N1CCN(c2cc(C(=O)Nc3cc4cc(-c5cncc(NC(C)(C)C)n5)ncc4cn3)ccn2)CC1]
4496
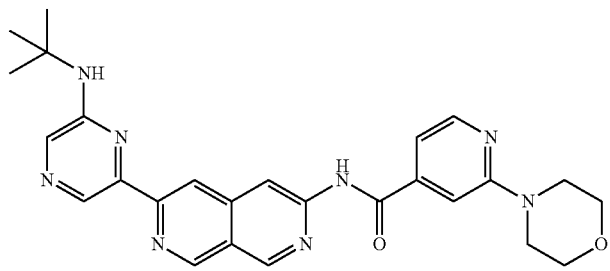 [SMILES: CC(C)(C)Nc1cncc(-c2cc3cc(NC(=O)c4ccnc(N5CCOCC5)c4)ncc3cn2)n1]
4497
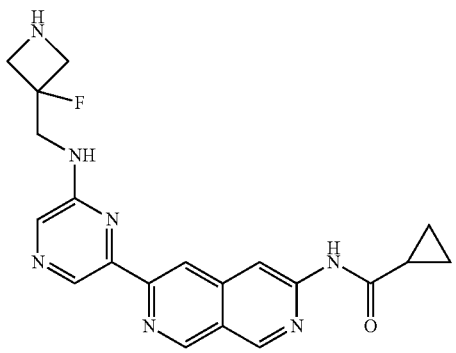 [SMILES: O=C(Nc1cc2cc(-c3cncc(NCC4(F)CNC4)n3)ncc2cn1)C1CC1]
4498
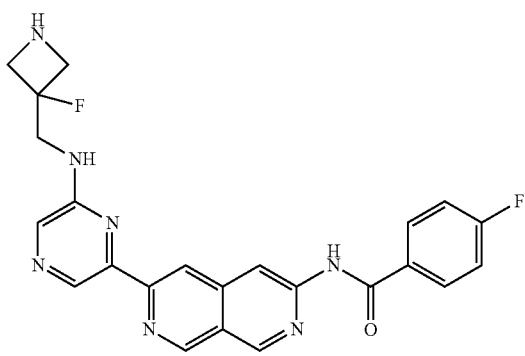 [SMILES: O=C(Nc1cc2cc(-c3cncc(NCC4(F)CNC4)n3)ncc2cn1)c1ccc(F)cc1]
4499
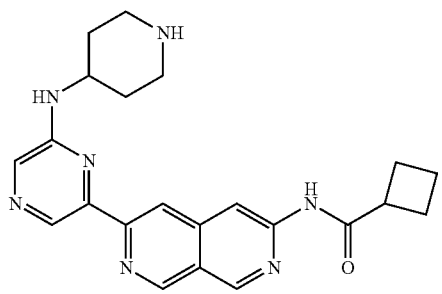 [SMILES: O=C(Nc1cc2cc(-c3cncc(NC4CCNCC4)n3)ncc2cn1)C1CCC1]
4500

TABLE 1-continued
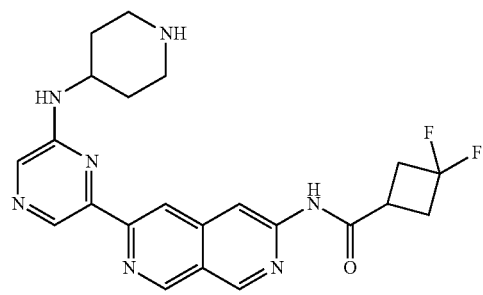 [SMILES: O=C(Nc1cc2cc(-c3cncc(NC4CCNCC4)n3)ncc2cn1)C1CC(F)(F)C1] 4501
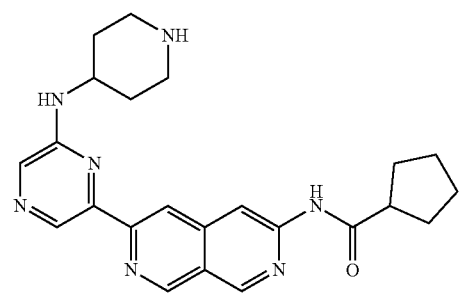 [SMILES: O=C(Nc1cc2cc(-c3cncc(NC4CCNCC4)n3)ncc2cn1)C1CCCC1] 4502
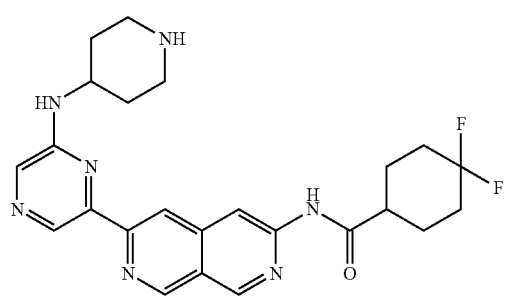 [SMILES: O=C(Nc1cc2cc(-c3cncc(NC4CCNCC4)n3)ncc2cn1)C1CCC(F)(F)CC1] 4503
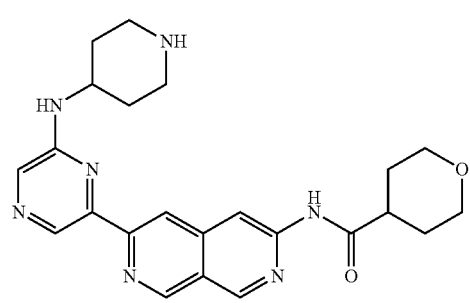 [SMILES: O=C(Nc1cc2cc(-c3cncc(NC4CCNCC4)n3)ncc2cn1)C1CCOCC1] 4504
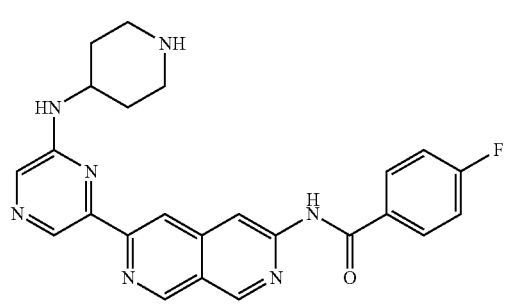 [SMILES: O=C(Nc1cc2cc(-c3cncc(NC4CCNCC4)n3)ncc2cn1)c1ccc(F)cc1] 4505

TABLE 1-continued
| | |
|---|---|
| 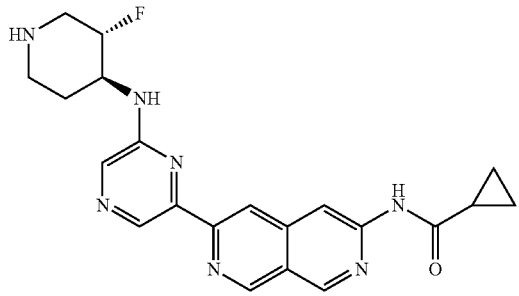 [SMILES: O=C(Nc1cc2cc(-c3cncc(N[C@H]4CCNC[C@@H]4F)n3)ncc2cn1)C1CC1] | 4506 |
| 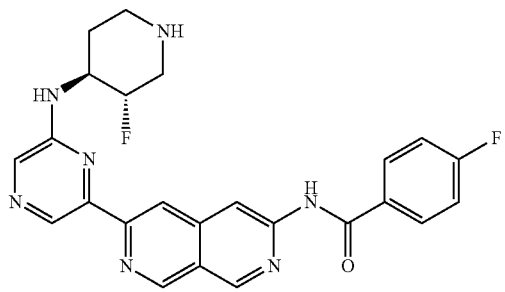 [SMILES: O=C(Nc1cc2cc(-c3cncc(N[C@H]4CCNC[C@@H]4F)n3)ncc2cn1)c1ccc(F)cc1] | 4507 |
| 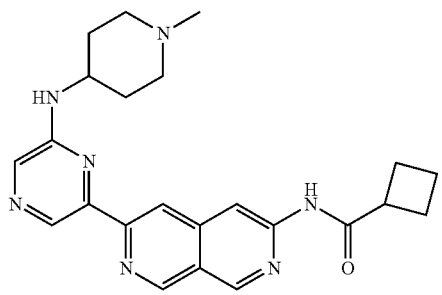 [SMILES: CN1CCC(Nc2cncc(-c3cc4cc(NC(=O)C5CCC5)ncc4cn3)n2)CC1] | 4508 |
| 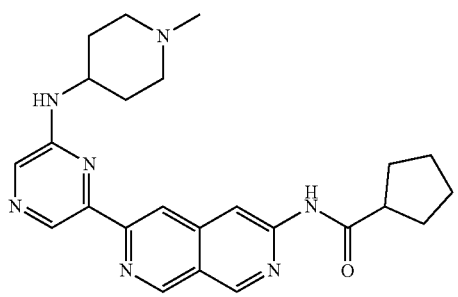 [SMILES: CN1CCC(Nc2cncc(-c3cc4cc(NC(=O)C5CCCC5)ncc4cn3)n2)CC1] | 4509 |
| 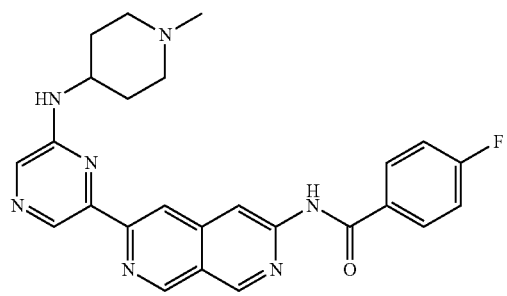 | 4510 |

TABLE 1-continued
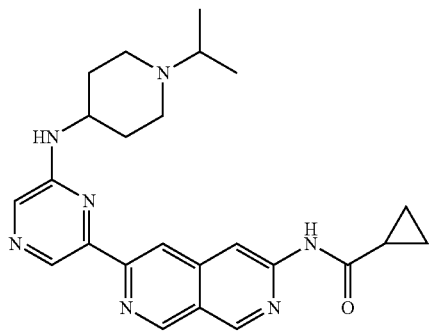 [SMILES: CC(C)N1CCC(Nc2cncc(-c3cc4cc(NC(=O)C5CC5)ncc4cn3)n2)CC1]
4511
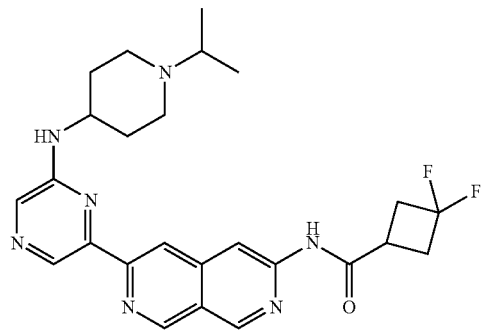
4512
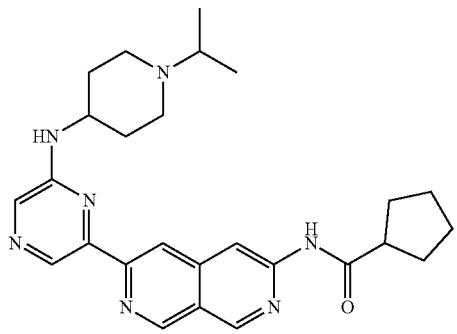 [SMILES: CC(C)N1CCC(Nc2cncc(-c3cc4cc(NC(=O)C5CCCC5)ncc4cn3)n2)CC1]
4513
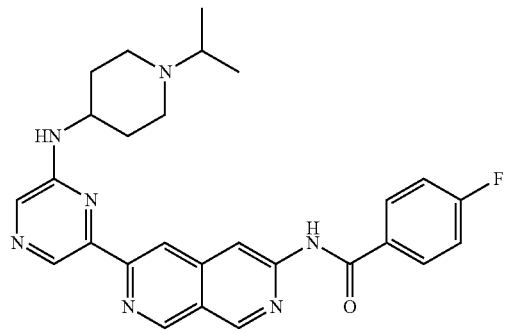 [SMILES: CC(C)N1CCC(Nc2cncc(-c3cc4cc(NC(=O)c5ccc(F)cc5)ncc4cn3)n2)CC1]
4514
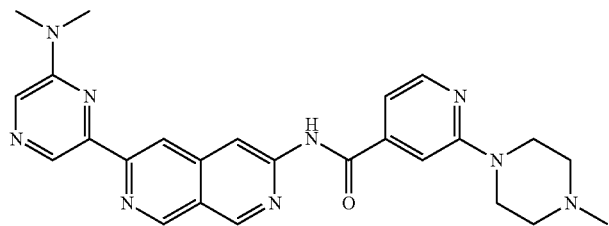 [SMILES: CN1CCN(c2cc(C(=O)Nc3cc4cc(-c5cncc(N(C)C)n5)ncc4cn3)ccn2)CC1]
4515

TABLE 1-continued
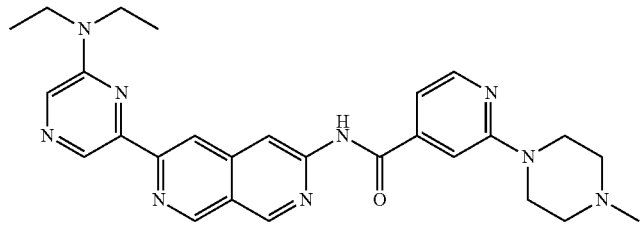 [SMILES: CCN(CC)c1cncc(-c2cc3cc(NC(=O)c4ccnc(N5CCN(C)CC5)c4)ncc3cn2)n1]
4516
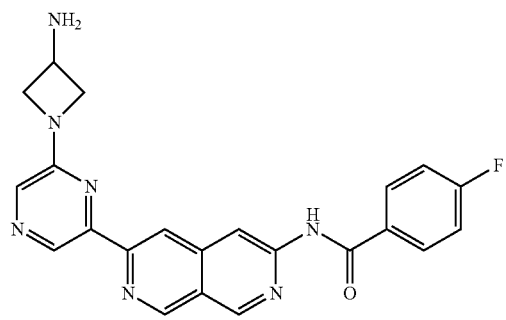 [SMILES: NC1CN(c2cncc(-c3cc4cc(NC(=O)c5ccc(F)cc5)ncc4cn3)n2)C1]
4517
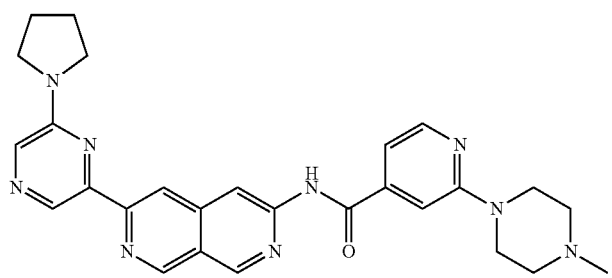 [SMILES: CN1CCN(c2cc(C(=O)Nc3cc4cc(-c5cncc(N6CCCC6)n5)ncc4cn3)ccn2)CC1]
4518
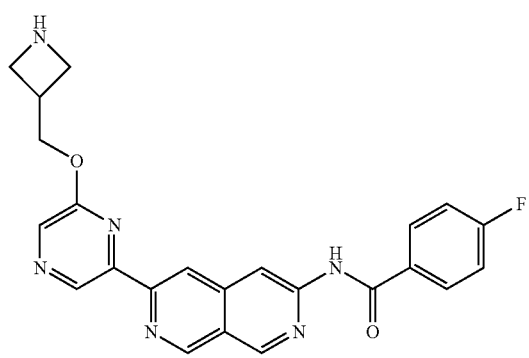 [SMILES: O=C(Nc1cc2cc(-c3cncc(OCC4CNC4)n3)ncc2cn1)c1ccc(F)cc1]
4519
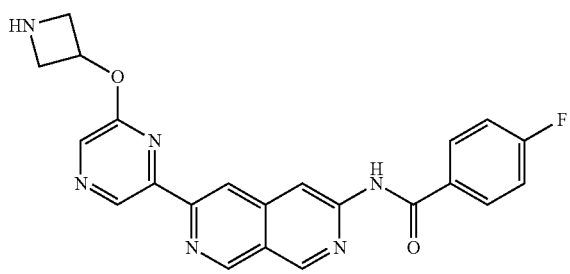 [SMILES: O=C(Nc1cc2cc(-c3cncc(OC4CNC4)n3)ncc2cn1)c1ccc(F)cc1]
4520

TABLE 1-continued
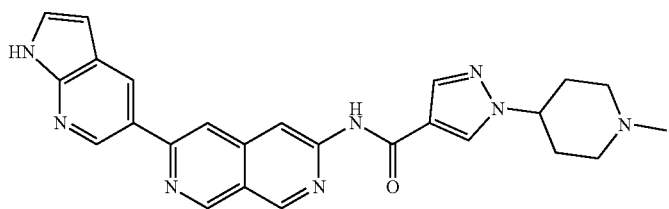 [SMILES: CN1CCC(n2cc(C(=O)Nc3cc4cc(-c5cnc6[nH]ccc6c5)ncc4cn3)cn2)CC1] 4521
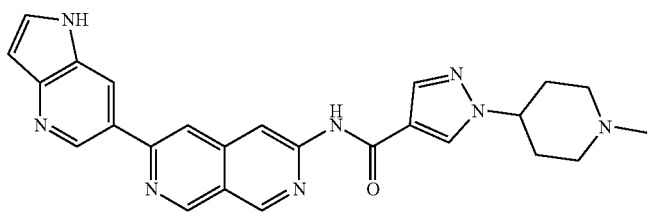 [SMILES: CN1CCC(n2cc(C(=O)Nc3cc4cc(-c5cnc6cc[nH]c6c5)ncc4cn3)cn2)CC1] 4522
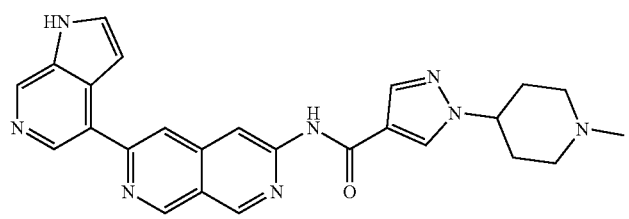 [SMILES: CN1CCC(n2cc(C(=O)Nc3cc4cc(-c5cncc6[nH]ccc56)ncc4cn3)cn2)CC1] 4523
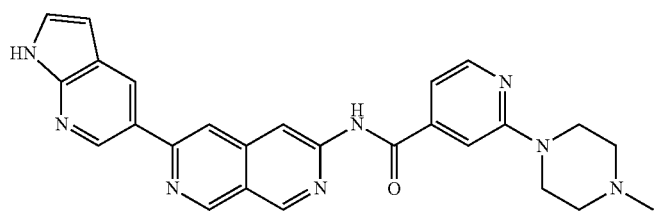 [SMILES: CN1CCN(c2cc(C(=O)Nc3cc4cc(-c5cnc6[nH]ccc6c5)ncc4cn3)ccn2)CC1] 4524
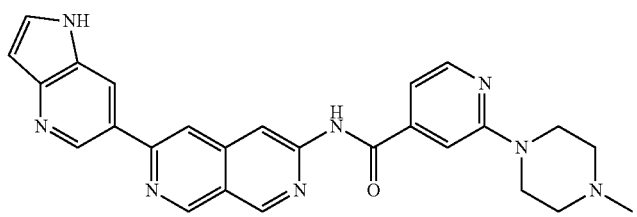 [SMILES: CN1CCN(c2cc(C(=O)Nc3cc4cc(-c5cnc6cc[nH]c6c5)ncc4cn3)ccn2)CC1] 4525
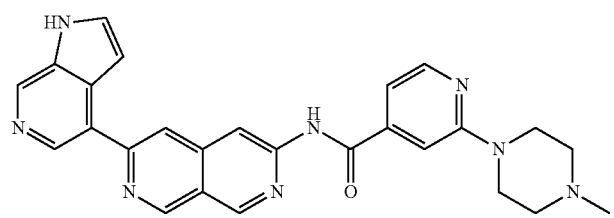 [SMILES: CN1CCN(c2cc(C(=O)Nc3cc4cc(-c5cncc6[nH]ccc56)ncc4cn3)ccn2)CC1] 4526
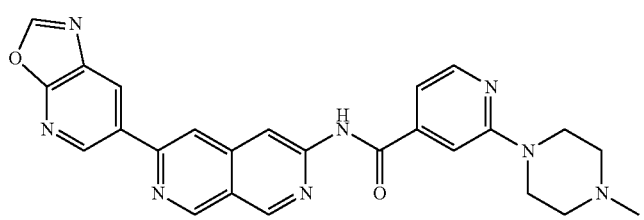 [SMILES: CN1CCN(c2cc(C(=O)Nc3cc4cc(-c5cnc6ocnc6c5)ncc4cn3)ccn2)CC1] 4527

TABLE 1-continued
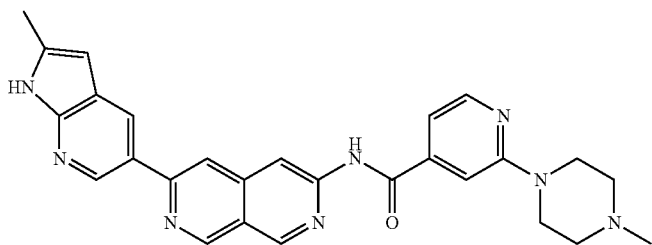
4528
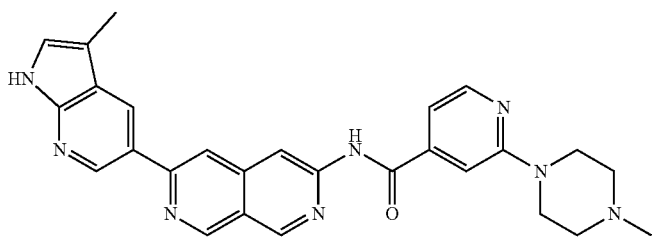 [SMILES: Cc1c[nH]c2ncc(-c3cc4cc(NC(=O)c5ccnc(N6CCN(C)CC6)c5)ncc4cn3)cc12]
4529
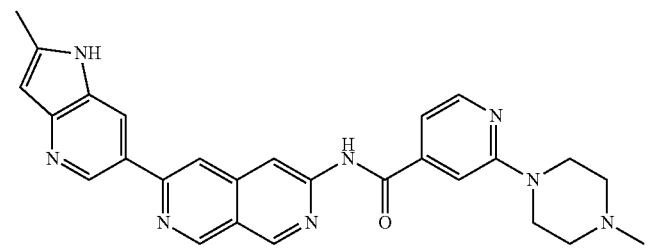
4530
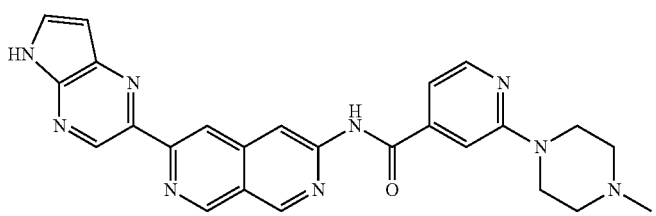
4531
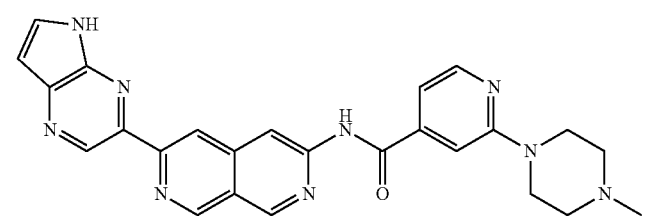 [SMILES: CN1CCN(c2cc(C(=O)Nc3cc4cc(-c5cnc6cc[nH]c6n5)ncc4cn3)ccn2)CC1]
4532
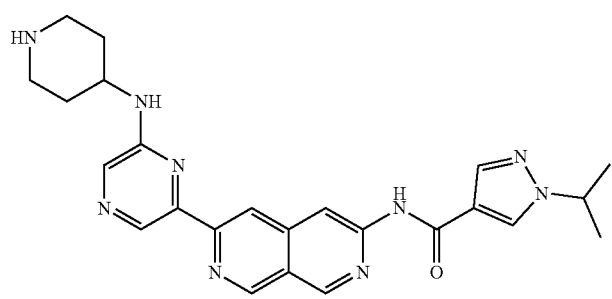 [SMILES: CC(C)n1cc(C(=O)Nc2cc3cc(-c4cncc(NC5CCNCC5)n4)ncc3cn2)cn1]
4533

TABLE 1-continued
| | |
|---|---|
| 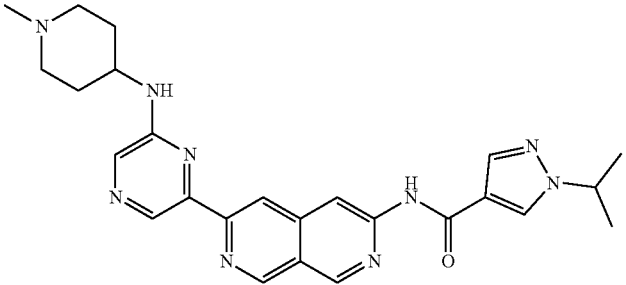 [SMILES: CC(C)n1cc(C(=O)Nc2cc3cc(-c4cncc(NC5CCN(C)CC5)n4)ncc3cn2)cn1] | 4534 |
| 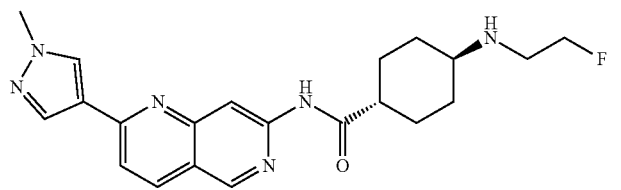 [SMILES: Cn1cc(-c2ccc3cnc(NC(=O)[C@H]4CC[C@H](NCCF)CC4)cc3n2)cn1] | 4535 |
| 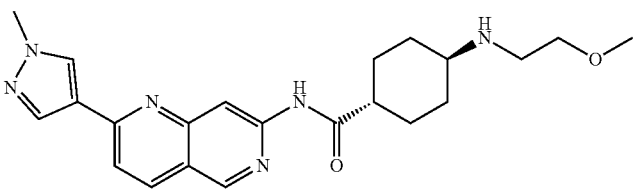 [SMILES: COCCN[C@H]1CC[C@H](C(=O)Nc2cc3nc(-c4cnn(C)c4)ccc3cn2)CC1] | 4536 |
| 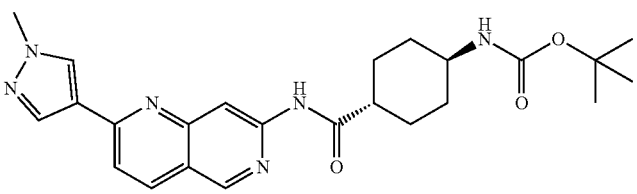 [SMILES: Cn1cc(-c2ccc3cnc(NC(=O)[C@H]4CC[C@H](NC(=O)OC(C)(C)C)CC4)cc3n2)cn1] | 4537 |
| 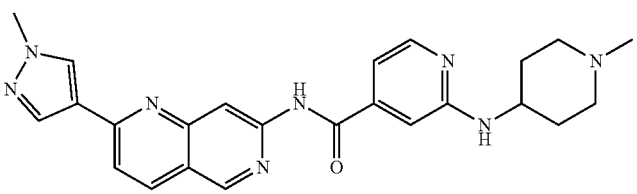 [SMILES: CN1CCC(Nc2cc(C(=O)Nc3cc4nc(-c5cnn(C)c5)ccc4cn3)ccn2)CC1] | 4538 |
| 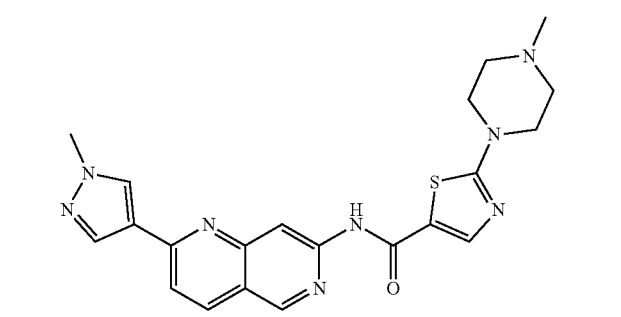 | 4539 |
| 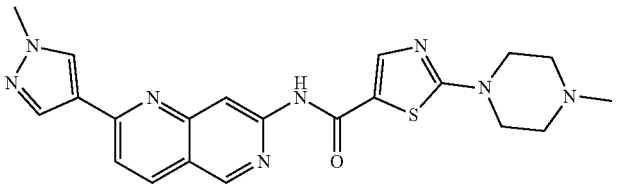 | 4540 |

TABLE 1-continued
| | |
|---|---|
| 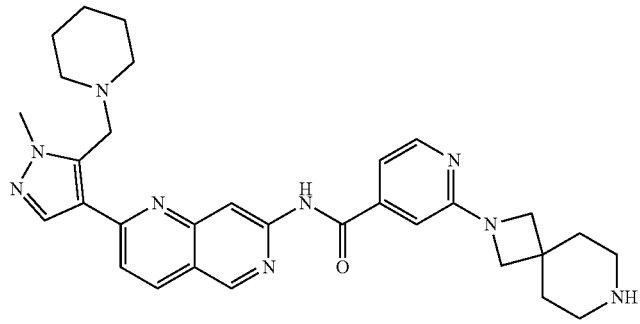 [SMILES: Cn1ncc(-c2ccc3cnc(NC(=O)c4ccnc(N5CC6(CCNCC6)C5)c4)cc3n2)c1CN1CCCCC1] | 4541 |
| 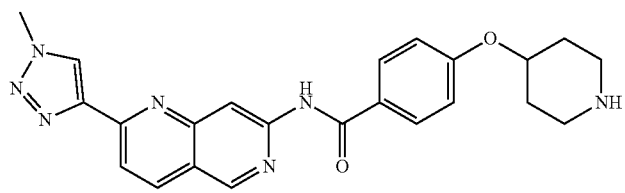 [SMILES: Cn1cc(-c2ccc3cnc(NC(=O)c4ccc(OC5CCNCC5)cc4)cc3n2)nn1] | 4542 |
| 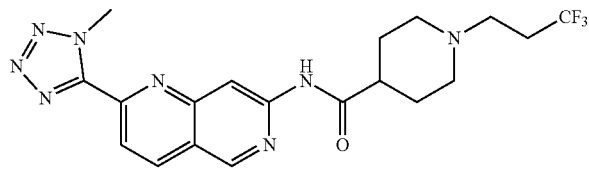 [SMILES: Cn1nnnc1-c1ccc2cnc(NC(=O)C3CCN(CCC(F)(F)F)CC3)cc2n1] | 4543 |
| 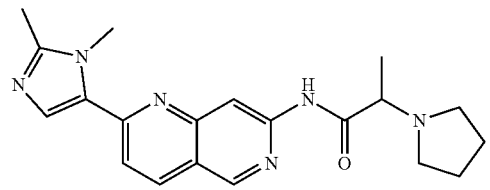 [SMILES: Cc1ncc(-c2ccc3cnc(NC(=O)C(C)N4CCCC4)cc3n2)n1C] | 4544 |
| 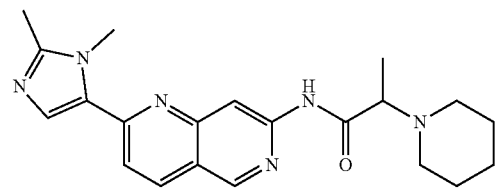 [SMILES: Cc1ncc(-c2ccc3cnc(NC(=O)C(C)N4CCCCC4)cc3n2)n1C] | 4545 |
| 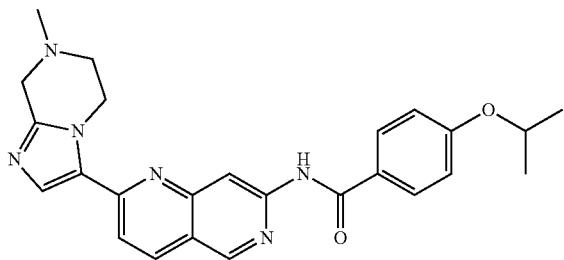 [SMILES: CC(C)Oc1ccc(C(=O)Nc2cc3nc(-c4cnc5n4CCN(C)C5)ccc3cn2)cc1] | 4546 |
| 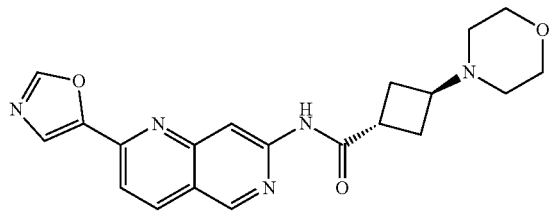 [SMILES: O=C(Nc1cc2nc(-c3cnco3)ccc2cn1)[C@H]1C[C@H](N2CCOCC2)C1] | 4547 |

TABLE 1-continued
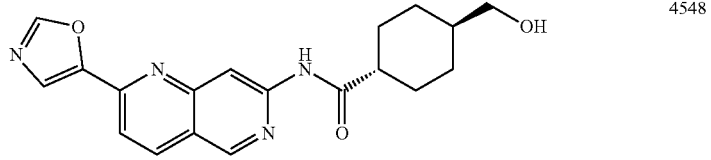 4548
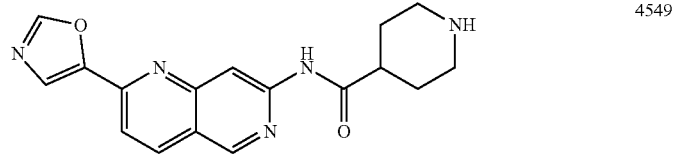 4549
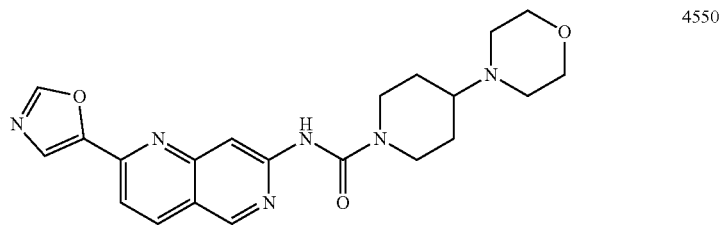 4550
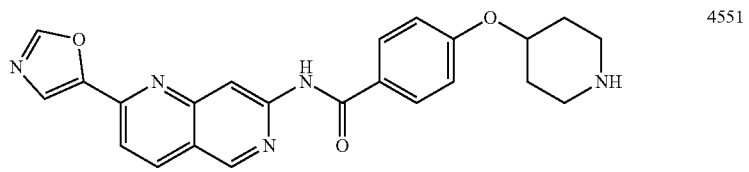 4551
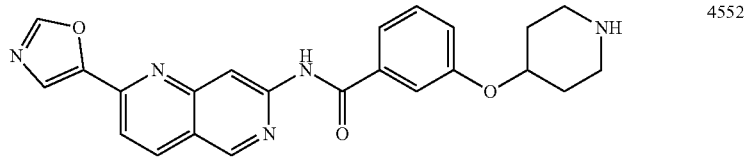 4552
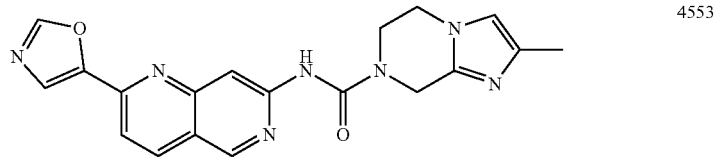 4553
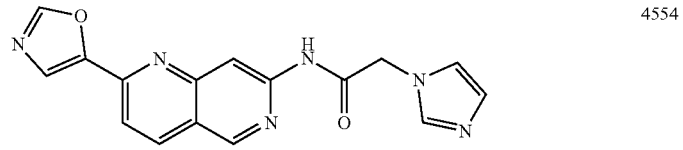 4554
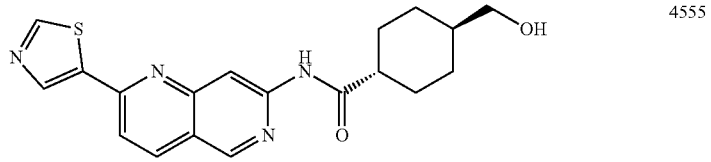 4555
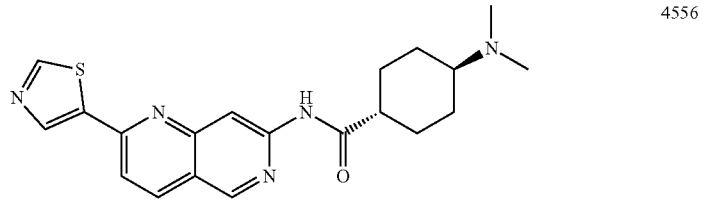 4556

TABLE 1-continued
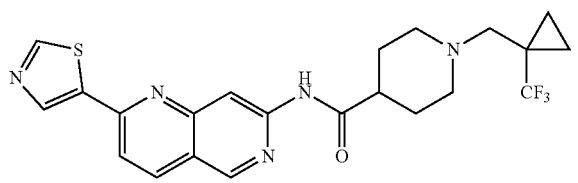 [SMILES: O=C(Nc1cc2nc(-c3cncs3)ccc2cn1)C1CCN(CC2(C(F)(F)F)CC2)CC1] 4557
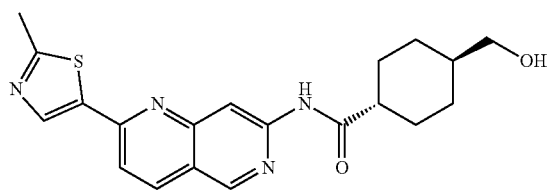 4558
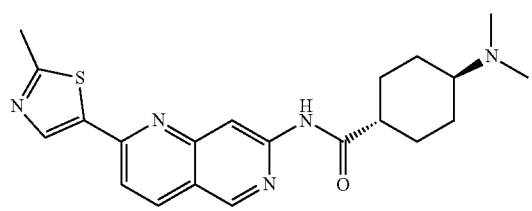 4559
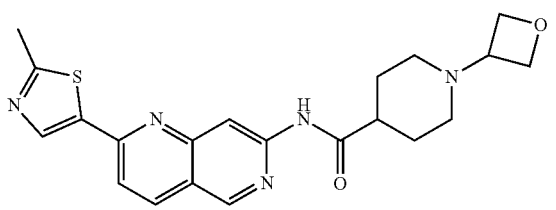 [SMILES: Cc1ncc(-c2ccc3cnc(NC(=O)C4CCN(C5COC5)CC4)cc3n2)s1] 4560
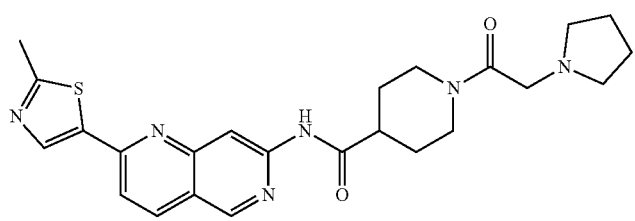 [SMILES: Cc1ncc(-c2ccc3cnc(NC(=O)C4CCN(C(=O)CN5CCCC5)CC4)cc3n2)s1] 4561
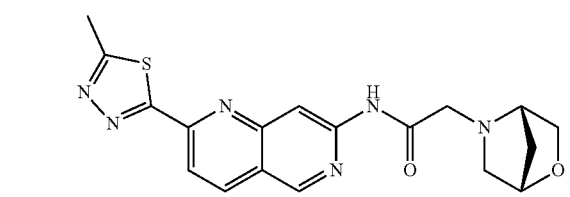 [SMILES: Cc1nnc(-c2ccc3cnc(NC(=O)CN4C[C@@H]5C[C@H]4CO5)cc3n2)s1] 4562
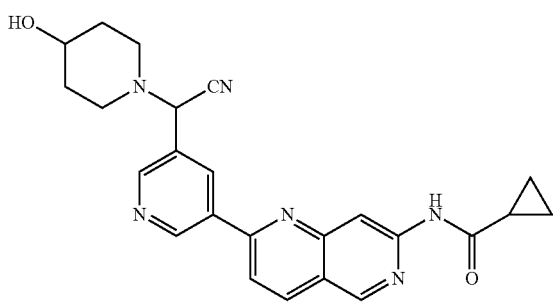 [SMILES: N#CC(c1cncc(-c2ccc3cnc(NC(=O)C4CC4)cc3n2)c1)N1CCC(O)CC1] 4563

TABLE 1-continued
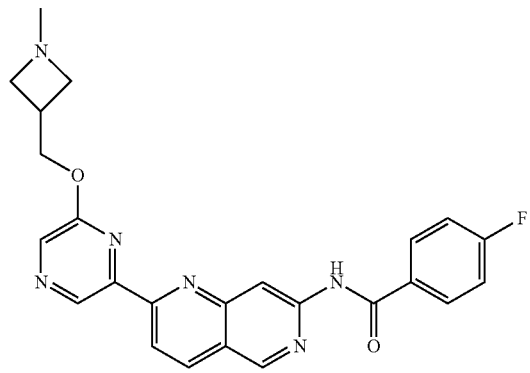 [SMILES: CN1CC(COc2cncc(-c3ccc4cnc(NC(=O)c5ccc(F)cc5)cc4n3)n2)C1]
4564
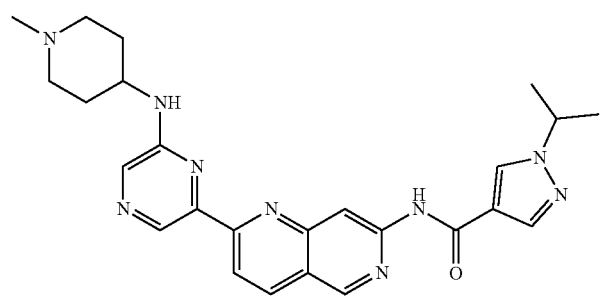 [SMILES: CC(C)n1cc(C(=O)Nc2cc3nc(-c4cncc(NC5CCN(C)CC5)n4)ccc3cn2)cn1]
4565
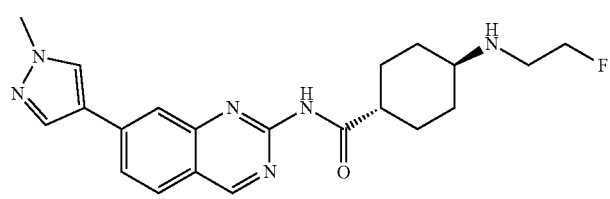 [SMILES: Cn1cc(-c2ccc3cnc(NC(=O)[C@H]4CC[C@H](NCCF)CC4)nc3c2)cn1]
4566
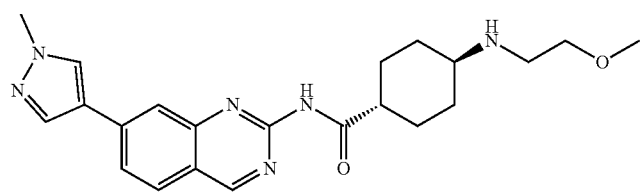 [SMILES: COCCN[C@H]1CC[C@H](C(=O)Nc2ncc3ccc(-c4cnn(C)c4)cc3n2)CC1]
4567
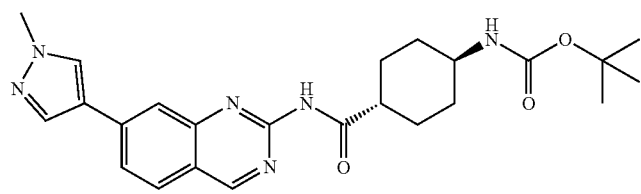 [SMILES: Cn1cc(-c2ccc3cnc(NC(=O)[C@H]4CC[C@H](NC(=O)OC(C)(C)C)CC4)nc3c2)cn1]
4568
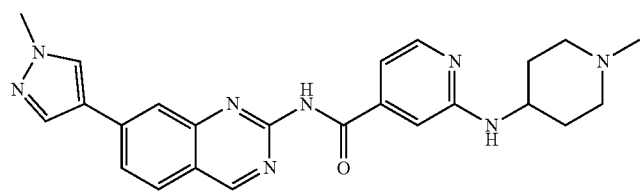 [SMILES: CN1CCC(Nc2cc(C(=O)Nc3ncc4ccc(-c5cnn(C)c5)cc4n3)ccn2)CC1]
4569

1391
TABLE 1-continued
| | |
|---|---|
| 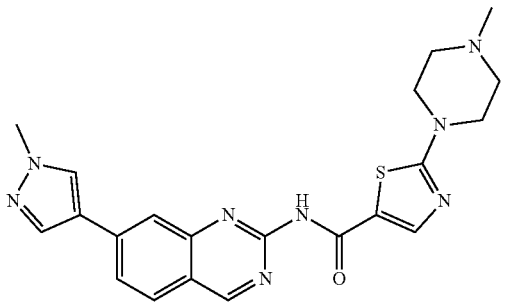 | 4570 |
| 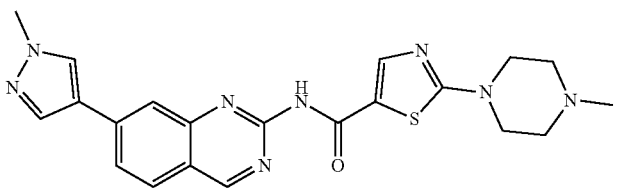 [SMILES: CN1CCN(c2ncc(C(=O)Nc3ncc4ccc(-c5cnn(C)c5)cc4n3)s2)CC1] | 4571 |
| 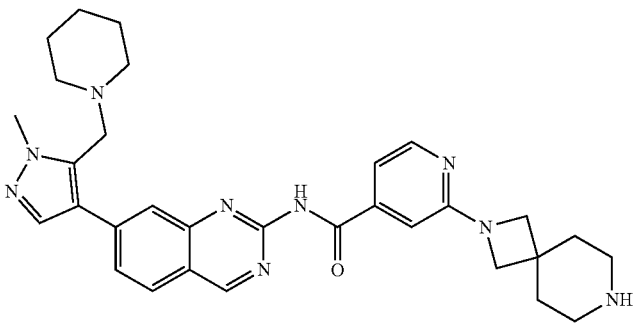 [SMILES: Cn1ncc(-c2ccc3cnc(NC(=O)c4ccnc(N5CC6(CCNCC6)C5)c4)nc3c2)c1CN1CCCCC1] | 4572 |
| 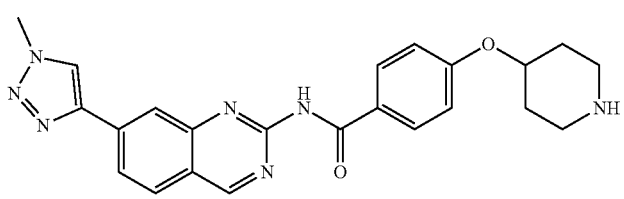 [SMILES: Cn1cc(-c2ccc3cnc(NC(=O)c4ccc(OC5CCNCC5)cc4)nc3c2)nn1] | 4573 |
| 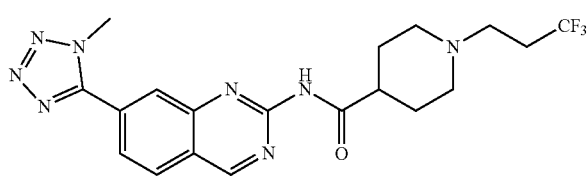 | 4574 |
| 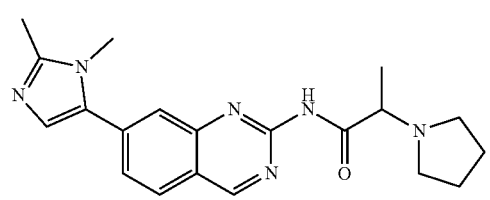 [SMILES: Cc1ncc(-c2ccc3cnc(NC(=O)C(C)N4CCCC4)nc3c2)n1C] | 4575 |
| 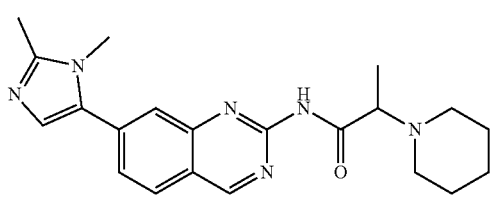 [SMILES: Cc1ncc(-c2ccc3cnc(NC(=O)C(C)N4CCCCC4)nc3c2)n1C] | 4576 |

TABLE 1-continued
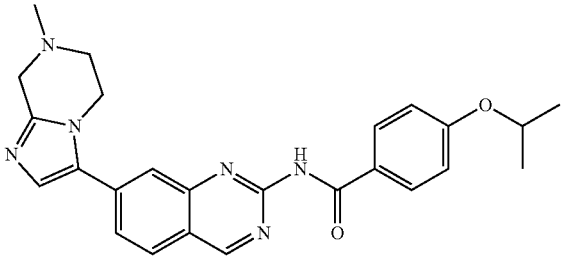 [SMILES: CC(C)Oc1ccc(C(=O)Nc2ncc3ccc(-c4cnc5n4CCN(C)C5)cc3n2)cc1] 4577
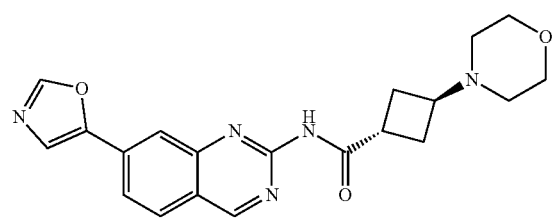 [SMILES: O=C(Nc1ncc2ccc(-c3cnco3)cc2n1)[C@H]1C[C@H](N2CCOCC2)C1] 4578
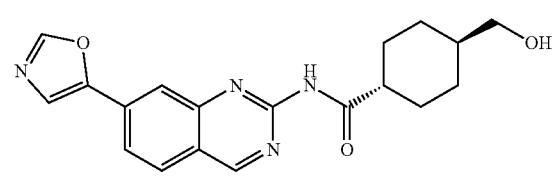 [SMILES: O=C(Nc1ncc2ccc(-c3cnco3)cc2n1)[C@H]1CC[C@H](CO)CC1] 4579
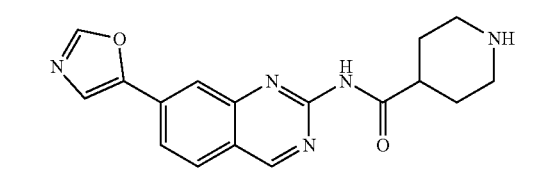 [SMILES: O=C(Nc1ncc2ccc(-c3cnco3)cc2n1)C1CCNCC1] 4580
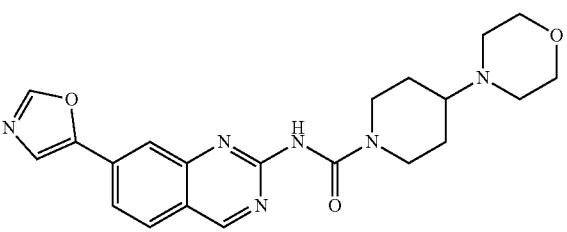 [SMILES: O=C(Nc1ncc2ccc(-c3cnco3)cc2n1)N1CCC(N2CCOCC2)CC1] 4581
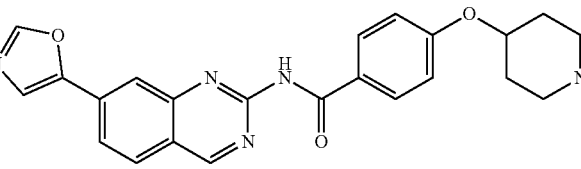 4582
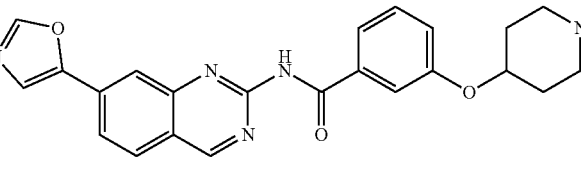 4583
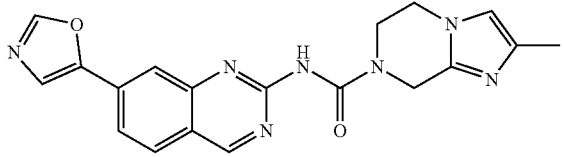 [SMILES: Cc1cn2c(n1)CN(C(=O)Nc1ncc3ccc(-c4cnco4)cc3n1)CC2] 4584

TABLE 1-continued

| | |
|---|---|
| (structure) | 4585 |
| (structure) | 4586 |
| (structure) | 4587 |
| (structure) | 4588 |
| (structure) | 4589 |
| (structure) | 4590 |
| (structure) | 4591 |
| (structure) | 4592 |

TABLE 1-continued
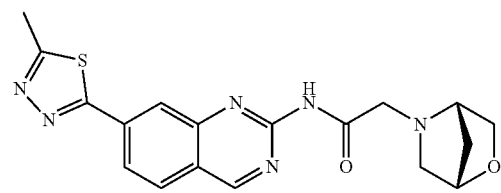 [SMILES: Cc1nnc(-c2ccc3cnc(NC(=O)CN4C[C@@H]5C[C@H]4CO5)nc3c2)s1]
4593
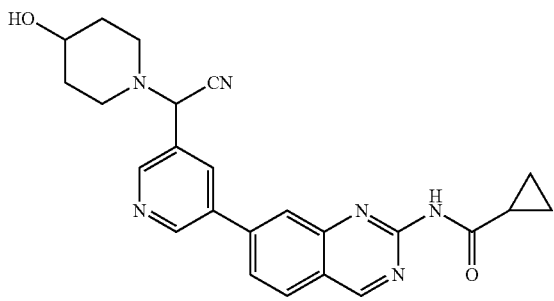 [SMILES: N#CC(c1cncc(-c2ccc3cnc(NC(=O)C4CC4)nc3c2)c1)N1CCC(O)CC1]
4594
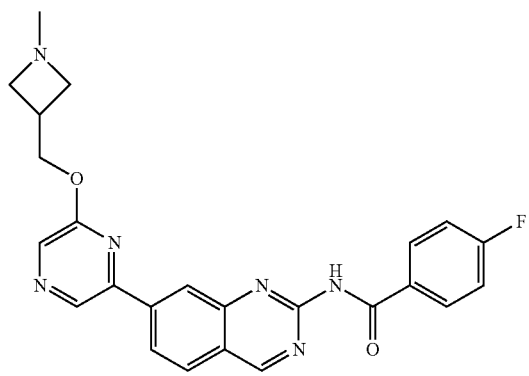 [SMILES: CN1CC(COc2cncc(-c3ccc4cnc(NC(=O)c5ccc(F)cc5)nc4c3)n2)C1]
4595
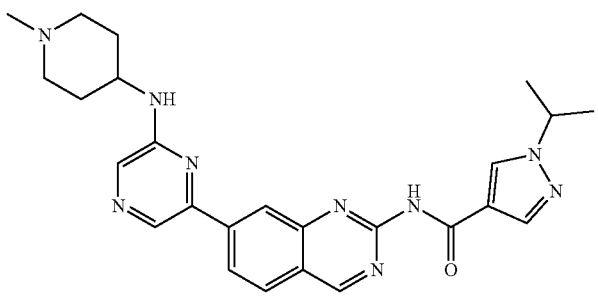 [SMILES: CC(C)n1cc(C(=O)Nc2ncc3ccc(-c4cncc(NC5CCN(C)CC5)n4)cc3n2)cn1]
4596
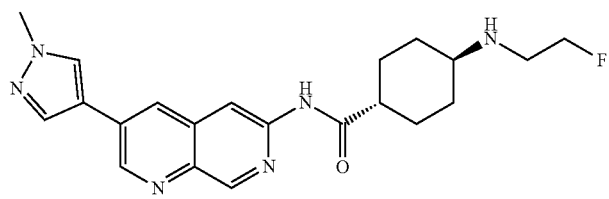 [SMILES: Cn1cc(-c2cnc3cnc(NC(=O)[C@H]4CC[C@H](NCCF)CC4)cc3c2)cn1]
4597
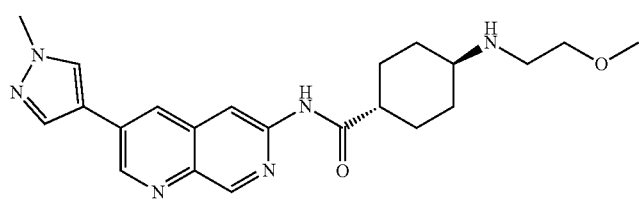 [SMILES: COCCN[C@H]1CC[C@H](C(=O)Nc2cc3cc(-c4cnn(C)c4)cnc3cn2)CC1]
4598

TABLE 1-continued
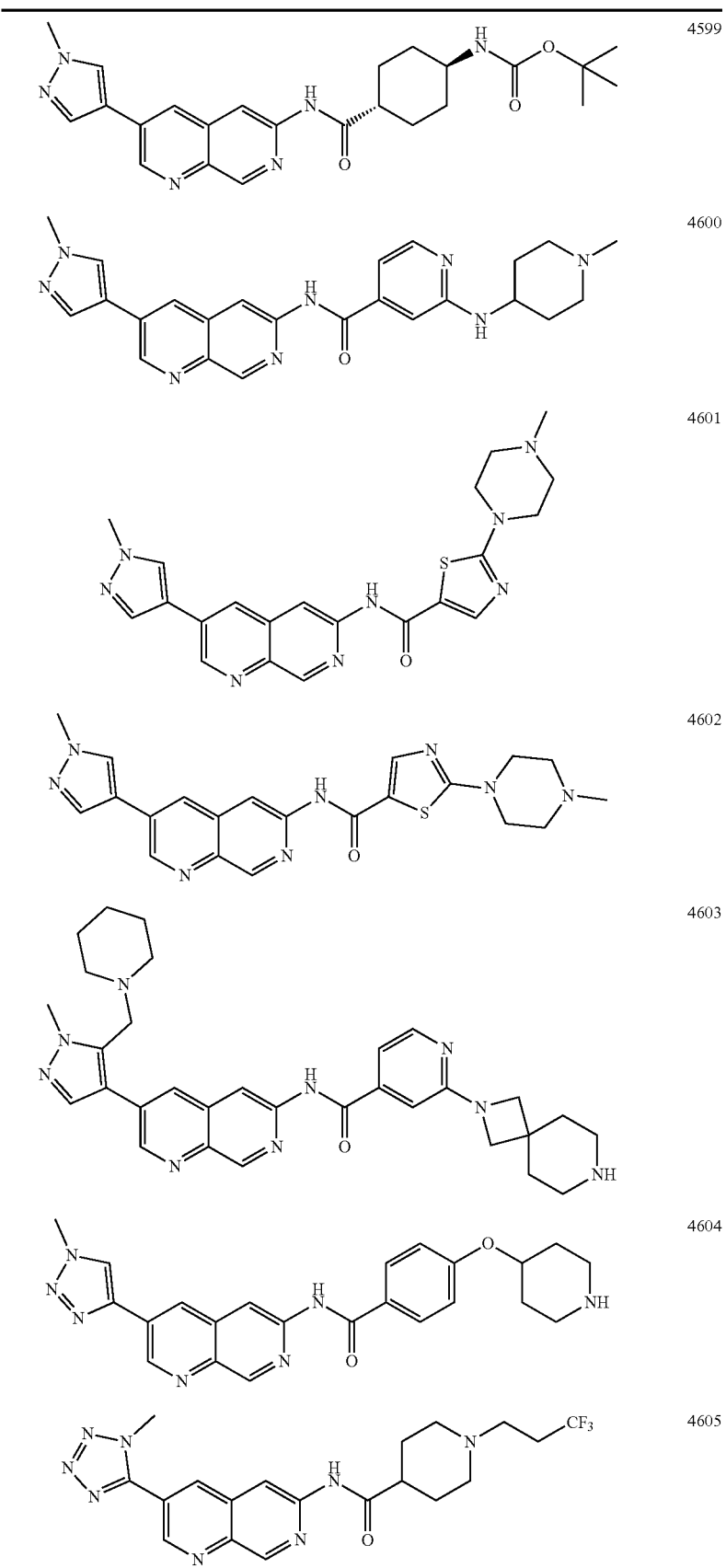

TABLE 1-continued
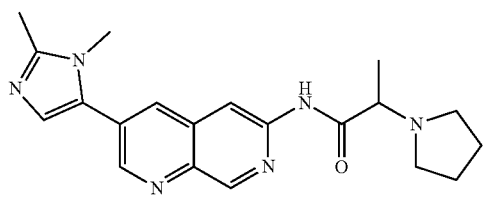 [SMILES: Cc1ncc(-c2cnc3cnc(NC(=O)C(C)N4CCCC4)cc3c2)n1C] 4606
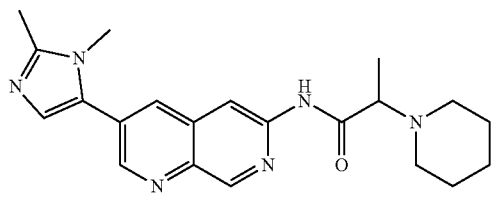 [SMILES: Cc1ncc(-c2cnc3cnc(NC(=O)C(C)N4CCCCC4)cc3c2)n1C] 4607
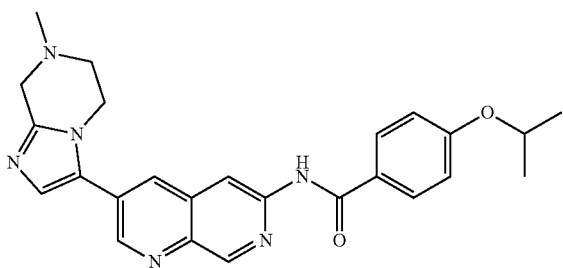 [SMILES: CC(C)Oc1ccc(C(=O)Nc2cc3cc(-c4cnc5n4CCN(C)C5)cnc3cn2)cc1] 4608
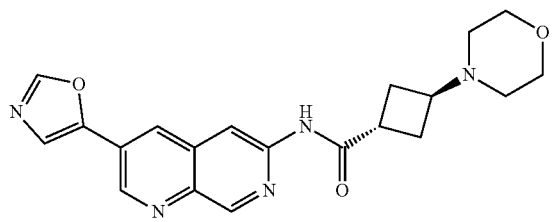 [SMILES: O=C(Nc1cc2cc(-c3cnco3)cnc2cn1)[C@H]1C[C@H](N2CCOCC2)C1] 4609
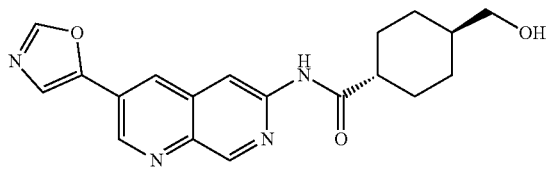 [SMILES: O=C(Nc1cc2cc(-c3cnco3)cnc2cn1)[C@H]1CC[C@H](CO)CC1] 4610
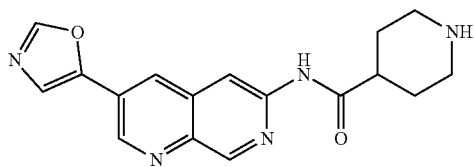 [SMILES: O=C(Nc1cc2cc(-c3cnco3)cnc2cn1)C1CCNCC1] 4611
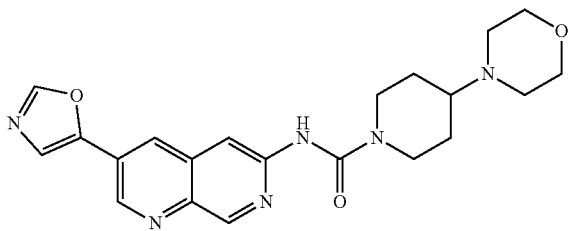 [SMILES: O=C(Nc1cc2cc(-c3cnco3)cnc2cn1)N1CCC(N2CCOCC2)CC1] 4612

TABLE 1-continued
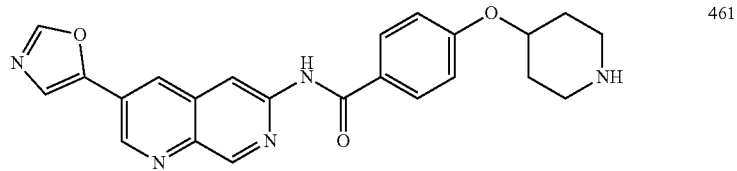 4613
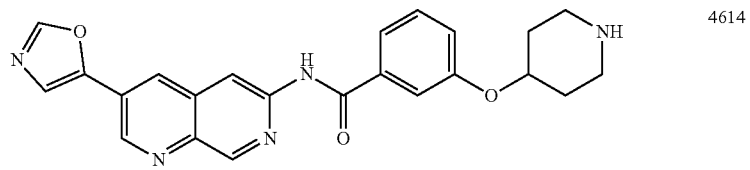 4614
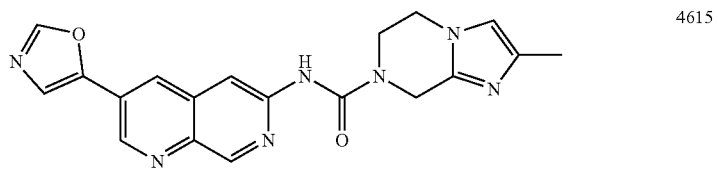 4615
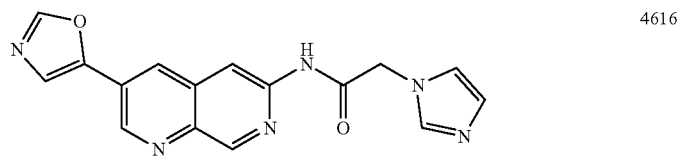 4616
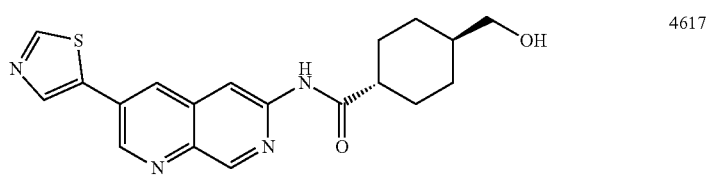 4617
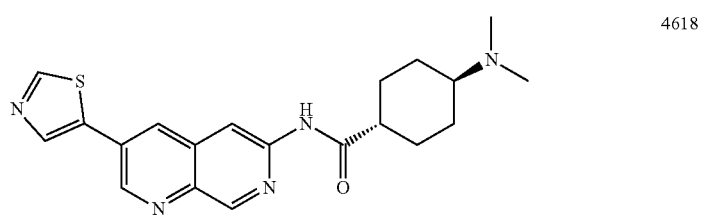 4618
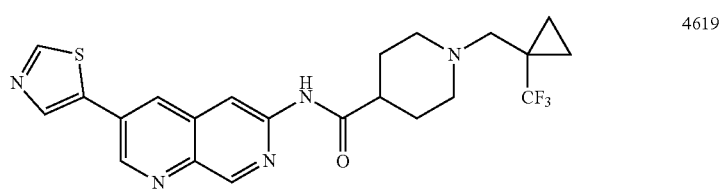 4619
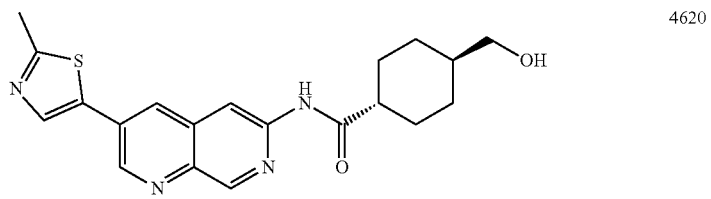 4620

TABLE 1-continued
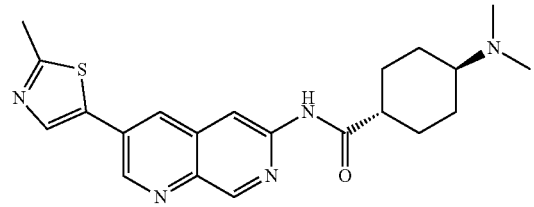 [SMILES: Cc1ncc(-c2cnc3cnc(NC(=O)[C@H]4CC[C@H](N(C)C)CC4)cc3c2)s1] 4621
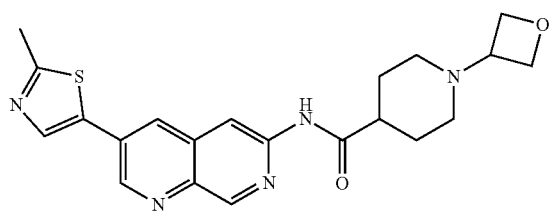 [SMILES: Cc1ncc(-c2cnc3cnc(NC(=O)C4CCN(C5COC5)CC4)cc3c2)s1] 4622
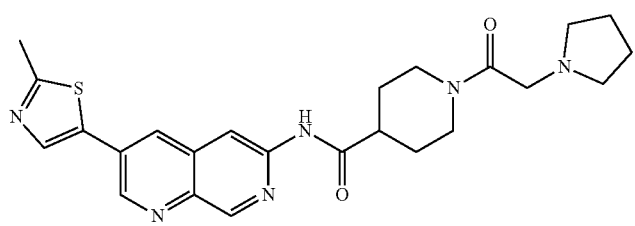 [SMILES: Cc1ncc(-c2cnc3cnc(NC(=O)C4CCN(C(=O)CN5CCCC5)CC4)cc3c2)s1] 4623
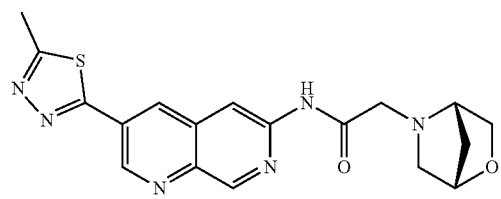 [SMILES: Cc1nnc(-c2cnc3cnc(NC(=O)CN4C[C@@H]5C[C@H]4CO5)cc3c2)s1] 4624
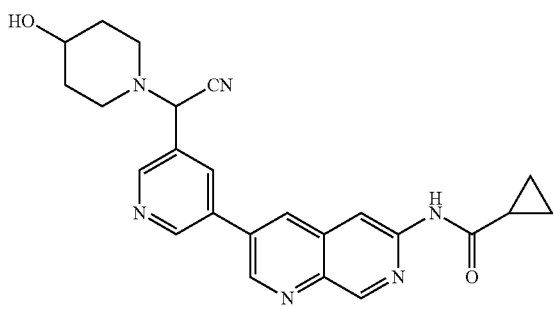 [SMILES: N#CC(c1cncc(-c2cnc3cnc(NC(=O)C4CC4)cc3c2)c1)N1CCC(O)CC1] 4625
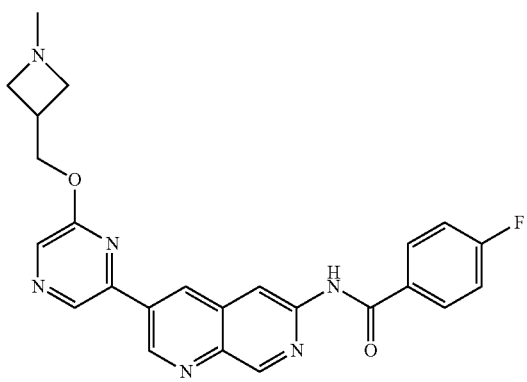 [SMILES: CN1CC(COc2cncc(-c3cnc4cnc(NC(=O)c5ccc(F)cc5)cc4c3)n2)C1] 4626

TABLE 1-continued
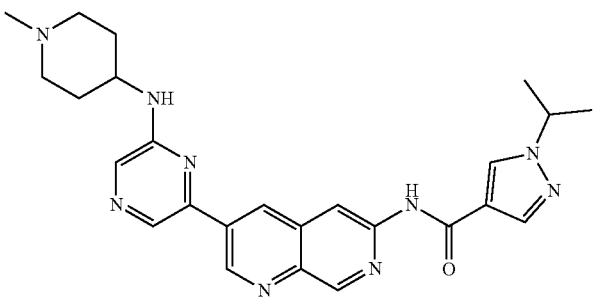 [SMILES: CC(C)n1cc(C(=O)Nc2cc3cc(-c4cncc(NC5CCN(C)CC5)n4)cnc3cn2)cn1]
4627
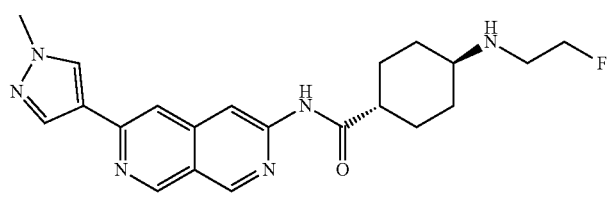 [SMILES: Cn1cc(-c2cc3cc(NC(=O)[C@H]4CC[C@H](NCCF)CC4)ncc3cn2)cn1]
4628
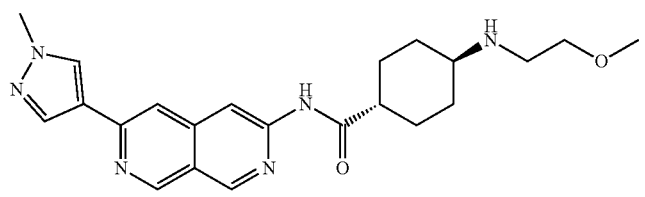 [SMILES: COCCN[C@H]1CC[C@H](C(=O)Nc2cc3cc(-c4cnn(C)c4)ncc3cn2)CC1]
4629
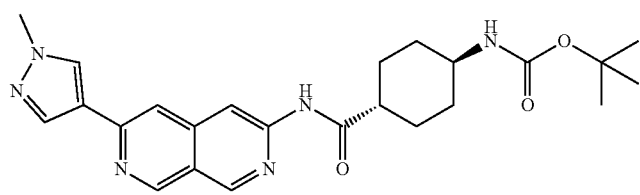 [SMILES: Cn1cc(-c2cc3cc(NC(=O)[C@H]4CC[C@H](NC(=O)OC(C)(C)C)CC4)ncc3cn2)cn1]
4630
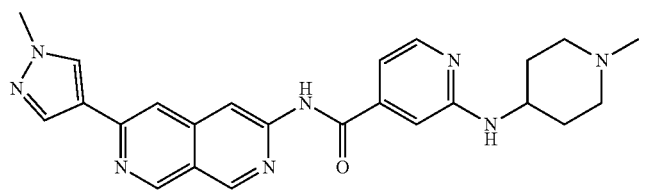 [SMILES: CN1CCC(Nc2cc(C(=O)Nc3cc4cc(-c5cnn(C)c5)ncc4cn3)ccn2)CC1]
4631
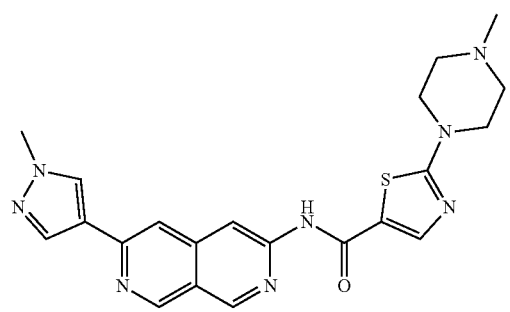 [SMILES: CN1CCN(c2ncc(C(=O)Nc3cc4cc(-c5cnn(C)c5)ncc4cn3)s2)CC1]
4632
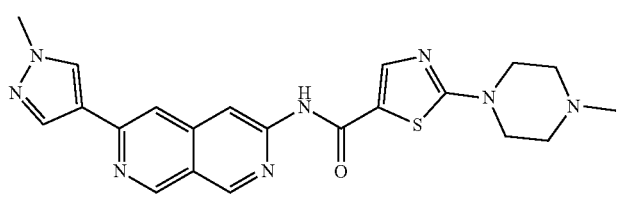 [SMILES: CN1CCN(c2ncc(C(=O)Nc3cc4cc(-c5cnn(C)c5)ncc4cn3)s2)CC1]
4633

TABLE 1-continued
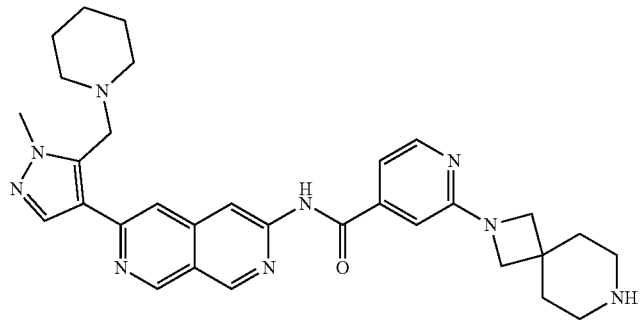 [SMILES: Cn1ncc(-c2cc3cc(NC(=O)c4ccnc(N5CC6(CCNCC6)C5)c4)ncc3cn2)c1CN1CCCCC1]
4634
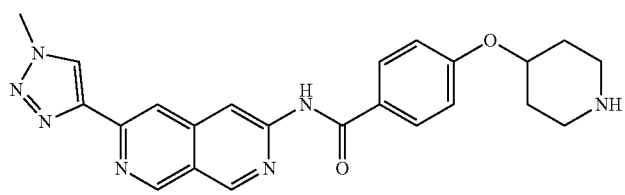
4635
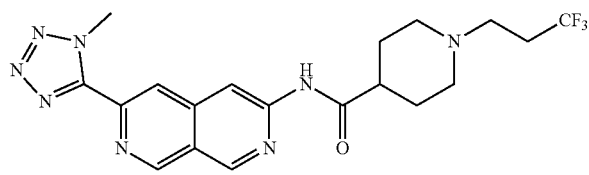
4636
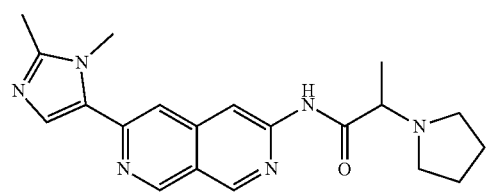 [SMILES: Cc1ncc(-c2cc3cc(NC(=O)C(C)N4CCCC4)ncc3cn2)n1C]
4637
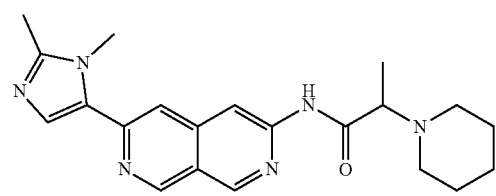
4638
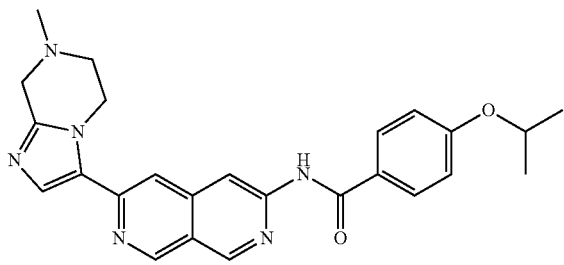 [SMILES: CC(C)Oc1ccc(C(=O)Nc2cc3cc(-c4cnc5n4CCN(C)C5)ncc3cn2)cc1]
4639
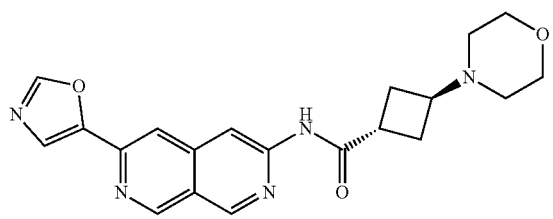 [SMILES: O=C(Nc1cc2cc(-c3cnco3)ncc2cn1)[C@H]1C[C@H](N2CCOCC2)C1]
4640

TABLE 1-continued
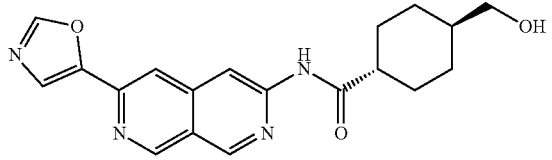 4641
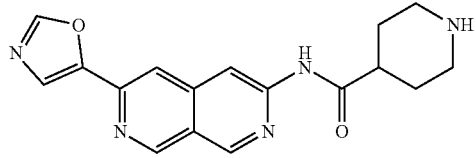 [SMILES: O=C(Nc1cc2cc(-c3cnco3)ncc2cn1)C1CCNCC1] 4642
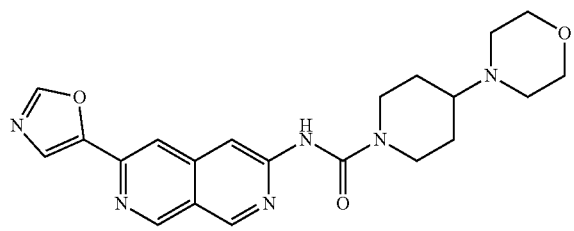 [SMILES: O=C(Nc1cc2cc(-c3cnco3)ncc2cn1)N1CCC(N2CCOCC2)CC1] 4643
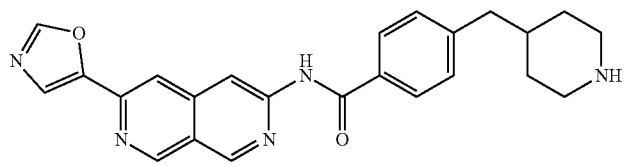 [SMILES: O=C(Nc1cc2cc(-c3cnco3)ncc2cn1)c1ccc(CC2CCNCC2)cc1] 4644
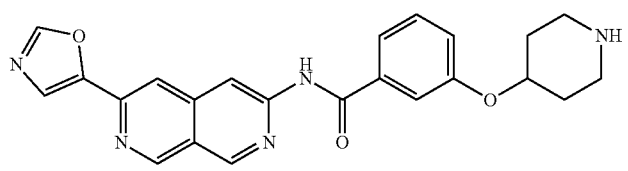 [SMILES: O=C(Nc1cc2cc(-c3cnco3)ncc2cn1)c1cccc(OC2CCNCC2)c1] 4645
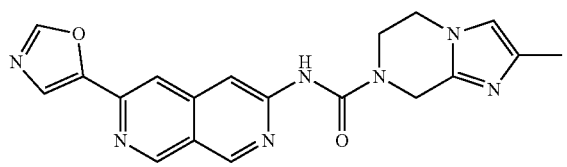 [SMILES: Cc1cn2c(n1)CN(C(=O)Nc1cc3cc(-c4cnco4)ncc3cn1)CC2] 4646
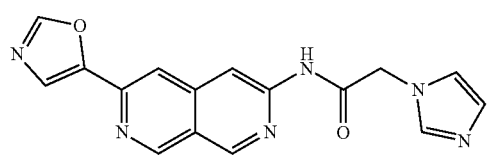 [SMILES: O=C(Cn1ccnc1)Nc1cc2cc(-c3cnco3)ncc2cn1] 4647
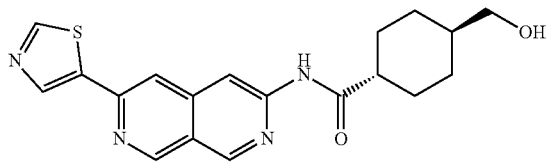 4648
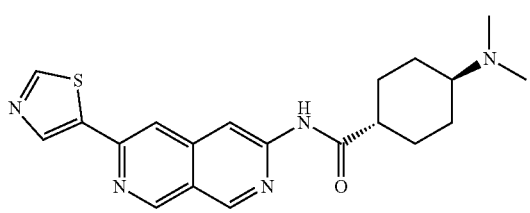 [SMILES: CN(C)[C@H]1CC[C@H](C(=O)Nc2cc3cc(-c4cncs4)ncc3cn2)CC1] 4649

TABLE 1-continued
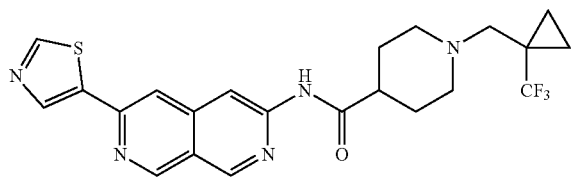 [SMILES: O=C(Nc1cc2cc(-c3cncs3)ncc2cn1)C1CCN(CC2(C(F)(F)F)CC2)CC1] 4650
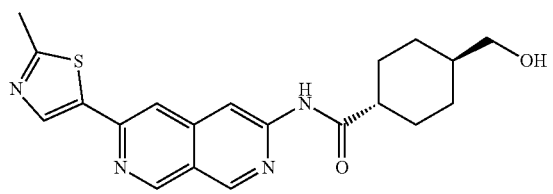 4651
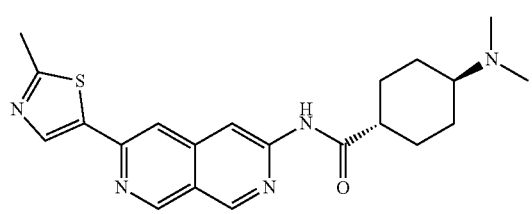 4652
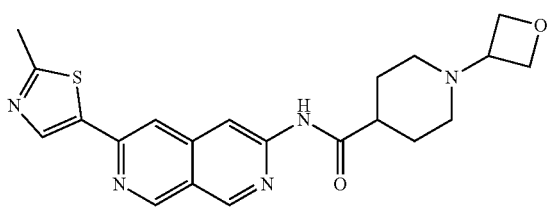 [SMILES: Cc1ncc(-c2cc3cc(NC(=O)C4CCN(C5COC5)CC4)ncc3cn2)s1] 4653
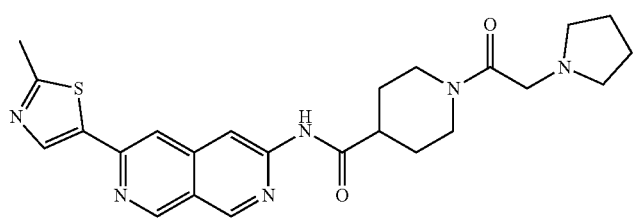 [SMILES: Cc1ncc(-c2cc3cc(NC(=O)C4CCN(C(=O)CN5CCCC5)CC4)ncc3cn2)s1] 4654
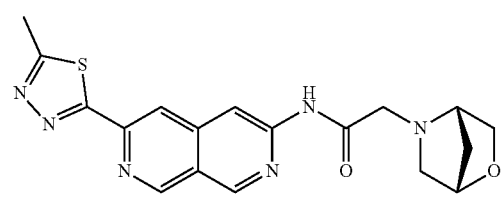 [SMILES: Cc1nnc(-c2cc3cc(NC(=O)CN4C[C@@H]5C[C@H]4CO5)ncc3cn2)s1] 4655
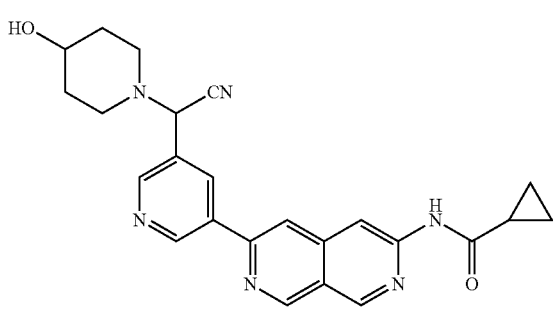 [SMILES: N#CC(c1cncc(-c2cc3cc(NC(=O)C4CC4)ncc3cn2)c1)N1CCC(O)CC1] 4656

TABLE 1-continued

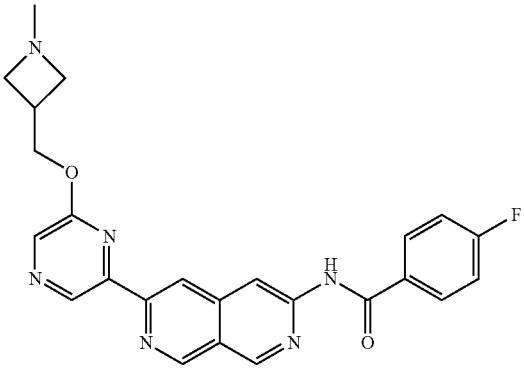 [SMILES: CN1CC(COc2cncc(-c3cc4cc(NC(=O)c5ccc(F)cc5)ncc4cn3)n2)C1]

4657

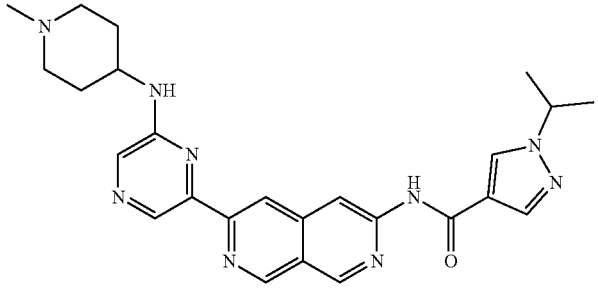 [SMILES: CC(C)n1cc(C(=O)Nc2cc3cc(-c4cncc(NC5CCN(C)CC5)n4)ncc3cn2)cn1]

4658

Administration and Pharmaceutical Compositions

Some embodiments include pharmaceutical compositions comprising: (a) a therapeutically effective amount of a compound provided herein, or its corresponding enantiomer, diastereoisomer or tautomer, or pharmaceutically acceptable salt; and (b) a pharmaceutically acceptable carrier.

The compounds provided herein may also be useful in combination (administered together or sequentially) with other known agents.

Non-limiting examples of diseases which can be treated with a combination of a compound of Formulas I, Ia, Ib, Ic, Id, or Ie and other another active agent are colorectal cancer, ovarian cancer, chronic inflammation, diabetic retinopathy, pulmonary fibrosis, and osteoarthritis. For example, a compound of Formula (I) can be combined with one or more chemotherapeutic compounds.

In some embodiments, colorectal cancer can be treated with a combination of a compound of Formulas I, Ia, Ib, Ic, Id, or Ie and one or more of the following drugs: 5-Fluorouracil (5-FU), which can be administered with the vitamin-like drug leucovorin (also called folinic acid); capecitabine (XELODA®), irinotecan (CAMPOSTAR®), oxaliplatin (ELOXATIN®). Examples of combinations of these drugs which could be further combined with a compound of Formulas I, Ia, Ib, Ic, Id, or Ie are FOLFOX (5-FU, leucovorin, and oxaliplatin), FOLFIRI (5-FU, leucovorin, and irinotecan), FOLFOXIRI (leucovorin, 5-FU, oxaliplatin, and irinotecan) and CapeOx (Capecitabine and oxaliplatin). For rectal cancer, chemo with 5-FU or capecitabine combined with radiation may be given before surgery (neoadjuvant treatment).

In some embodiments, ovarian cancer can be treated with a combination of a compound of Formula (I) and one or more of the following drugs: Topotecan, Liposomal doxorubicin (DOXIL®), Gemcitabine (GEMZAR®), Cyclophosphamide (CYTOXAN®), Vinorelbine (NAVELBINE®), Ifosfamide (IFEX®), Etoposide (VP-16), Altretamine (HEXALEN®), Capecitabine (XELODA®), Irinotecan (CPT-11, CAMPTOSAR®), Melphalan, Pemetrexed (ALIMTA®) and Albumin bound paclitaxel (nab-paclitaxel, ABRAXANE®). Examples of combinations of these drugs which could be further combined with a compound of Formulas I, Ia, Ib, Ic, Id, or Ie are TIP (paclitaxel [Taxol], ifosfamide, and cisplatin), VeIP (vinblastine, ifosfamide, and cisplatin) and VIP (etoposide [VP-16], ifosfamide, and cisplatin).

In some embodiments, a compound of Formulas I, Ia, Ib, Ic, Id, or Ie can be used to treat cancer in combination with any of the following methods: (a) Hormone therapy such as aromatase inhibitors, LHRH [luteinizing hormone-releasing hormone] analogs and inhibitors, and others; (b) Ablation or embolization procedures such as radiofrequency ablation (RFA), ethanol (alcohol) ablation, microwave thermotherapy and cryosurgery (cryotherapy); (c) Chemotherapy using alkylating agents such as cisplatin and carboplatin, oxaliplatin, mechlorethamine, cyclophosphamide, chlorambucil and ifosfamide; (d) Chemotherapy using anti-metabolites such as azathioprine and mercaptopurine; (e) Chemotherapy using plant alkaloids and terpenoids such as vinca alkaloids (i.e. Vincristine, Vinblastine, Vinorelbine and Vindesine) and taxanes; (f) Chemotherapy using podophyllotoxin, etoposide, teniposide and docetaxel; (g) Chemotherapy using topoisomerase inhibitors such as irinotecan, topotecan, amsacrine, etoposide, etoposide phosphate, and teniposide; (h) Chemotherapy using cytotoxic antibiotics such as actinomycin, anthracyclines, doxorubicin, daunorubicin, valrubicin, idarubicin, epirubicin, bleomycin, plicamycin and mitomycin; (i) Chemotherapy using tyrosine-kinase inhibitors such as Imatinib mesylate (GLEEVEC®, also known as STI-571), Gefitinib (Iressa, also known as ZD1839), Erlotinib (marketed as TARCEVA®), Bortezomib (VELCADE®), tamoxifen, tofacitinib, crizotinib, Bcl-2 inhibitors (e.g. obatoclax in clinical trials, ABT-263, and Gossypol), PARP inhibitors (e.g. Iniparib, Olaparib in clinical trials), PI3K inhibitors (e.g. perifosine in a phase III trial), VEGF Receptor 2 inhibitors (e.g. Apatinib), AN-152, (AEZS-108), Braf inhibitors (e.g. vemurafenib, dabrafenib and LGX818), MEK inhibitors (e.g. trametinib and MEK162), CDK inhibitors, (e.g. PD-0332991), salinomycin and Sorafenib; (j) Chemotherapy using monoclonal antibodies such as Rituximab (marketed as MABTHERA® or RITUXAN®), Trastuzumab (Herceptin also known as ErbB2), Cetuximab (marketed as ERBITUX®), and Bevacizumab (marketed as AVASTIN®); and (k) radiation therapy.

In some embodiments, diabetic retinopathy can be treated with a combination of a compound of Formulas I, Ia, Ib, Ic, Id, or Ie and one or more of the following natural supplements: Bilberry, Butcher's broom, Ginkgo, Grape seed extract, and Pycnogenol (Pine bark).

In some embodiments, idiopathic pulmonary fibrosis/pulmonary fibrosis can be treated with a combination of a compound of Formulas I, Ia, Ib, Ic, Id, or Ie and one or more of the following drugs: pirfenidone (pirfenidone was approved for use in 2011 in Europe under the brand name Esbriet®), prednisone, azathioprine, N-acetylcysteine, interferon-γ 1b, bosentan (bosentan is currently being studied in patients with IPF, [*The American Journal of Respiratory and Critical Care Medicine* (2011), 184(1), 92-9]), Nintedanib (BIBF 1120 and Vargatef), QAX576 [*British Journal of Pharmacology* (2011), 163(1), 141-172], and anti-inflammatory agents such as corticosteroids.

In some embodiments, a compound of Formulas I, Ia, Ib, Ic, Id, or Ie can be used to treat idiopathic pulmonary fibrosis/pulmonary fibrosis in combination with any of the following methods: oxygen therapy, pulmonary rehabilitation and surgery.

In some embodiments, a compound of Formulas I, Ia, Ib, Ic, Id, or Ie can be used to treat osteoarthritis in combination with any of the following methods: (a) Nonsteroidal anti-inflammatory drugs (NSAIDs) such as ibuprofen, naproxen, aspirin and acetaminophen; (b) physical therapy; (c) injections of corticosteroid medications; (d) injections of hyaluronic acid derivatives (e.g. Hyalgan, Synvisc); (e) narcotics, like codeine; (f) in combination with braces and/or shoe inserts or any device that can immobilize or support your joint to help you keep pressure off it (e.g., splints, braces, shoe inserts or other medical devices); (g) realigning bones (osteotomy); (h) joint replacement (arthroplasty); and (i) in combination with a chronic pain class.

In some embodiments, macular degeneration can be treated with a combination of a compound of Formulas I, Ia, Ib, Ic, Id, or Ie and one or more of the following drugs: Bevacizumab (Avastin®), Ranibizumab (Lucentis®), Pegaptanib (Macugen), Aflibercept (Eylea®), verteporfin (Visudyne®) in combination with photodynamic therapy (PDT) or with any of the following methods: (a) in combination with laser to destroy abnormal blood vessels (photocoagulation); and (b) in combination with increased vitamin intake of antioxidant vitamins and zinc.

In some embodiments, retinitis pigmentosa can be treated with a combination of a compound of Formulas I, Ia, Ib, Ic, Id, or Ie and one or more of the following drugs: UF-021 (Ocuseva™), vitamin A palmitate and pikachurin or with any of the following methods: (a) with the Argus® II retinal implant; and (b) with stem cell and/or gene therapy.

Administration of the compounds disclosed herein or the pharmaceutically acceptable salts thereof can be via any of the accepted modes of administration, including, but not limited to, orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. In some embodiments, the administration method includes oral or parenteral administration.

Compounds provided herein intended for pharmaceutical use may be administered as crystalline or amorphous products. Pharmaceutically acceptable compositions may include solid, semi-solid, liquid, solutions, colloidal, liposomes, emulsions, suspensions, complexes, coacervates and aerosols. Dosage forms, such as, e.g., tablets, capsules, powders, liquids, suspensions, suppositories, aerosols, implants, controlled release or the like. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants and the like, for prolonged and/or timed, pulsed administration at a predetermined rate.

The compounds can be administered either alone or in combination with a conventional pharmaceutical carrier, excipient or the like. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a compound as described herein in the range of 0.005% to 100% with the balance made up from non-toxic carrier may be prepared. The contemplated compositions may contain 0.001%-100% of a compound provided herein, in one embodiment 0.1-95%, in another embodiment 75-85%, in a further embodiment 20-80%. Actual methods of preparing such dosage forms are known, or will be apparent, to those skilled in this art; for example, see Remington: *The Science and Practice of Pharmacy*, 22$^{nd}$ Edition (Pharmaceutical Press, London, UK. 2012).

In one embodiment, the compositions will take the form of a unit dosage form such as a pill or tablet and thus the composition may contain, along with a compound provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more compounds provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Liquid pharmaceutically administrable compositions can, for example, be prepared by dissolving, dispersing, etc. a compound provided herein and optional pharmaceutical adjuvants in a carrier (e.g., water, saline, aqueous dextrose, glycerol, glycols, ethanol or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrin derivatives, sorbitan monolaurate, triethanolamine acetate, triethanolamine oleate, and the like).

In some embodiments, the unit dosage of compounds of Formulas I, Ia, Ib, Ic, Id, and Ie is about 0.25 mg/Kg to about 50 mg/Kg in humans.

In some embodiments, the unit dosage of compounds of Formulas I, Ia, Ib, Ic, Id, and Ie is about 0.25 mg/Kg to about 20 mg/Kg in humans.

In some embodiments, the unit dosage of compounds of Formulas I, Ia, Ib, Ic, Id, and Ie is about 0.50 mg/Kg to about 19 mg/Kg in humans.

In some embodiments, the unit dosage of compounds of Formulas I, Ia, Ib, Ic, Id, and Ie is about 0.75 mg/Kg to about 18 mg/Kg in humans.

In some embodiments, the unit dosage of compounds of Formulas I, Ia, Ib, Ic, Id, and Ie is about 1.0 mg/Kg to about 17 mg/Kg in humans.

In some embodiments, the unit dosage of compounds of Formulas I, Ia, Ib, Ic, Id, and Ie is about 1.25 mg/Kg to about 16 mg/Kg in humans.

In some embodiments, the unit dosage of compounds of Formulas I, Ia, Ib, Ic, Id, and Ie is about 1.50 mg/Kg to about 15 mg/Kg in humans.

In some embodiments, the unit dosage of compounds of Formulas I, Ia, Ib, Ic, Id, and Ie is about 1.75 mg/Kg to about 14 mg/Kg in humans.

In some embodiments, the unit dosage of compounds of Formulas I, Ia, Ib, Ic, Id, and Ie is about 2.0 mg/Kg to about 13 mg/Kg in humans.

In some embodiments, the unit dosage of compounds of Formulas I, Ia, Ib, Ic, Id, and Ie is about 3.0 mg/Kg to about 12 mg/Kg in humans.

In some embodiments, the unit dosage of compounds of Formulas I, Ia, Ib, Ic, Id, and Ie is about 4.0 mg/Kg to about 11 mg/Kg in humans.

In some embodiments, the unit dosage of compounds of Formulas I, Ia, Ib, Ic, Id, and Ie is about 5.0 mg/Kg to about 10 mg/Kg in humans.

In some embodiments, the compositions are provided in unit dosage forms suitable for single administration.

In some embodiments, the compositions are provided in unit dosage forms suitable for twice a day administration.

In some embodiments, the compositions are provided in unit dosage forms suitable for three times a day administration.

Injectables can be prepared in conventional forms, either as liquid solutions, colloid, liposomes, complexes, coacervate or suspensions, as emulsions, or in solid forms suitable for reconstitution in liquid prior to injection. The percentage of a compound provided herein contained in such parenteral compositions is highly dependent on the specific nature thereof, as well as the activity of the compound and the needs of the patient. However, percentages of active ingredient of 0.01% to 10% in solution are employable, and could be higher if the composition is a solid or suspension, which could be subsequently diluted to the above percentages.

In some embodiments, the composition will comprise about 0.1-10% of the active agent in solution.

In some embodiments, the composition will comprise about 0.1-5% of the active agent in solution.

In some embodiments, the composition will comprise about 0.1-4% of the active agent in solution.

In some embodiments, the composition will comprise about 0.15-3% of the active agent in solution.

In some embodiments, the composition will comprise about 0.2-2% of the active agent in solution.

In some embodiments, the compositions are provided in dosage forms suitable for continuous dosage by intravenous infusion over a period of about 1-96 hours.

In some embodiments, the compositions are provided in dosage forms suitable for continuous dosage by intravenous infusion over a period of about 1-72 hours.

In some embodiments, the compositions are provided in dosage forms suitable for continuous dosage by intravenous infusion over a period of about 1-48 hours.

In some embodiments, the compositions are provided in dosage forms suitable for continuous dosage by intravenous infusion over a period of about 1-24 hours.

In some embodiments, the compositions are provided in dosage forms suitable for continuous dosage by intravenous infusion over a period of about 1-12 hours.

In some embodiments, the compositions are provided in dosage forms suitable for continuous dosage by intravenous infusion over a period of about 1-6 hours.

In some embodiments, these compositions can be administered by intravenous infusion to humans at doses of about 5 mg/m$^2$ to about 300 mg/m$^2$.

In some embodiments, these compositions can be administered by intravenous infusion to humans at doses of about 5 mg/m$^2$ to about 200 mg/m$^2$.

In some embodiments, these compositions can be administered by intravenous infusion to humans at doses of about 5 mg/m$^2$ to about 100 mg/m$^2$.

In some embodiments, these compositions can be administered by intravenous infusion to humans at doses of about 10 mg/m$^2$ to about 50 mg/m$^2$.

In some embodiments, these compositions can be administered by intravenous infusion to humans at doses of about 50 mg/m$^2$ to about 200 mg/m$^2$.

In some embodiments, these compositions can be administered by intravenous infusion to humans at doses of about 75 mg/m$^2$ to about 175 mg/m$^2$.

In some embodiments, these compositions can be administered by intravenous infusion to humans at doses of about 100 mg/m² to about 150 mg/m².

It is to be noted that concentrations and dosage values may also vary depending on the specific compound and the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In one embodiment, the compositions can be administered to the respiratory tract (including nasal and pulmonary) e.g., through a nebulizer, metered-dose inhalers, atomizer, mister, aerosol, dry powder inhaler, insufflator, liquid instillation or other suitable device or technique.

In some embodiments, aerosols intended for delivery to the nasal mucosa are provided for inhalation through the nose. For optimal delivery to the nasal cavities, inhaled particle sizes of about 5 to about 100 microns are useful, with particle sizes of about 10 to about 60 microns being preferred. For nasal delivery, a larger inhaled particle size may be desired to maximize impaction on the nasal mucosa and to minimize or prevent pulmonary deposition of the administered formulation. In some embodiments, aerosols intended for delivery to the lung are provided for inhalation through the nose or the mouth. For delivery to the lung, inhaled aerodynamic particle sizes of about less than 10 µm are useful (e.g., about 1 to about 10 microns). Inhaled particles may be defined as liquid droplets containing dissolved drug, liquid droplets containing suspended drug particles (in cases where the drug is insoluble in the suspending medium), dry particles of pure drug substance, drug substance incorporated with excipients, liposomes, emulsions, colloidal systems, coacervates, aggregates of drug nanoparticles, or dry particles of a diluent which contain embedded drug nanoparticles.

In some embodiments, compounds of Formulas I, Ia, Ib, Ic, Id, and Ie disclosed herein intended for respiratory delivery (either systemic or local) can be administered as aqueous formulations, as non-aqueous solutions or suspensions, as suspensions or solutions in halogenated hydrocarbon propellants with or without alcohol, as a colloidal system, as emulsions, coacervates, or as dry powders. Aqueous formulations may be aerosolized by liquid nebulizers employing either hydraulic or ultrasonic atomization or by modified micropump systems (like the soft mist inhalers, the Aerodose® or the AERx® systems). Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

In some embodiments, the compositions of Formulas I, Ia, Ib, Ic, Id, and Ie disclosed herein can be administered to the ear by various methods. For example, a round window catheter (e.g., U.S. Pat. Nos. 6,440,102 and 6,648,873) can be used.

Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the disclosure can be incorporated into a gel formulation (e.g., U.S. Pat. Nos. 4,474,752 and 6,911,211).

In some embodiments, compounds of Formulas I, Ia, Ib, Ic, Id, and Ie disclosed herein intended for delivery to the ear can be administered via an implanted pump and delivery system through a needle directly into the middle or inner ear (cochlea) or through a cochlear implant stylet electrode channel or alternative prepared drug delivery channel such as but not limited to a needle through temporal bone into the cochlea.

Other options include delivery via a pump through a thin film coated onto a multichannel electrode or electrode with a specially imbedded drug delivery channel (pathways) carved into the thin film for this purpose. In other embodiments the acidic or basic solid compound of Formulas I, Ia, Ib, Ic, Id, and Ie can be delivered from the reservoir of an external or internal implanted pumping system.

Formulations of the disclosure also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In some embodiments, the compounds of Formulas I, Ia, Ib, Ic, Id, and Ie are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like.

Suppositories for rectal administration of the drug (either as a solution, colloid, suspension or a complex) can be prepared by mixing a compound provided herein with a suitable non-irritating excipient that is solid at ordinary temperatures but liquid at the rectal temperature and will therefore melt or erode/dissolve in the rectum and release the compound. Such materials include cocoa butter, glycerinated gelatin, hydrogenated vegetable oils, poloxamers, mixtures of polyethylene glycols of various molecular weights and fatty acid esters of polyethylene glycol. In suppository forms of the compositions, a low-melting wax such as, but not limited to, a mixture of fatty acid glycerides, optionally in combination with cocoa butter, is first melted.

Solid compositions can be provided in various different types of dosage forms, depending on the physicochemical properties of the compound provided herein, the desired dissolution rate, cost considerations, and other criteria. In one of the embodiments, the solid composition is a single unit. This implies that one unit dose of the compound is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In one embodiment, the solid composition is a highly porous lyophilized form. Such lyophilizates, sometimes also called wafers or lyophilized tablets, are particularly useful for their rapid disintegration, which also enables the rapid dissolution of the compound.

On the other hand, for some applications the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid drug dissolution is that of powders, granules, or pellets from water-soluble excipients which are coated with a compound provided herein so that the compound is located at the outer surface of the individual particles. In this type of system, the water-soluble low molecular weight excipient may be useful for preparing the cores of such coated particles, which can be subsequently coated with a coating composition comprising the compound and, for example, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided herein, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of hepatocellular carcinoma, colon cancer, leukemia, lymphoma, sarcoma, ovarian cancer, diabetic retinopathy, pulmonary fibrosis, rheumatoid arthritis, sepsis, ankylosing spondylitis, psoriasis, scleroderma, mycotic and viral infections, bone and cartilage diseases, Alzheimer's disease, lung disease, bone/osteoporotic (wrist, spine, shoulder and hip) fractures, articular cartilage (chondral) defects, degenerative disc disease (or intervertebral disc degeneration), polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

Methods of Treatment

The compounds and compositions provided herein can be used as inhibitors and/or modulators of one or more components of the Wnt pathway, which may include one or more Wnt proteins, and thus can be used to treat a variety of disorders and diseases in which aberrant Wnt signaling is implicated, such as cancer and other diseases associated with abnormal angiogenesis, cellular proliferation, and cell cycling. Accordingly, the compounds and compositions provided herein can be used to treat cancer, to reduce or inhibit angiogenesis, to reduce or inhibit cellular proliferation, to correct a genetic disorder, and/or to treat a neurological condition/disorder/disease due to mutations or dysregulation of the Wnt pathway and/or of one or more of Wnt signaling components. Non-limiting examples of diseases which can be treated with the compounds and compositions provided herein include a variety of cancers, diabetic retinopathy, pulmonary fibrosis, rheumatoid arthritis, scleroderma, mycotic and viral infections, bone and cartilage diseases, neurological conditions/diseases such as Alzheimer's disease, amyotrophic lateral sclerosis (ALS), motor neuron disease, multiple sclerosis or autism, lung disease, bone/osteoporotic (wrist, spine, shoulder and hip) fractures, polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

With respect to cancer, the Wnt pathway is known to be constitutively activated in a variety of cancers including, for example, colon cancer, hepatocellular carcinoma, lung cancer, ovarian cancer, prostate cancer, pancreatic cancer and leukemias such as CML, CLL and T-ALL. Accordingly, the compounds and compositions described herein may be used to treat these cancers in which the Wnt pathway is constitutively activated. In certain embodiments, the cancer is chosen from hepatocellular carcinoma, colon cancer, leukemia, lymphoma, sarcoma and ovarian cancer.

Other cancers can also be treated with the compounds and compositions described herein.

More particularly, cancers that may be treated by the compounds, compositions and methods described herein include, but are not limited to, the following:

1) Breast cancers, including, for example $ER^+$ breast cancer, $ER^-$ breast cancer, $her2^-$ breast cancer, $her2^+$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative (her2⁻). In some embodiments, the breast cancer may have a high risk Oncotype score.

2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.

3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, for example, hepatoma, e.g., hepatocellular carcinoma; cholangiocarcinoma; hepatoblastoma; angiosarcoma; hepatocellular adenoma; and hemangioma.

7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, oligodendrocytoma, schwannoma, retinoblastoma, and congenital tumors; and cancers of the spinal cord, e.g., neurofibroma, meningioma, glioma, and sarcoma.

9) Gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia.

11) Skin cancers and skin disorders, including, for example, malignant melanoma and metastatic melanoma, basal cell carcinoma, squamous cell carcinoma, Kaposi's sarcoma, moles dysplastic nevi, lipoma, angioma, dermatofibroma, keloids, and scleroderma.

12) Adrenal gland cancers, including, for example, neuroblastoma.

More particularly, tumors of the central nervous system that may be treated by the compounds, compositions and methods described herein include:

1) Astrocytic tumors, e.g., diffuse astrocytoma (fibrillary, protoplasmic, gemistocytic, mixed), anaplastic (malignant) astrocytoma, glioblastoma multiforme (giant cell glioblastoma and gliosarcoma), pilocytic astrocytoma (pilomyxoid astrocytoma), pleomorphic xanthoastrocytoma, subependymal giant cell astrocytoma, and gliomatosis cerebri.

2) Oligodendroglial tumors, e.g., oligodendroglioma and anaplastic oligodendroglioma.

3) Oligoastrocytic tumors, e.g., oligoastrocytoma and anaplastic oligoastrocytoma.

4) Ependymal tumors, e.g., subependymoma, myxopapillary ependymoma, ependymoma, (cellular, papillary, clear cell, tanycytic), and anaplastic (malignant) ependymoma.

5) Choroid plexus tumors, e.g., choroid plexus papilloma, atypical choroid plexus papilloma, and choroid plexus carcinoma.

6) Neuronal and mixed neuronal-glial tumors, e.g., gangliocytoma, ganglioglioma, dysembryoplastic neuroepithelial tumor (DNET), dysplastic gangliocytoma of the cerebellum (Lhermitte-Duclos), desmoplastic infantile astrocytoma/ganglioglioma, central neurocytoma, anaplastic ganglioglioma, extraventricular neurocytoma, cerebellar liponeurocytoma, Papillary glioneuronal tumor, Rosette-forming glioneuronal tumor of the fourth ventricle, and paraganglioma of the filum terminale.

7) Pineal tumors, e.g., pineocytoma, pineoblastoma, papillary tumors of the pineal region, and pineal parenchymal tumor of intermediate differentiation.

8) Embryonal tumors, e.g., medulloblastoma (medulloblastoma with extensive nodularity, anaplastic medulloblastoma, desmoplastic, large cell, melanotic, medullomyoblastoma), medulloepithelioma, supratentorial primitive neuroectodermal tumors, and primitive neuroectodermal tumors (PNETs) such as neuroblastoma, ganglioneuroblastoma, ependymoblastoma, and atypical teratoid/rhabdoid tumor.

9) Neuroblastic tumors, e.g., olfactory (esthesioneuroblastoma), olfactory neuroepithelioma, and neuroblastomas of the adrenal gland and sympathetic nervous system.

10) Glial tumors, e.g., astroblastoma, chordoid glioma of the third ventricle, and angiocentric glioma.

11) Tumors of cranial and paraspinal nerves, e.g., schwannoma, neurofibroma Perineurioma, and malignant peripheral nerve sheath tumor.

12) Tumors of the meninges such as tumors of meningothelial cells, e.g., meningioma (atypical meningioma and anaplastic meningioma); mesenchymal tumors, e.g., lipoma, angiolipoma, hibernoma, liposarcoma, solitary fibrous tumor, fibrosarcoma, malignant fibrous histiocytoma, leiomyoma, leiomyosarcoma, rhabdomyoma, rhabdomyosarcoma, chondroma, chondrosarcoma, osteoma, osteosarcoma, osteochondroma, haemangioma, epithelioid hemangioendothelioma, haemangiopericytoma, anaplastic haemangiopericytoma, angiosarcoma, Kaposi Sarcoma, and Ewing Sarcoma; primary melanocytic lesions, e.g., diffuse melanocytosis, melanocytoma, malignant melanoma, meningeal melanomatosis; and hemangioblastomas.

13) Tumors of the hematopoietic system, e.g., malignant Lymphomas, plasmocytoma, and granulocytic sarcoma.

14) Germ cell tumors, e.g., germinoma, embryonal carcinoma, yolk sac tumor, choriocarcinoma, teratoma, and mixed germ cell tumors.

15) Tumors of the sellar region, e.g., craniopharyngioma, granular cell tumor, pituicytoma, and spindle cell oncocytoma of the adenohypophysis.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent or treatment.

The compounds and compositions described herein can be used as anti-angiogenesis agents and as agents for modulating and/or inhibiting the activity of protein kinases, thus providing treatments for cancer and other diseases associated with cellular proliferation mediated by protein kinases. For example, the compounds described herein can inhibit the activity of one or more kinases. Accordingly, provided herein is a method of treating cancer or preventing or reducing angiogenesis through kinase inhibition.

In addition, and including treatment of cancer, the compounds and compositions described herein can function as cell-cycle control agents for treating proliferative disorders in a patient. Disorders associated with excessive proliferation include, for example, cancers, scleroderma, immunological disorders involving undesired proliferation of leukocytes, and restenosis and other smooth muscle disorders. Furthermore, such compounds may be used to prevent de-differentiation of post-mitotic tissue and/or cells.

Diseases or disorders associated with uncontrolled or abnormal cellular proliferation include, but are not limited to, the following:

a variety of cancers, including, but not limited to, carcinoma, hematopoietic tumors of lymphoid lineage, hematopoietic tumors of myeloid lineage, tumors of mesenchymal origin, tumors of the central and peripheral nervous system and other tumors including melanoma, seminoma and Kaposi's sarcoma.

a disease process which features abnormal cellular proliferation, e.g., benign prostatic hyperplasia, familial adenomatosis polyposis, neurofibromatosis, atherosclerosis, arthritis, glomerulonephritis, restenosis following angioplasty or vascular surgery, inflammatory bowel disease, transplantation rejection, endotoxic shock, and fungal infections. Fibrotic disorders such as skin fibrosis; scleroderma; progressive systemic fibrosis; lung fibrosis; muscle fibrosis; kidney fibrosis; glomerulosclerosis; glomerulonephritis; hypertrophic scar formation; uterine fibrosis; renal fibrosis; cirrhosis of the liver, liver fibrosis; fatty liver disease (FLD); adhesions, such as those occurring in the abdomen, pelvis, spine or tendons; chronic obstructive pulmonary disease; fibrosis following myocardial infarction; pulmonary fibrosis; fibrosis and scarring associated with diffuse/interstitial lung disease; central nervous system fibrosis, such as fibrosis following stroke; fibrosis associated with neuro-degenerative disorders such as Alzheimer's Disease or multiple sclerosis; fibrosis associated with proliferative vitreoretinopathy (PVR); restenosis; endometriosis; ischemic disease and radiation fibrosis.

defective apoptosis-associated conditions, such as cancers (including but not limited to those types mentioned herein), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus erythematosus, rheumatoid arthritis, sepsis, ankylosing spondylitis, psoriasis, scleroderma, autoimmune mediated glomerulonephritis, inflammatory bowel disease and autoimmune diabetes mellitus), neuro-degenerative disorders (including but not limited to Alzheimer's disease, lung disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis), tendinopathies such as tendinitis and tendinosis, aspirin-sensitive rhinosinusitis, cystic fibrosis, multiple sclerosis, kidney diseases and cancer pain.

genetic diseases due to mutations in Wnt signaling components, such as polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

The compounds and compositions provided herein have been found to possess immunomodulatory activities and are expected to control the innate and adaptive immune system (e.g. macrophages, microglia, dendritic cells, B and T cells) and suppress pro-inflammatory cytokine release (e.g. TNF, IL-6, IL-1, IFN) which is well known to be involved in chronic inflammation in a wide variety of disease areas. Therefore compounds and compositions provided herein can used to treat chronic inflammation associated with disorders and diseases including but not limited to eye disorders, joint pain, arthritis (rheumatoid, osteo, psoriatic gout), cancers (colon, breast, lung, pancreas, and others), gastrointestinal disorders (ulcerative colitis and inflammatory bowel diseases), pulmonary disorders (chronic obstructive pulmonary disorder and asthma), allergies, skin disorders (atopic dermatitis and psoriasis), diabetes, pancreatitis, tendonitis, hepatitis, heart disease, myocarditis, stroke, lupus, and neurological disorders such as multiple sclerosis, Parkinson's and dementia including Alzheimer's disease.

The compounds and compositions provided herein can be used as inhibitors and/or modulators of the enzyme DYRK1A, and thus can be used to treat a variety of disorders and diseases associated with tau protein, amyloid, alpha-synuclein, TDP-43 or FUS pathology including, but not limited to, Alzheimer's disease, amyotrophic lateral sclerosis (ALS), down syndrome, frontotemporal dementia (FTD) including FTD with Parkinsonism-17 (FTDP-17), behavioural variant frontotemporal dementia (bvFTD), FTD in patients with motor neuron disease (MND) (typically amyotrophic lateral sclerosis, also called FTD-ALS), corticobasal degeneration (CBD) (also called corticobasal ganglionic degeneration), progressive supranuclear palsy, primary progressive aphasia (PPA), globular glial tauopathy (GGT), myotonic dystrophy type 1 (DM1) (also called Steinert disease), myotonic dystrophy type 2 (DM2) (also called proximal myotonic myopathy), Guam complex, argyrophilic grain disease, dementia pugilistica, post-encephalitic parkinsonism, Lewy body dementia, Parkinson's disease, Pick's disease, and additional diseases with pronounced neurodegeneration such as autism, dementia, epilepsy, Huntington's disease, multiple sclerosis; diseases and disorders associated with acquired brain injury such as chronic traumatic encephalopathy, traumatic brain injury, tumor, and stroke.

Non-limiting examples of neurological disorders (e.g., neurological conditions and neurological diseases) which can be treated with the compounds and compositions provided herein include Alzheimer's disease, aphasia, apraxia, arachnoiditis, ataxia telangiectasia, attention deficit hyperactivity disorder, auditory processing disorder, autism, alcoholism, Bell's palsy, bipolar disorder, brachial plexus injury, Canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chronic fatigue syndrome, chronic inflammatory demyelinating polyneuropathy (CIDP), chronic pain, Coffin-Lowry syndrome, complex regional pain syndrome, compression neuropathy, congenital facial diplegia, corticobasal degeneration, cranial arteritis, craniosynostosis, Creutzfeldt-Jakob disease, cumulative trauma disorder, Cushing's syndrome, cytomegalic inclusion body disease (CIBD), Dandy-Walker syndrome, Dawson disease, De Morsier's syndrome, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, familial spastic paralysis, febrile seizure, Fisher syndrome, Friedreich's ataxia, fibromyalgia, Foville's syndrome, Gaucher's disease, Gerstmann's syndrome, giant cell arteritis, giant cell inclusion disease, globoid cell leukodystrophy, gray matter heterotopia, Guillain-Barre syndrome, HTLV-1 associated myelopathy, Hallervorden-Spatz disease, hemifacial spasm, hereditary spastic paraplegia, heredopathia atactica polyneuritiformis, herpes zoster oticus, herpes zoster, Hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile Refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease, Machado-Joseph disease (Spinocerebellar ataxia type 3), macrencephaly, macropsia, megalencephaly, Melkersson-Rosenthal syndrome, Meniere's disease, meningitis, Menkes disease, metachromatic leukodystrophy, microcephaly, micropsia, Miller Fisher syndrome, misophonia, mitochondrial myopathy, Mobius syndrome, monomelic amyotrophy, motor neuron disease, motor skills disorder, Moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myelinoclastic diffuse sclerosis, myoclonic Encephalopathy of infants, myoclonus, myopathy, myotubular myopathy, myotonia congenital, narcolepsy, neurofibromatosis, neuroleptic malignant syndrome, lupus erythematosus, neuromyotonia, neuronal ceroid lipofuscinosis, Niemann-Pick disease, O'Sullivan-McLeod syndrome, occipital Neuralgia, occult Spinal Dysraphism Sequence, Ohtahara syndrome, olivopontocerebellar atrophy, opsoclonus myoclonus syndrome, optic neuritis, orthostatic hypotension, palinopsia, paresthesia, Parkinson's disease, paramyotonia Congenita, paraneoplastic diseases, paroxysmal attacks, Parry-Romberg syndrome, Pelizaeus-Merzbacher disease, periodic paralyses, peripheral neuropathy, photic sneeze reflex, phytanic acid storage disease, Pick's disease, polymicrogyria (PMG), polymyositis, porencephaly, post-polio syndrome, postherpetic neuralgia (PHN), postural hypotension, Prader-Willi syndrome, primary lateral sclerosis, prion diseases, progressive hemifacial atrophy, progressive multifocal leukoencephalopathy, progressive supranuclear palsy, pseudotumor cerebri, Ramsay Hunt syndrome type I, Ramsay Hunt syndrome type II, Ramsay Hunt syndrome type III, Rasmussen's encephalitis, reflex neurovascular dystrophy, Refsum disease, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, Shy-Drager syndrome, Sjögren's syndrome, snatiation, Sotos syndrome, spasticity, spina bifida, spinal cord tumors, spinal muscular atrophy, spinocerebellar ataxia, Steele-Richardson-Olszewski syndrome, Stiff-person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, Tarlov cyst, Tay-Sachs disease, temporal arteritis, tetanus, tethered spinal cord syndrome, Thomsen disease, thoracic outlet syndrome, tic douloureux, Todd's paralysis, Tourette syndrome, toxic encephalopathy, transient ischemic attack, transmissible spongiform encephalopathies, transverse myelitis, tremor, trigeminal neuralgia, tropical spastic paraparesis, trypanosomiasis, tuberous sclerosis, ubisiosis, Von Hippel-Lindau disease (VHL), Viliuisk Encephalomyelitis (VE), Wallenberg's syndrome, Werdnig, Hoffman disease, west syndrome, Williams syndrome, Wilson's disease, and Zellweger syndrome.

The compounds and compositions may also be useful in the inhibition of the development of invasive cancer, tumor angiogenesis and metastasis.

In some embodiments, the disclosure provides a method for treating a disease or disorder associated with aberrant cellular proliferation by administering to a patient in need of such treatment an effective amount of one or more of the compounds of Formulas I, Ia, Ib, Ic, Id, and Ie, in combination (simultaneously or sequentially) with at least one other agent.

In some embodiments, the disclosure provides a method of treating or ameliorating in a patient a disorder or disease selected from the group consisting of: cancer, pulmonary fibrosis, idiopathic pulmonary fibrosis (IPF), degenerative disc disease, bone/osteoporotic fractures, bone or cartilage disease, and osteoarthritis, the method comprising administering to the patient a therapeutically effective amount of a compound according to Formulas I, Ia, Ib, Ic, Id, or Ie, or a pharmaceutically acceptable salt thereof.

In some embodiments, the disclosure provides a method of treating or ameliorating in a patient a disorder or disease selected from the group consisting of: chronic inflammation, systemic inflammation, diabetes, cancer, pulmonary fibrosis, idiopathic pulmonary fibrosis (IPF), degenerative disc disease, bone/osteoporotic fractures, a bone or cartilage disease, a neurological condition/disorder/disease, osteoarthritis, lung disease, a fibrotic disorder.

In some embodiments, the pharmaceutical composition comprises a therapeutically effective amount of a compound of Formulas I, Ia, Ib, Ic, Id, or Ie, or a pharmaceutically acceptable salt thereof, and a pharmaceutically acceptable excipient.

In some embodiments, the method of treats a disorder or disease in which aberrant Wnt signaling is implicated in a patient, the method comprises administering to the patient a therapeutically effective amount of a compound of Formulas I, Ia, Ib, Ic, Id, or Ie, or a pharmaceutically acceptable salt thereof.

In some embodiments, the disorder or disease is the pain and inflammation associated with cancer.

In some embodiments, the disorder or disease is the pain and inflammation associated with a joint.

In some embodiments, the disorder or disease is the pain and inflammation associated with the knee.

In some embodiments, the disorder or disease is the pain and inflammation associated with the hip.

In some embodiments, the disorder or disease is the pain and inflammation associated with the shoulder.

In some embodiments, the disorder or disease is the pain and inflammation associated with arthritis.

In some embodiments, the disorder or disease is the pain and inflammation associated with gastrointestinal disorders.

In some embodiments, the disorder or disease is the pain and inflammation associated with pulmonary disorders.

In some embodiments, the disorder or disease is the pain and inflammation associated with allergies.

In some embodiments, the disorder or disease is the pain and inflammation associated with skin disorders.

In some embodiments, the disorder or disease is the pain and inflammation associated with diabetes.

In some embodiments, the disorder or disease is the pain and inflammation associated with pancreatitis.

In some embodiments, the disorder or disease is the pain and inflammation associated with tendonitis.

In some embodiments, the disorder or disease is the pain and inflammation associated with heart disease.

In some embodiments, the disorder or disease is the pain and inflammation associated with lupus.

In some embodiments, the disorder or disease is the pain and inflammation associated with a neurological disorder.

In some embodiments, the disorder or disease is the pain and inflammation associated with multiple sclerosis.

In some embodiments, the disorder or disease is the pain and inflammation associated with Parkinson's.

In some embodiments, the disorder or disease is cancer.

In some embodiments, the disorder or disease is systemic inflammation.

In some embodiments, the disorder or disease is metastatic melanoma.

In some embodiments, the disorder or disease is fatty liver disease.

In some embodiments, the disorder or disease is liver fibrosis.

In some embodiments, the disorder or disease is tendon regeneration.

In some embodiments, the disorder or disease is diabetes.

In some embodiments, the disorder or disease is degenerative disc disease.

In some embodiments, the disorder or disease is osteoarthritis.

In some embodiments, the disorder or disease is diabetic retinopathy.

In some embodiments, the disorder or disease is pulmonary fibrosis.

In some embodiments, the disorder or disease is idiopathic pulmonary fibrosis (IPF).

In some embodiments, the disorder or disease is degenerative disc disease.

In some embodiments, the disorder or disease is rheumatoid arthritis.

In some embodiments, the disorder or disease is scleroderma.

In some embodiments, the disorder or disease is a mycotic or viral infection.

In some embodiments, the disorder or disease is a bone or cartilage disease.

In some embodiments, the disorder or disease is a neurological disorder.

In some embodiments, the disorder or disease is Alzheimer's disease.

In some embodiments, the disorder or disease is osteoarthritis.

In some embodiments, the disorder or disease is lung disease.

In some embodiments, the disorder or disease is a genetic disease caused by mutations in Wnt signaling components, wherein the genetic disease is selected from: polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

In some embodiments, the patient is a human.

In some embodiments, the cancer is chosen from: hepatocellular carcinoma, colon cancer, breast cancer, pancreatic cancer, chronic myeloid leukemia (CML), chronic myelomonocytic leukemia, chronic lymphocytic leukemia (CLL), acute myeloid leukemia, acute lymphocytic leukemia, Hodgkin lymphoma, lymphoma, sarcoma and ovarian cancer.

In some embodiments, the cancer is chosen from: lung cancer—non-small cell, lung cancer—small cell, multiple myeloma, nasopharyngeal cancer, neuroblastoma, osteosarcoma, penile cancer, pituitary tumors, prostate cancer, retinoblastoma, rhabdomyosarcoma, salivary gland cancer, skin cancer—basal and squamous cell, skin cancer—melanoma, small intestine cancer, stomach (gastric) cancers, testicular cancer, thymus cancer, thyroid cancer, uterine sarcoma, vaginal cancer, vulvar cancer, laryngeal or hypopharyngeal cancer, kidney cancer, Kaposi sarcoma, gestational trophoblastic disease, gastrointestinal stromal tumor, gastrointestinal carcinoid tumor, gallbladder cancer, eye cancer (melanoma and lymphoma), Ewing tumor, esophagus cancer, endometrial cancer, colorectal cancer, cervical cancer, brain or spinal cord tumor, bone metastasis, bone cancer, bladder cancer, bile duct cancer, anal cancer and adrenal cortical cancer.

In some embodiments, the cancer is hepatocellular carcinoma.

In some embodiments, the cancer is colon cancer.

In some embodiments, the cancer is colorectal cancer.

In some embodiments, the cancer is breast cancer.

In some embodiments, the cancer is pancreatic cancer.

In some embodiments, the cancer is chronic myeloid leukemia (CML).

In some embodiments, the cancer is chronic myelomonocytic leukemia.

In some embodiments, the cancer is chronic lymphocytic leukemia (CLL).

In some embodiments, the cancer is acute myeloid leukemia.

In some embodiments, the cancer is acute lymphocytic leukemia.

In some embodiments, the cancer is Hodgkin lymphoma.

In some embodiments, the cancer is lymphoma.

In some embodiments, the cancer is sarcoma.

In some embodiments, the cancer is ovarian cancer.

In some embodiments, the cancer is lung cancer—non-small cell.

In some embodiments, the cancer is lung cancer—small cell.

In some embodiments, the cancer is multiple myeloma.

In some embodiments, the cancer is nasopharyngeal cancer.

In some embodiments, the cancer is neuroblastoma.

In some embodiments, the cancer is osteosarcoma.

In some embodiments, the cancer is penile cancer.

In some embodiments, the cancer is pituitary tumors.

In some embodiments, the cancer is prostate cancer.

In some embodiments, the cancer is retinoblastoma.

In some embodiments, the cancer is rhabdomyosarcoma.

In some embodiments, the cancer is salivary gland cancer.

In some embodiments, the cancer is skin cancer—basal and squamous cell.

In some embodiments, the cancer is skin cancer—melanoma.

In some embodiments, the cancer is small intestine cancer.

In some embodiments, the cancer is stomach (gastric) cancers.

In some embodiments, the cancer is testicular cancer.

In some embodiments, the cancer is thymus cancer.

In some embodiments, the cancer is thyroid cancer.

In some embodiments, the cancer is uterine sarcoma.

In some embodiments, the cancer is vaginal cancer.

In some embodiments, the cancer is vulvar cancer.

In some embodiments, the cancer is Wilms tumor.

In some embodiments, the cancer is laryngeal or hypopharyngeal cancer.

In some embodiments, the cancer is kidney cancer.

In some embodiments, the cancer is Kaposi sarcoma.

In some embodiments, the cancer is gestational trophoblastic disease.

In some embodiments, the cancer is gastrointestinal stromal tumor.

In some embodiments, the cancer is gastrointestinal carcinoid tumor.

In some embodiments, the cancer is gallbladder cancer.

In some embodiments, the cancer is eye cancer (melanoma and lymphoma).

In some embodiments, the cancer is Ewing tumor.

In some embodiments, the cancer is esophagus cancer.

In some embodiments, the cancer is endometrial cancer.

In some embodiments, the cancer is colorectal cancer.

In some embodiments, the cancer is cervical cancer.

In some embodiments, the cancer is brain or spinal cord tumor.

In some embodiments, the cancer is bone metastasis.

In some embodiments, the cancer is bone cancer.

In some embodiments, the cancer is bladder cancer.

In some embodiments, the cancer is bile duct cancer.

In some embodiments, the cancer is anal cancer.

In some embodiments, the cancer is adrenal cortical cancer.

In some embodiments, the disorder or disease is a neurological condition/disorder/disease, wherein the neurological condition/disorder/disease is selected from: Alzheimer's disease, frontotemporal dementias, dementia with Lewy bodies, prion diseases, Parkinson's disease, Huntington's disease, progressive supranuclear palsy, corticobasal degeneration, multiple system atrophy, amyotrophic lateral sclerosis (ALS), inclusion body myositis, autism, degenerative myopathies, diabetic neuropathy, other metabolic neuropathies, endocrine neuropathies, orthostatic hypotension, multiple sclerosis and Charcot-Marie-Tooth disease.

In some embodiments, the disorder or disease is a neurological condition/disorder/disease associated with tau protein, amyloid, alpha-synuclein pathology, Tar DNA-binding Protein of 43KDa (TDP-43), Prion protein PrP or fused in sarcoma (FUS).

In some embodiments, the disorder or disease is a neurological condition/disorder/disease, wherein the neurological condition/disorder/disease is selected from the group consisting of: Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, and Stroke.

In some embodiments, the disorder or disease is a fibrotic disorder, wherein the fibrotic disorder is selected from the group consisting of: skin fibrosis; scleroderma; progressive systemic fibrosis; lung fibrosis; muscle fibrosis; kidney fibrosis; glomerulosclerosis; glomerulonephritis; hypertrophic scar formation; uterine fibrosis; renal fibrosis; cirrhosis of the liver, liver fibrosis; adhesions; chronic obstructive pulmonary disease; fibrosis following myocardial infarction; pulmonary fibrosis; fibrosis and scarring associated with diffuse/interstitial lung disease; central nervous system fibrosis; fibrosis associated with proliferative vitreoretinopathy (PVR); restenosis; endometriosis; ischemic disease, and radiation fibrosis.

In some embodiments, the disorder or disease is chronic inflammation associated with eye disorders, joint pain, arthritis (rheumatoid, osteo, psoriatic gout), cancers (colon, breast, lung, pancreas, and others), gastrointestinal disorders (ulcerative colitis and inflammatory bowel diseases), pulmonary disorders (chronic obstructive pulmonary disorder and asthma), allergies, skin disorders (atopic dermatitis and psoriasis), diabetes, pancreatitis, tendonitis, hepatitis, heart disease, myocarditis, stroke, lupus, and neurological disorders such as multiple sclerosis, Parkinson's and dementia including Alzheimer's disease.

In some embodiments, a compound of Formulas I, Ia, Ib, Ic, Id, or Ie inhibits DYRK1A.

In some embodiments, a compound of Formulas I, Ia, Ib, Ic, Id, or Ie inhibits GSK3.

In some embodiments, a compound of Formulas I, Ia, Ib, Ic, Id, or Ie inhibits GSK3β.

In some embodiments, a compound of Formulas I, Ia, Ib, Ic, Id, or Ie inhibits DYRK1A and GSK3β.

In some embodiments, the compound of Formulas I, Ia, Ib, Ic, Id, or Ie inhibits one or more proteins in the Wnt pathway.

In some embodiments, the compound of Formulas I, Ia, Ib, Ic, Id, or Ie inhibits signaling induced by one or more Wnt proteins.

In some embodiments, the Wnt proteins are chosen from: WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, and WNT16.

In some embodiments, the compound of Formulas I, Ia, Ib, Ic, Id, or Ie inhibits a kinase activity.

In some embodiments, the method treats a disease or disorder mediated by the Wnt pathway in a patient, the method comprises administering to the patient a therapeutically effective amount of a compound (or compounds) of Formulas I, Ia, Ib, Ic, Id, or Ie, or a pharmaceutically acceptable salt thereof.

In some embodiments, the compound of Formulas I, Ia, Ib, Ic, Id, or Ie inhibits one or more Wnt proteins.

In some embodiments, the method treats a disease or disorder mediated by kinase activity in a patient, the method comprises administering to the patient a therapeutically effective amount of a compound (or compounds) of Formulas I, Ia, Ib, Ic, Id, or Ie, or a pharmaceutically acceptable salt thereof.

In some embodiments, the disease or disorder comprises tumor growth, cell proliferation, or angiogenesis.

In some embodiments, the method inhibits the activity of a protein kinase receptor, the method comprises contacting the receptor with an effective amount of a compound (or compounds of Formulas I, Ia, Ib, Ic, Id, or Ie, or a pharmaceutically acceptable salt thereof.

In some embodiments, the method treats a disease or disorder associated with aberrant cellular proliferation in a patient; the method comprises administering to the patient a therapeutically effective amount of a compound (or compounds) of Formulas I, Ia, Ib, Ic, Id, or Ie, or a pharmaceutically acceptable salt thereof.

In some embodiments, the method prevents or reduces angiogenesis in a patient; the method comprises administering to the patient a therapeutically effective amount of a compound (or compounds) of Formulas I, Ia, Ib, Ic, Id, or Ie, or a pharmaceutically acceptable salt thereof.

In some embodiments, the method prevents or reduces abnormal cellular proliferation in a patient; the method comprises administering to the patient a therapeutically effective amount of a compound (or compounds) of Formulas I, Ia, Ib, Ic, Id, or Ie, or a pharmaceutically acceptable salt thereof.

In some embodiments, the method treats a disease or disorder associated with aberrant cellular proliferation in a patient, the method comprises administering to the patient a pharmaceutical composition comprising one or more of the compounds of claim 1 in combination with a pharmaceutically acceptable carrier and one or more other agents.

Moreover, the compounds and compositions, for example, as inhibitors of the cyclin-dependent kinases (CDKs), can modulate the level of cellular RNA and DNA synthesis and therefore are expected to be useful in the treatment of viral infections such as HIV, human papilloma virus, herpes virus, Epstein-Barr virus, adenovirus, Sindbis virus, pox virus and the like.

Compounds and compositions described herein can inhibit the kinase activity of, for example, CDK/cyclin complexes, such as those active in the $G_0$ or $G_1$ stage of the cell cycle, e.g., CDK2, CDK4, and/or CDK6 complexes.

Evaluation of Biological Activity

The biological activity of the compounds described herein can be tested using any suitable assay known to those of skill in the art, see, e.g., WO 2001/053268 and WO 2005/009997. For example, the activity of a compound may be tested using one or more of the test methods outlined below.

In one example, tumor cells may be screened for Wnt independent growth. In such a method, tumor cells of interest are contacted with a compound (i.e. inhibitor) of interest, and the proliferation of the cells, e.g. by uptake of tritiated thymidine, is monitored. In some embodiments, tumor cells may be isolated from a candidate patient who has been screened for the presence of a cancer that is associated with a mutation in the Wnt signaling pathway. Candidate cancers include, without limitation, those listed above.

In another example, one may utilize in vitro assays for Wnt biological activity, e.g. stabilization of β-catenin and promoting growth of stem cells. Assays for biological activity of Wnt include stabilization of β-catenin, which can be measured, for example, by serial dilutions of a candidate inhibitor composition. An exemplary assay for Wnt biological activity contacts a candidate inhibitor with cells containing constitutively active Wnt/β-catenin signaling. The cells are cultured for a period of time sufficient to stabilize β-catenin, usually at least about 1 hour, and lysed. The cell lysate is resolved by SDS PAGE, then transferred to nitrocellulose and probed with antibodies specific for β-catenin.

In a further example, the activity of a candidate compound can be measured in a *Xenopus* secondary axis bioassay (Leyns, L. et al. *Cell* (1997), 88(6), 747-756).

In another example, in vitro assays for DYRK1A biological activity may be used, e.g. regulation of microtubule-associated protein tau (MAPT/Tau) phosphorylation in neuronal cell line such as the human SH-SY5Y neuroblastoma cell line. Assays for DYRK1A-regulated level of phosphorylation can include monitoring levels of basal pSer396 Tau, which can be measured, for example, by serial dilutions of a candidate inhibitor composition using a ten micromolar top concentration and detected by ELISA or Western Blotting. An exemplary assay for DYRK-1A-regulated phosphorylation uses the SH-SY5Y cells cultured in a 96 well plate format for a period of time sufficient to stabilize microtubules and Tau phosphorylation, usually at least 2 days, then treated with a 1/3 serial dilution of compounds overnight and lysed. The cell lysate is resolved by SDS PAGE, then transferred to nitrocellulose and probed with an antibody specific for pSer396 Tau. The chemiluminescence signal for HRP-linked antibodies used in western blotting is detected using a Carestream Image Station and blot densitometry for pSer396 and beta-actin are analyzed using ImageJ (NIH).

In a further example, the activity of a candidate compound can be measured by ELISA by adding the lysate mentioned above onto total Tau-coated plates and detected with a specific pSer396 antibody. Colorimetric detection of ELISA signal is performed by Cytation3 plate reader (Biotek).

To further illustrate this disclosure, the following examples are included. The examples should not, of course, be construed as specifically limiting the disclosure. Variations of these examples within the scope of the claims are within the purview of one skilled in the art and are considered to fall within the scope of the disclosure as described, and claimed herein. The reader will recognize that the skilled artisan, armed with the present disclosure, and skill in the art is able to prepare and use the disclosure without exhaustive examples.

EXAMPLES

Compound Preparation

The starting materials used in preparing the compounds of the disclosure are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* 7$^{th}$ Ed., John Wiley & Sons (2013), Carey and Sundberg, *Advanced Organic Chemistry* 5$^{th}$ Ed., Springer (2007), *Comprehensive Organic Transformations: A Guide to Functional Group Transformations*, 2$^{nd}$ Ed., John Wiley & Sons (1999) (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in P. Wuts Greene's Protective Groups in Organic Synthesis, 5th Ed., John Wiley & Sons (2014), incorporated herein by reference in its entirety.

Trademarks used herein are examples only and reflect illustrative materials used at the time of the disclosure. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the disclosure.

($^{1}$H) nuclear magnetic resonance spectra (NMR) were measured in the indicated solvents on a Bruker NMR spectrometer (Avance™ DRX300, 300 MHz for $^{1}$H or Avance™ DRX500, 500 MHz for $^{1}$H) or Varian NMR spectrometer (Mercury 400BB, 400 MHz for $^{1}$H). Peak positions are expressed in parts per million (ppm) downfield from tetramethylsilane. The peak multiplicities are denoted as follows, s, singlet; d, doublet; t, triplet; q, quartet; ABq, AB quartet; quin, quintet; sex, sextet; sep, septet; non, nonet; dd, doublet of doublets; ddd, doublet of doublets of doublets; d/ABq, doublet of AB quartet; dt, doublet of triplets; td, triplet of doublets; dq, doublet of quartets; m, multiplet.

The following abbreviations have the indicated meanings:
AIBN=azobisisobutyronitrile
Boc$_2$O=di-tert-butyl dicarbonate
BrettPhos=2-(dicyclohexylphosphino)3,6-dimethoxy-2', 4',6'-triisopropyl-1,1'-biphenyl
BrettPhos Pd G3=[(2-Di-cyclohexylphosphino-3,6-dimethoxy-2',4',6'-triisopropyl-1,1'-biphenyl)-2-(2'-amino-1,1'-biphenyl)]palladium(II) methanesulfonate
brine=saturated aqueous sodium chloride
CDCl$_3$=deuterated chloroform
DABCO=1,4-diazabicyclo[2.2.2]octane
DBU=1,8-diazabicyclo[5.4.0]undec-7-ene
DCE=dichloroethane
DCM=dichloromethane
DEAD=diisopropyl azodicarboxylate
Dess-Martin periodinane=1,1,1-triacetoxy-1,1-dihydro-1,2-benziodoxol-3(1H)-one
DIPEA=N,N-diisopropylethylamine
DMA=dimethylacetamide
DMAP=4-dimethylaminopyridine
DME=dimethoxyethane
DMF=N,N-dimethylformamide
DMSO-d$_6$=deuterated dimethylsulfoxide
ESIMS=electron spray mass spectrometry
EtOAc=ethyl acetate
HATU=1-[Bis(dimethylamino)methylene]-1H-1,2,3-triazolo[4,5-b]pyridinium 3-oxid hexafluorophosphate
HCl=hydrochloric acid
HOAc=acetic acid
ISCO=Teledyne ISCO, Inc brand CombiFlash® Rf 200
KOAc=potassium acetate
LAH=lithium aluminum hydride
LC/MS=Liquid chromatography-mass spectrometry
LiHMDS=lithium bis(trimethylsilyl)amide
MCPBA=meta-chloroperoxybenzoic acid
MeCN=acetonitrile
MeOH=methanol
MPLC=:=medium-pressure liquid chromatography
MsCl=methanesulfonyl chloride (mesyl chloride)
MTBE=methyl tert-butyl ether
MW=microwave irradiation NaBH₃CN=sodium cyanoborohydride
NBS=N-bromosuccinimide
NaHCO₃=sodium bicarbonate
Na(OAc)₃BH=sodium triacetoxyborohydride
NMR=nuclear magnetic resonance
ON=overnight
Pd/C=palladium on carbon
Pd₂(dba)₃=tris(dibenzylideneacetone)dipalladium(0)
Pd(dppf)Cl₂=1,1'-bis(diphenylphosphino)ferrocene-palladium(II)dichloride
Pd(PPh₃)₄=tetrakis(triphenylphosphine)palladium(0)
Pd(OAc)₂=palladium(II) acetate
P(o-tolyl)₃=tris(o-tolyl)phosphine
r.t.=room temperature
TBDMSCl=tert-butyldimethylsilyl chloride example method for making the compounds provided herein. Furthermore, other methods for preparing compounds of the disclosure will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only and should not be construed as or confused with same numberings in other sections of the application. Unless otherwise indicated, all variables are as defined above.

General Procedures

Compounds of Formulas I and Ia of the present disclosure can be prepared as depicted in Scheme 1.

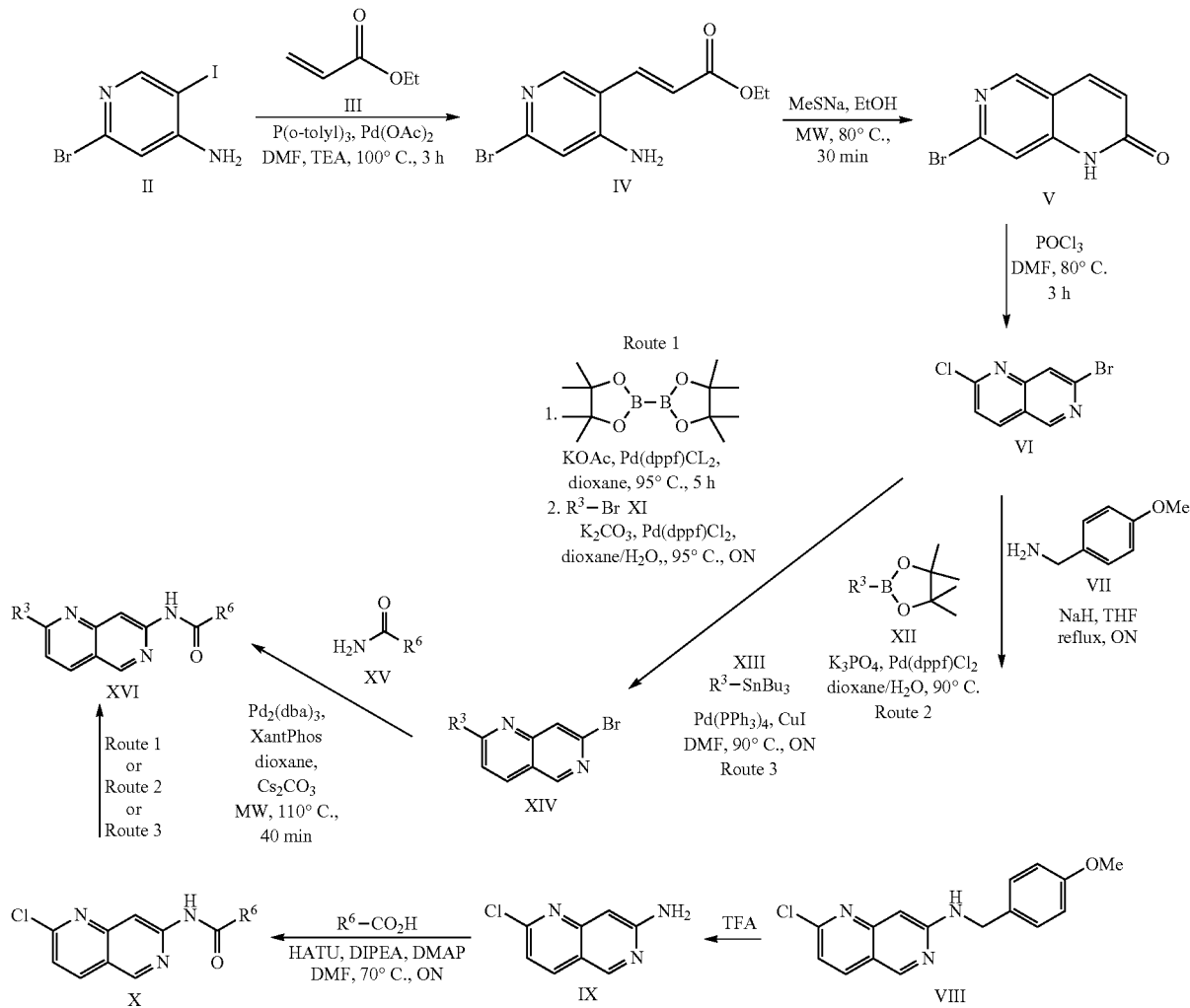

TEA=triethylamine
THF=tetrahydrofuran
TLC=thin layer chromatography
TMEDA=tetramethylethylenediamine
XantPhos=4,5-bis(diphenylphosphino)-9,9-dimethylxanthene The following example schemes are provided for the guidance of the reader, and collectively represent an Scheme 1 describes a method for preparation of 1,6-naphthyridin-7-yl-carboxamide derivatives (XVI) by first coupling 2-bromo-5-iodopyridin-4-amine (II) with ethyl acrylate (III) to produce ethyl (E)-3-(4-amino-6-bromopyridin-3-yl)acrylate (IV). The acrylate IV is then cyclized with MeSNa to give 7-bromo-1,6-naphthyridin-2(1H)-one (V). Aromatization with POCl₃ gave 7-bromo-2-chloro-1,6-naphthyridine (VI). Compound VI can either be reacted with (4-methoxyphenyl)methanamine (VII) followed by acid cleavage to give the amine (IX). Amine IX can be couple with a variety of acids followed by coupling to a variety of aromatic rings by any of three different routes to yield the desired 1,6-naphthyridin-7-yl-carboxamide derivatives (XVI). Compound VI can also be couple with by either of two Suzuki Coupling routes (Routes 1 or 2) or by a Stille reaction route (Route 3) to produce bromide (XIV) which can then be reacted with a variety of carboxamide (XV) to yield the desired 1,6-naphthyridin-7-yl-carboxamide derivatives (XVI).

In other embodiments, compounds of Formulas I and Ic of the present disclosure can be prepared as depicted in Scheme 2.

Scheme 2 describes a method for preparation of cinnolin-3-yl-carboxamide derivatives (XVI) by first nitrating 6-bromocinnolin-4-ol (XVII) to form 6-bromo-3-nitrocinnolin-4-ol (XVIII). Compound XVIII can be couple with by either of two Suzuki Coupling routes or by a Stille reaction route to produce various 3-nitrocinnolin-4-ol (XXIII) derivatives. Reduction of the hydroxy to chloride followed by reduction of the nitro to amine gives the 6-substituted cinnolin-3-amine (XXV). Amine XXV can be couple with a variety of acids (XXVI) to yield the desired cinnolin-3-yl-carboxamide derivatives (XVI).

In another embodiment, compounds of Formulas I and Ic of the present disclosure can be prepared as depicted in Scheme 3.

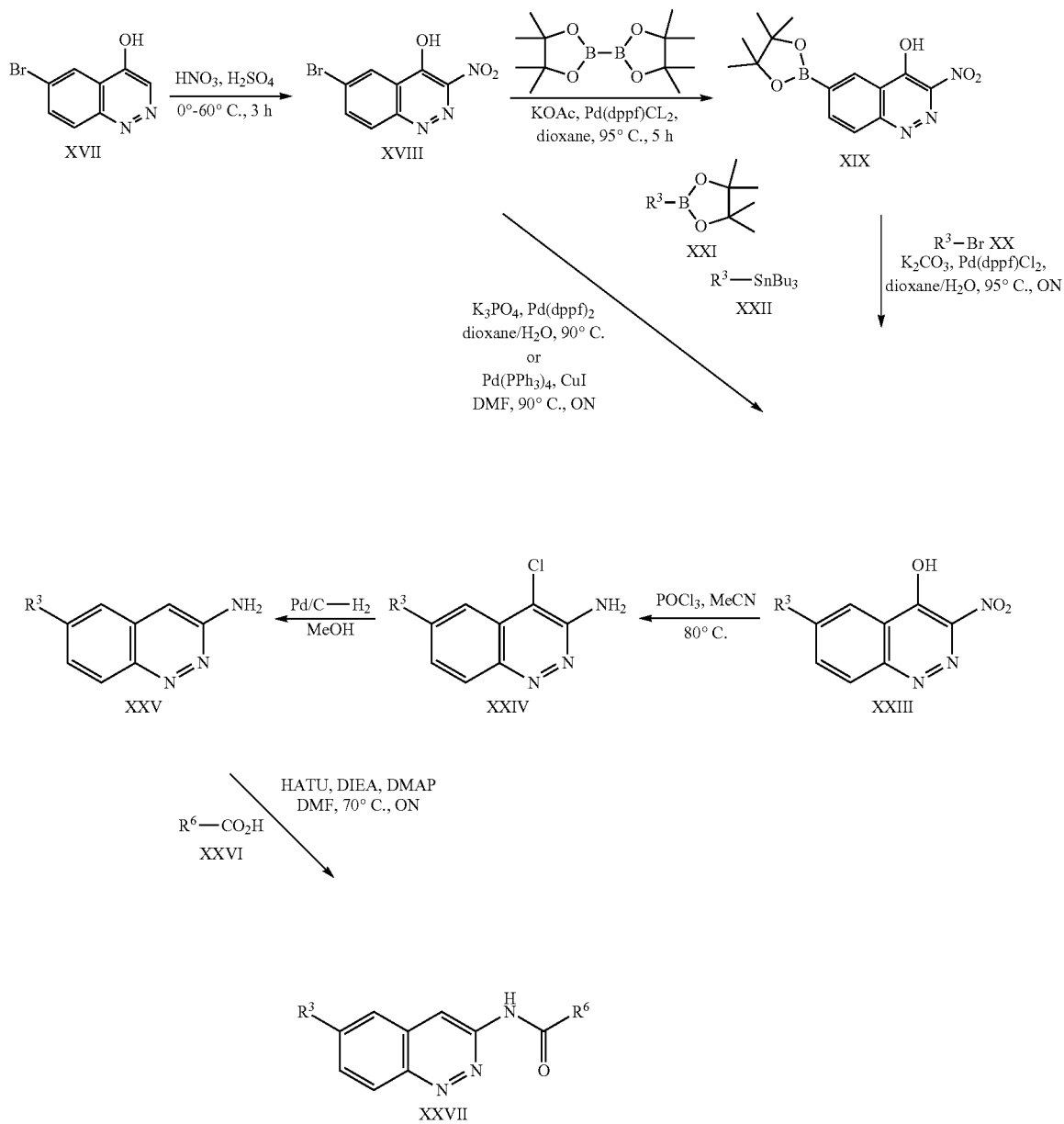

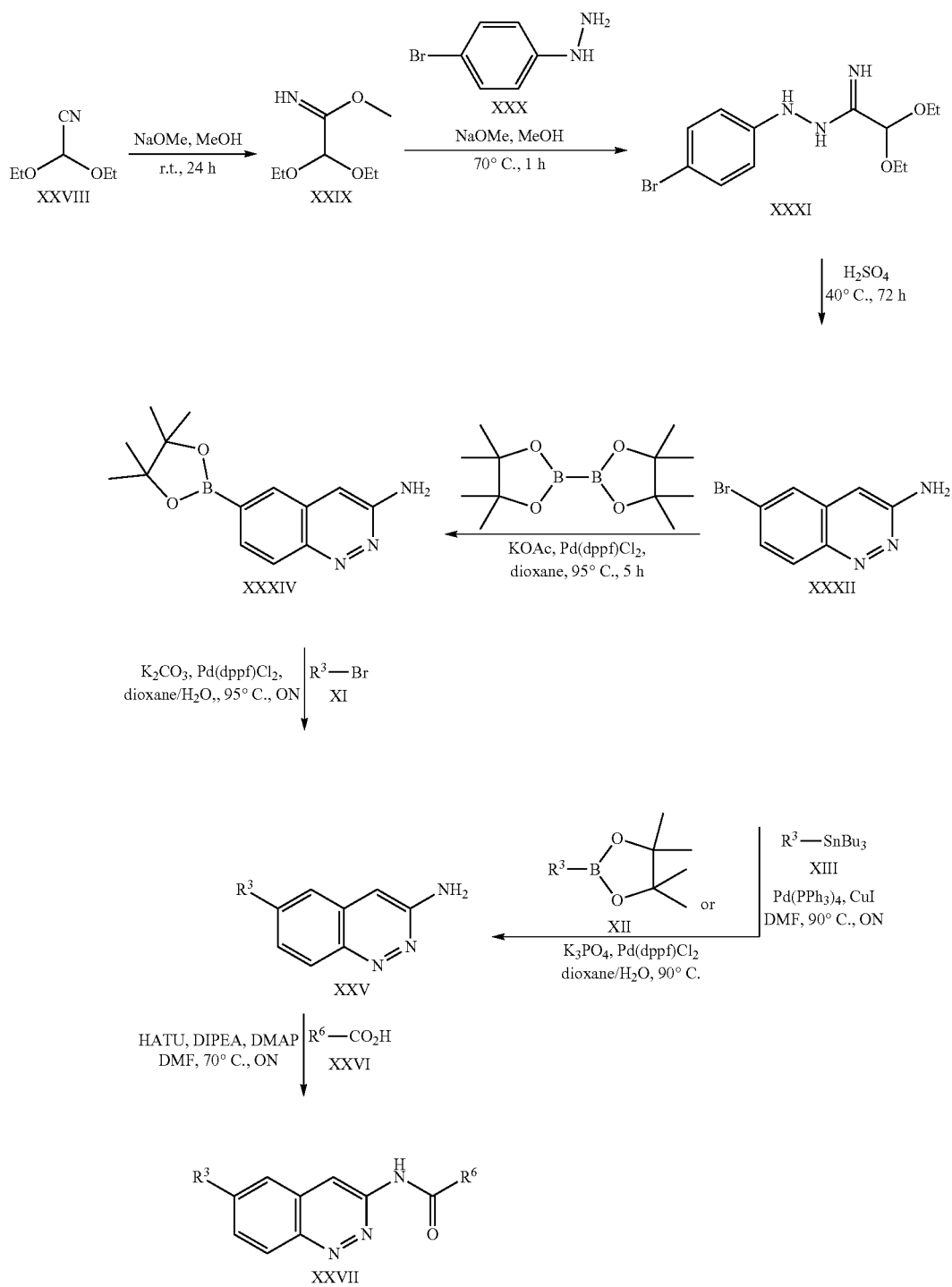

Scheme 3 describes an alternative method for preparation of cinnolin-3-yl-carboxamide derivatives (XXVII) starting with 2,2-diethoxyacetonitrile (XXVIII). The alkoxide-catalyzed formation of the imidate (XXIX). Reaction with (4-bromophenyl)hydrazine (XXX) forms the acetimidohydrazide (XXXI) which then cyclized by acid-catalyzation to the 6-bromocinnolin-3-amine (XXXII). Compound XXXII can be couple with by either of two Suzuki Coupling routes or by a Stille reaction route to produce various 6-substituted cinnolin-3-amine (XXV) derivatives. Amine XXV can be couple with a variety of acids (XXVI) to yield the desired cinnolin-3-yl-carboxamide derivatives (XVI).

In other embodiments, compounds of Formulas I and Id of the present disclosure can be prepared as depicted in Scheme 4.

Scheme 4

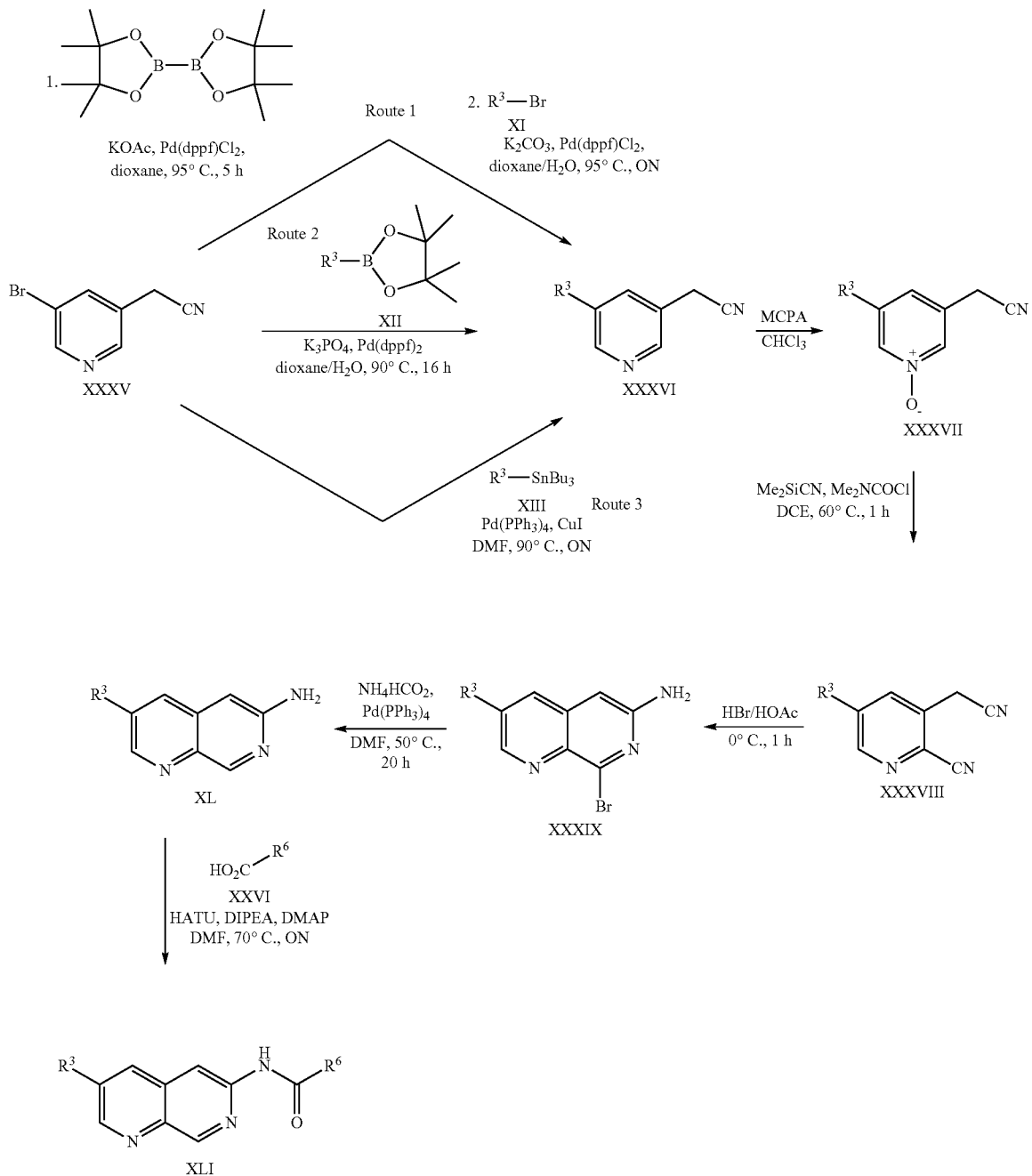

Scheme 4 describes a method for preparation of 1,7-naphthyridin-6-yl-carboxamide derivatives (XLI) by first coupling 2-(5-bromopyridin-3-yl)acetonitrile (XXXV) with a variety of R³-groups by either of two Suzuki Coupling routes (Routes 1 or 2) or by a Stille reaction route (Route 3) to produce various 2-(5-substituted pyridin-3-yl)acetonitrile (XXXVI) derivatives. Formation of the N-oxide (XXXVII) followed by the regioselective cyanation of the pyridine ring with trimethylsilanecarbonitrile leads after cyclization with HBr in HOAc to the 3-substituted-8-bromo-1,7-naphthyridin-6-amine (XXXIX). Palladium catalyzed reduction of the bromine with ammonium formate yields the 3-substituted-1,7-naphthyridin-6-amine (XL) which can be couple with a variety of acids (XXVI) to yield the desired 1,7-naphthyridin-6-yl-carboxamide derivatives (XLI).

In another embodiment, compounds of Formulas I and Id of the present disclosure can be prepared as depicted in Scheme 5.

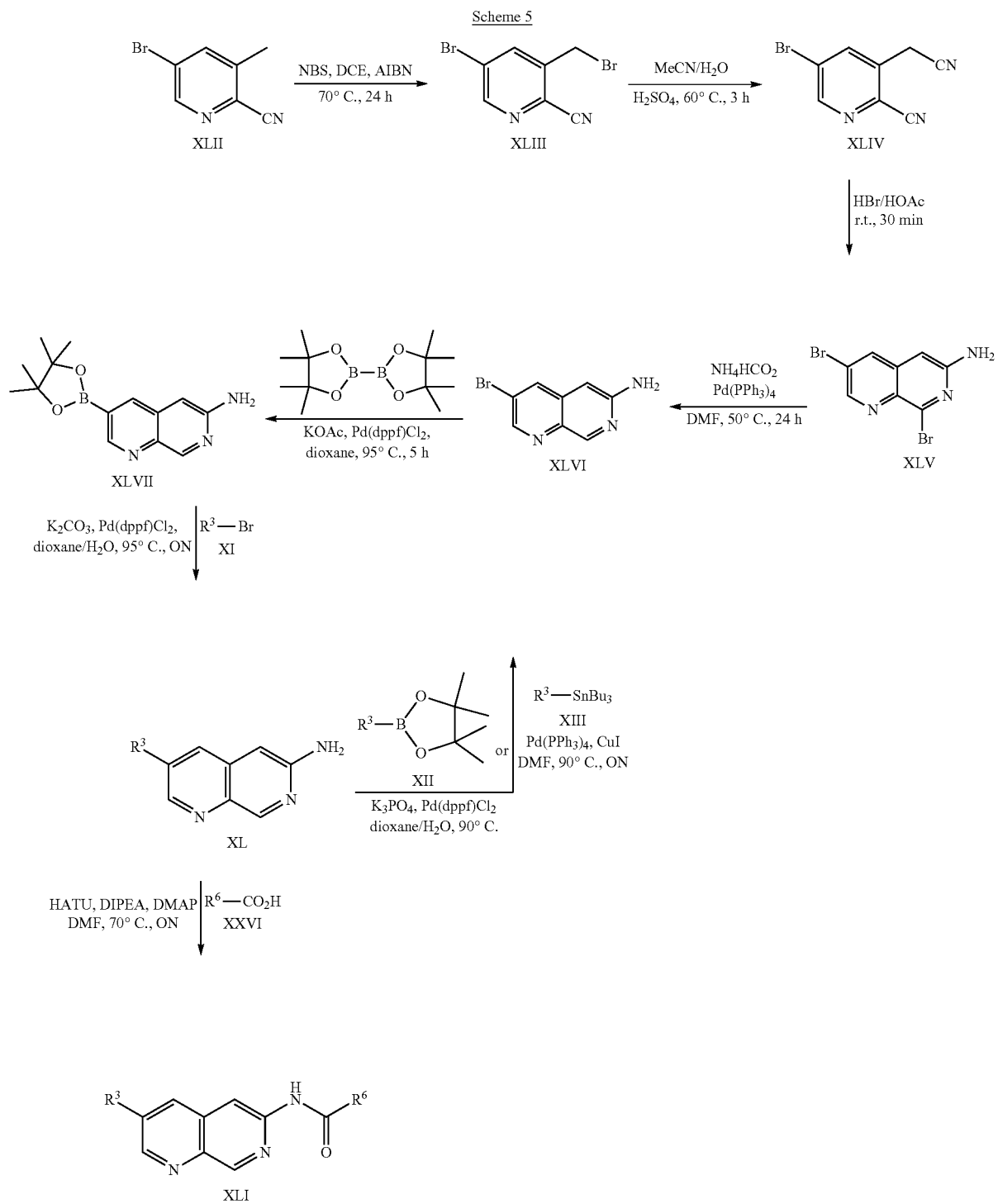

Scheme 5

Scheme 5 describes an alternative method for preparation of 1,7-naphthyridin-6-yl-carboxamide derivatives (XLI) by bromination of 5-bromo-3-methylpicolinonitrile (XLII) with NBS followed by $S_N2$ displacement of the bromine by cyanide to form compound XLIV. Cyclization of dicyano compound XLIV with HBr in HOAc provides 3,8-dibromo-1,7-naphthyridin-6-amine (XLV). Palladium catalyzed reduction of the bromine with ammonium formate yields the 3-bromo-1,7-naphthyridin-6-amine (XLVI) which can be coupled with a variety of $R^3$-groups by either of two Suzuki Coupling routes or by a Stille reaction route to produce various 3-substituted-1,7-naphthyridin-6-amine derivatives (XL) which can be couple with a variety of acids (XXVI) to yield the desired 1,7-naphthyridin-6-yl-carboxamide derivatives (XLI).

In other embodiments, compounds of Formulas I and Ie of the present disclosure can be prepared as depicted in Scheme 6.

Scheme 6

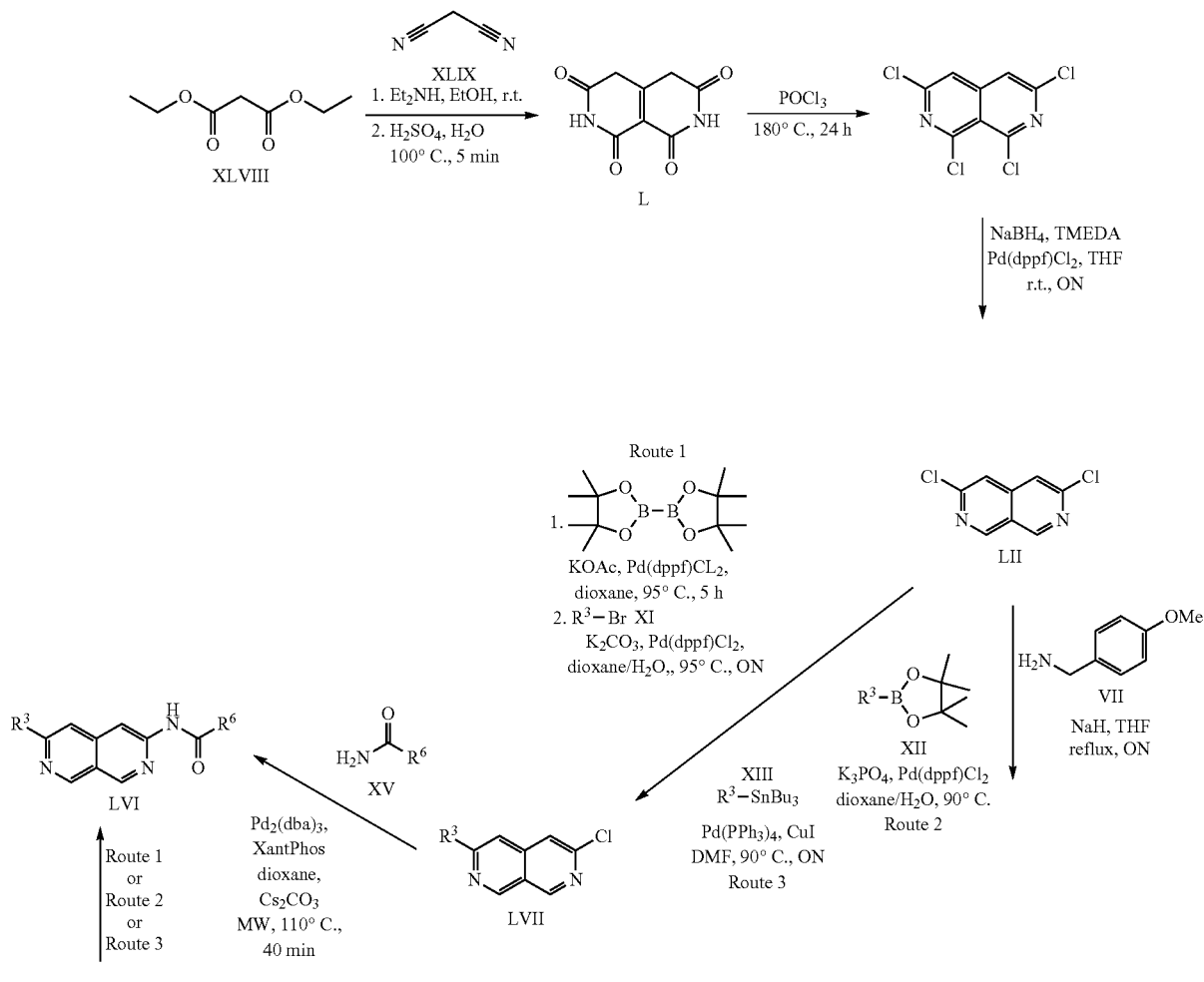

Scheme 6 describes a method for preparation of 2,7-naphthyridin-3-yl-carboxamide derivatives (LVI) by first reacting diethyl 3-oxopentanedioate (XLVIII) with malonitrile (XLIX) followed by acid cyclization to the 2,7-naphthyridinetetraone (L). Chlorodehydroxylation of compound L produces the 3,6-dichloro-2,7-naphth ridinme (LII). Compound LII can either be reacted with (4-methoxyphenyl)methanamine (VII) followed by acid cleavage to give the amine (LIV). Amine LIV can be couple with a variety of acids followed by coupling to a variety of aromatic rings by any of three different routes to yield the desired 2,7-naphthyridin-3-yl-carboxamide derivatives (LVI). Compound LII can also be couple with by either of two Suzuki Coupling routes (Routes 1 or 2) or by a Stille reaction route (Route 3) to produce chloride (LVII) which can then be reacted with a variety of carboxamide (XV) to yield the desired 2,7-naphthyridin-3-yl-carboxamide derivatives (LVI).

ILLUSTRATIVE COMPOUND EXAMPLES

Preparation of intermediate 7-bromo-2-chloro-1,6-naphthyridine (IX) is depicted below in Scheme 7.

Scheme 7

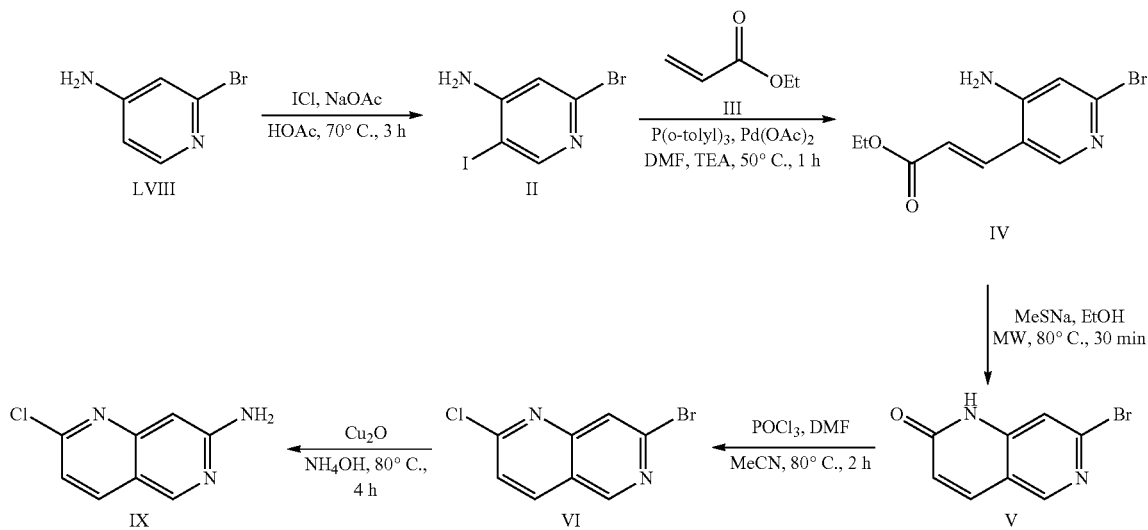

Step 1

To a solution of 2-bromopyridin-4-amine (LVIII) (584 g, 3.38 mol, 1 eq) and sodium acetate (554 g, 6.75 mol, 2 eq) in HOAc (2000 mL) was added a solution of iodine monochloride (559 g, 3.44 mol, 176 mL, 1.02 eq) in HOAc (1000 mL) drop-wise at 70° C., the resulting mixture was stirred at 70° C. for 3 h. The mixture was concentrated to remove HOAc and poured into water (20 L). The aqueous solution was extracted with EtOAc (10 L×3). The combined organic layers were washed with saturated aq. $Na_2CO_3$ (20 L), saturated aq. $Na_2S_2O_3$ (10 L), brine (10 L), dried over $Na_2SO_4$, filtered and concentrated to give a yellow residue, which was purified by column chromatography (1:1→1:0 petroleum ether:DCM) to obtain 2-bromo-5-iodopyridin-4-amine (II) as a yellow solid (340 g, 1.14 mol, 33.7% yield). $^1$H NMR (400 MHz, DMSO-$d_6$) δ ppm 6.56-6.53 (3H, m), 7.73-7.72 (1H, d, J=5.2 Hz); ESIMS found for $C_5H_4BrIN_2$ m/z 299.9 (M+1).

Step 2

2-Bromo-5-iodopyridin-4-amine (II) (340 g, 1.14 mol, 1 eq) was dissolved in DMF (1500 mL) and ethyl acrylate (III) (228 g, 2.27 mol, 247 mL, 2 eq), TEA (173 g, 1.71 mol, 237 mL, 1.5 eq), tris(o-tolyl)phosphine (34.6 g, 114 mmol, 0.1 eq) and Pd(OAc)$_2$ (12.8 g, 56.9 mmol, 0.05 eq) were added. The reaction was placed under nitrogen and heated at 100° C. for 3 h. The reaction mixture was concentrated and EtOAc (7 L) was added, filtered. The filtrate was washed with brine (15 L), dried over $Na_2SO_4$, filtered and concentrated to give ethyl (E)-3-(4-amino-6-bromopyridin-3-yl)acrylate (IV) (320 g, crude) as a yellow solid. It was used directly in next step without further purification. $^1$H NMR (400 MHz, DMSO-$d_6$) δ ppm 1.25 (3H, t, J=7.2 Hz), 4.20-4.15 (2H, m), 6.51 (1H, d, J=15.6 Hz), 6.76 (1H, s), 6.78 (2H, s), 7.73 (1H, d, J=16.0 Hz), 8.22 (1H, s); ESIMS found for $C_{10}H_{11}BrN_2O_2$ m/z 272.0 (M+1).

Step 3

To a solution of ethyl (E)-3-(4-amino-6-bromopyridin-3-yl)acrylate (IV) (300 g, 1.11 mol, 1 eq) in EtOH (1.5 L) was added NaSMe (85.3 g, 1.22 mol, 77.6 mL, 1.1 eq), the resulting mixture was stirred at 50° C. for 1 hour. The reaction mixture was poured into water (3.0 L) and acidified to pH-5 with 1.0 N aq. HCl and filtered. The collected solid was suspended in tert-butyl methyl ether (2.0 L), filtered and the collected solid was concentrated to give 7-bromo-1,6-naphthyridin-2(1H)-one (V) as a yellow solid (207 g, 920 mmol, 83.1% yield). It was used directly in next step. $^1$H NMR (400 MHz, DMSO-$d_6$) δ ppm 6.62-6.60 (1H, m), 7.36 (1H, s), 7.98 (1H, d, J=9.6 Hz), 8.87-8.55 (1H, m), 12.09 (1H, s); ESIMS found for $C_8H_5BrN_2O$ m/z 226.0 (M+1).

Step 4

To a solution of 7-bromo-1,6-naphthyridin-2(1H)-one (V) (140 g, 622 mmol, 1 eq) in MeCN (950 mL) was added POCl$_3$ (238 g, 1.56 mol, 145 mL, 2.5 eq) and DMF (19.0 g, 260 mmol, 20 mL, 0.42 eq), the resulting mixture was stirred at 80° C. for 2 h. After cooling to room temperature, the mixture was poured into water (2000 mL) and neutralized to pH-7 with 1.0 N aq. NaOH, it was extracted with EtOAc (1.0 L×3). The combined organic layers were washed with brine (2.0 L), dried over $Na_2SO_4$, filtered and concentrated to give a yellow residue, which was purified by column chromatography (10:1-5:1, petroleum ether:EtOAc) to give 7-bromo-2-chloro-1,6-naphthyridine (VI) (102 g, 400 mmol, 64.2% yield, 95.1% purity) as a light-yellow solid. $^1$H NMR (400 MHz, DMSO-$d_6$) δ ppm 7.54 (1H, d, J=8.8 Hz), 8.10 (1H, s), 8.24 (1H, m), 9.06 (1H, s); ESIMS found for $C_8H_4BrClN_2$ m/z 244.95 (M+1).

Step 5

A heavy walled resealable tube was loaded, under an argon atmosphere, with copper (I) oxide (3.0 g, 20.97 mmol), 7-bromo-2-chloro-1,6-naphthyridine (VI) (10.2 g, 41.89 mmol) and ammonia hydrate (60 mL, 431.38 mmol). The sealed flask was heated at 80° C. for 4 h. The reaction was cooled to room temperature and poured into water (500 mL). The solid was collected by filtration and dried under vacuum to give 2-chloro-1,6-naphthyridin-7-amine (IX) as yellow solid (5.68 g, 31.6 mmol, 75.5% yield). $^1$H NMR (499 MHz, DMSO-$d_6$) δ ppm 6.55 (2H, s), 6.58 (1H, s), 7.13 (1H, d, J=8.51 Hz), 8.23 (1H, d, J=8.51 Hz), 8.88 (1H, s); ESIMS found for $C_8H_6ClN_3$ m/z 180.0 (M+1).

Preparation of intermediate 6-bromocinnolin-3-amine (XXXII) is depicted below in Scheme 8.

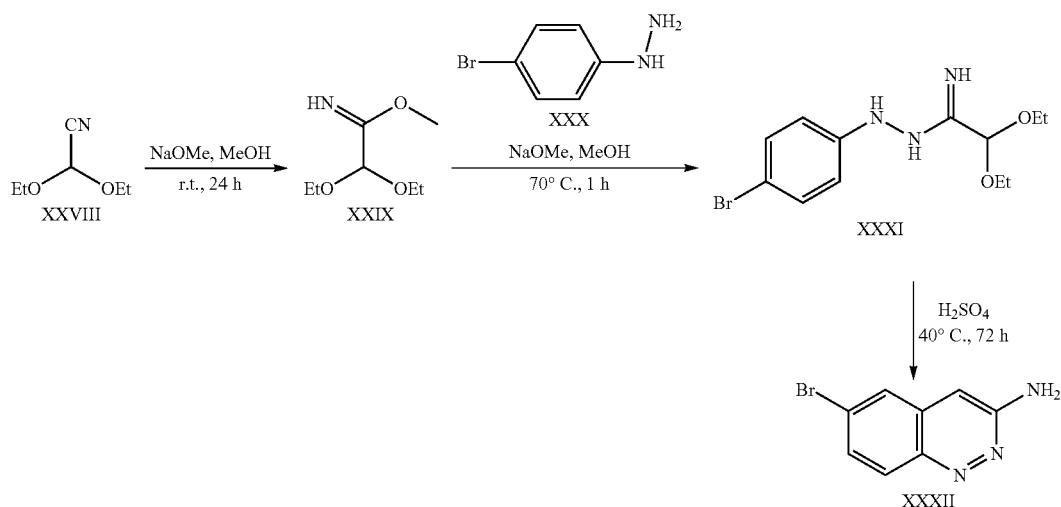

Scheme 8

Step 1

To a stirred solution of 2,2-diethoxyacetonitrile (XXVIII) (5.0 g, 38.71 mmol) in dry MeOH (80 mL) was added a 25% solution of sodium methoxide (1 mL). After the addition, the reaction mixture was stirred at room temperature for 24 h, quenched with dry ice, and then concentrated under vacuum. The resulting residue was diluted with water and EtOAc. The organic layer was separated and aqueous was extracted with EtOAc (3×100 mL). The combined organic layers were dried ($Na_2SO_4$) and the solvent was removed in vacuo to produce the product methyl 2,2-diethoxyacetimidate as colorless oil (XXIX) (4.7 g, 29.2 mmol, 75.3% yield). $^1$H NMR (499 MHz, DMSO-$d_6$) δ ppm 1.14 (6H, t, J=7.14 Hz), 3.51 (4H, qd, J=7.04, 1.10 Hz), 3.65 (3H, s), 4.81 (1H, s), 7.94 (1H, s); ESIMS found for $C_7H_{15}NO_3$ m/z 163.1 (M+2).

Step 2

To a solution of methyl 2,2-diethoxyacetimidate (XXIX) (4.7 g, 29.2 mmol) in anhydrous MeOH (20 mL) was added (4-bromophenyl)hydrazine hydrochloride (XXX) (supplier, CombiBlocks) (3.26 g, 14.6 mmol) and sodium methoxide (0.79 g, 14.58 mmol). the mixture was heated to 70° C. for 1 h. After completion, the MeOH was removed by vacuum and the residue was dissolve in EtOAc (100 mL), washed with brine (3×50 mL), dried, and evaporated to dryness. The crude product was purified by silica column (0→100% EtOAc/Hexanes) to yield N'-(4-bromophenyl)-2,2-diethoxyacetimidohydrazide (XXXI) as brown oil (2.09 g, 6.61 mmol, 22.7% yield). ESIMS found for $C_{12}H_{18}BrN_3O_2$ m/z 316.1 ($^{79}$BrM+1).

Step 3

The N'-(4-bromophenyl)-2,2-diethoxyacetimidohydrazide (XXXI) (2.09 g, 6.61 mmol) was mixed with sulfuric acid (4.0 mL, 75.1 mmol) and the reaction was stirred at 40° C. for 72 h. The solution was poured into ice and neutralized with 2 M NaOH to pH=7.0. The product was purified by silica column (0→20% 7N $NH_3$-MeOH/$CHCl_3$) to produce 6-bromocinnolin-3-amine (XXXII) as a red solid (177 mg, 0.79 mmol, 12.0% yield). ESIMS found for $C_8H_6BrN_3$ m/z 225.0 ($^{79}$BrM+1).

Preparation of intermediate 3-bromo-1,7-naphthyridin-6-amine (XLVI) is depicted below in Scheme 9.

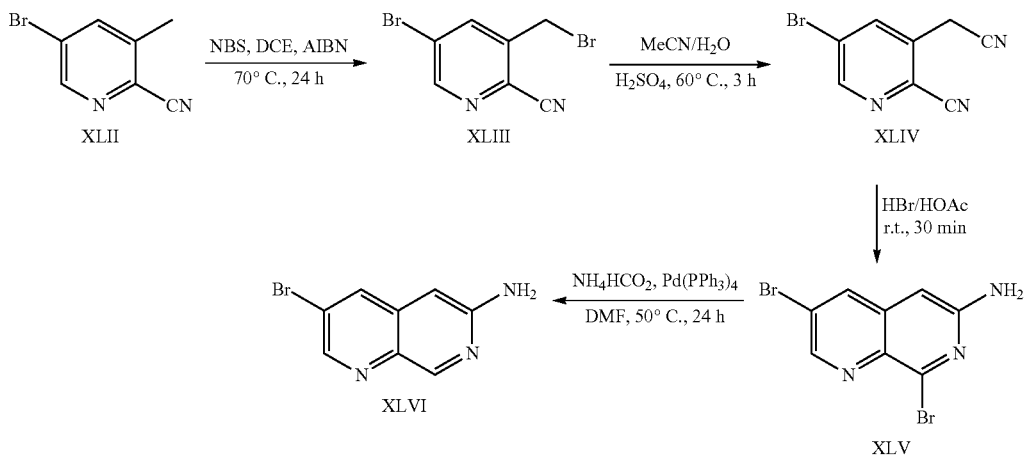

Scheme 9

Step 1

A heterogenous solution of 5-bromo-3-methylpicolinonitrile (XLII) (500 g, 2.54 mol), N-bromosuccinimide (452 g, 2.54 mol) in DCE (2.0 L) was added AIBN (416. g, 2.54 mol), and the resulted solution was stirred at 70° C. for 24 h. The mixture was diluted with water (1.0 L) and extracted with EtOAc (2.0 L). The organic layer was washed with brine (1.0 L) and concentrated to dryness. The residue was purified by chromatography on silica gel (100:1→1-20:1 petroleum ether/EtOAc) to obtain 5-bromo-3-(bromomethyl)picolinonitrile (XLIII) as a white solid (140 g, 507 mmol, 20.0% yield). $^1$H NMR (499 MHz, DMSO-$d_6$) δ ppm 4.78 (2H, s), 8.57 (1H, d, J=2.20 Hz), 8.88 (1H, d, J=2.20 Hz); ESIMS found for $C_7H_4Br_2N_2$ m/z 274.9 (M+1).

Step 2

To a mixture of 5-bromo-3-(bromomethyl)picolinonitrile (XLIII) (30.0 g, 108 mmol) in $CH_3CN$ (30.0 mL), $H_2O$ (30.0 mL) and EtOAc (30.0 mL) was added TMSCN (272 mL, 2.17 mol), then TBAF (1 M, 152 mL) was added. The resulted solution was stirred at 20° C. for 10 min. The mixture was diluted with water (300 mL) and extracted with EtOAc (300 mL×2). The organic layer was washed with brine (300 mL×2), dried over $Na_2SO_4$ and concentrated to dryness. The residue was purified by chromatography on silica gel (50:1→20:1 petroleum ether/EtOAc) to give 5-bromno-3-(cyanomnethyl)picolinonitrile (XLIV) as a light-yellow solid (9.20 g, 41.4 mmol, 38.1% yield). $^1$H NMR (499 MHz, DMSO-$d_6$) δ ppm 4.33 (2H, s), 8.40 (1H, d, J=2.20 Hz), 8.92 (1H, d, J=2.20 Hz); ESIMS found for $C_8H_4BrN_3$ m/z 221.95 (M+1).

Step 3

5-Bromo-3-(cyanomethyl)picolinonitrile (XLIV) (9.00 g, 40.5 mmol) was added slowly to a 40% solution of HBr in HOAc (5.5 mL, 40.5 mmol) and stirred at 20° C. for 1 h. The mixture was poured into water (150 mL) and filtered. The residue was dissolved in EtOAc (1.50 L) and washed with sat. $NaHCO_3$ (300 mL), then brine (500 mL×2). The organic layer was dried over $Na_2SO_4$ and concentrated to obtain 3,8-dibromo-1,7-naphthyridin-6-amine (XLV) as a yellow solid (11.5 g, 37.9 mmol, 93.6% yield). H NMR (499 MHz, DMSO-$d_6$) δ ppm 6.54 (1H, s), 6.69 (2H, br s), 8.42 (1H, d, J=2.20 Hz), 8.58 (1H, d, J=2.20 Hz); ESIMS found for $C_8H_5Br_2N_3$ m/z 301.9 (M+1).

Step 4

A mixture of 3,8-dibromo-1,7-naphthyridin-6-amine (XLV) (11.0 g. 36.3 mmol), ammonium formate (4.88 g, 77.3 mmol) in DMF (50.0 mL) was added $Pd(PPh_3)_4$ (3.36 g, 2.90 mmol) under $N_2$, the resulted solution was stirred at 50° C. for 16 h. The mixture was poured into water (150 mL) and extracted with EtOAc (150 mL×3). The organic layer was washed with brine (100 mL×2), dried over $Na_2SO_4$ and concentrated to give a residue. The residue was purified by Prep-HPLC (column: Phenomenex Synergi Max-RP 250*80 mm*10 μm; mobile phase: [water (0.1% TFA)-MeCN]; B %: 5%-35%, 35 MIN, 60% min) to obtain 3-bromo-1,7-naphthyridin-6-amine (XLVI) as a green solid (5.37 g, 24.0 mmol, yield: 66.1%). $^1$H NMR (400 MHz, DMSO-$d_6$) δ ppm 8.87 (1H, s), 6.37 (2H, s), 6.56 (1H, s), 8.35 (1H, d, J=2.4 Hz), 8.52 (1H, d, J=2.4 Hz); ESIMS found for $C_8H_6BrN_3$ m/z 224.0 (M+1).

Preparation of intermediate 6-chloro-2,7-naphthyridin-3-amine (LIV) is depicted below in Scheme 10.

Scheme 10

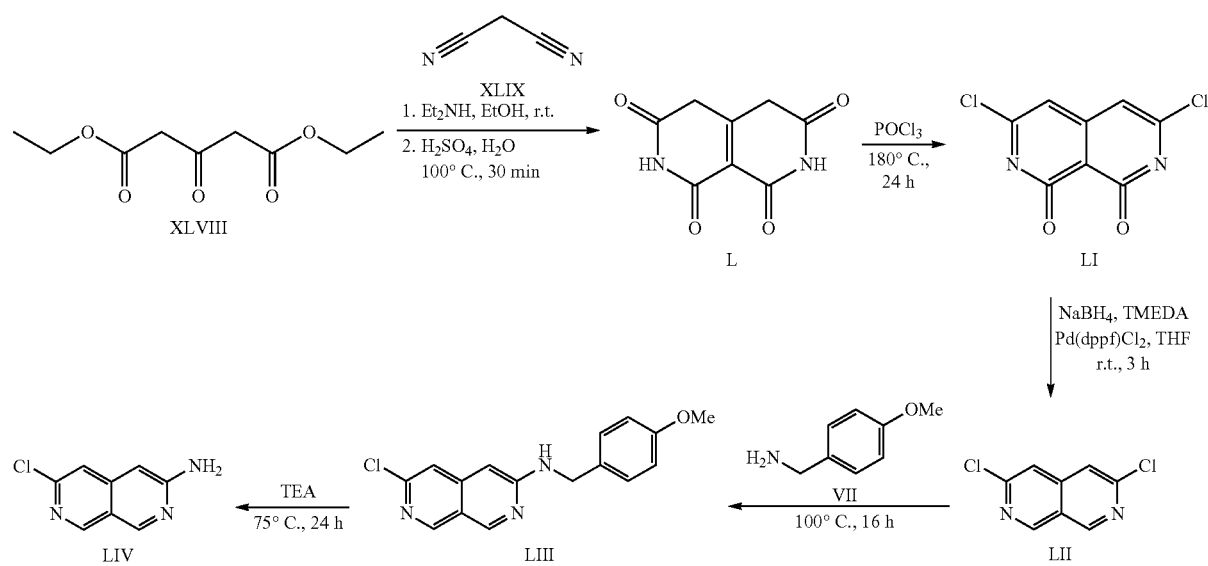

Step 1

Malonitrile (XLIX) (155 mL, 2.47 mol) and diethylamine (50.1 mL, 486 mmol) were added to EtOH (2.5 L) at room temperature. To the stirred solution was added diethyl 3-oxopentanedioate (XLVIII) (450 mL, 2.47 mol) in portions and the resulting dark yellow/orange solution was stirred at room temperature overnight. The mixture was cooled to 0° C., $H_2SO_4$ (1.2 L, 22.5 mol) and $H_2O$ (528 mL, 29.3 mol) was added slowly to the mixture. The resultant solution was stirred at 100° C. for 30 min. The mixture was cooled to 20° C. and slowly poured into water (800 mL), generating a yellow solid. The mixture solution was filtered and dried under vacuum at 60° C. to produce 2,7-naphthyridine-1,3,6,8(2H,4H,5H,7H)-tetraone (L) as a white solid (340 g, 1.75 mol, 70.8% yield). ESIMS found for $C_8H_6N_2O_4$ m/z 195.05 (M+1).

Step 2

2,7-Naphthyridine-1,3,6,8(2H,4H,5H,7H)-tetraone (L) (100 g, 515 mmol) was added to POCl$_3$ (500 mL, 5.38 mol). The mixture was heated to 160° C. in an autoclave for 24 hrs. The reaction mixture was quenched by addition to water (1.0 L) at 0° C. and Na$_2$CO$_3$ (500 g), the mixture was diluted with additional water (500 mL) and extracted with EtOAc (200 mL×3). The combined organic layers were washed with saturated salt solution (200 mL 3), dried over Na$_2$SO$_4$, filtered and concentrated under reduced pressure to give the crude product. The crude product was purified by silica gel column chromatography (50/1→20/1 petroleum ether/EtOAc) to produce 1,3,6,8-tetrachloro-2,7-naphthyridine (LI) as a white solid (25.7 g, 96.3 mmol, 18.7% yield).). $^1$H NMR (400 MHz, CDCl$_3$) δ ppm 7.58 (2H, s); ESIMS found for C$_8$H$_2$Cl$_4$N$_2$ m/z 268.9 (M+1).

Step 3

A mixture of 1,3,6,8-tetrachloro-2,7-naphthyridine (LI) (90.0 g, 336 mmol) in THF (900 mL) was degassed by bubbling N$_2$ for 2 min. Pd(dppf)Cl$_2$ (24.6 g, 33.6 mmol), TMEDA (127 mL, 839 mmol) and NaBH$_3$CN (105 g, 1.68 mmol) were added in sequence. The mixture was stirred at room temperature under argon for 3 h. The reaction was quenched by adding water (1.00 L) at 25° C. and extracted with EtOAc (500 mL×3). The combined organic layers were washed with brine (500 mL×3), dried over Na$_2$SO$_4$, filtered and concentrated under reduced pressure to give a residue. The residue was purified by MPLC (20:1 petroleum ether/EtOAc, R$_f$=0.6) to produce 3,6-dichloro-2,7-naphthyridine (LII) (100 g, 449 mmol, 66.8% yield) as yellow solid. $^1$H NMR (400 MHz, CDCl$_3$) δ ppm 7.67 (2H, s), 9.25 (2H, s); ESIMS found for C$_8$H$_4$Cl$_2$N$_2$ m/z 199.0 (M+1).

Step 4

4-Methoxybenzylamine (VII) (104 mL, 803 mmol) was added to 3,6-dichloro-2,7-naphthyridine (LII) (50 g, 251 mmol), and heated at 100° C. for 16 h. The reaction was purified without further work-up. The crude product was triturated with MTBE (300 mL) at 25° C. for 20 min and then filtrated to give 6-chloro-N-(4-methoxybenzyl)-2,7-naphthyridin-3-amine (LIII) as an off-white solid (180 g, crude). $^1$H NMR (400 MHz, DMSO-d$_6$) δ ppm 3.92 (3H, s), 4.44-4.45 (2H, d, J-=4.0 Hz), 6.44 (1H, s), 6.86-6.88 (2H, d, J=8.0 Hz), 7.27-7.29 (2H, d, J=8.0 Hz), 7.50 (1H, s), 7.81-7.84 (1H, t, J=6.2 Hz), 8.90 (1H, s), 9.07 (1H, s); ESIMS found for C$_{16}$H$_{14}$ClN$_3$O m/z 301.1 (M+1).

Step 5

6-Chloro-N-(4-methoxybenzyl)-2,7-naphthyridin-3-amine (LIII) (90.0 g, 300 mmol) was added to TFA (790 mL, 10.7 mol) and heated at 75° C. for 2.5 h under N$_2$. The reaction mixture was concentrated under reduced pressure to remove TFA. The residue was triturated with EtOH (400 mL) at 25° C. for 20 min and filtrated to produce 6-chloro-2,7-naphthyridin-3-amine (LIV) as a white solid (63.0 g, 328 mmol, 54.6% yield). $^1$H NMR (499 MHz, DMSO-d$_6$) δ ppm 6.48 (1H, s), 7.46 (1H, s), 8.87 (1H, s), 8.99 (1H, s); ESIMS found for C$_8$H$_6$ClN$_3$ m/z 180.0 (M+1).

Preparation of intermediate 1-(bromomethyl)-1-(trifluoromethyl) cyclopropane (LX) is depicted below in Scheme 11.

Scheme 11

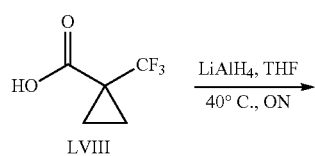

LVIII

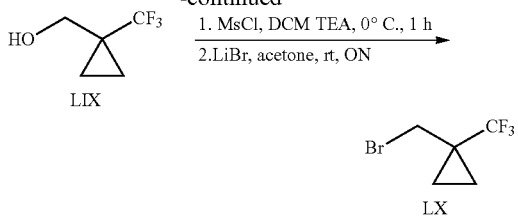

Step 1

1-(Trifluoromethyl)cyclopropane-1-carboxylic acid (LVIII) (3.7334 g, 24.23 mmol) was dissolved in THF (162 mL) and cooled to 0° C. LAH (1.1614 g, 29.07 mmol) was then added and the reaction heated to 40° C. overnight. The reaction was cooled to 0° C. Water (2 mL) was added to quench the reaction followed by 2 N NaOH (0.3 mL). The reaction was stirred forming a precipitate which was filtered off and washed with ether. The aqueous phase was removed, and the organic phase was washed with brine, dried, and carefully concentrated to give (1-(trifluoromethyl)cyclopropyl)methanol (LIX) (1.5376 g, 10.98 mmol, 45.3% yield) as a clear, volatile liquid.

Step 2

To a solution of (1-(trifluoromethyl)cyclopropyl)methanol (LIX) (1.6 g, 11.42 mmol) in DCM (23 mL) was added Et$_3$N (1.9 mL, 13.7 mmol). The reaction was cooled to 0° C. and MsCl was added dropwise. The reaction was stirred at 0° C. for 1 h. The reaction was poured into water and extracted with DCM. The organic phase was separated, washed with brine, dried, and concentrated. The crude mesylate was then dissolved in acetone (22 mL). LiBr (4.96 g, 57.1 mmol) was added, and the reaction stirred at room temperature overnight. The acetone was carefully removed, and the residue was partitioned between water and ether. The aqueous phase was separated and reextracted with ether. The organic phases were combined, washed with brine, dried, and carefully concentrated to give 1-(bromomethyl)-1-(trifluoromethyl)cyclopropane (LX) (1.2867 g, 6.34 mmol, 55.5% yield) as a gold liquid with residual amounts of acetone. $^1$H NMR (499 MHz, DMSO-d$_6$) δ ppm 1.04 (2H, tquin, J=5.17, 5.17, 1.74, 1.74, 1.74, 1.74 Hz), 1.23-1.27 (2H, m), 3.77 (2H, s).

Preparation of intermediate tert-butyl (5-bromothiazol-2-yl)(4-methoxybenzyl)carbamate (LXIV) is depicted below in Scheme 12.

Scheme 12

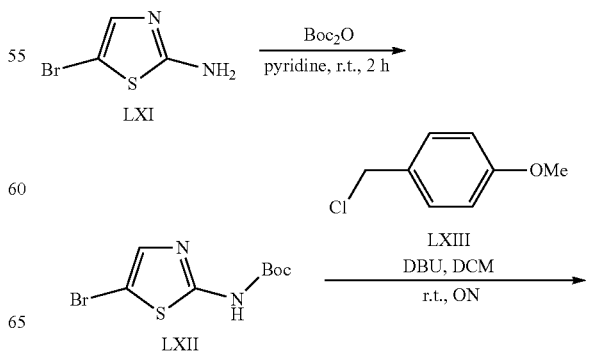

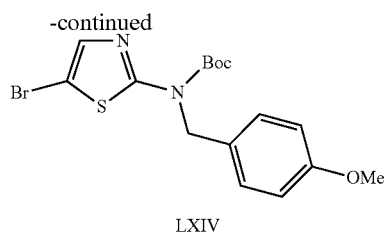

LXIV

Step 1

A mixture of 5-bromothiazol-2-amine hydrobromide (LXI) (1.99 g, 7.66 mmol) and Boc$_2$O (2.21 g, 10.1 mmol) in pyridine (6 mL) was stirred at room temperature for 2 h. The solvent was removed, and the residue was purified by silica gel column chromatography (40 g) (0→50% EtOAc/hexanes) to produce tert-butyl (5-bromothiazol-2-yl)carbamate (LXII) as a white solid (1.6 g, 5.73 mmol, 74.9% yield). ESIMS found for $C_8H_{11}BrN_2O_2S$ m/z 222.9 ($^{81}$BrM+H-$^t$Bu).

Step 2

To a solution of tert-butyl (5-bromothiazol-2-yl)carbamate (LXII) (1.3 g, 4.66 mmol) in DCM (23 mL) was added DBU (2.1 mL, 14.04 mmol) was followed by 1-(chloromethyl)-4-methoxybenzene (LXIII) (0.95 mL, 7.01 mmol). The reaction mixture was stirred at room temperature overnight. The solvent was removed under reduced pressure and the residue was purified by silica gel column chromatography (24 g) (0→10% EtOAc/hexanes) to produce tert-butyl (5-bromothiazol-2-yl)(4-methoxybenzyl)carbamate (LXIV) as an off-white solid (974 mg, 2.44 mmol, 52.4% yield). ESIMS found for $C_{16}H_{19}BrN_2O_3S$ m/z 399.1 (M+H).

Preparation of intermediate tert-butyl 4-((5-bromopyridin-3-yl)oxy)piperidine-1-carboxylate (XLVII) is depicted below in Scheme 13.

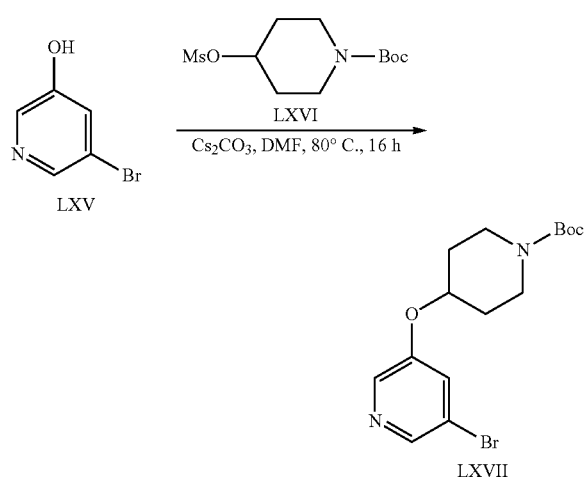

Scheme 13

LXV

LXVII

Step 1

A mixture of 5-bromopyridin-3-ol (LXV) (2 g, 11.49 mmol), tert-butyl 4-((methylsulfonyl)oxy)piperidine-1-carboxylate (LXVI) (3.53 g, 12.64 mmol) and Cs$_2$CO$_3$ (4.87 g, 14.94 mmol) in DMF (20 mL) was stirred at 80° C. for 16 h. The mixture was diluted with water and then extracted with EtOAc. The organic layer was washed with water, brine, and dried over anhydrous sodium sulfate, filtered and concentrated. The crude product was purified on a silica gel column (0→35% EtOAc/hexane) to give tert-butyl 4-((5-bromopyridin-3-yl)oxy)piperidine-1-carboxylate (LXVII) as a white solid (2.88 g, 8.06 mmol, 70.1% yield). ESIMS found for $C_{15}H_{21}BrN_2O_3$ m/z 357.05 (M+H).

Preparation of intermediate tert-butyl 3-(((6-bromopyrazin-2-yl)oxy)methyl) azetidine-1-carboxylate (LXX) is depicted below in Scheme 14.

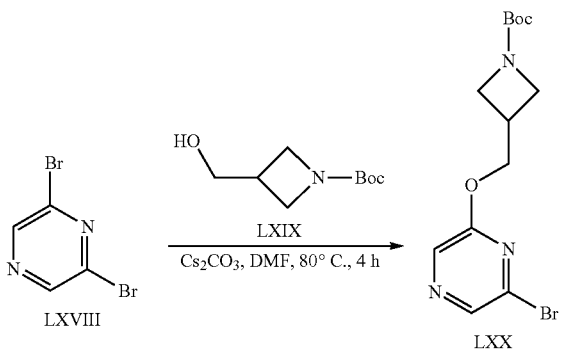

Scheme 14

LXVIII

LXX

Step 1

A mixture of 2,6-dibromopyrazine (LXVIII) (1.1 g, 4.62 mmol), tert-butyl 3-(hydroxymethyl)azetidine-1-carboxylate (LXIX) (0.95 g, 5.09 mmol) and Cs$_2$CO$_3$ (3.01 g, 9.25 mmol) in DMF (6 mL) was stirred at 80° C. for 4 h. The mixture was diluted with water and then extracted with EtOAc/brine. The organic layer was washed with water, brine, and dried over anhydrous sodium sulfate, filtered and concentrated. The crude product was purified on a silica gel column (0→100% EtOAc/hexane) to give tert-butyl 4-((5-bromopyridin-3-yl)oxy)piperidine-1-carboxylate (LXX) as a yellow oil (1.52 g, 4.416 mmol, 95.5% yield). ESIMS found for $C_{13}H_{18}BrN_3O_3$ m/z 344.05 (M+H).

Preparation of intermediate 2-(1-(tert-butoxycarbonyl)piperidin-4-yl)oxazole-4-carboxylic acid (LXXIII) is depicted below in Scheme 15.

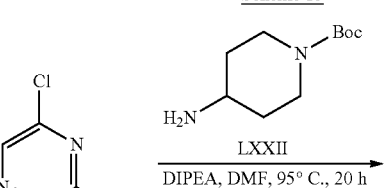

Scheme 15

LXXI

LXXIII

Step 1

To a solution of tert-butyl 4-aminopiperidine-1-carboxylate (LXXII) (2 g, 9.99 mmol) in dry DMF (9.99 ml) was added 2,6-dichloropyrazine (LXXI) (1.488 g, 9.99 mmol). To the mixture was added DIPEA (5.22 mL, 30.0 mmol) and the reaction was stirred at 95° C. or 20 h. The solution was poured into water (200 mL). The solution was allowed to stand for 16 h. The solid was filtered and dried under vacuum, to produce tert-butyl 4-((6-chloropyrazin-2-yl)amino)piperidine-1-carboxylate) (LXXIII) as an off-white solid (1.0172 g, 3.25 mmol, 32.6% yield. ESIMS found for $C_{14}H_{21}ClN_4O_2$ m/z 335.1 (M+Na).

The following intermediates were prepared in accordance with the procedure described in the above Scheme 15.

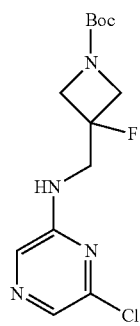

LXXIV tert-Butyl 3-[[(6-chloropyrazin-2-yl)amino]methyl]-3-fluoro-azetidine-1-carboxylate (LXXIV): Off-white solid, (56.4% yield). ESIMS found $C_{13}H_{18}ClFN_4O_2$ m/z 338.95 (M+Na).

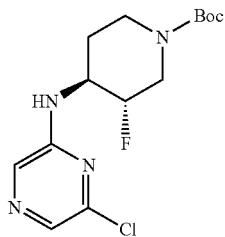

LXXV tert-Butyl (3S,4S)-4-((6-chloropyrazin-2-yl)amino)-3-fluoropiperidine-1-carboxylate (LXXV): Off white solid (54.0% yield). ESIMS found $C_{14}H_{20}ClFN_4O_2$ m/z 352.90 (M+H).

Preparation of intermediate 6-bromo-N-(tert-butyl)pyrazin-2-amine (LXXVII) is depicted below in Scheme 16.

Scheme 16

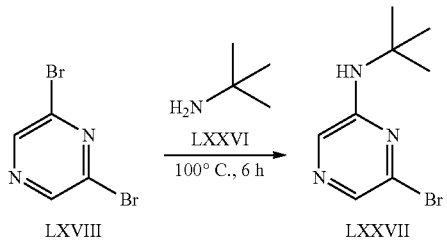

Step 1

2,6-Dibromopyrazine (LXVIII) (2 g, 8.41 mmol) was added to tert-butylamine (LXXVI) (4.4 mL, 41.87 mmol) and stirred at 100° C. for 6 h. Excess amine was removed under vacuum and the residue was purified by silica gel column chromatography (0→20% EtOAc/hexanes) to produce 6-bromo-N-(tert-butyl)pyrazin-2-amine (LXXVII) as an off-white solid (1.82 g, 7.91 mmol, 94.1% yield). ESIMS found for $C_8H_{12}BrN_3$ m/z 230. (M+H).

The following intermediate was prepared in accordance with the procedure described in the above Scheme 16.

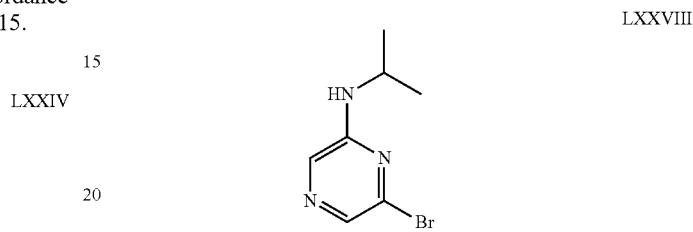

LXXVIII

6-Bromo-N-isopropylpyrazin-2-amine (LXXVIII): Yellow wax, (1.08 g, 5.00 mmol, 93.0% yield). ESIMS found $C_7H_{10}BrN_3$ m/z 218.0 ($^{81}$BrM+H).

Preparation of intermediate trans-4-((tert-butoxycarbonyl)(methyl)amino) cyclohexane-1-carboxylic acid (LXXXI) is depicted below in Scheme 17.

Scheme 17

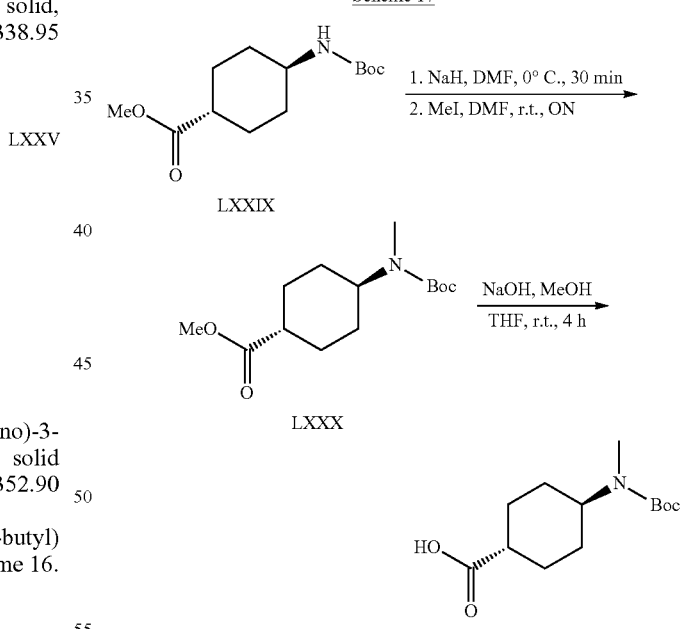

Step 1

To a solution of methyl trans-4-((tert-butoxycarbonyl)amino)cyclohexane-1-carboxylate (LXXIX) (1.3 g, 5 mmol) in DMF (15 mL) and cooled to 0° C. was added sodium hydride (60% in oil, 240 mg, 6 mmol) over 30 minutes. The mixture is stirred at room temperature for 1 h, then cooled to 0° C. and treated with iodomethane (0.38 mL, 6 mmol). After stirring overnight at room temperature, the mixture is poured into a saturated aqueous $NH_4Cl$ and extracted with EtOAc. The combined organic phase is washed with water and brine, dried over anhydrous Na₂SO₄ and concentrated under reduced pressure. The obtained residue is purified by column chromatography on silica gel (10:1 n-hexane-EtOAc) to obtain methyl trans-4-((tert-butoxycarbonyl)(methyl)amino)cyclohexane-1-carboxylate (LXXX) (1.3 g, 4.79 mmol, 94.8% yield).

Step 2

To a stirred solution of methyl trans-4-((tert-butoxycarbonyl)(methyl)amino) cyclohexane-1-carboxylate (LXXX) (130 mg, 4.79 mmol) in a mixture of MeOH (10 mL) and THF (10 mL) was added 2 N aqueous NaOH (4.79 mL, 9.58 mmol) and the mixture was stirred for 4 h. The solvent was concentrated, the residue taken in water and acidified with 1N HCl and extracted with EtOAc. The organics were washed with 2× water then 1× brine. The organics were then separated and dried (MgSO₄) before concentration to dryness to obtain trans-4-((tert-butoxycarbonyl)(methyl)amino)cyclohexane-1-carboxylic acid (LXXXI) as a thick gum (1.198 g, 4.65 mmol, 97.2% yield) which was used for next step without purification.

Preparation of intermediate 1-((3-methyloxetan-3-yl)methyl)piperidine-4-carboxylic acid (LXXXV) is depicted below in Scheme 18.

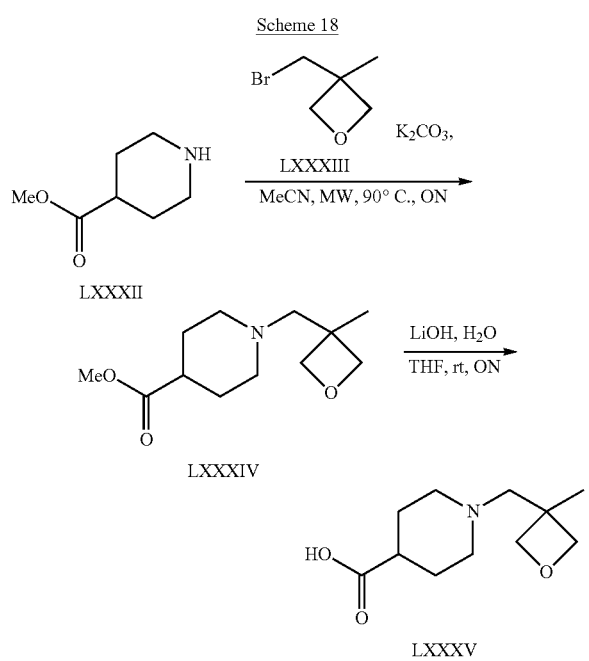

Step 1

A solution of methyl piperidine-4-carboxylate (LXXXII) (254 mg, 1.77 mmol), 3-(bromomethyl)-3-methyloxetane (LXXXIII) (439 mg, 2.66 mmol), and potassium carbonate (736 mg, 5.32 mmol) in MeOH (5 mL) was heated by microwave irradiation at 90° C. overnight. The solvent was removed under vacuum and the residue taken up in DCM and filtered. The organic layer was evaporated to give methyl 1-((3-methyloxetan-3-yl)methyl)piperidine-4-carboxylate (LXXXIV) as a brown oil (490 mg) which was used without further purification. ESIMS found for $C_{12}H_{21}NO_3$ m/z 228.2 (M+H).

Step 2

To a stirred solution of methyl 1-((3-methyloxetan-3-yl)methyl)piperidine-4-carboxylate (LXXXIV) (403 mg, 1.77 mmol) in THF (3 mL) and water (3 mL) was added lithium hydroxide (46.7 mg, 1.95 mmol). The reaction was stirred at room temperature for overnight. The reaction was evaporated and then treated twice with toluene to remove residue water. The crude product was mixed with DCM/hexane, filtered and dried to produce 1-((3-methyloxetan-3-yl)methyl)piperidine-4-carboxylic acid (LXXXV) as a light brown solid (405 mg) which was used without further purification. ESIMS found for $C_1H_{19}NO_3$ m/z 214.1 (M+H).

Preparation of intermediate 4-((dimethylamino)methyl)benzoic acid (LXXXIX) is depicted below in Scheme 19.

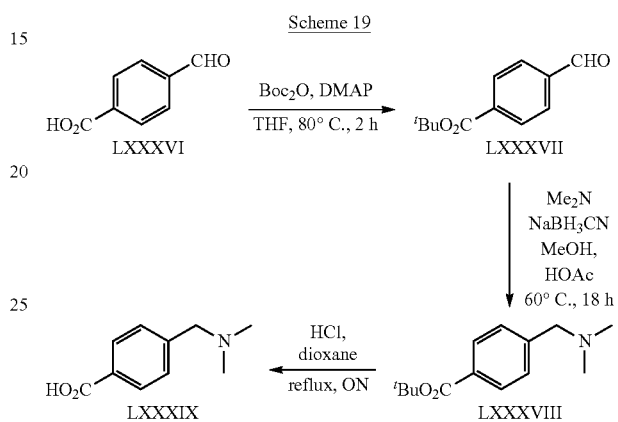

Step 1

To a solution of 4-formylbenzoic acid (LXXXVI) (2.12 g, 14.1 mmol) in THF (7.2 mL) was added Boc₂O (4.92 g, 28.2 mmol) and DMAP (0.35 g, 2.82 mmol). The reaction was stirred at 80° C. for 2 h. The reaction was extracted with EtOAc-saturated NaHCO₃ and the organic layer was separated, dried over Na₂SO₄ and evaporated to dryness under vacuum. The residue was purified by silica column (0→100% EtOAc-Hexanes) to give tert-butyl 4-formylbenzoate (LXXXVII) as off white solid (2.23 g, 10.8 mmol, 76.6% yield). ESIMS found for $C_{12}H_{14}O_3$ m/z 207.1 (M+H).

Step 2

A solution of tert-butyl 4-formylbenzoate (LXXXVII) (2.23 g, 10.8 mmol), 2.0 M solution of dimethylamine in MeOH (7 mL, 14.06 mmol) and HOAc (310 μL, 5.41 mmol) in MeOH (125.7 mL) was stirred at room temperature for 10 min. To the mixture was added with NaBH₃CN (883 mg, 14.06 mmol) and the mixture stirred at 60° C. for 18 h. The mixture was concentrated, and the residue was purified by column chromatography (0-+100% EtOAc-Hexanes). The fractions containing the product were concentrated to yield tert-butyl 4-((dimethylamino)methyl)benzoate (LXXXVIII) as a yellow oil (920 mg, 3.71 mmol, 34.4% yield). ESIMS found for $C_{14}H_{21}NO_2$ m/z 236.2 (M+H).

Step 3

To a suspension of HCl (7.23 mL, 14.5 mmol) in 1,4-dioxane (5 mL) was added tert-butyl 4-((dimethylamino)methyl)benzoate (LXXXVIII) (0.92 g, 3.91 mmol). The reaction was heated under reflux for 16 h. The reaction was then cooled and the solid was collected by filtration, washed with dioxane and dried under vacuum to produce 4-((dimethylamino)methyl)benzoic acid (LXXXIX) as a white solid (427 mg, 1.98 mmol, 50.6% yield). ESIMS found for $C_{10}H_{13}NO_2$ m/z 180. (M+H).

Preparation of intermediate 1'-methyl-1',2',3',6'-tetrahydro-[2,4'-bipyridine]-4-carboxylic acid (XCIII) is depicted below in Scheme 20.

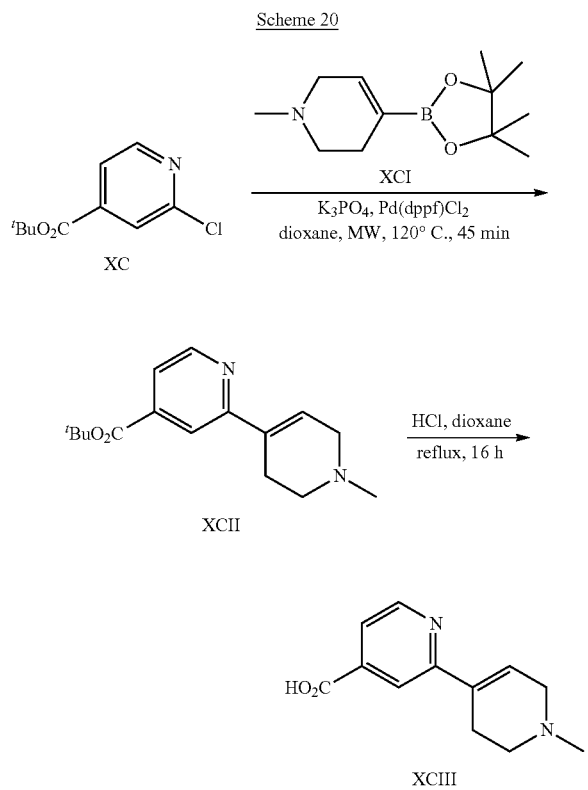

Step 1

A solution of tert-butyl 2-chloroisonicotinate (XC) (supplier: Synthonix) (2.0 g, 9.36 mmol), 1-methyl-4-(4,4,5,5-tetramethyl-1,3,2-dioxaborolan-2-yl)-1,2,3,6-tetrahydropyridine (XCI) (supplier: Ark Pharm) (2.55 g, 11.4 mmol), K$_3$PO$_4$ (5.96 g, 28.1 mmol), Pd(dppf)Cl$_2$ (870 mg, 1.07 mmol) in dioxane (85 mL). The solution was purged with Argon and heated by microwave irradiation at 120° C. The solvent was removed under vacuum and the residue was purified by silica gel column chromatography (24 g) (0→10% MeOH/CHCl$_3$) to produce tert-butyl 1'-methyl-1',2',3',6'-tetrahydro-[2,4'-bipyridine]-4-carboxylate (XCII) as a tan solid (2.5 g, 9.1 mmol, 97.3% yield). ESIMS found for C$_{16}$H$_{22}$N$_2$O$_2$ m/z 275.15 (M+H).

Step 2

To a suspension of HCl (23 mL, 91.9 mmol) in 1,4-dioxane (30 mL) was added tert-butyl 1'-methyl-1',2',3',6'-tetrahydro-[2,4'-bipyridine]-4-carboxylate (XCII) (2.5 g, 9.11 mmol). The reaction was heated under reflux for 16 h. The reaction was then cooled and the solid was collected by filtration, washed with MTBE and dried under vacuum to produce 1'-methyl-1',2',3',6'-tetrahydro-[2,4'-bipyridine]-4-carboxylic acid (XCIII) as a white solid (1.88 g, 7.38 mmol, 81.0% yield). ESIMS found for C$_{12}$H$_{14}$N$_2$O$_2$ m/z 219.1 (M+H).

Preparation of intermediate 2-((1-methylpiperidin-4-yl)thio)isonicotinic acid (XCVI) is depicted below in Scheme 21.

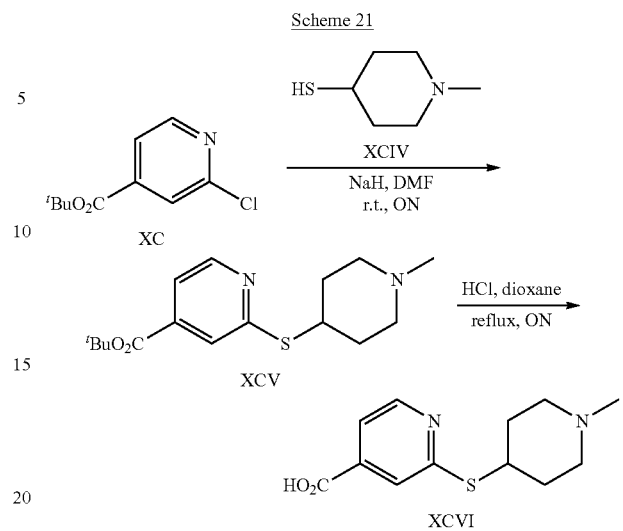

Step 1

To a solution of 1-methylpiperidine-4-thiol (XCIV) (200 mg, 1.52 mmol) in DMF (2 mL) was added NaH (61 mg, 1.53 mmol) at 0° C. stirred for 30 min. tert-Butyl-2-chloroisonicotinate (XC) (supplier: Synthonix) (400 mg, 1.87 mmol) was then added and the reaction mixture was stirred at room temperature overnight. The solvent was removed under vacuum and the residue was purified by silica gel column chromatography (24 g) (0→10% 1.7N NH$_3$ in MeOH/CHCl$_3$) to produce tert-butyl 2-((1-methylpiperidin-4-yl)thio)isonicotinate (XCV) as an off-white solid (271 mg, 0.88 mmol, 57.7% yield). ESIMS found for C$_{16}$H$_{24}$N$_2$O$_2$S m/z 309.2 (M+H).

Step 2

To a suspension of HCl (0.88 mL, 3.52 mmol) in 1,4-dioxane (0.88 mL) was added tert-butyl 2-((1-methylpiperidin-4-yl)thio)isonicotinate (XCV) (271 mg, 0.88 mmol). The reaction was heated at reflux overnight. The reaction was then cooled and the solid was collected by filtration, washed with diethyl ether and dried under vacuum to produce 2-((1-methylpiperidin-4-yl)thio)isonicotinic acid (XCVI) as a white solid (136 mg, 0.418 mmol, 47.8% yield). ESIMS found for C$_{12}$H$_{16}$N$_2$O$_2$S m/z 253.1 (M+H).

Preparation of intermediate 2-(4-(tert-butoxycarbonyl)piperazin-1-yl) isonicotinic acid (C) is depicted below in Scheme 22.

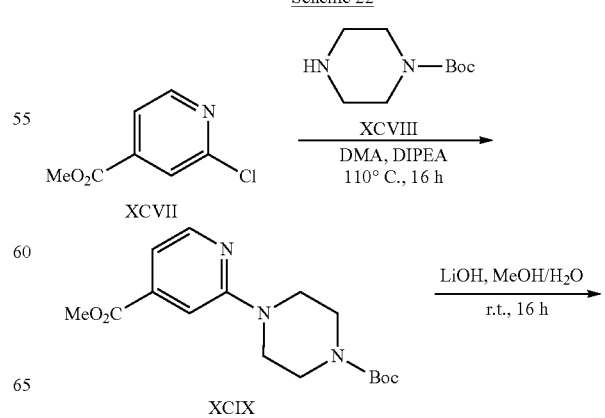

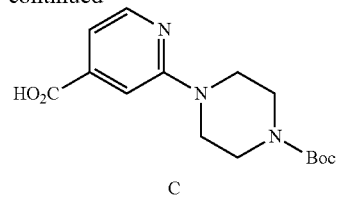

C

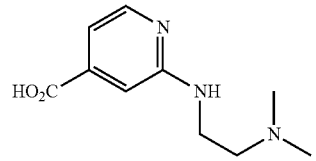

CIII 2-((2-(Dimethylamino)ethyl)amino)isonicotinic acid (CIII): White solid, (357 mg, 1.45 mmol, 93.6% yield). ESIMS found $C_{10}H_{15}N_3O_2$ m/z 210.1 (M+H).

Step 1

To a solution of ethyl 2-chloroisonicotinate (XCVII) (10 g, 53.88 mmol) in DMA (108 mL) was added tert-butyl piperazine-1-carboxylate (XCVIII) (0.32 mL, 2.89 mmol) and DIPEA (18.8 mL, 107.75 mmol). The reaction was stirred at 110° C. for 16 h. The mixture was poured into water, extracted with EtOAc, and dried over $Na_2SO_4$. The solvent was removed under high vacuum and the residue was purified on a silica gel column (120 g) (0→100% hexane/EtOAc) to give tert-butyl 4-(4-(ethoxycarbonyl)pyridin-2-yl)piperazine-1-carboxylate (XCIX) as a brown oil (10.84 g, 32.32 mmol, 60.0% yield). ESIMS found for $C_{17}H_{25}N_3O_4$ m/z 336.15 (M+H).

Step 2

To a solution of tert-butyl 4-(4-(ethoxycarbonyl)pyridin-2-yl)piperazine-1-carboxylate (XCIX) (10.7 g, 31.9 mmol) in MeOH (130 mL) and water (26 mL) was added 4 M aqueous lithium hydroxide (7.98 mL, 31.9 mmol). The reaction was stirred at room temperature for 16 h. The reaction was poured into water and neutralized with concentrated HCl (31.9 mL, 31.9 mmol) and extracted with EtOAc. The organic layer was dried over $Na_2SO_4$ and evaporated under high vacuum to produce 2-(4-(tert-butoxycarbonyl)piperazin-1-yl)isonicotinic acid (C) as a white solid (8.79 g, 28.6 mmol, 89.7% yield) which was used without further purification. ESIMS found for $C_{15}H_{21}N_3O_4$ m/z 308.15 (M+H).

The following intermediates were prepared in accordance with the procedure described in the above Scheme 22.

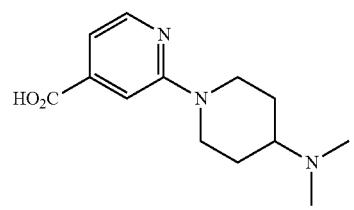

CIV 2-(4-(Dimethylamino)piperidin-1-yl)isonicotinic acid (CIV): Off-white solid, (1.2 g, 4.20 mmol, 98.7% yield). ESIMS found $C_{13}H_{19}N_3O_2$ m/z 250.1 (M+H).

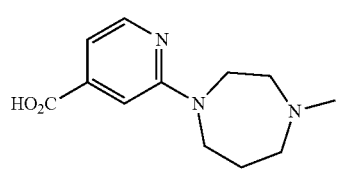

CV 2-(4-Methyl-1,4-diazepan-1-yl)isonicotinic acid (CV): Light brown solid, (1.0 g, 3.68 mmol, 97.5% yield). ESIMS found $C_{12}H_{17}N_3O_2$ m/z 236. (M+H).

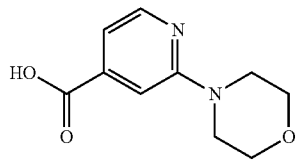

CI

2-Morpholinoisonicotinic acid (CI): Off-white solid, (631 mg, 3.03 mmol, 38.7% yield). ESIMS found $C_{10}H_{12}N_2O_3$ m/z 209.1 (M+H).

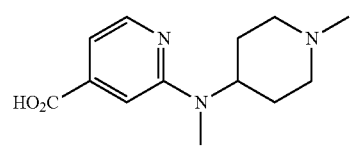

CVI 2-(Methyl(1-methylpiperidin-4-yl)amino)isonicotinic acid (CVI): Brown solid, (230 mg, 0.80 mmol, 91.0% yield). ESIMS found $C_{13}H_{19}N_3O_2$ m/z 250. (M+H).

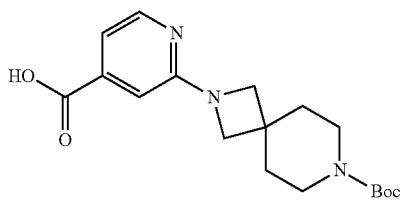

CII 2-(7-(tert-Butoxycarbonyl)-2,7-diazaspiro[3.5]nonan-2-yl)isonicotinic acid (CII): White solid, (360 mg, 1.04 mmol, 84.9% yield). ESIMS found $C_{18}H_{25}N_3O_4$ m/z 348. (M+H).

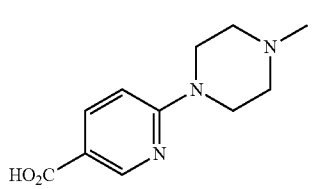

CVII 6-(4-Methylpiperazin-1-yl)nicotinic acid (CVII): White solid, (5.5 g, 21.3 mmol, 98.7% yield). ESIMS found $C_{11}H_{15}N_3O_2$ m/z 222.1 (M+H).

Preparation of intermediate 2-((1-(tert-butoxycarbonyl)piperidin-4-yl)oxy) isonicotinic acid (CX) is depicted below in Scheme 23.

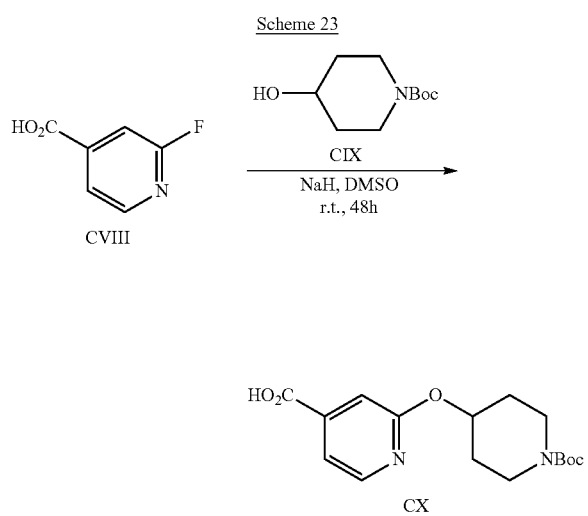

Step 1

To a solution of 2-fluoropyridine-4-carboxylic acid (CVIII) (6.65 g, 47.13 mmol) in DMSO (180 mL) was added tert-butyl 4-hydroxypiperidine-1-carboxylate (CIX) (14.23 g, 70.69 mmol) and 2-fluoropyridine-4-carboxylic acid (6.65 g, 47.13 mmol). To this mixture was added NaH (8.48 g, 212.08 mmol) in 3 portions. this mixture was stirred at room temperature for 48 h. The reaction was poured into 1 N NaOH, the water layer was washed with EtOAc, the water layer was then acidified with concentrated HCl (20 mL), extracted with EtOAc and dried over $Na_2SO_4$. The solvent was removed, and the residue was purified by C18 Silica Gel column chromatography (0→40% MeCN/0.1% formic acid in water) to produce 2-((1-(tert-butoxycarbonyl)piperidin-4-yl)oxy)isonicotinic acid (CX) (12.85 g, 39.9 mmol, 84.6% yield) as a white solid. $^1$H NMR (499 MHz, DMSO-$d_6$) δ ppm 1.41 (s, 9H), 1.52-1.62 (m, 2H), 1.90-1.98 (m, 2H), 3.12-3.23 (m, 2H), 3.64-3.72 (m, 2H), 5.21 (tt, J=8.13, 3.95 Hz, 1H), 7.15 (s, 1H), 7.36 (dd, J=5.21, 1.37 Hz, 1H), 8.31 (d, J=5.21 Hz, 1H), 13.62 (br s, 1H); ESIMS found for $C_{16}H_{22}N_2O_5$ m/z 323.1 (M+H).

Preparation of intermediate 4-((1-(tert-butoxycarbonyl)piperidin-4-yl)oxy) benzoic acid (CXIII) is depicted below in Scheme 24.

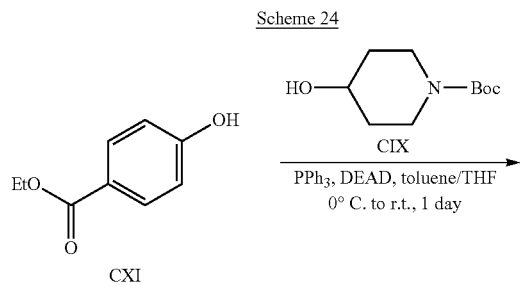

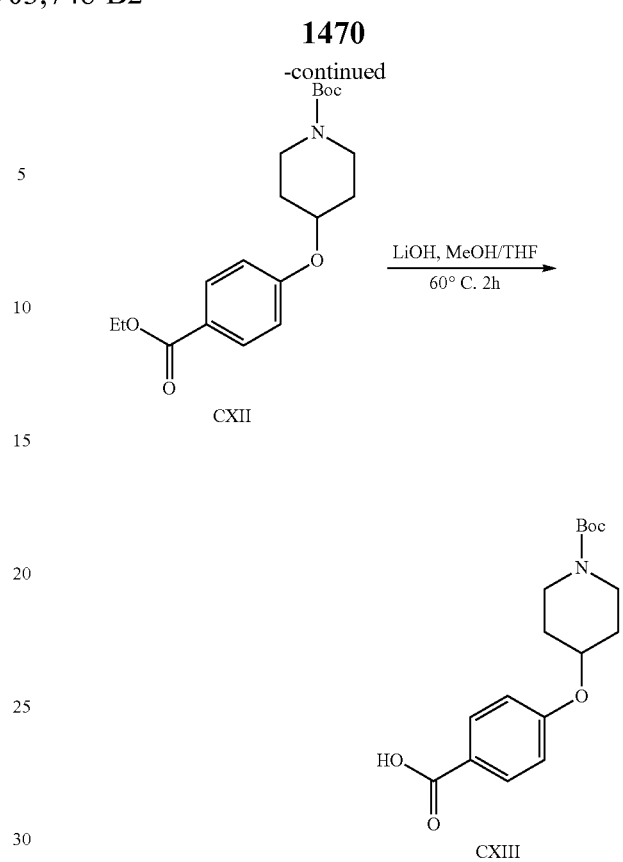

Step 1

To a solution of DEAD (12.3 mL, 27.08 mmol) (40% in toluene) was added to a mixture of ethyl 4-hydroxybenzoate (CXI) (3.0 g, 18.05 mmol), tert-butyl 4-hydroxypiperidine-1-carboxylate (CIX) (4.72 g, 23.47 mmol) and triphenylphosphane (6.16 g, 23.47 mmol) in THF (40 mL) at 0° C. The mixture was stirred from 0° C. to room temperature over 1 day before concentrating in vacuo. The residue was diluted with EtOAc, washed with 1 N NaOH and brine, and then evaporated under vacuum. The crude product was purified by chromatography (0→30% EtOAc/hexanes) to give tert-butyl 4-(4-ethoxycarbonylphenoxy)piperidine-1-carboxylate (CXII) (5.4 g, 15.45 mmol, 85.6% yield) as a colorless oil. ESIMS found for $C_{19}H_{27}NO_5$ m/z 372.1 (M+Na).

Step 2

To a solution of tert-butyl 4-(4-ethoxycarbonylphenoxy)piperidine-1-carboxylate (CXII) (5.4 g, 15.45 mmol) in MeOH (10 mL) and THF (10 mL) was added LiOH (15.5 mL, 61.82 mmol) and the mixture stirred at 60° C. for 2 h. The mixture was concentrated, and the residue triturated with water. The resulting solution was acidified with 2 N HCl until a solid precipitated. The solid was filtered and washed with water to afford 4-[(1-tert-butoxycarbonyl-4-piperidyl)oxy]benzoic acid (CXIII) (4.7 g, 14.63 mmol, 94.6% yield) as a white solid. $^1$H NMR (499 MHz, DMSO-$d_6$) δ ppm 1.40 (9H, s), 1.47-1.57 (2H, m), 1.89-1.97 (2H, m), 3.12-3.23 (2H, m), 3.63-3.70 (2H, m), 4.63-4.71 (1H, m), 7.04 (2H, d, J=9.06 Hz), 7.87 (2H, d, J=9.06 Hz); ESIMS found for $C_{17}H_{23}NO_5$ m/z 344.1 (M+Na).

Preparation of intermediate 1-(1-(tert-butoxycarbonyl)piperidin-4-yl)-1H-pyrazole-4-carboxylic acid (CXVII) is depicted below in Scheme 25.

Scheme 25

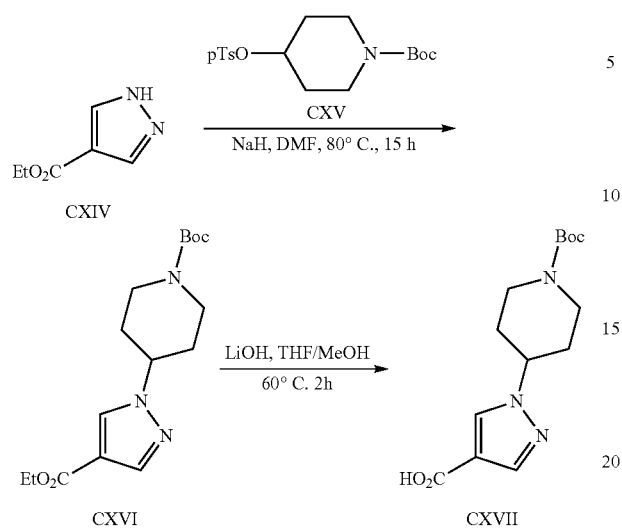

Step 1

To a suspension of NaH (0.24 g, 5.99 mmol) in DMF (15 mL) at 0° C. under argon was added ethyl 1H-pyrazole-4-carboxylate (CXIV) (0.7 g, 5 mmol). After stirring for 30 min, tert-butyl 4-(p-tolylsulfonyloxy)piperidine-1-carboxylate (CXV) (2.13 g, 5.99 mmol) was added and the mixture heated at 80° C. for 1 h. The reaction was poured into water and extracted with EtOAc. The organic layer was washed with brine, dried, filtered and concentrated under vacuum. The crude product was purified by silica gel chromatography (0→40% EtOAc/Hexanes) to afford tert-butyl 4-(4-(ethoxycarbonyl)-1H-pyrazol-1-yl)piperidine-1-carboxylate (CXVI) as a white solid (1.25 g, 3.87 mmol, 77.4% yield). ESIMS found for $C_{16}H_{25}N_3O_4$ m/z 346.2 (M+Na).

Step 2

To a solution of tert-butyl 4-(4-(ethoxycarbonyl)-1H-pyrazol-1-yl)piperidine-1-carboxylate (CXVI) (1.25 g, 3.87 mmol) in MeOH (4 mL) and THF (4 mL) was added LiOH (3.87 mL, 15.46 mmol). The reaction stirred at 60° C. for 2 h. The mixture was concentrated, and the residue triturated in water. The solution was acidified with 2 N HCl and the resulting solid was filtered to afford 1-(1-(tert-butoxycarbonyl)piperidin-4-yl)-1H-pyrazole-4-carboxylic acid (CXVII) as a white solid (1.04 g, 3.52 mmol, 91.1% yield). ESIMS found for $C_{14}H_{21}N_3O_4$ m/z 318.1 (M+Na).

Preparation of intermediate 2-(1-(tert-butoxycarbonyl)piperidin-4-yl)oxazole-4-carboxylic acid (CXXII) is depicted below in Scheme 26.

Scheme 26

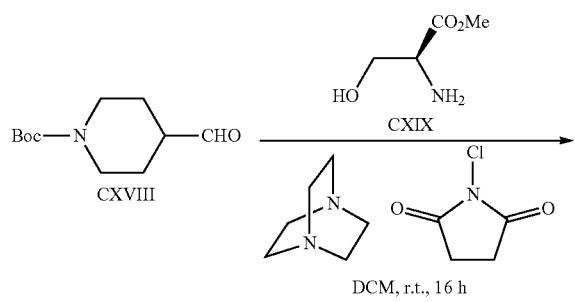

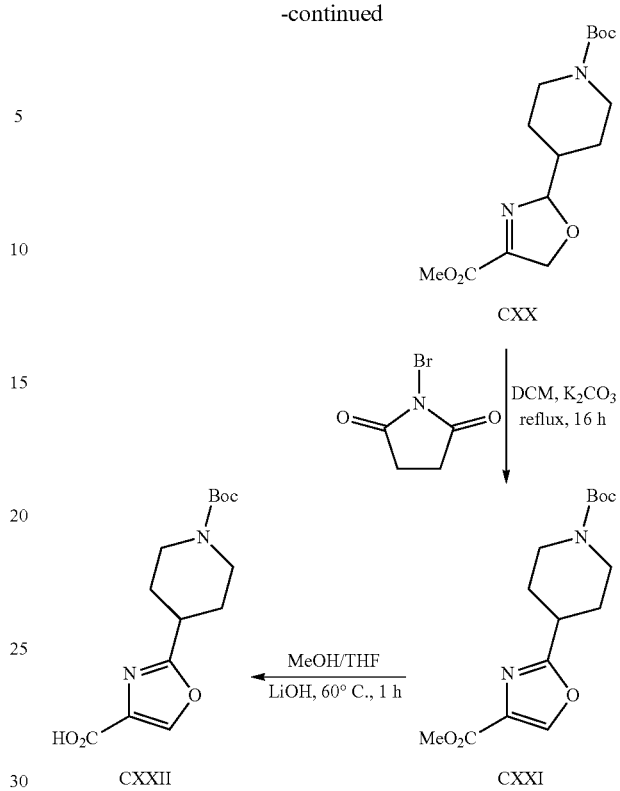

Step 1

To a suspension of methyl (2S)-2-amino-3-hydroxy-propanoate hydrochloride (CXIX) (3.21 g, 20.63 mmol) (1.1 eq) in DCM (40 mL) was added DABCO (6.31 g, 56.27 mmol) (3.0 eq). The reaction mixture was stirred at room temperature for 20 min before adding tert-butyl 4-formylpiperidine-1-carboxylate (CXVIII) (4.0 g, 18.76 mmol) (1.0 eq). The reaction mixture was stirred at room temperature for 30 min. The reaction mixture was cooled to 0° C., and 1-chloropyrrolidine-2,5-dione (2.75 g, 20.63 mmol) (1.1 eq) was added and stirred at the room temperature for 16 h. Saturated aqueous $Na_2S_2O_3$ was added to the reaction mixture and extracted with DCM. The organic layer was washed with saturated aqueous $NaHCO_3$ and brine, dried over $Na_2SO_4$, and evaporated in vacuo. The crude product was purified by silica gel chromatography (0→50% EtOAc/Hexanes) to afford methyl 2-(1-(tert-butoxycarbonyl)piperidin-4-yl)-2,5-dihydrooxazole-4-carboxylate (CXX) as a light brown oil (4.9 g, 15.7 mmol, 83.6% yield). ESIMS found for $C_{15}H_{24}N_2O_5$ m/z 213.1 (M+H-Boc).

Step 2

To a suspension of methyl 2-(1-(tert-butoxycarbonyl)piperidin-4-yl)-2,5-dihydrooxazole-4-carboxylate (CXX) (3.63 g, 20.39 mmol) (4.9 g, 15.69 mmol) and $K_2CO_3$ (2.82 g, 20.39 mmol) in DCM (50 mL) was added 1-bromopyrrolidine-2,5-dione (3.63 g, 20.39 mmol). The reaction mixture heated at reflux for 16 h. Water (100 mL) was then added and the mixture extracted with DCM. The organic layer was separated, washed with brine, dried over $Na_2SO_4$, and evaporated in vacuo. The crude product was purified by silica gel chromatography (0→50% EtOAc/hexanes) to give methyl 2-(1-(tert-butoxycarbonyl)piperidin-4-yl)oxazole-4-carboxylate (CXXI) as a light brown oil (3.7 g, 11.92 mmol, 76.0% yield). ESIMS found for $C_{15}H_{22}N_2O_5$ m/z 333.10 (M+Na).

Step 3

To a solution of methyl 2-(1-(tert-butoxycarbonyl)piperidin-4-yl)-2,5-dihydrooxazole-4-carboxylate (CXXI) in MeOH (20 mL) and THF (20 mL) was added 3 M aqueous LiOH (11.54 mL, 34.61 mmol). The mixture stirred at 60° C. for 1 h. The mixture was then concentrated to remove the organic solvents. The residual water was acidified with 2 N HCl and the mixture extracted with EtOAc. The organic layer was washed with brine, dried, filtered and concentrated to afford 2-(1-(tert-butoxycarbonyl)piperidin-4-yl)oxazole-4-carboxylic acid (CXXII) as a brown foam (4.6 g, 15.52 mmol, 89.7% yield). ESIMS found for $C_{14}H_{20}N_2O_5$ m/z 319.10 (M+Na).

Preparation of intermediate 2-(3-(dimethylamino)azetidin-1-yl)thiazole-4-carboxylic acid (CXXVII) is depicted below in Scheme 27.

Step 2

To a suspension of tert-butyl 2-chlorothiazole-4-carboxylate (CXXIV) (265 mg, 1.21 mmol) in DMSO (10 mL) was added N,N-dimethylazetidin-3-amine (CXXV) (313.2 mg, 1.81 mmol) and DIPEA (1.05 mL, 6.03 mmol). The mixture was heated at reflux for 1 day and the mixture was cooled to room temperature. The reaction was poured into water and the aqueous layer was extracted with EtOAc. The organic layer was dried and evaporated under vacuum. The residue was purified by column chromatography (0→40% 20% MeOH (7 N NH$_3$)—CHCl$_3$/CHCl$_3$) to afford tert-butyl 2-(3-(dimethylamino)azetidin-1-yl)thiazole-4-carboxylate (CXXVI) as a brown oil (67 mg, 0.24 mmol, 19.6% yield). ESIMS found for $C_{13}H_{21}N_3O_2S$ m/z 284.1 (M+H).

Step 3

To a stirred solution of tert-butyl 2-(3-(dimethylamino)azetidin-1-yl)thiazole-4-carboxylate (CXXVI) (200 mg, Scheme 27

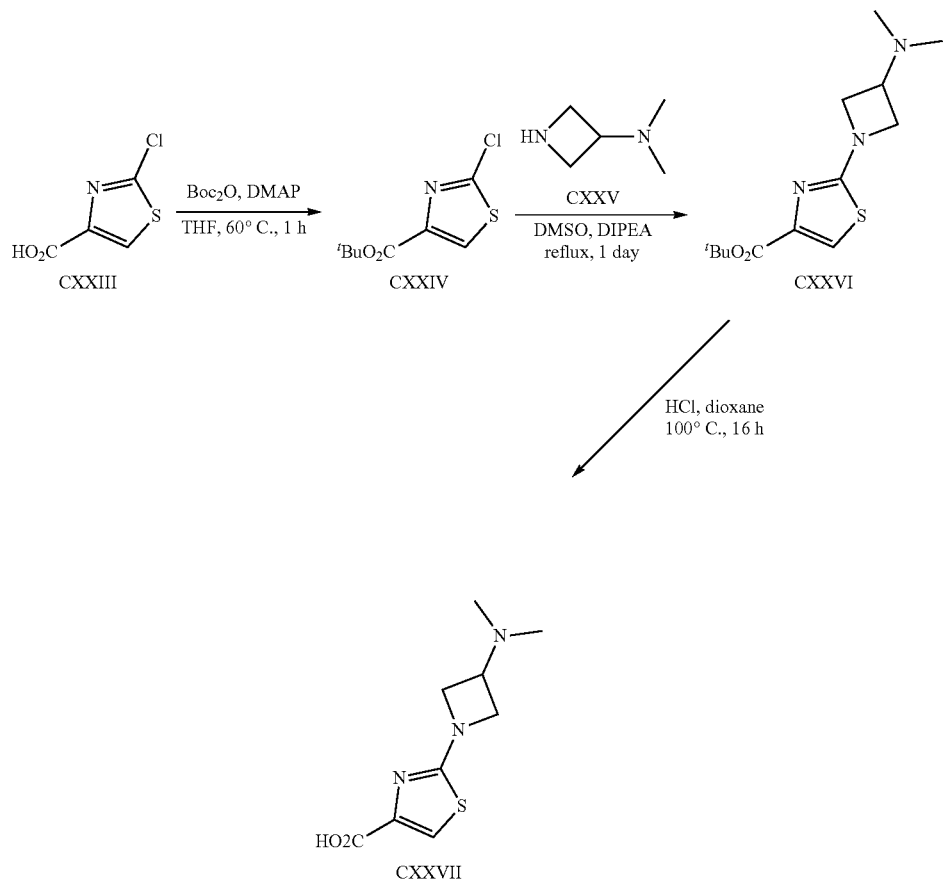

0.71 mmol) in dioxane (15 mL) was added HCl (4 N in dioxane) (1.76 mL, 7.06 mmol). The reaction was heated at 100° C. for 16 h. The white solid was filtered and washed with MTBE, brine and dried to produce 2-(3-(dimethylamino)azetidin-1-yl)thiazole-4-carboxylic acid (CXXVII) as a white solid (450 mg, 1.50 mmol, 212% yield). ESIMS found for $C_9H_{13}N_3O_2S$ m/z 228.1 (M+H).

The following intermediate was prepared in accordance with the procedure described in the above Scheme 27.

Step 1

To a solution of 2-chlorothiazole-5-carboxylic acid (CXXIII) (1.0 g, 6.11 mmol), di-tert-butyl dicarbonate (3.07 g, 14.06 mmol) in THF (19.8 mL) was added DMAP (0.15 g, 1.22 mmol). The reaction was heated at 60° C. for 1 h. The solvent was removed under vacuum and the residue was purified by silica gel (40 g) (0→50% EtOAc/hexanes) to produce tert-butyl 2-chlorothiazole-4-carboxylate (CXXIV) as a clear liquid (1.05 g, 4.79 mmol, 78.4% yield). ESIMS found for $C_8H_{10}ClNO_2S$ m/z 220.0 (M+H).

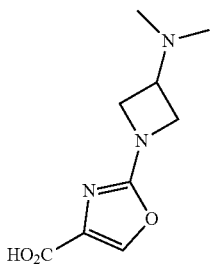

CXXVIII 2-(3-(Dimethylamino)azetidin-1-yl)oxazole-4-carboxylic acid (CXXVIII): White solid, (543.9 mg, 1.91 mmol, 90.1% yield). ESIMS found $C_9H_{13}N_3O_3$ m/z 212.0 (M+H).

Preparation of intermediate 1-(methyl-d3)-4-(4,4,5,5-tetramethyl-1,3,2-dioxaborolan-2-yl)-1H-pyrazole (CXXX) is depicted below in Scheme 28.

Scheme 28

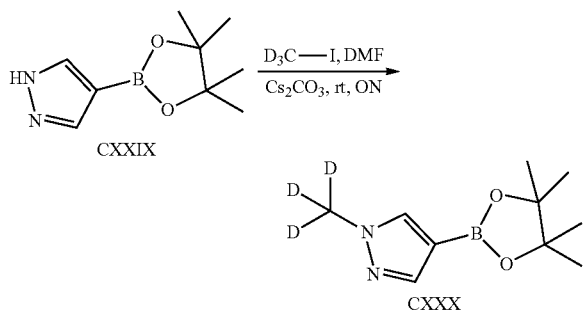

CXXIX

CXXX

Step 1

To a stirred suspension of 4-(4,4,5,5-tetramethyl-1,3,2-dioxaborolan-2-yl)-1H-pyrazole (CXXIX) (1.435 g, 7.4 mmol) and $Cs_2CO_3$ (2.89 g, 8.87 mmol) in DMF (15 mL) was added trideuterio(iodo)methane (0.51 mL, 8.13 mmol) and the mixture was stirred at room temperature overnight. The reaction mixture was filtered, and the filtrates were concentrated and dried under high vacuo to obtain 4-(4,4,5,5-tetramethyl-1,3,2-dioxaborolan-2-yl)-1-(trideuteriomethyl)pyrazole (CXXX) (3.9 g, 18.48 mmol, 249.8% yield) as a white solid which was used for next step without purification. ESIMS found for $C_{10}H_{14}[^2H_3]BN_2O_2$ m/z 212. (M+1).

Preparation of intermediate trans-4-[[tert-butyl(dimethyl)silyl]oxymethyl]cyclohexanecarboxylic acid (CXXXIII) is depicted below in Scheme 29.

Scheme 29

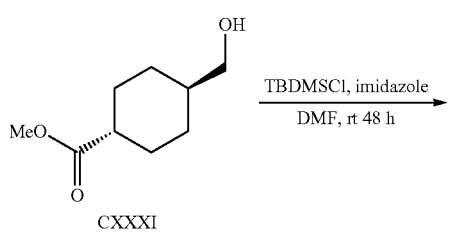

CXXXI

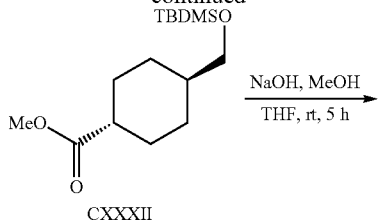

CXXXII

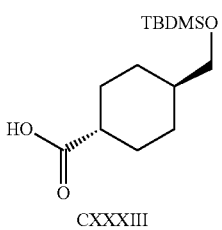

CXXXIII

Step 1

To a mixture of methyl trans-4-(hydroxymethyl)cyclohexanecarboxylate (CXXXI) (5.0 g, 29.03 mmol), imidazole (3.95 g, 58.07 mmol), and tert-butyl-chloro-dimethyl-silane (4.81 g, 31.94 mmol) in DMF (50 mL) was stirred at room temperature for 48 h. The solvents were concentrated to ½ volume, water (200 mL) was added and extracted with MTBE. The organic layer was separated and washed with 1 N HCl, $H_2O$ and brine. The organics were dried over anhydrous $Na_2SO_4$ and the solvent was concentrated to dryness to obtain methyl trans-4-[[tert-butyl(dimethyl)silyl]oxymethyl]cyclohexanecarboxylate (CXXXII) (8.09 g, 28.24 mmol, 97.3% yield) as a colorless oil. ESIMS found for $C_{15}H_{30}O_3Si$ m/z 287.1 (M+1).

Step 2

To a stirred solution of methyl trans-4-[[tert-butyl(dimethyl)silyl]oxymethyl]cyclohexanecarboxylate (CXXXII) (8.05 g, 28.1 mmol) in a mixture of THF (20 mL) and MeOH (20 mL) was added 2 M solution of NaOH (28.1 mL, 56.2 mmol). The mixture was stirred at room temperature for 5 h. The solvent was reduced to ⅓ volume, acidified with 1 N HCl and the resulting solid was filtered, washed with water and dried under high vacuo to obtain 5 grams of the desired product. The filtrates were extracted with EtOAc (2×), washed with water, brine, dried over anhydrous $Na_2SO_4$, concentrated, and dried in vacuo to obtain another 1.1 g of trans-4-[[tert-butyl(dimethyl)silyl]oxymethyl]cyclohexanecarboxylic acid (CXXXIII) (Total 6.1 g, 22.39 mmol, 79.7% yield) as a white solid. $^1H$ NMR (499 MHz, DMSO-$d_6$) δ ppm 0.01 (6H, s), 0.83-0.87 (8H, m), 0.88-0.96 (2H, m), 1.19-1.32 (2H, m), 1.32-1.43 (1H, m), 1.74 (2H, br dd, J=13.31, 3.16 Hz), 1.84-1.94 (2H, m), 2.09 (1H, tt, J=12.18, 3.46 Hz), 3.38 (2H, d, J=6.31 Hz), 11.98 (1H, br s); ESIMS found for $C_{14}H_{28}O_3Si$ m/z 273.1 (M+1).

Example 1

Preparation of N-(2-(1-methyl-1H-pyrazol-4-yl)-1,6-naphthyridin-7-yl)-4-((1-methylpiperidin-4-yl)oxy)benzamide (145), is depicted below in Scheme 30.

Scheme 30

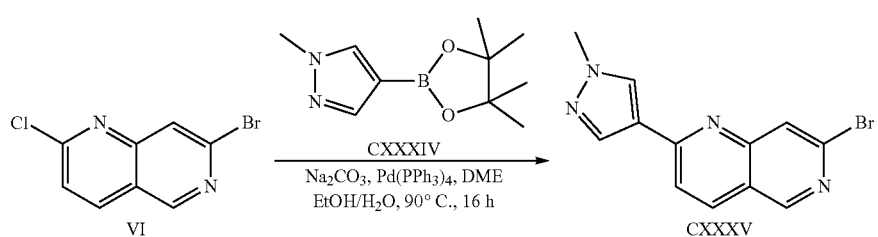

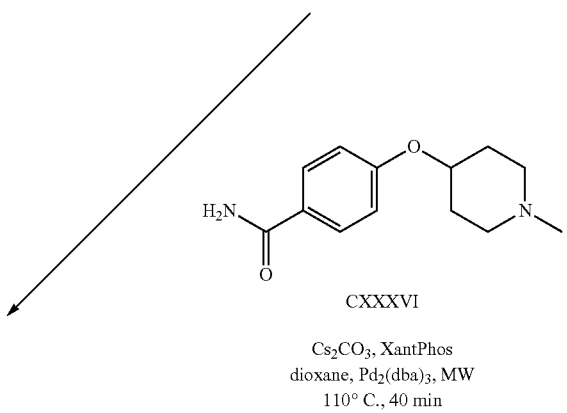

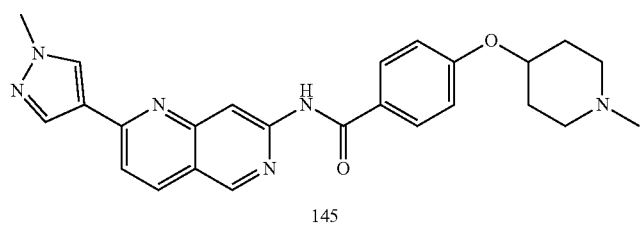

145

Step 1

To a solution of 7-bromo-2-chloro-1,6-naphthyridine (VI) (240 mg, 0.99 mmol) in DME (3 mL) and EtOH (4 mL) was added 1-methyl-4-(4,4,5,5-tetramethyl-1,3,2-dioxaborolan-2-yl)-1H-pyrazole (CXXXIV) (246 mg, 1.18 mmol), Na$_2$CO$_3$ (313 mg, 2.96 mmol) in water (2 mL). The mixture was purged with argon for 1 min before adding Pd(PPh$_3$)$_4$ (114 mg, 0.10 mmol). The reaction was heated at 90° C. for 16 h. The reaction was washed with EtOAc-brine and purified by silica column chromatography (0→100% EtOAc-hexanes) to give 7-bromo-2-(1-methyl-1H-pyrazol-4-yl)-1,6-naphthyridine (CXXXV) as a yellow solid (85 mg, 0.29 mmol, 29.8% yield). MS: 290.0 (M+1). $^1$H NMR (499 MHz, DMSO-d$_6$) δ ppm 3.94 (3H, s), 8.00-8.06 (2H, m), 8.24 (1H, s), 8.53 (1H, dd, J=8.78, 0.82 Hz), 8.57 (1H, s), 9.11 (1H, s); ESIMS found for C$_{12}$H$_9$BrN$_4$ m/z 289.0 (M+1).

Step 2

To a microwave tube was added 7-bromo-2-(1-methyl-1H-pyrazol-4-yl)-1,6-naphthyridine (CXXXV) (84 mg, 0.29 mmol), 4-((1-methylpiperidin-4-yl)oxy)benzamide (CXXXVI) (81.7 mg, 0.35 mmol), cesium carbonate (189 mg, 0.58 mmol), XantPhos (33.6 mg, 0.06 mmol), and Pd$_2$(dba)$_3$ (26.6 mg, 0.03 mmol) and 1,4-dioxane (2 mL). Argon gas was bubbled into the mixture for 1 min and then the mixture was heated under microwave irradiation at 110° C. for 40 min. The reaction mixture was washed with EtOAc-brine. The organics were combined and dried over Na$_2$SO$_4$, concentrated in vacuo and the crude was purified by prep TLC (10% NH$_3$/MeOH in CHCl$_3$). The pure fraction band were cut and washed with 10% NH$_3$/MeOH in CHCl$_3$ and filtered. The solvent was concentrated and dried under high vacuum to obtain 4-[(1-methyl-4-piperidyl)oxy]-N-[2-(1-methylpyrazol-4-yl)-1,6-naphthyridin-7-yl]benzamide 145 (12.8 mg, 0.03 mmol, 10.0% yield) as a yellow solid. $^1$H NMR (499 MHz, DMSO-d$_6$) δ ppm 1.62-1.72 (2H, m), 1.91-2.01 (2H, m), 2.14-2.25 (2H, m), 2.18 (3H, s), 2.57-2.66 (2H, m), 3.94 (3H, s), 4.51 (1H, tt, J=8.20, 4.01 Hz), 7.03-7.09 (2H, m), 7.84 (1H, d, J=8.78 Hz), 8.07 (2H, d, J=8.78 Hz), 8.24 (1H, d, J=0.82 Hz), 8.43 (1H, dd, J=8.51, 0.82 Hz), 8.58 (1H, s), 8.62 (1H, s), 9.13 (1H, d, J=0.82 Hz), 10.78 (1H, s); ESIMS found for C$_{25}$H$_{26}$N$_6$O$_2$ m/z 443.2 (M+1).

Example 2

Preparation of (S)—N-(2-(1-methyl-1H-pyrazol-4-yl)-1,6-naphthyridin-7-yl)-2-(2-methylpyrrolidin-1-yl)acetamide (47), is depicted below in Scheme 31.

Scheme 31

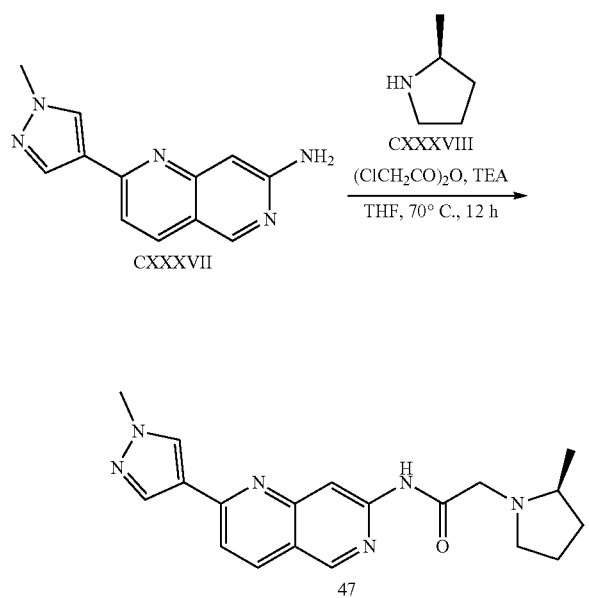

Step 1

To a stirred solution of 2-(1-methyl-1H-pyrazol-4-yl)-1,6-naphthyridin-7-amine (CXXXVII) (50 mg, 0.22 mmol) and TEA (80 µL, 0.55 mmol) in dry THF (5 mL) was chloroacetic anhydride (45.5 mg, 0.27 mmol) and the mixture was heated with microwave irradiation at 70° C. for 1 h. (2S)-2-Methylpyrrolidine (CXXXVIII) (38 mg, 0.44 mmol) was then added and the mixture was stirred at 70° C. for 12 h. Reaction mixture was concentrated and the resulting crude was purified by column chromatography (0→10% 7N $NH_3$ in $MeOH/CHCl_3$). The pure fractions were collected and concentrated the resulting solid was triturated with EtOAc to obtain (S)—N-(2-(1-methyl-1H-pyrazol-4-yl)-1,6-naphthyridin-7-yl)-2-(2-methylpyrrolidin-1-yl)acetamide 47 as a beige solid (30 mg, 0.09 mmol, 38.6% yield). $^1$H NMR (499 MHz, DMSO-d) δ ppm 1.09 (3H, d, J=6.04 Hz), 1.41 (1H, dddd, J=12.25, 10.33, 8.44, 6.31 Hz), 1.68-1.84 (2H, m), 1.91-2.01 (1H, m), 2.40 (1H, q, J=8.69 Hz), 2.56-2.66 (1H, m), 3.14 (1H, d, J=16.19 Hz), 3.13-3.20 (1H, m), 3.56 (1H, d, J=16.19 Hz), 3.93 (3H, s), 7.84 (1H, d, J=8.51 Hz), 8.23 (1H, s), 8.41 (1H, d, J=8.78 Hz), 8.48 (1H, s), 8.58 (1H, s), 9.07 (1H, s), 10.02 (1H, s); ESIMS found for C m/z 351.2 (M+1).

Example 3

Preparation of trans-4-amino-N-(2-(1-methyl-1H-pyrazol-4-yl)-1,6-naphthyridin-7-yl)cyclohexane-1-carboxamide (41) and trans-N-(2-(1-methyl-1H-pyrazol-4-yl)-1,6-naphthyridin-7-yl)-4-morpholinocyclohexane-1-carboxamide (5) are depicted below in Scheme 32.

Scheme 32

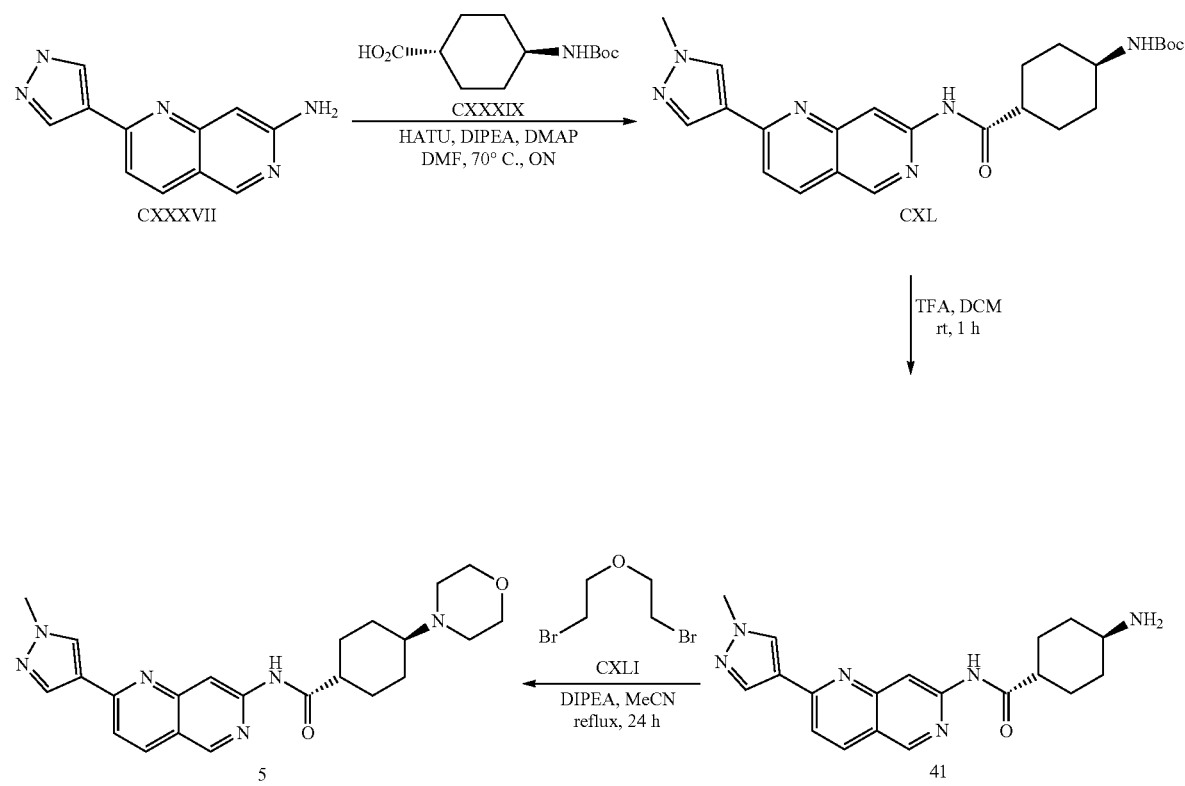

Step 1

A mixture of trans-4-((tert-butoxycarbonyl)amino)cyclohexane-1-carboxylic acid (CXXXIX) (supplier: Combi-Blocks) (324 mg, 1.33 mmol), DIEA (0.58 mL, 3.33 mmol) and HATU (506 mg, 1.33 mmol) in DMF (4 mL) was stirred for 5 min before adding 2-(1-methyl-1H-pyrazol-4-yl)-1,6-naphthyridin-7-amine (CXXXVII) (250 mg, 1.11 mmol) and the mixture was heated to 80° C. overnight. The reaction mixture was diluted with water, extracted with EtOAc, washed with saturated aqueous NaHCO$_3$, and brine. The organics were separated and concentrated in vacuo. The residue was suspended in EtOAc, sonicated and the solids were collected by filtration and dried under high vacuo to obtain tert-butyl (trans-4-((2-(1-methyl-1H-pyrazol-4-yl)-1,6-naphthyridin-7-yl)carbamoyl)cyclohexyl) carbamate (CXL) as an off-white solid (304 mg, 0.67 mmol, 60.8% yield). $^1$H NMR (499 MHz, DMSO-d$_6$) δ ppm 1.15-1.26 (2H, m), 1.39 (9H, s), 1.43-1.54 (2H, m), 1.86 (4H, brt, J=13.17 Hz), 2.44-2.49 (1H, m), 3.17-3.26 (1H, m), 3.93 (3H, s), 6.75 (1H, br d, J=7.68 Hz), 7.81 (1H, d, J=8.51 Hz), 8.21 (1H, s), 8.36-8.41 (1H, m), 8.46 (1H, s), 8.55 (1H, s), 9.05 (1H, s), 10.57 (1H, s); ESIMS found for C$_{24}$H$_{30}$N$_6$O$_3$ m/z 451.3 (M+1).

Step 2

To a stirred solution of tert-butyl (trans-4-((2-(1-methyl-1H-pyrazol-4-yl)-1,6-naphthyridin-7-yl)carbamoyl)cyclohexyl) carbamate (CXL) (300 mg, 0.67 mmol) in DCM (3 mL) was added TFA (1.0 mL, 12.98 mmol) and the mixture was stirred for 1 h. The solvent was concentrated, treated with 7N NH$_3$/MeOH, absorbed on silica gel and was purified by ISCO (10→100% CHCl$_3$/10% 7 N NH$_3$ MeOH in CHCl$_3$) to obtain trans-4-amino-N-(2-(1-methyl-1H-pyrazol-4-yl)-1,6-naphthyridin-7-yl)cyclohexane-1-carboxamide 41 as a white solid (233 mg, 0.66 mmol, 99.9% yield). $^1$H NMR (499 MHz, DMSO-d$_6$) δ ppm 1.00-1.10 (2H, m), 1.48 (2H, qd, J=12.85, 3.16 Hz), 1.79-1.87 (4H, m), 2.44-2.55 (2H, m), 3.93 (3H, s), 7.80 (1H, d, J=8.51 Hz), 8.21 (1H, s), 8.38 (1H, dd, J=8.60, 0.50 Hz), 8.47 (1H, s), 8.55 (1H, s), 9.05 (1H, s), 10.57 (1H, s); ESIMS found for C m/z 351.2 (M+1).

Step 3

A mixture of trans-4-amino-N-(2-(1-methyl-1H-pyrazol-4-yl)-1,6-naphthyridin-7-yl)cyclohexane-1-carboxamide 41 (110 mg, 0.31 mmol), 1-bromo-2-(2-bromoethoxy)ethane (CXLI) (80.1 mg, 0.35 mmol), and DIPEA (137 μL, 0.79 mmol) in MeCN (2 mL) was stirred at 90° C. for 24 h. The solvents were concentrated, and the residue taken in CHCl$_3$, washed with water and brine. The organic layer was dried over anhydrous Na$_2$SO$_4$ and evaporated to dryness under vacuum. The crude product was purified by preparative TLC (60% CHCl$_3$/10% 7 N NH$_3$ MeOH in CHCl$_3$) to obtain trans-N-(2-(1-methyl-1H-pyrazol-4-yl)-1,6-naphthyridin-7-yl)-4-morpholinocyclohexane-1-carboxamide 5 as an off-white solid (89 mg, 0.21 mmol, 67.4% yield). $^1$H NMR (499 MHz, DMSO-d$_6$) δ ppm 1.16-1.29 (2H, m), 1.43-1.56 (2H, m), 1.87-1.97 (4H, m), 2.18-2.26 (1H, m), 2.45-2.49 (4H, m), 2.51-2.54 (1H, m), 3.53-3.59 (4H, m), 3.93 (3H, s), 7.80 (1H, d, J=8.51 Hz), 8.21 (1H, s), 8.38 (1H, d, J=8.78 Hz), 8.47 (1H, s), 8.55 (1H, s), 9.05 (1H, s), 10.58 (1H, s); ESIMS found for C m/z 421.3 (M+1).

Example 4

Preparation of N-(2-(6-(isopropylamino)pyrazin-2-yl)-1,6-naphthyridin-7-yl)-1-(piperidin-4-yl)-1H-1,2,3-triazole-4-carboxamide (862) and 1-(1-(2-fluoroethyl)piperidin-4-yl)-N-(2-(6-(isopropylamino)pyrazin-2-yl)-1,6-naphthyridin-7-yl)-1H-1,2,3-triazole-4-carboxamide (863) are depicted below in Scheme 33.

Scheme 33

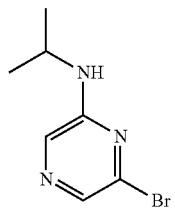

LXXVIII

Sn$_2$Bu$_6$, LiCl
dioxane, Pd(PPh$_3$)$_4$
MW, 120° C., 1 h

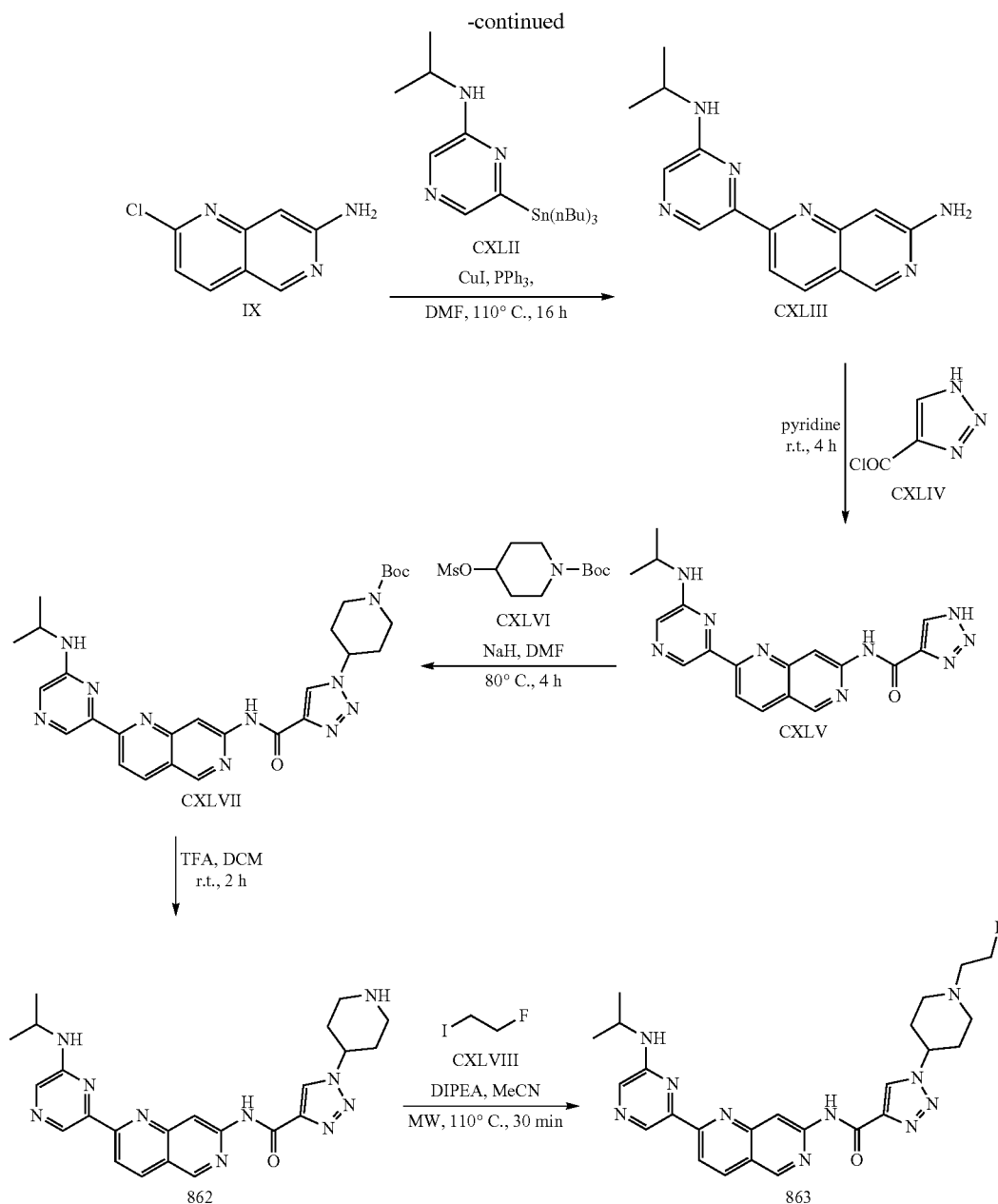

Step 1

To a microwave tube was added bis(tributyltin) (0.76 mL, 1.5 mmol), Pd(PPh$_3$)$_4$ (26 mg, 0.02 mmol), and 1,4-dioxane (10 mL). The mixture was purged with argon for 1 min before adding 6-bromo-N-isopropylpyrazin-2-amine (LXXVIII) (221 mg, 1.02 mmol) and LiCl (130 mg, 3.07 mmol). The reaction was heated microwave irradiation at 120° C. for 1 h. The reaction was washed with saturated NaHCO$_3$-EtOAc. The organic layers were dried the product was purified by silica column (0→70% [20% 7N NH$_3$-MeOH/EtOAc]/hexanes) to produce N-isopropyl-6-(tributylstannyl)pyrazin-2-amine (CXLII) as a white solid (302 mg, 0.71 mmol, 69.3% yield). ESIMS found for C$_{19}$H$_{37}$N$_3$Sn m/z 428.1 (M+1).

Step 2

To a sealed tube was added N-isopropyl-6-(tributylstannyl)pyrazin-2-amine (CXLII) (285 mg, 0.67 mmol), 2-chloro-1,6-naphthyridin-7-amine (IX) (120 mg, 0.67 mmol), and DMF (2 mL). The mixture was purged with argon for 1 min before adding CuI (25.4 mg, 0.13 mmol) and Pd(PPh$_3$)$_4$ (77.5 mg, 0.07 mmol). The reaction was heated using microwave irradiation at 125° C. for 1 h. The reaction was worked-up with saturated NaHCO$_3$-EtOAc extraction. The organic layers were separated, dried over NaSO$_4$ and evaporated to dryness. The residue was purified by silica column (0→70% [20% 7N NH$_3$-MeOH/EtOAc]/hexanes) to produce 2-(6-(isopropylamino) pyrazin-2-yl)-1,6-naphthyridin-7-amine (CXLIII) as a black wax (70 mg, 0.25 mmol, 37.4% yield). ESIMS found for C$_{15}$H$_{16}$N$_6$ m/z 281.2 (M+1).

Step 3

To a solution of 2-(6-(isopropylamino)pyrazin-2-yl)-1,6-naphthyridin-7-amine (CXLIII) (70 mg, 0.25 mmol) in pyridine (3 mL) was added 1H-1,2,3-triazole-4-carbonyl chloride (CXLIV) (59 mg, 0.45 mmol). The reaction was stirred at room temperature for 4 h. The reaction was worked-up with saturated NaHCO$_3$-EtOAc extraction. The organic layers were separated, dried over NaSO$_4$ and evaporated to dryness. The residue was purified by silica column (0→20% 7 N NH$_3$ in MeOH—CHCl$_3$) to give N-(2-(6-(isopropylamino)pyrazin-2-yl)-1,6-naphthyridin-7-yl)-1H-1,2,3-triazole-4-carboxamide (CXLV) as a white solid (9 mg, 0.02 mmol, 9.6% yield). ESIMS found for C$_{18}$H$_{17}$N$_9$O m/z 376.2 (M+1).

Step 4

To a suspension of N-(2-(6-(isopropylamino)pyrazin-2-yl)-1,6-naphthyridin-7-yl)-1H-1,2,3-triazole-4-carboxamide (CXLV) (22 mg, 0.06 mmol) in DMF (1 mL) at 0° C. under argon was added NaH (8.4 mg, 0.21 mmol). After stirring for 15 min, tert-butyl 4-((methylsulfonyl)oxy)piperidine-1-carboxylate (CXLVI) (20 mg, 0.07 mmol) was added and the mixture stirred at 80° C. for 4 h. The reaction was poured into water and extracted with EtOAc. The organic layer was washed with brine; dried over Na$_2$SO$_4$, filtered and concentrated. The crude product was purified by silica gel chromatography (0→70% EtOAc/hexanes) to afford tert-butyl 4-(4-((2-(6-(isopropylamino)pyrazin-2-yl)-1,6-naphthyridin-7-yl)carbamoyl)-1H-1,2,3-triazol-1-yl) piperidine-1-carboxylate (CXLVII) as a white solid (9 mg, 0.02 mmol, 27.5% yield). ESIMS found for C$_{28}$H$_{34}$N$_{10}$O$_3$ m/z 559.3 (M+1).

Step 5

To a solution of tert-butyl 4-(4-((2-(6-(isopropylamino) pyrazin-2-yl)-1,6-naphthyridin-7-yl)carbamoyl)-1H-1,2,3-triazol-1-yl) piperidine-1-carboxylate (CXLVII) (9 mg, 0.02 mmol) in DCM (2 mL) was added TFA (6.3 µL, 0.08 mmol). The solution was stirred at room temperature for 2 h. The reaction was worked-up with 2 N aqueous NaOH/EtOAc extraction. The organic layers were separated, dried over NaSO$_4$ and evaporated to dryness. The residue was purified by column chromatography (0→20% 7N NH$_3$-MeOH/CHCl$_3$) to yield N-(2-(6-(isopropylamino)pyrazin-2-yl)-1,6-naphthyridin-7-yl)-1-(piperidin-4-yl)-1H-1,2,3-triazole-4-carboxamide 862 as a yellow solid (2.2 mg, 0.005 mmol, 28.3% yield). $^1$H NMR (499 MHz, METHANOL-d$_4$) δ ppm 1.33 (6H, d, J=6.59 Hz), 2.16-2.25 (2H, m), 2.27-2.35 (2H, m), 2.85-2.93 (2H, m), 3.26 (2H, dt, J=13.04, 3.50 Hz), 4.31 (1H, spt, J=6.40 Hz), 4.78-4.83 (1H, m), 7.94 (1H, s), 8.28 (1H, s), 8.49-8.54 (1H, m), 8.54-8.59 (1H, m), 8.83 (1H, s), 8.85 (1H, s), 9.19 (1H, s); ESIMS found for C$_{23}$H$_{26}$N$_{10}$O m/z 459.3 (M+1).

Step 6

A suspension of N-(2-(6-(isopropylamino)pyrazin-2-yl)-1,6-naphthyridin-7-yl)-1-(piperidin-4-yl)-1H-1,2,3-triazole-4-carboxamide 862 (9 mg, 0.02 mmol), DIPEA (10.3 µL, 0.06 mmol) and 1-fluoro-2-iodo-ethane (CXLVIII) (3.2 µL, 0.04 mmol) in MeCN (2 mL) was heated with microwave irradiation in a sealed tube at 110° C. for 30 min. The mixture was concentrated, and the crude product purified by column chromatography (0→5% 7 N NH$_3$-MeOH/CHCl$_3$). The fractions containing the product were concentrated and the residue triturated in ether and the resulting solid was filtered and dried to afford 1-(1-(2-fluoroethyl)piperidin-4-yl)-N-(2-(6-(isopropylamino) pyrazin-2-yl)-1,6-naphthyridin-7-yl)-1H-1,2,3-triazole-4-carboxamide 863 as a yellow solid (1.1 mg, 0.002 mmol, 11.1% yield). $^1$H NMR (499 MHz, METHANOL-d$_4$) δ ppm 1.33 (6H, d, J=6.59 Hz), 2.25-2.38 (4H, m), 2.40-2.49 (2H, m), 2.80 (2H, dt, J=28.40, 4.70 Hz), 3.10-3.15 (2H, m), 4.30 (1H, dt, J=13.00, 6.60 Hz), 4.62 (2H, dt, J=47.90, 4.70 Hz), 7.94 (1H, s), 8.27 (1H, s), 8.51-8.54 (1H, m), 8.55 (1H, s), 8.83 (1H, s), 8.84 (1H, s), 9.19 (1H, s); ESIMS found for C$_{25}$H$_{29}$FN$_{10}$O m/z 505.3 (M+1).

Example 5

Preparation of N-(7-(1-methyl-1H-pyrazol-4-yl)quinazolin-2-yl)piperidine-4-carboxamide (918) and 1-isobutyl-N-(7-(1-methyl-1H-pyrazol-4-yl)quinazolin-2-yl)piperidine-4-carboxamide (923) are depicted below in Scheme 34.

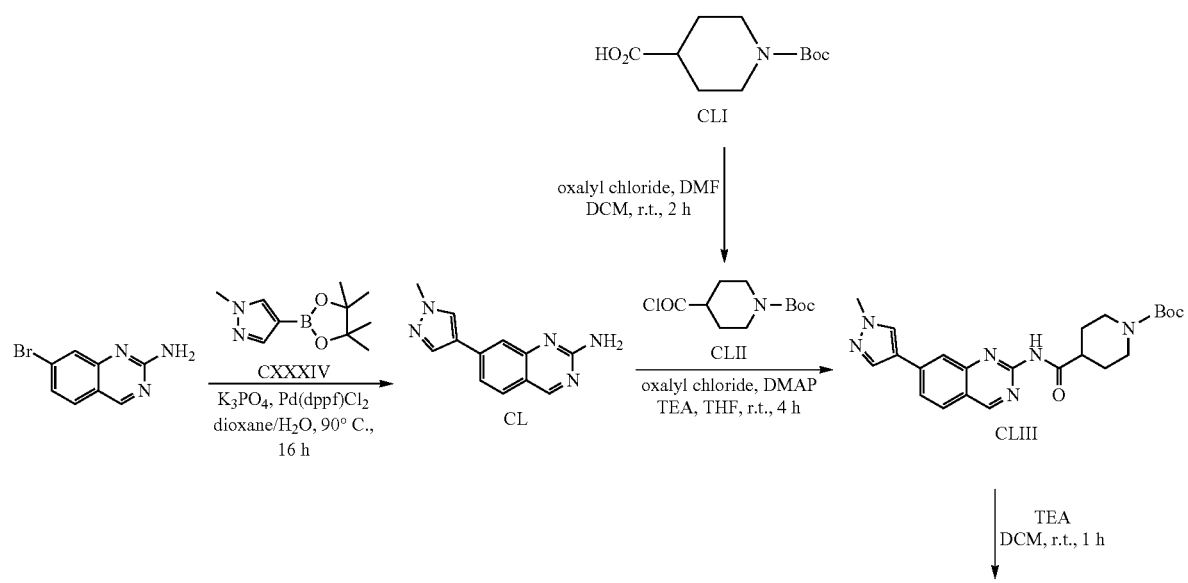

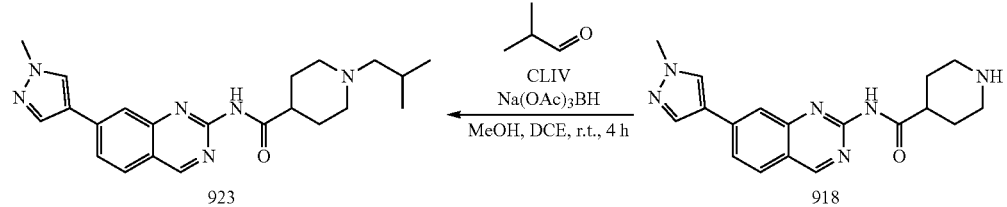

Step 1

A mixture of 7-bromoquinazolin-2-amine (CXLIX) (Supplier: CombiBlocks) (2.01 g, 8.97 mmol), 1-methyl-4-(4,4,5,5-tetramethyl-1,3,2-dioxaborolan-2-yl)-1H-pyrazole (XCXXXIV) (2.33 g, 11.21 mmol), Pd(dppf)Cl$_2$ (1.32 g, 1.61 mmol), and K$_3$PO$_4$ (11.21 mL, 22.41 mmol) in 1,4-dioxane (35 mL) was purged with N$_2$ gas for 15 min and then was heated to 90° C. for 16 h. The reaction mixture was added to water (300 mL), stirred for 1 h. The precipitate was collected by filtration and purified by ISCO (25→100% CHCl$_3$/10% 7N NH$_3$ MeOH in CHCl$_3$) to obtain 7-(1-methyl-1H-pyrazol-4-yl)quinazolin-2-amine (CL) as a grey solid (1.4 g, 6.22 mmol, 69.3% yield). ESIMS found for C$_{12}$H$_{11}$N$_5$ m/z 226.1 (M+1).

Step 2

To a stirred solution of 1-(tert-butoxycarbonyl)piperidine-4-carboxylic acid (CLI) (309.5 mg, 1.35 mmol) in DCM (5 mL) was added TEA (0.38 mL, 2.7 mmol) and few drops of DMF followed by the addition of oxalyl chloride (0.23 mL, 2.7 mmol) at 0° C. The reaction mixture was stirred for 2 h allowing the temperature to warm from 0° C. to room temperature. The solvent was concentrated and dried under high vacuo to obtain the acid chloride (CLII).

The acid chloride obtained above in DCE was added to a stirring mixture of 7-(1-methyl-1H-pyrazol-4-yl)quinazolin-2-amine (CL) (150 mg, 0.67 mmol), TEA (0.38 mL, 2.7 mmol) and DMAP (33 mg, 0.27 mmol) in THF (5 mL). The mixture was heated to 50° C. overnight. The reaction mixture was absorbed on silica gel and purified by ISCO (10→50% CHCl$_3$/10% 7N NH$_3$ MeOH in CHCl$_3$) to obtain tert-butyl 4-((7-(1-methyl-1H-pyrazol-4-yl)quinazolin-2-yl)carbamoyl)piperidine-1-carboxylate (CLIII) as a light brown solid (109 mg, 0.25 mmol, 18.5% yield). ESIMS found for C$_{23}$H$_{28}$N$_6$O$_3$ m/z 437.2 (M+1).

Step 3

To a stirred solution of tert-butyl 4-((7-(1-methyl-1H-pyrazol-4-yl)quinazolin-2-yl)carbamoyl)piperidine-1-carboxylate (CLIII) (100 mg, 0.23 mmol) in DCM (1 mL) was added TFA (0.5 mL, 6.49 mmol) and the mixture was stirred for 1 h. The solvent was concentrated, treated with 7N NH$_3$/MeOH, absorbed on silica gel and was purified by column chromatography (10→100% CHCl$_3$/10% 7N NH$_3$ MeOH in CHCl$_3$). The pure fractions were combined, concentrated, and dried under high vacuo to obtain N-(7-(1-methyl-1H-pyrazol-4-yl)quinazolin-2-yl)piperidine-4-carboxamide 918 as a beige solid (57 mg, 0.17 mmol, 74.0% yield). $^1$H NMR (499 MHz, DMSO-d$_6$) δ ppm 1.50 (2H, qd, J=12.17, 3.84 Hz), 1.72 (2H, br d, J=11.53 Hz), 2.45-2.53 (2H, m), 2.74-2.83 (1H, m), 2.97 (2H, br d, J=12.08 Hz), 3.91 (3H, s), 7.82 (1H, dd, J=8.23, 1.65 Hz), 7.91 (1H, s), 8.01 (1H, d, J=8.23 Hz), 8.14 (1H, s), 8.45 (1H, s), 9.34 (1H, s), 10.53 (1H, s); ESIMS found for C$_{18}$H$_{20}$N$_6$O m/z 337.2 (M+1).

Step 4

To a stirred solution of N-(7-(1-methyl-1H-pyrazol-4-yl)quinazolin-2-yl) piperidine-4-carboxamide 918 (50 mg, 0.15 mmol) and isobutyraldehyde (CLIV) (0.02 mL, 0.22 mmol) in a mixture of MeOH (0.75 mL) and DCE (0.75 mL) was added Na(OAc)$_3$BH (63 mg, 0.30 mmol). The mixture was stirred at room temperature for 4 h. The reaction mixture was diluted with DCM, washed with saturated NaHCO$_3$ and brine solution. The organics were dried over anhydrous Na$_2$SO$_4$, solvents concentrated, and the residue was purified by preparative TLC (50% CHCl$_3$/10% 7N NH$_3$ MeOH in CHCl$_3$) to obtain 1-isobutyl-N-(7-(1-methyl-1H-pyrazol-4-yl)quinazolin-2-yl)piperidine-4-carboxamide 923 as a white solid (18.0 mg, 0.046 mmol, 30.9% yield). $^1$H NMR (499 MHz, DMSO-d$_6$) δ ppm 0.86 (6H, d, J=6.59 Hz), 1.59-1.70 (2H, m), 1.72-1.83 (3H, m), 1.85-1.93 (2H, m), 2.02 (2H, d, J=7.41 Hz), 2.62-2.72 (1H, m), 2.86 (2H, br d, J=11.53 Hz), 3.91 (3H, s), 7.83 (1H, dd, J=8.51, 1.65 Hz), 7.91 (1H, s), 8.01 (1H, d, J=8.23 Hz), 8.14 (1H, s), 8.45 (1H, s), 9.35 (1H, s), 10.58 (1H, s); ESIMS found for C$_{22}$H$_{28}$N$_6$O m/z 393.2 (M+1).

Example 6

Preparation of N-(7-(1-methyl-1H-pyrazol-4-yl)quinazolin-2-yl)-1-(methylsulfonyl)piperidine-4-carboxamide (979) and N-(7-(1-methyl-1H-pyrazol-4-yl)quinazolin-2-yl)-1-(pyrimidin-2-ylmethyl)piperidine-4-carboxamide (1007) are depicted below in Scheme 35.

Scheme 35

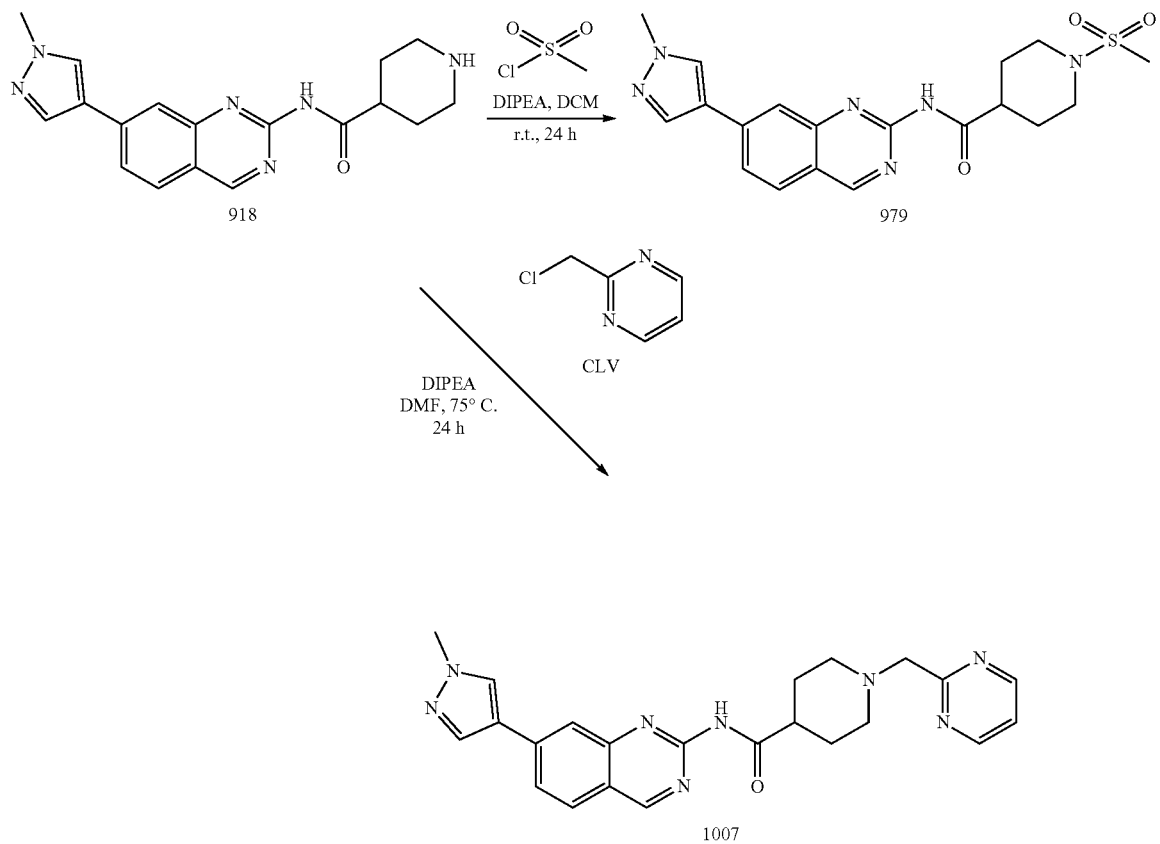

Step 1

A mixture of N-(7-(1-methyl-1H-pyrazol-4-yl)quinazolin-2-yl)piperidine-4-carboxamide 918 (60 mg, 0.18 mmol), methanesulfonyl chloride (20 µL, 0.19 mmol) and DIPEA (80 µL, 0.45 mmol) in DCM (1 mL) was stirred at room temperature for 24 h. The reaction mixture was diluted with EtOAc, washed with water, brine, dried over anhydrous Na$_2$SO$_4$, and concentrated. The crude product was purified by preparative TLC (60% 10% 7 N NH$_3$ MeOH in CHCl$_3$/CHCl$_3$) to obtain N-(7-(1-methyl-1H-pyrazol-4-yl)quinazolin-2-yl)-1-(methylsulfonyl)piperidine-4-carboxamide 979 as a beige solid (2 mg, 0.005 mmol, 2.6% yield). $^1$H NMR (499 MHz, DMSO-d$_6$) δ ppm 1.62-1.72 (2H, m), 1.97 (2H, br dd, J=13.17, 2.74 Hz), 2.78 (2H, td, J=11.94, 2.47 Hz), 2.82-2.88 (1H, m), 2.90 (3H, s), 3.59-3.66 (2H, m), 3.91 (3H, s), 7.84 (1H, dd, J=8.51, 1.65 Hz), 7.92 (1H, d, J=0.82 Hz), 8.02 (1H, d, J=8.51 Hz), 8.15 (1H, d, J=0.82 Hz), 8.45 (1H, s), 9.36 (1H, s), 10.72 (1H, s); ESIMS found for C$_{19}$H$_{22}$N$_6$O$_3$S m/z 415.1 (M+1).

Step 2

A mixture of N-(7-(1-methyl-1H-pyrazol-4-yl)quinazolin-2-yl)piperidine-4-carboxamide 918 (60 mg, 0.18 mmol), 2-(chloromethyl)pyrimidine (CLV) (34.4 mg, 0.27 mmol) and DIPEA (90 µL, 0.53 mmol) in DMF (0.75 mL) was stirred at 75° C. for 24 h. The reaction mixture was diluted with EtOAc, washed with water, brine, dried over anhydrous Na$_2$SO$_4$, and concentrated. The crude product was purified by preparative TLC (60% 10% 7 N NH$_3$ MeOH in CHCl$_3$/CHCl$_3$) to give N-(7-(1-methyl-1H-pyrazol-4-yl)quinazolin-2-yl)-1-(pyrimidin-2-ylmethyl)piperidine-4-carboxamide 1007 as a beige solid (23 mg, 0.05 mmol, 28.6% yield). $^1$H NMR (499 MHz, DMSO-d$_6$) δ ppm 1.65 (2H, qd, J=12.21, 3.70 Hz), 1.79 (2H, br d, J=10.70 Hz), 2.12-2.22 (2H, m), 2.61-2.69 (1H, m), 2.95 (2H, br d, J=11.53 Hz), 3.72 (2H, s), 3.91 (3H, s), 7.40 (1H, t, J=4.94 Hz), 7.82 (1H, dd, J=8.51, 1.65 Hz), 7.91 (1H, s), 8.01 (1H, d, J=8.23 Hz), 8.14 (1H, s), 8.44 (1H, s), 8.79 (2H, d, J=4.94 Hz), 9.34 (1H, s); ESIMS found for C$_{23}$H$_{24}$N$_8$O m/z 429.2 (M+1).

Example 7

Preparation of trans-4-(hydroxymethyl)-N-(7-(thiazol-5-yl)quinazolin-2-yl)cyclohexane-1-carboxamide (4586) and trans-4-((3-fluoroazetidin-1-yl)methyl)-N-(7-(thiazol-5-yl)quinazolin-2-yl)cyclohexane-1-carboxamide (1519) are depicted below in Scheme 36.

Scheme 36

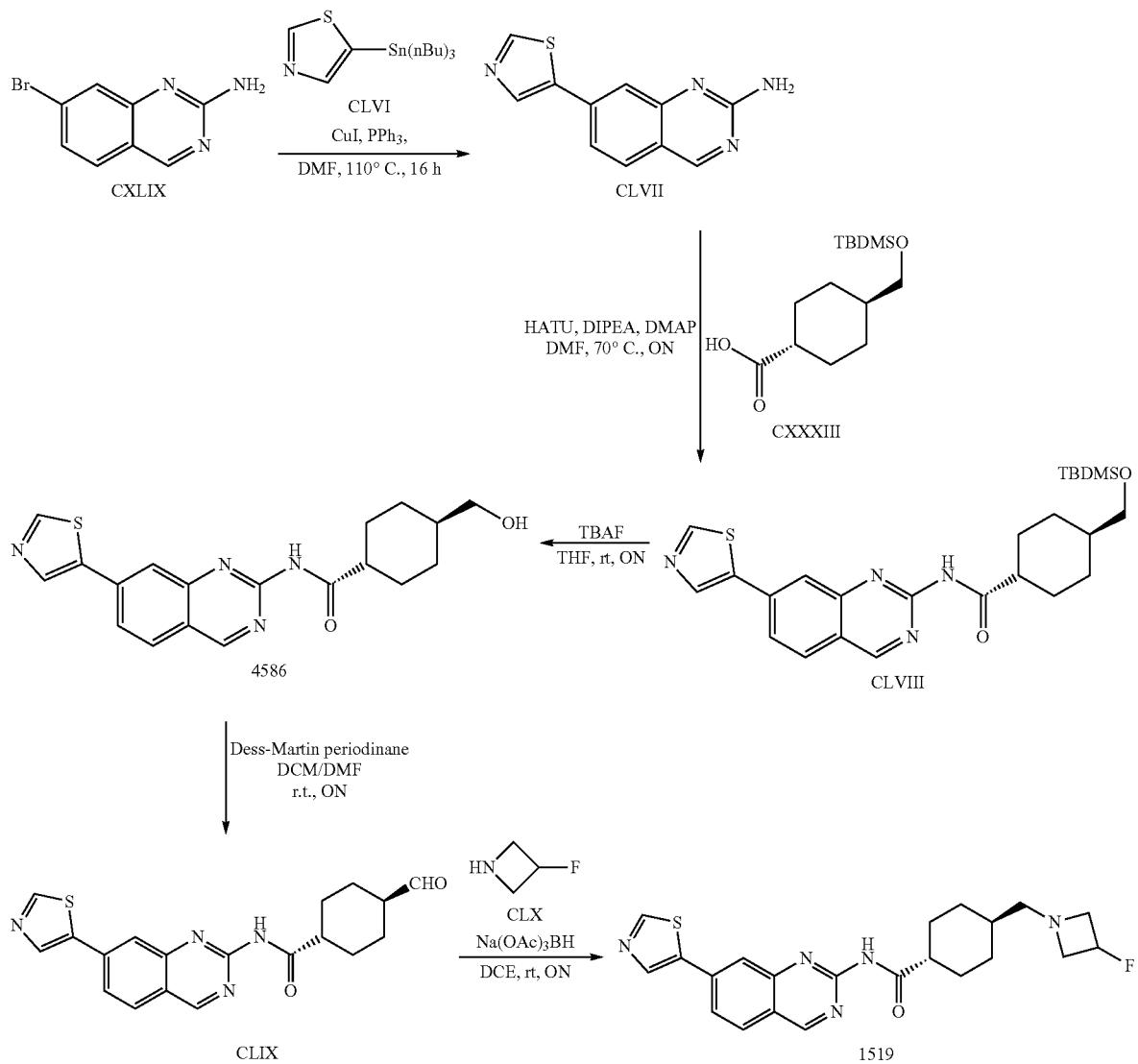

Step 1

To a sealed tube was added 5-(tributylstannyl)thiazole (CLVI) (supplier: CombiBlocks) (1.32 g, 3.51 mmol), copper(I)iodide (60 mg, 0.33 mmol), 2-amino-7-bromoquinazoline (CXLIX) (750 mg, 3.35 mmol) and PPh$_3$ (390 mg, 0.33 mmol) in DMF (12 mL). The mixture was purged with nitrogen for 1 min and then stirred at 110° C. for 16 h. The reaction was cooled to room temperature and filtered through Celite®. The filtrate was concentrated, and the residue purified by chromatography (0→15% 7 N NH$_3$-MeOH/CHCl$_3$). The fractions containing the product were concentrated, suspended in CHCl$_3$, the solid was collected by filtration and dried under high vacuo to afford 7-(thiazol-5-yl)quinazolin-2-amine (CLVII) as a brown solid (410 mg, 1.80 mmol, 53.7% yield). ESIMS found for C$_{11}$H$_8$N$_4$S m/z 229.0 (M+1).

Step 2

A mixture of DIPEA (0.94 mL, 5.39 mmol), DMAP (0.04 g, 0.36 mmol), HATU (0.85 g, 2.25 mmol), trans-4-(((tert-butyldimethylsilyl)oxy)methyl)cyclohexane-1-carboxylic acid (CXXXIII) (0.61 g, 2.25 mmol) and 7-(thiazol-5-yl)quinazolin-2-amine (CLVII) (0.41 g, 1.8 mmol) in DMF (10 mL) was stirred at 70° C. for 2 h. Then another equivalent of HATU was added and the mixture was stirred for another 2 h at the same temperature. The reaction mixture was then concentrated and the residue absorbed on silica and purified by ISCO (10→100% EtOAc/hexanes) to obtain trans-4-(((tert-butyldimethylsilyl)oxy)methyl)-N-(7-(thiazol-5-yl)quinazolin-2-yl) cyclohexane-1-carboxamide (CLVIII) as an off-white solid (425 mg, 0.88 mmol, 49.0% yield) which was used without further purification for the next step. ESIMS found for C$_{25}$H$_{34}$N$_4$O$_2$SSi m/z 483.2 (M+1).

Step 3

To a solution of trans-4-(((tert-butyldimethylsilyl)oxy)methyl)-N-(7-(thiazol-5-yl)quinazolin-2-yl)cyclohexane-1-carboxamide (CLVIII) (0.43 g, 0.88 mmol) in THF (5 mL) was added 1 M solution of TBAF (1.32 mL, 1.32 mmol). The mixture was stirred at room temperature for 16 h. The reaction mixture was absorbed on silica gel and was purified by chromatography (10→100% CHCl$_3$/10% 7 N NH$_3$ MeOH in CHCl₃) to obtain trans-4-(hydroxymethyl)-N-(7-(thiazol-5-yl)quinazolin-2-yl)cyclohexane-1-carboxamide 4586 as an off-white solid (125 mg, 0.34 mmol, 38.5% yield). ¹H NMR (499 MHz, DMSO-d₆) δ ppm 0.92-1.01 (2H, m), 1.26-1.36 (1H, m), 1.37-1.48 (2H, m), 1.80 (2H, br dd, J=12.90, 2.47 Hz), 1.87-1.93 (2H, m), 2.58-2.67 (1H, m), 3.24 (2H, t, J=5.76 Hz), 4.39 (1H, t, J=5.21 Hz), 7.95 (1H, dd, J=8.51, 1.65 Hz), 7.99-8.03 (1H, m), 8.12 (1H, d, J=8.51 Hz), 8.65 (1H, s), 9.24 (1H, s), 9.47 (1H, d, J=0.82 Hz), 10.67 (1H, s); ESIMS found for C₁₉H₂₀N₄O₂S m/z 369.1 (M+1).

Step 4

A suspension of Dess-Martin periodinane (120 mg, 0.29 mmol) and trans-4-(hydroxymethyl)-N-(7-(thiazol-5-yl)quinazolin-2-yl)cyclohexane-1-carboxamide 4586 (70 mg, 0.19 mmol) in a mixture of DCM (6 mL) and DMF (0.50 mL) was stirred at room temperature over the weekend. The reaction mixture was filtered, the solid was washed with DCM, and dried under high vacuo to obtain crude trans-4-formyl-N-(7-(thiazol-5-yl)quinazolin-2-yl)cyclohexane-1-carboxamide (CLIX) as an off-white color solid (62.6 mg, 0.17 mmol, 89.9% yield) which was used for next step without further purification. ESIMS found for C₁₉H₁₈N₄O₂S m/z 367.1 (M+1).

Step 5

A mixture of 3-fluoroazetidine hydrochloride (CLX) (30 mg, 0.28 mmol), trans-4-formyl-N-(7-(thiazol-5-yl)quinazolin-2-yl)cyclohexane-1-carboxamide (CLIX) (70 mg, 0.19 mmol) and TEA (0.04 mL, 0.29 mmol) in DCE (1.5 mL) was stirred for 20 min. Na(OAc)₃BH (60 mg, 0.28 mmol) was then added and the mixture was stirred at room temperature overnight. The reaction mixture was absorbed on silica gel and was purified by ISCO (10→80% CHCl₃/10% 7 N NH₃ MeOH in CHCl₃). The pure fraction was concentrated, the residue suspended in CHCl₃, the solid was collected by filtration, and dried under high vacuo to obtain trans-4-((3-fluoroazetidin-1-yl)methyl)-N-(7-(thiazol-5-yl)quinazolin-2-yl)cyclohexane-1-carboxamide 1519 as an off-white solid (30 mg, 0.07 mmol, 37.4% yield). ¹H NMR (499 MHz, DMSO-d₆) δ ppm 0.92 (2H, qd, J=12.72, 3.29 Hz), 1.22-1.32 (1H, m), 1.40 (2H, qd, J=12.76, 3.16 Hz), 1.80 (2H, br dd, J=13.04, 2.88 Hz), 1.88 (2H, br d, J=10.70 Hz), 2.29 (2H, d, J=6.86 Hz), 2.58-2.66 (1H, m), 2.97-3.08 (2H, m), 3.49-3.59 (2H, m), 5.12 (1H, dquin, J=58.00, 5.00, 5.00, 5.00, 5.00 Hz), 7.95 (1H, dd, J=8.37, 1.78 Hz), 8.00 (1H, d, J=1.65 Hz), 8.12 (1H, d, J=8.23 Hz), 8.65 (1H, s), 9.24 (1H, s), 9.46 (1H, s), 10.66 (1H, s); ESIMS found for C₂₂H₂₄FN₅OS m/z 426.2 (M+1).

Example 8

Preparation of N-(7-(2-aminothiazol-5-yl)quinazolin-2-yl)-2-(4-methylpiperazin-1-yl)isonicotinamide (1589) is depicted below in Scheme 37.

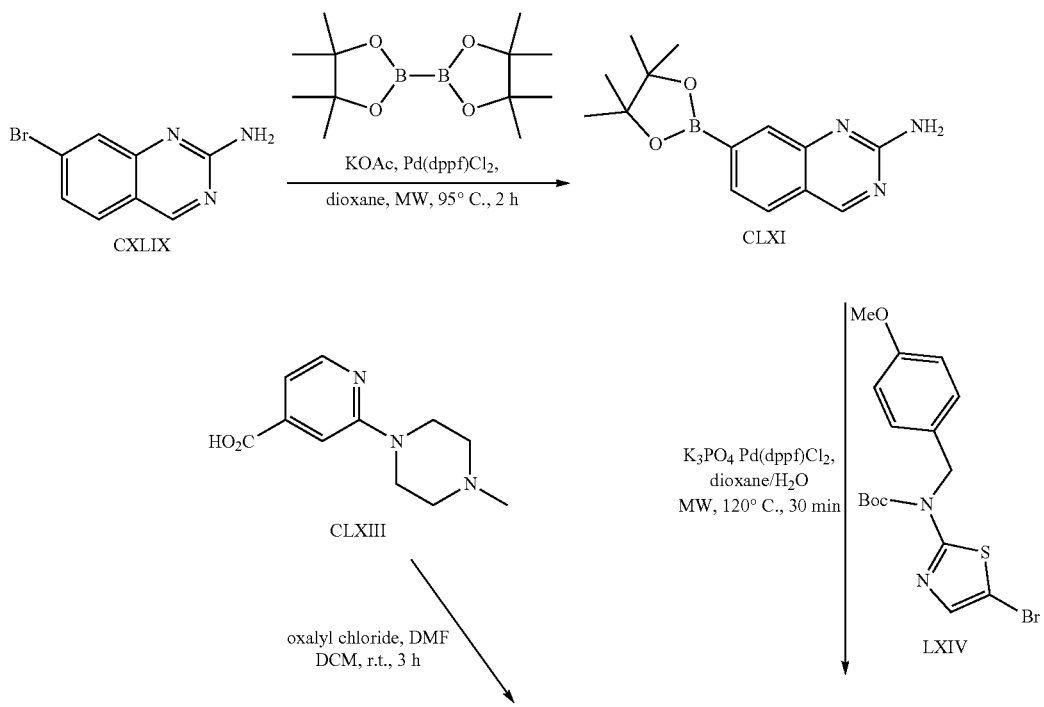

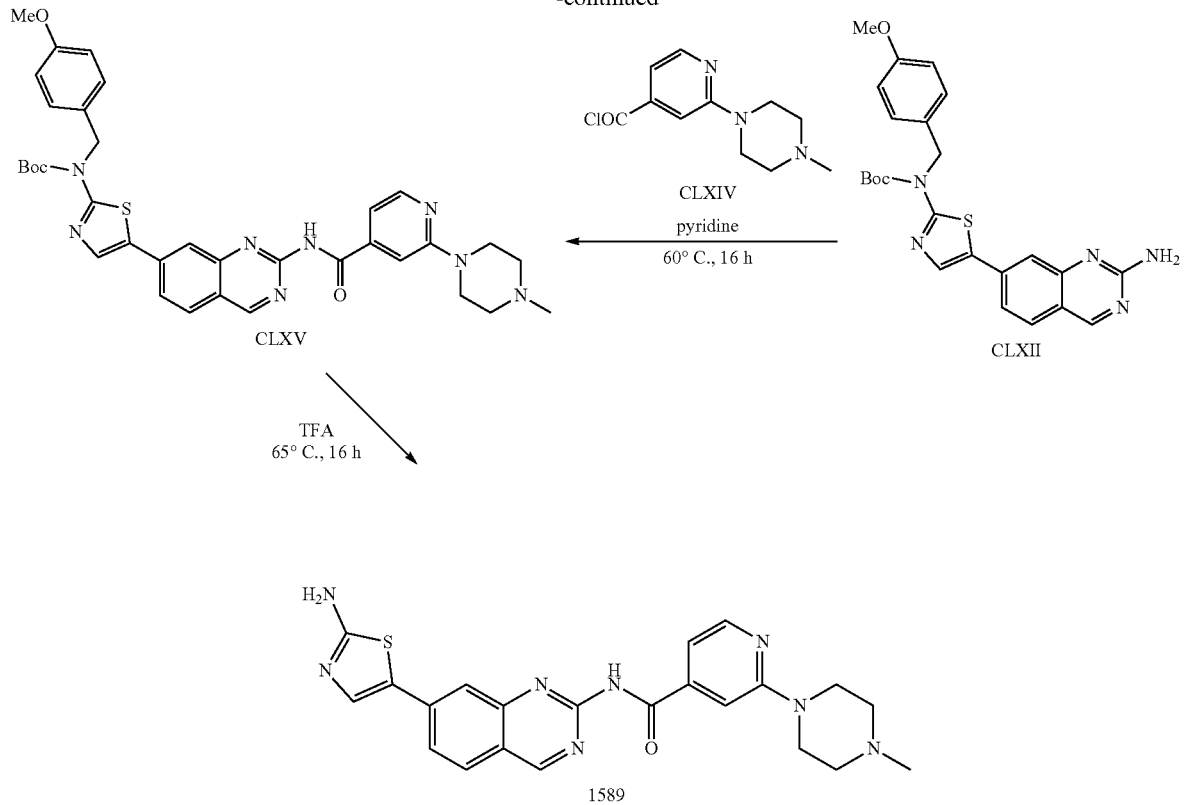

Steps 1-2

A mixture of KOAc (130 mg, 1.32 mmol), Pd(dppf)Cl₂ (36.5 mg, 0.04 mmol), 2-amino-7-bromoquinazoline (CXLIX) (supplier: CombiBlocks) (100 mg, 0.45 mmol), and 4,4,4',4',5,5,5',5'-octamethyl-2,2'-bi(1,3,2-dioxaborolane) (170 mg, 0.67 mmol) in 1,4-dioxane (4 mL) was added to a microwave vial purged with Argon for 1 min. The reaction was heated with microwave irradiation at 90° C. for 2 h. tert-Butyl (5-bromothiazol-2-yl)(4-methoxybenzyl) carbamate (LXIV) (178 mg, 0.45 mmol), Pd(dppf)Cl₂ (36.5 mg, 0.04 mmol), and K₃PO₄ (2 M in water) (0.68 mL, 1.36 mmol) were added and the mixture was purged with Argon for 1 min. The vial was resealed, and the mixture was heated with microwave irradiation at 120° C. for 30 min. The solvent was removed under vacuum and the residue was purified by silica gel column chromatography (12 g) (0→10% 1.7 n NH₃ in MeOH/CHCl₃) to produce tert-butyl (5-(2-aminoquinazolin-7-yl)thiazol-2-yl)(4-methoxybenzyl) carbamate (CLXI) as a tan solid (100 mg, 0.22 mmol, 48.3% yield). ESIMS found for C₂₄H₂₅N₅O₃S m/z 464.2 (M+1).

Step 3-4

To a suspension of 2-(4-methylpiperazin-1-yl)isonicotinic acid (CLXIII) (supplier: Enamine) (127 mg, 0.43 mmol) in DCM (3 mL) was added oxalyl chloride (60 μL, 0.69 mmol) followed by 2 drops of DMF. The mixture was stirred at room temperature for 3 h and concentrated. The crude acid chloride (CLXIV) was used in the next step without purification. To the residue was added pyridine (3 mL) followed by tert-butyl (5-(2-aminoquinazolin-7-yl)thiazol-2-yl)(4-methoxybenzyl) carbamate (CLXII) (100 mg, 0.22 mmol) and the reaction was stirred at 60° C. for 16 h. The solvent was stripped, and the residue was purified by silica gel column chromatography (12 g) (0→10% 1.7N NH₃ in MeOH/CHCl₃) to produce tert-butyl (4-methoxybenzyl)(5-(2-(2-(4-methylpiperazin-1-yl)isonicotinamido)quinazolin-7-yl)thiazol-2-yl)carbamate (CLXV) as a tan solid (62 mg, 0.09 mmol, 43.1% yield). ESIMS found for C₃₅H₃₈N₈O₄S m/z 667.3 (M+1).

Step 5

A solution of tert-butyl (4-methoxybenzyl)(5-(2-(2-(4-methylpiperazin-1-yl)isonicotinamido)quinazolin-7-yl)thiazol-2-yl)carbamate (CLXV) (62 mg, 0.09 mmol) in TFA (1 mL) was stirred at 65° C. for 16 h. The solvent was removed under reduced pressure and the residue was purified by silica gel column chromatography (12 g) (0→15% 1.7N NH₃ in MeOH/CHCl₃) to produce N-(7-(2-Aminothiazol-5-yl)quinazolin-2-yl)-2-(4-methylpiperazin-1-yl)isonicotinamide 1589 as a yellow solid (62.mg, 0.09 mmol, 26.5% yield). ¹H NMR (499 MHz, DMSO-d₆) δ ppm 2.23 (3H, s), 2.42 (4H, t, J=4.94 Hz), 3.55-3.63 (4H, m), 7.09 (1H, dd, J=5.08, 1.23 Hz), 7.38 (1H, s), 7.55 (3H, d, J=3.57 Hz), 7.83 (1H, s), 7.86 (1H, dd, J=8.64, 1.78 Hz), 8.02 (1H, d, J=8.51 Hz), 8.25 (1H, d, J=5.21 Hz), 9.41 (1H, s), 11.24 (1H, br s); ESIMS found for C₂₂H₂₂N₈OS m/z 447.2 (M+1).

Example 9

Preparation of N-(3-(1-methyl-1H-pyrazol-4-yl)-1,7-naphthyridin-6-yl)-2-(4-methylpiperazin-1-yl)isonicotinamide (2867) is depicted below in Scheme 38.

Scheme 38

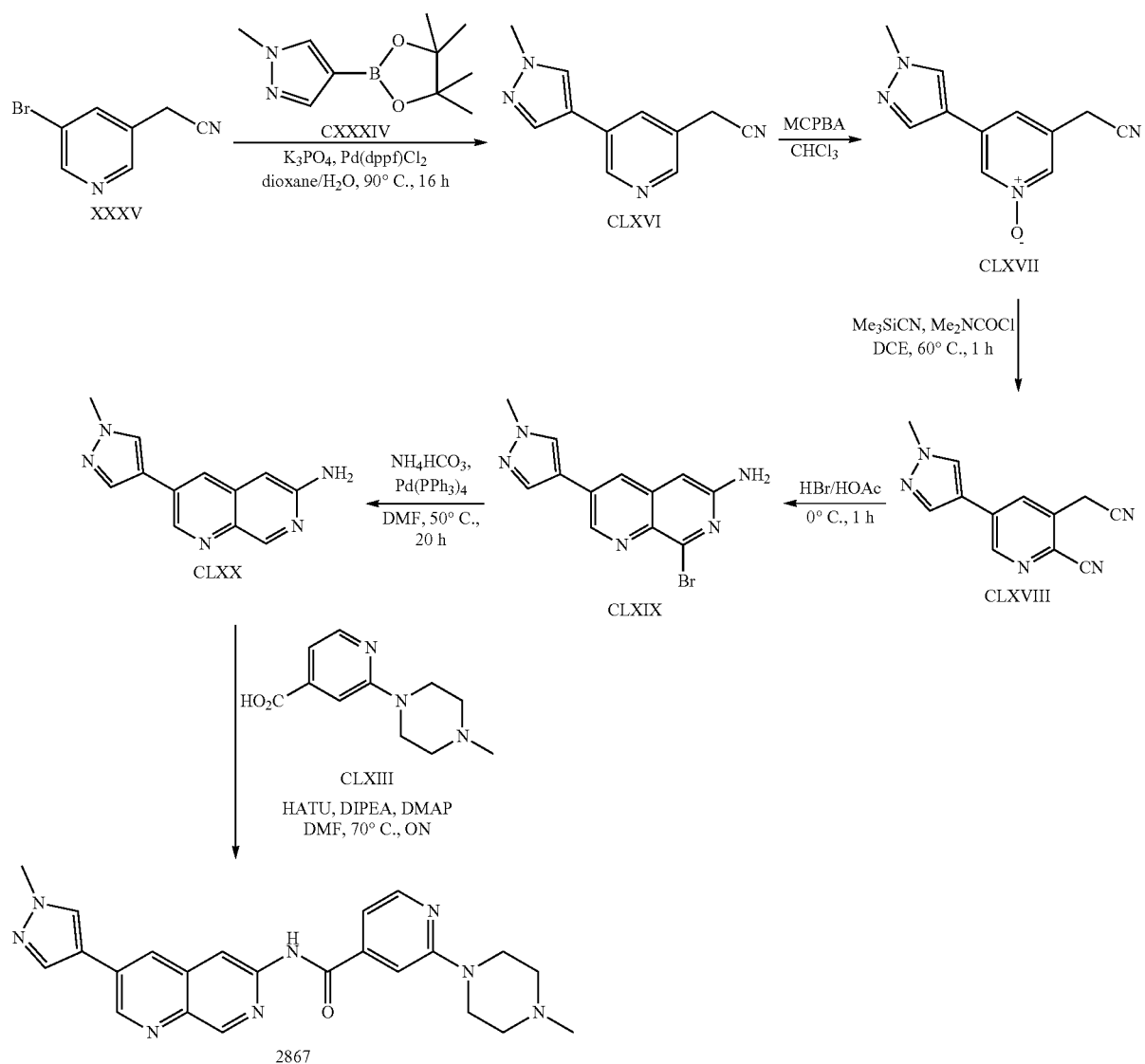

Step 1

A mixture of 1-methyl-4-(4,4,5,5-tetramethyl-1,3,2-dioxaborolan-2-yl)-1H-pyrazole (CXXXIV) (4.51 g, 21.7 mmol), Pd(dppf)Cl$_2$ (1.18 g, 1.45 mmol), K$_3$PO$_4$ (6.14 g, 28.93 mmol) and 2-(5-bromopyridin-3-yl)acetonitrile (XXXV) (2.85 g, 14.46 mmol) was suspended in a mixture of 1,4-dioxane (60 mL) and water (15 mL). The reaction was purged with Argon for 1 min and then heated to 90° C. for 16 h. The organic layer was separated, dried over Na$_2$SO$_4$ and evaporated under reduced vacuum. The residue was purified by silica gel column chromatography (12 g) (0→8% 1.7 N NH$_3$ in MeOH/DCM) to produce 2-(5-(1-methyl-1H-pyrazol-4-yl)pyridin-3-yl)acetonitrile (CLXVI) as a brown solid (2.29 g, 11.6 mmol, 79.9% yield). ESIMS found for C$_{11}$H$_{10}$N$_4$ m/z 199.1 (M+1).

Step 2

To a round bottom flask was added 2-(5-(1-methyl-1H-pyrazol-4-yl)pyridin-3-yl)acetonitrile (CLXVI) (2.29 g, 11.55 mmol) CHCl$_3$ (58 mL), followed by the addition of MCPBA (2.79 g, 16.17 mmol). The reaction mixture is stirred at room temperature for 16 h. The LCMS showed incomplete reaction so another 2-[5-(1-methylpyrazol-4-yl)-3-pyridyl]acetonitrile (2.29 g, 11.55 mmol) was added and stirred at room temperature for 6 h. The reaction mixture was concentrated under vacuum and the residue was purified by silica gel column chromatography (24 g) (0→5% MeOH/CHCl$_3$) to produce 3-(cyanomethyl)-5-(1-methyl-1H-pyrazol-4-yl)pyridine 1-oxide (CLXVII) (1.53 g, 7.14 mmol, 61.8% yield). ESIMS found for C$_{11}$H$_{10}$N$_4$O m/z 215.1 (M+1).

Step 3

To a solution of 3-(cyanomethyl)-5-(1-methyl-1H-pyrazol-4-yl)pyridine 1-oxide (CLXVII) (1.54 g, 7.19 mmol) in DCE (14.4 mL) was added TMSCN (0.04 mL, 0.31 mmol), This solution was stirred at room temperature for 5 min before adding dimethylcarbamyl chloride (0.66 mL, 7.19 mmol). The reaction was then heated at 60° C. for 1 h. The solvent was removed under vacuum and the product was purified by silica gel (40 g) (0→5% MeOH/CHCl3) to produce 3-(cyanomethyl)-5-(1-methyl-1H-pyrazol-4-yl)picolinonitrile (CLXVIII) as an off white solid (1.07 g, 4.79 mmol, 66.7% yield). ESIMS found for $C_{12}H_9N_5$ m/z 224.1 (M+1).

Step 4

A solution of 3-(cyanomethyl)-5-(1-methyl-1H-pyrazol-4-yl)picolinonitrile (CLXVIII) (1.07 g, 4.79 mmol) in HBr (33% in acetic Acid) (4.97 mL, 28.76 mmol) was stirred at 0° C. for 1 h. EtOAc was added, the precipitate was filtered, and the organic layer was neutralized with aqueous saturated $NaHCO_3$, extracted with EtOAc which was dried over $Na_2SO_4$. The organic layers were evaporated to dryness under vacuum and the residue purified by silica gel column Chromatography (40 g) (0→10% MeOH/CHCl$_3$) to produce 8-bromo-3-(1-methyl-1H-pyrazol-4-yl)-1,7-naphthyridin-6-amine (CLXIX) as a light-yellow solid (180 mg, 1.09 mmol, 12.3% yield). ESIMS found for $C_{12}H_{10}BrN_5$ m/z 304.0 (M+1).

Step 5

A mixture of 8-bromo-3-(1-methyl-1H-pyrazol-4-yl)-1,7-naphthyridin-6-amine (CLXIX) (181.3 mg, 0.60 mmol), ammonium formate (188 mg, 2.98 mmol) and Pd(PPh$_3$)$_4$ (69 mg, 0.06 mmol) in DMF (3.0 mL) was heated to 50° C. for 20 h. The reaction mixture was cooled, and the solvent removed. The crude product was adsorbed onto Celite and purified by silica gel (solid load) column chromatography (40 g) (0→10% MeOH/CHCl$_3$) to produce 3-(1-methyl-1H-pyrazol-4-yl)-1,7-naphthyridin-6-amine (CLXX) as an off-white solid (62 mg, 0.28 mmol, 46.2% yield). $^1$H NMR (499 MHz, DMSO-d$_6$) δ ppm 3.90 (3H, s), 6.11 (2H, s), 6.55 (1H, s), 8.07 (1H, d, J=1.92 Hz), 8.09 (1H, s), 8.40 (1H, s), 8.80 (1H, s), 8.82 (1H, d, J=2.20 Hz); ESIMS found for $C_{12}H_{11}N_5$ m/z 226.1 (M+1).

Step 6

To a suspension of 3-(1-methyl-1H-pyrazol-4-yl)-1,7-naphthyridin-6-amine (CLXX) (61 mg, 0.27 mmol), 2-(4-methylpiperazin-1-yl)isonicotinic acid dihydrochloride (CLXIII) (120 mg, 0.41 mmol), DMAP (33 mg, 0.27 mmol) and HATU (155 mg, 0.41 mmol) in DMF (2.7 mL) was added DIPEA (0.28 mL, 1.62 mmol). The resulting mixture was stirred at 80° C. for 16 h. The reaction mixture was cooled to room temperature and poured into water. The resulting solid was filtered and purified by silica gel chromatography (0→10% 1.7 N NH$_3$ in MeOH/CHCl$_3$) to produce N-(3-(1-methyl-1H-pyrazol-4-yl)-1,7-naphthyridin-6-yl)-2-(4-methylpiperazin-1-yl) isonicotinamide 2867 as a tan solid (50.0 mg, 0.117 mmol, 43.1% yield). $^1$H NMR (499 MHz, DMSO-d$_6$) δ ppm 2.23 (3H, s), 2.40-2.46 (4H, m), 3.56-3.65 (4H, m), 3.93 (3H, s), 7.15 (1H, dd, J=5.08, 1.23 Hz), 7.46 (1H, s), 8.21 (1H, s), 8.26 (1H, d, J=4.94 Hz), 8.51 (1H, s), 8.56 (1H, d, J=2.20 Hz), 8.65 (1H, s), 9.21 (1H, t, J=0.82 Hz), 9.24 (1H, d, J=2.20 Hz), 11.20 (1H, s); ESIMS found for $C_{23}H_{24}N_8O$ m/z 429.2 (M+1).

Example 10

Preparation of N-(3-(2-methylthiazol-5-yl)-1,7-naphthyridin-6-yl)-1-(oxetan-3-yl)piperidine-4-carboxamide (4622) is depicted below in Scheme 39.

Scheme 39

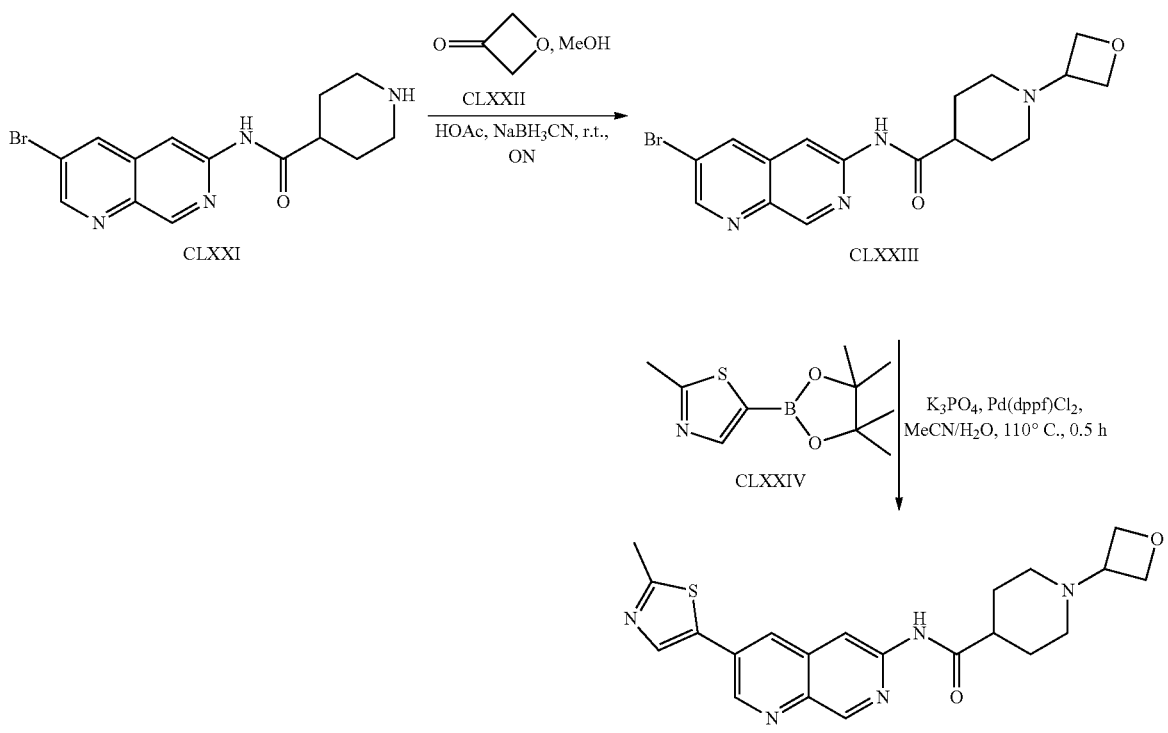

Step 1

A mixture of N-(3-bromo-1,7-naphthyridin-6-yl)piperidine-4-carboxamide (CLXXI) (50 mg, 0.15 mmol), oxetan-3-one (CLXXII) (20 μL, 0.59 mmol) and TEA (70 μL, 0.50 mmol) in DCE (2 mL) was stirred for 30 min at room temperature, then NaBH$_3$CN (160 mg, 0.75 mmol) was added and the mixture was stirred at 37° C. for 5 h. The reaction mixture was concentrated, and the resulting residue was adsorbed on silica gel and then purified by column chromatography (0→10% MeOH/CHCl$_3$). Pure fractions were collected and concentrated, and the resulting solid was triturated with DCM/hexane, filtered and dried under high vacuum to obtain N-(3-bromo-1,7-naphthyridin-6-yl)-1-(oxetan-3-yl)piperidine-4-carboxamide (CLXXIII) as a beige solid (52 mg, 0.13 mmol, 89.1% yield). ESIMS found for C$_{17}$H$_{19}$BrN$_4$O$_2$ m/z 391.1 (M+1).

Step 2

A mixture of N-(3-bromo-1,7-naphthyridin-6-yl)-1-(oxetan-3-yl)piperidine-4-carboxamide (CLXXIII) (52 mg, 0.13 mmol), 2-methyl-5-(4,4,5,5-tetramethyl-1,3,2-dioxaborolan-2-yl)thiazole (CLXXIV) (45 mg, 0.20 mmol), Pd(dppf)Cl$_2$ (10 mg, 0.01 mmol), and K$_3$PO$_4$ (0.2 mL, 0.40 mmol) in 1,4-dioxane (3 mL) was purged with N$_2$ gas for 5 min. The reaction mixture was heated with microwave irradiation at 110° C. for 30 min. Reaction mixture cooled down to room temperature, the organic layer was separated and concentrated, and the resulting residue was purified by column chromatography (0→10% MeOH/CHCl$_3$). The pure fractions were collected and concentrated, and the resulting solid was triturated with DCM, filtered and dried to obtain N-(6-(2-methylthiazol-5-yl)-2,7-naphthyridin-3-yl)-1-(oxetan-3-yl) piperidine-4-carboxamide 4622 as an off-white solid (35 mg, 0.09 mmol, 64.3% yield). $^1$H NMR (499 MHz, DMSO-d$_6$) δ ppm 1.64-1.74 (2H, m), 1.75-1.86 (4H, m), 2.54-2.63 (1H, m), 2.72-2.78 (5H, m), 3.35-3.42 (1H, m), 4.43 (2H, t, J=6.17 Hz), 4.53 (2H, t, J=6.45 Hz), 8.41 (1H, s), 8.53 (1H, d, J=1.92 Hz), 8.58 (1H, s), 9.17 (1H, s), 9.22 (1H, d, J=2.20 Hz), 10.72 (1H, s); ESIMS found for C$_{21}$H$_{23}$N$_5$O$_2$S m/z 410.15 (M+1).

Example 11

Preparation of N-(6-(1-methyl-1H-pyrazol-4-yl)-2,7-naphthyridin-3-yl)-2-(4-methylpiperazin-1-yl)thiazole-5-carboxamide (4632) is depicted below in Scheme 40.

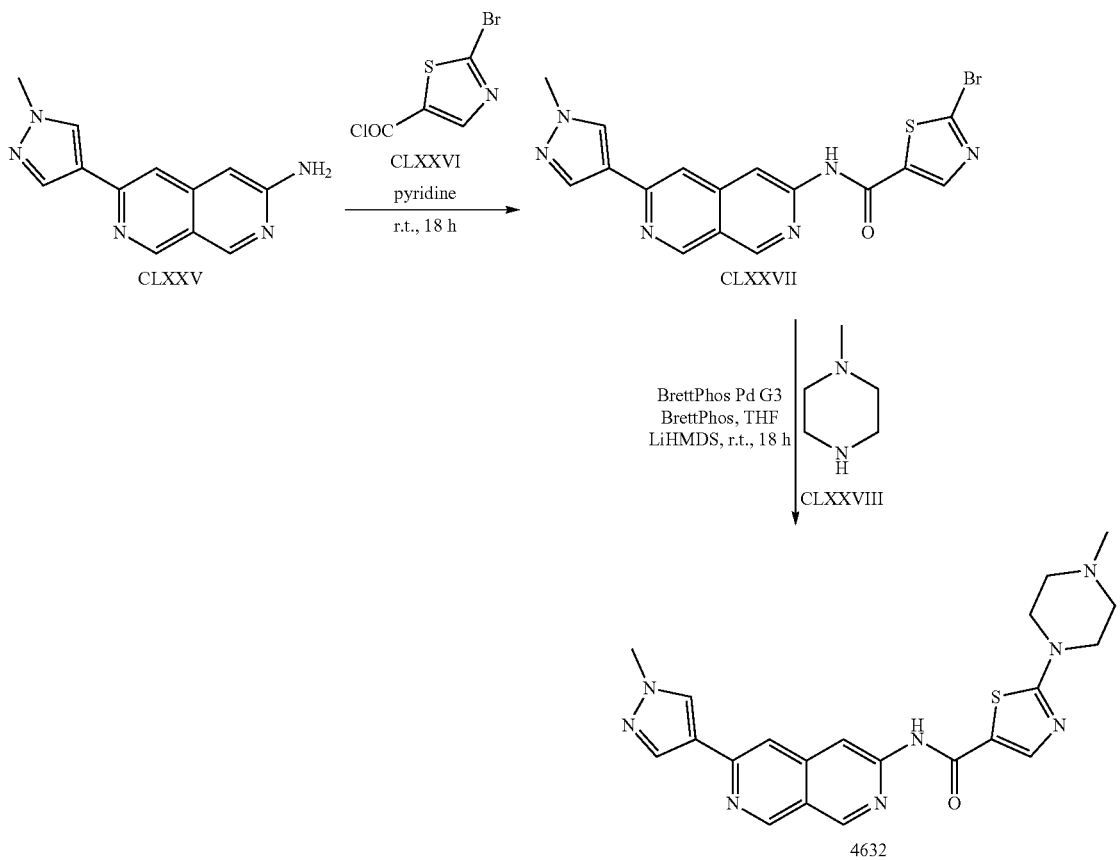

Step 1

To a solution of 6-(1-methyl-1H-pyrazol-4-yl)-2,7-naphthyridin-3-amine (CLXXV) (100 mg, 0.44 mmol) in pyridine (4 mL) was added 2-bromothiazole-5-carbonyl chloride (CLXXVI) (120.7 mg, 0.53 mmol). The reaction was stirred at room temperature for 18 h and worked-up with saturated NaHCO$_3$-EtOAc extraction. The organic layers were combined, dried over Na$_2$SO$_4$, and evaporated to dryness. The residue was purified by silica column (0→10% 7 N NH$_3$ MeOH/CHCl$_3$) to produce 2-bromo-N-(6-(1-methyl-1H-pyrazol-4-yl)-2,7-naphthyridin-3-yl)thiazole-5-carboxamide (CLXXII) as a white solid (107 mg, 0.26 mmol, 58.0% yield). ESIMS found for $C_{16}H_{11}BrN_6OS$ m/z 415.1 (M+1).

Step 2

A mixture of BrettPhos Pd G3 (11.7 mg, 0.01 mmol), BrettPhos (7 mg, 0.01 mmol), 2-bromo-N-(6-(1-methyl-1H-pyrazol-4-yl)-2,7-naphthyridin-3-yl)thiazole-5-carboxamide (CLXXII) (107 mg, 0.26 mmol) and 1-methylpiperazine (CLXXVIII) (40 µL, 0.36 mmol) in THF (8 mL) was purged with argon. LiHMDS (1.0 M solution in THF) (0.65 mL, 0.65 mmol) was added and the resulting mixture stirred in a sealed tube at room temperature under the argon atm for 18 h. The reaction was washed saturated $NaHCO_3$-EtOAc extraction. The organic layers were combined, dried over $Na_2SO_4$, and evaporated to dryness. The residue was purified by silica gel chromatography (0→10% 7 N $NH_3$-MeOH/CHCl$_3$). The fractions containing the product were concentrated and the resulting solid was filtered and dried under vacuo to afford N-(3-(1-methyl-1H-pyrazol-4-yl)-1,7-naphthyridin-6-yl)-2-(4-methylpiperazin-1-yl)thiazole-5-carboxamide 4632 as an orange solid (20.3 mg, 0.05 mmol, 18.1% yield). $^1$H NMR (499 MHz, DMSO-d$_6$) δ ppm 2.23 (3H, s), 2.40-2.46 (4H, m), 3.50-3.57 (4H, m), 3.92 (3H, s), 8.01 (1H, s), 8.14 (1H, s), 8.38 (2H, s), 8.42 (1H, s), 9.28 (1H, s), 9.34 (1H, s), 10.98 (1H, s); ESIMS found for $C_{21}H_{22}N_8OS$ m/z 435.2 (M+1).

Example 12

Preparation of trans-4-(dimethylamino)-N-(6-(thiazol-5-yl)-2,7-naphthyridin-3-yl) cyclohexane-1-carboxamide (4239) is depicted below in Scheme 41.

aldehyde (0.05 mL, 0.74 mmol). After stirring 15 min, Na(OAc)$_3$BH (160 mg, 0.74 mmol) was added and the mixture was stirred at room temperature for 2 h. The reaction mixture was concentrated, and the resulting residue partitioned between EtOAc and 1 N NaOH. The organic layer was separated, washed with water, brine, and dried over anhydrous $Na_2SO_4$, and concentrated to dryness under vacuum obtain trans-N-(6-chloro-2,7-naphthyridin-3-yl)-4-(dimethylamino) cyclohexane-1-carboxamide (CLXXX) as an off-white solid (76 mg, 0.22 mmol, 88.2% yield) which was used for next step without purification. ESIMS found for $C_{17}H_{21}ClN_4O$ m/z 333.1 (M+1).

Step 2

A mixture of trans-N-(6-chloro-2,7-naphthyridin-3-yl)-4-(dimethylamino) cyclohexane-1-carboxamide (CLXXX) (40 mg, 0.12 mmol), 5-(4,4,5,5-tetramethyl-1,3,2-dioxaborolan-2-yl)thiazole (CLXXXI) (30 mg, 0.15 mmol) and SPhos-Pd G4 (10 mg, 0.010 mmol) was taken in 1,4-dioxane (0.50 mL) and was added 2 M solution of $K_3PO_4$ (150 µL, 0.30 mmol). The mixture was purged with N$_2$ gas for 10 min and then stirred at 70° C. for 16 h. The organic layer was carefully separated, absorbed on silica gel and purified by ISCO followed by prep TLC using (60% CHCl$_3$/10% 7 N NH$_3$ MeOH in CHCl$_3$) to obtain trans-4-(dimethylamino)-N-(6-(thiazol-5-yl)-2,7-naphthyridin-3-yl) cyclohexane-1-carboxamide 4239 as a white solid (12 mg, 0.03 mmol, 26.2% yield). $^1$H NMR (499 MHz, DMSO-d$_6$) δ ppm 1.14-1.22 (2H, m), 1.42-1.53 (2H, m), 1.87 (2H, br d,

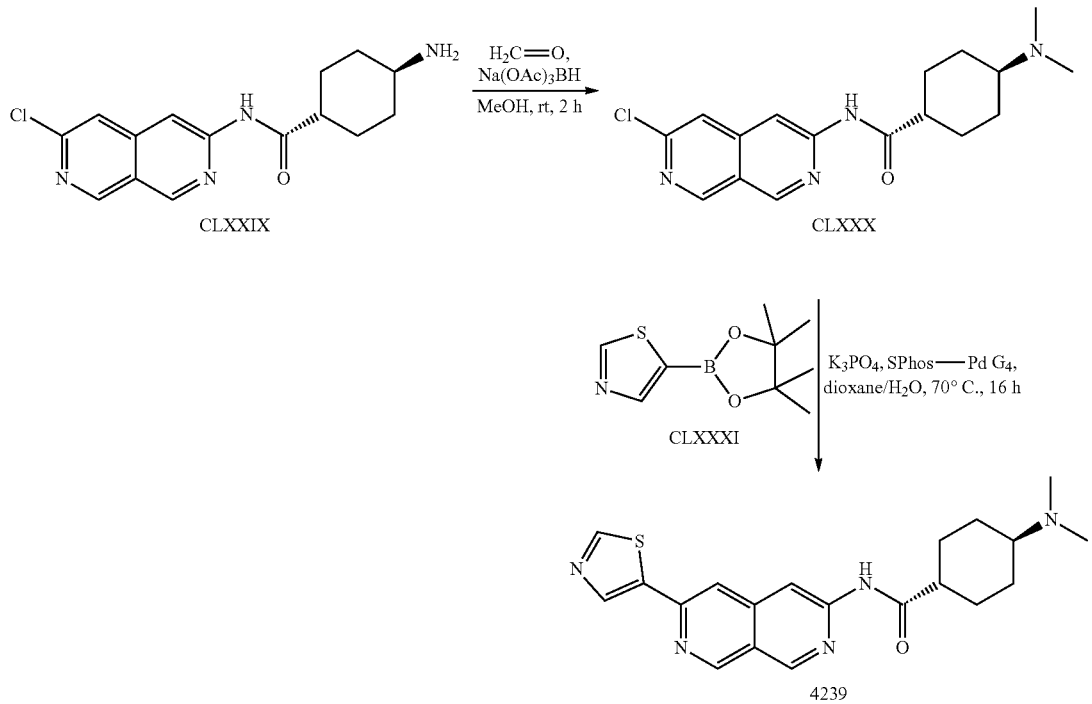

Scheme 41

Step 1

To a stirred solution of trans-4-amino-N-(6-chloro-2,7-naphthyridin-3-yl) cyclohexane-1-carboxamide (CLXXIX) (80 mg, 0.25 mmol) in MeOH (1.5 mL) was added form- J=10.98 Hz), 1.93 (2H, br d, J=11.53 Hz), 2.13-2.17 (1H, m), 2.18 (6H, s), 2.52-2.56 (1H, m), 8.43 (1H, s), 8.50 (1H, s), 8.73 (1H, s), 9.20 (1H, s), 9.32 (1H, s), 9.37 (1H, s), 10.78 (1H, s); ESIMS found for $C_{20}H_{23}N_5OS$ m/z 382.2 (M+1).

Example 13

Preparation of N-(6-(1-methyl-5-(morpholinomethyl)-1H-pyrazol-4-yl)-2,7-naphthyridin-3-yl)-2-morpholinoisonicotinamide (3941) is depicted below in Scheme 42.

mmol), K₃PO₄ (13.9 mL, 27.84 mmol), and Pd(dppf)Cl₂ (0.54 g, 0.66 mmol) were added and the mixture purged with Argon for 1 min. The tube was resealed and heated to 100° C. for 16 h. The solvent was evaporated under high vacuum and the residue purified by silica gel column chromatogra-

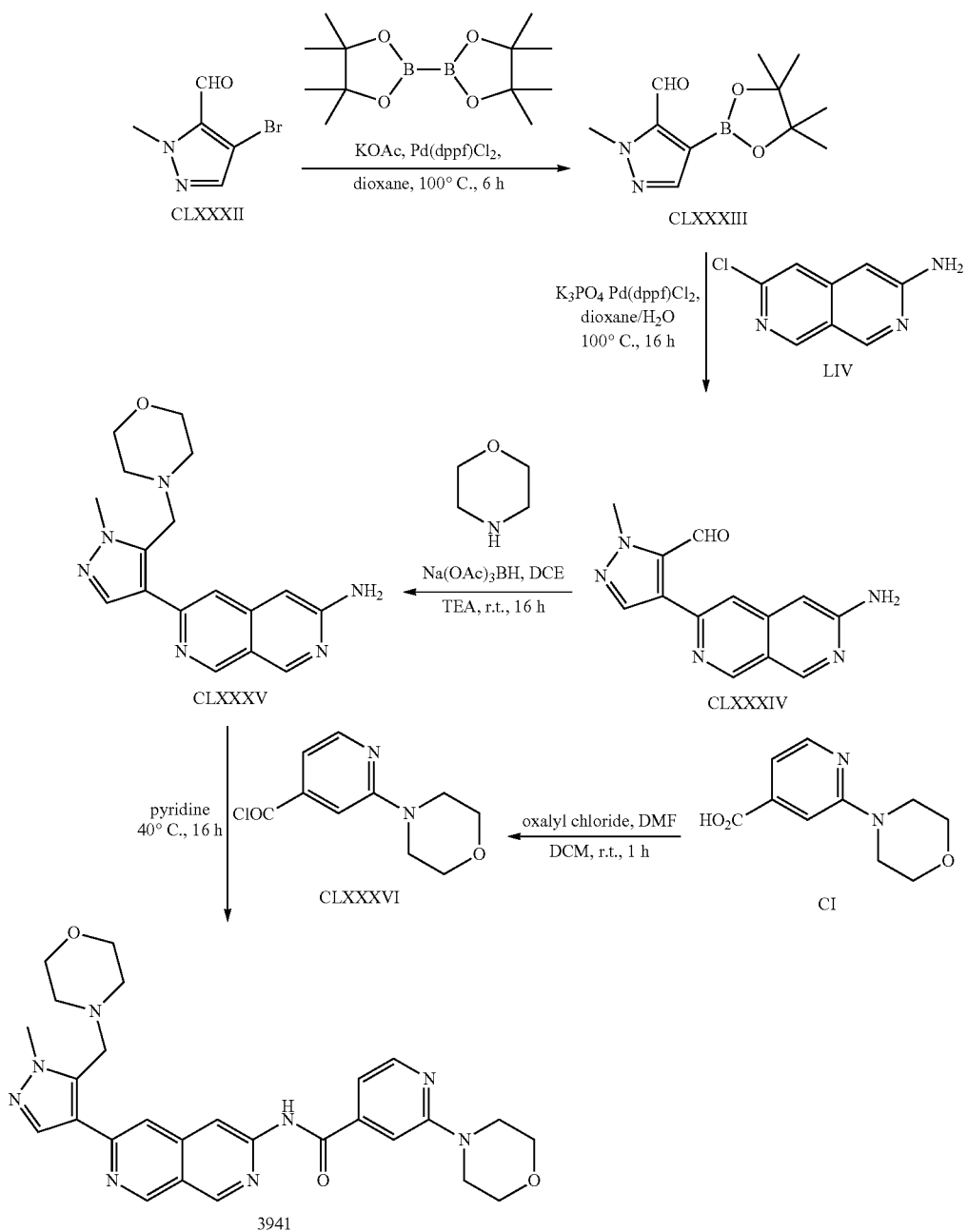

Steps 1-2

4-Bromo-1-methyl-1H-pyrazole-5-carbaldehyde (CLXXXII) (supplier: CombiBlocks) (2.18 g, 11.55 mmol), Pd(dppf)Cl₂ (0.54 g, 0.66 mmol), Bis(pinacolato)diboron (4.44 g, 17.49 mmol), and KOAc (2.2 g, 22.37 mmol) in 1,4-dioxane (35 mL) were added to a sealed tube, purged with Argon for 1 min, and then heated to 100° C. for 6 h. 6-Chloro-2,7-naphthyridin-3-amine (LIV) (1.0 g, 5.57 phy (0→10% MeOH/CHCl₃) to produce 4-(6-amino-2,7-naphthyridin-3-yl)-1-methyl-1H-pyrazole-5-carbaldehyde (CLXXXIV) as an off-white solid (390 mg, 1.54 mmol, 27.7% yield). ESIMS found for $C_{13}H_{11}N_5O$ m/z 254.1 (M+1).

Step 3

To a solution of 4-(6-amino-2,7-naphthyridin-3-yl)-2-methylpyrazole-3-carbaldehyde (CLXXXIV) (133 mg, 0.53 mmol), TEA (150 μL, 1.08 mmol), morpholine (100 μL, 1.16 mmol) in DCE (5 mL) was added Na(OAc)₃BH (342 mg, 1.61 mmol). The reaction was stirred at room temperature for 16 h. The solvent was evaporated under high vacuum and the residue purified by silica gel column chromatography (12 g) (0→10% 1.7 N NH₃ in MeOH/CHCl₃) to produce 6-(1-methyl-5-(morpholinomethyl)-1H-pyrazol-4-yl)-2,7-naphthyridin-3-amine (CLXXXV) as an off-white solid (69 mg, 0.21 mmol, 40.5% yield). ESIMS found for $C_{17}H_{20}N_6O$ m/z 325.2 (M+1).

Step 4-5

To a suspension of 2-morpholinoisonicotinic acid (CI) (30 mg, 0.16 mmol) in DCM (1 mL) was added oxalyl chloride (28 μL, 0.32 mmol) followed by 2 drops of DMF. The mixture was stirred at room temperature for 1 h and concentrated under vacuum. The crude acid chloride (CLXXXVI) was used in the next step without purification. To this solid was added pyridine (1 mL) and 6-(1-methyl-5-(morpholinomethyl)-1H-pyrazol-4-yl)-2,7-naphthyridin-3-amine (CLXXXV) (30 mg, 0.08 mmol). This mixture was heated to 40° C. for 16 h. To this mixture was added H₂O (20 mL) and brine (10 mL). The aqueous layer was extracted with DCM and the DCM was dried over Na₂SO₄, filtered and the solvent was removed under vacuum. The residue was purified by silica gel (12 g) (0→10% 1.7 N NH₃ in MeOH/CHCl₃) to produce N-(6-(1-Methyl-5-(morpholinomethyl)-1H-pyrazol-4-yl)-2,7-naphthyridin-3-yl)-2-morpholinoisonicotinamide 3941 as an off-white solid (10 mg, 0.02 mmol, 24.2% yield). ¹H NMR (499 MHz, DMSO-d₆) δ ppm 2.44 (4H, br s), 3.50-3.56 (4H, m), 3.56-3.61 (4H, m), 3.72-3.77 (4H, m), 3.93 (3H, s), 4.12 (2H, s), 7.20 (1H, dd, J=5.08, 1.23 Hz), 7.47 (1H, s), 8.08 (1H, s), 8.16 (1H, s), 8.29 (1H, d, J=5.21 Hz), 8.60 (1H, s), 9.35 (1H, s), 9.43 (1H, s), 11.28 (1H, s); ESIMS found for $C_{27}H_{30}N_8O_3$ m/z 515.3 (M+1).

The following compounds were prepared in accordance with the procedures described in the above Examples 1-13.

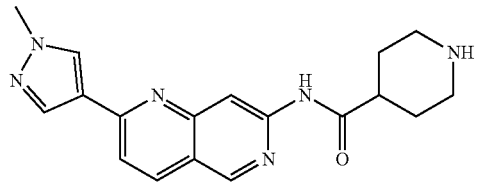

N-(2-(1-Methyl-1H-pyrazol-4-yl)-1,6-naphthyridin-7-yl)piperidine-4-carboxamide 11

White solid (120 mg, 0.36 mmol, 53.7% yield). ¹H NMR (499 MHz, DMSO-d) δ ppm 1.53 (2H, qd, J=12.17, 4.12 Hz), 1.71 (2H, br d, J=10.43 Hz), 2.43-2.49 (2H, m), 2.65 (1H, tt, J=11.53, 3.70 Hz), 2.94-3.02 (2H, m), 3.93 (3H, s), 7.80 (1H, d, J=8.51 Hz), 8.21 (1H, s), 8.38 (1H, d, J=8.51 Hz), 8.48 (1H, s), 8.55 (1H, s), 9.05 (1H, s), 10.56 (1H, s); ESIMS found for C m/z 337.2 (M+1).

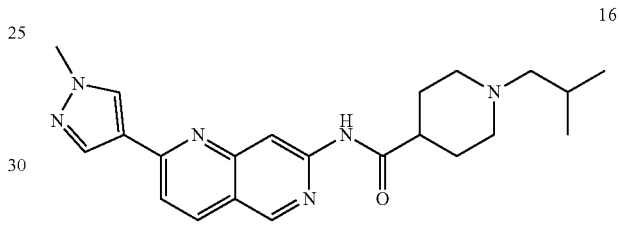

1-Isobutyl-N-(2-(1-methyl-1H-pyrazol-4-yl)-1,6-naphthyridin-7-yl) piperidine-4-carboxamide 16

White solid (8.0 mg, 0.020 mmol, 9.8% yield). ¹H NMR (500 MHz, DMSO-d₆) δ ppm 0.86 (6H, d, J=6.59 Hz), 1.62-1.72 (2H, m), 1.74-1.81 (3H, m), 1.86 (2H, td, J=11.53, 1.65 Hz), 2.02 (2H, d, J=7.41 Hz), 2.52-2.59 (1H, m), 2.84-2.90 (2H, m), 3.93 (3H, s), 7.81 (1H, d, J=8.78 Hz), 8.21 (1H, s), 8.39 (1H, d, J=0.82 Hz), 8.48 (1H, s), 8.55 (1H, s), 9.05 (1H, s), 10.61 (1H, s); ESIMS found for $C_{22}H_{28}N_6O$ m/z 393.2 (M+1).

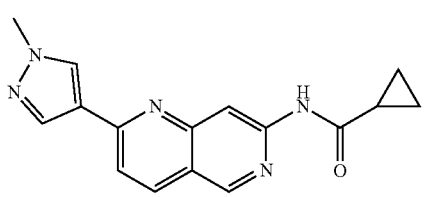

N-(2-(1-Methyl-1H-pyrazol-4-yl)-1,6-naphthyridin-7-yl) cyclopropanecarboxamide 2

White solid (8.7 mg, 0.030 mmol, 10.3% yield). ¹H NMR (499 MHz, DMSO-d₆) δ ppm 0.81-0.86 (2H, m), 0.86-0.91 (2H, m), 2.05-2.13 (1H, m), 3.93 (3H, s), 7.80 (1H, d, J=8.78 Hz), 8.21 (1H, d, J=0.82 Hz), 8.38 (1H, d, J=8.51 Hz), 8.45 (1H, s), 8.54 (1H, s), 9.06 (1H, s), 10.98 (1H, s); ESIMS found for $C_{16}H_{15}N_5O$ m/z 294.1 (M+1).

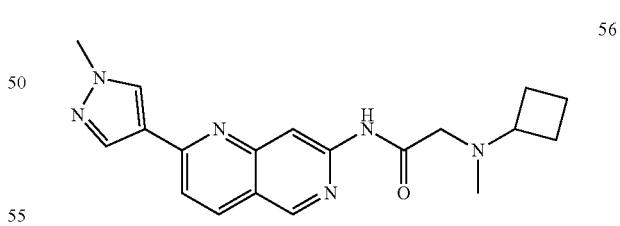

2-(Cyclobutyl(methyl)amino)-N-(2-(1-methyl-1H-pyrazol-4-yl)-1,6-naphthyridin-7-yl)acetamide 56

Off-white solid (30 mg, 0.09 mmol, 50.7% yield). ¹H NMR (499 MHz, DMSO-d₆) δ ppm 1.53-1.70 (2H, m), 1.80-1.93 (2H, m), 1.97-2.06 (2H, m), 2.22 (3H, s), 3.08 (3H, quin, J=7.75 Hz), 3.13 (2H, s), 3.93 (3H, s), 7.84 (1H, d, J=8.51 Hz), 8.23 (1H, s), 8.39-8.44 (1H, m), 8.47 (1H, s), 8.58 (1H, s), 9.07 (1H, s), 10.05 (1H, s); ESIMS found for C m/z 351.2 (M+1).

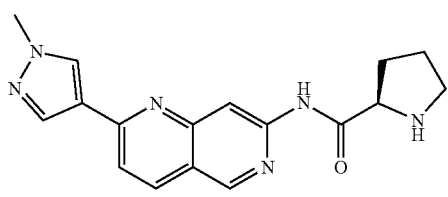

(R)—N-(2-(1-Methyl-1H-pyrazol-4-yl)-1,6-naphthyridin-7-yl)pyrrolidine-2-carboxamide 62

Yellow solid (20 mg, 0.06 mmol, 56.6% yield). $^1$H NMR (499 MHz, DMSO-d$_6$) δ ppm 1.68 (2H, quin, J=6.86 Hz), 1.80-1.90 (1H, m), 2.06-2.17 (1H, m), 2.87 (1H, dt, J=10.22, 6.42 Hz), 2.97 (1H, dt, J=10.09, 6.62 Hz), 3.82 (1H, dd, J=9.06, 5.49 Hz), 3.93 (3H, s), 7.83 (1H, d, J=8.51 Hz), 8.22 (1H, s), 8.41 (1H, d, J=8.51 Hz), 8.48 (1H, s), 8.57 (1H, s), 9.06 (1H, s), 10.46 (1H, s); ESIMS found for C m/z 323.15 (M+1).

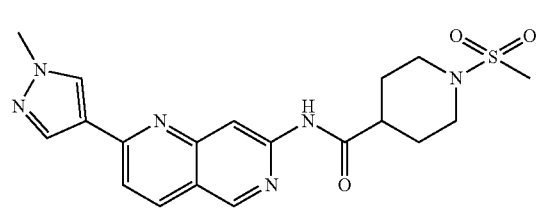

N-(2-(1-Methyl-1H-pyrazol-4-yl)-1,6-naphthyridin-7-yl)-1-(methylsulfonyl)piperidine-4-carboxamide 71

White solid (26 mg, 0.06 mmol, 33.4% yield). $^1$H NMR (499 MHz, DMSO-d$_6$) δ ppm 1.64-1.77 (2H, m), 1.96 (2H, br dd, J=13.31, 2.61 Hz), 2.66-2.72 (1H, m), 2.76 (2H, td, J=11.94, 2.20 Hz), 2.90 (3H, s), 3.60-3.67 (2H, m), 3.93 (3H, s), 7.82 (1H, d, J=8.51 Hz), 8.22 (1H, s), 8.39 (1H, d, J=8.51 Hz), 8.48 (1H, s), 8.56 (1H, s), 9.07 (1H, s), 10.76 (1H, s); ESIMS found for C m/z 415.15 (M+1).

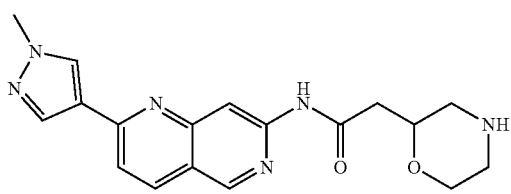

N-(2-(1-Methyl-1H-pyrazol-4-yl)-1,6-naphthyridin-7-yl)-2-(morpholin-2-yl)acetamide 86

Off-white solid (18 mg, 0.05 mmol, 35.6% yield). $^1$H NMR (499 MHz, DMSO-d$_6$) δ ppm 2.41 (1H, dd, J=12.08, 10.15 Hz), 2.45-2.49 (1H, m), 2.57-2.68 (2H, m), 2.82 (1H, dd, J=12.08, 1.92 Hz), 3.43 (1H, td, J=10.84, 3.29 Hz), 3.67-3.73 (1H, m), 3.79-3.86 (1H, m), 3.93 (3H, s), 7.82 (1H, d, J=8.51 Hz), 8.22 (1H, s), 8.39 (1H, d, J=8.78 Hz), 8.48 (1H, s), 8.56 (1H, s), 9.05 (1H, s), 10.63 (1H, s); ESIMS found for C m/z 353.2 (M+1).

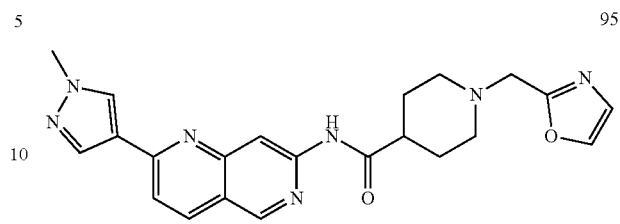

N-(2-(1-Methyl-1H-pyrazol-4-yl)-1,6-naphthyridin-7-yl)-1-(oxazol-2-ylmethyl)piperidine-4-carboxamide 95

White solid (26 mg, 0.06 mmol, 47.4% yield). $^1$H NMR (499 MHz, DMSO-d$_6$) δ ppm 1.62-1.73 (2H, m), 1.80 (2H, br d, J=10.70 Hz), 2.10 (2H, td, J=11.60, 2.06 Hz), 2.52-2.58 (1H, m), 2.89 (2H, br d, J=11.25 Hz), 3.67 (2H, s), 3.93 (3H, s), 7.18 (1H, d, J=0.82 Hz), 7.81 (1H, d, J=8.51 Hz), 8.08 (1H, d, J=0.82 Hz), 8.21 (1H, s), 8.38 (1H, d, J=7.96 Hz), 8.47 (1H, s), 8.55 (1H, s), 9.05 (1H, s), 10.60 (1H, s); ESIMS found for C m/z 418.2 (M+1).

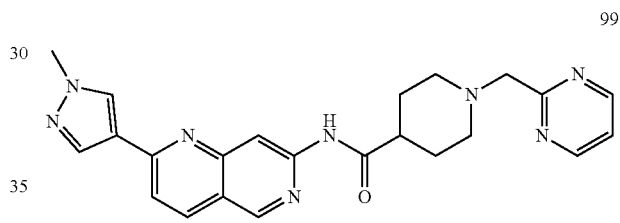

N-(2-(1-Methyl-1H-pyrazol-4-yl)-1,6-naphthyridin-7-yl)-1-(pyrimidin-2-ylmethyl)piperidine-4-carboxamide 99

Beige solid (15 mg, 0.04 mmol, 39.3% yield). $^1$H NMR (499 MHz, DMSO-d$_6$) δ ppm 1.68 (2H, qd, J=12.12, 3.70 Hz), 1.76-1.82 (2H, m), 2.12-2.20 (2H, m), 2.51-2.59 (1H, m), 2.96 (2H, br d, J=11.25 Hz), 3.72 (2H, s), 3.93 (3H, s), 7.40 (1H, t, J=4.94 Hz), 7.80 (1H, d, J=8.51 Hz), 8.21 (1H, s), 8.38 (1H, d, J=8.51 Hz), 8.47 (1H, s), 8.54 (1H, s), 8.79 (2H, d, J=4.94 Hz), 9.04 (1H, s), 10.60 (1H, s); ESIMS found for C m/z 429.2 (M+1).

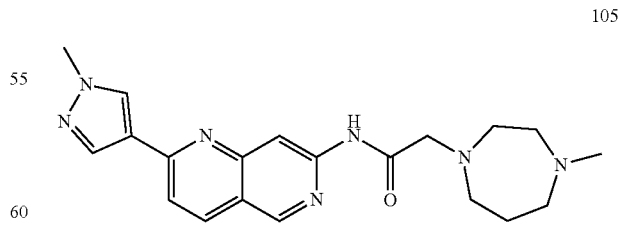

2-(4-Methyl-1,4-diazepan-1-yl)-N-(2-(1-methyl-1H-pyrazol-4-yl)-1,6-naphthyridin-7-yl)acetamide 105

Yellow gum (5 mg, 0.01 mmol, 5.9% yield). $^1$H NMR (499 MHz, DMSO-d$_6$) δ ppm 1.78 (2H, br s), 2.29 (3H, s), 2.59 (4H, br s), 2.83 (4H, br s), 3.38 (2H, s), 3.93 (3H, s), 7.83 (1H, br d, J=8.23 Hz), 8.23 (1H, s), 8.41 (1H, br d, J=8.51 Hz), 8.48 (1H, s), 8.58 (1H, s), 9.08 (1H, s), 10.09 (1H, br s); ESIMS found for C m/z 380.2 (M+1).

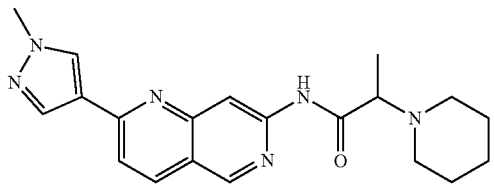

N-(2-(1-Methyl-1H-pyrazol-4-yl)-1,6-naphthyridin-7-yl)-2-(piperidin-1-yl)propanamide 112

Brown solid (49 mg, 0.13 mmol, 40.4% yield). $^1$H NMR (499 MHz, DMSO-d$_6$) δ ppm 1.20 (3H, d, J=6.86 Hz), 1.41-1.47 (2H, m), 1.58 (4H, dq, J=11.49, 5.87 Hz), 2.51-2.58 (4H, m), 3.47 (1H, q, J=6.86 Hz), 3.93 (3H, s), 7.83 (1H, d, J=8.51 Hz), 8.22 (1H, s), 8.38-8.43 (1H, m), 8.47 (1H, s), 8.57 (1H, s), 9.07 (1H, s), 10.23 (1H, s); ESIMS found for C m/z 365.2 (M+1).

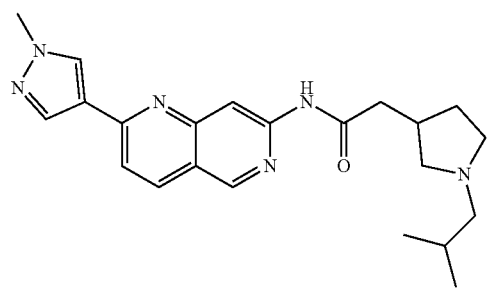

2-(1-Isobutylpyrrolidin-3-yl)-N-(2-(1-methyl-1H-pyrazol-4-yl)-1,6-naphthyridin-7-yl)acetamide 122

White solid (4 mg, 0.01 mmol, 13.7% yield). $^1$H NMR (499 MHz, DMSO-d$_6$) δ ppm 0.85 (6H, dd, J=6.59, 1.65 Hz), 1.37-1.46 (1H, m), 1.65 (1H, dquin, J=13.55, 6.84, 6.84, 6.84, 6.84 Hz), 1.89-1.99 (1H, m), 2.08-2.19 (3H, m), 2.38-2.49 (2H, m), 2.51-2.58 (3H, m), 2.63-2.69 (1H, m), 3.93 (3H, s), 7.80 (1H, d, J=8.78 Hz), 8.21 (1H, s), 8.38 (1H, d, J=8.51 Hz), 8.48 (1H, s), 8.55 (1H, s), 9.04 (1H, s), 10.65 (1H, s); ESIMS found for C m/z 393.3 (M+1).

N-(2-(1-Methyl-1H-pyrazol-4-yl)-1,6-naphthyridin-7-yl)-2-(4-methylpiperazin-1-yl)isonicotinamide 147

Yellow solid (21.3 mg, 0.050 mmol, 14.4% yield). $^1$H NMR (499 MHz, DMSO-d$_6$) δ ppm 2.23 (3H, s), 2.43 (4H, t, J=4.94 Hz), 3.57-3.64 (4H, m), 3.94 (3H, s), 7.13-7.20 (1H, m), 7.46 (1H, s), 7.87 (1H, d, J=8.51 Hz), 8.25 (1H, s), 8.26 (1H, d, J=4.94 Hz), 8.45 (1H, d, J=8.51 Hz), 8.59 (1H, s), 8.63 (1H, s), 9.15 (1H, s), 11.18 (1H, s); ESIMS found for C$_{23}$H$_{24}$N$_8$O m/z 429.2 (M+1).

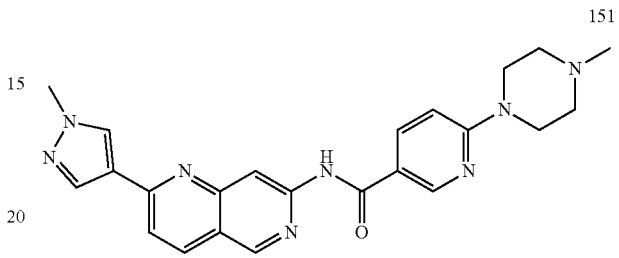

N-(2-(1-Methyl-1H-pyrazol-4-yl)-1,6-naphthyridin-7-yl)-6-(4-methylpiperazin-1-yl)nicotinamide 151

White solid (29.3 mg, 0.07 mmol, 24.8% yield). $^1$H NMR (499 MHz, DMSO-d$_6$) δ ppm 2.22 (3H, s), 2.37-2.43 (4H, m), 3.61-3.68 (4H, m), 3.94 (3H, s), 6.90 (1H, d, J=9.33 Hz), 7.84 (1H, d, J=8.78 Hz), 8.20 (1H, dd, J=9.06, 2.47 Hz), 8.24 (1H, s), 8.42 (1H, d, J=8.78 Hz), 8.58 (1H, s), 8.61 (1H, s), 8.85 (1H, d, J=2.47 Hz), 9.12 (1H, s), 10.78 (1H, s); ESIMS found for C m/z 429.2 (M+1).

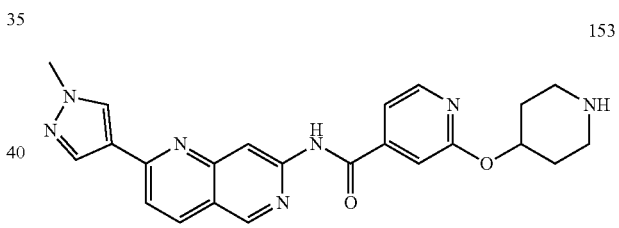

N-(2-(1-Methyl-1H-pyrazol-4-yl)-1,6-naphthyridin-7-yl)-2-(piperidin-4-yloxy)isonicotinamide 153

Yellow solid (5.3 mg, 0.01 mmol, 13.8% yield). $^1$H NMR (499 MHz, DMSO-d$_6$) δ ppm 1.47-1.58 (2H, m), 1.93-2.01 (2H, m), 2.56-2.63 (2H, m), 2.93-3.02 (2H, m), 3.94 (3H, s), 5.05-5.14 (1H, m), 7.34 (1H, s), 7.50 (1H, dd, J=5.35, 1.51 Hz), 7.88 (1H, d, J=8.51 Hz), 8.25 (1H, s), 8.31 (1H, d, J=5.21 Hz), 8.45 (1H, d, J=8.51 Hz), 8.60 (2H, d, J=8.51 Hz), 9.15 (1H, s), 11.20 (1H, br s); ESIMS found for C m/z 430.2 (M+1).

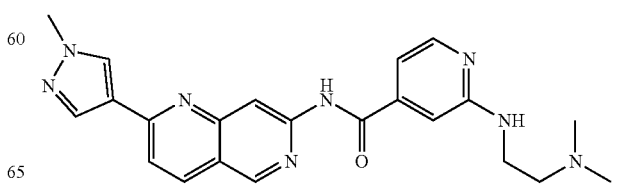

2-((2-(Dimethylamino)ethyl)amino)-N-(2-(1-methyl-1H-pyrazol-4-yl)-1,6-naphthyridin-7-yl)isonicotinamide 164

Light yellow wax (16.6 mg, 0.04 mmol, 7.0% yield). $^1$H NMR (499 MHz, DMSO-$d_6$) δ ppm 2.19 (6H, s), 2.43 (2H, t, J=6.72 Hz), 3.36-3.43 (2H, m), 3.94 (3H, s), 6.63 (1H, brt, J=5.35 Hz), 7.03 (1H, dd, J=5.21, 1.37 Hz), 7.05 (1H, s), 7.87 (1H, d, J=8.51 Hz), 8.11 (1H, d, J=5.49 Hz), 8.24 (1H, s), 8.45 (1H, d, J=8.23 Hz), 8.60 (2H, d, J=6.04 Hz), 9.14 (1H, s), 10.97 (1H, s); ESIMS found for C m/z 417.2 (M+1).

N-(2-(1-Methyl-1H-pyrazol-4-yl)-1,6-naphthyridin-7-yl)-3-phenylpropanamide 194

Yellow wax (31.4 mg, 0.09 mmol, 38.3% yield). $^1$H NMR (500 MHz, DMSO-$d_6$) δ ppm 2.74-2.81 (2H, m), 2.92-2.98 (2H, m), 3.93 (3H, s), 7.16-7.20 (1H, m), 7.28 (2H, s), 7.29 (1H, d, J=2.20 Hz), 7.81 (1H, d, J=8.51 Hz), 8.22 (1H, s), 8.38 (1H, d, J=8.51 Hz), 8.49 (1H, s), 8.57 (1H, s), 9.05 (1H, s), 10.70 (1H, s); ESIMS found for C m/z 358.2 (M+1).

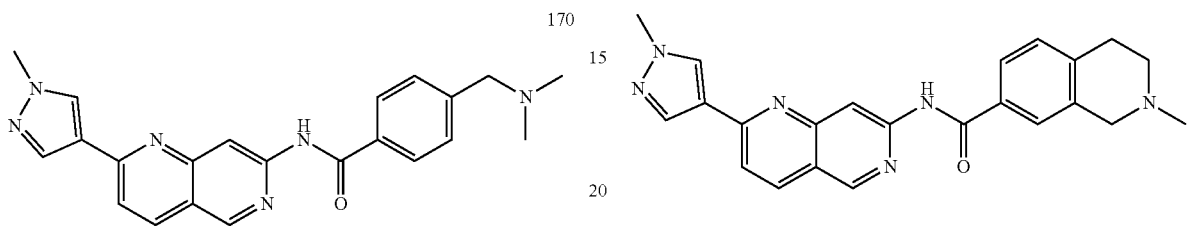

4-((Dimethylamino)methyl)-N-(2-(1-methyl-1H-pyrazol-4-yl)-1,6-naphthyridin-7-yl)benzamide 170

Yellow solid (20.5 mg, 0.05 mmol, 14.9% yield). $^1$H NMR (499 MHz, DMSO-$d_6$) δ ppm 2.18 (6H, s), 3.47 (2H, s), 3.94 (3H, s), 7.44 (2H, d, J=8.23 Hz), 7.86 (1H, d, J=8.51 Hz), 8.05 (2H, d, J=8.23 Hz), 8.24 (1H, s), 8.42-8.46 (1H, m), 8.59 (1H, s), 8.64 (1H, s), 9.14 (1H, s), 10.93 (1H, s); ESIMS found for C m/z 387.2 (M+1).

2-Methyl-N-(2-(1-methyl-1H-pyrazol-4-yl)-1,6-naphthyridin-7-yl)-1,2,3,4-tetrahydroisoquinoline-7-carboxamide 202

Yellow solid (30.4 mg, 0.07 mmol, 21.1% yield). $^1$H NMR (499 MHz, DMSO-$d_6$) δ ppm 2.37 (3H, s), 2.63 (2H, t, J=5.90 Hz), 2.89 (2H, t, J=5.76 Hz), 3.56 (2H, s), 3.94 (3H, s), 7.25 (1H, d, J=7.96 Hz), 7.81 (1H, s), 7.84 (1H, dd, J=7.96, 1.92 Hz), 7.85 (1H, d, J=8.78 Hz), 8.24 (1H, s), 8.41-8.47 (1H, m), 8.59 (1H, s), 8.63 (1H, s), 9.13 (1H, s), 10.84 (1H, s); ESIMS found for $C_{23}H_{22}N_6O$ m/z 399.2 (M+1).

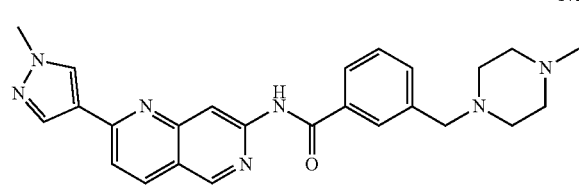

N-(2-(1-Methyl-1H-pyrazol-4-yl)-1,6-naphthyridin-7-yl)-3-((4-methylpiperazin-1-yl)methyl)benzamide 172

Yellow solid (12.4 mg, 0.03 mmol, 6.5% yield). $^1$H NMR (500 MHz, DMSO-$d_6$) δ ppm 2.15 (3H, s), 2.24-2.37 (4H, m), 2.37-2.47 (4H, m), 3.54 (2H, s), 3.94 (3H, s), 7.45-7.50 (1H, m), 7.51-7.57 (1H, m), 7.86 (1H, d, J=8.78 Hz), 7.97 (1H, d, J=7.68 Hz), 7.98 (1H, s), 8.25 (1H, s), 8.44 (1H, d, J=8.51 Hz), 8.59 (1H, s), 8.64 (1H, s), 9.14 (1H, s), 10.97 (1H, s); ESIMS found for C m/z 442.2 (M+1).

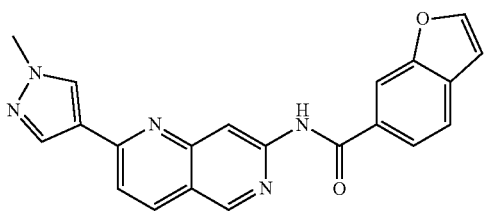

N-(2-(1-Methyl-1H-pyrazol-4-yl)-1,6-naphthyridin-7-yl)benzofuran-6-carboxamide 209

Yellow solid (18.6 mg, 0.05 mmol, 22.7% yield). H NMR (499 MHz, DMSO-$d_6$) δ ppm 3.95 (3H, s), 7.09 (1H, dd, J=2.20, 0.82 Hz), 7.80 (1H, d, J=8.23 Hz), 7.87 (1H, d, J=8.51 Hz), 8.02 (1H, dd, J=8.23, 1.37 Hz), 8.20 (1H, d, J=2.20 Hz), 8.25 (1H, s), 8.40 (1H, s), 8.45 (1H, d, J=8.51 Hz), 8.60 (1H, s), 8.67 (1H, s), 9.16 (1H, s), 11.03 (1H, s); ESIMS found for C m/z 370.1 (M+1).

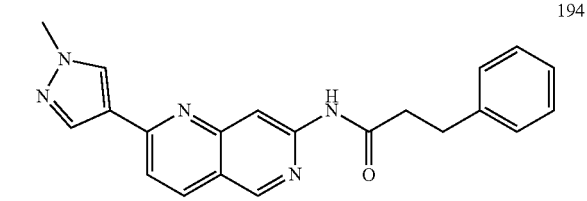 [SMILES: Cn1cc(-c2ccc3cnc(NC(=O)CCc4ccccc4)cc3n2)cn1]

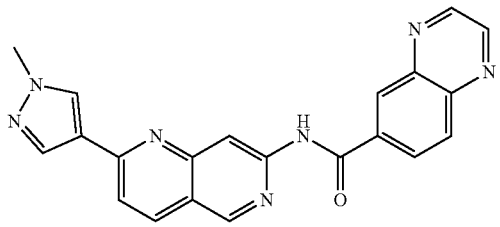

N-(2-(1-Methyl-1H-pyrazol-4-yl)-1,6-naphthyridin-7-yl)quinoxaline-6-carboxamide 216

Yellow solid (7.1 mg, 0.02 mmol, 4.2% yield). $^1$H NMR (499 MHz, DMSO-d$_6$) δ ppm 3.95 (3H, s), 7.89 (1H, d, J=8.78 Hz), 8.24 (1H, d, J=8.78 Hz), 8.26 (1H, s), 8.45 (1H, dd, J=8.78, 1.92 Hz), 8.47 (1H, d, J=8.51 Hz), 8.61 (1H, s), 8.70 (1H, s), 8.86 (1H, d, J=1.92 Hz), 9.08 (2H, dd, J=8.10, 1.78 Hz), 9.19 (1H, s), 11.46 (1H, s); ESIMS found for C m/z 382.1 (M+1).

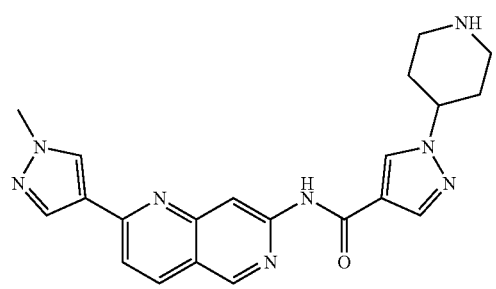

N-(2-(1-Methyl-1H-pyrazol-4-yl)-1,6-naphthyridin-7-yl)-1-(piperidin-4-yl)-1H-pyrazole-4-carboxamide 228

White solid (7.0 mg, 0.017 mmol, 29.1% yield). $^1$H NMR (500 MHz, DMSO-d$_6$) δ ppm 1.77 (2H, qd, J=11.94, 3.98 Hz), 2.00 (2H, br dd, J=11.80, 1.92 Hz), 2.56-2.63 (2H, m), 3.01-3.07 (2H, m), 3.94 (3H, s), 4.20-4.29 (1H, m), 7.83 (1H, d, J=8.78 Hz), 8.19 (1H, s), 8.23 (1H, s), 8.41 (1H, d, J=8.23 Hz), 8.58 (1H, s), 8.59 (1H, s), 8.62 (1H, s), 9.11 (1H, s), 10.65 (1H, s); ESIMS found for C$_{21}$H$_{22}$N$_8$O m/z 403.2 (M+1).

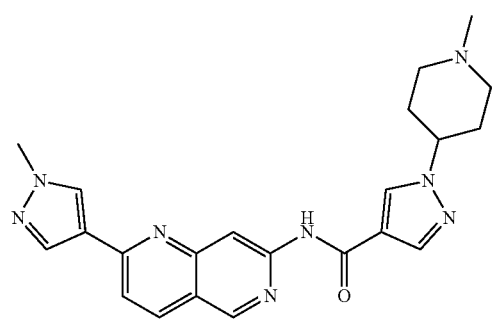

N-(2-(1-Methyl-1H-pyrazol-4-yl)-1,6-naphthyridin-7-yl)-1-(1-methylpiperidin-4-yl)-1H-pyrazole-4-carboxamide 229

Yellow solid (8 mg, 0.02 mmol, 22.3% yield). $^1$H NMR (499 MHz, DMSO-d$_6$) δ ppm 1.88-2.00 (2H, m), 2.01-2.10 (4H, m), 2.21 (3H, s), 2.86 (2H, br d, J=11.80 Hz), 3.94 (3H, s), 4.17 (1H, tt, J=11.11, 4.12 Hz), 7.83 (1H, d, J=8.51 Hz), 8.20 (1H, s), 8.23 (1H, s), 8.41 (1H, d, J=7.96 Hz), 8.58 (2H, d, J=6.59 Hz), 8.63 (1H, s), 9.11 (1H, s), 10.65 (1H, s); ESIMS found for C m/z 417.2 (M+1).

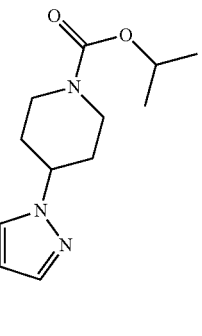

Isopropyl 4-(4-((2-(1-methyl-1H-pyrazol-4-yl)-1,6-naphthyridin-7-yl)carbamoyl)-1H-pyrazol-1-yl)piperidine-1-carboxylate 234

White solid (9.6 mg, 0.02 mmol, 24.0% yield). $^1$H NMR (499 MHz, DMSO-d$_6$) δ ppm 1.21 (6H, d, J=6.04 Hz), 1.80 (2H, qd, J=12.08, 4.39 Hz), 2.08 (2H, br dd, J=12.35, 2.20 Hz), 2.98 (2H, br s), 3.94 (3H, s), 4.04-4.12 (2H, m), 4.45 (1H, tt, J=11.32, 3.91 Hz), 4.80 (1H, spt, J=6.22 Hz), 7.83 (1H, d, J=8.78 Hz), 8.21 (1H, s), 8.23 (1H, s), 8.41 (1H, d, J=7.96 Hz), 8.58 (1H, s), 8.59 (1H, s), 8.65 (1H, s), 9.11 (1H, s), 10.65 (1H, s) ESIMS found for C m/z 489.3 (M+1).

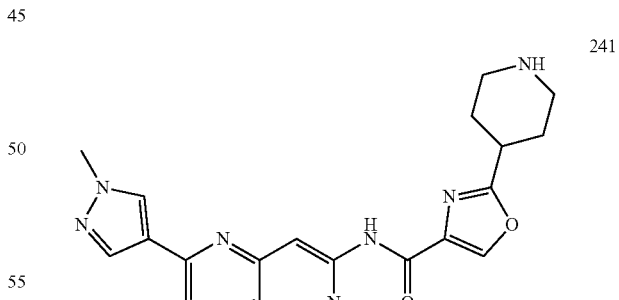

N-(2-(1-Methyl-1H-pyrazol-4-yl)-1,6-naphthyridin-7-yl)-2-(piperidin-4-yl) oxazole-4-carboxamide 241

Off-white solid (64.0 mg, 0.159 mmol, 61.4% yield). $^1$H NMR (499 MHz, DMSO-d$_6$) δ ppm 1.63 (2H, qd, J=11.85, 3.70 Hz), 1.95 (2H, br dd, J=12.49, 2.61 Hz), 2.59 (2H, td, J=11.80, 2.47 Hz), 2.96-3.05 (3H, m), 3.94 (3H, s), 7.87 (1H, d, J=8.51 Hz), 8.24 (1H, s), 8.45 (1H, d, J=8.51 Hz), 8.54

(1H, s), 8.60 (1H, s), 8.88 (1H, s), 9.12 (1H, d, J=0.82 Hz), 9.85 (1H, br s); ESIMS found for $C_{21}H_{21}N_7O_2$ m/z 404.2 (M+1).

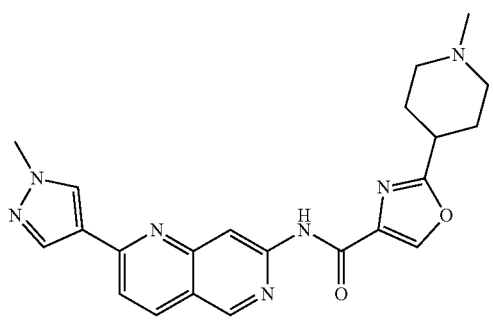

242

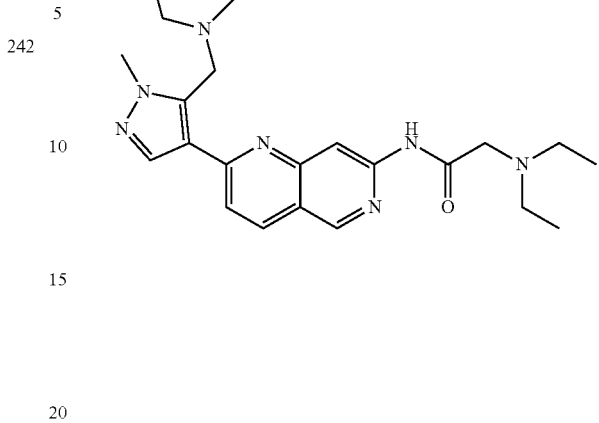

283

N-(2-(1-Methyl-1H-pyrazol-4-yl)-1,6-naphthyridin-7-yl)-2-(1-methylpiperidin-4-yl)oxazole-4-carboxamide 242

2-(Diethylamino)-N-(2-(1-methyl-5-(piperidin-1-ylmethyl)-1H-pyrazol-4-yl)-1,6-naphthyridin-7-yl)acetamide 283

White solid (31.0 mg, 0.074 mmol, 59.9% yield). $^1$H NMR (499 MHz, DMSO-d$_6$) δ ppm 1.73-1.85 (2H, m), 1.99-2.08 (4H, m), 2.19 (3H, s), 2.79 (2H, br d, J=11.25 Hz), 2.88 (1H, tt, J=11.25, 3.70 Hz), 3.94 (3H, s), 7.87 (1H, d, J=8.78 Hz), 8.24 (1H, s), 8.45 (1H, d, J=8.51 Hz), 8.54 (1H, s), 8.60 (1H, s), 8.88 (1H, s), 9.12 (1H, s), 9.86 (1H, s); ESIMS found for $C_{22}H_{23}N_7O_2$ m/z 418.2 (M+1).

Beige solid (3 mg, 0.007 mmol, 4.4% yield). $^1$H NMR (499 MHz, METHANOL-d$_4$) δ ppm 1.16 (6H, t, J=7.14 Hz), 1.40-1.48 (2H, m), 1.53 (4H, quin, J=5.56 Hz), 2.51 (4H, br s), 2.74 (4H, q, J=7.14 Hz), 3.30 (2H, br s), 4.01 (3H, s), 4.22 (2H, s), 7.86 (1H, d, J=8.51 Hz), 8.09 (1H, s), 8.36 (1H, d, J=8.51 Hz), 8.64 (1H, s), 9.02 (1H, s); ESIMS found for $C_{24}H_{33}N_7O$ m/z 436.3 (M+1).

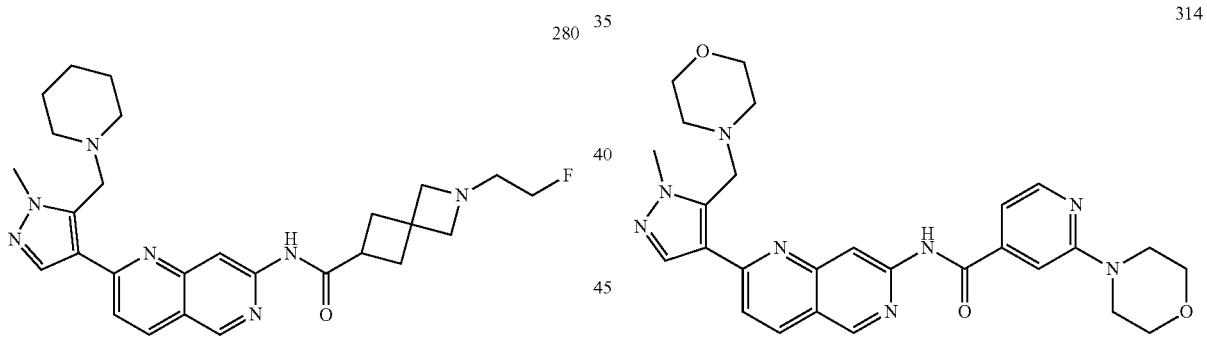

280

314

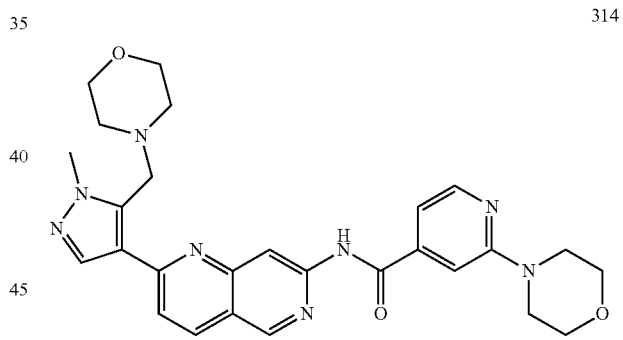

2-(2-Fluoroethyl)-N-(2-(1-methyl-5-(piperidin-1-ylmethyl)-1H-pyrazol-4-yl)-1,6-naphthyridin-7-yl)-2-azaspiro[3.3]heptane-6-carboxamide 280

N-(2-(1-Methyl-5-(morpholinomethyl)-1H-pyrazol-4-yl)-1,6-naphthyridin-7-yl)-2-morpholinoisonicotinamide 314

Beige solid (5 mg, 0.01 mmol, 20.6% yield). $^1$H NMR (499 MHz, METHANOL-d$_4$) δ ppm 1.41-1.47 (2H, m), 1.51-1.58 (4H, m), 2.41-2.48 (2H, m), 2.49-2.57 (5H, m), 2.76 (2H, dt, J=28.10, 5.00 Hz), 3.23-3.30 (2H, m), 3.35 (2H, s), 3.43 (2H, s), 4.01 (3H, s), 4.22 (2H, s), 4.44 (2H, dt, J=47.90, 5.00 Hz), 7.83 (1H, d, J=8.51 Hz), 8.07 (1H, s), 8.33 (1H, dd, J=8.51, 0.82 Hz), 8.59 (1H, s), 8.99 (1H, d, J=0.82 Hz); ESIMS found for $C_{27}H_{34}FN_7O$ m/z 492.3 (M+1).

Off-white solid (10.1 mg, 0.02 mmol, 14.5% yield). $^1$H NMR (499 MHz, DMSO-d$_6$) δ ppm 2.51-2.54 (4H, m), 3.50-3.56 (4H, m), 3.56-3.61 (4H, m), 3.70-3.77 (4H, m), 3.95 (3H, s), 4.30 (2H, s), 7.24 (1H, dd, J=5.08, 1.23 Hz), 7.49 (1H, s), 7.94 (1H, d, J=8.51 Hz), 8.21 (1H, s), 8.30 (1H, d, J=5.21 Hz), 8.43-8.48 (1H, m), 8.67 (1H, s), 9.17 (1H, s), 11.21 (1H, s); ESIMS found for $C_{27}H_{30}N_8O_3$ m/z 515.3 (M+1).

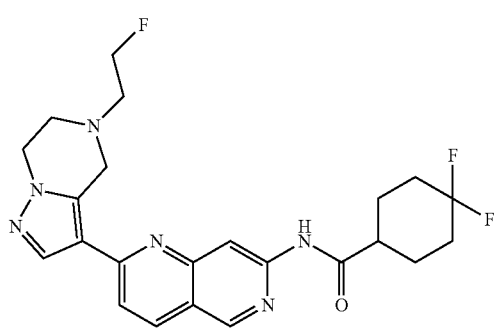

N-((4,4-Difluorocyclohexyl)methyl)-2-(5-(2-fluoro-
ethyl)-4,5,6,7-tetrahydropyrazolo[1,5-a]pyrazin-3-
yl)-1,6-naphthyridin-7-amine 317

Beige solid (8 mg, 0.02 mmol, 5.7% yield). $^1$H NMR (500 MHz, DMSO-$d_6$) δ ppm 1.66-1.76 (2H, m), 1.77-1.91 (2H, m), 1.93-1.99 (2H, m), 2.08-2.17 (2H, m), 2.68-2.77 (1H, m), 3.01 (3H, dt, J=29.10, 5.00 Hz), 3.08 (2H, br t, J=5.35 Hz), 4.20 (2H, br t, J=5.35 Hz), 4.29 (2H, s), 4.68 (3H, dt, J=47.80, 5.00 Hz), 7.85 (1H, d, J=8.78 Hz), 8.29 (1H, s), 8.37 (1H, d, J=8.78 Hz), 8.43 (1H, s), 9.05 (1H, s), 10.71 (1H, s); ESIMS found for $C_{23}H_{25}F_3N_6O$ m/z 459.2 (M+1).

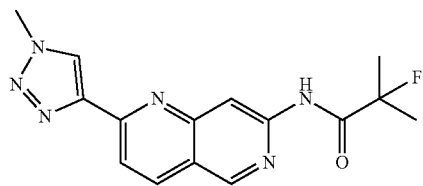

N-(2-(1-Methyl-1H-pyrazol-3-yl)-1,6-naphthyridin-
7-yl)-2-(4-methylpiperazin-1-yl)isonicotinamide 333

White solid (6 mg, 0.02 mmol, 8.6% yield). $^1$H NMR (499 MHz, DMSO-$d_6$) δ ppm 1.65 (6H, d, J=22.00 Hz), 4.52 (3H, s), 8.09 (1H, d, J=8.51 Hz), 8.58 (1H, s), 8.61 (1H, s), 8.66 (1H, d, J=8.78 Hz), 9.29 (1H, s), 10.23 (1H, br s); ESIMS found for $C_{15}H_{15}FN_6O$ m/z 315.1 (M+1).

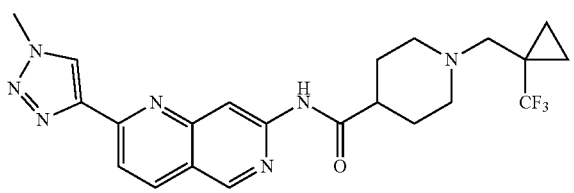

N-(2-(1-Methyl-1H-1,2,3-triazol-4-yl)-1,6-naphthy-
ridin-7-yl)-1-((1-(trifluoromethyl)cyclopropyl)
methyl)piperidine-4-carboxamide 347

White solid (35 mg, 0.08 mmol, 62.9% yield). $^1$H NMR (499 MHz, DMSO-$d_6$) δ ppm 0.73 (2H, s), 0.91-1.00 (2H, m), 1.59-1.71 (2H, m), 1.81 (2H, br d, J=10.98 Hz), 1.89-2.00 (2H, m), 2.55-2.66 (1H, m), 2.96 (2H, br d, J=11.25 Hz), 4.37 (3H, s), 8.06 (1H, s), 8.38 (1H, s), 8.48 (1H, d, J=9.06 Hz), 8.58 (1H, d, J=9.06 Hz), 9.38 (1H, s), 11.10 (1H, s); ESIMS found for $C_{22}H_{24}F_3N_7O$ m/z 460.2 (M+1)

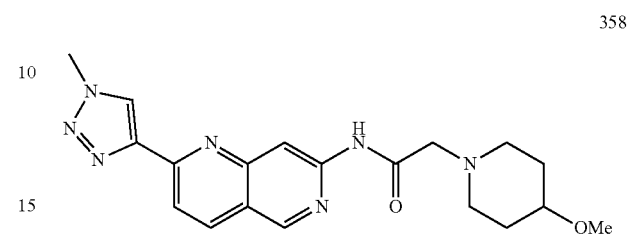

2-(4-Methoxypiperidin-1-yl)-N-(2-(1-methyl-1H-1,
2,3-triazol-4-yl)-1,6-naphthyridin-7-yl)acetamide
358

Off-white solid (12 mg, 0.03 mmol, 19.8% yield). $^1$H NMR (499 MHz, DMSO-$d_6$) δ ppm 1.47-1.57 (2H, m), 1.84-1.94 (2H, m), 2.34-2.42 (2H, m), 2.76-2.83 (2H, m), 3.20-3.24 (1H, m), 3.24 (3H, s), 3.25 (2H, s), 4.52 (3H, s), 8.06 (1H, d, J=8.78 Hz), 8.60 (2H, s), 8.64 (1H, d, J=8.51 Hz), 9.25 (1H, s), 10.25 (1H, s); ESIMS found for $C_{19}H_{23}N_7O_2$ m/z 382.2 (M+1).

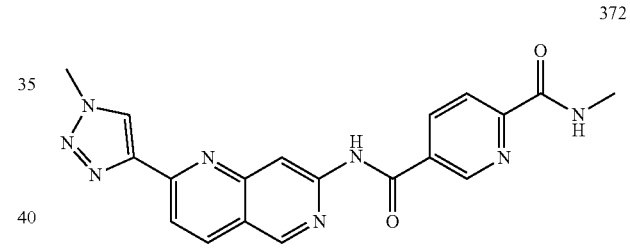

$N^2$-Methyl-$N^5$-(2-(1-methyl-1H-1,2,3-triazol-4-yl)-
1,6-naphthyridin-7-yl) pyridine-2,5-dicarboxamide
372

White solid (4 mg, 0.009 mmol, 7.0% yield). $^1$H NMR (499 MHz, DMSO-$d_6$) δ ppm 2.86 (3H, d, J=4.94 Hz), 4.55 (3H, s), 8.12 (1H, d, J=8.51 Hz), 8.15-8.19 (1H, m), 8.58 (1H, dd, J=8.10, 2.33 Hz), 8.62 (1H, s), 8.67-8.72 (1H, m), 8.81 (1H, s), 8.95 (1H, q, J=4.85 Hz), 9.23 (1H, dd, J=2.20, 0.82 Hz), 9.35 (1H, s), 11.60 (1H, br s); ESIMS found for $C_{19}H_{16}N_8O_2$ m/z 389.15 (M+1).

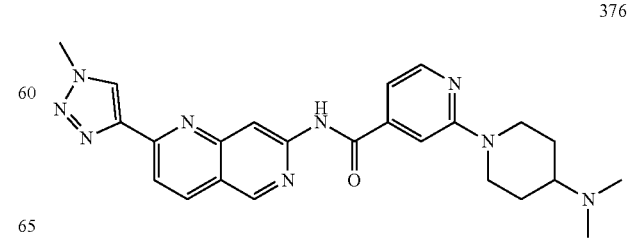

2-(4-(Dimethylamino)piperidin-1-yl)-N-(2-(1-methyl-1H-1,2,3-triazol-4-yl)-1,6-naphthyridin-7-yl) isonicotinamide 376

Off-white solid (15 mg, 0.03 mmol, 33.4% yield). $^1$H NMR (499 MHz, DMSO-$d_6$) δ ppm 1.31-1.44 (2H, m), 1.84 (2H, br d, J=10.98 Hz), 2.19 (6H, s), 2.32-2.39 (1H, m), 2.84-2.95 (2H, m), 4.44 (2H, br d, J=12.90 Hz), 4.54 (3H, s), 7.12 (1H, dd, J=5.21, 1.10 Hz), 7.47 (1H, s), 8.10 (1H, d, J=8.51 Hz), 8.25 (1H, d, J=4.94 Hz), 8.62 (1H, s), 8.68 (1H, d, J=8.51 Hz), 8.79 (1H, s), 9.33 (1H, s), 11.34 (1H, s); ESIMS found for $C_{24}H_{27}N_9O$ m/z 458.25 (M+1).

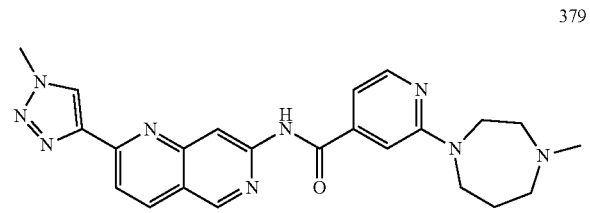 [SMILES: CN1CCCN(c2cc(C(=O)Nc3cc4nc(-c5cn(C)nn5)ccc4cn3)ccn2)CC1]

379

2-(4-Methyl-1,4-diazepan-1-yl)-N-(2-(1-methyl-1H-1,2,3-triazol-4-yl)-1,6-naphthyridin-7-yl)isonicotinamide 379

Beige solid (9.5 mg, 0.02 mmol, 25.7% yield). $^1$H NMR (499 MHz, DMSO-$d_6$) δ ppm 1.89-1.98 (2H, m), 2.27 (3H, s), 2.49 (2H, br s), 2.59-2.67 (2H, m), 3.69 (2H, t, J=6.17 Hz), 3.79-3.85 (2H, m), 4.54 (3H, s), 7.07 (1H, dd, J=5.08, 1.24 Hz), 7.23 (1H, s), 8.10 (1H, d, J=8.51 Hz), 8.22 (1H, d, J=4.94 Hz), 8.62 (1H, s), 8.66-8.73 (1H, m), 8.79 (1H, s), 9.33 (1H, s), 11.33 (1H, s); ESIMS found for $C_{23}H_{25}N_9O$ m/z 444.2 (M+1).

400

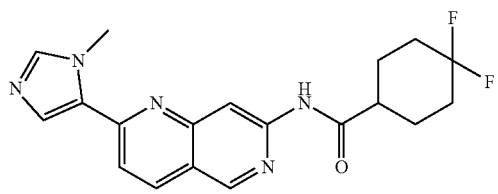

4,4-Difluoro-N-(2-(1-methyl-1H-imidazol-5-yl)-1,6-naphthyridin-7-yl) cyclohexane-1-carboxamide 400

Off-white solid (5 mg, 0.01 mmol, 5.6% yield). $^1$H NMR (499 MHz, DMSO-$d_6$) δ ppm 1.63-1.76 (2H, m), 1.76-1.92 (2H, m), 1.96 (2H, br d, J=13.17 Hz), 2.07-2.19 (2H, m), 2.68-2.78 (1H, m), 4.15 (3H, s), 7.90-7.97 (3H, m), 8.41 (1H, d, J=8.51 Hz), 8.51 (1H, s), 9.10 (1H, s), 10.78 (1H, s); ESIMS found for $C_{19}H_{19}F_2N_5O$ m/z 372.2 (M+1).

416

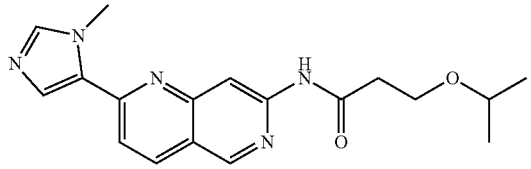

3-Isopropoxy-N-(2-(1-methyl-1H-imidazol-5-yl)-1,6-naphthyridin-7-yl) propanamide 416

White solid (3 mg, 0.009 mmol, 28.4% yield). $^1$H NMR (499 MHz, DMSO-$d_6$) δ ppm 1.08 (6H, d, J=6.04 Hz), 2.67 (2H, t, J=6.17 Hz), 3.58 (1H, dt, J=12.28, 6.07 Hz), 3.69 (2H, t, J=6.17 Hz), 4.15 (3H, s), 7.91 (1H, br s), 7.91 (1H, s), 7.93 (1H, d, J=8.78 Hz), 8.41 (1H, d, J=8.78 Hz), 8.52 (1H, s), 9.09 (1H, s), 10.69 (1H, s); ESIMS found for $C_{18}H_{21}N_5O_2$ m/z 340.2 (M+1).

447

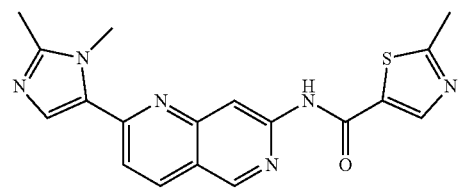

N-(2-(1,2-Dimethyl-1H-imidazol-5-yl)-1,6-naphthyridin-7-yl)-2-methylthiazole-5-carboxamide 447

Reddish brown solid (10 mg, 0.02 mmol, 16.9% yield). $^1$H NMR (499 MHz, DMSO-$d_6$) δ ppm 2.42 (3H, s), 2.72 (3H, s), 4.12 (3H, s), 7.81 (1H, s), 7.92 (1H, d, J=8.78 Hz), 8.41 (1H, d, J=8.78 Hz), 8.54 (1H, s), 8.71 (1H, s), 9.15 (1H, s), 11.32 (1H, s); ESIMS found for $C_{18}H_{16}N_6OS$ m/z 365.1 (M+1).

448

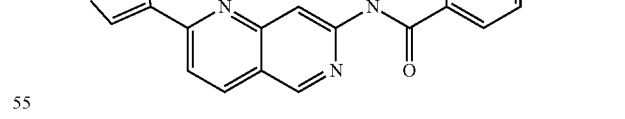

4-Fluoro-N-(2-(1-methyl-1H-imidazol-5-yl)-1,6-naphthyridin-7-yl)benzamide 448

Off-white solid (5 mg, 0.01 mmol, 5.9% yield). $^1$H NMR (499 MHz, DMSO-$d_6$) δ ppm 3.99 (3H, s), 7.34-7.42 (3H, m), 7.60 (1H, s), 7.81 (1H, s), 7.92 (1H, s), 8.14-8.21 (2H, m), 8.43 (1H, d, J=8.78 Hz), 8.57 (1H, d, J=9.06 Hz), 9.33 (1H, s), 11.46 (1H, br s); ESIMS found for $C_{19}H_{14}FN_5O$ m/z 348.15 (M+1).

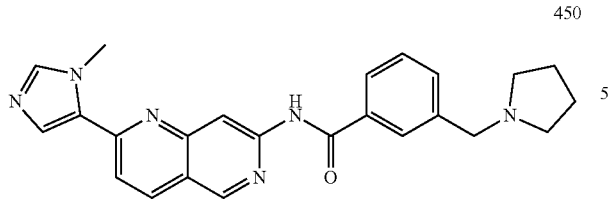

N-(2-(1-Methyl-1H-imidazol-5-yl)-1,6-naphthyridin-7-yl)-3-(pyrrolidin-1-ylmethyl)benzamide 450

Beige solid (5 mg, 0.01 mmol, 5.5% yield). $^1$H NMR (499 MHz, DMSO-$d_6$) δ ppm 1.72 (4H, br s), 2.48 (4H, br s), 3.67 (2H, s), 4.18 (3H, s), 7.45-7.50 (1H, m), 7.55 (1H, br d, J=7.68 Hz), 7.91-7.99 (4H, m), 8.02 (1H, s), 8.46 (1H, d, J=8.78 Hz), 8.67 (1H, s), 9.18 (1H, s), 11.02 (1H, s); ESIMS found for $C_{24}H_{24}N_6O$ m/z 413.2 (M+1).

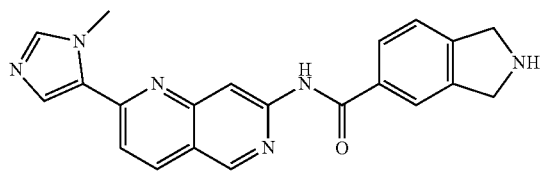

N-(2-(1-Methyl-1H-imidazol-5-yl)-1,6-naphthyridin-7-yl)isoindoline-5-carboxamide 477

Beige solid (23 mg, 0.06 mmol, 32.5% yield). $^1$H NMR (499 MHz, DMSO-$d_6$) δ ppm 4.14 (4H, s), 4.18 (3H, s), 7.40 (1H, d, J=7.68 Hz), 7.91-7.94 (3H, m), 7.96-7.99 (2H, m), 8.45 (1H, d, J=8.78 Hz), 8.67 (1H, s), 9.17 (1H, s), 10.93 (1H, s); ESIMS found for $C_{21}H_{18}N_6O$ m/z 371.1 (M+1).

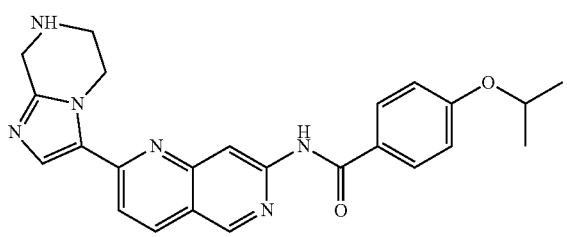

4-Isopropoxy-N-(2-(5,6,7,8-tetrahydroimidazo[1,2-a]pyrazin-3-yl)-1,6-naphthyridin-7-yl)benzamide 523

Yellow solid (2.9 mg, 0.006 mmol, 34.0% yield). $^1$H NMR (499 MHz, DMSO-$d_6$) δ ppm 1.31 (6H, d, J=6.04 Hz), 3.16 (2H, br t, J=5.35 Hz), 3.97 (2H, s), 4.57 (2H, t, J=5.49 Hz), 4.70-4.82 (1H, m), 7.03 (2H, d, J=9.06 Hz), 7.90-7.94 (2H, m), 8.07 (2H, d, J=8.78 Hz), 8.40 (1H, dd, J=8.78, 0.82 Hz), 8.62 (1H, s), 9.12 (1H, s), 10.81 (1H, s); ESIMS found for $C_{24}H_{24}N_6O_2$ m/z 429.2 (M+1)

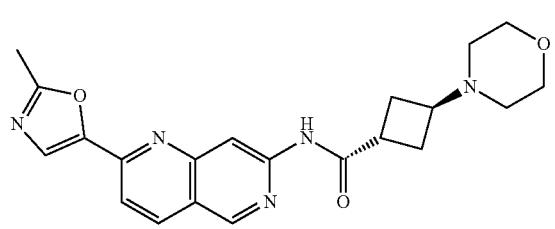

1-(2,2-Difluoropropyl)-N-(2-(oxazol-5-yl)-1,6-naphthyridin-7-yl)piperidine-4-carboxamide 540

White solid (6.7 mg, 0.02 mmol, 18.3% yield). $^1$H NMR (499 MHz, DMSO-$d_6$) δ ppm 1.63 (3H, t, J=19.21 Hz), 1.66-1.75 (2H, m), 1.75-1.83 (2H, m), 2.22 (2H, td, J=11.80, 2.20 Hz), 2.56 (1H, tt, J=11.66, 4.12 Hz), 2.71 (2H, t, J=14.13 Hz), 2.95 (2H, br d, J=11.53 Hz), 7.94 (1H, d, J=8.51 Hz), 8.17 (1H, s), 8.55-8.60 (2H, m), 8.69 (1H, s), 9.20 (1H, s), 10.76 (1H, s); ESIMS found for $C_{20}H_{21}F_2N_5O_2$ m/z 402.2 (M+1).

trans-N-(2-(2-Methyloxazol-5-yl)-1,6-naphthyridin-7-yl)-3-morpholinocyclobutane-1-carboxamide 556

Beige solid (14 mg, 0.04 mmol, 29.5% yield). $^1$H NMR (499 MHz, DMSO-$d_6$) δ ppm 2.08-2.17 (2H, m), 2.24-2.32 (6H, m), 2.58 (3H, s), 2.89 (1H, quin, J=7.07 Hz), 3.26-3.31 (1H, m), 3.59 (4H, t, J=4.39 Hz), 7.87 (1H, d, J=8.51 Hz), 8.03 (1H, s), 8.52 (1H, d, J=8.51 Hz), 8.57 (1H, s), 9.15 (1H, s), 10.67 (1H, s); ESIMS found for $C_{21}H_{23}N_5O_3$ m/z 394.2 (M+1).

N-(2-(2-Methyloxazol-5-yl)-1,6-naphthyridin-7-yl)-4-morpholinopiperidine-1-carboxamide 566

Beige solid (70 mg, 0.17 mmol, 37.5% yield). $^1$H NMR (499 MHz, DMSO-$d_6$) δ ppm 1.28-1.42 (2H, m), 1.80 (2H, br d, J=10.70 Hz), 2.36 (1H, tt, J=10.94, 3.60 Hz), 2.43-2.49

(4H, m), 2.57 (3H, s), 2.84 (2H, br t, J=11.80 Hz), 3.52-3.60 (4H, m), 4.23 (2H, br d, J=13.45 Hz), 7.80 (1H, d, J=8.78 Hz), 8.00 (1H, s), 8.25 (1H, s), 8.48 (1H, d, J=8.51 Hz), 9.10 (1H, s), 9.41 (1H, s); ESIMS found for $C_{22}H_{26}N_6O_3$ m/z 423.2 (M+1).

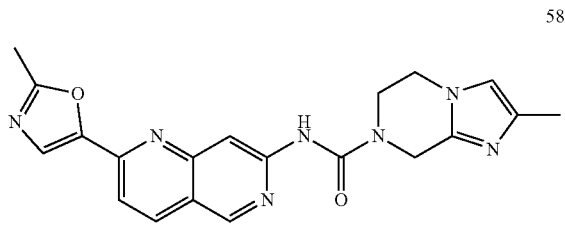

2-Methyl-N-(2-(2-methyloxazol-5-yl)-1,6-naphthyridin-7-yl)-5,6-dihydroimidazo[1,2-a]pyrazine-7(8H)-carboxamide 585

Beige solid (25 mg, 0.06 mmol, 14.5% yield). $^1$H NMR (499 MHz, DMSO-$d_6$) δ ppm 2.07 (3H, d, J=0.82 Hz), 2.58 (3H, s), 3.90-3.97 (2H, m), 3.97-4.02 (2H, m), 4.69 (2H, s), 6.79 (1H, d, J=0.82 Hz), 7.83 (1H, d, J=8.78 Hz), 8.01 (1H, s), 8.28 (1H, s), 8.50 (1H, d, J=7.96 Hz), 9.14 (1H, s), 9.80 (1H, s); ESIMS found for $C_{20}H_{19}N_7O_2$ m/z 390.2 (M+1).

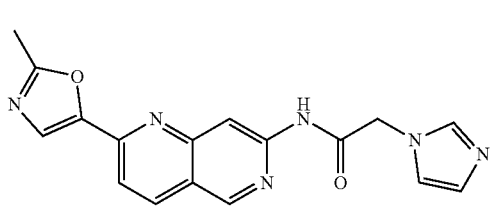

2-(1H-Imidazol-1-yl)-N-(2-(2-methyloxazol-5-yl)-1,6-naphthyridin-7-yl) acetamide 589

Beige solid (15 mg, 0.04 mmol, 18.3% yield). $^1$H NMR (499 MHz, DMSO-$d_6$) δ ppm 2.57 (3H, s), 5.07 (2H, s), 6.99 (1H, s), 7.26 (1H, s), 7.80 (1H, s), 7.91 (1H, d, J=8.78 Hz), 8.03 (1H, s), 8.46 (1H, s), 8.55 (1H, d, J=8.51 Hz), 9.21 (1H, s), 11.17 (1H, s); ESIMS found for $C_{17}H_{14}N_6O_2$ m/z 335.1 (M+1).

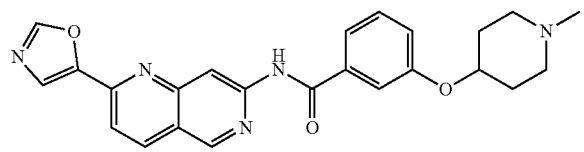

3-((1-Methylpiperidin-4-yl)oxy)-N-(2-(oxazol-5-yl)-1,6-naphthyridin-7-yl)benzamide 591

Yellow solid (5 mg, 0.01 mmol, 6.8% yield). $^1$H NMR (499 MHz, DMSO-$d_6$) δ ppm 1.64-1.73 (2H, m), 1.94-2.01 (2H, m), 2.15-2.25 (2H, m), 2.19 (3H, s), 2.60-2.66 (2H, m), 4.49-4.56 (1H, m), 7.14-7.23 (1H, m), 7.43 (1H, t, J=8.10 Hz), 7.63-7.66 (2H, m), 8.00 (1H, d, J=8.51 Hz), 8.21 (1H, s), 8.60-8.66 (1H, m), 8.71 (1H, s), 8.72 (1H, s), 9.29 (1H, s), 11.10 (1H, s); ESIMS found for $C_{24}H_{23}N_5O_3$ m/z 430.2 (M+1).

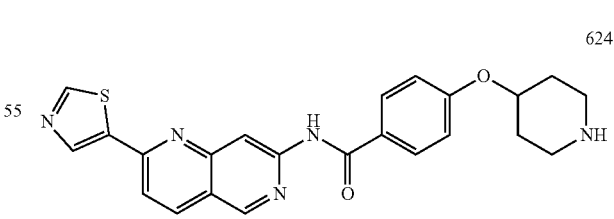

N-(2-(Oxazol-5-yl)-1,6-naphthyridin-7-yl)isonicotinamide 592

Beige solid (39.0 mg, 0.123 mmol, 33.9% yield). $^1$H NMR (499 MHz, DMSO-$d_6$) δ ppm 7.96-7.99 (2H, m), 8.01 (1H, d, J=8.51 Hz), 8.21 (1H, s), 8.64 (1H, dd, J=8.51, 0.82 Hz), 8.71 (1H, s), 8.73 (1H, s), 8.79-8.81 (2H, m), 9.30 (1H, s), 11.44 (1H, s); ESIMS found for $C_{17}H_{11}N_5O_2$ m/z 318.1 (M)+1.

trans-4-((3-Fluoroazetidin-1-yl)methyl)-N-(2-(thiazol-5-yl)-1,6-naphthyridin-7-yl)cyclohexane-1-carboxamide 613

Pale yellow solid (10.5 mg, 0.02 mmol, 15.1% yield). $^1$H NMR (499 MHz, DMSO-$d_6$) δ ppm 0.86-0.98 (2H, m), 1.25-1.34 (1H, m), 1.44 (2H, qd, J=12.76, 3.16 Hz), 1.77-1.83 (2H, m), 1.84-1.90 (2H, m), 2.29 (2H, d, J=6.59 Hz), 2.52-2.56 (1H, m), 2.97-3.08 (2H, m), 3.50-3.59 (2H, m), 5.12 (1H, dquin, J=58.00, 5.00, 5.00, 5.00, 5.00 Hz), 8.17 (1H, d, J=8.51 Hz), 8.50 (1H, s), 8.54 (1H, d, J=8.78 Hz), 8.87 (1H, s), 9.16 (1H, s), 9.29 (1H, s), 10.67 (1H, s); ESIMS found for $C_{22}H_{24}FN_5OS$ m/z 426.15 (M+1).

4-(Piperidin-4-yloxy)-N-(2-(thiazol-5-yl)-1,6-naphthyridin-7-yl)benzamide 624

Beige solid (13.0 mg, 0.030 mmol, 35.6% yield). $^1$H NMR (499 MHz, DMSO-$d_6$) δ ppm 1.41-1.54 (2H, m), 1.90-1.99 (2H, m), 2.56-2.63 (2H, m), 2.95 (2H, dt, J=12.62, 3.84 Hz), 3.17 (1H, d, J=4.39 Hz), 4.55 (1H, tt, J=8.88, 4.15 Hz), 7.06 (2H, d, J=9.06 Hz), 8.07 (2H, d, J=8.78 Hz), 8.21 (1H, d, J=8.51 Hz), 8.58 (1H, d, J=8.51 Hz), 8.66 (1H, s), 8.89 (1H, s), 9.24 (1H, s), 9.31 (1H, s), 10.89 (1H, s); ESIMS found for $C_{23}H_{21}N_5O_2S$ m/z 432.1 (M+1).

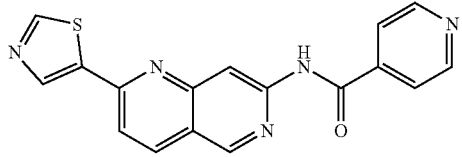

625

N-(2-(Thiazol-5-yl)-1,6-naphthyridin-7-yl)isonicotinamide 625

Beige solid (12.0 mg, 0.036 mmol, 7.0% yield). $^1$H NMR (500 MHz, DMSO-$d_6$) δ ppm 7.95-8.00 (2H, m), 8.26 (1H, d, J=8.51 Hz), 8.59-8.64 (1H, m), 8.67-8.68 (1H, m), 8.78-8.83 (2H, m), 8.91 (1H, s), 9.28 (1H, d, J=0.82 Hz), 9.32 (1H, s), 11.44 (1H, br s); ESIMS found for $C_{17}H_{11}N_5OS$ m/z 334.1 (M+1).

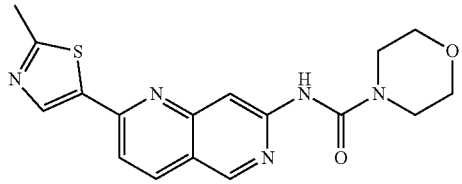

634

N-(2-(2-Methylthiazol-5-yl)-1,6-naphthyridin-7-yl) morpholine-4-carboxamide 634

Beige solid (27.0 mg, 0.076 mmol, 18.4% yield). $^1$H NMR (500 MHz, DMSO-$d_6$) δ ppm 2.73 (3H, s), 3.48-3.54 (4H, m), 3.59-3.65 (4H, m), 8.05 (1H, d, J=8.51 Hz), 8.19-8.23 (1H, m), 8.46 (1H, dd, J=8.78, 0.82 Hz), 8.59 (1H, s), 9.09 (1H, d, J=0.82 Hz), 9.48 (1H, s); ESIMS found for $C_{17}H_7N_5O_2S$ m/z 356.1 (M+1).

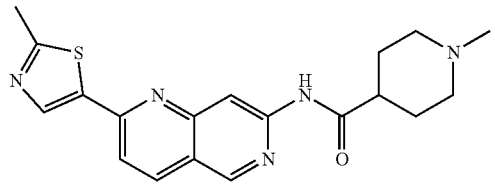

640

1-Methyl-N-(2-(2-methylthiazol-5-yl)-1,6-naphthyridin-7-yl)piperidine-4-carboxamide 640

Beige solid (9.0 mg, 0.025 mmol, 7.5% yield). $^1$H NMR (499 MHz, DMSO-$d_6$) δ ppm 1.63-1.74 (2H, m), 1.76-1.81 (2H, m), 1.84-1.91 (2H, m), 2.16 (3H, s), 2.52-2.56 (1H, m), 2.74 (3H, s), 2.82 (2H, br d, J=11.53 Hz), 8.11 (1H, d, J=8.51 Hz), 8.47 (1H, s), 8.49 (1H, d, J=8.51 Hz), 8.60 (1H, s), 9.13 (1H, s), 10.71 (1H, s); ESIMS found for $C_{19}H_{21}N_5OS$ m/z 368.2 (M+1).

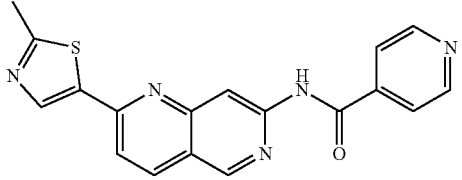

641

N-(2-(2-Methylthiazol-5-yl)-1,6-naphthyridin-7-yl) isonicotinamide 641

White solid (6.0 mg, 0.017 mmol, 4.6% yield). $^1$H NMR (499 MHz, DMSO-$d_6$) δ ppm 2.75 (3H, s), 7.94-8.00 (2H, m), 8.18 (1H, d, J=8.78 Hz), 8.57 (1H, d, J=8.78 Hz), 8.63 (2H, s), 8.77-8.82 (2H, m), 9.25 (1H, s), 11.41 (1H, br s); ESIMS found for $C_{18}H_{13}N_5OS$ m/z 348.1 (M+1).

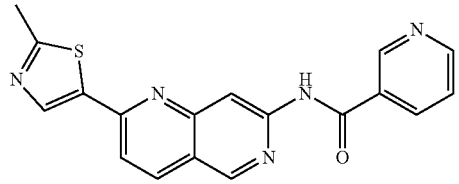

642

N-(2-(2-Methylthiazol-5-yl)-1,6-naphthyridin-7-yl) nicotinamide 642

White solid (9.0 mg, 0.026 mmol, 7.9% yield). $^1$H NMR (499 MHz, DMSO-$d_6$) δ ppm 2.75 (3H, s), 7.54-7.60 (1H, m), 8.17 (1H, d, J=8.78 Hz), 8.41 (1H, dt, J=7.96, 1.92 Hz), 8.56 (1H, d, J=8.51 Hz), 8.63 (1H, s), 8.64 (1H, s), 8.78 (1H, dd, J=4.80, 1.51 Hz), 9.19 (1H, d, J=1.65 Hz), 9.24 (1H, s), 11.37 (1H, s); ESIMS found for $C_{18}H_{13}N_5OS$ m/z 348.1 (M+1).

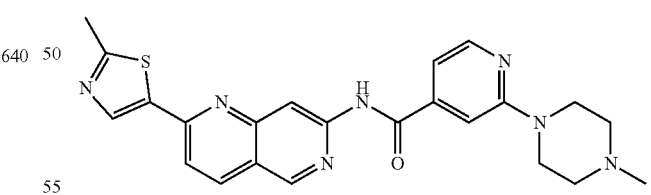

643

2-(4-Methylpiperazin-1-yl)-N-(2-(2-methylthiazol-5-yl)-1,6-naphthyridin-7-yl)isonicotinamide 643

Brown solid (6.0 mg, 0.014 mmol, 7.4% yield). $^1$H NMR (499 MHz, DMSO-$d_6$) δ ppm 2.24 (3H, s), 2.40-2.46 (4H, m), 2.74 (3H, s), 3.58-3.64 (4H, m), 7.16 (1H, dd, J=5.08, 1.23 Hz), 7.47 (1H, s), 8.17 (1H, d, J=8.51 Hz), 8.27 (1H, d, J=5.21 Hz), 8.56 (1H, dd, J=8.78, 0.82 Hz), 8.63 (2H, s), 9.24 (1H, d, J=0.82 Hz), 11.27 (1H, s); ESIMS found for $C_{23}H_{23}N_7OS$ m/z 446.2 (M+1).

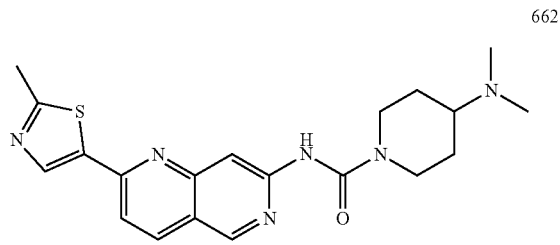

662

4-(Dimethylamino)-N-(2-(2-methylthiazol-5-yl)-1,6-naphthyridin-7-yl)piperidine-1-carboxamide 662

Beige solid (10.0 mg, 0.025 mmol, 12.2% yield). $^1$H NMR (500 MHz, DMSO-$d_6$) δ ppm 1.28-1.38 (2H, m), 1.74-1.80 (2H, m), 2.18 (6H, s), 2.27-2.34 (1H, m), 2.73 (3H, s), 2.80-2.89 (2H, m), 4.21 (2H, br d, J=13.45 Hz), 8.03 (1H, d, J=8.78 Hz), 8.18 (1H, s), 8.45 (1H, dd, J=8.78, 0.82 Hz), 8.58 (1H, s), 9.08 (1H, s), 9.41 (1H, s); ESIMS found for $C_{20}H_{24}N_6OS$ m/z 397.2 (M+1).

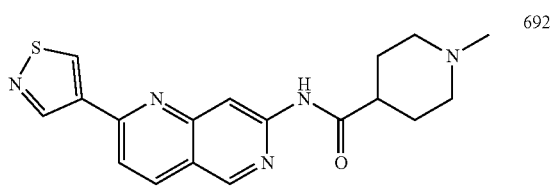 [SMILES: CN1CCC(C(=O)Nc2cc3nc(-c4cnsc4)ccc3cn2)CC1]

692

N-(2-(Isothiazol-4-yl)-1,6-naphthyridin-7-yl)-1-methylpiperidine-4-carboxamide 692

Beige solid (50 mg, 0.14 mmol, 32.3% yield). $^1$H NMR (499 MHz, DMSO-$d_6$) δ ppm 1.80-1.94 (2H, m), 2.03-2.14 (2H, m), 2.51-2.53 (1H, m), 2.81 (3H, s), 2.98 (2H, br s), 3.49 (2H, br s), 8.14 (1H, d, J=8.78 Hz), 8.53-8.62 (2H, m), 9.21 (1H, s), 9.38 (1H, s), 9.90 (1H, s), 10.96 (1H, s); ESIMS found for $C_{18}H_{19}N_5OS$ m/z 354.1 (M+1).

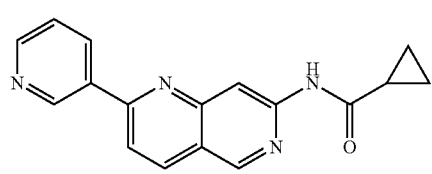

764

N-(2-(Pyridin-3-yl)-1,6-naphthyridin-7-yl)cyclopropanecarboxamide 764

White solid (30 mg, 0.10 mmol, 51.2% yield). $^1$H NMR (499 MHz, DMSO-$d_6$) δ ppm 0.82-0.91 (4H, m), 2.22-2.33 (1H, m), 7.57 (1H, dd, J=7.82, 4.80 Hz), 7.98 (1H, dd, J=8.23, 1.65 Hz), 8.08 (1H, s), 8.19 (1H, d, J=8.23 Hz), 8.30 (1H, dt, J=8.23, 1.78 Hz), 8.68 (1H, dd, J=4.67, 1.37 Hz), 9.08 (1H, d, J=1.92 Hz), 9.54 (1H, s), 11.04 (1H, s); ESIMS found for $C_{17}H_{14}N_4O$ m/z 291.1 (M+1).

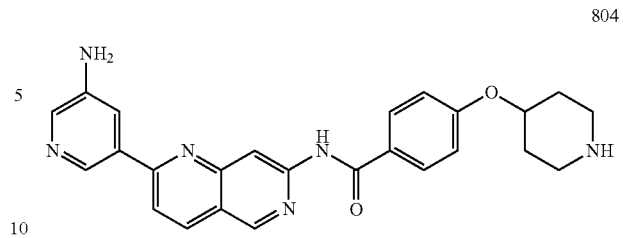

804

N-(2-(5-Aminopyridin-3-yl)-1,6-naphthyridin-7-yl)-4-(piperidin-4-yloxy)benzamide 804

Beige solid (1.3 mg, 0.003 mmol, 37.8% yield). $^1$H NMR (499 MHz, DMSO-$d_6$) δ ppm 1.47-1.59 (2H, m), 1.93-2.02 (2H, m), 2.62-2.72 (2H, m), 3.00 (2H, dt, J=12.76, 4.19 Hz), 4.53-4.65 (1H, m), 5.59 (2H, s), 7.07 (2H, d, J=8.78 Hz), 7.88 (1H, t, J=2.20 Hz), 8.05-8.10 (3H, m), 8.12 (1H, d, J=8.51 Hz), 8.54-8.60 (1H, m), 8.61 (1H, d, J=1.92 Hz), 8.76 (1H, s), 9.28 (1H, s), 10.90 (1H, s); ESIMS found for $C_{25}H_{24}N_6O_2$ m/z 441.2 (M+1).

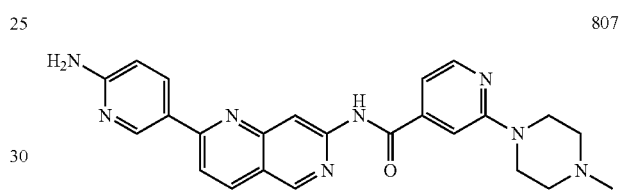

807

N-(2-(6-Aminopyridin-3-yl)-1,6-naphthyridin-7-yl)-2-(4-methylpiperazin-1-yl)isonicotinamide 807

Beige solid (25 mg, 0.06 mmol, 29.0% yield). $^1$H NMR (499 MHz, DMSO-$d_6$) δ ppm 2.23 (3H, s), 2.43 (4H, t, J=4.94 Hz), 3.56-3.66 (4H, m), 6.56-6.65 (3H, m), 7.16 (1H, dd, J=4.94, 1.10 Hz), 7.47 (1H, s), 8.08 (1H, d, J=8.78 Hz), 8.26 (1H, d, J=4.94 Hz), 8.35 (1H, dd, J=8.78, 2.20 Hz), 8.46 (1H, d, J=8.78 Hz), 8.66 (1H, s), 8.92 (1H, d, J=2.47 Hz), 9.18 (1H, s), 11.19 (1H, s); ESIMS found for $C_{24}H_{24}N_8O$ m/z 441.2 (M+1).

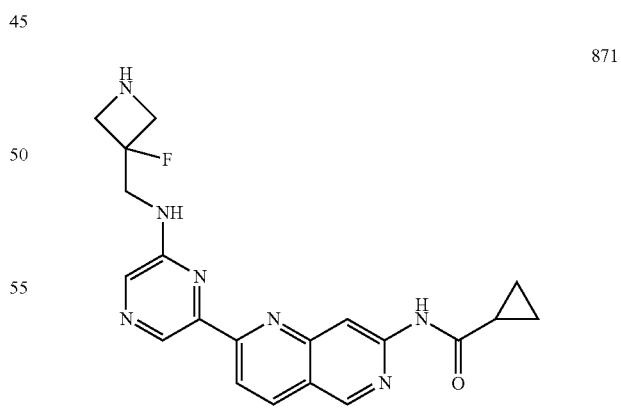

871

N-(2-(6-(((3-Fluoroazetidin-3-yl)methyl)amino)pyrazin-2-yl)-1,6-naphthyridin-7-yl)cyclopropanecarboxamide 871

Yellow solid (1 mg, 0.003 mmol, 24.1% yield). $^1$H NMR (499 MHz, METHANOL-$d_4$) δ ppm 0.91-0.98 (2H, m), 1.02-1.09 (2H, m), 1.94-2.01 (1H, m), 3.33-3.39 (2H, m), 3.64-3.69 (2H, m), 4.04 (2H, d, J=22.50 Hz), 8.06 (1H, s), 8.49-8.53 (1H, m), 8.55-8.58 (1H, m), 8.66 (1H, s), 8.89 (1H, s), 9.13 (1H, d, J=0.82 Hz); ESIMS found for C$_{21}$H$_{22}$FN$_7$O m/z 408.2 (M+1).

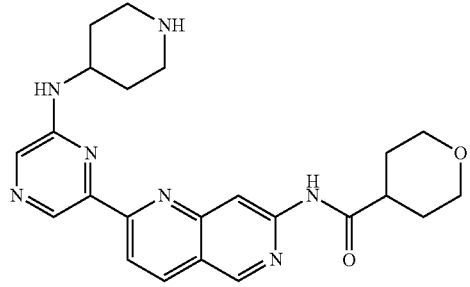

N-(2-(6-(Piperidin-4-ylamino)pyrazin-2-yl)-1,6-naphthyridin-7-yl)tetrahydro-2H-pyran-4-carboxamide 877

Beige solid (40 mg, 0.09 mmol, 70.3% yield). $^1$H NMR (500 MHz, DMSO-d$_6$) δ ppm 1.32-1.44 (2H, m), 1.64-1.81 (4H, m), 1.91-2.00 (2H, m), 2.57-2.67 (2H, m), 2.81-2.91 (1H, m), 2.96-3.04 (2H, m), 3.35-3.40 (2H, m), 3.93 (3H, dt, J=9.26, 1.96 Hz), 7.28 (1H, d, J=7.14 Hz), 8.05 (1H, s), 8.36 (1H, d, J=8.51 Hz), 8.60 (1H, d, J=8.51 Hz), 8.62 (1H, s), 8.78 (1H, s), 9.23 (1H, s), 10.78 (1H, s); ESIMS found for C$_{23}$H$_{27}$N$_7$O$_2$ m/z 434.2 (M+1).

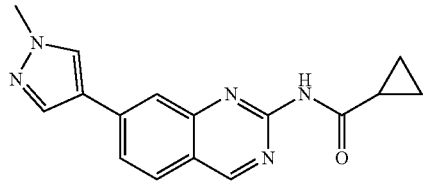

N-(2-(6-(Azetidin-3-ylmethoxy)pyrazin-2-yl)-1,6-naphthyridin-7-yl)-4-fluorobenzamide 892

Yellow solid (12 mg, 0.03 mmol, 58.5% yield). $^1$H NMR (499 MHz, DMSO-d$_6$) δ ppm 3.11 (1H, br d, J=4.12 Hz), 3.39-3.47 (2H, m), 3.62 (2H, br s), 4.65 (2H, br d, J=6.86 Hz), 7.38 (2H, t, J=8.78 Hz), 8.19 (2H, dd, J=8.78, 5.49 Hz), 8.47 (1H, s), 8.49 (1H, d, J=8.51 Hz), 8.70 (1H, d, J=8.51 Hz), 8.79 (1H, s), 9.33 (1H, s), 9.35 (1H, s), 11.14 (1H, br s); ESIMS found for C$_{23}$H$_{19}$FN$_6$O$_2$ m/z 431.2 (M+1).

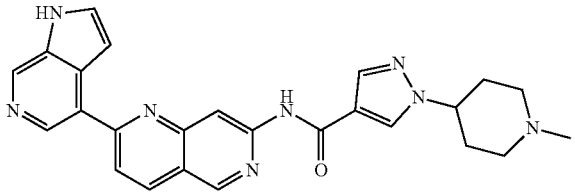

N-(2-(1H-Pyrrolo[2,3-c]pyridin-4-yl)-1,6-naphthyridin-7-yl)-1-(1-methylpiperidin-4-yl)-1H-pyrazole-4-carboxamide 896

Yellow solid (2 mg, 0.004 mmol, 21.5% yield). $^1$H NMR (499 MHz, METHANOL-d$_4$) δ ppm 2.12-2.23 (4H, m), 2.26-2.34 (2H, m), 2.36 (3H, s), 3.04 (2H, br d, J=12.08 Hz), 4.25-4.35 (1H, m), 7.27 (1H, d, J=2.74 Hz), 7.76 (1H, d, J=3.02 Hz), 8.11-8.19 (2H, m), 8.47 (1H, s), 8.56 (1H, d, J=8.78 Hz), 8.74 (1H, br s), 8.84 (1H, br s), 8.85 (1H, s), 9.20 (1H, s); ESIMS found for C$_{25}$H$_{24}$N$_8$O m/z 453.2 (M+1).

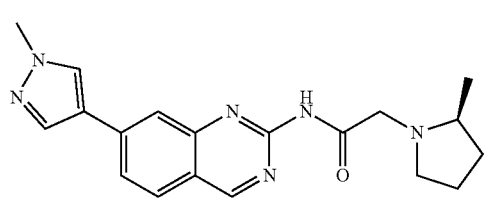

N-(7-(1-Methyl-1H-pyrazol-4-yl)quinazolin-2-yl)cyclopropanecarboxamide 909

White solid (12 mg, 0.04 mmol, 23.0% yield). $^1$H NMR (499 MHz, DMSO-d$_6$) δ ppm 0.81-0.90 (4H, m), 2.22-2.31 (1H, m), 3.91 (3H, s), 7.83 (1H, dd, J=8.51, 1.65 Hz), 7.89-7.92 (1H, m), 8.01 (1H, d, J=8.23 Hz), 8.14 (1H, d, J=0.82 Hz), 8.45 (1H, s), 9.36 (1H, s), 10.91 (1H, s); ESIMS found for C$_{16}$H$_{15}$N$_5$O m/z 294.1 (M+1).

(S)—N-(7-(1-Methyl-1H-pyrazol-4-yl)quinazolin-2-yl)-2-(2-methylpyrrolidin-1-yl)acetamide 954

White solid (30 mg, 0.09 mmol, 64.6% yield). $^1$H NMR (499 MHz, DMSO-d$_6$) δ ppm 1.09 (3H, d, J=6.04 Hz), 1.39 (1H, dddd, J=12.28, 10.29, 8.30, 6.45 Hz), 1.66-1.82 (2H, m), 1.90-1.98 (1H, m), 2.39 (1H, q, J=8.51 Hz), 2.56-2.66 (1H, m), 3.14 (1H, d, J=16.19 Hz), 3.14-3.21 (1H, m), 3.60 (1H, d, J=16.47 Hz), 3.91 (3H, s), 7.85 (1H, dd, J=8.37, 1.51

Hz), 7.98 (1H, d, J=0.82 Hz), 8.03 (1H, d, J=8.51 Hz), 8.16 (1H, s), 8.47 (1H, s), 9.37 (1H, s), 10.16 (1H, s); ESIMS found for $C_{19}H_{22}N_6O$ m/z 351.2 (M+1).

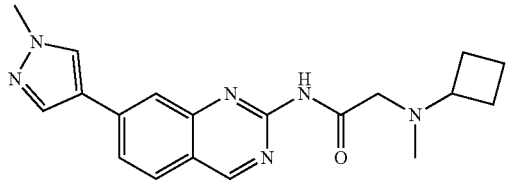

2-(Cyclobutyl(methyl)amino)-N-(7-(1-methyl-1H-pyrazol-4-yl)quinazolin-2-yl)acetamide 963

White solid (25 mg, 0.07 mmol, 43.1% yield). $^1$H NMR (499 MHz, DMSO-$d_6$) δ ppm 1.53-1.68 (2H, m), 1.78-1.91 (2H, m), 1.97-2.06 (2H, m), 2.22 (3H, s), 3.09 (1H, quin, J=7.82 Hz), 3.17 (2H, s), 3.91 (3H, s), 7.85 (1H, dd, J=8.51, 1.65 Hz), 7.98 (1H, d, J=1.37 Hz), 8.03 (1H, d, J=8.51 Hz), 8.16 (1H, s), 8.47 (1H, s), 9.37 (1H, s), 10.18 (1H, s); ESIMS found for $C_{19}H_{22}N_6O$ m/z 351.2 (M+1).

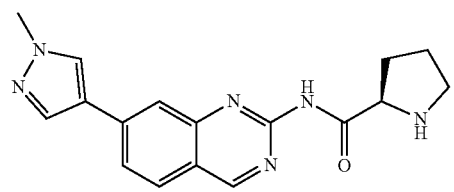

(R)—N-(7-(1-Methyl-1H-pyrazol-4-yl)quinazolin-2-yl)pyrrolidine-2-carboxamide 969

Off-white solid (5 mg, 0.02 mmol, 14.1% yield). $^1$H NMR (499 MHz, DMSO-$d_6$) δ ppm 1.90-2.04 (3H, m), 2.17-2.29 (1H, m), 3.58-3.70 (1H, m), 3.73-3.83 (1H, m), 3.87-3.90 (3H, m), 4.47-4.54 (1H, m), 6.88 (1H, br s), 7.35 (1H, br s), 7.50 (1H, dd, J=8.23, 1.65 Hz), 7.79 (1H, d, J=8.23 Hz), 8.07 (1H, br s), 8.38 (1H, s), 9.05 (1H, br s); ESIMS found for $C_{17}H_{18}N_6O$ m/z 323.2 (M+1).

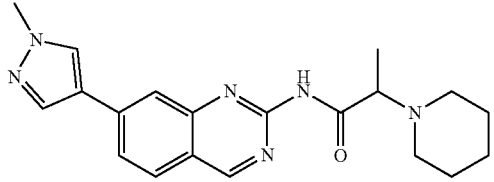

N-(7-(1-Methyl-1H-pyrazol-4-yl)quinazolin-2-yl)-2-(piperidin-1-yl)propanamide 978

Beige solid (26 mg, 0.07 mmol, 21.4% yield). $^1$H NMR (499 MHz, DMSO-$d_6$) δ ppm 1.18 (3H, d, J=6.86 Hz), 1.37-1.44 (2H, m), 1.55 (4H, br d, J=3.84 Hz), 2.51-2.57 (4H, m), 3.44-3.51 (1H, m), 3.91 (3H, s), 7.84 (1H, dd, J=8.37, 1.51 Hz), 7.97 (1H, s), 8.03 (1H, d, J=8.51 Hz), 8.16 (1H, s), 8.47 (1H, s), 9.37 (1H, s), 10.32 (1H, s); ESIMS found for $C_{20}H_{24}N_6O$ m/z 365.2 (M+1).

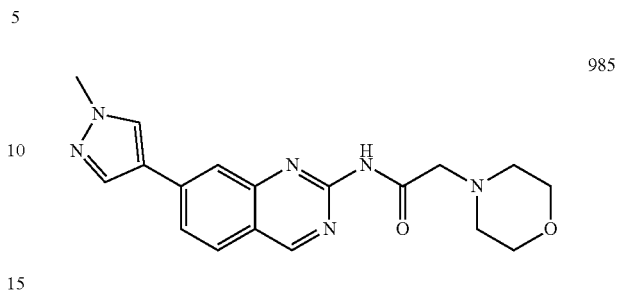

N-(7-(1-Methyl-1H-pyrazol-4-yl)quinazolin-2-yl)-2-morpholinoacetamide 985

Beige solid (14.0 mg, 0.040 mmol, 4.5% yield). $^1$H NMR (499 MHz, DMSO-$d_6$) δ ppm 2.54-2.61 (4H, m), 3.32 (2H, s), 3.60-3.66 (4H, m), 3.91 (3H, s), 7.85 (1H, dd, J=8.37, 1.51 Hz), 7.97 (1H, s), 8.03 (1H, d, J=8.51 Hz), 8.16 (1H, s), 8.47 (1H, s), 9.37 (1H, s), 10.28 (1H, s); ESIMS found for $C_{18}H_{20}N_6O_2$ m/z 353.15 (M+1).

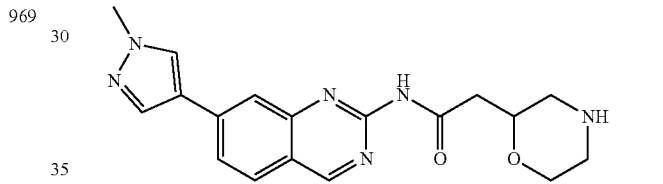

N-(7-(1-Methyl-1H-pyrazol-4-yl)quinazolin-2-yl)-2-(morpholin-2-yl)acetamide 994

Beige solid (35 mg, 0.10 mmol, 33.0% yield). $^{11}$H NMR (499 MHz, DMSO-d) δ ppm 2.40 (1H, dd, J=11.94, 10.29 Hz), 2.53-2.62 (2H, m), 2.64 (1H, br s), 2.70 (1H, br dd, J=14.82, 7.68 Hz), 2.81-2.88 (1H, m), 3.42 (1H, td, J=10.77, 3.43 Hz), 3.69 (1H, br d, J=10.70 Hz), 3.78-3.86 (1H, m), 3.91 (3H, s), 7.83 (1H, dd, J=8.37, 1.51 Hz), 7.92 (1H, d, J=1.37 Hz), 8.02 (1H, d, J=8.23 Hz), 8.15 (1H, s), 8.46 (1H, s), 9.35 (1H, s), 10.60 (1H, s); ESIMS found for $C_{18}H_{20}N_6O_2$ m/z 353.15 (M+1).

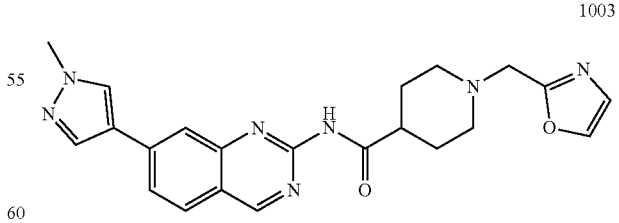

N-(7-(1-Methyl-1H-pyrazol-4-yl)quinazolin-2-yl)-1-(oxazol-2-ylmethyl) piperidine-4-carboxamide 1003

Off-white solid (22 mg, 0.05 mmol, 28.1% yield). $^1$H NMR (499 MHz, DMSO-$d_6$) δ ppm 1.64 (2H, qd, J=12.21, 3.70 Hz), 1.81 (2H, br d, J=11.25 Hz), 2.11 (2H, td, J=11.60, 2.06 Hz), 2.59-2.70 (1H, m), 2.88 (2H, br d, J=11.53 Hz), 3.67 (2H, s), 3.91 (3H, s), 7.17 (1H, d, J=0.82 Hz), 7.83 (1H, dd, J=8.37, 1.51 Hz), 7.91 (1H, d, J=0.82 Hz), 8.01 (1H, d, J=8.51 Hz), 8.08 (1H, s), 8.14 (1H, d, J=0.82 Hz), 8.44 (1H, s), 9.34 (1H, s), 10.59 (1H, s); ESIMS found for $C_{22}H_{23}N_7O_2$ m/z 418.2 (M+1).

1013

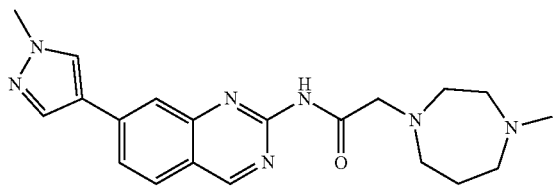

2-(4-Methyl-1,4-diazepan-1-yl)-N-(7-(1-methyl-1H-pyrazol-4-yl)quinazolin-2-yl)acetamide 1013

Beige solid (35 mg, 0.09 mmol, 61.8% yield). $^1$H NMR (499 MHz, DMSO-$d_6$) δ ppm 1.71-1.80 (2H, m), 2.26 (3H, s), 2.53-2.59 (4H, m), 2.79-2.85 (4H, m), 3.43 (2H, s), 3.91 (3H, s), 7.84 (1H, dd, J=8.37, 1.51 Hz), 7.97 (1H, s), 8.03 (1H, d, J=8.51 Hz), 8.16 (1H, s), 8.47 (1H, s), 9.37 (1H, s), 10.24 (1H, s); ESIMS found for $C_{20}H_{25}N_7O$ m/z 380.2 (M+1).

1029

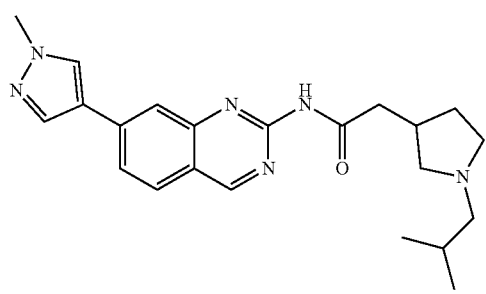

2-(1-Isobutylpyrrolidin-3-yl)-N-(7-(1-methyl-1H-pyrazol-4-yl)quinazolin-2-yl)acetamide 1029

Beige solid (4 mg, 0.01 mmol, 17.1% yield). $^1$H NMR (499 MHz, DMSO-$d_6$) δ ppm 0.86 (6H, d, J=6.59 Hz), 1.38-1.46 (1H, m), 1.66 (1H, dt, J=13.65, 6.76 Hz), 1.91-2.02 (1H, m), 2.09-2.21 (3H, m), 2.40-2.49 (2H, m), 2.52-2.58 (1H, m), 2.62-2.70 (3H, m), 3.91 (3H, s), 7.83 (1H, dd, J=8.23, 1.65 Hz), 7.91 (1H, d, J=0.82 Hz), 8.01 (1H, d, J=8.51 Hz), 8.14 (1H, s), 8.45 (1H, s), 9.34 (1H, s), 10.60 (1H, s); ESIMS found for $C_{22}H_{28}N_6O$ m/z 393.25 (M+1).

1047

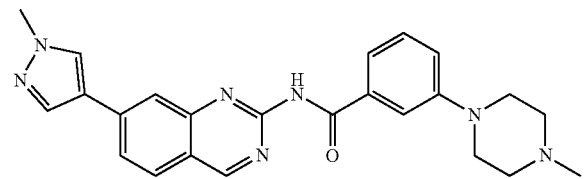

N-(7-(1-Methyl-1H-pyrazol-4-yl)quinazolin-2-yl)-3-(4-methylpiperazin-1-yl) benzamide 1047

Yellow solid (5.8 mg, 0.014 mmol, 8.7% yield). $^1$H NMR (499 MHz, DMSO-$d_6$) δ ppm 2.24 (3H, s), 2.45-2.49 (4H, m), 3.21-3.27 (4H, m), 3.92 (3H, s), 7.17 (1H, dd, J=8.23, 1.92 Hz), 7.34 (1H, t, J=7.82 Hz), 7.40-7.46 (1H, m), 7.55-7.60 (1H, m), 7.88 (1H, dd, J=8.51, 1.65 Hz), 7.99 (1H, d, J=1.37 Hz), 8.07 (1H, d, J=8.51 Hz), 8.16 (1H, s), 8.47 (1H, s), 9.44 (1H, s), 11.03 (1H, s); ESIMS found for $C_{24}H_{25}NO_7O$ m/z 428.2 (M+1).

1052

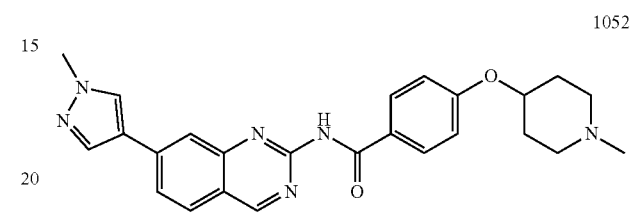

N-(7-(1-Methyl-1H-pyrazol-4-yl)quinazolin-2-yl)-4-((1-methylpiperidin-4-yl)oxy)benzamide 1052

Yellow solid (6.7 mg, 0.01 mmol, 30.8% yield). $^1$H NMR (499 MHz, DMSO-$d_6$) δ ppm 1.61-1.72 (2H, m), 1.93-2.01 (2H, m), 2.15-2.24 (2H, m), 2.19 (3H, s), 2.59-2.64 (2H, m), 3.91 (3H, s), 4.50-4.54 (1H, m), 7.03-7.09 (2H, m), 7.86-7.89 (1H, m), 7.97 (1H, d, J=0.82 Hz), 7.99 (2H, d, J=8.78 Hz), 8.06 (1H, d, J=8.51 Hz), 8.16 (1H, s), 8.47 (1H, s), 9.42 (1H, s), 10.91 (1H, br s); ESIMS found for $C_{25}H_{26}N_6O_2$ m/z 443.2 (M+1).

1054

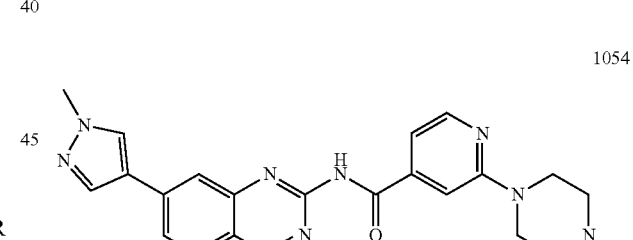

N-(7-(1-Methyl-1H-pyrazol-4-yl)quinazolin-2-yl)-2-(4-methylpiperazin-1-yl) isonicotinamide 1054

Yellow solid (3.0 mg, 0.07 mmol, 6.4% yield). $^1$H NMR (499 MHz, DMSO-$d_6$) δ ppm 2.23 (3H, s), 2.40-2.45 (4H, m), 3.55-3.63 (4H, m), 3.92 (3H, s), 7.10 (1H, dd, J=4.94, 1.10 Hz), 7.39 (1H, s), 7.90 (1H, dd, J=8.37, 1.51 Hz), 7.99 (1H, s), 8.08 (1H, d, J=8.51 Hz), 8.16 (1H, s), 8.25 (1H, d, J=5.21 Hz), 8.47 (1H, s), 9.45 (1H, s), 11.23 (1H, br s); ESIMS found for $C_{23}H_{24}N_8O$ m/z 429.2 (M+1).

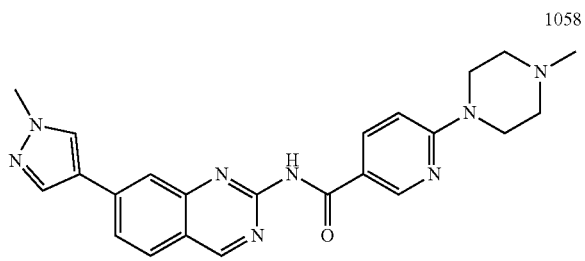 [SMILES: CN1CCN(c2ccc(C(=O)Nc3ncc4ccc(-c5cnn(C)c5)cc4n3)cn2)CC1]

N-(7-(1-Methyl-1H-pyrazol-4-yl)quinazolin-2-yl)-6-(4-methylpiperazin-1-yl)nicotinamide 1058

Yellow solid (11 mg, 0.03 mmol, 2.3% yield). $^1$H NMR (499 MHz, DMSO-$d_6$) δ ppm 2.23 (3H, s), 2.40 (4H, t, J=4.94 Hz), 3.63-3.67 (4H, m), 3.91 (3H, s), 6.90 (1H, d, J=9.06 Hz), 7.86 (1H, dd, J=8.37, 1.51 Hz), 7.96-7.99 (1H, m), 8.06 (1H, d, J=8.51 Hz), 8.10 (1H, dd, J=9.06, 2.47 Hz), 8.16 (1H, s), 8.46 (1H, s), 8.77 (1H, d, J=2.47 Hz), 9.41 (1H, s), 10.90 (1H, s) ESIMS found for $C_{23}H_{24}N_8O$ m/z 429.2 (M+1).

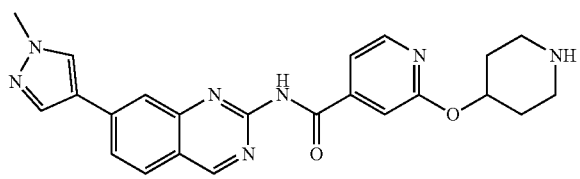

N-(7-(1-Methyl-1H-pyrazol-4-yl)quinazolin-2-yl)-2-(piperidin-4-yloxy)isonicotinamide 1060

Yellow solid (3.5 mg, 0.008 mmol, 5.6% yield). $^1$H NMR (499 MHz, DMSO-$d_6$) δ ppm 1.47-1.58 (2H, m), 1.92-1.99 (2H, m), 2.55-2.62 (2H, m), 2.92-3.01 (2H, m), 3.91 (3H, s), 5.05-5.13 (1H, m), 7.25-7.29 (2H, m), 7.42 (1H, dd, J=5.21, 1.37 Hz), 7.89 (1H, br d, J=9.33 Hz), 7.99 (1H, s), 8.07 (1H, d, J=8.51 Hz), 8.16 (1H, s), 8.29 (1H, d, J=5.21 Hz), 8.47 (1H, s), 9.43 (1H, s); ESIMS found for $C_{23}H_{23}N_7O_2$ m/z 430.2 (M+1).

2-((2-(Dimethylamino)ethyl)amino)-N-(7-(1-methyl-1H-pyrazol-4-yl)quinazolin-2-yl)isonicotinamide 1071

Light yellow wax (5.5 mg, 0.01 mmol, 2.7% yield). $^1$H NMR (499 MHz, DMSO-$d_6$) δ ppm 2.18 (6H, s), 2.42 (2H, t, J=6.72 Hz), 3.34-3.42 (2H, m), 3.91 (3H, s), 6.63 (1H, br t, J=5.49 Hz), 6.94 (1H, dd, J=5.21, 1.37 Hz), 6.98 (1H, s), 7.90 (1H, dd, J=8.51, 1.65 Hz), 7.99 (1H, s), 8.08 (1H, d, J=8.51 Hz), 8.10 (1H, d, J=5.21 Hz), 8.17 (1H, s), 8.48 (1H, s), 9.43 (1H, s), 11.08 (1H, br s); ESIMS found for $C_{22}H_{24}N_8O$ m/z 417.2 (M+1).

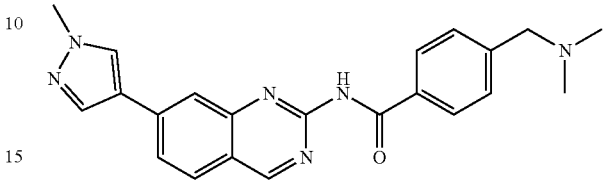

4-((Dimethylamino)methyl)-N-(7-(1-methyl-1H-pyrazol-4-yl)quinazolin-2-yl)benzamide 1077

Yellow solid (4.1 mg, 0.01 mmol, 3.0% yield). $^1$H NMR (499 MHz, DMSO-$d_6$) δ ppm 2.17 (6H, s), 3.47 (2H, s), 3.91 (3H, s), 7.43 (2H, d, J=8.23 Hz), 7.88 (1H, dd, J=8.51, 1.65 Hz), 7.96-8.00 (3H, m), 8.07 (1H, d, J=8.51 Hz), 8.16 (1H, s), 8.47 (1H, s), 9.43 (1H, s), 11.04 (1H, s); ESIMS found for $C_{22}H_{22}N_6O$ m/z 387.2 (M+1).

N-(7-(1-Methyl-1H-pyrazol-4-yl)quinazolin-2-yl)-3-((4-methylpiperazin-1-yl)methyl)benzamide 1079

Yellow solid (28 mg, 0.06 mmol, 14.3% yield). $^1$H NMR (499 MHz, DMSO-$d_6$) δ ppm 2.13 (3H, s), 2.22-2.35 (4H, m), 2.35-2.47 (3H, m), 3.52 (2H, s), 3.91 (3H, s), 7.43-7.49 (1H, m), 7.50-7.56 (1H, m), 7.88 (1H, brd, J=1.65 Hz), 7.89-7.91 (2H, m), 7.96-7.99 (1H, m), 8.07 (1H, d, J=8.23 Hz), 8.16 (1H, s), 8.47 (1H, s), 9.43 (1H, s), 11.08 (1H, br s); ESIMS found for $C_{25}H_{27}N_7O$ m/z 442.2 (M+1).

N-(7-(1-Methyl-1H-pyrazol-4-yl)quinazolin-2-yl)-3-phenylpropanamide 1101

Yellow solid (9.7 mg, 0.03 mmol, 11.8% yield). $^1$H NMR (499 MHz, DMSO-$d_6$) δ ppm 2.85-2.91 (2H, m), 2.91-2.98 (2H, m), 3.91 (3H, s), 7.17-7.22 (1H, m), 7.28 (2H, s), 7.29

(2H, d, J=1.37 Hz), 7.83 (1H, dd, J=8.23, 1.65 Hz), 7.91 (1H, d, J=1.37 Hz), 8.01 (1H, d, J=8.51 Hz), 8.14 (1H, s), 8.45 (1H, s), 9.35 (1H, s), 10.65 (1H, s); ESIMS found for $C_{21}H_9N_5O$ m/z 358.2 (M+1).

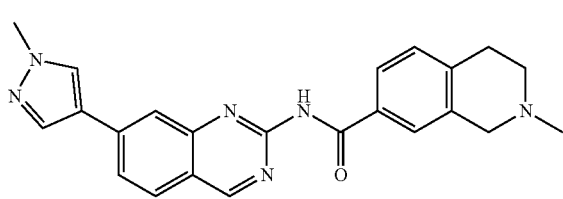

1109

2-Methyl-N-(7-(1-methyl-1H-pyrazol-4-yl)quinazolin-2-yl)-1,2,3,4-tetrahydroisoquinoline-7-carboxamide 1109

Yellow solid (2.6 mg, 0.006 mmol, 1.9% yield). $^1$H NMR (499 MHz, DMSO-$d_6$) δ ppm 2.37 (3H, s), 2.63 (2H, t, J=5.90 Hz), 2.89 (2H, t, J=5.76 Hz), 3.55 (2H, s), 3.91 (3H, s), 7.24 (1H, d, J=7.96 Hz), 7.74 (1H, s), 7.77 (1H, dd, J=7.96, 1.37 Hz), 7.88 (1H, dd, J=8.51, 1.65 Hz), 7.98 (1H, s), 8.07 (1H, d, J=8.51 Hz), 8.16 (1H, s), 8.47 (1H, s), 9.43 (1H, s), 10.98 (1H, br s); ESIMS found for $C_{23}H_{22}N_6O$ m/z 399.2 (M+1).

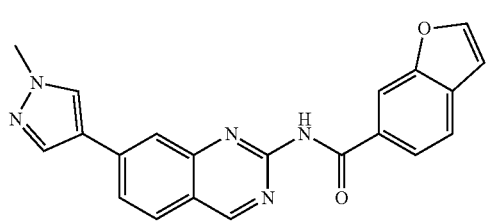

1116

N-(7-(1-Methyl-1H-pyrazol-4-yl)quinazolin-2-yl) benzofuran-6-carboxamide 1116

Brown solid (10.2 mg, 0.03 mmol, 12.4% yield). $^1$H NMR (500 MHz, DMSO-$d_6$) δ ppm 3.92 (3H, s), 7.09 (1H, dd, J=2.20, 0.82 Hz), 7.79 (1H, d, J=7.68 Hz), 7.89 (1H, dd, J=8.51, 1.65 Hz), 7.95 (1H, dd, J=8.10, 1.51 Hz), 8.00-8.03 (1H, m), 8.08 (1H, d, J=8.23 Hz), 8.17 (1H, d, J=0.82 Hz), 8.20 (1H, d, J=2.20 Hz), 8.31 (1H, d, J=0.82 Hz), 8.48 (1H, s), 9.45 (1H, d, J=0.82 Hz), 11.15 (1H, s); ESIMS found for $C_{21}H_{15}N_5O_2$ m/z 370.1 (M+1).

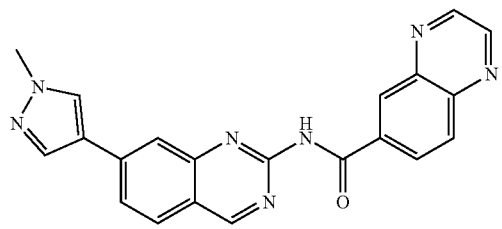

1123

N-(7-(1-Methyl-1H-pyrazol-4-yl)quinazolin-2-yl) quinoxaline-6-carboxamide 1123

Brown solid (15.8 mg, 0.04 mmol, 9.8% yield). $^1$H NMR (500 MHz, DMSO-$d_6$) δ ppm 3.92 (3H, s), 7.91 (1H, dd, J=8.51, 1.65 Hz), 8.01-8.04 (1H, m), 8.10 (1H, d, J=8.51 Hz), 8.18 (1H, s), 8.23 (1H, d, J=8.51 Hz), 8.38 (1H, dd, J=8.64, 2.06 Hz), 8.49 (1H, s), 8.78 (1H, d, J=1.92 Hz), 9.06-9.10 (2H, m), 9.48 (1H, s), 11.54 (1H, s); ESIMS found for $C_{21}H_{15}N_7O$ m/z 382.1 (M+1).

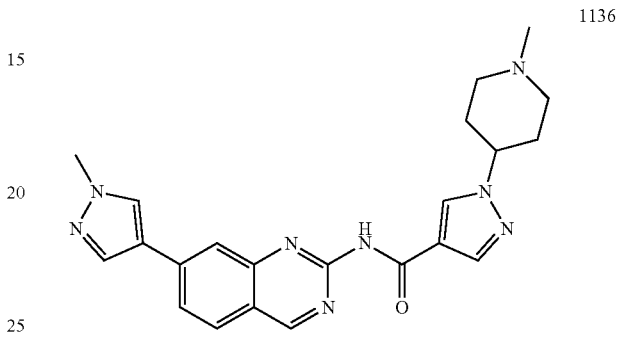

1136

N-(7-(1-Methyl-1H-pyrazol-4-yl)quinazolin-2-yl)-1-(1-methylpiperidin-4-yl)-1H-pyrazole-4-carboxamide 1136

Yellow solid (1.1 mg, 0.003 mmol, 10.01% yield). $^1$H NMR (499 MHz, METHANOL-$d_4$) δ ppm 2.11-2.23 (4H, m), 2.24-2.31 (2H, m), 2.35 (3H, s), 3.03 (2H, br d, J=11.80 Hz), 3.99 (3H, s), 4.25-4.33 (1H, m), 7.85 (1H, dd, J=8.37, 1.51 Hz), 8.00 (1H, d, J=8.51 Hz), 8.06 (1H, s), 8.08 (1H, s), 8.14 (1H, s), 8.25 (1H, s), 8.46 (1H, s), 9.31 (1H, s); ESIMS found for $C_{22}H_{24}N_8O$ m/z 417.2 (M+1).

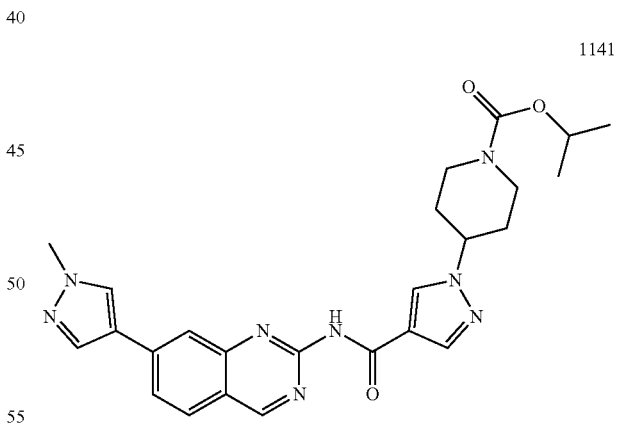

1141

Isopropyl 4-(4-((7-(1-methyl-1H-pyrazol-4-yl)quinazolin-2-yl)carbamoyl)-1H-pyrazol-1-yl)piperidine-1-carboxylate 1141

White solid (2 mg, 0.004 mmol, 16.5% yield). $^1$H NMR (499 MHz, METHANOL-$d_4$) δ ppm 1.28 (6H, d, J=6.31 Hz), 1.95-2.03 (2H, m), 2.16 (2H, br d, J=10.70 Hz), 3.04 (2H, br s), 3.98 (3H, s), 4.28 (2H, br d, J=13.17 Hz), 4.49 (1H, tt, J=11.53, 3.98 Hz), 4.90 (1H, dt, J=12.62, 6.31 Hz), 7.85 (1H, dd, J=8.51, 1.37 Hz), 8.00 (1H, d, J=8.51 Hz), 8.06

(1H, s), 8.08 (1H, s), 8.15 (1H, s), 8.25 (1H, s), 8.45 (1H, s), 9.31 (1H, s); ESIMS found for C$_{25}$H$_{25}$N$_8$O$_3$ m/z 489.3 (M+1).

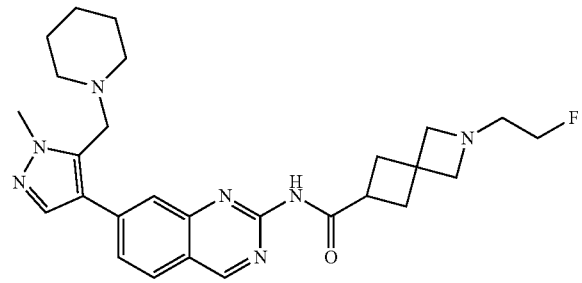

2-(2-Fluoroethyl)-N-(7-(1-methyl-5-(piperidin-1-ylmethyl)-1H-pyrazol-4-yl) quinazolin-2-yl)-2-azaspiro[3.3]heptane-6-carboxamide 1186

Beige solid (15 mg, 0.03 mmol, 27.2% yield). $^1$H NMR (499 MHz, DMSO-d$_6$) δ ppm 1.34-1.42 (2H, m), 1.45-1.53 (4H, m), 2.33 (4H, d, J=8.23 Hz), 2.35-2.44 (4H, m), 2.60-2.74 (2H, m), 3.19 (2H, br s), 3.57 (1H, quin, J=7.96 Hz), 3.67 (2H, s), 3.92 (3H, s), 4.37 (2H, dt, J=47.60, 5.00 Hz), 7.78 (1H, dd, J=8.51, 1.65 Hz), 7.86 (1H, s), 7.92 (1H, s), 8.04 (1H, d, J=8.23 Hz), 9.39 (1H, s), 10.50 (1H, s); ESIMS found for C$_{27}$H$_{34}$FN$_7$O m/z 492.3 (M+1).

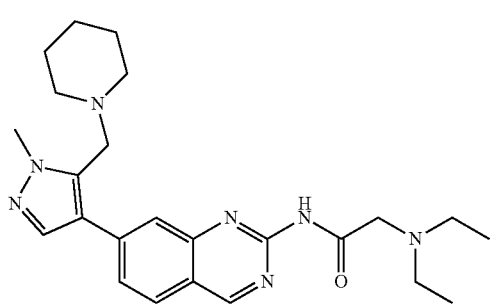

2-(Diethylamino)-N-(7-(1-methyl-5-(piperidin-1-ylmethyl)-1H-pyrazol-4-yl)quinazolin-2-yl)acetamide 1189

Beige gum (10 mg, 0.02 mmol, 14.8% yield). $^1$H NMR (499 MHz, DMSO-d$_6$) δ ppm 1.04 (6H, t, J=7.14 Hz), 1.37 (2H, br d, J=3.84 Hz), 1.43-1.51 (4H, m), 2.31-2.39 (4H, m), 2.65 (4H, q, J=7.14 Hz), 3.29 (2H, s), 3.67 (2H, s), 3.92 (3H, s), 7.81 (1H, dd, J=8.51, 1.65 Hz), 7.86 (1H, s), 7.94-7.98 (1H, m), 8.06 (1H, d, J=8.51 Hz), 9.43 (1H, s), 10.22 (1H, s); ESIMS found for C$_{24}$H$_{33}$N$_7$O m/z 436.35 (M+1).

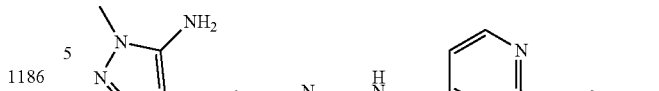

N-(7-(5-Amino-1-methyl-1H-pyrazol-4-yl)quinazolin-2-yl)-2-(4-methylpiperazin-1-yl)isonicotinamide 1210

Light yellow solid (14 mg, 0.03 mmol, 53.7% yield). $^1$H NMR (499 MHz, DMSO-d$_6$) δ ppm 2.23 (3H, s), 2.42 (4H, t, J=4.94 Hz), 3.56-3.61 (4H, m), 3.63 (3H, s), 5.82 (2H, s), 7.10 (1H, dd, J=5.21, 1.10 Hz), 7.39 (1H, s), 7.71 (1H, s), 7.78-7.83 (1H, m), 7.83 (1H, s), 8.01 (1H, d, J=8.51 Hz), 8.25 (1H, d, J=4.94 Hz), 9.39 (1H, s), 11.18 (1H, s); ESIMS found for C$_{23}$H$_{25}$N$_9$O m/z 444.2 (M+1).

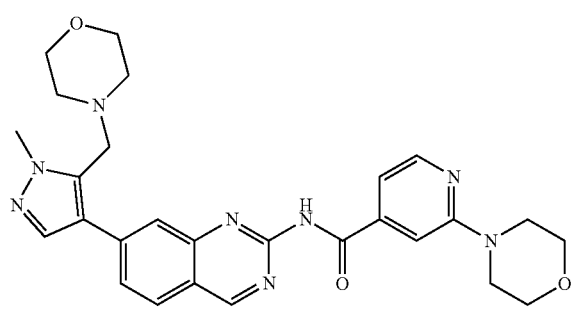

N-(7-(1-Methyl-5-(morpholinomethyl)-1H-pyrazol-4-yl)quinazolin-2-yl)-2-morpholinoisonicotinamide 1220

Off-white solid (55.1 mg, 0.11 mmol, 44.6% yield). $^1$H NMR (499 MHz, DMSO-d$_6$) δ ppm 2.39 (4H, br s), 3.51-3.59 (8H, m), 3.71-3.74 (4H, m), 3.75 (2H, s), 3.95 (3H, s), 7.14 (1H, dd, J=5.08, 0.96 Hz), 7.40 (1H, s), 7.86 (1H, dd, J=8.37, 1.51 Hz), 7.88 (1H, s), 7.95 (1H, s), 8.13 (1H, d, J=8.51 Hz), 8.28 (1H, d, J=5.21 Hz), 9.53 (1H, s), 11.28 (1H, s); ESIMS found for C$_{27}$H$_{30}$N$_8$O$_3$ m/z 515.3 (M+1).

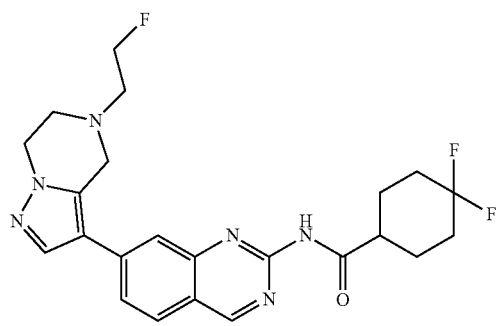

N-((4,4-Difluorocyclohexyl)methyl)-7-(5-(2-fluoroethyl)-4,5,6,7-tetrahydropyrazolo[1,5-a]pyrazin-3-yl)quinazolin-2-amine 1223

Beige solid (3 mg, 0.007 mmol, 4.1% yield). $^1$H NMR (499 MHz, METHANOL-$d_4$) δ ppm 1.85-1.97 (4H, m), 2.03-2.10 (2H, m), 2.14-2.23 (2H, m), 2.76 (1H, br s), 3.06 (2H, dt, J=28.30, 4.70 Hz), 3.17-3.23 (2H, m), 4.16 (2H, s), 4.28 (2H, t, J=5.49 Hz), 4.69 (2H, dt, J=47.90, 5.00 Hz), 7.75 (1H, dd, J=8.51, 1.65 Hz), 7.88 (1H, s), 7.98-8.03 (2H, m), 8.52 (1H, br s), 9.29 (1H, s); ESIMS found for $C_{23}H_{25}F_3N_6O$ m/z 459.2 (M+1).

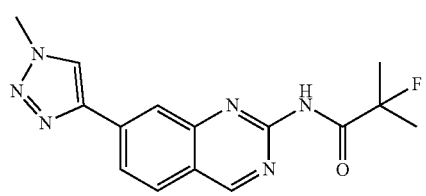

2-Fluoro-2-methyl-N-(7-(1-methyl-1H-1,2,3-triazol-4-yl)quinazolin-2-yl) propanamide 1239

Beige solid (8 mg, 0.03 mmol, 9.6% yield). $^1$H NMR (499 MHz, DMSO-$d_6$) δ ppm 1.63 (6H, d, J=22.00 Hz), 4.15 (3H, s), 8.13-8.22 (2H, m), 8.28 (1H, d, J=1.37 Hz), 8.87 (1H, s), 9.53 (1H, s), 10.36 (1H, d, J=3.02 Hz); ESIMS found for $C_{15}H_{15}FN_6O$ m/z 315.1 (M+1).

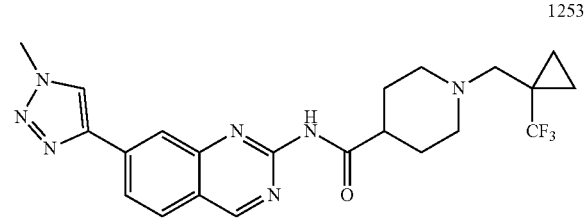 [SMILES: Cn1cc(-c2ccc3cnc(NC(=O)C4CCN(CC5(C(F)(F)F)CC5)CC4)nc3c2)nn1]

N-(7-(1-Methyl-1H-1,2,3-triazol-4-yl)quinazolin-2-yl)-1-((1-(trifluoromethyl)cyclopropyl)methyl)piperidine-4-carboxamide 1253

Off-white solid (30 mg, 0.07 mmol, 35.0% yield). $^1$H NMR (499 MHz, DMSO-$d_6$) δ ppm 0.73 (2H, s), 0.93-0.99 (2H, m), 1.64 (2H, qd, J=12.12, 3.70 Hz), 1.80 (2H, br d, J=10.43 Hz), 1.93-2.01 (2H, m), 2.67-2.77 (1H, m), 2.97 (2H, br d, J=11.53 Hz), 4.15 (3H, s), 8.07-8.11 (1H, m), 8.11-8.14 (1H, m), 8.19-8.22 (1H, m), 8.85 (1H, s), 9.45 (1H, s), 10.68 (1H, s); ESIMS found for $C_{22}H_{24}F_3N_7O$ m/z 460.2 (M+1).

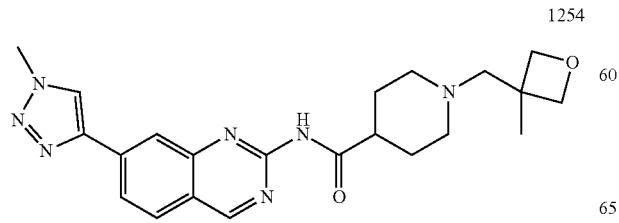

N-(7-(1-Methyl-1H-1,2,3-triazol-4-yl)quinazolin-2-yl)-1-((3-methyloxetan-3-yl)methyl)piperidine-4-carboxamide 1254

Tan solid (3 mg, 0.007 mmol, 4.0% yield). $^1$H NMR (499 MHz, DMSO-$d_6$) δ ppm 1.31 (3H, s), 1.60-1.69 (2H, m), 1.78 (2H, br dd, J=11.66, 1.23 Hz), 1.95-2.03 (2H, m), 2.59-2.64 (2H, m), 3.04-3.13 (2H, m), 3.35-3.39 (1H, m), 4.15 (3H, s), 4.19 (2H, d, J=5.49 Hz), 4.36 (2H, d, J=5.76 Hz), 8.06-8.11 (1H, m), 8.11-8.16 (1H, m), 8.19 (1H, s), 8.85 (1H, s), 9.44 (1H, s), 10.68 (1H, s); ESIMS found for $C_{22}H_{27}N_7O_2$ m/z 422.2 (M+1).

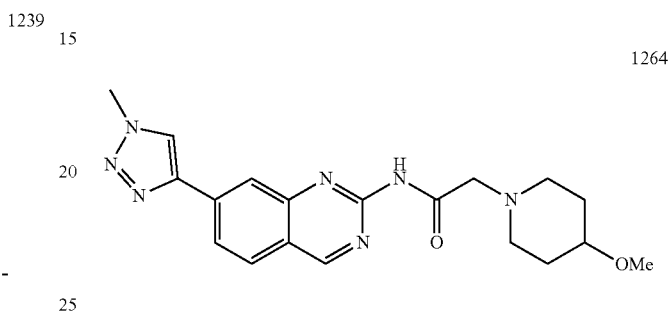

2-(4-Methoxypiperidin-1-yl)-N-(7-(1-methyl-1H-1,2,3-triazol-4-yl) quinazolin-2-yl)acetamide 1264

Beige solid (20 mg, 0.05 mmol, 23.7% yield). $^1$H NMR (499 MHz, DMSO-$d_6$) δ ppm 1.43-1.52 (2H, m), 1.86 (2H, br dd, J=9.47, 3.98 Hz), 2.31-2.40 (2H, m), 2.74-2.82 (2H, m), 3.16-3.22 (1H, m), 3.23 (3H, s), 3.28 (2H, s), 4.14 (3H, s), 8.09-8.13 (1H, m), 8.13-8.18 (1H, m), 8.24 (1H, s), 8.87 (1H, s), 9.47 (1H, s), 10.31 (1H, s); ESIMS found for $C_{19}H_{23}N_7O_2$ m/z 382.2 (M+1).

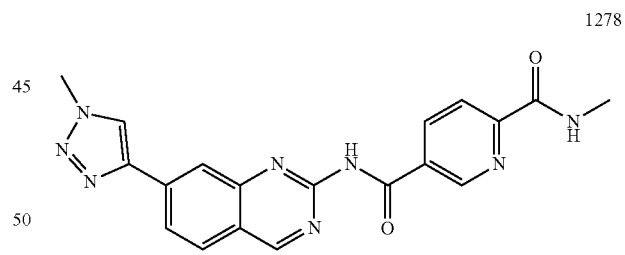

$N^2$-Methyl-$N^5$-(7-(1-methyl-1H-1,2,3-triazol-4-yl)quinazolin-2-yl)pyridine-2,5-dicarboxamide 1278

Beige solid (87 mg, 0.20 mmol, 45.6% yield). $^1$H NMR (499 MHz, DMSO-$d_6$) δ ppm 2.85 (3H, d, J=4.94 Hz), 4.15 (3H, s), 8.14-8.22 (3H, m), 8.26 (1H, s), 8.50 (1H, dd, J=8.23, 2.20 Hz), 8.88 (1H, s), 8.92-8.97 (1H, m), 9.15 (1H, d, J=2.20 Hz), 9.56 (1H, s), 11.58 (1H, s); ESIMS found for $C_{19}H_{16}N_8O_2$ m/z 389.1 (M+1).

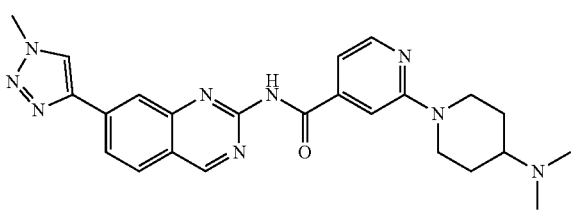

2-(4-(Dimethylamino)piperidin-1-yl)-N-(7-(1-methyl-1H-1,2,3-triazol-4-yl) quinazolin-2-yl)isonicotinamide 1282

Beige solid (11 mg, 0.02 mmol, 17.6% yield). $^1$H NMR (499 MHz, DMSO-d$_6$) δ ppm 1.30-1.44 (2H, m), 1.83 (2H, br d, J=12.35 Hz), 2.19 (6H, s), 2.28-2.36 (1H, m), 2.84-2.95 (2H, m), 4.15 (3H, s), 4.41 (2H, br d, J=13.17 Hz), 7.06 (1H, dd, J=4.94, 1.10 Hz), 7.39 (1H, s), 8.15-8.18 (1H, m), 8.18-8.22 (1H, m), 8.24 (1H, d, J=5.21 Hz), 8.28 (1H, s), 8.88 (1H, s), 9.55 (1H, s), 11.32 (1H, br s); ESIMS found for C$_{24}$H$_{27}$N$_9$O m/z 458.2 (M+1).

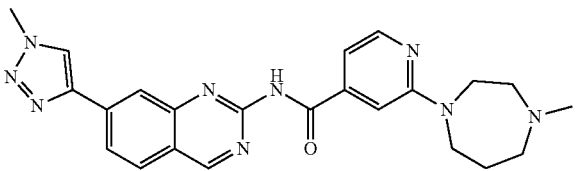

2-(4-Methyl-1,4-diazepan-1-yl)-N-(7-(1-methyl-1H-1,2,3-triazol-4-yl) quinazolin-2-yl)isonicotinamide 1285

Beige solid (10 mg, 0.02 mmol, 16.5% yield). $^1$H NMR (499 MHz, DMSO-d$_6$) δ ppm 1.87-1.97 (2H, m), 2.26 (3H, s), 2.47 (2H, br d, J=5.76 Hz), 2.59-2.66 (2H, m), 3.67 (2H, t, J=6.04 Hz), 3.77-3.83 (2H, m), 4.15 (3H, s), 7.00 (1H, dd, J=5.08, 0.96 Hz), 7.14 (1H, s), 8.13-8.18 (1H, m), 8.18-8.23 (2H, m), 8.27 (1H, s), 8.87 (1H, s), 9.55 (1H, s), 11.31 (1H, br s); ESIMS found for C$_{23}$H$_{25}$N$_9$O m/z 444.2 (M+1).

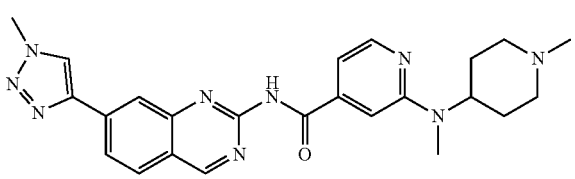

2-(Methyl(1-methylpiperidin-4-yl)amino)-N-(7-(1-methyl-1H-1,2,3-triazol-4-yl)quinazolin-2-yl)isonicotinamide 1288

Off-white solid (4 mg, 0.008 mmol, 4.5% yield). $^1$H NMR (499 MHz, DMSO-d$_6$) δ ppm 1.51-1.62 (2H, m), 1.74-1.85 (2H, m), 2.02 (2H, br t, J=10.84 Hz), 2.19 (3H, s), 2.85 (2H, br d, J=11.25 Hz), 2.92 (3H, s), 4.15 (3H, s), 4.43-4.55 (1H, m), 7.02 (1H, dd, J=5.08, 1.23 Hz), 7.13 (1H, s), 8.15-8.18 (1H, m), 8.19-8.21 (1H, m), 8.22 (1H, d, J=4.94 Hz), 8.28 (1H, s), 8.88 (1H, s), 9.55 (1H, s), 11.30 (1H, br s); ESIMS found for C$_{24}$H$_{27}$N$_9$O m/z 458.2 (M+1).

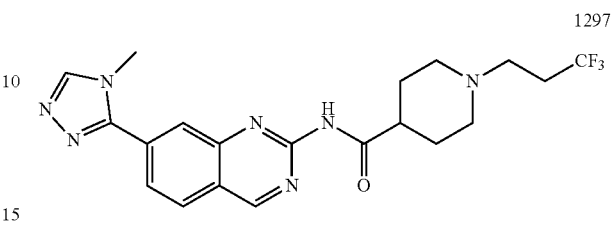

N-(7-(4-Methyl-4H-1,2,4-triazol-3-yl)quinazolin-2-yl)-1-(3,3,3-trifluoropropyl)piperidine-4-carboxamide 1297

Off-white solid (10 mg, 0.02 mmol, 14.8% yield). $^1$H NMR (499 MHz, DMSO-d$_6$) δ ppm 1.63 (2H, qd, J=12.21, 3.43 Hz), 1.83 (2H, br d, J=10.98 Hz), 1.94-2.03 (2H, m), 2.40-2.55 (4H, m), 2.70 (1H, br t, J=11.53 Hz), 2.93 (2H, br d, J=11.25 Hz), 3.88 (3H, s), 7.99 (1H, dd, J=8.37, 1.51 Hz), 8.10 (1H, s), 8.22 (1H, d, J=8.51 Hz), 8.69 (1H, s), 9.57 (1H, s), 10.80 (1H, s); ESIMS found for C$_{20}$H$_{22}$F$_3$N$_7$O m/z 434.2 (M+1).

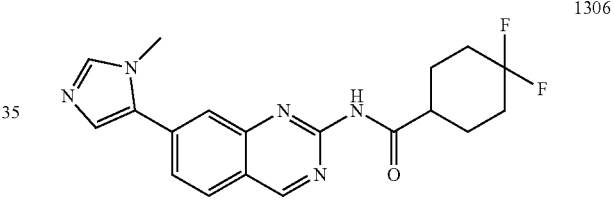

4,4-Difluoro-N-(7-(1-methyl-1H-imidazol-5-yl)quinazolin-2-yl)cyclohexane-1-carboxamide 1306

Dark pink solid (45 mg, 0.12 mmol, 27.3% yield). $^1$H NMR (499 MHz, DMSO-d$_6$) δ ppm 1.63-1.75 (2H, m), 1.76-1.94 (2H, m), 1.95-2.02 (2H, m), 2.07-2.18 (2H, m), 2.85-2.96 (1H, m), 3.84 (3H, s), 7.39 (1H, d, J=1.10 Hz), 7.77 (1H, dd, J=8.23, 1.65 Hz), 7.84 (1H, s), 7.85-7.87 (1H, m), 8.11 (1H, d, J=8.23 Hz), 9.47 (1H, s), 10.79 (1H, br s); ESIMS found for C$_{19}$H$_{19}$F$_2$N$_5$O m/z 372.2 (M+1).

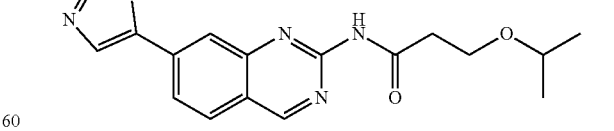

3-Isopropoxy-N-(7-(1-methyl-1H-imidazol-5-yl)quinazolin-2-yl)propanamide 1322

Beige solid (3 mg, 0.009 mmol, 4.3% yield). $^1$H NMR (500 MHz, DMSO-d$_6$) δ ppm 1.08 (6H, d, J=6.04 Hz), 2.76

(2H, t, J=6.17 Hz), 3.57 (1H, dquin, J=12.16, 6.08, 6.08, 6.08, 6.08 Hz), 3.68 (2H, t, J=6.31 Hz), 3.84 (3H, s), 7.39 (1H, s), 7.77 (1H, dd, J=8.51, 1.37 Hz), 7.84 (2H, s), 8.11 (1H, d, J=8.51 Hz), 9.47 (1H, s), 10.71 (1H, s); ESIMS found for $C_{18}H_{21}N_5O_2$ m/z 340.15 (M+1).

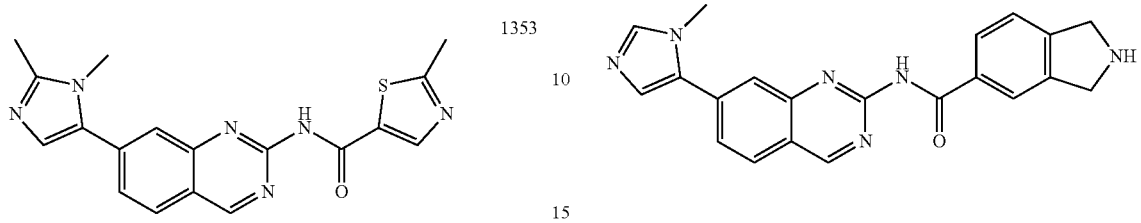

N-(7-(1,2-Dimethyl-1H-imidazol-5-yl)quinazolin-2-yl)-2-methylthiazole-5-carboxamide 1353

Beige solid (3 mg, 0.008 mmol, 4.9% yield). $^1$H NMR (500 MHz, DMSO-$d_6$) δ ppm 2.41 (3H, s), 2.72 (3H, s), 3.70 (3H, s), 7.25 (1H, s), 7.76 (1H, dd, J=8.51, 1.65 Hz), 7.81 (1H, s), 8.16 (1H, d, J=8.23 Hz), 8.60 (1H, s), 9.55 (1H, s), 11.43 (1H, s); ESIMS found for $C_{18}H_{16}N_6OS$ m/z 365.1 (M+1).

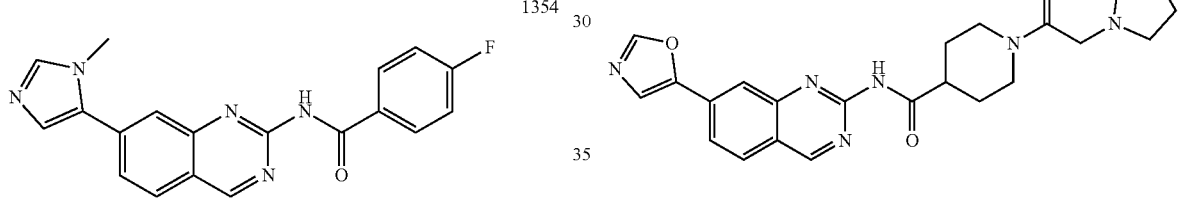

4-Fluoro-N-(7-(1-methyl-1H-imidazol-5-yl)quinazolin-2-yl)benzamide 1354

White solid (130 mg, 0.09 mmol, 19.5% yield). $^1$H NMR (499 MHz, DMSO-$d_6$) δ ppm 3.86 (3H, s), 7.36 (2H, t, J=8.92 Hz), 7.42 (1H, d, J=1.10 Hz), 7.83 (1H, dd, J=8.23, 1.65 Hz), 7.85 (1H, s), 7.91 (1H, s), 8.07-8.13 (2H, m), 8.17 (1H, d, J=8.51 Hz), 9.55 (1H, s), 11.25 (1H, s); ESIMS found for $C_{19}H_{14}FN_5O$ m/z 348.1 (M+1).

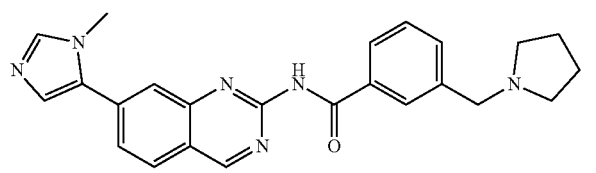

N-(7-(1-Methyl-1H-imidazol-5-yl)quinazolin-2-yl)-3-(pyrrolidin-1-ylmethyl)benzamide 1356

Pink solid (55 mg, 0.13 mmol, 30.0% yield). $^1$H NMR (499 MHz, DMSO-$d_6$) δ ppm 1.66-1.75 (4H, m), 2.45 (4H, br s), 3.65 (2H, s), 3.86 (3H, s), 7.42 (1H, d, J=7.96 Hz), 7.54 (1H, d, J=7.68 Hz), 7.82-7.86 (2H, m), 7.87-7.91 (2H, m), 7.94 (1H, s), 8.17 (1H, d, J=8.51 Hz), 9.55 (1H, s), 11.18 (1H, s); ESIMS found for $C_{24}H_{24}N_6O$ m/z 413.1 (M+1).

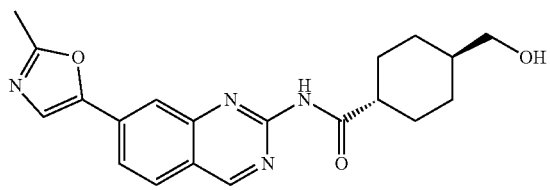

N-(7-(1-Methyl-1H-imidazol-5-yl)quinazolin-2-yl) isoindoline-5-carboxamide 1383

Brick red solid (15 mg, 0.04 mmol, 54.4% yield). $^1$H NMR (499 MHz, DMSO-$d_6$) δ ppm 3.86 (4H, s), 4.13 (3H, s), 7.39 (1H, d, J=7.68 Hz), 7.42 (1H, s), 7.83-7.86 (3H, m), 7.86-7.89 (1H, m), 7.91 (2H, s), 8.16 (1H, d, J=8.23 Hz), 9.55 (1H, s); ESIMS found for $C_{21}H_{18}N_6O$ m/z 371.15 (M+1).

N-(7-(Oxazol-5-yl)quinazolin-2-yl)-1-(2-(pyrrolidin-1-yl)acetyl)piperidine-4-carboxamide 1438

White solid (5.0 mg, 0.01 mmol, 4.7% yield). $^1$H NMR (499 MHz, DMSO-$d_6$) δ ppm 1.44-1.54 (1H, m), 1.62-1.73 (1H, m), 1.77-1.83 (2H, m), 1.86-1.90 (4H, m), 2.70-2.79 (1H, m), 2.86 (1H, br s), 3.07 (4H, br s), 3.08-3.13 (1H, m), 3.81 (1H, br d, J=13.17 Hz), 3.93-4.02 (1H, m), 4.08-4.17 (1H, m), 4.40 (1H, br d, J=12.90 Hz), 7.97 (1H, dd, J=8.51, 1.65 Hz), 8.04 (1H, s), 8.08 (1H, s), 8.16 (1H, d, J=8.51 Hz), 8.62 (1H, s), 9.48 (1H, s), 10.83 (1H, s); ESIMS found for $C_{23}H_{26}N_6O_3$ m/z 435.2 (M+1).

trans-4-(Hydroxymethyl)-N-(7-(2-methyloxazol-5-yl)quinazolin-2-yl)cyclohexane-1-carboxamide 1447

Off-white solid (7.5 mg, 0.02 mmol, 8.2% yield). $^1$H NMR (499 MHz, DMSO-d) δ ppm 0.90-1.01 (2H, m), 1.35

(1H, td, J=5.83, 3.43 Hz), 1.37-1.47 (2H, m), 1.80 (2H, br dd, J=13.17, 3.02 Hz), 1.90 (2H, br dd, J=12.90, 2.20 Hz), 2.55 (3H, s), 2.59-2.69 (1H, m), 3.24 (2H, t, J=5.76 Hz), 4.39 (1H, t, J=5.35 Hz), 7.89 (1H, dd, J=8.51, 1.65 Hz), 7.91 (1H, s), 7.95 (1H, s), 8.11 (1H, d, J=8.51 Hz), 9.43 (1H, s), 10.64 (1H, s); ESIMS found for $C_{20}H_{22}N_4O_3$ m/z 367.2 (M+1).

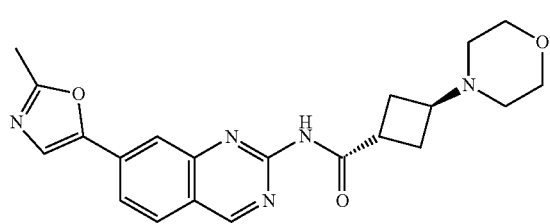

trans-N-(7-(2-Methyloxazol-5-yl)quinazolin-2-yl)-3-morpholinocyclobutane-1-carboxamide 1462

Off-white solid (2 mg, 0.005 mmol, 23.5% yield). $^1$H NMR (499 MHz, DMSO-d$_6$) δ ppm 2.11-2.18 (2H, m), 2.23-2.30 (6H, m), 2.55 (3H, s), 2.78-2.87 (1H, m), 3.55-3.62 (5H, m), 7.88 (1H, dd, J=8.51, 1.65 Hz), 7.92 (1H, s), 7.96 (1H, s), 8.08-8.14 (1H, m), 9.42 (1H, d, J=0.82 Hz), 10.63 (1H, br s); ESIMS found for $C_{21}H_{23}N_5O_3$ m/z 394.15 (M+1).

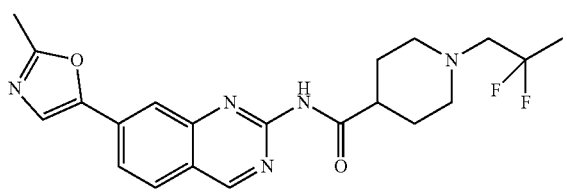

1-(2,2-Difluoropropyl)-N-(7-(2-methyloxazol-5-yl)quinazolin-2-yl)piperidine-4-carboxamide 1471

Brown solid (3.4 mg, 0.008 mmol, 9.0% yield). $^1$H NMR (499 MHz, DMSO-d$_6$) δ ppm 1.63 (3H, br t, J=19.21 Hz), 1.63-1.71 (2H, m), 1.79 (2H, br d, J=10.70 Hz), 2.24 (2H, td, J=11.66, 2.20 Hz), 2.55 (3H, s), 2.67-2.76 (3H, m), 2.95 (2H, br d, J=11.53 Hz), 7.89 (1 H, dd, J=8.51, 1.65 Hz), 7.92 (1H, s), 7.96 (1H, s), 8.12 (1H, d, J=8.23 Hz), 9.44 (1H, s), 10.70 (1H, s); ESIMS found for $C_{21}H_{23}F_2N_5O_2$ m/z 416.2 (M+1).

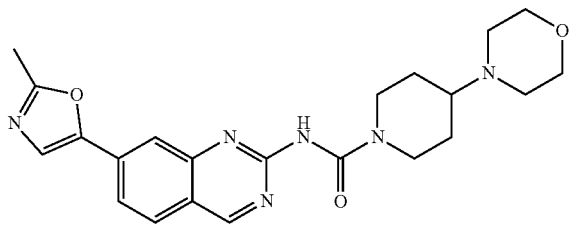

N-(7-(2-Methyloxazol-5-yl)quinazolin-2-yl)-4-morpholinopiperidine-1-carboxamide 1472

Yellow solid (25 mg, 0.06 mmol, 12.8% yield). $^1$H NMR (499 MHz, DMSO-d$_6$) δ ppm 1.33-1.46 (2H, m), 1.79 (2H, br d, J=11.25 Hz), 2.33-2.43 (1H, m), 2.45-2.49 (4H, m), 2.54 (3H, s), 2.87 (2H, br t, J=11.94 Hz), 3.51-3.61 (5H, m), 4.10 (2H, br d, J=12.90 Hz), 7.79 (1H, dd, J=8.51, 1.65 Hz), 7.85 (1H, s), 7.87 (1H, s), 8.05 (1H, d, J=8.23 Hz), 9.33 (1H, s), 9.66 (1H, br s); ESIMS found for $C_{22}H_{26}N_6O_3$ m/z 423.2 (M+1).

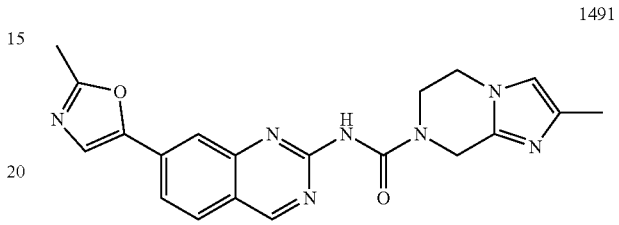

2-Methyl-N-(7-(2-methyloxazol-5-yl)quinazolin-2-yl)-5,6-dihydroimidazo[1,2-a]pyrazine-7(8H)-carboxamide 1491

Beige solid (15 mg, 0.04 mmol, 8.6% yield). $^1$H NMR (499 MHz, DMSO-d$_6$) δ ppm 2.05 (3H, s), 2.54 (3H, s), 3.87-3.93 (3H, m), 3.97-4.03 (2H, m), 4.62 (2H, s), 6.81 (1H, d, J=0.82 Hz), 7.80-7.83 (1H, m), 7.84 (1H, s), 7.87 (1H, s), 8.07 (1H, d, J=8.51 Hz), 9.37 (1H, s); ESIMS found for $C_{20}H_{19}N_7O_2$ m/z 390.2 (M+1).

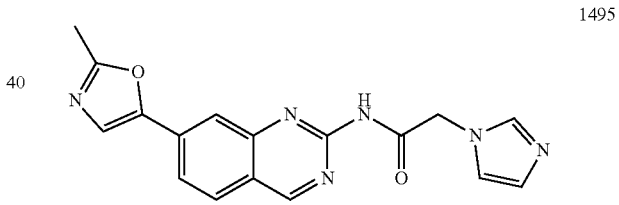

2-(1H-Imidazol-1-yl)-N-(7-(2-methyloxazol-5-yl)quinazolin-2-yl)acetamide 1495

Beige solid (6 mg, 0.02 mmol, 27.2% yield). $^1$H NMR (499 MHz, DMSO-d$_6$) δ ppm 2.54 (3H, s), 5.36 (2H, s), 6.90 (1H, s), 7.18 (1H, s), 7.65 (1H, s), 7.92 (1H, br dd, J=8.51, 1.65 Hz), 7.92 (1H, s), 8.03-8.06 (1H, m), 8.15 (1H, d, J=8.51 Hz), 9.48 (1H, s), 11.11 (1H, s); ESIMS found for $C_{17}H_{14}N_6O_2$ m/z 335.1 (M+1).

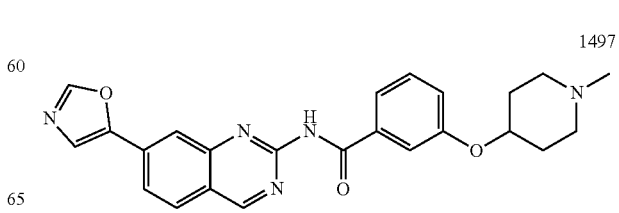

3-((1-Methylpiperidin-4-yl)oxy)-N-(7-(oxazol-5-yl)quinazolin-2-yl)benzamide 1497

Yellow solid (3 mg, 0.007 mmol, 3.2% yield). $^1$H NMR (499 MHz, DMSO-d$_6$) δ ppm 1.62-1.71 (2H, m), 1.92-2.00 (2H, m), 2.15-2.24 (2H, m), 2.18 (3H, s), 2.58-2.65 (2H, m), 4.46-4.53 (1H, m), 7.18 (1H, dt, J=8.23, 1.23 Hz), 7.42 (1H, t, J=7.96 Hz), 7.54-7.61 (2H, m), 8.01 (1H, dd, J=8.37, 1.51 Hz), 8.08-8.13 (2H, m), 8.22 (1H, d, J=8.23 Hz), 8.63 (1H, s), 9.56 (1H, s), 11.20 (1H, br s); ESIMS found for C$_{24}$H$_{23}$N$_5$O$_3$ m/z 430.2 (M+1).

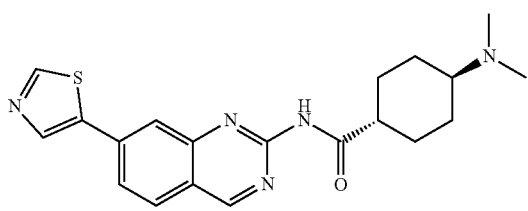

trans-4-(Dimethylamino)-N-(7-(thiazol-5-yl)quinazolin-2-yl)cyclohexane-1-carboxamide 1518

Off-white solid (5 mg, 0.01 mmol, 14.7% yield). $^1$H NMR (499 MHz, DMSO-d$_6$) δ ppm 1.14-1.22 (2H, m), 1.44 (2H, qd, J=12.72, 2.74 Hz), 1.82-1.90 (2H, m), 1.90-1.98 (2H, m), 2.13-2.17 (1H, m), 2.18 (6H, s), 2.59-2.66 (1H, m), 7.95 (1H, dd, J=8.51, 1.65 Hz), 8.00 (1H, d, J=1.37 Hz), 8.13 (1H, d, J=8.51 Hz), 8.65 (1H, s), 9.24 (1H, s), 9.47 (1H, s), 10.69 (1H, s); ESIMS found for C$_{20}$H$_{23}$N$_5$OS m/z 382.2 (M+1).

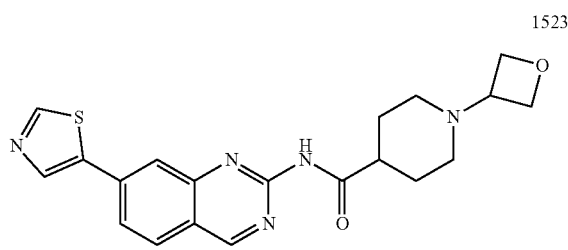 [SMILES: O=C(Nc1ncc2ccc(-c3cncs3)cc2n1)C1CCN(C2COC2)CC1]

1-(Oxetan-3-yl)-N-(7-(thiazol-5-yl)quinazolin-2-yl)piperidine-4-carboxamide 1523

Off-white solid (25 mg, 0.06 mmol, 28.6% yield). $^1$H NMR (499 MHz, DMSO-d$_6$) δ ppm 1.61-1.71 (2H, m), 1.76-1.88 (4H, m), 2.64-2.72 (1H, m), 2.72-2.78 (2H, m), 3.39 (1H, quin, J=6.38 Hz), 4.43 (2H, t, J=6.17 Hz), 4.53 (2H, t, J=6.59 Hz), 7.95 (1H, dd, J=8.37, 1.78 Hz), 7.99-8.03 (1H, m), 8.13 (1H, d, J=8.51 Hz), 8.66 (1H, s), 9.25 (1H, s), 9.47 (1H, s), 10.73 (1H, s); ESIMS found for C$_{20}$H$_{21}$N$_5$O$_2$S m/z 396.15 (M+1).

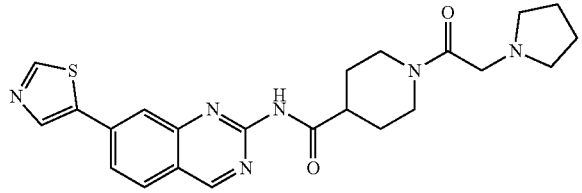

1-(2-(Pyrrolidin-1-yl)acetyl)-N-(7-(thiazol-5-yl)quinazolin-2-yl)piperidine-4-carboxamide 1524

Beige solid (15 mg, 0.03 mmol, 28.2% yield). $^1$H NMR (499 MHz, DMSO-d$_6$) δ ppm 1.37-1.51 (1H, m), 1.54-1.64 (1H, m), 1.69 (4H, br s), 1.79-1.91 (2H, m), 2.49 (4H, br s), 2.60-2.70 (1H, m), 2.95-3.11 (2H, m), 3.19 (1H, br d, J=13.45 Hz), 3.33-3.38 (1H, m), 4.10 (1H, br d, J=13.72 Hz), 4.39 (1H, br d, J=12.62 Hz), 7.96 (1H, dd, J=8.37, 1.78 Hz), 8.02 (1H, d, J=1.65 Hz), 8.13 (1H, d, J=8.23 Hz), 8.66 (1H, s), 9.25 (1H, s), 9.48 (1H, s), 10.79 (1H, s); ESIMS found for C$_{23}$H$_{26}$N$_6$O$_2$S m/z 451.2 (M+1).

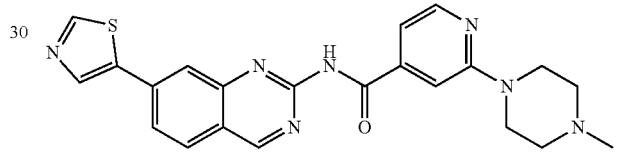

2-(4-Methylpiperazin-1-yl)-N-(7-(thiazol-5-yl)quinazolin-2-yl)isonicotinamide 1536

Brown solid (6.4 mg, 0.01 mmol, 4.8% yield). $^1$H NMR (499 MHz, DMSO-d$_6$) δ ppm 2.23 (3H, s), 2.39-2.45 (4H, m), 3.56-3.62 (4H, m), 7.10 (1H, dd, J=5.08, 1.24 Hz), 7.39 (1H, s), 8.02 (1H, dd, J=8.37, 1.78 Hz), 8.07-8.12 (1H, m), 8.20 (1H, d, J=8.23 Hz), 8.26 (1H, d, J=5.76 Hz), 8.68 (1H, s), 9.26 (1H, s), 9.57 (1H, d, J=0.82 Hz), 11.35 (1H, br s); ESIMS found for C$_{22}$H$_{21}$N$_7$OS m/z 432.2 (M+1).

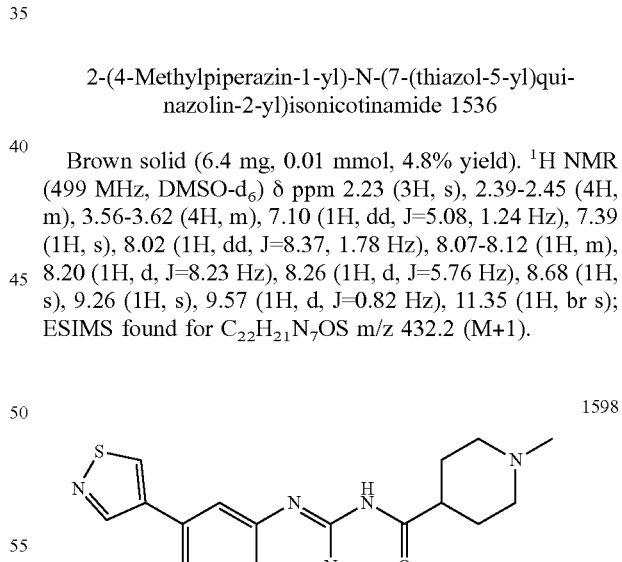

N-(7-(Isothiazol-4-yl)quinazolin-2-yl)-1-methylpiperidine-4-carboxamide 1598

Beige solid (80 mg, 0.23 mmol, 51.7% yield). $^1$H NMR (499 MHz, DMSO-d$_6$) δ ppm 1.77-1.90 (2H, m), 2.05-2.16 (2H, m), 2.50-2.53 (1H, m), 2.81 (3H, s), 2.95-3.07 (2H, m), 3.50 (2H, br d, J=9.06 Hz), 8.07 (1H, dd, J=8.37, 1.78 Hz), 8.16 (1H, d, J=8.23 Hz), 8.20-8.23 (1H, m), 9.31 (1H, s), 9.49 (1H, d, J=0.82 Hz), 9.72 (1H, s), 10.91 (1H, s); ESIMS found for C$_{18}$H$_{19}$N$_5$OS m/z 354.1 (M+1).

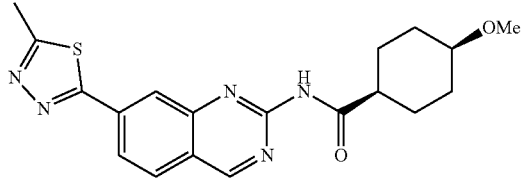

cis-4-Methoxy-N-(7-(5-methyl-1,3,4-thiadiazol-2-yl)quinazolin-2-yl)cyclohexane-1-carboxamide 1612

Brown solid (6 mg, 0.02 mmol, 5.1% yield). $^1$H NMR (499 MHz, DMSO-d$_6$) δ ppm 1.09-1.19 (2H, m), 1.41-1.52 (2H, m), 1.67-1.77 (1H, m), 1.86-1.97 (2H, m), 2.05-2.11 (1H, m), 2.66-2.74 (1H, m), 2.84 (3H, s), 3.13 (1H, tt, J=10.63, 4.19 Hz), 3.25 (3H, s), 8.12-8.17 (1H, m), 8.19-8.24 (2H, m), 9.56 (1H, s), 10.78 (1H, s); ESIMS found for C$_{19}$H$_{21}$N$_5$O$_2$S m/z 384.15 (M+1).

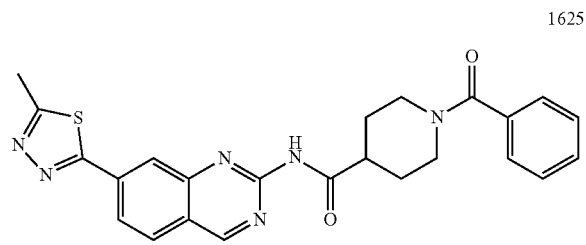 [SMILES: Cc1nnc(-c2ccc3cnc(NC(=O)C4CCN(C(=O)c5ccccc5)CC4)nc3c2)s1]

1-Benzoyl-N-(7-(5-methyl-1,3,4-thiadiazol-2-yl)quinazolin-2-yl)piperidine-4-carboxamide 1625

Beige solid (21 mg, 0.05 mmol, 32.5% yield). $^1$H NMR (499 MHz, DMSO-d$_6$) δ ppm 1.54-1.67 (2H, m), 1.76-1.91 (1H, m), 1.91-2.05 (1H, m), 2.84 (3H, s), 2.88-2.99 (1H, m), 3.01-3.19 (2H, m), 3.61-3.76 (1H, m), 4.43-4.62 (1H, m), 7.39-7.42 (2H, m), 7.44-7.48 (3H, m), 8.15-8.18 (1H, m), 8.21-8.24 (2H, m), 9.58 (1H, s), 10.90 (1H, s); ESIMS found for C$_{24}$H$_{22}$N$_6$O$_2$S m/z 459.2 (M+1).

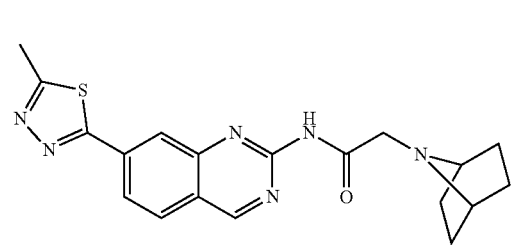

2-(7-Azabicyclo[2.2.1]heptan-7-yl)-N-(7-(5-methyl-1,3,4-thiadiazol-2-yl)quinazolin-2-yl)acetamide 1632

Off-white solid (30 mg, 0.08 mmol, 38.4% yield). $^1$H NMR (499 MHz, DMSO-d$_6$) δ ppm 1.33 (4H, d, J=7.14 Hz), 1.70-1.76 (4H, m), 2.84 (3H, s), 3.36-3.40 (2H, m), 8.18-8.21 (1H, m), 8.23-8.25 (1H, m), 8.26 (1H, d, J=0.82 Hz), 9.59 (1H, s), 10.51 (1H, s); ESIMS found for C$_{19}$H$_{20}$N$_6$OS m/z 381.2 (M+1).

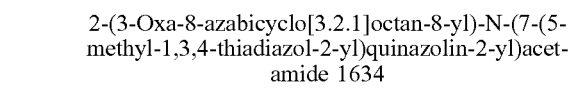

2-(3-Oxa-8-azabicyclo[3.2.1]octan-8-yl)-N-(7-(5-methyl-1,3,4-thiadiazol-2-yl)quinazolin-2-yl)acetamide 1634

Beige solid (4 mg, 0.01 mmol, 7.5% yield). $^1$H NMR (499 MHz, DMSO-d$_6$) δ ppm 1.76-1.82 (2H, m), 1.87-1.92 (2H, m), 2.84 (3H, s), 3.17 (2H, br s), 3.50 (2H, dd, J=10.43, 1.65 Hz), 3.64 (2H, d, J=10.15 Hz), 8.18-8.22 (1H, m), 8.23-8.26 (1H, m), 8.26-8.28 (1H, m), 9.61 (1H, s), 10.57 (1H, s); ESIMS found for C$_{19}$H$_{20}$N$_6$O$_2$S m/z 397.2 (M+1).

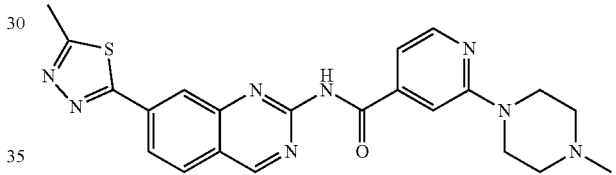

N-(7-(5-Methyl-1,3,4-thiadiazol-2-yl)quinazolin-2-yl)-2-(4-methylpiperazin-1-yl)isonicotinamide 1656

Yellow solid (13.8 mg, 0.03 mmol, 3.8% yield). $^1$H NMR (499 MHz, DMSO-d$_6$) δ ppm 2.23 (3H, s), 2.42 (4H, t, J=4.94 Hz), 2.85 (3H, s), 3.55-3.63 (4H, m), 7.10 (1H, dd, J=5.21, 1.37 Hz), 7.40 (1H, s), 8.21-8.24 (1H, m), 8.26 (1H, d, J=5.21 Hz), 8.28-8.31 (2H, m), 9.67 (1H, s), 11.43 (1H, s); ESIMS found for C$_{22}$H$_{22}$N$_8$OS m/z 447.2 (M+1).

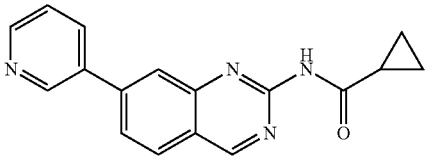

N-(7-(Pyridin-3-yl)quinazolin-2-yl)cyclopropanecarboxamide 1670

Beige solid (20 mg, 0.07 mmol, 31.1% yield). $^1$H NMR (499 MHz, DMSO-d$_6$) δ ppm 0.81-0.95 (4H, m), 2.07-2.16 (1H, m), 7.61 (1H, dd, J=7.82, 4.80 Hz), 8.22 (1H, d, J=8.78 Hz), 8.61 (2H, d, J=3.98 Hz), 8.64 (1H, dt, J=7.96, 1.92 Hz), 8.74 (1H, dd, J=4.67, 1.65 Hz), 9.25 (1H, s), 9.45 (1H, d, J=1.65 Hz), 11.10 (1H, s); ESIMS found for C$_{17}$H$_{14}$N$_4$O m/z 291.15 (M+1).

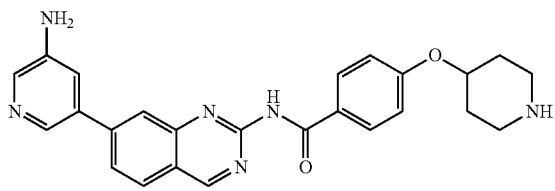

N-(7-(5-Aminopyridin-3-yl)quinazolin-2-yl)-4-(piperidin-4-yloxy)benzamide 1710

White solid (5.4 mg, 0.01 mmol, 78.5% yield). $^1$H NMR (499 MHz, DMSO-$d_6$) δ ppm 1.46-1.58 (2H, m), 1.91-2.01 (2H, m), 2.59-2.68 (2H, m), 2.98 (2H, dt, J=12.69, 4.08 Hz), 4.57 (1H, dt, J=8.85, 4.49 Hz), 5.53 (2H, s), 7.06 (2H, d, J=8.78 Hz), 7.34 (1H, t, J=2.33 Hz), 7.89 (1H, dd, J=8.51, 1.65 Hz), 7.98 (1H, s), 8.00 (2H, d, J=8.78 Hz), 8.03 (1H, d, J=2.74 Hz), 8.20 (1H, d, J=8.51 Hz), 8.22 (1H, d, J=1.92 Hz), 9.58 (1H, s), 11.04 (1H, br s); ESIMS found for $C_{25}H_{24}N_6O_2$ m/z 441.2 (M+1).

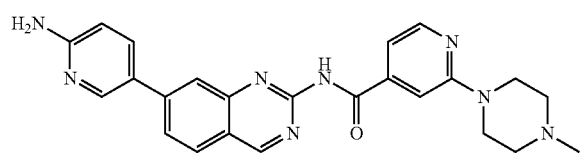

N-(7-(6-Aminopyridin-3-yl)quinazolin-2-yl)-2-(4-methylpiperazin-1-yl)isonicotinamide 1713

Beige solid (14 mg, 0.03 mmol, 19.4% yield). $^1$H NMR (500 MHz, DMSO-$d_6$) δ ppm 2.23 (3H, s), 2.42 (4H, br t, J=4.94 Hz), 3.54-3.63 (4H, m), 6.35 (2H, s), 6.59 (1H, d, J=8.51 Hz), 7.10 (1H, dd, J=5.08, 1.23 Hz), 7.40 (1H, s), 7.91-7.99 (3H, m), 8.13 (1H, d, J=8.23 Hz), 8.26 (1H, d, J=5.21 Hz), 8.50 (1H, d, J=1.92 Hz), 9.51 (1H, s), 11.28 (1H, br s); ESIMS found for $C_{24}H_{24}N_8O$ m/z 441.2 (M+1).

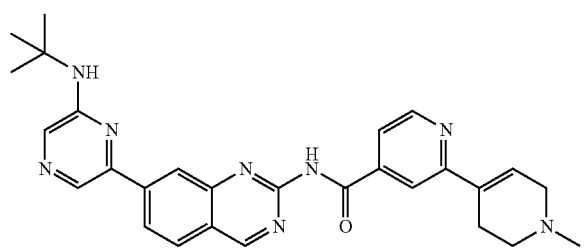

N-(7-(6-(tert-Butylamino)pyrazin-2-yl)quinazolin-2-yl)-1'-methyl-1',2',3',6'-tetrahydro-[2,4'-bipyridine]-4-carboxamide 1773

Tan solid (47.7 mg, 0.10 mmol, 26.3% yield). $^1$H NMR (499 MHz, DMSO-$d_6$) δ ppm 1.51 (9H, s), 2.31 (3H, s), 2.58-2.62 (2H, m), 2.63-2.67 (2H, m), 3.11 (2H, br d, J=3.02 Hz), 6.87 (1H, t, J=3.43 Hz), 7.07 (1H, s), 7.73 (1H, dd, J=4.94, 1.37 Hz), 8.00 (1H, s), 8.10 (1H, s), 8.19-8.25 (1H, m), 8.31 (1H, dd, J=8.64, 1.51 Hz), 8.48 (2H, s), 8.71 (1H, d, J=4.94 Hz), 9.62 (1H, s), 11.55 (1H, s); ESIMS found for $C_{28}H_{30}N_8O$ m/z 495.25 (M+1).

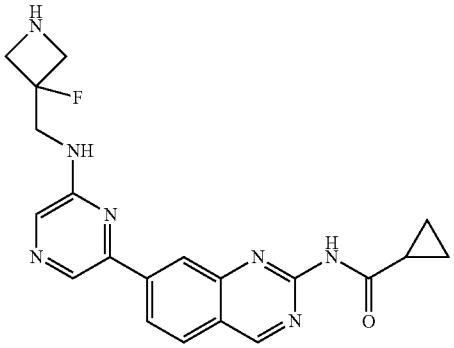

N-(7-(6-(((3-Fluoroazetidin-3-yl)methyl)amino)pyrazin-2-yl)quinazolin-2-yl)cyclopropanecarboxamide 1777

Yellow solid (25.1 mg, 0.06 mmol, 80.8% yield). $^1$H NMR (499 MHz, DMSO-$d_6$) δ ppm 0.83-0.89 (4H, m), 2.17-2.27 (1H, m), 4.00 (2H, dd, J=21.20, 6.10 Hz), 4.03-4.17 (4H, m), 7.64 (1H, t, J=6.04 Hz), 8.11 (1H, s), 8.16 (1H, d, J=8.51 Hz), 8.28 (1H, dd, J=8.37, 1.51 Hz), 8.43 (1H, s), 8.58 (1H, s), 9.53 (1H, s), 11.07 (1H, s); ESIMS found for $C_{20}H_{20}FNO_7O$ m/z 394.2 (M+1).

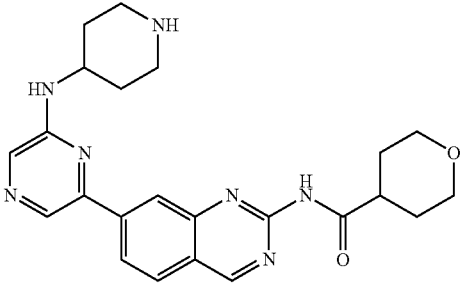

N-(7-(6-(Piperidin-4-ylamino)pyrazin-2-yl)quinazolin-2-yl)tetrahydro-2H-pyran-4-carboxamide 1783

Beige solid (10 mg, 0.02 mmol, 72.4% yield). $^1$H NMR (500 MHz, DMSO-$d_6$) δ ppm 1.31-1.44 (2H, m), 1.61-1.72 (2H, m), 1.74-1.81 (2H, m), 1.95 (2H, br dd, J=11.53, 2.74 Hz), 2.57-2.66 (2H, m), 2.94-3.08 (3H, m), 3.36-3.43 (2H, m), 3.89-3.97 (3H, m), 7.25 (1H, br d, J=7.41 Hz), 7.98 (1H, s), 8.14 (1H, d, J=8.51 Hz), 8.22 (1H, dd, J=8.37, 1.51 Hz), 8.39 (1H, s), 8.46 (1H, s), 9.50 (1H, s), 10.74 (1H, s); ESIMS found for $C_{23}H_{27}N_7O_2$ m/z 434.2 (M+1).

1785

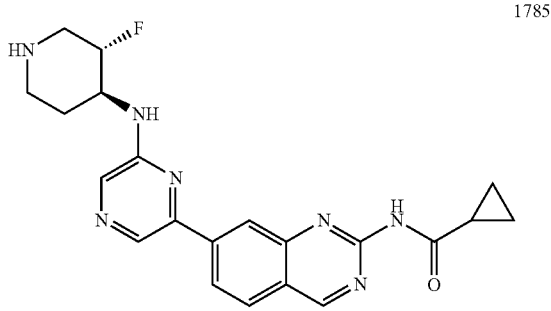 [SMILES: O=C(Nc1ncc2ccc(-c3cncc(N[C@H]4CCNC[C@@H]4F)n3)cc2n1)C1CC1]

N-(7-(6-(((3S,4S)-3-Fluoropiperidin-4-yl)amino)
pyrazin-2-yl)quinazolin-2-yl)cyclopropanecarboxamide 1785

Orange solid (1.8 mg, 0.004 mmol, 15.2% yield). $^1$H NMR (500 MHz, METHANOL-d$_4$) δ ppm 0.92-1.00 (2H, m), 1.07-1.12 (2H, m), 1.54-1.64 (1H, m), 2.05-2.11 (1H, m), 2.22-2.31 (1H, m), 2.74-2.87 (3H, m), 2.99-3.06 (1H, m), 4.32-4.43 (1H, m), 4.46-4.63 (1H, m), 7.95 (1H, s), 8.09 (1H, d, J=8.23 Hz), 8.24 (1H, dd, J=8.51, 1.65 Hz), 8.39 (1H, s), 8.58-8.62 (1H, m), 9.40 (1H, s); ESIMS found for C$_{21}$H$_{22}$FN$_7$O m/z 407.2 (M+1).

1802

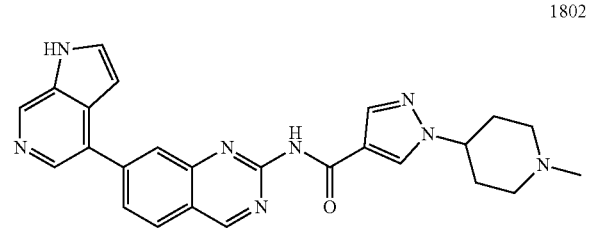 [SMILES: CN1CCC(n2cc(C(=O)Nc3ncc4ccc(-c5cncc6[nH]ccc56)cc4n3)cn2)CC1]

N-(7-(1H-Pyrrolo[2,3-c]pyridin-4-yl)quinazolin-2-yl)-1-(1-methylpiperidin-4-yl)-1H-pyrazole-4-carboxamide 1802

Yellow solid (3 mg, 0.007 mmol, 12.6% yield). $^1$H NMR (499 MHz, METHANOL-d$_4$) δ ppm 1.94 (6H, s), 2.11-2.23 (4H, m), 2.24-2.32 (2H, m), 3.03 (2H, br d, J=12.35 Hz), 4.24-4.35 (1H, m), 6.90 (1H, d, J=3.02 Hz), 7.72 (1H, d, J=3.02 Hz), 8.01 (1H, dd, J=8.23, 1.65 Hz), 8.16 (1H, s), 8.19 (1H, d, J=8.23 Hz), 8.33-8.40 (2H, m), 8.48 (1H, s), 8.78 (1H, s), 9.47 (1H, s); ESIMS found for C$_{25}$H$_{24}$N$_8$O m/z 453.2 (M+1).

1813

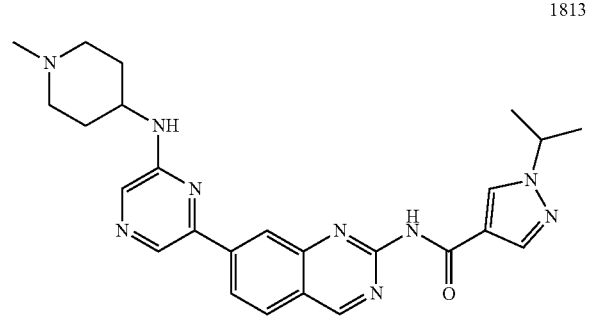 [SMILES: CC(C)n1cc(C(=O)Nc2ncc3ccc(-c4cncc(NC5CCN(C)CC5)n4)cc3n2)cn1]

1-Isopropyl-N-(7-(6-((1-methylpiperidin-4-yl)amino)pyrazin-2-yl)quinazolin-2-yl)-1H-pyrazole-4-carboxamide 1813

Brown wax (4.6 mg, 0.01 mmol, 5.0% yield). $^1$H NMR (499 MHz, DMSO-d$_6$) δ ppm 1.46 (6H, d, J=6.86 Hz), 1.49-1.60 (2H, m), 1.95-2.02 (2H, m), 2.06-2.15 (2H, m), 2.20 (3H, s), 2.76 (2H, br d, J=11.25 Hz), 3.80-3.91 (1H, m), 4.55 (1H, spt, J=6.63 Hz), 7.25 (1H, d, J=7.14 Hz), 7.99 (1H, s), 8.12 (1H, s), 8.16-8.21 (1H, m), 8.25 (1H, dd, J=8.51, 1.65 Hz), 8.42 (1H, d, J=1.37 Hz), 8.48 (1H, s), 8.56 (1H, s), 9.56 (1H, s), 10.82 (1H, s); ESIMS found for C$_{25}$H$_{29}$N$_9$O m/z 472.3 (M+1).

1815

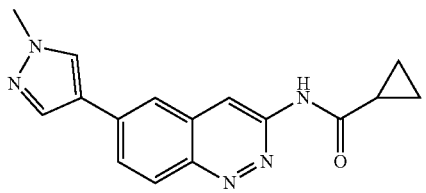

N-(6-(1-Methyl-1H-pyrazol-4-yl)cinnolin-3-yl)cyclopropanecarboxamide 1815

Yellow solid (1.4 mg, 0.005 mmol, 4.0% yield). $^1$H NMR (499 MHz, METHANOL-d$_4$) δ ppm 0.84-0.94 (4H, m), 2.01-2.08 (1H, m), 4.00 (3H, s), 7.99 (1H, s), 8.06 (1H, dd, J=6.17, 0.96 Hz), 8.14 (1H, s), 8.21 (1H, d, J=9.06 Hz), 8.42 (1H, dd, J=9.06, 0.82 Hz), 9.29 (1H, d, J=6.04 Hz); ESIMS found for C$_{16}$H$_{15}$N$_5$O m/z 294.1 (M+1).

1953

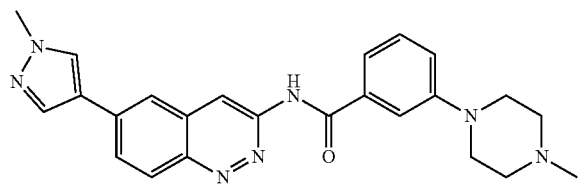

N-(6-(1-Methyl-1H-pyrazol-4-yl)cinnolin-3-yl)-3-(4-methylpiperazin-1-yl) benzamide 1953

Yellow solid (8.7 mg, 0.02 mmol, 21.7% yield). $^1$H NMR (500 MHz, DMSO-d$_6$) δ ppm 2.24 (3H, s), 2.48 (4H, br s), 3.24-3.29 (4H, m), 3.93 (3H, s), 7.19 (1H, dd, J=8.23, 1.92 Hz), 7.38 (2H, t, J=7.96 Hz), 7.52 (2H, br d, J=8.23 Hz), 7.70-7.74 (1H, m), 8.07 (1H, dd, J=9.06, 1.92 Hz), 8.16 (1H, d, J=0.82 Hz), 8.23 (1H, d, J=1.92 Hz), 8.37 (1H, d, J=9.06 Hz), 8.45 (1H, s), 8.81 (1H, d, J=0.82 Hz), 11.64 (1H, s); ESIMS found for C$_{24}$H$_{25}$N$_7$O m/z 428.2 (M+1).

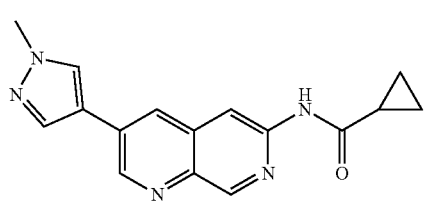

2722

N-(3-(1-Methyl-1H-pyrazol-4-yl)-1,7-naphthyridin-6-yl) cyclopropanecarboxamide 2722

White solid (9 mg, 0.03 mmol, 34.6% yield). $^1$H NMR (499 MHz, DMSO-$d_6$) δ ppm 0.80-0.90 (4H, m), 2.04-2.12 (1H, m), 3.92 (3H, s), 8.18 (1H, d, J=0.82 Hz), 8.44 (1H, d, J=1.92 Hz), 8.45 (1H, s), 8.48 (1H, s), 9.12 (1H, s), 9.17 (1H, d, J=2.20 Hz), 10.99 (1H, s); ESIMS found for $C_{16}H_{15}N_5O$ m/z 294.1 (M+1).

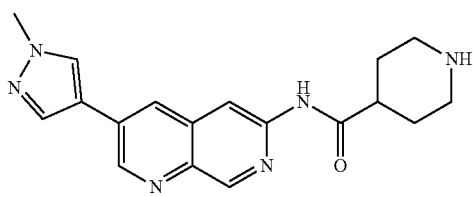

2731

N-(3-(1-Methyl-1H-pyrazol-4-yl)-1,7-naphthyridin-6-yl)piperidine-4-carboxamide 2731

Beige solid (30 mg, 0.09 mmol, 43.3% yield). $^1$H NMR (499 MHz, DMSO-$d_6$) δ ppm 1.53 (2H, qd, J=12.17, 3.57 Hz), 1.70 (2H, br d, J=10.15 Hz), 2.44-2.49 (2H, m), 2.63-2.71 (1H, m), 2.97 (2H, br d, J=13.45 Hz), 3.92 (3H, s), 8.18 (1H, s), 8.46 (1H, d, J=2.20 Hz), 8.48 (1H, s), 8.49 (1H, s), 9.11 (1H, s), 9.17 (1H, d, J=2.20 Hz), 10.58 (1H, s); ESIMS found for $C_{18}H_{20}N_6O$ m/z 337.2 (M+1).

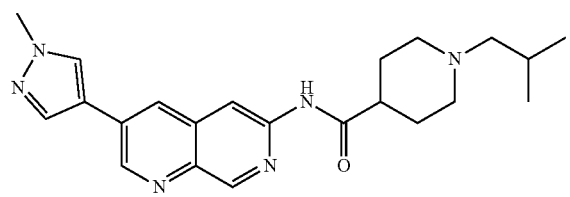

2736

1-Isobutyl-N-(3-(1-methyl-1H-pyrazol-4-yl)-1,7-naphthyridin-6-yl) piperidine-4-carboxamide 2736

Off-white solid (24 mg, 0.06 mmol, 73.5% yield). $^1$H NMR (499 MHz, DMSO-$d_6$) δ ppm 0.86 (6H, d, J=6.31 Hz), 1.62-1.72 (2H, m), 1.73-1.82 (3H, m), 1.87 (2H, td, J=11.66, 1.92 Hz), 2.02 (2H, d, J=7.41 Hz), 2.52-2.60 (1H, m), 2.86 (2H, br d, J=11.53 Hz), 3.92 (3H, s), 8.18 (1H, s), 8.46 (1H, d, J=1.65 Hz), 8.48 (1H, s), 8.49 (1H, s), 9.11 (1H, s), 9.17 (1H, d, J=2.20 Hz), 10.62 (1H, s); ESIMS found for $C_{22}H_{28}N_6O$ m/z 393.2 (M+1).

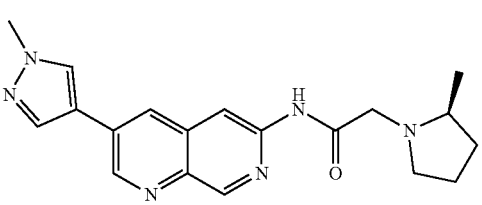

2767

(S)—N-(3-(1-Methyl-1H-pyrazol-4-yl)-1,7-naphthyridin-6-yl)-2-(2-methylpyrrolidin-1-yl)acetamide 2767

Beige solid (60 mg, 0.17 mmol, 77.1% yield). $^1$H NMR (499 MHz, DMSO-$d_6$) δ ppm 1.09 (3H, d, J=6.04 Hz), 1.41 (1H, dddd, J=12.32, 10.33, 8.37, 6.31 Hz), 1.67-1.84 (2H, m), 1.92-2.01 (1H, m), 2.40 (1H, q, J=8.69 Hz), 2.57-2.65 (1H, m), 3.14 (1H, d, J=16.47 Hz), 3.13-3.20 (1H, m), 3.56 (1H, d, J=16.19 Hz), 3.92 (3H, s), 8.20 (1H, d, J=0.82 Hz), 8.48 (1H, s), 8.49 (1H, s), 8.54 (1H, d, J=1.65 Hz), 9.12 (1H, s), 9.20 (1H, d, J=1.92 Hz), 10.05 (1H, s); ESIMS found for $C_{19}H_{22}N_6O$ m/z 351.2 (M+1).

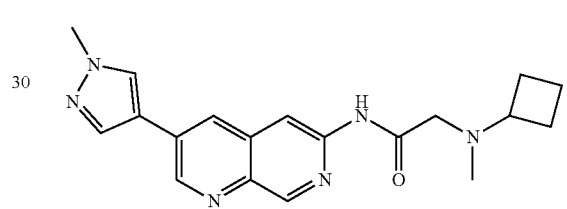

2776

2-(Cyclobutyl(methyl)amino)-N-(3-(1-methyl-1H-pyrazol-4-yl)-1,7-naphthyridin-6-yl)acetamide 2776

Beige solid (60 mg, 0.17 mmol, 77.1% yield). $^1$H NMR (499 MHz, DMSO-$d_6$) δ ppm 1.81-1.96 (2H, m), 2.09-2.20 (2H, m), 2.25-2.34 (2H, m), 2.50 (3H, s), 3.35 (1H, quin, J=7.82 Hz), 3.41 (2H, s), 4.20 (3H, s), 8.47 (1H, s), 8.75 (1H, s), 8.76 (1H, s), 8.81 (1H, d, J=1.65 Hz), 9.40 (1H, s), 9.47 (1H, d, J=2.20 Hz), 10.35 (1H, s); ESIMS found for $C_{19}H_{22}N_6O$ m/z 351.2 (M+1).

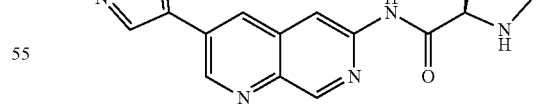

2782

(R)—N-(3-(1-Methyl-1H-pyrazol-4-yl)-1,7-naphthyridin-6-yl)pyrrolidine-2-carboxamide 2782

Beige solid (25 mg, 0.08 mmol, 35.4% yield). $^1$H NMR (499 MHz, DMSO-$d_6$) δ ppm 1.67 (2H, quin, J=6.86 Hz), 1.81-1.90 (1H, m), 2.06-2.16 (1H, m), 2.88 (1H, dt, J=10.15, 6.31 Hz), 2.97 (1H, dt, J=10.15, 6.72 Hz), 3.82 (1H, dd, J=9.06, 5.49 Hz), 3.92 (3H, s), 8.19 (1H, s), 8.49 (2H, s), 8.52 (1H, d, J=1.65 Hz), 9.11 (1H, s), 9.19 (1H, d, J=2.20 Hz), 10.47 (1H, s); ESIMS found for $C_{17}H_{18}N_6O$ m/z 323.2 (M+1).

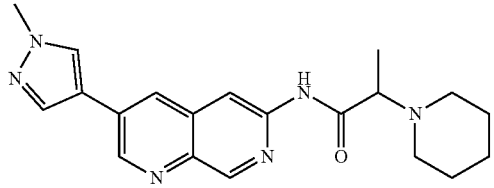

N-(3-(1-Methyl-1H-pyrazol-4-yl)-1,7-naphthyridin-6-yl)-2-(piperidin-1-yl) propanamide 2791

Off-white solid (34 mg, 0.09 mmol, 70.0% yield). $^1$H NMR (499 MHz, DMSO-$d_6$) δ ppm 1.20 (3H, d, J=6.86 Hz), 1.40-1.46 (2H, m), 1.53-1.63 (4H, m), 2.51-2.59 (4H, m), 3.46 (1H, q, J=6.86 Hz), 3.93 (3H, s), 8.19 (1H, s), 8.48 (1H, s), 8.49 (1H, s), 8.50 (1 H, d, J=1.92 Hz), 9.13 (1H, s), 9.19 (1H, d, J=2.20 Hz), 10.25 (1H, s); ESIMS found for $C_{20}H_{24}N_6O$ m/z 365.2 (M+1).

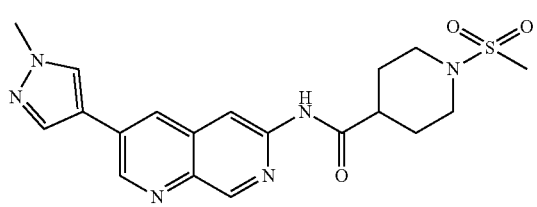

N-(3-(1-Methyl-1H-pyrazol-4-yl)-1,7-naphthyridin-6-yl)-1-(methylsulfonyl) piperidine-4-carboxamide 2792

White solid (11.3 mg, 0.03 mmol, 29.0% yield). $^1$H NMR (499 MHz, DMSO-$d_6$) δ ppm 1.70 (2H, qd, J=12.21, 3.98 Hz), 1.96 (2H, br dd, J=13.45, 2.74 Hz), 2.66-2.72 (1H, m), 2.76 (2H, td, J=11.94, 2.47 Hz), 2.90 (3H, s), 3.60-3.66 (2H, m), 3.93 (3H, s), 8.18 (1H, d, J=0.82 Hz), 8.45-8.53 (3H, m), 9.13 (1H, s), 9.18 (1H, d, J=2.20 Hz), 10.78 (1H, s); ESIMS found for $C_{19}H_{22}N_6O_3S$ m/z 415.2 (M+1).

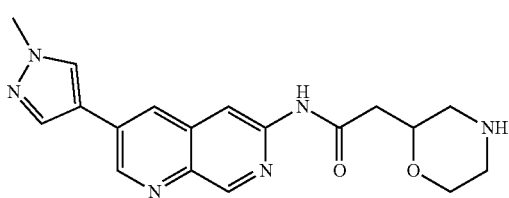

N-(3-(1-Methyl-1H-pyrazol-4-yl)-1,7-naphthyridin-6-yl)-2-(morpholin-2-yl) acetamide 2807

Brown solid (20 mg, 0.06 mmol, 52.4% yield). $^1$H NMR (499 MHz, DMSO-$d_6$) δ ppm 2.42 (1H, dd, J=12.08, 10.15 Hz), 2.45-2.49 (1H, m), 2.58-2.70 (3H, m), 2.81-2.87 (1H, m), 3.43 (1H, td, J=10.91, 3.16 Hz), 3.70 (1H, br d, J=10.70 Hz), 3.80-3.88 (1H, m), 3.92 (3H, s), 8.19 (1H, s), 8.46-8.52 (3H, m), 9.11 (1H, s), 9.18 (1H, d, J=2.20 Hz), 10.65 (1H, s); ESIMS found for $C_{18}H_{20}N_6O_2$ m/z 353.2 (M+1).

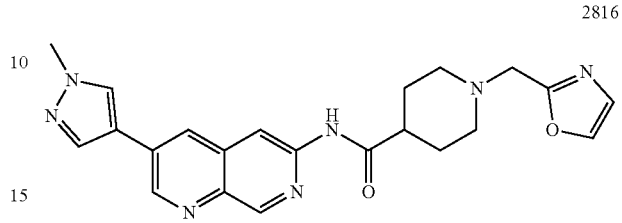

N-(3-(1-Methyl-1H-pyrazol-4-yl)-1,7-naphthyridin-6-yl)-1-(oxazol-2-ylmethyl)piperidine-4-carboxamide 2816

Brown solid (22 mg, 0.05 mmol, 56.1% yield). $^1$H NMR (499 MHz, DMSO-$d_6$) δ ppm 1.67 (2H, qd, J=12.21, 3.70 Hz), 1.80 (2H, br d, J=10.70 Hz), 2.10 (2H, td, J=11.53, 1.92 Hz), 2.52-2.58 (1H, m), 2.89 (1H, br d, J=3.02 Hz), 3.67 (2H, s), 3.92 (3H, s), 7.18 (1H, s), 8.08 (1H, s), 8.18 (1H, s), 8.46 (1H, d, J=1.92 Hz), 8.47 (1H, s), 8.49 (1H, s), 9.11 (1H, s), 9.17 (1H, d, J=1.92 Hz), 10.63 (1H, s); ESIMS found for $C_{22}H_{23}N_7O_2$ m/z 418.2 (M+1).

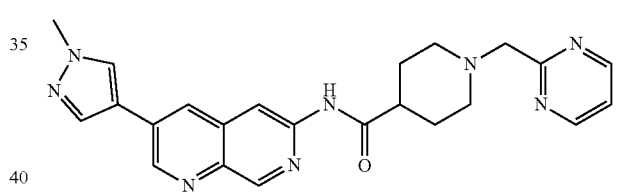

N-(3-(1-Methyl-1H-pyrazol-4-yl)-1,7-naphthyridin-6-yl)-1-(pyrimidin-2-ylmethyl)piperidine-4-carboxamide 2820

Biege solid (17 mg, 0.04 mmol, 42.3% yield). $^1$H NMR (499 MHz, DMSO-$d_6$) δ ppm 1.68 (2H, qd, J=12.21, 3.70 Hz), 1.76-1.82 (2H, m), 2.11-2.21 (2H, m), 2.52-2.59 (1H, m), 2.96 (2H, br d, J=11.53 Hz), 3.71 (2H, s), 3.92 (3H, s), 7.41 (1H, t, J=4.80 Hz), 8.17 (1H, s), 8.46 (1H, d, J=2.20 Hz), 8.47 (1H, s), 8.49 (1H, s), 8.79 (2H, d, J=4.94 Hz), 9.11 (1H, s), 9.17 (1H, d, J=2.20 Hz), 10.62 (1H, s); ESIMS found for $C_{23}H_{24}N_8O$ m/z 429.2 (M+1).

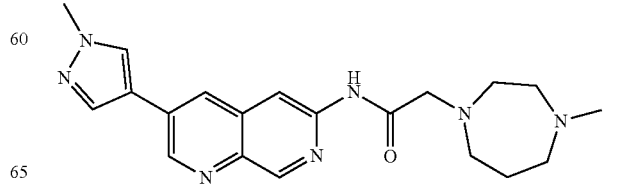

2-(4-Methyl-1,4-diazepan-1-yl)-N-(3-(1-methyl-1H-pyrazol-4-yl)-1,7-naphthyridin-6-yl)acetamide 2826

Beige solid (45 mg, 0.12 mmol, 53.4% yield). $^1$H NMR (499 MHz, DMSO-d$_6$) δ ppm 1.78 (2H, quin, J=5.97 Hz), 2.28 (3H, s), 2.57-2.63 (4H, m), 2.80-2.87 (4H, m), 3.38 (2H, s), 3.92 (3H, s), 8.19 (1H, s), 8.49 (2H, s), 8.54 (1H, d, J=1.92 Hz), 9.14 (1H, s), 9.20 (1H, d, J=2.20 Hz), 10.11 (1H, s); ESIMS found for $C_{20}H_{25}N_7O$ m/z 380.2 (M+1).

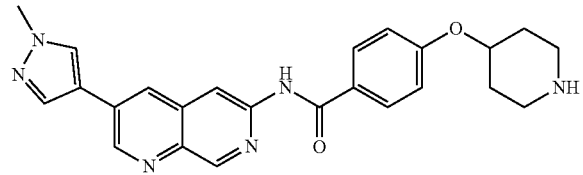

2864

N-(3-(1-Methyl-1H-pyrazol-4-yl)-1,7-naphthyridin-6-yl)-4-(piperidin-4-yloxy)benzamide 2864

Off-white solid (20 mg, 0.05 mmol, 89.8% yield). $^1$H NMR (499 MHz, DMSO-d$_6$) δ ppm 1.41-1.52 (2H, m), 1.94 (2H, br dd, J=11.94, 2.33 Hz), 2.60 (2H, brt, J=10.29 Hz), 2.91-3.00 (2H, m), 3.93 (3H, s), 4.51-4.60 (1H, m), 7.06 (2H, d, J=8.78 Hz), 8.06 (2H, d, J=8.78 Hz), 8.21 (1H, s), 8.50 (1H, s), 8.54 (1H, d, J=1.65 Hz), 8.64 (1H, s), 9.18 (1H, s), 9.21 (1H, d, J=2.20 Hz), 10.80 (1H, s); ESIMS found for $C_{24}H_{24}N_6O_2$ m/z 429.2 (M+1).

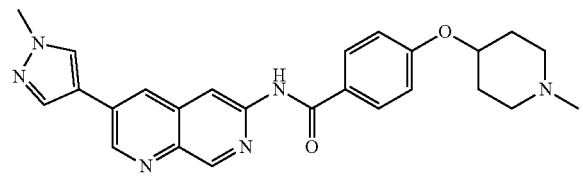

2865

N-(3-(1-Methyl-1H-pyrazol-4-yl)-1,7-naphthyridin-6-yl)-4-((1-methylpiperidin-4-yl)oxy)benzamide 2865

Off-white solid (18 mg, 0.04 mmol, 67.0% yield). $^1$H NMR (499 MHz, DMSO-d$_6$) δ ppm 1.61-1.72 (2H, m), 1.97 (2H, br dd, J=9.74, 3.70 Hz), 2.15-2.25 (2H, m), 2.19 (3H, s), 2.57-2.66 (2H, m), 3.93 (3H, s), 4.46-4.54 (1H, m), 7.07 (2H, d, J=9.06 Hz), 8.07 (2H, d, J=8.78 Hz), 8.21 (1H, s), 8.50 (1H, s), 8.54 (1H, d, J=1.92 Hz), 8.63 (1H, s), 9.18 (1H, s), 9.21 (1H, d, J=2.20 Hz), 10.82 (1H, s); ESIMS found for $C_{25}H_{26}N_6O_2$ m/z 443.2 (M+1).

2866

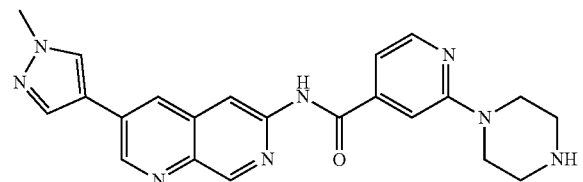

N-(3-(1-Methyl-1H-pyrazol-4-yl)-1,7-naphthyridin-6-yl)-2-(piperazin-1-yl) isonicotinamide 2866

Off-white solid (11.1 mg, 0.03 mmol, 35.3% yield). $^1$H NMR (499 MHz, DMSO-d$_6$) δ ppm 2.79-2.86 (4H, m), 3.50-3.58 (4H, m), 3.93 (3H, s), 7.14 (1H, dd, J=5.08, 1.24 Hz), 7.43 (1H, s), 8.21 (1H, s), 8.26 (1H, d, J=4.94 Hz), 8.51 (1H, s), 8.56 (1H, d, J=1.65 Hz), 8.65 (1H, s), 9.21 (1H, s), 9.24 (1H, d, J=2.20 Hz), 11.20 (1H, s); ESIMS found for $C_{22}H_{22}N_8O$ m/z 415.2 (M+1).

2871

![Structure 2871]

N-(3-(1-Methyl-1H-pyrazol-4-yl)-1,7-naphthyridin-6-yl)-6-(4-methylpiperazin-1-yl)nicotinamide 2871

Off-white solid (16 mg, 0.04 mmol, 64.5% yield). $^1$H NMR (499 MHz, DMSO-d$_6$) δ ppm 2.22 (3H, s), 2.38-2.43 (4H, m), 3.62-3.67 (4H, m), 3.93 (3H, s), 6.91 (1H, d, J=9.06 Hz), 8.17-8.23 (2H, m), 8.50 (1H, s), 8.52 (1H, d, J=1.92 Hz), 8.62 (1H, s), 8.85 (1 H, d, J=2.47 Hz), 9.18 (1H, s), 9.21 (1H, d, J=2.20 Hz), 10.80 (1H, s); ESIMS found for $C_{23}H_{24}N_8O$ m/z 429.2 (M+1).

2884

![Structure 2884]

2-((2-(Dimethylamino)ethyl)amino)-N-(3-(1-methyl-1H-pyrazol-4-yl)-1,7-naphthyridin-6-yl)isonicotinamide 2884

Off-white solid (15.1 mg, 0.04 mmol, 40.8% yield). $^1$H NMR (499 MHz, DMSO-d$_6$) δ ppm 2.21 (6H, s), 2.46 (2H, br t, J=6.59 Hz), 3.37-3.44 (2H, m), 3.93 (3H, s), 6.65 (1H, br t, J=5.35 Hz), 7.03 (1H, dd, J=5.35, 1.51 Hz), 7.04 (1H, s), 8.12 (1H, d, J=5.21 Hz), 8.21 (1H, s), 8.51 (1H, s), 8.57 (1H, d, J=2.20 Hz), 8.62 (1H, s), 9.19 (1H, s), 9.24 (1H, d, J=1.92 Hz), 11.00 (1H, s); ESIMS found for $C_{22}H_{24}N_8O$ m/z 417.2 (M+1).

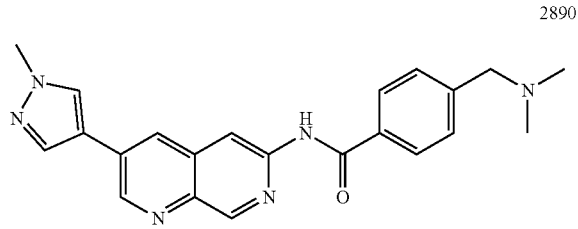 [SMILES: CN(C)Cc1ccc(C(=O)Nc2cc3cc(-c4cnn(C)c4)cnc3cn2)cc1]

4-((Dimethylamino)methyl)-N-(3-(1-methyl-1H-pyrazol-4-yl)-1,7-naphthyridin-6-yl)benzamide 2890

Off-white solid (22.9 mg, 0.06 mmol, 66.7% yield). $^1$H NMR (499 MHz, DMSO-$d_6$) δ ppm 2.17 (6H, s), 3.47 (2H, s), 3.93 (3H, s), 7.44 (2H, d, J=8.23 Hz), 8.05 (2H, d, J=7.96 Hz), 8.21 (1H, s), 8.50 (1H, s), 8.56 (1H, d, J=1.65 Hz), 8.65 (1H, s), 9.19 (1H, s), 9.22 (1H, d, J=2.20 Hz), 10.95 (1H, s); ESIMS found for $C_{22}H_{22}N_6O$ m/z 387.2 (M+1).

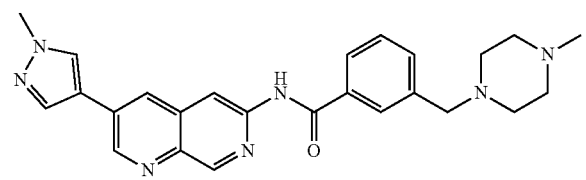

N-(3-(1-Methyl-1H-pyrazol-4-yl)-1,7-naphthyridin-6-yl)-3-((4-methylpiperazin-1-yl)methyl)benzamide 2892

Off-white solid (16.5 mg, 0.04 mmol, 31.1% yield). $^1$H NMR (499 MHz, DMSO-$d_6$) δ ppm 2.15 (3H, s), 2.23-2.37 (4H, m), 2.37-2.48 (4H, m), 3.54 (2H, s), 3.93 (3H, s), 7.45-7.51 (1H, m), 7.51-7.57 (1H, m), 7.96 (1H, d, J=7.68 Hz), 7.98 (1H, s), 8.22 (1H, s), 8.51 (1H, s), 8.56 (1H, d, J=1.65 Hz), 8.65 (1H, s), 9.20 (1H, s), 9.23 (1H, d, J=1.92 Hz), 10.99 (1H, s); ESIMS found for $C_{25}H_{27}N_7O$ m/z 442.2 (M+1).

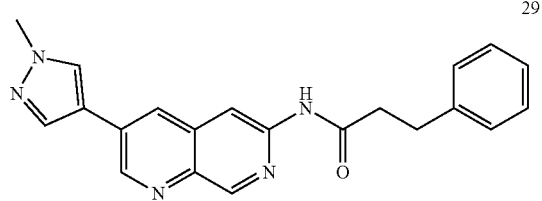

N-(3-(1-Methyl-1H-pyrazol-4-yl)-1,7-naphthyridin-6-yl)-3-phenylpropanamide 2914

Off-white solid (22 mg, 0.06 mmol, 51.4% yield). $^1$H NMR (499 MHz, DMSO-$d_6$) δ ppm 2.74-2.82 (2H, m), 2.92-2.99 (2H, m), 3.92 (3H, s), 7.14-7.22 (1H, m), 7.25-7.33 (4H, m), 8.19 (1H, s), 8.45-8.52 (3H, m), 9.11 (1H, s), 9.17 (1H, d, J=2.20 Hz), 10.71 (1H, s); ESIMS found for $C_{21}H_{19}N_5O$ m/z 358.2 (M+1).

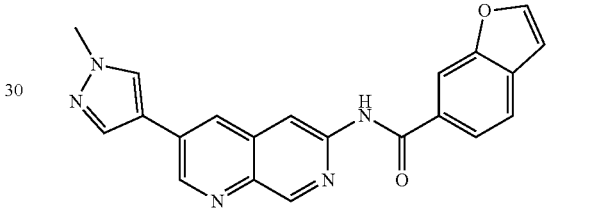

2-Methyl-N-(3-(1-methyl-1H-pyrazol-4-yl)-1,7-naphthyridin-6-yl)-1,2,3,4-tetrahydroisoquinoline-7-carboxamide 2922

Off-white solid (27 mg, 0.07 mmol, 59.2% yield). $^1$H NMR (499 MHz, DMSO-$d_6$) δ ppm 2.37 (3H, s), 2.59-2.66 (2H, m), 2.89 (2H, t, J=5.76 Hz), 3.56 (2H, s), 3.93 (3H, s), 7.26 (1H, d, J=7.96 Hz), 7.81 (1H, s), 7.84 (1H, dd, J=7.82, 1.51 Hz), 8.21 (1H, s), 8.51 (1H, s), 8.55 (1H, d, J=2.20 Hz), 8.64 (1H, s), 9.19 (1H, s), 9.22 (1H, d, J=2.20 Hz), 10.86 (1H, s); ESIMS found for $C_{23}H_{22}N_6O$ m/z 399.2 (M+1).

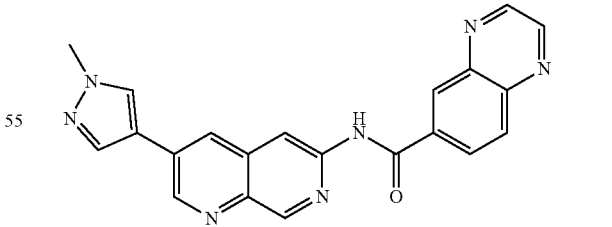

N-(3-(1-Methyl-1H-pyrazol-4-yl)-1,7-naphthyridin-6-yl)benzofuran-6-carboxamide 2929

Off-white solid (18 mg, 0.05 mmol, 40.7% yield). $^1$H NMR (499 MHz, DMSO-$d_6$) δ ppm 3.94 (3H, s), 7.09 (1H, dd, J=1.92, 0.82 Hz), 7.80 (1H, d, J=8.23 Hz), 8.01 (1H, dd, J=8.10, 1.51 Hz), 8.20 (1H, d, J=2.20 Hz), 8.22 (1H, s), 8.40 (1H, s), 8.51 (1H, s), 8.57 (1H, d, J=1.92 Hz), 8.68 (1H, s), 9.21 (1H, s), 9.23 (1H, d, J=2.20 Hz), 11.05 (1H, s); ESIMS found for $C_{21}H_{15}N_5O_2$ m/z 370.1 (M+1).

N-(3-(1-Methyl-1H-pyrazol-4-yl)-1,7-naphthyridin-6-yl)quinoxaline-6-carboxamide 2936

Off-white solid (26.8 mg, 0.07 mmol, 58.6% yield). $^1$H NMR (499 MHz, DMSO-$d_6$) δ ppm 3.94 (3H, s), 8.23 (1H, s), 8.24 (1H, d, J=8.78 Hz), 8.44 (1H, dd, J=8.64, 2.06 Hz), 8.52 (1H, s), 8.60 (1H, d, J=1.92 Hz), 8.72 (1H, s), 8.85 (1H, d, J=1.92 Hz), 9.05-9.08 (1H, m), 9.09 (1H, d, J=1.92 Hz), 9.24 (1H, s), 9.25 (1H, d, J=2.20 Hz), 11.48 (1H, s); ESIMS found for $C_{21}H_{15}N_7O$ m/z 382.1 (M+1).

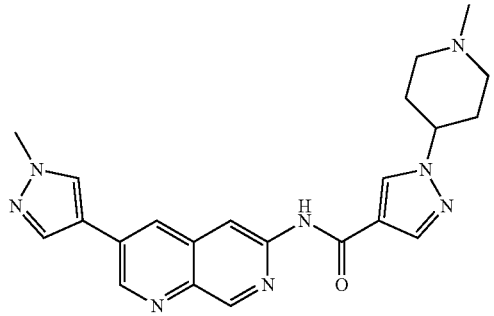

2949

N-(3-(1-Methyl-1H-pyrazol-4-yl)-1,7-naphthyridin-6-yl)-1-(1-methylpiperidin-4-yl)-1H-pyrazole-4-carboxamide 2949

White solid (23 mg, 0.06 mmol, 71.7% yield). $^1$H NMR (499 MHz, DMSO-$d_6$) δ ppm 1.89-2.00 (2H, m), 2.01-2.10 (4H, m), 2.21 (3H, s), 2.86 (2H, br d, J=11.53 Hz), 3.93 (3H, s), 4.17 (1H, tt, J=11.22, 4.15 Hz), 8.19 (1H, s), 8.21 (1H, d, J=0.82 Hz), 8.50 (1H, s), 8.51 (1H, d, J=1.92 Hz), 8.59 (1H, s), 8.63 (1H, s), 9.17 (1H, s), 9.20 (1H, d, J=2.20 Hz), 10.67 (1H, s); ESIMS found for $C_{22}H_{24}N_8O$ m/z 417.2 (M+1).

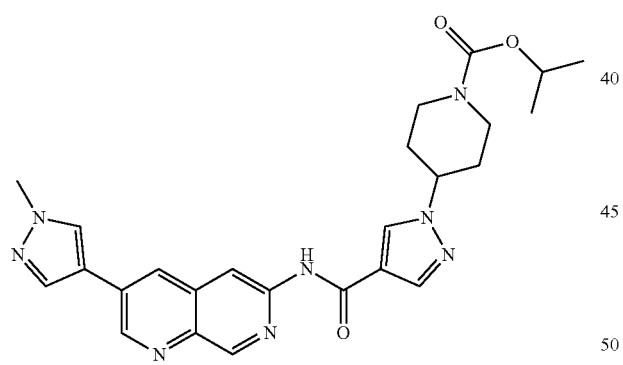

2954

Isopropyl 4-(4-((3-(1-methyl-1H-pyrazol-4-yl)-1,7-naphthyridin-6-yl) carbamoyl)-1H-pyrazol-1-yl) piperidine-1-carboxylate 2954

White solid (9.5 mg, 0.02 mmol, 31.3% yield). $^1$H NMR (499 MHz, DMSO-$d_6$) δ ppm 1.21 (6H, d, J=6.04 Hz), 1.80 (2H, qd, J=12.03, 4.25 Hz), 2.08 (2H, br dd, J=12.35, 2.20 Hz), 2.99 (2H, br s), 3.93 (3H, s), 4.07 (2H, br d, J=9.06 Hz), 4.45 (1H, tt, J=11.29, 3.95 Hz), 4.80 (1H, spt, J=6.22 Hz), 8.20 (1H, s), 8.21 (1H, d, J=0.55 Hz), 8.50 (1H, s), 8.51 (1H, d, J=1.92 Hz), 8.59 (1H, s), 8.64 (1H, s), 9.17 (1H, s), 9.20 (1H, d, J=2.20 Hz), 10.67 (1H, s); ESIMS found for $C_{25}H_{28}N_8O_3$ m/z 489.2 (M+1).

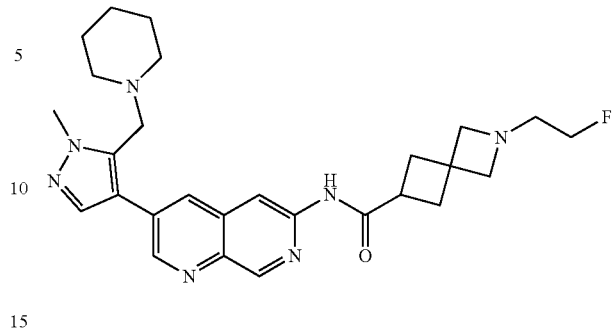

3000

2-(2-Fluoroethyl)-N-(3-(1-methyl-5-(piperidin-1-ylmethyl)-1H-pyrazol-4-yl)-1,7-naphthyridin-6-yl)-2-azaspiro[3.3]heptane-6-carboxamide 3000

Off-white solid (30 mg, 0.06 mmol, 54.4% yield). $^1$H NMR (499 MHz, DMSO-$d_6$) δ ppm 1.37 (2H, br d, J=3.84 Hz), 1.43-1.50 (4H, m), 2.25-2.33 (4H, m), 2.37 (4H, br s), 2.60 (2H, dt, J=28.90, 5.00 Hz), 3.12 (2H, s), 3.22 (2H, s), 3.24-3.31 (1H, m), 3.67 (2H, s), 3.92 (3H, s), 4.36 (2H, dt, J=47.90, 5.00 Hz), 7.94 (1H, s), 8.49 (1H, d, J=1.65 Hz), 8.52 (1H, s), 9.10 (1H, d, J=1.92 Hz), 9.14 (1H, s), 10.56 (1H, s); ESIMS found for $C_{27}H_{34}FN_7O$ m/z 492.3 (M+1).

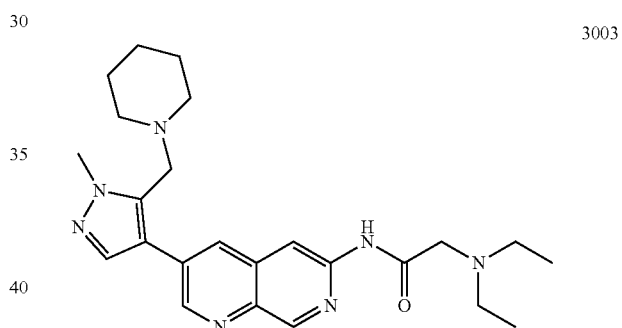

3003

2-(Diethylamino)-N-(3-(1-methyl-5-(piperidin-1-ylmethyl)-1H-pyrazol-4-yl)-1,7-naphthyridin-6-yl) acetamide 3003

Beige solid (10 mg, 0.02 mmol, 12.3% yield). $^1$H NMR (499 MHz, METHANOL-$d_4$) δ ppm 1.15 (6H, t, J=7.14 Hz), 1.41-1.49 (2H, m), 1.55 (4H, quin, J=5.49 Hz), 2.43 (4H, br s), 2.73 (4H, q, J=7.23 Hz), 3.30 (2H, s), 3.70 (2H, s), 3.99 (3H, s), 7.89 (1H, s), 8.55 (1H, d, J=1.65 Hz), 8.57 (1H, s), 9.12 (1H, d, J=2.20 Hz), 9.15 (1H, s); ESIMS found for $C_{24}H_{33}N_7O$ m/z 436.3 (M+1).

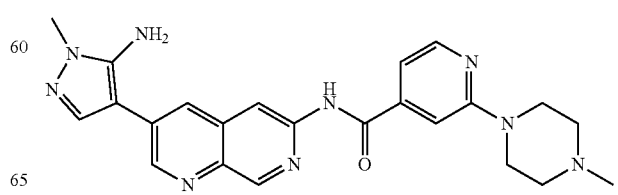

3024

N-(3-(5-Amino-1-methyl-1H-pyrazol-4-yl)-1,7-naphthyridin-6-yl)-2-(4-methylpiperazin-1-yl)isonicotinamide 3024

Light yellow solid (5.4 mg, 0.01 mmol, 8.7% yield). $^1$H NMR (499 MHz, DMSO-d$_6$) δ ppm 2.28 (3H, br s), 2.51-2.54 (4H, m), 3.57-3.68 (2H, m), 3.64 (4H, s), 5.96 (2H, s), 7.16 (1H, d, J=4.94 Hz), 7.48 (1H, s), 7.83 (1H, s), 8.27 (1H, d, J=4.94 Hz), 8.31 (1H, d, J=2.20 Hz), 8.64 (1H, s), 9.14 (2H, dd, J=2.47, 1.65 Hz), 11.15 (1H, s); ESIMS found for C$_{23}$H$_{25}$N$_9$O m/z 444.2 (M+1).

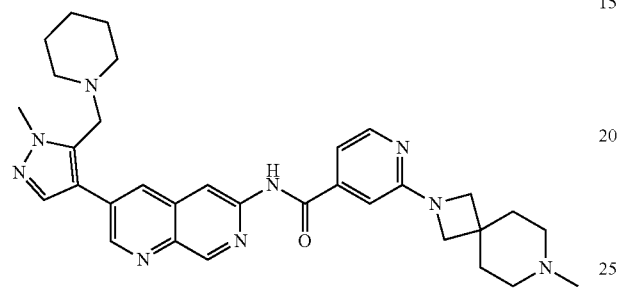

N-(3-(1-Methyl-5-(piperidin-1-ylmethyl)-1H-pyrazol-4-yl)-1,7-naphthyridin-6-yl)-2-(7-methyl-2,7-diazaspiro[3.5]nonan-2-yl)isonicotinamide 3032

Off-white solid (16 mg, 0.03 mmol, 50.3% yield). $^1$H NMR (499 MHz, DMSO-d$_6$) δ ppm 1.34-1.41 (2H, m), 1.43-1.52 (4H, m), 1.76 (4H, br t, J=5.08 Hz), 2.15 (3H, s), 2.27 (4H, br s), 2.39 (4H, br s), 3.69 (2H, s), 3.74 (4H, s), 3.93 (3H, s), 7.03 (1H, s), 7.13 (1H, dd, J=5.21, 1.37 Hz), 7.98 (1H, s), 8.20 (1H, d, J=5.49 Hz), 8.60 (1H, d, J=1.92 Hz), 8.66 (1H, s), 9.18 (1H, d, J=1.92 Hz), 9.24 (1H, s), 11.15 (1H, s); ESIMS found for C$_{32}$H$_{39}$N$_9$O m/z 566.35 (M+1).

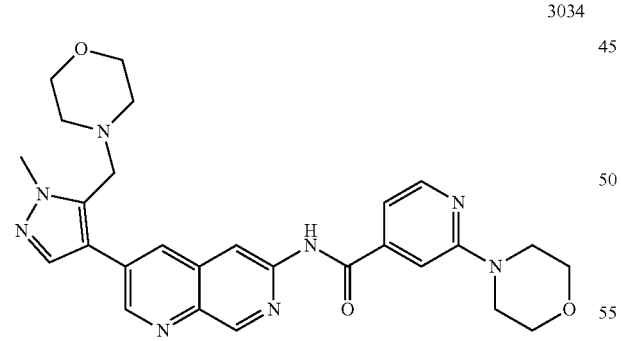

N-(3-(1-Methyl-5-(morpholinomethyl)-1H-pyrazol-4-yl)-1,7-naphthyridin-6-yl)-2-morpholinoisonicotinamide 3034

Off-white solid (39 mg, 0.08 mmol, 46.4% yield). $^1$H NMR (499 MHz, DMSO-d$_6$) δ ppm 2.41 (4H, br s), 3.51-3.55 (4H, m), 3.55-3.59 (4H, m), 3.71-3.76 (4H, m), 3.78 (2H, s), 3.95 (3H, s), 7.21 (1H, dd, J=5.08, 1.23 Hz), 7.47 (1H, s), 7.98 (1H, s), 8.29 (1H, d, J=5.21 Hz), 8.57 (1H, d, J=1.92 Hz), 8.69 (1H, s), 9.17 (1H, d, J=2.20 Hz), 9.25 (1H, s), 11.24 (1H, s); ESIMS found for C$_{27}$H$_{30}$N$_8$O$_3$ m/z 515.3 (M+1).

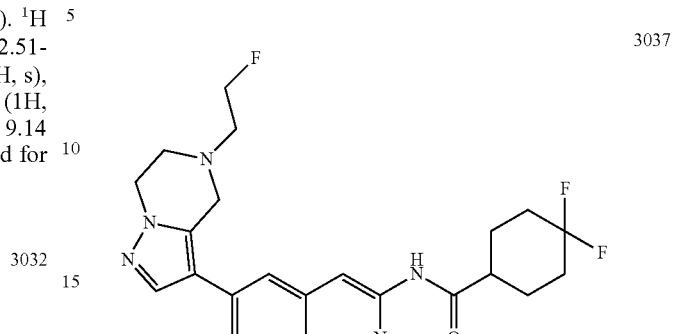

N-((4,4-Difluorocyclohexyl)methyl)-3-(5-(2-fluoroethyl)-4,5,6,7-tetrahydropyrazolo[1,5-a]pyrazin-3-yl)-1,7-naphthyridin-6-amine 3037

Off-white solid (10 mg, 0.02 mmol, 9.3% yield). $^1$H NMR (499 MHz, DMSO-d$_6$) δ ppm 1.66-1.76 (2H, m), 1.77-1.92 (2H, m), 1.96 (2H, br d, J=12.62 Hz), 2.08-2.19 (2H, m), 2.68-2.77 (1H, m), 2.98 (2H, dt, J=28.60, 5.00 Hz), 3.08 (2H, t, J=5.49 Hz), 4.11 (2H, s), 4.20 (2H, t, J=5.63 Hz), 4.67 (2H, dt, J=47.90, 5.00 Hz), 8.14 (1H, s), 8.20 (1H, d, J=1.92 Hz), 8.55 (1H, s), 9.07 (1H, d, J=2.20 Hz), 9.14 (1H, s), 10.75 (1H, s); ESIMS found for C$_{23}$H$_{25}$F$_3$N$_6$O m/z 459.2 (M+1).

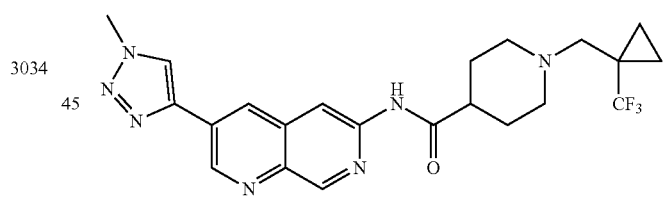

N-(3-(1-Methyl-1H-1,2,3-triazol-4-yl)-1,7-naphthyridin-6-yl)-1-((1-(trifluoromethyl)cyclopropyl)methyl)piperidine-4-carboxamide 3067

Off-white solid (20 mg, 0.04 mmol, 39.8% yield). $^1$H NMR (499 MHz, DMSO-d$_6$) δ ppm 0.73 (2H, s), 0.93-0.99 (2H, m), 1.61-1.73 (2H, m), 1.79 (2H, br d, J=9.88 Hz), 1.91-2.00 (2H, m), 2.56 (1H, tt, J=11.63, 3.88 Hz), 2.97 (2H, br d, J=11.25 Hz), 4.17 (3H, s), 8.57 (1H, s), 8.70 (1H, d, J=1.65 Hz), 8.83 (1H, s), 9.19 (1H, s), 9.38 (1H, d, J=2.20 Hz), 10.71 (1H, s); ESIMS found for C$_{22}$H$_{24}$F$_3$N$_7$O m/z 460.2 (M+1).

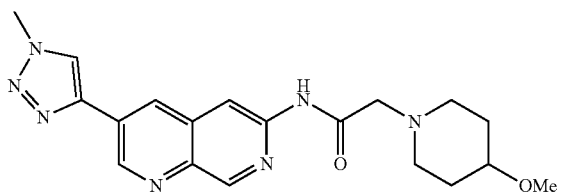

2-(4-Methoxypiperidin-1-yl)-N-(3-(1-methyl-1H-1,2,3-triazol-4-yl)-1,7-naphthyridin-6-yl)acetamide 3078

Beige solid (40 mg, 0.10 mmol, 44.2% yield). $^1$H NMR (499 MHz, DMSO-d$_6$) δ ppm 1.47-1.58 (2H, m), 1.84-1.94 (2H, m), 2.33-2.42 (2H, m), 2.75-2.83 (2H, m), 3.20-3.23 (1H, m), 3.24 (2H, s), 3.24 (3H, s), 4.17 (3H, s), 8.56 (1H, s), 8.75 (1H, d, J=1.65 Hz), 8.83 (1H, s), 9.21 (1H, s), 9.40 (1H, d, J=1.92 Hz), 10.17 (1H, s); ESIMS found for C$_{19}$H$_{23}$N$_7$O$_2$ m/z 382.2 (M+1).

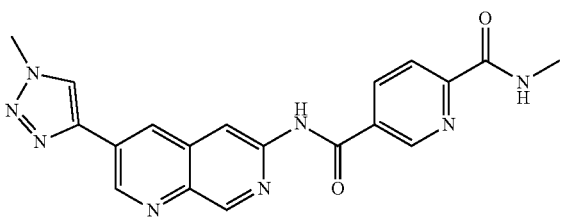

N$^2$-Methyl-N-(3-(1-methyl-1H-1,2,3-triazol-4-yl)-1,7-naphthyridin-6-yl) pyridine-2,5-dicarboxamide 3092

Off-white solid (0.40 mg, 0.001 mmol, 0.78% yield). ESIMS found for C$_{19}$H$_{16}$N$_8$O$_2$ m/z 389.15 (M+1).

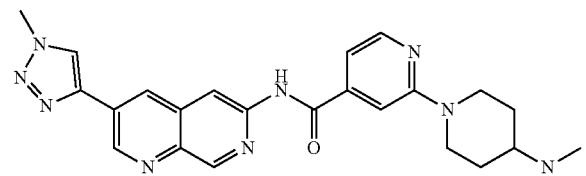

2-(4-(Dimethylamino)piperidin-1-yl)-N-(3-(1-methyl-1H-1,2,3-triazol-4-yl)-1,7-naphthyridin-6-yl) isonicotinamide 3096

Off-white solid (2.6 mg, 0.006 mmol, 4.3% yield). $^1$H NMR (499 MHz, DMSO-d$_6$) δ ppm 1.23 (6H, s), 1.37-1.48 (2H, m), 2.27-2.36 (3H, m), 2.83-2.94 (2H, m), 4.18 (3H, s), 4.45-4.54 (2H, m), 7.14 (1H, d, J=5.21 Hz), 7.49 (1H, s), 8.26 (1H, d, J=5.21 Hz), 8.74 (1H, s), 8.81 (1H, d, J=2.20 Hz), 8.87 (1H, s), 9.30 (1H, s), 9.45 (1H, d, J=1.92 Hz), 11.28 (1H, s); ESIMS found for C$_{24}$H$_{27}$N$_9$M m/z 458.25 (M+1).

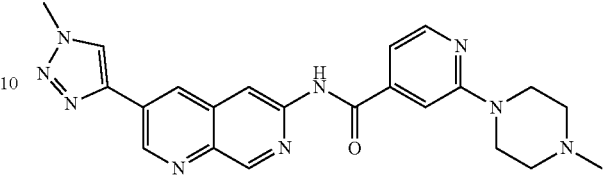

N-(3-(1-Methyl-1H-1,2,3-triazol-4-yl)-1,7-naphthyridin-6-yl)-2-(4-methylpiperazin-1-yl)isonicotinamide 3098

Off-white solid (30 mg, 0.07 mmol, 96.7% yield). $^1$H NMR (499 MHz, DMSO-d$_6$) δ ppm 2.24 (3H, s), 2.43 (4H, t, J=4.94 Hz), 3.58-3.65 (4H, m), 4.18 (3H, s), 7.17 (1H, dd, J=5.08, 1.24 Hz), 7.47 (1H, s), 8.27 (1H, d, J=4.94 Hz), 8.73 (1H, s), 8.80 (1H, d, J=1.92 Hz), 8.86 (1H, s), 9.29 (1H, s), 9.44 (1H, d, J=2.20 Hz), 11.27 (1H, s); ESIMS found for C$_{22}$H$_{23}$N$_9$O m/z 430.2 (M+1).

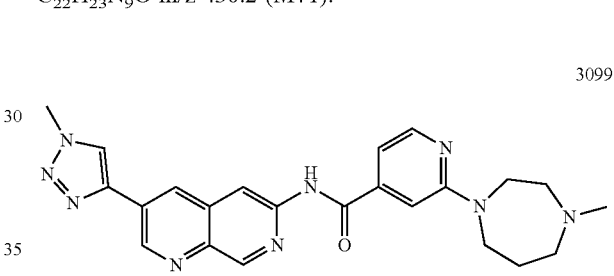

2-(4-Methyl-1,4-diazepan-1-yl)-N-(3-(1-methyl-1H-1,2,3-triazol-4-yl)-1,7-naphthyridin-6-yl)isonicotinamide 3099

Off-white solid (10.1 mg, 0.02 mmol, 17.2% yield). $^1$H NMR (499 MHz, DMSO-d$_6$) δ ppm 1.92-1.99 (2H, m), 2.30 (3H, s), 2.52-2.59 (2H, m), 2.68 (2H, br s), 3.69 (2H, t, J=6.17 Hz), 3.79-3.87 (2H, m), 4.18 (3H, s), 7.07 (1H, dd, J=4.94, 1.10 Hz), 7.23 (1H, s), 8.22 (1H, d, J=5.21 Hz), 8.73 (1H, s), 8.80 (1H, d, J=1.92 Hz), 8.86 (1H, s), 9.29 (1H, s), 9.44 (1H, d, J=2.20 Hz), 11.26 (1H, s); ESIMS found for C$_{23}$H$_{25}$N$_9$O m/z 444.2 (M+1).

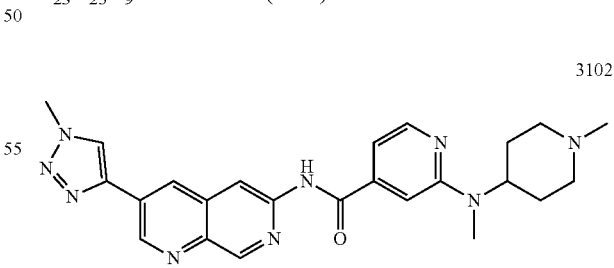

2-(Methyl(1-methylpiperidin-4-yl)amino)-N-(3-(1-methyl-1H-1,2,3-triazol-4-yl)-1,7-naphthyridin-6-yl) isonicotinamide 3102

Off-white solid (10 mg, 0.02 mmol, 11.2% yield). $^1$H NMR (499 MHz, DMSO-d$_6$) δ ppm 1.51-1.60 (2H, m), 1.81

(2H, qd, J=12.08, 3.57 Hz), 2.05 (2H, br t, J=10.98 Hz), 2.21 (3H, s), 2.87 (2H, br d, J=13.45 Hz), 2.93 (3H, s), 4.18 (3H, s), 4.48-4.57 (1H, m), 7.08 (1H, dd, J=5.08, 1.24 Hz), 7.19 (1H, s), 8.24 (1H, d, J=5.21 Hz), 8.73 (1H, s), 8.80 (1H, d, J=1.92 Hz), 8.86 (1H, s), 9.29 (1H, s), 9.44 (1H, d, J=1.92 Hz), 11.24 (1H, s); ESIMS found for $C_{24}H_{27}N_9O$ m/z 458.2 (M+1).

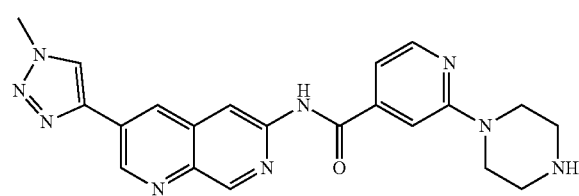

N-(3-(1-Methyl-1H-1,2,3-triazol-4-yl)-1,7-naphthyridin-6-yl)-2-(piperazin-1-yl)isonicotinamide 3105

Off-white solid (40 mg, 0.10 mmol, 46.4% yield). $^1$H NMR (500 MHz, DMSO-$d_6$) δ ppm 2.76-2.85 (4H, m), 3.50-3.56 (4H, m), 4.18 (3H, s), 7.14 (1H, dd, J=5.08, 1.23 Hz), 7.43 (1H, s), 8.26 (1H, d, J=4.67 Hz), 8.73 (1H, d, J=0.82 Hz), 8.80 (1H, d, J=1.92 Hz), 8.86 (1H, s), 9.29 (1H, s), 9.44 (1H, d, J=2.20 Hz), 11.27 (1H, br s); ESIMS found for $C_{21}H_{21}N_9O$ m/z 416.2 (M+1).

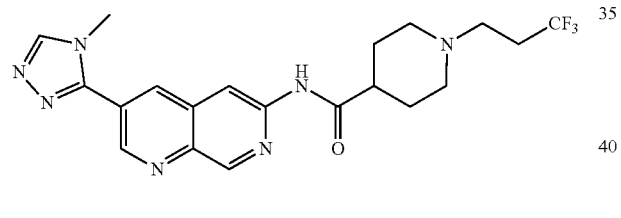

N-(3-(4-Methyl-4H-1,2,4-triazol-3-yl)-1,7-naphthyridin-6-yl)-1-(3,3,3-trifluoropropyl)piperidine-4-carboxamide 3111

Dark brown solid (1.6 mg, 0.004 mmol, 4.8% yield). $^1$H NMR (499 MHz, DMSO-$d_6$) δ ppm 1.62-1.74 (2H, m), 1.81 (2H, br d, J=11.25 Hz), 1.95-2.01 (2H, m), 2.40-2.54 (4H, m), 2.59 (1H, tt, J=11.70, 3.95 Hz), 2.94 (2H, br d, J=11.25 Hz), 3.91 (2H, s), 8.70 (1H, s), 8.72 (1H, s), 8.79 (1H, d, J=2.20 Hz), 9.26 (1H, d, J=2.20 Hz), 9.28 (1H, s), 10.80 (1H, s); ESIMS found for $C_{20}H_{22}F_3N_7O$ m/z 434.2 (M+1).

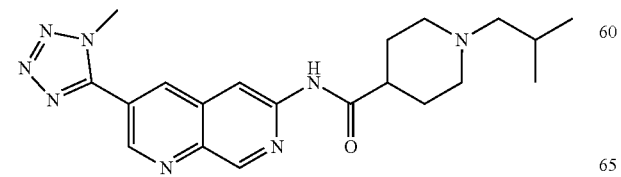

1-Isobutyl-N-(3-(1-methyl-1H-tetrazol-5-yl)-1,7-naphthyridin-6-yl) piperidine-4-carboxamide 3118

Brown solid (2.5 mg, 0.006 mmol, 2.9% yield). $^1$H NMR (499 MHz, DMSO-$d_6$) δ ppm 0.86 (6H, d, J=6.59 Hz), 1.63-1.73 (2H, m), 1.74-1.83 (3H, m), 1.88 (2H, td, J=11.60, 2.06 Hz), 2.03 (2H, d, J=7.41 Hz), 2.58 (1H, tt, J=11.49, 3.88 Hz), 2.87 (2H, br d, J=11.53 Hz), 4.32 (3H, s), 8.74 (1H, s), 8.97 (1H, d, J=2.20 Hz), 9.26 (1H, d, J=2.20 Hz), 9.32-9.35 (1H, m), 10.84 (1H, s); ESIMS found for $C_{20}H_{26}N_8O$ m/z 395.2 (M+1).

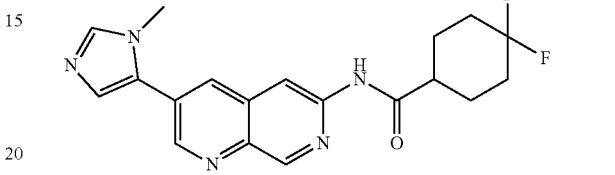

4,4-Difluoro-N-(3-(1-methyl-1H-imidazol-5-yl)-1,7-naphthyridin-6-yl) cyclohexane-1-carboxamide 3120

Off-white solid (15 mg, 0.04 mmol, 26.7% yield). $^1$H NMR (499 MHz, DMSO-$d_6$) δ ppm 1.66-1.77 (2H, m), 1.77-1.93 (2H, m), 1.97 (2H, br d, J=12.62 Hz), 2.08-2.19 (2H, m), 2.73 (1H, brt, J=10.98 Hz), 3.87 (3H, s), 7.48 (1H, d, J=0.82 Hz), 7.87 (1H, s), 8.50 (1H, d, J=1.92 Hz), 8.60 (1H, s), 9.08 (1H, d, J=2.20 Hz), 9.19 (1H, s), 10.80 (1H, s); ESIMS found for $C_{19}H_{19}F_2N_5O$ m/z 372.2 (M+1).

N-(3-(1-Methyl-1H-imidazol-5-yl)-1,7-naphthyridin-6-yl)-2-(pyrrolidin-1-yl) propanamide 3134

White solid (13.2 mg, 0.04 mmol, 20.9% yield). $^1$H NMR (499 MHz, DMSO-$d_6$) δ ppm 1.31 (3H, d, J=6.86 Hz), 1.74 (4H, br s), 2.59-2.70 (4H, m), 3.28-3.37 (1H, m), 3.87 (3H, s), 7.49 (1H, d, J=0.82 Hz), 7.87 (1H, s), 8.54 (1H, d, J=1.92 Hz), 8.60 (1H, s), 9.09 (1H, d, J=2.20 Hz), 9.19 (1H, s), 10.20 (1H, s); ESIMS found for $C_{19}H_{22}N_6O$ m/z 351.2 (M+1).

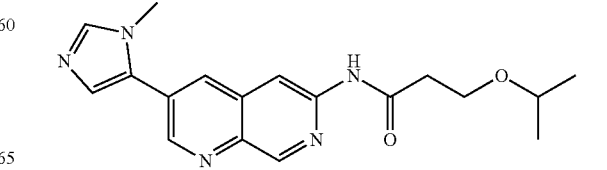

3-Isopropoxy-N-(3-(1-methyl-1H-imidazol-5-yl)-1,7-naphthyridin-6-yl) propanamide 3136

Grey solid (5 mg, 0.01 mmol, 6.6% yield). $^1$H NMR (500 MHz, DMSO-d$_6$) δ ppm 1.08 (6H, d, J=6.31 Hz), 2.68 (2H, br t, J=6.17 Hz), 3.58 (1H, dt, J=12.08, 6.04 Hz), 3.70 (2H, br t, J=6.04 Hz), 3.87 (3H, s), 7.48 (1H, s), 7.86 (1H, s), 8.51 (1H, s), 8.61 (1H, s), 9.07 (1H, d, J=1.37 Hz), 9.19 (1H, s), 10.71 (1H, s); ESIMS found for C$_{18}$H$_{21}$N$_5$O$_2$ m/z 340.2 (M+1).

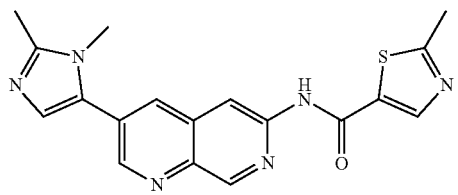

3167

N-(3-(1,2-Dimethyl-1H-imidazol-5-yl)-1,7-naphthyridin-6-yl)-2-methylthiazole-5-carboxamide 3167

Tan solid (12 mg, 0.03 mmol, 33.8% yield). $^1$H NMR (499 MHz, DMSO-d$_6$) δ ppm 2.42 (3H, s), 2.72 (3H, s), 3.72 (3H, s), 7.32 (1H, s), 8.46 (1H, d, J=1.92 Hz), 8.65 (1H, s), 8.70 (1H, s), 9.06 (1H, d, J=2.20 Hz), 9.26 (1H, s), 11.36 (1H, br s); ESIMS found for C$_{18}$H$_{16}$N$_6$OS m/z 365.1 (M+1).

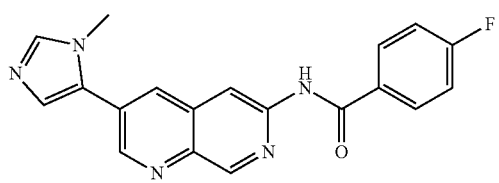

3168

4-Fluoro-N-(3-(1-methyl-1H-imidazol-5-yl)-1,7-naphthyridin-6-yl) benzamide 3168

Brown solid (18 mg, 0.05 mmol, 50.8% yield). $^1$H NMR (499 MHz, DMSO-d$_6$) δ ppm 3.89 (3H, s), 7.37 (2H, t, J=8.78 Hz), 7.51 (1H, d, J=0.82 Hz), 7.88 (1H, s), 8.13-8.22 (2H, m), 8.59 (1H, d, J=1.92 Hz), 8.76 (1H, s), 9.13 (1H, d, J=2.47 Hz), 9.27 (1H, s), 11.13 (1H, s); ESIMS found for C$_{19}$H$_{14}$FN$_5$O m/z 348.1 (M+1).

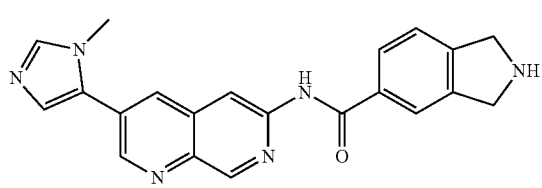

3194

N-(3-(1-Methyl-1H-imidazol-5-yl)-1,7-naphthyridin-6-yl)isoindoline-5-carboxamide 3194

Off-white solid (10 mg, 0.03 mmol, 52.9% yield). $^1$H NMR (499 MHz, DMSO-d$_6$) δ ppm 3.89 (3H, s), 4.14 (4H, br s), 7.40 (1H, d, J=7.96 Hz), 7.51 (1H, s), 7.88 (1H, s), 7.93 (1H, dd, J=7.96, 1.37 Hz), 7.98 (1H, s), 8.58 (1H, d, J=1.92 Hz), 8.77 (1H, s), 9.12 (1H, d, J=2.20 Hz), 9.27 (1H, s), 10.97 (1H, s); ESIMS found for C$_{21}$H$_{18}$N$_6$O m/z 371.15 (M+1).

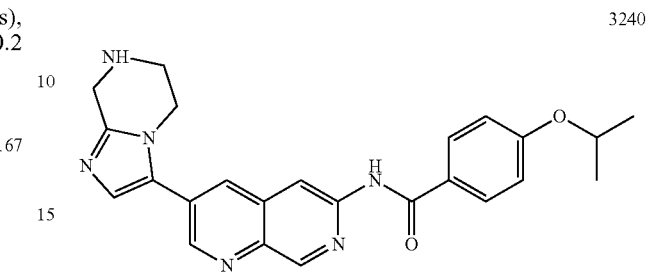

3240

4-Isopropoxy-N-(3-(5,6,7,8-tetrahydroimidazo[1,2-a]pyrazin-3-yl)-1,7-naphthyridin-6-yl)benzamide 3240

Yellow solid (24.2 mg, 0.05 mmol, 37.3% yield). $^1$H NMR (499 MHz, DMSO-d$_6$) δ ppm 1.31 (6H, d, J=6.04 Hz), 3.10 (2H, t, J=5.35 Hz), 3.97 (2H, s), 4.18 (2H, t, J=5.35 Hz), 4.76 (1H, spt, J=5.99 Hz), 7.03 (2H, d, J=9.06 Hz), 7.50 (1H, s), 8.08 (2H, d, J=9.06 Hz), 8.48 (1H, d, J=1.92 Hz), 8.74 (1H, s), 9.10 (1H, d, J=2.20 Hz), 9.23 (1H, s), 10.83 (1H, s); ESIMS found for C$_{24}$H$_{24}$N$_6$O$_2$ m/z 429.2 (M+1).

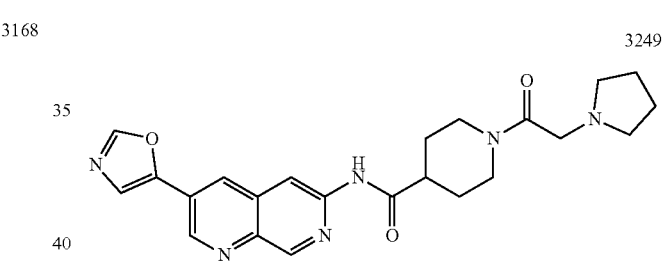

3249

N-(3-(Oxazol-5-yl)-1,7-naphthyridin-6-yl)-1-(2-(pyrrolidin-1-yl) acetyl)piperidine-4-carboxamide 3249

White solid (11.0 mg, 0.03 mmol, 34.1% yield). $^1$H NMR (499 MHz, DMSO-d$_6$) δ ppm 1.42-1.53 (1H, m), 1.55-1.67 (1H, m), 1.69 (4H, br s), 1.85 (2H, br d, J=10.70 Hz), 2.47 (4H, br s), 2.58-2.66 (1H, m), 2.84 (1H, tt, J=11.32, 3.77 Hz), 2.98-3.08 (1H, m), 3.15-3.21 (1H, m), 3.32-3.37 (1H, m), 4.11 (1H, br d, J=12.90 Hz), 4.40 (1H, br d, J=12.90 Hz), 8.10 (1H, s), 8.60 (1H, s), 8.62 (1H, d, J=1.92 Hz), 8.66 (1H, s), 9.19-9.23 (1H, m), 9.29 (1H, d, J=2.20 Hz), 10.80 (1H, s); ESIMS found for C$_{23}$H$_{26}$N$_6$O$_3$ m/z 435.2 (M+1).

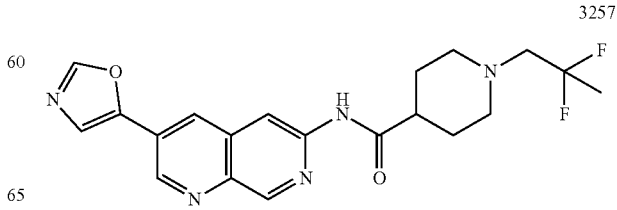

3257

1577

1-(2,2-Difluoropropyl)-N-(3-(oxazol-5-yl)-1,7-naphthyridin-6-yl)piperidine-4-carboxamide 3257

White solid (15 mg, 0.04 mmol, 38.3% yield). $^1$H NMR (499 MHz, DMSO-d$_6$) δ ppm 1.63 (3H, t, J=19.07 Hz), 1.65-1.74 (2H, m), 1.76-1.82 (2H, m), 2.22 (2H, td, J=11.80, 2.20 Hz), 2.52-2.61 (1H, m), 2.71 (2H, t, J=14.00 Hz), 2.95 (2H, br d, J=11.53 Hz), 8.10 (1H, s), 8.60 (1H, s), 8.63 (1H, d, J=1.92 Hz), 8.66 (1H, s), 9.21 (1H, s), 9.28 (1H, d, J=2.20 Hz), 10.74 (1H, s); ESIMS found for C$_{20}$H$_{21}$F$_2$N$_5$O$_2$ m/z 402.2 (M+1).

1578

2-(4-Methylpiperazin-1-yl)-N-(3-(2-methylthiazol-5-yl)-1,7-naphthyridin-6-yl)isonicotinamide 3363

Off-white solid (30 mg, 0.07 mmol, 74.2% yield). $^1$H NMR (499 MHz, DMSO-d$_6$) δ ppm 2.23 (3H, s), 2.42 (4H, t, J=4.94 Hz), 2.75 (3H, s), 3.57-3.64 (4H, m), 7.15 (1H, dd, J=5.08, 0.96 Hz), 7.46 (1H, s), 8.26 (1H, d, J=4.94 Hz), 8.45 (1H, s), 8.63 (1H, d, J=2.20 Hz), 8.72 (1H, s), 9.27 (1H, s), 9.28 (1H, d, J=2.20 Hz), 11.26 (1H, s); ESIMS found for C$_{23}$H$_{23}$N$_7$OS m/z 446.2 (M+1).

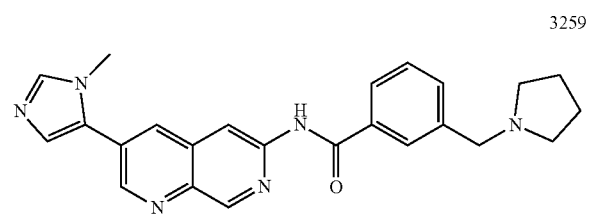 [SMILES: Cn1cncc1-c1cnc2cnc(NC(=O)c3cccc(CN4CCCC4)c3)cc2c1]

3259

N-(3-(1-Methyl-1H-imidazol-5-yl)-1,7-naphthyridin-6-yl)-3-(pyrrolidin-1-ylmethyl)benzamide 3259

Off-white solid (6.5 mg, 0.02 mmol, 16.1% yield). $^1$H NMR (499 MHz, DMSO-d$_6$) δ ppm 1.72 (4H, dt, J=6.66, 3.12 Hz), 2.44-2.49 (4H, m), 3.67 (2H, s), 3.89 (3H, s), 7.46-7.50 (1H, m), 7.51 (1H, s), 7.53-7.59 (1H, m), 7.88 (1H, s), 7.96 (1H, d, J=7.68 Hz), 8.01 (1H, s), 8.59 (1H, d, J=1.92 Hz), 8.76 (1H, s), 9.12 (1H, d, J=2.20 Hz), 9.27 (1H, s), 11.06 (1H, s); ESIMS found for C$_{24}$H$_{24}$N$_6$O m/z 413.2 (M+1).

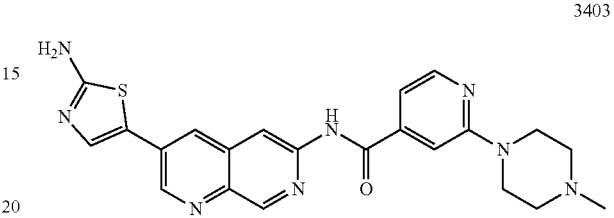

3403

N-(3-(2-Aminothiazol-5-yl)-1,7-naphthyridin-6-yl)-2-(4-methylpiperazin-1-yl)isonicotinamide 3403

Light yellow solid (25 mg, 0.06 mmol, 40.1% yield). $^1$H NMR (500 MHz, DMSO-d$_6$) δ ppm 2.23 (3H, s), 2.41-2.45 (3H, m), 3.57-3.62 (3H, m), 7.15 (1H, dd, J=5.08, 1.23 Hz), 7.46 (1H, s), 7.58 (2H, s), 7.90 (1H, s), 8.17 (1H, d, J=2.20 Hz), 8.26 (1H, d, J=5.49 Hz), 8.63 (1H, d, J=0.82 Hz), 9.16 (1H, t, J=0.82 Hz), 9.21 (1H, d, J=2.47 Hz), 11.18 (1H, br s); ESIMS found for C$_{22}$H$_{22}$N$_8$OS m/z 447.15 (M+1).

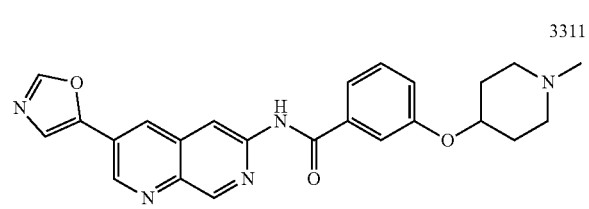 [SMILES: CN1CCC(Oc2cccc(C(=O)Nc3cc4cc(-c5cnco5)cnc4cn3)c2)CC1]

3311

3-((1-Methylpiperidin-4-yl)oxy)-N-(3-(oxazol-5-yl)-1,7-naphthyridin-6-yl) benzamide 3311

White solid (25 mg, 0.06 mmol, 86.4% yield). $^1$H NMR (499 MHz, DMSO-d$_6$) δ ppm 1.62-1.74 (2H, m), 1.97 (2H, br d, J=10.15 Hz), 2.14-2.26 (2H, m), 2.19 (3H, s), 2.58-2.67 (2H, m), 4.49-4.57 (1H, m), 7.18 (1H, dd, J=8.23, 1.65 Hz), 7.43 (1H, t, J=8.10 Hz), 7.62-7.67 (2H, m), 8.12 (1H, s), 8.68 (1H, s), 8.71 (1H, d, J=1.65 Hz), 8.75 (1H, s), 9.29 (1H, s), 9.34 (1H, d, J=1.92 Hz), 11.08 (1H, s); ESIMS found for C$_{24}$H$_{23}$N$_5$O$_3$ m/z 430.2 (M+1).

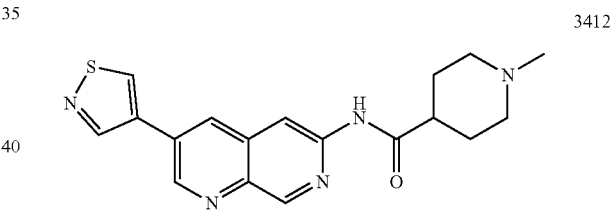

3412

N-(3-(Isothiazol-4-yl)-1,7-naphthyridin-6-yl)-1-methylpiperidine-4-carboxamide 3412

Off-white solid (25 mg, 0.07 mmol, 50.4% yield). $^1$H NMR (499 MHz, DMSO-d$_6$) δ ppm 1.62-1.74 (2H, m), 1.76-1.82 (2H, m), 1.87 (2H, td, J=11.66, 2.20 Hz), 2.16 (3H, s), 2.51-2.58 (1H, m), 2.81 (2H, br d, J=11.25 Hz), 8.59 (1H, s), 8.81 (1H, d, J=1.92 Hz), 9.21 (1H, s), 9.32 (1H, s), 9.37 (1H, d, J=2.20 Hz), 9.76 (1H, s), 10.72 (1H, s); ESIMS found for C$_{18}$H$_{19}$N$_5$OS m/z 354.15 (M+1).

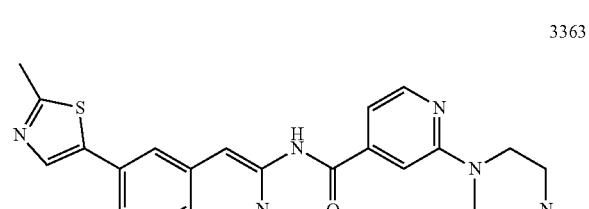

3363

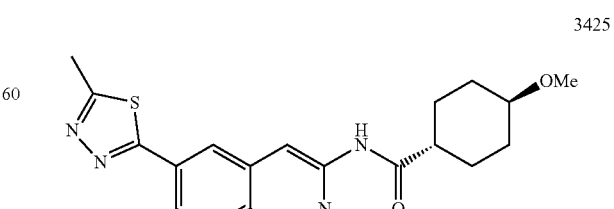

3425 trans-4-Methoxy-N-(3-(5-methyl-1,3,4-thiadiazol-2-yl)-1,7-naphthyridin-6-yl)cyclohexane-1-carboxamide 3425

Off-white solid (16 mg, 0.04 mmol, 50.8% yield). $^1$H NMR (499 MHz, DMSO-$d_6$) δ ppm 1.09-1.19 (2H, m), 1.46-1.56 (2H, m), 1.88-1.97 (2H, m), 2.05-2.12 (2H, m), 2.52-2.60 (1H, m), 2.85 (3H, s), 3.09-3.16 (1H, m), 3.25 (3H, s), 8.67 (1H, s), 8.92 (1H, d, J=2.20 Hz), 9.27 (1H, s), 9.43 (1H, d, J=2.20 Hz), 10.76 (1H, s); ESIMS found for $C_{19}H_{21}N_5O_2S$ m/z 384.2 (M+1).

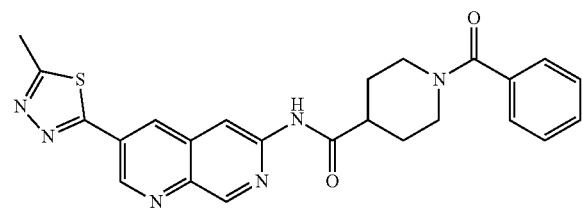

1-Benzoyl-N-(3-(5-methyl-1,3,4-thiadiazol-2-yl)-1,7-naphthyridin-6-yl) piperidine-4-carboxamide 3439

Beige solid (4 mg, 0.009 mmol, 10.6% yield). $^1$H NMR (499 MHz, DMSO-$d_6$) δ ppm 1.64 (2H, ddd, J=7.55, 3.02, 1.23 Hz), 1.77-1.90 (1H, m), 1.90-2.03 (1H, m), 2.86 (3H, s), 2.87-2.93 (2H, m), 3.04-3.17 (1H, m), 3.62-3.73 (1H, m), 4.47-4.61 (1H, m), 7.39-7.42 (2H, m), 7.44-7.47 (3H, m), 8.69 (1H, s), 8.95 (1H, d, J=1.65 Hz), 9.29 (1H, s), 9.44 (1H, d, J=2.20 Hz), 10.89 (1H, s); ESIMS found for $C_{24}H_{22}N_6O_2S$ m/z 459.2 (M+1).

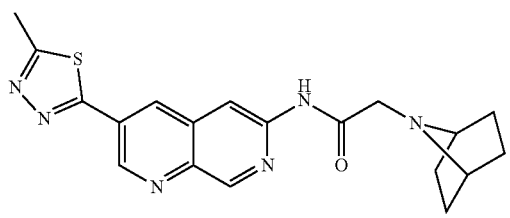

2-(7-Azabicyclo[2.2.1]heptan-7-yl)-N-(3-(5-methyl-1,3,4-thiadiazol-2-yl)-1,7-naphthyridin-6-yl)acetamide 3446

Beige solid (10 mg, 0.03 mmol, 21.6% yield). $^1$H NMR (499 MHz, DMSO-$d_6$) δ ppm 1.35 (4H, br d, J=6.86 Hz), 1.72-1.78 (4H, m), 2.86 (3H, s), 3.24 (2H, s), 3.36-3.41 (m), 8.70 (1H, d, J=0.82 Hz), 9.02 (1H, d, J=2.20 Hz), 9.30 (1H, s), 9.47 (1H, d, J=2.20 Hz), 10.35 (1H, s); ESIMS found for $C_{19}H_{20}N_6OS$ m/z 381.2 (M+1).

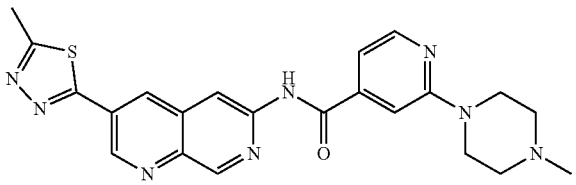

N-(3-(5-Methyl-1,3,4-thiadiazol-2-yl)-1,7-naphthyridin-6-yl)-2-(4-methylpiperazin-1-yl)isonicotinamide 3470

Brown solid (7 mg, 0.02 mmol, 21.2% yield). $^1$H NMR (499 MHz, DMSO-$d_6$) δ ppm 2.24 (3H, s), 2.43 (4H, t, J=5.08 Hz), 2.87 (3H, s), 3.58-3.66 (4H, m), 7.16 (1H, dd, J=5.21, 1.10 Hz), 7.48 (1H, s), 8.27 (1H, d, J=5.21 Hz), 8.85 (1H, s), 9.04 (1H, d, J=2.20 Hz), 9.37 (1H, s), 9.50 (1H, d, J=2.20 Hz), 11.35 (1H, s); ESIMS found for $C_{22}H_{22}N_8OS$ m/z 447.2 (M+1).

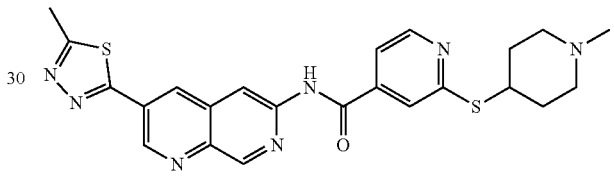

N-(3-(5-Methyl-1,3,4-thiadiazol-2-yl)-1,7-naphthyridin-6-yl)-2-((1-methylpiperidin-4-yl)thio)isonicotinamide 3474

Off-white solid (22 mg, 0.05 mmol, 36.2% yield). $^1$H NMR (499 MHz, DMSO-$d_6$) δ ppm 1.61-1.74 (2H, m), 1.99-2.07 (2H, m), 2.12 (2H, br t, J=10.29 Hz), 2.17 (3H, s), 2.65-2.74 (2H, m), 2.86 (3H, s), 3.80-3.89 (1H, m), 7.64 (1H, dd, J=5.08, 1.51 Hz), 7.82 (1H, s), 8.60-8.66 (1H, m), 8.83 (1H, s), 9.04 (1H, d, J=2.20 Hz), 9.37 (1H, s), 9.50 (1H, d, J=2.20 Hz), 11.45 (1H, s); ESIMS found for $C_{23}H_{23}N_7OS_2$ m/z 478.2 (M+1).

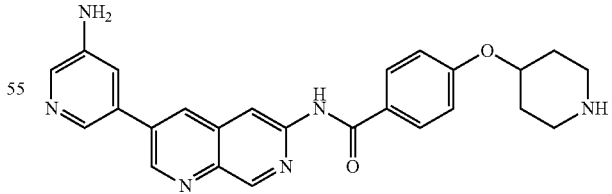

N-(3-(5-Aminopyridin-3-yl)-1,7-naphthyridin-6-yl)-4-(piperidin-4-yloxy) benzamide 3524

Beige solid (1.3 mg, 0.003 mmol, 7.6% yield). $^1$H NMR (499 MHz, DMSO-$d_6$) δ ppm 1.70-1.79 (2H, m), 2.04-2.13 (2H, m), 2.92-3.01 (2H, m), 3.15-3.21 (2H, m), 4.73 (1H, dt, J=7.89, 4.15 Hz), 5.55 (2H, s), 7.12 (2H, d, J=8.78 Hz), 7.38 (1H, t, J=2.33 Hz), 8.06 (1H, d, J=2.47 Hz), 8.11 (2H, d, J=8.78 Hz), 8.27 (1H, d, J=1.65 Hz), 8.66 (1H, d, J=1.65 Hz), 8.75 (1H, s), 9.18 (1H, d, J=2.20 Hz), 9.30 (1H, s), 10.92 (1H, s); ESIMS found for $C_{25}H_{24}N_6O_2$ m/z 441.2 (M+1).

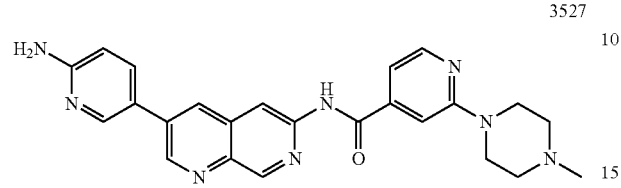

N-(3-(6-Aminopyridin-3-yl)-1,7-naphthyridin-6-yl)-2-(4-methylpiperazin-1-yl)isonicotinamide 3527

Beige solid (31.5 mg, 0.07 mmol, 50.9% yield). $^1$H NMR (499 MHz, DMSO-$d_6$) δ ppm 2.23 (3H, s), 2.43 (4H, t, J=4.94 Hz), 3.56-3.64 (4H, m), 6.37 (2H, s), 6.61 (1H, d, J=8.78 Hz), 7.16 (1H, dd, J=5.08, 0.96 Hz), 7.47 (1H, s), 8.01 (1H, dd, J=8.78, 2.47 Hz), 8.26 (1H, d, J=5.21 Hz), 8.58 (2H, dd, J=6.59, 2.20 Hz), 8.69 (1H, s), 9.24 (1H, s), 9.26 (1H, d, J=2.20 Hz), 11.21 (1H, s); ESIMS found for $C_{24}H_{24}N_8O$ m/z 441.2 (M+1).

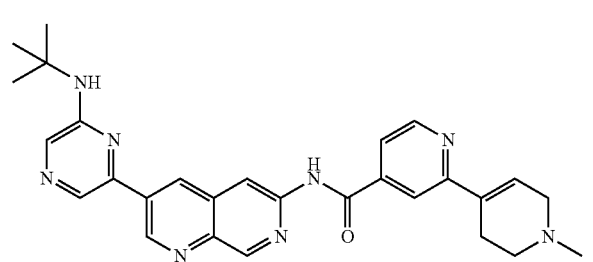

N-(3-(6-(tert-Butylamino)pyrazin-2-yl)-1,7-naphthyridin-6-yl)-1'-methyl-1',2',3',6'-tetrahydro-[2,4'-bipyridine]-4-carboxamide 3587

Tan solid (5.9 mg, 0.01 mmol, 6.8% yield). $^1$H NMR (499 MHz, DMSO-$d_6$) δ ppm 1.52 (9H, s), 2.31 (3H, s), 2.57-2.63 (2H, m), 2.63-2.69 (2H, m), 3.11 (2H, br d, J=3.02 Hz), 6.89 (1H, t, J=3.57 Hz), 7.12 (1H, s), 7.79 (1H, dd, J=4.94, 1.37 Hz), 8.02 (1H, s), 8.18 (1 H, s), 8.53 (1H, s), 8.72 (1H, d, J=4.94 Hz), 8.80 (1H, s), 8.98 (1H, d, J=1.65 Hz), 9.33 (1H, s), 9.58 (1H, d, J=2.20 Hz), 11.50 (1H, s); ESIMS found for $C_{28}H_{30}N_8O$ m/z 495.3 (M+1).

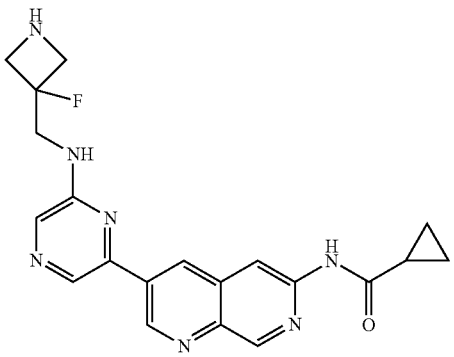

N-(3-(6-(((3-Fluoroazetidin-3-yl)methyl)amino) pyrazin-2-yl)-1,7-naphthyridin-6-yl)cyclopropanecarboxamide 3591

Orange solid (57.2 mg, 0.14 mmol, 87.4% yield). $^1$H NMR (499 MHz, DMSO-$d_6$) δ ppm 0.84-0.89 (4H, m), 2.07-2.15 (1H, m), 4.04 (2H, dd, J=20.60, 6.10 Hz), 4.17-4.38 (4H, m), 7.76 (1H, t, J=6.17 Hz), 8.11 (1H, s), 8.63 (1H, s), 8.64 (1H, s), 8.97 (1H, d, J=1.65 Hz), 9.25 (1H, s), 9.59 (1H, d, J=2.20 Hz), 11.11 (1H, s); ESIMS found for $C_{20}H_{20}FN_7O$ m/z 394.2 (M+1).

N-(3-(6-(Piperidin-4-ylamino)pyrazin-2-yl)-1,7-naphthyridin-6-yl) tetrahydro-2H-pyran-4-carboxamide 3597

Yellow solid (68 mg, 0.16 mmol, 79.7% yield). $^1$H NMR (499 MHz, DMSO-$d_6$) δ ppm 1.32-1.44 (2H, m), 1.65-1.80 (4H, m), 1.92-1.99 (2H, m), 2.58-2.70 (2H, m), 2.81-2.91 (1H, m), 2.96-3.04 (2H, m), 3.34-3.41 (2H, m), 3.88-4.01 (3H, m), 7.29 (1H, d, J=7.14 Hz), 8.00 (1H, s), 8.50 (1H, s), 8.63 (1H, s), 8.90 (1H, d, J=1.92 Hz), 9.23 (1H, s), 9.50 (1H, d, J=2.20 Hz), 10.77 (1H, s); ESIMS found for $C_{23}H_{27}N_7O_2$ m/z 434.2 (M+1).

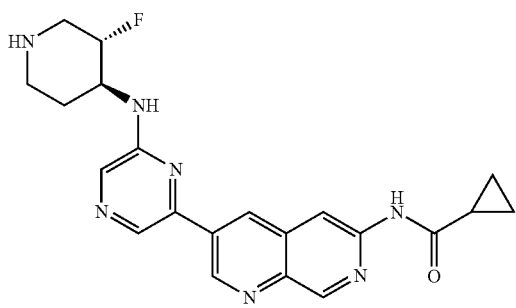

N-(3-(6-(((3S,4S)-3-Fluoropiperidin-4-yl)amino)
pyrazin-2-yl)-1,7-naphthyridin-6-yl)cyclopropan-
ecarboxamide 3599

Yellow solid (12 mg, 0.03 mmol, 49.0% yield). $^1$H NMR
(499 MHz, DMSO-d$_6$) δ ppm 0.82-0.92 (4H, m), 1.33-1.48
(1H, m), 2.02-2.15 (2H, m), 2.56-2.66 (2H, m), 2.84-2.94
(1H, m), 3.22 (1H, ddd, J=12.21, 7.55, 4.94 Hz), 4.18-4.28
(1H, m), 4.35-4.54 (1H, m), 7.52 (1H, d, J=7.68 Hz), 8.04
(1H, s), 8.54 (1H, s), 8.60 (1H, s), 8.90 (1H, d, J=1.65 Hz),
9.24 (1H, s), 9.51 (1H, d, J=1.92 Hz), 11.09 (1H, s); ESIMS
found for C$_{21}$H$_{22}$FN$_7$O m/z 408.2 (M+1).

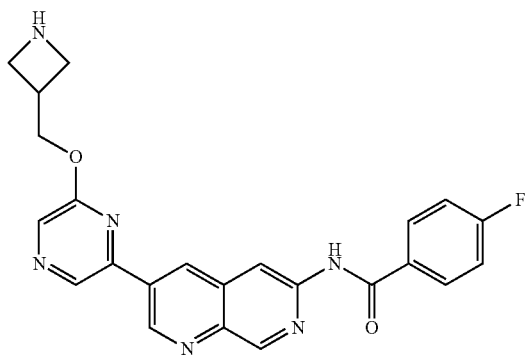

N-(3-(6-(Azetidin-3-ylmethoxy)pyrazin-2-yl)-1,7-
naphthyridin-6-yl)-4-fluorobenzamide 3612

Yellow solid (40.3 mg, 0.09 mmol, 70.4% yield). $^1$H
NMR (500 MHz, DMSO-d) δ ppm 3.08-3.17 (1H, m), 3.90
(2H, dd, J=10.57, 6.72 Hz), 4.03-4.12 (2H, m), 4.71 (2H, d,
J=6.04 Hz), 7.34-7.42 (2H, m), 8.15-8.23 (2H, m), 8.45 (1H,
s), 8.83 (1H, d, J=0.82 Hz), 9.17 (1H, s), 9.18 (1H, d, J=1.65
Hz), 9.36 (1H, s), 9.67 (1H, d, J=2.20 Hz), 11.20 (2H, br s);
ESIMS found for C$_{23}$H$_{19}$FN$_6$O$_2$ m/z 431.2 (M+1).

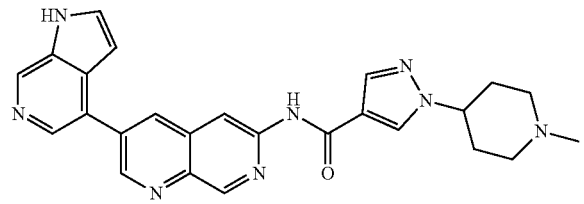

N-(3-(1H-Pyrrolo[2,3-c]pyridin-4-yl)-1,7-naphthyri-
din-6-yl)-1-(1-methylpiperidin-4-yl)-1H-pyrazole-4-
carboxamide 3616

Yellow solid (2 mg, 0.004 mmol, 38.8% yield). $^1$H NMR
(499 MHz, DMSO-d$_6$) δ ppm 1.89-1.99 (2H, m), 2.02-2.11
(4H, m), 2.21 (3H, s), 2.86 (2H, br d, J=11.53 Hz), 4.18 (1H,
tt, J=11.05, 4.19 Hz), 6.83 (1H, d, J=2.74 Hz), 7.79 (1H, d,
J=3.02 Hz), 8.20 (1H, s), 8.46 (1H, s), 8.64 (1H, s), 8.70 (1H,
d, J=1.92 Hz), 8.76 (1H, s), 8.87 (1H, s), 9.28 (1H, d, J=2.20
Hz), 9.31 (1H, s), 10.75 (1H, s); ESIMS found for
C$_{25}$H$_{24}$N$_8$O m/z 453.2 (M+1).

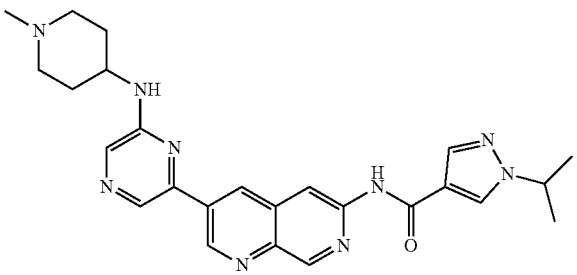

1-Isopropyl-N-(3-(6-((1-methylpiperidin-4-yl)
amino)pyrazin-2-yl)-1,7-naphthyridin-6-yl)-1H-
pyrazole-4-carboxamide 3627

Yellow solid (2.3 mg, 0.005 mmol, 3.0% yield). $^1$H NMR
(500 MHz, DMSO-d$_6$) δ ppm 1.46 (6H, d, J=6.59 Hz),
1.49-1.58 (2H, m), 1.96-2.04 (2H, m), 2.07-2.16 (2H, m),
2.21 (3H, s), 2.73-2.81 (2H, m), 3.82-3.94 (1H, m), 4.56
(1H, dt, J=13.38, 6.62 Hz), 7.29 (1H, br d, J=7.14 Hz), 8.01
(1H, s), 8.19 (1H, d, J=0.82 Hz), 8.54 (1H, s), 8.63 (1H, s),
8.72 (1H, d, J=0.82 Hz), 8.95 (1H, d, J=1.37 Hz), 9.28 (1H,
t, J=0.82 Hz), 9.53 (1H, d, J=2.20 Hz), 10.76 (1H, s); ESIMS
found for C$_{25}$H$_{29}$N$_9$O m/z 472.3 (M+1).

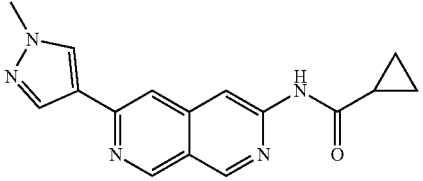

N-(6-(1-Methyl-1H-pyrazol-4-yl)-2,7-naphthyridin-
3-yl) cyclopropanecarboxamide 3629

White solid (8 mg, 0.03 mmol, 18.6% yield). $^1$H NMR
(499 MHz, DMSO-d$_6$) δ ppm 0.81-0.92 (4H, m), 2.06-2.14
(1H, m), 3.91 (3H, s), 7.96 (1H, s), 8.12 (1H, s), 8.37 (1H,
s), 8.37 (1H, s), 9.24 (1H, s), 9.31 (1H, t, J=0.82 Hz), 11.08
(1H, s); ESIMS found for C$_{16}$H$_{15}$N$_5$O m/z 294.1 (M+1).

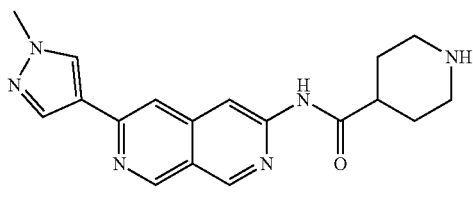

N-(6-(1-Methyl-1H-pyrazol-4-yl)-2,7-naphthyridin-3-yl)piperidine-4-carboxamide 3638

Beige solid (100 mg, 0.23 mmol, 56.7% yield). $^1$H NMR (500 MHz, DMSO-$d_6$) δ ppm 1.52 (2H, qd, J=12.21, 3.98 Hz), 1.67-1.74 (2H, m), 2.43-2.49 (2H, m), 2.66 (1H, tt, J=11.66, 3.43 Hz), 2.94-3.00 (2H, m), 3.91 (3H, s), 4.09 (1H, q, J=5.21 Hz), 7.98 (1H, s), 8.12 (1H, d, J=0.82 Hz), 8.38 (1H, s), 8.40 (1H, s), 9.23 (1H, s), 9.29-9.33 (1H, m), 10.66 (1H, s); ESIMS found for $C_{18}H_{20}N_6O$ m/z 337.2 (M+1).

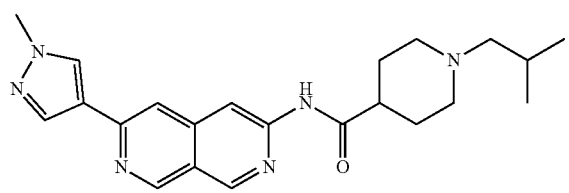

1-Isobutyl-N-(6-(1-methyl-1H-pyrazol-4-yl)-2,7-naphthyridin-3-yl) piperidine-4-carboxamide 3643

Off-white solid (123 mg, 0.06 mmol, 65.7% yield). $^1$H NMR (499 MHz, DMSO-$d_6$) δ ppm 0.84 (6H, d, J=6.59 Hz), 1.60-1.71 (2H, m), 1.72-1.80 (3H, m), 1.82-1.90 (2H, m), 2.00 (2H, d, J=7.41 Hz), 2.55 (1H, tt, J=11.60, 3.91 Hz), 2.85 (2H, br d, J=11.25 Hz), 3.91 (3H, s), 7.98 (1H, s), 8.12 (1H, s), 8.37 (1H, s), 8.41 (1H, s), 9.22 (1H, s), 9.30 (1H, s), 10.70 (1H, s); ESIMS found for $C_{22}H_{28}N_6O$ m/z 393.2 (M+1).

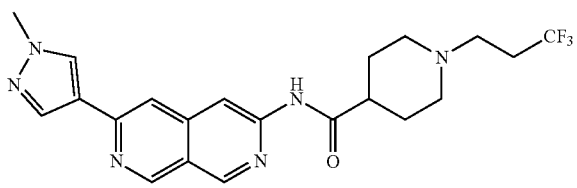

N-(6-(1-Methyl-1H-pyrazol-4-yl)-2,7-naphthyridin-3-yl)-1-(3,3,3-trifluoropropyl)piperidine-4-carboxamide 3646

Off-white solid ((35 mg, 0.08 mmol, 45.4% yield). $^1$H NMR (499 MHz, DMSO-$d_6$) δ ppm 1.65 (2H, qd, J=12.26, 3.57 Hz), 1.80 (2H, br d, J=11.53 Hz), 1.93-2.01 (2H, m), 2.41-2.55 (4H, m), 2.55-2.61 (1H, m), 2.93 (2H, br d, J=11.25 Hz), 3.91 (3H, s), 7.99 (1H, s), 8.12 (1H, s), 8.37 (1H, s), 8.41 (1H, s), 9.23 (1H, s), 9.31 (1H, s), 10.73 (1H, s); ESIMS found for $C_{21}H_{23}F_3N_6O$ m/z 433.2 (M+1).

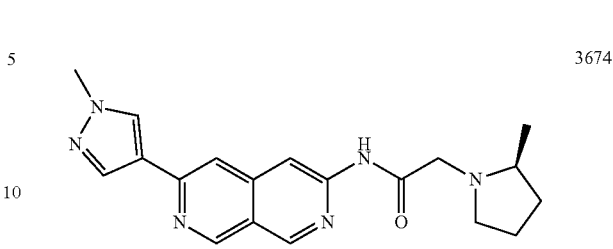

(S)—N-(6-(1-Methyl-1H-pyrazol-4-yl)-2,7-naphthyridin-3-yl)-2-(2-methylpyrrolidin-1-yl)acetamide 3674

Off-white solid (20 mg, 0.06 mmol, 49.4% yield). $^1$H NMR (499 MHz, DMSO-$d_6$) δ ppm 1.09 (3H, d, J=6.04 Hz), 1.41 (1H, dddd, J=12.28, 10.29, 8.30, 6.45 Hz), 1.67-1.84 (2H, m), 1.91-2.01 (1H, m), 2.40 (1H, q, J=8.51 Hz), 2.57-2.66 (1H, m), 3.12-3.19 (1 H, m), 3.15 (1H, d, J=16.47 Hz), 3.57 (1H, d, J=16.19 Hz), 3.91 (3H, s), 8.06 (1H, s), 8.14 (1H, s), 8.38 (1H, s), 8.40 (1H, s), 9.24 (1H, s), 9.34 (1H, s), 10.10 (1H, s); ESIMS found for $C_{19}H_{22}N_6O$ m/z 351.2 (M+1).

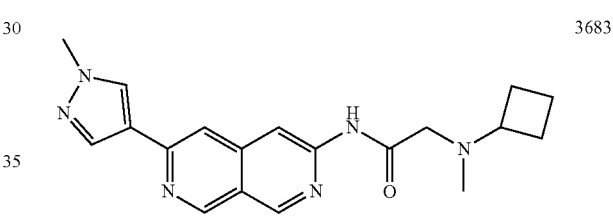

2-(Cyclobutyl(methyl)amino)-N-(6-(1-methyl-1H-pyrazol-4-yl)-2,7-naphthyridin-3-yl)acetamide 3683

White solid (25 mg, 0.07 mmol, 61.8% yield). $^1$H NMR (499 MHz, DMSO-$d_6$) δ ppm 1.54-1.70 (2H, m), 1.81-1.92 (2H, m), 1.97-2.05 (2H, m), 2.22 (3H, s), 3.08 (1H, quin, J=7.82 Hz), 3.14 (2H, s), 3.91 (3H, s), 8.06 (1H, s), 8.14 (1H, s), 8.38 (1H, s), 8.39 (1H, s), 9.25 (1H, s), 9.34 (1H, s), 10.13 (1H, s); ESIMS found for $C_{19}H_{22}N_6O$ m/z 351.2 (M+1).

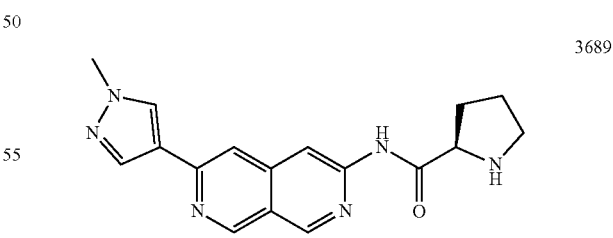

(R)—N-(6-(1-Methyl-1H-pyrazol-4-yl)-2,7-naphthyridin-3-yl)pyrrolidine-2-carboxamide 3689

Off-white solid (4 mg, 0.01 mmol, 37.8% yield). $^1$H NMR (499 MHz, DMSO-$d_6$) δ ppm 1.67 (2H, quin, J=6.86 Hz), 1.78-1.89 (1H, m), 2.05-2.17 (1H, m), 2.87 (1H, dt, J=10.15, 6.31 Hz), 2.97 (1H, dt, J=10.22, 6.69 Hz), 3.83 (1H, dd, J=9.06, 5.49 Hz), 3.91 (3H, s), 8.05 (1H, s), 8.13 (1H, s), 8.39 (1H, s), 8.40 (1H, s), 9.24 (1H, s), 9.34 (1H, s), 10.52 (1H, s); ESIMS found for $C_{17}H_{18}N_6O$ m/z 323.2 (M+1).

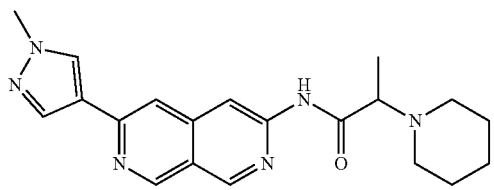

N-(6-(1-Methyl-1H-pyrazol-4-yl)-2,7-naphthyridin-3-yl)-2-(piperidin-1-yl) propanamide 3698

Off-white solid (21 mg, 0.06 mmol, 26.0% yield). $^1$H NMR (499 MHz, DMSO-$d_6$) δ ppm 1.20 (3H, d, J=7.14 Hz), 1.39-1.47 (2H, m), 1.53-1.62 (4H, m), 2.51-2.57 (4H, m), 3.48 (1H, q, J=6.95 Hz), 3.92 (3H, s), 8.03 (1H, s), 8.13 (1H, s), 8.39 (1H, s), 8.40 (1H, s), 9.25 (1H, s), 9.33 (1H, s), 10.30 (1H, s): ESIMS found for $C_{20}H_{24}N_6O$ m/z 365.2 (M+1).

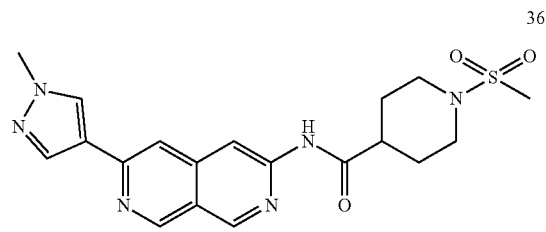

N-(6-(1-Methyl-1H-pyrazol-4-yl)-2,7-naphthyridin-3-yl)-1-(methylsulfonyl) piperidine-4-carboxamide 3699

Pale yellow solid (43 mg, 0.10 mmol, 66.3% yield). $^1$H NMR (499 MHz, DMSO-$d_6$) δ ppm 1.64-1.75 (2H, m), 1.96 (2H, br dd, J=13.17, 2.74 Hz), 2.67-2.72 (1H, m), 2.72-2.80 (2H, m), 2.90 (3H, s), 3.63 (2H, br d, J=12.08 Hz), 3.91 (3H, s), 8.00 (1H, s), 8.12 (1H, s), 8.38 (1H, s), 8.41 (1H, s), 9.24 (1H, s), 9.32 (1H, s), 10.85 (1H, s); ESIMS found for $C_{19}H_{22}N_6O_3S$ m/z 415.1 (M+1).

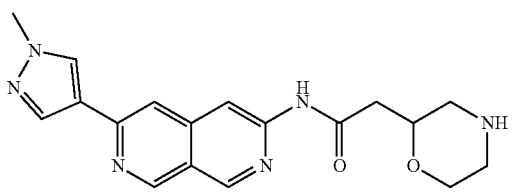

N-(6-(1-Methyl-1H-pyrazol-4-yl)-2,7-naphthyridin-3-yl)-2-(morpholin-2-yl) acetamide 3714

Brown solid (30 mg, 0.09 mmol, 30.6% yield). $^1$H NMR (499 MHz, DMSO-d) δ ppm 2.41 (1H, dd, J=12.08, 10.15 Hz), 2.47 (1H, br d, J=4.94 Hz), 2.57-2.68 (3H, m), 2.82 (1H, dd, J=12.08, 1.65 Hz), 3.42 (1H, td, J=10.77, 3.16 Hz), 3.66-3.71 (1H, m), 3.82 (1H, dtd, J=9.95, 5.18, 5.18, 2.47 Hz), 3.91 (3H, s), 8.01 (1H, s), 8.13 (1H, s), 8.38 (1H, s), 8.40 (1H, s), 9.23 (1H, s), 9.32 (1H, s), 10.72 (1H, s); ESIMS found for $C_{18}H_{20}N_6O_2$ m/z 353.2 (M+1).

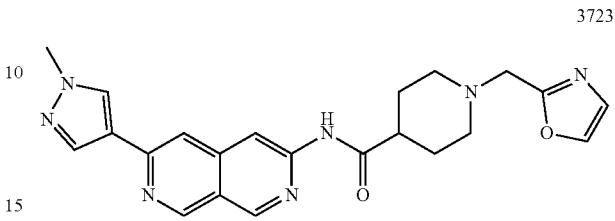

N-(6-(1-Methyl-1H-pyrazol-4-yl)-2,7-naphthyridin-3-yl)-1-(oxazol-2-ylmethyl)piperidine-4-carboxamide 3723

Brown solid (28 mg, 0.06 mmol, 42.9% yield). $^1$H NMR (499 MHz, DMSO-$d_6$) δ ppm 1.60-1.72 (2H, m), 1.80 (2H, br d, J=10.70 Hz), 2.10 (2H, td, J=11.80, 2.47 Hz), 2.52-2.58 (1H, m), 2.85-2.92 (2H, m), 3.67 (2H, s), 3.91 (3H, s), 7.17 (1H, s), 7.98 (1H, s), 8.08 (1H, d, J=0.82 Hz), 8.12 (1H, s), 8.37 (1H, s), 8.40 (1H, s), 9.22 (1H, s), 9.31 (1H, s), 10.70 (1H, s); ESIMS found for $C_{22}H_{23}N_7O_2$ m/z 418.2 (M+1).

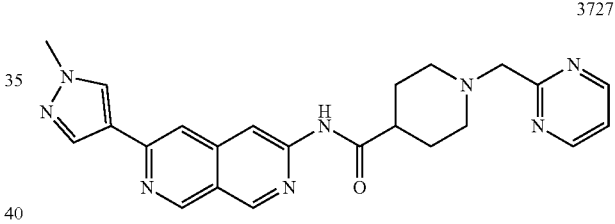

N-(6-(1-Methyl-1H-pyrazol-4-yl)-2,7-naphthyridin-3-yl)-1-(pyrimidin-2-ylmethyl)piperidine-4-carboxamide 3727

Brown solid (24 mg, 0.05 mmol, 36.0% yield). $^1$H NMR (499 MHz, DMSO-$d_6$) δ ppm 1.61-1.73 (2H, m), 1.78 (2H, br d, J=10.70 Hz), 2.10-2.19 (2H, m), 2.52-2.61 (1H, m), 2.95 (2H, br d, J=11.53 Hz), 3.71 (2H, s), 3.91 (3H, s), 7.40 (1H, t, J=4.94 Hz), 7.98 (1H, s), 8.11 (1H, s), 8.37 (1H, s), 8.41 (1H, s), 8.78 (2H, d, J=4.67 Hz), 9.22 (1H, s), 9.31 (1H, s), 10.70 (1H, s); ESIMS found for $C_{23}H_{24}N_8O$ m/z 429.2 (M+1).

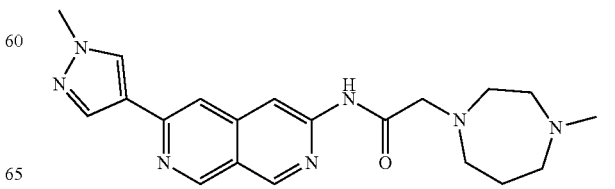

2-(4-Methyl-1,4-diazepan-1-yl)-N-(6-(1-methyl-1H-pyrazol-4-yl)-2,7-naphthyridin-3-yl)acetamide 3733

White solid (10 mg, 0.03 mmol, 22.8% yield). $^1$H NMR (499 MHz, DMSO-$d_6$) δ ppm 1.77 (2H, quin, J=5.90 Hz), 2.28 (3H, s), 2.55-2.63 (4H, m), 2.80-2.86 (4H, m), 3.39 (2H, s), 3.91 (3H, s), 8.06 (1H, s), 8.13 (1H, s), 8.38 (1H, s), 8.40 (1H, s), 9.25 (1H, s), 9.33 (1H, s), 10.17 (1H, s); ESIMS found for $C_{20}H_{25}N_7O$ m/z 380.2 (M+1).

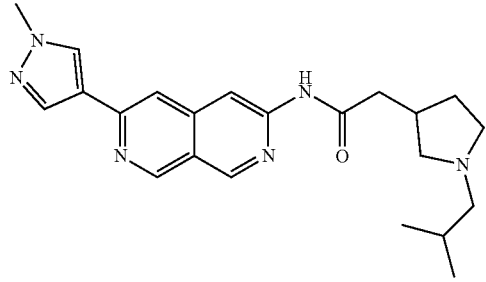

2-(1-Isobutylpyrrolidin-3-yl)-N-(6-(1-methyl-1H-pyrazol-4-yl)-2,7-naphthyridin-3-yl)acetamide 3749

White solid (4 mg, 0.01 mmol, 12.2% yield). $^1$H NMR (499 MHz, DMSO-$d_6$) δ ppm 0.85 (6H, dd, J=6.59, 1.92 Hz), 1.41 (1H, ddt, J=12.28, 7.89, 6.11, 6.11 Hz), 1.65 (1H, dquin, J=13.70, 6.80, 6.80, 6.80, 6.80 Hz), 1.89-2.00 (1H, m), 2.07-2.19 (3H, m), 2.38-2.48 (2H, m), 2.51-2.57 (3H, m), 2.62-2.68 (1H, m), 3.91 (3H, s), 7.99 (1H, s), 8.12 (1H, s), 8.37 (1H, s), 8.40 (1H, s), 9.22 (1H, s), 9.31 (1H, s), 10.74 (1H, s); ESIMS found for $C_{22}H_{28}N_6O$ m/z 393.2 (M+1).

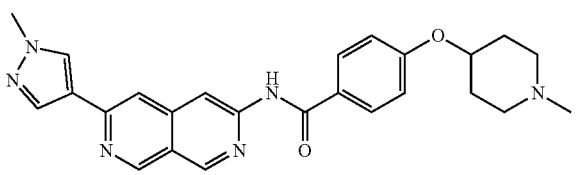

N-(6-(1-Methyl-1H-pyrazol-4-yl)-2,7-naphthyridin-3-yl)-4-((1-methylpiperidin-4-yl)oxy)benzamide 3772

Yellow solid (4.9 mg, 0.01 mmol, 27.9% yield). $^1$H NMR (499 MHz, DMSO-$d_6$) δ ppm 1.61-1.72 (2H, m), 1.92-2.01 (2H, m), 2.15-2.26 (2H, m), 2.18 (3H, s), 2.58-2.67 (2H, m), 3.92 (3H, s), 4.47-4.55 (1H, m), 7.07 (2H, d, J=8.78 Hz), 8.04-8.09 (3H, m), 8.15 (1H, s), 8.40 (1H, s), 8.56 (1H, s), 9.31 (1H, s), 9.36 (1H, s), 10.88 (1H, s); ESIMS found for $C_{25}H_{26}N_6O_2$ m/z 443.2 (M+1).

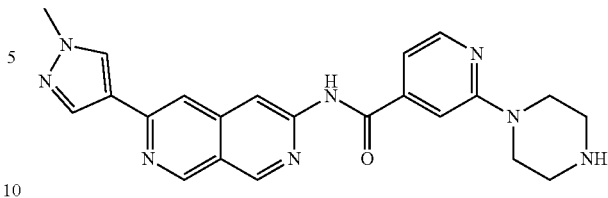

N-(6-(1-Methyl-1H-pyrazol-4-yl)-2,7-naphthyridin-3-yl)-2-(piperazin-1-yl) isonicotinamide 3773

Off-white solid (5.6 mg, 0.01 mmol, 29.3% yield). $^1$H NMR (499 MHz, DMSO-$d_6$) δ ppm 2.75-2.85 (4H, m), 3.48-3.57 (4H, m), 3.92 (3H, s), 7.12 (1H, dd, J=5.21, 1.10 Hz), 7.42 (1H, s), 8.09 (1H, s), 8.15 (1H, s), 8.25 (1H, d, J=5.21 Hz), 8.40 (1H, s), 8.57 (1H, s), 9.33 (1H, s), 9.39 (1H, s), 11.25 (1H, br s); ESIMS found for $C_{22}H_{22}N_8O$ m/z 415.2 (M+1).

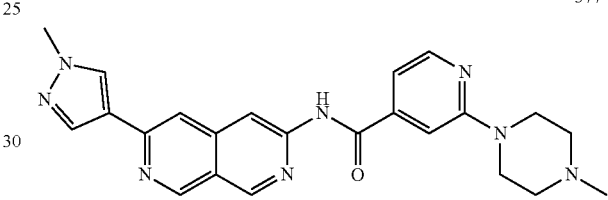

N-(6-(1-Methyl-1H-pyrazol-4-yl)-2,7-naphthyridin-3-yl)-2-(4-methylpiperazin-1-yl)isonicotinamide 3774

Off-white solid (22 mg, 0.05 mmol, 23.1% yield). $^1$H NMR (499 MHz, DMSO-$d_6$) δ ppm 2.24 (3H, s), 2.43 (4H, br t, J=4.94 Hz), 3.57-3.62 (4H, m), 3.92 (3H, s), 7.15 (1H, dd, J=5.08, 0.96 Hz), 7.46 (1H, s), 8.09 (1H, s), 8.16 (1H, s), 8.26 (1H, d, J=4.94 Hz), 8.41 (1H, s), 8.57 (1H, s), 9.33 (1H, s), 9.39 (1H, s), 11.27 (1H, s); ESIMS found for $C_{23}H_{24}N_8O$ m/z 429.2 (M+1).

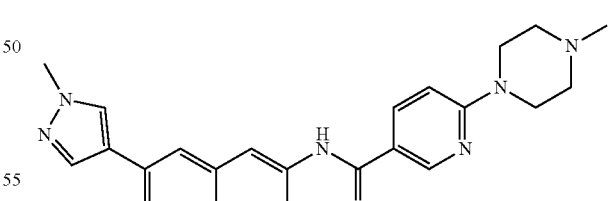

N-(6-(1-Methyl-1H-pyrazol-4-yl)-2,7-naphthyridin-3-yl)-6-(4-methylpiperazin-1-yl)nicotinamide 3778

Yellow solid (62.2 mg, 0.15 mmol, 35.3% yield). $^1$H NMR (499 MHz, DMSO-$d_6$) δ ppm 2.22 (3H, s), 2.39 (4H, t, J=5.08 Hz), 3.62-3.67 (4H, m), 3.92 (3H, s), 6.91 (1H, d, J=9.33 Hz), 8.04 (1H, s), 8.15 (1H, s), 8.19 (1H, dd, J=9.19, 2.61 Hz), 8.39 (1H, s), 8.55 (1H, s), 8.84 (1H, d, J=2.47 Hz), 9.30 (1H, s), 9.35 (1H, s), 10.86 (1H, s); ESIMS found for $C_{23}H_{24}N_8O$ m/z 429.2 (M+1).

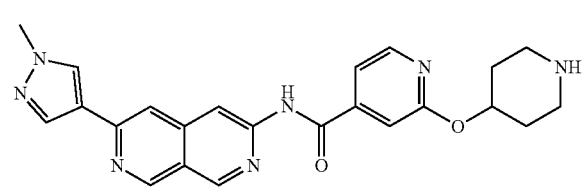

N-(6-(1-Methyl-1H-pyrazol-4-yl)-2,7-naphthyridin-3-yl)-2-(piperidin-4-yloxy)isonicotinamide 3780

Yellow solid (3.4 mg, 0.008 mmol, 9.5% yield). $^1$H NMR (500 MHz, METHANOL-d$_4$) δ ppm 1.72-1.85 (2H, m), 2.07-2.14 (2H, m), 2.82-2.89 (2H, m), 3.12-3.16 (2H, m), 3.99 (3H, s), 5.22-5.29 (1H, m), 7.30-7.34 (1H, m), 7.45 (1H, dd, J=5.21, 1.37 Hz), 8.01 (1H, s), 8.16 (1H, d, J=0.82 Hz), 8.29 (1H, s), 8.32 (1H, dd, J=5.21, 0.82 Hz), 8.64 (1H, s), 9.22-9.28 (1H, m), 9.29-9.35 (1H, m); ESIMS found for $C_{23}H_{23}N_7O_2$ m/z 430.2 (M+1).

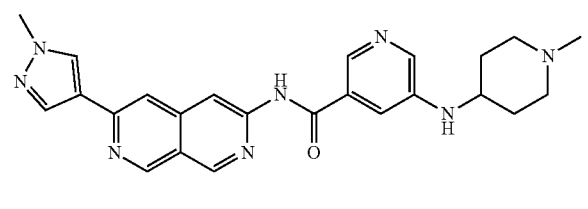

N-(6-(1-Methyl-1H-pyrazol-4-yl)-2,7-naphthyridin-3-yl)-5-(((1-methylpiperidin-4-yl)amino)nicotinamide 3783

Yellow solid (51.8 mg, 0.12 mmol, 36.2% yield). $^1$H NMR (499 MHz, DMSO-d$_6$) δ ppm 1.39-1.52 (2H, m), 1.84-1.92 (2H, m), 1.99 (2H, br t, J=10.70 Hz), 2.17 (3H, s), 2.73 (2H, br d, J=11.53 Hz), 3.63-3.77 (1H, m), 3.92 (3H, s), 6.72 (1H, d, J=7.68 Hz), 6.98 (1 H, s), 6.99 (1H, dd, J=5.21, 1.37 Hz), 8.09 (1H, s), 8.10 (1H, d, J=5.49 Hz), 8.15 (1H, s), 8.40 (1H, s), 8.54 (1H, s), 9.31 (1H, s), 9.37 (1H, s); ESIMS found for $C_{24}H_{26}N_8O$ m/z 443.2 (M+1).

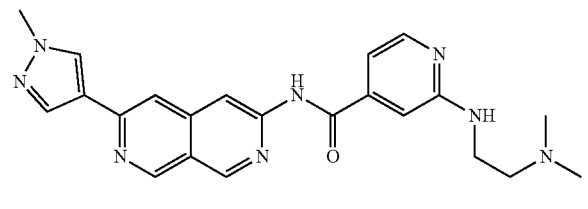

2-((2-(Dimethylamino)ethyl)amino)-N-(6-(1-methyl-1H-pyrazol-4-yl)-2,7-naphthyridin-3-yl)isonicotinamide 3791

Yellow solid (70.6 mg, 0.17 mmol, 49.9% yield). $^1$H NMR (499 MHz, DMSO-d$_6$) δ ppm 2.19 (6H, s), 2.43 (2H, t, J=6.72 Hz), 3.36-3.42 (2H, m), 3.92 (3H, s), 6.64 (1H, t, J=5.35 Hz), 7.01 (1H, dd, J=5.21, 1.65 Hz), 7.04 (1H, s), 8.09 (1H, s), 8.11 (1H, d, J=5.21 Hz), 8.15 (1H, s), 8.40 (1H, s), 8.54 (1H, s), 9.31 (1H, s), 9.38 (1H, s), 11.05 (1H, s); ESIMS found for $C_{22}H_{24}N_8O$ m/z 417.2 (M+1).

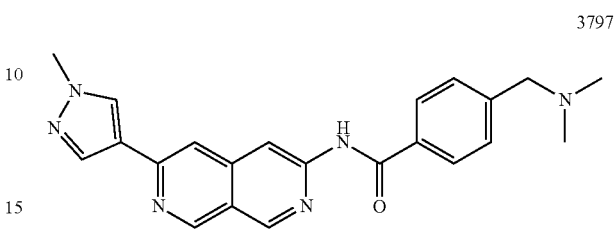

4-((Dimethylamino)methyl)-N-(6-(1-methyl-1H-pyrazol-4-yl)-2,7-naphthyridin-3-yl)benzamide 3797

White solid (4.2 mg, 0.01 mmol, 3.1% yield). $^1$H NMR (499 MHz, DMSO-d$_6$) δ ppm 2.17 (6H, s), 3.47 (2H, s), 3.92 (3H, s), 7.45 (2H, d, J=8.23 Hz), 8.05 (2H, d, J=8.23 Hz), 8.08 (1H, s), 8.15 (1H, s), 8.40 (1H, s), 8.58 (1H, s), 9.32 (1H, s), 9.37 (1H, s), 11.01 (1H, s); ESIMS found for $C_{22}H_{22}N_6O$ m/z 387.2 (M+1).

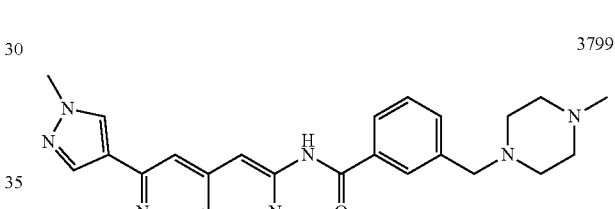

N-(6-(1-Methyl-1H-pyrazol-4-yl)-2,7-naphthyridin-3-yl)-3-((4-methylpiperazin-1-yl)methyl)benzamide 3799

White solid (8.1 mg, 0.02 mmol, 5.6% yield). $^1$H NMR (499 MHz, DMSO-d$_6$) δ ppm 2.15 (3H, s), 2.22-2.36 (4H, m), 2.37-2.47 (4H, m), 3.54 (2H, s), 3.93 (3H, s), 7.45-7.51 (1H, m), 7.53-7.57 (1H, m), 7.96 (1H, d, J=7.68 Hz), 7.98 (1H, s), 8.08 (1H, s), 8.16 (1H, s), 8.41 (1H, s), 8.57 (1H, s), 9.32 (1H, s), 9.38 (1H, s), 11.05 (1H, s); ESIMS found for $C_{25}H_{27}N_7O$ m/z 442.2 (M+1).

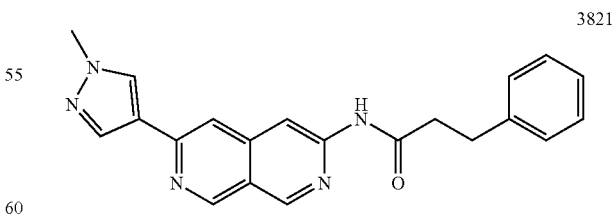

N-(6-(1-Methyl-1H-pyrazol-4-yl)-2,7-naphthyridin-3-yl)-3-phenylpropanamide 3821

White solid (15.1 mg, 0.04 mmol, 18.3% yield). $^1$H NMR (499 MHz, DMSO-d$_6$) δ ppm 2.73-2.83 (2H, m), 2.90-2.99

(2H, m), 3.91 (3H, s), 7.15-7.22 (1H, m), 7.26-7.33 (4H, m), 8.01 (1H, s), 8.13 (1H, s), 8.38 (1H, s), 8.41 (1H, s), 9.22 (1H, s), 9.31 (1H, s), 10.79 (1H, s); ESIMS found for $C_{21}H_9N_5O$ m/z 358.2 (M+1).

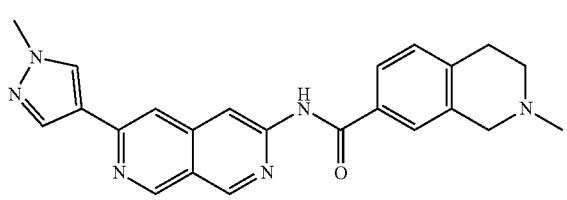

3829

2-Methyl-N-(6-(1-methyl-1H-pyrazol-4-yl)-2,7-naphthyridin-3-yl)-1,2,3,4-tetrahydroisoquinoline-7-carboxamide 3829

Yellow solid (4.2 mg, 0.01 mmol, 12.7% yield). $^1$H NMR (500 MHz, METHANOL-d$_4$) δ ppm 2.50 (3H, s), 2.80 (2H, t, J=6.17 Hz), 3.04 (2H, t, J=6.04 Hz), 3.72 (2H, s), 3.98 (3H, s), 7.32 (1H, d, J=7.96 Hz), 7.76 (1H, d, J=0.82 Hz), 7.81 (1H, dd, J=7.96, 1.92 Hz), 7.97 (1H, s), 8.15 (1H, s), 8.27 (1H, s), 8.60 (1H, s), 9.20-9.24 (1H, m), 9.28 (1H, t, J=0.82 Hz); ESIMS found for $C_{23}H_{22}N_6O$ m/z 399.2 (M+1).

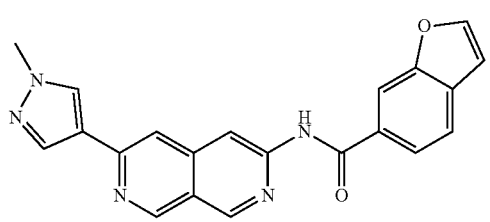

3836

N-(6-(1-Methyl-1H-pyrazol-4-yl)-2,7-naphthyridin-3-yl)benzofuran-6-carboxamide 3836

White solid (11.8 mg, 0.03 mmol, 9.0% yield). $^1$H NMR (500 MHz, DMSO-d$_6$) δ ppm 3.93 (3H, s), 7.09 (1H, dd, J=2.20, 0.82 Hz), 7.80 (1H, d, J=8.23 Hz), 8.01 (1H, dd, J=8.10, 1.51 Hz), 8.09 (1H, s), 8.16 (1H, d, J=0.82 Hz), 8.20 (1H, d, J=2.20 Hz), 8.40 (1H, d, J=0.82 Hz), 8.41 (1H, s), 8.61 (1H, s), 9.33 (1H, t, J=0.82 Hz), 9.38 (1H, t, J=0.82 Hz), 11.12 (1H, s); ESIMS found for $C_{21}H_{15}N_5O_2$ m/z 370.1 (M+1).

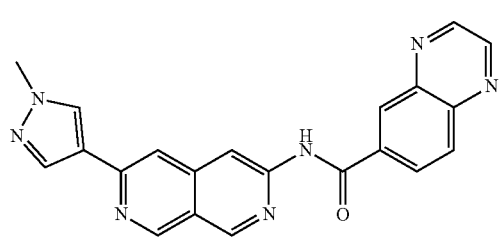

3843

N-(6-(1-Methyl-1H-pyrazol-4-yl)-2,7-naphthyridin-3-yl)quinoxaline-6-carboxamide 3843

White solid (4.6 mg, 0.01 mmol, 4.0% yield). $^1$H NMR (499 MHz, DMSO-d$_6$) δ ppm 3.93 (3H, s), 8.13 (1H, s), 8.17 (1H, s), 8.24 (1H, d, J=8.78 Hz), 8.41 (1H, s), 8.42-8.44 (1H, m), 8.64 (1H, s), 8.85 (1H, d, J=1.92 Hz), 9.06-9.11 (2H, m), 9.36 (1H, s), 9.40 (1H, s), 11.54 (1H, s); ESIMS found for $C_{21}H_{15}N_7O$ m/z 382.1 (M+1).

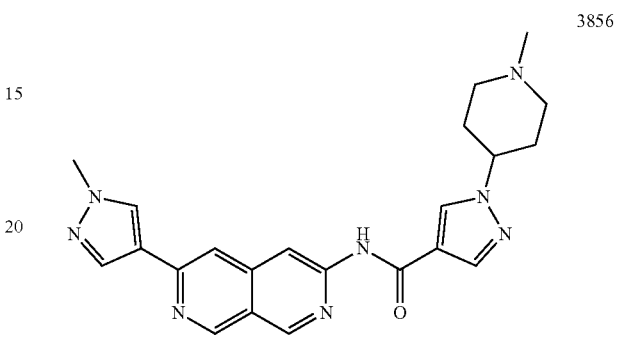

3856

N-(6-(1-Methyl-1H-pyrazol-4-yl)-2,7-naphthyridin-3-yl)-1-(1-methylpiperidin-4-yl)-1H-pyrazole-4-carboxamide 3856

Yellow solid (21.5 mg, 0.05 mmol, 65.8% yield). H NMR (499 MHz, DMSO-d$_6$) δ ppm 1.90-1.99 (2H, m), 2.01-2.10 (4H, m), 2.21 (3H, s), 2.85 (2H, br d, J=11.80 Hz), 3.92 (3H, s), 4.17 (1H, tt, J=11.11, 4.25 Hz), 8.03 (1H, s), 8.15 (1H, s), 8.20 (1H, s), 8.39 (1H, s), 8.51 (1H, s), 8.64 (1H, s), 9.29 (1H, s), 9.34 (1H, s), 10.73 (1H, s); ESIMS found for $C_{22}H_{24}N_8O$ m/z 417.2 (M+1).

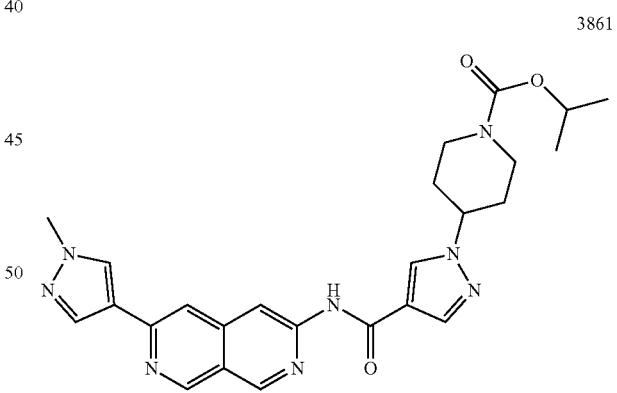

3861

Isopropyl 4-(4-((6-(1-methyl-1H-pyrazol-4-yl)-2,7-naphthyridin-3-yl) carbamoyl)-1H-pyrazol-1-yl) piperidine-1-carboxylate 3861

White solid (11 mg, 0.02 mmol, 27.5% yield). $^1$H NMR (499 MHz, DMSO-d$_6$) δ ppm 1.21 (6H, d, J=6.04 Hz), 1.76-1.85 (2H, m), 2.08 (2H, br dd, J=12.35, 1.92 Hz), 2.99 (2H, br s), 3.92 (3H, s), 4.07 (2H, br d, J=12.90 Hz), 4.45 (1H, tt, J=11.29, 3.95 Hz), 4.80 (1H, spt, J=6.27 Hz), 8.03 (1H, s), 8.15 (1H, s), 8.21 (1H, s), 8.39 (1H, s), 8.51 (1H, s), 8.66 (1H, s), 9.29 (1H, s), 9.34 (1H, s), 10.73 (1H, s); ESIMS found for C$_{25}$H$_{28}$N$_{8}$O$_{3}$ m/z 489.3 (M+1).

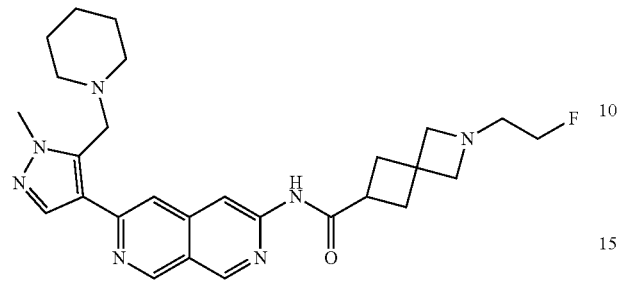

2-(2-Fluoroethyl)-N-(6-(1-methyl-5-(piperidin-1-ylmethyl)-1H-pyrazol-4-yl)-2,7-naphthyridin-3-yl)-2-azaspiro[3.3]heptane-6-carboxamide 3907

Beige solid (10 mg, 0.02 mmol, 45.3% yield). $^1$H NMR (499 MHz, METHANOL-d$_4$) δ ppm 1.45 (2H, br d, J=7.14 Hz), 1.51-1.60 (4H, m), 2.40-2.54 (8H, m), 2.75 (2H, dt, J=28.40, 5.00 Hz), 3.21-3.30 (1H, m), 3.34 (2H, s), 3.43 (2H, s), 3.97 (2H, br s), 3.99 (3H, s), 4.44 (2H, dt, J=47.90, 5.00 Hz), 7.98 (1H, s), 8.06 (1H, s), 8.47 (1H, s), 9.19 (1H, s), 9.29 (1H, s); ESIMS found for C$_{27}$H$_{34}$FN$_7$O m/z 492.3 (M+1).

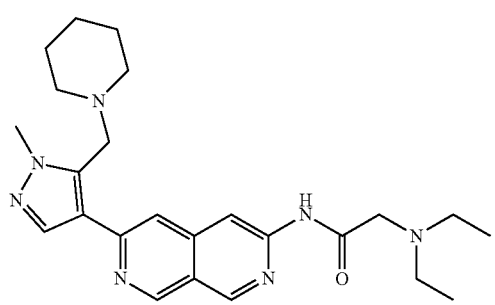

2-(Diethylamino)-N-(6-(1-methyl-5-(piperidin-1-ylmethyl)-1H-pyrazol-4-yl)-2,7-naphthyridin-3-yl)acetamide 3910

Beige solid (4 mg, 0.009 mmol, 5.9% yield). $^1$H NMR (499 MHz, METHANOL-d$_4$) δ ppm 1.15 (7H, t, J=7.14 Hz), 1.40-1.47 (2H, m), 1.56 (5H, dt, J=11.11, 5.42 Hz), 2.47 (4H, br s), 2.73 (4H, q, J=6.86 Hz), 3.30 (2H, br s), 3.99 (2H, s), 3.99 (3H, s), 8.00 (1H, s), 8.10 (1H, s), 8.51 (1H, s), 9.22 (1H, s), 9.34 (1H, s); ESIMS found for C$_{24}$H$_{33}$N$_7$O m/z 436.3 (M+1).

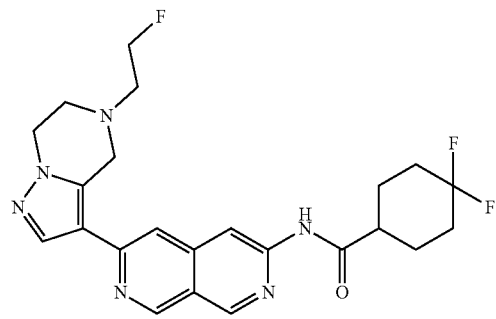

4,4-Difluoro-N-(6-(5-(2-fluoroethyl)-4,5,6,7-tetrahydropyrazolo[1,5-a]pyrazin-3-yl)-2,7-naphthyridin-3-yl)cyclohexane-1-carboxamide 3944

Off-white solid (40 mg, 0.09 mmol, 17.3% yield). $^1$H NMR (499 MHz, DMSO-d$_6$) δ ppm 1.65-1.75 (2H, m), 1.76-1.91 (2H, m), 1.96 (2H, br d, J=13.17 Hz), 2.07-2.17 (2H, m), 2.68-2.79 (1H, m), 2.97 (2H, dt, J=29.10, 5.00 Hz), 3.05 (2H, br t, J=5.35 Hz), 4.15-4.23 (4H, m), 4.66 (2H, dt, J=47.90, 5.00 Hz), 7.92 (1H, s), 8.17 (1H, s), 8.42 (1H, s), 9.23 (1H, s), 9.33 (1H, s), 10.82 (1H, s); ESIMS found for C$_{23}$H$_{25}$F$_3$N$_6$O m/z 459.2 (M+1).

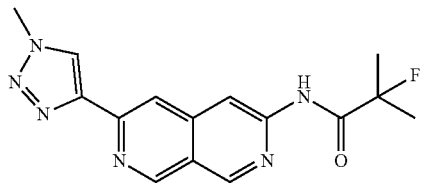

2-Fluoro-2-methyl-N-(6-(1-methyl-1H-1,2,3-triazol-4-yl)-2,7-naphthyridin-3-yl)propanamide 3960

White solid (3 mg, 0.01 mmol, 2.7% yield). $^1$H NMR (499 MHz, DMSO-d$_6$) δ ppm 1.65 (6H, d, J=22.00 Hz), 4.52 (3H, s), 8.10 (1H, d, J=8.51 Hz), 8.59 (1H, s), 8.61 (1H, s), 8.67 (1H, dd, J=8.51, 0.82 Hz), 9.29 (1H, s), 10.24 (1H, br d, J=3.29 Hz); ESIMS found for C$_{15}$H$_{15}$FN$_6$O m/z 315.1 (M+1).

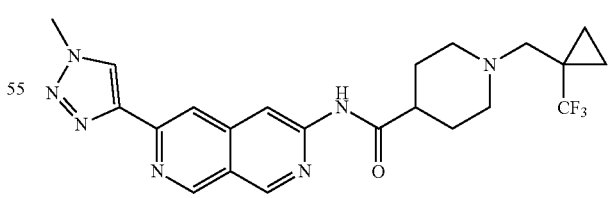

N-(6-(1-Methyl-1H-1,2,3-triazol-4-yl)-2,7-naphthyridin-3-yl)-1-((1-(trifluoromethyl)cyclopropyl)methyl)piperidine-4-carboxamide 3974

Off-white solid (5 mg, 0.01 mmol, 9.0% yield). $^1$H NMR (499 MHz, DMSO-d$_6$) δ ppm 1.61-1.73 (2H, m), 1.76-1.84

(2H, m), 1.91-1.99 (2H, m), 2.58 (1H, tt, J=11.53, 3.98 Hz), 2.97 (2H, br d, J=11.53 Hz), 4.39 (3H, s), 8.35 (1H, s), 8.36 (1H, s), 8.56 (1H, s), 9.41 (1H, s), 9.50 (1H, s), 10.89 (1H, s); ESIMS found for $C_{22}H_{24}F_3N_7O$ m/z 460.2 (M+1).

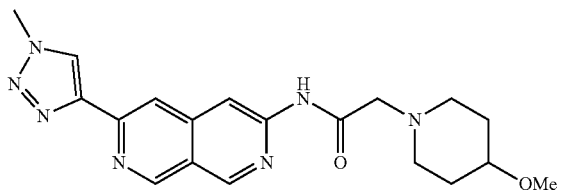

3985

2-(4-Methoxypiperidin-1-yl)-N-(6-(1-methyl-1H-1,2,3-triazol-4-yl)-2,7-naphthyridin-3-yl)acetamide 3985

Off-white solid (20 mg, 0.05 mmol, 8.8% yield). $^1$H NMR (499 MHz, DMSO-$d_6$) δ ppm 1.47-1.57 (2H, m), 1.84-1.92 (2H, m), 2.33-2.42 (2H, m), 2.74-2.83 (2H, m), 3.20-3.23 (1H, m), 3.24 (3H, s), 3.26 (2H, s), 4.39 (3H, s), 8.36 (1H, s), 8.42 (1H, s), 8.55 (1H, s), 9.42 (1H, s), 9.53 (1H, s), 10.32 (1H, s): ESIMS found for $C_{19}H_{23}N_7O_2$ m/z 382.2 (M+1).

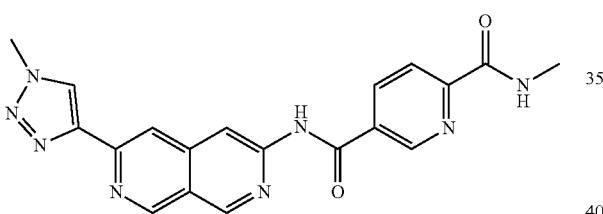

3999

$N^2$-Methyl-$N^5$-(6-(1-methyl-1H-1,2,3-triazol-4-yl)-2,7-naphthyridin-3-yl) pyridine-2,5-dicarboxamide 3999

White solid (10 mg, 0.02 mmol, 10.5% yield). $^1$H NMR (499 MHz, DMSO-$d_6$) δ ppm 2.86 (3H, d, J=4.94 Hz), 4.41 (3H, s), 8.15-8.20 (1H, m), 8.39 (1H, s), 8.48 (1H, s), 8.56 (1H, dd, J=8.10, 2.33 Hz), 8.75 (1H, s), 8.92-8.98 (1H, m), 9.22 (1H, dd, J=2.20, 0.82 Hz), 9.52 (1H, s), 9.58 (1H, s), 11.67 (1H, s); ESIMS found for $C_{19}H_{16}N_8O_2$ m/z 389.2 (M+1).

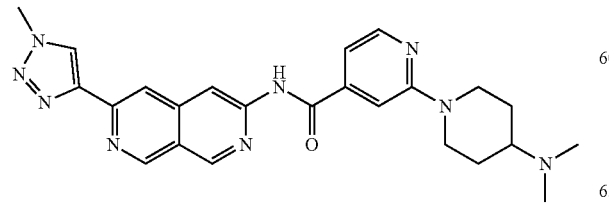

4003

2-(4-(Dimethylamino)piperidin-1-yl)-N-(6-(1-methyl-1H-1,2,3-triazol-4-yl)-2,7-naphthyridin-3-yl) isonicotinamide 4003

Beige solid (10 mg, 0.02 mmol, 28.6% yield). $^1$H NMR (499 MHz, DMSO-$d_6$) δ ppm 1.37 (2H, qd, J=11.94, 3.98 Hz), 1.80-1.88 (2H, m), 2.20 (6H, s), 2.32-2.42 (1H, m), 2.83-2.95 (2H, m), 4.38-4.41 (3H, m), 4.44 (2H, br d, J=13.45 Hz), 7.10 (1H, dd, J=4.94, 1.10 Hz), 7.46 (1H, s), 8.25 (1H, d, J=5.21 Hz), 8.38 (1H, s), 8.45 (1H, s), 8.73 (1H, s), 9.51 (1H, s), 9.57 (1H, s), 11.41 (1H, br s); ESIMS found for $C_{24}H_{27}N_9O$ m/z 458.3 (M+1).

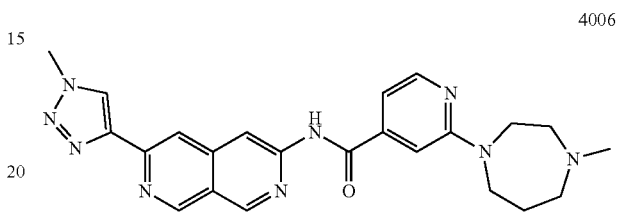

4006

2-(4-Methyl-1,4-diazepan-1-yl)-N-(6-(1-methyl-1H-1,2,3-triazol-4-yl)-2,7-naphthyridin-3-yl)isonicotinamide 4006

Beige solid (14 mg, 0.03 mmol, 38.5% yield). H NMR (499 MHz, DMSO-$d_6$) δ ppm 1.88-1.98 (2H, m), 2.27 (3H, s), 2.48 (2H, br s), 2.60-2.66 (2H, m), 3.69 (2H, t, J=6.17 Hz), 3.80-3.85 (2H, m), 4.40 (3H, s), 7.04 (1H, dd, J=5.21, 1.37 Hz), 7.21 (1H, s), 8.22 (1H, d, J=5.49 Hz), 8.38 (1H, s), 8.45 (1H, s), 8.73 (1H, s), 9.51 (1H, s), 9.58 (1H, s), 11.40 (1H, s); ESIMS found for $C_{23}H_{25}N_9O$ m/z 444.3 (M+1).

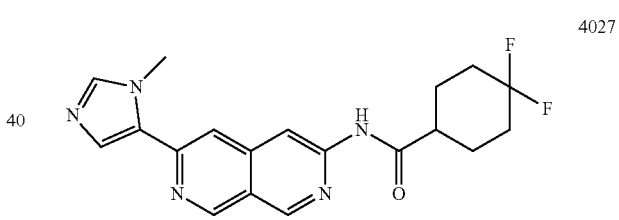

4027

4,4-Difluoro-N-(6-(1-methyl-1H-imidazol-5-yl)-2,7-naphthyridin-3-yl) cyclohexane-1-carboxamide 4027

Off-white solid (20 mg, 0.05 mmol, 24.3% yield). $^1$H NMR (499 MHz, DMSO-$d_6$) δ ppm 1.64-1.76 (2H, m), 1.77-1.92 (2H, m), 1.96 (2H, br d, J=12.62 Hz), 2.07-2.19 (2H, m), 2.69-2.79 (1H, m), 3.99 (3H, s), 7.61 (1H, s), 7.79 (1H, s), 8.10 (1H, s), 8.47 (1H, s), 9.31 (1H, s), 9.40 (1H, s), 10.87 (1H, s); ESIMS found for $C_{19}H_{19}F_2N_5O$ m/z 372.2 (M+1).

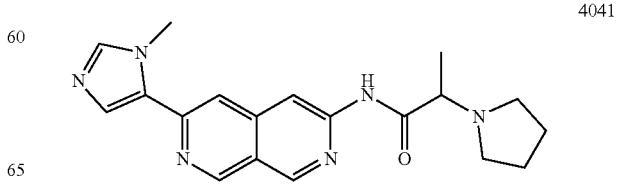

4041

N-(6-(1-Methyl-1H-imidazol-5-yl)-2,7-naphthyridin-3-yl)-2-(pyrrolidin-1-yl) propanamide 4041

Brown solid (12 mg, 0.03 mmol, 10.4% yield). $^1$H NMR (499 MHz, DMSO-d$_6$) δ ppm 1.30 (3H, d, J=6.86 Hz), 1.74 (4H, s), 2.55-2.71 (5H, m), 3.34-3.40 (1H, m), 4.00 (3H, s), 7.62 (1H, d, J=0.82 Hz), 7.80 (1H, s), 8.14 (1H, s), 8.47 (1H, s), 9.31 (1H, s), 9.42 (1H, s), 10.26 (1H, s); ESIMS found for C$_{19}$H$_{22}$N$_6$O m/z 351.2 (M+1).

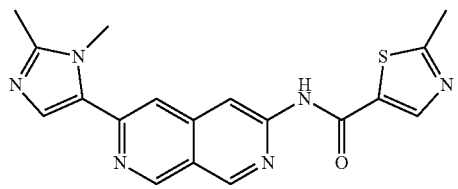

N-(6-(1,2-Dimethyl-1H-imidazol-5-yl)-2,7-naphthyridin-3-yl)-2-methylthiazole-5-carboxamide 4074

Light brown solid (0 mg, 0.05 mmol, 26.3% yield). $^1$H NMR (499 MHz, DMSO-d$_6$) δ ppm 2.40 (3H, s), 2.72 (3H, s), 3.90 (3H, s), 7.46 (1H, s), 8.08 (1H, s), 8.52 (1H, s), 8.71 (1H, s), 9.38 (1H, s), 9.45 (1H, s), 11.40 (1H, s); ESIMS found for C$_{18}$H$_{16}$N$_6$OS m/z 365.1 (M+1).

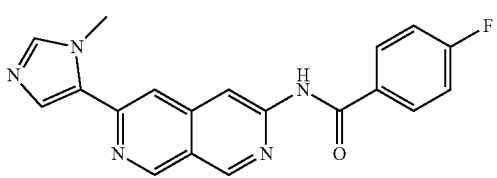

4-Fluoro-N-(6-(1-methyl-1H-imidazol-5-yl)-2,7-naphthyridin-3-yl) benzamide 4075

White solid (17 mg, 0.05 mmol, 15.7% yield). $^1$H NMR (499 MHz, DMSO-d$_6$) δ ppm 4.01 (3H, s), 7.37 (2H, t, J=8.78 Hz), 7.64 (1H, d, J=1.10 Hz), 7.81 (1H, s), 8.17 (2H, dd, J=8.92, 5.35 Hz), 8.19 (1H, s), 8.31 (1H, s), 8.64 (1H, s), 9.39 (1H, s), 9.46 (1H, s), 11.18 (1H, s); ESIMS found for C$_{19}$H$_{14}$FN$_5$O m/z 348.1 (M+1).

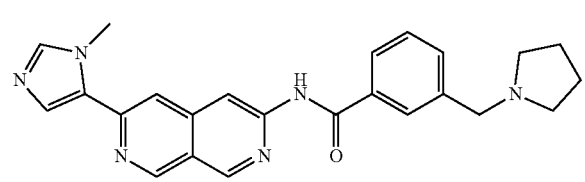

N-(6-(1-Methyl-1H-imidazol-5-yl)-2,7-naphthyridin-3-yl)-3-(pyrrolidin-1-ylmethyl)benzamide 4077

White solid (67 mg, 0.15 mmol, 50.7% yield). $^1$H NMR (499 MHz, DMSO-d$_6$) δ ppm 1.72 (4H, br s), 2.47 (4H, br s), 3.67 (2H, s), 4.01 (3H, s), 7.45-7.51 (1H, m), 7.55 (1H, d, J=7.68 Hz), 7.65 (1H, s), 7.81 (1H, s), 7.95 (1H, d, J=7.96 Hz), 8.01 (1H, s), 8.19 (1H, s), 8.65 (1H, s), 9.39 (1H, s), 9.46 (1H, s), 11.11 (1H, s); ESIMS found for C$_{24}$H$_{24}$N$_6$O m/z 413. (M+1).

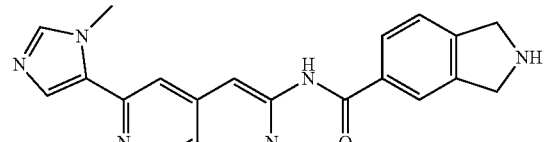

N-(6-(1-Methyl-1H-imidazol-5-yl)-2,7-naphthyridin-3-yl)isoindoline-5-carboxamide 4104

Off-white solid (0 mg, 0.03 mmol, 66.9% yield). $^1$H NMR (499 MHz, DMSO-d$_6$) δ ppm 4.01 (3H, s), 4.15 (4H, s), 7.41 (1H, d, J=7.96 Hz), 7.64 (1H, s), 7.81 (1H, s), 7.93 (1H, d, J=7.68 Hz), 7.98 (1H, s), 8.18 (1H, s), 8.65 (1H, s), 9.39 (1H, s), 9.45 (1H, s), 11.02 (1H, br s); ESIMS found for C$_{21}$H$_{18}$N$_6$O m/z 371.1 (M+1).

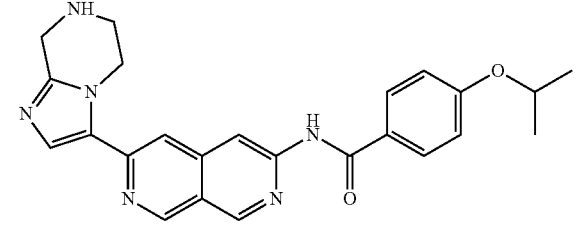

4-Isopropoxy-N-(6-(5,6,7,8-tetrahydroimidazo[1,2-a]pyrazin-3-yl)-2,7-naphthyridin-3-yl)benzamide 4150

White solid (5.6 mg, 0.01 mmol, 29.8% yield). $^1$H NMR (499 MHz, DMSO-d$_6$) δ ppm 1.31 (6H, d, J=6.04 Hz), 3.10 (2H, br t, J=5.35 Hz), 3.95 (2H, s), 4.35 (2H, t, J=5.49 Hz), 4.72-4.82 (1H, m), 7.03 (2H, d, J=9.06 Hz), 7.61 (1H, s), 8.04-8.09 (2H, m), 8.10 (1H, s), 8.61 (1H, s), 9.35 (1H, s), 9.40 (1H, s), 10.89 (1H, s); ESIMS found for C$_{24}$H$_{24}$N$_6$O$_2$ m/z 429.2 (M+1).

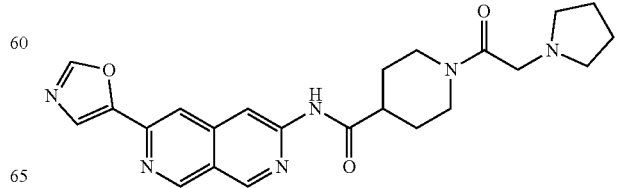

N-(6-(Oxazol-5-yl)-2,7-naphthyridin-3-yl)-1-(2-(pyrrolidin-1-yl)acetyl) piperidine-4-carboxamide 4159

Off-white solid (4 mg, 0.009 mmol, 43.0% yield). $^1$H NMR (499 MHz, DMSO-d$_6$) δ ppm 1.43-1.53 (1H, m), 1.56-1.66 (1H, m), 1.69 (4H, br s), 1.86 (2H, br dd, J=13.04, 2.06 Hz), 2.48 (4H, br s), 2.58-2.66 (1H, m), 2.80-2.90 (1H, m), 3.02 (1H, br t, J=11.80 Hz), 3.16-3.22 (1H, m), 3.35 (1H, br s), 4.11 (1H, br d, J=13.72 Hz), 4.37-4.43 (1H, m), 8.44 (1H, s), 8.51 (1H, s), 8.72 (1H, s), 9.20 (1H, s), 9.33 (1H, s), 9.38 (1H, s), 10.91 (1H, s); ESIMS found for C$_{23}$H$_{26}$N$_6$O$_2$S m/z 451.2 (M+1).

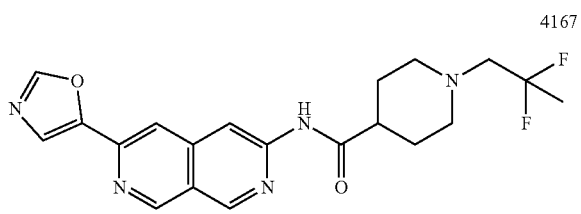 [SMILES: CC(F)(F)CN1CCC(C(=O)Nc2cc3cc(-c4cnco4)ncc3cn2)CC1]

1-(2,2-Difluoropropyl)-N-(6-(oxazol-5-yl)-2,7-naphthyridin-3-yl)piperidine-4-carboxamide 4167

White solid (17.6 mg, 0.04 mmol, 22.4% yield). $^1$H NMR (499 MHz, DMSO-d$_6$) δ ppm 1.63 (3H, t, J=19.21 Hz), 1.64-1.74 (2H, m), 1.77-1.83 (2H, m), 2.22 (2H, td, J=11.66, 1.92 Hz), 2.53-2.62 (1H, m), 2.71 (2H, t, J=14.00 Hz), 2.95 (2H, br d, J=11.53 Hz), 7.89 (1H, s), 8.11 (1H, s), 8.55 (1H, s), 8.62 (1H, s), 9.34 (1H, s), 9.41 (1H, s), 10.84 (1H, s); ESIMS found for C$_{20}$H$_{21}$F$_2$N$_5$O$_2$ m/z 402.2 (M+1).

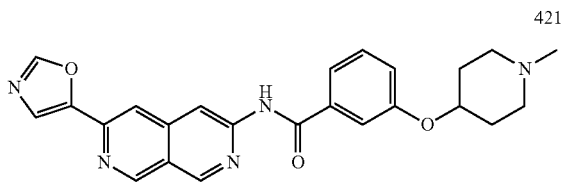

3-((1-Methylpiperidin-4-yl)oxy)-N-(6-(oxazol-5-yl)-2,7-naphthyridin-3-yl) benzamide 4218

Yellow solid (2.4 mg, 0.005 mmol, 18.4% yield). $^1$H NMR (499 MHz, DMSO-d$_6$) δ ppm 1.62-1.74 (2H, m), 1.93-2.02 (2H, m), 2.15-2.27 (2H, m), 2.19 (3H, s), 2.59-2.68 (2H, m), 4.50-4.59 (1H, m), 7.17-7.25 (1H, m), 7.43 (1H, t, J=8.23 Hz), 7.61-7.67 (2H, m), 7.92 (1H, s), 8.20 (1H, s), 8.64 (1H, s), 8.71 (1H, s), 9.44 (1H, s), 9.48 (1H, s), 11.17 (1H, s); ESIMS found for C$_{24}$H$_{23}$N$_5$O$_3$ m/z 430.2 (M+1).

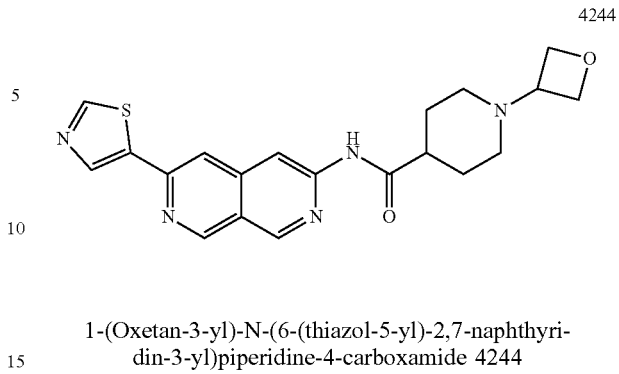

1-(Oxetan-3-yl)-N-(6-(thiazol-5-yl)-2,7-naphthyridin-3-yl)piperidine-4-carboxamide 4244

Off-white solid (55 mg, 0.14 mmol, 49.7% yield). $^1$H NMR (499 MHz, DMSO-d$_6$) δ ppm 1.64-1.74 (2H, m), 1.75-1.87 (4H, m), 2.59 (1H, tt, J=11.29, 3.81 Hz), 2.70-2.79 (2H, m), 3.38 (1H, quin, J=6.38 Hz), 4.43 (2H, t, J=6.17 Hz), 4.53 (2H, t, J=6.59 Hz), 8.43 (1H, s), 8.52 (1H, s), 8.72 (1H, s), 9.20 (1H, s), 9.32 (1H, s), 9.37 (1H, s), 10.83 (1H, s); ESIMS found for C$_{20}$H$_{21}$N$_5$O$_2$S m/z 396.15 (M+1).

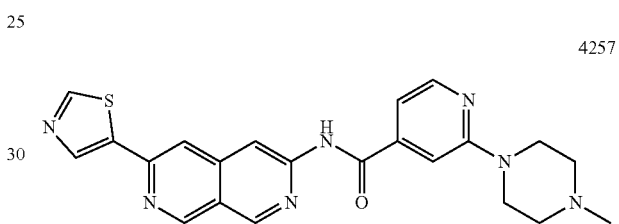

2-(4-Methylpiperazin-1-yl)-N-(6-(thiazol-5-yl)-2,7-naphthyridin-3-yl) isonicotinamide 4257

Yellow solid (59.6 mg, 0.14 mmol, 38.4% yield). $^1$H NMR (499 MHz, DMSO-d$_6$) δ ppm 2.25 (3H, s), 2.44 (4H, br s), 3.61 (4H, br s), 7.15 (1H, dd, J=5.08, 1.23 Hz), 7.47 (1H, s), 8.27 (1H, d, J=5.21 Hz), 8.54 (1H, s), 8.68 (1H, s), 8.76 (1H, s), 9.22 (1H, s), 9.43 (1H, s), 9.44-9.50 (1H, m), 11.37 (1H, s); ESIMS found for C$_{22}$H$_{21}$N$_7$OS m/z 432.2 (M+1).

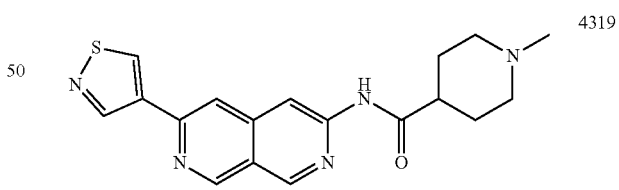

N-(6-(Isothiazol-4-yl)-2,7-naphthyridin-3-yl)-1-methylpiperidine-4-carboxamide 4319

Off-white solid (70 mg, 0.20 mmol, 60.4% yield). $^1$H NMR (499 MHz, DMSO-d$_6$) δ ppm 1.62-1.73 (2H, m), 1.76-1.82 (2H, m), 1.87 (2H, td, J=11.66, 2.20 Hz), 2.16 (3H, s), 2.52-2.58 (1H, m), 2.78-2.85 (2H, m), 8.39 (1H, s), 8.52 (1H, s), 9.32 (1H, s), 9.33 (1H, s), 9.43 (1H, s), 9.69 (1H, s), 10.81 (1H, s); ESIMS found for C$_{18}$H$_{19}$N$_5$OS m/z 354.1 (M+1).

4332

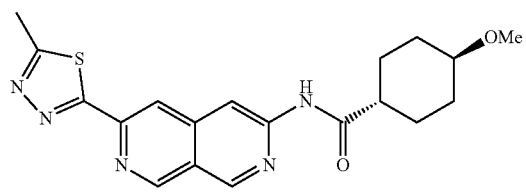

trans-4-Methoxy-N-(6-(5-methyl-1,3,4-thiadiazol-2-yl)-2,7-naphthyridin-3-yl)cyclohexane-1-carboxamide 4332

Off-white solid (2 mg, 0.005 mmol, 6.3% yield). $^1$H NMR (499 MHz, DMSO-$d_6$) δ ppm 1.08-1.17 (2H, m), 1.45-1.54 (2H, m), 1.92 (2H, br d, J=12.08 Hz), 2.06-2.12 (2H, m), 2.53-2.61 (1H, m), 2.81 (3H, s), 3.08-3.16 (1H, m), 3.25 (3H, s), 8.61 (2H, d, J=0.82 Hz), 9.42 (1H, s), 9.46 (1H, s), 10.88 (1H, s); ESIMS found for $C_{19}H_{21}N_5O_2S$ m/z 384.15 (M+1).

4346

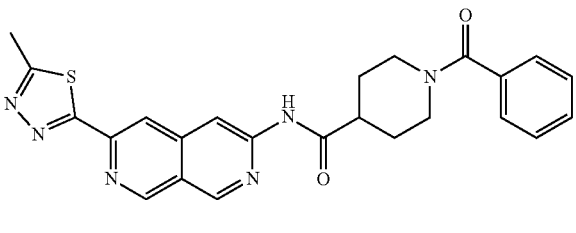

1-Benzoyl-N-(6-(5-methyl-1,3,4-thiadiazol-2-yl)-2,7-naphthyridin-3-yl) piperidine-4-carboxamide 4346

Off-white solid (8 mg, 0.02 mmol, 21.2% yield). $^1$H NMR (499 MHz, DMSO-$d_6$) δ ppm 1.55-1.71 (2H, m), 1.76-2.05 (2H, m), 2.82 (3H, s), 2.86-2.97 (2H, m), 3.02-3.18 (1H, m), 3.57-3.78 (1H, m), 4.40-4.63 (1H, m), 7.37-7.42 (2H, m), 7.44-7.49 (3H, m), 8.63 (1H, s), 8.64 (1H, s), 9.43 (1H, s), 9.47 (1H, s), 10.99 (1H, s); ESIMS found for $C_{24}H_{22}N_6O_2S$ m/z 459.2 (M+1).

4353

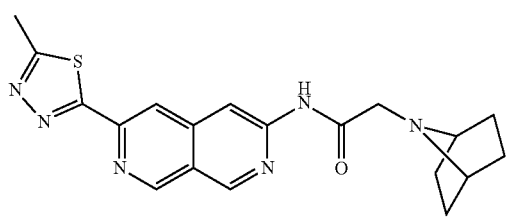

2-(7-Azabicyclo[2.2.1]heptan-7-yl)-N-(6-(5-methyl-1,3,4-thiadiazol-2-yl)-2,7-naphthyridin-3-yl)acetamide 4353

Beige solid (7 mg, 0.02 mmol, 58.8% yield). $^1$H NMR (499 MHz, DMSO-$d_6$) δ ppm 1.34 (4H, br d, J=7.14 Hz), 1.72-1.78 (4H, m), 2.82 (3H, s), 3.24 (2H, s), 3.36-3.41 (2H, m), 8.63 (1H, s), 8.69 (1H, s), 9.43 (1H, s), 9.50 (1H, s), 10.41 (1H, s); ESIMS found for $C_{19}H_{20}N_6OS$ m/z 381.1 (M+1).

4377

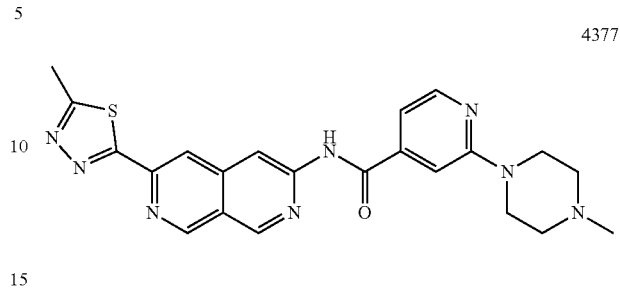

N-(6-(5-Methyl-1,3,4-thiadiazol-2-yl)-2,7-naphthyridin-3-yl)-2-(4-methylpiperazin-1-yl)isonicotinamide 4377

Yellow solid (13.9 mg, 0.03 mmol, 17.6% yield). $^1$H NMR (499 MHz, DMSO-$d_6$) δ ppm 2.23 (3H, s), 2.43 (4H, t, J=4.94 Hz), 2.82 (3H, s), 3.57-3.65 (4H, m), 7.16 (1H, dd, J=5.08, 0.96 Hz), 7.47 (1H, s), 8.27 (1H, d, J=5.21 Hz), 8.71 (1H, s), 8.79 (1H, s), 9.51 (1H, s), 9.53 (1H, s), 11.42 (1H, br s); ESIMS found for $C_{22}H_{22}N_8OS$ m/z 447.2 (M+1).

4431

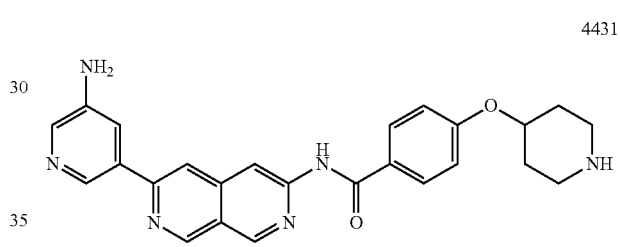

N-(6-(5-Aminopyridin-3-yl)-2,7-naphthyridin-3-yl)-4-(piperidin-4-yloxy) benzamide 4431

White solid (1 mg, 0.002 mmol, 29.1% yield). $^1$H NMR (499 MHz, DMSO-$d_6$) δ ppm 1.79-1.89 (2H, m), 2.09-2.15 (2H, m), 3.03-3.15 (2H, m), 3.21-3.28 (2H, m), 4.76-4.84 (1H, m), 5.50 (2H, s), 7.14 (2H, d, J=8.78 Hz), 7.79 (1H, t, J=2.33 Hz), 8.02 (1H, d, J=2.47 Hz), 8.09-8.16 (2H, m), 8.39 (1H, s), 8.59 (1H, d, J=1.37 Hz), 8.70 (1H, s), 9.42 (1H, s), 9.50 (1H, s), 10.99 (1H, s); ESIMS found for $C_{25}H_{24}N_6O_2$ m/z 441.2 (M+1).

4432

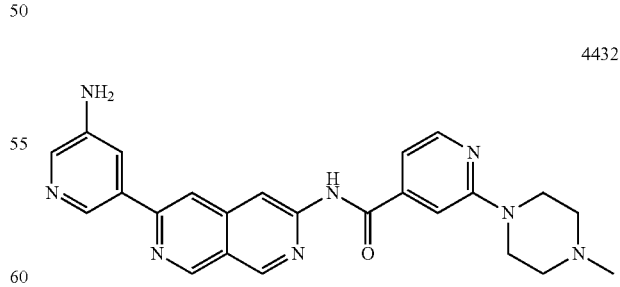

N-(6-(5-Aminopyridin-3-yl)-2,7-naphthyridin-3-yl)-2-(4-methylpiperazin-1-yl)isonicotinamide 4432

Brown solid (15 mg, 0.03 mmol, 18.6% yield). $^1$H NMR (499 MHz, DMSO-$d_6$) δ ppm 2.23 (3H, s), 2.43 (4H, t, J=4.94 Hz), 3.57-3.64 (4H, m), 5.50 (2H, s), 7.15 (1H, dd, J=5.08, 1.23 Hz), 7.47 (1H, s), 7.79 (1H, t, J=2.20 Hz), 8.02 (1H, d, J=2.47 Hz), 8.27 (1H, d, J=4.94 Hz), 8.42 (1H, s), 8.59 (1H, d, J=1.92 Hz), 8.71 (1H, s), 9.44 (1H, s), 9.52 (1H, s), 11.34 (1H, s); ESIMS found for $C_{24}H_{24}N_8O$ m/z 441.2 (M+1).

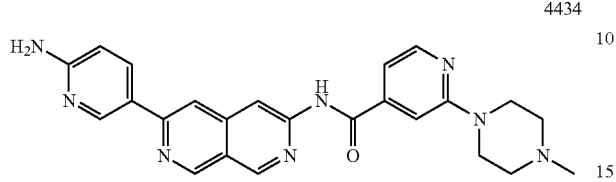

N-(6-(6-Aminopyridin-3-yl)-2,7-naphthyridin-3-yl)-2-(4-methylpiperazin-1-yl)isonicotinamide 4434

Beige solid (68 mg, 0.15 mmol, 84.4% yield). $^1$H NMR (499 MHz, DMSO-$d_6$) δ ppm 2.23 (3H, s), 2.42 (4H, t, J=5.08 Hz), 3.56-3.64 (4H, m), 6.38 (2H, s), 6.57 (1H, d, J=8.78 Hz), 7.15 (1H, dd, J=4.94, 1.10 Hz), 7.46 (1H, s), 8.21-8.29 (3H, m), 8.62 (1H, s), 8.88 (1H, d, J=2.47 Hz), 9.35 (1H, s), 9.43 (1H, s), 11.26 (1H, s); ESIMS found for $C_{24}H_{24}N_8O$ m/z 441.2 (M+1).

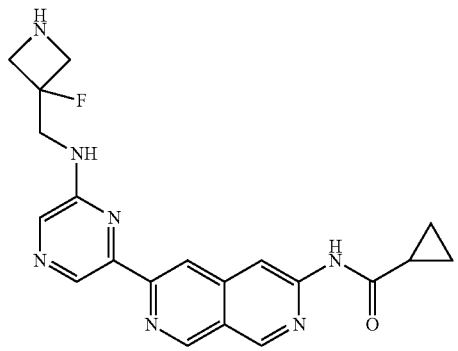

N-(6-(6-(((3-Fluoroazetidin-3-yl)methyl)amino)pyrazin-2-yl)-2,7-naphthyridin-3-yl)cyclopropanecarboxamide 4498

Orange solid (14.7 mg, 0.04 mmol, 76.2% yield). $^1$H NMR (499 MHz, DMSO-$d_6$) δ ppm 0.85-0.91 (4H, m), 2.07-2.15 (1H, m), 3.50-3.67 (4H, m), 4.01 (2H, dd, J=24.50, 5.80 Hz), 7.53 (1H, t, J=5.90 Hz), 8.11 (1H, s), 8.54 (1H, s), 8.63 (1H, s), 8.77 (1H, s), 9.38 (1H, s), 9.44 (1H, s), 11.20 (1H, s); ESIMS found for $C_{20}H_{20}FN_7O$ m/z 394.2 (M+1).

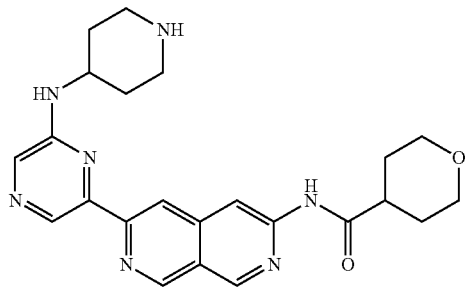

N-(6-(6-(Piperidin-4-ylamino)pyrazin-2-yl)-2,7-naphthyridin-3-yl) tetrahydro-2H-pyran-4-carboxamide 4504

Beige solid (19 mg, 0.04 mmol, 46.8% yield). $^1$H NMR (499 MHz, DMSO-$d_6$) δ ppm 1.36-1.47 (2H, m), 1.64-1.73 (2H, m), 1.73-1.79 (2H, m), 1.96-2.03 (2H, m), 2.71-2.79 (2H, m), 2.86 (1H, tt, J=11.08, 4.29 Hz), 3.02-3.09 (2H, m), 3.35-3.39 (2H, m), 3.92 (2H, dt, J=9.61, 2.06 Hz), 3.99-4.08 (1H, m), 7.24 (1H, d, J=7.14 Hz), 8.01 (1H, s), 8.51 (1H, s), 8.55 (1H, s), 8.71 (1H, s), 9.38 (1H, s), 9.44 (1H, s), 10.88 (1H, s); ESIMS found for $C_{23}H_{27}N_7O_2$ m/z 434.2 (M+1).

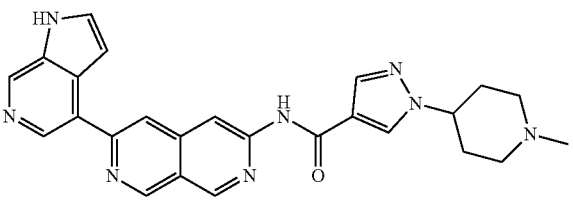

N-(6-(1H-Pyrrolo[2,3-c]pyridin-4-yl)-2,7-naphthyridin-3-yl)-1-(1-methylpiperidin-4-yl)-1H-pyrazole-4-carboxamide 4523

Yellow solid (1.2 mg, 0.003 mmol, 23.3% yield). $^1$H NMR (499 MHz, METHANOL-$d_4$) δ ppm 2.13-2.22 (4H, m), 2.25-2.34 (2H, m), 2.36 (3H, s), 3.03 (2H, br d, J=12.35 Hz), 4.23-4.35 (1H, m), 7.08 (1H, d, J=3.29 Hz), 7.73 (1H, d, J=3.02 Hz), 8.15 (1H, s), 8.30 (1H, s), 8.48 (1H, s), 8.69 (1H, br s), 8.71 (1H, s), 8.80 (1H, br s), 9.37 (1H, s), 9.50 (1H, s); ESIMS found for $C_{25}H_{24}N_8O$ m/z 453.2 (M+1)

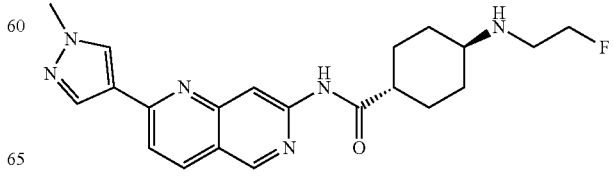

trans-4-((2-Fluoroethyl)amino)-N-(2-(1-methyl-1H-pyrazol-4-yl)-1,6-naphthyridin-7-yl) cyclohexane-1-carboxamide 4535

Off-white solid (25 mg, 0.06 mmol, 27.6% yield). $^1$H NMR (499 MHz, DMSO-$d_6$) δ ppm 0.97-1.10 (2H, m), 1.49 (2H, qd, J=12.81, 2.47 Hz), 1.87 (2H, br d, J=11.53 Hz), 1.92-2.01 (2H, m), 2.35-2.44 (1H, m), 2.52-2.57 (1H, m), 2.83 (2H, dt, J=26.90, 5.20 Hz), 3.93 (3H, s), 4.44 (2H, dt, J=47.90, 5.00 Hz), 7.80 (1H, d, J=8.51 Hz), 8.21 (1H, s), 8.38 (1H, d, J=8.51 Hz), 8.47 (1H, s), 8.55 (1H, s), 9.05 (1H, s), 10.57 (1H, s); ESIMS found for $C_{21}H_{25}FN_6O$ m/z 397.2 (M+1).

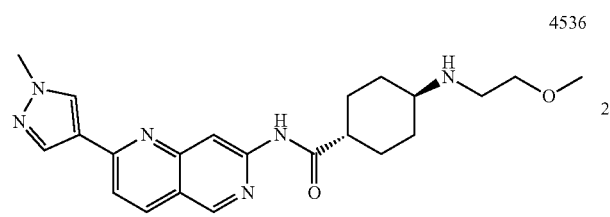

trans-4-((2-Methoxyethyl)amino)-N-(2-(1-methyl-1H-pyrazol-4-yl)-1,6-naphthyridin-7-yl) cyclohexane-1-carboxamide 4536

Off-white solid (14 mg, 0.03 mmol, 15.0% yield). $^1$H NMR (499 MHz, DMSO-$d_6$) δ ppm 0.96-1.08 (2H, m), 1.49 (3H, qd, J=12.85, 3.16 Hz), 1.86 (2H, br d, J=12.08 Hz), 1.94 (2H, br dd, J=12.76, 2.61 Hz), 2.32-2.40 (1H, m), 2.52-2.58 (1H, m), 2.69 (2H, t, J=5.76 Hz), 3.24 (3H, s), 3.37 (2H, t, J=5.76 Hz), 3.93 (3H, s), 7.80 (1H, d, J=8.51 Hz), 8.21 (1H, s), 8.38 (1H, d, J=8.78 Hz), 8.47 (1H, s), 8.55 (1H, s), 9.05 (1H, s), 10.57 (1H, s); ESIMS found for $C_{22}H_{28}N_6O_2$ m/z 409.2 (M+1).

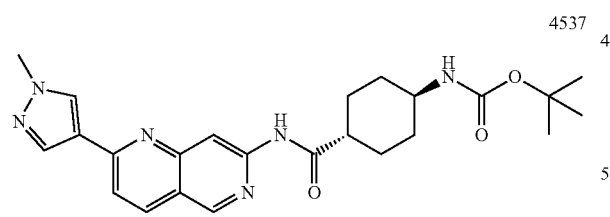

tert-Butyl (trans-4-((2-(1-methyl-1H-pyrazol-4-yl)-1,6-naphthyridin-7-yl) carbamoyl)cyclohexyl)carbamate 4537

Off-white solid (304 mg, 0.67 mmol, 60.8% yield). $^1$H NMR (499 MHz, DMSO-$d_6$) δ ppm 1.15-1.25 (2H, m), 1.39 (9H, s), 1.44-1.56 (2H, m), 1.86 (4H, brt, J=13.17 Hz), 2.43-2.48 (1H, m), 3.15-3.26 (1H, m), 3.93 (3H, s), 6.75 (1H, br d, J=7.68 Hz), 7.81 (1H, d, J=8.51 Hz), 8.21 (1H, s), 8.36-8.41 (1H, m), 8.46 (1H, s), 8.55 (1H, s), 9.05 (1H, s), 10.57 (1H, s); ESIMS found for $C_{24}H_{30}N_6O_3$ m/z 451.3 (M+1).

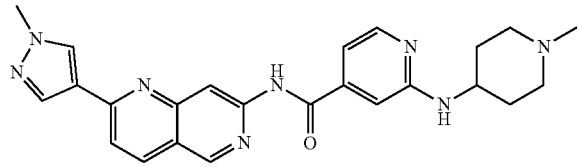

N-(2-(1-Methyl-1H-pyrazol-4-yl)-1,6-naphthyridin-7-yl)-2-((1-methylpiperidin-4-yl)amino)isonicotinamide 4538

Yellow wax (5.1 mg, 0.01 mmol, 3.7% yield). $^1$H NMR (499 MHz, DMSO-$d_6$) δ ppm 1.40-1.53 (2H, m), 1.89 (2H, br d, J=11.80 Hz), 2.00 (2H, br t, J=10.70 Hz), 2.17 (3H, s), 2.74 (2H, br d, J=11.80 Hz), 3.67-3.77 (1H, m), 3.94 (3H, s), 6.71 (1H, d, J=7.68 Hz), 6.99 (1H, s), 7.01 (1H, dd, J=5.35, 1.51 Hz), 7.87 (1H, d, J=8.78 Hz), 8.10 (1H, d, J=5.21 Hz), 8.24 (1H, s), 8.45 (1H, d, J=7.96 Hz), 8.59 (2H, d, J=3.57 Hz), 9.14 (1H, s), 10.96 (1H, s); ESIMS found for $C_{24}H_{26}N_8O$ m/z 443.2 (M+1).

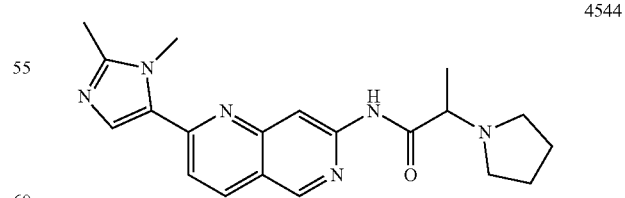

N-(2-(1-Methyl-1H-pyrazol-4-yl)-1,6-naphthyridin-7-yl)-2-(4-methylpiperazin-1-yl)thiazole-5-carboxamide 4539

Yellow solid (70 mg, 0.16 mmol, 45.5% yield). $^1$H NMR (499 MHz, DMSO-$d_6$) δ ppm 2.23 (3H, s), 2.40-2.46 (4H, m), 3.50-3.56 (4H, m), 3.94 (3H, s), 7.83 (1H, d, J=8.51 Hz), 8.22 (1H, s), 8.37 (1H, s), 8.41 (1H, d, J=7.96 Hz), 8.49 (1H, s), 8.57 (1H, s), 9.11 (1H, s), 10.91 (1H, s); ESIMS found for $C_{21}H_{22}N_8OS$ m/z 435.2 (M+1).

N-(2-(1,2-Dimethyl-1H-imidazol-5-yl)-1,6-naphthyridin-7-yl)-2-(pyrrolidin-1-yl)propanamide 4544

Off-white solid (47 mg, 0.13 mmol, 41.1% yield). $^1$H NMR (499 MHz, DMSO-$d_6$) δ ppm 1.30 (3H, d, J=6.86 Hz), 1.74 (4H, br s), 2.42 (3H, s), 2.57-2.69 (4H, m), 3.33-3.37 (1H, m), 4.10 (3H, s), 7.79 (1H, s), 7.88 (1H, d, J=8.78 Hz), 8.38 (1H, d, J=8.78 Hz), 8.49 (1H, s), 9.07 (1H, s), 10.16 (1H, s); ESIMS found for $C_{20}H_{24}N_6O$ m/z 365.2 (M+1).

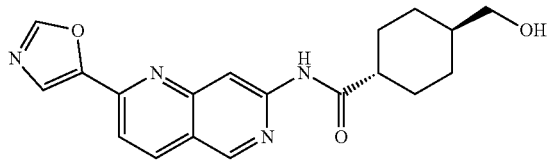

trans-4-(Hydroxymethyl)-N-(2-(oxazol-5-yl)-1,6-naphthyridin-7-yl) cyclohexane-1-carboxamide 4548

Beige solid (5 mg, 0.04 mmol, 10.2% yield). $^1$H NMR (499 MHz, DMSO-$d_6$) δ ppm 0.95 (2H, qd, J=12.81, 3.29 Hz), 1.37 (1H, dtt, J=15.04, 5.93, 5.93, 3.02, 3.02 Hz), 1.46 (2H, qd, J=12.76, 3.16 Hz), 1.81 (2H, br dd, J=13.31, 2.88 Hz), 1.86-1.93 (2H, m), 2.52-2.58 (1H, m), 3.24 (2H, t, J=5.76 Hz), 4.39 (1H, t, J=5.21 Hz), 7.94 (1H, d, J=8.51 Hz), 8.17 (1H, s), 8.55-8.59 (2H, m), 8.69 (1H, s), 9.19 (1H, s), 10.69 (1H, s); ESIMS found for $C_{19}H_{20}N_4O_3$ m/z 353.1 (M+1).

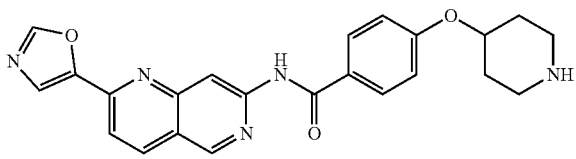

N-(2-(Oxazol-5-yl)-1,6-naphthyridin-7-yl)-4-(piperidin-4-yloxy)benzamide 4551

Beige solid (2 mg, 0.005 mmol, 16.5% yield). $^1$H NMR (499 MHz, DMSO-$d_6$) δ ppm 1.41-1.52 (2H, m), 1.91-1.99 (2H, m), 2.56-2.66 (2H, m), 2.95 (2H, dt, J=12.49, 4.05 Hz), 4.51-4.59 (1H, m), 7.06 (2H, d, J=8.78 Hz), 7.98 (1H, d, J=8.78 Hz), 8.07 (2H, d, J=8.78 Hz), 8.20 (1H, s), 8.62 (1H, d, J=8.51 Hz), 8.71 (2H, d, J=4.12 Hz), 9.27 (1H, s), 10.91 (1H, s); ESIMS found for $C_{23}H_{21}N_5O_3$ m/z 416.2 (M+1).

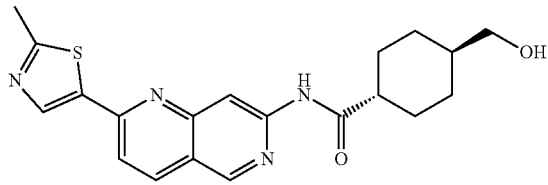

trans-4-(Hydroxymethyl)-N-(2-(2-methylthiazol-5-yl)-1,6-naphthyridin-7-yl) cyclohexane-1-carboxamide 4558

White solid (31 mg, 0.08 mmol, 45.8% yield). $^1$H NMR (499 MHz, DMSO-$d_6$) δ ppm 0.95 (2H, qd, J=12.76, 3.16 Hz), 1.36 (1H, tdd, J=11.94, 11.94, 6.17, 3.16 Hz), 1.45 (2H, qd, J=12.76, 3.16 Hz), 1.80 (2H, br dd, J=13.17, 2.74 Hz), 1.86-1.93 (2H, m), 2.51-2.56 (1H, m), 2.73 (3H, s), 3.24 (2H, t, J=5.63 Hz), 4.40 (1H, t, J=5.35 Hz), 8.10 (1H, d, J=8.51 Hz), 8.46-8.51 (2H, m), 8.60 (1H, s), 9.13 (1H, d, J=0.82 Hz), 10.66 (1H, s); ESIMS found for $C_{20}H_{22}N_4O_2S$ m/z 383.2 (M+1).

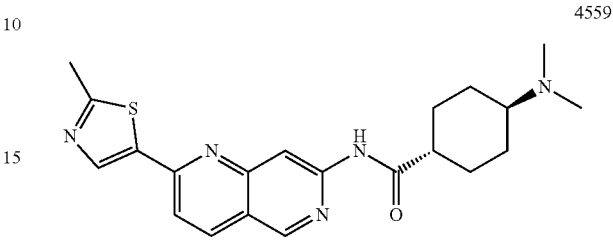

trans-4-(Dimethylamino)-N-(2-(2-methylthiazol-5-yl)-1,6-naphthyridin-7-yl) cyclohexane-1-carboxamide 4559

Beige solid (29 mg, 0.07 mmol, 53.3% yield). $^1$H NMR (499 MHz, DMSO-$d_6$) δ ppm 1.13-1.23 (2H, m), 1.48 (2H, qd, J=12.72, 3.02 Hz), 1.84-1.90 (2H, m), 1.93 (2H, br d, J=11.80 Hz), 2.11-2.17 (1H, m), 2.18 (6H, s), 2.45-2.49 (1H, m), 2.73 (3H, s), 8.10 (1H, d, J=8.78 Hz), 8.47 (1H, s), 8.48-8.52 (1H, m), 8.60 (1H, s), 9.13 (1H, s), 10.67 (1H, s); ESIMS found for $C_{21}H_{25}N_5OS$ m/z 396.2 (M+1).

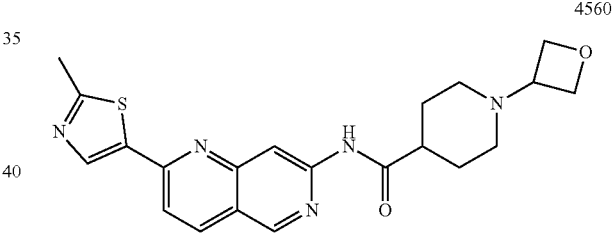

N-(2-(2-Methylthiazol-5-yl)-1,6-naphthyridin-7-yl)-1-(oxetan-3-yl) piperidine-4-carboxamide 4560

Beige solid (5 mg, 0.01 mmol, 9.2% yield). $^1$H NMR (499 MHz, METHANOL-$d_4$) δ ppm 1.88-2.04 (6H, m), 2.54-2.63 (1H, m), 2.78 (3H, s), 2.89 (2H, br d, J=10.98 Hz), 3.53 (1H, quin, J=6.45 Hz), 4.61-4.66 (2H, m), 4.67-4.74 (2H, m), 7.98 (1H, d, J=8.51 Hz), 8.39 (1H, d, J=8.51 Hz), 8.42 (1H, s), 8.56 (1H, s), 9.03 (1H, s); ESIMS found for $C_{21}H_{23}N_5O_2S$ m/z 410.1 (M+1).

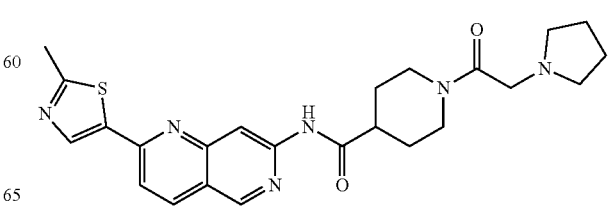

N-(2-(2-Methylthiazol-5-yl)-1,6-naphthyridin-7-yl)-1-(2-(pyrrolidin-1-yl) acetyl)piperidine-4-carboxamide 4561

White solid (22 mg, 0.05 mmol, 33.5% yield). $^1$H NMR (499 MHz, DMSO-d$_6$) δ ppm 1.41-1.54 (1H, m), 1.54-1.66 (1H, m), 1.67-1.72 (4H, m), 1.85 (2H, br d, J=10.43 Hz), 2.48 (4H, br s), 2.55-2.64 (1H, m), 2.73 (3H, s), 2.79-2.88 (1H, m), 2.98-3.06 (1H, m), 3.15-3.22 (1H, m), 3.34-3.40 (1H, m), 4.11 (1H, br d, J=13.72 Hz), 4.40 (1H, br d, J=12.62 Hz), 8.11 (1H, d, J=8.51 Hz), 8.47 (1H, s), 8.50 (1H, d, J=8.51 Hz), 8.60 (1H, s), 9.14 (1H, s), 10.79 (1H, s); ESIMS found for C$_{24}$H$_{28}$N$_6$O$_2$S m/z 465.2 (M+1).

4564

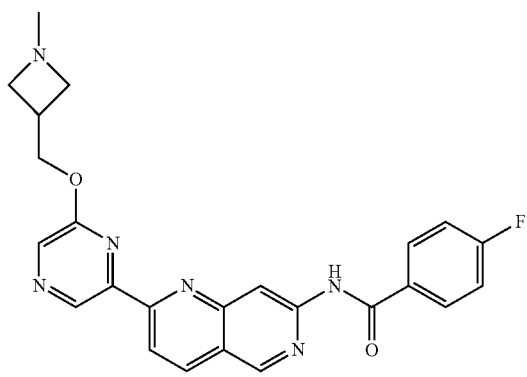

4-fluoro-N-(2-(6-((1-methylazetidin-3-yl)methoxy)pyrazin-2-yl)-1,6-naphthyridin-7-yl)benzamide 4564

Yellow solid (5 mg, 0.01 mmol, 40.4% yield). $^1$H NMR (499 MHz, DMSO-d$_6$) δ ppm 2.23 (3H, s), 2.81-2.92 (1H, m), 3.04 (2H, t, J=6.31 Hz), 3.27-3.31 (2H, m), 4.65 (2H, d, J=7.14 Hz), 7.38 (2H, t, J=8.78 Hz), 8.19 (2H, dd, J=8.78, 5.49 Hz), 8.49 (1H, s), 8.51 (1H, d, J=8.51 Hz), 8.73 (1H, d, J=8.51 Hz), 8.82 (1H, s), 9.35 (1H, s), 9.38 (1H, s), 11.21 (1H, s); ESIMS found for C$_{24}$H$_{21}$FN$_6$O$_2$ m/z 445.2 (M+1).

4565

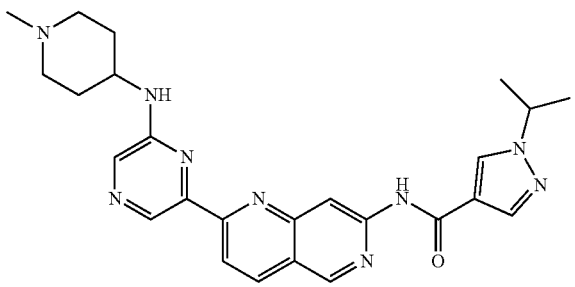

1-Isopropyl-N-(2-(6-((1-methylpiperidin-4-yl)amino)pyrazin-2-yl)-1,6-naphthyridin-7-yl)-1H-pyrazole-4-carboxamide 4565

Yellow solid (2.8 mg, 0.006 mmol, 3.1% yield). $^1$H NMR (499 MHz, DMSO-d$_6$) δ ppm 1.47 (6H, d, J=6.86 Hz), 1.49-1.59 (2H, m), 1.93-2.04 (2H, m), 2.07-2.14 (2H, m), 2.21 (3H, s), 2.77 (2H, br d, J=12.08 Hz), 3.81-3.92 (1H, m), 4.56 (2H, quin, J=6.66 Hz), 7.29 (1H, d, J=7.14 Hz), 8.07 (1H, s), 8.21 (1H, s), 8.38 (1H, d, J=8.51 Hz), 8.63 (1H, d, J=8.51 Hz), 8.65 (1H, s), 8.73 (1H, s), 8.81 (1H, s), 9.29 (1H, s), 10.77 (1H, s); ESIMS found for C$_{25}$H$_{29}$N$_9$O m/z 472.3 (M+1).

4569

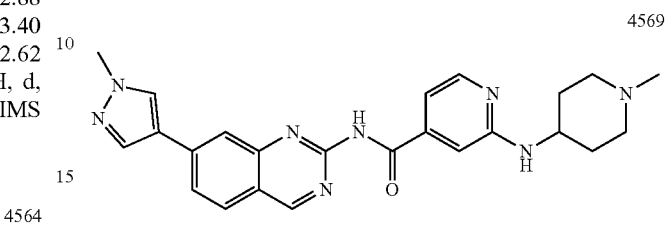

N-(7-(1-Methyl-1H-pyrazol-4-yl)quinazolin-2-yl)-2-((1-methylpiperidin-4-yl)amino)isonicotinamide 4569

Yellow solid (25.2 mg, 0.06 mmol, 34.6% yield). $^1$H NMR (499 MHz, DMSO-d$_6$) δ ppm 1.38-1.52 (2H, m), 1.84-1.93 (2H, m), 1.99 (2H, br t, J=10.70 Hz), 2.16 (3H, s), 2.73 (2H, br d, J=11.53 Hz), 3.65-3.75 (1H, m), 3.91 (3H, s), 6.70 (1H, d, J=7.68 Hz), 6.89-6.98 (2H, m), 7.89 (1H, dd, J=8.51, 1.65 Hz), 7.99 (1H, d, J=0.82 Hz), 8.06-8.10 (2H, m), 8.17 (1H, s), 8.47 (1H, s), 9.43 (1H, s), 11.06 (1H, br s); ESIMS found for C$_{24}$H$_{26}$N$_8$O m/z 443.2 (M+1).

4570

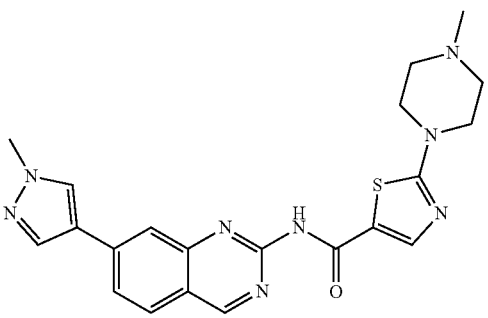

N-(7-(1-Methyl-1H-pyrazol-4-yl)quinazolin-2-yl)-2-(4-methylpiperazin-1-yl) thiazole-5-carboxamide 4570

Yellow solid (7.8 mg, 0.02 mmol, 11.7% yield). $^1$H NMR (499 MHz, DMSO-d$_6$) δ ppm 2.23 (3H, s), 2.40-2.45 (4H, m), 3.49-3.56 (4H, m), 3.91 (3H, s), 7.85 (1H, dd, J=8.51, 1.65 Hz), 7.93 (1H, d, J=0.82 Hz), 8.04 (1H, d, J=8.51 Hz), 8.15 (1H, s), 8.25 (1H, s), 8.45 (1H, s), 9.40 (1H, s), 10.97 (1H, s); ESIMS found for C$_{21}$H$_{22}$N$_8$OS m/z 435.2 (M+1).

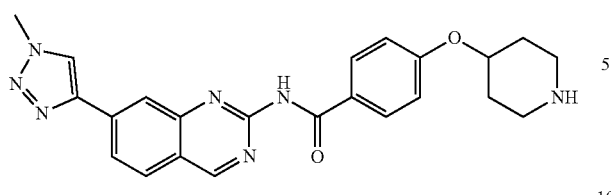

N-(7-(1-Methyl-1H-1,2,3-triazol-4-yl)quinazolin-2-yl)-4-(piperidin-4-yloxy) benzamide 4573

Beige solid (5 mg, 0.01 mmol, 12.3% yield). $^1$H NMR (499 MHz, DMSO-d$_6$) δ ppm 1.45-1.54 (2H, m), 1.93-2.00 (2H, m), 2.63 (2H, br t, J=9.88 Hz), 2.94-3.04 (2H, m), 4.15 (3H, s), 4.51-4.62 (1H, m), 7.06 (2H, br d, J=8.23 Hz), 8.00 (2H, br d, J=8.51 Hz), 8.11-8.21 (2H, m), 8.25 (1H, s), 8.87 (1H, s), 9.52 (1H, s), 11.00 (1H, br s); ESIMS found for C$_{23}$H$_{23}$N$_7$O$_2$ m/z 430.2 (M+1).

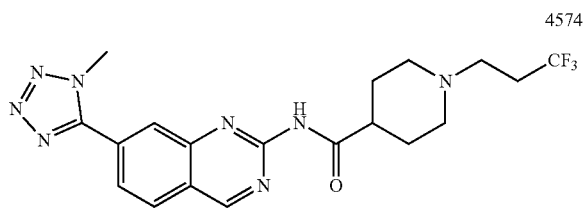 [SMILES: Cn1nnnc1-c1ccc2cnc(NC(=O)C3CCN(CCC(F)(F)F)CC3)nc2c1]

N-(7-(1-Methyl-1H-tetrazol-5-yl)quinazolin-2-yl)-1-(3,3,3-trifluoropropyl) piperidine-4-carboxamide 4574

Off-white solid (5.5 mg, 0.01 mmol, 20.3% yield). $^1$H NMR (499 MHz, DMSO-d$_6$) δ ppm 1.63 (2H, qd, J=12.21, 3.43 Hz), 1.83 (2H, br d, J=11.80 Hz), 1.94-2.04 (2H, m), 2.40-2.55 (4H, m), 2.66-2.75 (1H, m), 2.93 (2H, br d, J=11.53 Hz), 4.27 (3H, s), 7.99 (1H, dd, J=8.23, 1.65 Hz), 8.22-8.26 (1H, m), 8.29 (1H, d, J=8.23 Hz), 9.64 (1H, d, J=0.82 Hz), 10.87 (1H, s); ESIMS found for C$_{19}$H$_{21}$F$_3$N$_8$O m/z 435.2 (M+1).

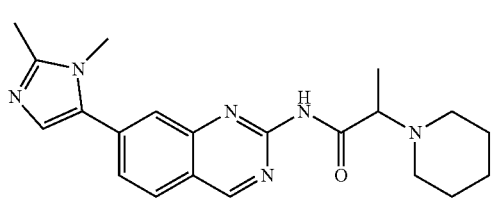

N-(7-(1,2-Dimethyl-1H-imidazol-5-yl)quinazolin-2-yl)-2-(piperidin-1-yl) propanamide 4576

Beige gum (16 mg, 0.04 mmol, 10.1% yield). $^1$H NMR (499 MHz, DMSO-d$_6$) δ ppm 1.18 (3H, d, J=6.86 Hz), 1.37-1.45 (2H, m), 1.55 (4H, br d, J=2.74 Hz), 2.40 (3H, s), 2.51-2.57 (4H, m), 3.49 (1H, q, J=6.68 Hz), 3.69 (3H, s), 7.22 (1H, s), 7.71 (1H, dd, J=8.37, 1.51 Hz), 7.78 (1H, d, J=8.51 Hz), 9.47 (1H, s), 10.39 (1H, s); ESIMS found for C$_{21}$H$_{26}$N$_6$O m/z 379.1 (M+1).

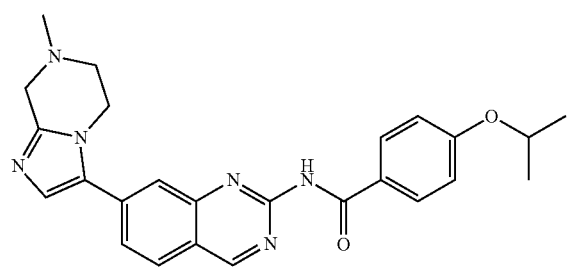

4-Isopropoxy-N-(7-(7-methyl-5,6,7,8-tetrahydroimidazo[1,2-a]pyrazin-3-yl) quinazolin-2-yl)benzamide 4577

Yellow solid (4.4 mg, 0.01 mmol, 47.3% yield). $^1$H NMR (499 MHz, DMSO-d$_6$) δ ppm 1.31 (6H, d, J=6.04 Hz), 2.42 (3H, s), 2.82 (2H, t, J=5.35 Hz), 3.65 (2H, s), 4.24 (2H, t, J=5.35 Hz), 4.75 (1H, spt, J=6.04 Hz), 6.99-7.05 (2H, m), 7.43 (1H, s), 7.82 (1H, dd, J=8.51, 1.65 Hz), 7.86 (1H, s), 7.98-8.04 (2H, m), 8.12 (1H, d, J=8.51 Hz), 9.51 (1H, s), 10.99 (1H, br s); ESIMS found for C$_{25}$H$_{26}$N$_6$O$_2$ m/z 443.2 (M+1).

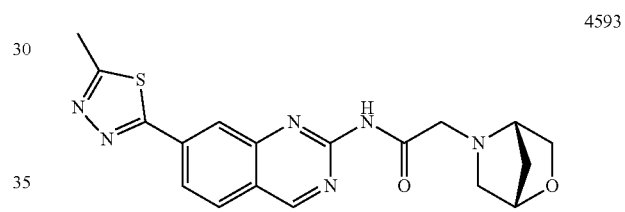

2-((1S,4S)-2-Oxa-5-azabicyclo[2.2.1]heptan-5-yl)-N-(7-(5-methyl-1,3,4-thiadiazol-2-yl)quinazolin-2-yl)acetamide 4593

Beige solid (3 mg, 0.008 mmol, 5.8% yield). $^1$H NMR (499 MHz, DMSO-d$_6$) δ ppm 1.65 (1H, br d, J=9.61 Hz), 1.84 (1H, dd, J=9.61, 1.65 Hz), 2.59 (1H, d, J=10.15 Hz), 2.84 (3H, s), 2.95 (1H, dd, J=10.02, 1.51 Hz), 3.55 (2H, d, J=6.04 Hz), 3.58 (1H, dd, J=7.55, 1.51 Hz), 3.63 (1H, s), 3.87 (1H, d, J=7.68 Hz), 4.39 (1H, s), 8.16-8.21 (1H, m), 8.22-8.25 (1H, m), 8.26 (1H, d, J=0.82 Hz), 9.59 (1H, s), 10.42 (1H, s); ESIMS found for C$_{18}$H$_{18}$N$_6$O$_2$S m/z 383.1 (M+1).

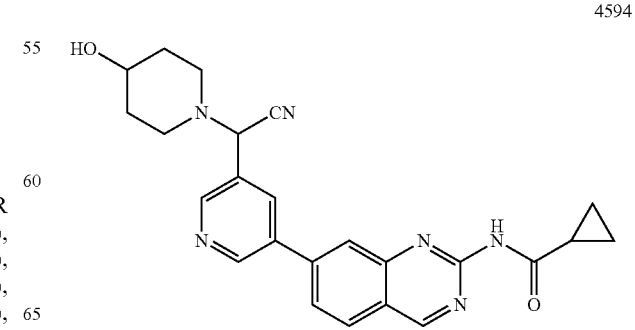

N-(7-(5-(Cyano(4-hydroxypiperidin-1-yl)methyl)pyridin-3-yl)quinazolin-2-yl)cyclopropanecarboxamide 4594

White solid (4 mg, 0.009 mmol, 5.2% yield). $^1$H NMR (499 MHz, DMSO-d$_6$) δ ppm 0.83-0.92 (4H, m), 1.35-1.43 (1H, m), 1.48-1.58 (1H, m), 1.73-1.80 (1H, m), 2.07-2.16 (1H, m), 2.25-2.33 (1H, m), 2.33-2.40 (1H, m), 2.55-2.62 (1H, m), 2.87-2.95 (1H, m), 3.51-3.59 (1H, m), 4.64 (1H, d, J=3.84 Hz), 5.63 (1H, s), 8.27 (1H, d, J=8.51 Hz), 8.59-8.66 (2H, m), 8.69 (1H, t, J=1.78 Hz), 8.77 (1H, d, J=1.92 Hz), 9.27 (1H, s), 9.46 (1H, d, J=2.20 Hz), 11.13 (1H, s); ESIMS found for C$_{24}$H$_{24}$N$_6$O$_2$ m/z 429.2 (M+1).

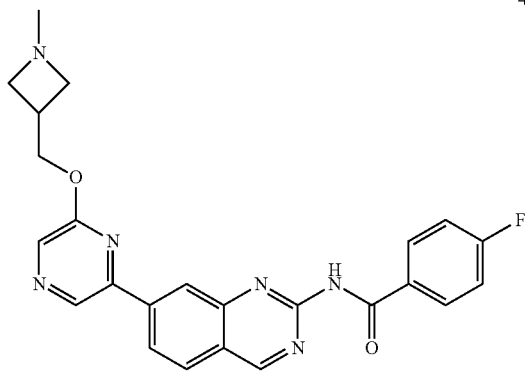

4-Fluoro-N-(7-(6-((1-methylazetidin-3-yl)methoxy)pyrazin-2-yl)quinazolin-2-yl)benzamide 4595

White solid (5 mg, 0.01 mmol, 60.5% yield). $^1$H NMR (499 MHz, DMSO-d$_6$) δ ppm 2.22 (3H, s), 2.79-2.91 (1H, m), 3.03 (2H, br t, J=6.17 Hz), 3.27-3.30 (2H, m), 4.63 (2H, d, J=7.14 Hz), 7.37 (2H, t, J=8.78 Hz), 8.11 (2H, dd, J=8.51, 5.49 Hz), 8.27 (1H, d, J=8.78 Hz), 8.40 (1H, br dd, J=8.51, 1.65 Hz), 8.39 (1H, s), 8.58 (1H, d, J=0.82 Hz), 9.09 (1H, s), 9.64 (1H, s), 11.30 (1H, s); ESIMS found for C$_{24}$H$_{21}$FN$_6$O$_2$ m/z 445.2 (M+1).

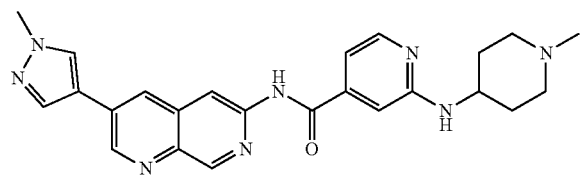

N-(6-(1-Methyl-1H-pyrazol-4-yl)-2,7-naphthyridin-3-yl)-2-((1-methylpiperidin-4-yl)amino)isonicotinamide 4600

Off-white solid (18.5 mg, 0.04 mmol, 31.4% yield). $^1$H NMR (499 MHz, DMSO-d$_6$) δ ppm 1.42-1.53 (2H, m), 1.86-1.92 (2H, m), 1.99 (2H, br t, J=11.39 Hz), 2.17 (3H, s), 2.73 (2H, br d, J=11.25 Hz), 3.67-3.76 (1H, m), 3.93 (3H, s), 6.71 (1H, d, J=7.68 Hz), 6.98 (1H, s), 7.00 (1H, dd, J=5.35, 1.51 Hz), 8.10 (1H, d, J=5.21 Hz), 8.21 (1H, s), 8.51 (1H, s), 8.57 (1H, d, J=1.92 Hz), 8.61 (1H, d, J=0.82 Hz), 9.19 (1H, s), 9.23 (1H, d, J=2.20 Hz), 10.98 (1H, s); ESIMS found for C$_{24}$H$_{26}$N$_8$O m/z 443.2 (M+1).

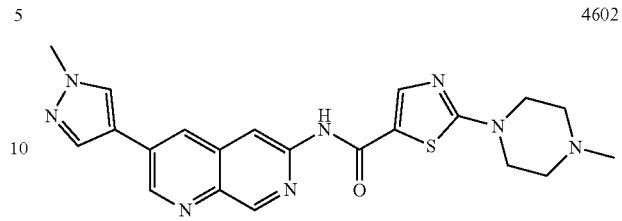

N-(6-(1-Methyl-1H-pyrazol-4-yl)-2,7-naphthyridin-3-yl)-2-(4-methylpiperazin-1-yl)thiazole-5-carboxamide 4602

Off-white solid (33 mg, 0.08 mmol, 34.9% yield). $^1$H NMR (499 MHz, DMSO-d$_6$) δ ppm 2.23 (3H, s), 2.43 (4H, br t, J=4.94 Hz), 3.49-3.55 (4H, m), 3.93 (3H, s), 8.20 (1H, s), 8.37 (1H, s), 8.49 (3H, s), 9.16 (1H, s), 9.19 (1H, d, J=1.92 Hz), 10.93 (1H, s); ESIMS found for C$_{21}$H$_{22}$N$_8$OS m/z 435.2 (M+1).

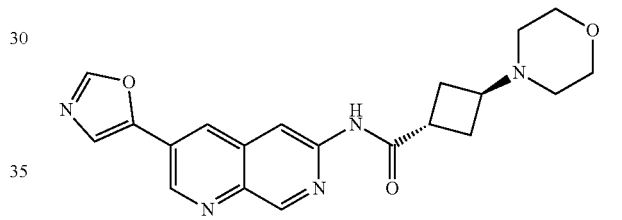

trans-3-Morpholino-N-(6-(oxazol-5-yl)-2,7-naphthyridin-3-yl)cyclobutane-1-carboxamide 4609

White solid (11 mg, 0.03 mmol, 13.3% yield). $^1$H NMR (500 MHz, DMSO-d$_6$) δ ppm 2.10-2.17 (2H, m), 2.22-2.31 (6H, m), 2.87-2.94 (1H, m), 3.26-3.29 (1H, m), 3.59 (4H, br t, J=4.39 Hz), 8.10 (1H, s), 8.62 (1H, d, J=1.92 Hz), 8.63 (1H, s), 8.67 (1H, s), 9.18-9.22 (1H, m), 9.29 (1H, d, J=2.20 Hz), 10.69 (1H, s); ESIMS found for C$_{20}$H$_{21}$N$_5$O$_3$ m/z 380.2 (M+1).

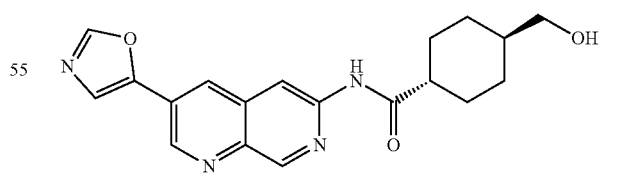

trans-4-(Hydroxymethyl)-N-(6-(oxazol-5-yl)-2,7-naphthyridin-3-yl) cyclohexane-1-carboxamide 4610

Pale yellow solid (7 mg, 0.02 mmol, 32.9% yield). $^1$H NMR (500 MHz, DMSO-d$_6$) δ ppm 0.95 (2H, qd, J=12.76, 2.88 Hz), 1.32-1.41 (1H, m), 1.45 (2H, qd, J=12.76, 3.43 Hz), 1.81 (2H, br dd, J=13.17, 3.02 Hz), 1.89 (2H, br dd, J=12.49, 2.33 Hz), 2.52-2.57 (1H, m), 3.24 (2H, t, J=5.76 Hz), 4.40 (1H, t, J=5.35 Hz), 8.10 (1H, s), 8.60 (1H, s), 8.61 (1H, d, J=1.92 Hz), 8.66-8.69 (1H, m), 9.20 (1H, t, J=0.82 Hz), 9.28 (1H, d, J=1.92 Hz), 10.67 (1H, s); ESIMS found for $C_{19}H_{20}N_4O_3$ m/z 353.1 (M+1).

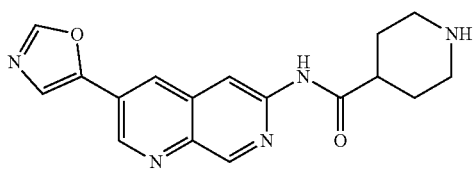

4611

N-(6-(Oxazol-5-yl)-2,7-naphthyridin-3-yl)piperidine-4-carboxamide 4611

Beige solid (57.0 mg, 0.18 mmol, 68.3% yield). $^1$H NMR (499 MHz, DMSO-d) δ ppm 1.54 (2H, qd, J=12.21, 3.98 Hz), 1.68-1.76 (2H, m), 2.44-2.49 (2H, m), 2.63-2.71 (1H, m), 2.95-3.02 (2H, m), 8.10 (1H, s), 8.60 (1H, s), 8.62 (1H, d, J=1.92 Hz), 8.66 (1H, s), 9.20 (1H, s), 9.28 (1H, d, J=2.20 Hz), 10.67 (1H, s); ESIMS found for $C_{17}H_{17}N_5O_2$ m/z 324.1

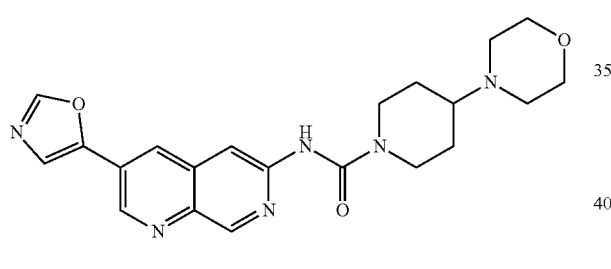

4612

4-Morpholino-N-(6-(oxazol-5-yl)-2,7-naphthyridin-3-yl)piperidine-1-carboxamide 4612

Beige solid (20 mg, 0.05 mmol, 27.3% yield). $^1$H NMR (499 MHz, DMSO-d$_6$) δ ppm 1.34 (2H, qd, J=11.94, 3.70 Hz), 1.80 (2H, br d, J=10.70 Hz), 2.37 (1H, tt, J=10.98, 3.57 Hz), 2.44-2.49 (4H, m), 2.84 (2H, br t, J=11.80 Hz), 3.53-3.61 (4H, m), 4.23 (2H, br d, J=13.17 Hz), 8.08 (1H, s), 8.28 (1H, s), 8.55 (1H, d, J=1.92 Hz), 8.65 (1H, s), 9.15 (1H, s), 9.22 (1H, d, J=2.20 Hz), 9.43 (1H, s); ESIMS found for $C_{21}H_{24}N_6O_3$ m/z 409.2 (M+1).

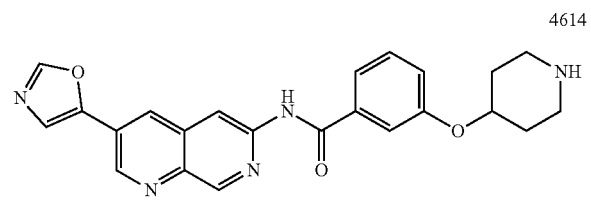 [SMILES: O=C(Nc1cc2cc(-c3cnco3)cnc2cn1)c1cccc(OC2CCNCC2)c1]

4614

N-(6-(Oxazol-5-yl)-2,7-naphthyridin-3-yl)-3-(piperidin-4-yloxy)benzamide 4614

White solid (30 mg, 0.07 mmol, 79.2% yield). $^1$H NMR (499 MHz, DMSO-d$_6$) δ ppm 1.43-1.56 (2H, m), 1.92-2.01 (2H, m), 2.55-2.66 (2H, m), 2.97 (2H, dt, J=12.62, 4.12 Hz), 4.52-4.60 (1H, m), 7.18 (1H, dd, J=8.10, 1.78 Hz), 7.43 (1H, t, J=8.10 Hz), 7.60-7.67 (2H, m), 8.12 (1H, s), 8.68 (1H, s), 8.71 (1H, d, J=2.20 Hz), 8.76 (1H, s), 9.30 (1H, s), 9.34 (1H, d, J=2.20 Hz), 11.08 (1H, s); ESIMS found for $C_{23}H_{21}N_5O_3$ m/z 416.15 (M+1).

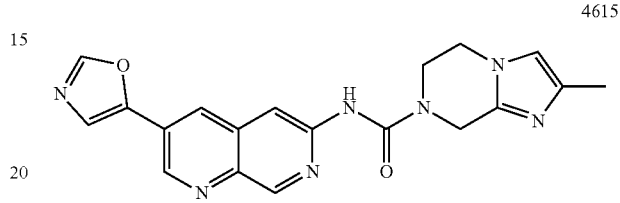

4615

2-Methyl-N-(6-(oxazol-5-yl)-2,7-naphthyridin-3-yl)-5,6-dihydroimidazo[1,2-a]pyrazine-7(8H)-carboxamide 4615

Beige solid (15 mg, 0.04 mmol, 22.3% yield). $^1$H NMR (499 MHz, DMSO-d$_6$) δ ppm 2.06 (3H, d, J=0.82 Hz), 3.92-3.97 (2H, m), 3.97-4.03 (2H, m), 4.68 (2H, s), 6.79 (1H, d, J=0.82 Hz), 8.09 (1H, s), 8.31 (1H, s), 8.57 (1H, d, J=1.92 Hz), 8.66 (1H, s), 9.19 (1H, s), 9.25 (1H, d, J=2.20 Hz), 9.82 (1H, s); ESIMS found for $C_{19}H_{17}N_7O_2$ m/z 376.2 (M+1).

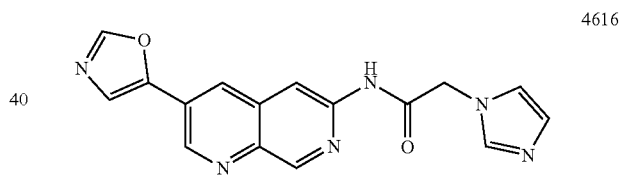

4616

2-(1H-Imidazol-1-yl)-N-(6-(oxazol-5-yl)-2,7-naphthyridin-3-yl)acetamide 4616

White solid (5.3 mg, 0.02 mmol, 8.8% yield). $^1$H NMR (499 MHz, DMSO-d$_6$) δ ppm 5.05 (2H, s), 6.91 (1H, s), 7.16-7.24 (1H, m), 7.67 (1H, s), 8.10 (1H, s), 8.54 (1H, s), 8.63 (1H, d, J=1.92 Hz), 8.66 (1H, s), 9.25 (1H, s), 9.31 (1H, d, J=2.20 Hz), 11.15 (1H, s); ESIMS found for $C_{16}H_{12}N_6O_2$ m/z 321.1 (M+1).

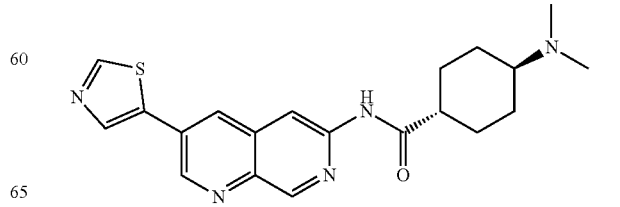

4618 trans-4-(Dimethylamino)-N-(6-(thiazol-5-yl)-2,7-naphthyridin-3-yl) cyclohexane-1-carboxamide 4618

Beige solid (21.6 mg, 0.06 mmol, 41.1% yield). $^1$H NMR (500 MHz, DMSO-d) δ ppm 1.14-1.25 (2H, m), 1.48 (2H, qd, J=12.67, 2.61 Hz), 1.85-1.90 (2H, m), 1.93 (2H, br d, J=12.35 Hz), 2.13-2.17 (1H, m), 2.18 (6H, s), 2.46-2.54 (1H, m), 8.58 (1H, s), 8.66 (1H, d, J=2.20 Hz), 8.69 (1H, s), 9.19-9.22 (1H, m), 9.27 (1H, s), 9.27 (1H, d, J=2.20 Hz), 10.67 (1H, s); ESIMS found for $C_{20}H_{23}N_5OS$ m/z 382.15 (M+1).

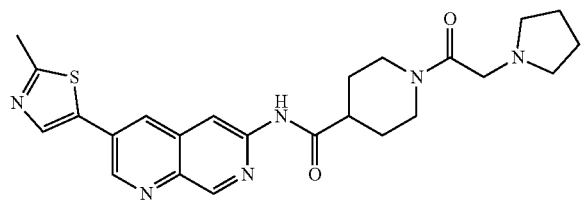

N-(6-(2-Methylthiazol-5-yl)-2,7-naphthyridin-3-yl)-1-(2-(pyrrolidin-1-yl) acetyl)piperidine-4-carboxamide 4623

Beige gum (15 mg, 0.03 mmol, 24.0% yield). $^1$H NMR (499 MHz, DMSO-d$_6$) δ ppm 1.47 (1H, qd, J=12.21, 3.70 Hz), 1.57-1.67 (1H, m), 1.69 (4H, br s), 1.82-1.89 (2H, m), 2.47 (4H, br s), 2.58-2.66 (1H, m), 2.75 (3H, s), 2.80-2.88 (1H, m), 2.98-3.07 (1H, m), 3.15-3.21 (1H, m), 3.37 (1H, d, J=14.27 Hz), 4.11 (1H, br d, J=13.17 Hz), 4.40 (1H, br d, J=13.45 Hz), 8.42 (1H, s), 8.54 (1H, d, J=2.20 Hz), 8.57 (1H, s), 9.17-9.20 (1H, m), 9.23 (1H, d, J=2.20 Hz), 10.79 (1H, s); ESIMS found for $C_{24}H_{28}N_6O_2S$ m/z 465.2 (M+1).

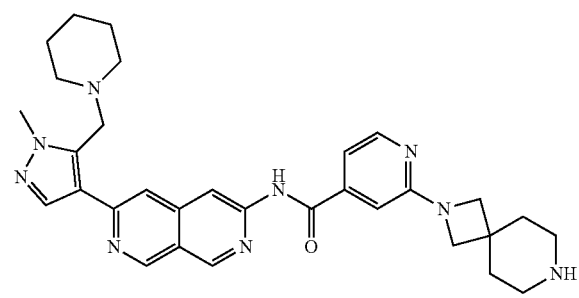

N-(3-(1-Methyl-5-(piperidin-1-ylmethyl)-1H-pyrazol-4-yl)-1,7-naphthyridin-6-yl)-2-(2,7-diazaspiro[3.5]nonan-2-yl)isonicotinamide 4634

White solid (3.2 mg, 0.006 mmol, 4.0% yield). $^1$H NMR (499 MHz, DMSO-d$_6$) δ ppm 1.33-1.41 (2H, m), 1.43-1.51 (4H, m), 1.68-1.75 (4H, m), 2.41 (4H, br s), 2.73 (4H, br s), 3.75 (4H, s), 3.92 (3H, s), 4.02 (2H, s), 7.02 (1H, s), 7.12 (1H, dd, J=5.21, 1.37 Hz), 8.05 (1H, s), 8.17 (1H, s), 8.20 (1H, d, J=5.49 Hz), 8.58 (1H, s), 9.34 (1H, s), 9.42 (1H, s), 11.20 (1H, br s); ESIMS found for $C_{31}H_{37}N_9O$ m/z 552.35 (M+1).

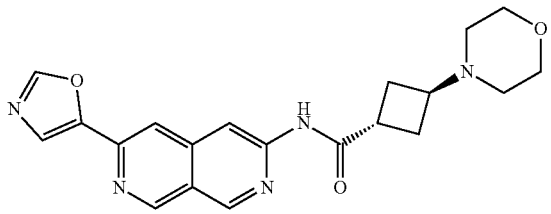

trans-3-Morpholino-N-(3-(oxazol-5-yl)-1,7-naphthyridin-6-yl)cyclobutane-1-carboxamide 4640

White solid (14 mg, 0.04 mmol, 36.6% yield). $^1$H NMR (499 MHz, DMSO-d$_6$) δ ppm 2.09-2.17 (2H, m), 2.22-2.31 (6H, m), 2.90 (1H, quin, J=7.07 Hz), 3.26-3.31 (1H, m), 3.59 (4H, t, J=4.39 Hz), 7.89 (1H, s), 8.11 (1H, s), 8.58 (1H, s), 8.63 (1H, s), 9.32-9.35 (1H, m), 9.40-9.44 (1H, m), 10.79 (1H, s); ESIMS found for $C_{20}H_{21}N_5O_3$ m/z 380.2 (M+1).

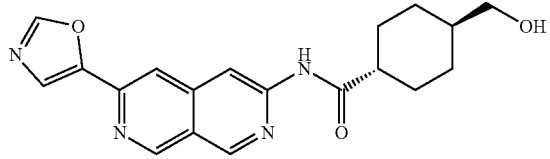

trans-4-(Hydroxymethyl)-N-(3-(oxazol-5-yl)-1,7-naphthyridin-6-yl) cyclohexane-1-carboxamide 4641

White solid (6.0 mg, 0.02 mmol, 6.7% yield). $^1$H NMR (499 MHz, DMSO-d$_6$) δ ppm 0.91-1.00 (2H, m), 1.35-1.39 (1H, m), 1.40-1.49 (2H, m), 1.80 (2H, br dd, J=13.45, 2.47 Hz), 1.89 (2H, br d, J=10.43 Hz), 2.52-2.58 (1H, m), 3.24 (2H, t, J=5.76 Hz), 4.40 (1H, t, J=5.35 Hz), 7.89 (1H, s), 8.10 (1H, s), 8.54 (1H, s), 8.62 (1H, s), 9.34 (1H, s), 9.41 (1H, s), 10.78 (1H, s); ESIMS found for $C_{19}H_{20}N_4O_3$ m/z 353.2 (M+1).

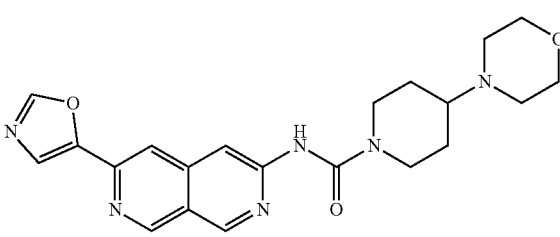

4-Morpholino-N-(3-(oxazol-5-yl)-1,7-naphthyridin-6-yl)piperidine-1-carboxamide 4643

Off-white solid (35 mg, 0.09 mmol, 36.4% yield). $^1$H NMR (499 MHz, DMSO-d$_6$) δ ppm 1.28-1.40 (2H, m), 1.80 (2H, br d, J=10.70 Hz), 2.37 (1H, tt, J=10.91, 3.50 Hz), 2.43-2.49 (4H, m), 2.85 (2H, brt, J=11.80 Hz), 3.53-3.60 (4H, m), 4.22 (2H, br d, J=13.45 Hz), 7.86 (1H, s), 8.02 (1H, s), 8.20 (1H, s), 8.60 (1H, s), 9.28 (1H, s), 9.36 (1H, s), 9.58 (1H, s); ESIMS found for $C_{21}H_{24}N_6O_3$ m/z 409.2 (M+1).

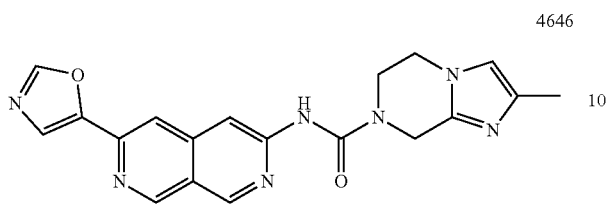

2-Methyl-N-(3-(oxazol-5-yl)-1,7-naphthyridin-6-yl)-5,6-dihydroimidazo[1,2-a]pyrazine-7(8H)-carboxamide 4646

Beige solid (30 mg, 0.08 mmol, 33.9% yield). $^1$H NMR (499 MHz, DMSO-$d_6$) δ ppm 2.06 (3H, s), 3.91-3.97 (2H, m), 3.97-4.03 (1H, m), 4.68 (2H, s), 6.79 (1H, s), 7.87 (1H, s), 8.05 (1H, s), 8.24 (1H, s), 8.61 (1H, s), 9.32 (1H, s), 9.38 (1H, s), 9.96 (1H, s); ESIMS found for $C_{19}H_{17}N_7O_2$ m/z 376.2 (M+1).

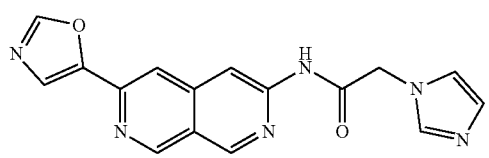

2-(1H-Imidazol-1-yl)-N-(3-(oxazol-5-yl)-1,7-naphthyridin-6-yl)acetamide 4647

Beige solid (10 mg, 0.03 mmol, 34.9% yield). $^1$H NMR (499 MHz, DMSO-$d_6$) δ ppm 5.06-5.11 (2H, m), 7.00 (1H, s), 7.26 (1H, s), 7.82 (1H, s), 7.89 (1H, s), 8.12 (1H, s), 8.48 (1H, s), 8.62 (1H, s), 9.39 (1H, s), 9.44 (1H, s), 11.28 (1H, s); ESIMS found for $C_{16}H_{12}N_6O_2$ m/z 321.1 (M+1).

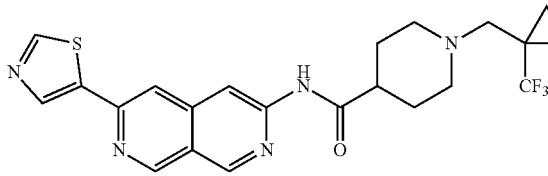

N-(3-(Thiazol-5-yl)-1,7-naphthyridin-6-yl)-1-((1-(trifluoromethyl) cyclopropyl)methyl)piperidine-4-carboxamide 4650

Off-white solid (15 mg, 0.03 mmol, 40.7% yield). $^1$H NMR (499 MHz, DMSO-$d_6$) δ ppm 0.73 (2H, s), 0.92-0.99 (2H, m), 1.62-1.74 (2H, m), 1.79 (2H, br d, J=10.15 Hz), 1.90-1.99 (2H, m), 2.57 (1H, tt, J=11.60, 3.77 Hz), 2.97 (2H, br d, J=11.53 Hz), 8.44 (1H, s), 8.51 (1H, s), 8.73 (1H, s), 9.20 (1H, s), 9.32 (1H, s), 9.35-9.39 (1H, m), 10.83 (1H, s); ESIMS found for $C_{22}H_{22}F_3N_5OS$ m/z 462.2 (M+1).

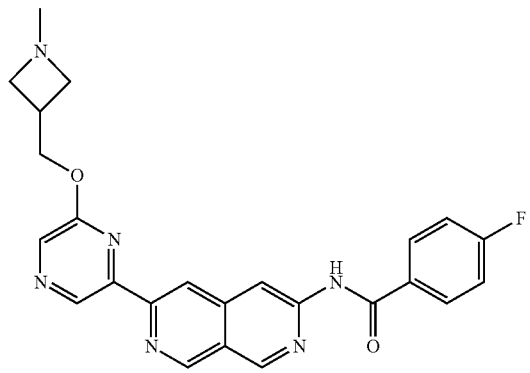

4-Fluoro-N-(3-(6-((1-methylazetidin-3-yl)methoxy)pyrazin-2-yl)-1,7-naphthyridin-6-yl)benzamide 4657

White solid (7.5 mg, 0.02 mmol, 40.4% yield). $^1$H NMR (499 MHz, DMSO-$d_6$) δ ppm 2.24 (3H, s), 2.80-2.94 (1H, m), 3.07 (2H, t, J=6.45 Hz), 3.33-3.36 (3H, m), 4.68 (2H, d, J=7.14 Hz), 7.38 (2H, t, J=8.92 Hz), 8.18 (2H, dd, J=8.78, 5.49 Hz), 8.40 (1H, s), 8.79 (2H, d, J=5.76 Hz), 9.22 (1H, s), 9.49 (1H, s), 9.55 (1H, s), 11.27 (1H, br s); ESIMS found for $C_{24}H_{21}FN_6O_2$ m/z 445.2 (M+1).

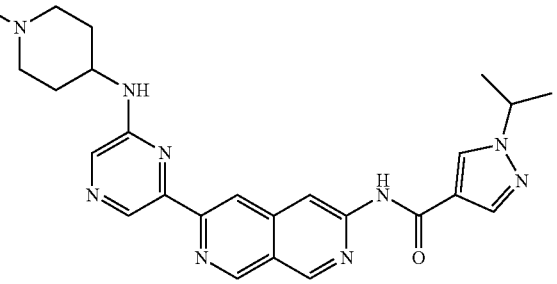

1-Isopropyl-N-(3-(6-((1-methylpiperidin-4-yl)amino)pyrazin-2-yl)-1,7-naphthyridin-6-yl)-1H-pyrazole-4-carboxamide 4658

Yellow solid (2.2 mg, 0.005 mmol, 5.1% yield). $^1$H NMR (499 MHz, DMSO-$d_6$) δ ppm 1.46 (6H, d, J=6.59 Hz), 1.50-1.60 (2H, m), 2.02 (2H, br dd, J=8.92, 3.43 Hz), 2.12-2.19 (2H, m), 2.23 (3H, s), 2.78 (2H, br d, J=10.98 Hz), 3.86-3.97 (1H, m), 4.52-4.61 (1H, m), 7.22 (1H, d, J=7.41 Hz), 8.02 (1H, s), 8.20 (1H, s), 8.52 (1H, s), 8.65 (1H, s), 8.66 (1H, s), 8.73 (1H, s), 9.43 (1H, s), 9.47 (1H, s), 10.86 (1H, s); ESIMS found for $C_{25}H_{29}N_9O$ m/z 472.3 (M+1).

Example 14

The screening assay for Wnt activity is described as follows. Reporter cell lines can be generated by stably transducing cancer cell lines (e.g., colon cancer) or primary cells (e.g., IEC-6 intestinal cells) with a lentiviral construct that includes a Wnt-responsive promoter driving expression of the firefly luciferase gene.

SW480 colon carcinoma cells were transduced with a lentiviral vector expressing luciferase with a human Sp5 promoter consisting of a sequence of eight TCF/LEF binding sites. SW480 cells stably expressing the Sp5-Luc reporter gene and a hygromycin resistance gene were selected by treatment with 150 μg/mL of hygromycin for 7 days. These stably transduced SW480 cells were expanded in cell culture and used for all further screening activities. Each compound was dissolved in DMSO as a 10 mM stock and used to prepare compound source plates. Serial dilution (1:3, 10-point dose-response curves starting from 10 μM) and compound transfer was performed using the ECHO 550 (Labcyte, Sunnyvale, Calif.) into 384-well white solid bottom assay plates (Greiner Bio-One) with appropriate DMSO backfill for a final DMSO concentration of 0.1%. For Sp5-Luc reporter gene assays, the cells were plated at 4,000 cells/well in 384-well plates with a DMEM medium containing 1% fetal bovine serum, and 1% Penicillin-Streptomycin and incubated for 36 to 48 hours at 37° C. and 5% $CO_2$. Following incubation, 15 μl of BriteLite Plus luminescence reagent (Perkin Elmer) was added to each well of the 384-well assay plates. The plates were placed on an orbital shaker for 2 min and then luminescence was quantified using the Envision (Perkin Elmer) plate reader. Readings were normalized to DMSO only treated cells, and normalized activities were utilized for $EC_{50}$ calculations using the dose-response log (inhibitor) vs. response-variable slope (four parameters) nonlinear regression feature available in GraphPad Prism 5.0 (or Dotmatics). For $EC_{50}$ of >10 μM, the percent inhibition at 10 μM is provided.

Table 2 shows the measured activity for representative compounds of Formulas I, Ia, Ib, Ic, Id, and Ie as described herein.

TABLE 2

| Compound | $EC_{50}$ (μM) |
|---|---|
| 2 | 2.945 |
| 5 | >10 (47.9%) |
| 11 | 3.186 |
| 16 | 1.535 |
| 41 | 1.314 |
| 47 | 5.209 |
| 56 | 3.389 |
| 62 | >10 (43.1%) |
| 71 | 0.559 |
| 86 | 1.888 |
| 95 | 1.544 |
| 99 | 1.308 |
| 105 | >10 (45.4%) |
| 112 | 3.647 |
| 122 | 2.536 |
| 145 | 0.259 |
| 147 | 0.102 |
| 151 | 0.498 |
| 153 | 0.111 |
| 164 | 0.585 |
| 170 | 0.396 |
| 172 | 0.445 |
| 194 | 0.596 |
| 202 | 0.686 |
| 209 | 0.485 |
| 216 | 0.447 |
| 228 | 0.076 |
| 229 | 0.090 |
| 234 | 0.124 |
| 241 | 0.388 |
| 242 | 0.268 |
| 280 | >10 (33.7%) |

TABLE 2-continued

| Compound | $EC_{50}$ (μM) |
|---|---|
| 283 | >10 (43.6%) |
| 314 | 0.368 |
| 317 | >10 (50.0%) |
| 333 | 0.504 |
| 347 | >10 (28.7%) |
| 358 | 0.189 |
| 372 | >10 (48.7%) |
| 376 | 3.423 |
| 379 | 1.599 |
| 400 | 1.353 |
| 416 | 0.386 |
| 447 | 0.107 |
| 448 | >10 (2.8%) |
| 450 | 0.279 |
| 477 | 0.962 |
| 523 | 0.530 |
| 540 | >10 (11.8%) |
| 556 | >10 (41.3%) |
| 566 | >10 (33.2%) |
| 585 | 2.076 |
| 589 | >10 (7.8%) |
| 591 | 6.058 |
| 592 | >10 (5.0%) |
| 613 | 8.808 |
| 624 | 0.750 |
| 625 | 0.964 |
| 634 | 8.614 |
| 640 | >10 (42.9%) |
| 641 | 0.977 |
| 642 | 0.869 |
| 643 | 0.688 |
| 662 | >10 (26.0%) |
| 692 | >10 (38.6%) |
| 764 | >10 (27.5%) |
| 804 | 0.289 |
| 807 | 0.484 |
| 862 | 3.965 |
| 863 | >10 (29.7%) |
| 871 | >10 (24.7%) |
| 877 | >10 (0%) |
| 892 | 4.277 |
| 896 | 0.121 |
| 909 | >10 (56.1%) |
| 918 | >10 (5.0%) |
| 923 | >10 (34.8%) |
| 954 | >10 (29.6%) |
| 963 | >10 (11.8%) |
| 969 | >10 (4.2%) |
| 978 | >10 (37.2%) |
| 979 | >10 (20.3%) |
| 985 | >10 (5.5%) |
| 994 | >10 (11.5%) |
| 1003 | >10 (19.3%) |
| 1007 | >10 (14.6%) |
| 1013 | >10 (0%) |
| 1029 | 2.909 |
| 1047 | 0.573 |
| 1052 | 3.149 |
| 1054 | 0.468 |
| 1058 | 2.152 |
| 1060 | 3.572 |
| 1071 | 1.527 |
| 1077 | 1.084 |
| 1079 | 1.000 |
| 1101 | 2.277 |
| 1109 | 1.918 |
| 1116 | 0.791 |
| 1123 | 1.965 |
| 1136 | 0.323 |
| 1141 | 0.414 |
| 1186 | >10 (35.8%) |
| 1189 | >10 (29.5%) |
| 1210 | 0.478 |
| 1220 | 1.822 |
| 1223 | 8.263 |
| 1239 | >10 (47.4%) |
| 1253 | 1.184 |
| 1254 | >10 (31.7%) |

TABLE 2-continued

| Compound | EC$_{50}$ (μM) |
|---|---|
| 1264 | 9.713 |
| 1278 | 3.701 |
| 1282 | 0.742 |
| 1285 | 1.651 |
| 1288 | 0.059 |
| 1297 | >10 (39.2%) |
| 1306 | >10 (42.4%) |
| 1322 | 1.174 |
| 1353 | 2.177 |
| 1354 | 2.378 |
| 1356 | 2.568 |
| 1383 | >10 (15.9%) |
| 1438 | >10 (10.0%) |
| 1447 | 0.617 |
| 1462 | >10 (13.6%) |
| 1471 | >10 (17.8%) |
| 1472 | >10 (1.6%) |
| 1491 | >10 (25.2%) |
| 1495 | 1.507 |
| 1497 | >10 (41.7%) |
| 1518 | >10 (24.8%) |
| 1519 | 2.275 |
| 1523 | >10 (13.7%) |
| 1524 | >10 (13.4%) |
| 1536 | 0.663 |
| 1589 | 0.184 |
| 1598 | >10 (15.5%) |
| 1612 | >10 (37.9%) |
| 1625 | >10 (37.3%) |
| 1632 | >10 (19.2%) |
| 1634 | >10 (16.4%) |
| 1656 | 1.199 |
| 1670 | 3.712 |
| 1710 | 3.384 |
| 1713 | 1.144 |
| 1773 | 0.088 |
| 1777 | >10 (35.4%) |
| 1783 | >10 (14.4%) |
| 1785 | 4.268 |
| 1802 | 1.402 |
| 1813 | 0.396 |
| 1815 | >10 (12.9%) |
| 1953 | >10 (9.7%) |
| 2722 | >10 (13.7%) |
| 2731 | >10 (30.9%) |
| 2736 | >10 (19.3%) |
| 2767 | >10 (20.7%) |
| 2776 | 0.836 |
| 2782 | >10 (2.2%) |
| 2791 | >10 (10.5%) |
| 2792 | >10 (38.1%) |
| 2807 | >10 (0%) |
| 2816 | >10 (15.4%) |
| 2820 | >10 (5.3%) |
| 2826 | >10 (11.2%) |
| 2864 | >10 (47.3%) |
| 2865 | 3.022 |
| 2866 | 2.203 |
| 2867 | 9.156 |
| 2871 | >10 (24.5%) |
| 2884 | >10 (44.1%) |
| 2890 | 3.578 |
| 2892 | >10 (46.9%) |
| 2914 | 0.751 |
| 2922 | 2.416 |
| 2929 | 0.835 |
| 2936 | >10 (11.9%) |
| 2949 | 0.059 |
| 2954 | 0.915 |
| 3000 | 1.949 |
| 3003 | >10 (33.5%) |
| 3024 | 2.610 |
| 3032 | 0.607 |
| 3034 | >10 (0%) |
| 3037 | >10 (14.9%) |
| 3067 | 4.497 |
| 3078 | >10 (11.7%) |
| 3092 | 2.283 |

TABLE 2-continued

| Compound | EC$_{50}$ (μM) |
|---|---|
| 3096 | 0.596 |
| 3098 | >10 (14.9%) |
| 3099 | 0.696 |
| 3102 | >10 (28.5%) |
| 3105 | 4.163 |
| 3111 | >10 (9.7%) |
| 3118 | >10 (31.2%) |
| 3120 | >10 (16.2%) |
| 3134 | >10 (10.2%) |
| 3136 | >10 (32.0%) |
| 3167 | >10 (0%) |
| 3168 | >10 (17.3%) |
| 3194 | 4.782 |
| 3240 | >10 (0%) |
| 3249 | >10 (31.5%) |
| 3257 | >10 (12.9%) |
| 3259 | 3.502 |
| 3311 | >10 (4.9%) |
| 3363 | >10 (32.9%) |
| 3403 | 0.849 |
| 3412 | >10 (47.1%) |
| 3425 | >10 (0%) |
| 3439 | >10 (2.1%) |
| 3446 | >10 (29.9%) |
| 3470 | 5.481 |
| 3474 | >10 (1.9%) |
| 3524 | 3.554 |
| 3527 | >10 (42.5%) |
| 3587 | 0.357 |
| 3591 | >10 (1.3%) |
| 3597 | >10 (7.6%) |
| 3599 | >10 (41.3%) |
| 3612 | 3.922 |
| 3616 | 0.485 |
| 3627 | 1.681 |
| 3629 | 0.396 |
| 3638 | 0.593 |
| 3643 | 0.073 |
| 3646 | 0.219 |
| 3674 | 0.512 |
| 3683 | 0.603 |
| 3689 | 0.370 |
| 3698 | 0.288 |
| 3699 | 0.234 |
| 3714 | 0.845 |
| 3723 | 0.842 |
| 3727 | 0.426 |
| 3733 | 0.515 |
| 3749 | 0.092 |
| 3772 | 0.221 |
| 3773 | 2.825 |
| 3774 | >10 (54.7%) |
| 3778 | 3.968 |
| 3780 | 1.526 |
| 3783 | 1.082 |
| 3791 | 0.482 |
| 3797 | 0.427 |
| 3799 | 2.115 |
| 3821 | 0.176 |
| 3829 | 0.994 |
| 3836 | 0.220 |
| 3843 | >10 (25.0%) |
| 3856 | 0.367 |
| 3861 | 0.824 |
| 3907 | 0.361 |
| 3910 | 1.236 |
| 3941 | 1.338 |
| 3944 | 0.962 |
| 3960 | >10 (44.8%) |
| 3974 | 0.760 |
| 3985 | >10 (49.8%) |
| 3999 | >10 (22.0%) |
| 4003 | >10 (34.0%) |
| 4006 | >10 (37.7%) |
| 4027 | >10 (17.5%) |
| 4041 | 0.291 |
| 4074 | 2.688 |
| 4075 | 5.596 |

TABLE 2-continued

| Compound | EC$_{50}$ (µM) |
|---|---|
| 4077 | 0.200 |
| 4104 | >10 (41.3%) |
| 4150 | 2.847 |
| 4159 | 0.972 |
| 4167 | >10 (8.9%) |
| 4218 | >10 (24.9%) |
| 4239 | >10 (41.9%) |
| 4244 | 0.863 |
| 4257 | 4.059 |
| 4319 | 1.525 |
| 4332 | >10 (9.6%) |
| 4346 | >10 (3.8%) |
| 4353 | >10 (2.1%) |
| 4377 | >10 (28.6%) |
| 4431 | 2.817 |
| 4432 | 2.003 |
| 4434 | 8.484 |
| 4498 | 0.383 |
| 4504 | 3.636 |
| 4523 | 0.718 |
| 4535 | 0.346 |
| 4536 | 0.832 |
| 4537 | >10 (25.3%) |
| 4538 | 0.278 |
| 4539 | 0.301 |
| 4544 | 0.059 |
| 4548 | >10 |
| 4551 | 1.024 |
| 4558 | 2.799 |
| 4559 | >10 (40.8%) |
| 4560 | >10 (49.7%) |
| 4561 | 0.953 |
| 4564 | >10 (33.3%) |
| 4565 | 1.949 |
| 4569 | 0.570 |
| 4570 | 3.264 |
| 4573 | 3.228 |
| 4574 | 3.874 |
| 4576 | >10 (35.3%) |
| 4577 | >10 (28.9%) |
| 4586 | >10 (29.6%) |
| 4593 | >10 (32.8%) |
| 4594 | >10 (35.6%) |
| 4595 | >10 (20.1%) |
| 4600 | 8.043 |
| 4602 | >10 (10.9%) |
| 4609 | >10 (0%) |
| 4610 | >10 (9.1%) |
| 4611 | >10 (35.7%) |
| 4612 | >10 (33.8%) |
| 4614 | 3.665 |
| 4615 | 3.831 |
| 4616 | >10 (0%) |
| 4618 | >10 (14.6%) |
| 4622 | >10 (50.0%) |
| 4623 | >10 (49.5%) |
| 4632 | 0.922 |
| 4634 | >10 (51.1%) |
| 4640 | 0.163 |
| 4641 | 3.717 |
| 4643 | 3.020 |
| 4646 | 0.495 |
| 4647 | >10 (34.5%) |
| 4650 | >10 (19.7%) |
| 4657 | 3.948 |
| 4658 | 0.164 |

Example 15

Representative compounds were screened using the assay procedure for DYRK1A kinase activity as described below.

Each compound was dissolved in DMSO as a 10 mM stock and used to prepare compound source plates. Serial dilution (1:3, 11-point dose-response curves from 10 µM to 0.00016 µM) and compound transfer was performed using the ECHO 550 (Labcyte, Sunnyvale, Calif.) into 1536-well black-walled round bottom plates (Corning).

The DYRK1A kinase assay was run using the Ser/Thr 18 peptide Z-lyte assay kit according to manufacturer's instructions (Life Technologies—a Division of Thermo-Fisher). This is a non-radioactive assay using fluorescence resonance energy transfer (FRET) between coumarin and fluorescein to detect kinase activity which is represented as a ratio of coumarin emission/fluorescein emission.

Briefly, recombinant DYRK1A kinase, ATP and Ser/Thr peptide 18 were prepared in 1× Kinase buffer to final concentrations of 0.19 µg/mL, 30 µM, and 4 µM respectively. The mixture was allowed to incubate with the representative compounds for one hour at room temperature. All reactions were performed in duplicate. Unphosphorylated ("0% Control") and phosphorylated ("100% control") forms of Ser/Thr 18 served as control reactions. Additionally, an 11-point dose-response curve of Staurosporine (1 uM top) was run to serve as a positive compound control.

After incubation, Development Reagent A was diluted in Development Buffer then added to the reaction and allowed to further incubate for one hour at room temperature. The plate was read at Ex 400 Em 455 to detect the coumarin signal and Ex 400 Em 520 to measure the signal (EnVision Multilabel Plate Reader, PerkinElmer).

The Emission ratio (Em) was calculated as a ratio of the coumarin (C) emission signal (at 445 nm)/Fluorescein (F) emission signal (at 520 nm). The percent phosphorylation was then calculated using the following formula: [1−((Em ratio×F100%)−C100%)/((C0%−C100%)+(Em ratio× (F100%−F0%)))]. Dose-response curves were generated and inhibitory concentration (IC$_{50}$) values were calculated using non-linear regression curve fit in the Dotmatics' Studies Software (Bishops Stortford, UK).

Table 3 shows the measured activity for representative compounds of Formulas I, Ia, Ib, Ic, Id, and Ie as described herein.

TABLE 3

| Compound | EC$_{50}$ (µM) |
|---|---|
| 2 | 0.018 |
| 5 | 0.007 |
| 11 | 0.014 |
| 16 | 0.040 |
| 41 | 0.010 |
| 47 | 0.036 |
| 56 | 0.021 |
| 62 | 0.056 |
| 71 | 0.003 |
| 86 | 0.012 |
| 95 | 0.006 |
| 99 | 0.009 |
| 105 | 0.071 |
| 112 | 0.088 |
| 122 | 0.016 |
| 145 | 0.005 |
| 147 | 0.007 |
| 151 | 0.002 |
| 153 | 0.004 |
| 164 | 0.006 |
| 170 | 0.006 |
| 172 | 0.013 |
| 194 | 0.023 |
| 202 | 0.009 |
| 209 | 0.005 |
| 216 | 0.007 |
| 228 | 0.006 |
| 229 | 0.011 |
| 234 | 0.004 |
| 241 | 0.067 |

TABLE 3-continued

| Compound | EC$_{50}$ (μM) |
|---|---|
| 242 | 0.060 |
| 280 | 0.150 |
| 283 | 0.698 |
| 314 | 0.008 |
| 317 | 0.006 |
| 333 | 0.880 |
| 347 | 9.990 |
| 358 | 0.364 |
| 372 | 0.067 |
| 376 | 0.019 |
| 379 | 0.011 |
| 400 | 0.121 |
| 416 | 0.031 |
| 447 | 0.001 |
| 448 | >10 |
| 450 | 0.001 |
| 477 | 0.001 |
| 523 | 0.004 |
| 540 | 0.022 |
| 556 | 0.054 |
| 566 | 0.077 |
| 585 | 0.009 |
| 589 | 0.050 |
| 591 | >10 |
| 592 | 0.029 |
| 613 | 0.003 |
| 624 | 0.003 |
| 625 | 0.004 |
| 634 | 0.029 |
| 640 | 0.038 |
| 641 | 0.008 |
| 642 | 0.006 |
| 643 | 0.010 |
| 662 | >10 |
| 692 | 1.011 |
| 764 | 0.008 |
| 804 | 0.002 |
| 807 | 0.007 |
| 862 | 0.203 |
| 863 | 0.388 |
| 871 | 0.025 |
| 877 | 0.016 |
| 892 | 0.142 |
| 896 | 0.005 |
| 909 | 0.013 |
| 918 | 0.062 |
| 923 | 0.044 |
| 954 | 0.069 |
| 963 | 0.045 |
| 969 | >10 |
| 978 | 0.171 |
| 979 | >10 |
| 985 | 0.126 |
| 994 | 0.015 |
| 1003 | 0.025 |
| 1007 | 0.106 |
| 1013 | 0.075 |
| 1029 | 0.045 |
| 1047 | 0.008 |
| 1052 | 0.035 |
| 1054 | 0.008 |
| 1058 | 0.009 |
| 1060 | 0.027 |
| 1071 | 0.010 |
| 1077 | 0.016 |
| 1079 | 0.019 |
| 1101 | 0.020 |
| 1109 | 0.018 |
| 1116 | 0.015 |
| 1123 | 0.013 |
| 1136 | 0.013 |
| 1141 | 0.008 |
| 1186 | 0.042 |
| 1189 | 0.186 |
| 1210 | 0.004 |
| 1220 | 0.019 |
| 1223 | 0.018 |
| 1239 | 0.171 |
| 1253 | 0.013 |
| 1254 | 0.104 |
| 1264 | 0.043 |
| 1278 | 0.007 |
| 1282 | 0.008 |
| 1285 | 0.013 |
| 1288 | 0.006 |
| 1297 | 0.057 |
| 1306 | 0.391 |
| 1322 | 0.052 |
| 1353 | 0.011 |
| 1354 | 0.002 |
| 1356 | 0.005 |
| 1383 | 0.002 |
| 1438 | 0.100 |
| 1447 | 0.056 |
| 1462 | 0.370 |
| 1471 | 0.046 |
| 1472 | 0.246 |
| 1491 | 0.039 |
| 1495 | 0.113 |
| 1497 | 0.030 |
| 1518 | 0.014 |
| 1519 | 0.011 |
| 1523 | 0.047 |
| 1524 | 0.007 |
| 1536 | 0.004 |
| 1589 | 0.005 |
| 1598 | 0.027 |
| 1612 | 0.021 |
| 1625 | 0.025 |
| 1632 | 0.500 |
| 1634 | 0.342 |
| 1656 | 0.065 |
| 1670 | 0.006 |
| 1710 | 0.002 |
| 1713 | 0.027 |
| 1773 | 0.001 |
| 1777 | 0.005 |
| 1783 | 0.007 |
| 1785 | 0.007 |
| 1802 | 0.007 |
| 1813 | 0.002 |
| 1815 | >10 |
| 1953 | 0.317 |
| 2722 | 0.023 |
| 2731 | 0.021 |
| 2736 | 0.030 |
| 2767 | 0.034 |
| 2776 | 0.056 |
| 2782 | 0.867 |
| 2791 | 0.513 |
| 2792 | 0.012 |
| 2807 | 0.074 |
| 2816 | 0.024 |
| 2820 | 0.037 |
| 2826 | 0.082 |
| 2864 | 0.039 |
| 2865 | 0.041 |
| 2866 | 0.041 |
| 2867 | 0.036 |
| 2871 | 0.016 |
| 2884 | 0.049 |
| 2890 | 0.035 |
| 2892 | 0.039 |
| 2914 | 0.028 |
| 2922 | 0.036 |
| 2929 | 0.017 |
| 2936 | >10 |
| 2949 | 0.024 |
| 2954 | 0.028 |
| 3000 | 0.010 |
| 3003 | 0.067 |
| 3024 | 0.017 |
| 3032 | 0.008 |
| 3034 | 0.119 |
| 3037 | 0.019 |
| 3067 | 0.058 |

TABLE 3-continued

| Compound | EC$_{50}$ (µM) |
|---|---|
| 3078 | 0.207 |
| 3092 | 0.269 |
| 3096 | 0.119 |
| 3098 | 0.096 |
| 3099 | 0.154 |
| 3102 | 0.088 |
| 3105 | 0.147 |
| 3111 | 0.377 |
| 3118 | 1.483 |
| 3120 | 0.009 |
| 3134 | 1.995 |
| 3136 | 0.123 |
| 3167 | 0.037 |
| 3168 | 0.008 |
| 3194 | 0.006 |
| 3240 | 1.049 |
| 3249 | 0.026 |
| 3257 | 0.016 |
| 3259 | 0.024 |
| 3311 | 0.007 |
| 3363 | 0.119 |
| 3403 | 0.581 |
| 3412 | 0.040 |
| 3425 | 0.157 |
| 3439 | 0.100 |
| 3446 | 2.092 |
| 3470 | 0.110 |
| 3474 | 0.071 |
| 3524 | 0.011 |
| 3527 | 0.294 |
| 3587 | 0.001 |
| 3591 | 0.010 |
| 3597 | 0.006 |
| 3599 | 0.008 |
| 3612 | 0.487 |
| 3616 | 0.029 |
| 3627 | 0.007 |
| 3629 | 0.007 |
| 3638 | 0.006 |
| 3643 | 0.010 |
| 3646 | 0.002 |
| 3674 | 0.007 |
| 3683 | 0.008 |
| 3689 | 0.071 |
| 3698 | 0.064 |
| 3699 | 0.002 |
| 3714 | 0.010 |
| 3723 | 0.002 |
| 3727 | 0.004 |
| 3733 | 0.016 |
| 3749 | 0.010 |
| 3772 | 0.008 |
| 3773 | 0.016 |
| 3774 | 0.010 |
| 3778 | 0.004 |
| 3780 | 0.016 |
| 3783 | 0.004 |
| 3791 | 0.010 |
| 3797 | 0.008 |
| 3799 | 0.012 |
| 3821 | 0.007 |
| 3829 | 0.010 |
| 3836 | 0.005 |
| 3843 | 0.006 |
| 3856 | 0.010 |
| 3861 | 0.005 |
| 3907 | 0.048 |
| 3910 | 0.059 |
| 3941 | 0.006 |
| 3944 | 0.006 |
| 3960 | 1.012 |
| 3974 | 0.184 |
| 3985 | 0.751 |
| 3999 | 0.454 |
| 4003 | 0.056 |
| 4006 | 0.056 |
| 4027 | 0.021 |
| 4041 | 0.630 |

TABLE 3-continued

| Compound | EC$_{50}$ (µM) |
|---|---|
| 4074 | 0.007 |
| 4075 | 0.008 |
| 4077 | 0.007 |
| 4104 | 0.003 |
| 4150 | 0.053 |
| 4159 | 0.004 |
| 4167 | 3.200 |
| 4218 | 0.014 |
| 4239 | 0.005 |
| 4244 | 0.004 |
| 4257 | 0.006 |
| 4319 | 0.039 |
| 4332 | 0.048 |
| 4346 | 0.037 |
| 4353 | 0.529 |
| 4377 | 0.253 |
| 4431 | 0.003 |
| 4432 | 0.002 |
| 4434 | 0.012 |
| 4498 | 0.002 |
| 4504 | 0.004 |
| 4523 | 0.010 |
| 4535 | 0.009 |
| 4536 | 0.014 |
| 4537 | 0.035 |
| 4538 | 0.003 |
| 4539 | 0.002 |
| 4544 | 0.033 |
| 4548 | 0.019 |
| 4551 | 0.005 |
| 4558 | 0.004 |
| 4559 | 0.014 |
| 4560 | 0.014 |
| 4561 | 0.007 |
| 4564 | 1.027 |
| 4565 | 0.012 |
| 4569 | 0.008 |
| 4570 | 0.003 |
| 4573 | 0.006 |
| 4574 | 1.411 |
| 4576 | 0.675 |
| 4577 | 0.175 |
| 4586 | 0.002 |
| 4593 | 0.131 |
| 4594 | 0.035 |
| 4595 | 0.038 |
| 4600 | 0.030 |
| 4602 | 0.018 |
| 4609 | 1.983 |
| 4610 | 0.029 |
| 4611 | 0.040 |
| 4612 | 0.159 |
| 4614 | 0.010 |
| 4615 | 0.027 |
| 4616 | 0.067 |
| 4618 | 0.018 |
| 4622 | 0.040 |
| 4623 | 0.027 |
| 4632 | 0.005 |
| 4634 | 0.037 |
| 4640 | 0.019 |
| 4641 | 0.016 |
| 4643 | 0.064 |
| 4646 | 0.009 |
| 4647 | 0.043 |
| 4650 | 0.003 |
| 4657 | 0.024 |
| 4658 | 0.001 |

Example 16

Representative compounds were screened using the assay procedure for GSK3β kinase activity as described below.

Each compound is dissolved in DMSO as a 10 mM stock and used to prepare compound source plates. Serial dilution (1:3, 11-point dose-response curves from 10 µM to 0.0003

µM) and compound transfer was performed using the ECHO 550 (Labcyte, Sunnyvale, Calif.) into 1536-well black-walled round bottom plates (Corning).

The GSK30 kinase assay is run using the Ser/Thr 09 peptide Z-lyte assay kit according to manufacturer's instructions (Life Technologies—a Division of Thermo-Fisher). This is a non-radioactive assay using fluorescence resonance energy transfer (FRET) between coumarin and fluorescein to detect kinase activity which is represented as ratio of coumarin emission/fluorescein emission.

Briefly, recombinant GSK33 kinase, ATP and Ser/Thr peptide 09 are prepared in 1× Kinase buffer to final concentrations of 0.04 µg/mL, 46 µM, and 4 µM respectively. The mixture is allowed to incubate with the representative compounds for one hour at room temperature. All reactions were performed in duplicate. Unphosphorylated ("0% Control") and phosphorylated ("100% control") forms of Ser/Thr 18 serve as control reactions.

After incubation, diluted Development Buffer is added to the reaction and allowed to further incubate for one hour at room temperature. The plate is read at Ex 400 Em 455 to detect the coumarin signal and Ex 400 Em 520 to measure the signal (EnVision Multilabel Plate Reader, PerkinElmer).

The Emission ratio (Em) is calculated as a ratio of the coumarin (C) emission signal (at 445 nm)/Fluorescein (F) emission signal (at 520 nm). The percent phosphorylation is then calculated using the following formula: [1−((Em ratio×F100%)−C100%)/((C0%−C100%)+(Em ratio×(F100%−F0%)))].

Dose-response curves are generated and inhibitory concentration ($IC_{50}$) values are calculated using non-linear regression curve fit in the Dotmatics' Studies Software (Bishops Stortford, UK).

Table 4 shows the activity of representative compounds of Formulas I, Ia, Ib, Ic, Id, and Ie as provided herein.

TABLE 4

| Compound | $EC_{50}$ (µM) |
|---|---|
| 2 | 0.020 |
| 5 | 0.138 |
| 11 | 0.101 |
| 16 | 0.277 |
| 41 | 0.429 |
| 47 | 0.200 |
| 56 | 0.059 |
| 62 | 0.009 |
| 71 | 0.018 |
| 86 | 0.068 |
| 95 | 0.084 |
| 99 | 0.180 |
| 105 | 0.541 |
| 112 | 0.062 |
| 122 | 0.070 |
| 145 | 1.997 |
| 147 | >10 |
| 151 | 0.571 |
| 153 | 6.003 |
| 164 | 4.007 |
| 170 | 1.869 |
| 172 | 0.765 |
| 194 | 0.017 |
| 202 | >10 |
| 209 | >10 |
| 216 | 4.846 |
| 228 | 0.753 |
| 229 | 2.896 |
| 234 | 2.251 |
| 241 | 0.166 |
| 242 | 6.854 |
| 280 | 0.335 |
| 283 | 1.183 |

TABLE 4-continued

| Compound | $EC_{50}$ (µM) |
|---|---|
| 314 | 2.606 |
| 317 | 0.007 |
| 333 | 2.772 |
| 347 | >10 |
| 358 | 0.560 |
| 372 | 0.255 |
| 376 | 0.665 |
| 379 | 0.359 |
| 400 | 0.036 |
| 416 | 0.049 |
| 447 | 0.048 |
| 448 | >10 |
| 450 | 0.350 |
| 477 | 0.084 |
| 523 | 0.362 |
| 540 | 0.644 |
| 556 | 0.086 |
| 566 | 0.621 |
| 585 | 0.109 |
| 589 | 0.156 |
| 591 | >10 |
| 592 | >10 |
| 613 | 0.219 |
| 624 | 2.928 |
| 625 | 8.265 |
| 634 | 1.147 |
| 640 | 0.401 |
| 641 | 2.564 |
| 642 | 3.063 |
| 643 | 8.559 |
| 662 | >10 |
| 692 | >10 |
| 764 | 0.243 |
| 804 | 4.683 |
| 807 | >10 |
| 862 | >10 |
| 863 | >10 |
| 871 | 0.360 |
| 877 | 9.917 |
| 892 | >10 |
| 896 | >10 |
| 909 | 0.025 |
| 918 | 0.236 |
| 923 | 0.204 |
| 954 | 0.195 |
| 963 | 0.045 |
| 969 | >10 |
| 978 | 0.087 |
| 979 | >10 |
| 985 | 0.035 |
| 994 | 0.776 |
| 1003 | 0.262 |
| 1007 | 0.349 |
| 1013 | 0.532 |
| 1029 | 0.238 |
| 1047 | 0.661 |
| 1052 | 9.426 |
| 1054 | 3.652 |
| 1058 | 3.130 |
| 1060 | >10 |
| 1071 | >10 |
| 1077 | 4.139 |
| 1079 | 9.742 |
| 1101 | 0.055 |
| 1109 | >10 |
| 1116 | >10 |
| 1123 | 4.798 |
| 1136 | 2.532 |
| 1141 | 4.059 |
| 1186 | 0.402 |
| 1189 | 1.693 |
| 1210 | >10 |
| 1220 | 5.605 |
| 1223 | 0.097 |
| 1239 | 0.112 |
| 1253 | 0.015 |
| 1254 | 0.069 |
| 1264 | 0.017 |

TABLE 4-continued

| Compound | EC$_{50}$ (μM) |
|---|---|
| 1278 | 0.134 |
| 1282 | 0.453 |
| 1285 | 0.832 |
| 1288 | 0.177 |
| 1297 | 0.038 |
| 1306 | 0.377 |
| 1322 | 0.094 |
| 1353 | 1.350 |
| 1354 | 1.169 |
| 1356 | 2.781 |
| 1383 | 0.453 |
| 1438 | 5.180 |
| 1447 | 0.952 |
| 1462 | 0.707 |
| 1471 | 0.578 |
| 1472 | 2.331 |
| 1491 | 0.166 |
| 1495 | 0.254 |
| 1497 | >10 |
| 1518 | 0.253 |
| 1519 | 0.772 |
| 1523 | 1.379 |
| 1524 | 0.407 |
| 1536 | 0.207 |
| 1589 | 9.985 |
| 1598 | 4.185 |
| 1612 | 0.049 |
| 1625 | 0.008 |
| 1632 | 0.943 |
| 1634 | 0.224 |
| 1656 | 0.340 |
| 1670 | 0.120 |
| 1710 | 8.036 |
| 1713 | >10 |
| 1773 | 0.995 |
| 1777 | 0.098 |
| 1783 | 0.536 |
| 1785 | 0.135 |
| 1802 | >10 |
| 1813 | >10 |
| 1815 | >10 |
| 1953 | 2.6237 |
| 2722 | 0.326 |
| 2731 | 5.506 |
| 2736 | 3.732 |
| 2767 | 2.520 |
| 2776 | >10 |
| 2782 | 2.454 |
| 2791 | 3.471 |
| 2792 | 1.152 |
| 2807 | 4.943 |
| 2816 | 5.256 |
| 2820 | 7.061 |
| 2826 | 5.373 |
| 2864 | >10 |
| 2865 | >10 |
| 2866 | >10 |
| 2867 | >10 |
| 2871 | >10 |
| 2884 | >10 |
| 2890 | >10 |
| 2892 | >10 |
| 2914 | 0.453 |
| 2922 | >10 |
| 2929 | >10 |
| 2936 | >10 |
| 2949 | >10 |
| 2954 | >10 |
| 3000 | 0.166 |
| 3003 | 1.516 |
| 3024 | >10 |
| 3032 | >10 |
| 3034 | >10 |
| 3037 | 1.584 |
| 3067 | 0.836 |
| 3078 | 0.760 |
| 3092 | >10 |
| 3096 | >10 |

TABLE 4-continued

| Compound | EC$_{50}$ (μM) |
|---|---|
| 3098 | >10 |
| 3099 | >10 |
| 3102 | >10 |
| 3105 | >10 |
| 3111 | 2.137 |
| 3118 | >10 |
| 3120 | 1.329 |
| 3134 | 2.593 |
| 3136 | 0.982 |
| 3167 | >10 |
| 3168 | >10 |
| 3194 | >10 |
| 3240 | >10 |
| 3249 | 6.123 |
| 3257 | 5.298 |
| 3259 | >10 |
| 3311 | >10 |
| 3363 | 9.990 |
| 3403 | >10 |
| 3412 | >10 |
| 3425 | 2.292 |
| 3439 | 0.463 |
| 3446 | >10 |
| 3470 | >10 |
| 3474 | >10 |
| 3524 | >10 |
| 3527 | >10 |
| 3587 | >10 |
| 3591 | 2.273 |
| 3597 | >10 |
| 3599 | 0.780 |
| 3612 | >10 |
| 3616 | >10 |
| 3627 | >10 |
| 3629 | 0.002 |
| 3638 | 0.027 |
| 3643 | 0.031 |
| 3646 | 0.004 |
| 3674 | 0.021 |
| 3683 | 0.010 |
| 3689 | 0.008 |
| 3698 | 0.009 |
| 3699 | 0.006 |
| 3714 | 0.008 |
| 3723 | 0.010 |
| 3727 | 0.018 |
| 3733 | 0.043 |
| 3749 | 0.006 |
| 3772 | 0.390 |
| 3773 | 0.852 |
| 3774 | 0.397 |
| 3778 | 0.187 |
| 3780 | 0.275 |
| 3783 | 2.339 |
| 3791 | 1.348 |
| 3797 | 0.409 |
| 3799 | 0.243 |
| 3821 | 0.001 |
| 3829 | 0.763 |
| 3836 | 1.471 |
| 3843 | 1.162 |
| 3856 | 1.749 |
| 3861 | 1.056 |
| 3907 | 0.039 |
| 3910 | 0.115 |
| 3941 | 0.079 |
| 3944 | 0.018 |
| 3960 | 1.499 |
| 3974 | 0.305 |
| 3985 | 1.238 |
| 3999 | >10 |
| 4003 | 1.724 |
| 4006 | 1.471 |
| 4027 | 0.072 |
| 4041 | 0.019 |
| 4074 | 0.416 |
| 4075 | 0.966 |
| 4077 | 2.283 |

TABLE 4-continued

| Compound | EC$_{50}$ (µM) |
|---|---|
| 4104 | 0.145 |
| 4150 | 5.141 |
| 4159 | 0.072 |
| 4167 | 0.127 |
| 4218 | 7.400 |
| 4239 | 0.187 |
| 4244 | 0.030 |
| 4257 | 1.622 |
| 4319 | 0.199 |
| 4332 | 0.828 |
| 4346 | 0.135 |
| 4353 | 2.450 |
| 4377 | >10 |
| 4431 | 3.780 |
| 4432 | >10 |
| 4434 | >10 |
| 4498 | 0.001 |
| 4504 | 0.077 |
| 4523 | >10 |
| 4535 | 0.188 |
| 4536 | 0.319 |
| 4537 | 0.543 |
| 4538 | >10 |
| 4539 | 2.227 |
| 4544 | 0.018 |
| 4548 | 0.785 |
| 4551 | 4.237 |
| 4558 | 0.100 |
| 4559 | 0.110 |
| 4560 | 0.127 |
| 4561 | 0.182 |
| 4564 | >10 |
| 4565 | >10 |
| 4569 | >10 |
| 4570 | 2.185 |
| 4573 | 0.161 |
| 4574 | 0.665 |
| 4576 | 0.346 |
| 4577 | >10 |
| 4586 | 0.336 |
| 4593 | 0.034 |
| 4594 | 0.528 |
| 4595 | >10 |
| 4600 | >10 |
| 4602 | >10 |
| 4609 | 8.371 |
| 4610 | >10 |
| 4611 | >10 |
| 4612 | >10 |
| 4614 | >10 |
| 4615 | 7.819 |
| 4616 | 2.611 |
| 4618 | 3.822 |
| 4622 | 4.628 |
| 4623 | 1.717 |
| 4632 | 0.321 |
| 4634 | 5.588 |
| 4640 | 0.012 |
| 4641 | 0.092 |
| 4643 | 0.165 |
| 4646 | 0.013 |
| 4647 | 0.015 |
| 4650 | 0.036 |
| 4657 | >10 |
| 4658 | 9.623 |

Example 17

Representative compounds were screened using the assay procedure for tau phosphorylation activity described below.

SH-SY5Y cells (human neuroblastoma) were cultured in DMEM/F-12 medium supplemented with 15% FBS, Non-essential Amino Acid and Penicillin/Streptomycin. Two days before treatment, cells were seeded onto 96 well plates at 5×10$^4$ cells/well.

The above synthesized compounds were screened using the cell assay procedure to assess decrease Tau phosphorylation at Ser396 (pSer396) described below.

DMSO-resuspended compounds were dispensed to 8 wells as a serial titration from 10 µM to 4.6 nM final in medium and cells were exposed overnight (16-18 h) in a humidified incubator at 36.6c before harvest. Wells were visually checked for cell death or change in morphology and supernatants were tested for cytotoxicity by measurement of lactate dehydrogenase release (LDH, CytoToxOne kit, Promega) if necessary. As controls, commercially available DYRK1A inhibitors, Harmine and Indy which were shown to have good DYRK1A inhibition in the kinase assay with no CDK1 activity (EC$_{50}$ 18 and 53 nM respectively, 6 µM for CDK1) but weak EC$_{50}$ in the Tau assay >10 µM.

Cells were lysed with RIPA buffer complemented with phosphatase and protease inhibitors then lysates were spun down at 12,000 g for 10 min to remove any cellular debris. Lysates are then either directly tested for pSer396 by ELISA (Life Technology, Kit KHB7031) or loaded on NuPage Bis-Tris gels for western blot analysis. Colorimetric detection of ELISA signal is performed by Cytation3 plate reader (Biotek) and the chemiluminescence signal for HRP-linked antibodies used in western blotting is detected using a Carestream Image Station. The same pSer396 antibody is used for detection of pTau in both assays.

Blot densitometry for pSer396 and 3-actin were analyzed using ImageJ (NIH) and pSer396 Tau ELISA signal was used to plot, draw the curve fitting, and determine each compounds EC$_{50}$ in Prism (GraphPad).

Table 5 shows the activity of representative compounds Formulas I, Ia, Ib, Ic, Id, and Ie as provided herein.

TABLE 5

| Compound | pSer396 Tau EC$_{50}$ (µM) |
|---|---|
| 2 | 0.396 |
| 5 | 2.000 |
| 11 | 3.500 |
| 16 | 0.923 |
| 41 | >10 |
| 47 | >10 |
| 56 | 1.500 |
| 62 | 0.699 |
| 71 | 0.426 |
| 86 | 1.000 |
| 95 | 1.700 |
| 99 | 0.967 |
| 112 | 1.100 |
| 122 | 0.481 |
| 194 | 3.000 |
| 317 | 0.035 |
| 358 | 1.500 |
| 447 | 0.562 |
| 450 | 3.755 |
| 477 | 10.000 |
| 523 | 3.937 |
| 556 | 0.487 |
| 585 | 0.374 |
| 589 | 10.000 |
| 613 | 0.157 |
| 634 | 7.900 |
| 640 | 0.877 |
| 764 | 0.807 |
| 909 | 0.372 |
| 918 | >10 |
| 923 | 1.300 |
| 954 | 1.700 |
| 963 | 1.624 |
| 985 | 5.400 |
| 994 | >10 |
| 1003 | 4.500 |
| 1007 | >10 |

TABLE 5-continued

| Compound | pSer396 Tau EC$_{50}$ (µM) |
|---|---|
| 1101 | 9.500 |
| 1186 | 5.400 |
| 1223 | 1.366 |
| 1253 | 0.188 |
| 1264 | 0.902 |
| 1278 | 5.053 |
| 1288 | 10.000 |
| 1322 | 0.168 |
| 1491 | 3.700 |
| 1518 | 5.400 |
| 1524 | >10 |
| 1536 | 1.178 |
| 1598 | >10 |
| 1612 | 1.100 |
| 1625 | 0.402 |
| 1670 | 0.604 |
| 1777 | 10.000 |
| 1785 | 5.655 |
| 1815 | >10 |
| 1953 | >10 |
| 2722 | 6.008 |
| 2731 | >10 |
| 2736 | >10 |
| 2864 | >10 |
| 2865 | >10 |
| 2866 | >10 |
| 2867 | >10 |
| 3000 | 1.831 |
| 3098 | >10 |
| 3105 | >10 |
| 3120 | 2.429 |
| 3249 | 10.000 |
| 3629 | 0.021 |
| 3638 | 1.500 |
| 3643 | 0.102 |
| 3646 | 0.079 |
| 3674 | 0.192 |
| 3683 | 0.179 |
| 3689 | 0.156 |
| 3698 | 0.076 |
| 3699 | 0.043 |
| 3714 | 0.210 |
| 3723 | 0.252 |
| 3727 | 0.398 |
| 3733 | 0.227 |
| 3749 | 0.087 |
| 3772 | 7.283 |
| 3773 | >10 |
| 3780 | >10 |
| 3799 | 3.645 |
| 3821 | 0.029 |
| 3907 | 0.367 |
| 3910 | 0.989 |
| 3941 | 0.571 |
| 3944 | 0.428 |
| 4027 | 0.219 |
| 4041 | 0.102 |
| 4104 | 10.000 |
| 4159 | 0.989 |
| 4239 | 0.491 |
| 4244 | 0.284 |
| 4319 | 0.553 |
| 4346 | 1.545 |
| 4498 | 0.037 |
| 4504 | 10.000 |
| 4535 | 0.925 |
| 4536 | >10 |
| 4544 | 0.076 |
| 4558 | 7.000 |
| 4559 | 2.400 |
| 4560 | 0.992 |
| 4561 | 2.100 |
| 4573 | 10.000 |
| 4586 | 8.800 |
| 4610 | >10 |
| 4618 | 1.054 |
| 4632 | 7.932 |
| 4640 | 0.033 |
| 4641 | 0.826 |
| 4643 | 0.195 |
| 4646 | 0.110 |
| 4647 | 0.177 |
| 4650 | 0.192 |

Example 18

Representative compounds were screened using the cell-based assay procedure for signal of Tau phosphorylation at Threonine 212 (pT212Tau) in a transiently double transfected (Dyrk1a- and MAPT-overexpressing) cell type as described below.

HEK293T cells (transfectable human embryonic kidney cells) were cultured in DMEM medium supplemented with 10% FBS and 1% penicillin/streptomycin.

HEK293T cells were transiently transfected to overexpress Dyrk1a and microtubule-associated protein Tau (MAPT) genes. Specifically, Dyrk1a and MAPT expression vectors were obtained from OriGene (10 µg of each, catalog numbers SC314641 and RC216166, respectively). A MaxiPrep for each vector was ordered and received from GeneWiz, yielding 874.5 µg (resuspended at 1.749 µg/L) of the Dyrk1a expression vector, and 898 µg (resuspended at 1.796 µg/L) of MAPT.

HEK293T cells were seeded at $1.0\times10^7$ cells in 10 mL per T-75 flask. After overnight incubation, HEK293T cells in the T-75 flasks were transfected by creating a master mix of 10 µg of each expression vector per flask, with Lipofectamine™ 3000 Transfection Reagent (Invitrogen, L3000015) diluted in Opti-MEM medium according to the manufacturer's suggested protocol. One T-75 flask was designated as a no-vector negative control for pT212Tau signal.

After 4-6 hours of incubation in transfection reagents, transiently double transfected HEK293T cells were dissociated by treatment with trypsin EDTA and seeded at $1.0\times10^5$ cells in 100 µL per well in 96-well plates. No-vector negative controls were seeded in separate 96-well plates to avoid the risk of the negative control cells picking up the overexpression during incubation. At the time of seeding, DMSO-resuspended Samumed compounds were dispensed to eight wells as a serial dilution from 10 µM to 4.6 nM final concentration in medium, or at 0.12 µM to 0.05 nM with particularly potent compounds. Cells were exposed to the representative compounds overnight (16-18 hours) in a 37° C. incubator.

96-Well flat-bottom plates were coated with 100 µL per well anti-HT7 capture antibody (ThermoFisher, MN1000) diluted 1:300 in 1xPBS at 4° C. overnight, with shaking at 500 rpm. After overnight capture antibody incubation, coated plates were washed four times with 200 µL per well of 1xPBS-0.05% Tween-20, and blocked for 1 hour with 200 µL per well of 1xPBS with 2% BSA. After 1 hour of blocking, plates were washed four times with 200 µL per well of 1xPBS-0.05% Tween-20, prior to sample loading.

Wells of compound-treated cells were visually checked for cell death before being washed with 200 µL per well of 1xDPBS supplemented with phosphatase inhibitor diluted to 1x. Cells were then lysed with 100 µL 1xRIPA buffer supplemented with phosphatase and protease inhibitors (each diluted to a final 1x). Cells were shaken at 500 rpm, 4° C. for 20 minutes prior to further lysis (via manual scraping) and transfer to 96-well V-bottom collection plates (Corning, 3894). V-bottom plates were centrifuged at 4000 rpm, 4° C., for 15 minutes, and 100 µL of lysate supernatant from each well was directly tested for pT212Tau signal by sandwich ELISA.

Specifically, lysates were directly transferred to the coated and blocked ELISA plates for 2 hours before plates were washed four times with 200 µL per well of 1×PBS-0.05% Tween-20 and probed with 100 µL per well of anti-pT212Tau antibody (ThermoFisher, 44-740G) diluted 1:200 in 1×PBS for 2 hours. Plates were washed four times with 200 µL per well of 1×PBS-0.05% Tween-20 and probed with 100 µL per well of anti-rabbit/HRP conjugate (Cell Signaling Technology, 7074S) diluted 1:600 in 1×PBS for 1 hour. Plates were washed four times with 200 µL per well of 1×PBS-0.05% Tween-20 before 100 µL per well of TMB substrate solution (ThermoFisher, N301) was added. When colour development was observed, 100 µL per well of stop solution (ThermoFisher, N600) was added, and colorimetric detection of pT212Tau signal was read at 450 nm with the Cytation 3 Cell Imaging Multi-Mode Reader (BioTek). The signal was used to plot, draw the curves fitting, and determine the $EC_{50}$ values in GraphPad Prism for tested representative compounds.

Table 6 shows the activity of representative compounds Formulas I, Ia, Ib, Ic, Id, and Ie as provided herein.

TABLE 6

| Compound | Thr212 $EC_{50}$ (µM) |
|---|---|
| 47 | 0.668 |
| 105 | 0.263 |
| 280 | 0.032 |
| 566 | 6.600 |
| 1354 | 0.006 |
| 1632 | 0.402 |
| 1815 | >10 |
| 1953 | >10 |
| 2864 | 0.310 |
| 2865 | 0.122 |
| 2866 | 1.600 |
| 2867 | 0.046 |
| 3098 | 2.000 |
| 3105 | 7.800 |
| 3638 | 0.112 |
| 3643 | 0.030 |
| 3727 | 0.015 |
| 3773 | 0.268 |
| 4244 | 0.157 |
| 4561 | 0.306 |
| 4565 | 0.042 |
| 4569 | 0.238 |

Example 19

Representative compounds were screened using the assay procedure to assess the effect on cell viability as described below.

SW480 colon carcinoma cells were transduced with a lentiviral vector expressing luciferase with a human Sp5 promoter consisting of a sequence of eight TCF/LEF binding sites. SW480 cells stably expressing the Sp5-Luc reporter gene and a hygromycin resistance gene were selected by treatment with 150 µg/mL of hygromycin for 7 days. These stably transduced SW480 cells were expanded in cell culture and used for all further screening activities. Each compound was dissolved in DMSO as a 10 mM stock and used to prepare compound source plates. Serial dilution (1:3, 8-point dose-response curves from 10 µM to 0.0045 µM) and compound transfer was performed using the ECHO 550 (Labcyte, Sunnyvale, Calif.) into 384-well white solid bottom assay plates (Greiner Bio-One) with appropriate DMSO backfill for a final DMSO concentration of 0.1%.

For the Cell Viability Assays, the cells were plated at 2,000 cells/well in 384-well plates with a DMEM medium containing 1% fetal bovine serum, and 1% Penicillin-Streptomycin and incubated for four days hours at 37° C. and 5% $CO_2$. Eight replicates of DMSO-treated cells served as controls and cells treated with compound were performed in duplicate.

After incubation, 10 µL of CellTiter-Glo (Promega) was added to each well allowed to incubate for approximately 12 minutes. This reagent "results in cell lysis and generation of a luminescent signal proportional to the amount of ATP present. The amount of ATP is directly proportional to the number of cells present in culture, in agreement with previous reports. The CellTiter-Glo Assay generates a "glow-type" luminescent signal, produced by the luciferase reaction (Promega.com)".

After incubation, the plates were read at Ex 560 nm Em 590 nm (Cytation 3, BioTek). Dose-response curves were generated and $EC_{50}$ concentration values were calculated using non-linear regression curve fit in the GraphPad Prism (San Diego, Calif.) or Dotmatics' Studies Software (Bishops Stortford, UK). For $EC_{50}$ of >10 µM, the percent inhibition at 10 µM is provided.

Table 6 shows the activity of representative compounds of Formulas I, Ia, Ib, Ic, Id, and Ie as provided herein.

TABLE 6

| Compound | $EC_{50}$ (µM) |
|---|---|
| 2 | 2.472 |
| 5 | >10 (39.9%) |
| 11 | 5.800 |
| 16 | >10 (45.1%) |
| 41 | >10 (31.8%) |
| 47 | >10 (35.2%) |
| 56 | >10 (35.0%) |
| 62 | >10 (38.3%) |
| 71 | >10 (40.7%) |
| 86 | 3.606 |
| 95 | >10 (38.6%) |
| 99 | >10 (37.0%) |
| 105 | >10 (38.9%) |
| 112 | 7.791 |
| 122 | 3.110 |
| 145 | 0.535 |
| 147 | 0.311 |
| 151 | 3.682 |
| 153 | 0.353 |
| 164 | 2.773 |
| 170 | 3.370 |
| 172 | 1.012 |
| 194 | 7.618 |
| 202 | 9.314 |
| 209 | 3.150 |
| 216 | 3.156 |
| 228 | 0.105 |
| 229 | 0.122 |
| 234 | 0.229 |
| 241 | 0.466 |
| 242 | 0.541 |
| 280 | 2.413 |
| 283 | 4.241 |
| 314 | 0.441 |
| 317 | 3.533 |
| 333 | >10 (35.6%) |
| 347 | >10 (10.7%) |
| 358 | >10 (38.0%) |
| 372 | >10 (23.2%) |
| 376 | 1.512 |

TABLE 6-continued

| Compound | EC$_{50}$ (µM) |
|---|---|
| 379 | 1.340 |
| 400 | 2.373 |
| 416 | >10 (52.1%) |
| 447 | 0.165 |
| 448 | >10 (16.2%) |
| 450 | 0.409 |
| 477 | 1.687 |
| 523 | 0.814 |
| 540 | >10 (5.3%) |
| 556 | >10 (29.4%) |
| 566 | >10 (19.7%) |
| 585 | 2.693 |
| 589 | >10 (22.9%) |
| 591 | 3.247 |
| 592 | >10 (11.7%) |
| 613 | 3.597 |
| 624 | 0.694 |
| 625 | >10 (47.8%) |
| 634 | >10 (41.2%) |
| 640 | >10 (40.4%) |
| 641 | 1.684 |
| 642 | 1.030 |
| 643 | 0.803 |
| 662 | >10 (17.3%) |
| 692 | >10 (28.7%) |
| 764 | >10 (24.7%) |
| 804 | 0.272 |
| 807 | 0.860 |
| 862 | 4.384 |
| 863 | >10 (27.5%) |
| 871 | >10 (33.5%) |
| 877 | >10 (11.7%) |
| 892 | 2.055 |
| 896 | 0.109 |
| 909 | >10 (45.6%) |
| 918 | >10 (10.2%) |
| 923 | >10 (33.9%) |
| 954 | >10 (45.1%) |
| 963 | >10 (27.9%) |
| 969 | >10 (16.3%) |
| 978 | >10 (50.0%) |
| 979 | >10 (16.7%) |
| 985 | >10 (9.6%) |
| 994 | >10 (24.8%) |
| 1003 | >10 (18.5%) |
| 1007 | >10 (17.9%) |
| 1013 | >10 (10.5%) |
| 1029 | >10 (38.5%) |
| 1047 | 8.467 |
| 1052 | 5.373 |
| 1054 | 0.719 |
| 1058 | 9.432 |
| 1060 | 6.960 |
| 1071 | 3.470 |
| 1077 | 3.395 |
| 1079 | 3.386 |
| 1101 | 4.475 |
| 1109 | 9.476 |
| 1116 | 3.034 |
| 1123 | 6.122 |
| 1136 | 2.905 |
| 1141 | 0.717 |
| 1186 | >10 (35.2%) |
| 1189 | >10 (17.4%) |
| 1210 | 0.695 |
| 1220 | 5.300 |
| 1223 | >10 (40.0%) |
| 1239 | >10 (17.2%) |
| 1253 | >10 (17.1%) |
| 1254 | >10 (11.2%) |
| 1264 | >10 (27.8%) |
| 1278 | 8.526 |
| 1282 | 1.343 |
| 1285 | 3.141 |
| 1288 | 1.088 |
| 1297 | >10 (35.1%) |
| 1306 | >10 (43.7%) |
| 1322 | >10 (22.2%) |
| 1353 | 4.480 |
| 1354 | 5.343 |
| 1356 | 8.596 |
| 1383 | >10 (26.1%) |
| 1438 | >10 (14.7%) |
| 1447 | >10 (8.5%) |
| 1462 | >10 (20.9%) |
| 1471 | >10 (11.3%) |
| 1472 | >10 (16.7%) |
| 1491 | 8.856 |
| 1495 | >10 (25.5%) |
| 1497 | >10 (23.7%) |
| 1518 | >10 (25.3%) |
| 1519 | >10 (17.1%) |
| 1523 | >10 (15.1%) |
| 1524 | >10 (18.1%) |
| 1536 | 1.042 |
| 1589 | 0.331 |
| 1598 | >10 (8.4%) |
| 1612 | >10 (23.8%) |
| 1625 | >10 (18.8%) |
| 1632 | >10 (21.3%) |
| 1634 | >10 (13.7%) |
| 1656 | 2.210 |
| 1670 | 9.050 |
| 1710 | >10 (39.6%) |
| 1713 | 1.565 |
| 1773 | 0.095 |
| 1777 | >10 (27.6%) |
| 1783 | >10 (38.8%) |
| 1785 | >10 (34.3%) |
| 1802 | 1.366 |
| 1813 | 1.003 |
| 1815 | >10 (15.8%) |
| 1953 | >10 (7.8%) |
| 2722 | >10 (31.0%) |
| 2731 | >10 (26.5%) |
| 2736 | >10 (10.7%) |
| 2767 | >10 (37.0%) |
| 2776 | >10 (8.1%) |
| 2782 | >10 (18.8%) |
| 2791 | >10 (24.8%) |
| 2792 | >10 (29.0%) |
| 2807 | >10 (7.9%) |
| 2816 | >10 (23.2%) |
| 2820 | >10 (22.4%) |
| 2826 | >10 (20.4%) |
| 2864 | 4.060 |
| 2865 | 4.376 |
| 2866 | 2.482 |
| 2867 | 4.052 |
| 2871 | 4.685 |
| 2884 | 3.876 |
| 2890 | 3.861 |
| 2892 | >10 (36.0%) |
| 2914 | 0.692 |
| 2922 | >10 (28.8%) |
| 2929 | 1.064 |
| 2936 | >10 (17.8%) |
| 2949 | 0.440 |
| 2954 | 1.502 |
| 3000 | 5.953 |
| 3003 | >10 (35.9%) |
| 3024 | 3.369 |
| 3032 | 0.599 |
| 3034 | >10 (10.5%) |
| 3037 | >10 (26.1%) |
| 3067 | >10 (42.2%) |
| 3078 | >10 (16.0%) |
| 3092 | >10 (10.5%) |
| 3096 | 4.095 |
| 3098 | >10 (14.4%) |
| 3099 | >10 (29.6%) |
| 3102 | 6.913 |
| 3105 | 9.749 |
| 3111 | >10 (16.1%) |
| 3118 | >10 (8.3%) |
| 3120 | >10 (21.4%) |

TABLE 6-continued

| Compound | EC$_{50}$ (µM) |
|---|---|
| 3134 | >10 (23.8%) |
| 3136 | >10 (18.4%) |
| 3167 | >10 (8.1%) |
| 3168 | >10 (25.8%) |
| 3194 | 4.065 |
| 3240 | >10 (18.6%) |
| 3249 | >10 (26.7%) |
| 3257 | >10 (15.0%) |
| 3259 | 1.936 |
| 3311 | >10 (5.4%) |
| 3363 | 3.955 |
| 3403 | 1.426 |
| 3412 | >10 (41.5%) |
| 3425 | >10 (29.9%) |
| 3439 | >10 (16.8%) |
| 3446 | >10 (16.1%) |
| 3470 | 3.961 |
| 3474 | >10 (17.1%) |
| 3524 | 3.706 |
| 3527 | >10 (41.8%) |
| 3587 | 0.821 |
| 3591 | >10 (6.1%) |
| 3597 | >10 (8.1%) |
| 3599 | 8.848 |
| 3612 | 2.828 |
| 3616 | 0.504 |
| 3627 | 3.422 |
| 3629 | 0.951 |
| 3638 | 6.925 |
| 3643 | 6.989 |
| 3646 | 9.577 |
| 3674 | 6.899 |
| 3683 | >10 (38.8%) |
| 3689 | >10 (28.8%) |
| 3698 | 6.904 |
| 3699 | 6.718 |
| 3714 | 6.023 |
| 3723 | >10 (43.7%) |
| 3727 | 6.660 |
| 3733 | >10 (37.3%) |
| 3749 | 3.614 |
| 3772 | 8.162 |
| 3773 | 5.642 |
| 3774 | 9.638 |
| 3778 | 7.717 |
| 3780 | 2.260 |
| 3783 | 1.969 |
| 3791 | 3.419 |
| 3797 | 7.024 |
| 3799 | 3.658 |
| 3821 | 0.231 |
| 3829 | 9.323 |
| 3836 | >10 (33.9%) |
| 3843 | >10 (14.0%) |
| 3856 | 0.446 |
| 3861 | 0.933 |
| 3907 | 1.295 |
| 3910 | 3.540 |
| 3941 | 2.379 |
| 3944 | 7.295 |
| 3960 | >10 (38.5%) |
| 3974 | 4.922 |
| 3985 | >10 (34.9%) |
| 3999 | >10 (27.3%) |
| 4003 | >10 (50.4%) |
| 4006 | 7.867 |
| 4027 | >10 (26.3%) |
| 4041 | 4.544 |
| 4074 | 2.312 |
| 4075 | >10 (35.4%) |
| 4077 | 2.785 |
| 4104 | 7.749 |
| 4150 | >10 (32.7%) |
| 4159 | 8.439 |
| 4167 | >10 (11.9%) |
| 4218 | 5.964 |
| 4239 | >10 (27.6%) |
| 4244 | >10 (19.9%) |
| 4257 | 2.464 |
| 4319 | >10 (43.0%) |
| 4332 | >10 (16.5%) |
| 4346 | >10 (12.2%) |
| 4353 | >10 (4.1%) |
| 4377 | 5.397 |
| 4431 | 3.152 |
| 4432 | 2.029 |
| 4434 | 5.152 |
| 4498 | 0.799 |
| 4504 | >10 (47.9%) |
| 4523 | 0.513 |
| 4535 | 4.050 |
| 4536 | >10 (45.9%) |
| 4537 | >10 (4.7%) |
| 4538 | 0.952 |
| 4539 | 0.782 |
| 4544 | 5.614 |
| 4548 | >10 (29.8%) |
| 4551 | 1.040 |
| 4558 | 5.798 |
| 4559 | >10 (44.8%) |
| 4560 | >10 (37.5%) |
| 4561 | >10 (49.5%) |
| 4564 | >10 (21.1%) |
| 4565 | 1.549 |
| 4569 | 2.220 |
| 4570 | 5.620 |
| 4573 | 2.696 |
| 4574 | >10 (20.2%) |
| 4576 | >10 (22.1%) |
| 4577 | >10 (19.7%) |
| 4586 | >10 (25.1%) |
| 4593 | >10 (27.4%) |
| 4594 | >10 (15.0%) |
| 4595 | 4.568 |
| 4600 | 2.894 |
| 4602 | >10 (26.1%) |
| 4609 | >10 (6.1%) |
| 4610 | >10 (24.6%) |
| 4611 | >10 (33.7%) |
| 4612 | >10 (20.4%) |
| 4614 | 3.341 |
| 4615 | 2.672 |
| 4616 | >10 (2.6%) |
| 4618 | >10 (36.1%) |
| 4622 | >10 (27.9%) |
| 4623 | >10 (14.1%) |
| 4632 | >10 (40.9%) |
| 4634 | >10 (50.0%) |
| 4640 | 0.545 |
| 4641 | >10 (42.6%) |
| 4643 | >10 (30.1%) |
| 4646 | 0.668 |
| 4647 | >10 (41.1%) |
| 4650 | >10 (10.9%) |
| 4657 | 1.698 |
| 4658 | 0.245 |

Example 20

Representative compounds were screened using primary human fibroblasts (derived from IPF patients) treated with TGF-β1 to determine their ability to inhibit the fibrotic process.

Human Fibroblast Cell Culture:

Primary human fibroblasts derived from IPF patients (LL29 cells) [[1]Xiaoqiu Liu, et. al., "Fibrotic Lung Fibroblasts Show Blunted Inhibition by cAMP Due to Deficient cAMP Response Element-Binding Protein Phosphorylation", *Journal of Pharmacology and Experimental Therapeutics* (2005), 315(2), 678-687; [2]Watts, K. L., et. al., "RhoA signaling modulates cyclin D1 expression in human lung fibroblasts; implications for idiopathic pulmonary fibrosis", Respiratory Research (2006), 7(1), 88] were obtained from American Type Culture Collection (ATCC) and expanded in F12 medium supplemented with 15% Fetal Bovine Serum and 1% Penicillin/Streptomycin.

Compound Screening:

Each compound was dissolved in DMSO as a 10 mM stock and used to prepare compound source plates. Serial dilution (1:2, 11-point dose-response curves from 10 µM to 0.94 nM) and compound transfer was performed using the ECHO 550 (Labcyte, Sunnyvale, Calif.) into 384-well clear bottom assay plates (Greiner Bio-One) with appropriate DMSO backfill for a final DMSO concentration of 0.1%. LL29 cells were plated at 1,500 cells/well in 70 µL/well F12 medium supplemented with 1% Fetal Bovine Serum. TGF-β1 (Peprotech; 20 ng/mL) was added to the plates to induce fibrosis (ref. 1 and 2 above). Wells treated with TGF-β1 and containing DMSO were used as positive control, and cells with only DMSO were negative control. Cells were incubated at 37° C. and 5% $CO_2$ for 4 days. Following incubation for 4 days, SYTOX green nucleic acid stain (Life Technologies [Thermo Fisher Scientific]) was added to the wells at a final concentration of 1 µM and incubated at room temperature for 30 min. Cells were then fixed using 4% formaldehyde (Electron Microscopy Sciences), washed 3 times with PBS followed by blocking and permeabilization using 3% Bovine Serum Albumin (BSA; Sigma) and 0.3% Triton X-100 (Sigma) in PBS. Cells were then stained with antibody specific to α-smooth muscle actin (aSMA; Abcam) (ref. 1 and 2 above) in 3% Bovine Serum Albumin (BSA; Sigma) and 0.3% Triton X-100 (Sigma) in PBS, and incubated overnight at 4° C. Cells were then washed 3 times with PBS, followed by incubation with Alexa Flor-647 conjugated secondary antibody (Life Technologies [Thermo Fisher Scientific]) and DAPI in 3% Bovine Serum Albumin (BSA; Sigma) and 0.3% Triton X-100 (Sigma) in PBS at room temperature for 1 hour. Cells were then washed 3 times with PBS and plates were sealed for imaging. aSMA staining was imaged by excitation at 630 nm and emission at 665 nm and quantified using the Compartmental Analysis program on the CellInsight CX5 (Thermo Scientific). Dead or apoptotic cells were excluded from analysis based on positive SYTOX green staining. % of total cells positive for aSMA were counted in each well and normalized to the average of 11 wells treated with TGF-β1 on the same plate using Dotmatics' Studies Software. The normalized averages (fold change over untreated) of 3 replicate wells for each compound concentration were used to create dose-responses curves and $EC_{50}$ values were calculated using non-linear regression curve fit in the Dotmatics' Studies Software. For $EC_{50}$ of >10 µM, the percent inhibition at 10 µM is provided.

Table 7 shows the activity of representative compounds of Formulas I, Ia, Ib, Ic, Id, and Ie as provided herein.

TABLE 7

| Compound | $EC_{50}$ (µM) |
| --- | --- |
| 2 | 0.677 |
| 5 | >10 (9.0%) |
| 11 | 2.536 |
| 16 | 0.251 |
| 41 | 0.663 |
| 47 | 7.196 |
| 56 | 5.179 |
| 62 | >10 (8.3%) |
| 71 | 0.420 |
| 86 | 1.894 |
| 95 | 0.444 |
| 99 | 4.060 |

TABLE 7-continued

| Compound | $EC_{50}$ (µM) |
| --- | --- |
| 105 | >10 (16.9%) |
| 112 | >10 (13.8%) |
| 122 | 4.020 |
| 145 | 0.369 |
| 147 | 0.410 |
| 151 | 0.432 |
| 153 | 1.105 |
| 164 | 0.717 |
| 170 | 1.298 |
| 172 | 0.393 |
| 194 | 0.935 |
| 202 | 0.530 |
| 209 | 0.436 |
| 216 | 0.598 |
| 228 | 0.376 |
| 229 | 0.318 |
| 234 | 0.329 |
| 241 | 1.577 |
| 242 | 1.416 |
| 280 | 2.521 |
| 283 | 3.912 |
| 314 | 0.989 |
| 317 | 0.935 |
| 333 | >10 (25.2%) |
| 347 | >10 (20.7%) |
| 358 | >10 (9.8%) |
| 372 | 3.636 |
| 376 | 3.485 |
| 379 | 2.145 |
| 400 | 1.475 |
| 416 | 0.355 |
| 447 | 0.517 |
| 448 | >10 (23.0%) |
| 450 | 0.517 |
| 477 | 0.632 |
| 523 | 1.634 |
| 540 | >10 (50.0%) |
| 556 | >10 (27.6%) |
| 566 | >10 (35.2%) |
| 585 | 2.513 |
| 589 | >10 (41.6%) |
| 591 | >10 (13.3%) |
| 592 | 0.009 |
| 613 | 0.650 |
| 624 | 0.491 |
| 625 | 3.009 |
| 634 | 2.130 |
| 640 | 0.671 |
| 641 | 0.347 |
| 642 | 0.988 |
| 643 | 1.433 |
| 662 | 7.653 |
| 692 | >10 (3.8%) |
| 764 | >10 (5.8%) |
| 804 | 0.482 |
| 807 | 1.408 |
| 862 | 5.032 |
| 863 | >10 (41.0%) |
| 871 | 8.053 |
| 877 | >10 (23.6%) |
| 892 | 3.978 |
| 896 | 0.335 |
| 909 | 1.385 |
| 918 | >10 (31.2%) |
| 923 | 2.724 |
| 954 | 2.135 |
| 963 | 1.570 |
| 969 | >10 (40.2%) |
| 978 | 2.734 |
| 979 | >10 (23.2%) |
| 985 | >10 (51.7%) |
| 994 | >10 (0%) |
| 1003 | >10 (4.8%) |
| 1007 | >10 (39.7%) |
| 1013 | >10 (12.4%) |
| 1029 | >10 (28.0%) |
| 1047 | 1.928 |
| 1052 | 8.737 |

TABLE 7-continued

| Compound | EC$_{50}$ (μM) |
|---|---|
| 1054 | 2.338 |
| 1058 | >10 (8.8%) |
| 1060 | >10 (28.6%) |
| 1071 | 6.842 |
| 1077 | 3.919 |
| 1079 | >10 (14.3%) |
| 1101 | >10 (12.7%) |
| 1109 | >10 (16.4%) |
| 1116 | 2.715 |
| 1123 | >10 (22.0%) |
| 1136 | 1.457 |
| 1141 | 1.387 |
| 1186 | >10 (24.5%) |
| 1189 | >10 (18.0%) |
| 1210 | 1.399 |
| 1220 | >10 (5.5%) |
| 1223 | 1.821 |
| 1239 | >10 (13.5%) |
| 1253 | >10 (47.2%) |
| 1254 | 6.970 |
| 1264 | >10 (5.7%) |
| 1278 | >10 (35.9%) |
| 1282 | 2.535 |
| 1285 | >10 (5.5%) |
| 1288 | 8.011 |
| 1297 | >10 (42.1%) |
| 1306 | 1.804 |
| 1322 | 1.997 |
| 1353 | >10 (42.0%) |
| 1354 | 5.092 |
| 1356 | 3.602 |
| 1383 | 3.290 |
| 1438 | >10 (29.6%) |
| 1447 | >10 (35.5%) |
| 1462 | >10 (14.5%) |
| 1471 | >10 (43.6%) |
| 1472 | >10 (33.9%) |
| 1491 | >10 (6.1%) |
| 1495 | >10 (48.5%) |
| 1497 | 2.427 |
| 1518 | 2.606 |
| 1519 | 2.399 |
| 1523 | >10 (24.9%) |
| 1524 | 4.775 |
| 1536 | 1.130 |
| 1589 | 0.911 |
| 1598 | 1.271 |
| 1612 | >10 (42.0%) |
| 1625 | 1.766 |
| 1632 | >10 (28.8%) |
| 1634 | >10 (18.3%) |
| 1656 | 1.756 |
| 1670 | 4.846 |
| 1710 | >10 (10.4%) |
| 1713 | 5.160 |
| 1773 | 0.163 |
| 1777 | >10 (41.1%) |
| 1783 | >10 (53.7%) |
| 1785 | 4.004 |
| 1802 | >10 (47.6%) |
| 1813 | 5.825 |
| 1815 | >10 (33.5%) |
| 1953 | >10 (55.5%) |
| 2722 | 1.011 |
| 2731 | 5.319 |
| 2736 | >10 (17.0%) |
| 2767 | >10 (13.8%) |
| 2776 | >10 (39.0%) |
| 2782 | 2.404 |
| 2791 | 6.131 |
| 2792 | >10 (44.8%) |
| 2807 | >10 (35.2%) |
| 2816 | >10 (27.3%) |
| 2820 | 8.909 |
| 2826 | >10 (37.9%) |
| 2864 | >10 (7.3%) |
| 2865 | 5.115 |
| 2866 | >10 (47.4%) |

TABLE 7-continued

| Compound | EC$_{50}$ (μM) |
|---|---|
| 2867 | 5.379 |
| 2871 | 9.773 |
| 2884 | 5.236 |
| 2890 | >10 (29.4%) |
| 2892 | 3.964 |
| 2914 | 0.893 |
| 2922 | >10 (47.2%) |
| 2929 | 2.254 |
| 2936 | >10 (21.6%) |
| 2949 | 5.151 |
| 2954 | 3.337 |
| 3000 | 9.890 |
| 3003 | >10 (27.8%) |
| 3024 | >10 (50.0%) |
| 3032 | 1.585 |
| 3034 | >10 (31.8%) |
| 3037 | >10 (31.2%) |
| 3067 | >10 (31.7%) |
| 3078 | >10 (41.0%) |
| 3092 | >10 (13.3%) |
| 3096 | >10 (32.7%) |
| 3098 | >10 (8.3%) |
| 3099 | >10 (44.4%) |
| 3102 | >10 (50.0%) |
| 3105 | >10 (21.8%) |
| 3111 | >10 (46.4%) |
| 3118 | 4.905 |
| 3120 | >10 (27.0%) |
| 3134 | >10 (19.7%) |
| 3136 | 0.135 |
| 3167 | 2.042 |
| 3168 | >10 (10.2%) |
| 3194 | >10 (47.3%) |
| 3240 | >10 (15.9%) |
| 3249 | 7.065 |
| 3257 | >10 (36.0%) |
| 3259 | >10 (48.4%) |
| 3311 | 1.441 |
| 3363 | >10 (34.7%) |
| 3403 | 2.429 |
| 3412 | >10 (46.2%) |
| 3425 | >10 (19.3%) |
| 3439 | >10 (14.3%) |
| 3446 | >10 (16.9%) |
| 3470 | 3.229 |
| 3474 | >10 (37.0%) |
| 3524 | >10 (50.0%) |
| 3527 | 3.496 |
| 3587 | 1.435 |
| 3591 | |
| 3597 | >10 (7.7%) |
| 3599 | 3.008 |
| 3612 | 3.901 |
| 3616 | 3.164 |
| 3627 | >10 (33.4%) |
| 3629 | 0.097 |
| 3638 | >10 (34.9%) |
| 3643 | 2.503 |
| 3646 | >10 (12.9%) |
| 3674 | 0.604 |
| 3683 | 0.597 |
| 3689 | 0.893 |
| 3698 | 1.070 |
| 3699 | 0.025 |
| 3714 | 1.539 |
| 3723 | >10 (9.1%) |
| 3727 | 0.149 |
| 3733 | 1.833 |
| 3749 | 0.167 |
| 3772 | 1.135 |
| 3773 | 3.318 |
| 3774 | 5.859 |
| 3778 | 0.694 |
| 3780 | 4.759 |
| 3783 | 2.101 |
| 3791 | 4.946 |
| 3797 | 2.696 |
| 3799 | 2.578 |

TABLE 7-continued

| Compound | EC$_{50}$ (µM) |
| --- | --- |
| 3821 | 0.313 |
| 3829 | 0.759 |
| 3836 | >10 (10.0%) |
| 3843 | 1.276 |
| 3856 | >10 (17.5%) |
| 3861 | 0.597 |
| 3907 | 1.823 |
| 3910 | 1.068 |
| 3941 | 1.194 |
| 3944 | 0.416 |
| 3960 | >10 (23.5%) |
| 3974 | 2.023 |
| 3985 | 8.385 |
| 3999 | >10 (34.6%) |
| 4003 | >10 (24.6%) |
| 4006 | >10 (5.2%) |
| 4027 | >10 (33.9%) |
| 4041 | 3.487 |
| 4074 | 3.189 |
| 4075 | >10 (39.2%) |
| 4077 | 1.018 |
| 4104 | 3.083 |
| 4150 | 3.571 |
| 4159 | 0.347 |
| 4167 | >10 (43.0%) |
| 4218 | 2.979 |
| 4239 | >10 (50.0%) |
| 4244 | >10 (4.9%) |
| 4257 | 2.516 |
| 4319 | 1.626 |
| 4332 | >10 (23.6%) |
| 4346 | >10 (21.4%) |
| 4353 | >10 (26.4%) |
| 4377 | 2.955 |
| 4431 | 2.489 |
| 4432 | 1.721 |
| 4434 | 1.603 |
| 4498 | 0.436 |
| 4504 | 0.384 |
| 4523 | 2.383 |
| 4535 | >10 (25.0%) |
| 4536 | 1.140 |
| 4537 | 5.274 |
| 4538 | 0.708 |
| 4539 | 1.098 |
| 4544 | 1.092 |
| 4548 | >10 (50.0%) |
| 4551 | 0.325 |
| 4558 | 0.277 |
| 4559 | 0.589 |
| 4560 | 0.779 |
| 4561 | 0.664 |
| 4564 | >10 (26.8%) |
| 4565 | >10 (31.0%) |
| 4569 | 4.095 |
| 4570 | >10 (5.5%) |
| 4573 | >10 (9.3%) |
| 4574 | >10 (32.8%) |
| 4576 | >10 (38.3%) |
| 4577 | >10 (42.7%) |
| 4586 | 4.440 |
| 4593 | >10 (41.4%) |
| 4594 | 3.250 |
| 4595 | >10 (2.8%) |
| 4600 | >10 (47.0%) |
| 4602 | >10 (14.3%) |
| 4609 | >10 (45.9%) |
| 4610 | 4.189 |
| 4611 | >10 (29.9%) |
| 4612 | >10 (13.2%) |
| 4614 | 2.256 |
| 4615 | >10 (35.6%) |
| 4616 | >10 (25.9%) |
| 4618 | 4.809 |
| 4622 | >10 (29.4%) |
| 4623 | >10 (4.2%) |
| 4632 | >10 (35.5%) |
| 4634 | >10 (39.9%) |

TABLE 7-continued

| Compound | EC$_{50}$ (µM) |
| --- | --- |
| 4640 | 0.896 |
| 4641 | 2.422 |
| 4643 | 1.512 |
| 4646 | 0.665 |
| 4647 | >10 (39.6%) |
| 4650 | >10 (23.0%) |
| 4657 | 4.805 |
| 4658 | 1.587 |

Example 21

Representative compounds were screened using the cell-based assay procedure for secreted cytokines in a Lipopolysaccharide-stimulated mouse glial cell line described below.

BV-2 cells (mouse microglial cells) were cultured in 1:1 DMEM medium supplemented with 10% FBS, and 1% penicillin/streptomycin.

BV-2 cells are plated at 35,000 cells/well in a volume of 100 µl for at least 4 hours before compounds are added. DMSO-resuspended compounds were first dispensed in a 96-well plate and serial diluted from 10 µM to 4.6 nM final concentration in medium. Compounds were added to cells overnight. 250 ng/mL of lipopolysaccharide (*Escherichia coli* O111:B4, SIGMA) was added for 5 hours. Supernatant is removed and saved for further cytokine detection. The original plates with seeded cells were tested for cytotoxicity by measure of adenosine triphosphate (ATP) release by adding CellTiter-Glo® diluted 1:4 in distilled water (G7573, Promega) and transferring lysed cells to a completely black 96-well plate to be read with the Cytation3. Supernatant was then diluted 1:2 with a diluent from V-PLEX cytokine Kit and directly tested for the secreted cytokines TNFα, IL-6 and KC-GRO using electrochemiluminescence (Meso Scale Discovery). The standard curve for each cytokine was used to convert the electrochemiluminescent signal into pg of protein per mL. The signal was used to plot, draw the curve fitting, and determine each compounds EC$_{50}$ in Prism (GraphPad).

Table 9 shows the activity of representative compounds of Formulas I, Ia, Ib, Ic, Id, and Ie as provided herein.

TABLE 9

| Compound | EC$_{50}$ (µM) |
| --- | --- |
| 2 | 1.700 |
| 5 | 0.400 |
| 11 | 0.926 |
| 16 | 0.111 |
| 41 | 0.408 |
| 47 | 0.260 |
| 56 | 1.140 |
| 62 | 0.557 |
| 71 | 0.093 |
| 86 | 0.201 |
| 95 | 0.066 |
| 99 | 0.177 |
| 105 | 1.130 |
| 112 | 5.400 |
| 122 | 0.590 |
| 145 | 0.212 |
| 147 | 0.122 |
| 151 | 0.088 |
| 153 | 0.159 |
| 164 | 0.165 |
| 170 | 0.055 |

TABLE 9-continued

| Compound | EC$_{50}$ (µM) |
|---|---|
| 172 | 0.214 |
| 194 | 0.819 |
| 202 | 0.300 |
| 209 | 0.864 |
| 216 | 0.378 |
| 228 | 0.207 |
| 229 | 0.062 |
| 234 | 0.026 |
| 314 | 0.138 |
| 317 | 0.066 |
| 376 | 1.700 |
| 379 | 0.734 |
| 416 | 3.300 |
| 447 | 0.083 |
| 450 | 3.000 |
| 477 | 4.800 |
| 523 | 0.799 |
| 540 | 10.000 |
| 556 | 2.200 |
| 585 | 0.257 |
| 592 | 0.449 |
| 613 | 0.106 |
| 624 | 8.800 |
| 625 | 0.130 |
| 634 | 0.542 |
| 640 | 0.504 |
| 641 | 0.433 |
| 642 | 1.300 |
| 643 | 10.000 |
| 764 | 5.100 |
| 804 | 0.104 |
| 807 | 0.265 |
| 871 | 0.306 |
| 877 | 2.700 |
| 896 | 0.266 |
| 909 | 1.900 |
| 918 | >10 |
| 923 | 1.070 |
| 963 | 0.354 |
| 985 | >10 |
| 994 | 1.300 |
| 1003 | 1.490 |
| 1007 | 1.800 |
| 1047 | 0.780 |
| 1054 | 1.200 |
| 1058 | 0.286 |
| 1060 | 0.280 |
| 1071 | 1.800 |
| 1077 | 0.203 |
| 1079 | 1.400 |
| 1101 | 3.100 |
| 1109 | 0.349 |
| 1116 | 0.960 |
| 1123 | 1.000 |
| 1136 | 0.554 |
| 1141 | 0.177 |
| 1186 | 5.600 |
| 1210 | 1.100 |
| 1220 | 0.877 |
| 1253 | >10 |
| 1278 | 7.200 |
| 1282 | 1.000 |
| 1285 | 6.800 |
| 1288 | 6.100 |
| 1297 | 10.000 |
| 1353 | 0.812 |
| 1356 | 1.100 |
| 1383 | 6.800 |
| 1447 | 0.605 |
| 1491 | 3.900 |
| 1497 | 0.334 |
| 1518 | 1.080 |
| 1519 | 0.069 |
| 1523 | 1.800 |
| 1524 | 3.600 |
| 1536 | 0.336 |
| 1589 | 0.221 |
| 1598 | 3.100 |
| 1612 | 2.200 |
| 1625 | 0.436 |
| 1670 | 2.900 |
| 1710 | 5.500 |
| 1713 | 1.000 |
| 1773 | 0.005 |
| 1783 | 6.800 |
| 1802 | 4.400 |
| 1813 | 0.952 |
| 1953 | 2.900 |
| 2722 | 0.822 |
| 2731 | 1.200 |
| 2736 | 0.109 |
| 2767 | 0.896 |
| 2776 | 1.000 |
| 2792 | 0.357 |
| 2807 | 0.919 |
| 2816 | 0.445 |
| 2820 | 0.895 |
| 2826 | 5.300 |
| 2865 | 0.160 |
| 2871 | 1.700 |
| 2914 | 0.131 |
| 2929 | 0.234 |
| 2949 | 0.454 |
| 2954 | 0.491 |
| 3000 | 0.307 |
| 3024 | 1.200 |
| 3032 | 0.127 |
| 3037 | 0.817 |
| 3067 | 3.900 |
| 3120 | 0.649 |
| 3168 | 2.600 |
| 3194 | 10.000 |
| 3249 | 1.200 |
| 3257 | 0.458 |
| 3259 | 1.200 |
| 3311 | 0.420 |
| 3412 | 1.500 |
| 3524 | 0.582 |
| 3587 | 0.011 |
| 3591 | 2.400 |
| 3597 | 10.000 |
| 3599 | 0.832 |
| 3616 | 1.200 |
| 3627 | 0.708 |
| 3629 | 5.700 |
| 3638 | 1.400 |
| 3643 | 3.900 |
| 3646 | >10 |
| 3674 | 6.800 |
| 3683 | >10 |
| 3689 | >10 |
| 3698 | 4.800 |
| 3699 | >10 |
| 3714 | 1.620 |
| 3723 | 0.094 |
| 3727 | >10 |
| 3733 | 3.700 |
| 3772 | 10.000 |
| 3773 | 0.305 |
| 3774 | 0.972 |
| 3778 | 0.720 |
| 3783 | 5.300 |
| 3791 | 3.900 |
| 3797 | 0.054 |
| 3799 | 0.079 |
| 3821 | 0.244 |
| 3829 | 0.533 |
| 3836 | 1.000 |
| 3843 | 10.000 |
| 3856 | 0.194 |
| 3861 | 0.343 |
| 3907 | 4.700 |
| 3944 | 0.471 |
| 4027 | 10.000 |
| 4041 | 3.900 |
| 4074 | 0.300 |

TABLE 9-continued

| Compound | EC$_{50}$ (μM) |
|---|---|
| 4075 | 10.000 |
| 4077 | 2.400 |
| 4104 | 1.200 |
| 4159 | 0.859 |
| 4218 | 5.100 |
| 4239 | 1.700 |
| 4244 | >10 |
| 4257 | 0.626 |
| 4319 | 0.516 |
| 4332 | >10 |
| 4431 | 0.040 |
| 4434 | 9.500 |
| 4504 | 0.524 |
| 4523 | 1.300 |
| 4535 | 0.162 |
| 4536 | 0.089 |
| 4538 | 0.047 |
| 4539 | 0.080 |
| 4544 | 0.353 |
| 4548 | 0.400 |
| 4551 | 0.400 |
| 4558 | 0.165 |
| 4559 | 0.411 |
| 4560 | 0.117 |
| 4561 | 0.129 |
| 4565 | 1.000 |
| 4570 | 0.128 |
| 4586 | 0.380 |
| 4593 | 2.500 |
| 4600 | 6.400 |
| 4602 | 2.900 |
| 4610 | 0.261 |
| 4614 | 0.718 |
| 4615 | 0.275 |
| 4618 | 0.108 |
| 4622 | 1.400 |
| 4623 | 1.300 |
| 4632 | 0.700 |
| 4640 | 7.100 |
| 4641 | 1.700 |
| 4643 | >10 |
| 4646 | 0.130 |
| 4650 | >10 |
| 4657 | 0.928 |
| 4658 | 0.058 |

Example 22

Representative compounds were screened using the following assay procedure to determine their ability to inhibit IL-6 and therefore demonstrate their anti-inflammatory properties.

Human Peripheral Blood Mononuclear Cells:

Fresh Normal PB MNC (Catalog # PB001, AllCells, Alameda, Calif.) were shipped overnight at 4° C. and resuspended in Roswell Park Memorial Institute (RPMI) 1640 Medium, with GlutaMAX Supplement (Catalog #61870127, ThermoFisher Scientific, Waltham, Mass.) supplemented with 1% Penicillin-Streptomycin (Catalog #15140163. ThermoFisher Scientific, Waltham, Mass.) and 1% fetal bovine serum (FBS) (Catalog #16140089, ThermoFisher Scientific, Waltham, Mass.) assay media.

Compound Screening:

Fresh normal human peripheral blood mononuclear cells (huPBMCs) were resuspended in 1% FBS-RPMI assay media with 1% Penicillin-Streptomycin 1% to a cell concentration of 1×10e6 cells/mL. Each compound was dissolved in DMSO (Catalog # D8418-100 ml, Sigma-Aldrich, St. Louis, Mo.) as a 10 mM stock and used to prepare compound source plates. Serial dilution (1:3, 10-point dose-response curves starting from 10 μM) and compound transfer was performed using the ECHO 550 (Labcyte, Sunnyvale, Calif.) into 384-well white Proxiplate-Plus assay plates (Catalog #6008289, PerkinElmer, Shelton, Conn.) with appropriate DMSO backfill for a final DMSO concentration of 0.25%. huPBMCs were plated at 5000 cells/well in the 384-well Proxiplate-Plus assay plates and incubated at 37° C.-5% CO$_2$ for 2 hours. 50 ng/mL of Lipopolysaccharides from *Escherichia coli* 0111:B4 (Catalog # L5293-2ML, Sigma-Aldrich, St. Louis, Mo.) was added after 2 hours and cells were incubated for another 22 hours at 37° C.-5% CO$_2$. After 22 hour incubation, a mixture of anti-IL6 XL665 and anti-IL-6 Cryptate diluted in reconstitution buffer (Catalog #62IL6PEC, Cisbio Inc., Bedford, Mass.) was added to each well. Following incubation for 3 hours at room temperature, Homogeneous Time-Resolved Fluorescence (HTRF) was measured using the Envision (Perkin Elmer, Shelton, Conn.) at 665 nm and 620 nM. The ratio of fluorescence at 665 nm to 620 nm was used as a readout for IL-6 quantification. All samples were processed in duplicate. Readings were normalized to DMSO treated cells and normalized activities were utilized for EC$_{50}$ calculations. EC$_{50}$ was determined using software generated by Dotmatics Limited (Windhill Bishops Stortford Herts, UK) using the Levenberg-Marquardt 4 parameter fitting procedure with finite different gradients. For EC$_{50}$ of >10 μM, the percent inhibition at 10 μM is provided.

Table 8 shows the activity of representative compounds of Formulas I, Ia, Ib, Ic, Id, and Ie as provided herein.

TABLE 8

| Compound | EC$_{50}$ (μM) |
|---|---|
| 2 | 3.161 |
| 5 | 3.297 |
| 11 | 2.831 |
| 16 | >10 (52.2%) |
| 41 | 2.766 |
| 47 | >10 (0%) |
| 56 | >10 (6.3%) |
| 62 | 4.832 |
| 71 | 5.491 |
| 86 | 1.020 |
| 95 | 9.094 |
| 99 | 8.605 |
| 105 | >10 (2.6%) |
| 112 | 9.404 |
| 122 | 3.170 |
| 145 | 3.251 |
| 147 | 2.202 |
| 151 | 3.675 |
| 153 | 2.069 |
| 164 | >10 (17.6%) |
| 170 | 8.089 |
| 172 | >10 (32.7%) |
| 194 | 8.943 |
| 202 | >10 (5.1%) |
| 209 | >10 (3.1%) |
| 216 | >10 (0%) |
| 228 | 0.723 |
| 229 | 0.859 |
| 234 | 1.887 |
| 241 | 3.717 |
| 242 | 3.615 |
| 280 | 5.707 |
| 283 | >10 (7.4%) |
| 314 | >10 (47.6%) |
| 317 | >10 (8.0%) |
| 333 | >10 (5.4%) |
| 347 | >10 (4.0%) |
| 358 | >10 (2.0%) |
| 372 | >10 (0%) |
| 376 | 7.962 |
| 379 | 2.075 |
| 400 | 3.655 |

TABLE 8-continued

| Compound | EC$_{50}$ (µM) |
|---|---|
| 416 | 5.757 |
| 447 | 4.250 |
| 448 | 5.128 |
| 450 | 3.514 |
| 477 | 9.828 |
| 523 | >10 (3.7%) |
| 540 | >10 (3.9%) |
| 556 | >10 (4.9%) |
| 566 | >10 (3.6%) |
| 585 | >10 (9.4%) |
| 589 | >10 (5.9%) |
| 591 | >10 (0%) |
| 592 | >10 (25.3%) |
| 613 | 1.099 |
| 624 | 3.082 |
| 625 | >10 (6.5%) |
| 634 | >10 (13.0%) |
| 640 | 7.340 |
| 641 | >10 (16.4%) |
| 642 | >10 (22.4%) |
| 643 | 9.218 |
| 662 | >10 (10.5%) |
| 692 | 6.732 |
| 764 | >10 (4.3%) |
| 804 | 1.594 |
| 807 | 4.204 |
| 862 | >10 (5.6%) |
| 863 | >10 (7.0%) |
| 871 | 3.423 |
| 877 | >10 (6.8%) |
| 892 | >10 (2.5%) |
| 896 | 1.685 |
| 909 | 4.861 |
| 918 | >10 (14.6%) |
| 923 | >10 (10.5%) |
| 954 | >10 (5.7%) |
| 963 | >10 (5.4%) |
| 969 | >10 (4.1%) |
| 978 | >10 (6.9%) |
| 979 | >10 (6.4%) |
| 985 | >10 (3.2%) |
| 994 | 8.314 |
| 1003 | >10 (6.6%) |
| 1007 | >10 (2.4%) |
| 1013 | >10 (3.1%) |
| 1029 | >10 (3.2%) |
| 1047 | 3.708 |
| 1052 | >10 (3.8%) |
| 1054 | 3.933 |
| 1058 | >10 (3.0%) |
| 1060 | >10 (4.9%) |
| 1071 | >10 (11.8%) |
| 1077 | 9.198 |
| 1079 | >10 (12.7%) |
| 1101 | >10 (10.6%) |
| 1109 | >10 (6.3%) |
| 1116 | >10 (3.8%) |
| 1123 | >10 (6.5%) |
| 1136 | 3.198 |
| 1141 | 3.130 |
| 1186 | >10 (6.7%) |
| 1189 | >10 (7.9%) |
| 1210 | 3.613 |
| 1220 | >10 (0%) |
| 1223 | >10 (6.1%) |
| 1239 | >10 (7.3%) |
| 1253 | >10 (4.4%) |
| 1254 | >10 (3.8%) |
| 1264 | >10 (7.9%) |
| 1278 | >10 (3.0%) |
| 1282 | >10 (42.4%) |
| 1285 | >10 (2.1%) |
| 1288 | >10 (9.8%) |
| 1297 | >10 (4.3%) |
| 1306 | 8.809 |
| 1322 | >10 (5.9%) |
| 1353 | >10 (4.1%) |
| 1354 | >10 (39.9%) |

TABLE 8-continued

| Compound | EC$_{50}$ (µM) |
|---|---|
| 1356 | 8.065 |
| 1383 | >10 (3.1%) |
| 1438 | >10 (9.6%) |
| 1447 | >10 (0%) |
| 1462 | >10 (0%) |
| 1471 | >10 (1.8%) |
| 1472 | >10 (7.6%) |
| 1491 | >10 (2.6%) |
| 1495 | >10 (3.2%) |
| 1497 | >10 (4.8%) |
| 1518 | >10 (30.1%) |
| 1519 | >10 (2.9%) |
| 1523 | >10 (6.2%) |
| 1524 | >10 (50.0%) |
| 1536 | >10 (49.6%) |
| 1589 | 2.876 |
| 1598 | >10 (7.5%) |
| 1612 | >10 (6.3%) |
| 1625 | >10 (4.0%) |
| 1632 | >10 (4.2%) |
| 1634 | >10 (5.4%) |
| 1656 | >10 (6.0%) |
| 1670 | >10 (7.2%) |
| 1710 | >10 (7.2%) |
| 1713 | >10 (5.7%) |
| 1773 | >10 (40.7%) |
| 1777 | >10 (2.4%) |
| 1783 | >10 (6.1%) |
| 1785 | >10 (8.9%) |
| 1802 | >10 (47.2%) |
| 1813 | >10 (42.0%) |
| 1815 | >10 (7.0%) |
| 1953 | >10 (12.8%) |
| 2722 | 8.903 |
| 2731 | >10 (2.8%) |
| 2736 | >10 (0%) |
| 2767 | >10 (0%) |
| 2776 | >10 (10.4%) |
| 2782 | >10 (4.3%) |
| 2791 | >10 (5.3%) |
| 2792 | >10 (4.0%) |
| 2807 | 7.313 |
| 2816 | >10 (2.2%) |
| 2820 | >10 (3.3%) |
| 2826 | >10 (2.1%) |
| 2864 | >10 (10.0%) |
| 2865 | 9.614 |
| 2866 | >10 (0%) |
| 2867 | >10 (5.2%) |
| 2871 | >10 (0%) |
| 2884 | >10 (9.4%) |
| 2890 | >10 (8.6%) |
| 2892 | >10 (16.5%) |
| 2914 | >10 (5.0%) |
| 2922 | >10 (3.8%) |
| 2929 | >10 (4.5%) |
| 2936 | >10 (8.3%) |
| 2949 | 9.147 |
| 2954 | >10 (45.0%) |
| 3000 | 2.265 |
| 3003 | >10 (7.3%) |
| 3024 | >10 (11.1%) |
| 3032 | 1.650 |
| 3034 | >10 (9.5%) |
| 3037 | >10 (5.9%) |
| 3067 | >10 (0%) |
| 3078 | >10 (7.9%) |
| 3092 | >10 (7.4%) |
| 3096 | >10 (0%) |
| 3098 | >10 (4.7%) |
| 3099 | >10 (0%) |
| 3102 | >10 (0%) |
| 3105 | >10 (8.0%) |
| 3111 | >10 (7.5%) |
| 3118 | >10 (5.3%) |
| 3120 | >10 (7.4%) |
| 3134 | >10 (3.9%) |
| 3136 | >10 (9.8%) |

TABLE 8-continued
| Compound | EC$_{50}$ (μM) |
|---|---|
| 3167 | >10 (5.4%) |
| 3168 | >10 (0%) |
| 3194 | >10 (8.9%) |
| 3240 | >10 (10.5%) |
| 3249 | 8.319 |
| 3257 | >10 (3.2%) |
| 3259 | >10 (4.1%) |
| 3311 | >10 (5.8%) |
| 3363 | >10 (5.6%) |
| 3403 | >10 (1.8%) |
| 3412 | >10 (2.7%) |
| 3425 | >10 (9.0%) |
| 3439 | >10 (12.7%) |
| 3446 | >10 (5.8%) |
| 3470 | >10 (9.4%) |
| 3474 | >10 (3.9%) |
| 3524 | >10 (5.6%) |
| 3527 | >10 (0%) |
| 3587 | 7.665 |
| 3591 | >10 (4.4%) |
| 3597 | >10 (0%) |
| 3599 | >10 (40.1%) |
| 3612 | 5.051 |
| 3616 | 2.368 |
| 3627 | >10 (10.6%) |
| 3629 | 2.765 |
| 3638 | >10 (6.3%) |
| 3643 | >10 (9.8%) |
| 3646 | 9.042 |
| 3674 | >10 (1.7%) |
| 3683 | >10 (4.6%) |
| 3689 | >10 (7.6%) |
| 3698 | >10 (4.6%) |
| 3699 | >10 (8.4%) |
| 3714 | 5.704 |
| 3723 | >10 (2.8%) |
| 3727 | >10 (6.2%) |
| 3733 | >10 (6.2%) |
| 3749 | 8.804 |
| 3772 | >10 (10.6%) |
| 3773 | >10 (1.1%) |
| 3774 | >10 (10.8%) |
| 3778 | >10 (4.2%) |
| 3780 | >10 (6.7%) |
| 3783 | >10 (1.7%) |
| 3791 | >10 (0%) |
| 3797 | >10 (7.0%) |
| 3799 | >10 (5.3%) |
| 3821 | 8.410 |
| 3829 | >10 (5.3%) |
| 3836 | >10 (1.4%) |
| 3843 | >10 (6.8%) |
| 3856 | 3.986 |
| 3861 | >10 (5.8%) |
| 3907 | 8.810 |
| 3910 | >10 (4.2%) |
| 3941 | >10 (5.5%) |
| 3944 | >10 (22.2%) |
| 3960 | >10 (7.0%) |
| 3974 | >10 (6.4%) |
| 3985 | >10 (5.2%) |
| 3999 | >10 (4.1%) |
| 4003 | >10 (3.7%) |
| 4006 | >10 (8.9%) |
| 4027 | >10 (4.0%) |
| 4041 | >10 (0%) |
| 4074 | >10 (14.0%) |
| 4075 | >10 (8.1%) |
| 4077 | >10 (3.6%) |
| 4104 | >10 (5.7%) |
| 4150 | >10 (4.6%) |
| 4159 | >10 (10.1%) |
| 4167 | >10 (4.9%) |
| 4218 | >10 (3.7%) |
| 4239 | >10 (10.5%) |
| 4244 | >10 (6.9%) |
| 4257 | >10 (5.3%) |
| 4319 | >10 (11.4%) |
| 4332 | >10 (0%) |
| 4346 | >10 (2.4%) |
| 4353 | >10 (8.5%) |
| 4377 | >10 (5.7%) |
| 4431 | >10 (3.6%) |
| 4432 | >10 (1.4%) |
| 4434 | 9.852 |
| 4498 | 3.087 |
| 4504 | >10 (7.3%) |
| 4523 | 3.258 |
| 4535 | 2.855 |
| 4536 | 3.023 |
| 4537 | >10 (3.0%) |
| 4538 | 3.432 |
| 4539 | >10 (37.4%) |
| 4544 | 7.770 |
| 4548 | >10 (3.2%) |
| 4551 | 2.989 |
| 4558 | 9.226 |
| 4559 | 8.502 |
| 4560 | >10 (2.7%) |
| 4561 | 4.563 |
| 4564 | >10 (0%) |
| 4565 | >10 (10.2%) |
| 4569 | >10 (42.3%) |
| 4570 | >10 (18.4%) |
| 4573 | >10 (9.6%) |
| 4574 | >10 (5.7%) |
| 4576 | >10 (0%) |
| 4577 | >10 (2.6%) |
| 4586 | >10 (4.8%) |
| 4593 | >10 (4.8%) |
| 4594 | >10 (2.4%) |
| 4595 | >10 (5.3%) |
| 4600 | >10 (6.3%) |
| 4609 | >10 (9.1%) |
| 4610 | >10 (10.3%) |
| 4611 | 8.678 |
| 4612 | >10 (4.4%) |
| 4614 | 2.817 |
| 4615 | >10 (5.8%) |
| 4616 | >10 (5.8%) |
| 4618 | >10 (6.3%) |
| 4622 | >10 (2.3%) |
| 4623 | >10 (8.1%) |
| 4632 | >10 (6.8%) |
| 4634 | >10 (1.9%) |
| 4640 | >10 (4.6%) |
| 4641 | >10 (6.3%) |
| 4643 | >10 (5.7%) |
| 4646 | >10 (3.2%) |
| 4647 | >10 (6.5%) |
| 4650 | >10 (7.1%) |
| 4657 | >10 (9.2%) |
| 4658 | 6.532 |
What is claimed is:
1. A compound, or a pharmaceutically acceptable salt thereof, of Formula I:
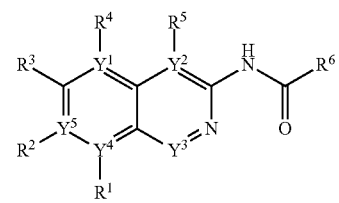
I wherein:

$R^1$, $R^2$, $R^4$, and $R^5$ are independently absent or selected from the group consisting of H, halide, unsubstituted —($C_{1-3}$ haloalkyl), and unsubstituted —($C_{1-3}$ alkyl);

$R^3$ is selected from the group consisting of -aryl optionally substituted with 1-5 $R^7$ and -heteroaryl optionally substituted with 1-4 $R^8$;

$R^6$ is selected from the group consisting of —($C_{1-4}$ alkylene)$_p$aryl substituted with 1-5 $R^9$, —($C_{2-4}$ alkenylene)$_p$aryl substituted with 1-5 $R^9$, —($C_{1-4}$ alkylene)$_p$heteroaryl optionally substituted with 1-6 $R^{10}$; —($C_{1-4}$ alkylene)$_p$heterocyclyl optionally substituted with 1-10 $R^{11}$, —($C_{1-4}$ alkylene)$_p$carbocyclyl optionally substituted with 1-12 $R^{12}$, —($C_{1-4}$ alkylene)N($R^{13}$)($R^{14}$), —N($R^{15}$)($R^{16}$), —CF($C_{1-9}$ alkyl)$_2$, —($C_{1-4}$ alkylene)$_p$O($C_{3-9}$ alkyl), and —($C_{2-9}$ alkynyl) optionally substituted with one or more halides; wherein each alkyl of —CF($C_{1-9}$ alkyl)$_2$ is, independently, optionally substituted with one or more halides; wherein each —($C_{1-4}$ alkylene) is, independently, optionally substituted with one or more substituents; wherein —($C_{1-4}$ alkenylene) is, optionally substituted with one or more substituents;

$R^7$ is selected from the group consisting of halide and —N($R^{17}$)$_2$;

each $R^8$ is independently selected from the group consisting of H, halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —N($R^{15}$)($R^{18}$), —($C_{1-4}$ alkylene)$_p$X$R^{19}$, —C(=O)N($R^5$)$_2$, —($C_{1-4}$ alkylene)$_p$heterocyclyl optionally substituted with 1-10 $R^{20}$, and -carbocyclyl optionally substituted with 1-12 $R^{21}$; wherein each —($C_{1-4}$ alkylene) is, independently, optionally substituted with one or more substituents;

alternatively, two adjacent $R^8$ are taken together to form a ring which is selected from the group consisting of -heterocyclyl optionally substituted with 1-10 $R^{22}$ and -carbocyclyl optionally substituted with 1-12 $R^{21}$;

each $R^9$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —X$R^{23}$, C(=O)N($R^5$)$_2$, —($C_{1-4}$ alkylene)$_p$N($R^{24}$)$_2$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

with the proviso that when $Y^2$ is N then $R^9$ is not —OMe or

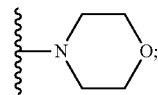

each $R^{10}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —CN, —X$R^{23}$, —C(=O)N($R^{15}$)$_2$, —($C_{1-4}$ alkylene)$_p$N($R^{24}$)$_2$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

each $R^{11}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$O$R^{19}$, —($C_{1-4}$ alkylene)$_p$heterocyclyl optionally substituted with 1-10 $R^{22}$, —($C_{1-4}$ alkylene)$_p$carbocyclyl optionally substituted with 1-12 $R^{21}$, —N($R^{15}$)($R^{25}$), —C(=O)($R^{26}$), —($C_{1-4}$ alkylene)C(=O)O$R^{27}$, —($C_{1-4}$ alkylene)aryl optionally substituted with one or more halides, —($C_{1-4}$ alkylene)$_p$heteroaryl optionally substituted with one or more halides, and —SO$_2$($R^{28}$); wherein each —($C_{1-4}$ alkylene) is, independently, optionally substituted with one or more substituents;

alternatively, two $R^{11}$ attached to the same carbon atom can together represent =O to form a carbonyl group;

each $R^{12}$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$O$R^{19}$, —N($R^{15}$)($R^{29}$), —C(=O)($R^{26}$), —C(=O)O$R^{27}$, —($C_{1-4}$ alkylene)$_p$heterocyclyl optionally substituted with 1-10 $R^{22}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

$R^{13}$ is selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{20}$, and -carbocyclyl optionally substituted with 1-12 $R^{21}$; wherein —($C_{1-4}$ alkylene) is, optionally substituted with one or more substituents;

$R^{14}$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$_p$heterocyclyl optionally substituted with 1-10 $R^{20}$, and -carbocyclyl optionally substituted with 1-12 $R^{21}$; wherein —($C_{1-4}$ alkylene) is, optionally substituted with one or more substituents;

each $R^{15}$ is selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

$R^{16}$ is selected from the group consisting of —($C_{1-4}$ alkylene)$_p$heterocyclyl optionally substituted with 1-10 $R^{20}$, and —($C_{1-4}$ alkylene)$_p$carbocyclyl optionally substituted with 1-12 $R^{21}$; wherein each —($C_{1-4}$ alkylene) is, independently, optionally substituted with one or more substituents;

$R^{17}$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

alternatively, two adjacent $R^{17}$ are taken together to form a -heterocyclyl ring optionally substituted with 1-10 $R^{22}$;

$R^{18}$ is independently selected from the group consisting of H, unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —C(=O)$R^5$, and —($C_{1-4}$ alkylene)$_p$heterocyclyl optionally substituted with one or more halides or one or more unsubstituted —($C_{1-5}$ alkyl); wherein —(C$_{1-4}$ alkylene) is, independently, optionally substituted with one or more substituents;

each R$^{19}$ is independently selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$heterocyclyl optionally substituted with one or more halides or one or more unsubstituted —(C$_{1-5}$ alkyl), and —(C$_{1-4}$ alkylene)$_p$carbocyclyl optionally substituted with 1-12 R$^{21}$; wherein each —(C$_{1-4}$ alkylene) is, independently, optionally substituted with one or more substituents;

each R$^{20}$ independently is selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —CN, —OH, —N(R$^5$)$_2$, and —(C$_{1-4}$ alkylene)$_p$carbocyclyl optionally substituted with 1-12 R$^{21}$; wherein each —(C$_{1-4}$ alkylene) is, independently, optionally substituted with one or more substituents;

each R$^{21}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), and —CN;

each R$^{22}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —CN, —OH, —N(R$^{15}$)$_2$, —C(=O)R$^{34}$, and —(C$_{1-4}$ alkylene)$_p$carbocyclyl optionally substituted with 1-12 R$^{21}$; wherein each —(C$_{1-4}$ alkylene) is, independently, optionally substituted with one or more substituents;

each R$^{23}$ is independently selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)N(R$^{15}$)$_2$, —(C$_{1-4}$ alkylene)$_p$aryl optionally substituted with 1-10 R$^{30}$, —(C$_{1-4}$ alkylene)$_p$heterocyclyl optionally substituted with 1-12 R$^{31}$, and —(C$_{1-4}$ alkylene)$_p$carbocyclyl optionally substituted with 1-12 R$^{21}$; wherein each —(C$_{1-4}$ alkylene) is, independently, optionally substituted with one or more substituents;

each R$^{24}$ is independently selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$heterocyclyl optionally substituted with one or more halides or one or more unsubstituted —(C$_{1-5}$ alkyl), and —(C$_{1-4}$ alkylene)N(R$^{15}$)$_2$; wherein each —(C$_{1-4}$ alkylene) is, independently, optionally substituted with one or more substituents;

each R$^{25}$ is selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$heterocyclyl optionally substituted with 1-10 R$^{32}$, —(C$_{1-4}$ alkylene)$_p$carbocyclyl optionally substituted with 1-12 R$^{21}$, —(C$_{1-4}$ alkylene)OR$^{33}$; wherein each —(C$_{1-4}$ alkylene) is, independently, optionally substituted with one or more substituents;

R$^{26}$ is selected from the group consisting of H, unsubstituted —(C$_{3-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$aryl optionally substituted with one or more halides or unsubstituted —(C$_{1-5}$ alkyl), —(C$_{1-4}$ alkylene)$_p$heteroaryl optionally substituted with one or more halides or one or more unsubstituted —(C$_{1-5}$ alkyl), and —(C$_{1-4}$ alkylene)$_p$heterocyclyl optionally substituted with one or more halides or one or more unsubstituted —(C$_{1-5}$ alkyl); wherein each —(C$_{1-4}$ alkylene) is, independently, optionally substituted with one or more substituents;

R$^{27}$ is selected from the group consisting of H, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$aryl optionally substituted with one or more halides or one or more unsubstituted —(C$_{1-5}$ alkyl), —(C$_{1-4}$ alkylene)$_p$heteroaryl optionally substituted with one or more halides or one or more unsubstituted —(C$_{1-5}$ alkyl), and —(C$_{1-4}$ alkylene)$_p$heterocyclyl optionally substituted with one or more halides or one or more unsubstituted —(C$_{1-5}$ alkyl); wherein each —(C$_{1-4}$ alkylene) is, independently, optionally substituted with one or more substituents;

R$^{28}$ is selected from the group consisting of unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —(C$_{1-4}$ alkylene)$_p$aryl optionally substituted with one or more halides or one or more unsubstituted —(C$_{1-5}$ alkyl), —(C$_{1-4}$ alkylene)$_p$heteroaryl optionally substituted with one or more halides or one or more unsubstituted —(C$_{1-5}$ alkyl), and —(C$_{1-4}$ alkylene)$_p$heterocyclyl optionally substituted with one or more halides or one or more unsubstituted —(C$_{1-5}$ alkyl); wherein —(C$_{1-4}$ alkylene) is, optionally substituted with one or more substituents;

each R$^{29}$ is selected from the group consisting of H, unsubstituted —(C$_{1-5}$ alkyl), unsubstituted —(C$_2$-5 alkenyl), unsubstituted —(C$_{2-5}$ alkynyl), unsubstituted —(C$_{1-5}$ haloalkyl), —(C$_{1-4}$ alkylene)$_p$heterocyclyl optionally substituted with 1-10 R$^{32}$, —(C$_{1-4}$ alkylene)$_p$carbocyclyl optionally substituted with 1-12 R$^{21}$, —(C$_{1-4}$ alkylene)OR$^{33}$, and —C(=O)O(C$_{1-5}$ alkyl); wherein each —(C$_{1-4}$ alkylene) is, independently, optionally substituted with one or more substituents;

each R$^{30}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), and —CN;

each R$^{31}$ is independently selected from the group consisting of halide, unsubstituted —(C$_{1-5}$ alkyl), unsubstituted —(C$_{2-5}$ alkenyl), unsubstituted —(C$_{2-5}$ alkynyl), unsubstituted —(C$_{1-5}$ haloalkyl), —CN, —OH, —C(=O)R$^{34}$, —N(R$^{24}$)$_2$, and —(C$_{1-4}$ alkylene)$_p$carbocyclyl optionally substituted with 1-12 R$^{21}$; wherein each —(C$_{1-4}$ alkylene) is, independently, optionally substituted with one or more substituents;

each R$^{32}$ is independently selected from the group consisting of halide and unsubstituted —(C$_{1-5}$ alkyl);

each R$^{33}$ is independently selected from the group consisting of H and unsubstituted —(C$_{1-5}$ alkyl);

each R$^{34}$ is independently selected from the group consisting of —O(C$_{15}$ alkyl) and a heteroaryl optionally substituted with 1-6 R$^{35}$;

each R$^{35}$ is a -heterocyclyl optionally substituted with one or more halides or one or more unsubstituted —(C$_{1-5}$ alkyl);

each X is selected from the group consisting of O and S;

Y$^3$ is CH or nitrogen;

Y$^1$, Y$^2$, Y$^4$, and Y$^5$ are independently selected from the group consisting of carbon and nitrogen;

wherein if Y$^1$ is nitrogen then Y$^2$, Y$^4$, and Y$^5$ are carbon, Y$^3$ is CH, and R$^4$ is absent;

if Y² is nitrogen then Y¹, Y⁴, and Y⁵ are carbon, Y³ is CH, and R⁵ is absent;
if Y³ is nitrogen then Y¹, Y², Y⁴, and Y⁵ are carbon;
if Y⁴ is nitrogen then Y¹, Y², and Y⁵ are carbon, Y³ is CH, and R¹ is absent;
if Y⁵ is nitrogen then Y¹, Y², and Y⁴ are carbon, Y³ is CH, and R² is absent;
each p is independently 0 or 1; and
wherein the compound of Formula I is selected from the group consisting of

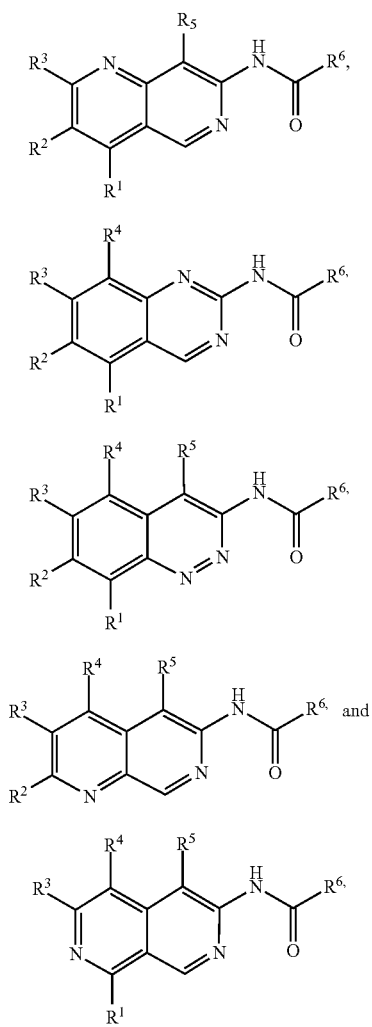

or a pharmaceutically acceptable salt thereof.

2. The compound of claim 1, wherein R¹, R², R⁴, and R⁵ are H.

3. The compound of claim 1, wherein R³ is selected from the group consisting of pyrazolyl, imidazolyl, triazolyl, thiadiazolyl, and oxazolyl, each optionally substituted with 1-4 R⁸.

4. The compound of claim 3, wherein R³ is a pyrazol-4-yl, substituted with one —(C$_{1-3}$ alkyl).

5. The compound of claim 3, wherein R³ is a imidazol-5-yl, substituted with one —(C$_{1-3}$ alkyl).

6. The compound of claim 3, wherein R³ is a imidazol-5-yl, substituted with two —(C$_{1-3}$ alkyl).

7. The compound of claim 3, wherein R³ is a 1,2,3-triazol-4-yl, substituted with one —(C$_{1-3}$ alkyl).

8. The compound of claim 3, wherein R³ is a thiadiazol-2-yl, substituted with one —(C$_{1-3}$ alkyl).

9. The compound of claim 3, wherein R³ is a oxazol-5-yl, substituted with one —(C$_{1-3}$ alkyl).

10. The compound of claim 3, wherein R⁶ is -heterocyclyl, optionally substituted with 1-2 R¹¹.

11. The compound of claim 3, wherein R⁶ is a —CH₂heterocyclyl optionally substituted with 1-2 R¹¹.

12. The compound of claim 1, wherein the compound of Formula I is selected from the group consisting of:

N-(2-(1H-pyrazol-4-yl)-1,6-naphthyridin-7-yl)-1-isobutylpiperidine-4-carboxamide [1];
N-(2-(1-methyl-1H-pyrazol-4-yl)-1,6-naphthyridin-7-yl) cyclopropanecarboxamide [2];
4,4-difluoro-N-(2-(1-methyl-1H-pyrazol-4-yl)-1,6-naphthyridin-7-yl)cyclohexane-1-carboxamide [3];
trans-4-methoxy-N-(2-(1-methyl-1H-pyrazol-4-yl)-1,6-naphthyridin-7-yl)cyclohexane-1-carboxamide [4];
trans-N-(2-(1-methyl-1H-pyrazol-4-yl)-1,6-naphthyridin-7-yl)-4-morpholinocyclohexane-1-carboxamide [5];
trans-4-((3-fluoroazetidin-1-yl)methyl)-N-(2-(1-methyl-1H-pyrazol-4-yl)-1,6-naphthyridin-7-yl) cyclohexane-1-carboxamide [6];
trans-N-(2-(1-methyl-1H-pyrazol-4-yl)-1,6-naphthyridin-7-yl)-4-((4-methylpiperazin-1-yl) methyl)cyclohexane-1-carboxamide [7];
N-(2-(1-methyl-1H-pyrazol-4-yl)-1,6-naphthyridin-7-yl)-2-(pyrrolidin-1-yl)acetamide [8];
(S)-2-(3-fluoropyrrolidin-1-yl)-N-(2-(1-methyl-1H-pyrazol-4-yl)-1,6-naphthyridin-7-yl) acetamide [9];
(S)—N-(2-(1-methyl-1H-pyrazol-4-yl)-1,6-naphthyridin-7-yl)tetrahydrofuran-2-carboxamide [10];
N-(2-(1-methyl-1H-pyrazol-4-yl)-1,6-naphthyridin-7-yl) piperidine-4-carboxamide [11];
1-methyl-N-(2-(1-methyl-1H-pyrazol-4-yl)-1,6-naphthyridin-7-yl)piperidine-4-carboxamide [12];
1-isopropyl-N-(2-(1-methyl-1H-pyrazol-4-yl)-1,6-naphthyridin-7-yl)piperidine-4-carboxamide [13];
1-(tert-butyl)-N-(2-(1-methyl-1H-pyrazol-4-yl)-1,6-naphthyridin-7-yl)piperidine-4-carboxamide [14];
1-cyclopropyl-N-(2-(1-methyl-1H-pyrazol-4-yl)-1,6-naphthyridin-7-yl)piperidine-4-carboxamide [15];
1-isobutyl-N-(2-(1-methyl-1H-pyrazol-4-yl)-1,6-naphthyridin-7-yl)piperidine-4-carboxamide [16];
N-(2-(1-methyl-1H-pyrazol-4-yl)-1,6-naphthyridin-7-yl)-1-neopentylpiperidine-4-carboxamide [17];
1-(2-fluoroethyl)-N-(2-(1-methyl-1H-pyrazol-4-yl)-1,6-naphthyridin-7-yl)piperidine-4-carboxamide [18];
N-(2-(1-methyl-1H-pyrazol-4-yl)-1,6-naphthyridin-7-yl)-1-(3,3,3-trifluoropropyl)piperidine-4-carboxamide [19];
1-butyl-N-(2-(1-methyl-1H-pyrazol-4-yl)-1,6-naphthyridin-7-yl)piperidine-4-carboxamide [20];
1-benzoyl-N-(2-(1-methyl-1H-pyrazol-4-yl)-1,6-naphthyridin-7-yl)piperidine-4-carboxamide [21];
1-(2,2-difluoropropyl)-N-(2-(1-methyl-1H-pyrazol-4-yl)-1,6-naphthyridin-7-yl)piperidine-4-carboxamide [22];
N-(2-(1-methyl-1H-pyrazol-4-yl)-1,6-naphthyridin-7-yl) azetidine-3-carboxamide [23];
1-(2,2-difluoroethyl)-N-(2-(1-methyl-1H-pyrazol-4-yl)-1,6-naphthyridin-7-yl)piperidine-4-carboxamide [24];
1-(2-fluoro-2-methylpropyl)-N-(2-(1-methyl-1H-pyrazol-4-yl)-1,6-naphthyridin-7-yl)piperidine-4-carboxamide [25];
N-(2-(1-methyl-1H-pyrazol-4-yl)-1,6-naphthyridin-7-yl)-1-(oxetan-3-yl)piperidine-4-carboxamide [26];

N-(2-(1-methyl-1H-pyrazol-4-yl)-1,6-naphthyridin-7-yl)-1-((3-methyloxetan-3-yl)methyl) piperidine-4-carboxamide [27];

1-(2-methoxyethyl)-N-(2-(1-methyl-1H-pyrazol-4-yl)-1,6-naphthyridin-7-yl)piperidine-4-carboxamide [28];

1-(2-isopropoxyethyl)-N-(2-(1-methyl-1H-pyrazol-4-yl)-1,6-naphthyridin-7-yl)piperidine-4-carboxamide [29];

1,1-diisobutyl-4-((2-(1-methyl-1H-pyrazol-4-yl)-1,6-naphthyridin-7-yl)carbamoyl)piperidin-1-ium [30];

4-fluoro-N-(2-(1-methyl-1H-pyrazol-4-yl)-1,6-naphthyridin-7-yl)piperidine-4-carboxamide [31];

4-fluoro-1-methyl-N-(2-(1-methyl-1H-pyrazol-4-yl)-1,6-naphthyridin-7-yl)piperidine-4-carboxamide [32];

4-fluoro-1-isobutyl-N-(2-(1-methyl-1H-pyrazol-4-yl)-1,6-naphthyridin-7-yl)piperidine-4-carboxamide [33];

(S)—N-(2-(1-methyl-1H-pyrazol-4-yl)-1,6-naphthyridin-7-yl)piperidine-3-carboxamide [34];

(R)—N-(2-(1-methyl-1H-pyrazol-4-yl)-1,6-naphthyridin-7-yl)piperidine-3-carboxamide [35];

(S)-1-isobutyl-N-(2-(1-methyl-1H-pyrazol-4-yl)-1,6-naphthyridin-7-yl)piperidine-3-carboxamide [36];

(R)-1-isobutyl-N-(2-(1-methyl-1H-pyrazol-4-yl)-1,6-naphthyridin-7-yl)piperidine-3-carboxamide [37];

N-(2-(1-methyl-1H-pyrazol-4-yl)-1,6-naphthyridin-7-yl) tetrahydro-2H-pyran-4-carboxamide [38];

N-(2-(1-methyl-1H-pyrazol-4-yl)-1,6-naphthyridin-7-yl)-2-(piperidin-1-yl)acetamide [39];

2-(4-fluoropiperidin-1-yl)-N-(2-(1-methyl-1H-pyrazol-4-yl)-1,6-naphthyridin-7-yl)acetamide [40];

trans-4-amino-N-(2-(1-methyl-1H-pyrazol-4-yl)-1,6-naphthyridin-7-yl)cyclohexane-1-carboxamide [41];

N-(2-(1-methyl-1H-pyrazol-4-yl)-1,6-naphthyridin-7-yl)-2-(4-methylpiperazin-1-yl)acetamide [42];

(S)—N-(2-(1-methyl-1H-pyrazol-4-yl)-1,6-naphthyridin-7-yl)piperidine-2-carboxamide [43];

2-(4-isobutylpiperazin-1-yl)-N-(2-(1-methyl-1H-pyrazol-4-yl)-1,6-naphthyridin-7-yl)acetamide [44];

2-(3,3-dimethylazetidin-1-yl)-N-(2-(1-methyl-1H-pyrazol-4-yl)-1,6-naphthyridin-7-yl)acetamide [45];

(R)-2-(3-fluoropyrrolidin-1-yl)-N-(2-(1-methyl-1H-pyrazol-4-yl)-1,6-naphthyridin-7-yl) acetamide [46];

(S)—N-(2-(1-methyl-1H-pyrazol-4-yl)-1,6-naphthyridin-7-yl)-2-(2-methylpyrrolidin-1-yl) acetamide [47];

2-(3-azabicyclo[3.1.0]hexan-3-yl)-N-(2-(1-methyl-1H-pyrazol-4-yl)-1,6-naphthyridin-7-yl) acetamide [48];

2-(7-azabicyclo[2.2.1]heptan-7-yl)-N-(2-(1-methyl-1H-pyrazol-4-yl)-1,6-naphthyridin-7-yl) acetamide [49];

N-(2-(1-methyl-1H-pyrazol-4-yl)-1,6-naphthyridin-7-yl)-2-(4-methylpiperidin-1-yl)acetamide [50];

N-(2-(1-methyl-1H-pyrazol-4-yl)-1,6-naphthyridin-7-yl)-2-(4-(trifluoromethyl)piperidin-1-yl) acetamide [51];

2-(4-(difluoromethyl)piperidin-1-yl)-N-(2-(1-methyl-1H-pyrazol-4-yl)-1,6-naphthyridin-7-yl) acetamide [52];

N-(2-(1-methyl-1H-pyrazol-4-yl)-1,6-naphthyridin-7-yl)-2-(6-azaspiro[2.5]octan-6-yl)acetamide [53];

N-(2-(1-methyl-1H-pyrazol-4-yl)-1,6-naphthyridin-7-yl)-2-(pyrrolidin-1-yl)propanamide [54];

(R)—N-(2-(1-methyl-1H-pyrazol-4-yl)-1,6-naphthyridin-7-yl)-2-(2-methylpyrrolidin-1-yl) acetamide [55];

2-(cyclobutyl(methyl)amino)-N-(2-(1-methyl-1H-pyrazol-4-yl)-1,6-naphthyridin-7-yl)acetamide [56];

2-(diethylamino)-N-(2-(1-methyl-1H-pyrazol-4-yl)-1,6-naphthyridin-7-yl)acetamide [57];

7-(2-fluoroethyl)-N-(2-(1-methyl-1H-pyrazol-4-yl)-1,6-naphthyridin-7-yl)-7-azaspiro[3.5]nonane-2-carboxamide [58];

4-methyl-N-(2-(1-methyl-1H-pyrazol-4-yl)-1,6-naphthyridin-7-yl)piperazine-1-carboxamide [59];

(S)—N-(2-(1-methyl-1H-pyrazol-4-yl)-1,6-naphthyridin-7-yl)-2-(pyrrolidin-1-yl)propanamide [60];

(R)—N-(2-(1-methyl-1H-pyrazol-4-yl)-1,6-naphthyridin-7-yl)-2-(pyrrolidin-1-yl)propanamide [61];

(R)—N-(2-(1-methyl-1H-pyrazol-4-yl)-1,6-naphthyridin-7-yl)pyrrolidine-2-carboxamide [62];

2-methyl-N-(2-(1-methyl-1H-pyrazol-4-yl)-1,6-naphthyridin-7-yl)-2-azaspiro[3.3]heptane-6-carboxamide [63];

N-(2-(1-methyl-1H-pyrazol-4-yl)-1,6-naphthyridin-7-yl)-2-(2,2,2-trifluoroacetyl)-2-azaspiro[3.3]heptane-6-carboxamide [64];

2-(2-fluoroethyl)-N-(2-(1-methyl-1H-pyrazol-4-yl)-1,6-naphthyridin-7-yl)-2-azaspiro[3.3]heptane-6-carboxamide [65];

trans-4-(dimethylamino)-N-(2-(1-methyl-1H-pyrazol-4-yl)-1,6-naphthyridin-7-yl)cyclohexane-1-carboxamide [66];

1-acetyl-N-(2-(1-methyl-1H-pyrazol-4-yl)-1,6-naphthyridin-7-yl)piperidine-4-carboxamide [67];

N-(2-(1-methyl-1H-pyrazol-4-yl)-1,6-naphthyridin-7-yl)-1-((1-(trifluoromethyl)cyclopropyl) methyl)piperidine-4-carboxamide [68];

(S)-1-(2-fluoropropyl)-N-(2-(1-methyl-1H-pyrazol-4-yl)-1,6-naphthyridin-7-yl)piperidine-4-carboxamide [69];

(R)-1-(2-fluoropropyl)-N-(2-(1-methyl-1H-pyrazol-4-yl)-1,6-naphthyridin-7-yl)piperidine-4-carboxamide [70];

N-(2-(1-methyl-1H-pyrazol-4-yl)-1,6-naphthyridin-7-yl)-1-(methylsulfonyl)piperidine-4-carboxamide [71];

1'-methyl-N-(2-(1-methyl-1H-pyrazol-4-yl)-1,6-naphthyridin-7-yl)-[1,4'-bipiperidine]-4-carboxamide [72];

trans-4-(hydroxymethyl)-N-(2-(1-methyl-1H-pyrazol-4-yl)-1,6-naphthyridin-7-yl)cyclohexane-1-carboxamide [73];

methyl 2-(4-((2-(1-methyl-1H-pyrazol-4-yl)-1,6-naphthyridin-7-yl)carbamoyl)piperidin-1-yl) acetate [74];

1-benzyl-N-(2-(1-methyl-1H-pyrazol-4-yl)-1,6-naphthyridin-7-yl)piperidine-4-carboxamide [75];

N-(2-(1-methyl-1H-pyrazol-4-yl)-1,6-naphthyridin-7-yl)-1-(2-(pyrrolidin-1-yl)acetyl)piperidine-4-carboxamide [76];

N-(2-(1-methyl-1H-pyrazol-4-yl)-1,6-naphthyridin-7-yl)-2-morpholinoacetamide [77];

(S)—N-(2-(1-methyl-1H-pyrazol-4-yl)-1,6-naphthyridin-7-yl)-2-(3-methylmorpholino)acetamide [78];

(R)—N-(2-(1-methyl-1H-pyrazol-4-yl)-1,6-naphthyridin-7-yl)-2-(3-methylmorpholino)acetamide [79];

(S)—N-(2-(1-methyl-1H-pyrazol-4-yl)-1,6-naphthyridin-7-yl)-2-(2-methylmorpholino)acetamide [80];

2-((2R,6S)-2,6-dimethylmorpholino)-N-(2-(1-methyl-1H-pyrazol-4-yl)-1,6-naphthyridin-7-yl) acetamide [81];

2-((1S,4S)-2-oxa-5-azabicyclo[2.2.1]heptan-5-yl)-N-(2-(1-methyl-1H-pyrazol-4-yl)-1,6-naphthyridin-7-yl)acetamide [82];

2-((1R,4R)-2-oxa-5-azabicyclo[2.2.1]heptan-5-yl)-N-(2-(1-methyl-1H-pyrazol-4-yl)-1,6-naphthyridin-7-yl)acetamide [83];

2-(3-oxa-8-azabicyclo[3.2.1]octan-8-yl)-N-(2-(1-methyl-1H-pyrazol-4-yl)-1,6-naphthyridin-7-yl) acetamide [84];

(S)—N-(2-(1-methyl-1H-pyrazol-4-yl)-1,6-naphthyridin-7-yl)-2-morpholinopropanamide [85];

N-(2-(1-methyl-1H-pyrazol-4-yl)-1,6-naphthyridin-7-yl)-2-(morpholin-2-yl)acetamide [86];
N-(2-(1-methyl-1H-pyrazol-4-yl)-1,6-naphthyridin-7-yl)-2-(4-methylmorpholin-2-yl)acetamide [87];
2-(4-ethylpiperazin-1-yl)-N-(2-(1-methyl-1H-pyrazol-4-yl)-1,6-naphthyridin-7-yl)acetamide [88];
2-(4-isopropylpiperazin-1-yl)-N-(2-(1-methyl-1H-pyrazol-4-yl)-1,6-naphthyridin-7-yl)acetamide [89];
2-(4-cyclopropylpiperazin-1-yl)-N-(2-(1-methyl-1H-pyrazol-4-yl)-1,6-naphthyridin-7-yl) acetamide [90];
2-(4-(2-fluoroethyl)piperazin-1-yl)-N-(2-(1-methyl-1H-pyrazol-4-yl)-1,6-naphthyridin-7-yl) acetamide [91];
(S)-2-(2,4-dimethylpiperazin-1-yl)-N-(2-(1-methyl-1H-pyrazol-4-yl)-1,6-naphthyridin-7-yl) acetamide [92];
1-(2-hydroxyethyl)-N-(2-(1-methyl-1H-pyrazol-4-yl)-1,6-naphthyridin-7-yl)piperidine-4-carboxamide [93];
N-(2-(1-methyl-1H-pyrazol-4-yl)-1,6-naphthyridin-7-yl)-1-(pyridin-2-ylmethyl)piperidine-4-carboxamide [94];
N-(2-(1-methyl-1H-pyrazol-4-yl)-1,6-naphthyridin-7-yl)-1-(oxazol-2-ylmethyl)piperidine-4-carboxamide [95];
(R)—N-(2-(1-methyl-1H-pyrazol-4-yl)-1,6-naphthyridin-7-yl)-1-oxotetrahydro-1H-pyrrolo[1,2-c]imidazole-2(3H)-carboxamide [96];
(R)-1-methyl-N-(2-(1-methyl-1H-pyrazol-4-yl)-1,6-naphthyridin-7-yl)pyrrolidine-2-carboxamide [97];
N-(2-(1-methyl-1H-pyrazol-4-yl)-1,6-naphthyridin-7-yl)-1-(tetrahydro-2H-pyran-4-yl)piperidine-4-carboxamide [98];
N-(2-(1-methyl-1H-pyrazol-4-yl)-1,6-naphthyridin-7-yl)-1-(pyrimidin-2-ylmethyl)piperidine-4-carboxamide [99];
N-(2-(1-methyl-1H-pyrazol-4-yl)-1,6-naphthyridin-7-yl)-1-(pyrazin-2-ylmethyl)piperidine-4-carboxamide [100];
1-((5-methyl-1,2,4-oxadiazol-3-yl)methyl)-N-(2-(1-methyl-1H-pyrazol-4-yl)-1,6-naphthyridin-7-yl)piperidine-4-carboxamide [101];
1-(2-hydroxy-2-methylpropyl)-N-(2-(1-methyl-1H-pyrazol-4-yl)-1,6-naphthyridin-7-yl) piperidine-4-carboxamide [102];
tert-butyl 2-(4-((2-(1-methyl-1H-pyrazol-4-yl)-1,6-naphthyridin-7-yl)carbamoyl)piperidin-1-yl)acetate [103];
2-(4-((2-(1-methyl-1H-pyrazol-4-yl)-1,6-naphthyridin-7-yl)carbamoyl)piperidin-1-yl)acetic acid [104];
2-(4-methyl-1,4-diazepan-1-yl)-N-(2-(1-methyl-1H-pyrazol-4-yl)-1,6-naphthyridin-7-yl) acetamide [105];
tert-butyl (2-(1-methyl-1H-pyrazol-4-yl)-1,6-naphthyridin-7-yl)carbamate [106];
N-(2-(1-methyl-1H-pyrazol-4-yl)-1,6-naphthyridin-7-yl) but-2-ynamide [107];
trans-4-((2-(1-methyl-1H-pyrazol-4-yl)-1,6-naphthyridin-7-yl)carbamoyl)cyclohexane-1-carboxylic acid [108];
N-(2-(1-methyl-1H-pyrazol-4-yl)-1,6-naphthyridin-7-yl)-3-morpholinopropanamide [109];
trans-N-(2-(1-methyl-1H-pyrazol-4-yl)-1,6-naphthyridin-7-yl)-3-morpholinocyclobutane-1-carboxamide [110];
N-(2-(1-methyl-1H-pyrazol-4-yl)-1,6-naphthyridin-7-yl) quinuclidine-4-carboxamide [111];
N-(2-(1-methyl-1H-pyrazol-4-yl)-1,6-naphthyridin-7-yl)-2-(piperidin-1-yl)propanamide [112];
1-isobutyl-N-(2-(1-methyl-1H-pyrazol-4-yl)-1,6-naphthyridin-7-yl)azepane-4-carboxamide [113];
2-(4-methoxypiperidin-1-yl)-N-(2-(1-methyl-1H-pyrazol-4-yl)-1,6-naphthyridin-7-yl)acetamide [114];
2-(4-hydroxypiperidin-1-yl)-N-(2-(1-methyl-1H-pyrazol-4-yl)-1,6-naphthyridin-7-yl)acetamide [115];
3-(hydroxymethyl)-N-(2-(1-methyl-1H-pyrazol-4-yl)-1,6-naphthyridin-7-yl)bicyclo[1.1.1]pentane-1-carboxamide [116];
1-methyl-N-(2-(1-methyl-1H-pyrazol-4-yl)-1,6-naphthyridin-7-yl)azepane-4-carboxamide [117];
trans-4-(dimethylamino)-N-(2-(1-methyl-1H-pyrazol-4-yl)-1,6-naphthyridin-7-yl)cyclohexane-1-carboxamide [118];
trans-4-(bis(methyl-d₃)amino)-N-(2-(1-methyl-1H-pyrazol-4-yl)-1,6-naphthyridin-7-yl) cyclohexane-1-carboxamide [119];
N-(2-(1-methyl-1H-pyrazol-4-yl)-1,6-naphthyridin-7-yl)-3-((4-methylpiperazin-1-yl)methyl) bicyclo[1.1.1]pentane-1-carboxamide [120];
methyl trans-4-((2-(1-methyl-1H-pyrazol-4-yl)-1,6-naphthyridin-7-yl)carbamoyl)cyclohexane-1-carboxylate [121];
2-(1-isobutylpyrrolidin-3-yl)-N-(2-(1-methyl-1H-pyrazol-4-yl)-1,6-naphthyridin-7-yl)acetamide [122];
trans-N-(2-(1-methyl-1H-pyrazol-4-yl)-1,6-naphthyridin-7-yl)-4-(4-methylpiperazine-1-carbonyl)cyclohexane-1-carboxamide [123];
1-isobutyl-N-(2-(1-methyl-1H-pyrazol-4-yl)-1,6-naphthyridin-7-yl)piperidine-4-carboxamide [124];
N-(2-(1-methyl-1H-pyrazol-4-yl)-1,6-naphthyridin-7-yl)-1-(phenylsulfonyl)piperidine-4-carboxamide [125];
8-methyl-N-(2-(1-methyl-1H-pyrazol-4-yl)-1,6-naphthyridin-7-yl)-3,8-diazabicyclo[3.2.1]octane-3-carboxamide [126];
3-methyl-N-(2-(1-methyl-1H-pyrazol-4-yl)-1,6-naphthyridin-7-yl)-3,8-diazabicyclo[3.2.1]octane-8-carboxamide [127];
(1R,3s,5S)-3-amino-N-(2-(1-methyl-1H-pyrazol-4-yl)-1,6-naphthyridin-7-yl)-8-azabicyclo[3.2.1] octane-8-carboxamide [128];
(1R,3s,5S)—N-(2-(1-methyl-1H-pyrazol-4-yl)-1,6-naphthyridin-7-yl)-3-((3,3,3-trifluoropropyl) amino)-8-azabicyclo[3.2.1]octane-8-carboxamide [129];
(1R,3s,5S)-3-((1,3-difluoropropan-2-yl)amino)-N-(2-(1-methyl-1H-pyrazol-4-yl)-1,6-naphthyridin-7-yl)-8-azabicyclo[3.2.1]octane-8-carboxamide [130];
N-(2-(1-methyl-1H-pyrazol-4-yl)-1,6-naphthyridin-7-yl) morpholine-4-carboxamide [131];
4-(dimethylamino)-N-(2-(1-methyl-1H-pyrazol-4-yl)-1,6-naphthyridin-7-yl)piperidine-1-carboxamide [132];
(S)-2,4-dimethyl-N-(2-(1-methyl-1H-pyrazol-4-yl)-1,6-naphthyridin-7-yl)piperazine-1-carboxamide [133];
1-methyl-3-(2-(1-methyl-1H-pyrazol-4-yl)-1,6-naphthyridin-7-yl)-1-(methylpiperidin-4-yl)urea [134];
1-(2-(1-methyl-1H-pyrazol-4-yl)-1,6-naphthyridin-7-yl)-3-(1-methylpiperidin-4-yl)urea [135];
4-isopropyl-N-(2-(1-methyl-1H-pyrazol-4-yl)-1,6-naphthyridin-7-yl)piperazine-1-carboxamide [136];
(R)-3,4-dimethyl-N-(2-(1-methyl-1H-pyrazol-4-yl)-1,6-naphthyridin-7-yl)piperazine-1-carboxamide [137];
N-(2-(1H-pyrazol-4-yl)-1,6-naphthyridin-7-yl)-2-(4-methylpiperazin-1-yl)isonicotinamide [138];
N-(2-(1-methyl-1H-pyrazol-4-yl)-1,6-naphthyridin-7-yl)-3-(piperazin-1-yl)benzamide [139];
N-(2-(1-methyl-1H-pyrazol-4-yl)-1,6-naphthyridin-7-yl)-3-(4-methylpiperazin-1-yl)benzamide [140];
N-(2-(1-methyl-1H-pyrazol-4-yl)-1,6-naphthyridin-7-yl)-3-(pyrrolidin-1-ylmethyl)benzamide [141];
N-(2-(1-methyl-1H-pyrazol-4-yl)-1,6-naphthyridin-7-yl)-3-(piperidin-4-yloxy)benzamide [142];
N-(2-(1-methyl-1H-pyrazol-4-yl)-1,6-naphthyridin-7-yl)-3-((1-methylpiperidin-4-yl)oxy) benzamide [143];

N-(2-(1-methyl-1H-pyrazol-4-yl)-1,6-naphthyridin-7-yl)-4-(piperidin-4-yloxy)benzamide [144];

N-(2-(1-methyl-1H-pyrazol-4-yl)-1,6-naphthyridin-7-yl)-4-((1-methylpiperidin-4-yl)oxy) benzamide [145];

N-(2-(1-methyl-1H-pyrazol-4-yl)-1,6-naphthyridin-7-yl)-2-(piperazin-1-yl)isonicotinamide [146];

N-(2-(1-methyl-1H-pyrazol-4-yl)-1,6-naphthyridin-7-yl)-2-(4-methylpiperazin-1-yl) isonicotinamide [147];

2-(4-isopropylpiperazin-1-yl)-N-(2-(1-methyl-1H-pyrazol-4-yl)-1,6-naphthyridin-7-yl) isonicotinamide [148];

2-(4-cyclopropylpiperazin-1-yl)-N-(2-(1-methyl-1H-pyrazol-4-yl)-1,6-naphthyridin-7-yl) isonicotinamide [149];

2-(4-(2-fluoroethyl)piperazin-1-yl)-N-(2-(1-methyl-1H-pyrazol-4-yl)-1,6-naphthyridin-7-yl) isonicotinamide [150];

N-(2-(1-methyl-1H-pyrazol-4-yl)-1,6-naphthyridin-7-yl)-6-(4-methylpiperazin-1-yl)nicotinamide [151];

N-(2-(1-methyl-1H-pyrazol-4-yl)-1,6-naphthyridin-7-yl)-5-(piperidin-4-yloxy)nicotinamide [152];

N-(2-(1-methyl-1H-pyrazol-4-yl)-1,6-naphthyridin-7-yl)-2-(piperidin-4-yloxy)isonicotinamide [153];

N-(2-(1-methyl-1H-pyrazol-4-yl)-1,6-naphthyridin-7-yl)-2-((1-methylpiperidin-4-yl)oxy) isonicotinamide [154];

N-(2-(1-methyl-1H-pyrazol-4-yl)-1,6-naphthyridin-7-yl)-5-(piperidin-4-ylamino)nicotinamide [155];

N-(2-(1-methyl-1H-pyrazol-4-yl)-1,6-naphthyridin-7-yl)-5-((1-methylpiperidin-4-yl)amino) nicotinamide [156];

2-(4-aminopiperidin-1-yl)-N-(2-(1-methyl-1H-pyrazol-4-yl)-1,6-naphthyridin-7-yl) isonicotinamide [157];

N-(2-(1-methyl-1H-pyrazol-4-yl)-1,6-naphthyridin-7-yl)-2-(4-(methylamino)piperidin-1-yl) isonicotinamide [158];

2-(4-(dimethylamino)piperidin-1-yl)-N-(2-(1-methyl-1H-pyrazol-4-yl)-1,6-naphthyridin-7-yl) isonicotinamide [159];

2-((1-isopropylpiperidin-4-yl)oxy)-N-(2-(1-methyl-1H-pyrazol-4-yl)-1,6-naphthyridin-7-yl) isonicotinamide [160];

2-(3-aminoazetidin-1-yl)-N-(2-(1-methyl-1H-pyrazol-4-yl)-1,6-naphthyridin-7-yl) isonicotinamide [161];

2-(3-(dimethylamino)azetidin-1-yl)-N-(2-(1-methyl-1H-pyrazol-4-yl)-1,6-naphthyridin-7-yl) isonicotinamide [162];

N-(2-(1-methyl-1H-pyrazol-4-yl)-1,6-naphthyridin-7-yl)-2-morpholinoisonicotinamide [163];

2-((2-(dimethylamino)ethyl)amino)-N-(2-(1-methyl-1H-pyrazol-4-yl)-1,6-naphthyridin-7-yl) isonicotinamide [164];

2-(2-(dimethylamino)ethoxy)-N-(2-(1-methyl-1H-pyrazol-4-yl)-1,6-naphthyridin-7-yl) isonicotinamide [165];

2-(4-isobutylpiperazin-1-yl)-N-(2-(1-methyl-1H-pyrazol-4-yl)-1,6-naphthyridin-7-yl) isonicotinamide [166];

2-(azetidin-3-yloxy)-N-(2-(1-methyl-1H-pyrazol-4-yl)-1,6-naphthyridin-7-yl)isonicotinamide [167];

N-(2-(1-methyl-1H-pyrazol-4-yl)-1,6-naphthyridin-7-yl)-2-((1-methylazetidin-3-yl)oxy) isonicotinamide [168];

2-(4-ethylpiperazin-1-yl)-N-(2-(1-methyl-1H-pyrazol-4-yl)-1,6-naphthyridin-7-yl) isonicotinamide [169];

4-((dimethylamino)methyl)-N-(2-(1-methyl-1H-pyrazol-4-yl)-1,6-naphthyridin-7-yl)benzamide [170];

N-(2-(1-methyl-1H-pyrazol-4-yl)-1,6-naphthyridin-7-yl)-3-(1-methylpiperidin-4-yl)benzamide [171];

N-(2-(1-methyl-1H-pyrazol-4-yl)-1,6-naphthyridin-7-yl)-3-((4-methylpiperazin-1-yl)methyl) benzamide [172];

N-(2-(1-methyl-1H-pyrazol-4-yl)-1,6-naphthyridin-7-yl) isonicotinamide [173];

2-hydroxy-N-(2-(1-methyl-1H-pyrazol-4-yl)-1,6-naphthyridin-7-yl)isonicotinamide [174];

2-isopropoxy-N-(2-(1-methyl-1H-pyrazol-4-yl)-1,6-naphthyridin-7-yl)isonicotinamide [175];

N-(2-(1-methyl-1H-pyrazol-4-yl)-1,6-naphthyridin-7-yl)-2-(1-methylpiperidin-4-yl) isonicotinamide [176];

1'-methyl-N-(2-(1-methyl-1H-pyrazol-4-yl)-1,6-naphthyridin-7-yl)-1',2',3',6'-tetrahydro-[2,4'-bipyridine]-4-carboxamide [177];

N-(2-(1-methyl-1H-pyrazol-4-yl)-1,6-naphthyridin-7-yl)-2-(4-(6-(4-methylpiperazin-1-yl) nicotinoyl)piperazin-1-yl)isonicotinamide [178];

2-(4-hydroxy-4-methyl-4$\lambda^4$-piperazin-1-yl)-N-(2-(1-methyl-1H-pyrazol-4-yl)-1,6-naphthyridin-7-yl)isonicotinamide [179];

2-methyl-N-(2-(1-methyl-1H-pyrazol-4-yl)-1,6-naphthyridin-7-yl)-6-(4-methylpiperazin-1-yl) isonicotinamide [180];

3-methyl-N-(2-(1-methyl-1H-pyrazol-4-yl)-1,6-naphthyridin-7-yl)-2-(4-methylpiperazin-1-yl) isonicotinamide [181];

2-(4-methyl-1,4-diazepan-1-yl)-N-(2-(1-methyl-1H-pyrazol-4-yl)-1,6-naphthyridin-7-yl) isonicotinamide [182];

2-((2S,6R)-2,6-dimethylmorpholino)-N-(2-(1-methyl-1H-pyrazol-4-yl)-1,6-naphthyridin-7-yl) isonicotinamide [183];

N-(2-(1-methyl-1H-pyrazol-4-yl)-1,6-naphthyridin-7-yl)-2-(2,7-diazaspiro[3.5]nonan-2-yl) isonicotinamide [184];

N-(2-(1-methyl-1H-pyrazol-4-yl)-1,6-naphthyridin-7-yl)-2-(7-methyl-2,7-diazaspiro[3.5]nonan-2-yl)isonicotinamide [185];

N-(2-(1-methyl-1H-pyrazol-4-yl)-1,6-naphthyridin-7-yl)-2-(2,7-diazaspiro[3.5]nonan-7-yl) isonicotinamide [186];

N-(2-(1-methyl-1H-pyrazol-4-yl)-1,6-naphthyridin-7-yl)-2-(2-methyl-2,7-diazaspiro[3.5]nonan-7-yl)isonicotinamide [187];

2-(methyl(1-methylpiperidin-4-yl)amino)-N-(2-(1-methyl-1H-pyrazol-4-yl)-1,6-naphthyridin-7-yl)isonicotinamide [188];

N-(2-(1-methyl-1H-pyrazol-4-yl)-1,6-naphthyridin-7-yl)-2-((1-methylpiperidin-4-yl)thio) isonicotinamide [189];

N-(2-(1-methyl-1H-pyrazol-4-yl)-1,6-naphthyridin-7-yl)-2-(4-methylpiperazin-1-yl)pyrimidine-4-carboxamide [190];

N-(2-(1-methyl-1H-pyrazol-4-yl)-1,6-naphthyridin-7-yl)-6-(4-methylpiperazin-1-yl)pyridazine-4-carboxamide [191];

N-(2-(1-methyl-1H-pyrazol-4-yl)-1,6-naphthyridin-7-yl)-6-(4-methylpiperazin-1-yl)pyrimidine-4-carboxamide [192];

N-(2-(1-methyl-1H-pyrazol-4-yl)-1,6-naphthyridin-7-yl)-2-phenylacetamide [193];

N-(2-(1-methyl-1H-pyrazol-4-yl)-1,6-naphthyridin-7-yl)-3-phenylpropanamide [194];

N-(2-(1-methyl-1H-pyrazol-4-yl)-1,6-naphthyridin-7-yl)-2-(pyridin-3-yl)acetamide [195];

N-(2-(1-methyl-1H-pyrazol-4-yl)-1,6-naphthyridin-7-yl)-3-(pyridin-3-yl)propanamide [196];

N-(2-(1-methyl-1H-pyrazol-4-yl)-1,6-naphthyridin-7-yl)-2-(pyridin-4-yl)acetamide [197];
N-(2-(1-methyl-1H-pyrazol-4-yl)-1,6-naphthyridin-7-yl)-3-(pyridin-4-yl)propanamide [198];
N-(2-(1-methyl-1H-pyrazol-4-yl)-1,6-naphthyridin-7-yl) isoindoline-5-carboxamide [199];
2-methyl-N-(2-(1-methyl-1H-pyrazol-4-yl)-1,6-naphthyridin-7-yl)isoindoline-5-carboxamide [200];
N-(2-(1-methyl-1H-pyrazol-4-yl)-1,6-naphthyridin-7-yl)-1,2,3,4-tetrahydroisoquinoline-7-carboxamide [201];
2-methyl-N-(2-(1-methyl-1H-pyrazol-4-yl)-1,6-naphthyridin-7-yl)-1,2,3,4-tetrahydroisoquinoline-7-carboxamide [202];
2-methyl-N-(2-(1-methyl-1H-pyrazol-4-yl)-1,6-naphthyridin-7-yl)-1,2,3,4-tetrahydroisoquinoline-6-carboxamide [203];
N-(2-(1-methyl-1H-pyrazol-4-yl)-1,6-naphthyridin-7-yl)-1,2,3,4-tetrahydroisoquinoline-6-carboxamide [204];
N-(2-(1-methyl-1H-pyrazol-4-yl)-1,6-naphthyridin-7-yl)-1H-indole-5-carboxamide [205];
N-(2-(1-methyl-1H-pyrazol-4-yl)-1,6-naphthyridin-7-yl)benzofuran-5-carboxamide [206];
N-(2-(1-methyl-1H-pyrazol-4-yl)-1,6-naphthyridin-7-yl)furo[2,3-c]pyridine-5-carboxamide [207];
N-(2-(1-methyl-1H-pyrazol-4-yl)-1,6-naphthyridin-7-yl)benzo[b]thiophene-5-carboxamide [208];
N-(2-(1-methyl-1H-pyrazol-4-yl)-1,6-naphthyridin-7-yl)benzofuran-6-carboxamide [209];
N-(2-(1-methyl-1H-pyrazol-4-yl)-1,6-naphthyridin-7-yl)benzo[d]oxazole-6-carboxamide [210];
N-(2-(1-methyl-1H-pyrazol-4-yl)-1,6-naphthyridin-7-yl)benzo[d]thiazole-6-carboxamide [211];
N-(2-(1-methyl-1H-pyrazol-4-yl)-1,6-naphthyridin-7-yl)benzo[d]oxazole-5-carboxamide [212];
N-(2-(1-methyl-1H-pyrazol-4-yl)-1,6-naphthyridin-7-yl)benzo[d]thiazole-5-carboxamide [213];
N-(2-(1-methyl-1H-pyrazol-4-yl)-1,6-naphthyridin-7-yl)quinoline-3-carboxamide [214];
N-(2-(1-methyl-1H-pyrazol-4-yl)-1,6-naphthyridin-7-yl)quinoline-6-carboxamide [215];
N-(2-(1-methyl-1H-pyrazol-4-yl)-1,6-naphthyridin-7-yl)quinoxaline-6-carboxamide [216];
5-chloro-N-(2-(1-methyl-1H-pyrazol-4-yl)-1,6-naphthyridin-7-yl)-2-(4-methylpiperazin-1-yl) isonicotinamide [217];
3-chloro-N-(2-(1-methyl-1H-pyrazol-4-yl)-1,6-naphthyridin-7-yl)-2-(4-methylpiperazin-1-yl) isonicotinamide [218];
2-(2,5-diazabicyclo [2.2.1]heptan-2-yl)-N-(2-(1-methyl-1H-pyrazol-4-yl)-1,6-naphthyridin-7-yl)isonicotinamide [219];
N-(2-(1-methyl-1H-pyrazol-4-yl)-1,6-naphthyridin-7-yl)-2-(5-methyl-2,5-diazabicyclo[2.2.1] heptan-2-yl)isonicotinamide [220];
3-fluoro-N-(2-(1-methyl-1H-pyrazol-4-yl)-1,6-naphthyridin-7-yl)-2-(4-methylpiperazin-1-yl) isonicotinamide [221];
N-(2-(1-methyl-1H-pyrazol-4-yl)-1,6-naphthyridin-7-yl)-2-((4-methylpiperazin-1-yl)methyl) isonicotinamide [222];
N-(2-(1-methyl-1H-pyrazol-4-yl)-1,6-naphthyridin-7-yl)-2-(morpholinomethyl)isonicotinamide [223];
N-(2-(1-methyl-1H-pyrazol-4-yl)-1,6-naphthyridin-7-yl)-2-(pyrrolidin-1-ylmethyl) isonicotinamide [224];
N-(2-(1-methyl-1H-pyrazol-4-yl)-1,6-naphthyridin-7-yl)-2-(2-(4-methylpiperazin-1-yl)pyridin-4-yl)acetamide [225];
1-methyl-N-(2-(1-methyl-1H-pyrazol-4-yl)-1,6-naphthyridin-7-yl)-1H-indazole-5-carboxamide [226];
1-methyl-N-(2-(1-methyl-1H-pyrazol-4-yl)-1,6-naphthyridin-7-yl)-1H-benzo[d]imidazole-5-carboxamide [227];
N-(2-(1-methyl-1H-pyrazol-4-yl)-1,6-naphthyridin-7-yl)-1-(piperidin-4-yl)-1H-pyrazole-4-carboxamide [228];
N-(2-(1-methyl-1H-pyrazol-4-yl)-1,6-naphthyridin-7-yl)-1-(1-methylpiperidin-4-yl)-1H-pyrazole-4-carboxamide [229];
1-(1-ethylpiperidin-4-yl)-N-(2-(1-methyl-1H-pyrazol-4-yl)-1,6-naphthyridin-7-yl)-1H-pyrazole-4-carboxamide [230];
1-(1-(2-fluoroethyl)piperidin-4-yl)-N-(2-(1-methyl-1H-pyrazol-4-yl)-1,6-naphthyridin-7-yl)-1H-pyrazole-4-carboxamide [231];
1-(1-isopropylpiperidin-4-yl)-N-(2-(1-methyl-1H-pyrazol-4-yl)-1,6-naphthyridin-7-yl)-1H-pyrazole-4-carboxamide [232];
1-(1-cyclopropylpiperidin-4-yl)-N-(2-(1-methyl-1H-pyrazol-4-yl)-1,6-naphthyridin-7-yl)-1H-pyrazole-4-carboxamide [233];
isopropyl 4-(4-((2-(1-methyl-1H-pyrazol-4-yl)-1,6-naphthyridin-7-yl)carbamoyl)-1H-pyrazol-1-yl)piperidine-1-carboxylate [234];
N-(2-(1-methyl-1H-pyrazol-4-yl)-1,6-naphthyridin-7-yl)-1-(piperidin-4-yl)-1H-1,2,3-triazole-4-carboxamide [235];
N-(2-(1-methyl-1H-pyrazol-4-yl)-1,6-naphthyridin-7-yl)-1-(1-methylpiperidin-4-yl)-1H-1,2,3-triazole-4-carboxamide [236];
1-(1-(2-fluoroethyl)piperidin-4-yl)-N-(2-(1-methyl-1H-pyrazol-4-yl)-1,6-naphthyridin-7-yl)-1H-1,2,3-triazole-4-carboxamide [237];
1-(1-isopropylpiperidin-4-yl)-N-(2-(1-methyl-1H-pyrazol-4-yl)-1,6-naphthyridin-7-yl)-1H-1,2,3-triazole-4-carboxamide [238];
N-(2-(1-methyl-1H-pyrazol-4-yl)-1,6-naphthyridin-7-yl)-2-(4-methylpiperazin-1-yl)oxazole-5-carboxamide [239];
2-(3-(dimethylamino)azetidin-1-yl)-N-(2-(1-methyl-1H-pyrazol-4-yl)-1,6-naphthyridin-7-yl) oxazole-4-carboxamide [240];
N-(2-(1-methyl-1H-pyrazol-4-yl)-1,6-naphthyridin-7-yl)-2-(piperidin-4-yl)oxazole-4-carboxamide [241];
N-(2-(1-methyl-1H-pyrazol-4-yl)-1,6-naphthyridin-7-yl)-2-(1-methylpiperidin-4-yl)oxazole-4-carboxamide [242];
2-(1-(2-fluoroethyl)piperidin-4-yl)-N-(2-(1-methyl-1H-pyrazol-4-yl)-1,6-naphthyridin-7-yl) oxazole-4-carboxamide [243];
2-(1-isopropylpiperidin-4-yl)-N-(2-(1-methyl-1H-pyrazol-4-yl)-1,6-naphthyridin-7-yl)oxazole-4-carboxamide [244];
N-(2-(1-methyl-1H-pyrazol-4-yl)-1,6-naphthyridin-7-yl)-2-(4-methylpiperazin-1-yl)oxazole-4-carboxamide [245];
2-(3-(dimethylamino)azetidin-1-yl)-N-(2-(1-methyl-1H-pyrazol-4-yl)-1,6-naphthyridin-7-yl) thiazole-5-carboxamide [246];
N-(2-(1-methyl-1H-pyrazol-4-yl)-1,6-naphthyridin-7-yl)-2-(piperidin-4-yl)thiazole-4-carboxamide [247];
N-(2-(1-methyl-1H-pyrazol-4-yl)-1,6-naphthyridin-7-yl)-2-(4-methylpiperazin-1-yl)thiazole-4-carboxamide [248];

2-(1-(2-fluoroethyl)piperidin-4-yl)-N-(2-(1-methyl-1H-pyrazol-4-yl)-1,6-naphthyridin-7-yl) thiazole-4-carboxamide [249];

2-(1-isopropylpiperidin-4-yl)-N-(2-(1-methyl-1H-pyrazol-4-yl)-1,6-naphthyridin-7-yl)thiazole-4-carboxamide [250];

1-methyl-N-(2-(1-methyl-1H-pyrazol-4-yl)-1,6-naphthyridin-7-yl-8-d)piperidine-4-carboxamide [251];

N-(2-(1-methyl-1H-pyrazol-4-yl)-1,6-naphthyridin-7-yl)-1-(2-(methyl-$d_3$)propyl-1,1,2,3,3,3-$d_6$) piperidine-4-carboxamide [252];

N-(2-(1-methyl-1H-pyrazol-4-yl)-1,6-naphthyridin-7-yl)-2-(pyrrolidin-1-yl-2,2,5,5-$d_4$)acetamide [253];

N-(2-(1-methyl-1H-pyrazol-4-yl)-1,6-naphthyridin-7-yl)-2-(4-(methyl-$d_3$)piperazin-1-yl) acetamide [254];

N-(2-(1-methyl-1H-pyrazol-4-yl)-1,6-naphthyridin-7-yl)-2-(morpholino-$d_8$)acetamide [255];

(S)—N-(2-(1-(methyl-$d_3$)-1H-pyrazol-4-yl)-1,6-naphthyridin-7-yl)-2-(pyrrolidin-1-yl)propanamide [256];

1-isobutyl-N-(2-(1-(methyl-$d_3$)-1H-pyrazol-4-yl)-1,6-naphthyridin-7-yl)piperidine-4-carboxamide [257];

N-(2-(1-(methyl-$d_3$)-1H-pyrazol-4-yl)-1,6-naphthyridin-7-yl)-2-(4-methylpiperazin-1-yl) acetamide [258];

N-(2-(1-(methyl-$d_3$)-1H-pyrazol-4-yl)-1,6-naphthyridin-7-yl)-2-(pyrrolidin-1-yl)acetamide [259];

N-(2-(1-(methyl-$d_3$)-1H-pyrazol-4-yl)-1,6-naphthyridin-7-yl)-2-(piperidin-1-yl)acetamide [260];

N-(2-(1-(methyl-$d_3$)-1H-pyrazol-4-yl)-1,6-naphthyridin-7-yl)-1-(3,3,3-trifluoropropyl)piperidine-4-carboxamide [261];

N-(2-(1H-pyrazol-4-yl)-1,6-naphthyridin-7-yl)-2-(4-(methyl-$d_3$)piperazin-1-yl)isonicotinamide [262];

N-(2-(1-methyl-1H-pyrazol-4-yl)-1,6-naphthyridin-7-yl)-2-(4-(methyl-$d_3$)piperazin-1-yl) isonicotinamide [263];

N-(2-(1-(methyl-$d_3$)-1H-pyrazol-4-yl)-1,6-naphthyridin-7-yl)-2-(4-methylpiperazin-1-yl) isonicotinamide [264];

N-(2-(1-(methyl-$d_3$)-1H-pyrazol-4-yl)-1,6-naphthyridin-7-yl)-2-(4-(methyl-$d_3$)piperazin-1-yl) isonicotinamide [265];

N-(2-(1-(methyl-$d_3$)-1H-pyrazol-4-yl)-1,6-naphthyridin-7-yl)-1-(piperidin-4-yl)-1H-pyrazole-4-carboxamide [266];

N-(2-(1-(methyl-$d_3$)-1H-pyrazol-4-yl)-1,6-naphthyridin-7-yl)-1-(1-methylpiperidin-4-yl)-1H-pyrazole-4-carboxamide [267];

N-(2-(1-(methyl-$d_3$)-1H-pyrazol-4-yl)-1,6-naphthyridin-7-yl)-2-(piperidin-4-yl)oxazole-4-carboxamide [268];

N-(2-(1-(methyl-$d_3$)-1H-pyrazol-4-yl)-1,6-naphthyridin-7-yl)-2-(1-methylpiperidin-4-yl)oxazole-4-carboxamide [269];

N-(2-(1-ethyl-1H-pyrazol-4-yl)-1,6-naphthyridin-7-yl)-2-(pyrrolidin-1-yl)acetamide [270];

N-(2-(1-cyclopropyl-1H-pyrazol-4-yl)-1,6-naphthyridin-7-yl)-2-(pyrrolidin-1-yl)acetamide [271];

N-(2-(1-cyclopropyl-1H-pyrazol-4-yl)-1,6-naphthyridin-7-yl)-1-(3,3,3-trifluoropropyl)piperidine-4-carboxamide [272];

N-(2-(1-(1-methylpiperidin-4-yl)-1H-pyrazol-4-yl)-1,6-naphthyridin-7-yl) cyclohexanecarboxamide [273];

2-(pyrrolidin-1-yl)-N-(2-(5-(trifluoromethyl)-1H-pyrazol-4-yl)-1,6-naphthyridin-7-yl)acetamide [274];

N-(2-(5-(hydroxymethyl)-1-methyl-1H-pyrazol-4-yl)-1,6-naphthyridin-7-yl)-1-methylpiperidine-4-carboxamide [275];

N-(2-(5-(hydroxymethyl)-1-methyl-1H-pyrazol-4-yl)-1,6-naphthyridin-7-yl)tetrahydro-2H-pyran-4-carboxamide [276];

N-(2-(1-isopropyl-1H-pyrazol-4-yl)-1,6-naphthyridin-7-yl)-3-(piperidin-4-yloxy)benzamide [294];

N-(2-(1-isopropyl-1H-pyrazol-4-yl)-1,6-naphthyridin-7-yl)-3-((1-methylpiperidin-4-yl)oxy) benzamide [295];

N-(2-(1-isopropyl-1H-pyrazol-4-yl)-1,6-naphthyridin-7-yl)-4-(piperidin-4-yloxy)benzamide [296];

N-(2-(1-cyclopropyl-1H-pyrazol-4-yl)-1,6-naphthyridin-7-yl)-2-(4-methylpiperazin-1-yl) isonicotinamide [297];

4-fluoro-N-(2-(1-(1-methylpiperidin-4-yl)-1H-pyrazol-4-yl)-1,6-naphthyridin-7-yl)benzamide [298];

4-(difluoromethoxy)-N-(2-(1-(1-methylpiperidin-4-yl)-1H-pyrazol-4-yl)-1,6-naphthyridin-7-yl) benzamide [299];

5-fluoro-N-(2-(1-(1-methylpiperidin-4-yl)-1H-pyrazol-4-yl)-1,6-naphthyridin-7-yl)nicotinamide [300];

$N^2$-methyl-$N^5$-(2-(1-(1-methylpiperidin-4-yl)-1H-pyrazol-4-yl)-1,6-naphthyridin-7-yl)pyridine-2,5-dicarboxamide [301];

1-isopropyl-N-(2-(1-(1-methylpiperidin-4-yl)-1H-pyrazol-4-yl)-1,6-naphthyridin-7-yl)-1H-pyrazole-4-carboxamide [302];

2-methyl-N-(2-(1-(1-methylpiperidin-4-yl)-1H-pyrazol-4-yl)-1,6-naphthyridin-7-yl)thiazole-5-carboxamide [303];

N-(2-(5-amino-1-methyl-1H-pyrazol-4-yl)-1,6-naphthyridin-7-yl)-2-(4-methylpiperazin-1-yl) isonicotinamide [304];

4-(difluoromethoxy)-N-(2-(5-(hydroxymethyl)-1-methyl-1H-pyrazol-4-yl)-1,6-naphthyridin-7-yl) benzamide [305];

N-(2-(5-(hydroxymethyl)-1-methyl-1H-pyrazol-4-yl)-1,6-naphthyridin-7-yl)-2-(4-methylpiperazin-1-yl)isonicotinamide [306];

N-(2-(5-(hydroxymethyl)-1-methyl-1H-pyrazol-4-yl)-1,6-naphthyridin-7-yl)-2-(7-methyl-2,7-diazaspiro[3.5]nonan-2-yl)isonicotinamide [307];

4-fluoro-N-(2-(1-methyl-5-(pyrrolidin-1-ylmethyl)-1H-pyrazol-4-yl)-1,6-naphthyridin-7-yl) benzamide [308];

4-fluoro-N-(2-(1-methyl-5-(piperidin-1-ylmethyl)-1H-pyrazol-4-yl)-1,6-naphthyridin-7-yl) benzamide [309];

4-(difluoromethoxy)-N-(2-(1-methyl-5-(piperidin-1-ylmethyl)-1H-pyrazol-4-yl)-1,6-naphthyridin-7-yl)benzamide [310];

N-(2-(1-methyl-5-(piperidin-1-ylmethyl)-1H-pyrazol-4-yl)-1,6-naphthyridin-7-yl)-3-(pyrrolidin-1-ylmethyl) benzamide [311];

N-(2-(1-methyl-5-(piperidin-1-ylmethyl)-1H-pyrazol-4-yl)-1,6-naphthyridin-7-yl)-2-(7-methyl-2,7-diazaspiro[3.5]nonan-2-yl)isonicotinamide [312];

N-(2-(1-methyl-5-(piperidin-1-ylmethyl)-1H-pyrazol-4-yl)-1,6-naphthyridin-7-yl)-2-morpholinoisonicotinamide [313];

N-(2-(1-methyl-5-(morpholinomethyl)-1H-pyrazol-4-yl)-1,6-naphthyridin-7-yl)-2-morpholinoisonicotinamide [314];

N-(2-(4,5,6,7-tetrahydropyrazolo[1,5-a]pyrazin-3-yl)-1,6-naphthyridin-7-yl)-1-((1-(trifluoromethyl)cyclopropyl)methyl)piperidine-4-carboxamide [315];

3,3-difluoro-N-(2-(5-methyl-4,5,6,7-tetrahydropyrazolo[1,5-a]pyrazin-3-yl)-1,6-naphthyridin-7-yl)cyclobutane-1-carboxamide [316];

N-((4,4-difluorocyclohexyl)methyl)-2-(5-(2-fluoroethyl)-4,5,6,7-tetrahydropyrazolo[1,5-a] pyrazin-3-yl)-1,6-naphthyridin-7-amine [317];

N-(2-(5-(2-fluoroethyl)-4,5,6,7-tetrahydropyrazolo[1,5-a]pyrazin-3-yl)-1,6-naphthyridin-7-yl)-1-((1-(trifluoromethyl)cyclopropyl)methyl)piperidine-4-carboxamide [318];

N-(2-(5-(2-fluoroethyl)-4,5,6,7-tetrahydropyrazolo[1,5-a]pyrazin-3-yl)-1,6-naphthyridin-7-yl)-2-(pyrrolidin-1-yl)acetamide [319];

2-(7-azabicyclo[2.2.1]heptan-7-yl)-N-(2-(5-(2-fluoroethyl)-4,5,6,7-tetrahydropyrazolo[1,5-a]pyrazin-3-yl)-1,6-naphthyridin-7-yl)acetamide [320];

(R)—N-(2-(5-(2-fluoroethyl)-4,5,6,7-tetrahydropyrazolo[1,5-a]pyrazin-3-yl)-1,6-naphthyridin-7-yl)-1-isobutylpiperidine-3-carboxamide [321];

N-(2-(5-(2-fluoroethyl)-4,5,6,7-tetrahydropyrazolo[1,5-a]pyrazin-3-yl)-1,6-naphthyridin-7-yl) piperidine-4-carboxamide [322];

4-fluoro-N-(2-(5-(2-fluoroethyl)-4,5,6,7-tetrahydropyrazolo[1,5-a]pyrazin-3-yl)-1,6-naphthyridin-7-yl)-1-isobutylpiperidine-4-carboxamide [323];

N-(2-(5-(2-fluoroethyl)-4,5,6,7-tetrahydropyrazolo[1,5-a]pyrazin-3-yl)-1,6-naphthyridin-7-yl)-2-(4-methylpiperazin-1-yl)acetamide [324];

4-fluoro-N-(2-(4,5,6,7-tetrahydropyrazolo[1,5-a]pyrazin-3-yl)-1,6-naphthyridin-7-yl)benzamide [325];

N-(2-(5-(2-fluoroethyl)-4,5,6,7-tetrahydropyrazolo[1,5-a]pyrazin-3-yl)-1,6-naphthyridin-7-yl)-3-(4-methylpiperazin-1-yl)benzamide [326];

$N^5$-(2-(5-(2-fluoroethyl)-4,5,6,7-tetrahydropyrazolo[1,5-a]pyrazin-3-yl)-1,6-naphthyridin-7-yl)-$N^2$-methylpyridine-2,5-dicarboxamide [327];

N-(2-(5-(2-fluoroethyl)-4,5,6,7-tetrahydropyrazolo[1,5-a]pyrazin-3-yl)-1,6-naphthyridin-7-yl)-6-(4-methylpiperazin-1-yl)nicotinamide [328];

2-(azetidin-3-yloxy)-N-(2-(5-(2-fluoroethyl)-4,5,6,7-tetrahydropyrazolo[1,5-a]pyrazin-1,6-naphthyridin-7-yl) isonicotinamide [329];

N-(2-(1-methyl-1H-pyrazol-5-yl)-1,6-naphthyridin-7-yl)-1-(3,3,3-trifluoropropyl)piperidine-4-carboxamide [330];

1-methyl-N-(2-(1-methyl-1H-pyrazol-3-yl)-1,6-naphthyridin-7-yl)piperidine-4-carboxamide [331];

N-(2-(1-methyl-1H-pyrazol-3-yl)-1,6-naphthyridin-7-yl)-2-(4-methylpiperazin-1-yl) isonicotinamide [332];

2-fluoro-2-methyl-N-(2-(1-methyl-1H-1,2,3-triazol-4-yl)-1,6-naphthyridin-7-yl)propanamide [333];

2,2,3,3-tetramethyl-N-(2-(1-methyl-1H-1,2,3-triazol-4-yl)-1,6-naphthyridin-7-yl)cyclopropane-1-carboxamide [334];

trans-N-(2-(1-methyl-1H-1,2,3-triazol-4-yl)-1,6-naphthyridin-7-yl)-4-(pyrrolidin-1-yl) cyclohexane-1-carboxamide [335];

trans-N-(2-(1-methyl-1H-1,2,3-triazol-4-yl)-1,6-naphthyridin-7-yl)-4-morpholinocyclohexane-1-carboxamide [336];

N-(2-(1-methyl-1H-1,2,3-triazol-4-yl)-1,6-naphthyridin-7-yl)-2-(piperidin-1-yl)acetamide [337];

1-ethyl-4-fluoro-N-(2-(1-methyl-1H-1,2,3-triazol-4-yl)-1,6-naphthyridin-7-yl)piperidine-4-carboxamide [338];

4-fluoro-1-isobutyl-N-(2-(1-methyl-1H-1,2,3-triazol-4-yl)-1,6-naphthyridin-7-yl)piperidine-4-carboxamide [339];

N-(2-(1-methyl-1H-1,2,3-triazol-4-yl)-1,6-naphthyridin-7-yl)-1-(3,3,3-trifluoropropyl)piperidine-4-carboxamide [340];

N-(2-(1-methyl-1H-1,2,3-triazol-4-yl)-1,6-naphthyridin-7-yl)cyclopropanecarboxamide [341];

4,4-difluoro-N-(2-(1-methyl-1H-1,2,3-triazol-4-yl)-1,6-naphthyridin-7-yl)cyclohexane-1-carboxamide [342];

trans-4-(dimethylamino)-N-(2-(1-methyl-1H-1,2,3-triazol-4-yl)-1,6-naphthyridin-7-yl) cyclohexane-1-carboxamide [343];

trans-N-(2-(1-methyl-1H-1,2,3-triazol-4-yl)-1,6-naphthyridin-7-yl)-4-((4-methylpiperazin-1-yl) methyl)cyclohexane-1-carboxamide [344];

N-(2-(1-methyl-1H-1,2,3-triazol-4-yl)-1,6-naphthyridin-7-yl)piperidine-4-carboxamide [345];

1-isobutyl-N-(2-(1-methyl-1H-1,2,3-triazol-4-yl)-1,6-naphthyridin-7-yl)piperidine-4-carboxamide [346];

N-(2-(1-methyl-1H-1,2,3-triazol-4-yl)-1,6-naphthyridin-7-yl)-1-((1-(trifluoromethyl)cyclopropyl) methyl)piperidine-4-carboxamide [347];

N-(2-(1-methyl-1H-1,2,3-triazol-4-yl)-1,6-naphthyridin-7-yl)-1-((3-methyloxetan-3-yl)methyl) piperidine-4-carboxamide [348];

N-(2-(1-methyl-1H-1,2,3-triazol-4-yl)-1,6-naphthyridin-7-yl)-1-(2-(pyrrolidin-1-yl)acetyl) piperidine-4-carboxamide [349];

1'-methyl-N-(2-(1-methyl-1H-1,2,3-triazol-4-yl)-1,6-naphthyridin-7-yl)-[1,4'-bipiperidine]-4-carboxamide [350];

(R)—N-(2-(1-methyl-1H-1,2,3-triazol-4-yl)-1,6-naphthyridin-7-yl)piperidine-3-carboxamide [351];

(R)-1-isobutyl-N-(2-(1-methyl-1H-1,2,3-triazol-4-yl)-1,6-naphthyridin-7-yl)piperidine-3-carboxamide [352];

N-(2-(1-methyl-1H-1,2,3-triazol-4-yl)-1,6-naphthyridin-7-yl)-2-(pyrrolidin-1-yl)acetamide [353];

N-(2-(1-methyl-1H-1,2,3-triazol-4-yl)-1,6-naphthyridin-7-yl)-2-(4-methylpiperazin-1-yl) acetamide [354];

2-(7-azabicyclo[2.2.1]heptan-7-yl)-N-(2-(1-methyl-1H-1,2,3-triazol-4-yl)-1,6-naphthyridin-7-yl) acetamide [355];

1-(2-hydroxy-2-methylpropyl)-N-(2-(1-methyl-1H-1,2,3-triazol-4-yl)-1,6-naphthyridin-7-yl) piperidine-4-carboxamide [356];

N-(2-(1-methyl-1H-1,2,3-triazol-4-yl)-1,6-naphthyridin-7-yl)-2-morpholinoacetamide [357];

2-(4-methoxypiperidin-1-yl)-N-(2-(1-methyl-1H-1,2,3-triazol-4-yl)-1,6-naphthyridin-7-yl) acetamide [358];

N-(2-(1-methyl-1H-1,2,3-triazol-4-yl)-1,6-naphthyridin-7-yl)morpholine-4-carboxamide [359];

N-(2-(1-methyl-1H-1,2,3-triazol-4-yl)-1,6-naphthyridin-7-yl)-1-(piperidin-4-yl)-1H-pyrazole-4-carboxamide [360];

N-(2-(1-methyl-1H-1,2,3-triazol-4-yl)-1,6-naphthyridin-7-yl)-1-(1-methylpiperidin-4-yl)-1H-pyrazole-4-carboxamide [361];

1-(1-ethylpiperidin-4-yl)-N-(2-(1-methyl-1H-1,2,3-triazol-4-yl)-1,6-naphthyridin-7-yl)-1H-pyrazole-4-carboxamide [362];

1-(1-isopropylpiperidin-4-yl)-N-(2-(1-methyl-1H-1,2,3-triazol-4-yl)-1,6-naphthyridin-7-yl)-1H-pyrazole-4-carboxamide [363];

N-(2-(1-methyl-1H-1,2,3-triazol-4-yl)-1,6-naphthyridin-7-yl)-1H-1,2,3-triazole-4-carboxamide [364];

1-(1-(2-fluoroethyl)piperidin-4-yl)-N-(2-(1-methyl-1H-1,2,3-triazol-4-yl)-1,6-naphthyridin-7-yl)-1H-1,2,3-triazole-4-carboxamide [365];

1-(1-isopropylpiperidin-4-yl)-N-(2-(1-methyl-1H-1,2,3-triazol-4-yl)-1,6-naphthyridin-7-yl)-1H-1,2,3-triazole-4-carboxamide [366];

N-(2-(1-methyl-1H-1,2,3-triazol-4-yl)-1,6-naphthyridin-7-yl)-2-(piperidin-4-yl)oxazole-4-carboxamide [367];

N-(2-(1-methyl-1H-1,2,3-triazol-4-yl)-1,6-naphthyridin-7-yl)-2-(1-methylpiperidin-4-yl)oxazole-4-carboxamide [368];

2-(1-isopropylpiperidin-4-yl)-N-(2-(1-methyl-1H-1,2,3-triazol-4-yl)-1,6-naphthyridin-7-yl) oxazole-4-carboxamide [369];

2-fluoro-N-(2-(1-methyl-1H-1,2,3-triazol-4-yl)-1,6-naphthyridin-7-yl)benzamide [370];

N-(2-(1-methyl-1H-1,2,3-triazol-4-yl)-1,6-naphthyridin-7-yl)-3-((1-methylpiperidin-4-yl)oxy) benzamide [371];

$N^2$-methyl-$N^5$-(2-(1-methyl-1H-1,2,3-triazol-4-yl)-1,6-naphthyridin-7-yl)pyridine-2,5-dicarboxamide [372];

N-(2-(1-methyl-1H-1,2,3-triazol-4-yl)-1,6-naphthyridin-7-yl)-6-(4-methylpiperazin-1-yl) nicotinamide [373];

2-(3-(dimethylamino)azetidin-1-yl)-N-(2-(1-methyl-1H-1,2,3-triazol-4-yl)-1,6-naphthyridin-7-yl) isonicotinamide [374];

N-(2-(1-methyl-1H-1,2,3-triazol-4-yl)-1,6-naphthyridin-7-yl)-2-(1-methylpiperidin-4-yl) isonicotinamide [375];

2-(4-(dimethylamino)piperidin-1-yl)-N-(2-(1-methyl-1H-1,2,3-triazol-4-yl)-1,6-naphthyridin-7-yl)isonicotinamide [376];

N-(2-(1-methyl-1H-1,2,3-triazol-4-yl)-1,6-naphthyridin-7-yl)-2-morpholinoisonicotinamide [377];

N-(2-(1-methyl-1H-1,2,3-triazol-4-yl)-1,6-naphthyridin-7-yl)-2-(4-methylpiperazin-1-yl) isonicotinamide [378];

2-(4-methyl-1,4-diazepan-1-yl)-N-(2-(1-methyl-1H-1,2,3-triazol-4-yl)-1,6-naphthyridin-7-yl) isonicotinamide [379];

2-(4-isopropylpiperazin-1-yl)-N-(2-(1-methyl-1H-1,2,3-triazol-4-yl)-1,6-naphthyridin-7-yl) isonicotinamide [380];

N-(2-(1-methyl-1H-1,2,3-triazol-4-yl)-1,6-naphthyridin-7-yl)-2-(piperidin-4-ylamino) isonicotinamide [381];

2-(methyl(1-methylpiperidin-4-yl)amino)-N-(2-(1-methyl-1H-1,2,3-triazol-4-yl)-1,6-naphthyridin-7-yl) isonicotinamide [382];

N-(2-(1-methyl-1H-1,2,3-triazol-4-yl)-1,6-naphthyridin-7-yl)-2-((1-methylpiperidin-4-yl)thio) isonicotinamide [383];

2-methyl-N-(2-(1-methyl-1H-1,2,3-triazol-4-yl)-1,6-naphthyridin-7-yl)-1,2,3,4-tetrahydroisoquinoline-6-carboxamide [384];

N-(2-(1-methyl-1H-1,2,3-triazol-4-yl)-1,6-naphthyridin-7-yl)-2-(piperazin-1-yl)isonicotinamide [385];

N-(2-(1-methyl-1H-1,2,3-triazol-4-yl)-1,6-naphthyridin-7-yl)-2-(2-(4-methylpiperazin-1-yl) pyridin-4-yl)acetamide [386];

1,1-bis(methyl-$d_3$)-4-(4-((2-(1-methyl-1H-1,2,3-triazol-4-yl)-1,6-naphthyridin-7-yl)carbamoyl) pyridin-2-yl) piperazin-1-ium [387];

N-(2-(1-methyl-1H-1,2,3-triazol-4-yl)-1,6-naphthyridin-7-yl)-2-(4-(methyl-d3)piperazin-1-yl) isonicotinamide [388];

N-(2-(1-methyl-1H-1,2,3-triazol-5-yl)-1,6-naphthyridin-7-yl)-1-(3,3,3-trifluoropropyl)piperidine-4-carboxamide [389];

N-(2-(4-methyl-4H-1,2,4-triazol-3-yl)-1,6-naphthyridin-7-yl)-2-morpholinoacetamide [390];

N-(2-(4-methyl-4H-1,2,4-triazol-3-yl)-1,6-naphthyridin-7-yl)-1-(3,3,3-trifluoropropyl)piperidine-4-carboxamide [391];

4-fluoro-1-isobutyl-N-(2-(4-methyl-4H-1,2,4-triazol-3-yl)-1,6-naphthyridin-7-yl)piperidine-4-carboxamide [392];

N-(2-(4,5-dimethyl-4H-1,2,4-triazol-3-yl)-1,6-naphthyridin-7-yl)-2-morpholinoacetamide [393];

N-(2-(4,5-dimethyl-4H-1,2,4-triazol-3-yl)-1,6-naphthyridin-7-yl)-1-(3,3,3-trifluoropropyl) piperidine-4-carboxamide [394];

N-(2-(1H-1,2,3-triazol-1-yl)-1,6-naphthyridin-7-yl)-4-fluoro-1-isobutylpiperidine-4-carboxamide [395];

N-(2-(2H-1,2,3-triazol-2-yl)-1,6-naphthyridin-7-yl)-4-fluoro-1-isobutylpiperidine-4-carboxamide [396];

N-(2-(1H-1,2,4-triazol-1-yl)-1,6-naphthyridin-7-yl)-2-(4-methylpiperazin-1-yl)isonicotinamide [397];

1-isobutyl-N-(2-(1-methyl-1H-tetrazol-5-yl)-1,6-naphthyridin-7-yl)piperidine-4-carboxamide [398];

2,2,3,3-tetramethyl-N-(2-(1-methyl-1H-imidazol-5-yl)-1,6-naphthyridin-7-yl)cyclopropane-1-carboxamide [399];

4,4-difluoro-N-(2-(1-methyl-1H-imidazol-5-yl)-1,6-naphthyridin-7-yl)cyclohexane-1-carboxamide [400];

N-(2-(1-methyl-1H-imidazol-5-yl)-1,6-naphthyridin-7-yl)-2-(piperidin-1-yl)acetamide [401];

2-fluoro-2-methyl-N-(2-(1-methyl-1H-imidazol-5-yl)-1,6-naphthyridin-7-yl)propanamide [402];

1-fluoro-N-(2-(1-methyl-1H-imidazol-5-yl)-1,6-naphthyridin-7-yl)cyclopropane-1-carboxamide [403];

2-methyl-N-(2-(1-methyl-1H-imidazol-5-yl)-1,6-naphthyridin-7-yl)-2-azaspiro [3.3]heptane-6-carboxamide [404];

1-fluoro-N-(2-(1-methyl-1H-imidazol-5-yl)-1,6-naphthyridin-7-yl)cyclohexane-1-carboxamide [405];

trans-4-methoxy-N-(2-(1-methyl-1H-imidazol-5-yl)-1,6-naphthyridin-7-yl)cyclohexane-1-carboxamide [406];

trans-4-(hydroxymethyl)-N-(2-(1-methyl-1H-imidazol-5-yl)-1,6-naphthyridin-7-yl)cyclohexane-1-carboxamide [407];

N-(2-(1-methyl-1H-imidazol-5-yl)-1,6-naphthyridin-7-yl)azetidine-3-carboxamide [408];

(R)—N-(2-(1-methyl-1H-imidazol-5-yl)-1,6-naphthyridin-7-yl)tetrahydrofuran-2-carboxamide [409];

1-(2-methoxyethyl)-N-(2-(1-methyl-1H-imidazol-5-yl)-1,6-naphthyridin-7-yl)piperidine-4-carboxamide [410];

N-(2-(1-methyl-1H-imidazol-5-yl)-1,6-naphthyridin-7-yl)-1-(3,3,3-trifluoropropyl)piperidine-4-carboxamide [411];

1-isobutyl-N-(2-(1-methyl-1H-imidazol-5-yl)-1,6-naphthyridin-7-yl)piperidine-4-carboxamide [412];

N-(2-(1-methyl-1H-imidazol-5-yl)-1,6-naphthyridin-7-yl)-1-(methylsulfonyl)piperidine-4-carboxamide [413];

N-(2-(1-methyl-1H-imidazol-5-yl)-1,6-naphthyridin-7-yl)-2-(pyrrolidin-1-yl)propanamide [414];

2-isopropoxy-N-(2-(1-methyl-1H-imidazol-5-yl)-1,6-naphthyridin-7-yl)acetamide [415];

3-isopropoxy-N-(2-(1-methyl-1H-imidazol-5-yl)-1,6-naphthyridin-7-yl)propanamide [416];

N-(2-(1,2-dimethyl-1H-imidazol-5-yl)-1,6-naphthyridin-7-yl)cyclopropanecarboxamide [417];

N-(2-(1,2-dimethyl-1H-imidazol-5-yl)-1,6-naphthyridin-7-yl)cyclohexanecarboxamide [418];

N-(2-(1,2-dimethyl-1H-imidazol-5-yl)-1,6-naphthyridin-7-yl)-4,4-difluorocyclohexane-1-carboxamide [419];

(S)—N-(2-(1,2-dimethyl-1H-imidazol-5-yl)-1,6-naphthyridin-7-yl)tetrahydrofuran-2-carboxamide [420];

N-(2-(1,2-dimethyl-1H-imidazol-5-yl)-1,6-naphthyridin-7-yl)-3,3-difluorocyclobutane-1-carboxamide [421];

N-(2-(1,2-dimethyl-1H-imidazol-5-yl)-1,6-naphthyridin-7-yl)-1-fluorocyclopropane-1-carboxamide [422];
N-(2-(1,2-dimethyl-1H-imidazol-5-yl)-1,6-naphthyridin-7-yl)morpholine-4-carboxamide [423];
N-(2-(1,2-dimethyl-1H-imidazol-5-yl)-1,6-naphthyridin-7-yl)morpholine-$d_8$-4-carboxamide [424];
1-methyl-N-(2-(1-methyl-1H-imidazol-5-yl)-1,6-naphthyridin-7-yl)-1H-pyrazole-4-carboxamide [425];
1-ethyl-N-(2-(1-methyl-1H-imidazol-5-yl)-1,6-naphthyridin-7-yl)-1H-pyrazole-4-carboxamide [426];
1-isopropyl-N-(2-(1-methyl-1H-imidazol-5-yl)-1,6-naphthyridin-7-yl)-1H-pyrazole-4-carboxamide [427];
1-cyclopropyl-N-(2-(1-methyl-1H-imidazol-5-yl)-1,6-naphthyridin-7-yl)-1H-pyrazole-4-carboxamide [428];
N-(2-(5-(azetidin-1-ylmethyl)-1-methyl-1H-pyrazol-4-yl)-1,6-naphthyridin-7-yl)-4,4-difluorocyclohexane-1-carboxamide [277];
4,4-difluoro-N-(2-(1-methyl-5-(pyrrolidin-1-ylmethyl)-1H-pyrazol-4-yl)-1,6-naphthyridin-7-yl) cyclohexane-1-carboxamide [278];
4,4-difluoro-N-(2-(1-methyl-5-(piperidin-1-ylmethyl)-1H-pyrazol-4-yl)-1,6-naphthyridin-7-yl) cyclohexane-1-carboxamide [279];
2-(2-fluoroethyl)-N-(2-(1-methyl-5-(piperidin-1-ylmethyl)-1H-pyrazol-4-yl)-1,6-naphthyridin-7-yl)-2-azaspiro[3.3]]heptane-6-carboxamide [280];
tert-butyl 6-((2-(1-methyl-5-(piperidin-1-ylmethyl)-1H-pyrazol-4-yl)-1,6-naphthyridin-7-yl)carbamoyl)-2-azaspiro[3.3]heptane-2-carboxylate [281];
2-fluoro-2-methyl-N-(2-(1-methyl-5-(piperidin-1-ylmethyl)-1H-pyrazol-4-yl)-1,6-naphthyridin-7-yl)propanamide [282];
2-(diethylamino)-N-(2-(1-methyl-5-(piperidin-1-ylmethyl)-1H-pyrazol-4-yl)-1,6-naphthyridin-7-yl)acetamide [283];
trans-4-methoxy-N-(2-(1-methyl-5-(piperidin-1-ylmethyl)-1H-pyrazol-4-yl)-1,6-naphthyridin-7-yl)cyclohexane-1-carboxamide [284];
trans-4-(hydroxymethyl)-N-(2-(1-methyl-5-(piperidin-1-ylmethyl)-1H-pyrazol-4-yl)-1,6-naphthyridin-7-yl)cyclohexane-1-carboxamide [285];
(R)—N-(2-(1-methyl-5-(piperidin-1-ylmethyl)-1H-pyrazol-4-yl)-1,6-naphthyridin-7-yl)pyrrolidine-2-carboxamide [286];
1-isobutyl-N-(2-(1-methyl-5-(piperidin-1-ylmethyl)-1H-pyrazol-4-yl)-1,6-naphthyridin-7-yl) piperidine-4-carboxamide [287];
N-(2-(1-methyl-5-(piperidin-1-ylmethyl)-1H-pyrazol-4-yl)-1,6-naphthyridin-7-yl)-1-(oxetan-3-yl)piperidine-4-carboxamide [288];
1-benzoyl-N-(2-(1-methyl-5-(piperidin-1-ylmethyl)-1H-pyrazol-4-yl)-1,6-naphthyridin-7-yl) piperidine-4-carboxamide [289];
N-(2-(1-methyl-5-(piperidin-1-ylmethyl)-1H-pyrazol-4-yl)-1,6-naphthyridin-7-yl)tetrahydro-2H-pyran-4-carboxamide [290];
N-(2-(1-methyl-5-(piperidin-1-ylmethyl)-1H-pyrazol-4-yl)-1,6-naphthyridin-7-yl)-2-(4-methylpiperidin-1-yl)acetamide [291];
N-(2-(1-(difluoromethyl)-1H-pyrazol-4-yl)-1,6-naphthyridin-7-yl)-2-(4-methylpiperazin-1-yl) isonicotinamide [292];
N-(2-(1-ethyl-1H-pyrazol-4-yl)-1,6-naphthyridin-7-yl)-2-(4-methylpiperazin-1-yl) isonicotinamide [293];
1-isobutyl-N-(2-(1-methyl-1H-imidazol-5-yl)-1,6-naphthyridin-7-yl)-1H-pyrazole-4-carboxamide [429];
1-methyl-N-(2-(1-methyl-1H-imidazol-5-yl)-1,6-naphthyridin-7-yl)-1H-pyrazole-3-carboxamide [430];
N-(2-(1-methyl-1H-imidazol-5-yl)-1,6-naphthyridin-7-yl)-2-(1-methyl-1H-pyrazol-4-yl) acetamide [431];
1-methyl-N-(2-(1-methyl-1H-imidazol-5-yl)-1,6-naphthyridin-7-yl)-1H-imidazole-4-carboxamide [432];
1-isopropyl-N-(2-(1-methyl-1H-imidazol-5-yl)-1,6-naphthyridin-7-yl)-1H-imidazole-4-carboxamide [433];
N-(2-(1-methyl-1H-imidazol-5-yl)-1,6-naphthyridin-7-yl)-1-(tetrahydro-2H-pyran-4-yl)-1H-imidazole-4-carboxamide [434];
1,2-dimethyl-N-(2-(1-methyl-1H-imidazol-5-yl)-1,6-naphthyridin-7-yl)-1H-imidazole-5-carboxamide [435];
1-methyl-N-(2-(1-methyl-1H-imidazol-5-yl)-1,6-naphthyridin-7-yl)-1H-1,2,4-triazole-3-carboxamide [436];
2-methyl-N-(2-(1-methyl-1H-imidazol-5-yl)-1,6-naphthyridin-7-yl)oxazole-4-carboxamide [437];
2-isopropyl-N-(2-(1-methyl-1H-imidazol-5-yl)-1,6-naphthyridin-7-yl)oxazole-4-carboxamide [438];
4-methyl-N-(2-(1-methyl-1H-imidazol-5-yl)-1,6-naphthyridin-7-yl)oxazole-2-carboxamide [439];
4-methyl-N-(2-(1-methyl-1H-imidazol-5-yl)-1,6-naphthyridin-7-yl)thiazole-2-carboxamide [440];
2-methyl-N-(2-(1-methyl-1H-imidazol-5-yl)-1,6-naphthyridin-7-yl)thiazole-4-carboxamide [441];
5-methyl-N-(2-(1-methyl-1H-imidazol-5-yl)-1,6-naphthyridin-7-yl)-1,3,4-oxadiazole-2-carboxamide [442];
5-methyl-N-(2-(1-methyl-1H-imidazol-5-yl)-1,6-naphthyridin-7-yl)-1,3,4-thiadiazole-2-carboxamide [443];
1-isopropyl-N-(2-(1-isopropyl-1H-imidazol-5-yl)-1,6-naphthyridin-7-yl)-1H-pyrazole-4-carboxamide [444];
N-(2-(1,2-dimethyl-1H-imidazol-5-yl)-1,6-naphthyridin-7-yl)-1-methyl-1H-pyrazole-4-carboxamide [445];
N-(2-(1,2-dimethyl-1H-imidazol-5-yl)-1,6-naphthyridin-7-yl)-1-isopropyl-1H-pyrazole-4-carboxamide [446];
N-(2-(1,2-dimethyl-1H-imidazol-5-yl)-1,6-naphthyridin-7-yl)-2-methylthiazole-5-carboxamide [447];
4-fluoro-N-(2-(1-methyl-1H-imidazol-5-yl)-1,6-naphthyridin-7-yl)benzamide [448];
4-(difluoromethoxy)-N-(2-(1-methyl-1H-imidazol-5-yl)-1,6-naphthyridin-7-yl)benzamide [449];
N-(2-(1-methyl-1H-imidazol-5-yl)-1,6-naphthyridin-7-yl)-3-(pyrrolidin-1-ylmethyl)benzamide [450];
2-fluoro-N-(2-(1-methyl-1H-imidazol-5-yl)-1,6-naphthyridin-7-yl)benzamide-3,4,5,6-$d_4$ [451];
4-fluoro-N-(2-(1-methyl-1H-imidazol-5-yl)-1,6-naphthyridin-7-yl)benzamide-2,3,5,6-$d_4$ [452];
2-chloro-N-(2-(1-methyl-1H-imidazol-5-yl)-1,6-naphthyridin-7-yl)benzamide-3,4,5,6-$d_4$ [453];
4-chloro-N-(2-(1-methyl-1H-imidazol-5-yl)-1,6-naphthyridin-7-yl)benzamide-2,3,5,6-$d_4$ [454];
4-(methyl-$d_3$)—N-(2-(1-methyl-1H-imidazol-5-yl)-1,6-naphthyridin-7-yl)benzamide [455];
4-methyl-N-(2-(1-methyl-1H-imidazol-5-yl)-1,6-naphthyridin-7-yl)benzamide-2,3,5,6-$d_4$ [456];
4-(methyl-$d_3$)—N-(2-(1-methyl-1H-imidazol-5-yl)-1,6-naphthyridin-7-yl)benzamide-2,3,5,6-$d_4$ [257];
4-(methoxy-$d_3$)—N-(2-(1-methyl-1H-imidazol-5-yl)-1,6-naphthyridin-7-yl)benzamide [458];
4-(methoxy-$d_3$)—N-(2-(1-methyl-1H-imidazol-5-yl)-1,6-naphthyridin-7-yl)benzamide-2,3,5,6-$d_4$ [459];
4-methoxy-N-(2-(1-methyl-1H-imidazol-5-yl)-1,6-naphthyridin-7-yl)benzamide-2,3,5,6-$d_4$ [460];
(E)-N-(2-(1,2-dimethyl-1H-imidazol-5-yl)-1,6-naphthyridin-7-yl)-3-(phenyl-2,3,4,5,6-$d_5$) acrylamide [461];

(E)-N-(2-(1,2-dimethyl-1H-imidazol-5-yl)-1,6-naphthyridin-7-yl)-3-(phenyl-2,3,4,5,6-d$_5$) acrylamide-2,3-d$_2$ [462];
N-(2-(1,2-dimethyl-1H-imidazol-5-yl)-1,6-naphthyridin-7-yl)-2-(4-fluorophenyl)acetamide-2,2-d$_2$ [463];
(E)-N-(2-(1-methyl-1H-imidazol-5-yl)-1,6-naphthyridin-7-yl)-3-(phenyl-2,3,4,5,6-d$_5$)acrylamide [464];
(E)-N-(2-(1-methyl-1H-imidazol-5-yl)-1,6-naphthyridin-7-yl)-3-(phenyl-2,3,4,5,6-d$_5$)acrylamide-2,3-d$_2$ [465];
2-(4-fluorophenyl)-N-(2-(1-methyl-1H-imidazol-5-yl)-1,6-naphthyridin-7-yl)acetamide-2,2-d$_2$ [466];
N-(2-(1-methyl-1H-imidazol-5-yl)-1,6-naphthyridin-7-yl)-2-(4-methylpiperazin-1-yl) isonicotinamide [467];
2-(dimethylamino)-N-(2-(1-methyl-1H-imidazol-5-yl)-1,6-naphthyridin-7-yl)isonicotinamide [468];
2-(3-aminoazetidin-1-yl)-N-(2-(1-methyl-1H-imidazol-5-yl)-1,6-naphthyridin-7-yl) isonicotinamide [469];
N-(2-(1-methyl-1H-imidazol-5-yl)-1,6-naphthyridin-7-yl)-2-(pyrrolidin-1-yl)isonicotinamide [470];
N-(2-(1-methyl-1H-imidazol-5-yl)-1,6-naphthyridin-7-yl)-2-(piperidin-1-yl)isonicotinamide [471];
N-(2-(1-methyl-1H-imidazol-5-yl)-1,6-naphthyridin-7-yl)-2-morpholinoisonicotinamide [472];
2-(4-isopropylpiperazin-1-yl)-N-(2-(1-methyl-1H-imidazol-5-yl)-1,6-naphthyridin-7-yl) isonicotinamide [473];
2-(4-cyclopropylpiperazin-1-yl)-N-(2-(1-methyl-1H-imidazol-5-yl)-1,6-naphthyridin-7-yl) isonicotinamide [474];
N-(2-(1-methyl-1H-imidazol-5-yl)-1,6-naphthyridin-7-yl)-2-(2,7-diazaspiro[3.5]nonan-2-yl) isonicotinamide [475];
N-(2-(1-methyl-1H-imidazol-5-yl)-1,6-naphthyridin-7-yl)-2-(7-methyl-2,7-diazaspiro[3.5]nonan-2-yl)isonicotinamide [476];
N-(2-(1-methyl-1H-imidazol-5-yl)-1,6-naphthyridin-7-yl)isoindoline-5-carboxamide [477];
2-methyl-N-(2-(1-methyl-1H-imidazol-5-yl)-1,6-naphthyridin-7-yl)isoindoline-5-carboxamide [478];
2-(azetidin-1-yl)-N-(2-(1-methyl-1H-imidazol-5-yl)-1,6-naphthyridin-7-yl)isonicotinamide [479];
2-methoxy-N-(2-(1-methyl-1H-imidazol-5-yl)-1,6-naphthyridin-7-yl)isonicotinamide [480];
2-methyl-N-(2-(1-methyl-1H-imidazol-5-yl)-1,6-naphthyridin-7-yl)isonicotinamide [481];
2-cyano-N-(2-(1-methyl-1H-imidazol-5-yl)-1,6-naphthyridin-7-yl)isonicotinamide [482];
2-(3,3-difluoroazetidin-1-yl)-N-(2-(1-methyl-1H-imidazol-5-yl)-1,6-naphthyridin-7-yl) isonicotinamide [483];
2-(4,4-difluoropiperidin-1-yl)-N-(2-(1-methyl-1H-imidazol-5-yl)-1,6-naphthyridin-7-yl) isonicotinamide [484];
2-isopropoxy-N-(2-(1-methyl-1H-imidazol-5-yl)-1,6-naphthyridin-7-yl)isonicotinamide [485];
N-(2-(1-methyl-1H-imidazol-5-yl)-1,6-naphthyridin-7-yl)-2-(pyrrolidin-1-yl-2,2,5,5-d$_4$) isonicotinamide [486];
N-(2-(1-methyl-1H-imidazol-5-yl)-1,6-naphthyridin-7-yl)-2-(pyrrolidin-1-yl-d$_8$)isonicotinamide [487];
N-(2-(1-methyl-1H-imidazol-5-yl)-1,6-naphthyridin-7-yl)-2-(piperidin-1-yl-d$_{10}$)isonicotinamide [488];
N-(2-(1-methyl-1H-imidazol-5-yl)-1,6-naphthyridin-7-yl)-2-(morpholino-d$_8$)isonicotinamide [489];
N-(2-(1,2-dimethyl-1H-imidazol-5-yl)-1,6-naphthyridin-7-yl)-4-isopropoxybenzamide [490];
N-(2-(1,2-dimethyl-1H-imidazol-5-yl)-1,6-naphthyridin-7-yl)-4-(piperidin-4-yloxy)benzamide [491];
4-(benzyloxy)-N-(2-(1,2-dimethyl-1H-imidazol-5-yl)-1,6-naphthyridin-7-yl)benzamide [492];
N-(2-(1,2-dimethyl-1H-imidazol-5-yl)-1,6-naphthyridin-7-yl)-2-fluorobenzamide-3,4,5,6-d$_4$ [493];
N-(2-(1,2-dimethyl-1H-imidazol-5-yl)-1,6-naphthyridin-7-yl)-4-fluorobenzamide-2,3,5,6-d$_4$ [494];
2-chloro-N-(2-(1,2-dimethyl-1H-imidazol-5-yl)-1,6-naphthyridin-7-yl)benzamide-3,4,5,6-d$_4$ [495];
4-chloro-N-(2-(1,2-dimethyl-1H-imidazol-5-yl)-1,6-naphthyridin-7-yl)benzamide-2,3,5,6-d$_4$ [496];
N-(2-(1,2-dimethyl-1H-imidazol-5-yl)-1,6-naphthyridin-7-yl)-4-(methyl-d$_3$)benzamide [497];
N-(2-(1,2-dimethyl-1H-imidazol-5-yl)-1,6-naphthyridin-7-yl)-4-methylbenzamide-2,3,5,6-d$_4$ [498];
N-(2-(1,2-dimethyl-1H-imidazol-5-yl)-1,6-naphthyridin-7-yl)-4-(methyl-d$_3$)benzamide-2,3,5,6-d$_4$ [499];
N-(2-(1,2-dimethyl-1H-imidazol-5-yl)-1,6-naphthyridin-7-yl)-4-(methoxy-d$_3$)benzamide [500];
N-(2-(1,2-dimethyl-1H-imidazol-5-yl)-1,6-naphthyridin-7-yl)-4-(methoxy-d$_3$)benzamide-2,3,5,6-d$_4$ [501];
N-(2-(1,2-dimethyl-1H-imidazol-5-yl)-1,6-naphthyridin-7-yl)-4-methoxybenzamide-2,3,5,6-d$_4$ [502];
N-(2-(1,2-dimethyl-1H-imidazol-5-yl)-1,6-naphthyridin-7-yl)-2-(4-methylpiperazin-1-yl) isonicotinamide [503];
N-(2-(1,2-dimethyl-1H-imidazol-5-yl)-1,6-naphthyridin-7-yl)-2-morpholinoisonicotinamide [504];
N-(2-(1,2-dimethyl-1H-imidazol-5-yl)-1,6-naphthyridin-7-yl)-2-(pyrrolidin-1-yl)isonicotinamide [505];
N-(2-(1,2-dimethyl-1H-imidazol-5-yl)-1,6-naphthyridin-7-yl)-2-(dimethylamino)isonicotinamide [506];
N-(2-(1,2-dimethyl-1H-imidazol-5-yl)-1,6-naphthyridin-7-yl)-2-(pyrrolidin-1-yl-2,2,5,5-d$_4$) isonicotinamide [507];
N-(2-(1,2-dimethyl-1H-imidazol-5-yl)-1,6-naphthyridin-7-yl)-2-(pyrrolidin-1-yl-d$_8$) isonicotinamide [508];
N-(2-(1,2-dimethyl-1H-imidazol-5-yl)-1,6-naphthyridin-7-yl)-2-(piperidin-1-yl-d$_{10}$) isonicotinamide [509];
N-(2-(1,2-dimethyl-1H-imidazol-5-yl)-1,6-naphthyridin-7-yl)-2-(morpholino-d$_8$)isonicotinamide [510];
N-(2-(5,6,7,8-tetrahydroimidazo[1,2-a]pyrazin-3-yl)-1,6-naphthyridin-7-yl) cyclopropanecarboxamide [511];
N-(2-(7-methyl-5,6,7,8-tetrahydroimidazo[1,2-a]pyrazin-3-yl)-1,6-naphthyridin-7-yl) cyclopropanecarboxamide [512];
3,3-difluoro-N-(2-(5,6,7,8-tetrahydroimidazo[1,2-a]pyrazin-3-yl)-1,6-naphthyridin-7-yl) cyclobutane-1-carboxamide [513];
(R)—N-(2-(5,6,7,8-tetrahydroimidazo[1,2-a]pyrazin-3-yl)-1,6-naphthyridin-7-yl)pyrrolidine-2-carboxamide [514];
(R)—N-(2-(5,6,7,8-tetrahydroimidazo[1,2-a]pyrazin-3-yl)-1,6-naphthyridin-7-yl)piperidine-3-carboxamide [515];
1-methyl-N-(2-(5,6,7,8-tetrahydroimidazo[1,2-a]pyrazin-3-yl)-1,6-naphthyridin-7-yl)piperidine-4-carboxamide [516];
N-(2-(5,6,7,8-tetrahydroimidazo[1,2-a]pyrazin-3-yl)-1,6-naphthyridin-7-yl)-1-((1-(trifluoromethyl)cyclopropyl)methyl)piperidine-4-carboxamide [517];
1-benzoyl-N-(2-(5,6,7,8-tetrahydroimidazo[1,2-a]pyrazin-3-yl)-1,6-naphthyridin-7-yl)piperidine-4-carboxamide [518];

4-fluoro-1-isobutyl-N-(2-(5,6,7,8-tetrahydroimidazo[1,2-a]pyrazin-3-yl)-1,6-naphthyridin-7-yl) piperidine-4-carboxamide [519];

(R)-2-(2-methylpyrrolidin-1-yl)-N-(2-(5,6,7,8-tetrahydroimidazo[1,2-a]pyrazin-3-yl)-1,6-naphthyridin-7-yl) acetamide [520];

2-(cyclobutyl(methyl)amino)-N-(2-(5,6,7,8-tetrahydroimidazo[1,2-a]pyrazin-3-yl)-1,6-naphthyridin-7-yl) acetamide [521];

4-fluoro-N-(2-(5,6,7,8-tetrahydroimidazo[1,2-a]pyrazin-3-yl)-1,6-naphthyridin-7-yl)benzamide [522];

4-isopropoxy-N-(2-(5,6,7,8-tetrahydroimidazo[1,2-a]pyrazin-3-yl)-1,6-naphthyridin-7-yl) benzamide [523];

4-(difluoromethoxy)-N-(2-(5,6,7,8-tetrahydroimidazo[1,2-a]pyrazin-3-yl)-1,6-naphthyridin-7-yl) benzamide [524];

2-((2-(dimethylamino)ethyl)amino)-N-(2-(5,6,7,8-tetrahydroimidazo[1,2-a]pyrazin-3-yl)-1,6-naphthyridin-7-yl)isonicotinamide [525];

2-((1-isopropylpiperidin-4-yl)oxy)-N-(2-(5,6,7,8-tetrahydroimidazo[1,2-a]pyrazin-3-yl)-1,6-naphthyridin-7-yl)isonicotinamide [526];

N-(2-(oxazol-5-yl)-1,6-naphthyridin-7-yl)-1-(3,3,3-trifluoropropyl)piperidine-4-carboxamide [527];

N-(2-(oxazol-5-yl)-1,6-naphthyridin-7-yl)cyclopropanecarboxamide [528];

(R)—N-(2-(oxazol-5-yl)-1,6-naphthyridin-7-yl)tetrahydrofuran-2-carboxamide [529];

(R)—N-(2-(oxazol-5-yl)-1,6-naphthyridin-7-yl)piperidine-3-carboxamide [530];

N-(2-(oxazol-5-yl)-1,6-naphthyridin-7-yl)tetrahydro-2H-pyran-4-carboxamide [531];

N-(2-(oxazol-5-yl)-1,6-naphthyridin-7-yl)-1-(2-(pyrrolidin-1-yl)acetyl)piperidine-4-carboxamide [532];

1'-methyl-N-(2-(oxazol-5-yl)-1,6-naphthyridin-7-yl)-[1,4'-bipiperidine]-4-carboxamide [533];

cis-4-morpholino-N-(2-(oxazol-5-yl)-1,6-naphthyridin-7-yl)cyclohexane-1-carboxamide [534];

2-(cyclobutyl(methyl)amino)-N-(2-(oxazol-5-yl)-1,6-naphthyridin-7-yl)acetamide [535];

N-(2-(oxazol-5-yl)-1,6-naphthyridin-7-yl)-2-(pyrrolidin-1-yl)acetamide [536];

(R)-2-(2-methylpyrrolidin-1-yl)-N-(2-(oxazol-5-yl)-1,6-naphthyridin-7-yl)acetamide [537];

2-(4-methylpiperazin-1-yl)-N-(2-(oxazol-5-yl)-1,6-naphthyridin-7-yl)acetamide [538];

trans-4-((4-methylpiperazin-1-yl)methyl)-N-(2-(oxazol-5-yl)-1,6-naphthyridin-7-yl)cyclohexane-1-carboxamide [539];

1-(2,2-difluoropropyl)-N-(2-(oxazol-5-yl)-1,6-naphthyridin-7-yl)piperidine-4-carboxamide [540];

trans-4-(hydroxymethyl)-N-(2-(2-methyloxazol-5-yl)-1,6-naphthyridin-7-yl)cyclohexane-1-carboxamide [541];

trans-4-(methylamino)-N-(2-(2-methyloxazol-5-yl)-1,6-naphthyridin-7-yl)cyclohexane-1-carboxamide [542];

trans-4-(((1,3-difluoropropan-2-yl)amino)-N-(2-(2-methyloxazol-5-yl)-1,6-naphthyridin-7-yl) cyclohexane-1-carboxamide [543];

trans-N-(2-(2-methyloxazol-5-yl)-1,6-naphthyridin-7-yl)-4-((propan-2-yl-1,1,1,3,3,3-d$_6$)amino) cyclohexane-1-carboxamide [544];

trans-4-((2,2-difluoroethyl)amino)-N-(2-(2-methyloxazol-5-yl)-1,6-naphthyridin-7-yl) cyclohexane-1-carboxamide [545];

trans-N-(2-(2-methyloxazol-5-yl)-1,6-naphthyridin-7-yl)-4-((3,3,3-trifluoropropyl)amino) cyclohexane-1-carboxamide [546];

trans-4-((2-methoxyethyl)amino)-N-(2-(2-methyloxazol-5-yl)-1,6-naphthyridin-7-yl) cyclohexane-1-carboxamide [547];

trans-4-(dimethylamino)-N-(2-(2-methyloxazol-5-yl)-1,6-naphthyridin-7-yl)cyclohexane-1-carboxamide [548];

trans-4-(bis(methyl-d$_3$)amino)-N-(2-(2-methyloxazol-5-yl)-1,6-naphthyridin-7-yl)cyclohexane-1-carboxamide [549];

cis-4-(dimethylamino)-N-(2-(2-methyloxazol-5-yl)-1,6-naphthyridin-7-yl)cyclohexane-1-carboxamide [550];

trans-4-((2,2-difluoroethyl)(methyl)amino)-N-(2-(2-methyloxazol-5-yl)-1,6-naphthyridin-7-yl) cyclohexane-1-carboxamide [551];

trans-4-(methyl(oxetan-3-yl)amino)-N-(2-(2-methyloxazol-5-yl)-1,6-naphthyridin-7-yl) cyclohexane-1-carboxamide [552];

trans-4-((2-fluoroethyl)amino)-N-(2-(2-methyloxazol-5-yl)-1,6-naphthyridin-7-yl)cyclohexane-1-carboxamide [553];

trans-4-(2-(fluoromethyl)aziridin-1-yl)-N-(2-(2-methyloxazol-5-yl)-1,6-naphthyridin-7-yl) cyclohexane-1-carboxamide [554];

trans-4-((3-fluoroazetidin-1-yl)methyl)-N-(2-(2-methyloxazol-5-yl)-1,6-naphthyridin-7-yl) cyclohexane-1-carboxamide [555];

trans-N-(2-(2-methyloxazol-5-yl)-1,6-naphthyridin-7-yl)-3-morpholinocyclobutane-1-carboxamide [556];

trans-N-(2-(2-methyloxazol-5-yl)-1,6-naphthyridin-7-yl)-4-morpholinocyclohexane-1-carboxamide [557];

N-(2-(2-methyloxazol-5-yl)-1,6-naphthyridin-7-yl)-2-(piperidin-1-yl)acetamide [558];

2-(4-methoxypiperidin-1-yl)-N-(2-(2-methyloxazol-5-yl)-1,6-naphthyridin-7-yl)acetamide [559];

N-(2-(2-methyloxazol-5-yl)-1,6-naphthyridin-7-yl)-2-(4-methylpiperazin-1-yl)acetamide [560];

N-(2-(2-methyloxazol-5-yl)-1,6-naphthyridin-7-yl)morpholine-4-carboxamide [561];

N-(2-(2-methyloxazol-5-yl)-1,6-naphthyridin-7-yl)-2-morpholinoacetamide [562];

N-(2-(2-methyloxazol-5-yl)-1,6-naphthyridin-7-yl)-3-morpholinopropanamide [563];

1-methyl-N-(2-(2-methyloxazol-5-yl)-1,6-naphthyridin-7-yl)piperidine-4-carboxamide [564];

1-(2,2-difluoropropyl)-N-(2-(2-methyloxazol-5-yl)-1,6-naphthyridin-7-yl)piperidine-4-carboxamide [565];

N-(2-(2-methyloxazol-5-yl)-1,6-naphthyridin-7-yl)-4-morpholinopiperidine-1-carboxamide [566];

4-((1,3-difluoropropan-2-yl)amino)-N-(2-(2-methyloxazol-5-yl)-1,6-naphthyridin-7-yl) piperidine-1-carboxamide [567];

(1R,3s,5S)-3-((1,3-difluoropropan-2-yl)amino)-N-(2-(2-methyloxazol-5-yl)-1,6-naphthyridin-7-yl)-8-azabicyclo[3.2.1]octane-8-carboxamide [568];

(1R,3s,5S)-3-((1,3-difluoropropan-2-yl)amino)-N-(2-(2-methyloxazol-5-yl)-1,6-naphthyridin-7-yl)-8-azabicyclo[3.2.1]octane-8-carboxamide [569];

4-(dimethylamino)-N-(2-(2-methyloxazol-5-yl)-1,6-naphthyridin-7-yl)piperidine-1-carboxamide [570];

4-((2,2-difluoroethyl)(methyl)amino)-N-(2-(2-methyloxazol-5-yl)-1,6-naphthyridin-7-yl) piperidine-1-carboxamide [571];

(3S,4S)-4-amino-3-fluoro-N-(2-(2-methyloxazol-5-yl)-1,6-naphthyridin-7-yl)piperidine-1-carboxamide [572];

(3S,4S)-3-fluoro-4-(methylamino)-N-(2-(2-methyloxazol-5-yl)-1,6-naphthyridin-7-yl)piperidine-1-carboxamide [573];

(3R,4R)-4-amino-3-fluoro-N-(2-(2-methyloxazol-5-yl)-1,6-naphthyridin-7-yl)piperidine-1-carboxamide [574];

(3R,4R)-3-fluoro-4-(methylamino)-N-(2-(2-methyloxazol-5-yl)-1,6-naphthyridin-7-yl)piperidine-1-carboxamide [575];

4-((2-fluoroethyl)amino)-N-(2-(2-methyloxazol-5-yl)-1,6-naphthyridin-7-yl)piperidine-1-carboxamide [576];

4-((2,2-difluoroethyl)amino)-N-(2-(2-methyloxazol-5-yl)-1,6-naphthyridin-7-yl)piperidine-1-carboxamide [577];

(1R,3s,5S)-3-amino-N-(2-(2-methyloxazol-5-yl)-1,6-naphthyridin-7-yl)-8-azabicyclo[3.2.1] octane-8-carboxamide [578];

(1R,3r,5S)-3-amino-N-(2-(2-methyloxazol-5-yl)-1,6-naphthyridin-7-yl)-8-azabicyclo[3.2.1] octane-8-carboxamide [579];

(1R,3r,5S)-3-((2-fluoroethyl)amino)-N-(2-(2-methyloxazol-5-yl)-1,6-naphthyridin-7-yl)-8-azabicyclo[3.2.1]octane-8-carboxamide [580];

(1R,3r,5S)-3-((2,2-difluoroethyl)amino)-N-(2-(2-methyloxazol-5-yl)-1,6-naphthyridin-7-yl)-8-azabicyclo[3.2.1]octane-8-carboxamide [581];

(1R,3s,5S)—N-(2-(2-methyloxazol-5-yl)-1,6-naphthyridin-7-yl)-3-((3,3,3-trifluoropropyl)amino)-8-azabicyclo[3.2.1]octane-8-carboxamide [582];

(3S,4S)-3-fluoro-4-(isopropylamino)-N-(2-(2-methyloxazol-5-yl)-1,6-naphthyridin-7-yl) piperidine-1-carboxamide [583];

N-(2-(2-methyloxazol-5-yl)-1,6-naphthyridin-7-yl)-5,6-dihydroimidazo[1,2-a]pyrazine-7(8H)-carboxamide [584];

2-methyl-N-(2-(2-methyloxazol-5-yl)-1,6-naphthyridin-7-yl)-5,6-dihydroimidazo[1,2-a]pyrazine-7(8H)-carboxamide [585];

N-(2-(2-methyloxazol-5-yl)-1,6-naphthyridin-7-yl)-2-(morpholino-$d_8$)acetamide [586];

trans-N-(2-(2-methyloxazol-4-yl)-1,6-naphthyridin-7-yl)-4-(4-methylpiperazin-1-yl)cyclohexane-1-carboxamide [587];

N-(2-(2-methyloxazol-5-yl)-1,6-naphthyridin-7-yl)-1-(1-methylpiperidin-4-yl)-1H-pyrazole-4-carboxamide [588];

2-(1H-imidazol-1-yl)-N-(2-(2-methyloxazol-5-yl)-1,6-naphthyridin-7-yl)acetamide [589];

4-(difluoromethoxy)-N-(2-(oxazol-5-yl)-1,6-naphthyridin-7-yl)benzamide [590];

3-((1-methylpiperidin-4-yl)oxy)-N-(2-(oxazol-5-yl)-1,6-naphthyridin-7-yl)benzamide [591];

N-(2-(oxazol-5-yl)-1,6-naphthyridin-7-yl)isonicotinamide [592];

2-(3-aminoazetidin-1-yl)-N-(2-(oxazol-5-yl)-1,6-naphthyridin-7-yl)isonicotinamide [593];

2-(1-methylpiperidin-4-yl)-N-(2-(oxazol-5-yl)-1,6-naphthyridin-7-yl)isonicotinamide [594];

1'-methyl-N-(2-(oxazol-5-yl)-1,6-naphthyridin-7-yl)-1',2',3',6'-tetrahydro-[2,4'-bipyridine]-4-carboxamide [595];

2-(4-methylpiperazin-1-yl)-N-(2-(oxazol-5-yl)-1,6-naphthyridin-7-yl)isonicotinamide [596];

2-(7-methyl-2,7-diazaspiro[3.5]nonan-2-yl)-N-(2-(oxazol-5-yl)-1,6-naphthyridin-7-yl) isonicotinamide [597];

N-(2-(oxazol-5-yl)-1,6-naphthyridin-7-yl)-2-(2,7-diazaspiro[3.5]nonan-7-yl)isonicotinamide [598];

N-(2-(oxazol-5-yl)-1,6-naphthyridin-7-yl)-2-(piperidin-4-ylamino)isonicotinamide [599];

2-methyl-N-(2-(oxazol-5-yl)-1,6-naphthyridin-7-yl)isoindoline-5-carboxamide [600];

N-(2-(oxazol-5-yl)-1,6-naphthyridin-7-yl)-1,2,3,4-tetrahydroisoquinoline-7-carboxamide [601];

N-(2-(2-methyloxazol-5-yl)-1,6-naphthyridin-7-yl)-2-(4-methylpiperazin-1-yl)isonicotinamide [602];

N-(2-(3-methylisoxazol-5-yl)-1,6-naphthyridin-7-yl)-1-(3,3,3-trifluoropropyl)piperidine-4-carboxamide [603];

4-fluoro-1-isobutyl-N-(2-(5-methyl-1,3,4-oxadiazol-2-yl)-1,6-naphthyridin-7-yl)piperidine-4-carboxamide [604];

1-isobutyl-N-(2-(5-methyl-1,3,4-oxadiazol-2-yl)-1,6-naphthyridin-7-yl)piperidine-4-carboxamide [605];

N-(2-(5-(dimethylamino)-1,3,4-oxadiazol-2-yl)-1,6-naphthyridin-7-yl)piperidine-4-carboxamide [606];

N-(2-(5-(dimethylamino)-1,3,4-oxadiazol-2-yl)-1,6-naphthyridin-7-yl)-1-methylpiperidine-4-carboxamide [607];

N-(2-(5-methyl-1,3,4-oxadiazol-2-yl)-1,6-naphthyridin-7-yl)-2-(4-methylpiperazin-1-yl) isonicotinamide [608];

3,3-difluoro-N-(2-(thiazol-5-yl)-1,6-naphthyridin-7-yl)cyclobutane-1-carboxamide [609];

2-methyl-N-(2-(thiazol-5-yl)-1,6-naphthyridin-7-yl)-2-azaspiro[3.3]heptane-6-carboxamide [610];

1-fluoro-N-(2-(thiazol-5-yl)-1,6-naphthyridin-7-yl)cyclohexane-1-carboxamide [611];

trans-4-(dimethylamino)-N-(2-(thiazol-5-yl)-1,6-naphthyridin-7-yl)cyclohexane-1-carboxamide [612];

trans-4-((3-fluoroazetidin-1-yl)methyl)-N-(2-(thiazol-5-yl)-1,6-naphthyridin-7-yl)cyclohexane-1-carboxamide [613];

N-(2-(thiazol-5-yl)-1,6-naphthyridin-7-yl)azetidine-3-carboxamide [614];

1-methyl-N-(2-(thiazol-5-yl)-1,6-naphthyridin-7-yl)piperidine-4-carboxamide [615];

1-(2,2-difluoropropyl)-N-(2-(thiazol-5-yl)-1,6-naphthyridin-7-yl)piperidine-4-carboxamide [616];

1-(oxetan-3-yl)-N-(2-(thiazol-5-yl)-1,6-naphthyridin-7-yl)piperidine-4-carboxamide [617];

1-(2-(pyrrolidin-1-yl)acetyl)-N-(2-(thiazol-5-yl)-1,6-naphthyridin-7-yl)piperidine-4-carboxamide [618];

1'-methyl-N-(2-(thiazol-5-yl)-1,6-naphthyridin-7-yl)-[1,4'-bipiperidine]-4-carboxamide [619];

2-(pyrrolidin-1-yl)-N-(2-(thiazol-5-yl)-1,6-naphthyridin-7-yl)propanamide [620];

2-(piperidin-1-yl)-N-(2-(thiazol-5-yl)-1,6-naphthyridin-7-yl)acetamide [621];

2-(4-methylpiperazin-1-yl)-N-(2-(thiazol-5-yl)-1,6-naphthyridin-7-yl)acetamide [622];

2-morpholino-N-(2-(thiazol-5-yl)-1,6-naphthyridin-7-yl)acetamide [623];

4-(piperidin-4-yloxy)-N-(2-(thiazol-5-yl)-1,6-naphthyridin-7-yl)benzamide [624];

N-(2-(thiazol-5-yl)-1,6-naphthyridin-7-yl)isonicotinamide [625];

6-(4-methylpiperazin-1-yl)-N-(2-(thiazol-5-yl)-1,6-naphthyridin-7-yl)nicotinamide [626];

1'-methyl-N-(2-(thiazol-5-yl)-1,6-naphthyridin-7-yl)-1',2',3',6'-tetrahydro-[2,4'-bipyridine]-4-carboxamide [627];

2-(3-(dimethylamino)azetidin-1-yl)-N-(2-(thiazol-5-yl)-1,6-naphthyridin-7-yl)isonicotinamide [628];

2-(4-(dimethylamino)piperidin-1-yl)-N-(2-(thiazol-5-yl)-1,6-naphthyridin-7-yl)isonicotinamide [629];

2-(4-methylpiperazin-1-yl)-N-(2-(thiazol-5-yl)-1,6-naphthyridin-7-yl)isonicotinamide [630];

2-((1-methylpiperidin-4-yl)thio)-N-(2-(thiazol-5-yl)-1,6-naphthyridin-7-yl)isonicotinamide [631];

N-(2-(thiazol-5-yl)-1,6-naphthyridin-7-yl)-1,2,3,4-tetrahydroisoquinoline-7-carboxamide [632];

trans-4-((1,3-difluoropropan-2-yl)amino)-N-(2-(5-methyl-1,3,4-thiadiazol-2-yl)-1,6-naphthyridin-7-yl)cyclohexane-1-carboxamide [633];

N-(2-(2-methylthiazol-5-yl)-1,6-naphthyridin-7-yl)morpholine-4-carboxamide [634];

N-(2-(2-methylthiazol-5-yl)-1,6-naphthyridin-7-yl)-2-(pyrrolidin-1-yl)acetamide [635];

2-((1R,4R)-2-oxa-5-azabicyclo[2.2.1]heptan-5-yl)-N-(2-(2-methylthiazol-5-yl)-1,6-naphthyridin-7-yl)acetamide [636];

N-(2-(2-methylthiazol-5-yl)-1,6-naphthyridin-7-yl)-2-morpholinoacetamide [637];

N-(2-(2-methylthiazol-5-yl)-1,6-naphthyridin-7-yl)-2-(morpholino-$d_8$)acetamide [638];

2-(4-methylpiperazin-1-yl)-N-(2-(2-methylthiazol-5-yl)-1,6-naphthyridin-7-yl)acetamide [639];

1-methyl-N-(2-(2-methylthiazol-5-yl)-1,6-naphthyridin-7-yl)piperidine-4-carboxamide [640];

N-(2-(2-methylthiazol-5-yl)-1,6-naphthyridin-7-yl)isonicotinamide [641];

N-(2-(2-methylthiazol-5-yl)-1,6-naphthyridin-7-yl)nicotinamide [642];

2-(4-methylpiperazin-1-yl)-N-(2-(2-methylthiazol-5-yl)-1,6-naphthyridin-7-yl)isonicotinamide [643];

trans-N-(2-(5-methyl-1,3,4-thiadiazol-2-yl)-1,6-naphthyridin-7-yl)-4-morpholinocyclohexane-1-carboxamide [644];

trans-N-(2-(5-methyl-1,3,4-thiadiazol-2-yl)-1,6-naphthyridin-7-yl)-4-(4-methylpiperazin-1-yl) cyclohexane-1-carboxamide [645];

4-isopropyl-N-(2-(5-methyl-1,3,4-thiadiazol-2-yl)-1,6-naphthyridin-7-yl)piperazine-1-carboxamide [646];

4-((2-methoxyethyl)(methyl)amino)-N-(2-(5-methyl-1,3,4-thiadiazol-2-yl)-1,6-naphthyridin-7-yl) piperidine-1-carboxamide [647];

4-((1,3-difluoropropan-2-yl)amino)-N-(2-(5-methyl-1,3,4-thiadiazol-2-yl)-1,6-naphthyridin-7-yl) piperidine-1-carboxamide [648];

N-(2-(5-methyl-1,3,4-thiadiazol-2-yl)-1,6-naphthyridin-7-yl)-4-((3,3,3-trifluoropropyl)amino) piperidine-1-carboxamide [649];

4-((2-fluoroethyl)amino)-N-(2-(5-methyl-1,3,4-thiadiazol-2-yl)-1,6-naphthyridin-7-yl)piperidine-1-carboxamide [650];

(3R,4S)-4-amino-3-fluoro-N-(2-(5-methyl-1,3,4-thiadiazol-2-yl)-1,6-naphthyridin-7-yl) piperidine-1-carboxamide [651];

(3R,4R)-4-amino-3-fluoro-N-(2-(5-methyl-1,3,4-thiadiazol-2-yl)-1,6-naphthyridin-7-yl) piperidine-1-carboxamide [652];

(3S,4S)-3-fluoro-N-(2-(5-methyl-1,3,4-thiadiazol-2-yl)-1,6-naphthyridin-7-yl)-4-(methylamino) piperidine-1-carboxamide [653];

(3R,4R)-3-fluoro-N-(2-(5-methyl-1,3,4-thiadiazol-2-yl)-1,6-naphthyridin-7-yl)-4-(methylamino) piperidine-1-carboxamide [654];

4-amino-3,3-difluoro-N-(2-(5-methyl-1,3,4-thiadiazol-2-yl)-1,6-naphthyridin-7-yl)piperidine-1-carboxamide [655];

(3R,4R)-3-fluoro-4-(isopropylamino)-N-(2-(5-methyl-1,3,4-thiadiazol-2-yl)-1,6-naphthyridin-7-yl)piperidine-1-carboxamide [656];

(3R,4S)-3-fluoro-4-(isopropylamino)-N-(2-(5-methyl-1,3,4-thiadiazol-2-yl)-1,6-naphthyridin-7-yl)piperidine-1-carboxamide [657];

3,3-difluoro-4-(isopropylamino)-N-(2-(5-methyl-1,3,4-thiadiazol-2-yl)-1,6-naphthyridin-7-yl) piperidine-1-carboxamide [658];

(3S,4S)-3-fluoro-N-(2-(5-methyl-1,3,4-thiadiazol-2-yl)-1,6-naphthyridin-7-yl)-4-((propan-2-yl-1,1,1,3,3,3-$d_6$)amino)piperidine-1-carboxamide [659];

(1R,3s,5S)-3-((1,3-difluoropropan-2-yl)amino)-N-(2-(5-methyl-1,3,4-thiadiazol-2-yl)-1,6-naphthyridin-7-yl)-8-azabicyclo[3.2.1]octane-8-carboxamide [660];

(1R,3s,5S)-3-((1,3-difluoropropan-2-yl)amino)-N-(2-(5-methyl-1,3,4-thiadiazol-2-yl)-1,6-naphthyridin-7-yl)-8-azabicyclo[3.2.1]octane-8-carboxamide [661];

4-(dimethylamino)-N-(2-(2-methylthiazol-5-yl)-1,6-naphthyridin-7-yl)piperidine-1-carboxamide [662];

4-((2,2-difluoroethyl)amino)-N-(2-(5-methyl-1,3,4-thiadiazol-2-yl)-1,6-naphthyridin-7-yl) piperidine-1-carboxamide [663];

4-((2,2-difluoroethyl)(methyl-$d_3$)amino)-N-(2-(5-methyl-1,3,4-thiadiazol-2-yl)-1,6-naphthyridin-7-yl)piperidine-1-carboxamide [664];

N-(2-(5-methyl-1,3,4-thiadiazol-2-yl)-1,6-naphthyridin-7-yl)-4-morpholinopiperidine-1-carboxamide [665];

N-(2-(5-methyl-1,3,4-thiadiazol-2-yl)-1,6-naphthyridin-7-yl)-4-(4-methylpiperazin-1-yl) piperidine-1-carboxamide [666];

(R)-3,4-dimethyl-N-(2-(5-methyl-1,3,4-thiadiazol-2-yl)-1,6-naphthyridin-7-yl)piperazine-1-carboxamide [667];

(S)-3,4-dimethyl-N-(2-(5-methyl-1,3,4-thiadiazol-2-yl)-1,6-naphthyridin-7-yl)piperazine-1-carboxamide [668];

(1R,3r,5S)-3-((2-fluoroethyl)amino)-N-(2-(5-methyl-1,3,4-thiadiazol-2-yl)-1,6-naphthyridin-7-yl)-8-azabicyclo[3.2.1]octane-8-carboxamide [669];

(1R,3r,5S)-3-((2,2-difluoroethyl)amino)-N-(2-(5-methyl-1,3,4-thiadiazol-2-yl)-1,6-naphthyridin-7-yl)-8-azabicyclo[3.2.1]octane-8-carboxamide [670];

(1R,3r,5S)-3-amino-N-(2-(5-methyl-1,3,4-thiadiazol-2-yl)-1,6-naphthyridin-7-yl)-8-azabicyclo [3.2.1]octane-8-carboxamide [671];

(1S,4S)-5-methyl-N-(2-(5-methyl-1,3,4-thiadiazol-2-yl)-1,6-naphthyridin-7-yl)-2,5-diazabicyclo [2.2.1]heptane-2-carboxamide [672];

(1R,4R)-5-methyl-N-(2-(5-methyl-1,3,4-thiadiazol-2-yl)-1,6-naphthyridin-7-yl)-2,5-diazabicyclo [2.2.1]heptane-2-carboxamide [673];

8-methyl-N-(2-(5-methyl-1,3,4-thiadiazol-2-yl)-1,6-naphthyridin-7-yl)-3,8-diazabicyclo [3.2.1]octane-3-carboxamide [674];

3-methyl-N-(2-(5-methyl-1,3,4-thiadiazol-2-yl)-1,6-naphthyridin-7-yl)-3,8-diazabicyclo [3.2.1]octane-8-carboxamide [675];

N-(2-(5-methyl-1,3,4-thiadiazol-2-yl)-1,6-naphthyridin-7-yl)-5,6-dihydroimidazo[1,2-a]pyrazine-7(8H)-carboxamide [676];

2-(4-methylpiperazin-1-yl)-N-(2-(5-methylthiazol-2-yl)-1,6-naphthyridin-7-yl)isonicotinamide [677];

2-(4-methylpiperazin-1-yl)-N-(2-(4-methylthiazol-2-yl)-1,6-naphthyridin-7-yl)isonicotinamide [678];

N-(2-(2-(methylamino)thiazol-5-yl)-1,6-naphthyridin-7-yl)piperidine-4-carboxamide [679];

1-methyl-N-(2-(2-(methylamino)thiazol-5-yl)-1,6-naphthyridin-7-yl)piperidine-4-carboxamide [680];

N-(2-(2-(diethylamino)thiazol-5-yl)-1,6-naphthyridin-7-yl)-2-(4-fluoropiperidin-1-yl)acetamide [681];

N-(2-(2-(diethylamino)thiazol-5-yl)-1,6-naphthyridin-7-yl)-2-(4-methylpiperazin-1-yl)acetamide [682];

N-(2-(2-aminothiazol-5-yl)-1,6-naphthyridin-7-yl)-2-(4-methylpiperazin-1-yl)isonicotinamide [683];

N-(2-(2-(methylamino)thiazol-5-yl)-1,6-naphthyridin-7-yl)-2-(4-methylpiperazin-1-yl) isonicotinamide [684];

N-(2-(2-(dimethylamino)thiazol-5-yl)-1,6-naphthyridin-7-yl)-2-(4-methylpiperazin-1-yl) isonicotinamide [685];

2-(4-isopropylpiperazin-1-yl)-N-(2-(2-(methylamino)thiazol-5-yl)-1,6-naphthyridin-7-yl) isonicotinamide [686];

2-(3-(dimethylamino)azetidin-1-yl)-N-(2-(2-(methylamino)thiazol-5-yl)-1,6-naphthyridin-7-yl) isonicotinamide [687];

2-(3-(dimethylamino)azetidin-1-yl)-N-(2-(2-(dimethylamino)thiazol-5-yl)-1,6-naphthyridin-7-yl) isonicotinamide [688];

2-(3-aminoazetidin-1-yl)-N-(2-(2-(dimethylamino)thiazol-5-yl)-1,6-naphthyridin-7-yl) isonicotinamide [689];

N-(2-(5-chlorothiazol-2-yl)-1,6-naphthyridin-7-yl)-2-(4-methylpiperazin-1-yl)isonicotinamide [690];

2-(7-(2-(4-methylpiperazin-1-yl)isonicotinamido)-1,6-naphthyridin-2-yl)thiazole-5-carboxamide [691];

N-(2-(isothiazol-4-yl)-1,6-naphthyridin-7-yl)-1-methylpiperidine-4-carboxamide [692];

N-(2-(1,3,4-thiadiazol-2-yl)-1,6-naphthyridin-7-yl)-4-(difluoromethoxy)benzamide [693];

N-(2-(1,3,4-thiadiazol-2-yl)-1,6-naphthyridin-7-yl)-4-(piperidin-4-yloxy)benzamide [694];

N-(2-(1,3,4-thiadiazol-2-yl)-1,6-naphthyridin-7-yl)-4-((1-methylpiperidin-4-yl)oxy)benzamide [695];

N-(2-(1,3,4-thiadiazol-2-yl)-1,6-naphthyridin-7-yl)-3-((1-methylpiperidin-4-yl)oxy)benzamide [696];

$N^5$-(2-(1,3,4-thiadiazol-2-yl)-1,6-naphthyridin-7-yl)-$N^2$-methylpyridine-2,5-dicarboxamide [697];

N-(2-(1,3,4-thiadiazol-2-yl)-1,6-naphthyridin-7-yl)-6-(4-methylpiperazin-1-yl)nicotinamide [698];

N-(2-(1,3,4-thiadiazol-2-yl)-1,6-naphthyridin-7-yl)-1'-methyl-1',2',3',6'-tetrahydro-[2,4'-bipyridine]-4-carboxamide [699];

N-(2-(1,3,4-thiadiazol-2-yl)-1,6-naphthyridin-7-yl)-2-(3-(dimethylamino)azetidin-1-yl) isonicotinamide [700];

N-(2-(1,3,4-thiadiazol-2-yl)-1,6-naphthyridin-7-yl)-2-(4-methylpiperazin-1-yl)isonicotinamide [701];

N-(2-(1,3,4-thiadiazol-2-yl)-1,6-naphthyridin-7-yl)-2-(4-isopropylpiperazin-1-yl)isonicotinamide [702];

N-(2-(1,3,4-thiadiazol-2-yl)-1,6-naphthyridin-7-yl)-2-morpholinoisonicotinamide [703];

1-fluoro-N-(2-(5-methyl-1,3,4-thiadiazol-2-yl)-1,6-naphthyridin-7-yl)cyclohexane-1-carboxamide [704];

trans-4-methoxy-N-(2-(5-methyl-1,3,4-thiadiazol-2-yl)-1,6-naphthyridin-7-yl)cyclohexane-1-carboxamide [705];

cis-4-methoxy-N-(2-(5-methyl-1,3,4-thiadiazol-2-yl)-1,6-naphthyridin-7-yl)cyclohexane-1-carboxamide [706];

trans-4-amino-N-(2-(5-methyl-1,3,4-thiadiazol-2-yl)-1,6-naphthyridin-7-yl)cyclohexane-1-carboxamide [707];

trans-4-(dimethylamino)-N-(2-(5-methyl-1,3,4-thiadiazol-2-yl)-1,6-naphthyridin-7-yl) cyclohexane-1-carboxamide [708];

trans-N-(2-(5-methyl-1,3,4-thiadiazol-2-yl)-1,6-naphthyridin-7-yl)-4-morpholinocyclohexane-1-carboxamide [709];

trans-4-(hydroxymethyl)-N-(2-(5-methyl-1,3,4-thiadiazol-2-yl)-1,6-naphthyridin-7-yl)cyclohexane-1-carboxamide [710];

N-(2-(5-methyl-1,3,4-thiadiazol-2-yl)-1,6-naphthyridin-7-yl)piperidine-4-carboxamide [711];

4-fluoro-N-(2-(5-methyl-1,3,4-thiadiazol-2-yl)-1,6-naphthyridin-7-yl)piperidine-4-carboxamide [712];

1-methyl-N-(2-(5-methyl-1,3,4-thiadiazol-2-yl)-1,6-naphthyridin-7-yl)piperidine-4-carboxamide [713];

4-fluoro-1-methyl-N-(2-(5-methyl-1,3,4-thiadiazol-2-yl)-1,6-naphthyridin-7-yl)piperidine-4-carboxamide [714];

1-(2-fluoroethyl)-N-(2-(5-methyl-1,3,4-thiadiazol-2-yl)-1,6-naphthyridin-7-yl)piperidine-4-carboxamide [715];

1-(2,2-difluoroethyl)-N-(2-(5-methyl-1,3,4-thiadiazol-2-yl)-1,6-naphthyridin-7-yl)piperidine-4-carboxamide [716];

N-(2-(5-methyl-1,3,4-thiadiazol-2-yl)-1,6-naphthyridin-7-yl)-1-(3,3,3-trifluoropropyl)piperidine-4-carboxamide [717];

1-(2,2-difluoropropyl)-N-(2-(5-methyl-1,3,4-thiadiazol-2-yl)-1,6-naphthyridin-7-yl)piperidine-4-carboxamide [718];

1-benzoyl-N-(2-(5-methyl-1,3,4-thiadiazol-2-yl)-1,6-naphthyridin-7-yl)piperidine-4-carboxamide [719];

N-(2-(5-methyl-1,3,4-thiadiazol-2-yl)-1,6-naphthyridin-7-yl)-2-(pyrrolidin-1-yl)acetamide [720];

N-(2-(5-methyl-1,3,4-thiadiazol-2-yl)-1,6-naphthyridin-7-yl)-2-(piperidin-1-yl)acetamide [721];

2-(4-methoxypiperidin-1-yl)-N-(2-(5-methyl-1,3,4-thiadiazol-2-yl)-1,6-naphthyridin-7-yl) acetamide [722];

N-(2-(5-methyl-1,3,4-thiadiazol-2-yl)-1,6-naphthyridin-7-yl)-2-(4-methylpiperazin-1-yl) acetamide [723];

N-(2-(5-methyl-1,3,4-thiadiazol-2-yl)-1,6-naphthyridin-7-yl)-2-morpholinoacetamide [724];

(R)—N-(2-(5-methyl-1,3,4-thiadiazol-2-yl)-1,6-naphthyridin-7-yl)-2-(3-methylmorpholino)acetamide [725];

2-(7-azabicyclo[2.2.1]heptan-7-yl)-N-(2-(5-methyl-1,3,4-thiadiazol-2-yl)-1,6-naphthyridin-7-yl) acetamide [726];

2-((1R,4R)-2-oxa-5-azabicyclo[2.2.1]heptan-5-yl)-N-(2-(5-methyl-1,3,4-thiadiazol-2-yl)-1,6-naphthyridin-7-yl)acetamide [727];

2-(3-oxa-8-azabicyclo[3.2.1]octan-8-yl)-N-(2-(5-methyl-1,3,4-thiadiazol-2-yl)-1,6-naphthyridin-7-yl)acetamide [728];

2-(8-oxa-3-azabicyclo[3.2.1]octan-3-yl)-N-(2-(5-methyl-1,3,4-thiadiazol-2-yl)-1,6-naphthyridin-7-yl)acetamide [729];

N-(2-(5-methyl-1,3,4-thiadiazol-2-yl)-1,6-naphthyridin-7-yl)-2-(1,4-oxazepan-4-yl)acetamide [730];

N-(2-(5-methyl-1,3,4-thiadiazol-2-yl)-1,6-naphthyridin-7-yl)-2-morpholinoacetamide-2,2-$d_2$ [731];

N-(2-(5-methyl-1,3,4-thiadiazol-2-yl)-1,6-naphthyridin-7-yl)-2-(morpholino-d)acetamide [732];

1-methyl-3-(2-(5-methyl-1,3,4-thiadiazol-2-yl)-1,6-naphthyridin-7-yl)-1-(1-methylpiperidin-4-yl)urea [733];

(3S,4S)-4-amino-3-fluoro-N-(2-(5-methyl-1,3,4-thiadiazol-2-yl)-1,6-naphthyridin-7-yl) piperidine-1-carboxamide [734];

(3S,4S)-4-(dimethylamino)-3-fluoro-N-(2-(5-methyl-1,3,4-thiadiazol-2-yl)-1,6-naphthyridin-7-yl)piperidine-1-carboxamide [735];

N-(2-(5-methyl-1,3,4-thiadiazol-2-yl)-1,6-naphthyridin-7-yl)morpholine-4-carboxamide [736];

N-(2-(5-methyl-1,3,4-thiadiazol-2-yl)-1,6-naphthyridin-7-yl)-4-(methylamino)piperidine-1-carboxamide [737];

4-(dimethylamino)-N-(2-(5-methyl-1,3,4-thiadiazol-2-yl)-1,6-naphthyridin-7-yl)piperidine-1-carboxamide [738];

4-((2,2-difluoroethyl)(methyl)amino)-N-(2-(5-methyl-1,3,4-thiadiazol-2-yl)-1,6-naphthyridin-7-yl)piperidine-1-carboxamide [739];

(3S,4S)-3-fluoro-4-(isopropylamino)-N-(2-(5-methyl-1,3,4-thiadiazol-2-yl)-1,6-naphthyridin-7-yl)piperidine-1-carboxamide [740];

2-methyl-N-(2-(5-methyl-1,3,4-thiadiazol-2-yl)-1,6-naphthyridin-7-yl)-5,6-dihydroimidazo[1,2-a]pyrazine-7(8H)-carboxamide [741];

4-methyl-N-(2-(5-methyl-1,3,4-thiadiazol-2-yl)-1,6-naphthyridin-7-yl)piperazine-1-carboxamide [742];

N-(2-(5-methyl-1,3,4-thiadiazol-2-yl)-1,6-naphthyridin-7-yl)-1-(1-methylpiperidin-4-yl)-1H-pyrazole-4-carboxamide [743];

1-(1-isopropylpiperidin-4-yl)-N-(2-(5-methyl-1,3,4-thiadiazol-2-yl)-1,6-naphthyridin-7-yl)-1H-pyrazole-4-carboxamide [744];

N-(2-(5-methyl-1,3,4-thiadiazol-2-yl)-1,6-naphthyridin-7-yl)-1-(1-methylpiperidin-4-yl)-1H-1,2,3-triazole-4-carboxamide [745];

N-(2-(5-methyl-1,3,4-thiadiazol-2-yl)-1,6-naphthyridin-7-yl)-2-(piperidin-4-yl)oxazole-4-carboxamide [746];

N-(2-(5-methyl-1,3,4-thiadiazol-2-yl)-1,6-naphthyridin-7-yl)-2-(1-methylpiperidin-4-yl)oxazole-4-carboxamide [747];

2-(3-(dimethylamino)azetidin-1-yl)-N-(2-(5-methyl-1,3,4-thiadiazol-2-yl)-1,6-naphthyridin-7-yl) isonicotinamide [748];

1'-methyl-N-(2-(5-methyl-1,3,4-thiadiazol-2-yl)-1,6-naphthyridin-7-yl)-1',2',3',6'-tetrahydro-[2,4'-bipyridine]-4-carboxamide [749];

N-(2-(5-methyl-1,3,4-thiadiazol-2-yl)-1,6-naphthyridin-7-yl)-2-(4-methylpiperazin-1-yl) isonicotinamide [750];

2-(methyl(1-methylpiperidin-4-yl)amino)-N-(2-(5-methyl-1,3,4-thiadiazol-2-yl)-1,6-naphthyridin-7-yl) isonicotinamide [751];

2-(azetidin-3-yloxy)-N-(2-(5-methyl-1,3,4-thiadiazol-2-yl)-1,6-naphthyridin-7-yl)isonicotinamide [752];

N-(2-(5-methyl-1,3,4-thiadiazol-2-yl)-1,6-naphthyridin-7-yl)-3-((1-methylpiperidin-4-yl)oxy) benzamide [753];

N-(2-(5-methyl-1,3,4-thiadiazol-2-yl)-1,6-naphthyridin-7-yl)-2-((1-methylpiperidin-4-yl)thio) isonicotinamide [754];

6-(4-methylpiperazin-1-yl)-N-(2-(5-(trifluoromethyl)-1,3,4-thiadiazol-2-yl)-1,6-naphthyridin-7-yl)nicotinamide [755];

2-(4-methylpiperazin-1-yl)-N-(2-(5-(trifluoromethyl)-1,3,4-thiadiazol-2-yl)-1,6-naphthyridin-7-yl)isonicotinamide [756];

N-(2-(5-amino-1,3,4-thiadiazol-2-yl)-1,6-naphthyridin-7-yl)-2-(4-methylpiperazin-1-yl) isonicotinamide [757];

N-(2-(5-(dimethylamino)-1,3,4-thiadiazol-2-yl)-1,6-naphthyridin-7-yl)-2-(4-methylpiperazin-1-yl)isonicotinamide [758];

N-(2-(3-amino-5-fluorophenyl)-1,6-naphthyridin-7-yl)-2-(4-methylpiperazin-1-yl) isonicotinamide [759];

N-(2-(3-fluoro-5-(isopropylamino)phenyl)-1,6-naphthyridin-7-yl)-2-(4-methylpiperazin-1-yl) isonicotinamide [760];

1-methyl-N-(2-(pyridin-2-yl)-1,6-naphthyridin-7-yl)piperidine-4-carboxamide [761];

2-(4-methylpiperazin-1-yl)-N-(2-(pyridin-2-yl)-1,6-naphthyridin-7-yl)isonicotinamide [762];

2-(4-methylpiperazin-1-yl)-N-(2-(pyridin-4-yl)-1,6-naphthyridin-7-yl)isonicotinamide [763];

N-(2-(pyridin-3-yl)-1,6-naphthyridin-7-yl)cyclopropanecarboxamide [764];

N-(2-(pyridin-3-yl)-1,6-naphthyridin-7-yl)-2-(pyrrolidin-1-yl)acetamide [765];

1-methyl-N-(2-(pyridin-3-yl)-1,6-naphthyridin-7-yl)piperidine-4-carboxamide [766];

N-(2-(pyridin-3-yl)-1,6-naphthyridin-7-yl)quinuclidine-4-carboxamide [767];

2-morpholino-N-(2-(pyridin-3-yl)-1,6-naphthyridin-7-yl)acetamide [768];

2-(morpholino-$d_8$)—N-(2-(pyridin-3-yl)-1,6-naphthyridin-7-yl)acetamide [769];

2-(4-methylpiperazin-1-yl)-N-(2-(pyridin-3-yl)-1,6-naphthyridin-7-yl)acetamide [770];

2-(4-methyl-1,4-diazepan-1-yl)-N-(2-(pyridin-3-yl)-1,6-naphthyridin-7-yl)acetamide [771];

2-(4-methylpiperazin-1-yl)-N-(2-(pyridin-3-yl)-1,6-naphthyridin-7-yl)isonicotinamide [772];

2-(2-methyl-1H-imidazol-1-yl)-N-(2-(pyridin-3-yl)-1,6-naphthyridin-7-yl)acetamide [773];

2-(1H-imidazol-1-yl)-N-(2-(pyridin-3-yl)-1,6-naphthyridin-7-yl)acetamide [774];

2-(piperidin-4-yl)-N-(2-(pyridin-3-yl)-1,6-naphthyridin-7-yl)oxazole-4-carboxamide [775];

2-(1-methylpiperidin-4-yl)-N-(2-(pyridin-3-yl)-1,6-naphthyridin-7-yl)oxazole-4-carboxamide [776];

2-(1-isopropylpiperidin-4-yl)-N-(2-(pyridin-3-yl)-1,6-naphthyridin-7-yl)oxazole-4-carboxamide [777];

trans-N-(2-(5-fluoropyridin-3-yl)-1,6-naphthyridin-7-yl)-3-morpholinocyclobutane-1-carboxamide [778];

trans-N-(2-(5-fluoropyridin-3-yl)-1,6-naphthyridin-7-yl)-4-((4-methylpiperazin-1-yl)methyl) cyclohexane-1-carboxamide [779];

N-(2-(5-fluoropyridin-3-yl)-1,6-naphthyridin-7-yl)-2-(pyrrolidin-1-yl)acetamide [780];

N-(2-(5-fluoropyridin-3-yl)-1,6-naphthyridin-7-yl)-1-methylpiperidine-4-carboxamide [781];

N-(2-(5-fluoropyridin-3-yl)-1,6-naphthyridin-7-yl)-2-(4-methylpiperazin-1-yl)acetamide [782];

N-(2-(6-fluoropyridin-3-yl)-1,6-naphthyridin-7-yl)-2-(4-methylpiperazin-1-yl)acetamide [783];

N-(2-(5-fluoropyridin-3-yl)-1,6-naphthyridin-7-yl)-2-morpholinoacetamide [784];

N-(2-(5-fluoropyridin-3-yl)-1,6-naphthyridin-7-yl)-3-morpholinopropanamide [785];

N-(2-(5-fluoropyridin-3-yl)-1,6-naphthyridin-7-yl)-2-(4-methylpiperazin-1-yl)isonicotinamide [786];

N-(2-(5-fluoropyridin-3-yl)-1,6-naphthyridin-7-yl)-2-(piperidin-4-yl)oxazole-4-carboxamide [787];

N-(2-(5-fluoropyridin-3-yl)-1,6-naphthyridin-7-yl)-2-(1-methylpiperidin-4-yl)oxazole-4-carboxamide [788];

N-(2-(5-fluoropyridin-3-yl)-1,6-naphthyridin-7-yl)-2-(1-isopropylpiperidin-4-yl)oxazole-4-carboxamide [789];

N-(2-(5-chloropyridin-3-yl)-1,6-naphthyridin-7-yl)-2-(4-methylpiperazin-1-yl)isonicotinamide [790];

N-(2-(5-methylpyridin-3-yl)-1,6-naphthyridin-7-yl)-2-morpholinoacetamide [791];

N-(2-(5-(difluoromethyl)pyridin-3-yl)-1,6-naphthyridin-7-yl)-3-(piperidin-4-yl)benzamide [792];

N-(2-(5-(difluoromethyl)pyridin-3-yl)-1,6-naphthyridin-7-yl)-3-(1-methylpiperidin-4-yl) benzamide [793];

N-(2-(5-(difluoromethyl)pyridin-3-yl)-1,6-naphthyridin-7-yl)-2-(4-methylpiperazin-1-yl) isonicotinamide [794];
2-(4-methylpiperazin-1-yl)-N-(2-(5-(trifluoromethyl)pyridin-3-yl)-1,6-naphthyridin-7-yl) acetamide [795];
2-(4-methylpiperazin-1-yl)-N-(2-(6-(trifluoromethyl)pyridin-3-yl)-1,6-naphthyridin-7-yl) acetamide [796];
N-(2-(5-(hydroxymethyl)pyridin-3-yl)-1,6-naphthyridin-7-yl)-1-methylpiperidine-4-carboxamide [797];
N-(2-(5-cyanopyridin-3-yl)-1,6-naphthyridin-7-yl)-1-methylpiperidine-4-carboxamide [798];
N-(2-(5-methoxypyridin-3-yl)-1,6-naphthyridin-7-yl)-1-methylpiperidine-4-carboxamide [799];
N-(2-(5-methoxypyridin-3-yl)-1,6-naphthyridin-7-yl)-2-morpholinoacetamide [800];
N-(2-(5-methoxypyridin-3-yl)-1,6-naphthyridin-7-yl)-2-(4-methylpiperazin-1-yl)isonicotinamide [801];
4-fluoro-N-(2-(5-(piperidin-4-yloxy)pyridin-3-yl)-1,6-naphthyridin-7-yl)benzamide [802];
N-(2-(5-aminopyridin-3-yl)-1,6-naphthyridin-7-yl)-4-fluorobenzamide [803];
N-(2-(5-aminopyridin-3-yl)-1,6-naphthyridin-7-yl)-4-(piperidin-4-yloxy)benzamide [804];
N-(2-(5-aminopyridin-3-yl)-1,6-naphthyridin-7-yl)-2-(4-methylpiperazin-1-yl)isonicotinamide [805];
N-(2-(5-aminopyridin-3-yl)-1,6-naphthyridin-7-yl)-2-(piperidin-4-yl)oxazole-4-carboxamide [806];
N-(2-(6-aminopyridin-3-yl)-1,6-naphthyridin-7-yl)-2-(4-methylpiperazin-1-yl)isonicotinamide [807];
N-(2-(6-(methylamino)pyridin-3-yl)-1,6-naphthyridin-7-yl)-2-(4-methylpiperazin-1-yl) isonicotinamide [808];
N-(2-(5-(isopropylamino)pyridin-3-yl)-1,6-naphthyridin-7-yl)-3-(piperidin-4-yl)benzamide [809];
N-(2-(5-(isopropylamino)pyridin-3-yl)-1,6-naphthyridin-7-yl)-3-(1-methylpiperidin-4-yl) benzamide [810];
N-(2-(5-(isopropylamino)pyridin-3-yl)-1,6-naphthyridin-7-yl)-2-(4-methylpiperazin-1-yl) isonicotinamide [811];
N-(2-(5-(piperidin-4-ylamino)pyridin-3-yl)-1,6-naphthyridin-7-yl)cyclohexanecarboxamide [812];
4-fluoro-N-(2-(5-(piperidin-4-ylamino)pyridin-3-yl)-1,6-naphthyridin-7-yl)benzamide [813];
4-fluoro-N-(2-(5-((1-methylpiperidin-4-yl)amino)pyridin-3-yl)-1,6-naphthyridin-7-yl)benzamide [814];
N-(2-(5-acetamidopyridin-3-yl)-1,6-naphthyridin-7-yl)-1-methylpiperidine-4-carboxamide [815];
N-(2-(5-(dimethylamino)pyridin-3-yl)-1,6-naphthyridin-7-yl)-2-(4-methylpiperazin-1-yl) isonicotinamide [816];
N-(2-(6-(dimethylamino)pyridin-3-yl)-1,6-naphthyridin-7-yl)-2-(4-methylpiperazin-1-yl) isonicotinamide [817];
1-methyl-N-(2-(5-(pyrrolidin-1-yl)pyridin-3-yl)-1,6-naphthyridin-7-yl)piperidine-4-carboxamide [818];
N-(2-(5-(pyrrolidin-1-ylmethyl)pyridin-3-yl)-1,6-naphthyridin-7-yl)cyclopropanecarboxamide [819];
4-fluoro-N-(2-(5-(pyrrolidin-1-ylmethyl)pyridin-3-yl)-1,6-naphthyridin-7-yl)benzamide [820];
N-(2-(5-((4-hydroxypiperidin-1-yl)methyl)pyridin-3-yl)-1,6-naphthyridin-7-yl) cyclopropanecarboxamide [821];
4-fluoro-N-(2-(5-((4-hydroxypiperidin-1-yl)methyl)pyridin-3-yl)-1,6-naphthyridin-7-yl) benzamide [822];
N-(2-(5-(piperazin-1-ylmethyl)pyridin-3-yl)-1,6-naphthyridin-7-yl)cyclopropanecarboxamide [823];
N-(2-(5-((4-methylpiperazin-1-yl)methyl)pyridin-3-yl)-1,6-naphthyridin-7-yl) cyclopropanecarboxamide [824];
N-(2-(5-(morpholinomethyl)pyridin-3-yl)-1,6-naphthyridin-7-yl)cyclopropanecarboxamide [825];
N-methyl-5-(7-(1-methylpiperidine-4-carboxamido)-1,6-naphthyridin-2-yl)nicotinamide [826];
N-methyl-5-(7-(2-(4-methylpiperazin-1-yl)isonicotinamido)-1,6-naphthyridin-2-yl)nicotinamide [827];
N-(2-(pyridin-3-yl-$d_4$)-1,6-naphthyridin-7-yl)-2-(pyrrolidin-1-yl)acetamide [828];
2-(4-methylpiperazin-1-yl)-N-(2-(pyridin-3-yl-$d_4$)-1,6-naphthyridin-7-yl)acetamide [829];
2-morpholino-N-(2-(pyridin-3-yl-$d_4$)-1,6-naphthyridin-7-yl)acetamide [830];
1-methyl-N-(2-(2-methylpyrimidin-5-yl)-1,6-naphthyridin-7-yl)piperidine-4-carboxamide [831];
2-(4-methylpiperazin-1-yl)-N-(2-(2-methylpyrimidin-5-yl)-1,6-naphthyridin-7-yl)isonicotinamide [832];
N-(2-(2-aminopyrimidin-5-yl)-1,6-naphthyridin-7-yl)-1-methylpiperidine-4-carboxamide [833];
2-morpholino-N-(2-(pyridazin-3-yl)-1,6-naphthyridin-7-yl)acetamide [834];
2-morpholino-N-(2-(pyridazin-4-yl)-1,6-naphthyridin-7-yl)acetamide [835];
N-(2-(pyridazin-4-yl)-1,6-naphthyridin-7-yl)-2-(pyrrolidin-1-yl)acetamide [836];
trans-3-morpholino-N-(2-(pyrazin-2-yl)-1,6-naphthyridin-7-yl)cyclobutane-1-carboxamide [837];
trans-4-(dimethylamino)-N-(2-(pyrazin-2-yl)-1,6-naphthyridin-7-yl)cyclohexane-1-carboxamide [838];
trans-4-morpholino-N-(2-(pyrazin-2-yl)-1,6-naphthyridin-7-yl)cyclohexane-1-carboxamide [839];
trans-4-((3-fluoroazetidin-1-yl)methyl)-N-(2-(pyrazin-2-yl)-1,6-naphthyridin-7-yl)cyclohexane-1-carboxamide [840];
trans-4-((4-methylpiperazin-1-yl)methyl)-N-(2-(pyrazin-2-yl)-1,6-naphthyridin-7-yl)cyclohexane-1-carboxamide [841];
N-(2-(pyrazin-2-yl)-1,6-naphthyridin-7-yl)-2-(pyrrolidin-1-yl)acetamide [842];
1-methyl-N-(2-(pyrazin-2-yl)-1,6-naphthyridin-7-yl)piperidine-4-carboxamide [843];
4-fluoro-1-methyl-N-(2-(pyrazin-2-yl)-1,6-naphthyridin-7-yl)piperidine-4-carboxamide [844];
1-(2-fluoroethyl)-N-(2-(pyrazin-2-yl)-1,6-naphthyridin-7-yl)piperidine-4-carboxamide [845];
1-(oxetan-3-yl)-N-(2-(pyrazin-2-yl)-1,6-naphthyridin-7-yl)piperidine-4-carboxamide [846];
2-morpholino-N-(2-(pyrazin-2-yl)-1,6-naphthyridin-7-yl) acetamide [847];
1-methyl-N-(2-(pyrazin-2-yl)-1,6-naphthyridin-7-yl) azepane-4-carboxamide [848];
1-isobutyl-N-(2-(pyrazin-2-yl)-1,6-naphthyridin-7-yl) azepane-4-carboxamide [849];
1-(2-hydroxy-2-methylpropyl)-N-(2-(pyrazin-2-yl)-1,6-naphthyridin-7-yl)azepane-4-carboxamide [850];
4-(morpholinomethyl)-N-(2-(pyrazin-2-yl)-1,6-naphthyridin-7-yl)benzamide [851];
2-(4-methylpiperazin-1-yl)-N-(2-(pyrazin-2-yl)-1,6-naphthyridin-7-yl)isonicotinamide [852];
N-(2-(6-(methylamino)pyrazin-2-yl)-1,6-naphthyridin-7-yl)-2-(4-methylpiperazin-1-yl) isonicotinamide [853];
N-(2-(6-(isopropylamino)pyrazin-2-yl)-1,6-naphthyridin-7-yl)azetidine-3-carboxamide [854];
N-(2-(6-(isopropylamino)pyrazin-2-yl)-1,6-naphthyridin-7-yl)-1-methylpiperidine-4-carboxamide [855];

N-(2-(6-(isopropylamino)pyrazin-2-yl)-1,6-naphthyridin-7-yl)-1-methylpiperidine-4-carboxamide [856];
1-(2-fluoroethyl)-N-(2-(6-(isopropylamino)pyrazin-2-yl)-1,6-naphthyridin-7-yl)piperidine-4-carboxamide [857];
1-isopropyl-N-(2-(6-(isopropylamino)pyrazin-2-yl)-1,6-naphthyridin-7-yl)piperidine-4-carboxamide [858];
1-isopentyl-N-(2-(6-(isopropylamino)pyrazin-2-yl)-1,6-naphthyridin-7-yl)piperidine-4-carboxamide [859];
N-(2-(6-(isopropylamino)pyrazin-2-yl)-1,6-naphthyridin-7-yl)-3-(piperidin-4-yl)benzamide [860];
N-(2-(6-(isopropylamino)pyrazin-2-yl)-1,6-naphthyridin-7-yl)-3-(1-methylpiperidin-4-yl) benzamide [861];
N-(2-(6-(isopropylamino)pyrazin-2-yl)-1,6-naphthyridin-7-yl)-1-(piperidin-4-yl)-1H-1,2,3-triazole-4-carboxamide [862];
1-(1-(2-fluoroethyl)piperidin-4-yl)-N-(2-(6-(isopropylamino)pyrazin-2-yl)-1,6-naphthyridin-7-yl)-1H-1,2,3-triazole-4-carboxamide [863];
N-(2-(6-(isopropylamino)pyrazin-2-yl)-1,6-naphthyridin-7-yl)-1-(1-isopropylpiperidin-4-yl)-1H-1,2,3-triazole-4-carboxamide [864];
N-(2-(6-(isopropylamino)pyrazin-2-yl)-1,6-naphthyridin-7-yl)-2-(4-methylpiperazin-1-yl) isonicotinamide [865];
N-(2-(6-(tert-butylamino)pyrazin-2-yl)-1,6-naphthyridin-7-yl)-2-(3-(dimethylamino)azetidin-1-yl)isonicotinamide [866];
N-(2-(6-(tert-butylamino)pyrazin-2-yl)-1,6-naphthyridin-7-yl)-1'-methyl-1',2',3',6'-tetrahydro-[2,4'-bipyridine]-4-carboxamide [867];
N-(2-(6-(tert-butylamino)pyrazin-2-yl)-1,6-naphthyridin-7-yl)-2-(4-methylpiperazin-1-yl) isonicotinamide [868];
N-(2-(6-(tert-butylamino)pyrazin-2-yl)-1,6-naphthyridin-7-yl)-2-(4-isopropylpiperazin-1-yl) isonicotinamide [869];
N-(2-(6-(tert-butylamino)pyrazin-2-yl)-1,6-naphthyridin-7-yl)-2-morpholinoisonicotinamide [870];
N-(2-(6-(((3-fluoroazetidin-3-yl)methyl)amino)pyrazin-2-yl)-1,6-naphthyridin-7-yl) cyclopropanecarboxamide [871];
4-fluoro-N-(2-(6-(((3-fluoroazetidin-3-yl)methyl)amino)pyrazin-2-yl)-1,6-naphthyridin-7-yl) benzamide [872];
N-(2-(6-(piperidin-4-ylamino)pyrazin-2-yl)-1,6-naphthyridin-7-yl)cyclobutanecarboxamide [873];
3,3-difluoro-N-(2-(6-(piperidin-4-ylamino)pyrazin-2-yl)-1,6-naphthyridin-7-yl)cyclobutane-1-carboxamide [874];
N-(2-(6-(piperidin-4-ylamino)pyrazin-2-yl)-1,6-naphthyridin-7-yl)cyclopentanecarboxamide [875];
4,4-difluoro-N-(2-(6-(piperidin-4-ylamino)pyrazin-2-yl)-1,6-naphthyridin-7-yl)cyclohexane-1-carboxamide [876];
N-(2-(6-(piperidin-4-ylamino)pyrazin-2-yl)-1,6-naphthyridin-7-yl)tetrahydro-2H-pyran-4-carboxamide [877];
4-fluoro-N-(2-(6-(piperidin-4-ylamino)pyrazin-2-yl)-1,6-naphthyridin-7-yl)benzamide [878];
N-(2-(6-(((3S,4S)-3-fluoropiperidin-4-yl)amino)pyrazin-2-yl)-1,6-naphthyridin-7-yl) cyclopropanecarboxamide [879];
4-fluoro-N-(2-(6-(((3S,4S)-3-fluoropiperidin-4-yl)amino)pyrazin-2-yl)-1,6-naphthyridin-7-yl) benzamide [880];
N-(2-(6-((1-methylpiperidin-4-yl)amino)pyrazin-2-yl)-1,6-naphthyridin-7-yl) cyclobutanecarboxamide [881];
N-(2-(6-((1-methylpiperidin-4-yl)amino)pyrazin-2-yl)-1,6-naphthyridin-7-yl) cyclopentanecarboxamide [882];
4-fluoro-N-(2-(6-((1-methylpiperidin-4-yl)amino)pyrazin-2-yl)-1,6-naphthyridin-7-yl)benzamide [883];
N-(2-(6-((1-isopropylpiperidin-4-yl)amino)pyrazin-2-yl)-1,6-naphthyridin-7-yl) cyclopropanecarboxamide [884];
3,3-difluoro-N-(2-(6-((1-isopropylpiperidin-4-yl)amino)pyrazin-2-yl)-1,6-naphthyridin-7-yl) cyclobutane-1-carboxamide [885];
N-(2-(6-((1-isopropylpiperidin-4-yl)amino)pyrazin-2-yl)-1,6-naphthyridin-7-yl) cyclopentanecarboxamide [886];
4-fluoro-N-(2-(6-((1-isopropylpiperidin-4-yl)amino)pyrazin-2-yl)-1,6-naphthyridin-7-yl) benzamide [887];
N-(2-(6-(dimethylamino)pyrazin-2-yl)-1,6-naphthyridin-7-yl)-2-(4-methylpiperazin-1-yl) isonicotinamide [888];
N-(2-(6-(diethylamino)pyrazin-2-yl)-1,6-naphthyridin-7-yl)-2-(4-methylpiperazin-1-yl) isonicotinamide [889];
N-(2-(6-(3-aminoazetidin-1-yl)pyrazin-2-yl)-1,6-naphthyridin-7-yl)-4-fluorobenzamide [890];
2-(4-methylpiperazin-1-yl)-N-(2-(6-(pyrrolidin-1-yl)pyrazin-2-yl)-1,6-naphthyridin-7-yl) isonicotinamide [891];
N-(2-(6-(azetidin-3-ylmethoxy)pyrazin-2-yl)-1,6-naphthyridin-7-yl)-4-fluorobenzamide [892];
N-(2-(6-(azetidin-3-yloxy)pyrazin-2-yl)-1,6-naphthyridin-7-yl)-4-fluorobenzamide [893];
N-(2-(1H-pyrrolo[2,3-b]pyridin-5-yl)-1,6-naphthyridin-7-yl)-1-(1-methylpiperidin-4-yl)-1H-pyrazole-4-carboxamide [894];
N-(2-(1H-pyrrolo[3,2-b]pyridin-6-yl)-1,6-naphthyridin-7-yl)-1-(1-methylpiperidin-4-yl)-1H-pyrazole-4-carboxamide [895];
N-(2-(1H-pyrrolo[2,3-c]pyridin-4-yl)-1,6-naphthyridin-7-yl)-1-(1-methylpiperidin-4-yl)-1H-pyrazole-4-carboxamide [896];
N-(2-(1H-pyrrolo[2,3-b]pyridin-5-yl)-1,6-naphthyridin-7-yl)-2-(4-methylpiperazin-1-yl) isonicotinamide [897];
N-(2-(1H-pyrrolo[3,2-b]pyridin-6-yl)-1,6-naphthyridin-7-yl)-2-(4-methylpiperazin-1-yl) isonicotinamide [898];
N-(2-(1H-pyrrolo[2,3-c]pyridin-4-yl)-1,6-naphthyridin-7-yl)-2-(4-methylpiperazin-1-yl) isonicotinamide [899];
2-(4-methylpiperazin-1-yl)-N-(2-(oxazolo[5,4-b]pyridin-6-yl)-1,6-naphthyridin-7-yl) isonicotinamide [900];
N-(2-(2-methyl-1H-pyrrolo[2,3-b]pyridin-5-yl)-1,6-naphthyridin-7-yl)-2-(4-methylpiperazin-1-yl)isonicotinamide [901];
N-(2-(3-methyl-1H-pyrrolo[2,3-b]pyridin-5-yl)-1,6-naphthyridin-7-yl)-2-(4-methylpiperazin-1-yl)isonicotinamide [902];
N-(2-(2-methyl-1H-pyrrolo[3,2-b]pyridin-6-yl)-1,6-naphthyridin-7-yl)-2-(4-methylpiperazin-1-yl)isonicotinamide [903];
N-(2-(5H-pyrrolo[2,3-b]pyrazin-2-yl)-1,6-naphthyridin-7-yl)-2-(4-methylpiperazin-1-yl) isonicotinamide [904];
N-(2-(5H-pyrrolo[2,3-b]pyrazin-3-yl)-1,6-naphthyridin-7-yl)-2-(4-methylpiperazin-1-yl)isonicotinamide [905];
1-isopropyl-N-(2-(6-(piperidin-4-ylamino)pyrazin-2-yl)-1,6-naphthyridin-7-yl)-1H-pyrazole-4-carboxamide [906];

1-isopropyl-N-(2-(6-((1-methylpiperidin-4-yl)amino) pyrazin-2-yl)-1,6-naphthyridin-7-yl)-1H-pyrazole-4-carboxamide [907];

trans-4-((2-fluoroethyl)amino)-N-(2-(1-methyl-1H-pyrazol-4-yl)-1,6-naphthyridin-7-yl) cyclohexane-1-carboxamide [4535];

trans-4-((2-methoxyethyl)amino)-N-(2-(1-methyl-1H-pyrazol-4-yl)-1,6-naphthyridin-7-yl) cyclohexane-1-carboxamide [4536];

tert-butyl (trans-4-((2-(1-methyl-1H-pyrazol-4-yl)-1,6-naphthyridin-7-yl)carbamoyl)cyclohexyl) carbamate [4537];

N-(2-(1-methyl-1H-pyrazol-4-yl)-1,6-naphthyridin-7-yl)-2-((1-methylpiperidin-4-yl)amino) isonicotinamide [4538];

N-(2-(1-methyl-1H-pyrazol-4-yl)-1,6-naphthyridin-7-yl)-2-(4-methylpiperazin-1-yl)thiazole-5-carboxamide [4539];

N-(2-(1-methyl-1H-pyrazol-4-yl)-1,6-naphthyridin-7-yl)-2-(4-methylpiperazin-1-yl)thiazole-5-carboxamide [4540];

N-(2-(1-methyl-5-(piperidin-1-ylmethyl)-1H-pyrazol-4-yl)-1,6-naphthyridin-7-yl)-2-(2,7-diazaspiro[3.5]nonan-2-yl)isonicotinamide [4541];

N-(2-(1-methyl-1H-1,2,3-triazol-4-yl)-1,6-naphthyridin-7-yl)-4-(piperidin-4-yloxy)benzamide [4542];

N-(2-(1-methyl-1H-tetrazol-5-yl)-1,6-naphthyridin-7-yl)-1-(3,3,3-trifluoropropyl)piperidine-4-carboxamide [4543];

N-(2-(1,2-dimethyl-1H-imidazol-5-yl)-1,6-naphthyridin-7-yl)-2-(pyrrolidin-1-yl)propanamide [4544];

N-(2-(1,2-dimethyl-1H-imidazol-5-yl)-1,6-naphthyridin-7-yl)-2-(piperidin-1-yl)propanamide [4545];

4-isopropoxy-N-(2-(7-methyl-5,6,7,8-tetrahydroimidazo[1,2-a]pyrazin-3-yl)-1,6-naphthyridin-7-yl)benzamide [4546];

trans-3-morpholino-N-(2-(oxazol-5-yl)-1,6-naphthyridin-7-yl)cyclobutane-1-carboxamide [4547];

trans-4-(hydroxymethyl)-N-(2-(oxazol-5-yl)-1,6-naphthyridin-7-yl)cyclohexane-1-carboxamide [4548];

N-(2-(oxazol-5-yl)-1,6-naphthyridin-7-yl)piperidine-4-carboxamide [4549];

4-morpholino-N-(2-(oxazol-5-yl)-1,6-naphthyridin-7-yl)piperidine-1-carboxamide [4550];

N-(2-(oxazol-5-yl)-1,6-naphthyridin-7-yl)-4-(piperidin-4-yloxy)benzamide [4551];

N-(2-(oxazol-5-yl)-1,6-naphthyridin-7-yl)-3-(piperidin-4-yloxy)benzamide [4552];

2-methyl-N-(2-(oxazol-5-yl)-1,6-naphthyridin-7-yl)-5,6-dihydroimidazo[1,2-a]pyrazine-7(8H)-carboxamide [4553];

2-(1H-imidazol-1-yl)-N-(2-(oxazol-5-yl)-1,6-naphthyridin-7-yl)acetamide [4554];

trans-4-(hydroxymethyl)-N-(2-(thiazol-5-yl)-1,6-naphthyridin-7-yl)cyclohexane-1-carboxamide [4555];

trans-4-(dimethylamino)-N-(2-(thiazol-5-yl)-1,6-naphthyridin-7-yl)cyclohexane-1-carboxamide [4556];

N-(2-(thiazol-5-yl)-1,6-naphthyridin-7-yl)-1-(((1-(trifluoromethyl)cyclopropyl)methyl)piperidine-4-carboxamide [4557];

trans-4-(hydroxymethyl)-N-(2-(2-methylthiazol-5-yl)-1,6-naphthyridin-7-yl)cyclohexane-1-carboxamide [4558];

trans-4-(dimethylamino)-N-(2-(2-methylthiazol-5-yl)-1,6-naphthyridin-7-yl)cyclohexane-1-carboxamide [4559];

N-(2-(2-methylthiazol-5-yl)-1,6-naphthyridin-7-yl)-1-(oxetan-3-yl)piperidine-4-carboxamide [4560];

N-(2-(2-methylthiazol-5-yl)-1,6-naphthyridin-7-yl)-1-(2-(pyrrolidin-1-yl)acetyl)piperidine-4-carboxamide [4561];

2-((1S,4S)-2-oxa-5-azabicyclo [2.2.1]heptan-5-yl)-N-(2-(5-methyl-1,3,4-thiadiazol-2-yl)-1,6-naphthyridin-7-yl)acetamide [4562];

N-(2-(5-(cyano(4-hydroxypiperidin-1-yl)methyl)pyridin-3-yl)-1,6-naphthyridin-7-yl) cyclopropanecarboxamide [4563];

4-fluoro-N-(2-(6-((1-methylazetidin-3-yl)methoxy) pyrazin-2-yl)-1,6-naphthyridin-7-yl) benzamide [4564];

1-isopropyl-N-(2-(6-((1-methylpiperidin-4-yl)amino) pyrazin-2-yl)-1,6-naphthyridin-7-yl)-1H-pyrazole-4-carboxamide [4565]; or a pharmaceutically acceptable salt thereof.

13. The compound of claim 1, wherein the compound of Formula I is selected from the group consisting of:

N-(7-(1H-pyrazol-4-yl)quinazolin-2-yl)-1-isobutylpiperidine-4-carboxamide [908];

N-(7-(1-methyl-1H-pyrazol-4-yl)quinazolin-2-yl)cyclopropanecarboxamide [909];

4,4-difluoro-N-(7-(1-methyl-1H-pyrazol-4-yl)quinazolin-2-yl)cyclohexane-1-carboxamide [910];

trans-4-methoxy-N-(7-(1-methyl-1H-pyrazol-4-yl)quinazolin-2-yl)cyclohexane-1-carboxamide [911];

trans-N-(7-(1-methyl-1H-pyrazol-4-yl)quinazolin-2-yl)-4-morpholinocyclohexane-1-carboxamide [912];

trans-4-((3-fluoroazetidin-1-yl)methyl)-N-(7-(1-methyl-1H-pyrazol-4-yl)quinazolin-2-yl) cyclohexane-1-carboxamide [913];

trans-N-(7-(1-methyl-1H-pyrazol-4-yl)quinazolin-2-yl)-4-((4-methylpiperazin-1-yl)methyl) cyclohexane-1-carboxamide [914];

N-(7-(1-methyl-1H-pyrazol-4-yl)quinazolin-2-yl)-2-(pyrrolidin-1-yl)acetamide [915];

(S)-2-(3-fluoropyrrolidin-1-yl)-N-(7-(1-methyl-1H-pyrazol-4-yl)quinazolin-2-yl)acetamide [916];

(S)—N-(7-(1-methyl-1H-pyrazol-4-yl)quinazolin-2-yl) tetrahydrofuran-2-carboxamide [917];

N-(7-(1-methyl-1H-pyrazol-4-yl)quinazolin-2-yl)piperidine-4-carboxamide [918];

1-methyl-N-(7-(1-methyl-1H-pyrazol-4-yl)quinazolin-2-yl)piperidine-4-carboxamide [919];

1-isopropyl-N-(7-(1-methyl-1H-pyrazol-4-yl)quinazolin-2-yl)piperidine-4-carboxamide [920];

1-(tert-butyl)-N-(7-(1-methyl-1H-pyrazol-4-yl)quinazolin-2-yl)piperidine-4-carboxamide [921];

1-cyclopropyl-N-(7-(1-methyl-1H-pyrazol-4-yl)quinazolin-2-yl)piperidine-4-carboxamide [922];

1-isobutyl-N-(7-(1-methyl-1H-pyrazol-4-yl)quinazolin-2-yl)piperidine-4-carboxamide [923];

N-(7-(1-methyl-1H-pyrazol-4-yl)quinazolin-2-yl)-1-neopentylpiperidine-4-carboxamide [924];

1-(2-fluoroethyl)-N-(7-(1-methyl-1H-pyrazol-4-yl)quinazolin-2-yl)piperidine-4-carboxamide [925];

N-(7-(1-methyl-1H-pyrazol-4-yl)quinazolin-2-yl)-1-(3,3,3-trifluoropropyl)piperidine-4-carboxamide [926];

1-butyl-N-(7-(1-methyl-1H-pyrazol-4-yl)quinazolin-2-yl)piperidine-4-carboxamide [927];

1-benzoyl-N-(7-(1-methyl-1H-pyrazol-4-yl)quinazolin-2-yl)piperidine-4-carboxamide [928];

1-(2,2-difluoropropyl)-N-(7-(1-methyl-1H-pyrazol-4-yl)quinazolin-2-yl)piperidine-4-carboxamide [929];

N-(7-(1-methyl-1H-pyrazol-4-yl)quinazolin-2-yl)azetidine-3-carboxamide [930];
1-(2,2-difluoroethyl)-N-(7-(1-methyl-1H-pyrazol-4-yl)quinazolin-2-yl)piperidine-4-carboxamide [931];
1-(2-fluoro-2-methylpropyl)-N-(7-(1-methyl-1H-pyrazol-4-yl)quinazolin-2-yl)piperidine-4-carboxamide [932];
N-(7-(1-methyl-1H-pyrazol-4-yl)quinazolin-2-yl)-1-(oxetan-3-yl)piperidine-4-carboxamide [933];
N-(7-(1-methyl-1H-pyrazol-4-yl)quinazolin-2-yl)-1-((3-methyloxetan-3-yl)methyl)piperidine-4-carboxamide [934];
1-(2-methoxyethyl)-N-(7-(1-methyl-1H-pyrazol-4-yl)quinazolin-2-yl)piperidine-4-carboxamide [935];
1-(2-isopropoxyethyl)-N-(7-(1-methyl-1H-pyrazol-4-yl)quinazolin-2-yl)piperidine-4-carboxamide [936];
1,1-diisobutyl-4-((7-(1-methyl-1H-pyrazol-4-yl)quinazolin-2-yl)carbamoyl)piperidin-1-ium [937];
4-fluoro-N-(7-(1-methyl-1H-pyrazol-4-yl)quinazolin-2-yl)piperidine-4-carboxamide [938];
4-fluoro-1-methyl-N-(7-(1-methyl-1H-pyrazol-4-yl)quinazolin-2-yl)piperidine-4-carboxamide [939];
4-fluoro-1-isobutyl-N-(7-(1-methyl-1H-pyrazol-4-yl)quinazolin-2-yl)piperidine-4-carboxamide [940];
(S)—N-(7-(1-methyl-1H-pyrazol-4-yl)quinazolin-2-yl)piperidine-3-carboxamide [941];
(R)—N-(7-(1-methyl-1H-pyrazol-4-yl)quinazolin-2-yl)piperidine-3-carboxamide [942];
(S)-1-isobutyl-N-(7-(1-methyl-1H-pyrazol-4-yl)quinazolin-2-yl)piperidine-3-carboxamide [943];
(R)-1-isobutyl-N-(7-(1-methyl-1H-pyrazol-4-yl)quinazolin-2-yl)piperidine-3-carboxamide [944];
N-(7-(1-methyl-1H-pyrazol-4-yl)quinazolin-2-yl)tetrahydro-2H-pyran-4-carboxamide [945];
N-(7-(1-methyl-1H-pyrazol-4-yl)quinazolin-2-yl)-2-(piperidin-1-yl)acetamide [946];
2-(4-fluoropiperidin-1-yl)-N-(7-(1-methyl-1H-pyrazol-4-yl)quinazolin-2-yl)acetamide [947];
trans-4-amino-N-(7-(1-methyl-1H-pyrazol-4-yl)quinazolin-2-yl)cyclohexane-1-carboxamide [948];
N-(7-(1-methyl-1H-pyrazol-4-yl)quinazolin-2-yl)-2-(4-methylpiperazin-1-yl)acetamide [949];
(S)—N-(7-(1-methyl-1H-pyrazol-4-yl)quinazolin-2-yl)piperidine-2-carboxamide [950];
2-(4-isobutylpiperazin-1-yl)-N-(7-(1-methyl-1H-pyrazol-4-yl)quinazolin-2-yl)acetamide [951];
2-(3,3-dimethylazetidin-1-yl)-N-(7-(1-methyl-1H-pyrazol-4-yl)quinazolin-2-yl)acetamide [952];
(R)-2-(3-fluoropyrrolidin-1-yl)-N-(7-(1-methyl-1H-pyrazol-4-yl)quinazolin-2-yl)acetamide [953];
(S)—N-(7-(1-methyl-1H-pyrazol-4-yl)quinazolin-2-yl)-2-(2-methylpyrrolidin-1-yl)acetamide [954];
2-(3-azabicyclo[3.1.0]hexan-3-yl)-N-(7-(1-methyl-1H-pyrazol-4-yl)quinazolin-2-yl)acetamide [955];
2-(7-azabicyclo[2.2.1]heptan-7-yl)-N-(7-(1-methyl-1H-pyrazol-4-yl)quinazolin-2-yl)acetamide [956];
N-(7-(1-methyl-1H-pyrazol-4-yl)quinazolin-2-yl)-2-(4-methylpiperidin-1-yl)acetamide [957];
N-(7-(1-methyl-1H-pyrazol-4-yl)quinazolin-2-yl)-2-(4-(trifluoromethyl)piperidin-1-yl)acetamide [958];
2-(4-(difluoromethyl)piperidin-1-yl)-N-(7-(1-methyl-1H-pyrazol-4-yl)quinazolin-2-yl)acetamide [959];
N-(7-(1-methyl-1H-pyrazol-4-yl)quinazolin-2-yl)-2-(6-azaspiro[2.5]octan-6-yl)acetamide [960];
N-(7-(1-methyl-1H-pyrazol-4-yl)quinazolin-2-yl)-2-(pyrrolidin-1-yl)propanamide [961];
(R)—N-(7-(1-methyl-1H-pyrazol-4-yl)quinazolin-2-yl)-2-(2-methylpyrrolidin-1-yl)acetamide [962];
2-(cyclobutyl(methyl)amino)-N-(7-(1-methyl-1H-pyrazol-4-yl)quinazolin-2-yl)acetamide [963];
2-(diethylamino)-N-(7-(1-methyl-1H-pyrazol-4-yl)quinazolin-2-yl)acetamide [964];
7-(2-fluoroethyl)-N-(7-(1-methyl-1H-pyrazol-4-yl)quinazolin-2-yl)-7-azaspiro[3.5]nonane-2-carboxamide [965];
4-methyl-N-(7-(1-methyl-1H-pyrazol-4-yl)quinazolin-2-yl)piperazine-1-carboxamide [966];
(S)—N-(7-(1-methyl-1H-pyrazol-4-yl)quinazolin-2-yl)-2-(pyrrolidin-1-yl)propanamide [967];
(R)—N-(7-(1-methyl-1H-pyrazol-4-yl)quinazolin-2-yl)-2-(pyrrolidin-1-yl)propanamide [968];
(R)—N-(7-(1-methyl-1H-pyrazol-4-yl)quinazolin-2-yl)pyrrolidine-2-carboxamide [969];
2-methyl-N-(7-(1-methyl-1H-pyrazol-4-yl)quinazolin-2-yl)-2-azaspiro[3.3]heptane-6-carboxamide [970];
N-(7-(1-methyl-1H-pyrazol-4-yl)quinazolin-2-yl)-2-(2,2,2-trifluoroacetyl)-2-azaspiro [3.3] heptane-6-carboxamide [971];
2-(2-fluoroethyl)-N-(7-(1-methyl-1H-pyrazol-4-yl)quinazolin-2-yl)-2-azaspiro [3.3]heptane-6-carboxamide [972];
trans-4-(dimethylamino)-N-(7-(1-methyl-1H-pyrazol-4-yl)quinazolin-2-yl)cyclohexane-1-carboxamide [973];
1-acetyl-N-(7-(1-methyl-1H-pyrazol-4-yl)quinazolin-2-yl)piperidine-4-carboxamide [974];
N-(7-(1-methyl-1H-pyrazol-4-yl)quinazolin-2-yl)-1-((1-(trifluoromethyl)cyclopropyl)methyl) piperidine-4-carboxamide [975];
(S)-1-(2-fluoropropyl)-N-(7-(1-methyl-1H-pyrazol-4-yl)quinazolin-2-yl)piperidine-4-carboxamide [976];
(R)-1-(2-fluoropropyl)-N-(7-(1-methyl-1H-pyrazol-4-yl)quinazolin-2-yl)piperidine-4-carboxamide [977];
N-(7-(1-methyl-1H-pyrazol-4-yl)quinazolin-2-yl)-2-(piperidin-1-yl)propanamide [978];
N-(7-(1-methyl-1H-pyrazol-4-yl)quinazolin-2-yl)-1-(methylsulfonyl)piperidine-4-carboxamide [979];
1'-methyl-N-(7-(1-methyl-1H-pyrazol-4-yl)quinazolin-2-yl)-[1,4'-bipiperidine]-4-carboxamide [980];
trans-4-(hydroxymethyl)-N-(7-(1-methyl-1H-pyrazol-4-yl)quinazolin-2-yl)cyclohexane-1-carboxamide [981];
methyl 2-(4-((7-(1-methyl-1H-pyrazol-4-yl)quinazolin-2-yl)carbamoyl)piperidin-1-yl)acetate [982];
1-benzyl-N-(7-(1-methyl-1H-pyrazol-4-yl)quinazolin-2-yl)piperidine-4-carboxamide [983];
N-(7-(1-methyl-1H-pyrazol-4-yl)quinazolin-2-yl)-1-(2-(pyrrolidin-1-yl)acetyl)piperidine-4-carboxamide [984];
N-(7-(1-methyl-1H-pyrazol-4-yl)quinazolin-2-yl)-2-morpholinoacetamide [985];
(S)—N-(7-(1-methyl-1H-pyrazol-4-yl)quinazolin-2-yl)-2-(3-methylmorpholino)acetamide [986];
(R)—N-(7-(1-methyl-1H-pyrazol-4-yl)quinazolin-2-yl)-2-(3-methylmorpholino)acetamide [987];
(S)—N-(7-(1-methyl-1H-pyrazol-4-yl)quinazolin-2-yl)-2-(2-methylmorpholino)acetamide [988];
2-((2R,6S)-2,6-dimethylmorpholino)-N-(7-(1-methyl-1H-pyrazol-4-yl)quinazolin-2-yl)acetamide [989];
2-((1S,4S)-2-oxa-5-azabicyclo [2.2.1]heptan-5-yl)-N-(7-(1-methyl-1H-pyrazol-4-yl)quinazolin-2-yl)acetamide [990];
2-((1R,4R)-2-oxa-5-azabicyclo [2.2.1]heptan-5-yl)-N-(7-(1-methyl-1H-pyrazol-4-yl)quinazolin-2-yl)acetamide [991];

2-(3-oxa-8-azabicyclo[3.2.1]octan-8-yl)-N-(7-(1-methyl-1H-pyrazol-4-yl)quinazolin-2-yl) acetamide [992];
(S)—N-(7-(1-methyl-1H-pyrazol-4-yl)quinazolin-2-yl)-2-morpholinopropanamide [993];
N-(7-(1-methyl-1H-pyrazol-4-yl)quinazolin-2-yl)-2-(morpholin-2-yl)acetamide [994];
N-(7-(1-methyl-1H-pyrazol-4-yl)quinazolin-2-yl)-2-(4-methylmorpholin-2-yl)acetamide [995];
2-(4-ethylpiperazin-1-yl)-N-(7-(1-methyl-1H-pyrazol-4-yl)quinazolin-2-yl)acetamide [996];
2-(4-isopropylpiperazin-1-yl)-N-(7-(1-methyl-1H-pyrazol-4-yl)quinazolin-2-yl)acetamide [997];
2-(4-cyclopropylpiperazin-1-yl)-N-(7-(1-methyl-1H-pyrazol-4-yl)quinazolin-2-yl)acetamide [998];
2-(4-(2-fluoroethyl)piperazin-1-yl)-N-(7-(1-methyl-1H-pyrazol-4-yl)quinazolin-2-yl)acetamide [999];
(S)-2-(2,4-dimethylpiperazin-1-yl)-N-(7-(1-methyl-1H-pyrazol-4-yl)quinazolin-2-yl)acetamide [1000];
1-(2-hydroxyethyl)-N-(7-(1-methyl-1H-pyrazol-4-yl)quinazolin-2-yl)piperidine-4-carboxamide [1001];
N-(7-(1-methyl-1H-pyrazol-4-yl)quinazolin-2-yl)-1-(pyridin-2-ylmethyl)piperidine-4-carboxamide [1002];
N-(7-(1-methyl-1H-pyrazol-4-yl)quinazolin-2-yl)-1-(oxazol-2-ylmethyl)piperidine-4-carboxamide [1003];
(R)—N-(7-(1-methyl-1H-pyrazol-4-yl)quinazolin-2-yl)-1-oxotetrahydro-1H-pyrrolo[1,2-c] imidazole-2(3H)-carboxamide [1004];
(R)-1-methyl-N-(7-(1-methyl-1H-pyrazol-4-yl)quinazolin-2-yl)pyrrolidine-2-carboxamide [1005];
N-(7-(1-methyl-1H-pyrazol-4-yl)quinazolin-2-yl)-1-(tetrahydro-2H-pyran-4-yl)piperidine-4-carboxamide [1006];
N-(7-(1-methyl-1H-pyrazol-4-yl)quinazolin-2-yl)-1-(pyrimidin-2-ylmethyl)piperidine-4-carboxamide [1007];
N-(7-(1-methyl-1H-pyrazol-4-yl)quinazolin-2-yl)-1-(pyrazin-2-ylmethyl)piperidine-4-carboxamide [1008];
1-((5-methyl-1,2,4-oxadiazol-3-yl)methyl)-N-(7-(1-methyl-1H-pyrazol-4-yl)quinazolin-2-yl)piperidine-4-carboxamide [1009];
1-(2-hydroxy-2-methylpropyl)-N-(7-(1-methyl-1H-pyrazol-4-yl)quinazolin-2-yl)piperidine-4-carboxamide [1010];
tert-butyl 2-(4-((7-(1-methyl-1H-pyrazol-4-yl)quinazolin-2-yl)carbamoyl)piperidin-1-yl)acetate [1011];
2-(4-((7-(1-methyl-1H-pyrazol-4-yl)quinazolin-2-yl)carbamoyl)piperidin-1-yl)acetic acid [1012];
2-(4-methyl-1,4-diazepan-1-yl)-N-(7-(1-methyl-1H-pyrazol-4-yl)quinazolin-2-yl)acetamide [1013];
tert-butyl (7-(1-methyl-1H-pyrazol-4-yl)quinazolin-2-yl) carbamate [1014];
N-(7-(1-methyl-1H-pyrazol-4-yl)quinazolin-2-yl)but-2-ynamide [1015];
trans-4-((7-(1-methyl-1H-pyrazol-4-yl)quinazolin-2-yl)carbamoyl)cyclohexane-1-carboxylic acid [1016];
N-(7-(1-methyl-1H-pyrazol-4-yl)quinazolin-2-yl)-3-morpholinopropanamide [1017];
trans-N-(7-(1-methyl-1H-pyrazol-4-yl)quinazolin-2-yl)-3-morpholinocyclobutane-1-carboxamide [1018];
N-(7-(1-methyl-1H-pyrazol-4-yl)quinazolin-2-yl)quinuclidine-4-carboxamide [1019];
1-isobutyl-N-(7-(1-methyl-1H-pyrazol-4-yl)quinazolin-2-yl)azepane-4-carboxamide [1020];
2-(4-methoxypiperidin-1-yl)-N-(7-(1-methyl-1H-pyrazol-4-yl)quinazolin-2-yl)acetamide [1021];
2-(4-hydroxypiperidin-1-yl)-N-(7-(1-methyl-1H-pyrazol-4-yl)quinazolin-2-yl)acetamide [1022];
3-(hydroxymethyl)-N-(7-(1-methyl-1H-pyrazol-4-yl)quinazolin-2-yl)bicyclo[1.1.1]pentane-1-carboxamide [1023];
1-methyl-N-(7-(1-methyl-1H-pyrazol-4-yl)quinazolin-2-yl)azepane-4-carboxamide [1024];
trans-4-(dimethylamino)-N-(7-(1-methyl-1H-pyrazol-4-yl)quinazolin-2-yl)cyclohexane-1-carboxamide [1025];
trans-4-(bis(methyl-$d_3$)amino)-N-(7-(1-methyl-1H-pyrazol-4-yl)quinazolin-2-yl)cyclohexane-1-carboxamide [1026];
N-(7-(1-methyl-1H-pyrazol-4-yl)quinazolin-2-yl)-3-((4-methylpiperazin-1-yl)methyl)bicyclo[1.1.1]pentane-1-carboxamide [1027];
methyl trans-4-((7-(1-methyl-1H-pyrazol-4-yl)quinazolin-2-yl)carbamoyl)cyclohexane-1-carboxylate [1028];
2-(1-isobutylpyrrolidin-3-yl)-N-(7-(1-methyl-1H-pyrazol-4-yl)quinazolin-2-yl)acetamide [1029];
trans-N-(7-(1-methyl-1H-pyrazol-4-yl)quinazolin-2-yl)-4-(4-methylpiperazine-1-carbonyl) cyclohexane-1-carboxamide [1030];
1-isobutyl-N-(7-(1-methyl-1H-pyrazol-4-yl)quinazolin-2-yl)piperidine-4-carboxamide [1031];
N-(7-(1-methyl-1H-pyrazol-4-yl)quinazolin-2-yl)-1-(phenylsulfonyl)piperidine-4-carboxamide [1032];
8-methyl-N-(7-(1-methyl-1H-pyrazol-4-yl)quinazolin-2-yl)-3,8-diazabicyclo[3.2.1]octane-3-carboxamide [1033];
3-methyl-N-(7-(1-methyl-1H-pyrazol-4-yl)quinazolin-2-yl)-3,8-diazabicyclo[3.2.1]octane-8-carboxamide [1034];
(1R,3s,5S)-3-amino-N-(7-(1-methyl-1H-pyrazol-4-yl)quinazolin-2-yl)-8-azabicyclo [3.2.1]octane-8-carboxamide [1035];
(1R,3s,5S)—N-(7-(1-methyl-1H-pyrazol-4-yl)quinazolin-2-yl)-3-((3,3,3-trifluoropropyl)amino)-8-azabicyclo[3.2.1]octane-8-carboxamide [1036];
(1R,3s,5S)-3-((1,3-difluoropropan-2-yl)amino)-N-(7-(1-methyl-1H-pyrazol-4-yl)quinazolin-2-yl)-8-azabicyclo[3.2.1]octane-8-carboxamide [1037];
N-(7-(1-methyl-1H-pyrazol-4-yl)quinazolin-2-yl)morpholine-4-carboxamide [1038];
4-(dimethylamino)-N-(7-(1-methyl-1H-pyrazol-4-yl)quinazolin-2-yl)piperidine-1-carboxamide [1039];
(S)-2,4-dimethyl-N-(7-(1-methyl-1H-pyrazol-4-yl)quinazolin-2-yl)piperazine-1-carboxamide [1040];
1-methyl-3-(7-(1-methyl-1H-pyrazol-4-yl)quinazolin-2-yl)-1-(1-methylpiperidin-4-yl)urea [1041];
1-(7-(1-methyl-1H-pyrazol-4-yl)quinazolin-2-yl)-3-(1-methylpiperidin-4-yl)urea [1042];
4-isopropyl-N-(7-(1-methyl-1H-pyrazol-4-yl)quinazolin-2-yl)piperazine-1-carboxamide [1043];
(R)-3,4-dimethyl-N-(7-(1-methyl-1H-pyrazol-4-yl)quinazolin-2-yl)piperazine-1-carboxamide [1044];
N-(7-(1H-pyrazol-4-yl)quinazolin-2-yl)-2-(4-methylpiperazin-1-yl)isonicotinamide [1045];
N-(7-(1-methyl-1H-pyrazol-4-yl)quinazolin-2-yl)-3-(piperazin-1-yl)benzamide [1046];
N-(7-(1-methyl-1H-pyrazol-4-yl)quinazolin-2-yl)-3-(4-methylpiperazin-1-yl)benzamide [1047];
N-(7-(1-methyl-1H-pyrazol-4-yl)quinazolin-2-yl)-3-(pyrrolidin-1-ylmethyl)benzamide [1048];
N-(7-(1-methyl-1H-pyrazol-4-yl)quinazolin-2-yl)-3-(piperidin-4-yloxy)benzamide [1049];
N-(7-(1-methyl-1H-pyrazol-4-yl)quinazolin-2-yl)-3-((1-methylpiperidin-4-yl)oxy)benzamide [1050];

N-(7-(1-methyl-1H-pyrazol-4-yl)quinazolin-2-yl)-4-(piperidin-4-yloxy)benzamide [1051];

N-(7-(1-methyl-1H-pyrazol-4-yl)quinazolin-2-yl)-4-((1-methylpiperidin-4-yl)oxy)benzamide [1052];

N-(7-(1-methyl-1H-pyrazol-4-yl)quinazolin-2-yl)-2-(piperazin-1-yl)isonicotinamide [1053];

[1054];

2-(4-isopropylpiperazin-1-yl)-N-(7-(1-methyl-1H-pyrazol-4-yl)quinazolin-2-yl)isonicotinamide [1055];

2-(4-cyclopropylpiperazin-1-yl)-N-(7-(1-methyl-1H-pyrazol-4-yl)quinazolin-2-yl) isonicotinamide [1056];

2-(4-(2-fluoroethyl)piperazin-1-yl)-N-(7-(1-methyl-1H-pyrazol-4-yl)quinazolin-2-yl) isonicotinamide [1057];

N-(7-(1-methyl-1H-pyrazol-4-yl)quinazolin-2-yl)-6-(4-methylpiperazin-1-yl)nicotinamide [1058];

N-(7-(1-methyl-1H-pyrazol-4-yl)quinazolin-2-yl)-5-(piperidin-4-yloxy)nicotinamide [1059];

N-(7-(1-methyl-1H-pyrazol-4-yl)quinazolin-2-yl)-2-(piperidin-4-yloxy)isonicotinamide [1060];

N-(7-(1-methyl-1H-pyrazol-4-yl)quinazolin-2-yl)-2-((1-methylpiperidin-4-yl)oxy) isonicotinamide [1061];

N-(7-(1-methyl-1H-pyrazol-4-yl)quinazolin-2-yl)-5-(piperidin-4-ylamino)nicotinamide [1062];

N-(7-(1-methyl-1H-pyrazol-4-yl)quinazolin-2-yl)-5-((1-methylpiperidin-4-yl)amino)nicotinamide [1063];

2-(4-aminopiperidin-1-yl)-N-(7-(1-methyl-1H-pyrazol-4-yl)quinazolin-2-yl)isonicotinamide [1064];

N-(7-(1-methyl-1H-pyrazol-4-yl)quinazolin-2-yl)-2-(4-(methylamino)piperidin-1-yl) isonicotinamide [1065];

2-(4-(dimethylamino)piperidin-1-yl)-N-(7-(1-methyl-1H-pyrazol-4-yl)quinazolin-2-yl) isonicotinamide [1066];

2-((1-isopropylpiperidin-4-yl)oxy)-N-(7-(1-methyl-1H-pyrazol-4-yl)quinazolin-2-yl) isonicotinamide [1067];

2-(3-aminoazetidin-1-yl)-N-(7-(1-methyl-1H-pyrazol-4-yl)quinazolin-2-yl)isonicotinamide [1068];

2-(3-(dimethylamino)azetidin-1-yl)-N-(7-(1-methyl-1H-pyrazol-4-yl)quinazolin-2-yl) isonicotinamide [1069];

N-(7-(1-methyl-1H-pyrazol-4-yl)quinazolin-2-yl)-2-morpholinoisonicotinamide [1070];

2-((2-(dimethylamino)ethyl)amino)-N-(7-(1-methyl-1H-pyrazol-4-yl)quinazolin-2-yl) isonicotinamide [1071];

2-(2-(dimethylamino)ethoxy)-N-(7-(1-methyl-1H-pyrazol-4-yl)quinazolin-2-yl)isonicotinamide [1072];

2-(4-isobutylpiperazin-1-yl)-N-(7-(1-methyl-1H-pyrazol-4-yl)quinazolin-2-yl)isonicotinamide [1073];

2-(azetidin-3-yloxy)-N-(7-(1-methyl-1H-pyrazol-4-yl)quinazolin-2-yl)isonicotinamide [1074];

N-(7-(1-methyl-1H-pyrazol-4-yl)quinazolin-2-yl)-2-((1-methylazetidin-3-yl)oxy)isonicotinamide [1075];

2-(4-ethylpiperazin-1-yl)-N-(7-(1-methyl-1H-pyrazol-4-yl)quinazolin-2-yl)isonicotinamide [1076];

4-((dimethylamino)methyl)-N-(7-(1-methyl-1H-pyrazol-4-yl)quinazolin-2-yl)benzamide [1077];

N-(7-(1-methyl-1H-pyrazol-4-yl)quinazolin-2-yl)-3-(1-methylpiperidin-4-yl)benzamide [1078];

N-(7-(1-methyl-1H-pyrazol-4-yl)quinazolin-2-yl)-3-((4-methylpiperazin-1-yl)methyl)benzamide [1079];

N-(7-(1-methyl-1H-pyrazol-4-yl)quinazolin-2-yl)isonicotinamide [1080];

2-hydroxy-N-(7-(1-methyl-1H-pyrazol-4-yl)quinazolin-2-yl)isonicotinamide [1081];

2-isopropoxy-N-(7-(1-methyl-1H-pyrazol-4-yl)quinazolin-2-yl)isonicotinamide [1082];

N-(7-(1-methyl-1H-pyrazol-4-yl)quinazolin-2-yl)-2-(1-methylpiperidin-4-yl)isonicotinamide [1083];

1'-methyl-N-(7-(1-methyl-1H-pyrazol-4-yl)quinazolin-2-yl)-1',2',3',6'-tetrahydro-[2,4'-bipyridine]-4-carboxamide [1084];

N-(7-(1-methyl-1H-pyrazol-4-yl)quinazolin-2-yl)-2-(4-(6-(4-methylpiperazin-1-yl) nicotinoyl)piperazin-1-yl) isonicotinamide [1085];

2-(4-hydroxy-4-methyl-4$\lambda^4$-piperazin-1-yl)-N-(7-(1-methyl-1H-pyrazol-4-yl)quinazolin-2-yl) isonicotinamide [1086];

2-methyl-N-(7-(1-methyl-1H-pyrazol-4-yl)quinazolin-2-yl)-6-(4-methylpiperazin-1-yl) isonicotinamide [1087];

3-methyl-N-(7-(1-methyl-1H-pyrazol-4-yl)quinazolin-2-yl)-2-(4-methylpiperazin-1-yl) isonicotinamide [1088];

2-(4-methyl-1,4-diazepan-1-yl)-N-(7-(-methyl-1H-pyrazol-4-yl)quinazolin-2-yl)isonicotinamide [1089];

2-((2S,6R)-2,6-dimethylmorpholino)-N-(7-(1-methyl-1H-pyrazol-4-yl)quinazolin-2-yl) isonicotinamide [1090];

N-(7-(1-methyl-1H-pyrazol-4-yl)quinazolin-2-yl)-2-(2,7-diazaspiro[3.5]nonan-2-yl) isonicotinamide [1091];

N-(7-(1-methyl-1H-pyrazol-4-yl)quinazolin-2-yl)-2-(7-methyl-2,7-diazaspiro[3.5]nonan-2-yl) isonicotinamide [1092];

N-(7-(1-methyl-1H-pyrazol-4-yl)quinazolin-2-yl)-2-(2,7-diazaspiro[3.5]nonan-7-yl) isonicotinamide [1093];

N-(7-(1-methyl-1H-pyrazol-4-yl)quinazolin-2-yl)-2-(2-methyl-2,7-diazaspiro[3.5]nonan-7-yl) isonicotinamide [1094];

2-(methyl(1-methylpiperidin-4-yl)amino)-N-(7-(1-methyl-1H-pyrazol-4-yl)quinazolin-2-yl) isonicotinamide [1095];

N-(7-(1-methyl-1H-pyrazol-4-yl)quinazolin-2-yl)-2-((1-methylpiperidin-4-yl)thio) isonicotinamide [1096];

N-(7-(1-methyl-1H-pyrazol-4-yl)quinazolin-2-yl)-2-(4-methylpiperazin-1-yl)pyrimidine-4-carboxamide [1097];

N-(7-(1-methyl-1H-pyrazol-4-yl)quinazolin-2-yl)-6-(4-methylpiperazin-1-yl)pyridazine-4-carboxamide [1098];

N-(7-(1-methyl-1H-pyrazol-4-yl)quinazolin-2-yl)-6-(4-methylpiperazin-1-yl)pyrimidine-4-carboxamide [1099];

N-(7-(1-methyl-1H-pyrazol-4-yl)quinazolin-2-yl)-2-phenylacetamide [1100];

N-(7-(1-methyl-1H-pyrazol-4-yl)quinazolin-2-yl)-3-phenylpropanamide [1101];

N-(7-(1-methyl-1H-pyrazol-4-yl)quinazolin-2-yl)-2-(pyridin-3-yl)acetamide [1102];

N-(7-(1-methyl-1H-pyrazol-4-yl)quinazolin-2-yl)-3-(pyridin-3-yl)propanamide [1103];

N-(7-(1-methyl-1H-pyrazol-4-yl)quinazolin-2-yl)-2-(pyridin-4-yl)acetamide [1104];

N-(7-(1-methyl-1H-pyrazol-4-yl)quinazolin-2-yl)-3-(pyridin-4-yl)propanamide [1105];

N-(7-(1-methyl-1H-pyrazol-4-yl)quinazolin-2-yl)isoindoline-5-carboxamide [1106];

2-methyl-N-(7-(1-methyl-1H-pyrazol-4-yl)quinazolin-2-yl)isoindoline-5-carboxamide [1107];

N-(7-(1-methyl-1H-pyrazol-4-yl)quinazolin-2-yl)-1,2,3,4-tetrahydroisoquinoline-7-carboxamide [1108];

2-methyl-N-(7-(1-methyl-1H-pyrazol-4-yl)quinazolin-2-yl)-1,2,3,4-tetrahydroisoquinoline-7-carboxamide [1109];

2-methyl-N-(7-(1-methyl-1H-pyrazol-4-yl)quinazolin-2-yl)-1,2,3,4-tetrahydroisoquinoline-6-carboxamide [1110];

N-(7-(1-methyl-1H-pyrazol-4-yl)quinazolin-2-yl)-1,2,3,4-tetrahydroisoquinoline-6-carboxamide [1111];
N-(7-(1-methyl-1H-pyrazol-4-yl)quinazolin-2-yl)-1H-indole-5-carboxamide [1112];
N-(7-(1-methyl-1H-pyrazol-4-yl)quinazolin-2-yl)benzofuran-5-carboxamide [1113];
N-(7-(1-methyl-1H-pyrazol-4-yl)quinazolin-2-yl)furo[2,3-c]pyridine-5-carboxamide [1114];
N-(7-(1-methyl-1H-pyrazol-4-yl)quinazolin-2-yl)benzo[b]thiophene-5-carboxamide [1115];
N-(7-(1-methyl-1H-pyrazol-4-yl)quinazolin-2-yl)benzofuran-6-carboxamide [1116];
N-(7-(1-methyl-1H-pyrazol-4-yl)quinazolin-2-yl)benzo[d]oxazole-6-carboxamide [1117];
N-(7-(1-methyl-1H-pyrazol-4-yl)quinazolin-2-yl)benzo[d]thiazole-6-carboxamide [1118];
N-(7-(1-methyl-1H-pyrazol-4-yl)quinazolin-2-yl)benzo[d]oxazole-5-carboxamide [1119];
N-(7-(1-methyl-1H-pyrazol-4-yl)quinazolin-2-yl)benzo[d]thiazole-5-carboxamide [1120];
N-(7-(1-methyl-1H-pyrazol-4-yl)quinazolin-2-yl)quinoline-3-carboxamide [1121];
N-(7-(1-methyl-1H-pyrazol-4-yl)quinazolin-2-yl)quinoline-6-carboxamide [1122];
N-(7-(1-methyl-1H-pyrazol-4-yl)quinazolin-2-yl)quinoxaline-6-carboxamide [1123];
5-chloro-N-(7-(1-methyl-1H-pyrazol-4-yl)quinazolin-2-yl)-2-(4-methylpiperazin-1-yl) isonicotinamide [1124];
3-chloro-N-(7-(1-methyl-1H-pyrazol-4-yl)quinazolin-2-yl)-2-(4-methylpiperazin-1-yl) isonicotinamide [1125];
2-(2,5-diazabicyclo[2.2.1]heptan-2-yl)-N-(7-(1-methyl-1H-pyrazol-4-yl)quinazolin-2-yl) isonicotinamide [1126];
N-(7-(1-methyl-1H-pyrazol-4-yl)quinazolin-2-yl)-2-(5-methyl-2,5-diazabicyclo [2.2.1]heptan-2-yl)isonicotinamide [1127];
3-fluoro-N-(7-(1-methyl-1H-pyrazol-4-yl)quinazolin-2-yl)-2-(4-methylpiperazin-1-yl) isonicotinamide [1128];
N-(7-(1-methyl-1H-pyrazol-4-yl)quinazolin-2-yl)-2-((4-methylpiperazin-1-yl)methyl) isonicotinamide [1129];
N-(7-(1-methyl-1H-pyrazol-4-yl)quinazolin-2-yl)-2-(morpholinomethyl)isonicotinamide [1130];
N-(7-(1-methyl-1H-pyrazol-4-yl)quinazolin-2-yl)-2-(pyrrolidin-1-ylmethyl)isonicotinamide [1131];
N-(7-(1-methyl-1H-pyrazol-4-yl)quinazolin-2-yl)-2-(2-(4-methylpiperazin-1-yl)pyridin-4-yl) acetamide [1132];
1-methyl-N-(7-(1-methyl-1H-pyrazol-4-yl)quinazolin-2-yl)-1H-indazole-5-carboxamide [1133];
1-methyl-N-(7-(1-methyl-1H-pyrazol-4-yl)quinazolin-2-yl)-1H-benzo[d]imidazole-5-carboxamide [1134];
N-(7-(1-methyl-1H-pyrazol-4-yl)quinazolin-2-yl)-1-(piperidin-4-yl)-1H-pyrazole-4-carboxamide [1135];
N-(7-(1-methyl-1H-pyrazol-4-yl)quinazolin-2-yl)-1-(1-methylpiperidin-4-yl)-1H-pyrazole-4-carboxamide [1136];
1-(1-ethylpiperidin-4-yl)-N-(7-(1-methyl-1H-pyrazol-4-yl)quinazolin-2-yl)-1H-pyrazole-4-carboxamide [1137];
1-(1-(2-fluoroethyl)piperidin-4-yl)-N-(7-(1-methyl-1H-pyrazol-4-yl)quinazolin-2-yl)-1H-pyrazole-4-carboxamide [1138];
1-(1-isopropylpiperidin-4-yl)-N-(7-(1-methyl-1H-pyrazol-4-yl)quinazolin-2-yl)-1H-pyrazole-4-carboxamide [1139];
1-(1-cyclopropylpiperidin-4-yl)-N-(7-(1-methyl-1H-pyrazol-4-yl)quinazolin-2-yl)-1H-pyrazole-4-carboxamide [1140];
isopropyl 4-(4-((7-(1-methyl-1H-pyrazol-4-yl)quinazolin-2-yl)carbamoyl)-1H-pyrazol-1-yl)piperidine-1-carboxylate [1141];
N-(7-(1-methyl-1H-pyrazol-4-yl)quinazolin-2-yl)-1-(piperidin-4-yl)-1H-1,2,3-triazole-4-carboxamide [1142];
N-(7-(1-methyl-1H-pyrazol-4-yl)quinazolin-2-yl)-1-(1-methylpiperidin-4-yl)-1H-1,2,3-triazole-4-carboxamide [1143];
1-(1-(2-fluoroethyl)piperidin-4-yl)-N-(7-(1-methyl-1H-pyrazol-4-yl)quinazolin-2-yl)-1H-1,2,3-triazole-4-carboxamide [1144];
1-(1-isopropylpiperidin-4-yl)-N-(7-(1-methyl-1H-pyrazol-4-yl)quinazolin-2-yl)-1H-1,2,3-triazole-4-carboxamide [1145];
N-(7-(1-methyl-1H-pyrazol-4-yl)quinazolin-2-yl)-2-(4-methylpiperazin-1-yl)oxazole-5-carboxamide [1146];
2-(3-(dimethylamino)azetidin-1-yl)-N-(7-(1-methyl-1H-pyrazol-4-yl)quinazolin-2-yl)oxazole-4-carboxamide [1147];
N-(7-(1-methyl-1H-pyrazol-4-yl)quinazolin-2-yl)-2-(piperidin-4-yl)oxazole-4-carboxamide [1148];
N-(7-(1-methyl-1H-pyrazol-4-yl)quinazolin-2-yl)-2-(1-methylpiperidin-4-yl)oxazole-4-carboxamide [1149];
2-(1-(2-fluoroethyl)piperidin-4-yl)-N-(7-(1-methyl-1H-pyrazol-4-yl)quinazolin-2-yl)oxazole-4-carboxamide [1150];
2-(1-isopropylpiperidin-4-yl)-N-(7-(1-methyl-1H-pyrazol-4-yl)quinazolin-2-yl)oxazole-4-carboxamide [1151];
N-(7-(1-methyl-1H-pyrazol-4-yl)quinazolin-2-yl)-2-(4-methylpiperazin-1-yl)oxazole-4-carboxamide [1152];
2-(3-(dimethylamino)azetidin-1-yl)-N-(7-(1-methyl-1H-pyrazol-4-yl)quinazolin-2-yl)thiazole-5-carboxamide [1153];
N-(7-(1-methyl-1H-pyrazol-4-yl)quinazolin-2-yl)-2-(piperidin-4-yl)thiazole-4-carboxamide [1154];
N-(7-(1-methyl-1H-pyrazol-4-yl)quinazolin-2-yl)-2-(4-methylpiperazin-1-yl)thiazole-4-carboxamide [1155];
2-(1-(2-fluoroethyl)piperidin-4-yl)-N-(7-(1-methyl-1H-pyrazol-4-yl)quinazolin-2-yl)thiazole-4-carboxamide [1156];
2-(1-isopropylpiperidin-4-yl)-N-(7-(1-methyl-1H-pyrazol-4-yl)quinazolin-2-yl)thiazole-4-carboxamide [1157];
N-(7-(1-methyl-1H-pyrazol-4-yl)quinazolin-2-yl)-1-(2-(methyl-$d_3$)propyl-1,1,2,3,3,3-$d_6$) piperidine-4-carboxamide [1158];
N-(7-(1-methyl-1H-pyrazol-4-yl)quinazolin-2-yl)-2-(pyrrolidin-1-yl-2,2,5,5-$d_4$)acetamide [1159];
N-(7-(1-methyl-1H-pyrazol-4-yl)quinazolin-2-yl)-2-(4-(methyl-$d_3$)piperazin-1-yl)acetamide [1160];
N-(7-(1-methyl-1H-pyrazol-4-yl)quinazolin-2-yl)-2-(morpholino-$d_8$)acetamide [1161];
(S)—N-(7-(1-(methyl-$d_3$)-1H-pyrazol-4-yl)quinazolin-2-yl)-2-(pyrrolidin-1-yl)propanamide [1162];
1-isobutyl-N-(7-(1-(methyl-$d_3$)-1H-pyrazol-4-yl)quinazolin-2-yl)piperidine-4-carboxamide [1163];
N-(7-(1-(methyl-$d_3$)-1H-pyrazol-4-yl)quinazolin-2-yl)-2-(4-methylpiperazin-1-yl)acetamide [1164];
N-(7-(1-(methyl-$d_3$)-1H-pyrazol-4-yl)quinazolin-2-yl)-2-(pyrrolidin-1-yl)acetamide [1165];
N-(7-(1-(methyl-$d_3$)-1H-pyrazol-4-yl)quinazolin-2-yl)-2-(piperidin-1-yl)acetamide [1166];

N-(7-(1-(methyl-d₃)-1H-pyrazol-4-yl)quinazolin-2-yl)-1-(3,3,3-trifluoropropyl)piperidine-4-carboxamide [1167];

N-(7-(1H-pyrazol-4-yl)quinazolin-2-yl)-2-(4-(methyl-d₃)piperazin-1-yl)isonicotinamide [1168];

N-(7-(1-methyl-1H-pyrazol-4-yl)quinazolin-2-yl)-2-(4-(methyl-d₃)piperazin-1-yl)isonicotinamide [1169];

N-(7-(1-(methyl-d₃)-1H-pyrazol-4-yl)quinazolin-2-yl)-2-(4-methylpiperazin-1-yl)isonicotinamide [1170];

N-(7-(1-(methyl-d₃)-1H-pyrazol-4-yl)quinazolin-2-yl)-2-(4-(methyl-d₃)piperazin-1-yl) isonicotinamide [1171];

N-(7-(1-(methyl-d₃)-1H-pyrazol-4-yl)quinazolin-2-yl)-1-(piperidin-4-yl)-1H-pyrazole-4-carboxamide [1172];

N-(7-(1-(methyl-d₃)-1H-pyrazol-4-yl)quinazolin-2-yl)-1-(1-methylpiperidin-4-yl)-1H-pyrazole-4-carboxamide [1173];

N-(7-(1-(methyl-d₃)-1H-pyrazol-4-yl)quinazolin-2-yl)-2-(piperidin-4-yl)oxazole-4-carboxamide [1174];

N-(7-(1-(methyl-d₃)-1H-pyrazol-4-yl)quinazolin-2-yl)-2-(1-methylpiperidin-4-yl)oxazole-4-carboxamide [1175];

N-(7-(1-ethyl-1H-pyrazol-4-yl)quinazolin-2-yl)-2-(pyrrolidin-1-yl)acetamide [1176];

N-(7-(1-cyclopropyl-1H-pyrazol-4-yl)quinazolin-2-yl)-2-(pyrrolidin-1-yl)acetamide [1177];

N-(7-(1-cyclopropyl-1H-pyrazol-4-yl)quinazolin-2-yl)-1-(3,3-trifluoropropyl)piperidine-4-carboxamide [1178];

N-(7-(1-(1-methylpiperidin-4-yl)-1H-pyrazol-4-yl)quinazolin-2-yl)cyclohexanecarboxamide [1179];

2-(pyrrolidin-1-yl)-N-(7-(5-(trifluoromethyl)-1H-pyrazol-4-yl)quinazolin-2-yl)acetamide [1180];

N-(7-(5-(hydroxymethyl)-1-methyl-1H-pyrazol-4-yl)quinazolin-2-yl)-1-methylpiperidine-4-carboxamide [1181];

N-(7-(5-(hydroxymethyl)-1-methyl-1H-pyrazol-4-yl)quinazolin-2-yl)tetrahydro-2H-pyran-4-carboxamide [1182];

N-(7-(5-(azetidin-1-ylmethyl)-1-methyl-1H-pyrazol-4-yl)quinazolin-2-yl)-4,4-difluorocyclohexane-1-carboxamide [1183];

4,4-difluoro-N-(7-(1-methyl-5-(pyrrolidin-1-ylmethyl)-1H-pyrazol-4-yl)quinazolin-2-yl) cyclohexane-1-carboxamide [1184];

4,4-difluoro-N-(7-(1-methyl-5-(piperidin-1-ylmethyl)-1H-pyrazol-4-yl)quinazolin-2-yl) cyclohexane-1-carboxamide [1185];

2-(2-fluoroethyl)-N-(7-(1-methyl-5-(piperidin-1-ylmethyl)-1H-pyrazol-4-yl)quinazolin-2-yl)-2-azaspiro[3.3]heptane-6-carboxamide [1186];

tert-butyl 6-((7-(1-methyl-5-(piperidin-1-ylmethyl)-1H-pyrazol-4-yl)quinazolin-2-yl)carbamoyl)-2-azaspiro[3.3]heptane-2-carboxylate [1187];

2-fluoro-2-methyl-N-(7-(1-methyl-5-(piperidin-1-ylmethyl)-1H-pyrazol-4-yl)quinazolin-2-yl) propanamide [1188];

2-(diethylamino)-N-(7-(1-methyl-5-(piperidin-1-ylmethyl)-1H-pyrazol-4-yl)quinazolin-2-yl) acetamide [1189];

trans-4-methoxy-N-(7-(1-methyl-5-(piperidin-1-ylmethyl)-1H-pyrazol-4-yl)quinazolin-2-yl) cyclohexane-1-carboxamide [1190];

trans-4-(hydroxymethyl)-N-(7-(1-methyl-5-(piperidin-1-ylmethyl)-1H-pyrazol-4-yl)quinazolin-2-yl)cyclohexane-1-carboxamide [1191];

(R)—N-(7-(1-methyl-5-(piperidin-1-ylmethyl)-1H-pyrazol-4-yl)quinazolin-2-yl)pyrrolidine-2-carboxamide [1192];

1-isobutyl-N-(7-(1-methyl-5-(piperidin-1-ylmethyl)-1H-pyrazol-4-yl)quinazolin-2-yl)piperidine-4-carboxamide [1193];

N-(7-(1-methyl-5-(piperidin-1-ylmethyl)-1H-pyrazol-4-yl)quinazolin-2-yl)-1-(oxetan-3-yl) piperidine-4-carboxamide [1194];

1-benzoyl-N-(7-(1-methyl-5-(piperidin-1-ylmethyl)-1H-pyrazol-4-yl)quinazolin-2-yl)piperidine-4-carboxamide [1195];

N-(7-(1-methyl-5-(piperidin-1-ylmethyl)-1H-pyrazol-4-yl)quinazolin-2-yl)tetrahydro-2H-pyran-4-carboxamide [1196];

N-(7-(1-methyl-5-(piperidin-1-ylmethyl)-1H-pyrazol-4-yl)quinazolin-2-yl)-2-(4-methylpiperidin-1-yl)acetamide [1197];

N-(7-(1-(difluoromethyl)-1H-pyrazol-4-yl)quinazolin-2-yl)-2-(4-methylpiperazin-1-yl) isonicotinamide [1198];

N-(7-(1-ethyl-1H-pyrazol-4-yl)quinazolin-2-yl)-2-(4-methylpiperazin-1-yl)isonicotinamide [1199];

N-(7-(1-isopropyl-1H-pyrazol-4-yl)quinazolin-2-yl)-3-(piperidin-4-yloxy)benzamide [1200];

N-(7-(1-isopropyl-1H-pyrazol-4-yl)quinazolin-2-yl)-3-((1-methylpiperidin-4-yl)oxy)benzamide [1201];

N-(7-(1-isopropyl-1H-pyrazol-4-yl)quinazolin-2-yl)-4-(piperidin-4-yloxy)benzamide [1202];

N-(7-(1-cyclopropyl-1H-pyrazol-4-yl)quinazolin-2-yl)-2-(4-methylpiperazin-1-yl) isonicotinamide [1203];

4-fluoro-N-(7-(1-(1-methylpiperidin-4-yl)-1H-pyrazol-4-yl)quinazolin-2-yl)benzamide [1204];

4-(difluoromethoxy)-N-(7-(1-(1-methylpiperidin-4-yl)-1H-pyrazol-4-yl)quinazolin-2-yl) benzamide [1205];

5-fluoro-N-(7-(1-(1-methylpiperidin-4-yl)-1H-pyrazol-4-yl)quinazolin-2-yl)nicotinamide [1206];

$N^2$-methyl-$N^5$-(7-(1-(1-methylpiperidin-4-yl)-1H-pyrazol-4-yl)quinazolin-2-yl)pyridine-2,5-dicarboxamide [1207];

1-isopropyl-N-(7-(1-(1-methylpiperidin-4-yl)-1H-pyrazol-4-yl)quinazolin-2-yl)-1H-pyrazole-4-carboxamide [1208];

2-methyl-N-(7-(1-(1-methylpiperidin-4-yl)-1H-pyrazol-4-yl)quinazolin-2-yl)thiazole-5-carboxamide [1209];

N-(7-(5-amino-1-methyl-1H-pyrazol-4-yl)quinazolin-2-yl)-2-(4-methylpiperazin-1-yl) isonicotinamide [1210];

4-(difluoromethoxy)-N-(7-(5-(hydroxymethyl)-1-methyl-1H-pyrazol-4-yl)quinazolin-2-yl) benzamide [1211];

N-(7-(5-(hydroxymethyl)-1-methyl-1H-pyrazol-4-yl)quinazolin-2-yl)-2-(4-methylpiperazin-1-yl) isonicotinamide [1212];

N-(7-(5-(hydroxymethyl)-1-methyl-1H-pyrazol-4-yl)quinazolin-2-yl)-2-(7-methyl-2,7-diazaspiro [3.5]nonan-2-yl)isonicotinamide [1213];

4-fluoro-N-(7-(1-methyl-5-(pyrrolidin-1-ylmethyl)-1H-pyrazol-4-yl)quinazolin-2-yl)benzamide [1214];

4-fluoro-N-(7-(1-methyl-5-(piperidin-1-ylmethyl)-1H-pyrazol-4-yl)quinazolin-2-yl)benzamide [1215];

4-(difluoromethoxy)-N-(7-(1-methyl-5-(piperidin-1-ylmethyl)-1H-pyrazol-4-yl)quinazolin-2-yl) benzamide [1216];

N-(7-(1-methyl-5-(piperidin-1-ylmethyl)-1H-pyrazol-4-yl)quinazolin-2-yl)-3-(pyrrolidin-1-ylmethyl)benzamide [1217];

N-(7-(1-methyl-5-(piperidin-1-ylmethyl)-1H-pyrazol-4-yl)quinazolin-2-yl)-2-(7-methyl-2,7-diazaspiro[3.5]nonan-2-yl)isonicotinamide [1218];

N-(7-(1-methyl-5-(piperidin-1-ylmethyl)-1H-pyrazol-4-yl)quinazolin-2-yl)-2-morpholinoisonicotinamide [1219];

N-(7-(1-methyl-5-(morpholinomethyl)-1H-pyrazol-4-yl) quinazolin-2-yl)-2-morpholinoisonicotinamide [1220];

N-(7-(4,5,6,7-tetrahydropyrazolo[1,5-a]pyrazin-3-yl)quinazolin-2-yl)-1-((1-(trifluoromethyl) cyclopropyl) methyl)piperidine-4-carboxamide [1221];

3,3-difluoro-N-(7-(5-methyl-4,5,6,7-tetrahydropyrazolo [1,5-a]pyrazin-3-yl)quinazolin-2-yl) cyclobutane-1-carboxamide [1222];

N-((4,4-difluorocyclohexyl)methyl)-7-(5-(2-fluoroethyl)-4,5,6,7-tetrahydropyrazolo[1,5-a] pyrazin-3-yl)quinazolin-2-amine [1223];

N-(7-(5-(2-fluoroethyl)-4,5,6,7-tetrahydropyrazolo[1,5-a]pyrazin-3-yl)quinazolin-2-yl)-1-((1-(trifluoromethyl) cyclopropyl)methyl)piperidine-4-carboxamide [1224];

N-(7-(5-(2-fluoroethyl)-4,5,6,7-tetrahydropyrazolo[1,5-a]pyrazin-3-yl)quinazolin-2-yl)-2-(pyrrolidin-1-yl)acetamide [1225];

2-(7-azabicyclo[2.2.1]heptan-7-yl)-N-(7-(5-(2-fluoroethyl)-4,5,6,7-tetrahydropyrazolo[1,5-a]pyrazin-3-yl) quinazolin-2-yl)acetamide [1226];

(R)—N-(7-(5-(2-fluoroethyl)-4,5,6,7-tetrahydropyrazolo [1,5-a]pyrazin-3-yl)quinazolin-2-yl)-1-isobutylpiperidine-3-carboxamide [1227];

N-(7-(5-(2-fluoroethyl)-4,5,6,7-tetrahydropyrazolo[1,5-a]pyrazin-3-yl)quinazolin-2-yl)piperidine-4-carboxamide [1228];

4-fluoro-N-(7-(5-(2-fluoroethyl)-4,5,6,7-tetrahydropyrazolo[1,5-a]pyrazin-3-yl)quinazolin-2-yl)-1-isobutylpiperidine-4-carboxamide [1229];

N-(7-(5-(2-fluoroethyl)-4,5,6,7-tetrahydropyrazolo[1,5-a]pyrazin-3-yl)quinazolin-2-yl)-2-(4-methylpiperazin-1-yl)acetamide [1230];

4-fluoro-N-(7-(4,5,6,7-tetrahydropyrazolo[1,5-a]pyrazin-3-yl)quinazolin-2-yl)benzamide [1231];

N-(7-(5-(2-fluoroethyl)-4,5,6,7-tetrahydropyrazolo[1,5-a]pyrazin-3-yl)quinazolin-2-yl)-3-(4-methylpiperazin-1-yl)benzamide [1232];

$N^5$-(7-(5-(2-fluoroethyl)-4,5,6,7-tetrahydropyrazolo[1,5-a]pyrazin-3-yl)quinazolin-2-yl)-$N^2$ methylpyridine-2,5-dicarboxamide [1233];

N-(7-(5-(2-fluoroethyl)-4,5,6,7-tetrahydropyrazolo[1,5-a]pyrazin-3-yl)quinazolin-2-yl)-6-(4-methylpiperazin-1-yl)nicotinamide [1234];

2-(azetidin-3-yloxy)-N-(7-(5-(2-fluoroethyl)-4,5,6,7-tetrahydropyrazolo[1,5-a]pyrazin-3-yl) quinazolin-2-yl) isonicotinamide [1235];

N-(7-(1-methyl-1H-pyrazol-5-yl)quinazolin-2-yl)-1-(3,3,3-trifluoropropyl)piperidine-4-carboxamide [1236];

1-methyl-N-(7-(1-methyl-1H-pyrazol-3-yl)quinazolin-2-yl)piperidine-4-carboxamide [1237];

N-(7-(1-methyl-1H-pyrazol-3-yl)quinazolin-2-yl)-2-(4-methylpiperazin-1-yl)isonicotinamide [1238];

2-fluoro-2-methyl-N-(7-(1-methyl-1H-1,2,3-triazol-4-yl) quinazolin-2-yl)propanamide [1239];

2,2,3,3-tetramethyl-N-(7-(1-methyl-1H-1,2,3-triazol-4-yl)quinazolin-2-yl)cyclopropane-1-carboxamide [1240];

trans-N-(7-(1-methyl-1H-1,2,3-triazol-4-yl)quinazolin-2-yl)-4-(pyrrolidin-1-yl)cyclohexane-1-carboxamide [1241];

trans-N-(7-(1-methyl-1H-1,2,3-triazol-4-yl)quinazolin-2-yl)-4-morpholinocyclohexane-1-carboxamide [1242];

N-(7-(1-methyl-1H-1,2,3-triazol-4-yl)quinazolin-2-yl)-2-(piperidin-1-yl)acetamide [1243];

1-ethyl-4-fluoro-N-(7-(1-methyl-1H-1,2,3-triazol-4-yl) quinazolin-2-yl)piperidine-4-carboxamide [1244];

4-fluoro-1-isobutyl-N-(7-(1-methyl-1H-1,2,3-triazol-4-yl)quinazolin-2-yl)piperidine-4-carboxamide [1245];

N-(7-(1-methyl-1H-1,2,3-triazol-4-yl)quinazolin-2-yl)-1-(3,3,3-trifluoropropyl)piperidine-4-carboxamide [1246];

N-(7-(1-methyl-1H-1,2,3-triazol-4-yl)quinazolin-2-yl)cyclopropanecarboxamide [1247];

4,4-difluoro-N-(7-(1-methyl-1H-1,2,3-triazol-4-yl)quinazolin-2-yl)cyclohexane-1-carboxamide [1248];

trans-4-(dimethylamino)-N-(7-(1-methyl-1H-1,2,3-triazol-4-yl)quinazolin-2-yl)cyclohexane-1-carboxamide [1249];

trans-N-(7-(1-methyl-1H-1,2,3-triazol-4-yl)quinazolin-2-yl)-4-((4-methylpiperazin-1-yl)methyl) cyclohexane-1-carboxamide [1250];

N-(7-(1-methyl-1H-1,2,3-triazol-4-yl)quinazolin-2-yl)piperidine-4-carboxamide [1251];

1-isobutyl-N-(7-(1-methyl-1H-1,2,3-triazol-4-yl)quinazolin-2-yl)piperidine-4-carboxamide [1252];

N-(7-(1-methyl-1H-1,2,3-triazol-4-yl)quinazolin-2-yl)-1-((1-(trifluoromethyl)cyclopropyl) methyl)piperidine-4-carboxamide [1253];

N-(7-(1-methyl-1H-1,2,3-triazol-4-yl)quinazolin-2-yl)-1-((3-methyloxetan-3-yl)methyl) piperidine-4-carboxamide [1254];

N-(7-(1-methyl-1H-1,2,3-triazol-4-yl)quinazolin-2-yl)-1-(2-(pyrrolidin-1-yl)acetyl)piperidine-4-carboxamide [1255];

1'-methyl-N-(7-(1-methyl-1H-1,2,3-triazol-4-yl)quinazolin-2-yl)-[1,4'-bipiperidine]-4-carboxamide [1256];

(R)—N-(7-(1-methyl-1H-1,2,3-triazol-4-yl)quinazolin-2-yl)piperidine-3-carboxamide [1257];

(R)-1-isobutyl-N-(7-(1-methyl-1H-1,2,3-triazol-4-yl)quinazolin-2-yl)piperidine-3-carboxamide [1258];

N-(7-(1-methyl-1H-1,2,3-triazol-4-yl)quinazolin-2-yl)-2-(pyrrolidin-1-yl)acetamide [1259];

N-(7-(1-methyl-1H-1,2,3-triazol-4-yl)quinazolin-2-yl)-2-(4-methylpiperazin-1-yl)acetamide [1260];

2-(7-azabicyclo[2.2.1]heptan-7-yl)-N-(7-(1-methyl-1H-1,2,3-triazol-4-yl)quinazolin-2-yl) acetamide [1261];

1-(2-hydroxy-2-methylpropyl)-N-(7-(1-methyl-1H-1,2,3-triazol-4-yl)quinazolin-2-yl)piperidine-4-carboxamide [1262];

N-(7-(1-methyl-1H-1,2,3-triazol-4-yl)quinazolin-2-yl)-2-morpholinoacetamide [1263];

2-(4-methoxypiperidin-1-yl)-N-(7-(1-methyl-1H-1,2,3-triazol-4-yl)quinazolin-2-yl)acetamide [1264];

N-(7-(1-methyl-1H-1,2,3-triazol-4-yl)quinazolin-2-yl) morpholine-4-carboxamide [1265];

N-(7-(1-methyl-1H-1,2,3-triazol-4-yl)quinazolin-2-yl)-1-(piperidin-4-yl)-1H-pyrazole-4-carboxamide [1266];

N-(7-(1-methyl-1H-1,2,3-triazol-4-yl)quinazolin-2-yl)-1-(1-methylpiperidin-4-yl)-1H-pyrazole-4-carboxamide [1267];

1-(1-ethylpiperidin-4-yl)-N-(7-(1-methyl-1H-1,2,3-triazol-4-yl)quinazolin-2-yl)-1H-pyrazole-4-carboxamide [1268];

1-(1-isopropylpiperidin-4-yl)-N-(7-(1-methyl-1H-1,2,3-triazol-4-yl)quinazolin-2-yl)-1H-pyrazole-4-carboxamide [1269];

N-(7-(1-methyl-1H-1,2,3-triazol-4-yl)quinazolin-2-yl)-1-(piperidin-4-yl)-1H-1,2,3-triazole-4-carboxamide [1270];

1-(1-(2-fluoroethyl)piperidin-4-yl)-N-(7-(1-methyl-1H-1,2,3-triazol-4-yl)quinazolin-2-yl)-1H-1,2,3-triazole-4-carboxamide [1271];

1-(1-isopropylpiperidin-4-yl)-N-(7-(1-methyl-1H-1,2,3-triazol-4-yl)quinazolin-2-yl)-1H-1,2,3-triazole-4-carboxamide [1272];
N-(7-(1-methyl-1H-1,2,3-triazol-4-yl)quinazolin-2-yl)-2-(piperidin-4-yl)oxazole-4-carboxamide [1273];
N-(7-(1-methyl-1H-1,2,3-triazol-4-yl)quinazolin-2-yl)-2-(1-methylpiperidin-4-yl)oxazole-4-carboxamide [1274];
2-(1-isopropylpiperidin-4-yl)-N-(7-(1-methyl-1H-1,2,3-triazol-4-yl)quinazolin-2-yl)oxazole-4-carboxamide [1275];
2-fluoro-N-(7-(1-methyl-1H-1,2,3-triazol-4-yl)quinazolin-2-yl)benzamide [1276];
N-(7-(1-methyl-1H-1,2,3-triazol-4-yl)quinazolin-2-yl)-3-((1-methylpiperidin-4-yl)oxy)benzamide [1277];
$N^2$-methyl-$N^5$-(7-(1-methyl-1H-1,2,3-triazol-4-yl)quinazolin-2-yl)pyridine-2,5-dicarboxamide [1278];
N-(7-(1-methyl-1H-1,2,3-triazol-4-yl)quinazolin-2-yl)-6-(4-methylpiperazin-1-yl)nicotinamide [1279];
2-(3-(dimethylamino)azetidin-1-yl)-N-(7-(1-methyl-1H-1,2,3-triazol-4-yl)quinazolin-2-yl) isonicotinamide [1280];
N-(7-(1-methyl-1H-1,2,3-triazol-4-yl)quinazolin-2-yl)-2-(1-methylpiperidin-4-yl)isonicotinamide [1281];
2-(4-(dimethylamino)piperidin-1-yl)-N-(7-(1-methyl-1H-1,2,3-triazol-4-yl)quinazolin-2-yl) isonicotinamide [1282];
N-(7-(1-methyl-1H-1,2,3-triazol-4-yl)quinazolin-2-yl)-2-morpholinoisonicotinamide [1283];
N-(7-(1-methyl-1H-1,2,3-triazol-4-yl)quinazolin-2-yl)-2-(4-methylpiperazin-1-yl)isonicotinamide [1284];
2-(4-methyl-1,4-diazepan-1-yl)-N-(7-(1-methyl-1H-1,2,3-triazol-4-yl)quinazolin-2-yl) isonicotinamide [1285];
2-(4-isopropylpiperazin-1-yl)-N-(7-(1-methyl-1H-1,2,3-triazol-4-yl)quinazolin-2-yl) isonicotinamide [1286];
N-(7-(1-methyl-1H-1,2,3-triazol-4-yl)quinazolin-2-yl)-2-(piperidin-4-ylamino)isonicotinamide [1287];
2-(methyl(1-methylpiperidin-4-yl)amino)-N-(7-(1-methyl-1H-1,2,3-triazol-4-yl)quinazolin-2-yl) isonicotinamide [1288];
N-(7-(1-methyl-1H-1,2,3-triazol-4-yl)quinazolin-2-yl)-2-((1-methylpiperidin-4-yl)thio) isonicotinamide [1289];
2-methyl-N-(7-(1-methyl-1H-1,2,3-triazol-4-yl)quinazolin-2-yl)-1,2,3,4-tetrahydroisoquinoline-6-carboxamide [1290];
N-(7-(1-methyl-1H-1,2,3-triazol-4-yl)quinazolin-2-yl)-2-(piperazin-1-yl)isonicotinamide [1291];
N-(7-(1-methyl-1H-1,2,3-triazol-4-yl)quinazolin-2-yl)-2-(2-(4-methylpiperazin-1-yl)pyridin-4-yl) acetamide [1292];
1,1-bis(methyl-$d_3$)-4-(4-((7-(1-methyl-1H-1,2,3-triazol-4-yl)quinazolin-2-yl)carbamoyl)pyridin-2-yl)piperazin-1-ium [1293];
N-(7-(1-methyl-1H-1,2,3-triazol-4-yl)quinazolin-2-yl)-2-(4-(methyl-$d_3$)piperazin-1-yl) isonicotinamide [1294];
N-(7-(1-methyl-1H-1,2,3-triazol-5-yl)quinazolin-2-yl)-1-(3,3,3-trifluoropropyl)piperidine-4-carboxamide [1295];
N-(7-(4-methyl-4H-1,2,4-triazol-3-yl)quinazolin-2-yl)-2-morpholinoacetamide [1296];
N-(7-(4-methyl-4H-1,2,4-triazol-3-yl)quinazolin-2-yl)-1-(3,3,3-trifluoropropyl)piperidine-4-carboxamide [1297];
4-fluoro-1-isobutyl-N-(7-(4-methyl-4H-1,2,4-triazol-3-yl)quinazolin-2-yl)piperidine-4-carboxamide [1298];
N-(7-(4,5-dimethyl-4H-1,2,4-triazol-3-yl)quinazolin-2-yl)-2-morpholinoacetamide [1299];
N-(7-(4,5-dimethyl-4H-1,2,4-triazol-3-yl)quinazolin-2-yl)-1-(3,3,3-trifluoropropyl)piperidine-4-carboxamide [1300];
N-(7-(1H-1,2,3-triazol-1-yl)quinazolin-2-yl)-4-fluoro-1-isobutylpiperidine-4-carboxamide [1301];
N-(7-(2H-1,2,3-triazol-2-yl)quinazolin-2-yl)-4-fluoro-1-isobutylpiperidine-4-carboxamide [1302];
N-(7-(1H-1,2,4-triazol-1-yl)quinazolin-2-yl)-2-(4-methylpiperazin-1-yl)isonicotinamide [1303];
1-isobutyl-N-(7-(1-methyl-1H-tetrazol-5-yl)quinazolin-2-yl)piperidine-4-carboxamide [1304];
2,2,3,3-tetramethyl-N-(7-(1-methyl-1H-imidazol-5-yl)quinazolin-2-yl)cyclopropane-1-carboxamide [1305];
4,4-difluoro-N-(7-(1-methyl-1H-imidazol-5-yl)quinazolin-2-yl)cyclohexane-1-carboxamide [1306];
N-(7-(1-methyl-1H-imidazol-5-yl)quinazolin-2-yl)-2-(piperidin-1-yl)acetamide [1307];
2-fluoro-2-methyl-N-(7-(1-methyl-1H-imidazol-5-yl)quinazolin-2-yl)propanamide [1308];
1-fluoro-N-(7-(1-methyl-1H-imidazol-5-yl)quinazolin-2-yl)cyclopropane-1-carboxamide [1309];
2-methyl-N-(7-(1-methyl-1H-imidazol-5-yl)quinazolin-2-yl)-2-azaspiro[3.3]heptane-6-carboxamide [1310];
1-fluoro-N-(7-(1-methyl-1H-imidazol-5-yl)quinazolin-2-yl)cyclohexane-1-carboxamide [1311];
trans-4-methoxy-N-(7-(1-methyl-1H-imidazol-5-yl)quinazolin-2-yl)cyclohexane-1-carboxamide [1312];
trans-4-(hydroxymethyl)-N-(7-(1-methyl-1H-imidazol-5-yl)quinazolin-2-yl)cyclohexane-1-carboxamide [1313];
N-(7-(1-methyl-1H-imidazol-5-yl)quinazolin-2-yl)azetidine-3-carboxamide [1314];
(R)—N-(7-(1-methyl-1H-imidazol-5-yl)quinazolin-2-yl) tetrahydrofuran-2-carboxamide [1315];
1-(2-methoxyethyl)-N-(7-(1-methyl-1H-imidazol-5-yl)quinazolin-2-yl)piperidine-4-carboxamide [1316];
N-(7-(1-methyl-1H-imidazol-5-yl)quinazolin-2-yl)-1-(3,3,3-trifluoropropyl)piperidine-4-carboxamide [1317];
1-isobutyl-N-(7-(1-methyl-1H-imidazol-5-yl)quinazolin-2-yl)piperidine-4-carboxamide [1318];
N-(7-(1-methyl-1H-imidazol-5-yl)quinazolin-2-yl)-1-(methylsulfonyl)piperidine-4-carboxamide [1319];
N-(7-(1-methyl-1H-imidazol-5-yl)quinazolin-2-yl)-2-(pyrrolidin-1-yl)propanamide [1320];
2-isopropoxy-N-(7-(1-methyl-1H-imidazol-5-yl)quinazolin-2-yl)acetamide [1321];
3-isopropoxy-N-(7-(1-methyl-1H-imidazol-5-yl)quinazolin-2-yl)propanamide [1322];
N-(7-(1,2-dimethyl-1H-imidazol-5-yl)quinazolin-2-yl) cyclopropanecarboxamide [1323];
N-(7-(1,2-dimethyl-1H-imidazol-5-yl)quinazolin-2-yl) cyclohexanecarboxamide [1324];
N-(7-(1,2-dimethyl-1H-imidazol-5-yl)quinazolin-2-yl)-4,4-difluorocyclohexane-1-carboxamide [1325];
(S)—N-(7-(1,2-dimethyl-1H-imidazol-5-yl)quinazolin-2-yl)tetrahydrofuran-2-carboxamide [1326];
N-(7-(1,2-dimethyl-1H-imidazol-5-yl)quinazolin-2-yl)-3,3-difluorocyclobutane-1-carboxamide [1327];
N-(7-(1,2-dimethyl-1H-imidazol-5-yl)quinazolin-2-yl)-1-fluorocyclopropane-1-carboxamide [1328];
N-(7-(1,2-dimethyl-1H-imidazol-5-yl)quinazolin-2-yl) morpholine-4-carboxamide [1329];
N-(7-(1,2-dimethyl-1H-imidazol-5-yl)quinazolin-2-yl) morpholine-$d_8$-4-carboxamide [1330];
1-methyl-N-(7-(1-methyl-1H-imidazol-5-yl)quinazolin-2-yl)-1H-pyrazole-4-carboxamide [1331];

1-ethyl-N-(7-(1-methyl-1H-imidazol-5-yl)quinazolin-2-yl)-1H-pyrazole-4-carboxamide [1332];
1-isopropyl-N-(7-(1-methyl-1H-imidazol-5-yl)quinazolin-2-yl)-1H-pyrazole-4-carboxamide [1333];
1-cyclopropyl-N-(7-(1-methyl-1H-imidazol-5-yl)quinazolin-2-yl)-1H-pyrazole-4-carboxamide [1334];
1-isobutyl-N-(7-(1-methyl-1H-imidazol-5-yl)quinazolin-2-yl)-1H-pyrazole-4-carboxamide [1335];
1-methyl-N-(7-(1-methyl-1H-imidazol-5-yl)quinazolin-2-yl)-1H-pyrazole-3-carboxamide [1336];
N-(7-(1-methyl-1H-imidazol-5-yl)quinazolin-2-yl)-2-(1-methyl-1H-pyrazol-4-yl)acetamide [1337];
1-methyl-N-(7-(1-methyl-1H-imidazol-5-yl)quinazolin-2-yl)-1H-imidazole-4-carboxamide [1338];
1-isopropyl-N-(7-(1-methyl-1H-imidazol-5-yl)quinazolin-2-yl)-1H-imidazole-4-carboxamide [1339];
N-(7-(1-methyl-1H-imidazol-5-yl)quinazolin-2-yl)-1-(tetrahydro-2H-pyran-4-yl)-1H-imidazole-4-carboxamide [1340];
1,2-dimethyl-N-(7-(1-methyl-1H-imidazol-5-yl)quinazolin-2-yl)-1H-imidazole-5-carboxamide [1341];
1-methyl-N-(7-(1-methyl-1H-imidazol-5-yl)quinazolin-2-yl)-1H-1,2,4-triazole-3-carboxamide [1342];
2-methyl-N-(7-(1-methyl-1H-imidazol-5-yl)quinazolin-2-yl)oxazole-4-carboxamide [1343];
2-isopropyl-N-(7-(1-methyl-1H-imidazol-5-yl)quinazolin-2-yl)oxazole-4-carboxamide [1344];
4-methyl-N-(7-(1-methyl-1H-imidazol-5-yl)quinazolin-2-yl)oxazole-2-carboxamide [1345];
4-methyl-N-(7-(1-methyl-1H-imidazol-5-yl)quinazolin-2-yl)thiazole-2-carboxamide [1346];
2-methyl-N-(7-(1-methyl-1H-imidazol-5-yl)quinazolin-2-yl)thiazole-4-carboxamide [1347];
5-methyl-N-(7-(1-methyl-1H-imidazol-5-yl)quinazolin-2-yl)-1,3,4-oxadiazole-2-carboxamide [1348];
5-methyl-N-(7-(1-methyl-1H-imidazol-5-yl)quinazolin-2-yl)-1,3,4-thiadiazole-2-carboxamide [1349];
1-isopropyl-N-(7-(1-isopropyl-1H-imidazol-5-yl)quinazolin-2-yl)-1H-pyrazole-4-carboxamide [1350];
N-(7-(1,2-dimethyl-1H-imidazol-5-yl)quinazolin-2-yl)-1-methyl-1H-pyrazole-4-carboxamide [1351];
N-(7-(1,2-dimethyl-1H-imidazol-5-yl)quinazolin-2-yl)-1-isopropyl-1H-pyrazole-4-carboxamide [1352];
N-(7-(1,2-dimethyl-1H-imidazol-5-yl)quinazolin-2-yl)-2-methylthiazole-5-carboxamide [1353];
4-fluoro-N-(7-(1-methyl-1H-imidazol-5-yl)quinazolin-2-yl)benzamide [1354];
4-(difluoromethoxy)-N-(7-(1-methyl-1H-imidazol-5-yl)quinazolin-2-yl)benzamide [1355];
N-(7-(1-methyl-1H-imidazol-5-yl)quinazolin-2-yl)-3-(pyrrolidin-1-ylmethyl)benzamide [1356];
2-fluoro-N-(7-(1-methyl-1H-imidazol-5-yl)quinazolin-2-yl)benzamide-3,4,5,6-d$_4$ [1357];
4-fluoro-N-(7-(1-methyl-1H-imidazol-5-yl)quinazolin-2-yl)benzamide-2,3,5,6-d$_4$ [1358];
2-chloro-N-(7-(1-methyl-1H-imidazol-5-yl)quinazolin-2-yl)benzamide-3,4,5,6-d$_4$ [1359];
4-chloro-N-(7-(1-methyl-1H-imidazol-5-yl)quinazolin-2-yl)benzamide-2,3,5,6-d$_4$ [1360];
4-(methyl-d$_3$)—N-(7-(1-methyl-1H-imidazol-5-yl)quinazolin-2-yl)benzamide [1361];
4-methyl-N-(7-(1-methyl-1H-imidazol-5-yl)quinazolin-2-yl)benzamide-2,3,5,6-d$_4$ [1362];
4-(methyl-d$_3$)—N-(7-(1-methyl-1H-imidazol-5-yl)quinazolin-2-yl)benzamide-2,3,5,6-d$_4$ [1363];
4-(methoxy-d$_3$)—N-(7-(1-methyl-1H-imidazol-5-yl)quinazolin-2-yl)benzamide [1364];
4-(methoxy-d$_3$)—N-(7-(1-methyl-1H-imidazol-5-yl)quinazolin-2-yl)benzamide-2,3,5,6-d$_4$ [1365];
4-methoxy-N-(7-(1-methyl-1H-imidazol-5-yl)quinazolin-2-yl)benzamide-2,3,5,6-d$_4$ [1366];
(E)-N-(7-(1,2-dimethyl-1H-imidazol-5-yl)quinazolin-2-yl)-3-(phenyl-2,3,4,5,6-d$_5$)acrylamide [1367];
(E)-N-(7-(1,2-dimethyl-1H-imidazol-5-yl)quinazolin-2-yl)-3-(phenyl-2,3,4,5,6-d$_5$)acrylamide-2,3-d$_2$ [1368];
N-(7-(1,2-dimethyl-1H-imidazol-5-yl)quinazolin-2-yl)-2-(4-fluorophenyl)acetamide-2,2-d$_2$ [1369];
(E)-N-(7-(1-methyl-1H-imidazol-5-yl)quinazolin-2-yl)-3-(phenyl-2,3,4,5,6-d$_5$)acrylamide [1370];
(E)-N-(7-(1-methyl-1H-imidazol-5-yl)quinazolin-2-yl)-3-(phenyl-2,3,4,5,6-d$_5$)acrylamide-2,3-d$_2$ [1371];
2-(4-fluorophenyl)-N-(7-(1-methyl-1H-imidazol-5-yl)quinazolin-2-yl)acetamide-2,2-d$_2$ [1372];
N-(7-(1-methyl-1H-imidazol-5-yl)quinazolin-2-yl)-2-(4-methylpiperazin-1-yl)isonicotinamide [1373];
2-(dimethylamino)-N-(7-(1-methyl-1H-imidazol-5-yl)quinazolin-2-yl)isonicotinamide [1374];
2-(3-aminoazetidin-1-yl)-N-(7-(1-methyl-1H-imidazol-5-yl)quinazolin-2-yl)isonicotinamide [1375];
N-(7-(1-methyl-1H-imidazol-5-yl)quinazolin-2-yl)-2-(pyrrolidin-1-yl)isonicotinamide [1376];
N-(7-(1-methyl-1H-imidazol-5-yl)quinazolin-2-yl)-2-(piperidin-1-yl)isonicotinamide [1377];
N-(7-(1-methyl-1H-imidazol-5-yl)quinazolin-2-yl)-2-morpholinoisonicotinamide [1378];
2-(4-isopropylpiperazin-1-yl)-N-(7-(1-methyl-1H-imidazol-5-yl)quinazolin-2-yl)isonicotinamide [1379];
2-(4-cyclopropylpiperazin-1-yl)-N-(7-(1-methyl-1H-imidazol-5-yl)quinazolin-2-yl) isonicotinamide [1380];
N-(7-(1-methyl-1H-imidazol-5-yl)quinazolin-2-yl)-2-(2,7-diazaspiro[3.5]nonan-2-yl) isonicotinamide [1381];
N-(7-(1-methyl-1H-imidazol-5-yl)quinazolin-2-yl)-2-(7-methyl-2,7-diazaspiro[3.5]nonan-2-yl) isonicotinamide [1382];
N-(7-(1-methyl-1H-imidazol-5-yl)quinazolin-2-yl)isoindoline-5-carboxamide [1383];
2-methyl-N-(7-(1-methyl-1H-imidazol-5-yl)quinazolin-2-yl)isoindoline-5-carboxamide [1384];
2-(azetidin-1-yl)-N-(7-(1-methyl-1H-imidazol-5-yl)quinazolin-2-yl)isonicotinamide [1385];
2-methoxy-N-(7-(1-methyl-1H-imidazol-5-yl)quinazolin-2-yl)isonicotinamide [1386];
2-methyl-N-(7-(1-methyl-1H-imidazol-5-yl)quinazolin-2-yl)isonicotinamide [1387];
2-cyano-N-(7-(1-methyl-1H-imidazol-5-yl)quinazolin-2-yl)isonicotinamide [1388];
2-(3,3-difluoroazetidin-1-yl)-N-(7-(1-methyl-1H-imidazol-5-yl)quinazolin-2-yl)isonicotinamide [1389];
2-(4,4-difluoropiperidin-1-yl)-N-(7-(1-methyl-1H-imidazol-5-yl)quinazolin-2-yl)isonicotinamide [1390];
2-isopropoxy-N-(7-(1-methyl-1H-imidazol-5-yl)quinazolin-2-yl)isonicotinamide [1391];
N-(7-(1-methyl-1H-imidazol-5-yl)quinazolin-2-yl)-2-(pyrrolidin-1-yl-2,2,5,5-d$_4$)isonicotinamide [1392];
N-(7-(1-methyl-1H-imidazol-5-yl)quinazolin-2-yl)-2-(pyrrolidin-1-yl-d$_8$)isonicotinamide [1393];
N-(7-(1-methyl-1H-imidazol-5-yl)quinazolin-2-yl)-2-(piperidin-1-yl-d$_{10}$)isonicotinamide [1394];
N-(7-(1-methyl-1H-imidazol-5-yl)quinazolin-2-yl)-2-(morpholino-d$_8$)isonicotinamide [1395];
N-(7-(1,2-dimethyl-1H-imidazol-5-yl)quinazolin-2-yl)-4-isopropoxybenzamide [1396];
N-(7-(1,2-dimethyl-1H-imidazol-5-yl)quinazolin-2-yl)-4-(piperidin-4-yloxy)benzamide [1397];

4-(benzyloxy)-N-(7-(1,2-dimethyl-1H-imidazol-5-yl)quinazolin-2-yl)benzamide [1398];
N-(7-(1,2-dimethyl-1H-imidazol-5-yl)quinazolin-2-yl)-2-fluorobenzamide-3,4,5,6-d$_4$ [1399];
N-(7-(1,2-dimethyl-1H-imidazol-5-yl)quinazolin-2-yl)-4-fluorobenzamide-2,3,5,6-d$_4$ [1400];
2-chloro-N-(7-(1,2-dimethyl-1H-imidazol-5-yl)quinazolin-2-yl)benzamide-3,4,5,6-d$_4$ [1401];
4-chloro-N-(7-(1,2-dimethyl-1H-imidazol-5-yl)quinazolin-2-yl)benzamide-2,3,5,6-d$_4$ [1402];
N-(7-(1,2-dimethyl-1H-imidazol-5-yl)quinazolin-2-yl)-4-(methyl-d$_3$)benzamide [1403];
N-(7-(1,2-dimethyl-1H-imidazol-5-yl)quinazolin-2-yl)-4-methylbenzamide-2,3,5,6-d$_4$ [1404];
N-(7-(1,2-dimethyl-1H-imidazol-5-yl)quinazolin-2-yl)-4-(methyl-d$_3$)benzamide-2,3,5,6-d$_4$ [1405];
N-(7-(1,2-dimethyl-1H-imidazol-5-yl)quinazolin-2-yl)-4-(methoxy-d$_3$)benzamide [1406];
N-(7-(1,2-dimethyl-1H-imidazol-5-yl)quinazolin-2-yl)-4-(methoxy-d$_3$)benzamide-2,3,5,6-d$_4$ [1407];
N-(7-(1,2-dimethyl-1H-imidazol-5-yl)quinazolin-2-yl)-4-methoxybenzamide-2,3,5,6-d$_4$ [1408];
N-(7-(1,2-dimethyl-1H-imidazol-5-yl)quinazolin-2-yl)-2-(4-methylpiperazin-1-yl) isonicotinamide [1409];
N-(7-(1,2-dimethyl-1H-imidazol-5-yl)quinazolin-2-yl)-2-morpholinoisonicotinamide [1410];
N-(7-(1,2-dimethyl-1H-imidazol-5-yl)quinazolin-2-yl)-2-(pyrrolidin-1-yl)isonicotinamide [1411];
N-(7-(1,2-dimethyl-1H-imidazol-5-yl)quinazolin-2-yl)-2-(dimethylamino)isonicotinamide [1412];
N-(7-(1,2-dimethyl-1H-imidazol-5-yl)quinazolin-2-yl)-2-(pyrrolidin-1-yl-2,2,5,5-d$_4$) isonicotinamide [1413];
N-(7-(1,2-dimethyl-1H-imidazol-5-yl)quinazolin-2-yl)-2-(pyrrolidin-1-yl-d$_8$)isonicotinamide [1414];
N-(7-(1,2-dimethyl-1H-imidazol-5-yl)quinazolin-2-yl)-2-(piperidin-1-yl-d$_{10}$)isonicotinamide [1415];
N-(7-(1,2-dimethyl-1H-imidazol-5-yl)quinazolin-2-yl)-2-(morpholino-d$_8$)isonicotinamide [1416];
N-(7-(5,6,7,8-tetrahydroimidazo[1,2-a]pyrazin-3-yl)quinazolin-2-yl)cyclopropanecarboxamide [1417];
N-(7-(7-methyl-5,6,7,8-tetrahydroimidazo[1,2-a]pyrazin-3-yl)quinazolin-2-yl) cyclopropanecarboxamide [1418];
3,3-difluoro-N-(7-(5,6,7,8-tetrahydroimidazo[1,2-a]pyrazin-3-yl)quinazolin-2-yl)cyclobutane-1-carboxamide [1419];
(R)—N-(7-(5,6,7,8-tetrahydroimidazo[1,2-a]pyrazin-3-yl)quinazolin-2-yl)pyrrolidine-2-carboxamide [1420];
(R)—N-(7-(5,6,7,8-tetrahydroimidazo[1,2-a]pyrazin-3-yl)quinazolin-2-yl)piperidine-3-carboxamide [1421];
1-methyl-N-(7-(5,6,7,8-tetrahydroimidazo[1,2-a]pyrazin-3-yl)quinazolin-2-yl)piperidine-4-carboxamide [1422];
N-(7-(5,6,7,8-tetrahydroimidazo[1,2-a]pyrazin-3-yl)quinazolin-2-yl)-1-((1-(trifluoromethyl) cyclopropyl) methyl)piperidine-4-carboxamide [1423];
1-benzoyl-N-(7-(5,6,7,8-tetrahydroimidazo[1,2-a]pyrazin-3-yl)quinazolin-2-yl)piperidine-4-carboxamide [1424];
4-fluoro-1-isobutyl-N-(7-(5,6,7,8-tetrahydroimidazo[1,2-a]pyrazin-3-yl)quinazolin-2-yl) piperidine-4-carboxamide [1425];
(R)-2-(2-methylpyrrolidin-1-yl)-N-(7-(5,6,7,8-tetrahydroimidazo[1,2-a]pyrazin-3-yl)quinazolin-2-yl)acetamide [1426];
2-(cyclobutyl(methyl)amino)-N-(7-(5,6,7,8-tetrahydroimidazo[1,2-a]pyrazin-3-yl)quinazolin-2-yl)acetamide [1427];
4-fluoro-N-(7-(5,6,7,8-tetrahydroimidazo[1,2-a]pyrazin-3-yl)quinazolin-2-yl)benzamide [1428];
4-isopropoxy-N-(7-(5,6,7,8-tetrahydroimidazo[1,2-a]pyrazin-3-yl)quinazolin-2-yl)benzamide [1429];
4-(difluoromethoxy)-N-(7-(5,6,7,8-tetrahydroimidazo[1,2-a]pyrazin-3-yl)quinazolin-2-yl) benzamide [1430];
2-((2-(dimethylamino)ethyl)amino)-N-(7-(5,6,7,8-tetrahydroimidazo[1,2-a]pyrazin-3-yl) quinazolin-2-yl) isonicotinamide [1431];
2-((1-isopropylpiperidin-4-yl)oxy)-N-(7-(5,6,7,8-tetrahydroimidazo[1,2-a]pyrazin-3-yl) quinazolin-2-yl)isonicotinamide [1432];
N-(7-(oxazol-5-yl)quinazolin-2-yl)-1-(3,3,3-trifluoropropyl)piperidine-4-carboxamide [1433];
N-(7-(oxazol-5-yl)quinazolin-2-yl)cyclopropanecarboxamide [1434];
(R)—N-(7-(oxazol-5-yl)quinazolin-2-yl)tetrahydrofuran-2-carboxamide [1435];
(R)—N-(7-(oxazol-5-yl)quinazolin-2-yl)piperidine-3-carboxamide [1436];
N-(7-(oxazol-5-yl)quinazolin-2-yl)tetrahydro-2H-pyran-4-carboxamide [1437];
N-(7-(oxazol-5-yl)quinazolin-2-yl)-1-(2-(pyrrolidin-1-yl)acetyl)piperidine-4-carboxamide [1438];
1'-methyl-N-(7-(oxazol-5-yl)quinazolin-2-yl)-[1,4'-bipiperidine]-4-carboxamide [1439];
cis-4-morpholino-N-(7-(oxazol-5-yl)quinazolin-2-yl)cyclohexane-1-carboxamide [1440];
2-(cyclobutyl(methyl)amino)-N-(7-(oxazol-5-yl)quinazolin-2-yl)acetamide [1441];
N-(7-(oxazol-5-yl)quinazolin-2-yl)-2-(pyrrolidin-1-yl)acetamide [1442];
(R)-2-(2-methylpyrrolidin-1-yl)-N-(7-(oxazol-5-yl)quinazolin-2-yl)acetamide [1443];
2-(4-methylpiperazin-1-yl)-N-(7-(oxazol-5-yl)quinazolin-2-yl)acetamide [1444];
trans-4-((4-methylpiperazin-1-yl)methyl)-N-(7-(oxazol-5-yl)quinazolin-2-yl)cyclohexane-1-carboxamide [1445];
1-(2,2-difluoropropyl)-N-(7-(oxazol-5-yl)quinazolin-2-yl)piperidine-4-carboxamide [1446];
trans-4-(hydroxymethyl)-N-(7-(2-methyloxazol-5-yl)quinazolin-2-yl)cyclohexane-1-carboxamide [1447];
trans-4-(methylamino)-N-(7-(2-methyloxazol-5-yl)quinazolin-2-yl)cyclohexane-1-carboxamide [1448];
trans-4-((1,3-difluoropropan-2-yl)amino)-N-(7-(2-methyloxazol-5-yl)quinazolin-2-yl) cyclohexane-1-carboxamide [1449];
trans-N-(7-(2-methyloxazol-5-yl)quinazolin-2-yl)-4-((propan-2-yl-1,1,1,3,3,3-d$_6$)amino) cyclohexane-1-carboxamide [1450];
trans-4-((2,2-difluoroethyl)amino)-N-(7-(2-methyloxazol-5-yl)quinazolin-2-yl)cyclohexane-1-carboxamide [1451];
trans-N-(7-(2-methyloxazol-5-yl)quinazolin-2-yl)-4-((3,3,3-trifluoropropyl)amino)cyclohexane-1-carboxamide [1452];
trans-4-((2-methoxyethyl)amino)-N-(7-(2-methyloxazol-5-yl)quinazolin-2-yl)cyclohexane-1-carboxamide [1453];
trans-4-(dimethylamino)-N-(7-(2-methyloxazol-5-yl)quinazolin-2-yl)cyclohexane-1-carboxamide [1454];
trans-4-(bis(methyl-d$_3$)amino)-N-(7-(2-methyloxazol-5-yl)quinazolin-2-yl)cyclohexane-1-carboxamide [1455];
cis-4-(dimethylamino)-N-(7-(2-methyloxazol-5-yl)quinazolin-2-yl)cyclohexane-1-carboxamide [1456];

trans-4-((2,2-difluoroethyl)(methyl)amino)-N-(7-(2-methyloxazol-5-yl)quinazolin-2-yl) cyclohexane-1-carboxamide [1457];
trans-4-(methyl(oxetan-3-yl)amino)-N-(7-(2-methyloxazol-5-yl)quinazolin-2-yl)cyclohexane-1-carboxamide [1458];
trans-4-((2-fluoroethyl)amino)-N-(7-(2-methyloxazol-5-yl)quinazolin-2-yl)cyclohexane-1-carboxamide [1459];
trans-4-(2-(fluoromethyl)aziridin-1-yl)-N-(7-(2-methyloxazol-5-yl)quinazolin-2-yl)cyclohexane-1-carboxamide [1460];
trans-4-((3-fluoroazetidin-1-yl)methyl)-N-(7-(2-methyloxazol-5-yl)quinazolin-2-yl)cyclohexane-1-carboxamide [1461];
trans-N-(7-(2-methyloxazol-5-yl)quinazolin-2-yl)-3-morpholinocyclobutane-1-carboxamide [1462];
trans-N-(7-(2-methyloxazol-5-yl)quinazolin-2-yl)-4-morpholinocyclohexane-1-carboxamide [1463];
N-(7-(2-methyloxazol-5-yl)quinazolin-2-yl)-2-(piperidin-1-yl)acetamide [1464];
2-(4-methoxypiperidin-1-yl)-N-(7-(2-methyloxazol-5-yl)quinazolin-2-yl)acetamide [1465];
N-(7-(2-methyloxazol-5-yl)quinazolin-2-yl)-2-(4-methylpiperazin-1-yl)acetamide [1466];
N-(7-(2-methyloxazol-5-yl)quinazolin-2-yl)morpholine-4-carboxamide [1467];
N-(7-(2-methyloxazol-5-yl)quinazolin-2-yl)-2-morpholinoacetamide [1468];
N-(7-(2-methyloxazol-5-yl)quinazolin-2-yl)-3-morpholinopropanamide [1469];
1-methyl-N-(7-(2-methyloxazol-5-yl)quinazolin-2-yl)piperidine-4-carboxamide [1470];
1-(2,2-difluoropropyl)-N-(7-(2-methyloxazol-5-yl)quinazolin-2-yl)piperidine-4-carboxamide [1471];
N-(7-(2-methyloxazol-5-yl)quinazolin-2-yl)-4-morpholinopiperidine-1-carboxamide [1472];
4-(((1,3-difluoropropan-2-yl)amino)-N-(7-(2-methyloxazol-5-yl)quinazolin-2-yl)piperidine-1-carboxamide [1473];
(1R,3s,5S)-3-((1,3-difluoropropan-2-yl)amino)-N-(7-(2-methyloxazol-5-yl)quinazolin-2-yl)-8-azabicyclo [3.2.1]octane-8-carboxamide [1474];
(1R,3s,5S)-3-((1,3-difluoropropan-2-yl)amino)-N-(7-(2-methyloxazol-5-yl)quinazolin-2-yl)-8-azabicyclo [3.2.1]octane-8-carboxamide [1475];
4-(dimethylamino)-N-(7-(2-methyloxazol-5-yl)quinazolin-2-yl)piperidine-1-carboxamide [1476];
4-((2,2-difluoroethyl)(methyl)amino)-N-(7-(2-methyloxazol-5-yl)quinazolin-2-yl)piperidine-1-carboxamide [1477];
(3S,4S)-4-amino-3-fluoro-N-(7-(2-methyloxazol-5-yl)quinazolin-2-yl)piperidine-1-carboxamide [1478];
(3S,4S)-3-fluoro-4-(methylamino)-N-(7-(2-methyloxazol-5-yl)quinazolin-2-yl)piperidine-1-carboxamide [1479];
(3R,4R)-4-amino-3-fluoro-N-(7-(2-methyloxazol-5-yl)quinazolin-2-yl)piperidine-1-carboxamide [1480];
(3R,4R)-3-fluoro-4-(methylamino)-N-(7-(2-methyloxazol-5-yl)quinazolin-2-yl)piperidine-1-carboxamide [1481];
4-((2-fluoroethyl)amino)-N-(7-(2-methyloxazol-5-yl)quinazolin-2-yl)piperidine-1-carboxamide [1482];
4-((2,2-difluoroethyl)amino)-N-(7-(2-methyloxazol-5-yl)quinazolin-2-yl)piperidine-1-carboxamide [1483];
(1R,3s,5S)-3-amino-N-(7-(2-methyloxazol-5-yl)quinazolin-2-yl)-8-azabicyclo [3.2.1]octane-8-carboxamide [1484];
(1R,3r,5S)-3-amino-N-(7-(2-methyloxazol-5-yl)quinazolin-2-yl)-8-azabicyclo [3.2.1]octane-8-carboxamide [1485];
(1R,3r,5S)-3-((2-fluoroethyl)amino)-N-(7-(2-methyloxazol-5-yl)quinazolin-2-yl)-8-azabicyclo [3.2.1]octane-8-carboxamide [1486];
(1R,3r,5S)-3-((2,2-difluoroethyl)amino)-N-(7-(2-methyloxazol-5-yl)quinazolin-2-yl)-8-azabicyclo[3.2.1]octane-8-carboxamide [1487];
(1R,3s,5S)—N-(7-(2-methyloxazol-5-yl)quinazolin-2-yl)-3-((3,3,3-trifluoropropyl)amino)-8-azabicyclo [3.2.1]octane-8-carboxamide [1488];
(3S,4S)-3-fluoro-4-(isopropylamino)-N-(7-(2-methyloxazol-5-yl)quinazolin-2-yl)piperidine-1-carboxamide [1489];
N-(7-(2-methyloxazol-5-yl)quinazolin-2-yl)-5,6-dihydroimidazo[1,2-a]pyrazine-7(8H)-carboxamide [1490];
2-methyl-N-(7-(2-methyloxazol-5-yl)quinazolin-2-yl)-5,6-dihydroimidazo[1,2-a]pyrazine-7(8H)-carboxamide [1491];
N-(7-(2-methyloxazol-5-yl)quinazolin-2-yl)-2-(morpholino-$d_8$)acetamide [1492];
trans-N-(7-(2-methyloxazol-4-yl)quinazolin-2-yl)-4-(4-methylpiperazin-1-yl)cyclohexane-1-carboxamide [1493];
N-(7-(2-methyloxazol-5-yl)quinazolin-2-yl)-1-(1-methylpiperidin-4-yl)-1H-pyrazole-4-carboxamide [1494];
2-(1H-imidazol-1-yl)-N-(7-(2-methyloxazol-5-yl)quinazolin-2-yl)acetamide [1495];
4-(difluoromethoxy)-N-(7-(oxazol-5-yl)quinazolin-2-yl)benzamide [1496];
3-((1-methylpiperidin-4-yl)oxy)-N-(7-(oxazol-5-yl)quinazolin-2-yl)benzamide [1497];
N-(7-(oxazol-5-yl)quinazolin-2-yl)isonicotinamide [1498];
2-(3-aminoazetidin-1-yl)-N-(7-(oxazol-5-yl)quinazolin-2-yl)isonicotinamide [1499];
2-(1-methylpiperidin-4-yl)-N-(7-(oxazol-5-yl)quinazolin-2-yl)isonicotinamide [1500];
1'-methyl-N-(7-(oxazol-5-yl)quinazolin-2-yl)-1',2',3',6'-tetrahydro-[2,4'-bipyridine]-4-carboxamide [1501];
2-(4-methylpiperazin-1-yl)-N-(7-(oxazol-5-yl)quinazolin-2-yl)isonicotinamide [1502];
2-(7-methyl-2,7-diazaspiro[3.5]nonan-2-yl)-N-(7-(oxazol-5-yl)quinazolin-2-yl)isonicotinamide [1503];
N-(7-(oxazol-5-yl)quinazolin-2-yl)-2-(2,7-diazaspiro[3.5]nonan-7-yl)isonicotinamide [1504];
N-(7-(oxazol-5-yl)quinazolin-2-yl)-2-(piperidin-4-ylamino)isonicotinamide [1505];
2-methyl-N-(7-(oxazol-5-yl)quinazolin-2-yl)isoindoline-5-carboxamide [1506];
N-(7-(oxazol-5-yl)quinazolin-2-yl)-1,2,3,4-tetrahydroisoquinoline-7-carboxamide [1507];
N-(7-(2-methyloxazol-5-yl)quinazolin-2-yl)-2-(4-methylpiperazin-1-yl)isonicotinamide [1508];
N-(7-(3-methylisoxazol-5-yl)quinazolin-2-yl)-1-(3,3,3-trifluoropropyl)piperidine-4-carboxamide [1509];
4-fluoro-1-isobutyl-N-(7-(5-methyl-1,3,4-oxadiazol-2-yl)quinazolin-2-yl)piperidine-4-carboxamide [1510];
1-isobutyl-N-(7-(5-methyl-1,3,4-oxadiazol-2-yl)quinazolin-2-yl)piperidine-4-carboxamide [1511];
N-(7-(5-(dimethylamino)-1,3,4-oxadiazol-2-yl)quinazolin-2-yl)piperidine-4-carboxamide [1512];

N-(7-(5-(dimethylamino)-1,3,4-oxadiazol-2-yl)quinazo-lin-2-yl)-1-methylpiperidine-4-carboxamide [1513];

N-(7-(5-methyl-1,3,4-oxadiazol-2-yl)quinazolin-2-yl)-2-(4-methylpiperazin-1-yl)isonicotinamide [1514];

3,3-difluoro-N-(7-(thiazol-5-yl)quinazolin-2-yl)cyclobu-tane-1-carboxamide [1515];

2-methyl-N-(7-(thiazol-5-yl)quinazolin-2-yl)-2-azaspiro [3.3]heptane-6-carboxamide [1516];

1-fluoro-N-(7-(thiazol-5-yl)quinazolin-2-yl)cyclohexane-1-carboxamide [1517];

trans-4-(dimethylamino)-N-(7-(thiazol-5-yl)quinazolin-2-yl)cyclohexane-1-carboxamide [1518];

trans-4-((3-fluoroazetidin-1-yl)methyl)-N-(7-(thiazol-5-yl)quinazolin-2-yl)cyclohexane-1-carboxamide [1519];

N-(7-(thiazol-5-yl)quinazolin-2-yl)azetidine-3-carbox-amide [1520];

1-methyl-N-(7-(thiazol-5-yl)quinazolin-2-yl)piperidine-4-carboxamide [1521];

1-(2,2-difluoropropyl)-N-(7-(thiazol-5-yl)quinazolin-2-yl)piperidine-4-carboxamide [1522];

1-(oxetan-3-yl)-N-(7-(thiazol-5-yl)quinazolin-2-yl)pip-eridine-4-carboxamide [1523];

1-(2-(pyrrolidin-1-yl)acetyl)-N-(7-(thiazol-5-yl)quinazo-lin-2-yl)piperidine-4-carboxamide [1524];

1'-methyl-N-(7-(thiazol-5-yl)quinazolin-2-yl)-[1,4'-bipip-eridine]-4-carboxamide [1525];

2-(pyrrolidin-1-yl)-N-(7-(thiazol-5-yl)quinazolin-2-yl) propanamide [1526];

2-(piperidin-1-yl)-N-(7-(thiazol-5-yl)quinazolin-2-yl)ac-etamide [1527];

2-(4-methylpiperazin-1-yl)-N-(7-(thiazol-5-yl)quinazo-lin-2-yl)acetamide [1528];

2-morpholino-N-(7-(thiazol-5-yl)quinazolin-2-yl)acet-amide [1529];

4-(piperidin-4-yloxy)-N-(7-(thiazol-5-yl)quinazolin-2-yl) benzamide [1530];

N-(7-(thiazol-5-yl)quinazolin-2-yl)isonicotinamide [1531];

6-(4-methylpiperazin-1-yl)-N-(7-(thiazol-5-yl)quinazo-lin-2-yl)nicotinamide [1532];

1'-methyl-N-(7-(thiazol-5-yl)quinazolin-2-yl)-1',2',3',6'-tetrahydro-[2,4'-bipyridine]-4-carboxamide [1533];

2-(3-(dimethylamino)azetidin-1-yl)-N-(7-(thiazol-5-yl) quinazolin-2-yl)isonicotinamide [1534];

2-(4-(dimethylamino)piperidin-1-yl)-N-(7-(thiazol-5-yl) quinazolin-2-yl)isonicotinamide [1535];

2-(4-methylpiperazin-1-yl)-N-(7-(thiazol-5-yl)quinazo-lin-2-yl)isonicotinamide [1536];

2-((1-methylpiperidin-4-yl)thio)-N-(7-(thiazol-5-yl)qui-nazolin-2-yl)isonicotinamide [1537];

N-(7-(thiazol-5-yl)quinazolin-2-yl)-1,2,3,4-tetrahy-droisoquinoline-7-carboxamide [1538];

trans-4-((1,3-difluoropropan-2-yl)amino)-N-(7-(5-methyl-1,3,4-thiadiazol-2-yl)quinazolin-2-yl) cyclo-hexane-1-carboxamide [1539];

N-(7-(2-methylthiazol-5-yl)quinazolin-2-yl)morpholine-4-carboxamide [1540];

N-(7-(2-methylthiazol-5-yl)quinazolin-2-yl)-2-(pyrroli-din-1-yl)acetamide [1541];

2-((1R,4R)-2-oxa-5-azabicyclo[2.2.1]heptan-5-yl)-N-(7-(2-methylthiazol-5-yl)quinazolin-2-yl) acetamide [1542];

N-(7-(2-methylthiazol-5-yl)quinazolin-2-yl)-2-mor-pholinoacetamide [1543];

N-(7-(2-methylthiazol-5-yl)quinazolin-2-yl)-2-(mor-pholino-$d_8$)acetamide [1544];

2-(4-methylpiperazin-1-yl)-N-(7-(2-methylthiazol-5-yl) quinazolin-2-yl)acetamide [1545];

1-methyl-N-(7-(2-methylthiazol-5-yl)quinazolin-2-yl)pi-peridine-4-carboxamide [1546];

N-(7-(2-methylthiazol-5-yl)quinazolin-2-yl)isonicotina-mide [1547];

N-(7-(2-methylthiazol-5-yl)quinazolin-2-yl)nicotinamide [1548];

2-(4-methylpiperazin-1-yl)-N-(7-(2-methylthiazol-5-yl) quinazolin-2-yl)isonicotinamide [1549];

trans-N-(7-(5-methyl-1,3,4-thiadiazol-2-yl)quinazolin-2-yl)-4-morpholinocyclohexane-1-carboxamide [1550];

trans-N-(7-(5-methyl-1,3,4-thiadiazol-2-yl)quinazolin-2-yl)-4-(4-methylpiperazin-1-yl) cyclohexane-1-carbox-amide [1551];

4-isopropyl-N-(7-(5-methyl-1,3,4-thiadiazol-2-yl)qui-nazolin-2-yl)piperazine-1-carboxamide [1552];

4-((2-methoxyethyl)(methyl)amino)-N-(7-(5-methyl-1,3, 4-thiadiazol-2-yl)quinazolin-2-yl) piperidine-1-car-boxamide [1553];

4-((1,3-difluoropropan-2-yl)amino)-N-(7-(5-methyl-1,3, 4-thiadiazol-2-yl)quinazolin-2-yl) piperidine-1-car-boxamide [1554];

N-(7-(5-methyl-1,3,4-thiadiazol-2-yl)quinazolin-2-yl)-4-((3,3,3-trifluoropropyl)amino)piperidine-1-carboxam-ide [1555];

4-((2-fluoroethyl)amino)-N-(7-(5-methyl-1,3,4-thiadi-azol-2-yl)quinazolin-2-yl)piperidine-1-carboxamide [1556];

(3R,4S)-4-amino-3-fluoro-N-(7-(5-methyl-1,3,4-thiadi-azol-2-yl)quinazolin-2-yl)piperidine-1-carboxamide [1557];

(3R,4R)-4-amino-3-fluoro-N-(7-(5-methyl-1,3,4-thiadi-azol-2-yl)quinazolin-2-yl)piperidine-1-carboxamide [1558];

(3S,4S)-3-fluoro-N-(7-(5-methyl-1,3,4-thiadiazol-2-yl) quinazolin-2-yl)-4-(methylamino) piperidine-1-car-boxamide [1559];

(3R,4R)-3-fluoro-N-(7-(5-methyl-1,3,4-thiadiazol-2-yl) quinazolin-2-yl)-4-(methylamino) piperidine-1-car-boxamide [1560];

4-amino-3,3-difluoro-N-(7-(5-methyl-1,3,4-thiadiazol-2-yl)quinazolin-2-yl)piperidine-1-carboxamide [1561];

(3R,4R)-3-fluoro-4-(isopropylamino)-N-(7-(5-methyl-1, 3,4-thiadiazol-2-yl)quinazolin-2-yl) piperidine-1-car-boxamide [1562];

(3R,4S)-3-fluoro-4-(isopropylamino)-N-(7-(5-methyl-1, 3,4-thiadiazol-2-yl)quinazolin-2-yl) piperidine-1-car-boxamide [1563];

3,3-difluoro-4-(isopropylamino)-N-(7-(5-methyl-1,3,4-thiadiazol-2-yl)quinazolin-2-yl)piperidine-1-carbox-amide [1564];

(3S,4S)-3-fluoro-N-(7-(5-methyl-1,3,4-thiadiazol-2-yl) quinazolin-2-yl)-4-((propan-2-yl-1,1,1,3,3,3-$d_6$) amino)piperidine-1-carboxamide [1565];

(1R,3s,5S)-3-((1,3-difluoropropan-2-yl)amino)-N-(7-(5-methyl-1,3,4-thiadiazol-2-yl)quinazolin-2-yl)-8-azabi-cyclo[3.2.1]octane-8-carboxamide [1566];

(1R,3s,5S)-3-((1,3-difluoropropan-2-yl)amino)-N-(7-(5-methyl-1,3,4-thiadiazol-2-yl)quinazolin-2-yl)-8-azabi-cyclo[3.2.1]octane-8-carboxamide [1567];

4-(dimethylamino)-N-(7-(2-methylthiazol-5-yl)quinazo-lin-2-yl)piperidine-1-carboxamide [1568];

4-((2,2-difluoroethyl)amino)-N-(7-(5-methyl-1,3,4-thia-diazol-2-yl)quinazolin-2-yl)piperidine-1-carboxamide [1569];

4-((2,2-difluoroethyl)(methyl-d$_3$)amino)-N-(7-(5-methyl-1,3,4-thiadiazol-2-yl)quinazolin-2-yl) piperidine-1-carboxamide [1570];

N-(7-(5-methyl-1,3,4-thiadiazol-2-yl)quinazolin-2-yl)-4-morpholinopiperidine-1-carboxamide [1571];

N-(7-(5-methyl-1,3,4-thiadiazol-2-yl)quinazolin-2-yl)-4-(4-methylpiperazin-1-yl)piperidine-1-carboxamide [1572];

(R)-3,4-dimethyl-N-(7-(5-methyl-1,3,4-thiadiazol-2-yl)quinazolin-2-yl)piperazine-1-carboxamide [1573];

(S)-3,4-dimethyl-N-(7-(5-methyl-1,3,4-thiadiazol-2-yl)quinazolin-2-yl)piperazine-1-carboxamide [1574];

(1R,3r,5 S)-3-((2-fluoroethyl)amino)-N-(7-(5-methyl-1,3,4-thiadiazol-2-yl)quinazolin-2-yl)-8-azabicyclo[3.2.1]octane-8-carboxamide [1575];

(1R,3r,5S)-3-((2,2-difluoroethyl)amino)-N-(7-(5-methyl-1,3,4-thiadiazol-2-yl)quinazolin-2-yl)-8-azabicyclo[3.2.1]octane-8-carboxamide [1576];

(1R,3r,5S)-3-amino-N-(7-(5-methyl-1,3,4-thiadiazol-2-yl)quinazolin-2-yl)-8-azabicyclo[3.2.1] octane-8-carboxamide [1577];

(1S,4S)-5-methyl-N-(7-(5-methyl-1,3,4-thiadiazol-2-yl)quinazolin-2-yl)-2,5-diazabicyclo[2.2.1]heptane-2-carboxamide [1578];

(1R,4R)-5-methyl-N-(7-(5-methyl-1,3,4-thiadiazol-2-yl)quinazolin-2-yl)-2,5-diazabicyclo[2.2.1] heptane-2-carboxamide [1579];

8-methyl-N-(7-(5-methyl-1,3,4-thiadiazol-2-yl)quinazolin-2-yl)-3,8-diazabicyclo[3.2.1]octane-3-carboxamide [1580];

3-methyl-N-(7-(5-methyl-1,3,4-thiadiazol-2-yl)quinazolin-2-yl)-3,8-diazabicyclo[3.2.1]octane-8-carboxamide [1581];

N-(7-(5-methyl-1,3,4-thiadiazol-2-yl)quinazolin-2-yl)-5,6-dihydroimidazo[1,2-a]pyrazine-7(8H)-carboxamide [1582];

2-(4-methylpiperazin-1-yl)-N-(7-(5-methylthiazol-2-yl)quinazolin-2-yl)isonicotinamide [1583];

2-(4-methylpiperazin-1-yl)-N-(7-(4-methylthiazol-2-yl)quinazolin-2-yl)isonicotinamide [1584];

N-(7-(2-(methylamino)thiazol-5-yl)quinazolin-2-yl)piperidine-4-carboxamide [1585];

1-methyl-N-(7-(2-(methylamino)thiazol-5-yl)quinazolin-2-yl)piperidine-4-carboxamide [1586];

N-(7-(2-(diethylamino)thiazol-5-yl)quinazolin-2-yl)-2-(4-fluoropiperidin-1-yl)acetamide [1587];

N-(7-(2-(diethylamino)thiazol-5-yl)quinazolin-2-yl)-2-(4-methylpiperazin-1-yl)acetamide [1588];

N-(7-(2-aminothiazol-5-yl)quinazolin-2-yl)-2-(4-methylpiperazin-1-yl)isonicotinamide [1589];

N-(7-(2-(methylamino)thiazol-5-yl)quinazolin-2-yl)-2-(4-methylpiperazin-1-yl)isonicotinamide [1590];

N-(7-(2-(dimethylamino)thiazol-5-yl)quinazolin-2-yl)-2-(4-methylpiperazin-1-yl)isonicotinamide [1591];

2-(4-isopropylpiperazin-1-yl)-N-(7-(2-(methylamino)thiazol-5-yl)quinazolin-2-yl) isonicotinamide [1592];

2-(3-(dimethylamino)azetidin-1-yl)-N-(7-(2-(methylamino)thiazol-5-yl)quinazolin-2-yl) isonicotinamide [1593];

2-(3-(dimethylamino)azetidin-1-yl)-N-(7-(2-(dimethylamino)thiazol-5-yl)quinazolin-2-yl) isonicotinamide [1594];

2-(3-aminoazetidin-1-yl)-N-(7-(2-(dimethylamino)thiazol-5-yl)quinazolin-2-yl)isonicotinamide [1595];

N-(7-(5-chlorothiazol-2-yl)quinazolin-2-yl)-2-(4-methylpiperazin-1-yl)isonicotinamide [1596];

2-(2-(2-(4-methylpiperazin-1-yl)isonicotinamido)quinazolin-7-yl)thiazole-5-carboxamide [1597];

N-(7-(isothiazol-4-yl)quinazolin-2-yl)-1-methylpiperidine-4-carboxamide [1598];

N-(7-(1,3,4-thiadiazol-2-yl)quinazolin-2-yl)-4-(difluoromethoxy)benzamide [1599];

N-(7-(1,3,4-thiadiazol-2-yl)quinazolin-2-yl)-4-(piperidin-4-yloxy)benzamide [1600];

N-(7-(1,3,4-thiadiazol-2-yl)quinazolin-2-yl)-4-((1-methylpiperidin-4-yl)oxy)benzamide [1601];

N-(7-(1,3,4-thiadiazol-2-yl)quinazolin-2-yl)-3-((1-methylpiperidin-4-yl)oxy)benzamide [1602];

$N^5$-(7-(1,3,4-thiadiazol-2-yl)quinazolin-2-yl)-$N^2$-methylpyridine-2,5-dicarboxamide [1603];

N-(7-(1,3,4-thiadiazol-2-yl)quinazolin-2-yl)-6-(4-methylpiperazin-1-yl)nicotinamide [1604];

N-(7-(1,3,4-thiadiazol-2-yl)quinazolin-2-yl)-1'-methyl-1',2',3',6'-tetrahydro-[2,4'-bipyridine]-4-carboxamide [1605];

N-(7-(1,3,4-thiadiazol-2-yl)quinazolin-2-yl)-2-(3-(dimethylamino)azetidin-1-yl)isonicotinamide [1606];

N-(7-(1,3,4-thiadiazol-2-yl)quinazolin-2-yl)-2-(4-methylpiperazin-1-yl)isonicotinamide [1607];

N-(7-(1,3,4-thiadiazol-2-yl)quinazolin-2-yl)-2-(4-isopropylpiperazin-1-yl)isonicotinamide [1608];

N-(7-(1,3,4-thiadiazol-2-yl)quinazolin-2-yl)-2-morpholinoisonicotinamide [1609];

1-fluoro-N-(7-(5-methyl-1,3,4-thiadiazol-2-yl)quinazolin-2-yl)cyclohexane-1-carboxamide [1610];

trans-4-methoxy-N-(7-(5-methyl-1,3,4-thiadiazol-2-yl)quinazolin-2-yl)cyclohexane-1-carboxamide [1611];

cis-4-methoxy-N-(7-(5-methyl-1,3,4-thiadiazol-2-yl)quinazolin-2-yl)cyclohexane-1-carboxamide [1612];

trans-4-amino-N-(7-(5-methyl-1,3,4-thiadiazol-2-yl)quinazolin-2-yl)cyclohexane-1-carboxamide [1613];

trans-4-(dimethylamino)-N-(7-(5-methyl-1,3,4-thiadiazol-2-yl)quinazolin-2-yl)cyclohexane-1-carboxamide [1614];

trans-N-(7-(5-methyl-1,3,4-thiadiazol-2-yl)quinazolin-2-yl)-4-morpholinocyclohexane-1-carboxamide [1615];

trans-4-(hydroxymethyl)-N-(7-(5-methyl-1,3,4-thiadiazol-2-yl)quinazolin-2-yl)cyclohexane-1-carboxamide [1616];

N-(7-(5-methyl-1,3,4-thiadiazol-2-yl)quinazolin-2-yl)piperidine-4-carboxamide [1617];

4-fluoro-N-(7-(5-methyl-1,3,4-thiadiazol-2-yl)quinazolin-2-yl)piperidine-4-carboxamide [1618];

1-methyl-N-(7-(5-methyl-1,3,4-thiadiazol-2-yl)quinazolin-2-yl)piperidine-4-carboxamide [1619];

4-fluoro-1-methyl-N-(7-(5-methyl-1,3,4-thiadiazol-2-yl)quinazolin-2-yl)piperidine-4-carboxamide [1620];

1-(2-fluoroethyl)-N-(7-(5-methyl-1,3,4-thiadiazol-2-yl)quinazolin-2-yl)piperidine-4-carboxamide [1621];

1-(2,2-difluoroethyl)-N-(7-(5-methyl-1,3,4-thiadiazol-2-yl)quinazolin-2-yl)piperidine-4-carboxamide [1622];

N-(7-(5-methyl-1,3,4-thiadiazol-2-yl)quinazolin-2-yl)-1-(3,3,3-trifluoropropyl)piperidine-4-carboxamide [1623];

1-(2,2-difluoropropyl)-N-(7-(5-methyl-1,3,4-thiadiazol-2-yl)quinazolin-2-yl)piperidine-4-carboxamide [1624];

1-benzoyl-N-(7-(5-methyl-1,3,4-thiadiazol-2-yl)quinazolin-2-yl)piperidine-4-carboxamide [1625];

N-(7-(5-methyl-1,3,4-thiadiazol-2-yl)quinazolin-2-yl)-2-(pyrrolidin-1-yl)acetamide [1626];

N-(7-(5-methyl-1,3,4-thiadiazol-2-yl)quinazolin-2-yl)-2-(piperidin-1-yl)acetamide [1627];

2-(4-methoxypiperidin-1-yl)-N-(7-(5-methyl-1,3,4-thiadiazol-2-yl)quinazolin-2-yl)acetamide [1628];

N-(7-(5-methyl-1,3,4-thiadiazol-2-yl)quinazolin-2-yl)-2-(4-methylpiperazin-1-yl)acetamide [1629];

N-(7-(5-methyl-1,3,4-thiadiazol-2-yl)quinazolin-2-yl)-2-morpholinoacetamide [1630];

(R)—N-(7-(5-methyl-1,3,4-thiadiazol-2-yl)quinazolin-2-yl)-2-(3-methylmorpholino)acetamide [1631];

2-(7-azabicyclo[2.2.1]heptan-7-yl)-N-(7-(5-methyl-1,3,4-thiadiazol-2-yl)quinazolin-2-yl) acetamide [1632];

2-((1R,4R)-2-oxa-5-azabicyclo[2.2.1]heptan-5-yl)-N-(7-(5-methyl-1,3,4-thiadiazol-2-yl) quinazolin-2-yl)acetamide [1633];

2-(3-oxa-8-azabicyclo[3.2.1]octan-8-yl)-N-(7-(5-methyl-1,3,4-thiadiazol-2-yl)quinazolin-2-yl) acetamide [1634];

2-(8-oxa-3-azabicyclo[3.2.1]octan-3-yl)-N-(7-(5-methyl-1,3,4-thiadiazol-2-yl)quinazolin-2-yl) acetamide [1635];

N-(7-(5-methyl-1,3,4-thiadiazol-2-yl)quinazolin-2-yl)-2-(1,4-oxazepan-4-yl)acetamide [1636];

N-(7-(5-methyl-1,3,4-thiadiazol-2-yl)quinazolin-2-yl)-2-morpholinoacetamide-2,2-$d_2$ [1637];

N-(7-(5-methyl-1,3,4-thiadiazol-2-yl)quinazolin-2-yl)-2-(morpholino-$d_8$)acetamide [1638];

1-methyl-3-(7-(5-methyl-1,3,4-thiadiazol-2-yl)quinazolin-2-yl)-1-(1-methylpiperidin-4-yl)urea [1639];

(3S,4S)-4-amino-3-fluoro-N-(7-(5-methyl-1,3,4-thiadiazol-2-yl)quinazolin-2-yl)piperidine-1-carboxamide [1640];

(3S,4S)-4-(dimethylamino)-3-fluoro-N-(7-(5-methyl-1,3,4-thiadiazol-2-yl)quinazolin-2-yl) piperidine-1-carboxamide [1641];

N-(7-(5-methyl-1,3,4-thiadiazol-2-yl)quinazolin-2-yl) morpholine-4-carboxamide [1642];

N-(7-(5-methyl-1,3,4-thiadiazol-2-yl)quinazolin-2-yl)-4-(methylamino)piperidine-1-carboxamide [1643];

4-(dimethylamino)-N-(7-(5-methyl-1,3,4-thiadiazol-2-yl)quinazolin-2-yl)piperidine-1-carboxamide [1644];

4-((2,2-difluoroethyl)(methyl)amino)-N-(7-(5-methyl-1,3,4-thiadiazol-2-yl)quinazolin-2-yl) piperidine-1-carboxamide [1645];

(3S,4S)-3-fluoro-4-(isopropylamino)-N-(7-(5-methyl-1,3,4-thiadiazol-2-yl)quinazolin-2-yl) piperidine-1-carboxamide [1646];

2-methyl-N-(7-(5-methyl-1,3,4-thiadiazol-2-yl)quinazolin-2-yl)-5,6-dihydroimidazo[1,2-a] pyrazine-7(8H)-carboxamide [1647];

4-methyl-N-(7-(5-methyl-1,3,4-thiadiazol-2-yl)quinazolin-2-yl)piperazine-1-carboxamide [1648];

N-(7-(5-methyl-1,3,4-thiadiazol-2-yl)quinazolin-2-yl)-1-(1-methylpiperidin-4-yl)-1H-pyrazole-4-carboxamide [1649];

1-(1-isopropylpiperidin-4-yl)-N-(7-(5-methyl-1,3,4-thiadiazol-2-yl)quinazolin-2-yl)-1H-pyrazole-4-carboxamide [1650];

N-(7-(5-methyl-1,3,4-thiadiazol-2-yl)quinazolin-2-yl)-1-(1-methylpiperidin-4-yl)-1H-1,2,3-triazole-4-carboxamide [1651];

N-(7-(5-methyl-1,3,4-thiadiazol-2-yl)quinazolin-2-yl)-2-(piperidin-4-yl)oxazole-4-carboxamide [1652];

N-(7-(5-methyl-1,3,4-thiadiazol-2-yl)quinazolin-2-yl)-2-(1-methylpiperidin-4-yl)oxazole-4-carboxamide [1653];

2-(3-(dimethylamino)azetidin-1-yl)-N-(7-(5-methyl-1,3,4-thiadiazol-2-yl)quinazolin-2-yl) isonicotinamide [1654];

1'-methyl-N-(7-(5-methyl-1,3,4-thiadiazol-2-yl)quinazolin-2-yl)-1',2',3',6'-tetrahydro-[2,4'-bipyridine]-4-carboxamide [1655];

N-(7-(5-methyl-1,3,4-thiadiazol-2-yl)quinazolin-2-yl)-2-(4-methylpiperazin-1-yl)isonicotinamide [1656];

2-(methyl(1-methylpiperidin-4-yl)amino)-N-(7-(5-methyl-1,3,4-thiadiazol-2-yl)quinazolin-2-yl) isonicotinamide [1657];

2-(azetidin-3-yloxy)-N-(7-(5-methyl-1,3,4-thiadiazol-2-yl)quinazolin-2-yl)isonicotinamide [1658];

N-(7-(5-methyl-1,3,4-thiadiazol-2-yl)quinazolin-2-yl)-3-((1-methylpiperidin-4-yl)oxy)benzamide [1659];

N-(7-(5-methyl-1,3,4-thiadiazol-2-yl)quinazolin-2-yl)-2-((1-methylpiperidin-4-yl)thio) isonicotinamide [1660];

6-(4-methylpiperazin-1-yl)-N-(7-(5-(trifluoromethyl)-1,3,4-thiadiazol-2-yl)quinazolin-2-yl) nicotinamide [1661];

2-(4-methylpiperazin-1-yl)-N-(7-(5-(trifluoromethyl)-1,3,4-thiadiazol-2-yl)quinazolin-2-yl) isonicotinamide [1662];

N-(7-(5-amino-1,3,4-thiadiazol-2-yl)quinazolin-2-yl)-2-(4-methylpiperazin-1-yl)isonicotinamide [1663];

N-(7-(5-(dimethylamino)-1,3,4-thiadiazol-2-yl)quinazolin-2-yl)-2-(4-methylpiperazin-1-yl) isonicotinamide [1664];

N-(7-(3-amino-5-fluorophenyl)quinazolin-2-yl)-2-(4-methylpiperazin-1-yl)isonicotinamide [1665];

N-(7-(3-fluoro-5-(isopropylamino)phenyl)quinazolin-2-yl)-2-(4-methylpiperazin-1-yl) isonicotinamide [1666];

1-methyl-N-(7-(pyridin-2-yl)quinazolin-2-yl)piperidine-4-carboxamide [1667];

2-(4-methylpiperazin-1-yl)-N-(7-(pyridin-2-yl)quinazolin-2-yl)isonicotinamide [1668];

2-(4-methylpiperazin-1-yl)-N-(7-(pyridin-4-yl)quinazolin-2-yl)isonicotinamide [1669];

N-(7-(pyridin-3-yl)quinazolin-2-yl)cyclopropanecarboxamide [1670];

N-(7-(pyridin-3-yl)quinazolin-2-yl)-2-(pyrrolidin-1-yl)acetamide [1671];

1-methyl-N-(7-(pyridin-3-yl)quinazolin-2-yl)piperidine-4-carboxamide [1672];

N-(7-(pyridin-3-yl)quinazolin-2-yl)quinuclidine-4-carboxamide [1673];

2-morpholino-N-(7-(pyridin-3-yl)quinazolin-2-yl)acetamide [1674];

2-(morpholino-$d_8$)—N-(7-(pyridin-3-yl)quinazolin-2-yl) acetamide [1675];

2-(4-methylpiperazin-1-yl)-N-(7-(pyridin-3-yl)quinazolin-2-yl)acetamide [1676];

2-(4-methyl-1,4-diazepan-1-yl)-N-(7-(pyridin-3-yl)quinazolin-2-yl)acetamide [1677];

2-(4-methylpiperazin-1-yl)-N-(7-(pyridin-3-yl)quinazolin-2-yl)isonicotinamide [1678];

2-(2-methyl-1H-imidazol-1-yl)-N-(7-(pyridin-3-yl)quinazolin-2-yl)acetamide [1679];

2-(1H-imidazol-1-yl)-N-(7-(pyridin-3-yl)quinazolin-2-yl)acetamide [1680];

2-(piperidin-4-yl)-N-(7-(pyridin-3-yl)quinazolin-2-yl)oxazole-4-carboxamide [1681];

2-(1-methylpiperidin-4-yl)-N-(7-(pyridin-3-yl)quinazolin-2-yl)oxazole-4-carboxamide [1682];

2-(1-isopropylpiperidin-4-yl)-N-(7-(pyridin-3-yl)quinazolin-2-yl)oxazole-4-carboxamide [1683];

trans-N-(7-(5-fluoropyridin-3-yl)quinazolin-2-yl)-3-morpholinocyclobutane-1-carboxamide [1684];

trans-N-(7-(5-fluoropyridin-3-yl)quinazolin-2-yl)-4-((4-methylpiperazin-1-yl)methyl) cyclohexane-1-carboxamide [1685];
N-(7-(5-fluoropyridin-3-yl)quinazolin-2-yl)-2-(pyrrolidin-1-yl)acetamide [1686];
N-(7-(5-fluoropyridin-3-yl)quinazolin-2-yl)-1-methylpiperidine-4-carboxamide [1687];
N-(7-(5-fluoropyridin-3-yl)quinazolin-2-yl)-2-(4-methylpiperazin-1-yl)acetamide [1688];
N-(7-(6-fluoropyridin-3-yl)quinazolin-2-yl)-2-(4-methylpiperazin-1-yl)acetamide [1689];
N-(7-(5-fluoropyridin-3-yl)quinazolin-2-yl)-2-morpholinoacetamide [1690];
N-(7-(5-fluoropyridin-3-yl)quinazolin-2-yl)-3-morpholinopropanamide [1691];
N-(7-(5-fluoropyridin-3-yl)quinazolin-2-yl)-2-(4-methylpiperazin-1-yl)isonicotinamide [1692];
N-(7-(5-fluoropyridin-3-yl)quinazolin-2-yl)-2-(piperidin-4-yl)oxazole-4-carboxamide [1693];
N-(7-(5-fluoropyridin-3-yl)quinazolin-2-yl)-2-(1-methylpiperidin-4-yl)oxazole-4-carboxamide [1694];
N-(7-(5-fluoropyridin-3-yl)quinazolin-2-yl)-2-(1-isopropylpiperidin-4-yl)oxazole-4-carboxamide [1695];
N-(7-(5-chloropyridin-3-yl)quinazolin-2-yl)-2-(4-methylpiperazin-1-yl)isonicotinamide [1696];
N-(7-(5-methylpyridin-3-yl)quinazolin-2-yl)-2-morpholinoacetamide [1697];
N-(7-(5-(difluoromethyl)pyridin-3-yl)quinazolin-2-yl)-3-(piperidin-4-yl)benzamide [1698];
N-(7-(5-(difluoromethyl)pyridin-3-yl)quinazolin-2-yl)-3-(1-methylpiperidin-4-yl)benzamide [1699];
N-(7-(5-(difluoromethyl)pyridin-3-yl)quinazolin-2-yl)-2-(4-methylpiperazin-1-yl)isonicotinamide [1700];
2-(4-methylpiperazin-1-yl)-N-(7-(5-(trifluoromethyl)pyridin-3-yl)quinazolin-2-yl)acetamide [1701];
2-(4-methylpiperazin-1-yl)-N-(7-(6-(trifluoromethyl)pyridin-3-yl)quinazolin-2-yl)acetamide [1702];
N-(7-(5-(hydroxymethyl)pyridin-3-yl)quinazolin-2-yl)-1-methylpiperidine-4-carboxamide [1703];
N-(7-(5-cyanopyridin-3-yl)quinazolin-2-yl)-1-methylpiperidine-4-carboxamide [1704];
N-(7-(5-methoxypyridin-3-yl)quinazolin-2-yl)-1-methylpiperidine-4-carboxamide [1705];
N-(7-(5-methoxypyridin-3-yl)quinazolin-2-yl)-2-morpholinoacetamide [1706];
N-(7-(5-methoxypyridin-3-yl)quinazolin-2-yl)-2-(4-methylpiperazin-1-yl)isonicotinamide [1707];
4-fluoro-N-(7-(5-(piperidin-4-yloxy)pyridin-3-yl)quinazolin-2-yl)benzamide [1708];
N-(7-(5-aminopyridin-3-yl)quinazolin-2-yl)-4-fluorobenzamide [1709];
N-(7-(5-aminopyridin-3-yl)quinazolin-2-yl)-4-(piperidin-4-yloxy)benzamide [1710];
N-(7-(5-aminopyridin-3-yl)quinazolin-2-yl)-2-(4-methylpiperazin-1-yl)isonicotinamide [1711];
N-(7-(5-aminopyridin-3-yl)quinazolin-2-yl)-2-(piperidin-4-yl)oxazole-4-carboxamide [1712];
N-(7-(6-aminopyridin-3-yl)quinazolin-2-yl)-2-(4-methylpiperazin-1-yl)isonicotinamide [1713];
N-(7-(6-(methylamino)pyridin-3-yl)quinazolin-2-yl)-2-(4-methylpiperazin-1-yl)isonicotinamide [1714];
N-(7-(5-(isopropylamino)pyridin-3-yl)quinazolin-2-yl)-3-(piperidin-4-yl)benzamide [1715];
N-(7-(5-(isopropylamino)pyridin-3-yl)quinazolin-2-yl)-3-(1-methylpiperidin-4-yl)benzamide [1716];
N-(7-(5-(isopropylamino)pyridin-3-yl)quinazolin-2-yl)-2-(4-methylpiperazin-1l-yl) isonicotinamide [1717];
N-(7-(5-(piperidin-4-ylamino)pyridin-3-yl)quinazolin-2-yl)cyclohexanecarboxamide [1718];
4-fluoro-N-(7-(5-(piperidin-4-ylamino)pyridin-3-yl)quinazolin-2-yl)benzamide [1719];
4-fluoro-N-(7-(5-((1-methylpiperidin-4-yl)amino)pyridin-3-yl)quinazolin-2-yl)benzamide [1720];
N-(7-(5-acetamidopyridin-3-yl)quinazolin-2-yl)-1-methylpiperidine-4-carboxamide [1721];
N-(7-(5-(dimethylamino)pyridin-3-yl)quinazolin-2-yl)-2-(4-methylpiperazin-1-yl)isonicotinamide [1722];
N-(7-(6-(dimethylamino)pyridin-3-yl)quinazolin-2-yl)-2-(4-methylpiperazin-1-yl)isonicotinamide [1723];
1-methyl-N-(7-(5-(pyrrolidin-1-yl)pyridin-3-yl)quinazolin-2-yl)piperidine-4-carboxamide [1724];
N-(7-(5-(pyrrolidin-1-ylmethyl)pyridin-3-yl)quinazolin-2-yl)cyclopropanecarboxamide [1725];
4-fluoro-N-(7-(5-(pyrrolidin-1-ylmethyl)pyridin-3-yl)quinazolin-2-yl)benzamide [1726];
N-(7-(5-((4-hydroxypiperidin-1-yl)methyl)pyridin-3-yl)quinazolin-2-yl) cyclopropanecarboxamide [1727];
4-fluoro-N-(7-(5-((4-hydroxypiperidin-1-yl)methyl)pyridin-3-yl)quinazolin-2-yl)benzamide [1728];
N-(7-(5-(piperazin-1-ylmethyl)pyridin-3-yl)quinazolin-2-yl)cyclopropanecarboxamide [1729];
N-(7-(5-((4-methylpiperazin-1-yl)methyl)pyridin-3-yl)quinazolin-2-yl)cyclopropanecarboxamide [1730];
N-(7-(5-(morpholinomethyl)pyridin-3-yl)quinazolin-2-yl)cyclopropanecarboxamide [1731];
N-methyl-5-(2-(1-methylpiperidine-4-carboxamido)quinazolin-7-yl)nicotinamide [1732];
N-methyl-5-(2-(2-(4-methylpiperazin-1-yl)isonicotinamido)quinazolin-7-yl)nicotinamide [1733];
N-(7-(pyridin-3-yl-$d_4$)quinazolin-2-yl)-2-(pyrrolidin-1-yl)acetamide [1734];
2-(4-methylpiperazin-1-yl)-N-(7-(pyridin-3-yl-$d_4$)quinazolin-2-yl)acetamide [1735];
2-morpholino-N-(7-(pyridin-3-yl-$d_4$)quinazolin-2-yl)acetamide [1736];
1-methyl-N-(7-(2-methylpyrimidin-5-yl)quinazolin-2-yl)piperidine-4-carboxamide [1737];
2-(4-methylpiperazin-1-yl)-N-(7-(2-methylpyrimidin-5-yl)quinazolin-2-yl)isonicotinamide [1738];
N-(7-(2-aminopyrimidin-5-yl)quinazolin-2-yl)-1-methylpiperidine-4-carboxamide [1739];
2-morpholino-N-(7-(pyridazin-3-yl)quinazolin-2-yl)acetamide [1740];
2-morpholino-N-(7-(pyridazin-4-yl)quinazolin-2-yl)acetamide [1741];
N-(7-(pyridazin-4-yl)quinazolin-2-yl)-2-(pyrrolidin-1-yl)acetamide [1742];
trans-3-morpholino-N-(7-(pyrazin-2-yl)quinazolin-2-yl)cyclobutane-1-carboxamide [1743];
trans-4-(dimethylamino)-N-(7-(pyrazin-2-yl)quinazolin-2-yl)cyclohexane-1-carboxamide [1744];
trans-4-morpholino-N-(7-(pyrazin-2-yl)quinazolin-2-yl)cyclohexane-1-carboxamide [1745];
trans-4-((3-fluoroazetidin-1-yl)methyl)-N-(7-(pyrazin-2-yl)quinazolin-2-yl)cyclohexane-1-carboxamide [1746];
trans-4-((4-methylpiperazin-1-yl)methyl)-N-(7-(pyrazin-2-yl)quinazolin-2-yl)cyclohexane-1-carboxamide [1747];
N-(7-(pyrazin-2-yl)quinazolin-2-yl)-2-(pyrrolidin-1-yl)acetamide [1748];
1-methyl-N-(7-(pyrazin-2-yl)quinazolin-2-yl)piperidine-4-carboxamide [1749];

4-fluoro-1-methyl-N-(7-(pyrazin-2-yl)quinazolin-2-yl)piperidine-4-carboxamide [1750];
1-(2-fluoroethyl)-N-(7-(pyrazin-2-yl)quinazolin-2-yl)piperidine-4-carboxamide [1751];
1-(oxetan-3-yl)-N-(7-(pyrazin-2-yl)quinazolin-2-yl)piperidine-4-carboxamide [1752];
2-morpholino-N-(7-(pyrazin-2-yl)quinazolin-2-yl)acetamide [1753];
1-methyl-N-(7-(pyrazin-2-yl)quinazolin-2-yl)azepane-4-carboxamide [1754];
1-isobutyl-N-(7-(pyrazin-2-yl)quinazolin-2-yl)azepane-4-carboxamide [1755];
1-(2-hydroxy-2-methylpropyl)-N-(7-(pyrazin-2-yl)quinazolin-2-yl)azepane-4-carboxamide [1756];
4-(morpholinomethyl)-N-(7-(pyrazin-2-yl)quinazolin-2-yl)benzamide [1757];
2-(4-methylpiperazin-1-yl)-N-(7-(pyrazin-2-yl)quinazolin-2-yl)isonicotinamide [1758];
N-(7-(6-(methylamino)pyrazin-2-yl)quinazolin-2-yl)-2-(4-methylpiperazin-1-yl)isonicotinamide [1759];
N-(7-(6-(isopropylamino)pyrazin-2-yl)quinazolin-2-yl)azetidine-3-carboxamide [1760];
N-(7-(6-(isopropylamino)pyrazin-2-yl)quinazolin-2-yl)piperidine-4-carboxamide [1761];
N-(7-(6-(isopropylamino)pyrazin-2-yl)quinazolin-2-yl)-1-methylpiperidine-4-carboxamide [1762];
1-(2-fluoroethyl)-N-(7-(6-(isopropylamino)pyrazin-2-yl)quinazolin-2-yl)piperidine-4-carboxamide [1763];
1-isopropyl-N-(7-(6-(isopropylamino)pyrazin-2-yl)quinazolin-2-yl)piperidine-4-carboxamide [1764];
1-isopentyl-N-(7-(6-(isopropylamino)pyrazin-2-yl)quinazolin-2-yl)piperidine-4-carboxamide [1765];
N-(7-(6-(isopropylamino)pyrazin-2-yl)quinazolin-2-yl)-3-(piperidin-4-yl)benzamide [1766];
N-(7-(6-(isopropylamino)pyrazin-2-yl)quinazolin-2-yl)-3-(1-methylpiperidin-4-yl)benzamide [1767];
N-(7-(6-(isopropylamino)pyrazin-2-yl)quinazolin-2-yl)-1-(piperidin-4-yl)-1H-1,2,3-triazole-4-carboxamide [1768];
1-(1-(2-fluoroethyl)piperidin-4-yl)-N-(7-(6-(isopropylamino)pyrazin-2-yl)quinazolin-2-yl)-1H-1,2,3-triazole-4-carboxamide [1769];
N-(7-(6-(isopropylamino)pyrazin-2-yl)quinazolin-2-yl)-1-(1-isopropylpiperidin-4-yl)-1H-1,2,3-triazole-4-carboxamide [1770];
N-(7-(6-(isopropylamino)pyrazin-2-yl)quinazolin-2-yl)-2-(4-methylpiperazin-1-yl) isonicotinamide [1771];
N-(7-(6-(tert-butylamino)pyrazin-2-yl)quinazolin-2-yl)-2-(3-(dimethylamino)azetidin-1-yl) isonicotinamide [1772];
N-(7-(6-(tert-butylamino)pyrazin-2-yl)quinazolin-2-yl)-1'-methyl-1',2',3',6'-tetrahydro-[2,4'-bipyridine]-4-carboxamide [1773];
N-(7-(6-(tert-butylamino)pyrazin-2-yl)quinazolin-2-yl)-2-(4-methylpiperazin-1-yl) isonicotinamide [1774];
N-(7-(6-(tert-butylamino)pyrazin-2-yl)quinazolin-2-yl)-2-(4-isopropylpiperazin-1-yl) isonicotinamide [1775];
N-(7-(6-(tert-butylamino)pyrazin-2-yl)quinazolin-2-yl)-2-morpholinoisonicotinamide [1776];
N-(7-(6-(((3-fluoroazetidin-3-yl)methyl)amino)pyrazin-2-yl)quinazolin-2-yl) cyclopropanecarboxamide [1777];
4-fluoro-N-(7-(6-(((3-fluoroazetidin-3-yl)methyl)amino)pyrazin-2-yl)quinazolin-2-yl)benzamide [1778];
N-(7-(6-(piperidin-4-ylamino)pyrazin-2-yl)quinazolin-2-yl)cyclobutanecarboxamide [1779];
3,3-difluoro-N-(7-(6-(piperidin-4-ylamino)pyrazin-2-yl)quinazolin-2-yl)cyclobutane-1-carboxamide [1780];
N-(7-(6-(piperidin-4-ylamino)pyrazin-2-yl)quinazolin-2-yl)cyclopentanecarboxamide [1781];
4,4-difluoro-N-(7-(6-(piperidin-4-ylamino)pyrazin-2-yl)quinazolin-2-yl)cyclohexane-1-carboxamide [1782];
N-(7-(6-(piperidin-4-ylamino)pyrazin-2-yl)quinazolin-2-yl)tetrahydro-2H-pyran-4-carboxamide [1783];
4-fluoro-N-(7-(6-(piperidin-4-ylamino)pyrazin-2-yl)quinazolin-2-yl)benzamide [1784];
N-(7-(6-(((3S,4S)-3-fluoropiperidin-4-yl)amino)pyrazin-2-yl)quinazolin-2-yl) cyclopropanecarboxamide [1785];
4-fluoro-N-(7-(6-(((3S,4S)-3-fluoropiperidin-4-yl)amino)pyrazin-2-yl)quinazolin-2-yl)benzamide [1786];
N-(7-(6-((1-methylpiperidin-4-yl)amino)pyrazin-2-yl)quinazolin-2-yl)cyclobutanecarboxamide [1787];
N-(7-(6-((1-methylpiperidin-4-yl)amino)pyrazin-2-yl)quinazolin-2-yl)cyclopentanecarboxamide [1788];
4-fluoro-N-(7-(6-((1-methylpiperidin-4-yl)amino)pyrazin-2-yl)quinazolin-2-yl)benzamide [1789];
N-(7-(6-((1-isopropylpiperidin-4-yl)amino)pyrazin-2-yl)quinazolin-2-yl) cyclopropanecarboxamide [1790];
3,3-difluoro-N-(7-(6-((1-isopropylpiperidin-4-yl)amino)pyrazin-2-yl)quinazolin-2-yl) cyclobutane-1-carboxamide [1791];
N-(7-(6-((1-isopropylpiperidin-4-yl)amino)pyrazin-2-yl)quinazolin-2-yl) cyclopentanecarboxamide [1792];
4-fluoro-N-(7-(6-((1-isopropylpiperidin-4-yl)amino)pyrazin-2-yl)quinazolin-2-yl)benzamide [1793];
N-(7-(6-(dimethylamino)pyrazin-2-yl)quinazolin-2-yl)-2-(4-methylpiperazin-1-yl)isonicotinamide [1794];
N-(7-(6-(diethylamino)pyrazin-2-yl)quinazolin-2-yl)-2-(4-methylpiperazin-1-yl)isonicotinamide [1795];
N-(7-(6-(3-aminoazetidin-1-yl)pyrazin-2-yl)quinazolin-2-yl)-4-fluorobenzamide [1796];
2-(4-methylpiperazin-1-yl)-N-(7-(6-(pyrrolidin-1-yl)pyrazin-2-yl)quinazolin-2-yl)isonicotinamide [1797];
N-(7-(6-(azetidin-3-ylmethoxy)pyrazin-2-yl)quinazolin-2-yl)-4-fluorobenzamide [1798];
N-(7-(6-(azetidin-3-yloxy)pyrazin-2-yl)quinazolin-2-yl)-4-fluorobenzamide [1799];
N-(7-(1H-pyrrolo[2,3-b]pyridin-5-yl)quinazolin-2-yl)-1-(1-methylpiperidin-4-yl)-1H-pyrazole-4-carboxamide [1800];
N-(7-(1H-pyrrolo[3,2-b]pyridin-6-yl)quinazolin-2-yl)-1-(1-methylpiperidin-4-yl)-1H-pyrazole-4-carboxamide [1801];
N-(7-(1H-pyrrolo[2,3-c]pyridin-4-yl)quinazolin-2-yl)-1-(1-methylpiperidin-4-yl)-1H-pyrazole-4-carboxamide [1802];
N-(7-(1H-pyrrolo[2,3-b]pyridin-5-yl)quinazolin-2-yl)-2-(4-methylpiperazin-1-yl)isonicotinamide [1803];
N-(7-(1H-pyrrolo[3,2-b]pyridin-6-yl)quinazolin-2-yl)-2-(4-methylpiperazin-1-yl)isonicotinamide [1804];
N-(7-(1H-pyrrolo[2,3-c]pyridin-4-yl)quinazolin-2-yl)-2-(4-methylpiperazin-1-yl)isonicotinamide [1805];
2-(4-methylpiperazin-1-yl)-N-(7-(oxazolo[5,4-b]pyridin-6-yl)quinazolin-2-yl)isonicotinamide [1806];
N-(7-(2-methyl-1H-pyrrolo[2,3-b]pyridin-5-yl)quinazolin-2-yl)-2-(4-methylpiperazin-1-yl) isonicotinamide [1807];
N-(7-(3-methyl-1H-pyrrolo[2,3-b]pyridin-5-yl)quinazolin-2-yl)-2-(4-methylpiperazin-1-yl) isonicotinamide [1808];

N-(7-(2-methyl-1H-pyrrolo[3,2-b]pyridin-6-yl)quinazolin-2-yl)-2-(4-methylpiperazin-1-yl) isonicotinamide [1809];

N-(7-(5H-pyrrolo[2,3-b]pyrazin-2-yl)quinazolin-2-yl)-2-(4-methylpiperazin-1-yl)isonicotinamide [1810];

N-(7-(5H-pyrrolo[2,3-b]pyrazin-3-yl)quinazolin-2-yl)-2-(4-methylpiperazin-1-yl)isonicotinamide [1811];

1-isopropyl-N-(7-(6-(piperidin-4-ylamino)pyrazin-2-yl)quinazolin-2-yl)-1H-pyrazole-4-carboxamide [1812];

1-isopropyl-N-(7-(6-((1-methylpiperidin-4-yl)amino)pyrazin-2-yl)quinazolin-2-yl)-1H-pyrazole-4-carboxamide [1813];

trans-4-((2-fluoroethyl)amino)-N-(7-(1-methyl-1H-pyrazol-4-yl)quinazolin-2-yl)cyclohexane-1-carboxamide [4566];

trans-4-((2-methoxyethyl)amino)-N-(7-(1-methyl-1H-pyrazol-4-yl)quinazolin-2-yl)cyclohexane-1-carboxamide [4567];

tert-butyl (trans-4-((7-(1-methyl-1H-pyrazol-4-yl)quinazolin-2-yl)carbamoyl)cyclohexyl) carbamate [4568];

N-(7-(1-methyl-1H-pyrazol-4-yl)quinazolin-2-yl)-2-((1-methylpiperidin-4-yl)amino) isonicotinamide [4569];

N-(7-(1-methyl-1H-pyrazol-4-yl)quinazolin-2-yl)-2-(4-methylpiperazin-1-yl)thiazole-5-carboxamide [4570];

N-(7-(1-methyl-1H-pyrazol-4-yl)quinazolin-2-yl)-2-(4-methylpiperazin-1-yl)thiazole-5-carboxamide [4571];

N-(7-(1-methyl-5-(piperidin-1-ylmethyl)-1H-pyrazol-4-yl)quinazolin-2-yl)-2-(2,7-diazaspiro[3.5] nonan-2-yl) isonicotinamide [4572];

N-(7-(1-methyl-1H-1,2,3-triazol-4-yl)quinazolin-2-yl)-4-(piperidin-4-yloxy)benzamide [4573];

N-(7-(1-methyl-1H-tetrazol-5-yl)quinazolin-2-yl)-1-(3,3,3-trifluoropropyl)piperidine-4-carboxamide [4574];

N-(7-(1,2-dimethyl-1H-imidazol-5-yl)quinazolin-2-yl)-2-(pyrrolidin-1-yl)propanamide [4575];

N-(7-(1,2-dimethyl-1H-imidazol-5-yl)quinazolin-2-yl)-2-(piperidin-1-yl)propanamide [4576];

4-isopropoxy-N-(7-(7-methyl-5,6,7,8-tetrahydroimidazo[1,2-a]pyrazin-3-yl)quinazolin-2-yl) benzamide [4577];

trans-3-morpholino-N-(7-(oxazol-5-yl)quinazolin-2-yl)cyclobutane-1-carboxamide [4578];

trans-4-(hydroxymethyl)-N-(7-(oxazol-5-yl)quinazolin-2-yl)cyclohexane-1-carboxamide [4579];

N-(7-(oxazol-5-yl)quinazolin-2-yl)piperidine-4-carboxamide [4580];

4-morpholino-N-(7-(oxazol-5-yl)quinazolin-2-yl)piperidine-1-carboxamide [4581];

N-(7-(oxazol-5-yl)quinazolin-2-yl)-4-(piperidin-4-yloxy)benzamide [4582];

N-(7-(oxazol-5-yl)quinazolin-2-yl)-3-(piperidin-4-yloxy)benzamide [4583];

2-methyl-N-(7-(oxazol-5-yl)quinazolin-2-yl)-5,6-dihydroimidazo[1,2-a]pyrazine-7(8H)-carboxamide [4584];

2-(1H-imidazol-1-yl)-N-(7-(oxazol-5-yl)quinazolin-2-yl)acetamide [4585];

trans-4-(hydroxymethyl)-N-(7-(thiazol-5-yl)quinazolin-2-yl)cyclohexane-1-carboxamide [4586];

trans-4-(dimethylamino)-N-(7-(thiazol-5-yl)quinazolin-2-yl)cyclohexane-1-carboxamide [4587];

N-(7-(thiazol-5-yl)quinazolin-2-yl)-1-((1-(trifluoromethyl)cyclopropyl)methyl)piperidine-4-carboxamide [4588];

trans-4-(hydroxymethyl)-N-(7-(2-methylthiazol-5-yl)quinazolin-2-yl)cyclohexane-1-carboxamide [4589];

trans-4-(dimethylamino)-N-(7-(2-methylthiazol-5-yl)quinazolin-2-yl)cyclohexane-1-carboxamide [4590];

N-(7-(2-methylthiazol-5-yl)quinazolin-2-yl)-1-(oxetan-3-yl)piperidine-4-carboxamide [4591];

N-(7-(2-methylthiazol-5-yl)quinazolin-2-yl)-1-(2-(pyrrolidin-1-yl)acetyl)piperidine-4-carboxamide [4592];

2-((1S,4S)-2-oxa-5-azabicyclo[2.2.1]heptan-5-yl)-N-(7-(5-methyl-1,3,4-thiadiazol-2-yl) quinazolin-2-yl)acetamide [4593];

N-(7-(5-(cyano(4-hydroxypiperidin-1-yl)methyl)pyridin-3-yl)quinazolin-2-yl) cyclopropanecarboxamide [4594];

4-fluoro-N-(7-(6-((1-methylazetidin-3-yl)methoxy)pyrazin-2-yl)quinazolin-2-yl)benzamide [4595];

1-isopropyl-N-(7-(6-((1-methylpiperidin-4-yl)amino)pyrazin-2-yl)quinazolin-2-yl)-1H-pyrazole-4-carboxamide [4596]; or a pharmaceutically acceptable salt thereof.

14. The compound of claim 1, wherein the compound of Formula I is selected from the group consisting of:

N-(6-(1H-pyrazol-4-yl)cinnolin-3-yl)-1-isobutylpiperidine-4-carboxamide [1814];

N-(6-(1-methyl-1H-pyrazol-4-yl)cinnolin-3-yl)cyclopropanecarboxamide [1815];

4,4-difluoro-N-(6-(1-methyl-1H-pyrazol-4-yl)cinnolin-3-yl)cyclohexane-1-carboxamide [1816];

trans-4-methoxy-N-(6-(1-methyl-1H-pyrazol-4-yl)cinnolin-3-yl)cyclohexane-1-carboxamide [1817];

trans-N-(6-(1-methyl-1H-pyrazol-4-yl)cinnolin-3-yl)-4-morpholinocyclohexane-1-carboxamide [1818];

trans-4-((3-fluoroazetidin-1-yl)methyl)-N-(6-(1-methyl-1H-pyrazol-4-yl)cinnolin-3-yl) cyclohexane-1-carboxamide [1819];

trans-N-(6-(1-methyl-1H-pyrazol-4-yl)cinnolin-3-yl)-4-((4-methylpiperazin-1-yl)methyl) cyclohexane-1-carboxamide [1820];

N-(6-(1-methyl-1H-pyrazol-4-yl)cinnolin-3-yl)-2-(pyrrolidin-1-yl)acetamide [1821];

(S)-2-(3-fluoropyrrolidin-1-yl)-N-(6-(1-methyl-1H-pyrazol-4-yl)cinnolin-3-yl)acetamide [1822];

(S)—N-(6-(1-methyl-1H-pyrazol-4-yl)cinnolin-3-yl)tetrahydrofuran-2-carboxamide [1823];

N-(6-(1-methyl-1H-pyrazol-4-yl)cinnolin-3-yl)piperidine-4-carboxamide [1824];

1-methyl-N-(6-(1-methyl-1H-pyrazol-4-yl)cinnolin-3-yl)piperidine-4-carboxamide [1825];

1-isopropyl-N-(6-(1-methyl-1H-pyrazol-4-yl)cinnolin-3-yl)piperidine-4-carboxamide [1826];

1-(tert-butyl)-N-(6-(1-methyl-1H-pyrazol-4-yl)cinnolin-3-yl)piperidine-4-carboxamide [1827];

1-cyclopropyl-N-(6-(1-methyl-1H-pyrazol-4-yl)cinnolin-3-yl)piperidine-4-carboxamide [1828];

1-isobutyl-N-(6-(1-methyl-1H-pyrazol-4-yl)cinnolin-3-yl)piperidine-4-carboxamide [1829];

N-(6-(1-methyl-1H-pyrazol-4-yl)cinnolin-3-yl)-1-neopentylpiperidine-4-carboxamide [1830];

1-(2-fluoroethyl)-N-(6-(1-methyl-1H-pyrazol-4-yl)cinnolin-3-yl)piperidine-4-carboxamide [1831];

N-(6-(1-methyl-1H-pyrazol-4-yl)cinnolin-3-yl)-1-(3,3,3-trifluoropropyl)piperidine-4-carboxamide [1832];

1-butyl-N-(6-(1-methyl-1H-pyrazol-4-yl)cinnolin-3-yl) piperidine-4-carboxamide [1833];

1-benzoyl-N-(6-(1-methyl-1H-pyrazol-4-yl)cinnolin-3-yl)piperidine-4-carboxamide [1834];

1-(2,2-difluoropropyl)-N-(6-(1-methyl-1H-pyrazol-4-yl)cinnolin-3-yl)piperidine-4-carboxamide [1835];

N-(6-(1-methyl-1H-pyrazol-4-yl)cinnolin-3-yl)azetidine-3-carboxamide [1836];
1-(2,2-difluoroethyl)-N-(6-(1-methyl-1H-pyrazol-4-yl)cinnolin-3-yl)piperidine-4-carboxamide [1837];
1-(2-fluoro-2-methylpropyl)-N-(6-(1-methyl-1H-pyrazol-4-yl)cinnolin-3-yl)piperidine-4-carboxamide [1838];
N-(6-(1-methyl-1H-pyrazol-4-yl)cinnolin-3-yl)-1-(oxetan-3-yl)piperidine-4-carboxamide [1839];
N-(6-(1-methyl-1H-pyrazol-4-yl)cinnolin-3-yl)-1-((3-methyloxetan-3-yl)methyl)piperidine-4-carboxamide [1840];
1-(2-methoxyethyl)-N-(6-(1-methyl-1H-pyrazol-4-yl)cinnolin-3-yl)piperidine-4-carboxamide [1841];
1-(2-isopropoxyethyl)-N-(6-(1-methyl-1H-pyrazol-4-yl)cinnolin-3-yl)piperidine-4-carboxamide [1842];
1,1-diisobutyl-4-((6-(1-methyl-1H-pyrazol-4-yl)cinnolin-3-yl)carbamoyl)piperidin-1-ium [1843];
4-fluoro-N-(6-(1-methyl-1H-pyrazol-4-yl)cinnolin-3-yl)piperidine-4-carboxamide [1844];
4-fluoro-1-methyl-N-(6-(1-methyl-1H-pyrazol-4-yl)cinnolin-3-yl)piperidine-4-carboxamide [1845];
4-fluoro-1-isobutyl-N-(6-(1-methyl-1H-pyrazol-4-yl)cinnolin-3-yl)piperidine-4-carboxamide [1846];
(S)—N-(6-(1-methyl-1H-pyrazol-4-yl)cinnolin-3-yl)piperidine-3-carboxamide [1847];
(R)—N-(6-(1-methyl-1H-pyrazol-4-yl)cinnolin-3-yl)piperidine-3-carboxamide [1848];
(S)-1-isobutyl-N-(6-(1-methyl-1H-pyrazol-4-yl)cinnolin-3-yl)piperidine-3-carboxamide [1849];
(R)-1-isobutyl-N-(6-(1-methyl-1H-pyrazol-4-yl)cinnolin-3-yl)piperidine-3-carboxamide [1850];
N-(6-(1-methyl-1H-pyrazol-4-yl)cinnolin-3-yl)tetrahydro-2H-pyran-4-carboxamide [1851];
N-(6-(1-methyl-1H-pyrazol-4-yl)cinnolin-3-yl)-2-(piperidin-1-yl)acetamide [1852];
2-(4-fluoropiperidin-1-yl)-N-(6-(1-methyl-1H-pyrazol-4-yl)cinnolin-3-yl)acetamide [1853];
trans-4-amino-N-(6-(1-methyl-1H-pyrazol-4-yl)cinnolin-3-yl)cyclohexane-1-carboxamide [1854];
N-(6-(1-methyl-1H-pyrazol-4-yl)cinnolin-3-yl)-2-(4-methylpiperazin-1-yl)acetamide [1855];
(S)—N-(6-(1-methyl-1H-pyrazol-4-yl)cinnolin-3-yl)piperidine-2-carboxamide [1856];
2-(4-isobutylpiperazin-1-yl)-N-(6-(1-methyl-1H-pyrazol-4-yl)cinnolin-3-yl)acetamide [1857];
2-(3,3-dimethylazetidin-1-yl)-N-(6-(1-methyl-1H-pyrazol-4-yl)cinnolin-3-yl)acetamide [1858];
(R)-2-(3-fluoropyrrolidin-1-yl)-N-(6-(1-methyl-1H-pyrazol-4-yl)cinnolin-3-yl)acetamide [1859];
(S)—N-(6-(1-methyl-1H-pyrazol-4-yl)cinnolin-3-yl)-2-(2-methylpyrrolidin-1-yl)acetamide [1860];
2-(3-azabicyclo[3.1.0]hexan-3-yl)-N-(6-(1-methyl-1H-pyrazol-4-yl)cinnolin-3-yl)acetamide [1861];
2-(7-azabicyclo[2.2.1]heptan-7-yl)-N-(6-(1-methyl-1H-pyrazol-4-yl)cinnolin-3-yl)acetamide [1862];
N-(6-(1-methyl-1H-pyrazol-4-yl)cinnolin-3-yl)-2-(4-methylpiperidin-1-yl)acetamide [1863];
N-(6-(1-methyl-1H-pyrazol-4-yl)cinnolin-3-yl)-2-(4-(trifluoromethyl)piperidin-1-yl)acetamide [1864];
2-(4-(difluoromethyl)piperidin-1-yl)-N-(6-(1-methyl-1H-pyrazol-4-yl)cinnolin-3-yl)acetamide [1865];
N-(6-(1-methyl-1H-pyrazol-4-yl)cinnolin-3-yl)-2-(6-azaspiro[2.5]octan-6-yl)acetamide [1866];
N-(6-(1-methyl-1H-pyrazol-4-yl)cinnolin-3-yl)-2-(pyrrolidin-1-yl)propanamide [1867];
(R)—N-(6-(1-methyl-1H-pyrazol-4-yl)cinnolin-3-yl)-2-(2-methylpyrrolidin-1-yl)acetamide [1868];
2-(cyclobutyl(methyl)amino)-N-(6-(1-methyl-1H-pyrazol-4-yl)cinnolin-3-yl)acetamide [1869];
2-(diethylamino)-N-(6-(1-methyl-1H-pyrazol-4-yl)cinnolin-3-yl)acetamide [1870];
7-(2-fluoroethyl)-N-(6-(1-methyl-1H-pyrazol-4-yl)cinnolin-3-yl)-7-azaspiro[3.5]nonane-2-carboxamide [1871];
4-methyl-N-(6-(1-methyl-1H-pyrazol-4-yl)cinnolin-3-yl)piperazine-1-carboxamide [1872];
(S)—N-(6-(1-methyl-1H-pyrazol-4-yl)cinnolin-3-yl)-2-(pyrrolidin-1-yl)propanamide [1873];
(R)—N-(6-(1-methyl-1H-pyrazol-4-yl)cinnolin-3-yl)-2-(pyrrolidin-1-yl)propanamide [1874];
(R)—N-(6-(1-methyl-1H-pyrazol-4-yl)cinnolin-3-yl)pyrrolidine-2-carboxamide [1875];
2-methyl-N-(6-(1-methyl-1H-pyrazol-4-yl)cinnolin-3-yl)-2-azaspiro[3.3]heptane-6-carboxamide [1876];
N-(6-(1-methyl-1H-pyrazol-4-yl)cinnolin-3-yl)-2-(2,2,2-trifluoroacetyl)-2-azaspiro[3.3]heptane-6-carboxamide [1877];
2-(2-fluoroethyl)-N-(6-(1-methyl-1H-pyrazol-4-yl)cinnolin-3-yl)-2-azaspiro[3.3]heptane-6-carboxamide [1878];
trans-4-(dimethylamino)-N-(6-(1-methyl-1H-pyrazol-4-yl)cinnolin-3-yl)cyclohexane-1-carboxamide [1879];
1-acetyl-N-(6-(1-methyl-1H-pyrazol-4-yl)cinnolin-3-yl)piperidine-4-carboxamide [1880];
N-(6-(1-methyl-1H-pyrazol-4-yl)cinnolin-3-yl)-1-((1-(trifluoromethyl)cyclopropyl)methyl) piperidine-4-carboxamide [1881];
(S)-1-(2-fluoropropyl)-N-(6-(1-methyl-1H-pyrazol-4-yl)cinnolin-3-yl)piperidine-4-carboxamide [1882];
(R)-1-(2-fluoropropyl)-N-(6-(1-methyl-1H-pyrazol-4-yl)cinnolin-3-yl)piperidine-4-carboxamide [1883];
N-(6-(1-methyl-1H-pyrazol-4-yl)cinnolin-3-yl)-2-(piperidin-1-yl)propanamide [1884];
N-(6-(1-methyl-1H-pyrazol-4-yl)cinnolin-3-yl)-1-(methylsulfonyl)piperidine-4-carboxamide [1885];
1'-methyl-N-(6-(1-methyl-1H-pyrazol-4-yl)cinnolin-3-yl)-[1,4'-bipiperidine]-4-carboxamide [1886];
trans-4-(hydroxymethyl)-N-(6-(1-methyl-1H-pyrazol-4-yl)cinnolin-3-yl)cyclohexane-1-carboxamide [1887];
methyl 2-(4-((6-(1-methyl-1H-pyrazol-4-yl)cinnolin-3-yl)carbamoyl)piperidin-1-yl)acetate [1888];
1-benzyl-N-(6-(1-methyl-1H-pyrazol-4-yl)cinnolin-3-yl)piperidine-4-carboxamide [1889];
N-(6-(1-methyl-1H-pyrazol-4-yl)cinnolin-3-yl)-1-(2-(pyrrolidin-1-yl)acetyl)piperidine-4-carboxamide [1890];
N-(6-(1-methyl-1H-pyrazol-4-yl)cinnolin-3-yl)-2-morpholinoacetamide [1891];
(S)—N-(6-(1-methyl-1H-pyrazol-4-yl)cinnolin-3-yl)-2-(3-methylmorpholino)acetamide [1892];
(R)—N-(6-(1-methyl-1H-pyrazol-4-yl)cinnolin-3-yl)-2-(3-methylmorpholino)acetamide [1893];
(S)—N-(6-(1-methyl-1H-pyrazol-4-yl)cinnolin-3-yl)-2-(2-methylmorpholino)acetamide [1894];
2-((2R,6S)-2,6-dimethylmorpholino)-N-(6-(1-methyl-1H-pyrazol-4-yl)cinnolin-3-yl)acetamide [1895];
2-((1S,4S)-2-oxa-5-azabicyclo [2.2.1]heptan-5-yl)-N-(6-(1-methyl-1H-pyrazol-4-yl)cinnolin-3-yl)acetamide [1896];
2-((1R,4R)-2-oxa-5-azabicyclo[2.2.1]heptan-5-yl)-N-(6-(1-methyl-1H-pyrazol-4-yl)cinnolin-3-yl)acetamide [1897];

2-(3-oxa-8-azabicyclo[3.2.1]octan-8-yl)-N-(6-(1-methyl-1H-pyrazol-4-yl)cinnolin-3-yl)acetamide [1898];
(S)—N-(6-(1-methyl-1H-pyrazol-4-yl)cinnolin-3-yl)-2-morpholinopropanamide [1899];
N-(6-(1-methyl-1H-pyrazol-4-yl)cinnolin-3-yl)-2-(morpholin-2-yl)acetamide [1900];
N-(6-(1-methyl-1H-pyrazol-4-yl)cinnolin-3-yl)-2-(4-methylmorpholin-2-yl)acetamide [1901];
2-(4-ethylpiperazin-1-yl)-N-(6-(1-methyl-1H-pyrazol-4-yl)cinnolin-3-yl)acetamide [1902];
2-(4-isopropylpiperazin-1-yl)-N-(6-(1-methyl-1H-pyrazol-4-yl)cinnolin-3-yl)acetamide [1903];
2-(4-cyclopropylpiperazin-1-yl)-N-(6-(1-methyl-1H-pyrazol-4-yl)cinnolin-3-yl)acetamide [1904];
2-(4-(2-fluoroethyl)piperazin-1-yl)-N-(6-(1-methyl-1H-pyrazol-4-yl)cinnolin-3-yl)acetamide [1905];
(S)-2-(2,4-dimethylpiperazin-1-yl)-N-(6-(1-methyl-1H-pyrazol-4-yl)cinnolin-3-yl)acetamide [1906];
1-(2-hydroxyethyl)-N-(6-(1-methyl-1H-pyrazol-4-yl)cinnolin-3-yl)piperidine-4-carboxamide [1907];
N-(6-(1-methyl-1H-pyrazol-4-yl)cinnolin-3-yl)-1-(pyridin-2-ylmethyl)piperidine-4-carboxamide [1908];
N-(6-(1-methyl-1H-pyrazol-4-yl)cinnolin-3-yl)-1-(oxazol-2-ylmethyl)piperidine-4-carboxamide [1909];
(R)—N-(6-(1-methyl-1H-pyrazol-4-yl)cinnolin-3-yl)-1-oxotetrahydro-1H-pyrrolo[1,2-c]imidazole-2(3H)-carboxamide [1910];
(R)-1-methyl-N-(6-(1-methyl-1H-pyrazol-4-yl)cinnolin-3-yl)pyrrolidine-2-carboxamide [1911];
N-(6-(1-methyl-1H-pyrazol-4-yl)cinnolin-3-yl)-1-(tetrahydro-2H-pyran-4-yl)piperidine-4-carboxamide [1912];
N-(6-(1-methyl-1H-pyrazol-4-yl)cinnolin-3-yl)-1-(pyrimidin-2-ylmethyl)piperidine-4-carboxamide [1913];
N-(6-(1-methyl-1H-pyrazol-4-yl)cinnolin-3-yl)-1-(pyrazin-2-ylmethyl)piperidine-4-carboxamide [1914];
1-((5-methyl-1,2,4-oxadiazol-3-yl)methyl)-N-(6-(1-methyl-1H-pyrazol-4-yl)cinnolin-3-yl) piperidine-4-carboxamide [1915];
1-(2-hydroxy-2-methylpropyl)-N-(6-(1-methyl-1H-pyrazol-4-yl)cinnolin-3-yl)piperidine-4-carboxamide [1916];
tert-butyl 2-(4-((6-(1-methyl-1H-pyrazol-4-yl)cinnolin-3-yl)carbamoyl)piperidin-1-yl)acetate [1917];
2-(4-((6-(1-methyl-1H-pyrazol-4-yl)cinnolin-3-yl)carbamoyl)piperidin-1-yl)acetic acid [1918];
2-(4-methyl-1,4-diazepan-1-yl)-N-(6-(1-methyl-1H-pyrazol-4-yl)cinnolin-3-yl)acetamide [1919];
tert-butyl (6-(1-methyl-1H-pyrazol-4-yl)cinnolin-3-yl) carbamate [1920];
N-(6-(1-methyl-1H-pyrazol-4-yl)cinnolin-3-yl)but-2-ynamide [1921];
trans-4-((6-(1-methyl-1H-pyrazol-4-yl)cinnolin-3-yl)carbamoyl)cyclohexane-1-carboxylic acid [1922];
N-(6-(1-methyl-1H-pyrazol-4-yl)cinnolin-3-yl)-3-morpholinopropanamide [1923];
trans-N-(6-(1-methyl-1H-pyrazol-4-yl)cinnolin-3-yl)-3-morpholinocyclobutane-1-carboxamide [1924];
N-(6-(1-methyl-1H-pyrazol-4-yl)cinnolin-3-yl)quinuclidine-4-carboxamide [1925];
1-isobutyl-N-(6-(1-methyl-1H-pyrazol-4-yl)cinnolin-3-yl)azepane-4-carboxamide [1926];
2-(4-methoxypiperidin-1-yl)-N-(6-(1-methyl-1H-pyrazol-4-yl)cinnolin-3-yl)acetamide [1927];
2-(4-hydroxypiperidin-1-yl)-N-(6-(1-methyl-1H-pyrazol-4-yl)cinnolin-3-yl)acetamide [1928];
3-(hydroxymethyl)-N-(6-(1-methyl-1H-pyrazol-4-yl)cinnolin-3-yl)bicyclo[1.1.1]pentane-1-carboxamide [1929];
1-methyl-N-(6-(1-methyl-1H-pyrazol-4-yl)cinnolin-3-yl)azepane-4-carboxamide [1930];
trans-4-(dimethylamino)-N-(6-(1-methyl-1H-pyrazol-4-yl)cinnolin-3-yl)cyclohexane-1-carboxamide [1931];
trans-4-(bis(methyl-d3)amino)-N-(6-(1-methyl-1H-pyrazol-4-yl)cinnolin-3-yl)cyclohexane-1-carboxamide [1932];
N-(6-(1-methyl-1H-pyrazol-4-yl)cinnolin-3-yl)-3-((4-methylpiperazin-1-yl)methyl)bicyclo [1.1.1]pentane-1-carboxamide [1933];
methyl trans-4-((6-(1-methyl-1H-pyrazol-4-yl)cinnolin-3-yl)carbamoyl)cyclohexane-1-carboxylate [1934];
2-(1-isobutylpyrrolidin-3-yl)-N-(6-(1-methyl-1H-pyrazol-4-yl)cinnolin-3-yl)acetamide [1935];
trans-N-(6-(1-methyl-1H-pyrazol-4-yl)cinnolin-3-yl)-4-(4-methylpiperazine-1-carbonyl) cyclohexane-1-carboxamide [1936];
1-isobutyl-N-(6-(1-methyl-1H-pyrazol-4-yl)cinnolin-3-yl)piperidine-4-carboxamide [1937];
N-(6-(1-methyl-1H-pyrazol-4-yl)cinnolin-3-yl)-1-(phenylsulfonyl)piperidine-4-carboxamide [1938];
8-methyl-N-(6-(1-methyl-1H-pyrazol-4-yl)cinnolin-3-yl)-3,8-diazabicyclo[3.2.1]octane-3-carboxamide [1939];
3-methyl-N-(6-(1-methyl-1H-pyrazol-4-yl)cinnolin-3-yl)-3,8-diazabicyclo[3.2.1]octane-8-carboxamide [1940];
(1R,3 s,5 S)-3-amino-N-(6-(1-methyl-1H-pyrazol-4-yl) cinnolin-3-yl)-8-azabicyclo[3.2.1]octane-8-carboxamide [1941];
(1R,3s,5S)—N-(6-(1-methyl-1H-pyrazol-4-yl)cinnolin-3-yl)-3-((3,3,3-trifluoropropyl)amino)-8-azabicyclo [3.2.1]octane-8-carboxamide [1942];
(1R,3s,5S)-3-((1,3-difluoropropan-2-yl)amino)-N-(6-(1-methyl-1H-pyrazol-4-yl)cinnolin-3-yl)-8-azabicyclo [3.2.1]octane-8-carboxamide [1943];
N-(6-(1-methyl-1H-pyrazol-4-yl)cinnolin-3-yl)morpholine-4-carboxamide [1944];
4-(dimethylamino)-N-(6-(1-methyl-1H-pyrazol-4-yl)cinnolin-3-yl)piperidine-1-carboxamide [1945];
(S)-2,4-dimethyl-N-(6-(1-methyl-1H-pyrazol-4-yl)cinnolin-3-yl)piperazine-1-carboxamide [1946];
1-methyl-3-(6-(1-methyl-1H-pyrazol-4-yl)cinnolin-3-yl)-1-(1-methylpiperidin-4-yl)urea [1947];
1-(6-(1-methyl-1H-pyrazol-4-yl)cinnolin-3-yl)-3-(1-methylpiperidin-4-yl)urea [1948];
4-isopropyl-N-(6-(1-methyl-1H-pyrazol-4-yl)cinnolin-3-yl)piperazine-1-carboxamide [1949];
(R)-3,4-dimethyl-N-(6-(1-methyl-1H-pyrazol-4-yl)cinnolin-3-yl)piperazine-1-carboxamide [1950];
N-(6-(1H-pyrazol-4-yl)cinnolin-3-yl)-2-(4-methylpiperazin-1-yl)isonicotinamide [1951];
N-(6-(1-methyl-1H-pyrazol-4-yl)cinnolin-3-yl)-3-(piperazin-1-yl)benzamide [1952];
N-(6-(1-methyl-1H-pyrazol-4-yl)cinnolin-3-yl)-3-(4-methylpiperazin-1-yl)benzamide [1953];
N-(6-(1-methyl-1H-pyrazol-4-yl)cinnolin-3-yl)-3-(pyrrolidin-1-ylmethyl)benzamide [1954];
N-(6-(1-methyl-1H-pyrazol-4-yl)cinnolin-3-yl)-3-(piperidin-4-yloxy)benzamide [1955];
N-(6-(1-methyl-1H-pyrazol-4-yl)cinnolin-3-yl)-3-((1-methylpiperidin-4-yl)oxy)benzamide [1956];
N-(6-(1-methyl-1H-pyrazol-4-yl)cinnolin-3-yl)-4-(piperidin-4-yloxy)benzamide [1957];

N-(6-(1-methyl-1H-pyrazol-4-yl)cinnolin-3-yl)-4-((1-methylpiperidin-4-yl)oxy)benzamide [1958];
N-(6-(1-methyl-1H-pyrazol-4-yl)cinnolin-3-yl)-2-(piperazin-1-yl)isonicotinamide [1959];
N-(6-(1-methyl-1H-pyrazol-4-yl)cinnolin-3-yl)-2-(4-methylpiperazin-1-yl)isonicotinamide [1960];
2-(4-isopropylpiperazin-1-yl)-N-(6-(1-methyl-1H-pyrazol-4-yl)cinnolin-3-yl)isonicotinamide [1961];
2-(4-cyclopropylpiperazin-1-yl)-N-(6-(1-methyl-1H-pyrazol-4-yl)cinnolin-3-yl)isonicotinamide [1962];
2-(4-(2-fluoroethyl)piperazin-1-yl)-N-(6-(1-methyl-1H-pyrazol-4-yl)cinnolin-3-yl) isonicotinamide [1963];
N-(6-(1-methyl-1H-pyrazol-4-yl)cinnolin-3-yl)-6-(4-methylpiperazin-1-yl)nicotinamide [1964];
N-(6-(1-methyl-1H-pyrazol-4-yl)cinnolin-3-yl)-5-(piperidin-4-yloxy)nicotinamide [1965];
N-(6-(1-methyl-1H-pyrazol-4-yl)cinnolin-3-yl)-2-(piperidin-4-yloxy)isonicotinamide [1966];
N-(6-(1-methyl-1H-pyrazol-4-yl)cinnolin-3-yl)-2-((1-methylpiperidin-4-yl)oxy)isonicotinamide [1967];
N-(6-(1-methyl-1H-pyrazol-4-yl)cinnolin-3-yl)-5-(piperidin-4-ylamino)nicotinamide [1968];
N-(6-(1-methyl-1H-pyrazol-4-yl)cinnolin-3-yl)-5-((1-methylpiperidin-4-yl)amino)nicotinamide [1969];
2-(4-aminopiperidin-1-yl)-N-(6-(1-methyl-1H-pyrazol-4-yl)cinnolin-3-yl)isonicotinamide [1970];
N-(6-(1-methyl-1H-pyrazol-4-yl)cinnolin-3-yl)-2-(4-(methylamino)piperidin-1-yl) isonicotinamide [1971];
2-(4-(dimethylamino)piperidin-1-yl)-N-(6-(1-methyl-1H-pyrazol-4-yl)cinnolin-3-yl) isonicotinamide [1972];
2-((1-isopropylpiperidin-4-yl)oxy)-N-(6-(1-methyl-1H-pyrazol-4-yl)cinnolin-3-yl) isonicotinamide [1973];
2-(3-aminoazetidin-1-yl)-N-(6-(1-methyl-1H-pyrazol-4-yl)cinnolin-3-yl)isonicotinamide [1974];
2-(3-(dimethylamino)azetidin-1-yl)-N-(6-(1-methyl-1H-pyrazol-4-yl)cinnolin-3-yl) isonicotinamide [1975];
N-(6-(1-methyl-1H-pyrazol-4-yl)cinnolin-3-yl)-2-morpholinoisonicotinamide [1976];
2-((2-(dimethylamino)ethyl)amino)-N-(6-(1-methyl-1H-pyrazol-4-yl)cinnolin-3-yl) isonicotinamide [1977];
2-(2-(dimethylamino)ethoxy)-N-(6-(1-methyl-1H-pyrazol-4-yl)cinnolin-3-yl)isonicotinamide [1978];
2-(4-isobutylpiperazin-1-yl)-N-(6-(1-methyl-1H-pyrazol-4-yl)cinnolin-3-yl)isonicotinamide [1979];
2-(azetidin-3-yloxy)-N-(6-(1-methyl-1H-pyrazol-4-yl)cinnolin-3-yl)isonicotinamide [1980];
N-(6-(1-methyl-1H-pyrazol-4-yl)cinnolin-3-yl)-2-((1-methylazetidin-3-yl)oxy)isonicotinamide [1981];
2-(4-ethylpiperazin-1-yl)-N-(6-(1-methyl-1H-pyrazol-4-yl)cinnolin-3-yl)isonicotinamide [1982];
4-((dimethylamino)methyl)-N-(6-(1-methyl-1H-pyrazol-4-yl)cinnolin-3-yl)benzamide [1983];
N-(6-(1-methyl-1H-pyrazol-4-yl)cinnolin-3-yl)-3-(1-methylpiperidin-4-yl)benzamide [1984];
N-(6-(1-methyl-1H-pyrazol-4-yl)cinnolin-3-yl)-3-((4-methylpiperazin-1-yl)methyl)benzamide [1985];
N-(6-(1-methyl-1H-pyrazol-4-yl)cinnolin-3-yl)isonicotinamide [1986];
2-hydroxy-N-(6-(1-methyl-1H-pyrazol-4-yl)cinnolin-3-yl)isonicotinamide [1987];
2-isopropoxy-N-(6-(1-methyl-1H-pyrazol-4-yl)cinnolin-3-yl)isonicotinamide [1988];
N-(6-(1-methyl-1H-pyrazol-4-yl)cinnolin-3-yl)-2-(1-methylpiperidin-4-yl)isonicotinamide [1989];
1'-methyl-N-(6-(1-methyl-1H-pyrazol-4-yl)cinnolin-3-yl)-1',2',3',6'-tetrahydro-[2,4'-bipyridine]-4-carboxamide [1990];
N-(6-(1-methyl-1H-pyrazol-4-yl)cinnolin-3-yl)-2-(4-(6-(4-methylpiperazin-1-yl) nicotinoyl)piperazin-1-yl) isonicotinamide [1991];
2-(4-hydroxy-4-methyl-4$\lambda^4$-piperazin-1-yl)-N-(6-(1-methyl-1H-pyrazol-4-yl)cinnolin-3-yl) isonicotinamide [1992];
2-methyl-N-(6-(1-methyl-1H-pyrazol-4-yl)cinnolin-3-yl)-6-(4-methylpiperazin-1-yl) isonicotinamide [1993];
3-methyl-N-(6-(1-methyl-1H-pyrazol-4-yl)cinnolin-3-yl)-2-(4-methylpiperazin-1-yl) isonicotinamide [1994];
2-(4-methyl-1,4-diazepan-1-yl)-N-(6-(1-methyl-1H-pyrazol-4-yl)cinnolin-3-yl)isonicotinamide [1995];
2-((2S,6R)-2,6-dimethylmorpholino)-N-(6-(1-methyl-1H-pyrazol-4-yl)cinnolin-3-yl) isonicotinamide [1996];
N-(6-(1-methyl-1H-pyrazol-4-yl)cinnolin-3-yl)-2-(2,7-diazaspiro[3.5]nonan-2-yl)isonicotinamide [1997];
N-(6-(1-methyl-1H-pyrazol-4-yl)cinnolin-3-yl)-2-(7-methyl-2,7-diazaspiro[3.5]nonan-2-yl) isonicotinamide [1998];
N-(6-(1-methyl-1H-pyrazol-4-yl)cinnolin-3-yl)-2-(2,7-diazaspiro[3.5]nonan-7-yl)isonicotinamide [1999];
N-(6-(1-methyl-1H-pyrazol-4-yl)cinnolin-3-yl)-2-(2-methyl-2,7-diazaspiro[3.5]nonan-7-yl) isonicotinamide [2000];
2-(methyl(1-methylpiperidin-4-yl)amino)-N-(6-(1-methyl-1H-pyrazol-4-yl)cinnolin-3-yl) isonicotinamide [2001];
N-(6-(1-methyl-1H-pyrazol-4-yl)cinnolin-3-yl)-2-((1-methylpiperidin-4-yl)thio)isonicotinamide [2002];
N-(6-(1-methyl-1H-pyrazol-4-yl)cinnolin-3-yl)-2-(4-methylpiperazin-1-yl)pyrimidine-4-carboxamide [2003];
N-(6-(1-methyl-1H-pyrazol-4-yl)cinnolin-3-yl)-6-(4-methylpiperazin-1-yl)pyridazine-4-carboxamide [2004];
N-(6-(1-methyl-1H-pyrazol-4-yl)cinnolin-3-yl)-6-(4-methylpiperazin-1-yl)pyrimidine-4-carboxamide [2005];
N-(6-(1-methyl-1H-pyrazol-4-yl)cinnolin-3-yl)-2-phenylacetamide [2006];
N-(6-(1-methyl-1H-pyrazol-4-yl)cinnolin-3-yl)-3-phenylpropanamide [2007];
N-(6-(1-methyl-1H-pyrazol-4-yl)cinnolin-3-yl)-2-(pyridin-3-yl)acetamide [2008];
N-(6-(1-methyl-1H-pyrazol-4-yl)cinnolin-3-yl)-3-(pyridin-3-yl)propanamide [2009];
N-(6-(1-methyl-1H-pyrazol-4-yl)cinnolin-3-yl)-2-(pyridin-4-yl)acetamide [2010];
N-(6-(1-methyl-1H-pyrazol-4-yl)cinnolin-3-yl)-3-(pyridin-4-yl)propanamide [2011];
N-(6-(1-methyl-1H-pyrazol-4-yl)cinnolin-3-yl)isoindoline-5-carboxamide [2012];
2-methyl-N-(6-(1-methyl-1H-pyrazol-4-yl)cinnolin-3-yl)isoindoline-5-carboxamide [2013];
N-(6-(1-methyl-1H-pyrazol-4-yl)cinnolin-3-yl)-1,2,3,4-tetrahydroisoquinoline-7-carboxamide [2014];
2-methyl-N-(6-(1-methyl-1H-pyrazol-4-yl)cinnolin-3-yl)-1,2,3,4-tetrahydroisoquinoline-7-carboxamide [2015];
2-methyl-N-(6-(1-methyl-1H-pyrazol-4-yl)cinnolin-3-yl)-1,2,3,4-tetrahydroisoquinoline-6-carboxamide [2016];
N-(6-(1-methyl-1H-pyrazol-4-yl)cinnolin-3-yl)-1,2,3,4-tetrahydroisoquinoline-6-carboxamide [2017];
N-(6-(1-methyl-1H-pyrazol-4-yl)cinnolin-3-yl)-1H-indole-5-carboxamide [2018];

N-(6-(1-methyl-1H-pyrazol-4-yl)cinnolin-3-yl)benzofuran-5-carboxamide [2019];
N-(6-(1-methyl-1H-pyrazol-4-yl)cinnolin-3-yl)furo[2,3-c]pyridine-5-carboxamide [2020];
N-(6-(1-methyl-1H-pyrazol-4-yl)cinnolin-3-yl)benzo[b]thiophene-5-carboxamide [2021];
N-(6-(1-methyl-1H-pyrazol-4-yl)cinnolin-3-yl)benzofuran-6-carboxamide [2022];
N-(6-(1-methyl-1H-pyrazol-4-yl)cinnolin-3-yl)benzo[d]oxazole-6-carboxamide [2023];
N-(6-(1-methyl-1H-pyrazol-4-yl)cinnolin-3-yl)benzo[d]thiazole-6-carboxamide [2024];
N-(6-(1-methyl-1H-pyrazol-4-yl)cinnolin-3-yl)benzo[d]oxazole-5-carboxamide [2025];
N-(6-(1-methyl-1H-pyrazol-4-yl)cinnolin-3-yl)benzo[d]thiazole-5-carboxamide [2026];
N-(6-(1-methyl-1H-pyrazol-4-yl)cinnolin-3-yl)quinoline-3-carboxamide [2027];
N-(6-(1-methyl-1H-pyrazol-4-yl)cinnolin-3-yl)quinoline-6-carboxamide [2028];
N-(6-(1-methyl-1H-pyrazol-4-yl)cinnolin-3-yl)quinoxaline-6-carboxamide [2029];
5-chloro-N-(6-(1-methyl-1H-pyrazol-4-yl)cinnolin-3-yl)-2-(4-methylpiperazin-1-yl) isonicotinamide [2030];
3-chloro-N-(6-(1-methyl-1H-pyrazol-4-yl)cinnolin-3-yl)-2-(4-methylpiperazin-1-yl) isonicotinamide [2031];
2-(2,5-diazabicyclo[2.2.1]heptan-2-yl)-N-(6-(1-methyl-1H-pyrazol-4-yl)cinnolin-3-yl) isonicotinamide [2032];
N-(6-(1-methyl-1H-pyrazol-4-yl)cinnolin-3-yl)-2-(5-methyl-2,5-diazabicyclo [2.2.1]heptan-2-yl)isonicotinamide [2033];
3-fluoro-N-(6-(1-methyl-1H-pyrazol-4-yl)cinnolin-3-yl)-2-(4-methylpiperazin-1-yl) isonicotinamide [2034];
N-(6-(1-methyl-1H-pyrazol-4-yl)cinnolin-3-yl)-2-((4-methylpiperazin-1-yl)methyl) isonicotinamide [2035];
N-(6-(1-methyl-1H-pyrazol-4-yl)cinnolin-3-yl)-2-(morpholinomethyl)isonicotinamide [2036];
N-(6-(1-methyl-1H-pyrazol-4-yl)cinnolin-3-yl)-2-(pyrrolidin-1-ylmethyl)isonicotinamide [2037];
N-(6-(1-methyl-1H-pyrazol-4-yl)cinnolin-3-yl)-2-(2-(4-methylpiperazin-1-yl)pyridin-4-yl) acetamide [2038];
1-methyl-N-(6-(1-methyl-1H-pyrazol-4-yl)cinnolin-3-yl)-1H-indazole-5-carboxamide [2039];
1-methyl-N-(6-(1-methyl-1H-pyrazol-4-yl)cinnolin-3-yl)-1H-benzo[d]imidazole-5-carboxamide [2040];
N-(6-(1-methyl-1H-pyrazol-4-yl)cinnolin-3-yl)-1-(piperidin-4-yl)-1H-pyrazole-4-carboxamide [2041];
N-(6-(1-methyl-1H-pyrazol-4-yl)cinnolin-3-yl)-1-(1-methylpiperidin-4-yl)-1H-pyrazole-4-carboxamide [2042];
1-(1-ethylpiperidin-4-yl)-N-(6-(1-methyl-1H-pyrazol-4-yl)cinnolin-3-yl)-1H-pyrazole-4-carboxamide [2043];
1-(1-(2-fluoroethyl)piperidin-4-yl)-N-(6-(1-methyl-1H-pyrazol-4-yl)cinnolin-3-yl)-1H-pyrazole-4-carboxamide [2044];
1-(1-isopropylpiperidin-4-yl)-N-(6-(1-methyl-1H-pyrazol-4-yl)cinnolin-3-yl)-1H-pyrazole-4-carboxamide [2045];
1-(1-cyclopropylpiperidin-4-yl)-N-(6-(1-methyl-1H-pyrazol-4-yl)cinnolin-3-yl)-1H-pyrazole-4-carboxamide [2046];
isopropyl 4-(4-(((6-(1-methyl-1H-pyrazol-4-yl)cinnolin-3-yl)carbamoyl)-1H-pyrazol-1-yl) piperidine-1-carboxylate [2047];
N-(6-(1-methyl-1H-pyrazol-4-yl)cinnolin-3-yl)-1-(piperidin-4-yl)-1H-1,2,3-triazole-4-carboxamide [2048];
N-(6-(1-methyl-1H-pyrazol-4-yl)cinnolin-3-yl)-1-(1-methylpiperidin-4-yl)-1H-1,2,3-triazole-4-carboxamide [2049];
1-(1-(2-fluoroethyl)piperidin-4-yl)-N-(6-(1-methyl-1H-pyrazol-4-yl)cinnolin-3-yl)-1H-1,2,3-triazole-4-carboxamide [2050];
1-(1-isopropylpiperidin-4-yl)-N-(6-(1-methyl-1H-pyrazol-4-yl)cinnolin-3-yl)-1H-1,2,3-triazole-4-carboxamide [2051];
N-(6-(1-methyl-1H-pyrazol-4-yl)cinnolin-3-yl)-2-(4-methylpiperazin-1-yl)oxazole-5-carboxamide [2052];
2-(3-(dimethylamino)azetidin-1-yl)-N-(6-(1-methyl-1H-pyrazol-4-yl)cinnolin-3-yl)oxazole-4-carboxamide [2053];
N-(6-(1-methyl-1H-pyrazol-4-yl)cinnolin-3-yl)-2-(piperidin-4-yl)oxazole-4-carboxamide [2054];
N-(6-(1-methyl-1H-pyrazol-4-yl)cinnolin-3-yl)-2-(1-methylpiperidin-4-yl)oxazole-4-carboxamide [2055];
2-(1-(2-fluoroethyl)piperidin-4-yl)-N-(6-(1-methyl-1H-pyrazol-4-yl)cinnolin-3-yl)oxazole-4-carboxamide [2056];
2-(1-isopropylpiperidin-4-yl)-N-(6-(1-methyl-1H-pyrazol-4-yl)cinnolin-3-yl)oxazole-4-carboxamide [2057];
N-(6-(1-methyl-1H-pyrazol-4-yl)cinnolin-3-yl)-2-(4-methylpiperazin-1-yl)oxazole-4-carboxamide [2058];
2-(3-(dimethylamino)azetidin-1-yl)-N-(6-(1-methyl-1H-pyrazol-4-yl)cinnolin-3-yl)thiazole-5-carboxamide [2059];
N-(6-(1-methyl-1H-pyrazol-4-yl)cinnolin-3-yl)-2-(piperidin-4-yl)thiazole-4-carboxamide [2060];
N-(6-(1-methyl-1H-pyrazol-4-yl)cinnolin-3-yl)-2-(4-methylpiperazin-1-yl)thiazole-4-carboxamide [2061];
2-(1-(2-fluoroethyl)piperidin-4-yl)-N-(6-(1-methyl-1H-pyrazol-4-yl)cinnolin-3-yl)thiazole-4-carboxamide [2062];
2-(1-isopropylpiperidin-4-yl)-N-(6-(1-methyl-1H-pyrazol-4-yl)cinnolin-3-yl)thiazole-4-carboxamide [2063];
1-methyl-N-(6-(1-methyl-1H-pyrazol-4-yl)cinnolin-3-yl-4-d)piperidine-4-carboxamide [2064];
N-(6-(1-methyl-1H-pyrazol-4-yl)cinnolin-3-yl)-1-(2-(methyl-d3)propyl-1,1,2,3,3,3-$d_6$)piperidine-4-carboxamide [2065];
N-(6-(1-methyl-1H-pyrazol-4-yl)cinnolin-3-yl)-2-(pyrrolidin-1-yl-2,2,5,5-$d_4$)acetamide [2066];
N-(6-(1-methyl-1H-pyrazol-4-yl)cinnolin-3-yl)-2-(4-(methyl-$d_3$)piperazin-1-yl)acetamide [2067];
N-(6-(1-methyl-1H-pyrazol-4-yl)cinnolin-3-yl)-2-(morpholino-$d_8$)acetamide [2068];
(S)—N-(6-(1-(methyl-$d_3$)-1H-pyrazol-4-yl)cinnolin-3-yl)-2-(pyrrolidin-1-yl)propanamide [2069];
1-isobutyl-N-(6-(1-(methyl-$d_3$)-1H-pyrazol-4-yl)cinnolin-3-yl)piperidine-4-carboxamide [2070];
N-(6-(1-(methyl-$d_3$)-1H-pyrazol-4-yl)cinnolin-3-yl)-2-(4-methylpiperazin-1-yl)acetamide [2071];
N-(6-(1-(methyl-$d_3$)-1H-pyrazol-4-yl)cinnolin-3-yl)-2-(pyrrolidin-1-yl)acetamide [2072];
N-(6-(1-(methyl-$d_3$)-1H-pyrazol-4-yl)cinnolin-3-yl)-2-(piperidin-1-yl)acetamide [2073];
N-(6-(1-(methyl-$d_3$)-1H-pyrazol-4-yl)cinnolin-3-yl)-1-(3,3,3-trifluoropropyl)piperidine-4-carboxamide [2074];
N-(6-(1H-pyrazol-4-yl)cinnolin-3-yl)-2-(4-(methyl-$d_3$)piperazin-1-yl)isonicotinamide [2075];
N-(6-(1H-pyrazol-4-yl)cinnolin-3-yl)-2-(4-(methyl-$d_3$)piperazin-1-yl)isonicotinamide [2076];
N-(6-(1-(methyl-$d_3$)-1H-pyrazol-4-yl)cinnolin-3-yl)-2-(4-methylpiperazin-1-yl)isonicotinamide [2077];

N-(6-(1-(methyl-d₃)-1H-pyrazol-4-yl)cinnolin-3-yl)-2-(4-(methyl-d₃)piperazin-1-yl) isonicotinamide [2078];

N-(6-(1-(methyl-d₃)-1H-pyrazol-4-yl)cinnolin-3-yl)-1-(piperidin-4-yl)-1H-pyrazole-4-carboxamide [2079];

N-(6-(1-(methyl-d₃)-1H-pyrazol-4-yl)cinnolin-3-yl)-1-(1-methylpiperidin-4-yl)-1H-pyrazole-4-carboxamide [2080];

N-(6-(1-(methyl-d₃)-1H-pyrazol-4-yl)cinnolin-3-yl)-2-(piperidin-4-yl)oxazole-4-carboxamide [2081];

N-(6-(1-(methyl-d₃)-1H-pyrazol-4-yl)cinnolin-3-yl)-2-(1-methylpiperidin-4-yl)oxazole-4-carboxamide [2082];

N-(6-(1-ethyl-1H-pyrazol-4-yl)cinnolin-3-yl)-2-(pyrrolidin-1-yl)acetamide [2083];

N-(6-(1-cyclopropyl-1H-pyrazol-4-yl)cinnolin-3-yl)-2-(pyrrolidin-1-yl)acetamide [2084];

N-(6-(1-cyclopropyl-1H-pyrazol-4-yl)cinnolin-3-yl)-1-(3,3,3-trifluoropropyl)piperidine-4-carboxamide [2085];

N-(6-(1-(1-methylpiperidin-4-yl)-1H-pyrazol-4-yl)cinnolin-3-yl)cyclohexanecarboxamide [2086];

2-(pyrrolidin-1-yl)-N-(6-(5-(trifluoromethyl)-1H-pyrazol-4-yl)cinnolin-3-yl)acetamide [2087];

N-(6-(5-(hydroxymethyl)-1-methyl-1H-pyrazol-4-yl)cinnolin-3-yl)-1-methylpiperidine-4-carboxamide [2088];

N-(6-(5-(hydroxymethyl)-1-methyl-1H-pyrazol-4-yl)cinnolin-3-yl)tetrahydro-2H-pyran-4-carboxamide [2089];

N-(6-(5-(azetidin-1-ylmethyl)-1-methyl-1H-pyrazol-4-yl)cinnolin-3-yl)-4,4-difluorocyclohexane-1-carboxamide [2090];

4,4-difluoro-N-(6-(1-methyl-5-(pyrrolidin-1-ylmethyl)-1H-pyrazol-4-yl)cinnolin-3-yl) cyclohexane-1-carboxamide [2091];

4,4-difluoro-N-(6-(1-methyl-5-(piperidin-1-ylmethyl)-1H-pyrazol-4-yl)cinnolin-3-yl) cyclohexane-1-carboxamide [2092];

2-(2-fluoroethyl)-N-(6-(1-methyl-5-(piperidin-1-ylmethyl)-1H-pyrazol-4-yl)cinnolin-3-yl)-2-azaspiro[3.3]heptane-6-carboxamide [2093];

tert-butyl 6-((6-(1-methyl-5-(piperidin-1-ylmethyl)-1H-pyrazol-4-yl)cinnolin-3-yl)carbamoyl)-2-azaspiro[3.3]heptane-2-carboxylate [2094];

2-fluoro-2-methyl-N-(6-(1-methyl-5-(piperidin-1-ylmethyl)-1H-pyrazol-4-yl)cinnolin-3-yl) propanamide [2095];

2-(diethylamino)-N-(6-(1-methyl-5-(piperidin-1-ylmethyl)-1H-pyrazol-4-yl)cinnolin-3-yl) acetamide [2096];

trans-4-methoxy-N-(6-(1-methyl-5-(piperidin-1-ylmethyl)-1H-pyrazol-4-yl)cinnolin-3-yl) cyclohexane-1-carboxamide [2097];

trans-4-(hydroxymethyl)-N-(6-(1-methyl-5-(piperidin-1-ylmethyl)-1H-pyrazol-4-yl)cinnolin-3-yl)cyclohexane-1-carboxamide [2098];

(R)—N-(6-(1-methyl-5-(piperidin-1-ylmethyl)-1H-pyrazol-4-yl)cinnolin-3-yl)pyrrolidine-2-carboxamide [2099];

1-isobutyl-N-(6-(1-methyl-5-(piperidin-1-ylmethyl)-1H-pyrazol-4-yl)cinnolin-3-yl)piperidine-4-carboxamide [2100];

N-(6-(1-methyl-5-(piperidin-1-ylmethyl)-1H-pyrazol-4-yl)cinnolin-3-yl)-1-(oxetan-3-yl) piperidine-4-carboxamide [2101];

1-benzoyl-N-(6-(1-methyl-5-(piperidin-1-ylmethyl)-1H-pyrazol-4-yl)cinnolin-3-yl)piperidine-4-carboxamide [2102];

N-(6-(1-methyl-5-(piperidin-1-ylmethyl)-1H-pyrazol-4-yl)cinnolin-3-yl)tetrahydro-2H-pyran-4-carboxamide [2103];

N-(6-(1-methyl-5-(piperidin-1-ylmethyl)-1H-pyrazol-4-yl)cinnolin-3-yl)-2-(4-methylpiperidin-1-yl)acetamide [2104];

N-(6-(1-(difluoromethyl)-1H-pyrazol-4-yl)cinnolin-3-yl)-2-(4-methylpiperazin-1-yl) isonicotinamide [2105];

N-(6-(1-ethyl-1H-pyrazol-4-yl)cinnolin-3-yl)-2-(4-methylpiperazin-1-yl)isonicotinamide [2106];

N-(6-(1-isopropyl-1H-pyrazol-4-yl)cinnolin-3-yl)-3-(piperidin-4-yloxy)benzamide [2107];

N-(6-(1-isopropyl-1H-pyrazol-4-yl)cinnolin-3-yl)-3-((1-methylpiperidin-4-yl)oxy)benzamide [2108];

N-(6-(1-isopropyl-1H-pyrazol-4-yl)cinnolin-3-yl)-4-(piperidin-4-yloxy)benzamide [2109];

N-(6-(1-cyclopropyl-1H-pyrazol-4-yl)cinnolin-3-yl)-2-(4-methylpiperazin-1-yl)isonicotinamide [2110];

4-fluoro-N-(6-(1-(1-methylpiperidin-4-yl)-1H-pyrazol-4-yl)cinnolin-3-yl)benzamide [2111];

4-(difluoromethoxy)-N-(6-(1-(1-methylpiperidin-4-yl)-1H-pyrazol-4-yl)cinnolin-3-yl)benzamide [2112];

5-fluoro-N-(6-(1-(1-methylpiperidin-4-yl)-1H-pyrazol-4-yl)cinnolin-3-yl)nicotinamide [2113];

N²-methyl-N⁵-(6-(1-(1-methylpiperidin-4-yl)-1H-pyrazol-4-yl)cinnolin-3-yl)pyridine-2,5-dicarboxamide [2114];

1-isopropyl-N-(6-(1-(1-methylpiperidin-4-yl)-1H-pyrazol-4-yl)cinnolin-3-yl)-1H-pyrazole-4-carboxamide [2115];

2-methyl-N-(6-(1-(1-methylpiperidin-4-yl)-1H-pyrazol-4-yl)cinnolin-3-yl)thiazole-5-carboxamide [2116];

N-(6-(5-amino-1-methyl-1H-pyrazol-4-yl)cinnolin-3-yl)-2-(4-methylpiperazin-1-yl) isonicotinamide [2117];

4-(difluoromethoxy)-N-(6-(5-(hydroxymethyl)-1-methyl-1H-pyrazol-4-yl)cinnolin-3-yl) benzamide [2118];

N-(6-(5-(hydroxymethyl)-1-methyl-1H-pyrazol-4-yl)cinnolin-3-yl)-2-(4-methylpiperazin-1-yl) isonicotinamide [2119];

N-(6-(5-(hydroxymethyl)-1-methyl-1H-pyrazol-4-yl)cinnolin-3-yl)-2-(7-methyl-2,7-diazaspiro [3.5]nonan-2-yl)isonicotinamide [2120];

4-fluoro-N-(6-(1-methyl-5-(pyrrolidin-1-ylmethyl)-1H-pyrazol-4-yl)cinnolin-3-yl)benzamide [2121];

4-fluoro-N-(6-(1-methyl-5-(piperidin-1-ylmethyl)-1H-pyrazol-4-yl)cinnolin-3-yl)benzamide [2122];

4-(difluoromethoxy)-N-(6-(1-methyl-5-(piperidin-1-ylmethyl)-1H-pyrazol-4-yl)cinnolin-3-yl)benzamide [2123];

N-(6-(1-methyl-5-(piperidin-1-ylmethyl)-1H-pyrazol-4-yl)cinnolin-3-yl)-3-(pyrrolidin-1-ylmethyl)benzamide [2124];

N-(6-(1-methyl-5-(piperidin-1-ylmethyl)-1H-pyrazol-4-yl)cinnolin-3-yl)-2-(7-methyl-2,7-diazaspiro[3.5]nonan-2-yl)isonicotinamide [2125];

N-(6-(1-methyl-5-(piperidin-1-ylmethyl)-1H-pyrazol-4-yl)cinnolin-3-yl)-2-morpholinoisonicotinamide [2126];

N-(6-(1-methyl-5-(morpholinomethyl)-1H-pyrazol-4-yl)cinnolin-3-yl)-2-morpholinoisonicotinamide [2127];

N-(6-(4,5,6,7-tetrahydropyrazolo[1,5-a]pyrazin-3-yl)cinnolin-3-yl)-1-((1-(trifluoromethyl) cyclopropyl)methyl)piperidine-4-carboxamide [2128];

3,3-difluoro-N-(6-(5-methyl-4,5,6,7-tetrahydropyrazolo[1,5-a]pyrazin-3-yl)cinnolin-3-yl)cyclobutane-1-carboxamide [2129];

N-((4,4-difluorocyclohexyl)methyl)-6-(5-(2-fluoroethyl)-4,5,6,7-tetrahydropyrazolo[1,5-a]pyrazin-3-yl)cinnolin-3-amine [2130];

N-(6-(5-(2-fluoroethyl)-4,5,6,7-tetrahydropyrazolo[1,5-a]pyrazin-3-yl)cinnolin-3-yl)-1-((1-(trifluoromethyl)cyclopropyl)methyl)piperidine-4-carboxamide [2131];

N-(6-(5-(2-fluoroethyl)-4,5,6,7-tetrahydropyrazolo[1,5-a]pyrazin-3-yl)cinnolin-3-yl)-2-(pyrrolidin-1-yl)acetamide [2132];

2-(7-azabicyclo[2.2.1]heptan-7-yl)-N-(6-(5-(2-fluoroethyl)-4,5,6,7-tetrahydropyrazolo[1,5-a]pyrazin-3-yl)cinnolin-3-yl)acetamide [2133];

(R)—N-(6-(5-(2-fluoroethyl)-4,5,6,7-tetrahydropyrazolo[1,5-a]pyrazin-3-yl)cinnolin-3-yl)-1-isobutylpiperidine-3-carboxamide [2134];

N-(6-(5-(2-fluoroethyl)-4,5,6,7-tetrahydropyrazolo[1,5-a]pyrazin-3-yl)cinnolin-3-yl)piperidine-4-carboxamide [2135];

4-fluoro-N-(6-(5-(2-fluoroethyl)-4,5,6,7-tetrahydropyrazolo[1,5-a]pyrazin-3-yl)cinnolin-3-yl)-1-isobutylpiperidine-4-carboxamide [2136];

N-(6-(5-(2-fluoroethyl)-4,5,6,7-tetrahydropyrazolo[1,5-a]pyrazin-3-yl)cinnolin-3-yl)-2-(4-methylpiperazin-1-yl)acetamide [2137];

4-fluoro-N-(6-(4,5,6,7-tetrahydropyrazolo[1,5-a]pyrazin-3-yl)cinnolin-3-yl)benzamide [2138];

N-(6-(5-(2-fluoroethyl)-4,5,6,7-tetrahydropyrazolo[1,5-a]pyrazin-3-yl)cinnolin-3-yl)-3-(4-methylpiperazin-1-yl)benzamide [2139];

$N^5$-(6-(5-(2-fluoroethyl)-4,5,6,7-tetrahydropyrazolo[1,5-a]pyrazin-3-yl)cinnolin-3-yl)-$N^2$-methylpyridine-2,5-dicarboxamide [2140];

N-(6-(5-(2-fluoroethyl)-4,5,6,7-tetrahydropyrazolo[1,5-a]pyrazin-3-yl)cinnolin-3-yl)-6-(4-methylpiperazin-1-yl)nicotinamide [2141];

2-(azetidin-3-yloxy)-N-(6-(5-(2-fluoroethyl)-4,5,6,7-tetrahydropyrazolo[1,5-a]pyrazin-3-yl)cinnolin-3-yl)isonicotinamide [2142];

N-(6-(1-methyl-1H-pyrazol-5-yl)cinnolin-3-yl)-1-(3,3,3-trifluoropropyl)piperidine-4-carboxamide [2143];

1-methyl-N-(6-(1-methyl-1H-pyrazol-3-yl)cinnolin-3-yl)piperidine-4-carboxamide [2144];

N-(6-(1-methyl-1H-pyrazol-3-yl)cinnolin-3-yl)-2-(4-methylpiperazin-1-yl)isonicotinamide [2145];

2-fluoro-2-methyl-N-(6-(1-methyl-1H-1,2,3-triazol-4-yl)cinnolin-3-yl)propanamide [2146];

2,2,3,3-tetramethyl-N-(6-(1-methyl-1H-1,2,3-triazol-4-yl)cinnolin-3-yl)cyclopropane-1-carboxamide [2147];

trans-N-(6-(1-methyl-1H-1,2,3-triazol-4-yl)cinnolin-3-yl)-4-(pyrrolidin-1-yl)cyclohexane-1-carboxamide [2148];

trans-N-(6-(1-methyl-1H-1,2,3-triazol-4-yl)cinnolin-3-yl)-4-morpholinocyclohexane-1-carboxamide [2149];

N-(6-(1-methyl-1H-1,2,3-triazol-4-yl)cinnolin-3-yl)-2-(piperidin-1-yl)acetamide [2150];

1-ethyl-4-fluoro-N-(6-(1-methyl-1H-1,2,3-triazol-4-yl)cinnolin-3-yl)piperidine-4-carboxamide [2151];

4-fluoro-1-isobutyl-N-(6-(1-methyl-1H-1,2,3-triazol-4-yl)cinnolin-3-yl)piperidine-4-carboxamide [2152];

N-(6-(1-methyl-1H-1,2,3-triazol-4-yl)cinnolin-3-yl)-1-(3,3,3-trifluoropropyl)piperidine-4-carboxamide [2153];

N-(6-(1-methyl-1H-1,2,3-triazol-4-yl)cinnolin-3-yl)cyclopropanecarboxamide [2154];

4,4-difluoro-N-(6-(1-methyl-1H-1,2,3-triazol-4-yl)cinnolin-3-yl)cyclohexane-1-carboxamide [2155];

trans-4-(dimethylamino)-N-(6-(1-methyl-1H-1,2,3-triazol-4-yl)cinnolin-3-yl)cyclohexane-1-carboxamide [2156];

trans-N-(6-(1-methyl-1H-1,2,3-triazol-4-yl)cinnolin-3-yl)-4-((4-methylpiperazin-1-yl)methyl) cyclohexane-1-carboxamide [2157];

N-(6-(1-methyl-1H-1,2,3-triazol-4-yl)cinnolin-3-yl)piperidine-4-carboxamide [2158];

1-isobutyl-N-(6-(1-methyl-1H-1,2,3-triazol-4-yl)cinnolin-3-yl)piperidine-4-carboxamide [2159];

N-(6-(1-methyl-1H-1,2,3-triazol-4-yl)cinnolin-3-yl)-1-((1-(trifluoromethyl)cyclopropyl)methyl) piperidine-4-carboxamide [2160];

N-(6-(1-methyl-1H-1,2,3-triazol-4-yl)cinnolin-3-yl)-1-((3-methyloxetan-3-yl)methyl)piperidine-4-carboxamide [2161];

N-(6-(1-methyl-1H-1,2,3-triazol-4-yl)cinnolin-3-yl)-1-(2-(pyrrolidin-1-yl)acetyl)piperidine-4-carboxamide [2162];

1'-methyl-N-(6-(1-methyl-1H-1,2,3-triazol-4-yl)cinnolin-3-yl)-[1,4'-bipiperidine]-4-carboxamide [2163];

(R)—N-(6-(1-methyl-1H-1,2,3-triazol-4-yl)cinnolin-3-yl)piperidine-3-carboxamide [2164];

(R)-1-isobutyl-N-(6-(1-methyl-1H-1,2,3-triazol-4-yl)cinnolin-3-yl)piperidine-3-carboxamide [2165];

N-(6-(1-methyl-1H-1,2,3-triazol-4-yl)cinnolin-3-yl)-2-(pyrrolidin-1-yl)acetamide [2166];

N-(6-(1-methyl-1H-1,2,3-triazol-4-yl)cinnolin-3-yl)-2-(4-methylpiperazin-1-yl)acetamide [2167];

2-(7-azabicyclo[2.2.1]heptan-7-yl)-N-(6-(1-methyl-1H-1,2,3-triazol-4-yl)cinnolin-3-yl)acetamide [2168];

1-(2-hydroxy-2-methylpropyl)-N-(6-(1-methyl-1H-1,2,3-triazol-4-yl)cinnolin-3-yl)piperidine-4-carboxamide [2169];

N-(6-(1-methyl-1H-1,2,3-triazol-4-yl)cinnolin-3-yl)-2-morpholinoacetamide [2170];

2-(4-methoxypiperidin-1-yl)-N-(6-(1-methyl-1H-1,2,3-triazol-4-yl)cinnolin-3-yl)acetamide [2171];

N-(6-(1-methyl-1H-1,2,3-triazol-4-yl)cinnolin-3-yl)morpholine-4-carboxamide [2172];

N-(6-(1-methyl-1H-1,2,3-triazol-4-yl)cinnolin-3-yl)-1-(piperidin-4-yl)-1H-pyrazole-4-carboxamide [2173];

N-(6-(1-methyl-1H-1,2,3-triazol-4-yl)cinnolin-3-yl)-1-(1-methylpiperidin-4-yl)-1H-pyrazole-4-carboxamide [2174];

1-(1-ethylpiperidin-4-yl)-N-(6-(1-methyl-1H-1,2,3-triazol-4-yl)cinnolin-3-yl)-1H-pyrazole-4-carboxamide [2175];

1-(1-isopropylpiperidin-4-yl)-N-(6-(1-methyl-1H-1,2,3-triazol-4-yl)cinnolin-3-yl)-1H-pyrazole-4-carboxamide [2176];

N-(6-(1-methyl-1H-1,2,3-triazol-4-yl)cinnolin-3-yl)-1-(piperidin-4-yl)-1H-1,2,3-triazole-4-carboxamide [2177];

1-(1-(2-fluoroethyl)piperidin-4-yl)-N-(6-(1-methyl-1H-1,2,3-triazol-4-yl)cinnolin-3-yl)-1H-1,2,3-triazole-4-carboxamide [2178];

1-(1-isopropylpiperidin-4-yl)-N-(6-(1-methyl-1H-1,2,3-triazol-4-yl)cinnolin-3-yl)-1H-1,2,3-triazole-4-carboxamide [2179];

N-(6-(1-methyl-1H-1,2,3-triazol-4-yl)cinnolin-3-yl)-2-(piperidin-4-yl)oxazole-4-carboxamide [2180];

N-(6-(1-methyl-1H-1,2,3-triazol-4-yl)cinnolin-3-yl)-2-(1-methylpiperidin-4-yl)oxazole-4-carboxamide [2181];

2-(1-isopropylpiperidin-4-yl)-N-(6-(1-methyl-1H-1,2,3-triazol-4-yl)cinnolin-3-yl)oxazole-4-carboxamide [2182];
2-fluoro-N-(6-(1-methyl-1H-1,2,3-triazol-4-yl)cinnolin-3-yl)benzamide [2183];
N-(6-(1-methyl-1H-1,2,3-triazol-4-yl)cinnolin-3-yl)-3-((1-methylpiperidin-4-yl)oxy)benzamide [2184];
N$^2$-methyl-N$^5$-(6-(1-methyl-1H-1,2,3-triazol-4-yl)cinnolin-3-yl)pyridine-2,5-dicarboxamide [2185];
N-(6-(1-methyl-1H-1,2,3-triazol-4-yl)cinnolin-3-yl)-6-(4-methylpiperazin-1-yl)nicotinamide [2186];
2-(3-(dimethylamino)azetidin-1-yl)-N-(6-(1-methyl-1H-1,2,3-triazol-4-yl)cinnolin-3-yl) isonicotinamide [2187];
N-(6-(1-methyl-1H-1,2,3-triazol-4-yl)cinnolin-3-yl)-2-(1-methylpiperidin-4-yl)isonicotinamide [2188];
2-(4-(dimethylamino)piperidin-1-yl)-N-(6-(1-methyl-1H-1,2,3-triazol-4-yl)cinnolin-3-yl) isonicotinamide [2189];
N-(6-(1-methyl-1H-1,2,3-triazol-4-yl)cinnolin-3-yl)-2-morpholinoisonicotinamide [2190];
N-(6-(1-methyl-1H-1,2,3-triazol-4-yl)cinnolin-3-yl)-2-(4-methylpiperazin-1-yl)isonicotinamide [2191];
2-(4-methyl-1,4-diazepan-1-yl)-N-(6-(1-methyl-1H-1,2,3-triazol-4-yl)cinnolin-3-yl) isonicotinamide [2192];
2-(4-isopropylpiperazin-1-yl)-N-(6-(1-methyl-1H-1,2,3-triazol-4-yl)cinnolin-3-yl)isonicotinamide [2193];
N-(6-(1-methyl-1H-1,2,3-triazol-4-yl)cinnolin-3-yl)-2-(piperidin-4-ylamino)isonicotinamide [2194];
2-(methyl(1-methylpiperidin-4-yl)amino)-N-(6-(1-methyl-1H-1,2,33-triazol-4-yl)cinnolin-3-yl)isonicotinamide [2195];
N-(6-(1-methyl-1H-1,2,3-triazol-4-yl)cinnolin-3-yl)-2-((1-methylpiperidin-4-yl)thio) isonicotinamide [2196];
2-methyl-N-(6-(1-methyl-1H-1,2,3-triazol-4-yl)cinnolin-3-yl)-1,2,3,4-tetrahydroisoquinoline-6-carboxamide [2197];
N-(6-(1-methyl-1H-1,2,3-triazol-4-yl)cinnolin-3-yl)-2-(piperazin-1-yl)isonicotinamide [2198];
N-(6-(1-methyl-1H-1,2,3-triazol-4-yl)cinnolin-3-yl)-2-(2-(4-methylpiperazin-1-yl)pyridin-4-yl)acetamide [2199];
1,1-bis(methyl-d$_3$)-4-(4-(((6-(1-methyl-1H-1,2,3-triazol-4-yl)cinnolin-3-yl)carbamoyl)pyridin-2-yl)piperazin-1-ium [2200];
N-(6-(1-methyl-1H-1,2,3-triazol-4-yl)cinnolin-3-yl)-2-(4-(methyl-d$_3$)piperazin-1-yl) isonicotinamide [2201];
N-(6-(1-methyl-1H-1,2,3-triazol-5-yl)cinnolin-3-yl)-1-(3,3,3-trifluoropropyl)piperidine-4-carboxamide [2202];
N-(6-(4-methyl-4H-1,2,4-triazol-3-yl)cinnolin-3-yl)-2-morpholinoacetamide [2203];
N-(6-(4-methyl-4H-1,2,4-triazol-3-yl)cinnolin-3-yl)-1-(3,3,3-trifluoropropyl)piperidine-4-carboxamide [2204];
4-fluoro-1-isobutyl-N-(6-(4-methyl-4H-1,2,4-triazol-3-yl)cinnolin-3-yl)piperidine-4-carboxamide [2205];
N-(6-(4,5-dimethyl-4H-1,2,4-triazol-3-yl)cinnolin-3-yl)-2-morpholinoacetamide [2206];
N-(6-(4,5-dimethyl-4H-1,2,4-triazol-3-yl)cinnolin-3-yl)-1-(3,3,3-trifluoropropyl)piperidine-4-carboxamide [2207];
N-(6-(1H-1,2,3-triazol-1-yl)cinnolin-3-yl)-4-fluoro-1-isobutylpiperidine-4-carboxamide [2208];
N-(6-(2H-1,2,3-triazol-2-yl)cinnolin-3-yl)-4-fluoro-1-isobutylpiperidine-4-carboxamide [2209];
N-(6-(1H-1,2,4-triazol-1-yl)cinnolin-3-yl)-2-(4-methylpiperazin-1-yl)isonicotinamide [2210];
1-isobutyl-N-(6-(1-methyl-1H-tetrazol-5-yl)cinnolin-3-yl)piperidine-4-carboxamide [2211];
2,2,3,3-tetramethyl-N-(6-(1-methyl-1H-imidazol-5-yl)cinnolin-3-yl)cyclopropane-1-carboxamide [2212];
4,4-difluoro-N-(6-(1-methyl-1H-imidazol-5-yl)cinnolin-3-yl)cyclohexane-1-carboxamide [2213];
N-(6-(1-methyl-1H-imidazol-5-yl)cinnolin-3-yl)-2-(piperidin-1-yl)acetamide [2214];
2-fluoro-2-methyl-N-(6-(1-methyl-1H-imidazol-5-yl)cinnolin-3-yl)propanamide [2215];
1-fluoro-N-(6-(1-methyl-1H-imidazol-5-yl)cinnolin-3-yl)cyclopropane-1-carboxamide [2216];
2-methyl-N-(6-(1-methyl-1H-imidazol-5-yl)cinnolin-3-yl)-2-azaspiro[3.3]heptane-6-carboxamide [2217];
1-fluoro-N-(6-(1-methyl-1H-imidazol-5-yl)cinnolin-3-yl)cyclohexane-1-carboxamide [2218];
trans-4-methoxy-N-(6-(1-methyl-1H-imidazol-5-yl)cinnolin-3-yl)cyclohexane-1-carboxamide [2219];
trans-4-(hydroxymethyl)-N-(6-(1-methyl-1H-imidazol-5-yl)cinnolin-3-yl)cyclohexane-1-carboxamide [2220];
N-(6-(1-methyl-1H-imidazol-5-yl)cinnolin-3-yl)azetidine-3-carboxamide [2221];
(R)—N-(6-(1-methyl-1H-imidazol-5-yl)cinnolin-3-yl)tetrahydrofuran-2-carboxamide [2222];
1-(2-methoxyethyl)-N-(6-(1-methyl-1H-imidazol-5-yl)cinnolin-3-yl)piperidine-4-carboxamide [2223];
N-(6-(1-methyl-1H-imidazol-5-yl)cinnolin-3-yl)-1-(3,3,3-trifluoropropyl)piperidine-4-carboxamide [2224];
1-isobutyl-N-(6-(1-methyl-1H-imidazol-5-yl)cinnolin-3-yl)piperidine-4-carboxamide [2225];
N-(6-(1-methyl-1H-imidazol-5-yl)cinnolin-3-yl)-1-(methylsulfonyl)piperidine-4-carboxamide [2226];
N-(6-(1-methyl-1H-imidazol-5-yl)cinnolin-3-yl)-2-(pyrrolidin-1-yl)propanamide [2227];
2-isopropoxy-N-(6-(1-methyl-1H-imidazol-5-yl)cinnolin-3-yl)acetamide [2228];
3-isopropoxy-N-(6-(1-methyl-1H-imidazol-5-yl)cinnolin-3-yl)propanamide [2229];
N-(6-(1,2-dimethyl-1H-imidazol-5-yl)cinnolin-3-yl)cyclopropanecarboxamide [2230];
N-(6-(1,2-dimethyl-1H-imidazol-5-yl)cinnolin-3-yl)cyclohexanecarboxamide [2231];
N-(6-(1,2-dimethyl-1H-imidazol-5-yl)cinnolin-3-yl)-4,4-difluorocyclohexane-1-carboxamide [2232];
(S)—N-(6-(1,2-dimethyl-1H-imidazol-5-yl)cinnolin-3-yl)tetrahydrofuran-2-carboxamide [2233];
N-(6-(1,2-dimethyl-1H-imidazol-5-yl)cinnolin-3-yl)-3,3-difluorocyclobutane-1-carboxamide [2234];
N-(6-(1,2-dimethyl-1H-imidazol-5-yl)cinnolin-3-yl)-1-fluorocyclopropane-1-carboxamide [2235];
N-(6-(1,2-dimethyl-1H-imidazol-5-yl)cinnolin-3-yl)morpholine-4-carboxamide [2236];
N-(6-(1,2-dimethyl-1H-imidazol-5-yl)cinnolin-3-yl)morpholine-d$_8$-4-carboxamide [2237];
1-methyl-N-(6-(1-methyl-1H-imidazol-5-yl)cinnolin-3-yl)-1H-pyrazole-4-carboxamide [2238];
1-ethyl-N-(6-(1-methyl-1H-imidazol-5-yl)cinnolin-3-yl)-1H-pyrazole-4-carboxamide [2239];
1-isopropyl-N-(6-(1-methyl-1H-imidazol-5-yl)cinnolin-3-yl)-1H-pyrazole-4-carboxamide [2240];
1-cyclopropyl-N-(6-(1-methyl-1H-imidazol-5-yl)cinnolin-3-yl)-1H-pyrazole-4-carboxamide [2241];
1-isobutyl-N-(6-(1-methyl-1H-imidazol-5-yl)cinnolin-3-yl)-1H-pyrazole-4-carboxamide [2242];

1-methyl-N-(6-(1-methyl-1H-imidazol-5-yl)cinnolin-3-yl)-1H-pyrazole-3-carboxamide [2243];
N-(6-(1-methyl-1H-imidazol-5-yl)cinnolin-3-yl)-2-(1-methyl-1H-pyrazol-4-yl)acetamide [2244];
1-methyl-N-(6-(1-methyl-1H-imidazol-5-yl)cinnolin-3-yl)-1H-imidazole-4-carboxamide [2245];
1-isopropyl-N-(6-(1-methyl-1H-imidazol-5-yl)cinnolin-3-yl)-1H-imidazole-4-carboxamide [2246];
N-(6-(1-methyl-1H-imidazol-5-yl)cinnolin-3-yl)-1-(tetrahydro-2H-pyran-4-yl)-1H-imidazole-4-carboxamide [2247];
1,2-dimethyl-N-(6-(1-methyl-1H-imidazol-5-yl)cinnolin-3-yl)-1H-imidazole-5-carboxamide [2248];
1-methyl-N-(6-(1-methyl-1H-imidazol-5-yl)cinnolin-3-yl)-1H-1,2,4-triazole-3-carboxamide [2249];
2-methyl-N-(6-(1-methyl-1H-imidazol-5-yl)cinnolin-3-yl)oxazole-4-carboxamide [2250];
2-isopropyl-N-(6-(1-methyl-1H-imidazol-5-yl)cinnolin-3-yl)oxazole-4-carboxamide [2251];
4-methyl-N-(6-(1-methyl-1H-imidazol-5-yl)cinnolin-3-yl)oxazole-2-carboxamide [2252];
4-methyl-N-(6-(1-methyl-1H-imidazol-5-yl)cinnolin-3-yl)thiazole-2-carboxamide [2253];
2-methyl-N-(6-(1-methyl-1H-imidazol-5-yl)cinnolin-3-yl)thiazole-4-carboxamide [2254];
5-methyl-N-(6-(1-methyl-1H-imidazol-5-yl)cinnolin-3-yl)-1,3,4-oxadiazole-2-carboxamide [2255];
5-methyl-N-(6-(1-methyl-1H-imidazol-5-yl)cinnolin-3-yl)-1,3,4-thiadiazole-2-carboxamide [2256];
1-isopropyl-N-(6-(1-isopropyl-1H-imidazol-5-yl)cinnolin-3-yl)-1H-pyrazole-4-carboxamide [2257];
N-(6-(1,2-dimethyl-1H-imidazol-5-yl)cinnolin-3-yl)-1-methyl-1H-pyrazole-4-carboxamide [2258];
N-(6-(1,2-dimethyl-1H-imidazol-5-yl)cinnolin-3-yl)-1-isopropyl-1H-pyrazole-4-carboxamide [2259];
N-(6-(1,2-dimethyl-1H-imidazol-5-yl)cinnolin-3-yl)-2-methylthiazole-5-carboxamide [2260];
4-fluoro-N-(6-(1-methyl-1H-imidazol-5-yl)cinnolin-3-yl)benzamide [2261];
4-(difluoromethoxy)-N-(6-(1-methyl-1H-imidazol-5-yl)cinnolin-3-yl)benzamide [2262];
N-(6-(1-methyl-1H-imidazol-5-yl)cinnolin-3-yl)-3-(pyrrolidin-1-ylmethyl)benzamide [2263];
2-fluoro-N-(6-(1-methyl-1H-imidazol-5-yl)cinnolin-3-yl)benzamide-3,4,5,6-$d_4$ [2264];
4-fluoro-N-(6-(1-methyl-1H-imidazol-5-yl)cinnolin-3-yl)benzamide-2,3,5,6-$d_4$ [2265];
2-chloro-N-(6-(1-methyl-1H-imidazol-5-yl)cinnolin-3-yl)benzamide-3,4,5,6-$d_4$ [2266];
4-chloro-N-(6-(1-methyl-1H-imidazol-5-yl)cinnolin-3-yl)benzamide-2,3,5,6-$d_4$ [2267];
4-(methyl-$d_3$)—N-(6-(1-methyl-1H-imidazol-5-yl)cinnolin-3-yl)benzamide [2268];
4-methyl-N-(6-(1-methyl-1H-imidazol-5-yl)cinnolin-3-yl)benzamide-2,3,5,6-$d_4$ [2269];
4-(methyl-$d_3$)—N-(6-(1-methyl-1H-imidazol-5-yl)cinnolin-3-yl)benzamide-2,3,5,6-$d_4$ [2270];
4-(methoxy-$d_3$)—N-(6-(1-methyl-1H-imidazol-5-yl)cinnolin-3-yl)benzamide [2271];
4-(methoxy-$d_3$)—N-(6-(1-methyl-1H-imidazol-5-yl)cinnolin-3-yl)benzamide-2,3,5,6-$d_4$ [2272];
4-methoxy-N-(6-(1-methyl-1H-imidazol-5-yl)cinnolin-3-yl)benzamide-2,3,5,6-$d_4$ [2273];
(E)-N-(6-(1,2-dimethyl-1H-imidazol-5-yl)cinnolin-3-yl)-3-(phenyl-2,3,4,5,6-$d_5$)acrylamide [2274];
(E)-N-(6-(1,2-dimethyl-1H-imidazol-5-yl)cinnolin-3-yl)-3-(phenyl-2,3,4,5,6-$d_5$)acrylamide-2,3-$d_2$ [2275];
N-(6-(1,2-dimethyl-1H-imidazol-5-yl)cinnolin-3-yl)-2-(4-fluorophenyl)acetamide-2,2-$d_2$ [2276];
(E)-N-(6-(1-methyl-1H-imidazol-5-yl)cinnolin-3-yl)-3-(phenyl-2,3,4,5,6-$d_5$)acrylamide [2277];
(E)-N-(6-(1-methyl-1H-imidazol-5-yl)cinnolin-3-yl)-3-(phenyl-2,3,4,5,6-$d_5$)acrylamide-2,3-$d_2$ [2278];
2-(4-fluorophenyl)-N-(6-(1-methyl-1H-imidazol-5-yl)cinnolin-3-yl)acetamide-2,2-$d_2$ [2279];
N-(6-(1-methyl-1H-imidazol-5-yl)cinnolin-3-yl)-2-(4-methylpiperazin-1-yl)isonicotinamide [2280];
2-(dimethylamino)-N-(6-(1-methyl-1H-imidazol-5-yl)cinnolin-3-yl)isonicotinamide [2281];
2-(3-aminoazetidin-1-yl)-N-(6-(1-methyl-1H-imidazol-5-yl)cinnolin-3-yl)isonicotinamide [2282];
N-(6-(1-methyl-1H-imidazol-5-yl)cinnolin-3-yl)-2-(pyrrolidin-1-yl)isonicotinamide [2283];
N-(6-(1-methyl-1H-imidazol-5-yl)cinnolin-3-yl)-2-(piperidin-1-yl)isonicotinamide [2284];
N-(6-(1-methyl-1H-imidazol-5-yl)cinnolin-3-yl)-2-morpholinoisonicotinamide [2285];
2-(4-isopropylpiperazin-1-yl)-N-(6-(1-methyl-1H-imidazol-5-yl)cinnolin-3-yl)isonicotinamide [2286];
2-(4-cyclopropylpiperazin-1-yl)-N-(6-(1-methyl-1H-imidazol-5-yl)cinnolin-3-yl)isonicotinamide [2287];
N-(6-(1-methyl-1H-imidazol-5-yl)cinnolin-3-yl)-2-(2,7-diazaspiro[3.5]nonan-2-yl) isonicotinamide [2288];
N-(6-(1-methyl-1H-imidazol-5-yl)cinnolin-3-yl)-2-(7-methyl-2,7-diazaspiro[3.5]nonan-2-yl) isonicotinamide [2289];
N-(6-(1-methyl-1H-imidazol-5-yl)cinnolin-3-yl)isoindoline-5-carboxamide [2290];
2-methyl-N-(6-(1-methyl-1H-imidazol-5-yl)cinnolin-3-yl)isoindoline-5-carboxamide [2291];
2-(azetidin-1-yl)-N-(6-(1-methyl-1H-imidazol-5-yl)cinnolin-3-yl)isonicotinamide [2292];
2-methoxy-N-(6-(1-methyl-1H-imidazol-5-yl)cinnolin-3-yl)isonicotinamide [2293];
2-methyl-N-(6-(1-methyl-1H-imidazol-5-yl)cinnolin-3-yl)isonicotinamide [2294];
2-cyano-N-(6-(1-methyl-1H-imidazol-5-yl)cinnolin-3-yl)isonicotinamide [2295];
2-(3,3-difluoroazetidin-1-yl)-N-(6-(1-methyl-1H-imidazol-5-yl)cinnolin-3-yl)isonicotinamide [2296];
2-(4,4-difluoropiperidin-1-yl)-N-(6-(1-methyl-1H-imidazol-5-yl)cinnolin-3-yl)isonicotinamide [2297];
2-isopropoxy-N-(6-(1-methyl-1H-imidazol-5-yl)cinnolin-3-yl)isonicotinamide [2298];
N-(6-(1-methyl-1H-imidazol-5-yl)cinnolin-3-yl)-2-(pyrrolidin-1-yl-2,2,5,5-$d_4$)isonicotinamide [2299];
N-(6-(1-methyl-1H-imidazol-5-yl)cinnolin-3-yl)-2-(pyrrolidin-1-yl-$d_8$)isonicotinamide [2300];
N-(6-(1-methyl-1H-imidazol-5-yl)cinnolin-3-yl)-2-(piperidin-1-yl-$d_{10}$)isonicotinamide [2301];
N-(6-(1-methyl-1H-imidazol-5-yl)cinnolin-3-yl)-2-(morpholino-$d_8$)isonicotinamide [2302];
N-(6-(1,2-dimethyl-1H-imidazol-5-yl)cinnolin-3-yl)-4-isopropoxybenzamide [2303];
N-(6-(1,2-dimethyl-1H-imidazol-5-yl)cinnolin-3-yl)-4-(piperidin-4-yloxy)benzamide [2304];
4-(benzyloxy)-N-(6-(1,2-dimethyl-1H-imidazol-5-yl)cinnolin-3-yl)benzamide [2305];
N-(6-(1,2-dimethyl-1H-imidazol-5-yl)cinnolin-3-yl)-2-fluorobenzamide-3,4,5,6-$d_4$ [2206];
N-(6-(1,2-dimethyl-1H-imidazol-5-yl)cinnolin-3-yl)-4-fluorobenzamide-2,3,5,6-$d_4$ [2307];
2-chloro-N-(6-(1,2-dimethyl-1H-imidazol-5-yl)cinnolin-3-yl)benzamide-3,4,5,6-$d_4$ [2308];

4-chloro-N-(6-(1,2-dimethyl-1H-imidazol-5-yl)cinnolin-3-yl)benzamide-2,3,5,6-d$_4$ [2309];
N-(6-(1,2-dimethyl-1H-imidazol-5-yl)cinnolin-3-yl)-4-(methyl-d$_3$)benzamide [2310];
N-(6-(1,2-dimethyl-1H-imidazol-5-yl)cinnolin-3-yl)-4-methylbenzamide-2,3,5,6-d$_4$ [2311];
N-(6-(1,2-dimethyl-1H-imidazol-5-yl)cinnolin-3-yl)-4-(methyl-d$_3$)benzamide-2,3,5,6-d$_4$ [2312];
N-(6-(1,2-dimethyl-1H-imidazol-5-yl)cinnolin-3-yl)-4-(methoxy-d$_3$)benzamide [2313];
N-(6-(1,2-dimethyl-1H-imidazol-5-yl)cinnolin-3-yl)-4-(methoxy-d$_3$)benzamide-2,3,5,6-d$_4$ [2314];
N-(6-(1,2-dimethyl-1H-imidazol-5-yl)cinnolin-3-yl)-4-methoxybenzamide-2,3,5,6-d$_4$ [2315];
N-(6-(1,2-dimethyl-1H-imidazol-5-yl)cinnolin-3-yl)-2-(4-methylpiperazin-1-yl)isonicotinamide [2316];
N-(6-(1,2-dimethyl-1H-imidazol-5-yl)cinnolin-3-yl)-2-morpholinoisonicotinamide [2317];
N-(6-(1,2-dimethyl-1H-imidazol-5-yl)cinnolin-3-yl)-2-(pyrrolidin-1-yl)isonicotinamide [2318];
N-(6-(1,2-dimethyl-1H-imidazol-5-yl)cinnolin-3-yl)-2-(dimethylamino)isonicotinamide [2319];
N-(6-(1,2-dimethyl-1H-imidazol-5-yl)cinnolin-3-yl)-2-(pyrrolidin-1-yl-2,2,5,5-d$_4$) isonicotinamide [2320];
N-(6-(1,2-dimethyl-1H-imidazol-5-yl)cinnolin-3-yl)-2-(pyrrolidin-1-yl-d$_8$)isonicotinamide [2321];
N-(6-(1,2-dimethyl-1H-imidazol-5-yl)cinnolin-3-yl)-2-(piperidin-1-yl-d$_{10}$)isonicotinamide [2322];
N-(6-(1,2-dimethyl-1H-imidazol-5-yl)cinnolin-3-yl)-2-(morpholino-d$_8$)isonicotinamide [2323];
N-(6-(5,6,7,8-tetrahydroimidazo[1,2-a]pyrazin-3-yl)cinnolin-3-yl)cyclopropanecarboxamide [2324];
N-(6-(7-methyl-5,6,7,8-tetrahydroimidazo[1,2-a]pyrazin-3-yl)cinnolin-3-yl) cyclopropanecarboxamide [2325];
3,3-difluoro-N-(6-(5,6,7,8-tetrahydroimidazo[1,2-a]pyrazin-3-yl)cinnolin-3-yl)cyclobutane-1-carboxamide [2326];
(R)—N-(6-(5,6,7,8-tetrahydroimidazo[1,2-a]pyrazin-3-yl)cinnolin-3-yl)pyrrolidine-2-carboxamide [2327];
(R)—N-(6-(5,6,7,8-tetrahydroimidazo[1,2-a]pyrazin-3-yl)cinnolin-3-yl)piperidine-3-carboxamide [2328];
1-methyl-N-(6-(5,6,7,8-tetrahydroimidazo[1,2-a]pyrazin-3-yl)cinnolin-3-yl)piperidine-4-carboxamide [2329];
N-(6-(5,6,7,8-tetrahydroimidazo[1,2-a]pyrazin-3-yl)cinnolin-3-yl)-1-((1-(trifluoromethyl) cyclopropyl)methyl)piperidine-4-carboxamide [2330];
1-benzoyl-N-(6-(5,6,7,8-tetrahydroimidazo[1,2-a]pyrazin-3-yl)cinnolin-3-yl)piperidine-4-carboxamide [2331];
4-fluoro-1-isobutyl-N-(6-(5,6,7,8-tetrahydroimidazo[1,2-a]pyrazin-3-yl)cinnolin-3-yl)piperidine-4-carboxamide [2332];
(R)-2-(2-methylpyrrolidin-1-yl)-N-(6-(5,6,7,8-tetrahydroimidazo[1,2-a]pyrazin-3-yl)cinnolin-3-yl)acetamide [2333];
2-(cyclobutyl(methyl)amino)-N-(6-(5,6,7,8-tetrahydroimidazo[1,2-a]pyrazin-3-yl)cinnolin-3-yl)acetamide [2334];
4-fluoro-N-(6-(5,6,7,8-tetrahydroimidazo[1,2-a]pyrazin-3-yl)cinnolin-3-yl)benzamide [2335];
4-isopropoxy-N-(6-(5,6,7,8-tetrahydroimidazo[1,2-a]pyrazin-3-yl)cinnolin-3-yl)benzamide [2336];
4-(difluoromethoxy)-N-(6-(5,6,7,8-tetrahydroimidazo[1,2-a]pyrazin-3-yl)cinnolin-3-yl) benzamide [2337];
2-((2-(dimethylamino)ethyl)amino)-N-(6-(5,6,7,8-tetrahydroimidazo[1,2-a]pyrazin-3-yl)cinnolin-3-yl)isonicotinamide [2338];
2-((1-isopropylpiperidin-4-yl)oxy)-N-(6-(5,6,7,8-tetrahydroimidazo[1,2-a]pyrazin-3-yl)cinnolin-3-yl)isonicotinamide [2339];
N-(6-(oxazol-5-yl)cinnolin-3-yl)-1-(3,3,3-trifluoropropyl)piperidine-4-carboxamide [2340];
N-(6-(oxazol-5-yl)cinnolin-3-yl)cyclopropanecarboxamide [2341];
(R)—N-(6-(oxazol-5-yl)cinnolin-3-yl)tetrahydrofuran-2-carboxamide [2342];
(R)—N-(6-(oxazol-5-yl)cinnolin-3-yl)piperidine-3-carboxamide [2343];
N-(6-(oxazol-5-yl)cinnolin-3-yl)tetrahydro-2H-pyran-4-carboxamide [2344];
N-(6-(oxazol-5-yl)cinnolin-3-yl)-1-(2-(pyrrolidin-1-yl)acetyl)piperidine-4-carboxamide [2345];
1'-methyl-N-(6-(oxazol-5-yl)cinnolin-3-yl)-[1,4'-bipiperidine]-4-carboxamide [2346];
cis-4-morpholino-N-(6-(oxazol-5-yl)cinnolin-3-yl)cyclohexane-1-carboxamide [2347];
2-(cyclobutyl(methyl)amino)-N-(6-(oxazol-5-yl)cinnolin-3-yl)acetamide [2348];
N-(6-(oxazol-5-yl)cinnolin-3-yl)-2-(pyrrolidin-1-yl)acetamide [2349];
(R)-2-(2-methylpyrrolidin-1-yl)-N-(6-(oxazol-5-yl)cinnolin-3-yl)acetamide [2350];
2-(4-methylpiperazin-1-yl)-N-(6-(oxazol-5-yl)cinnolin-3-yl)acetamide [2351];
trans-4-((4-methylpiperazin-1-yl)methyl)-N-(6-(oxazol-5-yl)cinnolin-3-yl)cyclohexane-1-carboxamide [2352];
1-(2,2-difluoropropyl)-N-(6-(oxazol-5-yl)cinnolin-3-yl) piperidine-4-carboxamide [2353];
trans-4-(hydroxymethyl)-N-(6-(2-methyloxazol-5-yl)cinnolin-3-yl)cyclohexane-1-carboxamide [2354];
trans-4-(methylamino)-N-(6-(2-methyloxazol-5-yl)cinnolin-3-yl)cyclohexane-1-carboxamide [2355];
trans-4-((1,3-difluoropropan-2-yl)amino)-N-(6-(2-methyloxazol-5-yl)cinnolin-3-yl)cyclohexane-1-carboxamide [2356];
trans-N-(6-(2-methyloxazol-5-yl)cinnolin-3-yl)-4-((propan-2-yl-1,1,1,3,3,3-d$_6$)amino) cyclohexane-1-carboxamide [2357];
trans-4-((2,2-difluoroethyl)amino)-N-(6-(2-methyloxazol-5-yl)cinnolin-3-yl)cyclohexane-1-carboxamide [2358];
trans-N-(6-(2-methyloxazol-5-yl)cinnolin-3-yl)-4-((3,3,3-trifluoropropyl)amino)cyclohexane-1-carboxamide [2359];
trans-4-((2-methoxyethyl)amino)-N-(6-(2-methyloxazol-5-yl)cinnolin-3-yl)cyclohexane-1-carboxamide [2360];
trans-4-(dimethylamino)-N-(6-(2-methyloxazol-5-yl)cinnolin-3-yl)cyclohexane-1-carboxamide [2361];
trans-4-(bis(methyl-d$_3$)amino)-N-(6-(2-methyloxazol-5-yl)cinnolin-3-yl)cyclohexane-1-carboxamide [2362];
cis-4-(dimethylamino)-N-(6-(2-methyloxazol-5-yl)cinnolin-3-yl)cyclohexane-1-carboxamide [2363];
trans-4-((2,2-difluoroethyl)(methyl)amino)-N-(6-(2-methyloxazol-5-yl)cinnolin-3-yl) cyclohexane-1-carboxamide [2364];
trans-4-(methyl(oxetan-3-yl)amino)-N-(6-(2-methyloxazol-5-yl)cinnolin-3-yl)cyclohexane-1-carboxamide [2365];
trans-4-((2-fluoroethyl)amino)-N-(6-(2-methyloxazol-5-yl)cinnolin-3-yl)cyclohexane-1-carboxamide [2366];
trans-4-(2-(fluoromethyl)aziridin-1-yl)-N-(6-(2-methyloxazol-5-yl)cinnolin-3-yl)cyclohexane-1-carboxamide [2367];

trans-4-((3-fluoroazetidin-1-yl)methyl)-N-(6-(2-methyloxazol-5-yl)cinnolin-3-yl)cyclohexane-1-carboxamide [2368];
trans-N-(6-(2-methyloxazol-5-yl)cinnolin-3-yl)-3-morpholinocyclobutane-1-carboxamide [2369];
trans-N-(6-(2-methyloxazol-5-yl)cinnolin-3-yl)-4-morpholinocyclohexane-1-carboxamide [2370];
N-(6-(2-methyloxazol-5-yl)cinnolin-3-yl)-2-(piperidin-1-yl)acetamide [2371];
2-(4-methoxypiperidin-1-yl)-N-(6-(2-methyloxazol-5-yl)cinnolin-3-yl)acetamide [2372];
N-(6-(2-methyloxazol-5-yl)cinnolin-3-yl)-2-(4-methylpiperazin-1-yl)acetamide [2373];
N-(6-(2-methyloxazol-5-yl)cinnolin-3-yl)morpholine-4-carboxamide [2374];
N-(6-(2-methyloxazol-5-yl)cinnolin-3-yl)-2-morpholinoacetamide [2375];
N-(6-(2-methyloxazol-5-yl)cinnolin-3-yl)-3-morpholinopropanamide [2376];
1-methyl-N-(6-(2-methyloxazol-5-yl)cinnolin-3-yl)piperidine-4-carboxamide [2377];
1-(2,2-difluoropropyl)-N-(6-(2-methyloxazol-5-yl)cinnolin-3-yl)piperidine-4-carboxamide [2378];
N-(6-(2-methyloxazol-5-yl)cinnolin-3-yl)-4-morpholinopiperidine-1-carboxamide [2379];
4-((1,3-difluoropropan-2-yl)amino)-N-(6-(2-methyloxazol-5-yl)cinnolin-3-yl)piperidine-1-carboxamide [2380];
(1R,3s,5S)-3-((1,3-difluoropropan-2-yl)amino)-N-(6-(2-methyloxazol-5-yl)cinnolin-3-yl)-8-azabicyclo[3.2.1]octane-8-carboxamide [2381];
(1R,3s,5S)-3-((1,3-difluoropropan-2-yl)amino)-N-(6-(2-methyloxazol-5-yl)cinnolin-3-yl)-8-azabicyclo[3.2.1]octane-8-carboxamide [2382];
4-(dimethylamino)-N-(6-(2-methyloxazol-5-yl)cinnolin-3-yl)piperidine-1-carboxamide [2383];
4-((2,2-difluoroethyl)(methyl)amino)-N-(6-(2-methyloxazol-5-yl)cinnolin-3-yl)piperidine-1-carboxamide [2384];
(3S,4S)-4-amino-3-fluoro-N-(6-(2-methyloxazol-5-yl)cinnolin-3-yl)piperidine-1-carboxamide [2385];
(3S,4S)-3-fluoro-4-(methylamino)-N-(6-(2-methyloxazol-5-yl)cinnolin-3-yl)piperidine-1-carboxamide [2386];
(3R,4R)-4-amino-3-fluoro-N-(6-(2-methyloxazol-5-yl)cinnolin-3-yl)piperidine-1-carboxamide [2387];
(3R,4R)-3-fluoro-4-(methylamino)-N-(6-(2-methyloxazol-5-yl)cinnolin-3-yl)piperidine-1-carboxamide [2388];
4-((2-fluoroethyl)amino)-N-(6-(2-methyloxazol-5-yl)cinnolin-3-yl)piperidine-1-carboxamide [2389];
4-((2,2-difluoroethyl)amino)-N-(6-(2-methyloxazol-5-yl)cinnolin-3-yl)piperidine-1-carboxamide [2390];
(1R,3s,5S)-3-amino-N-(6-(2-methyloxazol-5-yl)cinnolin-3-yl)-8-azabicyclo[3.2.1]octane-8-carboxamide [2391];
(1R,3r,5S)-3-amino-N-(6-(2-methyloxazol-5-yl)cinnolin-3-yl)-8-azabicyclo[3.2.1]octane-8-carboxamide [2392];
(1R,3r,5S)-3-((2-fluoroethyl)amino)-N-(6-(2-methyloxazol-5-yl)cinnolin-3-yl)-8-azabicyclo[3.2.1]octane-8-carboxamide [2393];
(1R,3r,5S)-3-((2,2-difluoroethyl)amino)-N-(6-(2-methyloxazol-5-yl)cinnolin-3-yl)-8-azabicyclo[3.2.1]octane-8-carboxamide [2394];
(1R,3s,5S)—N-(6-(2-methyloxazol-5-yl)cinnolin-3-yl)-3-((3,3,3-trifluoropropyl)amino)-8-azabicyclo [3.2.1]octane-8-carboxamide [2395];
(3S,4S)-3-fluoro-4-(isopropylamino)-N-(6-(2-methyloxazol-5-yl)cinnolin-3-yl)piperidine-1-carboxamide [2396];
N-(6-(2-methyloxazol-5-yl)cinnolin-3-yl)-5,6-dihydroimidazo[1,2-a]pyrazine-7(8H)-carboxamide [2397];
2-methyl-N-(6-(2-methyloxazol-5-yl)cinnolin-3-yl)-5,6-dihydroimidazo[1,2-a]pyrazine-7(8H)-carboxamide [2398];
N-(6-(2-methyloxazol-5-yl)cinnolin-3-yl)-2-(morpholino-$d_8$)acetamide [2399];
trans-N-(6-(2-methyloxazol-4-yl)cinnolin-3-yl)-4-(4-methylpiperazin-1-yl)cyclohexane-1-carboxamide [2400];
N-(6-(2-methyloxazol-5-yl)cinnolin-3-yl)-1-(1-methylpiperidin-4-yl)-1H-pyrazole-4-carboxamide [2401];
2-(1H-imidazol-1-yl)-N-(6-(2-methyloxazol-5-yl)cinnolin-3-yl)acetamide [2402];
4-(difluoromethoxy)-N-(6-(oxazol-5-yl)cinnolin-3-yl)benzamide [2403];
3-((1-methylpiperidin-4-yl)oxy)-N-(6-(oxazol-5-yl)cinnolin-3-yl)benzamide [2404];
N-(6-(oxazol-5-yl)cinnolin-3-yl)isonicotinamide [2405];
2-(3-aminoazetidin-1-yl)-N-(6-(oxazol-5-yl)cinnolin-3-yl)isonicotinamide [2406];
2-(1-methylpiperidin-4-yl)-N-(6-(oxazol-5-yl)cinnolin-3-yl)isonicotinamide [2407];
1'-methyl-N-(6-(oxazol-5-yl)cinnolin-3-yl)-1',2',3',6'-tetrahydro-[2,4'-bipyridine]-4-carboxamide [2408];
2-(4-methylpiperazin-1-yl)-N-(6-(oxazol-5-yl)cinnolin-3-yl)isonicotinamide [2409];
2-(7-methyl-2,7-diazaspiro[3.5]nonan-2-yl)-N-(6-(oxazol-5-yl)cinnolin-3-yl)isonicotinamide [2410];
N-(6-(oxazol-5-yl)cinnolin-3-yl)-2-(2,7-diazaspiro[3.5]nonan-7-yl)isonicotinamide [2411];
N-(6-(oxazol-5-yl)cinnolin-3-yl)-2-(piperidin-4-ylamino)isonicotinamide [2412];
2-methyl-N-(6-(oxazol-5-yl)cinnolin-3-yl)isoindoline-5-carboxamide [2413];
N-(6-(oxazol-5-yl)cinnolin-3-yl)-1,2,3,4-tetrahydroisoquinoline-7-carboxamide [2414];
N-(6-(2-methyloxazol-5-yl)cinnolin-3-yl)-2-(4-methylpiperazin-1-yl)isonicotinamide [2415];
N-(6-(3-methylisoxazol-5-yl)cinnolin-3-yl)-1-(3,3,3-trifluoropropyl)piperidine-4-carboxamide [2416];
4-fluoro-1-isobutyl-N-(6-(5-methyl-1,3,4-oxadiazol-2-yl)cinnolin-3-yl)piperidine-4-carboxamide [2417];
1-isobutyl-N-(6-(5-methyl-1,3,4-oxadiazol-2-yl)cinnolin-3-yl)piperidine-4-carboxamide [2418];
N-(6-(5-(dimethylamino)-1,3,4-oxadiazol-2-yl)cinnolin-3-yl)piperidine-4-carboxamide [2419];
N-(6-(5-(dimethylamino)-1,3,4-oxadiazol-2-yl)cinnolin-3-yl)-1-methylpiperidine-4-carboxamide [2420];
N-(6-(5-methyl-1,3,4-oxadiazol-2-yl)cinnolin-3-yl)-2-(4-methylpiperazin-1-yl)isonicotinamide [2421];
3,3-difluoro-N-(6-(thiazol-5-yl)cinnolin-3-yl)cyclobutane-1-carboxamide [2422];
2-methyl-N-(6-(thiazol-5-yl)cinnolin-3-yl)-2-azaspiro[3.3]heptane-6-carboxamide [2423];
1-fluoro-N-(6-(thiazol-5-yl)cinnolin-3-yl)cyclohexane-1-carboxamide [2424];
trans-4-(dimethylamino)-N-(6-(thiazol-5-yl)cinnolin-3-yl)cyclohexane-1-carboxamide [2425];

trans-4-((3-fluoroazetidin-1-yl)methyl)-N-(6-(thiazol-5-yl)cinnolin-3-yl)cyclohexane-1-carboxamide [2426];
N-(6-(thiazol-5-yl)cinnolin-3-yl)azetidine-3-carboxamide [2427];
1-methyl-N-(6-(thiazol-5-yl)cinnolin-3-yl)piperidine-4-carboxamide [2428];
1-(2,2-difluoropropyl)-N-(6-(thiazol-5-yl)cinnolin-3-yl) piperidine-4-carboxamide [2429];
1-(oxetan-3-yl)-N-(6-(thiazol-5-yl)cinnolin-3-yl)piperidine-4-carboxamide [2430];
1-(2-(pyrrolidin-1-yl)acetyl)-N-(6-(thiazol-5-yl)cinnolin-3-yl)piperidine-4-carboxamide [2431];
1'-methyl-N-(6-(thiazol-5-yl)cinnolin-3-yl)-[1 1,4'-bipiperidine]-4-carboxamide [2432];
2-(pyrrolidin-1-yl)-N-(6-(thiazol-5-yl)cinnolin-3-yl)propanamide [2433];
2-(piperidin-1-yl)-N-(6-(thiazol-5-yl)cinnolin-3-yl)acetamide [2434];
2-(4-methylpiperazin-1-yl)-N-(6-(thiazol-5-yl)cinnolin-3-yl)acetamide [2435];
2-morpholino-N-(6-(thiazol-5-yl)cinnolin-3-yl)acetamide [2436];
4-(piperidin-4-yloxy)-N-(6-(thiazol-5-yl)cinnolin-3-yl)benzamide [2437];
N-(6-(thiazol-5-yl)cinnolin-3-yl)isonicotinamide [2438];
6-(4-methylpiperazin-1-yl)-N-(6-(thiazol-5-yl)cinnolin-3-yl)nicotinamide [2439];
1'-methyl-N-(6-(thiazol-5-yl)cinnolin-3-yl)-1',2',3',6'-tetrahydro-[2,4'-bipyridine]-4-carboxamide [2440];
2-(3-(dimethylamino)azetidin-1-yl)-N-(6-(thiazol-5-yl)cinnolin-3-yl)isonicotinamide [2441];
2-(4-(dimethylamino)piperidin-1-yl)-N-(6-(thiazol-5-yl)cinnolin-3-yl)isonicotinamide [2442];
2-(4-methylpiperazin-1-yl)-N-(6-(thiazol-5-yl)cinnolin-3-yl)isonicotinamide [2443];
2-((1-methylpiperidin-4-yl)thio)-N-(6-(thiazol-5-yl)cinnolin-3-yl)isonicotinamide [2444];
N-(6-(thiazol-5-yl)cinnolin-3-yl)-1,2,3,4-tetrahydroisoquinoline-7-carboxamide [2445];
trans-4-((1,3-difluoropropan-2-yl)amino)-N-(6-(5-methyl-1,3,4-thiadiazol-2-yl)cinnolin-3-yl) cyclohexane-1-carboxamide [2446];
N-(6-(2-methylthiazol-5-yl)cinnolin-3-yl)morpholine-4-carboxamide [2447];
N-(6-(2-methylthiazol-5-yl)cinnolin-3-yl)-2-(pyrrolidin-1-yl)acetamide [2448];
2-((1R,4R)-2-oxa-5-azabicyclo[2.2.1]heptan-5-yl)-N-(6-(2-methylthiazol-5-yl)cinnolin-3-yl)acetamide [2449];
N-(6-(2-methylthiazol-5-yl)cinnolin-3-yl)-2-morpholinoacetamide [2450];
N-(6-(2-methylthiazol-5-yl)cinnolin-3-yl)-2-(morpholino-d$_8$)acetamide [2451];
2-(4-methylpiperazin-1-yl)-N-(6-(2-methylthiazol-5-yl)cinnolin-3-yl)acetamide [2452];
1-methyl-N-(6-(2-methylthiazol-5-yl)cinnolin-3-yl)piperidine-4-carboxamide [2453];
N-(6-(2-methylthiazol-5-yl)cinnolin-3-yl)isonicotinamide [2454];
N-(6-(2-methylthiazol-5-yl)cinnolin-3-yl)nicotinamide [2455];
2-(4-methylpiperazin-1-yl)-N-(6-(2-methylthiazol-5-yl)cinnolin-3-yl)isonicotinamide [2456];
trans-N-(6-(5-methyl-1,3,4-thiadiazol-2-yl)cinnolin-3-yl)-4-morpholinocyclohexane-1-carboxamide [2457];
trans-N-(6-(5-methyl-1,3,4-thiadiazol-2-yl)cinnolin-3-yl)-4-(4-methylpiperazin-1-yl) cyclohexane-1-carboxamide [2458];
4-isopropyl-N-(6-(5-methyl-1,3,4-thiadiazol-2-yl)cinnolin-3-yl)piperazine-1-carboxamide [2459];
4-((2-methoxyethyl)(methyl)amino)-N-(6-(5-methyl-1,3,4-thiadiazol-2-yl)cinnolin-3-yl) piperidine-1-carboxamide [2460];
4-((1,3-difluoropropan-2-yl)amino)-N-(6-(5-methyl-1,3,4-thiadiazol-2-yl)cinnolin-3-yl) piperidine-1-carboxamide [2461];
N-(6-(5-methyl-1,3,4-thiadiazol-2-yl)cinnolin-3-yl)-4-((3,3,3-trifluoropropyl)amino)piperidine-1-carboxamide [2462];
4-((2-fluoroethyl)amino)-N-(6-(5-methyl-1,3,4-thiadiazol-2-yl)cinnolin-3-yl)piperidine-1-carboxamide [2463];
(3R,4S)-4-amino-3-fluoro-N-(6-(5-methyl-1,3,4-thiadiazol-2-yl)cinnolin-3-yl)piperidine-1-carboxamide [2464];
(3R,4R)-4-amino-3-fluoro-N-(6-(5-methyl-1,3,4-thiadiazol-2-yl)cinnolin-3-yl)piperidine-1-carboxamide [2465];
(3S,4S)-3-fluoro-N-(6-(5-methyl-1,3,4-thiadiazol-2-yl)cinnolin-3-yl)-4-(methylamino)piperidine-1-carboxamide [2466];
(3R,4R)-3-fluoro-N-(6-(5-methyl-1,3,4-thiadiazol-2-yl)cinnolin-3-yl)-4-(methylamino) piperidine-1-carboxamide [2467];
4-amino-3,3-difluoro-N-(6-(5-methyl-1,3,4-thiadiazol-2-yl)cinnolin-3-yl)piperidine-1-carboxamide [2468];
(3R,4R)-3-fluoro-4-(isopropylamino)-N-(6-(5-methyl-1,3,4-thiadiazol-2-yl)cinnolin-3-yl) piperidine-1-carboxamide [2469];
(3R,4S)-3-fluoro-4-(isopropylamino)-N-(6-(5-methyl-1,3,4-thiadiazol-2-yl)cinnolin-3-yl) piperidine-1-carboxamide [2470];
3,3-difluoro-4-(isopropylamino)-N-(6-(5-methyl-1,3,4-thiadiazol-2-yl)cinnolin-3-yl)piperidine-1-carboxamide [2471];
(3S,4S)-3-fluoro-N-(6-(5-methyl-1,3,4-thiadiazol-2-yl)cinnolin-3-yl)-4-((propan-2-yl-1,1,1,3,3,3-d$_6$)amino)piperidine-1-carboxamide [2472];
(1R,3s,5S)-3-((1,3-difluoropropan-2-yl)amino)-N-(6-(5-methyl-1,3,4-thiadiazol-2-yl)cinnolin-3-yl)-8-azabicyclo[3.2.1]octane-8-carboxamide [2473];
(1R,3s,5S)-3-((1,3-difluoropropan-2-yl)amino)-N-(6-(5-methyl-1,3,4-thiadiazol-2-yl)cinnolin-3-yl)-8-azabicyclo[3.2.1]octane-8-carboxamide [2474];
4-(dimethylamino)-N-(6-(2-methylthiazol-5-yl)cinnolin-3-yl)piperidine-1-carboxamide [2475];
4-((2,2-difluoroethyl)amino)-N-(6-(5-methyl-1,3,4-thiadiazol-2-yl)cinnolin-3-yl)piperidine-1-carboxamide [2476];
4-((2,2-difluoroethyl)(methyl-d$_3$)amino)-N-(6-(5-methyl-1,3,4-thiadiazol-2-yl)cinnolin-3-yl)piperidine-1-carboxamide [2477];
N-(6-(5-methyl-1,3,4-thiadiazol-2-yl)cinnolin-3-yl)-4-morpholinopiperidine-1-carboxamide [2478];
N-(6-(5-methyl-1,3,4-thiadiazol-2-yl)cinnolin-3-yl)-4-(4-methylpiperazin-1-yl)piperidine-1-carboxamide [2479];
(R)-3,4-dimethyl-N-(6-(5-methyl-1,3,4-thiadiazol-2-yl)cinnolin-3-yl)piperazine-1-carboxamide [2480];
(S)-3,4-dimethyl-N-(6-(5-methyl-1,3,4-thiadiazol-2-yl)cinnolin-3-yl)piperazine-1-carboxamide [2481];
(1R,3r,5 S)-3-((2-fluoroethyl)amino)-N-(6-(5-methyl-1,3,4-thiadiazol-2-yl)cinnolin-3-yl)-8-azabicyclo[3.2.1]octane-8-carboxamide [2482];

(1R,3r,5S)-3-((2,2-difluoroethyl)amino)-N-(6-(5-methyl-1,3,4-thiadiazol-2-yl)cinnolin-3-yl)-8-azabicyclo[3.2.1]octane-8-carboxamide [2483];

(1R,3r,5 S)-3-amino-N-(6-(5-methyl-1,3,4-thiadiazol-2-yl)cinnolin-3-yl)-8-azabicyclo[3.2.1] octane-8-carboxamide [2484];

(1S,4S)-5-methyl-N-(6-(5-methyl-1,3,4-thiadiazol-2-yl)cinnolin-3-yl)-2,5-diazabicyclo[2.2.1] heptane-2-carboxamide [2485];

(1R,4R)-5-methyl-N-(6-(5-methyl-1,3,4-thiadiazol-2-yl)cinnolin-3-yl)-2,5-diazabicyclo[2.2.1] heptane-2-carboxamide [2486];

8-methyl-N-(6-(5-methyl-1,3,4-thiadiazol-2-yl)cinnolin-3-yl)-3,8-diazabicyclo[3.2.1]octane-3-carboxamide [2487];

3-methyl-N-(6-(5-methyl-1,3,4-thiadiazol-2-yl)cinnolin-3-yl)-3,8-diazabicyclo[3.2.1]octane-8-carboxamide [2488];

N-(6-(5-methyl-1,3,4-thiadiazol-2-yl)cinnolin-3-yl)-5,6-dihydroimidazo[1,2-a]pyrazine-7(8H)-carboxamide [2489];

2-(4-methylpiperazin-1-yl)-N-(6-(5-methylthiazol-2-yl)cinnolin-3-yl)isonicotinamide [2490];

2-(4-methylpiperazin-1-yl)-N-(6-(4-methylthiazol-2-yl)cinnolin-3-yl)isonicotinamide [2491];

N-(6-(2-(methylamino)thiazol-5-yl)cinnolin-3-yl)piperidine-4-carboxamide [2492];

1-methyl-N-(6-(2-(methylamino)thiazol-5-yl)cinnolin-3-yl)piperidine-4-carboxamide [2493];

N-(6-(2-(diethylamino)thiazol-5-yl)cinnolin-3-yl)-2-(4-fluoropiperidin-1-yl)acetamide [2494];

N-(6-(2-(diethylamino)thiazol-5-yl)cinnolin-3-yl)-2-(4-methylpiperazin-1-yl)acetamide [2495];

N-(6-(2-aminothiazol-5-yl)cinnolin-3-yl)-2-(4-methylpiperazin-1-yl)isonicotinamide [2496];

N-(6-(2-(methylamino)thiazol-5-yl)cinnolin-3-yl)-2-(4-methylpiperazin-1-yl)isonicotinamide [2497];

N-(6-(2-(dimethylamino)thiazol-5-yl)cinnolin-3-yl)-2-(4-methylpiperazin-1-yl)isonicotinamide [2498];

2-(4-isopropylpiperazin-1-yl)-N-(6-(2-(methylamino)thiazol-5-yl)cinnolin-3-yl)isonicotinamide [2499];

2-(3-(dimethylamino)azetidin-1-yl)-N-(6-(2-(methylamino)thiazol-5-yl)cinnolin-3-yl) isonicotinamide [2500];

2-(3-(dimethylamino)azetidin-1-yl)-N-(6-(2-(dimethylamino)thiazol-5-yl)cinnolin-3-yl) isonicotinamide [2501];

2-(3-aminoazetidin-1-yl)-N-(6-(2-(dimethylamino)thiazol-5-yl)cinnolin-3-yl)isonicotinamide [2502];

N-(6-(5-chlorothiazol-2-yl)cinnolin-3-yl)-2-(4-methylpiperazin-1-yl)isonicotinamide [2503];

2-(3-(2-(4-methylpiperazin-1-yl)isonicotinamido)cinnolin-6-yl)thiazole-5-carboxamide [2504];

N-(6-(isothiazol-4-yl)cinnolin-3-yl)-1-methylpiperidine-4-carboxamide [2505];

N-(6-(1,3,4-thiadiazol-2-yl)cinnolin-3-yl)-4-(difluoromethoxy)benzamide [2506];

N-(6-(1,3,4-thiadiazol-2-yl)cinnolin-3-yl)-4-(piperidin-4-yloxy)benzamide [2507];

N-(6-(1,3,4-thiadiazol-2-yl)cinnolin-3-yl)-4-((l-methylpiperidin-4-yl)oxy)benzamide [2508];

N-(6-(1,3,4-thiadiazol-2-yl)cinnolin-3-yl)-3-((1-methylpiperidin-4-yl)oxy)benzamide [2509];

$N^5$-(6-(1,3,4-thiadiazol-2-yl)cinnolin-3-yl)-$N^2$-methylpyridine-2,5-dicarboxamide [2510];

N-(6-(1,3,4-thiadiazol-2-yl)cinnolin-3-yl)-6-(4-methylpiperazin-1-yl)nicotinamide [2511];

N-(6-(1,3,4-thiadiazol-2-yl)cinnolin-3-yl)-1'-methyl-1',2',3',6'-tetrahydro-[2,4'-bipyridine]-4-carboxamide [2512];

N-(6-(1,3,4-thiadiazol-2-yl)cinnolin-3-yl)-2-(3-(dimethylamino)azetidin-1-yl)isonicotinamide [2513];

N-(6-(1,3,4-thiadiazol-2-yl)cinnolin-3-yl)-2-(4-methylpiperazin-1-yl)isonicotinamide [2514];

N-(6-(1,3,4-thiadiazol-2-yl)cinnolin-3-yl)-2-(4-isopropylpiperazin-1-yl)isonicotinamide [2515];

N-(6-(1,3,4-thiadiazol-2-yl)cinnolin-3-yl)-2-morpholinoisonicotinamide [2516];

1-fluoro-N-(6-(5-methyl-1,3,4-thiadiazol-2-yl)cinnolin-3-yl)cyclohexane-1-carboxamide [2517];

trans-4-methoxy-N-(6-(5-methyl-1,3,4-thiadiazol-2-yl)cinnolin-3-yl)cyclohexane-1-carboxamide [2518];

cis-4-methoxy-N-(6-(5-methyl-1,3,4-thiadiazol-2-yl)cinnolin-3-yl)cyclohexane-1-carboxamide [2519];

trans-4-amino-N-(6-(5-methyl-1,3,4-thiadiazol-2-yl)cinnolin-3-yl)cyclohexane-1-carboxamide [2520];

trans-4-(dimethylamino)-N-(6-(5-methyl-1,3,4-thiadiazol-2-yl)cinnolin-3-yl)cyclohexane-1-carboxamide [2521];

trans-N-(6-(5-methyl-1,3,4-thiadiazol-2-yl)cinnolin-3-yl)-4-morpholinocyclohexane-1-carboxamide [2522];

trans-4-(hydroxymethyl)-N-(6-(5-methyl-1,3,4-thiadiazol-2-yl)cinnolin-3-yl)cyclohexane-1-carboxamide [2523];

N-(6-(5-methyl-1,3,4-thiadiazol-2-yl)cinnolin-3-yl)piperidine-4-carboxamide [2524];

4-fluoro-N-(6-(5-methyl-1,3,4-thiadiazol-2-yl)cinnolin-3-yl)piperidine-4-carboxamide [2525];

1-methyl-N-(6-(5-methyl-1,3,4-thiadiazol-2-yl)cinnolin-3-yl)piperidine-4-carboxamide [2526];

4-fluoro-1-methyl-N-(6-(5-methyl-1,3,4-thiadiazol-2-yl)cinnolin-3-yl)piperidine-4-carboxamide [2527];

1-(2-fluoroethyl)-N-(6-(5-methyl-1,3,4-thiadiazol-2-yl)cinnolin-3-yl)piperidine-4-carboxamide [2528];

1-(2,2-difluoroethyl)-N-(6-(5-methyl-1,3,4-thiadiazol-2-yl)cinnolin-3-yl)piperidine-4-carboxamide [2529];

N-(6-(5-methyl-1,3,4-thiadiazol-2-yl)cinnolin-3-yl)-1-(3,3,3-trifluoropropyl)piperidine-4-carboxamide [2530];

1-(2,2-difluoropropyl)-N-(6-(5-methyl-1,3,4-thiadiazol-2-yl)cinnolin-3-yl)piperidine-4-carboxamide [2531];

1-benzoyl-N-(6-(5-methyl-1,3,4-thiadiazol-2-yl)cinnolin-3-yl)piperidine-4-carboxamide [2532];

N-(6-(5-methyl-1,3,4-thiadiazol-2-yl)cinnolin-3-yl)-2-(pyrrolidin-1-yl)acetamide [2533];

N-(6-(5-methyl-1,3,4-thiadiazol-2-yl)cinnolin-3-yl)-2-(piperidin-1-yl)acetamide [2534];

2-(4-methoxypiperidin-1-yl)-N-(6-(5-methyl-1,3,4-thiadiazol-2-yl)cinnolin-3-yl)acetamide [2535];

N-(6-(5-methyl-1,3,4-thiadiazol-2-yl)cinnolin-3-yl)-2-(4-methylpiperazin-1-yl)acetamide [2536];

N-(6-(5-methyl-1,3,4-thiadiazol-2-yl)cinnolin-3-yl)-2-morpholinoacetamide [2537];

(R)—N-(6-(5-methyl-1,3,4-thiadiazol-2-yl)cinnolin-3-yl)-2-(3-methylmorpholino)acetamide [2538];

2-(7-azabicyclo[2.2.1]heptan-7-yl)-N-(6-(5-methyl-1,3,4-thiadiazol-2-yl)cinnolin-3-yl)acetamide [2539];

2-((1R,4R)-2-oxa-5-azabicyclo[2.2.1]heptan-5-yl)-N-(6-(5-methyl-1,3,4-thiadiazol-2-yl)cinnolin-3-yl)acetamide [2540];

2-(3-oxa-8-azabicyclo[3.2.1]octan-8-yl)-N-(6-(5-methyl-1,3,4-thiadiazol-2-yl)cinnolin-3-yl)acetamide [2541];

2-(8-oxa-3-azabicyclo[3.2.1]octan-3-yl)-N-(6-(5-methyl-1,3,4-thiadiazol-2-yl)cinnolin-3-yl)acetamide [2542];

N-(6-(5-methyl-1,3,4-thiadiazol-2-yl)cinnolin-3-yl)-2-(1,4-oxazepan-4-yl)acetamide [2543];
N-(6-(5-methyl-1,3,4-thiadiazol-2-yl)cinnolin-3-yl)-2-morpholinoacetamide-2,2-$d_2$ [2544];
N-(6-(5-methyl-1,3,4-thiadiazol-2-yl)cinnolin-3-yl)-2-(morpholino-$d_8$)acetamide [2545];
1-methyl-3-(6-(5-methyl-1,3,4-thiadiazol-2-yl)cinnolin-3-yl)-1-(1-methylpiperidin-4-yl)urea [2546];
(3S,4S)-4-amino-3-fluoro-N-(6-(5-methyl-1,3,4-thiadiazol-2-yl)cinnolin-3-yl)piperidine-1-carboxamide [2547];
(3S,4S)-4-(dimethylamino)-3-fluor N-(6-(5-methyl-1,3,4-thiadiazol-2-yl)cinnolin-3-yl) piperidine-1-carboxamide [2548];
N-(6-(5-methyl-1,3,4-thiadiazol-2-yl)cinnolin-3-yl)morpholine-4-carboxamide [2549];
N-(6-(5-methyl-1,3,4-thiadiazol-2-yl)cinnolin-3-yl)-4-(methylamino)piperidine-1-carboxamide [2550];
4-(dimethylamino)-N-(6-(5-methyl-1,3,4-thiadiazol-2-yl)cinnolin-3-yl)piperidine-1-carboxamide [2551];
4-((2,2-difluoroethyl)(methyl)amino)-N-(6-(5-methyl-1,3,4-thiadiazol-2-yl)cinnolin-3-yl) piperidine-1-carboxamide [2552];
(3S,4S)-3-fluoro-4-(isopropylamino)-N-(6-(5-methyl-1,3,4-thiadiazol-2-yl)cinnolin-3-yl) piperidine-1-carboxamide [2553];
2-methyl-N-(6-(5-methyl-1,3,4-thiadiazol-2-yl)cinnolin-3-yl)-5,6-dihydroimidazo[1,2-a]pyrazine-7(8H)-carboxamide [2554];
4-methyl-N-(6-(5-methyl-1,3,4-thiadiazol-2-yl)cinnolin-3-yl)piperazine-1-carboxamide [2555];
N-(6-(5-methyl-1,3,4-thiadiazol-2-yl)cinnolin-3-yl)-1-(1-methylpiperidin-4-yl)-1H-pyrazole-4-carboxamide [2556];
1-(1-isopropylpiperidin-4-yl)-N-(6-(5-methyl-1,3,4-thiadiazol-2-yl)cinnolin-3-yl)-1H-pyrazole-4-carboxamide [2557];
N-(6-(5-methyl-1,3,4-thiadiazol-2-yl)cinnolin-3-yl)-1-(1-methylpiperidin-4-yl)-1H-1,2,3-triazole-4-carboxamide [2558];
N-(6-(5-methyl-1,3,4-thiadiazol-2-yl)cinnolin-3-yl)-2-(piperidin-4-yl)oxazole-4-carboxamide [2559];
N-(6-(5-methyl-1,3,4-thiadiazol-2-yl)cinnolin-3-yl)-2-(1-methylpiperidin-4-yl)oxazole-4-carboxamide [2560];
2-(3-(dimethylamino)azetidin-1-yl)-N-(6-(5-methyl-1,3,4-thiadiazol-2-yl)cinnolin-3-yl)isonicotinamide [2561];
1'-methyl-N-(6-(5-methyl-1,3,4-thiadiazol-2-yl)cinnolin-3-yl)-1',2',3',6'-tetrahydro-[2,4'-bipyridine]-4-carboxamide [2562];
N-(6-(5-methyl-1,3,4-thiadiazol-2-yl)cinnolin-3-yl)-2-(4-methylpiperazin-1-yl)isonicotinamide [2563];
2-(methyl(1-methylpiperidin-4-yl)amino)-N-(6-(5-methyl-1,3,4-thiadiazol-2-yl)cinnolin-3-yl) isonicotinamide [2564];
2-(azetidin-3-yloxy)-N-(6-(5-methyl-1,3,4-thiadiazol-2-yl)cinnolin-3-yl)isonicotinamide [2565];
N-(6-(5-methyl-1,3,4-thiadiazol-2-yl)cinnolin-3-yl)-3-((1-methylpiperidin-4-yl)oxy)benzamide [2566];
N-(6-(5-methyl-1,3,4-thiadiazol-2-yl)cinnolin-3-yl)-2-((1-methylpiperidin-4-yl)thio) isonicotinamide [2567];
6-(4-methylpiperazin-1-yl)-N-(6-(5-(trifluoromethyl)-1,3,4-thiadiazol-2-yl)cinnolin-3-yl) nicotinamide [2568];
2-(4-methylpiperazin-1-yl)-N-(6-(5-(trifluoromethyl)-1,3,4-thiadiazol-2-yl)cinnolin-3-yl) isonicotinamide [2569];
N-(6-(5-amino-1,3,4-thiadiazol-2-yl)cinnolin-3-yl)-2-(4-methylpiperazin-1-yl)isonicotinamide [2570];
N-(6-(5-(dimethylamino)-1,3,4-thiadiazol-2-yl)cinnolin-3-yl)-2-(4-methylpiperazin-1-yl) isonicotinamide [2571];
N-(6-(3-amino-5-fluorophenyl)cinnolin-3-yl)-2-(4-methylpiperazin-1-yl)isonicotinamide [2572];
N-(6-(3-fluoro-5-(isopropylamino)phenyl)cinnolin-3-yl)-2-(4-methylpiperazin-1-yl) isonicotinamide [2573];
1-methyl-N-(6-(pyridin-2-yl)cinnolin-3-yl)piperidine-4-carboxamide [2574];
2-(4-methylpiperazin-1-yl)-N-(6-(pyridin-2-yl)cinnolin-3-yl)isonicotinamide [2575];
2-(4-methylpiperazin-1-yl)-N-(6-(pyridin-4-yl)cinnolin-3-yl)isonicotinamide [2576];
N-(6-(pyridin-3-yl)cinnolin-3-yl)cyclopropanecarboxamide [2577];
N-(6-(pyridin-3-yl)cinnolin-3-yl)-2-(pyrrolidin-1-yl)acetamide [2578];
1-methyl-N-(6-(pyridin-3-yl)cinnolin-3-yl)piperidine-4-carboxamide [2579];
N-(6-(pyridin-3-yl)cinnolin-3-yl)quinuclidine-4-carboxamide [2580];
2-morpholino-N-(6-(pyridin-3-yl)cinnolin-3-yl)acetamide [2581];
2-(morpholino-$d_8$)—N-(6-(pyridin-3-yl)cinnolin-3-yl)acetamide [2582];
2-(4-methylpiperazin-1-yl)-N-(6-(pyridin-3-yl)cinnolin-3-yl)acetamide [2583];
2-(4-methyl-1,4-diazepan-1-yl)-N-(6-(pyridin-3-yl)cinnolin-3-yl)acetamide [2584];
2-(4-methylpiperazin-1-yl)-N-(6-(pyridin-3-yl)cinnolin-3-yl)isonicotinamide [2585];
2-(2-methyl-1H-imidazol-1-yl)-N-(6-(pyridin-3-yl)cinnolin-3-yl)acetamide [2586];
2-(1H-imidazol-1-yl)-N-(6-(pyridin-3-yl)cinnolin-3-yl)acetamide [2587];
2-(piperidin-4-yl)-N-(6-(pyridin-3-yl)cinnolin-3-yl)oxazole-4-carboxamide [2588];
2-(1-methylpiperidin-4-yl)-N-(6-(pyridin-3-yl)cinnolin-3-yl)oxazole-4-carboxamide [2589];
2-(1-isopropylpiperidin-4-yl)-N-(6-(pyridin-3-yl)cinnolin-3-yl)oxazole-4-carboxamide [2590];
trans-N-(6-(5-fluoropyridin-3-yl)cinnolin-3-yl)-3-morpholinocyclobutane-1-carboxamide [2591];
trans-N-(6-(5-fluoropyridin-3-yl)cinnolin-3-yl)-4-((4-methylpiperazin-1-yl)methyl)cyclohexane-1-carboxamide [2592];
N-(6-(5-fluoropyridin-3-yl)cinnolin-3-yl)-2-(pyrrolidin-1-yl)acetamide [2593];
N-(6-(5-fluoropyridin-3-yl)cinnolin-3-yl)-1-methylpiperidine-4-carboxamide [2594];
N-(6-(5-fluoropyridin-3-yl)cinnolin-3-yl)-2-(4-methylpiperazin-1-yl)acetamide [2595];
N-(6-(6-fluoropyridin-3-yl)cinnolin-3-yl)-2-(4-methylpiperazin-1-yl)acetamide [2596];
N-(6-(5-fluoropyridin-3-yl)cinnolin-3-yl)-2-morpholinoacetamide [2597];
N-(6-(5-fluoropyridin-3-yl)cinnolin-3-yl)-3-morpholinopropanamide [2598];
N-(6-(5-fluoropyridin-3-yl)cinnolin-3-yl)-2-(4-methylpiperazin-1-yl)isonicotinamide [2599];
N-(6-(5-fluoropyridin-3-yl)cinnolin-3-yl)-2-(piperidin-4-yl)oxazole-4-carboxamide [2600];
N-(6-(5-fluoropyridin-3-yl)cinnolin-3-yl)-2-(1-methylpiperidin-4-yl)oxazole-4-carboxamide [2601];

N-(6-(5-fluoropyridin-3-yl)cinnolin-3-yl)-2-(1-isopropylpiperidin-4-yl)oxazole-4-carboxamide [2602];
N-(6-(5-chloropyridin-3-yl)cinnolin-3-yl)-2-(4-methylpiperazin-1-yl)isonicotinamide [2603];
N-(6-(5-methylpyridin-3-yl)cinnolin-3-yl)-2-morpholinoacetamide [2604];
N-(6-(5-(difluoromethyl)pyridin-3-yl)cinnolin-3-yl)-3-(piperidin-4-yl)benzamide [2605];
N-(6-(5-(difluoromethyl)pyridin-3-yl)cinnolin-3-yl)-3-(1-methylpiperidin-4-yl)benzamide [2606];
N-(6-(5-(difluoromethyl)pyridin-3-yl)cinnolin-3-yl)-2-(4-methylpiperazin-1-yl)isonicotinamide [2607];
2-(4-methylpiperazin-1-yl)-N-(6-(5-(trifluoromethyl)pyridin-3-yl)cinnolin-3-yl)acetamide [2608];
2-(4-methylpiperazin-1-yl)-N-(6-(6-(trifluoromethyl)pyridin-3-yl)cinnolin-3-yl)acetamide [2609];
N-(6-(5-(hydroxymethyl)pyridin-3-yl)cinnolin-3-yl)-1-methylpiperidine-4-carboxamide [2610];
N-(6-(5-cyanopyridin-3-yl)cinnolin-3-yl)-1-methylpiperidine-4-carboxamide [2611];
N-(6-(5-methoxypyridin-3-yl)cinnolin-3-yl)-1-methylpiperidine-4-carboxamide [2612];
N-(6-(5-methoxypyridin-3-yl)cinnolin-3-yl)-2-morpholinoacetamide [2613];
N-(6-(5-methoxypyridin-3-yl)cinnolin-3-yl)-2-(4-methylpiperazin-1-yl)isonicotinamide [2614];
4-fluoro-N-(6-(5-(piperidin-4-yloxy)pyridin-3-yl)cinnolin-3-yl)benzamide [2615];
N-(6-(5-aminopyridin-3-yl)cinnolin-3-yl)-4-fluorobenzamide [2616];
N-(6-(5-aminopyridin-3-yl)cinnolin-3-yl)-4-(piperidin-4-yloxy)benzamide [2617];
N-(6-(5-aminopyridin-3-yl)cinnolin-3-yl)-2-(4-methylpiperazin-1-yl)isonicotinamide [2618];
N-(6-(5-aminopyridin-3-yl)cinnolin-3-yl)-2-(piperidin-4-yl)oxazole-4-carboxamide [2619];
N-(6-(6-aminopyridin-3-yl)cinnolin-3-yl)-2-(4-methylpiperazin-1-yl)isonicotinamide [2620];
N-(6-(6-(methylamino)pyridin-3-yl)cinnolin-3-yl)-2-(4-methylpiperazin-1-yl)isonicotinamide [2621];
N-(6-(5-(isopropylamino)pyridin-3-yl)cinnolin-3-yl)-3-(piperidin-4-yl)benzamide [2622];
N-(6-(5-(isopropylamino)pyridin-3-yl)cinnolin-3-yl)-3-(1-methylpiperidin-4-yl)benzamide [2623];
N-(6-(5-(isopropylamino)pyridin-3-yl)cinnolin-3-yl)-2-(4-methylpiperazin-1-yl)isonicotinamide [2624];
N-(6-(5-(piperidin-4-ylamino)pyridin-3-yl)cinnolin-3-yl)cyclohexanecarboxamide [2625];
4-fluoro-N-(6-(5-(piperidin-4-ylamino)pyridin-3-yl)cinnolin-3-yl)benzamide [2626];
4-fluoro-N-(6-(5-((1-methylpiperidin-4-yl)amino)pyridin-3-yl)cinnolin-3-yl)benzamide [2627];
N-(6-(5-acetamidopyridin-3-yl)cinnolin-3-yl)-1-methylpiperidine-4-carboxamide [2628];
N-(6-(5-(dimethylamino)pyridin-3-yl)cinnolin-3-yl)-2-(4-methylpiperazin-1-yl)isonicotinamide [2629];
N-(6-(6-(dimethylamino)pyridin-3-yl)cinnolin-3-yl)-2-(4-methylpiperazin-1-yl)isonicotinamide [2630];
1-methyl-N-(6-(5-(pyrrolidin-1-yl)pyridin-3-yl)cinnolin-3-yl)piperidine-4-carboxamide [2631];
N-(6-(5-(pyrrolidin-1-ylmethyl)pyridin-3-yl)cinnolin-3-yl)cyclopropanecarboxamide [2632];
4-fluoro-N-(6-(5-(pyrrolidin-1-ylmethyl)pyridin-3-yl)cinnolin-3-yl)benzamide [2633];
N-(6-(5-((4-hydroxypiperidin-1-yl)methyl)pyridin-3-yl)cinnolin-3-yl)cyclopropanecarboxamide [2634];
4-fluoro-N-(6-(5-((4-hydroxypiperidin-1-yl)methyl)pyridin-3-yl)cinnolin-3-yl)benzamide [2635];
N-(6-(5-(piperazin-1-ylmethyl)pyridin-3-yl)cinnolin-3-yl)cyclopropanecarboxamide [2636];
N-(6-(5-((4-methylpiperazin-1-yl)methyl)pyridin-3-yl)cinnolin-3-yl)cyclopropanecarboxamide [2637];
N-(6-(5-(morpholinomethyl)pyridin-3-yl)cinnolin-3-yl)cyclopropanecarboxamide [2638];
N-methyl-5-(3-(1-methylpiperidine-4-carboxamido)cinnolin-6-yl)nicotinamide [2639];
N-methyl-5-(3-(2-(4-methylpiperazin-1-yl)isonicotinamido)cinnolin-6-yl)nicotinamide [2640];
N-(6-(pyridin-3-yl-d$_4$)cinnolin-3-yl)-2-(pyrrolidin-1-yl)acetamide [2641];
2-(4-methylpiperazin-1-yl)-N-(6-(pyridin-3-yl-d$_4$)cinnolin-3-yl)acetamide [2642];
2-morpholino-N-(6-(pyridin-3-yl-d$_4$)cinnolin-3-yl)acetamide [2643];
1-methyl-N-(6-(2-methylpyrimidin-5-yl)cinnolin-3-yl)piperidine-4-carboxamide [2644];
2-(4-methylpiperazin-1-yl)-N-(6-(2-methylpyrimidin-5-yl)cinnolin-3-yl)isonicotinamide [2645];
N-(6-(2-aminopyrimidin-5-yl)cinnolin-3-yl)-1-methylpiperidine-4-carboxamide [2646];
2-morpholino-N-(6-(pyridazin-3-yl)cinnolin-3-yl)acetamide [2647];
2-morpholino-N-(6-(pyridazin-4-yl)cinnolin-3-yl)acetamide [2648];
N-(6-(pyridazin-4-yl)cinnolin-3-yl)-2-(pyrrolidin-1-yl)acetamide [2649];
trans-3-morpholino-N-(6-(pyrazin-2-yl)cinnolin-3-yl)cyclobutane-1-carboxamide [2650];
trans-4-(dimethylamino)-N-(6-(pyrazin-2-yl)cinnolin-3-yl)cyclohexane-1-carboxamide [2651];
trans-4-morpholino-N-(6-(pyrazin-2-yl)cinnolin-3-yl)cyclohexane-1-carboxamide [2652];
trans-4-((3-fluoroazetidin-1-yl)methyl)-N-(6-(pyrazin-2-yl)cinnolin-3-yl)cyclohexane-1-carboxamide [2653];
trans-4-((4-methylpiperazin-1-yl)methyl)-N-(6-(pyrazin-2-yl)cinnolin-3-yl)cyclohexane-1-carboxamide [2654];
N-(6-(pyrazin-2-yl)cinnolin-3-yl)-2-(pyrrolidin-1-yl)acetamide [2655];
1-methyl-N-(6-(pyrazin-2-yl)cinnolin-3-yl)piperidine-4-carboxamide [2656];
4-fluoro-1-methyl-N-(6-(pyrazin-2-yl)cinnolin-3-yl)piperidine-4-carboxamide [2657];
1-(2-fluoroethyl)-N-(6-(pyrazin-2-yl)cinnolin-3-yl)piperidine-4-carboxamide [2658];
1-(oxetan-3-yl)-N-(6-(pyrazin-2-yl)cinnolin-3-yl)piperidine-4-carboxamide [2659];
2-morpholino-N-(6-(pyrazin-2-yl)cinnolin-3-yl)acetamide [2660];
1-methyl-N-(6-(pyrazin-2-yl)cinnolin-3-yl)azepane-4-carboxamide [2661];
1-isobutyl-N-(6-(pyrazin-2-yl)cinnolin-3-yl)azepane-4-carboxamide [2662];
1-(2-hydroxy-2-methylpropyl)-N-(6-(pyrazin-2-yl)cinnolin-3-yl)azepane-4-carboxamide [2663];
4-(morpholinomethyl)-N-(6-(pyrazin-2-yl)cinnolin-3-yl)benzamide [2664];
2-(4-methylpiperazin-1-yl)-N-(6-(pyrazin-2-yl)cinnolin-3-yl)isonicotinamide [2665];
N-(6-(6-(methylamino)pyrazin-2-yl)cinnolin-3-yl)-2-(4-methylpiperazin-1-yl)isonicotinamide [2666];
N-(6-(6-(isopropylamino)pyrazin-2-yl)cinnolin-3-yl)azetidine-3-carboxamide [2667];

N-(6-(6-(isopropylamino)pyrazin-2-yl)cinnolin-3-yl)piperidine-4-carboxamide [2668];

N-(6-(6-(isopropylamino)pyrazin-2-yl)cinnolin-3-yl)-1-methylpiperidine-4-carboxamide [2669];

1-(2-fluoroethyl)-N-(6-(6-(isopropylamino)pyrazin-2-yl)cinnolin-3-yl)piperidine-4-carboxamide [2670];

1-isopropyl-N-(6-(6-(isopropylamino)pyrazin-2-yl)cinnolin-3-yl)piperidine-4-carboxamide [2671];

1-isopentyl-N-(6-(6-(isopropylamino)pyrazin-2-yl)cinnolin-3-yl)piperidine-4-carboxamide [2672];

N-(6-(6-(isopropylamino)pyrazin-2-yl)cinnolin-3-yl)-3-(piperidin-4-yl)benzamide [2673];

N-(6-(6-(isopropylamino)pyrazin-2-yl)cinnolin-3-yl)-3-(1-methylpiperidin-4-yl)benzamide [2674];

N-(6-(6-(isopropylamino)pyrazin-2-yl)cinnolin-3-yl)-1-(piperidin-4-yl)-1H-1,2,3-triazole-4-carboxamide [2675];

1-(1-(2-fluoroethyl)piperidin-4-yl)-N-(6-(6-(isopropylamino)pyrazin-2-yl)cinnolin-3-yl)-1H-1,2,3-triazole-4-carboxamide [2676];

N-(6-(6-(isopropylamino)pyrazin-2-yl)cinnolin-3-yl)-1-(1-isopropylpiperidin-4-yl)-1H-1,2,3-triazole-4-carboxamide [2677];

N-(6-(6-(isopropylamino)pyrazin-2-yl)cinnolin-3-yl)-2-(4-methylpiperazin-1-yl)isonicotinamide [2678];

N-(6-(6-(tert-butylamino)pyrazin-2-yl)cinnolin-3-yl)-2-(3-(dimethylamino)azetidin-1-yl) isonicotinamide [2679];

N-(6-(6-(tert-butylamino)pyrazin-2-yl)cinnolin-3-yl)-1'-methyl-1',2',3',6'-tetrahydro-[2,4'-bipyridine]-4-carboxamide [2680];

N-(6-(6-(tert-butylamino)pyrazin-2-yl)cinnolin-3-yl)-2-(4-methylpiperazin-1-yl)isonicotinamide [2681];

N-(6-(6-(tert-butylamino)pyrazin-2-yl)cinnolin-3-yl)-2-(4-isopropylpiperazin-1-yl) isonicotinamide [2682];

N-(6-(6-(tert-butylamino)pyrazin-2-yl)cinnolin-3-yl)-2-morpholinoisonicotinamide [2683];

N-(6-(6-(((3-fluoroazetidin-3-yl)methyl)amino)pyrazin-2-yl)cinnolin-3-yl) cyclopropanecarboxamide [2684];

4-fluoro-N-(6-(6-(((3-fluoroazetidin-3-yl)methyl)amino)pyrazin-2-yl)cinnolin-3-yl)benzamide [2685];

N-(6-(6-(piperidin-4-ylamino)pyrazin-2-yl)cinnolin-3-yl)cyclobutanecarboxamide [2686];

3,3-difluoro-N-(6-(6-(piperidin-4-ylamino)pyrazin-2-yl)cinnolin-3-yl)cyclobutane-1-carboxamide [2687];

N-(6-(6-(piperidin-4-ylamino)pyrazin-2-yl)cinnolin-3-yl)cyclopentanecarboxamide [2688];

4,4-difluoro-N-(6-(6-(piperidin-4-ylamino)pyrazin-2-yl)cinnolin-3-yl)cyclohexane-1-carboxamide [2689];

N-(6-(6-(piperidin-4-ylamino)pyrazin-2-yl)cinnolin-3-yl)tetrahydro-2H-pyran-4-carboxamide [2690];

4-fluoro-N-(6-(6-(piperidin-4-ylamino)pyrazin-2-yl)cinnolin-3-yl)benzamide [2691];

N-(6-(6-(((3S,4S)-3-fluoropiperidin-4-yl)amino)pyrazin-2-yl)cinnolin-3-yl) cyclopropanecarboxamide [2692];

4-fluoro-N-(6-(6-(((3S,4S)-3-fluoropiperidin-4-yl)amino)pyrazin-2-yl)cinnolin-3-yl)benzamide [2693];

N-(6-(6-((1-methylpiperidin-4-yl)amino)pyrazin-2-yl)cinnolin-3-yl)cyclobutanecarboxamide [2694];

N-(6-(6-((1-methylpiperidin-4-yl)amino)pyrazin-2-yl)cinnolin-3-yl)cyclopentanecarboxamide [2695];

4-fluoro-N-(6-(6-((1-methylpiperidin-4-yl)amino)pyrazin-2-yl)cinnolin-3-yl)benzamide [2696];

N-(6-(6-((1-isopropylpiperidin-4-yl)amino)pyrazin-2-yl)cinnolin-3-yl)cyclopropanecarboxamide [2697];

3,3-difluoro-N-(6-(6-((1-isopropylpiperidin-4-yl)amino)pyrazin-2-yl)cinnolin-3-yl)cyclobutane-1-carboxamide [2698];

N-(6-(6-((1-isopropylpiperidin-4-yl)amino)pyrazin-2-yl)cinnolin-3-yl)cyclopentanecarboxamide [2699];

4-fluoro-N-(6-(6-((1-isopropylpiperidin-4-yl)amino)pyrazin-2-yl)cinnolin-3-yl)benzamide [2700];

N-(6-(6-(dimethylamino)pyrazin-2-yl)cinnolin-3-yl)-2-(4-methylpiperazin-1-yl)isonicotinamide [2701];

N-(6-(6-(diethylamino)pyrazin-2-yl)cinnolin-3-yl)-2-(4-methylpiperazin-1-yl)isonicotinamide [2702];

N-(6-(6-(3-aminoazetidin-1-yl)pyrazin-2-yl)cinnolin-3-yl)-4-fluorobenzamide [2703];

2-(4-methylpiperazin-1-yl)-N-(6-(6-(pyrrolidin-1-yl)pyrazin-2-yl)cinnolin-3-yl)isonicotinamide [2704];

N-(6-(6-(azetidin-3-ylmethoxy)pyrazin-2-yl)cinnolin-3-yl)-4-fluorobenzamide [2705];

N-(6-(6-(azetidin-3-yloxy)pyrazin-2-yl)cinnolin-3-yl)-4-fluorobenzamide [2706];

N-(6-(1H-pyrrolo[2,3-b]pyridin-5-yl)cinnolin-3-yl)-1-(1-methylpiperidin-4-yl)-1H-pyrazole-4-carboxamide [2707];

N-(6-(1H-pyrrolo[3,2-b]pyridin-6-yl)cinnolin-3-yl)-1-(1-methylpiperidin-4-yl)-1H-pyrazole-4-carboxamide [2708];

N-(6-(1H-pyrrolo[2,3-c]pyridin-4-yl)cinnolin-3-yl)-1-(1-methylpiperidin-4-yl)-1H-pyrazole-4-carboxamide [2709];

N-(6-(1H-pyrrolo[2,3-b]pyridin-5-yl)cinnolin-3-yl)-2-(4-methylpiperazin-1-yl)isonicotinamide [2710];

N-(6-(1H-pyrrolo[3,2-b]pyridin-6-yl)cinnolin-3-yl)-2-(4-methylpiperazin-1-yl)isonicotinamide [2711];

N-(6-(1H-pyrrolo[2,3-c]pyridin-4-yl)cinnolin-3-yl)-2-(4-methylpiperazin-1-yl)isonicotinamide [2712];

2-(4-methylpiperazin-1-yl)-N-(6-(oxazolo[5,4-b]pyridin-6-yl)cinnolin-3-yl)isonicotinamide [2713];

N-(6-(2-methyl-1H-pyrrolo[2,3-b]pyridin-5-yl)cinnolin-3-yl)-2-(4-methylpiperazin-1-yl) isonicotinamide [2714];

N-(6-(3-methyl-1H-pyrrolo[2,3-b]pyridin-5-yl)cinnolin-3-yl)-2-(4-methylpiperazin-1-yl) isonicotinamide [2715];

N-(6-(2-methyl-1H-pyrrolo[3,2-b]pyridin-6-yl)cinnolin-3-yl)-2-(4-methylpiperazin-1-yl) isonicotinamide [2716];

N-(6-(5H-pyrrolo[2,3-b]pyrazin-2-yl)cinnolin-3-yl)-2-(4-methylpiperazin-1-yl)isonicotinamide [2717];

N-(6-(5H-pyrrolo[2,3-b]pyrazin-3-yl)cinnolin-3-yl)-2-(4-methylpiperazin-1-yl)isonicotinamide [2718];

1-isopropyl-N-(6-(6-(piperidin-4-ylamino)pyrazin-2-yl)cinnolin-3-yl)-1H-pyrazole-4-carboxamide [2719];

1-isopropyl-N-(6-(6-((1-methylpiperidin-4-yl)amino)pyrazin-2-yl)cinnolin-3-yl)-1H-pyrazole-4-carboxamide [2720]; or a pharmaceutically acceptable salt thereof.

15. The compound of claim 1, wherein the compound of Formula I is selected from the group consisting of:

N-(3-(1H-pyrazol-4-yl)-1,7-naphthyridin-6-yl)-1-isobutylpiperidine-4-carboxamide [2721];

N-(3-(1-methyl-1H-pyrazol-4-yl)-1,7-naphthyridin-6-yl)cyclopropanecarboxamide [2722];

4,4-difluoro-N-(3-(1-methyl-1H-pyrazol-4-yl)-1,7-naphthyridin-6-yl)cyclohexane-1-carboxamide [2723];

trans-4-methoxy-N-(3-(1-methyl-1H-pyrazol-4-yl)-1,7-naphthyridin-6-yl)cyclohexane-1-carboxamide [2724];

trans-N-(3-(1-methyl-1H-pyrazol-4-yl)-1,7-naphthyridin-6-yl)-4-morpholinocyclohexane-1-carboxamide [2725];

trans-4-((3-fluoroazetidin-1-yl)methyl)-N-(3-(1-methyl-1H-pyrazol-4-yl)-1,7-naphthyridin-6-yl) cyclohexane-1-carboxamide [2726];

trans-N-(3-(1-methyl-1H-pyrazol-4-yl)-1,7-naphthyridin-6-yl)-4-((4-methylpiperazin-1-yl) methyl)cyclohexane-1-carboxamide [2727];

N-(3-(1-methyl-1H-pyrazol-4-yl)-1,7-naphthyridin-6-yl)-2-(pyrrolidin-1-yl)acetamide [2728];

(S)-2-(3-fluoropyrrolidin-1-yl)-N-(3-(1-methyl-1H-pyrazol-4-yl)-1,7-naphthyridin-6-yl) acetamide [2729];

(S)—N-(3-(1-methyl-1H-pyrazol-4-yl)-1,7-naphthyridin-6-yl)tetrahydrofuran-2-carboxamide [2730];

N-(3-(1-methyl-1H-pyrazol-4-yl)-1,7-naphthyridin-6-yl) piperidine-4-carboxamide [2731];

1-methyl-N-(3-(1-methyl-1H-pyrazol-4-yl)-1,7-naphthyridin-6-yl)piperidine-4-carboxamide [2732];

1-isopropyl-N-(3-(1-methyl-1H-pyrazol-4-yl)-1,7-naphthyridin-6-yl)piperidine-4-carboxamide [2733];

1-(tert-butyl)-N-(3-(1-methyl-1H-pyrazol-4-yl)-1,7-naphthyridin-6-yl)piperidine-4-carboxamide [2734];

1-cyclopropyl-N-(3-(1-methyl-1H-pyrazol-4-yl)-1,7-naphthyridin-6-yl)piperidine-4-carboxamide [2735];

1-isobutyl-N-(3-(1-methyl-1H-pyrazol-4-yl)-1,7-naphthyridin-6-yl)piperidine-4-carboxamide [2736];

N-(3-(1-methyl-1H-pyrazol-4-yl)-1,7-naphthyridin-6-yl)-1-neopentylpiperidine-4-carboxamide [2737];

1-(2-fluoroethyl)-N-(3-(1-methyl-1H-pyrazol-4-yl)-1,7-naphthyridin-6-yl)piperidine-4-carboxamide [2738];

N-(3-(1-methyl-1H-pyrazol-4-yl)-1,7-naphthyridin-6-yl)-1-(3,3,3-trifluoropropyl)piperidine-4-carboxamide [2739];

1-butyl-N-(3-(1-methyl-1H-pyrazol-4-yl)-1,7-naphthyridin-6-yl)piperidine-4-carboxamide [2740];

1-benzoyl-N-(3-(1-methyl-1H-pyrazol-4-yl)-1,7-naphthyridin-6-yl)piperidine-4-carboxamide [2741];

1-(2,2-difluoropropyl)-N-(3-(1-methyl-1H-pyrazol-4-yl)-1,7-naphthyridin-6-yl)piperidine-4-carboxamide [2742];

N-(3-(1-methyl-1H-pyrazol-4-yl)-1,7-naphthyridin-6-yl) azetidine-3-carboxamide [2743];

1-(2,2-difluoroethyl)-N-(3-(1-methyl-1H-pyrazol-4-yl)-1,7-naphthyridin-6-yl)piperidine-4-carboxamide [2744];

1-(2-fluoro-2-methylpropyl)-N-(3-(1-methyl-1H-pyrazol-4-yl)-1,7-naphthyridin-6-yl)piperidine-4-carboxamide [2745];

N-(3-(1-methyl-1H-pyrazol-4-yl)-1,7-naphthyridin-6-yl)-1-(oxetan-3-yl)piperidine-4-carboxamide [2746];

N-(3-(1-methyl-1H-pyrazol-4-yl)-1,7-naphthyridin-6-yl)-1-((3-methyloxetan-3-yl)methyl) piperidine-4-carboxamide [2747];

1-(2-methoxyethyl)-N-(3-(1-methyl-1H-pyrazol-4-yl)-1,7-naphthyridin-6-yl)piperidine-4-carboxamide [2748];

1-(2-isopropoxyethyl)-N-(3-(1-methyl-1H-pyrazol-4-yl)-1,7-naphthyridin-6-yl)piperidine-4-carboxamide [2749];

1,1-diisobutyl-4-((3-(1-methyl-1H-pyrazol-4-yl)-1,7-naphthyridin-6-yl)carbamoyl)piperidin-1-ium [2750];

4-fluoro-N-(3-(1-methyl-1H-pyrazol-4-yl)-1,7-naphthyridin-6-yl)piperidine-4-carboxamide [2751];

4-fluoro-1-methyl-N-(3-(1-methyl-1H-pyrazol-4-yl)-1,7-naphthyridin-6-yl)piperidine-4-carboxamide [2752];

4-fluoro-1-isobutyl-N-(3-(1-methyl-1H-pyrazol-4-yl)-1,7-naphthyridin-6-yl)piperidine-4-carboxamide [2753];

(S)—N-(3-(1-methyl-1H-pyrazol-4-yl)-1,7-naphthyridin-6-yl)piperidine-3-carboxamide [2754];

(R)—N-(3-(1-methyl-1H-pyrazol-4-yl)-1,7-naphthyridin-6-yl)piperidine-3-carboxamide [2755];

(S)-1-isobutyl-N-(3-(1-methyl-1H-pyrazol-4-yl)-1,7-naphthyridin-6-yl)piperidine-3-carboxamide [2756];

(R)-1-isobutyl-N-(3-(1-methyl-1H-pyrazol-4-yl)-1,7-naphthyridin-6-yl)piperidine-3-carboxamide [2757];

N-(3-(1-methyl-1H-pyrazol-4-yl)-1,7-naphthyridin-6-yl) tetrahydro-2H-pyran-4-carboxamide [2758];

N-(3-(1-methyl-1H-pyrazol-4-yl)-1,7-naphthyridin-6-yl)-2-(piperidin-1-yl)acetamide [2759];

2-(4-fluoropiperidin-1-yl)-N-(3-(1-methyl-1H-pyrazol-4-yl)-1,7-naphthyridin-6-yl)acetamide [2760];

trans-4-amino-N-(3-(1-methyl-1H-pyrazol-4-yl)-1,7-naphthyridin-6-yl)cyclohexane-1-carboxamide [2761];

N-(3-(1-methyl-1H-pyrazol-4-yl)-1,7-naphthyridin-6-yl)-2-(4-methylpiperazin-1-yl)acetamide [2762];

(S)—N-(3-(1-methyl-1H-pyrazol-4-yl)-1,7-naphthyridin-6-yl)piperidine-2-carboxamide [2763];

2-(4-isobutylpiperazin-1-yl)-N-(3-(1-methyl-1H-pyrazol-4-yl)-1,7-naphthyridin-6-yl)acetamide [2764];

2-(3,3-dimethylazetidin-1-yl)-N-(3-(1-methyl-1H-pyrazol-4-yl)-1,7-naphthyridin-6-yl)acetamide [2765];

(R)-2-(3-fluoropyrrolidin-1-yl)-N-(3-(1-methyl-1H-pyrazol-4-yl)-1,7-naphthyridin-6-yl) acetamide [2766];

(S)—N-(3-(1-methyl-1H-pyrazol-4-yl)-1,7-naphthyridin-6-yl)-2-(2-methylpyrrolidin-1-yl) acetamide [2767];

2-(3-azabicyclo[3.1.0]hexan-3-yl)-N-(3-(1-methyl-1H-pyrazol-4-yl)-1,7-naphthyridin-6-yl) acetamide [2768];

2-(7-azabicyclo[2.2.1]heptan-7-yl)-N-(3-(1-methyl-1H-pyrazol-4-yl)-1,7-naphthyridin-6-yl) acetamide [2769];

N-(3-(1-methyl-1H-pyrazol-4-yl)-1,7-naphthyridin-6-yl)-2-(4-methylpiperidin-1-yl)acetamide [2770];

N-(3-(1-methyl-1H-pyrazol-4-yl)-1,7-naphthyridin-6-yl)-2-(4-(trifluoromethyl)piperidin-1-yl) acetamide [2771];

2-(4-(difluoromethyl)piperidin-1-yl)-N-(3-(1-methyl-1H-pyrazol-4-yl)-1,7-naphthyridin-6-yl) acetamide [2772];

N-(3-(1-methyl-1H-pyrazol-4-yl)-1,7-naphthyridin-6-yl)-2-(6-azaspiro[2.5]octan-6-yl)acetamide [2773];

N-(3-(1-methyl-1H-pyrazol-4-yl)-1,7-naphthyridin-6-yl)-2-(pyrrolidin-1-yl)propanamide [2774];

(R)—N-(3-(1-methyl-1H-pyrazol-4-yl)-1,7-naphthyridin-6-yl)-2-(2-methylpyrrolidin-1-yl) acetamide [2775];

2-(cyclobutyl(methyl)amino)-N-(3-(1-methyl-1H-pyrazol-4-yl)-1,7-naphthyridin-6-yl)acetamide [2776];

2-(diethylamino)-N-(3-(1-methyl-1H-pyrazol-4-yl)-1,7-naphthyridin-6-yl)acetamide [2777];

7-(2-fluoroethyl)-N-(3-(1-methyl-1H-pyrazol-4-yl)-1,7-naphthyridin-6-yl)-7-azaspiro[3.5]nonane-2-carboxamide [2778];

4-methyl-N-(3-(1-methyl-1H-pyrazol-4-yl)-1,7-naphthyridin-6-yl)piperazine-1-carboxamide [2779];

(S)—N-(3-(1-methyl-1H-pyrazol-4-yl)-1,7-naphthyridin-6-yl)-2-(pyrrolidin-1-yl)propanamide [2780];

(R)—N-(3-(1-methyl-1H-pyrazol-4-yl)-1,7-naphthyridin-6-yl)-2-(pyrrolidin-1-yl)propanamide [2781];

(R)—N-(3-(1-methyl-1H-pyrazol-4-yl)-1,7-naphthyridin-6-yl)pyrrolidine-2-carboxamide [2782];

2-methyl-N-(3-(1-methyl-1H-pyrazol-4-yl)-1,7-naphthyridin-6-yl)-2-azaspiro [3.3]heptane-6-carboxamide [2783];

N-(3-(1-methyl-1H-pyrazol-4-yl)-1,7-naphthyridin-6-yl)-2-(2,2,2-trifluoroacetyl)-2-azaspiro [3.3]heptane-6-carboxamide [2784];

2-(2-fluoroethyl)-N-(3-(1-methyl-1H-pyrazol-4-yl)-1,7-naphthyridin-6-yl)-2-azaspiro[3.3]heptane-6-carboxamide [2785];
trans-4-(dimethylamino)-N-(3-(1-methyl-1H-pyrazol-4-yl)-1,7-naphthyridin-6-yl)cyclohexane-1-carboxamide [2786];
1-acetyl-N-(3-(1-methyl-1H-pyrazol-4-yl)-1,7-naphthyridin-6-yl)piperidine-4-carboxamide [2787];
N-(3-(1-methyl-1H-pyrazol-4-yl)-1,7-naphthyridin-6-yl)-1-((1-(trifluoromethyl)cyclopropyl) methyl)piperidine-4-carboxamide [2788];
(S)-1-(2-fluoropropyl)-N-(3-(1-methyl-1H-pyrazol-4-yl)-1,7-naphthyridin-6-yl)piperidine-4-carboxamide [2789];
(R)-1-(2-fluoropropyl)-N-(3-(1-methyl-1H-pyrazol-4-yl)-1,7-naphthyridin-6-yl)piperidine-4-carboxamide [2790];
N-(3-(1-methyl-1H-pyrazol-4-yl)-1,7-naphthyridin-6-yl)-2-(piperidin-1-yl)propanamide [2791];
N-(3-(1-methyl-1H-pyrazol-4-yl)-1,7-naphthyridin-6-yl)-1-(methylsulfonyl)piperidine-4-carboxamide [2792];
1'-methyl-N-(3-(1-methyl-1H-pyrazol-4-yl)-1,7-naphthyridin-6-yl)-[1,4'-bipiperidine]-4-carboxamide [2793];
trans-4-(hydroxymethyl)-N-(3-(1-methyl-1H-pyrazol-4-yl)-1,7-naphthyridin-6-yl)cyclohexane-1-carboxamide [2794];
methyl 2-(4-((3-(1-methyl-1H-pyrazol-4-yl)-1,7-naphthyridin-6-yl)carbamoyl)piperidin-1-yl) acetate [2795];
1-benzyl-N-(3-(1-methyl-1H-pyrazol-4-yl)-1,7-naphthyridin-6-yl)piperidine-4-carboxamide [2796];
N-(3-(1-methyl-1H-pyrazol-4-yl)-1,7-naphthyridin-6-yl)-1-(2-(pyrrolidin-1-yl)acetyl)piperidine-4-carboxamide [2797];
N-(3-(1-methyl-1H-pyrazol-4-yl)-1,7-naphthyridin-6-yl)-2-morpholinoacetamide [2798];
(S)—N-(3-(1-methyl-1H-pyrazol-4-yl)-1,7-naphthyridin-6-yl)-2-(3-methylmorpholino)acetamide [2799];
(R)—N-(3-(1-methyl-1H-pyrazol-4-yl)-1,7-naphthyridin-6-yl)-2-(3-methylmorpholino)acetamide [2800];
(S)—N-(3-(1-methyl-1H-pyrazol-4-yl)-1,7-naphthyridin-6-yl)-2-(2-methylmorpholino)acetamide [2801];
2-((2R,6S)-2,6-dimethylmorpholino)-N-(3-(1-methyl-1H-pyrazol-4-yl)-1,7-naphthyridin-6-yl) acetamide [2802];
2-((1S,4S)-2-oxa-5-azabicyclo[2.2.1]heptan-5-yl)-N-(3-(1-methyl-1H-pyrazol-4-yl)-1,7-naphthyridin-6-yl)acetamide [2803];
2-((1R,4R)-2-oxa-5-azabicyclo[2.2.1]heptan-5-yl)-N-(3-(1-methyl-1H-pyrazol-4-yl)-1,7-naphthyridin-6-yl)acetamide [2804];
2-(3-oxa-8-azabicyclo[3.2.1]octan-8-yl)-N-(3-(1-methyl-1H-pyrazol-4-yl)-1,7-naphthyridin-6-yl) acetamide [2805];
(S)—N-(3-(1-methyl-1H-pyrazol-4-yl)-1,7-naphthyridin-6-yl)-2-morpholinopropanamide [2806];
N-(3-(1-methyl-1H-pyrazol-4-yl)-1,7-naphthyridin-6-yl)-2-(morpholin-2-yl)acetamide [2807];
N-(3-(1-methyl-1H-pyrazol-4-yl)-1,7-naphthyridin-6-yl)-2-(4-methylmorpholin-2-yl)acetamide [2808];
2-(4-ethylpiperazin-1-yl)-N-(3-(1-methyl-1H-pyrazol-4-yl)-1,7-naphthyridin-6-yl)acetamide [2809];
2-(4-isopropylpiperazin-1-yl)-N-(3-(1-methyl-1H-pyrazol-4-yl)-1,7-naphthyridin-6-yl)acetamide [2810];
2-(4-cyclopropylpiperazin-1-yl)-N-(3-(1-methyl-1H-pyrazol-4-yl)-1,7-naphthyridin-6-yl) acetamide [2911];
2-(4-(2-fluoroethyl)piperazin-1-yl)-N-(3-(1-methyl-1H-pyrazol-4-yl)-1,7-naphthyridin-6-yl) acetamide [2812];
(S)-2-(2,4-dimethylpiperazin-1-yl)-N-(3-(1-methyl-1H-pyrazol-4-yl)-1,7-naphthyridin-6-yl) acetamide [2813];
1-(2-hydroxyethyl)-N-(3-(1-methyl-1H-pyrazol-4-yl)-1,7-naphthyridin-6-yl)piperidine-4-carboxamide [2814];
N-(3-(1-methyl-1H-pyrazol-4-yl)-1,7-naphthyridin-6-yl)-1-(pyridin-2-ylmethyl)piperidine-4-carboxamide [2815];
N-(3-(1-methyl-1H-pyrazol-4-yl)-1,7-naphthyridin-6-yl)-1-(oxazol-2-ylmethyl)piperidine-4-carboxamide [2816];
(R)—N-(3-(1-methyl-1H-pyrazol-4-yl)-1,7-naphthyridin-6-yl)-1-oxotetrahydro-1H-pyrrolo[1,2-c]imidazole-2(3H)-carboxamide [2817];
(R)-1-methyl-N-(3-(1-methyl-1H-pyrazol-4-yl)-1,7-naphthyridin-6-yl)pyrrolidine-2-carboxamide [2818];
N-(3-(1-methyl-1H-pyrazol-4-yl)-1,7-naphthyridin-6-yl)-1-(tetrahydro-2H-pyran-4-yl)piperidine-4-carboxamide [2819];
N-(3-(1-methyl-1H-pyrazol-4-yl)-1,7-naphthyridin-6-yl)-1-(pyrimidin-2-ylmethyl)piperidine-4-carboxamide [2820];
N-(3-(1-methyl-1H-pyrazol-4-yl)-1,7-naphthyridin-6-yl)-1-(pyrazin-2-ylmethyl)piperidine-4-carboxamide [2821];
1-((5-methyl-1,2,4-oxadiazol-3-yl)methyl)-N-(3-(1-methyl-1H-pyrazol-4-yl)-1,7-naphthyridin-6-yl)piperidine-4-carboxamide [2822];
1-(2-hydroxy-2-methylpropyl)-N-(3-(1-methyl-1H-pyrazol-4-yl)-1,7-naphthyridin-6-yl) piperidine-4-carboxamide [2823];
tert-butyl 2-(4-((3-(1-methyl-1H-pyrazol-4-yl)-1,7-naphthyridin-6-yl)carbamoyl)piperidin-1-yl) acetate [2824];
2-(4-((3-(1-methyl-1H-pyrazol-4-yl)-1,7-naphthyridin-6-yl)carbamoyl)piperidin-1-yl)acetic acid [2825];
2-(4-methyl-1,4-diazepan-1-yl)-N-(3-(1-methyl-1H-pyrazol-4-yl)-1,7-naphthyridin-6-yl) acetamide [2826];
tert-butyl (3-(1-methyl-1H-pyrazol-4-yl)-1,7-naphthyridin-6-yl)carbamate [2827];
N-(3-(1-methyl-1H-pyrazol-4-yl)-1,7-naphthyridin-6-yl) but-2-ynamide [2828];
trans-4-((3-(1-methyl-1H-pyrazol-4-yl)-1,7-naphthyridin-6-yl)carbamoyl)cyclohexane-1-carboxylic acid [2829];
N-(3-(1-methyl-1H-pyrazol-4-yl)-1,7-naphthyridin-6-yl)-3-morpholinopropanamide [2830];
trans-N-(3-(1-methyl-1H-pyrazol-4-yl)-1,7-naphthyridin-6-yl)-3-morpholinocyclobutane-1-carboxamide [2831];
N-(3-(1-methyl-1H-pyrazol-4-yl)-1,7-naphthyridin-6-yl) quinuclidine-4-carboxamide [2832];
1-isobutyl-N-(3-(1-methyl-1H-pyrazol-4-yl)-1,7-naphthyridin-6-yl)azepane-4-carboxamide [2833];
2-(4-methoxypiperidin-1-yl)-N-(3-(1-methyl-1H-pyrazol-4-yl)-1,7-naphthyridin-6-yl)acetamide [2834];
2-(4-hydroxypiperidin-1-yl)-N-(3-(1-methyl-1H-pyrazol-4-yl)-1,7-naphthyridin-6-yl)acetamide [2835];
3-(hydroxymethyl)-N-(3-(1-methyl-1H-pyrazol-4-yl)-1,7-naphthyridin-6-yl)bicyclo[1.1.1]pentane-1-carboxamide [2836];
1-methyl-N-(3-(1-methyl-1H-pyrazol-4-yl)-1,7-naphthyridin-6-yl)azepane-4-carboxamide [2837];
trans-4-(dimethylamino)-N-(3 (1-methyl-1H-pyrazol-4-yl)-1,7-naphthyridin-6-yl)cyclohexane-1,7-naphthyridin-6-yl)c carboxamide [2838];
trans-4-(bis(methyl-d$_3$)amino)-N-(3-(1-methyl-1H-pyrazol-4-yl)-1,7-naphthyridin-6-yl) cyclohexane-1-carboxamide [2839];

N-(3-(1-methyl-1H-pyrazol-4-yl)-1,7-naphthyridin-6-yl)-3-((4-methylpiperazin-1-yl)methyl) bicyclo[1.1.1]pentane-1-carboxamide [2840];

methyl trans-4-((3-(1-methyl-1H-pyrazol-4-yl)-1,7-naphthyridin-6-yl)carbamoyl)cyclohexane-1-carboxylate [2841];

2-(1-isobutylpyrrolidin-3-yl)-N-(3-(1-methyl-1H-pyrazol-4-yl)-1,7-naphthyridin-6-yl)acetamide [2842];

trans-N-(3-(1-methyl-1H-pyrazol-4-yl)-1,7-naphthyridin-6-yl)-4-(4-methylpiperazine-1-carbonyl)cyclohexane-1-carboxamide [2843];

1-isobutyl-N-(3-(1-methyl-1H-pyrazol-4-yl)-1,7-naphthyridin-6-yl)piperidine-4-carboxamide [2844];

N-(3-(1-methyl-1H-pyrazol-4-yl)-1,7-naphthyridin-6-yl)-1-(phenylsulfonyl)piperidine-4-carboxamide [2845];

8-methyl-N-(3-(1-methyl-1H-pyrazol-4-yl)-1,7-naphthyridin-6-yl)-3,8-diazabicyclo[3.2.1]octane-3-carboxamide [2846];

3-methyl-N-(3-(1-methyl-1H-pyrazol-4-yl)-1,7-naphthyridin-6-yl)-3,8-diazabicyclo[3.2.1]octane-8-carboxamide [2847];

(1R,3s,5S)-3-amino-N-(3-(1-methyl-1H-pyrazol-4-yl)-1,7-naphthyridin-6-yl)-8-azabicyclo[3.2.1] octane-8-carboxamide [2848];

(1R,3s,5S)—N-(3-(1-methyl-1H-pyrazol-4-yl)-1,7-naphthyridin-6-yl)-3-((3,3,3-trifluoropropyl) amino)-8-azabicyclo[3.2.1]octane-8-carboxamide [2849];

(1R,3s,5S)-3-((1,3-difluoropropan-2-yl)amino)-N-(3-(1-methyl-1H-pyrazol-4-yl)-1,7-naphthyridin-6-yl)-8-azabicyclo[3.2.1]octane-8-carboxamide [2850];

N-(3-(1-methyl-1H-pyrazol-4-yl)-1,7-naphthyridin-6-yl) morpholine-4-carboxamide [2851];

4-(dimethylamino)-N-(3-(1-methyl-1H-pyrazol-4-yl)-1,7-naphthyridin-6-yl)piperidine-1-carboxamide [2852];

(S)-2,4-dimethyl-N-(3-(1-methyl-1H-pyrazol-4-yl)-1,7-naphthyridin-6-yl)piperazine-1-carboxamide [2853];

1-methyl-3-(3-(1-methyl-1H-pyrazol-4-yl)-1,7-naphthyridin-6-yl)-1-(1-methylpiperidin-4-yl)urea [2854];

1-(3-(1-methyl-1H-pyrazol-4-yl)-1,7-naphthyridin-6-yl)-3-(1-methylpiperidin-4-yl)urea [2855];

4-isopropyl-N-(3-(1-methyl-1H-pyrazol-4-yl)-1,7-naphthyridin-6-yl)piperazine-1-carboxamide [2856];

(R)-3,4-dimethyl-N-(3-(1-methyl-1H-pyrazol-4-yl)-1,7-naphthyridin-6-yl)piperazine-1-carboxamide [2857];

N-(3-(1H-pyrazol-4-yl)-1,7-naphthyridin-6-yl)-2-(4-methylpiperazin-1-yl)isonicotinamide [2858];

N-(3-(1-methyl-1H-pyrazol-4-yl)-1,7-naphthyridin-6-yl)-3-(piperazin-1-yl)benzamide [2859];

N-(3-(1-methyl-1H-pyrazol-4-yl)-1,7-naphthyridin-6-yl)-3-(4-methylpiperazin-1-yl)benzamide [2860];

N-(3-(1-methyl-1H-pyrazol-4-yl)-1,7-naphthyridin-6-yl)-3-(pyrrolidin-1-ylmethyl)benzamide [2861];

N-(3-(1-methyl-1H-pyrazol-4-yl)-1,7-naphthyridin-6-yl)-3-(piperidin-4-yloxy)benzamide [2862];

N-(3-(1-methyl-1H-pyrazol-4-yl)-1,7-naphthyridin-6-yl)-3-((1-methylpiperidin-4-yl)oxy) benzamide [2863];

N-(3-(1-methyl-1H-pyrazol-4-yl)-1,7-naphthyridin-6-yl)-4-(piperidin-4-yloxy)benzamide [2864];

N-(3-(1-methyl-1H-pyrazol-4-yl)-1,7-naphthyridin-6-yl)-4-((1-methylpiperidin-4-yl)oxy) benzamide [2865];

N-(3-(1-methyl-1H-pyrazol-4-yl)-1,7-naphthyridin-6-yl)-2-(piperazin-1-yl)isonicotinamide [2866];

N-(3-(1-methyl-1H-pyrazol-4-yl)-1,7-naphthyridin-6-yl)-2-(4-methylpiperazin-1-yl) isonicotinamide [2867];

2-(4-isopropylpiperazin-1-yl)-N-(3-(1-methyl-1H-pyrazol-4-yl)-1,7-naphthyridin-6-yl) isonicotinamide [2868];

2-(4-cyclopropylpiperazin-1-yl)-N-(3-(1-methyl-1H-pyrazol-4-yl)-1,7-naphthyridin-6-yl) isonicotinamide [2869];

2-(4-(2-fluoroethyl)piperazin-1-yl)-N-(3-(1-methyl-1H-pyrazol-4-yl)-1,7-naphthyridin-6-yl) isonicotinamide [2870];

N-(3-(1-methyl-1H-pyrazol-4-yl)-1,7-naphthyridin-6-yl)-6-(4-methylpiperazin-1-yl)nicotinamide [2871];

N-(3-(1-methyl-1H-pyrazol-4-yl)-1,7-naphthyridin-6-yl)-5-(piperidin-4-yloxy)nicotinamide [2872];

N-(3-(1-methyl-1H-pyrazol-4-yl)-1,7-naphthyridin-6-yl)-2-(piperidin-4-yloxy)isonicotinamide [2873];

N-(3-(1-methyl-1H-pyrazol-4-yl)-1,7-naphthyridin-6-yl)-2-((1-methylpiperidin-4-yl)oxy) isonicotinamide [2874];

N-(3-(1-methyl-1H-pyrazol-4-yl)-1,7-naphthyridin-6-yl)-5-(piperidin-4-ylamino)nicotinamide [2875];

N-(3-(1-methyl-1H-pyrazol-4-yl)-1,7-naphthyridin-6-yl)-5-((1-methylpiperidin-4-yl)amino) nicotinamide [2876];

2-(4-aminopiperidin-1-yl)-N-(3-(1-methyl-1H-pyrazol-4-yl)-1,7-naphthyridin-6-yl) isonicotinamide [2877];

N-(3-(1-methyl-1H-pyrazol-4-yl)-1,7-naphthyridin-6-yl)-2-(4-(methylamino)piperidin-1-yl) isonicotinamide [2878];

2-(4-(dimethylamino)piperidin-1-yl)-N-(3-(1-methyl-1H-pyrazol-4-yl)-1,7-naphthyridin-6-yl) isonicotinamide [2879];

2-((1-isopropylpiperidin-4-yl)oxy)-N-(3-(1-methyl-1H-pyrazol-4-yl)-1,7-naphthyridin-6-yl) isonicotinamide [2880];

2-(3-aminoazetidin-1-yl)-N-(3-(1-methyl-1H-pyrazol-4-yl)-1,7-naphthyridin-6-yl) isonicotinamide [2881];

2-(3-(dimethylamino)azetidin-1-yl)-N-(3-(1-methyl-1H-pyrazol-4-yl)-1,7-naphthyridin-6-yl) isonicotinamide [2882];

N-(3-(1-methyl-1H-pyrazol-4-yl)-1,7-naphthyridin-6-yl)-2-morpholinoisonicotinamide [2883];

2-((2-(dimethylamino)ethyl)amino)-N-(3-(1-methyl-1H-pyrazol-4-yl)-1,7-naphthyridin-6-yl) isonicotinamide [2884];

2-(2-(dimethylamino)ethoxy)-N-(3-(1-methyl-1H-pyrazol-4-yl)-1,7-naphthyridin-6-yl) isonicotinamide [2885];

2-(4-isobutylpiperazin-1-yl)-N-(3-(1-methyl-1H-pyrazol-4-yl)-1,7-naphthyridin-6-yl) isonicotinamide [2886];

2-(azetidin-3-yloxy)-N-(3-(1-methyl-1H-pyrazol-4-yl)-1,7-naphthyridin-6-yl)isonicotinamide [2887];

N-(3-(1-methyl-1H-pyrazol-4-yl)-1,7-naphthyridin-6-yl)-2-((1-methylazetidin-3-yl)oxy) isonicotinamide [2888];

2-(4-ethylpiperazin-1-yl)-N-(3-(1-methyl-1H-pyrazol-4-yl)-1,7-naphthyridin-6-yl) isonicotinamide [2889];

4-((dimethylamino)methyl)-N-(3-(1-methyl-1H-pyrazol-4-yl)-1,7-naphthyridin-6-yl)benzamide [2890];

N-(3-(1-methyl-1H-pyrazol-4-yl)-1,7-naphthyridin-6-yl)-3-(1-methylpiperidin-4-yl)benzamide [2891];

N-(3-(1-methyl-1H-pyrazol-4-yl)-1,7-naphthyridin-6-yl)-3-((4-methylpiperazin-1-yl)methyl) benzamide [2892];

N-(3-(1-methyl-1H-pyrazol-4-yl)-1,7-naphthyridin-6-yl) isonicotinamide [2893];

2-hydroxy-N-(3-(1-methyl-1H-pyrazol-4-yl)-1,7-naphthyridin-6-yl)isonicotinamide [2894];

2-isopropoxy-N-(3-(1-methyl-1H-pyrazol-4-yl)-1,7-naphthyridin-6-yl)isonicotinamide [2895];

N-(3-(1-methyl-1H-pyrazol-4-yl)-1,7-naphthyridin-6-yl)-2-(1-methylpiperidin-4-yl) isonicotinamide [2896];

1'-methyl-N-(3-(1-methyl-1H-pyrazol-4-yl)-1,7-naphthyridin-6-yl)-1',2',3',6'-tetrahydro-[2,4'-bipyridine]-4-carboxamide [2897];
N-(3-(1-methyl-1H-pyrazol-4-yl)-1,7-naphthyridin-6-yl)-2-(4-(6-(4-methylpiperazin-1-yl) nicotinoyl)piperazin-1-yl)isonicotinamide [2898];
2-(4-hydroxy-4-methyl-4λ4-piperazin-1-yl)-N-(3-(1-methyl-1H-pyrazol-4-yl)-1,7-naphthyridin-6-yl)isonicotinamide [2899];
2-methyl-N-(3-(1-methyl-1H-pyrazol-4-yl)-1,7-naphthyridin-6-yl)-6-(4-methylpiperazin-1-yl) isonicotinamide [2900];
3-methyl-N-(3-(1-methyl-1H-pyrazol-4-yl)-1,7-naphthyridin-6-yl)-2-(4-methylpiperazin-1-yl) isonicotinamide [2901];
2-(4-methyl-1,4-diazepan-1-yl)-N-(3-(1-methyl-1H-pyrazol-4-yl)-1,7-naphthyridin-6-yl) isonicotinamide [2902];
2-((2S,6R)-2,6-dimethylmorpholino)-N-(3-(1-methyl-1H-pyrazol-4-yl)-1,7-naphthyridin-6-yl)isonicotinamide [2903];
N-(3-(1-methyl-1H-pyrazol-4-yl)-1,7-naphthyridin-6-yl)-2-(2,7-diazaspiro[3.5]nonan-2-yl) isonicotinamide [2904];
N-(3-(1-methyl-1H-pyrazol-4-yl)-1,7-naphthyridin-6-yl)-2-(7-methyl-2,7-diazaspiro[3.5]nonan-2-yl)isonicotinamide [2905];
N-(3-(1-methyl-1H-pyrazol-4-yl)-1,7-naphthyridin-6-yl)-2-(2,7-diazaspiro[3.5]nonan-7-yl) isonicotinamide [2906];
N-(3-(1-methyl-1H-pyrazol-4-yl)-1,7-naphthyridin-6-yl)-2-(2-methyl-2,7-diazaspiro[3.5]nonan-7-yl)isonicotinamide [2907];
2-(methyl(1-methylpiperidin-4-yl)amino)-N-(3-(1-methyl-1H-pyrazol-4-yl)-1,7-naphthyridin-6-yl)isonicotinamide [2908];
N-(3-(1-methyl-1H-pyrazol-4-yl)-1,7-naphthyridin-6-yl)-2-((1-methylpiperidin-4-yl)thio) isonicotinamide [2909];
N-(3-(1-methyl-1H-pyrazol-4-yl)-1,7-naphthyridin-6-yl)-2-(4-methylpiperazin-1-yl)pyrimidine-4-carboxamide [2910];
N-(3-(1-methyl-1H-pyrazol-4-yl)-1,7-naphthyridin-6-yl)-6-(4-methylpiperazin-1-yl)pyridazine-4-carboxamide [2911];
N-(3-(1-methyl-1H-pyrazol-4-yl)-1,7-naphthyridin-6-yl)-6-(4-methylpiperazin-1-yl)pyrimidine-4-carboxamide [2912];
N-(3-(1-methyl-1H-pyrazol-4-yl)-1,7-naphthyridin-6-yl)-2-phenylacetamide [2913];
N-(3-(1-methyl-1H-pyrazol-4-yl)-1,7-naphthyridin-6-yl)-3-phenylpropanamide [2914];
N-(3-(1-methyl-1H-pyrazol-4-yl)-1,7-naphthyridin-6-yl)-2-(pyridin-3-yl)acetamide [2915];
N-(3-(1-methyl-1H-pyrazol-4-yl)-1,7-naphthyridin-6-yl)-3-(pyridin-3-yl)propanamide [2916];
N-(3-(1-methyl-1H-pyrazol-4-yl)-1,7-naphthyridin-6-yl)-2-(pyridin-4-yl)acetamide [2917];
N-(3-(1-methyl-1H-pyrazol-4-yl)-1,7-naphthyridin-6-yl)-3-(pyridin-4-yl)propanamide [2918];
N-(3-(1-methyl-1H-pyrazol-4-yl)-1,7-naphthyridin-6-yl) isoindoline-5-carboxamide [2919];
2-methyl-N-(3-(1-methyl-1H-pyrazol-4-yl)-1,7-naphthyridin-6-yl)isoindoline-5-carboxamide [2920];
N-(3-(1-methyl-1H-pyrazol-4-yl)-1,7-naphthyridin-6-yl)-1,2,3,4-tetrahydroisoquinoline-7-carboxamide [2921];
2-methyl-N-(3-(1-methyl-1H-pyrazol-4-yl)-1,7-naphthyridin-6-yl)-1,2,3,4-tetrahydroisoquinoline-7-carboxamide [2922];
2-methyl-N-(3-(1-methyl-1H-pyrazol-4-yl)-1,7-naphthyridin-6-yl)-1,2,3,4-tetrahydroisoquinoline-6-carboxamide [2923];
N-(3-(1-methyl-1H-pyrazol-4-yl)-1,7-naphthyridin-6-yl)-1,2,3,4-tetrahydroisoquinoline-6-carboxamide [2924];
N-(3-(1-methyl-1H-pyrazol-4-yl)-1,7-naphthyridin-6-yl)-1H-indole-5-carboxamide [2925];
N-(3-(1-methyl-1H-pyrazol-4-yl)-1,7-naphthyridin-6-yl) benzofuran-5-carboxamide [2926];
N-(3-(1-methyl-1H-pyrazol-4-yl)-1,7-naphthyridin-6-yl) furo[2,3-c]pyridine-5-carboxamide [2927];
N-(3-(1-methyl-1H-pyrazol-4-yl)-1,7-naphthyridin-6-yl) benzo[b]thiophene-5-carboxamide [2928];
N-(3-(1-methyl-1H-pyrazol-4-yl)-1,7-naphthyridin-6-yl) benzofuran-6-carboxamide [2929];
N-(3-(1-methyl-1H-pyrazol-4-yl)-1,7-naphthyridin-6-yl) benzo[d]oxazole-6-carboxamide [2930];
N-(3-(1-methyl-1H-pyrazol-4-yl)-1,7-naphthyridin-6-yl) benzo[d]thiazole-6-carboxamide [2931];
N-(3-(1-methyl-1H-pyrazol-4-yl)-1,7-naphthyridin-6-yl) benzo[d]oxazole-5-carboxamide [2932];
N-(3-(1-methyl-1H-pyrazol-4-yl)-1,7-naphthyridin-6-yl) benzo[d]thiazole-5-carboxamide [2933];
N-(3-(1-methyl-1H-pyrazol-4-yl)-1,7-naphthyridin-6-yl) quinoline-3-carboxamide [2934];
N-(3-(1-methyl-1H-pyrazol-4-yl)-1,7-naphthyridin-6-yl) quinoline-6-carboxamide [2935];
N-(3-(1-methyl-1H-pyrazol-4-yl)-1,7-naphthyridin-6-yl) quinoxaline-6-carboxamide [2936];
5-chloro-N-(3-(1-methyl-1H-pyrazol-4-yl)-1,7-naphthyridin-6-yl)-2-(4-methylpiperazin-1-yl) isonicotinamide [2937];
3-chloro-N-(3-(1-methyl-1H-pyrazol-4-yl)-1,7-naphthyridin-6-yl)-2-(4-methylpiperazin-1-yl) isonicotinamide [2938];
2-(2,5-diazabicyclo[2.2.1]heptan-2-yl)-N-(3-(1-methyl-1H-pyrazol-4-yl)-1,7-naphthyridin-6-yl) isonicotinamide [2939];
N-(3-(1-methyl-1H-pyrazol-4-yl)-1,7-naphthyridin-6-yl)-2-(5-methyl-2,5-diazabicyclo[2.2.1] heptan-2-yl)isonicotinamide [2940];
3-fluoro-N-(3-(1-methyl-1H-pyrazol-4-yl)-1,7-naphthyridin-6-yl)-2-(4-methylpiperazin-1-yl) isonicotinamide [2941];
N-(3-(1-methyl-1H-pyrazol-4-yl)-1,7-naphthyridin-6-yl)-2-((4-methylpiperazin-1-yl)methyl) isonicotinamide [2942];
N-(3-(1-methyl-1H-pyrazol-4-yl)-1,7-naphthyridin-6-yl)-2-(morpholinomethyl)isonicotinamide [2943];
N-(3-(1-methyl-1H-pyrazol-4-yl)-1,7-naphthyridin-6-yl)-2-(pyrrolidin-1-ylmethyl) isonicotinamide [2944];
N-(3-(1-methyl-1H-pyrazol-4-yl)-1,7-naphthyridin-6-yl)-2-(2-(4-methylpiperazin-1-yl)pyridin-4-yl)acetamide [2945];
1-methyl-N-(3-(1-methyl-1H-pyrazol-4-yl)-1,7-naphthyridin-6-yl)-1H-indazole-5-carboxamide [2946];
1-methyl-N-(3-(1-methyl-1H-pyrazol-4-yl)-1,7-naphthyridin-6-yl)-1H-benzo[d]imidazole-5-carboxamide [2947];
N-(3-(1-methyl-1H-pyrazol-4-yl)-1,7-naphthyridin-6-yl)-1-(piperidin-4-yl)-1H-pyrazole-4-carboxamide [2948];
N-(3-(1-methyl-1H-pyrazol-4-yl)-1,7-naphthyridin-6-yl)-1-(1-methylpiperidin-4-yl)-1H-pyrazole-4-carboxamide [2949];

1-(1-ethylpiperidin-4-yl)-N-(3-(1-methyl-1H-pyrazol-4-yl)-1,7-naphthyridin-6-yl)-1H-pyrazole-4-carboxamide [2950];

1-(1-(2-fluoroethyl)piperidin-4-yl)-N-(3-(1-methyl-1H-pyrazol-4-yl)-1,7-naphthyridin-6-yl)-1H-pyrazole-4-carboxamide [2951];

1-(1-isopropylpiperidin-4-yl)-N-(3-(1-methyl-1H-pyrazol-4-yl)-1,7-naphthyridin-6-yl)-1H-pyrazole-4-carboxamide [2952];

1-(1-cyclopropylpiperidin-4-yl)-N-(3-(1-methyl-1H-pyrazol-4-yl)-1,7-naphthyridin-6-yl)-1H-pyrazole-4-carboxamide [2953];

isopropyl 4-(4-((3-(1-methyl-1H-pyrazol-4-yl)-1,7-naphthyridin-6-yl)carbamoyl)-1H-pyrazol-1-yl)piperidine-1-carboxylate [2954];

N-(3-(1-methyl-1H-pyrazol-4-yl)-1,7-naphthyridin-6-yl)-1-(piperidin-4-yl)-1H-1,2,3-triazole-4-carboxamide [2955];

N-(3-(1-methyl-1H-pyrazol-4-yl)-1,7-naphthyridin-6-yl)-1-(1-methylpiperidin-4-yl)-1H-1,2,3-triazole-4-carboxamide [2956];

1-(1-(2-fluoroethyl)piperidin-4-yl)-N-(3-(1-methyl-1H-pyrazol-4-yl)-1,7-naphthyridin-6-yl)-1H-1,2,3-triazole-4-carboxamide [2957];

1-(1-isopropylpiperidin-4-yl)-N-(3-(1-methyl-1H-pyrazol-4-yl)-1,7-naphthyridin-6-yl)-1H-1,2,3-triazole-4-carboxamide [2958];

N-(3-(1-methyl-1H-pyrazol-4-yl)-1,7-naphthyridin-6-yl)-2-(4-methylpiperazin-1-yl)oxazole-5-carboxamide [2959];

2-(3-(dimethylamino)azetidin-1-yl)-N-(3-(1-methyl-1H-pyrazol-4-yl)-1,7-naphthyridin-6-yl) oxazole-4-carboxamide [2960];

N-(3-(1-methyl-1H-pyrazol-4-yl)-1,7-naphthyridin-6-yl)-2-(piperidin-4-yl)oxazole-4-carboxamide [2961];

N-(3-(1-methyl-1H-pyrazol-4-yl)-1,7-naphthyridin-6-yl)-2-(1-methylpiperidin-4-yl)oxazole-4-carboxamide [2962];

2-(1-(2-fluoroethyl)piperidin-4-yl)-N-(3-(1-methyl-1H-pyrazol-4-yl)-1,7-naphthyridin-6-yl) oxazole-4-carboxamide [2963];

2-(1-isopropylpiperidin-4-yl)-N-(3-(1-methyl-1H-pyrazol-4-yl)-1,7-naphthyridin-6-yl)oxazole-4-carboxamide [2964];

N-(3-(1-methyl-1H-pyrazol-4-yl)-1,7-naphthyridin-6-yl)-2-(4-methylpiperazin-1-yl)oxazole-4-carboxamide [2965];

2-(3-(dimethylamino)azetidin-1-yl)-N-(3-(1-methyl-1H-pyrazol-4-yl)-1,7-naphthyridin-6-yl) thiazole-5-carboxamide [2966];

N-(3-(1-methyl-1H-pyrazol-4-yl)-1,7-naphthyridin-6-yl)-2-(piperidin-4-yl)thiazole-4-carboxamide [2967];

N-(3-(1-methyl-1H-pyrazol-4-yl)-1,7-naphthyridin-6-yl)-2-(4-methylpiperazin-1-yl)thiazole-4-carboxamide [2968];

2-(1-(2-fluoroethyl)piperidin-4-yl)-N-(3-(1-methyl-1H-pyrazol-4-yl)-1,7-naphthyridin-6-yl) thiazole-4-carboxamide [2969];

2-(1-isopropylpiperidin-4-yl)-N-(3-(1-methyl-1H-pyrazol-4-yl)-1,7-naphthyridin-6-yl)thiazole-4-carboxamide [2970];

1-methyl-N-(3-(1-methyl-1H-pyrazol-4-yl)-1,7-naphthyridin-6-yl-5-d)piperidine-4-carboxamide [2971];

N-(3-(1-methyl-1H-pyrazol-4-yl)-1,7-naphthyridin-6-yl)-1-(2-(methyl-d$_3$)propyl-1,1,2,3,3,3-d$_6$) piperidine-4-carboxamide [2972];

N-(3-(1-methyl-1H-pyrazol-4-yl)-1,7-naphthyridin-6-yl)-2-(pyrrolidin-1-yl-2,2,5,5-d$_4$)acetamide [2973];

N-(3-(1-methyl-1H-pyrazol-4-yl)-1,7-naphthyridin-6-yl)-2-(4-(methyl-d$_3$)piperazin-1-yl) acetamide [2974];

N-(3-(1-methyl-1H-pyrazol-4-yl)-1,7-naphthyridin-6-yl)-2-(morpholino-d$_8$)acetamide [2975];

(S)—N-(3-(1-(methyl-d$_3$)-1H-pyrazol-4-yl)-1,7-naphthyridin-6-yl)-2-(pyrrolidin-1-yl)propanamide [2976];

1-isobutyl-N-(3-(1-(methyl-d$_3$)-1H-pyrazol-4-yl)-1,7-naphthyridin-6-yl)piperidine-4-carboxamide [2977];

N-(3-(1-(methyl-d$_3$)-1H-pyrazol-4-yl)-1,7-naphthyridin-6-yl)-2-(4-methylpiperazin-1-yl) acetamide [2978];

N-(3-(1-(methyl-d$_3$)-1H-pyrazol-4-yl)-1,7-naphthyridin-6-yl)-2-(pyrrolidin-1-yl)acetamide [2979];

N-(3-(1-(methyl-d$_3$)-1H-pyrazol-4-yl)-1,7-naphthyridin-6-yl)-2-(piperidin-1-yl)acetamide [2980];

N-(3-(1-(methyl-d$_3$)-1H-pyrazol-4-yl)-1,7-naphthyridin-6-yl)-1-(3,3,3-trifluoropropyl)piperidine-4-carboxamide [2981];

N-(3-(1H-pyrazol-4-yl)-1,7-naphthyridin-6-yl)-2-(4-(methyl-d$_3$)piperazin-1-yl)isonicotinamide [2982];

N-(3-(1-methyl-1H-pyrazol-4-yl)-1,7-naphthyridin-6-yl)-2-(4-(methyl-d$_3$)piperazin-1-yl) isonicotinamide [2983];

N-(3-(1-(methyl-d$_3$)-1H-pyrazol-4-yl)-1,7-naphthyridin-6-yl)-2-(4-methylpiperazin-1-yl) isonicotinamide [2984];

N-(3-(1-(methyl-d$_3$)-1H-pyrazol-4-yl)-1,7-naphthyridin-6-yl)-2-(4-(methyl-d$_3$)piperazin-1-yl) isonicotinamide [2985];

N-(3-(1-(methyl-d$_3$)-1H-pyrazol-4-yl)-1,7-naphthyridin-6-yl)-1-(piperidin-4-yl)-1H-pyrazole-4-carboxamide [2986];

N-(3-(1-(methyl-d$_3$)-1H-pyrazol-4-yl)-1,7-naphthyridin-6-yl)-1-(1-methylpiperidin-4-yl)-1H-pyrazole-4-carboxamide [2987];

N-(3-(1-(methyl-d$_3$)-1H-pyrazol-4-yl)-1,7-naphthyridin-6-yl)-2-(piperidin-4-yl)oxazole-4-carboxamide [2988];

N-(3-(1-(methyl-d$_3$)-1H-pyrazol-4-yl)-1,7-naphthyridin-6-yl)-2-(1-methylpiperidin-4-yl)oxazole-4-carboxamide [2989];

N-(3-(1-ethyl-1H-pyrazol-4-yl)-1,7-naphthyridin-6-yl)-2-(pyrrolidin-1-yl)acetamide [2990];

N-(3-(1-cyclopropyl-1H-pyrazol-4-yl)-1,7-naphthyridin-6-yl)-2-(pyrrolidin-1-yl)acetamide [2991];

N-(3-(1-cyclopropyl-1H-pyrazol-4-yl)-1,7-naphthyridin-6-yl)-1-(3,3,3-trifluoropropyl)piperidine-4-carboxamide [2992];

N-(3-(1-(1-methylpiperidin-4-yl)-1H-pyrazol-4-yl)-1,7-naphthyridin-6-yl) cyclohexanecarboxamide [2993];

2-(pyrrolidin-1-yl)-N-(3-(5-(trifluoromethyl)-1H-pyrazol-4-yl)-1,7-naphthyridin-6-yl)acetamide [2994];

N-(3-(5-(hydroxymethyl)-1-methyl-1H-pyrazol-4-yl)-1,7-naphthyridin-6-yl)-1-methylpiperidine-4-carboxamide [2995];

N-(3-(5-(hydroxymethyl)-1-methyl-1H-pyrazol-4-yl)-1,7-naphthyridin-6-yl)tetrahydro-2H-pyran-4-carboxamide [2996];

N-(3-(5-(azetidin-1-ylmethyl)-1-methyl-1H-pyrazol-4-yl)-1,7-naphthyridin-6-yl)-4,4-difluorocyclohexane-1-carboxamide [2997];

4,4-difluoro-N-(3-(1-methyl-5-(pyrrolidin-1-ylmethyl)-1H-pyrazol-4-yl)-1,7-naphthyridin-6-yl) cyclohexane-1-carboxamide [2998];

4,4-difluoro-N-(3-(1-methyl-5-(piperidin-1-ylmethyl)-1H-pyrazol-4-yl)-1,7-naphthyridin-6-yl) cyclohexane-1-carboxamide [2999];

2-(2-fluoroethyl)-N-(3-(1-methyl-5-(piperidin-1-ylmethyl)-1H-pyrazol-4-yl)-1,7-naphthyridin-6-yl)-2-azaspiro[3.3]heptane-6-carboxamide [3000];

tert-butyl 6-((3-(1-methyl-5-(piperidin-1-ylmethyl)-1H-pyrazol-4-yl)-1,7-naphthyridin-6-yl) carbamoyl)-2-azaspiro[3.3]heptane-2-carboxylate [3001];

2-fluoro-2-methyl-N-(3-(1-methyl-5-(piperidin-1-ylmethyl)-1H-pyrazol-4-yl)-1,7-naphthyridin-6-yl)propanamide [3002];

2-(diethylamino)-N-(3-(1-methyl-5-(piperidin-1-ylmethyl)-1H-pyrazol-4-yl)-1,7-naphthyridin-6-yl)acetamide [3003];

trans-4-methoxy-N-(3-(1-methyl-5-(piperidin-1-ylmethyl)-1H-pyrazol-4-yl)-1,7-naphthyridin-6-yl)cyclohexane-1-carboxamide [3004];

trans-4-(hydroxymethyl)-N-(3-(1-methyl-5-(piperidin-1-ylmethyl)-1H-pyrazol-4-yl)-1,7-naphthyridin-6-yl)cyclohexane-1-carboxamide [3005];

(R)—N-(3-(1-methyl-5-(piperidin-1-ylmethyl)-1H-pyrazol-4-yl)-1,7-naphthyridin-6-yl)pyrrolidine-2-carboxamide [3006];

1-isobutyl-N-(3-(1-methyl-5-(piperidin-1-ylmethyl)-1H-pyrazol-4-yl)-1,7-naphthyridin-6-yl) piperidine-4-carboxamide [3007];

N-(3-(1-methyl-5-(piperidin-1-ylmethyl)-1H-pyrazol-4-yl)-1,7-naphthyridin-6-yl)-1-(oxetan-3-yl) piperidine-4-carboxamide [3008];

1-benzoyl-N-(3-(1-methyl-5-(piperidin-1-ylmethyl)-1H-pyrazol-4-yl)-1,7-naphthyridin-6-yl) piperidine-4-carboxamide [3009];

N-(3-(1-methyl-5-(piperidin-1-ylmethyl)-1H-pyrazol-4-yl)-1,7-naphthyridin-6-yl)tetrahydro-2H-pyran-4-carboxamide [3010];

N-(3-(1-methyl-5-(piperidin-1-ylmethyl)-1H-pyrazol-4-yl)-1,7-naphthyridin-6-yl)-2-(4-methylpiperidin-1-yl)acetamide [3011];

N-(3-(1-(difluoromethyl)-1H-pyrazol-4-yl)-1,7-naphthyridin-6-yl)-2-(4-methylpiperazin-1-yl) isonicotinamide [3012];

N-(3-(1-ethyl-1H-pyrazol-4-yl)-1,7-naphthyridin-6-yl)-2-(4-methylpiperazin-1-yl) isonicotinamide [3013];

N-(3-(1-isopropyl-1H-pyrazol-4-yl)-1,7-naphthyridin-6-yl)-3-(piperidin-4-yloxy)benzamide [3014];

N-(3-(1-isopropyl-1H-pyrazol-4-yl)-1,7-naphthyridin-6-yl)-3-((1-methylpiperidin-4-yl)oxy) benzamide [3015];

N-(3-(1-isopropyl-1H-pyrazol-4-yl)-1,7-naphthyridin-6-yl)-4-(piperidin-4-yloxy)benzamide [3016];

N-(3-(1-cyclopropyl-1H-pyrazol-4-yl)-1,7-naphthyridin-6-yl)-2-(4-methylpiperazin-1-yl) isonicotinamide [3017];

4-fluoro-N-(3-(1-(1-methylpiperidin-4-yl)-1H-pyrazol-4-yl)-1,7-naphthyridin-6-yl)benzamide [3018];

4-(difluoromethoxy)-N-(3-(1-(1-methylpiperidin-4-yl)-1H-pyrazol-4-yl)-1,7-naphthyridin-6-yl) benzamide [3019];

5-fluoro-N-(3-(1-(1-methylpiperidin-4-yl)-1H-pyrazol-4-yl)-1,7-naphthyridin-6-yl)nicotinamide [3020];

$N^2$-methyl-$N^5$-(3-(1-(1-methylpiperidin-4-yl)-1H-pyrazol-4-yl)-1,7-naphthyridin-6-yl)pyridine-2,5-dicarboxamide [3021];

1-isopropyl-N-(3-(1-(1-methylpiperidin-4-yl)-1H-pyrazol-4-yl)-1,7-naphthyridin-6-yl)-1H-pyrazole-4-carboxamide [3022];

2-methyl-N-(3-(1-(1-methylpiperidin-4-yl)-1H-pyrazol-4-yl)-1,7-naphthyridin-6-yl)thiazole-5-carboxamide [3023];

N-(3-(5-amino-1-methyl-1H-pyrazol-4-yl)-1,7-naphthyridin-6-yl)-2-(4-methylpiperazin-1-yl) isonicotinamide [3024];

4-(difluoromethoxy)-N-(3-(5-(hydroxymethyl)-1-methyl-1H-pyrazol-4-yl)-1,7-naphthyridin-6-yl) benzamide [3025];

N-(3-(5-(hydroxymethyl)-1-methyl-1H-pyrazol-4-yl)-1,7-naphthyridin-6-yl)-2-(4-methylpiperazin-1-yl)isonicotinamide [3026];

N-(3-(5-(hydroxymethyl)-1-methyl-1H-pyrazol-4-yl)-1,7-naphthyridin-6-yl)-2-(7-methyl-2,7-diazaspiro[3.5]nonan-2-yl)isonicotinamide [3027];

4-fluoro-N-(3-(1-methyl-5-(pyrrolidin-1-ylmethyl)-1H-pyrazol-4-yl)-1,7-naphthyridin-6-yl) benzamide [3028];

4-fluoro-N-(3-(1-methyl-5-(piperidin-1-ylmethyl)-1H-pyrazol-4-yl)-1,7-naphthyridin-6-yl) benzamide [3029];

4-(difluoromethoxy)-N-(3-(1-methyl-5-(piperidin-1-ylmethyl)-1H-pyrazol-4-yl)-1,7-naphthyridin-6-yl)benzamide [3030];

N-(3-(1-methyl-5-(piperidin-1-ylmethyl)-1H-pyrazol-4-yl)-1,7-naphthyridin-6-yl)-3-(pyrrolidin-1-ylmethyl) benzamide [3031];

N-(3-(1-methyl-5-(piperidin-1-ylmethyl)-1H-pyrazol-4-yl)-1,7-naphthyridin-6-yl)-2-(7-methyl-2,7-diazaspiro[3.5]nonan-2-yl)isonicotinamide [3032];

N-(3-(1-methyl-5-(piperidin-1-ylmethyl)-1H-pyrazol-4-yl)-1,7-naphthyridin-6-yl)-2-morpholinoisonicotinamide [3033];

N-(3-(1-methyl-5-(morpholinomethyl)-1H-pyrazol-4-yl)-1,7-naphthyridin-6-yl)-2-morpholinoisonicotinamide [3034];

N-(3-(4,5,6,7-tetrahydropyrazolo[1,5-a]pyrazin-3-yl)-1,7-naphthyridin-6-yl)-1-((1-(trifluoromethyl)cyclopropyl)methyl)piperidine-4-carboxamide [3035];

3,3-difluoro-N-(3-(5-methyl-4,5,6,7-tetrahydropyrazolo[1,5-a]pyrazin-3-yl)-1,7-naphthyridin-6-yl)cyclobutane-1-carboxamide [3036];

N-((4,4-difluorocyclohexyl)methyl)-3-(5-(2-fluoroethyl)-4,5,6,7-tetrahydropyrazolo[1,5-a] pyrazin-3-yl)-1,7-naphthyridin-6-amine [3037];

N-(3-(5-(2-fluoroethyl)-4,5,6,7-tetrahydropyrazolo[1,5-a]pyrazin-3-yl)-1,7-naphthyridin-6-yl)-1-((1-(trifluoromethyl)cyclopropyl)methyl)piperidine-4-carboxamide [3038];

N-(3-(5-(2-fluoroethyl)-4,5,6,7-tetrahydropyrazolo[1,5-a]pyrazin-3-yl)-1,7-naphthyridin-6-yl)-2-(pyrrolidin-1-yl)acetamide [3039];

2-(7-azabicyclo[2.2.1]heptan-7-yl)-N-(3-(5-(2-fluoroethyl)-4,5,6,7-tetrahydropyrazolo[1,5-a]pyrazin-3-yl)-1,7-naphthyridin-6-yl)acetamide [3040];

(R)—N-(3-(5-(2-fluoroethyl)-4,5,6,7-tetrahydropyrazolo[1,5-a]pyrazin-3-yl)-1,7-naphthyridin-6-yl)-1-isobutylpiperidine-3-carboxamide [3041];

N-(3-(5-(2-fluoroethyl)-4,5,6,7-tetrahydropyrazolo[1,5-a]pyrazin-3-yl)-1,7-naphthyridin-6-yl) piperidine-4-carboxamide [3042];

4-fluoro-N-(3-(5-(2-fluoroethyl)-4,5,6,7-tetrahydropyrazolo[1,5-a]pyrazin-3-yl)-1,7-naphthyridin-6-yl)-1-isobutylpiperidine-4-carboxamide [3043];

N-(3-(5-(2-fluoroethyl)-4,5,6,7-tetrahydropyrazolo[1,5-a]pyrazin-3-yl)-1,7-naphthyridin-6-yl)-2-(4-methylpiperazin-1-yl)acetamide [3044];

4-fluoro-N-(3-(4,5,6,7-tetrahydropyrazolo[1,5-a]pyrazin-3-yl)-1,7-naphthyridin-6-yl)benzamide [3045];

N-(3-(5-(2-fluoroethyl)-4,5,6,7-tetrahydropyrazolo[1,5-a]pyrazin-3-yl)-1,7-naphthyridin-6-yl)-3-(4-methylpiperazin-1-yl)benzamide [3046];

$N^5$-(3-(5-(2-fluoroethyl)-4,5,6,7-tetrahydropyrazolo[1,5-a]pyrazin-3-yl)-1,7-naphthyridin-6-yl)-$N^2$-methylpyridine-2,5-dicarboxamide [3047];

N-(3-(5-(2-fluoroethyl)-4,5,6,7-tetrahydropyrazolo[1,5-a]pyrazin-3-yl)-1,7-naphthyridin-6-yl)-6-(4-methylpiperazin-1-yl)nicotinamide [3048];

2-(azetidin-3-yloxy)-N-(3-(5-(2-fluoroethyl)-4,5,6,7-tetrahydropyrazolo[1,5-a]pyrazin-3-yl)-1,7-naphthyridin-6-yl)isonicotinamide [3049];

N-(3-(1-methyl-1H-pyrazol-5-yl)-1,7-naphthyridin-6-yl)-1-(3,3,3-trifluoropropyl)piperidine-4-carboxamide [3050];

1-methyl-N-(3-(1-methyl-1H-pyrazol-3-yl)-1,7-naphthyridin-6-yl)piperidine-4-carboxamide [3051];

N-(3-(1-methyl-1H-pyrazol-3-yl)-1,7-naphthyridin-6-yl)-2-(4-methylpiperazin-1-yl) isonicotinamide [3052];

2-fluoro-2-methyl-N-(3-(1-methyl-1H-1,2,3-triazol-4-yl)-1,7-naphthyridin-6-yl)propanamide [3053];

2,2,3,3-tetramethyl-N-(3-(1-methyl-1H-1,2,3-triazol-4-yl)-1,7-naphthyridin-6-yl)cyclopropane-1-carboxamide [3054];

trans-N-(3-(1-methyl-1H-1,2,3-triazol-4-yl)-1,7-naphthyridin-6-yl)-4-(pyrrolidin-1-yl) cyclohexane-1-carboxamide [3055];

trans-N-(3-(1-methyl-1H-1,2,3-triazol-4-yl)-1,7-naphthyridin-6-yl)-4-morpholinocyclohexane-1-carboxamide [3056];

N-(3-(1-methyl-1H-1,2,3-triazol-4-yl)-1,7-naphthyridin-6-yl)-2-(piperidin-1-yl)acetamide [3057];

1-ethyl-4-fluoro-N-(3-(1-methyl-1H-1,2,3-triazol-4-yl)-1,7-naphthyridin-6-yl)piperidine-4-carboxamide [3058];

4-fluoro-1-isobutyl-N-(3-(1-methyl-1H-1,2,3-triazol-4-yl)-1,7-naphthyridin-6-yl)piperidine-4-carboxamide [3059];

N-(3-(1-methyl-1H-1,2,3-triazol-4-yl)-1,7-naphthyridin-6-yl)-1-(3,3,3-trifluoropropyl)piperidine-4-carboxamide [3060];

N-(3-(1-methyl-1H-1,2,3-triazol-4-yl)-1,7-naphthyridin-6-yl)cyclopropanecarboxamide [3061];

4,4-difluoro-N-(3-(1-methyl-1H-1,2,3-triazol-4-yl)-1,7-naphthyridin-6-yl)cyclohexane-1-carboxamide [3062];

trans-4-(dimethylamino)-N-(3-(1-methyl-1H-1,2,3-triazol-4-yl)-1,7-naphthyridin-6-yl) cyclohexane-1-carboxamide [3063];

trans-N-(3-(1-methyl-1H-1,2,3-triazol-4-yl)-1,7-naphthyridin-6-yl)-4-((4-methylpiperazin-1-yl) methyl)cyclohexane-1-carboxamide [3064];

N-(3-(1-methyl-1H-1,2,3-triazol-4-yl)-1,7-naphthyridin-6-yl)piperidine-4-carboxamide [3065];

1-isobutyl-N-(3-(1-methyl-1H-1,2,3-triazol-4-yl)-1,7-naphthyridin-6-yl)piperidine-4-carboxamide [3066];

N-(3-(1-methyl-1H-1,2,3-triazol-4-yl)-1,7-naphthyridin-6-yl)-1-((1-(trifluoromethyl)cyclopropyl) methyl)piperidine-4-carboxamide [3067];

N-(3-(1-methyl-1H-1,2,3-triazol-4-yl)-1,7-naphthyridin-6-yl)-1-((3-methyloxetan-3-yl) methyl)piperidine-4-carboxamide [3068];

N-(3-(1-methyl-1H-1,2,3-triazol-4-yl)-1,7-naphthyridin-6-yl)-1-(2-(pyrrolidin-1-yl) acetyl)piperidine-4-carboxamide [3069];

1'-methyl-N-(3-(1-methyl-1H-1,2,3-triazol-4-yl)-1,7-naphthyridin-6-yl)-[1,4'-bipiperidine]-4-carboxamide [3070];

(R)—N-(3-(1-methyl-1H-1,2,3-triazol-4-yl)-1,7-naphthyridin-6-yl)piperidine-3-carboxamide [3071];

(R)-1-isobutyl-N-(3-(1-methyl-1H-1,2,3-triazol-4-yl)-1,7-naphthyridin-6-yl)piperidine-3-carboxamide [3072];

N-(3-(1-methyl-1H-1,2,3-triazol-4-yl)-1,7-naphthyridin-6-yl)-2-(pyrrolidin-1-yl)acetamide [3073];

N-(3-(1-methyl-1H-1,2,3-triazol-4-yl)-1,7-naphthyridin-6-yl)-2-(4-methylpiperazin-1-yl) acetamide [3074];

2-(7-azabicyclo[2.2.1]heptan-7-yl)-N-(3-(1-methyl-1H-1,2,3-triazol-4-yl)-1,7-naphthyridin-6-yl) acetamide [3075];

1-(2-hydroxy-2-methylpropyl)-N-(3-(1-methyl-1H-1,2,3-triazol-4-yl)-1,7-naphthyridin-6-yl) piperidine-4-carboxamide [3076];

N-(3-(1-methyl-1H-1,2,3-triazol-4-yl)-1,7-naphthyridin-6-yl)-2-morpholinoacetamide [3077];

2-(4-methoxypiperidin-1-yl)-N-(3-(1-methyl-1H-1,2,3-triazol-4-yl)-1,7-naphthyridin-6-yl) acetamide [3078];

N-(3-(1-methyl-1H-1,2,3-triazol-4-yl)-1,7-naphthyridin-6-yl)morpholine-4-carboxamide [3079];

N-(3-(1-methyl-1H-1,2,3-triazol-4-yl)-1,7-naphthyridin-6-yl)-1-(piperidin-4-yl)-1H-pyrazole-4-carboxamide [3080];

N-(3-(1-methyl-1H-1,2,3-triazol-4-yl)-1,7-naphthyridin-6-yl)-1-(1-methylpiperidin-4-yl)-1H-pyrazole-4-carboxamide [3081];

1-(1-ethylpiperidin-4-yl)-N-(3-(1-methyl-1H-1,2,3-triazol-4-yl)-1,7-naphthyridin-6-yl)-1H-pyrazole-4-carboxamide [3082];

1-(1-isopropylpiperidin-4-yl)-N-(3-(1-methyl-1H-1,2,3-triazol-4-yl)-1,7-naphthyridin-6-yl)-1H-pyrazole-4-carboxamide [3083];

N-(3-(1-methyl-1H-1,2,3-triazol-4-yl)-1,7-naphthyridin-6-yl)-1-(piperidin-4-yl)-1H-1,2,3-triazole-4-carboxamide [3084];

1-(1-(2-fluoroethyl)piperidin-4-yl)-N-(3-(1-methyl-1H-1,2,3-triazol-4-yl)-1,7-naphthyridin-6-yl)-1H-1,2,3-triazole-4-carboxamide [3085];

1-(1-isopropylpiperidin-4-yl)-N-(3-(1-methyl-1H-1,2,3-triazol-4-yl)-1,7-naphthyridin-6-yl)-1H-1,2,3-triazole-4-carboxamide [3086];

N-(3-(1-methyl-1H-1,2,3-triazol-4-yl)-1,7-naphthyridin-6-yl)-2-(piperidin-4-yl)oxazole-4-carboxamide [3087];

N-(3-(1-methyl-1H-1,2,3-triazol-4-yl)-1,7-naphthyridin-6-yl)-2-(1-methylpiperidin-4-yl)oxazole-4-carboxamide [3088];

2-(1-isopropylpiperidin-4-yl)-N-(3-(1-methyl-1H-1,2,3-triazol-4-yl)-1,7-naphthyridin-6-yl) oxazole-4-carboxamide [3089];

2-fluoro-N-(3-(1-methyl-1H-1,2,3-triazol-4-yl)-1,7-naphthyridin-6-yl)benzamide [3090];

N-(3-(1-methyl-1H-1,2,3-triazol-4-yl)-1,7-naphthyridin-6-yl)-3-((1-methylpiperidin-4-yl)oxy) benzamide [3091];

$N^2$-methyl-$N^5$-(3-(1-methyl-1H-1,2,3-triazol-4-yl)-1,7-naphthyridin-6-yl)pyridine-2,5-dicarboxamide [3092];

N-(3-(1-methyl-1H-1,2,3-triazol-4-yl)-1,7-naphthyridin-6-yl)-6-(4-methylpiperazin-1-yl) nicotinamide [3093];

2-(3-(dimethylamino)azetidin-1-yl)-N-(3-(1-methyl-1H-1,2,3-triazol-4-yl)-1,7-naphthyridin-6-yl) isonicotinamide [3094];

N-(3-(1-methyl-1H-1,2,3-triazol-4-yl)-1,7-naphthyridin-6-yl)-2-(1-methylpiperidin-4-yl) isonicotinamide [3095];

2-(4-(dimethylamino)piperidin-1-yl)-N-(3-(1-methyl-1H-1,2,3-triazol-4-yl)-1,7-naphthyridin-6-yl)isonicotinamide [3096];

N-(3-(1-methyl-1H-1,2,3-triazol-4-yl)-1,7-naphthyridin-6-yl)-2-morpholinoisonicotinamide [3097];
N-(3-(1-methyl-1H-1,2,3-triazol-4-yl)-1,7-naphthyridin-6-yl)-2-(4-methylpiperazin-1-yl) isonicotinamide [3098];
2-(4-methyl-1,4-diazepan-1-yl)-N-(3-(1-methyl-1H-1,2,3-triazol-4-yl)-1,7-naphthyridin-6-yl) isonicotinamide [3099];
2-(4-isopropylpiperazin-1-yl)-N-(3-(1-methyl-1H-1,2,3-triazol-4-yl)-1,7-naphthyridin-6-yl) isonicotinamide [3100];
N-(3-(1-methyl-1H-1,2,3-triazol-4-yl)-1,7-naphthyridin-6-yl)-2-(piperidin-4-ylamino) isonicotinamide [3101];
2-(methyl(1-methylpiperidin-4-yl)amino)-N-(3-(1-methyl-1H-1,2,3-triazol-4-yl)-1,7-naphthyridin-6-yl) isonicotinamide [3102];
N-(3-(1-methyl-1H-1,2,3-triazol-4-yl)-1,7-naphthyridin-6-yl)-2-((1-methylpiperidin-4-yl)thio) isonicotinamide [3103];
2-methyl-N-(3-(1-methyl-1H-1,2,3-triazol-4-yl)-1,7-naphthyridin-6-yl)-1,2,3,4-tetrahydroisoquinoline-6-carboxamide [3104];
N-(3-(1-methyl-1H-1,2,3-triazol-4-yl)-1,7-naphthyridin-6-yl)-2-(piperazin-1-yl)isonicotinamide [3105];
N-(3-(1-methyl-1H-1,2,3-triazol-4-yl)-1,7-naphthyridin-6-yl)-2-(2-(4-methylpiperazin-1-yl) pyridin-4-yl)acetamide [3106];
1,1-bis(methyl-$d_3$)-4-(4-((3-(1-methyl-1H-1,2,3-triazol-4-yl)-1,7-naphthyridin-6-yl)carbamoyl) pyridin-2-yl) piperazin-1-ium iodide [3107];
N-(3-(1-methyl-1H-1,2,3-triazol-4-yl)-1,7-naphthyridin-6-yl)-2-(4-(methyl-$d_3$)piperazin-1-yl) isonicotinamide [3108];
N-(3-(1-methyl-1H-1,2,3-triazol-5-yl)-1,7-naphthyridin-6-yl)-1-(3,3,3-trifluoropropyl)piperidine-4-carboxamide [3109];
N-(3-(4-methyl-4H-1,2,4-triazol-3-yl)-1,7-naphthyridin-6-yl)-2-morpholinoacetamide [3110];
N-(3-(4-methyl-4H-1,2,4-triazol-3-yl)-1,7-naphthyridin-6-yl)-1-(3,3,3-trifluoropropyl)piperidine-4-carboxamide [3111];
4-fluoro-1-isobutyl-N-(3-(4-methyl-4H-1,2,4-triazol-3-yl)-1,7-naphthyridin-6-yl)piperidine-4-carboxamide [3112];
N-(3-(4,5-dimethyl-4H-1,2,4-triazol-3-yl)-1,7-naphthyridin-6-yl)-2-morpholinoacetamide [3113];
N-(3-(4,5-dimethyl-4H-1,2,4-triazol-3-yl)-1,7-naphthyridin-6-yl)-1-(3,3,3-trifluoropropyl)piperidine-4-carboxamide [3114];
N-(3-(1H-1,2,3-triazol-1-yl)-1,7-naphthyridin-6-yl)-4-fluoro-1-isobutylpiperidine-4-carboxamide [3115];
N-(3-(2H-1,2,3-triazol-2-yl)-1,7-naphthyridin-6-yl)-4-fluoro-1-isobutylpiperidine-4-carboxamide [3116];
N-(3-(1H-1,2,4-triazol-1-yl)-1,7-naphthyridin-6-yl)-2-(4-methylpiperazin-1-yl)isonicotinamide [3117];
1-isobutyl-N-(3-(1-methyl-1H-tetrazol-5-yl)-1,7-naphthyridin-6-yl)piperidine-4-carboxamide [3118];
2,2,3,3-tetramethyl-N-(3-(1-methyl-1H-imidazol-5-yl)-1,7-naphthyridin-6-yl)cyclopropane-1-carboxamide [3119];
4,4-difluoro-N-(3-(1-methyl-1H-imidazol-5-yl)-1,7-naphthyridin-6-yl)cyclohexane-1-carboxamide [3120];
N-(3-(1-methyl-1H-imidazol-5-yl)-1,7-naphthyridin-6-yl)-2-(piperidin-1-yl)acetamide [3121];
2-fluoro-2-methyl-N-(3-(1-methyl-1H-imidazol-5-yl)-1,7-naphthyridin-6-yl)propanamide [3122];
1-fluoro-N-(3-(1-methyl-1H-imidazol-5-yl)-1,7-naphthyridin-6-yl)cyclopropane-1-carboxamide [3123];
2-methyl-N-(3-(1-methyl-1H-imidazol-5-yl)-1,7-naphthyridin-6-yl)-2-azaspiro[3.3]heptane-6-carboxamide [3124];
1-fluoro-N-(3-(1-methyl-1H-imidazol-5-yl)-1,7-naphthyridin-6-yl)cyclohexane-1-carboxamide [3125];
trans-4-methoxy-N-(3-(1-methyl-1H-imidazol-5-yl)-1,7-naphthyridin-6-yl)cyclohexane-1-carboxamide [3126];
trans-4-(hydroxymethyl)-N-(3-(1-methyl-1H-imidazol-5-yl)-1,7-naphthyridin-6-yl)cyclohexane-1-carboxamide [3127];
N-(3-(1-methyl-1H-imidazol-5-yl)-1,7-naphthyridin-6-yl)azetidine-3-carboxamide [3128];
(R)—N-(3-(1-methyl-1H-imidazol-5-yl)-1,7-naphthyridin-6-yl)tetrahydrofuran-2-carboxamide [3129];
1-(2-methoxyethyl)-N-(3-(1-methyl-1H-imidazol-5-yl)-1,7-naphthyridin-6-yl)piperidine-4-carboxamide [3130];
N-(3-(1-methyl-1H-imidazol-5-yl)-1,7-naphthyridin-6-yl)-1-(3,3,3-trifluoropropyl)piperidine-4-carboxamide [3131];
1-isobutyl-N-(3-(1-methyl-1H-imidazol-5-yl)-1,7-naphthyridin-6-yl)piperidine-4-carboxamide [3132];
N-(3-(1-methyl-1H-imidazol-5-yl)-1,7-naphthyridin-6-yl)-1-(methylsulfonyl)piperidine-4-carboxamide [3133];
N-(3-(1-methyl-1H-imidazol-5-yl)-1,7-naphthyridin-6-yl)-2-(pyrrolidin-1-yl)propanamide [3134];
2-isopropoxy-N-(3-(1-methyl-1H-imidazol-5-yl)-1,7-naphthyridin-6-yl)acetamide [3135];
3-isopropoxy-N-(3-(1-methyl-1H-imidazol-5-yl)-1,7-naphthyridin-6-yl)propanamide [3136];
N-(3-(1,2-dimethyl-1H-imidazol-5-yl)-1,7-naphthyridin-6-yl)cyclopropanecarboxamide [3137];
N-(3-(1,2-dimethyl-1H-imidazol-5-yl)-1,7-naphthyridin-6-yl)cyclohexanecarboxamide [3138];
N-(3-(1,2-dimethyl-1H-imidazol-5-yl)-1,7-naphthyridin-6-yl)-4,4-difluorocyclohexane-1-carboxamide [3139];
(S)—N-(3-(1,2-dimethyl-1H-imidazol-5-yl)-1,7-naphthyridin-6-yl)tetrahydrofuran-2-carboxamide [3140];
N-(3-(1,2-dimethyl-1H-imidazol-5-yl)-1,7-naphthyridin-6-yl)-3,3-difluorocyclobutane-1-carboxamide [3141];
N-(3-(1,2-dimethyl-1H-imidazol-5-yl)-1,7-naphthyridin-6-yl)-1-fluorocyclopropane-1-carboxamide [3142];
N-(3-(1,2-dimethyl-1H-imidazol-5-yl)-1,7-naphthyridin-6-yl)morpholine-4-carboxamide [3143];
N-(3-(1,2-dimethyl-1H-imidazol-5-yl)-1,7-naphthyridin-6-yl)morpholine-$d_8$-4-carboxamide [3144];
1-methyl-N-(3-(1-methyl-1H-imidazol-5-yl)-1,7-naphthyridin-6-yl)-1H-pyrazole-4-carboxamide [3145];
1-ethyl-N-(3-(1-methyl-1H-imidazol-5-yl)-1,7-naphthyridin-6-yl)-1H-pyrazole-4-carboxamide [3146];
1-isopropyl-N-(3-(1-methyl-1H-imidazol-5-yl)-1,7-naphthyridin-6-yl)-1H-pyrazole-4-carboxamide [3147];
1-cyclopropyl-N-(3-(1-methyl-1H-imidazol-5-yl)-1,7-naphthyridin-6-yl)-1H-pyrazole-4-carboxamide [3148];
1-isobutyl-N-(3-(1-methyl-1H-imidazol-5-yl)-1,7-naphthyridin-6-yl)-1H-pyrazole-4-carboxamide [3149];
1-methyl-N-(3-(1-methyl-1H-imidazol-5-yl)-1,7-naphthyridin-6-yl)-1H-pyrazole-3-carboxamide [3150];
N-(3-(1-methyl-1H-imidazol-5-yl)-1,7-naphthyridin-6-yl)-2-(1-methyl-1H-pyrazol-4-yl) acetamide [3151];
1-methyl-N-(3-(1-methyl-1H-imidazol-5-yl)-1,7-naphthyridin-6-yl)-1H-imidazole-4-carboxamide [3152];

1-isopropyl-N-(3-(1-methyl-1H-imidazol-5-yl)-1,7-naphthyridin-6-yl)-1H-imidazole-4-carboxamide [3153];
N-(3-(1-methyl-1H-imidazol-5-yl)-1,7-naphthyridin-6-yl)-1-(tetrahydro-2H-pyran-4-yl)-1H-imidazole-4-carboxamide [3154];
1,2-dimethyl-N-(3-(1-methyl-1H-imidazol-5-yl)-1,7-naphthyridin-6-yl)-1H-imidazole-5-carboxamide [3155];
1-methyl-N-(3-(1-methyl-1H-imidazol-5-yl)-1,7-naphthyridin-6-yl)-1H-1,2,4-triazole-3-carboxamide [3156];
2-methyl-N-(3-(1-methyl-1H-imidazol-5-yl)-1,7-naphthyridin-6-yl)oxazole-4-carboxamide [3157];
2-isopropyl-N-(3-(1-methyl-1H-imidazol-5-yl)-1,7-naphthyridin-6-yl)oxazole-4-carboxamide [3158];
4-methyl-N-(3-(1-methyl-1H-imidazol-5-yl)-1,7-naphthyridin-6-yl)oxazole-2-carboxamide [3159];
4-methyl-N-(3-(1-methyl-1H-imidazol-5-yl)-1,7-naphthyridin-6-yl)thiazole-2-carboxamide [3160];
2-methyl-N-(3-(1-methyl-1H-imidazol-5-yl)-1,7-naphthyridin-6-yl)thiazole-4-carboxamide [3161];
5-methyl-N-(3-(1-methyl-1H-imidazol-5-yl)-1,7-naphthyridin-6-yl)-1,3,4-oxadiazole-2-carboxamide [3162];
5-methyl-N-(3-(1-methyl-1H-imidazol-5-yl)-1,7-naphthyridin-6-yl)-1,3,4-thiadiazole-2-carboxamide [3163];
1-isopropyl-N-(3-(1-isopropyl-1H-imidazol-5-yl)-1,7-naphthyridin-6-yl)-1H-pyrazole-4-carboxamide [3164];
N-(3-(1,2-dimethyl-1H-imidazol-5-yl)-1,7-naphthyridin-6-yl)-1-methyl-1H-pyrazole-4-carboxamide [3165];
N-(3-(1,2-dimethyl-1H-imidazol-5-yl)-1,7-naphthyridin-6-yl)-1-isopropyl-1H-pyrazole-4-carboxamide [3166];
N-(3-(1,2-dimethyl-1H-imidazol-5-yl)-1,7-naphthyridin-6-yl)-2-methylthiazole-5-carboxamide [3167];
4-fluoro-N-(3-(1-methyl-1H-imidazol-5-yl)-1,7-naphthyridin-6-yl)benzamide [3168];
4-fluoro-N-(3-(1-methyl-1H-imidazol-5-yl)-1,7-naphthyridin-6-yl)benzamide-2,3,5,6-$d_4$ [3169];
2-chloro-N-(3-(1-methyl-1H-imidazol-5-yl)-1,7-naphthyridin-6-yl)benzamide-3,4,5,6-$d_4$ [3170];
4-chloro-N-(3-(1-methyl-1H-imidazol-5-yl)-1,7-naphthyridin-6-yl)benzamide-2,3,5,6-$d_4$ [3171];
4-(methyl-$d_3$)—N-(3-(1-methyl-1H-imidazol-5-yl)-1,7-naphthyridin-6-yl)benzamide [3172];
4-methyl-N-(3-(1-methyl-1H-imidazol-5-yl)-1,7-naphthyridin-6-yl)benzamide-2,3,5,6-$d_4$ [3173];
4-(methyl-$d_3$)—N-(3-(1-methyl-1H-imidazol-5-yl)-1,7-naphthyridin-6-yl)benzamide-2,3,5,6-$d_4$ [3174];
4-(methoxy-$d_3$)—N-(3-(1-methyl-1H-imidazol-5-yl)-1,7-naphthyridin-6-yl)benzamide [3175];
4-(methoxy-$d_3$)—N-(3-(1-methyl-1H-imidazol-5-yl)-1,7-naphthyridin-6-yl)benzamide-2,3,56-$d_4$ [3176];
4-methoxy-N-(3-(1-methyl-1H-imidazol-5-yl)-1,7-naphthyridin-6-yl)benzamide-2,3,5,6-$d_4$ [3177];
(E)-N-(3-(1,2-dimethyl-1H-imidazol-5-yl)-1,7-naphthyridin-6-yl)-3-(phenyl-2,3,4,5,6-$d_5$) acrylamide [3178];
(E)-N-(3-(1,2-dimethyl-1H-imidazol-5-yl)-1,7-naphthyridin-6-yl)-3-(phenyl-2,3,4,5,6-$d_5$) acrylamide-2,3-$d_2$ [3179];
N-(3-(1,2-dimethyl-1H-imidazol-5-yl)-1,7-naphthyridin-6-yl)-2-(4-fluorophenyl)acetamide-2,2-$d_2$ [3180];
(E)-N-(3-(1-methyl-1H-imidazol-5-yl)-1,7-naphthyridin-6-yl)-3-(phenyl-2,3,4,5,6-$d_5$)acrylamide [3181];
(E)-N-(3-(1-methyl-1H-imidazol-5-yl)-1,7-naphthyridin-6-yl)-3-(phenyl-2,3,4,5,6-$d_5$)acrylamide-2,3-$d_2$ [3182];
2-(4-fluorophenyl)-N-(3-(1-methyl-1H-imidazol-5-yl)-1,7-naphthyridin-6-yl)acetamide-2,2-$d_2$ [3183];
N-(3-(1-methyl-1H-imidazol-5-yl)-1,7-naphthyridin-6-yl)-2-(4-methylpiperazin-1-yl) isonicotinamide [3184];
2-(dimethylamino)-N-(3-(1-methyl-1H-imidazol-5-yl)-1,7-naphthyridin-6-yl)isonicotinamide [3185];
2-(3-aminoazetidin-1-yl)-N-(3-(1-methyl-1H-imidazol-5-yl)-1,7-naphthyridin-6-yl) isonicotinamide [3186];
N-(3-(1-methyl-1H-imidazol-5-yl)-1,7-naphthyridin-6-yl)-2-(pyrrolidin-1-yl)isonicotinamide [3187];
N-(3-(1-methyl-1H-imidazol-5-yl)-1,7-naphthyridin-6-yl)-2-(piperidin-1-yl)isonicotinamide [3188];
N-(3-(1-methyl-1H-imidazol-5-yl)-1,7-naphthyridin-6-yl)-2-morpholinoisonicotinamide [3189];
2-(4-isopropylpiperazin-1-yl)-N-(3-(1-methyl-1H-imidazol-5-yl)-1,7-naphthyridin-6-yl) isonicotinamide [3190];
2-(4-cyclopropylpiperazin-1-yl)-N-(3-(1-methyl-1H-imidazol-5-yl)-1,7-naphthyridin-6-yl) isonicotinamide [3191];
N-(3-(1-methyl-1H-imidazol-5-yl)-1,7-naphthyridin-6-yl)-2-(2,7-diazaspiro[3.5]nonan-2-yl) isonicotinamide [3192];
N-(3-(1-methyl-1H-imidazol-5-yl)-1,7-naphthyridin-6-yl)-2-(7-methyl-2,7-diazaspiro[3.5]nonan-2-yl)isonicotinamide [3193];
N-(3-(1-methyl-1H-imidazol-5-yl)-1,7-naphthyridin-6-yl)isoindoline-5-carboxamide [3194];
2-methyl-N-(3-(1-methyl-1H-imidazol-5-yl)-1,7-naphthyridin-6-yl)isoindoline-5-carboxamide [3195];
2-(azetidin-1-yl)-N-(3-(1-methyl-1H-imidazol-5-yl)-1,7-naphthyridin-6-yl)isonicotinamide [3196];
2-methoxy-N-(3-(1-methyl-1H-imidazol-5-yl)-1,7-naphthyridin-6-yl)isonicotinamide [3197];
2-methyl-N-(3-(1-methyl-1H-imidazol-5-yl)-1,7-naphthyridin-6-yl)isonicotinamide [3198];
2-cyano-N-(3-(1-methyl-1H-imidazol-5-yl)-1,7-naphthyridin-6-yl)isonicotinamide [3199];
2-(3,3-difluoroazetidin-1-yl)-N-(3-(1-methyl-1H-imidazol-5-yl)-1,7-naphthyridin-6-yl) isonicotinamide [3200];
2-(4,4-difluoropiperidin-1-yl)-N-(3-(1-methyl-1H-imidazol-5-yl)-1,7-naphthyridin-6-yl) isonicotinamide [3201];
2-isopropoxy-N-(3-(1-methyl-1H-imidazol-5-yl)-1,7-naphthyridin-6-yl)isonicotinamide [3202];
N-(3-(1-methyl-1H-imidazol-5-yl)-1,7-naphthyridin-6-yl)-2-(pyrrolidin-1-yl-2,2,5,5-$d_4$) isonicotinamide [3203];
N-(3-(1-methyl-1H-imidazol-5-yl)-1,7-naphthyridin-6-yl)-2-(pyrrolidin-1-yl-$d_8$)isonicotinamide [3204];
N-(3-(1-methyl-1H-imidazol-5-yl)-1,7-naphthyridin-6-yl)-2-(piperidin-1-yl-$d_{10}$)isonicotinamide [3205];
N-(3-(1-methyl-1H-imidazol-5-yl)-1,7-naphthyridin-6-yl)-2-(morpholino-$d_8$)isonicotinamide [3206];
N-(3-(1,2-dimethyl-1H-imidazol-5-yl)-1,7-naphthyridin-6-yl)-4-isopropoxybenzamide [3207];
N-(3-(1,2-dimethyl-1H-imidazol-5-yl)-1,7-naphthyridin-6-yl)-4-(piperidin-4-yloxy)benzamide [3208];
4-(benzyloxy)-N-(3-(1,2-dimethyl-1H-imidazol-5-yl)-1,7-naphthyridin-6-yl)benzamide [3209];
N-(3-(1,2-dimethyl-1H-imidazol-5-yl)-1,7-naphthyridin-6-yl)-2-fluorobenzamide-3,4,5,6-$d_4$ [3210];
N-(3-(1,2-dimethyl-1H-imidazol-5-yl)-1,7-naphthyridin-6-yl)-4-fluorobenzamide-2,3,5,6-$d_4$ [3211];
2-chloro-N-(3-(1,2-dimethyl-1H-imidazol-5-yl)-1,7-naphthyridin-6-yl)benzamide-3,4,5,6-$d_4$ [3212];
4-chloro-N-(3-(1,2-dimethyl-1H-imidazol-5-yl)-1,7-naphthyridin-6-yl)benzamide-2,3,5,6-$d_4$ [3213];

N-(3-(1,2-dimethyl-1H-imidazol-5-yl)-1,7-naphthyridin-6-yl)-4-(methyl-d$_3$)benzamide [3214];
N-(3-(1,2-dimethyl-1H-imidazol-5-yl)-1,7-naphthyridin-6-yl)-4-methylbenzamide-2,3,5,6-d$_4$ [3215];
N-(3-(1,2-dimethyl-1H-imidazol-5-yl)-1,7-naphthyridin-6-yl)-4-(methyl-d3)benzamide-2,3,5,6-d$_4$ [3216];
N-(3-(1,2-dimethyl-1H-imidazol-5-yl)-1,7-naphthyridin-6-yl)-4-(methoxy-d$_3$)benzamide [3217];
N-(3-(1,2-dimethyl-1H-imidazol-5-yl)-1,7-naphthyridin-6-yl)-4-(methoxy-d$_3$)benzamide-2,3,5,6-d$_4$ [3218];
N-(3-(1,2-dimethyl-1H-imidazol-5-yl)-1,7-naphthyridin-6-yl)-4-methoxybenzamide-2,3,5,6-d$_4$ [3219];
N-(3-(1,2-dimethyl-1H-imidazol-5-yl)-1,7-naphthyridin-6-yl)-2-(4-methylpiperazin-1-yl) isonicotinamide [3220];
N-(3-(1,2-dimethyl-1H-imidazol-5-yl)-1,7-naphthyridin-6-yl)-2-morpholinoisonicotinamide [3221];
N-(3-(1,2-dimethyl-1H-imidazol-5-yl)-1,7-naphthyridin-6-yl)-2-(pyrrolidin-1-yl)isonicotinamide [3222];
N-(3-(1,2-dimethyl-1H-imidazol-5-yl)-1,7-naphthyridin-6-yl)-2-(dimethylamino)isonicotinamide [3223];
N-(3-(1,2-dimethyl-1H-imidazol-5-yl)-1,7-naphthyridin-6-yl)-2-(pyrrolidin-1-yl-2,2,5,5-d$_4$) isonicotinamide [3324];
N-(3-(1,2-dimethyl-1H-imidazol-5-yl)-1,7-naphthyridin-6-yl)-2-(pyrrolidin-1-yl-d$_8$) isonicotinamide [3225];
N-(3-(1,2-dimethyl-1H-imidazol-5-yl)-1,7-naphthyridin-6-yl)-2-(piperidin-1-yl-d$_{10}$) isonicotinamide [3226];
N-(3-(1,2-dimethyl-1H-imidazol-5-yl)-1,7-naphthyridin-6-yl)-2-(morpholino-d$_8$)isonicotinamide [3227];
N-(3-(5,6,7,8-tetrahydroimidazo[1,2-a]pyrazin-3-yl)-1,7-naphthyridin-6-yl) cyclopropanecarboxamide [3228];
N-(3-(7-methyl-5,6,7,8-tetrahydroimidazo[1,2-a]pyrazin-3-yl)-1,7-naphthyridin-6-yl) cyclopropanecarboxamide [3229];
3,3-difluoro-N-(3-(5,6,7,8-tetrahydroimidazo[1,2-a]pyrazin-3-yl)-1,7-naphthyridin-6-yl) cyclobutane-1-carboxamide [3230];
(R)—N-(3-(5,6,7,8-tetrahydroimidazo[1,2-a]pyrazin-3-yl)-1,7-naphthyridin-6-yl)pyrrolidine-2-carboxamide [3231];
(R)—N-(3-(5,6,7,8-tetrahydroimidazo[1,2-a]pyrazin-3-yl)-1,7-naphthyridin-6-yl)piperidine-3-carboxamide [3232];
1-methyl-N-(3-(5,6,7,8-tetrahydroimidazo[1,2-a]pyrazin-3-yl)-1,7-naphthyridin-6-yl)piperidine-4-carboxamide [3233];
N-(3-(5,6,7,8-tetrahydroimidazo[1,2-a]pyrazin-3-yl)-1,7-naphthyridin-6-yl)-1-((1-(trifluoromethyl)cyclopropyl)methyl)piperidine-4-carboxamide [3234];
1-benzoyl-N-(3-(5,6,7,8-tetrahydroimidazo[1,2-a]pyrazin-3-yl)-1,7-naphthyridin-6-yl)piperidine-4-carboxamide [3235];
4-fluoro-1-isobutyl-N-(3-(5,6,7,8-tetrahydroimidazo[1,2-a]pyrazin-3-yl)-1,7-naphthyridin-6-yl) piperidine-4-carboxamide [3236];
(R)-2-(2-methylpyrrolidin-1-yl)-N-(3-(5,6,7,8-tetrahydroimidazo[1,2-a]pyrazin-3-yl)-1,7-naphthyridin-6-yl)acetamide [3237];
2-(cyclobutyl(methyl)amino)-N-(3-(5,6,7,8-tetrahydroimidazo[1,2-a]pyrazin-3-yl)-1,7-naphthyridin-6-yl)acetamide [3238];
4-fluoro-N-(3-(5,6,7,8-tetrahydroimidazo[1,2-a]pyrazin-3-yl)-1,7-naphthyridin-6-yl)benzamide [3239];
4-isopropoxy-N-(3-(5,6,7,8-tetrahydroimidazo[1,2-a]pyrazin-3-yl)-1,7-naphthyridin-6-yl) benzamide [3240];
4-(difluoromethoxy)-N-(3-(5,6,7,8-tetrahydroimidazo[1,2-a]pyrazin-3-yl)-1,7-naphthyridin-6-yl)benzamide [3241];
2-((2-(dimethylamino)ethyl)amino)-N-(3-(5,6,7,8-tetrahydroimidazo[1,2-a]pyrazin-3-yl)-1,7-naphthyridin-6-yl)isonicotinamide [3242];
2-((1-isopropylpiperidin-4-yl)oxy)-N-(3-(5,6,7,8-tetrahydroimidazo[1,2-a]pyrazin-3-yl)-1,7-naphthyridin-6-yl) isonicotinamide [3243];
N-(3-(oxazol-5-yl)-1,7-naphthyridin-6-yl)-1-(3,3,3-trifluoropropyl)piperidine-4-carboxamide [3244];
N-(3-(oxazol-5-yl)-1,7-naphthyridin-6-yl)cyclopropanecarboxamide [3245];
(R)—N-(3-(oxazol-5-yl)-1,7-naphthyridin-6-yl)tetrahydrofuran-2-carboxamide [3246];
(R)—N-(3-(oxazol-5-yl)-1,7-naphthyridin-6-yl)piperidine-3-carboxamide [3247];
N-(3-(oxazol-5-yl)-1,7-naphthyridin-6-yl)tetrahydro-2H-pyran-4-carboxamide [3248];
N-(3-(oxazol-5-yl)-1,7-naphthyridin-6-yl)-1-(2-(pyrrolidin-1-yl)acetyl)piperidine-4-carboxamide [3249];
1'-methyl-N-(3-(oxazol-5-yl)-1,7-naphthyridin-6-yl)-[1,4'-bipiperidine]-4-carboxamide [3250];
cis-4-morpholino-N-(3-(oxazol-5-yl)-1,7-naphthyridin-6-yl)cyclohexane-1-carboxamide [3251];
2-(cyclobutyl(methyl)amino)-N-(3-(oxazol-5-yl)-1,7-naphthyridin-6-yl)acetamide [3252];
N-(3-(oxazol-5-yl)-1,7-naphthyridin-6-yl)-2-(pyrrolidin-1-yl)acetamide [3253];
(R)-2-(2-methylpyrrolidin-1-yl)-N-(3-(oxazol-5-yl)-1,7-naphthyridin-6-yl)acetamide [3254];
2-(4-methylpiperazin-1-yl)-N-(3-(oxazol-5-yl)-1,7-naphthyridin-6-yl)acetamide [3255];
trans-4-((4-methylpiperazin-1-yl)methyl)-N-(3-(oxazol-5-yl)-1,7-naphthyridin-6-yl)cyclohexane-1-carboxamide [3256];
1-(2,2-difluoropropyl)-N-(3-(oxazol-5-yl)-1,7-naphthyridin-6-yl)piperidine-4-carboxamide [3257];
4-(difluoromethoxy)-N-(3-(1-methyl-1H-imidazol-5-yl)-1,7-naphthyridin-6-yl)benzamide [3258];
N-(3-(1-methyl-1H-imidazol-5-yl)-1,7-naphthyridin-6-yl)-3-(pyrrolidin-1-ylmethyl)benzamide [3259];
2-fluoro-N-(3-(1-methyl-1H-imidazol-5-yl)-1,7-naphthyridin-6-yl)benzamide-3,4,5,6-d$_4$ [3260];
trans-4-(hydroxymethyl)-N-(3-(2-methyloxazol-5-yl)-1,7-naphthyridin-6-yl)cyclohexane-1-carboxamide [3261];
trans-4-(methylamino)-N-(3-(2-methyloxazol-5-yl)-1,7-naphthyridin-6-yl)cyclohexane-1-carboxamide [3262];
trans-4-((1,3-difluoropropan-2-yl)amino)-N-(3-(2-methyloxazol-5-yl)-1,7-naphthyridin-6-yl) cyclohexane-1-carboxamide [3263];
trans-N-(3-(2-methyloxazol-5-yl)-1,7-naphthyridin-6-yl)-4-((propan-2-yl-1,1,1,3,3,3-d$_6$) amino)cyclohexane-1-carboxamide [3264];
trans-4-((2,2-difluoroethyl)amino)-N-(3-(2-methyloxazol-5-yl)-1,7-naphthyridin-6-yl) cyclohexane-1-carboxamide [3265];
trans-N-(3-(2-methyloxazol-5-yl)-1,7-naphthyridin-6-yl)-4-((3,3,3-trifluoropropyl)amino)cyclohexane-1-carboxamide [3266];
trans-4-((2-methoxyethyl)amino)-N-(3-(2-methyloxazol-5-yl)-1,7-naphthyridin-6-yl) cyclohexane-1-carboxamide [3267];
trans-4-(dimethylamino)-N-(3-(2-methyloxazol-5-yl)-1,7-naphthyridin-6-yl)cyclohexane-1-carboxamide [3268];

trans-4-(bis(methyl-d$_3$)amino)-N-(3-(2-methyloxazol-5-yl)-1,7-naphthyridin-6-yl)cyclohexane-1-carboxamide [3269];
cis-4-(dimethylamino)-N-(3-(2-methyloxazol-5-yl)-1,7-naphthyridin-6-yl)cyclohexane-1-carboxamide [3270];
trans-4-((2,2-difluoroethyl)(methyl)amino)-N-(3-(2-methyloxazol-5-yl)-1,7-naphthyridin-6-yl) cyclohexane-1-carboxamide [3271];
trans-4-(methyl(oxetan-3-yl)amino)-N-(3-(2-methyloxazol-5-yl)-1,7-naphthyridin-6-yl) cyclohexane-1-carboxamide [3272];
trans-4-((2-fluoroethyl)amino)-N-(3-(2-methyloxazol-5-yl)-1,7-naphthyridin-6-yl)cyclohexane-1-carboxamide [3273];
trans-4-(2-(fluoromethyl)aziridin-1-yl)-N-(3-(2-methyloxazol-5-yl)-1,7-naphthyridin-6-yl) cyclohexane-1-carboxamide [3274];
trans-4-((3-fluoroazetidin-1-yl)methyl)-N-(3-(2-methyloxazol-5-yl)-1,7-naphthyridin-6-yl) cyclohexane-1-carboxamide [3275];
trans-N-(3-(2-methyloxazol-5-yl)-1,7-naphthyridin-6-yl)-3-morpholinocyclobutane-1-carboxamide [3276];
trans-N-(3-(2-methyloxazol-5-yl)-1,7-naphthyridin-6-yl)-4-morpholinocyclohexane-1-carboxamide [3277];
N-(3-(2-methyloxazol-5-yl)-1,7-naphthyridin-6-yl)-2-(piperidin-1-yl)acetamide [3278];
2-(4-methoxypiperidin-1-yl)-N-(3-(2-methyloxazol-5-yl)-1,7-naphthyridin-6-yl)acetamide [3279];
N-(3-(2-methyloxazol-5-yl)-1,7-naphthyridin-6-yl)-2-(4-methylpiperazin-1-yl)acetamide [3280];
N-(3-(2-methyloxazol-5-yl)-1,7-naphthyridin-6-yl)morpholine-4-carboxamide [3281];
N-(3-(2-methyloxazol-5-yl)-1,7-naphthyridin-6-yl)-2-morpholinoacetamide [3282];
N-(3-(2-methyloxazol-5-yl)-1,7-naphthyridin-6-yl)-3-morpholinopropanamide [3283];
1-methyl-N-(3-(2-methyloxazol-5-yl)-1,7-naphthyridin-6-yl)piperidine-4-carboxamide [3284];
1-(2,2-difluoropropyl)-N-(3-(2-methyloxazol-5-yl)-1,7-naphthyridin-6-yl)piperidine-4-carboxamide [3285];
N-(3-(2-methyloxazol-5-yl)-1,7-naphthyridin-6-yl)-4-morpholinopiperidine-1-carboxamide [3286];
4-((1,3-difluoropropan-2-yl)amino)-N-(3-(2-methyloxazol-5-yl)-1,7-naphthyridin-6-yl) piperidine-1-carboxamide [3287];
(1R,3s,5S)-3-((1,3-difluoropropan-2-yl)amino)-N-(3-(2-methyloxazol-5-yl)-1,7-naphthyridin-6-yl)-8-azabicyclo[3.2.1]octane-8-carboxamide [3288];
(1R,3s,5S)-3-((1,3-difluoropropan-2-yl)amino)-N-(3-(2-methyloxazol-5-yl)-1,7-naphthyridin-6-yl)-8-azabicyclo[3.2.1]octane-8-carboxamide [3289];
4-(dimethylamino)-N-(3-(2-methyloxazol-5-yl)-1,7-naphthyridin-6-yl)piperidine-1-carboxamide [3290];
4-((2,2-difluoroethyl)(methyl)amino)-N-(3-(2-methyloxazol-5-yl)-1,7-naphthyridin-6-yl) piperidine-1-carboxamide [3291];
(3S,4S)-4-amino-3-fluoro-N-(3-(2-methyloxazol-5-yl)-1,7-naphthyridin-6-yl)piperidine-1-carboxamide [3292];
(3S,4S)-3-fluoro-4-(methylamino)-N-(3-(2-methyloxazol-5-yl)-1,7-naphthyridin-6-yl)piperidine-1-carboxamide [3293];
(3R,4R)-4-amino-3-fluoro-N-(3-(2-methyloxazol-5-yl)-1,7-naphthyridin-6-yl)piperidine-1-carboxamide [3294];
(3R,4R)-3-fluoro-4-(methylamino)-N-(3-(2-methyloxazol-5-yl)-1,7-naphthyridin-6-yl)piperidine-1-carboxamide [3295];
4-((2-fluoroethyl)amino)-N-(3-(2-methyloxazol-5-yl)-1,7-naphthyridin-6-yl)piperidine-1-carboxamide [3296];
4-((2,2-difluoroethyl)amino)-N-(3-(2-methyloxazol-5-yl)-1,7-naphthyridin-6-yl)piperidine-1-carboxamide [3297];
(1R,3s,5S)-3-amino-N-(3-(2-methyloxazol-5-yl)-1,7-naphthyridin-6-yl)-8-azabicyclo[3.2.1] octane-8-carboxamide [3298];
(1R,3r,5S)-3-amino-N-(3-(2-methyloxazol-5-yl)-1,7-naphthyridin-6-yl)-8-azabicyclo[3.2.1] octane-8-carboxamide [3299];
(1R,3r,5S)-3-((2-fluoroethyl)amino)-N-(3-(2-methyloxazol-5-yl)-1,7-naphthyridin-6-yl)-8-azabicyclo[3.2.1] octane-8-carboxamide [3300];
(1R,3r,5S)-3-((2,2-difluoroethyl)amino)-N-(3-(2-methyloxazol-5-yl)-1,7-naphthyridin-6-yl)-8-azabicyclo[3.2.1]octane-8-carboxamide [3301];
(1R,3s,5S)—N-(3-(2-methyloxazol-5-yl)-1,7-naphthyridin-6-yl)-3-((3,3,3-trifluoropropyl)amino)-8-azabicyclo[3.2.1]octane-8-carboxamide [3302];
(3S,4S)-3-fluoro-4-(isopropylamino)-N-(3-(2-methyloxazol-5-yl)-1,7-naphthyridin-6-yl)piperidine-1-carboxamide [3303];
N-(3-(2-methyloxazol-5-yl)-1,7-naphthyridin-6-yl)-5,6-dihydroimidazo[1,2-a]pyrazine-7(8H)-carboxamide [3304];
2-methyl-N-(3-(2-methyloxazol-5-yl)-1,7-naphthyridin-6-yl)-5,6-dihydroimidazo[1,2-a]pyrazine-7(8H)-carboxamide [3305];
N-(3-(2-methyloxazol-5-yl)-1,7-naphthyridin-6-yl)-2-(morpholino-d$_8$)acetamide [3306];
trans-N-(3-(2-methyloxazol-4-yl)-1,7-naphthyridin-6-yl)-4-(4-methylpiperazin-1-yl)cyclohexane-1-carboxamide [3307];
N-(3-(2-methyloxazol-5-yl)-1,7-naphthyridin-6-yl)-1-(1-methylpiperidin-4-yl)-1H-pyrazole-4-carboxamide [3308];
2-(1H-imidazol-1-yl)-N-(3-(2-methyloxazol-5-yl)-1,7-naphthyridin-6-yl)acetamide [3309];
4-(difluoromethoxy)-N-(3-(oxazol-5-yl)-1,7-naphthyridin-6-yl)benzamide [3310];
3-((1-methylpiperidin-4-yl)oxy)-N-(3-(oxazol-5-yl)-1,7-naphthyridin-6-yl)benzamide [3311];
N-(3-(oxazol-5-yl)-1,7-naphthyridin-6-yl)isonicotinamide [3312];
2-(3-aminoazetidin-1-yl)-N-(3-(oxazol-5-yl)-1,7-naphthyridin-6-yl)isonicotinamide [3313];
2-(1-methylpiperidin-4-yl)-N-(3-(oxazol-5-yl)-1,7-naphthyridin-6-yl)isonicotinamide [3314];
1'-methyl-N-(3-(oxazol-5-yl)-1,7-naphthyridin-6-yl)-1',2',3',6'-tetrahydro-[2,4'-bipyridine]-4-carboxamide [3315];
2-(4-methylpiperazin-1-yl)-N-(3-(oxazol-5-yl)-1,7-naphthyridin-6-yl)isonicotinamide [3316];
2-(7-methyl-2,7-diazaspiro[3.5]nonan-2-yl)-N-(3-(oxazol-5-yl)-1,7-naphthyridin-6-yl) isonicotinamide [3317];
N-(3-(oxazol-5-yl)-1,7-naphthyridin-6-yl)-2-(2,7-diazaspiro[3.5]nonan-7-yl)isonicotinamide [3318];
N-(3-(oxazol-5-yl)-1,7-naphthyridin-6-yl)-2-(piperidin-4-ylamino)isonicotinamide [3319];
2-methyl-N-(3-(oxazol-5-yl)-1,7-naphthyridin-6-yl)isoindoline-5-carboxamide [3320];
N-(3-(oxazol-5-yl)-1,7-naphthyridin-6-yl)-1,2,3,4-tetrahydroisoquinoline-7-carboxamide [3321];
N-(3-(2-methyloxazol-5-yl)-1,7-naphthyridin-6-yl)-2-(4-methylpiperazin-1-yl)isonicotinamide [3322];

N-(3-(3-methylisoxazol-5-yl)-1,7-naphthyridin-6-yl)-1-(3,3,3-trifluoropropyl)piperidine-4-carboxamide [3323];

4-fluoro-1-isobutyl-N-(3-(5-methyl-1,3,4-oxadiazol-2-yl)-1,7-naphthyridin-6-yl)piperidine-4-carboxamide [3324];

1-isobutyl-N-(3-(5-methyl-1,3,4-oxadiazol-2-yl)-1,7-naphthyridin-6-yl)piperidine-4-carboxamide [3325];

N-(3-(5-(dimethylamino)-1,3,4-oxadiazol-2-yl)-1,7-naphthyridin-6-yl)piperidine-4-carboxamide [3326];

N-(3-(5-(dimethylamino)-1,3,4-oxadiazol-2-yl)-1,7-naphthyridin-6-yl)-1-methylpiperidine-4-carboxamide [3327];

N-(3-(5-methyl-1,3,4-oxadiazol-2-yl)-1,7-naphthyridin-6-yl)-2-(4-methylpiperazin-1-yl) isonicotinamide [3328];

3,3-difluoro-N-(3-(thiazol-5-yl)-1,7-naphthyridin-6-yl)cyclobutane-1-carboxamide [3329];

2-methyl-N-(3-(thiazol-5-yl)-1,7-naphthyridin-6-yl)-2-azaspiro [3.3]heptane-6-carboxamide [3330];

1-fluoro-N-(3-(thiazol-5-yl)-1,7-naphthyridin-6-yl)cyclohexane-1-carboxamide [3331];

trans-4-(dimethylamino)-N-(3-(thiazol-5-yl)-1,7-naphthyridin-6-yl)cyclohexane-1-carboxamide [3332];

trans-4-((3-fluoroazetidin-1-yl)methyl)-N-(3-(thiazol-5-yl)-1,7-naphthyridin-6-yl)cyclohexane-1-carboxamide [3333];

N-(3-(thiazol-5-yl)-1,7-naphthyridin-6-yl)azetidine-3-carboxamide [3334];

1-methyl-N-(3-(thiazol-5-yl)-1,7-naphthyridin-6-yl)piperidine-4-carboxamide [3335];

1-(2,2-difluoropropyl)-N-(3-(thiazol-5-yl)-1,7-naphthyridin-6-yl)piperidine-4-carboxamide [3336];

1-(oxetan-3-yl)-N-(3-(thiazol-5-yl)-1,7-naphthyridin-6-yl)piperidine-4-carboxamide [3337];

1-(2-(pyrrolidin-1-yl)acetyl)-N-(3-(thiazol-5-yl)-1,7-naphthyridin-6-yl)piperidine-4-carboxamide [3338];

1'-methyl-N-(3-(thiazol-5-yl)-1,7-naphthyridin-6-yl)-[1,4'-bipiperidine]-4-carboxamide [3339];

2-(pyrrolidin-1-yl)-N-(3-(thiazol-5-yl)-1,7-naphthyridin-6-yl)propanamide [3340];

2-(piperidin-1-yl)-N-(3-(thiazol-5-yl)-1,7-naphthyridin-6-yl)acetamide [3341];

2-(4-methylpiperazin-1-yl)-N-(3-(thiazol-5-yl)-1,7-naphthyridin-6-yl)acetamide [3342];

2-morpholino-N-(3-(thiazol-5-yl)-1,7-naphthyridin-6-yl)acetamide [3343];

4-(piperidin-4-yloxy)-N-(3-(thiazol-5-yl)-1,7-naphthyridin-6-yl)benzamide [3344];

N-(3-(thiazol-5-yl)-1,7-naphthyridin-6-yl)isonicotinamide [3345];

6-(4-methylpiperazin-1-yl)-N-(3-(thiazol-5-yl)-1,7-naphthyridin-6-yl)nicotinamide [3346];

1'-methyl-N-(3-(thiazol-5-yl)-1,7-naphthyridin-6-yl)-1',2',3',6'-tetrahydro-[2,4'-bipyridine]-4-carboxamide [3347];

2-(3-(dimethylamino)azetidin-1-yl)-N-(3-(thiazol-5-yl)-1,7-naphthyridin-6-yl)isonicotinamide [3348];

2-(4-(dimethylamino)piperidin-1-yl)-N-(3-(thiazol-5-yl)-1,7-naphthyridin-6-yl)isonicotinamide [3349];

2-(4-methylpiperazin-1-yl)-N-(3-(thiazol-5-yl)-1,7-naphthyridin-6-yl)isonicotinamide [3350];

2-((1-methylpiperidin-4-yl)thio)-N-(3-(thiazol-5-yl)-1,7-naphthyridin-6-yl)isonicotinamide [3351];

N-(3-(thiazol-5-yl)-1,7-naphthyridin-6-yl)-1,2,3,4-tetrahydroisoquinoline-7-carboxamide [3352];

trans-4-((1,3-difluoropropan-2-yl)amino)-N-(3-(5-methyl-1,3,4-thiadiazol-2-yl)-1,7-naphthyridin-6-yl) cyclohexane-1-carboxamide [3353];

N-(3-(2-methylthiazol-5-yl)-1,7-naphthyridin-6-yl)morpholine-4-carboxamide [3354];

N-(3-(2-methylthiazol-5-yl)-1,7-naphthyridin-6-yl)-2-(pyrrolidin-1-yl)acetamide [3355];

2-((1R,4R)-2-oxa-5-azabicyclo [2.2.1]heptan-5-yl)-N-(3-(2-methylthiazol-5-yl)-1,7-naphthyridin-6-yl)acetamide [3356];

N-(3-(2-methylthiazol-5-yl)-1,7-naphthyridin-6-yl)-2-morpholinoacetamide [3357];

N-(3-(2-methylthiazol-5-yl)-1,7-naphthyridin-6-yl)-2-(morpholino-$d_8$)acetamide [3358];

2-(4-methylpiperazin-1-yl)-N-(3-(2-methylthiazol-5-yl)-1,7-naphthyridin-6-yl)acetamide [3359];

1-methyl-N-(3-(2-methylthiazol-5-yl)-1,7-naphthyridin-6-yl)piperidine-4-carboxamide [3360];

N-(3-(2-methylthiazol-5-yl)-1,7-naphthyridin-6-yl)isonicotinamide [3361];

N-(3-(2-methylthiazol-5-yl)-1,7-naphthyridin-6-yl)nicotinamide [3362];

2-(4-methylpiperazin-1-yl)-N-(3-(2-methylthiazol-5-yl)-1,7-naphthyridin-6-yl)isonicotinamide [3363];

trans-N-(3-(5-methyl-1,3,4-thiadiazol-2-yl)-1,7-naphthyridin-6-yl)-4-morpholinocyclohexane-1-carboxamide [3364];

trans-N-(3-(5-methyl-1,3,4-thiadiazol-2-yl)-1,7-naphthyridin-6-yl)-4-(4-methylpiperazin-1-yl) cyclohexane-1-carboxamide [3365];

4-isopropyl-N-(3-(5-methyl-1,3,4-thiadiazol-2-yl)-1,7-naphthyridin-6-yl)piperazine-1-carboxamide [3366];

4-((2-methoxyethyl)(methyl)amino)-N-(3-(5-methyl-1,3,4-thiadiazol-2-yl)-1,7-naphthyridin-6-yl) piperidine-1-carboxamide [3367];

4-((1,3-difluoropropan-2-yl)amino)-N-(3-(5-methyl-1,3,4-thiadiazol-2-yl)-1,7-naphthyridin-6-yl) piperidine-1-carboxamide [3368];

N-(3-(5-methyl-1,3,4-thiadiazol-2-yl)-1,7-naphthyridin-6-yl)-4-((3,3,3-trifluoropropyl)amino) piperidin 1-carboxamide [3369];

4-((2-fluoroethyl)amino)-N-(3-(5-methyl-1,3,4-thiadiazol-2-yl)-1,7-naphthyridin-6-yl)piperidine-1-carboxamide [3370];

(3R,4S)-4-amino-3-fluoro-N-(3-(5-methyl-1,3,4-thiadiazol-2-yl)-1,7-naphthyridin-6-yl) piperidine-1-carboxamide [3371];

(3R,4R)-4-amino-3-fluoro-N-(3-(5-methyl-1,3,4-thiadiazol-2-yl)-1,7-naphthyridin-6-yl) piperidine-1-carboxamide [3372];

(3 S,4S)-3-fluoro-N-(3-(5-methyl-1,3,4-thiadiazol-2-yl)-1,7-naphthyridin-6-yl)-4-(methylamino) piperidine-1-carboxamide [3373];

(3R,4R)-3-fluoro-N-(3-(5-methyl-1,3,4-thiadiazol-2-yl)-1,7-naphthyridin-6-yl)-4-(methylamino) piperidine-1-carboxamide [3374];

4-amino-3,3-difluoro-N-(3-(5-methyl-1,3,4-thiadiazol-2-yl)-1,7-naphthyridin-6-yl)piperidine-1-carboxamide [3375];

(3R,4R)-3-fluoro-4-(isopropylamino)-N-(3-(5-methyl-1,3,4-thiadiazol-2-yl)-1,7-naphthyridin-6-yl)piperidine-1-carboxamide [3376];

(3R,4S)-3-fluoro-4-(isopropylamino)-N-(3-(5-methyl-1,3,4-thiadiazol-2-yl)-1,7-naphthyridin-6-yl)piperidine-1-carboxamide [3377];

3,3-difluoro-4-(isopropylamino)-N-(3-(5-methyl-1,3,4-thiadiazol-2-yl)-1,7-naphthyridin-6-yl) piperidine-1-carboxamide [3378];

(3 S,4S)-3-fluoro-N-(3-(5-methyl-1,3,4-thiadiazol-2-yl)-1,7-naphthyridin-6-yl)-4-((propan-2-yl-1,1,1,3,3,3-$d_6$)amino)piperidine-1-carboxamide [3379];

(1R,3s,5S)-3-((1,3-difluoropropan-2-yl)amino)-N-(3-(5-methyl-1,3,4-thiadiazol-2-yl)-1,7-naphthyridin-6-yl)-8-azabicyclo[3.2.1]octane-8-carboxamide [3380];

(1R,3 s,5 S)-3-((1,3-difluoropropan-2-yl)amino)-N-(3-(5-methyl-1,3,4-thiadiazol-2-yl)-1,7-naphthyridin-6-yl)-8-azabicyclo[3.2.1]octane-8-carboxamide [3381];

4-(dimethylamino)-N-(3-(2-methylthiazol-5-yl)-1,7-naphthyridin-6-yl)piperidine-1-carboxamide [3382];

4-((2,2-difluoroethyl)amino)-N-(3-(5-methyl-1,3,4-thiadiazol-2-yl)-1,7-naphthyridin-6-yl) piperidine-1-carboxamide [3383];

4-((2,2-difluoroethyl)(methyl-d3)amino)-N-(3-(5-methyl-1,3,4-thiadiazol-2-yl)-1,7-naphthyridin-6-yl) piperidine-1-carboxamide [3384];

N-(3-(5-methyl-1,3,4-thiadiazol-2-yl)-1,7-naphthyridin-6-yl)-4-morpholinopiperidine-1-carboxamide [3385];

N-(3-(5-methyl-1,3,4-thiadiazol-2-yl)-1,7-naphthyridin-6-yl)-4-(4-methylpiperazin-1-yl) piperidine-1-carboxamide [3386];

(R)-3,4-dimethyl-N-(3-(5-methyl-1,3,4-thiadiazol-2-yl)-1,7-naphthyridin-6-yl)piperazine-1-carboxamide [3387];

(S)-3,4-dimethyl-N-(3-(5-methyl-1,3,4-thiadiazol-2-yl)-1,7-naphthyridin-6-yl)piperazine-1-carboxamide [3388];

(1R,3r,5 S)-3-((2-fluoroethyl)amino)-N-(3-(5-methyl-1,3,4-thiadiazol-2-yl)-1,7-naphthyridin-6-yl)-8-azabicyclo[3.2.1]octane-8-carboxamide [3389];

(1R,3r,5 S)-3-((2,2-difluoroethyl)amino)-N-(3-(5-methyl-1,3,4-thiadiazol-2-yl)-1,7-naphthyridin-6-yl)-8-azabicyclo[3.2.1]octane-8-carboxamide [3390];

(1R,3r,5 S)-3-amino-N-(3-(5-methyl-1,3,4-thiadiazol-2-yl)-1,7-naphthyridin-6-yl)-8-azabicyclo [3.2.1]octane-8-carboxamide [3391];

(1 S,4S)-5-methyl-N-(3-(5-methyl-1,3,4-thiadiazol-2-yl)-1,7-naphthyridin-6-yl)-2,5-diazabicyclo [2.2.1]heptane-2-carboxamide [3392];

(1R,4R)-5-methyl-N-(3-(5-methyl-1,3,4-thiadiazol-2-yl)-1,7-naphthyridin-6-yl)-2,5-diazabicyclo [2.2.1]heptane-2-carboxamide [3393];

8-methyl-N-(3-(5-methyl-1,3,4-thiadiazol-2-yl)-1,7-naphthyridin-6-yl)-3,8-diazabicyclo [3.2.1]octane-3-carboxamide [3394];

3-methyl-N-(3-(5-methyl-1,3,4-thiadiazol-2-yl)-1,7-naphthyridin-6-yl)-3,8-diazabicyclo [3.2.1]octane-8-carboxamide [3395];

N-(3-(5-methyl-1,3,4-thiadiazol-2-yl)-1,7-naphthyridin-6-yl)-5,6-dihydroimidazo[1,2-a]pyrazine-7(8H)-carboxamide [3396];

2-(4-methylpiperazin-1-yl)-N-(3-(5-methylthiazol-2-yl)-1,7-naphthyridin-6-yl)isonicotinamide [3397];

2-(4-methylpiperazin-1-yl)-N-(3-(4-methylthiazol-2-yl)-1,7-naphthyridin-6-yl)isonicotinamide [3398];

N-(3-(2-(methylamino)thiazol-5-yl)-1,7-naphthyridin-6-yl)piperidine-4-carboxamide [3399];

1-methyl-N-(3-(2-(methylamino)thiazol-5-yl)-1,7-naphthyridin-6-yl)piperidine-4-carboxamide [3400];

N-(3-(2-(diethylamino)thiazol-5-yl)-1,7-naphthyridin-6-yl)-2-(4-fluoropiperidin-1-yl)acetamide [3401];

N-(3-(2-(diethylamino)thiazol-5-yl)-1,7-naphthyridin-6-yl)-2-(4-methylpiperazin-1-yl)acetamide [3402];

N-(3-(2-aminothiazol-5-yl)-1,7-naphthyridin-6-yl)-2-(4-methylpiperazin-1-yl)isonicotinamide [3403];

N-(3-(2-(methylamino)thiazol-5-yl)-1,7-naphthyridin-6-yl)-2-(4-methylpiperazin-1-yl) isonicotinamide [3404];

N-(3-(2-(dimethylamino)thiazol-5-yl)-1,7-naphthyridin-6-yl)-2-(4-methylpiperazin-1-yl) isonicotinamide [3405];

2-(4-isopropylpiperazin-1-yl)-N-(3-(2-(methylamino)thiazol-5-yl)-1,7-naphthyridin-6-yl) isonicotinamide [3406];

2-(3-(dimethylamino)azetidin-1-yl)-N-(3-(2-(methylamino)thiazol-5-yl)-1,7-naphthyridin-6-yl) isonicotinamide [3407];

2-(3-(dimethylamino)azetidin-1-yl)-N-(3-(2-(dimethylamino)thiazol-5-yl)-1,7-naphthyridin-6-yl) isonicotinamide [3408];

2-(3-aminoazetidin-1-yl)-N-(3-(2-(dimethylamino)thiazol-5-yl)-1,7-naphthyridin-6-yl) isonicotinamide [3409];

N-(3-(5-chlorothiazol-2-yl)-1,7-naphthyridin-6-yl)-2-(4-methylpiperazin-1-yl)isonicotinamide [3410];

2-(6-(2-(4-methylpiperazin-1-yl)isonicotinamido)-1,7-naphthyridin-3-yl)thiazole-5-carboxamide [3411];

N-(3-(isothiazol-4-yl)-1,7-naphthyridin-6-yl)-1-methylpiperidine-4-carboxamide [3412];

N-(3-(1,3,4-thiadiazol-2-yl)-1,7-naphthyridin-6-yl)-4-(difluoromethoxy)benzamide [3413];

N-(3-(1,3,4-thiadiazol-2-yl)-1,7-naphthyridin-6-yl)-4-(piperidin-4-yloxy)benzamide [3414];

N-(3-(1,3,4-thiadiazol-2-yl)-1,7-naphthyridin-6-yl)-4-((1-methylpiperidin-4-yl)oxy)benzamide [3415];

N-(3-(1,3,4-thiadiazol-2-yl)-1,7-naphthyridin-6-yl)-3-((1-methylpiperidin-4-yl)oxy)benzamide [3416];

$N^5$-(3-(1,3,4-thiadiazol-2-yl)-1,7-naphthyridin-6-yl)-$N^2$-methylpyridine-2,5-dicarboxamide [3417];

N-(3-(1,3,4-thiadiazol-2-yl)-1,7-naphthyridin-6-yl)-6-(4-methylpiperazin-1-yl)nicotinamide [3418];

N-(3-(1,3,4-thiadiazol-2-yl)-1,7-naphthyridin-6-yl)-1'-methyl-1',2',3',6'-tetrahydro-[2,4'-bipyridine]-4-carboxamide [3419];

N-(3-(1,3,4-thiadiazol-2-yl)-1,7-naphthyridin-6-yl)-2-(3-(dimethylamino)azetidin-1-yl) isonicotinamide [3420];

N-(3-(1,3,4-thiadiazol-2-yl)-1,7-naphthyridin-6-yl)-2-(4-methylpiperazin-1-yl)isonicotinamide [3421];

N-(3-(1,3,4-thiadiazol-2-yl)-1,7-naphthyridin-6-yl)-2-(4-isopropylpiperazin-1-yl)isonicotinamide [3422];

N-(3-(1,3,4-thiadiazol-2-yl)-1,7-naphthyridin-6-yl)-2-morpholinoisonicotinamide [3423];

1-fluoro-N-(3-(5-methyl-1,3,4-thiadiazol-2-yl)-1,7-naphthyridin-6-yl)cyclohexane-1-carboxamide [3424];

trans-4-methoxy-N-(3-(5-methyl-1,3,4-thiadiazol-2-yl)-1,7-naphthyridin-6-yl)cyclohexane-1-carboxamide [3425];

cis-4-methoxy-N-(3-(5-methyl-1,3,4-thiadiazol-2-yl)-1,7-naphthyridin-6-yl)cyclohexane-1-carboxamide [3426];

trans-4-amino-N-(3-(5-methyl-1,3,4-thiadiazol-2-yl)-1,7-naphthyridin-6-yl)cyclohexane-1-carboxamide [3427];

trans-4-(dimethylamino)-N-(3-(5-methyl-1,3,4-thiadiazol-2-yl)-1,7-naphthyridin-6-yl) cyclohexane-1-carboxamide [3428];

trans-N-(3-(5-methyl-1,3,4-thiadiazol-2-yl)-1,7-naphthyridin-6-yl)-4-morpholinocyclohexane-1-carboxamide [3429];

trans-4-(hydroxymethyl)-N-(3-(5-methyl-1,3,4-thiadiazol-2-yl)-1,7-naphthyridin-6-yl) cyclohexane-1-carboxamide [3430];

N-(3-(5-methyl-1,3,4-thiadiazol-2-yl)-1,7-naphthyridin-6-yl)piperidine-4-carboxamide [3431];
4-fluoro-N-(3-(5-methyl-1,3,4-thiadiazol-2-yl)-1,7-naphthyridin-6-yl)piperidine-4-carboxamide [3432];
1-methyl-N-(3-(5-methyl-1,3,4-thiadiazol-2-yl)-1,7-naphthyridin-6-yl)piperidine-4-carboxamide [3433];
4-fluoro-1-methyl-N-(3-(5-methyl-1,3,4-thiadiazol-2-yl)-1,7-naphthyridin-6-yl)piperidine-4-carboxamide [3434];
1-(2-fluoroethyl)-N-(3-(5-methyl-1,3,4-thiadiazol-2-yl)-1,7-naphthyridin-6-yl)piperidine-4-carboxamide [3435];
1-(2,2-difluoroethyl)-N-(3-(5-methyl-1,3,4-thiadiazol-2-yl)-1,7-naphthyridin-6-yl)piperidine-4-carboxamide [3436];
N-(3-(5-methyl-1,3,4-thiadiazol-2-yl)-1,7-naphthyridin-6-yl)-1-(3,3,3-trifluoropropyl)piperidine-4-carboxamide [3437];
1-(2,2-difluoropropyl)-N-(3-(5-methyl-1,3,4-thiadiazol-2-yl)-1,7-naphthyridin-6-yl)piperidine-4-carboxamide [3438];
1-benzoyl-N-(3-(5-methyl-1,3,4-thiadiazol-2-yl)-1,7-naphthyridin-6-yl)piperidine-4-carboxamide [3439];
N-(3-(5-methyl-1,3,4-thiadiazol-2-yl)-1,7-naphthyridin-6-yl)-2-(pyrrolidin-1-yl)acetamide [3440];
N-(3-(5-methyl-1,3,4-thiadiazol-2-yl)-1,7-naphthyridin-6-yl)-2-(piperidin-1-yl)acetamide [3441];
2-(4-methoxypiperidin-1-yl)-N-(3-(5-methyl-1,3,4-thiadiazol-2-yl)-1,7-naphthyridin-6-yl) acetamide [3442];
N-(3-(5-methyl-1,3,4-thiadiazol-2-yl)-1,7-naphthyridin-6-yl)-2-(4-methylpiperazin-1-yl) acetamide [3443];
N-(3-(5-methyl-1,3,4-thiadiazol-2-yl)-1,7-naphthyridin-6-yl)-2-morpholinoacetamide [3444];
(R)—N-(3-(5-methyl-1,3,4-thiadiazol-2-yl)-1,7-naphthyridin-6-yl)-2-(3-methylmorpholino) acetamide [3445];
2-(7-azabicyclo[2.2.1]heptan-7-yl)-N-(3-(5-methyl-1,3,4-thiadiazol-2-yl)-1,7-naphthyridin-6-yl) acetamide [3446];
2-((1R,4R)-2-oxa-5-azabicyclo [2.2.1]heptan-5-yl)-N-(3-(5-methyl-1,3,4-thiadiazol-2-yl)-1,7-naphthyridin-6-yl)acetamide [3447];
2-(3-oxa-8-azabicyclo[3.2.1]octan-8-yl)-N-(3-(5-methyl-1,3,4-thiadiazol-2-yl)-1,7-naphthyridin-6-yl)acetamide [3448];
2-(8-oxa-3-azabicyclo[3.2.1]octan-3-yl)-N-(3-(5-methyl-1,3,4-thiadiazol-2-yl)-1,7-naphthyridin-6-yl)acetamide [3449];
N-(3-(5-methyl-1,3,4-thiadiazol-2-yl)-1,7-naphthyridin-6-yl)-2-(1,4-oxazepan-4-yl)acetamide [3450];
N-(3-(5-methyl-1,3,4-thiadiazol-2-yl)-1,7-naphthyridin-6-yl)-2-morpholinoacetamide-2,2-d$_2$ [3451];
N-(3-(5-methyl-1,3,4-thiadiazol-2-yl)-1,7-naphthyridin-6-yl)-2-(morpholino-d)acetamide [3452];
1-methyl-3-(3-(5-methyl-1,3,4-thiadiazol-2-yl)-1,7-naphthyridin-6-yl)-1-(1-methylpiperidin-4-yl) urea [3453];
(3S,4S)-4-amino-3-fluoro-N-(3-(5-methyl-1,3,4-thiadiazol-2-yl)-1,7-naphthyridin-6-yl) piperidine-1-carboxamide [3454];
(3S,4S)-4-(dimethylamino)-3-fluoro-N-(3-(5-methyl-1,3,4-thiadiazol-2-yl)-1,7-naphthyridin-6-yl) piperidine-1-carboxamide [3455];
N-(3-(5-methyl-1,3,4-thiadiazol-2-yl)-1,7-naphthyridin-6-yl)morpholine-4-carboxamide [3456];
N-(3-(5-methyl-1,3,4-thiadiazol-2-yl)-1,7-naphthyridin-6-yl)-4-(methylamino)piperidine-1-carboxamide [3457];
4-(dimethylamino)-N-(3-(5-methyl-1,3,4-thiadiazol-2-yl)-1,7-naphthyridin-6-yl)piperidine-1-carboxamide [3458];
4-((2,2-difluoroethyl)(methyl)amino)-N-(3-(5-methyl-1,3,4-thiadiazol-2-yl)-1,7-naphthyridin-6-yl)piperidine-1-carboxamide [3459];
(3 S,4S)-3-fluoro-4-(isopropylamino)-N-(3-(5-methyl-1,3,4-thiadiazol-2-yl)-1,7-naphthyridin-6-yl)piperidine-1-carboxamide [3460];
2-methyl-N-(3-(5-methyl-1,3,4-thiadiazol-2-yl)-1,7-naphthyridin-6-yl)-5,6-dihydroimidazo[1,2-a]pyrazine-7(8H)-carboxamide [3461];
4-methyl-N-(3-(5-methyl-1,3,4-thiadiazol-2-yl)-1,7-naphthyridin-6-yl)piperazine-1-carboxamide [3462];
N-(3-(5-methyl-1,3,4-thiadiazol-2-yl)-1,7-naphthyridin-6-yl)-1-(1-methylpiperidin-4-yl)-1H-pyrazole-4-carboxamide [3463];
1-(1-isopropylpiperidin-4-yl)-N-(3-(5-methyl-1,3,4-thiadiazol-2-yl)-1,7-naphthyridin-6-yl)-1H-pyrazole-4-carboxamide [3464];
N-(3-(5-methyl-1,3,4-thiadiazol-2-yl)-1,7-naphthyridin-6-yl)-1-(1-methylpiperidin-4-yl)-1H-1,2,3-triazole-4-carboxamide [3465];
N-(3-(5-methyl-1,3,4-thiadiazol-2-yl)-1,7-naphthyridin-6-yl)-2-(piperidin-4-yl)oxazole-4-carboxamide [3466];
N-(3-(5-methyl-1,3,4-thiadiazol-2-yl)-1,7-naphthyridin-6-yl)-2-(1-methylpiperidin-4-yl)oxazole-4-carboxamide [3467];
2-(3-(dimethylamino)azetidin-1-yl)-N-(3-(5-methyl-1,3,4-thiadiazol-2-yl)-1,7-naphthyridin-6-yl) isonicotinamide [3468];
1'-methyl-N-(3-(5-methyl-1,3,4-thiadiazol-2-yl)-1,7-naphthyridin-6-yl)-1',2',3',6'-tetrahydro-[2,4'-bipyridine]-4-carboxamide [3469];
N-(3-(5-methyl-1,3,4-thiadiazol-2-yl)-1,7-naphthyridin-6-yl)-2-(4-methylpiperazin-1-yl) isonicotinamide [3470];
2-(methyl(1-methylpiperidin-4-yl)amino)-N-(3-(5-methyl-1,3,4-thiadiazol-2-yl)-1,7-naphthyridin-6-yl) isonicotinamide [3471];
2-(azetidin-3-yloxy)-N-(3-(5-methyl-1,3,4-thiadiazol-2-yl)-1,7-naphthyridin-6-yl)isonicotinamide [3472];
N-(3-(5-methyl-1,3,4-thiadiazol-2-yl)-1,7-naphthyridin-6-yl)-3-((1-methylpiperidin-4-yl)oxy) benzamide [3473];
N-(3-(5-methyl-1,3,4-thiadiazol-2-yl)-1,7-naphthyridin-6-yl)-2-((1-methylpiperidin-4-yl)thio) isonicotinamide [3474];
6-(4-methylpiperazin-1-yl)-N-(3-(5-(trifluoromethyl)-1,3,4-thiadiazol-2-yl)-1,7-naphthyridin-6-yl)nicotinamide [3475];
2-(4-methylpiperazin-1-yl)-N-(3-(5-(trifluoromethyl)-1,3,4-thiadiazol-2-yl)-1,7-naphthyridin-6-yl)isonicotinamide [3476];
N-(3-(5-amino-1,3,4-thiadiazol-2-yl)-1,7-naphthyridin-6-yl)-2-(4-methylpiperazin-1-yl) isonicotinamide [3477];
N-(3-(5-(dimethylamino)-1,3,4-thiadiazol-2-yl)-1,7-naphthyridin-6-yl)-2-(4-methylpiperazin-1-yl)isonicotinamide [3478];
N-(3-(3-amino-5-fluorophenyl)-1,7-naphthyridin-6-yl)-2-(4-methylpiperazin-1-yl) isonicotinamide [3479];
N-(3-(3-fluoro-5-(isopropylamino)phenyl)-1,7-naphthyridin-6-yl)-2-(4-methylpiperazin-1-yl) isonicotinamide [3480];
1-methyl-N-(3-(pyridin-2-yl)-1,7-naphthyridin-6-yl)piperidine-4-carboxamide [3481];

2-(4-methylpiperazin-1-yl)-N-(3-(pyridin-2-yl)-1,7-naphthyridin-6-yl)isonicotinamide [3482];
2-(4-methylpiperazin-1-yl)-N-(3-(pyridin-4-yl)-1,7-naphthyridin-6-yl)isonicotinamide [3483];
N-(3-(pyridin-3-yl)-1,7-naphthyridin-6-yl)cyclopropanecarboxamide [3484];
N-(3-(pyridin-3-yl)-1,7-naphthyridin-6-yl)-2-(pyrrolidin-1-yl)acetamide [3485];
1-methyl-N-(3-(pyridin-3-yl)-1,7-naphthyridin-6-yl)piperidine-4-carboxamide [3486];
N-(3-(pyridin-3-yl)-1,7-naphthyridin-6-yl)quinuclidine-4-carboxamide [3487];
2-morpholino-N-(3-(pyridin-3-yl)-1,7-naphthyridin-6-yl)acetamide [3488];
2-(morpholino-$d_8$)—N-(3-(pyridin-3-yl)-1,7-naphthyridin-6-yl)acetamide [3489];
2-(4-methylpiperazin-1-yl)-N-(3-(pyridin-3-yl)-1,7-naphthyridin-6-yl)acetamide [3490];
2-(4-methyl-1,4-diazepan-1-yl)-N-(3-(pyridin-3-yl)-1,7-naphthyridin-6-yl)acetamide [3491];
2-(4-methylpiperazin-1-yl)-N-(3-(pyridin-3-yl)-1,7-naphthyridin-6-yl)isonicotinamide [3492];
2-(2-methyl-1H-imidazol-1-yl)-N-(3-(pyridin-3-yl)-1,7-naphthyridin-6-yl)acetamide [3493];
2-(1H-imidazol-1-yl)-N-(3-(pyridin-3-yl)-1,7-naphthyridin-6-yl)acetamide [3494];
2-(piperidin-4-yl)-N-(3-(pyridin-3-yl)-1,7-naphthyridin-6-yl)oxazole-4-carboxamide [3495];
2-(1-methylpiperidin-4-yl)-N-(3-(pyridin-3-yl)-1,7-naphthyridin-6-yl)oxazole-4-carboxamide [3496];
2-(1-isopropylpiperidin-4-yl)-N-(3-(pyridin-3-yl)-1,7-naphthyridin-6-yl)oxazole-4-carboxamide [3497];
trans-N-(3-(5-fluoropyridin-3-yl)-1,7-naphthyridin-6-yl)-3-morpholinocyclobutane-1-carboxamide [3498];
trans-N-(3-(5-fluoropyridin-3-yl)-1,7-naphthyridin-6-yl)-4-((4-methylpiperazin-1-yl)methyl) cyclohexane-1-carboxamide [3499];
N-(3-(5-fluoropyridin-3-yl)-1,7-naphthyridin-6-yl)-2-(pyrrolidin-1-yl)acetamide [3500];
N-(3-(5-fluoropyridin-3-yl)-1,7-naphthyridin-6-yl)-1-methylpiperidine-4-carboxamide [3501];
N-(3-(5-fluoropyridin-3-yl)-1,7-naphthyridin-6-yl)-2-(4-methylpiperazin-1-yl)acetamide [3502];
N-(3-(6-fluoropyridin-3-yl)-1,7-naphthyridin-6-yl)-2-(4-methylpiperazin-1-yl)acetamide [3503];
N-(3-(5-fluoropyridin-3-yl)-1,7-naphthyridin-6-yl)-2-morpholinoacetamide [3504];
N-(3-(5-fluoropyridin-3-yl)-1,7-naphthyridin-6-yl)-3-morpholinopropanamide [3505];
N-(3-(5-fluoropyridin-3-yl)-1,7-naphthyridin-6-yl)-2-(4-methylpiperazin-1-yl)isonicotinamide [3506];
N-(3-(5-fluoropyridin-3-yl)-1,7-naphthyridin-6-yl)-2-(piperidin-4-yl)oxazole-4-carboxamide [3507];
N-(3-(5-fluoropyridin-3-yl)-1,7-naphthyridin-6-yl)-2-(1-methylpiperidin-4-yl)oxazole-4-carboxamide [3508];
N-(3-(5-fluoropyridin-3-yl)-1,7-naphthyridin-6-yl)-2-(1-isopropylpiperidin-4-yl)oxazole-4-carboxamide [3509];
N-(3-(5-chloropyridin-3-yl)-1,7-naphthyridin-6-yl)-2-(4-methylpiperazin-1-yl)isonicotinamide [3510];
N-(3-(5-methylpyridin-3-yl)-1,7-naphthyridin-6-yl)-2-morpholinoacetamide [3511];
N-(3-(5-(difluoromethyl)pyridin-3-yl)-1,7-naphthyridin-6-yl)-3-(piperidin-4-yl)benzamide [3512];
N-(3-(5-(difluoromethyl)pyridin-3-yl)-1,7-naphthyridin-6-yl)-3-(1-methylpiperidin-4-yl) benzamide [3513];
N-(3-(5-(difluoromethyl)pyridin-3-yl)-1,7-naphthyridin-6-yl)-2-(4-methylpiperazin-1-yl) isonicotinamide [3514];
2-(4-methylpiperazin-1-yl)-N-(3-(5-(trifluoromethyl)pyridin-3-yl)-1,7-naphthyridin-6-yl) acetamide [3515];
2-(4-methylpiperazin-1-yl)-N-(3-(6-(trifluoromethyl)pyridin-3-yl)-1,7-naphthyridin-6-yl) acetamide [3516];
N-(3-(5-(hydroxymethyl)pyridin-3-yl)-1,7-naphthyridin-6-yl)-1-methylpiperidine-4-carboxamide [3517];
N-(3-(5-cyanopyridin-3-yl)-1,7-naphthyridin-6-yl)-1-methylpiperidine-4-carboxamide [3518];
N-(3-(5-methoxypyridin-3-yl)-1,7-naphthyridin-6-yl)-1-methylpiperidine-4-carboxamide [3519];
N-(3-(5-methoxypyridin-3-yl)-1,7-naphthyridin-6-yl)-2-morpholinoacetamide [3520];
N-(3-(5-methoxypyridin-3-yl)-1,7-naphthyridin-6-yl)-2-(4-methylpiperazin-1-yl)isonicotinamide [3521];
4-fluoro-N-(3-(5-(piperidin-4-yloxy)pyridin-3-yl)-1,7-naphthyridin-6-yl)benzamide [3522];
N-(3-(5-aminopyridin-3-yl)-1,7-naphthyridin-6-yl)-4-fluorobenzamide [3523];
N-(3-(5-aminopyridin-3-yl)-1,7-naphthyridin-6-yl)-4-(piperidin-4-yloxy)benzamide [3524];
N-(3-(5-aminopyridin-3-yl)-1,7-naphthyridin-6-yl)-2-(4-methylpiperazin-1-yl)isonicotinamide [3525];
N-(3-(5-aminopyridin-3-yl)-1,7-naphthyridin-6-yl)-2-(piperidin-4-yl)oxazole-4-carboxamide [3526];
N-(3-(6-aminopyridin-3-yl)-1,7-naphthyridin-6-yl)-2-(4-methylpiperazin-1-yl)isonicotinamide [3527];
N-(3-(6-(methylamino)pyridin-3-yl)-1,7-naphthyridin-6-yl)-2-(4-methylpiperazin-1-yl) isonicotinamide [3528];
N-(3-(5-(isopropylamino)pyridin-3-yl)-1,7-naphthyridin-6-yl)-3-(piperidin-4-yl)benzamide [3529];
N-(3-(5-(isopropylamino)pyridin-3-yl)-1,7-naphthyridin-6-yl)-3-(1-methylpiperidin-4-yl) benzamide [3530];
N-(3-(5-(isopropylamino)pyridin-3-yl)-1,7-naphthyridin-6-yl)-2-(4-methylpiperazin-1-yl) isonicotinamide [3531];
N-(3-(5-(piperidin-4-ylamino)pyridin-3-yl)-1,7-naphthyridin-6-yl)cyclohexanecarboxamide [3532];
4-fluoro-N-(3-(5-(piperidin-4-ylamino)pyridin-3-yl)-1,7-naphthyridin-6-yl)benzamide [3533];
4-fluoro-N-(3-(5-((1-methylpiperidin-4-yl)amino)pyridin-3-yl)-1,7-naphthyridin-6-yl)benzamide [3534];
N-(3-(5-acetamidopyridin-3-yl)-1,7-naphthyridin-6-yl)-1-methylpiperidine-4-carboxamide [3535];
N-(3-(5-(dimethylamino)pyridin-3-yl)-1,7-naphthyridin-6-yl)-2-(4-methylpiperazin-1-yl) isonicotinamide [3536];
N-(3-(6-(dimethylamino)pyridin-3-yl)-1,7-naphthyridin-6-yl)-2-(4-methylpiperazin-1-yl) isonicotinamide [3537];
1-methyl-N-(3-(5-(pyrrolidin-1-yl)pyridin-3-yl)-1,7-naphthyridin-6-yl)piperidine-4-carboxamide [3538];
N-(3-(5-(pyrrolidin-1-ylmethyl)pyridin-3-yl)-1,7-naphthyridin-6-yl)cyclopropanecarboxamide [3539];
4-fluoro-N-(3-(5-(pyrrolidin-1-ylmethyl)pyridin-3-yl)-1,7-naphthyridin-6-yl)benzamide [3540];
N-(3-(5-((4-hydroxypiperidin-1-yl)methyl)pyridin-3-yl)-1,7-naphthyridin-6-yl) cyclopropanecarboxamide [3541];
4-fluoro-N-(3-(5-((4-hydroxypiperidin-1-yl)methyl)pyridin-3-yl)-1,7-naphthyridin-6-yl) benzamide [3542];
N-(3-(5-(piperazin-1-ylmethyl)pyridin-3-yl)-1,7-naphthyridin-6-yl)cyclopropanecarboxamide [3543];

N-(3-(5-((4-methylpiperazin-1-yl)methyl)pyridin-3-yl)-1,7-naphthyridin-6-yl) cyclopropanecarboxamide [3544];
N-(3-(5-(morpholinomethyl)pyridin-3-yl)-1,7-naphthyridin-6-yl)cyclopropanecarboxamide [3545];
N-methyl-5-(6-(1-methylpiperidine-4-carboxamido)-1,7-naphthyridin-3-yl)nicotinamide [3546];
N-methyl-5-(6-(2-(4-methylpiperazin-1-yl)isonicotinamido)-1,7-naphthyridin-3-yl)nicotinamide [3547];
N-(3-(pyridin-3-yl-d₄)-1,7-naphthyridin-6-yl)-2-(pyrrolidin-1-yl)acetamide [3548];
2-(4-methylpiperazin-1-yl)-N-(3-(pyridin-3-yl-d₄)-1,7-naphthyridin-6-yl)acetamide [3549];
2-morpholino-N-(3-(pyridin-3-yl-d₄)-1,7-naphthyridin-6-yl)acetamide [3550];
1-methyl-N-(3-(2-methylpyrimidin-5-yl)-1,7-naphthyridin-6-yl)piperidine-4-carboxamide [3551];
2-(4-methylpiperazin-1-yl)-N-(3-(2-methylpyrimidin-5-yl)-1,7-naphthyridin-6-yl)isonicotinamide [3552];
N-(3-(2-aminopyrimidin-5-yl)-1,7-naphthyridin-6-yl)-1-methylpiperidine-4-carboxamide [3553];
2-morpholino-N-(3-(pyridazin-3-yl)-1,7-naphthyridin-6-yl)acetamide [3554];
2-morpholino-N-(3-(pyridazin-4-yl)-1,7-naphthyridin-6-yl)acetamide [3555];
N-(3-(pyridazin-4-yl)-1,7-naphthyridin-6-yl)-2-(pyrrolidin-1-yl)acetamide [3556];
trans-3-morpholino-N-(3-(pyrazin-2-yl)-1,7-naphthyridin-6-yl)cyclobutane-1-carboxamide [3557];
trans-4-(dimethylamino)-N-(3-(pyrazin-2-yl)-1,7-naphthyridin-6-yl)cyclohexane-1-carboxamide [3558];
trans-4-morpholino-N-(3-(pyrazin-2-yl)-1,7-naphthyridin-6-yl)cyclohexane-1-carboxamide [3559];
trans-4-((3-fluoroazetidin-1-yl)methyl)-N-(3-(pyrazin-2-yl)-1,7-naphthyridin-6-yl)cyclohexane-1-carboxamide [3560];
trans-4-((4-methylpiperazin-1-yl)methyl)-N-(3-(pyrazin-2-yl)-1,7-naphthyridin-6-yl) cyclohexane-1-carboxamide [3561];
N-(3-(pyrazin-2-yl)-1,7-naphthyridin-6-yl)-2-(pyrrolidin-1-yl)acetamide [3562];
1-methyl-N-(3-(pyrazin-2-yl)-1,7-naphthyridin-6-yl)piperidine-4-carboxamide [3563];
4-fluoro-1-methyl-N-(3-(pyrazin-2-yl)-1,7-naphthyridin-6-yl)piperidine-4-carboxamide [3564];
1-(2-fluoroethyl)-N-(3-(pyrazin-2-yl)-1,7-naphthyridin-6-yl)piperidine-4-carboxamide [3565];
1-(oxetan-3-yl)-N-(3-(pyrazin-2-yl)-1,7-naphthyridin-6-yl)piperidine-4-carboxamide [3566];
2-morpholino-N-(3-(pyrazin-2-yl)-1,7-naphthyridin-6-yl)acetamide [3567];
1-methyl-N-(3-(pyrazin-2-yl)-1,7-naphthyridin-6-yl)azepane-4-carboxamide [3568];
1-isobutyl-N-(3-(pyrazin-2-yl)-1,7-naphthyridin-6-yl)azepane-4-carboxamide [3569];
1-(2-hydroxy-2-methylpropyl)-N-(3-(pyrazin-2-yl)-1,7-naphthyridin-6-yl)azepane-4-carboxamide [3570];
4-(morpholinomethyl)-N-(3-(pyrazin-2-yl)-1,7-naphthyridin-6-yl)benzamide [3571];
2-(4-methylpiperazin-1-yl)-N-(3-(pyrazin-2-yl)-1,7-naphthyridin-6-yl)isonicotinamide[3572];
N-(3-(6-(methylamino)pyrazin-2-yl)-1,7-naphthyridin-6-yl)-2-(4-methylpiperazin-1-yl) isonicotinamide [3573];
N-(3-(6-(isopropylamino)pyrazin-2-yl)-1,7-naphthyridin-6-yl)azetidine-3-carboxamide [3574];
N-(3-(6-(isopropylamino)pyrazin-2-yl)-1,7-naphthyridin-6-yl)piperidine-4-carboxamide [3575];
N-(3-(6-(isopropylamino)pyrazin-2-yl)-1,7-naphthyridin-6-yl)-1-methylpiperidine-4-carboxamide [3576];
1-(2-fluoroethyl)-N-(3-(6-(isopropylamino)pyrazin-2-yl)-1,7-naphthyridin-6-yl)piperidine-4-carboxamide [3577];
1-isopropyl-N-(3-(6-(isopropylamino)pyrazin-2-yl)-1,7-naphthyridin-6-yl)piperidine-4-carboxamide [3578];
1-isopentyl-N-(3-(6-(isopropylamino)pyrazin-2-yl)-1,7-naphthyridin-6-yl)piperidine-4-carboxamide [3579];
N-(3-(6-(isopropylamino)pyrazin-2-yl)-1,7-naphthyridin-6-yl)-3-(piperidin-4-yl)benzamide [3580];
N-(3-(6-(isopropylamino)pyrazin-2-yl)-1,7-naphthyridin-6-yl)-3-(1-methylpiperidin-4-yl) benzamide [3581];
N-(3-(6-(isopropylamino)pyrazin-2-yl)-1,7-naphthyridin-6-yl)-1-(piperidin-4-yl)-1H-1,2,3-triazole-4-carboxamide [3582];
1-(1-(2-fluoroethyl)piperidin-4-yl)-N-(3-(6-(isopropylamino)pyrazin-2-yl)-1,7-naphthyridin-6-yl)-1H-1,2,3-triazole-4-carboxamide [3583];
N-(3-(6-(isopropylamino)pyrazin-2-yl)-1,7-naphthyridin-6-yl)-1-(1-isopropylpiperidin-4-yl)-1H-1,2,3-triazole-4-carboxamide [3584];
N-(3-(6-(isopropylamino)pyrazin-2-yl)-1,7-naphthyridin-6-yl)-2-(4-methylpiperazin-1-yl) isonicotinamide [3585];
N-(3-(6-(tert-butylamino)pyrazin-2-yl)-1,7-naphthyridin-6-yl)-2-(3-(dimethylamino)azetidin-1-yl)isonicotinamide [3586];
N-(3-(6-(tert-butylamino)pyrazin-2-yl)-1,7-naphthyridin-6-yl)-1'-methyl-1',2',3',6'-tetrahydro-[2,4'-bipyridine]-4-carboxamide [3587];
N-(3-(6-(tert-butylamino)pyrazin-2-yl)-1,7-naphthyridin-6-yl)-2-(4-methylpiperazin-1l-yl) isonicotinamide [3588];
N-(3-(6-(tert-butylamino)pyrazin-2-yl)-1,7-naphthyridin-6-yl)-2-(4-isopropylpiperazin-1l-yl) isonicotinamide [3589];
N-(3-(6-(tert-butylamino)pyrazin-2-yl)-1,7-naphthyridin-6-yl)-2-morpholinoisonicotinamide [3590];
N-(3-(6-(((3-fluoroazetidin-3-yl)methyl)amino)pyrazin-2-yl)-1,7-naphthyridin-6-yl) cyclopropanecarboxamide [3591];
4-fluoro-N-(3-(6-(((3-fluoroazetidin-3-yl)methyl)amino) pyrazin-2-yl)-1,7-naphthyridin-6-yl) benzamide [3592];
N-(3-(6-(piperidin-4-ylamino)pyrazin-2-yl)-1,7-naphthyridin-6-yl)cyclobutanecarboxamide [3593];
3,3-difluoro-N-(3-(6-(piperidin-4-ylamino)pyrazin-2-yl)-1,7-naphthyridin-6-yl)cyclobutane-1-carboxamide [3594];
N-(3-(6-(piperidin-4-ylamino)pyrazin-2-yl)-1,7-naphthyridin-6-yl)cyclopentanecarboxamide [3595];
4,4-difluoro-N-(3-(6-(piperidin-4-ylamino)pyrazin-2-yl)-1,7-naphthyridin-6-yl)cyclohexane-1-carboxamide [3596];
N-(3-(6-(piperidin-4-ylamino)pyrazin-2-yl)-1,7-naphthyridin-6-yl)tetrahydro-2H-pyran-4-carboxamide [3597];
4-fluoro-N-(3-(6-(piperidin-4-ylamino)pyrazin-2-yl)-1,7-naphthyridin-6-yl)benzamide [3598];
N-(3-(6-(((3S,4S)-3-fluoropiperidin-4-yl)amino)pyrazin-2-yl)-1,7-naphthyridin-6-yl) cyclopropanecarboxamide [3599];
4-fluoro-N-(3-(6-(((3S,4S)-3-fluoropiperidin-4-yl) amino)pyrazin-2-yl)-1,7-naphthyridin-6-yl) benzamide [3600];
N-(3-(6-((1-methylpiperidin-4-yl)amino)pyrazin-2-yl)-1,7-naphthyridin-6-yl) cyclobutanecarboxamide [3601];

N-(3-(6-((1-methylpiperidin-4-yl)amino)pyrazin-2-yl)-1,7-naphthyridin-6-yl) cyclopentanecarboxamide [3602];

4-fluoro-N-(3-(6-((1-methylpiperidin-4-yl)amino)pyrazin-2-yl)-1,7-naphthyridin-6-yl)benzamide [3603];

N-(3-(6-((1-isopropylpiperidin-4-yl)amino)pyrazin-2-yl)-1,7-naphthyridin-6-yl) cyclopropanecarboxamide [3604];

3,3-difluoro-N-(3-(6-((1-isopropylpiperidin-4-yl)amino)pyrazin-2-yl)-1,7-naphthyridin-6-yl) cyclobutane-1-carboxamide [3605];

N-(3-(6-((1-isopropylpiperidin-4-yl)amino)pyrazin-2-yl)-1,7-naphthyridin-6-yl) cyclopentanecarboxamide [3606];

4-fluoro-N-(3-(6-((1-isopropylpiperidin-4-yl)amino)pyrazin-2-yl)-1,7-naphthyridin-6-yl) benzamide [3607];

N-(3-(6-(dimethylamino)pyrazin-2-yl)-1,7-naphthyridin-6-yl)-2-(4-methylpiperazin-1-yl) isonicotinamide [3608];

N-(3-(6-(diethylamino)pyrazin-2-yl)-1,7-naphthyridin-6-yl)-2-(4-methylpiperazin-1-yl) isonicotinamide [3609];

N-(3-(6-(3-aminoazetidin-1-yl)pyrazin-2-yl)-1,7-naphthyridin-6-yl)-4-fluorobenzamide [3610];

2-(4-methylpiperazin-1-yl)-N-(3-(6-(pyrrolidin-1-yl)pyrazin-2-yl)-1,7-naphthyridin-6-yl) isonicotinamide [3611];

N-(3-(6-(azetidin-3-ylmethoxy)pyrazin-2-yl)-1,7-naphthyridin-6-yl)-4-fluorobenzamide [3612];

N-(3-(6-(azetidin-3-yloxy)pyrazin-2-yl)-1,7-naphthyridin-6-yl)-4-fluorobenzamide [3613];

N-(3-(1H-pyrrolo[2,3-b]pyridin-5-yl)-1,7-naphthyridin-6-yl)-1-(1-methylpiperidin-4-yl)-1H-pyrazole-4-carboxamide [3614];

N-(3-(1H-pyrrolo[3,2-b]pyridin-6-yl)-1,7-naphthyridin-6-yl)-1-(1-methylpiperidin-4-yl)-1H-pyrazole-4-carboxamide [3615];

N-(3-(1H-pyrrolo[2,3-c]pyridin-4-yl)-1,7-naphthyridin-6-yl)-1-(1-methylpiperidin-4-yl)-1H-pyrazole-4-carboxamide [3616];

N-(3-(1H-pyrrolo[2,3-b]pyridin-5-yl)-1,7-naphthyridin-6-yl)-2-(4-methylpiperazin-1-yl) isonicotinamide [3617];

N-(3-(1H-pyrrolo[3,2-b]pyridin-6-yl)-1,7-naphthyridin-6-yl)-2-(4-methylpiperazin-1-yl) isonicotinamide [3618];

N-(3-(1H-pyrrolo[2,3-c]pyridin-4-yl)-1,7-naphthyridin-6-yl)-2-(4-methylpiperazin-1-yl) isonicotinamide [3619];

2-(4-methylpiperazin-1-yl)-N-(3-(oxazolo[5,4-b]pyridin-6-yl)-1,7-naphthyridin-6-yl) isonicotinamide [3620];

N-(3-(2-methyl-1H-pyrrolo[2,3-b]pyridin-5-yl)-1,7-naphthyridin-6-yl)-2-(4-methylpiperazin-1-yl)isonicotinamide [3621];

N-(3-(3-methyl-1H-pyrrolo[2,3-b]pyridin-5-yl)-1,7-naphthyridin-6-yl)-2-(4-methylpiperazin-1-yl)isonicotinamide [3622];

N-(3-(2-methyl-1H-pyrrolo[3,2-b]pyridin-6-yl)-1,7-naphthyridin-6-yl)-2-(4-methylpiperazin-1-yl)isonicotinamide [3623];

N-(3-(5H-pyrrolo[2,3-b]pyrazin-2-yl)-1,7-naphthyridin-6-yl)-2-(4-methylpiperazin-1-yl) isonicotinamide [3624];

N-(3-(5H-pyrrolo[2,3-b]pyrazin-3-yl)-1,7-naphthyridin-6-yl)-2-(4-methylpiperazin-1-yl) isonicotinamide [3625];

1-isopropyl-N-(3-(6-(piperidin-4-ylamino)pyrazin-2-yl)-1,7-naphthyridin-6-yl)-1H-pyrazole-4-carboxamide [3626];

1-isopropyl-N-(3-(6-((1-methylpiperidin-4-yl)amino)pyrazin-2-yl)-1,7-naphthyridin-6-yl)-1H-pyrazole-4-carboxamide [3627];

trans-4-((2-fluoroethyl)amino)-N-(6-(1-methyl-1H-pyrazol-4-yl)-2,7-naphthyridin-3-yl) cyclohexane-1-carboxamide [4597];

trans-4-((2-methoxyethyl)amino)-N-(6-(1-methyl-1H-pyrazol-4-yl)-2,7-naphthyridin-3-yl) cyclohexane-1-carboxamide [4598];

tert-butyl (trans-4-((6-(1-methyl-1H-pyrazol-4-yl)-2,7-naphthyridin-3-yl)carbamoyl)cyclohexyl) carbamate [4599];

N-(6-(1-methyl-1H-pyrazol-4-yl)-2,7-naphthyridin-3-yl)-2-((1-methylpiperidin-4-yl)amino) isonicotinamide [4600];

N-(6-(1-methyl-1H-pyrazol-4-yl)-2,7-naphthyridin-3-yl)-2-(4-methylpiperazin-1-yl)thiazole-5-carboxamide [4601];

N-(6-(1-methyl-1H-pyrazol-4-yl)-2,7-naphthyridin-3-yl)-2-(4-methylpiperazin-1-yl)thiazole-5-carboxamide [4602];

N-(6-(1-methyl-5-(piperidin-1-ylmethyl)-1H-pyrazol-4-yl)-2,7-naphthyridin-3-yl)-2-(2,7-diazaspiro[3.5]nonan-2-yl)isonicotinamide [4603];

N-(6-(1-methyl-1H-1,2,3-triazol-4-yl)-2,7-naphthyridin-3-yl)-4-(piperidin-4-yloxy)benzamide [4604];

N-(6-(1-methyl-1H-tetrazol-5-yl)-2,7-naphthyridin-3-yl)-1-(3,3,3-trifluoropropyl)piperidine-4-carboxamide [4605];

N-(6-(1,2-dimethyl-1H-imidazol-5-yl)-2,7-naphthyridin-3-yl)-2-(pyrrolidin-1-yl)propanamide [4606];

N-(6-(1,2-dimethyl-1H-imidazol-5-yl)-2,7-naphthyridin-3-yl)-2-(piperidin-1-yl)propanamide [4607];

4-isopropoxy-N-(6-(7-methyl-5,6,7,8-tetrahydroimidazo[1,2-a]pyrazin-3-yl)-2,7-naphthyridin-3-yl)benzamide [4608];

trans-3-morpholino-N-(6-(oxazol-5-yl)-2,7-naphthyridin-3-yl)cyclobutane-1-carboxamide [4609];

trans-4-(hydroxymethyl)-N-(6-(oxazol-5-yl)-2,7-naphthyridin-3-yl)cyclohexane-1-carboxamide [4610];

N-(6-(oxazol-5-yl)-2,7-naphthyridin-3-yl)piperidine-4-carboxamide [4611];

4-morpholino-N-(6-(oxazol-5-yl)-2,7-naphthyridin-3-yl) piperidine-1-carboxamide [4612];

N-(6-(oxazol-5-yl)-2,7-naphthyridin-3-yl)-4-(piperidin-4-yloxy)benzamide [4613];

N-(6-(oxazol-5-yl)-2,7-naphthyridin-3-yl)-3-(piperidin-4-yloxy)benzamide [4614];

2-methyl-N-(6-(oxazol-5-yl)-2,7-naphthyridin-3-yl)-5,6-dihydroimidazo[1,2-a]pyrazine-7(8H)-carboxamide [4615];

2-(1H-imidazol-1-yl)-N-(6-(oxazol-5-yl)-2,7-naphthyridin-3-yl)acetamide [4616];

trans-4-(hydroxymethyl)-N-(6-(thiazol-5-yl)-2,7-naphthyridin-3-yl)cyclohexane-1-carboxamide [4617];

trans-4-(dimethylamino)-N-(6-(thiazol-5-yl)-2,7-naphthyridin-3-yl)cyclohexane-1-carboxamide [4618];

N-(6-(thiazol-5-yl)-2,7-naphthyridin-3-yl)-1-((1-(trifluoromethyl)cyclopropyl)methyl)piperidine-4-carboxamide [4619];

trans-4-(hydroxymethyl)-N-(6-(2-methylthiazol-5-yl)-2,7-naphthyridin-3-yl)cyclohexane-1-carboxamide [4620];

trans-4-(dimethylamino)-N-(6-(2-methylthiazol-5-yl)-2,7-naphthyridin-3-yl)cyclohexane-1-carboxamide [4621];

N-(6-(2-methylthiazol-5-yl)-2,7-naphthyridin-3-yl)-1-(oxetan-3-yl)piperidine-4-carboxamide [4622];

N-(6-(2-methylthiazol-5-yl)-2,7-naphthyridin-3-yl)-1-(2-(pyrrolidin-1-yl)acetyl)piperidine-4-carboxamide [4623];

2-((1S,4S)-2-oxa-5-azabicyclo [2.2.1]heptan-5-yl)-N-(6-(5-methyl-1,3,4-thiadiazol-2-yl)-2,7-naphthyridin-3-yl)acetamide [4624];

N-(6-(5-(cyano(4-hydroxypiperidin-1-yl)methyl)pyridin-3-yl)-2,7-naphthyridin-3-yl) cyclopropanecarboxamide [4625];

4-fluoro-N-(6-(6-((1-methylazetidin-3-yl)methoxy)pyrazin-2-yl)-2,7-naphthyridin-3-yl) benzamide [4626];

1-isopropyl-N-(6-(6-((1-methylpiperidin-4-yl)amino)pyrazin-2-yl)-2,7-naphthyridin-3-yl)-1H-pyrazole-4-carboxamide [4627]; or a pharmaceutically acceptable salt thereof.

16. The compound of claim 1, wherein the compound of Formula I is selected from the group consisting of:

N-(6-(1H-pyrazol-4-yl)-2,7-naphthyridin-3-yl)-1-isobutylpiperidine-4-carboxamide [3628];

N-(6-(1-methyl-1H-pyrazol-4-yl)-2,7-naphthyridin-3-yl) cyclopropanecarboxamide [3629];

4,4-difluoro-N-(6-(1-methyl-1H-pyrazol-4-yl)-2,7-naphthyridin-3-yl)cyclohexane-1-carboxamide [3630];

trans-4-methoxy-N-(6-(1-methyl-1H-pyrazol-4-yl)-2,7-naphthyridin-3-yl)cyclohexane-1-carboxamide [3631];

trans-N-(6-(1-methyl-1H-pyrazol-4-yl)-2,7-naphthyridin-3-yl)-4-morpholinocyclohexane-1-carboxamide [3632];

trans-4-((3-fluoroazetidin-1-yl)methyl)-N-(6-(1-methyl-1H-pyrazol-4-yl)-2,7-naphthyridin-3-yl) cyclohexane-1-carboxamide [3633];

trans-N-(6-(1-methyl-1H-pyrazol-4-yl)-2,7-naphthyridin-3-yl)-4-((4-methylpiperazin-1-yl) methyl)cyclohexane-1-carboxamide [3634];

N-(6-(1-methyl-1H-pyrazol-4-yl)-2,7-naphthyridin-3-yl)-2-(pyrrolidin-1-yl)acetamide [3635];

(S)-2-(3-fluoropyrrolidin-1-yl)-N-(6-(1-methyl-1H-pyrazol-4-yl)-2,7-naphthyridin-3-yl) acetamide [3636];

(S)—N-(6-(1-methyl-1H-pyrazol-4-yl)-2,7-naphthyridin-3-yl)tetrahydrofuran-2-carboxamide [3637];

N-(6-(1-methyl-1H-pyrazol-4-yl)-2,7-naphthyridin-3-yl) piperidine-4-carboxamide [3638];

1-methyl-N-(6-(1-methyl-1H-pyrazol-4-yl)-2,7-naphthyridin-3-yl)piperidine-4-carboxamide [3639];

1-isopropyl-N-(6-(1-methyl-1H-pyrazol-4-yl)-2,7-naphthyridin-3-yl)piperidine-4-carboxamide [3640];

1-(tert-butyl)-N-(6-(1-methyl-1H-pyrazol-4-yl)-2,7-naphthyridin-3-yl)piperidine-4-carboxamide [3641];

1-cyclopropyl-N-(6-(1-methyl-1H-pyrazol-4-yl)-2,7-naphthyridin-3-yl)piperidine-4-carboxamide [3642];

1-isobutyl-N-(6-(1-methyl-1H-pyrazol-4-yl)-2,7-naphthyridin-3-yl)piperidine-4-carboxamide [3643];

N-(6-(1-methyl-1H-pyrazol-4-yl)-2,7-naphthyridin-3-yl)-1-neopentylpiperidine-4-carboxamide [3644];

1-(2-fluoroethyl)-N-(6-(1-methyl-1H-pyrazol-4-yl)-2,7-naphthyridin-3-yl)piperidine-4-carboxamide [3645];

N-(6-(1-methyl-1H-pyrazol-4-yl)-2,7-naphthyridin-3-yl)-1-(3,3,3-trifluoropropyl)piperidine-4-carboxamide [3646];

1-butyl-N-(6-(1-methyl-1H-pyrazol-4-yl)-2,7-naphthyridin-3-yl)piperidine-4-carboxamide [3647];

1-benzoyl-N-(6-(1-methyl-1H-pyrazol-4-yl)-2,7-naphthyridin-3-yl)piperidine-4-carboxamide [3648];

1-(2,2-difluoropropyl)-N-(6-(1-methyl-1H-pyrazol-4-yl)-2,7-naphthyridin-3-yl)piperidine-4-carboxamide [3649];

N-(6-(1-methyl-1H-pyrazol-4-yl)-2,7-naphthyridin-3-yl) azetidine-3-carboxamide [3650];

1-(2,2-difluoroethyl)-N-(6-(1-methyl-1H-pyrazol-4-yl)-2,7-naphthyridin-3-yl)piperidine-4-carboxamide [3651];

1-(2-fluoro-2-methylpropyl)-N-(6-(1-methyl-1H-pyrazol-4-yl)-2,7-naphthyridin-3-yl)piperidine-4-carboxamide [3652];

N-(6-(1-methyl-1H-pyrazol-4-yl)-2,7-naphthyridin-3-yl)-1-(oxetan-3-yl)piperidine-4-carboxamide [3653];

N-(6-(1-methyl-1H-pyrazol-4-yl)-2,7-naphthyridin-3-yl)-1-((3-methyloxetan-3-yl)methyl) piperidine-4-carboxamide [3654];

1-(2-methoxyethyl)-N-(6-(1-methyl-1H-pyrazol-4-yl)-2,7-naphthyridin-3-yl)piperidine-4-carboxamide [3655];

1-(2-isopropoxyethyl)-N-(6-(1-methyl-1H-pyrazol-4-yl)-2,7-naphthyridin-3-yl)piperidine-4-carboxamide [3656];

1,1-diisobutyl-4-((6-(1-methyl-1H-pyrazol-4-yl)-2,7-naphthyridin-3-yl)carbamoyl)piperidin-1-ium [3657];

4-fluoro-N-(6-(1-methyl-1H-pyrazol-4-yl)-2,7-naphthyridin-3-yl)piperidine-4-carboxamide [3658];

4-fluoro-1-methyl-N-(6-(1-methyl-1H-pyrazol-4-yl)-2,7-naphthyridin-3-yl)piperidine-4-carboxamide [3659];

4-fluoro-1-isobutyl-N-(6-(1-methyl-1H-pyrazol-4-yl)-2,7-naphthyridin-3-yl)piperidine-4-carboxamide [3660];

(S)—N-(6-(1-methyl-1H-pyrazol-4-yl)-2,7-naphthyridin-3-yl)piperidine-3-carboxamide [3661];

(R)—N-(6-(1-methyl-1H-pyrazol-4-yl)-2,7-naphthyridin-3-yl)piperidine-3-carboxamide [3662];

(S)-1-isobutyl-N-(6-(1-methyl-1H-pyrazol-4-yl)-2,7-naphthyridin-3-yl)piperidine-3-carboxamide [3663];

(R)-1-isobutyl-N-(6-(1-methyl-1H-pyrazol-4-yl)-2,7-naphthyridin-3-yl)piperidine-3-carboxamide [3664];

N-(6-(1-methyl-1H-pyrazol-4-yl)-2,7-naphthyridin-3-yl) tetrahydro-2H-pyran-4-carboxamide [3665];

N-(6-(1-methyl-1H-pyrazol-4-yl)-2,7-naphthyridin-3-yl)-2-(piperidin-1-yl)acetamide [3666];

2-(4-fluoropiperidin-1-yl)-N-(6-(1-methyl-1H-pyrazol-4-yl)-2,7-naphthyridin-3-yl)acetamide [3667];

trans-4-amino-N-(6-(1-methyl-1H-pyrazol-4-yl)-2,7-naphthyridin-3-yl)cyclohexane-1-carboxamide [3668];

N-(6-(1-methyl-1H-pyrazol-4-yl)-2,7-naphthyridin-3-yl)-2-(4-methylpiperazin-1-yl)acetamide [3669];

(S)—N-(6-(1-methyl-1H-pyrazol-4-yl)-2,7-naphthyridin-3-yl)piperidine-2-carboxamide [3670];

2-(4-isobutylpiperazin-1-yl)-N-(6-(1-methyl-1H-pyrazol-4-yl)-2,7-naphthyridin-3-yl)acetamide [3671];

2-(3,3-dimethylazetidin-1-yl)-N-(6-(1-methyl-1H-pyrazol-4-yl)-2,7-naphthyridin-3-yl)acetamide [3672];

(R)-2-(3-fluoropyrrolidin-1-yl)-N-(6-(1-methyl-1H-pyrazol-4-yl)-2,7-naphthyridin-3-yl) acetamide [3673];

(S)—N-(6-(1-methyl-1H-pyrazol-4-yl)-2,7-naphthyridin-3-yl)-2-(2-methylpyrrolidin-1-yl) acetamide [3674];

2-(3-azabicyclo[3.1.0]hexan-3-yl)-N-(6-(1-methyl-1H-pyrazol-4-yl)-2,7-naphthyridin-3-yl) acetamide [3675];

2-(7-azabicyclo[2.2.1]heptan-7-yl)-N-(6-(1-methyl-1H-pyrazol-4-yl)-2,7-naphthyridin-3-yl) acetamide [3676];

N-(6-(1-methyl-1H-pyrazol-4-yl)-2,7-naphthyridin-3-yl)-2-(4-methylpiperidin-1-yl)acetamide [3677];

N-(6-(1-methyl-1H-pyrazol-4-yl)-2,7-naphthyridin-3-yl)-2-(4-(trifluoromethyl)piperidin-1-yl) acetamide [3678];

2-(4-(difluoromethyl)piperidin-1-yl)-N-(6-(1-methyl-1H-pyrazol-4-yl)-2,7-naphthyridin-3-yl) acetamide [3679];

N-(6-(1-methyl-1H-pyrazol-4-yl)-2,7-naphthyridin-3-yl)-2-(6-azaspiro[2.5]octan-6-yl)acetamide [3680];

N-(6-(1-methyl-1H-pyrazol-4-yl)-2,7-naphthyridin-3-yl)-2-(pyrrolidin-1-yl)propanamide [3681];

(R)—N-(6-(1-methyl-1H-pyrazol-4-yl)-2,7-naphthyridin-3-yl)-2-(2-methylpyrrolidin-1-yl) acetamide [3682];

2-(cyclobutyl(methyl)amino)-N-(6-(1-methyl-1H-pyrazol-4-yl)-2,7-naphthyridin-3-yl)acetamide [3683];

2-(diethylamino)-N-(6-(1-methyl-1H-pyrazol-4-yl)-2,7-naphthyridin-3-yl)acetamide [3684];

7-(2-fluoroethyl)-N-(6-(1-methyl-1H-pyrazol-4-yl)-2,7-naphthyridin-3-yl)-7-azaspiro[3.5]nonane-2-carboxamide [3685];

4-methyl-N-(6-(1-methyl-1H-pyrazol-4-yl)-2,7-naphthyridin-3-yl)piperazine-1-carboxamide [3686];

(S)—N-(6-(1-methyl-1H-pyrazol-4-yl)-2,7-naphthyridin-3-yl)-2-(pyrrolidin-1-yl)propanamide [3687];

(R)—N-(6-(1-methyl-1H-pyrazol-4-yl)-2,7-naphthyridin-3-yl)-2-(pyrrolidin-1-yl)propanamide [3688];

(R)—N-(6-(1-methyl-1H-pyrazol-4-yl)-2,7-naphthyridin-3-yl)pyrrolidine-2-carboxamide [3689];

2-methyl-N-(6-(1-methyl-1H-pyrazol-4-yl)-2,7-naphthyridin-3-yl)-2-azaspiro[3.3]heptane-6-carboxamide [3690];

N-(6-(1-methyl-1H-pyrazol-4-yl)-2,7-naphthyridin-3-yl)-2-(2,2,2-trifluoroacetyl)-2-azaspiro[3.3]heptane-6-carboxamide [3691];

2-(2-fluoroethyl)-N-(6-(1-methyl-1H-pyrazol-4-yl)-2,7-naphthyridin-3-yl)-2-azaspiro[3.3]heptane-6-carboxamide [3692];

trans-4-(dimethylamino)-N-(6-(1-methyl-1H-pyrazol-4-yl)-2,7-naphthyridin-3-yl)cyclohexane-1-carboxamide [3693];

1-acetyl-N-(6-(1-methyl-1H-pyrazol-4-yl)-2,7-naphthyridin-3-yl)piperidine-4-carboxamide [3694];

N-(6-(1-methyl-1H-pyrazol-4-yl)-2,7-naphthyridin-3-yl)-1-((1-(trifluoromethyl)cyclopropyl) methyl)piperidine-4-carboxamide [3695];

(S)-1-(2-fluoropropyl)-N-(6-(1-methyl-1H-pyrazol-4-yl)-2,7-naphthyridin-3-yl)piperidine-4-carboxamide [3696];

(R)-1-(2-fluoropropyl)-N-(6-(1-methyl-1H-pyrazol-4-yl)-2,7-naphthyridin-3-yl)piperidine-4-carboxamide [3697];

N-(6-(1-methyl-1H-pyrazol-4-yl)-2,7-naphthyridin-3-yl)-2-(piperidin-1-yl)propanamide [3698];

N-(6-(1-methyl-1H-pyrazol-4-yl)-2,7-naphthyridin-3-yl)-1-(methylsulfonyl)piperidine-4-carboxamide [3699];

1'-methyl-N-(6-(1-methyl-1H-pyrazol-4-yl)-2,7-naphthyridin-3-yl)-[1,4'-bipiperidine]-4-carboxamide [3700];

trans-4-(hydroxymethyl)-N-(6-(1-methyl-1H-pyrazol-4-yl)-2,7-naphthyridin-3-yl)cyclohexane-1-carboxamide [3701];

methyl 2-(4-((6-(1-methyl-1H-pyrazol-4-yl)-2,7-naphthyridin-3-yl)carbamoyl)piperidin-1-yl) acetate [3702];

1-benzyl-N-(6-(1-methyl-1H-pyrazol-4-yl)-2,7-naphthyridin-3-yl)piperidine-4-carboxamide [3703];

N-(6-(1-methyl-1H-pyrazol-4-yl)-2,7-naphthyridin-3-yl)-1-(2-(pyrrolidin-1-yl)acetyl)piperidine-4-carboxamide [3704];

N-(6-(1-methyl-1H-pyrazol-4-yl)-2,7-naphthyridin-3-yl)-2-morpholinoacetamide [3705];

(S)—N-(6-(1-methyl-1H-pyrazol-4-yl)-2,7-naphthyridin-3-yl)-2-(3-methylmorpholino)acetamide [3706];

(R)—N-(6-(1-methyl-1H-pyrazol-4-yl)-2,7-naphthyridin-3-yl)-2-(3-methylmorpholino)acetamide [3707];

(S)—N-(6-(1-methyl-1H-pyrazol-4-yl)-2,7-naphthyridin-3-yl)-2-(2-methylmorpholino)acetamide [3708];

2-((2R,6S)-2,6-dimethylmorpholino)-N-(6-(1-methyl-1H-pyrazol-4-yl)-2,7-naphthyridin-3-yl) acetamide [3709];

2-((1S,4S)-2-oxa-5-azabicyclo [2.2.1]heptan-5-yl)-N-(6-(1-methyl-1H-pyrazol-4-yl)-2,7-naphthyridin-3-yl)acetamide [3710];

2-((1R,4R)-2-oxa-5-azabicyclo[2.2.1]heptan-5-yl)-N-(6-(1-methyl-1H-pyrazol-4-yl)-2,7-naphthyridin-3-yl)acetamide [3711];

2-(3-oxa-8-azabicyclo[3.2.1]octan-8-yl)-N-(6-(1-methyl-1H-pyrazol-4-yl)-2,7-naphthyridin-3-yl) acetamide [3712];

(S)—N-(6-(1-methyl-1H-pyrazol-4-yl)-2,7-naphthyridin-3-yl)-2-morpholinopropanamide [3713];

N-(6-(1-methyl-1H-pyrazol-4-yl)-2,7-naphthyridin-3-yl)-2-(morpholin-2-yl)acetamide [3714];

N-(6-(1-methyl-1H-pyrazol-4-yl)-2,7-naphthyridin-3-yl)-2-(4-methylmorpholin-2-yl)acetamide [3715];

2-(4-ethylpiperazin-1-yl)-N-(6-(1-methyl-1H-pyrazol-4-yl)-2,7-naphthyridin-3-yl)acetamide [3716];

2-(4-isopropylpiperazin-1-yl)-N-(6-(1-methyl-1H-pyrazol-4-yl)-2,7-naphthyridin-3-yl)acetamide [3717];

2-(4-cyclopropylpiperazin-1-yl)-N-(6-(1-methyl-1H-pyrazol-4-yl)-2,7-naphthyridin-3-yl) acetamide [3718];

2-(4-(2-fluoroethyl)piperazin-1-yl)-N-(6-(1-methyl-1H-pyrazol-4-yl)-2,7-naphthyridin-3-yl) acetamide [3719];

(S)-2-(2,4-dimethylpiperazin-1-yl)-N-(6-(1-methyl-1H-pyrazol-4-yl)-2,7-naphthyridin-3-yl) acetamide [3720];

1-(2-hydroxyethyl)-N-(6-(1-methyl-1H-pyrazol-4-yl)-2,7-naphthyridin-3-yl)piperidine-4-carboxamide [3721];

N-(6-(1-methyl-1H-pyrazol-4-yl)-2,7-naphthyridin-3-yl)-1-(pyridin-2-ylmethyl)piperidine-4-carboxamide [3722];

N-(6-(1-methyl-1H-pyrazol-4-yl)-2,7-naphthyridin-3-yl)-1-(oxazol-2-ylmethyl)piperidine-4-carboxamide [3723];

(R)—N-(6-(1-methyl-1H-pyrazol-4-yl)-2,7-naphthyridin-3-yl)-1-oxotetrahydro-1H-pyrrolo[1,2-c]imidazole-2(3H)-carboxamide [3724];

(R)-1-methyl-N-(6-(1-methyl-1H-pyrazol-4-yl)-2,7-naphthyridin-3-yl)pyrrolidine-2-carboxamide [3725];

N-(6-(1-methyl-1H-pyrazol-4-yl)-2,7-naphthyridin-3-yl)-1-(tetrahydro-2H-pyran-4-yl)piperidine-4-carboxamide [3726];

N-(6-(1-methyl-1H-pyrazol-4-yl)-2,7-naphthyridin-3-yl)-1-(pyrimidin-2-ylmethyl)piperidine-4-carboxamide [3727];

N-(6-(1-methyl-1H-pyrazol-4-yl)-2,7-naphthyridin-3-yl)-1-(pyrazin-2-ylmethyl)piperidine-4-carboxamide [3728];

1-((5-methyl-1,2,4-oxadiazol-3-yl)methyl)-N-(6-(1-methyl-1H-pyrazol-4-yl)-2,7-naphthyridin-3-yl)piperidine-4-carboxamide [3729];

1-(2-hydroxy-2-methylpropyl)-N-(6-(1-methyl-1H-pyrazol-4-yl)-2,7-naphthyridin-3-yl) piperidine-4-carboxamide [3730];

tert-butyl 2-(4-((6-(1-methyl-1H-pyrazol-4-yl)-2,7-naphthyridin-3-yl)carbamoyl)piperidin-1-yl) acetate [3731];

2-(4-((6-(1-methyl-1H-pyrazol-4-yl)-2,7-naphthyridin-3-yl)carbamoyl)piperidin-1-yl)acetic acid [3732];

2-(4-methyl-1,4-diazepan-1-yl)-N-(6-(1-methyl-1H-pyrazol-4-yl)-2,7-naphthyridin-3-yl) acetamide [3733];

tert-butyl (6-(1-methyl-1H-pyrazol-4-yl)-2,7-naphthyridin-3-yl)carbamate [3734];

N-(6-(1-methyl-1H-pyrazol-4-yl)-2,7-naphthyridin-3-yl)but-2-ynamide [3735];

trans-4-((6-(1-methyl-1H-pyrazol-4-yl)-2,7-naphthyridin-3-yl)carbamoyl)cyclohexane-1-carboxylic acid [3736];

N-(6-(1-methyl-1H-pyrazol-4-yl)-2,7-naphthyridin-3-yl)-3-morpholinopropanamide [3737];

trans-N-(6-(1-methyl-1H-pyrazol-4-yl)-2,7-naphthyridin-3-yl)-3-morpholinocyclobutane-1-carboxamide [3738];

N-(6-(1-methyl-1H-pyrazol-4-yl)-2,7-naphthyridin-3-yl)quinuclidine-4-carboxamide [3739];

1-isobutyl-N-(6-(1-methyl-1H-pyrazol-4-yl)-2,7-naphthyridin-3-yl)azepane-4-carboxamide [3740];

2-(4-methoxypiperidin-1-yl)-N-(6-(1-methyl-1H-pyrazol-4-yl)-2,7-naphthyridin-3-yl)acetamide [3741];

2-(4-hydroxypiperidin-1-yl)-N-(6-(1-methyl-1H-pyrazol-4-yl)-2,7-naphthyridin-3-yl)acetamide [3742];

3-(hydroxymethyl)-N-(6-(1-methyl-1H-pyrazol-4-yl)-2,7-naphthyridin-3-yl)bicyclo[1.1.1]pentane-1-carboxamide [3743];

1-methyl-N-(6-(1-methyl-1H-pyrazol-4-yl)-2,7-naphthyridin-3-yl)azepane-4-carboxamide [3744];

trans-4-(dimethylamino)-N-(6-(1-methyl-1H-pyrazol-4-yl)-2,7-naphthyridin-3-yl)cyclohexane-1-carboxamide [3745];

trans-4-(bis(methyl-$d_3$)amino)-N-(6-(1-methyl-1H-pyrazol-4-yl)-2,7-naphthyridin-3-yl) cyclohexane-1-carboxamide [3746];

N-(6-(1-methyl-1H-pyrazol-4-yl)-2,7-naphthyridin-3-yl)-3-((4-methylpiperazin-1-yl)methyl) bicyclo[1.1.1]pentane-1-carboxamide [3747];

methyl trans-4-((6-(1-methyl-1H-pyrazol-4-yl)-2,7-naphthyridin-3-yl)carbamoyl)cyclohexane-1-carboxylate [3748];

2-(1-isobutylpyrrolidin-3-yl)-N-(6-(1-methyl-1H-pyrazol-4-yl)-2,7-naphthyridin-3-yl)acetamide [3749];

trans-N-(6-(1-methyl-1H-pyrazol-4-yl)-2,7-naphthyridin-3-yl)-4-(4-methylpiperazine-1-carbonyl)cyclohexane-1-carboxamide [3750];

1-isobutyl-N-(6-(1-methyl-1H-pyrazol-4-yl)-2,7-naphthyridin-3-yl)piperidine-4-carboxamide [3751];

N-(6-(1-methyl-1H-pyrazol-4-yl)-2,7-naphthyridin-3-yl)-1-(phenylsulfonyl)piperidine-4-carboxamide [3752];

8-methyl-N-(6-(1-methyl-1H-pyrazol-4-yl)-2,7-naphthyridin-3-yl)-3,8-diazabicyclo[3.2.1]octane-3-carboxamide [3753];

3-methyl-N-(6-(1-methyl-1H-pyrazol-4-yl)-2,7-naphthyridin-3-yl)-3,8-diazabicyclo[3.2.1]octane-8-carboxamide [3754];

(1R,3s,5S)-3-amino-N-(6-(1-methyl-1H-pyrazol-4-yl)-2,7-naphthyridin-3-yl)-8-azabicyclo[3.2.1] octane-8-carboxamide [3755];

(1R,3s,5S)—N-(6-(1-methyl-1H-pyrazol-4-yl)-2,7-naphthyridin-3-yl)-3-((3,3,3-trifluoropropyl) amino)-8-azabicyclo[3.2.1]octane-8-carboxamide [3756];

(1R,3s,5S)-3-(((1,3-difluoropropan-2-yl)amino)-N-(6-(1-methyl-1H-pyrazol-4-yl)-2,7-naphthyridin-3-yl)-8-azabicyclo[3.2.1]octane-8-carboxamide [3757];

N-(6-(1-methyl-1H-pyrazol-4-yl)-2,7-naphthyridin-3-yl)morpholine-4-carboxamide [3758];

4-(dimethylamino)-N-(6-(1-methyl-1H-pyrazol-4-yl)-2,7-naphthyridin-3-yl)piperidine-1-carboxamide [3759];

(S)-2,4-dimethyl-N-(6-(1-methyl-1H-pyrazol-4-yl)-2,7-naphthyridin-3-yl)piperazine-1-carboxamide [3760];

1-methyl-3-(6-(1-methyl-1H-pyrazol-4-yl)-2,7-naphthyridin-3-yl)-1-(1-methylpiperidin-4-yl)urea [3761];

1-(6-(1-methyl-1H-pyrazol-4-yl)-2,7-naphthyridin-3-yl)-3-(1-methylpiperidin-4-yl)urea [3762];

4-isopropyl-N-(6-(1-methyl-1H-pyrazol-4-yl)-2,7-naphthyridin-3-yl)piperazine-1-carboxamide [3763];

(R)-3,4-dimethyl-N-(6-(1-methyl-1H-pyrazol-4-yl)-2,7-naphthyridin-3-yl)piperazine-1-carboxamide [3764];

N-(6-(1H-pyrazol-4-yl)-2,7-naphthyridin-3-yl)-2-(4-methylpiperazin-1-yl)isonicotinamide [3765];

N-(6-(1-methyl-1H-pyrazol-4-yl)-2,7-naphthyridin-3-yl)-3-(piperazin-1-yl)benzamide [3766];

N-(6-(1-methyl-1H-pyrazol-4-yl)-2,7-naphthyridin-3-yl)-3-(4-methylpiperazin-1-yl)benzamide [3767];

N-(6-(1-methyl-1H-pyrazol-4-yl)-2,7-naphthyridin-3-yl)-3-(pyrrolidin-1-ylmethyl)benzamide [3768];

N-(6-(1-methyl-1H-pyrazol-4-yl)-2,7-naphthyridin-3-yl)-3-(piperidin-4-yloxy)benzamide [3769];

N-(6-(1-methyl-1H-pyrazol-4-yl)-2,7-naphthyridin-3-yl)-3-((1-methylpiperidin-4-yl)oxy) benzamide [3770];

N-(6-(1-methyl-1H-pyrazol-4-yl)-2,7-naphthyridin-3-yl)-4-(piperidin-4-yloxy)benzamide [3771];

N-(6-(1-methyl-1H-pyrazol-4-yl)-2,7-naphthyridin-3-yl)-4-((1-methylpiperidin-4-yl)oxy) benzamide [3772];

N-(6-(1-methyl-1H-pyrazol-4-yl)-2,7-naphthyridin-3-yl)-2-(piperazin-1-yl)isonicotinamide [3773];

N-(6-(1-methyl-1H-pyrazol-4-yl)-2,7-naphthyridin-3-yl)-2-(4-methylpiperazin-1-yl) isonicotinamide [3774];

2-(4-isopropylpiperazin-1-yl)-N-(6-(1-methyl-1H-pyrazol-4-yl)-2,7-naphthyridin-3-yl) isonicotinamide [3775];

2-(4-cyclopropylpiperazin-1-yl)-N-(6-(1-methyl-1H-pyrazol-4-yl)-2,7-naphthyridin-3-yl) isonicotinamide [3776];

2-(4-(2-fluoroethyl)piperazin-1-yl)-N-(6-(1-methyl-1H-pyrazol-4-yl)-2,7-naphthyridin-3-yl) isonicotinamide [3777];

N-(6-(1-methyl-1H-pyrazol-4-yl)-2,7-naphthyridin-3-yl)-6-(4-methylpiperazin-1-yl)nicotinamide [3778];

N-(6-(1-methyl-1H-pyrazol-4-yl)-2,7-naphthyridin-3-yl)-5-(piperidin-4-yloxy)nicotinamide [3779];

N-(6-(1-methyl-1H-pyrazol-4-yl)-2,7-naphthyridin-3-yl)-2-(piperidin-4-yloxy)isonicotinamide [3780];

N-(6-(1-methyl-1H-pyrazol-4-yl)-2,7-naphthyridin-3-yl)-2-((1-methylpiperidin-4-yl)oxy) isonicotinamide [3781];

N-(6-(1-methyl-1H-pyrazol-4-yl)-2,7-naphthyridin-3-yl)-5-(piperidin-4-ylamino)nicotinamide [3782];

N-(6-(1-methyl-1H-pyrazol-4-yl)-2,7-naphthyridin-3-yl)-5-((1-methylpiperidin-4-yl)amino) nicotinamide [3783];

2-(4-aminopiperidin-1-yl)-N-(6-(1-methyl-1H-pyrazol-4-yl)-2,7-naphthyridin-3-yl) isonicotinamide [3784];

N-(6-(1-methyl-1H-pyrazol-4-yl)-2,7-naphthyridin-3-yl)-2-(4-(methylamino)piperidin-1-yl) isonicotinamide [3785];

2-(4-(dimethylamino)piperidin-1-yl)-N-(6-(1-methyl-1H-pyrazol-4-yl)-2,7-naphthyridin-3-yl) isonicotinamide [3786];

2-((1-isopropylpiperidin-4-yl)oxy)-N-(6-(1-methyl-1H-pyrazol-4-yl)-2,7-naphthyridin-3-yl) isonicotinamide [3787];

2-(3-aminoazetidin-1-yl)-N-(6-(1-methyl-1H-pyrazol-4-yl)-2,7-naphthyridin-3-yl) isonicotinamide [3788];

2-(3-(dimethylamino)azetidin-1-yl)-N-(6-(1-methyl-1H-pyrazol-4-yl)-2,7-naphthyridin-3-yl) isonicotinamide [3789];

N-(6-(1-methyl-1H-pyrazol-4-yl)-2,7-naphthyridin-3-yl)-2-morpholinoisonicotinamide [3790];

2-((2-(dimethylamino)ethyl)amino)-N-(6-(1-methyl-1H-pyrazol-4-yl)-2,7-naphthyridin-3-yl) isonicotinamide [3791];

2-(2-(dimethylamino)ethoxy)-N-(6-(1-methyl-1H-pyrazol-4-yl)-2,7-naphthyridin-3-yl) isonicotinamide [3792];

2-(4-isobutylpiperazin-1-yl)-N-(6-(1-methyl-1H-pyrazol-4-yl)-2,7-naphthyridin-3-yl) isonicotinamide [3793];

2-(azetidin-3-yloxy)-N-(6-(1-methyl-1H-pyrazol-4-yl)-2,7-naphthyridin-3-yl)isonicotinamide [3794];

N-(6-(1-methyl-1H-pyrazol-4-yl)-2,7-naphthyridin-3-yl)-2-((1-methylazetidin-3-yl)oxy) isonicotinamide [3795];

2-(4-ethylpiperazin-1-yl)-N-(6-(1-methyl-1H-pyrazol-4-yl)-2,7-naphthyridin-3-yl) isonicotinamide [3796];

4-((dimethylamino)methyl)-N-(6-(1-methyl-1H-pyrazol-4-yl)-2,7-naphthyridin-3-yl)benzamide [3797];

N-(6-(1-methyl-1H-pyrazol-4-yl)-2,7-naphthyridin-3-yl)-3-(1-methylpiperidin-4-yl)benzamide [3798];

N-(6-(1-methyl-1H-pyrazol-4-yl)-2,7-naphthyridin-3-yl)-3-((4-methylpiperazin-1-yl)methyl) benzamide [3799];

N-(6-(1-methyl-1H-pyrazol-4-yl)-2,7-naphthyridin-3-yl) isonicotinamide [3800];

2-hydroxy-N-(6-(1-methyl-1H-pyrazol-4-yl)-2,7-naphthyridin-3-yl)isonicotinamide [3801];

2-isopropoxy-N-(6-(1-methyl-1H-pyrazol-4-yl)-2,7-naphthyridin-3-yl)isonicotinamide [3802];

N-(6-(1-methyl-1H-pyrazol-4-yl)-2,7-naphthyridin-3-yl)-2-(1-methylpiperidin-4-yl) isonicotinamide [3803];

1'-methyl-N-(6-(1-methyl-1H-pyrazol-4-yl)-2,7-naphthyridin-3-yl)-1',2',3',6'-tetrahydro-[2,4'-bipyridine]-4-carboxamide [3804];

N-(6-(1-methyl-1H-pyrazol-4-yl)-2,7-naphthyridin-3-yl)-2-(4-(6-(4-methylpiperazin-1-yl) nicotinoyl)piperazin-1-yl)isonicotinamide [3805];

2-(4-hydroxy-4-methyl-4λ4-piperazin-1-yl)-N-(6-(1-methyl-1H-pyrazol-4-yl)-2,7-naphthyridin-3-yl)isonicotinamide [3806];

2-methyl-N-(6-(1-methyl-1H-pyrazol-4-yl)-2,7-naphthyridin-3-yl)-6-(4-methylpiperazin-1-yl) isonicotinamide [3807];

3-methyl-N-(6-(1-methyl-1H-pyrazol-4-yl)-2,7-naphthyridin-3-yl)-2-(4-methylpiperazin-1-yl) isonicotinamide [3808];

2-(4-methyl-1,4-diazepan-1-yl)-N-(6-(1-methyl-1H-pyrazol-4-yl)-2,7-naphthyridin-3-yl) isonicotinamide [3809];

2-((2S,6R)-2,6-dimethylmorpholino)-N-(6-(1-methyl-1H-pyrazol-4-yl)-2,7-naphthyridin-3-yl) isonicotinamide [3810];

N-(6-(1-methyl-1H-pyrazol-4-yl)-2,7-naphthyridin-3-yl)-2-(2,7-diazaspiro[3.5]nonan-2-yl) isonicotinamide [3811];

N-(6-(1-methyl-1H-pyrazol-4-yl)-2,7-naphthyridin-3-yl)-2-(7-methyl-2,7-diazaspiro[3.5]nonan-2-yl)isonicotinamide [3812];

N-(6-(1-methyl-1H-pyrazol-4-yl)-2,7-naphthyridin-3-yl)-2-(2,7-diazaspiro[3.5]nonan-7-yl) isonicotinamide [3813];

N-(6-(1-methyl-1H-pyrazol-4-yl)-2,7-naphthyridin-3-yl)-2-(2-methyl-2,7-diazaspiro[3.5]nonan-7-yl)isonicotinamide [3814];

2-(methyl(1-methylpiperidin-4-yl)amino)-N-(6-(1-methyl-1H-pyrazol-4-yl)-2,7-naphthyridin-3-yl)isonicotinamide [3815];

N-(6-(1-methyl-1H-pyrazol-4-yl)-2,7-naphthyridin-3-yl)-2-((1-methylpiperidin-4-yl)thio) isonicotinamide [3816];

N-(6-(1-methyl-1H-pyrazol-4-yl)-2,7-naphthyridin-3-yl)-2-(4-methylpiperazin-1-yl)pyrimidine-4-carboxamide [3817];

N-(6-(1-methyl-1H-pyrazol-4-yl)-2,7-naphthyridin-3-yl)-6-(4-methylpiperazin-1-yl)pyridazine-4-carboxamide [3818];

N-(6-(1-methyl-1H-pyrazol-4-yl)-2,7-naphthyridin-3-yl)-6-(4-methylpiperazin-1-yl)pyrimidine-4-carboxamide [3819];

N-(6-(1-methyl-1H-pyrazol-4-yl)-2,7-naphthyridin-3-yl)-2-phenylacetamide [3820];

N-(6-(1-methyl-1H-pyrazol-4-yl)-2,7-naphthyridin-3-yl)-3-phenylpropanamide [3821];

N-(6-(1-methyl-1H-pyrazol-4-yl)-2,7-naphthyridin-3-yl)-2-(pyridin-3-yl)acetamide [3822];

N-(6-(1-methyl-1H-pyrazol-4-yl)-2,7-naphthyridin-3-yl)-3-(pyridin-3-yl)propanamide [3823];

N-(6-(1-methyl-1H-pyrazol-4-yl)-2,7-naphthyridin-3-yl)-2-(pyridin-4-yl)acetamide [3824];

N-(6-(1-methyl-1H-pyrazol-4-yl)-2,7-naphthyridin-3-yl)-3-(pyridin-4-yl)propanamide [3825];

N-(6-(1-methyl-1H-pyrazol-4-yl)-2,7-naphthyridin-3-yl) isoindoline-5-carboxamide [3826];

2-methyl-N-(6-(1-methyl-1H-pyrazol-4-yl)-2,7-naphthyridin-3-yl)isoindoline-5-carboxamide [3827];

N-(6-(1-methyl-1H-pyrazol-4-yl)-2,7-naphthyridin-3-yl)-1,2,3,4-tetrahydroisoquinoline-7-carboxamide [3828];

2-methyl-N-(6-(1-methyl-1H-pyrazol-4-yl)-2,7-naphthyridin-3-yl)-1,2,3,4-tetrahydroisoquinoline-7-carboxamide [3829];

2-methyl-N-(6-(1-methyl-1H-pyrazol-4-yl)-2,7-naphthyridin-3-yl)-1,2,3,4-tetrahydroisoquinoline-6-carboxamide [3830];

N-(6-(1-methyl-1H-pyrazol-4-yl)-2,7-naphthyridin-3-yl)-1,2,3,4-tetrahydroisoquinoline-6-carboxamide [3831];

N-(6-(1-methyl-1H-pyrazol-4-yl)-2,7-naphthyridin-3-yl)-1H-indole-5-carboxamide [3832];

N-(6-(1-methyl-1H-pyrazol-4-yl)-2,7-naphthyridin-3-yl) benzofuran-5-carboxamide [3833];

N-(6-(1-methyl-1H-pyrazol-4-yl)-2,7-naphthyridin-3-yl) furo[2,3-c]pyridine-5-carboxamide [3834];

N-(6-(1-methyl-1H-pyrazol-4-yl)-2,7-naphthyridin-3-yl) benzo[b]thiophene-5-carboxamide [3835];

N-(6-(1-methyl-1H-pyrazol-4-yl)-2,7-naphthyridin-3-yl) benzofuran-6-carboxamide [3836];

N-(6-(1-methyl-1H-pyrazol-4-yl)-2,7-naphthyridin-3-yl) benzo[d]oxazole-6-carboxamide [3837];

N-(6-(1-methyl-1H-pyrazol-4-yl)-2,7-naphthyridin-3-yl) benzo[d]thiazole-6-carboxamide [3838];

N-(6-(1-methyl-1H-pyrazol-4-yl)-2,7-naphthyridin-3-yl) benzo[d]oxazole-5-carboxamide [3839];

N-(6-(1-methyl-1H-pyrazol-4-yl)-2,7-naphthyridin-3-yl) benzo[d]thiazole-5-carboxamide [3840];

N-(6-(1-methyl-1H-pyrazol-4-yl)-2,7-naphthyridin-3-yl) quinoline-3-carboxamide [3841];

N-(6-(1-methyl-1H-pyrazol-4-yl)-2,7-naphthyridin-3-yl) quinoline-6-carboxamide [3842];

N-(6-(1-methyl-1H-pyrazol-4-yl)-2,7-naphthyridin-3-yl) quinoxaline-6-carboxamide [3843];

5-chloro-N-(6-(1-methyl-1H-pyrazol-4-yl)-2,7-naphthyridin-3-yl)-2-(4-methylpiperazin-1-yl) isonicotinamide [3844];

3-chloro-N-(6-(1-methyl-1H-pyrazol-4-yl)-2,7-naphthyridin-3-yl)-2-(4-methylpiperazin-1-yl) isonicotinamide [3845];
2-(2,5-diazabicyclo[2.2.1]heptan-2-yl)-N-(6-(1-methyl-1H-pyrazol-4-yl)-2,7-naphthyridin-3-yl) isonicotinamide [3846];
N-(6-(1-methyl-1H-pyrazol-4-yl)-2,7-naphthyridin-3-yl)-2-(5-methyl-2,5-diazabicyclo[2.2.1] heptan-2-yl)isonicotinamide [3847];
3-fluoro-N-(6-(1-methyl-1H-pyrazol-4-yl)-2,7-naphthyridin-3-yl)-2-(4-methylpiperazin-1-yl) isonicotinamide [3848];
N-(6-(1-methyl-1H-pyrazol-4-yl)-2,7-naphthyridin-3-yl)-2-((4-methylpiperazin-1-yl)methyl) isonicotinamide [3849];
N-(6-(1-methyl-1H-pyrazol-4-yl)-2,7-naphthyridin-3-yl)-2-(morpholinomethyl)isonicotinamide [3850];
N-(6-(1-methyl-1H-pyrazol-4-yl)-2,7-naphthyridin-3-yl)-2-(pyrrolidin-1-ylmethyl) isonicotinamide [3851];
N-(6-(1-methyl-1H-pyrazol-4-yl)-2,7-naphthyridin-3-yl)-2-(2-(4-methylpiperazin-1-yl)pyridin-4-yl)acetamide [3852];
1-methyl-N-(6-(1-methyl-1H-pyrazol-4-yl)-2,7-naphthyridin-3-yl)-1H-indazole-5-carboxamide [3853];
1-methyl-N-(6-(1-methyl-1H-pyrazol-4-yl)-2,7-naphthyridin-3-yl)-1H-benzo[d]imidazole-5-carboxamide [3854];
N-(6-(1-methyl-1H-pyrazol-4-yl)-2,7-naphthyridin-3-yl)-1-(piperidin-4-yl)-1H-pyrazole-4-carboxamide [3855];
N-(6-(1-methyl-1H-pyrazol-4-yl)-2,7-naphthyridin-3-yl)-1-(1-methylpiperidin-4-yl)-1H-pyrazole-4-carboxamide [3856];
1-(1-ethylpiperidin-4-yl)-N-(6-(1-methyl-1H-pyrazol-4-yl)-2,7-naphthyridin-3-yl)-1H-pyrazole-4-carboxamide [3857];
1-(1-(2-fluoroethyl)piperidin-4-yl)-N-(6-(1-methyl-1H-pyrazol-4-yl)-2,7-naphthyridin-3-yl)-1H-pyrazole-4-carboxamide [3858];
1-(1-isopropylpiperidin-4-yl)-N-(6-(1-methyl-1H-pyrazol-4-yl)-2,7-naphthyridin-3-yl)-1H-pyrazole-4-carboxamide [3859];
1-(1-cyclopropylpiperidin-4-yl)-N-(6-(1-methyl-1H-pyrazol-4-yl)-2,7-naphthyridin-3-yl)-1H-pyrazole-4-carboxamide [3860];
isopropyl 4-(4-((6-(1-methyl-1H-pyrazol-4-yl)-2,7-naphthyridin-3-yl)carbamoyl)-1H-pyrazol-1-yl)piperidine-1-carboxylate [3861];
N-(6-(1-methyl-1H-pyrazol-4-yl)-2,7-naphthyridin-3-yl)-1-(piperidin-4-yl)-1H-1,2,3-triazole-4-carboxamide [3862];
N-(6-(1-methyl-1H-pyrazol-4-yl)-2,7-naphthyridin-3-yl)-1-(1-methylpiperidin-4-yl)-1H-1,2,3-triazole-4-carboxamide [3863];
1-(1-(2-fluoroethyl)piperidin-4-yl)-N-(6-(1-methyl-1H-pyrazol-4-yl)-2,7-naphthyridin-3-yl)-1H-1,2,3-triazole-4-carboxamide [3864];
1-(1-isopropylpiperidin-4-yl)-N-(6-(1-methyl-1H-pyrazol-4-yl)-2,7-naphthyridin-3-yl)-1H-1,2,3-triazole-4-carboxamide [3865];
N-(6-(1-methyl-1H-pyrazol-4-yl)-2,7-naphthyridin-3-yl)-2-(4-methylpiperazin-1-yl)oxazole-5-carboxamide [3866];
2-(3-(dimethylamino)azetidin-1-yl)-N-(6-(1-methyl-1H-pyrazol-4-yl)-2,7-naphthyridin-3-yl) oxazole-4-carboxamide [3867];
N-(6-(1-methyl-1H-pyrazol-4-yl)-2,7-naphthyridin-3-yl)-2-(piperidin-4-yl)oxazole-4-carboxamide [3868];
N-(6-(1-methyl-1H-pyrazol-4-yl)-2,7-naphthyridin-3-yl)-2-(1-methylpiperidin-4-yl)oxazole-4-carboxamide [3869];
2-(1-(2-fluoroethyl)piperidin-4-yl)-N-(6-(1-methyl-1H-pyrazol-4-yl)-2,7-naphthyridin-3-yl) oxazole-4-carboxamide [3870];
2-(1-isopropylpiperidin-4-yl)-N-(6-(1-methyl-1H-pyrazol-4-yl)-2,7-naphthyridin-3-yl)oxazole-4-carboxamide [3871];
N-(6-(1-methyl-1H-pyrazol-4-yl)-2,7-naphthyridin-3-yl)-2-(4-methylpiperazin-1-yl)oxazole-4-carboxamide [3872];
2-(3-(dimethylamino)azetidin-1-yl)-N-(6-(1-methyl-1H-pyrazol-4-yl)-2,7-naphthyridin-3-yl) thiazole-5-carboxamide [3873];
N-(6-(1-methyl-1H-pyrazol-4-yl)-2,7-naphthyridin-3-yl)-2-(piperidin-4-yl)thiazole-4-carboxamide [3874];
N-(6-(1-methyl-1H-pyrazol-4-yl)-2,7-naphthyridin-3-yl)-2-(4-methylpiperazin-1-yl)thiazole-4-carboxamide [3875];
2-(1-(2-fluoroethyl)piperidin-4-yl)-N-(6-(1-methyl-1H-pyrazol-4-yl)-2,7-naphthyridin-3-yl) thiazole-4-carboxamide [3876];
2-(1-isopropylpiperidin-4-yl)-N-(6-(1-methyl-1H-pyrazol-4-yl)-2,7-naphthyridin-3-yl)thiazole-4-carboxamide [3877];
1-methyl-N-(6-(1-methyl-1H-pyrazol-4-yl)-2,7-naphthyridin-3-yl-4-d)piperidine-4-carboxamide [3878];
N-(6-(1-methyl-1H-pyrazol-4-yl)-2,7-naphthyridin-3-yl)-1-(2-(methyl-d3)propyl-1,1,2,3,3,3-d6) piperidine-4-carboxamide [3879];
N-(6-(1-methyl-1H-pyrazol-4-yl)-2,7-naphthyridin-3-yl)-2-(pyrrolidin-1-yl-2,2,5,5-d$_4$)acetamide [3880];
N-(6-(1-methyl-1H-pyrazol-4-yl)-2,7-naphthyridin-3-yl)-2-(4-(methyl-d$_3$)piperazin-1-yl) acetamide [3881];
N-(6-(1-methyl-1H-pyrazol-4-yl)-2,7-naphthyridin-3-yl)-2-(morpholino-d$_8$)acetamide [3882];
(S)—N-(6-(1-(methyl-d$_3$)-1H-pyrazol-4-yl)-2,7-naphthyridin-3-yl)-2-(pyrrolidin-1-yl)propanamide [3883];
1-isobutyl-N-(6-(1-(methyl-d$_3$)-1H-pyrazol-4-yl)-2,7-naphthyridin-3-yl)piperidine-4-carboxamide [3884];
N-(6-(1-(methyl-d$_3$)-1H-pyrazol-4-yl)-2,7-naphthyridin-3-yl)-2-(4-methylpiperazin-1-yl) acetamide [3885];
N-(6-(1-(methyl-d$_3$)-1H-pyrazol-4-yl)-2,7-naphthyridin-3-yl)-2-(pyrrolidin-1-yl)acetamide [3886];
N-(6-(1-(methyl-d$_3$)-1H-pyrazol-4-yl)-2,7-naphthyridin-3-yl)-2-(piperidin-1-yl)acetamide [3887];
N-(6-(1-(methyl-d$_3$)-1H-pyrazol-4-yl)-2,7-naphthyridin-3-yl)-1-(3,3,3-trifluoropropyl)piperidine-4-carboxamide [3888];
N-(6-(1H-pyrazol-4-yl)-2,7-naphthyridin-3-yl)-2-(4-(methyl-d$_3$)piperazin-1-yl)isonicotinamide [3889];
N-(6-(1-methyl-1H-pyrazol-4-yl)-2,7-naphthyridin-3-yl)-2-(4-(methyl-d$_3$)piperazin-1-yl) isonicotinamide [3890];
N-(6-(1-(methyl-d$_3$)-1H-pyrazol-4-yl)-2,7-naphthyridin-3-yl)-2-(4-methylpiperazin-1-yl) isonicotinamide [3891];
N-(6-(1-(methyl-d$_3$)-1H-pyrazol-4-yl)-2,7-naphthyridin-3-yl)-2-(4-(methyl-d$_3$)piperazin-1-yl) isonicotinamide [3892];
N-(6-(1-(methyl-d$_3$)-1H-pyrazol-4-yl)-2,7-naphthyridin-3-yl)-1-(piperidin-4-yl)-1H-pyrazole-4-carboxamide [3893];
N-(6-(1-(methyl-d$_3$)-1H-pyrazol-4-yl)-2,7-naphthyridin-3-yl)-1-(1-methylpiperidin-4-yl)-1H-pyrazole-4-carboxamide [3894];

N-(6-(1-(methyl-d₃)-1H-pyrazol-4-yl)-2,7-naphthyridin-3-yl)-2-(piperidin-4-yl)oxazole-4-carboxamide [3895];

N-(6-(1-(methyl-d₃)-1H-pyrazol-4-yl)-2,7-naphthyridin-3-yl)-2-(1-methylpiperidin-4-yl)oxazole-4-carboxamide [3896];

N-(6-(1-ethyl-1H-pyrazol-4-yl)-2,7-naphthyridin-3-yl)-2-(pyrrolidin-1-yl)acetamide [3897];

N-(6-(1-cyclopropyl-1H-pyrazol-4-yl)-2,7-naphthyridin-3-yl)-2-(pyrrolidin-1-yl)acetamide [3898];

N-(6-(1-cyclopropyl-1H-pyrazol-4-yl)-2,7-naphthyridin-3-yl)-1-(3,3,3-trifluoropropyl)piperidine-4-carboxamide [3899];

N-(6-(1-(1-methylpiperidin-4-yl)-1H-pyrazol-4-yl)-2,7-naphthyridin-3-yl) cyclohexanecarboxamide [3900];

2-(pyrrolidin-1-yl)-N-(6-(5-(trifluoromethyl)-1H-pyrazol-4-yl)-2,7-naphthyridin-3-yl)acetamide [3901];

N-(6-(5-(hydroxymethyl)-1-methyl-1H-pyrazol-4-yl)-2,7-naphthyridin-3-yl)-1-methylpiperidine-4-carboxamide [3902];

N-(6-(5-(hydroxymethyl)-1-methyl-1H-pyrazol-4-yl)-2,7-naphthyridin-3-yl)tetrahydro-2H-pyran-4-carboxamide [3903];

N-(6-(5-(azetidin-1-ylmethyl)-1-methyl-1H-pyrazol-4-yl)-2,7-naphthyridin-3-yl)-4,4-difluorocyclohexane-1-carboxamide [3904];

4,4-difluoro-N-(6-(1-methyl-5-(pyrrolidin-1-ylmethyl)-1H-pyrazol-4-yl)-2,7-naphthyridin-3-yl) cyclohexane-1-carboxamide [3905];

4,4-difluoro-N-(6-(1-methyl-5-(piperidin-1-ylmethyl)-1H-pyrazol-4-yl)-2,7-naphthyridin-3-yl) cyclohexane-1-carboxamide [3906];

2-(2-fluoroethyl)-N-(6-(1-methyl-5-(piperidin-1-ylmethyl)-1H-pyrazol-4-yl)-2,7-naphthyridin-3-yl)-2-azaspiro[3.3]heptane-6-carboxamide [3907];

tert-butyl 6-((6-(1-methyl-5-(piperidin-1-ylmethyl)-1H-pyrazol-4-yl)-2,7-naphthyridin-3-yl) carbamoyl)-2-azaspiro[3.3]heptane-2-carboxylate [3908];

2-fluoro-2-methyl-N-(6-(1-methyl-5-(piperidin-1-ylmethyl)-1H-pyrazol-4-yl)-2,7-naphthyridin-3-yl)propanamide [3909];

2-(diethylamino)-N-(6-(1-methyl-5-(piperidin-1-ylmethyl)-1H-pyrazol-4-yl)-2,7-naphthyridin-3-yl)acetamide [3910];

trans-4-methoxy-N-(6-(1-methyl-5-(piperidin-1-ylmethyl)-1H-pyrazol-4-yl)-2,7-naphthyridin-3-yl)cyclohexane-1-carboxamide [3911];

trans-4-(hydroxymethyl)-N-(6-(1-methyl-5-(piperidin-1-ylmethyl)-1H-pyrazol-4-yl)-2,7-naphthyridin-3-yl)cyclohexane-1-carboxamide [3912];

(R)—N-(6-(1-methyl-5-(piperidin-1-ylmethyl)-1H-pyrazol-4-yl)-2,7-naphthyridin-3-yl)pyrrolidine-2-carboxamide [3913];

1-isobutyl-N-(6-(1-methyl-5-(piperidin-1-ylmethyl)-1H-pyrazol-4-yl)-2,7-naphthyridin-3-yl) piperidine-4-carboxamide [3914];

N-(6-(1-methyl-5-(piperidin-1-ylmethyl)-1H-pyrazol-4-yl)-2,7-naphthyridin-3-yl)-1-(oxetan-3-yl) piperidine-4-carboxamide [3915];

1-benzoyl-N-(6-(1-methyl-5-(piperidin-1-ylmethyl)-1H-pyrazol-4-yl)-2,7-naphthyridin-3-yl) piperidine-4-carboxamide [3916];

N-(6-(1-methyl-5-(piperidin-1-ylmethyl)-1H-pyrazol-4-yl)-2,7-naphthyridin-3-yl)tetrahydro-2H-pyran-4-carboxamide [3917];

N-(6-(1-methyl-5-(piperidin-1-ylmethyl)-1H-pyrazol-4-yl)-2,7-naphthyridin-3-yl)-2-(4-methylpiperidin-1-yl)acetamide [3918];

N-(6-(1-(difluoromethyl)-1H-pyrazol-4-yl)-2,7-naphthyridin-3-yl)-2-(4-methylpiperazin-1-yl) isonicotinamide [3919];

N-(6-(1-ethyl-1H-pyrazol-4-yl)-2,7-naphthyridin-3-yl)-2-(4-methylpiperazin-1-yl) isonicotinamide [3920];

N-(6-(1-isopropyl-1H-pyrazol-4-yl)-2,7-naphthyridin-3-yl)-3-(piperidin-4-yloxy)benzamide [3921];

N-(6-(1-isopropyl-1H-pyrazol-4-yl)-2,7-naphthyridin-3-yl)-3-((1-methylpiperidin-4-yl)oxy) benzamide [3922];

N-(6-(1-isopropyl-1H-pyrazol-4-yl)-2,7-naphthyridin-3-yl)-4-(piperidin-4-yloxy)benzamide [3923];

N-(6-(1-cyclopropyl-1H-pyrazol-4-yl)-2,7-naphthyridin-3-yl)-2-(4-methylpiperazin-1-yl) isonicotinamide [3924];

4-fluoro-N-(6-(1-(1-methylpiperidin-4-yl)-1H-pyrazol-4-yl)-2,7-naphthyridin-3-yl)benzamide [3925];

4-(difluoromethoxy)-N-(6-(1-(1-methylpiperidin-4-yl)-1H-pyrazol-4-yl)-2,7-naphthyridin-3-yl) benzamide [3926];

5-fluoro-N-(6-(1-(1-methylpiperidin-4-yl)-1H-pyrazol-4-yl)-2,7-naphthyridin-3-yl)nicotinamide [3927];

$N^2$-methyl-$N^5$-(6-(1-(1-methylpiperidin-4-yl)-1H-pyrazol-4-yl)-2,7-naphthyridin-3-yl)pyridine-2,5-dicarboxamide [3928];

1-isopropyl-N-(6-(1-(1-methylpiperidin-4-yl)-1H-pyrazol-4-yl)-2,7-naphthyridin-3-yl)-1H-pyrazole-4-carboxamide [3929];

2-methyl-N-(6-(1-(1-methylpiperidin-4-yl)-1H-pyrazol-4-yl)-2,7-naphthyridin-3-yl)thiazole-5-carboxamide [3930];

N-(6-(5-amino-1-methyl-1H-pyrazol-4-yl)-2,7-naphthyridin-3-yl)-2-(4-methylpiperazin-1-yl) isonicotinamide [3931];

4-(difluoromethoxy)-N-(6-(5-(hydroxymethyl)-1-methyl-1H-pyrazol-4-yl)-2,7-naphthyridin-3-yl) benzamide [3932];

N-(6-(5-(hydroxymethyl)-1-methyl-1H-pyrazol-4-yl)-2,7-naphthyridin-3-yl)-2-(4-methylpiperazin-1-yl)isonicotinamide [3933];

N-(6-(5-(hydroxymethyl)-1-methyl-1H-pyrazol-4-yl)-2,7-naphthyridin-3-yl)-2-(7-methyl-2,7-diazaspiro[3.5]nonan-2-yl)isonicotinamide [3934];

4-fluoro-N-(6-(1-methyl-5-(pyrrolidin-1-ylmethyl)-1H-pyrazol-4-yl)-2,7-naphthyridin-3-yl) benzamide [3935];

4-fluoro-N-(6-(1-methyl-5-(piperidin-1-ylmethyl)-1H-pyrazol-4-yl)-2,7-naphthyridin-3-yl) benzamide [3936];

4-(difluoromethoxy)-N-(6-(1-methyl-5-(piperidin-1-ylmethyl)-1H-pyrazol-4-yl)-2,7-naphthyridin-3-yl)benzamide [3937];

N-(6-(1-methyl-5-(piperidin-1-ylmethyl)-1H-pyrazol-4-yl)-2,7-naphthyridin-3-yl)-3-(pyrrolidin-1-ylmethyl) benzamide [3938];

N-(6-(1-methyl-5-(piperidin-1-ylmethyl)-1H-pyrazol-4-yl)-2,7-naphthyridin-3-yl)-2-(7-methyl-2,7-diazaspiro[3.5]nonan-2-yl)isonicotinamide [3939];

N-(6-(1-methyl-5-(piperidin-1-ylmethyl)-1H-pyrazol-4-yl)-2,7-naphthyridin-3-yl)-2-morpholinoisonicotinamide [3940];

N-(6-(1-methyl-5-(morpholinomethyl)-1H-pyrazol-4-yl)-2,7-naphthyridin-3-yl)-2-morpholinoisonicotinamide [3941];

N-(6-(4,5,6,7-tetrahydropyrazolo[1,5-a]pyrazin-3-yl)-2,7-naphthyridin-3-yl)-1-((1-(trifluoromethyl)cyclopropyl)methyl)piperidine-4-carboxamide [3942];

3,3-difluoro-N-(6-(5-methyl-4,5,6,7-tetrahydropyrazolo [1,5-a]pyrazin-3-yl)-2,7-naphthyridin-3-yl)cyclobutane-1-carboxamide [3943];

4,4-difluoro-N-(6-(5-(2-fluoroethyl)-4,5,6,7-tetrahydropyrazolo[1,5-a]pyrazin-3-yl)-2,7-naphthyridin-3-yl) cyclohexane-1-carboxamide [3944];

N-(6-(5-(2-fluoroethyl)-4,5,6,7-tetrahydropyrazolo[1,5-a]pyrazin-3-yl)-2,7-naphthyridin-3-yl)-1-((1-(trifluoromethyl)cyclopropyl)methyl)piperidine-4-carboxamide [3945];

N-(6-(5-(2-fluoroethyl)-4,5,6,7-tetrahydropyrazolo[1,5-a]pyrazin-3-yl)-2,7-naphthyridin-3-yl)-2-(pyrrolidin-1-yl)acetamide [3946];

2-(7-azabicyclo[2.2.1]heptan-7-yl)-N-(6-(5-(2-fluoroethyl)-4,5,6,7-tetrahydropyrazolo[1,5-a]pyrazin-3-yl)-2,7-naphthyridin-3-yl)acetamide [3947];

(R)—N-(6-(5-(2-fluoroethyl)-4,5,6,7-tetrahydropyrazolo [1,5-a]pyrazin-3-yl)-2,7-naphthyridin-3-yl)-1-isobutylpiperidine-3-carboxamide [3948];

N-(6-(5-(2-fluoroethyl)-4,5,6,7-tetrahydropyrazolo[1,5-a]pyrazin-3-yl)-2,7-naphthyridin-3-yl) piperidine-4-carboxamide [3949];

4-fluoro-N-(6-(5-(2-fluoroethyl)-4,5,6,7-tetrahydropyrazolo[1,5-a]pyrazin-3-yl)-2,7-naphthyridin-3-yl)-1-isobutylpiperidine-4-carboxamide [3950];

N-(6-(5-(2-fluoroethyl)-4,5,6,7-tetrahydropyrazolo[1,5-a]pyrazin-3-yl)-2,7-naphthyridin-3-yl)-2-(4-methylpiperazin-1-yl)acetamide [3951];

4-fluoro-N-(6-(4,5,6,7-tetrahydropyrazolo[1,5-a]pyrazin-3-yl)-2,7-naphthyridin-3-yl)benzamide [3952];

N-(6-(5-(2-fluoroethyl)-4,5,6,7-tetrahydropyrazolo[1,5-a]pyrazin-3-yl)-2,7-naphthyridin-3-yl)-3-(4-methylpiperazin-1-yl)benzamide [3953];

$N^5$-(6-(5-(2-fluoroethyl)-4,5,6,7-tetrahydropyrazolo[1,5-a]pyrazin-3-yl)-2,7-naphthyridin-3-yl)-$N^2$-methylpyridine-2,5-dicarboxamide [3954];

N-(6-(5-(2-fluoroethyl)-4,5,6,7-tetrahydropyrazolo[1,5-a]pyrazin-3-yl)-2,7-naphthyridin-3-yl)-6-(4-methylpiperazin-1-yl)nicotinamide [3955];

2-(azetidin-3-yloxy)-N-(6-(5-(2-fluoroethyl)-4,5,6,7-tetrahydropyrazolo[1,5-a]pyrazin-3-yl)-2,7-naphthyridin-3-yl)isonicotinamide [3956];

N-(6-(1-methyl-1H-pyrazol-5-yl)-2,7-naphthyridin-3-yl)-1-(3,3,3-trifluoropropyl)piperidine-4-carboxamide [3957];

1-methyl-N-(6-(1-methyl-1H-pyrazol-3-yl)-2,7-naphthyridin-3-yl)piperidine-4-carboxamide [3958];

N-(6-(1-methyl-1H-pyrazol-3-yl)-2,7-naphthyridin-3-yl)-2-(4-methylpiperazin-1-yl) isonicotinamide [3959];

2-fluoro-2-methyl-N-(6-(1-methyl-1H-1,2,3-triazol-4-yl)-2,7-naphthyridin-3-yl)propanamide [3960];

2,2,3,3-tetramethyl-N-(6-(1-methyl-1H-1,2,3-triazol-4-yl)-2,7-naphthyridin-3-yl)cyclopropane-1-carboxamide [3961];

trans-N-(6-(1-methyl-1H-1,2,3-triazol-4-yl)-2,7-naphthyridin-3-yl)-4-(pyrrolidin-1-yl) cyclohexane-1-carboxamide [3962];

trans-N-(6-(1-methyl-1H-1,2,3-triazol-4-yl)-2,7-naphthyridin-3-yl)-4-morpholinocyclohexane-1-carboxamide [3963];

N-(6-(1-methyl-1H-1,2,3-triazol-4-yl)-2,7-naphthyridin-3-yl)-2-(piperidin-1-yl)acetamide [3964];

1-ethyl-4-fluoro-N-(6-(1-methyl-1H-1,2,3-triazol-4-yl)-2,7-naphthyridin-3-yl)piperidine-4-carboxamide [3965];

4-fluoro-1-isobutyl-N-(6-(1-methyl-1H-1,2,3-triazol-4-yl)-2,7-naphthyridin-3-yl)piperidine-4-carboxamide [3966];

N-(6-(1-methyl-1H-1,2,3-triazol-4-yl)-2,7-naphthyridin-3-yl)-1-(3,3,3-trifluoropropyl)piperidine-4-carboxamide [3967];

N-(6-(1-methyl-1H-1,2,3-triazol-4-yl)-2,7-naphthyridin-3-yl)cyclopropanecarboxamide [3968];

4,4-difluoro-N-(6-(1-methyl-1H-1,2,3-triazol-4-yl)-2,7-naphthyridin-3-yl)cyclohexane-1-carboxamide [3969];

trans-4-(dimethylamino)-N-(6-(1-methyl-1H-1,2,3-triazol-4-yl)-2,7-naphthyridin-3-yl) cyclohexane-1-carboxamide [3970];

trans-N-(6-(1-methyl-1H-1,2,3-triazol-4-yl)-2,7-naphthyridin-3-yl)-4-((4-methylpiperazin-1-yl) methyl)cyclohexane-1-carboxamide [3971];

N-(6-(1-methyl-1H-1,2,3-triazol-4-yl)-2,7-naphthyridin-3-yl)piperidine-4-carboxamide [3972];

1-isobutyl-N-(6-(1-methyl-1H-1,2,3-triazol-4-yl)-2,7-naphthyridin-3-yl)piperidine-4-carboxamide [3973];

N-(6-(1-methyl-1H-1,2,3-triazol-4-yl)-2,7-naphthyridin-3-yl)-1-((1-(trifluoromethyl)cyclopropyl) methyl)piperidine-4-carboxamide [3974];

N-(6-(1-methyl-1H-1,2,3-triazol-4-yl)-2,7-naphthyridin-3-yl)-1-((3-methyloxetan-3-yl)methyl) piperidine-4-carboxamide [3975];

N-(6-(1-methyl-1H-1,2,3-triazol-4-yl)-2,7-naphthyridin-3-yl)-1-(2-(pyrrolidin-1-yl)acetyl) piperidine-4-carboxamide [3976];

1'-methyl-N-(6-(1-methyl-1H-1,2,3-triazol-4-yl)-2,7-naphthyridin-3-yl)-[1,4'-bipiperidine]-4-carboxamide [3977];

(R)—N-(6-(1-methyl-1H-1,2,3-triazol-4-yl)-2,7-naphthyridin-3-yl)piperidine-3-carboxamide [3978];

(R)-1-isobutyl-N-(6-(1-methyl-1H-1,2,3-triazol-4-yl)-2,7-naphthyridin-3-yl)piperidine-3-carboxamide [3979];

N-(6-(1-methyl-1H-1,2,3-triazol-4-yl)-2,7-naphthyridin-3-yl)-2-(pyrrolidin-1-yl)acetamide [3980];

N-(6-(1-methyl-1H-1,2,3-triazol-4-yl)-2,7-naphthyridin-3-yl)-2-(4-methylpiperazin-1-yl) acetamide [3981];

2-(7-azabicyclo[2.2.1]heptan-7-yl)-N-(6-(1-methyl-1H-1,2,3-triazol-4-yl)-2,7-naphthyridin-3-yl) acetamide [3982];

1-(2-hydroxy-2-methylpropyl)-N-(6-(1-methyl-1H-1,2,3-triazol-4-yl)-2,7-naphthyridin-3-yl) piperidine-4-carboxamide [3983];

N-(6-(1-methyl-1H-1,2,3-triazol-4-yl)-2,7-naphthyridin-3-yl)-2-morpholinoacetamide [3984];

2-(4-methoxypiperidin-1-yl)-N-(6-(1-methyl-1H-1,2,3-triazol-4-yl)-2,7-naphthyridin-3-yl) acetamide [3985];

N-(6-(1-methyl-1H-1,2,3-triazol-4-yl)-2,7-naphthyridin-3-yl)morpholine-4-carboxamide [3986];

N-(6-(1-methyl-1H-1,2,3-triazol-4-yl)-2,7-naphthyridin-3-yl)-1-(piperidin-4-yl)-1H-pyrazole-4-carboxamide [3987];

N-(6-(1-methyl-1H-1,2,3-triazol-4-yl)-2,7-naphthyridin-3-yl)-1-(1-methylpiperidin-4-yl)-1H-pyrazole-4-carboxamide [3988];

1-(1-ethylpiperidin-4-yl)-N-(6-(1-methyl-1H-1,2,3-triazol-4-yl)-2,7-naphthyridin-3-yl)-1H-pyrazole-4-carboxamide [3989];

1-(1-isopropylpiperidin-4-yl)-N-(6-(1-methyl-1H-1,2,3-triazol-4-yl)-2,7-naphthyridin-3-yl)-1H-pyrazole-4-carboxamide [3990];

N-(6-(1-methyl-1H-1,2,3-triazol-4-yl)-2,7-naphthyridin-3-yl)-1-(piperidin-4-yl)-1H-1,2,3-triazole-4-carboxamide [3991];

1-(1-(2-fluoroethyl)piperidin-4-yl)-N-(6-(1-methyl-1H-1,2,3-triazol-4-yl)-2,7-naphthyridin-3-yl)-1H-1,2,3-triazole-4-carboxamide [3992];
1-(1-isopropylpiperidin-4-yl)-N-(6-(1-methyl-1H-1,2,3-triazol-4-yl)-2,7-naphthyridin-3-yl)-1H-1,2,3-triazole-4-carboxamide [3993];
N-(6-(1-methyl-1H-1,2,3-triazol-4-yl)-2,7-naphthyridin-3-yl)-2-(piperidin-4-yl)oxazole-4-carboxamide [3994];
N-(6-(1-methyl-1H-1,2,3-triazol-4-yl)-2,7-naphthyridin-3-yl)-2-(1-methylpiperidin-4-yl)oxazole-4-carboxamide [3995];
2-(1-isopropylpiperidin-4-yl)-N-(6-(1-methyl-1H-1,2,3-triazol-4-yl)-2,7-naphthyridin-3-yl) oxazole-4-carboxamide [3996];
2-fluoro-N-(6-(1-methyl-1H-1,2,3-triazol-4-yl)-2,7-naphthyridin-3-yl)benzamide [3997];
N-(6-(1-methyl-1H-1,2,3-triazol-4-yl)-2,7-naphthyridin-3-yl)-3-((1-methylpiperidin-4-yl)oxy) benzamide [3998];
$N^2$-methyl-$N^5$-(6-(1-methyl-1H-1,2,3-triazol-4-yl)-2,7-naphthyridin-3-yl)pyridine-2,5-dicarboxamide [3999];
N-(6-(1-methyl-1H-1,2,3-triazol-4-yl)-2,7-naphthyridin-3-yl)-6-(4-methylpiperazin-1-yl) nicotinamide [4000];
2-(3-(dimethylamino)azetidin-1-yl)-N-(6-(1-methyl-1H-1,2,3-triazol-4-yl)-2,7-naphthyridin-3-yl) isonicotinamide [4001];
N-(6-(1-methyl-1H-1,2,3-triazol-4-yl)-2,7-naphthyridin-3-yl)-2-(1-methylpiperidin-4-yl) isonicotinamide [4002];
2-(4-(dimethylamino)piperidin-1-yl)-N-(6-(1-methyl-1H-1,2,3-triazol-4-yl)-2,7-naphthyridin-3-yl)isonicotinamide [4003];
N-(6-(1-methyl-1H-1,2,3-triazol-4-yl)-2,7-naphthyridin-3-yl)-2-morpholinoisonicotinamide [4004];
N-(6-(1-methyl-1H-1,2,3-triazol-4-yl)-2,7-naphthyridin-3-yl)-2-(4-methylpiperazin-1-yl) isonicotinamide [4005];
2-(4-methyl-1,4-diazepan-1-yl)-N-(6-(1-methyl-1H-1,2,3-triazol-4-yl)-2,7-naphthyridin-3-yl) isonicotinamide [4006];
2-(4-isopropylpiperazin-1-yl)-N-(6-(1-methyl-1H-1,2,3-triazol-4-yl)-2,7-naphthyridin-3-yl) isonicotinamide [4007];
N-(6-(1-methyl-1H-1,2,3-triazol-4-yl)-2,7-naphthyridin-3-yl)-2-(piperidin-4-ylamino) isonicotinamide [4008];
2-(methyl(1-methylpiperidin-4-yl)amino)-N-(6-(1-methyl-1H-1,2,3-triazol-4-yl)-2,7-naphthyridin-3-yl) isonicotinamide [4009];
N-(6-(1-methyl-1H-1,2,3-triazol-4-yl)-2,7-naphthyridin-3-yl)-2-((1-methylpiperidin-4-yl)thio) isonicotinamide [4010];
2-methyl-N-(6-(1-methyl-1H-1,2,3-triazol-4-yl)-2,7-naphthyridin-3-yl)-1,2,3,4-tetrahydroisoquinoline-6-carboxamide [4011];
N-(6-(1-methyl-1H-1,2,3-triazol-4-yl)-2,7-naphthyridin-3-yl)-2-(piperazin-1-yl)isonicotinamide [4012];
N-(6-(1-methyl-1H-1,2,3-triazol-4-yl)-2,7-naphthyridin-3-yl)-2-(2-(4-methylpiperazin-1-yl) pyridin-4-yl)acetamide [4013];
1,1-bis(methyl-$d_3$)-4-(4-((6-(1-methyl-1H-1,2,3-triazol-4-yl)-2,7-naphthyridin-3-yl)carbamoyl) pyridin-2-yl)piperazin-1-ium iodide [4014];
N-(6-(1-methyl-1H-1,2,3-triazol-4-yl)-2,7-naphthyridin-3-yl)-2-(4-(methyl-$d_3$)piperazin-1-yl) isonicotinamide [4015];
N-(6-(1-methyl-1H-1,2,3-triazol-5-yl)-2,7-naphthyridin-3-yl)-1-(3,3,3-trifluoropropyl)piperidine-4-carboxamide [4016];
N-(6-(4-methyl-4H-1,2,4-triazol-3-yl)-2,7-naphthyridin-3-yl)-2-morpholinoacetamide [4017];
N-(6-(4-methyl-4H-1,2,4-triazol-3-yl)-2,7-naphthyridin-3-yl)-1-(3,3,3-trifluoropropyl)piperidine-4-carboxamide [4018];
4-fluoro-1-isobutyl-N-(6-(4-methyl-4H-1,2,4-triazol-3-yl)-2,7-naphthyridin-3-yl)piperidine-4-carboxamide [4019];
N-(6-(4,5-dimethyl-4H-1,2,4-triazol-3-yl)-2,7-naphthyridin-3-yl)-2-morpholinoacetamide [4020];
N-(6-(4,5-dimethyl-4H-1,2,4-triazol-3-yl)-2,7-naphthyridin-3-yl)-1-(3,3,3-trifluoropropyl) piperidine-4-carboxamide [4021];
N-(6-(1H-1,2,3-triazol-1-yl)-2,7-naphthyridin-3-yl)-4-fluoro-1-isobutylpiperidine-4-carboxamide [4022];
N-(6-(2H-1,2,3-triazol-2-yl)-2,7-naphthyridin-3-yl)-4-fluoro-1-isobutylpiperidine-4-carboxamide [4023];
N-(6-(1H-1,2,4-triazol-1-yl)-2,7-naphthyridin-3-yl)-2-(4-methylpiperazin-1-yl)isonicotinamide [4024];
1-isobutyl-N-(6-(1-methyl-1H-tetrazol-5-yl)-2,7-naphthyridin-3-yl)piperidine-4-carboxamide [4025];
2,2,3,3-tetramethyl-N-(6-(1-methyl-1H-imidazol-5-yl)-2,7-naphthyridin-3-yl)cyclopropane-1-carboxamide [4026];
4,4-difluoro-N-(6-(1-methyl-1H-imidazol-5-yl)-2,7-naphthyridin-3-yl)cyclohexane-1-carboxamide [4027];
N-(6-(1-methyl-1H-imidazol-5-yl)-2,7-naphthyridin-3-yl)-2-(piperidin-1-yl)acetamide [4028];
2-fluoro-2-methyl-N-(6-(1-methyl-1H-imidazol-5-yl)-2,7-naphthyridin-3-yl)propanamide [4029];
1-fluoro-N-(6-(1-methyl-1H-imidazol-5-yl)-2,7-naphthyridin-3-yl)cyclopropane-1-carboxamide [4030];
2-methyl-N-(6-(1-methyl-1H-imidazol-5-yl)-2,7-naphthyridin-3-yl)-2-azaspiro[3.3]heptane-6-carboxamide [4031];
1-fluoro-N-(6-(1-methyl-1H-imidazol-5-yl)-2,7-naphthyridin-3-yl)cyclohexane-1-carboxamide [4032];
trans-4-methoxy-N-(6-(1-methyl-1H-imidazol-5-yl)-2,7-naphthyridin-3-yl)cyclohexane-1-carboxamide [4033];
trans-4-(hydroxymethyl)-N-(6-(1-methyl-1H-imidazol-5-yl)-2,7-naphthyridin-3-yl)cyclohexane-1-carboxamide [4034];
N-(6-(1-methyl-1H-imidazol-5-yl)-2,7-naphthyridin-3-yl)azetidine-3-carboxamide [4035];
(R)—N-(6-(1-methyl-1H-imidazol-5-yl)-2,7-naphthyridin-3-yl)tetrahydrofuran-2-carboxamide [4036];
1-(2-methoxyethyl)-N-(6-(1-methyl-1H-imidazol-5-yl)-2,7-naphthyridin-3-yl)piperidine-4-carboxamide [4037];
N-(6-(1-methyl-1H-imidazol-5-yl)-2,7-naphthyridin-3-yl)-1-(3,3,3-trifluoropropyl)piperidine-4-carboxamide [4038];
1-isobutyl-N-(6-(1-methyl-1H-imidazol-5-yl)-2,7-naphthyridin-3-yl)piperidine-4-carboxamide [4039];
N-(6-(1-methyl-1H-imidazol-5-yl)-2,7-naphthyridin-3-yl)-1-(methylsulfonyl)piperidine-4-carboxamide [4040];
N-(6-(1-methyl-1H-imidazol-5-yl)-2,7-naphthyridin-3-yl)-2-(pyrrolidin-1-yl)propanamide [4041];
2-isopropoxy-N-(6-(1-methyl-1H-imidazol-5-yl)-2,7-naphthyridin-3-yl)acetamide [4042];
3-isopropoxy-N-(6-(1-methyl-1H-imidazol-5-yl)-2,7-naphthyridin-3-yl)propanamide [4043];

N-(6-(1,2-dimethyl-1H-imidazol-5-yl)-2,7-naphthyridin-3-yl)cyclopropanecarboxamide [4044];
N-(6-(1,2-dimethyl-1H-imidazol-5-yl)-2,7-naphthyridin-3-yl)cyclohexanecarboxamide [4045];
N-(6-(1,2-dimethyl-1H-imidazol-5-yl)-2,7-naphthyridin-3-yl)-4,4-difluorocyclohexane-1-carboxamide [4046];
(S)—N-(6-(1,2-dimethyl-1H-imidazol-5-yl)-2,7-naphthyridin-3-yl)tetrahydrofuran-2-carboxamide [4047];
N-(6-(1,2-dimethyl-1H-imidazol-5-yl)-2,7-naphthyridin-3-yl)-3,3-difluorocyclobutane-1-carboxamide [4048];
N-(6-(1,2-dimethyl-1H-imidazol-5-yl)-2,7-naphthyridin-3-yl)-1-fluorocyclopropane-1-carboxamide [4049];
N-(6-(1,2-dimethyl-1H-imidazol-5-yl)-2,7-naphthyridin-3-yl)morpholine-4-carboxamide [4050];
N-(6-(1,2-dimethyl-1H-imidazol-5-yl)-2,7-naphthyridin-3-yl)morpholine-$d_8$-4-carboxamide [4051];
1-methyl-N-(6-(1-methyl-1H-imidazol-5-yl)-2,7-naphthyridin-3-yl)-1H-pyrazole-4-carboxamide [4052];
1-ethyl-N-(6-(1-methyl-1H-imidazol-5-yl)-2,7-naphthyridin-3-yl)-1H-pyrazole-4-carboxamide [4053];
1-isopropyl-N-(6-(1-methyl-1H-imidazol-5-yl)-2,7-naphthyridin-3-yl)-1H-pyrazole-4-carboxamide [4054];
1-cyclopropyl-N-(6-(1-methyl-1H-imidazol-5-yl)-2,7-naphthyridin-3-yl)-1H-pyrazole-4-carboxamide [4055];
1-isobutyl-N-(6-(1-methyl-1H-imidazol-5-yl)-2,7-naphthyridin-3-yl)-1H-pyrazole-4-carboxamide [4056];
1-methyl-N-(6-(1-methyl-1H-imidazol-5-yl)-2,7-naphthyridin-3-yl)-1H-pyrazole-3-carboxamide [4057];
N-(6-(1-methyl-1H-imidazol-5-yl)-2,7-naphthyridin-3-yl)-2-(1-methyl-1H-pyrazol-4-yl) acetamide [4058];
1-methyl-N-(6-(1-methyl-1H-imidazol-5-yl)-2,7-naphthyridin-3-yl)-1H-imidazole-4-carboxamide [4059];
1-isopropyl-N-(6-(1-methyl-1H-imidazol-5-yl)-2,7-naphthyridin-3-yl)-1H-imidazole-4-carboxamide [4060];
N-(6-(1-methyl-1H-imidazol-5-yl)-2,7-naphthyridin-3-yl)-1-(tetrahydro-2H-pyran-4-yl)-1H-imidazole-4-carboxamide [4061];
1,2-dimethyl-N-(6-(1-methyl-1H-imidazol-5-yl)-2,7-naphthyridin-3-yl)-1H-imidazole-5-carboxamide [4062];
1-methyl-N-(6-(1-methyl-1H-imidazol-5-yl)-2,7-naphthyridin-3-yl)-1H-1,2,4-triazole-3-carboxamide [4063];
2-methyl-N-(6-(1-methyl-1H-imidazol-5-yl)-2,7-naphthyridin-3-yl)oxazole-4-carboxamide [4064];
2-isopropyl-N-(6-(1-methyl-1H-imidazol-5-yl)-2,7-naphthyridin-3-yl)oxazole-4-carboxamide [4065];
4-methyl-N-(6-(1-methyl-1H-imidazol-5-yl)-2,7-naphthyridin-3-yl)oxazole-2-carboxamide [4066];
4-methyl-N-(6-(1-methyl-1H-imidazol-5-yl)-2,7-naphthyridin-3-yl)thiazole-2-carboxamide [4067];
2-methyl-N-(6-(1-methyl-1H-imidazol-5-yl)-2,7-naphthyridin-3-yl)thiazole-4-carboxamide [4068];
5-methyl-N-(6-(1-methyl-1H-imidazol-5-yl)-2,7-naphthyridin-3-yl)-1,3,4-oxadiazole-2-carboxamide [4069];
5-methyl-N-(6-(1-methyl-1H-imidazol-5-yl)-2,7-naphthyridin-3-yl)-1,3,4-thiadiazole-2-carboxamide [4070];
1-isopropyl-N-(6-(1-isopropyl-1H-imidazol-5-yl)-2,7-naphthyridin-3-yl)-1H-pyrazole-4-carboxamide [4071];
N-(6-(1,2-dimethyl-1H-imidazol-5-yl)-2,7-naphthyridin-3-yl)-1-methyl-1H-pyrazole-4-carboxamide [4072];
N-(6-(1,2-dimethyl-1H-imidazol-5-yl)-2,7-naphthyridin-3-yl)-1-isopropyl-1H-pyrazole-4-carboxamide [4073];
N-(6-(1,2-dimethyl-1H-imidazol-5-yl)-2,7-naphthyridin-3-yl)-2-methylthiazole-5-carboxamide [4074];
4-fluoro-N-(6-(1-methyl-1H-imidazol-5-yl)-2,7-naphthyridin-3-yl)benzamide [4075];
4-(difluoromethoxy)-N-(6-(1-methyl-1H-imidazol-5-yl)-2,7-naphthyridin-3-yl)benzamide [4076];
N-(6-(1-methyl-1H-imidazol-5-yl)-2,7-naphthyridin-3-yl)-3-(pyrrolidin-1-ylmethyl)benzamide [4077];
2-fluoro-N-(6-(1-methyl-1H-imidazol-5-yl)-2,7-naphthyridin-3-yl)benzamide-3,4,5,6-$d_4$ [4078];
4-fluoro-N-(6-(1-methyl-1H-imidazol-5-yl)-2,7-naphthyridin-3-yl)benzamide-2,3,5,6-$d_4$ [4079];
2-chloro-N-(6-(1-methyl-1H-imidazol-5-yl)-2,7-naphthyridin-3-yl)benzamide-3,4,5,6-$d_4$ [4080];
4-chloro-N-(6-(1-methyl-1H-imidazol-5-yl)-2,7-naphthyridin-3-yl)benzamide-2,3,5,6-$d_4$ [4081];
4-(methyl-$d_3$)—N-(6-(1-methyl-1H-imidazol-5-yl)-2,7-naphthyridin-3-yl)benzamide [4082];
4-methyl-N-(6-(1-methyl-1H-imidazol-5-yl)-2,7-naphthyridin-3-yl)benzamide-2,3,5,6-$d_4$ [4083];
4-(methyl-$d_3$)—N-(6-(1-methyl-1H-imidazol-5-yl)-2,7-naphthyridin-3-yl)benzamide-2,3,5,6-$d_4$ [4084];
4-(methoxy-$d_3$)—N-(6-(1-methyl-1H-imidazol-5-yl)-2,7-naphthyridin-3-yl)benzamide [4085];
4-(methoxy-$d_3$)—N-(6-(1-methyl-1H-imidazol-5-yl)-2,7-naphthyridin-3-yl)benzamide-2,3,5,6-$d_4$ [4086];
4-methoxy-N-(6-(1-methyl-1H-imidazol-5-yl)-2,7-naphthyridin-3-yl)benzamide-2,3,5,6-$d_4$ [4087];
(E)-N-(6-(1,2-dimethyl-1H-imidazol-5-yl)-2,7-naphthyridin-3-yl)-3-(phenyl-2,3,4,5,6-$d_5$) acrylamide [4088];
(E)-N-(6-(1,2-dimethyl-1H-imidazol-5-yl)-2,7-naphthyridin-3-yl)-3-(phenyl-2,3,4,5,6-$d_5$) acrylamide-2,3-$d_2$ [4089];
N-(6-(1,2-dimethyl-1H-imidazol-5-yl)-2,7-naphthyridin-3-yl)-2-(4-fluorophenyl)acetamide-2,2-$d_2$ [4090];
(E)-N-(6-(1-methyl-1H-imidazol-5-yl)-2,7-naphthyridin-3-yl)-3-(phenyl-2,3,4,5,6-$d_5$)acrylamide [4091];
(E)-N-(6-(1-methyl-1H-imidazol-5-yl)-2,7-naphthyridin-3-yl)-3-(phenyl-2,3,4,5,6-$d_5$)acrylamide-2,3-$d_2$ [4092];
2-(4-fluorophenyl)-N-(6-(1-methyl-1H-imidazol-5-yl)-2,7-naphthyridin-3-yl)acetamide-2,2-$d_2$ [4093];
N-(6-(1-methyl-1H-imidazol-5-yl)-2,7-naphthyridin-3-yl)-2-(4-methylpiperazin-1-yl) isonicotinamide [4094];
2-(dimethylamino)-N-(6-(1-methyl-1H-imidazol-5-yl)-2,7-naphthyridin-3-yl)isonicotinamide [4095];
2-(3-aminoazetidin-1-yl)-N-(6-(1-methyl-1H-imidazol-5-yl)-2,7-naphthyridin-3-yl) isonicotinamide [4096];
N-(6-(1-methyl-1H-imidazol-5-yl)-2,7-naphthyridin-3-yl)-2-(pyrrolidin-1-yl)isonicotinamide [4097];
N-(6-(1-methyl-1H-imidazol-5-yl)-2,7-naphthyridin-3-yl)-2-(piperidin-1-yl)isonicotinamide [4098];
N-(6-(1-methyl-1H-imidazol-5-yl)-2,7-naphthyridin-3-yl)-2-morpholinoisonicotinamide [4099];
2-(4-isopropylpiperazin-1-yl)-N-(6-(1-methyl-1H-imidazol-5-yl)-2,7-naphthyridin-3-yl) isonicotinamide [4100];
2-(4-cyclopropylpiperazin-1-yl)-N-(6-(1-methyl-1H-imidazol-5-yl)-2,7-naphthyridin-3-yl) isonicotinamide [4101];
N-(6-(1-methyl-1H-imidazol-5-yl)-2,7-naphthyridin-3-yl)-2-(2,7-diazaspiro[3.5]nonan-2-yl) isonicotinamide [4102];
N-(6-(1-methyl-1H-imidazol-5-yl)-2,7-naphthyridin-3-yl)-2-(7-methyl-2,7-diazaspiro[3.5]nonan-2-yl)isonicotinamide [4103];
N-(6-(1-methyl-1H-imidazol-5-yl)-2,7-naphthyridin-3-yl)isoindoline-5-carboxamide [4104];
2-methyl-N-(6-(1-methyl-1H-imidazol-5-yl)-2,7-naphthyridin-3-yl)isoindoline-5-carboxamide [4105];

2-(azetidin-1-yl)-N-(6-(1-methyl-1H-imidazol-5-yl)-2,7-naphthyridin-3-yl)isonicotinamide [4106];
2-methoxy-N-(6-(1-methyl-1H-imidazol-5-yl)-2,7-naphthyridin-3-yl)isonicotinamide [4107];
2-methyl-N-(6-(1-methyl-1H-imidazol-5-yl)-2,7-naphthyridin-3-yl)isonicotinamide [4108];
2-cyano-N-(6-(1-methyl-1H-imidazol-5-yl)-2,7-naphthyridin-3-yl)isonicotinamide [4109];
2-(3,3-difluoroazetidin-1-yl)-N-(6-(1-methyl-1H-imidazol-5-yl)-2,7-naphthyridin-3-yl) isonicotinamide [4110];
2-(4,4-difluoropiperidin-1-yl)-N-(6-(1-methyl-1H-imidazol-5-yl)-2,7-naphthyridin-3-yl) isonicotinamide [4111];
2-isopropoxy-N-(6-(1-methyl-1H-imidazol-5-yl)-2,7-naphthyridin-3-yl)isonicotinamide [4112];
N-(6-(1-methyl-1H-imidazol-5-yl)-2,7-naphthyridin-3-yl)-2-(pyrrolidin-1-yl-2,2,5,5-$d_4$) isonicotinamide [4113];
N-(6-(1-methyl-1H-imidazol-5-yl)-2,7-naphthyridin-3-yl)-2-(pyrrolidin-1-yl-$d_8$)isonicotinamide [4114];
N-(6-(1-methyl-1H-imidazol-5-yl)-2,7-naphthyridin-3-yl)-2-(piperidin-1-yl-$d_{10}$)isonicotinamide [4115];
N-(6-(1-methyl-1H-imidazol-5-yl)-2,7-naphthyridin-3-yl)-2-(morpholino-$d_8$)isonicotinamide [4116];
N-(6-(1,2-dimethyl-1H-imidazol-5-yl)-2,7-naphthyridin-3-yl)-4-isopropoxybenzamide [4117];
N-(6-(1,2-dimethyl-1H-imidazol-5-yl)-2,7-naphthyridin-3-yl)-4-(piperidin-4-yloxy)benzamide [4118];
4-(benzyloxy)-N-(6-(1,2-dimethyl-1H-imidazol-5-yl)-2,7-naphthyridin-3-yl)benzamide [4119];
N-(6-(1,2-dimethyl-1H-imidazol-5-yl)-2,7-naphthyridin-3-yl)-2-fluorobenzamide-3,4,5,6-$d_4$ [4120];
N-(6-(1,2-dimethyl-1H-imidazol-5-yl)-2,7-naphthyridin-3-yl)-4-fluorobenzamide-2,3,5,6-$d_4$ [4121];
2-chloro-N-(6-(1,2-dimethyl-1H-imidazol-5-yl)-2,7-naphthyridin-3-yl)benzamide-3,4,5,6-$d_4$ [4122];
4-chloro-N-(6-(1,2-dimethyl-1H-imidazol-5-yl)-2,7-naphthyridin-3-yl)benzamide-2,3,5,6-$d_4$ [4123];
N-(6-(1,2-dimethyl-1H-imidazol-5-yl)-2,7-naphthyridin-3-yl)-4-(methyl-$d_3$)benzamide [4124];
N-(6-(1,2-dimethyl-1H-imidazol-5-yl)-2,7-naphthyridin-3-yl)-4-methylbenzamide-2,3,5,6-$d_4$ [4125];
N-(6-(1,2-dimethyl-1H-imidazol-5-yl)-2,7-naphthyridin-3-yl)-4-(methyl-$d_3$)benzamide-2,3,5,6-$d_4$ [4126];
N-(6-(1,2-dimethyl-1H-imidazol-5-yl)-2,7-naphthyridin-3-yl)-4-(methoxy-$d_3$)benzamide [4127];
N-(6-(1,2-dimethyl-1H-imidazol-5-yl)-2,7-naphthyridin-3-yl)-4-(methoxy-$d_3$)benzamide-2,3,5,6-$d_4$ [4128];
N-(6-(1,2-dimethyl-1H-imidazol-5-yl)-2,7-naphthyridin-3-yl)-4-methoxybenzamide-2,3,5,6-$d_4$ [4129];
N-(6-(1,2-dimethyl-1H-imidazol-5-yl)-2,7-naphthyridin-3-yl)-2-(4-methylpiperazin-1-yl) isonicotinamide [4130];
N-(6-(1,2-dimethyl-1H-imidazol-5-yl)-2,7-naphthyridin-3-yl)-2-morpholinoisonicotinamide [4131];
N-(6-(1,2-dimethyl-1H-imidazol-5-yl)-2,7-naphthyridin-3-yl)-2-(pyrrolidin-1-yl)isonicotinamide [4132];
N-(6-(1,2-dimethyl-1H-imidazol-5-yl)-2,7-naphthyridin-3-yl)-2-(dimethylamino)isonicotinamide [4133];
N-(6-(1,2-dimethyl-1H-imidazol-5-yl)-2,7-naphthyridin-3-yl)-2-(pyrrolidin-1-yl-2,2,5,5-$d_4$) isonicotinamide [4134];
N-(6-(1,2-dimethyl-1H-imidazol-5-yl)-2,7-naphthyridin-3-yl)-2-(pyrrolidin-1-yl-$d_8$) isonicotinamide [4135];
N-(6-(1,2-dimethyl-1H-imidazol-5-yl)-2,7-naphthyridin-3-yl)-2-(piperidin-1-yl-$d_{10}$) isonicotinamide [4136];
N-(6-(1,2-dimethyl-1H-imidazol-5-yl)-2,7-naphthyridin-3-yl)-2-(morpholino-$d_8$)isonicotinamide [4137];
N-(6-(5,6,7,8-tetrahydroimidazo[1,2-a]pyrazin-3-yl)-2,7-naphthyridin-3-yl) cyclopropanecarboxamide [4138];
N-(6-(7-methyl-5,6,7,8-tetrahydroimidazo[1,2-a]pyrazin-3-yl)-2,7-naphthyridin-3-yl) cyclopropanecarboxamide [4139];
3,3-difluoro-N-(6-(5,6,7,8-tetrahydroimidazo[1,2-a]pyrazin-3-yl)-2,7-naphthyridin-3-yl) cyclobutane-1-carboxamide [4140];
(R)—N-(6-(5,6,7,8-tetrahydroimidazo[1,2-a]pyrazin-3-yl)-2,7-naphthyridin-3-yl)pyrrolidine-2-carboxamide [4141];
(R)—N-(6-(5,6,7,8-tetrahydroimidazo[1,2-a]pyrazin-3-yl)-2,7-naphthyridin-3-yl)piperidine-3-carboxamide [4142];
1-methyl-N-(6-(5,6,7,8-tetrahydroimidazo[1,2-a]pyrazin-3-yl)-2,7-naphthyridin-3-yl)piperidine-4-carboxamide [4143];
N-(6-(5,6,7,8-tetrahydroimidazo[1,2-a]pyrazin-3-yl)-2,7-naphthyridin-3-yl)-1-((1-(trifluoromethyl)cyclopropyl)methyl)piperidine-4-carboxamide [4144];
1-benzoyl-N-(6-(5,6,7,8-tetrahydroimidazo[1,2-a]pyrazin-3-yl)-2,7-naphthyridin-3-yl)piperidine-4-carboxamide [4145];
4-fluoro-1-isobutyl-N-(6-(5,6,7,8-tetrahydroimidazo[1,2-a]pyrazin-3-yl)-2,7-naphthyridin-3-yl) piperidine-4-carboxamide [4146];
(R)-2-(2-methylpyrrolidin-1-yl)-N-(6-(5,6,7,8-tetrahydroimidazo[1,2-a]pyrazin-3-yl)-2,7-naphthyridin-3-yl) acetamide [4147];
2-(cyclobutyl(methyl)amino)-N-(6-(5,6,7,8-tetrahydroimidazo[1,2-a]pyrazin-3-yl)-2,7-naphthyridin-3-yl) acetamide [4148];
4-fluoro-N-(6-(5,6,7,8-tetrahydroimidazo[1,2-a]pyrazin-3-yl)-2,7-naphthyridin-3-yl)benzamide [4149];
4-isopropoxy-N-(6-(5,6,7,8-tetrahydroimidazo[1,2-a]pyrazin-3-yl)-2,7-naphthyridin-3-yl) benzamide [4150];
4-(difluoromethoxy)-N-(6-(5,6,7,8-tetrahydroimidazo[1,2-a]pyrazin-3-yl)-2,7-naphthyridin-3-yl) benzamide [4151];
2-((2-(dimethylamino)ethyl)amino)-N-(6-(5,6,7,8-tetrahydroimidazo[1,2-a]pyrazin-3-yl)-2,7-naphthyridin-3-yl)isonicotinamide [4152];
2-((1-isopropylpiperidin-4-yl)oxy)-N-(6-(5,6,7,8-tetrahydroimidazo[1,2-a]pyrazin-3-yl)-2,7-naphthyridin-3-yl) isonicotinamide [4153];
N-(6-(oxazol-5-yl)-2,7-naphthyridin-3-yl)-1-(3,3,3-trifluoropropyl)piperidine-4-carboxamide [4154];
N-(6-(oxazol-5-yl)-2,7-naphthyridin-3-yl)cyclopropanecarboxamide [4155];
(R)—N-(6-(oxazol-5-yl)-2,7-naphthyridin-3-yl)tetrahydrofuran-2-carboxamide [4156];
(R)—N-(6-(oxazol-5-yl)-2,7-naphthyridin-3-yl)piperidine-3-carboxamide [4157];
N-(6-(oxazol-5-yl)-2,7-naphthyridin-3-yl)tetrahydro-2H-pyran-4-carboxamide [4158];
N-(6-(oxazol-5-yl)-2,7-naphthyridin-3-yl)-1-(2-(pyrrolidin-1-yl)acetyl)piperidine-4-carboxamide [4159];
1'-methyl-N-(6-(oxazol-5-yl)-2,7-naphthyridin-3-yl)-[1,4'-bipiperidine]-4-carboxamide [4160];
cis-4-morpholino-N-(6-(oxazol-5-yl)-2,7-naphthyridin-3-yl)cyclohexane-1-carboxamide [4161];
2-(cyclobutyl(methyl)amino)-N-(6-(oxazol-5-yl)-2,7-naphthyridin-3-yl)acetamide [4162];

N-(6-(oxazol-5-yl)-2,7-naphthyridin-3-yl)-2-(pyrrolidin-1-yl)acetamide [4163];
(R)-2-(2-methylpyrrolidin-1-yl)-N-(6-(oxazol-5-yl)-2,7-naphthyridin-3-yl)acetamide [4164];
2-(4-methylpiperazin-1-yl)-N-(6-(oxazol-5-yl)-2,7-naphthyridin-3-yl)acetamide [4165];
trans-4-((4-methylpiperazin-1-yl)methyl)-N-(6-(oxazol-5-yl)-2,7-naphthyridin-3-yl)cyclohexane-1-carboxamide [4166];
1-(2,2-difluoropropyl)-N-(6-(oxazol-5-yl)-2,7-naphthyridin-3-yl)piperidine-4-carboxamide [4167];
trans-4-(hydroxymethyl)-N-(6-(2-methyloxazol-5-yl)-2,7-naphthyridin-3-yl)cyclohexane-1-carboxamide [4168];
trans-4-(methylamino)-N-(6-(2-methyloxazol-5-yl)-2,7-naphthyridin-3-yl)cyclohexane-1-carboxamide [4169];
trans-4-((1,3-difluoropropan-2-yl)amino)-N-(6-(2-methyloxazol-5-yl)-2,7-naphthyridin-3-yl) cyclohexane-1-carboxamide [4170];
trans-N-(6-(2-methyloxazol-5-yl)-2,7-naphthyridin-3-yl)-4-((propan-2-yl-1,1,1,3,3,3-d$_6$)amino) cyclohexane-1-carboxamide [4171];
trans-4-((2,2-difluoroethyl)amino)-N-(6-(2-methyloxazol-5-yl)-2,7-naphthyridin-3-yl) cyclohexane-1-carboxamide [4172];
trans-N-(6-(2-methyloxazol-5-yl)-2,7-naphthyridin-3-yl)-4-((3,3,3-trifluoropropyl)amino) cyclohexane-1-carboxamide [4173];
trans-4-((2-methoxyethyl)amino)-N-(6-(2-methyloxazol-5-yl)-2,7-naphthyridin-3-yl) cyclohexane-1-carboxamide [4174];
trans-4-(dimethylamino)-N-(6-(2-methyloxazol-5-yl)-2,7-naphthyridin-3-yl)cyclohexane-1-carboxamide [4175];
trans-4-(bis(methyl-d$_3$)amino)-N-(6-(2-methyloxazol-5-yl)-2,7-naphthyridin-3-yl)cyclohexane-1-carboxamide [4176];
cis-4-(dimethylamino)-N-(6-(2-methyloxazol-5-yl)-2,7-naphthyridin-3-yl)cyclohexane-1-carboxamide [4177];
trans-4-((2,2-difluoroethyl)(methyl)amino)-N-(6-(2-methyloxazol-5-yl)-2,7-naphthyridin-3-yl) cyclohexane-1-carboxamide [4178];
trans-4-(methyl(oxetan-3-yl)amino)-N-(6-(2-methyloxazol-5-yl)-2,7-naphthyridin-3-yl) cyclohexane-1-carboxamide [4179];
trans-4-((2-fluoroethyl)amino)-N-(6-(2-methyloxazol-5-yl)-2,7-naphthyridin-3-yl)cyclohexane-1-carboxamide [4180];
trans-4-(2-(fluoromethyl)aziridin-1-yl)-N-(6-(2-methyloxazol-5-yl)-2,7-naphthyridin-3-yl) cyclohexane-1-carboxamide [4181];
trans-4-((3-fluoroazetidin-1-yl)methyl)-N-(6-(2-methyloxazol-5-yl)-2,7-naphthyridin-3-yl) cyclohexane-1-carboxamide [4182];
trans-N-(6-(2-methyloxazol-5-yl)-2,7-naphthyridin-3-yl)-3-morpholinocyclobutane-1-carboxamide [4183];
trans-N-(6-(2-methyloxazol-5-yl)-2,7-naphthyridin-3-yl)-4-morpholinocyclohexane-1-carboxamide [4184];
N-(6-(2-methyloxazol-5-yl)-2,7-naphthyridin-3-yl)-2-(piperidin-1-yl)acetamide [4185];
2-(4-methoxypiperidin-1-yl)-N-(6-(2-methyloxazol-5-yl)-2,7-naphthyridin-3-yl)acetamide [4186];
N-(6-(2-methyloxazol-5-yl)-2,7-naphthyridin-3-yl)-2-(4-methylpiperazin-1-yl)acetamide [4187];
N-(6-(2-methyloxazol-5-yl)-2,7-naphthyridin-3-yl)morpholine-4-carboxamide [4188];
N-(6-(2-methyloxazol-5-yl)-2,7-naphthyridin-3-yl)-2-morpholinoacetamide [4189];
N-(6-(2-methyloxazol-5-yl)-2,7-naphthyridin-3-yl)-3-morpholinopropanamide [4190];
1-methyl-N-(6-(2-methyloxazol-5-yl)-2,7-naphthyridin-3-yl)piperidine-4-carboxamide [4191];
1-(2,2-difluoropropyl)-N-(6-(2-methyloxazol-5-yl)-2,7-naphthyridin-3-yl)piperidine-4-carboxamide [4192];
N-(6-(2-methyloxazol-5-yl)-2,7-naphthyridin-3-yl)-4-morpholinopiperidine-1-carboxamide [4193];
4-((1,3-difluoropropan-2-yl)amino)-N-(6-(2-methyloxazol-5-yl)-2,7-naphthyridin-3-yl) piperidine-1-carboxamide [4194];
(1R,3s,5S)-3-((1,3-difluoropropan-2-yl)amino)-N-(6-(2-methyloxazol-5-yl)-2,7-naphthyridin-3-yl)-8-azabicyclo[3.2.1]octane-8-carboxamide [4195];
(1R,3s,5S)-3-((1,3-difluoropropan-2-yl)amino)-N-(6-(2-methyloxazol-5-yl)-2,7-naphthyridin-3-yl)-8-azabicyclo[3.2.1]octane-8-carboxamide [4196];
4-(dimethylamino)-N-(6-(2-methyloxazol-5-yl)-2,7-naphthyridin-3-yl)piperidine-1-carboxamide [4197];
4-((2,2-difluoroethyl)(methyl)amino)-N-(6-(2-methyloxazol-5-yl)-2,7-naphthyridin-3-yl) piperidine-1-carboxamide [4198];
(3S,4S)-4-amino-3-fluoro-N-(6-(2-methyloxazol-5-yl)-2,7-naphthyridin-3-yl)piperidine-1-carboxamide [4199];
(3S,4S)-3-fluoro-4-(methylamino)-N-(6-(2-methyloxazol-5-yl)-2,7-naphthyridin-3-yl)piperidine-1-carboxamide [4200];
(3 R,4R)-4-amino-3-fluoro-N-(6-(2-methyloxazol-5-yl)-2,7-naphthyridin-3-yl)piperidine-1-carboxamide [4201];
(3R,4R)-3-fluoro-4-(methylamino)-N-(6-(2-methyloxazol-5-yl)-2,7-naphthyridin-3-yl)piperidine-1-carboxamide [4202];
4-((2-fluoroethyl)amino)-N-(6-(2-methyloxazol-5-yl)-2,7-naphthyridin-3-yl)piperidine-1-carboxamide [4203];
4-((2,2-difluoroethyl)amino)-N-(6-(2-methyloxazol-5-yl)-2,7-naphthyridin-3-yl)piperidine-1-carboxamide [4204];
(1R,3s,5S)-3-amino-N-(6-(2-methyloxazol-5-yl)-2,7-naphthyridin-3-yl)-8-azabicyclo[3.2.1] octane-8-carboxamide [4205];
(1R,3r,5S)-3-amino-N-(6-(2-methyloxazol-5-yl)-2,7-naphthyridin-3-yl)-8-azabicyclo[3.2.1] octane-8-carboxamide [4206];
(1R,3r,5S)-3-((2-fluoroethyl)amino)-N-(6-(2-methyloxazol-5-yl)-2,7-naphthyridin-3-yl)-8-azabicyclo[3.2.1] octane-8-carboxamide [4207];
(1R,3r,5S)-3-((2,2-difluoroethyl)amino)-N-(6-(2-methyloxazol-5-yl)-2,7-naphthyridin-3-yl)-8-azabicyclo [3.2.1]octane-8-carboxamide [4208];
(1R,3s,5 S)—N-(6-(2-methyloxazol-5-yl)-2,7-naphthyridin-3-yl)-3-((3,3,3-trifluoropropyl)amino)-8-azabicyclo[3.2.1]octane-8-carboxamide [4209];
(3 S,4S)-3-fluoro-4-(isopropylamino)-N-(6-(2-methyloxazol-5-yl)-2,7-naphthyridin-3-yl) piperidine-1-carboxamide [4210];
N-(6-(2-methyloxazol-5-yl)-2,7-naphthyridin-3-yl)-5,6-dihydroimidazo[1,2-a]pyrazine-7(8H)-carboxamide [4211];
2-methyl-N-(6-(2-methyloxazol-5-yl)-2,7-naphthyridin-3-yl)-5,6-dihydroimidazo[1,2-a]pyrazine-7(8H)-carboxamide [4212];
N-(6-(2-methyloxazol-5-yl)-2,7-naphthyridin-3-yl)-2-(morpholino-d$_8$)acetamide [4213];

trans-N-(6-(2-methyloxazol-4-yl)-2,7-naphthyridin-3-yl)-4-(4-methylpiperazin-1-yl)cyclohexane-1-carboxamide [4214];
N-(6-(2-methyloxazol-5-yl)-2,7-naphthyridin-3-yl)-1-(1-methylpiperidin-4-yl)-1H-pyrazole-4-carboxamide [4215];
2-(1H-imidazol-1-yl)-N-(6-(2-methyloxazol-5-yl)-2,7-naphthyridin-3-yl)acetamide [4216];
4-(difluoromethoxy)-N-(6-(oxazol-5-yl)-2,7-naphthyridin-3-yl)benzamide [4217];
3-((1-methylpiperidin-4-yl)oxy)-N-(6-(oxazol-5-yl)-2,7-naphthyridin-3-yl)benzamide [4218];
N-(6-(oxazol-5-yl)-2,7-naphthyridin-3-yl)isonicotinamide [4219];
2-(3-aminoazetidin-1-yl)-N-(6-(oxazol-5-yl)-2,7-naphthyridin-3-yl)isonicotinamide [4220];
2-(1-methylpiperidin-4-yl)-N-(6-(oxazol-5-yl)-2,7-naphthyridin-3-yl)isonicotinamide [4221];
1'-methyl-N-(6-(oxazol-5-yl)-2,7-naphthyridin-3-yl)-1',2',3',6'-tetrahydro-[2,4'-bipyridine]-4-carboxamide [4222];
2-(4-methylpiperazin-1-yl)-N-(6-(oxazol-5-yl)-2,7-naphthyridin-3-yl)isonicotinamide [4223];
2-(7-methyl-2,7-diazaspiro[3.5]nonan-2-yl)-N-(6-(oxazol-5-yl)-2,7-naphthyridin-3-yl) isonicotinamide [4224];
N-(6-(oxazol-5-yl)-2,7-naphthyridin-3-yl)-2-(2,7-diazaspiro[3.5]nonan-7-yl)isonicotinamide [4225];
N-(6-(oxazol-5-yl)-2,7-naphthyridin-3-yl)-2-(piperidin-4-ylamino)isonicotinamide [4226];
2-methyl-N-(6-(oxazol-5-yl)-2,7-naphthyridin-3-yl)isoindoline-5-carboxamide [4227];
N-(6-(oxazol-5-yl)-2,7-naphthyridin-3-yl)-1,2,3,4-tetrahydroisoquinoline-7-carboxamide [4228];
N-(6-(2-methyloxazol-5-yl)-2,7-naphthyridin-3-yl)-2-(4-methylpiperazin-1-yl)isonicotinamide [4229];
N-(6-(3-methylisoxazol-5-yl)-2,7-naphthyridin-3-yl)-1-(3,3,3-trifluoropropyl)piperidine-4-carboxamide [4230];
4-fluoro-1-isobutyl-N-(6-(5-methyl-1,3,4-oxadiazol-2-yl)-2,7-naphthyridin-3-yl)piperidine-4-carboxamide [4231];
1-isobutyl-N-(6-(5-methyl-1,3,4-oxadiazol-2-yl)-2,7-naphthyridin-3-yl)piperidine-4-carboxamide [4232];
N-(6-(5-(dimethylamino)-1,3,4-oxadiazol-2-yl)-2,7-naphthyridin-3-yl)piperidine-4-carboxamide [4233];
N-(6-(5-(dimethylamino)-1,3,4-oxadiazol-2-yl)-2,7-naphthyridin-3-yl)-1-methylpiperidine-4-carboxamide [4234];
N-(6-(5-methyl-1,3,4-oxadiazol-2-yl)-2,7-naphthyridin-3-yl)-2-(4-methylpiperazin-1-yl) isonicotinamide [4235];
3,3-difluoro-N-(6-(thiazol-5-yl)-2,7-naphthyridin-3-yl)cyclobutane-1-carboxamide [4236];
2-methyl-N-(6-(thiazol-5-yl)-2,7-naphthyridin-3-yl)-2-azaspiro[3.3]heptane-6-carboxamide [4237];
1-fluoro-N-(6-(thiazol-5-yl)-2,7-naphthyridin-3-yl)cyclohexane-1-carboxamide [4238];
trans-4-(dimethylamino)-N-(6-(thiazol-5-yl)-2,7-naphthyridin-3-yl)cyclohexane-1-carboxamide [4239];
trans-4-(((3-fluoroazetidin-1-yl)methyl)-N-(6-(thiazol-5-yl)-2,7-naphthyridin-3-yl)cyclohexane-1-carboxamide [4240];
N-(6-(thiazol-5-yl)-2,7-naphthyridin-3-yl)azetidine-3-carboxamide [4241];
1-methyl-N-(6-(thiazol-5-yl)-2,7-naphthyridin-3-yl)piperidine-4-carboxamide [4242];
1-(2,2-difluoropropyl)-N-(6-(thiazol-5-yl)-2,7-naphthyridin-3-yl)piperidine-4-carboxamide [4243];
1-(oxetan-3-yl)-N-(6-(thiazol-5-yl)-2,7-naphthyridin-3-yl)piperidine-4-carboxamide [4244];
1-(2-(pyrrolidin-1-yl)acetyl)-N-(6-(thiazol-5-yl)-2,7-naphthyridin-3-yl)piperidine-4-carboxamide [4245];
1'-methyl-N-(6-(thiazol-5-yl)-2,7-naphthyridin-3-yl)-[1,4'-bipiperidine]-4-carboxamide [4246];
2-(pyrrolidin-1-yl)-N-(6-(thiazol-5-yl)-2,7-naphthyridin-3-yl)propanamide [4247];
2-(piperidin-1-yl)-N-(6-(thiazol-5-yl)-2,7-naphthyridin-3-yl)acetamide [4248];
2-(4-methylpiperazin-1-yl)-N-(6-(thiazol-5-yl)-2,7-naphthyridin-3-yl)acetamide [4249];
2-morpholino-N-(6-(thiazol-5-yl)-2,7-naphthyridin-3-yl)acetamide [4250];
4-(piperidin-4-yloxy)-N-(6-(thiazol-5-yl)-2,7-naphthyridin-3-yl)benzamide [4251];
N-(6-(thiazol-5-yl)-2,7-naphthyridin-3-yl)isonicotinamide [4252];
6-(4-methylpiperazin-1-yl)-N-(6-(thiazol-5-yl)-2,7-naphthyridin-3-yl)nicotinamide [5253];
1'-methyl-N-(6-(thiazol-5-yl)-2,7-naphthyridin-3-yl)-1',2',3',6'-tetrahydro-[2,4'-bipyridine]-4-carboxamide [4254];
2-(3-(dimethylamino)azetidin-1-yl)-N-(6-(thiazol-5-yl)-2,7-naphthyridin-3-yl)isonicotinamide [4255];
2-(4-(dimethylamino)piperidin-1-yl)-N-(6-(thiazol-5-yl)-2,7-naphthyridin-3-yl)isonicotinamide [4256];
2-(4-methylpiperazin-1-yl)-N-(6-(thiazol-5-yl)-2,7-naphthyridin-3-yl)isonicotinamide [4257];
2-((1-methylpiperidin-4-yl)thio)-N-(6-(thiazol-5-yl)-2,7-naphthyridin-3-yl)isonicotinamide [4258];
N-(6-(thiazol-5-yl)-2,7-naphthyridin-3-yl)-1,2,3,4-tetrahydroisoquinoline-7-carboxamide [4259];
trans-4-((1,3-difluoropropan-2-yl)amino)-N-(6-(5-methyl-1,3,4-thiadiazol-2-yl)-2,7-naphthyridin-3-yl)cyclohexane-1-carboxamide [4260];
N-(6-(2-methylthiazol-5-yl)-2,7-naphthyridin-3-yl)morpholine-4-carboxamide [4261];
N-(6-(2-methylthiazol-5-yl)-2,7-naphthyridin-3-yl)-2-(pyrrolidin-1-yl)acetamide [4262];
2-((1R,4R)-2-oxa-5-azabicyclo[2.2.1]heptan-5-yl)-N-(6-(2-methylthiazol-5-yl)-2,7-naphthyridin-3-yl)acetamide [4263];
N-(6-(2-methylthiazol-5-yl)-2,7-naphthyridin-3-yl)-2-morpholinoacetamide [4264];
N-(6-(2-methylthiazol-5-yl)-2,7-naphthyridin-3-yl)-2-(morpholino-$d_8$)acetamide [4265];
2-(4-methylpiperazin-1-yl)-N-(6-(2-methylthiazol-5-yl)-2,7-naphthyridin-3-yl)acetamide [4266];
1-methyl-N-(6-(2-methylthiazol-5-yl)-2,7-naphthyridin-3-yl)piperidine-4-carboxamide [4267];
N-(6-(2-methylthiazol-5-yl)-2,7-naphthyridin-3-yl)isonicotinamide [4268];
N-(6-(2-methylthiazol-5-yl)-2,7-naphthyridin-3-yl)nicotinamide [4269];
2-(4-methylpiperazin-1-yl)-N-(6-(2-methylthiazol-5-yl)-2,7-naphthyridin-3-yl)isonicotinamide [4270];
trans-N-(6-(5-methyl-1,3,4-thiadiazol-2-yl)-2,7-naphthyridin-3-yl)-4-morpholinocyclohexane-1-carboxamide [4271];
trans-N-(6-(5-methyl-1,3,4-thiadiazol-2-yl)-2,7-naphthyridin-3-yl)-4-(4-methylpiperazin-1-yl) cyclohexane-1-carboxamide [4272];
4-isopropyl-N-(6-(5-methyl-1,3,4-thiadiazol-2-yl)-2,7-naphthyridin-3-yl)piperazine-1-carboxamide [4273];

4-((2-methoxyethyl)(methyl)amino)-N-(6-(5-methyl-1,3,4-thiadiazol-2-yl)-2,7-naphthyridin-3-yl) piperidine-1-carboxamide [4274];

4-((1,3-difluoropropan-2-yl)amino)-N-(6-(5-methyl-1,3,4-thiadiazol-2-yl)-2,7-naphthyridin-3-yl) piperidine-1-carboxamide [4275];

N-(6-(5-methyl-1,3,4-thiadiazol-2-yl)-2,7-naphthyridin-3-yl)-4-((3,3,3-trifluoropropyl)amino) piperidine-1-carboxamide [4276];

4-((2-fluoroethyl)amino)-N-(6-(5-methyl-1,3,4-thiadiazol-2-yl)-2,7-naphthyridin-3-yl)piperidine-1-carboxamide [4277];

(3R,4S)-4-amino-3-fluoro-N-(6-(5-methyl-1,3,4-thiadiazol-2-yl)-2,7-naphthyridin-3-yl) piperidine-1-carboxamide [4278];

(3R,4R)-4-amino-3-fluoro-N-(6-(5-methyl-1,3,4-thiadiazol-2-yl)-2,7-naphthyridin-3-yl) piperidine-1-carboxamide [4279];

(3S,4S)-3-fluoro-N-(6-(5-methyl-1,3,4-thiadiazol-2-yl)-2,7-naphthyridin-3-yl)-4-(methylamino) piperidine-1-carboxamide [4280];

(3R,4R)-3-fluoro-N-(6-(5-methyl-1,3,4-thiadiazol-2-yl)-2,7-naphthyridin-3-yl)-4-(methylamino) piperidine-1-carboxamide [4281];

4-amino-3,3-difluoro-N-(6-(5-methyl-1,3,4-thiadiazol-2-yl)-2,7-naphthyridin-3-yl)piperidine-1-carboxamide [4282];

(3R,4R)-3-fluoro-4-(isopropylamino)-N-(6-(5-methyl-1,3,4-thiadiazol-2-yl)-2,7-naphthyridin-3-yl)piperidine-1-carboxamide [4283];

(3R,4S)-3-fluoro-4-(isopropylamino)-N-(6-(5-methyl-1,3,4-thiadiazol-2-yl)-2,7-naphthyridin-3-yl)piperidine-1-carboxamide [4284];

3,3-difluoro-4-(isopropylamino)-N-(6-(5-methyl-1,3,4-thiadiazol-2-yl)-2,7-naphthyridin-3-yl) piperidine-1-carboxamide [4285];

(3S,4S)-3-fluoro-N-(6-(5-methyl-1,3,4-thiadiazol-2-yl)-2,7-naphthyridin-3-yl)-4-((propan-2-yl-1,1,1,3,3,3-$d_6$)amino)piperidine-1-carboxamide [4286];

(1R,3s,5S)-3-((1,3-difluoropropan-2-yl)amino)-N-(6-(5-methyl-1,3,4-thiadiazol-2-yl)-2,7-naphthyridin-3-yl)-8-azabicyclo[3.2.1]octane-8-carboxamide [4287];

(1R,3s,5S)-3-((1,3-difluoropropan-2-yl)amino)-N-(6-(5-methyl-1,3,4-thiadiazol-2-yl)-2,7-naphthyridin-3-yl)-8-azabicyclo[3.2.1]octane-8-carboxamide [4288];

4-(dimethylamino)-N-(6-(2-methylthiazol-5-yl)-2,7-naphthyridin-3-yl)piperidine-1-carboxamide [4289];

4-((2,2-difluoroethyl)amino)-N-(6-(5-methyl-1,3,4-thiadiazol-2-yl)-2,7-naphthyridin-3-yl) piperidine-1-carboxamide [4290];

4-((2,2-difluoroethyl)(methyl-d3)amino)-N-(6-(5-methyl-1,3,4-thiadiazol-2-yl)-2,7-naphthyridin-3-yl) piperidine-1-carboxamide [4291];

N-(6-(5-methyl-1,3,4-thiadiazol-2-yl)-2,7-naphthyridin-3-yl)-4-morpholinopiperidine-1-carboxamide [4292];

N-(6-(5-methyl-1,3,4-thiadiazol-2-yl)-2,7-naphthyridin-3-yl)-4-(4-methylpiperazin-1-yl) piperidine-1-carboxamide [4293];

(R)-3,4-dimethyl-N-(6-(5-methyl-1,3,4-thiadiazol-2-yl)-2,7-naphthyridin-3-yl)piperazine-1-carboxamide [4294];

(S)-3,4-dimethyl-N-(6-(5-methyl-1,3,4-thiadiazol-2-yl)-2,7-naphthyridin-3-yl)piperazine-1-carboxamide [4295];

(1R,3r,5S)-3-((2-fluoroethyl)amino)-N-(6-(5-methyl-1,3,4-thiadiazol-2-yl)-2,7-naphthyridin-3-yl)-8-azabicyclo[3.2.1]octane-8-carboxamide [4296];

(1R,3r,5S)-3-((2,2-difluoroethyl)amino)-N-(6-(5-methyl-1,3,4-thiadiazol-2-yl)-2,7-naphthyridin-3-yl)-8-azabicyclo[3.2.1]octane-8-carboxamide [4297];

(1R,3r,5S)-3-amino-N-(6-(5-methyl-1,3,4-thiadiazol-2-yl)-2,7-naphthyridin-3-yl)-8-azabicyclo [3.2.1]octane-8-carboxamide [4298];

(1 S,4S)-5-methyl-N-(6-(5-methyl-1,3,4-thiadiazol-2-yl)-2,7-naphthyridin-3-yl)-2,5-diazabicyclo [2.2.1]heptane-2-carboxamide [4299];

(1R,4R)-5-methyl-N-(6-(5-methyl-1,3,4-thiadiazol-2-yl)-2,7-naphthyridin-3-yl)-2,5-diazabicyclo [2.2.1]heptane-2-carboxamide [4300];

8-methyl-N-(6-(5-methyl-1,3,4-thiadiazol-2-yl)-2,7-naphthyridin-3-yl)-3,8-diazabicyclo[3.2.1]octane-3-carboxamide [4301];

3-methyl-N-(6-(5-methyl-1,3,4-thiadiazol-2-yl)-2,7-naphthyridin-3-yl)-3,8-diazabicyclo[3.2.1]octane-8-carboxamide [4302];

N-(6-(5-methyl-1,3,4-thiadiazol-2-yl)-2,7-naphthyridin-3-yl)-5,6-dihydroimidazo[1,2-a]pyrazine-7(8H)-carboxamide [4303];

2-(4-methylpiperazin-1-yl)-N-(6-(5-methylthiazol-2-yl)-2,7-naphthyridin-3-yl)isonicotinamide [4304];

2-(4-methylpiperazin-1-yl)-N-(6-(4-methylthiazol-2-yl)-2,7-naphthyridin-3-yl)isonicotinamide [4305];

N-(6-(2-(methylamino)thiazol-5-yl)-2,7-naphthyridin-3-yl)piperidine-4-carboxamide [4306];

1-methyl-N-(6-(2-(methylamino)thiazol-5-yl)-2,7-naphthyridin-3-yl)piperidine-4-carboxamide [4307];

N-(6-(2-(diethylamino)thiazol-5-yl)-2,7-naphthyridin-3-yl)-2-(4-fluoropiperidin-1-yl)acetamide [4308];

N-(6-(2-(diethylamino)thiazol-5-yl)-2,7-naphthyridin-3-yl)-2-(4-methylpiperazin-1-yl)acetamide [4309];

N-(6-(2-aminothiazol-5-yl)-2,7-naphthyridin-3-yl)-2-(4-methylpiperazin-1-yl)isonicotinamide [4310];

N-(6-(2-(methylamino)thiazol-5-yl)-2,7-naphthyridin-3-yl)-2-(4-methylpiperazin-1-yl) isonicotinamide [4311];

N-(6-(2-(dimethylamino)thiazol-5-yl)-2,7-naphthyridin-3-yl)-2-(4-methylpiperazin-1-yl) isonicotinamide [4312];

2-(4-isopropylpiperazin-1-yl)-N-(6-(2-(methylamino)thiazol-5-yl)-2,7-naphthyridin-3-yl) isonicotinamide [4313];

2-(3-(dimethylamino)azetidin-1-yl)-N-(6-(2-(methylamino)thiazol-5-yl)-2,7-naphthyridin-3-yl) isonicotinamide [4314];

2-(3-(dimethylamino)azetidin-1-yl)-N-(6-(2-(dimethylamino)thiazol-5-yl)-2,7-naphthyridin-3-yl) isonicotinamide [4315];

2-(3-aminoazetidin-1-yl)-N-(6-(2-(dimethylamino)thiazol-5-yl)-2,7-naphthyridin-3-yl) isonicotinamide [4316];

N-(6-(5-chlorothiazol-2-yl)-2,7-naphthyridin-3-yl)-2-(4-methylpiperazin-1-yl)isonicotinamide [4317];

2-(6-(2-(4-methylpiperazin-1-yl)isonicotinamido)-2,7-naphthyridin-3-yl)thiazole-5-carboxamide [4318];

N-(6-(isothiazol-4-yl)-2,7-naphthyridin-3-yl)-1-methylpiperidine-4-carboxamide [4319];

N-(6-(1,3,4-thiadiazol-2-yl)-2,7-naphthyridin-3-yl)-4-(difluoromethoxy)benzamide [4320];

N-(6-(1,3,4-thiadiazol-2-yl)-2,7-naphthyridin-3-yl)-4-(piperidin-4-yloxy)benzamide [4321];

N-(6-(1,3,4-thiadiazol-2-yl)-2,7-naphthyridin-3-yl)-4-((1-methylpiperidin-4-yl)oxy)benzamide [4322];

N-(6-(1,3,4-thiadiazol-2-yl)-2,7-naphthyridin-3-yl)-3-((1-methylpiperidin-4-yl)oxy)benzamide [4323];

$N^5$-(6-(1,3,4-thiadiazol-2-yl)-2,7-naphthyridin-3-yl)-$N^2$-methylpyridine-2,5-dicarboxamide [4324];
N-(6-(1,3,4-thiadiazol-2-yl)-2,7-naphthyridin-3-yl)-6-(4-methylpiperazin-1-yl)nicotinamide [4325];
N-(6-(1,3,4-thiadiazol-2-yl)-2,7-naphthyridin-3-yl)-1'-methyl-1',2',3',6'-tetrahydro-[2,4'-bipyridine]-4-carboxamide [4326];
N-(6-(1,3,4-thiadiazol-2-yl)-2,7-naphthyridin-3-yl)-2-(3-(dimethylamino)azetidin-1-yl) isonicotinamide [4327];
N-(6-(1,3,4-thiadiazol-2-yl)-2,7-naphthyridin-3-yl)-2-(4-methylpiperazin-1-yl)isonicotinamide [4328];
N-(6-(1,3,4-thiadiazol-2-yl)-2,7-naphthyridin-3-yl)-2-(4-isopropylpiperazin-1-yl)isonicotinamide [4329];
N-(6-(1,3,4-thiadiazol-2-yl)-2,7-naphthyridin-3-yl)-2-morpholinoisonicotinamide [4330];
1-fluoro-N-(6-(5-methyl-1,3,4-thiadiazol-2-yl)-2,7-naphthyridin-3-yl)cyclohexane-1-carboxamide [4331];
trans-4-methoxy-N-(6-(5-methyl-1,3,4-thiadiazol-2-yl)-2,7-naphthyridin-3-yl)cyclohexane-1-carboxamide [4332];
cis-4-methoxy-N-(6-(5-methyl-1,3,4-thiadiazol-2-yl)-2,7-naphthyridin-3-yl)cyclohexane-1-carboxamide [4333];
trans-4-amino-N-(6-(5-methyl-1,3,4-thiadiazol-2-yl)-2,7-naphthyridin-3-yl)cyclohexane-1-carboxamide [4334];
trans-4-(dimethylamino)-N-(6-(5-methyl-1,3,4-thiadiazol-2-yl)-2,7-naphthyridin-3-yl) cyclohexane-1-carboxamide [4335];
trans-N-(6-(5-methyl-1,3,4-thiadiazol-2-yl)-2,7-naphthyridin-3-yl)-4-morpholinocyclohexane-1-carboxamide [4336];
trans-4-(hydroxymethyl)-N-(6-(5-methyl-1,3,4-thiadiazol-2-yl)-2,7-naphthyridin-3-yl) cyclohexane-1-carboxamide [4337];
N-(6-(5-methyl-1,3,4-thiadiazol-2-yl)-2,7-naphthyridin-3-yl)piperidine-4-carboxamide [4338];
4-fluoro-N-(6-(5-methyl-1,3,4-thiadiazol-2-yl)-2,7-naphthyridin-3-yl)piperidine-4-carboxamide [4339];
1-methyl-N-(6-(5-methyl-1,3,4-thiadiazol-2-yl)-2,7-naphthyridin-3-yl)piperidine-4-carboxamide [4340];
4-fluoro-1-methyl-N-(6-(5-methyl-1,3,4-thiadiazol-2-yl)-2,7-naphthyridin-3-yl)piperidine-4-carboxamide [4341];
1-(2-fluoroethyl)-N-(6-(5-methyl-1,3,4-thiadiazol-2-yl)-2,7-naphthyridin-3-yl)piperidine-4-carboxamide [4342];
1-(2,2-difluoroethyl)-N-(6-(5-methyl-1,3,4-thiadiazol-2-yl)-2,7-naphthyridin-3-yl)piperidine-4-carboxamide [4343];
N-(6-(5-methyl-1,3,4-thiadiazol-2-yl)-2,7-naphthyridin-3-yl)-1-(3,3,3-trifluoropropyl)piperidine-4-carboxamide [4344];
1-(2,2-difluoropropyl)-N-(6-(5-methyl-1,3,4-thiadiazol-2-yl)-2,7-naphthyridin-3-yl)piperidine-4-carboxamide [4345];
1-benzoyl-N-(6-(5-methyl-1,3,4-thiadiazol-2-yl)-2,7-naphthyridin-3-yl)piperidine-4-carboxamide [4346];
N-(6-(5-methyl-1,3,4-thiadiazol-2-yl)-2,7-naphthyridin-3-yl)-2-(pyrrolidin-1-yl)acetamide [4347];
N-(6-(5-methyl-1,3,4-thiadiazol-2-yl)-2,7-naphthyridin-3-yl)-2-(piperidin-1-yl)acetamide [4348];
2-(4-methoxypiperidin-1-yl)-N-(6-(5-methyl-1,3,4-thiadiazol-2-yl)-2,7-naphthyridin-3-yl) acetamide [4349];
N-(6-(5-methyl-1,3,4-thiadiazol-2-yl)-2,7-naphthyridin-3-yl)-2-(4-methylpiperazin-1-yl) acetamide [4350];
N-(6-(5-methyl-1,3,4-thiadiazol-2-yl)-2,7-naphthyridin-3-yl)-2-morpholinoacetamide [4351];
(R)—N-(6-(5-methyl-1,3,4-thiadiazol-2-yl)-2,7-naphthyridin-3-yl)-2-(3-methylmorpholino) acetamide [4352];
2-(7-azabicyclo[2.2.1]heptan-7-yl)-N-(6-(5-methyl-1,3,4-thiadiazol-2-yl)-2,7-naphthyridin-3-yl) acetamide [4353];
2-((1R,4R)-2-oxa-5-azabicyclo[2.2.1]heptan-5-yl)-N-(6-(5-methyl-1,3,4-thiadiazol-2-yl)-2,7-naphthyridin-3-yl)acetamide [4354];
2-(3-oxa-8-azabicyclo[3.2.1]octan-8-yl)-N-(6-(5-methyl-1,3,4-thiadiazol-2-yl)-2,7-naphthyridin-3-yl)acetamide [4355];
2-(8-oxa-3-azabicyclo[3.2.1]octan-3-yl)-N-(6-(5-methyl-1,3,4-thiadiazol-2-yl)-2,7-naphthyridin-3-yl)acetamide [4356];
N-(6-(5-methyl-1,3,4-thiadiazol-2-yl)-2,7-naphthyridin-3-yl)-2-(1,4-oxazepan-4-yl)acetamide [4357];
N-(6-(5-methyl-1,3,4-thiadiazol-2-yl)-2,7-naphthyridin-3-yl)-2-morpholinoacetamide-2,2-$d_2$ [4358];
N-(6-(5-methyl-1,3,4-thiadiazol-2-yl)-2,7-naphthyridin-3-yl)-2-(morpholino-$d_8$)acetamide [4359];
1-methyl-3-(6-(5-methyl-1,3,4-thiadiazol-2-yl)-2,7-naphthyridin-3-yl)-1-(1-methylpiperidin-4-yl) urea [4360];
(3S,4S)-4-amino-3-fluoro-N-(6-(5-methyl-1,3,4-thiadiazol-2-yl)-2,7-naphthyridin-3-yl) piperidine-1-carboxamide [4361];
(3 S,4S)-4-(dimethylamino)-3-fluoro-N-(6-(5-methyl-1,3,4-thiadiazol-2-yl)-2,7-naphthyridin-3-yl) piperidine-1-carboxamide [4362];
N-(6-(5-methyl-1,3,4-thiadiazol-2-yl)-2,7-naphthyridin-3-yl)morpholine-4-carboxamide [4363];
N-(6-(5-methyl-1,3,4-thiadiazol-2-yl)-2,7-naphthyridin-3-yl)-4-(methylamino)piperidine-1-carboxamide [4364];
4-(dimethylamino)-N-(6-(5-methyl-1,3,4-thiadiazol-2-yl)-2,7-naphthyridin-3-yl)piperidine-1-carboxamide [4365];
4-((2,2-difluoroethyl)(methyl)amino)-N-(6-(5-methyl-1,3,4-thiadiazol-2-yl)-2,7-naphthyridin-3-yl)piperidine-1-carboxamide [4366];
(3S,4S)-3-fluoro-4-(isopropylamino)-N-(6-(5-methyl-1,3,4-thiadiazol-2-yl)-2,7-naphthyridin-3-yl)piperidine-1-carboxamide [4367];
2-methyl-N-(6-(5-methyl-1,3,4-thiadiazol-2-yl)-2,7-naphthyridin-3-yl)-5,6-dihydroimidazo[1,2-a]pyrazine-7(8H)-carboxamide [4368];
4-methyl-N-(6-(5-methyl-1,3,4-thiadiazol-2-yl)-2,7-naphthyridin-3-yl)piperazine-1-carboxamide [4369];
N-(6-(5-methyl-1,3,4-thiadiazol-2-yl)-2,7-naphthyridin-3-yl)-1-(1-methylpiperidin-4-yl)-1H-pyrazole-4-carboxamide [4370];
1-(1-isopropylpiperidin-4-yl)-N-(6-(5-methyl-1,3,4-thiadiazol-2-yl)-2,7-naphthyridin-3-yl)-1H-pyrazole-4-carboxamide [4371];
N-(6-(5-methyl-1,3,4-thiadiazol-2-yl)-2,7-naphthyridin-3-yl)-1-(1-methylpiperidin-4-yl)-1H-1,2,3-triazole-4-carboxamide [4372];
N-(6-(5-methyl-1,3,4-thiadiazol-2-yl)-2,7-naphthyridin-3-yl)-2-(piperidin-4-yl)oxazole-4-carboxamide [4373];
N-(6-(5-methyl-1,3,4-thiadiazol-2-yl)-2,7-naphthyridin-3-yl)-2-(1-methylpiperidin-4-yl)oxazole-4-carboxamide [4374];
2-(3-(dimethylamino)azetidin-1-yl)-N-(6-(5-methyl-1,3,4-thiadiazol-2-yl)-2,7-naphthyridin-3-yl) isonicotinamide [4375];
1'-methyl-N-(6-(5-methyl-1,3,4-thiadiazol-2-yl)-2,7-naphthyridin-3-yl)-1',2',3',6'-tetrahydro-[2,4'-bipyridine]-4-carboxamide [4376];

N-(6-(5-methyl-1,3,4-thiadiazol-2-yl)-2,7-naphthyridin-3-yl)-2-(4-methylpiperazin-1-yl) isonicotinamide [4377];
2-(methyl(1-methylpiperidin-4-yl)amino)-N-(6-(5-methyl-1,3,4-thiadiazol-2-yl)-2,7-naphthyridin-3-yl) isonicotinamide [4378];
2-(azetidin-3-yloxy)-N-(6-(5-methyl-1,3,4-thiadiazol-2-yl)-2,7-naphthyridin-3-yl)isonicotinamide [4379];
N-(6-(5-methyl-1,3,4-thiadiazol-2-yl)-2,7-naphthyridin-3-yl)-3-((1-methylpiperidin-4-yl)oxy) benzamide [4380];
N-(6-(5-methyl-1,3,4-thiadiazol-2-yl)-2,7-naphthyridin-3-yl)-2-((1-methylpiperidin-4-yl)thio) isonicotinamide [4381];
6-(4-methylpiperazin-1-yl)-N-(6-(5-(trifluoromethyl)-1,3,4-thiadiazol-2-yl)-2,7-naphthyridin-3-yl)nicotinamide [4382];
2-(4-methylpiperazin-1-yl)-N-(6-(5-(trifluoromethyl)-1,3,4-thiadiazol-2-yl)-2,7-naphthyridin-3-yl)isonicotinamide [4383];
N-(6-(5-amino-1,3,4-thiadiazol-2-yl)-2,7-naphthyridin-3-yl)-2-(4-methylpiperazin-1-yl) isonicotinamide [4384];
N-(6-(5-(dimethylamino)-1,3,4-thiadiazol-2-yl)-2,7-naphthyridin-3-yl)-2-(4-methylpiperazin-1-yl)isonicotinamide [4385];
N-(6-(3-amino-5-fluorophenyl)-2,7-naphthyridin-3-yl)-2-(4-methylpiperazin-1-yl) isonicotinamide [4386];
N-(6-(3-fluoro-5-(isopropylamino)phenyl)-2,7-naphthyridin-3-yl)-2-(4-methylpiperazin-1-yl) isonicotinamide [4387];
1-methyl-N-(6-(pyridin-2-yl)-2,7-naphthyridin-3-yl)piperidine-4-carboxamide [4388];
2-(4-methylpiperazin-1-yl)-N-(6-(pyridin-2-yl)-2,7-naphthyridin-3-yl)isonicotinamide [4389];
2-(4-methylpiperazin-1-yl)-N-(6-(pyridin-4-yl)-2,7-naphthyridin-3-yl)isonicotinamide [4390];
N-(6-(pyridin-3-yl)-2,7-naphthyridin-3-yl)cyclopropanecarboxamide [4391];
N-(6-(pyridin-3-yl)-2,7-naphthyridin-3-yl)-2-(pyrrolidin-1-yl)acetamide [4392];
1-methyl-N-(6-(pyridin-3-yl)-2,7-naphthyridin-3-yl)piperidine-4-carboxamide [4393];
N-(6-(pyridin-3-yl)-2,7-naphthyridin-3-yl)quinuclidine-4-carboxamide [4394];
2-morpholino-N-(6-(pyridin-3-yl)-2,7-naphthyridin-3-yl) acetamide [4395];
2-(morpholino-d$_8$)—N-(6-(pyridin-3-yl)-2,7-naphthyridin-3-yl)acetamide [4396];
2-(4-methylpiperazin-1-yl)-N-(6-(pyridin-3-yl)-2,7-naphthyridin-3-yl)acetamide [4397];
2-(4-methyl-1,4-diazepan-1-yl)-N-(6-(pyridin-3-yl)-2,7-naphthyridin-3-yl)acetamide [4398];
2-(4-methylpiperazin-1-yl)-N-(6-(pyridin-3-yl)-2,7-naphthyridin-3-yl)isonicotinamide [4399];
2-(2-methyl-1H-imidazol-1-yl)-N-(6-(pyridin-3-yl)-2,7-naphthyridin-3-yl)acetamide [4400];
2-(1H-imidazol-1-yl)-N-(6-(pyridin-3-yl)-2,7-naphthyridin-3-yl)acetamide [4401];
2-(piperidin-4-yl)-N-(6-(pyridin-3-yl)-2,7-naphthyridin-3-yl)oxazole-4-carboxamide [4402];
2-(1-methylpiperidin-4-yl)-N-(6-(pyridin-3-yl)-2,7-naphthyridin-3-yl)oxazole-4-carboxamide [4403];
2-(1-isopropylpiperidin-4-yl)-N-(6-(pyridin-3-yl)-2,7-naphthyridin-3-yl)oxazole-4-carboxamide [4404];
trans-N-(6-(5-fluoropyridin-3-yl)-2,7-naphthyridin-3-yl)-3-morpholinocyclobutane-1-carboxamide [4405];
trans-N-(6-(5-fluoropyridin-3-yl)-2,7-naphthyridin-3-yl)-4-((4-methylpiperazin-1-yl)methyl) cyclohexane-1-carboxamide [4406];
N-(6-(5-fluoropyridin-3-yl)-2,7-naphthyridin-3-yl)-2-(pyrrolidin-1-yl)acetamide [4407];
N-(6-(5-fluoropyridin-3-yl)-2,7-naphthyridin-3-yl)-1-methylpiperidine-4-carboxamide [4408];
N-(6-(5-fluoropyridin-3-yl)-2,7-naphthyridin-3-yl)-2-(4-methylpiperazin-1-yl)acetamide [4409];
N-(6-(6-fluoropyridin-3-yl)-2,7-naphthyridin-3-yl)-2-(4-methylpiperazin-1-yl)acetamide [4410];
N-(6-(5-fluoropyridin-3-yl)-2,7-naphthyridin-3-yl)-2-morpholinoacetamide [4411];
N-(6-(5-fluoropyridin-3-yl)-2,7-naphthyridin-3-yl)-3-morpholinopropanamide [4412];
N-(6-(5-fluoropyridin-3-yl)-2,7-naphthyridin-3-yl)-2-(4-methylpiperazin-1-yl)isonicotinamide [4413];
N-(6-(5-fluoropyridin-3-yl)-2,7-naphthyridin-3-yl)-2-(piperidin-4-yl)oxazole-4-carboxamide [4414];
N-(6-(5-fluoropyridin-3-yl)-2,7-naphthyridin-3-yl)-2-(1-methylpiperidin-4-yl)oxazole-4-carboxamide [4415];
N-(6-(5-fluoropyridin-3-yl)-2,7-naphthyridin-3-yl)-2-(1-isopropylpiperidin-4-yl)oxazole-4-carboxamide [4416];
N-(6-(5-chloropyridin-3-yl)-2,7-naphthyridin-3-yl)-2-(4-methylpiperazin-1-yl)isonicotinamide [4417];
N-(6-(5-methylpyridin-3-yl)-2,7-naphthyridin-3-yl)-2-morpholinoacetamide [4418];
N-(6-(5-(difluoromethyl)pyridin-3-yl)-2,7-naphthyridin-3-yl)-3-(piperidin-4-yl)benzamide [4419];
N-(6-(5-(difluoromethyl)pyridin-3-yl)-2,7-naphthyridin-3-yl)-3-(1-methylpiperidin-4-yl) benzamide [4420];
N-(6-(5-(difluoromethyl)pyridin-3-yl)-2,7-naphthyridin-3-yl)-2-(4-methylpiperazin-1-yl) isonicotinamide [4421];
2-(4-methylpiperazin-1-yl)-N-(6-(5-(trifluoromethyl)pyridin-3-yl)-2,7-naphthyridin-3-yl) acetamide [4422];
2-(4-methylpiperazin-1-yl)-N-(6-(6-(trifluoromethyl)pyridin-3-yl)-2,7-naphthyridin-3-yl) acetamide [4423];
N-(6-(5-(hydroxymethyl)pyridin-3-yl)-2,7-naphthyridin-3-yl)-1-methylpiperidine-4-carboxamide [4424];
N-(6-(5-cyanopyridin-3-yl)-2,7-naphthyridin-3-yl)-1-methylpiperidine-4-carboxamide [4425];
N-(6-(5-methoxypyridin-3-yl)-2,7-naphthyridin-3-yl)-1-methylpiperidine-4-carboxamide [4426];
N-(6-(5-methoxypyridin-3-yl)-2,7-naphthyridin-3-yl)-2-morpholinoacetamide [4427];
N-(6-(5-methoxypyridin-3-yl)-2,7-naphthyridin-3-yl)-2-(4-methylpiperazin-1-yl)isonicotinamide [4428];
4-fluoro-N-(6-(5-(piperidin-4-yloxy)pyridin-3-yl)-2,7-naphthyridin-3-yl)benzamide [4429];
N-(6-(5-aminopyridin-3-yl)-2,7-naphthyridin-3-yl)-4-fluorobenzamide [4430];
N-(6-(5-aminopyridin-3-yl)-2,7-naphthyridin-3-yl)-4-(piperidin-4-yloxy)benzamide [4431];
N-(6-(5-aminopyridin-3-yl)-2,7-naphthyridin-3-yl)-2-(4-methylpiperazin-1-yl)isonicotinamide [4432];
N-(6-(5-aminopyridin-3-yl)-2,7-naphthyridin-3-yl)-2-(piperidin-4-yl)oxazole-4-carboxamide [4433];
N-(6-(6-aminopyridin-3-yl)-2,7-naphthyridin-3-yl)-2-(4-methylpiperazin-1-yl)isonicotinamide [4434];
N-(6-(6-(methylamino)pyridin-3-yl)-2,7-naphthyridin-3-yl)-2-(4-methylpiperazin-1-yl) isonicotinamide [4435];
N-(6-(5-(isopropylamino)pyridin-3-yl)-2,7-naphthyridin-3-yl)-3-(piperidin-4-yl)benzamide [4436];
N-(6-(5-(isopropylamino)pyridin-3-yl)-2,7-naphthyridin-3-yl)-3-(1-methylpiperidin-4-yl) benzamide [4437];

N-(6-(5-(isopropylamino)pyridin-3-yl)-2,7-naphthyridin-3-yl)-2-(4-methylpiperazin-1-yl) isonicotinamide [4438];
N-(6-(5-(piperidin-4-ylamino)pyridin-3-yl)-2,7-naphthyridin-3-yl)cyclohexanecarboxamide [4439];
4-fluoro-N-(6-(5-(piperidin-4-ylamino)pyridin-3-yl)-2,7-naphthyridin-3-yl)benzamide [4440];
4-fluoro-N-(6-(5-((1-methylpiperidin-4-yl)amino)pyridin-3-yl)-2,7-naphthyridin-3-yl)benzamide [4441];
N-(6-(5-acetamidopyridin-3-yl)-2,7-naphthyridin-3-yl)-1-methylpiperidine-4-carboxamide [4442];
N-(6-(5-(dimethylamino)pyridin-3-yl)-2,7-naphthyridin-3-yl)-2-(4-methylpiperazin-1-yl) isonicotinamide [4443];
N-(6-(6-(dimethylamino)pyridin-3-yl)-2,7-naphthyridin-3-yl)-2-(4-methylpiperazin-1-yl) isonicotinamide [4444];
1-methyl-N-(6-(5-(pyrrolidin-1-yl)pyridin-3-yl)-2,7-naphthyridin-3-yl)piperidine-4-carboxamide [4445];
N-(6-(5-(pyrrolidin-1-ylmethyl)pyridin-3-yl)-2,7-naphthyridin-3-yl)cyclopropanecarboxamide [4446];
4-fluoro-N-(6-(5-(pyrrolidin-1-ylmethyl)pyridin-3-yl)-2,7-naphthyridin-3-yl)benzamide [4447];
N-(6-(5-((4-hydroxypiperidin-1-yl)methyl)pyridin-3-yl)-2,7-naphthyridin-3-yl) cyclopropanecarboxamide [4448];
4-fluoro-N-(6-(5-((4-hydroxypiperidin-1-yl)methyl)pyridin-3-yl)-2,7-naphthyridin-3-yl) benzamide [4449];
N-(6-(5-(piperazin-1-ylmethyl)pyridin-3-yl)-2,7-naphthyridin-3-yl)cyclopropanecarboxamide [4450];
N-(6-(5-((4-methylpiperazin-1-yl)methyl)pyridin-3-yl)-2,7-naphthyridin-3-yl) cyclopropanecarboxamide [4451];
N-(6-(5-(morpholinomethyl)pyridin-3-yl)-2,7-naphthyridin-3-yl)cyclopropanecarboxamide [4452];
N-methyl-5-(6-(1-methylpiperidine-4-carboxamido)-2,7-naphthyridin-3-yl)nicotinamide [4453];
N-methyl-5-(6-(2-(4-methylpiperazin-1-yl)isonicotinamido)-2,7-naphthyridin-3-yl)nicotinamide [4454];
N-(6-(pyridin-3-yl-d$_4$)-2,7-naphthyridin-3-yl)-2-(pyrrolidin-1-yl)acetamide [4455];
2-(4-methylpiperazin-1-yl)-N-(6-(pyridin-3-yl-d$_4$)-2,7-naphthyridin-3-yl)acetamide [4456];
2-morpholino-N-(6-(pyridin-3-yl-d$_4$)-2,7-naphthyridin-3-yl)acetamide [4457];
1-methyl-N-(6-(2-methylpyrimidin-5-yl)-2,7-naphthyridin-3-yl)piperidine-4-carboxamide [4458];
2-(4-methylpiperazin-1-yl)-N-(6-(2-methylpyrimidin-5-yl)-2,7-naphthyridin-3-yl)isonicotinamide [4459];
N-(6-(2-aminopyrimidin-5-yl)-2,7-naphthyridin-3-yl)-1-methylpiperidine-4-carboxamide [4460];
2-morpholino-N-(6-(pyridazin-3-yl)-2,7-naphthyridin-3-yl)acetamide [4461];
2-morpholino-N-(6-(pyridazin-4-yl)-2,7-naphthyridin-3-yl)acetamide [4462];
N-(6-(pyridazin-4-yl)-2,7-naphthyridin-3-yl)-2-(pyrrolidin-1-yl)acetamide [4463];
trans-3-morpholino-N-(6-(pyrazin-2-yl)-2,7-naphthyridin-3-yl)cyclobutane-1-carboxamide [4464];
trans-4-(dimethylamino)-N-(6-(pyrazin-2-yl)-2,7-naphthyridin-3-yl)cyclohexane-1-carboxamide [4465];
trans-4-morpholino-N-(6-(pyrazin-2-yl)-2,7-naphthyridin-3-yl)cyclohexane-1-carboxamide [4466];
trans-4-((3-fluoroazetidin-1-yl)methyl)-N-(6-(pyrazin-2-yl)-2,7-naphthyridin-3-yl) cyclohexane-1-carboxamide [4467];
trans-4-((4-methylpiperazin-1-yl)methyl)-N-(6-(pyrazin-2-yl)-2,7-naphthyridin-3-yl) cyclohexane-1-carboxamide [4468];
N-(6-(pyrazin-2-yl)-2,7-naphthyridin-3-yl)-2-(pyrrolidin-1-yl)acetamide [4469];
1-methyl-N-(6-(pyrazin-2-yl)-2,7-naphthyridin-3-yl)piperidine-4-carboxamide [4470];
4-fluoro-1-methyl-N-(6-(pyrazin-2-yl)-2,7-naphthyridin-3-yl)piperidine-4-carboxamide [4471];
1-(2-fluoroethyl)-N-(6-(pyrazin-2-yl)-2,7-naphthyridin-3-yl)piperidine-4-carboxamide [4472];
1-(oxetan-3-yl)-N-(6-(pyrazin-2-yl)-2,7-naphthyridin-3-yl)piperidine-4-carboxamide [4473];
2-morpholino-N-(6-(pyrazin-2-yl)-2,7-naphthyridin-3-yl) acetamide [4474];
1-methyl-N-(6-(pyrazin-2-yl)-2,7-naphthyridin-3-yl) azepane-4-carboxamide [4475];
1-isobutyl-N-(6-(pyrazin-2-yl)-2,7-naphthyridin-3-yl) azepane-4-carboxamide [4476];
1-(2-hydroxy-2-methylpropyl)-N-(6-(pyrazin-2-yl)-2,7-naphthyridin-3-yl)azepane-4-carboxamide [4477];
4-(morpholinomethyl)-N-(6-(pyrazin-2-yl)-2,7-naphthyridin-3-yl)benzamide [4478];
2-(4-methylpiperazin-1-yl)-N-(6-(pyrazin-2-yl)-2,7-naphthyridin-3-yl)isonicotinamide [4479], N-(6-(6-(methylamino)pyrazin-2-yl)-2,7-naphthyridin-3-yl)-2-(4-methylpiperazin-1-yl) isonicotinamide [4480];
N-(6-(6-(isopropylamino)pyrazin-2-yl)-2,7-naphthyridin-3-yl)azetidine-3-carboxamide [4481];
N-(6-(6-(isopropylamino)pyrazin-2-yl)-2,7-naphthyridin-3-yl)piperidine-4-carboxamide [4482];
N-(6-(6-(isopropylamino)pyrazin-2-yl)-2,7-naphthyridin-3-yl)-1-methylpiperidine-4-carboxamide [4483];
1-(2-fluoroethyl)-N-(6-(6-(isopropylamino)pyrazin-2-yl)-2,7-naphthyridin-3-yl)piperidine-4-carboxamide [4484];
1-isopropyl-N-(6-(6-(isopropylamino)pyrazin-2-yl)-2,7-naphthyridin-3-yl)piperidine-4-carboxamide [4485];
1-isopentyl-N-(6-(6-(isopropylamino)pyrazin-2-yl)-2,7-naphthyridin-3-yl)piperidine-4-carboxamide [4486];
N-(6-(6-(isopropylamino)pyrazin-2-yl)-2,7-naphthyridin-3-yl)-3-(piperidin-4-yl)benzamide [4487];
N-(6-(6-(isopropylamino)pyrazin-2-yl)-2,7-naphthyridin-3-yl)-3-(1-methylpiperidin-4-yl) benzamide [4488];
N-(6-(6-(isopropylamino)pyrazin-2-yl)-2,7-naphthyridin-3-yl)-1-(piperidin-4-yl)-1H-1,2,3-triazole-4-carboxamide [4489];
1-(1-(2-fluoroethyl)piperidin-4-yl)-N-(6-(6-(isopropylamino)pyrazin-2-yl)-2,7-naphthyridin-3-yl)-1H-1,2,3-triazole-4-carboxamide [4490];
N-(6-(6-(isopropylamino)pyrazin-2-yl)-2,7-naphthyridin-3-yl)-1-(1-isopropylpiperidin-4-yl)-1H-1,2,3-triazole-4-carboxamide [4491];
N-(6-(6-(isopropylamino)pyrazin-2-yl)-2,7-naphthyridin-3-yl)-2-(4-methylpiperazin-1-yl) isonicotinamide [4492], N-(6-(6-(tert-butylamino)pyrazin-2-yl)-2,7-naphthyridin-3-yl)-2-(3-(dimethylamino)azetidin-1-yl) isonicotinamide [4493];
N-(6-(6-(tert-butylamino)pyrazin-2-yl)-2,7-naphthyridin-3-yl)-1'-methyl-1',2',3',6'-tetrahydro-[2,4'-bipyridine]-4-carboxamide [4494];
N-(6-(6-(tert-butylamino)pyrazin-2-yl)-2,7-naphthyridin-3-yl)-2-(4-methylpiperazin-11-yl) isonicotinamide [4495];
N-(6-(6-(tert-butylamino)pyrazin-2-yl)-2,7-naphthyridin-3-yl)-2-(4-isopropylpiperazin-11-yl) isonicotinamide [4496];

N-(6-(6-(tert-butylamino)pyrazin-2-yl)-2,7-naphthyridin-3-yl)-2-morpholinoisonicotinamide [4497];

N-(6-(6-(((3-fluoroazetidin-3-yl)methyl)amino)pyrazin-2-yl)-2,7-naphthyridin-3-yl) cyclopropanecarboxamide [4498];

4-fluoro-N-(6-(6-(((3-fluoroazetidin-3-yl)methyl)amino) pyrazin-2-yl)-2,7-naphthyridin-3-yl) benzamide [4499];

N-(6-(6-(piperidin-4-ylamino)pyrazin-2-yl)-2,7-naphthyridin-3-yl)cyclobutanecarboxamide [4500];

3,3-difluoro-N-(6-(6-(piperidin-4-ylamino)pyrazin-2-yl)-2,7-naphthyridin-3-yl)cyclobutane-1-carboxamide [4501];

N-(6-(6-(piperidin-4-ylamino)pyrazin-2-yl)-2,7-naphthyridin-3-yl)cyclopentanecarboxamide [4502];

4,4-difluoro-N-(6-(6-(piperidin-4-ylamino)pyrazin-2-yl)-2,7-naphthyridin-3-yl)cyclohexane-1-carboxamide [4503];

N-(6-(6-(piperidin-4-ylamino)pyrazin-2-yl)-2,7-naphthyridin-3-yl)tetrahydro-2H-pyran-4-carboxamide [4504];

4-fluoro-N-(6-(6-(piperidin-4-ylamino)pyrazin-2-yl)-2,7-naphthyridin-3-yl)benzamide [4505];

N-(6-(6-(((3 S,4S)-3-fluoropiperidin-4-yl)amino)pyrazin-2-yl)-2,7-naphthyridin-3-yl) cyclopropanecarboxamide [4506];

4-fluoro-N-(6-(6-(((3 S,4S)-3-fluoropiperidin-4-yl) amino)pyrazin-2-yl)-2,7-naphthyridin-3-yl) benzamide [4507];

N-(6-(6-((1-methylpiperidin-4-yl)amino)pyrazin-2-yl)-2,7-naphthyridin-3-yl) cyclobutanecarboxamide [4508];

N-(6-(6-((1-methylpiperidin-4-yl)amino)pyrazin-2-yl)-2,7-naphthyridin-3-yl) cyclopentanecarboxamide [4509];

4-fluoro-N-(6-(6-((1-methylpiperidin-4-yl)amino) pyrazin-2-yl)-2,7-naphthyridin-3-yl)benzamide [4510];

N-(6-(6-((1-isopropylpiperidin-4-yl)amino)pyrazin-2-yl)-2,7-naphthyridin-3-yl) cyclopropanecarboxamide [4511];

3,3-difluoro-N-(6-(6-((1-isopropylpiperidin-4-yl)amino) pyrazin-2-yl)-2,7-naphthyridin-3-yl) cyclobutane-1-carboxamide [4512];

N-(6-(6-((1-isopropylpiperidin-4-yl)amino)pyrazin-2-yl)-2,7-naphthyridin-3-yl) cyclopentanecarboxamide [4513];

4-fluoro-N-(6-(6-((1-isopropylpiperidin-4-yl)amino) pyrazin-2-yl)-2,7-naphthyridin-3-yl) benzamide [4514];

N-(6-(6-(dimethylamino)pyrazin-2-yl)-2,7-naphthyridin-3-yl)-2-(4-methylpiperazin-1-yl) isonicotinamide [4515];

N-(6-(6-(diethylamino)pyrazin-2-yl)-2,7-naphthyridin-3-yl)-2-(4-methylpiperazin-1-yl) isonicotinamide [4516];

N-(6-(6-(3-aminoazetidin-1-yl)pyrazin-2-yl)-2,7-naphthyridin-3-yl)-4-fluorobenzamide [4517];

2-(4-methylpiperazin-1-yl)-N-(6-(6-(pyrrolidin-1-yl) pyrazin-2-yl)-2,7-naphthyridin-3-yl) isonicotinamide [4518];

N-(6-(6-(azetidin-3-ylmethoxy)pyrazin-2-yl)-2,7-naphthyridin-3-yl)-4-fluorobenzamide [4519];

N-(6-(6-(azetidin-3-yloxy)pyrazin-2-yl)-2,7-naphthyridin-3-yl)-4-fluorobenzamide [4520];

N-(6-(1H-pyrrolo[2,3-b]pyridin-5-yl)-2,7-naphthyridin-3-yl)-1-(1-methylpiperidin-4-yl)-1H-pyrazole-4-carboxamide [4521];

N-(6-(1H-pyrrolo[3,2-b]pyridin-6-yl)-2,7-naphthyridin-3-yl)-1-(1-methylpiperidin-4-yl)-1H-pyrazole-4-carboxamide [4522];

N-(6-(1H-pyrrolo[2,3-c]pyridin-4-yl)-2,7-naphthyridin-3-yl)-1-(1-methylpiperidin-4-yl)-1H-pyrazole-4-carboxamide [4523];

N-(6-(1H-pyrrolo[2,3-b]pyridin-5-yl)-2,7-naphthyridin-3-yl)-2-(4-methylpiperazin-1-yl) isonicotinamide [4524];

N-(6-(1H-pyrrolo[3,2-b]pyridin-6-yl)-2,7-naphthyridin-3-yl)-2-(4-methylpiperazin-1-yl) isonicotinamide [4525];

N-(6-(1H-pyrrolo[2,3-c]pyridin-4-yl)-2,7-naphthyridin-3-yl)-2-(4-methylpiperazin-1-yl) isonicotinamide [4526];

2-(4-methylpiperazin-1-yl)-N-(6-(oxazolo[5,4-b]pyridin-6-yl)-2,7-naphthyridin-3-yl) isonicotinamide [4527];

N-(6-(2-methyl-1H-pyrrolo[2,3-b]pyridin-5-yl)-2,7-naphthyridin-3-yl)-2-(4-methylpiperazin-1-yl)isonicotinamide [4528];

N-(6-(3-methyl-1H-pyrrolo[2,3-b]pyridin-5-yl)-2,7-naphthyridin-3-yl)-2-(4-methylpiperazin-1-yl)isonicotinamide [4529];

N-(6-(2-methyl-1H-pyrrolo[3,2-b]pyridin-6-yl)-2,7-naphthyridin-3-yl)-2-(4-methylpiperazin-1-yl)isonicotinamide [4530];

N-(6-(5H-pyrrolo[2,3-b]pyrazin-2-yl)-2,7-naphthyridin-3-yl)-2-(4-methylpiperazin-1-yl) isonicotinamide [4531];

N-(6-(5H-pyrrolo[2,3-b]pyrazin-3-yl)-2,7-naphthyridin-3-yl)-2-(4-methylpiperazin-1-yl) isonicotinamide [4532];

1-isopropyl-N-(6-(6-(piperidin-4-ylamino)pyrazin-2-yl)-2,7-naphthyridin-3-yl)-1H-pyrazole-4-carboxamide [4533];

1-isopropyl-N-(6-(6-((1-methylpiperidin-4-yl)amino) pyrazin-2-yl)-2,7-naphthyridin-3-yl)-1H-pyrazole-4-carboxamide [4534];

trans-4-((2-fluoroethyl)amino)-N-(3-(1-methyl-1H-pyrazol-4-yl)-1,7-naphthyridin-6-yl) cyclohexane-1-carboxamide [4628];

trans-4-((2-methoxyethyl)amino)-N-(3-(1-methyl-1H-pyrazol-4-yl)-1,7-naphthyridin-6-yl) cyclohexane-1-carboxamide [4629];

tert-butyl (trans-4-((3-(1-methyl-1H-pyrazol-4-yl)-1,7-naphthyridin-6-yl)carbamoyl)cyclohexyl) carbamate [4630];

N-(3-(1-methyl-1H-pyrazol-4-yl)-1,7-naphthyridin-6-yl)-2-((1-methylpiperidin-4-yl)amino) isonicotinamide [4631];

N-(3-(1-methyl-1H-pyrazol-4-yl)-1,7-naphthyridin-6-yl)-2-(4-methylpiperazin-1-yl)thiazole-5-carboxamide [4632];

N-(3-(1-methyl-1H-pyrazol-4-yl)-1,7-naphthyridin-6-yl)-2-(4-methylpiperazin-1-yl)thiazole-5-carboxamide [4633];

N-(3-(1-methyl-5-(piperidin-1-ylmethyl)-1H-pyrazol-4-yl)-1,7-naphthyridin-6-yl)-2-(2,7-diazaspiro[3.5] nonan-2-yl)isonicotinamide [4634];

N-(3-(1-methyl-1H-1,2,3-triazol-4-yl)-1,7-naphthyridin-6-yl)-4-(piperidin-4-yloxy)benzamide [4635];

N-(3-(1-methyl-1H-tetrazol-5-yl)-1,7-naphthyridin-6-yl)-1-(3,3,3-trifluoropropyl)piperidine-4-carboxamide [4636];

N-(3-(1,2-dimethyl-1H-imidazol-5-yl)-1,7-naphthyridin-6-yl)-2-(pyrrolidin-1-yl)propanamide [4637];

N-(3-(1,2-dimethyl-1H-imidazol-5-yl)-1,7-naphthyridin-6-yl)-2-(piperidin-1-yl)propanamide [4638];

4-isopropoxy-N-(3-(7-methyl-5,6,7,8-tetrahydroimidazo[1,2-a]pyrazin-3-yl)-1,7-naphthyridin-6-yl)benzamide [4639];
trans-3-morpholino-N-(3-(oxazol-5-yl)-1,7-naphthyridin-6-yl)cyclobutane-1-carboxamide [4640];
trans-4-(hydroxymethyl)-N-(3-(oxazol-5-yl)-1,7-naphthyridin-6-yl)cyclohexane-1-carboxamide [4641];
N-(3-(oxazol-5-yl)-1,7-naphthyridin-6-yl)piperidine-4-carboxamide [4642];
4-morpholino-N-(3-(oxazol-5-yl)-1,7-naphthyridin-6-yl)piperidine-1-carboxamide [4643];
N-(3-(oxazol-5-yl)-1,7-naphthyridin-6-yl)-4-(piperidin-4-yloxy)benzamide [4644];
N-(3-(oxazol-5-yl)-1,7-naphthyridin-6-yl)-3-(piperidin-4-yloxy)benzamide [4645];
2-methyl-N-(3-(oxazol-5-yl)-1,7-naphthyridin-6-yl)-5,6-dihydroimidazo[1,2-a]pyrazine-7(8H)-carboxamide [4646];
2-(1H-imidazol-1-yl)-N-(3-(oxazol-5-yl)-1,7-naphthyridin-6-yl)acetamide [4647];
trans-4-(hydroxymethyl)-N-(3-(thiazol-5-yl)-1,7-naphthyridin-6-yl)cyclohexane-1-carboxamide [4648];
trans-4-(dimethylamino)-N-(3-(thiazol-5-yl)-1,7-naphthyridin-6-yl)cyclohexane-1-carboxamide [4649];
N-(3-(thiazol-5-yl)-1,7-naphthyridin-6-yl)-1-((1-(trifluoromethyl)cyclopropyl)methyl)piperidine-4-carboxamide [4650];
trans-4-(hydroxymethyl)-N-(3-(2-methylthiazol-5-yl)-1,7-naphthyridin-6-yl)cyclohexane-1-carboxamide [4651];
trans-4-(dimethylamino)-N-(3-(2-methylthiazol-5-yl)-1,7-naphthyridin-6-yl)cyclohexane-1-carboxamide [4652];
N-(3-(2-methylthiazol-5-yl)-1,7-naphthyridin-6-yl)-1-(oxetan-3-yl)piperidine-4-carboxamide [4653];
N-(3-(2-methylthiazol-5-yl)-1,7-naphthyridin-6-yl)-1-(2-(pyrrolidin-1-yl)acetyl)piperidine-4-carboxamide [4654];
2-((1S,4S)-2-oxa-5-azabicyclo [2.2.1]heptan-5-yl)-N-(3-(5-methyl-1,3,4-thiadiazol-2-yl)-1,7-naphthyridin-6-yl)acetamide [4655];
N-(3-(5-(cyano(4-hydroxypiperidin-1-yl)methyl)pyridin-3-yl)-1,7-naphthyridin-6-yl) cyclopropanecarboxamide [4656];
4-fluoro-N-(3-(6-((1-methylazetidin-3-yl)methoxy)pyrazin-2-yl)-1,7-naphthyridin-6-yl) benzamide [4657];
1-isopropyl-N-(3-(6-((1-methylpiperidin-4-yl)amino)pyrazin-2-yl)-1,7-naphthyridin-6-yl)-1H-pyrazole-4-carboxamide [4658]; or a pharmaceutically acceptable salt thereof.

17. A pharmaceutical composition comprising a therapeutically effective amount of a compound of claim 1, or a pharmaceutically acceptable salt thereof, and a pharmaceutically acceptable excipient.

\* \* \* \* \*

UNITED STATES PATENT AND TRADEMARK OFFICE
CERTIFICATE OF CORRECTION

PATENT NO. : 10,703,748 B2
APPLICATION NO. : 16/177149
DATED : July 7, 2020
INVENTOR(S) : Sunil Kumar KC et al.

It is certified that error appears in the above-identified patent and that said Letters Patent is hereby corrected as shown below:

On the Title Page (Other Publications), Line 2, delete "Internationa" and insert -- International --, therefor.

(Other Publications), Line 6, delete "inhibiotrs," and insert -- inhibitors," --, therefor.

(Other Publications), Line 12, delete "Internationa" and insert -- International --, therefor.

In the Claims

Column 1661, Line 31, in Claim 1, delete "N($R^5$)$_2$," and insert -- N($R^{15}$)$_2$, --, therefor.

Column 1661, Line 45-46, in Claim 1, delete "C(=O)N($R^5$)$_2$," and insert -- —C(=O)N($R^{15}$)$_2$, --, therefor.

Column 1662, Line 46, in Claim 1, delete "($C_{1-s}$ alkyl)," and insert -- ($C_{1-5}$ alkyl), --, therefor.

Column 1662, Line 65, in Claim 1, delete "$R^5$," and insert -- $R^{15}$, --, therefor.

Column 1663, Line 4, in Claim 1, delete "($C_{1-s}$ alkyl)," and insert -- ($C_{1-5}$ alkyl), --, therefor.

Column 1663, Line 17, in Claim 1, delete "N($R^5$)$_2$," and insert -- N($R^{15}$)$_2$, --, therefor.

Column 1664, Line 30, in Claim 1, delete "($C_{1-s}$ alkyl)," and insert -- ($C_{1-5}$ alkyl), --, therefor.

Column 1664, Line 30-31, in Claim 1, delete "($C_2$-5 alkenyl)," and insert -- ($C_{2-5}$ alkenyl), --, therefor.

Column 1664, Line 56, in Claim 1, delete "($C_{15}$ alkyl)" and insert -- ($C_{1-5}$ alkyl) --, therefor.

Signed and Sealed this
Sixth Day of October, 2020

Andrei Iancu
*Director of the United States Patent and Trademark Office*

CERTIFICATE OF CORRECTION (continued)
U.S. Pat. No. 10,703,748 B2

Column 1676, Line 4, in Claim 12, insert as a new paragraph -- N-(2-(5-(azetidin-1-ylmethyl)-1-methyl-1H-pyrazol-4-yl)-1,6-naphthyridin-7-yl)-4,4-difluorocyclohexane-1-carboxamide [277]; 4,4-difluoro-N-(2-(1-methyl-5-(pyrrolidin-1-ylmethyl)-1H-pyrazol-4-yl)-1,6-naphthyridin-7-yl) cyclohexane-1-carboxamide [278]; 4,4-difluoro-N-(2-(1-methyl-5-(piperidin-1-ylmethyl)-1H-pyrazol-4-yl)-1,6-naphthyridin-7-yl) cyclohexane-1-carboxamide [279]; 2-(2-fluoroethyl)-N-(2-(1-methyl-5-(piperidin-1-ylmethyl)-1H-pyrazol-4-yl)-1,6-naphthyridin-7-yl)-2-azaspiro[3.3]]heptane-6-carboxamide [280]; tert-butyl 6-((2-(1-methyl-5-(piperidin-1-ylmethyl)-1H-pyrazol-4-yl)-1,6-naphthyridin-7-yl)carbamoyl)-2-azaspiro[3.3]heptane-2-carboxylate [281]; 2-fluoro-2-methyl-N-(2-(1-methyl-5-(piperidin-1-ylmethyl)-1H-pyrazol-4-yl)-1,6-naphthyridin-7-yl)propanamide [282]; 2-(diethylamino)-N-(2-(1-methyl-5-(piperidin-1-ylmethyl)-1H-pyrazol-4-yl)-1,6-naphthyridin-7-yl)acetamide [283]; trans-4-methoxy-N-(2-(1-methyl-5-(piperidin-1-ylmethyl)-1H-pyrazol-4-yl)-1,6-naphthyridin-7-yl)cyclohexane-1-carboxamide [284]; trans-4-(hydroxymethyl)-N-(2-(1-methyl-5-(piperidin-1-ylmethyl)-1H-pyrazol-4-yl)-1,6-naphthyridin-7-yl)cyclohexane-1-carboxamide [285]; (R)—N-(2-(1-methyl-5-(piperidin-1-ylmethyl)-1H-pyrazol-4-yl)-1,6-naphthyridin-7-yl)pyrrolidine-2-carboxamide [286]; 1-isobutyl-N-(2-(1-methyl-5-(piperidin-1-ylmethyl)-1H-pyrazol-4-yl)-1,6-naphthyridin-7-yl)piperidine-4-carboxamide [287]; N-(2-(1-methyl-5-(piperidin-1-ylmethyl)-1H-pyrazol-4-yl)-1,6-naphthyridin-7-yl)-1-(oxetan-3-yl)piperidine-4-carboxamide [288]; 1-benzoyl-N-(2-(1-methyl-5-(piperidin-1-ylmethyl)-1H-pyrazol-4-yl)-1,6-naphthyridin-7-yl)piperidine-4-carboxamide [289]; N-(2-(1-methyl-5-(piperidin-1-ylmethyl)-1H-pyrazol-4-yl)-1,6-naphthyridin-7-yl)tetrahydro-2H-pyran-4-carboxamide [290]; N-(2-(1-methyl-5-(piperidin-1-ylmethyl)-1H-pyrazol-4-yl)-1,6-naphthyridin-7-yl)-2-(4-methylpiperidin-1-yl)acetamide [291]; N-(2-(1-(difluoromethyl)-1H-pyrazol-4-yl)-1,6-naphthyridin-7-yl)-2-(4-methylpiperazin-1-yl) isonicotinamide [292];N-(2-(1-ethyl-1H-pyrazol-4-yl)-1,6-naphthyridin-7-yl)-2-(4-methylpiperazin-1-yl) isonicotinamide [293]; --.

Column 1677, Line 38, in Claim 12, delete "pyrazin" and insert -- pyrazin-3-yl) --, therefor.

Column 1678, Line 61, in Claim 12, delete ")-1H-" and insert -- )-1-(piperidin-4-yl)-1H- --, therefor.

Column 1681, Line 16-65, in Claim 12, delete "N-(2-(5-(azetidin-1-ylmethyl)-1-methyl-1H-pyrazol-4-yl)-1,6-naphthyridin-7-yl)-4,4-difluorocyclohexane-1-carboxamide [277]; 4,4-difluoro-N-(2-(1-methyl-5-(pyrrolidin-1-ylmethyl)-1H-pyrazol-4-yl)-1,6-naphthyridin-7-yl) cyclohexane-1-carboxamide [278]; 4,4-difluoro-N-(2-(1-methyl-5-(piperidin-1-ylmethyl)-1H-pyrazol-4-yl)-1,6-naphthyridin-7-yl) cyclohexane-1-carboxamide [279]; 2-(2-fluoroethyl)-N-(2-(1-methyl-5-(piperidin-1-ylmethyl)-1H-pyrazol-4-yl)-1,6-naphthyridin-7-yl)-2-azaspiro[3.3]]heptane-6-carboxamide [280]; tert-butyl 6-((2-(1-methyl-5-(piperidin-1-ylmethyl)-1H-pyrazol-4-yl)-1,6-naphthyridin-7-yl)carbamoyl)-2-azaspiro[3.3]heptane-2-carboxylate [281]; 2-fluoro-2-methyl-N-(2-(1-methyl-5-(piperidin-1-ylmethyl)-1H-pyrazol-4-yl)-1,6-naphthyridin-7-yl)propanamide [282]; 2-(diethylamino)-N-(2-(1-methyl-5-(piperidin-1-ylmethyl)-1H-pyrazol-4-yl)-1,6-naphthyridin-7-yl)acetamide [283]; trans-4-methoxy-N-(2-(1-methyl-5-(piperidin-1-ylmethyl)-1H-pyrazol-4-yl)-1,6-naphthyridin-7-yl)cyclohexane-1-carboxamide [284]; trans-4-(hydroxymethyl)-N-(2-(1-methyl-5-(piperidin-1-ylmethyl)-1H-pyrazol-4-yl)-1,6-naphthyridin-7-yl)cyclohexane-1-carboxamide [285]; (R)—N-(2-(1-methyl-5-(piperidin-1-ylmethyl)-1H-pyrazol-4-yl)-1,6-naphthyridin-7-yl)pyrrolidine-2-carboxamide [286]; 1-isobutyl-N-(2-(1-methyl-5-(piperidin-1-ylmethyl)-1H-pyrazol-4-yl)-1,6-naphthyridin-7-yl)piperidine-4-carboxamide [287]; N-(2-(1-methyl-5-(piperidin-1-ylmethyl)-1H-pyrazol-4-yl)-1,6-naphthyridin-7-yl)-1-(oxetan-3-yl)piperidine-4-carboxamide [288]; 1-benzoyl-N-(2-(1-methyl-5-(piperidin-1-ylmethyl)-1H-pyrazol-4-yl)-1,6-naphthyridin-7-yl)piperidine-4-carboxamide [289]; N-(2-

(1-methyl-5-(piperidin-1-ylmethyl)-1H-pyrazol-4-yl)-1,6-naphthyridin-7-yl)tetrahydro-2H-pyran-4-carboxamide [290]; N-(2-(1-methyl-5-(piperidin-1-ylmethyl)-1H-pyrazol-4-yl)-1,6-naphthyridin-7-yl)-2-(4-methylpiperidin-1-yl)acetamide [291]; N-(2-(1-(difluoromethyl)-1H-pyrazol-4-yl)-1,6-naphthyridin-7-yl)-2-(4-methylpiperazin-1-yl) isonicotinamide [292];N-(2-(1-ethyl-1H-pyrazol-4-yl)-1,6-naphthyridin-7-yl)-2-(4-methylpiperazin-1-yl) isonicotinamide [293];".

Column 1681, Line 27, in Claim 12, delete "[3.3]]" and insert -- [3.3] --, therefor.

Column 1682, Line 59, in Claim 12, delete "[257];" and insert -- [457]; --, therefor.

Column 1690, Line 41, in Claim 12, delete "5 S" and insert -- 5S --, therefor.

Column 1690, Line 44, in Claim 12, delete "5 S" and insert -- 5S --, therefor.

Column 1690, Line 47, in Claim 12, delete "(1 S," and insert -- (1S, --, therefor.

Column 1692, Line 57, in Claim 12, delete "(morpholino-d)" and insert -- (morpholino-d8) --, therefor.

Column 1704, Line 33, in Claim 13, delete "(1R,3 s,5 S)" and insert -- (1R,3s,5S) --, therefor.

Column 1706, Approximately Line 15, in Claim 13, delete "(-methyl" and insert -- (1-methyl --, therefor.

Column 1709, Line 27, in Claim 13, delete "(3,3" and insert -- (3,3,3 --, therefor.

Column 1711, Line 40, in Claim 13, delete "-N$^2$ methylpyridine-" and insert -- -N$^2$-methylpyridine- --, therefor.

Column 1723, Approximately Line 13, in Claim 13, delete "5 S" and insert -- 5S --, therefor.

Column 1727, Line 67, in Claim 13, delete "-1l-" and insert -- -1- --, therefor.

Column 1730, Line 11, in Claim 13, delete "3 S," and insert -- 3S, --, therefor.

Column 1736, Line 31, in Claim 14, delete "3 s,5 S" and insert -- 3s,5S --, therefor.

Column 1745, Line 32, in Claim 14, delete "33" and insert -- 3 --, therefor.

Column 1751, Line 56, in Claim 14, delete "3 s,5 S" and insert -- 3s,5S --, therefor.

Column 1751, Line 59, in Claim 14, delete "5 S" and insert -- 5S --, therefor.

Column 1751, Line 62, in Claim 14, delete "5 S" and insert -- 5S --, therefor.

Column 1753, Line 13-14, in Claim 14, delete "[1 1,4'-bipiperidine]" and insert

CERTIFICATE OF CORRECTION (continued)
U.S. Pat. No. 10,703,748 B2

-- [1,4'-bipiperidine] --, therefor.

Column 1754, Line 65, in Claim 14, delete "5 S" and insert -- 5S --, therefor.

Column 1755, Line 4, in Claim 14, delete "5 S" and insert -- 5S --, therefor.

Column 1755, Line 60-61, in Claim 14, delete "((l-methylpiperidin" and insert -- ((1-methylpiperidin --, therefor.

Column 1757, Line 13, in Claim 14, delete "fluor" and insert -- fluoro- --, therefor.

Column 1761, Line 56, in Claim 14, delete "3 S," and insert -- 3S, --, therefor.

Column 1766, Line 62-64, in Claim 15, delete "trans-4-(dimethylamino)-N-(3(1-methyl-1H-pyrazol-4-yl)-1,7-naphthyridin-6-yl)cyclohexane-1,7-naphthyridin-6-yl)ccarboxamide [2838];" and insert -- trans-4-(dimethylamino)-N-(3-(1-methyl-1H-pyrazol-4-yl)-1,7-naphthyridin-6-yl)cyclohexane-1-carboxamide [2838]; --, therefor.

Column 1779, Line 52, in Claim 15, delete "56" and insert -- 5,6 --, therefor.

Column 1786, Line 42, in Claim 15, delete "piperidin 1" and insert -- piperidine-1 --, therefor.

Column 1786, Line 53, in Claim 15, delete "(3 S," and insert -- (3S, --, therefor.

Column 1787, Line 4, in Claim 15, delete "(3 S," and insert -- (3S, --, therefor.

Column 1787, Line 10, in Claim 15, delete "3 s,5 S)" and insert -- 3s,5S) --, therefor.

Column 1787, Line 32, in Claim 15, delete "5 S" and insert -- 5S --, therefor.

Column 1787, Line 35, in Claim 15, delete "5 S" and insert -- 5S --, therefor.

Column 1787, Line 38, in Claim 15, delete "5 S" and insert -- 5S --, therefor.

Column 1787, Line 41, in Claim 15, delete "(1 S," and insert -- (1S, --, therefor.

Column 1789, Line 54, in Claim 15, delete "(morpholino-d)" and insert -- (morpholino-d8) --, therefor.

Column 1790, Line 7, in Claim 15, delete "(3 S," and insert -- (3S, --, therefor.

Column 1794, Line 33, in Claim 15, delete "-1l-" and insert -- -1- --, therefor.

Column 1794, Line 36, in Claim 15, delete "-1l-" and insert -- -1- --, therefor.

Column 1818, Line 31, in Claim 16, delete "(3 R," and insert -- (3R, --, therefor.

CERTIFICATE OF CORRECTION (continued)
U.S. Pat. No. 10,703,748 B2

Column 1818, Line 54, in Claim 16, delete "5 S" and insert -- 5S --, therefor.

Column 1818, Line 57, in Claim 16, delete "(3 S," and insert -- (3S, --, therefor.

Column 1820, Line 22, in Claim 16, delete "[5253];" and insert -- [4253]; --, therefor.

Column 1822, Line 7, in Claim 16, delete "(1 S," and insert -- (1S, --, therefor.

Column 1823, Line 5, in Claim 16, delete "-'-" and insert -- -1'- --, therefor.

Column 1824, Line 26, in Claim 16, delete "(3 S," and insert -- (3S, --, therefor.

Column 1828, Line 25, in Claim 16, delete "[4479]," and insert -- [4479]; --, therefor.

Column 1828, Line 56, in Claim 16, delete "[4492]," and insert -- [4492]; --, therefor.

Column 1828, Line 63, in Claim 16, delete "-1l-" and insert -- -1- --, therefor.

Column 1828, Line 66, in Claim 16, delete "-1l-" and insert -- -1- --, therefor.

Column 1829, Line 23, in Claim 16, delete "(((3 S," and insert -- (((3S, --, therefor.

Column 1829, Line 26, in Claim 16, delete "(((3 S," and insert -- (((3S, --, therefor.